US012747230B2

(12) United States Patent
Arnold et al.

(10) Patent No.: US 12,747,230 B2
(45) Date of Patent: Sep. 29, 2026

(54) INHIBITORS OF CYSTEINE PROTEASES AND METHODS OF USE THEREOF

(71) Applicant: Pardes Biosciences, Inc., Carlsbad, CA (US)

(72) Inventors: Lee D. Arnold, Rancho Santa Fe, CA (US); Uri Lopatin, Berkeley, CA (US); Walter Keung, Encinitas, CA (US)

(73) Assignee: Pardes Biosciences, Inc., Carlsbad, CA (US)

( * ) Notice: Subject to any disclaimer, the term of this patent is extended or adjusted under 35 U.S.C. 154(b) by 800 days.

(21) Appl. No.: 17/247,000

(22) Filed: May 3, 2021

(65) Prior Publication Data

US 2022/0380347 A1 Dec. 1, 2022

Related U.S. Application Data

(63) Continuation of application No. PCT/US2021/027780, filed on Apr. 16, 2021.

(60) Provisional application No. 63/111,248, filed on Nov. 9, 2020, provisional application No. 63/067,666, filed on Aug. 19, 2020, provisional application No. 63/039,290, filed on Jun. 15, 2020, provisional application No. 63/031,357, filed on May 28, 2020, provisional application No. 63/012,039, filed on Apr. 17, 2020.

(51) Int. Cl.

| | |
|---|---|
| ***C07D 403/12*** | (2006.01) |
| ***A61K 45/06*** | (2006.01) |
| ***C07D 401/12*** | (2006.01) |
| ***C07D 401/14*** | (2006.01) |

(52) U.S. Cl.

CPC ............ *C07D 403/12* (2013.01); *A61K 45/06* (2013.01); *C07D 401/12* (2013.01); *C07D 401/14* (2013.01)

(58) Field of Classification Search

CPC .... A61K 31/496; A61K 31/53; C07D 401/12; C07D 401/14; C07D 403/12; A61P 3/12

See application file for complete search history.

(56) References Cited

U.S. PATENT DOCUMENTS

| | | | |
|---|---|---|---|
| 6,514,997 | B2 | 2/2003 | Dragovich et al. |
| 7,504,382 | B2 | 3/2009 | Cai et al. |
| 7,504,392 | B2 | 3/2009 | Forbes et al. |
| 9,309,284 | B2 | 4/2016 | Chang et al. |
| 9,474,759 | B2 | 10/2016 | Chang et al. |
| 9,975,885 | B2 | 5/2018 | St. John et al. |
| 11,124,497 | B1 | 9/2021 | Arnold et al. |
| 11,358,953 | B2 | 6/2022 | Panarese et al. |
| 11,952,365 | B2 | 4/2024 | Vandyck et al. |
| 2004/0235952 | A1 | 11/2004 | Fuhrman et al. |
| 2005/0143319 | A1 | 6/2005 | Yang et al. |
| 2005/0143320 | A1 | 6/2005 | Yang et al. |
| 2006/0014821 | A1 | 1/2006 | He et al. |
| 2014/0243341 | A1 | 8/2014 | Chang et al. |
| 2019/0151400 | A1 | 5/2019 | Chang et al. |
| 2021/0008150 | A1 | 1/2021 | Schinazi et al. |
| 2022/0324844 | A1 | 10/2022 | Arnold et al. |

FOREIGN PATENT DOCUMENTS

| | | | |
|---|---|---|---|
| CN | 102838523 | A | 12/2012 |
| CN | 103130710 | A | 6/2013 |
| CN | 103145608 | B | 9/2015 |
| CN | 110105348 | A | 8/2019 |
| CN | 110818691 | A | 2/2020 |
| CN | 107459511 | B | 5/2020 |
| CN | 111135167 | A | 5/2020 |
| CN | 113444144 | A | 9/2021 |
| CN | 114057702 | | 2/2022 |
| JP | 2006169176 | A | 6/2006 |
| KR | 2021/0158591 | A | 12/2021 |
| WO | WO-97/31939 | A1 | 9/1997 |
| WO | WO-99/24460 | A2 | 5/1999 |
| WO | WO-2000/049008 | A1 | 8/2000 |
| WO | WO-2001/010894 | A2 | 2/2001 |
| WO | WO-01/19816 | A1 | 3/2001 |
| WO | WO-2001/40189 | A1 | 6/2001 |
| WO | WO-01/49288 | A1 | 7/2001 |
| WO | WO-2002/032884 | A2 | 4/2002 |
| WO | WO-2004/020441 | A1 | 3/2004 |
| WO | WO-2004/092360 | A2 | 10/2004 |
| WO | WO-2004/093860 | A1 | 11/2004 |
| WO | WO-2005058821 | A1 | 6/2005 |
| WO | WO-2005/113580 | A1 | 12/2005 |
| WO | WO-2006/061714 | A2 | 6/2006 |
| WO | WO-2007/120160 | A2 | 10/2007 |
| WO | WO-2013/049382 | A2 | 4/2013 |
| WO | WO-2017/114509 | A1 | 7/2017 |
| WO | WO-2017/197377 | A1 | 11/2017 |
| WO | WO-2017/222935 | A1 | 12/2017 |
| WO | WO-2018/042343 | A2 | 3/2018 |

(Continued)

OTHER PUBLICATIONS

Stille et. al., ChemRxiv, pp. 1-31, publ. 2020 (Year: 2020).*

(Continued)

*Primary Examiner* — Sarah Pihonak

(74) *Attorney, Agent, or Firm* — Goodwin Procter LLP

(57) ABSTRACT

The disclosure provides compounds with warheads and their use in treating medical diseases or disorders, such as viral infections. Pharmaceutical compositions and methods of making various compounds with warheads are provided. The compounds are contemplated to inhibit proteases, such as the 3C, CL- or 3CL-like protease.

14 Claims, 4 Drawing Sheets

(56) References Cited

FOREIGN PATENT DOCUMENTS

| | | | | | |
|---|---|---|---|---|---|
| WO | WO-2020/030143 | A1 | | 2/2020 | |
| WO | WO-2020/247665 | A1 | | 12/2020 | |
| WO | WO-2021/176369 | A1 | | 9/2021 | |
| WO | WO-2021/191827 | A1 | | 9/2021 | |
| WO | WO-2021/206876 | A1 | | 10/2021 | |
| WO | WO-2021/216195 | A1 | | 10/2021 | |
| WO | WO-2021205298 | A1 | | 10/2021 | |
| WO | WO-2021226546 | A1 | | 11/2021 | |
| WO | WO-2021230973 | A1 | * | 11/2021 | ......... A61K 31/4406 |
| WO | WO-2021/252644 | A1 | | 12/2021 | |
| WO | WO-2021250648 | A1 | | 12/2021 | |
| WO | WO-202202042 | A1 | | 1/2022 | |
| WO | WO-2022020242 | A1 | | 1/2022 | |
| WO | WO-2022036018 | A1 | | 2/2022 | |

OTHER PUBLICATIONS

CAS STN abstracts, RN 1030853-23-6, RN 1032752-48-9, RN 478482-86-9, publ. 2003 & 2008 (Year: 2008).*

Abranyi-Balogh, et al. "A road map for prioritizing warheads for cysteine targeting covalent inhibitors," European Journal of Medicinal Chemistry, vol. 160, 2018, pp. 94-107.

Adedeji, et al. "Antiviral drugs specific for coronaviruses in preclinical development," Curr Opin Virol. Oct. 2014;8:45-53.

Albuquerque, et al. "MurineHepatitis Virus Strain 1 Produces a Clinically Relevant Model of Severe Acute Respiratory Syndrome in A/J Mice," Journal of Virology Oct. 2006, 80 (21) 10382-10394.

Amblard, et al., "Synthesis and antiviral evaluation of novel peptidomimetics as norovirus protease inhibitors," Bioorganic & Medicinal Chemistry Letters, vol. 28, Issue 12, 2018, pp. 2165-2170.

Bandyopadhyay, et al. "Targeting biomolecules with reversible covalent chemistry," Current Opinion in Chemical Biology, vol. 34, 2016, pp. 110-116.

Bernassola, et al. "HECT-Type E3 Ubiquitin Ligases in Cancer," Trends Biochem Sci. Dec. 2019;44(12):1057-1075.

Berteottti, et al. "Predicting the Reactivity of Nitrile-Carrying Compounds with Cysteine: A Combined Computational and Experimental Study," ACS Med. Chem. Lett. 2014, 5, 5, 501-505.

Boras, et al., "Discovery of a Novel Inhibitor of Coronavirus 3CL Protease for the Potential Treatment of COVID-19," bioRxiv 2020. 09.12.293498; doi: https://doi.org/10.1101/2020.09.12.293498.

Cai, et al. "4-(3-Trifluoromethylphenyl)-pyrimidine-2-carbonitrile as cathepsin S inhibitors: N3, not N1 is critically important," Bioorg Med Chem Lett . Aug. 1, 2010;20(15):4507-10.

Casimiro-Garcia, et al. "Identification of Cyanamide-Based Janus Kinase 3 (JAK3) Covalent Inhibitors," J. Med. Chem. 2018, 61, 23, 10665-10699.

Chatterjee, et al. "Can Relative Binding Free Energy Predict Selectivity of Reversible Covalent Inhibitors?," J. Am. Chem. Soc. 2017, 139, 49, 17945-17952.

Chuck, et al., "Design, synthesis and crystallographic analysis of nitrile-based broad-spectrum peptidomimetic inhibitors for coronavirus 3C-like proteases," Eur J Med Chem. Jan. 2013;59:1-6.

Chuck, et al., "Supplementary Material: Design, synthesis and crystallographic analysis of nitrile-based broad-spectrum peptidomimetic inhibitors for coronavirus 3C-like proteases," Eur J Med Chem. Jan. 2013;59:1-6.

Coteron, et al. "Falcipain Inhibitors: Optimization Studies of the 2-Pyrimidinecarbonitrile Lead Series," J. Med. Chem. 2010, 53, 16, 6129-6152.

Dai, et al., "Structure-based design of antiviral drug candidates targeting the SARS-CoV-2 main protease," Science Jun. 19, 2020: vol. 368, Issue 6497, pp. 1331-1335.

Damalanka, et al., "Structure-guided design, synthesis and evaluation of oxazolidinone-based inhibitors of norovirus 3CL protease," European Journal of Medicinal Chemistry, vol. 143, 2018, pp. 881-890.

De Cesco, et al. "Covalent inhibitors design and discovery," Eur J Med Chem . Sep. 29, 2017;138:96-114.

Doheny, et al. "Are Human Challenge Trials for COVID-19 Vaccine Worth the Risk?" Medscape, Medscape, Oct. 7, 2020, www.medscape.com/viewarticle/935377#:~:text=The%20trials%20could%20effectively%20deliver,or%20potentially%20the%20life%2C%20of.

Dong, et al. "Discovering drugs to treat coronavirus disease 2019 (COVID-19)," Drug Discov Ther. 2020;14(1):58-60.

Dragovich, et al. "Structure-Based Design, Synthesis, and Biological Evaluation of Irreversible Human Rhinovirus 3C Protease Inhibitors. 4. Incorporation of P1 Lactam Moieties as I-Glutamine Replacements," J. Med. Chem. 1999, 42, 7, 1213-1224.

Eaton, et al. "Selective covalent targeting of GPX4 using masked nitrile-oxide electrophiles," Nature Chemical Biology vol. 16, pp. 497-506(2020).

Ehmke, et al., "Tuning and predicting biological affinity: arylnitriles as cysteine protease inhibitors," Org. Biomol. Chem., 2012,10, 5764-5768.

Fischer, et al. "Inhibitors for Novel Coronavirus Protease Identified by Virtual Screening of 687 Million Compounds," Mar. 2020; Preprint. https://doi.org/10.26434/chemrxiv.11923239.v1.

Flanagan, et al., "Chemical and Computational Methods for the Characterization of Covalent Reactive Groups for the Prospective Design of Irreversible Inhibitors," Journal of Medicinal Chemistry, 2014, 57, 23, 10072-10079.

Fleming, et al. "Nitrile-Containing Pharmaceuticals: Efficacious Roles of the Nitrile Pharmacophore," J. Med. Chem. 2010, 53, 22, 7902-7917.

Gehringer, et al., "Emerging and Re-Emerging Warheads for Targeted Covalent Inhibitors: Applications in Medicinal Chemistry and Chemical Biology," J. Med. Chem. Jun. 27, 2019;62(12):5673-5724.

Hou, et al. "SARS-CoV-2 Reverse Genetics Reveals a Variable Infection Gradient in the Respiratory Tract," Cell . Jul. 23, 2020;182(2):429-446.e14.

Jeon, et al. "Identification of Antiviral Drug Candidates against SARS-CoV-2 from FDA-Approved Drugs," Antimicrobial Agents and Chemotherapy Jun. 2020, 64 (7) e00819-20.

Johnson, et al. "Structure-based design of a parallel synthetic array directed toward the discovery of irreversible inhibitors of human rhinovirus 3C protease," J Med Chem. May 9, 2002;45(10):2016-23.

Keyser, et al. "Computation-Guided Rational Design of a Peptide Motif That Reacts with Cyanobenzothiazoles via Internal Cysteine-Lysine Relay," J. Org. Chem. 2018, 83, 14, 7467-7479.

Kim, et al., "Broad-spectrum antivirals against 3C or 3C-like proteases of picornaviruses, noroviruses, and coronaviruses," J Virol . Nov. 2012;86(21):11754-62.

Kim, et al., "Broad-spectrum inhibitors against 3C-like proteases of feline coronaviruses and feline caliciviruses," J Virol . May 2015;89(9):4942-50.

Kim, et al., "Reversal of the Progression of Fatal Coronavirus Infection in Cats by a Broad-Spectrum Coronavirus Protease Inhibitor," PLoS Pathog . Mar. 30, 2016;12(3):e1005531.

Kitamura, et al., "Expedited Approach toward the Rational Design of Noncovalent SARS-CoV-2 Main Protease Inhibitors," J. Med. Chem., 2021, Publication Date:Apr. 23, 2021; https://doi.org/10.1021/acs.jmedchem.1c00509.

Konno, et al., "Design and synthesis of new tripeptide-type SARS-CoV 3CL protease inhibitors containing an electrophilic arylketone moiety," Bioorg Med Chem, Jan. 15, 2013;21(2):412-24.

Kruse, et al., "Therapeutic strategies in an outbreak scenario to treat the novel coronavirus originating in Wuhan, China," F1000Res. Jan. 31, 2020;9:72.

Kuhn, et al. "Prospective Evaluation of Free Energy Calculations for the Prioritization of Cathepsin L Inhibitors," J. Med. Chem. 2017, 60, 6, 2485-2497.

Lagoutte, et al. "Covalent inhibitors: an opportunity for rational target selectivity," Curr Opin Chem Biol . Aug. 2017;39:54-63.

Laine, et al. "Discovery of Novel Cyanamide-Based Inhibitors of Cathepsin C," ACS Med. Chem. Lett. 2011, 2, 2, 142-147.

(56) References Cited

OTHER PUBLICATIONS

Liu, et al. "Research and Development on Therapeutic Agents and Vaccines for COVID-19 and Related Human Coronavirus Diseases," ACS Cent. Sci. 2020, 6, 3, 315-331.
Lonsdale, et al. "Structure-based design of targeted covalent inhibitors," Chem. Soc. Rev., 2018, 47, 3816-3830.
Ma, et al., "Boceprevir, GC-376, and calpain inhibitors II, XII inhibit SARS-CoV-2 viral replication by targeting the viral main protease," Cell Res. Aug. 2020; 30(8): 678-692.
Macfaul, et al. "A simple in vitro assay for assessing the reactivity of nitrile containing compounds," Bioorganic & Medicinal Chemistry Letters, vol. 19, Issue 4, 2009, pp. 1136-1138.
Martin, et al., "Characterising covalent warhead reactivity," Bioorganic & Medicinal Chemistry, May 15, 2019;27(10):2066-2074.
Montagutelli, et al. "The B1.351 and P.1 variants extend SARS-CoV-2 host range to mice," bioRxiv 2021.03.18.436013.
Mott, et al., "Identification and optimization of inhibitors of Trypanosomal cysteine proteases: cruzain, rhodesain, and TbCatB," Journal of Medicinal Chemistry, Jan. 14, 2010;53(1):52-60.
Namoto, et al. "Structure-based design and synthesis of macrocyclic human rhinovirus 3C protease inhibitors," Bioorg Med Chem Lett. Mar. 1, 2018;28(5):906-909.
Oballa, et al., "A generally applicable method for assessing the electrophilicity and reactivity of diverse nitrile-containing compounds," Bioorganic & Medicinal Chemistry Letters, vol. 17, Issue 4, 2007, pp. 998-1002.
Paasche, et al. "Mechanistic Insights into SARS Coronavirus Main Protease by Computational Chemistry Methods," 2012: n. pag. Print. Doctoral Thesis, University of Würzburg. https://d-nb.info/1037687825/34.
Patick, et al. "Protease Inhibitors as Antiviral Agents," Clin Microbiol Rev. Oct. 1998; 11(4): 614-627.
Pillaiyar, et al., "An Overview of Severe Acute Respiratory Syndrome-Coronavirus (SARS-CoV) 3CL Protease Inhibitors: Peptidomimetics and Small Molecule Chemotherapy," J. Med. Chem. 2016, 59, 14, 6595-6628.
Prior, et al., "Design, synthesis, and bioevaluation of viral 3C and 3C-like protease inhibitors," Bioorganic & Medicinal Chemistry Letters, vol. 23, Issue 23, 2013, pp. 6317-6320.
Rathnayake, et al., "3C-like protease inhibitors block coronavirus replication in vitro and improve survival in MERS-CoV-infected mice," Science Translational Medicine, Aug. 19, 2020: vol. 12, Issue 557, eabc5332.
Ray, et al. "New Electrophiles and Strategies for Mechanism-Based and Targeted Covalent Inhibitor Design," Biochemistry 2019, 58, 52, 5234-5244.
Santos, et al., "Experimental study and computational modelling of cruzain cysteine protease inhibition by dipeptidyl nitriles," Phys. Chem. Chem. Phys., 2018, 20, 24317-24328.
Santos, et al., "Michael acceptors as cysteine protease inhibitors," Mini Rev Med Chem . Oct. 2007;7(10):1040-50.
Schade, et al. "Highly Selective Sub-Nanomolar Cathepsin S Inhibitors by Merging Fragment Binders with Nitrile Inhibitors," J. Med. Chem. 2020, 63, 20, 11801-11808.
Schnute, et al. "Aminopyrazole Carboxamide Bruton's Tyrosine Kinase Inhibitors. Irreversible to Reversible Covalent Reactive Group Tuning," ACS Med. Chem. Lett. 2019, 10, 1, 80-85.
Serafimova, et al. (2013). Reversible targeting of noncatalytic cysteines with chemically tuned electrophiles. UCSF. ProQuest ID: Serafimova_ucsf_0034D_10695.REDACTED. Merritt ID: ark:/13030/m5x36bhx. Retrieved from https://escholarship.org/uc/item/0cj6m628.
Silva, et al. "A comparative study of warheads for design of cysteine protease inhibitors," Bioorg Med Chem Lett. Nov. 15, 2017;27(22):5031-5035.
Simplicio, et al., "Prodrugs for Amines," Molecules (Basel, Switzerland), 13(3), 519-547.
Sinha, et al. "Electrophilicity of pyridazine-3-carbonitrile, pyrimidine-2-carbonitrile, and pyridine-carbonitrile derivatives: a chemical model to describe the formation of thiazoline derivatives in human liver microsomes," Chem Res Toxicol. Dec. 15, 2014;27(12):2052-61.
Steinhauer, et al., "Rapid evolution of RNA viruses," Annu Rev Microbiol. 1987;41:409-33.
Steuten, et al. "Challenges for Targeting SARS-CoV-2 Proteases as a Therapeutic Strategy for COVID-19," ACS Infect. Dis. 2021, Publication date: Feb. 11, 2021; https://doi.org/10.1021/acsinfecdis.0c00815.
STN Registry Database Entry for 1831065-26-9 entered STN Dec. 16, 2015.
STN Registry Database Entry for 2248095-92-1 entered STN Nov. 13, 2018.
STN Registry Database Entry for 2628280-40-8 entered STN Apr. 7, 2021.
Tomar, et al. "Understanding the determinants for substrate recognition, regulation of enzymatic activity and the development of broad-spectrum inhibitors of coronavirus 3-chymotrypsin-like proteases," (2015). Open Access Dissertations. 1322. https://docs.lib.purdue.edu/open_access_dissertations/1322.
Totura, et al. "Broad-spectrum coronavirus antiviral drug discovery," Expert Opin Drug Discov. Apr. 2019;14(4):397-412.
Vuong, et al., "Feline coronavirus drug inhibits the main protease of SARS-CoV-2 and blocks virus replication," Nat Commun . Aug. 27, 2020;11(1):4282.
Wang, et al., "Covalent binding design strategy: A prospective method for discovery of potent targeted anticancer agents," European Journal of Medicinal Chemistry, vol. 142, 2017, pp. 493-505.
Wang, et al., "Inhibition of enterovirus 71 replication by an a-hydroxy-nitrile derivative NK-1.9k," Antiviral Res . May 2017;141:91-100.
White, et al., "Plitidepsin has potent preclinical efficacy against SARS-CoV-2 by targeting the host protein eEF1A," Science Feb. 26, 2021: vol. 371, Issue 6532, pp. 926-931.
Ye, et al., "Structural Basis for Inhibiting Porcine Epidemic Diarrhea Virus Replication with the 3C-Like Protease Inhibitor GC376," Viruses. Feb. 21, 2020;12(2):240.
Zaidman, et al. "An automatic pipeline for the design of irreversible derivatives identifies a potent SARS-CoV-2 Mpro inhibitor," bioRxiv 2020.09.21.299776.
Zhai, et al., "Cyanohydrin as an Anchoring Group for Potent and Selective Inhibitors of Enterovirus 71 3C Protease," J. Med. Chem. 2015, 58, 23, 9414-9420.
Zhao, et al. "Progress with covalent small-molecule kinase inhibitors," vol. 23, Issue 3, 2018, pp. 727-735, ISSN 1359-6446.
Dai, et al. "Design, Synthesis, and Biological Evaluation of Peptidomimetic Aldehydes as Broad-Spectrum Inhibitors against Enterovirus and SARS-CoV-2," Journal of Medicinal Chemistry, (Ahead of Print), 2021 (available online on Apr. 19, 2021), pp. A-O, ISSN: 0022-2623.
Hoffman, et al. "Discovery of Ketone-Based Covalent Inhibitors of Coronavirus 3CL Proteases for the Ptential Therapeutic Treatment of COVID-19," Journal of Medicinal Chemistry, vol. 63(21), 2020 (published on Oct. 15, 2020), pp. 12725-12747.
Masand, et al. "Structure features of peptide-type SARS-CoV main protease inhibitors: Quantitative structure activity relationship study," Chemometrics and Intelligent Laboratory Systems, vol. 206, 104172, 2020 (available online on Oct. 3, 2020).
Thanigaimalai, et al. "Development of potent dipeptide-type SARS-CoV 3CL protease inhibitors with novel P3 scaffolds: Design, synthesis, biological evaluation, and docking studies," European Journal of Medicinal Chemistry, vol. 68, 2013, pp. 372-384, ISSN: 0223-5234.
Jacobs, et al. "Discovery, synthesis, and structure-based optimization of a Series of N-(tert-butyl)-2-(N-arylamido)-2-(pyridine-3-yl) acetamides (ML188) as potent noncovalent small molecule inhibitors of the severe acute respiratory syndrome coronavirus (SARS-CoV) 3CL protease," Journal of Medicinal Chemistry, 2013, vol. 56, No. 2, 534-546.
St. John, et al. "Targeting zoonotic viruses: Structure-based inhibition of the 3C-like protease from bat coronavirus HKU4—The likely reservoir host to the human coronavirus that causes Middle East Respiratory Syndrome (MERS)," Bioorganic & Medicinal Chemistry, vol. 23, No. 17, 6036-6048.

(56) References Cited

OTHER PUBLICATIONS

Wang, et al., "Recent progress in the discovery of inhibitors targeting coronavirus proteases," Virologica Sinica, Springer, DE, vol. 31, No. 1, 24-30.
Thanigaimalai Pillaiyar et al: "Design, synthesis, and biological evaluation of novel dipeptide-type SARS-CoV 3CL protease inhibitors: Structure-activity relationships," European Journal of Medicinal Chemistry, Elsevier, Amsterdam, NL, vol. 65, May 20, 2013 (May 20, 2013), pp. 436-447, DOI: 10.1016/J.EJMECH.2013.05.005.
Vuong et al: "Improved Synthesis of a Cyclic Glutamine Analogue Used in Antiviral Agents Targeting 3C and 3CL Proteases Including SARS-CoV-2 MPRO," The Journal of Organic Chemistry 2021 86 (18), 13104-13110 DOI: 10.1021/acs.joc.1c01299.
Bai et al: "Peptidomimetic nitrile warheads as SARS-CoV-2 3CL protease inhibitors," RSC Med. Chem., 2021,12, 1722-1730 DOI:10.1039/D1MD00247C.
Owen et al: "An Oral SARS-CoV-2 Mpro Inhibitor Clinical Candidate for the Treatment of COVID-19," medRxiv 2021.07.28.21261232; DOI: https://doi.org/10.1101/2021.07.28.21261232.
Westberg et al: "Rational design of a new class of protease inhibitors for the potential treatment of coronavirus diseases," bioRxiv 2020.09.15.275891; DOI: https://doi.org/10.1101/2020.09.15.275891.
Qiao et al: "SARS-CoV-2 M pro inhibitors with antiviral activity in a transgenic mouse model," Science. Mar. 26, 2021;371(6536):1374-1378. DOI: 10.1126/science.abf1611. Epub Feb. 18, 2021.
Good, et al: "AT-527, a double prodrug of a guanosine nucleotide analog, is a potent inhibitor of SARS-CoV-2 in vitro and a promising oral antiviral for treatment of COVID-19," Antimicrob Agents Chemother 65:e02479-20.
De Vries, et al: "Comparative study of a 3CLpro inhibitor and remdesivir against both major SARS-CoV-2 clades in human airway models" bioRxiv 2020.08.28.272880.
Iketani, et al: "Lead compounds for the development of SARS-CoV-2 3CL protease inhibitors." Nat Commun. Apr. 1, 2021;12(1):2016. doi: 10.1038/s41467-021-22362-2. Erratum in: Nat Commun. May 5, 2021;12(1):2708.
Vandyck, et al: "ALG-097111, a potent and selective SARS-CoV-2 3-chymotrypsin-like cysteine protease inhibitor exhibits in vivo efficacy in a Syrian Hamster model." Biochem Biophys Res Commun. May 28, 2021;555:134-139. doi: 10.1016/j.bbrc.2021.03.096. Epub Mar. 26, 2021.
Liu, et al: "The development of Coronavirus 3C-Like protease (3CLpro) inhibitors from 2010 to 2020." Eur J Med Chem. Nov. 15, 2020;206:112711. doi: 10.1016/j.ejmech.2020.112711. Epub Aug. 6, 2020.
Korkmaz, et al: "Lung Protection by Cathepsin C Inhibition: A New Hope for COVID-19 and ARDS?" J Med Chem. Nov. 25, 2020;63(22):13258-13265. doi: 10.1021/acs.jmedchem.0c00776. Epub Aug. 7, 2020.
Rathnayake, et al "Structure-Guided Optimization of Dipeptidyl Inhibitors of Norovirus 3CL Protease." J Med Chem. Oct. 22, 2020;63(20):11945-11963. doi: 10.1021/acs.jmedchem.0c01252.
Boras, et al "Discovery of a Novel Inhibitor of Coronavirus 3CL Protease as a Clinical Candidate for the Potential Treatment of COVID-19" bioRxiv 2020.09.12.293498; doi: https://doi.org/10.1101/2020.09.12.293498.
Qin, et al "Acrylamide Fragment Inhibitors that Induce Unprecedented Conformational Distortions in Enterovirus 71 3C and SARS-CoV-2 Main Protease" bioRxiv 2020.11.06.370916; doi: <https://doi.org/10.1101/2020.11.06.370916>.
Zhang, et al Supplementary Materials for: Crystal structure of SARS-CoV-2 main protease provides a basis for design of improved ?-ketoamide inhibitors. Science. 2020;368(6489):409-412. doi:10.1126/science.abb3405.
Lockbaum, et al "Pan-3C Protease Inhibitor Rupintrivir Binds SARS-CoV-2 Main Protease in a Unique Binding Mode. Biochemistry." Oct. 5, 2021;60(39):2925-2931. doi: 10.1021/acs.biochem.1c00414. Epub Sep. 10, 2021.
Kneller, et al "Direct Observation of Protonation State Modulation in SARS-CoV-2 Main Protease upon Inhibitor Binding with Neutron Crystallography." J Med Chem. Apr. 22, 2021;64(8):4991-5000. doi: 10.1021/acs.jmedchem.1c00058.
Wang, et al "Comprehensive Insights into the Catalytic Mechanism of Middle East Respiratory Syndrome 3C-Like Protease and Severe Acute Respiratory Syndrome 3C-Like Protease." ACS Catal. 2020;10:5871-5890. doi: 10.1021/acscatal.0c00110. Epub Apr. 28, 2020.
Altmann, et al "Dipeptide nitrile inhibitors of cathepsin K." Bioorg Med Chem Lett. May 1, 2006;16(9):2549-54. doi: 10.1016/j.bmcl.2006.01.104. Epub Feb. 9, 2006.
Frizler, et al "Development of nitrile-based peptidic inhibitors of cysteine cathepsins." Curr Top Med Chem. 2010;10(3):294-322. doi: 10.2174/156802610790725452.
Dragovich et al "Structure-based design, synthesis, and biological evaluation of irreversible human rhinovirus 3C protease inhibitors. 2. Peptide structure-activity studies." J Med Chem. Jul. 16, 1998;41(15):2819-34. doi: 10.1021/jm9800696. PMID: 9667971.
Dragovich, Peter S. et al. "Structure-based design, synthesis, and biological evaluation of irreversible human rhinovirus 3C protease inhibitors. 1. Michael acceptor structure-activity studies." Journal of medicinal chemistry 41 15 (1998): 2806-18.
Dragovich, P S et al. "Structure-based design, synthesis, and biological evaluation of irreversible human rhinovirus 3C protease inhibitors. 3. Structure-activity studies of ketomethylene-containing peptidomimetics." Journal of medicinal chemistry vol. 42,7 (1999): 1203-12. doi:10.1021/jm980537b.
Dragovich, Peter S et al. "Structure-based design, synthesis, and biological evaluation of irreversible human rhinovirus 3C protease inhibitors. 6. Structure-activity studies of orally bioavailable, 2-pyridone-containing peptidomimetics." Journal of medicinal chemistry vol. 45,8 (2002): 1607-23. doi:10.1021/jm010469k.
Dragovich, Peter S et al. "Structure-based design, synthesis, and biological evaluation of irreversible human rhinovirus 3C protease inhibitors. Part 7: structure-activity studies of bicyclic 2-pyridone-containing peptidomimetics." Bioorganic & medicinal chemistry letters vol. 12,5 (2002): 733-8. doi:10.1016/s0960-894x(02)00008-2.
Dragovich, Peter S. et al. "Structure-Based Design, Synthesis, and Biological Evaluation of Irreversible Human Rhinovirus 3C Protease Inhibitors. 8. Pharmacological Optimization ofOrally Bioavailable 2-Pyridone-Containing Peptidomimetics." Journal of medicinal chemistry 46 21 (2003): 4572-85.
Schuller, Marion et al. "Fragment binding to the Nsp3 macrodomain of SARS-CoV-2 identified through crystallographic screening and computational docking." Science advances vol. 7,16 eabf8711. Apr. 14, 2021, doi:10.1126/sciadv.abf8711.
Dai, Rongchen et al. "Cathepsin K: The Action in and Beyond Bone." Frontiers in cell and developmental biology vol. 8 433. Jun. 4, 2020, doi:10.3389/fcell.2020.00433.
Jeong, Gi Uk et al. "Therapeutic Strategies Against COVID-19 and Structural Characterization of SARS-CoV-2: A Review." Frontiers in microbiology vol. 11 1723. Jul. 14, 2020, doi:10.3389/fmicb.2020.01723.
Verma, Sonia et al. "Cysteine Proteases: Modes of Activation and Future Prospects as Pharmacological Targets." Frontiers in pharmacology vol. 7 107. Apr. 25, 2016, doi:10.3389/fphar.2016.00107.
Ghosh, Arun K., and Sandra Gemma. "Design of Cysteine Protease Inhibitors." Structure-Based Design of Drugs and Other Bioactive Molecules, May 29, 2015, pp. 131-142, 10.1002/9783527665211.ch5. Accessed Feb. 14, 2022.
Yang, Syaulan et al. "Synthesis, crystal structure, structure-activity relationships, and antiviral activity of a potent SARS coronavirus 3CL protease inhibitor." Journal of medicinal chemistry vol. 49,16 (2006): 4971-80. doi:10.1021/jm0603926.
Hoffman, Robert L et al. "Discovery of Ketone-Based Covalent Inhibitors of Coronavirus 3CL Proteases for the Potential Therapeutic Treatment of COVID-19." Journal of medicinal chemistry vol. 63,21 (2020): 12725-12747. doi:10.1021/acs.jmedchem.0c01063.

(56) References Cited

OTHER PUBLICATIONS

Zhang, Linlin et al. "Crystal structure of SARS-CoV-2 main protease provides a basis for design of improved ?-ketoamide inhibitors." Science (New York, N.Y.) vol. 368,6489 (2020): 409-412. doi:10.1126/science.abb3405.
Ono, Yasuko et al. "Calpain research for drug discovery: challenges and potential." Nature reviews. Drug discovery vol. 15,12 (2016): 854-876. doi:10.1038/nrd.2016.212.
Douangamath, Alice et al. "Crystallographic and electrophilic fragment screening of the SARS-CoV-2 main protease." Nature communications vol. 11,1 5047. Oct. 7, 2020, doi:10.1038/s41467-020-18709-w.
Gurard-Levin, Zachary A et al. "Evaluation of SARS-CoV-2 3C-like protease inhibitors using self-assembled monolayer desorption ionization mass spectrometry." Antiviral research vol. 182 (2020): 104924. doi:10.1016/j.antiviral.2020.104924.
Sacco, Michael Dominic et al. "Structure and inhibition of the SARS-CoV-2 main protease reveals strategy for developing dual inhibitors against Mpro and cathepsin L." bioRxiv : the preprint server for biology 2020.07.27.223727. Jul. 27, 2020, doi:10.1101/2020.07.27.223727.
Günther, Sebastian et al. "X-ray screening identifies active site and allosteric inhibitors of SARS-CoV-2 main protease." Science (New York, N.Y.) vol. 372,6542 (2021): 642-646. doi:10.1126/science.abf7945.
Dai, Wenhao et al. "Supplementary Materials for: Structure-based design of antiviral drug candidates targeting the SARS-CoV-2 main protease." Science (New York, N.Y.) vol. 368,6497 (2020): 1331-1335. doi:10.1126/science.abb4489.
Chang, Kyeong-Ok et al. "Antiviral Drug Discovery: Norovirus Proteases and Development of Inhibitors." Viruses vol. 11,2 197. Feb. 25, 2019, doi:10.3390/v11020197.
Zhang, Chun-Hui et al. "Potent Noncovalent Inhibitors of the Main Protease of SARS-CoV-2 from Molecular Sculpting of the Drug Perampanel Guided by Free Energy Perturbation Calculations." ACS central science vol. 7,3 (2021): 467-475. doi:10.1021/acscentsci.1c00039.
Amin, Sk Abdul et al. "Protease targeted COVID-19 drug discovery and its challenges: Insight into viral main protease (Mpro) and papain-like protease (PLpro) inhibitors." Bioorganic & medicinal chemistry vol. 29 (2021): 115860. doi:10.1016/j.bmc.2020.115860.
He, Jun et al. "Potential of coronavirus 3C-like protease inhibitors for the development of new anti-SARS-CoV-2 drugs: Insights from structures of protease and inhibitors." International journal of antimicrobial agents vol. 56,2 (2020): 106055. doi:10.1016/j.ijantimicag.2020.106055.
Rut Wioletta et al "Substrate specificity profiling of SARS-CoV-2 Mpro protease provides basis for anti-COVID-19 drug design" Marcin Drag bioRxiv 2020.03.07.981928; doi: https://doi.org/10.1101/2020.03.07.981928.
Yuto Unoh et al "Discovery of S-217622, a Non-Covalent Oral SARS-CoV-2 3CL Protease Inhibitor Clinical Candidate for Treating COVID-19", bioRxiv 2022.01.26.477782; doi: https://doi.org/10.1101/2022.01.26.477782.
Cianni, et al. "Optimization strategy of single-digit nanomolar cross-class inhibitors of mammalian and protozoa cysteine proteases," Bioorganic Chemistry 101. Jun. 2020; 1-20.
Macchiagodena et al. "inhibition of main protease 3CLPro of the coronavirus disease 19 via structure-based ligand design and molecular modeling," Mar. 2, 2020, https://arxiv.org/pdf/2002.09937, pp. 1-28.
Cianni, et al. "Optimization strategy of single-digit nanomolar cross-class inhibitors of mammalian and protozoa cysteine proteases," Bioorganic Chemistry 101 Jun. 2020; pp. 1-20.
IPRP for International Application No. PCT/US2021/036638, date of issuance Dec. 22, 2022.
Halford Bethany: "Pfizer unveils its oral SARS-CoV-2 inhibitor," ACS meeting news, vol. 99, No. 13, Apr. 7, 2021, pp. 1-2.
Ramos-Guzman Carlos A. et al: "Computational simulations on the binding and reactivity of a nitrile inhibitor of the SARS-CoV-2 main protease", Chemical Communications, vol. 57, No. 72, Aug. 10, 2021, pp. 9096-9099, UK.
Wang Yaxin et al: "Inhibition of enterovirus 71 replication by an [alpha]-hydroxy-nitrile derivative NK-1.9k" Antiviral Research, Elsevier BV, NL, vol. 141, Jan. 5, 2017, pp. 91-100.
Bai Bing et al: "Peptidomimetic nitrile warheads as SARS-CoV-2 3CL protease inhibitors," RSC Medicinal Chemistry, vol. 12, No. 10, Aug. 20, 2021, pp. 1722-1730.
Banerjee Abhisek et al: "Development of potent and selective Cathepsin C inhibitors free of aortic binding liability by application of a conformational restriction strategy," Bioorganic & Medicinal Chemistry Letters, vol. 47, Jun. 15, 2021, pp. 128202, Amsterdam NL.
Dai, Wenhao et al. "Structure-based design of antiviral drug candidates targeting the SARS-CoV-2 main protease." (American Association for the Advancement of Science), Apr. 22, 2020, p. eabb4489, United States.
Liu Cheng et al: "Dual inhibition of SARS-CoV-2 and human rhinovirus with protease inhibitors in clinical development," Antiviral Research, vol. 187, Jan. 27, 2021, p. 105020, NL.
IPRP for International Application No. PCT /US2021 /027780, date of issuance Oct. 27, 2022.
International Preliminary Report on Patentability mailed Oct. 27, 2022, for International Application No. PCT/US2021/027780 filed Apr. 16, 2021. (8 pages).

* cited by examiner

INHIBITORS OF CYSTEINE PROTEASES AND METHODS OF USE THEREOF

CROSS REFERENCE TO RELATED APPLICATIONS

This application is a continuation of PCT/US2021/027780, filed Apr. 16, 2021, which claims the benefit of, and priority to, U.S. Ser. No. 63/012,039 filed Apr. 17, 2020; U.S. Ser. No. 63/031,357 filed May 28, 2020; U.S. Ser. No. 63/039,290 filed Jun. 15, 2020; U.S. Ser. No. 63/067,666 filed Aug. 19, 2020; and U.S. Ser. No. 63/111,248 filed Nov. 9, 2020, the contents of each of which are hereby incorporated by reference in their entirety.

BACKGROUND

The Coronaviridae family of viruses are enveloped, single-stranded, positive-sense RNA viruses and include 141 species that are classified into four genera according to their phylogenetic relationships: α-, β-, γ-, and δ-coronavirus. Coronaviruses (CoVs) are zoonotic viruses that infect a variety of animals from whales to birds, bats, cats, and humans. Typically, CoV infection results in mild to moderate respiratory tract infections; however, some CoV species are extremely virulent and can result in widespread fatality. Severe acute respiratory syndrome coronavirus (SARS-CoV) is a human CoV that was responsible for the first pandemic of the $21^{st}$ century, infecting over 8,000 people with a 10% mortality rate. Middle East respiratory syndrome coronavirus (MERS-CoV) was identified in November 2012 and had since infected over 1,600 people in 26 countries with 36% mortality rate. More recently, COVID-19 (SARS CoV2) coronaviruses have raised a global pandemic since they had been first identified in China in late 2019: Therefore, it is important to identify coronavirus drug targets that can be utilized for the development of broad-spectrum anti-coronaviral therapeutics to combat infections of existing and emerging coronaviruses.

All CoVs express a >800 kDa replicase polyprotein that contains either two or three cysteine proteases, the papain-like protease(s) (PLPpro, nsp3, or PLP1 and PLP2) and the 3C-like protease (3CLpro, nsp5, or Mpro). These proteases process the CoV replicase polyprotein by cleaving it into 16 non-structural proteins, which are responsible for a variety of aspects of CoV replication. The CoV 3CLpro is responsible for processing 11 cleavage sites of within the replicase polyprotein and is essential for CoV replication, making it a highly valuable target for therapeutic development. The overall active site architecture and substrate recognition pockets are structurally conserved across CoV 3CLpros, increasing its attractiveness as a target for the development of broad-spectrum anti-CoV therapeutics. Moreover, high sequence conservation in the vicinity of active site among CoV 3CLpros from different coronavirus subclasses make them an excellent target for the development of broad-spectrum therapeutics for coronavirus infections. Accordingly, the development of CoV 3CLpro inhibitors is a promising path for the treatment of respiratory tract infections and related diseases.

Numerous studies on targeting the immediate zoonotic reservoirs of coronaviruses with small molecule inhibitors have helped inform structure-based design strategies aimed at creating molecular scaffolds that may aid in the development of therapeutic against coronaviral infection; however, small molecule antiviral agents nor effective commercially available broad-spectrum therapeutics have not yet been identified. There is a critical need for the development of broad-spectrum CoV therapeutics to overcome the challenges of traditional anti-CoV therapeutic development, as broad-spectrum therapeutics can be rapidly implemented upon zoonotic disease outbreak.

SUMMARY

The disclosure is directed to, in part, viral protease inhibitor compounds. The disclosure is also directed to, in part, broad spectrum inhibitors of coronaviral 3CL proteases. Also provided are pharmaceutical compositions comprising at least one disclosed compound and a pharmaceutically acceptable carrier.

In an embodiment, provided herein is a broad spectrum, 3CL or 3C protease antiviral compound, comprising a warhead covalently bound to a 3CL protease inhibitor, wherein the antiviral compound covalently binds to Cys on the protease, and wherein the antiviral compound is active against one or more viruses.

In an embodiment, provided herein are compounds represented by Formula I:

Formula I

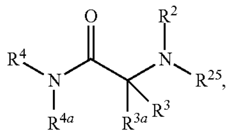

wherein: $R^{25}$ is selected from the group consisting of —C(O)$R^1$, phenyl, 3-10 membered heterocyclyl, and 5-10 membered heteroaryl, wherein the phenyl, 3-10 membered heterocyclyl, or 5-10 membered heteroaryl is optionally substituted by one, two or three substituents each selected from $R^a$, or $R^{25}$ is a warhead; $R^1$ is selected from the group consisting of $C_1$-$C_6$alkyl-N($R^bR^c$), $C_3$-$C_{10}$cycloalkyl, $C_6$-$C_{14}$aryl, 3-10 membered heterocyclyl, and 5-10 membered heteroaryl, wherein $R^1$ is optionally substituted by one, two or three substituents each selected from $R^a$, or $R^1$ is a warhead; $R^2$ is selected from the group consisting of $C_6$-$C_{14}$aryl, 3-10 membered heterocyclyl, 5-10 membered heteroaryl and $C_3$-$C_{10}$cycloalkyl, wherein $R^2$ is optionally substituted by one, two or three substituents each selected from the group consisting of halogen, —C(O)—N($R^bR^c$) and $R^5$, or $R^2$ is a warhead; $R^5$ is independently selected, for each occurrence, from the group consisting of $C_1$-$C_6$haloalkyl, hydroxyl, oxo, $SF_5$, cyano, halogen, $C_1$-$C_6$alkyl, $C_1$-$C_6$alkoxy, $C_6$-$C_{14}$aryl, $C_1$-$C_6$alkyl-phenyl, $C_1$-$C_6$alkenyl-phenyl, $C_1$-$C_6$alkoxy-phenyl, $C_3$-$C_{10}$cycloalkyl, and 5-9 membered heteroaryl; wherein $R^5$ is optionally substituted by one, two or three substituents each selected from $R^a$; $R^3$ is selected from the group consisting of $C_6$-$C_{14}$aryl, 3-10 membered heterocyclyl, 5-6 membered monocyclic heteroaryl and 8-10 membered bicyclic heteroaryl, wherein the heteroaryl contains at least one ring nitrogen and may have one, two or three optional substituents each selected from $R^a$, or $R^3$ is a warhead; $R^{3a}$ is selected from the group consisting of hydrogen, $C_1$-$C_6$alkyl, $C_1$-$C_6$haloalkyl, halogen and deuterium; or $R^3$ and $R^{3a}$ may be joined together to form, together with the carbon to which they are attached, a 3-10 membered heterocyclyl, or $R^{3a}$ is a warhead; or $R^{3a}$ and $R^{4a}$ may be form, together with the carbon and nitrogen to which they are attached, respectively, a 5-10 membered heterocycle, wherein the heterocycle is optionally substituted by one, two or three substituents each selected from $R^a$; $R^4$ is selected from the group consisting of hydrogen, $C_1$-$C_6$alkyl, $C_1$-$C_6$alkoxy, $C_1$-$C_6$alkyl-N($R^bR^c$), $C_1$-$C_6$alkyl-($C_6$-$C_{14}$aryl), $C_1$-$C_6$alkyl-(3-10 membered heterocyclyl), $C_1$-$C_6$alkyl-(5-9 membered heteroaryl), $C_3$-$C_{10}$cycloalkyl, $C_6$-$C_{14}$aryl, 3-10 membered heterocyclyl and 5-10 membered heteroaryl, wherein the aryl, heteroaryl, alkyl, $C_1$-$C_6$alkoxy, or $C_3$-$C_{10}$cycloalkyl is optionally substituted by one, two or three substituents each selected from $R^a$; $R^{4a}$ is selected from the group consisting of hydrogen, $C_1$-$C_6$alkyl, $C_1$-$C_6$alkoxy, $C_3$-$C_{10}$cycloalkyl, 3-10 membered heterocyclyl, $C_6$-$C_{14}$aryl, and 5-10 membered heteroaryl, wherein the aryl, heteroaryl, $C_1$-$C_6$alkyl, $C_1$-$C_6$alkoxy, or $C_3$-$C_{10}$cycloalkyl is optionally substituted by one, two or three substituents each selected from $R^a$; or $R^4$ and $R^{4a}$ may form, together with the nitrogen to which they are attached, a 4-10 membered heterocycle, wherein the heterocycle is optionally substituted by one, two or three substituents each selected from $R^a$; $R^a$ is independently selected, for each occurrence, from the group consisting of halogen, hydroxyl, oxo, cyano, $SF_5$, —$OR^{aa}$, $S(O)_2$—($C_1$-$C_6$alkyl), $C_1$-$C_6$alkyl, $C_1$-$C_6$alkyl-OH, $C_1$-$C_6$haloalkyl, $C_1$-$C_6$alkoxy, $C_3$-$C_{10}$cycloalkyl, $C_6$-$C_{14}$aryl, 3-10 membered heterocyclyl, 5-10 membered heteroaryl, —C(O)—O—$C(CH_3)_3$, —C(O)—O—($CH_2$)—($C_{13}H_9$), —NH—C(O)—O—$C(CH_3)_3$, —C(O)—O—($CH_2$)-(phenyl), —C(O)—N($R^bR^c$), and —N($R^bR^c$), wherein the aryl, heteroaryl, or heterocyclyl is optionally substituted by one, two, or three substituents of halogen; and $R^{aa}$ is selected from the group consisting of $C_1$-$C_6$haloalkyl, $C_1$-$C_6$alkyl-phenyl and $C_6$-$C_{14}$aryl; $R^b$ and $R^c$ are each selected from the group consisting of hydrogen, $C_1$-$C_6$alkyl, and $C_3$-$C_{10}$cycloalkyl; wherein the $C_1$-$C_6$alkyl or $C_3$-$C_{10}$cycloalkyl may optionally be substituted by one or more substituents selected from the group consisting of halogen, cyano, oxo, and hydroxyl; or $R^b$ and $R^c$ may form, together with the nitrogen to which they are attached, a 4-6 membered heterocycle, wherein the heterocycle is optionally substituted by one, two or three substituents each selected from $R^a$; wherein one of $R^{25}$, $R^1$, $R^2$, and $R^3$ is a warhead; and pharmaceutically acceptable salts, stereoisomers, esters, and prodrugs thereof.

In some embodiments, the compound of Formula I is represented by

Formula I-A-I

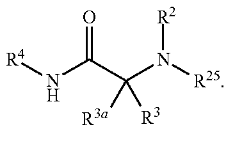

In some embodiments, the compound of Formula I is represented by

Formula I-A

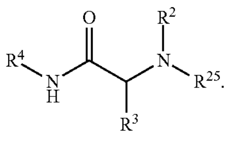

In some embodiments, the compound of Formula I is represented by

Formula I-B

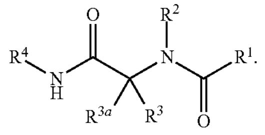

In some embodiments, the compound of Formula I is represented by

Formula I-C

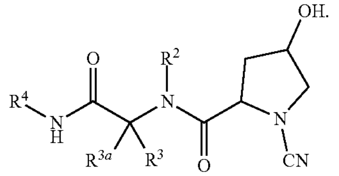

In an embodiment, provided herein are compounds represented by Formula II:

Formula II

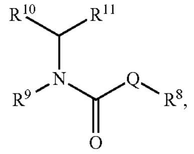

wherein: $R^8$ is selected from the group consisting of

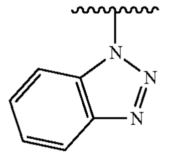

and

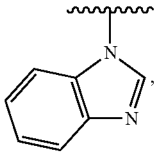

wherein $R^8$ may be optionally substituted on an available carbon by $R^d$, or $R^8$ is a warhead; Q is $CH_2$ or NH; $R^9$ is a phenyl, or monocyclic or 8-10 membered bicyclic heteroaryl optionally substituted by one, two or three substituents each selected from $R^{12}$, or $R^9$ is a warhead; $R^{12}$ is independently selected, for each occurrence, from the group consisting of $C_1$-$C_6$alkyl, $C_3$-$C_{10}$cycloalkyl, phenyl, 5-6 membered heteroaryl, —N($R^eR^f$), —N($R^e$)—C(O)—($R^f$), and —N($R^e$)—$S(O)_2$—($R^f$), wherein the 5-6 membered heteroaryl may have one, two or three optional substituents each selected from $R^h$; $R^{10}$ is a phenyl, 5-6 membered monocyclic heteroaryl, or 7-10 membered heteroaryl, wherein $R^{10}$ is optionally substituted by one, two or three substituents each selected from $R^g$; $R^g$, for each occurrence, is selected from the group consisting of halogen, —$NO_2$, $C_1$-$C_5$alkyl, $C_1$-$C_5$alkoxy, $C_1$-$C_5$alkoxy-N($R^eR^f$), —N($R^eR^f$), phenyl, and 5-6 membered heteroaryl, wherein the phenyl or heteroaryl may have one, two or three optional substituents each selected from $R^h$; $R^{11}$ is selected from the group consisting of hydrogen, $C_1$-$C_5$alkyl, $C_3$-$C_6$cycloalkyl, and —C(O)—N($R^eR^f$); $R^d$, for each occurrence, is selected from the group consisting of halogen, hydroxyl, $C_1$-$C_5$alkyl, $C_1$-$C_6$haloalkyl, $C_1$-$C_5$alkoxy, —C(O)—N(RRI), and —$N(R^eR^f)$; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, and hydroxyl; or $R^e$ and $R^f$ may form, together with the nitrogen to which they are attached, a 4-6 membered heterocycle; $R^h$, for each occurrence, is selected from the group consisting of halogen, $C_1$-$C_5$alkyl, $C_1$-$C_6$haloalkyl, and $C_1$-$C_5$alkoxy; wherein one of $R^8$ and $R^9$ is a warhead; and pharmaceutically acceptable salts, stereoisomers, esters, and prodrugs thereof.

In an embodiment, provided herein are compounds represented by Formula X:

Formula X

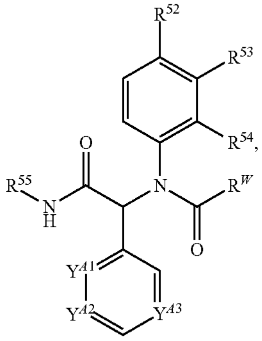

wherein: $Y^{A1}$ is N or $CR^{50}$, wherein $R^{50}$ is selected from the group consisting of H, $CF_3$, halogen, cyano, $C_1$-$C_3$alkoxy, and $C_1$-$C_3$alkyl; $Y^{A2}$ is N or $CR^{51}$, wherein $R^{51}$ is selected from the group consisting of H, halogen, and cyano; $Y^{A3}$ is N or CH; $R^{52}$ is selected from the group consisting of H, $SF_5$, $C_1$-$C_6$alkyl, $C_3$-$C_6$cycloalkyl (optionally substituted by one, two or three $CF_3$), and phenyl; $R^{53}$ is H or halogen; or $R^{52}$ and $R^{53}$ may be joined together to form, together with the carbons to which they are attached, a 5-10 membered heterocycle (optionally substituted by one, two or three $C_1$-$C_6$alkyl); $R^{54}$ is H or halogen; $R^{55}$ is selected from the group consisting of $C_1$-$C_6$alkyl (optionally substituted by one, two or three phenyl), $C_3$-$C_6$cycloalkyl (optionally substituted by one, two or three halogen), 5-6 membered monocyclic or 7-8 membered bicyclic heterocycle (optionally substituted by one, two or three methyl), and 5-6 membered heteroaryl (optionally substituted by one, two or three methoxy); $R^w$ is selected from the group consisting of

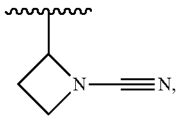,
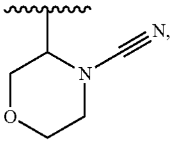,
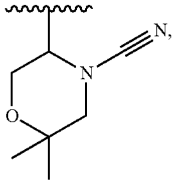,
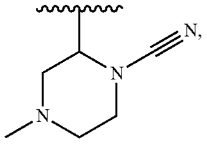,

-continued

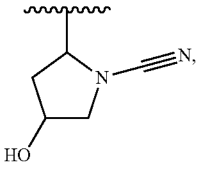,
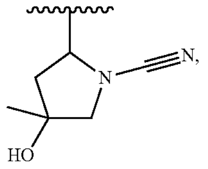,
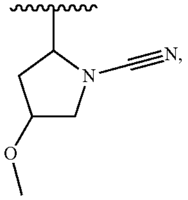,
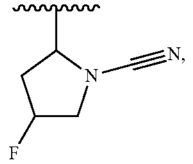,
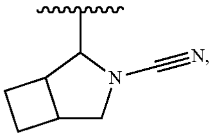,
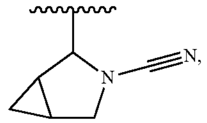,
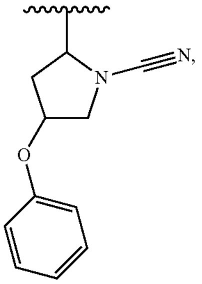,
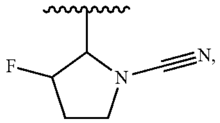,
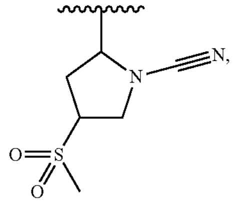,
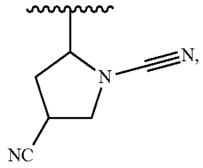,
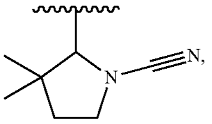, and
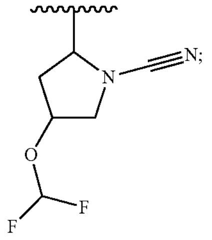;

and pharmaceutically acceptable salts, stereoisomers, esters, and prodrugs thereof.

In some embodiments, provide herein are conjugates represented by:

Formula VI

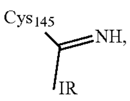, wherein $Cys_{145}$ is cysteine at position 145 or equivalent active site cysteine on a CL protease; and IR is a viral protease inhibitor.

In some embodiments, provide herein are conjugates represented by:

Formula VII

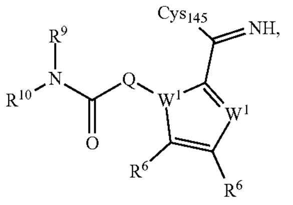

wherein: $Cys_{145}$ is cysteine at position 145 or equivalent active site cysteine on the 3CL protease; $W^1$ is independently selected, for each occurrence, from the group consisting of C, CH, S, and N; Q is $CH_2$ or NH; $R^6$ is independently selected, for each occurrence, from the group consisting of: hydrogen, halogen, $C_1$-$C_5$alkyl, $C_1$-$C_6$haloalkyl, and $C_1$-$C_5$alkoxy; or $R^6$ can be taken together with the two carbons where $R^6$ are attached to form a phenyl or 5-7 membered heteroaryl ring; $R^9$ is a phenyl, or monocyclic or 8-10 membered bicyclic heteroaryl optionally substituted by one, two or three substituents each selected from $R^{12}$; $R^{12}$ is independently selected, for each occurrence, from the group consisting of phenyl, 5-6 membered heteroaryl, —$N(R^eR^f)$, —$N(R^e)$—C(O)—$(R^f)$, and —$N(R^e)$—$S(O)_2$—$(R^f)$, wherein the 5-6 membered heteroaryl may have one, two or three optional substituents each selected from $R^h$; $R^{10}$ is a phenyl, 5-6 membered monocyclic heteroaryl, or 7-10 membered heteroaryl, wherein $R^{10}$ is optionally substituted by one, two or three substituents each selected from $R^g$; $R^g$, for each occurrence, is selected from the group consisting of halogen, —$NO_2$, $C_1$-$C_5$alkyl, $C_1$-$C_5$alkoxy, $C_1$-$C_5$alkoxy-$N(R^eR^f)$, —$N(R^eR^f)$, phenyl, and 5-6 membered heteroaryl, wherein the phenyl or heteroaryl may have one, two or three optional substituents each selected from $R^h$; $R^d$, for each occurrence, is selected from the group consisting of halogen, hydroxyl, $C_1$-$C_5$alkyl, $C_1$-$C_6$haloalkyl, $C_1$-$C_5$alkoxy, —C(O)—N$(R^eR^f)$, and —$N(R^eR^f)$; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, and hydroxyl; or $R^e$ and $R^f$ may form, together with the nitrogen to which they are attached, a 4-6 membered heterocycle; $R^h$, for each occurrence, is selected from the group consisting of halogen, $C_1$-$C_5$alkyl, $C_1$-$C_6$haloalkyl, and $C_1$-$C_5$alkoxy; and pharmaceutically acceptable salts, stereoisomers, esters, and prodrugs thereof.

Also provided herein are methods of ameliorating or treating a viral infection in a patient in need thereof, comprising administering to the patient a therapeutically effective amount of any of the compounds described herein.

In some embodiments, provided herein are methods of inhibiting transmission of a virus, a method of inhibiting viral replication, a method of minimizing expression of viral proteins, or a method of inhibiting virus release, comprising administering a therapeutically effective amount of a compound described herein to a patient suffering from the virus, and/or contacting an effective amount of a compound described herein with a virally infected cell.

DETAILED DESCRIPTION

Figure 1:
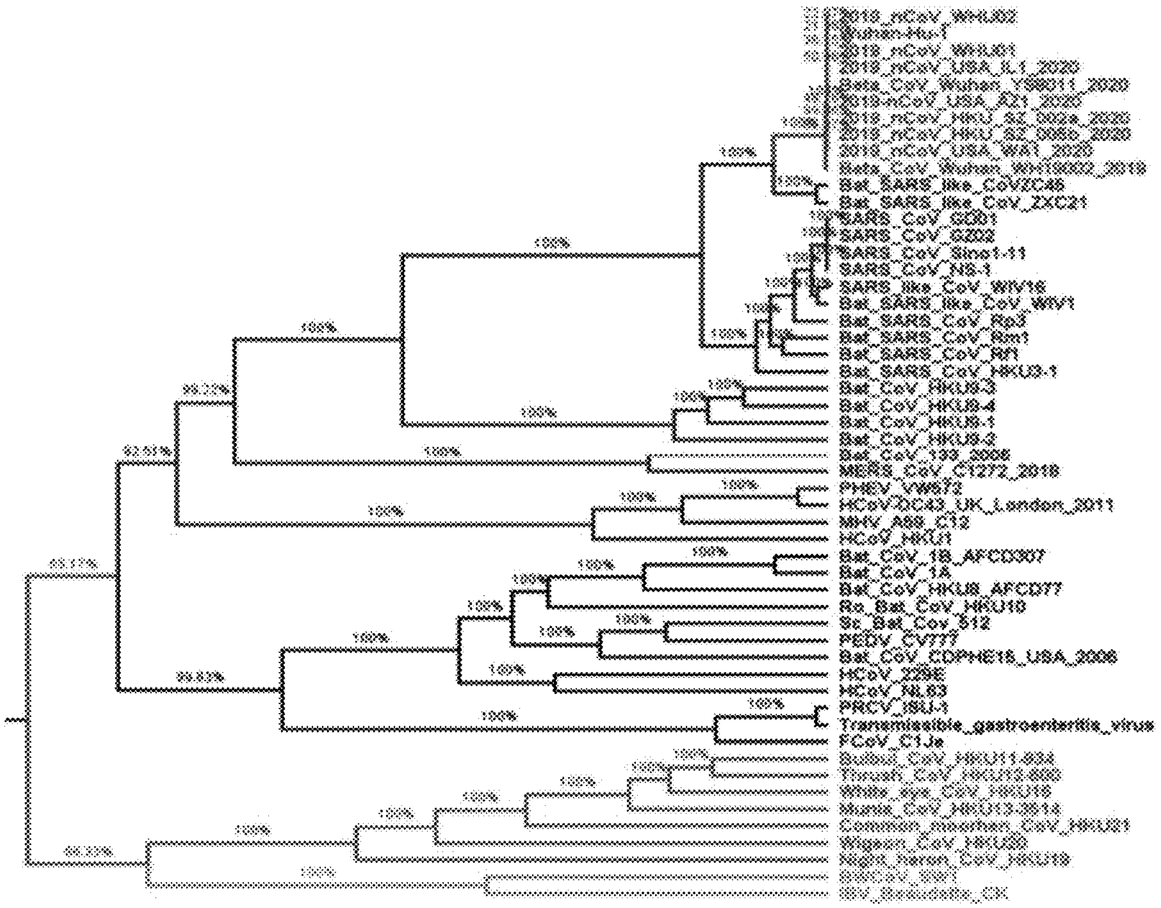
FIG. 1 depicts an evolutionary phylogenetic tree analysis of Coronaviruses: shows a schematic phylogenetic tree (phylogram) of full 3CLpro sequences of a number of coronaviruses obtained from National Center for Biotechnology Information (NCBI), which were aligned and phylogenetically compared. Branches with different colors represent different genera of Coronaviruses: black, alpha coronavirus, blue, beta coronavirus; red, SARS-CoV-2; green, delta coronavirus; and purple, gamma coronavirus.

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

The term "treating" includes any effect, e.g., lessening, reducing, modulating, or eliminating, that results in the improvement of the condition, disease, disorder and the like, including a reduction of viral shedding in asymptomatic individuals and prophylaxis of exposed individuals, independent of symptoms.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_1$-$C_5$alkenyl, $C_2$-$C_6$alkenyl, and $C_3$-$C_4$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_1$-$C_5$alkoxy, $C_1$-$C_6$alkoxy, and $C_2$-$C_6$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$ alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylene bridge" refers to a straight or branched divalent hydrocarbon bridge, linking two different carbons of the same ring structure. The alkylene bridge may link any two carbons within the ring structure. In some embodiments, alkylene bridges can be an indicated number of carbon atoms, for example, $C_1$-$C_6$ alkylene bridge, $C_1$-$C_5$ alkylene bridge, $C_1$-$C_4$ alkylene bridge, $C_1$-$C_3$ alkylene bridge, or $C_1$-$C_2$ alkylene bridge. Unless otherwise specified, each instance of an alkylene bridge is independently optionally substituted, i.e., unsubstituted (an "unsubstituted alkylene bridge") or substituted (a "substituted alkylene bridge") with one or more substituents (for instance from 1 to 4 substituents, 1 to 3 substituents, or 1 substituent) which may be halo, —$NO_2$, —OH, $C_1$-$C_6$ alkoxy, $C_1$-$C_6$ alkyl, or $C_1$-$C_6$ cycloalkyl. Examples of alkylene bridge include, but are not limited to, methylene, ethylene, propylene, tetramethylene, and n-butylene.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

Examples of representative substituted aryls include the following

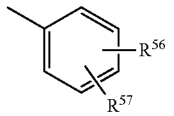
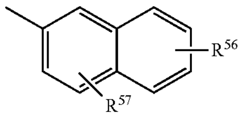
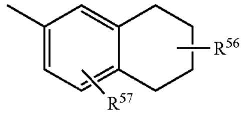
and
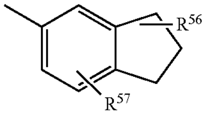

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_5$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{18}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{16}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are each independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_3$-$C_{10}$cycloalkyl, $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "haloalkyl" as used herein refers to an alkyl radical in which the alkyl group is substituted with one or more halogens. Typical haloalkyl groups include, but are not limited to, trifluoromethyl (i.e. $CF_3$), difluoromethyl, fluoromethyl, chloromethyl, dichloromethyl, dibromoethyl, tribromomethyl, tetrafluoroethyl, and the like. Exemplary haloalkyl groups include, but are not limited to, straight or branched hydrocarbons of 1-6, 1-4, or 1-3 carbon atoms substituted with a halogen (i.e. Cl, F, Br and I), referred to herein as $C_{1-6}$ haloalkyl, $C_{1-4}$ haloalkyl, and $C_{1-3}$haloalkyl, respectively.

The term "hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

The terms "heteroaryl" or "heteroaromatic group" as used herein refers to an aromatic 5-10 membered ring system containing one or more heteroatoms, for example one to three heteroatoms, such as nitrogen, oxygen, and sulfur. The term may also be used to refer to a 5-7 membered monocyclic heteroaryl or an 8-10 membered bicyclic heteroaryl. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

Examples of representative heteroaryls include the following:

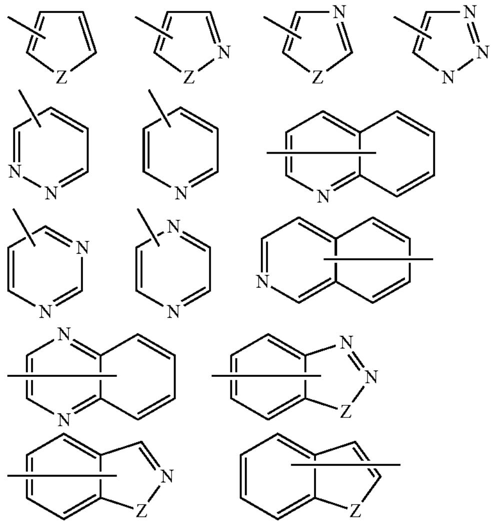

wherein each Z is selected from carbonyl, N, $NR^{65}$, O, and S; and $R^{65}$ is each independently hydrogen, $C_1$-$C_8$ alkyl, $C_3$-$C_{10}$ cycloalkyl, 4-10 membered heterocyclyl, $C_6$-$C_{10}$ aryl, or 5-10 membered heteroaryl.

The terms "heterocyclyl," "heterocycle," or "heterocyclic group" are art-recognized and refer to saturated or partially unsaturated 4-10 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran, dihydrofuran etc. In some embodiments, the heterocyclyl group is a bridged heterocyclyl, a monocyclic, a bicyclic heterocyclyl, or a spirocyclic heterocyclyl. In some embodiments, the heterocycle is a spiro heterocycle (e.g. 2,8-diazaspiro[4.5]decane). In some embodiments, the heterocycle is a bridged heterocycle (e.g. octahydro-1H-4,7-methanoisoindole). "Spiro heterocyclyl," or "spiro heterocycle" refers to a polycyclic heterocyclyl with rings connected through one common atom (called a spiro atom), wherein the rings have one or more heteroatoms selected from the group consisting of N, O, and $S(O)_m$ (wherein m is an integer of 0 to 2) as ring atoms. Representative examples of heterocyclyl include, for example:

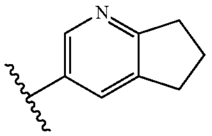, 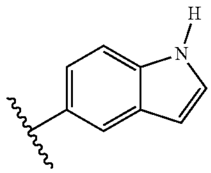,

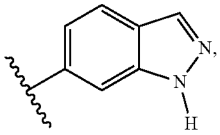 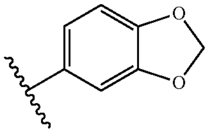,

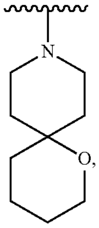 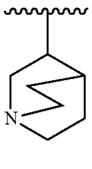, and 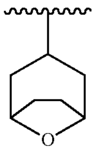.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the disclosure are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(f)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the disclosure can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the disclosure or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as 3-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the disclosure contains an alcohol functional group, a prodrug can be formed by the replacement of the hydrogen atom of the alcohol group with a group such as $(C_{1-6})$alkylcarbonyloxymethyl, 1-($(C_{1-6})$alkylcarbonyloxy)ethyl, 1-methyl-1-($(C_{1-6})$alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino(CIA)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

If a compound of the disclosure incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

The term "warhead" or "warhead group" as used herein refers to a functional group present on a compound wherein that functional group is capable of reversibly or irreversibly participating in a reaction with a protein, e.g., 3C or 3CL protease (e.g., with a cysteine on the protease such as Cys 145). Warheads may, for example, form covalent bonds with the protein, or may create stable transition states, or be a reversible or an irreversible alkylating agent. For example, the warhead moiety can be a functional group on an inhibitor that can participate in a bond-forming reaction, wherein a new covalent bond is formed between a portion of the warhead and a donor, for example an amino acid residue of a protein. In embodiments, the warhead is an electrophile and the "donor" is a nucleophile such as the side chain of a cysteine residue. As provided herein, a warhead may include a nitrile or halo group. As also provided herein, a warhead may include an aldehyde, ketoamides, hydroxybisulfite salts, heterocyclic moieties, aziridine, oxirane, epoxy ketones, halomethyl ketones, hydroxymethyl ketones, electrophilic ketones (e.g. trifluoromethyl ketones), acyloxymethyl ketones, benzothiazolyl ketones and a Michael acceptor. For example, nitriles may be reversible covalent warheads for cysteine protease inhibition. For example, where the mechanism of action may involve a formation of reversible covalent bond between the nitrile and the active cysteine to form a thioimidate adduct. Reaction of cysteine of glutathione or other proteins is generally reversible, while the reaction with cysteine or aminoethylthiols generally irreversibly forms a thiazolidine adduct. It can be appreciated that contemplated compounds herein may be a reversible or an irreversible inhibitor.

Examples of exemplary warheads include, but not limited to, a moiety with a cyano or halo moiety, e.g.:

—CN, 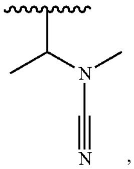 , 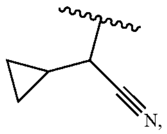 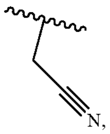

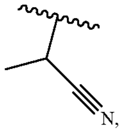 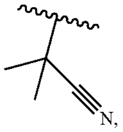 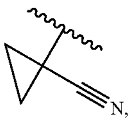

-continued
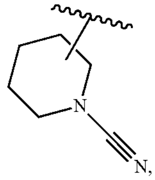 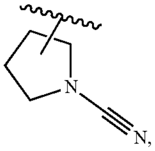 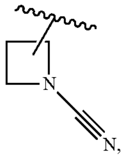
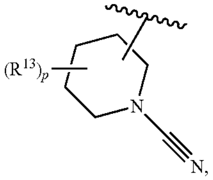 (e.g., 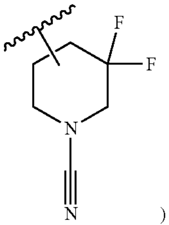 )
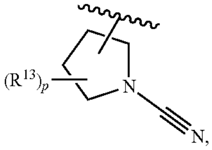 (e.g., 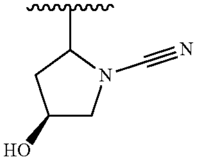 ,
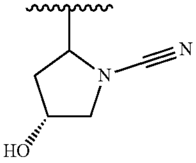 , 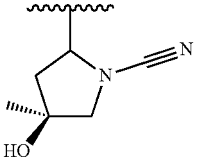 ,
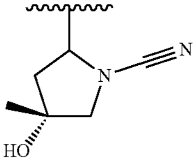 , 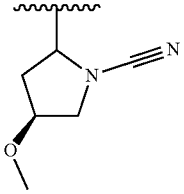 ,
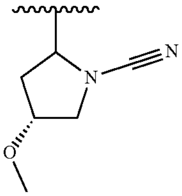 , 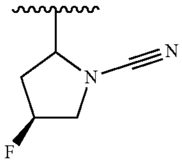 ,
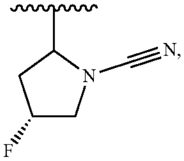 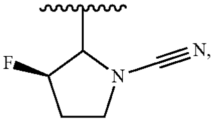
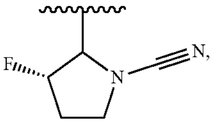 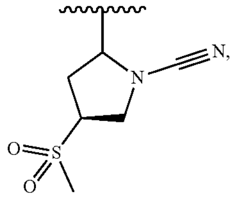
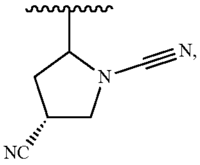 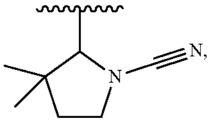
-continued
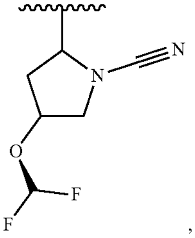 , and 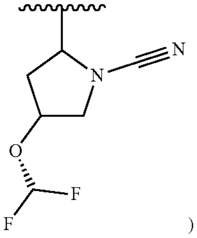 )
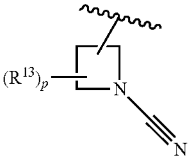 (e.g., 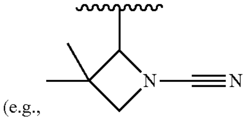 ,
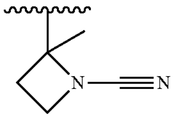 , and 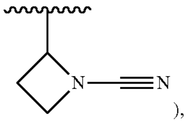 ),
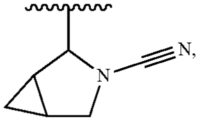 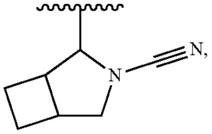
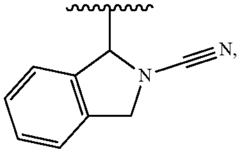 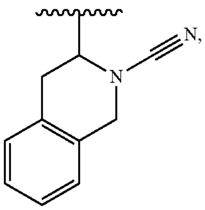
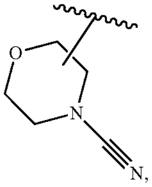 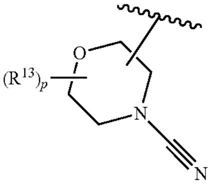
(e.g., 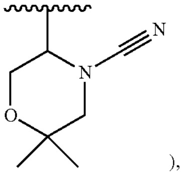 ), 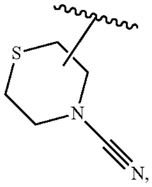
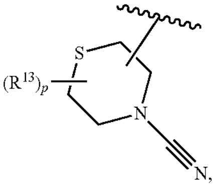 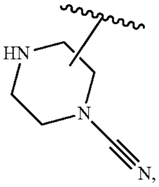
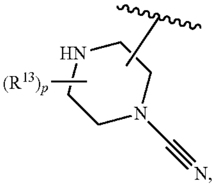 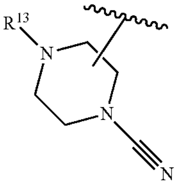

-continued
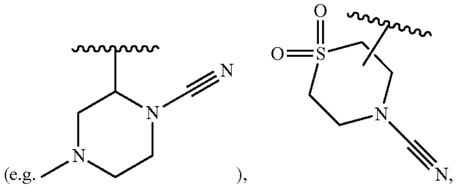
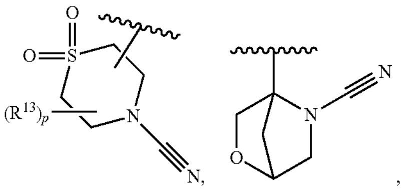
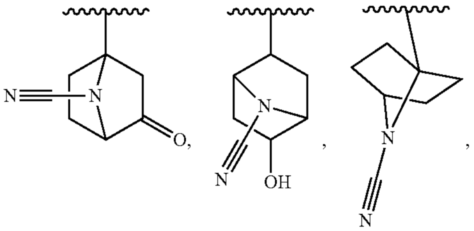
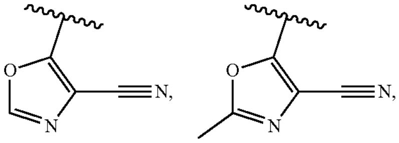
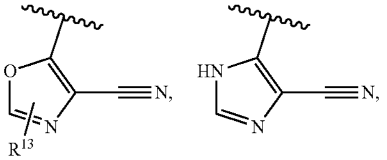
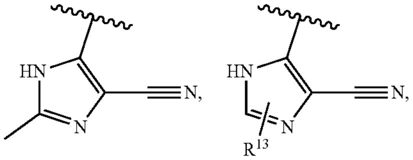
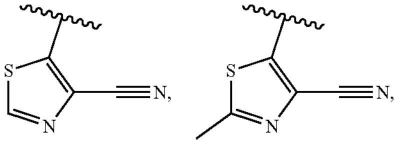
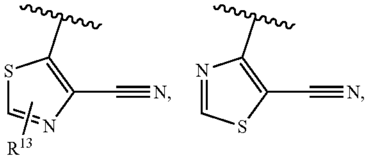
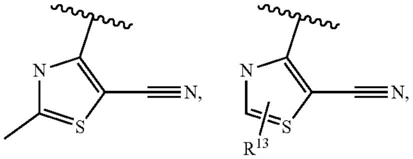
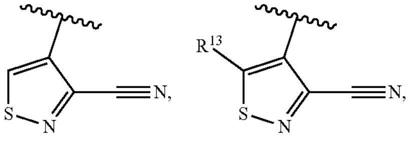
-continued
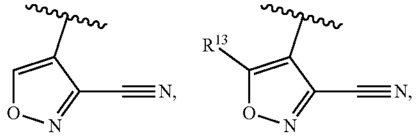
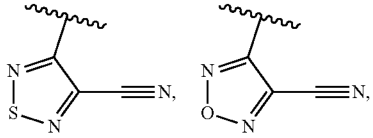
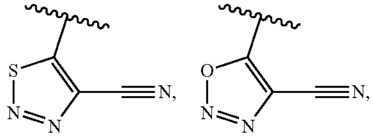
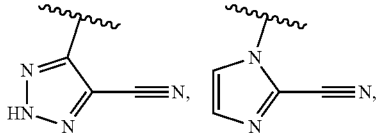
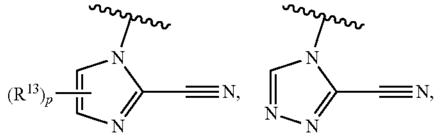
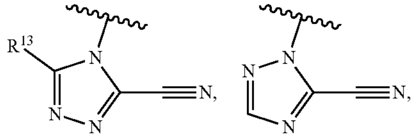
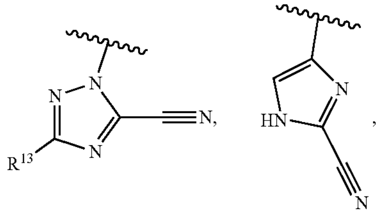
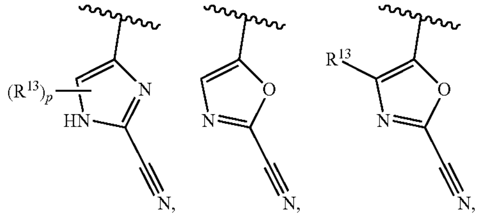
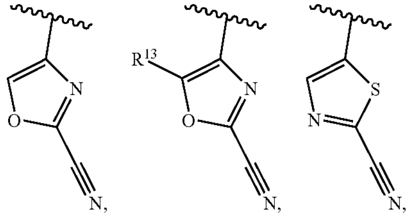
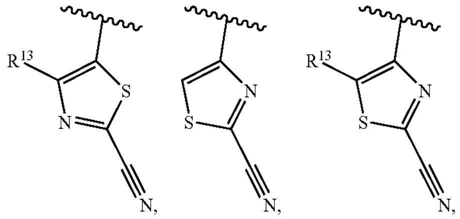

-continued
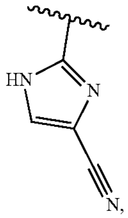
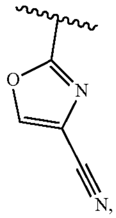
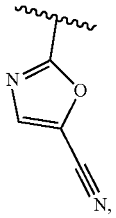
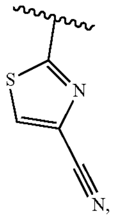
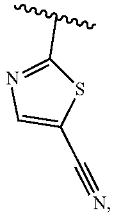
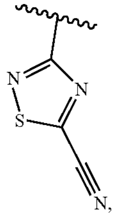
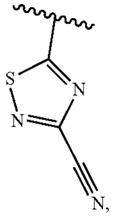
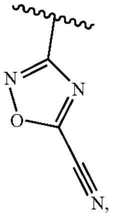
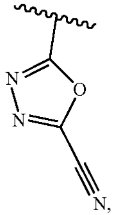
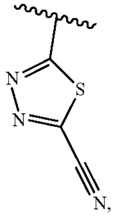
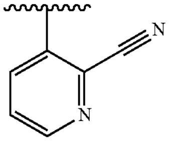
,
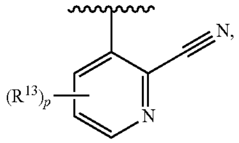
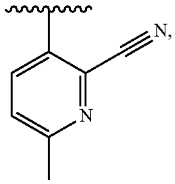
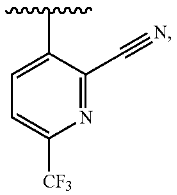
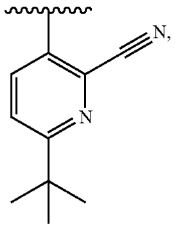
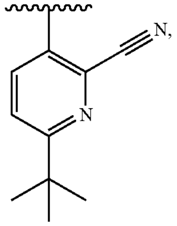
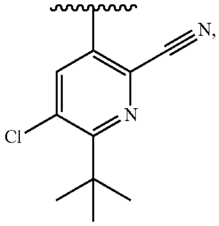
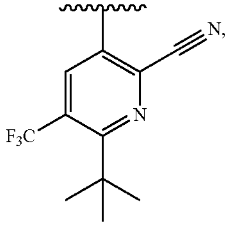
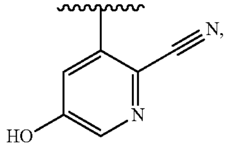
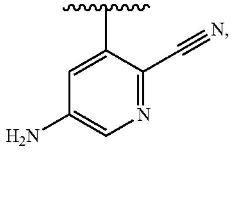
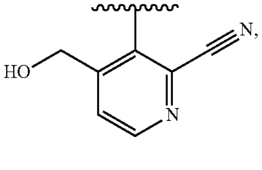
-continued
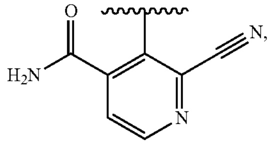
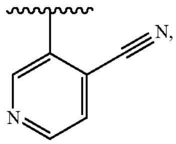
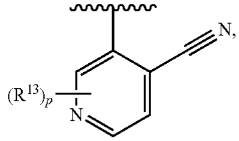
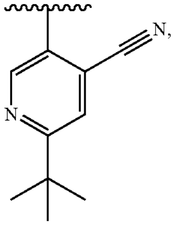
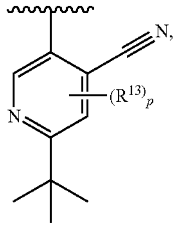
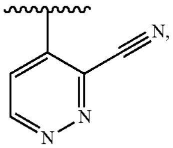
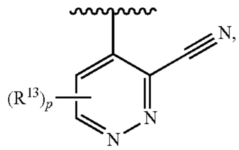
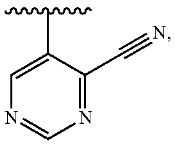
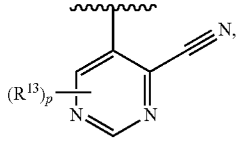
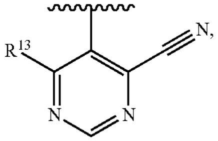
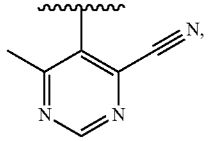
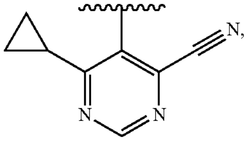
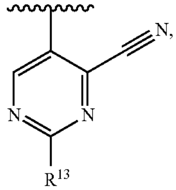
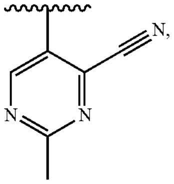
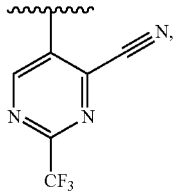
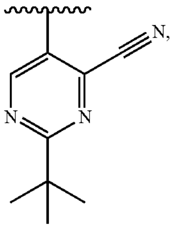
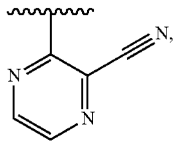
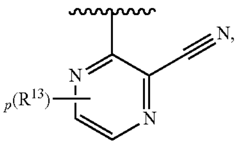

-continued
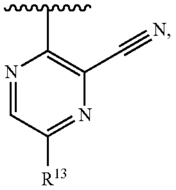
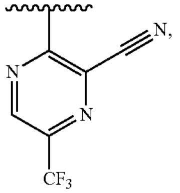
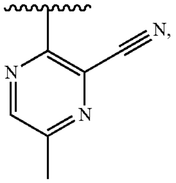
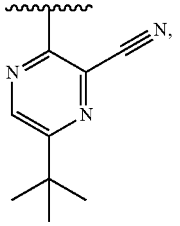
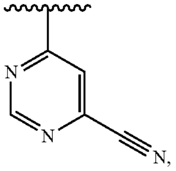
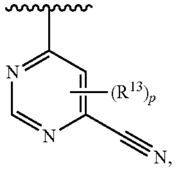
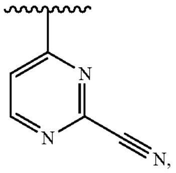
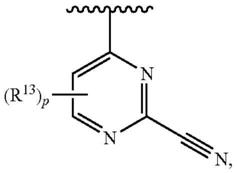
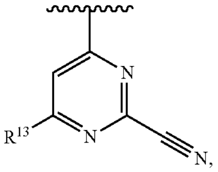
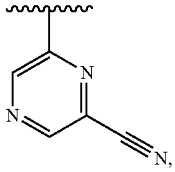
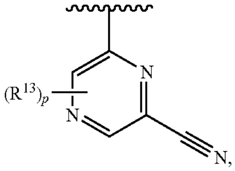
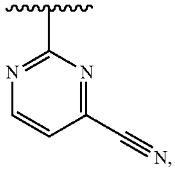
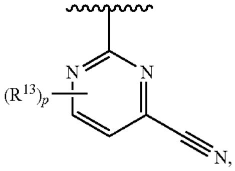
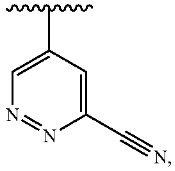
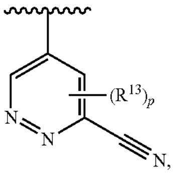
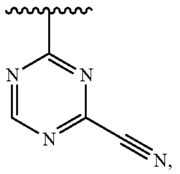
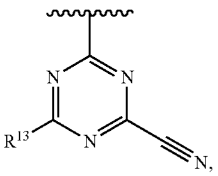
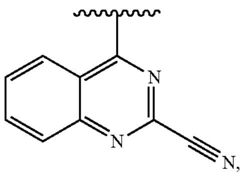
-continued
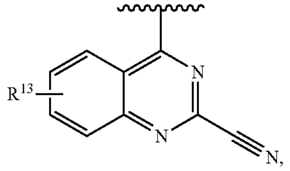
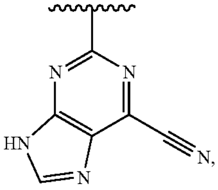
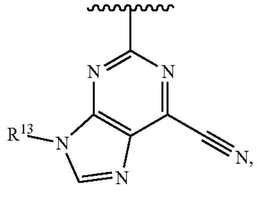
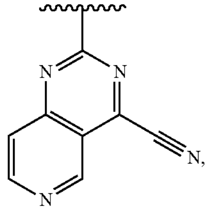
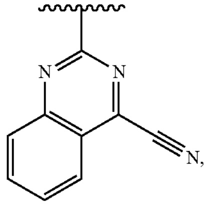
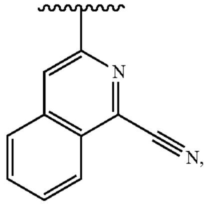
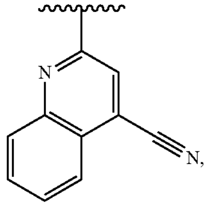
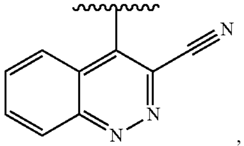
,
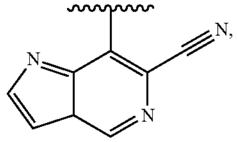
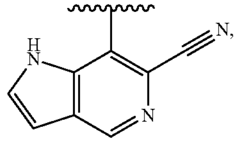
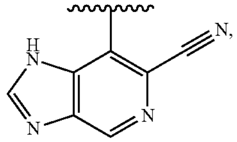
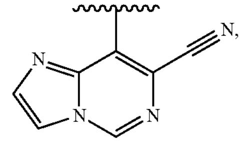
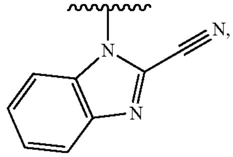
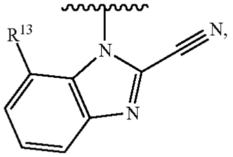
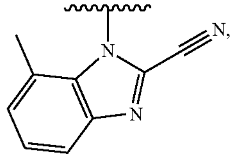
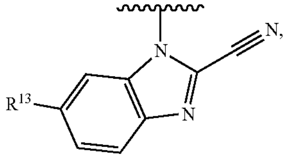
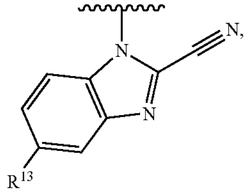
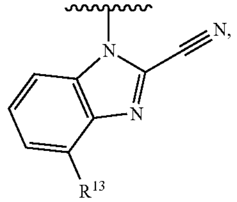

-continued

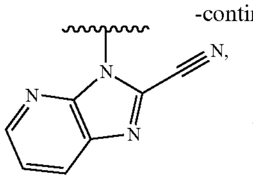
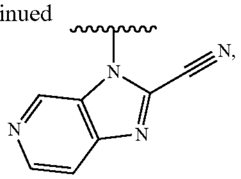
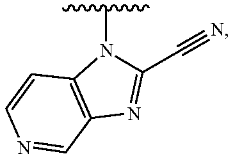
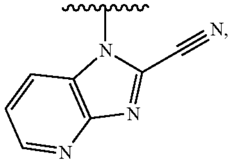
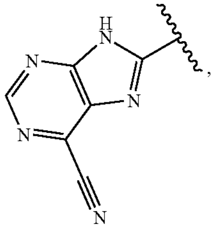
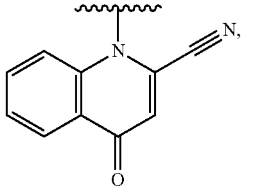
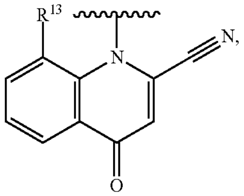
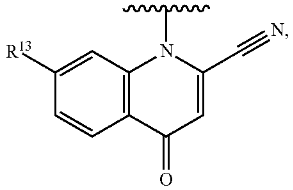
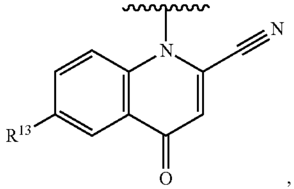

, and

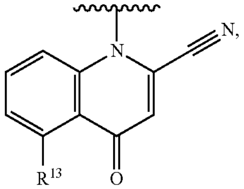

wherein $R^{13}$ is independently selected, for each occurrence, from the group consisting of halogen, hydroxyl, oxo, cyano, —$SO_2$, —$SF_5$, and $R^{13a}$; $R^{13a}$ is selected from the group consisting of —$OR^{13b}$, $C_1$-$C_6$alkyl, $C_1$-$C_6$haloalkyl, $C_1$-$C_6$alkoxy, $C_3$-$C_{10}$cycloalkyl, —$N(R^eR^f)$, —$N(R^e)$—C(O)—$(R^f)$, 3-10 membered heterocyclyl, $C_6$-$C_{14}$aryl and 5-10 membered heteroaryl; wherein $R^{13a}$ may be optionally substituted by one, two or three substituents each selected from $R^h$; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, hydroxyl, 3-10 membered heterocyclyl, $C_6$-$C_{14}$aryl, and 5-10 membered heteroaryl; or $R^e$ and $R^f$ may form, together with the nitrogen to which they are attached, a 4-6 membered heterocycle; $R^h$, for each occurrence, is selected from the group consisting of halogen, $C_1$-$C_6$alkyl, $C_1$-$C_6$haloalkyl, and $C_1$-$C_6$alkoxy; $R^{13b}$ is selected from the group consisting of $C_1$-$C_6$alkyl-(3-10 membered heterocyclyl), $C_1$-$C_6$alkyl-(5-10 membered heteroaryl), $C_1$-$C_6$alkyl-($C_6$-$C_{14}$aryl), $C_1$-$C_6$haloalkyl, $C_3$-$C_{10}$cycloalkyl, $C_6$-$C_{14}$aryl, 3-10 membered heterocyclyl and 5-10 membered heteroaryl; and p is 0, 1, 2, 3, or 4, as valency permits.

In some embodiments, the warhead is a moiety with a cyanohydrin or cyanoacrylate moiety. Examples of exemplary cyanohydrin and cyanoacrylate warheads include, but not limited to:

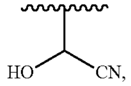
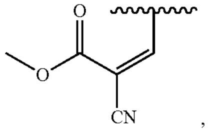

,

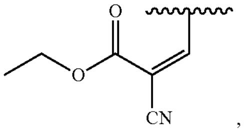

,

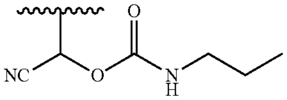

,

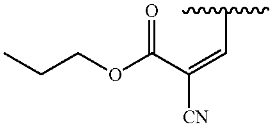

,

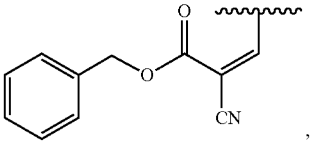

,

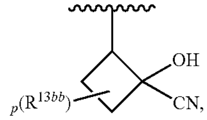
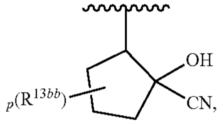
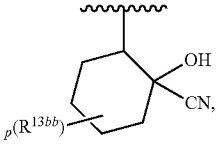
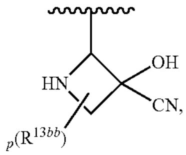
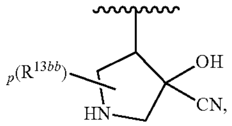
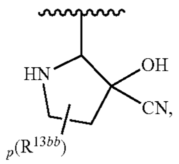
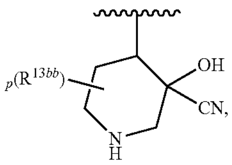
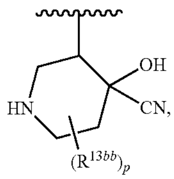
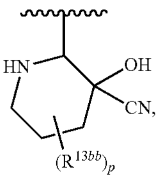

-continued

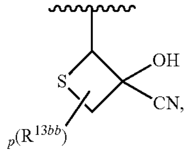
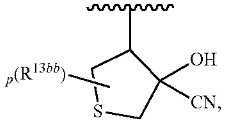
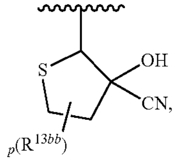
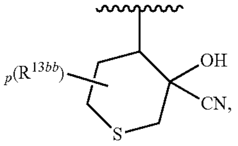
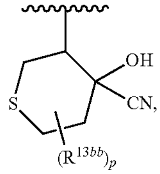
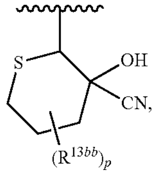
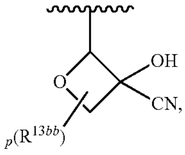
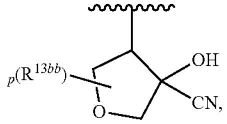
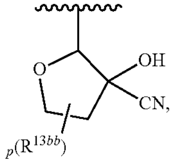
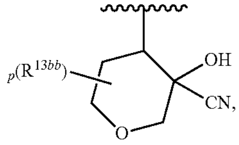
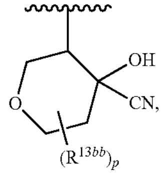
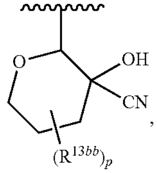
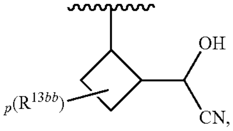
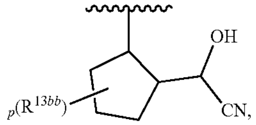

and

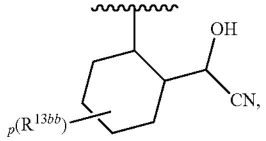

wherein $R^{13bb}$ is independently selected, for each occurrence, from the group consisting of halogen, $C_1$-$C_6$alkyl, $C_1$-$C_6$haloalkyl, $C_1$-$C_6$alkoxy, $C_3$-$C_{10}$cycloalkyl, —$N(R^eR^f)$, and —C(O)—$N(R^eR^f)$; $R^e$ and $R^f$ are each independently selected, for each occurrence, from the group consisting of hydrogen and $C_1$-$C_6$alkyl; or $R^e$ and $R^f$ may form, together with the nitrogen to which they are attached, a 4-6 membered heterocycle; and p is 0, 1, 2, 3, or 4, as valency permits.

In some embodiments, the warhead is a moiety with a cyano amine or cyano amide moiety. Examples of exemplary cyano amine warheads include, but not limited to:

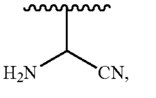
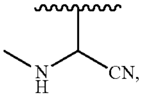
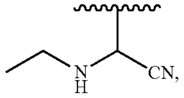
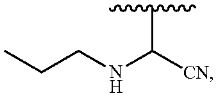
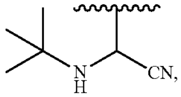
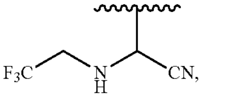
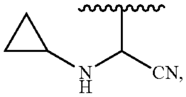
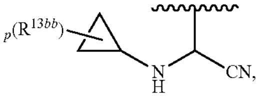
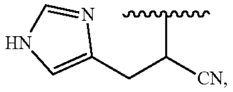
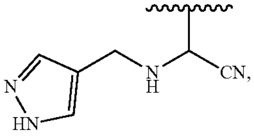
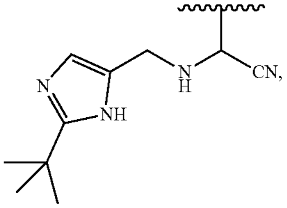
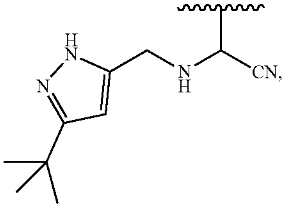
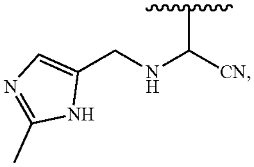
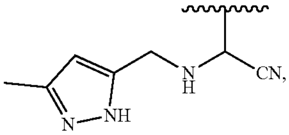
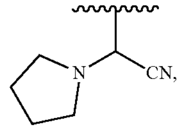
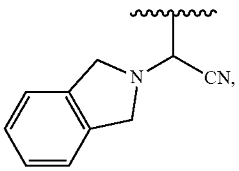
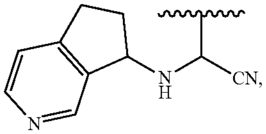
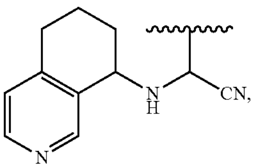
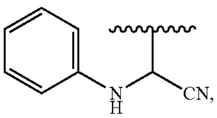
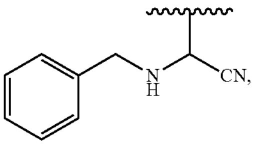
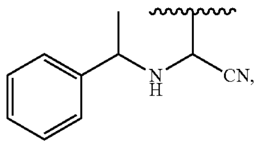

-continued

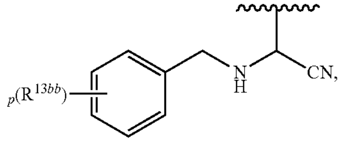

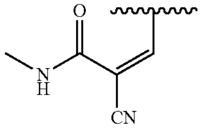
,
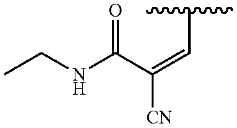
,
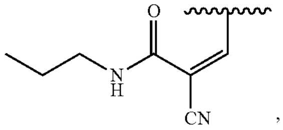
,
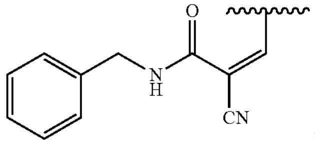
,
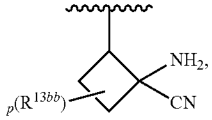

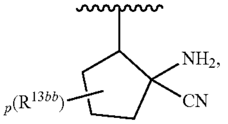

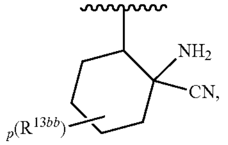

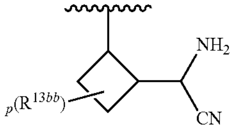
,
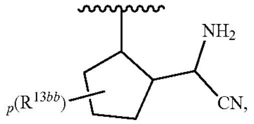
and
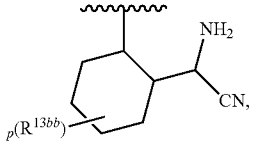

wherein $R^{13bb}$ is independently selected, for each occurrence, from the group consisting of halogen, $C_1$-$C_6$alkyl, $C_1$-$C_6$haloalkyl, $C_1$-$C_6$alkoxy, $C_3$-$C_{10}$cycloalkyl, —$N(R^eR^f)$, and —C(O)—$N(R^eR^f)$; $R^e$ and $R^f$ are each independently selected, for each occurrence, from the group consisting of hydrogen and $C_1$-$C_6$alkyl; or $R^e$ and $R^f$ may form, together with the nitrogen to which they are attached, a 4-6 membered heterocycle; and p is 0, 1, 2, 3, or 4, as valency permits.

In some embodiments, the warhead is a moiety with an imino-oxazolidinone moiety. Examples of exemplary imino-oxazolidinone warheads include, but not limited to:

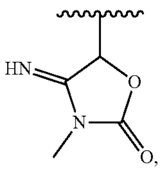

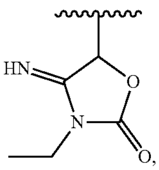

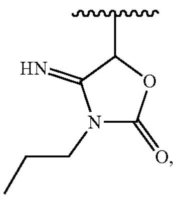

-continued

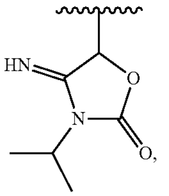

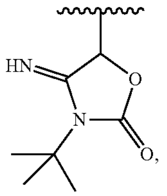
and
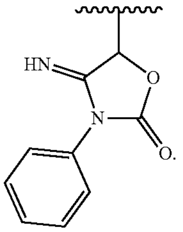

In some embodiments, the warhead is a moiety with an iminoimidazolidinone. Examples of exemplary iminoimidazolidinone warheads include, but not limited to:

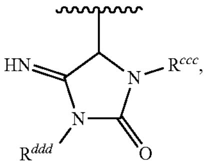

wherein each $R^{ccc}$ and $R^{ddd}$ is selected from the group consisting of hydrogen, $C_1$-$C_5$alkyl, $C_3$-$C_6$cycloalkyl, —($C_1$-$C_5$alkyl)-($C_6$-$C_{14}$aryl), and $C_6$-$C_{14}$aryl. In some embodiments, the warhead is selected from the group consisting of

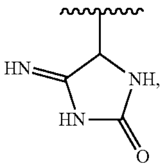

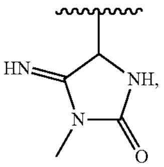

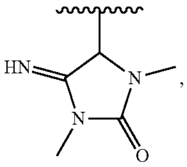
,
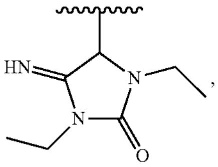
,
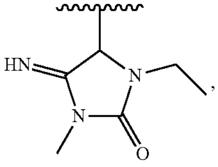
,
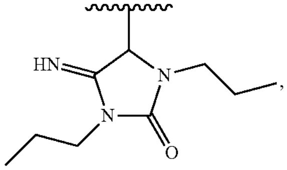
,
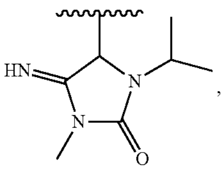
,
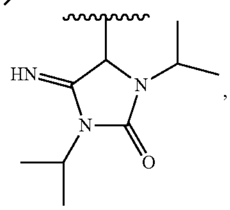
, and -continued

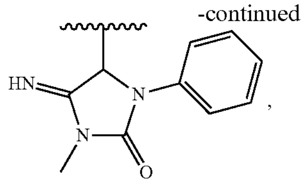

In some embodiments, the examples of exemplary warheads include, but not limited to:

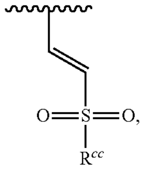

wherein $R^{cc}$ is selected from the group consisting of hydrogen, $C_1$-$C_5$alkyl, $C_3$-$C_6$cycloalkyl, —($C_1$-$C_8$alkyl)-($C_6$-$C_{14}$aryl), $C_6$-$C_{14}$aryl, 5-10 membered heteroaryl, —($C_1$-$C_8$alkyl)-(5-10 membered heteroaryl), 5-10 membered heterocycle and —N($R^bR^c$), wherein $R^b$ and $R^c$ are each selected from the group consisting of hydrogen, $C_1$-$C_5$alkyl, and $C_3$-$C_6$cycloalkyl, or $R^b$ and $R^c$ may be joined together to form, together with the nitrogen to which they are attached, a 5-10 membered heterocycle.

Some other examples of exemplary warheads include, but not limited to:

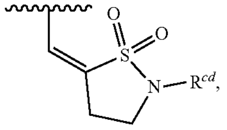

wherein $R^{cd}$ is selected from the group consisting of hydrogen, $C_1$-$C_8$alkyl, and $C_3$-$C_6$cycloalkyl.

It will be appreciated to one of skilled in the art that the compounds disclosed herein that include the warheads above also contemplate the precursors to those compounds, for example, where a cyano moiety involved in a warheads may be replaced with e.g., a halo moiety.

It will be appreciated to one of skilled in the art that the compounds disclosed herein can also irreversibly bind, or may otherwise inhibit e.g., a virus protein via any other mechanism of action.

The term "inhibitor" as used herein refers to a compound that binds to and/or inhibits a target protease with measurable affinity.

The term "reversible" or "reversible inhibitor" as used herein refers to a protease inhibitor that associates with a protease in such a way as to inhibit the activity of the protease while the protease and inhibitor are bound, but does not associate with a protease in such a way as to inhibit the activity of the protease when the protease and inhibitor are no longer bound. Reversible inhibitors can effect inhibition by competing with substrate for binding to the active site of the protease (competitive reversible inhibitor), or by associating with the protease bound to its substrate in a way to make the complex inactive (uncompetitive reversible inhibitor), or by associating with the protease and/or protease-substrate complex in a way that inhibits the activity of either and/or both.

As used herein, the term "irreversible" or "irreversible inhibitor" refers to an inhibitor (i.e. a compound) that is able to be covalently bonded to a target protease in a substantially non-reversible manner. An irreversible inhibitor will remain substantially bound to the target protease once covalent bond formation has occurred. Irreversible inhibitors usually display time dependency, whereby the degree of inhibition increases with the time with which the inhibitor is in contact with the enzyme. In certain embodiments, an irreversible inhibitor will remain substantially bound to target protease once covalent bond formation has occurred and will remain bound for a time period that is longer than the life of the protein.

I. Reversible or Irreversible Viral Protease Inhibitor Compounds

The disclosure is directed to, in part, compounds that inhibit a viral protease. Examples of viral proteases include, but not limited to, Cathepsin K, coronavirus main protease (Mpro), Caspase 3, Calpain 1, and Cathepsin S. Accordingly, in various embodiments, a compound of the present disclosure (e.g. a compound of Formula I, I-A-I, I-A, I-B, I-C, II, III, III-A, X, or X-A) is a viral protease inhibitor, wherein the viral protease is selected from the group consisting of Cathepsin K, coronavirus main protease (Mpro), Caspase 3, Calpain 1, and Cathepsin S. In certain embodiments, the viral protease is a coronavirus main protease (Mpro). In some embodiments, the viral protease is Cathepsin K. In some embodiments, the viral protease is Caspase 3. In some embodiments, the viral protease is Calpain 1. In some embodiments, the viral protease is Cathepsin S.

In an embodiment, provided herein are compounds represented by Formula I:

Formula I

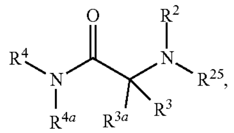

wherein: $R^{25}$ is selected from the group consisting of —C(O)$R^1$, phenyl, 3-10 membered heterocyclyl, and 5-10 membered heteroaryl (e.g., a 5-6 membered monocyclic or 7-10 membered bicyclic heteroaryl), wherein the phenyl, 3-10 membered heterocyclyl, or 5-10 membered heteroaryl is optionally substituted by one, two or three substituents each selected from $R^a$, or $R^{25}$ is a warhead; $R^1$ is selected from the group consisting of $C_1$-$C_6$alkyl-N($R^bR^c$), $C_3$-$C_{10}$cycloalkyl, $C_6$-$C_{14}$aryl (e.g., phenyl), 3-10 membered heterocyclyl, and 5-10 membered heteroaryl (e.g., a 5-6 membered monocyclic or 7-10 membered bicyclic heteroaryl), wherein $R^1$ is optionally substituted by one, two or three substituents each selected from $R^a$, or $R^1$ is a warhead; $R^2$ is selected from the group consisting of $C_6$-$C_{14}$aryl (e.g., phenyl), 3-10 membered heterocyclyl, 5-10 membered heteroaryl (e.g., a 5-6 membered monocyclic or 7-10 membered bicyclic heteroaryl), and $C_3$-$C_{10}$cycloalkyl, wherein $R^2$ is optionally substituted by one, two or three substituents each selected from the group consisting of halogen, —C(O)—N($R^bR^c$) and $R^5$, or $R^2$ is a warhead; $R^3$ is independently selected, for each occurrence, from the group consisting of $C_1$-$C_6$haloalkyl, hydroxyl, oxo, $SF_5$, cyano, halogen, $C_1$-$C_6$alkyl, $C_1$-$C_6$alkoxy, $C_6$-$C_{14}$aryl, $C_1$-$C_6$alkyl-phenyl, $C_1$-$C_6$alkenyl-phenyl, $C_1$-$C_6$alkoxy-phenyl, $C_3$-$C_{10}$cycloalkyl, and 5-9 membered heteroaryl; wherein $R^5$ is optionally substituted by one, two or three substituents each selected from $R^a$; $R^3$ is selected from the group consisting of $C_6$-$C_{14}$aryl (e.g., phenyl), 3-10 membered heterocyclyl, 5-6 membered monocyclic heteroaryl, and 8-10 membered bicyclic heteroaryl, wherein the heteroaryl contains at least one ring nitrogen and may have one, two or three optional substituents each selected from $R^a$, or $R^3$ is a warhead; $R^{3a}$ is selected from the group consisting of hydrogen, $C_1$-$C_6$alkyl, $C_1$-$C_6$haloalkyl, halogen and deuterium; or $R^3$ and $R^{3a}$ may be joined together to form, together with the carbon to which they are attached, a 3-10 membered heterocyclyl, or $R^{3a}$ is a warhead; or $R^{3a}$ and $R^{4a}$ may form, together with the carbon and nitrogen to which they are attached, respectively, a 5-10 membered heterocycle, wherein the heterocycle is optionally substituted by one, two or three substituents each selected from $R^a$; $R^4$ is selected from the group consisting of hydrogen, halogen, $C_1$-$C_6$alkyl, $C_1$-$C_6$alkoxy, $C_1$-$C_6$alkyl-N($R^bR^c$), $C_1$-$C_6$alkyl-($C_6$-$C_{14}$aryl), $C_1$-$C_6$alkyl-(3-10 membered heterocyclyl), $C_1$-$C_6$alkyl-(5-9 membered heteroaryl), $C_3$-$C_{10}$cycloalkyl, $C_6$-$C_{14}$aryl (e.g., phenyl), 3-10 membered heterocyclyl, and 5-10 membered heteroaryl (e.g., a 5-6 membered monocyclic or 7-10 membered bicyclic heteroaryl), wherein the aryl, heteroaryl, alkyl, alkoxy, or cycloalkyl is optionally substituted by one, two or three substituents each selected from $R^a$; $R^{4a}$ is selected from the group consisting of hydrogen, $C_1$-$C_6$alkyl, $C_1$-$C_6$alkoxy, $C_3$-$C_{10}$cycloalkyl, 3-10 membered heterocyclyl, $C_6$-$C_{14}$aryl (e.g., phenyl), and 5-10 membered heteroaryl (e.g., a 5-6 membered monocyclic or 7-10 membered bicyclic heteroaryl), wherein the aryl, heteroaryl, alkyl, alkoxy, or cycloalkyl is optionally substituted by one, two or three substituents each selected from $R^a$; or $R^4$ and $R^{4a}$ may form, together with the nitrogen to which they are attached, a 4-10 membered heterocycle, wherein the heterocycle is optionally substituted by one, two or three substituents each selected from $R^a$; $R^a$ is independently selected, for each occurrence, from the group consisting of halogen, hydroxyl, oxo, cyano, $SF_5$, —$OR^{aa}$, $S(O)_2$—($C_1$-$C_6$alkyl), $C_1$-$C_6$alkyl, $C_1$-$C_6$alkyl-OH, $C_1$-$C_6$haloalkyl, $C_1$-$C_6$alkoxy, $C_3$-$C_{10}$cycloalkyl, $C_6$-$C_{14}$aryl (e.g., phenyl), 3-10 membered heterocyclyl, 5-10 membered heteroaryl (e.g., a 5-6 membered monocyclic or 7-10 membered bicyclic heteroaryl), —C(O)—O—$C(CH_3)_3$, —C(O)—O—($CH_2$)—($C_{13}H_9$), —NH—C(O)—O—$C(CH_3)_3$, —C(O)—O—($CH_2$)-(phenyl), —C(O)—N($R^bR^c$), and —N($R^bR^c$), wherein the aryl, heteroaryl, or heterocyclyl is optionally substituted by one, two, or three substituents of halogen; and $R^{aa}$ is selected from the group consisting of $C_1$-$C_6$haloalkyl, $C_1$-$C_6$alkyl-phenyl and $C_6$-$C_{14}$aryl; $R^b$ and $R^c$ are each selected from the group consisting of hydrogen, $C_1$-$C_6$alkyl, and $C_3$-$C_{10}$cycloalkyl; wherein the $C_1$-$C_6$alkyl or $C_3$-$C_{10}$cycloalkyl may optionally be substituted by one or more substituents selected from the group consisting of halogen, cyano, oxo, and hydroxyl; or $R^b$ and $R^c$ may form, together with the nitrogen to which they are attached, a 4-6 membered heterocycle, wherein the 4-6 membered heterocycle is optionally substituted by one, two or three substituents each selected from $R^a$; wherein one of $R^{25}$, $R^1$, $R^2$, and $R^3$ is a warhead; and pharmaceutically acceptable salts, stereoisomers, esters, and prodrugs thereof.

In some embodiments, the compound of Formula I is represented by

Formula I-A-I

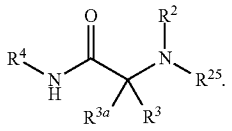

In some embodiments, the compound of Formula I is represented by

Formula I-A

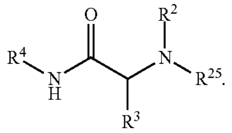

In some embodiments, the compound of Formula I is represented by

Formula I-B

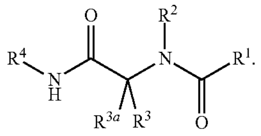

In some embodiments, the compound of Formula I is represented by

Formula I-C

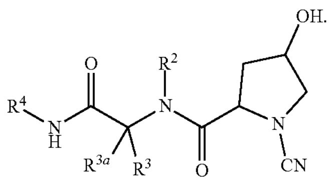

In certain embodiments, the warhead is selected from the group consisting of:

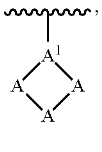 , 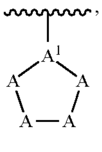 , 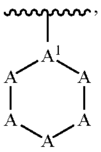 , 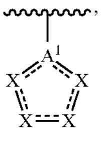 ,

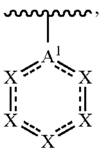 , 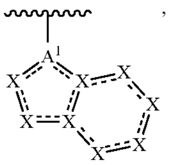 , 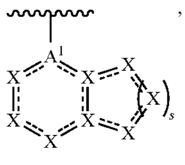 ,

-continued

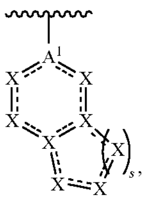, and 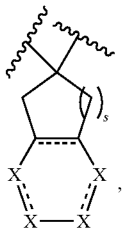, wherein A is independently selected, for each occurrence, from the group consisting of S, O, $C(R^{13c})_2$, $N(R^{13c})_2$ and $S(O)_2$, or two A may form, together with the carbons to which they are attached, a $C_1$-$C_3$ alkylene bridge, wherein the alkylene bridge may optionally be substituted by one, two or three substituents selected from the group consisting of $C_1$-$C_6$alkyl, $C_1$-$C_6$haloalkyl, oxo, hydroxyl and halogen; $A^1$ is selected from the group consisting of C, N, CH and $C(C_1$-$C_6$alkyl); X is independently selected, for each occurrence, from the group consisting of S, O, C, N, $CR^{13C}$ and $NR^{13c}$; $R^{13c}$ is independently selected, for each occurrence, from the group consisting of hydrogen, cyano, halogen, hydroxyl, oxo, —CH(CN)(OH), —$SR^{13e}$, —$S(R^{13e})$, —$S(O)R^{13e}$, —$S(O)_2R^{13e}$, and $R^{13a}$, as valency permits; $R^{13a}$ is selected from the group consisting of —$OR^{13b}$, —$N(R^eR^f)$, —$N(R^e)$—C(O)—$(R^f)$, $C_1$-$C_6$alkyl, $C_1$-$C_6$haloalkyl, $C_1$-$C_6$alkoxy, $C_3$-$C_{10}$cycloalkyl, 3-10 membered heterocyclyl, $C_6$-$C_{14}$aryl (e.g., phenyl) and 5-10 membered heteroaryl (e.g., a 5-6 membered monocyclic or 7-10 membered bicyclic heteroaryl); wherein $R^{13a}$ may be optionally substituted by one, two or three substituents each selected from $R^h$; $R^{13b}$ is selected from the group consisting of $C_1$-$C_6$alkyl-(3-10 membered heterocyclyl), $C_1$-$C_6$alkyl-(5-10 membered heteroaryl), $C_1$-$C_6$alkyl-($C_6$-$C_{14}$aryl), $C_1$-$C_6$haloalkyl, $C_3$-$C_{10}$cycloalkyl, $C_6$-$C_{14}$aryl, 3-10 membered heterocyclyl and 5-10 membered heteroaryl; $R^{13e}$ is independently selected, for each occurrence, from the group consisting of hydrogen, halogen, $C_1$-$C_6$alkyl, $C_1$-$C_6$haloalkyl, $C_3$-$C_{10}$cycloalkyl, and $C_1$-$C_6$alkoxy; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, hydroxyl, 3-10 membered heterocyclyl, $C_6$-$C_{14}$aryl, and 5-10 membered heteroaryl; or $R^e$ and $R^f$ may form, together with the nitrogen to which they are attached, a 4-6 membered heterocycle; $R^h$ is independently selected, for each occurrence, from the group consisting of halogen, $C_1$-$C_6$alkyl, $C_1$-$C_6$haloalky, and $C_1$-$C_6$alkoxy; ══════ denotes a bond that may be a single or double bond; and s is selected from 1 and 2. It can be appreciated that the warhead, in this and other certain embodiments, may be either a reversible or an irreversible warhead.

In embodiments, $R^{25}$ is the warhead. It can be appreciated that the warhead, in this and other certain embodiments, may be a reversible warhead.

In embodiments, $R^{25}$ is the warhead selected from the group consisting of

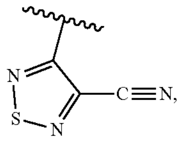 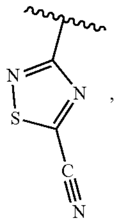,

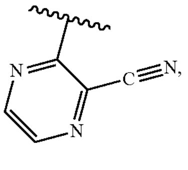 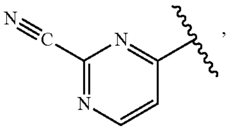,

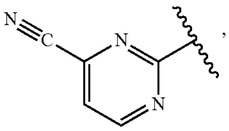, 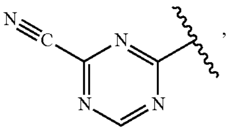,

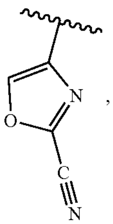, 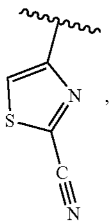, 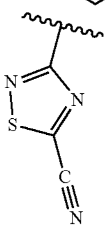,

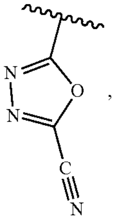, 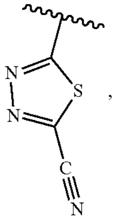, 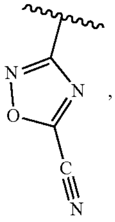,

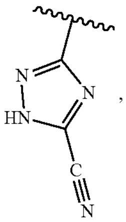, 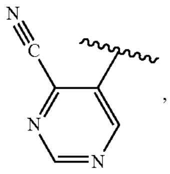, 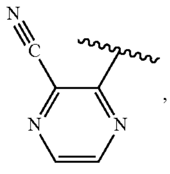,

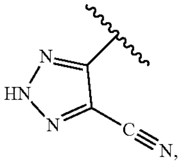 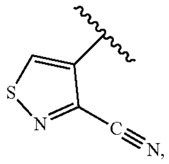

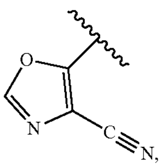 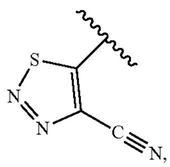

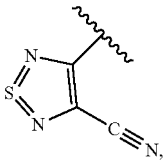 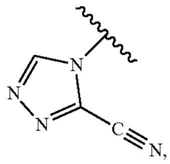

-continued
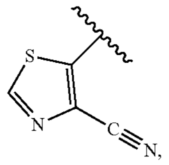
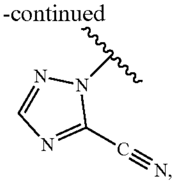
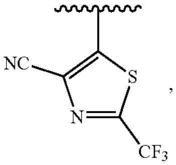
,
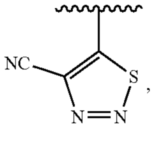
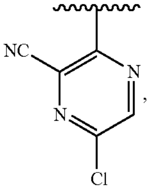
and
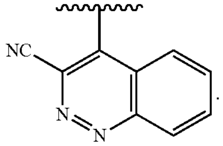
In embodiments, $R^1$ is the warhead. It can be appreciated that the warhead, in this and other certain embodiments, may be a reversible warhead.
In embodiments, $R^1$ is the warhead selected from the group consisting of
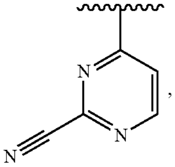
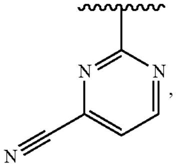
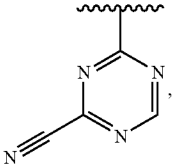
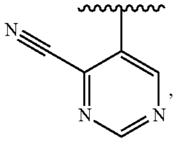
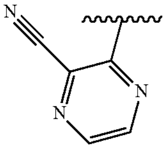
,
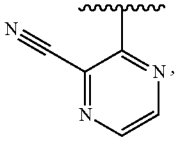
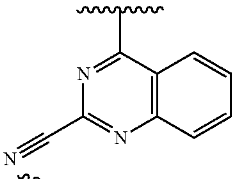
,
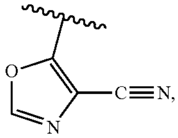
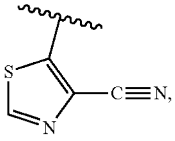
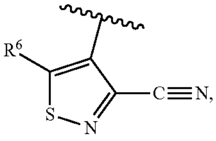
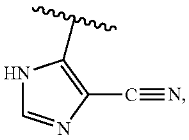
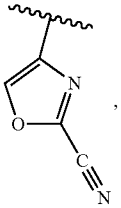
,
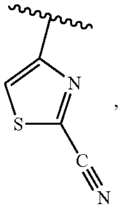
,
-continued
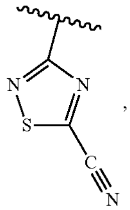
,
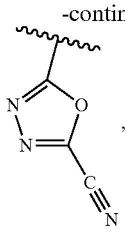
,
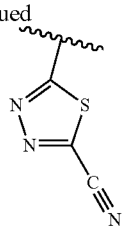
,
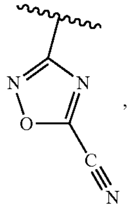
,
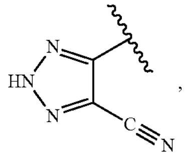
,
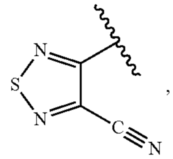
,
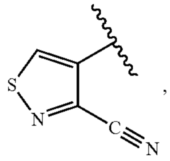
,
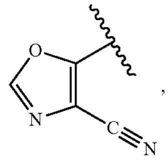
,
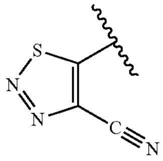
,
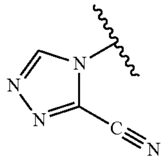
,
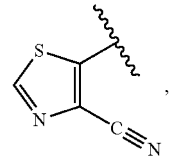
,
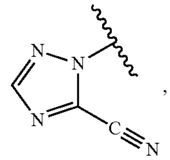
,
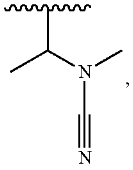
,
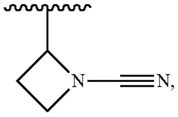
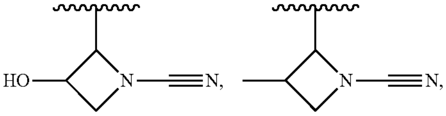
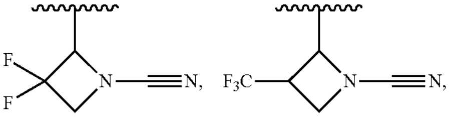
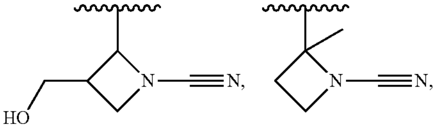
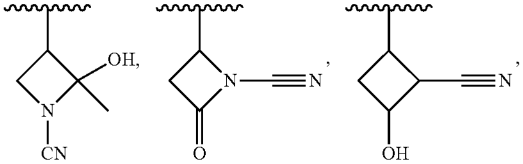
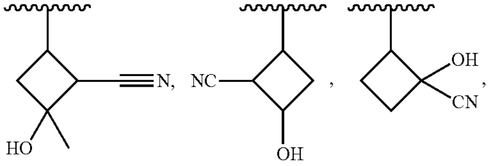
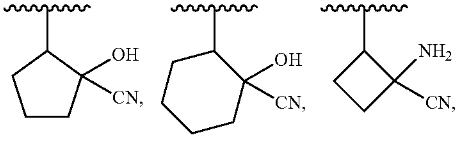

-continued
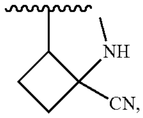
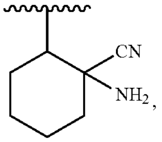
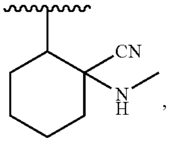
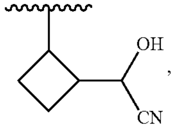
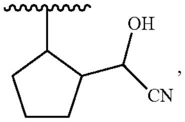
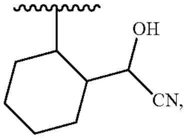
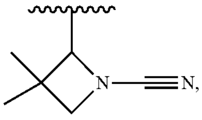
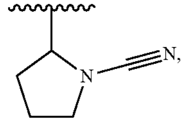
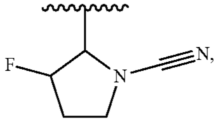
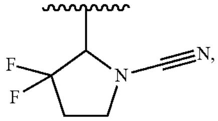
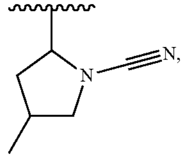
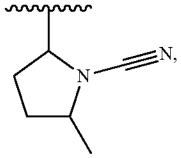
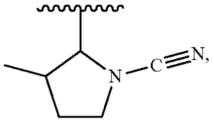
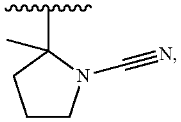
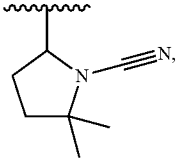
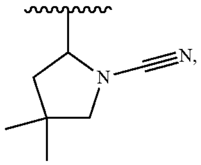
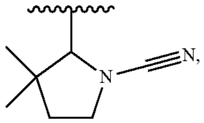
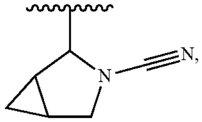
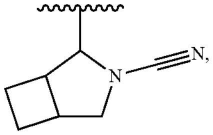
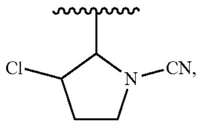
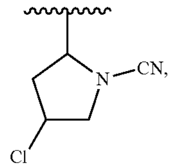
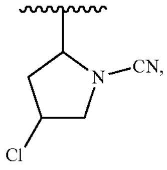
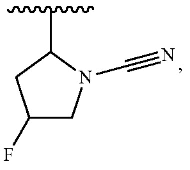
-continued
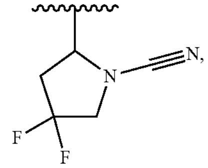
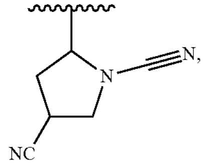
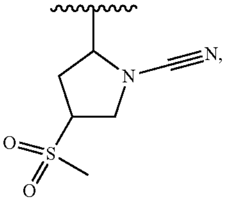
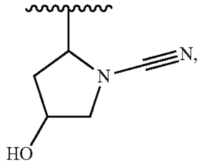
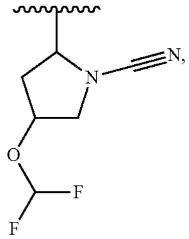
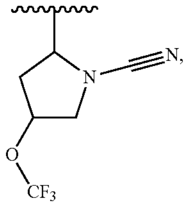
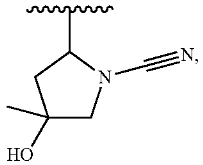
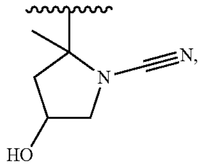
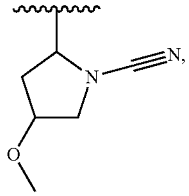
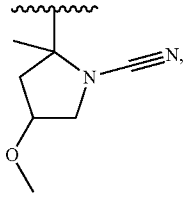
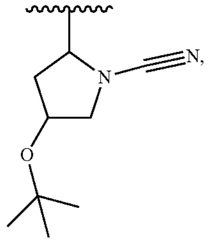
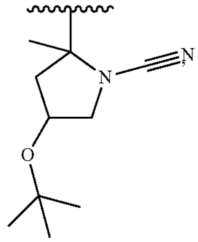
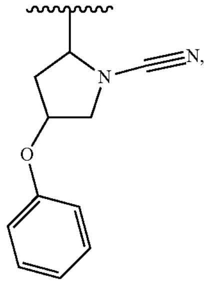
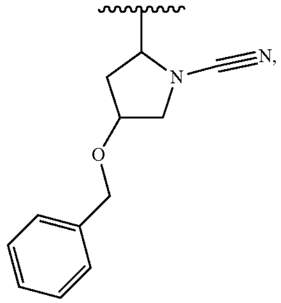
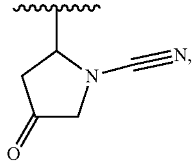
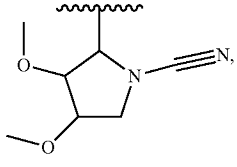

-continued
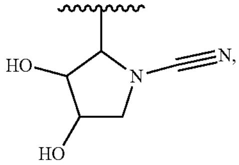
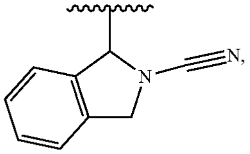
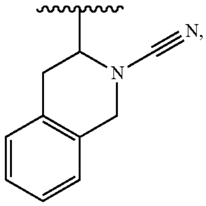
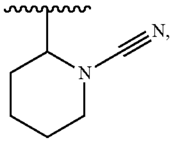
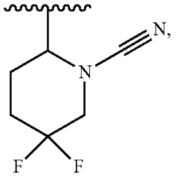
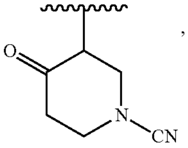
,
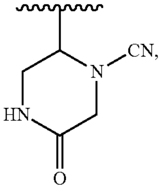
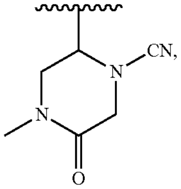
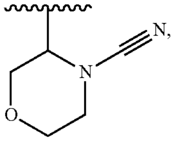
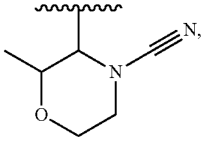
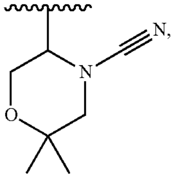
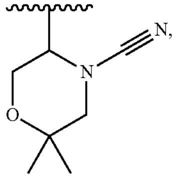
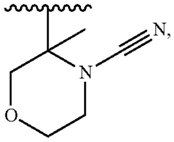
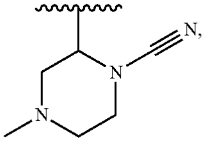
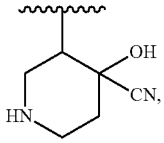
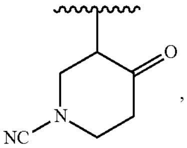
,
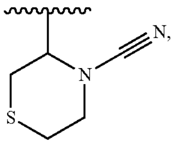
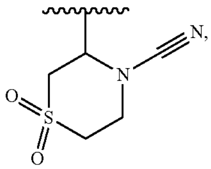
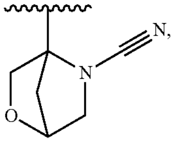
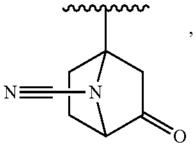
,
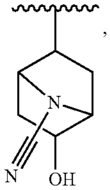
,
-continued
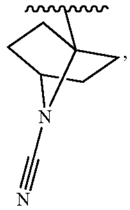
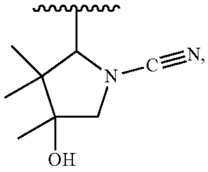
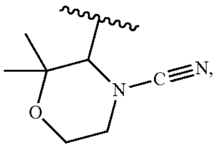
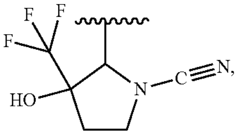
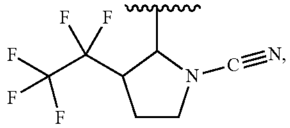
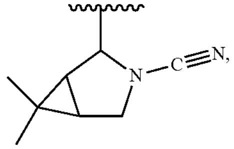
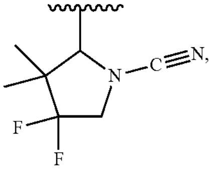
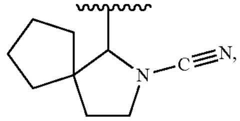
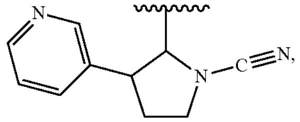
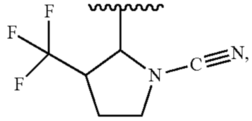
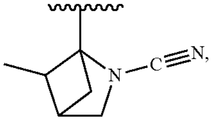
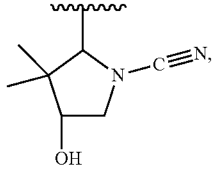
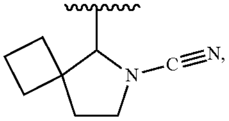
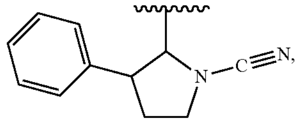
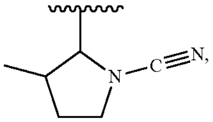
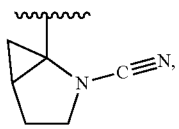
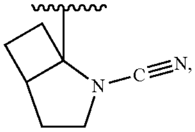
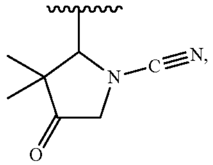
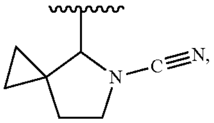

-continued
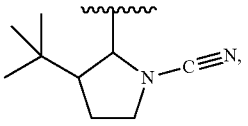
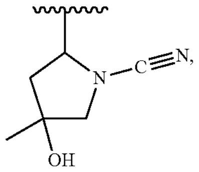 and
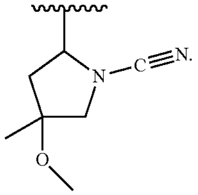
In embodiments, $R^1$ is the warhead selected from the group consisting of
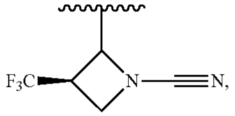
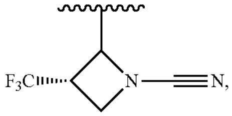
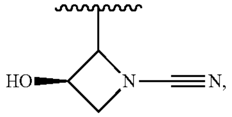
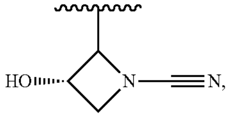
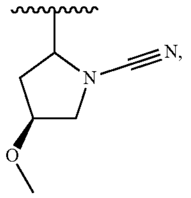 and
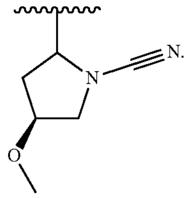
In some embodiments, $R^1$ is selected from the group consisting of:
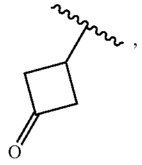
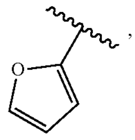
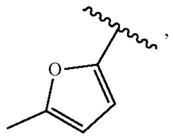
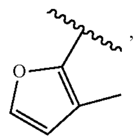
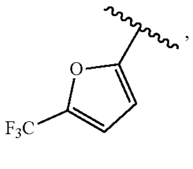
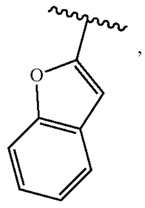
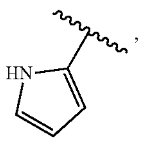
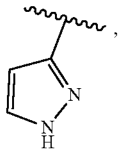
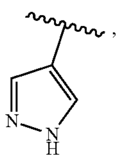
-continued
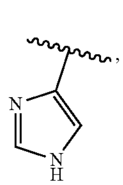
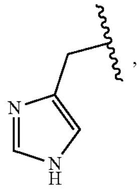
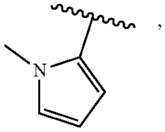
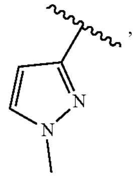
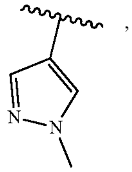
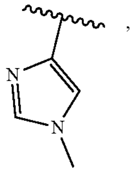
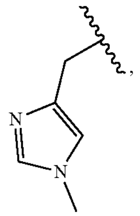
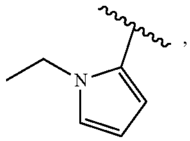
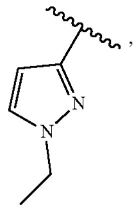
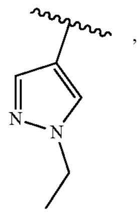
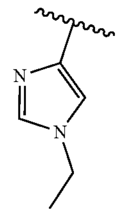 and
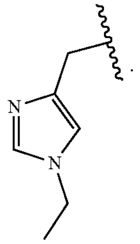
In some embodiments, $R^1$ is the warhead selected from
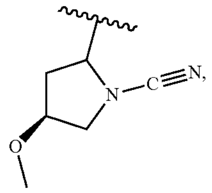
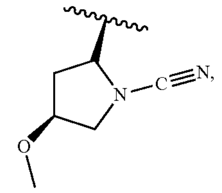
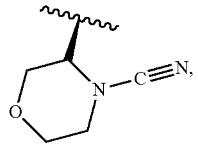
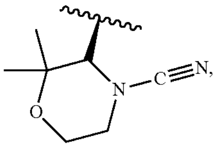
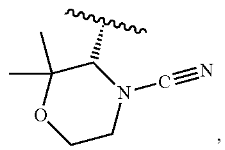
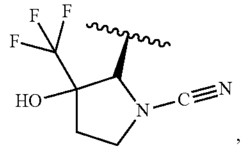
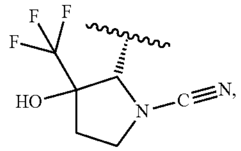

-continued
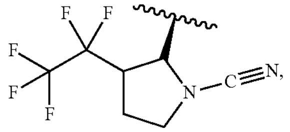
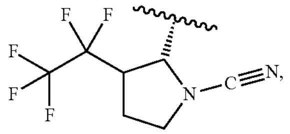
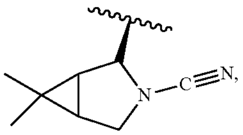
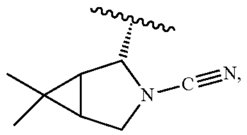
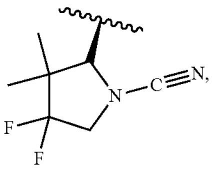
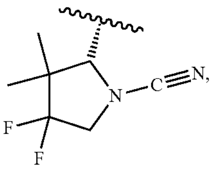
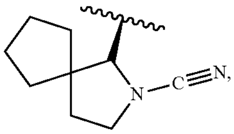
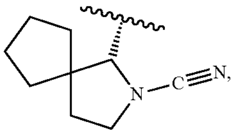
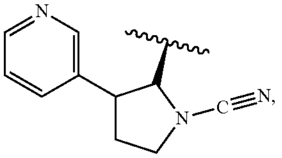
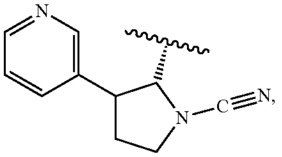
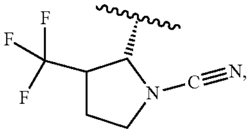
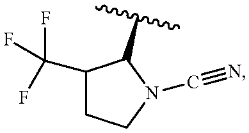
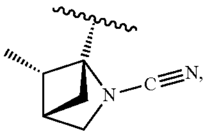
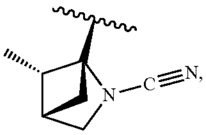
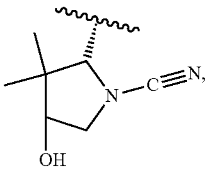
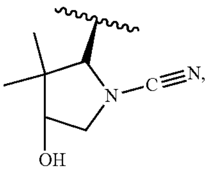
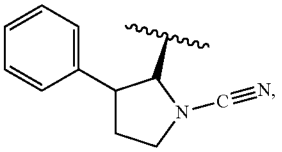
-continued
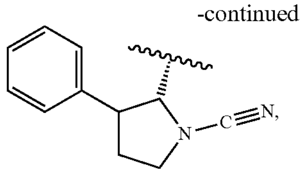
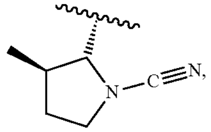
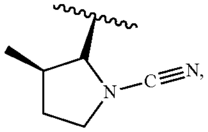
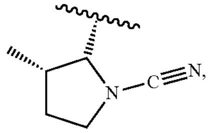
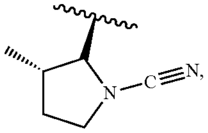
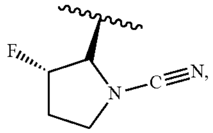
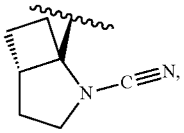
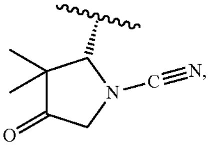
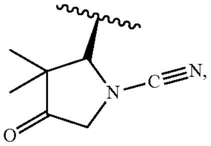
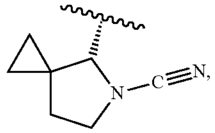
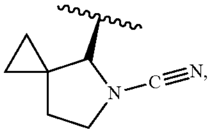
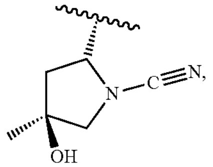
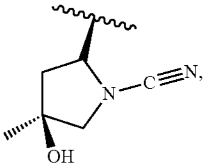
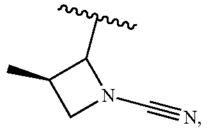
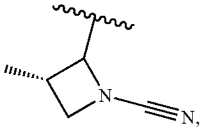
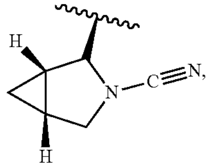
and
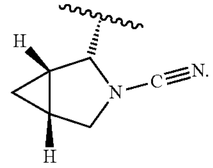
In some embodiments, $R^2$ is the warhead. It can be appreciated that the warhead, in this and other certain embodiments, may be a reversible warhead.
In some embodiments, $R^2$ is the warhead selected from
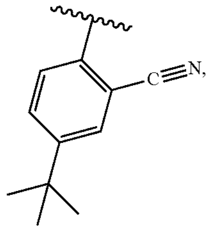
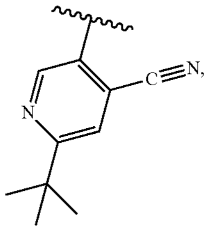

-continued
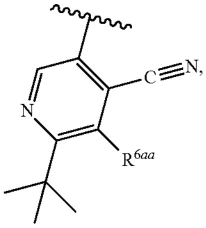
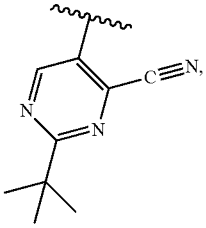
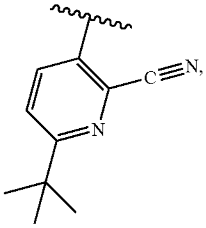
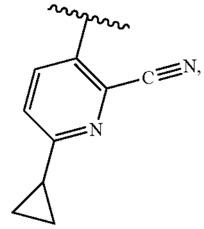
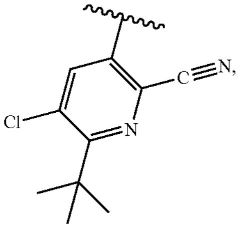
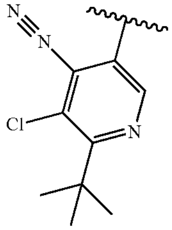
,
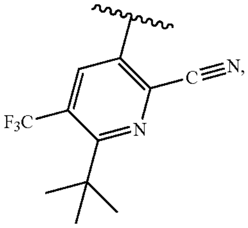
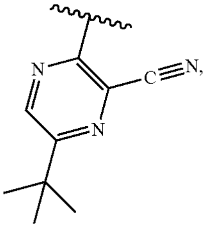
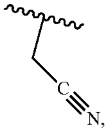
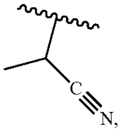
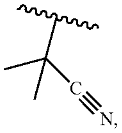
and
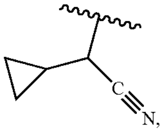
wherein $R^{6aa}$ is independently selected, for each occurrence, from the group consisting of: hydrogen, halogen, $C_1$-$C_5$alkyl, $C_1$-$C_6$haloalkyl, and $C_1$-$C_5$alkoxy.
In some embodiments, $R^2$ is selected from the group consisting of:
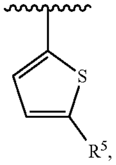
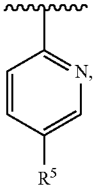
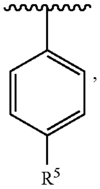
,
-continued
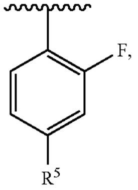
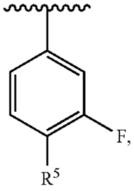
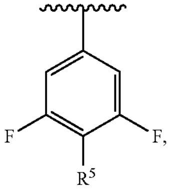
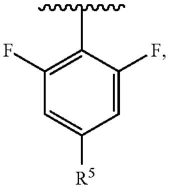
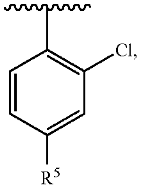
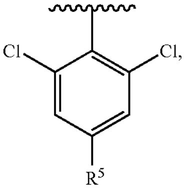
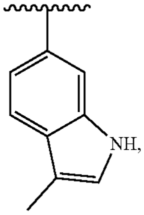
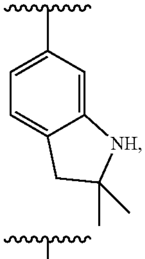
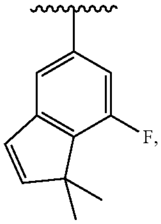
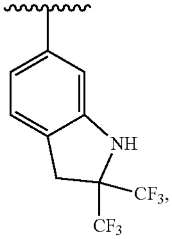
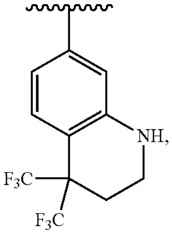
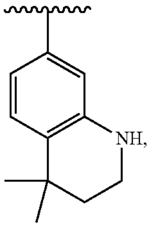
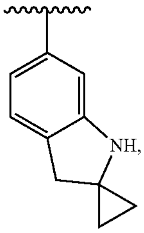
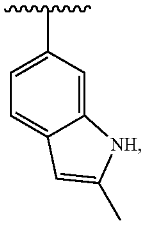
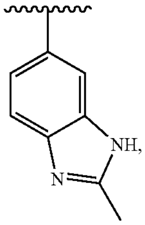

-continued

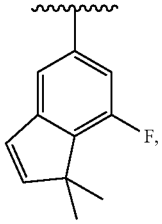

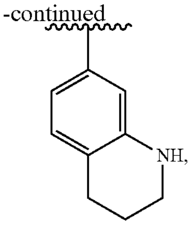

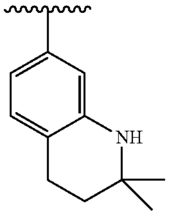

,

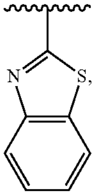

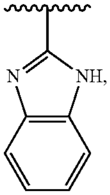

and

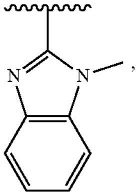

wherein $R^5$ is independently selected, for each occurrence, from the group consisting of $C_1$-$C_6$haloalkyl, hydroxyl, oxo, $SF_5$, cyano, $C_1$-$C_6$alkyl, $C_1$-$C_6$alkoxy, $C_6$-$C_{14}$aryl, $C_1$-$C_6$alkyl-phenyl, $C_1$-$C_6$alkenyl-phenyl, $C_1$-$C_6$alkoxy-phenyl, $C_3$-$C_{10}$cycloalkyl, and 5-9 membered heteroaryl.

In some embodiments, $R^5$ is selected from the group consisting of

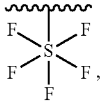

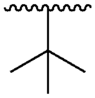

,

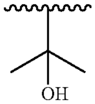

,

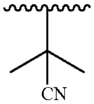

,

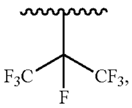

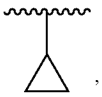

, and

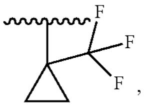

,

In embodiments, $R^{3a}$ is selected from the group consisting of hydrogen, deuterium, F, $CH_3$, and $CF_3$.

In embodiments, $R^3$ is the warhead. It can be appreciated that the warhead, in this and other certain embodiments, may be a reversible warhead.

In embodiments, $R^3$ is the warhead selected from the group consisting of

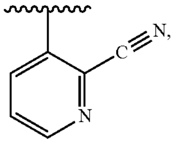

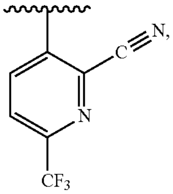

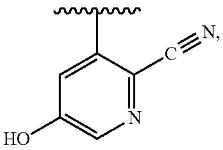

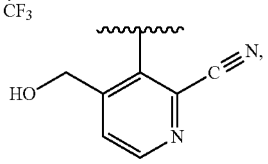

-continued

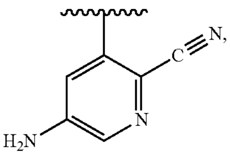

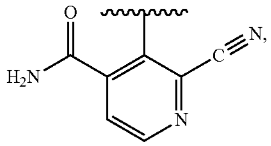

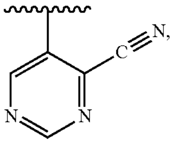

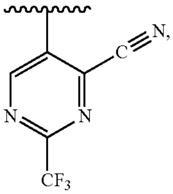

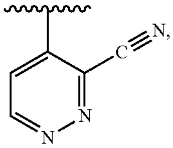

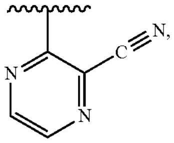

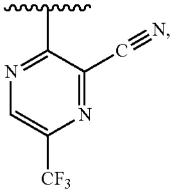

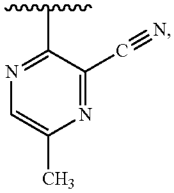

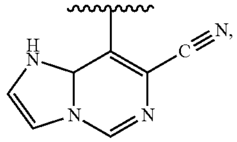

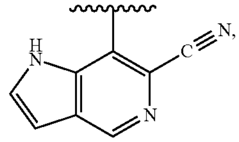

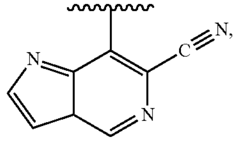

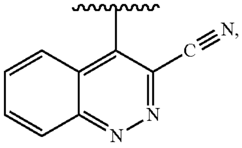

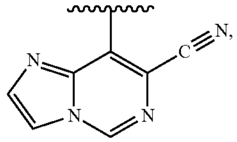

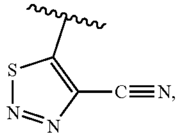

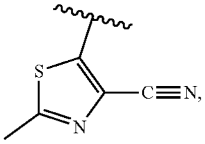

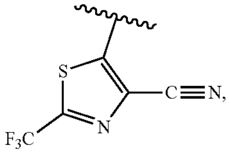

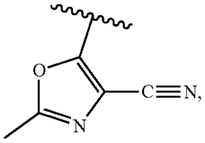

and

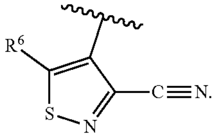

In embodiments, $R^3$ is selected from the group consisting of
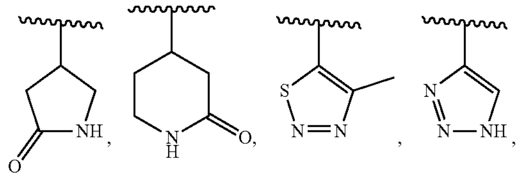
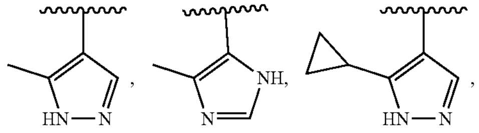
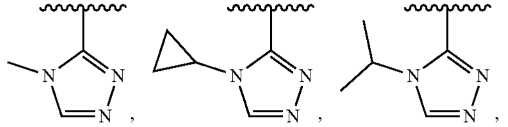
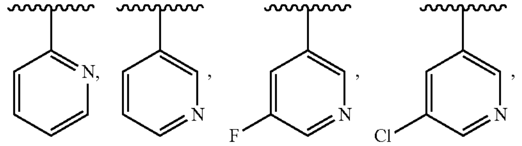
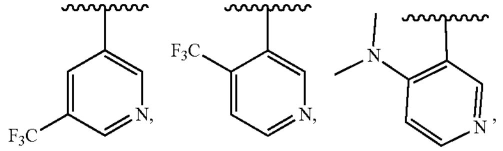
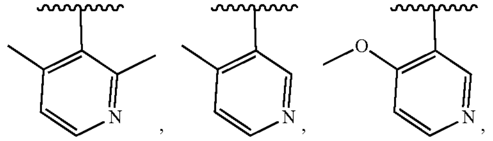
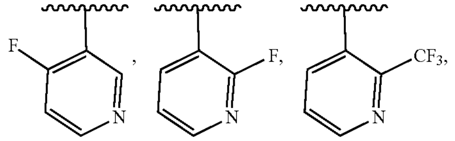
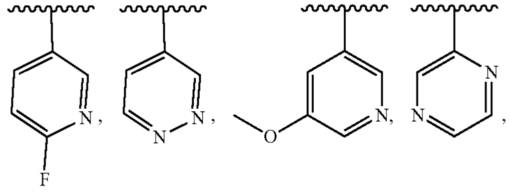
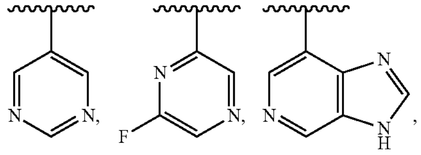
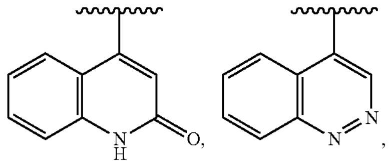
-continued
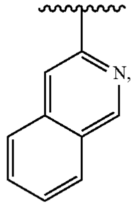
and
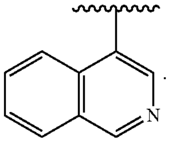
In some embodiments, $R^4$ is selected from the group consisting of
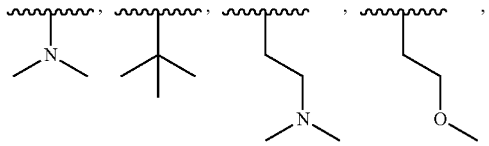
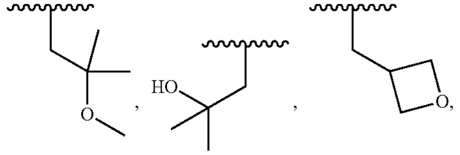
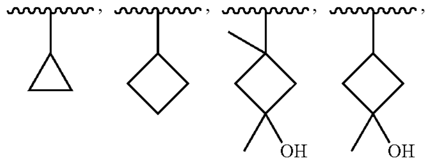
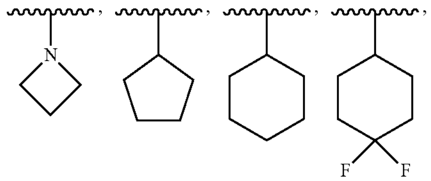
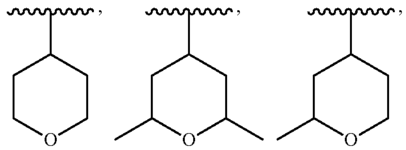
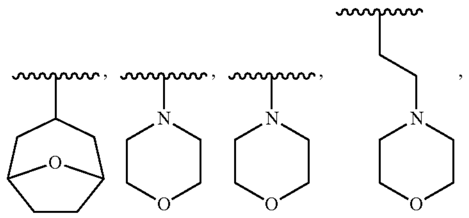
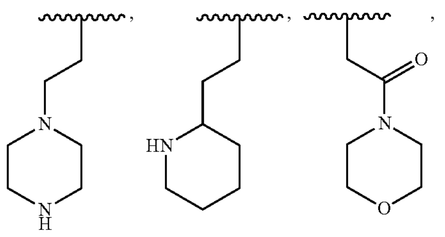

-continued
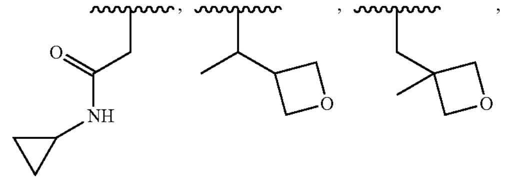
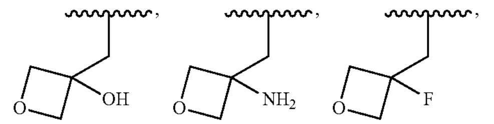
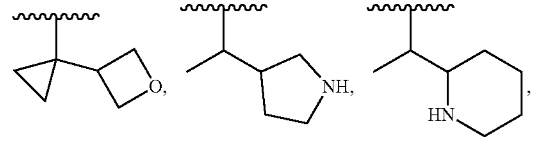
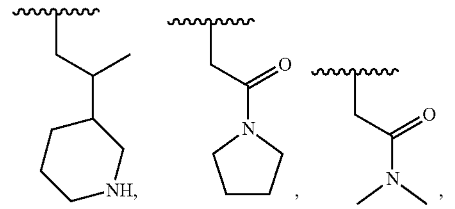
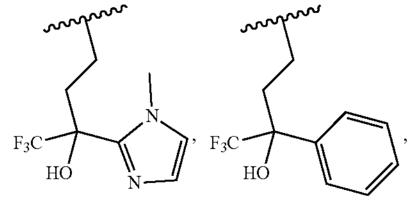
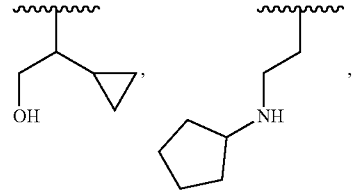
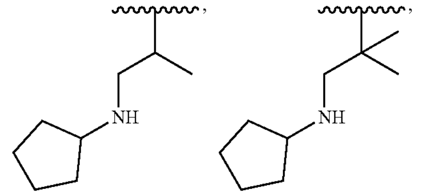
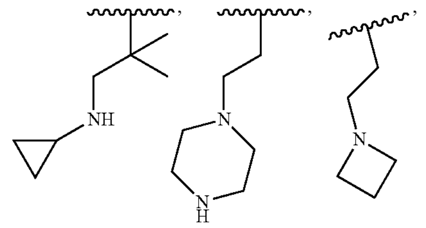
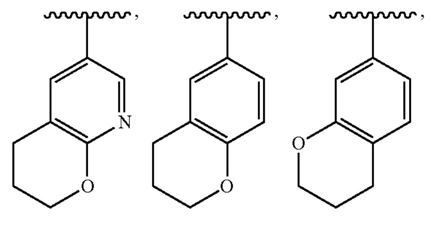
-continued
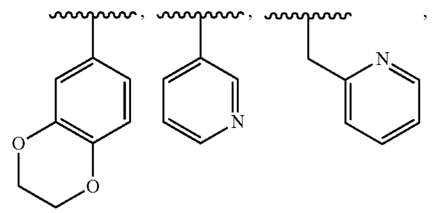
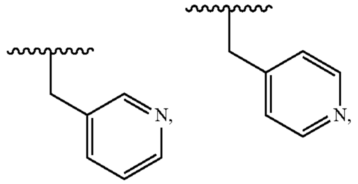
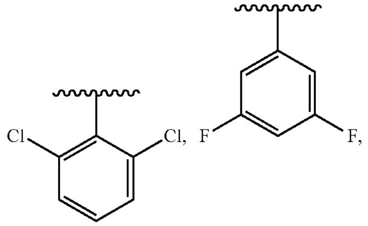
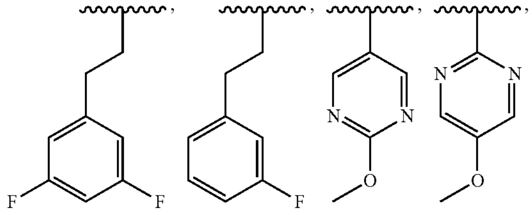
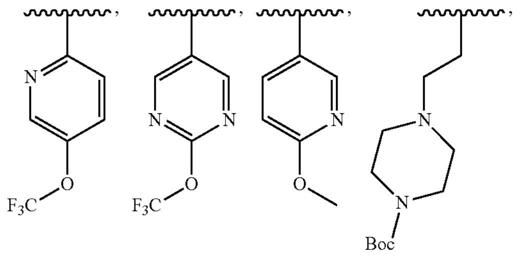
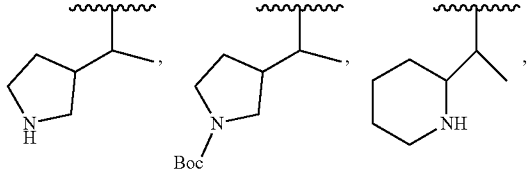
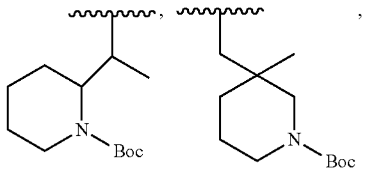
, and
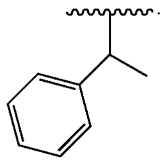

In some embodiments, $R^4$ is

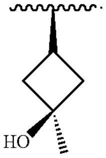

In some embodiments, $R^4$ and $R^{4a}$ are joined together to form the heterocycle selected from the group consisting of:

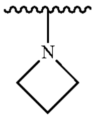, 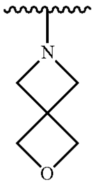, 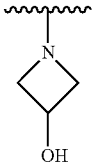, 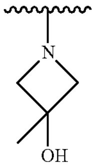, 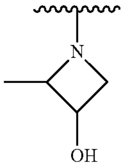, 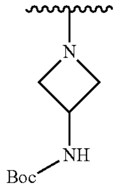, 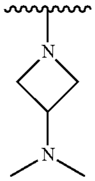, 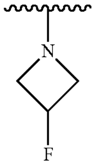, 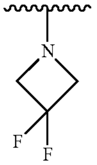, 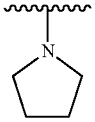, 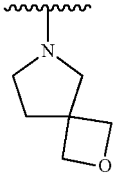, 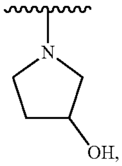 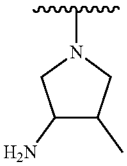 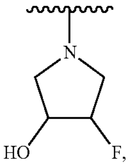, 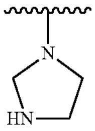, 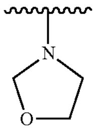, 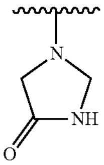, 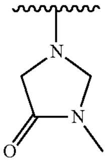, 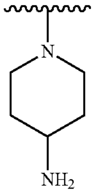, 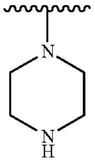, 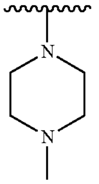, 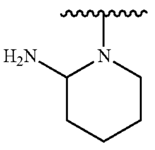, 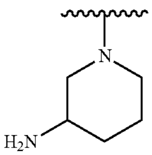, 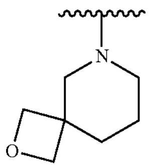, -continued

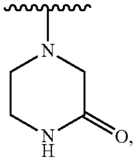 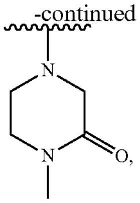 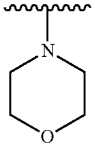, and

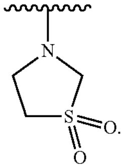

In some embodiments, the $R^{4a}$ and $R^{3a}$ joined together to form the heterocycle

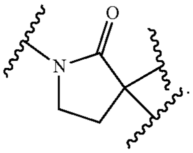 [SMILES: *N1CCC(*)(*)C1=O]

In an embodiment, provided herein are compounds represented by Formula II:

Formula II

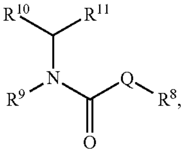

wherein: $R^8$ is selected from the group consisting of

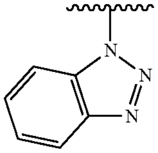 and 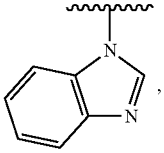, wherein $R^8$ may be optionally substituted on an available carbon by $R^d$, or $R^8$ is a warhead; Q is $CH_2$ or NH; $R^9$ is a phenyl, or monocyclic or 8-10 membered bicyclic heteroaryl optionally substituted by one, two or three substituents each selected from $R^{12}$, or $R^9$ is a warhead; $R^{12}$ is independently selected, for each occurrence, from the group consisting of $C_1$-$C_6$alkyl, $C_3$-$C_{10}$cycloalkyl, phenyl, 5-6 membered heteroaryl, —N($R^eR^f$), —N($R^e$)—C(O)—($R^f$), and —N($R^e$)—S$(O)_2$—($R^f$), wherein the 5-6 membered heteroaryl may have one, two or three optional substituents each selected from $R^h$; $R^{10}$ is a phenyl, 5-6 membered monocyclic heteroaryl, or 7-10 membered heteroaryl, wherein $R^{10}$ is optionally substituted by one, two or three substituents each selected from $R^g$; $R^g$, for each occurrence, is selected from the group consisting of halogen, —$NO_2$, $C_1$-$C_5$alkyl, $C_1$-$C_5$alkoxy, $C_1$-$C_5$alkoxy-N($R^eR^f$), —N($R^eR^f$), phenyl, and 5-6 membered heteroaryl, wherein the phenyl or heteroaryl may have one, two or three optional substituents each selected from $R^h$; $R^{11}$ is selected from the group consisting of hydrogen, $C_1$-$C_5$alkyl, $C_3$-$C_6$cycloalkyl, and —C(O)—N($R^eR^f$); $R^d$, for each occurrence, is selected from the group consisting of halogen, hydroxyl, $C_1$-$C_5$alkyl, $C_1$-$C_6$haloalkyl, $C_1$-$C_5$alkoxy, —C(O)—N($R^eR^f$), and —N($R^eR^f$); $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, and hydroxyl; or $R^e$ and $R^f$ may form, together with the nitrogen to which they are attached, a 4-6 membered heterocycle; $R^h$, for each occurrence, is selected from the group consisting of halogen, $C_1$-$C_5$alkyl, $C_1$-$C_6$haloalkyl, and $C_1$-$C_5$alkoxy; wherein one of $R^8$ and $R^9$ is a warhead; and pharmaceutically acceptable salts, stereoisomers, esters, and prodrugs thereof.

In some embodiments, the warhead is independently selected from the group consisting of:

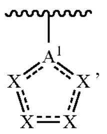, 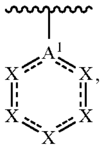, 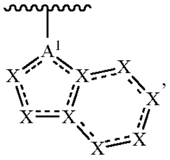, 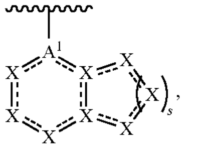, and 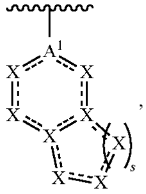, wherein $A^1$ is selected from the group consisting of C, N, CH and C($C_1$-$C_6$alkyl); X is independently selected, for each occurrence, from the group consisting of S, O, C, N, $CR^{13c}$ and $NR^{13c}$; $R^{13c}$ is independently selected, for each occurrence, from the group consisting of hydrogen, cyano, halogen, hydroxyl, oxo, —$SR^{13e}$, —S($R^{13e}$)$_5$, —S(O)$R^{13e}$, —S(O)$_2R^{13e}$, and $R^{13a}$, as valency permits; $R^{13a}$ is selected from the group consisting of —$OR^{13b}$, —N($R^eR^f$), —N($R^e$)—C(O)—($R^f$), $C_1$-$C_6$alkyl, $C_1$-$C_6$haloalkyl, $C_1$-$C_6$alkoxy, $C_3$-$C_{10}$cycloalkyl, 3-10 membered heterocyclyl, $C_6$-$C_{14}$aryl and 5-10 membered heteroaryl; wherein $R^{13a}$ may be optionally substituted by one, two or three substituents each selected from $R^h$; $R^{13b}$ is selected from the group consisting of $C_1$-$C_6$alkyl-(3-10 membered heterocyclyl), $C_1$-$C_6$alkyl-(5-10 membered heteroaryl), $C_1$-$C_6$alkyl-($C_6$-$C_{14}$aryl), $C_1$-$C_6$haloalkyl, $C_3$-$C_{10}$cycloalkyl, $C_6$-$C_{14}$aryl, 3-10 membered heterocyclyl and 5-10 membered heteroaryl; $R^{13e}$ is independently selected, for each occurrence, from the group consisting of hydrogen, halogen, $C_1$-$C_6$alkyl, $C_1$-$C_6$haloalkyl, $C_3$-$C_{10}$cycloalkyl, and $C_1$-$C_6$alkoxy; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, hydroxyl, 3-10 membered heterocyclyl, $C_6$-$C_{14}$aryl, and 5-10 membered heteroaryl; or $R^e$ and $R^f$ may form, together with the nitrogen to which they are attached, a 4-6 membered heterocycle; $R^h$ is independently selected, for each occurrence, from the group consisting of halogen, $C_1$-$C_6$alkyl, $C_1$-$C_6$haloalky, and $C_1$-$C_6$alkoxy; ⎓ denotes a bond that may be a single or double bond; and s is selected from 1 and 2. It can be appreciated that the warhead, in this and other certain embodiments, may be either a reversible or an irreversible warhead.

In some embodiments, $R^8$ is the warhead. It can be appreciated that the warhead, in this and other certain embodiments, may be a reversible warhead.

In some embodiments, $R^8$ is the warhead selected from the group consisting of:

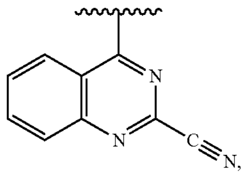 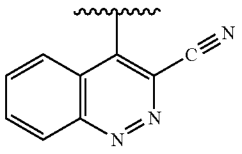,

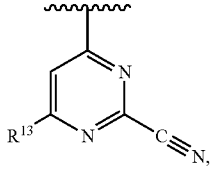 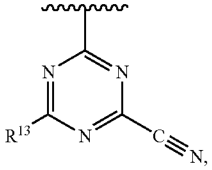

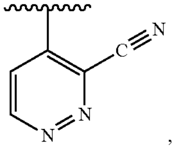, 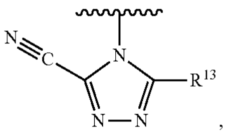,

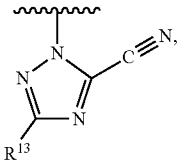 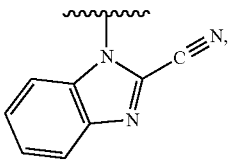

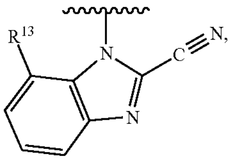 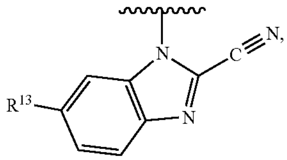

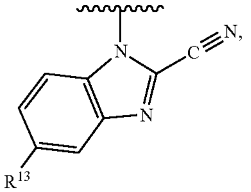 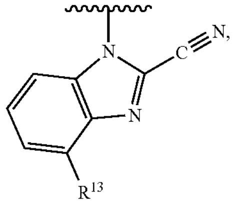

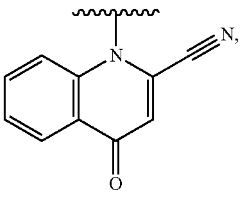 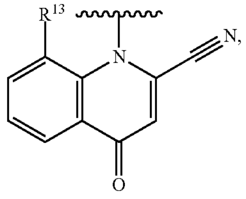

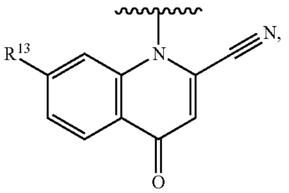

-continued

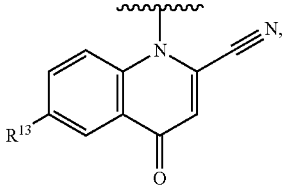

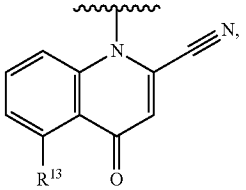

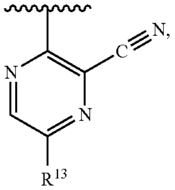

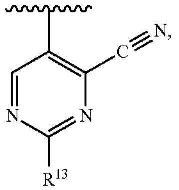

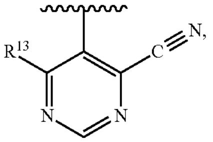

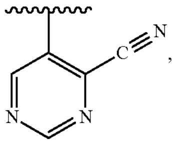,

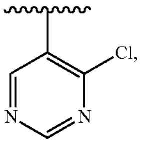

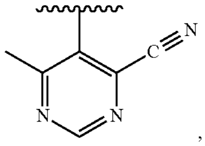,

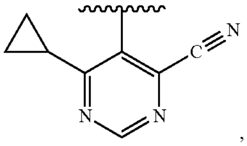, and

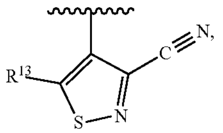

wherein $R^{13}$ is selected from the group consisting of halogen, phenyl, cyano, —$N(R^eR^f)$, —$N(R^e)$—C(O)—$(R^f)$, $C_1$-$C_6$alkyl, $C_1$-$C_6$haloalkyl, $C_1$-$C_6$alkoxy, $C_3$-$C_{10}$cycloalkyl, 3-10 membered heterocyclyl, $C_6$-$C_{14}$aryl and 5-10 membered heteroaryl; wherein $R^{13}$ may be optionally substituted by one, two or three substituents each selected from $R^h$; and $R^h$ is independently selected, for each occurrence, from the group consisting of halogen, $C_1$-$C_6$alkyl, $C_1$-$C_6$haloalky, and $C_1$-$C_6$alkoxy.

In certain embodiments, $R^8$ is

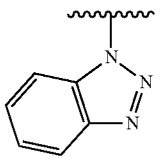 or 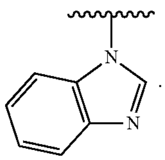.

In certain embodiments, Q is NH. In embodiments, Q is $CH_2$.

In embodiments, $R^9$ is the warhead. It can be appreciated that the warhead, in this and other certain embodiments, may be a reversible warhead.

In some embodiments, $R^9$ is a warhead selected from the group consisting of:

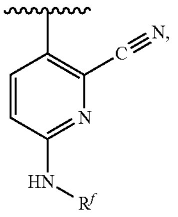

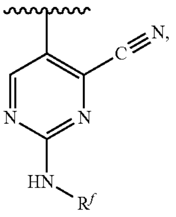 and

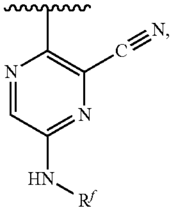

wherein $R^f$ is selected from the group consisting of hydrogen and $C_1$-$C_6$alkyl; wherein $C_1$-$C_6$alkyl may optionally be substituted by one or more substituents selected from the group consisting of halogen, cyano, oxo, and hydroxyl.

In some embodiments, $R^9$ is

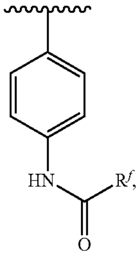

wherein $R^f$ is selected from the group consisting of hydrogen and $C_1$-$C_6$alkyl; wherein $C_1$-$C_6$alkyl may optionally be substituted by one or more substituents selected from the group consisting of halogen, cyano, oxo, and hydroxyl.

In some embodiments, $R^f$ is hydrogen or methyl.

In embodiments, $R^{10}$ is selected from the group consisting of:

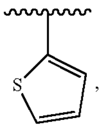,

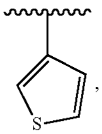,

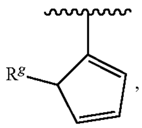,

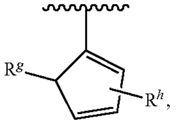

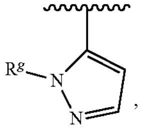,

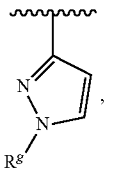, and

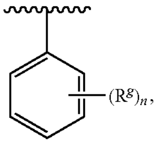

wherein $R^g$, for each occurrence, is selected from the group consisting of halogen, —$NO_2$, $C_1$-$C_5$alkyl, $C_1$-$C_5$alkoxy, $C_1$-$C_5$alkoxy-N($R^eR^f$), —N($R^eR^f$), phenyl, and 5-6 membered heteroaryl, wherein the phenyl or heteroaryl may have one, two or three optional substituents each selected from $R^h$; and $R^h$, for each occurrence, is selected from the group consisting of halogen, $C_1$-$C_5$alkyl, $C_1$-$C_6$haloalkyl, and $C_1$-$C_5$alkoxy.

In embodiments, $R^{10}$ is selected from the group consisting of:

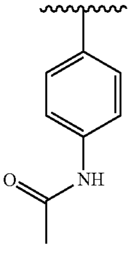
,
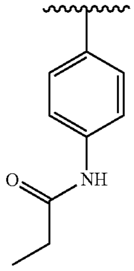
,
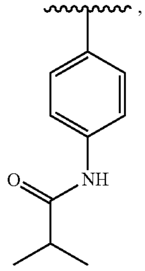
,
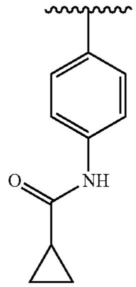
,
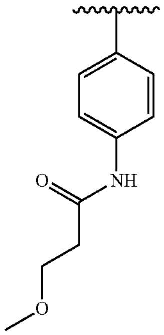
,
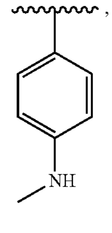
,
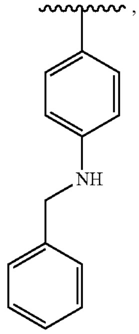
,
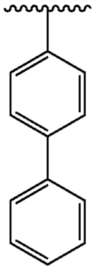
,
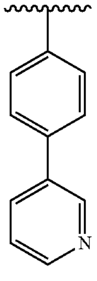
,
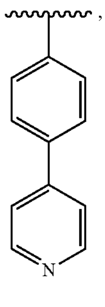
, and
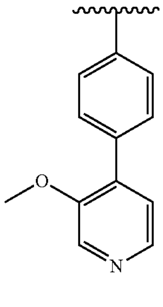
, In certain embodiments, $R^1$ is H. In certain embodiments, $R^{11}$ is selected from the group consisting of:

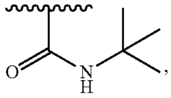
,
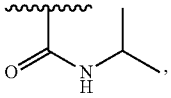
,

-continued

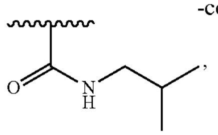
, and
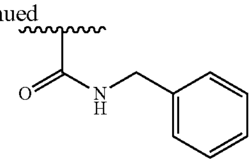
,

In an embodiment, provided herein are compounds represented by Formula III:

Formula III

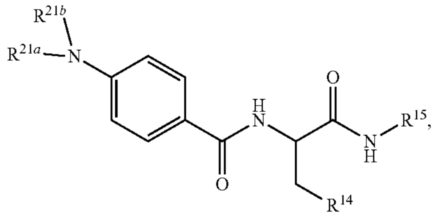

wherein: $R^{14}$ is a phenyl or 5-10 membered heteroaryl optionally substituted by one, two or three substituents each selected from $R^i$, or $R^{14}$ is a warhead; $R^i$, for each occurrence, is selected from the group consisting of halogen, —$NH_2$, and $C_1$-$C_5$alkyl; $R^{15}$ is selected from 5-6 membered heteroaryl and phenyl, wherein $R^{15}$ may optionally be substituted by one, two or three substituents each selected from R', or $R^{15}$ is a warhead; R', for each occurrence, is selected from the group consisting of halogen, —$NO_2$, $C_1$-$C_5$alkyl, $C_1$-$C_5$alkoxy, and 5-6 membered heteroaryl containing one, two three, or four nitrogen; $R^{21a}$ and $R^{21b}$ are each independently hydrogen or $C_1$-$C_5$alkyl; or $R^{21a}$ and $R^{21b}$ may form, together with the nitrogen to which they are attached, a 5-10 membered heterocycle; wherein one of $R^{14}$ and $R^{15}$ is a warhead; and pharmaceutically acceptable salts, stereoisomers, esters, and prodrugs thereof.

In some embodiments, the compound of Formula III is represented by

Formula III-A

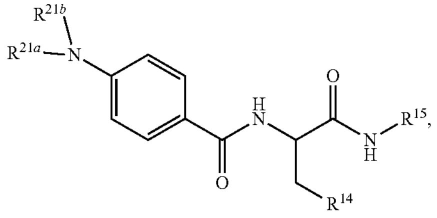

wherein: $R^{14}$ is a phenyl or 5-10 membered heteroaryl optionally substituted by one, two or three substituents each selected from $R^i$, or $R^{14}$ is a warhead; $R^i$, for each occurrence, is selected from the group consisting of halogen, —$NH_2$, and $C_1$-$C_5$alkyl; $R^{15}$ is a phenyl optionally substituted by one, two or three substituents each selected from R', or $R^{15}$ is a warhead; R', for each occurrence, is selected from the group consisting of halogen, —$NO_2$, $C_1$-$C_5$alkyl, $C_1$-$C_5$alkoxy, and 5-6 membered heteroaryl containing one, two three, or four nitrogen; $R^{21a}$ and $R^{21b}$ are each independently hydrogen or $C_1$-$C_5$alkyl; or $R^{21a}$ and $R^{21b}$ may form, together with the nitrogen to which they are attached, a 5-10 membered heterocycle; wherein one of $R^{14}$ and $R^{15}$ is a warhead; and pharmaceutically acceptable salts, stereoisomers, esters, and prodrugs thereof.

In embodiments, the warhead is each independently selected from the group consisting of:

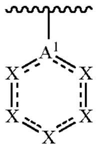 and 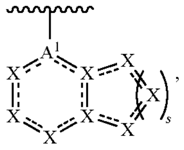

wherein $A^1$ is selected from the group consisting of C, N, CH and C($C_1$-$C_6$alkyl); X is independently selected, for each occurrence, from the group consisting of S, O, C, N, $CR^{13c}$ and $NR^{13c}$; $R^{13c}$ is independently selected, for each occurrence, from the group consisting of hydrogen, cyano, halogen, hydroxyl, oxo, —$SR^{13e}$, —$S(R^{13e})_5$, —$S(O)R^{13e}$, —$S(O)_2R^{13e}$, and $R^{13a}$, as valency permits; $R^{13a}$ is selected from the group consisting of —$OR^{13b}$, —$N(R^eR^f)$, —$N(R^e)$—C(O)—$(R^f)$, $C_1$-$C_6$alkyl, $C_1$-$C_6$haloalkyl, $C_1$-$C_6$alkoxy, $C_3$-$C_{10}$cycloalkyl, 3-10 membered heterocyclyl, $C_6$-$C_{14}$aryl and 5-10 membered heteroaryl; wherein $R^{13a}$ may be optionally substituted by one, two or three substituents each selected from $R^h$; $R^{13b}$ is selected from the group consisting of $C_1$-$C_6$alkyl-(3-10 membered heterocyclyl), $C_1$-$C_6$alkyl-(5-10 membered heteroaryl), $C_1$-$C_6$alkyl-($C_6$-$C_{14}$aryl), $C_1$-$C_6$haloalkyl, $C_3$-$C_{10}$cycloalkyl, $C_6$-$C_{14}$aryl, 3-10 membered heterocyclyl and 5-10 membered heteroaryl; $R^{13o}$ is independently selected, for each occurrence, from the group consisting of hydrogen, halogen, $C_1$-$C_6$alkyl, $C_1$-$C_6$haloalkyl, $C_3$-$C_{10}$cycloalkyl, and $C_1$-$C_6$alkoxy; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, hydroxyl, 3-10 membered heterocyclyl, $C_6$-$C_{14}$aryl, and 5-10 membered heteroaryl; or $R^e$ and $R^f$ may form, together with the nitrogen to which they are attached, a 4-6 membered heterocycle; $R^h$ is independently selected, for each occurrence, from the group consisting of halogen, $C_1$-$C_6$alkyl, $C_1$-$C_6$haloalky, and $C_1$-$C_6$alkoxy; ═ denotes a bond that may be a single or double bond; and s is selected from 1 and 2. It can be appreciated that the warhead, in this and other certain embodiments, may be either a reversible or an irreversible warhead.

In some embodiments, $R^{14}$ is the warhead. It can be appreciated that the warhead, in this and other certain embodiments, may be a reversible warhead.

In some embodiments, $R^{14}$ is the warhead selected from the group consisting of:

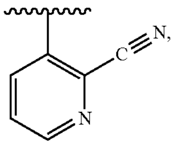 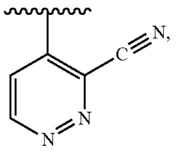

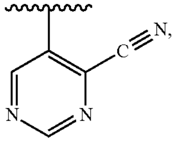 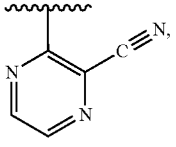

-continued

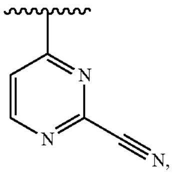 and 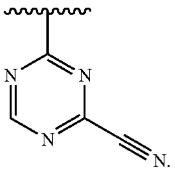

In embodiments, $R^{14}$ is phenyl.

In some embodiments, $R^{15}$ is the warhead. It can be appreciated that the warhead, in this and other certain embodiments, may be a reversible warhead.

In some embodiments, $R^{15}$ is the warhead selected from the group consisting of:

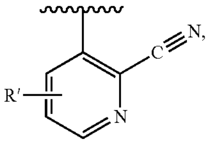 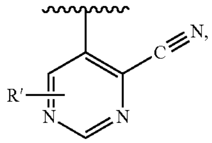 and

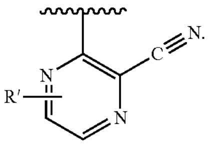

In embodiments, R' is selected from the group consisting of: —Cl, —Br, —F, —$CH_3$, —$CF_3$, —$NO_2$,

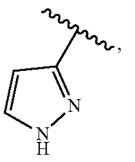 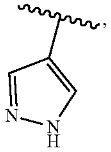 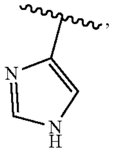 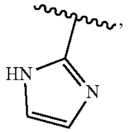

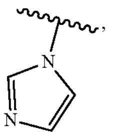 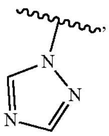 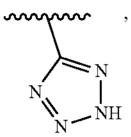 , and

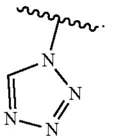

In some embodiments, $R^{15}$ is

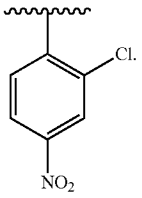 [SMILES: *c1ccc([N+](=O)[O-])cc1Cl]

In some embodiments, the compound of Formula III is selected from the group consisting of:

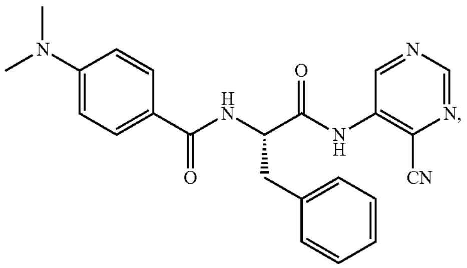

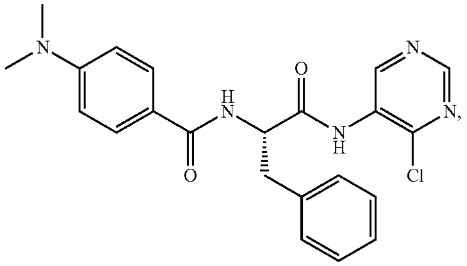

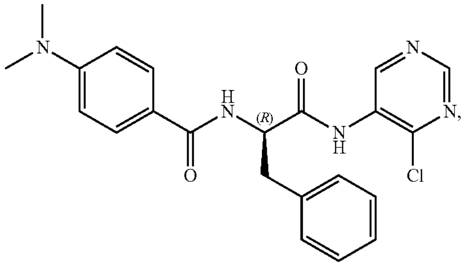

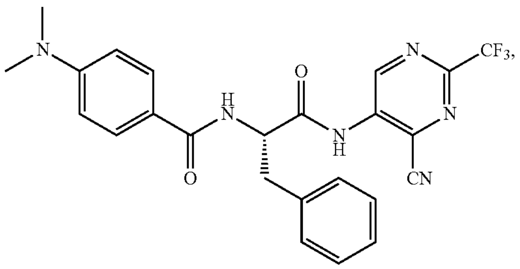

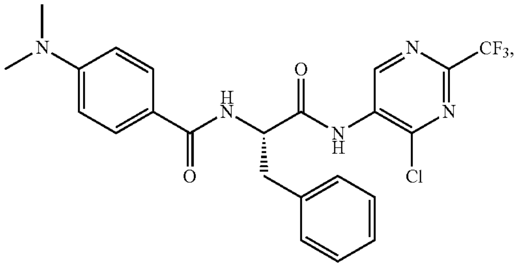

and

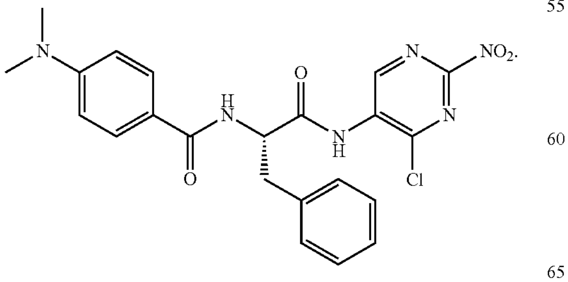

In an embodiment, provided herein are compounds represented by Formula X:

Formula X

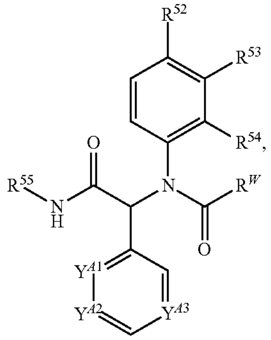

wherein: $Y^{A1}$ is N or $CR^{50}$, wherein $R^{50}$ is selected from the group consisting of H, $CF_3$, halogen, cyano, $C_1$-$C_3$alkoxy, and $C_1$-$C_3$alkyl; $Y^{A2}$ is N or $CR^{51}$, wherein $R^{51}$ is selected from the group consisting of H, halogen, and cyano; $Y^{A3}$ is N or CH; $R^{52}$ is selected from the group consisting of H, $SF_5$, $C_1$-$C_6$alkyl, $C_3$-$C_6$cycloalkyl (optionally substituted by one, two or three $CF_3$), and phenyl; $R^{53}$ is H or halogen; or $R^{52}$ and $R^{53}$ may be joined together to form, together with the carbons to which they are attached, a 5-10 membered heterocycle (optionally substituted by one, two or three $C_1$-$C_6$alkyl); $R^{54}$ is H or halogen; $R^{55}$ is selected from the group consisting of $C_1$-$C_6$alkyl (optionally substituted by one, two or three phenyl), $C_3$-$C_6$cycloalkyl (optionally substituted by one, two or three halogen), 5-8 membered bicyclic heterocycle (optionally substituted by one, two or three methyl), and 5-6 membered heteroaryl (optionally substituted by one, two or three methoxy); $R^w$ is selected from the group consisting of

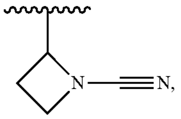

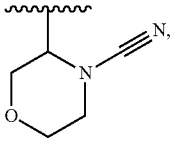

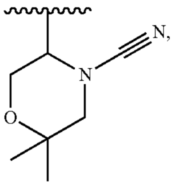

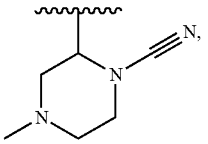

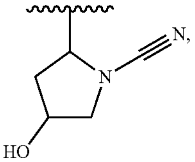

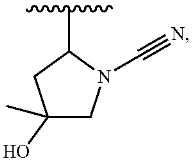

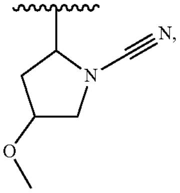

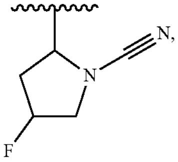

-continued

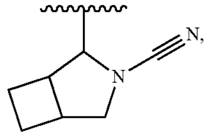
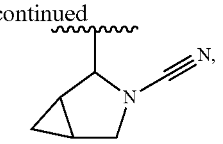
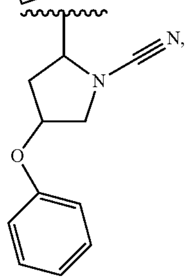
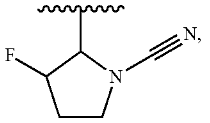
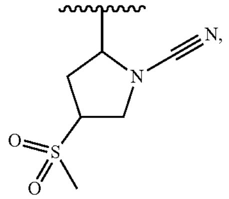
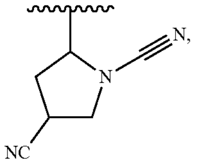
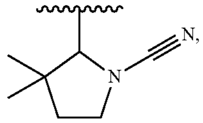
and
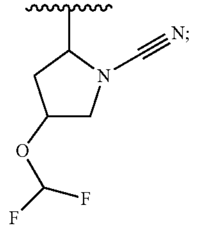

and pharmaceutically acceptable salts, stereoisomers, esters, and prodrugs thereof.

In embodiments, the compound of Formula X is represented by

Formula X-A

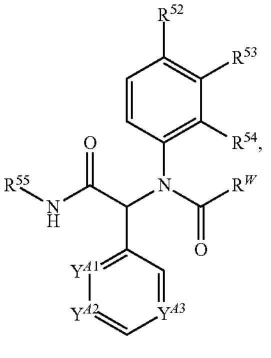

wherein: $Y^{A1}$ is N or $CR^{50}$, wherein $R^{50}$ is selected from the group consisting of H, F, $CF_3$, cyano, methoxy, and methyl; $Y^{A2}$ is N or $CR^{51}$, wherein $R^{51}$ is selected from the group consisting of H, F and cyano; $Y^{A3}$ is N or CH; $R^{52}$ is selected from the group consisting of H, $SF_5$, t-butyl, cyclopropyl (optionally substituted by one, two or three $CF_3$), and phenyl; $R^{53}$ is H or F; or $R^{52}$ and $R^{53}$ may be joined together to form, together with the carbons to which they are attached, a 5-10 membered heterocycle (optionally substituted by one, two or three methyl); $R^{54}$ is H or F; $R^{55}$ is selected from the group consisting of t-butyl, cyclopentyl, cyclohexyl (optionally substituted by one, two or three fluorine), tetrahydropyran (optionally substituted by one, two or three methyl), 8-oxabicyclo[3.2.1]octane, pyridine (optionally substituted by one, two or three methoxy) and ethyl (optionally substituted by one, two or three phenyl); $R^W$ is selected from the group consisting of

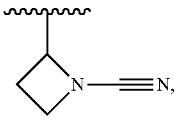
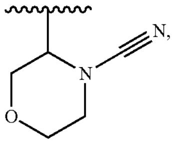
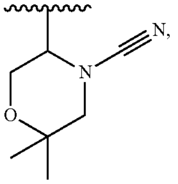
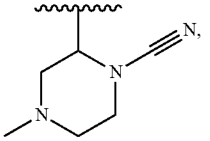
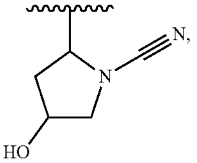
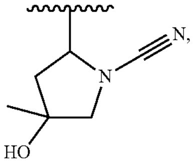
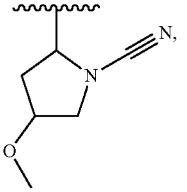
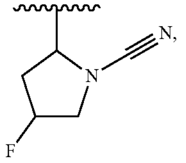
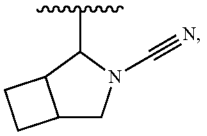
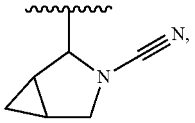
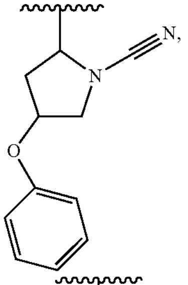
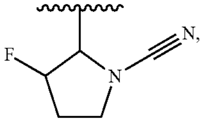
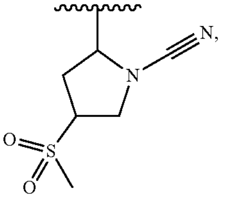
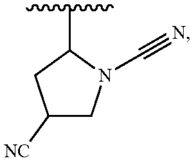
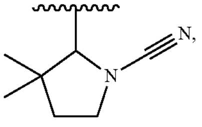
and
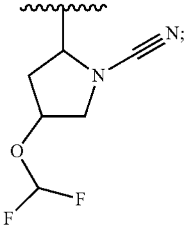

and pharmaceutically acceptable salts, stereoisomers, esters, and prodrugs thereof.
In some embodiments, $R^W$ is selected from the group consisting of:
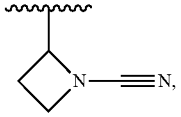
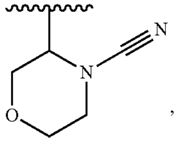
,
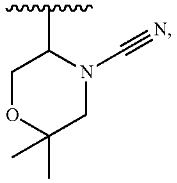
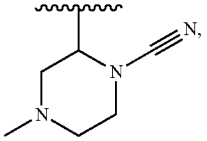
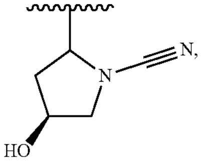
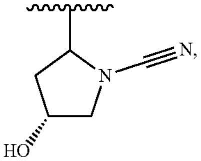
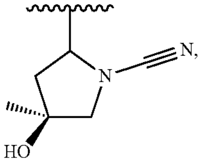
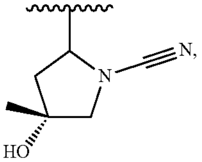
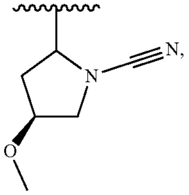
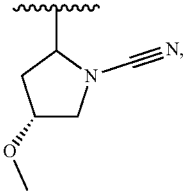
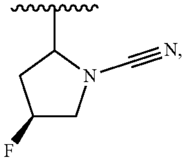
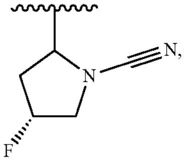
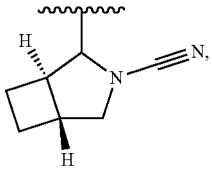
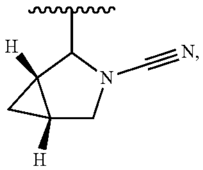
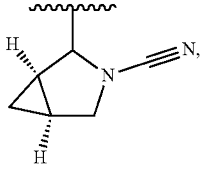
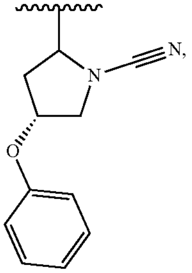
-continued
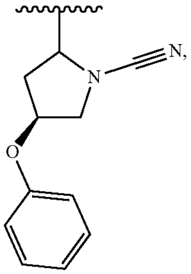
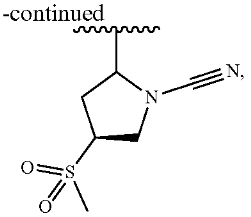
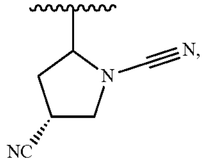
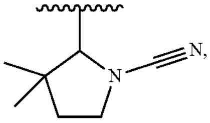
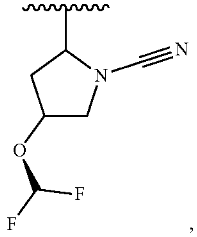
, and
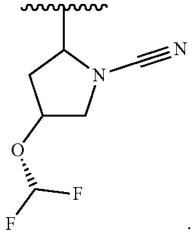
.
In some embodiments, $R^W$ is selected from the group consisting of:
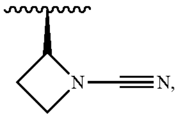
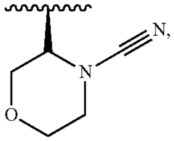
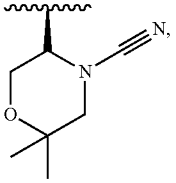
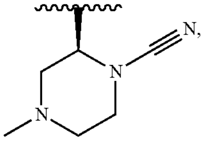
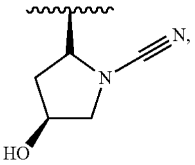
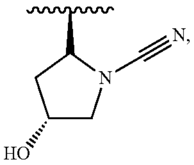
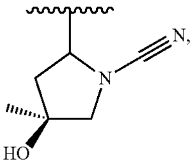
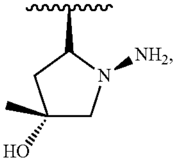
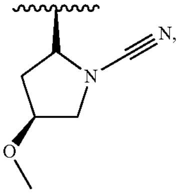
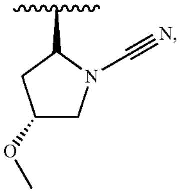

-continued
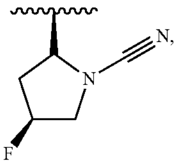
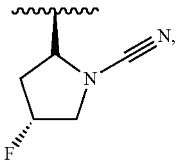
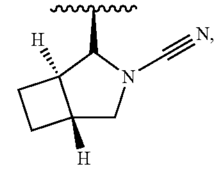
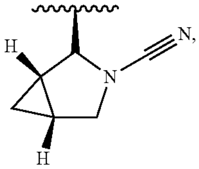
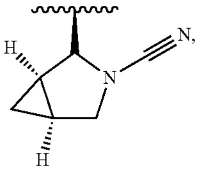
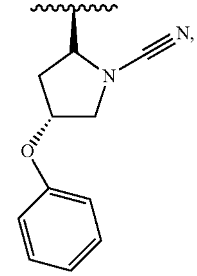
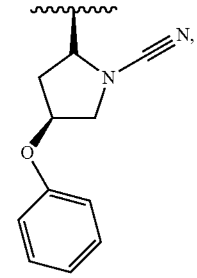
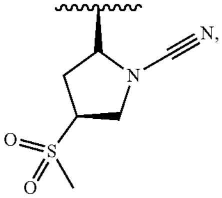
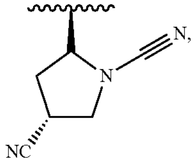
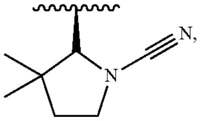
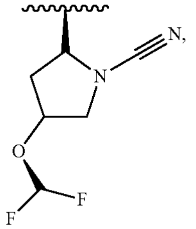
and
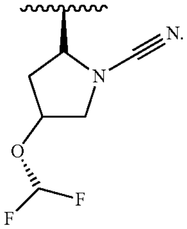
In some embodiments, the compound is selected from the group consisting of:
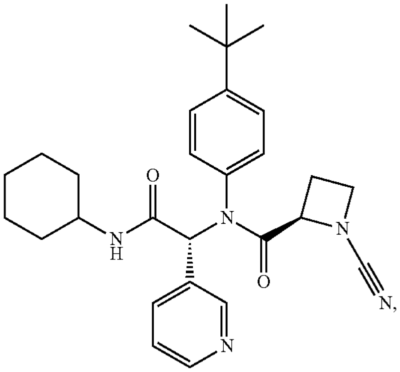
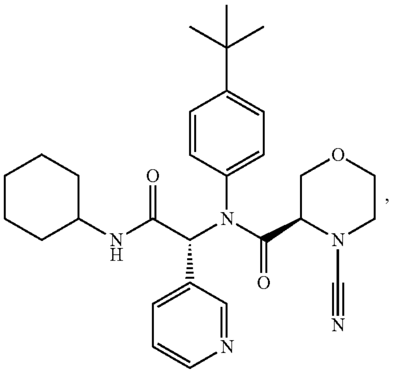
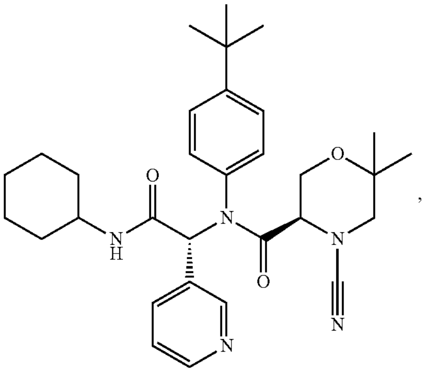
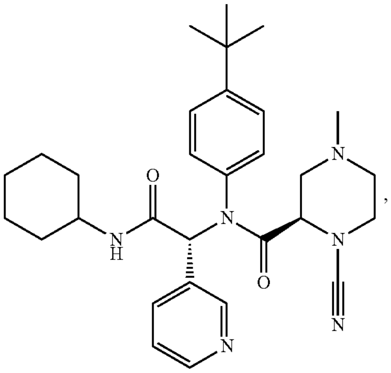

-continued
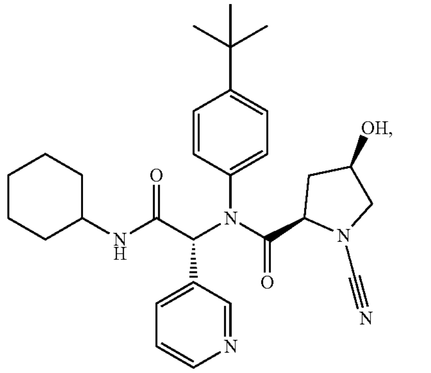
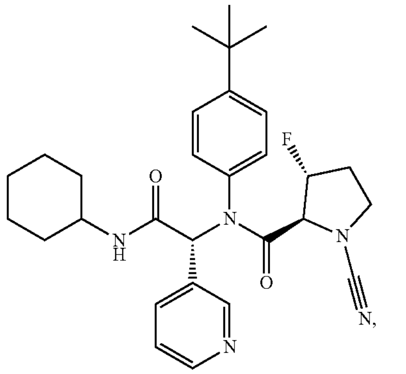
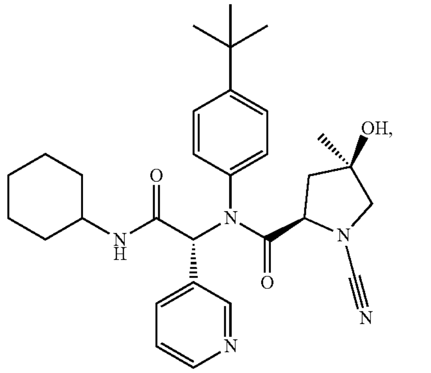
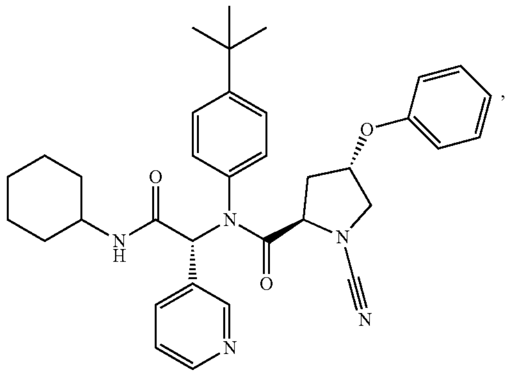
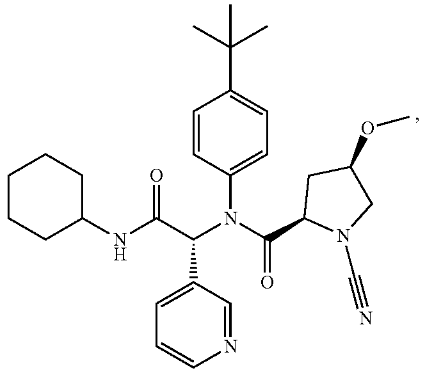
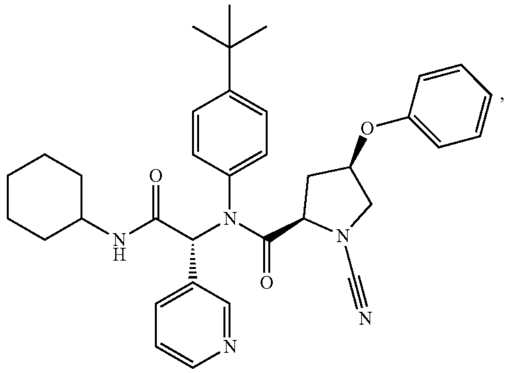
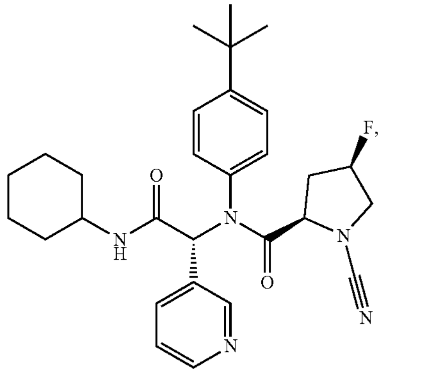
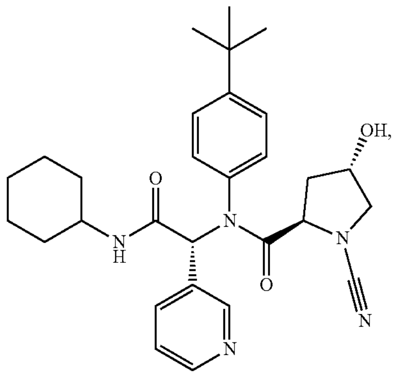

-continued
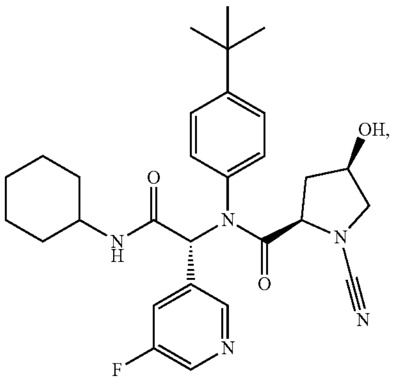
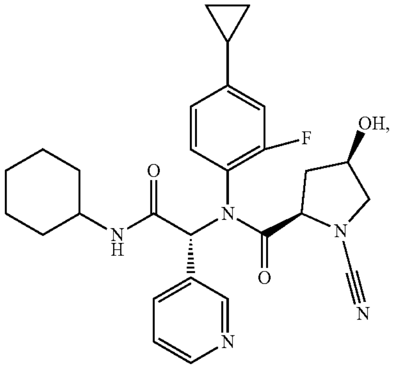
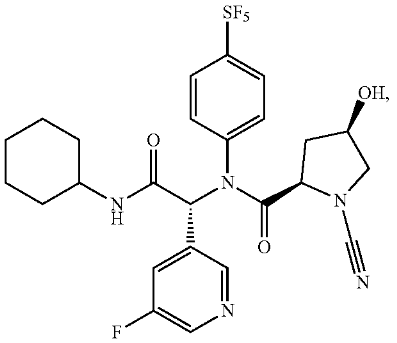
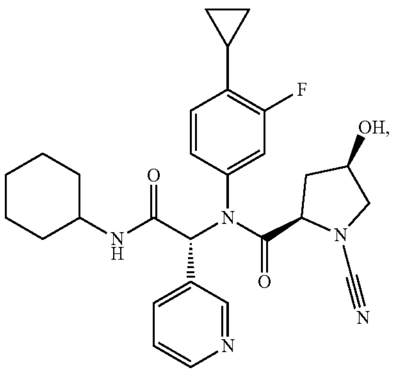
-continued
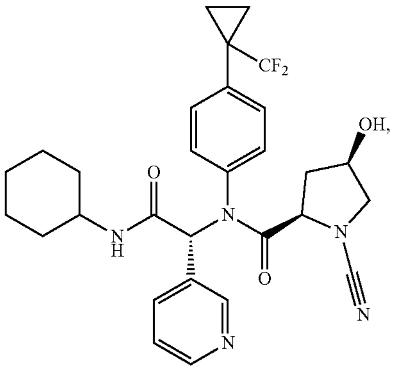
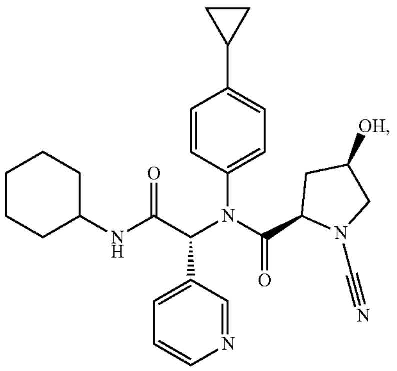
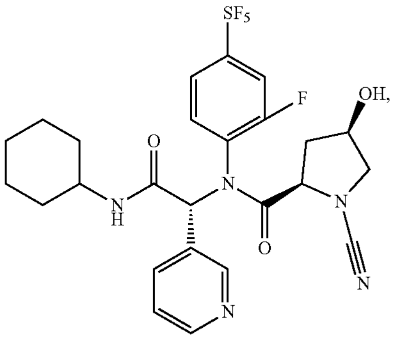
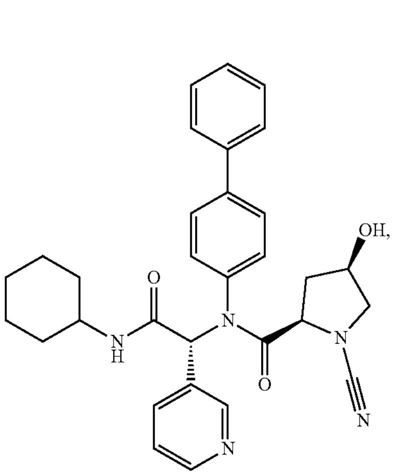

-continued
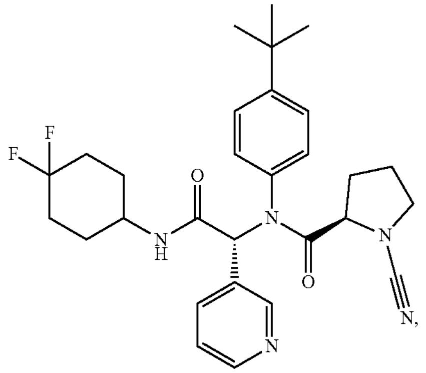
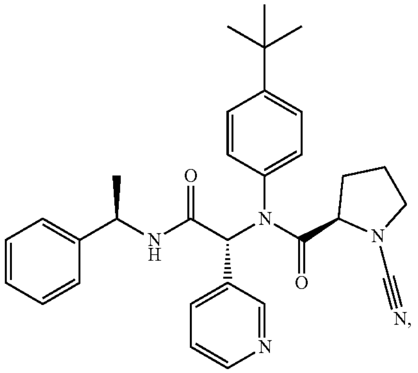
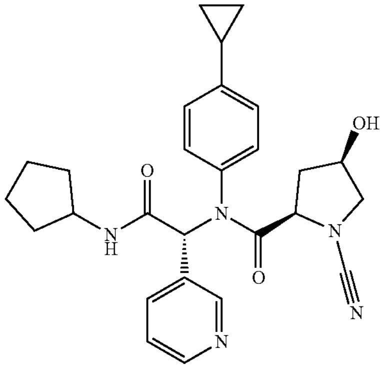
and
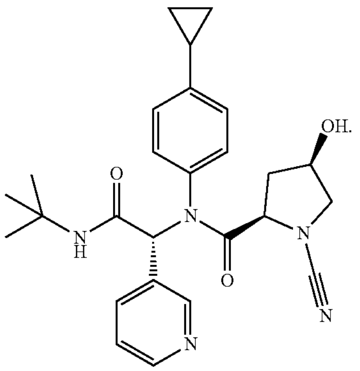
In some embodiments, the compound is selected from the group consisting of
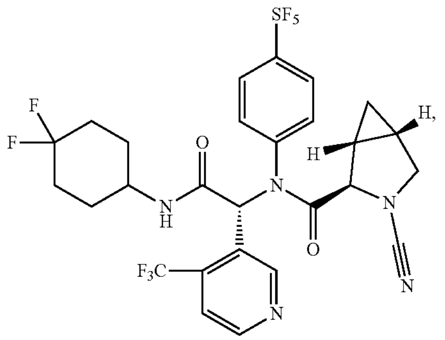
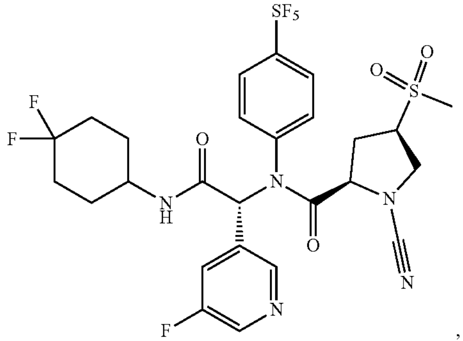
,
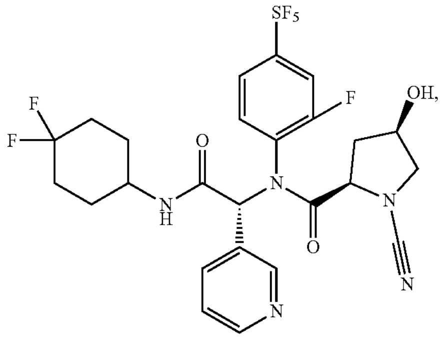
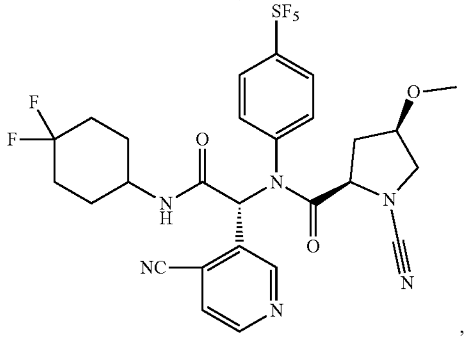
,
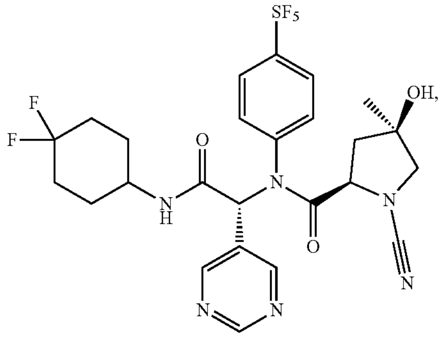

-continued
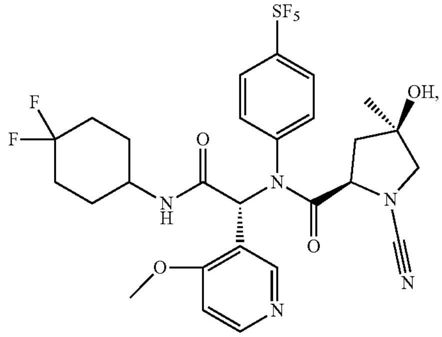
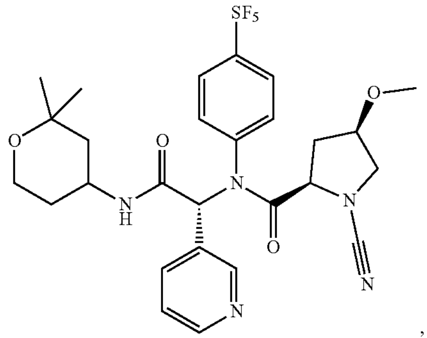
,
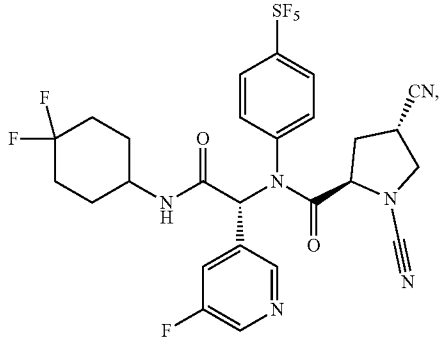
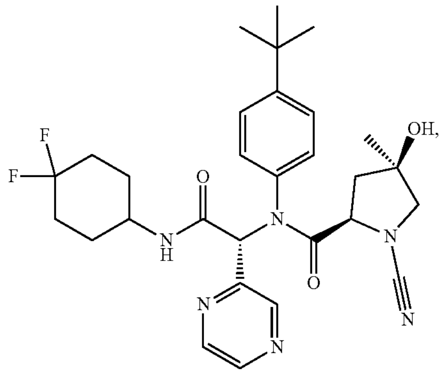
-continued
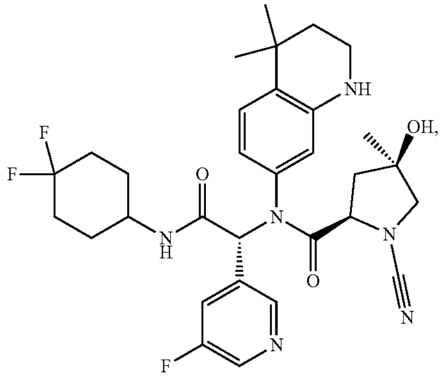
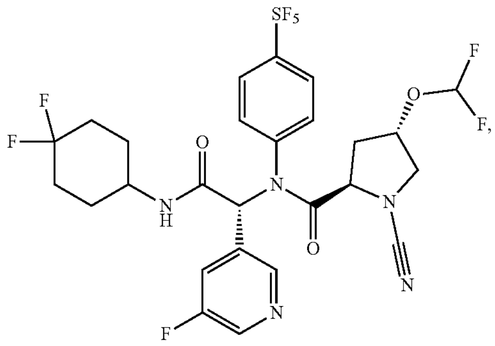
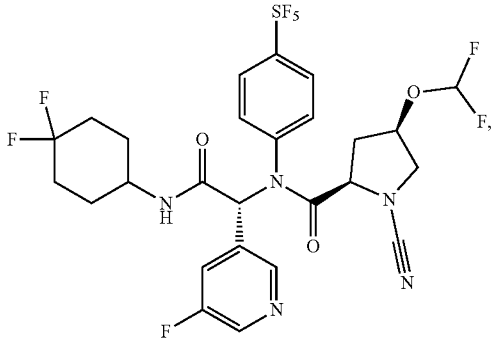
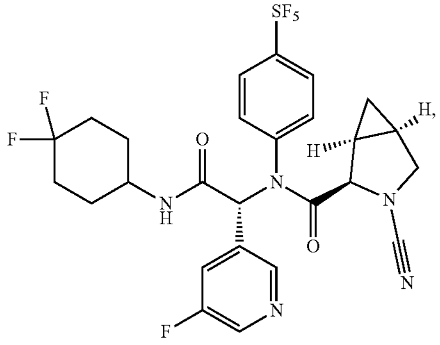

-continued

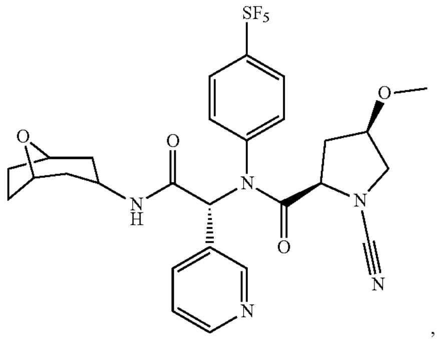

,

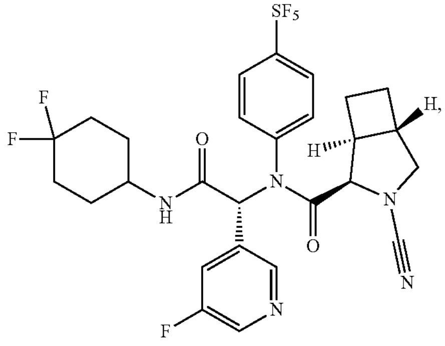

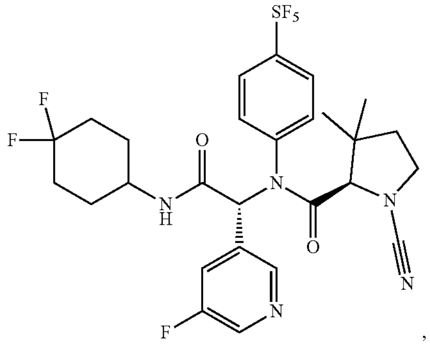

,

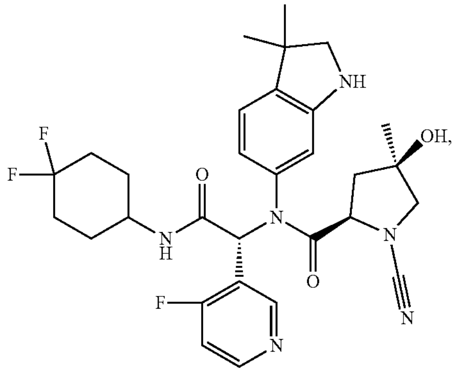

-continued

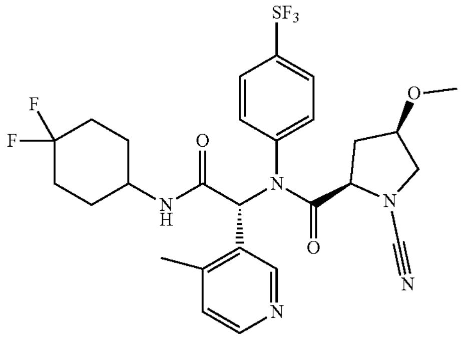

, and

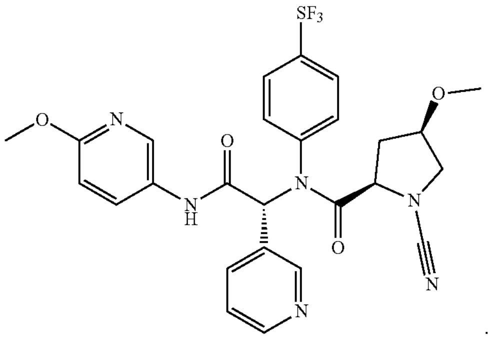

.

In some embodiments, $R^{52}$ is selected from the group consisting of t-butyl, cyclopropyl, cyclopropyl substituted with $CF_3$, $SF_5$, and phenyl. In embodiments, $R^{52}$ and $R^{53}$ are joined together to form, together with the carbons to which they are attached, an indoline substituted with two methyls. $R^{55}$ is selected from the group consisting of cyclohexyl, cyclohexyl substituted with two fluorines, cyclopentyl, ethyl substituted with phenyl, t-butyl, tetrahydropyran substituted with two methyls, 8-oxabicyclo[3.2.1]octane, pyridine and pyridine substituted with methoxy.

In some embodiments, the compound is selected from the group consisting of the compounds identified in Table 1 below:

TABLE 1

| Exemplary compounds. | |
|---|---|
| Cmpd No. | Structure |
| 100 | 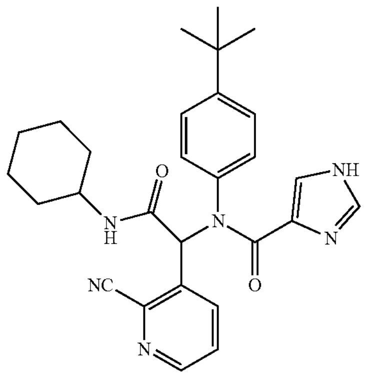 [SMILES: CC(C)(C)c1ccc(N(C(=O)c2c[nH]cn2)C(C(=O)NC2CCCCC2)c2cccnc2C#N)cc1] |

TABLE 1-continued
| Exemplary compounds. | |
|---|---|
| Cmpd No. | Structure |
| 100a | 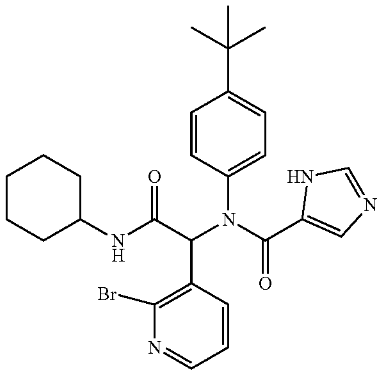 [SMILES: CC(C)(C)c1ccc(N(C(=O)c2cnc[nH]2)C(C(=O)NC2CCCCC2)c2cccnc2Br)cc1] |
| 101 | 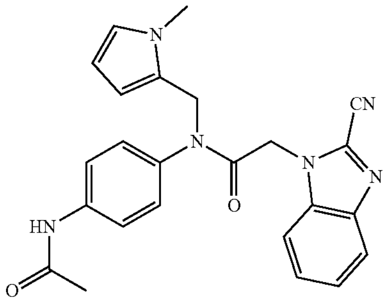 [SMILES: CC(=O)Nc1ccc(N(Cc2cccn2C)C(=O)Cn2c(C#N)nc3ccccc32)cc1] |
| 102 | 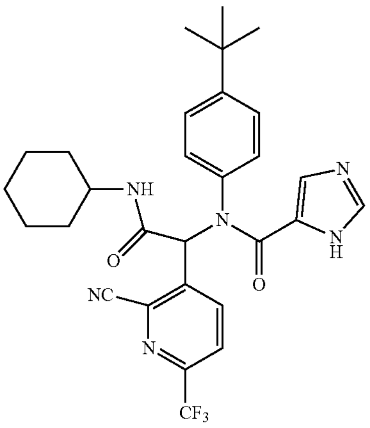 [SMILES: CC(C)(C)c1ccc(N(C(=O)c2cnc[nH]2)C(C(=O)NC2CCCCC2)c2ccc(C(F)(F)F)nc2C#N)cc1] |
TABLE 1-continued
| Exemplary compounds. | |
|---|---|
| Cmpd No. | Structure |
| 102a | 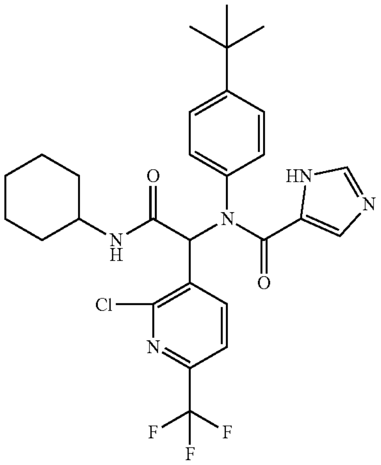 [SMILES: CC(C)(C)c1ccc(N(C(=O)c2cnc[nH]2)C(C(=O)NC2CCCCC2)c2ccc(C(F)(F)F)nc2Cl)cc1] |
| 103 | 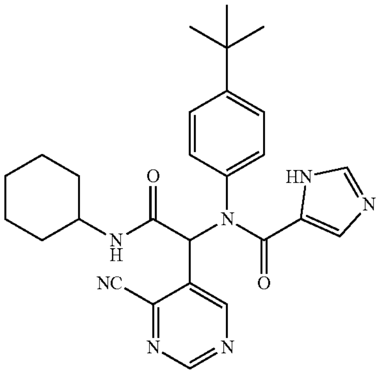 [SMILES: CC(C)(C)c1ccc(N(C(=O)c2cnc[nH]2)C(C(=O)NC2CCCCC2)c2cncnc2C#N)cc1] |
| 104 | 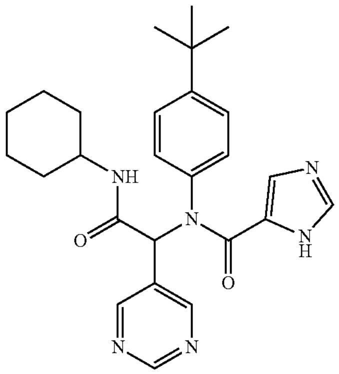 [SMILES: CC(C)(C)c1ccc(N(C(=O)c2cnc[nH]2)C(C(=O)NC2CCCCC2)c2cncnc2)cc1] |

TABLE 1-continued
| Exemplary compounds. | |
|---|---|
| Cmpd No. | Structure |
| 105 | 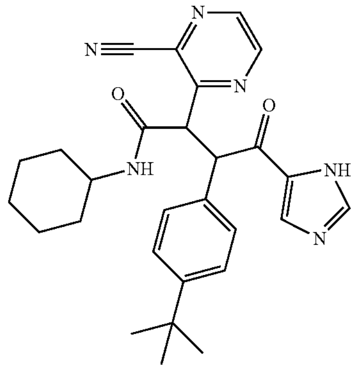 [SMILES: CC(C)(C)c1ccc(C(C(=O)c2cnc[nH]2)C(C(=O)NC2CCCCC2)c2nccnc2C#N)cc1] |
| 105a | 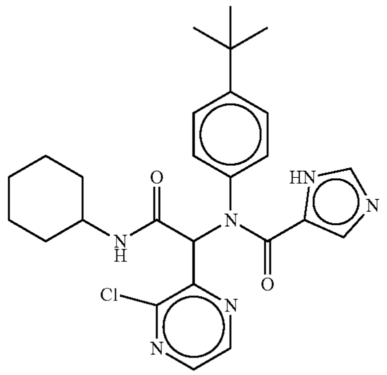 |
| 106 | 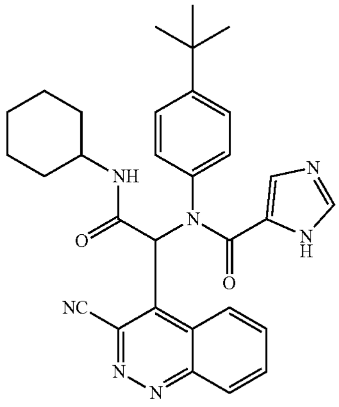 [SMILES: CC(C)(C)c1ccc(N(C(=O)c2cnc[nH]2)C(C(=O)NC2CCCCC2)c2c(C#N)nnc3ccccc23)cc1] |
| 107 | 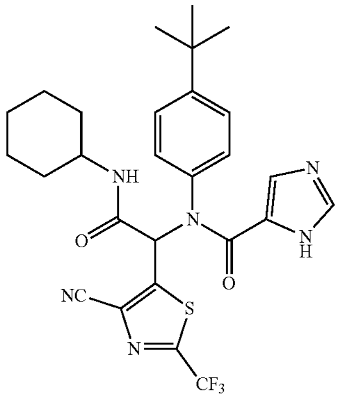 [SMILES: CC(C)(C)c1ccc(N(C(=O)c2cnc[nH]2)C(C(=O)NC2CCCCC2)c2sc(C(F)(F)F)nc2C#N)cc1] |
TABLE 1-continued
| Exemplary compounds. | |
|---|---|
| Cmpd No. | Structure |
| 108 | 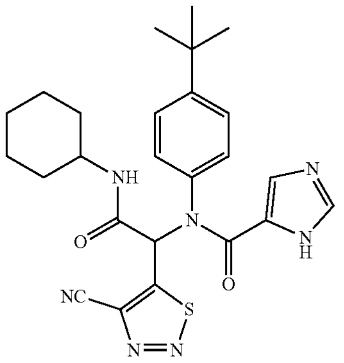 [SMILES: CC(C)(C)c1ccc(N(C(=O)c2cnc[nH]2)C(C(=O)NC2CCCCC2)c2snnc2C#N)cc1] |
| 109 | 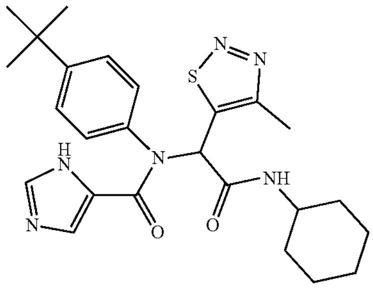 [SMILES: Cc1nnsc1C(C(=O)NC1CCCCC1)N(C(=O)c1cnc[nH]1)c1ccc(C(C)(C)C)cc1] |
| 110 | 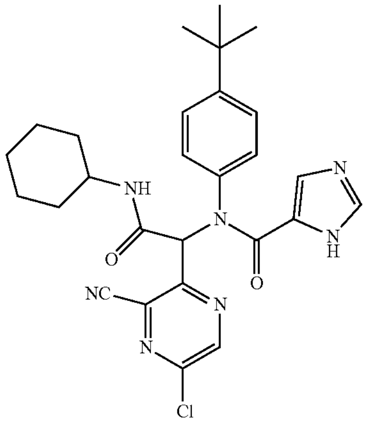 [SMILES: CC(C)(C)c1ccc(N(C(=O)c2cnc[nH]2)C(C(=O)NC2CCCCC2)c2ncc(Cl)nc2C#N)cc1] |
| 111 | 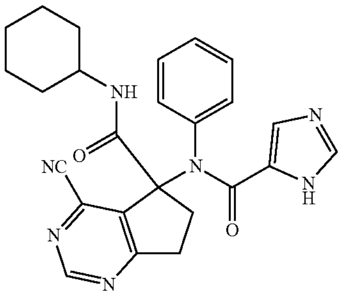 [SMILES: N#Cc1ncnc2c1C(C(=O)NC1CCCCC1)(N(C(=O)c1cnc[nH]1)c1ccccc1)CC2] |

TABLE 1-continued
| Exemplary compounds. | |
|---|---|
| Cmpd No. | Structure |
| 112 | 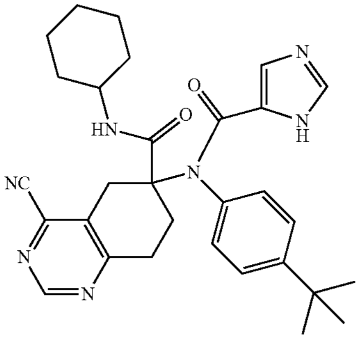 [SMILES: CC(C)(C)c1ccc(N(C(=O)c2cnc[nH]2)C2(C(=O)NC3CCCCC3)CCc3ncnc(C#N)c3C2)cc1] |
| 113 | 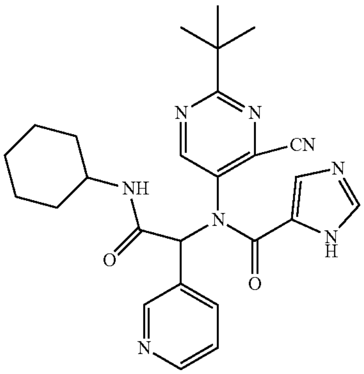 [SMILES: CC(C)(C)c1ncc(N(C(=O)c2cnc[nH]2)C(C(=O)NC2CCCCC2)c2cccnc2)c(C#N)n1] |
| 114 | 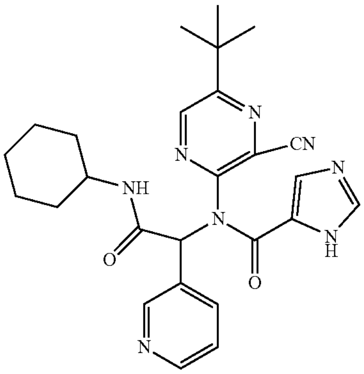 [SMILES: CC(C)(C)c1cnc(N(C(=O)c2cnc[nH]2)C(C(=O)NC2CCCCC2)c2cccnc2)c(C#N)n1] |
| 115 | 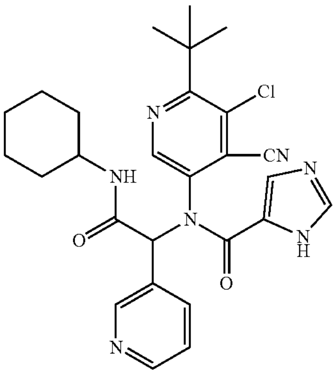 [SMILES: CC(C)(C)c1ncc(N(C(=O)c2cnc[nH]2)C(C(=O)NC2CCCCC2)c2cccnc2)c(C#N)c1Cl] |
| 116 | 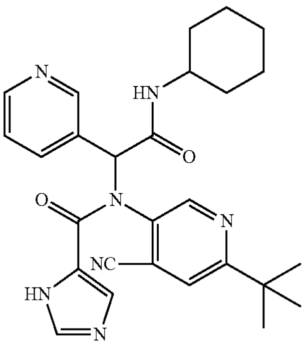 [SMILES: CC(C)(C)c1cc(C#N)c(N(C(=O)c2cnc[nH]2)C(C(=O)NC2CCCCC2)c2cccnc2)cn1] |
| 117 | 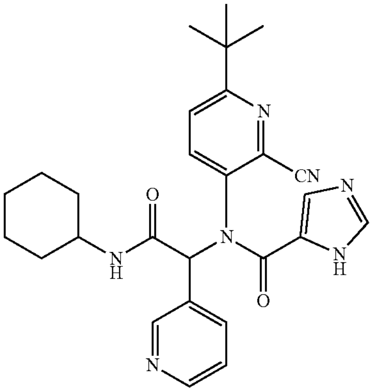 [SMILES: CC(C)(C)c1ccc(N(C(=O)c2cnc[nH]2)C(C(=O)NC2CCCCC2)c2cccnc2)c(C#N)n1] |
| 118 | 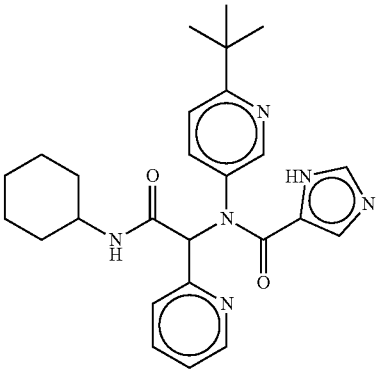 |
| 119 | 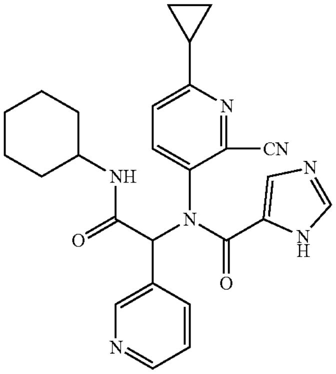 [SMILES: N#Cc1nc(C2CC2)ccc1N(C(=O)c1cnc[nH]1)C(C(=O)NC1CCCCC1)c1cccnc1] |

TABLE 1-continued
| Exemplary compounds. | |
|---|---|
| Cmpd No. | Structure |
| 120 | 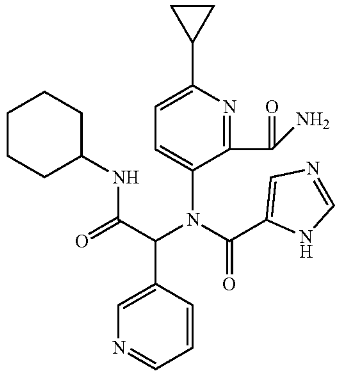 [SMILES: NC(=O)c1nc(C2CC2)ccc1N(C(=O)c1cnc[nH]1)C(C(=O)NC1CCCCC1)c1cccnc1] |
| 121 | 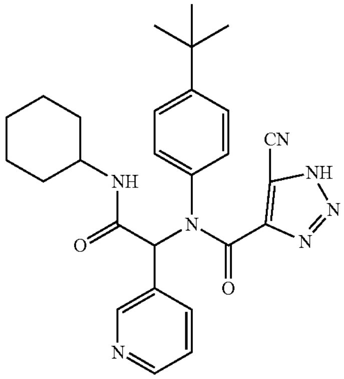 [SMILES: CC(C)(C)c1ccc(N(C(=O)c2nn[nH]c2C#N)C(C(=O)NC2CCCCC2)c2cccnc2)cc1] |
| 122 | 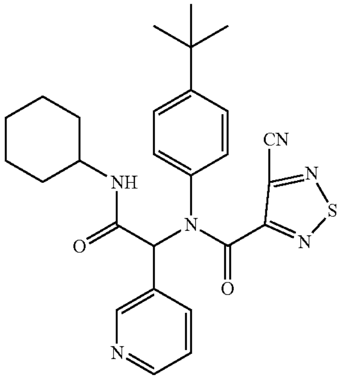 [SMILES: CC(C)(C)c1ccc(N(C(=O)c2nsnc2C#N)C(C(=O)NC2CCCCC2)c2cccnc2)cc1] |
| 123 | 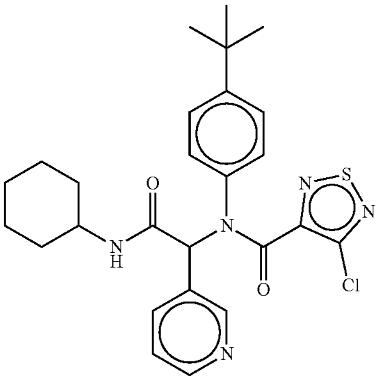 |
TABLE 1-continued
| Exemplary compounds. | |
|---|---|
| Cmpd No. | Structure |
| 123a | 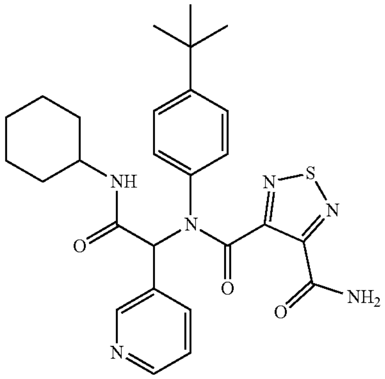 [SMILES: CC(C)(C)c1ccc(N(C(=O)c2nsnc2C(N)=O)C(C(=O)NC2CCCCC2)c2cccnc2)cc1] |
| 124 | 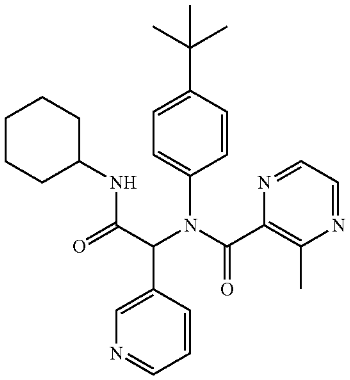 [SMILES: Cc1nccnc1C(=O)N(c1ccc(C(C)(C)C)cc1)C(C(=O)NC1CCCCC1)c1cccnc1] |
| 124a | 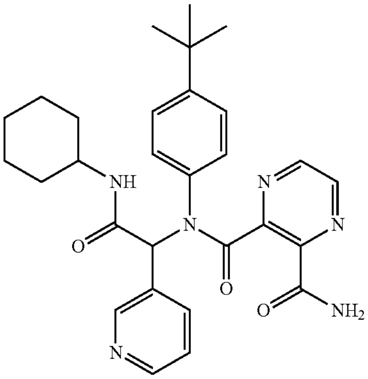 [SMILES: CC(C)(C)c1ccc(N(C(=O)c2nccnc2C(N)=O)C(C(=O)NC2CCCCC2)c2cccnc2)cc1] |
| 125 | 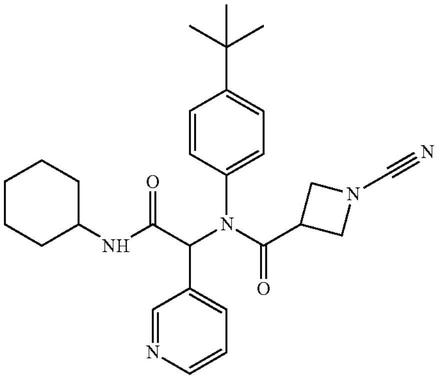 [SMILES: CC(C)(C)c1ccc(N(C(=O)C2CN(C#N)C2)C(C(=O)NC2CCCCC2)c2cccnc2)cc1] |

TABLE 1-continued
Exemplary compounds.
| Cmpd No. | Structure |
|---|---|
| 126 | 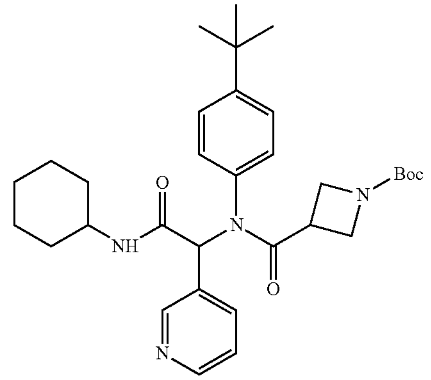 [SMILES: CC(C)(C)OC(=O)N1CC(C(=O)N(c2ccc(C(C)(C)C)cc2)C(C(=O)NC2CCCCC2)c2cccnc2)C1] |
| 127 | 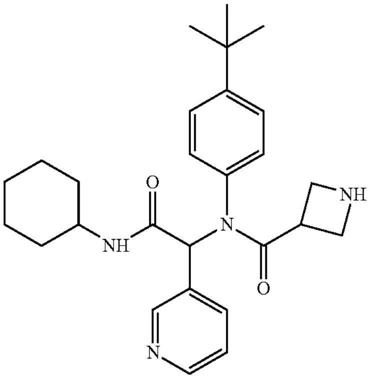 [SMILES: CC(C)(C)c1ccc(N(C(=O)C2CNC2)C(C(=O)NC2CCCCC2)c2cccnc2)cc1] |
| 128 | 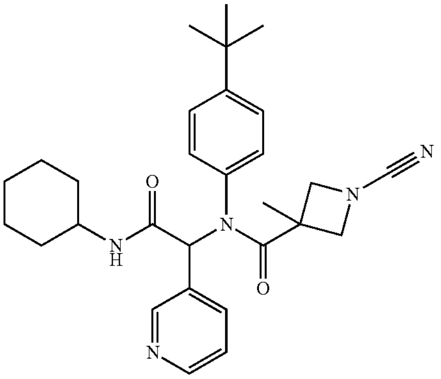 [SMILES: CC1(C(=O)N(c2ccc(C(C)(C)C)cc2)C(C(=O)NC2CCCCC2)c2cccnc2)CN(C#N)C1] |
| 129 | 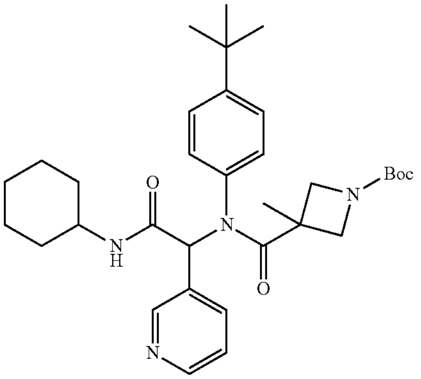 [SMILES: CC(C)(C)OC(=O)N1CC(C)(C(=O)N(c2ccc(C(C)(C)C)cc2)C(C(=O)NC2CCCCC2)c2cccnc2)C1] |
TABLE 1-continued
Exemplary compounds.
| Cmpd No. | Structure |
|---|---|
| 129a | 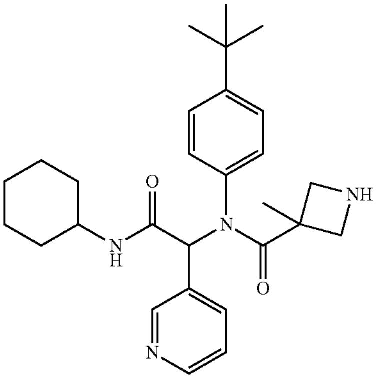 [SMILES: CC1(C(=O)N(c2ccc(C(C)(C)C)cc2)C(C(=O)NC2CCCCC2)c2cccnc2)CNC1] |
| 130 | 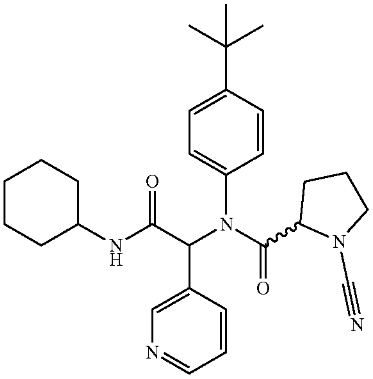 [SMILES: CC(C)(C)c1ccc(N(C(=O)C2CCCN2C#N)C(C(=O)NC2CCCCC2)c2cccnc2)cc1] |
| 130a | 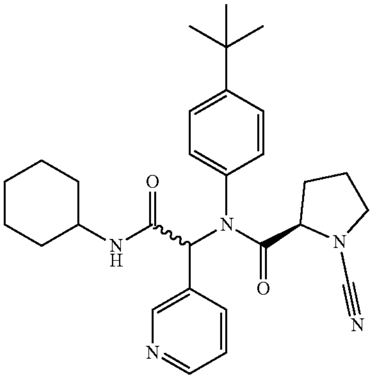 [SMILES: CC(C)(C)c1ccc(N(C(=O)[C@H]2CCCN2C#N)C(C(=O)NC2CCCCC2)c2cccnc2)cc1] |
| 130b | 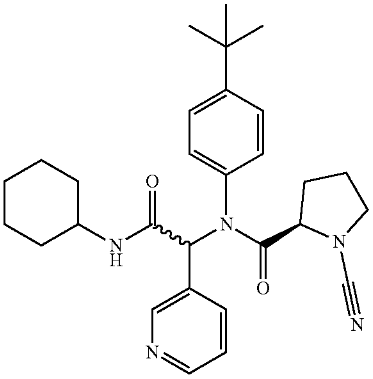 [SMILES: CC(C)(C)c1ccc(N(C(=O)[C@H]2CCCN2C#N)C(C(=O)NC2CCCCC2)c2cccnc2)cc1] |

TABLE 1-continued
Exemplary compounds.
| Cmpd No. | Structure |
|---|---|
| 130c | 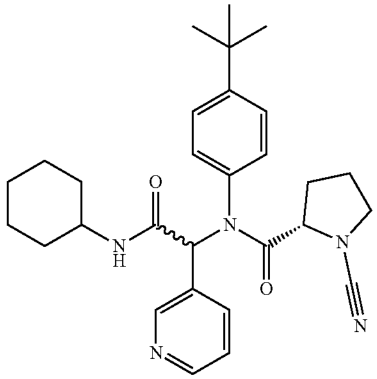 [SMILES: CC(C)(C)c1ccc(N(C(=O)[C@@H]2CCCN2C#N)C(C(=O)NC2CCCCC2)c2cccnc2)cc1] |
| 130d | 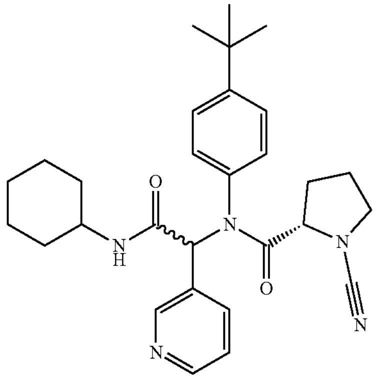 [SMILES: CC(C)(C)c1ccc(N(C(=O)[C@@H]2CCCN2C#N)C(C(=O)NC2CCCCC2)c2cccnc2)cc1] |
| 131 | 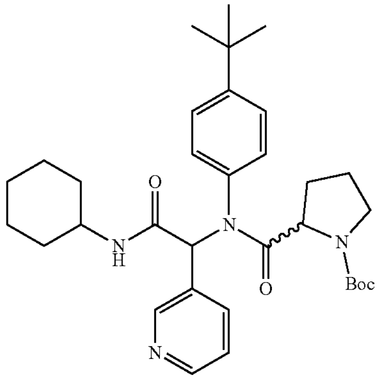 [SMILES: CC(C)(C)OC(=O)N1CCCC1C(=O)N(c1ccc(C(C)(C)C)cc1)C(C(=O)NC1CCCCC1)c1cccnc1] |
| 131a | 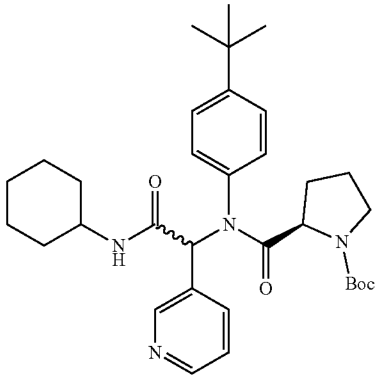 [SMILES: CC(C)(C)OC(=O)N1CCC[C@@H]1C(=O)N(c1ccc(C(C)(C)C)cc1)C(C(=O)NC1CCCCC1)c1cccnc1] |
| 131b | 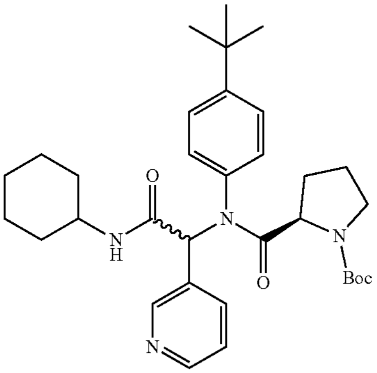 [SMILES: CC(C)(C)OC(=O)N1CCC[C@@H]1C(=O)N(c1ccc(C(C)(C)C)cc1)C(C(=O)NC1CCCCC1)c1cccnc1] |
| 131c | 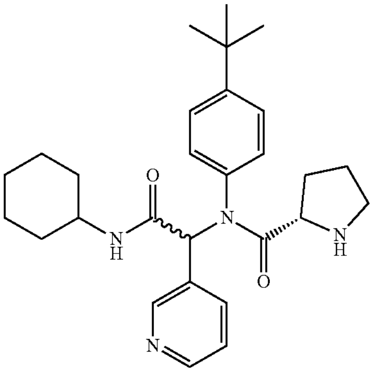 [SMILES: CC(C)(C)c1ccc(N(C(=O)[C@@H]2CCCN2)C(C(=O)NC2CCCCC2)c2cccnc2)cc1] |
| 131d | 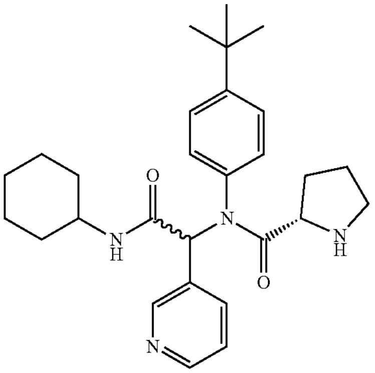 [SMILES: CC(C)(C)c1ccc(N(C(=O)[C@@H]2CCCN2)C(C(=O)NC2CCCCC2)c2cccnc2)cc1] |
| 132 | 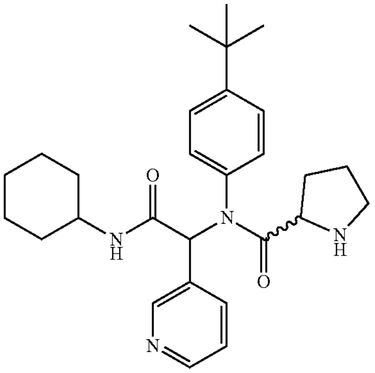 [SMILES: CC(C)(C)c1ccc(N(C(=O)C2CCCN2)C(C(=O)NC2CCCCC2)c2cccnc2)cc1] |

TABLE 1-continued
Exemplary compounds.
| Cmpd No. | Structure |
|---|---|
| 133 | 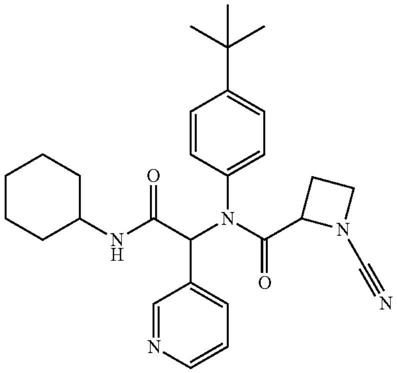 [SMILES: CC(C)(C)c1ccc(N(C(=O)C2CCN2C#N)C(C(=O)NC2CCCCC2)c2cccnc2)cc1] |
| 134 | 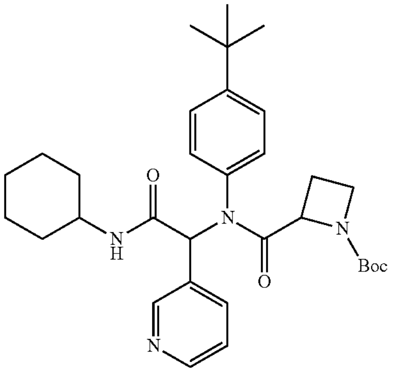 [SMILES: CC(C)(C)OC(=O)N1CCC1C(=O)N(c1ccc(C(C)(C)C)cc1)C(C(=O)NC1CCCCC1)c1cccnc1] |
| 135 | 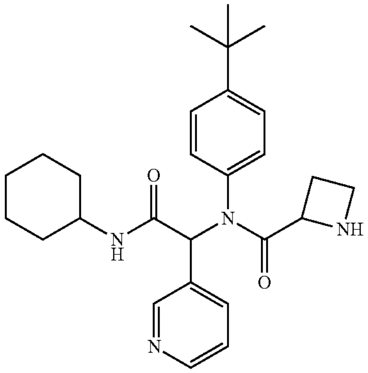 [SMILES: CC(C)(C)c1ccc(N(C(=O)C2CCN2)C(C(=O)NC2CCCCC2)c2cccnc2)cc1] |
| 135a | 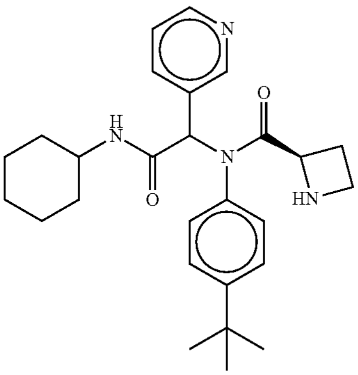 |
TABLE 1-continued
Exemplary compounds.
| Cmpd No. | Structure |
|---|---|
| 136a | 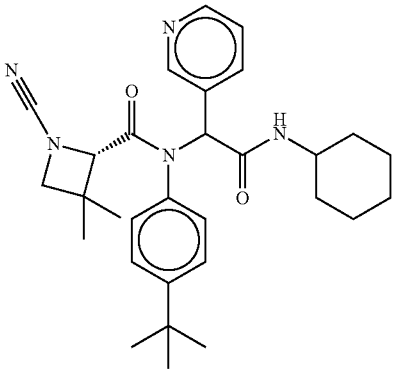 |
| 136 | 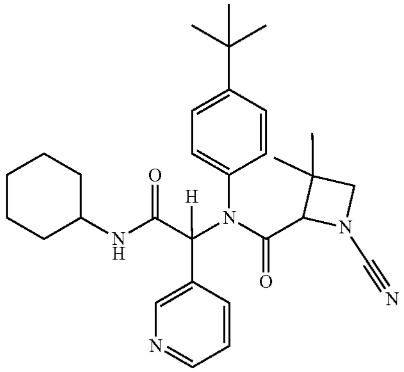 [SMILES: CC(C)(C)c1ccc(N(C(=O)C2N(C#N)CC2(C)C)C(C(=O)NC2CCCCC2)c2cccnc2)cc1] |
| 136b | 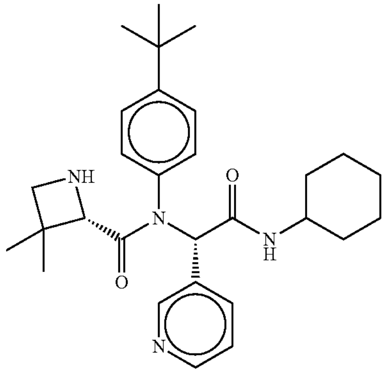 |
| 136c | 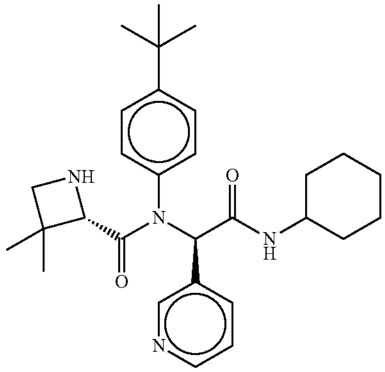 |

TABLE 1-continued
| Exemplary compounds. | |
|---|---|
| Cmpd No. | Structure |
| 137a | 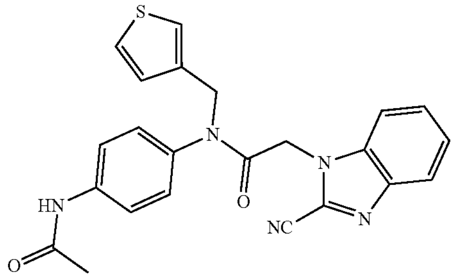 [SMILES: CC(=O)Nc1ccc(N(Cc2ccsc2)C(=O)Cn2c(C#N)nc3ccccc32)cc1] |
| 137b | 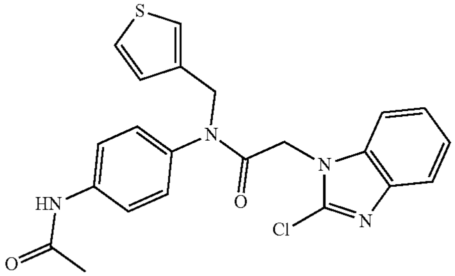 [SMILES: CC(=O)Nc1ccc(N(Cc2ccsc2)C(=O)Cn2c(Cl)nc3ccccc32)cc1] |
| 137c | 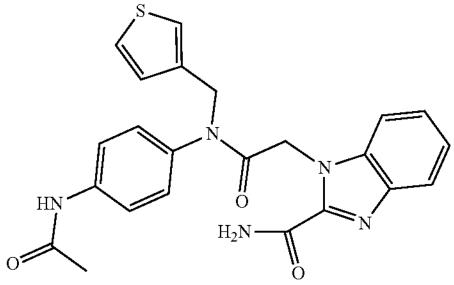 [SMILES: CC(=O)Nc1ccc(N(Cc2ccsc2)C(=O)Cn2c(C(N)=O)nc3ccccc32)cc1] |
| 137 | 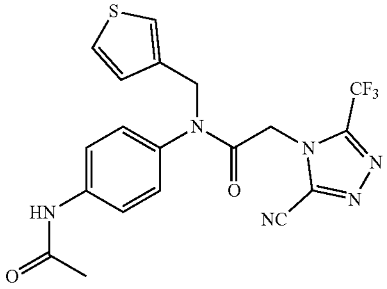 [SMILES: CC(=O)Nc1ccc(N(Cc2ccsc2)C(=O)Cn2c(C#N)nnc2C(F)(F)F)cc1] |
| 137d | 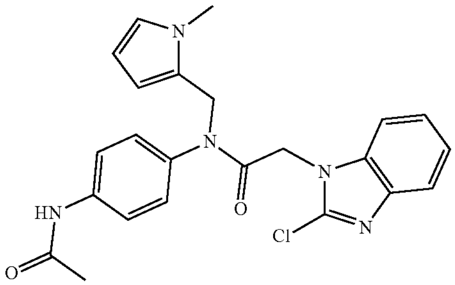 [SMILES: CC(=O)Nc1ccc(N(Cc2cccn2C)C(=O)Cn2c(Cl)nc3ccccc32)cc1] |
TABLE 1-continued
| Exemplary compounds. | |
|---|---|
| Cmpd No. | Structure |
| 137e | 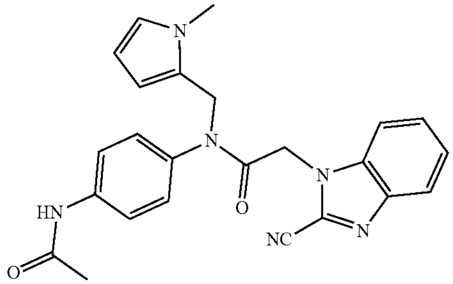 [SMILES: CC(=O)Nc1ccc(N(Cc2cccn2C)C(=O)Cn2c(C#N)nc3ccccc32)cc1] |
| 137f | 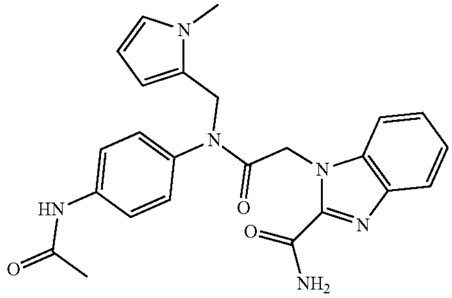 [SMILES: CC(=O)Nc1ccc(N(Cc2cccn2C)C(=O)Cn2c(C(N)=O)nc3ccccc32)cc1] |
| 137g | 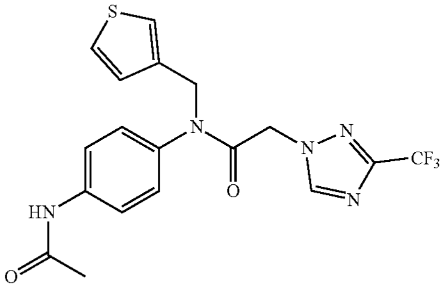 [SMILES: CC(=O)Nc1ccc(N(Cc2ccsc2)C(=O)Cn2cnc(C(F)(F)F)n2)cc1] |
| 138 | 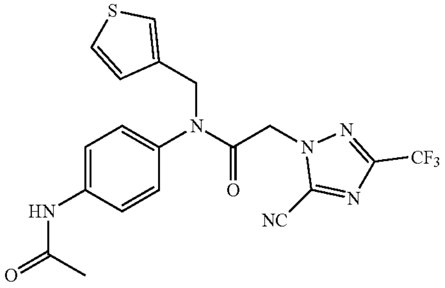 [SMILES: CC(=O)Nc1ccc(N(Cc2ccsc2)C(=O)Cn2nc(C(F)(F)F)nc2C#N)cc1] |
| 139 | 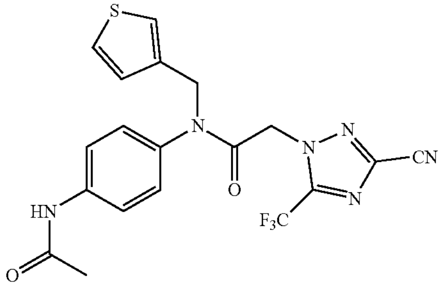 [SMILES: CC(=O)Nc1ccc(N(Cc2ccsc2)C(=O)Cn2nc(C#N)nc2C(F)(F)F)cc1] |

TABLE 1-continued
| Exemplary compounds. | |
|---|---|
| Cmpd No. | Structure |
| 140 | 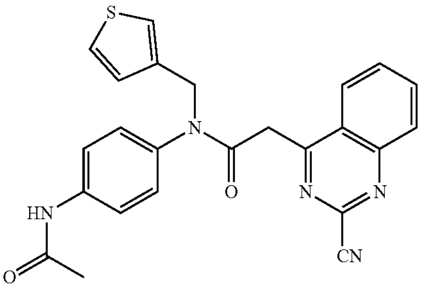 [SMILES: CC(=O)Nc1ccc(N(Cc2ccsc2)C(=O)Cc2nc(C#N)nc3ccccc23)cc1] |
| 140a | 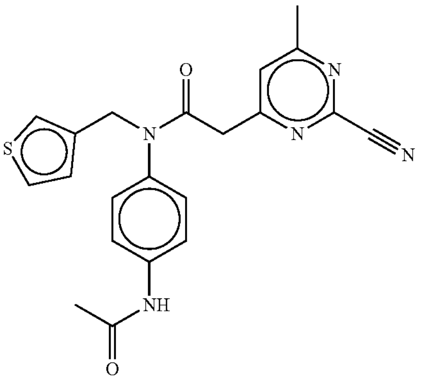 |
| 140b | 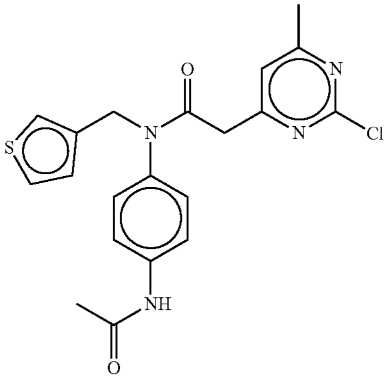 |
| 141 | 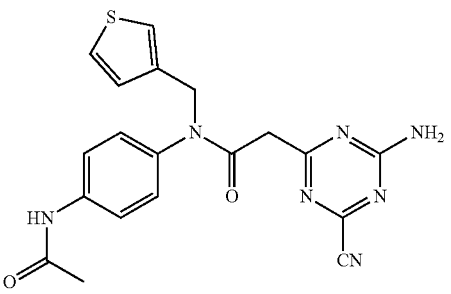 [SMILES: CC(=O)Nc1ccc(N(Cc2ccsc2)C(=O)Cc2nc(N)nc(C#N)n2)cc1] |
| 141a | 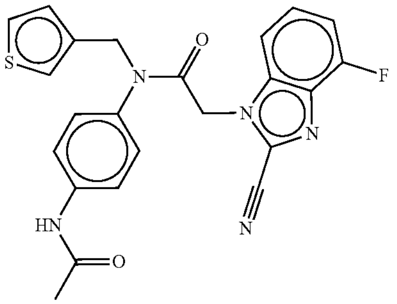 |
| 141b | 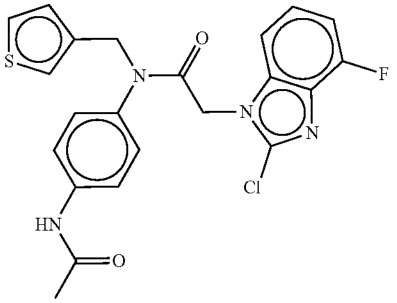 |
| 141c | 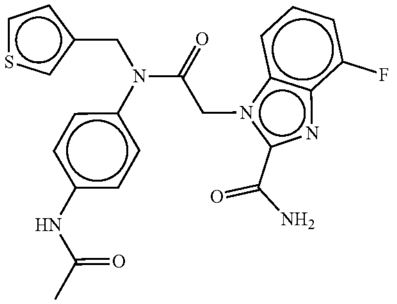 |
| 141d | 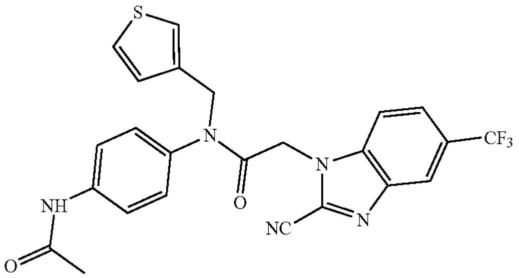 [SMILES: CC(=O)Nc1ccc(N(Cc2ccsc2)C(=O)Cn2c(C#N)nc3cc(C(F)(F)F)ccc32)cc1] |
| 141e | 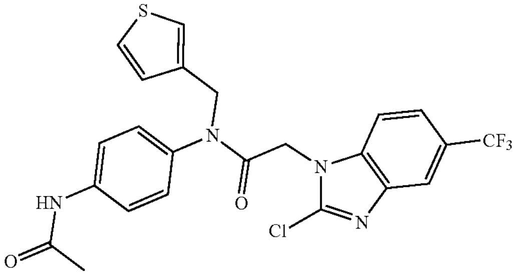 [SMILES: CC(=O)Nc1ccc(N(Cc2ccsc2)C(=O)Cn2c(Cl)nc3cc(C(F)(F)F)ccc32)cc1] |

TABLE 1-continued
| Exemplary compounds. | |
|---|---|
| Cmpd No. | Structure |
| 141f | 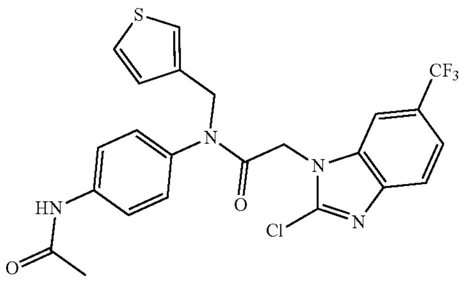 [SMILES: CC(=O)Nc1ccc(N(Cc2ccsc2)C(=O)Cn2c(Cl)nc3ccc(C(F)(F)F)cc32)cc1] |
| 141g | 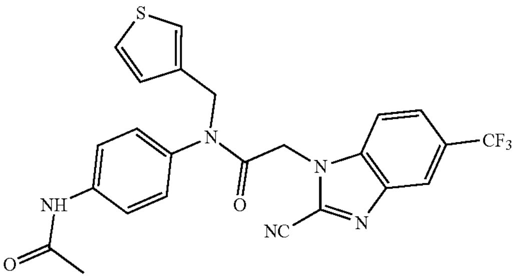 [SMILES: CC(=O)Nc1ccc(N(Cc2ccsc2)C(=O)Cn2c(C#N)nc3cc(C(F)(F)F)ccc32)cc1] |
| 141h | 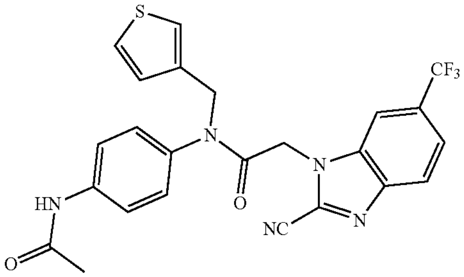 [SMILES: CC(=O)Nc1ccc(N(Cc2ccsc2)C(=O)Cn2c(C#N)nc3ccc(C(F)(F)F)cc32)cc1] |
| 142 | 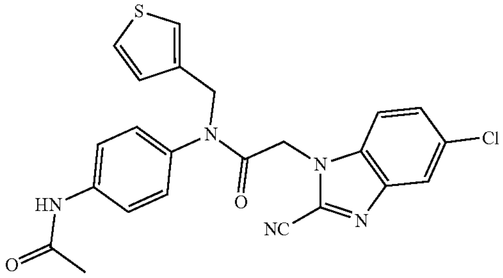 [SMILES: CC(=O)Nc1ccc(N(Cc2ccsc2)C(=O)Cn2c(C#N)nc3cc(Cl)ccc32)cc1] |
| 142a | 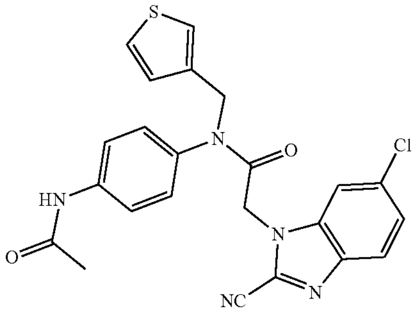 [SMILES: CC(=O)Nc1ccc(N(Cc2ccsc2)C(=O)Cn2c(C#N)nc3ccc(Cl)cc32)cc1] |
TABLE 1-continued
| Exemplary compounds. | |
|---|---|
| Cmpd No. | Structure |
| 142b | 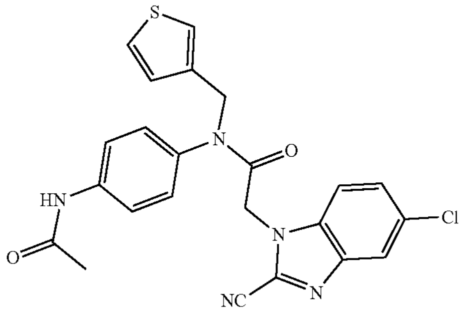 [SMILES: CC(=O)Nc1ccc(N(Cc2ccsc2)C(=O)Cn2c(C#N)nc3cc(Cl)ccc32)cc1] |
| 143 | 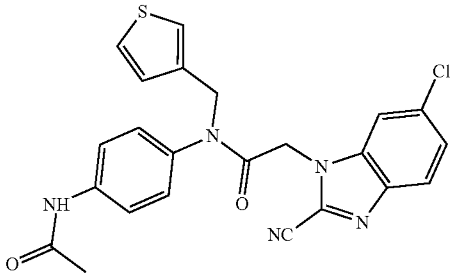 [SMILES: CC(=O)Nc1ccc(N(Cc2ccsc2)C(=O)Cn2c(C#N)nc3ccc(Cl)cc32)cc1] |
| 144 | 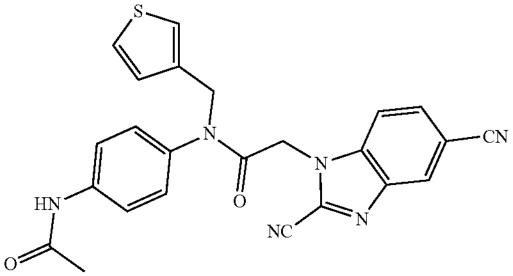 [SMILES: CC(=O)Nc1ccc(N(Cc2ccsc2)C(=O)Cn2c(C#N)nc3cc(C#N)ccc32)cc1] |
| 145 | 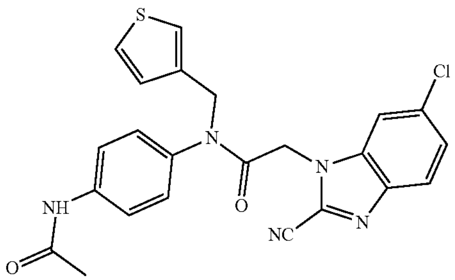 [SMILES: CC(=O)Nc1ccc(N(Cc2ccsc2)C(=O)Cn2c(C#N)nc3ccc(Cl)cc32)cc1] |
| 145a | 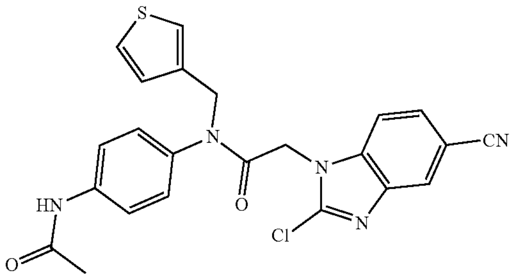 [SMILES: CC(=O)Nc1ccc(N(Cc2ccsc2)C(=O)Cn2c(Cl)nc3cc(C#N)ccc32)cc1] |

TABLE 1-continued
| Exemplary compounds. | |
|---|---|
| Cmpd No. | Structure |
| 145b | 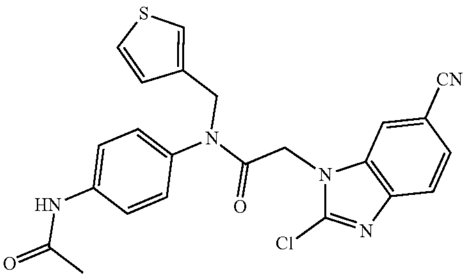 [SMILES: CC(=O)Nc1ccc(N(Cc2ccsc2)C(=O)Cn2c(Cl)nc3ccc(C#N)cc32)cc1] |
| 146 | 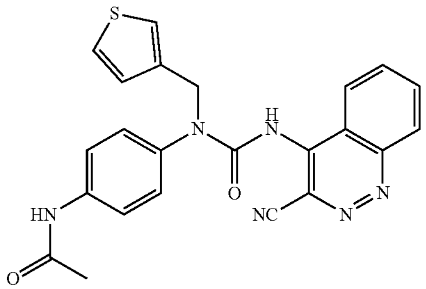 [SMILES: CC(=O)Nc1ccc(N(Cc2ccsc2)C(=O)Nc2c(C#N)nnc3ccccc23)cc1] |
| 147 | 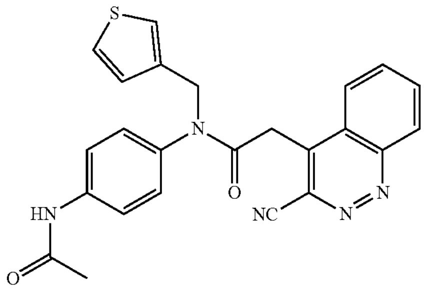 [SMILES: CC(=O)Nc1ccc(N(Cc2ccsc2)C(=O)Cc2c(C#N)nnc3ccccc23)cc1] |
| 148 | 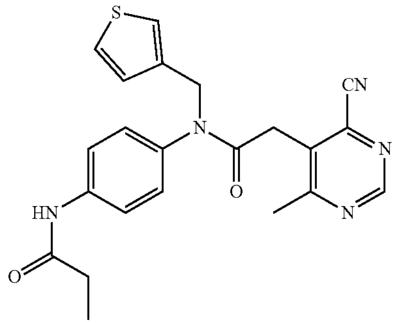 [SMILES: CCC(=O)Nc1ccc(N(Cc2ccsc2)C(=O)Cc2c(C)ncnc2C#N)cc1] |
| 149 | 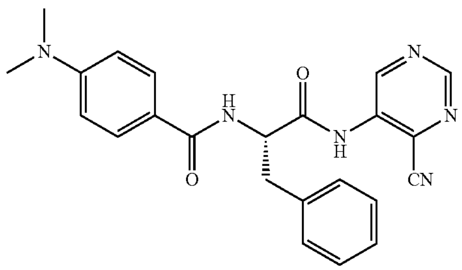 [SMILES: CN(C)c1ccc(C(=O)N[C@@H](Cc2ccccc2)C(=O)Nc2cncnc2C#N)cc1] |
TABLE 1-continued
| Exemplary compounds. | |
|---|---|
| Cmpd No. | Structure |
| 150 | 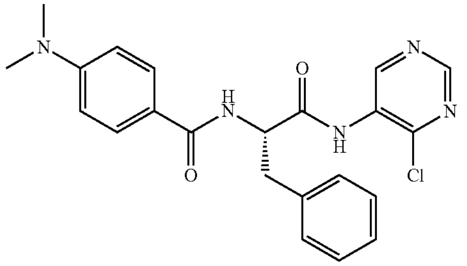 [SMILES: CN(C)c1ccc(C(=O)N[C@@H](Cc2ccccc2)C(=O)Nc2cncnc2Cl)cc1] |
| 151 | 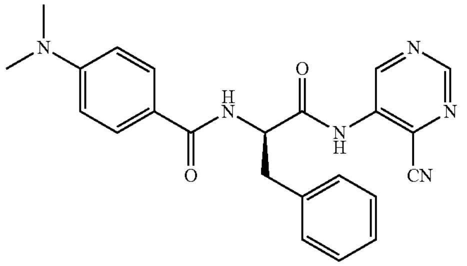 [SMILES: CN(C)c1ccc(C(=O)N[C@H](Cc2ccccc2)C(=O)Nc2cncnc2C#N)cc1] |
| 151a | 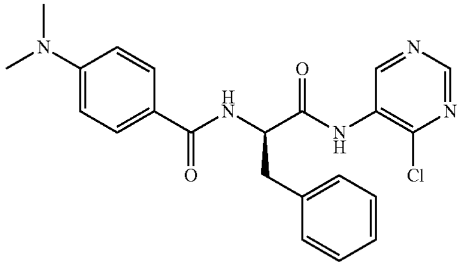 [SMILES: CN(C)c1ccc(C(=O)N[C@H](Cc2ccccc2)C(=O)Nc2cncnc2Cl)cc1] |
| 152a | 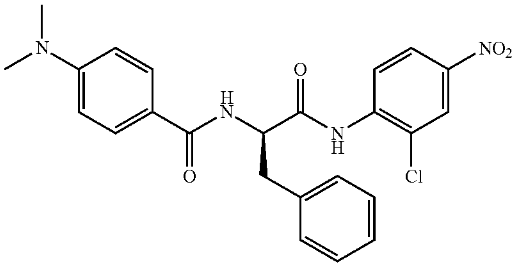 [SMILES: CN(C)c1ccc(C(=O)N[C@H](Cc2ccccc2)C(=O)Nc2ccc([N+](=O)[O-])cc2Cl)cc1] |
| 152 | 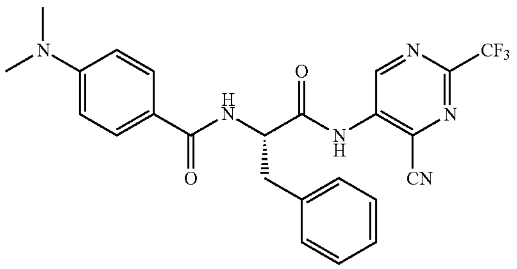 [SMILES: CN(C)c1ccc(C(=O)N[C@@H](Cc2ccccc2)C(=O)Nc2cnc(C(F)(F)F)nc2C#N)cc1] |

TABLE 1-continued
| Exemplary compounds. | |
|---|---|
| Cmpd No. | Structure |
| 153 | 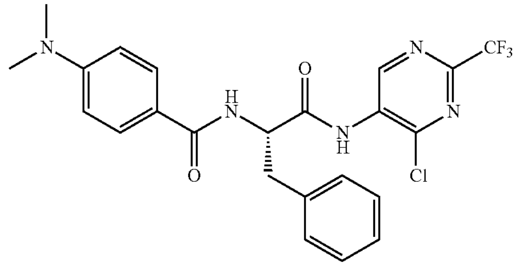 [SMILES: CN(C)c1ccc(C(=O)N[C@@H](Cc2ccccc2)C(=O)Nc2cnc(C(F)(F)F)nc2Cl)cc1] |
| 154 | 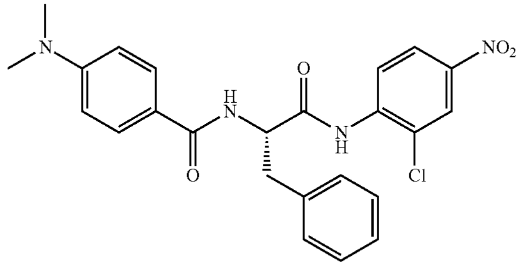 [SMILES: CN(C)c1ccc(C(=O)N[C@@H](Cc2ccccc2)C(=O)Nc2ccc([N+](=O)[O-])cc2Cl)cc1] |
| 155 | 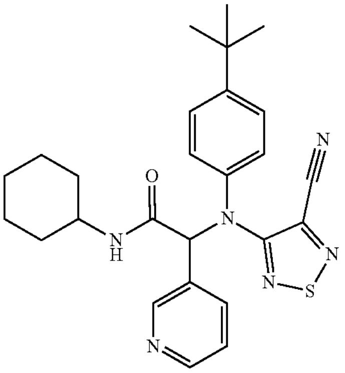 [SMILES: CC(C)(C)c1ccc(N(c2nsnc2C#N)C(C(=O)NC2CCCCC2)c2cccnc2)cc1] |
| 156 | 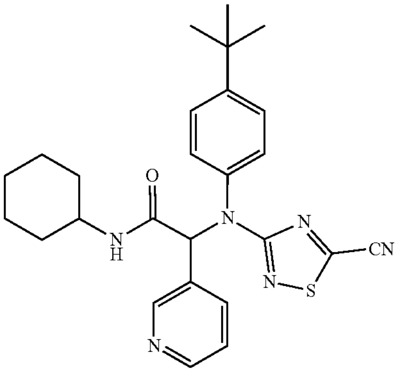 [SMILES: CC(C)(C)c1ccc(N(c2nsc(C#N)n2)C(C(=O)NC2CCCCC2)c2cccnc2)cc1] |
TABLE 1-continued
| Exemplary compounds. | |
|---|---|
| Cmpd No. | Structure |
| 157 | 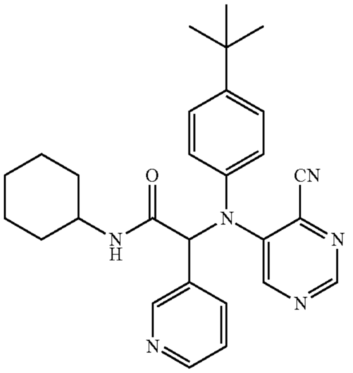 [SMILES: CC(C)(C)c1ccc(N(c2cncnc2C#N)C(C(=O)NC2CCCCC2)c2cccnc2)cc1] |
| 158 | 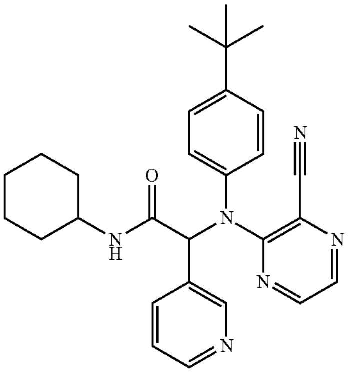 [SMILES: CC(C)(C)c1ccc(N(c2nccnc2C#N)C(C(=O)NC2CCCCC2)c2cccnc2)cc1] |
| 159 | 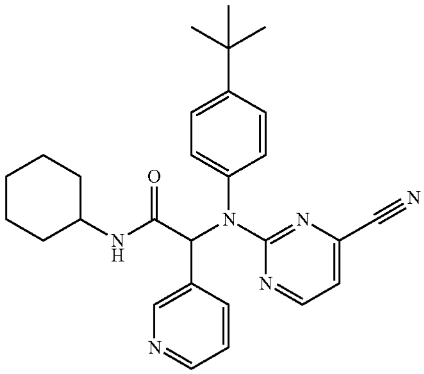 [SMILES: CC(C)(C)c1ccc(N(c2nccc(C#N)n2)C(C(=O)NC2CCCCC2)c2cccnc2)cc1] |
| 160 | 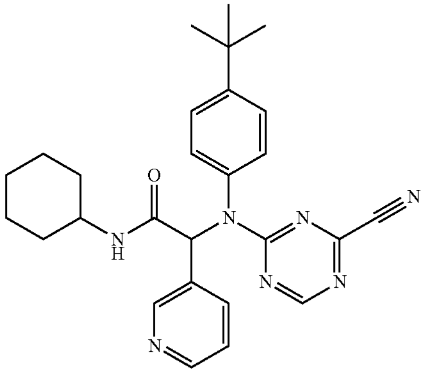 [SMILES: CC(C)(C)c1ccc(N(c2ncnc(C#N)n2)C(C(=O)NC2CCCCC2)c2cccnc2)cc1] |

TABLE 1-continued
| Cmpd No. | Structure |
| --- | --- |
| | Exemplary compounds. |
| 161 | 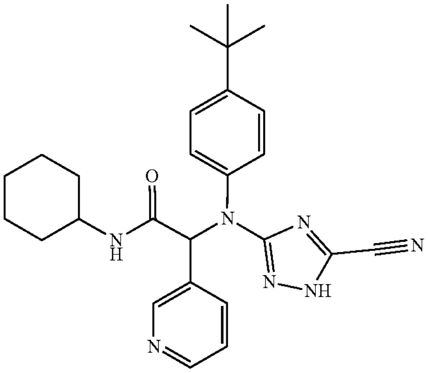 [SMILES: CC(C)(C)c1ccc(N(c2n[nH]c(C#N)n2)C(C(=O)NC2CCCCC2)c2cccnc2)cc1] |
| 162 | 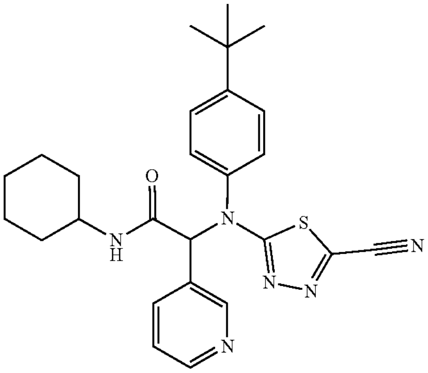 [SMILES: CC(C)(C)c1ccc(N(c2nnc(C#N)s2)C(C(=O)NC2CCCCC2)c2cccnc2)cc1] |
| 163 | 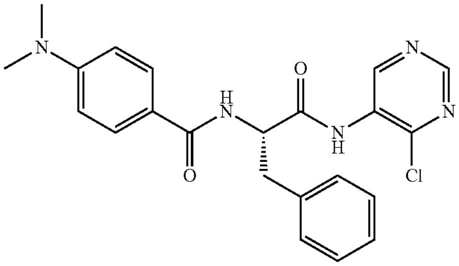 [SMILES: CN(C)c1ccc(C(=O)N[C@@H](Cc2ccccc2)C(=O)Nc2cncnc2Cl)cc1] |
| 164 | 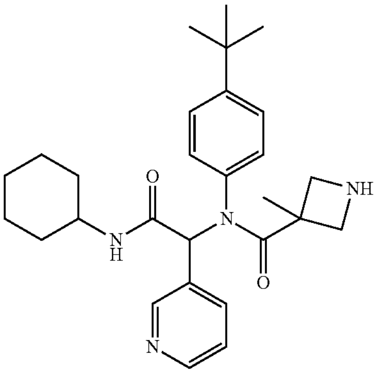 [SMILES: CC1(C(=O)N(c2ccc(C(C)(C)C)cc2)C(C(=O)NC2CCCCC2)c2cccnc2)CNC1] |
TABLE 1-continued
| Cmpd No. | Structure |
| --- | --- |
| | Exemplary compounds. |
| 165 | 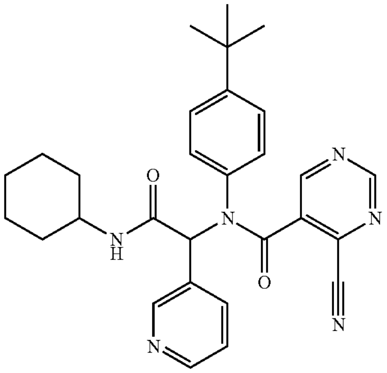 [SMILES: CC(C)(C)c1ccc(N(C(=O)c2cncnc2C#N)C(C(=O)NC2CCCCC2)c2cccnc2)cc1] |
| 166 | 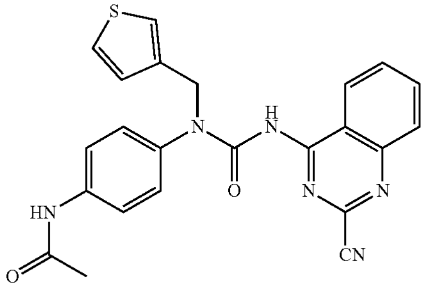 [SMILES: CC(=O)Nc1ccc(N(Cc2ccsc2)C(=O)Nc2nc(C#N)nc3ccccc23)cc1] |
| 167 | 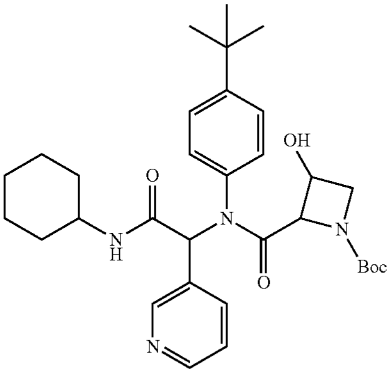 [SMILES: CC(C)(C)OC(=O)N1CC(O)C1C(=O)N(c1ccc(C(C)(C)C)cc1)C(C(=O)NC1CCCCC1)c1cccnc1] |
| 168 | 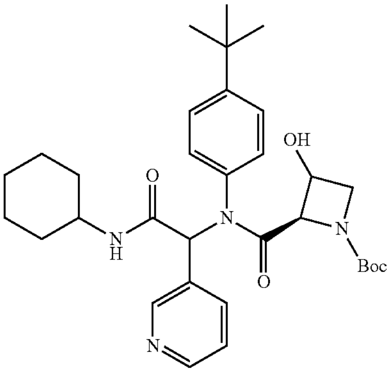 [SMILES: CC(C)(C)OC(=O)N1CC(O)[C@@H]1C(=O)N(c1ccc(C(C)(C)C)cc1)C(C(=O)NC1CCCCC1)c1cccnc1] |

TABLE 1-continued
Exemplary compounds.
| Cmpd No. | Structure |
| --- | --- |
| 169 | 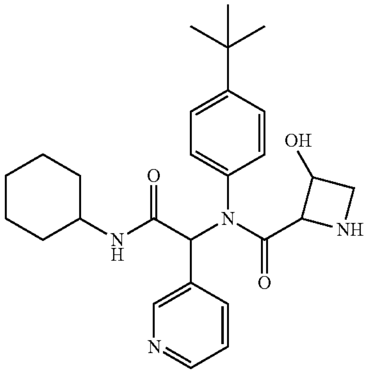 [SMILES: CC(C)(C)c1ccc(N(C(=O)C2NCC2O)C(C(=O)NC2CCCCC2)c2cccnc2)cc1] |
| 170 | 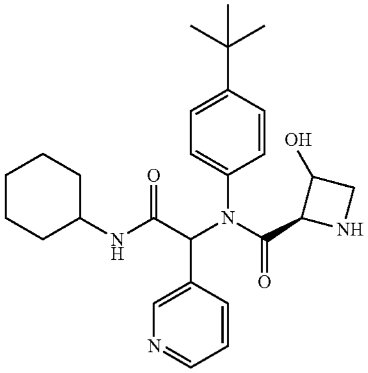 [SMILES: CC(C)(C)c1ccc(N(C(=O)[C@@H]2NCC2O)C(C(=O)NC2CCCCC2)c2cccnc2)cc1] |
| 171 | 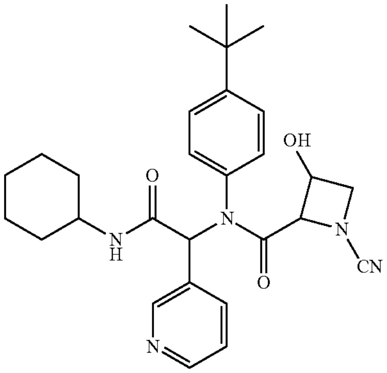 [SMILES: CC(C)(C)c1ccc(N(C(=O)C2C(O)CN2C#N)C(C(=O)NC2CCCCC2)c2cccnc2)cc1] |
| 172 | 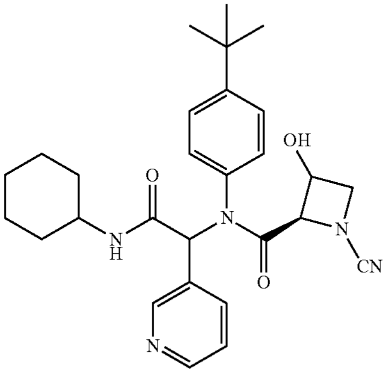 [SMILES: CC(C)(C)c1ccc(N(C(=O)[C@H]2C(O)CN2C#N)C(C(=O)NC2CCCCC2)c2cccnc2)cc1] |
TABLE 1-continued
Exemplary compounds.
| Cmpd No. | Structure |
| --- | --- |
| 173 | 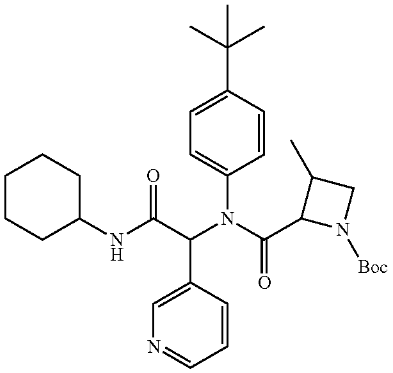 [SMILES: CC1CN(C(=O)OC(C)(C)C)C1C(=O)N(c1ccc(C(C)(C)C)cc1)C(C(=O)NC1CCCCC1)c1cccnc1] |
| 174 | 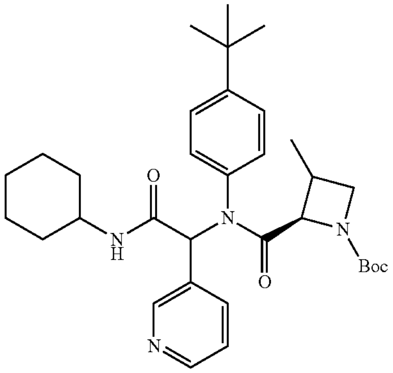 [SMILES: CC1CN(C(=O)OC(C)(C)C)[C@H]1C(=O)N(c1ccc(C(C)(C)C)cc1)C(C(=O)NC1CCCCC1)c1cccnc1] |
| 175 | 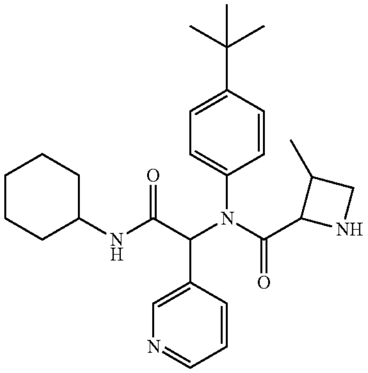 [SMILES: CC1CNC1C(=O)N(c1ccc(C(C)(C)C)cc1)C(C(=O)NC1CCCCC1)c1cccnc1] |
| 176 | 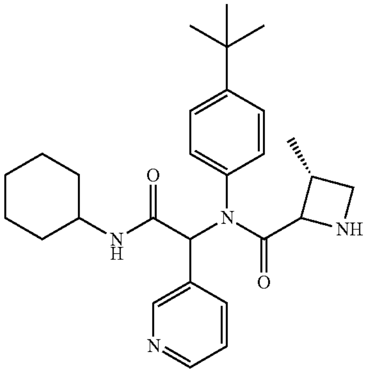 [SMILES: C[C@@H]1CNC1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 177 | 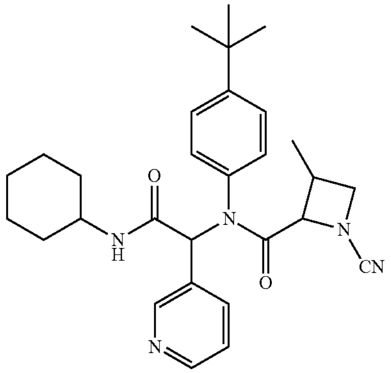 [SMILES: CC1CN(C#N)C1C(=O)N(c1ccc(C(C)(C)C)cc1)C(C(=O)NC1CCCCC1)c1cccnc1] |
| 178 | 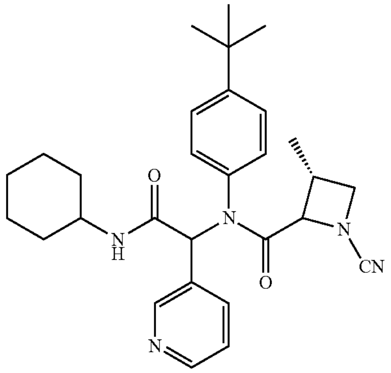 [SMILES: C[C@@H]1CN(C#N)C1C(=O)N(c1ccc(C(C)(C)C)cc1)C(C(=O)NC1CCCCC1)c1cccnc1] |
| 179 | 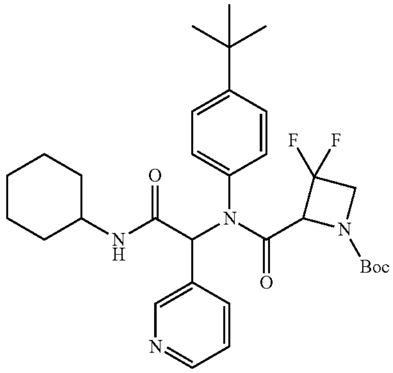 [SMILES: CC(C)(C)OC(=O)N1CC(F)(F)C1C(=O)N(c1ccc(C(C)(C)C)cc1)C(C(=O)NC1CCCCC1)c1cccnc1] |
| 180 | 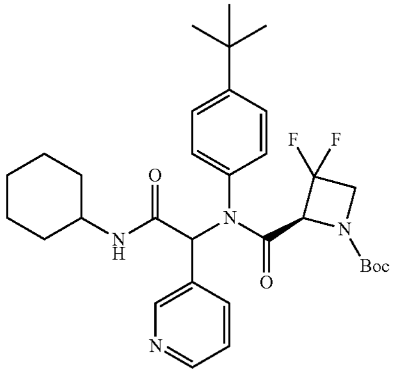 [SMILES: CC(C)(C)OC(=O)N1CC(F)(F)[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 181 | 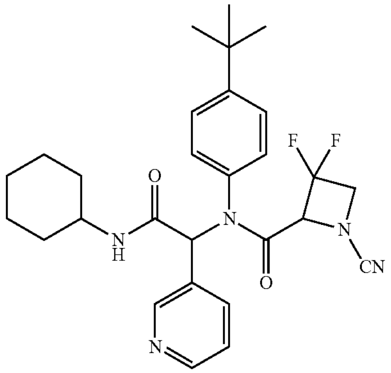 [SMILES: CC(C)(C)c1ccc(N(C(=O)C2N(C#N)CC2(F)F)C(C(=O)NC2CCCCC2)c2cccnc2)cc1] |
| 182 | 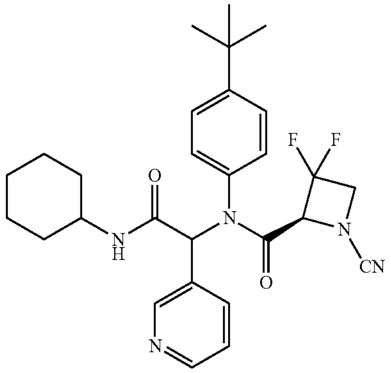 [SMILES: CC(C)(C)c1ccc(N(C(=O)[C@@H]2N(C#N)CC2(F)F)C(C(=O)NC2CCCCC2)c2cccnc2)cc1] |
| 183 | 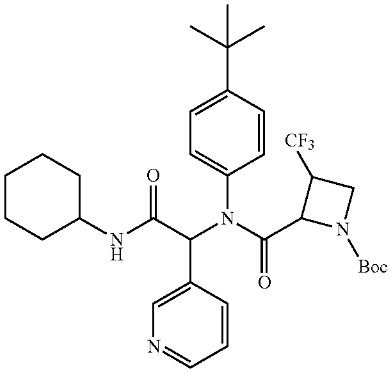 [SMILES: CC(C)(C)OC(=O)N1CC(C(F)(F)F)C1C(=O)N(c1ccc(C(C)(C)C)cc1)C(C(=O)NC1CCCCC1)c1cccnc1] |
| 184 | 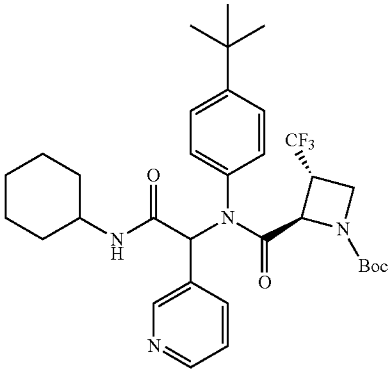 [SMILES: CC(C)(C)OC(=O)N1C[C@@H](C(F)(F)F)[C@@H]1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 185 | 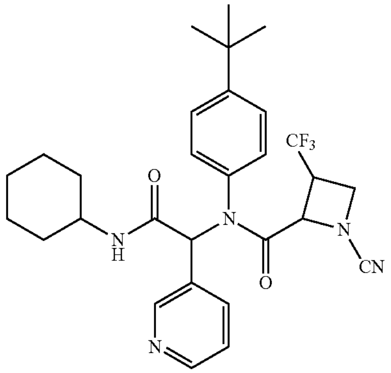 [SMILES: CC(C)(C)c1ccc(N(C(=O)C2C(C(F)(F)F)CN2C#N)C(C(=O)NC2CCCCC2)c2cccnc2)cc1] |
| 186 | 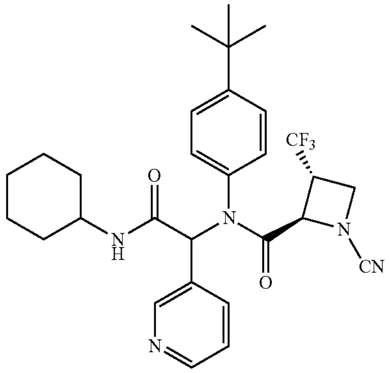 |
| 187 | 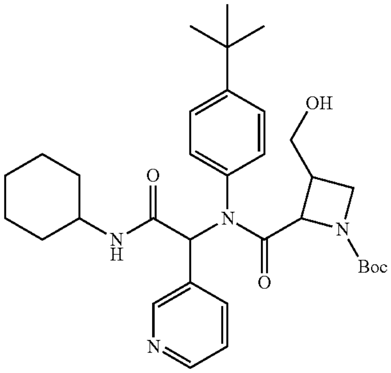 [SMILES: CC(C)(C)OC(=O)N1CC(CO)C1C(=O)N(c1ccc(C(C)(C)C)cc1)C(C(=O)NC1CCCCC1)c1cccnc1] |
| 188 | 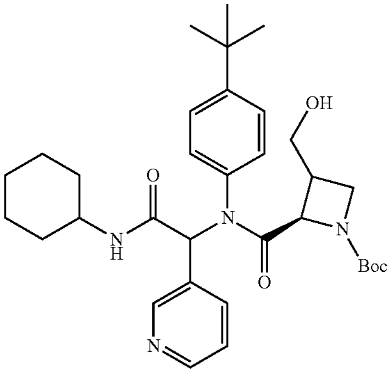 [SMILES: CC(C)(C)OC(=O)N1CC(CO)[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 189 | 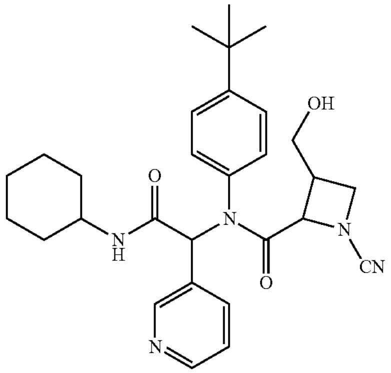 [SMILES: CC(C)(C)c1ccc(N(C(=O)C2C(CO)CN2C#N)C(C(=O)NC2CCCCC2)c2cccnc2)cc1] |
| 190 | 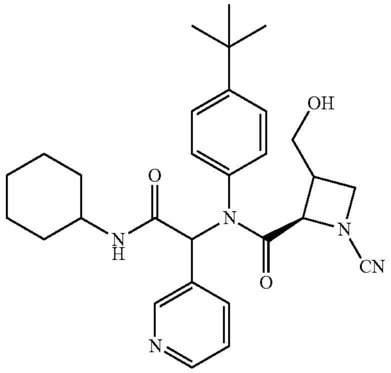 [SMILES: CC(C)(C)c1ccc(N(C(=O)[C@H]2C(CO)CN2C#N)C(C(=O)NC2CCCCC2)c2cccnc2)cc1] |
| 191 | 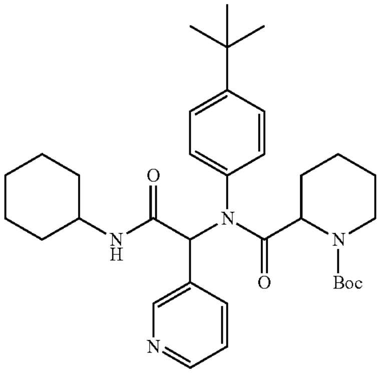 [SMILES: CC(C)(C)OC(=O)N1CCCCC1C(=O)N(c1ccc(C(C)(C)C)cc1)C(C(=O)NC1CCCCC1)c1cccnc1] |
| 192 | 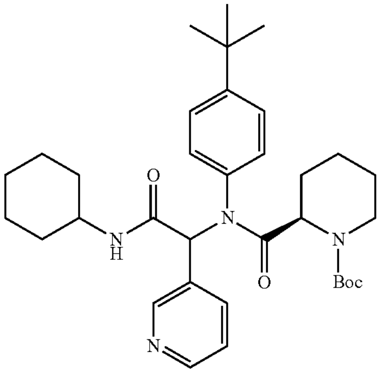 [SMILES: CC(C)(C)OC(=O)N1CCCC[C@@H]1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 193 | 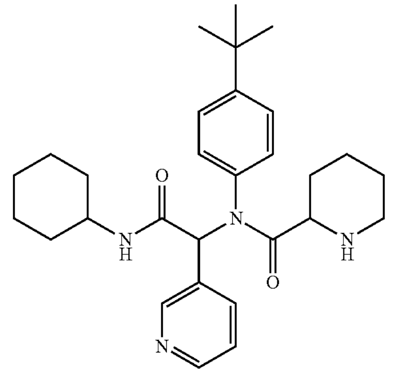 [SMILES: CC(C)(C)c1ccc(N(C(=O)C2CCCCN2)C(C(=O)NC2CCCCC2)c2cccnc2)cc1] |
| 194 | 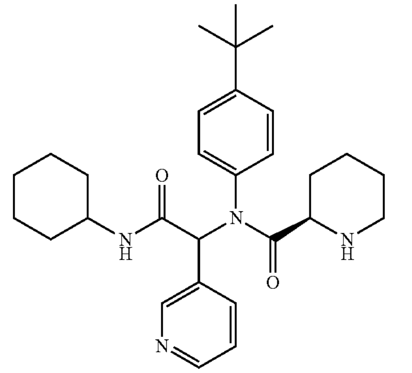 [SMILES: CC(C)(C)c1ccc(N(C(=O)[C@H]2CCCCN2)C(C(=O)NC2CCCCC2)c2cccnc2)cc1] |
| 195 | 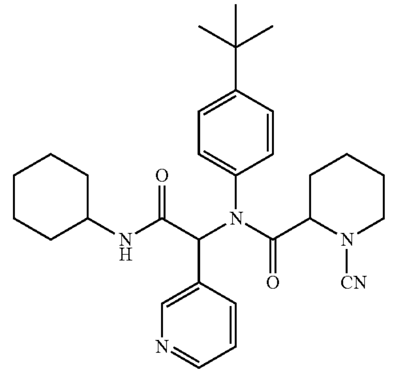 [SMILES: CC(C)(C)c1ccc(N(C(=O)C2CCCCN2C#N)C(C(=O)NC2CCCCC2)c2cccnc2)cc1] |
| 196 | 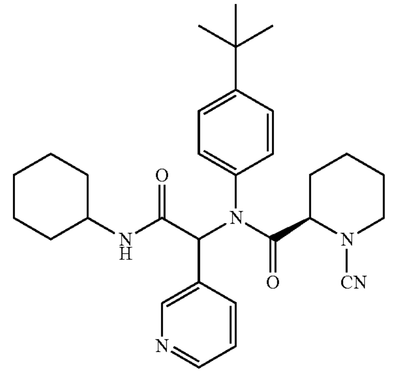 [SMILES: CC(C)(C)c1ccc(N(C(=O)[C@H]2CCCCN2C#N)C(C(=O)NC2CCCCC2)c2cccnc2)cc1] |
TABLE 1-continued
| Exemplary compounds. | |
|---|---|
| Cmpd No. | Structure |
| 197 | 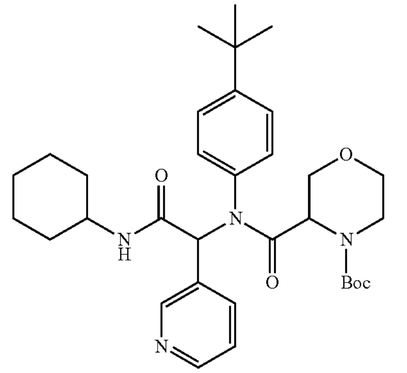 [SMILES: CC(C)(C)OC(=O)N1CCOCC1C(=O)N(c1ccc(C(C)(C)C)cc1)C(C(=O)NC1CCCCC1)c1cccnc1] |
| 198 | 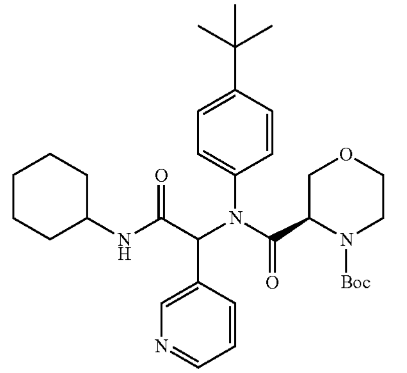 |
| 199 | 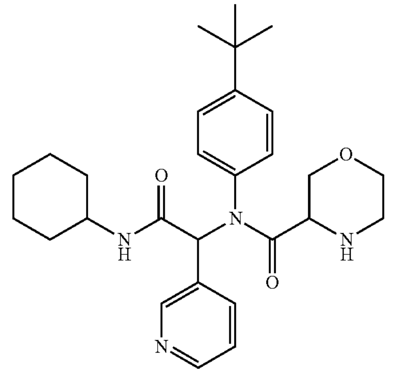 [SMILES: CC(C)(C)c1ccc(N(C(=O)C2COCCN2)C(C(=O)NC2CCCCC2)c2cccnc2)cc1] |
| 200 | 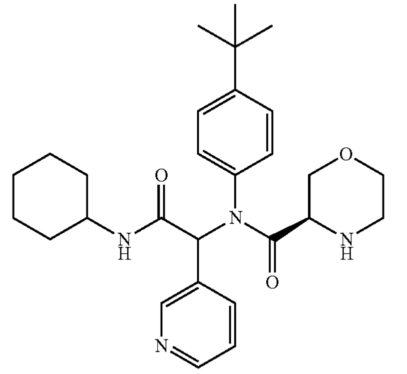 [SMILES: CC(C)(C)c1ccc(N(C(=O)[C@H]2COCCN2)C(C(=O)NC2CCCCC2)c2cccnc2)cc1] |

TABLE 1-continued
| Exemplary compounds. | |
|---|---|
| Cmpd No. | Structure |
| 201 | 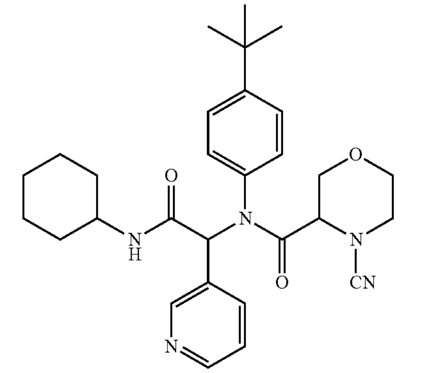 [SMILES: CC(C)(C)c1ccc(N(C(=O)C2COCCN2C#N)C(C(=O)NC2CCCCC2)c2cccnc2)cc1] |
| 202 | 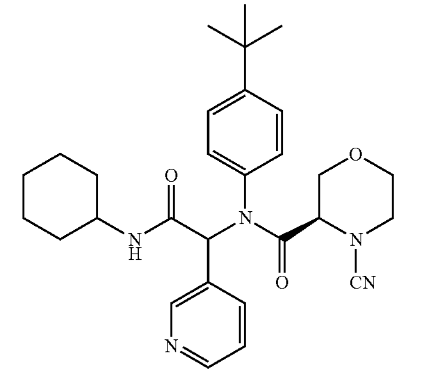 [SMILES: CC(C)(C)c1ccc(N(C(=O)[C@H]2COCCN2C#N)C(C(=O)NC2CCCCC2)c2cccnc2)cc1] |
| 203 | 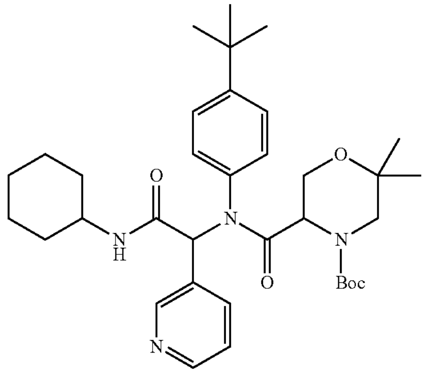 [SMILES: CC(C)(C)OC(=O)N1CC(C)(C)OCC1C(=O)N(c1ccc(C(C)(C)C)cc1)C(C(=O)NC1CCCCC1)c1cccnc1] |
| 204 | 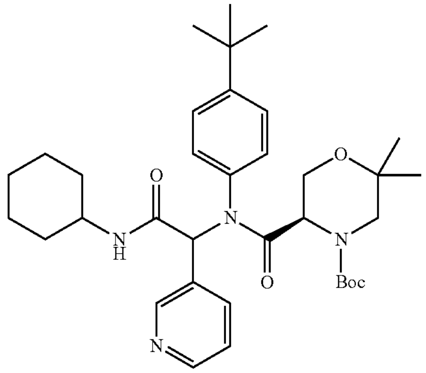 [SMILES: CC(C)(C)OC(=O)N1CC(C)(C)OC[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 205 | 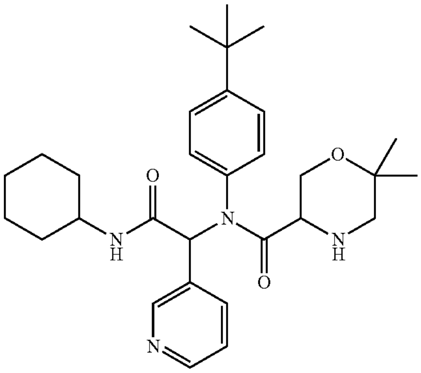 [SMILES: CC1(C)CNC(C(=O)N(c2ccc(C(C)(C)C)cc2)C(C(=O)NC2CCCCC2)c2cccnc2)CO1] |
| 206 | 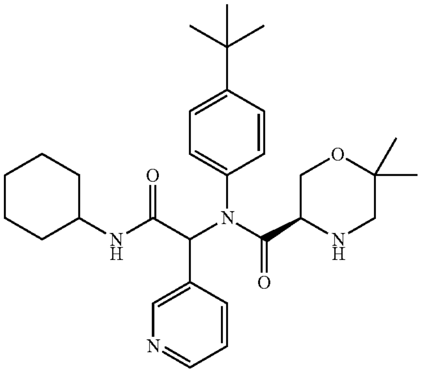 [SMILES: CC1(C)CN[C@@H](C(=O)N(c2ccc(C(C)(C)C)cc2)C(C(=O)NC2CCCCC2)c2cccnc2)CO1] |
| 207 | 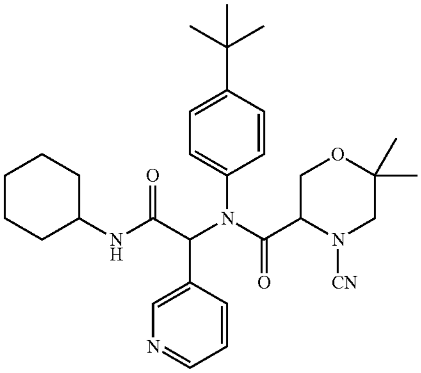 [SMILES: CC1(C)CN(C#N)C(C(=O)N(c2ccc(C(C)(C)C)cc2)C(C(=O)NC2CCCCC2)c2cccnc2)CO1] |
| 208 | 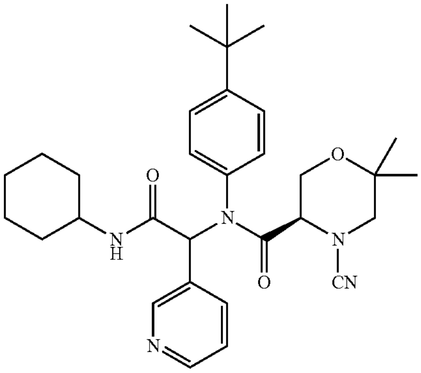 [SMILES: CC1(C)CN(C#N)[C@@H](C(=O)N(c2ccc(C(C)(C)C)cc2)C(C(=O)NC2CCCCC2)c2cccnc2)CO1] |

TABLE 1-continued
| Exemplary compounds. | |
|---|---|
| Cmpd No. | Structure |
| 209 | 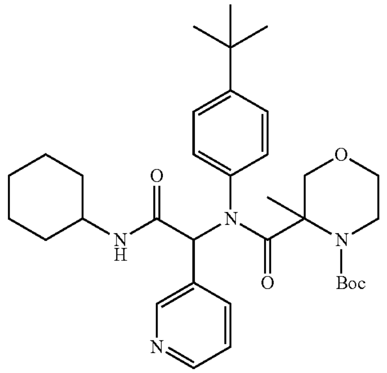 [SMILES: CC(C)(C)OC(=O)N1CCOCC1(C)C(=O)N(c1ccc(C(C)(C)C)cc1)C(C(=O)NC1CCCCC1)c1cccnc1] |
| 210 | 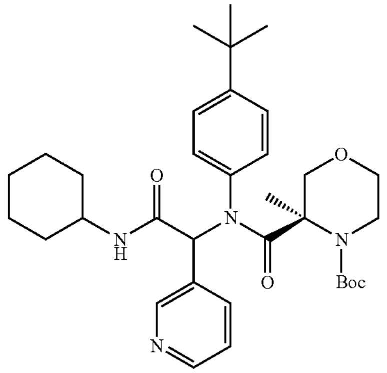 [SMILES: CC(C)(C)OC(=O)N1CCOC[C@]1(C)C(=O)N(c1ccc(C(C)(C)C)cc1)C(C(=O)NC1CCCCC1)c1cccnc1] |
| 211 | 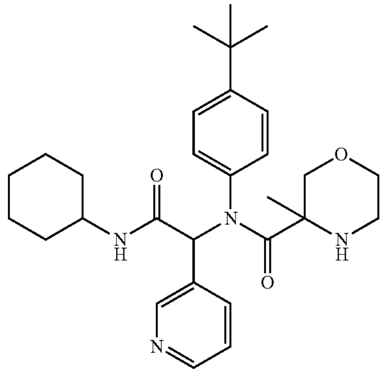 [SMILES: CC1(C(=O)N(c2ccc(C(C)(C)C)cc2)C(C(=O)NC2CCCCC2)c2cccnc2)COCCN1] |
| 212 | 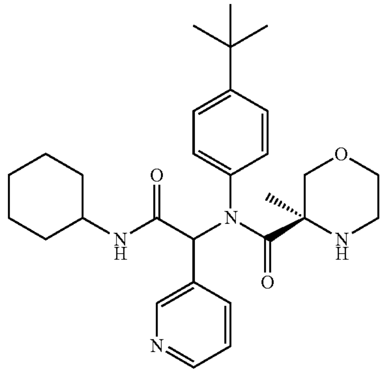 [SMILES: CC(C)(C)c1ccc(N(C(=O)[C@@]2(C)COCCN2)C(C(=O)NC2CCCCC2)c2cccnc2)cc1] |
TABLE 1-continued
| Exemplary compounds. | |
|---|---|
| Cmpd No. | Structure |
| 213 | 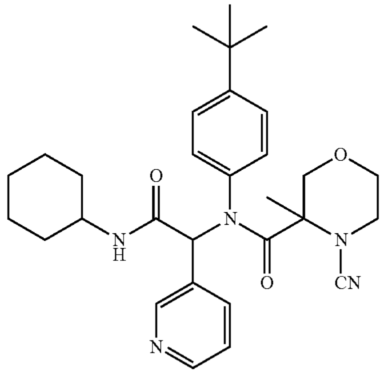 [SMILES: CC(C)(C)c1ccc(N(C(=O)C2(C)COCCN2C#N)C(C(=O)NC2CCCCC2)c2cccnc2)cc1] |
| 214 | 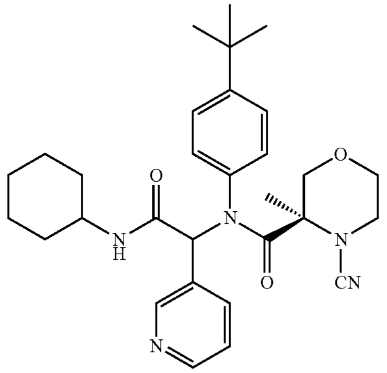 [SMILES: CC(C)(C)c1ccc(N(C(=O)[C@@]2(C)COCCN2C#N)C(C(=O)NC2CCCCC2)c2cccnc2)cc1] |
| 215 | 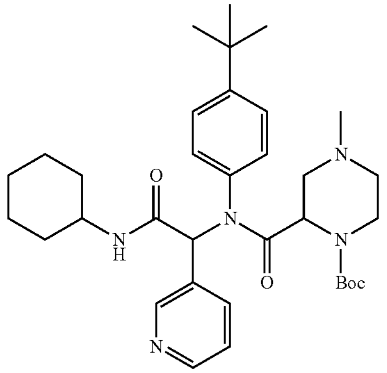 [SMILES: CN1CCN(C(=O)OC(C)(C)C)C(C(=O)N(c2ccc(C(C)(C)C)cc2)C(C(=O)NC2CCCCC2)c2cccnc2)C1] |
| 216 | 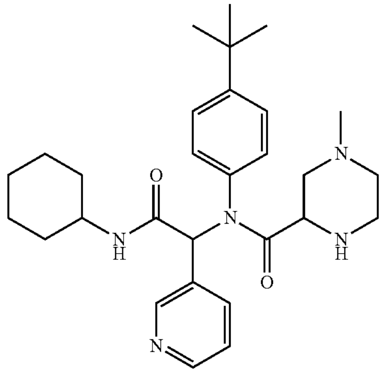 [SMILES: CN1CCNC(C(=O)N(c2ccc(C(C)(C)C)cc2)C(C(=O)NC2CCCCC2)c2cccnc2)C1] |

TABLE 1-continued
| Exemplary compounds. | |
|---|---|
| Cmpd No. | Structure |
| 217 | 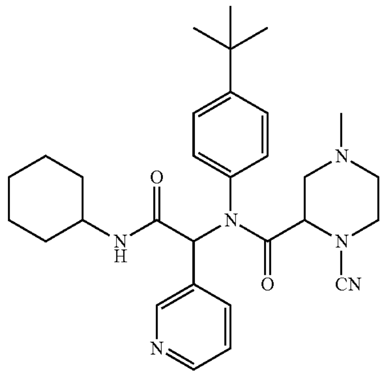 [SMILES: CN1CCN(C#N)C(C(=O)N(c2ccc(C(C)(C)C)cc2)C(C(=O)NC2CCCCC2)c2cccnc2)C1] |
| 218 | 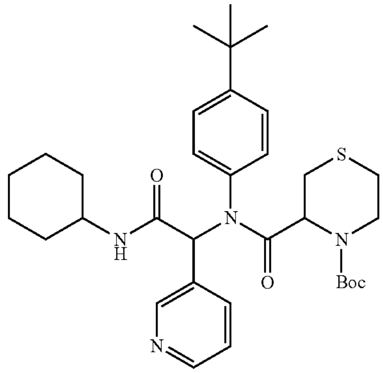 [SMILES: CC(C)(C)OC(=O)N1CCSCC1C(=O)N(c1ccc(C(C)(C)C)cc1)C(C(=O)NC1CCCCC1)c1cccnc1] |
| 219 | 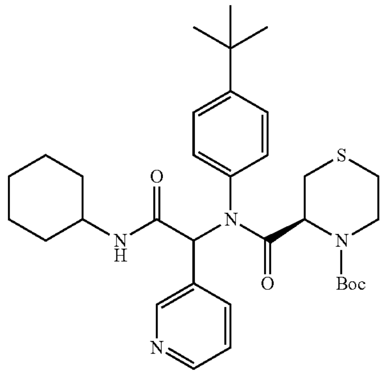 |
| 220 | 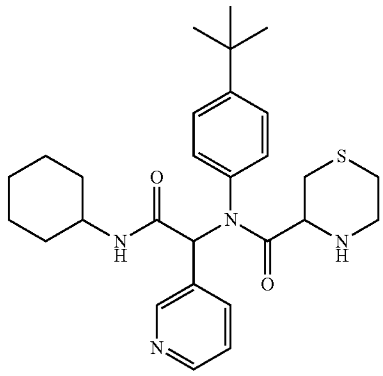 [SMILES: CC(C)(C)c1ccc(N(C(=O)C2CSCCN2)C(C(=O)NC2CCCCC2)c2cccnc2)cc1] |
TABLE 1-continued
| Exemplary compounds. | |
|---|---|
| Cmpd No. | Structure |
| 221 | 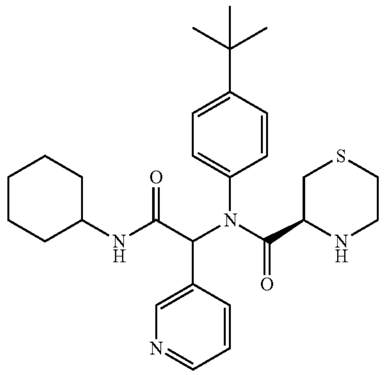 [SMILES: CC(C)(C)c1ccc(N(C(=O)[C@H]2CSCCN2)C(C(=O)NC2CCCCC2)c2cccnc2)cc1] |
| 222 | 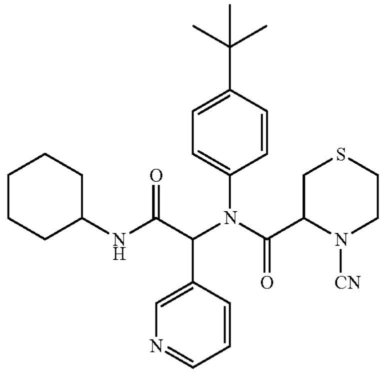 [SMILES: CC(C)(C)c1ccc(N(C(=O)C2CSCCN2C#N)C(C(=O)NC2CCCCC2)c2cccnc2)cc1] |
| 223 | 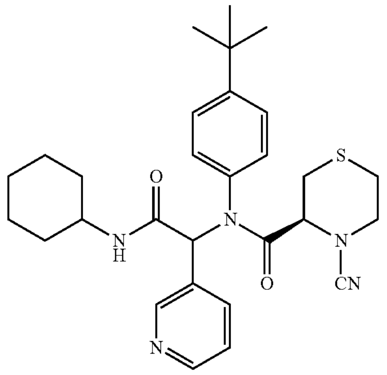 [SMILES: CC(C)(C)c1ccc(N(C(=O)[C@H]2CSCCN2C#N)C(C(=O)NC2CCCCC2)c2cccnc2)cc1] |
| 224 | 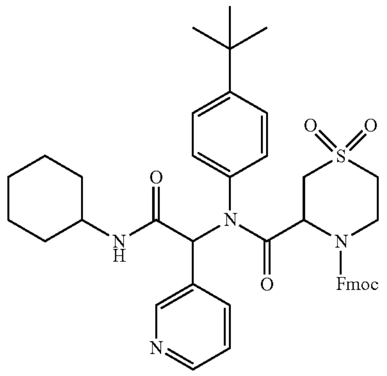 |

TABLE 1-continued
| Exemplary compounds. | |
| --- | --- |
| Cmpd No. | Structure |
| 225 | 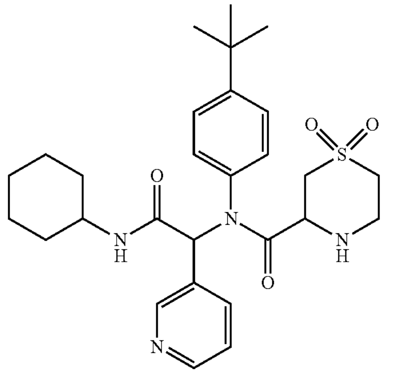 [SMILES: CC(C)(C)c1ccc(N(C(=O)C2CS(=O)(=O)CCN2)C(C(=O)NC2CCCCC2)c2cccnc2)cc1] |
| 226 | 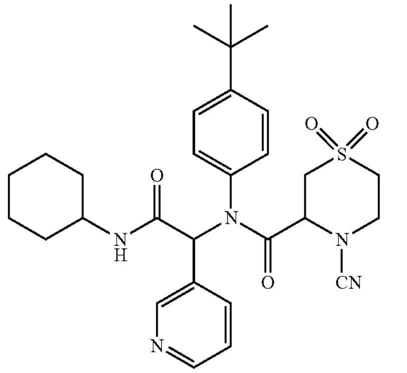 [SMILES: CC(C)(C)c1ccc(N(C(=O)C2CS(=O)(=O)CCN2C#N)C(C(=O)NC2CCCCC2)c2cccnc2)cc1] |
| 227 | 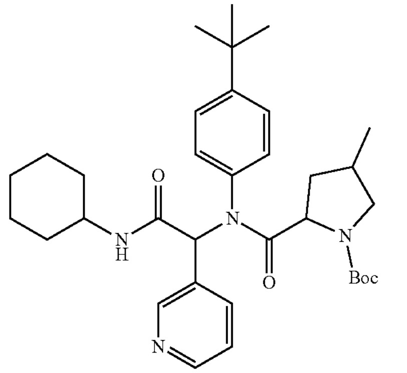 [SMILES: CC1CC(C(=O)N(c2ccc(C(C)(C)C)cc2)C(C(=O)NC2CCCCC2)c2cccnc2)N(C(=O)OC(C)(C)C)C1] |
| 228 | 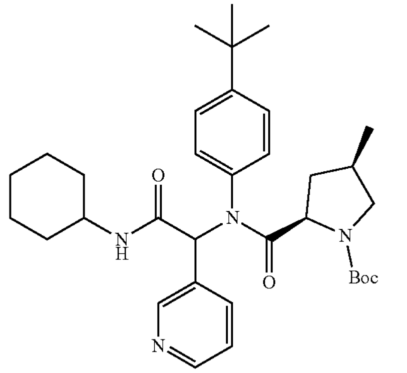 [SMILES: C[C@@H]1C[C@H](C(=O)N(c2ccc(C(C)(C)C)cc2)C(C(=O)NC2CCCCC2)c2cccnc2)N(C(=O)OC(C)(C)C)C1] |
| 229 | 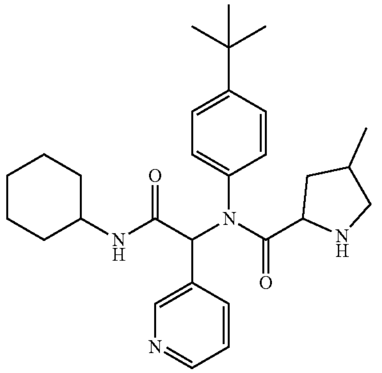 [SMILES: CC1CNC(C(=O)N(c2ccc(C(C)(C)C)cc2)C(C(=O)NC2CCCCC2)c2cccnc2)C1] |
| 230 | 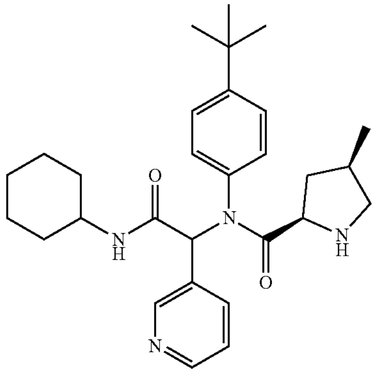 [SMILES: C[C@H]1CN[C@@H](C(=O)N(c2ccc(C(C)(C)C)cc2)C(C(=O)NC2CCCCC2)c2cccnc2)C1] |
| 231 | 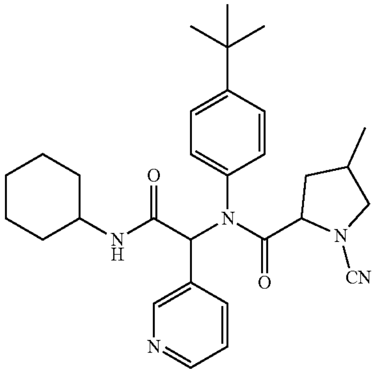 [SMILES: CC1CC(C(=O)N(c2ccc(C(C)(C)C)cc2)C(C(=O)NC2CCCCC2)c2cccnc2)N(C#N)C1] |
| 232 | 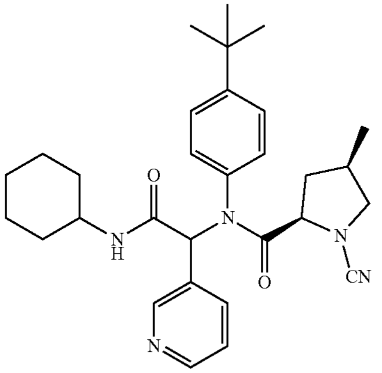 [SMILES: C[C@@H]1C[C@H](C(=O)N(c2ccc(C(C)(C)C)cc2)C(C(=O)NC2CCCCC2)c2cccnc2)N(C#N)C1] |

TABLE 1-continued
| Exemplary compounds. | |
|---|---|
| Cmpd No. | Structure |
| 233 | 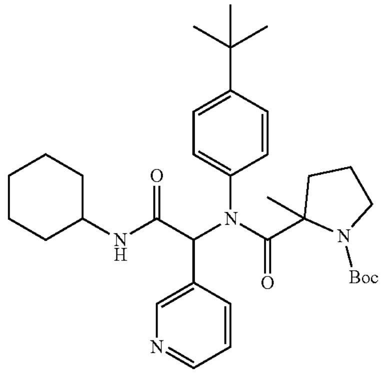 [SMILES: CC(C)(C)OC(=O)N1CCCC1(C)C(=O)N(c1ccc(C(C)(C)C)cc1)C(C(=O)NC1CCCCC1)c1cccnc1] |
| 234 | 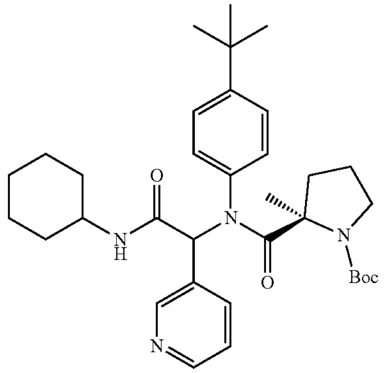 [SMILES: CC(C)(C)OC(=O)N1CCC[C@]1(C)C(=O)N(c1ccc(C(C)(C)C)cc1)C(C(=O)NC1CCCCC1)c1cccnc1] |
| 235 | 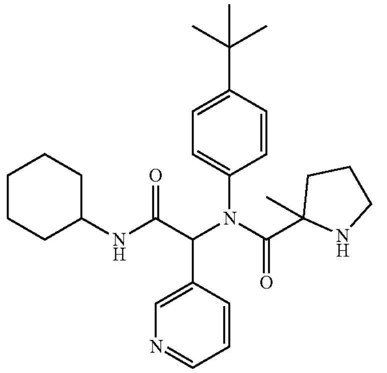 [SMILES: CC1(C(=O)N(c2ccc(C(C)(C)C)cc2)C(C(=O)NC2CCCCC2)c2cccnc2)CCCN1] |
| 236 | 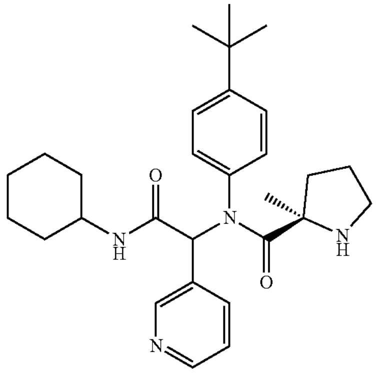 [SMILES: CC(C)(C)c1ccc(N(C(=O)[C@@]2(C)CCCN2)C(C(=O)NC2CCCCC2)c2cccnc2)cc1] |
TABLE 1-continued
| Exemplary compounds. | |
|---|---|
| Cmpd No. | Structure |
| 237 | 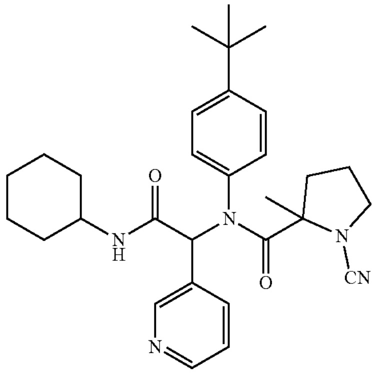 [SMILES: CC(C)(C)c1ccc(N(C(=O)C2(C)CCCN2C#N)C(C(=O)NC2CCCCC2)c2cccnc2)cc1] |
| 238 | 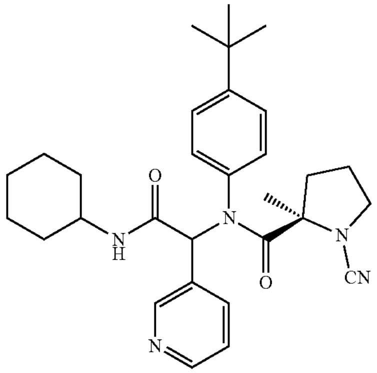 [SMILES: CC(C)(C)c1ccc(N(C(=O)[C@@]2(C)CCCN2C#N)C(C(=O)NC2CCCCC2)c2cccnc2)cc1] |
| 239 | 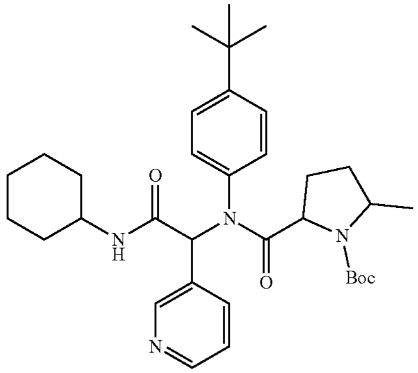 [SMILES: CC1CCC(C(=O)N(c2ccc(C(C)(C)C)cc2)C(C(=O)NC2CCCCC2)c2cccnc2)N1C(=O)OC(C)(C)C] |
| 240 | 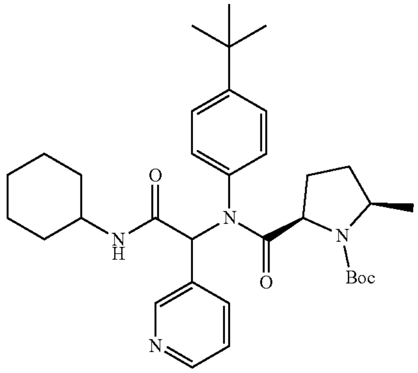 [SMILES: C[C@@H]1CC[C@H](C(=O)N(c2ccc(C(C)(C)C)cc2)C(C(=O)NC2CCCCC2)c2cccnc2)N1C(=O)OC(C)(C)C] |

TABLE 1-continued
| Exemplary compounds. | |
|---|---|
| Cmpd No. | Structure |
| 241 | 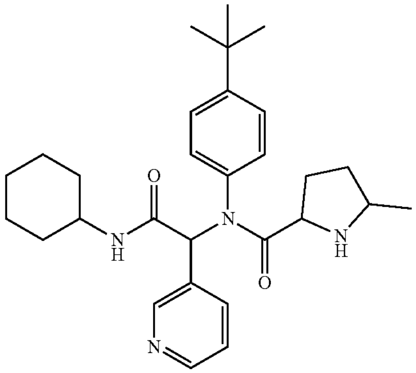 [SMILES: CC1CCC(C(=O)N(c2ccc(C(C)(C)C)cc2)C(C(=O)NC2CCCCC2)c2cccnc2)N1] |
| 242 | 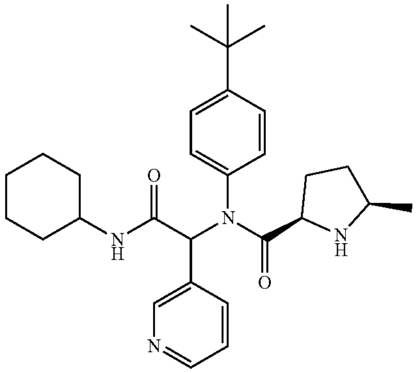 [SMILES: C[C@@H]1CC[C@H](C(=O)N(c2ccc(C(C)(C)C)cc2)C(C(=O)NC2CCCCC2)c2cccnc2)N1] |
| 243 | 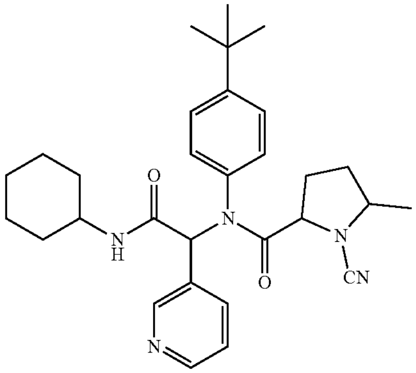 [SMILES: CC1CCC(C(=O)N(c2ccc(C(C)(C)C)cc2)C(C(=O)NC2CCCCC2)c2cccnc2)N1C#N] |
| 244 | 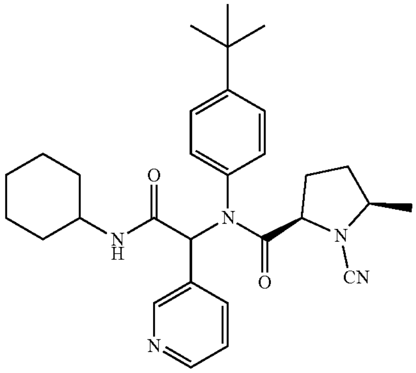 [SMILES: C[C@@H]1CC[C@H](C(=O)N(c2ccc(C(C)(C)C)cc2)C(C(=O)NC2CCCCC2)c2cccnc2)N1C#N] |
TABLE 1-continued
| Exemplary compounds. | |
|---|---|
| Cmpd No. | Structure |
| 245 | 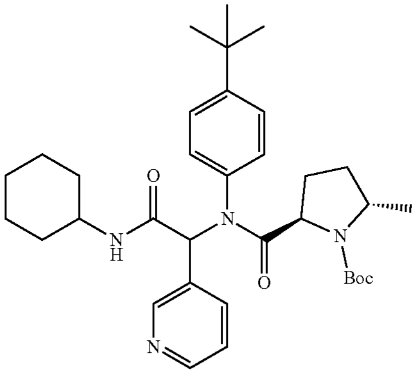 [SMILES: C[C@H]1CC[C@H](C(=O)N(c2ccc(C(C)(C)C)cc2)C(C(=O)NC2CCCCC2)c2cccnc2)N1C(=O)OC(C)(C)C] |
| 246 | 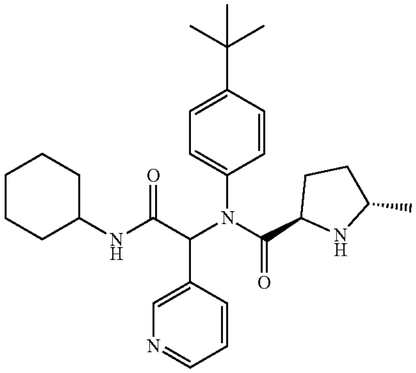 [SMILES: C[C@H]1CC[C@H](C(=O)N(c2ccc(C(C)(C)C)cc2)C(C(=O)NC2CCCCC2)c2cccnc2)N1] |
| 247 | 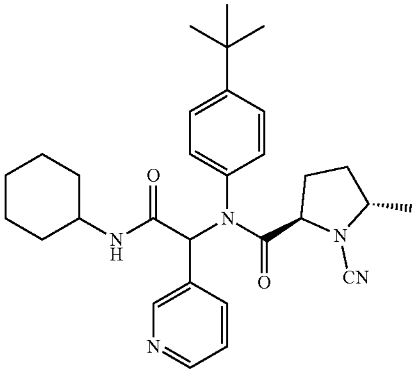 [SMILES: C[C@H]1CC[C@H](C(=O)N(c2ccc(C(C)(C)C)cc2)C(C(=O)NC2CCCCC2)c2cccnc2)N1C#N] |
| 248 | 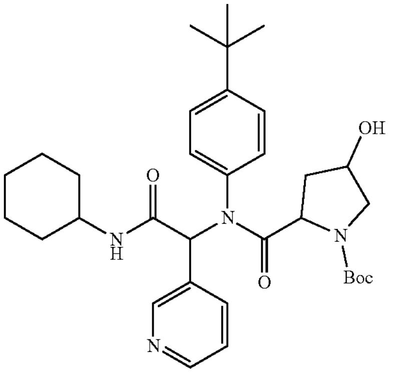 [SMILES: CC(C)(C)OC(=O)N1CC(O)CC1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 249 | 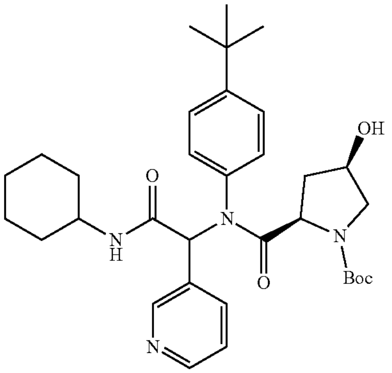 [SMILES: CC(C)(C)OC(=O)N1C[C@H](O)C[C@@H]1C(=O)N(c1ccc(C(C)(C)C)cc1)C(C(=O)NC1CCCCC1)c1cccnc1] |
| 250 | 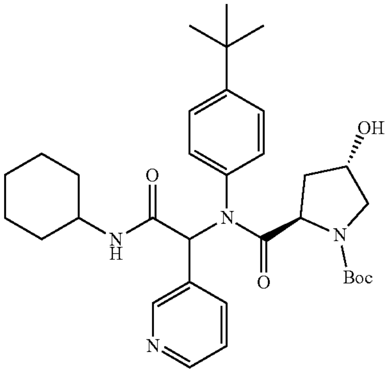 [SMILES: CC(C)(C)OC(=O)N1C[C@@H](O)C[C@@H]1C(=O)N(c1ccc(C(C)(C)C)cc1)C(C(=O)NC1CCCCC1)c1cccnc1] |
| 251 | 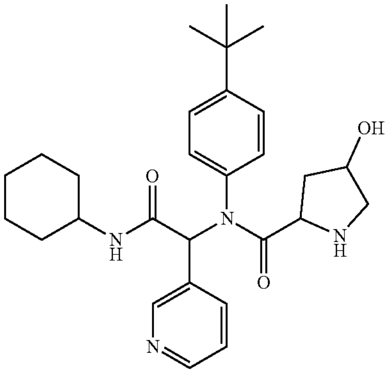 [SMILES: CC(C)(C)c1ccc(N(C(=O)C2CC(O)CN2)C(C(=O)NC2CCCCC2)c2cccnc2)cc1] |
| 252 | 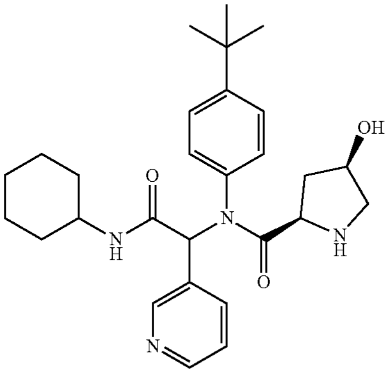 [SMILES: CC(C)(C)c1ccc(N(C(=O)[C@H]2C[C@@H](O)CN2)C(C(=O)NC2CCCCC2)c2cccnc2)cc1] |
TABLE 1-continued
| Exemplary compounds. | |
|---|---|
| Cmpd No. | Structure |
| 253 | 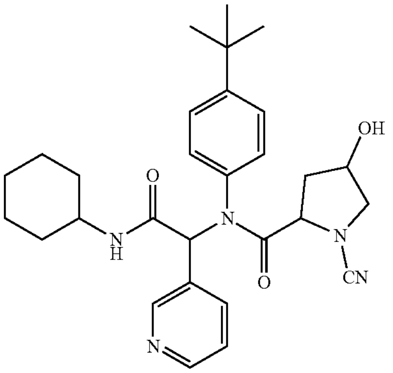 [SMILES: CC(C)(C)c1ccc(N(C(=O)C2CC(O)CN2C#N)C(C(=O)NC2CCCCC2)c2cccnc2)cc1] |
| 254 | 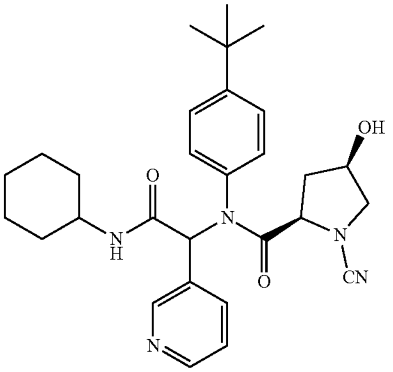 [SMILES: CC(C)(C)c1ccc(N(C(=O)[C@H]2C[C@@H](O)CN2C#N)C(C(=O)NC2CCCCC2)c2cccnc2)cc1] |
| 255 | 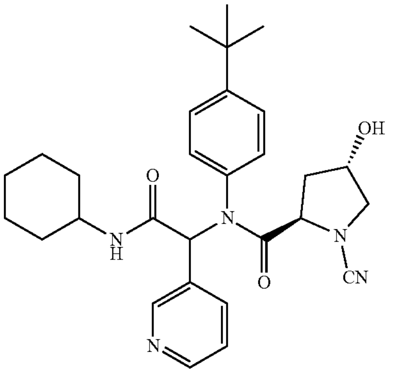 [SMILES: CC(C)(C)c1ccc(N(C(=O)[C@H]2C[C@H](O)CN2C#N)C(C(=O)NC2CCCCC2)c2cccnc2)cc1] |
| 255a | 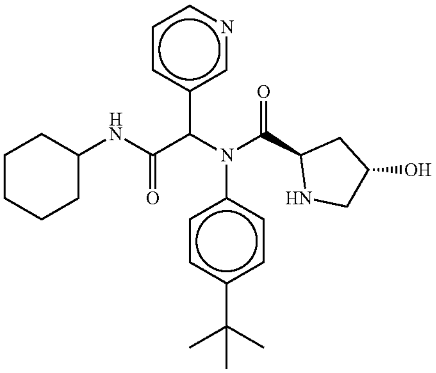 |

TABLE 1-continued
| Exemplary compounds. | |
|---|---|
| Cmpd No. | Structure |
| 256 | 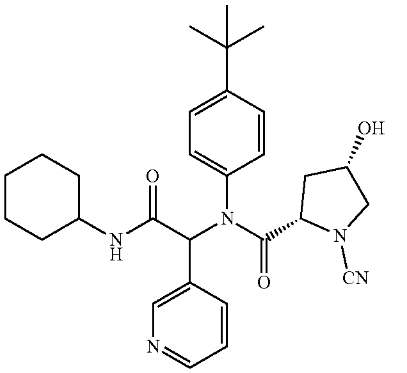 [SMILES: CC(C)(C)c1ccc(N(C(=O)[C@@H]2C[C@H](O)CN2C#N)C(C(=O)NC2CCCCC2)c2cccnc2)cc1] |
| 256a | 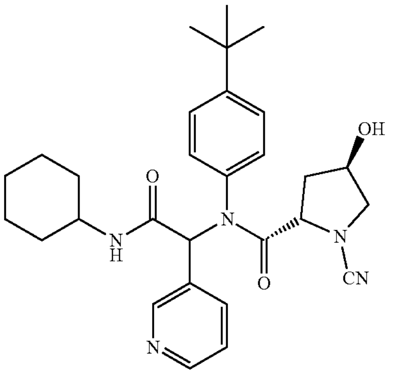 |
| 257 | 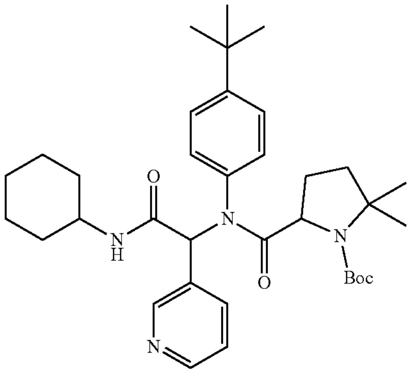 [SMILES: CC(C)(C)OC(=O)N1C(C(=O)N(c2ccc(C(C)(C)C)cc2)C(C(=O)NC2CCCCC2)c2cccnc2)CCC1(C)C] |
| 258 | 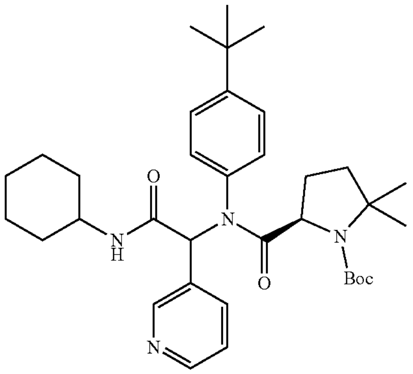 [SMILES: CC(C)(C)OC(=O)N1[C@@H](C(=O)N(c2ccc(C(C)(C)C)cc2)C(C(=O)NC2CCCCC2)c2cccnc2)CCC1(C)C] |
TABLE 1-continued
| Exemplary compounds. | |
|---|---|
| Cmpd No. | Structure |
| 259 | 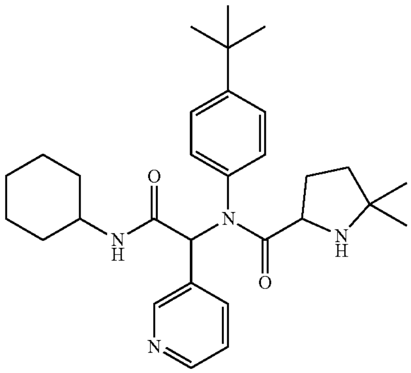 [SMILES: CC1(C)CCC(C(=O)N(c2ccc(C(C)(C)C)cc2)C(C(=O)NC2CCCCC2)c2cccnc2)N1] |
| 260 | 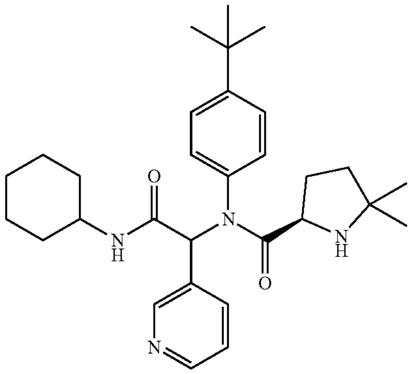 [SMILES: CC1(C)CC[C@H](C(=O)N(c2ccc(C(C)(C)C)cc2)C(C(=O)NC2CCCCC2)c2cccnc2)N1] |
| 261 | 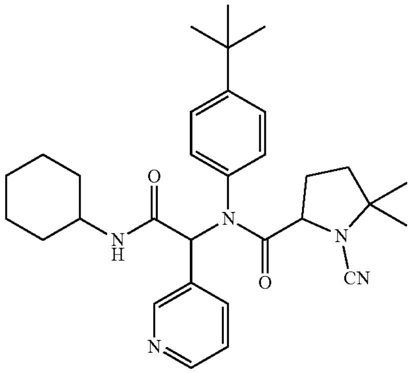 [SMILES: CC(C)(C)c1ccc(N(C(=O)C2CCC(C)(C)N2C#N)C(C(=O)NC2CCCCC2)c2cccnc2)cc1] |
| 262 | 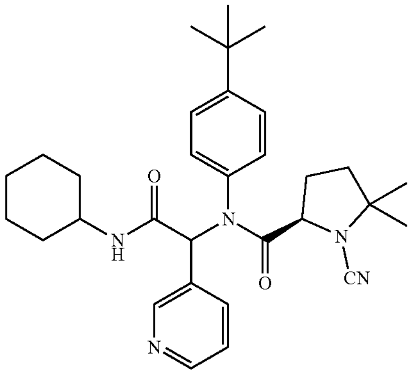 [SMILES: CC(C)(C)c1ccc(N(C(=O)[C@H]2CCC(C)(C)N2C#N)C(C(=O)NC2CCCCC2)c2cccnc2)cc1] |

TABLE 1-continued
| Exemplary compounds. | |
|---|---|
| Cmpd No. | Structure |
| 263 | 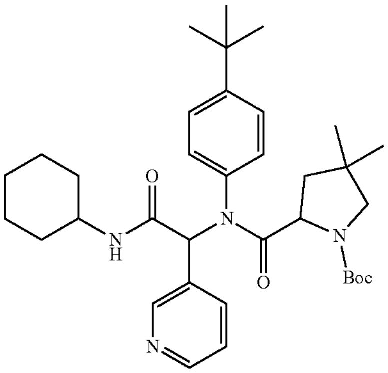 [SMILES: CC1(C)CC(C(=O)N(c2ccc(C(C)(C)C)cc2)C(C(=O)NC2CCCCC2)c2cccnc2)N(C(=O)OC(C)(C)C)C1] |
| 264 | 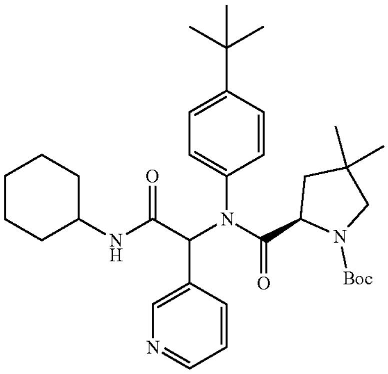 [SMILES: CC1(C)C[C@H](C(=O)N(c2ccc(C(C)(C)C)cc2)C(C(=O)NC2CCCCC2)c2cccnc2)N(C(=O)OC(C)(C)C)C1] |
| 265 | 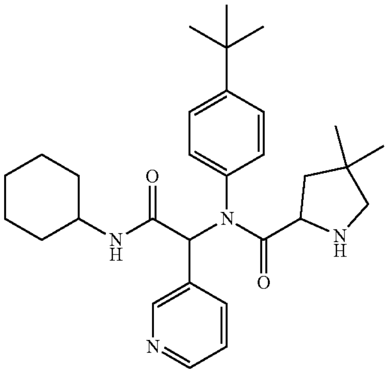 [SMILES: CC1(C)CNC(C(=O)N(c2ccc(C(C)(C)C)cc2)C(C(=O)NC2CCCCC2)c2cccnc2)C1] |
| 266 | 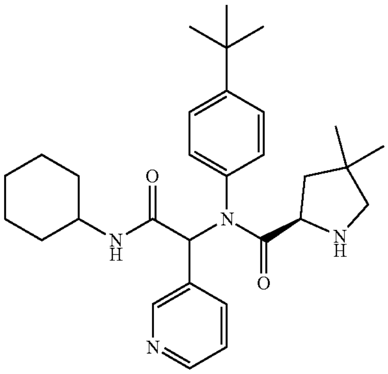 [SMILES: CC1(C)CN[C@@H](C(=O)N(c2ccc(C(C)(C)C)cc2)C(C(=O)NC2CCCCC2)c2cccnc2)C1] |
TABLE 1-continued
| Exemplary compounds. | |
|---|---|
| Cmpd No. | Structure |
| 268 | 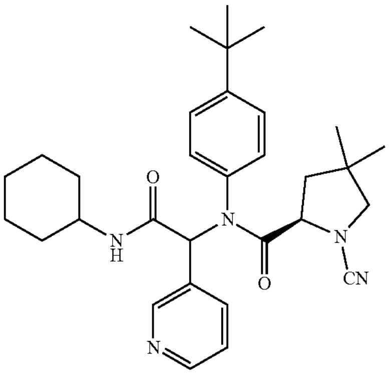 [SMILES: CC1(C)C[C@H](C(=O)N(c2ccc(C(C)(C)C)cc2)C(C(=O)NC2CCCCC2)c2cccnc2)N(C#N)C1] |
| 269 | 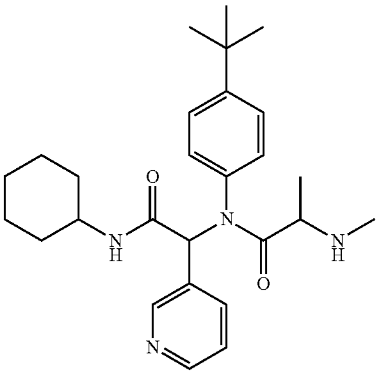 [SMILES: CNC(C)C(=O)N(c1ccc(C(C)(C)C)cc1)C(C(=O)NC1CCCCC1)c1cccnc1] |
| 270 | 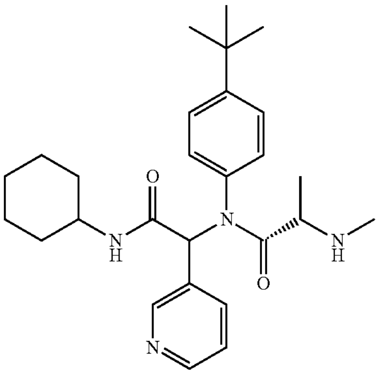 |
| 271a | 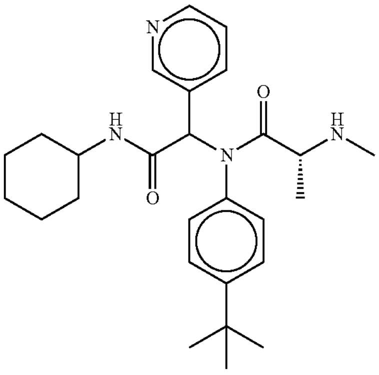 |

TABLE 1-continued
| Exemplary compounds. | |
|---|---|
| Cmpd No. | Structure |
| 271 | 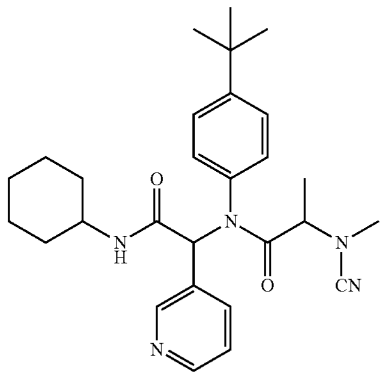 [SMILES: CC(C(=O)N(c1ccc(C(C)(C)C)cc1)C(C(=O)NC1CCCCC1)c1cccnc1)N(C)C#N] |
| 272 | 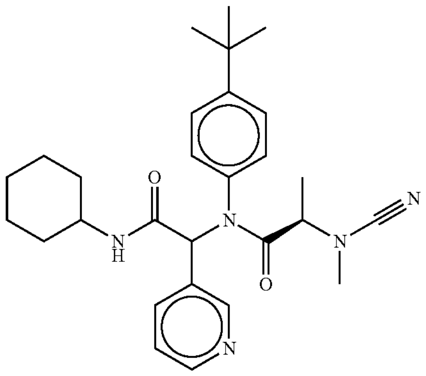 |
| 273 | 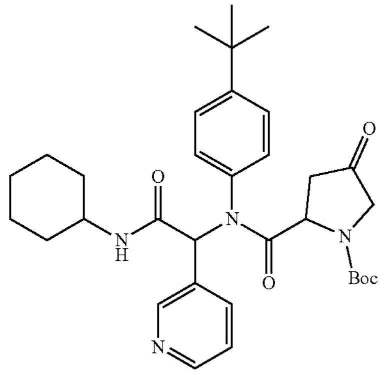 [SMILES: CC(C)(C)OC(=O)N1CC(=O)CC1C(=O)N(c1ccc(C(C)(C)C)cc1)C(C(=O)NC1CCCCC1)c1cccnc1] |
| 274 | 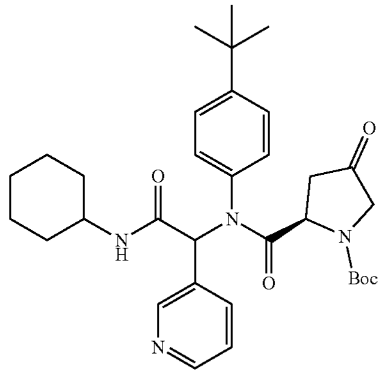 [SMILES: CC(C)(C)OC(=O)N1CC(=O)C[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 275 | 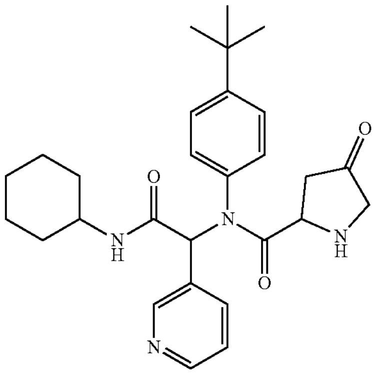 [SMILES: CC(C)(C)c1ccc(N(C(=O)C2CC(=O)CN2)C(C(=O)NC2CCCCC2)c2cccnc2)cc1] |
| 276 | 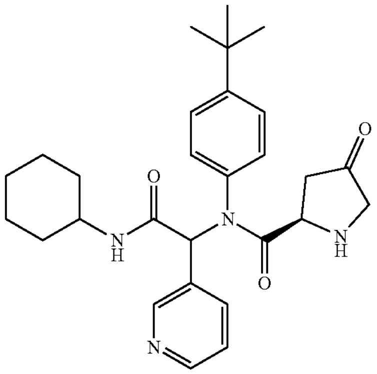 [SMILES: CC(C)(C)c1ccc(N(C(=O)[C@H]2CC(=O)CN2)C(C(=O)NC2CCCCC2)c2cccnc2)cc1] |
| 277 | 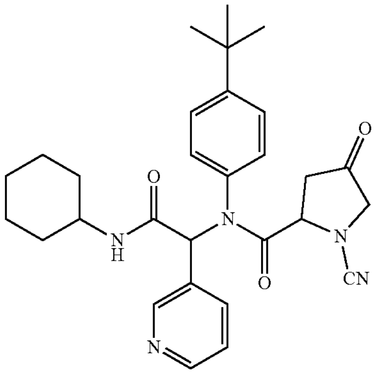 [SMILES: CC(C)(C)c1ccc(N(C(=O)C2CC(=O)CN2C#N)C(C(=O)NC2CCCCC2)c2cccnc2)cc1] |
| 278 | 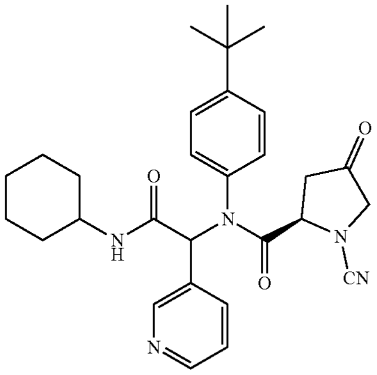 [SMILES: CC(C)(C)c1ccc(N(C(=O)[C@H]2CC(=O)CN2C#N)C(C(=O)NC2CCCCC2)c2cccnc2)cc1] |

TABLE 1-continued
| Cmpd No. | Structure |
|---|---|
| 279 | 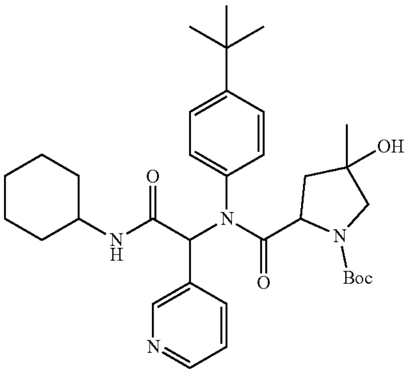 [SMILES: CC1(O)CC(C(=O)N(c2ccc(C(C)(C)C)cc2)C(C(=O)NC2CCCCC2)c2cccnc2)N(C(=O)OC(C)(C)C)C1] |
| 280 | 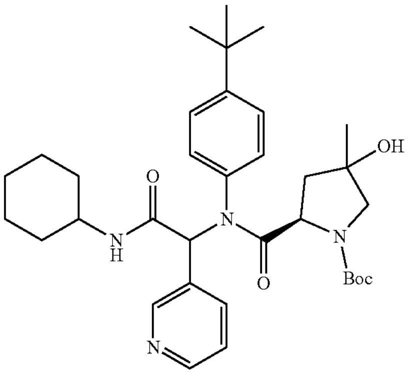 [SMILES: CC1(O)C[C@H](C(=O)N(c2ccc(C(C)(C)C)cc2)C(C(=O)NC2CCCCC2)c2cccnc2)N(C(=O)OC(C)(C)C)C1] |
| 281 | 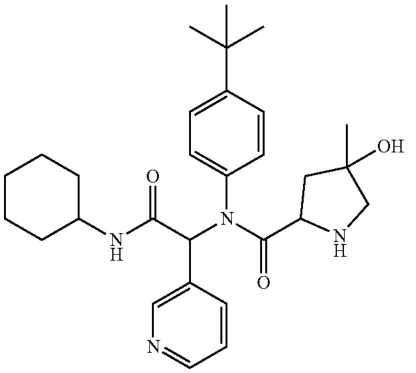 [SMILES: CC1(O)CNC(C(=O)N(c2ccc(C(C)(C)C)cc2)C(C(=O)NC2CCCCC2)c2cccnc2)C1] |
| 282 | 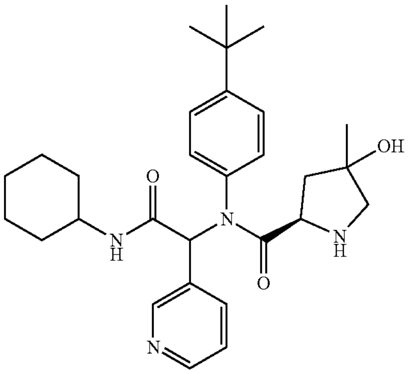 [SMILES: CC1(O)CN[C@@H](C(=O)N(c2ccc(C(C)(C)C)cc2)C(C(=O)NC2CCCCC2)c2cccnc2)C1] |
| 283 | 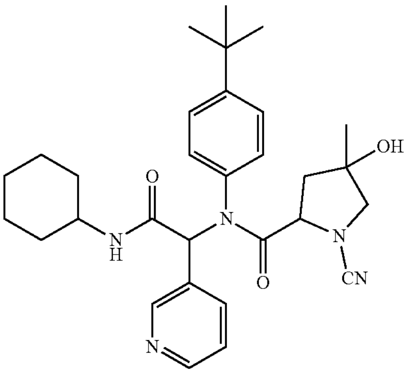 [SMILES: CC1(O)CC(C(=O)N(c2ccc(C(C)(C)C)cc2)C(C(=O)NC2CCCCC2)c2cccnc2)N(C#N)C1] |
| 284 | 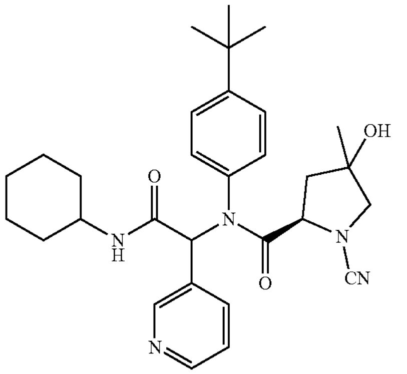 [SMILES: CC1(O)C[C@H](C(=O)N(c2ccc(C(C)(C)C)cc2)C(C(=O)NC2CCCCC2)c2cccnc2)N(C#N)C1] |
| 284a | 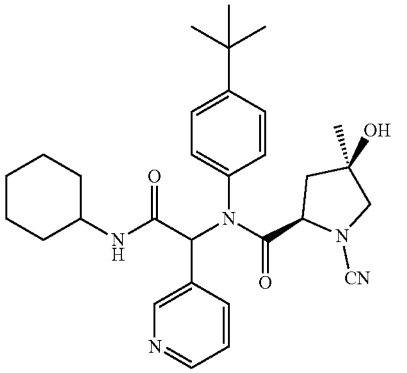 [SMILES: CC(C)(C)c1ccc(N(C(=O)[C@H]2C[C@@](C)(O)CN2C#N)C(C(=O)NC2CCCCC2)c2cccnc2)cc1] |
| 285 | 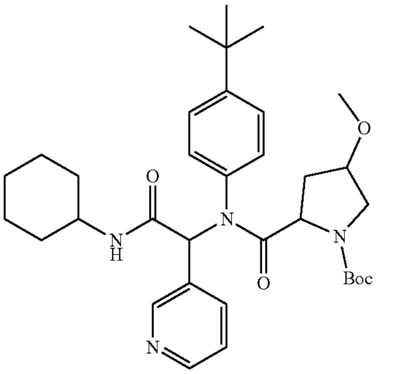 [SMILES: COC1CC(C(=O)N(c2ccc(C(C)(C)C)cc2)C(C(=O)NC2CCCCC2)c2cccnc2)N(C(=O)OC(C)(C)C)C1] |
Exemplary compounds.

TABLE 1-continued
Exemplary compounds.
| Cmpd No. | Structure |
|---|---|
| 286 | 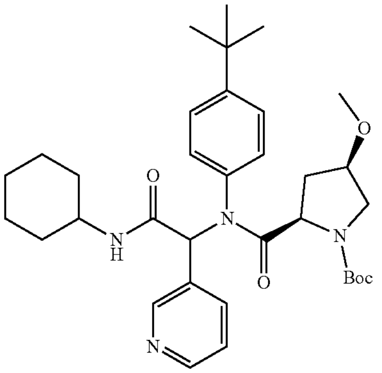 [SMILES: CO[C@@H]1C[C@H](C(=O)N(c2ccc(C(C)(C)C)cc2)C(C(=O)NC2CCCCC2)c2cccnc2)N(C(=O)OC(C)(C)C)C1] |
| 287 | 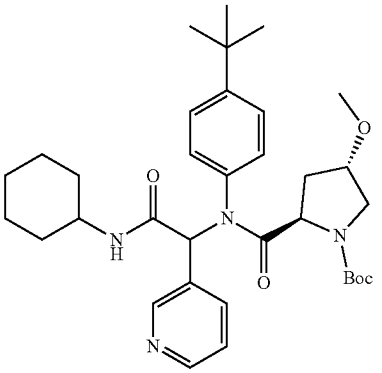 [SMILES: CO[C@H]1C[C@H](C(=O)N(c2ccc(C(C)(C)C)cc2)C(C(=O)NC2CCCCC2)c2cccnc2)N(C(=O)OC(C)(C)C)C1] |
| 288 | 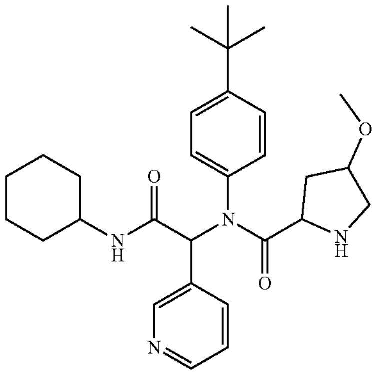 [SMILES: COC1CNC(C(=O)N(c2ccc(C(C)(C)C)cc2)C(C(=O)NC2CCCCC2)c2cccnc2)C1] |
| 289 | 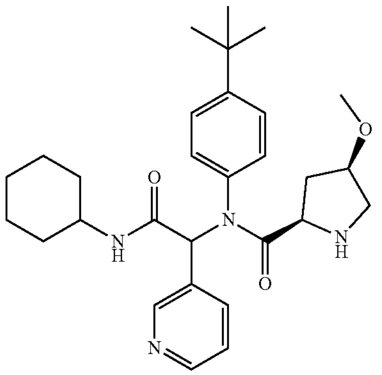 [SMILES: CO[C@H]1CN[C@@H](C(=O)N(c2ccc(C(C)(C)C)cc2)C(C(=O)NC2CCCCC2)c2cccnc2)C1] |
| 290 | 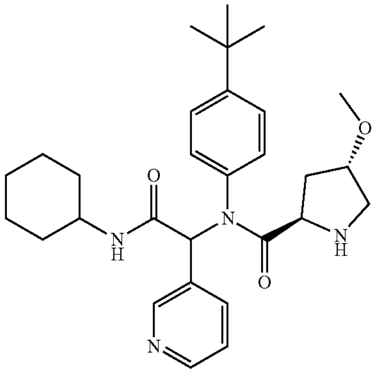 [SMILES: CO[C@@H]1CN[C@@H](C(=O)N(c2ccc(C(C)(C)C)cc2)C(C(=O)NC2CCCCC2)c2cccnc2)C1] |
| 291 | 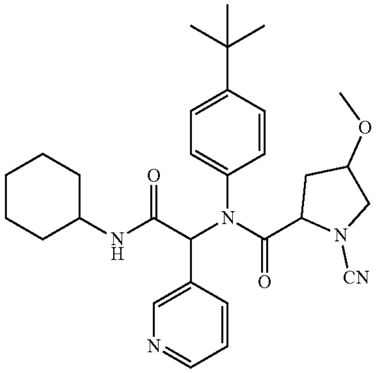 [SMILES: COC1CC(C(=O)N(c2ccc(C(C)(C)C)cc2)C(C(=O)NC2CCCCC2)c2cccnc2)N(C#N)C1] |
| 292 | 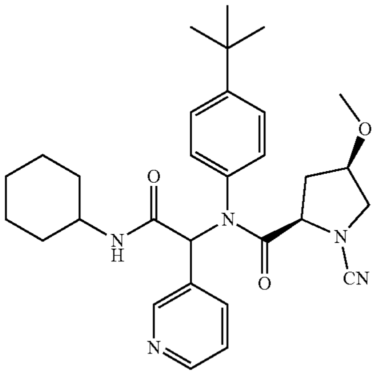 [SMILES: CO[C@@H]1C[C@H](C(=O)N(c2ccc(C(C)(C)C)cc2)C(C(=O)NC2CCCCC2)c2cccnc2)N(C#N)C1] |
| 293 | 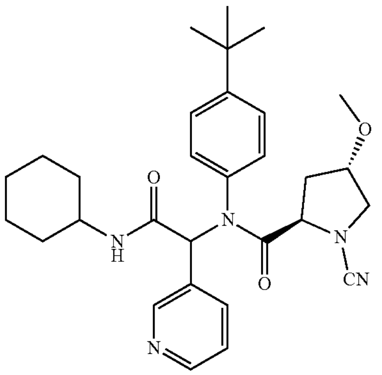 [SMILES: CO[C@H]1C[C@H](C(=O)N(c2ccc(C(C)(C)C)cc2)C(C(=O)NC2CCCCC2)c2cccnc2)N(C#N)C1] |

TABLE 1-continued
Exemplary compounds.
| Cmpd No. | Structure |
|---|---|
| 294 | 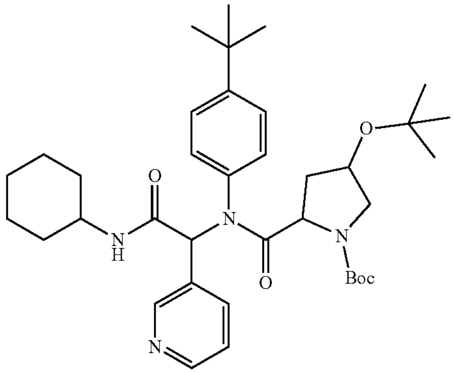 [SMILES: CC(C)(C)OC(=O)N1CC(OC(C)(C)C)CC1C(=O)N(c1ccc(C(C)(C)C)cc1)C(C(=O)NC1CCCCC1)c1cccnc1] |
| 295 | 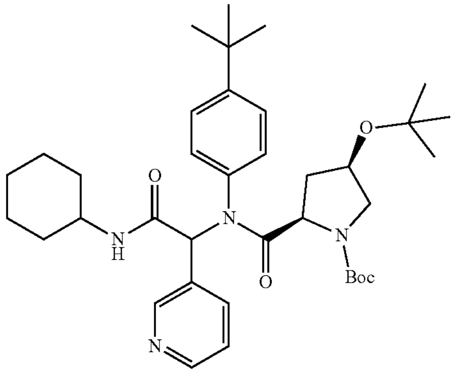 [SMILES: CC(C)(C)OC(=O)N1C[C@H](OC(C)(C)C)C[C@@H]1C(=O)N(c1ccc(C(C)(C)C)cc1)C(C(=O)NC1CCCCC1)c1cccnc1] |
| 296 | 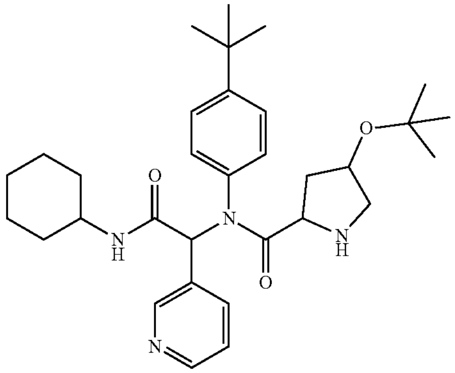 [SMILES: CC(C)(C)OC1CNC(C(=O)N(c2ccc(C(C)(C)C)cc2)C(C(=O)NC2CCCCC2)c2cccnc2)C1] |
| 297 | 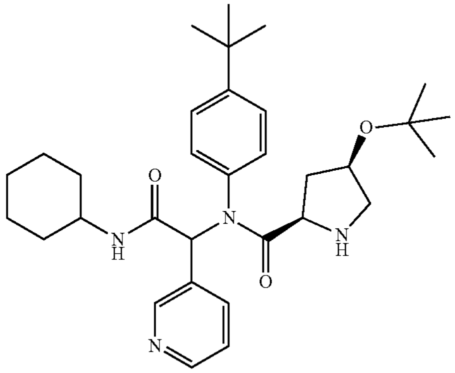 [SMILES: CC(C)(C)O[C@H]1CN[C@@H](C(=O)N(c2ccc(C(C)(C)C)cc2)C(C(=O)NC2CCCCC2)c2cccnc2)C1] |
| 298 | 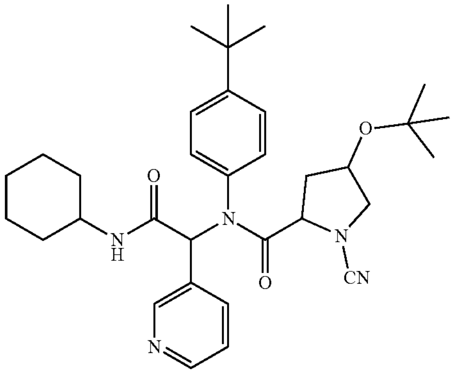 [SMILES: CC(C)(C)OC1CC(C(=O)N(c2ccc(C(C)(C)C)cc2)C(C(=O)NC2CCCCC2)c2cccnc2)N(C#N)C1] |
| 299 | 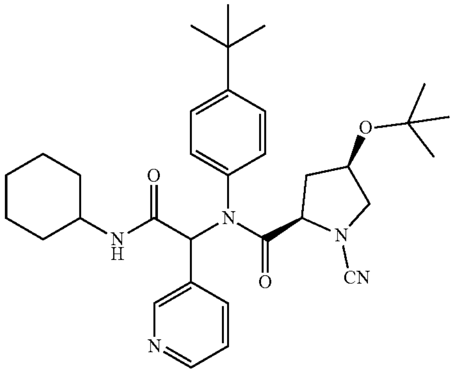 [SMILES: CC(C)(C)O[C@@H]1C[C@H](C(=O)N(c2ccc(C(C)(C)C)cc2)C(C(=O)NC2CCCCC2)c2cccnc2)N(C#N)C1] |
| 300 | 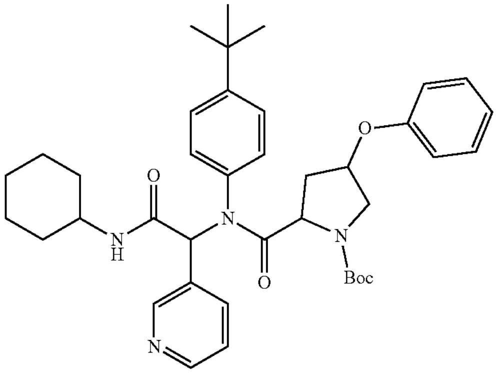 [SMILES: CC(C)(C)OC(=O)N1CC(Oc2ccccc2)CC1C(=O)N(c1ccc(C(C)(C)C)cc1)C(C(=O)NC1CCCCC1)c1cccnc1] |
| 301 | 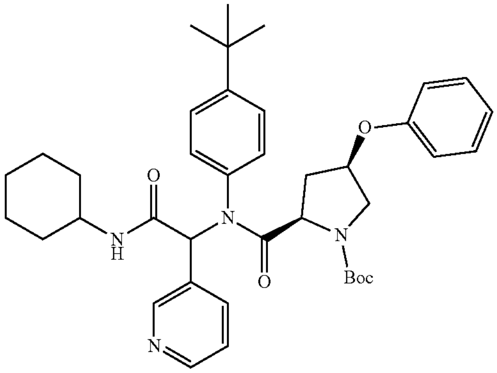 [SMILES: CC(C)(C)OC(=O)N1C[C@H](Oc2ccccc2)C[C@@H]1C(=O)N(c1ccc(C(C)(C)C)cc1)C(C(=O)NC1CCCCC1)c1cccnc1] |

TABLE 1-continued
Exemplary compounds.
| Cmpd No. | Structure |
|---|---|
| 302 | 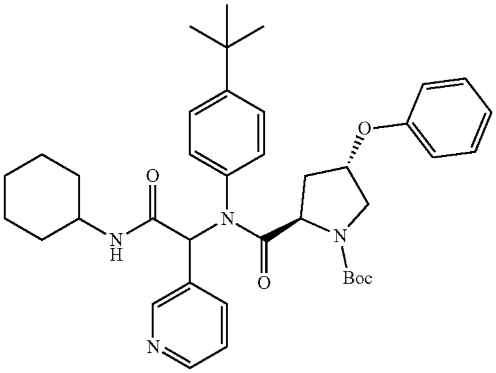 [SMILES: CC(C)(C)OC(=O)N1C[C@@H](Oc2ccccc2)C[C@@H]1C(=O)N(c1ccc(C(C)(C)C)cc1)C(C(=O)NC1CCCCC1)c1cccnc1] |
| 303 | 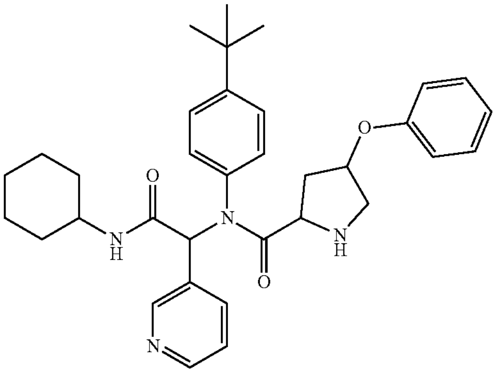 [SMILES: CC(C)(C)c1ccc(N(C(=O)C2CC(Oc3ccccc3)CN2)C(C(=O)NC2CCCCC2)c2cccnc2)cc1] |
| 304 | 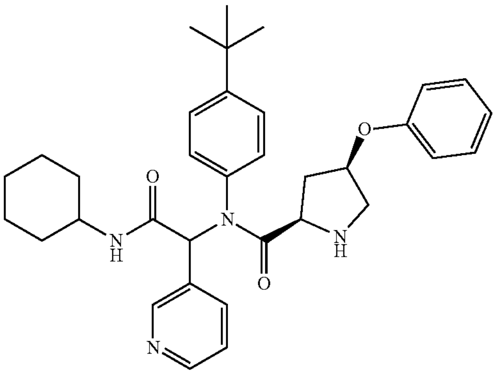 [SMILES: CC(C)(C)c1ccc(N(C(=O)[C@H]2C[C@@H](Oc3ccccc3)CN2)C(C(=O)NC2CCCCC2)c2cccnc2)cc1] |
| 305 | 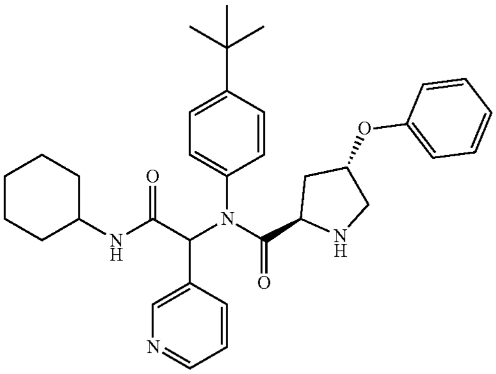 [SMILES: CC(C)(C)c1ccc(N(C(=O)[C@H]2C[C@H](Oc3ccccc3)CN2)C(C(=O)NC2CCCCC2)c2cccnc2)cc1] |
| 306 | 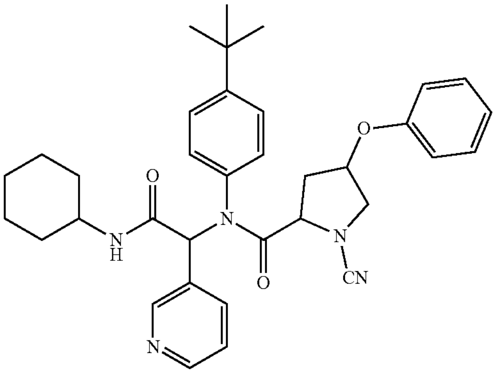 [SMILES: CC(C)(C)c1ccc(N(C(=O)C2CC(Oc3ccccc3)CN2C#N)C(C(=O)NC2CCCCC2)c2cccnc2)cc1] |
| 307 | 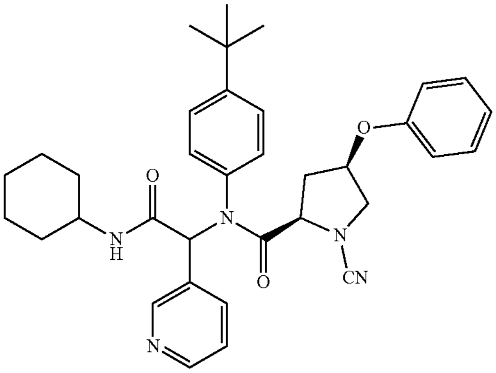 [SMILES: CC(C)(C)c1ccc(N(C(=O)[C@H]2C[C@@H](Oc3ccccc3)CN2C#N)C(C(=O)NC2CCCCC2)c2cccnc2)cc1] |
| 308 | 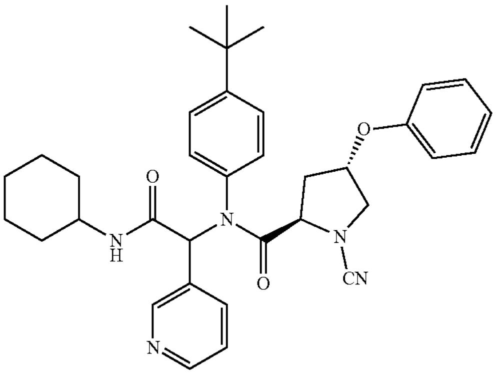 [SMILES: CC(C)(C)c1ccc(N(C(=O)[C@H]2C[C@H](Oc3ccccc3)CN2C#N)C(C(=O)NC2CCCCC2)c2cccnc2)cc1] |
| 309 | 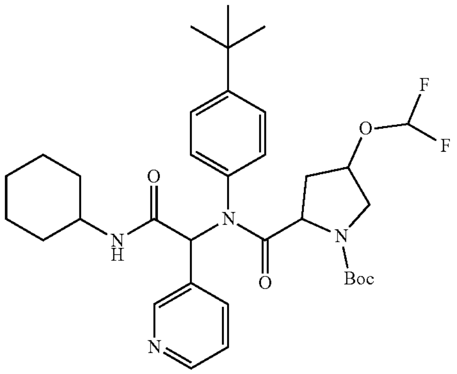 [SMILES: CC(C)(C)OC(=O)N1CC(OC(F)F)CC1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 310 | 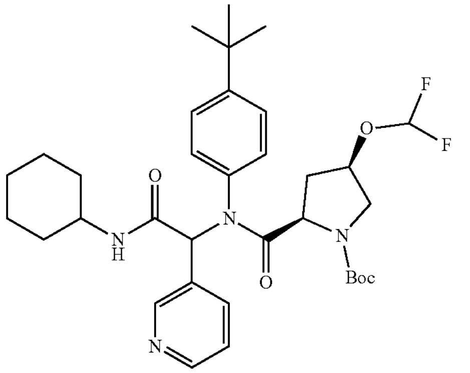 [SMILES: CC(C)(C)OC(=O)N1C[C@H](OC(F)F)C[C@@H]1C(=O)N(c1ccc(C(C)(C)C)cc1)C(C(=O)NC1CCCCC1)c1cccnc1] |
| 311 | 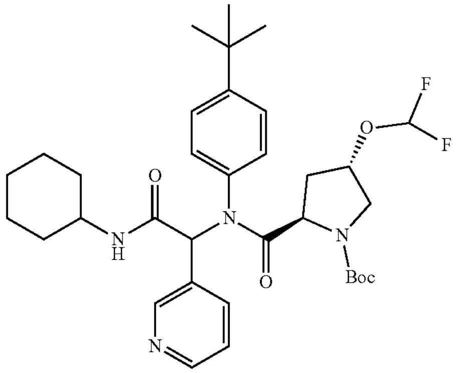 [SMILES: CC(C)(C)OC(=O)N1C[C@@H](OC(F)F)C[C@@H]1C(=O)N(c1ccc(C(C)(C)C)cc1)C(C(=O)NC1CCCCC1)c1cccnc1] |
| 312 | 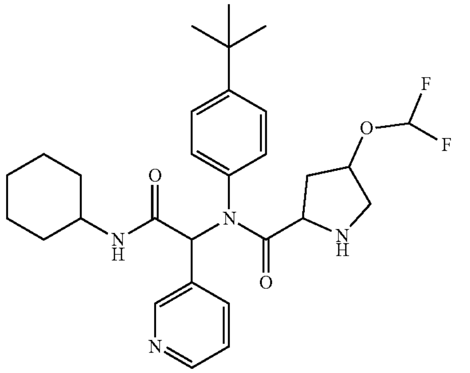 [SMILES: CC(C)(C)c1ccc(N(C(=O)C2CC(OC(F)F)CN2)C(C(=O)NC2CCCCC2)c2cccnc2)cc1] |
| 313 | 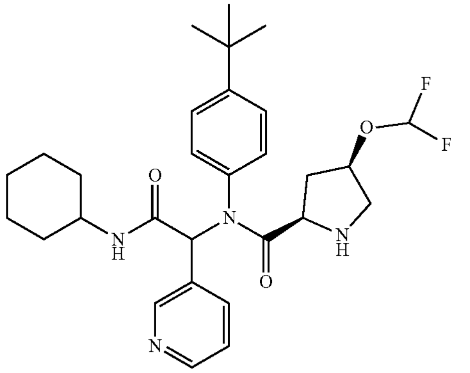 [SMILES: CC(C)(C)c1ccc(N(C(=O)[C@H]2C[C@@H](OC(F)F)CN2)C(C(=O)NC2CCCCC2)c2cccnc2)cc1] |
TABLE 1-continued
| Exemplary compounds. | |
|---|---|
| Cmpd No. | Structure |
| 314 | 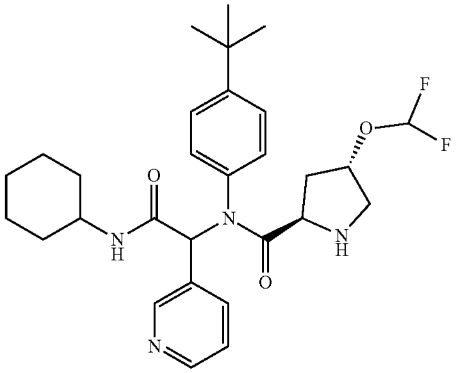 [SMILES: CC(C)(C)c1ccc(N(C(=O)[C@H]2C[C@H](OC(F)F)CN2)C(C(=O)NC2CCCCC2)c2cccnc2)cc1] |
| 315 | 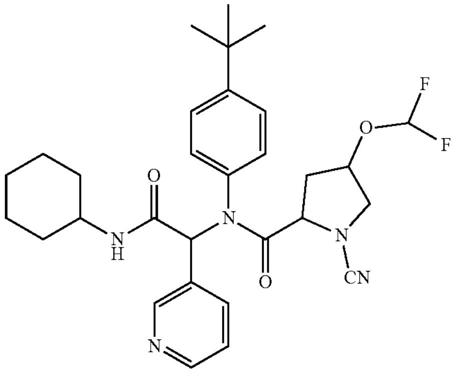 [SMILES: CC(C)(C)c1ccc(N(C(=O)C2CC(OC(F)F)CN2C#N)C(C(=O)NC2CCCCC2)c2cccnc2)cc1] |
| 316 | 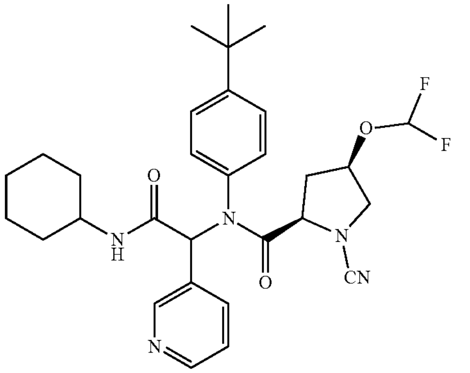 [SMILES: CC(C)(C)c1ccc(N(C(=O)[C@H]2C[C@@H](OC(F)F)CN2C#N)C(C(=O)NC2CCCCC2)c2cccnc2)cc1] |
| 317 | 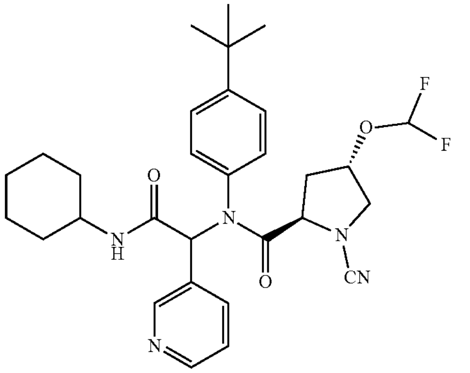 [SMILES: CC(C)(C)c1ccc(N(C(=O)[C@H]2C[C@H](OC(F)F)CN2C#N)C(C(=O)NC2CCCCC2)c2cccnc2)cc1] |

TABLE 1-continued
| Exemplary compounds. | |
|---|---|
| Cmpd No. | Structure |
| 318 | 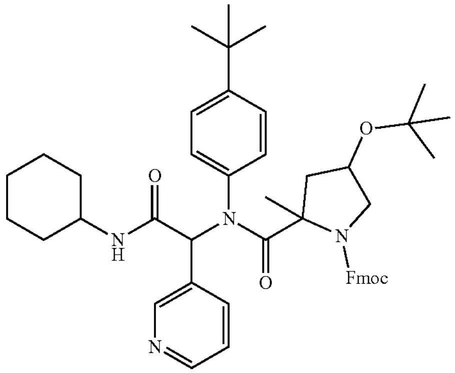 |
| 319 | 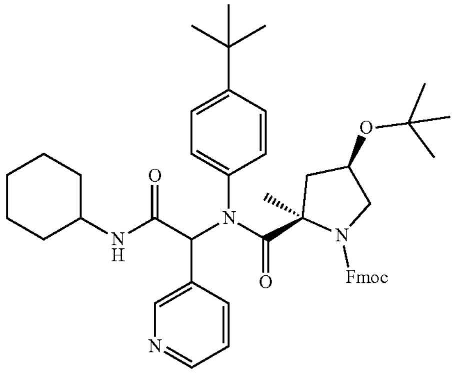 |
| 320 | 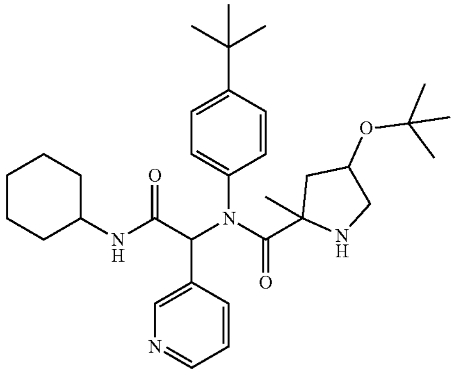 [SMILES: CC(C)(C)OC1CNC(C)(C(=O)N(c2ccc(C(C)(C)C)cc2)C(C(=O)NC2CCCCC2)c2cccnc2)C1] |
| 321 | 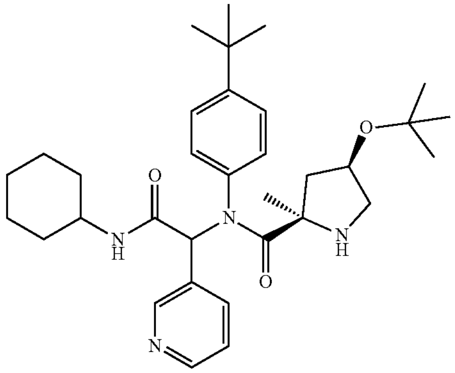 [SMILES: CC(C)(C)O[C@H]1CN[C@@](C)(C(=O)N(c2ccc(C(C)(C)C)cc2)C(C(=O)NC2CCCCC2)c2cccnc2)C1] |
TABLE 1-continued
| Exemplary compounds. | |
|---|---|
| Cmpd No. | Structure |
| 322 | 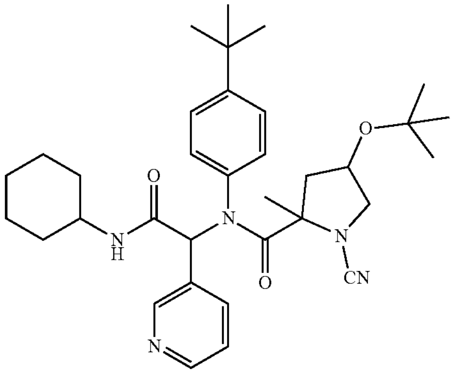 [SMILES: CC(C)(C)OC1CN(C#N)C(C)(C(=O)N(c2ccc(C(C)(C)C)cc2)C(C(=O)NC2CCCCC2)c2cccnc2)C1] |
| 323 | 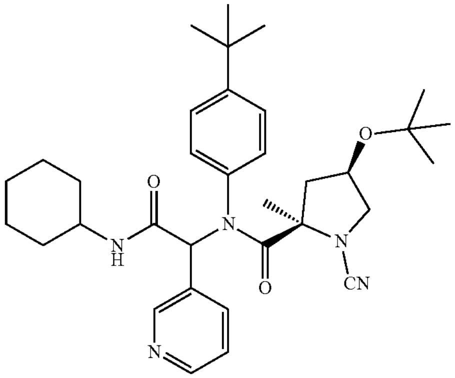 [SMILES: CC(C)(C)O[C@H]1CN(C#N)[C@@](C)(C(=O)N(c2ccc(C(C)(C)C)cc2)C(C(=O)NC2CCCCC2)c2cccnc2)C1] |
| 324 | 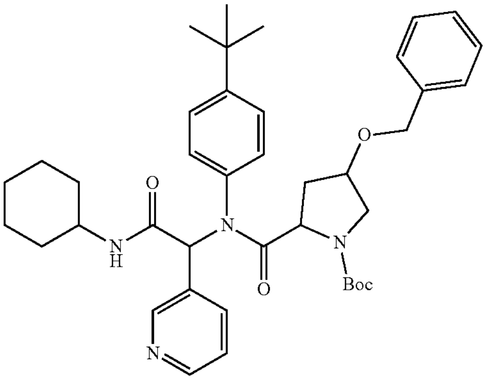 [SMILES: CC(C)(C)OC(=O)N1CC(OCc2ccccc2)CC1C(=O)N(c1ccc(C(C)(C)C)cc1)C(C(=O)NC1CCCCC1)c1cccnc1] |
| 325 | 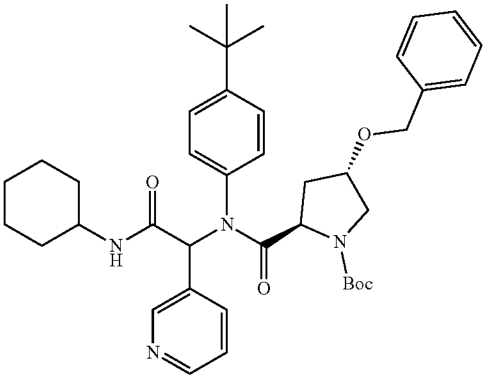 [SMILES: CC(C)(C)OC(=O)N1C[C@@H](OCc2ccccc2)C[C@@H]1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 326 | 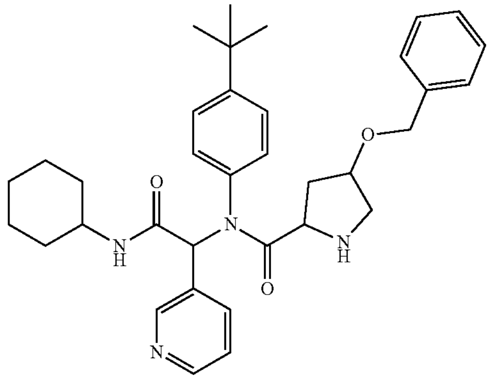 [SMILES: CC(C)(C)c1ccc(N(C(=O)C2CC(OCc3ccccc3)CN2)C(C(=O)NC2CCCCC2)c2cccnc2)cc1] |
| 327 | 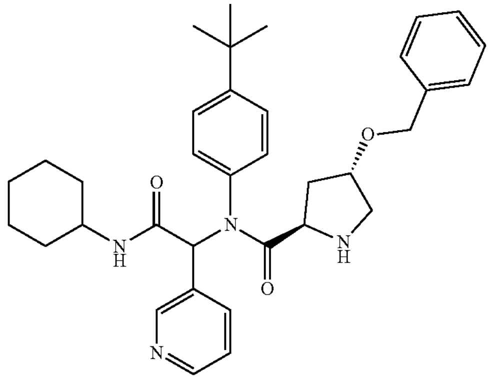 [SMILES: CC(C)(C)c1ccc(N(C(=O)[C@H]2C[C@H](OCc3ccccc3)CN2)C(C(=O)NC2CCCCC2)c2cccnc2)cc1] |
| 328 | 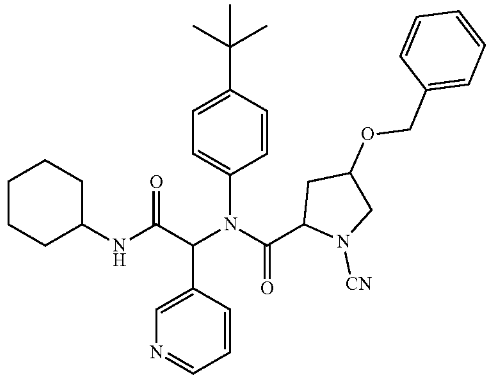 [SMILES: CC(C)(C)c1ccc(N(C(=O)C2CC(OCc3ccccc3)CN2C#N)C(C(=O)NC2CCCCC2)c2cccnc2)cc1] |
| 329 | 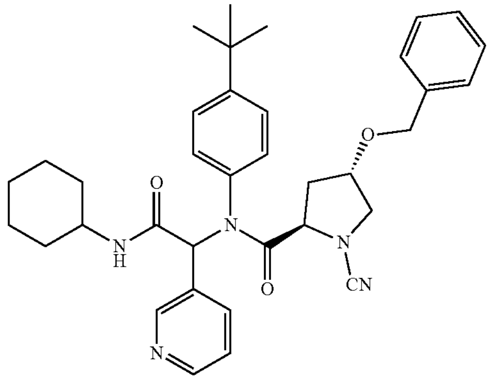 [SMILES: CC(C)(C)c1ccc(N(C(=O)[C@H]2C[C@H](OCc3ccccc3)CN2C#N)C(C(=O)NC2CCCCC2)c2cccnc2)cc1] |
TABLE 1-continued
| Exemplary compounds. | |
|---|---|
| Cmpd No. | Structure |
| 330 | 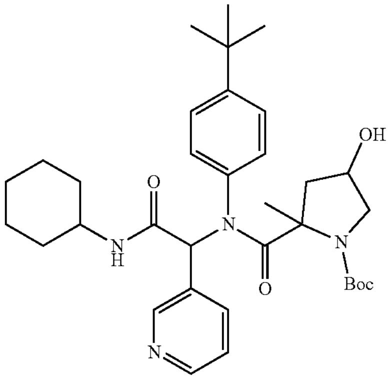 [SMILES: CC(C)(C)OC(=O)N1CC(O)CC1(C)C(=O)N(c1ccc(C(C)(C)C)cc1)C(C(=O)NC1CCCCC1)c1cccnc1] |
| 331 | 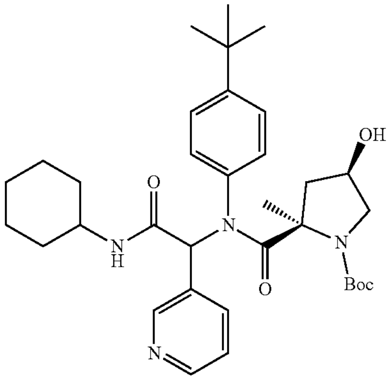 [SMILES: CC(C)(C)OC(=O)N1C[C@H](O)C[C@]1(C)C(=O)N(c1ccc(C(C)(C)C)cc1)C(C(=O)NC1CCCCC1)c1cccnc1] |
| 332 | 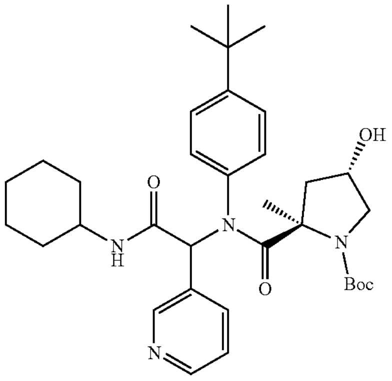 [SMILES: CC(C)(C)OC(=O)N1C[C@@H](O)C[C@]1(C)C(=O)N(c1ccc(C(C)(C)C)cc1)C(C(=O)NC1CCCCC1)c1cccnc1] |
| 333 | 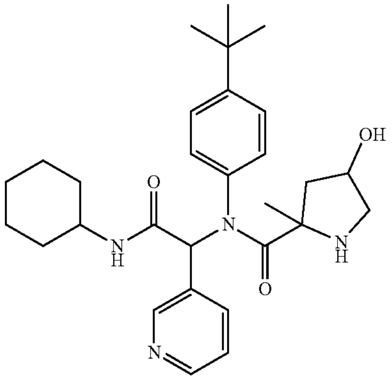 [SMILES: CC1(C(=O)N(c2ccc(C(C)(C)C)cc2)C(C(=O)NC2CCCCC2)c2cccnc2)CC(O)CN1] |

TABLE 1-continued
| Cmpd No. | Structure |
|---|---|
| 334 | 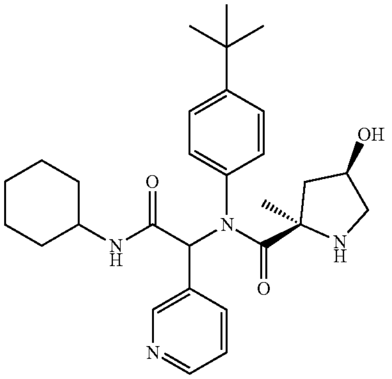 [SMILES: CC(C)(C)c1ccc(N(C(=O)[C@@]2(C)C[C@@H](O)CN2)C(C(=O)NC2CCCCC2)c2cccnc2)cc1] |
| 335 | 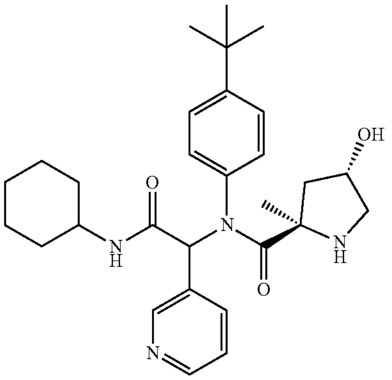 [SMILES: CC(C)(C)c1ccc(N(C(=O)[C@@]2(C)C[C@H](O)CN2)C(C(=O)NC2CCCCC2)c2cccnc2)cc1] |
| 336 | 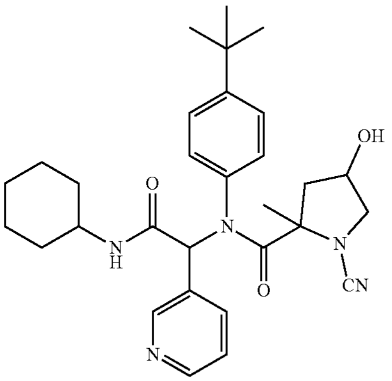 [SMILES: CC(C)(C)c1ccc(N(C(=O)C2(C)CC(O)CN2C#N)C(C(=O)NC2CCCCC2)c2cccnc2)cc1] |
| 337 | 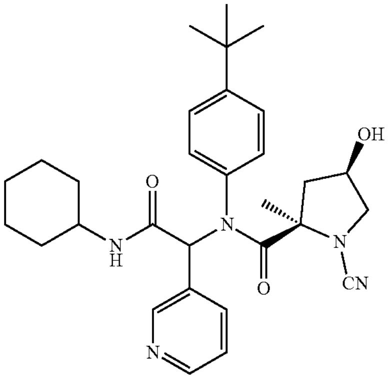 [SMILES: CC(C)(C)c1ccc(N(C(=O)[C@@]2(C)C[C@@H](O)CN2C#N)C(C(=O)NC2CCCCC2)c2cccnc2)cc1] |
TABLE 1-continued
| Cmpd No. | Structure |
|---|---|
| 338 | 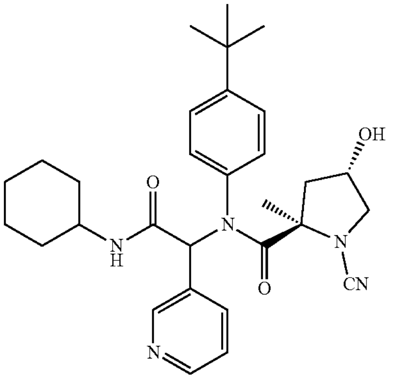 [SMILES: CC(C)(C)c1ccc(N(C(=O)[C@@]2(C)C[C@H](O)CN2C#N)C(C(=O)NC2CCCCC2)c2cccnc2)cc1] |
| 339 | 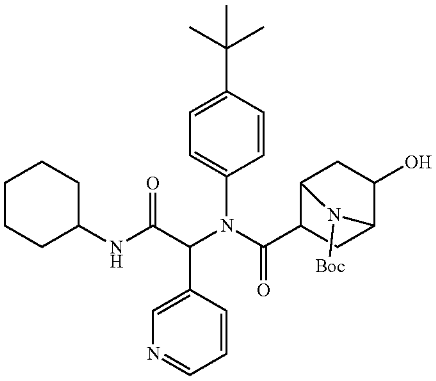 [SMILES: CC(C)(C)OC(=O)N1C2CC(C(=O)N(c3ccc(C(C)(C)C)cc3)C(C(=O)NC3CCCCC3)c3cccnc3)C1CC2O] |
| 340 | 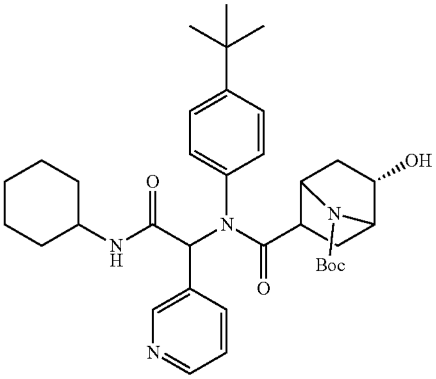 [SMILES: CC(C)(C)OC(=O)N1C2C[C@H](O)C1CC2C(=O)N(c1ccc(C(C)(C)C)cc1)C(C(=O)NC1CCCCC1)c1cccnc1] |
| 341 | 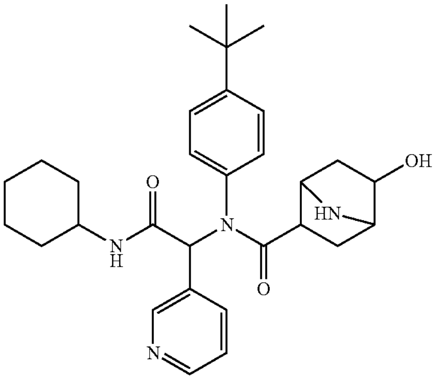 [SMILES: CC(C)(C)c1ccc(N(C(=O)C2CC3NC2CC3O)C(C(=O)NC2CCCCC2)c2cccnc2)cc1] |

TABLE 1-continued
Exemplary compounds.
| Cmpd No. | Structure |
| --- | --- |
| 342 | 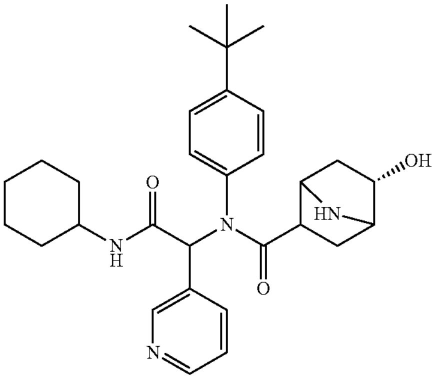 [SMILES: CC(C)(C)c1ccc(N(C(=O)C2CC3NC2C[C@@H]3O)C(C(=O)NC2CCCCC2)c2cccnc2)cc1] |
| 343 | 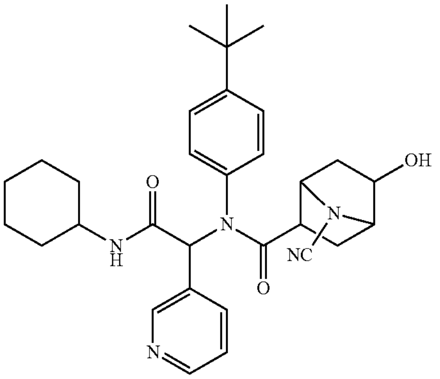 |
| 344 | 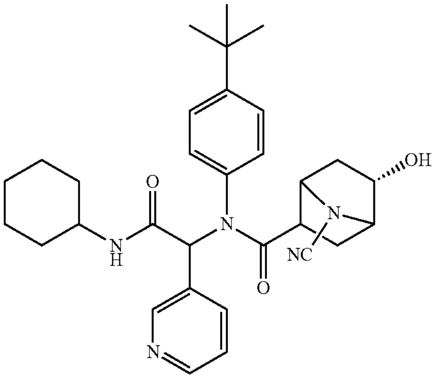 [SMILES: CC(C)(C)c1ccc(N(C(=O)C2CC3[C@@H](O)CC2N3C#N)C(C(=O)NC2CCCCC2)c2cccnc2)cc1] |
| 345 | 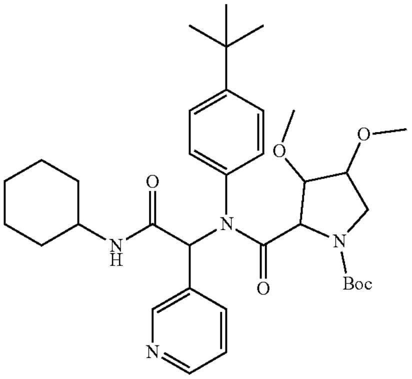 [SMILES: COC1CN(C(=O)OC(C)(C)C)C(C(=O)N(c2ccc(C(C)(C)C)cc2)C(C(=O)NC2CCCCC2)c2cccnc2)C1OC] |
TABLE 1-continued
Exemplary compounds.
| Cmpd No. | Structure |
| --- | --- |
| 346 | 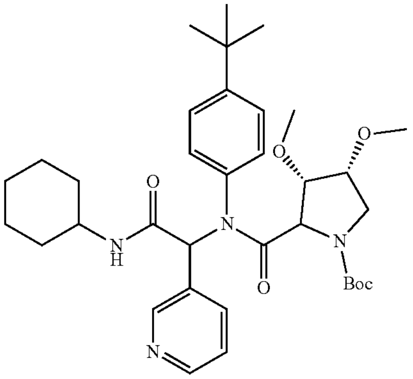 |
| 347 | 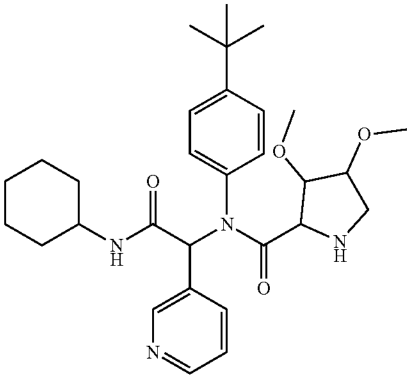 [SMILES: COC1CNC(C(=O)N(c2ccc(C(C)(C)C)cc2)C(C(=O)NC2CCCCC2)c2cccnc2)C1OC] |
| 348 | 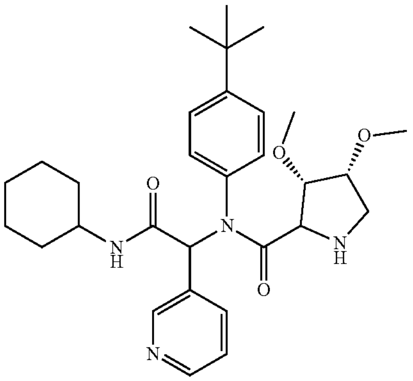 [SMILES: CO[C@@H]1CNC(C(=O)N(c2ccc(C(C)(C)C)cc2)C(C(=O)NC2CCCCC2)c2cccnc2)[C@@H]1OC] |
| 349 | 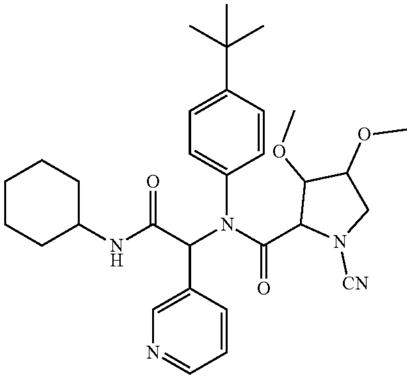 [SMILES: COC1CN(C#N)C(C(=O)N(c2ccc(C(C)(C)C)cc2)C(C(=O)NC2CCCCC2)c2cccnc2)C1OC] |

TABLE 1-continued
Exemplary compounds.
| Cmpd No. | Structure |
| --- | --- |
| 350 | 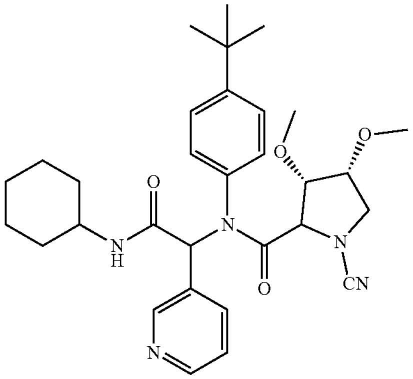 [SMILES: CO[C@@H]1CN(C#N)C(C(=O)N(c2ccc(C(C)(C)C)cc2)C(C(=O)NC2CCCCC2)c2cccnc2)[C@@H]1OC] |
| 351 | 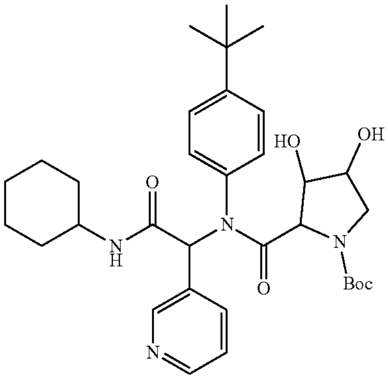 [SMILES: CC(C)(C)OC(=O)N1CC(O)C(O)C1C(=O)N(c1ccc(C(C)(C)C)cc1)C(C(=O)NC1CCCCC1)c1cccnc1] |
| 352 | 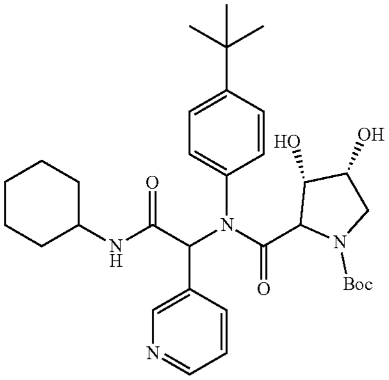 [SMILES: CC(C)(C)OC(=O)N1C[C@@H](O)[C@@H](O)C1C(=O)N(c1ccc(C(C)(C)C)cc1)C(C(=O)NC1CCCCC1)c1cccnc1] |
| 353 | 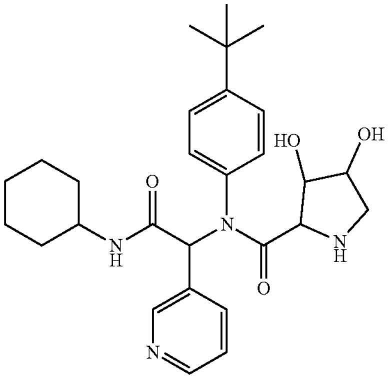 [SMILES: CC(C)(C)c1ccc(N(C(=O)C2NCC(O)C2O)C(C(=O)NC2CCCCC2)c2cccnc2)cc1] |
| 354 | 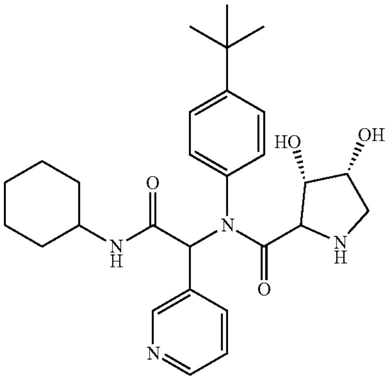 |
| 355 | 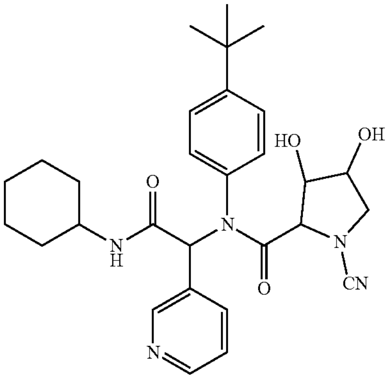 [SMILES: CC(C)(C)c1ccc(N(C(=O)C2C(O)C(O)CN2C#N)C(C(=O)NC2CCCCC2)c2cccnc2)cc1] |
| 356 | 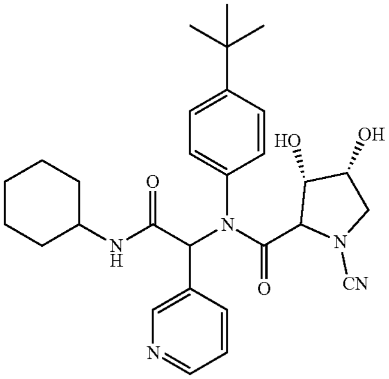 [SMILES: CC(C)(C)c1ccc(N(C(=O)C2[C@H](O)[C@H](O)CN2C#N)C(C(=O)NC2CCCCC2)c2cccnc2)cc1] |
| 357 | 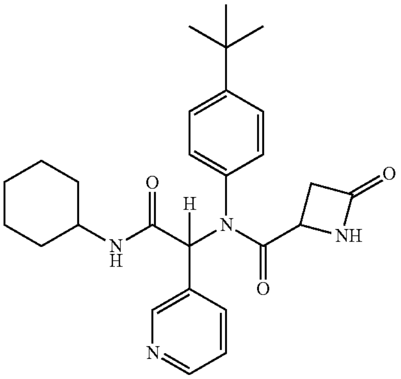 [SMILES: CC(C)(C)c1ccc(N(C(=O)C2CC(=O)N2)C(C(=O)NC2CCCCC2)c2cccnc2)cc1] |

TABLE 1-continued
| Exemplary compounds. | |
|---|---|
| Cmpd No. | Structure |
| 358 | 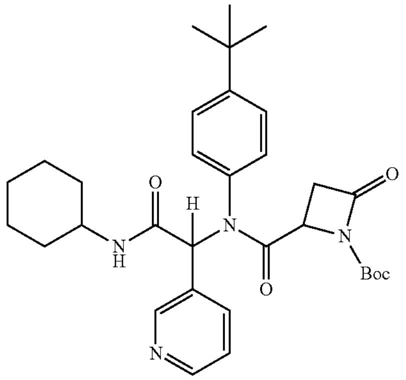 [SMILES: CC(C)(C)OC(=O)N1C(=O)CC1C(=O)N(c1ccc(C(C)(C)C)cc1)C(C(=O)NC1CCCCC1)c1cccnc1] |
| 359 | 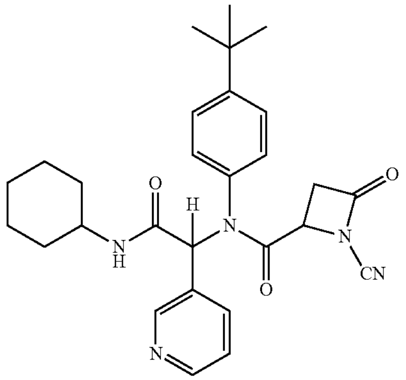 [SMILES: CC(C)(C)c1ccc(N(C(=O)C2CC(=O)N2C#N)C(C(=O)NC2CCCCC2)c2cccnc2)cc1] |
| 360 | 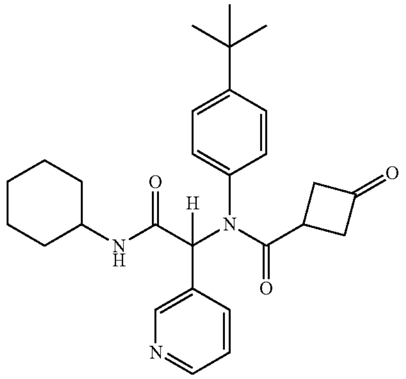 |
| 361 | 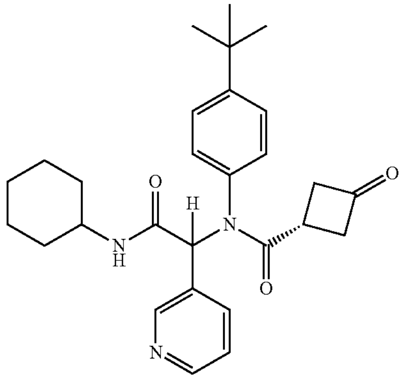 |
TABLE 1-continued
| Exemplary compounds. | |
|---|---|
| Cmpd No. | Structure |
| 362 | 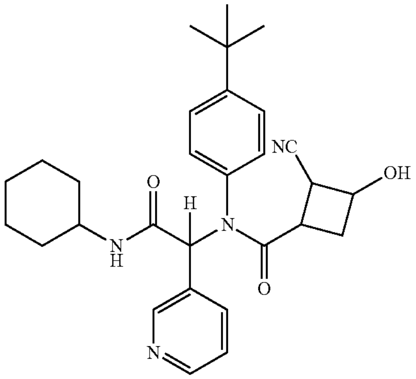 [SMILES: CC(C)(C)c1ccc(N(C(=O)C2CC(O)C2C#N)C(C(=O)NC2CCCCC2)c2cccnc2)cc1] |
| 363 | 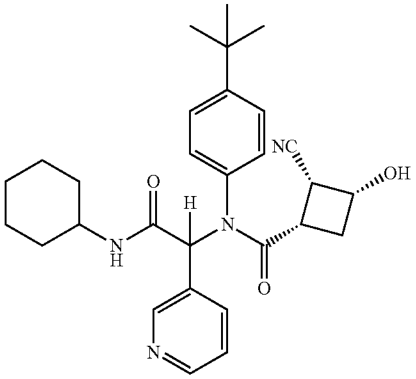 [SMILES: CC(C)(C)c1ccc(N(C(=O)[C@H]2C[C@@H](O)[C@H]2C#N)C(C(=O)NC2CCCCC2)c2cccnc2)cc1] |
| 364 | 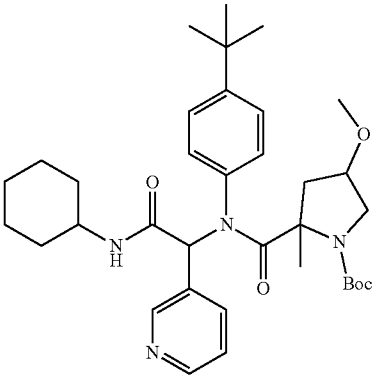 [SMILES: COC1CN(C(=O)OC(C)(C)C)C(C)(C(=O)N(c2ccc(C(C)(C)C)cc2)C(C(=O)NC2CCCCC2)c2cccnc2)C1] |
| 365 | 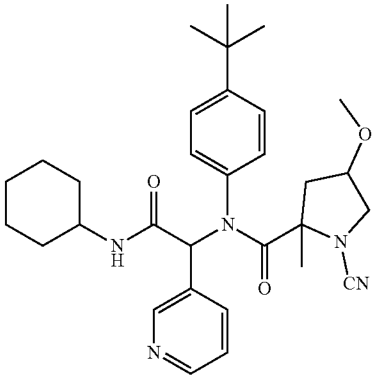 [SMILES: COC1CN(C#N)C(C)(C(=O)N(c2ccc(C(C)(C)C)cc2)C(C(=O)NC2CCCCC2)c2cccnc2)C1] |

TABLE 1-continued
Exemplary compounds.
| Cmpd No. | Structure |
|---|---|
| 366 | 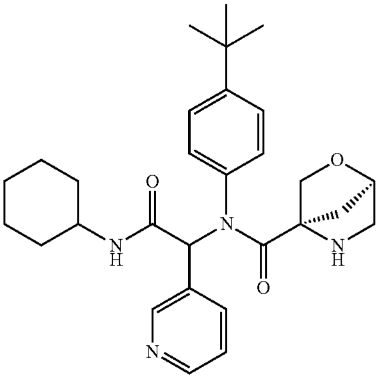 [SMILES: CC(C)(C)c1ccc(N(C(=O)[C@@]23CO[C@@H](CN2)C3)C(C(=O)NC2CCCCC2)c2cccnc2)cc1] |
| 367 | 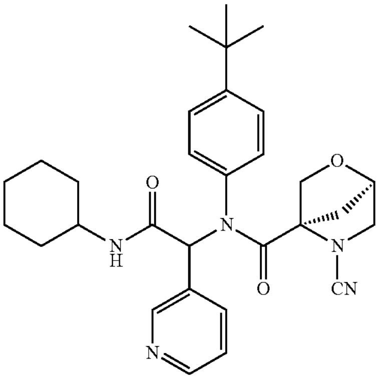 [SMILES: CC(C)(C)c1ccc(N(C(=O)[C@@]23CO[C@@H](CN2C#N)C3)C(C(=O)NC2CCCCC2)c2cccnc2)cc1] |
| 368 | 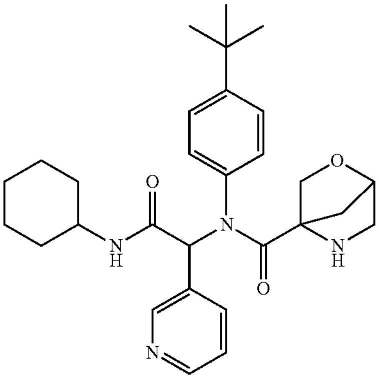 [SMILES: CC(C)(C)c1ccc(N(C(=O)C23COC(CN2)C3)C(C(=O)NC2CCCCC2)c2cccnc2)cc1] |
| 369 | 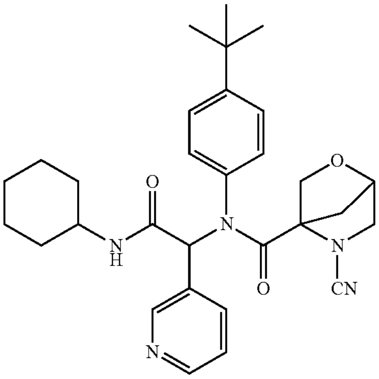 [SMILES: CC(C)(C)c1ccc(N(C(=O)C23COC(CN2C#N)C3)C(C(=O)NC2CCCCC2)c2cccnc2)cc1] |
| 370 | 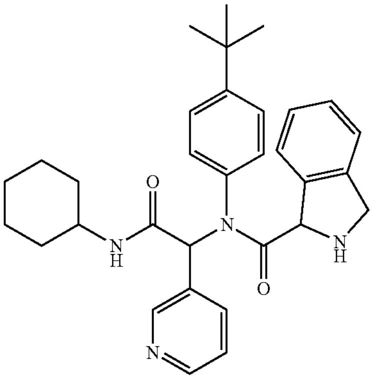 [SMILES: CC(C)(C)c1ccc(N(C(=O)C2NCc3ccccc32)C(C(=O)NC2CCCCC2)c2cccnc2)cc1] |
| 371 | 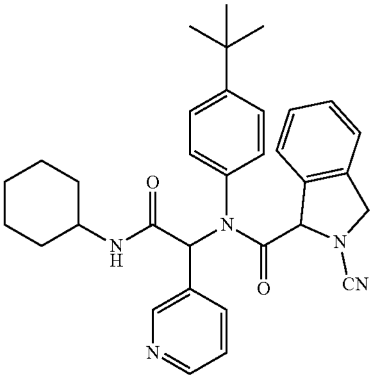 [SMILES: CC(C)(C)c1ccc(N(C(=O)C2c3ccccc3CN2C#N)C(C(=O)NC2CCCCC2)c2cccnc2)cc1] |
| 371a | 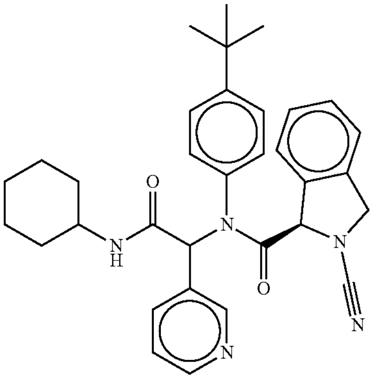 |
| 372 | 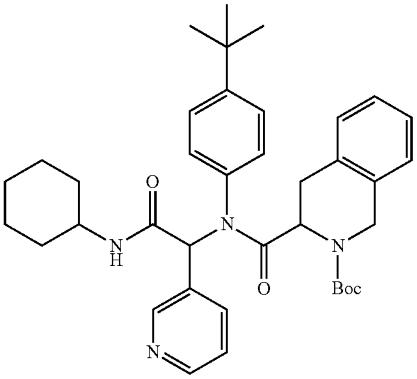 [SMILES: CC(C)(C)OC(=O)N1Cc2ccccc2CC1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 373 | 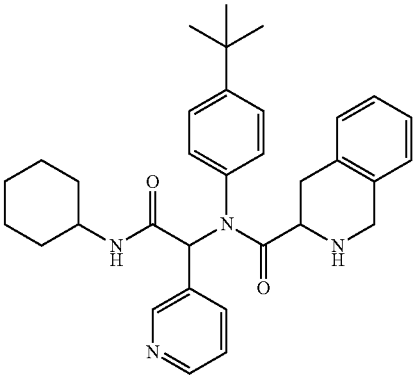 [SMILES: CC(C)(C)c1ccc(N(C(=O)C2Cc3ccccc3CN2)C(C(=O)NC2CCCCC2)c2cccnc2)cc1] |
| 373a | 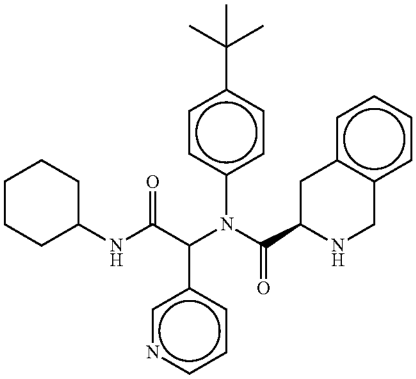 |
| 374 | 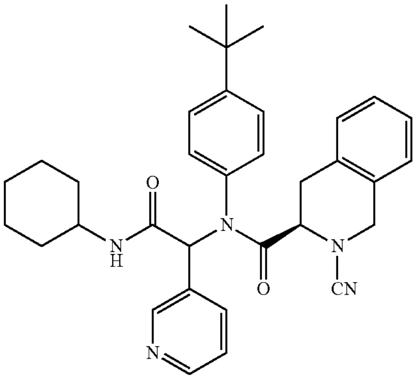 [SMILES: CC(C)(C)c1ccc(N(C(=O)[C@H]2Cc3ccccc3CN2C#N)C(C(=O)NC2CCCCC2)c2cccnc2)cc1] |
| 375 | 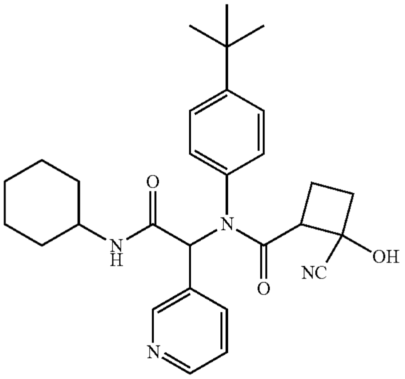 [SMILES: CC(C)(C)c1ccc(N(C(=O)C2CCC2(O)C#N)C(C(=O)NC2CCCCC2)c2cccnc2)cc1] |
TABLE 1-continued
| Exemplary compounds. | |
|---|---|
| Cmpd No. | Structure |
| 376 | 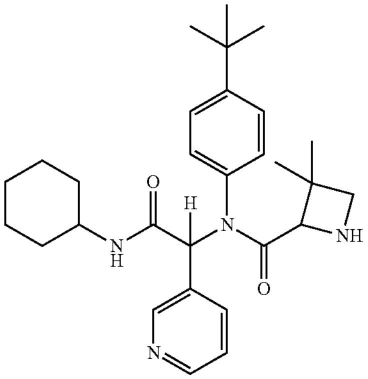 [SMILES: CC(C)(C)c1ccc(N(C(=O)C2NCC2(C)C)C(C(=O)NC2CCCCC2)c2cccnc2)cc1] |
| 378 | 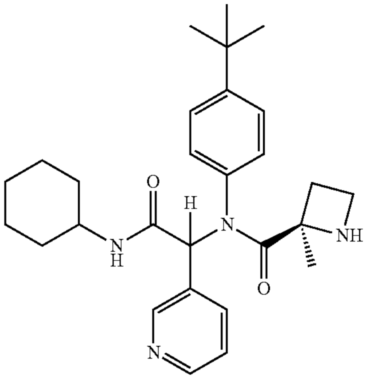 [SMILES: CC(C)(C)c1ccc(N(C(=O)[C@@]2(C)CCN2)C(C(=O)NC2CCCCC2)c2cccnc2)cc1] |
| 379 | 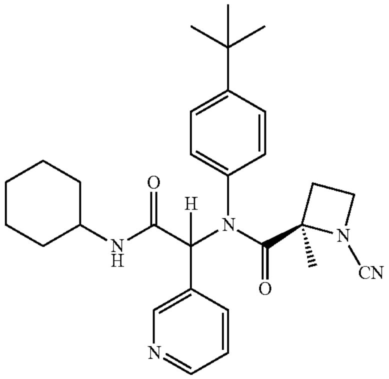 [SMILES: CC(C)(C)c1ccc(N(C(=O)[C@@]2(C)CCN2C#N)C(C(=O)NC2CCCCC2)c2cccnc2)cc1] |
| 380 | 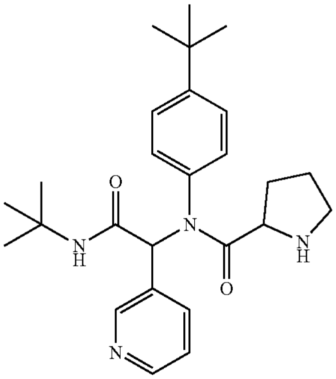 [SMILES: CC(C)(C)NC(=O)C(c1cccnc1)N(C(=O)C1CCCN1)c1ccc(C(C)(C)C)cc1] |

TABLE 1-continued
Exemplary compounds.
| Cmpd No. | Structure |
|---|---|
| 381 | 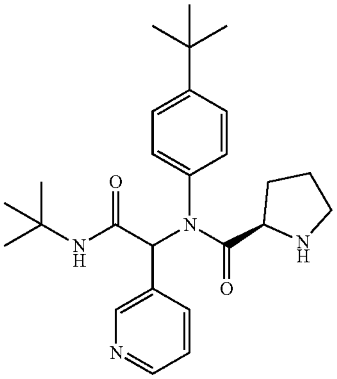 [SMILES: CC(C)(C)NC(=O)C(c1cccnc1)N(C(=O)[C@H]1CCCN1)c1ccc(C(C)(C)C)cc1] |
| 382 | 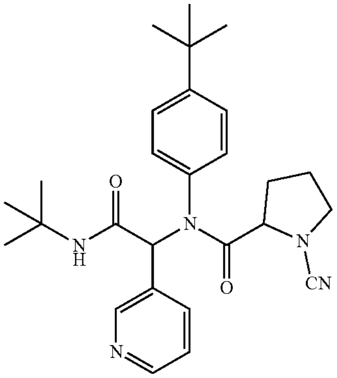 [SMILES: CC(C)(C)NC(=O)C(c1cccnc1)N(C(=O)C1CCCN1C#N)c1ccc(C(C)(C)C)cc1] |
| 383 | 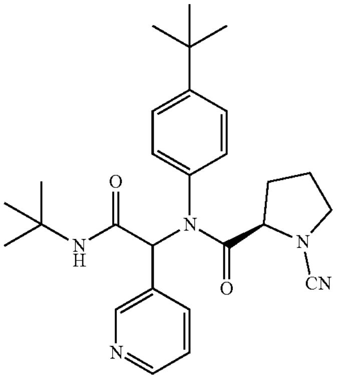 [SMILES: CC(C)(C)NC(=O)C(c1cccnc1)N(C(=O)[C@H]1CCCN1C#N)c1ccc(C(C)(C)C)cc1] |
| 384 | 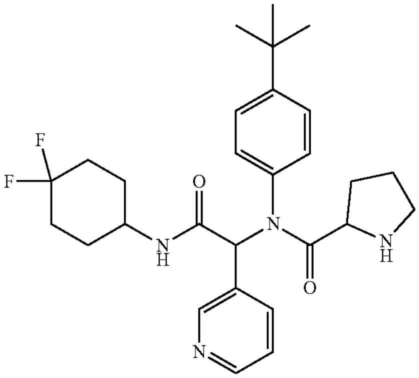 [SMILES: CC(C)(C)c1ccc(N(C(=O)C2CCCN2)C(C(=O)NC2CCC(F)(F)CC2)c2cccnc2)cc1] |
TABLE 1-continued
Exemplary compounds.
| Cmpd No. | Structure |
|---|---|
| 385 | 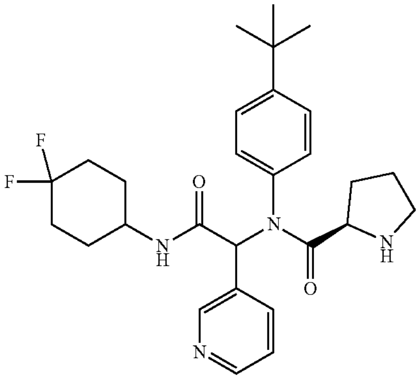 [SMILES: CC(C)(C)c1ccc(N(C(=O)[C@H]2CCCN2)C(C(=O)NC2CCC(F)(F)CC2)c2cccnc2)cc1] |
| 386 | 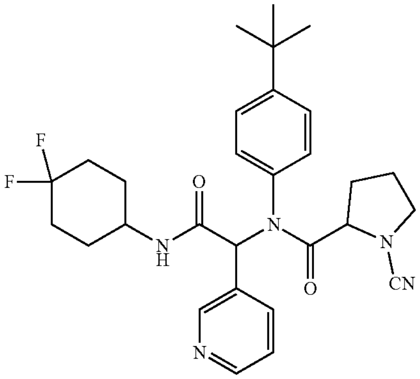 [SMILES: CC(C)(C)c1ccc(N(C(=O)C2CCCN2C#N)C(C(=O)NC2CCC(F)(F)CC2)c2cccnc2)cc1] |
| 387 | 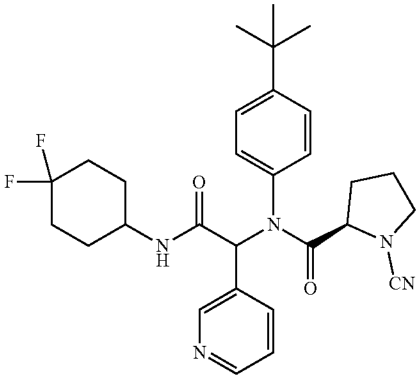 [SMILES: CC(C)(C)c1ccc(N(C(=O)[C@H]2CCCN2C#N)C(C(=O)NC2CCC(F)(F)CC2)c2cccnc2)cc1] |
| 388 | 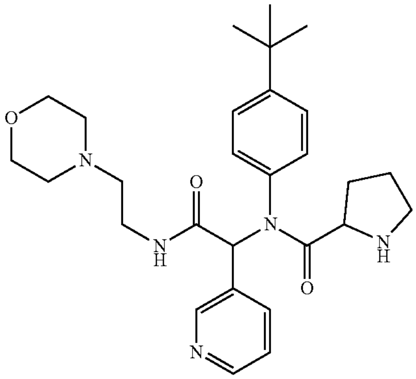 [SMILES: CC(C)(C)c1ccc(N(C(=O)C2CCCN2)C(C(=O)NCCN2CCOCC2)c2cccnc2)cc1] |

TABLE 1-continued
| Exemplary compounds. | |
|---|---|
| Cmpd No. | Structure |
| 389 | 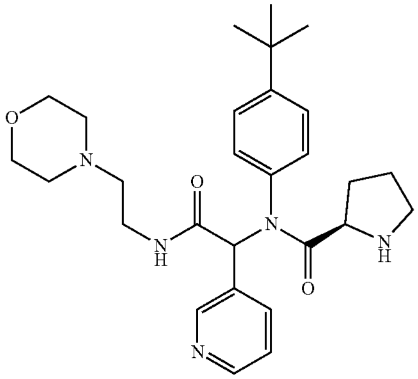 [SMILES: CC(C)(C)c1ccc(N(C(=O)[C@H]2CCCN2)C(C(=O)NCCN2CCOCC2)c2cccnc2)cc1] |
| 390 | 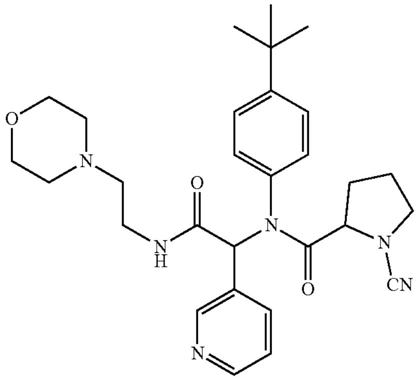 [SMILES: CC(C)(C)c1ccc(N(C(=O)C2CCCN2C#N)C(C(=O)NCCN2CCOCC2)c2cccnc2)cc1] |
| 391 | 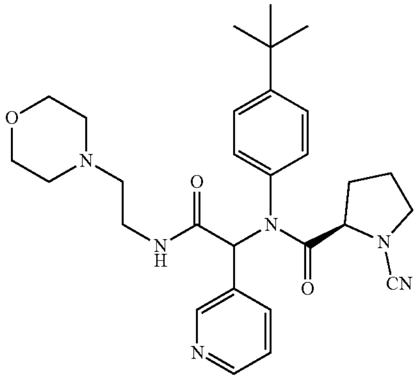 [SMILES: CC(C)(C)c1ccc(N(C(=O)[C@H]2CCCN2C#N)C(C(=O)NCCN2CCOCC2)c2cccnc2)cc1] |
| 392 | 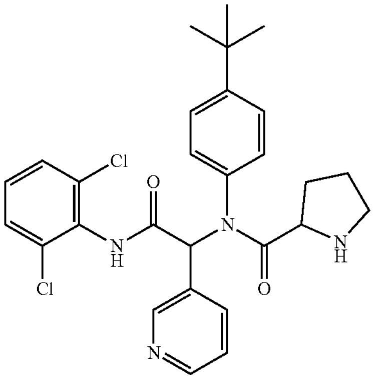 [SMILES: CC(C)(C)c1ccc(N(C(=O)C2CCCN2)C(C(=O)Nc2c(Cl)cccc2Cl)c2cccnc2)cc1] |
TABLE 1-continued
| Exemplary compounds. | |
|---|---|
| Cmpd No. | Structure |
| 393 | 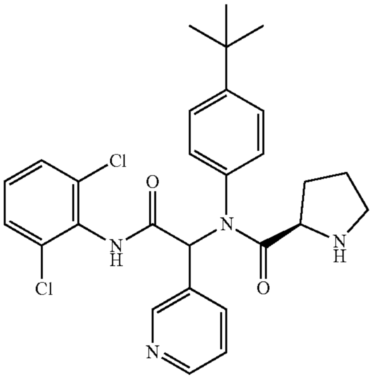 [SMILES: CC(C)(C)c1ccc(N(C(=O)[C@H]2CCCN2)C(C(=O)Nc2c(Cl)cccc2Cl)c2cccnc2)cc1] |
| 394 | 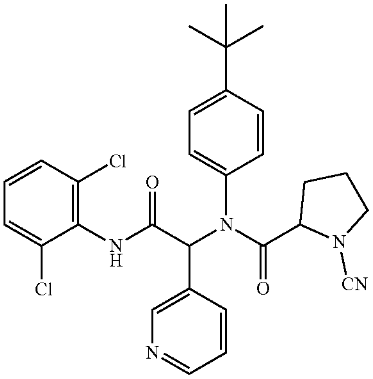 [SMILES: CC(C)(C)c1ccc(N(C(=O)C2CCCN2C#N)C(C(=O)Nc2c(Cl)cccc2Cl)c2cccnc2)cc1] |
| 395 | 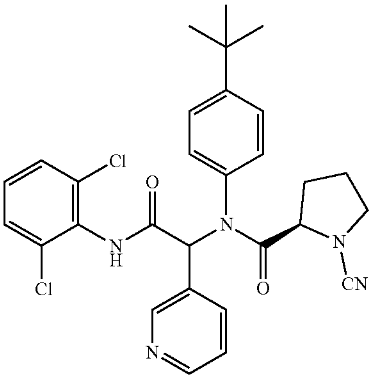 [SMILES: CC(C)(C)c1ccc(N(C(=O)[C@H]2CCCN2C#N)C(C(=O)Nc2c(Cl)cccc2Cl)c2cccnc2)cc1] |
| 396 | 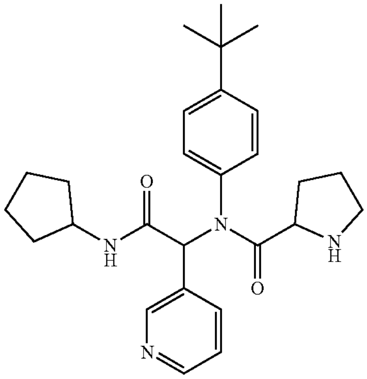 [SMILES: CC(C)(C)c1ccc(N(C(=O)C2CCCN2)C(C(=O)NC2CCCC2)c2cccnc2)cc1] |

TABLE 1-continued
Exemplary compounds.
| Cmpd No. | Structure |
|---|---|
| 397 | 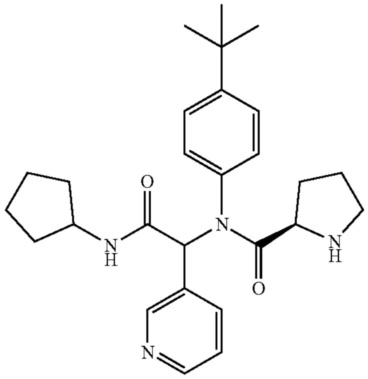 [SMILES: CC(C)(C)c1ccc(N(C(=O)[C@H]2CCCN2)C(C(=O)NC2CCCC2)c2cccnc2)cc1] |
| 398 | 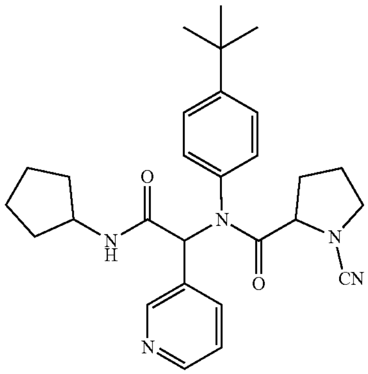 [SMILES: CC(C)(C)c1ccc(N(C(=O)C2CCCN2C#N)C(C(=O)NC2CCCC2)c2cccnc2)cc1] |
| 399 | 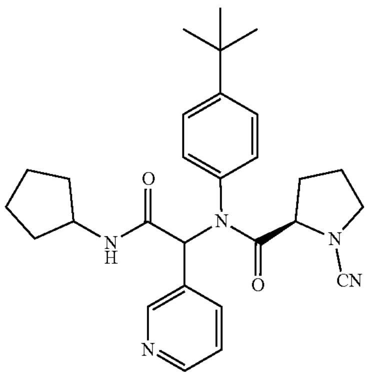 [SMILES: CC(C)(C)c1ccc(N(C(=O)[C@H]2CCCN2C#N)C(C(=O)NC2CCCC2)c2cccnc2)cc1] |
| 400 | 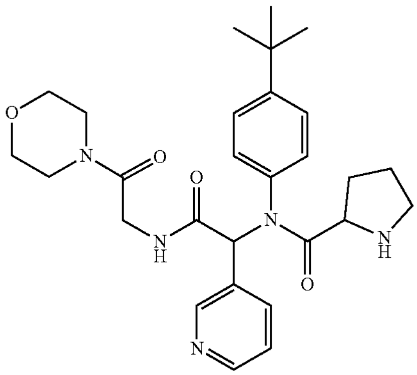 [SMILES: CC(C)(C)c1ccc(N(C(=O)C2CCCN2)C(C(=O)NCC(=O)N2CCOCC2)c2cccnc2)cc1] |
TABLE 1-continued
Exemplary compounds.
| Cmpd No. | Structure |
|---|---|
| 401 | 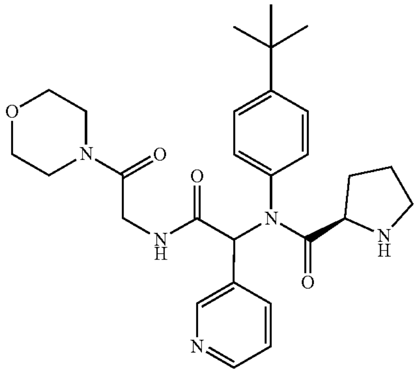 [SMILES: CC(C)(C)c1ccc(N(C(=O)[C@H]2CCCN2)C(C(=O)NCC(=O)N2CCOCC2)c2cccnc2)cc1] |
| 402 | 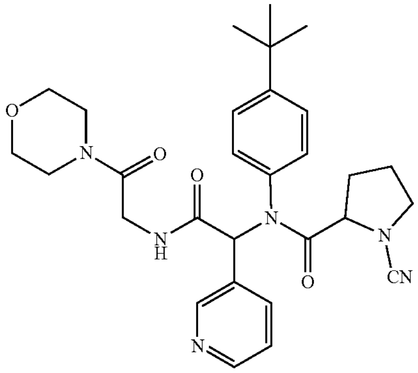 [SMILES: CC(C)(C)c1ccc(N(C(=O)C2CCCN2C#N)C(C(=O)NCC(=O)N2CCOCC2)c2cccnc2)cc1] |
| 403 | 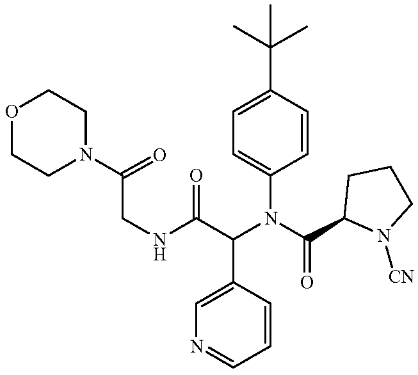 [SMILES: CC(C)(C)c1ccc(N(C(=O)[C@H]2CCCN2C#N)C(C(=O)NCC(=O)N2CCOCC2)c2cccnc2)cc1] |
| 404 | 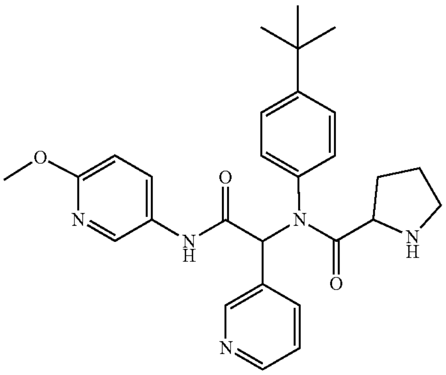 [SMILES: COc1ccc(NC(=O)C(c2cccnc2)N(C(=O)C2CCCN2)c2ccc(C(C)(C)C)cc2)cn1] |

TABLE 1-continued
Exemplary compounds.
| Cmpd No. | Structure |
|---|---|
| 405 | 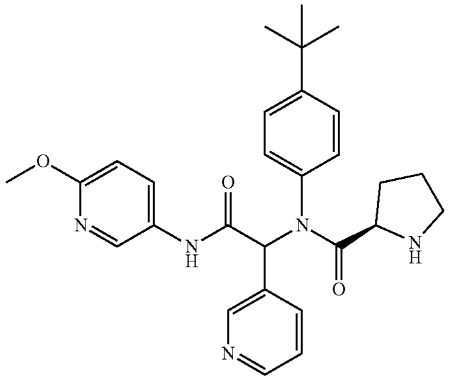 [SMILES: COc1ccc(NC(=O)C(c2cccnc2)N(C(=O)[C@H]2CCCN2)c2ccc(C(C)(C)C)cc2)cn1] |
| 406 | 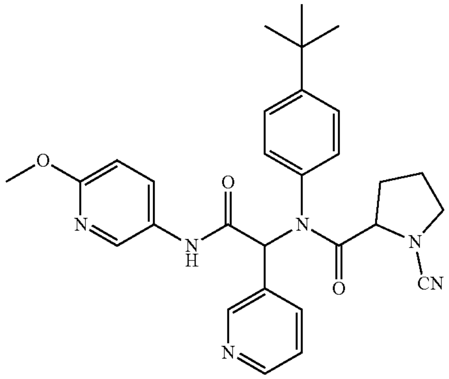 [SMILES: COc1ccc(NC(=O)C(c2cccnc2)N(C(=O)C2CCCN2C#N)c2ccc(C(C)(C)C)cc2)cn1] |
| 407 | 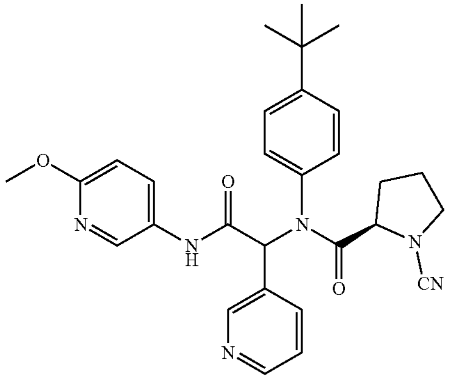 [SMILES: COc1ccc(NC(=O)C(c2cccnc2)N(C(=O)[C@H]2CCCN2C#N)c2ccc(C(C)(C)C)cc2)cn1] |
| 408 | 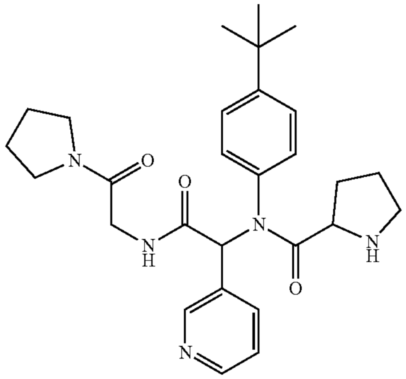 [SMILES: CC(C)(C)c1ccc(N(C(=O)C2CCCN2)C(C(=O)NCC(=O)N2CCCC2)c2cccnc2)cc1] |
| 409 | 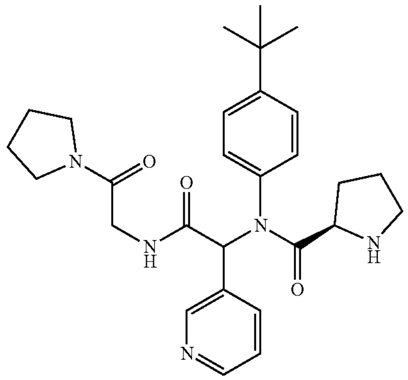 [SMILES: CC(C)(C)c1ccc(N(C(=O)[C@H]2CCCN2)C(C(=O)NCC(=O)N2CCCC2)c2cccnc2)cc1] |
| 410 | 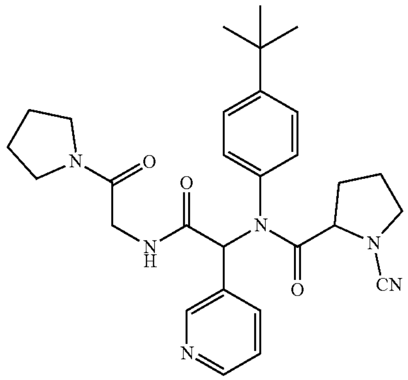 [SMILES: CC(C)(C)c1ccc(N(C(=O)C2CCCN2C#N)C(C(=O)NCC(=O)N2CCCC2)c2cccnc2)cc1] |
| 411 | 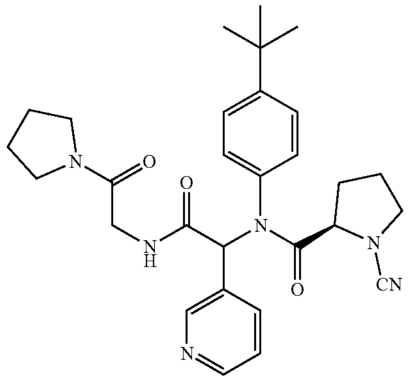 [SMILES: CC(C)(C)c1ccc(N(C(=O)[C@H]2CCCN2C#N)C(C(=O)NCC(=O)N2CCCC2)c2cccnc2)cc1] |
| 412 | 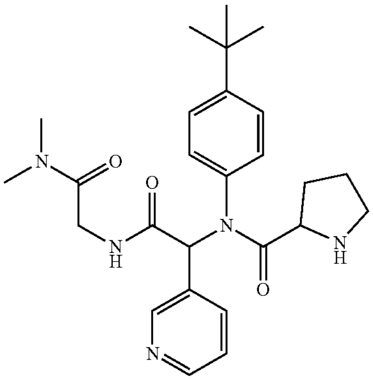 [SMILES: CN(C)C(=O)CNC(=O)C(c1cccnc1)N(C(=O)C1CCCN1)c1ccc(C(C)(C)C)cc1] |

TABLE 1-continued
Exemplary compounds.
| Cmpd No. | Structure |
|---|---|
| 413 | 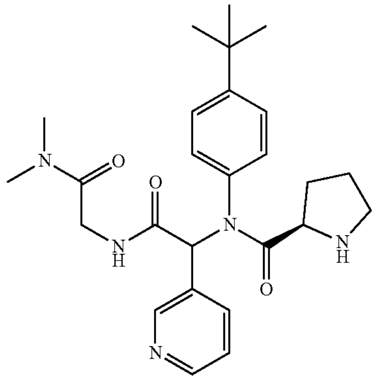 [SMILES: CN(C)C(=O)CNC(=O)C(c1cccnc1)N(C(=O)[C@H]1CCCN1)c1ccc(C(C)(C)C)cc1] |
| 414 | 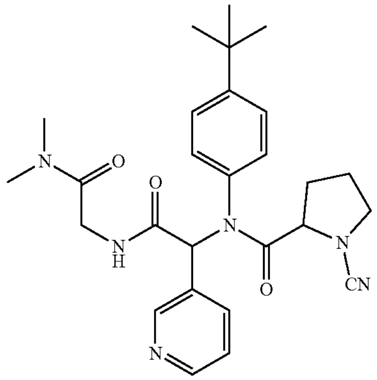 [SMILES: CN(C)C(=O)CNC(=O)C(c1cccnc1)N(C(=O)C1CCCN1C#N)c1ccc(C(C)(C)C)cc1] |
| 415 | 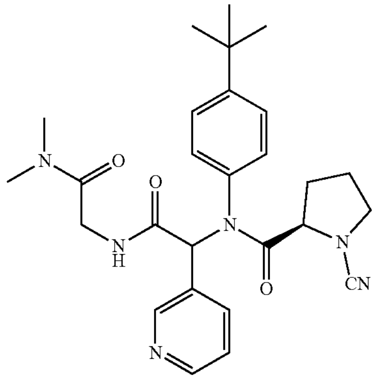 [SMILES: CN(C)C(=O)CNC(=O)C(c1cccnc1)N(C(=O)[C@H]1CCCN1C#N)c1ccc(C(C)(C)C)cc1] |
| 416 | 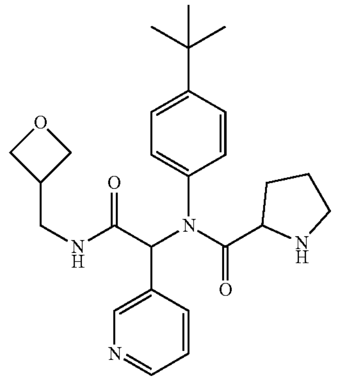 [SMILES: CC(C)(C)c1ccc(N(C(=O)C2CCCN2)C(C(=O)NCC2COC2)c2cccnc2)cc1] |
| 417 | 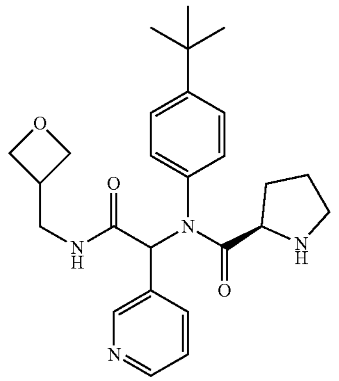 [SMILES: CC(C)(C)c1ccc(N(C(=O)[C@H]2CCCN2)C(C(=O)NCC2COC2)c2cccnc2)cc1] |
| 418 | 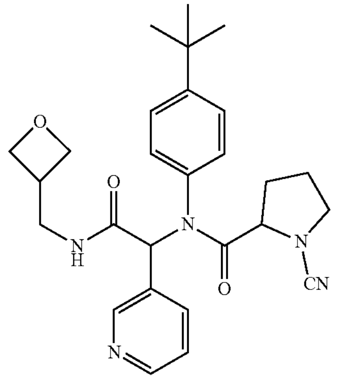 [SMILES: CC(C)(C)c1ccc(N(C(=O)C2CCCN2C#N)C(C(=O)NCC2COC2)c2cccnc2)cc1] |
| 419 | 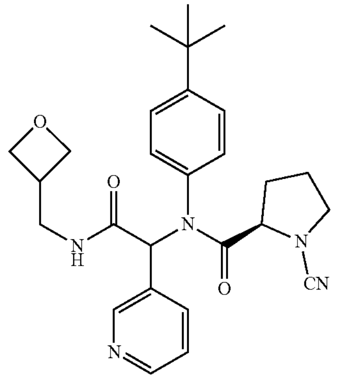 [SMILES: CC(C)(C)c1ccc(N(C(=O)[C@H]2CCCN2C#N)C(C(=O)NCC2COC2)c2cccnc2)cc1] |
| 420 | 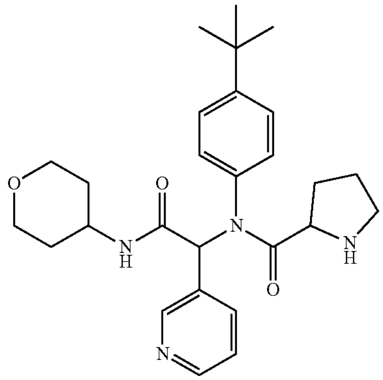 [SMILES: CC(C)(C)c1ccc(N(C(=O)C2CCCN2)C(C(=O)NC2CCOCC2)c2cccnc2)cc1] |

TABLE 1-continued
Exemplary compounds.
| Cmpd No. | Structure |
| --- | --- |
| 421 | 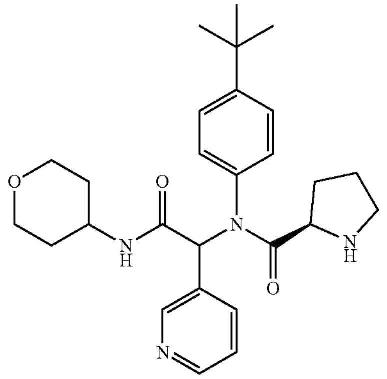 [SMILES: CC(C)(C)c1ccc(N(C(=O)[C@H]2CCCN2)C(C(=O)NC2CCOCC2)c2cccnc2)cc1] |
| 422 | 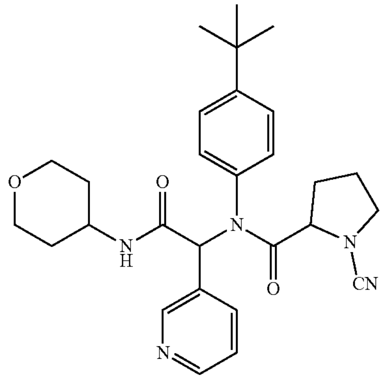 [SMILES: CC(C)(C)c1ccc(N(C(=O)C2CCCN2C#N)C(C(=O)NC2CCOCC2)c2cccnc2)cc1] |
| 423 | 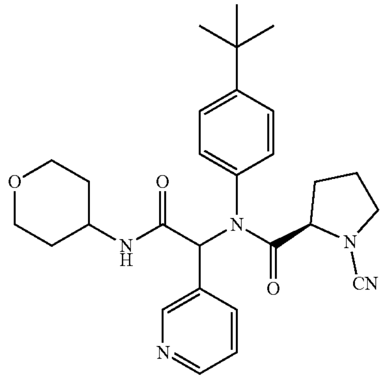 [SMILES: CC(C)(C)c1ccc(N(C(=O)[C@H]2CCCN2C#N)C(C(=O)NC2CCOCC2)c2cccnc2)cc1] |
| 424 | 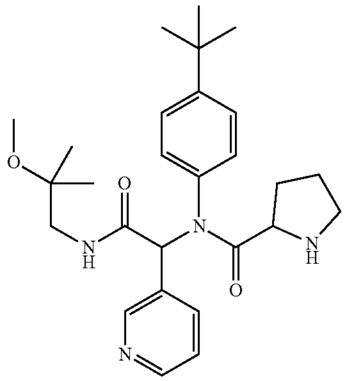 [SMILES: COC(C)(C)CNC(=O)C(c1cccnc1)N(C(=O)C1CCCN1)c1ccc(C(C)(C)C)cc1] |
TABLE 1-continued
Exemplary compounds.
| Cmpd No. | Structure |
| --- | --- |
| 425 | 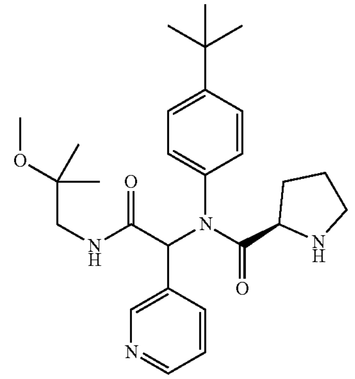 [SMILES: COC(C)(C)CNC(=O)C(c1cccnc1)N(C(=O)[C@H]1CCCN1)c1ccc(C(C)(C)C)cc1] |
| 426 | 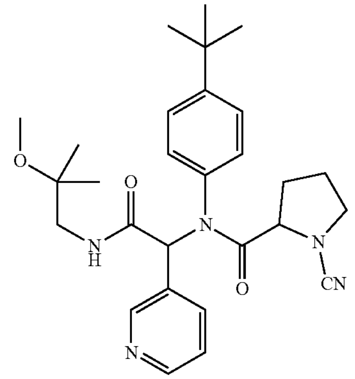 [SMILES: COC(C)(C)CNC(=O)C(c1cccnc1)N(C(=O)C1CCCN1C#N)c1ccc(C(C)(C)C)cc1] |
| 427 | 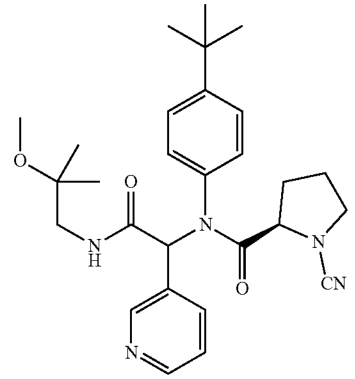 [SMILES: COC(C)(C)CNC(=O)C(c1cccnc1)N(C(=O)[C@H]1CCCN1C#N)c1ccc(C(C)(C)C)cc1] |
| 428 | 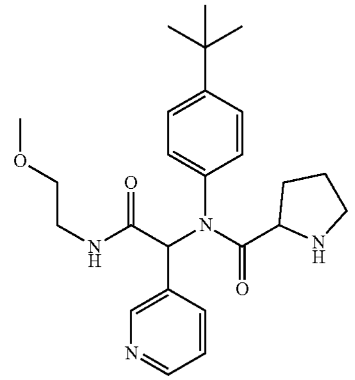 [SMILES: COCCNC(=O)C(c1cccnc1)N(C(=O)C1CCCN1)c1ccc(C(C)(C)C)cc1] |

TABLE 1-continued
| Exemplary compounds. | |
|---|---|
| Cmpd No. | Structure |
| 429 | 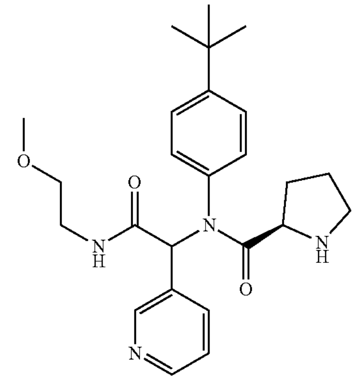 [SMILES: COCCNC(=O)C(c1cccnc1)N(C(=O)[C@H]1CCCN1)c1ccc(C(C)(C)C)cc1] |
| 430 | 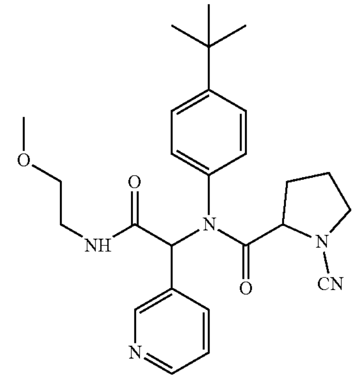 |
| 431 | 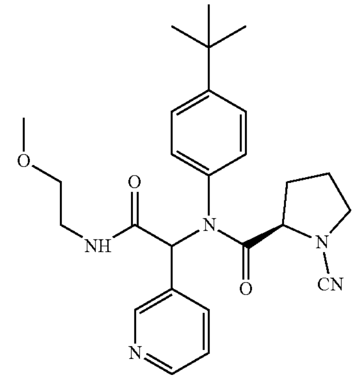 |
| 432 | 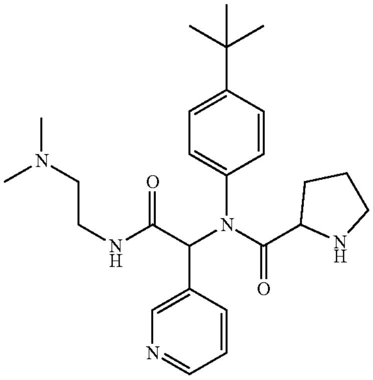 [SMILES: CN(C)CCNC(=O)C(c1cccnc1)N(C(=O)C1CCCN1)c1ccc(C(C)(C)C)cc1] |
TABLE 1-continued
| Exemplary compounds. | |
|---|---|
| Cmpd No. | Structure |
| 433 | 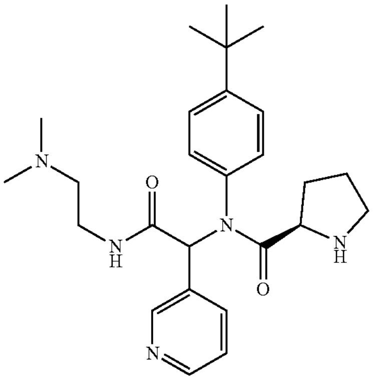 [SMILES: CN(C)CCNC(=O)C(c1cccnc1)N(C(=O)[C@H]1CCCN1)c1ccc(C(C)(C)C)cc1] |
| 434 | 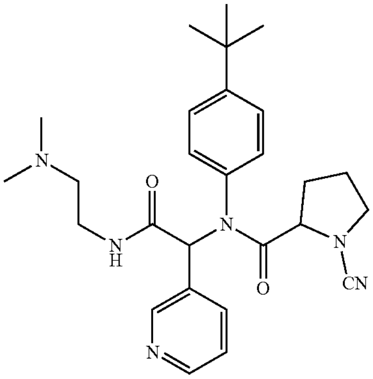 [SMILES: CN(C)CCNC(=O)C(c1cccnc1)N(C(=O)C1CCCN1C#N)c1ccc(C(C)(C)C)cc1] |
| 435 | 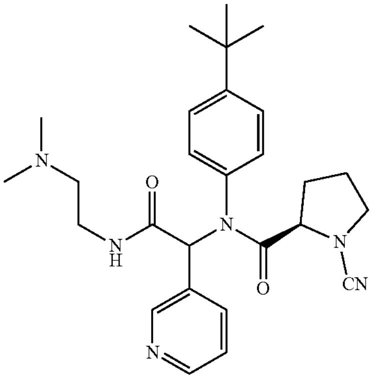 [SMILES: CN(C)CCNC(=O)C(c1cccnc1)N(C(=O)[C@H]1CCCN1C#N)c1ccc(C(C)(C)C)cc1] |
| 436 | 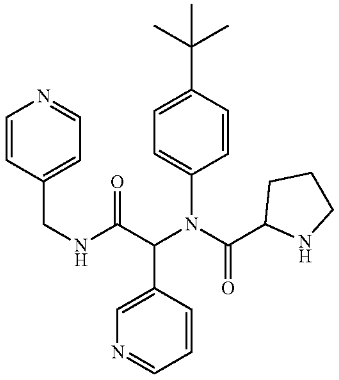 [SMILES: CC(C)(C)c1ccc(N(C(=O)C2CCCN2)C(C(=O)NCc2ccncc2)c2cccnc2)cc1] |

TABLE 1-continued
| Cmpd No. | Structure |
|---|---|
| 437 | 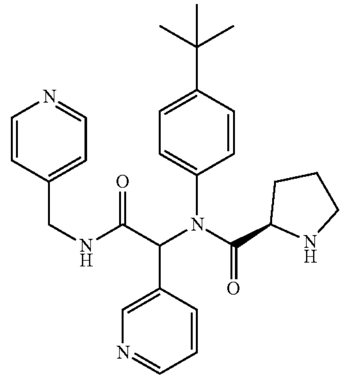 [SMILES: CC(C)(C)c1ccc(N(C(=O)[C@H]2CCCN2)C(C(=O)NCc2ccncc2)c2cccnc2)cc1] |
| 438 | 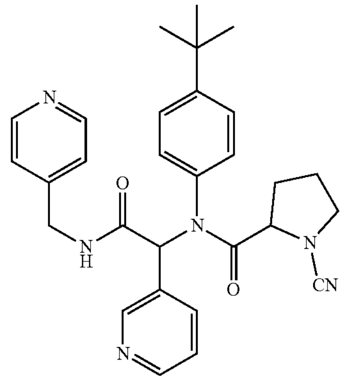 [SMILES: CC(C)(C)c1ccc(N(C(=O)C2CCCN2C#N)C(C(=O)NCc2ccncc2)c2cccnc2)cc1] |
| 439 | 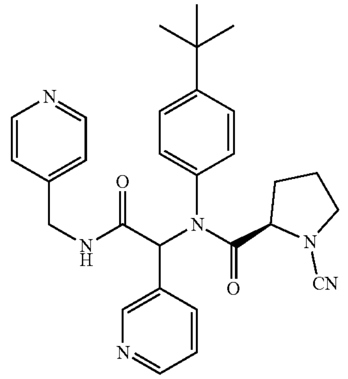 [SMILES: CC(C)(C)c1ccc(N(C(=O)[C@H]2CCCN2C#N)C(C(=O)NCc2ccncc2)c2cccnc2)cc1] |
| 440 | 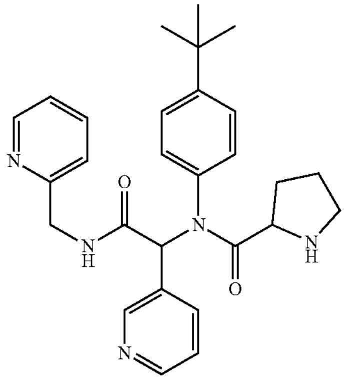 [SMILES: CC(C)(C)c1ccc(N(C(=O)C2CCCN2)C(C(=O)NCc2ccccn2)c2cccnc2)cc1] |
TABLE 1-continued
| Cmpd No. | Structure |
|---|---|
| 441 | 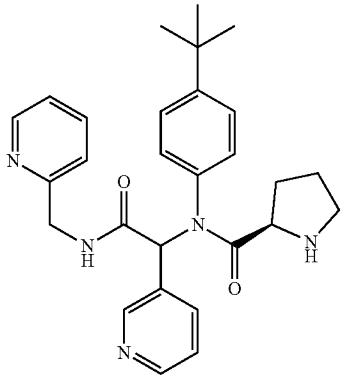 [SMILES: CC(C)(C)c1ccc(N(C(=O)[C@H]2CCCN2)C(C(=O)NCc2ccccn2)c2cccnc2)cc1] |
| 442 | 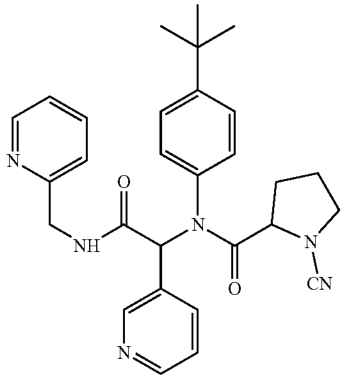 |
| 443 | 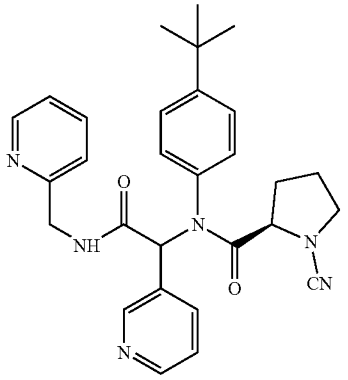 |
| 444 | 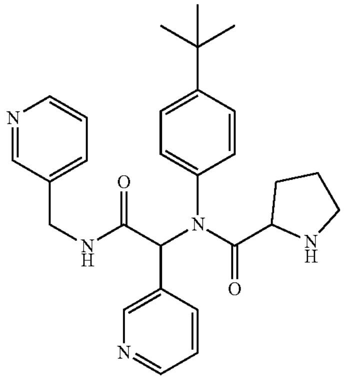 [SMILES: CC(C)(C)c1ccc(N(C(=O)C2CCCN2)C(C(=O)NCc2cccnc2)c2cccnc2)cc1] |

TABLE 1-continued
| Exemplary compounds. | |
|---|---|
| Cmpd No. | Structure |
| 445 | 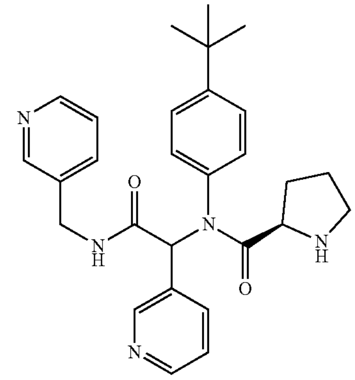 [SMILES: CC(C)(C)c1ccc(N(C(=O)[C@H]2CCCN2)C(C(=O)NCc2cccnc2)c2cccnc2)cc1] |
| 446 | 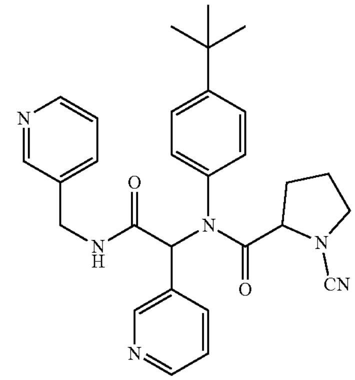 [SMILES: CC(C)(C)c1ccc(N(C(=O)C2CCCN2C#N)C(C(=O)NCc2cccnc2)c2cccnc2)cc1] |
| 447 | 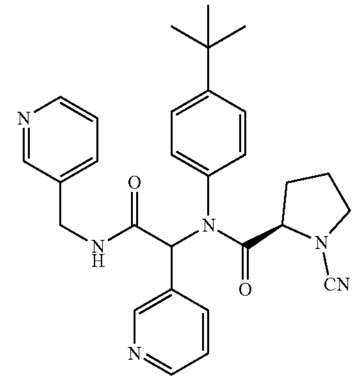 [SMILES: CC(C)(C)c1ccc(N(C(=O)[C@H]2CCCN2C#N)C(C(=O)NCc2cccnc2)c2cccnc2)cc1] |
| 448 | 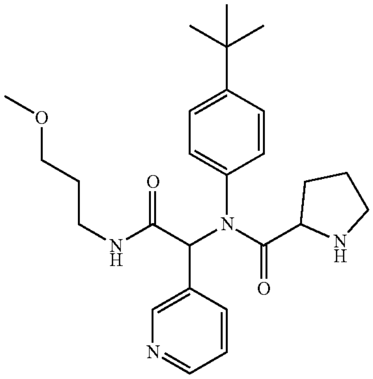 [SMILES: COCCCNC(=O)C(c1cccnc1)N(C(=O)C1CCCN1)c1ccc(C(C)(C)C)cc1] |
TABLE 1-continued
| Exemplary compounds. | |
|---|---|
| Cmpd No. | Structure |
| 449 | 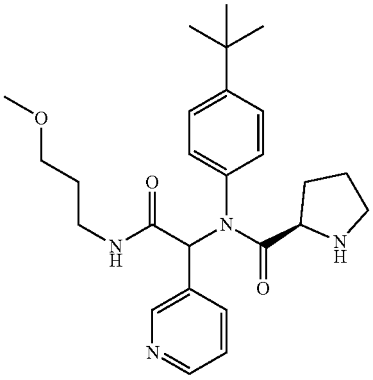 [SMILES: COCCCNC(=O)C(c1cccnc1)N(C(=O)[C@H]1CCCN1)c1ccc(C(C)(C)C)cc1] |
| 450 | 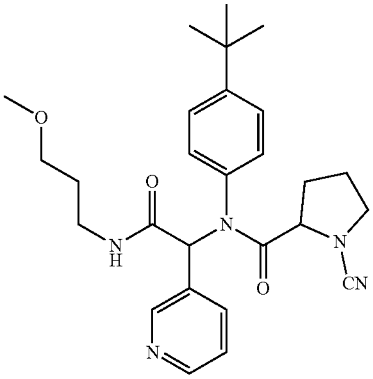 [SMILES: COCCCNC(=O)C(c1cccnc1)N(C(=O)C1CCCN1C#N)c1ccc(C(C)(C)C)cc1] |
| 451 | 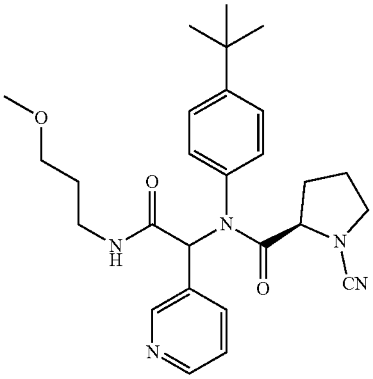 [SMILES: COCCCNC(=O)C(c1cccnc1)N(C(=O)[C@H]1CCCN1C#N)c1ccc(C(C)(C)C)cc1] |
| 452 | 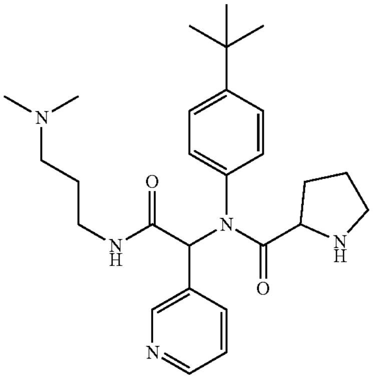 [SMILES: CN(C)CCCNC(=O)C(c1cccnc1)N(C(=O)C1CCCN1)c1ccc(C(C)(C)C)cc1] |

TABLE 1-continued
| Exemplary compounds. | |
|---|---|
| Cmpd No. | Structure |
| 453 | 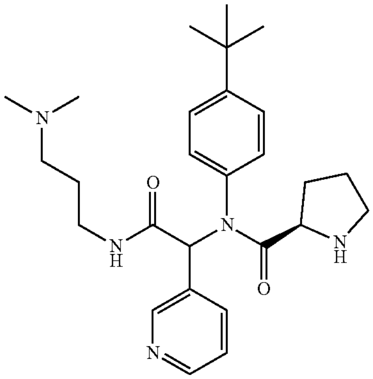 [SMILES: CN(C)CCCNC(=O)C(c1cccnc1)N(C(=O)[C@H]1CCCN1)c1ccc(C(C)(C)C)cc1] |
| 454 | 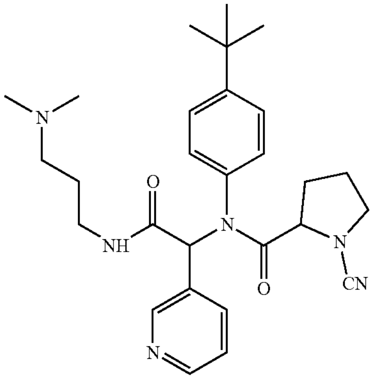 [SMILES: CN(C)CCCNC(=O)C(c1cccnc1)N(C(=O)C1CCCN1C#N)c1ccc(C(C)(C)C)cc1] |
| 455 | 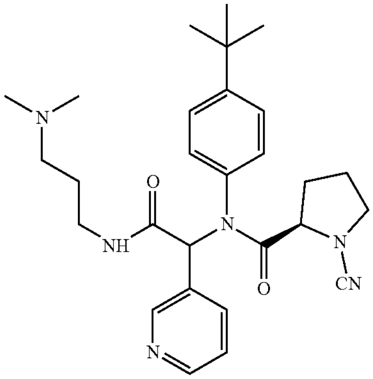 |
| 456 | 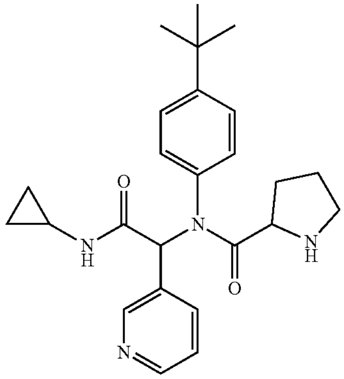 [SMILES: CC(C)(C)c1ccc(N(C(=O)C2CCCN2)C(C(=O)NC2CC2)c2cccnc2)cc1] |
TABLE 1-continued
| Exemplary compounds. | |
|---|---|
| Cmpd No. | Structure |
| 457 | 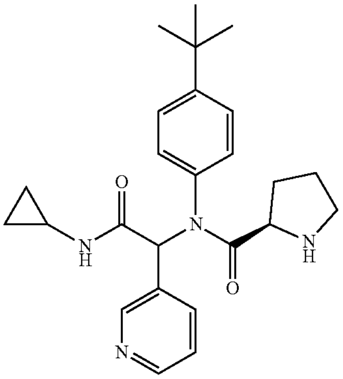 [SMILES: CC(C)(C)c1ccc(N(C(=O)[C@H]2CCCN2)C(C(=O)NC2CC2)c2cccnc2)cc1] |
| 458 | 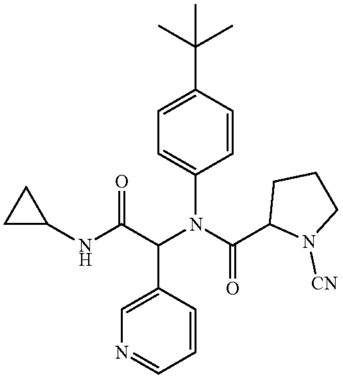 [SMILES: CC(C)(C)c1ccc(N(C(=O)C2CCCN2C#N)C(C(=O)NC2CC2)c2cccnc2)cc1] |
| 459 | 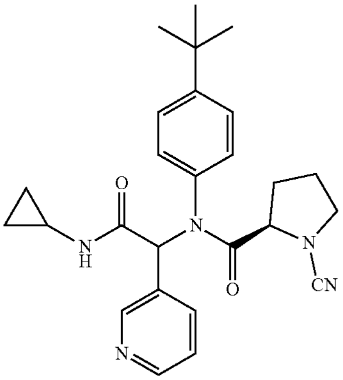 [SMILES: CC(C)(C)c1ccc(N(C(=O)[C@H]2CCCN2C#N)C(C(=O)NC2CC2)c2cccnc2)cc1] |
| 460 | 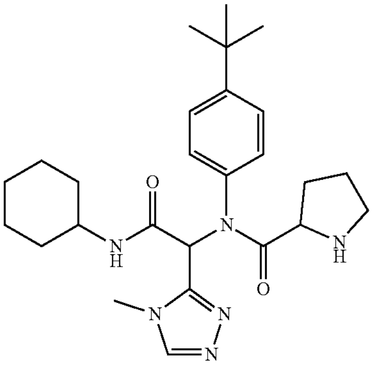 [SMILES: Cn1cnnc1C(C(=O)NC1CCCCC1)N(C(=O)C1CCCN1)c1ccc(C(C)(C)C)cc1] |

TABLE 1-continued
| Cmpd No. | Structure |
|---|---|
| | Exemplary compounds. |
| 461 | 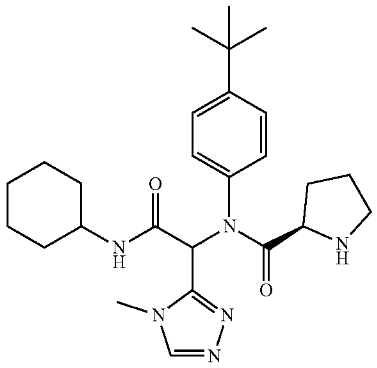 [SMILES: Cn1cnnc1C(C(=O)NC1CCCCC1)N(C(=O)[C@H]1CCCN1)c1ccc(C(C)(C)C)cc1] |
| 462 | 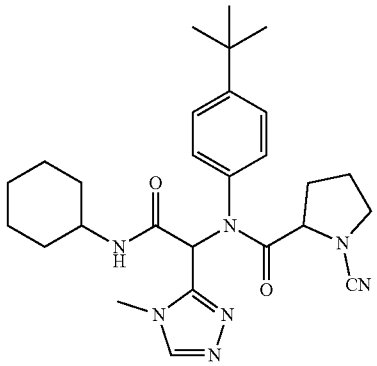 [SMILES: Cn1cnnc1C(C(=O)NC1CCCCC1)N(C(=O)C1CCCN1C#N)c1ccc(C(C)(C)C)cc1] |
| 463 | 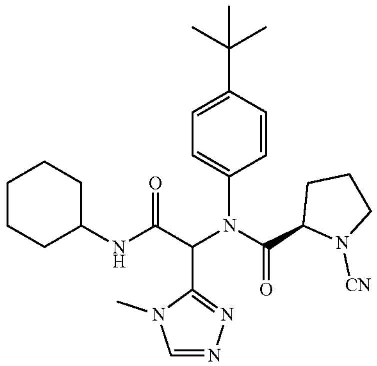 [SMILES: Cn1cnnc1C(C(=O)NC1CCCCC1)N(C(=O)[C@H]1CCCN1C#N)c1ccc(C(C)(C)C)cc1] |
| 464 | 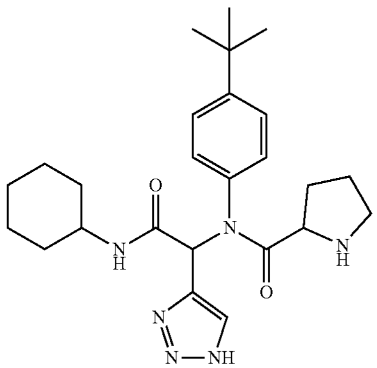 [SMILES: CC(C)(C)c1ccc(N(C(=O)C2CCCN2)C(C(=O)NC2CCCCC2)c2c[nH]nn2)cc1] |
TABLE 1-continued
| Cmpd No. | Structure |
|---|---|
| | Exemplary compounds. |
| 465 | 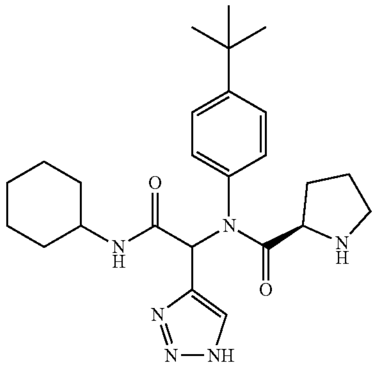 [SMILES: CC(C)(C)c1ccc(N(C(=O)[C@H]2CCCN2)C(C(=O)NC2CCCCC2)c2c[nH]nn2)cc1] |
| 466 | 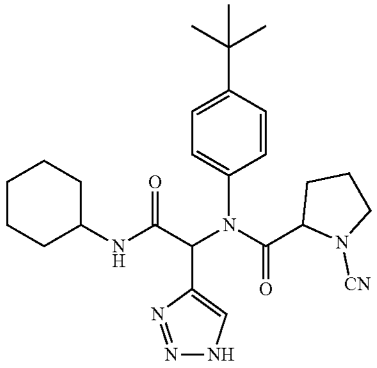 [SMILES: CC(C)(C)c1ccc(N(C(=O)C2CCCN2C#N)C(C(=O)NC2CCCCC2)c2c[nH]nn2)cc1] |
| 467 | 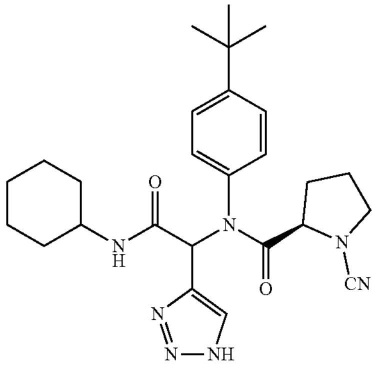 [SMILES: CC(C)(C)c1ccc(N(C(=O)[C@H]2CCCN2C#N)C(C(=O)NC2CCCCC2)c2c[nH]nn2)cc1] |
| 468 | 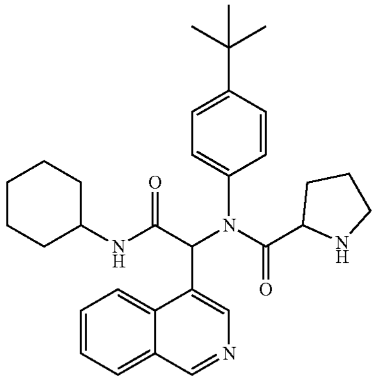 [SMILES: CC(C)(C)c1ccc(N(C(=O)C2CCCN2)C(C(=O)NC2CCCCC2)c2cncc3ccccc23)cc1] |

TABLE 1-continued
| Cmpd No. | Structure |
|---|---|
| 469 | 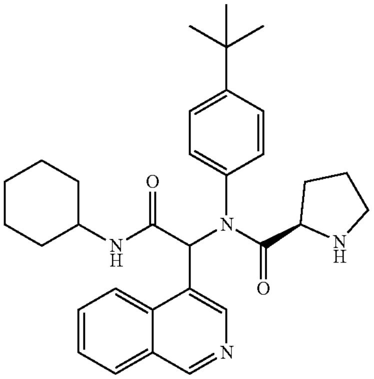 [SMILES: CC(C)(C)c1ccc(N(C(=O)[C@H]2CCCN2)C(C(=O)NC2CCCCC2)c2cncc3ccccc23)cc1] |
| 470 | 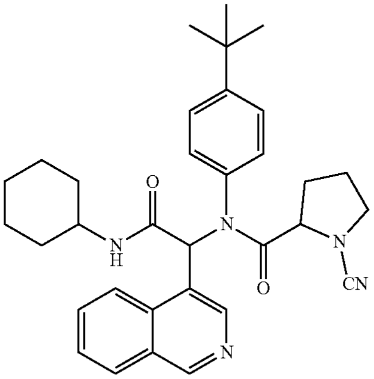 [SMILES: CC(C)(C)c1ccc(N(C(=O)C2CCCN2C#N)C(C(=O)NC2CCCCC2)c2cncc3ccccc23)cc1] |
| 471 | 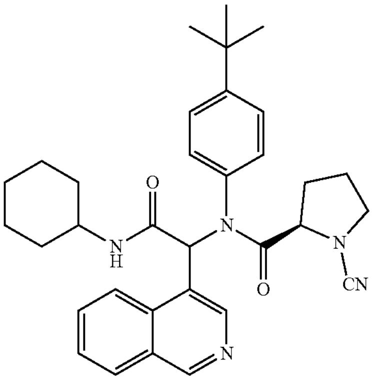 [SMILES: CC(C)(C)c1ccc(N(C(=O)[C@H]2CCCN2C#N)C(C(=O)NC2CCCCC2)c2cncc3ccccc23)cc1] |
| 472 | 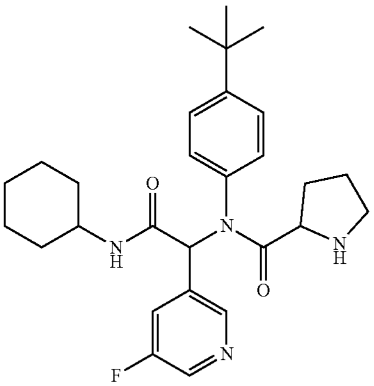 [SMILES: CC(C)(C)c1ccc(N(C(=O)C2CCCN2)C(C(=O)NC2CCCCC2)c2cncc(F)c2)cc1] |
| 473 | 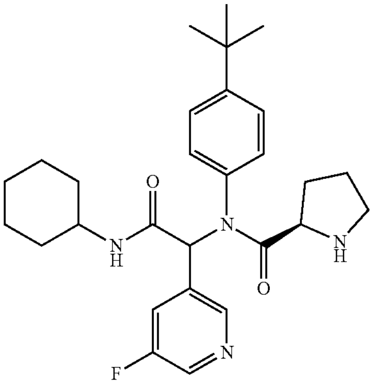 [SMILES: CC(C)(C)c1ccc(N(C(=O)[C@H]2CCCN2)C(C(=O)NC2CCCCC2)c2cncc(F)c2)cc1] |
| 474 | 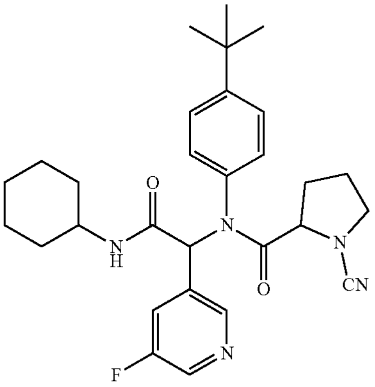 |
| 475 | 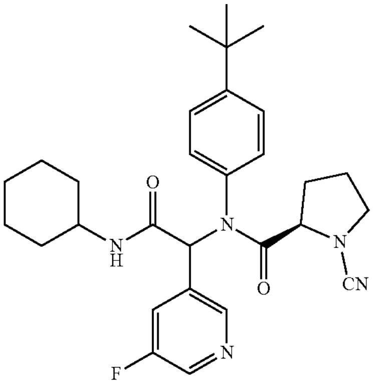 [SMILES: CC(C)(C)c1ccc(N(C(=O)[C@H]2CCCN2C#N)C(C(=O)NC2CCCCC2)c2cncc(F)c2)cc1] |
Exemplary compounds.

TABLE 1-continued
| Exemplary compounds. | |
|---|---|
| Cmpd No. | Structure |
| 476 | 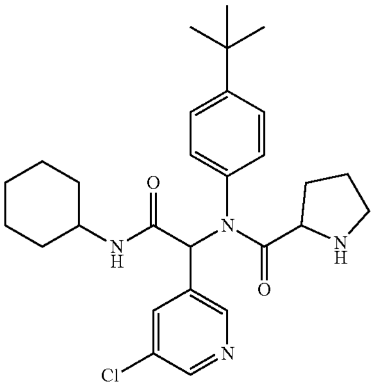 [SMILES: CC(C)(C)c1ccc(N(C(=O)C2CCCN2)C(C(=O)NC2CCCCC2)c2cncc(Cl)c2)cc1] |
| 477 | 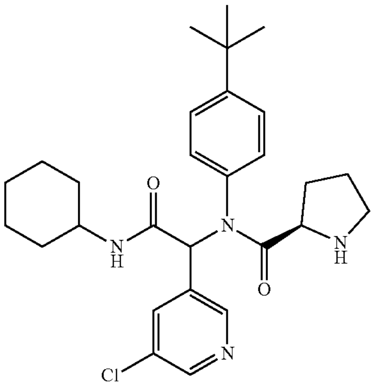 [SMILES: CC(C)(C)c1ccc(N(C(=O)[C@H]2CCCN2)C(C(=O)NC2CCCCC2)c2cncc(Cl)c2)cc1] |
| 478 | 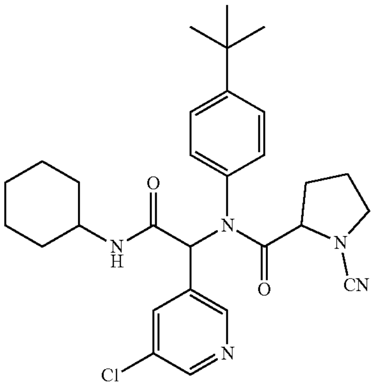 [SMILES: CC(C)(C)c1ccc(N(C(=O)C2CCCN2C#N)C(C(=O)NC2CCCCC2)c2cncc(Cl)c2)cc1] |
| 479 | 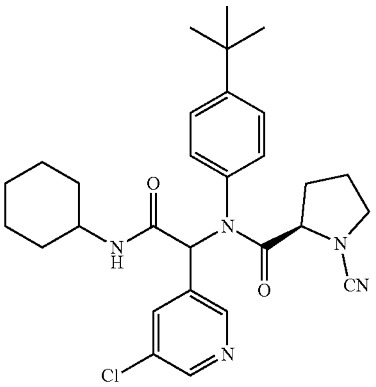 [SMILES: CC(C)(C)c1ccc(N(C(=O)[C@H]2CCCN2C#N)C(C(=O)NC2CCCCC2)c2cncc(Cl)c2)cc1] |
TABLE 1-continued
| Exemplary compounds. | |
|---|---|
| Cmpd No. | Structure |
| 480 | 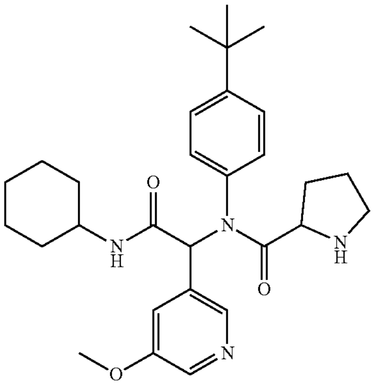 [SMILES: COc1cncc(C(C(=O)NC2CCCCC2)N(C(=O)C2CCCN2)c2ccc(C(C)(C)C)cc2)c1] |
| 481 | 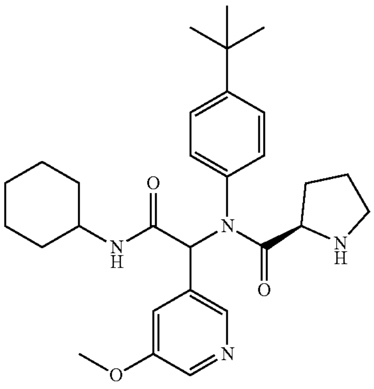 [SMILES: COc1cncc(C(C(=O)NC2CCCCC2)N(C(=O)[C@H]2CCCN2)c2ccc(C(C)(C)C)cc2)c1] |
| 482 | 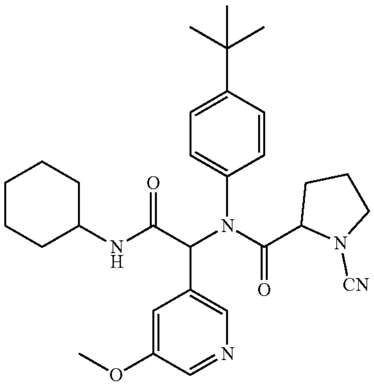 [SMILES: COc1cncc(C(C(=O)NC2CCCCC2)N(C(=O)C2CCCN2C#N)c2ccc(C(C)(C)C)cc2)c1] |

TABLE 1-continued
Exemplary compounds.
| Cmpd No. | Structure |
|---|---|
| 483 | 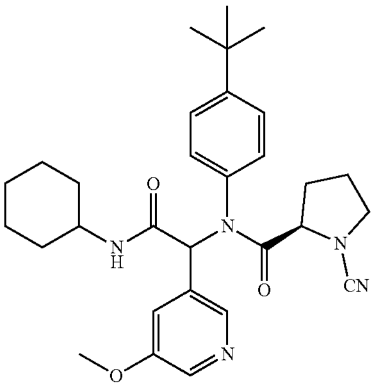 [SMILES: COc1cncc(C(C(=O)NC2CCCCC2)N(C(=O)[C@H]2CCCN2C#N)c2ccc(C(C)(C)C)cc2)c1] |
| 484 | 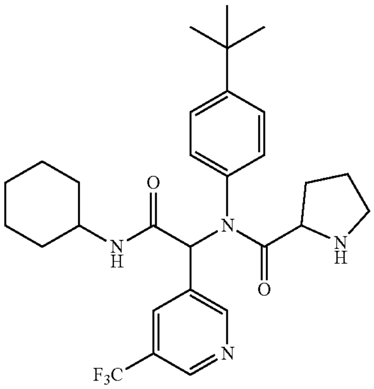 [SMILES: CC(C)(C)c1ccc(N(C(=O)C2CCCN2)C(C(=O)NC2CCCCC2)c2cncc(C(F)(F)F)c2)cc1] |
| 485 | 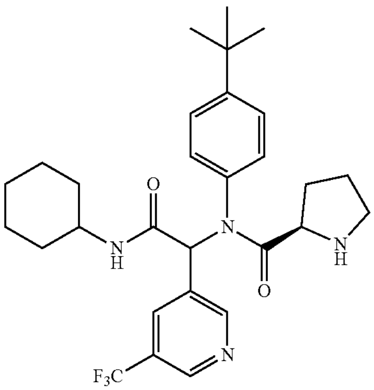 [SMILES: CC(C)(C)c1ccc(N(C(=O)[C@H]2CCCN2)C(C(=O)NC2CCCCC2)c2cncc(C(F)(F)F)c2)cc1] |
| 486 | 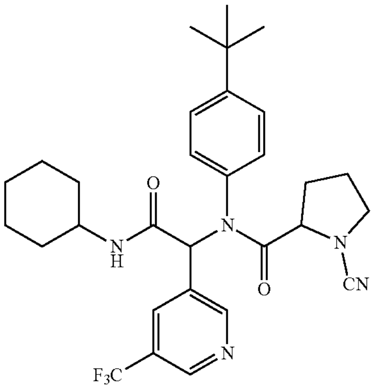 [SMILES: CC(C)(C)c1ccc(N(C(=O)C2CCCN2C#N)C(C(=O)NC2CCCCC2)c2cncc(C(F)(F)F)c2)cc1] |
| 487 | 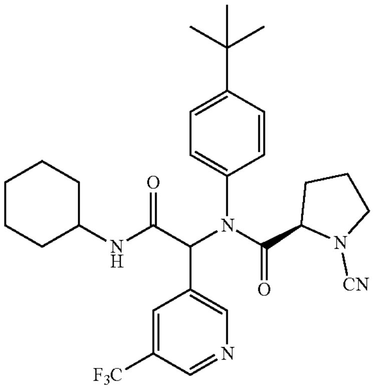 [SMILES: CC(C)(C)c1ccc(N(C(=O)[C@H]2CCCN2C#N)C(C(=O)NC2CCCCC2)c2cncc(C(F)(F)F)c2)cc1] |
| 488 | 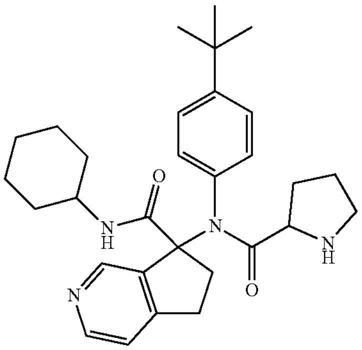 [SMILES: CC(C)(C)c1ccc(N(C(=O)C2CCCN2)C2(C(=O)NC3CCCCC3)CCc3ccncc32)cc1] |
| 489 | 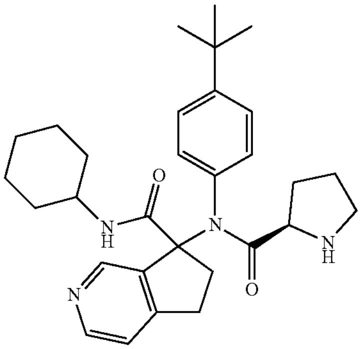 [SMILES: CC(C)(C)c1ccc(N(C(=O)[C@H]2CCCN2)C2(C(=O)NC3CCCCC3)CCc3ccncc32)cc1] |

TABLE 1-continued
| Exemplary compounds. | |
|---|---|
| Cmpd No. | Structure |
| 490 | 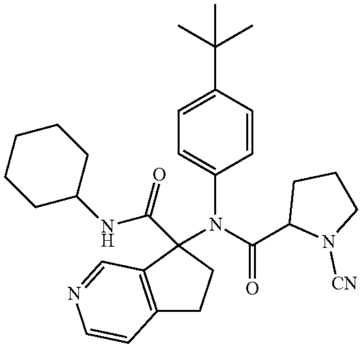 [SMILES: CC(C)(C)c1ccc(N(C(=O)C2CCCN2C#N)C2(C(=O)NC3CCCCC3)CCc3ccncc32)cc1] |
| 491 | 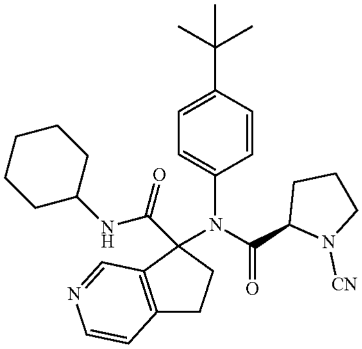 [SMILES: CC(C)(C)c1ccc(N(C(=O)[C@H]2CCCN2C#N)C2(C(=O)NC3CCCCC3)CCc3ccncc32)cc1] |
| 492 | 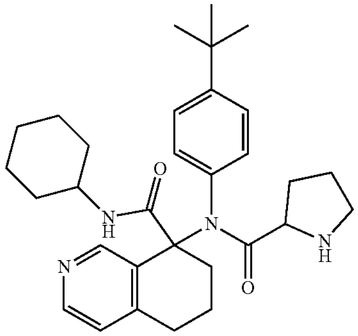 [SMILES: CC(C)(C)c1ccc(N(C(=O)C2CCCN2)C2(C(=O)NC3CCCCC3)CCCc3ccncc32)cc1] |
| 493 | 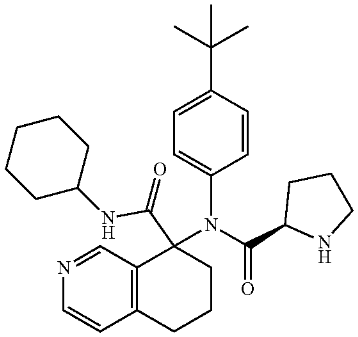 [SMILES: CC(C)(C)c1ccc(N(C(=O)[C@H]2CCCN2)C2(C(=O)NC3CCCCC3)CCCc3ccncc32)cc1] |
TABLE 1-continued
| Exemplary compounds. | |
|---|---|
| Cmpd No. | Structure |
| 494 | 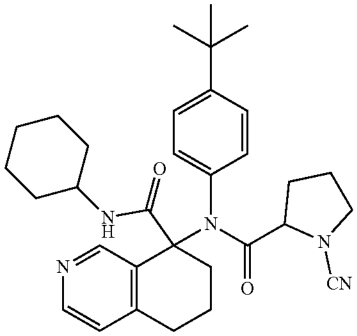 [SMILES: CC(C)(C)c1ccc(N(C(=O)C2CCCN2C#N)C2(C(=O)NC3CCCCC3)CCCc3ccncc32)cc1] |
| 495 | 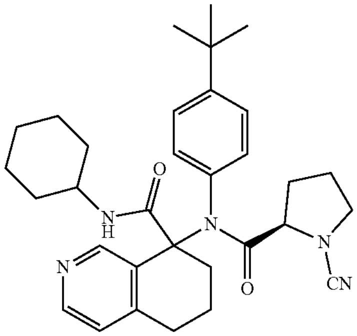 [SMILES: CC(C)(C)c1ccc(N(C(=O)[C@H]2CCCN2C#N)C2(C(=O)NC3CCCCC3)CCCc3ccncc32)cc1] |
| 496 | 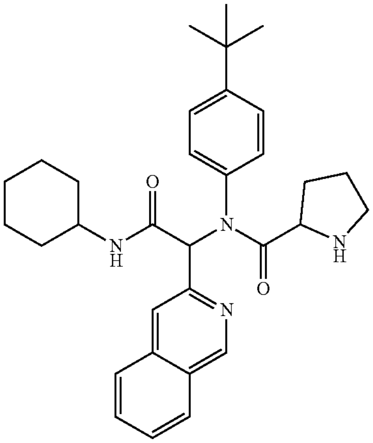 [SMILES: CC(C)(C)c1ccc(N(C(=O)C2CCCN2)C(C(=O)NC2CCCCC2)c2cc3ccccc3cn2)cc1] |

TABLE 1-continued
| Cmpd No. | Structure |
|---|---|
| 497 | 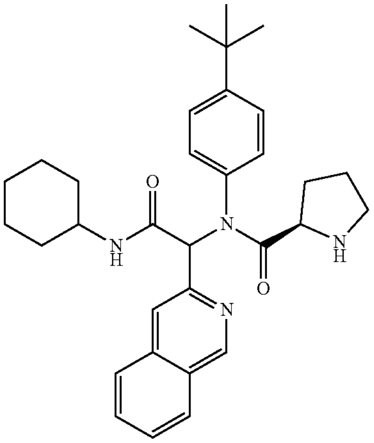 [SMILES: CC(C)(C)c1ccc(N(C(=O)[C@H]2CCCN2)C(C(=O)NC2CCCCC2)c2cc3ccccc3cn2)cc1] |
| 498 | 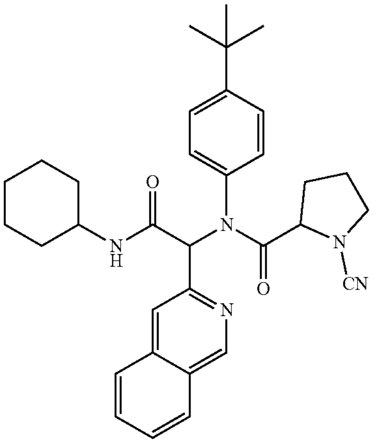 [SMILES: CC(C)(C)c1ccc(N(C(=O)C2CCCN2C#N)C(C(=O)NC2CCCCC2)c2cc3ccccc3cn2)cc1] |
| 499 | 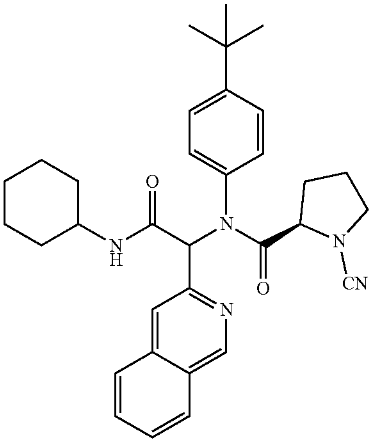 [SMILES: CC(C)(C)c1ccc(N(C(=O)[C@H]2CCCN2C#N)C(C(=O)NC2CCCCC2)c2cc3ccccc3cn2)cc1] |
TABLE 1-continued
| Cmpd No. | Structure |
|---|---|
| 500 | 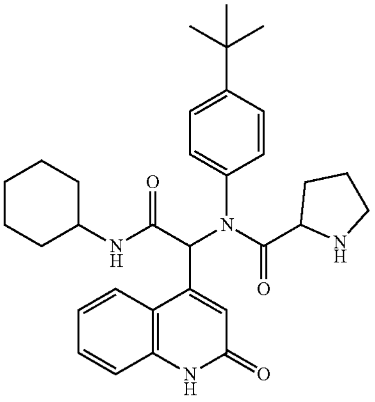 [SMILES: CC(C)(C)c1ccc(N(C(=O)C2CCCN2)C(C(=O)NC2CCCCC2)c2cc(=O)[nH]c3ccccc23)cc1] |
| 501 | 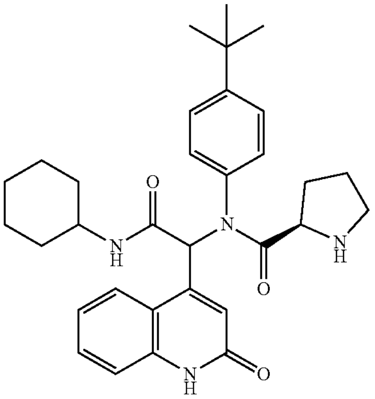 [SMILES: CC(C)(C)c1ccc(N(C(=O)[C@H]2CCCN2)C(C(=O)NC2CCCCC2)c2cc(=O)[nH]c3ccccc23)cc1] |
| 502 | 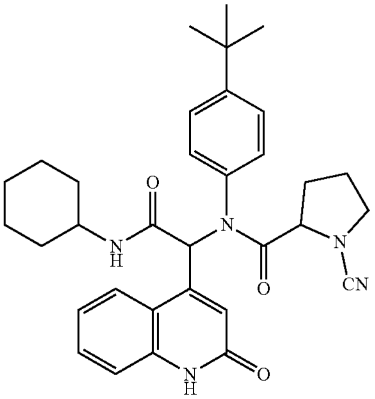 [SMILES: CC(C)(C)c1ccc(N(C(=O)C2CCCN2C#N)C(C(=O)NC2CCCCC2)c2cc(=O)[nH]c3ccccc23)cc1] |
Exemplary compounds.

TABLE 1-continued
| Cmpd No. | Structure |
|---|---|
| 503 | 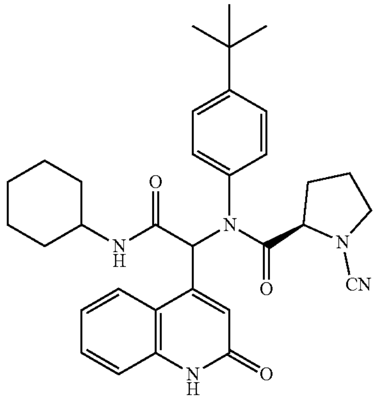 [SMILES: CC(C)(C)c1ccc(N(C(=O)[C@H]2CCCN2C#N)C(C(=O)NC2CCCCC2)c2cc(=O)[nH]c3ccccc23)cc1] |
| 504 | 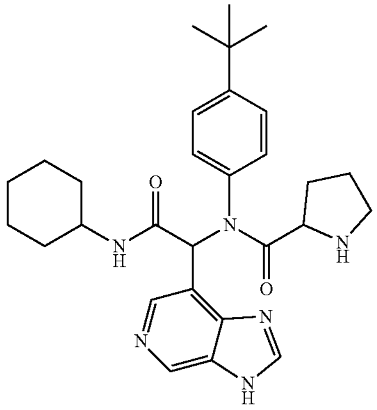 [SMILES: CC(C)(C)c1ccc(N(C(=O)C2CCCN2)C(C(=O)NC2CCCCC2)c2cncc3[nH]cnc23)cc1] |
| 505 | 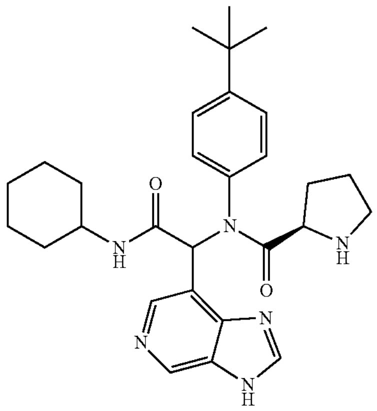 [SMILES: CC(C)(C)c1ccc(N(C(=O)[C@H]2CCCN2)C(C(=O)NC2CCCCC2)c2cncc3[nH]cnc23)cc1] |
TABLE 1-continued
| Cmpd No. | Structure |
|---|---|
| 506 | 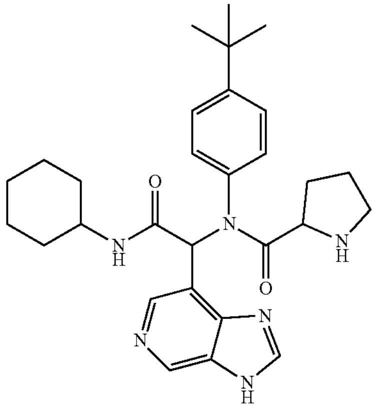 [SMILES: CC(C)(C)c1ccc(N(C(=O)C2CCCN2)C(C(=O)NC2CCCCC2)c2cncc3[nH]cnc23)cc1] |
| 507 | 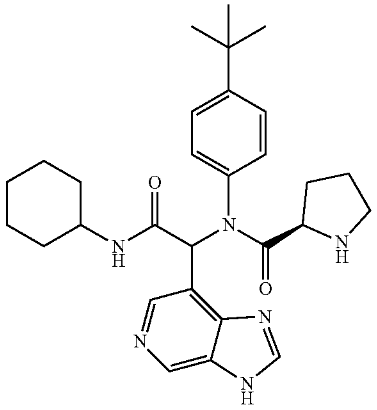 [SMILES: CC(C)(C)c1ccc(N(C(=O)[C@H]2CCCN2)C(C(=O)NC2CCCCC2)c2cncc3[nH]cnc23)cc1] |
| 508 | 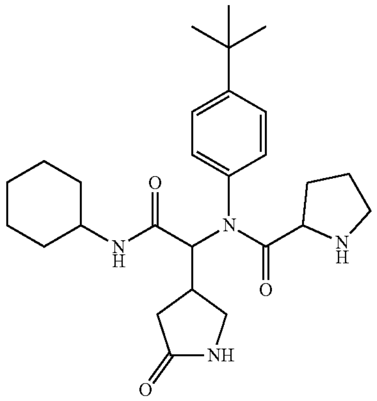 [SMILES: CC(C)(C)c1ccc(N(C(=O)C2CCCN2)C(C(=O)NC2CCCCC2)C2CNC(=O)C2)cc1] |

TABLE 1-continued
| Cmpd No. | Structure |
|---|---|
| Exemplary compounds. | |
| 509 | 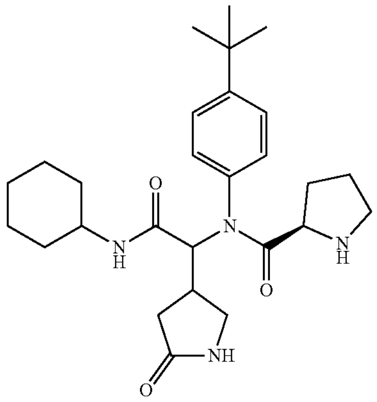 [SMILES: CC(C)(C)c1ccc(N(C(=O)[C@H]2CCCN2)C(C(=O)NC2CCCCC2)C2CNC(=O)C2)cc1] |
| 510 | 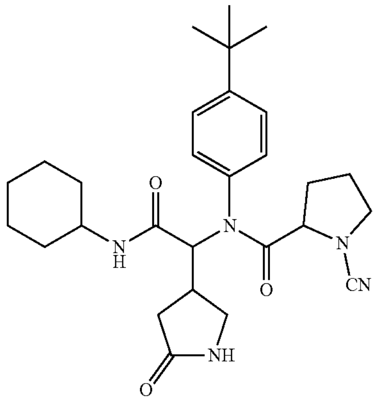 [SMILES: CC(C)(C)c1ccc(N(C(=O)C2CCCN2C#N)C(C(=O)NC2CCCCC2)C2CNC(=O)C2)cc1] |
| 511 | 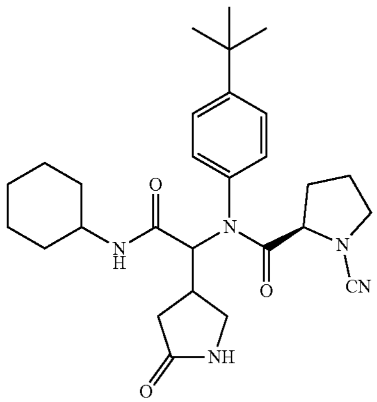 [SMILES: CC(C)(C)c1ccc(N(C(=O)[C@H]2CCCN2C#N)C(C(=O)NC2CCCCC2)C2CNC(=O)C2)cc1] |
TABLE 1-continued
| Cmpd No. | Structure |
|---|---|
| Exemplary compounds. | |
| 512 | 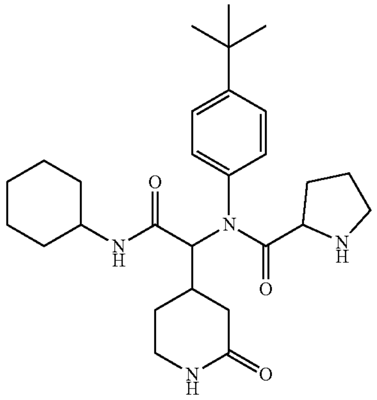 [SMILES: CC(C)(C)c1ccc(N(C(=O)C2CCCN2)C(C(=O)NC2CCCCC2)C2CCNC(=O)C2)cc1] |
| 513 | 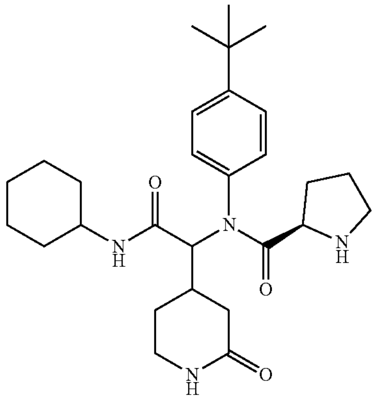 [SMILES: CC(C)(C)c1ccc(N(C(=O)[C@H]2CCCN2)C(C(=O)NC2CCCCC2)C2CCNC(=O)C2)cc1] |
| 514 | 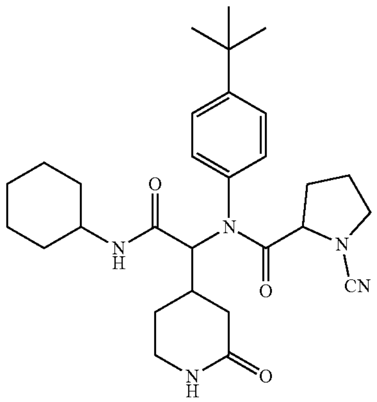 [SMILES: CC(C)(C)c1ccc(N(C(=O)C2CCCN2C#N)C(C(=O)NC2CCCCC2)C2CCNC(=O)C2)cc1] |

TABLE 1-continued
| Exemplary compounds. | |
|---|---|
| Cmpd No. | Structure |
| 515 | 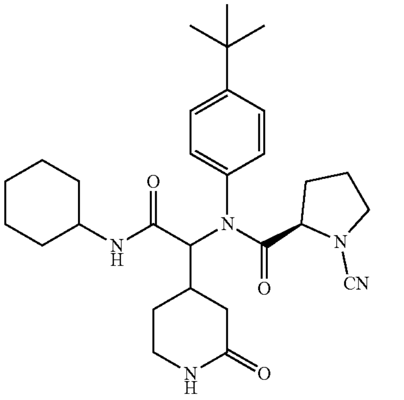 [SMILES: CC(C)(C)c1ccc(N(C(=O)[C@H]2CCCN2C#N)C(C(=O)NC2CCCCC2)C2CCNC(=O)C2)cc1] |
| 516 | 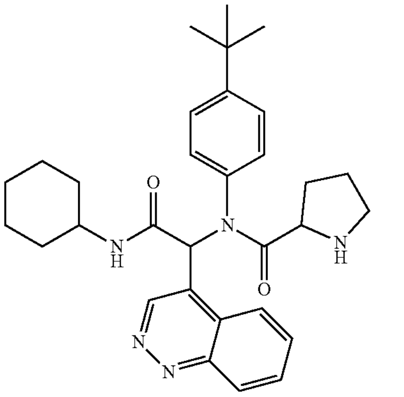 [SMILES: CC(C)(C)c1ccc(N(C(=O)C2CCCN2)C(C(=O)NC2CCCCC2)c2cnnc3ccccc23)cc1] |
| 517 | 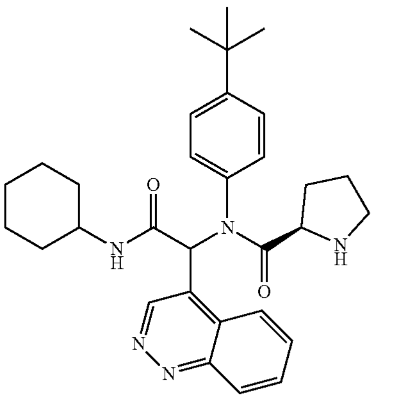 [SMILES: CC(C)(C)c1ccc(N(C(=O)[C@H]2CCCN2)C(C(=O)NC2CCCCC2)c2cnnc3ccccc23)cc1] |
TABLE 1-continued
| Exemplary compounds. | |
|---|---|
| Cmpd No. | Structure |
| 518 | 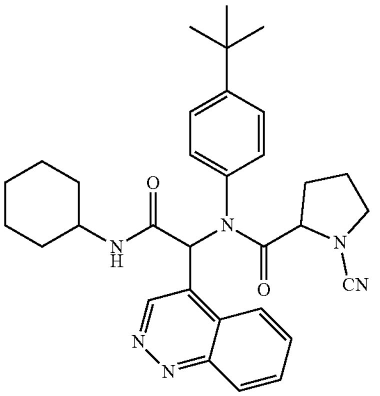 [SMILES: CC(C)(C)c1ccc(N(C(=O)C2CCCN2C#N)C(C(=O)NC2CCCCC2)c2cnnc3ccccc23)cc1] |
| 519 | 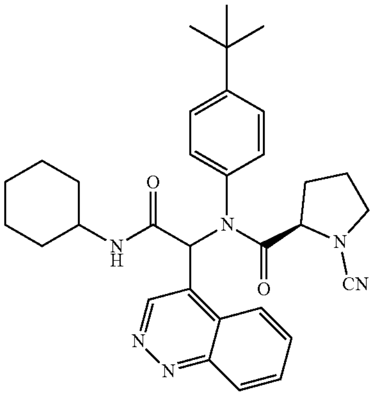 [SMILES: CC(C)(C)c1ccc(N(C(=O)[C@H]2CCCN2C#N)C(C(=O)NC2CCCCC2)c2cnnc3ccccc23)cc1] |
| 520 | 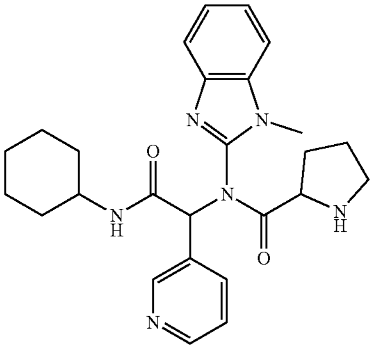 [SMILES: Cn1c(N(C(=O)C2CCCN2)C(C(=O)NC2CCCCC2)c2cccnc2)nc2ccccc21] |
| 521 | 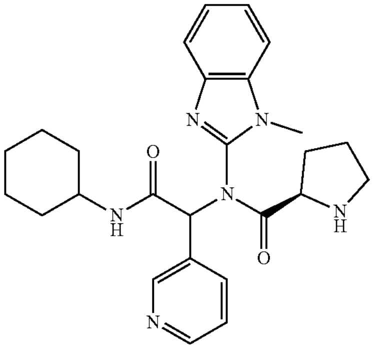 [SMILES: Cn1c(N(C(=O)[C@H]2CCCN2)C(C(=O)NC2CCCCC2)c2cccnc2)nc2ccccc21] |

TABLE 1-continued
Exemplary compounds.
| Cmpd No. | Structure |
|---|---|
| 522 | 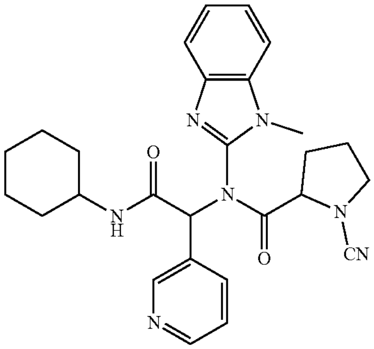 [SMILES: Cn1c(N(C(=O)C2CCCN2C#N)C(C(=O)NC2CCCCC2)c2cccnc2)nc2ccccc21] |
| 523 | 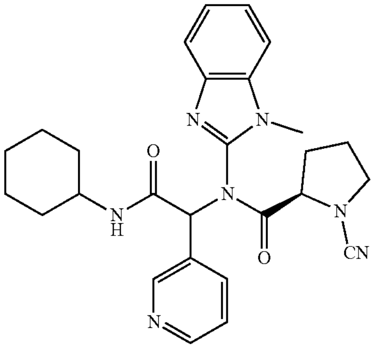 [SMILES: Cn1c(N(C(=O)[C@H]2CCCN2C#N)C(C(=O)NC2CCCCC2)c2cccnc2)nc2ccccc21] |
| 524 | 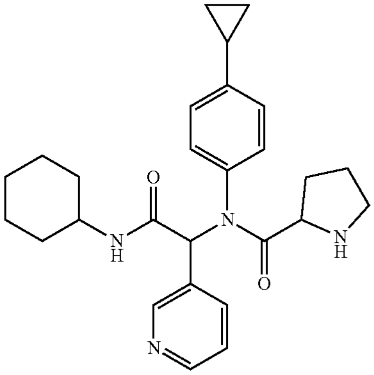 [SMILES: O=C(NC1CCCCC1)C(c1cccnc1)N(C(=O)C1CCCN1)c1ccc(C2CC2)cc1] |
| 525 | 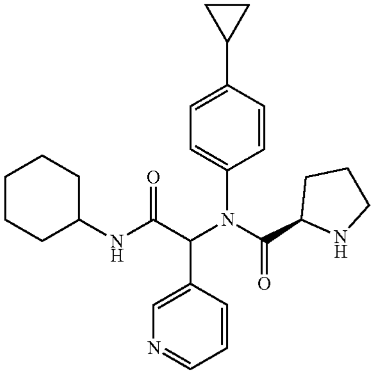 [SMILES: O=C(NC1CCCCC1)C(c1cccnc1)N(C(=O)[C@H]1CCCN1)c1ccc(C2CC2)cc1] |
TABLE 1-continued
Exemplary compounds.
| Cmpd No. | Structure |
|---|---|
| 526 | 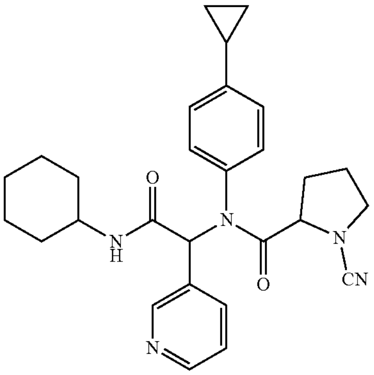 [SMILES: N#CN1CCCC1C(=O)N(c1ccc(C2CC2)cc1)C(C(=O)NC1CCCCC1)c1cccnc1] |
| 527 | 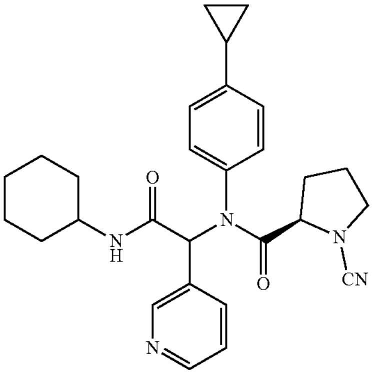 [SMILES: N#CN1CCC[C@@H]1C(=O)N(c1ccc(C2CC2)cc1)C(C(=O)NC1CCCCC1)c1cccnc1] |
| 528 | 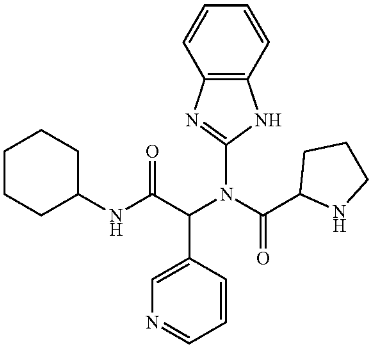 [SMILES: O=C(NC1CCCCC1)C(c1cccnc1)N(C(=O)C1CCCN1)c1nc2ccccc2[nH]1] |
| 529 | 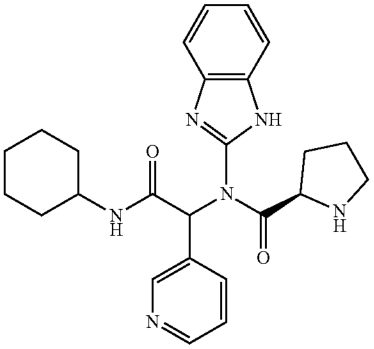 [SMILES: O=C(NC1CCCCC1)C(c1cccnc1)N(C(=O)[C@H]1CCCN1)c1nc2ccccc2[nH]1] |

TABLE 1-continued
Exemplary compounds.
| Cmpd No. | Structure |
|---|---|
| 530 | 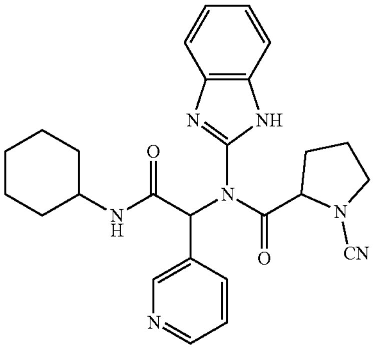 [SMILES: N#CN1CCCC1C(=O)N(c1nc2ccccc2[nH]1)C(C(=O)NC1CCCCC1)c1cccnc1] |
| 531 | 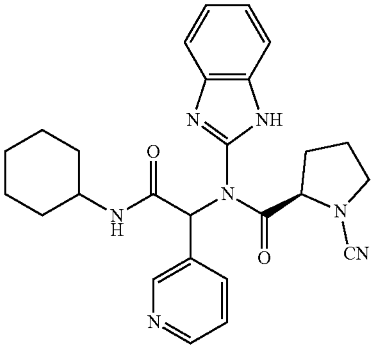 |
| 532 | 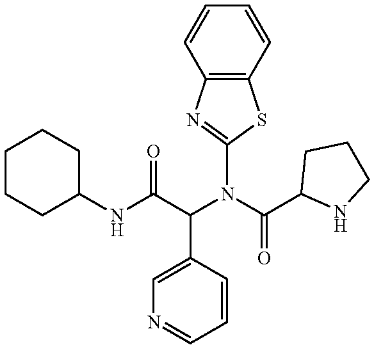 |
| 533 | 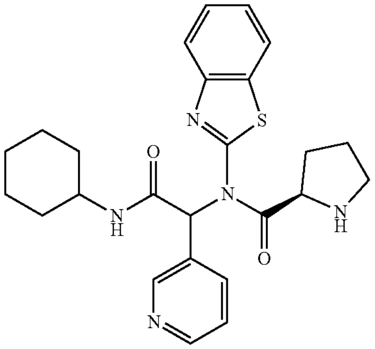 [SMILES: O=C(NC1CCCCC1)C(c1cccnc1)N(C(=O)[C@H]1CCCN1)c1nc2ccccc2s1] |
| 534 | 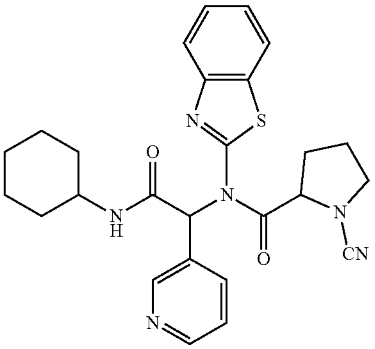 [SMILES: N#CN1CCCC1C(=O)N(c1nc2ccccc2s1)C(C(=O)NC1CCCCC1)c1cccnc1] |
| 535 | 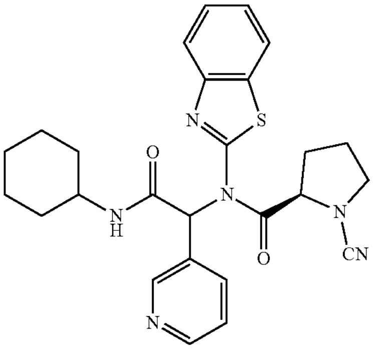 [SMILES: N#CN1CCC[C@@H]1C(=O)N(c1nc2ccccc2s1)C(C(=O)NC1CCCCC1)c1cccnc1] |
| 536 | 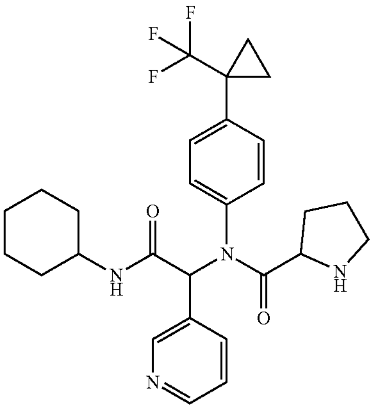 [SMILES: O=C(NC1CCCCC1)C(c1cccnc1)N(C(=O)C1CCCN1)c1ccc(C2(C(F)(F)F)CC2)cc1] |
| 537 | 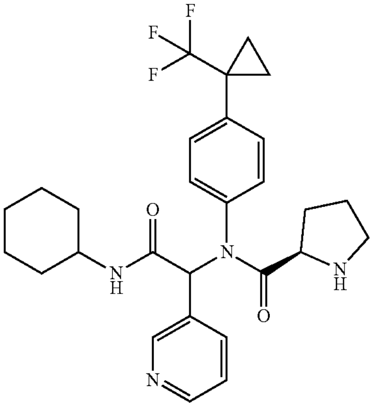 [SMILES: O=C(NC1CCCCC1)C(c1cccnc1)N(C(=O)[C@H]1CCCN1)c1ccc(C2(C(F)(F)F)CC2)cc1] |

TABLE 1-continued
Exemplary compounds.
| Cmpd No. | Structure |
| --- | --- |
| 538 | 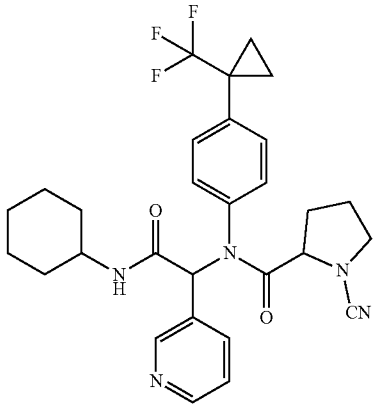 [SMILES: N#CN1CCCC1C(=O)N(c1ccc(C2(C(F)(F)F)CC2)cc1)C(C(=O)NC1CCCCC1)c1cccnc1] |
| 539 | 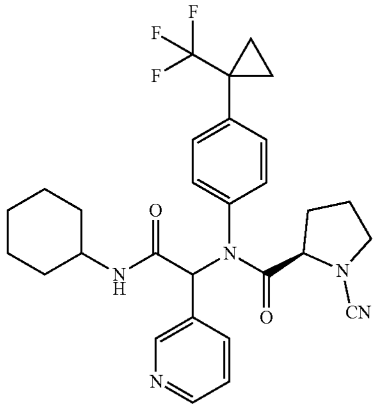 [SMILES: N#CN1CCC[C@@H]1C(=O)N(c1ccc(C2(C(F)(F)F)CC2)cc1)C(C(=O)NC1CCCCC1)c1cccnc1] |
| 540 | 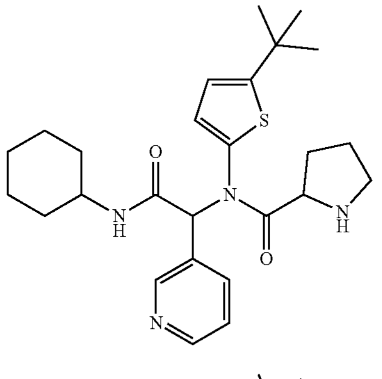 |
| 541 | 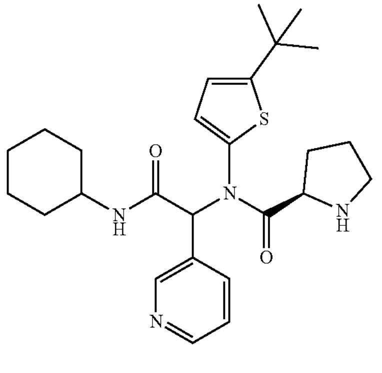 [SMILES: CC(C)(C)c1ccc(N(C(=O)[C@H]2CCCN2)C(C(=O)NC2CCCCC2)c2cccnc2)s1] |
TABLE 1-continued
Exemplary compounds.
| Cmpd No. | Structure |
| --- | --- |
| 542 | 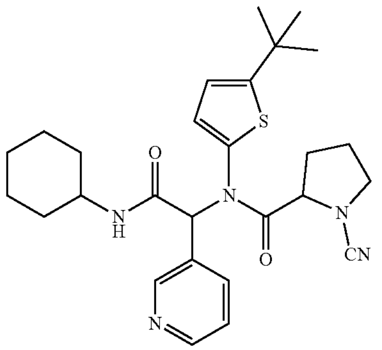 [SMILES: CC(C)(C)c1ccc(N(C(=O)C2CCCN2C#N)C(C(=O)NC2CCCCC2)c2cccnc2)s1] |
| 543 | 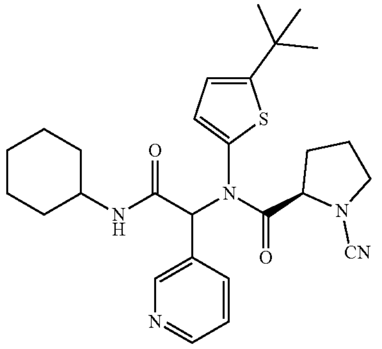 [SMILES: CC(C)(C)c1ccc(N(C(=O)[C@H]2CCCN2C#N)C(C(=O)NC2CCCCC2)c2cccnc2)s1] |
| 544 | 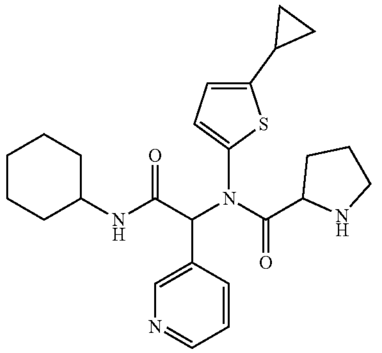 [SMILES: O=C(NC1CCCCC1)C(c1cccnc1)N(C(=O)C1CCCN1)c1ccc(C2CC2)s1] |
| 545 | 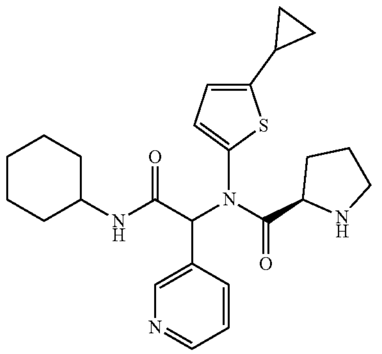 [SMILES: O=C(NC1CCCCC1)C(c1cccnc1)N(C(=O)[C@H]1CCCN1)c1ccc(C2CC2)s1] |

TABLE 1-continued
| Exemplary compounds. | |
|---|---|
| Cmpd No. | Structure |
| 546 | 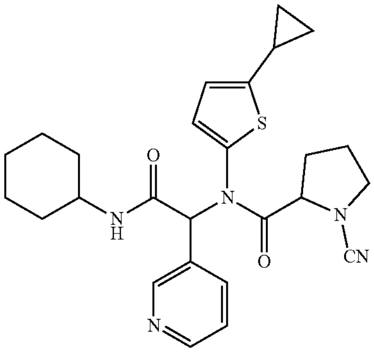 [SMILES: N#CN1CCCC1C(=O)N(c1ccc(C2CC2)s1)C(C(=O)NC1CCCCC1)c1cccnc1] |
| 547 | 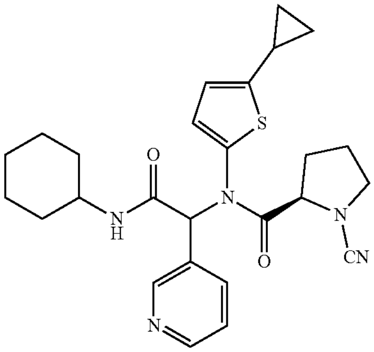 [SMILES: N#CN1CCC[C@@H]1C(=O)N(c1ccc(C2CC2)s1)C(C(=O)NC1CCCCC1)c1cccnc1] |
| 548 | 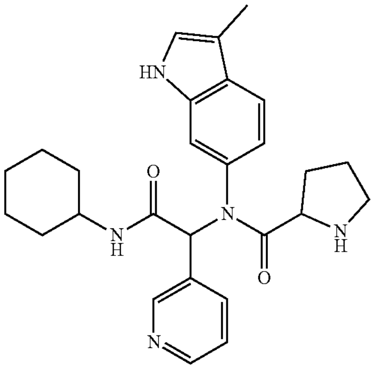 [SMILES: Cc1c[nH]c2cc(N(C(=O)C3CCCN3)C(C(=O)NC3CCCCC3)c3cccnc3)ccc12] |
| 549 | 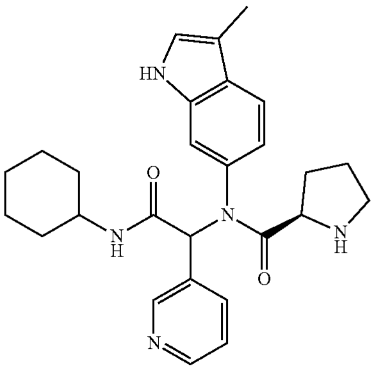 [SMILES: Cc1c[nH]c2cc(N(C(=O)[C@H]3CCCN3)C(C(=O)NC3CCCCC3)c3cccnc3)ccc12] |
TABLE 1-continued
| Exemplary compounds. | |
|---|---|
| Cmpd No. | Structure |
| 550 | 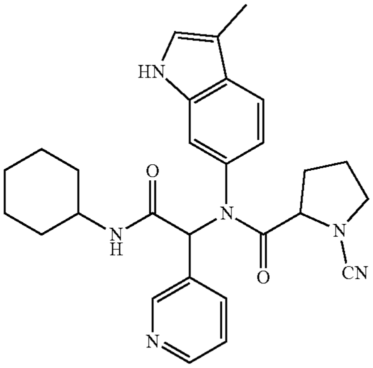 [SMILES: Cc1c[nH]c2cc(N(C(=O)C3CCCN3C#N)C(C(=O)NC3CCCCC3)c3cccnc3)ccc12] |
| 551 | 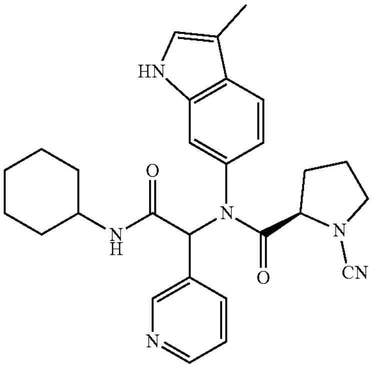 [SMILES: Cc1c[nH]c2cc(N(C(=O)[C@H]3CCCN3C#N)C(C(=O)NC3CCCCC3)c3cccnc3)ccc12] |
| 552 | 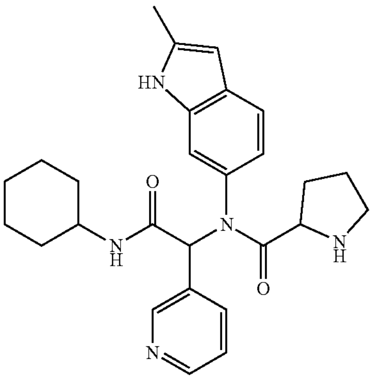 [SMILES: Cc1cc2ccc(N(C(=O)C3CCCN3)C(C(=O)NC3CCCCC3)c3cccnc3)cc2[nH]1] |
| 553 | 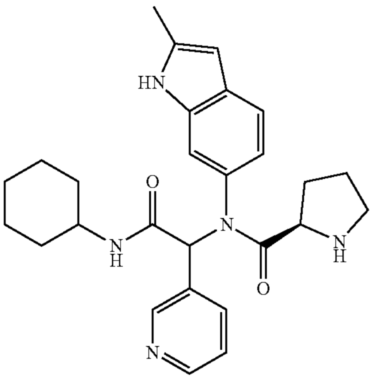 [SMILES: Cc1cc2ccc(N(C(=O)[C@H]3CCCN3)C(C(=O)NC3CCCCC3)c3cccnc3)cc2[nH]1] |

TABLE 1-continued
Exemplary compounds.
| Cmpd No. | Structure |
| --- | --- |
| 554 | 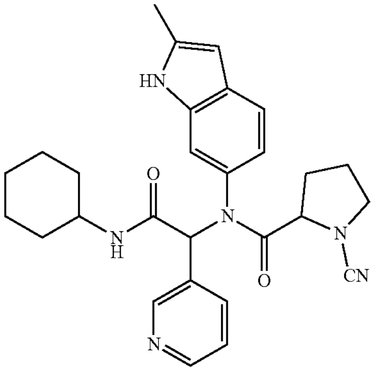 [SMILES: Cc1cc2ccc(N(C(=O)C3CCCN3C#N)C(C(=O)NC3CCCCC3)c3cccnc3)cc2[nH]1] |
| 555 | 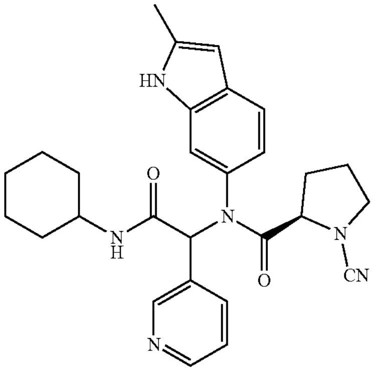 [SMILES: Cc1cc2ccc(N(C(=O)[C@H]3CCCN3C#N)C(C(=O)NC3CCCCC3)c3cccnc3)cc2[nH]1] |
| 556 | 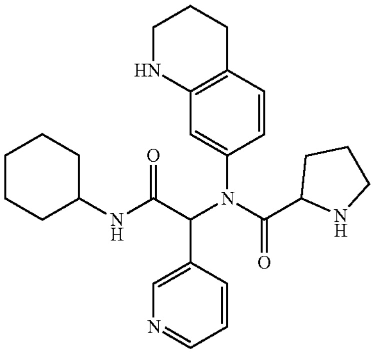 [SMILES: O=C(NC1CCCCC1)C(c1cccnc1)N(C(=O)C1CCCN1)c1ccc2c(c1)NCCC2] |
| 557 | 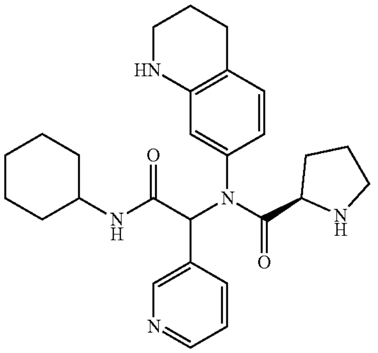 [SMILES: O=C(NC1CCCCC1)C(c1cccnc1)N(C(=O)[C@H]1CCCN1)c1ccc2c(c1)NCCC2] |
| 558 | 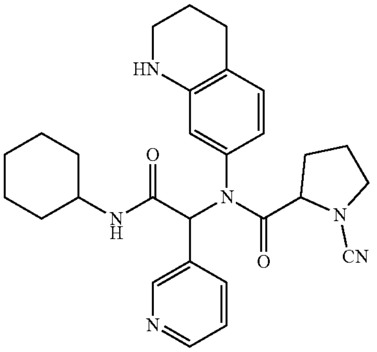 [SMILES: N#CN1CCCC1C(=O)N(c1ccc2c(c1)NCCC2)C(C(=O)NC1CCCCC1)c1cccnc1] |
| 559 | 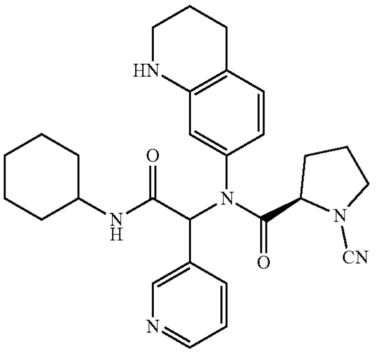 [SMILES: N#CN1CCC[C@@H]1C(=O)N(c1ccc2c(c1)NCCC2)C(C(=O)NC1CCCCC1)c1cccnc1] |
| 560 | 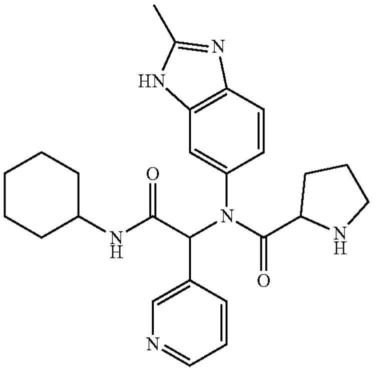 [SMILES: Cc1nc2ccc(N(C(=O)C3CCCN3)C(C(=O)NC3CCCCC3)c3cccnc3)cc2[nH]1] |
| 561 | 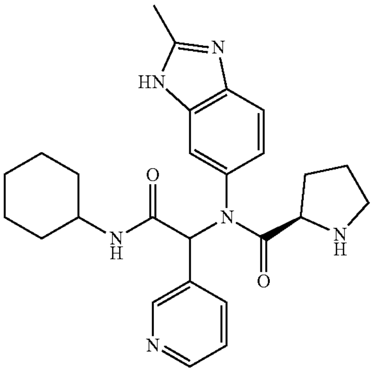 [SMILES: Cc1nc2ccc(N(C(=O)[C@H]3CCCN3)C(C(=O)NC3CCCCC3)c3cccnc3)cc2[nH]1] |

TABLE 1-continued
Exemplary compounds.
| Cmpd No. | Structure |
| --- | --- |
| 562 | 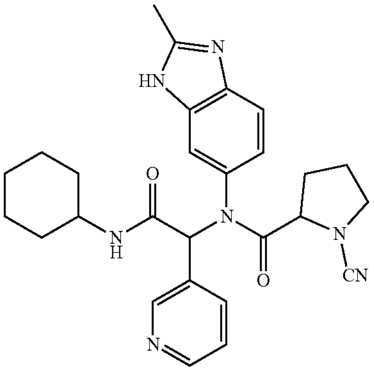 [SMILES: Cc1nc2ccc(N(C(=O)C3CCCN3C#N)C(C(=O)NC3CCCCC3)c3cccnc3)cc2[nH]1] |
| 563 | 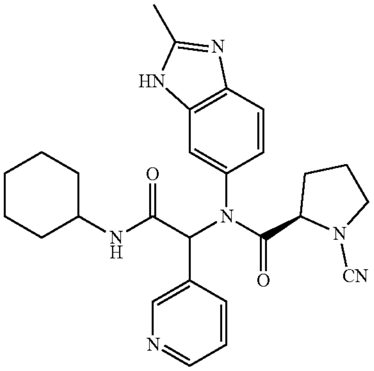 [SMILES: Cc1nc2ccc(N(C(=O)[C@H]3CCCN3C#N)C(C(=O)NC3CCCCC3)c3cccnc3)cc2[nH]1] |
| 564 | 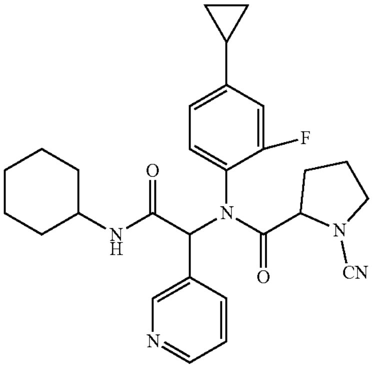 [SMILES: N#CN1CCCC1C(=O)N(c1ccc(C2CC2)cc1F)C(C(=O)NC1CCCCC1)c1cccnc1] |
| 565 | 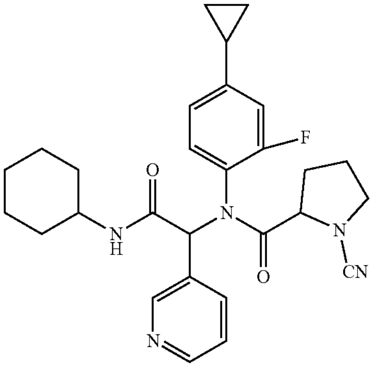 [SMILES: N#CN1CCCC1C(=O)N(c1ccc(C2CC2)cc1F)C(C(=O)NC1CCCCC1)c1cccnc1] |
| 566 | 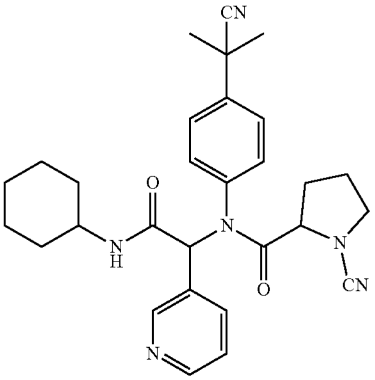 [SMILES: CC(C)(C#N)c1ccc(N(C(=O)C2CCCN2C#N)C(C(=O)NC2CCCCC2)c2cccnc2)cc1] |
| 567 | 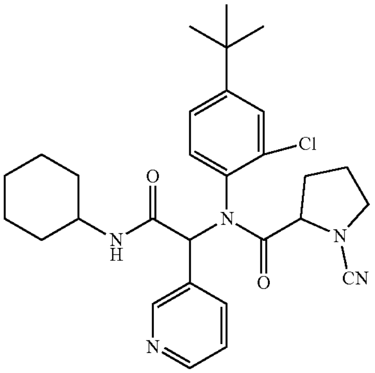 [SMILES: CC(C)(C)c1ccc(N(C(=O)C2CCCN2C#N)C(C(=O)NC2CCCCC2)c2cccnc2)c(Cl)c1] |
| 568 | 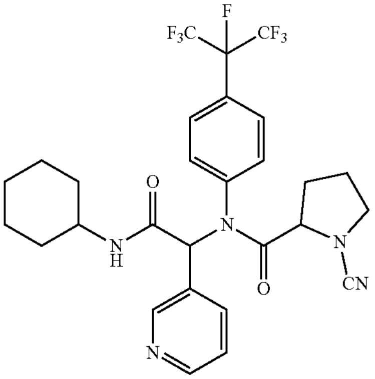 [SMILES: N#CN1CCCC1C(=O)N(c1ccc(C(F)(C(F)(F)F)C(F)(F)F)cc1)C(C(=O)NC1CCCCC1)c1cccnc1] |
| 569 | 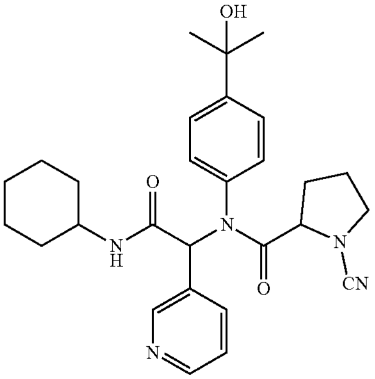 |

TABLE 1-continued
| Exemplary compounds. | |
|---|---|
| Cmpd No. | Structure |
| 570 | 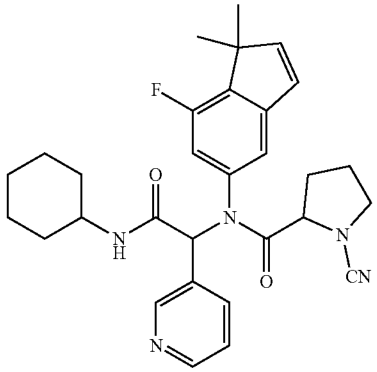 [SMILES: CC1(C)C=Cc2cc(N(C(=O)C3CCCN3C#N)C(C(=O)NC3CCCCC3)c3cccnc3)cc(F)c21] |
| 571 | 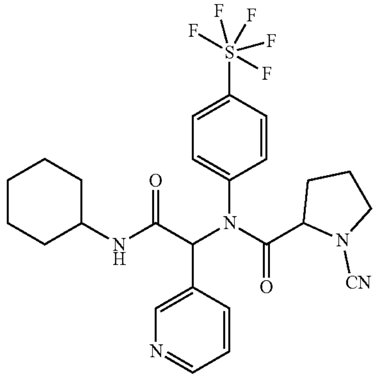 [SMILES: N#CN1CCCC1C(=O)N(c1ccc(S(F)(F)(F)(F)F)cc1)C(C(=O)NC1CCCCC1)c1cccnc1] |
| 572 | 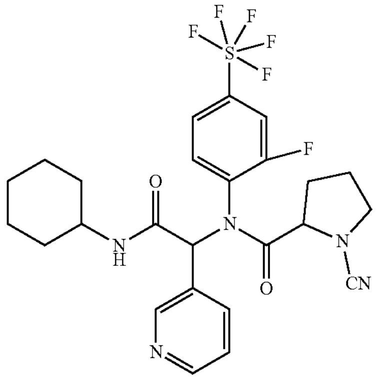 [SMILES: N#CN1CCCC1C(=O)N(c1ccc(S(F)(F)(F)(F)F)cc1F)C(C(=O)NC1CCCCC1)c1cccnc1] |
| 573 | 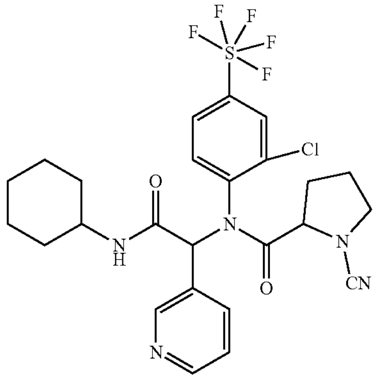 [SMILES: N#CN1CCCC1C(=O)N(c1ccc(S(F)(F)(F)(F)F)cc1Cl)C(C(=O)NC1CCCCC1)c1cccnc1] |
TABLE 1-continued
| Exemplary compounds. | |
|---|---|
| Cmpd No. | Structure |
| 574 | 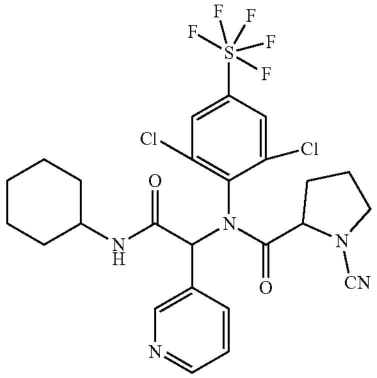 [SMILES: N#CN1CCCC1C(=O)N(c1c(Cl)cc(S(F)(F)(F)(F)F)cc1Cl)C(C(=O)NC1CCCCC1)c1cccnc1] |
| 575 | 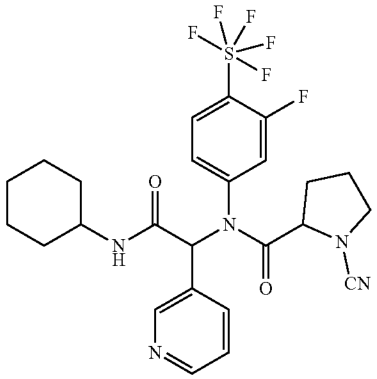 [SMILES: N#CN1CCCC1C(=O)N(c1ccc(S(F)(F)(F)(F)F)c(F)c1)C(C(=O)NC1CCCCC1)c1cccnc1] |
| 576 | 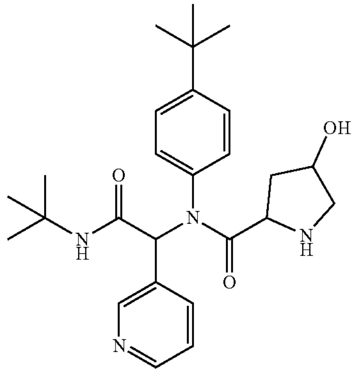 [SMILES: CC(C)(C)NC(=O)C(c1cccnc1)N(C(=O)C1CC(O)CN1)c1ccc(C(C)(C)C)cc1] |
| 577 | 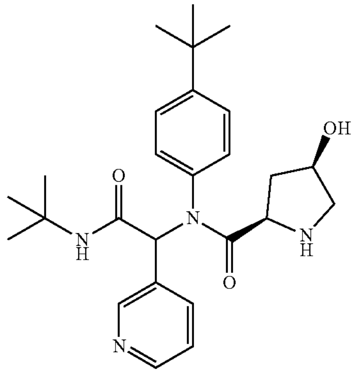 [SMILES: CC(C)(C)NC(=O)C(c1cccnc1)N(C(=O)[C@H]1C[C@@H](O)CN1)c1ccc(C(C)(C)C)cc1] |

TABLE 1-continued
| Exemplary compounds. | |
|---|---|
| Cmpd No. | Structure |
| 578 | 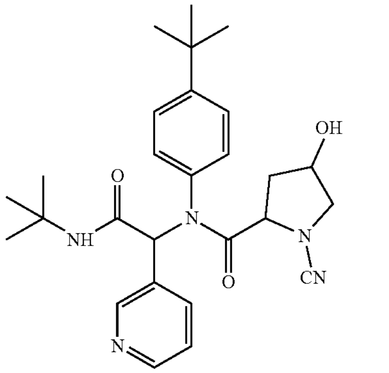 |
| 579 | 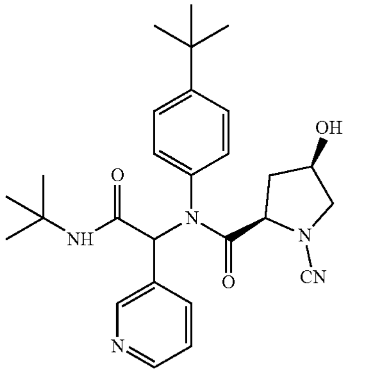 |
| 580 | 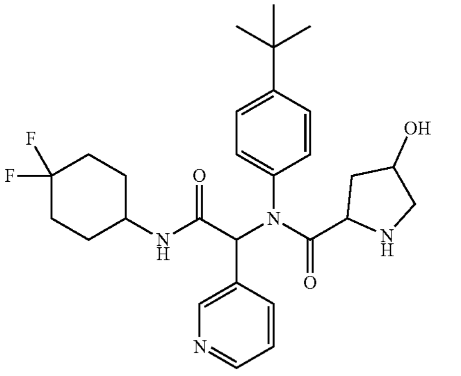 [SMILES: CC(C)(C)c1ccc(N(C(=O)C2CC(O)CN2)C(C(=O)NC2CCC(F)(F)CC2)c2cccnc2)cc1] |
| 581 | 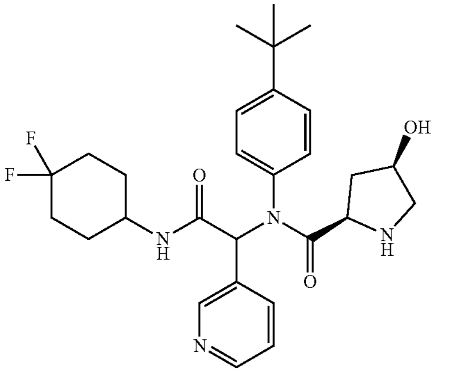 [SMILES: CC(C)(C)c1ccc(N(C(=O)[C@H]2C[C@@H](O)CN2)C(C(=O)NC2CCC(F)(F)CC2)c2cccnc2)cc1] |
TABLE 1-continued
| Exemplary compounds. | |
|---|---|
| Cmpd No. | Structure |
| 582 | 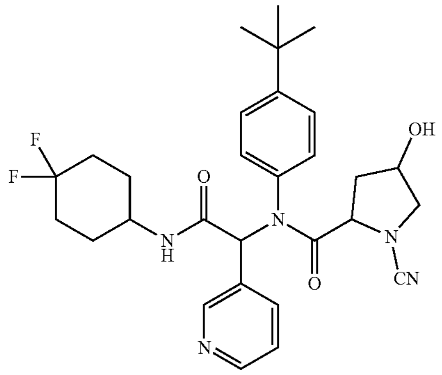 [SMILES: CC(C)(C)c1ccc(N(C(=O)C2CC(O)CN2C#N)C(C(=O)NC2CCC(F)(F)CC2)c2cccnc2)cc1] |
| 583 | 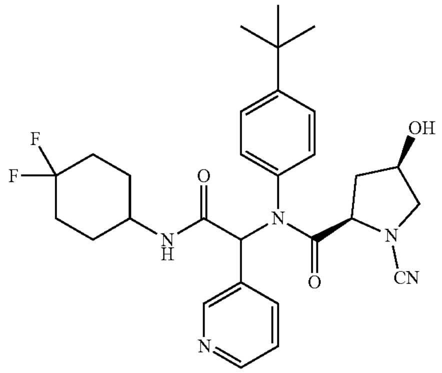 [SMILES: CC(C)(C)c1ccc(N(C(=O)[C@H]2C[C@@H](O)CN2C#N)C(C(=O)NC2CCC(F)(F)CC2)c2cccnc2)cc1] |
| 584 | 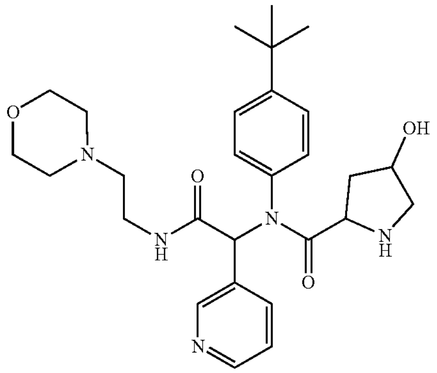 [SMILES: CC(C)(C)c1ccc(N(C(=O)C2CC(O)CN2)C(C(=O)NCCN2CCOCC2)c2cccnc2)cc1] |
| 585 | 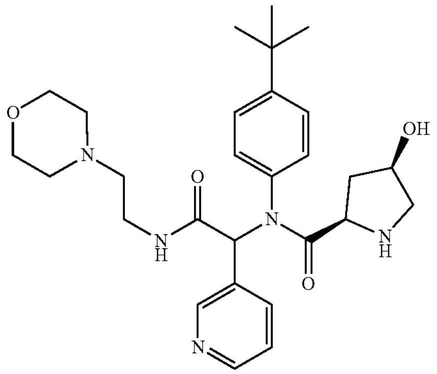 [SMILES: CC(C)(C)c1ccc(N(C(=O)[C@H]2C[C@@H](O)CN2)C(C(=O)NCCN2CCOCC2)c2cccnc2)cc1] |

TABLE 1-continued
| Exemplary compounds. | |
|---|---|
| Cmpd No. | Structure |
| 586 | 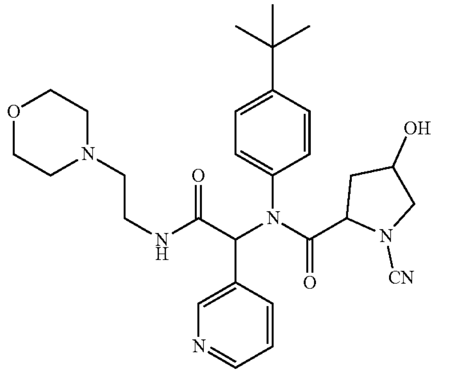 [SMILES: CC(C)(C)c1ccc(N(C(=O)C2CC(O)CN2C#N)C(C(=O)NCCN2CCOCC2)c2cccnc2)cc1] |
| 587 | 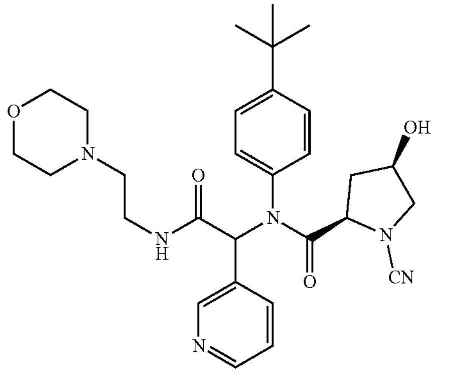 [SMILES: CC(C)(C)c1ccc(N(C(=O)[C@H]2C[C@@H](O)CN2C#N)C(C(=O)NCCN2CCOCC2)c2cccnc2)cc1] |
| 588 | 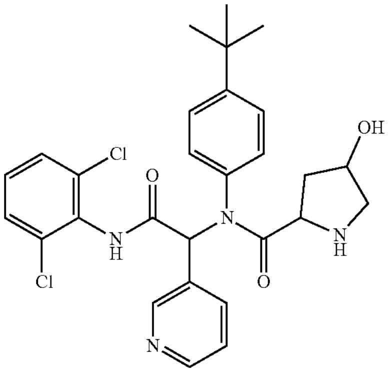 [SMILES: CC(C)(C)c1ccc(N(C(=O)C2CC(O)CN2)C(C(=O)Nc2c(Cl)cccc2Cl)c2cccnc2)cc1] |
| 589 | 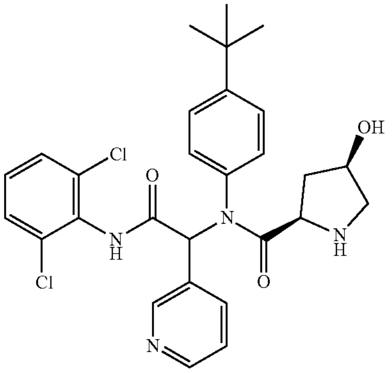 [SMILES: CC(C)(C)c1ccc(N(C(=O)[C@H]2C[C@@H](O)CN2)C(C(=O)Nc2c(Cl)cccc2Cl)c2cccnc2)cc1] |
TABLE 1-continued
| Exemplary compounds. | |
|---|---|
| Cmpd No. | Structure |
| 590 | 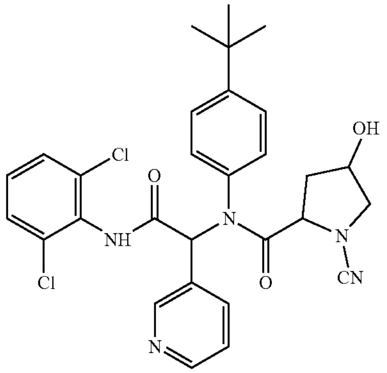 |
| 591 | 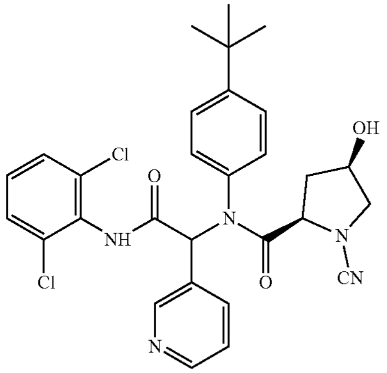 |
| 592 | 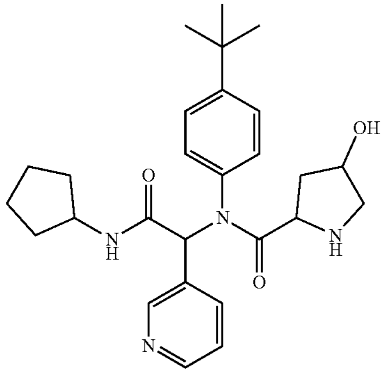 [SMILES: CC(C)(C)c1ccc(N(C(=O)C2CC(O)CN2)C(C(=O)NC2CCCC2)c2cccnc2)cc1] |
| 593 | 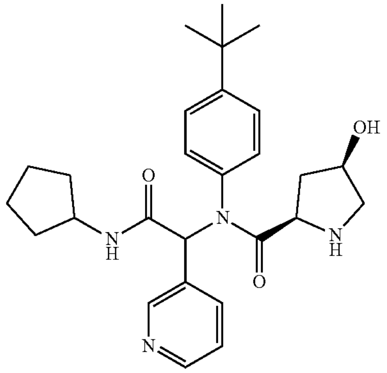 [SMILES: CC(C)(C)c1ccc(N(C(=O)[C@H]2C[C@@H](O)CN2)C(C(=O)NC2CCCC2)c2cccnc2)cc1] |

TABLE 1-continued
| Exemplary compounds. | |
|---|---|
| Cmpd No. | Structure |
| 594 | 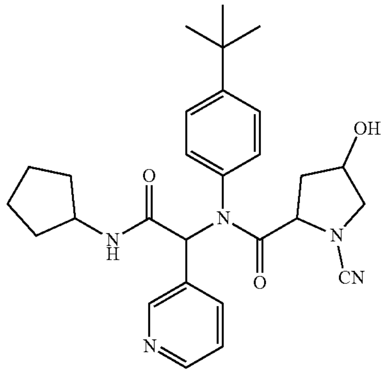 [SMILES: CC(C)(C)c1ccc(N(C(=O)C2CC(O)CN2C#N)C(C(=O)NC2CCCC2)c2cccnc2)cc1] |
| 595 | 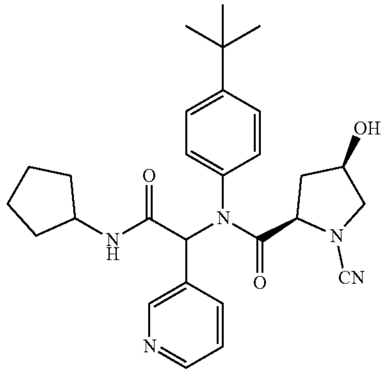 [SMILES: CC(C)(C)c1ccc(N(C(=O)[C@H]2C[C@@H](O)CN2C#N)C(C(=O)NC2CCCC2)c2cccnc2)cc1] |
| 596 | 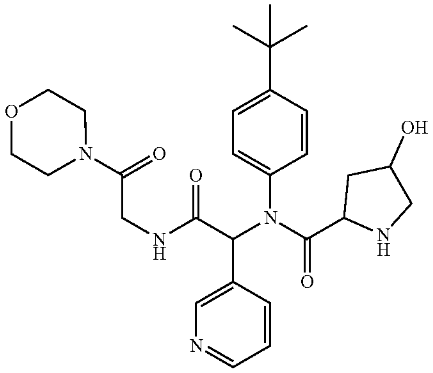 [SMILES: CC(C)(C)c1ccc(N(C(=O)C2CC(O)CN2)C(C(=O)NCC(=O)N2CCOCC2)c2cccnc2)cc1] |
| 597 | 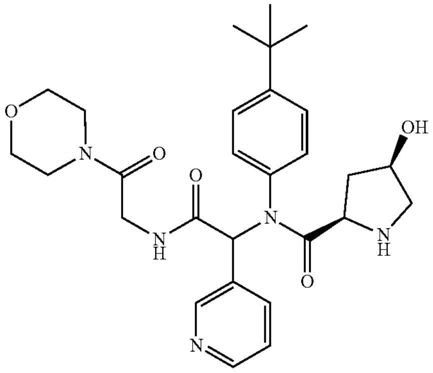 [SMILES: CC(C)(C)c1ccc(N(C(=O)[C@H]2C[C@@H](O)CN2)C(C(=O)NCC(=O)N2CCOCC2)c2cccnc2)cc1] |
TABLE 1-continued
| Exemplary compounds. | |
|---|---|
| Cmpd No. | Structure |
| 598 | 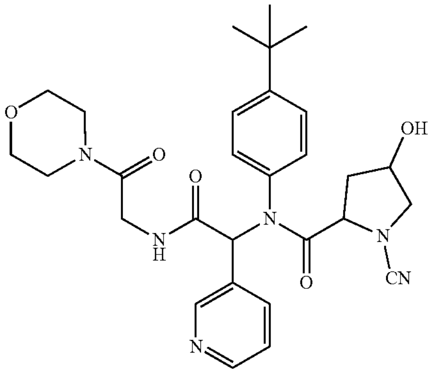 [SMILES: CC(C)(C)c1ccc(N(C(=O)C2CC(O)CN2C#N)C(C(=O)NCC(=O)N2CCOCC2)c2cccnc2)cc1] |
| 599 | 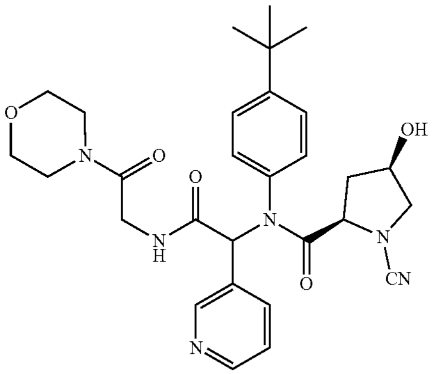 [SMILES: CC(C)(C)c1ccc(N(C(=O)[C@H]2C[C@@H](O)CN2C#N)C(C(=O)NCC(=O)N2CCOCC2)c2cccnc2)cc1] |
| 600 | 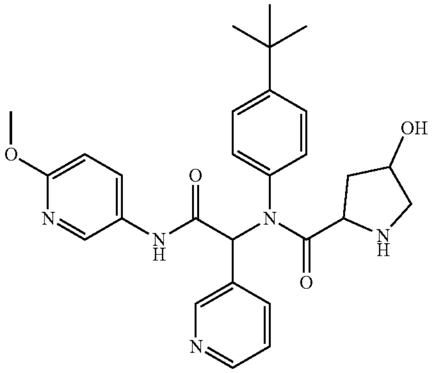 [SMILES: COc1ccc(NC(=O)C(c2cccnc2)N(C(=O)C2CC(O)CN2)c2ccc(C(C)(C)C)cc2)cn1] |
| 601 | 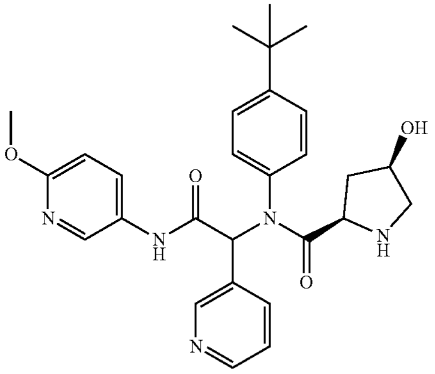 [SMILES: COc1ccc(NC(=O)C(c2cccnc2)N(C(=O)[C@H]2C[C@@H](O)CN2)c2ccc(C(C)(C)C)cc2)cn1] |

TABLE 1-continued
| Exemplary compounds. | |
|---|---|
| Cmpd No. | Structure |
| 602 | 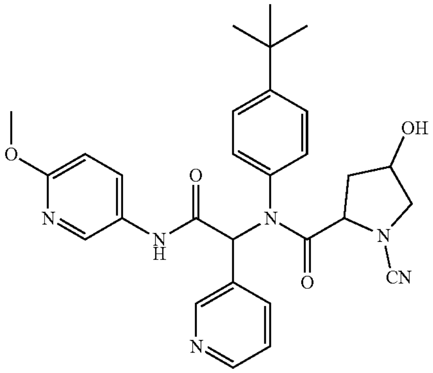 [SMILES: COc1ccc(NC(=O)C(c2cccnc2)N(C(=O)C2CC(O)CN2C#N)c2ccc(C(C)(C)C)cc2)cn1] |
| 603 | 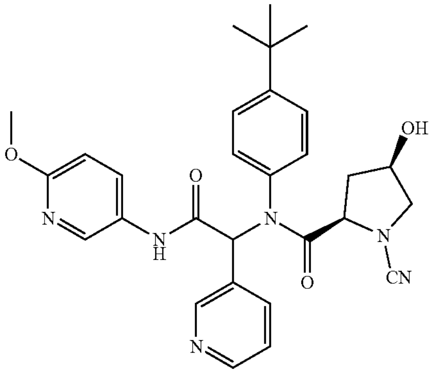 [SMILES: COc1ccc(NC(=O)C(c2cccnc2)N(C(=O)[C@H]2C[C@@H](O)CN2C#N)c2ccc(C(C)(C)C)cc2)cn1] |
| 604 | 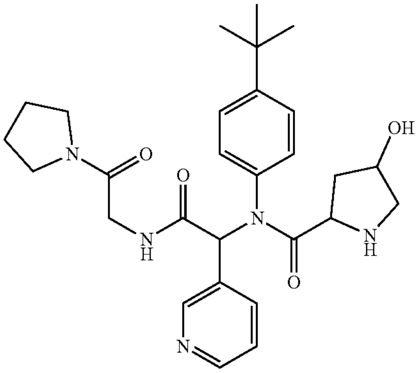 [SMILES: CC(C)(C)c1ccc(N(C(=O)C2CC(O)CN2)C(C(=O)NCC(=O)N2CCCC2)c2cccnc2)cc1] |
| 605 | 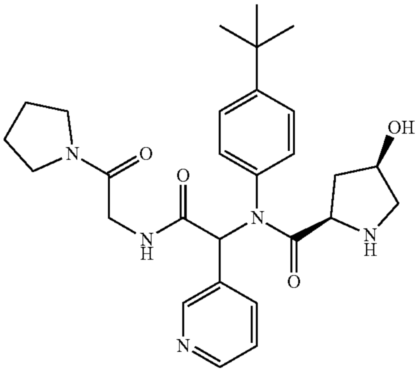 [SMILES: CC(C)(C)c1ccc(N(C(=O)[C@H]2C[C@@H](O)CN2)C(C(=O)NCC(=O)N2CCCC2)c2cccnc2)cc1] |
TABLE 1-continued
| Exemplary compounds. | |
|---|---|
| Cmpd No. | Structure |
| 606 | 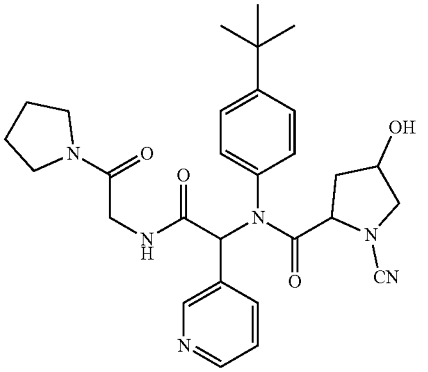 [SMILES: CC(C)(C)c1ccc(N(C(=O)C2CC(O)CN2C#N)C(C(=O)NCC(=O)N2CCCC2)c2cccnc2)cc1] |
| 607 | 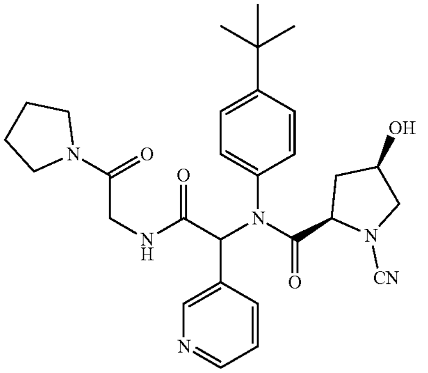 [SMILES: CC(C)(C)c1ccc(N(C(=O)[C@H]2C[C@@H](O)CN2C#N)C(C(=O)NCC(=O)N2CCCC2)c2cccnc2)cc1] |
| 608 | 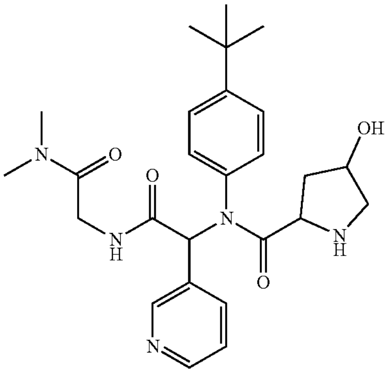 [SMILES: CN(C)C(=O)CNC(=O)C(c1cccnc1)N(C(=O)C1CC(O)CN1)c1ccc(C(C)(C)C)cc1] |
| 609 | 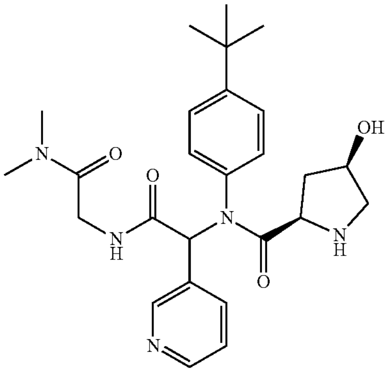 [SMILES: CN(C)C(=O)CNC(=O)C(c1cccnc1)N(C(=O)[C@H]1C[C@@H](O)CN1)c1ccc(C(C)(C)C)cc1] |

TABLE 1-continued
| Exemplary compounds. | |
|---|---|
| Cmpd No. | Structure |
| 610 | 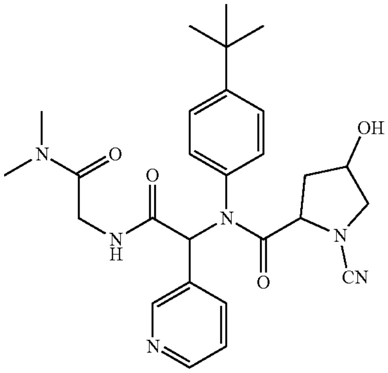 [SMILES: CN(C)C(=O)CNC(=O)C(c1cccnc1)N(C(=O)C1CC(O)CN1C#N)c1ccc(C(C)(C)C)cc1] |
| 611 | 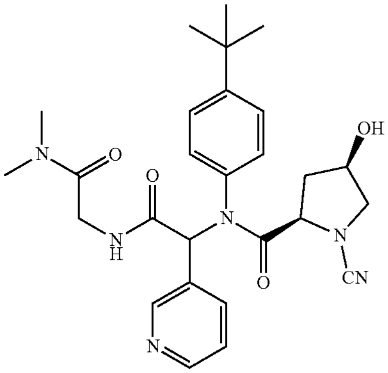 [SMILES: CN(C)C(=O)CNC(=O)C(c1cccnc1)N(C(=O)[C@H]1C[C@@H](O)CN1C#N)c1ccc(C(C)(C)C)cc1] |
| 612 | 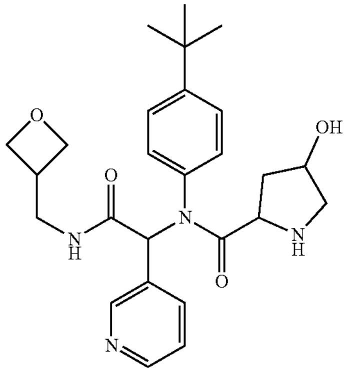 [SMILES: CC(C)(C)c1ccc(N(C(=O)C2CC(O)CN2)C(C(=O)NCC2COC2)c2cccnc2)cc1] |
| 613 | 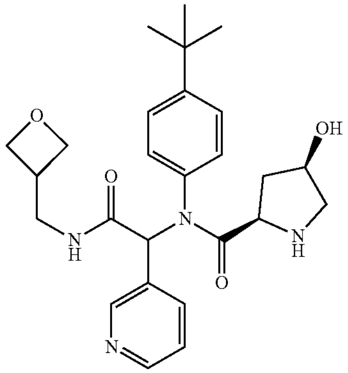 [SMILES: CC(C)(C)c1ccc(N(C(=O)[C@H]2C[C@@H](O)CN2)C(C(=O)NCC2COC2)c2cccnc2)cc1] |
TABLE 1-continued
| Exemplary compounds. | |
|---|---|
| Cmpd No. | Structure |
| 614 | 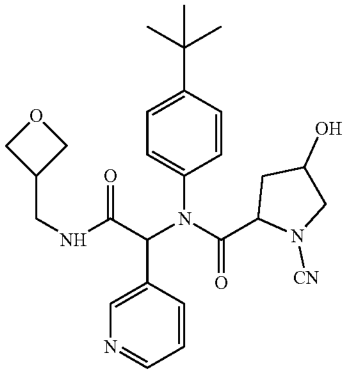 |
| 615 | 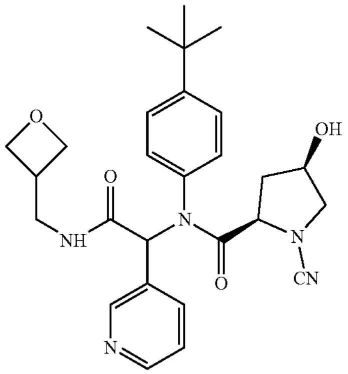 |
| 616 | 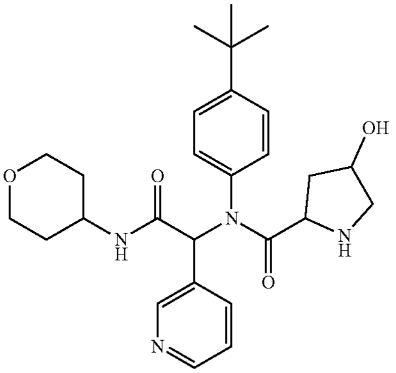 [SMILES: CC(C)(C)c1ccc(N(C(=O)C2CC(O)CN2)C(C(=O)NC2CCOCC2)c2cccnc2)cc1] |
| 617 | 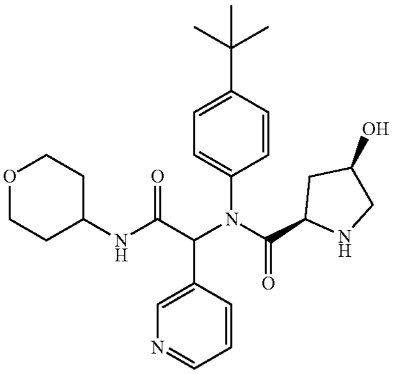 [SMILES: CC(C)(C)c1ccc(N(C(=O)[C@H]2C[C@@H](O)CN2)C(C(=O)NC2CCOCC2)c2cccnc2)cc1] |

TABLE 1-continued
| Exemplary compounds. | |
|---|---|
| Cmpd No. | Structure |
| 618 | 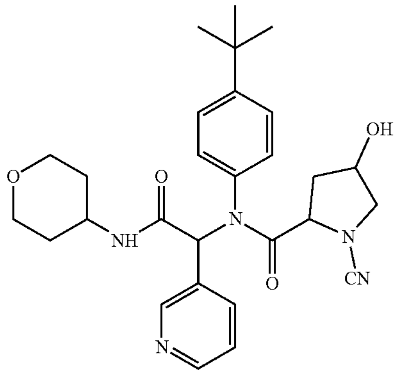 |
| 619 | 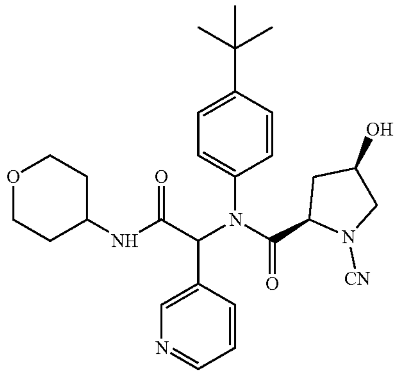 |
| 620 | 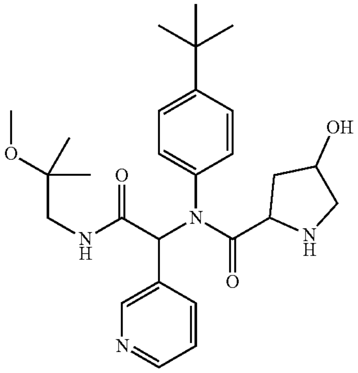 [SMILES: COC(C)(C)CNC(=O)C(c1cccnc1)N(C(=O)C1CC(O)CN1)c1ccc(C(C)(C)C)cc1] |
| 621 | 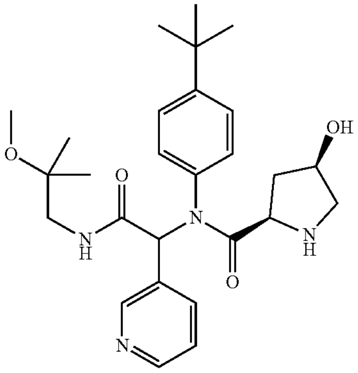 [SMILES: COC(C)(C)CNC(=O)C(c1cccnc1)N(C(=O)[C@H]1C[C@@H](O)CN1)c1ccc(C(C)(C)C)cc1] |
TABLE 1-continued
| Exemplary compounds. | |
|---|---|
| Cmpd No. | Structure |
| 622 | 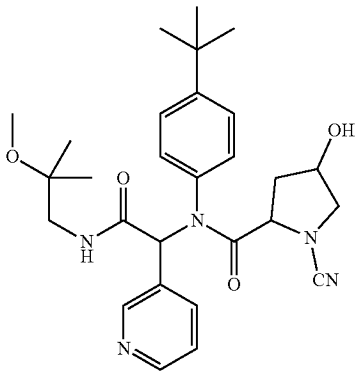 [SMILES: COC(C)(C)CNC(=O)C(c1cccnc1)N(C(=O)C1CC(O)CN1C#N)c1ccc(C(C)(C)C)cc1] |
| 623 | 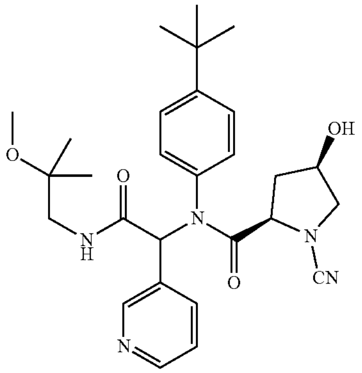 [SMILES: COC(C)(C)CNC(=O)C(c1cccnc1)N(C(=O)[C@H]1C[C@@H](O)CN1C#N)c1ccc(C(C)(C)C)cc1] |
| 624 | 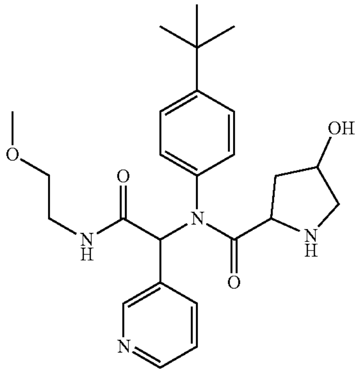 [SMILES: COCCNC(=O)C(c1cccnc1)N(C(=O)C1CC(O)CN1)c1ccc(C(C)(C)C)cc1] |
| 625 | 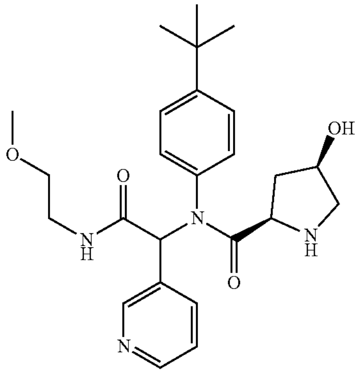 [SMILES: COCCNC(=O)C(c1cccnc1)N(C(=O)[C@H]1C[C@@H](O)CN1)c1ccc(C(C)(C)C)cc1] |

TABLE 1-continued
| Exemplary compounds. | |
|---|---|
| Cmpd No. | Structure |
| 626 | 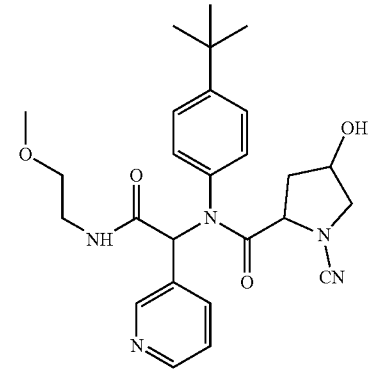 |
| 627 | 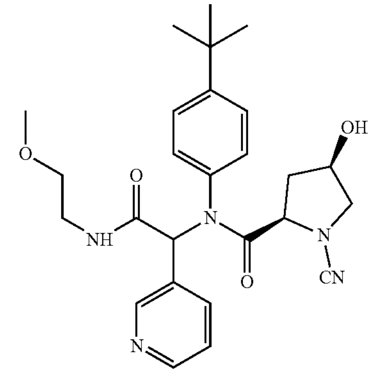 |
| 628 | 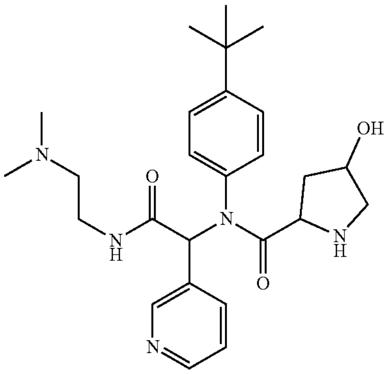 [SMILES: CN(C)CCNC(=O)C(c1cccnc1)N(C(=O)C1CC(O)CN1)c1ccc(C(C)(C)C)cc1] |
| 629 | 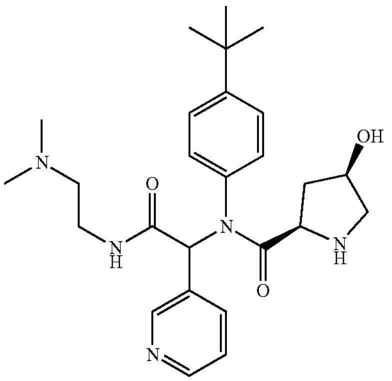 [SMILES: CN(C)CCNC(=O)C(c1cccnc1)N(C(=O)[C@H]1C[C@@H](O)CN1)c1ccc(C(C)(C)C)cc1] |
TABLE 1-continued
| Exemplary compounds. | |
|---|---|
| Cmpd No. | Structure |
| 630 | 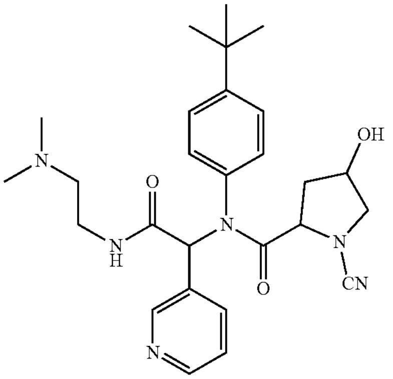 [SMILES: CN(C)CCNC(=O)C(c1cccnc1)N(C(=O)C1CC(O)CN1C#N)c1ccc(C(C)(C)C)cc1] |
| 631 | 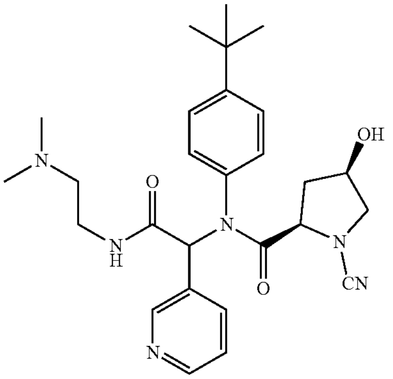 [SMILES: CN(C)CCNC(=O)C(c1cccnc1)N(C(=O)[C@H]1C[C@@H](O)CN1C#N)c1ccc(C(C)(C)C)cc1] |
| 632 | 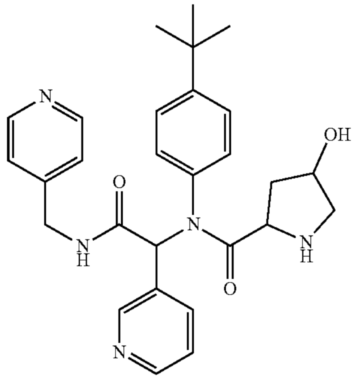 [SMILES: CC(C)(C)c1ccc(N(C(=O)C2CC(O)CN2)C(C(=O)NCc2ccncc2)c2cccnc2)cc1] |
| 633 | 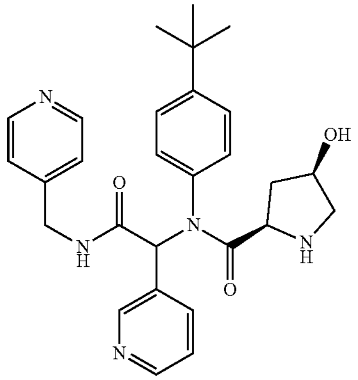 [SMILES: CC(C)(C)c1ccc(N(C(=O)[C@H]2C[C@@H](O)CN2)C(C(=O)NCc2ccncc2)c2cccnc2)cc1] |

TABLE 1-continued
| Exemplary compounds. | |
|---|---|
| Cmpd No. | Structure |
| 634 | 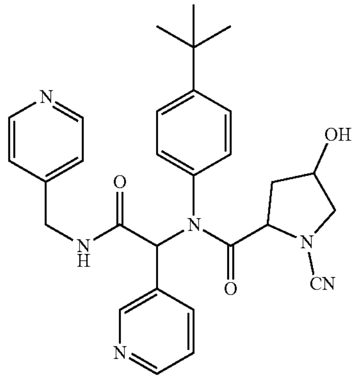 [SMILES: CC(C)(C)c1ccc(N(C(=O)C2CC(O)CN2C#N)C(C(=O)NCc2ccncc2)c2cccnc2)cc1] |
| 635 | 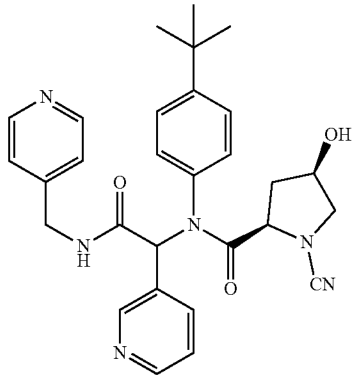 [SMILES: CC(C)(C)c1ccc(N(C(=O)[C@H]2C[C@@H](O)CN2C#N)C(C(=O)NCc2ccncc2)c2cccnc2)cc1] |
| 636 | 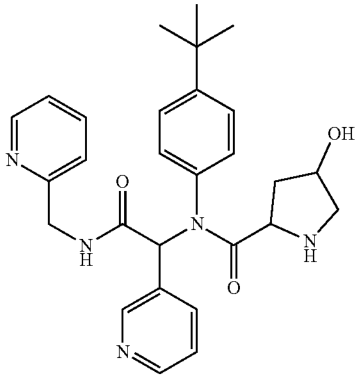 [SMILES: CC(C)(C)c1ccc(N(C(=O)C2CC(O)CN2)C(C(=O)NCc2ccccn2)c2cccnc2)cc1] |
| 637 | 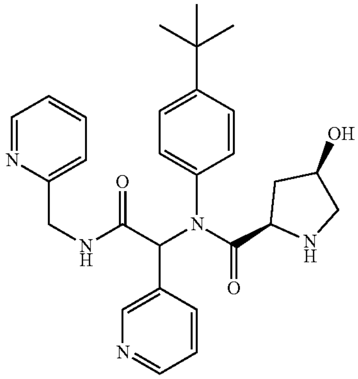 [SMILES: CC(C)(C)c1ccc(N(C(=O)[C@H]2C[C@@H](O)CN2)C(C(=O)NCc2ccccn2)c2cccnc2)cc1] |
TABLE 1-continued
| Exemplary compounds. | |
|---|---|
| Cmpd No. | Structure |
| 638 | 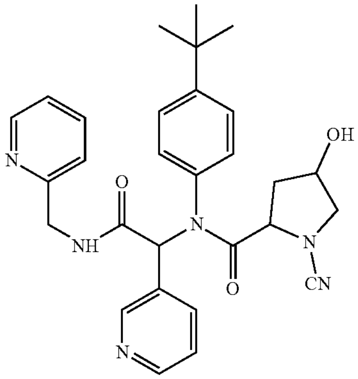 |
| 639 | 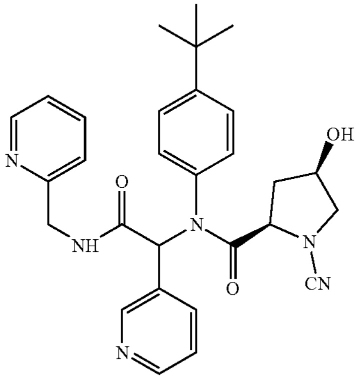 |
| 640 | 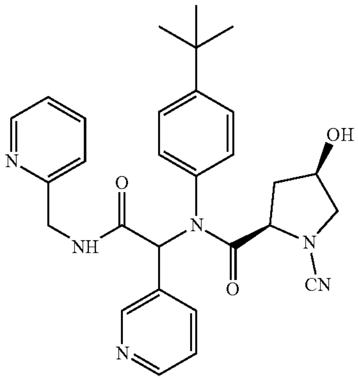 |
| 641 | 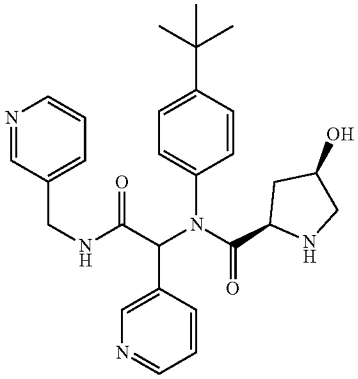 [SMILES: CC(C)(C)c1ccc(N(C(=O)[C@H]2C[C@@H](O)CN2)C(C(=O)NCc2cccnc2)c2cccnc2)cc1] |

TABLE 1-continued
| Exemplary compounds. | |
|---|---|
| Cmpd No. | Structure |
| 642 | 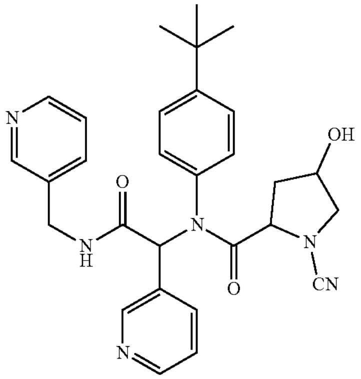 [SMILES: CC(C)(C)c1ccc(N(C(=O)C2CC(O)CN2C#N)C(C(=O)NCc2cccnc2)c2cccnc2)cc1] |
| 643 | 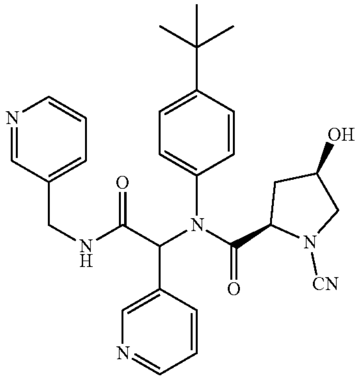 [SMILES: CC(C)(C)c1ccc(N(C(=O)[C@H]2C[C@@H](O)CN2C#N)C(C(=O)NCc2cccnc2)c2cccnc2)cc1] |
| 644 | 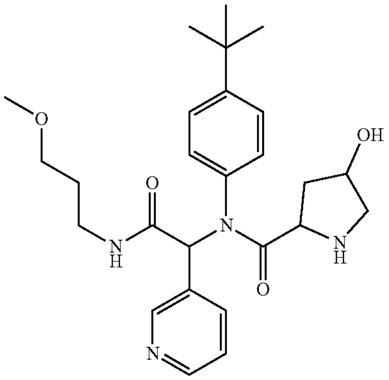 [SMILES: COCCCNC(=O)C(c1cccnc1)N(C(=O)C1CC(O)CN1)c1ccc(C(C)(C)C)cc1] |
| 645 | 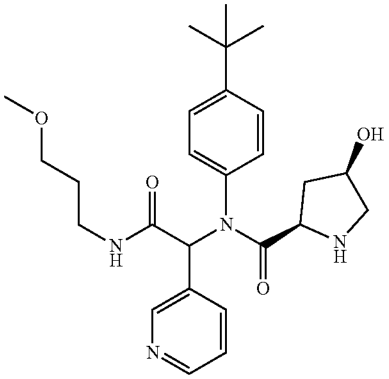 [SMILES: COCCCNC(=O)C(c1cccnc1)N(C(=O)[C@H]1C[C@@H](O)CN1)c1ccc(C(C)(C)C)cc1] |
TABLE 1-continued
| Exemplary compounds. | |
|---|---|
| Cmpd No. | Structure |
| 646 | 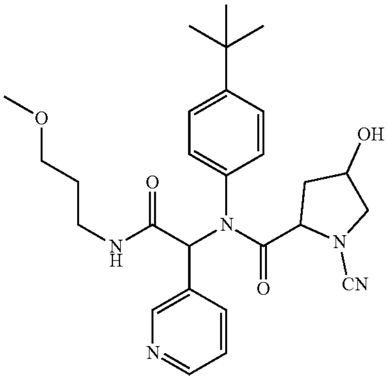 [SMILES: COCCCNC(=O)C(c1cccnc1)N(C(=O)C1CC(O)CN1C#N)c1ccc(C(C)(C)C)cc1] |
| 647 | 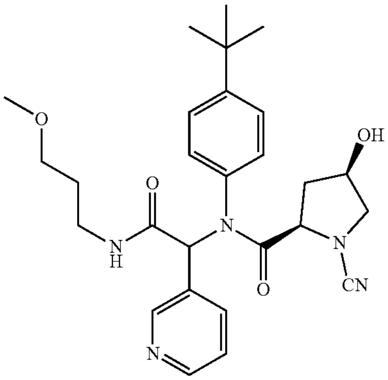 [SMILES: COCCCNC(=O)C(c1cccnc1)N(C(=O)[C@H]1C[C@@H](O)CN1C#N)c1ccc(C(C)(C)C)cc1] |
| 648 | 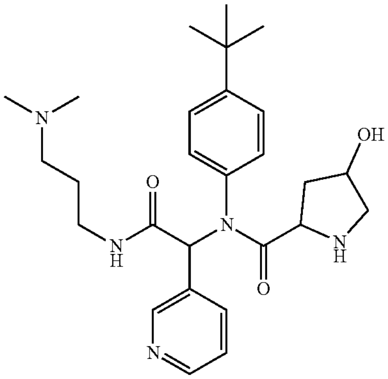 [SMILES: CN(C)CCCNC(=O)C(c1cccnc1)N(C(=O)C1CC(O)CN1)c1ccc(C(C)(C)C)cc1] |
| 649 | 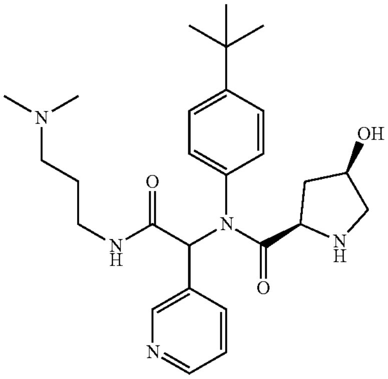 [SMILES: CN(C)CCCNC(=O)C(c1cccnc1)N(C(=O)[C@H]1C[C@@H](O)CN1)c1ccc(C(C)(C)C)cc1] |

TABLE 1-continued
| Cmpd No. | Structure |
| --- | --- |
| Exemplary compounds. | |
| 650 | 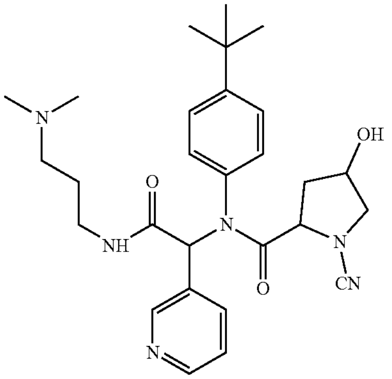 |
| 651 | 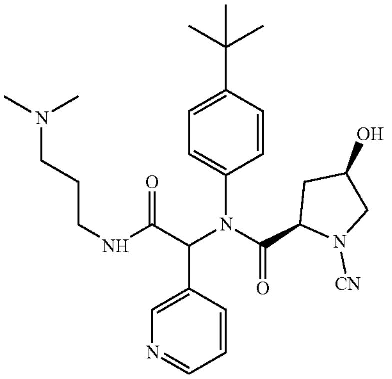 |
| 652 | 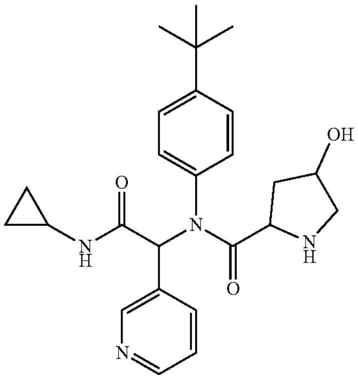 [SMILES: CC(C)(C)c1ccc(N(C(=O)C2CC(O)CN2)C(C(=O)NC2CC2)c2cccnc2)cc1] |
| 653 | 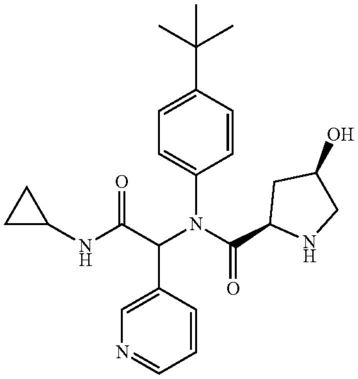 [SMILES: CC(C)(C)c1ccc(N(C(=O)[C@H]2C[C@@H](O)CN2)C(C(=O)NC2CC2)c2cccnc2)cc1] |
TABLE 1-continued
| Cmpd No. | Structure |
| --- | --- |
| Exemplary compounds. | |
| 654 | 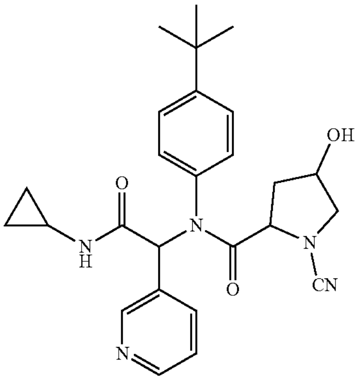 [SMILES: CC(C)(C)c1ccc(N(C(=O)C2CC(O)CN2C#N)C(C(=O)NC2CC2)c2cccnc2)cc1] |
| 655 | 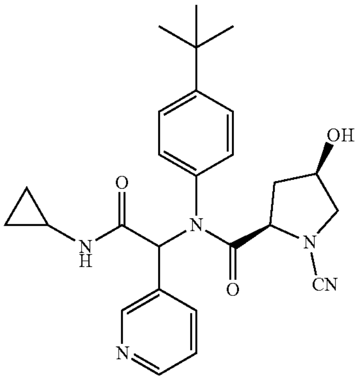 [SMILES: CC(C)(C)c1ccc(N(C(=O)[C@H]2C[C@@H](O)CN2C#N)C(C(=O)NC2CC2)c2cccnc2)cc1] |
| 656 | 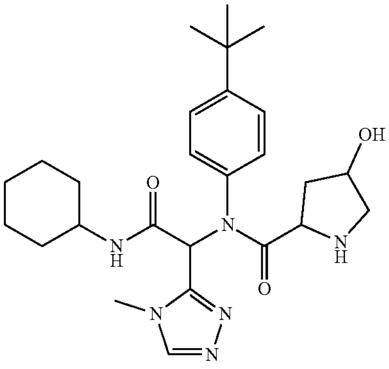 [SMILES: Cn1cnnc1C(C(=O)NC1CCCCC1)N(C(=O)C1CC(O)CN1)c1ccc(C(C)(C)C)cc1] |
| 657 | 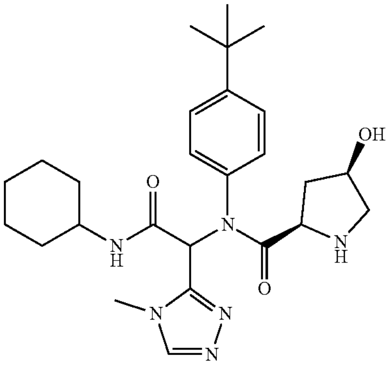 [SMILES: Cn1cnnc1C(C(=O)NC1CCCCC1)N(C(=O)[C@H]1C[C@@H](O)CN1)c1ccc(C(C)(C)C)cc1] |

TABLE 1-continued
Exemplary compounds.
| Cmpd No. | Structure |
|---|---|
| 658 | 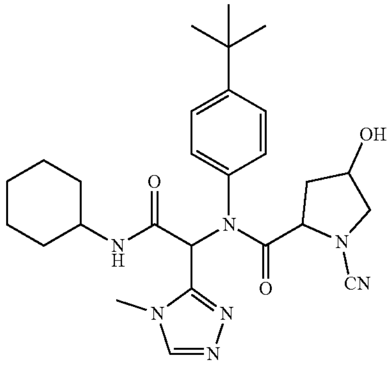 [SMILES: Cn1cnnc1C(C(=O)NC1CCCCC1)N(C(=O)C1CC(O)CN1C#N)c1ccc(C(C)(C)C)cc1] |
| 659 | 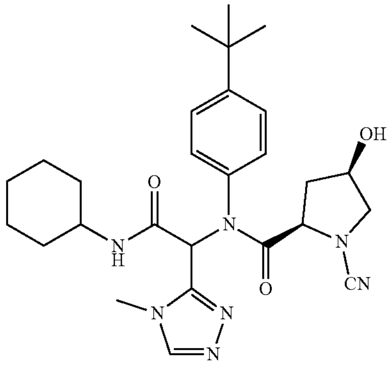 [SMILES: Cn1cnnc1C(C(=O)NC1CCCCC1)N(C(=O)[C@H]1C[C@@H](O)CN1C#N)c1ccc(C(C)(C)C)cc1] |
| 660 | 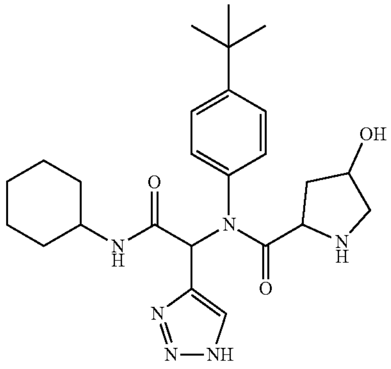 [SMILES: CC(C)(C)c1ccc(N(C(=O)C2CC(O)CN2)C(C(=O)NC2CCCCC2)c2c[nH]nn2)cc1] |
| 661 | 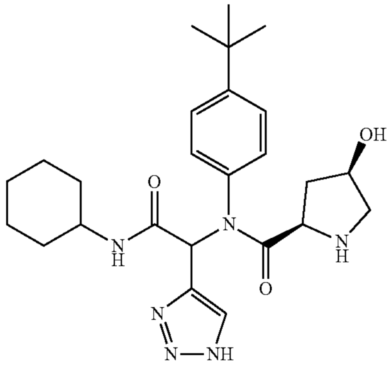 [SMILES: CC(C)(C)c1ccc(N(C(=O)[C@H]2C[C@@H](O)CN2)C(C(=O)NC2CCCCC2)c2c[nH]nn2)cc1] |
TABLE 1-continued
Exemplary compounds.
| Cmpd No. | Structure |
|---|---|
| 662 | 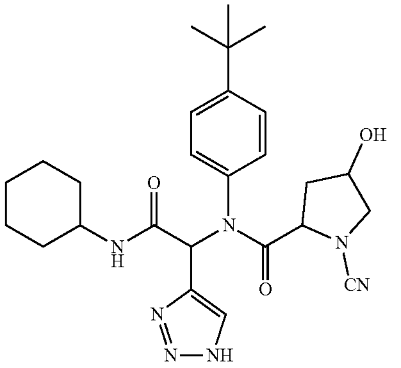 [SMILES: CC(C)(C)c1ccc(N(C(=O)C2CC(O)CN2C#N)C(C(=O)NC2CCCCC2)c2c[nH]nn2)cc1] |
| 663 | 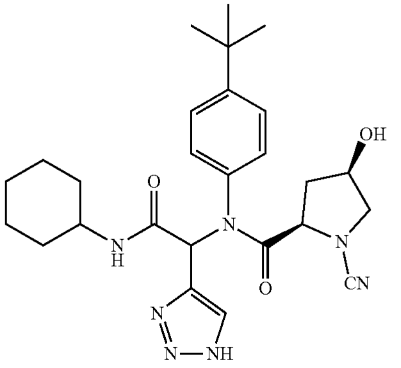 [SMILES: CC(C)(C)c1ccc(N(C(=O)[C@H]2C[C@@H](O)CN2C#N)C(C(=O)NC2CCCCC2)c2c[nH]nn2)cc1] |
| 664 | 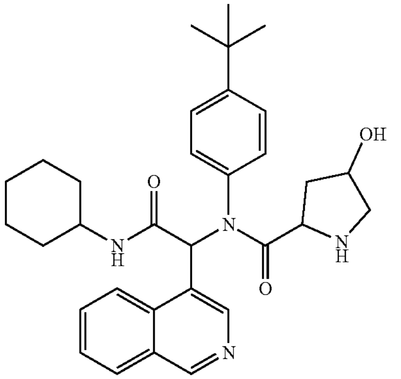 [SMILES: CC(C)(C)c1ccc(N(C(=O)C2CC(O)CN2)C(C(=O)NC2CCCCC2)c2cncc3ccccc23)cc1] |
| 665 | 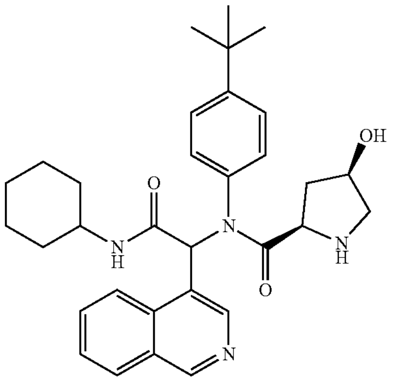 [SMILES: CC(C)(C)c1ccc(N(C(=O)[C@H]2C[C@@H](O)CN2)C(C(=O)NC2CCCCC2)c2cncc3ccccc23)cc1] |

TABLE 1-continued
| Exemplary compounds. | |
|---|---|
| Cmpd No. | Structure |
| 666 | 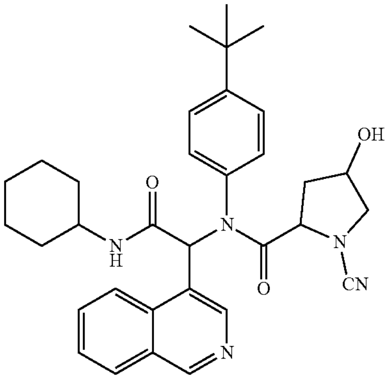 [SMILES: CC(C)(C)c1ccc(N(C(=O)C2CC(O)CN2C#N)C(C(=O)NC2CCCCC2)c2cncc3ccccc23)cc1] |
| 667 | 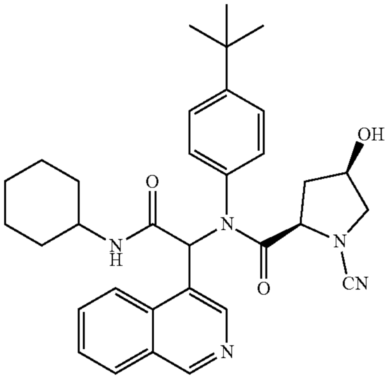 [SMILES: CC(C)(C)c1ccc(N(C(=O)[C@H]2C[C@@H](O)CN2C#N)C(C(=O)NC2CCCCC2)c2cncc3ccccc23)cc1] |
| 668 | 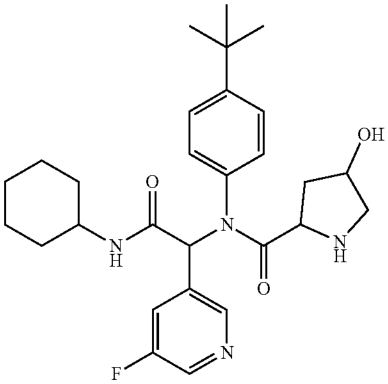 [SMILES: CC(C)(C)c1ccc(N(C(=O)C2CC(O)CN2)C(C(=O)NC2CCCCC2)c2cncc(F)c2)cc1] |
| 669 | 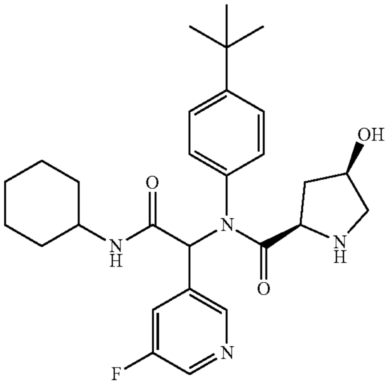 [SMILES: CC(C)(C)c1ccc(N(C(=O)[C@H]2C[C@@H](O)CN2)C(C(=O)NC2CCCCC2)c2cncc(F)c2)cc1] |
TABLE 1-continued
| Exemplary compounds. | |
|---|---|
| Cmpd No. | Structure |
| 670 | 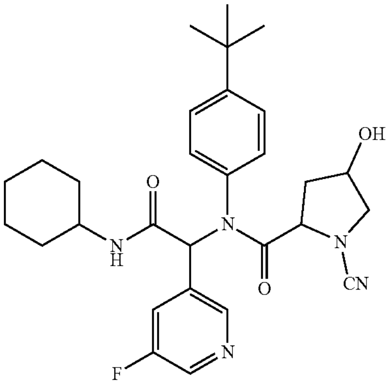 [SMILES: CC(C)(C)c1ccc(N(C(=O)C2CC(O)CN2C#N)C(C(=O)NC2CCCCC2)c2cncc(F)c2)cc1] |
| 671 | 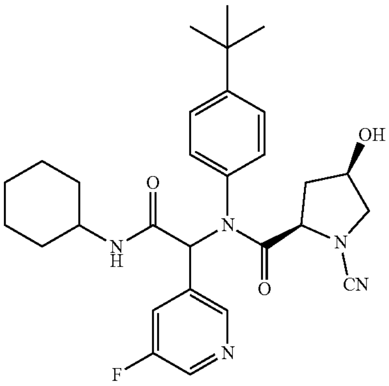 [SMILES: CC(C)(C)c1ccc(N(C(=O)[C@H]2C[C@@H](O)CN2C#N)C(C(=O)NC2CCCCC2)c2cncc(F)c2)cc1] |
| 672 | 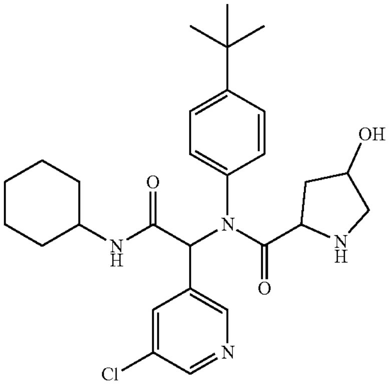 [SMILES: CC(C)(C)c1ccc(N(C(=O)C2CC(O)CN2)C(C(=O)NC2CCCCC2)c2cncc(Cl)c2)cc1] |

TABLE 1-continued
| Cmpd No. | Structure |
|---|---|
| 673 | 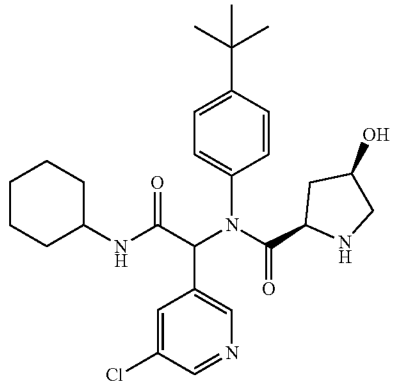 [SMILES: CC(C)(C)c1ccc(N(C(=O)[C@H]2C[C@@H](O)CN2)C(C(=O)NC2CCCCC2)c2cncc(Cl)c2)cc1] |
| 674 | 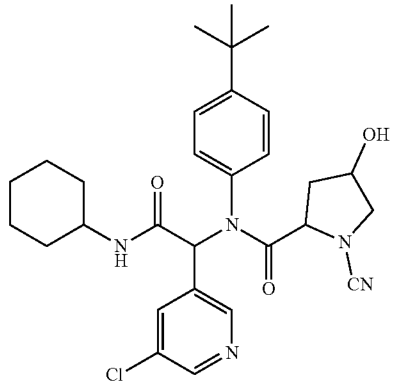 [SMILES: CC(C)(C)c1ccc(N(C(=O)C2CC(O)CN2C#N)C(C(=O)NC2CCCCC2)c2cncc(Cl)c2)cc1] |
| 675 | 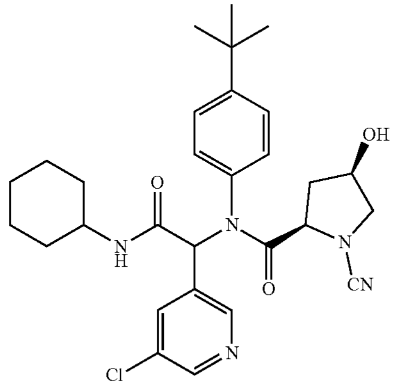 [SMILES: CC(C)(C)c1ccc(N(C(=O)[C@H]2C[C@@H](O)CN2C#N)C(C(=O)NC2CCCCC2)c2cncc(Cl)c2)cc1] |
| 676 | 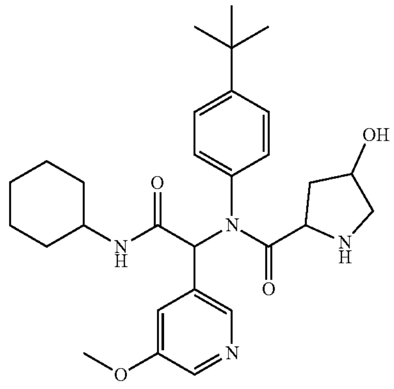 [SMILES: COc1cncc(C(C(=O)NC2CCCCC2)N(C(=O)C2CC(O)CN2)c2ccc(C(C)(C)C)cc2)c1] |
TABLE 1-continued
| Cmpd No. | Structure |
|---|---|
| 677 | 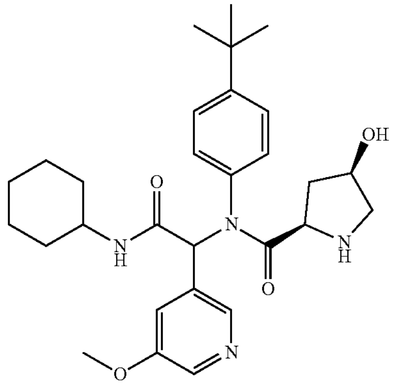 [SMILES: COc1cncc(C(C(=O)NC2CCCCC2)N(C(=O)[C@H]2C[C@@H](O)CN2)c2ccc(C(C)(C)C)cc2)c1] |
| 678 | 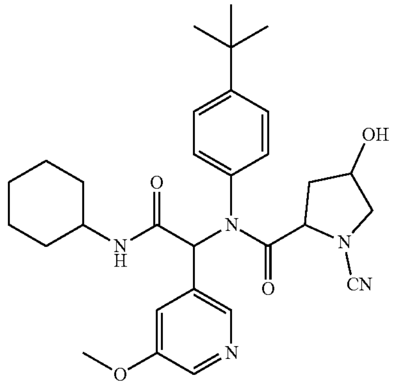 [SMILES: COc1cncc(C(C(=O)NC2CCCCC2)N(C(=O)C2CC(O)CN2C#N)c2ccc(C(C)(C)C)cc2)c1] |
| 679 | 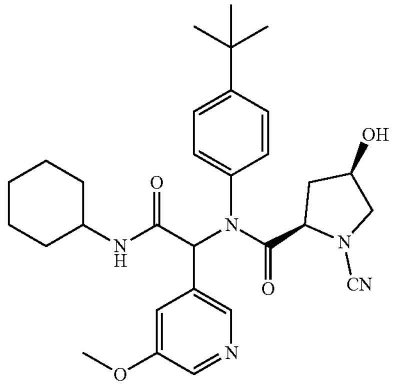 [SMILES: COc1cncc(C(C(=O)NC2CCCCC2)N(C(=O)[C@H]2C[C@@H](O)CN2C#N)c2ccc(C(C)(C)C)cc2)c1] |

TABLE 1-continued
Exemplary compounds.
| Cmpd No. | Structure |
|---|---|
| 680 | 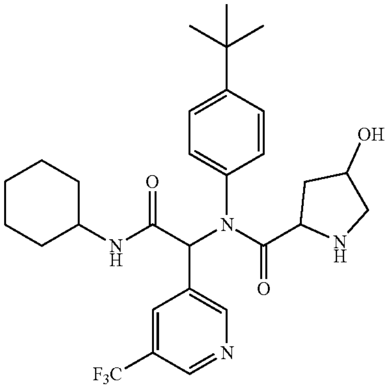 [SMILES: CC(C)(C)c1ccc(N(C(=O)C2CC(O)CN2)C(C(=O)NC2CCCCC2)c2cncc(C(F)(F)F)c2)cc1] |
| 681 | 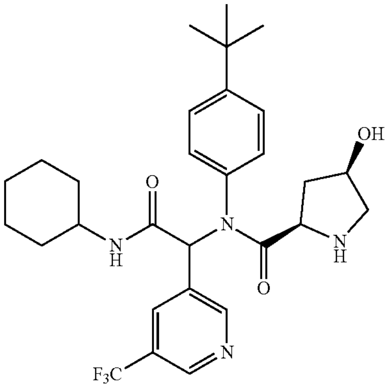 [SMILES: CC(C)(C)c1ccc(N(C(=O)[C@H]2C[C@@H](O)CN2)C(C(=O)NC2CCCCC2)c2cncc(C(F)(F)F)c2)cc1] |
| 682 | 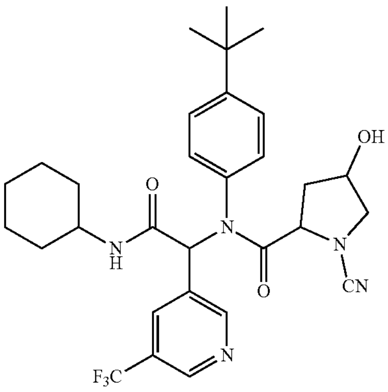 [SMILES: CC(C)(C)c1ccc(N(C(=O)C2CC(O)CN2C#N)C(C(=O)NC2CCCCC2)c2cncc(C(F)(F)F)c2)cc1] |
TABLE 1-continued
Exemplary compounds.
| Cmpd No. | Structure |
|---|---|
| 683 | 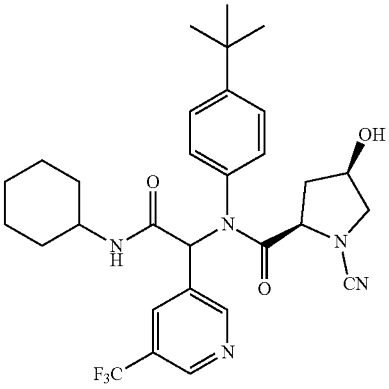 [SMILES: CC(C)(C)c1ccc(N(C(=O)[C@H]2C[C@@H](O)CN2C#N)C(C(=O)NC2CCCCC2)c2cncc(C(F)(F)F)c2)cc1] |
| 684 | 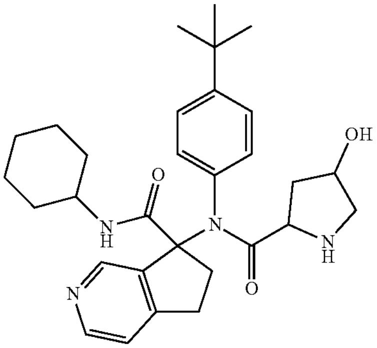 [SMILES: CC(C)(C)c1ccc(N(C(=O)C2CC(O)CN2)C2(C(=O)NC3CCCCC3)CCc3ccncc32)cc1] |
| 685 | 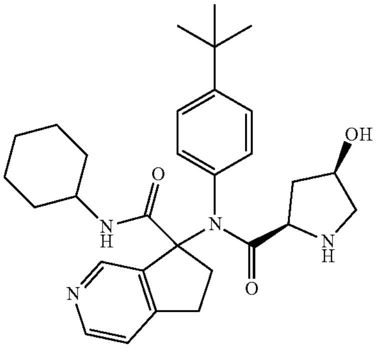 [SMILES: CC(C)(C)c1ccc(N(C(=O)[C@H]2C[C@@H](O)CN2)C2(C(=O)NC3CCCCC3)CCc3ccncc32)cc1] |
| 686a | 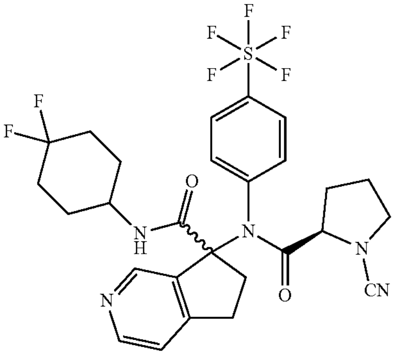 [SMILES: N#CN1CCC[C@@H]1C(=O)N(c1ccc(S(F)(F)(F)(F)F)cc1)C1(C(=O)NC2CCC(F)(F)CC2)CCc2ccncc21] |

TABLE 1-continued
| Exemplary compounds. | |
|---|---|
| Cmpd No. | Structure |
| 686b | 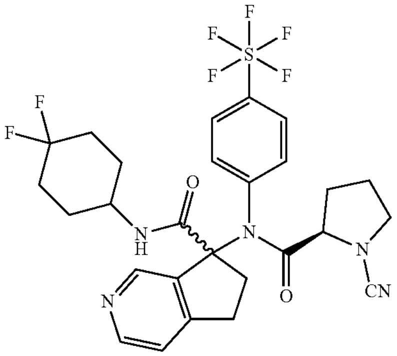 [SMILES: N#CN1CCC[C@@H]1C(=O)N(c1ccc(S(F)(F)(F)(F)F)cc1)C1(C(=O)NC2CCC(F)(F)CC2)CCc2ccncc21] |
| 686 | 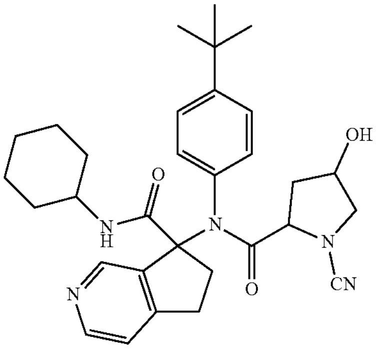 [SMILES: CC(C)(C)c1ccc(N(C(=O)C2CC(O)CN2C#N)C2(C(=O)NC3CCCCC3)CCc3ccncc32)cc1] |
| 687 | 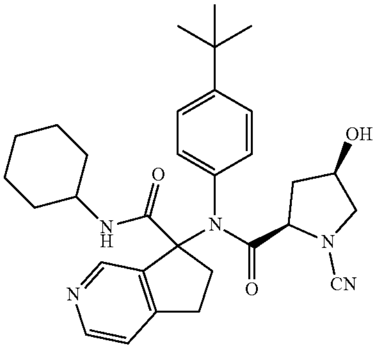 [SMILES: CC(C)(C)c1ccc(N(C(=O)[C@H]2C[C@@H](O)CN2C#N)C2(C(=O)NC3CCCCC3)CCc3ccncc32)cc1] |
| 688 | 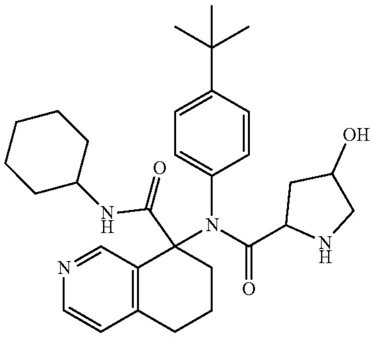 [SMILES: CC(C)(C)c1ccc(N(C(=O)C2CC(O)CN2)C2(C(=O)NC3CCCCC3)CCCc3ccncc32)cc1] |
TABLE 1-continued
| Exemplary compounds. | |
|---|---|
| Cmpd No. | Structure |
| 689 | 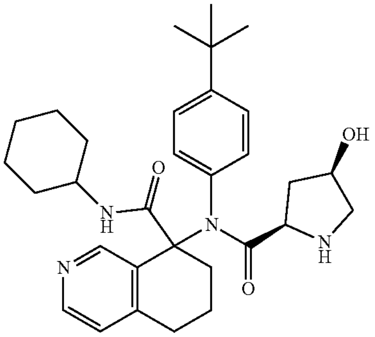 [SMILES: CC(C)(C)c1ccc(N(C(=O)[C@H]2C[C@@H](O)CN2)C2(C(=O)NC3CCCCC3)CCCc3ccncc32)cc1] |
| 690 | 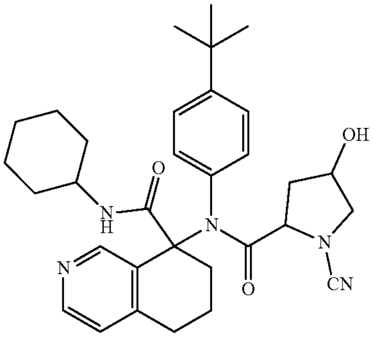 [SMILES: CC(C)(C)c1ccc(N(C(=O)C2CC(O)CN2C#N)C2(C(=O)NC3CCCCC3)CCCc3ccncc32)cc1] |
| 690a | 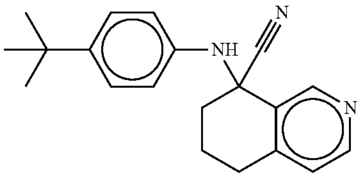 |
| 690b | 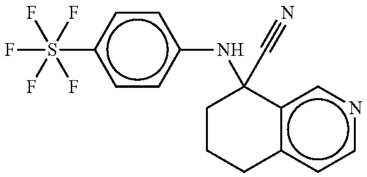 |
| 691 | 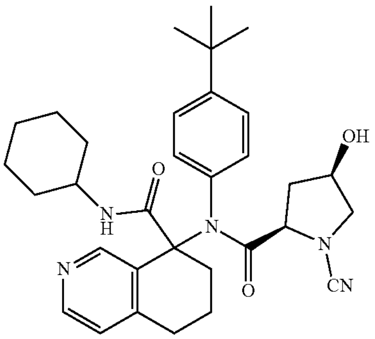 [SMILES: CC(C)(C)c1ccc(N(C(=O)[C@H]2C[C@@H](O)CN2C#N)C2(C(=O)NC3CCCCC3)CCCc3ccncc32)cc1] |

TABLE 1-continued
| Exemplary compounds. | |
|---|---|
| Cmpd No. | Structure |
| 692 | 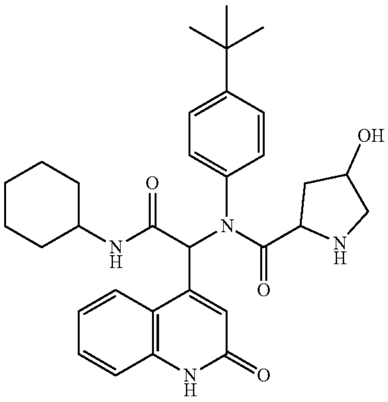 [SMILES: CC(C)(C)c1ccc(N(C(=O)C2CC(O)CN2)C(C(=O)NC2CCCCC2)c2cc(=O)[nH]c3ccccc23)cc1] |
| 692a | 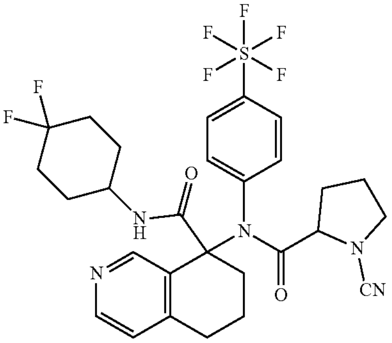 [SMILES: N#CN1CCCC1C(=O)N(c1ccc(S(F)(F)(F)(F)F)cc1)C1(C(=O)NC2CCC(F)(F)CC2)CCCc2ccncc21] |
| 692b | 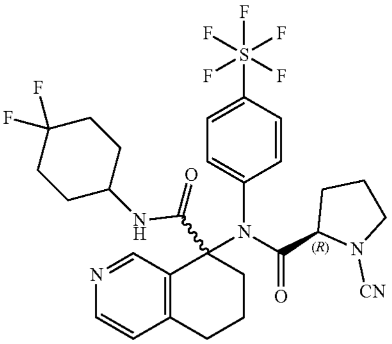 |
| 693 | 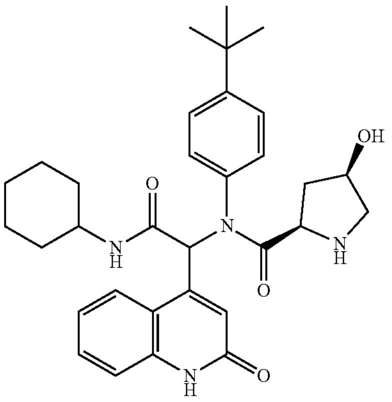 [SMILES: CC(C)(C)c1ccc(N(C(=O)[C@H]2C[C@@H](O)CN2)C(C(=O)NC2CCCCC2)c2cc(=O)[nH]c3ccccc23)cc1] |
TABLE 1-continued
| Exemplary compounds. | |
|---|---|
| Cmpd No. | Structure |
| 694 | 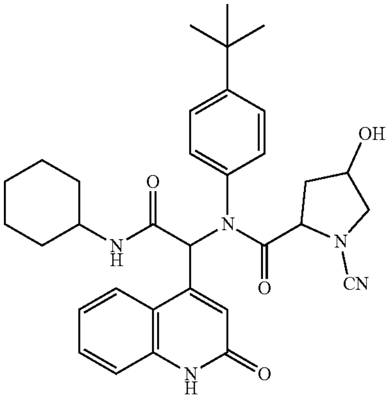 [SMILES: CC(C)(C)c1ccc(N(C(=O)C2CC(O)CN2C#N)C(C(=O)NC2CCCCC2)c2cc(=O)[nH]c3ccccc23)cc1] |
| 695 | 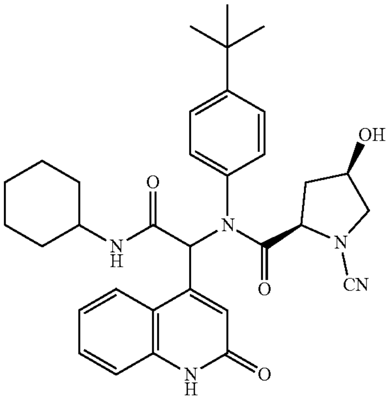 [SMILES: CC(C)(C)c1ccc(N(C(=O)[C@H]2C[C@@H](O)CN2C#N)C(C(=O)NC2CCCCC2)c2cc(=O)[nH]c3ccccc23)cc1] |
| 695b | 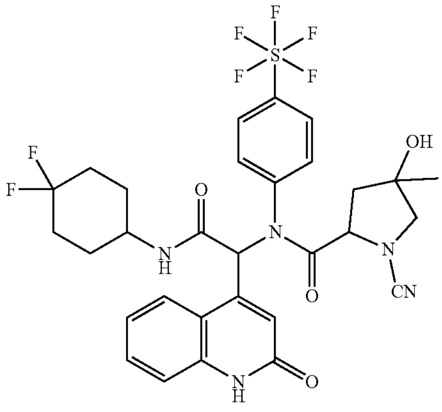 [SMILES: CC1(O)CC(C(=O)N(c2ccc(S(F)(F)(F)(F)F)cc2)C(C(=O)NC2CCC(F)(F)CC2)c2cc(=O)[nH]c3ccccc23)N(C#N)C1] |

TABLE 1-continued
| Exemplary compounds. | |
|---|---|
| Cmpd No. | Structure |
| 695a | 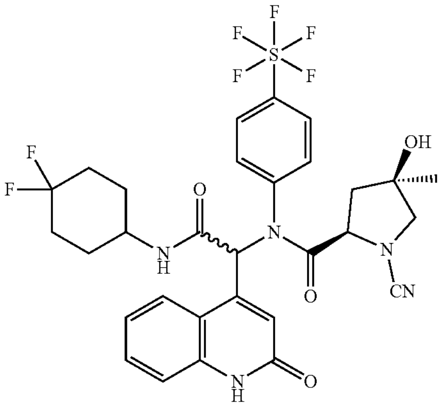 [SMILES: C[C@@]1(O)C[C@H](C(=O)N(c2ccc(S(F)(F)(F)(F)F)cc2)C(C(=O)NC2CCC(F)(F)CC2)c2cc(=O)[nH]c3ccccc23)N(C#N)C1] |
| 696 | 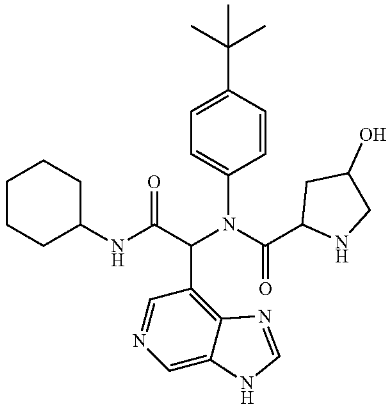 [SMILES: CC(C)(C)c1ccc(N(C(=O)C2CC(O)CN2)C(C(=O)NC2CCCCC2)c2cncc3[nH]cnc23)cc1] |
| 697 | 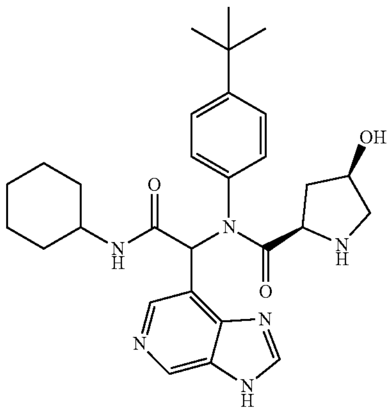 [SMILES: CC(C)(C)c1ccc(N(C(=O)[C@H]2C[C@@H](O)CN2)C(C(=O)NC2CCCCC2)c2cncc3[nH]cnc23)cc1] |
TABLE 1-continued
| Exemplary compounds. | |
|---|---|
| Cmpd No. | Structure |
| 698 | 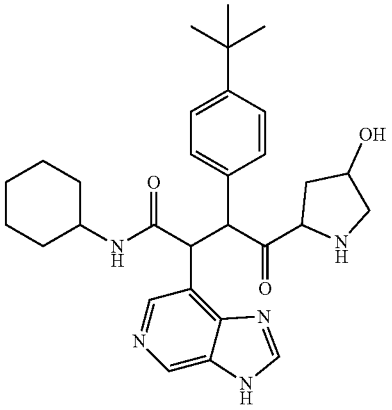 |
| 699a | 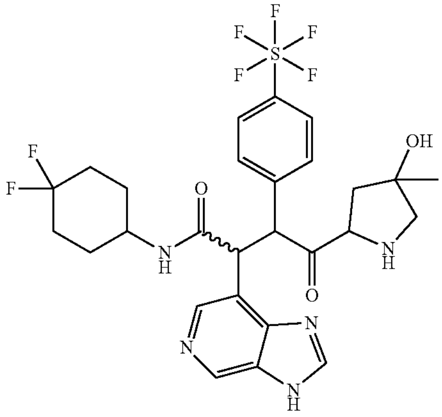 [SMILES: CC1(O)CNC(C(=O)C(c2ccc(S(F)(F)(F)(F)F)cc2)C(C(=O)NC2CCC(F)(F)CC2)c2cncc3[nH]cnc23)C1] |
| 699b | 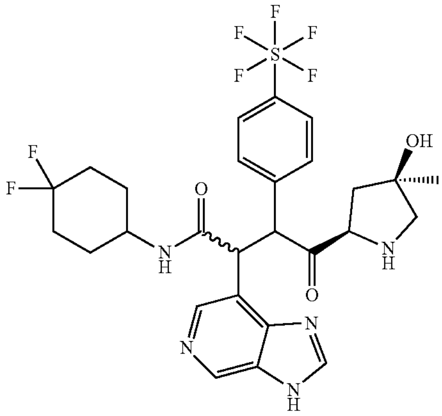 [SMILES: C[C@]1(O)CN[C@@H](C(=O)C(c2ccc(S(F)(F)(F)(F)F)cc2)C(C(=O)NC2CCC(F)(F)CC2)c2cncc3[nH]cnc23)C1] |

TABLE 1-continued
| Exemplary compounds. | |
|---|---|
| Cmpd No. | Structure |
| 699 | 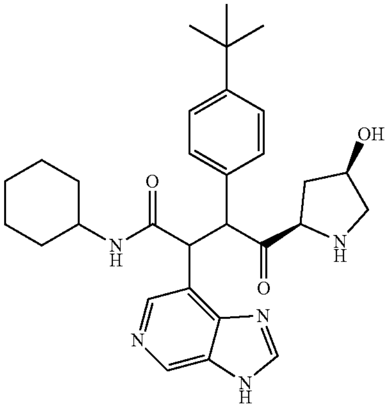 |
| 700 | 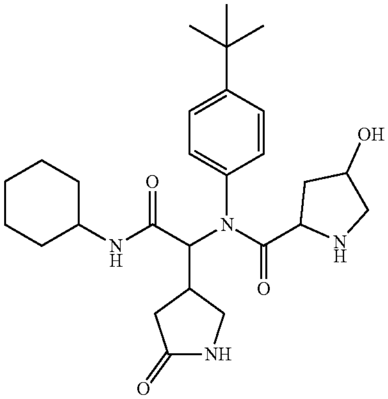 [SMILES: CC(C)(C)c1ccc(N(C(=O)C2CC(O)CN2)C(C(=O)NC2CCCCC2)C2CNC(=O)C2)cc1] |
| 701 | 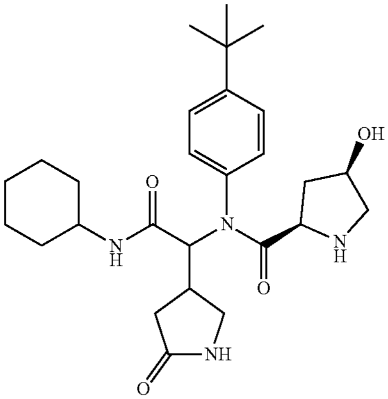 [SMILES: CC(C)(C)c1ccc(N(C(=O)[C@H]2C[C@@H](O)CN2)C(C(=O)NC2CCCCC2)C2CNC(=O)C2)cc1] |
TABLE 1-continued
| Exemplary compounds. | |
|---|---|
| Cmpd No. | Structure |
| 702 | 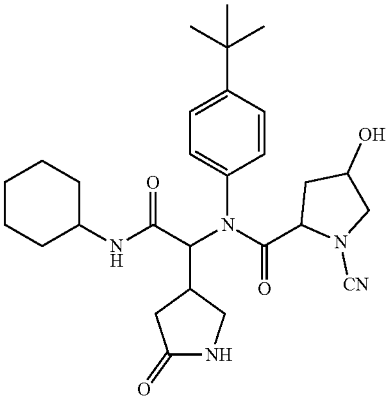 [SMILES: CC(C)(C)c1ccc(N(C(=O)C2CC(O)CN2C#N)C(C(=O)NC2CCCCC2)C2CNC(=O)C2)cc1] |
| 703a | 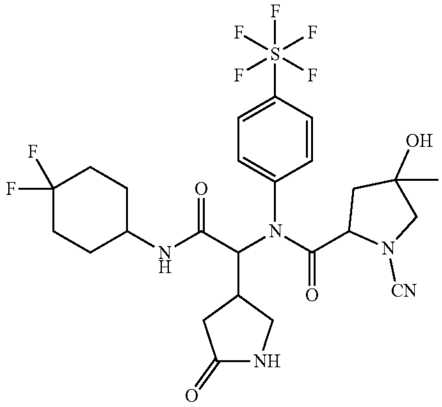 [SMILES: CC1(O)CC(C(=O)N(c2ccc(S(F)(F)(F)(F)F)cc2)C(C(=O)NC2CCC(F)(F)CC2)C2CNC(=O)C2)N(C#N)C1] |
| 703b | 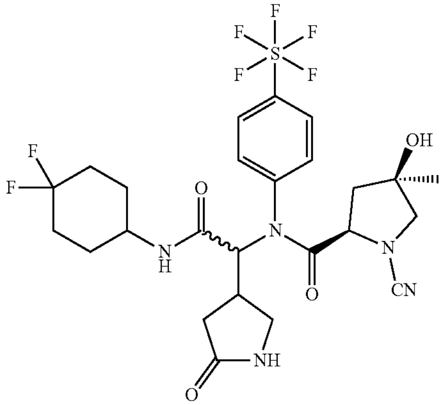 [SMILES: C[C@@]1(O)C[C@H](C(=O)N(c2ccc(S(F)(F)(F)(F)F)cc2)C(C(=O)NC2CCC(F)(F)CC2)C2CNC(=O)C2)N(C#N)C1] |

TABLE 1-continued
| Exemplary compounds. | |
|---|---|
| Cmpd No. | Structure |
| 703 | 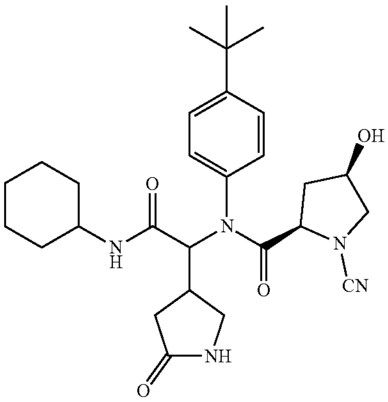 [SMILES: CC(C)(C)c1ccc(N(C(=O)[C@H]2C[C@@H](O)CN2C#N)C(C(=O)NC2CCCCC2)C2CNC(=O)C2)cc1] |
| 704 | 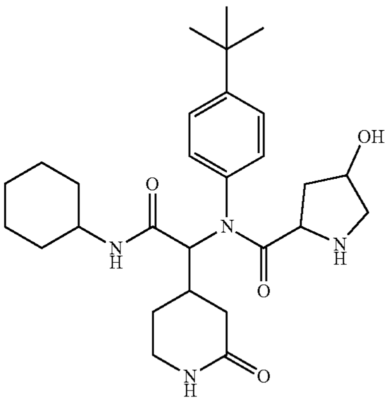 [SMILES: CC(C)(C)c1ccc(N(C(=O)C2CC(O)CN2)C(C(=O)NC2CCCCC2)C2CCNC(=O)C2)cc1] |
| 705 | 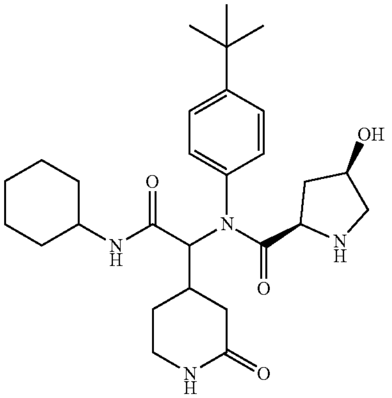 [SMILES: CC(C)(C)c1ccc(N(C(=O)[C@H]2C[C@@H](O)CN2)C(C(=O)NC2CCCCC2)C2CCNC(=O)C2)cc1] |
TABLE 1-continued
| Exemplary compounds. | |
|---|---|
| Cmpd No. | Structure |
| 706 | 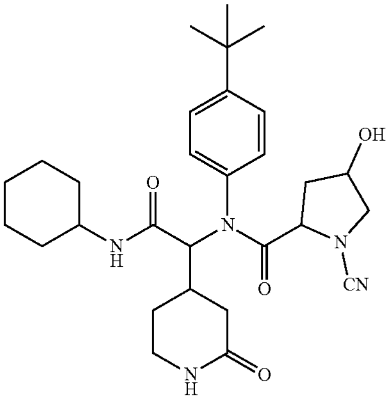 [SMILES: CC(C)(C)c1ccc(N(C(=O)C2CC(O)CN2C#N)C(C(=O)NC2CCCCC2)C2CCNC(=O)C2)cc1] |
| 707 | 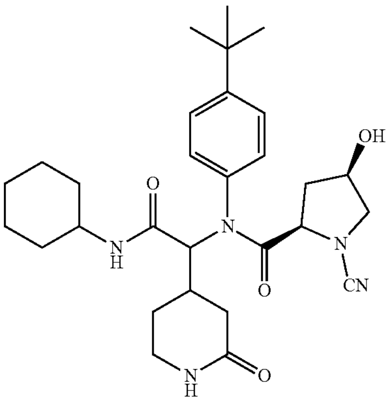 [SMILES: CC(C)(C)c1ccc(N(C(=O)[C@H]2C[C@@H](O)CN2C#N)C(C(=O)NC2CCCCC2)C2CCNC(=O)C2)cc1] |
| 707a | 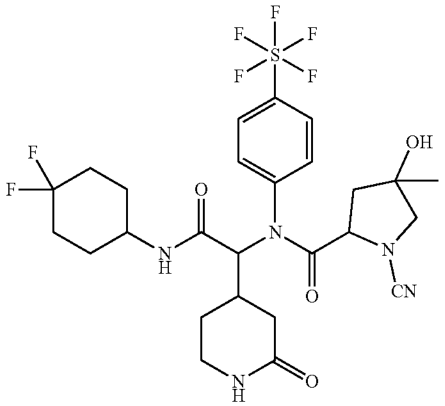 [SMILES: CC1(O)CC(C(=O)N(c2ccc(S(F)(F)(F)(F)F)cc2)C(C(=O)NC2CCC(F)(F)CC2)C2CCNC(=O)C2)N(C#N)C1] |

| Cmpd No. | Structure |
|---|---|
| 707b | 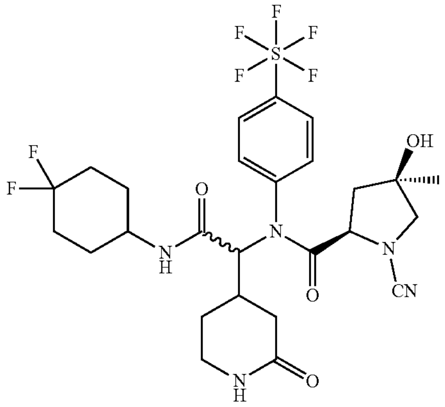 [SMILES: C[C@@]1(O)C[C@H](C(=O)N(c2ccc(S(F)(F)(F)(F)F)cc2)C(C(=O)NC2CCC(F)(F)CC2)C2CCNC(=O)C2)N(C#N)C1] |
| 708 | 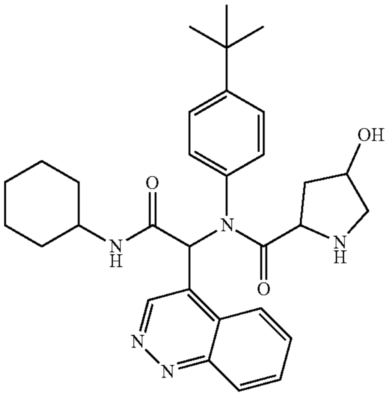 [SMILES: CC(C)(C)c1ccc(N(C(=O)C2CC(O)CN2)C(C(=O)NC2CCCCC2)c2cnnc3ccccc23)cc1] |
| 709 | 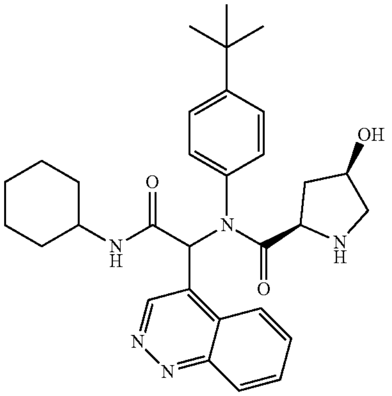 [SMILES: CC(C)(C)c1ccc(N(C(=O)[C@H]2C[C@@H](O)CN2)C(C(=O)NC2CCCCC2)c2cnnc3ccccc23)cc1] |
| Cmpd No. | Structure |
|---|---|
| 710 | 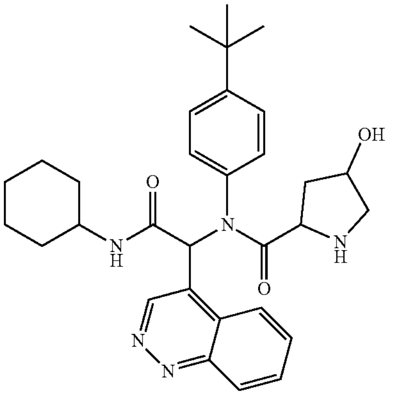 [SMILES: CC(C)(C)c1ccc(N(C(=O)C2CC(O)CN2)C(C(=O)NC2CCCCC2)c2cnnc3ccccc23)cc1] |
| 711 | 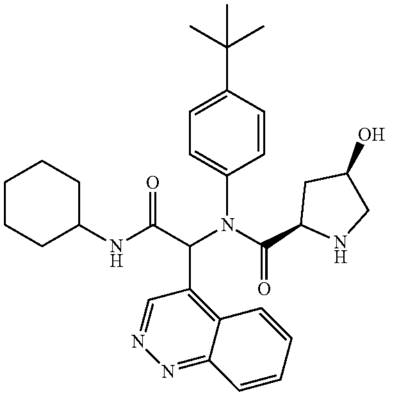 [SMILES: CC(C)(C)c1ccc(N(C(=O)[C@H]2C[C@@H](O)CN2)C(C(=O)NC2CCCCC2)c2cnnc3ccccc23)cc1] |
| 711b | 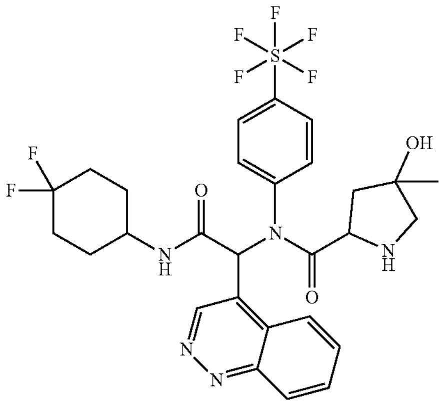 [SMILES: CC1(O)CNC(C(=O)N(c2ccc(S(F)(F)(F)(F)F)cc2)C(C(=O)NC2CCC(F)(F)CC2)c2cnnc3ccccc23)C1] |

TABLE 1-continued
Exemplary compounds.
| Cmpd No. | Structure |
|---|---|
| 711a | 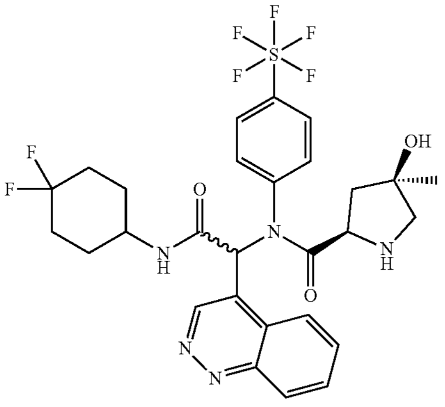 [SMILES: C[C@]1(O)CN[C@@H](C(=O)N(c2ccc(S(F)(F)(F)(F)F)cc2)C(C(=O)NC2CCC(F)(F)CC2)c2cnnc3ccccc23)C1] |
| 712b | 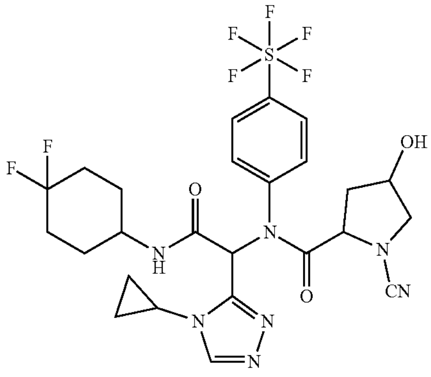 [SMILES: N#CN1CC(O)CC1C(=O)N(c1ccc(S(F)(F)(F)(F)F)cc1)C(C(=O)NC1CCC(F)(F)CC1)c1nncn1C1CC1] |
| 712a | 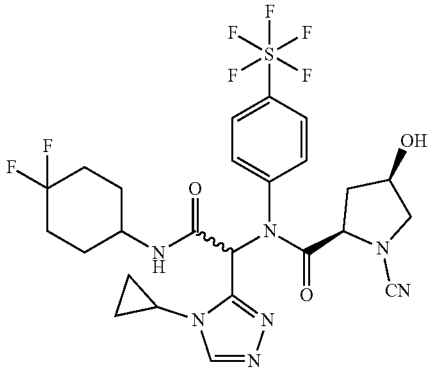 [SMILES: N#CN1C[C@H](O)C[C@@H]1C(=O)N(c1ccc(S(F)(F)(F)(F)F)cc1)C(C(=O)NC1CCC(F)(F)CC1)c1nncn1C1CC1] |
| 712 | 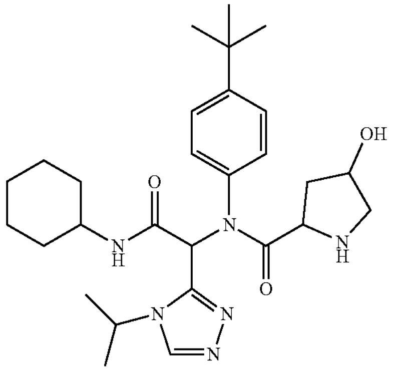 [SMILES: CC(C)n1cnnc1C(C(=O)NC1CCCCC1)N(C(=O)C1CC(O)CN1)c1ccc(C(C)(C)C)cc1] |
| 713 | 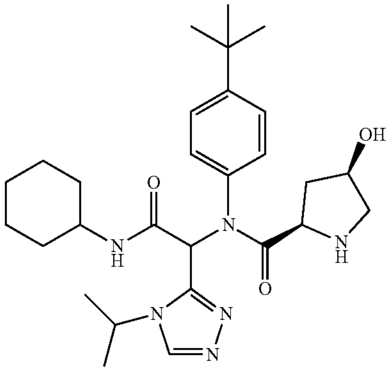 [SMILES: CC(C)n1cnnc1C(C(=O)NC1CCCCC1)N(C(=O)[C@H]1C[C@@H](O)CN1)c1ccc(C(C)(C)C)cc1] |
| 714 | 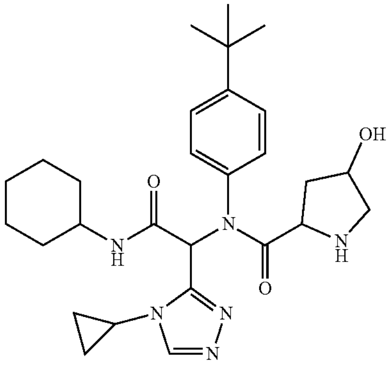 [SMILES: CC(C)(C)c1ccc(N(C(=O)C2CC(O)CN2)C(C(=O)NC2CCCCC2)c2nncn2C2CC2)cc1] |
| 715 | 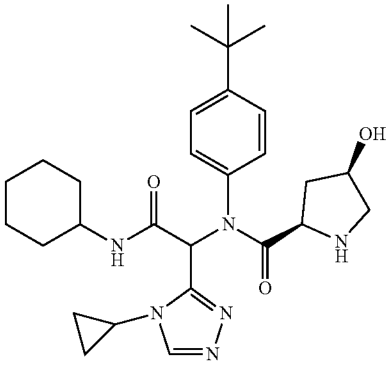 [SMILES: CC(C)(C)c1ccc(N(C(=O)[C@H]2C[C@@H](O)CN2)C(C(=O)NC2CCCCC2)c2nncn2C2CC2)cc1] |
| 716 | 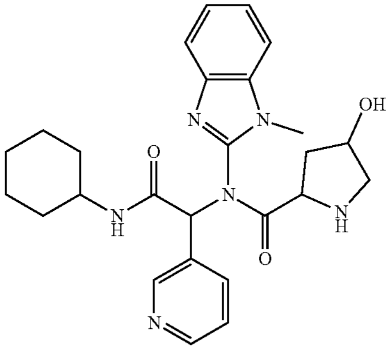 [SMILES: Cn1c(N(C(=O)C2CC(O)CN2)C(C(=O)NC2CCCCC2)c2cccnc2)nc2ccccc21] |

TABLE 1-continued
Exemplary compounds.
| Cmpd No. | Structure |
| --- | --- |
| 717 | 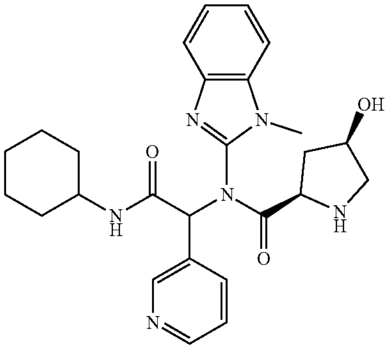 [SMILES: Cn1c(N(C(=O)[C@H]2C[C@@H](O)CN2)C(C(=O)NC2CCCCC2)c2cccnc2)nc2ccccc21] |
| 718 | 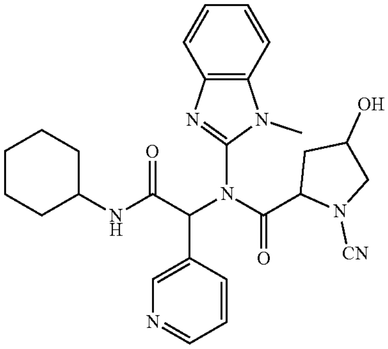 [SMILES: Cn1c(N(C(=O)C2CC(O)CN2C#N)C(C(=O)NC2CCCCC2)c2cccnc2)nc2ccccc21] |
| 719 | 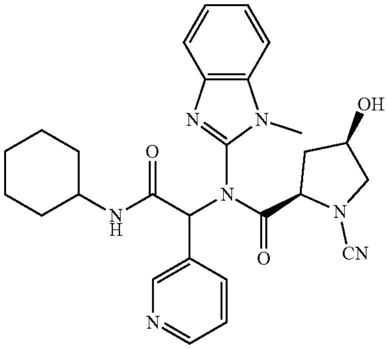 [SMILES: Cn1c(N(C(=O)[C@H]2C[C@@H](O)CN2C#N)C(C(=O)NC2CCCCC2)c2cccnc2)nc2ccccc21] |
| 720 | 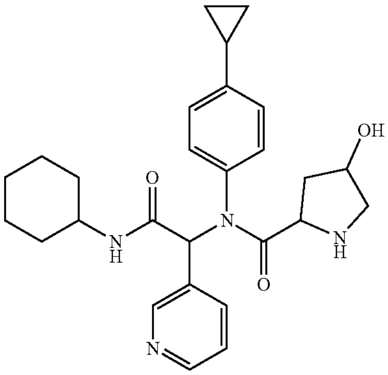 [SMILES: O=C(NC1CCCCC1)C(c1cccnc1)N(C(=O)C1CC(O)CN1)c1ccc(C2CC2)cc1] |
| 721 | 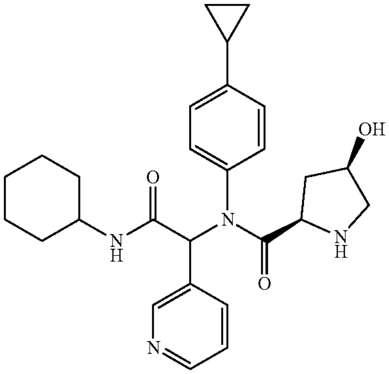 [SMILES: O=C(NC1CCCCC1)C(c1cccnc1)N(C(=O)[C@H]1C[C@@H](O)CN1)c1ccc(C2CC2)cc1] |
| 722 | 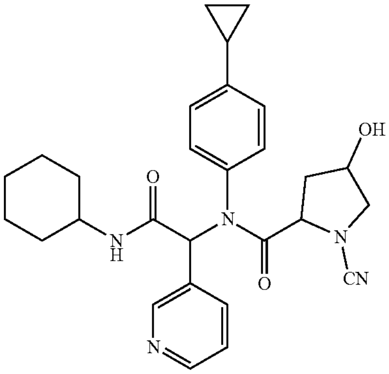 [SMILES: N#CN1CC(O)CC1C(=O)N(c1ccc(C2CC2)cc1)C(C(=O)NC1CCCCC1)c1cccnc1] |
| 723 | 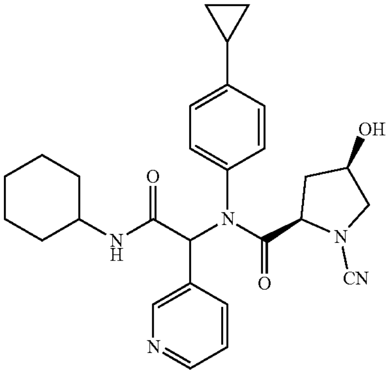 [SMILES: N#CN1C[C@H](O)C[C@@H]1C(=O)N(c1ccc(C2CC2)cc1)C(C(=O)NC1CCCCC1)c1cccnc1] |
| 724 | 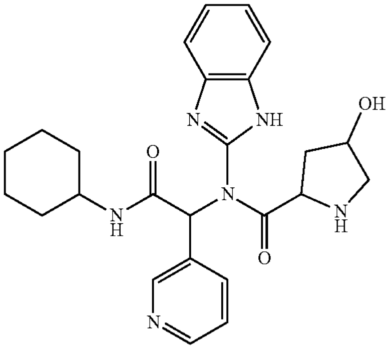 [SMILES: O=C(NC1CCCCC1)C(c1cccnc1)N(C(=O)C1CC(O)CN1)c1nc2ccccc2[nH]1] |

TABLE 1-continued
| Exemplary compounds. | |
|---|---|
| Cmpd No. | Structure |
| 725 | 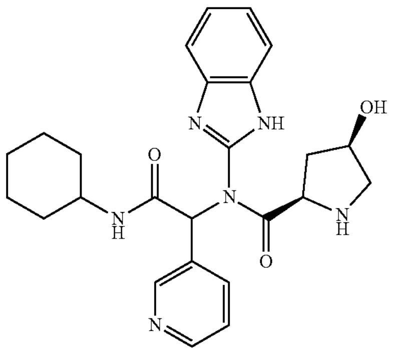 [SMILES: O=C(NC1CCCCC1)C(c1cccnc1)N(C(=O)[C@H]1C[C@@H](O)CN1)c1nc2ccccc2[nH]1] |
| 726 | 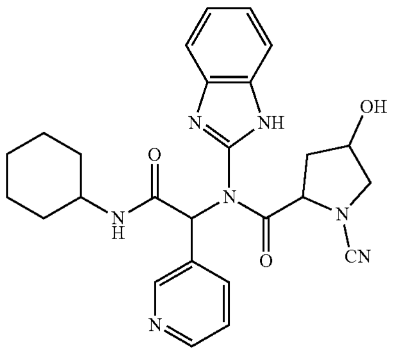 [SMILES: N#CN1CC(O)CC1C(=O)N(c1nc2ccccc2[nH]1)C(C(=O)NC1CCCCC1)c1cccnc1] |
| 727 | 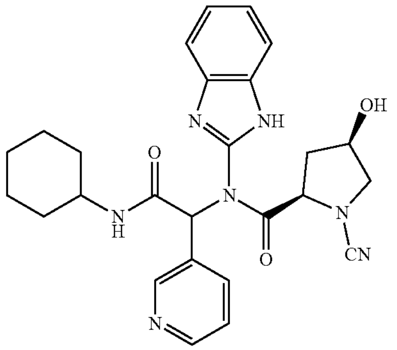 [SMILES: N#CN1C[C@H](O)C[C@@H]1C(=O)N(c1nc2ccccc2[nH]1)C(C(=O)NC1CCCCC1)c1cccnc1] |
| 728 | 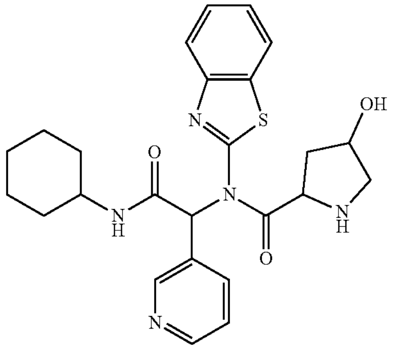 [SMILES: O=C(NC1CCCCC1)C(c1cccnc1)N(C(=O)C1CC(O)CN1)c1nc2ccccc2s1] |
TABLE 1-continued
| Exemplary compounds. | |
|---|---|
| Cmpd No. | Structure |
| 729 | 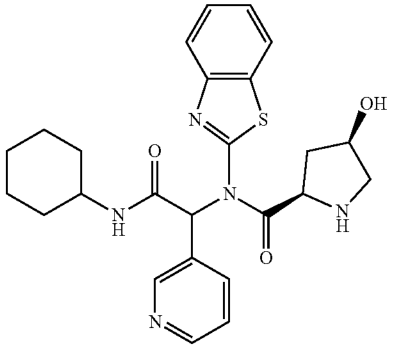 [SMILES: O=C(NC1CCCCC1)C(c1cccnc1)N(C(=O)[C@H]1C[C@@H](O)CN1)c1nc2ccccc2s1] |
| 730 | 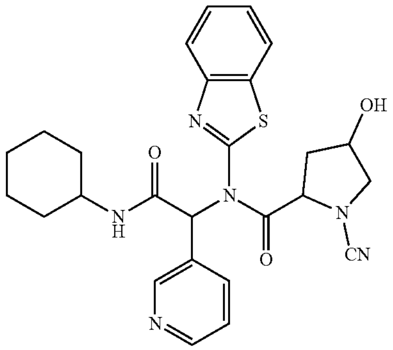 [SMILES: N#CN1CC(O)CC1C(=O)N(c1nc2ccccc2s1)C(C(=O)NC1CCCCC1)c1cccnc1] |
| 731 | 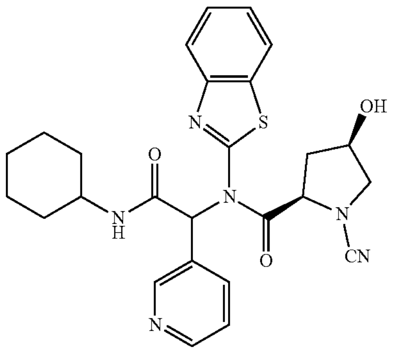 [SMILES: N#CN1C[C@H](O)C[C@@H]1C(=O)N(c1nc2ccccc2s1)C(C(=O)NC1CCCCC1)c1cccnc1] |
| 732 | 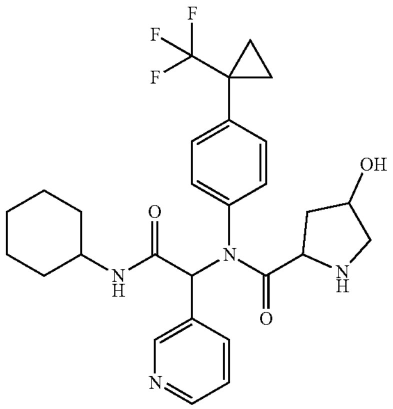 [SMILES: O=C(NC1CCCCC1)C(c1cccnc1)N(C(=O)C1CC(O)CN1)c1ccc(C2(C(F)(F)F)CC2)cc1] |

TABLE 1-continued
| Exemplary compounds. | |
|---|---|
| Cmpd No. | Structure |
| 733 | 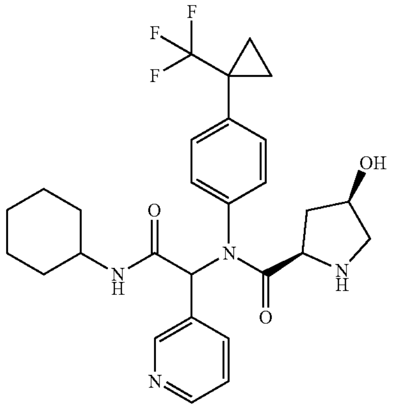 [SMILES: O=C(NC1CCCCC1)C(c1cccnc1)N(C(=O)[C@H]1C[C@@H](O)CN1)c1ccc(C2(C(F)(F)F)CC2)cc1] |
| 734 | 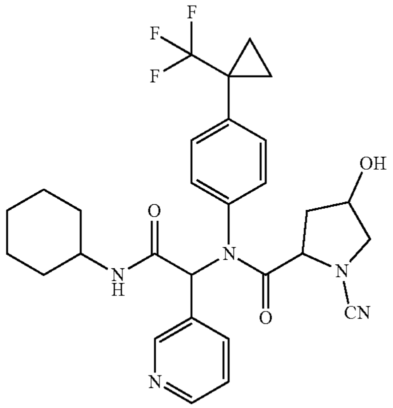 [SMILES: N#CN1CC(O)CC1C(=O)N(c1ccc(C2(C(F)(F)F)CC2)cc1)C(C(=O)NC1CCCCC1)c1cccnc1] |
| 735 | 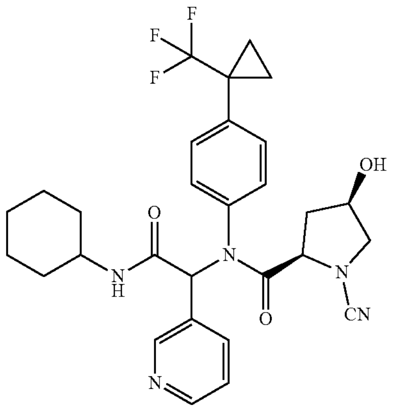 [SMILES: N#CN1C[C@H](O)C[C@@H]1C(=O)N(c1ccc(C2(C(F)(F)F)CC2)cc1)C(C(=O)NC1CCCCC1)c1cccnc1] |
TABLE 1-continued
| Exemplary compounds. | |
|---|---|
| Cmpd No. | Structure |
| 736 | 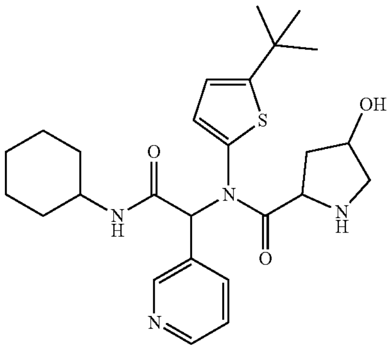 [SMILES: CC(C)(C)c1ccc(N(C(=O)C2CC(O)CN2)C(C(=O)NC2CCCCC2)c2cccnc2)s1] |
| 737 | 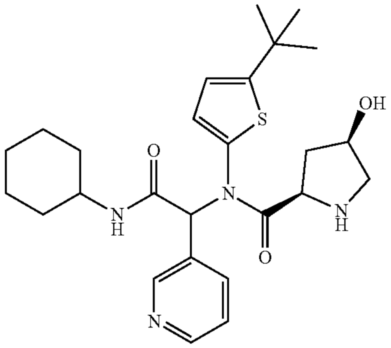 [SMILES: CC(C)(C)c1ccc(N(C(=O)[C@H]2C[C@@H](O)CN2)C(C(=O)NC2CCCCC2)c2cccnc2)s1] |
| 738 | 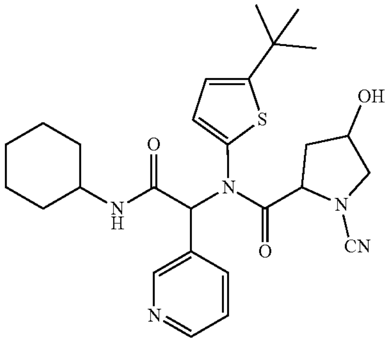 [SMILES: CC(C)(C)c1ccc(N(C(=O)C2CC(O)CN2C#N)C(C(=O)NC2CCCCC2)c2cccnc2)s1] |
| 739 | 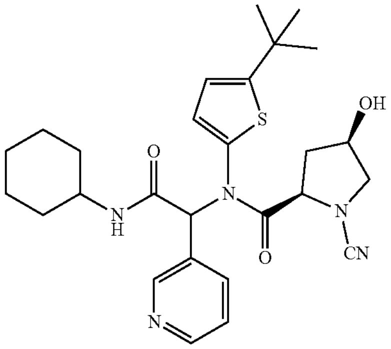 [SMILES: CC(C)(C)c1ccc(N(C(=O)[C@H]2C[C@@H](O)CN2C#N)C(C(=O)NC2CCCCC2)c2cccnc2)s1] |

TABLE 1-continued
| Exemplary compounds. | |
|---|---|
| Cmpd No. | Structure |
| 740 | 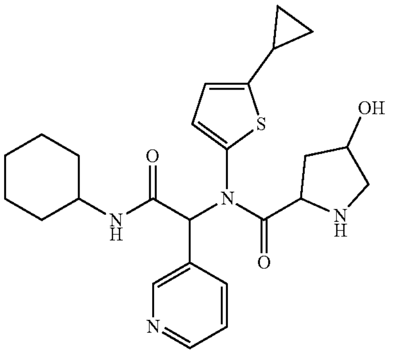 [SMILES: O=C(NC1CCCCC1)C(c1cccnc1)N(C(=O)C1CC(O)CN1)c1ccc(C2CC2)s1] |
| 741 | 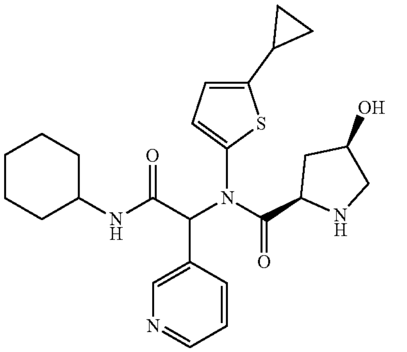 [SMILES: O=C(NC1CCCCC1)C(c1cccnc1)N(C(=O)[C@H]1C[C@@H](O)CN1)c1ccc(C2CC2)s1] |
| 742 | 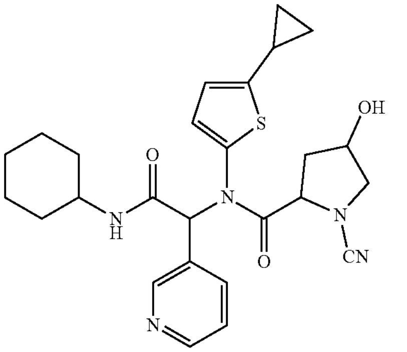 [SMILES: N#CN1CC(O)CC1C(=O)N(c1ccc(C2CC2)s1)C(C(=O)NC1CCCCC1)c1cccnc1] |
| 743 | 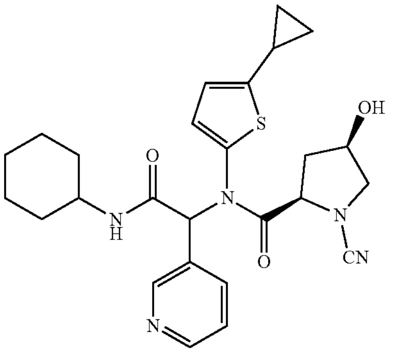 [SMILES: N#CN1C[C@H](O)C[C@@H]1C(=O)N(c1ccc(C2CC2)s1)C(C(=O)NC1CCCCC1)c1cccnc1] |
TABLE 1-continued
| Exemplary compounds. | |
|---|---|
| Cmpd No. | Structure |
| 744 | 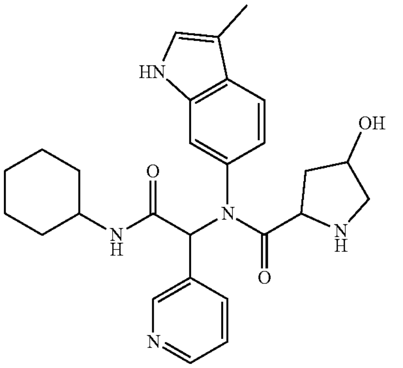 [SMILES: Cc1c[nH]c2cc(N(C(=O)C3CC(O)CN3)C(C(=O)NC3CCCCC3)c3cccnc3)ccc12] |
| 745 | 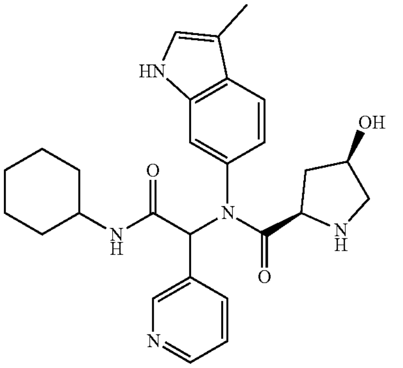 [SMILES: Cc1c[nH]c2cc(N(C(=O)[C@H]3C[C@@H](O)CN3)C(C(=O)NC3CCCCC3)c3cccnc3)ccc12] |
| 746 | 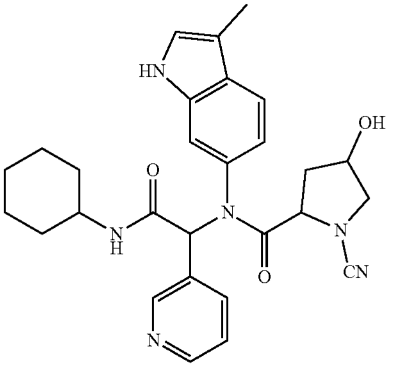 [SMILES: Cc1c[nH]c2cc(N(C(=O)C3CC(O)CN3C#N)C(C(=O)NC3CCCCC3)c3cccnc3)ccc12] |
| 747 | 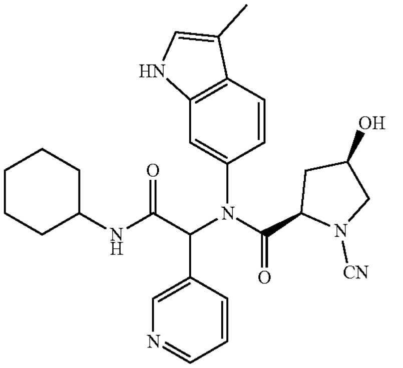 [SMILES: Cc1c[nH]c2cc(N(C(=O)[C@H]3C[C@@H](O)CN3C#N)C(C(=O)NC3CCCCC3)c3cccnc3)ccc12] |

TABLE 1-continued
| Exemplary compounds. | |
|---|---|
| Cmpd No. | Structure |
| 747a | 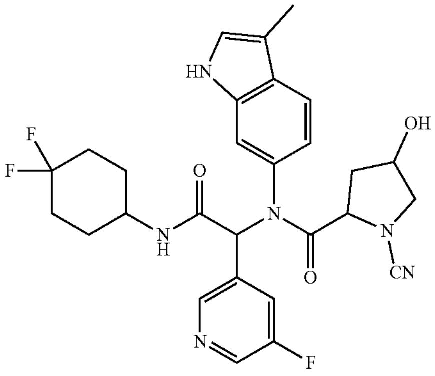 [SMILES: Cc1c[nH]c2cc(N(C(=O)C3CC(O)CN3C#N)C(C(=O)NC3CCC(F)(F)CC3)c3cncc(F)c3)ccc12] |
| 747b | 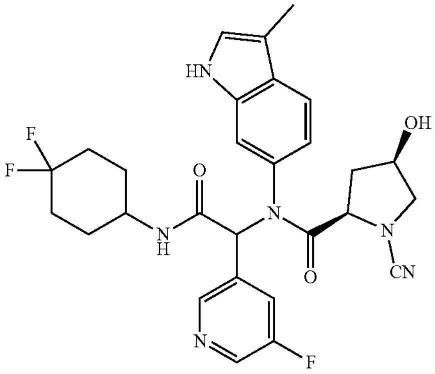 [SMILES: Cc1c[nH]c2cc(N(C(=O)[C@H]3C[C@@H](O)CN3C#N)C(C(=O)NC3CCC(F)(F)CC3)c3cncc(F)c3)ccc12] |
| 748 | 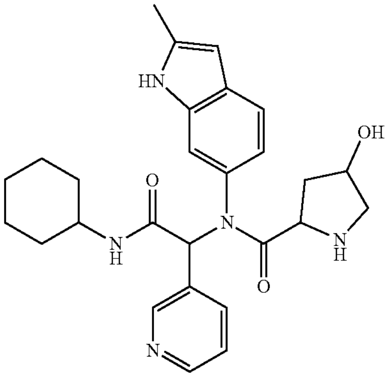 [SMILES: Cc1cc2ccc(N(C(=O)C3CC(O)CN3)C(C(=O)NC3CCCCC3)c3cccnc3)cc2[nH]1] |
| 749 | 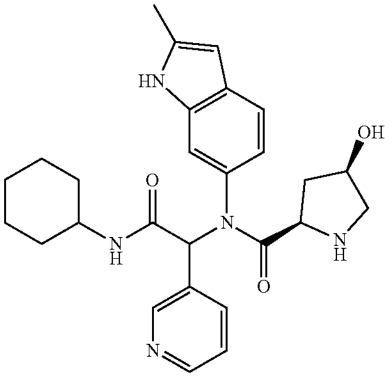 [SMILES: Cc1cc2ccc(N(C(=O)[C@H]3C[C@@H](O)CN3)C(C(=O)NC3CCCCC3)c3cccnc3)cc2[nH]1] |
TABLE 1-continued
| Exemplary compounds. | |
|---|---|
| Cmpd No. | Structure |
| 750 | 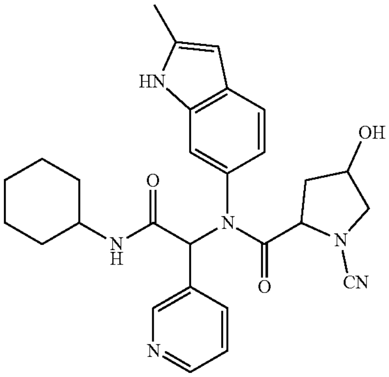 [SMILES: Cc1cc2ccc(N(C(=O)C3CC(O)CN3C#N)C(C(=O)NC3CCCCC3)c3cccnc3)cc2[nH]1] |
| 751 | 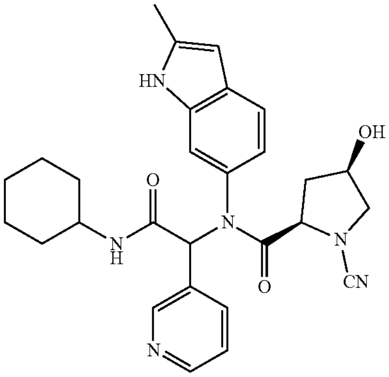 [SMILES: Cc1cc2ccc(N(C(=O)[C@H]3C[C@@H](O)CN3C#N)C(C(=O)NC3CCCCC3)c3cccnc3)cc2[nH]1] |
| 752 | 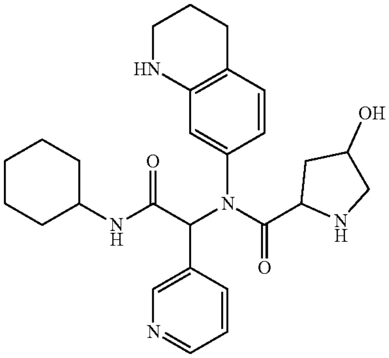 [SMILES: O=C(NC1CCCCC1)C(c1cccnc1)N(C(=O)C1CC(O)CN1)c1ccc2c(c1)NCCC2] |
| 753 | 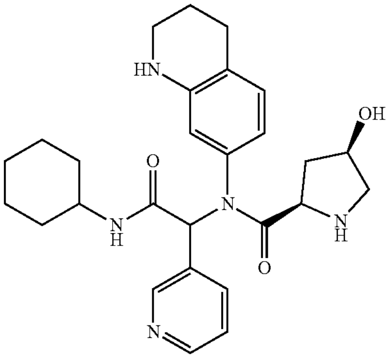 [SMILES: O=C(NC1CCCCC1)C(c1cccnc1)N(C(=O)[C@H]1C[C@@H](O)CN1)c1ccc2c(c1)NCCC2] |

TABLE 1-continued
| Exemplary compounds. | |
|---|---|
| Cmpd No. | Structure |
| 754 | 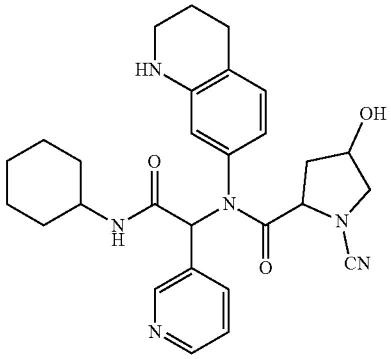 [SMILES: N#CN1CC(O)CC1C(=O)N(c1ccc2c(c1)NCCC2)C(C(=O)NC1CCCCC1)c1cccnc1] |
| 755 | 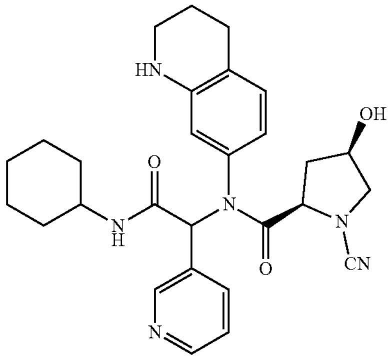 [SMILES: N#CN1C[C@H](O)C[C@@H]1C(=O)N(c1ccc2c(c1)NCCC2)C(C(=O)NC1CCCCC1)c1cccnc1] |
| 756 | 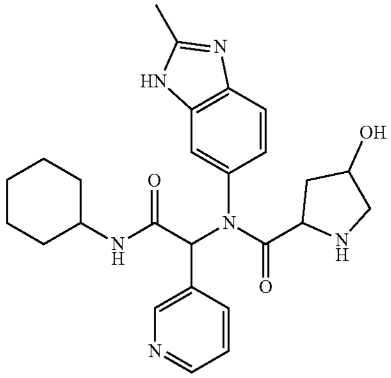 [SMILES: Cc1nc2ccc(N(C(=O)C3CC(O)CN3)C(C(=O)NC3CCCCC3)c3cccnc3)cc2[nH]1] |
| 757 | 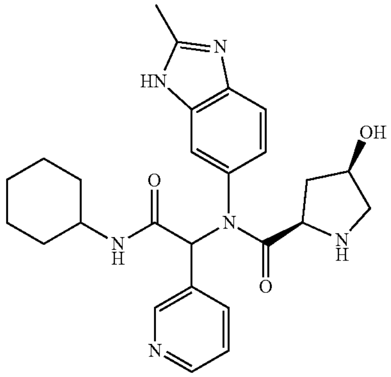 [SMILES: Cc1nc2ccc(N(C(=O)[C@H]3C[C@@H](O)CN3)C(C(=O)NC3CCCCC3)c3cccnc3)cc2[nH]1] |
TABLE 1-continued
| Exemplary compounds. | |
|---|---|
| Cmpd No. | Structure |
| 758 | 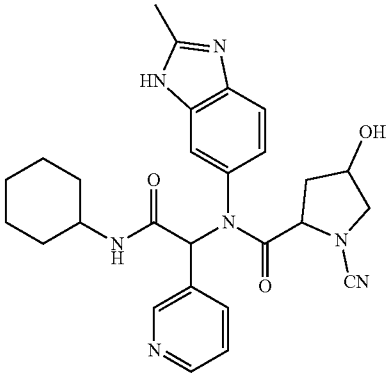 [SMILES: Cc1nc2ccc(N(C(=O)C3CC(O)CN3C#N)C(C(=O)NC3CCCCC3)c3cccnc3)cc2[nH]1] |
| 759 | 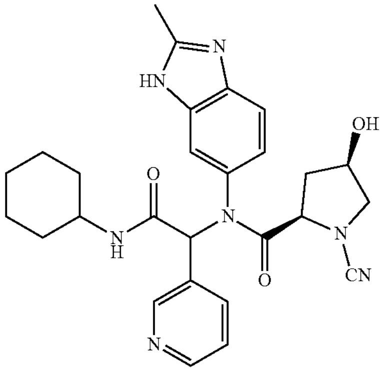 [SMILES: Cc1nc2ccc(N(C(=O)[C@H]3C[C@@H](O)CN3C#N)C(C(=O)NC3CCCCC3)c3cccnc3)cc2[nH]1] |
| 760 | 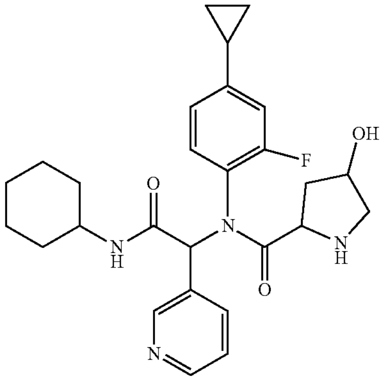 [SMILES: O=C(NC1CCCCC1)C(c1cccnc1)N(C(=O)C1CC(O)CN1)c1ccc(C2CC2)cc1F] |
| 761 | 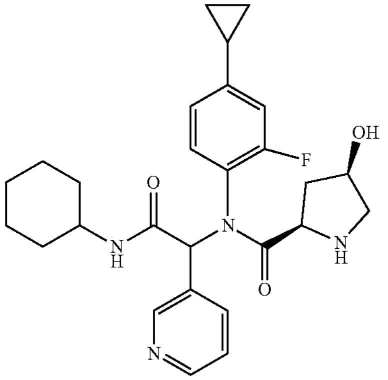 [SMILES: O=C(NC1CCCCC1)C(c1cccnc1)N(C(=O)[C@H]1C[C@@H](O)CN1)c1ccc(C2CC2)cc1F] |

TABLE 1-continued
| Exemplary compounds. | |
|---|---|
| Cmpd No. | Structure |
| 762 | 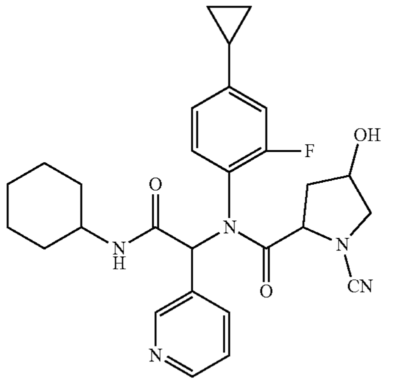 [SMILES: N#CN1CC(O)CC1C(=O)N(c1ccc(C2CC2)cc1F)C(C(=O)NC1CCCCC1)c1cccnc1] |
| 763 | 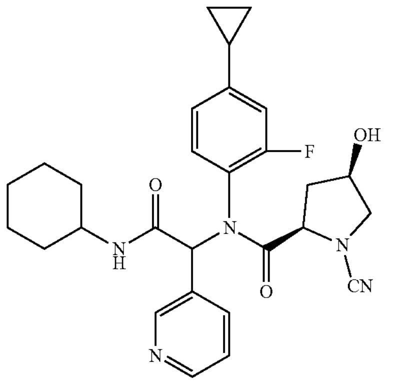 [SMILES: N#CN1C[C@H](O)C[C@@H]1C(=O)N(c1ccc(C2CC2)cc1F)C(C(=O)NC1CCCCC1)c1cccnc1] |
| 764 | 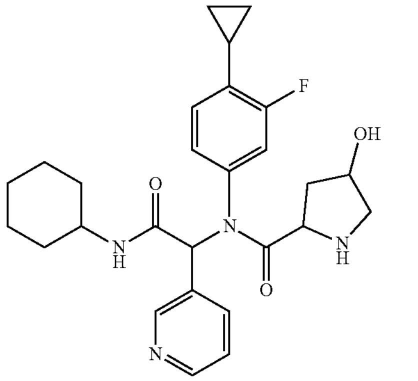 [SMILES: O=C(NC1CCCCC1)C(c1cccnc1)N(C(=O)C1CC(O)CN1)c1ccc(C2CC2)c(F)c1] |
| 765 | 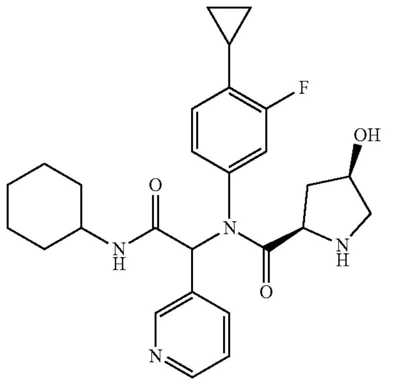 [SMILES: O=C(NC1CCCCC1)C(c1cccnc1)N(C(=O)[C@H]1C[C@@H](O)CN1)c1ccc(C2CC2)c(F)c1] |
TABLE 1-continued
| Exemplary compounds. | |
|---|---|
| Cmpd No. | Structure |
| 766 | 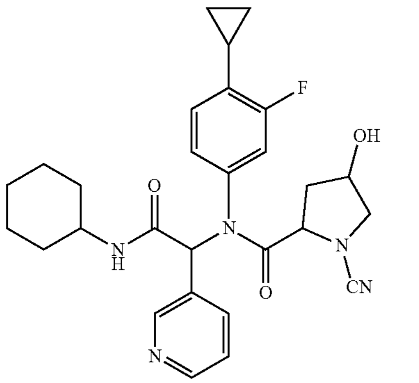 [SMILES: N#CN1CC(O)CC1C(=O)N(c1ccc(C2CC2)c(F)c1)C(C(=O)NC1CCCCC1)c1cccnc1] |
| 767 | 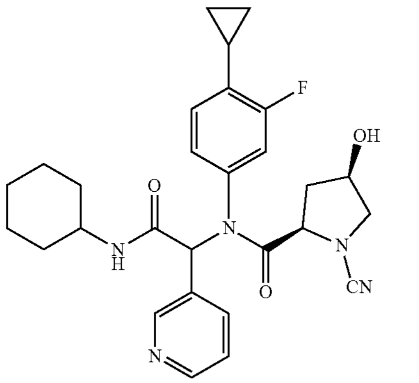 [SMILES: N#CN1C[C@H](O)C[C@@H]1C(=O)N(c1ccc(C2CC2)c(F)c1)C(C(=O)NC1CCCCC1)c1cccnc1] |
| 768 | 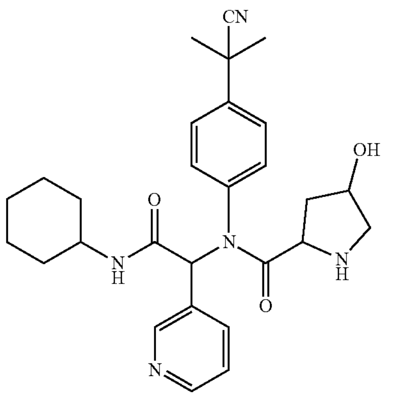 [SMILES: CC(C)(C#N)c1ccc(N(C(=O)C2CC(O)CN2)C(C(=O)NC2CCCCC2)c2cccnc2)cc1] |

TABLE 1-continued
| Exemplary compounds. | |
|---|---|
| Cmpd No. | Structure |
| 769 | 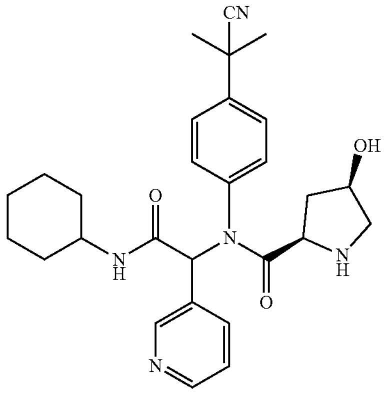 [SMILES: CC(C)(C#N)c1ccc(N(C(=O)[C@H]2C[C@@H](O)CN2)C(C(=O)NC2CCCCC2)c2cccnc2)cc1] |
| 770 | 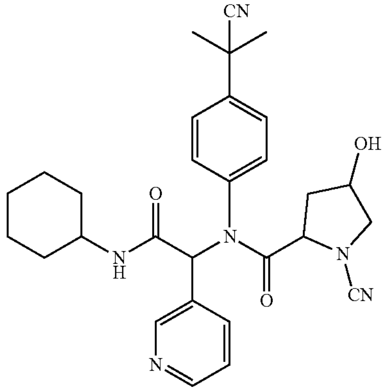 [SMILES: CC(C)(C#N)c1ccc(N(C(=O)C2CC(O)CN2C#N)C(C(=O)NC2CCCCC2)c2cccnc2)cc1] |
| 771 | 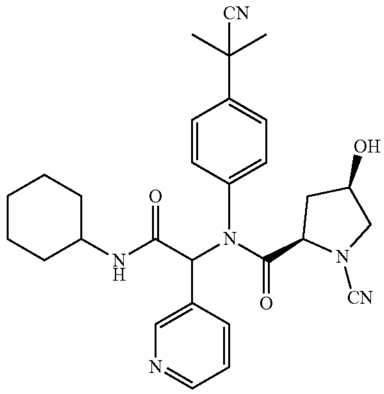 [SMILES: CC(C)(C#N)c1ccc(N(C(=O)[C@H]2C[C@@H](O)CN2C#N)C(C(=O)NC2CCCCC2)c2cccnc2)cc1] |
TABLE 1-continued
| Exemplary compounds. | |
|---|---|
| Cmpd No. | Structure |
| 772 | 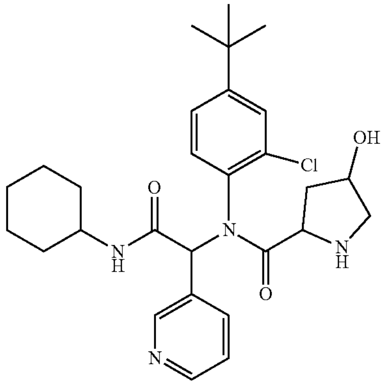 [SMILES: CC(C)(C)c1ccc(N(C(=O)C2CC(O)CN2)C(C(=O)NC2CCCCC2)c2cccnc2)c(Cl)c1] |
| 773 | 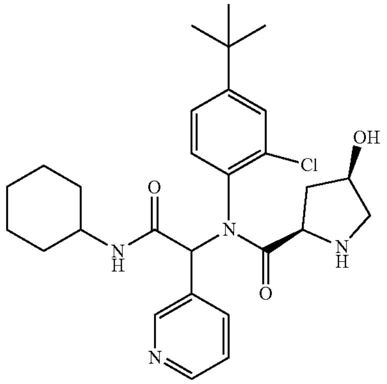 [SMILES: CC(C)(C)c1ccc(N(C(=O)[C@H]2C[C@@H](O)CN2)C(C(=O)NC2CCCCC2)c2cccnc2)c(Cl)c1] |
| 774 | 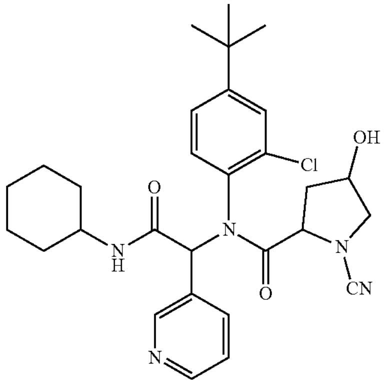 [SMILES: CC(C)(C)c1ccc(N(C(=O)C2CC(O)CN2C#N)C(C(=O)NC2CCCCC2)c2cccnc2)c(Cl)c1] |
| 775 | 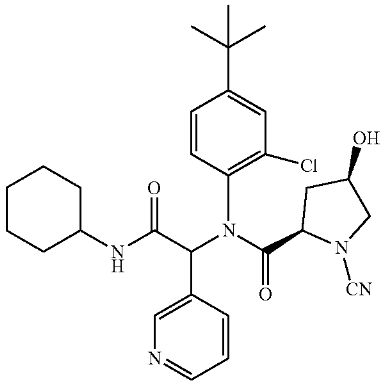 [SMILES: CC(C)(C)c1ccc(N(C(=O)[C@H]2C[C@@H](O)CN2C#N)C(C(=O)NC2CCCCC2)c2cccnc2)c(Cl)c1] |

TABLE 1-continued
Exemplary compounds.
| Cmpd No. | Structure |
|---|---|
| 776 | 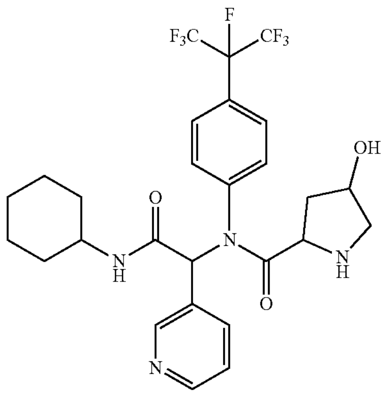 [SMILES: O=C(NC1CCCCC1)C(c1cccnc1)N(C(=O)C1CC(O)CN1)c1ccc(C(F)(C(F)(F)F)C(F)(F)F)cc1] |
| 777 | 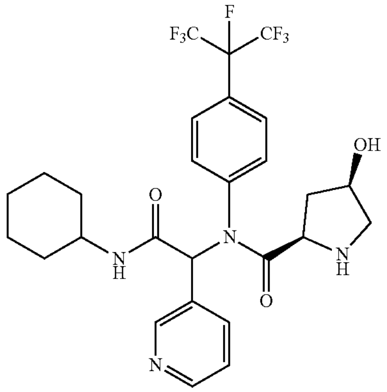 [SMILES: O=C(NC1CCCCC1)C(c1cccnc1)N(C(=O)[C@H]1C[C@@H](O)CN1)c1ccc(C(F)(C(F)(F)F)C(F)(F)F)cc1] |
| 778 | 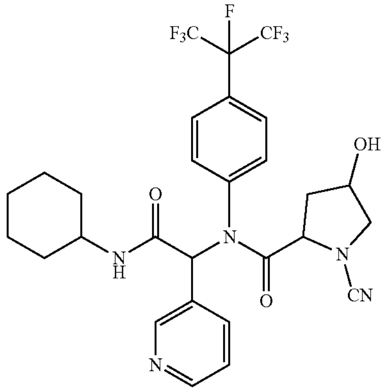 [SMILES: N#CN1CC(O)CC1C(=O)N(c1ccc(C(F)(C(F)(F)F)C(F)(F)F)cc1)C(C(=O)NC1CCCCC1)c1cccnc1] |
| 779 | 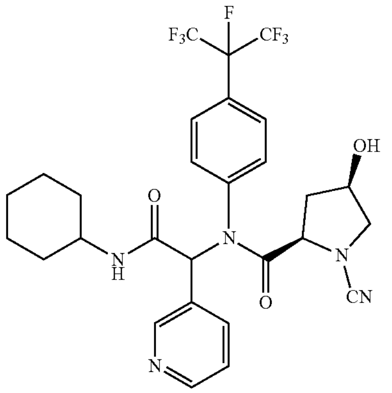 [SMILES: N#CN1C[C@H](O)C[C@@H]1C(=O)N(c1ccc(C(F)(C(F)(F)F)C(F)(F)F)cc1)C(C(=O)NC1CCCCC1)c1cccnc1] |
| 780 | 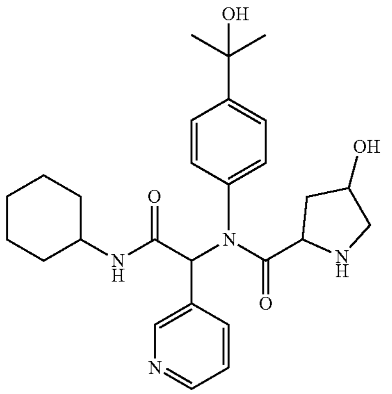 |
| 781 | 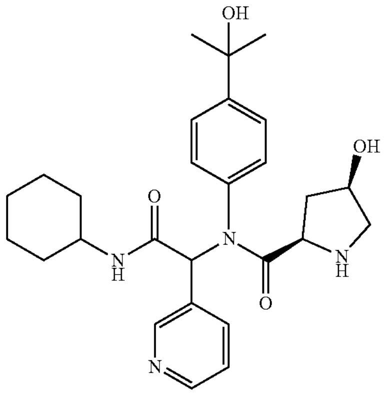 [SMILES: CC(C)(O)c1ccc(N(C(=O)[C@H]2C[C@@H](O)CN2)C(C(=O)NC2CCCCC2)c2cccnc2)cc1] |

TABLE 1-continued
| Exemplary compounds. | |
|---|---|
| Cmpd No. | Structure |
| 782 | 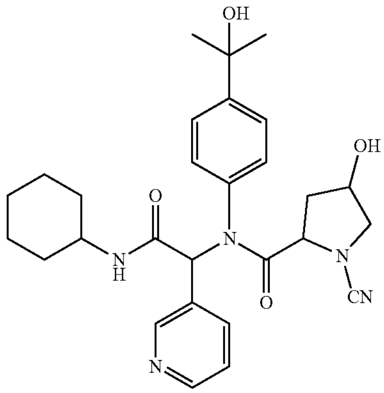 |
| 783 | 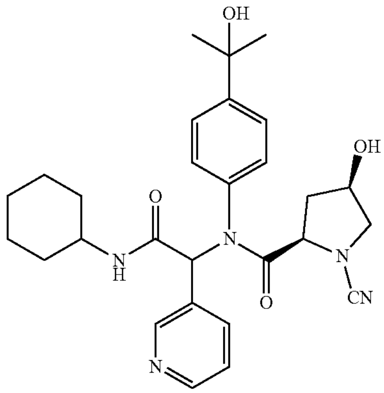 [SMILES: CC(C)(O)c1ccc(N(C(=O)[C@H]2C[C@@H](O)CN2C#N)C(C(=O)NC2CCCCC2)c2cccnc2)cc1] |
| 784 | 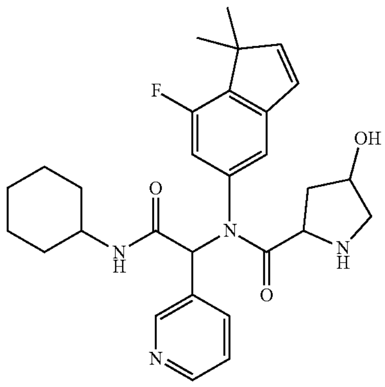 [SMILES: CC1(C)C=Cc2cc(N(C(=O)C3CC(O)CN3)C(C(=O)NC3CCCCC3)c3cccnc3)cc(F)c21] |
TABLE 1-continued
| Exemplary compounds. | |
|---|---|
| Cmpd No. | Structure |
| 785 | 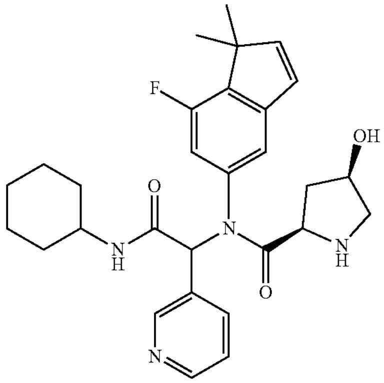 [SMILES: CC1(C)C=Cc2cc(N(C(=O)[C@H]3C[C@@H](O)CN3)C(C(=O)NC3CCCCC3)c3cccnc3)cc(F)c21] |
| 786 | 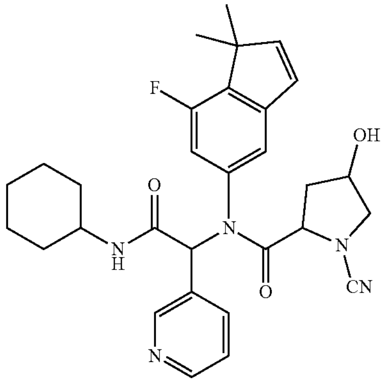 [SMILES: CC1(C)C=Cc2cc(N(C(=O)C3CC(O)CN3C#N)C(C(=O)NC3CCCCC3)c3cccnc3)cc(F)c21] |
| 787 | 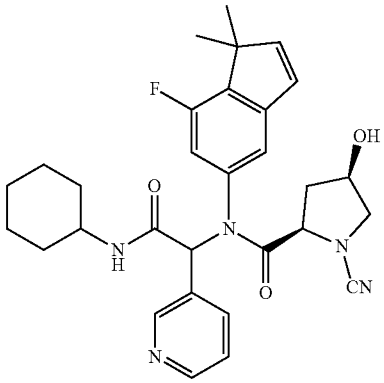 [SMILES: CC1(C)C=Cc2cc(N(C(=O)[C@H]3C[C@@H](O)CN3C#N)C(C(=O)NC3CCCCC3)c3cccnc3)cc(F)c21] |
| 788 | 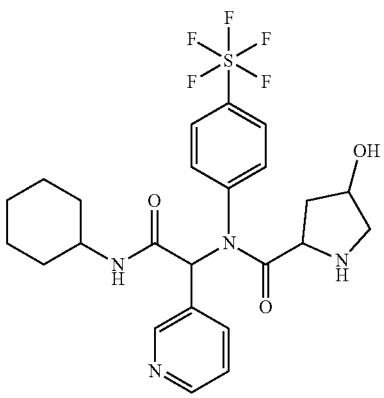 [SMILES: O=C(NC1CCCCC1)C(c1cccnc1)N(C(=O)C1CC(O)CN1)c1ccc(S(F)(F)(F)(F)F)cc1] |

TABLE 1-continued
| Exemplary compounds. | |
|---|---|
| Cmpd No. | Structure |
| 789 | 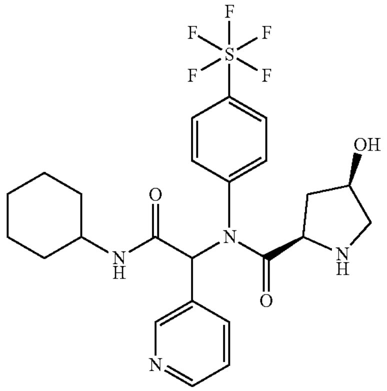 [SMILES: O=C(NC1CCCCC1)C(c1cccnc1)N(C(=O)[C@H]1C[C@@H](O)CN1)c1ccc(S(F)(F)(F)(F)F)cc1] |
| 790 | 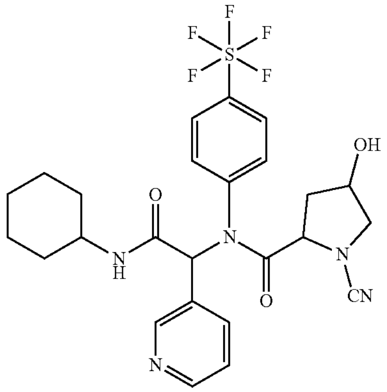 [SMILES: N#CN1CC(O)CC1C(=O)N(c1ccc(S(F)(F)(F)(F)F)cc1)C(C(=O)NC1CCCCC1)c1cccnc1] |
| 791 | 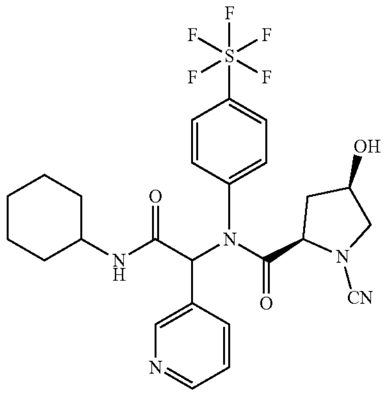 [SMILES: N#CN1C[C@H](O)C[C@@H]1C(=O)N(c1ccc(S(F)(F)(F)(F)F)cc1)C(C(=O)NC1CCCCC1)c1cccnc1] |
TABLE 1-continued
| Exemplary compounds. | |
|---|---|
| Cmpd No. | Structure |
| 792 | 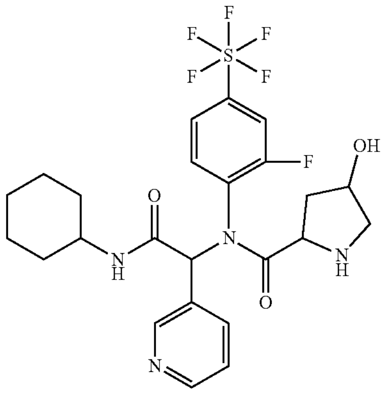 [SMILES: O=C(NC1CCCCC1)C(c1cccnc1)N(C(=O)C1CC(O)CN1)c1ccc(S(F)(F)(F)(F)F)cc1F] |
| 793 | 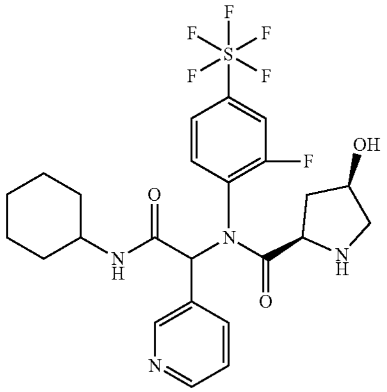 [SMILES: O=C(NC1CCCCC1)C(c1cccnc1)N(C(=O)[C@H]1C[C@@H](O)CN1)c1ccc(S(F)(F)(F)(F)F)cc1F] |
| 794 | 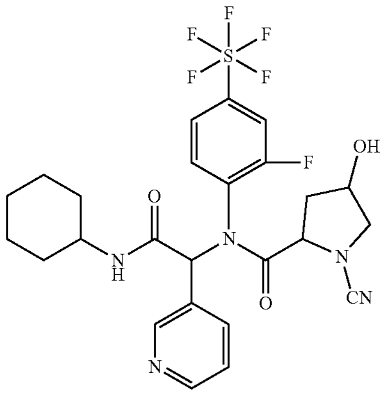 [SMILES: N#CN1CC(O)CC1C(=O)N(c1ccc(S(F)(F)(F)(F)F)cc1F)C(C(=O)NC1CCCCC1)c1cccnc1] |

TABLE 1-continued
| Exemplary compounds. | |
|---|---|
| Cmpd No. | Structure |
| 795 | 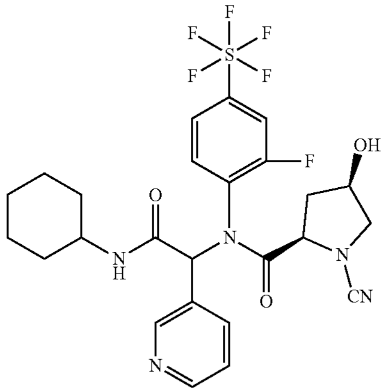 [SMILES: N#CN1C[C@H](O)C[C@@H]1C(=O)N(c1ccc(S(F)(F)(F)(F)F)cc1F)C(C(=O)NC1CCCCC1)c1cccnc1] |
| 796 | 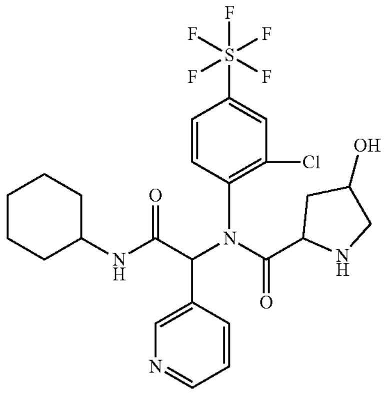 [SMILES: O=C(NC1CCCCC1)C(c1cccnc1)N(C(=O)C1CC(O)CN1)c1ccc(S(F)(F)(F)(F)F)cc1Cl] |
| 797 | 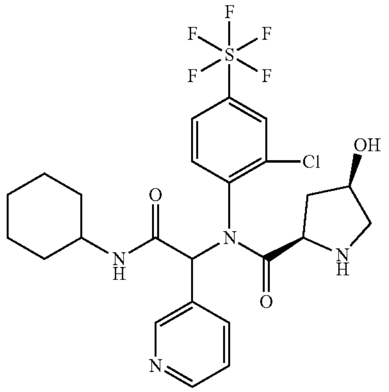 [SMILES: O=C(NC1CCCCC1)C(c1cccnc1)N(C(=O)[C@H]1C[C@@H](O)CN1)c1ccc(S(F)(F)(F)(F)F)cc1Cl] |
| 798 | 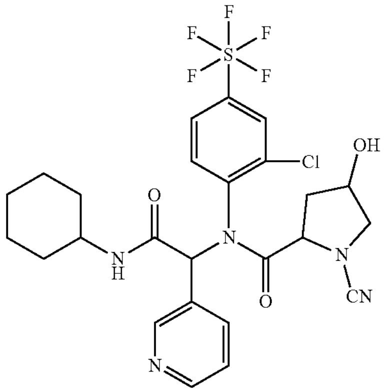 [SMILES: N#CN1CC(O)CC1C(=O)N(c1ccc(S(F)(F)(F)(F)F)cc1Cl)C(C(=O)NC1CCCCC1)c1cccnc1] |
| 799 | 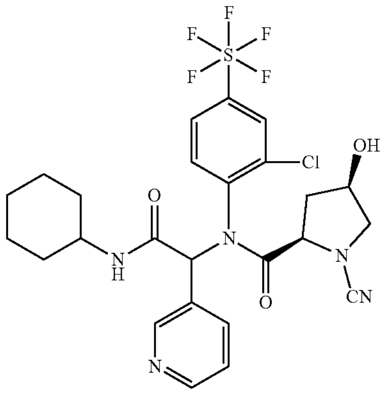 [SMILES: N#CN1C[C@H](O)C[C@@H]1C(=O)N(c1ccc(S(F)(F)(F)(F)F)cc1Cl)C(C(=O)NC1CCCCC1)c1cccnc1] |
| 800 | 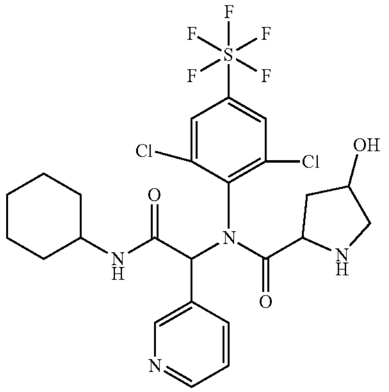 [SMILES: O=C(NC1CCCCC1)C(c1cccnc1)N(C(=O)C1CC(O)CN1)c1c(Cl)cc(S(F)(F)(F)(F)F)cc1Cl] |

TABLE 1-continued
| Exemplary compounds. | |
|---|---|
| Cmpd No. | Structure |
| 801 | 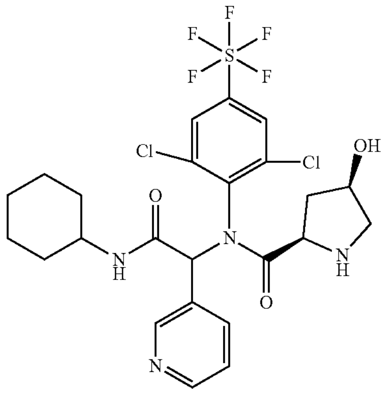 [SMILES: O=C(NC1CCCCC1)C(c1cccnc1)N(C(=O)[C@H]1C[C@@H](O)CN1)c1c(Cl)cc(S(F)(F)(F)(F)F)cc1Cl] |
| 802 | 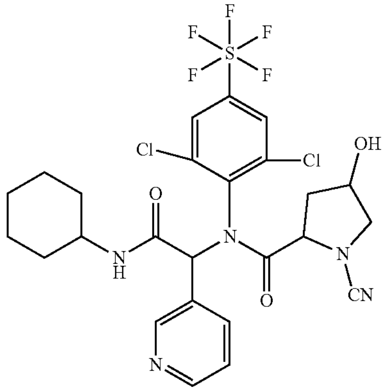 [SMILES: N#CN1CC(O)CC1C(=O)N(c1c(Cl)cc(S(F)(F)(F)(F)F)cc1Cl)C(C(=O)NC1CCCCC1)c1cccnc1] |
| 803 | 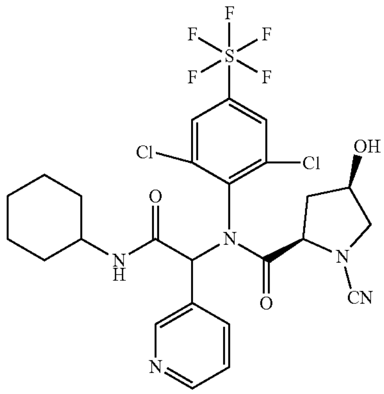 [SMILES: N#CN1C[C@H](O)C[C@@H]1C(=O)N(c1c(Cl)cc(S(F)(F)(F)(F)F)cc1Cl)C(C(=O)NC1CCCCC1)c1cccnc1] |
TABLE 1-continued
| Exemplary compounds. | |
|---|---|
| Cmpd No. | Structure |
| 804 | 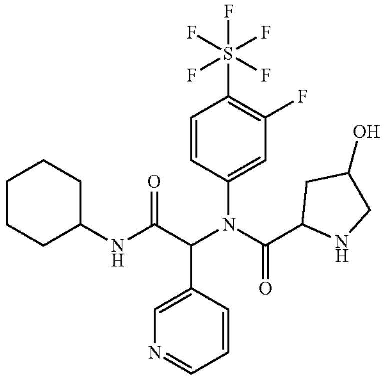 [SMILES: O=C(NC1CCCCC1)C(c1cccnc1)N(C(=O)C1CC(O)CN1)c1ccc(S(F)(F)(F)(F)F)c(F)c1] |
| 805 | 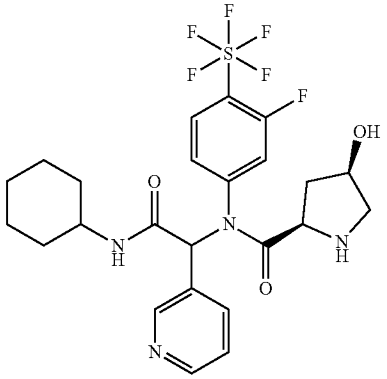 [SMILES: O=C(NC1CCCCC1)C(c1cccnc1)N(C(=O)[C@H]1C[C@@H](O)CN1)c1ccc(S(F)(F)(F)(F)F)c(F)c1] |
| 806 | 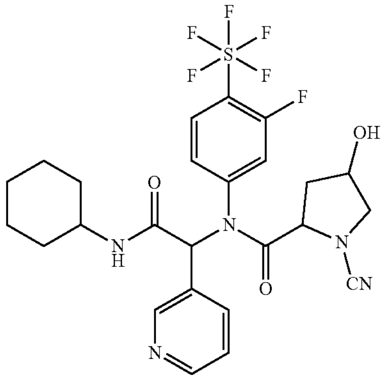 [SMILES: N#CN1CC(O)CC1C(=O)N(c1ccc(S(F)(F)(F)(F)F)c(F)c1)C(C(=O)NC1CCCCC1)c1cccnc1] |
| 807 | 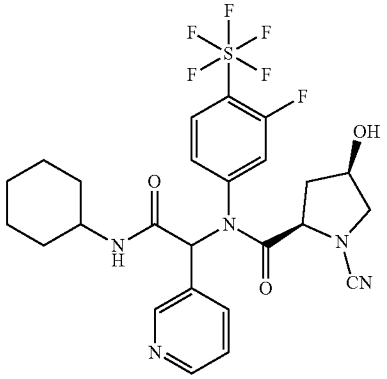 [SMILES: N#CN1C[C@H](O)C[C@@H]1C(=O)N(c1ccc(S(F)(F)(F)(F)F)c(F)c1)C(C(=O)NC1CCCCC1)c1cccnc1] |

TABLE 1-continued
| Exemplary compounds. | |
|---|---|
| Cmpd No. | Structure |
| 808 | 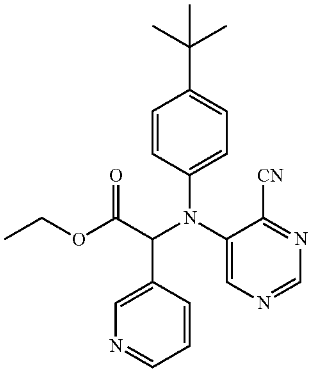 [SMILES: CCOC(=O)C(c1cccnc1)N(c1ccc(C(C)(C)C)cc1)c1cncnc1C#N] |
| 809 | 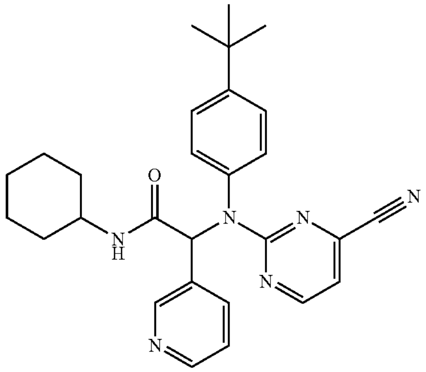 [SMILES: CC(C)(C)c1ccc(N(c2nccc(C#N)n2)C(C(=O)NC2CCCCC2)c2cccnc2)cc1] |
| 810 | 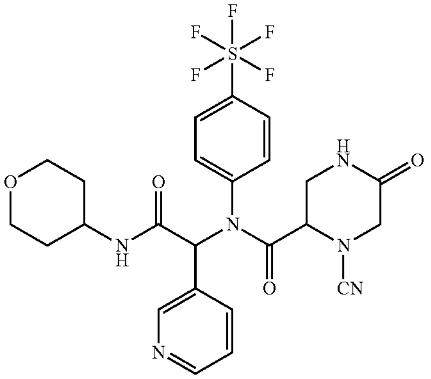 [SMILES: N#CN1CC(=O)NCC1C(=O)N(c1ccc(S(F)(F)(F)(F)F)cc1)C(C(=O)NC1CCOCC1)c1cccnc1] |
| 811 | 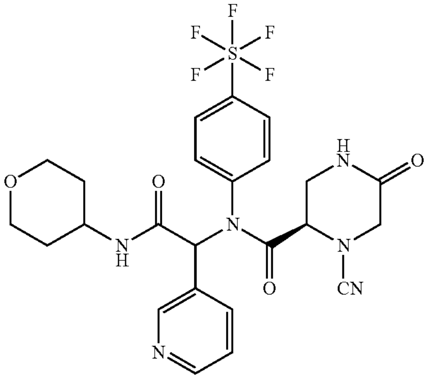 [SMILES: N#CN1CC(=O)NC[C@@H]1C(=O)N(c1ccc(S(F)(F)(F)(F)F)cc1)C(C(=O)NC1CCOCC1)c1cccnc1] |
TABLE 1-continued
| Exemplary compounds. | |
|---|---|
| Cmpd No. | Structure |
| 812 | 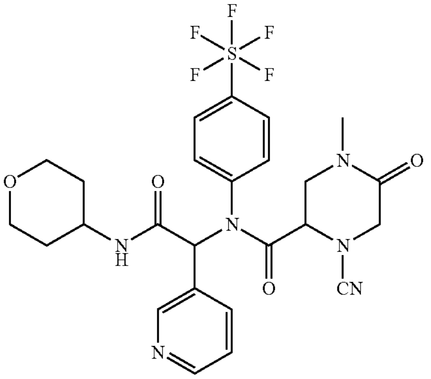 [SMILES: CN1CC(C(=O)N(c2ccc(S(F)(F)(F)(F)F)cc2)C(C(=O)NC2CCOCC2)c2cccnc2)N(C#N)CC1=O] |
| 813 | 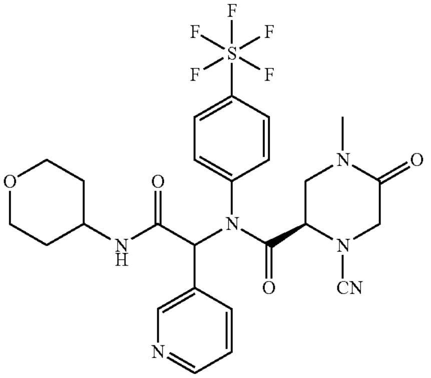 [SMILES: CN1C[C@H](C(=O)N(c2ccc(S(F)(F)(F)(F)F)cc2)C(C(=O)NC2CCOCC2)c2cccnc2)N(C#N)CC1=O] |
| 814 | 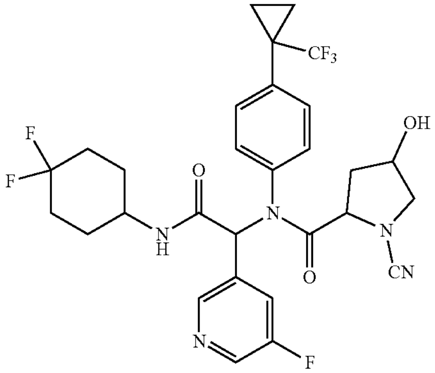 [SMILES: N#CN1CC(O)CC1C(=O)N(c1ccc(C2(C(F)(F)F)CC2)cc1)C(C(=O)NC1CCC(F)(F)CC1)c1cncc(F)c1] |
| 815 | 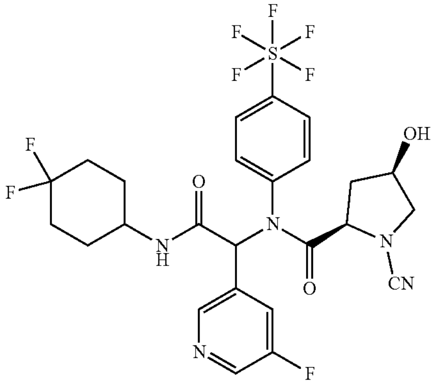 [SMILES: N#CN1C[C@H](O)C[C@@H]1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 815a | 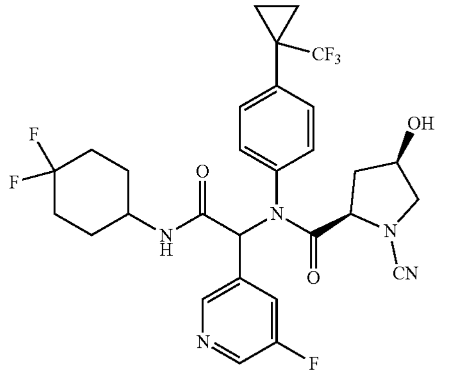 [SMILES: N#CN1C[C@H](O)C[C@@H]1C(=O)N(c1ccc(C2(C(F)(F)F)CC2)cc1)C(C(=O)NC1CCC(F)(F)CC1)c1cncc(F)c1] |
| 816 | 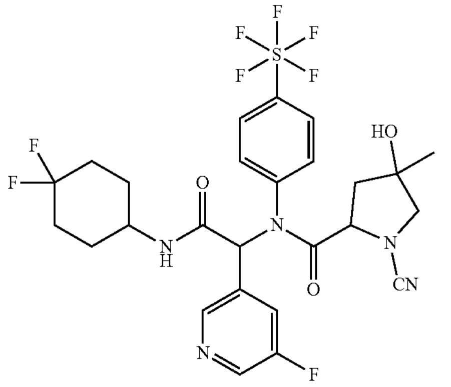 [SMILES: CC1(O)CC(C(=O)N(c2ccc(S(F)(F)(F)(F)F)cc2)C(C(=O)NC2CCC(F)(F)CC2)c2cncc(F)c2)N(C#N)C1] |
| 817 | 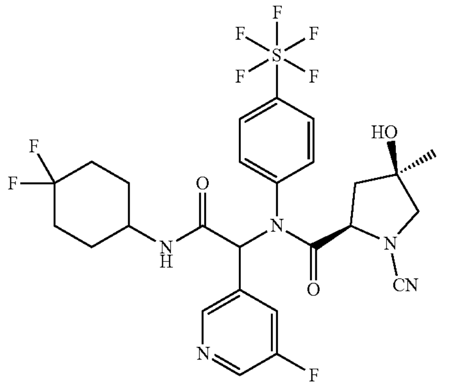 [SMILES: C[C@@]1(O)C[C@H](C(=O)N(c2ccc(S(F)(F)(F)(F)F)cc2)C(C(=O)NC2CCC(F)(F)CC2)c2cncc(F)c2)N(C#N)C1] |
| 818 | 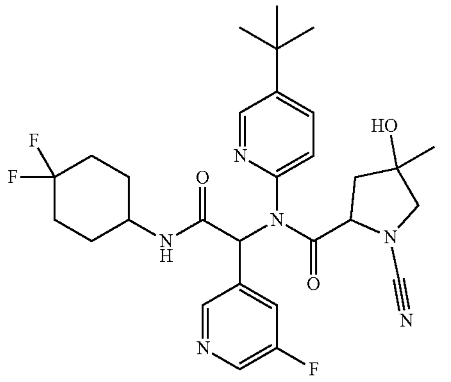 [SMILES: CC1(O)CC(C(=O)N(c2ccc(C(C)(C)C)cn2)C(C(=O)NC2CCC(F)(F)CC2)c2cncc(F)c2)N(C#N)C1] |
TABLE 1-continued
| Exemplary compounds. | |
|---|---|
| Cmpd No. | Structure |
| 819 | 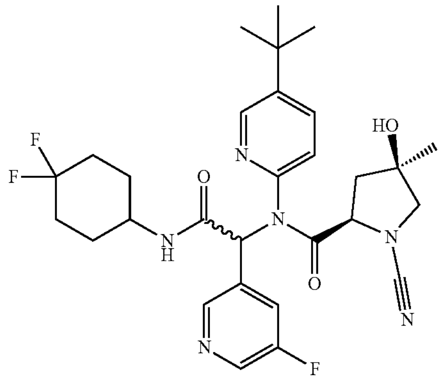 [SMILES: CC(C)(C)c1ccc(N(C(=O)[C@H]2C[C@@](C)(O)CN2C#N)C(C(=O)NC2CCC(F)(F)CC2)c2cncc(F)c2)nc1] |
| 820 | 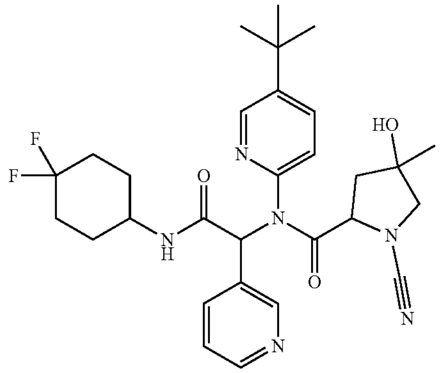 [SMILES: CC1(O)CC(C(=O)N(c2ccc(C(C)(C)C)cn2)C(C(=O)NC2CCC(F)(F)CC2)c2cccnc2)N(C#N)C1] |
| 821 | 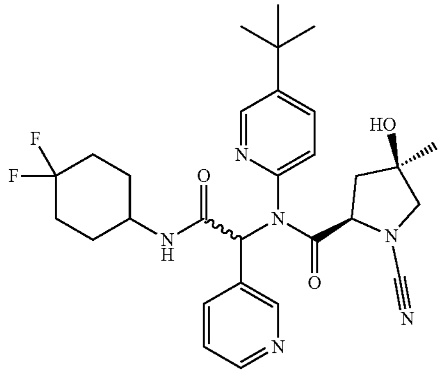 [SMILES: CC(C)(C)c1ccc(N(C(=O)[C@H]2C[C@@](C)(O)CN2C#N)C(C(=O)NC2CCC(F)(F)CC2)c2cccnc2)nc1] |
| 822 | 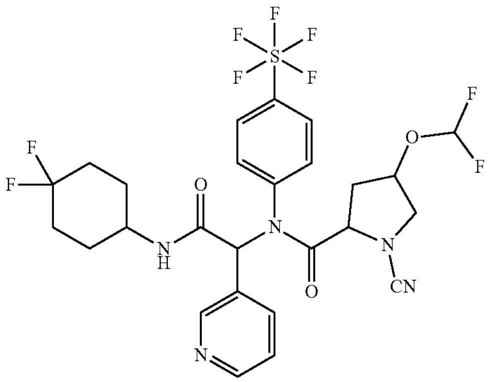 [SMILES: N#CN1CC(OC(F)F)CC1C(=O)N(c1ccc(S(F)(F)(F)(F)F)cc1)C(C(=O)NC1CCC(F)(F)CC1)c1cccnc1] |

TABLE 1-continued
| Exemplary compounds. | |
|---|---|
| Cmpd No. | Structure |
| 823 | 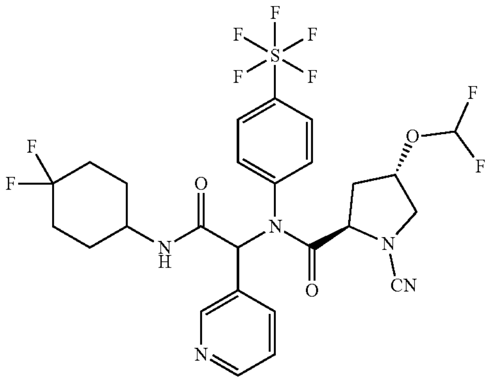 [SMILES: N#CN1C[C@@H](OC(F)F)C[C@@H]1C(=O)N(c1ccc(S(F)(F)(F)(F)F)cc1)C(C(=O)NC1CCC(F)(F)CC1)c1cccnc1] |
| 824 | 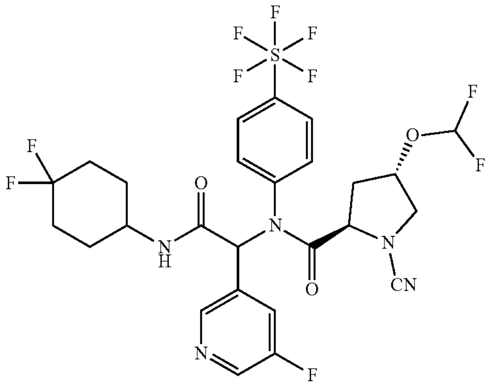 [SMILES: N#CN1C[C@@H](OC(F)F)C[C@@H]1C(=O)N(c1ccc(S(F)(F)(F)(F)F)cc1)C(C(=O)NC1CCC(F)(F)CC1)c1cncc(F)c1] |
| 825 | 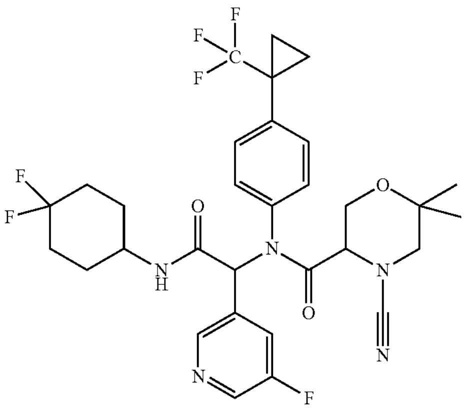 [SMILES: CC1(C)CN(C#N)C(C(=O)N(c2ccc(C3(C(F)(F)F)CC3)cc2)C(C(=O)NC2CCC(F)(F)CC2)c2cncc(F)c2)CO1] |
| 826 | 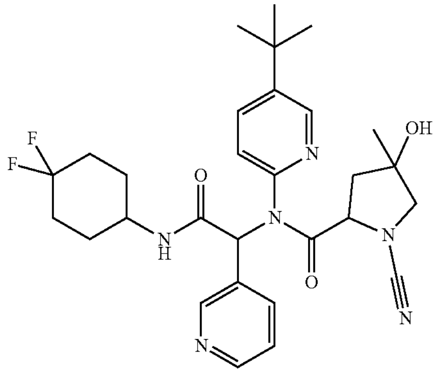 [SMILES: CC1(O)CC(C(=O)N(c2ccc(C(C)(C)C)cn2)C(C(=O)NC2CCC(F)(F)CC2)c2cccnc2)N(C#N)C1] |
| 827 | 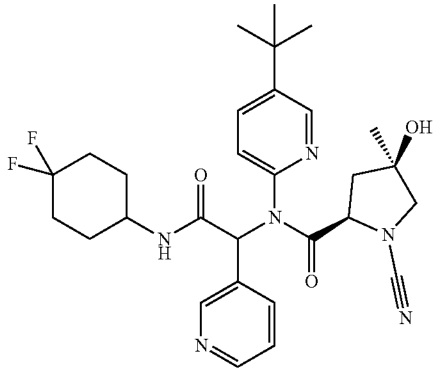 [SMILES: CC(C)(C)c1ccc(N(C(=O)[C@H]2C[C@@](C)(O)CN2C#N)C(C(=O)NC2CCC(F)(F)CC2)c2cccnc2)nc1] |
| 828 | 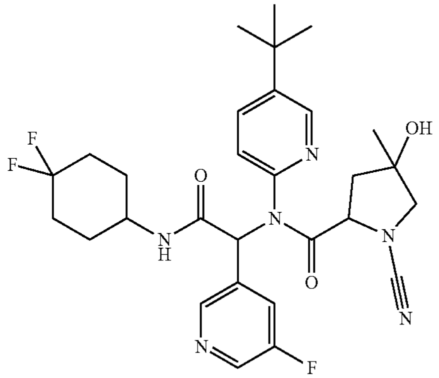 [SMILES: CC1(O)CC(C(=O)N(c2ccc(C(C)(C)C)cn2)C(C(=O)NC2CCC(F)(F)CC2)c2cncc(F)c2)N(C#N)C1] |
| 829 | 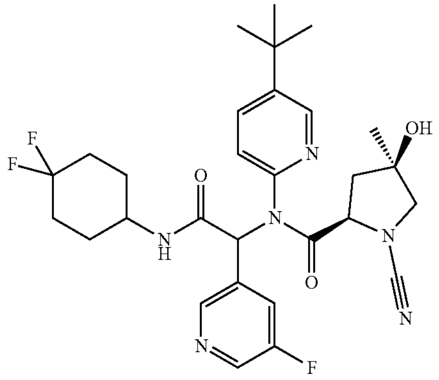 [SMILES: CC(C)(C)c1ccc(N(C(=O)[C@H]2C[C@@](C)(O)CN2C#N)C(C(=O)NC2CCC(F)(F)CC2)c2cncc(F)c2)nc1] |

TABLE 1-continued
| Exemplary compounds. | |
|---|---|
| Cmpd No. | Structure |
| 830 | 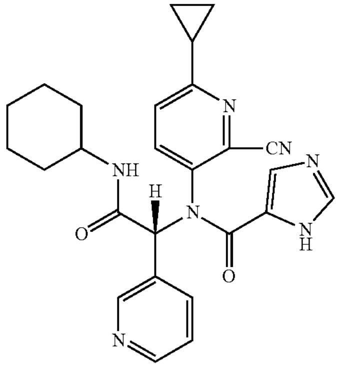 [SMILES: N#Cc1nc(C2CC2)ccc1N(C(=O)c1cnc[nH]1)[C@@H](C(=O)NC1CCCCC1)c1cccnc1] |
| 831 | 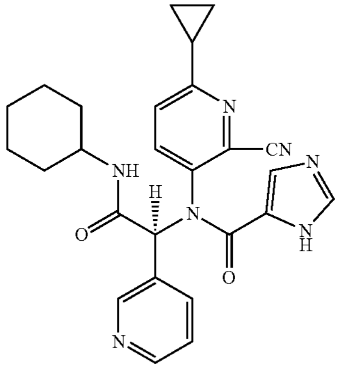 [SMILES: N#Cc1nc(C2CC2)ccc1N(C(=O)c1cnc[nH]1)[C@H](C(=O)NC1CCCCC1)c1cccnc1] |
| 832 | 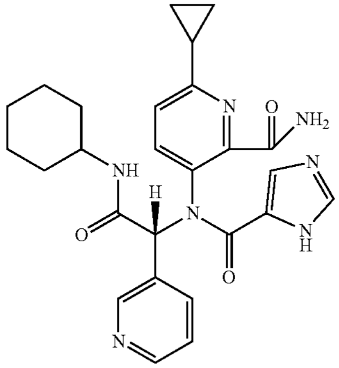 [SMILES: NC(=O)c1nc(C2CC2)ccc1N(C(=O)c1cnc[nH]1)[C@@H](C(=O)NC1CCCCC1)c1cccnc1] |
| 833 | 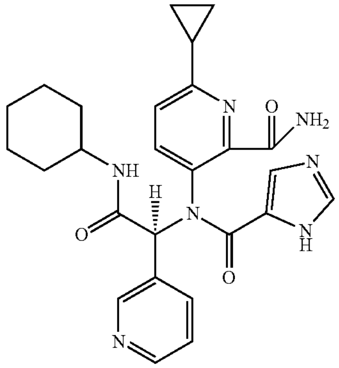 [SMILES: NC(=O)c1nc(C2CC2)ccc1N(C(=O)c1cnc[nH]1)[C@H](C(=O)NC1CCCCC1)c1cccnc1] |
TABLE 1-continued
| Exemplary compounds. | |
|---|---|
| Cmpd No. | Structure |
| 834 | 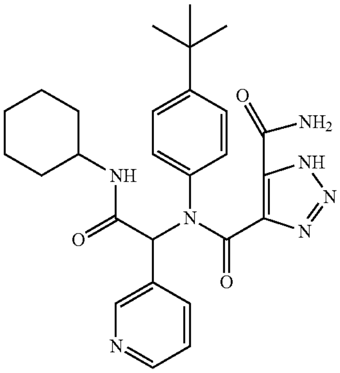 [SMILES: CC(C)(C)c1ccc(N(C(=O)c2nn[nH]c2C(N)=O)C(C(=O)NC2CCCCC2)c2cccnc2)cc1] |
| 835 | 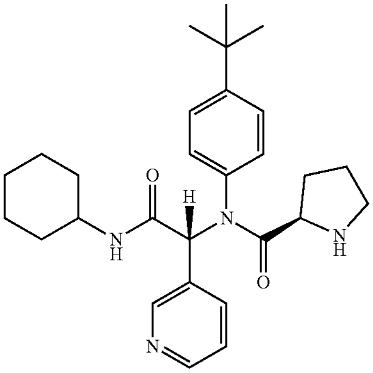 [SMILES: CC(C)(C)c1ccc(N(C(=O)[C@H]2CCCN2)[C@@H](C(=O)NC2CCCCC2)c2cccnc2)cc1] |
| 836 | 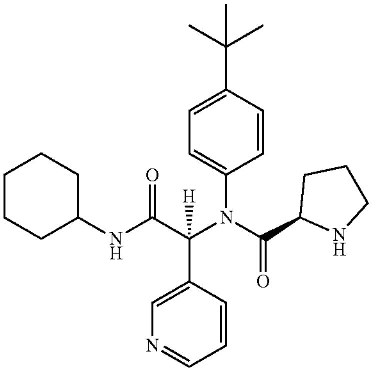 [SMILES: CC(C)(C)c1ccc(N(C(=O)[C@H]2CCCN2)[C@H](C(=O)NC2CCCCC2)c2cccnc2)cc1] |
| 837 | 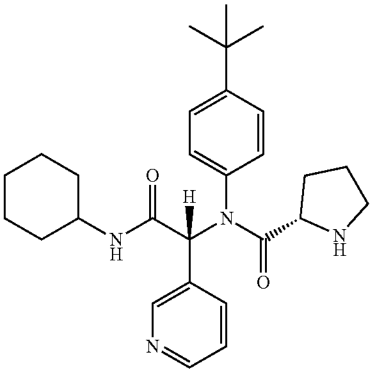 [SMILES: CC(C)(C)c1ccc(N(C(=O)[C@@H]2CCCN2)[C@@H](C(=O)NC2CCCCC2)c2cccnc2)cc1] |

TABLE 1-continued
| Exemplary compounds. | |
|---|---|
| Cmpd No. | Structure |
| 838 | 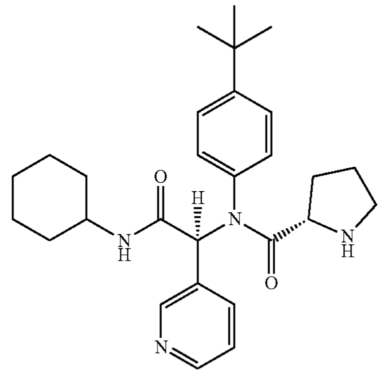 [SMILES: CC(C)(C)c1ccc(N(C(=O)[C@@H]2CCCN2)[C@H](C(=O)NC2CCCCC2)c2cccnc2)cc1] |
| 839 | 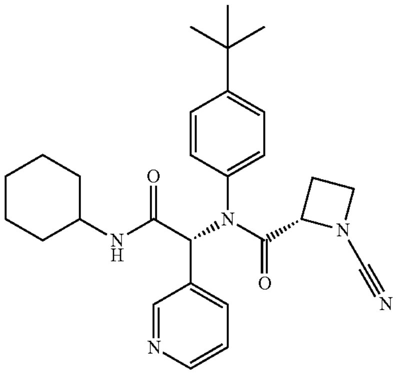 [SMILES: CC(C)(C)c1ccc(N(C(=O)[C@@H]2CCN2C#N)[C@@H](C(=O)NC2CCCCC2)c2cccnc2)cc1] |
| 840 | 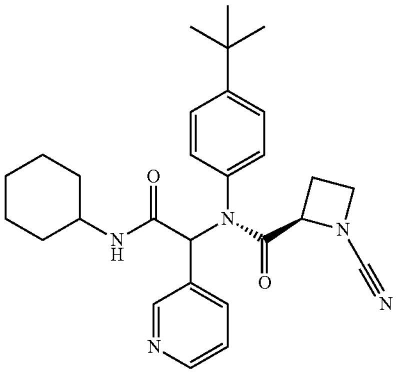 |
| 841 | 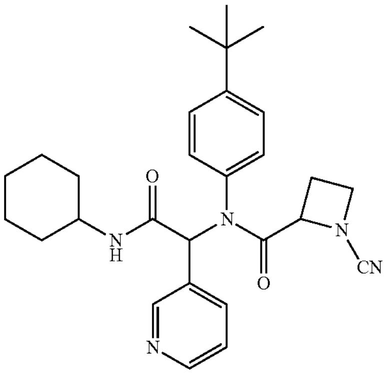 [SMILES: CC(C)(C)c1ccc(N(C(=O)C2CCN2C#N)C(C(=O)NC2CCCCC2)c2cccnc2)cc1] |
TABLE 1-continued
| Exemplary compounds. | |
|---|---|
| Cmpd No. | Structure |
| 841a | 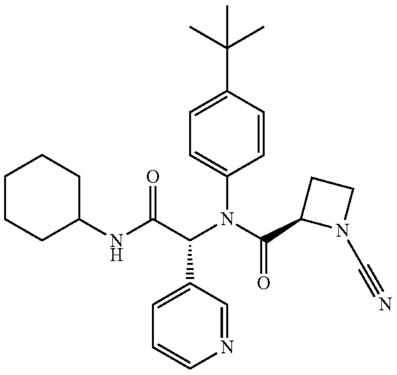 [SMILES: CC(C)(C)c1ccc(N(C(=O)[C@H]2CCN2C#N)[C@@H](C(=O)NC2CCCCC2)c2cccnc2)cc1] |
| 844 | 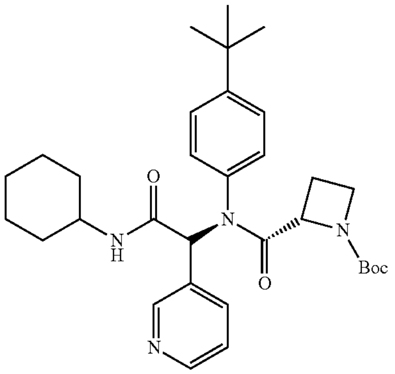 |
| 845 | 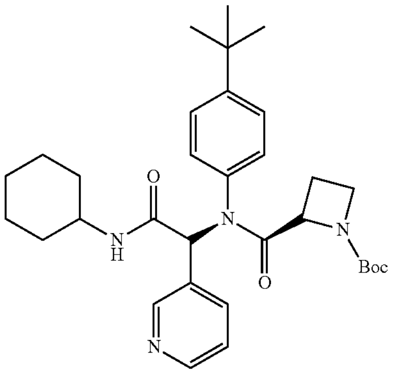 |
| 846 | 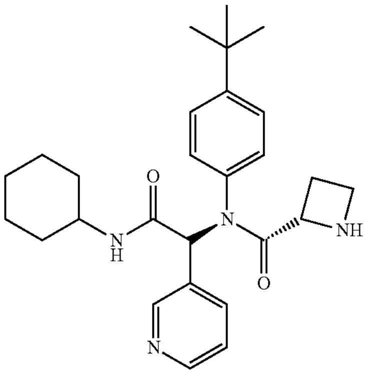 |

TABLE 1-continued
Exemplary compounds.
| Cmpd No. | Structure |
|---|---|
| 847 | 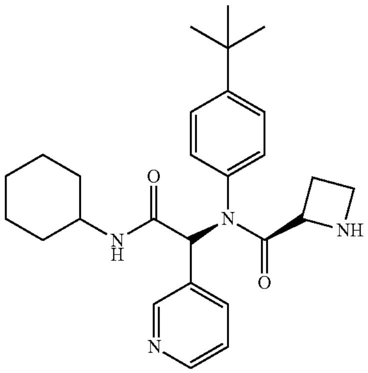 |
| 848 | 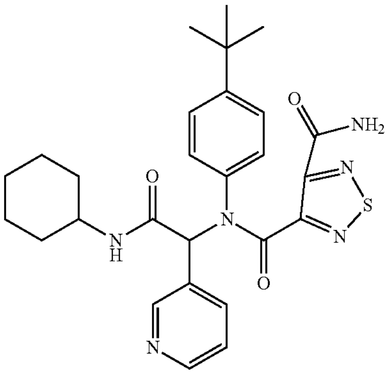 [SMILES: CC(C)(C)c1ccc(N(C(=O)c2nsnc2C(N)=O)C(C(=O)NC2CCCCC2)c2cccnc2)cc1] |
| 849 | 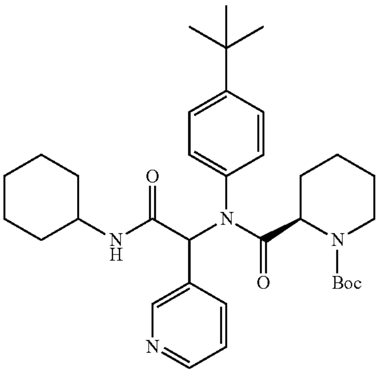 [SMILES: CC(C)(C)OC(=O)N1CCCC[C@@H]1C(=O)N(c1ccc(C(C)(C)C)cc1)C(C(=O)NC1CCCCC1)c1cccnc1] |
| 850 | 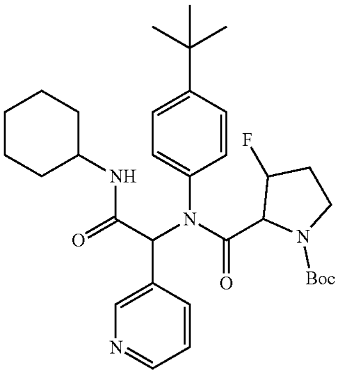 [SMILES: CC(C)(C)OC(=O)N1CCC(F)C1C(=O)N(c1ccc(C(C)(C)C)cc1)C(C(=O)NC1CCCCC1)c1cccnc1] |
| 851 | 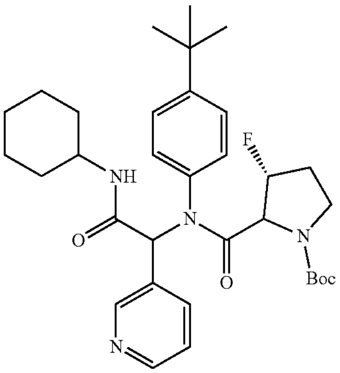 [SMILES: CC(C)(C)OC(=O)N1CC[C@@H](F)C1C(=O)N(c1ccc(C(C)(C)C)cc1)C(C(=O)NC1CCCCC1)c1cccnc1] |
| 852 | 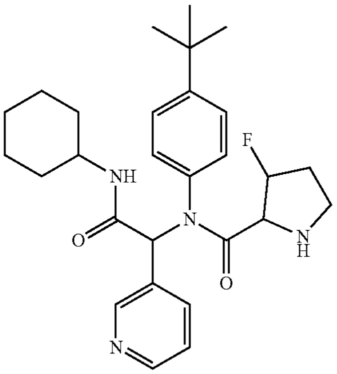 [SMILES: CC(C)(C)c1ccc(N(C(=O)C2NCCC2F)C(C(=O)NC2CCCCC2)c2cccnc2)cc1] |
| 853 | 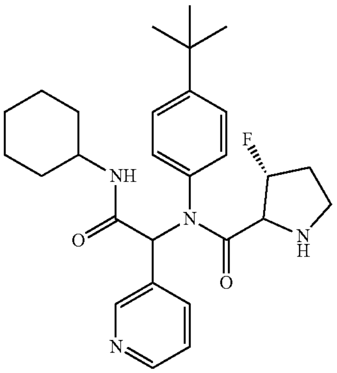 [SMILES: CC(C)(C)c1ccc(N(C(=O)C2NCC[C@H]2F)C(C(=O)NC2CCCCC2)c2cccnc2)cc1] |
| 854 | 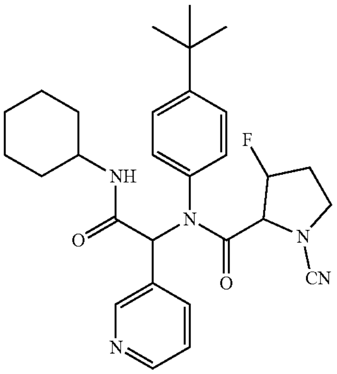 [SMILES: CC(C)(C)c1ccc(N(C(=O)C2C(F)CCN2C#N)C(C(=O)NC2CCCCC2)c2cccnc2)cc1] |

TABLE 1-continued
| Exemplary compounds. | |
|---|---|
| Cmpd No. | Structure |
| 855 | 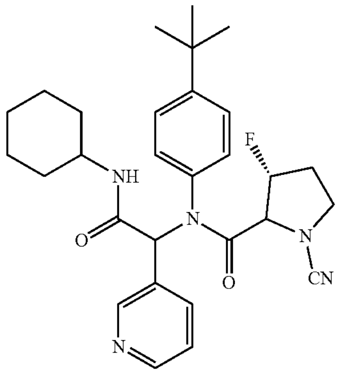 [SMILES: CC(C)(C)c1ccc(N(C(=O)C2[C@H](F)CCN2C#N)C(C(=O)NC2CCCCC2)c2cccnc2)cc1] |
| 856 | 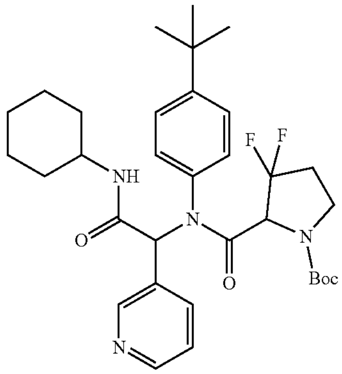 [SMILES: CC(C)(C)OC(=O)N1CCC(F)(F)C1C(=O)N(c1ccc(C(C)(C)C)cc1)C(C(=O)NC1CCCCC1)c1cccnc1] |
| 857 | 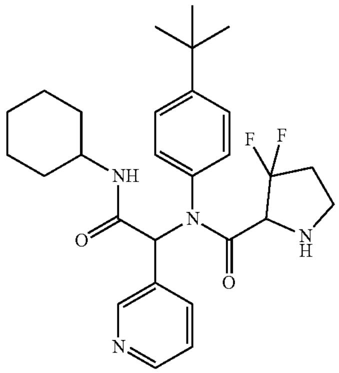 [SMILES: CC(C)(C)c1ccc(N(C(=O)C2NCCC2(F)F)C(C(=O)NC2CCCCC2)c2cccnc2)cc1] |
| 858 | 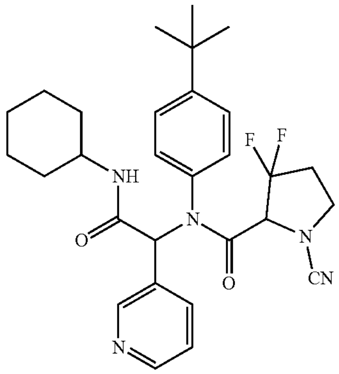 |
TABLE 1-continued
| Exemplary compounds. | |
|---|---|
| Cmpd No. | Structure |
| 859 | 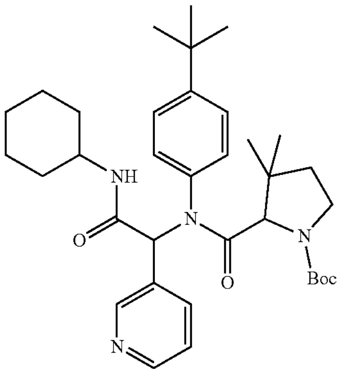 [SMILES: CC(C)(C)OC(=O)N1CCC(C)(C)C1C(=O)N(c1ccc(C(C)(C)C)cc1)C(C(=O)NC1CCCCC1)c1cccnc1] |
| 860 | 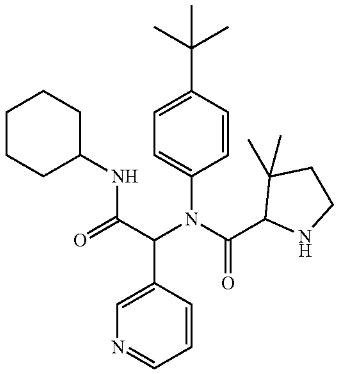 [SMILES: CC(C)(C)c1ccc(N(C(=O)C2NCCC2(C)C)C(C(=O)NC2CCCCC2)c2cccnc2)cc1] |
| 861 | 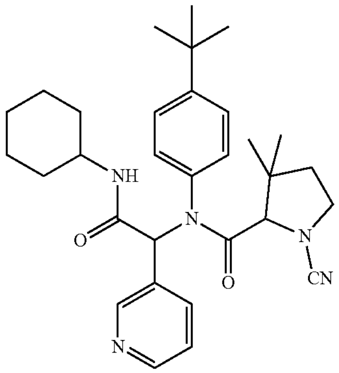 [SMILES: CC(C)(C)c1ccc(N(C(=O)C2N(C#N)CCC2(C)C)C(C(=O)NC2CCCCC2)c2cccnc2)cc1] |
| 862 | 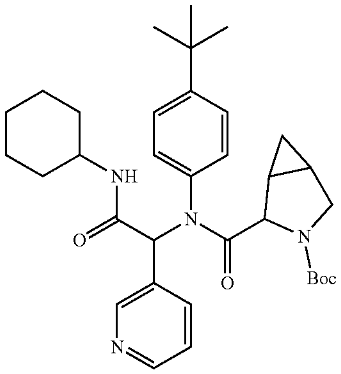 [SMILES: CC(C)(C)OC(=O)N1CC2CC2C1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 863 | 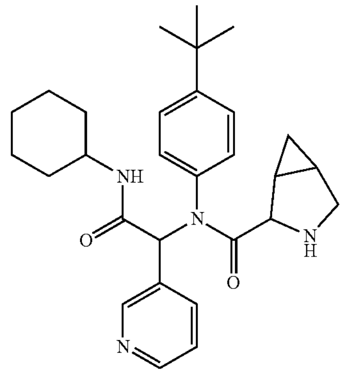 [SMILES: CC(C)(C)c1ccc(N(C(=O)C2NCC3CC32)C(C(=O)NC2CCCCC2)c2cccnc2)cc1] |
| 864 | 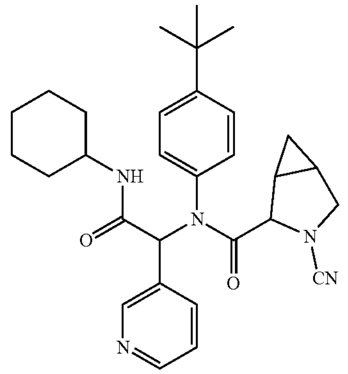 [SMILES: CC(C)(C)c1ccc(N(C(=O)C2C3CC3CN2C#N)C(C(=O)NC2CCCCC2)c2cccnc2)cc1] |
| 864a | 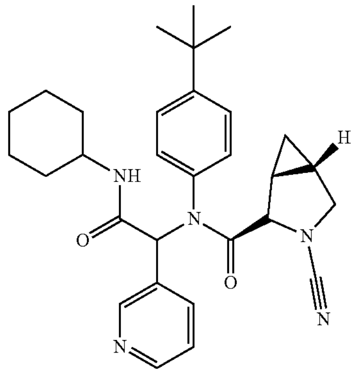 |
| 864b | 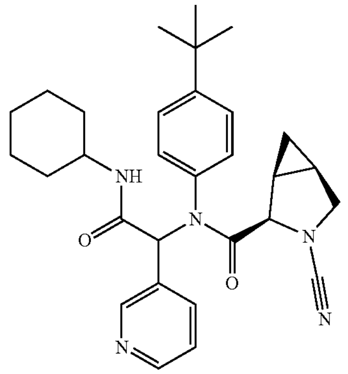 [SMILES: CC(C)(C)c1ccc(N(C(=O)[C@H]2[C@H]3C[C@H]3CN2C#N)C(C(=O)NC2CCCCC2)c2cccnc2)cc1] |
TABLE 1-continued
| Exemplary compounds. | |
|---|---|
| Cmpd No. | Structure |
| 865 | 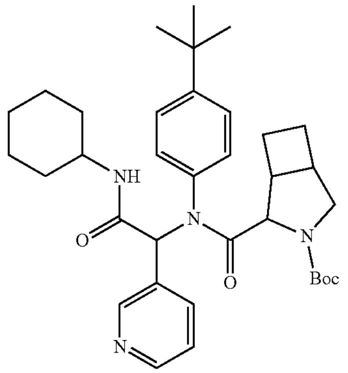 [SMILES: CC(C)(C)OC(=O)N1CC2CCC2C1C(=O)N(c1ccc(C(C)(C)C)cc1)C(C(=O)NC1CCCCC1)c1cccnc1] |
| 866 | 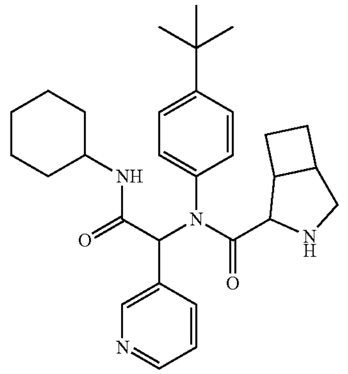 [SMILES: CC(C)(C)c1ccc(N(C(=O)C2NCC3CCC32)C(C(=O)NC2CCCCC2)c2cccnc2)cc1] |
| 867 | 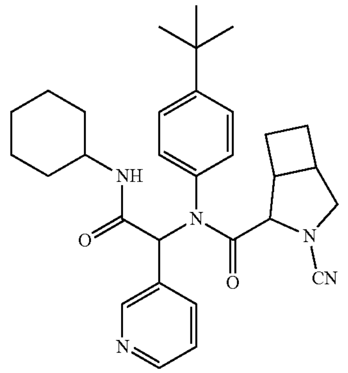 [SMILES: CC(C)(C)c1ccc(N(C(=O)C2C3CCC3CN2C#N)C(C(=O)NC2CCCCC2)c2cccnc2)cc1] |
| 868 | 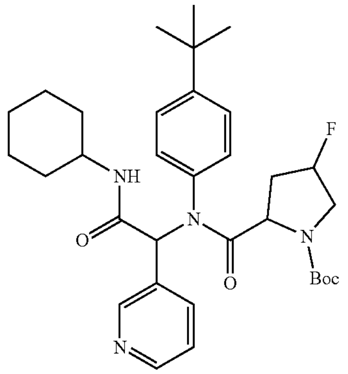 [SMILES: CC(C)(C)OC(=O)N1CC(F)CC1C(=O)N(c1ccc(C(C)(C)C)cc1)C(C(=O)NC1CCCCC1)c1cccnc1] |

TABLE 1-continued
Exemplary compounds.
| Cmpd No. | Structure |
|---|---|
| 869 | 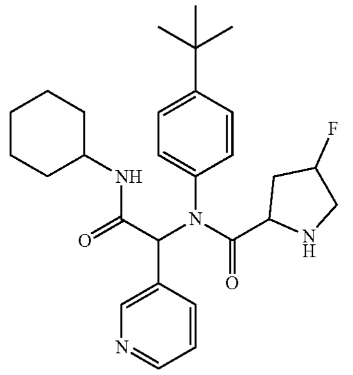 [SMILES: CC(C)(C)c1ccc(N(C(=O)C2CC(F)CN2)C(C(=O)NC2CCCCC2)c2cccnc2)cc1] |
| 870 | 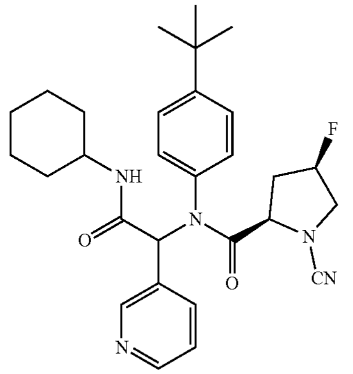 [SMILES: CC(C)(C)c1ccc(N(C(=O)[C@H]2C[C@@H](F)CN2C#N)C(C(=O)NC2CCCCC2)c2cccnc2)cc1] |
| 871 | 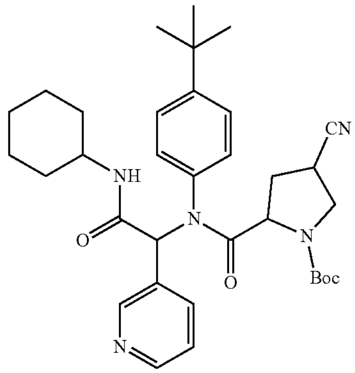 [SMILES: CC(C)(C)OC(=O)N1CC(C#N)CC1C(=O)N(c1ccc(C(C)(C)C)cc1)C(C(=O)NC1CCCCC1)c1cccnc1] |
| 872 | 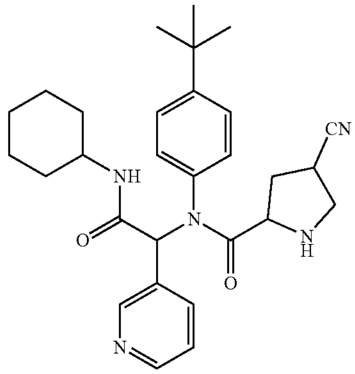 [SMILES: CC(C)(C)c1ccc(N(C(=O)C2CC(C#N)CN2)C(C(=O)NC2CCCCC2)c2cccnc2)cc1] |
TABLE 1-continued
Exemplary compounds.
| Cmpd No. | Structure |
|---|---|
| 873 | 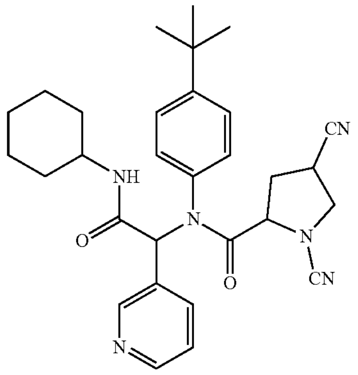 [SMILES: CC(C)(C)c1ccc(N(C(=O)C2CC(C#N)CN2C#N)C(C(=O)NC2CCCCC2)c2cccnc2)cc1] |
| 874 | 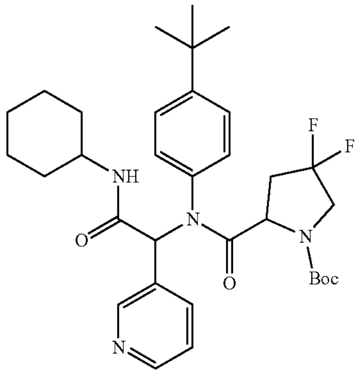 [SMILES: CC(C)(C)OC(=O)N1CC(F)(F)CC1C(=O)N(c1ccc(C(C)(C)C)cc1)C(C(=O)NC1CCCCC1)c1cccnc1] |
| 875 | 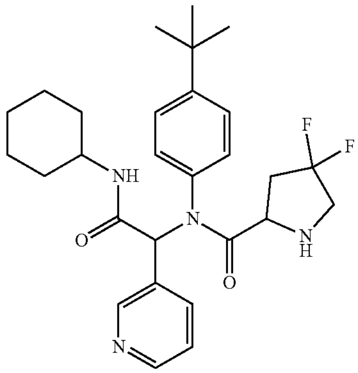 [SMILES: CC(C)(C)c1ccc(N(C(=O)C2CC(F)(F)CN2)C(C(=O)NC2CCCCC2)c2cccnc2)cc1] |
| 876 | 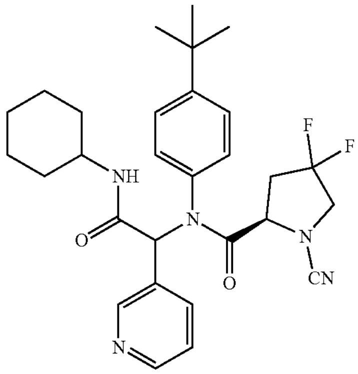 [SMILES: CC(C)(C)c1ccc(N(C(=O)[C@H]2CC(F)(F)CN2C#N)C(C(=O)NC2CCCCC2)c2cccnc2)cc1] |

TABLE 1-continued
| Exemplary compounds. | |
|---|---|
| Cmpd No. | Structure |
| 877 | 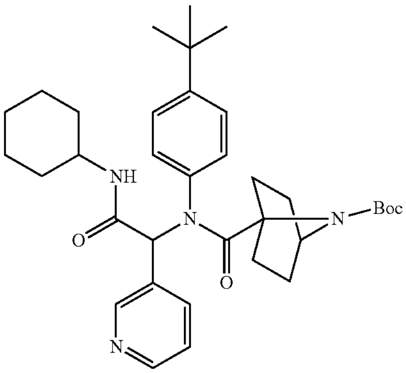 [SMILES: CC(C)(C)OC(=O)N1C2CCC1(C(=O)N(c1ccc(C(C)(C)C)cc1)C(C(=O)NC1CCCCC1)c1cccnc1)CC2] |
| 878 | 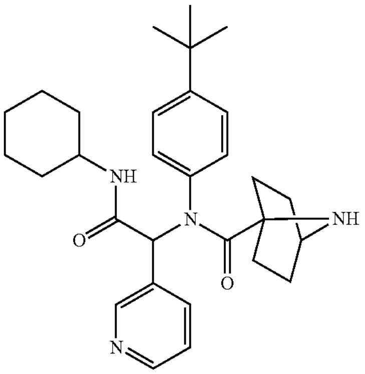 [SMILES: CC(C)(C)c1ccc(N(C(=O)C23CCC(CC2)N3)C(C(=O)NC2CCCCC2)c2cccnc2)cc1] |
| 879 | 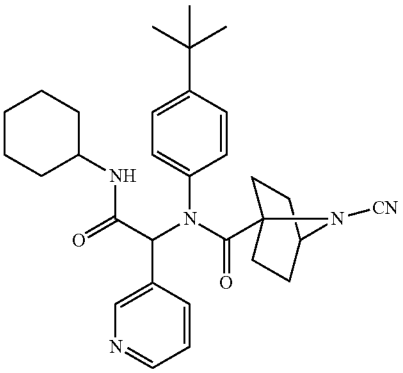 [SMILES: CC(C)(C)c1ccc(N(C(=O)C23CCC(CC2)N3C#N)C(C(=O)NC2CCCCC2)c2cccnc2)cc1] |
| 880 | 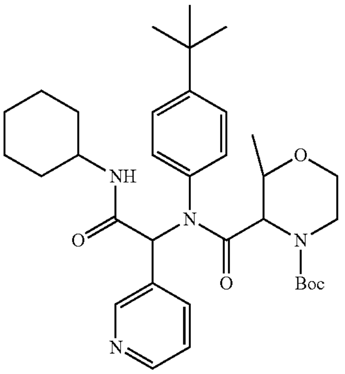 [SMILES: CC1OCCN(C(=O)OC(C)(C)C)C1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 881 | 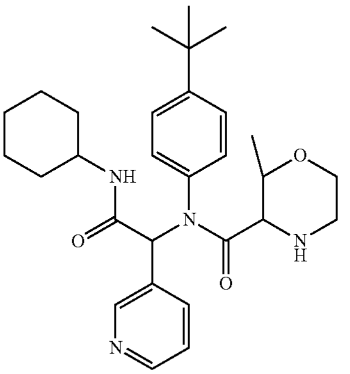 [SMILES: CC1OCCNC1C(=O)N(c1ccc(C(C)(C)C)cc1)C(C(=O)NC1CCCCC1)c1cccnc1] |
| 882 | 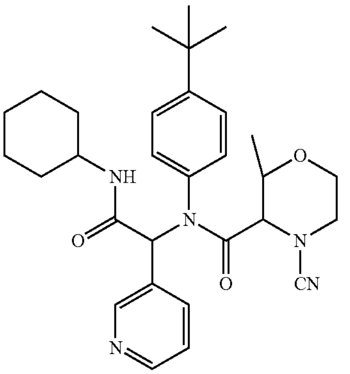 [SMILES: CC1OCCN(C#N)C1C(=O)N(c1ccc(C(C)(C)C)cc1)C(C(=O)NC1CCCCC1)c1cccnc1] |
| 883 | 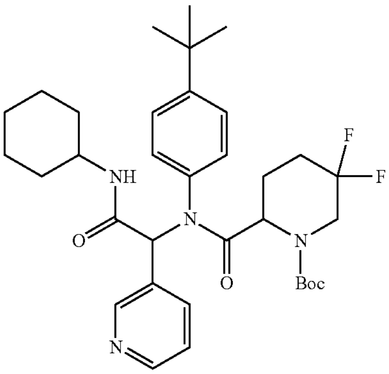 [SMILES: CC(C)(C)OC(=O)N1CC(F)(F)CCC1C(=O)N(c1ccc(C(C)(C)C)cc1)C(C(=O)NC1CCCCC1)c1cccnc1] |
| 884 | 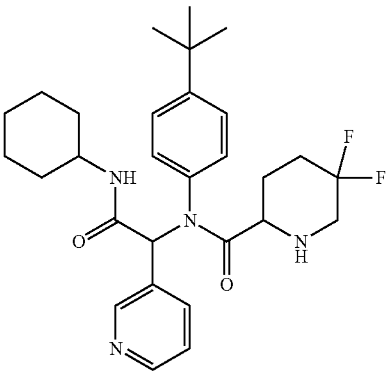 [SMILES: CC(C)(C)c1ccc(N(C(=O)C2CCC(F)(F)CN2)C(C(=O)NC2CCCCC2)c2cccnc2)cc1] |

TABLE 1-continued
Exemplary compounds.
| Cmpd No. | Structure |
|---|---|
| 885 | 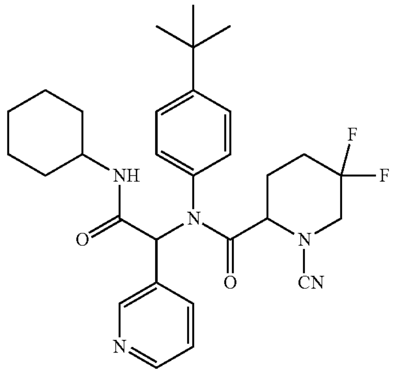 [SMILES: CC(C)(C)c1ccc(N(C(=O)C2CCC(F)(F)CN2C#N)C(C(=O)NC2CCCCC2)c2cccnc2)cc1] |
| 886 | 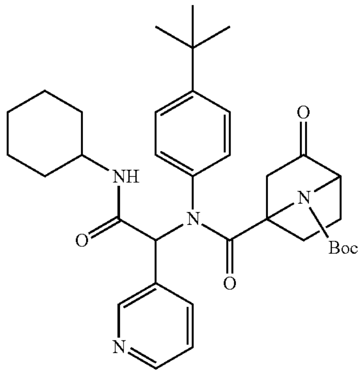 [SMILES: CC(C)(C)OC(=O)N1C2CCC1(C(=O)N(c1ccc(C(C)(C)C)cc1)C(C(=O)NC1CCCCC1)c1cccnc1)CC2=O] |
| 887 | 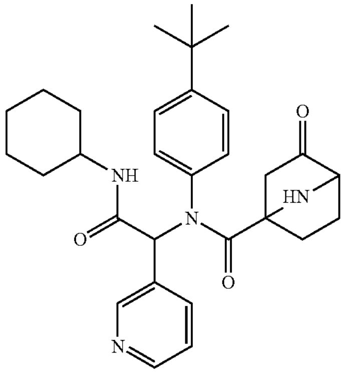 [SMILES: CC(C)(C)c1ccc(N(C(=O)C23CCC(N2)C(=O)C3)C(C(=O)NC2CCCCC2)c2cccnc2)cc1] |
| 888 | 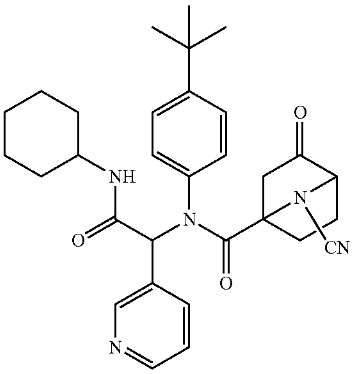 [SMILES: CC(C)(C)c1ccc(N(C(=O)C23CCC(C(=O)C2)N3C#N)C(C(=O)NC2CCCCC2)c2cccnc2)cc1] |
| 889 | 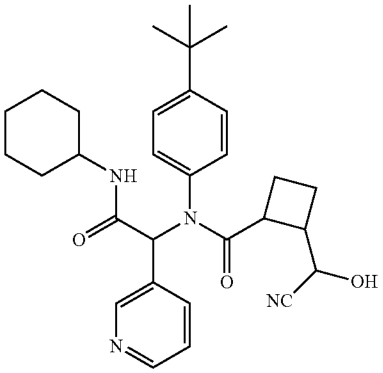 [SMILES: CC(C)(C)c1ccc(N(C(=O)C2CCC2C(O)C#N)C(C(=O)NC2CCCCC2)c2cccnc2)cc1] |
| 890 | 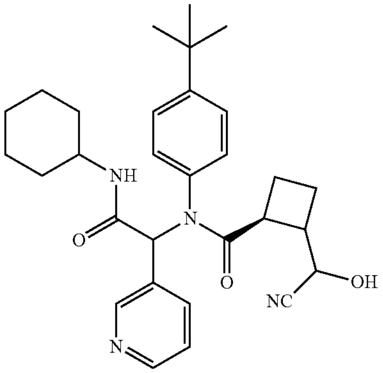 [SMILES: CC(C)(C)c1ccc(N(C(=O)[C@H]2CCC2C(O)C#N)C(C(=O)NC2CCCCC2)c2cccnc2)cc1] |
| 891 | 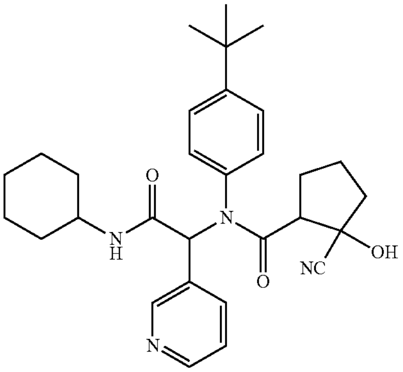 [SMILES: CC(C)(C)c1ccc(N(C(=O)C2CCCC2(O)C#N)C(C(=O)NC2CCCCC2)c2cccnc2)cc1] |
| 892 | 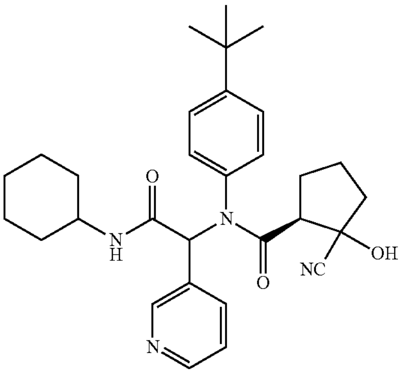 [SMILES: CC(C)(C)c1ccc(N(C(=O)[C@H]2CCCC2(O)C#N)C(C(=O)NC2CCCCC2)c2cccnc2)cc1] |

TABLE 1-continued
| Exemplary compounds. | |
|---|---|
| Cmpd No. | Structure |
| 893 | 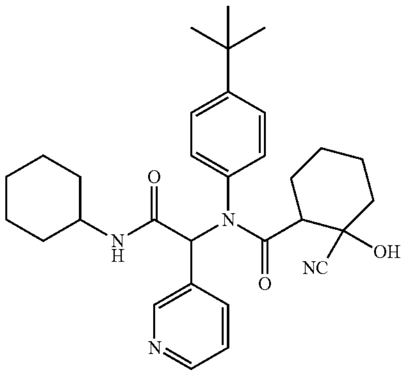 [SMILES: CC(C)(C)c1ccc(N(C(=O)C2CCCCC2(O)C#N)C(C(=O)NC2CCCCC2)c2cccnc2)cc1] |
| 894 | 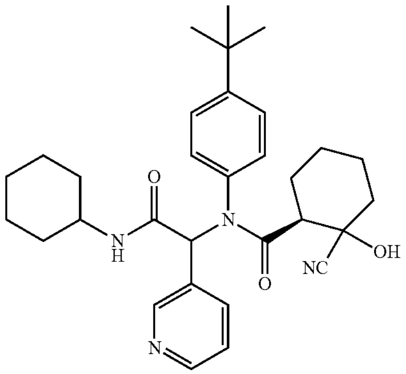 [SMILES: CC(C)(C)c1ccc(N(C(=O)[C@H]2CCCCC2(O)C#N)C(C(=O)NC2CCCCC2)c2cccnc2)cc1] |
| 895 | 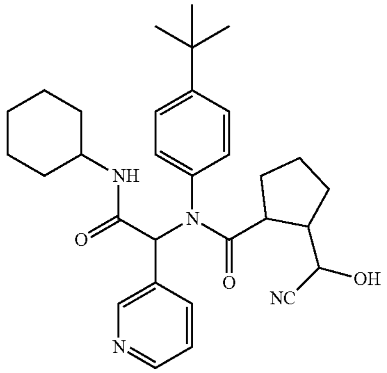 [SMILES: CC(C)(C)c1ccc(N(C(=O)C2CCCC2C(O)C#N)C(C(=O)NC2CCCCC2)c2cccnc2)cc1] |
| 896 | 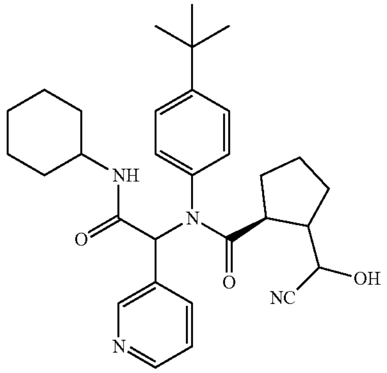 [SMILES: CC(C)(C)c1ccc(N(C(=O)[C@H]2CCCC2C(O)C#N)C(C(=O)NC2CCCCC2)c2cccnc2)cc1] |
TABLE 1-continued
| Exemplary compounds. | |
|---|---|
| Cmpd No. | Structure |
| 897 | 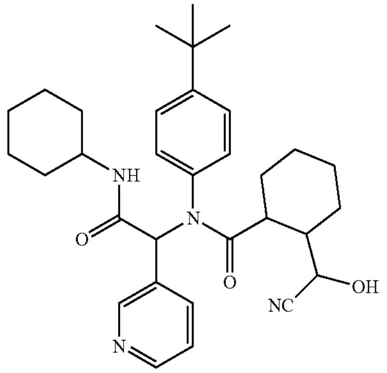 [SMILES: CC(C)(C)c1ccc(N(C(=O)C2CCCCC2C(O)C#N)C(C(=O)NC2CCCCC2)c2cccnc2)cc1] |
| 898 | 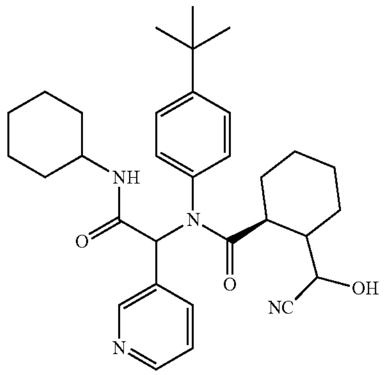 [SMILES: CC(C)(C)c1ccc(N(C(=O)[C@H]2CCCCC2C(O)C#N)C(C(=O)NC2CCCCC2)c2cccnc2)cc1] |
| 899 | 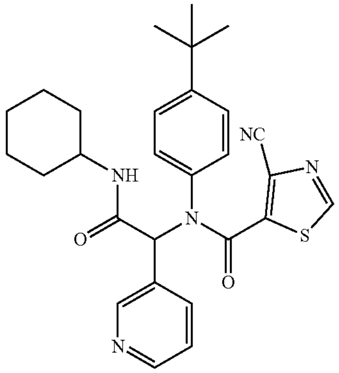 [SMILES: CC(C)(C)c1ccc(N(C(=O)c2scnc2C#N)C(C(=O)NC2CCCCC2)c2cccnc2)cc1] |
| 899a | 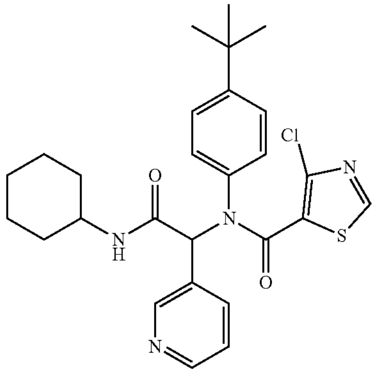 [SMILES: CC(C)(C)c1ccc(N(C(=O)c2scnc2Cl)C(C(=O)NC2CCCCC2)c2cccnc2)cc1] |

TABLE 1-continued
Exemplary compounds.
| Cmpd No. | Structure |
|---|---|
| 900 | 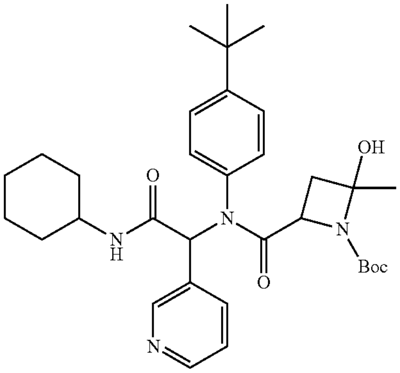 [SMILES: CC(C)(C)OC(=O)N1C(C(=O)N(c2ccc(C(C)(C)C)cc2)C(C(=O)NC2CCCCC2)c2cccnc2)CC1(C)O] |
| 901 | 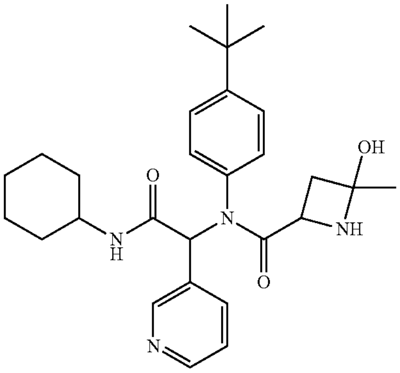 [SMILES: CC1(O)CC(C(=O)N(c2ccc(C(C)(C)C)cc2)C(C(=O)NC2CCCCC2)c2cccnc2)N1] |
| 902 | 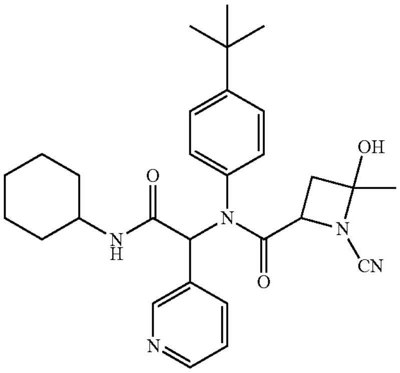 [SMILES: CC(C)(C)c1ccc(N(C(=O)C2CC(C)(O)N2C#N)C(C(=O)NC2CCCCC2)c2cccnc2)cc1] |
| 903 | 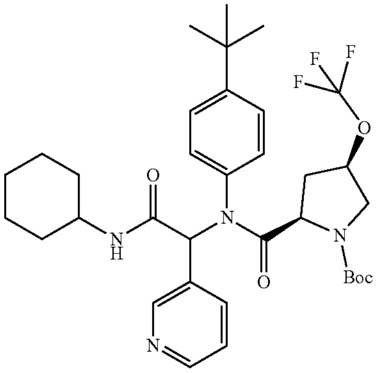 [SMILES: CC(C)(C)OC(=O)N1C[C@H](OC(F)(F)F)C[C@@H]1C(=O)N(c1ccc(C(C)(C)C)cc1)C(C(=O)NC1CCCCC1)c1cccnc1] |
TABLE 1-continued
Exemplary compounds.
| Cmpd No. | Structure |
|---|---|
| 904 | 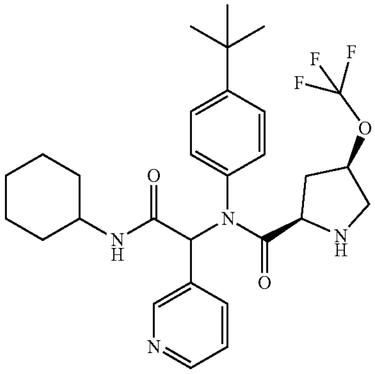 [SMILES: CC(C)(C)c1ccc(N(C(=O)[C@H]2C[C@@H](OC(F)(F)F)CN2)C(C(=O)NC2CCCCC2)c2cccnc2)cc1] |
| 905 | 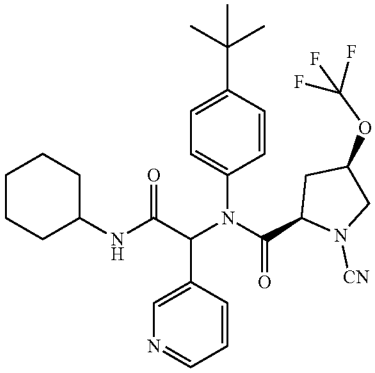 [SMILES: CC(C)(C)c1ccc(N(C(=O)[C@H]2C[C@@H](OC(F)(F)F)CN2C#N)C(C(=O)NC2CCCCC2)c2cccnc2)cc1] |
| 906 | 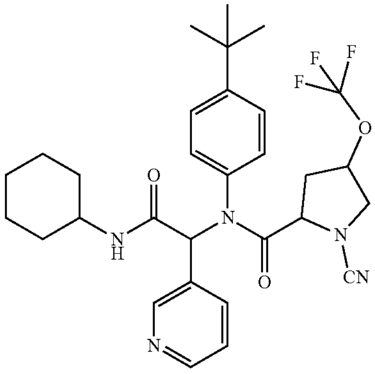 [SMILES: CC(C)(C)c1ccc(N(C(=O)C2CC(OC(F)(F)F)CN2C#N)C(C(=O)NC2CCCCC2)c2cccnc2)cc1] |
| 907 | 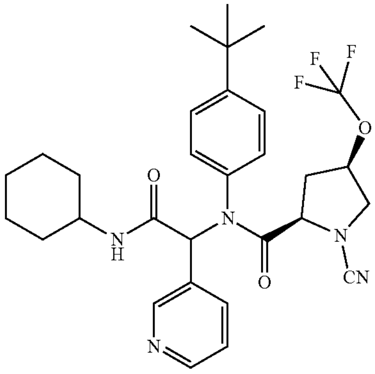 [SMILES: CC(C)(C)c1ccc(N(C(=O)[C@H]2C[C@@H](OC(F)(F)F)CN2C#N)C(C(=O)NC2CCCCC2)c2cccnc2)cc1] |

TABLE 1-continued
| Cmpd No. | Structure |
|---|---|
| 908 | 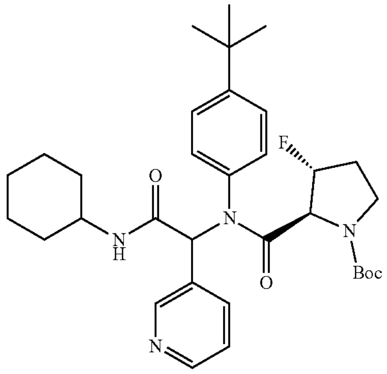 [SMILES: CC(C)(C)OC(=O)N1CC[C@@H](F)[C@@H]1C(=O)N(c1ccc(C(C)(C)C)cc1)C(C(=O)NC1CCCCC1)c1cccnc1] |
| 909 | 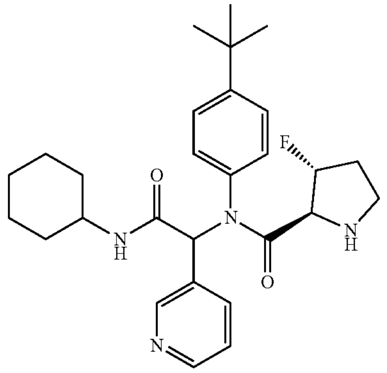 [SMILES: CC(C)(C)c1ccc(N(C(=O)[C@@H]2NCC[C@H]2F)C(C(=O)NC2CCCCC2)c2cccnc2)cc1] |
| 901a | 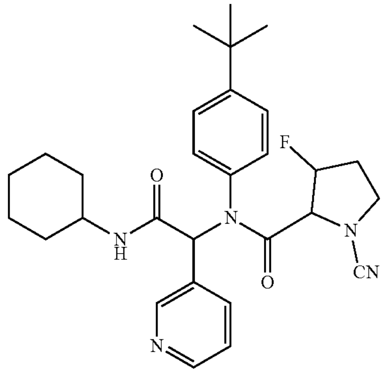 [SMILES: CC(C)(C)c1ccc(N(C(=O)C2C(F)CCN2C#N)C(C(=O)NC2CCCCC2)c2cccnc2)cc1] |
| 910 | 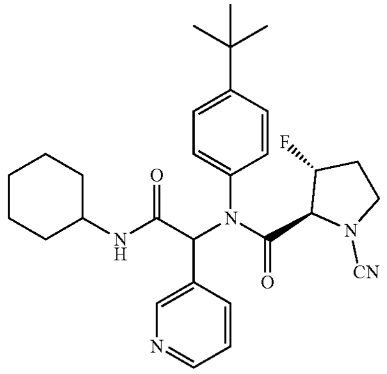 [SMILES: CC(C)(C)c1ccc(N(C(=O)[C@H]2[C@H](F)CCN2C#N)C(C(=O)NC2CCCCC2)c2cccnc2)cc1] |
| 911 | 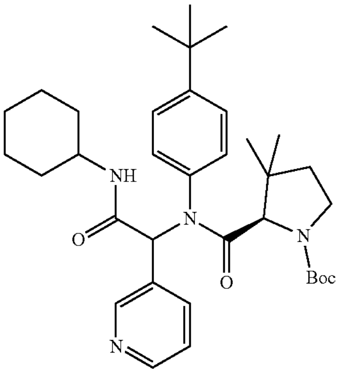 [SMILES: CC(C)(C)OC(=O)N1CCC(C)(C)[C@@H]1C(=O)N(c1ccc(C(C)(C)C)cc1)C(C(=O)NC1CCCCC1)c1cccnc1] |
| 912 | 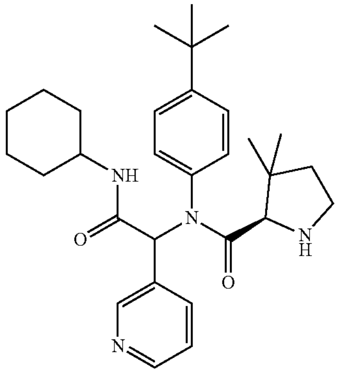 [SMILES: CC(C)(C)c1ccc(N(C(=O)[C@@H]2NCCC2(C)C)C(C(=O)NC2CCCCC2)c2cccnc2)cc1] |
| 913a | 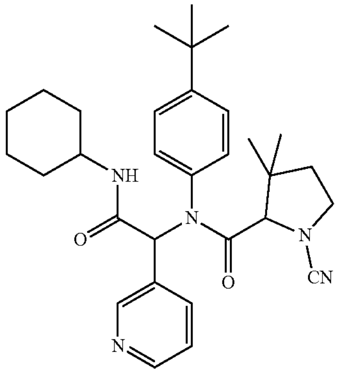 [SMILES: CC(C)(C)c1ccc(N(C(=O)C2N(C#N)CCC2(C)C)C(C(=O)NC2CCCCC2)c2cccnc2)cc1] |
| 913 | 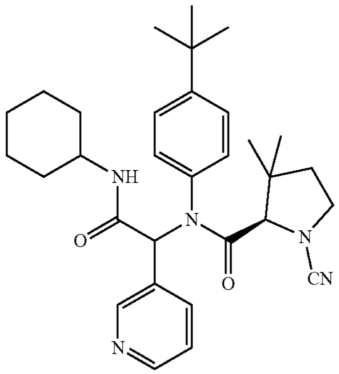 [SMILES: CC(C)(C)c1ccc(N(C(=O)[C@@H]2N(C#N)CCC2(C)C)C(C(=O)NC2CCCCC2)c2cccnc2)cc1] |
Exemplary compounds.

TABLE 1-continued
| Exemplary compounds. | |
|---|---|
| Cmpd No. | Structure |
| 914 | 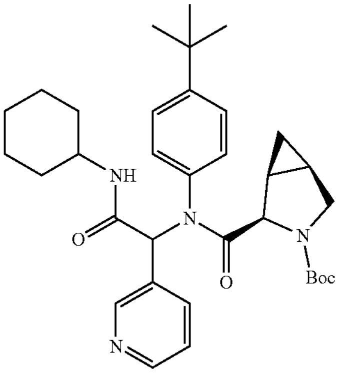 [SMILES: CC(C)(C)OC(=O)N1C[C@@H]2C[C@@H]2[C@@H]1C(=O)N(c1ccc(C(C)(C)C)cc1)C(C(=O)NC1CCCCC1)c1cccnc1] |
| 915 | 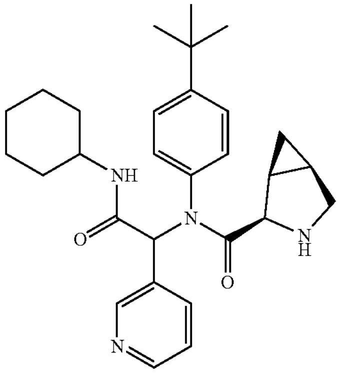 [SMILES: CC(C)(C)c1ccc(N(C(=O)[C@@H]2NC[C@@H]3C[C@@H]32)C(C(=O)NC2CCCCC2)c2cccnc2)cc1] |
| 916a | 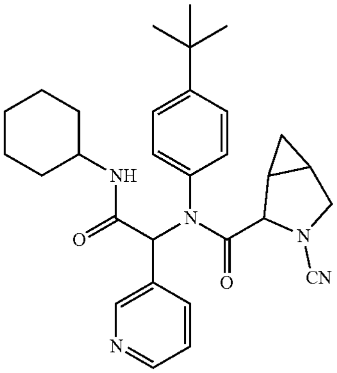 [SMILES: CC(C)(C)c1ccc(N(C(=O)C2C3CC3CN2C#N)C(C(=O)NC2CCCCC2)c2cccnc2)cc1] |
| 916 | 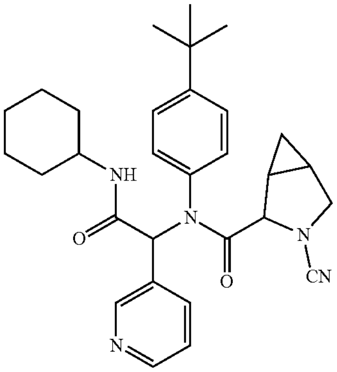 [SMILES: CC(C)(C)c1ccc(N(C(=O)C2C3CC3CN2C#N)C(C(=O)NC2CCCCC2)c2cccnc2)cc1] |
TABLE 1-continued
| Exemplary compounds. | |
|---|---|
| Cmpd No. | Structure |
| 917 | 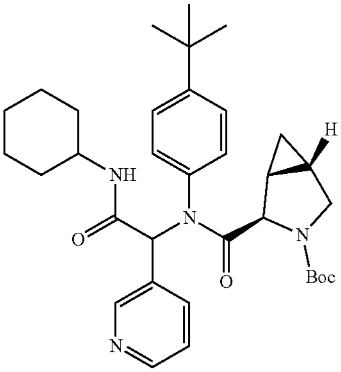 [SMILES: CC(C)(C)OC(=O)N1C[C@H]2C[C@H]2[C@@H]1C(=O)N(c1ccc(C(C)(C)C)cc1)C(C(=O)NC1CCCCC1)c1cccnc1] |
| 918 | 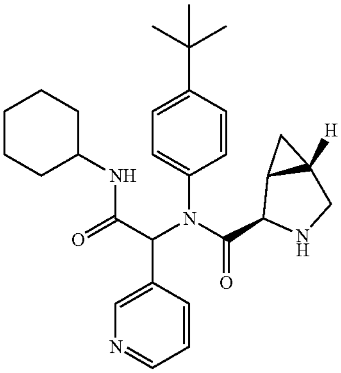 [SMILES: CC(C)(C)c1ccc(N(C(=O)[C@@H]2NC[C@H]3C[C@H]32)C(C(=O)NC2CCCCC2)c2cccnc2)cc1] |
| 919 | 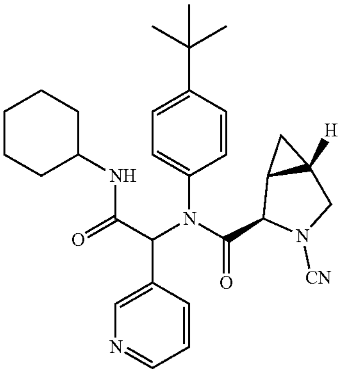 [SMILES: CC(C)(C)c1ccc(N(C(=O)[C@H]2[C@@H]3C[C@@H]3CN2C#N)C(C(=O)NC2CCCCC2)c2cccnc2)cc1] |
| 920 | 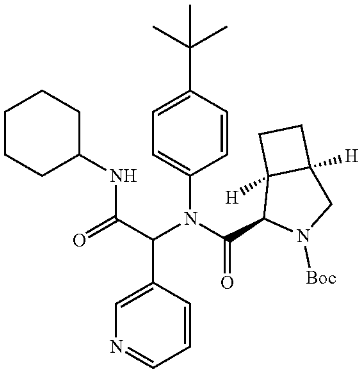 [SMILES: CC(C)(C)OC(=O)N1C[C@@H]2CC[C@@H]2[C@@H]1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 921 | 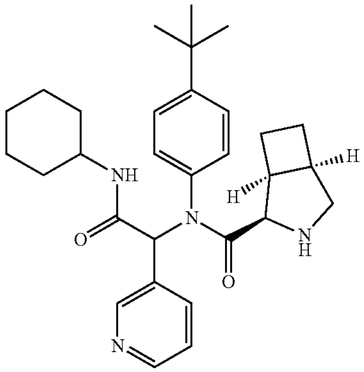 [SMILES: CC(C)(C)c1ccc(N(C(=O)[C@@H]2NC[C@@H]3CC[C@@H]32)C(C(=O)NC2CCCCC2)c2cccnc2)cc1] |
| 922a | 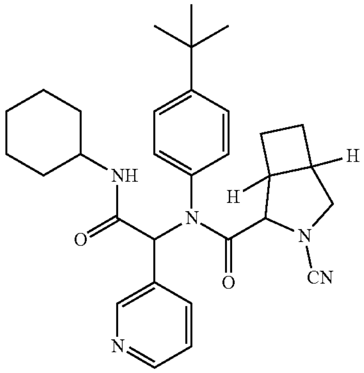 [SMILES: CC(C)(C)c1ccc(N(C(=O)C2C3CCC3CN2C#N)C(C(=O)NC2CCCCC2)c2cccnc2)cc1] |
| 922 | 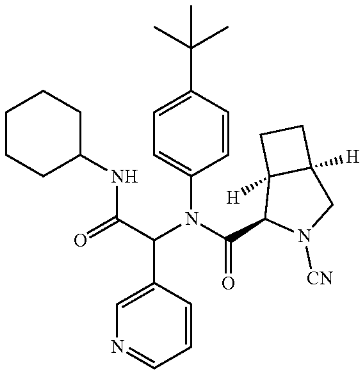 |
| 923 | 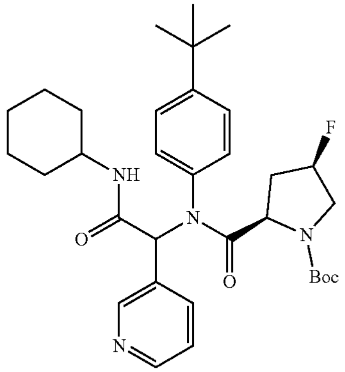 [SMILES: CC(C)(C)OC(=O)N1C[C@H](F)C[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 924 | 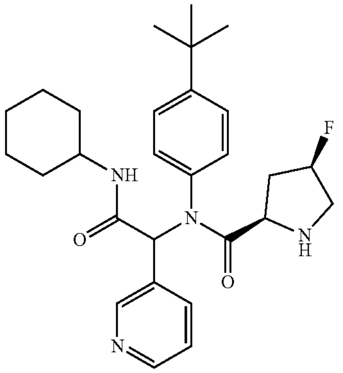 [SMILES: CC(C)(C)c1ccc(N(C(=O)[C@H]2C[C@@H](F)CN2)C(C(=O)NC2CCCCC2)c2cccnc2)cc1] |
| 925a | 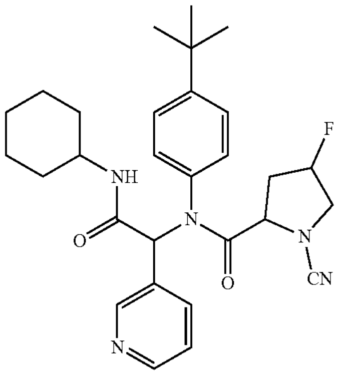 [SMILES: CC(C)(C)c1ccc(N(C(=O)C2CC(F)CN2C#N)C(C(=O)NC2CCCCC2)c2cccnc2)cc1] |
| 925 | 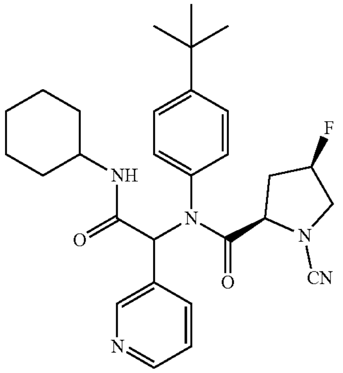 [SMILES: CC(C)(C)c1ccc(N(C(=O)[C@H]2C[C@@H](F)CN2C#N)C(C(=O)NC2CCCCC2)c2cccnc2)cc1] |
| 926 | 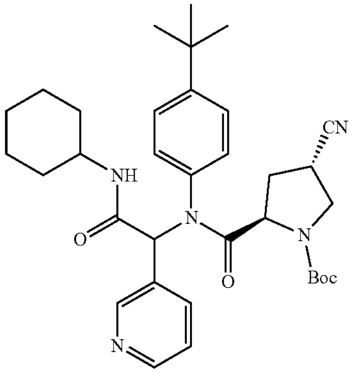 [SMILES: CC(C)(C)OC(=O)N1C[C@@H](C#N)C[C@@H]1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 927 | 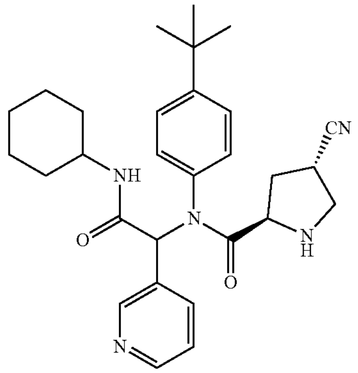 [SMILES: CC(C)(C)c1ccc(N(C(=O)[C@H]2C[C@H](C#N)CN2)C(C(=O)NC2CCCCC2)c2cccnc2)cc1] |
| 928a | 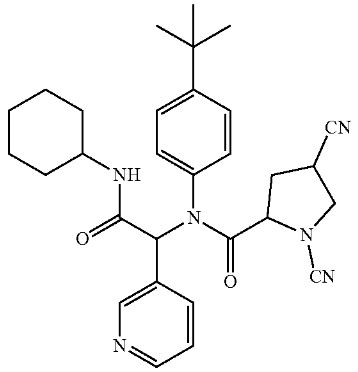 [SMILES: CC(C)(C)c1ccc(N(C(=O)C2CC(C#N)CN2C#N)C(C(=O)NC2CCCCC2)c2cccnc2)cc1] |
| 928 | 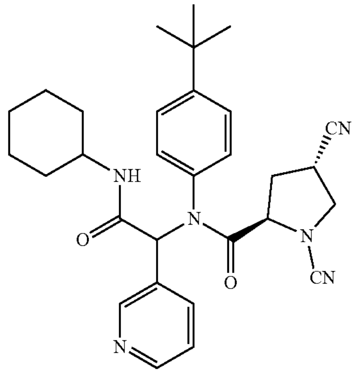 [SMILES: CC(C)(C)c1ccc(N(C(=O)[C@H]2C[C@H](C#N)CN2C#N)C(C(=O)NC2CCCCC2)c2cccnc2)cc1] |
| 929 | 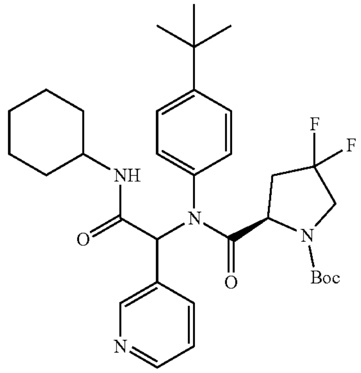 [SMILES: CC(C)(C)OC(=O)N1CC(F)(F)C[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 930 | 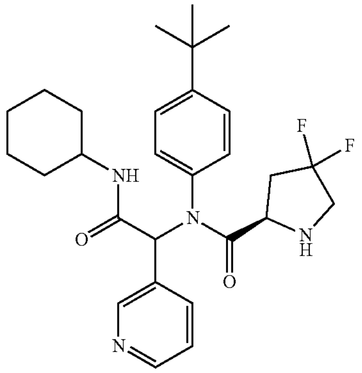 [SMILES: CC(C)(C)c1ccc(N(C(=O)[C@H]2CC(F)(F)CN2)C(C(=O)NC2CCCCC2)c2cccnc2)cc1] |
| 931a | 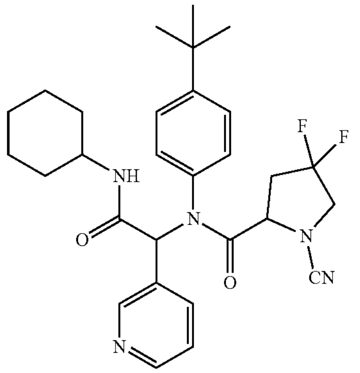 [SMILES: CC(C)(C)c1ccc(N(C(=O)C2CC(F)(F)CN2C#N)C(C(=O)NC2CCCCC2)c2cccnc2)cc1] |
| 931 | 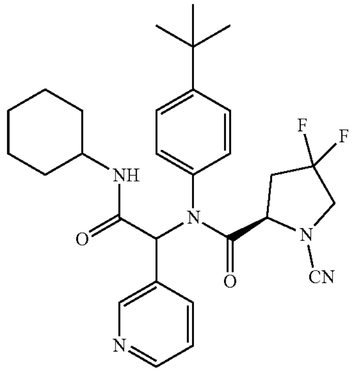 [SMILES: CC(C)(C)c1ccc(N(C(=O)[C@H]2CC(F)(F)CN2C#N)C(C(=O)NC2CCCCC2)c2cccnc2)cc1] |
| 932 | 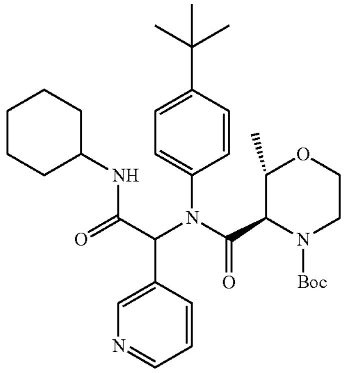 [SMILES: C[C@@H]1OCCN(C(=O)OC(C)(C)C)[C@H]1C(=O)N(c1ccc(C(C)(C)C)cc1)C(C(=O)NC1CCCCC1)c1cccnc1] |

TABLE 1-continued
| Exemplary compounds. | |
|---|---|
| Cmpd No. | Structure |
| 933 | 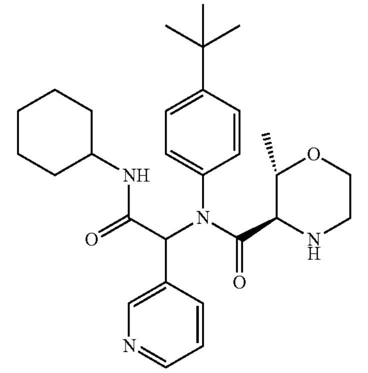 [SMILES: C[C@@H]1OCCN[C@H]1C(=O)N(c1ccc(C(C)(C)C)cc1)C(C(=O)NC1CCCCC1)c1cccnc1] |
| 934a | 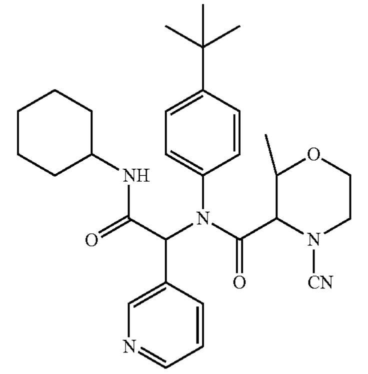 [SMILES: CC1OCCN(C#N)C1C(=O)N(c1ccc(C(C)(C)C)cc1)C(C(=O)NC1CCCCC1)c1cccnc1] |
| 934 | 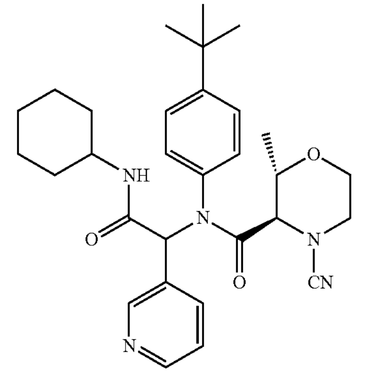 [SMILES: C[C@@H]1OCCN(C#N)[C@H]1C(=O)N(c1ccc(C(C)(C)C)cc1)C(C(=O)NC1CCCCC1)c1cccnc1] |
| 935 | 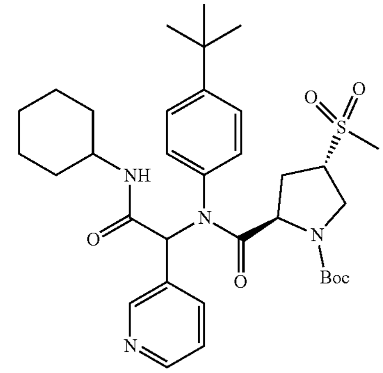 [SMILES: CC(C)(C)OC(=O)N1C[C@@H](S(C)(=O)=O)C[C@@H]1C(=O)N(c1ccc(C(C)(C)C)cc1)C(C(=O)NC1CCCCC1)c1cccnc1] |
TABLE 1-continued
| Exemplary compounds. | |
|---|---|
| Cmpd No. | Structure |
| 936 | 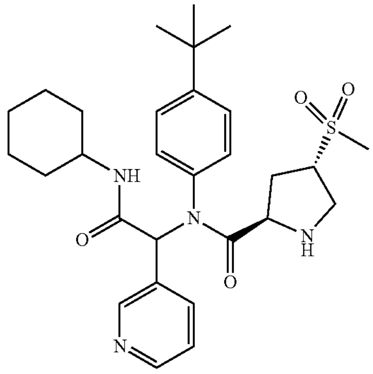 [SMILES: CC(C)(C)c1ccc(N(C(=O)[C@H]2C[C@H](S(C)(=O)=O)CN2)C(C(=O)NC2CCCCC2)c2cccnc2)cc1] |
| 937a | 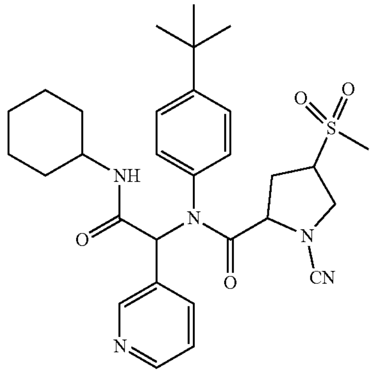 [SMILES: CC(C)(C)c1ccc(N(C(=O)C2CC(S(C)(=O)=O)CN2C#N)C(C(=O)NC2CCCCC2)c2cccnc2)cc1] |
| 937 | 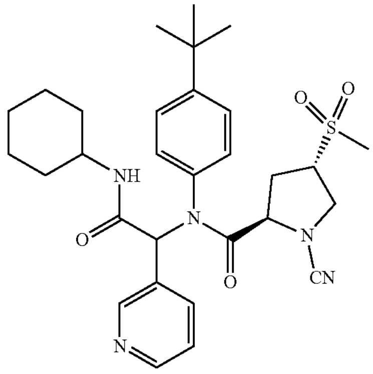 [SMILES: CC(C)(C)c1ccc(N(C(=O)[C@H]2C[C@H](S(C)(=O)=O)CN2C#N)C(C(=O)NC2CCCCC2)c2cccnc2)cc1] |
| 938 | 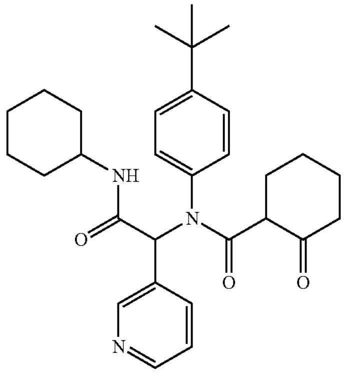 [SMILES: CC(C)(C)c1ccc(N(C(=O)C2CCCCC2=O)C(C(=O)NC2CCCCC2)c2cccnc2)cc1] |

TABLE 1-continued
| Exemplary compounds. | |
|---|---|
| Cmpd No. | Structure |
| 939 | 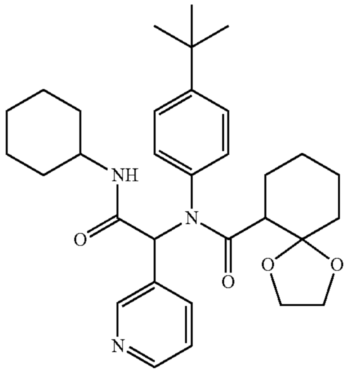 [SMILES: CC(C)(C)c1ccc(N(C(=O)C2CCCCC23OCCO3)C(C(=O)NC2CCCCC2)c2cccnc2)cc1] |
| 940 | 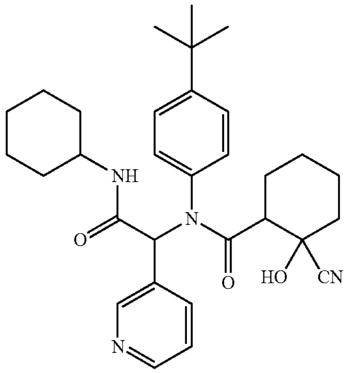 [SMILES: CC(C)(C)c1ccc(N(C(=O)C2CCCCC2(O)C#N)C(C(=O)NC2CCCCC2)c2cccnc2)cc1] |
| 941 | 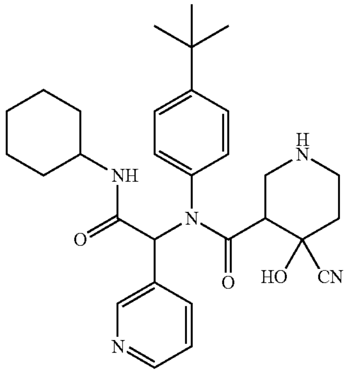 [SMILES: CC(C)(C)c1ccc(N(C(=O)C2CNCCC2(O)C#N)C(C(=O)NC2CCCCC2)c2cccnc2)cc1] |
| 942 | 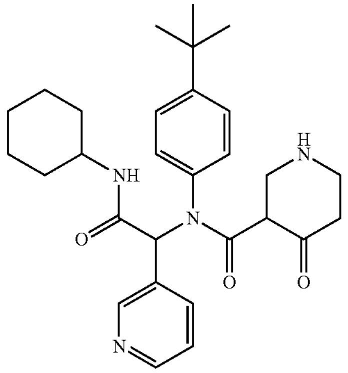 [SMILES: CC(C)(C)c1ccc(N(C(=O)C2CNCCC2=O)C(C(=O)NC2CCCCC2)c2cccnc2)cc1] |
TABLE 1-continued
| Exemplary compounds. | |
|---|---|
| Cmpd No. | Structure |
| 943 | 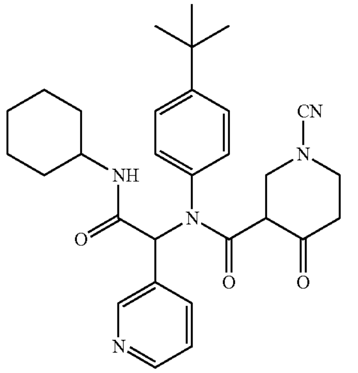 [SMILES: CC(C)(C)c1ccc(N(C(=O)C2CN(C#N)CCC2=O)C(C(=O)NC2CCCCC2)c2cccnc2)cc1] |
| 944 | 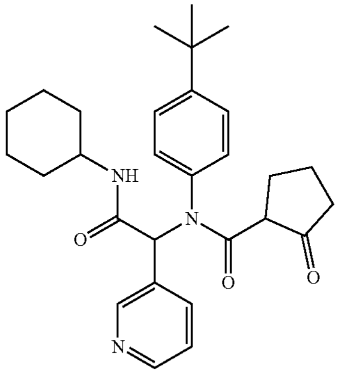 [SMILES: CC(C)(C)c1ccc(N(C(=O)C2CCCC2=O)C(C(=O)NC2CCCCC2)c2cccnc2)cc1] |
| 945 | 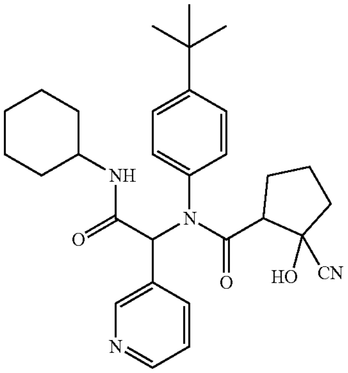 [SMILES: CC(C)(C)c1ccc(N(C(=O)C2CCCC2(O)C#N)C(C(=O)NC2CCCCC2)c2cccnc2)cc1] |
| 946a | 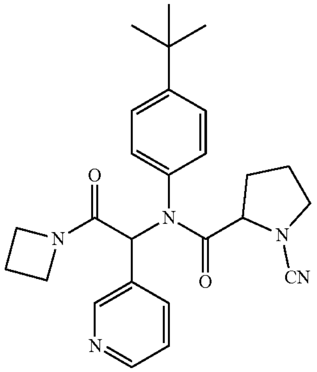 [SMILES: CC(C)(C)c1ccc(N(C(=O)C2CCCN2C#N)C(C(=O)N2CCC2)c2cccnc2)cc1] |

TABLE 1-continued
| Exemplary compounds. | |
|---|---|
| Cmpd No. | Structure |
| 946 | 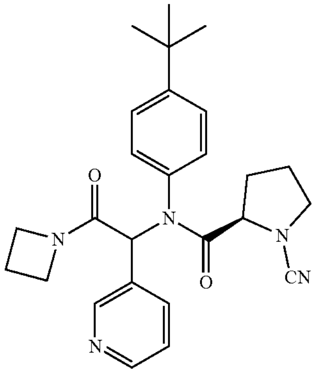 [SMILES: CC(C)(C)c1ccc(N(C(=O)[C@H]2CCCN2C#N)C(C(=O)N2CCC2)c2cccnc2)cc1] |
| 946c | 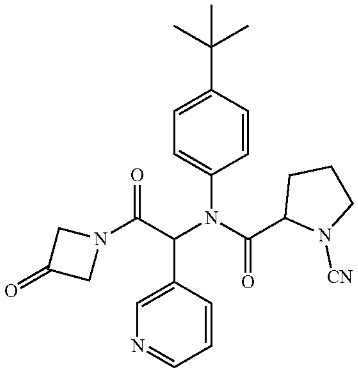 [SMILES: CC(C)(C)c1ccc(N(C(=O)C2CCCN2C#N)C(C(=O)N2CC(=O)C2)c2cccnc2)cc1] |
| 946b | 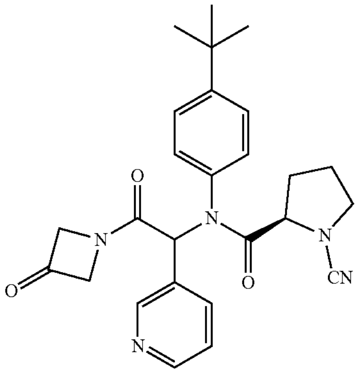 [SMILES: CC(C)(C)c1ccc(N(C(=O)[C@H]2CCCN2C#N)C(C(=O)N2CC(=O)C2)c2cccnc2)cc1] |
| 947a | 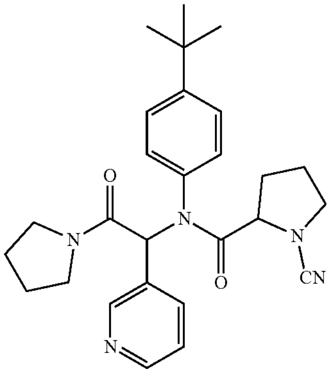 [SMILES: CC(C)(C)c1ccc(N(C(=O)C2CCCN2C#N)C(C(=O)N2CCCC2)c2cccnc2)cc1] |
TABLE 1-continued
| Exemplary compounds. | |
|---|---|
| Cmpd No. | Structure |
| 947 | 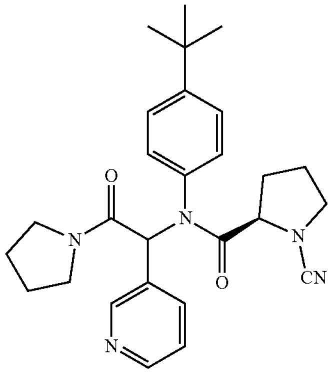 [SMILES: CC(C)(C)c1ccc(N(C(=O)[C@H]2CCCN2C#N)C(C(=O)N2CCCC2)c2cccnc2)cc1] |
| 948a | 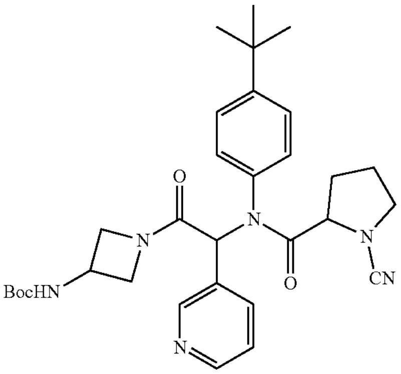 [SMILES: CC(C)(C)OC(=O)NC1CN(C(=O)C(c2cccnc2)N(C(=O)C2CCCN2C#N)c2ccc(C(C)(C)C)cc2)C1] |
| 948 | 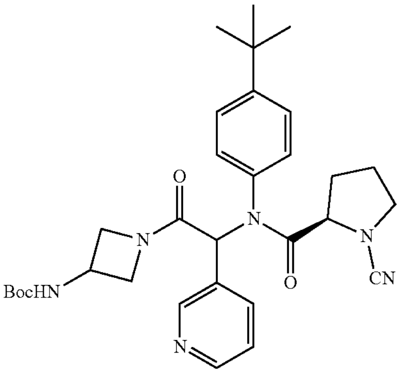 [SMILES: CC(C)(C)OC(=O)NC1CN(C(=O)C(c2cccnc2)N(C(=O)[C@H]2CCCN2C#N)c2ccc(C(C)(C)C)cc2)C1] |
| 949a | 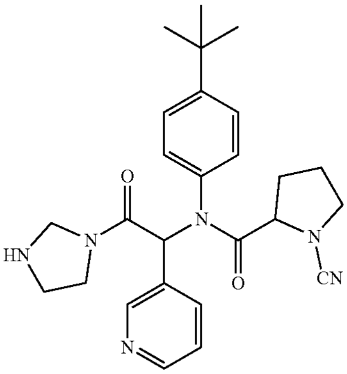 [SMILES: CC(C)(C)c1ccc(N(C(=O)C2CCCN2C#N)C(C(=O)N2CCNC2)c2cccnc2)cc1] |

TABLE 1-continued
| Exemplary compounds. | |
|---|---|
| Cmpd No. | Structure |
| 949 | 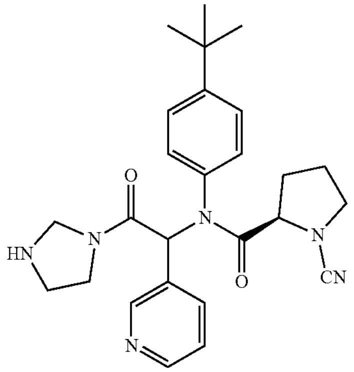 [SMILES: CC(C)(C)c1ccc(N(C(=O)[C@H]2CCCN2C#N)C(C(=O)N2CCNC2)c2cccnc2)cc1] |
| 950a | 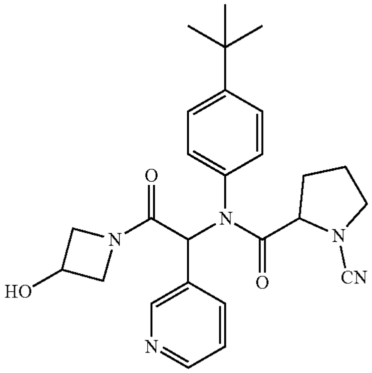 [SMILES: CC(C)(C)c1ccc(N(C(=O)C2CCCN2C#N)C(C(=O)N2CC(O)C2)c2cccnc2)cc1] |
| 950 | 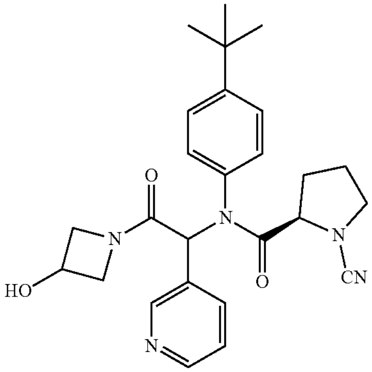 [SMILES: CC(C)(C)c1ccc(N(C(=O)[C@H]2CCCN2C#N)C(C(=O)N2CC(O)C2)c2cccnc2)cc1] |
| 951a | 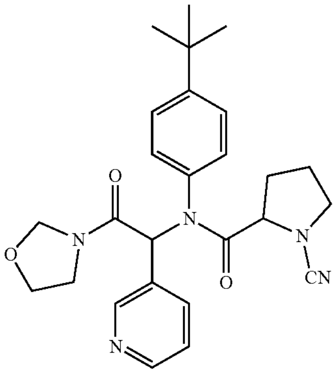 [SMILES: CC(C)(C)c1ccc(N(C(=O)C2CCCN2C#N)C(C(=O)N2CCOC2)c2cccnc2)cc1] |
TABLE 1-continued
| Exemplary compounds. | |
|---|---|
| Cmpd No. | Structure |
| 951 | 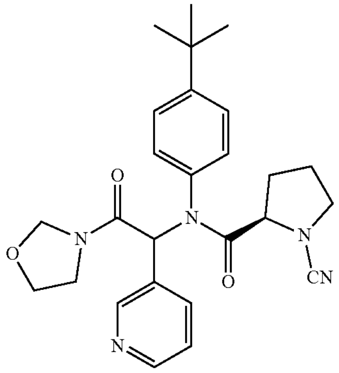 [SMILES: CC(C)(C)c1ccc(N(C(=O)[C@H]2CCCN2C#N)C(C(=O)N2CCOC2)c2cccnc2)cc1] |
| 952a | 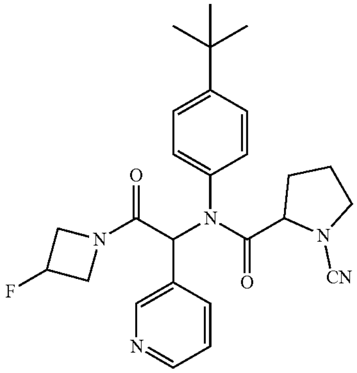 [SMILES: CC(C)(C)c1ccc(N(C(=O)C2CCCN2C#N)C(C(=O)N2CC(F)C2)c2cccnc2)cc1] |
| 952 | 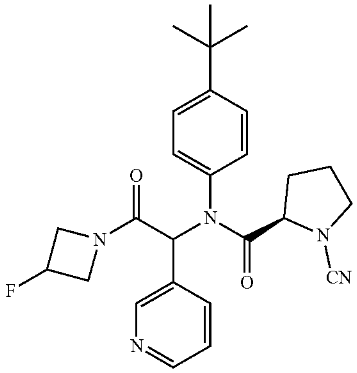 [SMILES: CC(C)(C)c1ccc(N(C(=O)[C@H]2CCCN2C#N)C(C(=O)N2CC(F)C2)c2cccnc2)cc1] |
| 953a | 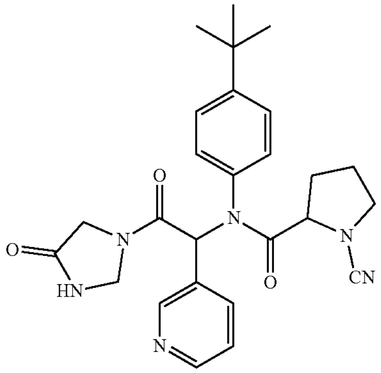 [SMILES: CC(C)(C)c1ccc(N(C(=O)C2CCCN2C#N)C(C(=O)N2CNC(=O)C2)c2cccnc2)cc1] |

TABLE 1-continued
| Exemplary compounds. | |
|---|---|
| Cmpd No. | Structure |
| 953 | 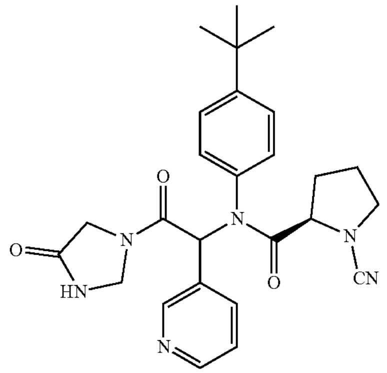 [SMILES: CC(C)(C)c1ccc(N(C(=O)[C@H]2CCCN2C#N)C(C(=O)N2CNC(=O)C2)c2cccnc2)cc1] |
| 954a | 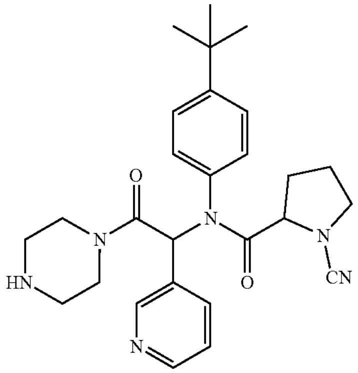 [SMILES: CC(C)(C)c1ccc(N(C(=O)C2CCCN2C#N)C(C(=O)N2CCNCC2)c2cccnc2)cc1] |
| 954 | 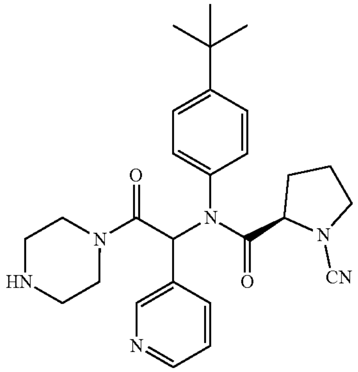 [SMILES: CC(C)(C)c1ccc(N(C(=O)[C@H]2CCCN2C#N)C(C(=O)N2CCNCC2)c2cccnc2)cc1] |
| 954b | 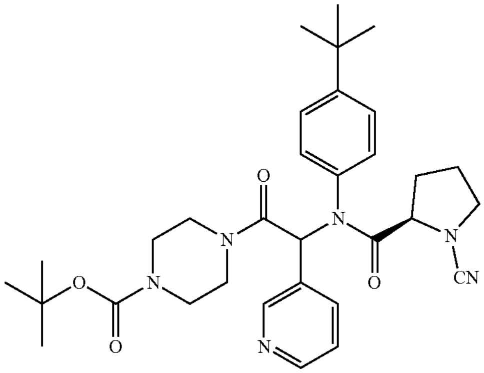 [SMILES: CC(C)(C)OC(=O)N1CCN(C(=O)C(c2cccnc2)N(C(=O)[C@H]2CCCN2C#N)c2ccc(C(C)(C)C)cc2)CC1] |
TABLE 1-continued
| Exemplary compounds. | |
|---|---|
| Cmpd No. | Structure |
| 955a | 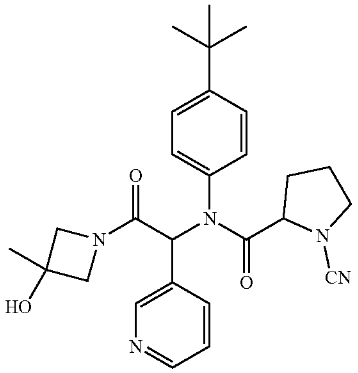 [SMILES: CC1(O)CN(C(=O)C(c2cccnc2)N(C(=O)C2CCCN2C#N)c2ccc(C(C)(C)C)cc2)C1] |
| 955 | 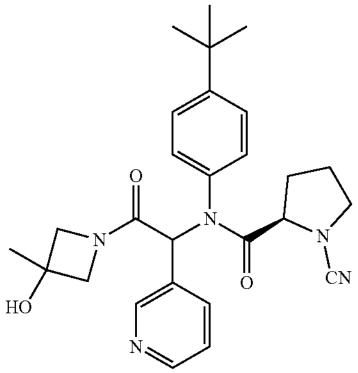 [SMILES: CC1(O)CN(C(=O)C(c2cccnc2)N(C(=O)[C@H]2CCCN2C#N)c2ccc(C(C)(C)C)cc2)C1] |
| 956a | 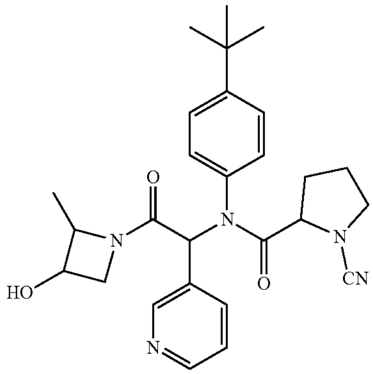 [SMILES: CC1C(O)CN1C(=O)C(c1cccnc1)N(C(=O)C1CCCN1C#N)c1ccc(C(C)(C)C)cc1] |
| 956 | 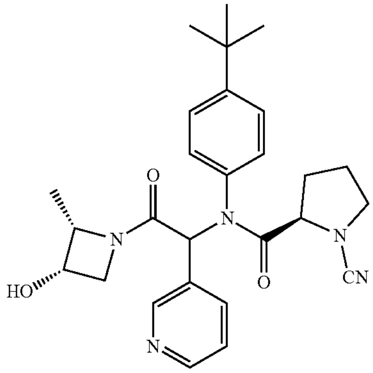 [SMILES: C[C@H]1[C@@H](O)CN1C(=O)C(c1cccnc1)N(C(=O)[C@H]1CCCN1C#N)c1ccc(C(C)(C)C)cc1] |

TABLE 1-continued
| Exemplary compounds. | |
|---|---|
| Cmpd No. | Structure |
| 657a | 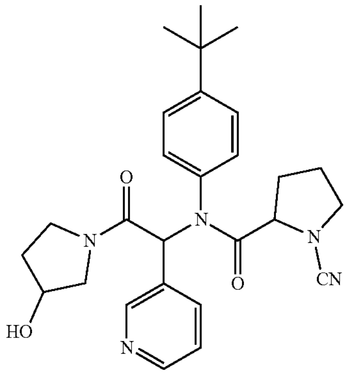 [SMILES: CC(C)(C)c1ccc(N(C(=O)C2CCCN2C#N)C(C(=O)N2CCC(O)C2)c2cccnc2)cc1] |
| 957 | 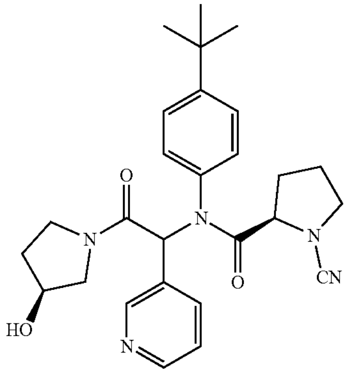 [SMILES: CC(C)(C)c1ccc(N(C(=O)[C@H]2CCCN2C#N)C(C(=O)N2CC[C@H](O)C2)c2cccnc2)cc1] |
| 958a | 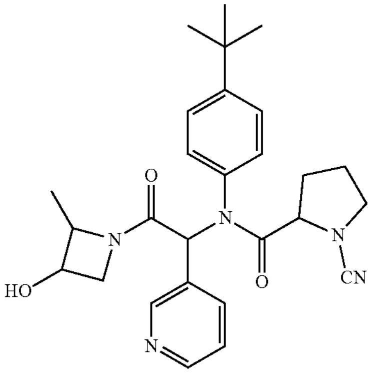 [SMILES: CC1C(O)CN1C(=O)C(c1cccnc1)N(C(=O)C1CCCN1C#N)c1ccc(C(C)(C)C)cc1] |
| 958 | 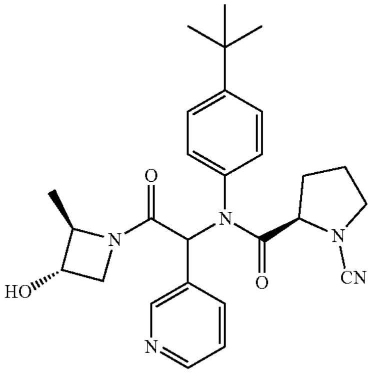 [SMILES: C[C@@H]1[C@@H](O)CN1C(=O)C(c1cccnc1)N(C(=O)[C@H]1CCCN1C#N)c1ccc(C(C)(C)C)cc1] |
TABLE 1-continued
| Exemplary compounds. | |
|---|---|
| Cmpd No. | Structure |
| 959a | 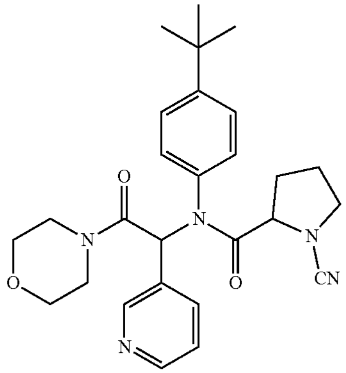 [SMILES: CC(C)(C)c1ccc(N(C(=O)C2CCCN2C#N)C(C(=O)N2CCOCC2)c2cccnc2)cc1] |
| 959 | 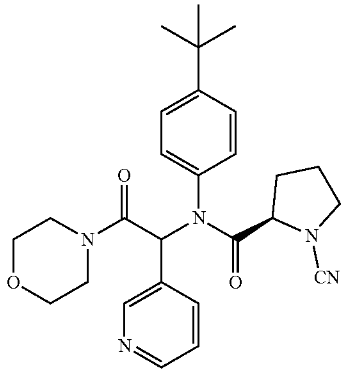 [SMILES: CC(C)(C)c1ccc(N(C(=O)[C@H]2CCCN2C#N)C(C(=O)N2CCOCC2)c2cccnc2)cc1] |
| 960a | 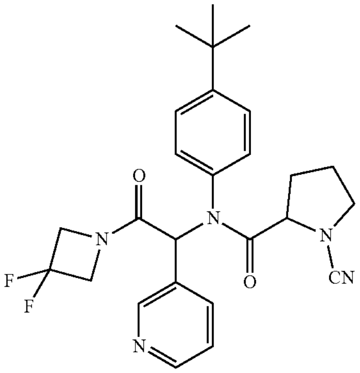 [SMILES: CC(C)(C)c1ccc(N(C(=O)C2CCCN2C#N)C(C(=O)N2CC(F)(F)C2)c2cccnc2)cc1] |
| 960 | 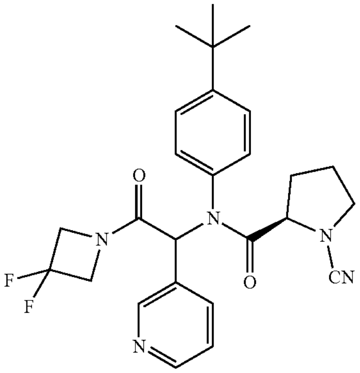 [SMILES: CC(C)(C)c1ccc(N(C(=O)[C@H]2CCCN2C#N)C(C(=O)N2CC(F)(F)C2)c2cccnc2)cc1] |

TABLE 1-continued
Exemplary compounds.
| Cmpd No. | Structure |
| --- | --- |
| 961a | 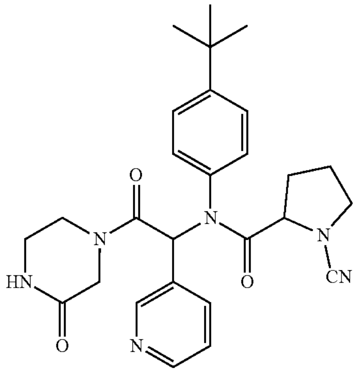 [SMILES: CC(C)(C)c1ccc(N(C(=O)C2CCCN2C#N)C(C(=O)N2CCNC(=O)C2)c2cccnc2)cc1] |
| 961 | 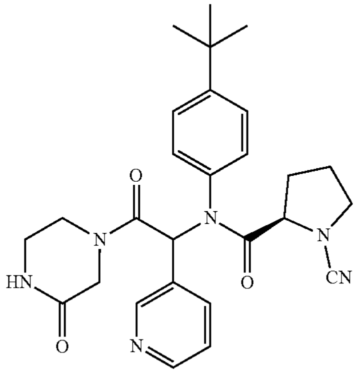 [SMILES: CC(C)(C)c1ccc(N(C(=O)[C@H]2CCCN2C#N)C(C(=O)N2CCNC(=O)C2)c2cccnc2)cc1] |
| 962a | 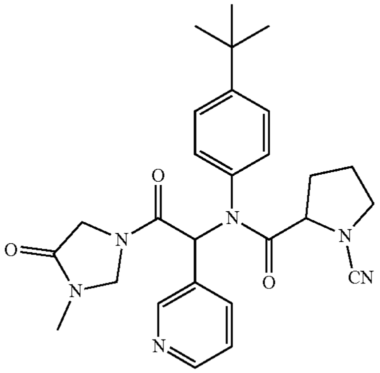 [SMILES: CN1CN(C(=O)C(c2cccnc2)N(C(=O)C2CCCN2C#N)c2ccc(C(C)(C)C)cc2)CC1=O] |
| 962 | 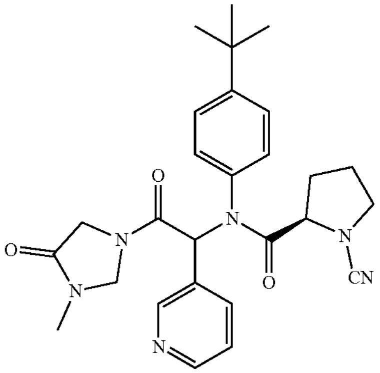 [SMILES: CN1CN(C(=O)C(c2cccnc2)N(C(=O)[C@H]2CCCN2C#N)c2ccc(C(C)(C)C)cc2)CC1=O] |
TABLE 1-continued
Exemplary compounds.
| Cmpd No. | Structure |
| --- | --- |
| 963a | 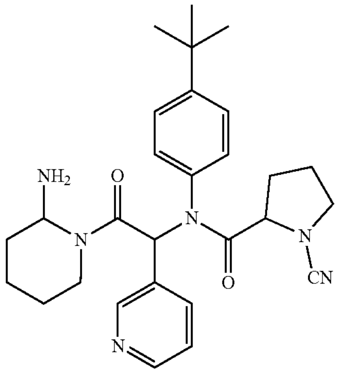 [SMILES: CC(C)(C)c1ccc(N(C(=O)C2CCCN2C#N)C(C(=O)N2CCCCC2N)c2cccnc2)cc1] |
| 963 | 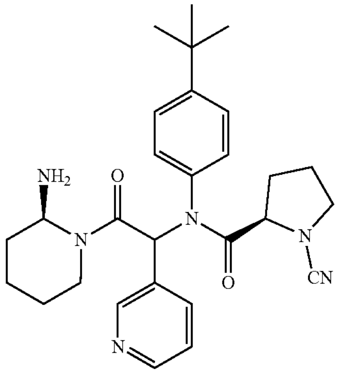 [SMILES: CC(C)(C)c1ccc(N(C(=O)[C@H]2CCCN2C#N)C(C(=O)N2CCCC[C@H]2N)c2cccnc2)cc1] |
| 964a | 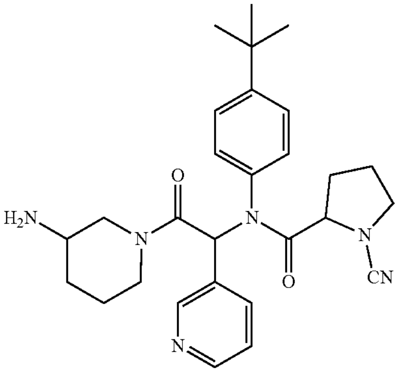 [SMILES: CC(C)(C)c1ccc(N(C(=O)C2CCCN2C#N)C(C(=O)N2CCCC(N)C2)c2cccnc2)cc1] |
| 964 | 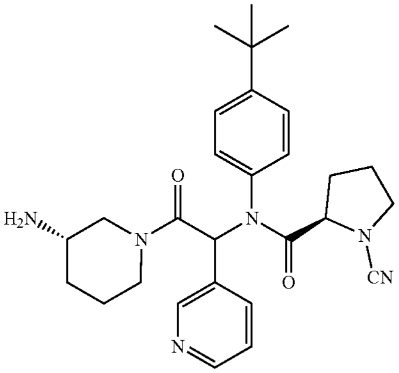 [SMILES: CC(C)(C)c1ccc(N(C(=O)[C@H]2CCCN2C#N)C(C(=O)N2CCC[C@H](N)C2)c2cccnc2)cc1] |

TABLE 1-continued
| Exemplary compounds. | |
|---|---|
| Cmpd No. | Structure |
| 965a | 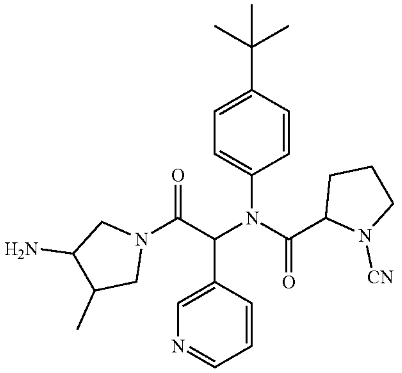 [SMILES: CC1CN(C(=O)C(c2cccnc2)N(C(=O)C2CCCN2C#N)c2ccc(C(C)(C)C)cc2)CC1N] |
| 965 | 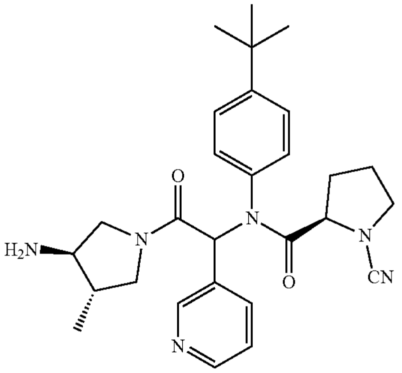 [SMILES: C[C@H]1CN(C(=O)C(c2cccnc2)N(C(=O)[C@H]2CCCN2C#N)c2ccc(C(C)(C)C)cc2)C[C@@H]1N] |
| 966a | 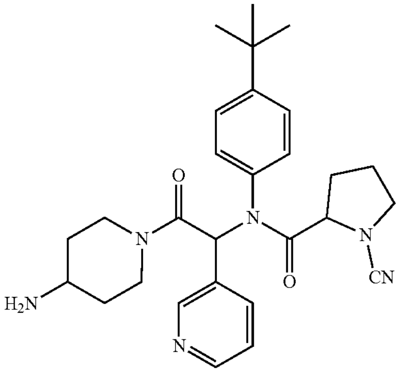 [SMILES: CC(C)(C)c1ccc(N(C(=O)C2CCCN2C#N)C(C(=O)N2CCC(N)CC2)c2cccnc2)cc1] |
| 966 | 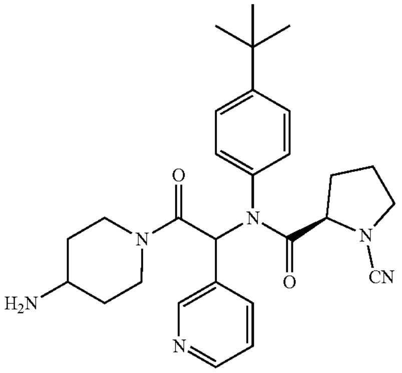 [SMILES: CC(C)(C)c1ccc(N(C(=O)[C@H]2CCCN2C#N)C(C(=O)N2CCC(N)CC2)c2cccnc2)cc1] |
TABLE 1-continued
| Exemplary compounds. | |
|---|---|
| Cmpd No. | Structure |
| 966b | 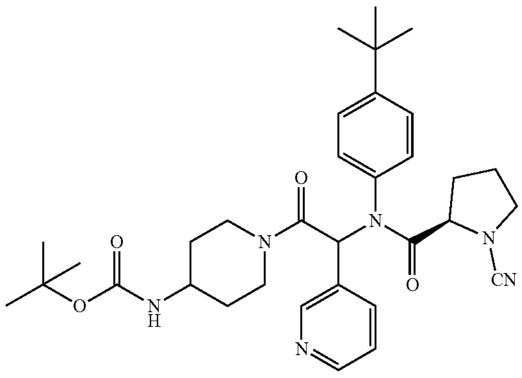 [SMILES: CC(C)(C)OC(=O)NC1CCN(C(=O)C(c2cccnc2)N(C(=O)[C@H]2CCCN2C#N)c2ccc(C(C)(C)C)cc2)CC1] |
| 967a | 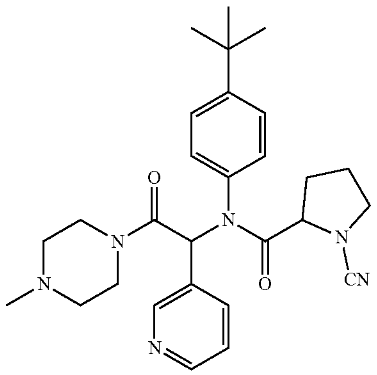 [SMILES: CN1CCN(C(=O)C(c2cccnc2)N(C(=O)C2CCCN2C#N)c2ccc(C(C)(C)C)cc2)CC1] |
| 967 | 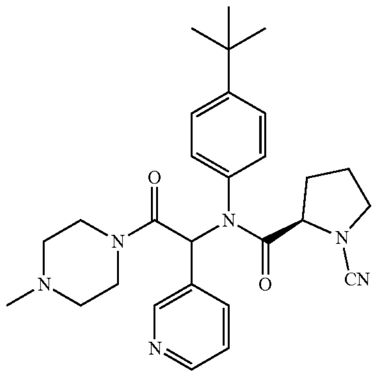 [SMILES: CN1CCN(C(=O)C(c2cccnc2)N(C(=O)[C@H]2CCCN2C#N)c2ccc(C(C)(C)C)cc2)CC1] |
| 968a | 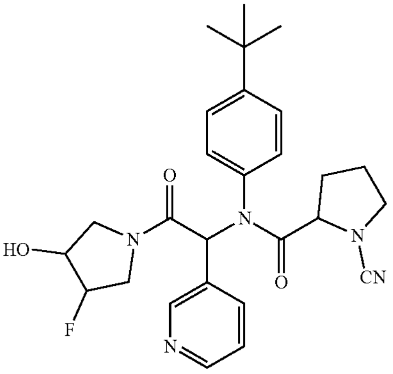 [SMILES: CC(C)(C)c1ccc(N(C(=O)C2CCCN2C#N)C(C(=O)N2CC(O)C(F)C2)c2cccnc2)cc1] |

TABLE 1-continued
| Exemplary compounds. | |
|---|---|
| Cmpd No. | Structure |
| 968 | 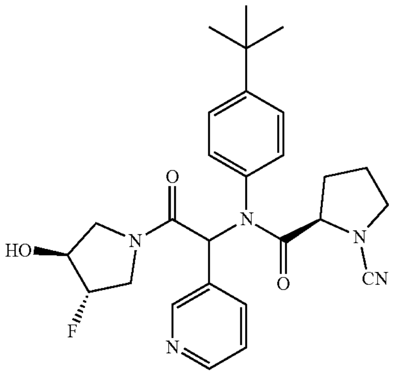 [SMILES: CC(C)(C)c1ccc(N(C(=O)[C@H]2CCCN2C#N)C(C(=O)N2C[C@H](O)[C@@H](F)C2)c2cccnc2)cc1] |
| 969a | 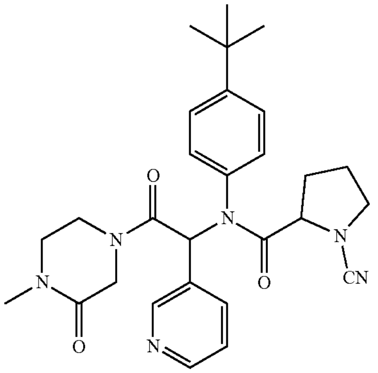 [SMILES: CN1CCN(C(=O)C(c2cccnc2)N(C(=O)C2CCCN2C#N)c2ccc(C(C)(C)C)cc2)CC1=O] |
| 969 | 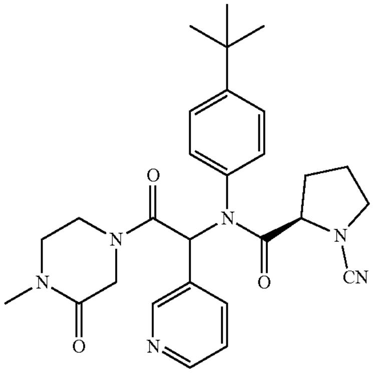 [SMILES: CN1CCN(C(=O)C(c2cccnc2)N(C(=O)[C@H]2CCCN2C#N)c2ccc(C(C)(C)C)cc2)CC1=O] |
| 970a | 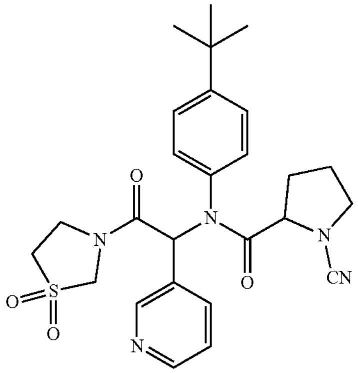 [SMILES: CC(C)(C)c1ccc(N(C(=O)C2CCCN2C#N)C(C(=O)N2CCS(=O)(=O)C2)c2cccnc2)cc1] |
TABLE 1-continued
| Exemplary compounds. | |
|---|---|
| Cmpd No. | Structure |
| 970 | 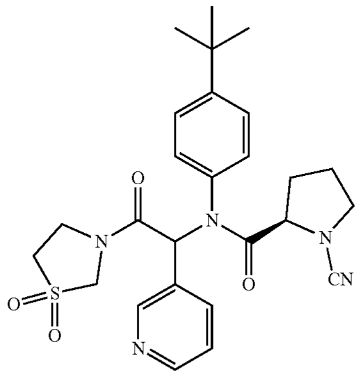 [SMILES: CC(C)(C)c1ccc(N(C(=O)[C@H]2CCCN2C#N)C(C(=O)N2CCS(=O)(=O)C2)c2cccnc2)cc1] |
| 971a | 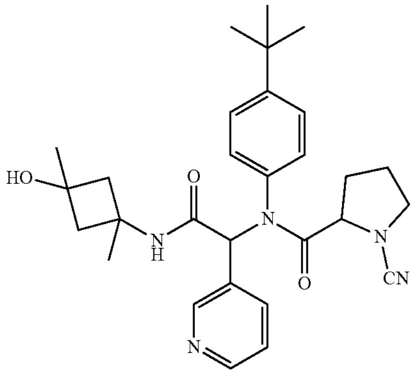 [SMILES: CC1(O)CC(C)(NC(=O)C(c2cccnc2)N(C(=O)C2CCCN2C#N)c2ccc(C(C)(C)C)cc2)C1] |
| 971 | 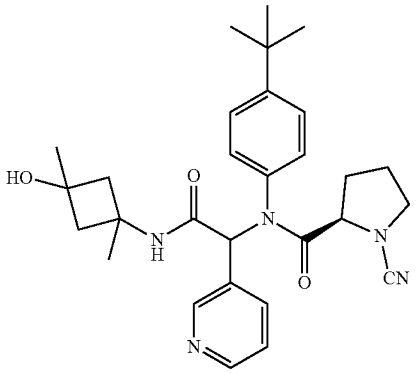 [SMILES: CC1(O)CC(C)(NC(=O)C(c2cccnc2)N(C(=O)[C@H]2CCCN2C#N)c2ccc(C(C)(C)C)cc2)C1] |
| 972a | 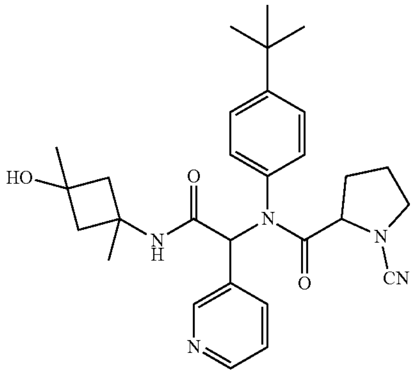 [SMILES: CC1(O)CC(C)(NC(=O)C(c2cccnc2)N(C(=O)C2CCCN2C#N)c2ccc(C(C)(C)C)cc2)C1] |

TABLE 1-continued
| Exemplary compounds. | |
|---|---|
| Cmpd No. | Structure |
| 972 | 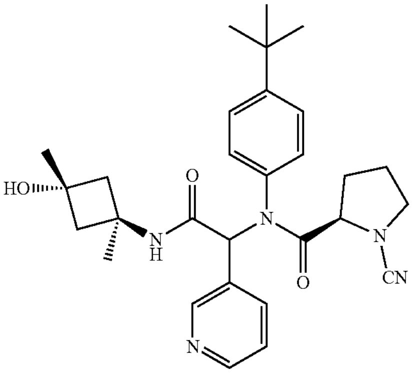 [SMILES: CC(C)(C)c1ccc(N(C(=O)[C@H]2CCCN2C#N)C(C(=O)N[C@]2(C)C[C@@](C)(O)C2)c2cccnc2)cc1] |
| 973a | 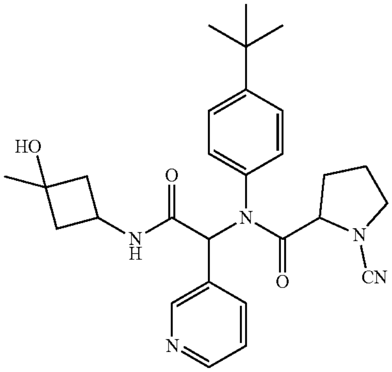 [SMILES: CC1(O)CC(NC(=O)C(c2cccnc2)N(C(=O)C2CCCN2C#N)c2ccc(C(C)(C)C)cc2)C1] |
| 973 | 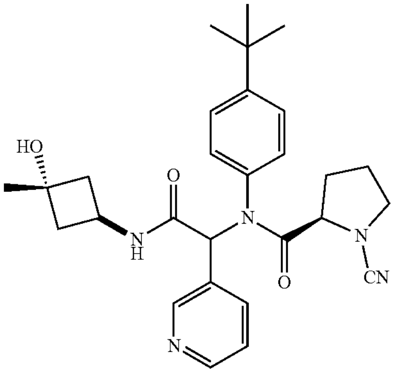 |
| 974a | 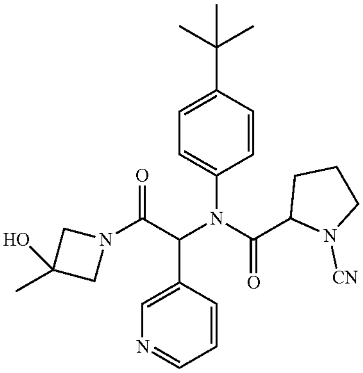 [SMILES: CC1(O)CN(C(=O)C(c2cccnc2)N(C(=O)C2CCCN2C#N)c2ccc(C(C)(C)C)cc2)C1] |
TABLE 1-continued
| Exemplary compounds. | |
|---|---|
| Cmpd No. | Structure |
| 974 | 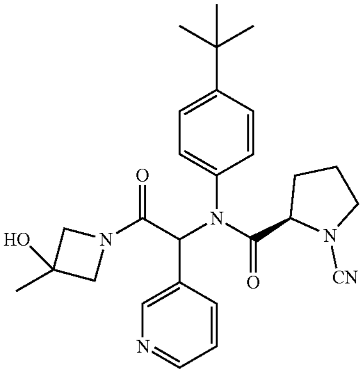 [SMILES: CC1(O)CN(C(=O)C(c2cccnc2)N(C(=O)[C@H]2CCCN2C#N)c2ccc(C(C)(C)C)cc2)C1] |
| 975a | 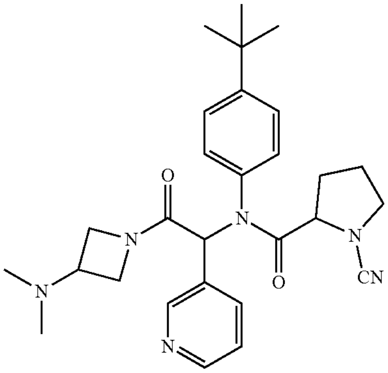 [SMILES: CN(C)C1CN(C(=O)C(c2cccnc2)N(C(=O)C2CCCN2C#N)c2ccc(C(C)(C)C)cc2)C1] |
| 975 | 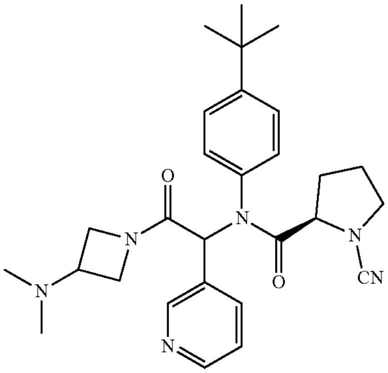 [SMILES: CN(C)C1CN(C(=O)C(c2cccnc2)N(C(=O)[C@H]2CCCN2C#N)c2ccc(C(C)(C)C)cc2)C1] |
| 976a | 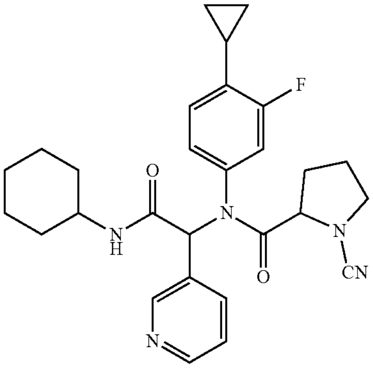 [SMILES: N#CN1CCCC1C(=O)N(c1ccc(C2CC2)c(F)c1)C(C(=O)NC1CCCCC1)c1cccnc1] |

TABLE 1-continued
| Exemplary compounds. | |
|---|---|
| Cmpd No. | Structure |
| 976 | 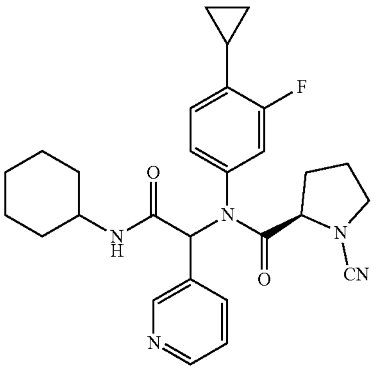 [SMILES: N#CN1CCC[C@@H]1C(=O)N(c1ccc(C2CC2)c(F)c1)C(C(=O)NC1CCCCC1)c1cccnc1] |
| 977a | 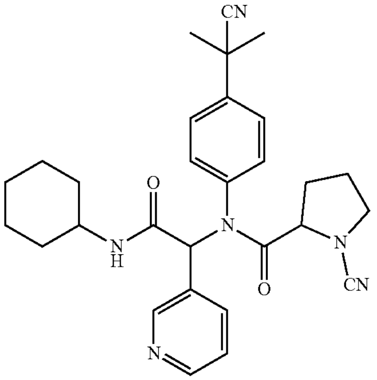 [SMILES: CC(C)(C#N)c1ccc(N(C(=O)C2CCCN2C#N)C(C(=O)NC2CCCCC2)c2cccnc2)cc1] |
| 977 | 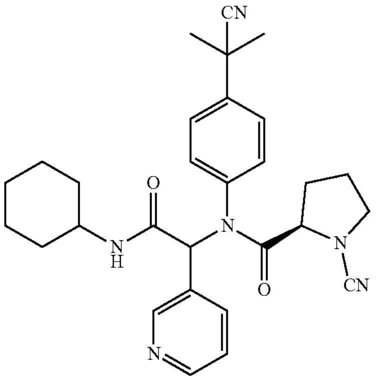 [SMILES: CC(C)(C#N)c1ccc(N(C(=O)[C@H]2CCCN2C#N)C(C(=O)NC2CCCCC2)c2cccnc2)cc1] |
| 978a | 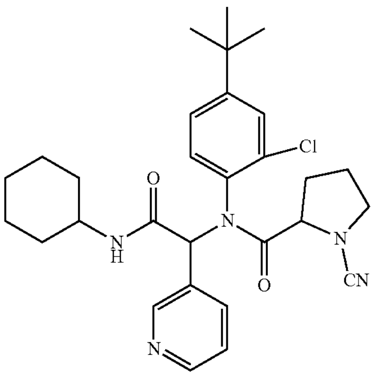 [SMILES: CC(C)(C)c1ccc(N(C(=O)C2CCCN2C#N)C(C(=O)NC2CCCCC2)c2cccnc2)c(Cl)c1] |
TABLE 1-continued
| Exemplary compounds. | |
|---|---|
| Cmpd No. | Structure |
| 978 | 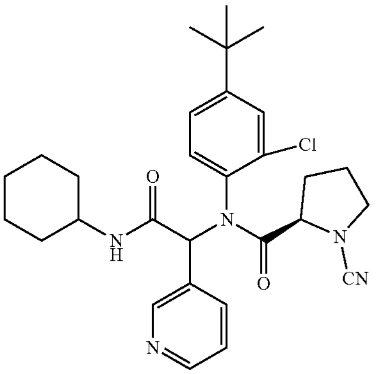 [SMILES: CC(C)(C)c1ccc(N(C(=O)[C@H]2CCCN2C#N)C(C(=O)NC2CCCCC2)c2cccnc2)c(Cl)c1] |
| 979a | 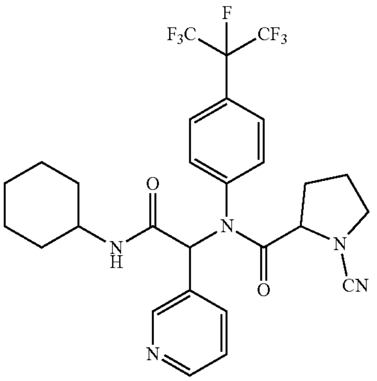 [SMILES: N#CN1CCCC1C(=O)N(c1ccc(C(F)(C(F)(F)F)C(F)(F)F)cc1)C(C(=O)NC1CCCCC1)c1cccnc1] |
| 979 | 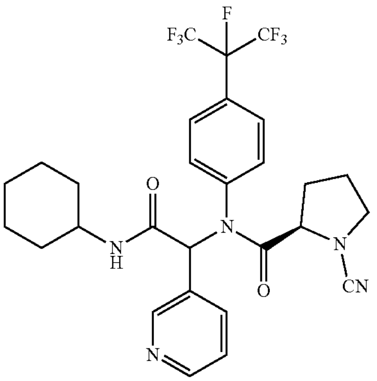 [SMILES: N#CN1CCC[C@@H]1C(=O)N(c1ccc(C(F)(C(F)(F)F)C(F)(F)F)cc1)C(C(=O)NC1CCCCC1)c1cccnc1] |
| 980a | 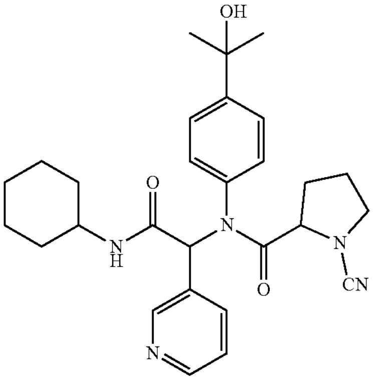 |

TABLE 1-continued
Exemplary compounds.
| Cmpd No. | Structure |
|---|---|
| 980 | 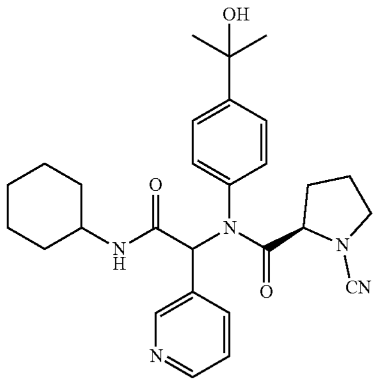 [SMILES: CC(C)(O)c1ccc(N(C(=O)[C@H]2CCCN2C#N)C(C(=O)NC2CCCCC2)c2cccnc2)cc1] |
| 981a | 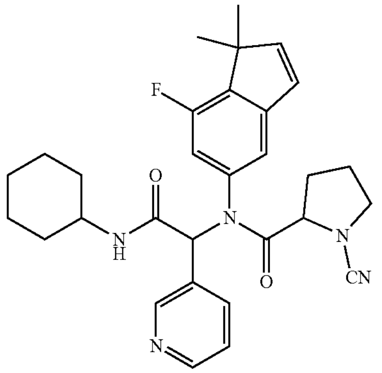 [SMILES: CC1(C)C=Cc2cc(N(C(=O)C3CCCN3C#N)C(C(=O)NC3CCCCC3)c3cccnc3)cc(F)c21] |
| 981 | 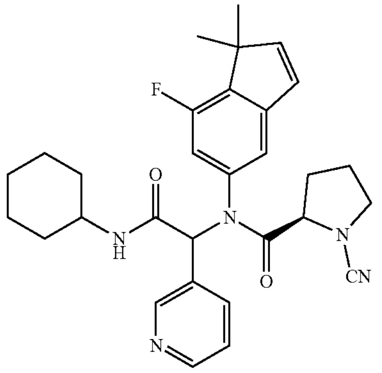 [SMILES: CC1(C)C=Cc2cc(N(C(=O)[C@H]3CCCN3C#N)C(C(=O)NC3CCCCC3)c3cccnc3)cc(F)c21] |
| 982a | 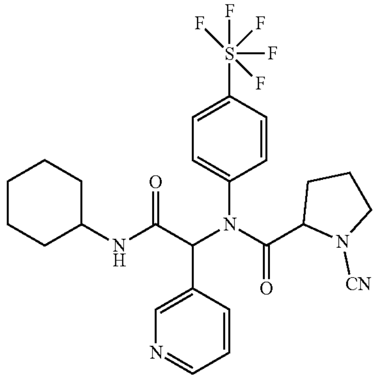 [SMILES: N#CN1CCCC1C(=O)N(c1ccc(S(F)(F)(F)(F)F)cc1)C(C(=O)NC1CCCCC1)c1cccnc1] |
TABLE 1-continued
Exemplary compounds.
| Cmpd No. | Structure |
|---|---|
| 982 | 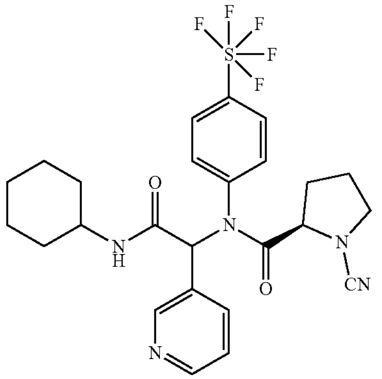 [SMILES: N#CN1CCC[C@@H]1C(=O)N(c1ccc(S(F)(F)(F)(F)F)cc1)C(C(=O)NC1CCCCC1)c1cccnc1] |
| 983a | 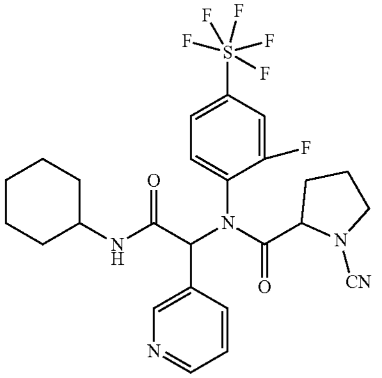 [SMILES: N#CN1CCCC1C(=O)N(c1ccc(S(F)(F)(F)(F)F)cc1F)C(C(=O)NC1CCCCC1)c1cccnc1] |
| 983 | 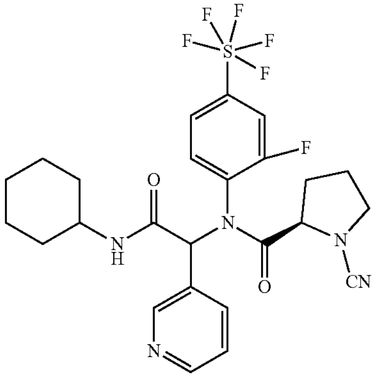 [SMILES: N#CN1CCC[C@@H]1C(=O)N(c1ccc(S(F)(F)(F)(F)F)cc1F)C(C(=O)NC1CCCCC1)c1cccnc1] |
| 984a | 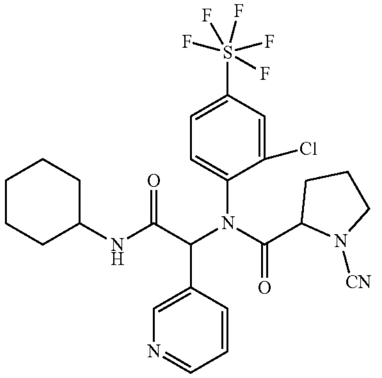 [SMILES: N#CN1CCCC1C(=O)N(c1ccc(S(F)(F)(F)(F)F)cc1Cl)C(C(=O)NC1CCCCC1)c1cccnc1] |

TABLE 1-continued
Exemplary compounds.
| Cmpd No. | Structure |
| --- | --- |
| 984 | 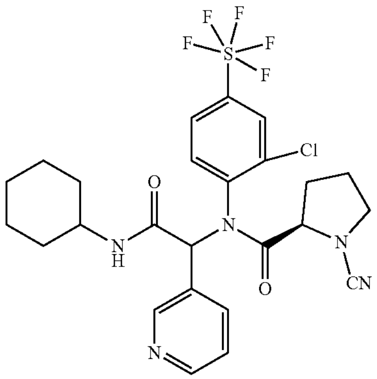 [SMILES: N#CN1CCC[C@@H]1C(=O)N(c1ccc(S(F)(F)(F)(F)F)cc1Cl)C(C(=O)NC1CCCCC1)c1cccnc1] |
| 985a | 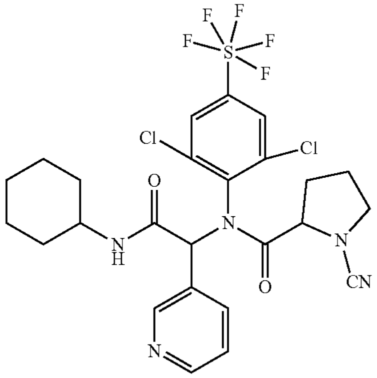 [SMILES: N#CN1CCCC1C(=O)N(c1c(Cl)cc(S(F)(F)(F)(F)F)cc1Cl)C(C(=O)NC1CCCCC1)c1cccnc1] |
| 985 | 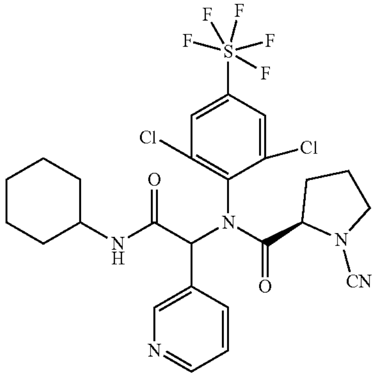 [SMILES: N#CN1CCC[C@@H]1C(=O)N(c1c(Cl)cc(S(F)(F)(F)(F)F)cc1Cl)C(C(=O)NC1CCCCC1)c1cccnc1] |
| 986a | 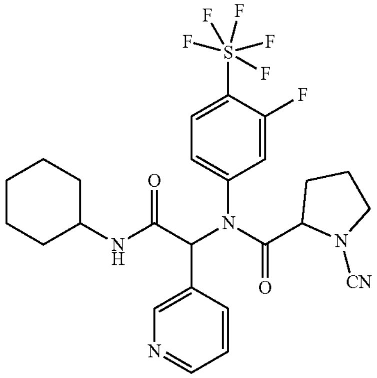 [SMILES: N#CN1CCCC1C(=O)N(c1ccc(S(F)(F)(F)(F)F)c(F)c1)C(C(=O)NC1CCCCC1)c1cccnc1] |
| 986 | 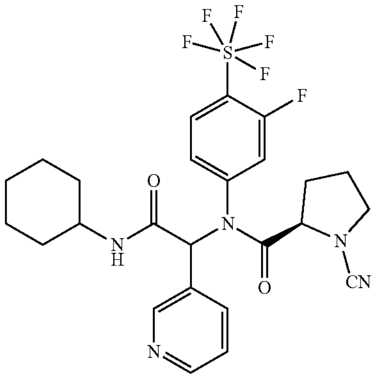 [SMILES: N#CN1CCC[C@@H]1C(=O)N(c1ccc(S(F)(F)(F)(F)F)c(F)c1)C(C(=O)NC1CCCCC1)c1cccnc1] |
| 987a | 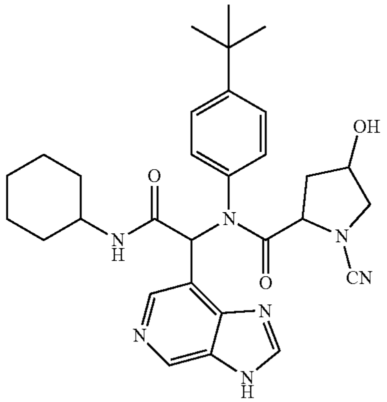 [SMILES: CC(C)(C)c1ccc(N(C(=O)C2CC(O)CN2C#N)C(C(=O)NC2CCCCC2)c2cncc3[nH]cnc23)cc1] |
| 987 | 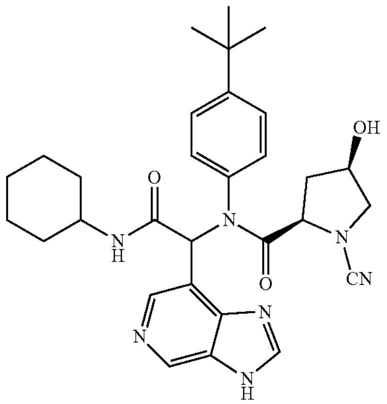 [SMILES: CC(C)(C)c1ccc(N(C(=O)[C@H]2C[C@@H](O)CN2C#N)C(C(=O)NC2CCCCC2)c2cncc3[nH]cnc23)cc1] |

TABLE 1-continued
| Exemplary compounds. | |
|---|---|
| Cmpd No. | Structure |
| 988a | 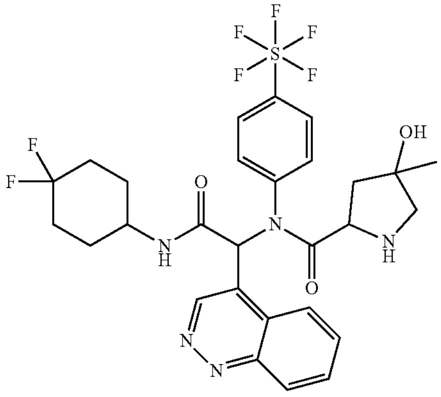 [SMILES: CC1(O)CNC(C(=O)N(c2ccc(S(F)(F)(F)(F)F)cc2)C(C(=O)NC2CCC(F)(F)CC2)c2cnnc3ccccc23)C1] |
| 988 | 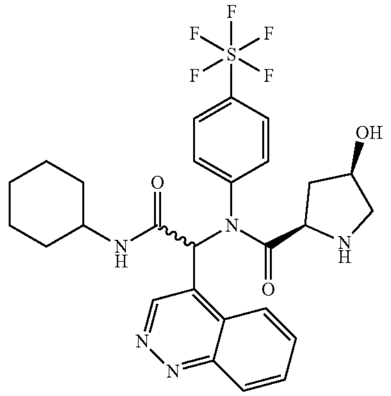 [SMILES: O=C(NC1CCCCC1)C(c1cnnc2ccccc12)N(C(=O)[C@H]1C[C@@H](O)CN1)c1ccc(S(F)(F)(F)(F)F)cc1] |
| 988b | 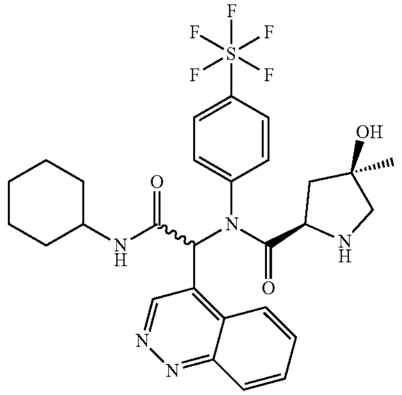 [SMILES: C[C@]1(O)CN[C@@H](C(=O)N(c2ccc(S(F)(F)(F)(F)F)cc2)C(C(=O)NC2CCCCC2)c2cnnc3ccccc23)C1] |
| 989b | 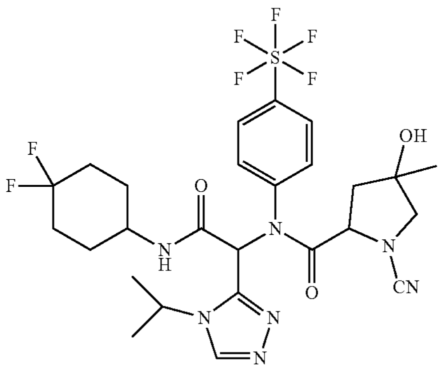 [SMILES: CC(C)n1cnnc1C(C(=O)NC1CCC(F)(F)CC1)N(C(=O)C1CC(C)(O)CN1C#N)c1ccc(S(F)(F)(F)(F)F)cc1] |
TABLE 1-continued
| Exemplary compounds. | |
|---|---|
| Cmpd No. | Structure |
| 989c | 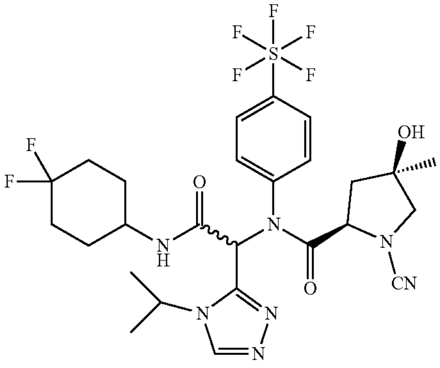 [SMILES: CC(C)n1cnnc1C(C(=O)NC1CCC(F)(F)CC1)N(C(=O)[C@H]1C[C@@](C)(O)CN1C#N)c1ccc(S(F)(F)(F)(F)F)cc1] |
| 989a | 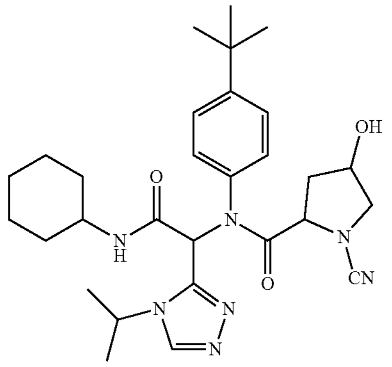 [SMILES: CC(C)n1cnnc1C(C(=O)NC1CCCCC1)N(C(=O)C1CC(O)CN1C#N)c1ccc(C(C)(C)C)cc1] |
| 989 | 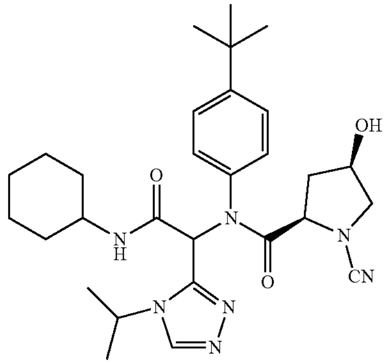 [SMILES: CC(C)n1cnnc1C(C(=O)NC1CCCCC1)N(C(=O)[C@H]1C[C@@H](O)CN1C#N)c1ccc(C(C)(C)C)cc1] |
| 990b | 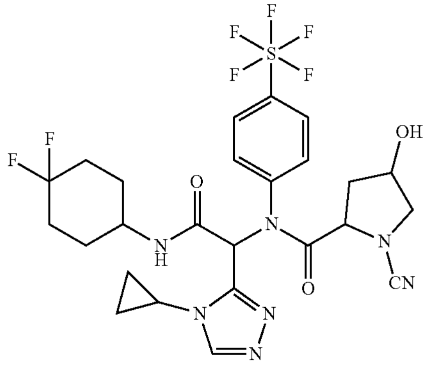 [SMILES: N#CN1CC(O)CC1C(=O)N(c1ccc(S(F)(F)(F)(F)F)cc1)C(C(=O)NC1CCC(F)(F)CC1)c1nncn1C1CC1] |

TABLE 1-continued
Exemplary compounds.
| Cmpd No. | Structure |
|---|---|
| 990c | 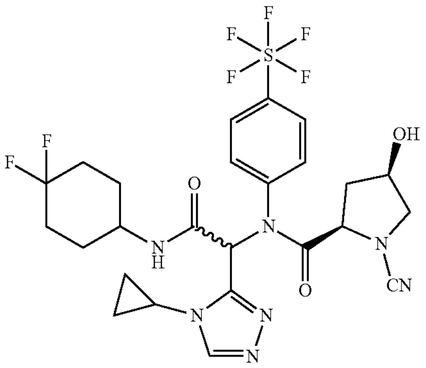 [SMILES: N#CN1C[C@H](O)C[C@@H]1C(=O)N(c1ccc(S(F)(F)(F)(F)F)cc1)C(C(=O)NC1CCC(F)(F)CC1)c1nncn1C1CC1] |
| 990a | 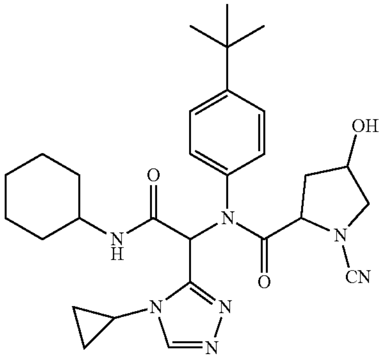 [SMILES: CC(C)(C)c1ccc(N(C(=O)C2CC(O)CN2C#N)C(C(=O)NC2CCCCC2)c2nncn2C2CC2)cc1] |
| 990 | 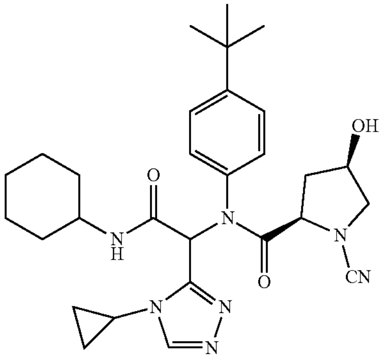 [SMILES: CC(C)(C)c1ccc(N(C(=O)[C@H]2C[C@@H](O)CN2C#N)C(C(=O)NC2CCCCC2)c2nncn2C2CC2)cc1] |
| 991a | 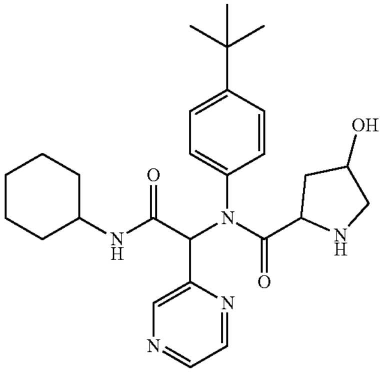 [SMILES: CC(C)(C)c1ccc(N(C(=O)C2CC(O)CN2)C(C(=O)NC2CCCCC2)c2cnccn2)cc1] |
TABLE 1-continued
Exemplary compounds.
| Cmpd No. | Structure |
|---|---|
| 991 | 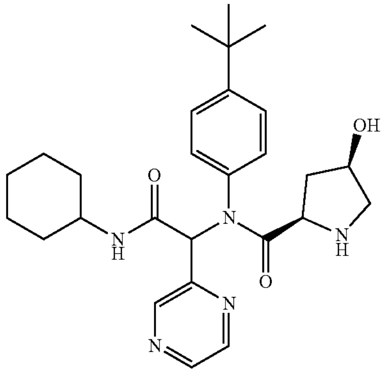 [SMILES: CC(C)(C)c1ccc(N(C(=O)[C@H]2C[C@@H](O)CN2)C(C(=O)NC2CCCCC2)c2cnccn2)cc1] |
| 993b | 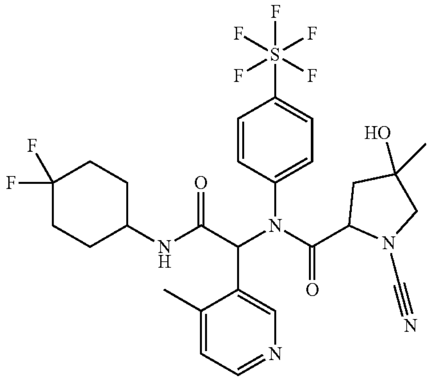 [SMILES: Cc1ccncc1C(C(=O)NC1CCC(F)(F)CC1)N(C(=O)C1CC(C)(O)CN1C#N)c1ccc(S(F)(F)(F)(F)F)cc1] |
| 993c | 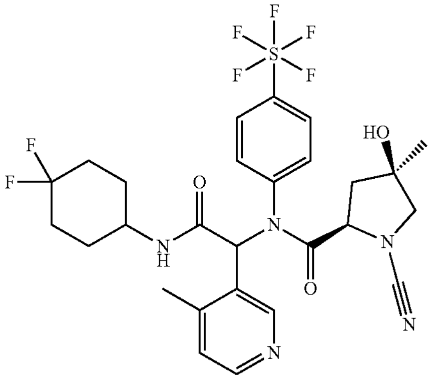 [SMILES: Cc1ccncc1C(C(=O)NC1CCC(F)(F)CC1)N(C(=O)[C@H]1C[C@@](C)(O)CN1C#N)c1ccc(S(F)(F)(F)(F)F)cc1] |
| 993a | 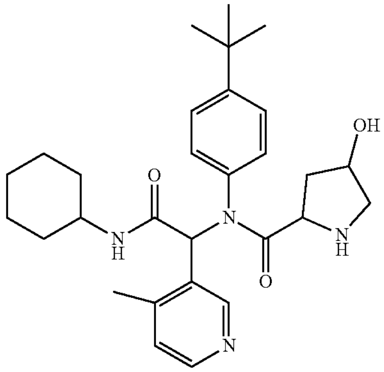 [SMILES: Cc1ccncc1C(C(=O)NC1CCCCC1)N(C(=O)C1CC(O)CN1)c1ccc(C(C)(C)C)cc1] |

TABLE 1-continued
Exemplary compounds.
| Cmpd No. | Structure |
| --- | --- |
| 993 | 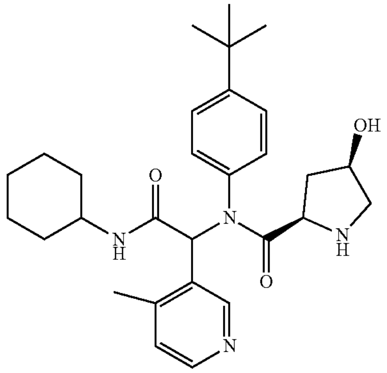 [SMILES: Cc1ccncc1C(C(=O)NC1CCCCC1)N(C(=O)[C@H]1C[C@@H](O)CN1)c1ccc(C(C)(C)C)cc1] |
| 994a | 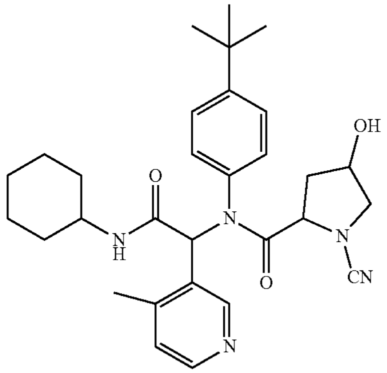 [SMILES: Cc1ccncc1C(C(=O)NC1CCCCC1)N(C(=O)C1CC(O)CN1C#N)c1ccc(C(C)(C)C)cc1] |
| 994 | 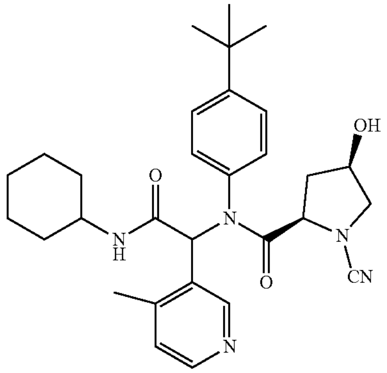 [SMILES: Cc1ccncc1C(C(=O)NC1CCCCC1)N(C(=O)[C@H]1C[C@@H](O)CN1C#N)c1ccc(C(C)(C)C)cc1] |
| 995b | 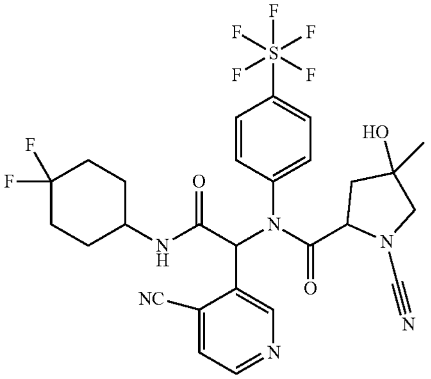 [SMILES: CC1(O)CC(C(=O)N(c2ccc(S(F)(F)(F)(F)F)cc2)C(C(=O)NC2CCC(F)(F)CC2)c2cnccc2C#N)N(C#N)C1] |
| 995c | 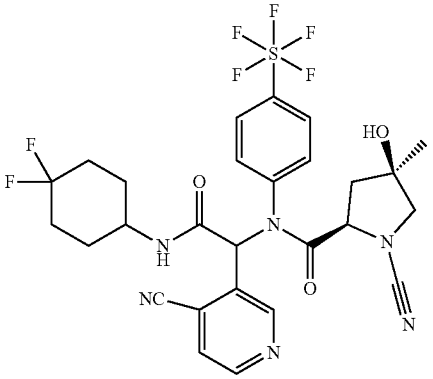 [SMILES: C[C@@]1(O)C[C@H](C(=O)N(c2ccc(S(F)(F)(F)(F)F)cc2)C(C(=O)NC2CCC(F)(F)CC2)c2cnccc2C#N)N(C#N)C1] |
| 995a | 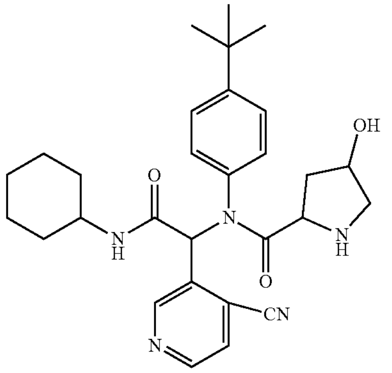 [SMILES: CC(C)(C)c1ccc(N(C(=O)C2CC(O)CN2)C(C(=O)NC2CCCCC2)c2cnccc2C#N)cc1] |
| 995 | 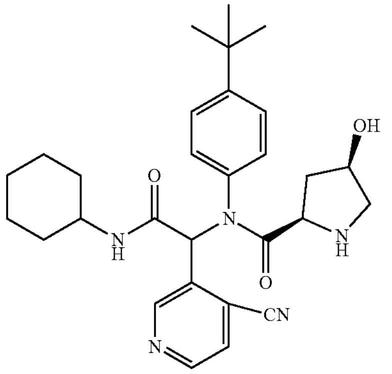 [SMILES: CC(C)(C)c1ccc(N(C(=O)[C@H]2C[C@@H](O)CN2)C(C(=O)NC2CCCCC2)c2cnccc2C#N)cc1] |
| 996a | 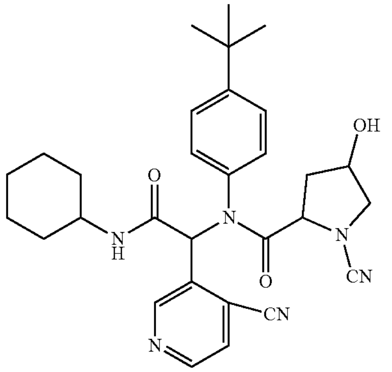 [SMILES: CC(C)(C)c1ccc(N(C(=O)C2CC(O)CN2C#N)C(C(=O)NC2CCCCC2)c2cnccc2C#N)cc1] |

TABLE 1-continued
| Exemplary compounds. | |
|---|---|
| Cmpd No. | Structure |
| 996 | 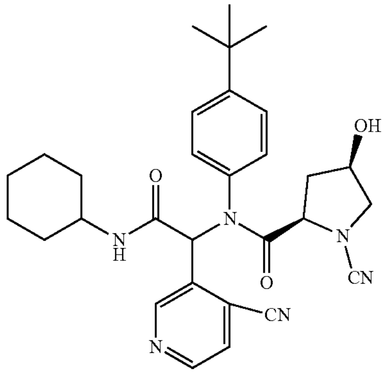 [SMILES: CC(C)(C)c1ccc(N(C(=O)[C@H]2C[C@@H](O)CN2C#N)C(C(=O)NC2CCCCC2)c2cnccc2C#N)cc1] |
| 997b | 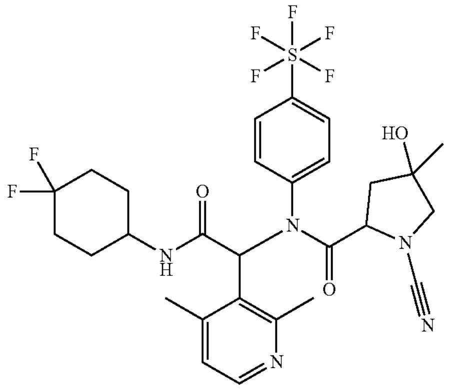 [SMILES: Cc1ccnc(C)c1C(C(=O)NC1CCC(F)(F)CC1)N(C(=O)C1CC(C)(O)CN1C#N)c1ccc(S(F)(F)(F)(F)F)cc1] |
| 997c | 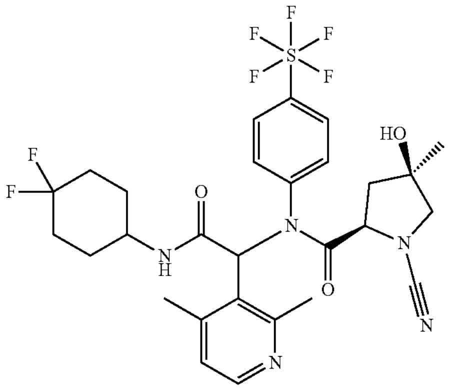 [SMILES: Cc1ccnc(C)c1C(C(=O)NC1CCC(F)(F)CC1)N(C(=O)[C@H]1C[C@@](C)(O)CN1C#N)c1ccc(S(F)(F)(F)(F)F)cc1] |
| 997a | 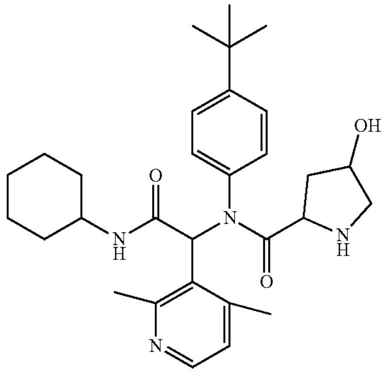 [SMILES: Cc1ccnc(C)c1C(C(=O)NC1CCCCC1)N(C(=O)C1CC(O)CN1)c1ccc(C(C)(C)C)cc1] |
TABLE 1-continued
| Exemplary compounds. | |
|---|---|
| Cmpd No. | Structure |
| 997 | 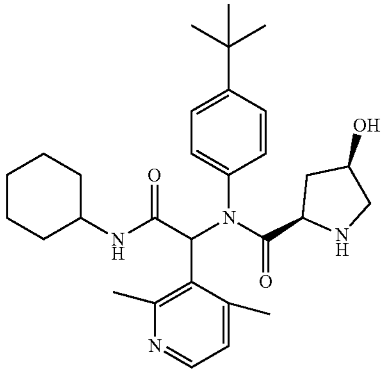 [SMILES: Cc1ccnc(C)c1C(C(=O)NC1CCCCC1)N(C(=O)[C@H]1C[C@@H](O)CN1)c1ccc(C(C)(C)C)cc1] |
| 998a | 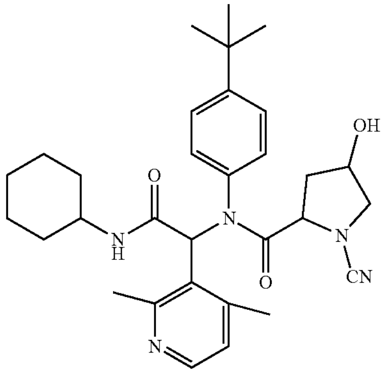 [SMILES: Cc1ccnc(C)c1C(C(=O)NC1CCCCC1)N(C(=O)C1CC(O)CN1C#N)c1ccc(C(C)(C)C)cc1] |
| 998 | 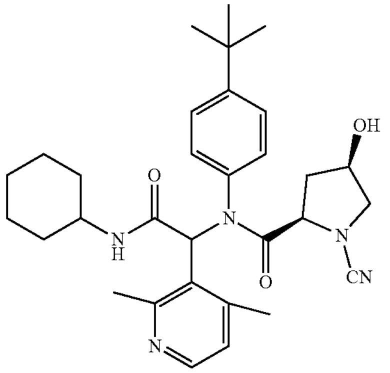 [SMILES: Cc1ccnc(C)c1C(C(=O)NC1CCCCC1)N(C(=O)[C@H]1C[C@@H](O)CN1C#N)c1ccc(C(C)(C)C)cc1] |
| 990d | 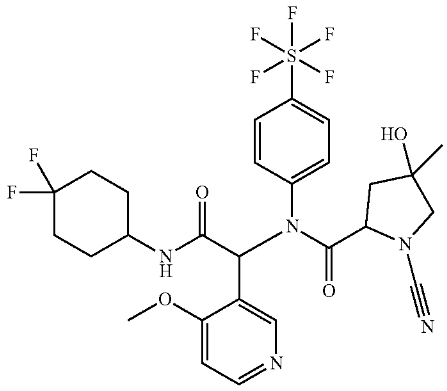 [SMILES: COc1ccncc1C(C(=O)NC1CCC(F)(F)CC1)N(C(=O)C1CC(C)(O)CN1C#N)c1ccc(S(F)(F)(F)(F)F)cc1] |

TABLE 1-continued
| Cmpd No. | Structure |
|---|---|
| 990e | 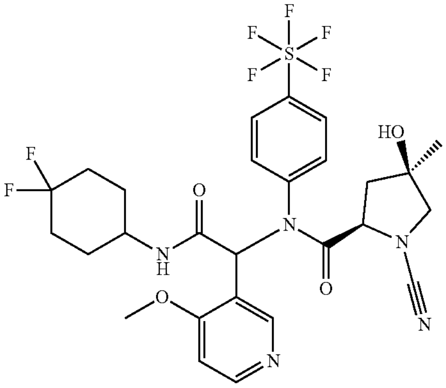 [SMILES: COc1ccncc1C(C(=O)NC1CCC(F)(F)CC1)N(C(=O)[C@H]1C[C@@](C)(O)CN1C#N)c1ccc(S(F)(F)(F)(F)F)cc1] |
| 999a | 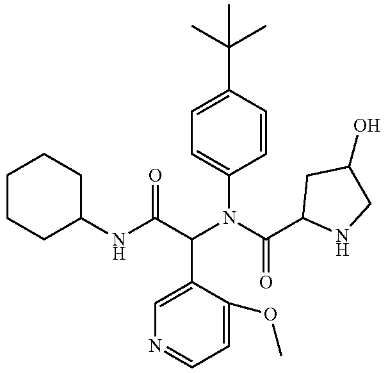 [SMILES: COc1ccncc1C(C(=O)NC1CCCCC1)N(C(=O)C1CC(O)CN1)c1ccc(C(C)(C)C)cc1] |
| 999 | 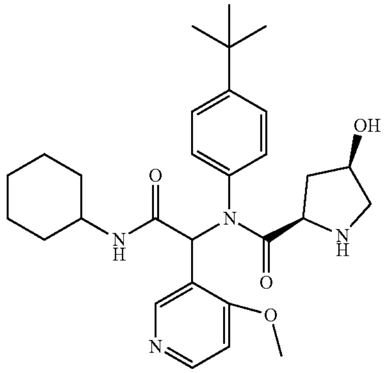 [SMILES: COc1ccncc1C(C(=O)NC1CCCCC1)N(C(=O)[C@H]1C[C@@H](O)CN1)c1ccc(C(C)(C)C)cc1] |
| 1000a | 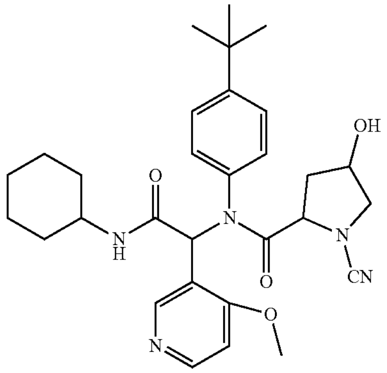 [SMILES: COc1ccncc1C(C(=O)NC1CCCCC1)N(C(=O)C1CC(O)CN1C#N)c1ccc(C(C)(C)C)cc1] |
TABLE 1-continued
| Cmpd No. | Structure |
|---|---|
| 1000 | 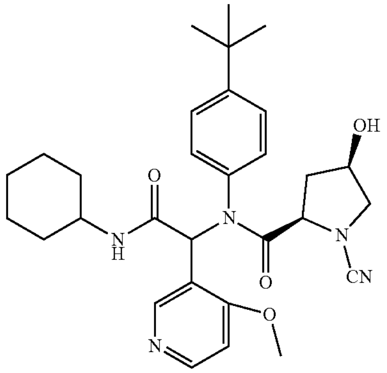 [SMILES: COc1ccncc1C(C(=O)NC1CCCCC1)N(C(=O)[C@H]1C[C@@H](O)CN1C#N)c1ccc(C(C)(C)C)cc1] |
| 1001b | 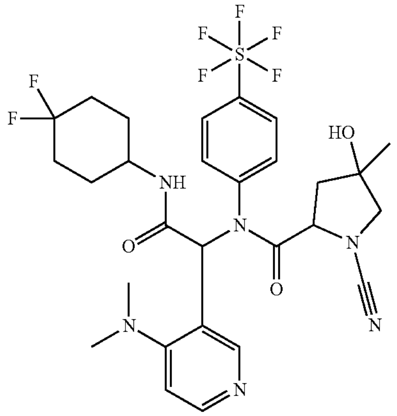 [SMILES: CN(C)c1ccncc1C(C(=O)NC1CCC(F)(F)CC1)N(C(=O)C1CC(C)(O)CN1C#N)c1ccc(S(F)(F)(F)(F)F)cc1] |
| 1001c | 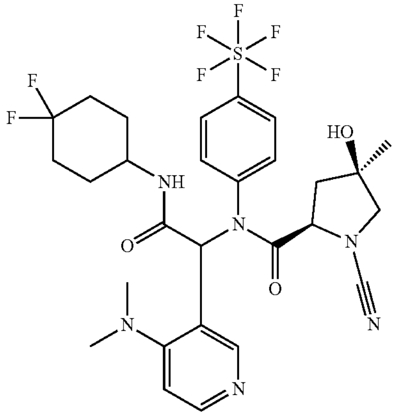 [SMILES: CN(C)c1ccncc1C(C(=O)NC1CCC(F)(F)CC1)N(C(=O)[C@H]1C[C@@](C)(O)CN1C#N)c1ccc(S(F)(F)(F)(F)F)cc1] |

Exemplary compounds.
| Cmpd No. | Structure |
|---|---|
| 1001a | 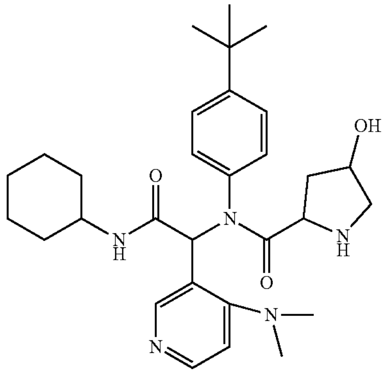 [SMILES: CN(C)c1ccncc1C(C(=O)NC1CCCCC1)N(C(=O)C1CC(O)CN1)c1ccc(C(C)(C)C)cc1] |
| 1001 | 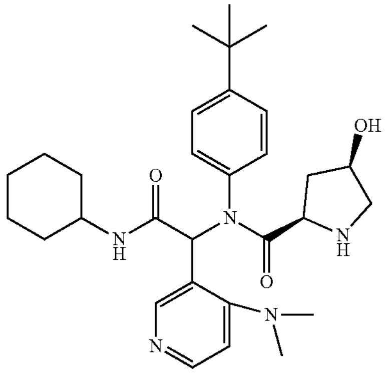 [SMILES: CN(C)c1ccncc1C(C(=O)NC1CCCCC1)N(C(=O)[C@H]1C[C@@H](O)CN1)c1ccc(C(C)(C)C)cc1] |
| 1002a | 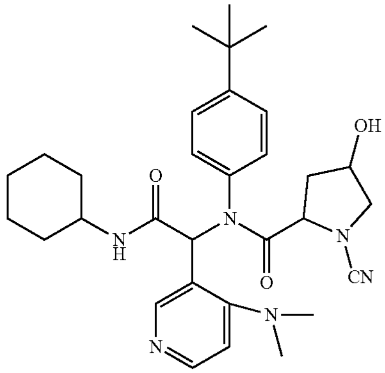 [SMILES: CN(C)c1ccncc1C(C(=O)NC1CCCCC1)N(C(=O)C1CC(O)CN1C#N)c1ccc(C(C)(C)C)cc1] |
| 1002 | 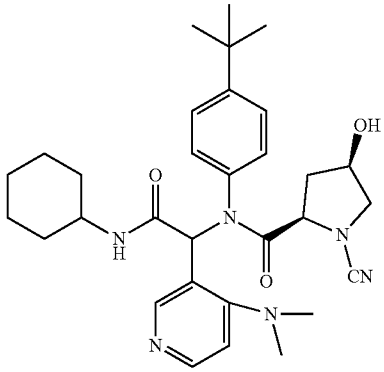 [SMILES: CN(C)c1ccncc1C(C(=O)NC1CCCCC1)N(C(=O)[C@H]1C[C@@H](O)CN1C#N)c1ccc(C(C)(C)C)cc1] |
Exemplary compounds.
| Cmpd No. | Structure |
|---|---|
| 1003b | 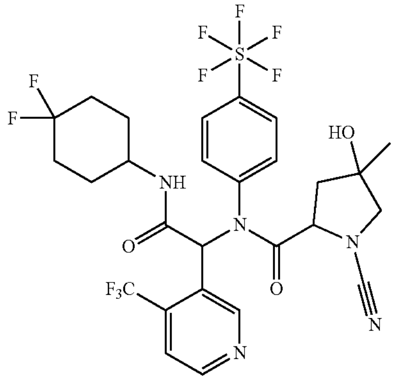 [SMILES: CC1(O)CC(C(=O)N(c2ccc(S(F)(F)(F)(F)F)cc2)C(C(=O)NC2CCC(F)(F)CC2)c2cnccc2C(F)(F)F)N(C#N)C1] |
| 1003c | 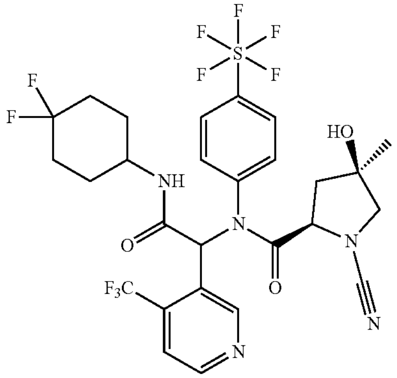 [SMILES: C[C@@]1(O)C[C@H](C(=O)N(c2ccc(S(F)(F)(F)(F)F)cc2)C(C(=O)NC2CCC(F)(F)CC2)c2cnccc2C(F)(F)F)N(C#N)C1] |
| 1003a | 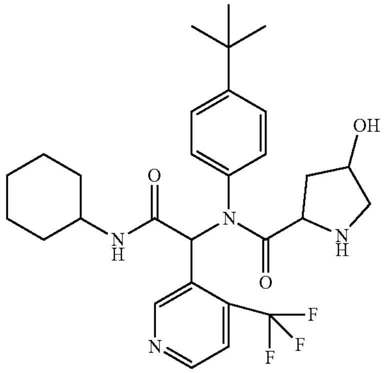 [SMILES: CC(C)(C)c1ccc(N(C(=O)C2CC(O)CN2)C(C(=O)NC2CCCCC2)c2cnccc2C(F)(F)F)cc1] |
| 1003 | 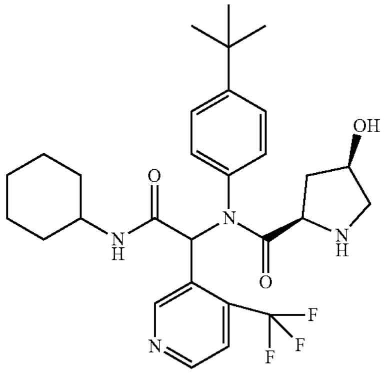 [SMILES: CC(C)(C)c1ccc(N(C(=O)[C@H]2C[C@@H](O)CN2)C(C(=O)NC2CCCCC2)c2cnccc2C(F)(F)F)cc1] |

TABLE 1-continued
| Exemplary compounds. | |
|---|---|
| Cmpd No. | Structure |
| 1004a | 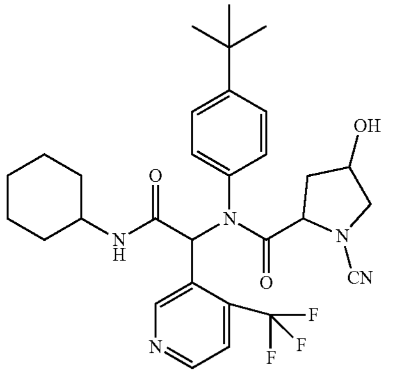 [SMILES: CC(C)(C)c1ccc(N(C(=O)C2CC(O)CN2C#N)C(C(=O)NC2CCCCC2)c2cnccc2C(F)(F)F)cc1] |
| 1004 | 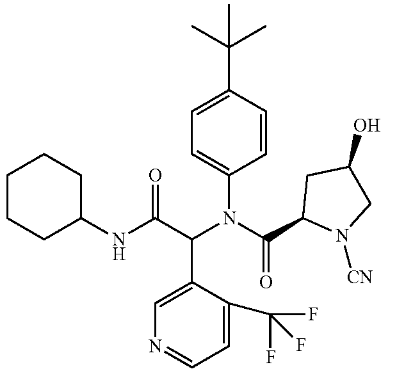 [SMILES: CC(C)(C)c1ccc(N(C(=O)[C@H]2C[C@@H](O)CN2C#N)C(C(=O)NC2CCCCC2)c2cnccc2C(F)(F)F)cc1] |
| 1005b | 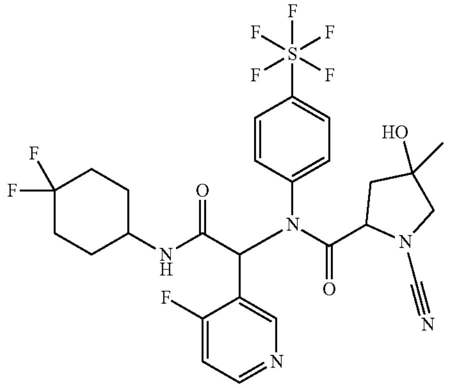 [SMILES: CC1(O)CC(C(=O)N(c2ccc(S(F)(F)(F)(F)F)cc2)C(C(=O)NC2CCC(F)(F)CC2)c2cnccc2F)N(C#N)C1] |
| 1005c | 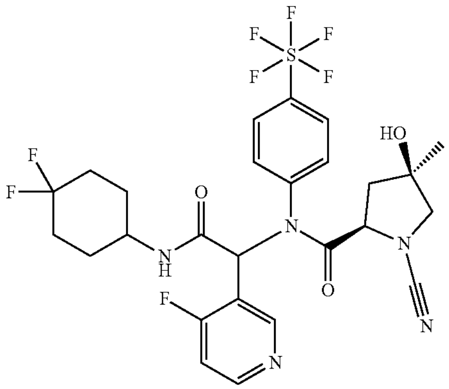 [SMILES: C[C@@]1(O)C[C@H](C(=O)N(c2ccc(S(F)(F)(F)(F)F)cc2)C(C(=O)NC2CCC(F)(F)CC2)c2cnccc2F)N(C#N)C1] |
TABLE 1-continued
| Exemplary compounds. | |
|---|---|
| Cmpd No. | Structure |
| 1005a | 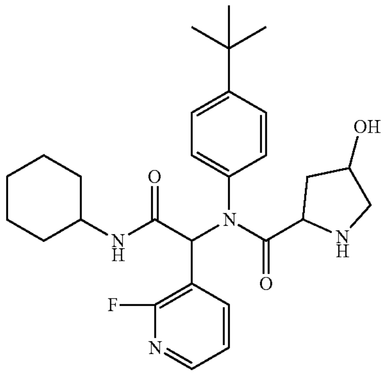 [SMILES: CC(C)(C)c1ccc(N(C(=O)C2CC(O)CN2)C(C(=O)NC2CCCCC2)c2cccnc2F)cc1] |
| 1005 | 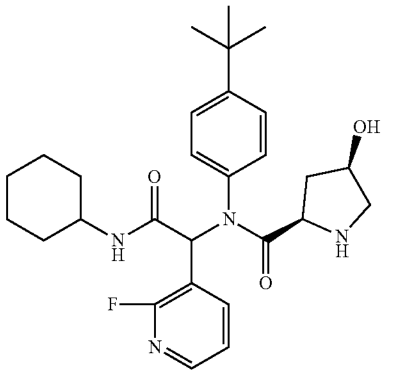 [SMILES: CC(C)(C)c1ccc(N(C(=O)[C@H]2C[C@@H](O)CN2)C(C(=O)NC2CCCCC2)c2cccnc2F)cc1] |
| 1006a | 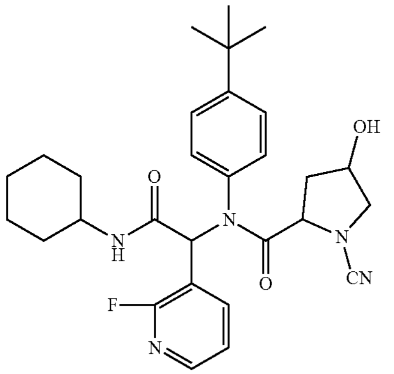 [SMILES: CC(C)(C)c1ccc(N(C(=O)C2CC(O)CN2C#N)C(C(=O)NC2CCCCC2)c2cccnc2F)cc1] |
| 1006 | 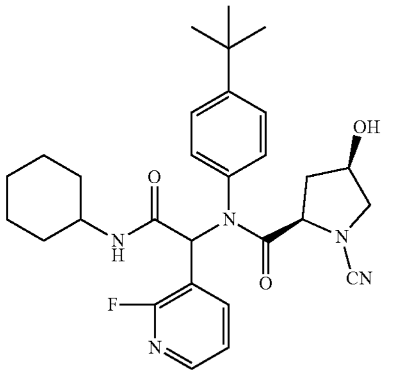 [SMILES: CC(C)(C)c1ccc(N(C(=O)[C@H]2C[C@@H](O)CN2C#N)C(C(=O)NC2CCCCC2)c2cccnc2F)cc1] |

TABLE 1-continued
| Cmpd No. | Structure |
| --- | --- |
| 1007b | 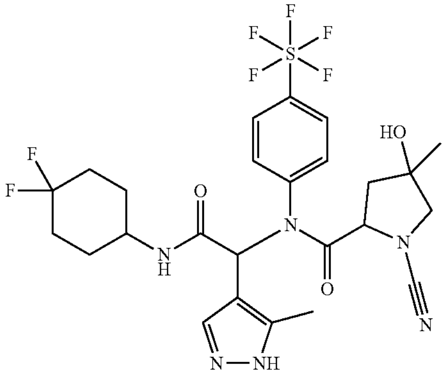 [SMILES: Cc1[nH]ncc1C(C(=O)NC1CCC(F)(F)CC1)N(C(=O)C1CC(C)(O)CN1C#N)c1ccc(S(F)(F)(F)(F)F)cc1] |
| 1007c | 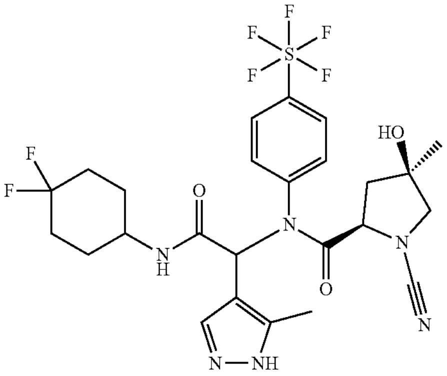 [SMILES: Cc1[nH]ncc1C(C(=O)NC1CCC(F)(F)CC1)N(C(=O)[C@H]1C[C@@](C)(O)CN1C#N)c1ccc(S(F)(F)(F)(F)F)cc1] |
| 1007a | 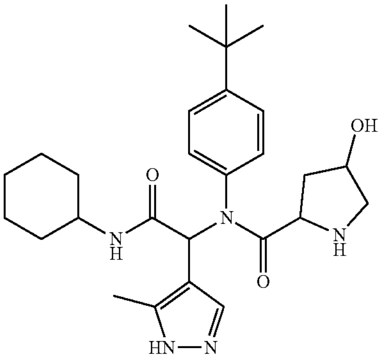 [SMILES: Cc1[nH]ncc1C(C(=O)NC1CCCCC1)N(C(=O)C1CC(O)CN1)c1ccc(C(C)(C)C)cc1] |
| 1007 | 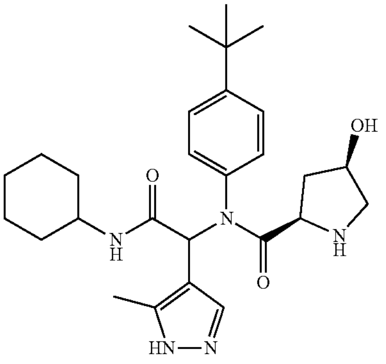 [SMILES: Cc1[nH]ncc1C(C(=O)NC1CCCCC1)N(C(=O)[C@H]1C[C@@H](O)CN1)c1ccc(C(C)(C)C)cc1] |
Exemplary compounds.
TABLE 1-continued
| Cmpd No. | Structure |
| --- | --- |
| 1009b | 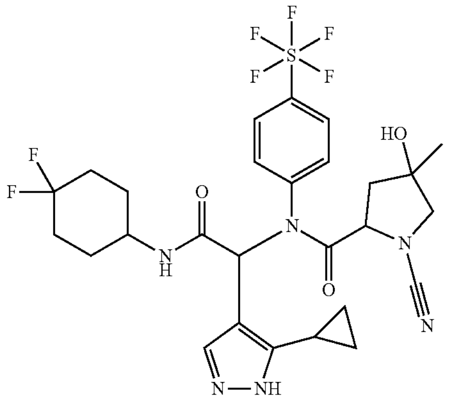 [SMILES: CC1(O)CC(C(=O)N(c2ccc(S(F)(F)(F)(F)F)cc2)C(C(=O)NC2CCC(F)(F)CC2)c2cn[nH]c2C2CC2)N(C#N)C1] |
| 1009c | 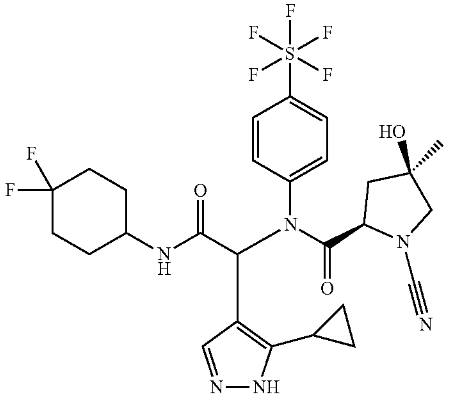 [SMILES: C[C@@]1(O)C[C@H](C(=O)N(c2ccc(S(F)(F)(F)(F)F)cc2)C(C(=O)NC2CCC(F)(F)CC2)c2cn[nH]c2C2CC2)N(C#N)C1] |
| 1009a | 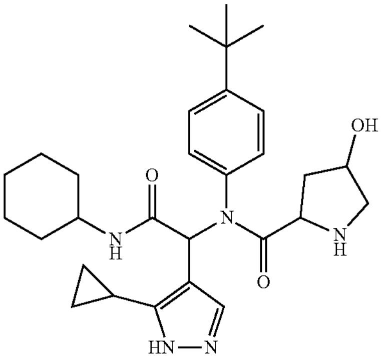 [SMILES: CC(C)(C)c1ccc(N(C(=O)C2CC(O)CN2)C(C(=O)NC2CCCCC2)c2cn[nH]c2C2CC2)cc1] |
| 1009 | 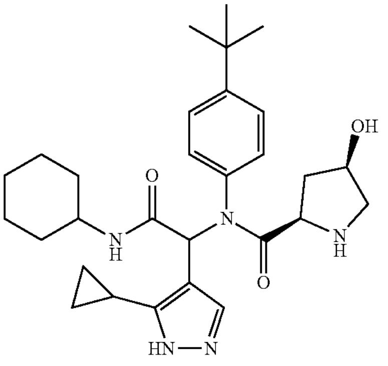 [SMILES: CC(C)(C)c1ccc(N(C(=O)[C@H]2C[C@@H](O)CN2)C(C(=O)NC2CCCCC2)c2cn[nH]c2C2CC2)cc1] |
Exemplary compounds.

TABLE 1-continued
| Exemplary compounds. | |
|---|---|
| Cmpd No. | Structure |
| 1010a | 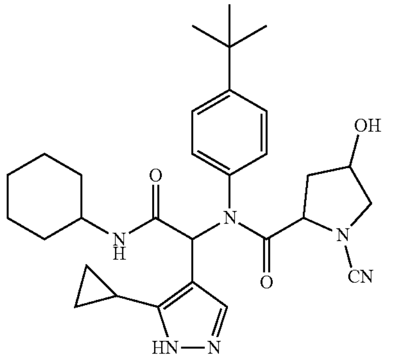 [SMILES: CC(C)(C)c1ccc(N(C(=O)C2CC(O)CN2C#N)C(C(=O)NC2CCCCC2)c2cn[nH]c2C2CC2)cc1] |
| 1010 | 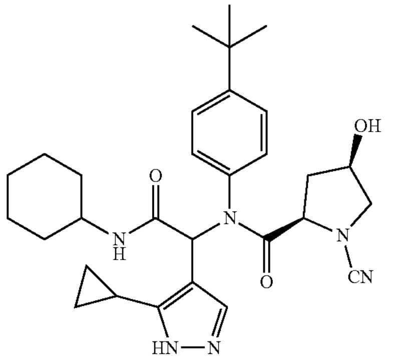 [SMILES: CC(C)(C)c1ccc(N(C(=O)[C@H]2C[C@@H](O)CN2C#N)C(C(=O)NC2CCCCC2)c2cn[nH]c2C2CC2)cc1] |
| 1011b | 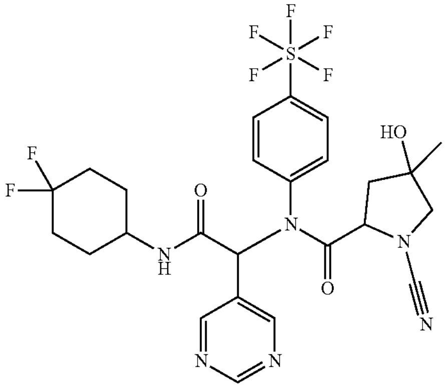 [SMILES: CC1(O)CC(C(=O)N(c2ccc(S(F)(F)(F)(F)F)cc2)C(C(=O)NC2CCC(F)(F)CC2)c2cncnc2)N(C#N)C1] |
| 1011c | 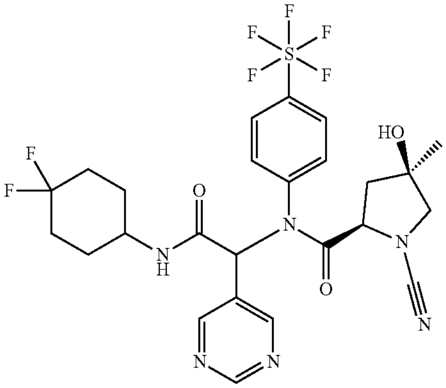 [SMILES: C[C@@]1(O)C[C@H](C(=O)N(c2ccc(S(F)(F)(F)(F)F)cc2)C(C(=O)NC2CCC(F)(F)CC2)c2cncnc2)N(C#N)C1] |
| 1011a | 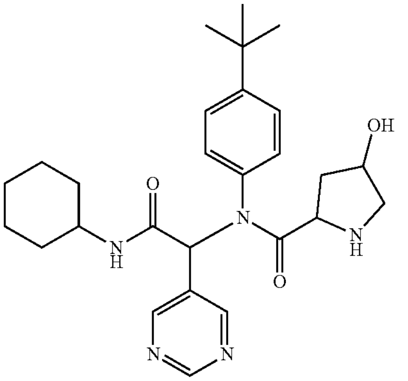 [SMILES: CC(C)(C)c1ccc(N(C(=O)C2CC(O)CN2)C(C(=O)NC2CCCCC2)c2cncnc2)cc1] |
| 1011 | 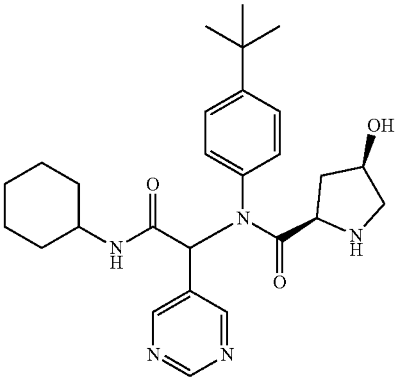 [SMILES: CC(C)(C)c1ccc(N(C(=O)[C@H]2C[C@@H](O)CN2)C(C(=O)NC2CCCCC2)c2cncnc2)cc1] |
| 1012a | 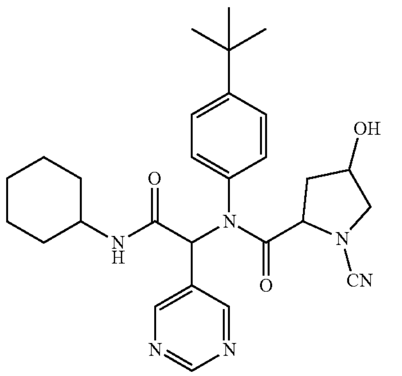 [SMILES: CC(C)(C)c1ccc(N(C(=O)C2CC(O)CN2C#N)C(C(=O)NC2CCCCC2)c2cncnc2)cc1] |
| 1012 | 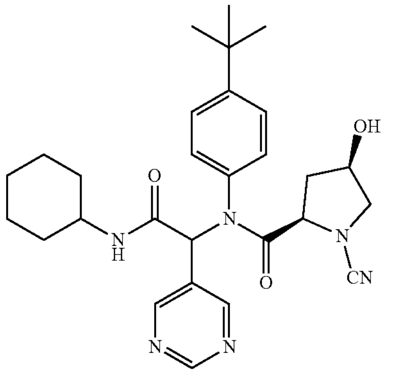 [SMILES: CC(C)(C)c1ccc(N(C(=O)[C@H]2C[C@@H](O)CN2C#N)C(C(=O)NC2CCCCC2)c2cncnc2)cc1] |

TABLE 1-continued
| Exemplary compounds. | |
|---|---|
| Cmpd No. | Structure |
| 1013a | 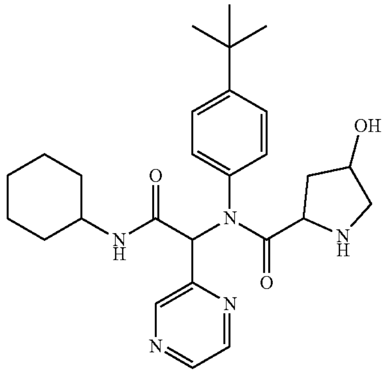 [SMILES: CC(C)(C)c1ccc(N(C(=O)C2CC(O)CN2)C(C(=O)NC2CCCCC2)c2cnccn2)cc1] |
| 1013 | 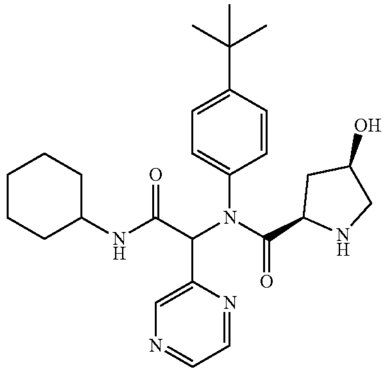 [SMILES: CC(C)(C)c1ccc(N(C(=O)[C@H]2C[C@@H](O)CN2)C(C(=O)NC2CCCCC2)c2cnccn2)cc1] |
| 1014a | 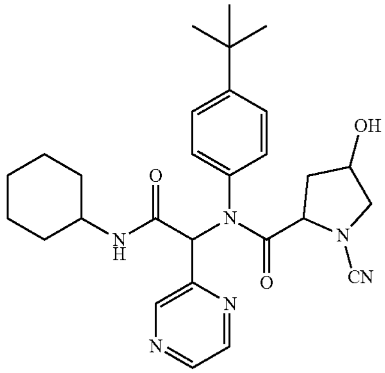 [SMILES: CC(C)(C)c1ccc(N(C(=O)C2CC(O)CN2C#N)C(C(=O)NC2CCCCC2)c2cnccn2)cc1] |
| 1014 | 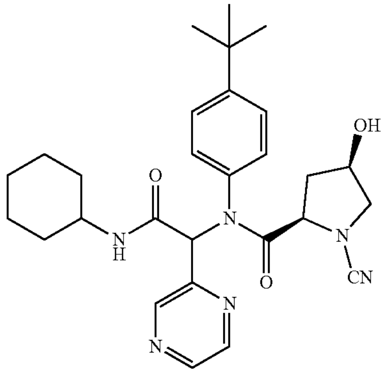 [SMILES: CC(C)(C)c1ccc(N(C(=O)[C@H]2C[C@@H](O)CN2C#N)C(C(=O)NC2CCCCC2)c2cnccn2)cc1] |
| 1015a | 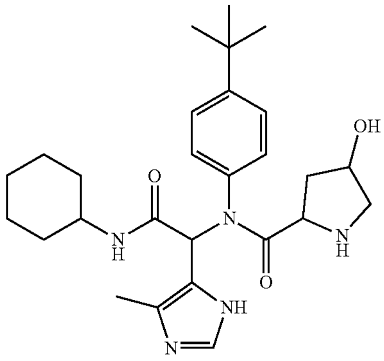 [SMILES: Cc1nc[nH]c1C(C(=O)NC1CCCCC1)N(C(=O)C1CC(O)CN1)c1ccc(C(C)(C)C)cc1] |
| 1015 | 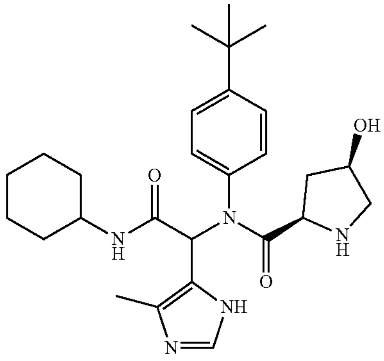 [SMILES: Cc1nc[nH]c1C(C(=O)NC1CCCCC1)N(C(=O)[C@H]1C[C@@H](O)CN1)c1ccc(C(C)(C)C)cc1] |
| 1016a | 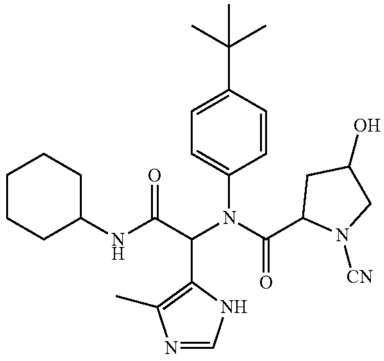 [SMILES: Cc1nc[nH]c1C(C(=O)NC1CCCCC1)N(C(=O)C1CC(O)CN1C#N)c1ccc(C(C)(C)C)cc1] |
| 1016 | 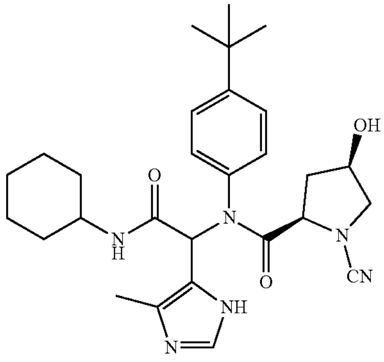 [SMILES: Cc1nc[nH]c1C(C(=O)NC1CCCCC1)N(C(=O)[C@H]1C[C@@H](O)CN1C#N)c1ccc(C(C)(C)C)cc1] |

TABLE 1-continued
| Exemplary compounds. | |
| --- | --- |
| Cmpd No. | Structure |
| 1017b | 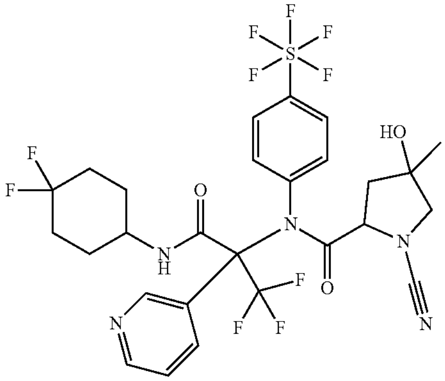 |
| 1017c | 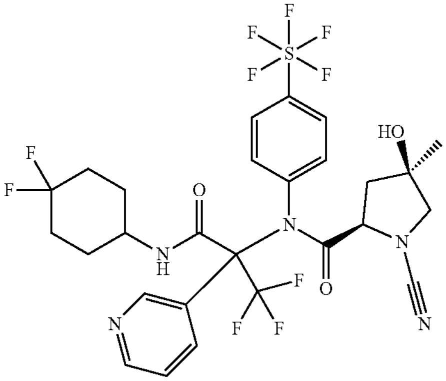 [SMILES: C[C@@]1(O)C[C@H](C(=O)N(c2ccc(S(F)(F)(F)(F)F)cc2)C(C(=O)NC2CCC(F)(F)CC2)(c2cccnc2)C(F)(F)F)N(C#N)C1] |
| 1017a | 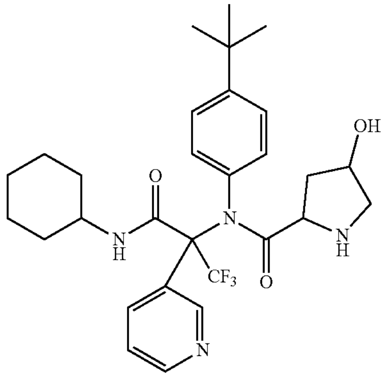 [SMILES: CC(C)(C)c1ccc(N(C(=O)C2CC(O)CN2)C(C(=O)NC2CCCCC2)(c2cccnc2)C(F)(F)F)cc1] |
| 1017 | 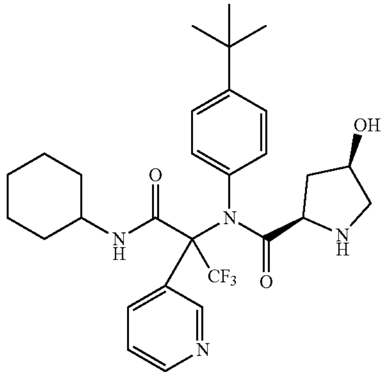 [SMILES: CC(C)(C)c1ccc(N(C(=O)[C@H]2C[C@@H](O)CN2)C(C(=O)NC2CCCCC2)(c2cccnc2)C(F)(F)F)cc1] |
TABLE 1-continued
| Exemplary compounds. | |
| --- | --- |
| Cmpd No. | Structure |
| 1018a | 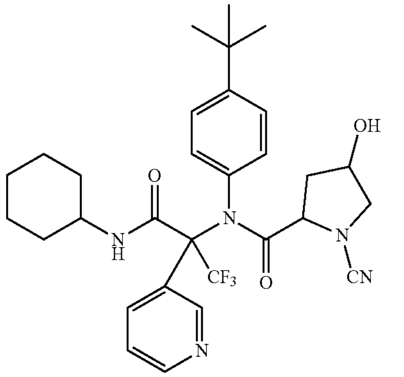 [SMILES: CC(C)(C)c1ccc(N(C(=O)C2CC(O)CN2C#N)C(C(=O)NC2CCCCC2)(c2cccnc2)C(F)(F)F)cc1] |
| 1018 | 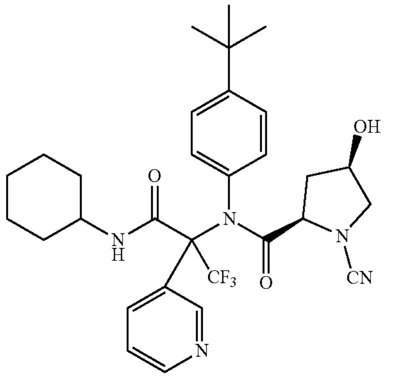 [SMILES: CC(C)(C)c1ccc(N(C(=O)[C@H]2C[C@@H](O)CN2C#N)C(C(=O)NC2CCCCC2)(c2cccnc2)C(F)(F)F)cc1] |
| 1019b | 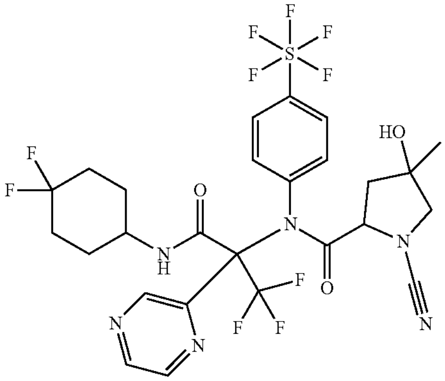 [SMILES: CC1(O)CC(C(=O)N(c2ccc(S(F)(F)(F)(F)F)cc2)C(C(=O)NC2CCC(F)(F)CC2)(c2cnccn2)C(F)(F)F)N(C#N)C1] |
| 1019c | 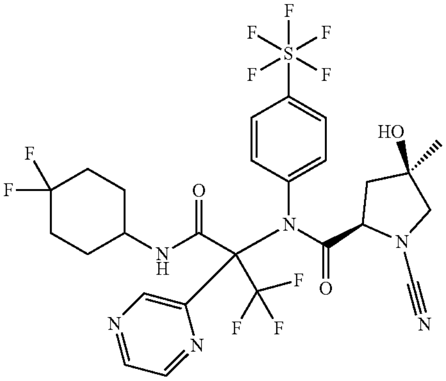 [SMILES: C[C@@]1(O)C[C@H](C(=O)N(c2ccc(S(F)(F)(F)(F)F)cc2)C(C(=O)NC2CCC(F)(F)CC2)(c2cnccn2)C(F)(F)F)N(C#N)C1] |

TABLE 1-continued
| Exemplary compounds. | |
|---|---|
| Cmpd No. | Structure |
| 1019a | 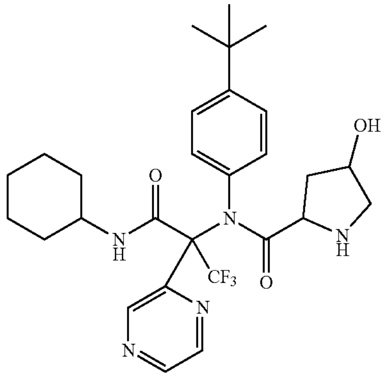 [SMILES: CC(C)(C)c1ccc(N(C(=O)C2CC(O)CN2)C(C(=O)NC2CCCCC2)(c2cnccn2)C(F)(F)F)cc1] |
| 1019 | 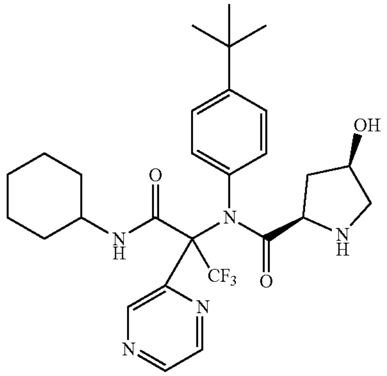 [SMILES: CC(C)(C)c1ccc(N(C(=O)[C@H]2C[C@@H](O)CN2)C(C(=O)NC2CCCCC2)(c2cnccn2)C(F)(F)F)cc1] |
| 1020a | 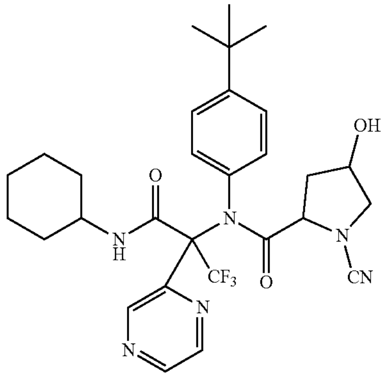 [SMILES: CC(C)(C)c1ccc(N(C(=O)C2CC(O)CN2C#N)C(C(=O)NC2CCCCC2)(c2cnccn2)C(F)(F)F)cc1] |
| 1020 | 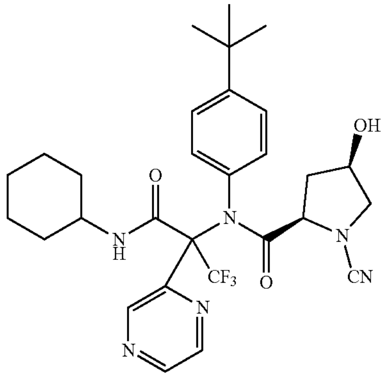 [SMILES: CC(C)(C)c1ccc(N(C(=O)[C@H]2C[C@@H](O)CN2C#N)C(C(=O)NC2CCCCC2)(c2cnccn2)C(F)(F)F)cc1] |
TABLE 1-continued
| Exemplary compounds. | |
|---|---|
| Cmpd No. | Structure |
| 1021a | 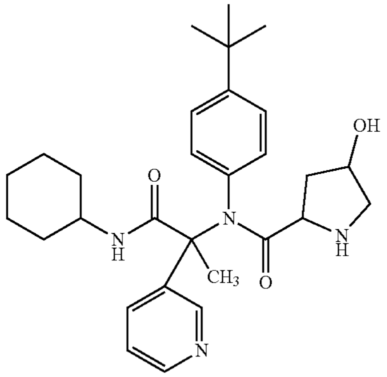 [SMILES: CC(C)(C)c1ccc(N(C(=O)C2CC(O)CN2)C(C)(C(=O)NC2CCCCC2)c2cccnc2)cc1] |
| 1021 | 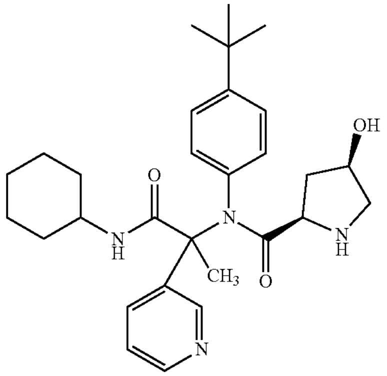 |
| 1022a | 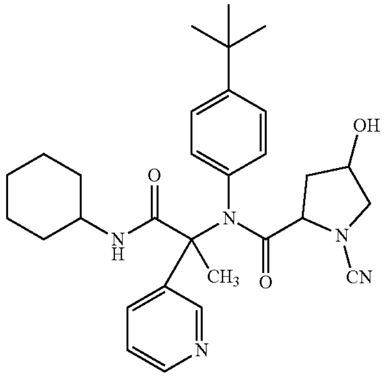 [SMILES: CC(C)(C)c1ccc(N(C(=O)C2CC(O)CN2C#N)C(C)(C(=O)NC2CCCCC2)c2cccnc2)cc1] |
| 1022 | 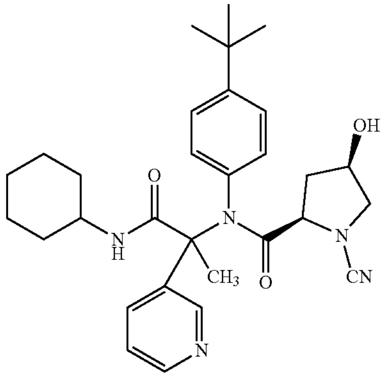 [SMILES: CC(C)(C)c1ccc(N(C(=O)[C@H]2C[C@@H](O)CN2C#N)C(C)(C(=O)NC2CCCCC2)c2cccnc2)cc1] |

TABLE 1-continued
Exemplary compounds.
| Cmpd No. | Structure |
|---|---|
| 1023a | 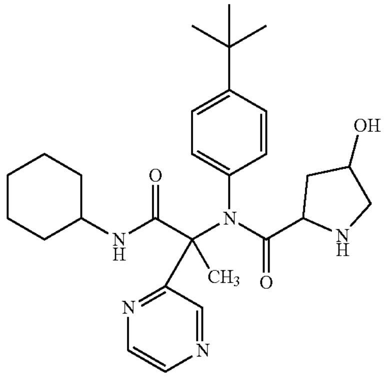 [SMILES: CC(C)(C)c1ccc(N(C(=O)C2CC(O)CN2)C(C)(C(=O)NC2CCCCC2)c2cnccn2)cc1] |
| 1023 | 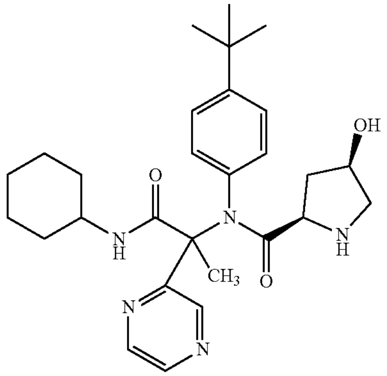 [SMILES: CC(C)(C)c1ccc(N(C(=O)[C@H]2C[C@@H](O)CN2)C(C)(C(=O)NC2CCCCC2)c2cnccn2)cc1] |
| 1024a | 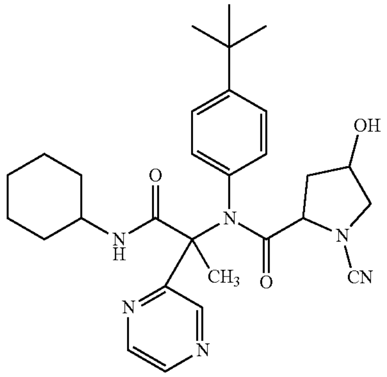 [SMILES: CC(C)(C)c1ccc(N(C(=O)C2CC(O)CN2C#N)C(C)(C(=O)NC2CCCCC2)c2cnccn2)cc1] |
| 1024 | 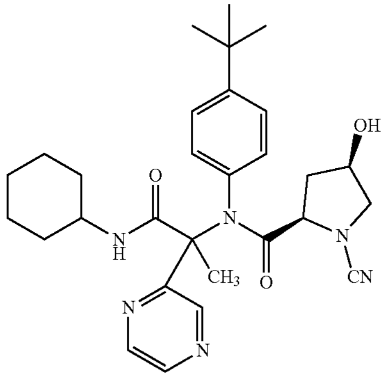 [SMILES: CC(C)(C)c1ccc(N(C(=O)[C@H]2C[C@@H](O)CN2C#N)C(C)(C(=O)NC2CCCCC2)c2cnccn2)cc1] |
TABLE 1-continued
Exemplary compounds.
| Cmpd No. | Structure |
|---|---|
| 1025a | 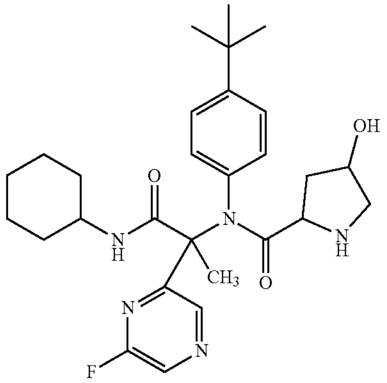 [SMILES: CC(C)(C)c1ccc(N(C(=O)C2CC(O)CN2)C(C)(C(=O)NC2CCCCC2)c2cncc(F)n2)cc1] |
| 1025 | 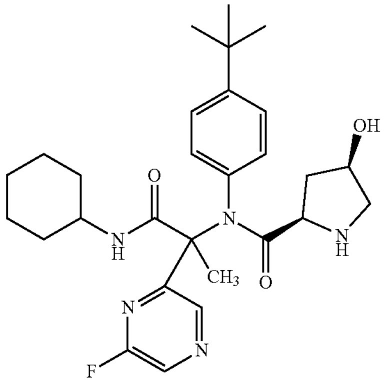 [SMILES: CC(C)(C)c1ccc(N(C(=O)[C@H]2C[C@@H](O)CN2)C(C)(C(=O)NC2CCCCC2)c2cncc(F)n2)cc1] |
| 1026a | 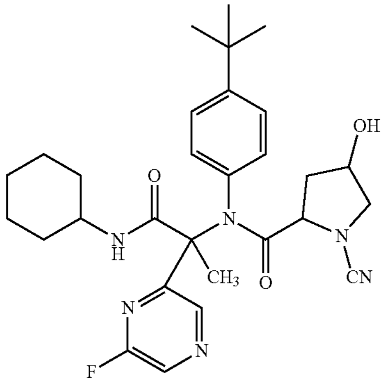 [SMILES: CC(C)(C)c1ccc(N(C(=O)C2CC(O)CN2C#N)C(C)(C(=O)NC2CCCCC2)c2cncc(F)n2)cc1] |
| 1027 | 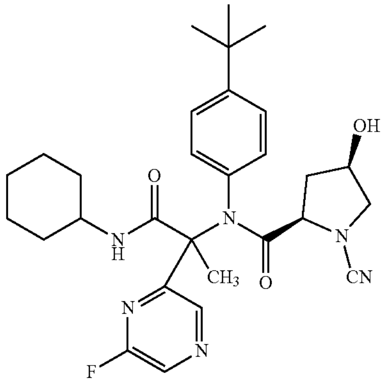 [SMILES: CC(C)(C)c1ccc(N(C(=O)[C@H]2C[C@@H](O)CN2C#N)C(C)(C(=O)NC2CCCCC2)c2cncc(F)n2)cc1] |

TABLE 1-continued
Exemplary compounds.
| Cmpd No. | Structure |
|---|---|
| 1027a | 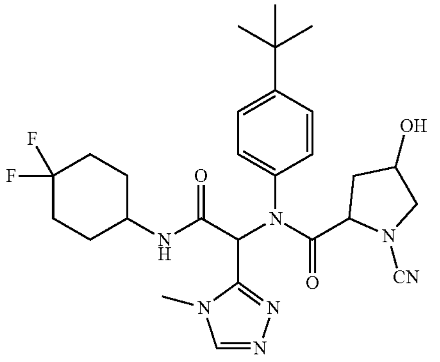 [SMILES: Cn1cnnc1C(C(=O)NC1CCC(F)(F)CC1)N(C(=O)C1CC(O)CN1C#N)c1ccc(C(C)(C)C)cc1] |
| 1027 | 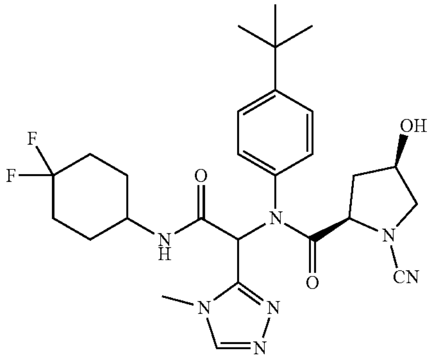 [SMILES: Cn1cnnc1C(C(=O)NC1CCC(F)(F)CC1)N(C(=O)[C@H]1C[C@@H](O)CN1C#N)c1ccc(C(C)(C)C)cc1] |
| 1028a | 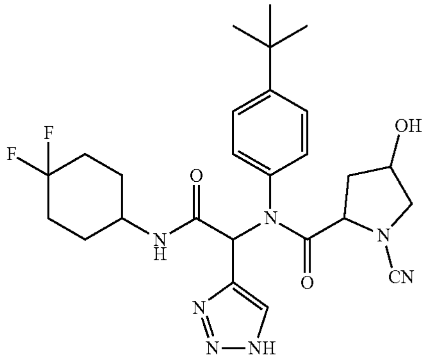 [SMILES: CC(C)(C)c1ccc(N(C(=O)C2CC(O)CN2C#N)C(C(=O)NC2CCC(F)(F)CC2)c2c[nH]nn2)cc1] |
| 1028 | 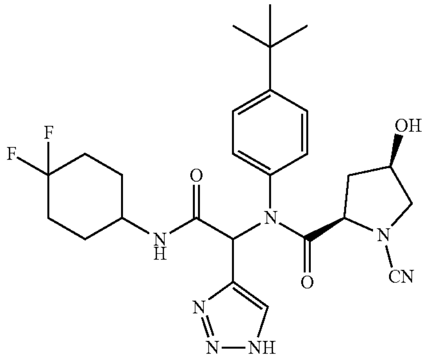 [SMILES: CC(C)(C)c1ccc(N(C(=O)[C@H]2C[C@@H](O)CN2C#N)C(C(=O)NC2CCC(F)(F)CC2)c2c[nH]nn2)cc1] |
TABLE 1-continued
Exemplary compounds.
| Cmpd No. | Structure |
|---|---|
| 1029a | 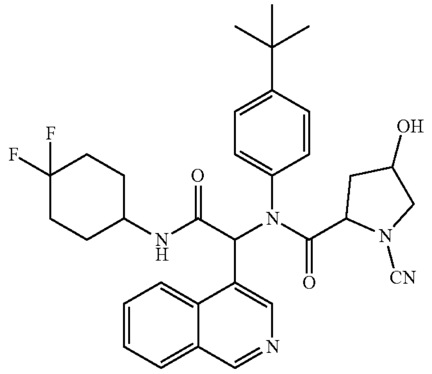 [SMILES: CC(C)(C)c1ccc(N(C(=O)C2CC(O)CN2C#N)C(C(=O)NC2CCC(F)(F)CC2)c2cncc3ccccc23)cc1] |
| 1029 | 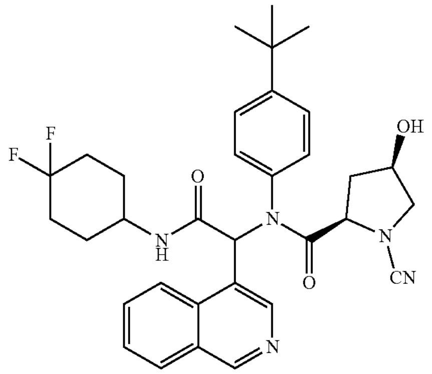 [SMILES: CC(C)(C)c1ccc(N(C(=O)[C@H]2C[C@@H](O)CN2C#N)C(C(=O)NC2CCC(F)(F)CC2)c2cncc3ccccc23)cc1] |
| 1030a | 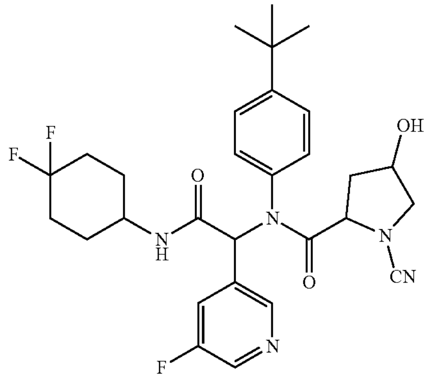 [SMILES: CC(C)(C)c1ccc(N(C(=O)C2CC(O)CN2C#N)C(C(=O)NC2CCC(F)(F)CC2)c2cncc(F)c2)cc1] |
| 1030 | 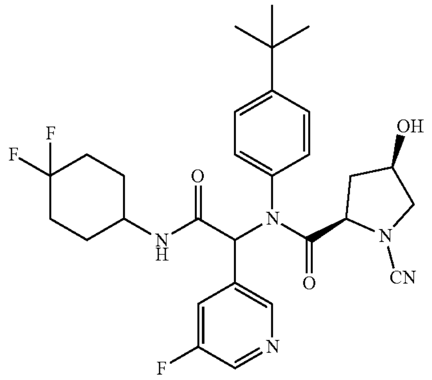 [SMILES: CC(C)(C)c1ccc(N(C(=O)[C@H]2C[C@@H](O)CN2C#N)C(C(=O)NC2CCC(F)(F)CC2)c2cncc(F)c2)cc1] |

TABLE 1-continued
| Exemplary compounds. | |
|---|---|
| Cmpd No. | Structure |
| 1031a | 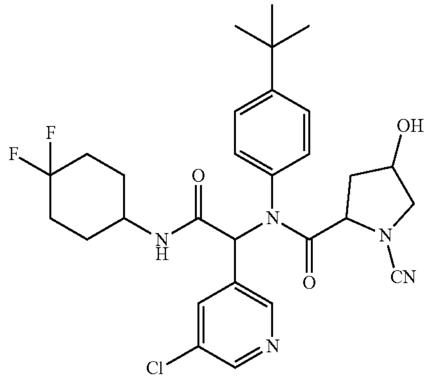 [SMILES: CC(C)(C)c1ccc(N(C(=O)C2CC(O)CN2C#N)C(C(=O)NC2CCC(F)(F)CC2)c2cncc(Cl)c2)cc1] |
| 1031 | 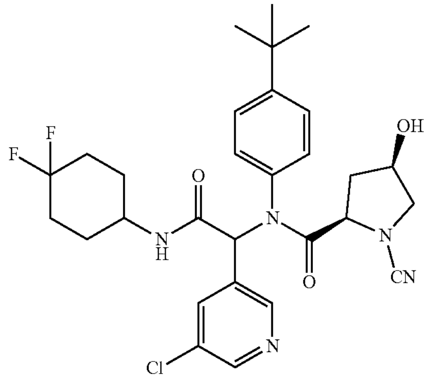 [SMILES: CC(C)(C)c1ccc(N(C(=O)[C@H]2C[C@@H](O)CN2C#N)C(C(=O)NC2CCC(F)(F)CC2)c2cncc(Cl)c2)cc1] |
| 1032a | 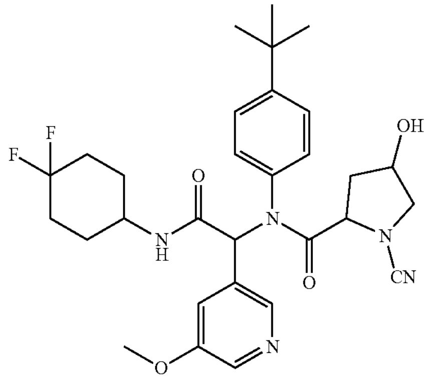 [SMILES: COc1cncc(C(C(=O)NC2CCC(F)(F)CC2)N(C(=O)C2CC(O)CN2C#N)c2ccc(C(C)(C)C)cc2)c1] |
| 1032 | 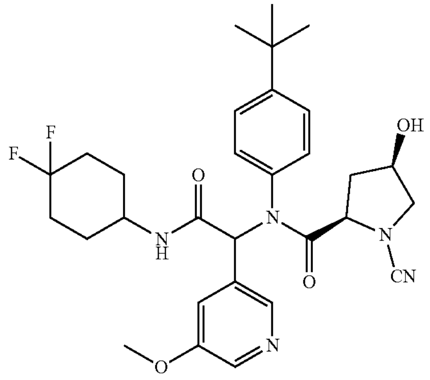 [SMILES: COc1cncc(C(C(=O)NC2CCC(F)(F)CC2)N(C(=O)[C@H]2C[C@@H](O)CN2C#N)c2ccc(C(C)(C)C)cc2)c1] |
TABLE 1-continued
| Exemplary compounds. | |
|---|---|
| Cmpd No. | Structure |
| 1033a | 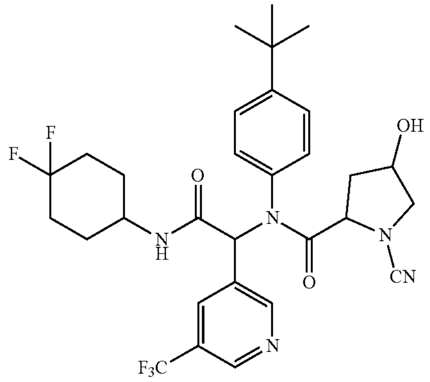 [SMILES: CC(C)(C)c1ccc(N(C(=O)C2CC(O)CN2C#N)C(C(=O)NC2CCC(F)(F)CC2)c2cncc(C(F)(F)F)c2)cc1] |
| 1033 | 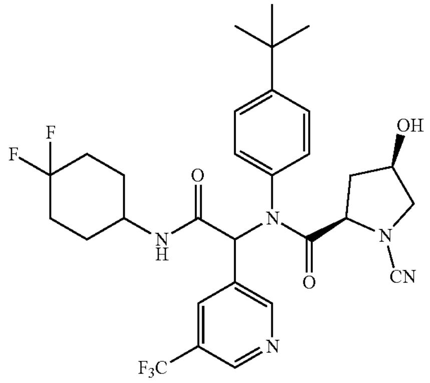 [SMILES: CC(C)(C)c1ccc(N(C(=O)[C@H]2C[C@@H](O)CN2C#N)C(C(=O)NC2CCC(F)(F)CC2)c2cncc(C(F)(F)F)c2)cc1] |
| 1034a | 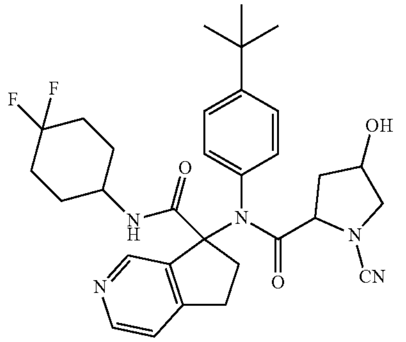 [SMILES: CC(C)(C)c1ccc(N(C(=O)C2CC(O)CN2C#N)C2(C(=O)NC3CCC(F)(F)CC3)CCc3ccncc32)cc1] |
| 1034 | 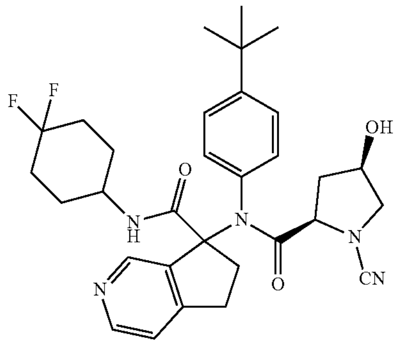 [SMILES: CC(C)(C)c1ccc(N(C(=O)[C@H]2C[C@@H](O)CN2C#N)C2(C(=O)NC3CCC(F)(F)CC3)CCc3ccncc32)cc1] |

TABLE 1-continued
| Exemplary compounds. | |
|---|---|
| Cmpd No. | Structure |
| 1035a | 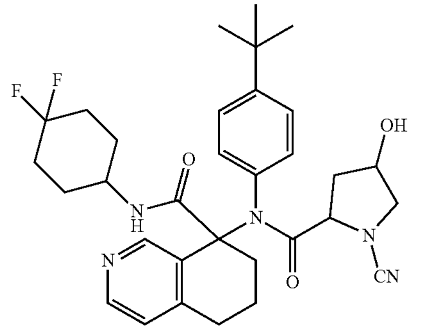 [SMILES: CC(C)(C)c1ccc(N(C(=O)C2CC(O)CN2C#N)C2(C(=O)NC3CCC(F)(F)CC3)CCCc3ccncc32)cc1] |
| 1035 | 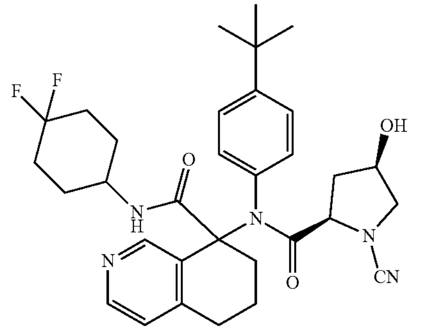 [SMILES: CC(C)(C)c1ccc(N(C(=O)[C@H]2C[C@@H](O)CN2C#N)C2(C(=O)NC3CCC(F)(F)CC3)CCCc3ccncc32)cc1] |
| 1036a | 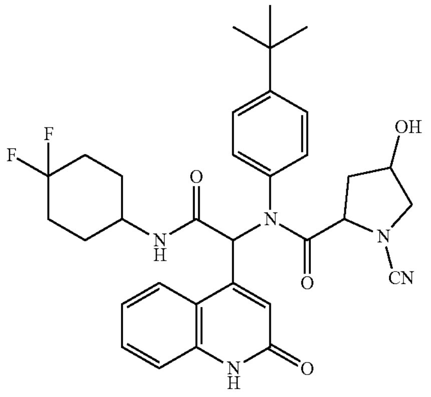 [SMILES: CC(C)(C)c1ccc(N(C(=O)C2CC(O)CN2C#N)C(C(=O)NC2CCC(F)(F)CC2)c2cc(=O)[nH]c3ccccc23)cc1] |
| 1036 | 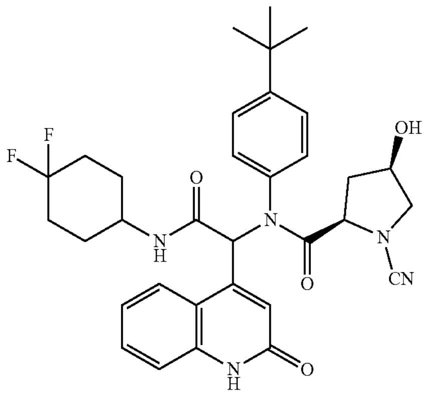 [SMILES: CC(C)(C)c1ccc(N(C(=O)[C@H]2C[C@@H](O)CN2C#N)C(C(=O)NC2CCC(F)(F)CC2)c2cc(=O)[nH]c3ccccc23)cc1] |
TABLE 1-continued
| Exemplary compounds. | |
|---|---|
| Cmpd No. | Structure |
| 1037a | 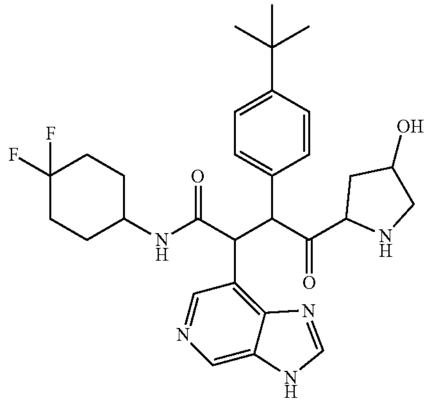 [SMILES: CC(C)(C)c1ccc(C(C(=O)C2CC(O)CN2)C(C(=O)NC2CCC(F)(F)CC2)c2cncc3[nH]cnc23)cc1] |
| 1037 | 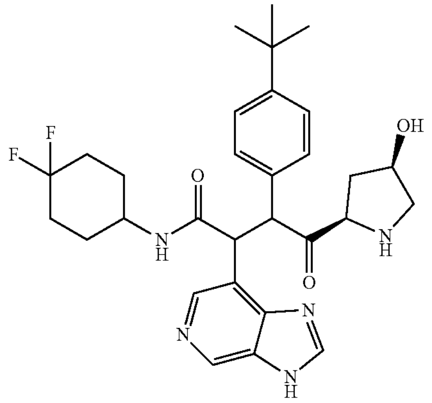 [SMILES: CC(C)(C)c1ccc(C(C(=O)[C@H]2C[C@@H](O)CN2)C(C(=O)NC2CCC(F)(F)CC2)c2cncc3[nH]cnc23)cc1] |
| 1038a | 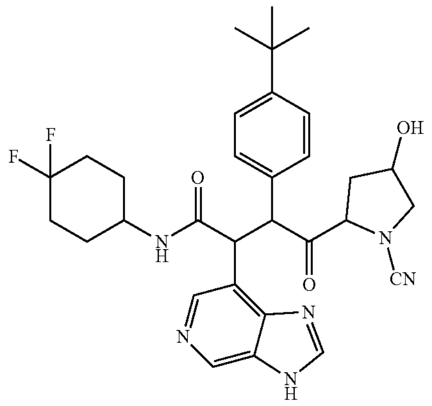 [SMILES: CC(C)(C)c1ccc(C(C(=O)C2CC(O)CN2C#N)C(C(=O)NC2CCC(F)(F)CC2)c2cncc3[nH]cnc23)cc1] |

TABLE 1-continued
| Cmpd No. | Structure |
|---|---|
| 1038 | 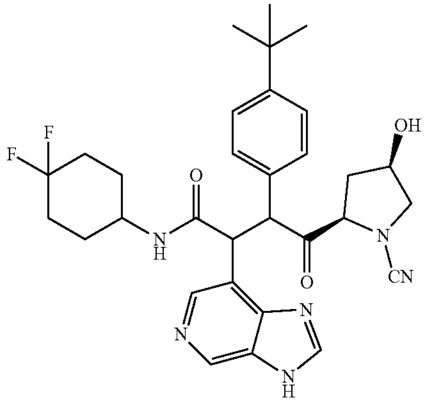 [SMILES: CC(C)(C)c1ccc(C(C(=O)[C@H]2C[C@@H](O)CN2C#N)C(C(=O)NC2CCC(F)(F)CC2)c2cncc3[nH]cnc23)cc1] |
| 1039a | 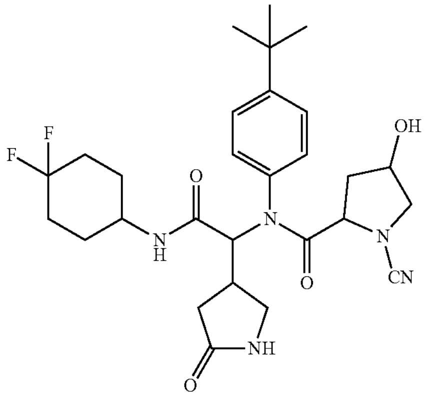 [SMILES: CC(C)(C)c1ccc(N(C(=O)C2CC(O)CN2C#N)C(C(=O)NC2CCC(F)(F)CC2)C2CNC(=O)C2)cc1] |
| 1039 | 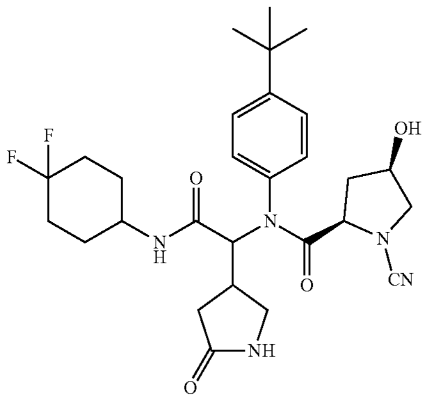 [SMILES: CC(C)(C)c1ccc(N(C(=O)[C@H]2C[C@@H](O)CN2C#N)C(C(=O)NC2CCC(F)(F)CC2)C2CNC(=O)C2)cc1] |
TABLE 1-continued
| Cmpd No. | Structure |
|---|---|
| 1040a | 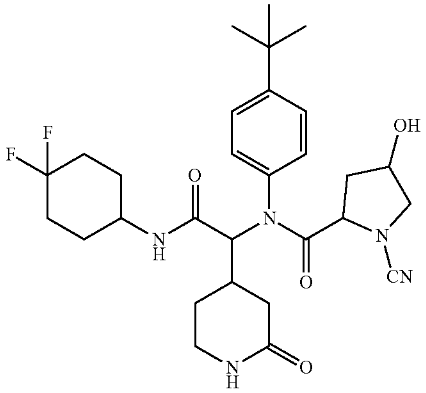 [SMILES: CC(C)(C)c1ccc(N(C(=O)C2CC(O)CN2C#N)C(C(=O)NC2CCC(F)(F)CC2)C2CCNC(=O)C2)cc1] |
| 1040 | 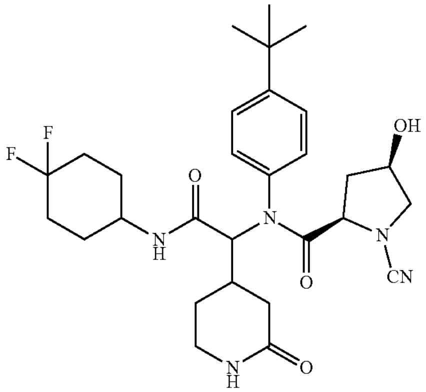 [SMILES: CC(C)(C)c1ccc(N(C(=O)[C@H]2C[C@@H](O)CN2C#N)C(C(=O)NC2CCC(F)(F)CC2)C2CCNC(=O)C2)cc1] |
| 1041a | 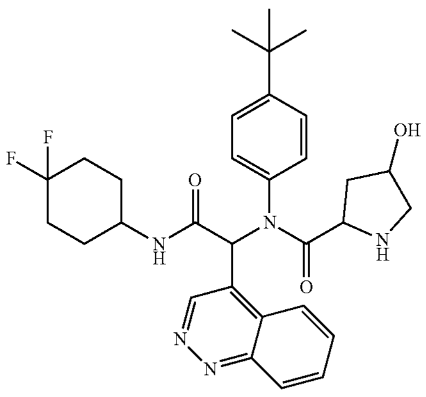 [SMILES: CC(C)(C)c1ccc(N(C(=O)C2CC(O)CN2)C(C(=O)NC2CCC(F)(F)CC2)c2cnnc3ccccc23)cc1] |

TABLE 1-continued
Exemplary compounds.
| Cmpd No. | Structure |
| --- | --- |
| 1041 | 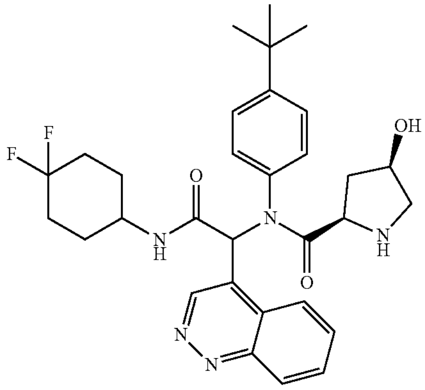 [SMILES: CC(C)(C)c1ccc(N(C(=O)[C@H]2C[C@@H](O)CN2)C(C(=O)NC2CCC(F)(F)CC2)c2cnnc3ccccc23)cc1] |
| 1042a | 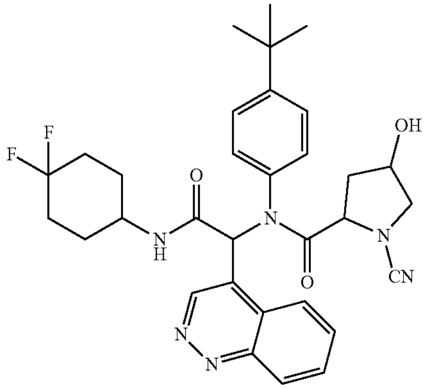 [SMILES: CC(C)(C)c1ccc(N(C(=O)C2CC(O)CN2C#N)C(C(=O)NC2CCC(F)(F)CC2)c2cnnc3ccccc23)cc1] |
| 1042 | 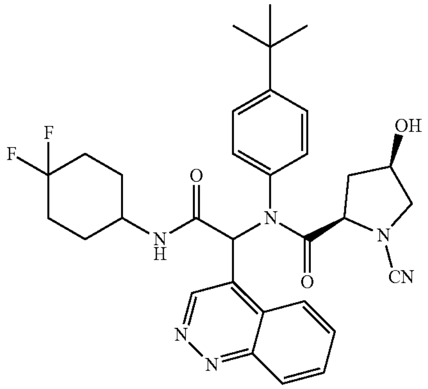 [SMILES: CC(C)(C)c1ccc(N(C(=O)[C@H]2C[C@@H](O)CN2C#N)C(C(=O)NC2CCC(F)(F)CC2)c2cnnc3ccccc23)cc1] |
| 1043a | 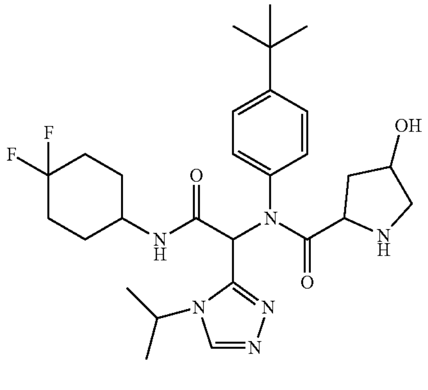 [SMILES: CC(C)n1cnnc1C(C(=O)NC1CCC(F)(F)CC1)N(C(=O)C1CC(O)CN1)c1ccc(C(C)(C)C)cc1] |
| 1043 | 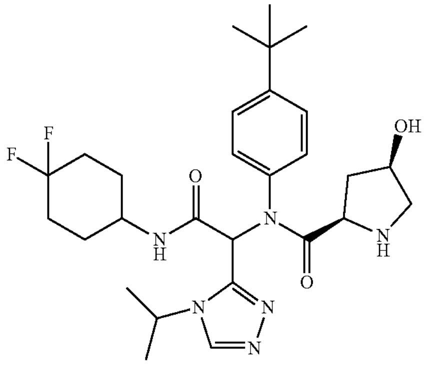 [SMILES: CC(C)n1cnnc1C(C(=O)NC1CCC(F)(F)CC1)N(C(=O)[C@H]1C[C@@H](O)CN1)c1ccc(C(C)(C)C)cc1] |
| 1044a | 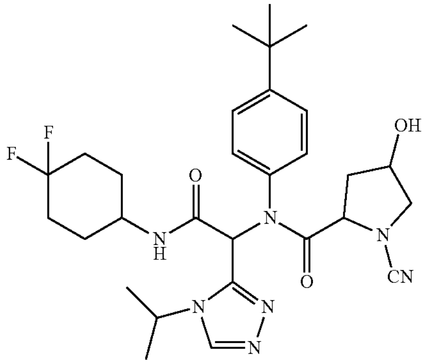 [SMILES: CC(C)n1cnnc1C(C(=O)NC1CCC(F)(F)CC1)N(C(=O)C1CC(O)CN1C#N)c1ccc(C(C)(C)C)cc1] |
| 1044 | 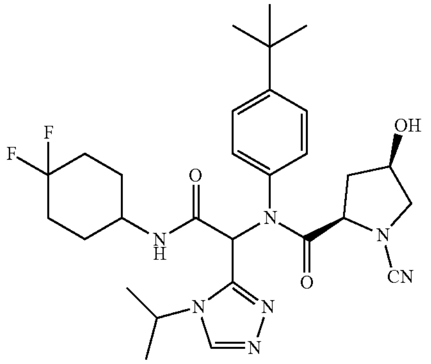 [SMILES: CC(C)n1cnnc1C(C(=O)NC1CCC(F)(F)CC1)N(C(=O)[C@H]1C[C@@H](O)CN1C#N)c1ccc(C(C)(C)C)cc1] |
| 1045a | 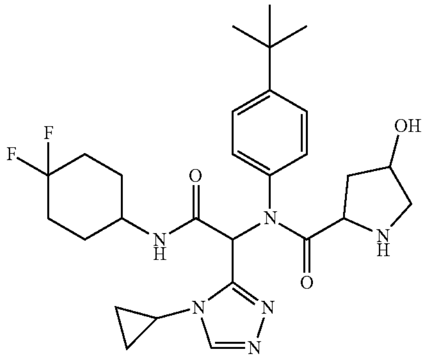 [SMILES: CC(C)(C)c1ccc(N(C(=O)C2CC(O)CN2)C(C(=O)NC2CCC(F)(F)CC2)c2nncn2C2CC2)cc1] |

TABLE 1-continued
| Exemplary compounds. | |
|---|---|
| Cmpd No. | Structure |
| 1045 | 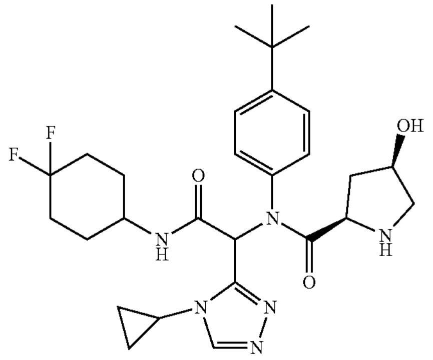 [SMILES: CC(C)(C)c1ccc(N(C(=O)[C@H]2C[C@@H](O)CN2)C(C(=O)NC2CCC(F)(F)CC2)c2nncn2C2CC2)cc1] |
| 1046a | 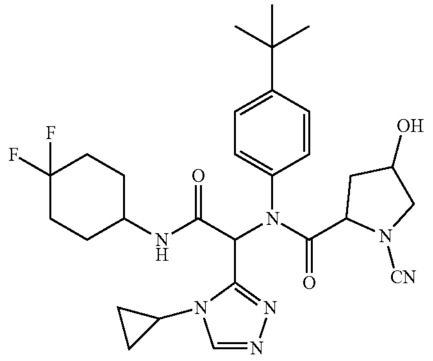 [SMILES: CC(C)(C)c1ccc(N(C(=O)C2CC(O)CN2C#N)C(C(=O)NC2CCC(F)(F)CC2)c2nncn2C2CC2)cc1] |
| 1046 | 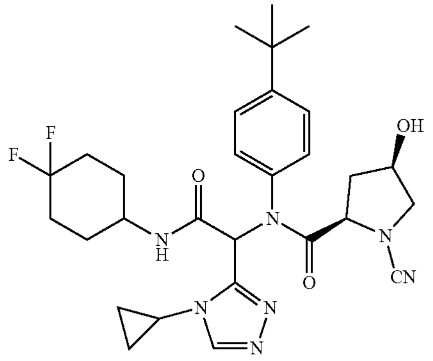 [SMILES: CC(C)(C)c1ccc(N(C(=O)[C@H]2C[C@@H](O)CN2C#N)C(C(=O)NC2CCC(F)(F)CC2)c2nncn2C2CC2)cc1] |
| 1047a | 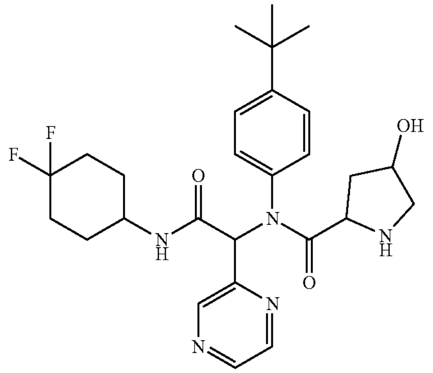 [SMILES: CC(C)(C)c1ccc(N(C(=O)C2CC(O)CN2)C(C(=O)NC2CCC(F)(F)CC2)c2cnccn2)cc1] |
TABLE 1-continued
| Exemplary compounds. | |
|---|---|
| Cmpd No. | Structure |
| 1047 | 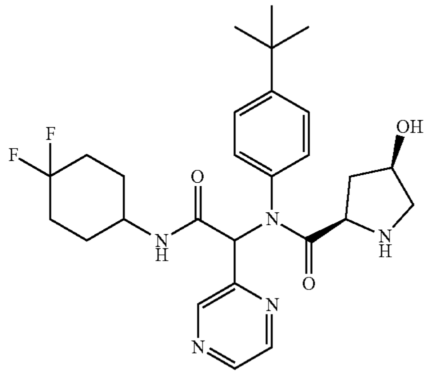 [SMILES: CC(C)(C)c1ccc(N(C(=O)[C@H]2C[C@@H](O)CN2)C(C(=O)NC2CCC(F)(F)CC2)c2cnccn2)cc1] |
| 1048a | 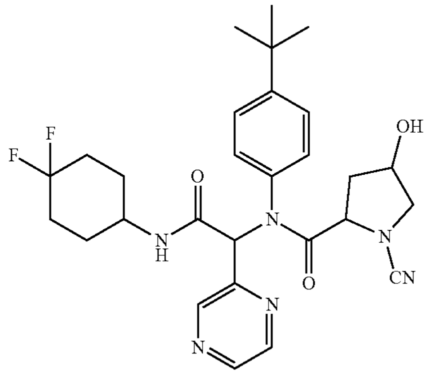 [SMILES: CC(C)(C)c1ccc(N(C(=O)C2CC(O)CN2C#N)C(C(=O)NC2CCC(F)(F)CC2)c2cnccn2)cc1] |
| 1048 | 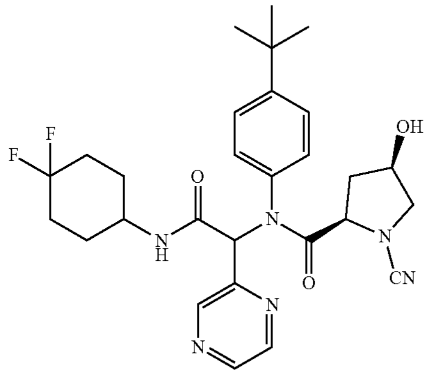 [SMILES: CC(C)(C)c1ccc(N(C(=O)[C@H]2C[C@@H](O)CN2C#N)C(C(=O)NC2CCC(F)(F)CC2)c2cnccn2)cc1] |
| 1049a | 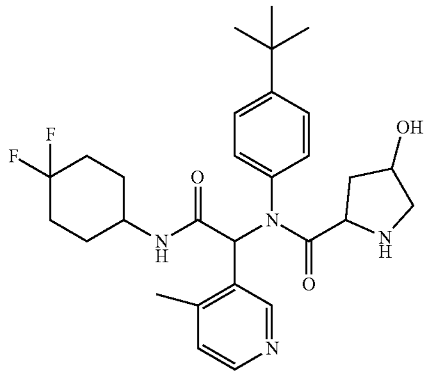 [SMILES: Cc1ccncc1C(C(=O)NC1CCC(F)(F)CC1)N(C(=O)C1CC(O)CN1)c1ccc(C(C)(C)C)cc1] |

TABLE 1-continued
| Exemplary compounds. | |
|---|---|
| Cmpd No. | Structure |
| 1049 | 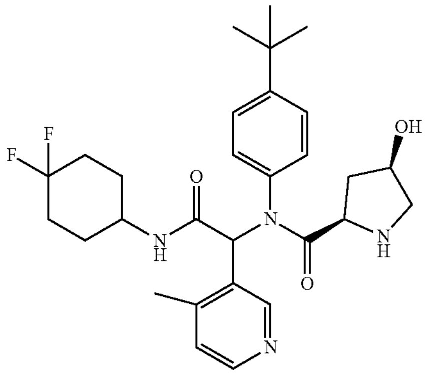 [SMILES: Cc1ccncc1C(C(=O)NC1CCC(F)(F)CC1)N(C(=O)[C@H]1C[C@@H](O)CN1)c1ccc(C(C)(C)C)cc1] |
| 1050a | 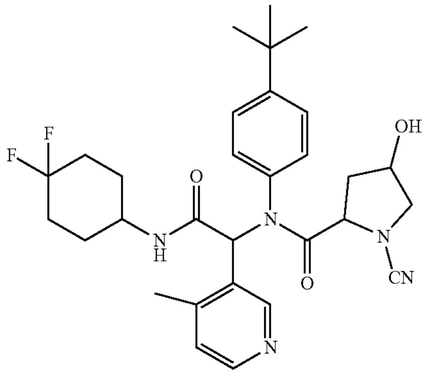 [SMILES: Cc1ccncc1C(C(=O)NC1CCC(F)(F)CC1)N(C(=O)C1CC(O)CN1C#N)c1ccc(C(C)(C)C)cc1] |
| 1050 | 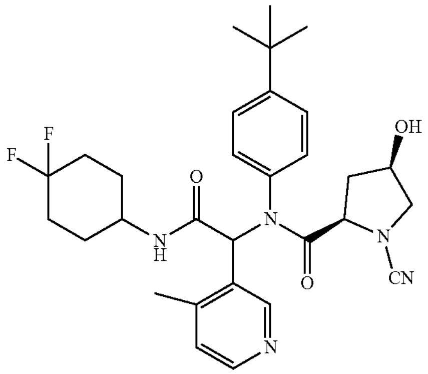 [SMILES: Cc1ccncc1C(C(=O)NC1CCC(F)(F)CC1)N(C(=O)[C@H]1C[C@@H](O)CN1C#N)c1ccc(C(C)(C)C)cc1] |
| 1051a | 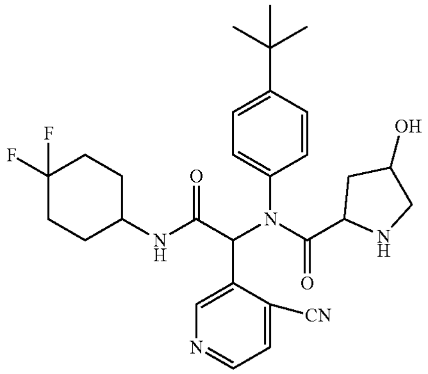 [SMILES: CC(C)(C)c1ccc(N(C(=O)C2CC(O)CN2)C(C(=O)NC2CCC(F)(F)CC2)c2cnccc2C#N)cc1] |
TABLE 1-continued
| Exemplary compounds. | |
|---|---|
| Cmpd No. | Structure |
| 1051 | 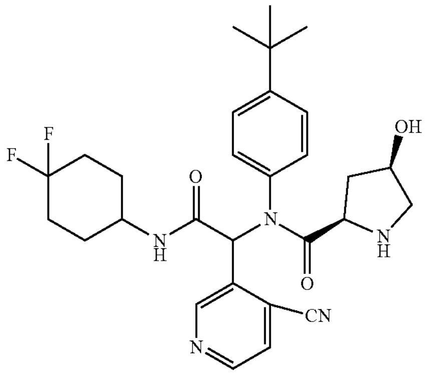 [SMILES: CC(C)(C)c1ccc(N(C(=O)[C@H]2C[C@@H](O)CN2)C(C(=O)NC2CCC(F)(F)CC2)c2cnccc2C#N)cc1] |
| 1052a | 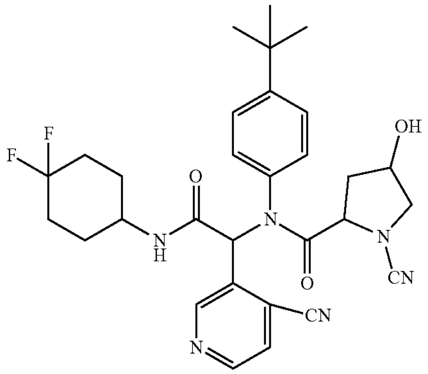 [SMILES: CC(C)(C)c1ccc(N(C(=O)C2CC(O)CN2C#N)C(C(=O)NC2CCC(F)(F)CC2)c2cnccc2C#N)cc1] |
| 1052 | 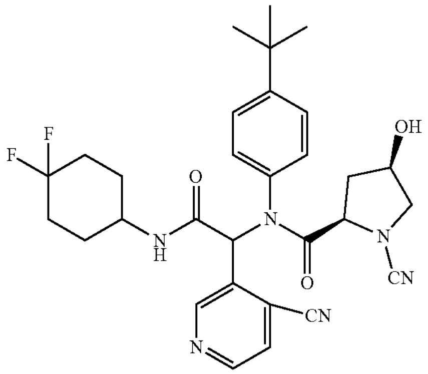 [SMILES: CC(C)(C)c1ccc(N(C(=O)[C@H]2C[C@@H](O)CN2C#N)C(C(=O)NC2CCC(F)(F)CC2)c2cnccc2C#N)cc1] |
| 1053a | 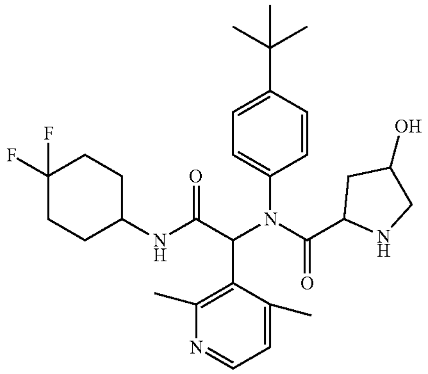 [SMILES: Cc1ccnc(C)c1C(C(=O)NC1CCC(F)(F)CC1)N(C(=O)C1CC(O)CN1)c1ccc(C(C)(C)C)cc1] |

TABLE 1-continued
Exemplary compounds.
| Cmpd No. | Structure |
|---|---|
| 1053 | 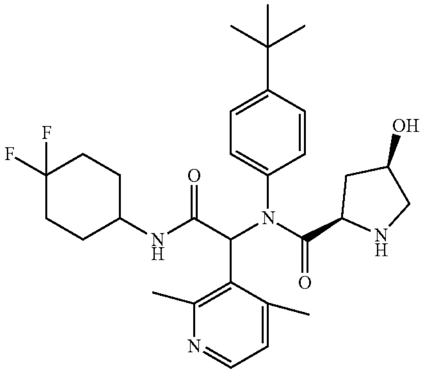 [SMILES: Cc1ccnc(C)c1C(C(=O)NC1CCC(F)(F)CC1)N(C(=O)[C@H]1C[C@@H](O)CN1)c1ccc(C(C)(C)C)cc1] |
| 1054a | 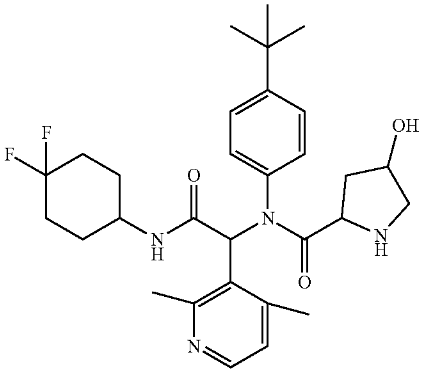 [SMILES: Cc1ccnc(C)c1C(C(=O)NC1CCC(F)(F)CC1)N(C(=O)C1CC(O)CN1)c1ccc(C(C)(C)C)cc1] |
| 1054 | 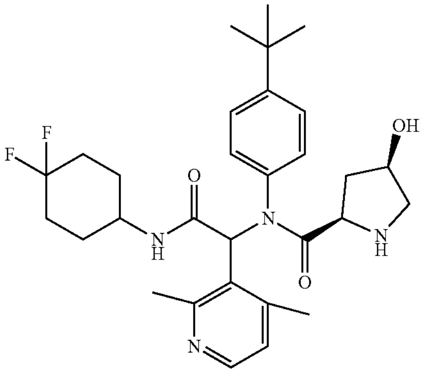 [SMILES: Cc1ccnc(C)c1C(C(=O)NC1CCC(F)(F)CC1)N(C(=O)[C@H]1C[C@@H](O)CN1)c1ccc(C(C)(C)C)cc1] |
| 1055a | 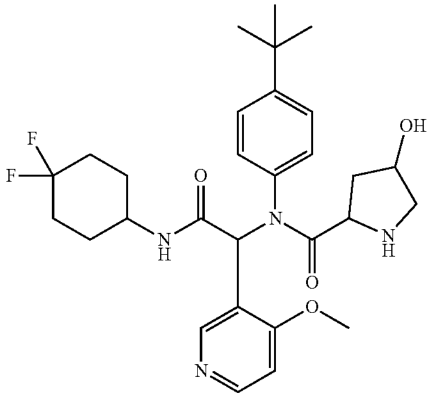 [SMILES: COc1ccncc1C(C(=O)NC1CCC(F)(F)CC1)N(C(=O)C1CC(O)CN1)c1ccc(C(C)(C)C)cc1] |
TABLE 1-continued
Exemplary compounds.
| Cmpd No. | Structure |
|---|---|
| 1055 | 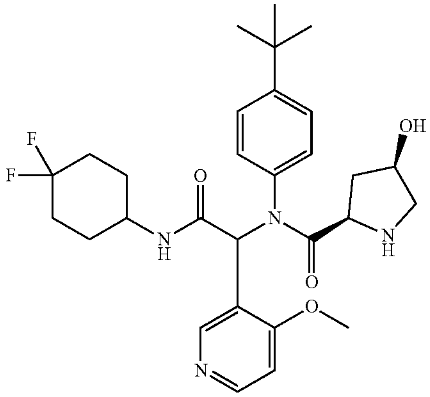 [SMILES: COc1ccncc1C(C(=O)NC1CCC(F)(F)CC1)N(C(=O)[C@H]1C[C@@H](O)CN1)c1ccc(C(C)(C)C)cc1] |
| 1056a | 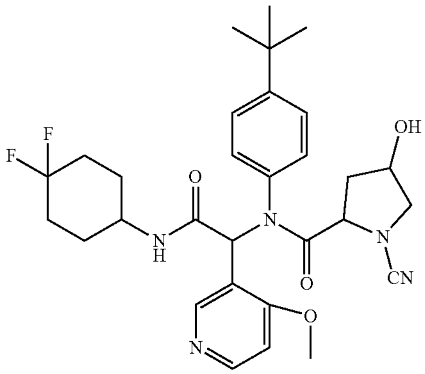 [SMILES: COc1ccncc1C(C(=O)NC1CCC(F)(F)CC1)N(C(=O)C1CC(O)CN1C#N)c1ccc(C(C)(C)C)cc1] |
| 1056 | 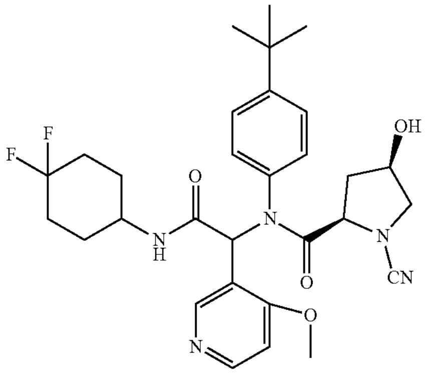 [SMILES: COc1ccncc1C(C(=O)NC1CCC(F)(F)CC1)N(C(=O)[C@H]1C[C@@H](O)CN1C#N)c1ccc(C(C)(C)C)cc1] |
| 1057a | 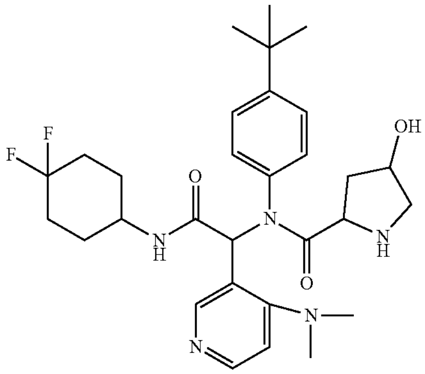 [SMILES: CN(C)c1ccncc1C(C(=O)NC1CCC(F)(F)CC1)N(C(=O)C1CC(O)CN1)c1ccc(C(C)(C)C)cc1] |

TABLE 1-continued
| Exemplary compounds. | |
|---|---|
| Cmpd No. | Structure |
| 1057 | 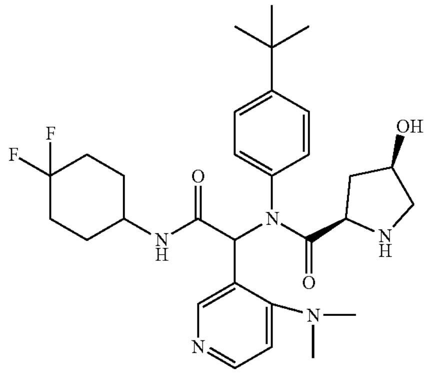 [SMILES: CN(C)c1ccncc1C(C(=O)NC1CCC(F)(F)CC1)N(C(=O)[C@H]1C[C@@H](O)CN1)c1ccc(C(C)(C)C)cc1] |
| 1058a | 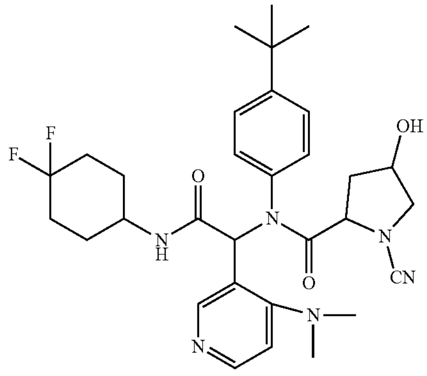 [SMILES: CN(C)c1ccncc1C(C(=O)NC1CCC(F)(F)CC1)N(C(=O)C1CC(O)CN1C#N)c1ccc(C(C)(C)C)cc1] |
| 1058 | 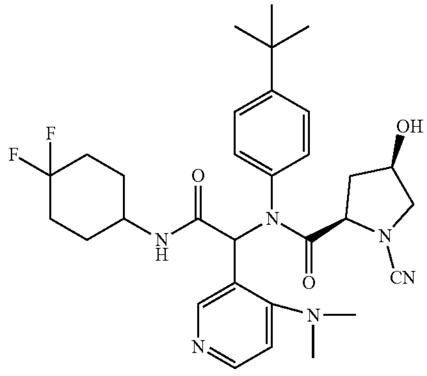 [SMILES: CN(C)c1ccncc1C(C(=O)NC1CCC(F)(F)CC1)N(C(=O)[C@H]1C[C@@H](O)CN1C#N)c1ccc(C(C)(C)C)cc1] |
| 1059a | 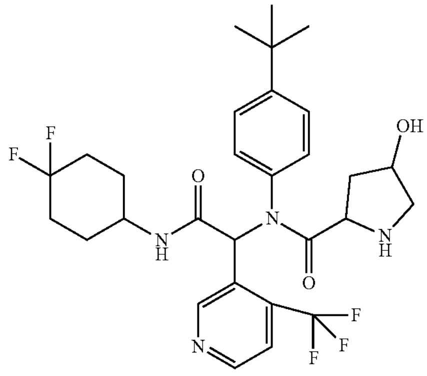 [SMILES: CC(C)(C)c1ccc(N(C(=O)C2CC(O)CN2)C(C(=O)NC2CCC(F)(F)CC2)c2cnccc2C(F)(F)F)cc1] |
TABLE 1-continued
| Exemplary compounds. | |
|---|---|
| Cmpd No. | Structure |
| 1059 | 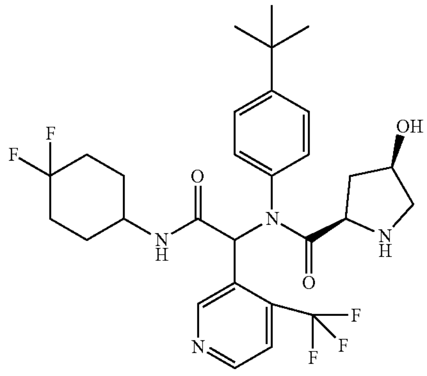 [SMILES: CC(C)(C)c1ccc(N(C(=O)[C@H]2C[C@@H](O)CN2)C(C(=O)NC2CCC(F)(F)CC2)c2cnccc2C(F)(F)F)cc1] |
| 1060a | 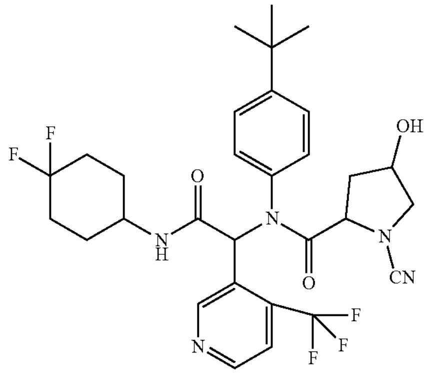 [SMILES: CC(C)(C)c1ccc(N(C(=O)C2CC(O)CN2C#N)C(C(=O)NC2CCC(F)(F)CC2)c2cnccc2C(F)(F)F)cc1] |
| 1060 | 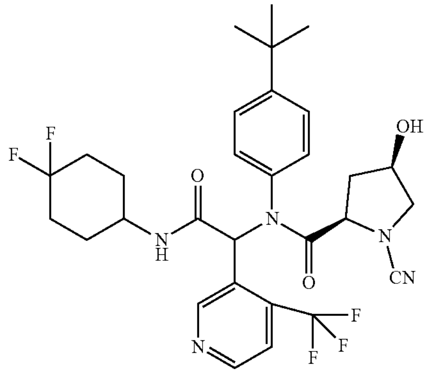 [SMILES: CC(C)(C)c1ccc(N(C(=O)[C@H]2C[C@@H](O)CN2C#N)C(C(=O)NC2CCC(F)(F)CC2)c2cnccc2C(F)(F)F)cc1] |
| 1061a | 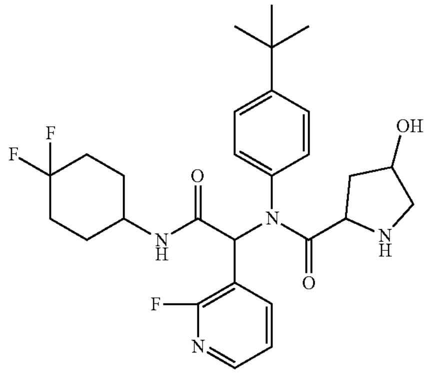 [SMILES: CC(C)(C)c1ccc(N(C(=O)C2CC(O)CN2)C(C(=O)NC2CCC(F)(F)CC2)c2cccnc2F)cc1] |

TABLE 1-continued
Exemplary compounds.
| Cmpd No. | Structure |
| --- | --- |
| 1061 | 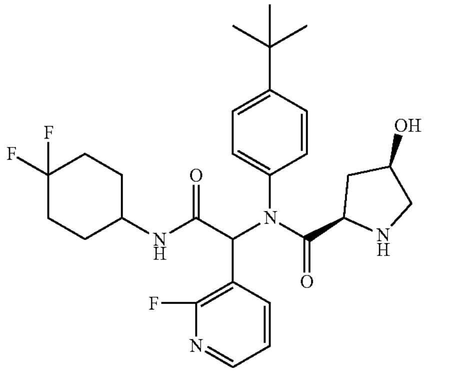 [SMILES: CC(C)(C)c1ccc(N(C(=O)[C@H]2C[C@@H](O)CN2)C(C(=O)NC2CCC(F)(F)CC2)c2cccnc2F)cc1] |
| 1062a | 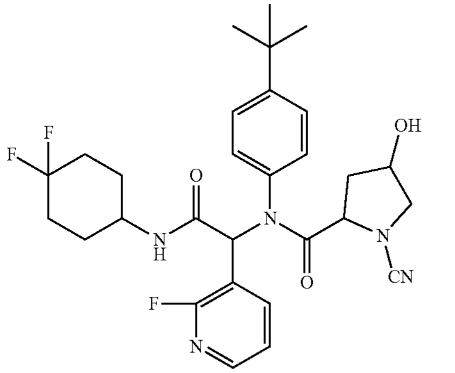 [SMILES: CC(C)(C)c1ccc(N(C(=O)C2CC(O)CN2C#N)C(C(=O)NC2CCC(F)(F)CC2)c2cccnc2F)cc1] |
| 1062 | 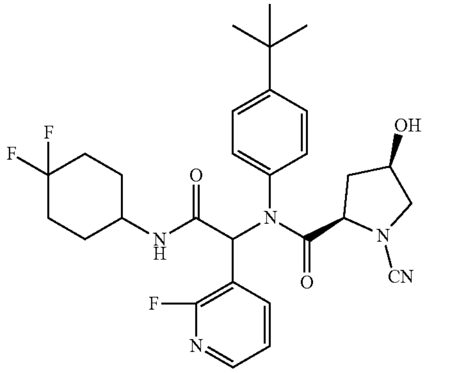 [SMILES: CC(C)(C)c1ccc(N(C(=O)[C@H]2C[C@@H](O)CN2C#N)C(C(=O)NC2CCC(F)(F)CC2)c2cccnc2F)cc1] |
| 1063a | 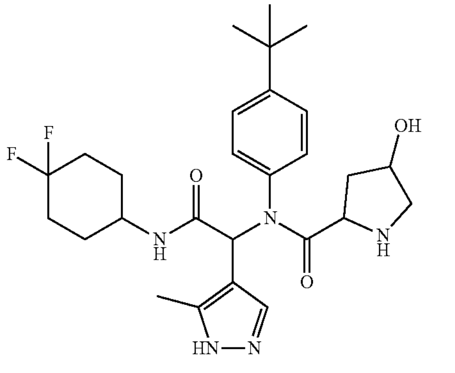 [SMILES: Cc1[nH]ncc1C(C(=O)NC1CCC(F)(F)CC1)N(C(=O)C1CC(O)CN1)c1ccc(C(C)(C)C)cc1] |
TABLE 1-continued
Exemplary compounds.
| Cmpd No. | Structure |
| --- | --- |
| 1063 | 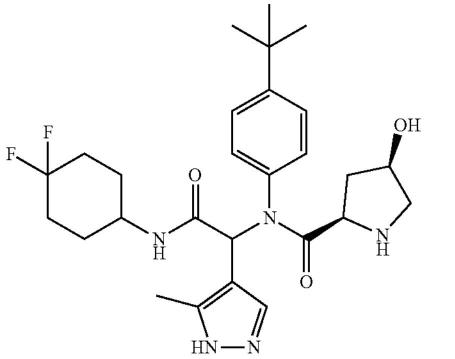 [SMILES: Cc1[nH]ncc1C(C(=O)NC1CCC(F)(F)CC1)N(C(=O)[C@H]1C[C@@H](O)CN1)c1ccc(C(C)(C)C)cc1] |
| 1064a | 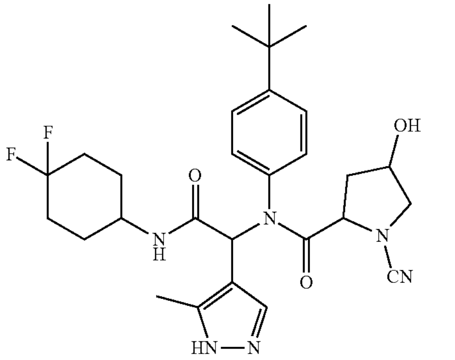 [SMILES: Cc1[nH]ncc1C(C(=O)NC1CCC(F)(F)CC1)N(C(=O)C1CC(O)CN1C#N)c1ccc(C(C)(C)C)cc1] |
| 1064 | 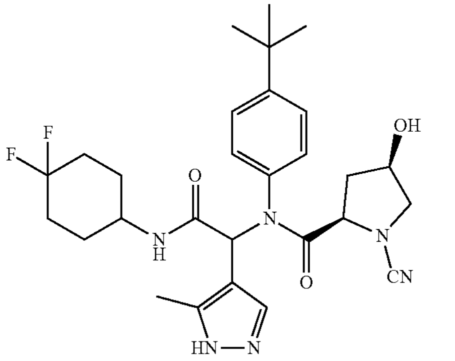 [SMILES: Cc1[nH]ncc1C(C(=O)NC1CCC(F)(F)CC1)N(C(=O)[C@H]1C[C@@H](O)CN1C#N)c1ccc(C(C)(C)C)cc1] |
| 1065a | 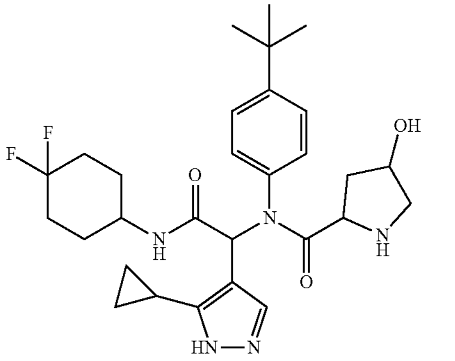 [SMILES: CC(C)(C)c1ccc(N(C(=O)C2CC(O)CN2)C(C(=O)NC2CCC(F)(F)CC2)c2cn[nH]c2C2CC2)cc1] |

TABLE 1-continued
| Exemplary compounds. | |
|---|---|
| Cmpd No. | Structure |
| 1065 | 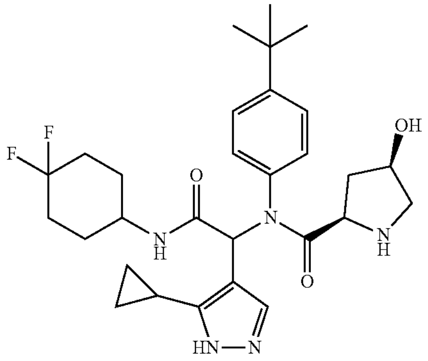 [SMILES: CC(C)(C)c1ccc(N(C(=O)[C@H]2C[C@@H](O)CN2)C(C(=O)NC2CCC(F)(F)CC2)c2cn[nH]c2C2CC2)cc1] |
| 1066a | 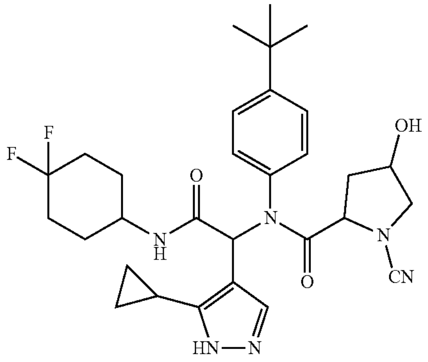 [SMILES: CC(C)(C)c1ccc(N(C(=O)C2CC(O)CN2C#N)C(C(=O)NC2CCC(F)(F)CC2)c2cn[nH]c2C2CC2)cc1] |
| 1066 | 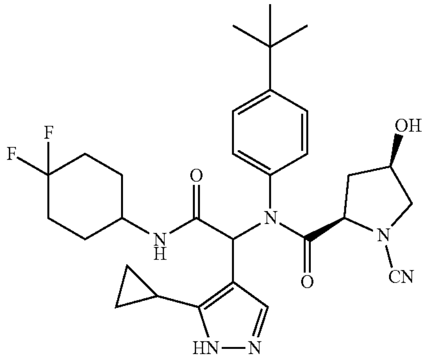 [SMILES: CC(C)(C)c1ccc(N(C(=O)[C@H]2C[C@@H](O)CN2C#N)C(C(=O)NC2CCC(F)(F)CC2)c2cn[nH]c2C2CC2)cc1] |
| 1067a | 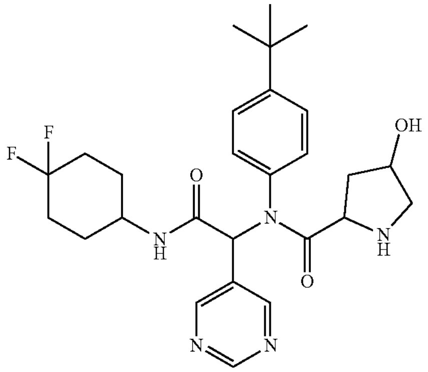 [SMILES: CC(C)(C)c1ccc(N(C(=O)C2CC(O)CN2)C(C(=O)NC2CCC(F)(F)CC2)c2cncnc2)cc1] |
TABLE 1-continued
| Exemplary compounds. | |
|---|---|
| Cmpd No. | Structure |
| 1067 | 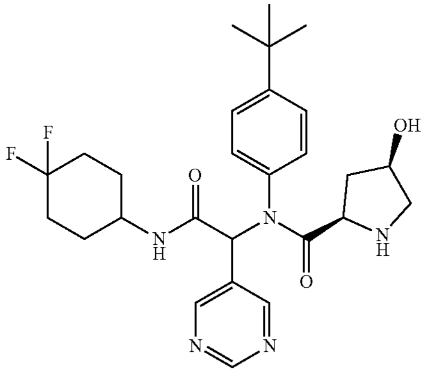 [SMILES: CC(C)(C)c1ccc(N(C(=O)[C@H]2C[C@@H](O)CN2)C(C(=O)NC2CCC(F)(F)CC2)c2cncnc2)cc1] |
| 1068a | 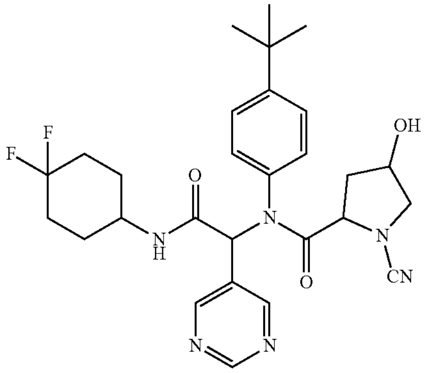 [SMILES: CC(C)(C)c1ccc(N(C(=O)C2CC(O)CN2C#N)C(C(=O)NC2CCC(F)(F)CC2)c2cncnc2)cc1] |
| 1068 | 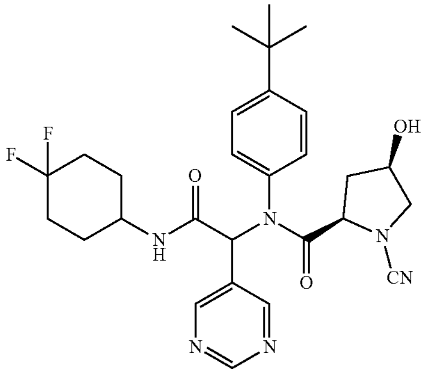 [SMILES: CC(C)(C)c1ccc(N(C(=O)[C@H]2C[C@@H](O)CN2C#N)C(C(=O)NC2CCC(F)(F)CC2)c2cncnc2)cc1] |
| 1069a | 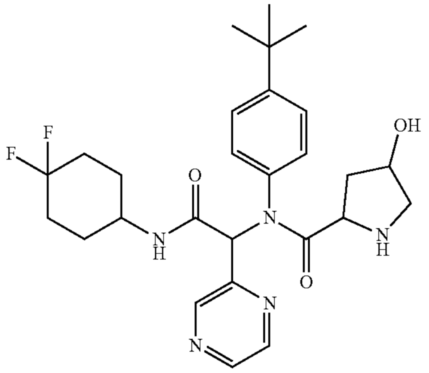 [SMILES: CC(C)(C)c1ccc(N(C(=O)C2CC(O)CN2)C(C(=O)NC2CCC(F)(F)CC2)c2cnccn2)cc1] |

TABLE 1-continued
| Exemplary compounds. | |
|---|---|
| Cmpd No. | Structure |
| 1069 | 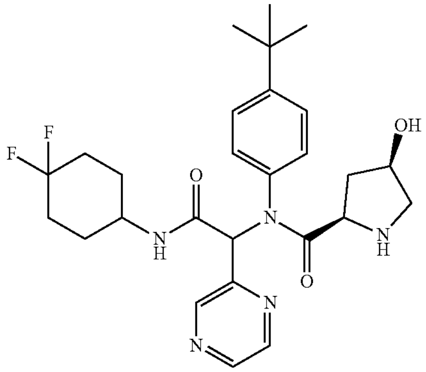 [SMILES: CC(C)(C)c1ccc(N(C(=O)[C@H]2C[C@@H](O)CN2)C(C(=O)NC2CCC(F)(F)CC2)c2cnccn2)cc1] |
| 1070a | 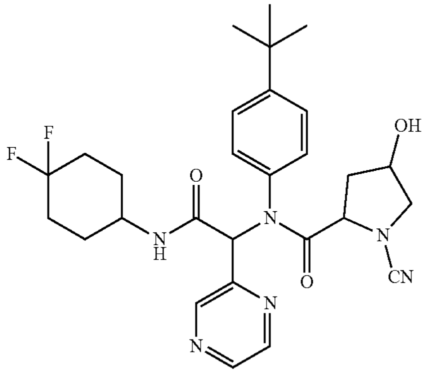 [SMILES: CC(C)(C)c1ccc(N(C(=O)C2CC(O)CN2C#N)C(C(=O)NC2CCC(F)(F)CC2)c2cnccn2)cc1] |
| 1070 | 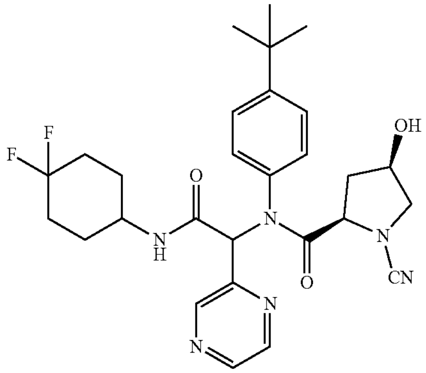 [SMILES: CC(C)(C)c1ccc(N(C(=O)[C@H]2C[C@@H](O)CN2C#N)C(C(=O)NC2CCC(F)(F)CC2)c2cnccn2)cc1] |
| 1071a | 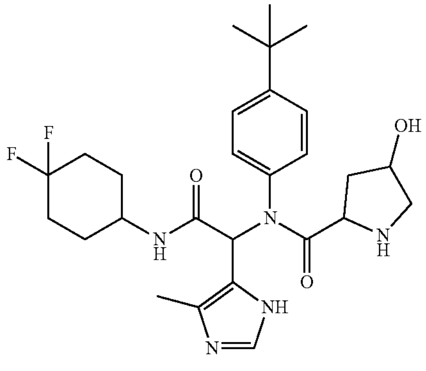 [SMILES: Cc1nc[nH]c1C(C(=O)NC1CCC(F)(F)CC1)N(C(=O)C1CC(O)CN1)c1ccc(C(C)(C)C)cc1] |
TABLE 1-continued
| Exemplary compounds. | |
|---|---|
| Cmpd No. | Structure |
| 1071 | 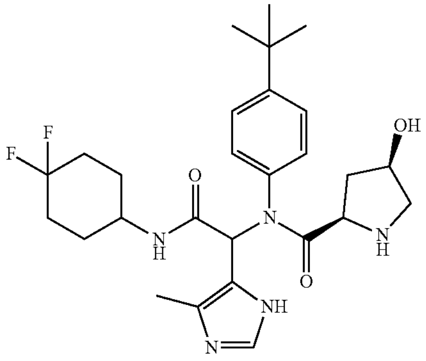 [SMILES: Cc1nc[nH]c1C(C(=O)NC1CCC(F)(F)CC1)N(C(=O)[C@H]1C[C@@H](O)CN1)c1ccc(C(C)(C)C)cc1] |
| 1072a | 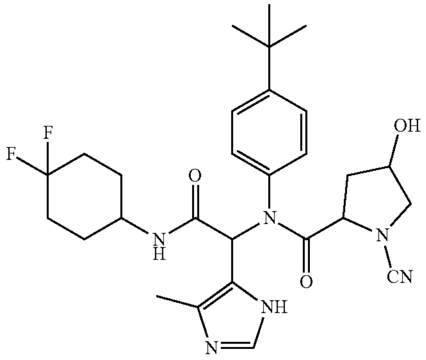 [SMILES: Cc1nc[nH]c1C(C(=O)NC1CCC(F)(F)CC1)N(C(=O)C1CC(O)CN1C#N)c1ccc(C(C)(C)C)cc1] |
| 1072 | 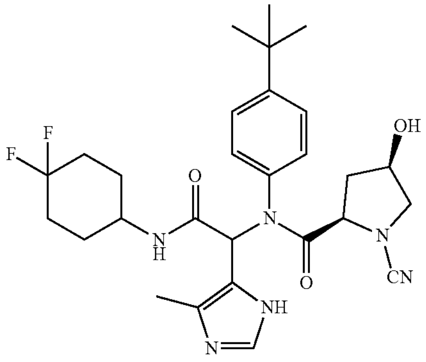 [SMILES: Cc1nc[nH]c1C(C(=O)NC1CCC(F)(F)CC1)N(C(=O)[C@H]1C[C@@H](O)CN1C#N)c1ccc(C(C)(C)C)cc1] |
| 1073a | 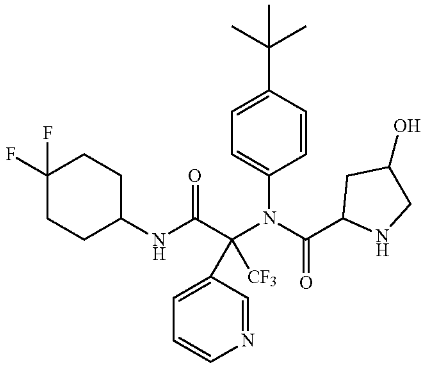 [SMILES: CC(C)(C)c1ccc(N(C(=O)C2CC(O)CN2)C(C(=O)NC2CCC(F)(F)CC2)(c2cccnc2)C(F)(F)F)cc1] |

TABLE 1-continued
Exemplary compounds.
| Cmpd No. | Structure |
| --- | --- |
| 1073 | 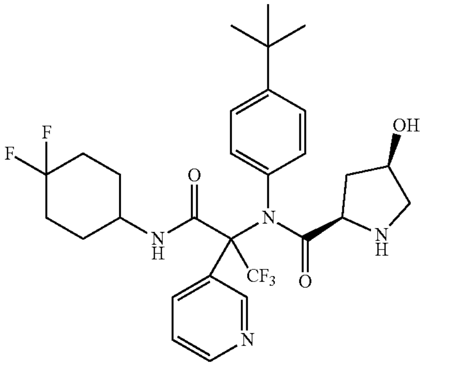 [SMILES: CC(C)(C)c1ccc(N(C(=O)[C@H]2C[C@@H](O)CN2)C(C(=O)NC2CCC(F)(F)CC2)(c2cccnc2)C(F)(F)F)cc1] |
| 1074a | 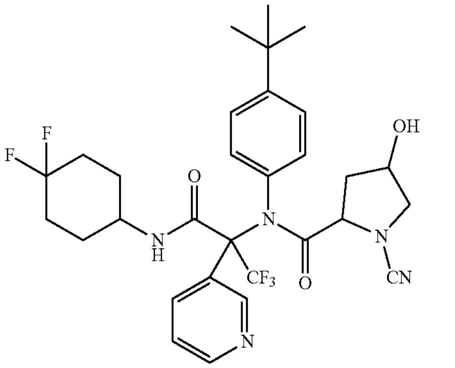 [SMILES: CC(C)(C)c1ccc(N(C(=O)C2CC(O)CN2C#N)C(C(=O)NC2CCC(F)(F)CC2)(c2cccnc2)C(F)(F)F)cc1] |
| 1074 | 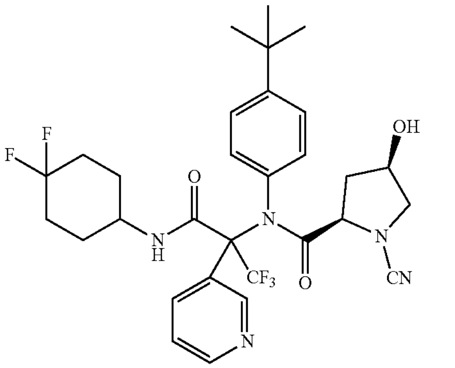 [SMILES: CC(C)(C)c1ccc(N(C(=O)[C@H]2C[C@@H](O)CN2C#N)C(C(=O)NC2CCC(F)(F)CC2)(c2cccnc2)C(F)(F)F)cc1] |
| 1075a | 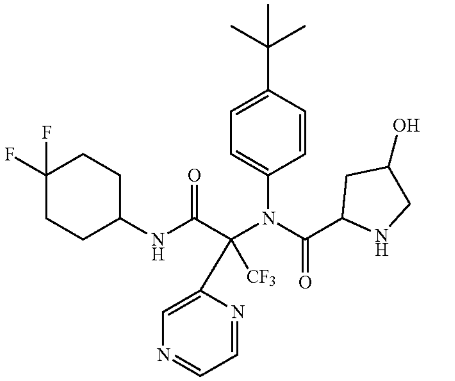 [SMILES: CC(C)(C)c1ccc(N(C(=O)C2CC(O)CN2)C(C(=O)NC2CCC(F)(F)CC2)(c2cnccn2)C(F)(F)F)cc1] |
TABLE 1-continued
Exemplary compounds.
| Cmpd No. | Structure |
| --- | --- |
| 1075 | 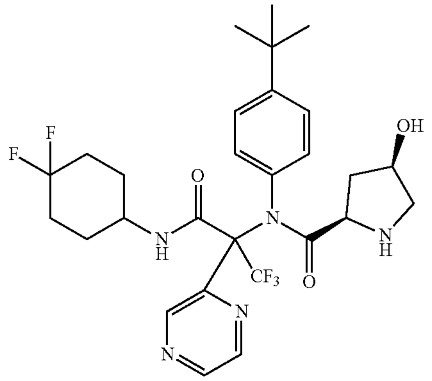 [SMILES: CC(C)(C)c1ccc(N(C(=O)[C@H]2C[C@@H](O)CN2)C(C(=O)NC2CCC(F)(F)CC2)(c2cnccn2)C(F)(F)F)cc1] |
| 1076a | 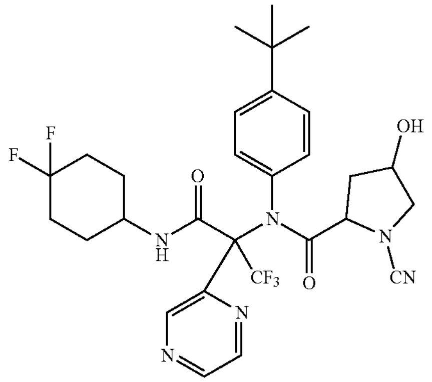 [SMILES: CC(C)(C)c1ccc(N(C(=O)C2CC(O)CN2C#N)C(C(=O)NC2CCC(F)(F)CC2)(c2cnccn2)C(F)(F)F)cc1] |
| 1076 | 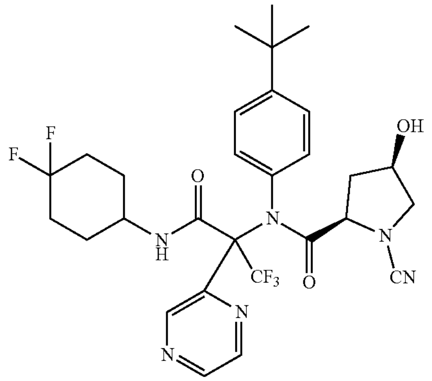 [SMILES: CC(C)(C)c1ccc(N(C(=O)[C@H]2C[C@@H](O)CN2C#N)C(C(=O)NC2CCC(F)(F)CC2)(c2cnccn2)C(F)(F)F)cc1] |
| 1077a | 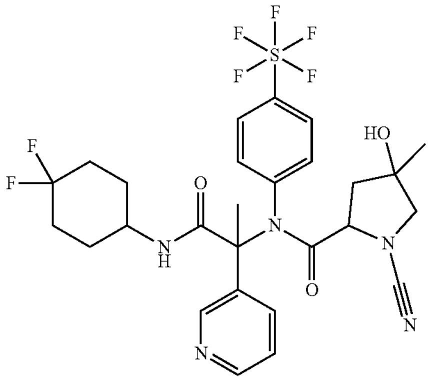 [SMILES: CC1(O)CC(C(=O)N(c2ccc(S(F)(F)(F)(F)F)cc2)C(C)(C(=O)NC2CCC(F)(F)CC2)c2cccnc2)N(C#N)C1] |

TABLE 1-continued
Exemplary compounds.
| Cmpd No. | Structure |
| --- | --- |
| 1077 | 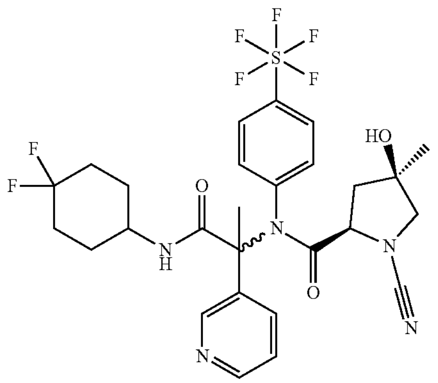 [SMILES: CC(C(=O)NC1CCC(F)(F)CC1)(c1cccnc1)N(C(=O)[C@H]1C[C@@](C)(O)CN1C#N)c1ccc(S(F)(F)(F)(F)F)cc1] |
| 1078a | 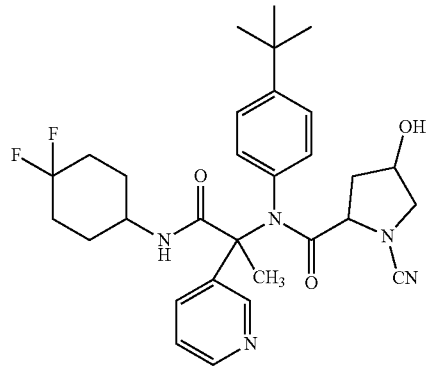 [SMILES: CC(C)(C)c1ccc(N(C(=O)C2CC(O)CN2C#N)C(C)(C(=O)NC2CCC(F)(F)CC2)c2cccnc2)cc1] |
| 1078 | 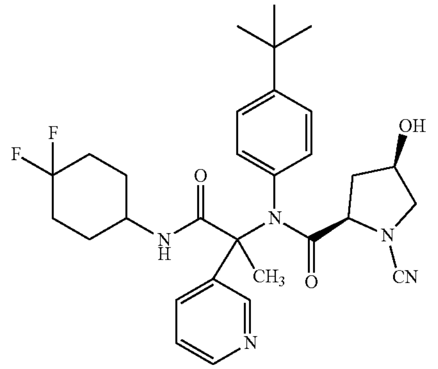 [SMILES: CC(C)(C)c1ccc(N(C(=O)[C@H]2C[C@@H](O)CN2C#N)C(C)(C(=O)NC2CCC(F)(F)CC2)c2cccnc2)cc1] |
| 1079a | 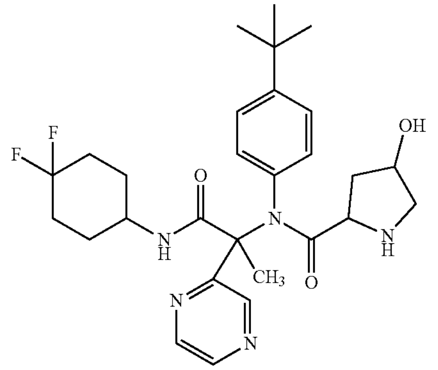 [SMILES: CC(C)(C)c1ccc(N(C(=O)C2CC(O)CN2)C(C)(C(=O)NC2CCC(F)(F)CC2)c2cnccn2)cc1] |
TABLE 1-continued
Exemplary compounds.
| Cmpd No. | Structure |
| --- | --- |
| 1079 | 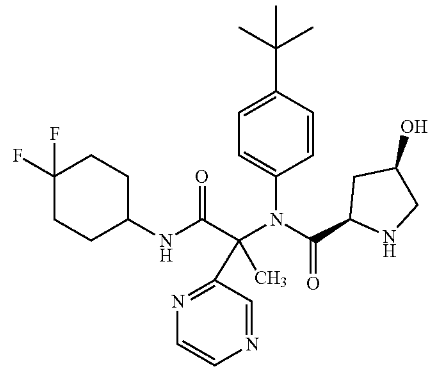 [SMILES: CC(C)(C)c1ccc(N(C(=O)[C@H]2C[C@@H](O)CN2)C(C)(C(=O)NC2CCC(F)(F)CC2)c2cnccn2)cc1] |
| 1080a | 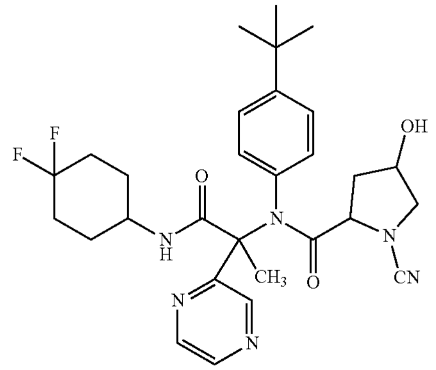 [SMILES: CC(C)(C)c1ccc(N(C(=O)C2CC(O)CN2C#N)C(C)(C(=O)NC2CCC(F)(F)CC2)c2cnccn2)cc1] |
| 1080 | 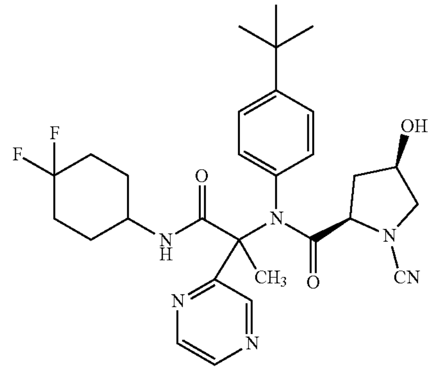 [SMILES: CC(C)(C)c1ccc(N(C(=O)[C@H]2C[C@@H](O)CN2C#N)C(C)(C(=O)NC2CCC(F)(F)CC2)c2cnccn2)cc1] |
| 1081b | 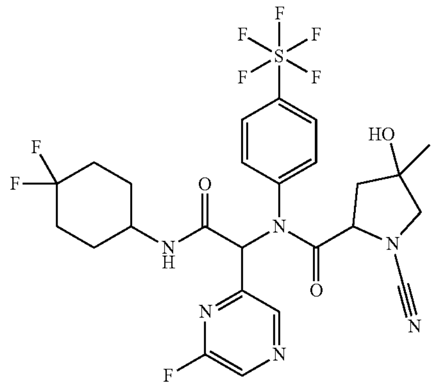 [SMILES: CC1(O)CC(C(=O)N(c2ccc(S(F)(F)(F)(F)F)cc2)C(C(=O)NC2CCC(F)(F)CC2)c2cncc(F)n2)N(C#N)C1] |

TABLE 1-continued
| Exemplary compounds. | |
|---|---|
| Cmpd No. | Structure |
| 1081c | 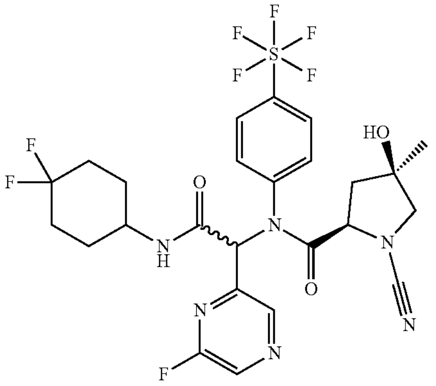 [SMILES: C[C@@]1(O)C[C@H](C(=O)N(c2ccc(S(F)(F)(F)(F)F)cc2)C(C(=O)NC2CCC(F)(F)CC2)c2cncc(F)n2)N(C#N)C1] |
| 1081a | 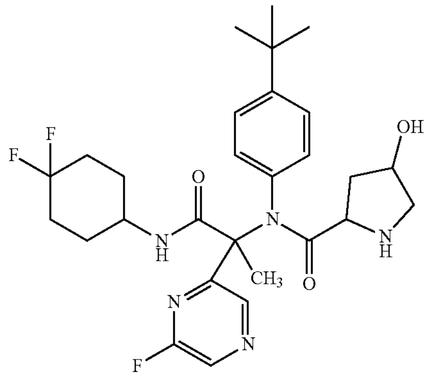 [SMILES: CC(C)(C)c1ccc(N(C(=O)C2CC(O)CN2)C(C)(C(=O)NC2CCC(F)(F)CC2)c2cncc(F)n2)cc1] |
| 1081 | 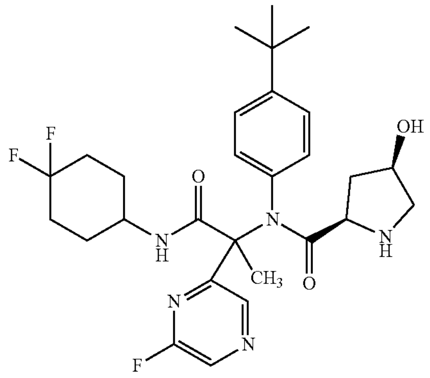 [SMILES: CC(C)(C)c1ccc(N(C(=O)[C@H]2C[C@@H](O)CN2)C(C)(C(=O)NC2CCC(F)(F)CC2)c2cncc(F)n2)cc1] |
| 1082a | 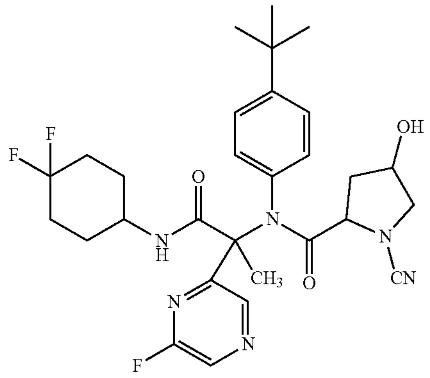 [SMILES: CC(C)(C)c1ccc(N(C(=O)C2CC(O)CN2C#N)C(C)(C(=O)NC2CCC(F)(F)CC2)c2cncc(F)n2)cc1] |
TABLE 1-continued
| Exemplary compounds. | |
|---|---|
| Cmpd No. | Structure |
| 1082 | 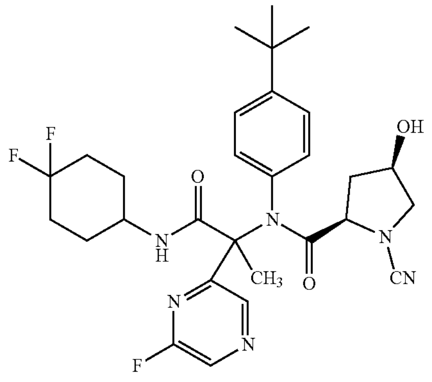 [SMILES: CC(C)(C)c1ccc(N(C(=O)[C@H]2C[C@@H](O)CN2C#N)C(C)(C(=O)NC2CCC(F)(F)CC2)c2cncc(F)n2)cc1] |
| 1083a | 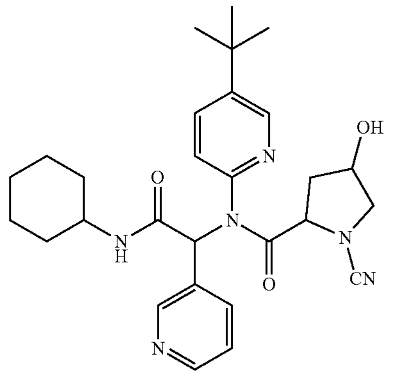 [SMILES: CC(C)(C)c1ccc(N(C(=O)C2CC(O)CN2C#N)C(C(=O)NC2CCCCC2)c2cccnc2)nc1] |
| 1083 | 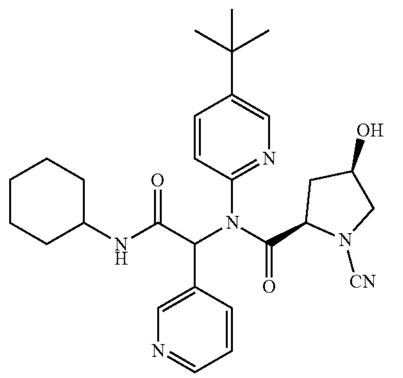 [SMILES: CC(C)(C)c1ccc(N(C(=O)[C@H]2C[C@@H](O)CN2C#N)C(C(=O)NC2CCCCC2)c2cccnc2)nc1] |
| 1084a | 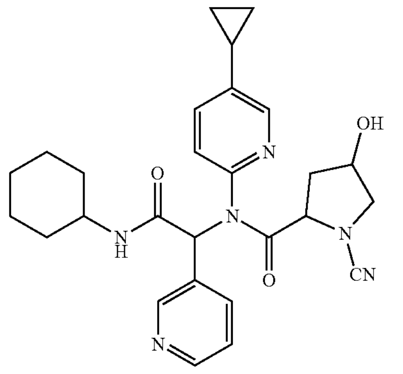 [SMILES: N#CN1CC(O)CC1C(=O)N(c1ccc(C2CC2)cn1)C(C(=O)NC1CCCCC1)c1cccnc1] |

TABLE 1-continued
| Exemplary compounds. | |
| --- | --- |
| Cmpd No. | Structure |
| 1084 | 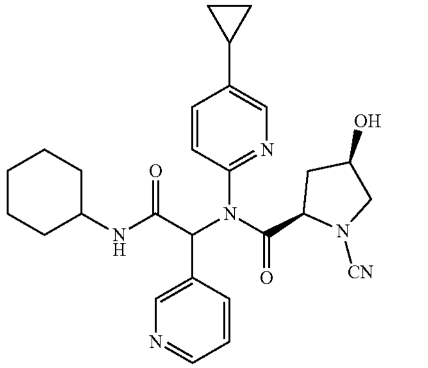 [SMILES: N#CN1C[C@H](O)C[C@@H]1C(=O)N(c1ccc(C2CC2)cn1)C(C(=O)NC1CCCCC1)c1cccnc1] |
| 1805a | 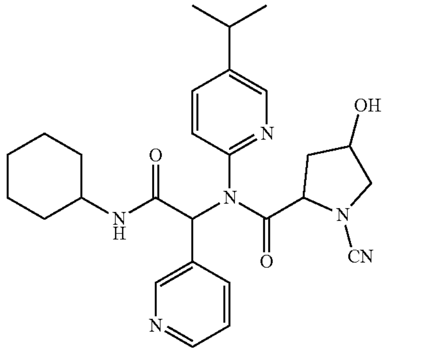 [SMILES: CC(C)c1ccc(N(C(=O)C2CC(O)CN2C#N)C(C(=O)NC2CCCCC2)c2cccnc2)nc1] |
| 1085 | 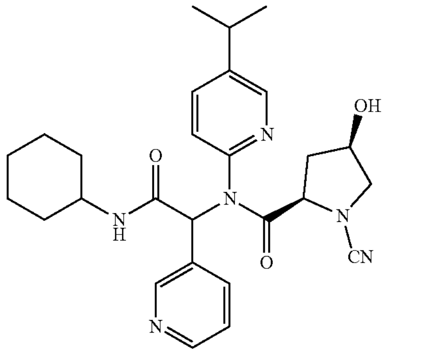 [SMILES: CC(C)c1ccc(N(C(=O)[C@H]2C[C@@H](O)CN2C#N)C(C(=O)NC2CCCCC2)c2cccnc2)nc1] |
| 1086a | 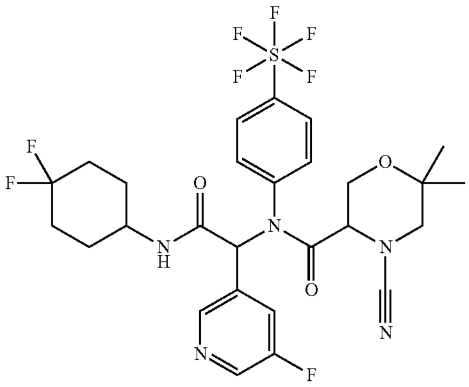 [SMILES: CC1(C)CN(C#N)C(C(=O)N(c2ccc(S(F)(F)(F)(F)F)cc2)C(C(=O)NC2CCC(F)(F)CC2)c2cncc(F)c2)CO1] |
TABLE 1-continued
| Exemplary compounds. | |
| --- | --- |
| Cmpd No. | Structure |
| 1086 | 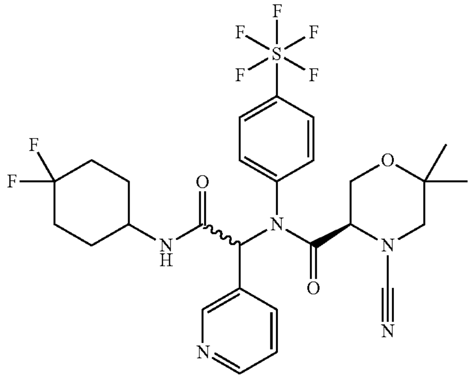 [SMILES: CC1(C)CN(C#N)[C@@H](C(=O)N(c2ccc(S(F)(F)(F)(F)F)cc2)C(C(=O)NC2CCC(F)(F)CC2)c2cccnc2)CO1] |
| 1086b | 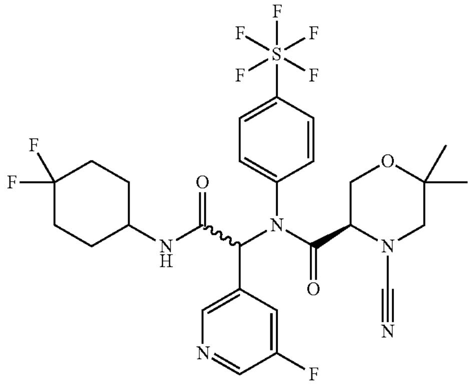 [SMILES: CC1(C)CN(C#N)[C@@H](C(=O)N(c2ccc(S(F)(F)(F)(F)F)cc2)C(C(=O)NC2CCC(F)(F)CC2)c2cncc(F)c2)CO1] |
| 1087a | 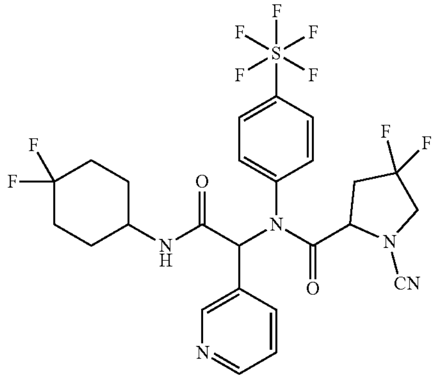 [SMILES: N#CN1CC(F)(F)CC1C(=O)N(c1ccc(S(F)(F)(F)(F)F)cc1)C(C(=O)NC1CCC(F)(F)CC1)c1cccnc1] |
| 1087 | 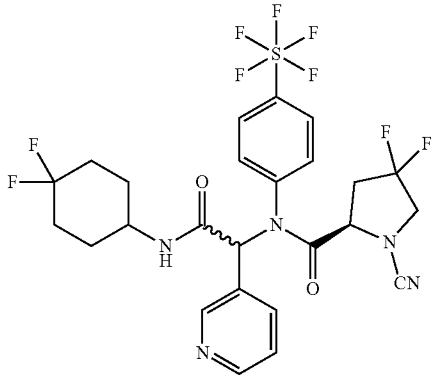 [SMILES: N#CN1CC(F)(F)C[C@@H]1C(=O)N(c1ccc(S(F)(F)(F)(F)F)cc1)C(C(=O)NC1CCC(F)(F)CC1)c1cccnc1] |

TABLE 1-continued
| Exemplary compounds. | |
|---|---|
| Cmpd No. | Structure |
| 1088a | 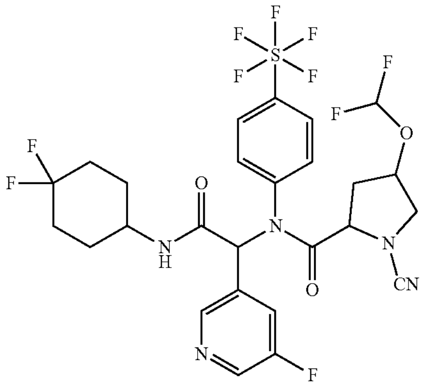 [SMILES: N#CN1CC(OC(F)F)CC1C(=O)N(c1ccc(S(F)(F)(F)(F)F)cc1)C(C(=O)NC1CCC(F)(F)CC1)c1cncc(F)c1] |
| 1088 | 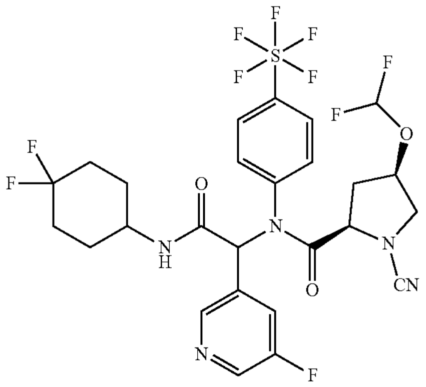 [SMILES: N#CN1C[C@H](OC(F)F)C[C@@H]1C(=O)N(c1ccc(S(F)(F)(F)(F)F)cc1)C(C(=O)NC1CCC(F)(F)CC1)c1cncc(F)c1] |
| 1089 | 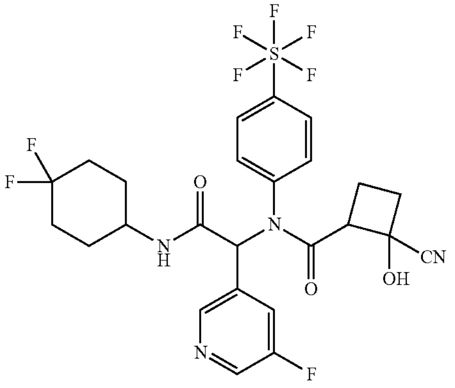 [SMILES: N#CC1(O)CCC1C(=O)N(c1ccc(S(F)(F)(F)(F)F)cc1)C(C(=O)NC1CCC(F)(F)CC1)c1cncc(F)c1] |
TABLE 1-continued
| Exemplary compounds. | |
|---|---|
| Cmpd No. | Structure |
| 1089a | 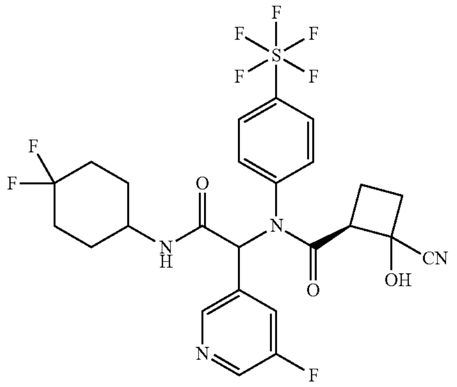 [SMILES: N#CC1(O)CC[C@@H]1C(=O)N(c1ccc(S(F)(F)(F)(F)F)cc1)C(C(=O)NC1CCC(F)(F)CC1)c1cncc(F)c1] |
| 1090a | 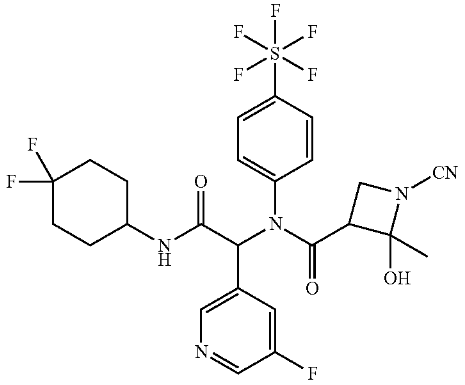 [SMILES: CC1(O)C(C(=O)N(c2ccc(S(F)(F)(F)(F)F)cc2)C(C(=O)NC2CCC(F)(F)CC2)c2cncc(F)c2)CN1C#N] |
| 1090 | 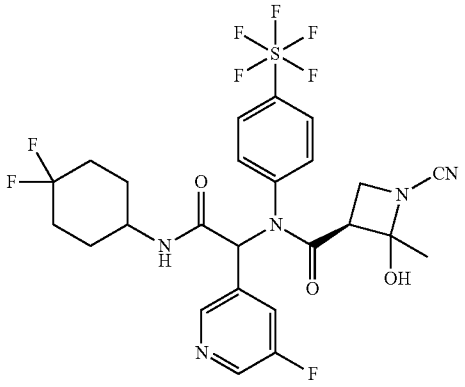 [SMILES: CC1(O)[C@@H](C(=O)N(c2ccc(S(F)(F)(F)(F)F)cc2)C(C(=O)NC2CCC(F)(F)CC2)c2cncc(F)c2)CN1C#N] |
| 1091a | 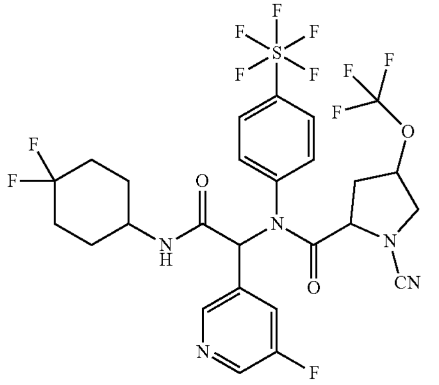 [SMILES: N#CN1CC(OC(F)(F)F)CC1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1091 | 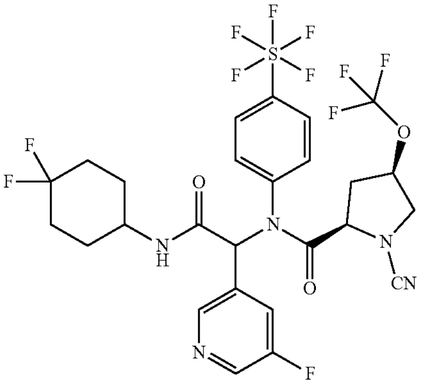 [SMILES: N#CN1C[C@H](OC(F)(F)F)C[C@@H]1C(=O)N(c1ccc(S(F)(F)(F)(F)F)cc1)C(C(=O)NC1CCC(F)(F)CC1)c1cncc(F)c1] |
| 1092a | 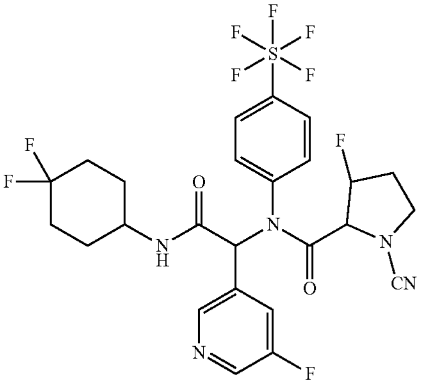 [SMILES: N#CN1CCC(F)C1C(=O)N(c1ccc(S(F)(F)(F)(F)F)cc1)C(C(=O)NC1CCC(F)(F)CC1)c1cncc(F)c1] |
| 1092 | 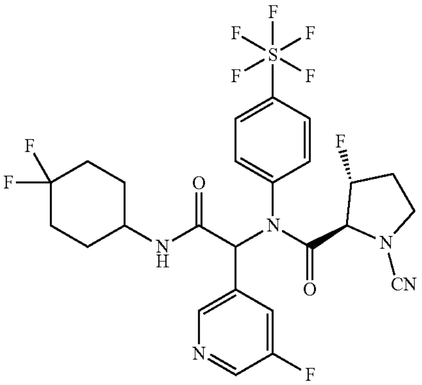 [SMILES: N#CN1CC[C@@H](F)[C@@H]1C(=O)N(c1ccc(S(F)(F)(F)(F)F)cc1)C(C(=O)NC1CCC(F)(F)CC1)c1cncc(F)c1] |
TABLE 1-continued
| Exemplary compounds. | |
|---|---|
| Cmpd No. | Structure |
| 1093 | 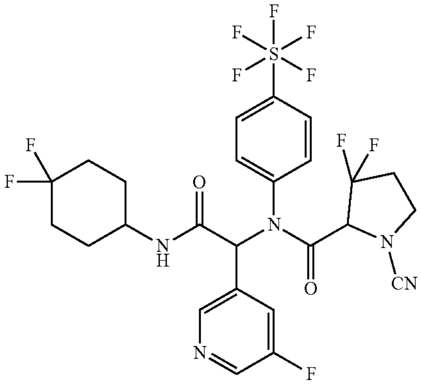 [SMILES: N#CN1CCC(F)(F)C1C(=O)N(c1ccc(S(F)(F)(F)(F)F)cc1)C(C(=O)NC1CCC(F)(F)CC1)c1cncc(F)c1] |
| 1093a | 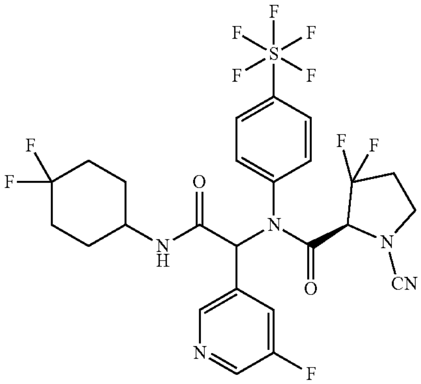 [SMILES: N#CN1CCC(F)(F)[C@@H]1C(=O)N(c1ccc(S(F)(F)(F)(F)F)cc1)C(C(=O)NC1CCC(F)(F)CC1)c1cncc(F)c1] |
| 1094a | 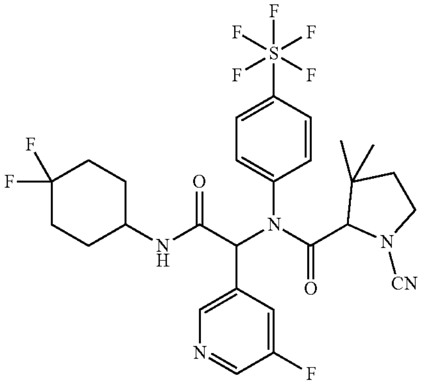 [SMILES: CC1(C)CCN(C#N)C1C(=O)N(c1ccc(S(F)(F)(F)(F)F)cc1)C(C(=O)NC1CCC(F)(F)CC1)c1cncc(F)c1] |
| 1094 | 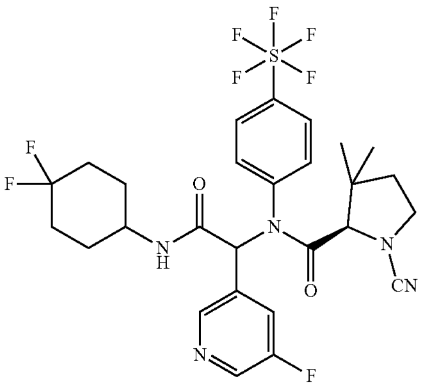 [SMILES: CC1(C)CCN(C#N)[C@H]1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1095a | 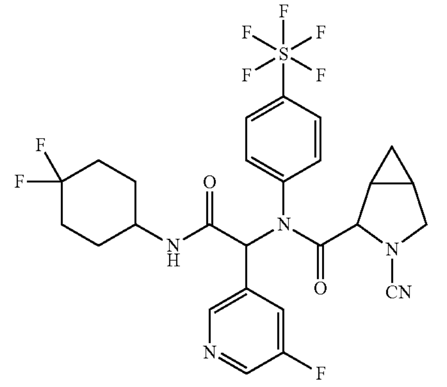 [SMILES: N#CN1CC2CC2C1C(=O)N(c1ccc(S(F)(F)(F)(F)F)cc1)C(C(=O)NC1CCC(F)(F)CC1)c1cncc(F)c1] |
| 1095 | 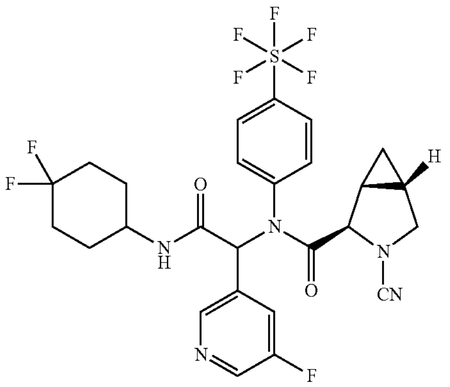 [SMILES: N#CN1C[C@H]2C[C@H]2[C@@H]1C(=O)N(c1ccc(S(F)(F)(F)(F)F)cc1)C(C(=O)NC1CCC(F)(F)CC1)c1cncc(F)c1] |
| 1095b | 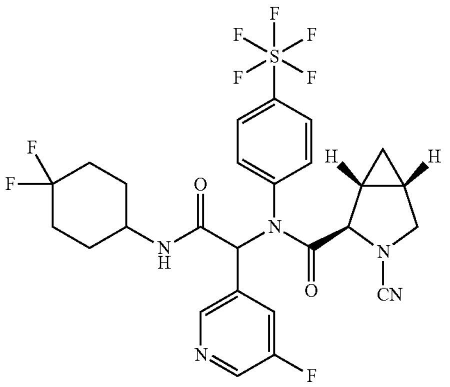 [SMILES: N#CN1C[C@H]2C[C@H]2[C@@H]1C(=O)N(c1ccc(S(F)(F)(F)(F)F)cc1)C(C(=O)NC1CCC(F)(F)CC1)c1cncc(F)c1] |
TABLE 1-continued
| Exemplary compounds. | |
|---|---|
| Cmpd No. | Structure |
| 1096a | 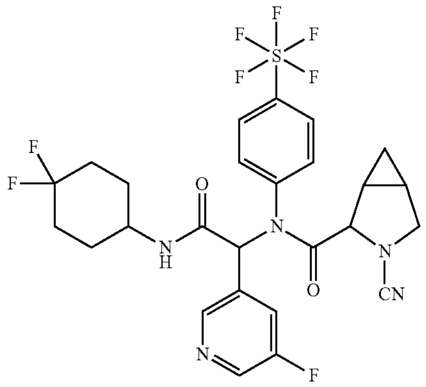 [SMILES: N#CN1CC2CC2C1C(=O)N(c1ccc(S(F)(F)(F)(F)F)cc1)C(C(=O)NC1CCC(F)(F)CC1)c1cncc(F)c1] |
| 1096 | 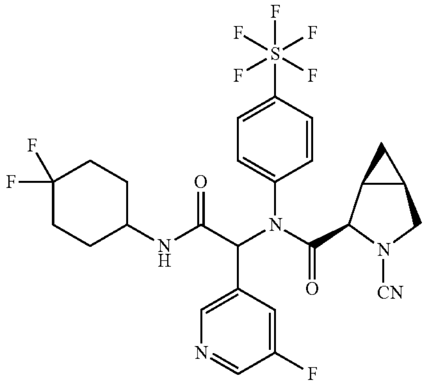 [SMILES: N#CN1C[C@@H]2C[C@@H]2[C@@H]1C(=O)N(c1ccc(S(F)(F)(F)(F)F)cc1)C(C(=O)NC1CCC(F)(F)CC1)c1cncc(F)c1] |
| 1097a | 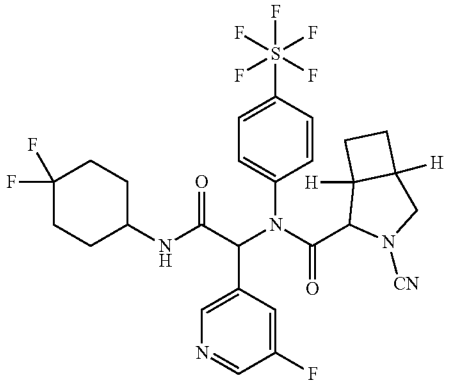 [SMILES: N#CN1CC2CCC2C1C(=O)N(c1ccc(S(F)(F)(F)(F)F)cc1)C(C(=O)NC1CCC(F)(F)CC1)c1cncc(F)c1] |
| 1097 | 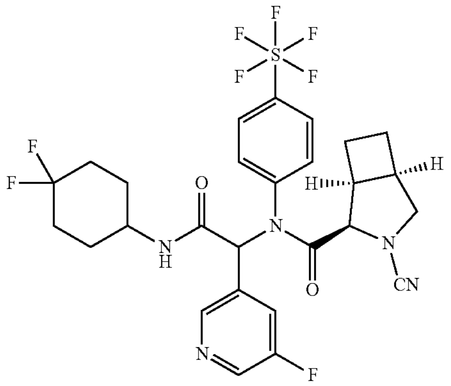 [SMILES: N#CN1C[C@@H]2CC[C@@H]2[C@@H]1C(=O)N(c1ccc(S(F)(F)(F)(F)F)cc1)C(C(=O)NC1CCC(F)(F)CC1)c1cncc(F)c1] |

TABLE 1-continued
| Cmpd No. | Structure |
|---|---|
| Exemplary compounds. | |
| 1098a | 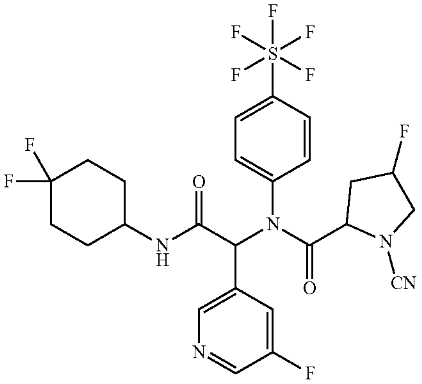 [SMILES: N#CN1CC(F)CC1C(=O)N(c1ccc(S(F)(F)(F)(F)F)cc1)C(C(=O)NC1CCC(F)(F)CC1)c1cncc(F)c1] |
| 1098 | 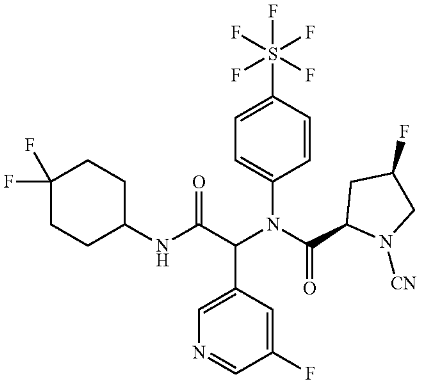 [SMILES: N#CN1C[C@H](F)C[C@@H]1C(=O)N(c1ccc(S(F)(F)(F)(F)F)cc1)C(C(=O)NC1CCC(F)(F)CC1)c1cncc(F)c1] |
| 1099 | 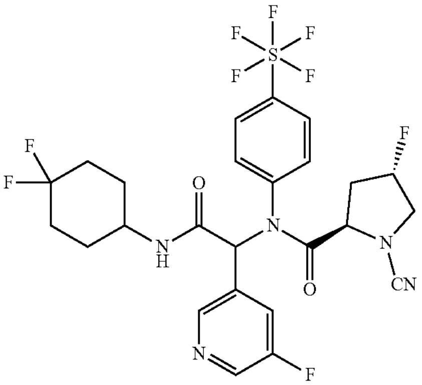 [SMILES: N#CN1C[C@@H](F)C[C@@H]1C(=O)N(c1ccc(S(F)(F)(F)(F)F)cc1)C(C(=O)NC1CCC(F)(F)CC1)c1cncc(F)c1] |
| 1100a | 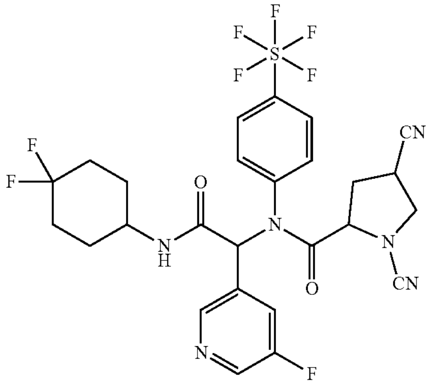 [SMILES: N#CC1CC(C(=O)N(c2ccc(S(F)(F)(F)(F)F)cc2)C(C(=O)NC2CCC(F)(F)CC2)c2cncc(F)c2)N(C#N)C1] |
| 1100 | 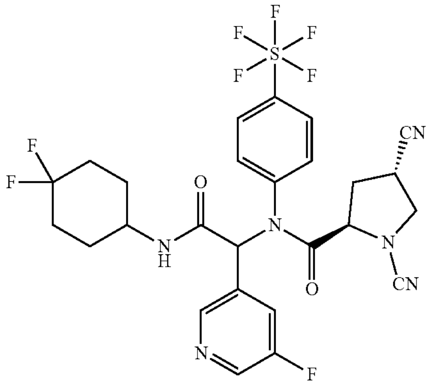 [SMILES: N#C[C@H]1C[C@H](C(=O)N(c2ccc(S(F)(F)(F)(F)F)cc2)C(C(=O)NC2CCC(F)(F)CC2)c2cncc(F)c2)N(C#N)C1] |
| 1101 | 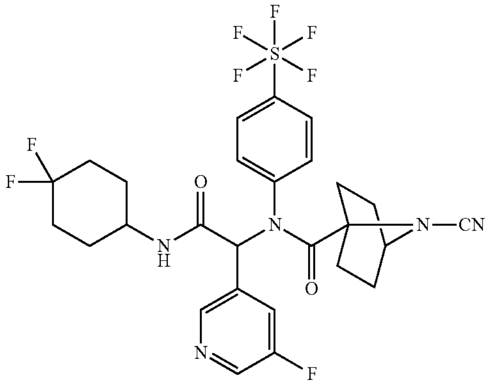 [SMILES: N#CN1C2CCC1(C(=O)N(c1ccc(S(F)(F)(F)(F)F)cc1)C(C(=O)NC1CCC(F)(F)CC1)c1cncc(F)c1)CC2] |
| 1102a | 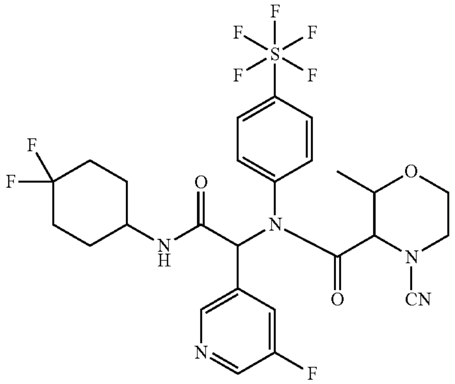 [SMILES: CC1OCCN(C#N)C1C(=O)N(c1ccc(S(F)(F)(F)(F)F)cc1)C(C(=O)NC1CCC(F)(F)CC1)c1cncc(F)c1] |

TABLE 1-continued
| Cmpd No. | Structure |
|---|---|
| 1102 | 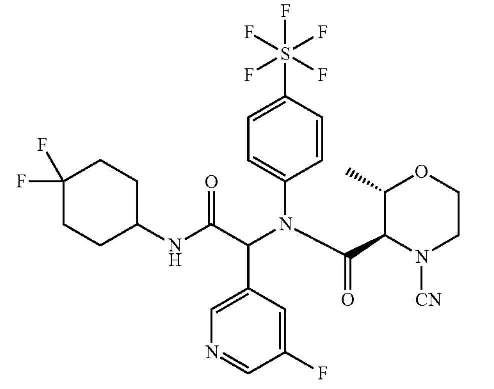 [SMILES: C[C@@H]1OCCN(C#N)[C@H]1C(=O)N(c1ccc(S(F)(F)(F)(F)F)cc1)C(C(=O)NC1CCC(F)(F)CC1)c1cncc(F)c1] |
| 1103 | 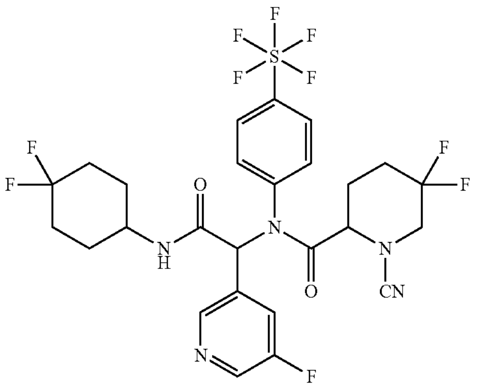 [SMILES: N#CN1CC(F)(F)CCC1C(=O)N(c1ccc(S(F)(F)(F)(F)F)cc1)C(C(=O)NC1CCC(F)(F)CC1)c1cncc(F)c1] |
| 1103a | 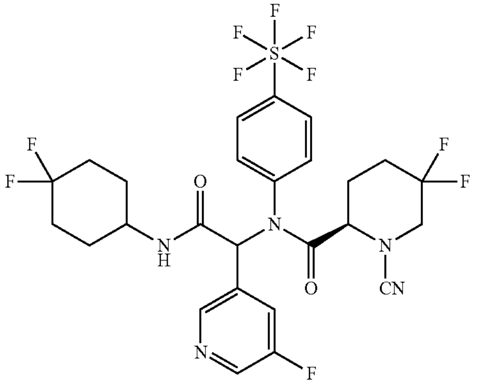 [SMILES: N#CN1CC(F)(F)CC[C@@H]1C(=O)N(c1ccc(S(F)(F)(F)(F)F)cc1)C(C(=O)NC1CCC(F)(F)CC1)c1cncc(F)c1] |
TABLE 1-continued
| Cmpd No. | Structure |
|---|---|
| 1104 | 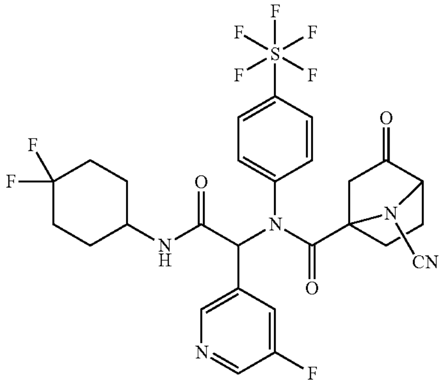 [SMILES: N#CN1C2CCC1(C(=O)N(c1ccc(S(F)(F)(F)(F)F)cc1)C(C(=O)NC1CCC(F)(F)CC1)c1cncc(F)c1)CC2=O] |
| 1105a | 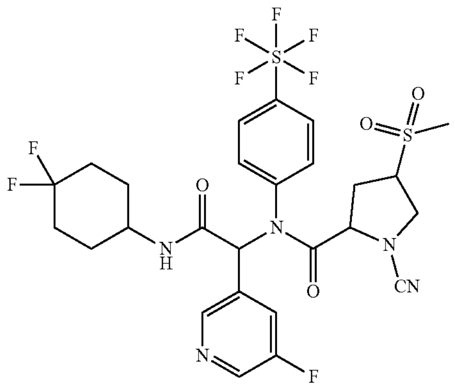 [SMILES: CS(=O)(=O)C1CC(C(=O)N(c2ccc(S(F)(F)(F)(F)F)cc2)C(C(=O)NC2CCC(F)(F)CC2)c2cncc(F)c2)N(C#N)C1] |
| 1105 | 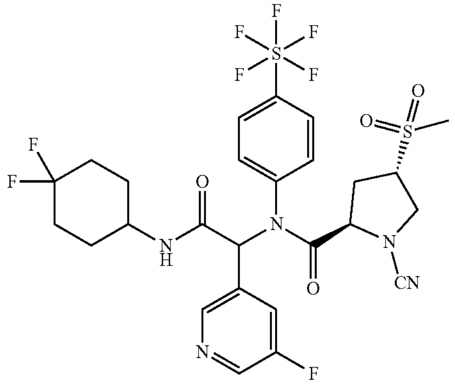 [SMILES: CS(=O)(=O)[C@H]1C[C@H](C(=O)N(c2ccc(S(F)(F)(F)(F)F)cc2)C(C(=O)NC2CCC(F)(F)CC2)c2cncc(F)c2)N(C#N)C1] |

TABLE 1-continued
| Exemplary compounds. | |
|---|---|
| Cmpd No. | Structure |
| 1106a | 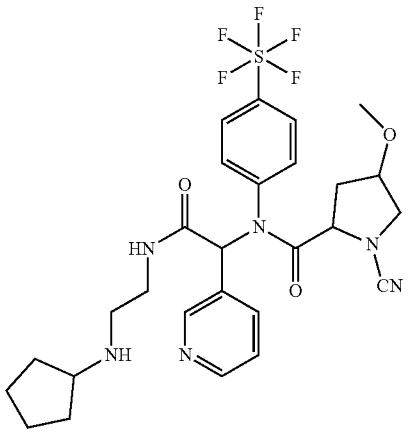 [SMILES: COC1CC(C(=O)N(c2ccc(S(F)(F)(F)(F)F)cc2)C(C(=O)NCCNC2CCCC2)c2cccnc2)N(C#N)C1] |
| 1106 | 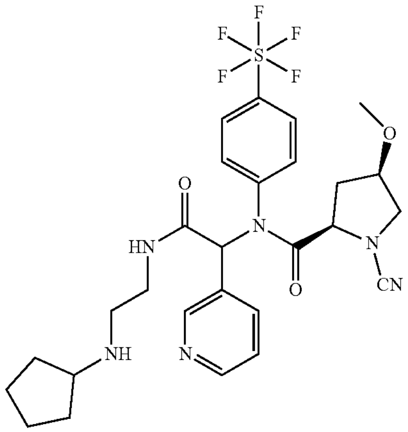 [SMILES: CO[C@@H]1C[C@H](C(=O)N(c2ccc(S(F)(F)(F)(F)F)cc2)C(C(=O)NCCNC2CCCC2)c2cccnc2)N(C#N)C1] |
| 1107a | 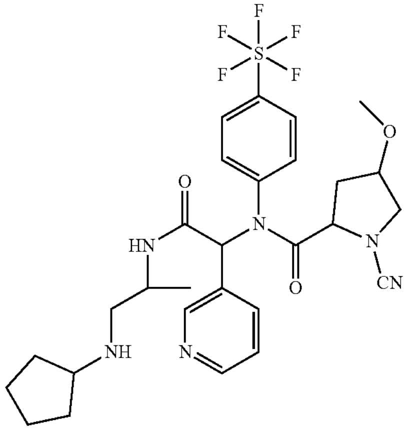 [SMILES: COC1CC(C(=O)N(c2ccc(S(F)(F)(F)(F)F)cc2)C(C(=O)NC(C)CNC2CCCC2)c2cccnc2)N(C#N)C1] |
TABLE 1-continued
| Exemplary compounds. | |
|---|---|
| Cmpd No. | Structure |
| 1107 | 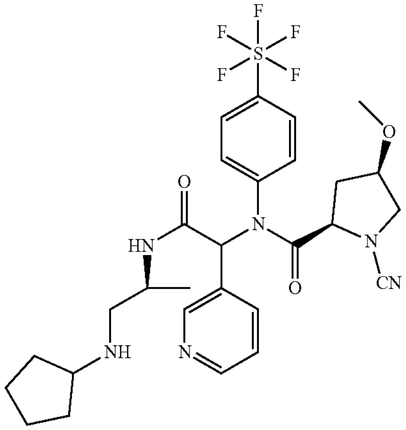 [SMILES: CO[C@@H]1C[C@H](C(=O)N(c2ccc(S(F)(F)(F)(F)F)cc2)C(C(=O)N[C@@H](C)CNC2CCCC2)c2cccnc2)N(C#N)C1] |
| 1108a | 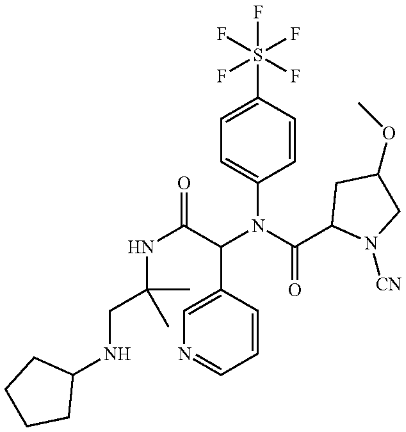 [SMILES: COC1CC(C(=O)N(c2ccc(S(F)(F)(F)(F)F)cc2)C(C(=O)NC(C)(C)CNC2CCCC2)c2cccnc2)N(C#N)C1] |
| 1108 | 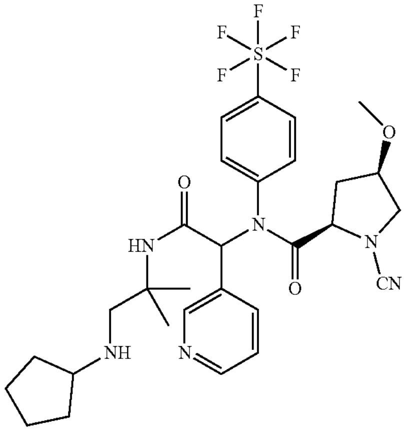 [SMILES: CO[C@@H]1C[C@H](C(=O)N(c2ccc(S(F)(F)(F)(F)F)cc2)C(C(=O)NC(C)(C)CNC2CCCC2)c2cccnc2)N(C#N)C1] |

TABLE 1-continued
| Exemplary compounds. | |
|---|---|
| Cmpd No. | Structure |
| 1109a | 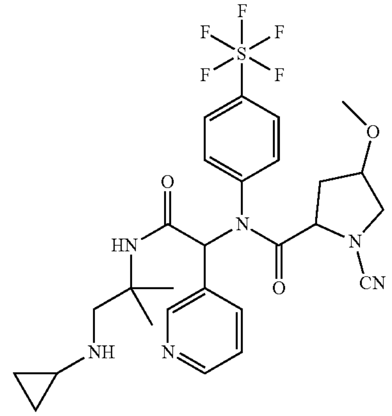 [SMILES: COC1CC(C(=O)N(c2ccc(S(F)(F)(F)(F)F)cc2)C(C(=O)NC(C)(C)CNC2CC2)c2cccnc2)N(C#N)C1] |
| 1109 | 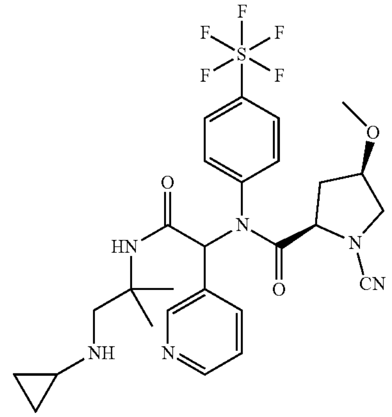 [SMILES: CO[C@@H]1C[C@H](C(=O)N(c2ccc(S(F)(F)(F)(F)F)cc2)C(C(=O)NC(C)(C)CNC2CC2)c2cccnc2)N(C#N)C1] |
| 1110a | 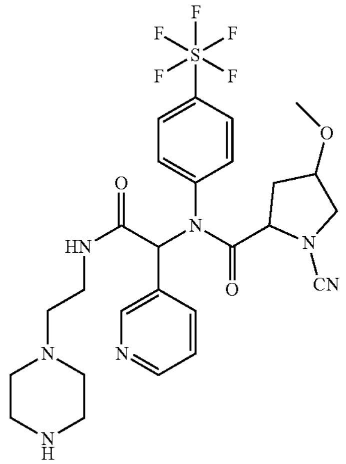 [SMILES: COC1CC(C(=O)N(c2ccc(S(F)(F)(F)(F)F)cc2)C(C(=O)NCCN2CCNCC2)c2cccnc2)N(C#N)C1] |
TABLE 1-continued
| Exemplary compounds. | |
|---|---|
| Cmpd No. | Structure |
| 1110 | 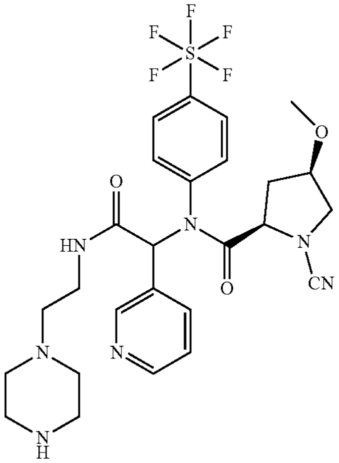 [SMILES: CO[C@@H]1C[C@H](C(=O)N(c2ccc(S(F)(F)(F)(F)F)cc2)C(C(=O)NCCN2CCNCC2)c2cccnc2)N(C#N)C1] |
| 1111a | 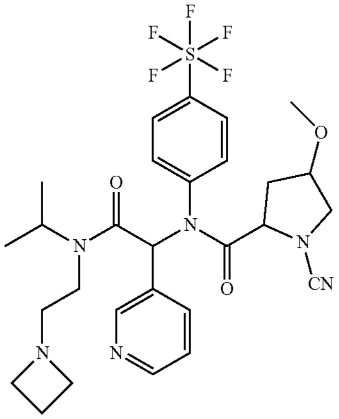 [SMILES: COC1CC(C(=O)N(c2ccc(S(F)(F)(F)(F)F)cc2)C(C(=O)N(CCN2CCC2)C(C)C)c2cccnc2)N(C#N)C1] |
| 1111 | 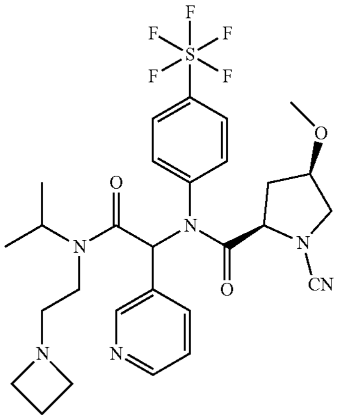 [SMILES: CO[C@@H]1C[C@H](C(=O)N(c2ccc(S(F)(F)(F)(F)F)cc2)C(C(=O)N(CCN2CCC2)C(C)C)c2cccnc2)N(C#N)C1] |

TABLE 1-continued
| Exemplary compounds. | |
|---|---|
| Cmpd No. | Structure |
| 1112a | 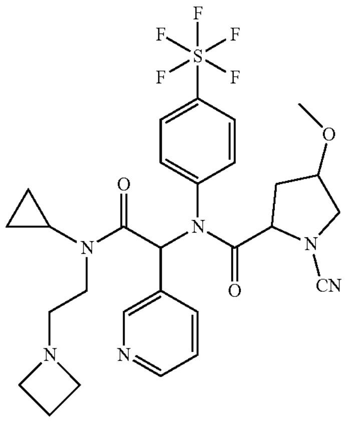 [SMILES: COC1CC(C(=O)N(c2ccc(S(F)(F)(F)(F)F)cc2)C(C(=O)N(CCN2CCC2)C2CC2)c2cccnc2)N(C#N)C1] |
| 1112 | 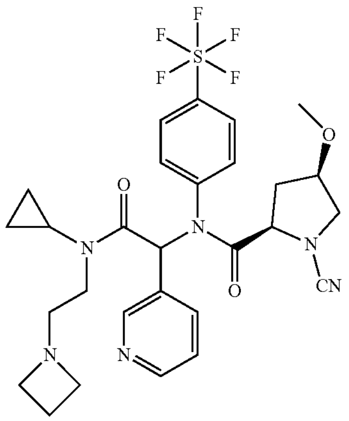 [SMILES: CO[C@@H]1C[C@H](C(=O)N(c2ccc(S(F)(F)(F)(F)F)cc2)C(C(=O)N(CCN2CCC2)C2CC2)c2cccnc2)N(C#N)C1] |
| 1113a | 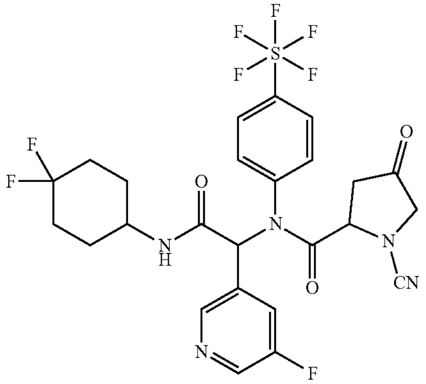 [SMILES: N#CN1CC(=O)CC1C(=O)N(c1ccc(S(F)(F)(F)(F)F)cc1)C(C(=O)NC1CCC(F)(F)CC1)c1cncc(F)c1] |
TABLE 1-continued
| Exemplary compounds. | |
|---|---|
| Cmpd No. | Structure |
| 1113 | 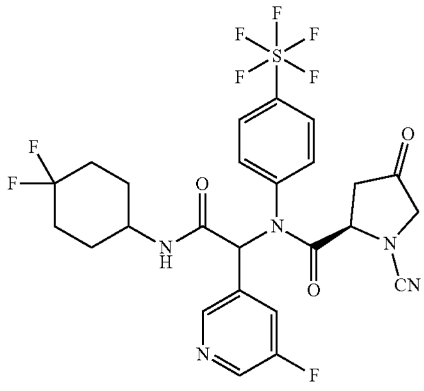 [SMILES: N#CN1CC(=O)C[C@@H]1C(=O)N(c1ccc(S(F)(F)(F)(F)F)cc1)C(C(=O)NC1CCC(F)(F)CC1)c1cncc(F)c1] |
| 1114 | 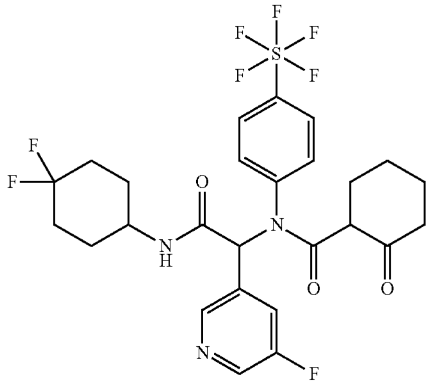 [SMILES: O=C1CCCCC1C(=O)N(c1ccc(S(F)(F)(F)(F)F)cc1)C(C(=O)NC1CCC(F)(F)CC1)c1cncc(F)c1] |
| 1115 | 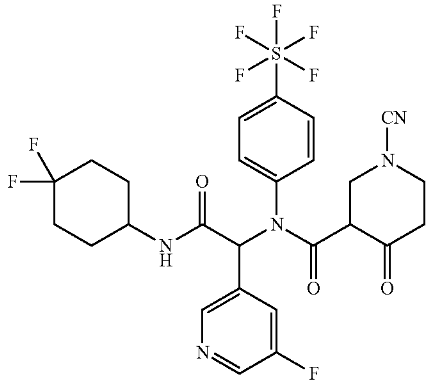 [SMILES: N#CN1CCC(=O)C(C(=O)N(c2ccc(S(F)(F)(F)(F)F)cc2)C(C(=O)NC2CCC(F)(F)CC2)c2cncc(F)c2)C1] |
| 1115a | 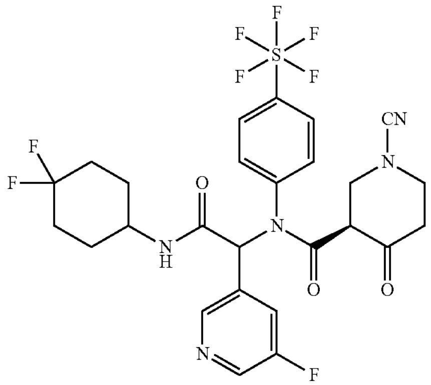 [SMILES: N#CN1CCC(=O)[C@@H](C(=O)N(c2ccc(S(F)(F)(F)(F)F)cc2)C(C(=O)NC2CCC(F)(F)CC2)c2cncc(F)c2)C1] |

TABLE 1-continued
| Exemplary compounds. | |
|---|---|
| Cmpd No. | Structure |
| 1116 | 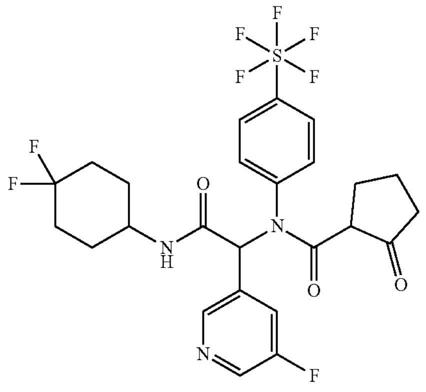 [SMILES: O=C1CCCC1C(=O)N(c1ccc(S(F)(F)(F)(F)F)cc1)C(C(=O)NC1CCC(F)(F)CC1)c1cncc(F)c1] |
| 1117a | 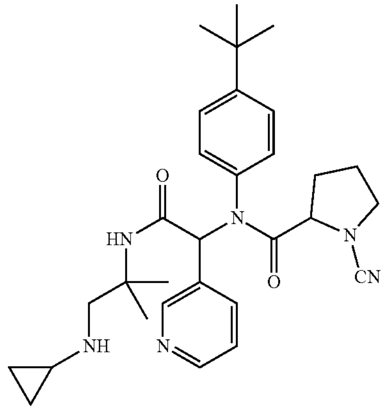 [SMILES: CC(C)(CNC1CC1)NC(=O)C(c1cccnc1)N(C(=O)C1CCCN1C#N)c1ccc(C(C)(C)C)cc1] |
| 1117 | 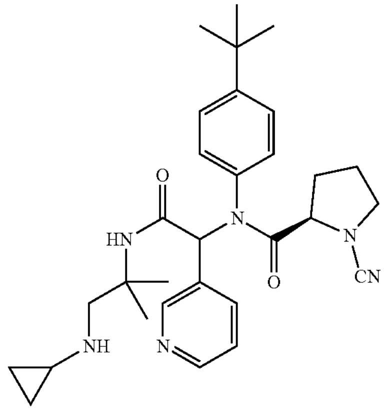 [SMILES: CC(C)(CNC1CC1)NC(=O)C(c1cccnc1)N(C(=O)[C@H]1CCCN1C#N)c1ccc(C(C)(C)C)cc1] |
TABLE 1-continued
| Exemplary compounds. | |
|---|---|
| Cmpd No. | Structure |
| 1118a | 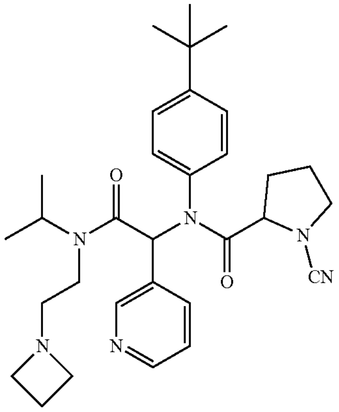 [SMILES: CC(C)N(CCN1CCC1)C(=O)C(c1cccnc1)N(C(=O)C1CCCN1C#N)c1ccc(C(C)(C)C)cc1] |
| 1118 | 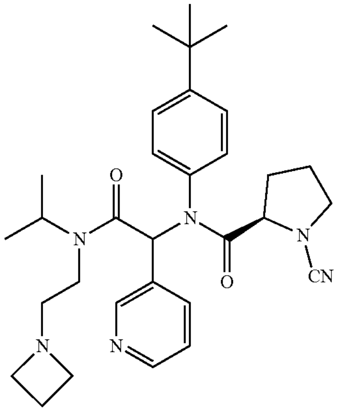 [SMILES: CC(C)N(CCN1CCC1)C(=O)C(c1cccnc1)N(C(=O)[C@H]1CCCN1C#N)c1ccc(C(C)(C)C)cc1] |
| 1119a | 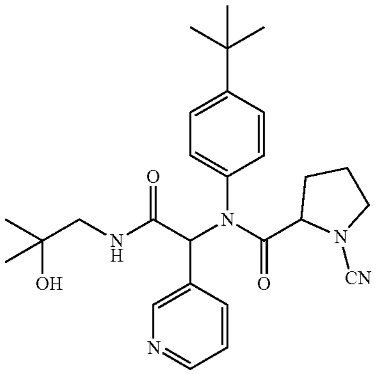 [SMILES: CC(C)(O)CNC(=O)C(c1cccnc1)N(C(=O)C1CCCN1C#N)c1ccc(C(C)(C)C)cc1] |

TABLE 1-continued
| Exemplary compounds. | |
|---|---|
| Cmpd No. | Structure |
| 1119 | 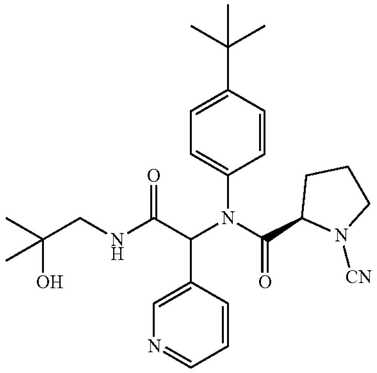 [SMILES: CC(C)(O)CNC(=O)C(c1cccnc1)N(C(=O)[C@H]1CCCN1C#N)c1ccc(C(C)(C)C)cc1] |
| 1120a | 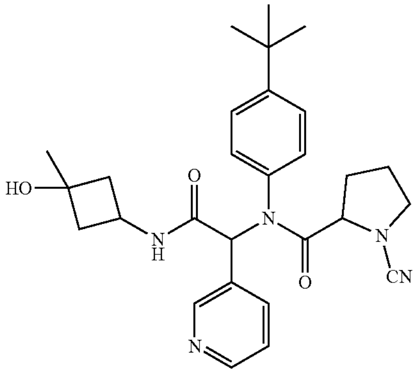 [SMILES: CC1(O)CC(NC(=O)C(c2cccnc2)N(C(=O)C2CCCN2C#N)c2ccc(C(C)(C)C)cc2)C1] |
| 1120 | 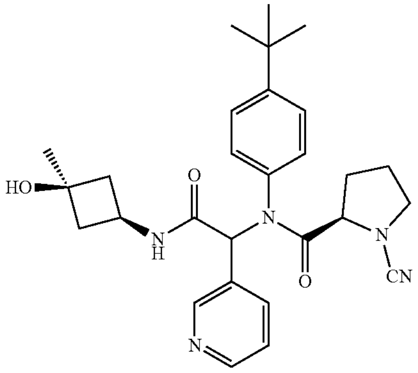 [SMILES: CC(C)(C)c1ccc(N(C(=O)[C@H]2CCCN2C#N)C(C(=O)N[C@H]2C[C@@](C)(O)C2)c2cccnc2)cc1] |
TABLE 1-continued
| Exemplary compounds. | |
|---|---|
| Cmpd No. | Structure |
| 1121a | 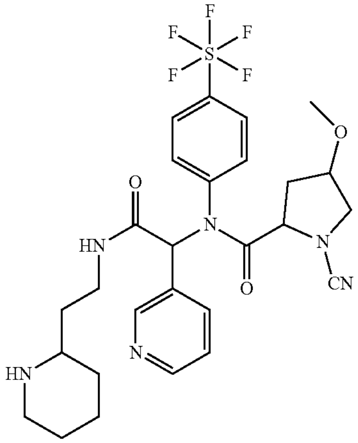 [SMILES: COC1CC(C(=O)N(c2ccc(S(F)(F)(F)(F)F)cc2)C(C(=O)NCCC2CCCCN2)c2cccnc2)N(C#N)C1] |
| 1121 | 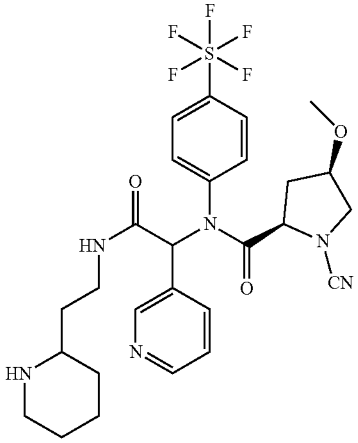 [SMILES: CO[C@@H]1C[C@H](C(=O)N(c2ccc(S(F)(F)(F)(F)F)cc2)C(C(=O)NCCC2CCCCN2)c2cccnc2)N(C#N)C1] |
| 1121b | 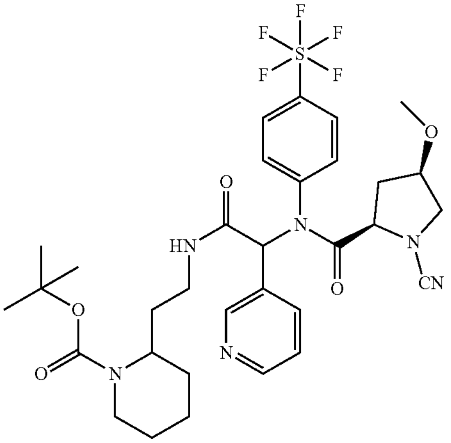 [SMILES: CO[C@@H]1C[C@H](C(=O)N(c2ccc(S(F)(F)(F)(F)F)cc2)C(C(=O)NCCC2CCCCN2C(=O)OC(C)(C)C)c2cccnc2)N(C#N)C1] |

TABLE 1-continued
| Exemplary compounds. | |
|---|---|
| Cmpd No. | Structure |
| 1122a | 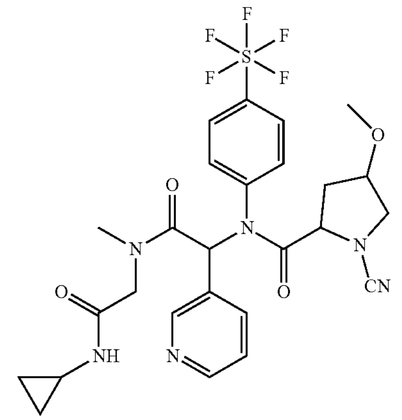 [SMILES: COC1CC(C(=O)N(c2ccc(S(F)(F)(F)(F)F)cc2)C(C(=O)N(C)CC(=O)NC2CC2)c2cccnc2)N(C#N)C1] |
| 1122 | 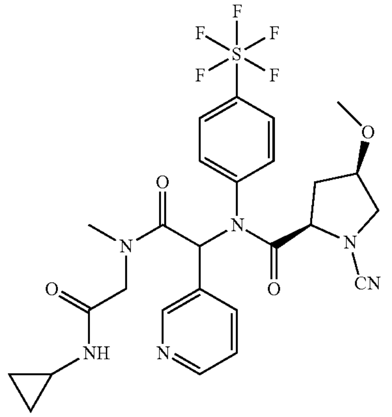 [SMILES: CO[C@@H]1C[C@H](C(=O)N(c2ccc(S(F)(F)(F)(F)F)cc2)C(C(=O)N(C)CC(=O)NC2CC2)c2cccnc2)N(C#N)C1] |
| 1123a | 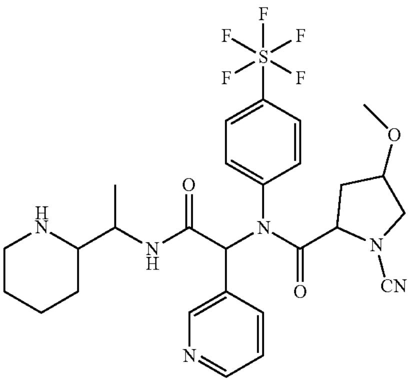 [SMILES: COC1CC(C(=O)N(c2ccc(S(F)(F)(F)(F)F)cc2)C(C(=O)NC(C)C2CCCCN2)c2cccnc2)N(C#N)C1] |
| 1123 | 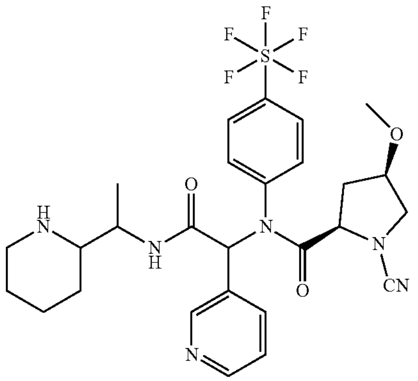 [SMILES: CO[C@@H]1C[C@H](C(=O)N(c2ccc(S(F)(F)(F)(F)F)cc2)C(C(=O)NC(C)C2CCCCN2)c2cccnc2)N(C#N)C1] |
| 1124a | 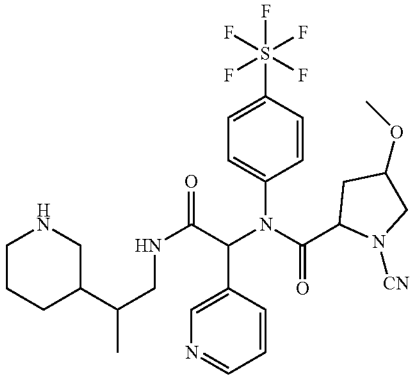 [SMILES: COC1CC(C(=O)N(c2ccc(S(F)(F)(F)(F)F)cc2)C(C(=O)NCC(C)C2CCCNC2)c2cccnc2)N(C#N)C1] |
| 1124 | 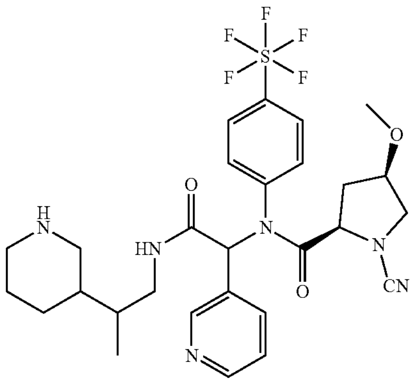 [SMILES: CO[C@@H]1C[C@H](C(=O)N(c2ccc(S(F)(F)(F)(F)F)cc2)C(C(=O)NCC(C)C2CCCNC2)c2cccnc2)N(C#N)C1] |
| 1125a | 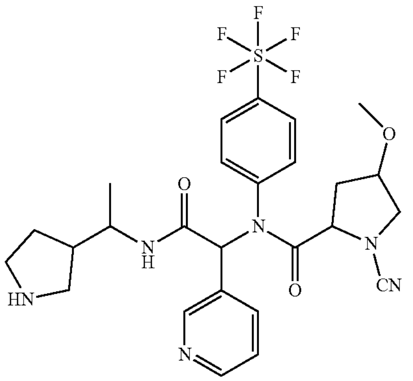 [SMILES: COC1CC(C(=O)N(c2ccc(S(F)(F)(F)(F)F)cc2)C(C(=O)NC(C)C2CCNC2)c2cccnc2)N(C#N)C1] |

TABLE 1-continued
Exemplary compounds.
| Cmpd No. | Structure |
| --- | --- |
| 1125 | 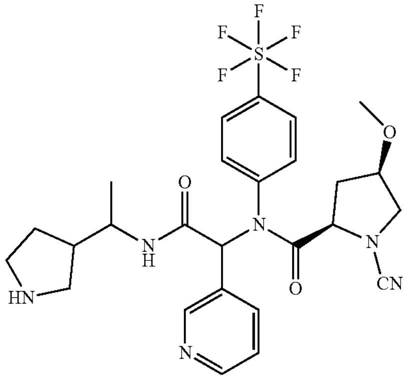 [SMILES: CO[C@@H]1C[C@H](C(=O)N(c2ccc(S(F)(F)(F)(F)F)cc2)C(C(=O)NC(C)C2CCNC2)c2cccnc2)N(C#N)C1] |
| 1125a | 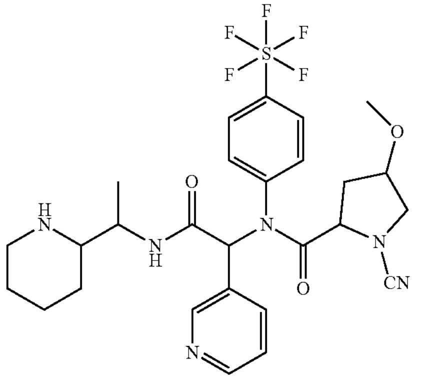 [SMILES: COC1CC(C(=O)N(c2ccc(S(F)(F)(F)(F)F)cc2)C(C(=O)NC(C)C2CCCCN2)c2cccnc2)N(C#N)C1] |
| 1125b | 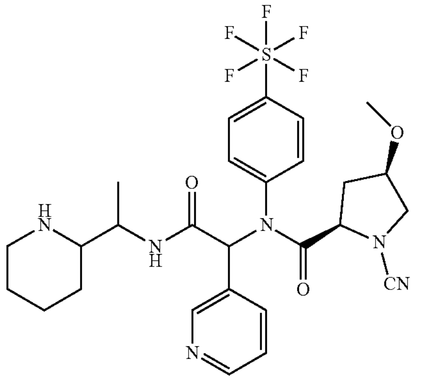 [SMILES: CO[C@@H]1C[C@H](C(=O)N(c2ccc(S(F)(F)(F)(F)F)cc2)C(C(=O)NC(C)C2CCCCN2)c2cccnc2)N(C#N)C1] |
| 1126a | 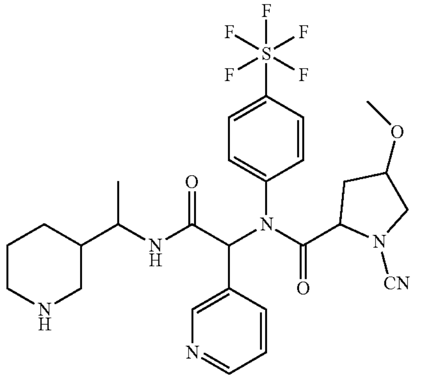 [SMILES: COC1CC(C(=O)N(c2ccc(S(F)(F)(F)(F)F)cc2)C(C(=O)NC(C)C2CCCNC2)c2cccnc2)N(C#N)C1] |
| 1126 | 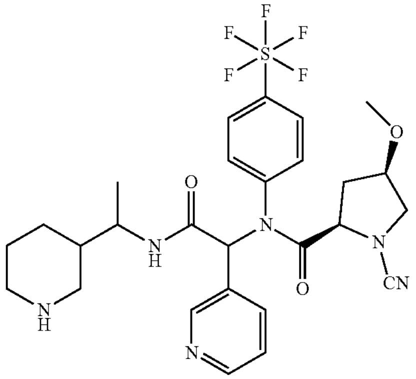 [SMILES: CO[C@@H]1C[C@H](C(=O)N(c2ccc(S(F)(F)(F)(F)F)cc2)C(C(=O)NC(C)C2CCCNC2)c2cccnc2)N(C#N)C1] |
| 1127a | 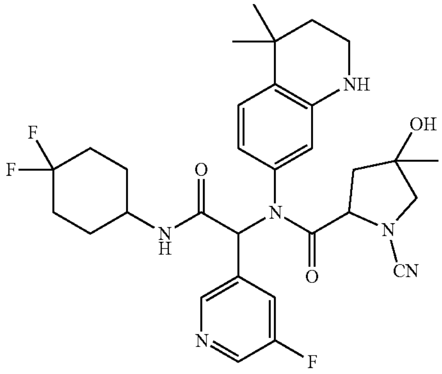 [SMILES: CC1(O)CC(C(=O)N(c2ccc3c(c2)NCCC3(C)C)C(C(=O)NC2CCC(F)(F)CC2)c2cncc(F)c2)N(C#N)C1] |
| 1127 | 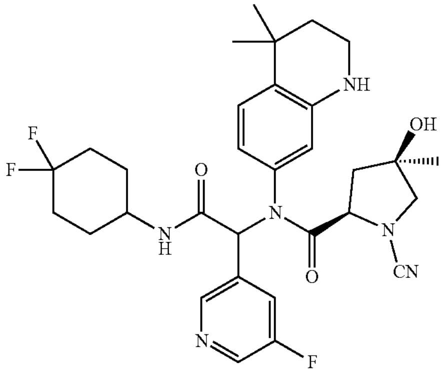 [SMILES: CC1(C)CCNc2cc(N(C(=O)[C@H]3C[C@@](C)(O)CN3C#N)C(C(=O)NC3CCC(F)(F)CC3)c3cncc(F)c3)ccc21] |
| 1128a | 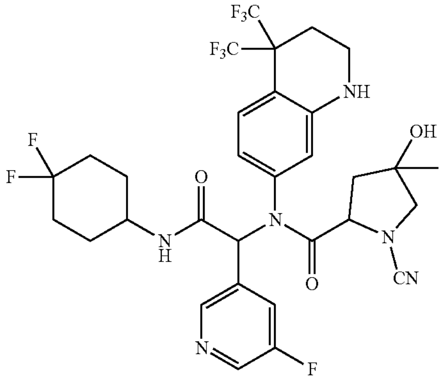 [SMILES: CC1(O)CC(C(=O)N(c2ccc3c(c2)NCCC3(C(F)(F)F)C(F)(F)F)C(C(=O)NC2CCC(F)(F)CC2)c2cncc(F)c2)N(C#N)C1] |

TABLE 1-continued
Exemplary compounds.
| Cmpd No. | Structure |
|---|---|
| 1128 | 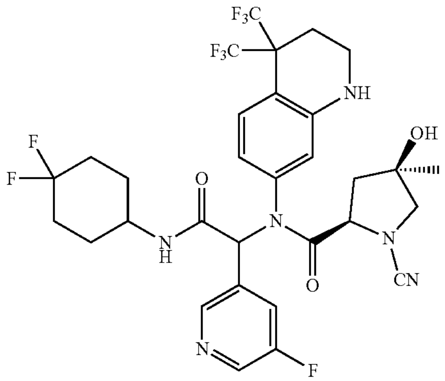 [SMILES: C[C@@]1(O)C[C@H](C(=O)N(c2ccc3c(c2)NCCC3(C(F)(F)F)C(F)(F)F)C(C(=O)NC2CCC(F)(F)CC2)c2cncc(F)c2)N(C#N)C1] |
| 1129a | 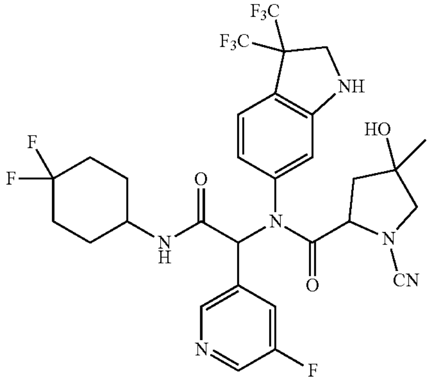 [SMILES: CC1(O)CC(C(=O)N(c2ccc3c(c2)NCC3(C(F)(F)F)C(F)(F)F)C(C(=O)NC2CCC(F)(F)CC2)c2cncc(F)c2)N(C#N)C1] |
| 1129 | 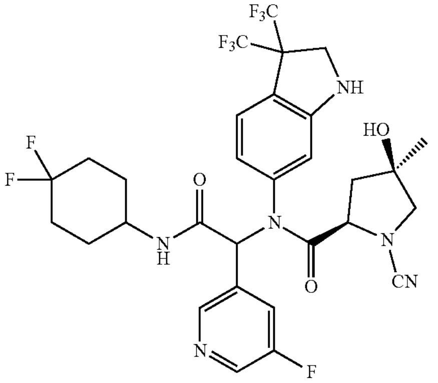 [SMILES: C[C@@]1(O)C[C@H](C(=O)N(c2ccc3c(c2)NCC3(C(F)(F)F)C(F)(F)F)C(C(=O)NC2CCC(F)(F)CC2)c2cncc(F)c2)N(C#N)C1] |
| 1130a | 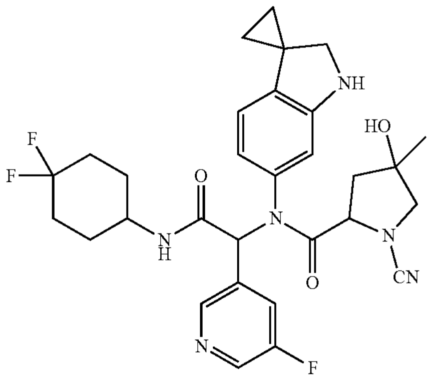 [SMILES: CC1(O)CC(C(=O)N(c2ccc3c(c2)NCC32CC2)C(C(=O)NC2CCC(F)(F)CC2)c2cncc(F)c2)N(C#N)C1] |
TABLE 1-continued
Exemplary compounds.
| Cmpd No. | Structure |
|---|---|
| 1130 | 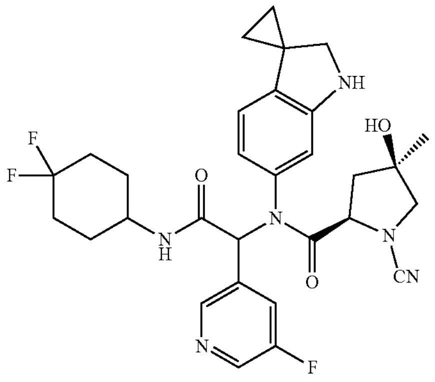 [SMILES: C[C@@]1(O)C[C@H](C(=O)N(c2ccc3c(c2)NCC32CC2)C(C(=O)NC2CCC(F)(F)CC2)c2cncc(F)c2)N(C#N)C1] |
| 1131a | 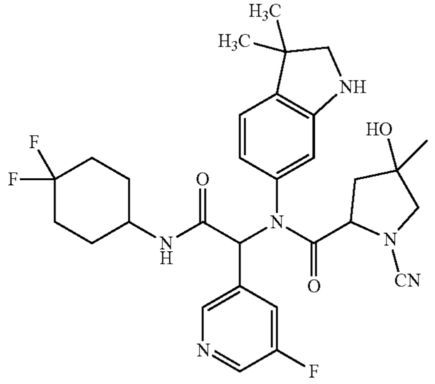 [SMILES: CC1(O)CC(C(=O)N(c2ccc3c(c2)NCC3(C)C)C(C(=O)NC2CCC(F)(F)CC2)c2cncc(F)c2)N(C#N)C1] |
| 1131 | 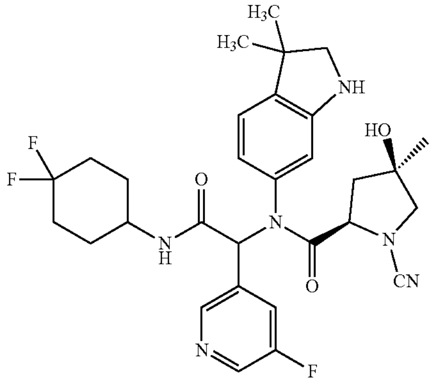 [SMILES: CC1(C)CNc2cc(N(C(=O)[C@H]3C[C@@](C)(O)CN3C#N)C(C(=O)NC3CCC(F)(F)CC3)c3cncc(F)c3)ccc21] |

TABLE 1-continued
Exemplary compounds.
| Cmpd No. | Structure |
| --- | --- |
| 1132a | 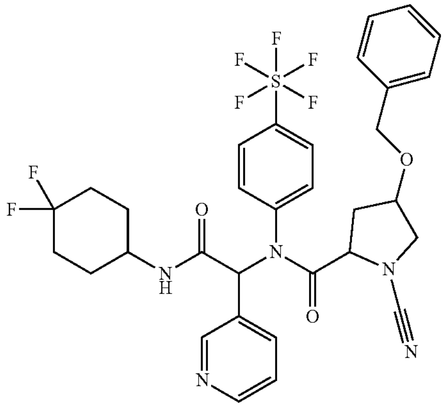 [SMILES: N#CN1CC(OCc2ccccc2)CC1C(=O)N(c1ccc(S(F)(F)(F)(F)F)cc1)C(C(=O)NC1CCC(F)(F)CC1)c1cccnc1] |
| 1132 | 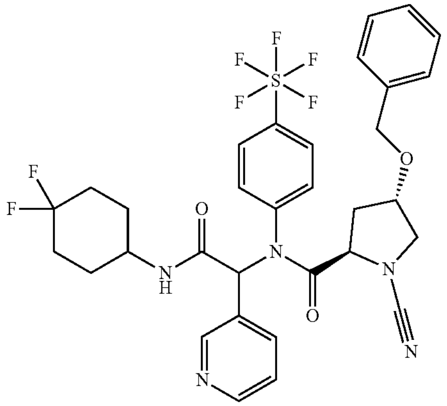 [SMILES: N#CN1C[C@@H](OCc2ccccc2)C[C@@H]1C(=O)N(c1ccc(S(F)(F)(F)(F)F)cc1)C(C(=O)NC1CCC(F)(F)CC1)c1cccnc1] |
| 1133a | 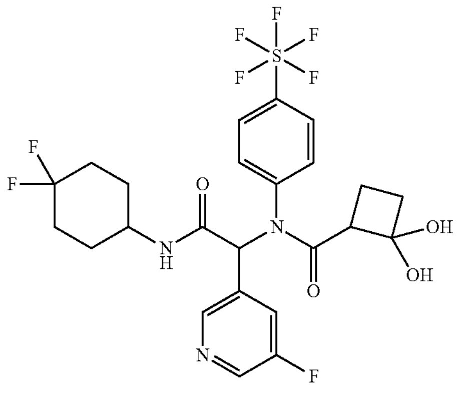 [SMILES: O=C(NC1CCC(F)(F)CC1)C(c1cncc(F)c1)N(C(=O)C1CCC1(O)O)c1ccc(S(F)(F)(F)(F)F)cc1] |
| 1134a | 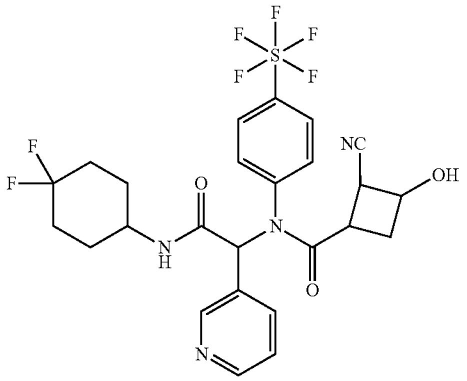 [SMILES: N#CC1C(O)CC1C(=O)N(c1ccc(S(F)(F)(F)(F)F)cc1)C(C(=O)NC1CCC(F)(F)CC1)c1cccnc1] |
| 1134 | 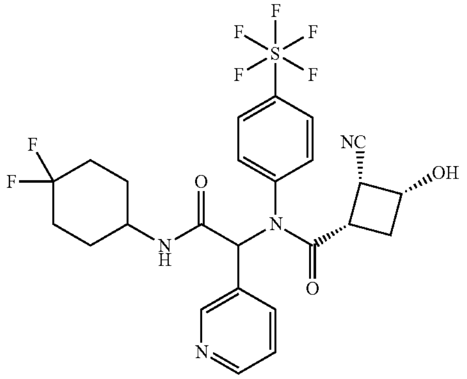 [SMILES: N#C[C@@H]1[C@H](O)C[C@@H]1C(=O)N(c1ccc(S(F)(F)(F)(F)F)cc1)C(C(=O)NC1CCC(F)(F)CC1)c1cccnc1] |
| 1135a | 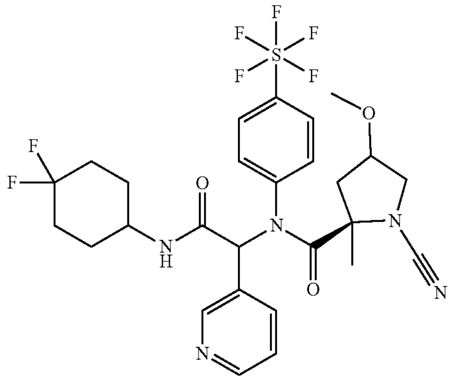 [SMILES: COC1CN(C#N)[C@@](C)(C(=O)N(c2ccc(S(F)(F)(F)(F)F)cc2)C(C(=O)NC2CCC(F)(F)CC2)c2cccnc2)C1] |
| 1135 | 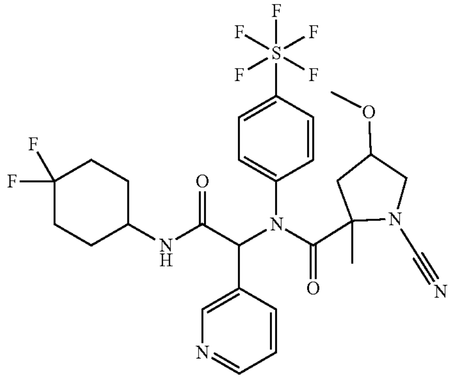 [SMILES: COC1CN(C#N)C(C)(C(=O)N(c2ccc(S(F)(F)(F)(F)F)cc2)C(C(=O)NC2CCC(F)(F)CC2)c2cccnc2)C1] |

TABLE 1-continued
Exemplary compounds.
| Cmpd No. | Structure |
|---|---|
| 1135b | 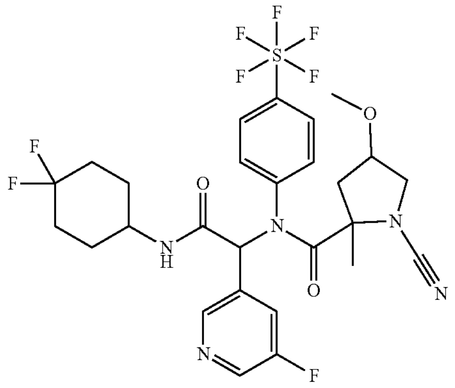 [SMILES: COC1CN(C#N)C(C)(C(=O)N(c2ccc(S(F)(F)(F)(F)F)cc2)C(C(=O)NC2CCC(F)(F)CC2)c2cncc(F)c2)C1] |
| 1136a | 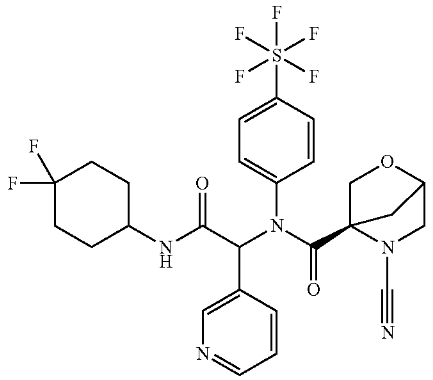 [SMILES: N#CN1CC2C[C@@]1(C(=O)N(c1ccc(S(F)(F)(F)(F)F)cc1)C(C(=O)NC1CCC(F)(F)CC1)c1cccnc1)CO2] |
| 1136 | 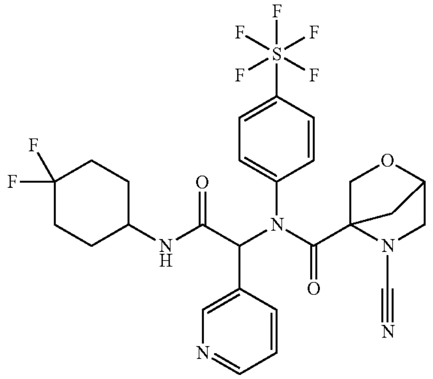 [SMILES: N#CN1CC2CC1(C(=O)N(c1ccc(S(F)(F)(F)(F)F)cc1)C(C(=O)NC1CCC(F)(F)CC1)c1cccnc1)CO2] |
| 1136b | 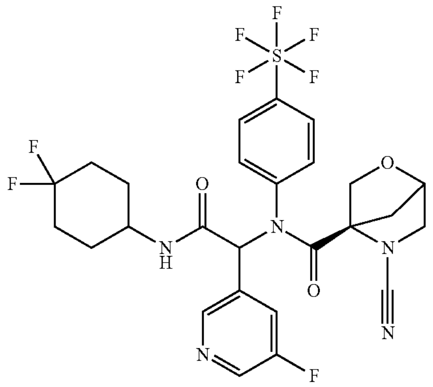 [SMILES: N#CN1CC2C[C@@]1(C(=O)N(c1ccc(S(F)(F)(F)(F)F)cc1)C(C(=O)NC1CCC(F)(F)CC1)c1cncc(F)c1)CO2] |
TABLE 1-continued
Exemplary compounds.
| Cmpd No. | Structure |
|---|---|
| 1136c | 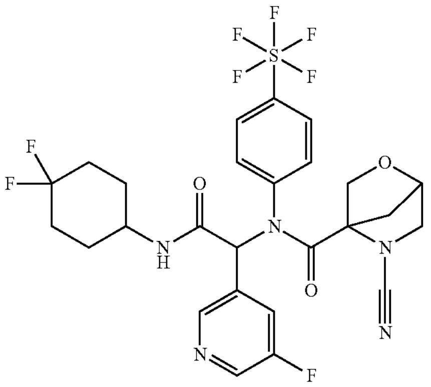 [SMILES: N#CN1CC2CC1(C(=O)N(c1ccc(S(F)(F)(F)(F)F)cc1)C(C(=O)NC1CCC(F)(F)CC1)c1cncc(F)c1)CO2] |
| 1137a | 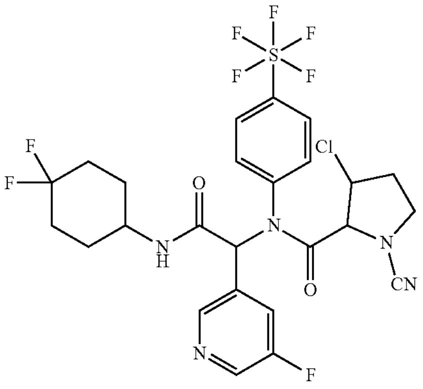 [SMILES: N#CN1CCC(Cl)C1C(=O)N(c1ccc(S(F)(F)(F)(F)F)cc1)C(C(=O)NC1CCC(F)(F)CC1)c1cncc(F)c1] |
| 1137 | 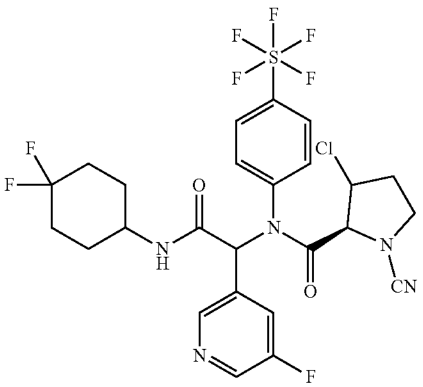 [SMILES: N#CN1CCC(Cl)[C@@H]1C(=O)N(c1ccc(S(F)(F)(F)(F)F)cc1)C(C(=O)NC1CCC(F)(F)CC1)c1cncc(F)c1] |

TABLE 1-continued
Exemplary compounds.
| Cmpd No. | Structure |
| --- | --- |
| 1138a | 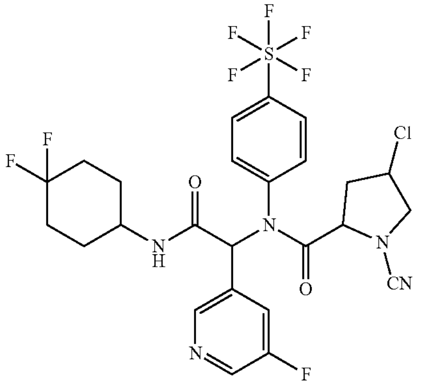 [SMILES: N#CN1CC(Cl)CC1C(=O)N(c1ccc(S(F)(F)(F)(F)F)cc1)C(C(=O)NC1CCC(F)(F)CC1)c1cncc(F)c1] |
| 1138 | 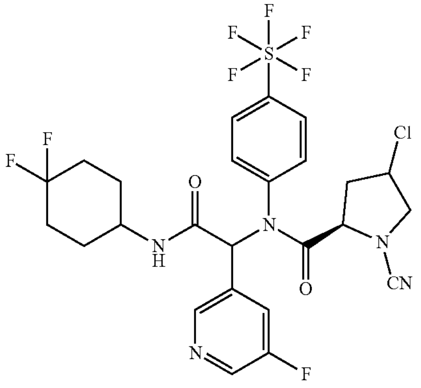 [SMILES: N#CN1CC(Cl)C[C@@H]1C(=O)N(c1ccc(S(F)(F)(F)(F)F)cc1)C(C(=O)NC1CCC(F)(F)CC1)c1cncc(F)c1] |
| 1139a | 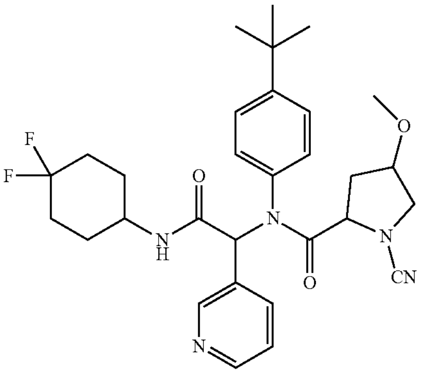 [SMILES: COC1CC(C(=O)N(c2ccc(C(C)(C)C)cc2)C(C(=O)NC2CCC(F)(F)CC2)c2cccnc2)N(C#N)C1] |
| 1139 | 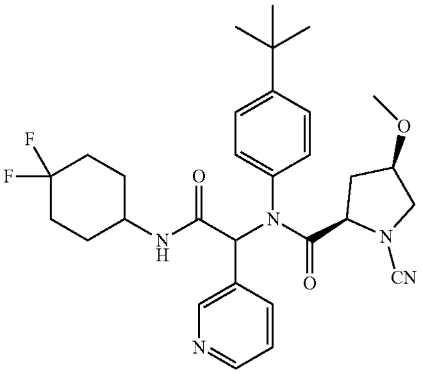 [SMILES: CO[C@@H]1C[C@H](C(=O)N(c2ccc(C(C)(C)C)cc2)C(C(=O)NC2CCC(F)(F)CC2)c2cccnc2)N(C#N)C1] |
TABLE 1-continued
Exemplary compounds.
| Cmpd No. | Structure |
| --- | --- |
| 1140a | 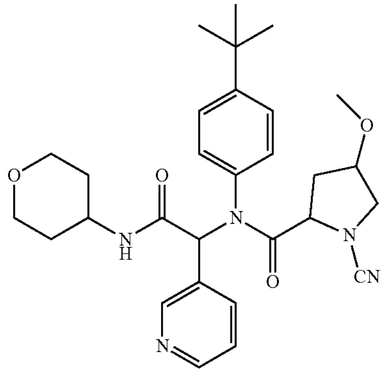 [SMILES: COC1CC(C(=O)N(c2ccc(C(C)(C)C)cc2)C(C(=O)NC2CCOCC2)c2cccnc2)N(C#N)C1] |
| 1140 | 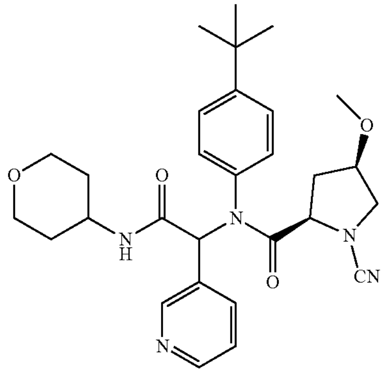 [SMILES: CO[C@@H]1C[C@H](C(=O)N(c2ccc(C(C)(C)C)cc2)C(C(=O)NC2CCOCC2)c2cccnc2)N(C#N)C1] |
| 1141a | 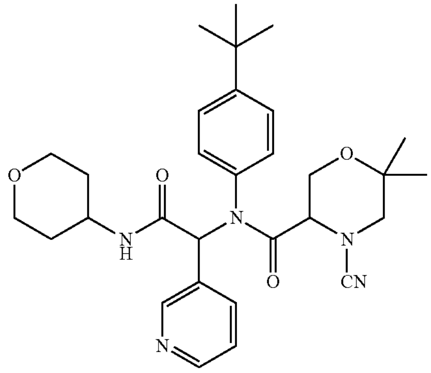 [SMILES: CC1(C)CN(C#N)C(C(=O)N(c2ccc(C(C)(C)C)cc2)C(C(=O)NC2CCOCC2)c2cccnc2)CO1] |
| 1141 | 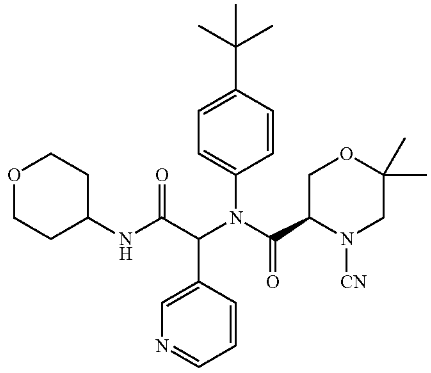 [SMILES: CC1(C)CN(C#N)[C@@H](C(=O)N(c2ccc(C(C)(C)C)cc2)C(C(=O)NC2CCOCC2)c2cccnc2)CO1] |

TABLE 1-continued
Exemplary compounds.
| Cmpd No. | Structure |
|---|---|
| 1142a | 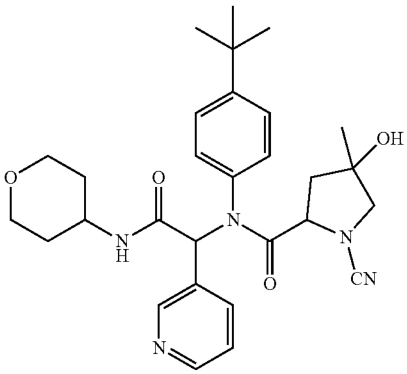 [SMILES: CC1(O)CC(C(=O)N(c2ccc(C(C)(C)C)cc2)C(C(=O)NC2CCOCC2)c2cccnc2)N(C#N)C1] |
| 1142 | 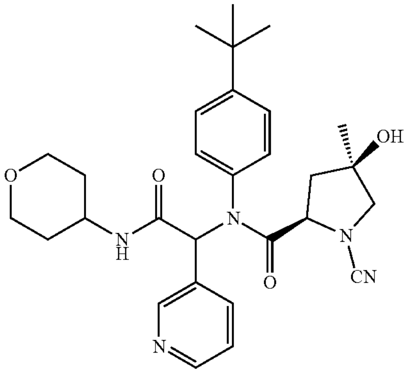 [SMILES: CC(C)(C)c1ccc(N(C(=O)[C@H]2C[C@@](C)(O)CN2C#N)C(C(=O)NC2CCOCC2)c2cccnc2)cc1] |
| 1143a | 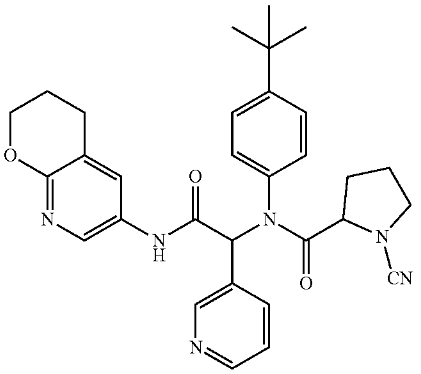 [SMILES: CC(C)(C)c1ccc(N(C(=O)C2CCCN2C#N)C(C(=O)Nc2cnc3c(c2)CCCO3)c2cccnc2)cc1] |
| 1143 | 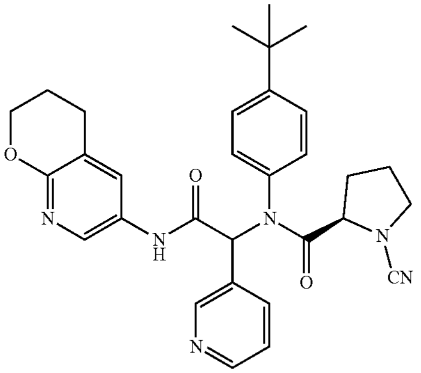 [SMILES: CC(C)(C)c1ccc(N(C(=O)[C@H]2CCCN2C#N)C(C(=O)Nc2cnc3c(c2)CCCO3)c2cccnc2)cc1] |
TABLE 1-continued
Exemplary compounds.
| Cmpd No. | Structure |
|---|---|
| 1144a | 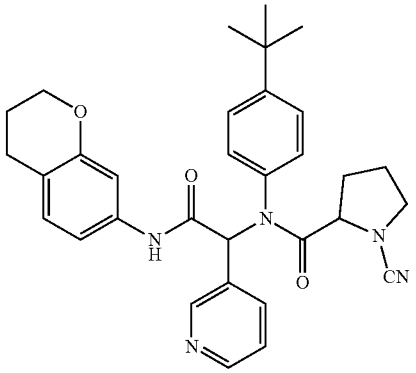 [SMILES: CC(C)(C)c1ccc(N(C(=O)C2CCCN2C#N)C(C(=O)Nc2ccc3c(c2)OCCC3)c2cccnc2)cc1] |
| 1144 | 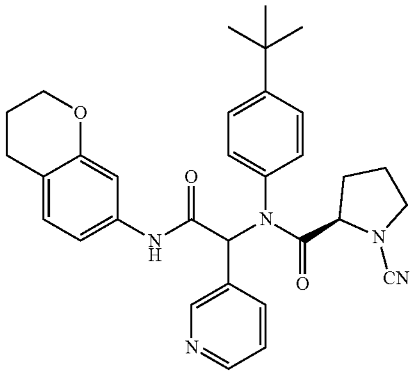 [SMILES: CC(C)(C)c1ccc(N(C(=O)[C@H]2CCCN2C#N)C(C(=O)Nc2ccc3c(c2)OCCC3)c2cccnc2)cc1] |
| 1145a | 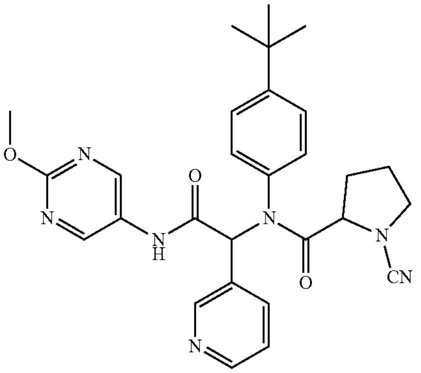 [SMILES: COc1ncc(NC(=O)C(c2cccnc2)N(C(=O)C2CCCN2C#N)c2ccc(C(C)(C)C)cc2)cn1] |
| 1145 | 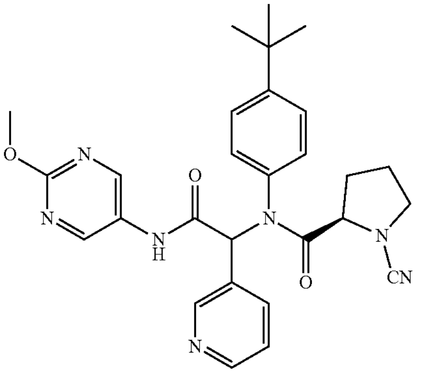 [SMILES: COc1ncc(NC(=O)C(c2cccnc2)N(C(=O)[C@H]2CCCN2C#N)c2ccc(C(C)(C)C)cc2)cn1] |

TABLE 1-continued
Exemplary compounds.
| Cmpd No. | Structure |
|---|---|
| 1146a | 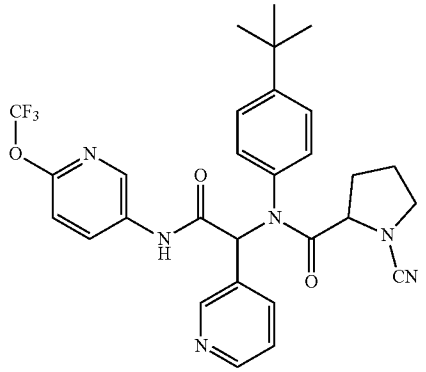 [SMILES: CC(C)(C)c1ccc(N(C(=O)C2CCCN2C#N)C(C(=O)Nc2ccc(OC(F)(F)F)nc2)c2cccnc2)cc1] |
| 1146 | 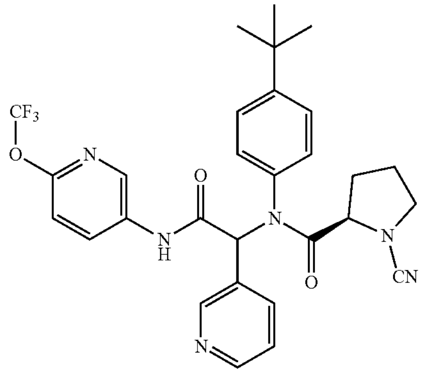 [SMILES: CC(C)(C)c1ccc(N(C(=O)[C@H]2CCCN2C#N)C(C(=O)Nc2ccc(OC(F)(F)F)nc2)c2cccnc2)cc1] |
| 1147a | 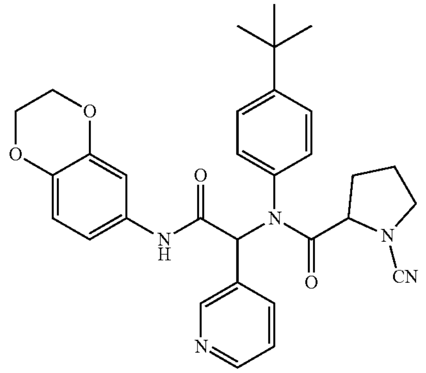 [SMILES: CC(C)(C)c1ccc(N(C(=O)C2CCCN2C#N)C(C(=O)Nc2ccc3c(c2)OCCO3)c2cccnc2)cc1] |
| 1147 | 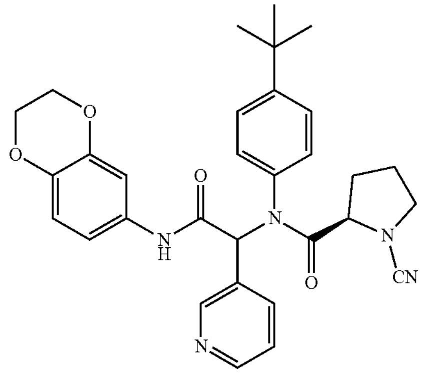 [SMILES: CC(C)(C)c1ccc(N(C(=O)[C@H]2CCCN2C#N)C(C(=O)Nc2ccc3c(c2)OCCO3)c2cccnc2)cc1] |
TABLE 1-continued
Exemplary compounds.
| Cmpd No. | Structure |
|---|---|
| 1148c | 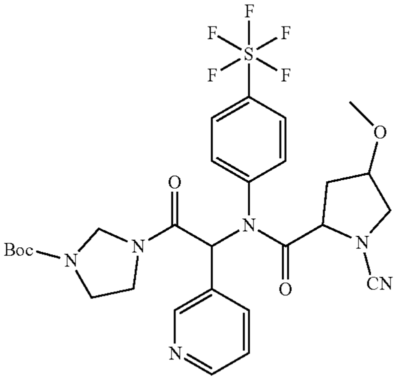 [SMILES: COC1CC(C(=O)N(c2ccc(S(F)(F)(F)(F)F)cc2)C(C(=O)N2CCN(C(=O)OC(C)(C)C)C2)c2cccnc2)N(C#N)C1] |
| 1148b | 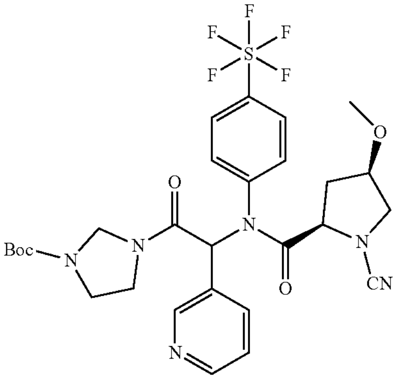 [SMILES: CO[C@@H]1C[C@H](C(=O)N(c2ccc(S(F)(F)(F)(F)F)cc2)C(C(=O)N2CCN(C(=O)OC(C)(C)C)C2)c2cccnc2)N(C#N)C1] |
| 1148a | 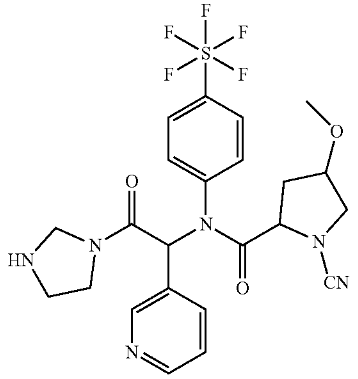 [SMILES: COC1CC(C(=O)N(c2ccc(S(F)(F)(F)(F)F)cc2)C(C(=O)N2CCNC2)c2cccnc2)N(C#N)C1] |
| 1148 | 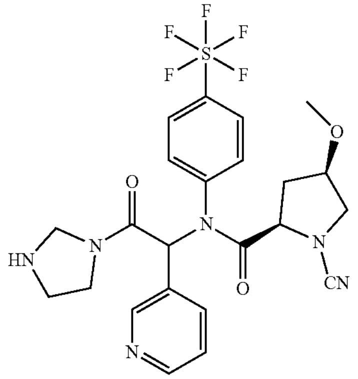 [SMILES: CO[C@@H]1C[C@H](C(=O)N(c2ccc(S(F)(F)(F)(F)F)cc2)C(C(=O)N2CCNC2)c2cccnc2)N(C#N)C1] |

TABLE 1-continued
| Exemplary compounds. | |
|---|---|
| Cmpd No. | Structure |
| 1148d | 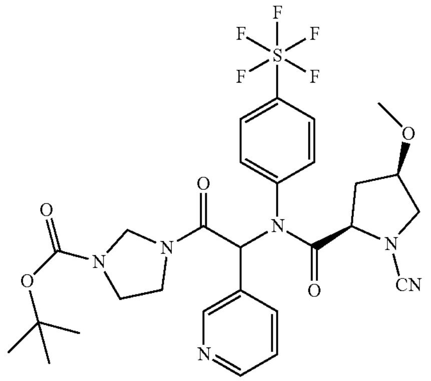 [SMILES: CO[C@@H]1C[C@H](C(=O)N(c2ccc(S(F)(F)(F)(F)F)cc2)C(C(=O)N2CCN(C(=O)OC(C)(C)C)C2)c2cccnc2)N(C#N)C1] |
| 1149a | 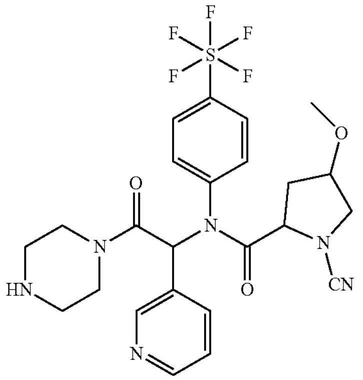 [SMILES: COC1CC(C(=O)N(c2ccc(S(F)(F)(F)(F)F)cc2)C(C(=O)N2CCNCC2)c2cccnc2)N(C#N)C1] |
| 1149 | 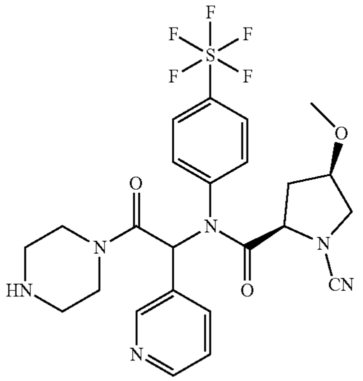 [SMILES: CO[C@@H]1C[C@H](C(=O)N(c2ccc(S(F)(F)(F)(F)F)cc2)C(C(=O)N2CCNCC2)c2cccnc2)N(C#N)C1] |
| 1149b | 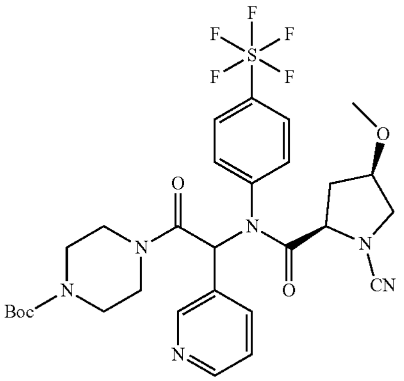 [SMILES: CO[C@@H]1C[C@H](C(=O)N(c2ccc(S(F)(F)(F)(F)F)cc2)C(C(=O)N2CCN(C(=O)OC(C)(C)C)CC2)c2cccnc2)N(C#N)C1] |
TABLE 1-continued
| Exemplary compounds. | |
|---|---|
| Cmpd No. | Structure |
| 1150a | 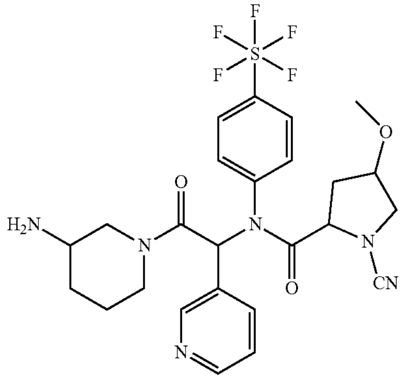 [SMILES: COC1CC(C(=O)N(c2ccc(S(F)(F)(F)(F)F)cc2)C(C(=O)N2CCCC(N)C2)c2cccnc2)N(C#N)C1] |
| 1150 | 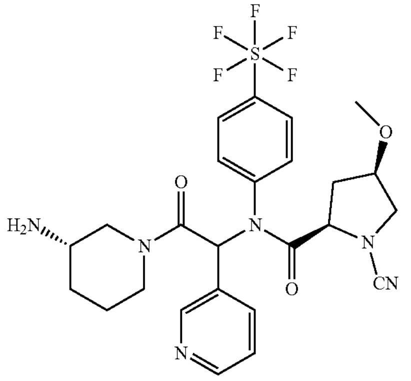 [SMILES: CO[C@@H]1C[C@H](C(=O)N(c2ccc(S(F)(F)(F)(F)F)cc2)C(C(=O)N2CCC[C@H](N)C2)c2cccnc2)N(C#N)C1] |
| 1151a | 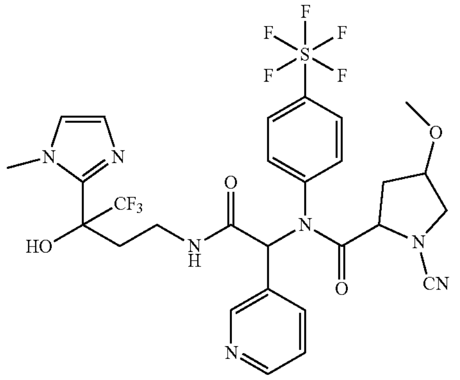 [SMILES: COC1CC(C(=O)N(c2ccc(S(F)(F)(F)(F)F)cc2)C(C(=O)NCCC(O)(c2nccn2C)C(F)(F)F)c2cccnc2)N(C#N)C1] |
| 1151 | 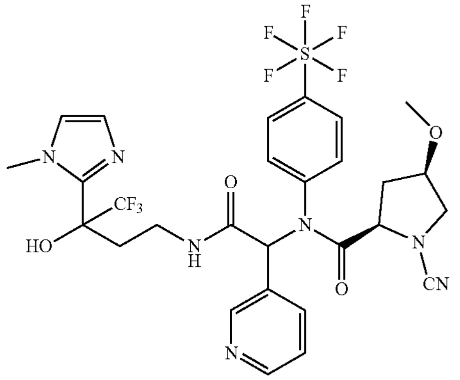 [SMILES: CO[C@@H]1C[C@H](C(=O)N(c2ccc(S(F)(F)(F)(F)F)cc2)C(C(=O)NCCC(O)(c2nccn2C)C(F)(F)F)c2cccnc2)N(C#N)C1] |

TABLE 1-continued
| Exemplary compounds. | |
|---|---|
| Cmpd No. | Structure |
| 1152a | 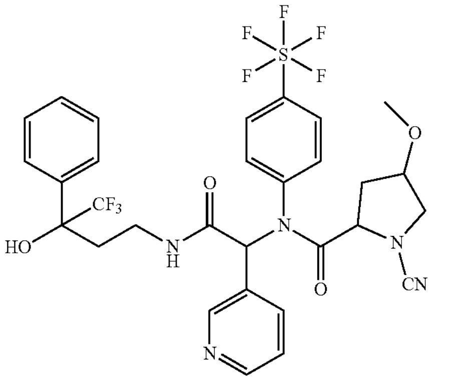 [SMILES: COC1CC(C(=O)N(c2ccc(S(F)(F)(F)(F)F)cc2)C(C(=O)NCCC(O)(c2ccccc2)C(F)(F)F)c2cccnc2)N(C#N)C1] |
| 1152 | 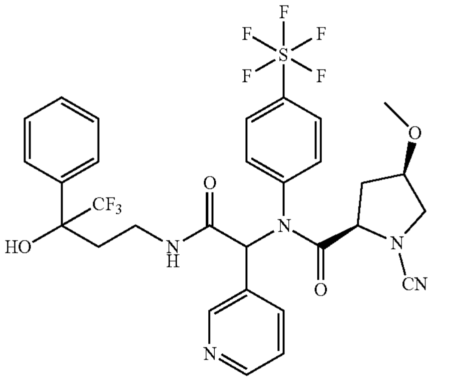 [SMILES: CO[C@@H]1C[C@H](C(=O)N(c2ccc(S(F)(F)(F)(F)F)cc2)C(C(=O)NCCC(O)(c2ccccc2)C(F)(F)F)c2cccnc2)N(C#N)C1] |
| 1153a | 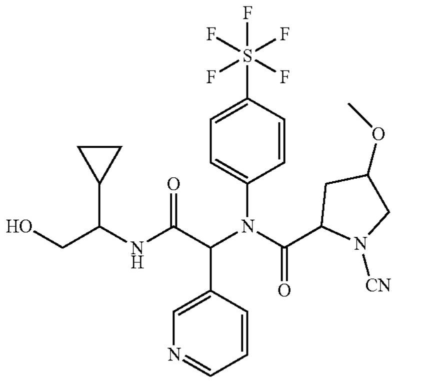 [SMILES: COC1CC(C(=O)N(c2ccc(S(F)(F)(F)(F)F)cc2)C(C(=O)NC(CO)C2CC2)c2cccnc2)N(C#N)C1] |
| 1153 | 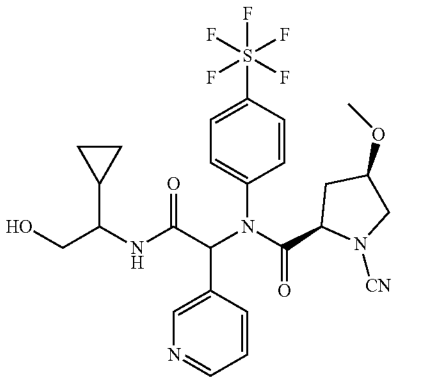 [SMILES: CO[C@@H]1C[C@H](C(=O)N(c2ccc(S(F)(F)(F)(F)F)cc2)C(C(=O)NC(CO)C2CC2)c2cccnc2)N(C#N)C1] |
TABLE 1-continued
| Exemplary compounds. | |
|---|---|
| Cmpd No. | Structure |
| 1154a | 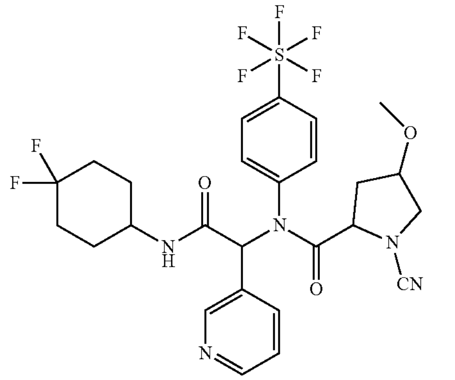 [SMILES: COC1CC(C(=O)N(c2ccc(S(F)(F)(F)(F)F)cc2)C(C(=O)NC2CCC(F)(F)CC2)c2cccnc2)N(C#N)C1] |
| 1154 | 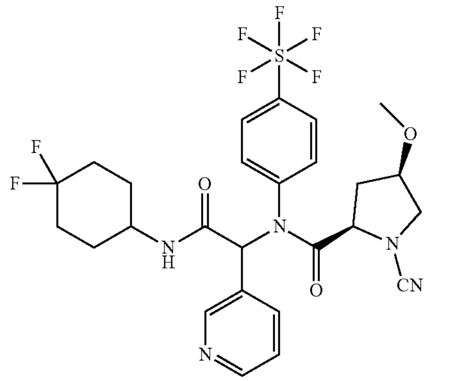 [SMILES: CO[C@@H]1C[C@H](C(=O)N(c2ccc(S(F)(F)(F)(F)F)cc2)C(C(=O)NC2CCC(F)(F)CC2)c2cccnc2)N(C#N)C1] |
| 1155a | 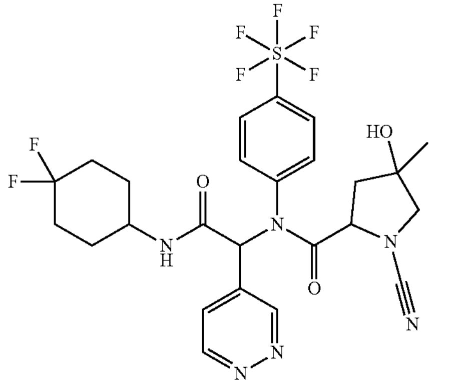 [SMILES: CC1(O)CC(C(=O)N(c2ccc(S(F)(F)(F)(F)F)cc2)C(C(=O)NC2CCC(F)(F)CC2)c2ccnnc2)N(C#N)C1] |
| 1155 | 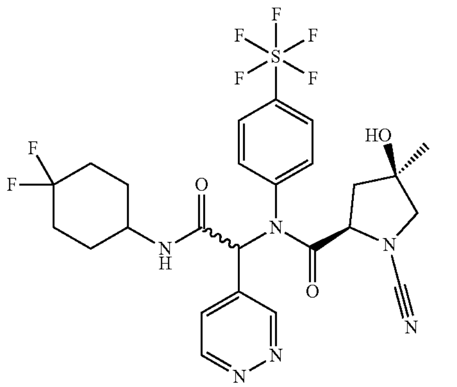 [SMILES: C[C@@]1(O)C[C@H](C(=O)N(c2ccc(S(F)(F)(F)(F)F)cc2)C(C(=O)NC2CCC(F)(F)CC2)c2ccnnc2)N(C#N)C1] |

TABLE 1-continued
| Exemplary compounds. | |
|---|---|
| Cmpd No. | Structure |
| 1156a | 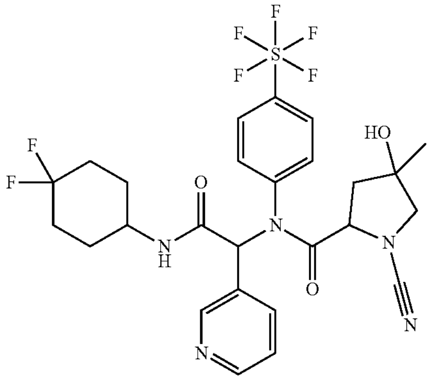 [SMILES: CC1(O)CC(C(=O)N(c2ccc(S(F)(F)(F)(F)F)cc2)C(C(=O)NC2CCC(F)(F)CC2)c2cccnc2)N(C#N)C1] |
| 1156 | 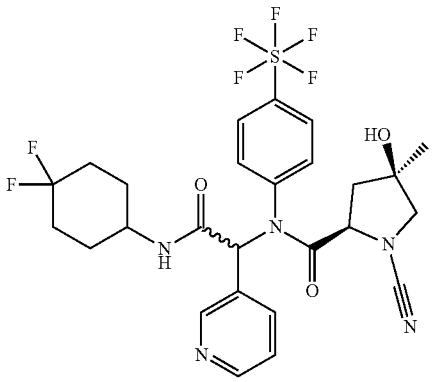 [SMILES: C[C@@]1(O)C[C@H](C(=O)N(c2ccc(S(F)(F)(F)(F)F)cc2)C(C(=O)NC2CCC(F)(F)CC2)c2cccnc2)N(C#N)C1] |
| 1157a | 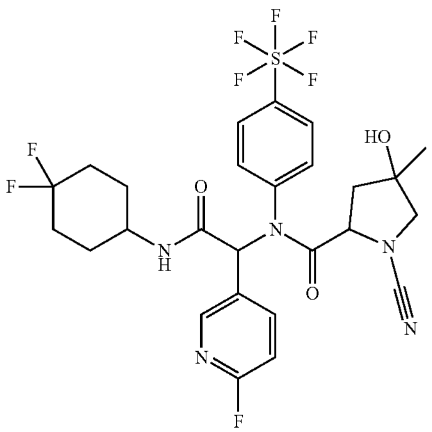 [SMILES: CC1(O)CC(C(=O)N(c2ccc(S(F)(F)(F)(F)F)cc2)C(C(=O)NC2CCC(F)(F)CC2)c2ccc(F)nc2)N(C#N)C1] |
TABLE 1-continued
| Exemplary compounds. | |
|---|---|
| Cmpd No. | Structure |
| 1157 | 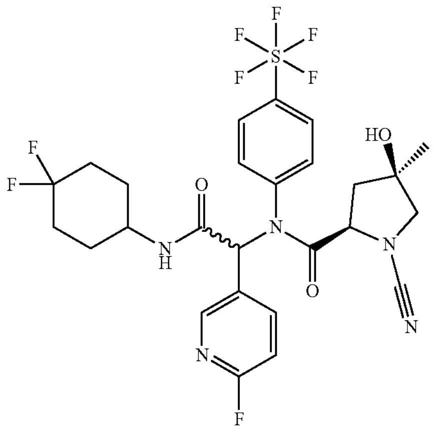 [SMILES: C[C@@]1(O)C[C@H](C(=O)N(c2ccc(S(F)(F)(F)(F)F)cc2)C(C(=O)NC2CCC(F)(F)CC2)c2ccc(F)nc2)N(C#N)C1] |
| 1158a | 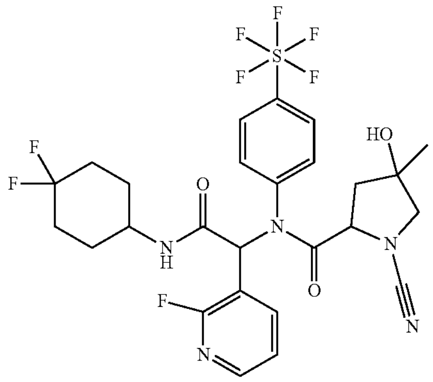 [SMILES: CC1(O)CC(C(=O)N(c2ccc(S(F)(F)(F)(F)F)cc2)C(C(=O)NC2CCC(F)(F)CC2)c2cccnc2F)N(C#N)C1] |
| 1158 | 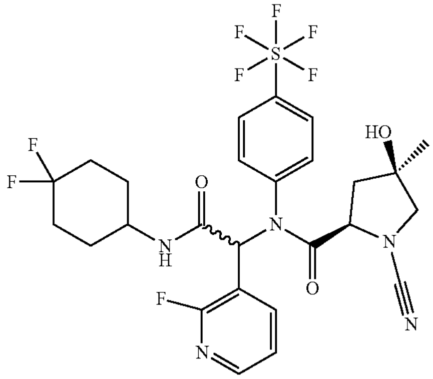 [SMILES: C[C@@]1(O)C[C@H](C(=O)N(c2ccc(S(F)(F)(F)(F)F)cc2)C(C(=O)NC2CCC(F)(F)CC2)c2cccnc2F)N(C#N)C1] |

TABLE 1-continued
| Exemplary compounds. | |
|---|---|
| Cmpd No. | Structure |
| 1159a | 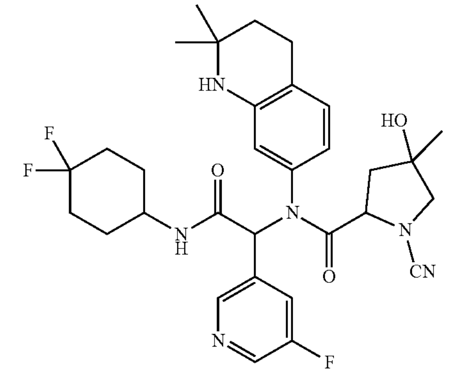 [SMILES: CC1(O)CC(C(=O)N(c2ccc3c(c2)NC(C)(C)CC3)C(C(=O)NC2CCC(F)(F)CC2)c2cncc(F)c2)N(C#N)C1] |
| 1159 | 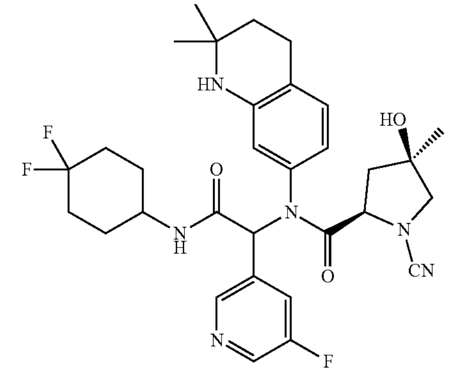 [SMILES: CC1(C)CCc2ccc(N(C(=O)[C@H]3C[C@@](C)(O)CN3C#N)C(C(=O)NC3CCC(F)(F)CC3)c3cncc(F)c3)cc2N1] |
| 1160 | 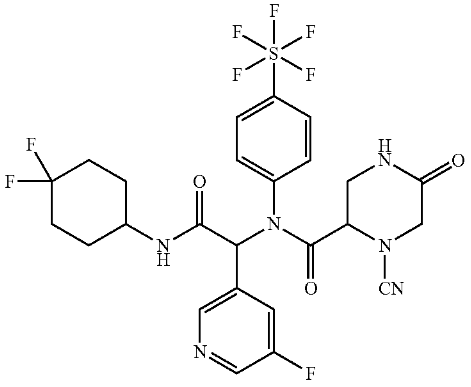 [SMILES: N#CN1CC(=O)NCC1C(=O)N(c1ccc(S(F)(F)(F)(F)F)cc1)C(C(=O)NC1CCC(F)(F)CC1)c1cncc(F)c1] |
| 1161 | 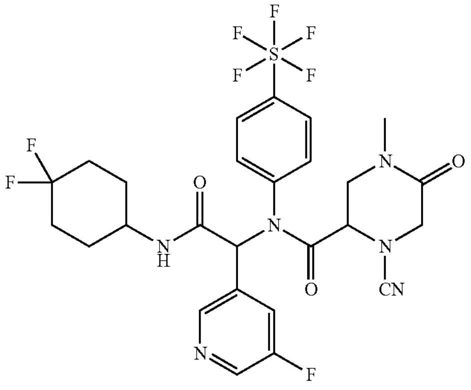 [SMILES: CN1CC(C(=O)N(c2ccc(S(F)(F)(F)(F)F)cc2)C(C(=O)NC2CCC(F)(F)CC2)c2cncc(F)c2)N(C#N)CC1=O] |
TABLE 1-continued
| Exemplary compounds. | |
|---|---|
| Cmpd No. | Structure |
| 1162a | 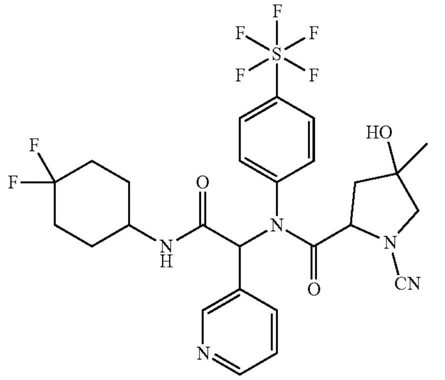 [SMILES: CC1(O)CC(C(=O)N(c2ccc(S(F)(F)(F)(F)F)cc2)C(C(=O)NC2CCC(F)(F)CC2)c2cccnc2)N(C#N)C1] |
| 1162 | 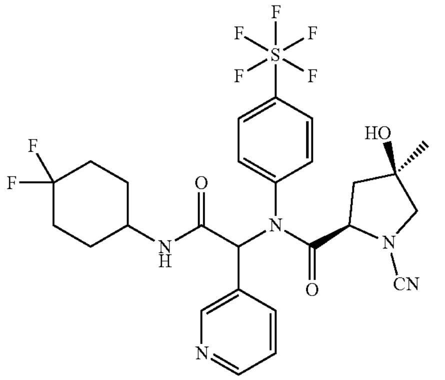 [SMILES: C[C@@]1(O)C[C@H](C(=O)N(c2ccc(S(F)(F)(F)(F)F)cc2)C(C(=O)NC2CCC(F)(F)CC2)c2cccnc2)N(C#N)C1] |
| 1163a | 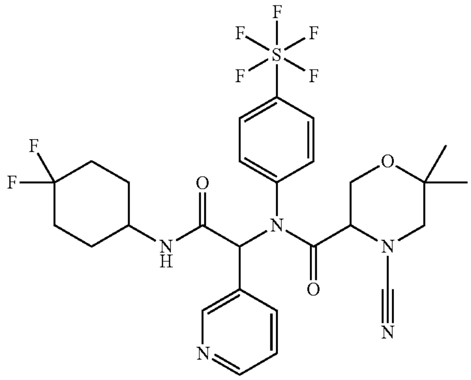 [SMILES: CC1(C)CN(C#N)C(C(=O)N(c2ccc(S(F)(F)(F)(F)F)cc2)C(C(=O)NC2CCC(F)(F)CC2)c2cccnc2)CO1] |
| 1163 | 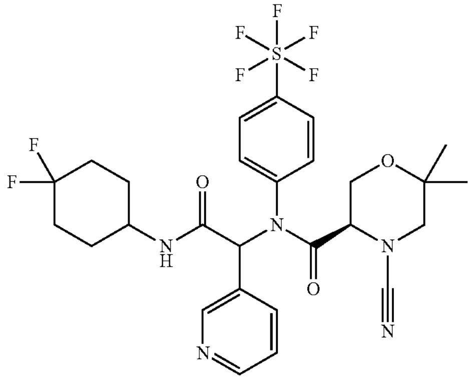 [SMILES: CC1(C)CN(C#N)[C@@H](C(=O)N(c2ccc(S(F)(F)(F)(F)F)cc2)C(C(=O)NC2CCC(F)(F)CC2)c2cccnc2)CO1] |

TABLE 1-continued
| Exemplary compounds. | |
|---|---|
| Cmpd No. | Structure |
| 1163b | 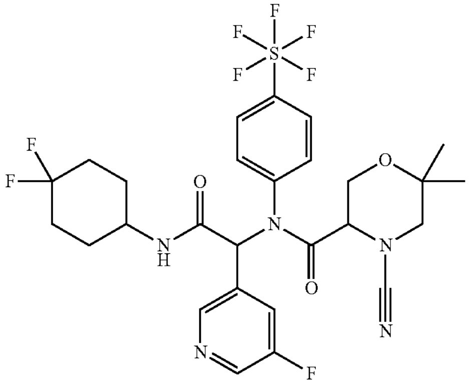 [SMILES: CC1(C)CN(C#N)C(C(=O)N(c2ccc(S(F)(F)(F)(F)F)cc2)C(C(=O)NC2CCC(F)(F)CC2)c2cncc(F)c2)CO1] |
| 1163c | 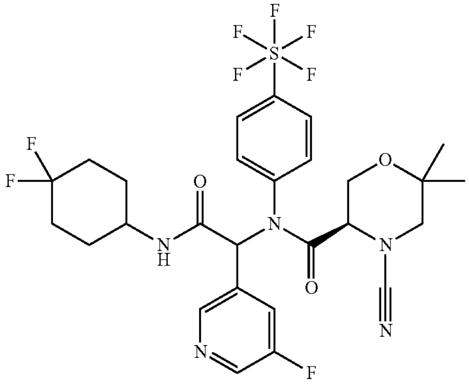 [SMILES: CC1(C)CN(C#N)[C@@H](C(=O)N(c2ccc(S(F)(F)(F)(F)F)cc2)C(C(=O)NC2CCC(F)(F)CC2)c2cncc(F)c2)CO1] |
| 1164 | 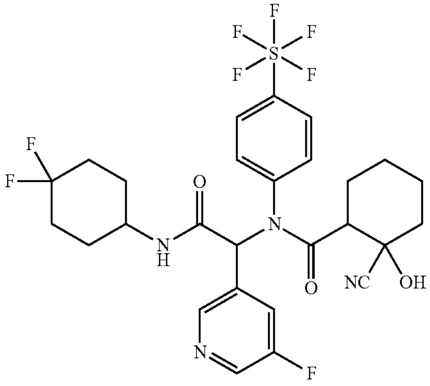 [SMILES: N#CC1(O)CCCCC1C(=O)N(c1ccc(S(F)(F)(F)(F)F)cc1)C(C(=O)NC1CCC(F)(F)CC1)c1cncc(F)c1] |
| 1165a | 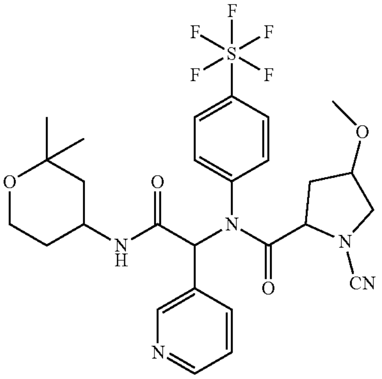 [SMILES: COC1CC(C(=O)N(c2ccc(S(F)(F)(F)(F)F)cc2)C(C(=O)NC2CCOC(C)(C)C2)c2cccnc2)N(C#N)C1] |
TABLE 1-continued
| Exemplary compounds. | |
|---|---|
| Cmpd No. | Structure |
| 1165 | 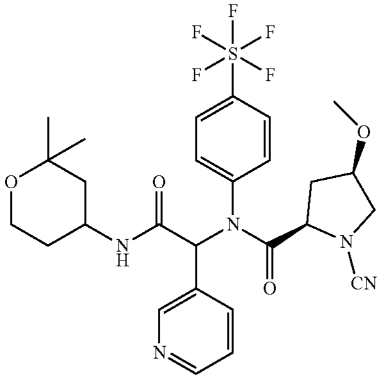 [SMILES: CO[C@@H]1C[C@H](C(=O)N(c2ccc(S(F)(F)(F)(F)F)cc2)C(C(=O)NC2CCOC(C)(C)C2)c2cccnc2)N(C#N)C1] |
| 1166a | 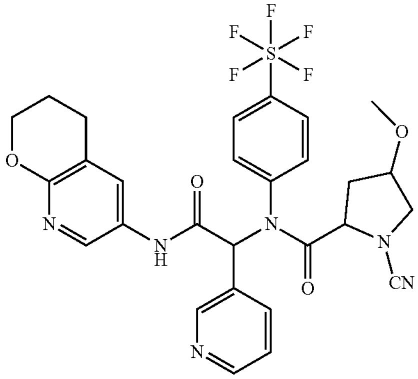 [SMILES: COC1CC(C(=O)N(c2ccc(S(F)(F)(F)(F)F)cc2)C(C(=O)Nc2cnc3c(c2)CCCO3)c2cccnc2)N(C#N)C1] |
| 1166 | 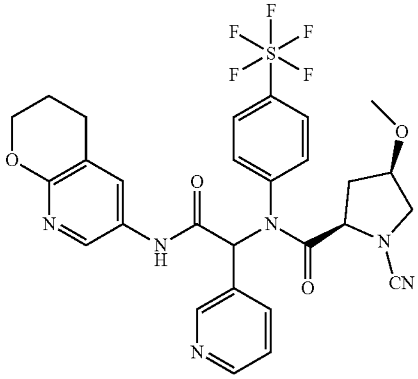 [SMILES: CO[C@@H]1C[C@H](C(=O)N(c2ccc(S(F)(F)(F)(F)F)cc2)C(C(=O)Nc2cnc3c(c2)CCCO3)c2cccnc2)N(C#N)C1] |
| 1167a | 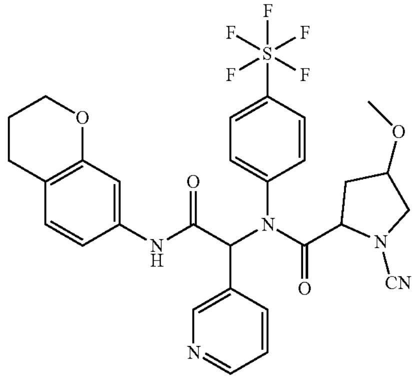 [SMILES: COC1CC(C(=O)N(c2ccc(S(F)(F)(F)(F)F)cc2)C(C(=O)Nc2ccc3c(c2)OCCC3)c2cccnc2)N(C#N)C1] |

TABLE 1-continued
| Exemplary compounds. | |
|---|---|
| Cmpd No. | Structure |
| 1167 | 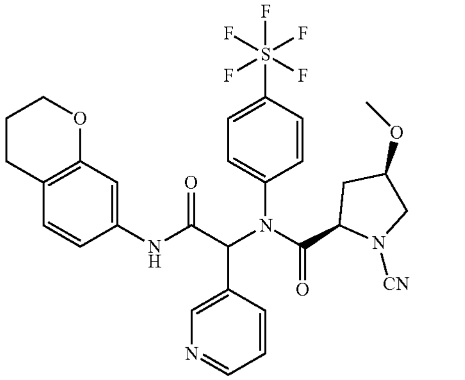 [SMILES: CO[C@@H]1C[C@H](C(=O)N(c2ccc(S(F)(F)(F)(F)F)cc2)C(C(=O)Nc2ccc3c(c2)OCCC3)c2cccnc2)N(C#N)C1] |
| 1168a | 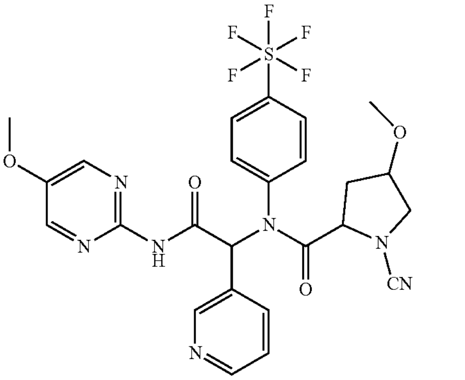 [SMILES: COc1cnc(NC(=O)C(c2cccnc2)N(C(=O)C2CC(OC)CN2C#N)c2ccc(S(F)(F)(F)(F)F)cc2)nc1] |
| 1168 | 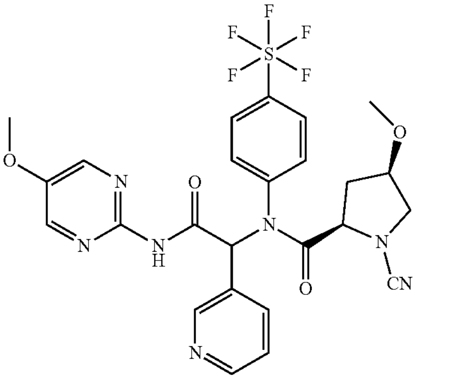 [SMILES: COc1cnc(NC(=O)C(c2cccnc2)N(C(=O)[C@H]2C[C@@H](OC)CN2C#N)c2ccc(S(F)(F)(F)(F)F)cc2)nc1] |
| 1169a | 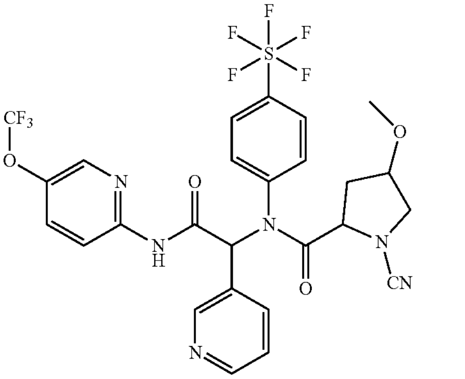 [SMILES: COC1CC(C(=O)N(c2ccc(S(F)(F)(F)(F)F)cc2)C(C(=O)Nc2ccc(OC(F)(F)F)cn2)c2cccnc2)N(C#N)C1] |
TABLE 1-continued
| Exemplary compounds. | |
|---|---|
| Cmpd No. | Structure |
| 1169 | 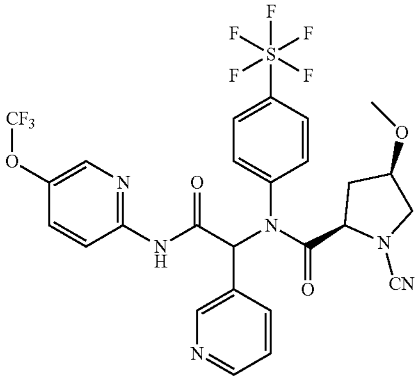 [SMILES: CO[C@@H]1C[C@H](C(=O)N(c2ccc(S(F)(F)(F)(F)F)cc2)C(C(=O)Nc2ccc(OC(F)(F)F)cn2)c2cccnc2)N(C#N)C1] |
| 1170a | 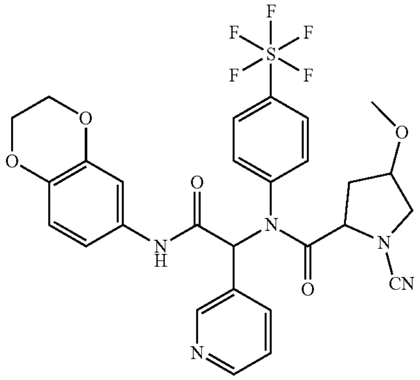 [SMILES: COC1CC(C(=O)N(c2ccc(S(F)(F)(F)(F)F)cc2)C(C(=O)Nc2ccc3c(c2)OCCO3)c2cccnc2)N(C#N)C1] |
| 1170 | 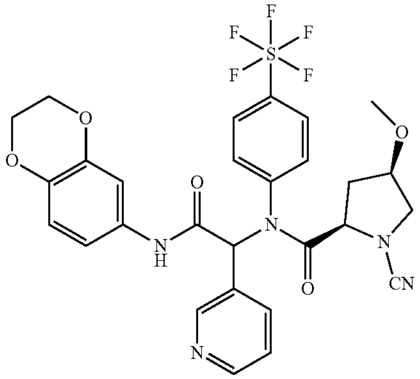 [SMILES: CO[C@@H]1C[C@H](C(=O)N(c2ccc(S(F)(F)(F)(F)F)cc2)C(C(=O)Nc2ccc3c(c2)OCCO3)c2cccnc2)N(C#N)C1] |
| 1171a | 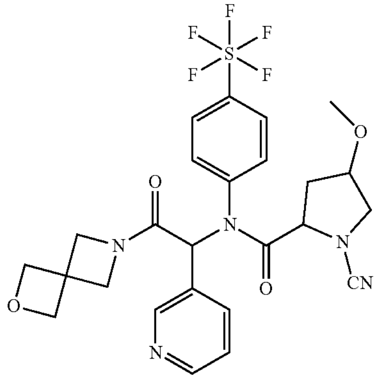 [SMILES: COC1CC(C(=O)N(c2ccc(S(F)(F)(F)(F)F)cc2)C(C(=O)N2CC3(COC3)C2)c2cccnc2)N(C#N)C1] |

TABLE 1-continued
Exemplary compounds.
| Cmpd No. | Structure |
| --- | --- |
| 1171 | 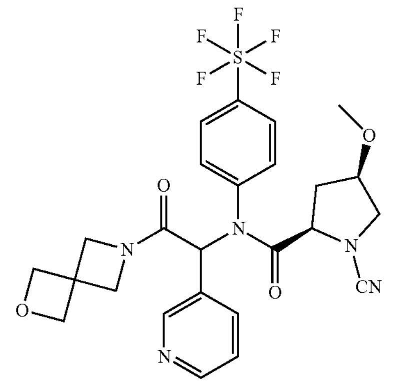 [SMILES: CO[C@@H]1C[C@H](C(=O)N(c2ccc(S(F)(F)(F)(F)F)cc2)C(C(=O)N2CC3(COC3)C2)c2cccnc2)N(C#N)C1] |
| 1172a | 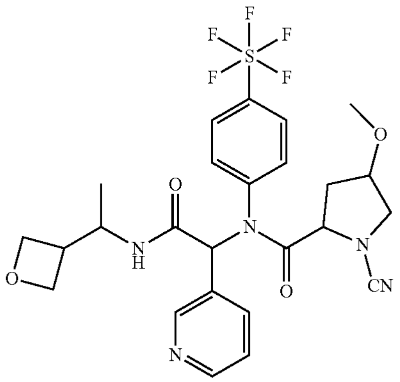 [SMILES: COC1CC(C(=O)N(c2ccc(S(F)(F)(F)(F)F)cc2)C(C(=O)NC(C)C2COC2)c2cccnc2)N(C#N)C1] |
| 1172 | 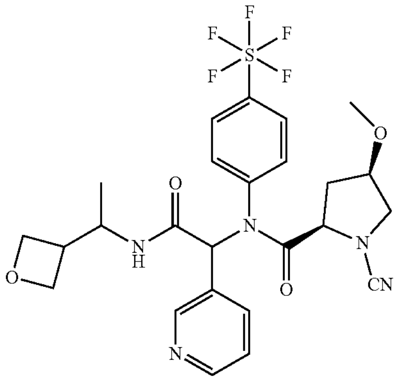 [SMILES: CO[C@@H]1C[C@H](C(=O)N(c2ccc(S(F)(F)(F)(F)F)cc2)C(C(=O)NC(C)C2COC2)c2cccnc2)N(C#N)C1] |
| 1173a | 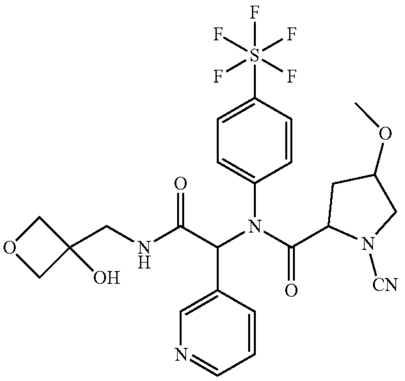 [SMILES: COC1CC(C(=O)N(c2ccc(S(F)(F)(F)(F)F)cc2)C(C(=O)NCC2(O)COC2)c2cccnc2)N(C#N)C1] |
| 1173 | 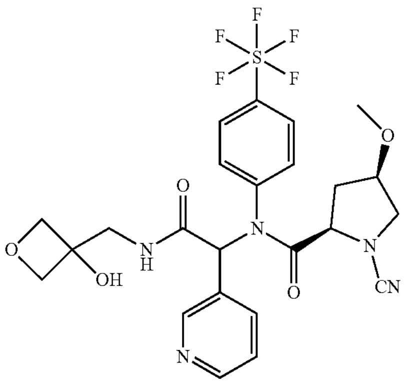 [SMILES: CO[C@@H]1C[C@H](C(=O)N(c2ccc(S(F)(F)(F)(F)F)cc2)C(C(=O)NCC2(O)COC2)c2cccnc2)N(C#N)C1] |
| 1174a | 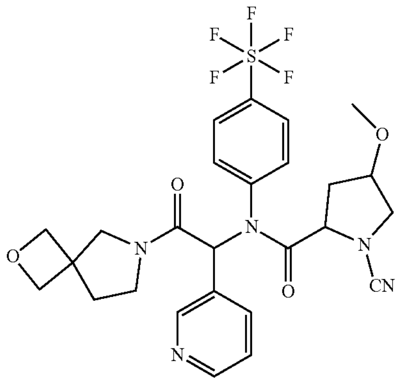 [SMILES: COC1CC(C(=O)N(c2ccc(S(F)(F)(F)(F)F)cc2)C(C(=O)N2CCC3(COC3)C2)c2cccnc2)N(C#N)C1] |
| 1174 | 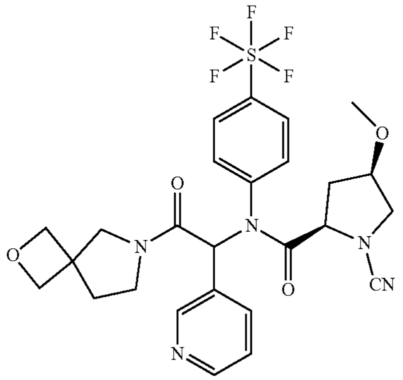 [SMILES: CO[C@@H]1C[C@H](C(=O)N(c2ccc(S(F)(F)(F)(F)F)cc2)C(C(=O)N2CCC3(COC3)C2)c2cccnc2)N(C#N)C1] |
| 1175a | 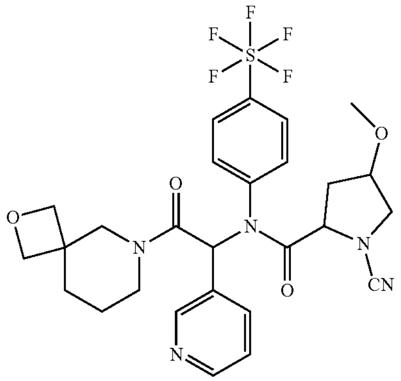 [SMILES: COC1CC(C(=O)N(c2ccc(S(F)(F)(F)(F)F)cc2)C(C(=O)N2CCCC3(COC3)C2)c2cccnc2)N(C#N)C1] |

TABLE 1-continued
Exemplary compounds.
| Cmpd No. | Structure |
|---|---|
| 1175 | 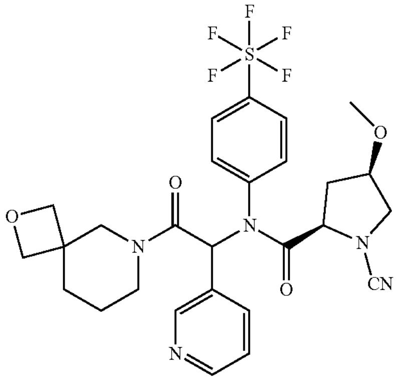 [SMILES: CO[C@@H]1C[C@H](C(=O)N(c2ccc(S(F)(F)(F)(F)F)cc2)C(C(=O)N2CCCC3(COC3)C2)c2cccnc2)N(C#N)C1] |
| 1176a | 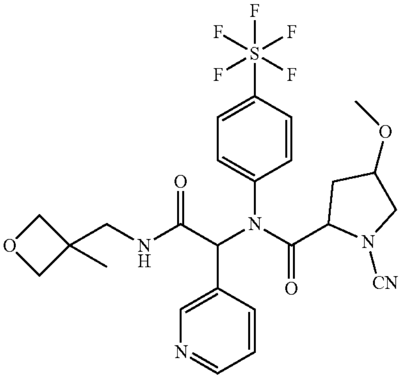 [SMILES: COC1CC(C(=O)N(c2ccc(S(F)(F)(F)(F)F)cc2)C(C(=O)NCC2(C)COC2)c2cccnc2)N(C#N)C1] |
| 1176 | 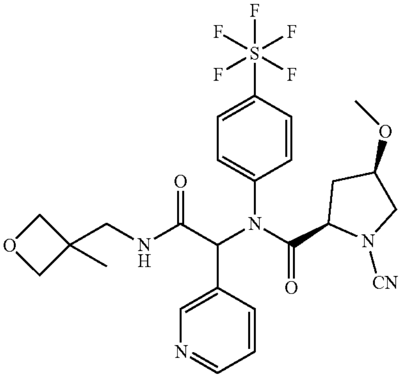 [SMILES: CO[C@@H]1C[C@H](C(=O)N(c2ccc(S(F)(F)(F)(F)F)cc2)C(C(=O)NCC2(C)COC2)c2cccnc2)N(C#N)C1] |
| 1177a | 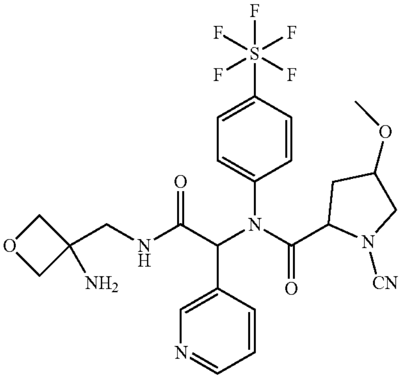 [SMILES: COC1CC(C(=O)N(c2ccc(S(F)(F)(F)(F)F)cc2)C(C(=O)NCC2(N)COC2)c2cccnc2)N(C#N)C1] |
TABLE 1-continued
Exemplary compounds.
| Cmpd No. | Structure |
|---|---|
| 1177 | 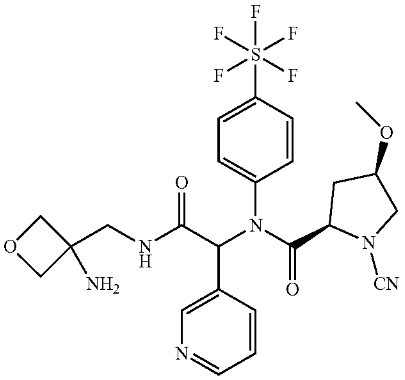 [SMILES: CO[C@@H]1C[C@H](C(=O)N(c2ccc(S(F)(F)(F)(F)F)cc2)C(C(=O)NCC2(N)COC2)c2cccnc2)N(C#N)C1] |
| 1178a | 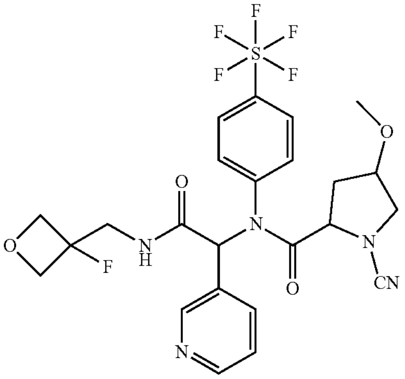 [SMILES: COC1CC(C(=O)N(c2ccc(S(F)(F)(F)(F)F)cc2)C(C(=O)NCC2(F)COC2)c2cccnc2)N(C#N)C1] |
| 1178 | 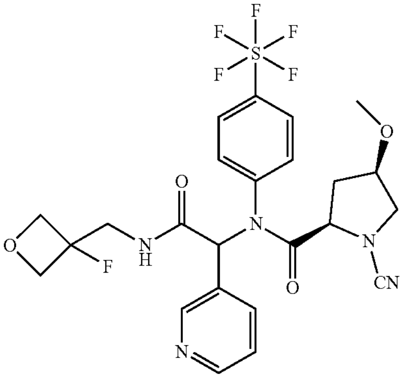 [SMILES: CO[C@@H]1C[C@H](C(=O)N(c2ccc(S(F)(F)(F)(F)F)cc2)C(C(=O)NCC2(F)COC2)c2cccnc2)N(C#N)C1] |
| 1179a | 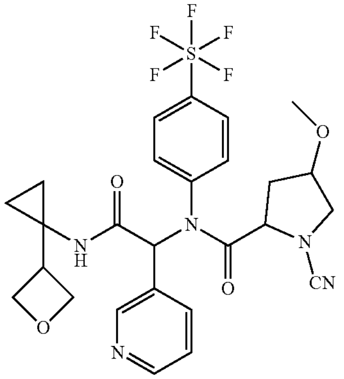 [SMILES: COC1CC(C(=O)N(c2ccc(S(F)(F)(F)(F)F)cc2)C(C(=O)NC2(C3COC3)CC2)c2cccnc2)N(C#N)C1] |

TABLE 1-continued
Exemplary compounds.
| Cmpd No. | Structure |
| --- | --- |
| 1179 | 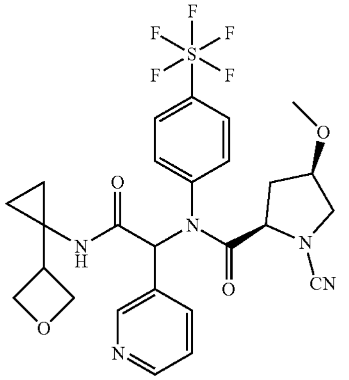 [SMILES: CO[C@@H]1C[C@H](C(=O)N(c2ccc(S(F)(F)(F)(F)F)cc2)C(C(=O)NC2(C3COC3)CC2)c2cccnc2)N(C#N)C1] |
| 1180a | 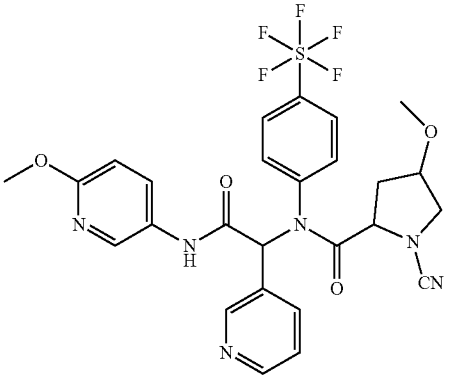 [SMILES: COc1ccc(NC(=O)C(c2cccnc2)N(C(=O)C2CC(OC)CN2C#N)c2ccc(S(F)(F)(F)(F)F)cc2)cn1] |
| 1180 | 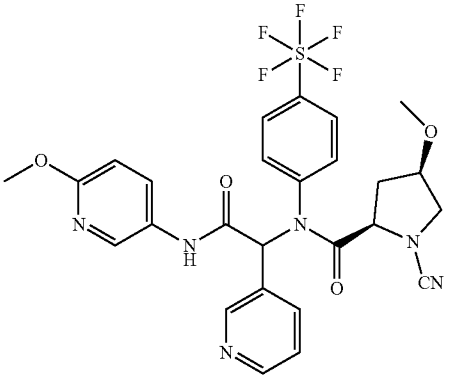 [SMILES: COc1ccc(NC(=O)C(c2cccnc2)N(C(=O)[C@H]2C[C@@H](OC)CN2C#N)c2ccc(S(F)(F)(F)(F)F)cc2)cn1] |
| 1181a | 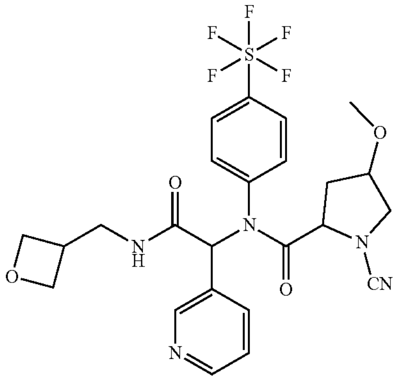 [SMILES: COC1CC(C(=O)N(c2ccc(S(F)(F)(F)(F)F)cc2)C(C(=O)NCC2COC2)c2cccnc2)N(C#N)C1] |
| 1181 | 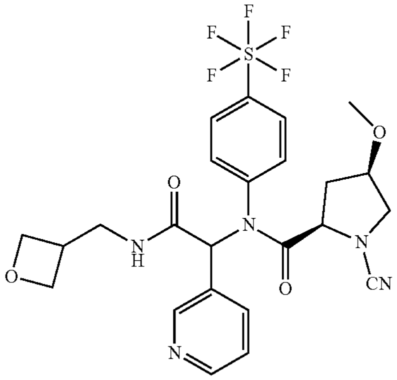 [SMILES: CO[C@@H]1C[C@H](C(=O)N(c2ccc(S(F)(F)(F)(F)F)cc2)C(C(=O)NCC2COC2)c2cccnc2)N(C#N)C1] |
| 1182a | 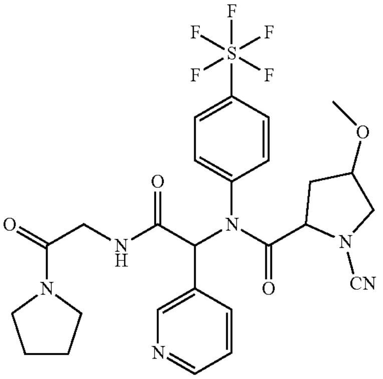 [SMILES: COC1CC(C(=O)N(c2ccc(S(F)(F)(F)(F)F)cc2)C(C(=O)NCC(=O)N2CCCC2)c2cccnc2)N(C#N)C1] |
| 1182 | 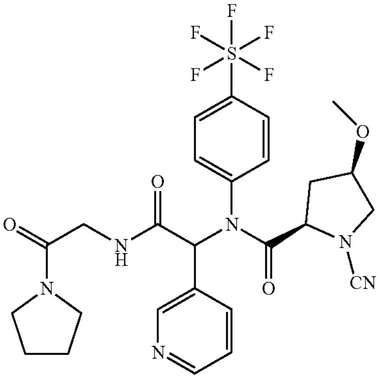 [SMILES: CO[C@@H]1C[C@H](C(=O)N(c2ccc(S(F)(F)(F)(F)F)cc2)C(C(=O)NCC(=O)N2CCCC2)c2cccnc2)N(C#N)C1] |
| 1183a | 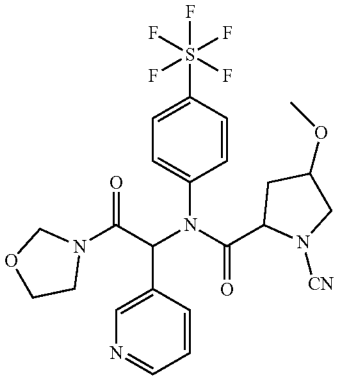 [SMILES: COC1CC(C(=O)N(c2ccc(S(F)(F)(F)(F)F)cc2)C(C(=O)N2CCOC2)c2cccnc2)N(C#N)C1] |

TABLE 1-continued
Exemplary compounds.
| Cmpd No. | Structure |
|---|---|
| 1183 | 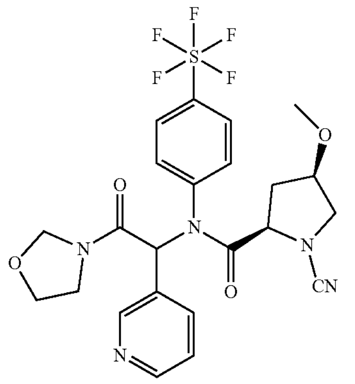 [SMILES: CO[C@@H]1C[C@H](C(=O)N(c2ccc(S(F)(F)(F)(F)F)cc2)C(C(=O)N2CCOC2)c2cccnc2)N(C#N)C1] |
| 1184a | 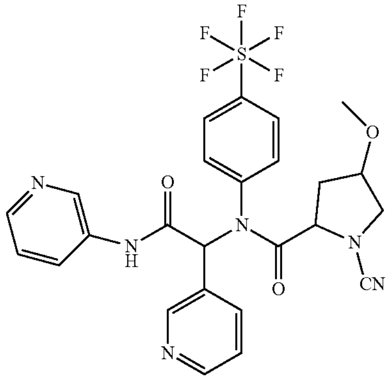 [SMILES: COC1CC(C(=O)N(c2ccc(S(F)(F)(F)(F)F)cc2)C(C(=O)Nc2cccnc2)c2cccnc2)N(C#N)C1] |
| 1184 | 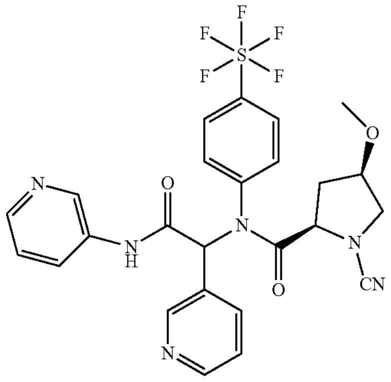 [SMILES: CO[C@@H]1C[C@H](C(=O)N(c2ccc(S(F)(F)(F)(F)F)cc2)C(C(=O)Nc2cccnc2)c2cccnc2)N(C#N)C1] |
| 1185a | 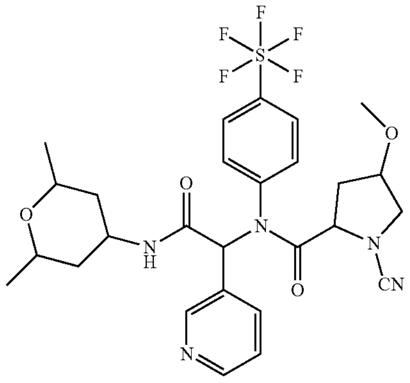 [SMILES: COC1CC(C(=O)N(c2ccc(S(F)(F)(F)(F)F)cc2)C(C(=O)NC2CC(C)OC(C)C2)c2cccnc2)N(C#N)C1] |
TABLE 1-continued
Exemplary compounds.
| Cmpd No. | Structure |
|---|---|
| 1185 | 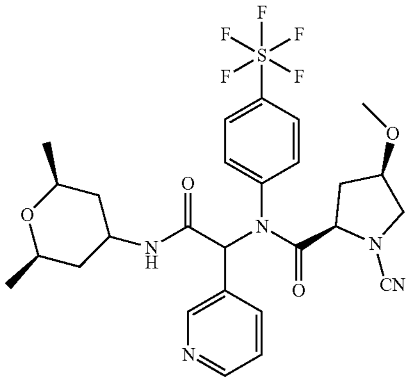 [SMILES: CO[C@@H]1C[C@H](C(=O)N(c2ccc(S(F)(F)(F)(F)F)cc2)C(C(=O)NC2C[C@@H](C)O[C@@H](C)C2)c2cccnc2)N(C#N)C1] |
| 1186a | 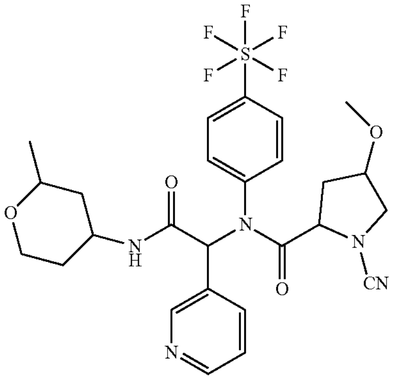 [SMILES: COC1CC(C(=O)N(c2ccc(S(F)(F)(F)(F)F)cc2)C(C(=O)NC2CCOC(C)C2)c2cccnc2)N(C#N)C1] |
| 1186 | 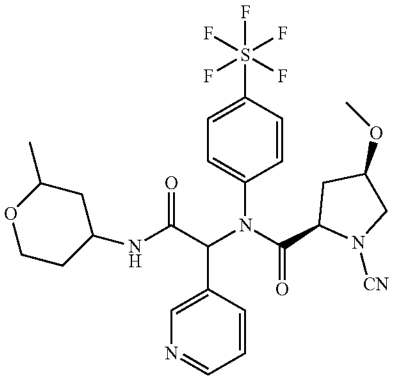 [SMILES: CO[C@@H]1C[C@H](C(=O)N(c2ccc(S(F)(F)(F)(F)F)cc2)C(C(=O)NC2CCOC(C)C2)c2cccnc2)N(C#N)C1] |
| 1187a | 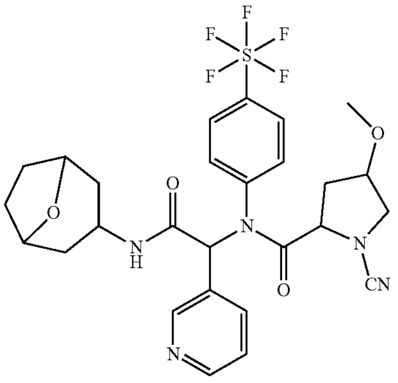 [SMILES: COC1CC(C(=O)N(c2ccc(S(F)(F)(F)(F)F)cc2)C(C(=O)NC2CC3CCC(C2)O3)c2cccnc2)N(C#N)C1] |

TABLE 1-continued
| Exemplary compounds. | |
|---|---|
| Cmpd No. | Structure |
| 1187 | 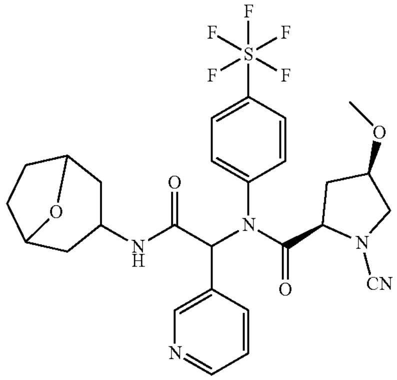 [SMILES: CO[C@@H]1C[C@H](C(=O)N(c2ccc(S(F)(F)(F)(F)F)cc2)C(C(=O)NC2CC3CCC(C2)O3)c2cccnc2)N(C#N)C1] |
| 1188a | 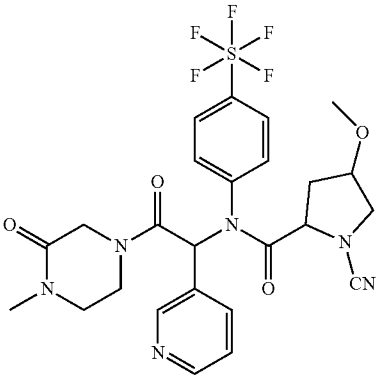 [SMILES: COC1CC(C(=O)N(c2ccc(S(F)(F)(F)(F)F)cc2)C(C(=O)N2CCN(C)C(=O)C2)c2cccnc2)N(C#N)C1] |
| 1188 | 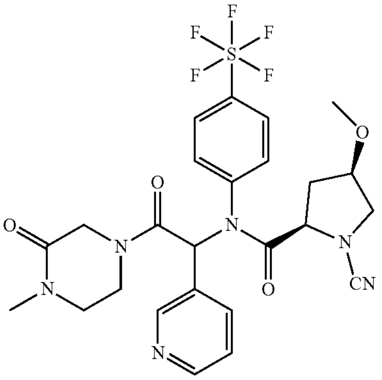 [SMILES: CO[C@@H]1C[C@H](C(=O)N(c2ccc(S(F)(F)(F)(F)F)cc2)C(C(=O)N2CCN(C)C(=O)C2)c2cccnc2)N(C#N)C1] |
| 1189a | 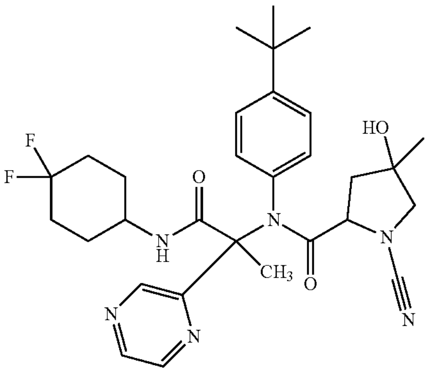 [SMILES: CC1(O)CC(C(=O)N(c2ccc(C(C)(C)C)cc2)C(C)(C(=O)NC2CCC(F)(F)CC2)c2cnccn2)N(C#N)C1] |
TABLE 1-continued
| Exemplary compounds. | |
|---|---|
| Cmpd No. | Structure |
| 1189 | 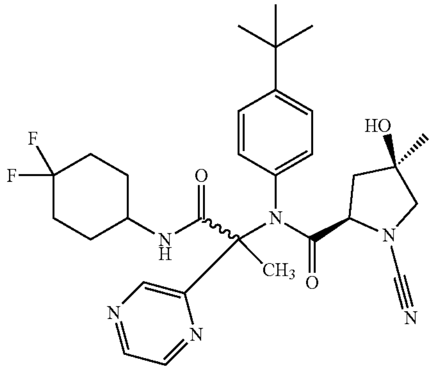 [SMILES: CC(C)(C)c1ccc(N(C(=O)[C@H]2C[C@@](C)(O)CN2C#N)C(C)(C(=O)NC2CCC(F)(F)CC2)c2cnccn2)cc1] |
| 1190 | 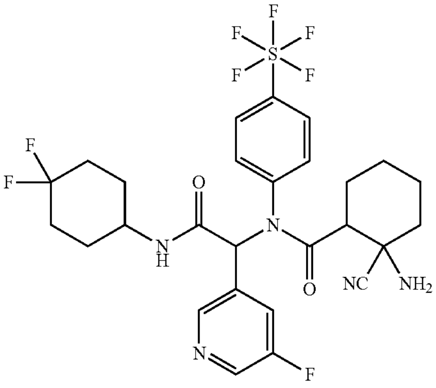 [SMILES: N#CC1(N)CCCCC1C(=O)N(c1ccc(S(F)(F)(F)(F)F)cc1)C(C(=O)NC1CCC(F)(F)CC1)c1cncc(F)c1] |
| 1191 | 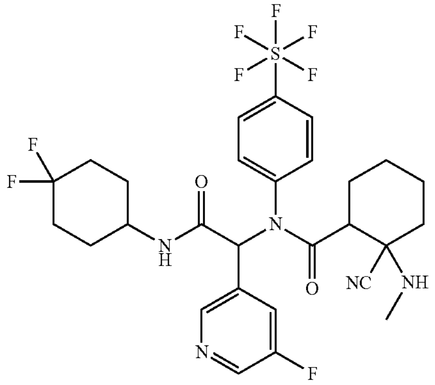 [SMILES: CNC1(C#N)CCCCC1C(=O)N(c1ccc(S(F)(F)(F)(F)F)cc1)C(C(=O)NC1CCC(F)(F)CC1)c1cncc(F)c1] |
| 1192 | 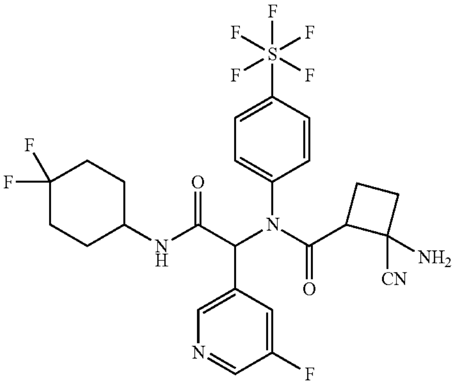 [SMILES: N#CC1(N)CCC1C(=O)N(c1ccc(S(F)(F)(F)(F)F)cc1)C(C(=O)NC1CCC(F)(F)CC1)c1cncc(F)c1] |

TABLE 1-continued
| Cmpd No. | Structure |
|---|---|
| Exemplary compounds. | |
| 1193 | 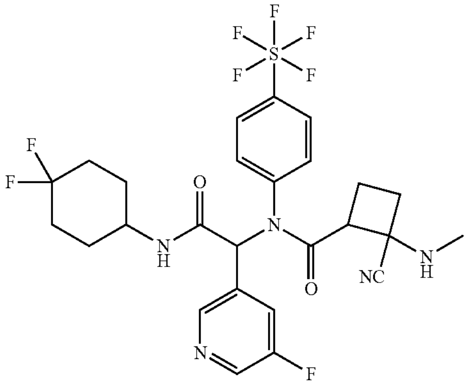 [SMILES: CNC1(C#N)CCC1C(=O)N(c1ccc(S(F)(F)(F)(F)F)cc1)C(C(=O)NC1CCC(F)(F)CC1)c1cncc(F)c1] |
| 1194a | 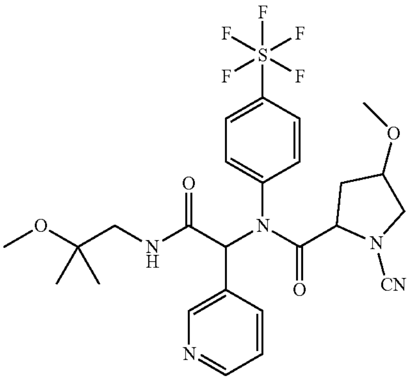 [SMILES: COC1CC(C(=O)N(c2ccc(S(F)(F)(F)(F)F)cc2)C(C(=O)NCC(C)(C)OC)c2cccnc2)N(C#N)C1] |
| 1194 | 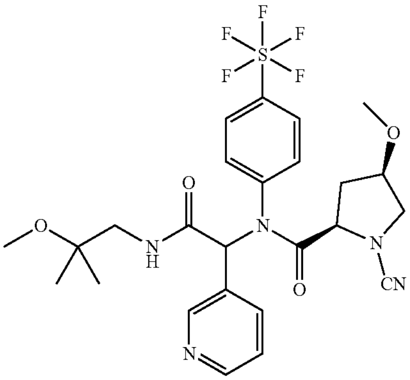 [SMILES: CO[C@@H]1C[C@H](C(=O)N(c2ccc(S(F)(F)(F)(F)F)cc2)C(C(=O)NCC(C)(C)OC)c2cccnc2)N(C#N)C1] |
| 1195a | 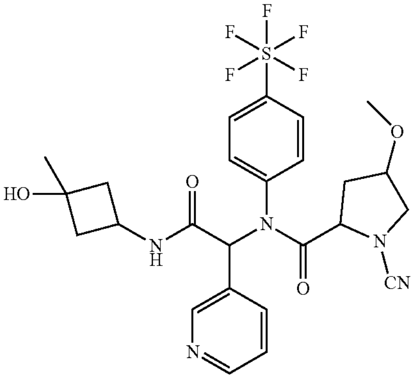 [SMILES: COC1CC(C(=O)N(c2ccc(S(F)(F)(F)(F)F)cc2)C(C(=O)NC2CC(C)(O)C2)c2cccnc2)N(C#N)C1] |
TABLE 1-continued
| Cmpd No. | Structure |
|---|---|
| Exemplary compounds. | |
| 1196a | 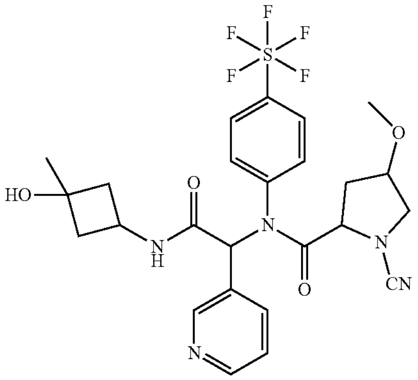 [SMILES: COC1CC(C(=O)N(c2ccc(S(F)(F)(F)(F)F)cc2)C(C(=O)NC2CC(C)(O)C2)c2cccnc2)N(C#N)C1] |
| 1195 | 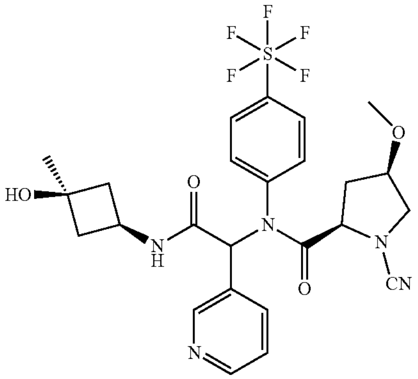 [SMILES: CO[C@@H]1C[C@H](C(=O)N(c2ccc(S(F)(F)(F)(F)F)cc2)C(C(=O)N[C@H]2C[C@@](C)(O)C2)c2cccnc2)N(C#N)C1] |
| 1196a | 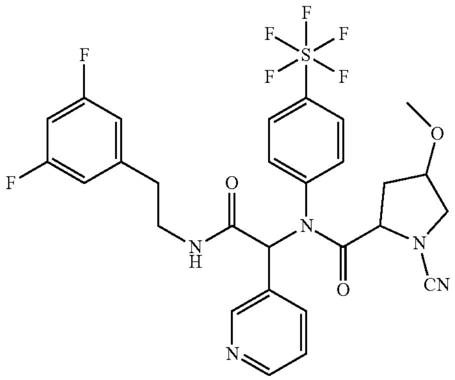 [SMILES: COC1CC(C(=O)N(c2ccc(S(F)(F)(F)(F)F)cc2)C(C(=O)NCCc2cc(F)cc(F)c2)c2cccnc2)N(C#N)C1] |
| 1196 | 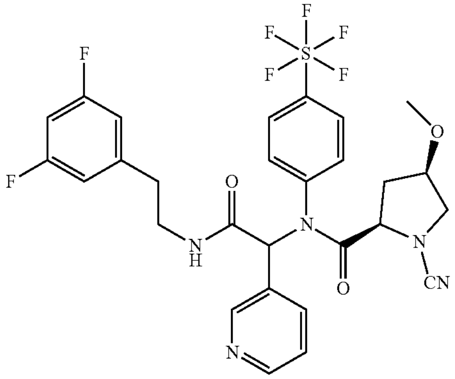 [SMILES: CO[C@@H]1C[C@H](C(=O)N(c2ccc(S(F)(F)(F)(F)F)cc2)C(C(=O)NCCc2cc(F)cc(F)c2)c2cccnc2)N(C#N)C1] |

TABLE 1-continued
| Exemplary compounds. | |
|---|---|
| Cmpd No. | Structure |
| 1197a | 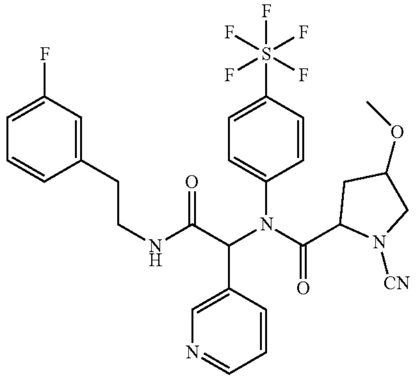 [SMILES: COC1CC(C(=O)N(c2ccc(S(F)(F)(F)(F)F)cc2)C(C(=O)NCCc2cccc(F)c2)c2cccnc2)N(C#N)C1] |
| 1197 | 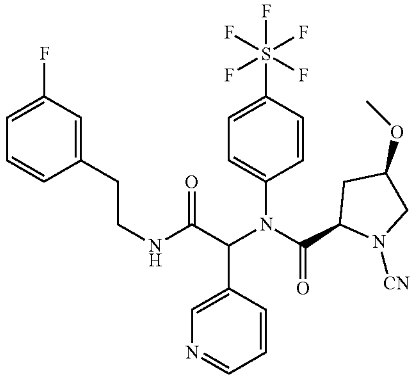 [SMILES: CO[C@@H]1C[C@H](C(=O)N(c2ccc(S(F)(F)(F)(F)F)cc2)C(C(=O)NCCc2cccc(F)c2)c2cccnc2)N(C#N)C1] |
| 1198a | 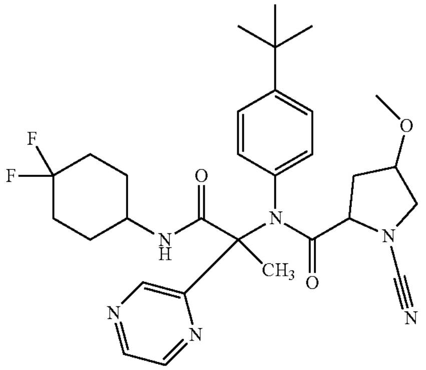 [SMILES: COC1CC(C(=O)N(c2ccc(C(C)(C)C)cc2)C(C)(C(=O)NC2CCC(F)(F)CC2)c2cnccn2)N(C#N)C1] |
| 1198 | 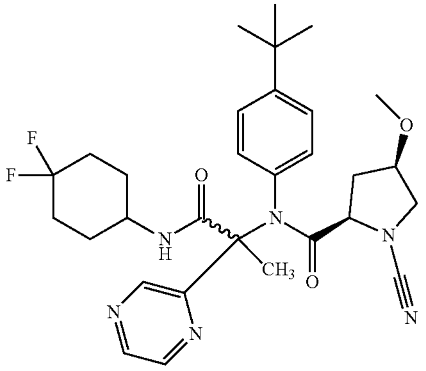 [SMILES: CO[C@@H]1C[C@H](C(=O)N(c2ccc(C(C)(C)C)cc2)C(C)(C(=O)NC2CCC(F)(F)CC2)c2cnccn2)N(C#N)C1] |
TABLE 1-continued
| Exemplary compounds. | |
|---|---|
| Cmpd No. | Structure |
| 1199a | 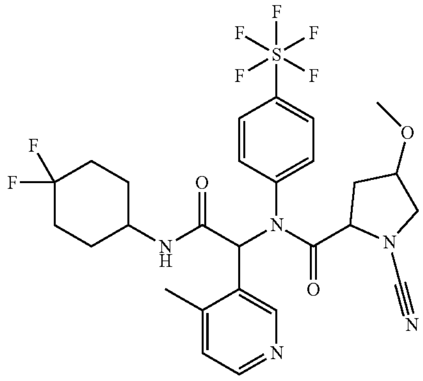 [SMILES: COC1CC(C(=O)N(c2ccc(S(F)(F)(F)(F)F)cc2)C(C(=O)NC2CCC(F)(F)CC2)c2cnccc2C)N(C#N)C1] |
| 1199 | 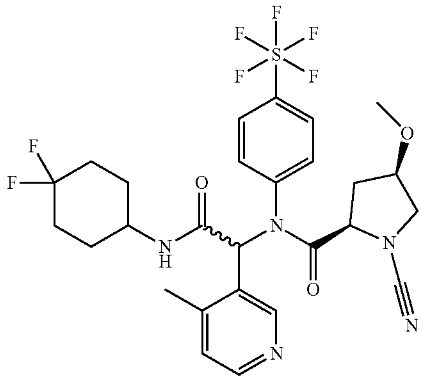 [SMILES: CO[C@@H]1C[C@H](C(=O)N(c2ccc(S(F)(F)(F)(F)F)cc2)C(C(=O)NC2CCC(F)(F)CC2)c2cnccc2C)N(C#N)C1] |
| 1200a | 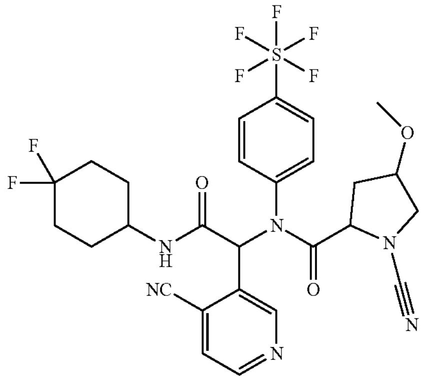 [SMILES: COC1CC(C(=O)N(c2ccc(S(F)(F)(F)(F)F)cc2)C(C(=O)NC2CCC(F)(F)CC2)c2cnccc2C#N)N(C#N)C1] |
| 1200 | 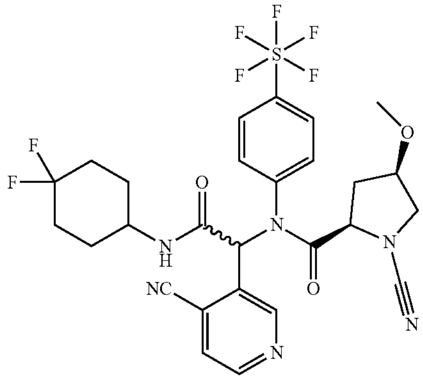 [SMILES: CO[C@@H]1C[C@H](C(=O)N(c2ccc(S(F)(F)(F)(F)F)cc2)C(C(=O)NC2CCC(F)(F)CC2)c2cnccc2C#N)N(C#N)C1] |

TABLE 1-continued
| Exemplary compounds. | |
|---|---|
| Cmpd No. | Structure |
| 1201a | 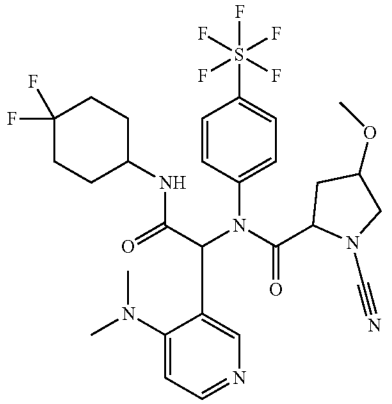 [SMILES: COC1CC(C(=O)N(c2ccc(S(F)(F)(F)(F)F)cc2)C(C(=O)NC2CCC(F)(F)CC2)c2cnccc2N(C)C)N(C#N)C1] |
| 1201 | 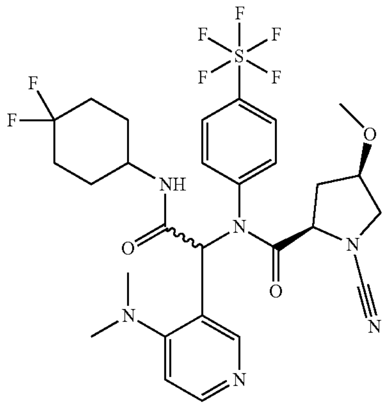 [SMILES: CO[C@@H]1C[C@H](C(=O)N(c2ccc(S(F)(F)(F)(F)F)cc2)C(C(=O)NC2CCC(F)(F)CC2)c2cnccc2N(C)C)N(C#N)C1] |
| 1202a | 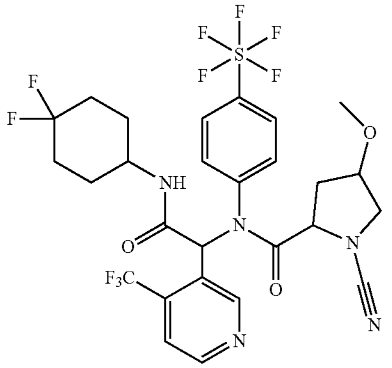 [SMILES: COC1CC(C(=O)N(c2ccc(S(F)(F)(F)(F)F)cc2)C(C(=O)NC2CCC(F)(F)CC2)c2cnccc2C(F)(F)F)N(C#N)C1] |
TABLE 1-continued
| Exemplary compounds. | |
|---|---|
| Cmpd No. | Structure |
| 1202 | 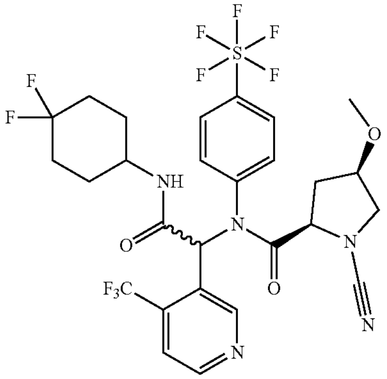 [SMILES: CO[C@@H]1C[C@H](C(=O)N(c2ccc(S(F)(F)(F)(F)F)cc2)C(C(=O)NC2CCC(F)(F)CC2)c2cnccc2C(F)(F)F)N(C#N)C1] |
| 1203a | 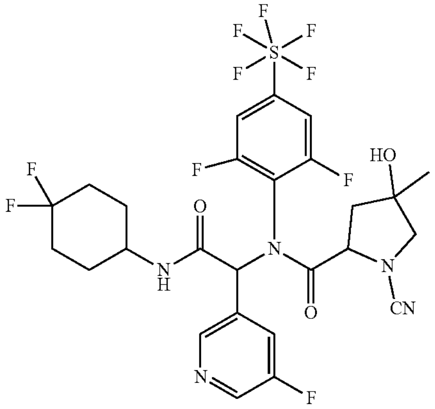 [SMILES: CC1(O)CC(C(=O)N(c2c(F)cc(S(F)(F)(F)(F)F)cc2F)C(C(=O)NC2CCC(F)(F)CC2)c2cncc(F)c2)N(C#N)C1] |
| 1203 | 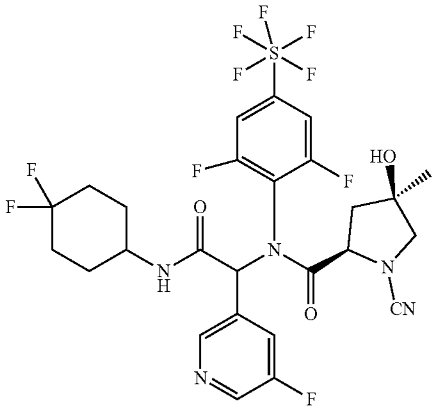 [SMILES: C[C@@]1(O)C[C@H](C(=O)N(c2c(F)cc(S(F)(F)(F)(F)F)cc2F)C(C(=O)NC2CCC(F)(F)CC2)c2cncc(F)c2)N(C#N)C1] |

TABLE 1-continued
| Exemplary compounds. | |
|---|---|
| Cmpd No. | Structure |
| 1204a | 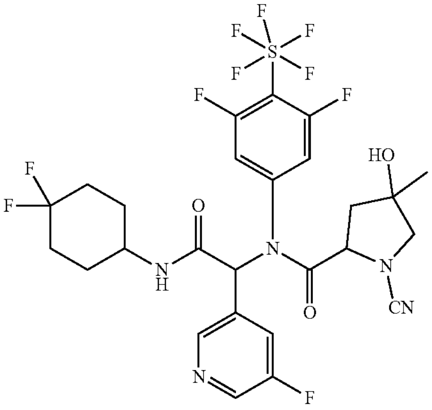 [SMILES: CC1(O)CC(C(=O)N(c2cc(F)c(S(F)(F)(F)(F)F)c(F)c2)C(C(=O)NC2CCC(F)(F)CC2)c2cncc(F)c2)N(C#N)C1] |
| 1204 | 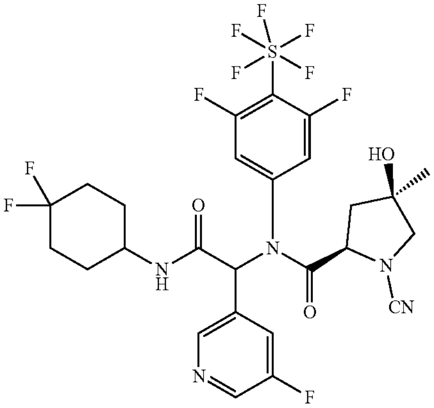 [SMILES: C[C@@]1(O)C[C@H](C(=O)N(c2cc(F)c(S(F)(F)(F)(F)F)c(F)c2)C(C(=O)NC2CCC(F)(F)CC2)c2cncc(F)c2)N(C#N)C1] |
| 1205a | 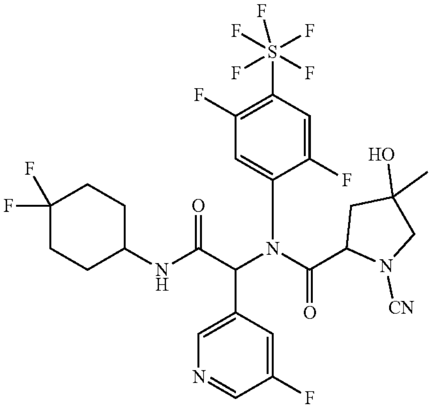 [SMILES: CC1(O)CC(C(=O)N(c2cc(F)c(S(F)(F)(F)(F)F)cc2F)C(C(=O)NC2CCC(F)(F)CC2)c2cncc(F)c2)N(C#N)C1] |
TABLE 1-continued
| Exemplary compounds. | |
|---|---|
| Cmpd No. | Structure |
| 1205 | 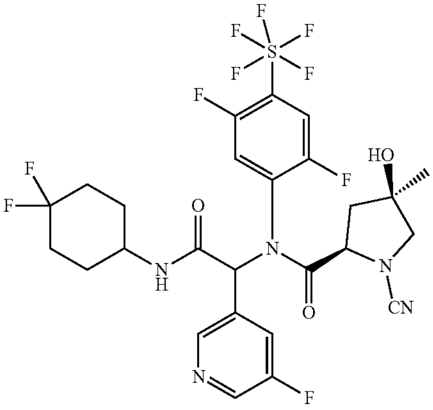 [SMILES: C[C@@]1(O)C[C@H](C(=O)N(c2cc(F)c(S(F)(F)(F)(F)F)cc2F)C(C(=O)NC2CCC(F)(F)CC2)c2cncc(F)c2)N(C#N)C1] |
| 1206a | 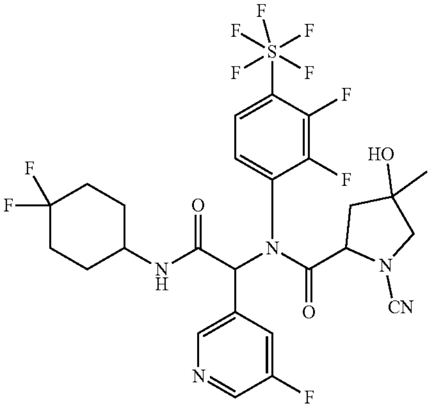 [SMILES: CC1(O)CC(C(=O)N(c2ccc(S(F)(F)(F)(F)F)c(F)c2F)C(C(=O)NC2CCC(F)(F)CC2)c2cncc(F)c2)N(C#N)C1] |
| 1206 | 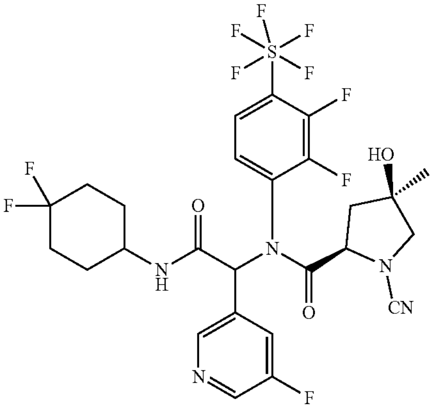 [SMILES: C[C@@]1(O)C[C@H](C(=O)N(c2ccc(S(F)(F)(F)(F)F)c(F)c2F)C(C(=O)NC2CCC(F)(F)CC2)c2cncc(F)c2)N(C#N)C1] |

TABLE 1-continued
| Exemplary compounds. | |
|---|---|
| Cmpd No. | Structure |
| 1207a | 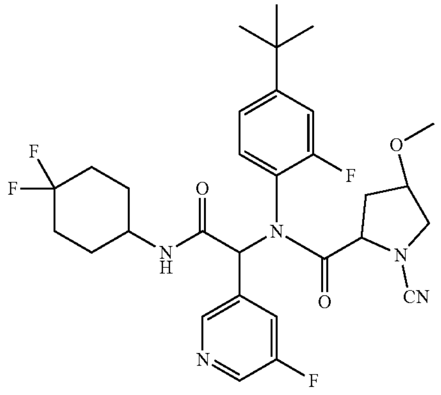 [SMILES: COC1CC(C(=O)N(c2ccc(C(C)(C)C)cc2F)C(C(=O)NC2CCC(F)(F)CC2)c2cncc(F)c2)N(C#N)C1] |
| 1207 | 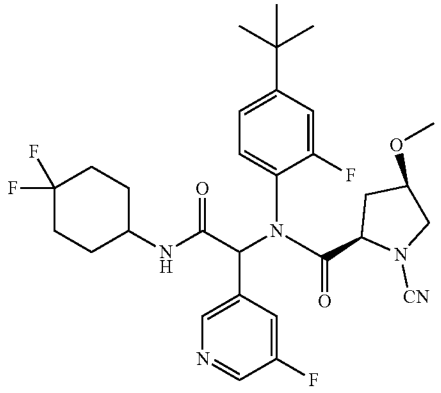 [SMILES: CO[C@@H]1C[C@H](C(=O)N(c2ccc(C(C)(C)C)cc2F)C(C(=O)NC2CCC(F)(F)CC2)c2cncc(F)c2)N(C#N)C1] |
| 1208a | 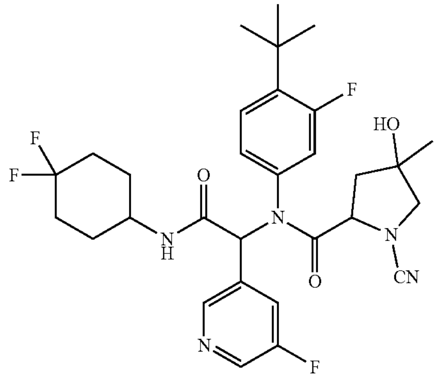 [SMILES: CC1(O)CC(C(=O)N(c2ccc(C(C)(C)C)c(F)c2)C(C(=O)NC2CCC(F)(F)CC2)c2cncc(F)c2)N(C#N)C1] |
| 1208 | 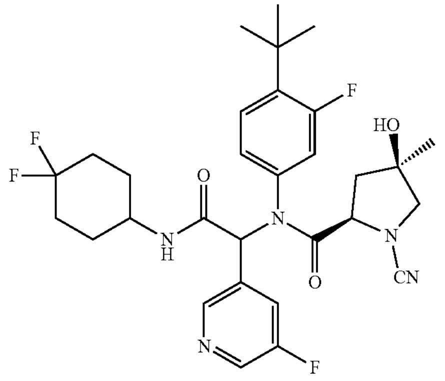 [SMILES: CC(C)(C)c1ccc(N(C(=O)[C@H]2C[C@@](C)(O)CN2C#N)C(C(=O)NC2CCC(F)(F)CC2)c2cncc(F)c2)cc1F] |
TABLE 1-continued
| Exemplary compounds. | |
|---|---|
| Cmpd No. | Structure |
| 1209 | 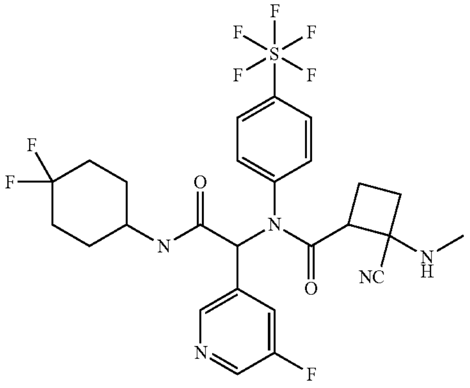 |
| 1210a | 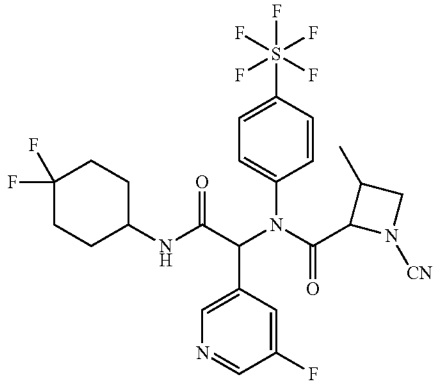 [SMILES: CC1CN(C#N)C1C(=O)N(c1ccc(S(F)(F)(F)(F)F)cc1)C(C(=O)NC1CCC(F)(F)CC1)c1cncc(F)c1] |
| 1210 | 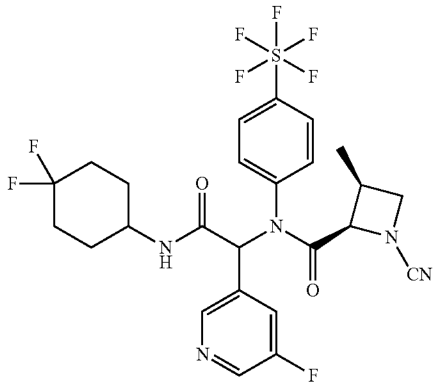 [SMILES: C[C@H]1CN(C#N)[C@H]1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1211 | 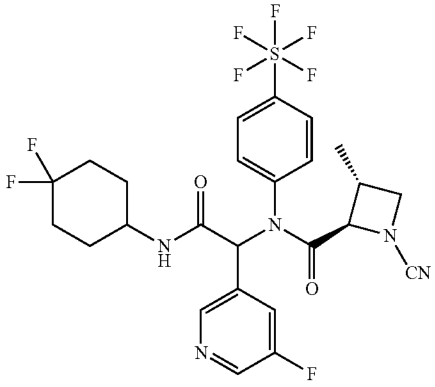 [SMILES: C[C@@H]1CN(C#N)[C@H]1C(=O)N(c1ccc(S(F)(F)(F)(F)F)cc1)C(C(=O)NC1CCC(F)(F)CC1)c1cncc(F)c1] |
| 1212a | 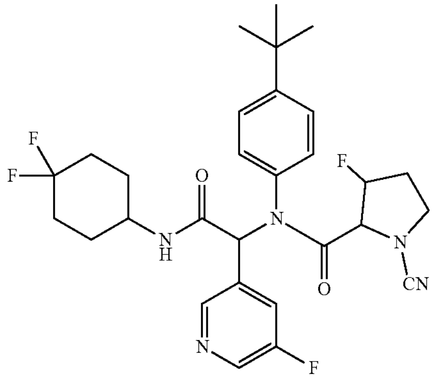 [SMILES: CC(C)(C)c1ccc(N(C(=O)C2C(F)CCN2C#N)C(C(=O)NC2CCC(F)(F)CC2)c2cncc(F)c2)cc1] |
| 1212 | 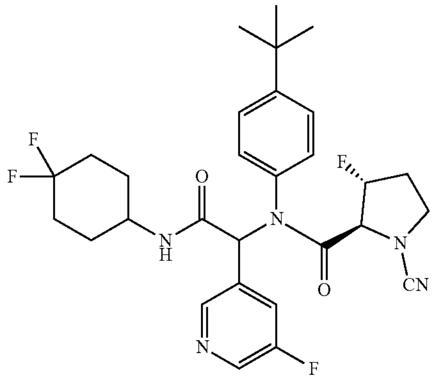 [SMILES: CC(C)(C)c1ccc(N(C(=O)[C@H]2[C@H](F)CCN2C#N)C(C(=O)NC2CCC(F)(F)CC2)c2cncc(F)c2)cc1] |
| 1213 | 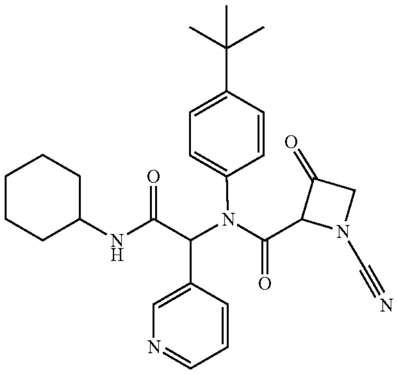 [SMILES: CC(C)(C)c1ccc(N(C(=O)C2C(=O)CN2C#N)C(C(=O)NC2CCCCC2)c2cccnc2)cc1] |
TABLE 1-continued
| Exemplary compounds. | |
|---|---|
| Cmpd No. | Structure |
| 1214a | 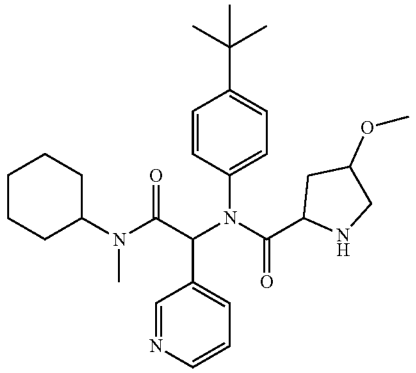 |
| 1214 | 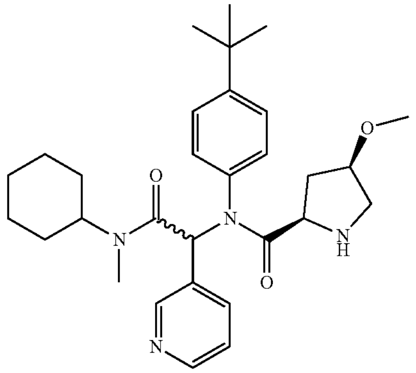 [SMILES: CO[C@H]1CN[C@@H](C(=O)N(c2ccc(C(C)(C)C)cc2)C(C(=O)N(C)C2CCCCC2)c2cccnc2)C1] |
| 1215a | 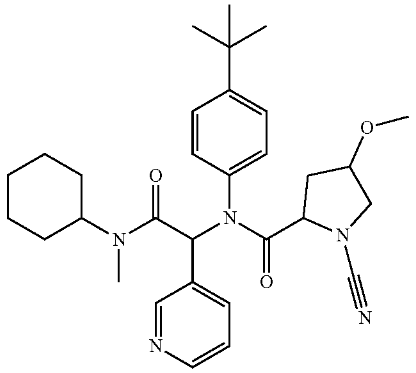 |
| 1215 | 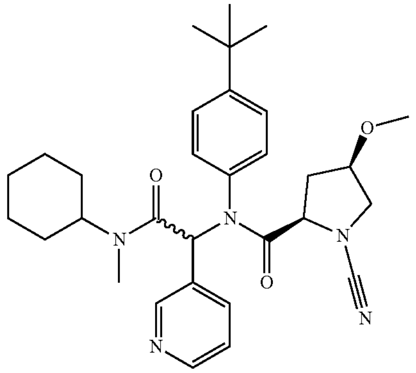 [SMILES: CO[C@@H]1C[C@H](C(=O)N(c2ccc(C(C)(C)C)cc2)C(C(=O)N(C)C2CCCCC2)c2cccnc2)N(C#N)C1] |

TABLE 1-continued
| Exemplary compounds. | |
|---|---|
| Cmpd No. | Structure |
| 1216a | 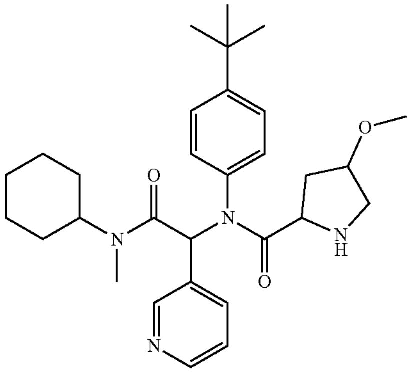 |
| 1216 | 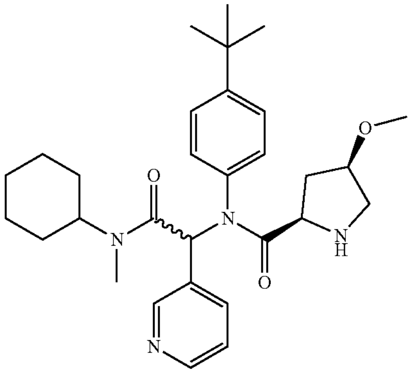 [SMILES: CO[C@H]1CN[C@@H](C(=O)N(c2ccc(C(C)(C)C)cc2)C(C(=O)N(C)C2CCCCC2)c2cccnc2)C1] |
| 1217a | 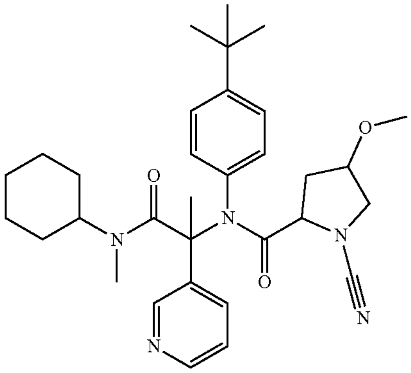 [SMILES: COC1CC(C(=O)N(c2ccc(C(C)(C)C)cc2)C(C)(C(=O)N(C)C2CCCCC2)c2cccnc2)N(C#N)C1] |
| 1217 | 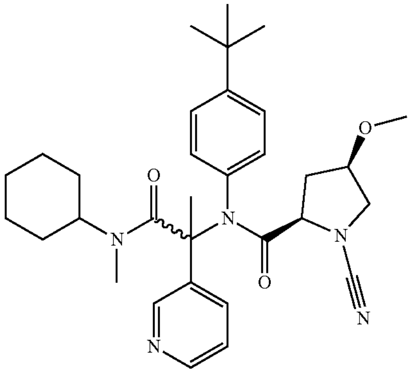 [SMILES: CO[C@@H]1C[C@H](C(=O)N(c2ccc(C(C)(C)C)cc2)C(C)(C(=O)N(C)C2CCCCC2)c2cccnc2)N(C#N)C1] |
TABLE 1-continued
| Exemplary compounds. | |
|---|---|
| Cmpd No. | Structure |
| 1218a | 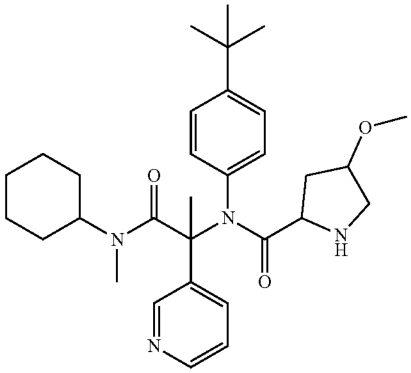 [SMILES: COC1CNC(C(=O)N(c2ccc(C(C)(C)C)cc2)C(C)(C(=O)N(C)C2CCCCC2)c2cccnc2)C1] |
| 1218 | 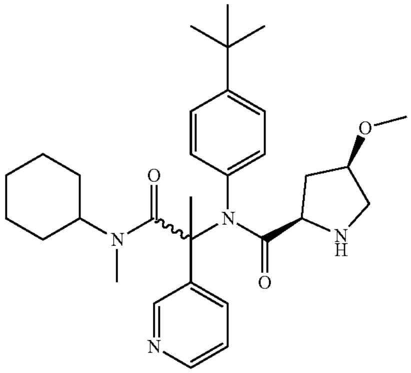 [SMILES: CO[C@H]1CN[C@@H](C(=O)N(c2ccc(C(C)(C)C)cc2)C(C)(C(=O)N(C)C2CCCCC2)c2cccnc2)C1] |
| 1219a | 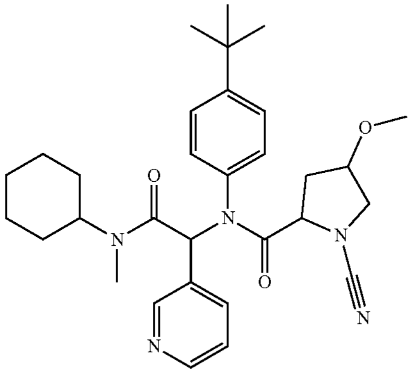 |
| 1219 | 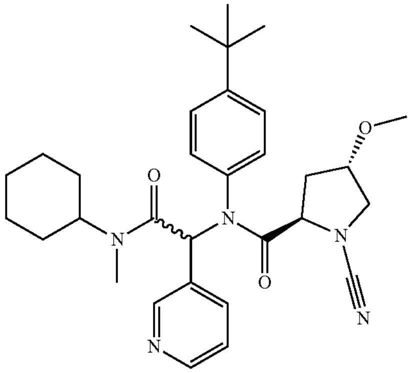 [SMILES: CO[C@H]1C[C@H](C(=O)N(c2ccc(C(C)(C)C)cc2)C(C(=O)N(C)C2CCCCC2)c2cccnc2)N(C#N)C1] |

TABLE 1-continued
| Exemplary compounds. | |
|---|---|
| Cmpd No. | Structure |
| 1220 | 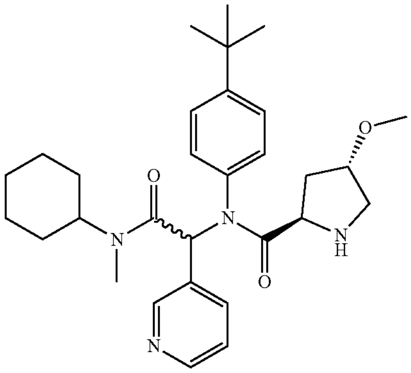 |
| 1221a | 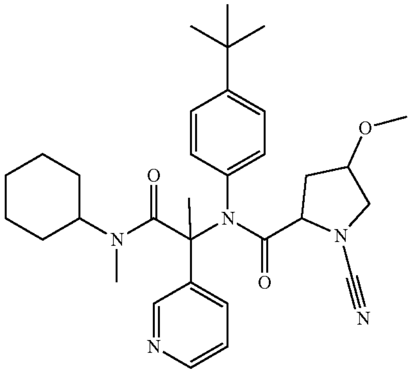 [SMILES: COC1CC(C(=O)N(c2ccc(C(C)(C)C)cc2)C(C)(C(=O)N(C)C2CCCCC2)c2cccnc2)N(C#N)C1] |
| 1221 | 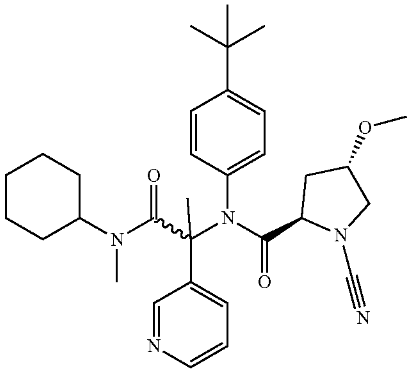 [SMILES: CO[C@H]1C[C@H](C(=O)N(c2ccc(C(C)(C)C)cc2)C(C)(C(=O)N(C)C2CCCCC2)c2cccnc2)N(C#N)C1] |
| 1222a | 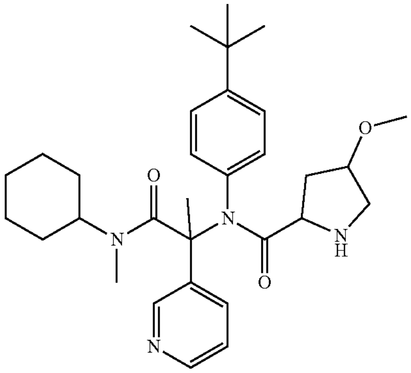 [SMILES: COC1CNC(C(=O)N(c2ccc(C(C)(C)C)cc2)C(C)(C(=O)N(C)C2CCCCC2)c2cccnc2)C1] |
TABLE 1-continued
| Exemplary compounds. | |
|---|---|
| Cmpd No. | Structure |
| 1222 | 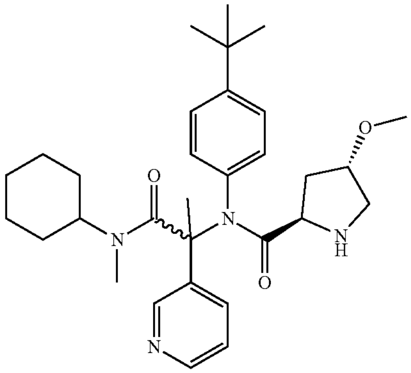 [SMILES: CO[C@@H]1CN[C@@H](C(=O)N(c2ccc(C(C)(C)C)cc2)C(C)(C(=O)N(C)C2CCCCC2)c2cccnc2)C1] |
| 1223a | 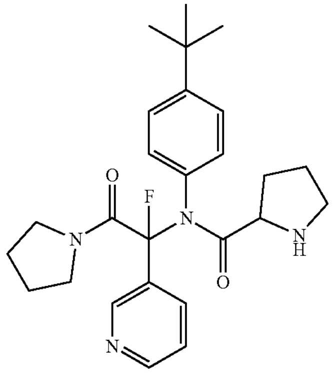 [SMILES: CC(C)(C)c1ccc(N(C(=O)C2CCCN2)C(F)(C(=O)N2CCCC2)c2cccnc2)cc1] |
| 1223 | 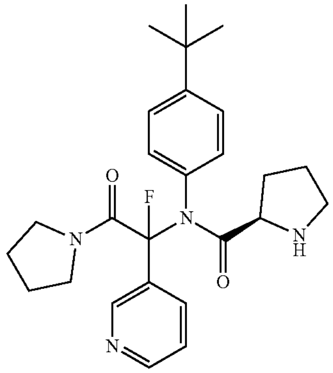 [SMILES: CC(C)(C)c1ccc(N(C(=O)[C@H]2CCCN2)C(F)(C(=O)N2CCCC2)c2cccnc2)cc1] |
| 1224a | 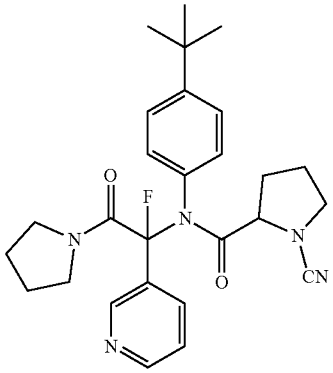 [SMILES: CC(C)(C)c1ccc(N(C(=O)C2CCCN2C#N)C(F)(C(=O)N2CCCC2)c2cccnc2)cc1] |

TABLE 1-continued
| Exemplary compounds. | |
|---|---|
| Cmpd No. | Structure |
| 1224 | 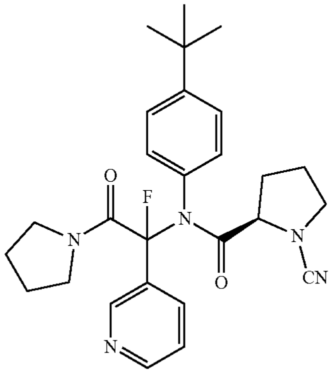 [SMILES: CC(C)(C)c1ccc(N(C(=O)[C@H]2CCCN2C#N)C(F)(C(=O)N2CCCC2)c2cccnc2)cc1] |
| 1225a | 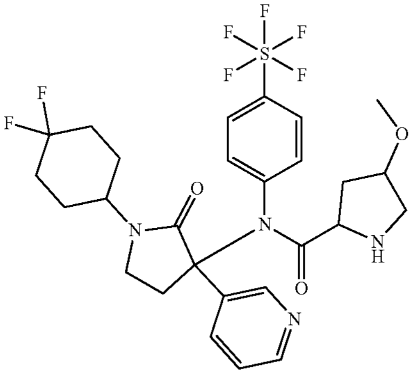 [SMILES: COC1CNC(C(=O)N(c2ccc(S(F)(F)(F)(F)F)cc2)C2(c3cccnc3)CCN(C3CCC(F)(F)CC3)C2=O)C1] |
| 1225 | 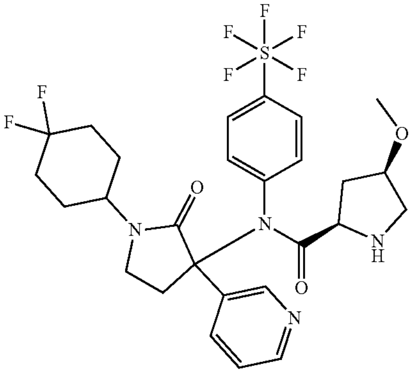 [SMILES: CO[C@H]1CN[C@@H](C(=O)N(c2ccc(S(F)(F)(F)(F)F)cc2)C2(c3cccnc3)CCN(C3CCC(F)(F)CC3)C2=O)C1] |
| 1226a | 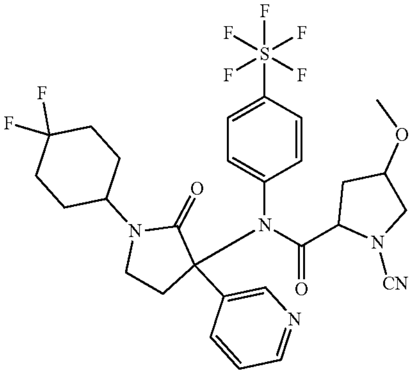 [SMILES: COC1CC(C(=O)N(c2ccc(S(F)(F)(F)(F)F)cc2)C2(c3cccnc3)CCN(C3CCC(F)(F)CC3)C2=O)N(C#N)C1] |
TABLE 1-continued
| Exemplary compounds. | |
|---|---|
| Cmpd No. | Structure |
| 1226 | 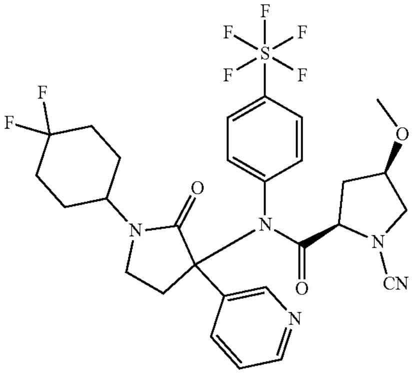 [SMILES: CO[C@@H]1C[C@H](C(=O)N(c2ccc(S(F)(F)(F)(F)F)cc2)C2(c3cccnc3)CCN(C3CCC(F)(F)CC3)C2=O)N(C#N)C1] |
| 1227a | 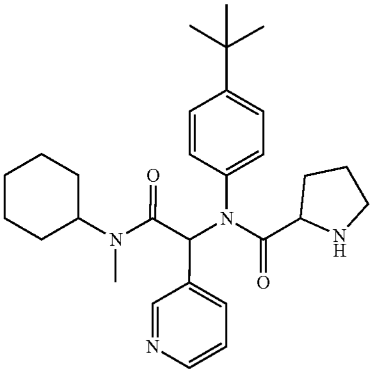 [SMILES: CN(C(=O)C(c1cccnc1)N(C(=O)C1CCCN1)c1ccc(C(C)(C)C)cc1)C1CCCCC1] |
| 1227 | 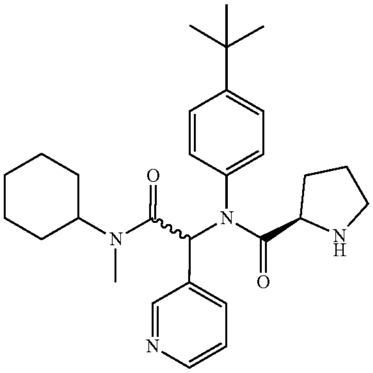 [SMILES: CN(C(=O)C(c1cccnc1)N(C(=O)[C@H]1CCCN1)c1ccc(C(C)(C)C)cc1)C1CCCCC1] |
| 1228a | 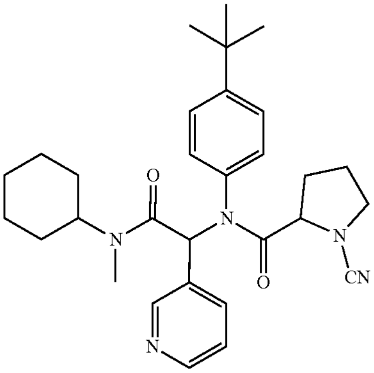 [SMILES: CN(C(=O)C(c1cccnc1)N(C(=O)C1CCCN1C#N)c1ccc(C(C)(C)C)cc1)C1CCCCC1] |

TABLE 1-continued
| Exemplary compounds. | |
|---|---|
| Cmpd No. | Structure |
| 1228 | 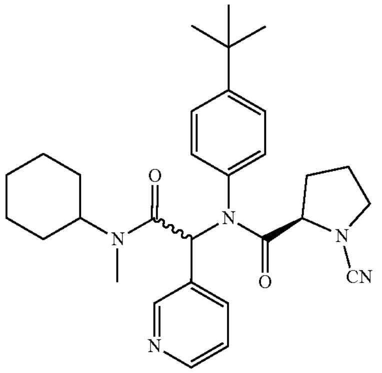 [SMILES: CN(C(=O)C(c1cccnc1)N(C(=O)[C@H]1CCCN1C#N)c1ccc(C(C)(C)C)cc1)C1CCCCC1] |
| 1229a | 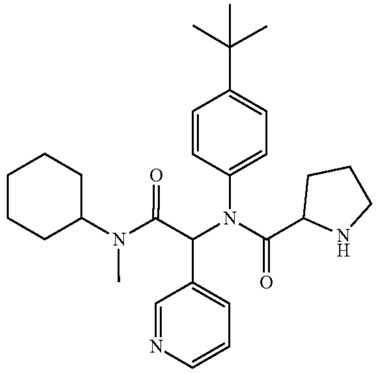 [SMILES: CN(C(=O)C(c1cccnc1)N(C(=O)C1CCCN1)c1ccc(C(C)(C)C)cc1)C1CCCCC1] |
| 1229 | 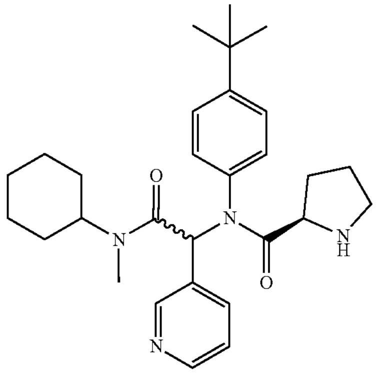 [SMILES: CN(C(=O)C(c1cccnc1)N(C(=O)[C@H]1CCCN1)c1ccc(C(C)(C)C)cc1)C1CCCCC1] |
| 1230a | 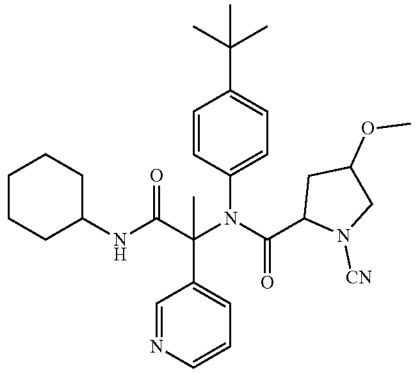 [SMILES: COC1CC(C(=O)N(c2ccc(C(C)(C)C)cc2)C(C)(C(=O)NC2CCCCC2)c2cccnc2)N(C#N)C1] |
TABLE 1-continued
| Exemplary compounds. | |
|---|---|
| Cmpd No. | Structure |
| 1230 | 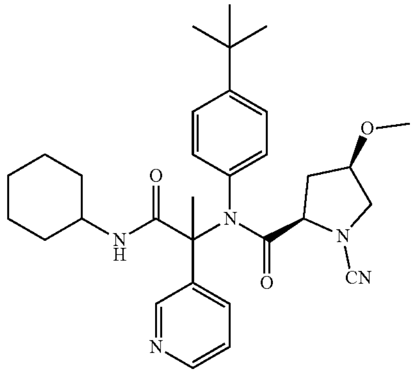 [SMILES: CO[C@@H]1C[C@H](C(=O)N(c2ccc(C(C)(C)C)cc2)C(C)(C(=O)NC2CCCCC2)c2cccnc2)N(C#N)C1] |
| 1231a | 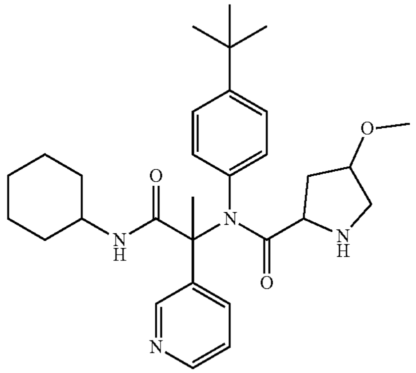 [SMILES: COC1CNC(C(=O)N(c2ccc(C(C)(C)C)cc2)C(C)(C(=O)NC2CCCCC2)c2cccnc2)C1] |
| 1231 | 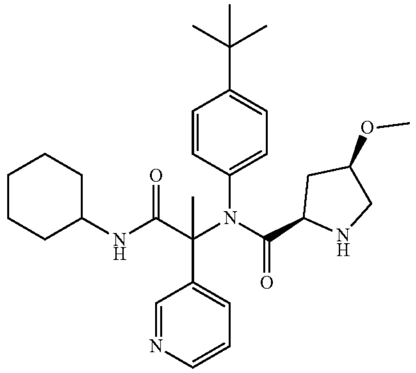 [SMILES: CO[C@H]1CN[C@@H](C(=O)N(c2ccc(C(C)(C)C)cc2)C(C)(C(=O)NC2CCCCC2)c2cccnc2)C1] |
| 1232a | 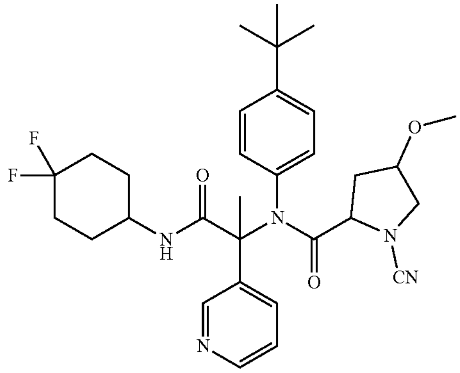 [SMILES: COC1CC(C(=O)N(c2ccc(C(C)(C)C)cc2)C(C)(C(=O)NC2CCC(F)(F)CC2)c2cccnc2)N(C#N)C1] |

TABLE 1-continued
| Exemplary compounds. | |
|---|---|
| Cmpd No. | Structure |
| 1232 | 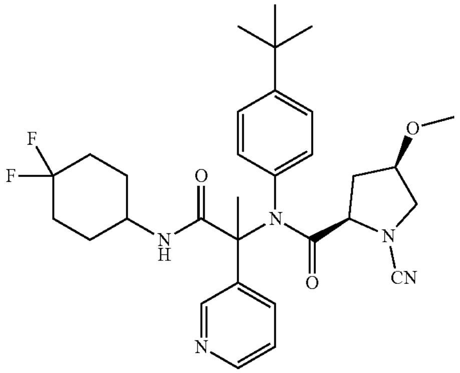 [SMILES: CO[C@@H]1C[C@H](C(=O)N(c2ccc(C(C)(C)C)cc2)C(C)(C(=O)NC2CCC(F)(F)CC2)c2cccnc2)N(C#N)C1] |
| 1233a | 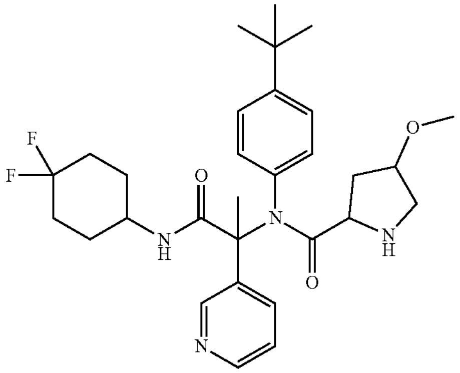 [SMILES: COC1CNC(C(=O)N(c2ccc(C(C)(C)C)cc2)C(C)(C(=O)NC2CCC(F)(F)CC2)c2cccnc2)C1] |
| 1233 | 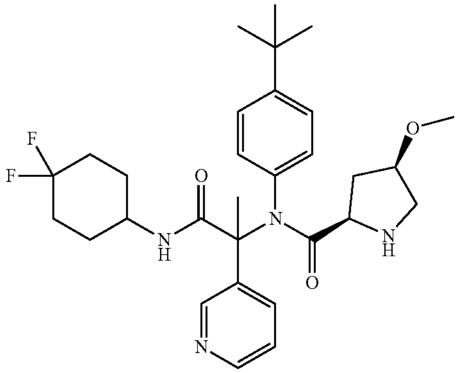 [SMILES: CO[C@H]1CN[C@@H](C(=O)N(c2ccc(C(C)(C)C)cc2)C(C)(C(=O)NC2CCC(F)(F)CC2)c2cccnc2)C1] |
| 1234a | 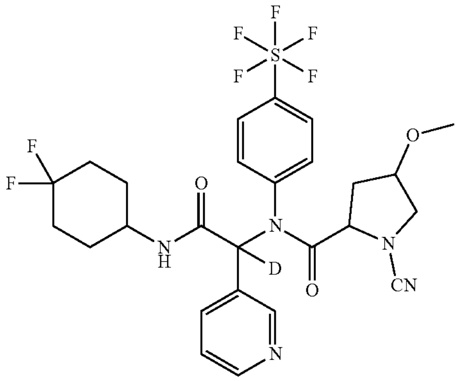 [SMILES: [2H]C(C(=O)NC1CCC(F)(F)CC1)(c1cccnc1)N(C(=O)C1CC(OC)CN1C#N)c1ccc(S(F)(F)(F)(F)F)cc1] |
TABLE 1-continued
| Exemplary compounds. | |
|---|---|
| Cmpd No. | Structure |
| 1234 | 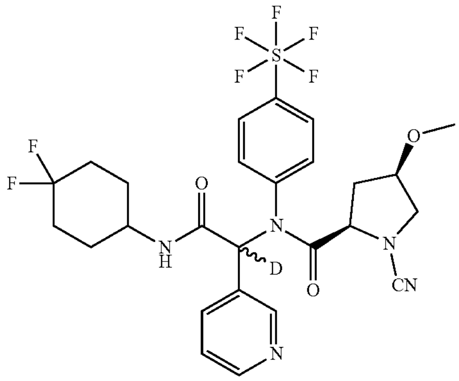 [SMILES: [2H]C(C(=O)NC1CCC(F)(F)CC1)(c1cccnc1)N(C(=O)[C@H]1C[C@@H](OC)CN1C#N)c1ccc(S(F)(F)(F)(F)F)cc1] |
| 1235a | 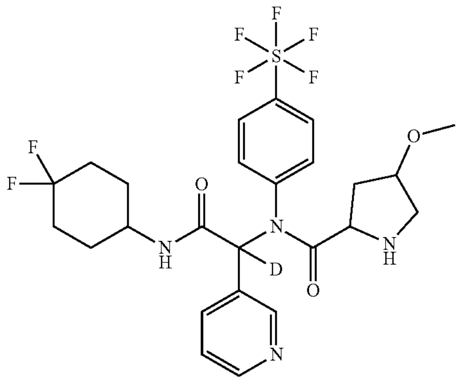 [SMILES: [2H]C(C(=O)NC1CCC(F)(F)CC1)(c1cccnc1)N(C(=O)C1CC(OC)CN1)c1ccc(S(F)(F)(F)(F)F)cc1] |
| 1235 | 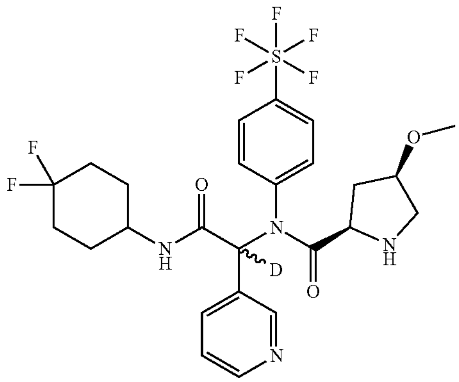 [SMILES: [2H]C(C(=O)NC1CCC(F)(F)CC1)(c1cccnc1)N(C(=O)[C@H]1C[C@@H](OC)CN1)c1ccc(S(F)(F)(F)(F)F)cc1] |
| 1236a | 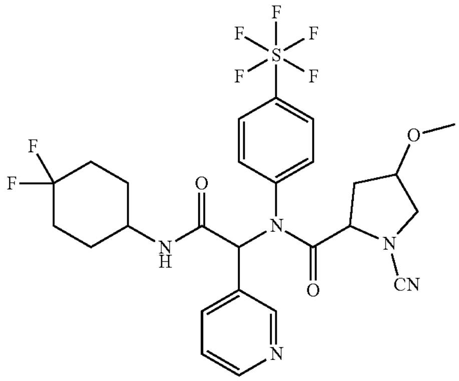 [SMILES: COC1CC(C(=O)N(c2ccc(S(F)(F)(F)(F)F)cc2)C(C(=O)NC2CCC(F)(F)CC2)c2cccnc2)N(C#N)C1] |

TABLE 1-continued
Exemplary compounds.
| Cmpd No. | Structure |
|---|---|
| 1236 | 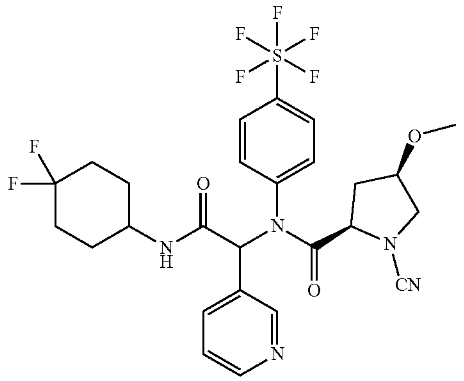 [SMILES: CO[C@@H]1C[C@H](C(=O)N(c2ccc(S(F)(F)(F)(F)F)cc2)C(C(=O)NC2CCC(F)(F)CC2)c2cccnc2)N(C#N)C1] |
| 1237a | 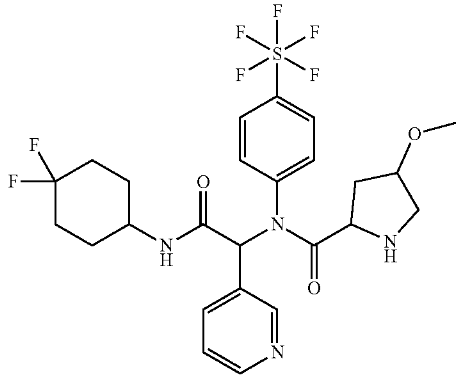 [SMILES: COC1CNC(C(=O)N(c2ccc(S(F)(F)(F)(F)F)cc2)C(C(=O)NC2CCC(F)(F)CC2)c2cccnc2)C1] |
| 1237 | 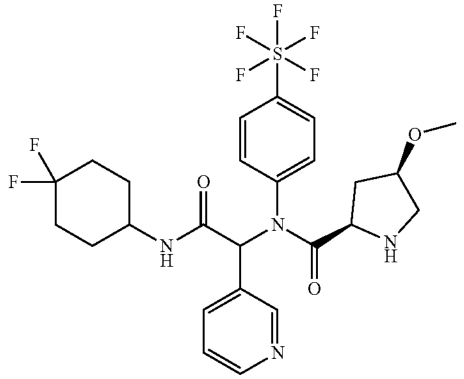 [SMILES: CO[C@H]1CN[C@@H](C(=O)N(c2ccc(S(F)(F)(F)(F)F)cc2)C(C(=O)NC2CCC(F)(F)CC2)c2cccnc2)C1] |
| 1238a | 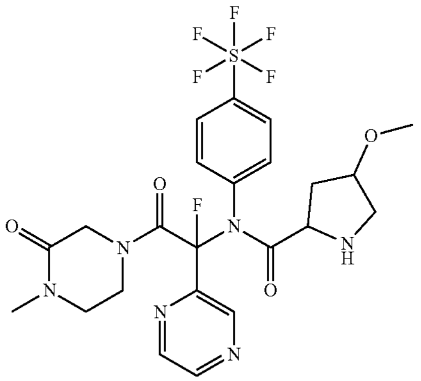 [SMILES: COC1CNC(C(=O)N(c2ccc(S(F)(F)(F)(F)F)cc2)C(F)(C(=O)N2CCN(C)C(=O)C2)c2cnccn2)C1] |
| 1238 | 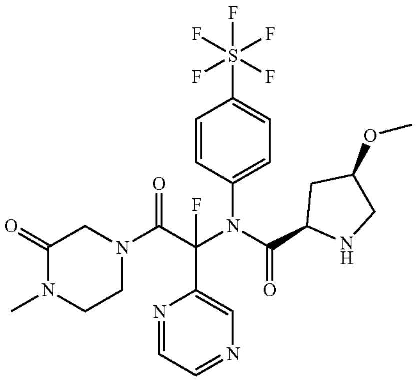 [SMILES: CO[C@H]1CN[C@@H](C(=O)N(c2ccc(S(F)(F)(F)(F)F)cc2)C(F)(C(=O)N2CCN(C)C(=O)C2)c2cnccn2)C1] |
| 1239a | 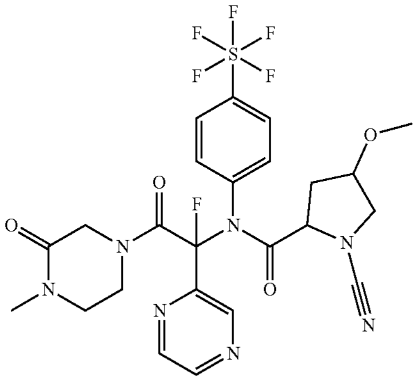 [SMILES: COC1CC(C(=O)N(c2ccc(S(F)(F)(F)(F)F)cc2)C(F)(C(=O)N2CCN(C)C(=O)C2)c2cnccn2)N(C#N)C1] |
| 1239 | 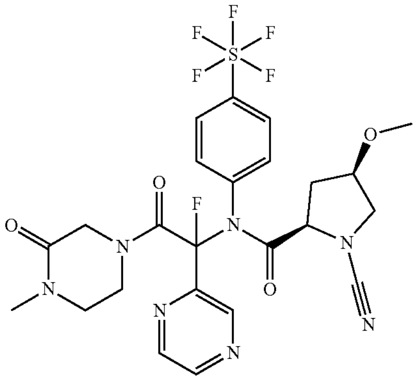 [SMILES: CO[C@@H]1C[C@H](C(=O)N(c2ccc(S(F)(F)(F)(F)F)cc2)C(F)(C(=O)N2CCN(C)C(=O)C2)c2cnccn2)N(C#N)C1] |
| 1240a | 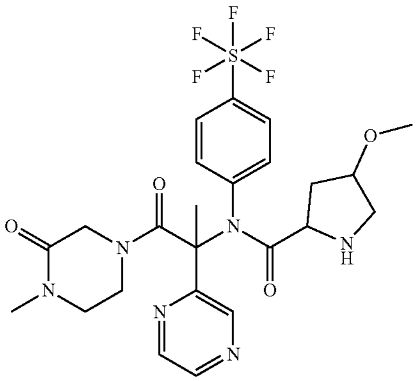 [SMILES: COC1CNC(C(=O)N(c2ccc(S(F)(F)(F)(F)F)cc2)C(C)(C(=O)N2CCN(C)C(=O)C2)c2cnccn2)C1] |

TABLE 1-continued
| Exemplary compounds. | |
|---|---|
| Cmpd No. | Structure |
| 1240 | 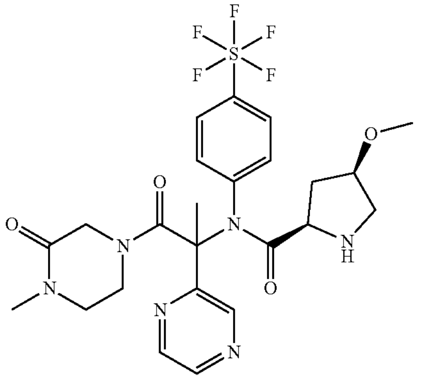 [SMILES: CO[C@H]1CN[C@@H](C(=O)N(c2ccc(S(F)(F)(F)(F)F)cc2)C(C)(C(=O)N2CCN(C)C(=O)C2)c2cnccn2)C1] |
| 1241a | 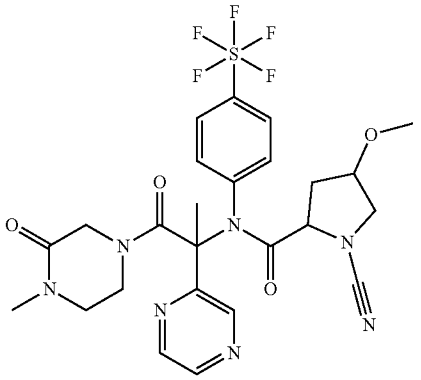 [SMILES: COC1CC(C(=O)N(c2ccc(S(F)(F)(F)(F)F)cc2)C(C)(C(=O)N2CCN(C)C(=O)C2)c2cnccn2)N(C#N)C1] |
| 1241 | 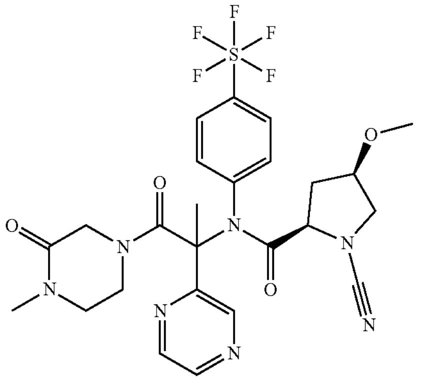 [SMILES: CO[C@@H]1C[C@H](C(=O)N(c2ccc(S(F)(F)(F)(F)F)cc2)C(C)(C(=O)N2CCN(C)C(=O)C2)c2cnccn2)N(C#N)C1] |
| 1242a | 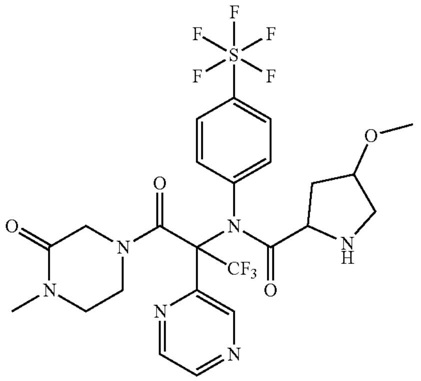 [SMILES: COC1CNC(C(=O)N(c2ccc(S(F)(F)(F)(F)F)cc2)C(C(=O)N2CCN(C)C(=O)C2)(c2cnccn2)C(F)(F)F)C1] |
TABLE 1-continued
| Exemplary compounds. | |
|---|---|
| Cmpd No. | Structure |
| 1242 | 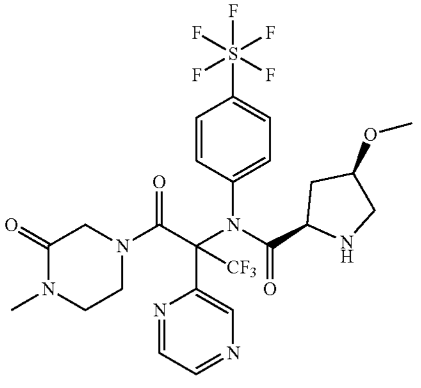 [SMILES: CO[C@H]1CN[C@@H](C(=O)N(c2ccc(S(F)(F)(F)(F)F)cc2)C(C(=O)N2CCN(C)C(=O)C2)(c2cnccn2)C(F)(F)F)C1] |
| 1243a | 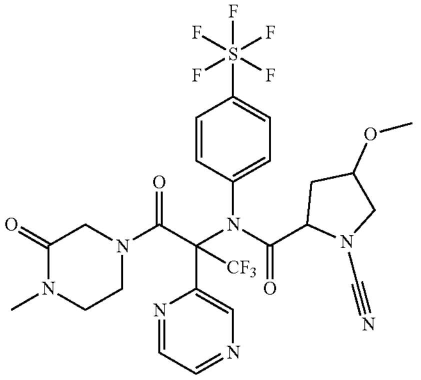 [SMILES: COC1CC(C(=O)N(c2ccc(S(F)(F)(F)(F)F)cc2)C(C(=O)N2CCN(C)C(=O)C2)(c2cnccn2)C(F)(F)F)N(C#N)C1] |
| 1243 | 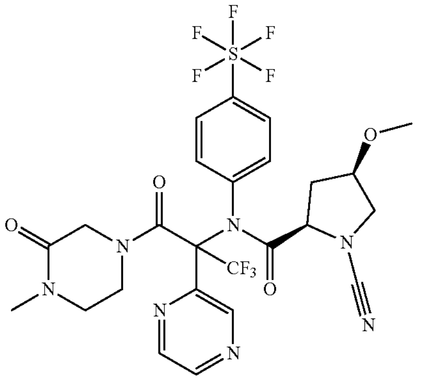 [SMILES: CO[C@@H]1C[C@H](C(=O)N(c2ccc(S(F)(F)(F)(F)F)cc2)C(C(=O)N2CCN(C)C(=O)C2)(c2cnccn2)C(F)(F)F)N(C#N)C1] |
| 1244a | 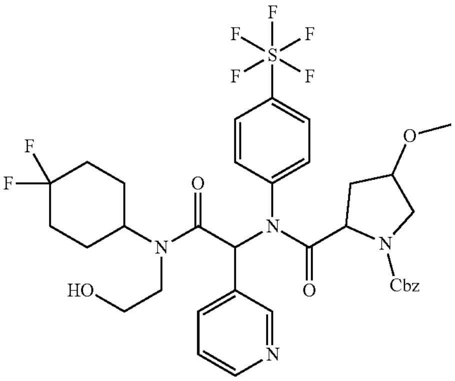 [SMILES: COC1CC(C(=O)N(c2ccc(S(F)(F)(F)(F)F)cc2)C(C(=O)N(CCO)C2CCC(F)(F)CC2)c2cccnc2)N(C(=O)OCc2ccccc2)C1] |

TABLE 1-continued
Exemplary compounds.
| Cmpd No. | Structure |
|---|---|
| 1244 | 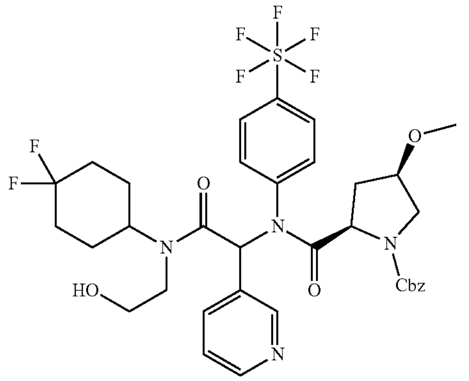 [SMILES: CO[C@@H]1C[C@H](C(=O)N(c2ccc(S(F)(F)(F)(F)F)cc2)C(C(=O)N(CCO)C2CCC(F)(F)CC2)c2cccnc2)N(C(=O)OCc2ccccc2)C1] |
| 1245a | 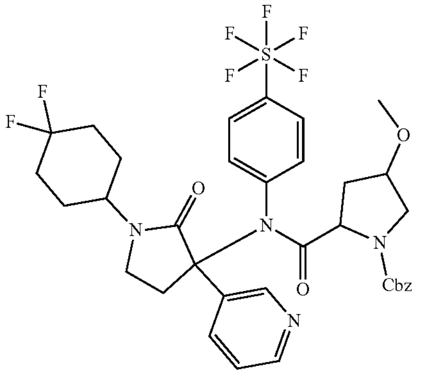 [SMILES: COC1CC(C(=O)N(c2ccc(S(F)(F)(F)(F)F)cc2)C2(c3cccnc3)CCN(C3CCC(F)(F)CC3)C2=O)N(C(=O)OCc2ccccc2)C1] |
| 1245 | 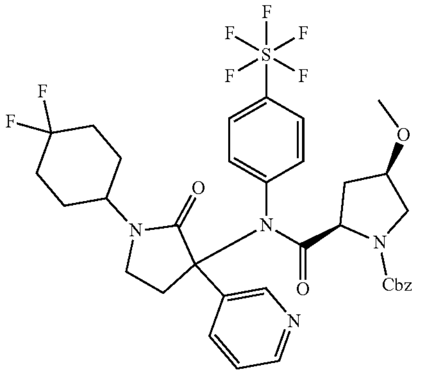 [SMILES: CO[C@@H]1C[C@H](C(=O)N(c2ccc(S(F)(F)(F)(F)F)cc2)C2(c3cccnc3)CCN(C3CCC(F)(F)CC3)C2=O)N(C(=O)OCc2ccccc2)C1] |
| 1246 | 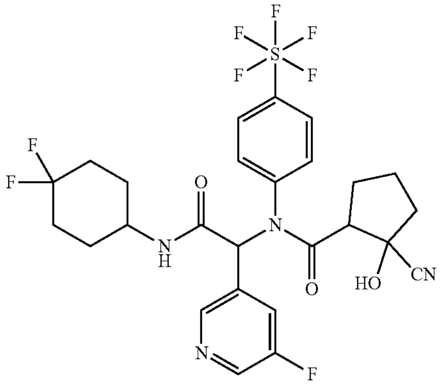 [SMILES: N#CC1(O)CCCC1C(=O)N(c1ccc(S(F)(F)(F)(F)F)cc1)C(C(=O)NC1CCC(F)(F)CC1)c1cncc(F)c1] |
TABLE 1-continued
Exemplary compounds.
| Cmpd No. | Structure |
|---|---|
| 1247 | 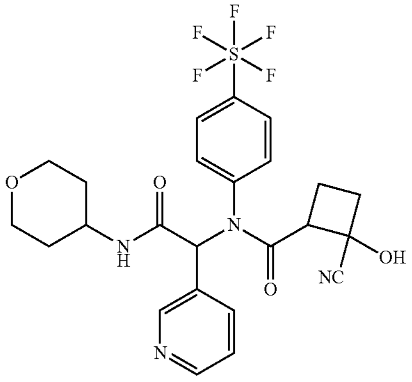 [SMILES: N#CC1(O)CCC1C(=O)N(c1ccc(S(F)(F)(F)(F)F)cc1)C(C(=O)NC1CCOCC1)c1cccnc1] |
| 1248a | 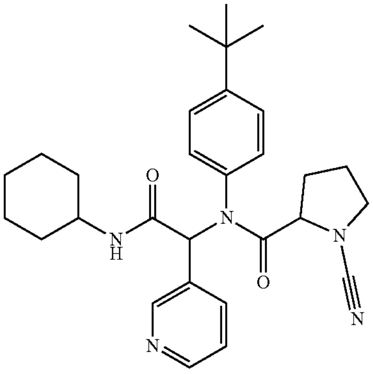 [SMILES: CC(C)(C)c1ccc(N(C(=O)C2CCCN2C#N)C(C(=O)NC2CCCCC2)c2cccnc2)cc1] |
| 1248 | 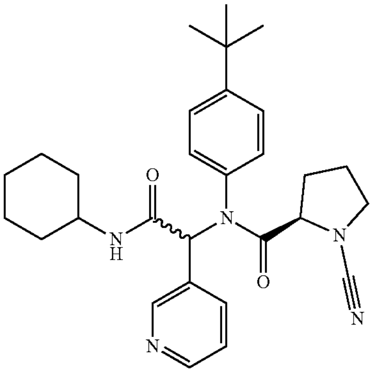 [SMILES: CC(C)(C)c1ccc(N(C(=O)[C@H]2CCCN2C#N)C(C(=O)NC2CCCCC2)c2cccnc2)cc1] |
| 1249 | 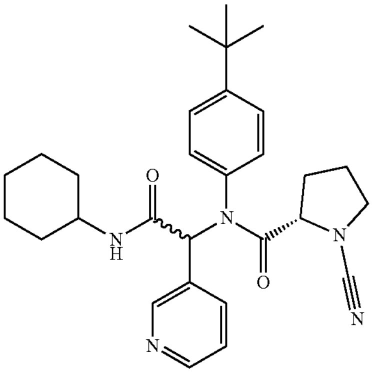 [SMILES: CC(C)(C)c1ccc(N(C(=O)[C@@H]2CCCN2C#N)C(C(=O)NC2CCCCC2)c2cccnc2)cc1] |

TABLE 1-continued
| Exemplary compounds. | |
|---|---|
| Cmpd No. | Structure |
| 1250 | 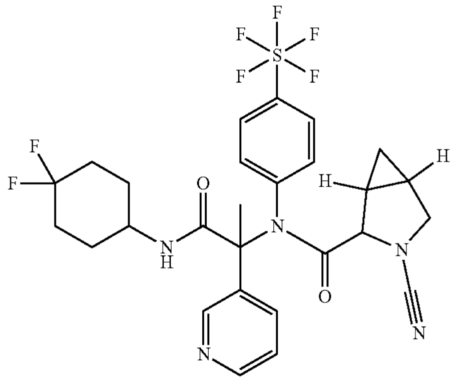 [SMILES: CC(C(=O)NC1CCC(F)(F)CC1)(c1cccnc1)N(C(=O)C1C2CC2CN1C#N)c1ccc(S(F)(F)(F)(F)F)cc1] |
| 1251 | 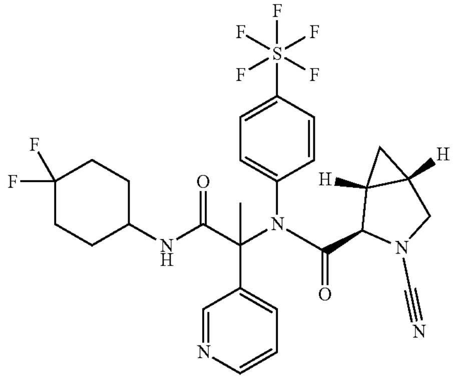 [SMILES: CC(C(=O)NC1CCC(F)(F)CC1)(c1cccnc1)N(C(=O)[C@H]1[C@@H]2C[C@@H]2CN1C#N)c1ccc(S(F)(F)(F)(F)F)cc1] |
| 1258 | 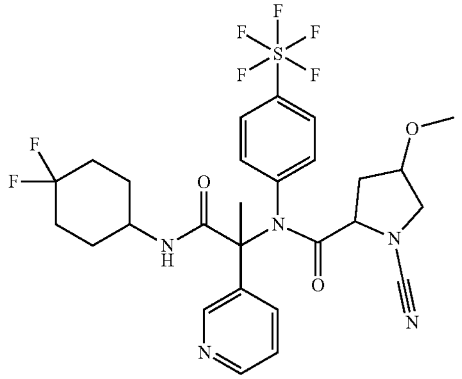 [SMILES: COC1CC(C(=O)N(c2ccc(S(F)(F)(F)(F)F)cc2)C(C)(C(=O)NC2CCC(F)(F)CC2)c2cccnc2)N(C#N)C1] |
| 1259 | 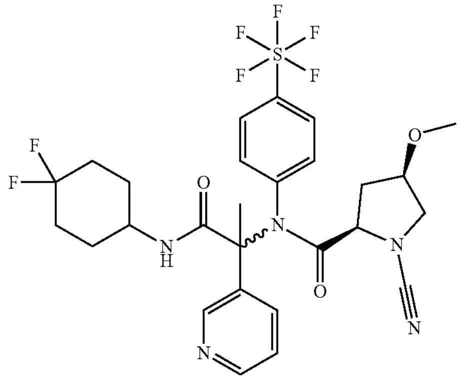 [SMILES: CO[C@@H]1C[C@H](C(=O)N(c2ccc(S(F)(F)(F)(F)F)cc2)C(C)(C(=O)NC2CCC(F)(F)CC2)c2cccnc2)N(C#N)C1] |
TABLE 1-continued
| Exemplary compounds. | |
|---|---|
| Cmpd No. | Structure |
| 1260 | 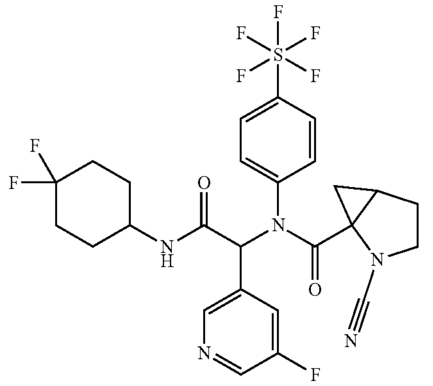 [SMILES: N#CN1CCC2CC21C(=O)N(c1ccc(S(F)(F)(F)(F)F)cc1)C(C(=O)NC1CCC(F)(F)CC1)c1cncc(F)c1] |
| 1261 | 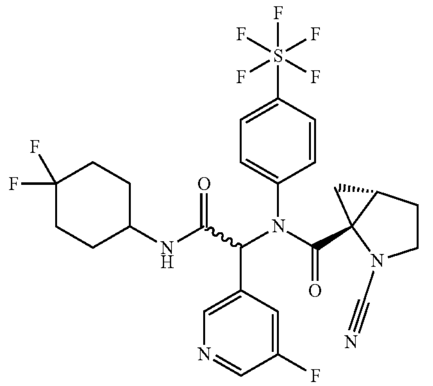 [SMILES: N#CN1CC[C@H]2C[C@]21C(=O)N(c1ccc(S(F)(F)(F)(F)F)cc1)C(C(=O)NC1CCC(F)(F)CC1)c1cncc(F)c1] |
| 1262 | 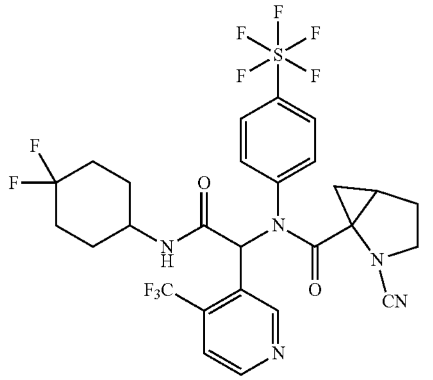 [SMILES: N#CN1CCC2CC21C(=O)N(c1ccc(S(F)(F)(F)(F)F)cc1)C(C(=O)NC1CCC(F)(F)CC1)c1cnccc1C(F)(F)F] |
| 1263 | 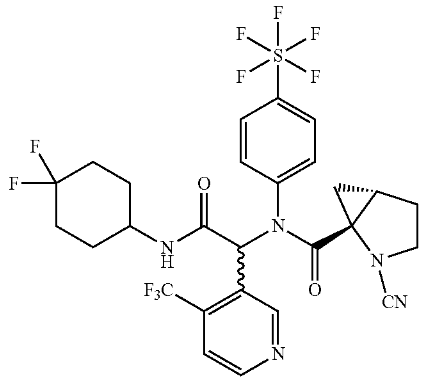 [SMILES: N#CN1CC[C@H]2C[C@]21C(=O)N(c1ccc(S(F)(F)(F)(F)F)cc1)C(C(=O)NC1CCC(F)(F)CC1)c1cnccc1C(F)(F)F] |

TABLE 1-continued
| Exemplary compounds. | |
|---|---|
| Cmpd No. | Structure |
| 1264 | 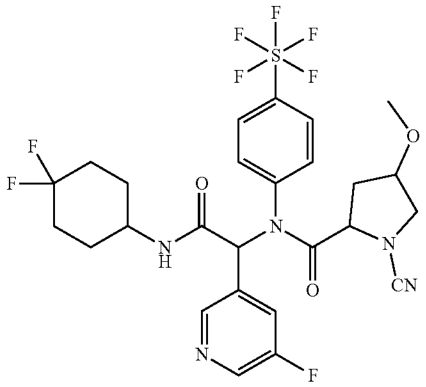 [SMILES: COC1CC(C(=O)N(c2ccc(S(F)(F)(F)(F)F)cc2)C(C(=O)NC2CCC(F)(F)CC2)c2cncc(F)c2)N(C#N)C1] |
| 1265 | 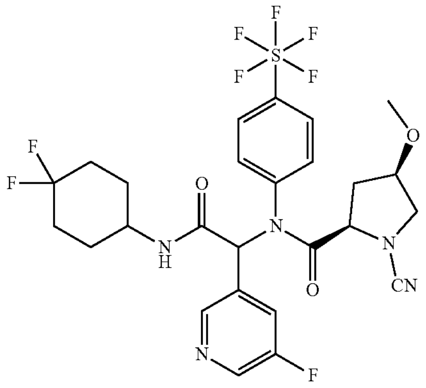 [SMILES: CO[C@@H]1C[C@H](C(=O)N(c2ccc(S(F)(F)(F)(F)F)cc2)C(C(=O)NC2CCC(F)(F)CC2)c2cncc(F)c2)N(C#N)C1] |
| 1266 | 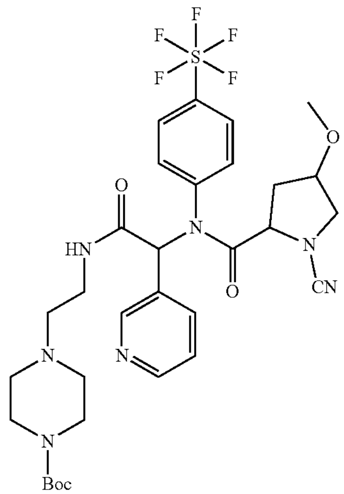 [SMILES: COC1CC(C(=O)N(c2ccc(S(F)(F)(F)(F)F)cc2)C(C(=O)NCCN2CCN(C(=O)OC(C)(C)C)CC2)c2cccnc2)N(C#N)C1] |
| 1267 | 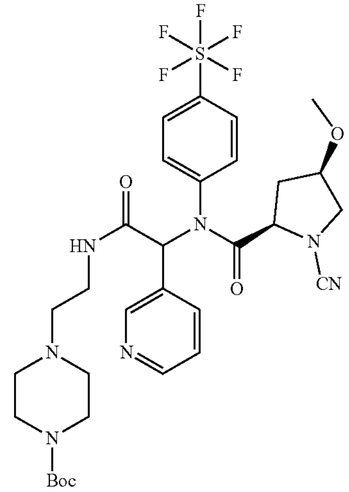 [SMILES: CO[C@@H]1C[C@H](C(=O)N(c2ccc(S(F)(F)(F)(F)F)cc2)C(C(=O)NCCN2CCN(C(=O)OC(C)(C)C)CC2)c2cccnc2)N(C#N)C1] |
| 1274 | 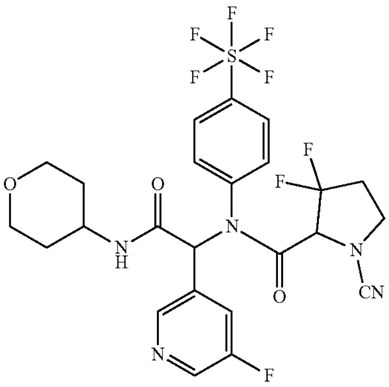 [SMILES: N#CN1CCC(F)(F)C1C(=O)N(c1ccc(S(F)(F)(F)(F)F)cc1)C(C(=O)NC1CCOCC1)c1cncc(F)c1] |
| 1279 | 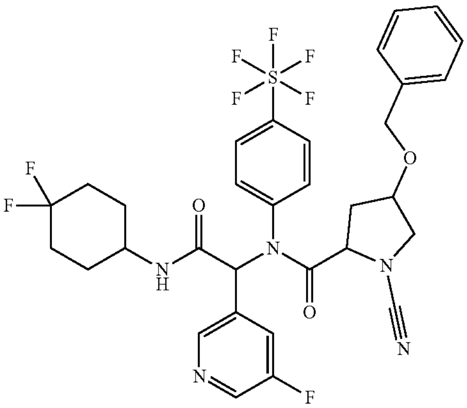 [SMILES: N#CN1CC(OCc2ccccc2)CC1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1280 | 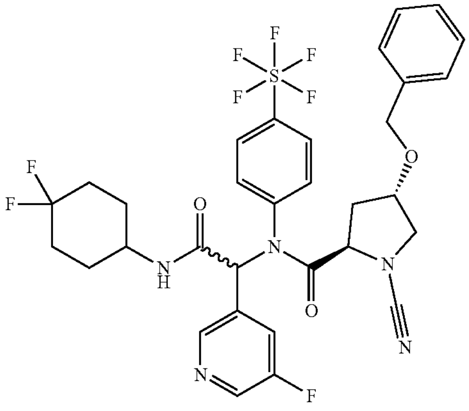 [SMILES: N#CN1C[C@@H](OCc2ccccc2)C[C@@H]1C(=O)N(c1ccc(S(F)(F)(F)(F)F)cc1)C(C(=O)NC1CCC(F)(F)CC1)c1cncc(F)c1] |
| 1287 | 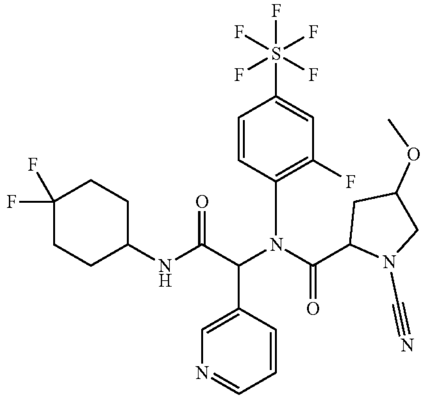 [SMILES: COC1CC(C(=O)N(c2ccc(S(F)(F)(F)(F)F)cc2F)C(C(=O)NC2CCC(F)(F)CC2)c2cccnc2)N(C#N)C1] |
| 1288 | 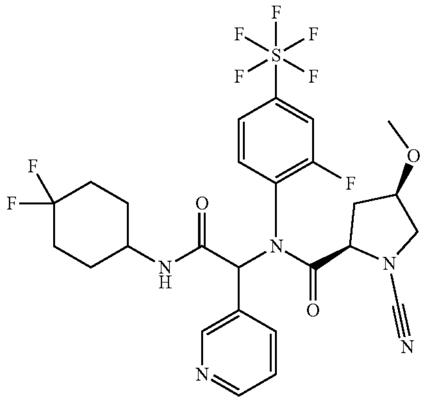 [SMILES: CO[C@@H]1C[C@H](C(=O)N(c2ccc(S(F)(F)(F)(F)F)cc2F)C(C(=O)NC2CCC(F)(F)CC2)c2cccnc2)N(C#N)C1] |
TABLE 1-continued
| Exemplary compounds. | |
|---|---|
| Cmpd No. | Structure |
| 1288a | 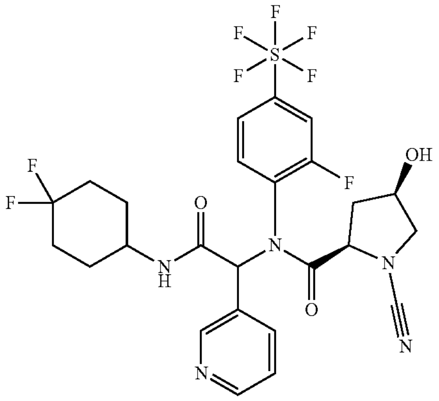 [SMILES: N#CN1C[C@H](O)C[C@@H]1C(=O)N(c1ccc(S(F)(F)(F)(F)F)cc1F)C(C(=O)NC1CCC(F)(F)CC1)c1cccnc1] |
| 1289 | 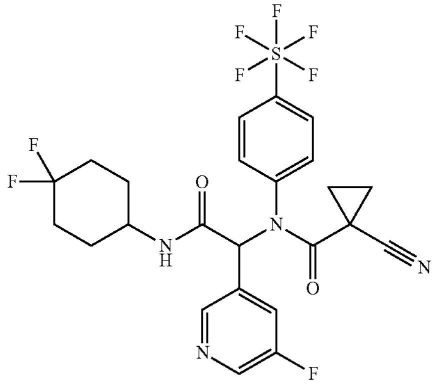 [SMILES: N#CC1(C(=O)N(c2ccc(S(F)(F)(F)(F)F)cc2)C(C(=O)NC2CCC(F)(F)CC2)c2cncc(F)c2)CC1] |
| 1290 | 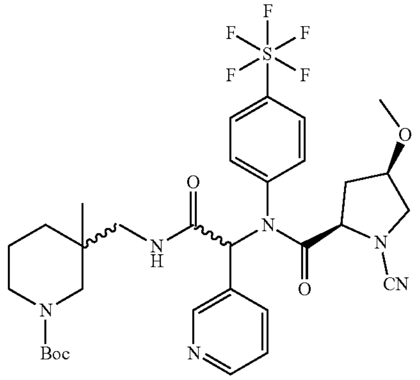 [SMILES: CO[C@@H]1C[C@H](C(=O)N(c2ccc(S(F)(F)(F)(F)F)cc2)C(C(=O)NCC2(C)CCCN(C(=O)OC(C)(C)C)C2)c2cccnc2)N(C#N)C1] |
| 1291 | 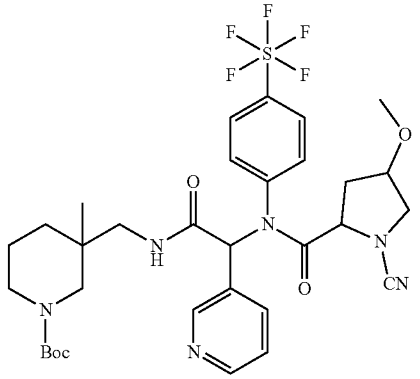 [SMILES: COC1CC(C(=O)N(c2ccc(S(F)(F)(F)(F)F)cc2)C(C(=O)NCC2(C)CCCN(C(=O)OC(C)(C)C)C2)c2cccnc2)N(C#N)C1] |

TABLE 1-continued
| Exemplary compounds. | |
|---|---|
| Cmpd No. | Structure |
| 1292 | 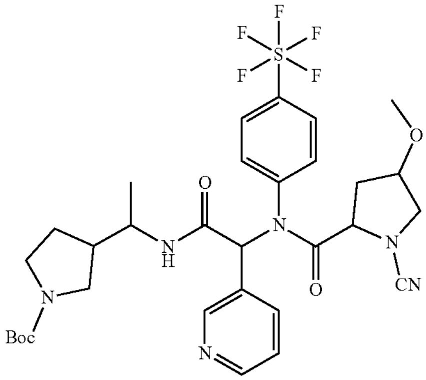 [SMILES: COC1CC(C(=O)N(c2ccc(S(F)(F)(F)(F)F)cc2)C(C(=O)NC(C)C2CCN(C(=O)OC(C)(C)C)C2)c2cccnc2)N(C#N)C1] |
| 1293 | 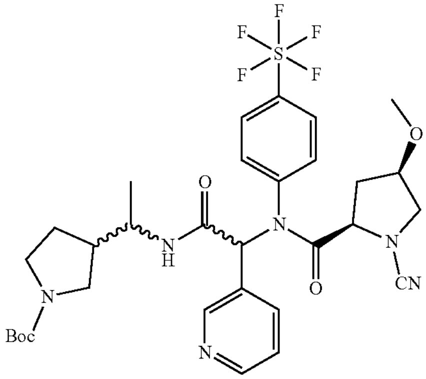 |
| 1296 | 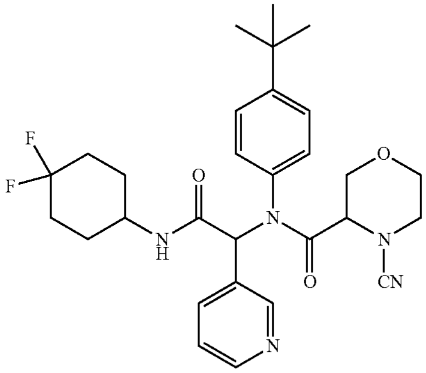 [SMILES: CC(C)(C)c1ccc(N(C(=O)C2COCCN2C#N)C(C(=O)NC2CCC(F)(F)CC2)c2cccnc2)cc1] |
| 1297 | 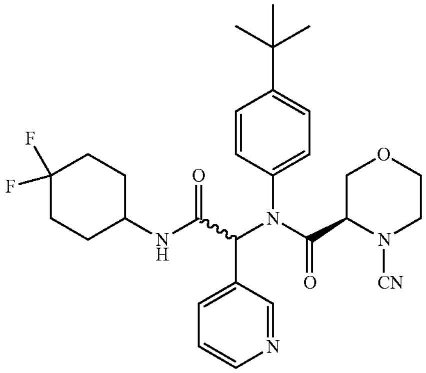 [SMILES: CC(C)(C)c1ccc(N(C(=O)[C@H]2COCCN2C#N)C(C(=O)NC2CCC(F)(F)CC2)c2cccnc2)cc1] |
TABLE 1-continued
| Exemplary compounds. | |
|---|---|
| Cmpd No. | Structure |
| 1298 | 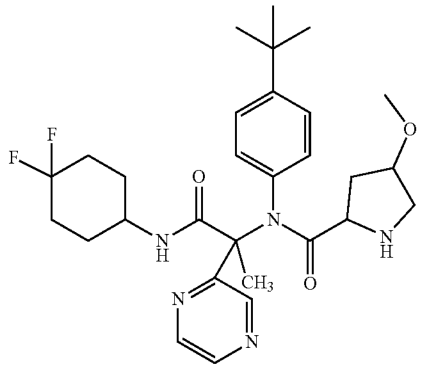 [SMILES: COC1CNC(C(=O)N(c2ccc(C(C)(C)C)cc2)C(C)(C(=O)NC2CCC(F)(F)CC2)c2cnccn2)C1] |
| 1298a | 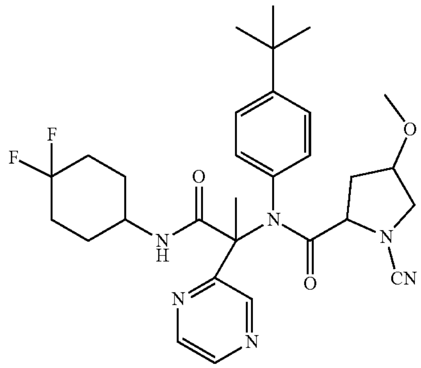 [SMILES: COC1CC(C(=O)N(c2ccc(C(C)(C)C)cc2)C(C)(C(=O)NC2CCC(F)(F)CC2)c2cnccn2)N(C#N)C1] |
| 1298b | 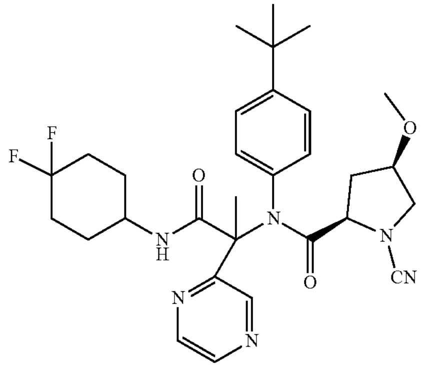 [SMILES: CO[C@@H]1C[C@H](C(=O)N(c2ccc(C(C)(C)C)cc2)C(C)(C(=O)NC2CCC(F)(F)CC2)c2cnccn2)N(C#N)C1] |
| 1299a | 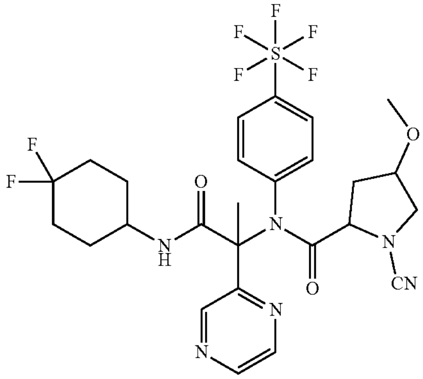 [SMILES: COC1CC(C(=O)N(c2ccc(S(F)(F)(F)(F)F)cc2)C(C)(C(=O)NC2CCC(F)(F)CC2)c2cnccn2)N(C#N)C1] |

TABLE 1-continued
| Exemplary compounds. | |
|---|---|
| Cmpd No. | Structure |
| 1299 | 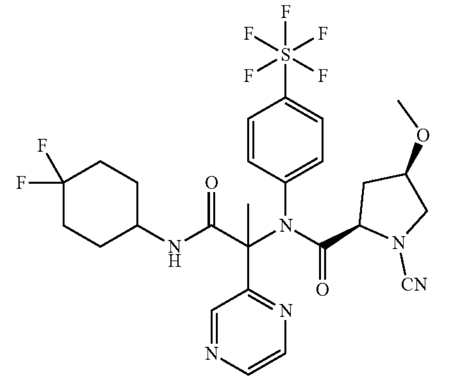 [SMILES: CO[C@@H]1C[C@H](C(=O)N(c2ccc(S(F)(F)(F)(F)F)cc2)C(C)(C(=O)NC2CCC(F)(F)CC2)c2cnccn2)N(C#N)C1] |
| 1300 | 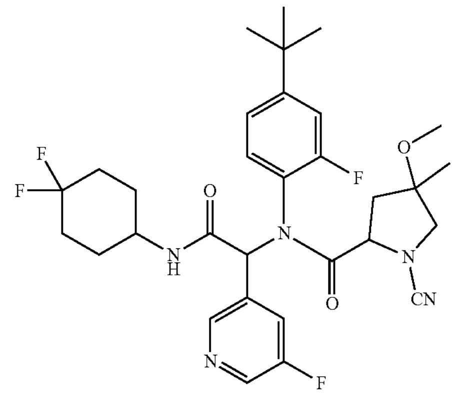 [SMILES: COC1(C)CC(C(=O)N(c2ccc(C(C)(C)C)cc2F)C(C(=O)NC2CCC(F)(F)CC2)c2cncc(F)c2)N(C#N)C1] |
| 1301 | 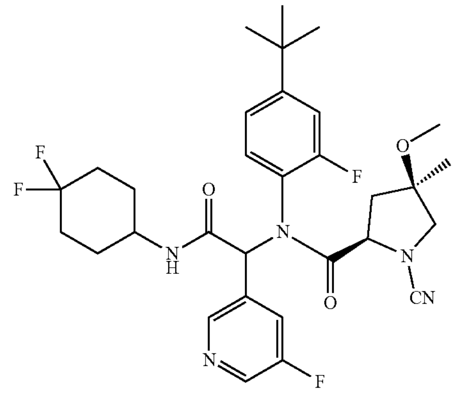 [SMILES: CO[C@]1(C)C[C@H](C(=O)N(c2ccc(C(C)(C)C)cc2F)C(C(=O)NC2CCC(F)(F)CC2)c2cncc(F)c2)N(C#N)C1] |
| 1302 | 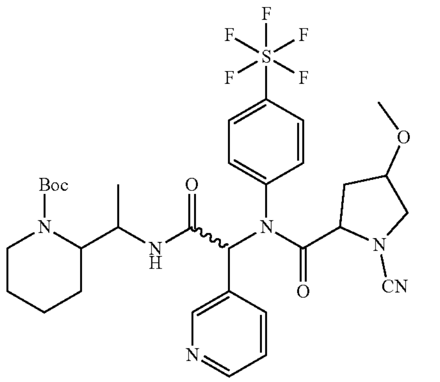 [SMILES: COC1CC(C(=O)N(c2ccc(S(F)(F)(F)(F)F)cc2)C(C(=O)NC(C)C2CCCCN2C(=O)OC(C)(C)C)c2cccnc2)N(C#N)C1] |
TABLE 1-continued
| Exemplary compounds. | |
|---|---|
| Cmpd No. | Structure |
| 1303 | 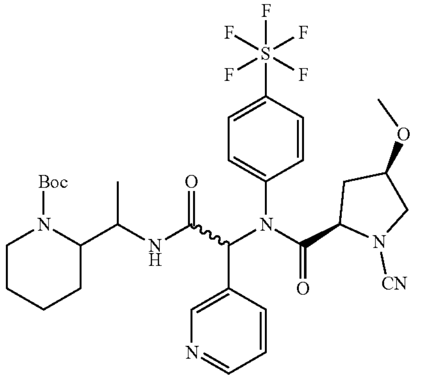 [SMILES: CO[C@@H]1C[C@H](C(=O)N(c2ccc(S(F)(F)(F)(F)F)cc2)C(C(=O)NC(C)C2CCCCN2C(=O)OC(C)(C)C)c2cccnc2)N(C#N)C1] |
| 1304 | 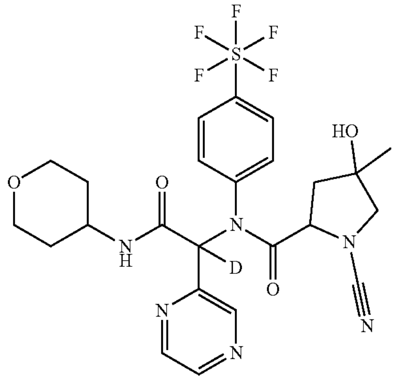 [SMILES: [2H]C(C(=O)NC1CCOCC1)(c1cnccn1)N(C(=O)C1CC(C)(O)CN1C#N)c1ccc(S(F)(F)(F)(F)F)cc1] |
| 1305 | 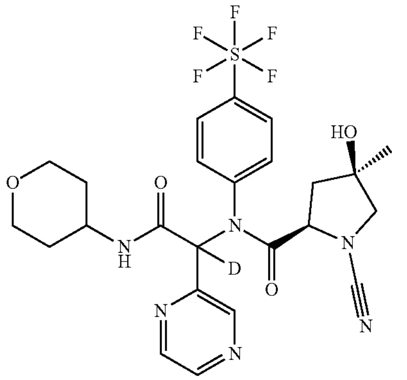 [SMILES: [2H]C(C(=O)NC1CCOCC1)(c1cnccn1)N(C(=O)[C@H]1C[C@@](C)(O)CN1C#N)c1ccc(S(F)(F)(F)(F)F)cc1] |
| 1306 | 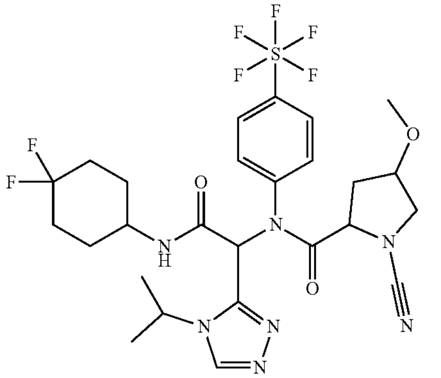 [SMILES: COC1CC(C(=O)N(c2ccc(S(F)(F)(F)(F)F)cc2)C(C(=O)NC2CCC(F)(F)CC2)c2nncn2C(C)C)N(C#N)C1] |

TABLE 1-continued
Exemplary compounds.
| Cmpd No. | Structure |
|---|---|
| 1307 | 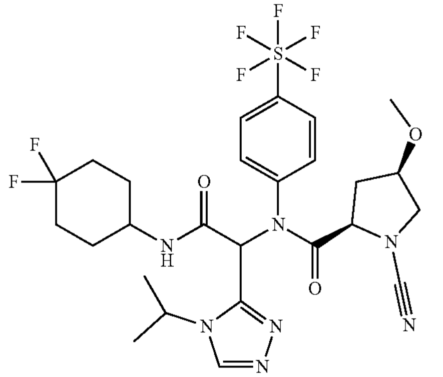 [SMILES: CO[C@@H]1C[C@H](C(=O)N(c2ccc(S(F)(F)(F)(F)F)cc2)C(C(=O)NC2CCC(F)(F)CC2)c2nncn2C(C)C)N(C#N)C1] |
| 1308 | 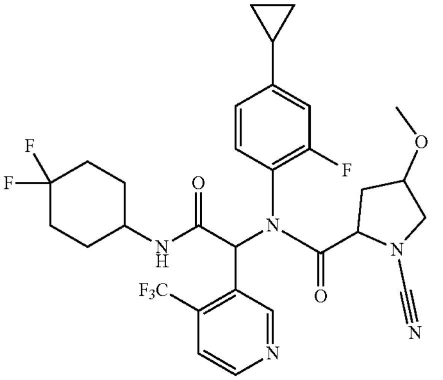 [SMILES: COC1CC(C(=O)N(c2ccc(C3CC3)cc2F)C(C(=O)NC2CCC(F)(F)CC2)c2cnccc2C(F)(F)F)N(C#N)C1] |
| 1309 | 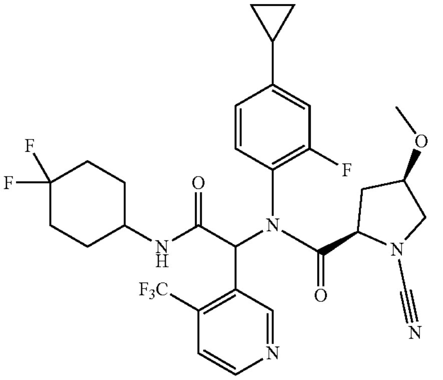 [SMILES: CO[C@@H]1C[C@H](C(=O)N(c2ccc(C3CC3)cc2F)C(C(=O)NC2CCC(F)(F)CC2)c2cnccc2C(F)(F)F)N(C#N)C1] |
| 1310 | 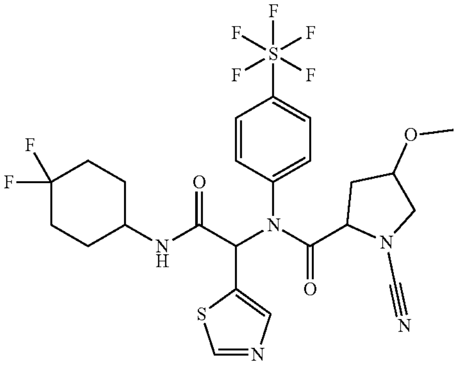 [SMILES: COC1CC(C(=O)N(c2ccc(S(F)(F)(F)(F)F)cc2)C(C(=O)NC2CCC(F)(F)CC2)c2cncs2)N(C#N)C1] |
| 1311 | 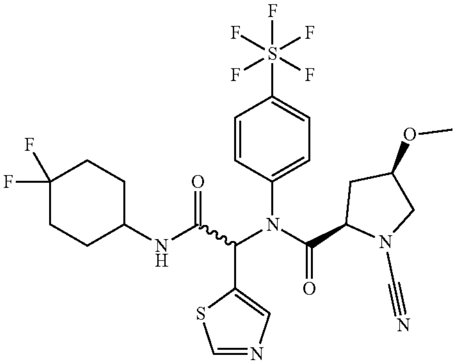 [SMILES: CO[C@@H]1C[C@H](C(=O)N(c2ccc(S(F)(F)(F)(F)F)cc2)C(C(=O)NC2CCC(F)(F)CC2)c2cncs2)N(C#N)C1] |
| 1312 | 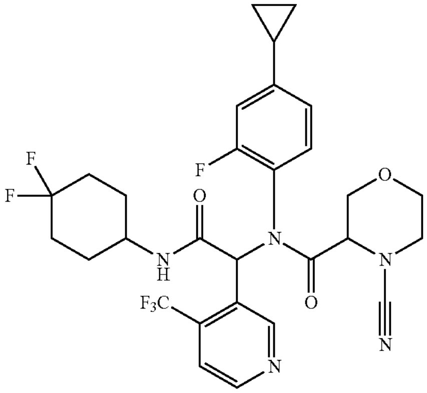 [SMILES: N#CN1CCOCC1C(=O)N(c1ccc(C2CC2)cc1F)C(C(=O)NC1CCC(F)(F)CC1)c1cnccc1C(F)(F)F] |
| 1313 | 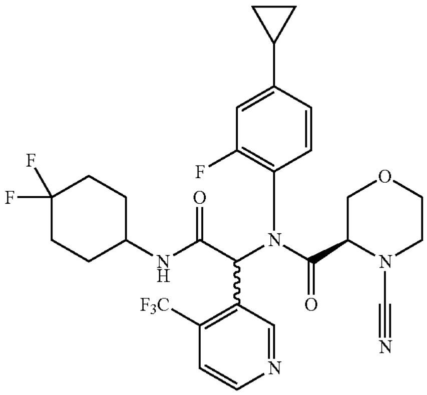 [SMILES: N#CN1CCOC[C@@H]1C(=O)N(c1ccc(C2CC2)cc1F)C(C(=O)NC1CCC(F)(F)CC1)c1cnccc1C(F)(F)F] |

TABLE 1-continued
Exemplary compounds.
| Cmpd No. | Structure |
|---|---|
| 1314 | 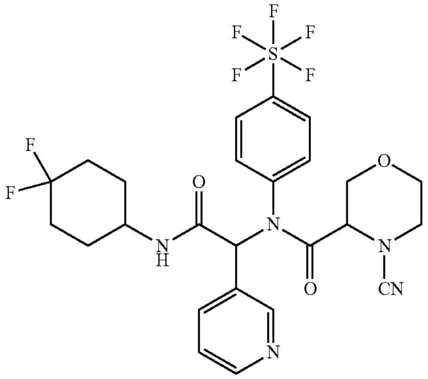 [SMILES: N#CN1CCOCC1C(=O)N(c1ccc(S(F)(F)(F)(F)F)cc1)C(C(=O)NC1CCC(F)(F)CC1)c1cccnc1] |
| 1315 | 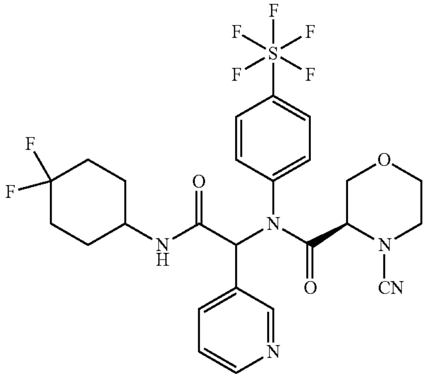 [SMILES: N#CN1CCOC[C@@H]1C(=O)N(c1ccc(S(F)(F)(F)(F)F)cc1)C(C(=O)NC1CCC(F)(F)CC1)c1cccnc1] |
| 1316 | 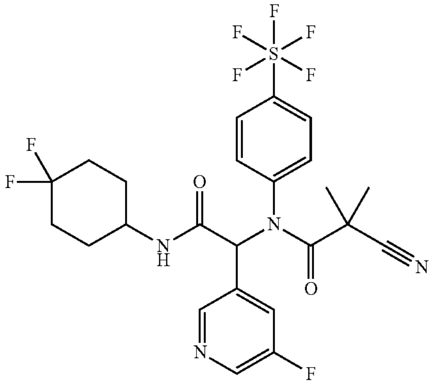 [SMILES: CC(C)(C#N)C(=O)N(c1ccc(S(F)(F)(F)(F)F)cc1)C(C(=O)NC1CCC(F)(F)CC1)c1cncc(F)c1] |
| 1317a | 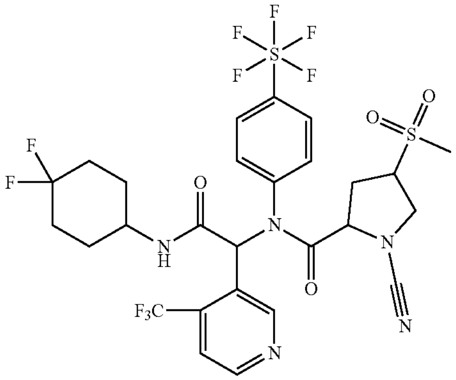 [SMILES: CS(=O)(=O)C1CC(C(=O)N(c2ccc(S(F)(F)(F)(F)F)cc2)C(C(=O)NC2CCC(F)(F)CC2)c2cnccc2C(F)(F)F)N(C#N)C1] |
TABLE 1-continued
Exemplary compounds.
| Cmpd No. | Structure |
|---|---|
| 1317b | 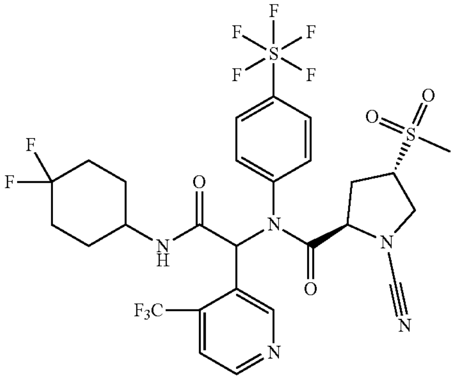 [SMILES: CS(=O)(=O)[C@H]1C[C@H](C(=O)N(c2ccc(S(F)(F)(F)(F)F)cc2)C(C(=O)NC2CCC(F)(F)CC2)c2cnccc2C(F)(F)F)N(C#N)C1] |
| 1317 | 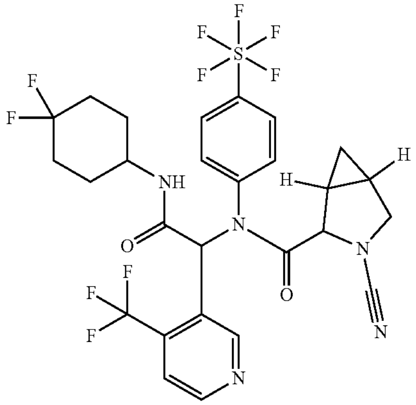 [SMILES: N#CN1CC2CC2C1C(=O)N(c1ccc(S(F)(F)(F)(F)F)cc1)C(C(=O)NC1CCC(F)(F)CC1)c1cnccc1C(F)(F)F] |
| 1318 | 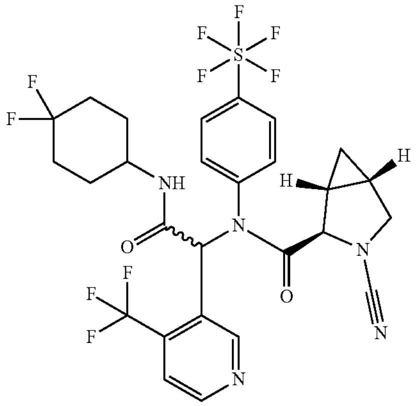 [SMILES: N#CN1C[C@H]2C[C@H]2[C@@H]1C(=O)N(c1ccc(S(F)(F)(F)(F)F)cc1)C(C(=O)NC1CCC(F)(F)CC1)c1cnccc1C(F)(F)F] |

TABLE 1-continued
Exemplary compounds.
| Cmpd No. | Structure |
|---|---|
| 1319 | 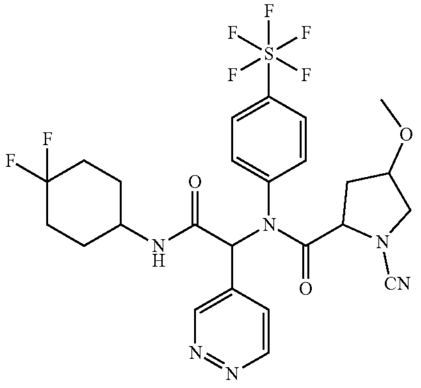 [SMILES: COC1CC(C(=O)N(c2ccc(S(F)(F)(F)(F)F)cc2)C(C(=O)NC2CCC(F)(F)CC2)c2ccnnc2)N(C#N)C1] |
| 1320 | 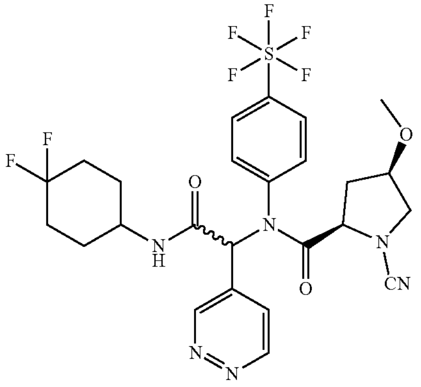 [SMILES: CO[C@@H]1C[C@H](C(=O)N(c2ccc(S(F)(F)(F)(F)F)cc2)C(C(=O)NC2CCC(F)(F)CC2)c2ccnnc2)N(C#N)C1] |
| 1321 | 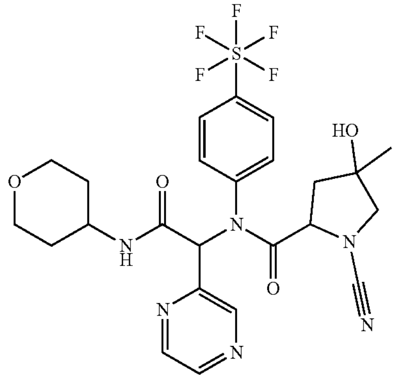 [SMILES: CC1(O)CC(C(=O)N(c2ccc(S(F)(F)(F)(F)F)cc2)C(C(=O)NC2CCOCC2)c2cnccn2)N(C#N)C1] |
| 1322 | 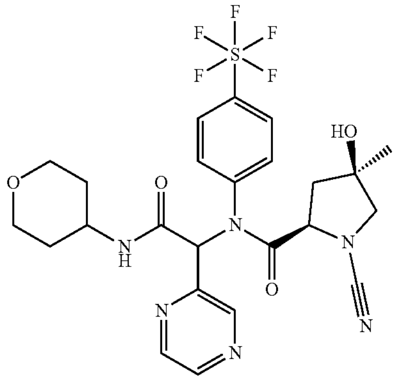 [SMILES: C[C@@]1(O)C[C@H](C(=O)N(c2ccc(S(F)(F)(F)(F)F)cc2)C(C(=O)NC2CCOCC2)c2cnccn2)N(C#N)C1] |
TABLE 1-continued
Exemplary compounds.
| Cmpd No. | Structure |
|---|---|
| 1323 | 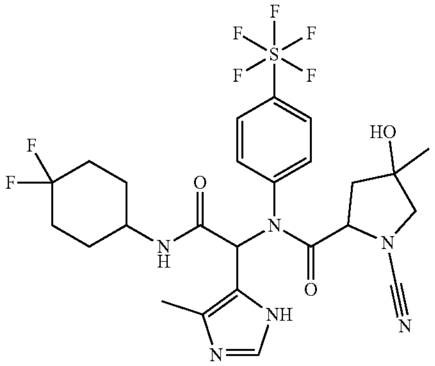 [SMILES: Cc1nc[nH]c1C(C(=O)NC1CCC(F)(F)CC1)N(C(=O)C1CC(C)(O)CN1C#N)c1ccc(S(F)(F)(F)(F)F)cc1] |
| 1324 | 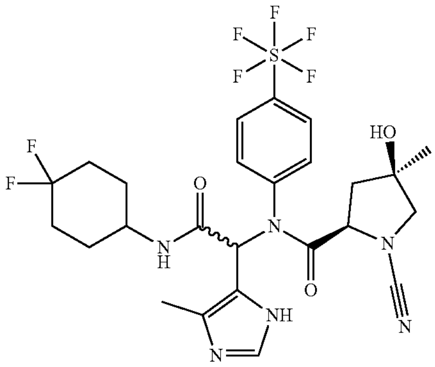 [SMILES: Cc1nc[nH]c1C(C(=O)NC1CCC(F)(F)CC1)N(C(=O)[C@H]1C[C@@](C)(O)CN1C#N)c1ccc(S(F)(F)(F)(F)F)cc1] |
| 1325 | 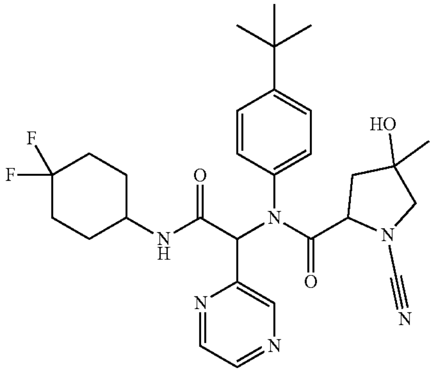 [SMILES: CC1(O)CC(C(=O)N(c2ccc(C(C)(C)C)cc2)C(C(=O)NC2CCC(F)(F)CC2)c2cnccn2)N(C#N)C1] |
| 1326 | 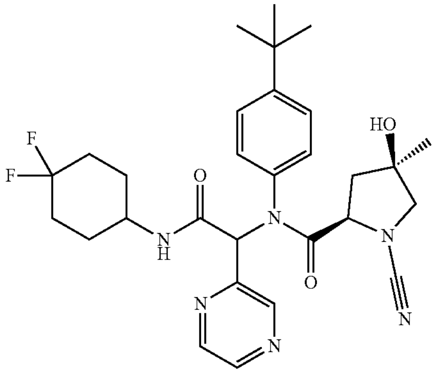 [SMILES: CC(C)(C)c1ccc(N(C(=O)[C@H]2C[C@@](C)(O)CN2C#N)C(C(=O)NC2CCC(F)(F)CC2)c2cnccn2)cc1] |

TABLE 1-continued
Exemplary compounds.
| Cmpd No. | Structure |
|---|---|
| 1327 | 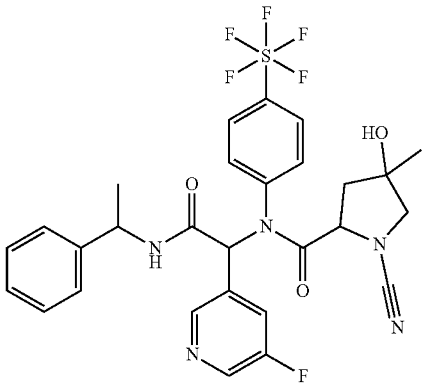 [SMILES: CC(NC(=O)C(c1cncc(F)c1)N(C(=O)C1CC(C)(O)CN1C#N)c1ccc(S(F)(F)(F)(F)F)cc1)c1ccccc1] |
| 1328 | 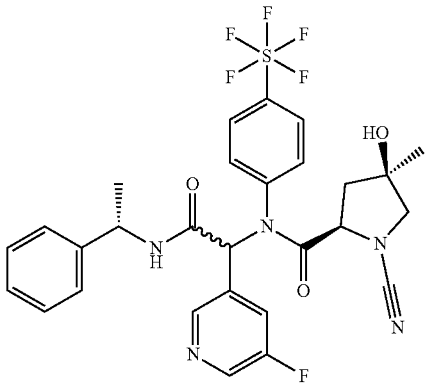 [SMILES: C[C@H](NC(=O)C(c1cncc(F)c1)N(C(=O)[C@H]1C[C@@](C)(O)CN1C#N)c1ccc(S(F)(F)(F)(F)F)cc1)c1ccccc1] |
| 1329 | 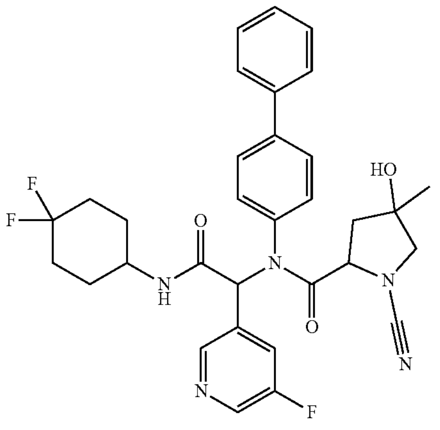 [SMILES: CC1(O)CC(C(=O)N(c2ccc(-c3ccccc3)cc2)C(C(=O)NC2CCC(F)(F)CC2)c2cncc(F)c2)N(C#N)C1] |
TABLE 1-continued
Exemplary compounds.
| Cmpd No. | Structure |
|---|---|
| 1330 | 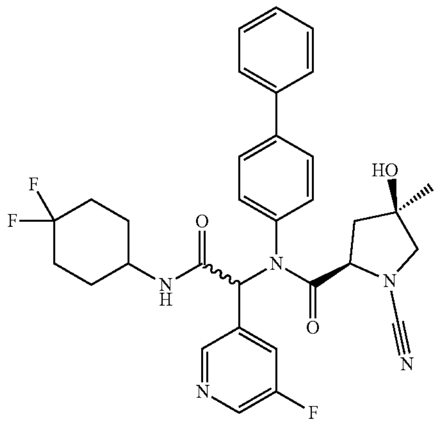 [SMILES: C[C@@]1(O)C[C@H](C(=O)N(c2ccc(-c3ccccc3)cc2)C(C(=O)NC2CCC(F)(F)CC2)c2cncc(F)c2)N(C#N)C1] |
| 1331 | 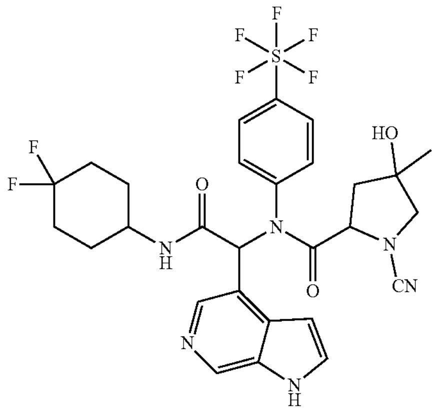 [SMILES: CC1(O)CC(C(=O)N(c2ccc(S(F)(F)(F)(F)F)cc2)C(C(=O)NC2CCC(F)(F)CC2)c2cncc3[nH]ccc23)N(C#N)C1] |
| 1332 | 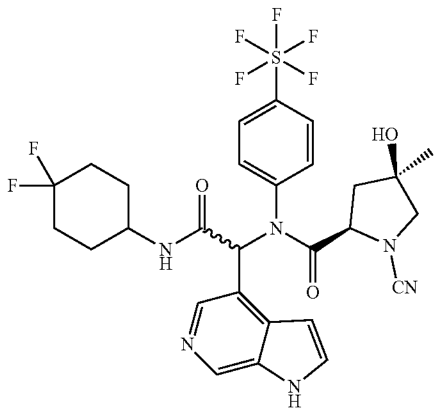 [SMILES: C[C@@]1(O)C[C@H](C(=O)N(c2ccc(S(F)(F)(F)(F)F)cc2)C(C(=O)NC2CCC(F)(F)CC2)c2cncc3[nH]ccc23)N(C#N)C1] |

TABLE 1-continued
| Exemplary compounds. | |
|---|---|
| Cmpd No. | Structure |
| 1333 | 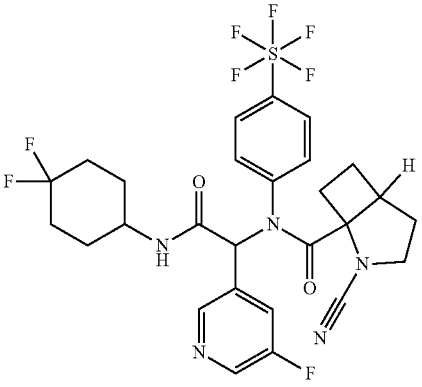 [SMILES: N#CN1CCC2CCC21C(=O)N(c1ccc(S(F)(F)(F)(F)F)cc1)C(C(=O)NC1CCC(F)(F)CC1)c1cncc(F)c1] |
| 1334 | 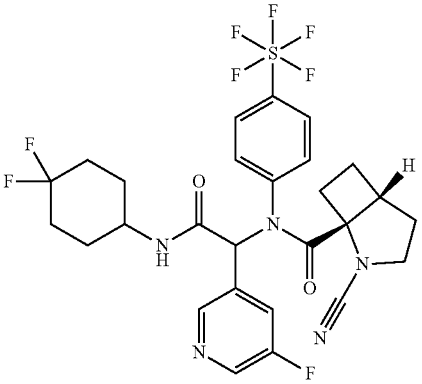 [SMILES: N#CN1CC[C@H]2CC[C@]21C(=O)N(c1ccc(S(F)(F)(F)(F)F)cc1)C(C(=O)NC1CCC(F)(F)CC1)c1cncc(F)c1] |
| 1335 | 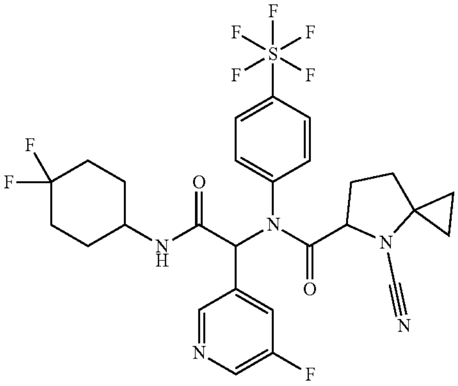 [SMILES: N#CN1C(C(=O)N(c2ccc(S(F)(F)(F)(F)F)cc2)C(C(=O)NC2CCC(F)(F)CC2)c2cncc(F)c2)CCC12CC2] |
| 1336 | 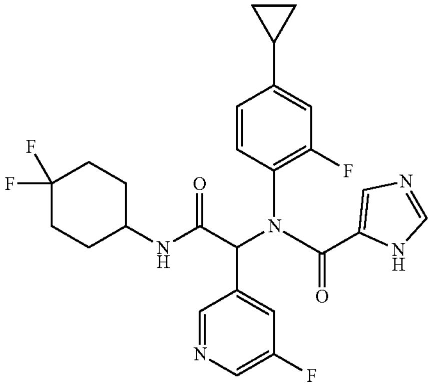 [SMILES: O=C(NC1CCC(F)(F)CC1)C(c1cncc(F)c1)N(C(=O)c1cnc[nH]1)c1ccc(C2CC2)cc1F] |
TABLE 1-continued
| Exemplary compounds. | |
|---|---|
| Cmpd No. | Structure |
| 1337 | 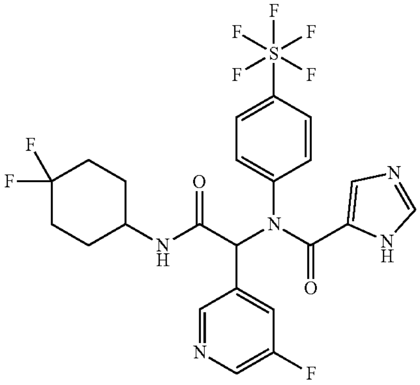 [SMILES: O=C(NC1CCC(F)(F)CC1)C(c1cncc(F)c1)N(C(=O)c1cnc[nH]1)c1ccc(S(F)(F)(F)(F)F)cc1] |
| 1338 | 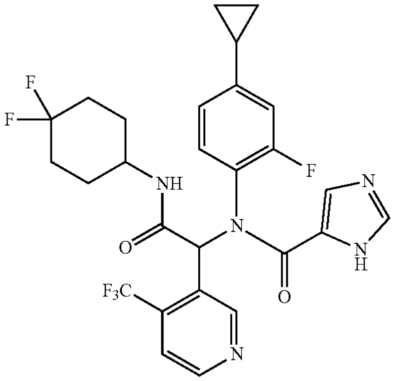 [SMILES: O=C(NC1CCC(F)(F)CC1)C(c1cnccc1C(F)(F)F)N(C(=O)c1cnc[nH]1)c1ccc(C2CC2)cc1F] |
| 1339 | 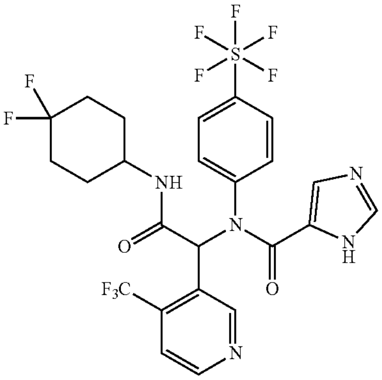 [SMILES: O=C(NC1CCC(F)(F)CC1)C(c1cnccc1C(F)(F)F)N(C(=O)c1cnc[nH]1)c1ccc(S(F)(F)(F)(F)F)cc1] |

TABLE 1-continued
| Exemplary compounds. | |
|---|---|
| Cmpd No. | Structure |
| 1344 | 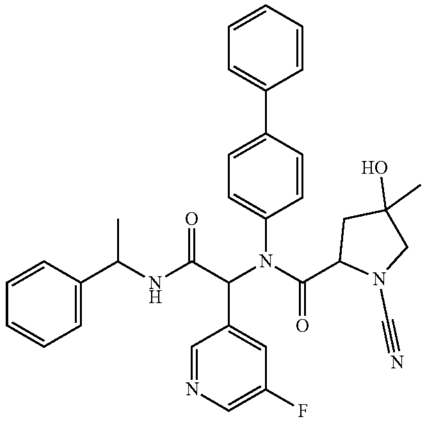 [SMILES: CC(NC(=O)C(c1cncc(F)c1)N(C(=O)C1CC(C)(O)CN1C#N)c1ccc(-c2ccccc2)cc1)c1ccccc1] |
| 1345 | 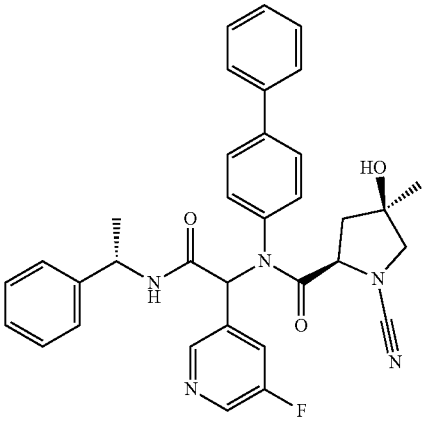 [SMILES: C[C@H](NC(=O)C(c1cncc(F)c1)N(C(=O)[C@H]1C[C@@](C)(O)CN1C#N)c1ccc(-c2ccccc2)cc1)c1ccccc1] |
| 1346 | 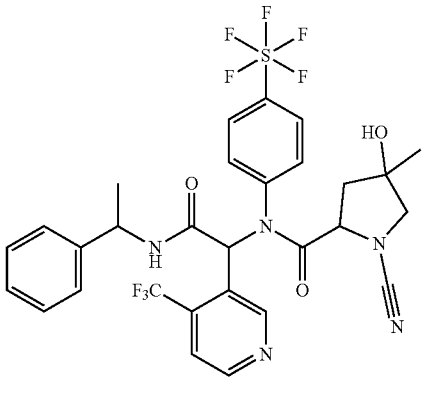 [SMILES: CC(NC(=O)C(c1cnccc1C(F)(F)F)N(C(=O)C1CC(C)(O)CN1C#N)c1ccc(S(F)(F)(F)(F)F)cc1)c1ccccc1] |
TABLE 1-continued
| Exemplary compounds. | |
|---|---|
| Cmpd No. | Structure |
| 1347 | 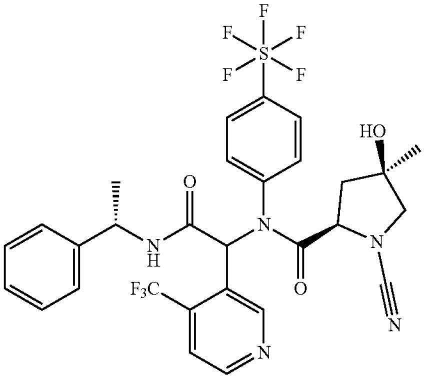 [SMILES: C[C@H](NC(=O)C(c1cnccc1C(F)(F)F)N(C(=O)[C@H]1C[C@@](C)(O)CN1C#N)c1ccc(S(F)(F)(F)(F)F)cc1)c1ccccc1] |
| 1348 | 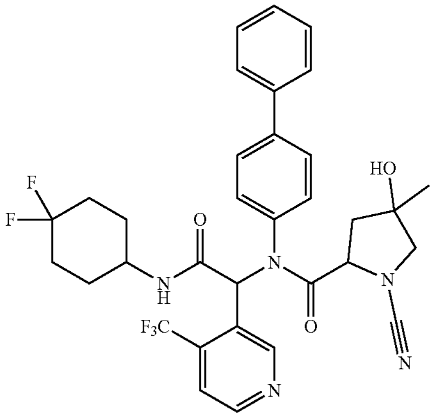 [SMILES: CC1(O)CC(C(=O)N(c2ccc(-c3ccccc3)cc2)C(C(=O)NC2CCC(F)(F)CC2)c2cnccc2C(F)(F)F)N(C#N)C1] |
| 1349 | 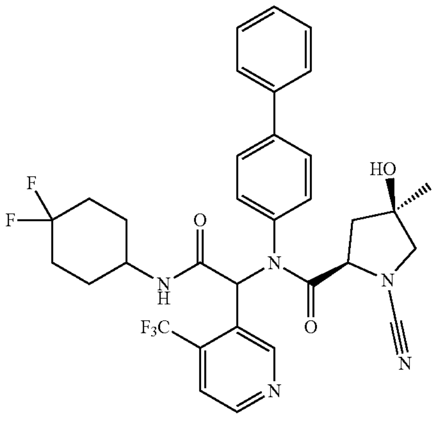 [SMILES: C[C@@]1(O)C[C@H](C(=O)N(c2ccc(-c3ccccc3)cc2)C(C(=O)NC2CCC(F)(F)CC2)c2cnccc2C(F)(F)F)N(C#N)C1] |

TABLE 1-continued
| Exemplary compounds. | |
|---|---|
| Cmpd No. | Structure |
| 1350 | 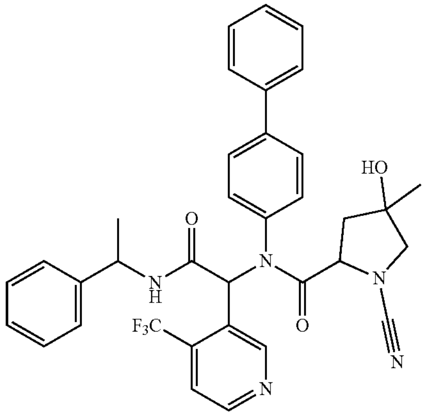 [SMILES: CC(NC(=O)C(c1cnccc1C(F)(F)F)N(C(=O)C1CC(C)(O)CN1C#N)c1ccc(-c2ccccc2)cc1)c1ccccc1] |
| 1351 | 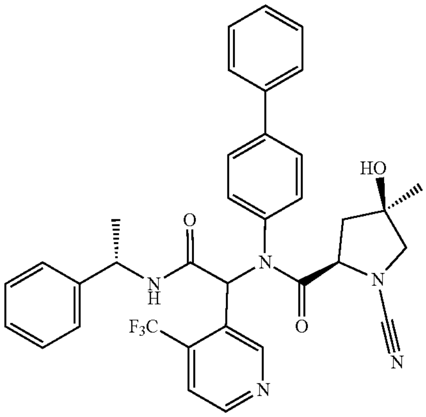 [SMILES: C[C@H](NC(=O)C(c1cnccc1C(F)(F)F)N(C(=O)[C@H]1C[C@@](C)(O)CN1C#N)c1ccc(-c2ccccc2)cc1)c1ccccc1] |
| 1352 | 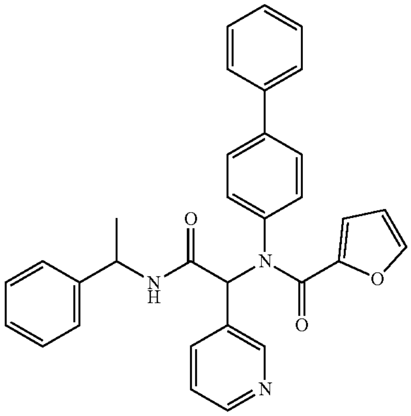 [SMILES: CC(NC(=O)C(c1cccnc1)N(C(=O)c1ccco1)c1ccc(-c2ccccc2)cc1)c1ccccc1] |
TABLE 1-continued
| Exemplary compounds. | |
|---|---|
| Cmpd No. | Structure |
| 1353 | 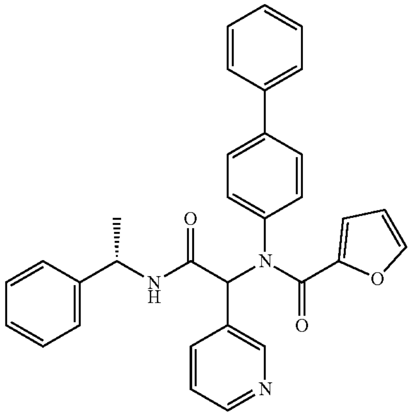 [SMILES: C[C@H](NC(=O)C(c1cccnc1)N(C(=O)c1ccco1)c1ccc(-c2ccccc2)cc1)c1ccccc1] |
| 1354 | 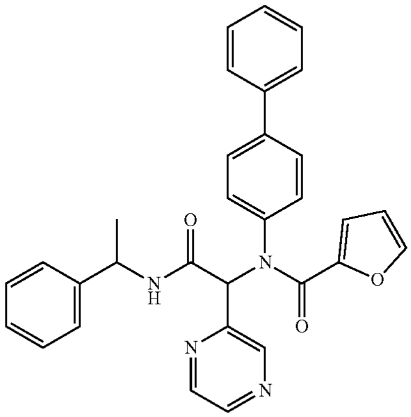 [SMILES: CC(NC(=O)C(c1cnccn1)N(C(=O)c1ccco1)c1ccc(-c2ccccc2)cc1)c1ccccc1] |
| 1355 | 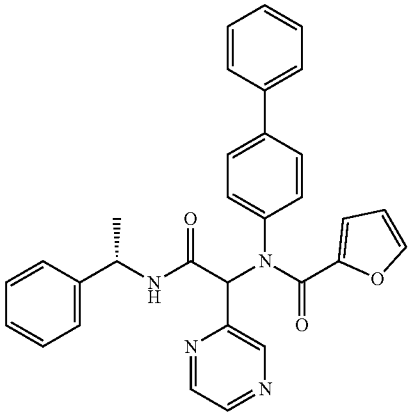 [SMILES: C[C@H](NC(=O)C(c1cnccn1)N(C(=O)c1ccco1)c1ccc(-c2ccccc2)cc1)c1ccccc1] |

TABLE 1-continued
| Exemplary compounds. | |
|---|---|
| Cmpd No. | Structure |
| 1356 | 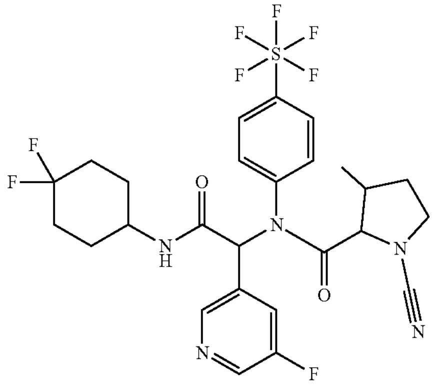 [SMILES: CC1CCN(C#N)C1C(=O)N(c1ccc(S(F)(F)(F)(F)F)cc1)C(C(=O)NC1CCC(F)(F)CC1)c1cncc(F)c1] |
| 1357 | 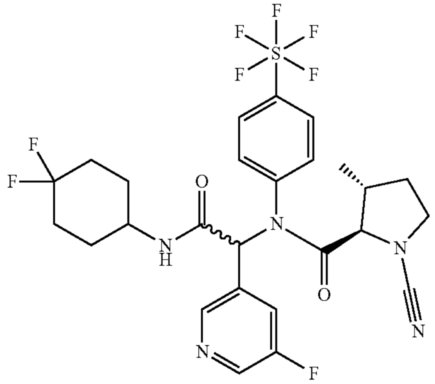 [SMILES: C[C@@H]1CCN(C#N)[C@H]1C(=O)N(c1ccc(S(F)(F)(F)(F)F)cc1)C(C(=O)NC1CCC(F)(F)CC1)c1cncc(F)c1] |
| 1358 | 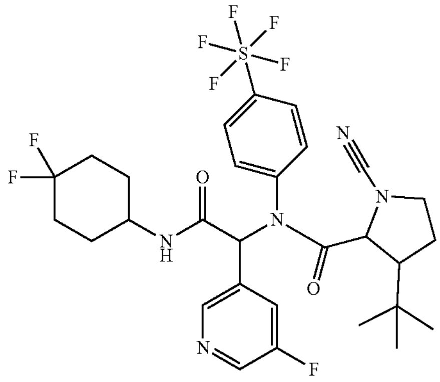 [SMILES: CC(C)(C)C1CCN(C#N)C1C(=O)N(c1ccc(S(F)(F)(F)(F)F)cc1)C(C(=O)NC1CCC(F)(F)CC1)c1cncc(F)c1] |
| 1359 | 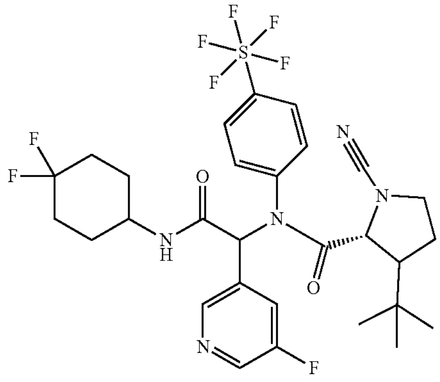 [SMILES: CC(C)(C)C1CCN(C#N)[C@H]1C(=O)N(c1ccc(S(F)(F)(F)(F)F)cc1)C(C(=O)NC1CCC(F)(F)CC1)c1cncc(F)c1] |
TABLE 1-continued
| Exemplary compounds. | |
|---|---|
| Cmpd No. | Structure |
| 1360 | 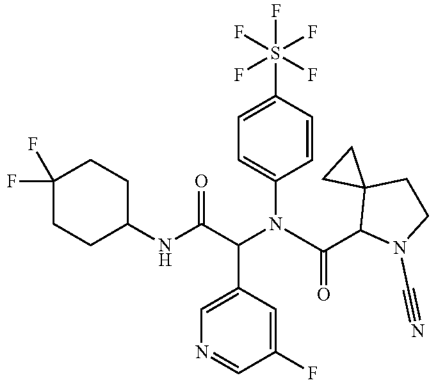 [SMILES: N#CN1CCC2(CC2)C1C(=O)N(c1ccc(S(F)(F)(F)(F)F)cc1)C(C(=O)NC1CCC(F)(F)CC1)c1cncc(F)c1] |
| 1361 | 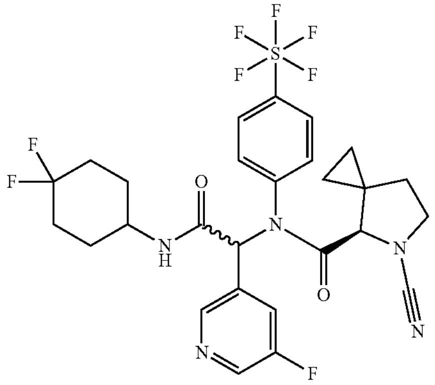 [SMILES: N#CN1CCC2(CC2)[C@@H]1C(=O)N(c1ccc(S(F)(F)(F)(F)F)cc1)C(C(=O)NC1CCC(F)(F)CC1)c1cncc(F)c1] |
| 1362 | 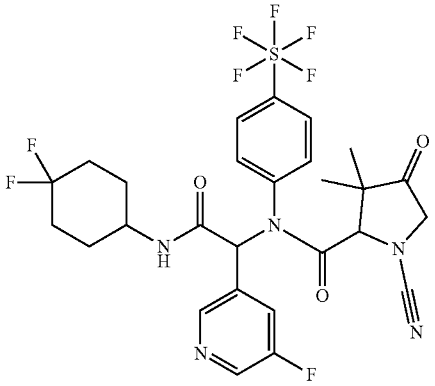 [SMILES: CC1(C)C(=O)CN(C#N)C1C(=O)N(c1ccc(S(F)(F)(F)(F)F)cc1)C(C(=O)NC1CCC(F)(F)CC1)c1cncc(F)c1] |
| 1363 | 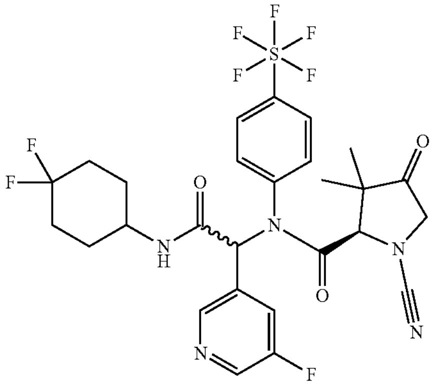 [SMILES: CC1(C)C(=O)CN(C#N)[C@H]1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1364 | 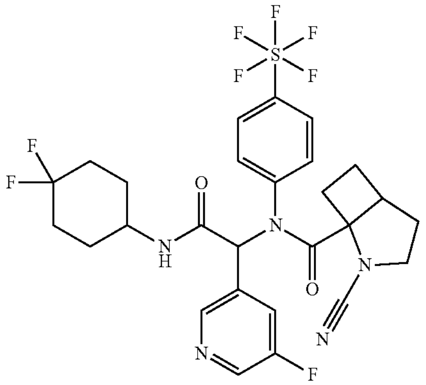 [SMILES: N#CN1CCC2CCC21C(=O)N(c1ccc(S(F)(F)(F)(F)F)cc1)C(C(=O)NC1CCC(F)(F)CC1)c1cncc(F)c1] |
| 1365 | 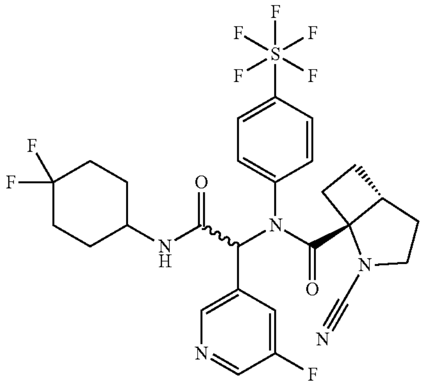 [SMILES: N#CN1CC[C@H]2CC[C@]21C(=O)N(c1ccc(S(F)(F)(F)(F)F)cc1)C(C(=O)NC1CCC(F)(F)CC1)c1cncc(F)c1] |
| 1366 | 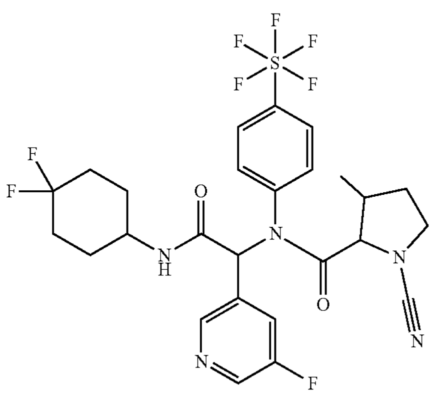 [SMILES: CC1CCN(C#N)C1C(=O)N(c1ccc(S(F)(F)(F)(F)F)cc1)C(C(=O)NC1CCC(F)(F)CC1)c1cncc(F)c1] |
| 1367 | 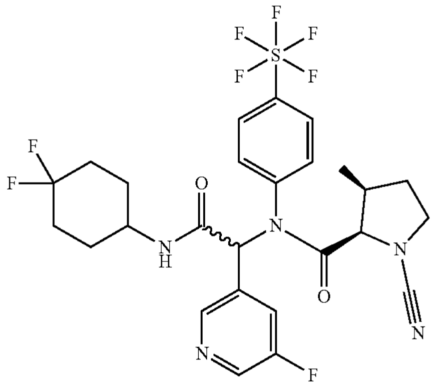 [SMILES: C[C@H]1CCN(C#N)[C@H]1C(=O)N(c1ccc(S(F)(F)(F)(F)F)cc1)C(C(=O)NC1CCC(F)(F)CC1)c1cncc(F)c1] |
| 1368 | 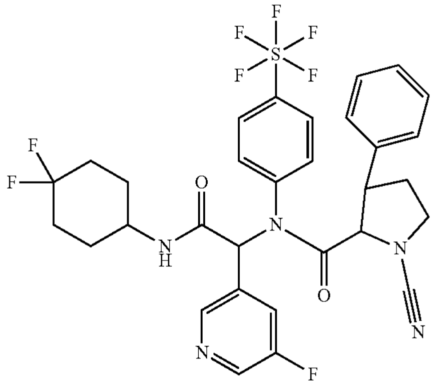 [SMILES: N#CN1CCC(c2ccccc2)C1C(=O)N(c1ccc(S(F)(F)(F)(F)F)cc1)C(C(=O)NC1CCC(F)(F)CC1)c1cncc(F)c1] |
| 1369 | 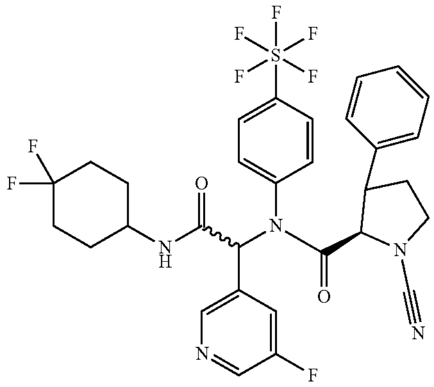 [SMILES: N#CN1CCC(c2ccccc2)[C@@H]1C(=O)N(c1ccc(S(F)(F)(F)(F)F)cc1)C(C(=O)NC1CCC(F)(F)CC1)c1cncc(F)c1] |
| 1370 | 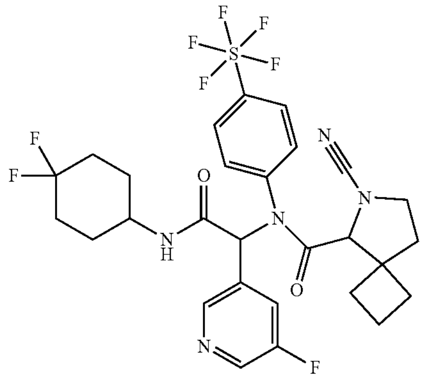 [SMILES: N#CN1CCC2(CCC2)C1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1371 | 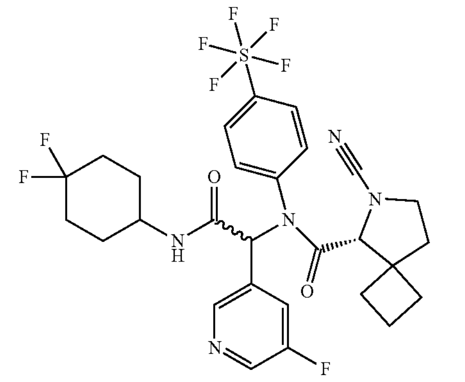 [SMILES: N#CN1CCC2(CCC2)[C@@H]1C(=O)N(c1ccc(S(F)(F)(F)(F)F)cc1)C(C(=O)NC1CCC(F)(F)CC1)c1cncc(F)c1] |
| 1372 | 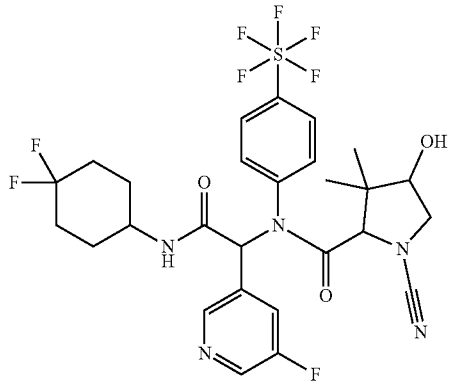 [SMILES: CC1(C)C(O)CN(C#N)C1C(=O)N(c1ccc(S(F)(F)(F)(F)F)cc1)C(C(=O)NC1CCC(F)(F)CC1)c1cncc(F)c1] |
| 1373 | 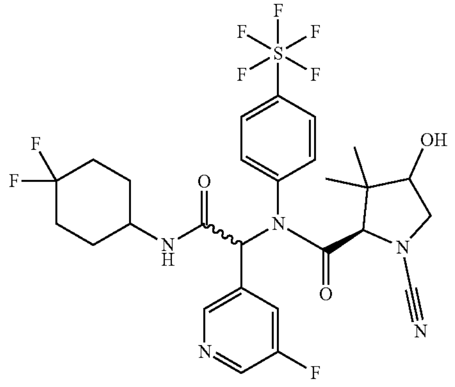 [SMILES: CC1(C)C(O)CN(C#N)[C@H]1C(=O)N(c1ccc(S(F)(F)(F)(F)F)cc1)C(C(=O)NC1CCC(F)(F)CC1)c1cncc(F)c1] |
| 1374 | 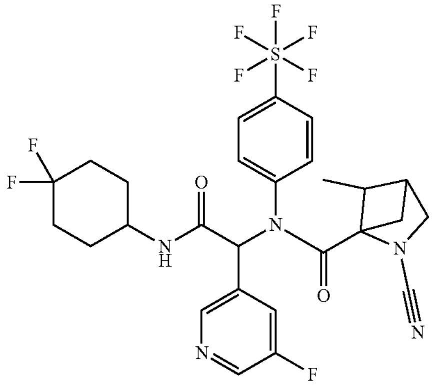 [SMILES: CC1C2CN(C#N)C1(C(=O)N(c1ccc(S(F)(F)(F)(F)F)cc1)C(C(=O)NC1CCC(F)(F)CC1)c1cncc(F)c1)C2] |
| 1375 | 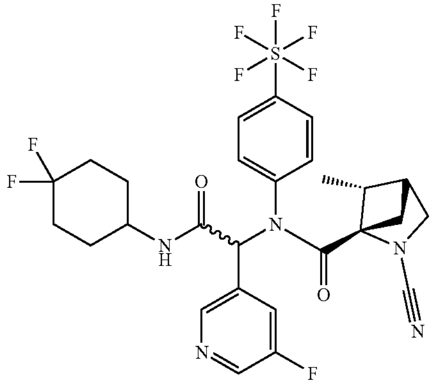 |
| 1376 | 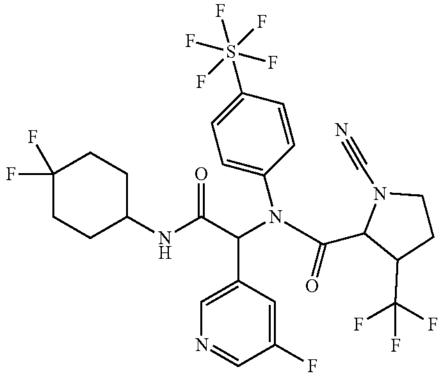 [SMILES: N#CN1CCC(C(F)(F)F)C1C(=O)N(c1ccc(S(F)(F)(F)(F)F)cc1)C(C(=O)NC1CCC(F)(F)CC1)c1cncc(F)c1] |
| 1377 | 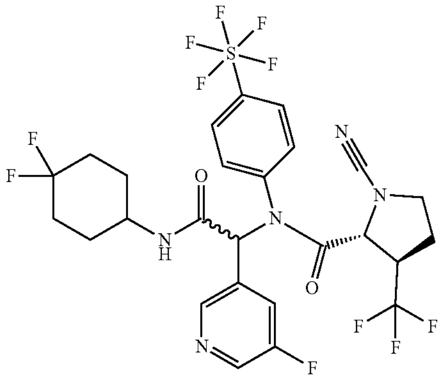 [SMILES: N#CN1CC[C@@H](C(F)(F)F)[C@@H]1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1378 | 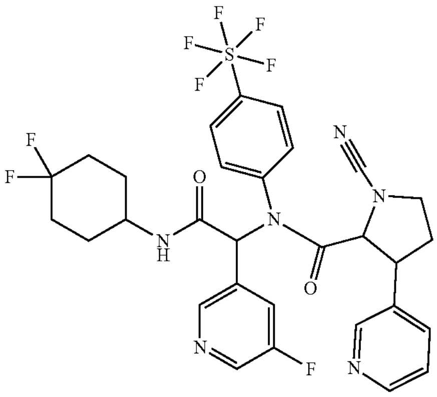 [SMILES: N#CN1CCC(c2cccnc2)C1C(=O)N(c1ccc(S(F)(F)(F)(F)F)cc1)C(C(=O)NC1CCC(F)(F)CC1)c1cncc(F)c1] |
| 1379 | 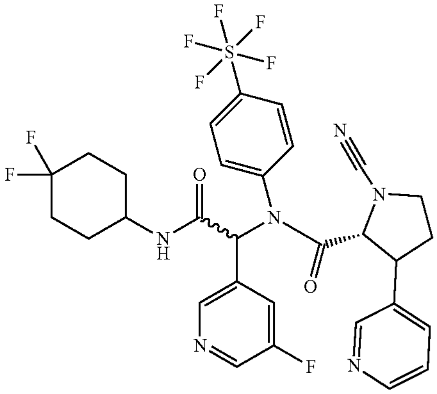 [SMILES: N#CN1CCC(c2cccnc2)[C@@H]1C(=O)N(c1ccc(S(F)(F)(F)(F)F)cc1)C(C(=O)NC1CCC(F)(F)CC1)c1cncc(F)c1] |
| 1380 | 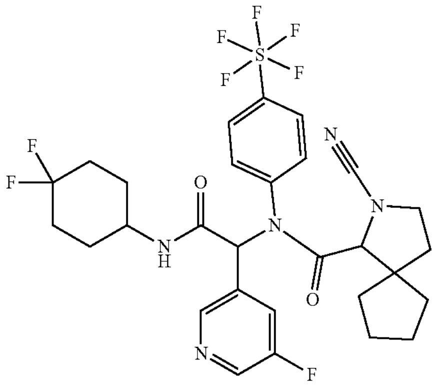 [SMILES: N#CN1CCC2(CCCC2)C1C(=O)N(c1ccc(S(F)(F)(F)(F)F)cc1)C(C(=O)NC1CCC(F)(F)CC1)c1cncc(F)c1] |
| 1381 | 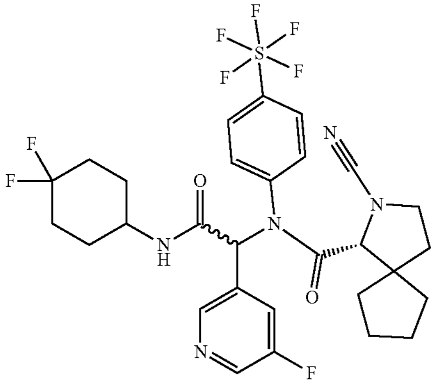 [SMILES: N#CN1CCC2(CCCC2)[C@@H]1C(=O)N(c1ccc(S(F)(F)(F)(F)F)cc1)C(C(=O)NC1CCC(F)(F)CC1)c1cncc(F)c1] |
| 1382 | 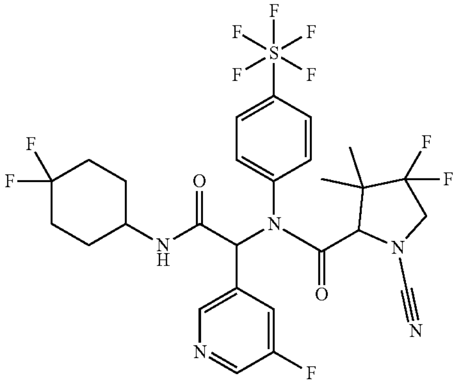 [SMILES: CC1(C)C(C(=O)N(c2ccc(S(F)(F)(F)(F)F)cc2)C(C(=O)NC2CCC(F)(F)CC2)c2cncc(F)c2)N(C#N)CC1(F)F] |
| 1383 | 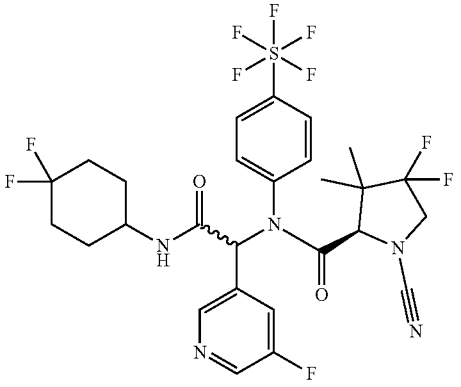 [SMILES: CC1(C)[C@H](C(=O)N(c2ccc(S(F)(F)(F)(F)F)cc2)C(C(=O)NC2CCC(F)(F)CC2)c2cncc(F)c2)N(C#N)CC1(F)F] |
| 1384 | 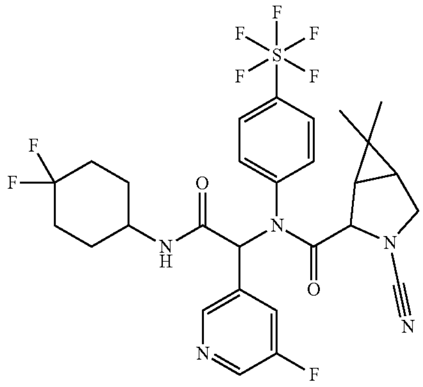 [SMILES: CC1(C)C2CN(C#N)C(C(=O)N(c3ccc(S(F)(F)(F)(F)F)cc3)C(C(=O)NC3CCC(F)(F)CC3)c3cncc(F)c3)C21] |

TABLE 1-continued
Exemplary compounds.
| Cmpd No. | Structure |
|---|---|
| 1385 | 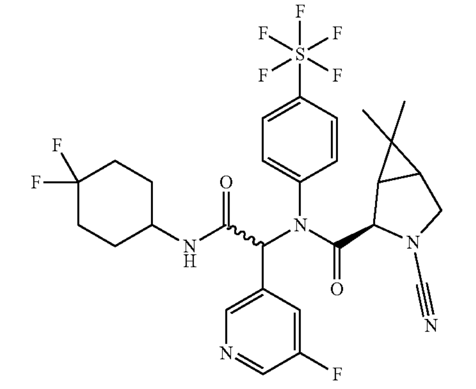 [SMILES: CC1(C)C2CN(C#N)[C@@H](C(=O)N(c3ccc(S(F)(F)(F)(F)F)cc3)C(C(=O)NC3CCC(F)(F)CC3)c3cncc(F)c3)C21] |
| 1386 | 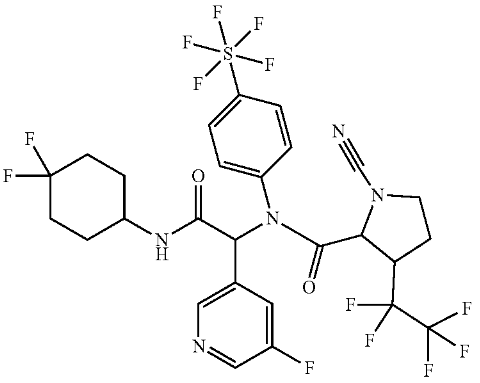 [SMILES: N#CN1CCC(C(F)(F)C(F)(F)F)C1C(=O)N(c1ccc(S(F)(F)(F)(F)F)cc1)C(C(=O)NC1CCC(F)(F)CC1)c1cncc(F)c1] |
| 1387 | 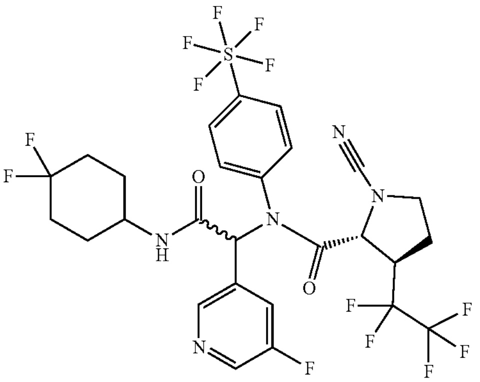 [SMILES: N#CN1CC[C@@H](C(F)(F)C(F)(F)F)[C@@H]1C(=O)N(c1ccc(S(F)(F)(F)(F)F)cc1)C(C(=O)NC1CCC(F)(F)CC1)c1cncc(F)c1] |
| 1388 | 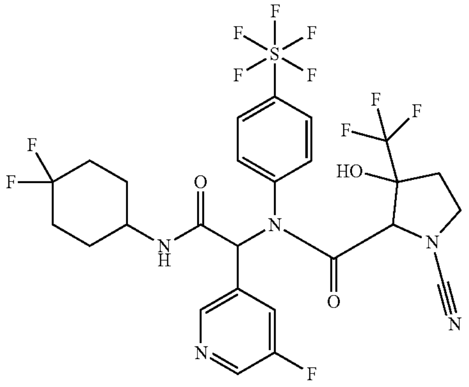 [SMILES: N#CN1CCC(O)(C(F)(F)F)C1C(=O)N(c1ccc(S(F)(F)(F)(F)F)cc1)C(C(=O)NC1CCC(F)(F)CC1)c1cncc(F)c1] |
| 1389 | 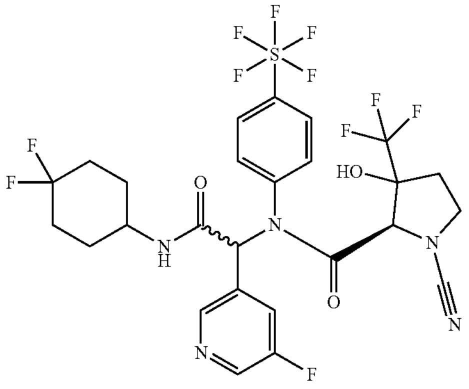 [SMILES: N#CN1CCC(O)(C(F)(F)F)[C@@H]1C(=O)N(c1ccc(S(F)(F)(F)(F)F)cc1)C(C(=O)NC1CCC(F)(F)CC1)c1cncc(F)c1] |
| 1390 | 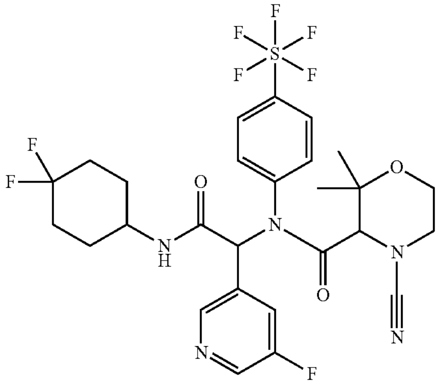 [SMILES: CC1(C)OCCN(C#N)C1C(=O)N(c1ccc(S(F)(F)(F)(F)F)cc1)C(C(=O)NC1CCC(F)(F)CC1)c1cncc(F)c1] |
| 1391 | 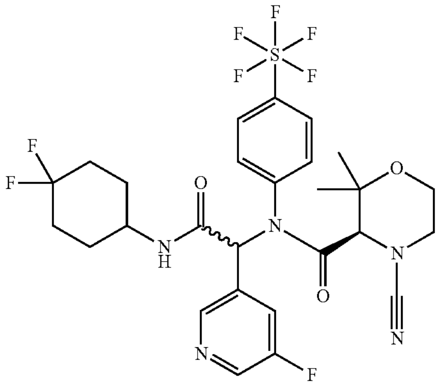 [SMILES: CC1(C)OCCN(C#N)[C@H]1C(=O)N(c1ccc(S(F)(F)(F)(F)F)cc1)C(C(=O)NC1CCC(F)(F)CC1)c1cncc(F)c1] |

TABLE 1-continued
| Exemplary compounds. | |
|---|---|
| Cmpd No. | Structure |
| 1403 | 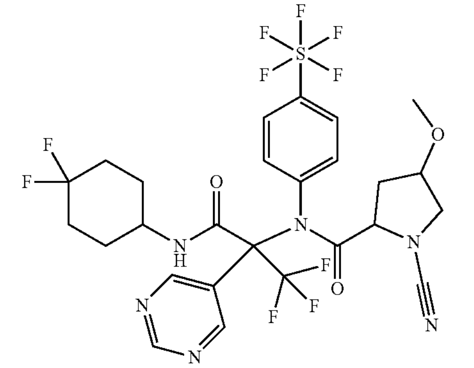 [SMILES: COC1CC(C(=O)N(c2ccc(S(F)(F)(F)(F)F)cc2)C(C(=O)NC2CCC(F)(F)CC2)(c2cncnc2)C(F)(F)F)N(C#N)C1] |
| 1404 | 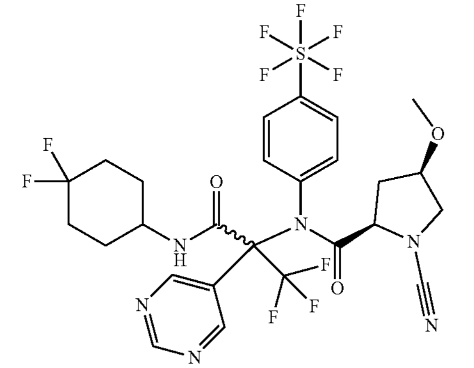 [SMILES: CO[C@@H]1C[C@H](C(=O)N(c2ccc(S(F)(F)(F)(F)F)cc2)C(C(=O)NC2CCC(F)(F)CC2)(c2cncnc2)C(F)(F)F)N(C#N)C1] |
| 1405 | 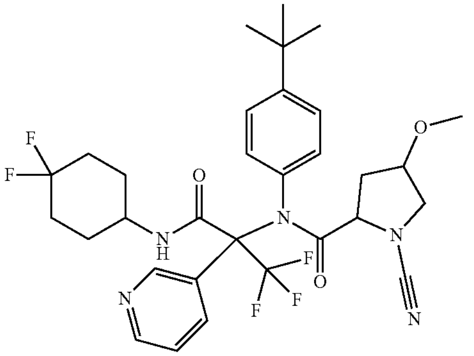 [SMILES: COC1CC(C(=O)N(c2ccc(C(C)(C)C)cc2)C(C(=O)NC2CCC(F)(F)CC2)(c2cccnc2)C(F)(F)F)N(C#N)C1] |
| 1406 | 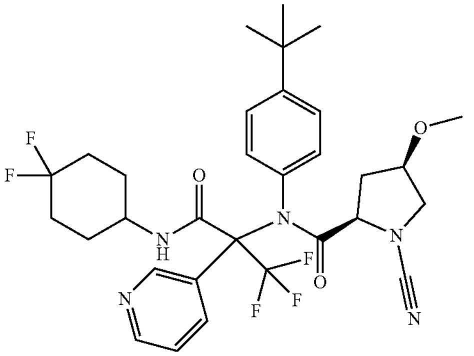 [SMILES: CO[C@@H]1C[C@H](C(=O)N(c2ccc(C(C)(C)C)cc2)C(C(=O)NC2CCC(F)(F)CC2)(c2cccnc2)C(F)(F)F)N(C#N)C1] |
TABLE 1-continued
| Exemplary compounds. | |
|---|---|
| Cmpd No. | Structure |
| 1407 | 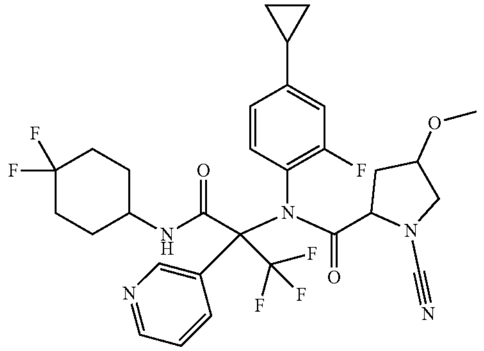 [SMILES: COC1CC(C(=O)N(c2ccc(C3CC3)cc2F)C(C(=O)NC2CCC(F)(F)CC2)(c2cccnc2)C(F)(F)F)N(C#N)C1] |
| 1408 | 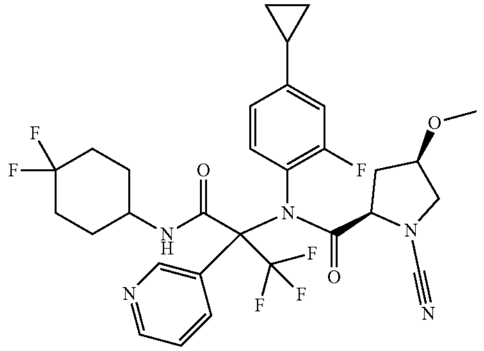 [SMILES: CO[C@@H]1C[C@H](C(=O)N(c2ccc(C3CC3)cc2F)C(C(=O)NC2CCC(F)(F)CC2)(c2cccnc2)C(F)(F)F)N(C#N)C1] |
| 1409 | 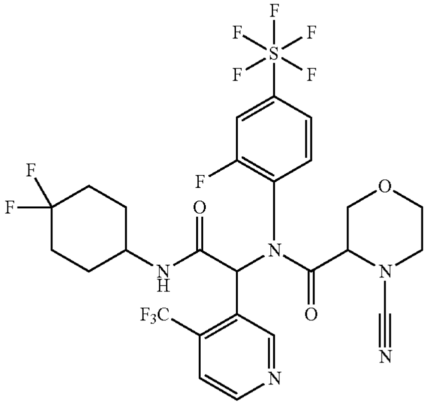 [SMILES: N#CN1CCOCC1C(=O)N(c1ccc(S(F)(F)(F)(F)F)cc1F)C(C(=O)NC1CCC(F)(F)CC1)c1cnccc1C(F)(F)F] |
| 1410 | 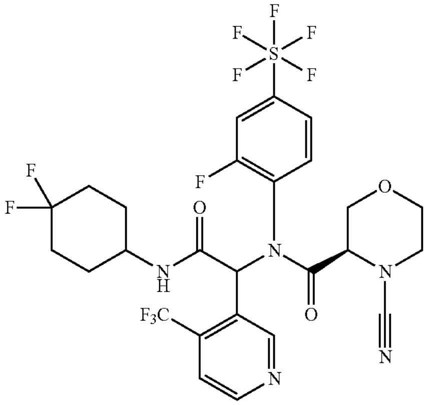 [SMILES: N#CN1CCOC[C@@H]1C(=O)N(c1ccc(S(F)(F)(F)(F)F)cc1F)C(C(=O)NC1CCC(F)(F)CC1)c1cnccc1C(F)(F)F] |

TABLE 1-continued
| Exemplary compounds. | |
|---|---|
| Cmpd No. | Structure |
| 1411 | 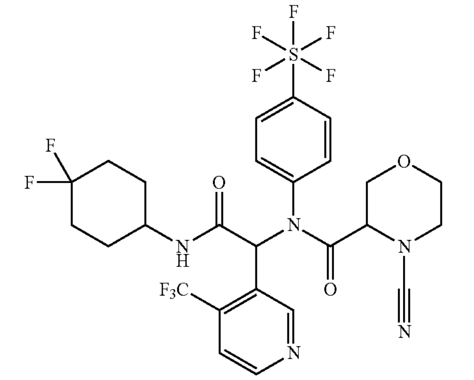 [SMILES: N#CN1CCOCC1C(=O)N(c1ccc(S(F)(F)(F)(F)F)cc1)C(C(=O)NC1CCC(F)(F)CC1)c1cnccc1C(F)(F)F] |
| 1412 | 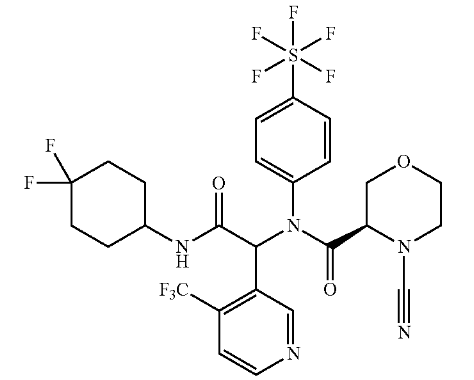 [SMILES: N#CN1CCOC[C@@H]1C(=O)N(c1ccc(S(F)(F)(F)(F)F)cc1)C(C(=O)NC1CCC(F)(F)CC1)c1cnccc1C(F)(F)F] |
| 1413 | 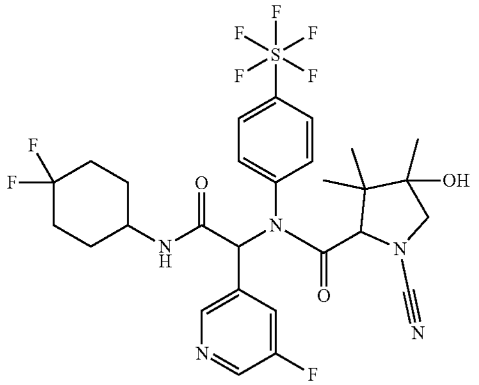 [SMILES: CC1(O)CN(C#N)C(C(=O)N(c2ccc(S(F)(F)(F)(F)F)cc2)C(C(=O)NC2CCC(F)(F)CC2)c2cncc(F)c2)C1(C)C] |
| 1414 | 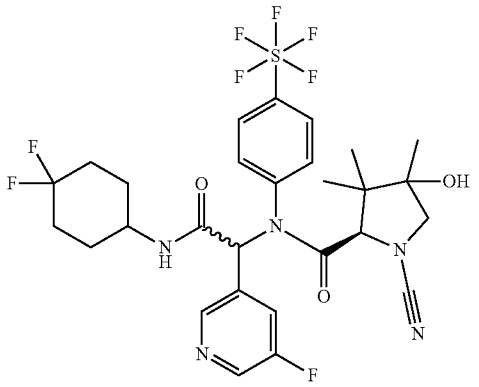 [SMILES: CC1(O)CN(C#N)[C@@H](C(=O)N(c2ccc(S(F)(F)(F)(F)F)cc2)C(C(=O)NC2CCC(F)(F)CC2)c2cncc(F)c2)C1(C)C] |
TABLE 1-continued
| Exemplary compounds. | |
|---|---|
| Cmpd No. | Structure |
| 1415 | 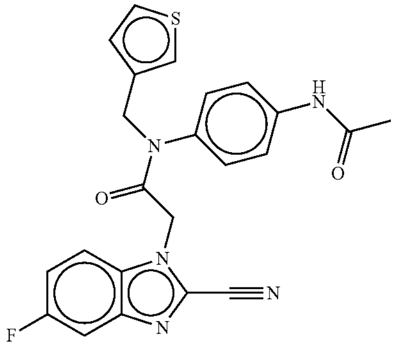 |
| 1416 | 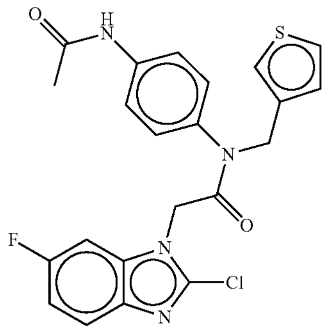 |
| 1417 | 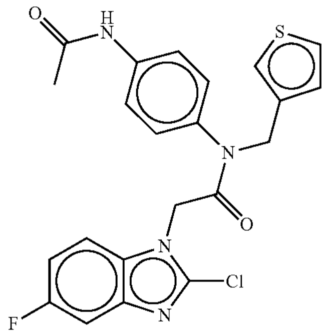 |
| 1418 | 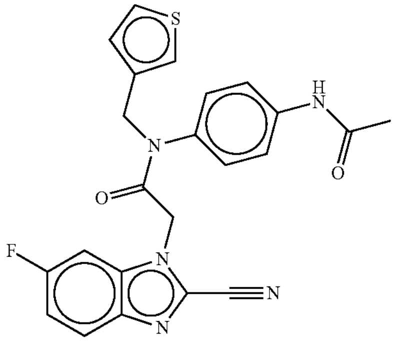 |

TABLE 1-continued

Exemplary compounds.

| Cmpd No. | Structure |
|---|---|
| 1419 | 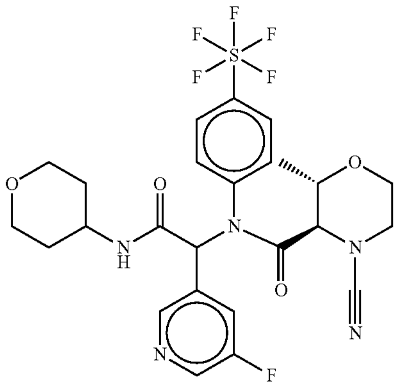 |

Procedures for making compounds described herein are provided in the examples below. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, *Protective Groups in Organic Synthesis. 2nd Ed.* (1999)). The deprotection step may be the final step in the synthesis such that the removal of protecting groups affords compounds of Formula I, I-A-I, I-A, I-B, I-C, II, III, III-A, X, or X-A, as disclosed herein. Starting materials used in the following scheme can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of any of Formula I, I-A-I, I-A, I-B, I-C, II, III, III-A, X, or X-A, depicted below, or any of the intermediates described in the schemes above, can be further derivatised by using one or more standard synthetic methods known to those skilled in the art. Such methods can involve substitution, oxidation or reduction reactions. These methods can also be used to obtain or modify compounds of Formula I, I-A-I, I-A, I-B, I-C, II, III, III-A, X, or X-A, or any preceding intermediates by modifying, introducing or removing appropriate functional groups.

Where it is desired to obtain a particular enantiomer of a compound of Formula I, I-A-I, I-A, I-B, I-C, II, III, III-A, X, or X-A, this may be produced from a corresponding mixture of enantiomers by employing any suitable conventional procedure for resolving enantiomers known to those skilled in the art. For example, diastereomeric derivatives (such as salts) can be produced by reaction of a mixture of enantiomers of a compound of Formula I, I-A-I, I-A, I-B, I-C, II, III, III-A, X, or X-A, (such a racemate) and an appropriate chiral compound (such as a chiral base). The diastereomers can then be separated by any conventional means such as crystallization or chromatography, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel Stereoselective Biocatalysts, Marcel Decker; New York 2000).

In another resolution process a racemate of compounds of Formula I, I-A-I, I-A, I-B, I-C, II, III, III-A, X, or X-A, can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the disclosure.

Also provided herein is a broad spectrum, covalent 3CL or 3C protease antiviral compound, comprising a nitrile warhead covalently bound to a 3CL protease inhibitor, wherein the antiviral compound covalently binds to Cys on the protease, and wherein the antiviral compound is active against multiple viruses. In some embodiments, the broad spectrum covalent compound of Formula I, wherein the compound is active against caliciviruses, picornaviruses and coronaviruses. In some embodiments, the broad spectrum covalent compound of Formula I, I-A-I, I-A, I-B, I-C, II, III, III-A, X, or X-A, wherein the compound is active against caliciviruses, picornaviruses and coronaviruses. In some embodiments, the broad spectrum covalent compound of Formula II, wherein the compound is active against caliciviruses, picornaviruses and coronaviruses. In certain embodiments, the broad spectrum covalent compound of Formula III, wherein the compound is active against caliciviruses, picornaviruses and coronaviruses.

II. Methods

Another aspect of the disclosure provides methods of treating patients suffering from a viral infection, e.g., a coronaviral infection. In particular, in certain embodiments, the disclosure provides a method of treating the below medical indications comprising administering to a subject in need thereof a therapeutically effective amount of a compound described herein, such as a compound of Formula I, I-A-I, I-A, I-B, I-C, II, III, III-A, X, or X-A.

In certain embodiments, the disclosure provides a method of ameliorating or treating a viral infection in a patient in need thereof, comprising administering to the patient a therapeutically effective amount of any of the compounds described herein. In some embodiments, the viral infection is from a virus selected from the group consisting of an RNA virus, a DNA virus, a coronavirus, a papillomavirus, a pneumovirus, a picornavirus, an influenza virus, an adenovirus, a cytomegalovirus, a polyomavirus, a poxvirus, a flavivirus, an alphavirus, an ebola virus, a morbillivirus, an enterovirus, an orthopneumovirus, a lentivirus, arenavirus, a herpes virus, and a hepatovirus. In certain embodiments, the viral infection is a coronavirus infection. In some embodiments, the viral infection is a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2 (COVID-19). In embodiments, the viral infection is SARS-CoV-2.

In some embodiments, the viral infection is from a virus selected from the group consisting of caliciviruses, MD145, murine norovirus, vesicular exanthema of swine virus, abbit hemorrhagic disease virus, porcine teschovirus, bovine coronavirus, feline infectious peritonitis virus, EV-68 virus, EV-71 virus, poliovirus, norovirus, human rhinovirus (HRV), hepatitis A virus (HAV) and foot-and-mouth disease virus (FMDV).

In embodiments, the viral infection is an arenovirus infection. In some embodiments, the arenovirus is selected from the group consisting of: Junin virus, Lassa virus, Lujo virus, Machupo virus, and Sabia virus. In some embodiments, the viral infection is an influenza infection. In some embodiments, the influenza is influenza H1N1, H3N2 or H5N1.

Another aspect of the disclosure provides methods of treating patients suffering from a viral infection, e.g., a noroviral infection. In some embodiments, the disclosure provides a method of treating a viral infection from a norovirus in a patient in need thereof, comprising administering to the patient a therapeutically effective amount of any of the compounds described herein.

Also provided herein, in certain embodiments, is a method of inhibiting transmission of a virus, a method of inhibiting viral replication, a method of minimizing expression of viral proteins, or a method of inhibiting virus release, comprising administering a therapeutically effective amount of a compound described herein to a patient suffering from the virus, and/or contacting an effective amount of a compound described herein with a virally infected cell. In some embodiments, the method further comprises administering another therapeutic. In some embodiments, the method further comprises administering an additional anti-viral therapeutic. In embodiments, the anti-viral therapeutic is selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of protease inhibitors, fusion inhibitors, M2 proton channel blockers, polymerase inhibitors, 6-endonuclease inhibitors, neuraminidase inhibitors, reverse transcriptase inhibitor, aciclovir, acyclovir, protease inhibitors, arbidol, atazanavir, atripla, boceprevir, cidofovir, combivir, darunavir, docosanol, edoxudine, entry inhibitors, entecavir, famciclovir, fomivirsen, fosamprenavir, foscarnet, fosfonet, ganciclovir, ibacitabine, immunovir, idoxuridine, imiquimod, inosine, integrase inhibitor, interferons, lopinavir, loviride, moroxydine, nexavir, nucleoside analogues, penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine. In embodiments, the additional anti-viral therapeutic is selected from the group consisting of lamivudine, an interferon alpha, a VAP anti-idiotypic antibody, enfuvirtide, amantadine, rimantadine, pleconaril, aciclovir, zidovudine, fomivirsen, a morpholino, a protease inhibitor, double-stranded RNA activated caspase oligomerizer (DRACO), rifampicin, zanamivir, oseltamivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfinavir, nevirapine, nitazoxanide, norvir, plerixafor, PRO 140, raltegravir, pyramidine, saquinavir, telbivudine, TNX-355, valacyclovir, VIR-576, and zalcitabine.

Contemplated patients include not only humans, but other animals such as companion animals (e.g. dogs, cats), domestic animals (e.g. cow, swine), and wild animals (e.g. monkeys, bats, snakes).

Accordingly, in one embodiment, described herein is a method of ameliorating or treating a viral infection in a patient in need thereof, comprising administering to the patient a therapeutically effective amount of a compound described herein (e.g., a compound of Formula I, I-A-I, I-A, I-B, I-C, II, III, III-A, X, or X-A, described herein) or a pharmaceutically acceptable salt thereof.

Other contemplated methods of treatment include method of treating or ameliorating a virus infection condition or co-morbidity, by administering a compound disclosed herein to a subject.

Exemplary co-morbidities include lung diseases, cardiac disorders, endocrine disorders, respiratory disorders, hepatic disorders, skeletal disorders, psychiatric disorders, metabolic disorders, and reproductive disorders.

In some embodiments, the viral infection is from a virus selected from the group consisting of an RNA virus, a DNA virus, a coronavirus, a papillomavirus, a pneumovirus, a picornavirus, an influenza virus, an adenovirus, a cytomegalovirus, a polyomavirus, a poxvirus, a flavivirus, an alphavirus, an ebola virus, a morbillivirus, an enterovirus, an orthopneumovirus, a lentivirus, arenovirus, a herpes virus, and a hepatovirus. In some embodiments, the viral infection is a coronavirus infection. In some embodiments, the viral infection is a coronavirus selected from the group consisting of: 229E alpha coronavirus, NL63 alpha coronavirus, OC43 beta coronavirus, HKU1 beta coronavirus, Middle East Respiratory Syndrome (MERS) coronavirus (MERS-CoV), severe acute respiratory syndrome (SARS) coronavirus (SARS-CoV), and SARS-CoV-2 (COVID-19). In some embodiments, the viral infection is SARS-CoV-2. In some embodiments, the viral infection is an arenovirus infection. In some embodiments, the arenovirus is selected from the group consisting of: Junin virus, Lassa virus, Lujo virus, Machupo virus, and Sabia virus. In some embodiments, the viral infection is an influenza infection. In some embodiments, the influenza is influenza H1N1, H3N2 or H5N1. In some embodiments, the viral infection is a respiratory viral infection. In some embodiments, the viral infection is an upper respiratory viral infection or a lower respiratory viral infection. In some embodiments, the method further comprises administering another therapeutic.

In certain embodiments, the virus is selected from the group consisting of a retrovirus (e.g., human immunodeficiency virus (HIV), simian immunodeficiency virus (SIV), human T-cell lymphotropic virus (HTLV)-1, HTLV-2, HTLV-3, HTLV-4), Ebola virus, hepatitis A virus, hepatitis B virus, hepatitis C virus, a herpes simplex virus (HSV) (e.g., HSV-1, HSV-2, varicella zoster virus, cytomegalovirus), an adenovirus, an orthomyxovirus (e.g., influenza virus A, influenza virus B, influenza virus C, influenza virus D, thogotovirus), a flavivirus (e.g., dengue virus, Zika virus), West Nile virus, Rift Valley fever virus, an arenavirus, Crimean-Congo hemorrhagic fever virus, an echovirus, a rhinovirus, coxsackie virus, a coronavirus (e.g., Severe acute respiratory syndrome coronavirus 2 (SARS-CoV-2), coronavirus disease 2019 (COVID-19), a respiratory syncytial virus, a mumps virus, a rotavirus, measles virus, rubella virus, a parvovirus (e.g., an adeno-associated virus), a vaccinia virus, a variola virus, a molluscum virus, bovine leukemia virus, bovine diarrhea virus, a poliovirus, St. Louis encephalitis virus, Japanese encephalitis virus, a tick-borne encephalitis virus, Murray Valley virus, Powassan virus, Rocio virus, louping-ill virus, Banzi virus, Ilheus virus, Kokobera virus, Kunjin virus, Alfuy virus, a rabies virus, a polyomavirus (e.g., JC virus, BK virus), an alphavirus, and a rubivirus (e.g., rubella virus).

In certain embodiments, the disease or disorder is a viral infection, e.g., a disease or disorder selected from the group consisting of acquired immune deficiency syndrome (AIDS), HTLV-1 associated myelopathy/tropical spastic paraparesis, Ebola virus disease, hepatitis A, hepatitis B, hepatitis C, herpes, herpes zoster, acute varicella, mononucleosis, respiratory infections, pneumonia, influenza, dengue fever, encephalitis (e.g., Japanese encephalitis, St. Louis encephalitis, or tick-borne encephalitis such as Powassan encephalitis), West Nile fever, Rift Valley fever, Crimean-Congo hemorrhagic fever, Kyasanur Forest disease, Yellow fever, Zika fever, aseptic meningitis, myocarditis, common cold, lung infections, molloscum contagiosum, enzootic bovine leucosis, coronavirus disease 2019 (COVID-19), mumps, gastroenteritis, measles, rubella, slapped-cheek disease, smallpox, warts (e.g., genital warts), molluscum contagiosum, polio, rabies, and *Pityriasis rosea.*

In some embodiments, the virus is an RNA virus (having a genome that is composed of RNA). RNA viruses may be single-stranded RNA (ssRNA) or double-stranded RNA (dsRNA). RNA viruses have high mutation rates compared to DNA viruses, as RNA polymerase lacks proofreading capability (see Steinhauer D A, Holland J J (1987). "*Rapid evolution of RNA viruses*". *Annu. Rev. Microbiol.* 41: 409-33). In some embodiments, the RNA virus is a positive-strand RNA virus (e.g., a SARS-CoV virus, polio virus, Coxsackie virus, Enterovirus, Human rhinovirus, Foot/Mouth disease virus, encephalomyocarditis virus, Dengue virus, Zika virus, Hepatitis C virus, or New Castle Disease virus).

RNA viruses are classified by the type of genome (double-stranded, negative (−), or positive (+) single-stranded). Double-stranded RNA viruses contain a number of different RNA molecules, each coding for one or more viral proteins. Positive-sense ssRNA viruses utilize their genome directly as mRNA; ribosomes within the host cell translate mRNA into a single protein that is then modified to form the various proteins needed for viral replication. One such protein is RNA-dependent RNA polymerase (RNA replicase), which copies the viral RNA in order to form a double-stranded, replicative form. Negative-sense ssRNA viruses have their genome copied by an RNA replicase enzyme to produce positive-sense RNA for replication. Therefore, the virus comprises an RNA replicase enzyme. The resultant positive-sense RNA then acts as viral mRNA and is translated by the host ribosomes. In some embodiments, the virus is a dsRNA virus. In some embodiments, the virus is a negative ssRNA virus. In some embodiments, the virus is a positive ssRNA virus. In some embodiments, the positive ssRNA virus is a coronavirus.

SARS-CoV2, also sometimes referred to as the novel coronavirus of 2019 or 2019-nCoV, is a positive-sense single-stranded RNA virus. SARS-CoV-2 has four structural proteins, known as the S (spike), E (envelope), M (membrane), and N (nucleocapsid) proteins. The N protein holds the RNA genome together; the S, E, and M proteins form the viral envelope. Spike allows the virus to attach to the membrane of a host cell, such as the ACE2 receptor in human cells (Kruse R. L. (2020), Therapeutic strategies in an outbreak scenario to treat the novel coronavirus originating in Wuhan, China (version 2). *F*1000*Research,* 9:72). SARS-CoV2 is the highly contagious, causative viral agent of coronavirus disease 2019 (COVID19), a global pandemic.

In some embodiments, the virus is a DNA virus (having a genome that is composed of DNA). Exemplary DNA viruses include, without limitation, parvoviruses (e.g., adeno-associated viruses), adenoviruses, asfarviruses, herpesviruses (e.g., herpes simplex virus 1 and 2 (HSV-1 and HSV-2), Epstein-Barr virus (EBV), cytomegalovirus (CMV)), papillomoviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). Exemplary RNA viruses include, without limitation, bunyaviruses (e.g., hantavirus), coronaviruses, flaviviruses (e.g., yellow fever virus, west nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, noroviruses (e.g., Norwalk virus), poliovirus, respiratory syncytial virus (RSV), retroviruses (e.g., human immunodeficiency virus-1 (HIV-1)) and toroviruses.

The methods described herein may inhibit viral replication transmission, replication, assembly, or release, or minimize expression of viral proteins. In one embodiment, described herein is a method of inhibiting transmission of a virus, a method of inhibiting viral replication, a method of minimizing expression of viral proteins, or a method of inhibiting virus release, comprising administering a therapeutically effective amount of a compound described herein, or a pharmaceutically acceptable salt thereof, to a patient suffering from the virus, and/or contacting an effective amount of a compound described herein or a pharmaceutically acceptable salt thereof, with a virally infected cell.

Also described herein is a method of treating a respiratory disorder in a subject in need thereof, comprising administering to the patient a therapeutically effective amount of a compound described herein (e.g., a compound of Formula I, I-A-I, I-A, I-B, I-C, II, III, III-A, X, X-A etc. described herein) or a pharmaceutically acceptable salt thereof. In embodiments, the respiratory disorder is selected from the group consisting of chronic obstructive pulmonary disease (COPD), asthma, fibrosis, chronic asthma, acute asthma, lung disease secondary to environmental exposures, acute lung infection, chronic lung infection, al antitrypsin disease, cystic fibrosis and an autoimmune disease. In some embodiments, the respiratory disorder is associated with a heart attack.

Also described herein is a method of treating a disorder associated with cathepsin (e.g. Cathepsin K) in a subject in need thereof, comprising administering to the patient a therapeutically effective amount of a compound described herein (e.g., a compound of Formula I, I-A-I, I-A, I-B, I-C, II, III, III-A, X, X-A, etc. described herein) or a pharmaceutically acceptable salt thereof. In some embodiments, the disorder is a cathepsin dependent condition or disease. In embodiments, the disorder is selected from the group consisting of breast cancer, pycnodysostosis, glioblastoma, osteosclerosis, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy, and multiple myeloma.

Compounds described herein, e.g., a compound of Formula I, I-A-I, I-A, I-B, I-C, II, III, III-A, X, X-A, etc. as defined herein, can be administered in combination with one or more additional therapeutic agents to treat a disorder described herein, such as an infection by a pathogen described herein, e.g., a virus, fungus, or protozoan. For clarity, contemplated herein are both a fixed composition comprising a disclosed compound and another therapeutic agent such as disclosed herein, and methods of administering, separately a disclosed compound and a disclosed therapeutic. For example, provided in the present disclosure is a pharmaceutical composition comprising a compound described herein, e.g., a compound of Formula I as defined herein, one or more additional therapeutic agents, and a pharmaceutically acceptable excipient. In some embodiments, a compound of Formula I, I-A-I, I-A, I-B, I-C, II, III, III-A, X, or X-A as defined herein and one additional therapeutic agent is administered. In some embodiments, a disclosed compound as defined herein and two additional therapeutic agents are administered. In some embodiments, a disclosed compound as defined herein and three additional therapeutic agents are administered. Combination therapy can be achieved by administering two or more therapeutic agents, each of which is formulated and administered separately. For example, a compound of Formula I, I-A-I, I-A, I-B, I-C, II, III, III-A, X, X-A, etc., as defined herein and an additional therapeutic agent can be formulated and administered separately. Combination therapy can also be achieved by administering two or more therapeutic agents in a single formulation, for example a pharmaceutical composition comprising a compound of Formula I as one therapeutic agent and one or more additional therapeutic agents such as an antibiotic, a viral protease inhibitor, or an anti-viral nucleoside anti-metabolite. For example, a compound of Formula I as defined herein and an additional therapeutic agent can be administered in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

In some embodiments, the one or more additional therapeutic agents that may be administered in combination with a compound provided herein can be an antibiotic, a viral protease inhibitor, an anti-viral anti-metabolite, a lysosomotropic agent, a M2 proton channel blocker, a polymerase inhibitor (e.g., EIDD-2801, which is also known as MOLNUPIRAVIR), a neuraminidase inhibitor, a reverse transcriptase inhibitor, a viral entry inhibitor, an integrase inhibitor, interferons (e.g., types I, II, and III), or a nucleoside analogue. In some embodiments, the one or more additional therapeutic agents that may be administered in combination with a compounds provided herein can be a steroid (e.g., corticosteroids, such as bethamethasone, prednisone, prednisolone, triamcinolone, methylprednisolone, dexamethasone; mineralcorticoid such as fludrocortisone; glucocorticoids, such as hydrocortisone, cortisone, ethamethasoneb, prednisone, prednisolone, triamcinolone, dexamethasone; vitamin D such as dihydrotachysterol; androgens such as apoptone, oxandrolone, oxabolone, testosterone, nandrolone (also known as anabolic steroids), oestrogens such as diethylstilbestrol, progestins such as danazol, norethindrone, medroxyprogesterone acetate, 17-Hydroxyprogesterone caproate; and progestins such as mifepristone and gestrinone) or an immunomodulator (e.g., 6-Mercaptopurine, 6MP, Alferon N, anakinra, Arcalyst, Avonex, AVOSTARTGRIP, Bafiertam, Berinert, Betaseron, BG-12, C1 esterase inhibitor recombinant, C1 inhibitor human, Cinryze, Copaxone, dimethyl fumarate, diroximel fumarate, ecallantide, emapalumab, emapalumab-lzsg, Extavia, fingolimod, Firazyr, Gamifant, Gilenya, glatiramer, Glatopa, Haegarda, icatibant, Infergen, interferon alfa n3, interferon alfacon 1, interferon beta 1a, interferon beta 1b, Kalbitor, Kineret, mercaptopurine, monomethyl fumarate, peginterferon beta-1a, Plegridy, Purinethol, Purixan, Rebif, Rebif Rebidose, remestemcel-L, rilonacept, ropeginterferon alfa 2b, Ruconest, Ryoncil, siltuximab, sutimlimab, Sylvant, Tecfidera, and Vumerity). In some embodiments, the one or more additional therapeutic agent is Cathepsin L. In some embodiments, the one or more additional therapeutic agent is dehydrodidemnin B (also known as Plitidepsin or APLIDIN) or Zotatifin (eFT226).

In some embodiments, methods described herein further comprise administering an additional anti-viral therapeutic. In some embodiments, the anti-viral therapeutic is selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of protease inhibitors (e.g., nafamostat, camostat, gabexate, epsilon-aminocapronic acid and aprotinin), fusion inhibitors (e.g., BMY-27709, CL 61917, and CL 62554), M2 proton channel blockers (e.g., amantadine and rimantadine), polymerase inhibitors (e.g., 2-deoxy-2'fluoroguanosides (2'-fluoroGuo), 6-endonuclease inhibitors (e.g., L-735,822 and flutamide)

neuraminidase inhibitors (e.g., zanamivir (Relenza), oseltamivir, peramivir and ABT-675 (A-315675), reverse transcriptase inhibitor (e.g., abacavir, adefovir, delavirdine, didanosine, efavirenz, emtricitabine, lamivudine, nevirapine, stavudine, tenofovir, tenofovir disoproxil, and zalcitabine), acyclovir, acyclovir, protease inhibitors (e.g., amprenavir, indinavir, nelfinavir, ritonavir, and saquinavir), arbidol, atazanavir, atripla, boceprevir, cidofovir, combivir, darunavir, docosanol, edoxudine, entry inhibitors (e.g., enfuvirtide and maraviroc), entecavir, famciclovir, fomivirsen, fosamprenavir, foscarnet, fosfonet, ganciclovir, ibacitabine, immunovir, idoxuridine, imiquimod, inosine, integrase inhibitor (e.g., raltegravir), interferons (e.g., types I, II, and III), lopinavir, loviride, moroxydine, nexavir, nucleoside analogues (e.g., aciclovir), penciclovir, pleconaril, podophyllotoxin, ribavirin, tipranavir, trifluridine, trizivir, tromantadine, truvada, valaciclovir, valganciclovir, vicriviroc, vidarabine, viramidine, and zodovudine. In some embodiments, the additional anti-viral therapeutic is selected from the group consisting of lamivudine, an interferon alpha, a VAP anti-idiotypic antibody, enfuvirtide, amantadine, rimantadine, pleconaril, aciclovir, zidovudine, fomivirsen, a morpholino, a protease inhibitor, double-stranded RNA activated caspase oligomerizer (DRACO), rifampicin, zanamivir, oseltamivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmnavir, nevirapine, nitazoxanide, norvir, plerixafor, PRO 140, raltegravir, pyramidine, saquinavir, telbivudine, TNX-355, valacyclovir, VIR-576, and zalcitabine. In some embodiments, the another therapeutic is selected from the group consisting of quinine (optionally in combination with clindamycin), chloroquine, amodiaquine, artemisinin and its derivatives (e.g., artemether, artesunate, dihydroartemisinin, arteether), doxycycline, pyrimethamine, mefloquine, halofantrine, hydroxychloroquine, eflornithine, nitazoxanide, ornidazole, paromomycin, pentamidine, primaquine, pyrimethamine, proguanil (optionally in combination with atovaquone), a sulfonamide (e.g., sulfadoxine, sulfamethoxypyridazine), tafenoquine, tinidazole and a PPT1 inhibitor (including Lys05 and DC661). In some embodiments, the another therapeutic is an antibiotic. In some embodiments, the antibiotic is a penicillin antibiotic, a quinolone antibiotic, a tetracycline antibiotic, a macrolide antibiotic, a lincosamide antibiotic, a cephalosporin antibiotic, or an RNA synthetase inhibitor. In some embodiments, the antibiotic is selected from the group consisting of azithromycin, vancomycin, metronidazole, gentamicin, colistin, fidaxomicin, telavancin, oritavancin, dalbavancin, daptomycin, cephalexin, cefuroxime, cefadroxil, cefazolin, cephalothin, cefaclor, cefamandole, cefoxitin, cefprozil, ceftobiprole, cipro, Levaquin, floxin, tequin, avelox, norflox, tetracycline, minocycline, oxytetracycline, doxycycline, amoxicillin, ampicillin, penicillin V, dicloxacillin, carbenicillin, methicillin, ertapenem, doripenem, imipenem/cilastatin, meropenem, amikacin, kanamycin, neomycin, netilmicin, tobramycin, paromomycin, cefixime, cefdinir, cefditoren, cefoperazone, cefotaxime, ceftazidime, ceftibuten, ceftizoxime, ceftriaxone, cefoxotin, and streptomycin. In some embodiments, the antibiotic is azithromycin.

In some embodiments, the one or more additional therapeutic agents that may be administered in combination with a compound provided herein can be selected from the group consisting of ribavirin, favipiravir, ST-193, oseltamivir, zanamivir, peramivir, danoprevir, ritonavir, remdesivir, cobicistat, elvitegravir, emtricitabine, tenofovir, tenofovir disoproxil, tenofovir alafenamide hemifumarate, abacavir, dolutegravir, efavirenz, elbasvir, ledipasvir, glecaprevir, sofosbuvir, bictegravir, dasabuvir, lamivudine, atazanavir, ombitasvir, lamivudine, stavudine, nevirapine, rilpivirine, paritaprevir, simeprevir, daclatasvir, grazoprevir, pibrentasvir, adefovir, amprenavir, ampligen, aplaviroc, anti-caprine antibody, balavir, cabotegravir, cytarabine, ecoliever, epigallocatechin gallate, etravirine, fostemsavir, gemcitabine, griffithsin, imunovir, indinavir, maraviroc, methisazone, MK-2048, nelfmavir, nevirapine, nitazoxanide, norvir, plerixafor, PRO 140, raltegravir, pyramidine, saquinavir, telbivudine, TNX-355, valacyclovir, VIR-576, and zalcitabine.

In some embodiments, the compounds described herein (e.g. a compound of Formula I, I-A-I, I-A, I-B, I-C, II, III, III-A, X, or X-A, etc.) and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g. muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, anthelmintic agents, antimalarial agents, antiprotozoal agents and antituberculosis agents.

In some embodiments, the additional therapeutic agents can be kinase inhibitors including but not limited to erlotinib, gefitinib, neratinib, afatinib, osimertinib, lapatanib, crizotinib, brigatinib, ceritinib, alectinib, lorlatinib, everolimus, temsirolimus, abemaciclib, LEE011, palbociclib, cabozantinib, sunitinib, pazopanib, sorafenib, regorafenib, sunitinib, axitinib, dasatinib, imatinib, nilotinib, ponatinib, idelalisib, ibrutinib, Loxo 292, larotrectinib, and quizartinib.

In some embodiments, the additional therapeutic agents can be therapeutic anti-viral vaccines.

In some embodiments, the additional therapeutic agents can be immunomodulatory agents including but not limited to anti-PD-lor anti-PDL-1 therapeutics including pembrolizumab, nivolumab, atezolizumab, durvalumab, BMS-936559, or avelumab, anti-TIM3 (anti-HAVcr2) therapeutics including but not limited to TSR-022 or MBG453, anti-LAG3 therapeutics including but not limited to relatlimab, LAG525, or TSR-033, anti-4-1BB (anti-CD37, anti-TNFRSF9), CD40 agonist therapeutics including but not limited to SGN-40, CP-870,893 or R07009789, anti-CD47 therapeutics including but not limited to Hu5F9-G4, anti-CD20 therapeutics, anti-CD38 therapeutics, STING agonists including but not limited to ADU-S100, MK-1454, ASA404, or amidobenzimidazoles, anthracyclines including but not limited to doxorubicin or mitoxanthrone, hypomethylating agents including but not limited to azacytidine or decitabine, other immunomodulatory therapeutics including but not limited to epidermal growth factor inhibitors, statins, metformin, angiotensin receptor blockers, thalidomide, lenalidomide, pomalidomide, prednisone, or dexamethasone. In some embodiments, the additional therapeutic agent is a p2-adrenoreceptor agonist including, but not limited to, vilanterol, salmeterol, salbutamol.formoterol, salmefamol, fenoterol carmoterol, etanterol, naminterol, clenbuterol, pirbuterol.flerbuterol, reproterol, bambuterol, indacaterol, terbutaline and salts thereof, for example the xinafoate (1-hydroxy-2-naphthalenecarboxylate) salt of salmeterol, the sulphate salt of salbutamol or the fumarate salt of formoterol. In some embodiments, the additional therapeutic agent is an anticholinergic agent, including, but not limited to, umeclidinium (for example, as the bromide), ipratropium (for example, as the bromide), oxitropium (for example, as the bromide) and tiotropium (for example, as the bromide).

In particular, in certain embodiments, the disclosure provides a method of treating the above medical indications comprising administering a subject in need thereof a therapeutically effective amount of a compound described herein, such as a disclosed compound.

The term "boosting amount" or "boosting dose" is the amount of a compound needed to improve the pharmacokinetics of a second compound (or increase availability or exposure). The boosting amount or boosting dose may improve the pharmacokinetics (or increase availability or exposure) of the second compound to a level to therapeutic levels in a subject.

In one embodiment, the disclosure provides for a disclosed compound to be administered together with an anti-viral therapeutic such as disclosed herein, and e.g., thereby boosting the dose of the anti-viral therapeutic or therapeutics. Such a boost combination may be used, e.g., as prophylactic or therapeutic treatment of a viral infection in a subject in need thereof. In one embodiment, the protease inhibitor is a compound described herein (e.g. a compound of Formula I, I-A-I, I-A, I-B, I-C, II, III, III-A, X, X-A, etc).

III. Pharmaceutical Compositions and Kits

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this disclosure may be used in the form of a pharmaceutical preparation, for example, in solid, semisolid or liquid form, which contains one or more of the compound of the disclosure, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present disclosure may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this disclosure suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the disclosure provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present disclosure.

Advantageously, the disclosure also provides kits for use by a e.g. a consumer in need of 3CL inhibitor. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc., Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to having a viral infection, a subject or patient can further have viral infection- or virus-related co-morbidities, i.e., diseases and other adverse health conditions associated with, exacerbated by, or precipitated by being infected by a virus. Contemplated herein are disclosed compounds in combination with at least one other agent that has previously been shown to treat these virus-related conditions.

IV. Reversible or Irreversible Conjugates

In some embodiments, provide herein are conjugates represented by:

Formula VI

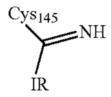

wherein $Cys_{145}$ is cysteine at position 145 or equivalent active site cysteine on a CL protease; and IR is a viral protease inhibitor.

In some embodiments, provide herein are conjugates represented by:

Formula VII

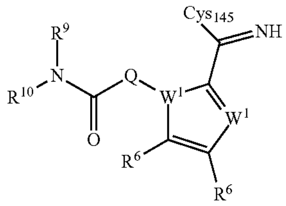

wherein: $Cys_{145}$ is cysteine at position 145 or equivalent active site cysteine on the 3CL protease; $W^1$ is, for each occurrence, selected from the group consisting of C, CH, S, and N; Q is $CH_2$ or NH; $R^6$ is independently selected, for each occurrence, from the group consisting of: hydrogen, halogen, $C_1$-$C_5$alkyl, $C_1$-$C_6$haloalkyl, and $C_1$-$C_5$alkoxy; or $R^6$ can be taken together with the two carbons where $R^6$ are attached to form a phenyl or 5-7 membered heteroaryl ring; $R^9$ is a phenyl, or monocyclic or 8-10 membered bicyclic heteroaryl optionally substituted by one, two or three substituents each selected from $R^{12}$; $R^{12}$ is independently selected, for each occurrence, from the group consisting of phenyl, 5-6 membered heteroaryl, —$N(R^eR^f)$, —$N(R^e)$—C(O)—$(R^f)$, and —$N(R^e)$—$S(O)_2$—$(R^f)$, wherein the 5-6 membered heteroaryl may have one, two or three optional substituents each selected from $R^h$; $R^{10}$ is a phenyl, 5-6 membered monocyclic heteroaryl, or 7-10 membered heteroaryl, wherein $R^{10}$ is optionally substituted by one, two or three substituents each selected from $R^g$; $R^g$, for each occurrence, is selected from the group consisting of halogen, —$NO_2$, $C_1$-$C_5$alkyl, $C_1$-$C_5$alkoxy, $C_1$-$C_5$alkoxy-$N(R^eR^f)$, —$N(R^eR^f)$, phenyl, and 5-6 membered heteroaryl, wherein the phenyl or heteroaryl may have one, two or three optional substituents each selected from $R^h$; $R^d$, for each occurrence, is selected from the group consisting of halogen, hydroxyl, $C_1$-$C_5$alkyl, $C_1$-$C_6$haloalkyl, $C_1$-$C_5$alkoxy, —C(O)—$N(R^eR^f)$, and —$N(R^eR^f)$; $R^e$ and $R^f$ are each selected from the group consisting of hydrogen and $C_1$-$C_6$alkyl; wherein $C_1$-$C_6$alkyl may optionally be substituted by one or more substituents selected from the group consisting of halogen, cyano, oxo, and hydroxyl; or $R^e$ and $R^f$ may form, together with the nitrogen to which they are attached, a 4-6 membered heterocycle; $R^h$, for each occurrence, is selected from the group consisting of halogen, $C_1$-$C_5$alkyl, $C_1$-$C_6$haloalkyl, and $C_1$-$C_5$alkoxy; and pharmaceutically acceptable salts, stereoisomers, esters, and prodrugs thereof.

In some embodiments, $R^9$ is

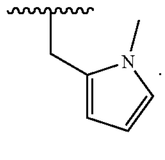 [SMILES: *Cc1cccn1C].

In some embodiments, $R^{10}$ is

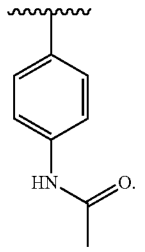 [SMILES: *c1ccc(NC(C)=O)cc1]

In embodiments, Q is $CH_2$.

In some embodiments, the compound of Formula VII is

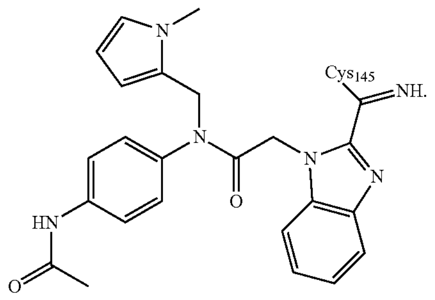

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

The compounds described herein can be synthesized using methods disclosed in Tanaka, Y.; Hasui, T.; Suginome, M. *Organic Letters* 2007 9(22), 4407-4410, and Pan, S. C.; List, B. *Angew. Chem. Int. Ed.* 2008, 47, 3622-3625, which are incorporated herein by reference.

At least some of the compounds identified as "Intermediates" herein are contemplated as compounds of the disclosure.

$^1$H NMR spectra are recorded at ambient temperature using e.g., a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet, d=doublet, dd=double doublet, dt=double triplet, ddd=double double doublet, t=triplet, td=triple doublet, tdd=triple double doublet, q=quartet, m=multiplet.

Mass Spectrometry (LCMS) experiments to determine retention times and associated mass ions were performed using the following methods:

Abbreviations

ACN acetonitrile

DCM dichloromethane

DMF N,N-dimethylformamide

DMSO dimethyl sulfoxide

DPPF 1,2-bis(diphenylphosphino)ethane

EA ethyl acetate

EtOAc ethyl acetate

EtOH ethanol

HPLC high-performance liquid chromatography

MeOH methanol

MS mass spectrometry

NMR nuclear magnetic resonance

PE petroleum ether

PyBOP (benzotriazol-1-yloxytris(dimethylamino)phosphonium hexafluorophosphate)

TEA triethylamine

THF tetrahydrofuran

TFA trifluoroacetic acid

TFAA Trifluoroacetic anhydride

General Chemistry

Exemplary compounds described herein are available by the general synthetic method(s) illustrated in the Scheme(s) below, including preparations of Intermediates and preparation of accompanying Examples.

Synthetic Scheme(s)

Scheme 1

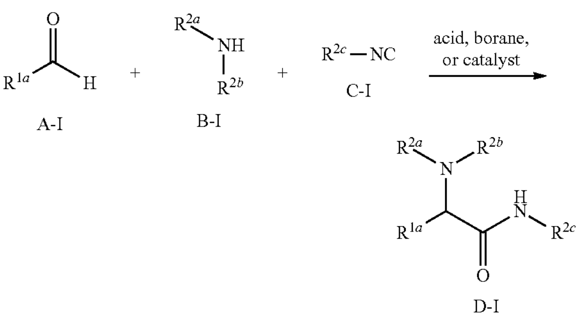

Scheme 1 illustrates an exemplary preparation of amino amide D-I. Reacting a solution of aldehyde A-I, amine B-I, and cyanide C-I with an acid, borane, or catalyst in the presence of a solvent affords amino amide D-I.

In Scheme 1, examples of Ria include heteroaryl and warheads, examples of each $R^{2a}$ and $R^{2a}$ include phenyl, cycloalkyl, heterocyclyl, heteroaryl, substituted carbonyls, and warheads, and examples of $R^{2c}$ include hydrogen, halogen, phenyl, alkyl, alkoxyl, and cycloalkyl.

Compounds of Table 1 can be prepared following general Scheme 1, which follows examples described below.

Example 1: Synthesis of Covalent Viral Protease Inhibitor Compounds

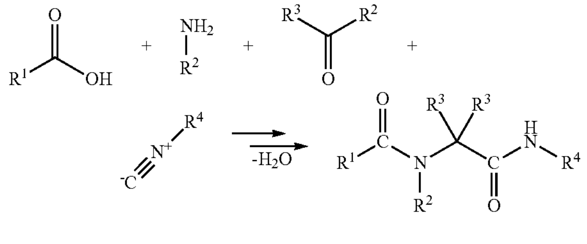

A mixture of aldehyde, amine, isocyanide and acid in methanol were stirred overnight at room temperature to 40° C. The resultant mixture was cooled and concentrated in vacuo or gentle stream of nitrogen. The residue was diluted with $CH_3CN$, and then $K_2CO_3$ was added. The residue was cooled to room temperature, and then diluted with ethyl acetate and washed with water and brine. The organic layer was dried with $Na_2SO_4$, filtered and concentrated. The residue was purified by chromatography on silica, eluting with a mixture of ethyl acetate and hexanes with a gradient of 15-30% to afford the relative targeted product.

Example 2: Synthesis of N-(4-(tert-butyl)phenyl)-N-(2-(cyclohexylamino)-2-oxo-1-(pyridin-3-yl) ethyl)-1H-imidazole-4-carboxamide

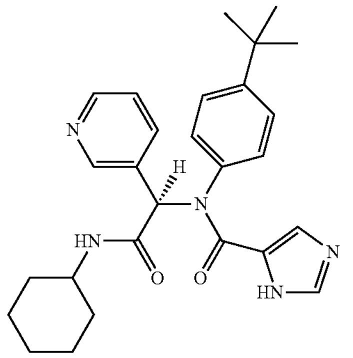 [SMILES: CC(C)(C)c1ccc(N(C(=O)c2cnc[nH]2)[C@@H](C(=O)NC2CCCCC2)c2cccnc2)cc1]

Equimolar amounts of amine, aldehyde, and acid in MeOH (0.2 M) were added to a 1-dram vial containing a magnetic stir bar and allowed to stir at ambient temperature for 30 minutes. The isocyanide (0.90 eq.) was then added. The reaction vessel was allowed to stir for 18 hours at ambient temperature before it was diluted with MeOH, filtered through a celite pad, and purified by HPLC.

$^1$H NMR (400 MHz, DMSO-$d_6$) δ (ppm): 8.40-8.29 (m, 2H), 8.13 (d, 1H), 7.58 (s, 1H), 7.39 (dt, 1H), 7.36-7.15 (m, 3H), 7.14 (dd, 1H), 6.19 (s, 1H), 5.27 (s, 1H), 3.58 (ddt, 11H), 1.83-1.45 (m, 5H), 1.41-1.24 (m, 3H), 1.22 (s, 9H), 1.20-0.91 (m, 3H). ESI-MS(+): 460.2 [M+1].

Figure 2A:
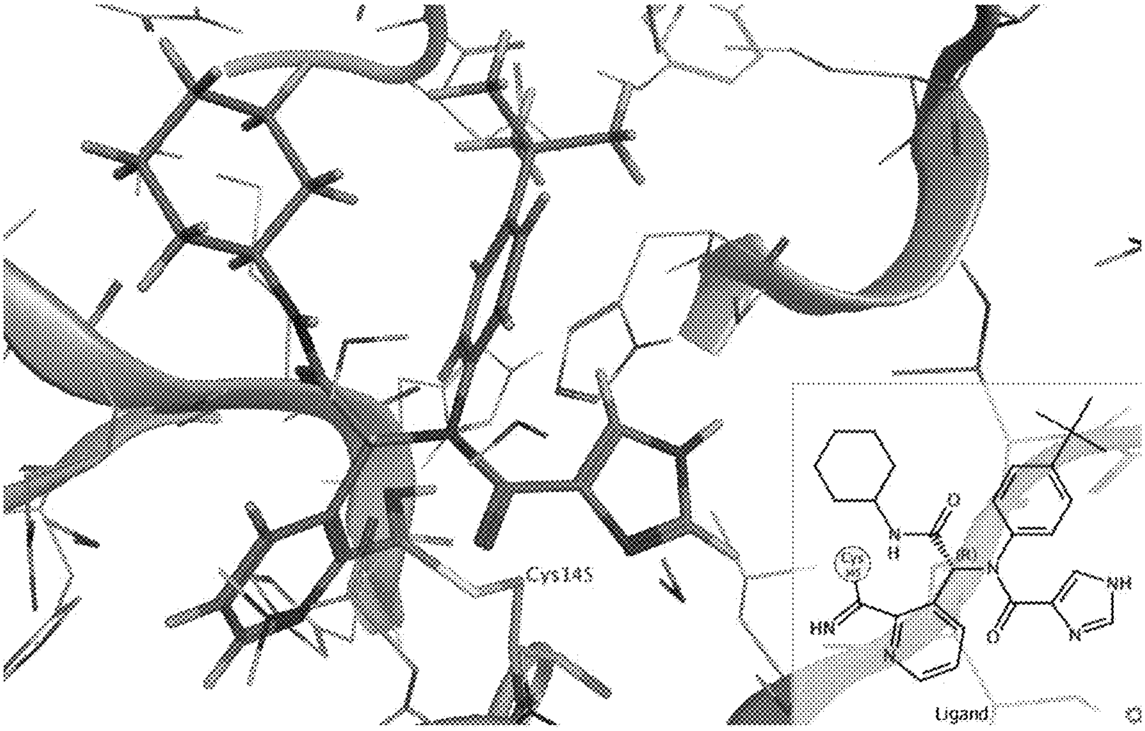
FIG. 2A depicts a predicted thioimidate adduct formed from an alternative Formula I type inhibitor with COVID-19 3CL protease produced upon reaction with active site $Cys_{145}$.
Figure 2B:
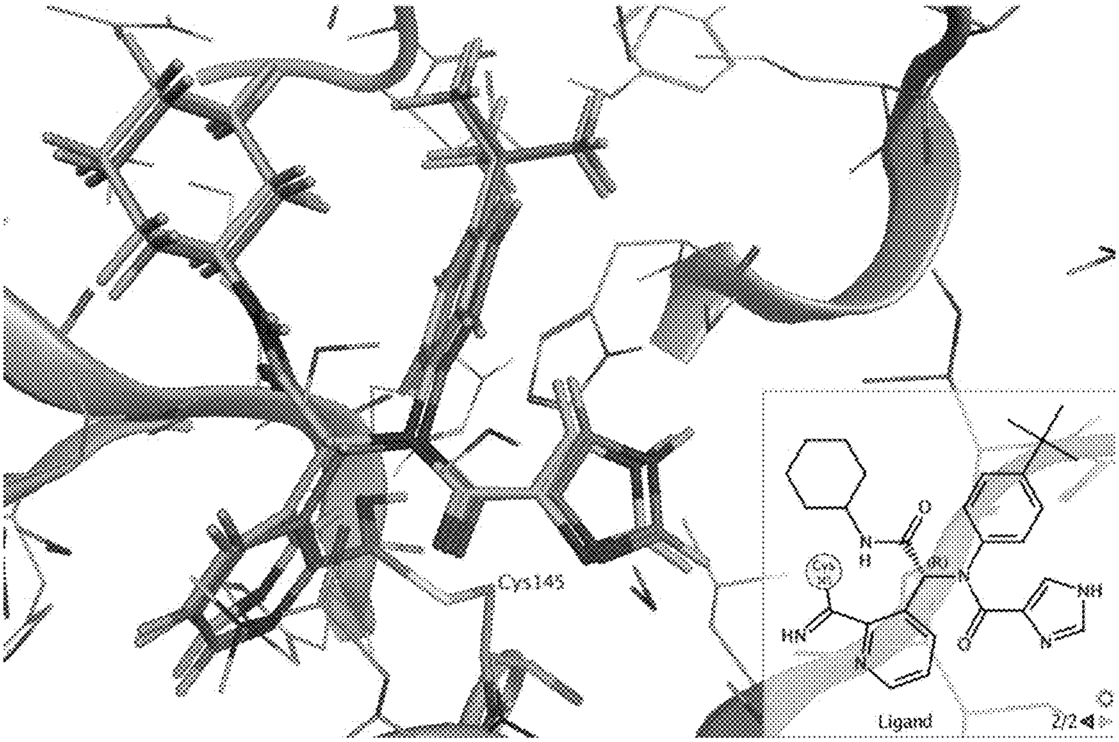
FIG. 2B depicts an overlay of non-covalent inhibitor (S)—N-(4-(tert-butyl)phenyl)-N-(1-(2-cyanopyridin-3-yl)-2-(cyclohexylamino)-2-oxoethyl)-1H-imidazole-5-carboxamide in active site from 6W63 PDB with predicted reversible covalent nitrile adduct.
Figure 3:
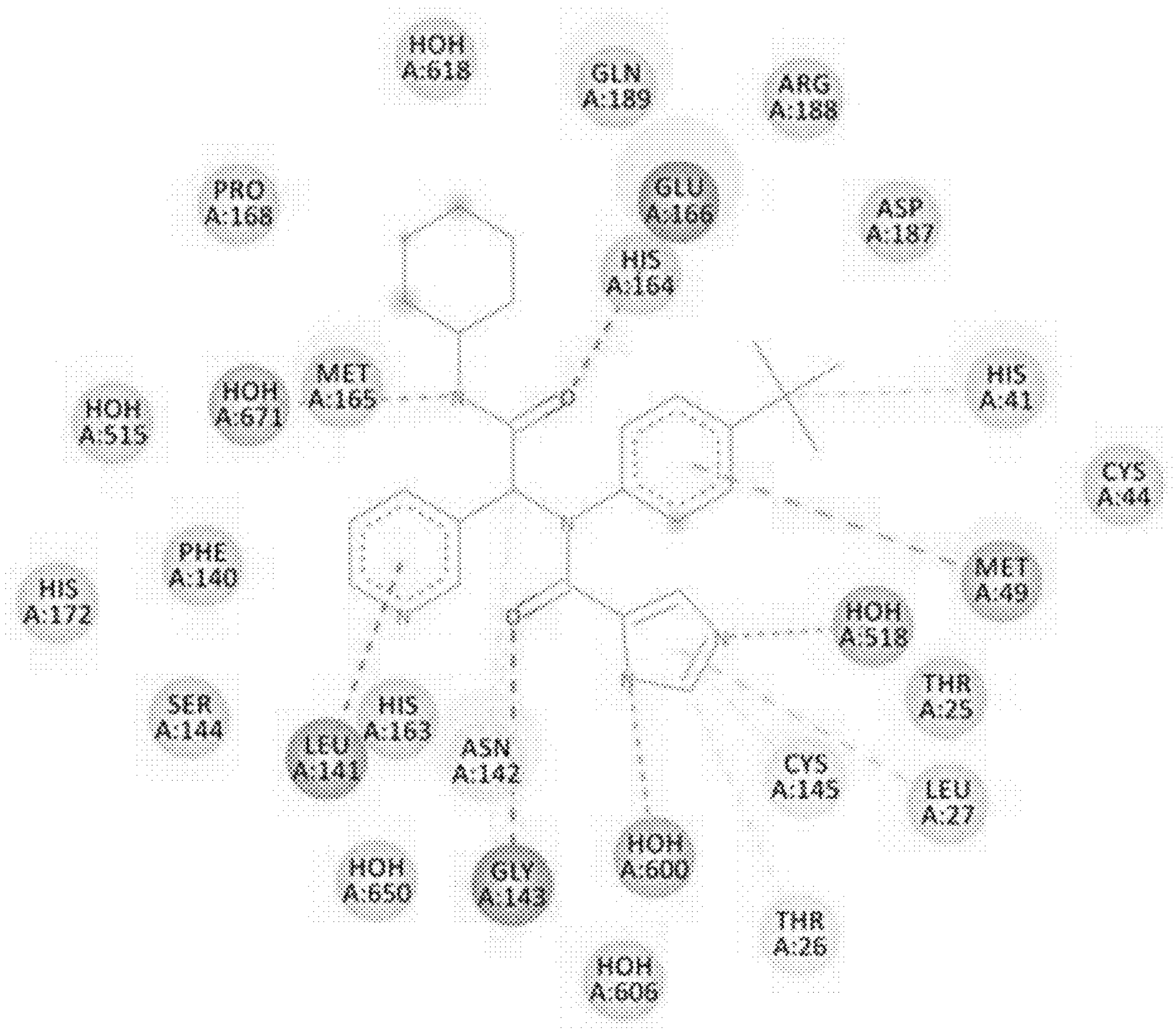
FIG. 3 depicts a 2D representation of predicted non-covalent interactions of (S)—N-(4-(tert-butyl)phenyl)-N-(1-(2-cyanopyridin-3-yl)-2-(cyclohexylamino)-2-oxoethyl)-1H-imidazole-5-carboxamide bound to COVID-19 Main Protease (PDB 6W63).

Example 4: Properties of thioimidate 3CL protease adduct formed with (S)—N-(4-(tert-butyl)phenyl)-N-(1-(2-cyanopyridin-3-yl)-2-(cyclohexylamino)-2-oxoethyl)-1H-imidazole-5-carboxamide A simulation model was used to predict the thiomidate adduct with COVID-19 3CL protease produced upon reaction with active site Cys145, as shown in FIG. 2A. An overlay of the non-covalent inhibitor ((S)—N-(4-(tert-butyl) phenyl)-N-(1-(2-cyanopyridin-3-yl)-2-(cyclohexylamino)-2-oxoethyl)-1H-imidazole-5-carboxamide) in active site from 6W63 PDB with predicted reversible covalent nitrile adduct, as shown in FIG. 2B, suggests that all bonding interactions of the non-covalent inhibitor are maintained in the thiomidate adduct. In addition, it is anticipated by the model that the thioimidate is further stabilized by H-bonding with His164 backbone carbonyl. The inhibitor also docks well into the COV229E protease structure. This model suggests that analogs of the inhibitor have a broad spectrum of activity across CoV 3CL proteases.

Figure 4:
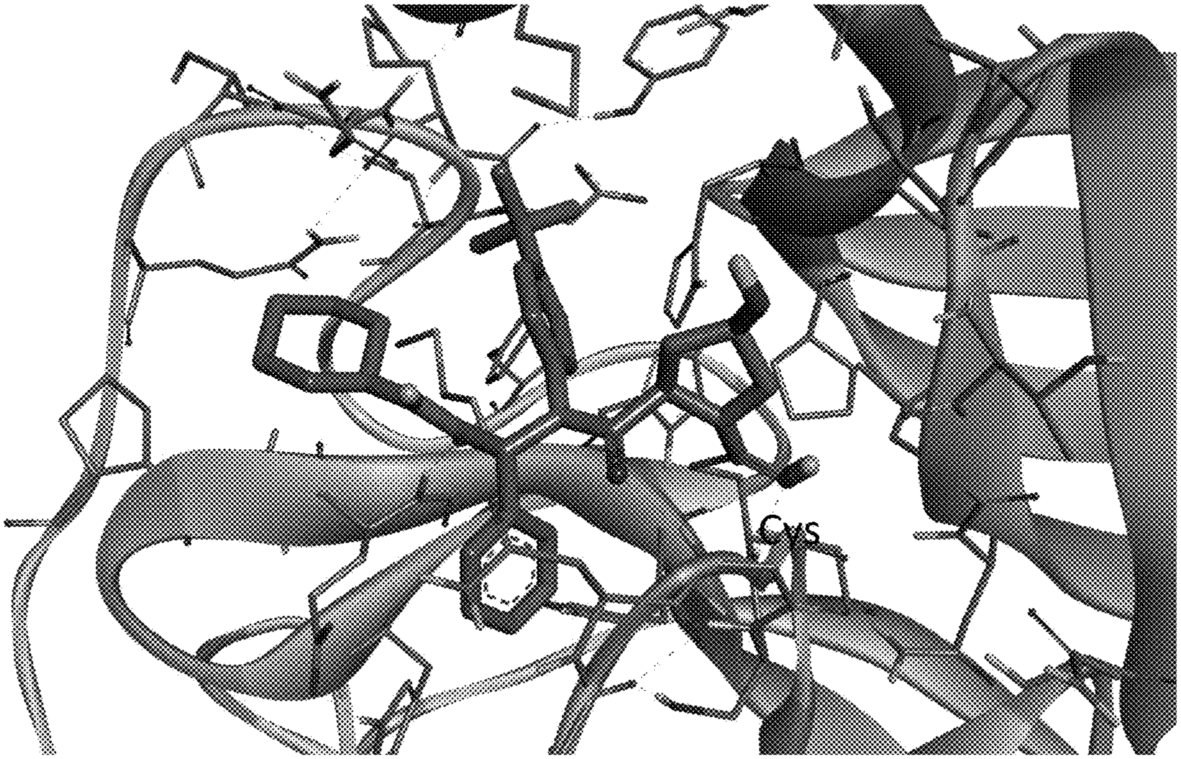
FIG. 4 depicts in 3D and 2D the reversible covalent isothiourea conjugate formed from the reaction of active site Cys 145 of SARS-CoV2 main protease with cyanamide inhibitor (2R,4R)—N-(4-(tert-butyl)phenyl)-1-cyano-N—((R)-2-(cyclohexylamino)-2-oxo-1-(pyridin-3-yl)ethyl)-4-hydroxypyrrolidine-2-carboxamide.
Figure 4:
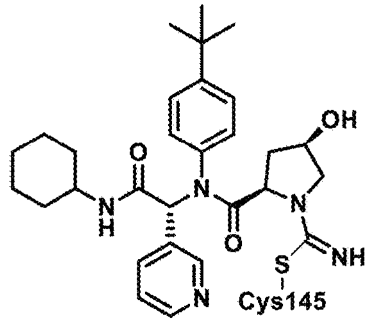

Example 5: Properties of thioimidate 3CL protease adduct formed with (2R,4R)—N-(4-(tert-butyl)phenyl)-1-cyano-N—((R)-2-(cyclohexylamino)-2-oxo-1-(pyridin-3-yl)ethyl)-4-hydroxypyrrolidine-2-carboxamide A simulation model was used to predict the thiomidate adduct with SARS CoV 3CL protease produced upon reaction with active site Cys145, as shown in FIG. 4. The model suggests that all significant bonding interactions of non-covalent inhibitor in SARS CoV PDB and in MERS CoV 3CL proteases are expected to be maintained in isothiourea adduct. It additionally shows that the isothiourea adduct may be further stabilized by H-bonding with Thr26 backbone carbonyl and the Cys145 NH. The inhibitor also docks well into the CoV229E protease structure, as well as SARS CoV and MERS CoV 3CL proteases without significant perturbations. Analogs of the structure may be anticipated to have a broad spectrum of activity across CoV 3CL proteases.

Example 6: Synthesis of Covalent Viral Protease Inhibitor Compounds

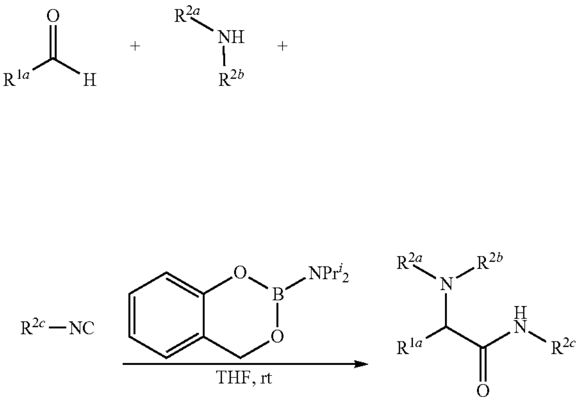

A solution of (diisopropylamino)borane (0.6 mmol) in THF (1.0 L) were added amine (0.6-0.8 mmol), aldehyde (0.4 mmol), and isocyanide (0.6 mmol) at room temperature. The mixture was stirred for 12-16 h, quenched with water, and extracted with ethyl acetate. The organic layer was dried over $Na_2SO_4$ and evaporated under vacuum. The resulting product was purified by silica gel column chromatography with ether and dichloromethane, or ethyl acetate and hexanes.

Example 7: Synthesis of Covalent Viral Protease Inhibitor Compounds

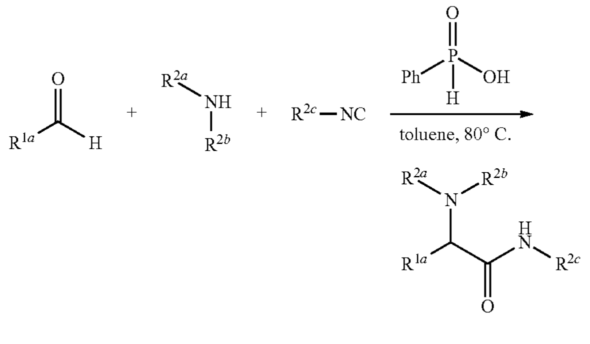

A solution of aldehyde (0.5 mmol), amine (0.5 mmol), isocyanide (0.5 mmol), and phenylphosphinic acid were stirred at 80° C. in toluene (0.5 mL). The mixture was stirred for 12-36 h and then directly subjected to silica gel column chromatography (ethyl acetate/hexanes) to afford the product.

Example 8: Synthesis of Compound 253

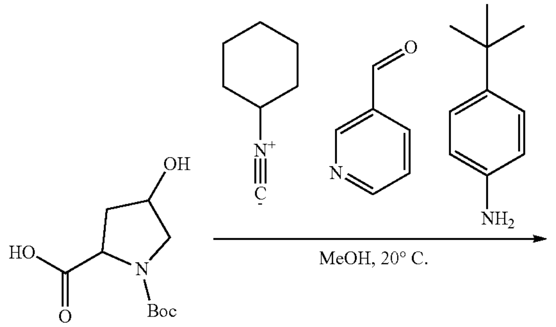

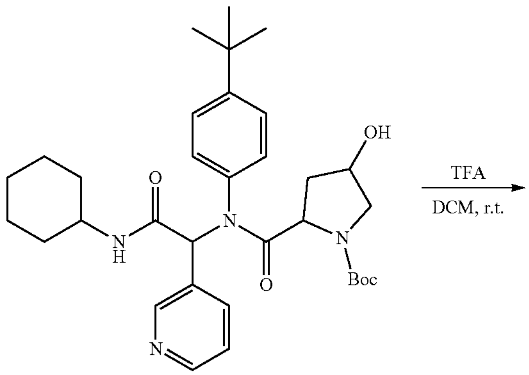

-continued

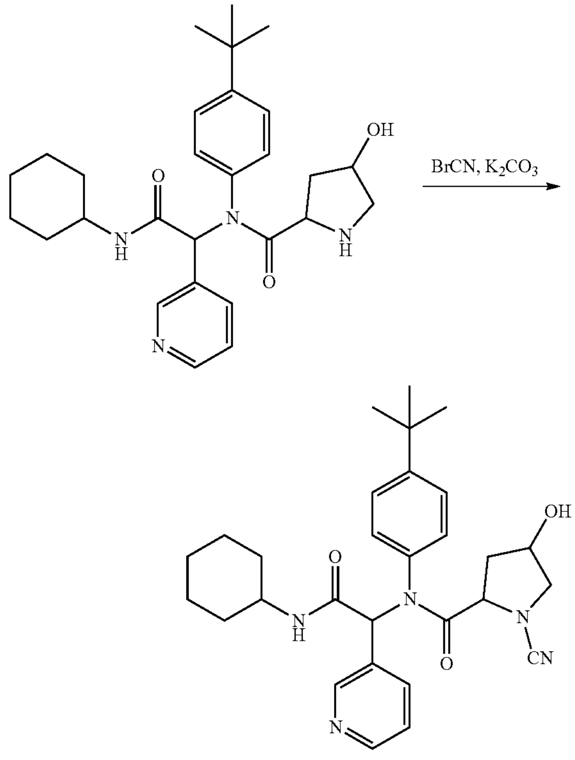

A mixture of 1-(tert-butoxycarbonyl)-4-hydroxypyrrolidine-2-carboxylic acid, isocyanocyclohexane, nicotinaldehyde, and 4-(tert-butyl)aniline in methanol were stirred at 20° C. The resultant mixture was concentrated in vacuo or gentle stream of nitrogen and then purified by column chromatography. Then, tert-butyl 2-((4-(tert-butyl)phenyl)(2-(cyclohexylamino)-2-oxo-1-(pyridin-3-yl)ethyl)carbamoyl)-4-hydroxypyrrolidine-1-carboxylate was treated with trifluoroacetic acid in dichloromethane at room temperature. Once the reaction was complete, the resultant mixture was purified to afford N-(4-(tert-butyl)phenyl)-N-(2-(cyclohexylamino)-2-oxo-1-(pyridin-3-yl)ethyl)-4-hydroxypyrrolidine-2-carboxamide. N-(4-(tert-butyl)phenyl)-N-(2-(cyclohexylamino)-2-oxo-1-(pyridin-3-yl)ethyl)-4-hydroxypyrrolidine-2-carboxamide was then treated with cyanogen bromide and potassium carbonate in dimethylformamide to afford the product.

Example 9: Synthesis of Compound 100

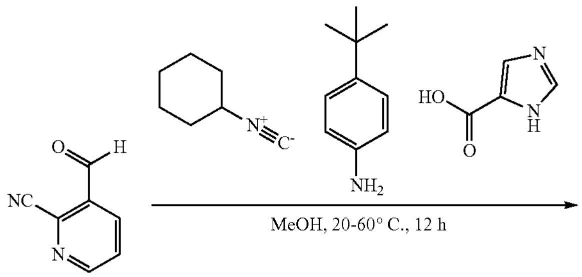

-continued

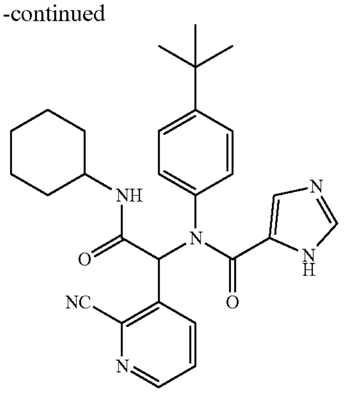

2-isocyanopyridine-3-carbaldehyde (50 mg, 378.45 umol, 1 eq), 4-tert-butylaniline (56.48 mg, 378.45 umol, 59.76 uL, 1 eq) and 1H-imidazole-5-carboxylic acid (42.42 mg, 378.45 umol, 1 eq) in MeOH (0.3 mL) was stirred at 20° C. for 0.5 h, then the isocyanocyclohexane (37.18 mg, 340.60 umol, 42.35 uL, 0.9 eq) was added and the solution was stirred at 60° C. for 11.5 h. Upon completion, the solution was filtrated and the filtrate was concentrated to give the product. The residue was purified by prep-HPLC (neutral condition), column: Waters Xbridge BEH C18 100*25 mm*5 um; mobile phase: [water (10 mM $NH_4HCO_3$)-ACN]; B %: 30%-55%, 10 min. N-(4-tert-butylphenyl)-N-[1-(2-cyano-3-pyridyl)-2-(cyclohexylamino)-2-oxo-ethyl]-1H-imidazole-5-carboxamide (4.5 mg, 9.29 umol) was obtained as a solid. $^1$H NMR (400 MHz, METHANOL-$d_4$) δ ppm 8.51-8.50 (m, J=3.6 Hz, 1H), 7.64 (s, 2H), 7.43-7.33 (m, 5H), 6.60 (br s, 1H), 5.36 (br s, 1H), 3.69 (br t, J=10.8 Hz, 1H), 1.91-1.57 (m, 5H), 1.43-1.30 (m, 2H), 1.26 (s, 9H), 1.22-1.04 (m, 3H). MS (ESI) m/z 485.2 $[M+H]^+$.

Example 10: Synthesis of N-(1-(2-bromopyridin-3-yl)-2-(cyclohexylamino)-2-oxoethyl)-N-(4-(tert-butyl)phenyl)-1H-imidazole-5-carboxamide

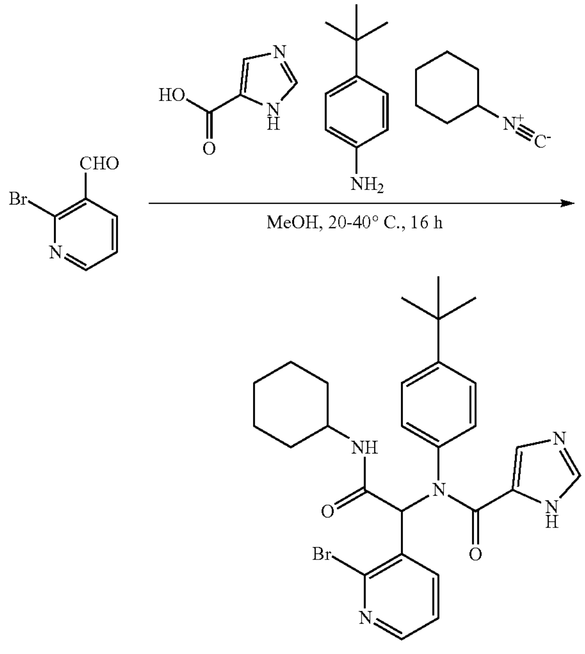

To a stirred solution of 2-bromopyridine-3-carbaldehyde (300 mg, 1.61 mmol, 1 eq), 4-tert-butylaniline (240.26 mg, 1.61 mmol, 254.25 uL, 1 eq) and 1H-imidazole-5-carboxylic acid (180.46 mg, 1.61 mmol, 1 eq) in MeOH (6 mL), and the mixture was stirred at 20° C. for 0.5 h, and then isocyano-cyclohexane (158.19 mg, 1.45 mmol, 180.17 uL, 0.9 eq) was added into the mixture, the mixture was stirred at 40° C. for 15.5 h. Upon the reaction was completely. The mixture was filtered through an injector directly to get the liquid, and the mixture was concentrated in vacuum directly to get the product. The product was purified by prep-TLC (petroleum ether:ethyl acetate=2:1) to get the N-(1-(2-bromophenyl)-2-(cyclohexylamino)-2-oxoethyl)-N-(4-(tert-butyl)phenyl)-1H-imidazole-5-carboxamide (32 mg, 56.75 umol) as a solid. MS (ESI) m/z 538.2 $[M+H]^+$. $^1$H NMR (400 MHz, CHLOROFORM-d) δ ppm 8.22-8.20 (m, 1H), 7.64 (s, 1H), 7.47-7.43 (m, 1H), 7.27 (s, 4H), 6.96-6.93 (m, 1H), 6.54 (s, 1H), 5.89-5.88 (d, J=5.6, 1H), 5.51 (s, 1H), 3.87-3.83 (m, 1H), 2.05-1.95 (m, 1H), 1.92-1.82 (m, 1H), 1.79-1.56 (m, 3H), 1.45-1.31 (m, 2H), 1.26 (s, 9H), 1.24-1.02 (m, 3H).

Example 11: Synthesis of N-(4-(tert-butyl)phenyl)-N-(1-(2-chloro-6-(trifluoromethyl)pyridin-3-yl)-2-(cyclohexylamino)-2-oxoethyl)-1H-imidazole-5-carboxamide

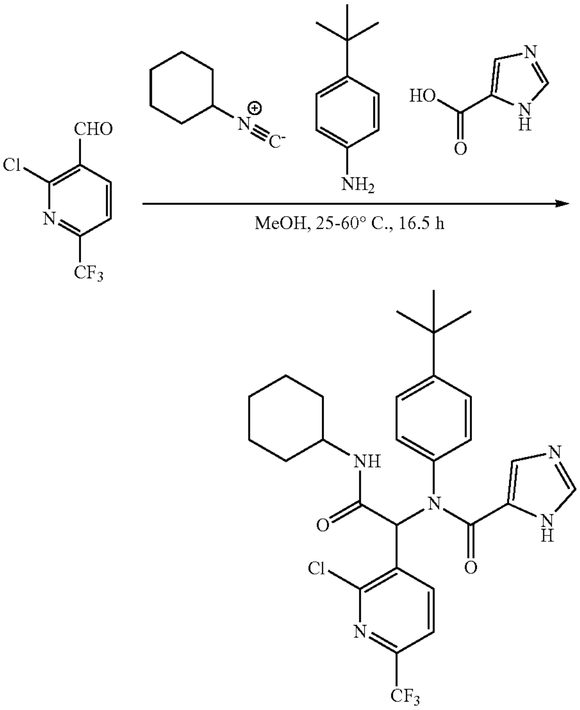

2-chloro-6-(trifluoromethyl)pyridine-3-carbaldehyde (150 mg, 715.81 umol, 1 eq), 4-tert-butylaniline (106.82 mg, 715.81 umol, 113.04 uL, 1 eq), 1H-imidazole-5-carboxylic acid (80.23 mg, 715.81 umol, 1 eq) was added the MeOH (0.3 mL) and the solution was stirred at 25° C. for 0.5 h, then the isocyanocyclohexane (70.33 mg, 644.23 umol, 80.10 uL, 0.9 eq) was added and the solution was stirred at 60° C. for 16 h. Upon completion, the solution was filtrated and the filtrate was concentrated to give the product. The residue was purified by prep-HPLC (neutral condition), column: Phenomenex Gemini-NX 80*40 mm*3 um; mobile phase:

[water (10 mM $NH_4HCO_3$)-ACN]; B %: 50%-70%, 8 min. N-(4-tert-butylphenyl)-N-[1-[2-chloro-6-(trifluoromethyl)-3-pyridyl]-2-(cyclohexylamino)-2-oxo-ethyl]-1H-imidazole-5-carboxamide (23 mg, 39.70 umol) was obtained as a solid. $^1H$ NMR (400 MHz, DMSO-$d_6$) δ ppm 12.74 (br s, 1H), 8.37 (br d, J=6.2 Hz, 1H), 8.15-6.66 (m, 7H), 6.45 (br s, 1H), 5.30 (br s, 1H), 3.55 (br s, 1H), 1.67-1.50 (m, 5H), 1.25-1.03 (m, 14H). MS (ESI) m/z 562.1 $[M+H]^+$.

Example 12: Synthesis of Compound 103

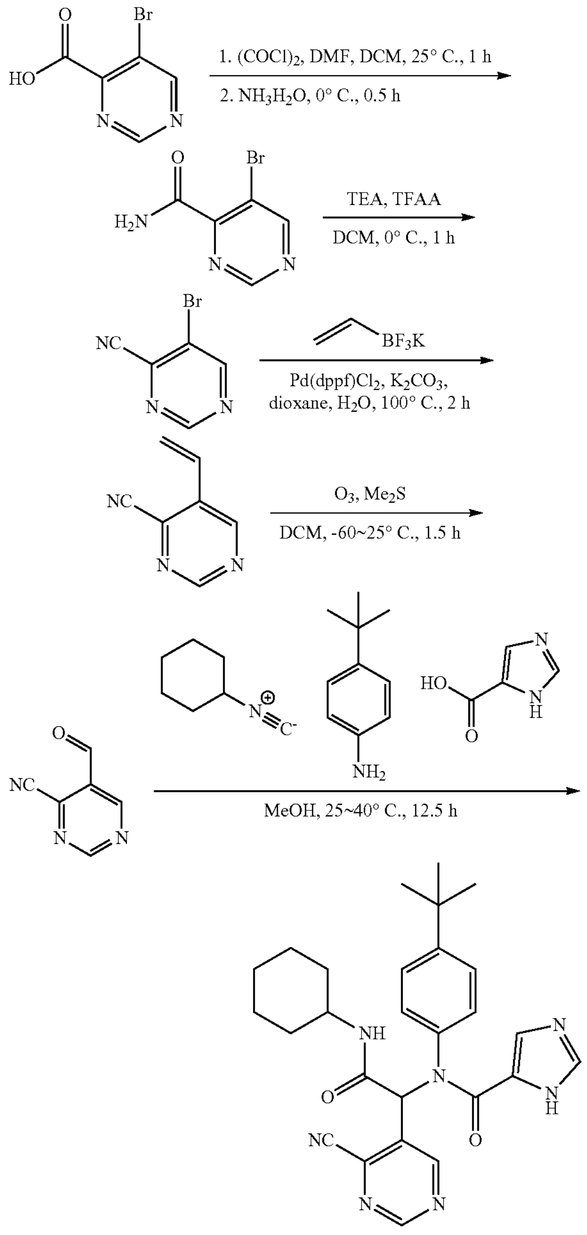

Step 1: 5-bromopyrimidine-4-carboxamide

To a solution of 5-bromopyrimidine-4-carboxylic acid (4.5 g, 22.17 mmol, 1 eq) in DCM (45 mL) was added $(COCl)_2$ (8.44 g, 66.50 mmol, 5.82 mL, 3 eq) and DMF (16.20 mg, 221.68 umol, 17.06 uL, 0.01 eq). The mixture was stirred at 25° C. for 1 h. Upon completion, the solution was-concentrated to remove the DCM, and then re-dissolved with THF (2 mL). The resulting solution was added to the $NH_3 \cdot H_2O$ (41.99 g, 443.36 mmol, 46.15 mL, 20 eq) at 0° C. and the solution was stirred at 0° C. for 0.5 h. Upon completion, the solution was diluted with $H_2O$ (40 mL), extracted with ethyl acetate (50 mL*3), the combined organic phase was dried over $Na_2SO_4$, filtrated and concentrated to give the product. The product was used to next step directly and without further purification. 5-bromopyrimidine-4-carboxamide (3.86 g, 19.03 mmol) was obtained as a solid. MS (ESI) m/z 202.0 $[M+H]^+$.

Step 2: 5-bromopyrimidine-4-carbonitrile

5-Bromopyrimidine-4-carboxamide (3.85 g, 19.06 mmol, 1 eq) and TEA (5.01 g, 49.55 mmol, 6.90 mL, 2.6 eq) in DCM (40 mL) was cooled to 0° C., then the TFAA (5.20 g, 24.78 mmol, 3.45 mL, 1.3 eq) was added drop wise and the solution was stirred at 0° C. for 1 h. Upon completion, the solution was diluted with $H_2O$ (50 mL), extracted with DCM (60 mL*3), the combined organic phase was dried over $Na_2SO_4$, filtrated and concentrated to give the product. The residue was purified by column chromatography ($SiO_2$, petroleum ether/ethyl acetate=20/1 to 1/1). 5-bromopyrimidine-4-carbonitrile (2.9 g, 14.97 mmol) was obtained as an oil. MS (ESI) m/z 184.0 $[M+H]^+$.

Step 3: 5-vinylpyrimidine-4-carbonitrile

5-Bromopyrimidine-4-carbonitrile (1.5 g, 8.15 mmol, 1 eq), potassium; trifluoro (vinyl)boranuide (1.64 g, 12.23 mmol, 1.5 eq) in dioxane (15 mL)/$H_2O$ (1.5 mL) was added the $K_2CO_3$ (2.25 g, 16.30 mmol, 2 eq), Pd(dppf)$Cl_2$ (596.52 mg, 815.25 umol, 0.1 eq) and the solution was stirred at 100° C. for 2 h. Upon completion, the solution was diluted with $H_2O$ (20 mL), extracted with ethyl acetate (EtOAc) (30 mL×3). The combined organic phase was dried over $Na_2SO_4$, filtered and concentrated to give the product. The residue was purified by column chromatography ($SiO_2$, petroleum ether/EtOAc=20/1 to 1/1). 5-vinylpyrimidine-4-carbonitrile (650 mg, 4.96 mmol) was obtained as a solid. MS (ESI) m/z 132.1 $[M+H]^+$.

Step 4: 5-formylpyrimidine-4-carbonitrile

5-Vinylpyrimidine-4-carbonitrile (150 mg, 1.14 mmol, 1 eq) in DCM (10 mL) was cooled to −60° C. and ozone (54.90 mg, 1.14 mmol, 1.0 eq) was added into the solution and the resulting solution was stirred at −60° C. for 0.5 h. Upon completion, the solution was purged with $O_2$ for 0.5 h and any remaining ozone was removed. The solution was added with $Me_2S$ (142.15 mg, 2.29 mmol, 168.02 uL, 2 eq) and stirred at 25° C. for 1 h. Upon completion, the solution was diluted with DCM (20 mL), washed with $H_2O$ (20 mL*3), the combined organic phase was dried over $Na_2SO_4$, filtered and concentrated to give the product. The product was used for the next step directly and without further purification. 5-formylpyrimidine-4-carbonitrile (150 mg) was obtained as an oil.

Step 5: N-(4-(tert-butyl)phenyl)-N-(1-(4-cyanopyrimidin-5-yl)-2-(cyclohexylamino)-2-oxoethyl)-1H-imidazole-5-carboxamide 5-Formylpyrimidine-4-carbonitrile (150 mg, 1.13 mmol, 1 eq) and 4-tert-butylaniline (168.17 mg, 1.13 mmol, 177.96 uL, 1 eq) in MeOH (1 mL) was stirred at 25° C. for 0.5 h, and then 1H-imidazole-5-carboxylic acid (126.31 mg, 1.13 mmol, 1 eq) and isocyanocyclohexane (110.72 mg, 1.01 mmol, 126.11 uL, 0.9 eq) were added. The resulting solution was stirred at 40° C. for 12 h. Upon completion, the solution was filtered and the filtrate was concentrated to give the product. The residue was purified by prep-HPLC (TFA condition), column: Phenomenex luna C18 100*40 mm*5 um; mobile phase: [water (0.1% TFA)-ACN]; B %: 20%-60%, 8 min. N-(4-tert-butylphenyl)-N-[1-(4-cyanopyrimidin-5-yl)-2-(cyclohexylamino)-2-oxo-ethyl]-1H-imidazole-5-carboxamide (3 mg, 6.18 umol) was obtained as a solid. $^1$H NMR (400 MHz, METHANOL-$d_4$) S=9.16 (s, 1H), 8.73 (s, 1H), 8.60 (s, 1H), 8.47 (br d, J=7.3 Hz, 1H), 7.60-7.21 (m, 4H), 6.53 (s, 1H), 5.61 (s, 1H), 3.79-3.64 (m, 1H), 1.86-1.60 (m, 5H), 1.38-1.33 (m, 3H), 1.30 (s, 9H), 1.22-1.12 (m, 211). MS (ESI) m/z 486.3 $[M+H]^+$.

Example 13: Synthesis of Compound 104

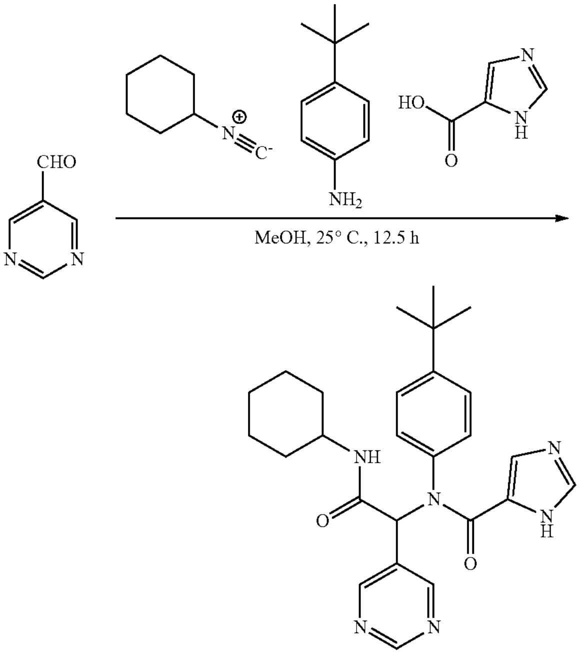

Pyrimidine-5-carbaldehyde (200 mg, 1.85 mmol, 1 eq), 4-tert-butylaniline (276.11 mg, 1.85 mmol, 292.18 uL, 1 eq) and 1H-imidazole-5-carboxylic acid (207.38 mg, 1.85 mmol, 1 eq) in MeOH (0.6 mL) were stirred at 25° C. for 0.5 h, and then the isocyanocyclohexane (201.98 mg, 1.85 mmol, 230.05 uL, 1 eq) was added. The solution was stirred at 25° C. for 12 h. Upon completion, the solution was filtered and the filtrate was concentrated to give the product. The product was purified by prep-TLC (DCM:MeOH=10:1). N-(4-tert-butylphenyl)-N-[2-(cyclohexylamino)-2-oxo-1-pyrimidin-5-yl-ethyl]-1H-imidazole-5-carboxamide (200 mg, 419.25 umol) was obtained as a solid. $^1$H NMR (400 MHz, DMSO-$d_6$) δ=12.79 (br s, 1H), 8.96 (s, 1H), 8.56-8.44 (m, 2H), 8.16 (d, J=7.7 Hz, 1H), 7.77-7.06 (m, 511), 6.16 (s, 1H), 5.16 (s, 1H), 3.66-3.51 (m, 1H), 1.75-1.62 (m, 5H), 1.24 (s, 9H), 1.20-1.07 (m, 5H). MS (ESI) m/z 461.2 $[M+H]^+$.

Example 14: Synthesis of Compound 118

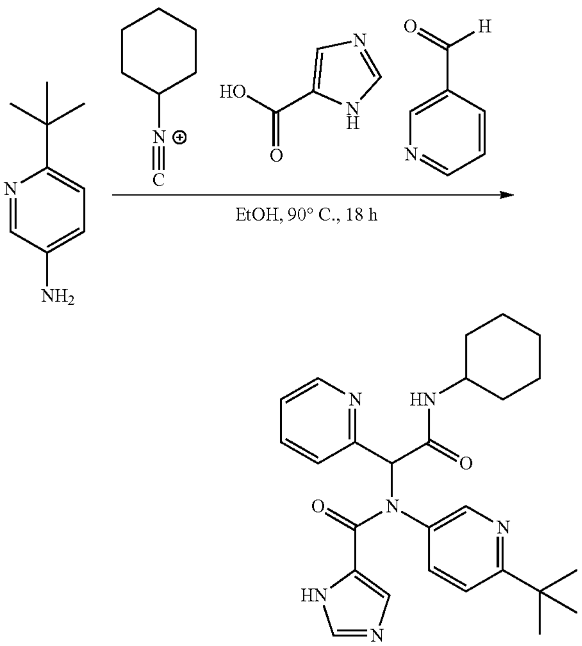

To a stirred solution of 1H-imidazole-5-carboxylic acid (7.46 mg, 66.57 umol, 1 eq), 6-(tert-butyl)pyridin-3-amine (0.01 g, 66.57 umol, 1 eq), and nicotinaldehyde (7.13 mg, 66.57 umol, 6.25 uL, 1 eq) in EtOH (1 mL) was added isocyanocyclohexane (6.54 mg, 59.91 umol, 7.45 uL, 0.9 eq). The resulting mixture was stirred at 90° C. for 18 h. Upon completion, the residue was purified by prep-HPLC (column: Phenomenex Gemini-NX 80*40 mm*3 um; mobile phase: [water (10 mM $NH_4HCO_3$)-ACN]; B %: 25%-45%, 8 min). N-(6-(tert-butyl)pyridin-3-yl)-N-(2-(cyclohexylamino)-2-oxo-1-(pyridin-2-yl)ethyl)-1H-imidazole-5-carboxamide (16.12 mg, 32.75 umol) was obtained as a solid. $^1$H NMR (400 MHz, Methanol-$d_4$) δ ppm 8.32-8.40 (m, 2H) 8.05-8.30 (m, 1H) 7.57 (br s, 3H) 7.33-7.45 (m, 1H) 7.22-7.31 (m, 1H) 6.30-6.48 (m, 1H) 5.64-5.96 (m, 1H) 3.64-3.77 (m, 1H) 1.83 (m, 2H) 1.59-1.78 (m, 4H) 1.33-1.44 (m, 2H) 1.26-1.31 (m, 9H) 1.07-1.21 (m, 2H). MS (ESI) m/z 461.3 $[M+H]^+$.

Example 15: Synthesis of Compound 899

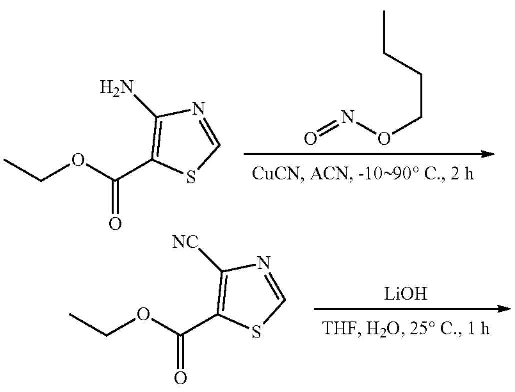

-continued

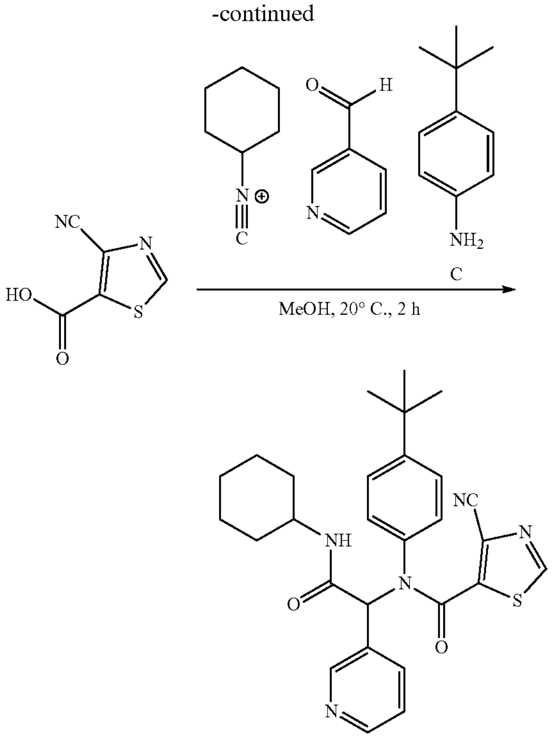

Step 1: ethyl 4-cyanothiazole-5-carboxylate

To a mixture of ethyl 4-aminothiazole-5-carboxylate (1 g, 5.81 mmol, 1 eq) and copper (I) cyanide (572.11 mg, 6.39 mmol, 1.40 mL, 1.1 eq) in ACN (25 mL) was added isopentyl nitrite (952.38 mg, 8.13 mmol, 1.09 mL, 1.4 eq) at −10° C. After stirring the mixture at 90° C. for 2 h, the mixture was filtered and concentrated. The product was purified by prep-HPLC (TFA condition), column: Phenomenex luna C18 250*50 mm*10 um; mobile phase: [water (0.1% TFA)-ACN]; B %: 30%-60%, 10 min. ethyl 4-cyanothiazole-5-carboxylate (150 mg, 740.95 umol) was obtained as a solid. MS (ESI) m/z 183.0 $[M+H]^+$.

Step 2: 4-cyanothiazole-5-carboxylic acid

To a mixture of ethyl 4-cyanothiazole-5-carboxylate (60 mg, 296.38 umol) in THF (6 mL) and $H_2O$ (1 mL) was added LiOH (14.20 mg, 592.76 umol, 2 eq). After stirring the mixture at 25° C. for 1 h, the mixture was filtered and concentrated. The reaction mixture was adjusted to pH=3 by addition HCl (1 M) at 25° C., and then diluted with $H_2O$ (20 mL) and extracted with EtOAc (30 mL*3). The combined organic layers were washed with brine 30 mL, dried over $Na_2SO_4$, filtered and concentrated under reduced pressure to give a residue 4-cyanothiazole-5-carboxylic acid (40 mg, 233.54 umol) as a solid. MS (ESI) m/z 155.0 $[M+H]^+$.

Step 3: N-(4-tert-butylphenyl)-4-cyano-N-[2-(cyclohexylamino)-2-oxo-1-(3-pyridyl)ethyl]thiazole-5-carboxamide To a mixture of 4-tert-butylaniline (41.80 mg, 280.09 umol, 44.23 uL, 1 eq) and pyridine-3-carbaldehyde (30 mg, 280.09 umol, 26.32 uL, 1 eq) in MeOH (2 mL) was added 4-cyanothiazole-5-carboxylic acid (47.97 mg, 280.09 umol) at 20° C. The mixture was stirred at 20° C. for 30 min, and then isocyanocyclohexane (27.52 mg, 252.08 umol, 31.34 uL, 0.9 eq) was added at 25° C. The mixture was stirred at 20° C. for 1.5 h and a solid was observed. The mixture was filtered to afford the product N-(4-tert-butylphenyl)-4-cyano-N-[2-(cyclohexylamino)-2-oxo-1-(3-pyridyl)ethyl]thiazole-5-carboxamide (30 mg, 59.80 umol) as a solid. MS (ESI) m/z 502.3 $[M+H]^+$. $^1H$ NMR (400 MHz, DMSO-$d_6$) δ ppm 9.10 (s, 1H), 8.39-8.31 (m, 2H), 8.21 (d, J=7.6 Hz, 1H), 7.91-6.67 (m, 6H), 6.23 (s, 1H), 3.70-3.50 (m, 1H), 1.84-1.46 (m, 5H), 1.32-0.99 (m, 14H).

Example 16: Synthesis of 4-bromo-N-(4-tert-butylphenyl)-N-[2-(cyclohexylamino)-2-oxo-1-(3-pyridyl)ethyl]thiazole-5-carboxamide

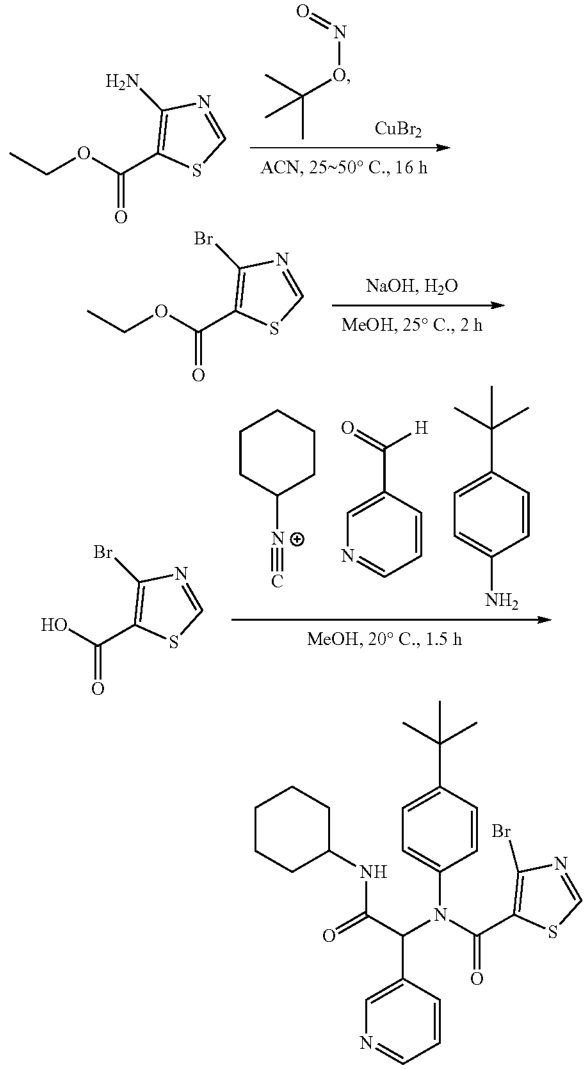

Step 1: ethyl 4-bromothiazole-5-carboxylate

To a mixture of tert-butyl nitrite (179.65 mg, 1.74 mmol, 207.21 uL, 1.5 eq) in ACN (4 mL) was added $CuBr_2$ (311.29 mg, 1.39 mmol, 65.26 uL, 1.2 eq). The mixture was stirred at 50° C. for 1 h, and then ethyl 4-aminothiazole-5-carboxylate (200 mg, 1.16 mmol, 1 eq) was added under 25° C. After stirring the mixture 25° C. for 15 h, the mixture was poured into water (30 mL). The solution was filtered and washed with water (30 mL*3) and then dried to afford the product. The residue was purified by column chromatography ($SiO_2$, petroleum ether/ethyl acetate=8/1 to 3/1) to get the compound ethyl 4-bromothiazole-5-carboxylate (40 mg, 152.49 umol) as a solid. MS (ESI) m/z 235.9 $[M+H]^+$.

Step 2: 4-bromothiazole-5-carboxylic acid

To a mixture of ethyl 4-bromothiazole-5-carboxylate (30 mg, 114.37 umol) in MeOH (2 mL) and $H_2O$ (0.5 mL) was added NaOH (9.15 mg, 228.73 umol, 2 eq). The mixture was stirred under 25° C. for 2 h, and then the resulting mixture was adjusted pH=3 by addition HCl (1 M) at 25° C. The solution was diluted with $H_2O$ (20 mL) and extracted with ethyl acetate (30 mL*3). The combined organic layers were washed with brine 30 mL dried over $Na_2SO_4$, filtered and concentrated under reduced pressure to give the compound 4-bromothiazole-5-carboxylic acid (20 mg, 86.52 umol) as a solid. MS (ESI) m/z 207.9 $[M+H]^+$.

Step 3: 4-bromo-N-(4-tert-butylphenyl)-N-[2-(cyclohexylamino)-2-oxo-J-(3-pyridyl)ethyl]thiazole-5-carboxamide To a mixture of 4-tert-butylaniline (16.72 mg, 112.03 umol, 17.69 uL, 1 eq) and pyridine-3-carbaldehyde (12 mg, 112.03 umol, 10.53 uL, 1 eq) in MeOH (2 mL) was added 4-bromothiazole-5-carboxylic acid (23.31 mg, 112.03 umol, 1 eq). The mixture was stirred at 20° C. for 30 min, and then isocyanocyclohexane (11.01 mg, 100.83 umol, 12.54 uL, 0.9 eq) was added to the solution. The mixture was stirred at 20° C. for 1 h, and then filtered and concentrated. The concentrate was purified with prep-HPLC, column: Waters Xbridge BEH C18 100*30 mm*10 um; mobile phase: [water (10 mM NH4HCO3)-ACN]; B %: 40%-70%, 6 min to afford the product 4-bromo-N-(4-tert-butylphenyl)-N-[2-(cyclohexylamino)-2-oxo-1-(3-pyridyl)ethyl]thiazole-5-carboxamide (30 mg, 54.00 umol) as a solid. MS (ESI) m/z 555.2 $[M+H]^+$. $^1H$ NMR (400 MHz, DMSO-$d_6$) δ ppm 8.96 (s, 1H), 8.35 (dt, J=1.7, 5.0 Hz, 2H), 8.12 (br d, J=7.7 Hz, 1H), 7.41 (br d, J=7.9 Hz, 1H), 7.20-6.94 (m, 5H), 6.17 (s, 1H), 3.67-3.51 (m, 1H), 1.80-1.47 (m, 5H), 1.29-0.97 (m, 14H).

Example 17: Synthesis of Compound 121

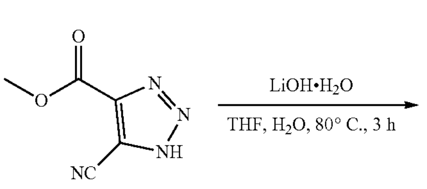

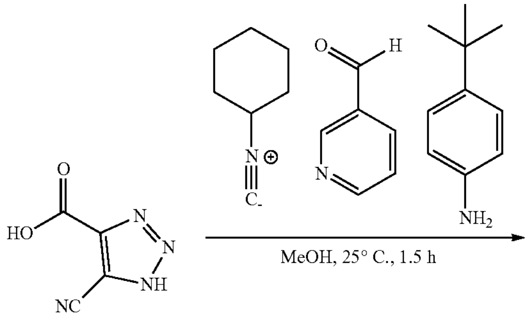

-continued

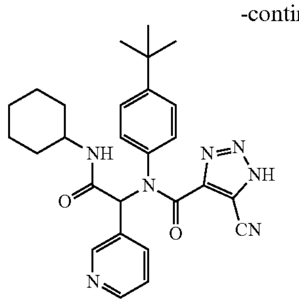

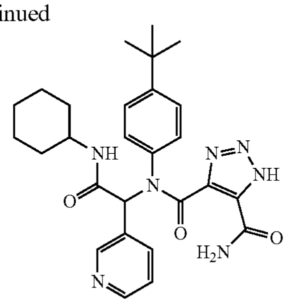

Step 1: 5-cyano-1H-triazole-4-carboxylic acid

To a solution of methyl 5-cyano-1H-triazole-4-carboxylate (50 mg, 328.71 umol, 1 eq) in THF (1 mL) and $H_2O$ (1 mL) was added $LiOH{\cdot}H_2O$ (41.38 mg, 986.12 umol, 3 eq). The resulting solution was stirred at 80° C. for 3 h. The solution was diluted with $H_2O$ (10 mL), extracted with DCM (3*20 mL), the combined organic phase was dried over $Na_2SO_4$, filtered and concentrated to afford the product. The product was not purified and used directly for the next step. Get 5-cyano-1H-triazole-4-carboxylic acid (50 mg, 289.68 umol) as an oil. MS (ESI) m/z 139.1 [M+H]+.

Step 2: N-(4-tert-butylphenyl)-5-cyano-N-[2-(cyclohexylamino)-2-oxo-1-(3-pyridyl)ethyl]-1H-triazole-4-carboxamide and N4-(4=tert-butylphenyl)-N4-[2-(cyclohexylamino)-2-oxo-1-(3-pyridyl)ethyl]-1H-triazole-4,5-dicarboxamide A solution of pyridine-3-carbaldehyde (38.78 mg, 362.10 umol, 34.02 uL, 1 eq), 4-tert-butylaniline (54.04 mg, 362.10 umol, 57.18 uL, 1 eq), isocyanocyclohexane (39.53 mg, 362.10 umol, 45.02 uL, 1 eq), 5-cyano-1H-triazole-4-carboxylic acid (50 mg, 362.10 umol, 1 eq) in MeOH (5 mL) was stirred at 25° C. for 1.5 h. The solution was diluted with $H_2O$ (10 mL) and extracted with DCM (3*20 mL). The combined organic phase was dried over $Na_2SO_4$, filtered and concentrated to afford the product. The product was purified by prep-HPLC (column: Waters Xbridge BEH C18 100*30 mm*10 um; mobile phase: [water (10 mM $NH_4HCO_3$)-ACN]; B %: 25%-55%, 10 min) to afford N-(4-tert-butylphenyl)-5-cyano-N-[2-(cyclohexylamino)-2-oxo-1-(3-pyridyl)ethyl]-1H-triazole-4-carboxamide (30 mg, 61.78 umol) as a solid. MS (ESI) m/z 504.2 $[M+H]^+$. $^1H$ NMR (400 MHz, DMSO-$d_6$) δ ppm 0.95-1.12 (m, 3H) 1.14 (s, 9H) 1.19-1.24 (m, 2H) 1.48-1.66 (m, 5H) 3.50-3.60 (m, 1H) 6.30 (br s, 1H) 6.91-7.11 (m, 5H) 7.14-7.22 (m, 1H) 7.40-7.42 (m, 1H) 8.11 (d, J=7.70 Hz, 1H) 8.33-8.36 (m, 2H); and N4-(4-tert-butylphenyl)-N4-[2-(cyclohexylamino)-2-oxo-1-(3-pyridyl)ethyl]-1H-triazole-4,5-dicarboxamide (10 mg, 18.86 umol) as a solid. MS (ESI) m/z 486.2 $[M+H]^+$. $^1H$ NMR (400 MHz, DMSO-$d_6$) δ ppm 1.09-1.31 (m, 14H) 1.56-1.79 (m, 5H) 3.68 (br s, 1H) 6.13 (br s, 1H) 6.88 (br d, J=7.70 Hz, 2H) 7.04 (br d, J=8.31 Hz, 2H) 7.18 (dd, J=7.82, 4.77 Hz, 1H) 7.44-7.63 (m, 2H) 7.78 (br s, 1H) 8.32-8.35 (m, 2H) 8.51 (br s, 1H).

Example 18: Synthesis of Compound 122

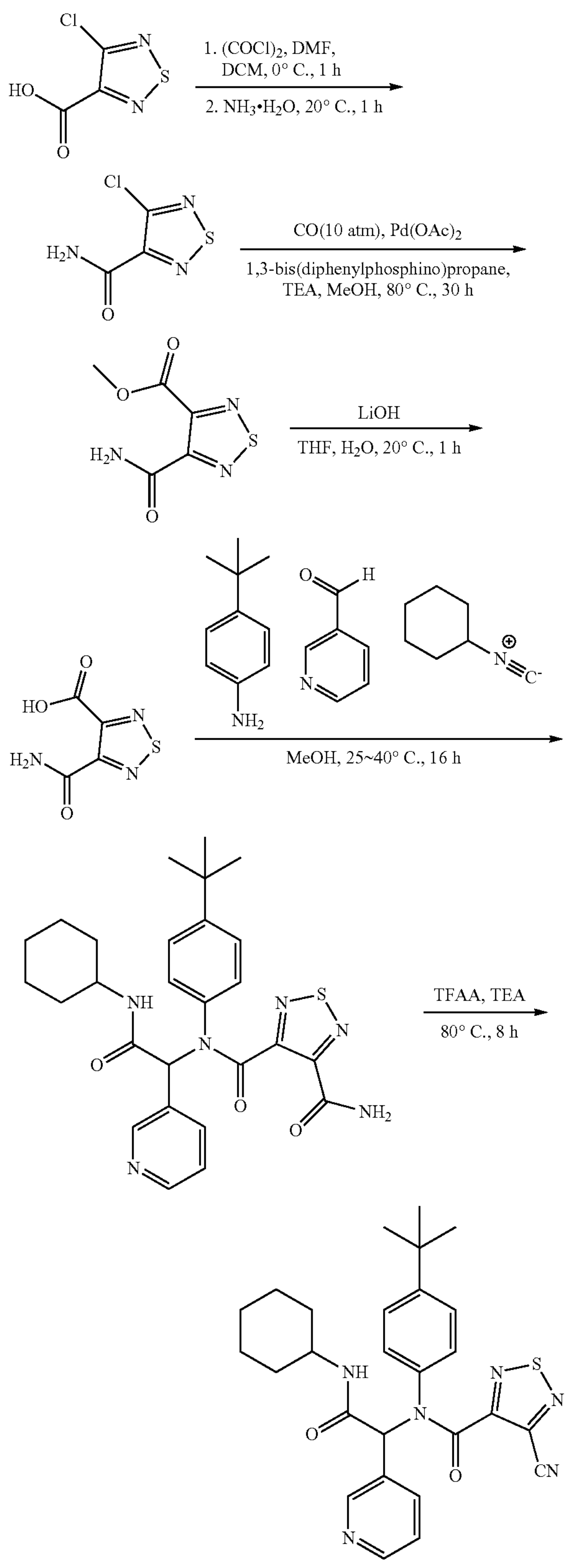

Step 1: 4-chloro-1,2,5-thiadiazole-3-carboxamide

A solution of 4-chloro-1,2,5-thiadiazole-3-carboxylic acid (1000 mg, 6.08 mmol, 1 eq) in DCM (15 mL) was added with DMF (44.44 mg, 608.00 umol, 46.78 uL, 0.1 eq) and oxalyl dichloride (848.88 mg, 6.69 mmol, 585.44 uL, 1.1 eq). The solution was stirred for 1 h at 0° C. NH3·$H_2O$ (1.25 g, 6.08 mmol, 1.38 ml) was added and the mixture was stirred for 1 h at 20° C. Upon completion, the mixture was diluted with $H_2O$ (50 mL) and then extracted with DCM (50 mL*3). The organic layer was washed with $NaHCO_3$ (50 mL*2), dried over $Na_2SO_4$ and concentrated to give product. 4-chloro-1,2,5-thiadiazole-3-carboxamide (500 mg) was obtained as a solid. MS (ESI) m/z 164.1 [M+H]+.

Step 2: methyl 4-carbamoyl-1,2,5-thiadiazole-3-carboxylate

A solution of 4-chloro-1,2,5-thiadiazole-3-carboxamide (100 mg, 611.30 umol, 1 eq) in MeOH (12 mL) saturated with 3-diphenylphosphanylpropyl(diphenyl)phosphane (50.43 mg, 122.26 umol, 0.2 eq), diacetoxypalladium (13.72 mg, 61.13 umol, 0.1 eq), TEA (185.57 mg, 1.83 mmol, 255.26 uL, 3 eq) and CO was stirred under 150 Psi at 80° C. for 30 h in a 100 mL of autoclave. Upon completion, the mixture was filtered and concentrated to give product. The product was purified by pre-TLC ($SiO_2$, petroleum ether: EtOAc=1:1). Methyl 4-carbamoyl-1,2,5-thiadiazole-3-carboxylate (45 mg, 192.33 umol) was obtained as a solid. MS (ESI) m/z 188.3 $[M+H]^+$.

Step 3: 4-carbamoyl-1,2,5-thiadiazole-3-carboxylic acid

To a solution of methyl 4-carbamoyl-1,2,5-thiadiazole-3-carboxylate (10 mg, 53.43 umol, 1 eq) in THF (0.5 mL) and $H_2O$ (0.5 mL) was added LiOH·$H_2O$ (0.05 M, 1.07 mL, 1 eq). The solution was stirred for 1 h at 20° C. Upon completion, the solution was diluted with $H_2O$ (15 mL), adjusted to pH=3-4 with HCl and then extracted with EtOAc (50 mL*6). The resulting solution was washed with brine (60 mL) and dried over $Na_2SO_4$ and concentrated to give product. 4-carbamoyl-1,2,5-thiadiazole-3-carboxylic acid (9 mg) was obtained as a solid, and the product was used directly for the next step. MS (ESI) m/z 172.2 $[M+H]^+$.

Step 4: N3-(4-tert-butylphenyl)-N3-[2-(cyclohexylamino)-2-oxo-1-(3-pyridyl)ethyl]-1,2,5-thiadiazole-3,4-dicarboxamide A solution of pyridine-3-carbaldehyde (6.19 mg, 57.75 umol, 5.43 uL, 1 eq) and 4-tert-butylaniline (8.62 mg, 57.75 umol, 9.12 uL, 1 eq) in MeOH (1 mL) was stirred at 25° C. for 1 h, and then 4-carbamoyl-1, 2, 5-thiadiazole-3-carboxylic acid (10 mg, 57.75 umol, 1 eq) and isocyanocyclohexane (6.30 mg, 57.75 umol, 7.18 uL, 1 eq) were added. The mixture was stirred for 15 h at 40° C. Upon completion, the reaction was filtered and purified by pre-HPLC, column: Phenomenex Gemini-NX C18 75*30 mm*3 um; mobile phase: [water (0.05% $NH_3H_2O$+10 mM $NH_4HCO_3$)-ACN]; B %: 35%-55%, 8 min. N3-(4-tert-butylphenyl)-N3-[2-(cyclohexylamino)-2-oxo-1-(3-pyridyl)ethyl]-1,2,5-thiadiazole-3,4-dicarboxamide (3 mg, 5.47 umol) was obtained as a solid. MS (ESI) m/z 521.3 $[M+H]^+$, $^1H$ NMR (400 MHz, DMSO-$d_6$) δ ppm 8.38-8.28 (m, 3H), 8.22 (s, 1H), 7.97 (s, 1H), 7.50-7.40 (m, 1H), 7.22-7.13 (m, 1H), 7.00-6.90 (m, 4H), 6.24 (s, 1H), 3.70-3.57 (m, 1H), 1.83-1.52 (m, 5H), 1.35-1.18 (m, 5H), 1.04 (s, 9H).

Step 5: N-(4-tert-butylphenyl)-4-cyano-N-[2-(cyclohexylamino)-2-oxo-1-(3-pyridyl)ethyl]-1,2,5-thiadiazole-3-carboxamide A solution of N3-(4-tert-butylphenyl)-N3-[2-(cyclohexylamino)-2-oxo-1-(3-pyridyl) ethyl]-1, 2, 5-thiadiazole-3,4-dicarboxamide (15 mg, 28.81 umol, 1 eq) and $POCl_3$ (220.88 mg, 1.44 mmol, 133.87 uL, 50 eq) in ACN (2 mL). was stirred for 8 h at 80° C. Upon completion, the reaction was filtered and purified directly by pre-HPLC, column: Phenomenex Gemini-NX C18 75*30 mm*3 um; mobile phase: [water (0.05% NH3H2O+10 mM $NH_4HCO_3$)-ACN]; B %: 45%-65%, 8 min. N-(4-tert-butylphenyl)-4-cyano-N-[2-(cyclohexylamino)-2-oxo-1-(3-pyridyl)ethyl]-1,2,5-thiadiazole-3-carboxamide (3 mg, 5.67 umol) was obtained as a solid. MS (ESI) m/z 503.1 $[M+H]^+$. $^1H$ NMR (400 MHz, DMSO-$d_6$) δ ppm 8.54-8.39 (m, 2H), 8.28 (br s, 1H), 7.53 (br d, J=6.72 Hz, 1H), 7.30-7.14 (m, 5H), 6.33 (s, 1H), 3.65 (br s, 1H), 1.81-1.60 (m, 5H), 1.38-1.17 (m, 14H).

Example 19: Synthesis of Compound 123

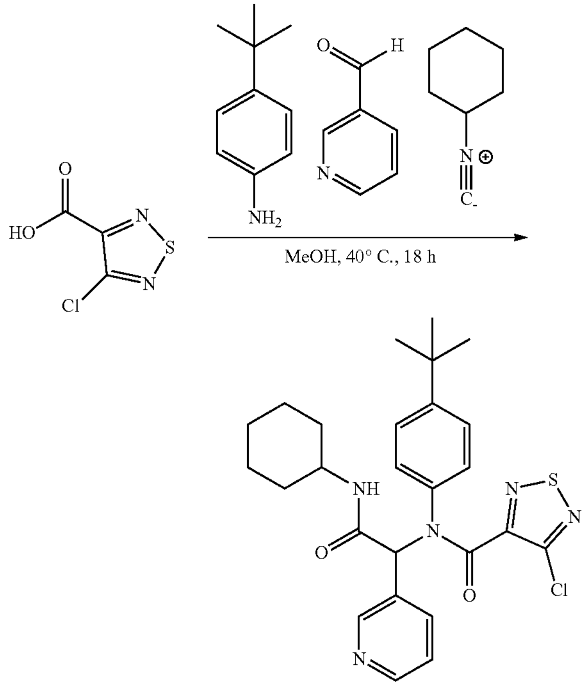

To a stirred solution of 4-chloro-1,2,5-thiadiazole-3-carboxylic acid (0.05 g, 303.82 umol, 1 eq), 4-(tert-butyl) aniline (45.34 mg, 303.82 umol, 47.98 uL, 1 eq), nicotinaldehyde (32.54 mg, 303.82 umol, 28.55 uL, 1 eq) in MeOH (1 mL), isocyanocyclohexane (29.85 mg, 273.44 umol, 34.00 uL, 0.9 eq) was added, and the mixture was stirred at 40° C. for 18 h. Upon completion, the solution was concentrated to give a residue, and the residue was purified by prep-TLC (petroleum ether:EtOAc=1:1). N-(4-(tert-butyl) phenyl)-4-chloro-N-(2-(cyclohexylamino)-2-oxo-1-(pyridin-3-yl)ethyl)-1,2,5-thiadiazole-3-carboxamide (0.12 g, 234.35 umol) was obtained as a solid. 1H NMR (400 MHz, methanol-d4) δ ppm 8.42 (s, 1H) 8.33-8.39 (m, 1H) 7.57-7.71 (m, 1H) 7.20-7.29 (m, 1H) 6.82-7.19 (m, 4H) 6.21-6.32 (m, 1H) 3.55-3.86 (m, 1H) 1.88-2.01 (m, 1H) 1.74-1.84 (m, 2H) 1.57-1.73 (m, 2H) 1.21-1.42 (m, 4H) 1.09-1.15 (m, 10H). MS (ESI) m/z 512.1 $[M+H]^+$.

Example 20: Synthesis of Compound 124

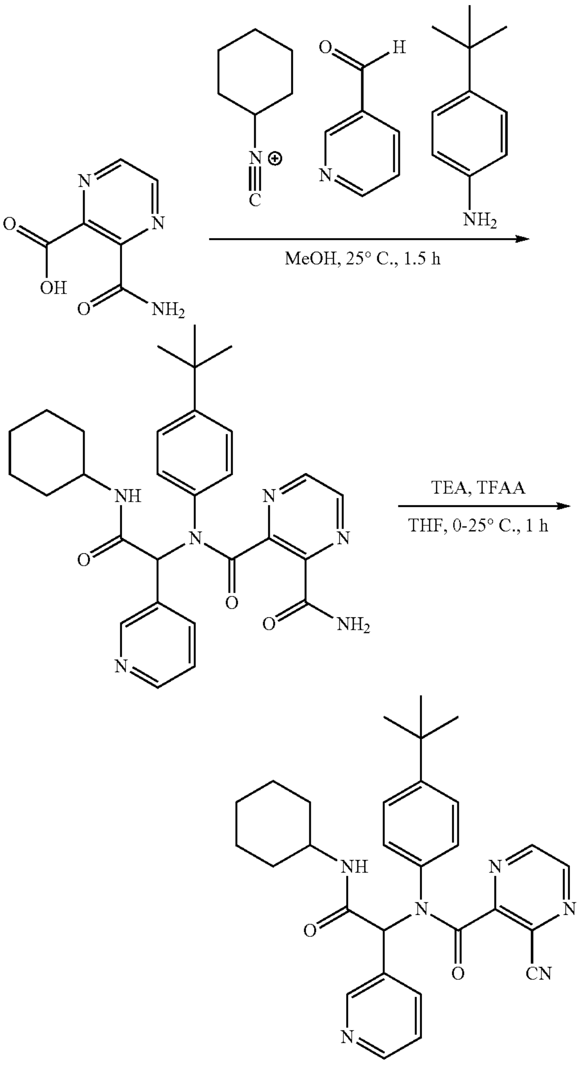

Step 1: N2-(4-(tert-butyl)phenyl)-N2-(2-(cyclohexylamino)-2-oxo-1-(pyridin-3-yl)ethyl)pyrazine-2,3-dicarboxamide A solution of 3-carbamoylpyrazine-2-carboxylic acid (320.45 mg, 2.99 mmol, 281.10 uL, 1 eq) and 4-tert-butylaniline (446.48 mg, 2.99 mmol, 472.46 uL, 1 eq) in MeOH (10 mL) was stirred at 25° C. for 0.5 h, and then 3-carbamoylpyrazine-2-carboxylic acid (500 mg, 2.99 mmol, 1 eq) and isocyanocyclohexane (293.95 mg, 2.69 mmol, 334.80 uL, 0.9 eq) were added. The resulting mixture was stirred at 25° C. for 1 h. Upon the completion of the reaction, the mixture was concentrated in vacuum directly to get the N2-(4-(tert-butyl) phenyl)-N2-(2-(cyclohexylamino)-2-oxo-1-(pyridin-3-yl) ethyl) pyrazine-2,3-dicarboxamide (1.3 g) as a solid. MS (ESI) m/z 515.2 $[M+H]^+$.

Step 2: N-(4-(tert-butyl)phenyl)-3-cyano-N-(2-(cyclohexylamino)-2-oxo-1-(pyridin-3-yl)ethyl)pyrazine-2-carboxamide To a stirred solution of N2-(4-(tert-butyl)phenyl)-N2-(2-(cyclohexylamino)-2-oxo-1-(pyridin-3-yl)ethyl)pyrazine-2,3-dicarboxamide (330 mg, 641.25 umol, 1 eq) in THF (10 mL) was added TFAA (161.62 mg, 769.50 umol, 107.03 uL, 1.2 eq) and TEA (77.87 mg, 769.50 umol, 107.11 uL, 1.2 eq) at 0° C. The resulting mixture was stirred at 25° C. for 1 h. The resulting mixture was concentrated in vacuum directly to remove the solution, and washed with DCM (10 mL*2). The product was dissolved in DMF, and purified by prep-HPLC (column: Phenomenex luna C18 80*40 mm*3 um; mobile phase: [water (0.04% HCl)-ACN]; B %: 30%-60%, 7 min) to get the N-(4-(tert-butyl)phenyl)-3-cyano-N-(2-(cyclohexylamino)-2-oxo-1-(pyridin-3-yl)ethyl)pyrazine-2-carboxamide (18.71 mg, 36.60 umol) as a solid. MS (ESI) m/z 497.3 $[M+H]^+$. $^1H$ NMR (400 MHz, METHANOL-$d_4$) δ ppm 9.03-8.90 (m, 1H), 8.85-8.79 (m, 1H), 8.71-8.65 (m, 1H), 8.64-8.58 (m, 2H), 8.42-8.36 (m, 1H), 8.09-8.01 (m, 1H), 7.33-7.09 (m, 4H), 6.42 (s, 1H), 3.78-3.50 (m, 1H), 1.90-1.56 (m, 5H), 1.40-1.03 (m, 14H).

Example 21: Synthesis of Compound 125

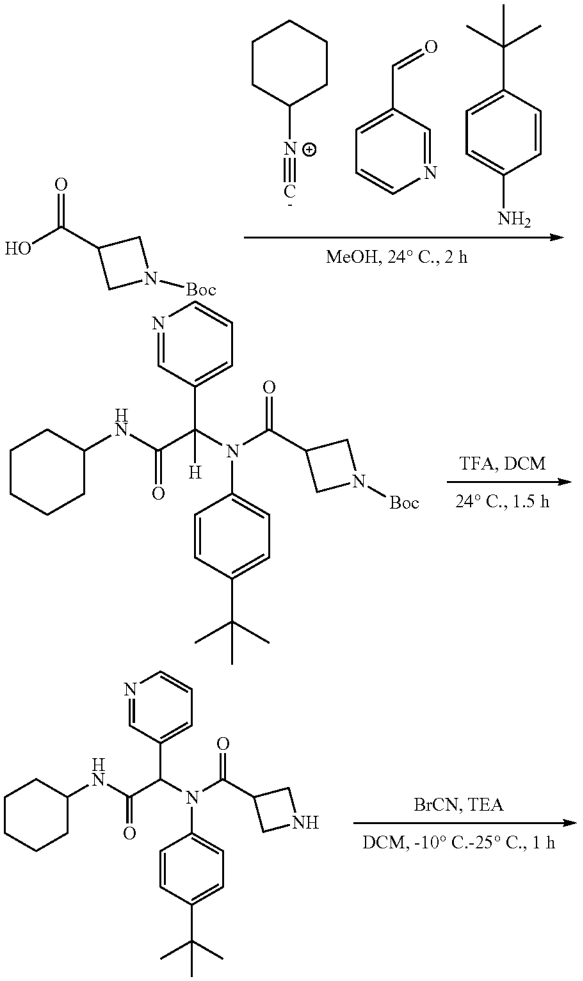

-continued

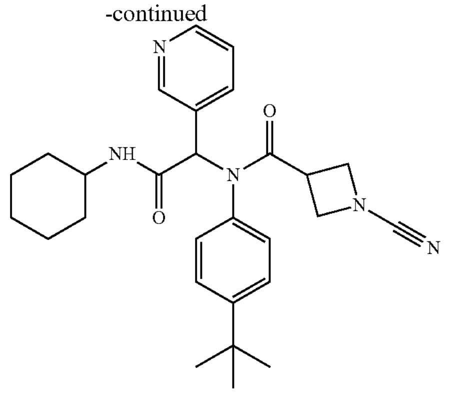

Step 1: tert-butyl 3-[(4-tert-butylphenyl)-[2-(cyclohexylamino)-2-oxo-1-(3-pyridyl)ethyl]carbamoyl]azetidine-1-carboxylate A solution of 4-tert-butylaniline (741.64 mg, 4.97 mmol, 784.80 uL, 1 eq) and pyridine-3-carbaldehyde (532.30 mg, 4.97 mmol, 466.93 uL, 1 eq) in MeOH (5 mL) were stirred at 24° C. for 0.5 h. 1-Tert-butoxycarbonylazetidine-3-carboxylic acid (1 g, 4.97 mmol, 1 eq) and isocyanocyclohexane (542.54 mg, 4.97 mmol, 617.92 uL, 1 eq) were added to the solution and stirred at 25° C. for 1.5 h. The solution was diluted with $H_2O$ (50 mL), extracted with EtOAc (3*40 mL), and the combined organic phase was dried over $Na_2SO_4$, filtrated and concentrated to afford tert-butyl 3-[(4-tert-butylphenyl)-[2-(cyclohexylamino)-2-oxo-1-(3-pyridyl)ethyl]carbamoyl]azetidine-1-carboxylate (800 mg, 1.17 mmol) as a solid. MS (ESI) m/z 549.1 $[M+H]^+$. $^1H$ NMR (400 MHz, DMSO-$d_6$) δ ppm 0.94-1.24 (m, 14H) 1.31-1.39 (m, 9H) 1.47-1.85 (m, 5H) 3.13 (br s, 1H) 3.43-3.70 (m, 3H) 3.74-4.07 (m, 2H) 6.02-6.09 (m, 1H) 6.39-7.88 (m, 6H) 8.04 (br s, 1H) 8.28 (br s, 2H).

Step 2: N-(4-tert-butylphenyl)-N-[2-(cyclohexylamino)-2-oxo-1-(3-pyridyl)ethyl]azetidine-3-carboxamide To a solution of tert-butyl 3-[(4-tert-butylphenyl)-[2-(cyclohexylamino)-2-oxo-1-(3-pyridyl)ethyl]carbamoyl]azetidine-1-carboxylate (500 mg, 911.22 umol, 1 eq) in DCM (4 mL) was added TFA (2 mL). The mixture was stirred at 24° C. for 1.5 h. The solution was diluted with $H_2O$ (50 mL) and extracted with EtOAc (3*30 mL). The organic phase was combined, dried over $Na_2SO_4$, and filtered. The resulting solution was concentrated and purified by prep-HPLC (column: Phenomenex Gemini-NX 80*30 mm*3 um; mobile phase: [water (10 mM $NH_4HCO_3$)-ACN]; B %: 10%-55%, 10 min) to afford N-(4-tert-butylphenyl)-N-[2-(cyclohexylamino)-2-oxo-1-(3-pyridyl)ethyl]azetidine-3-carboxamide (200 mg, 423.54 umol) as a solid. MS (ESI) m/z 449.1 $[M+H]^+$. $^1H$ NMR (400 MHz, DMSO-$d_6$) δ ppm 0.88-1.12 (m, 3H) 1.18 (s, 11H) 1.48-1.77 (m, 6H) 2.82 (br t, J=7.89 Hz, 1H) 2.92 (br t, J=7.52 Hz, 1H) 3.54-3.63 (m, 3H) 3.67 (br t, J=7.64 Hz, 1H) 6.02 (s, 1H) 7.01-7.37 (m, 6H) 8.01 (br d, J=7.46 Hz, 1H) 8.23-8.32 (m, 2H).

Step 3: N-(4-tert-butylphenyl)-1-cyano-N-[2-(cyclohexylamino)-2-oxo-1-(3-pyridyl)ethyl]azetidine-3-carboxamide To a mixture of N-(4-tert-butylphenyl)-N-[2-(cyclohexylamino)-2-oxo-1-(3-pyridyl)ethyl]azetidine-3-carboxamide (100 mg, 222.92 umol, 1 eq) in DCM (3 mL) was added TEA (67.67 mg, 668.75 umol, 93.08 uL, 3 eq) and BrCN (47.22 mg, 2.36 mmol, 1.11 mol, 5 eq) in one portion at −10° C. The mixture was stirred at 25° C. for 1 h. The aqueous phase was extracted with ethyl acetate (3*20 mL). The combined organic phase was washed with brine (3*20 mL), dried with anhydrous $Na_2SO_4$, filtered and concentrated in vacuum. The residue was purified by prep-HPLC (column: Phenomenex Gemini-NX C18 75*30 mm*3 um; mobile phase: [water (10 mM $NH_4HCO_3$)-ACN]; B %: 30%-60%, 6 min) to get N-(4-tert-butylphenyl)-1-cyano-N-[2-(cyclohexylamino)-2-oxo-1-(3-pyridyl)ethyl]azetidine-3-carboxamide (30 mg, 60.18 umol) as a solid. MS (ESI) m/z 474.1 $[M+H]^+$. 1H NMR (400 MHz, DMSO-$d_6$) δ ppm 0.94-1.19 (m, 13H) 1.48-1.78 (m, 6H) 3.37 (br s, 1H) 3.53-3.63 (m, 1H) 3.74 (br t, J=8.13 Hz, 2H) 4.11 (t, J=7.15 Hz, 1H) 4.24 (t, J=7.09 Hz, 1H) 6.04 (s, 1H) 7.00-7.39 (m, 6H) 8.06 (br d, J=7.70 Hz, 1H) 8.28 (td, J=4.10, 1.71 Hz, 2H). $^1H$ NMR (400 MHz, DMSO-$d_6$) δ ppm 1.21-1.25 (m, 1H) 1.47-1.76 (m, 5H) 3.33 (quin, J=7.86 Hz, 1H) 4.12 (t, J=7.21 Hz, 1H) 4.22 (br t, J=7.09 Hz, 1H) 6.00 (br s, 1H) 6.94-7.48 (m, 6H) 8.09 (br d, J=7.58 Hz, 1H) 8.21-8.37 (m, 2H).

Example 22: Synthesis of Compound 128

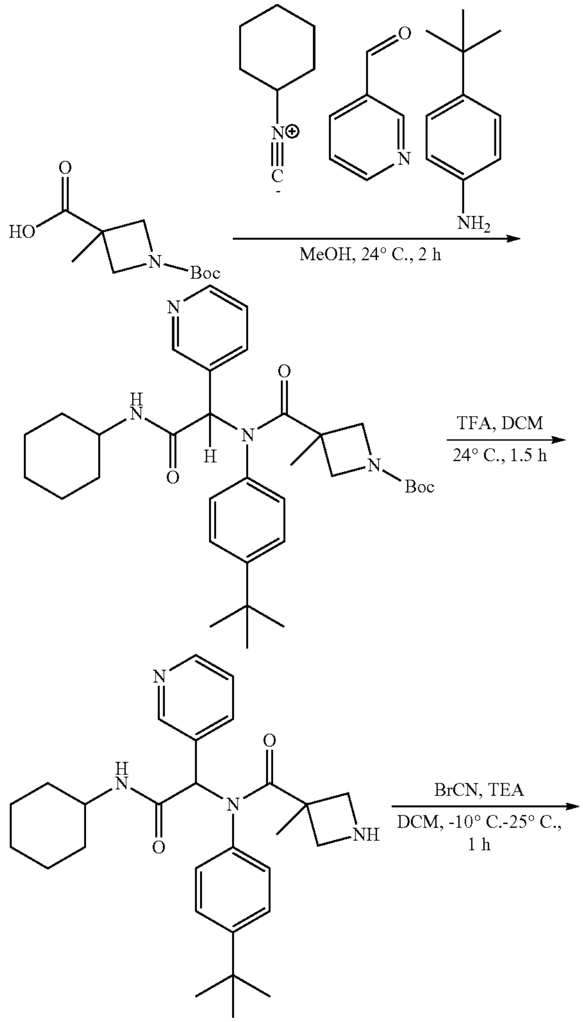

-continued

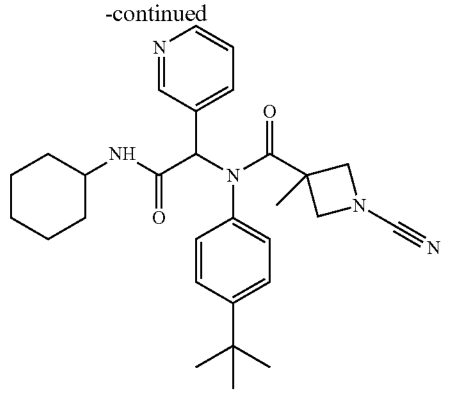

Step 1: tert-butyl 3-[(4-tert-butylphenyl)-[2-(cyclohexylamino)-2-oxo-1-(3-pyridyl)ethyl]carbamoyl]-3-methyl-azetidine-1-carboxylate A solution of 4-tert-butylaniline (693.31 mg, 4.65 mmol, 733.66 uL, 1 eq) and pyridine-3-carbaldehyde (497.62 mg, 4.65 mmol, 436.51 uL, 1 eq) in MeOH (1 mL) were stirred at 24° C. for 0.5 h. To the resulting mixture was added 1-tert-butoxycarbonyl-3-methyl-azetidine-3-carboxylic acid (1 g, 4.65 mmol, 1 eq) and isocyanocyclohexane (507.18 mg, 4.65 mmol, 577.66 uL, 1 eq), and the resulting solution was stirred at 24° C. for 1.5 h. The solution was diluted with $H_2O$ (10 mL), and extracted with EtOAc (3*20 mL). The organic phase was combined, dried over $Na_2SO_4$, filtered and concentrated to afford tert-butyl 3-[(4-tert-butylphenyl)-[2-(cyclohexylamino)-2-oxo-1-(3-pyridyl)ethyl]carbamoyl]-3-methyl-azetidine-1-carboxylate (900 mg, 1.44 mmol) as a solid. MS (ESI) m/z 563.3 $[M+H]^+$. $^1H$ NMR (400 MHz, DMSO-$d_6$) δ ppm 0.87-1.18 (m, 14H) 1.32 (s, 9H) 1.36 (s, 4H) 1.46-1.77 (m, 4H) 3.41-3.63 (m, 3H) 3.94 (br s, 2H) 5.95 (s, 1H) 6.97-7.47 (m, 6H) 7.96 (br d, J=7.58 Hz, 1H) 8.20-8.31 (m, 2H).

Step 2: N-(4-tert-butylphenyl)-N-[2-(cyclohexylamino)-2-oxo-1-(3-pyridyl)ethyl]-3-methyl-azetidine-3-carboxamide To a solution of tert-butyl 3-[(4-tert-butylphenyl)-[2-(cyclohexylamino)-2-oxo-1-(3-pyridyl)ethyl]carbamoyl]-3-methyl-azetidine-1-carboxylate (500 mg, 888.51 umol, 1 eq) in DCM (4 mL) was added TFA (2 mL). The resulting mixture was stirred at 24° C. for 1.5 h. The solution was diluted with $H_2O$ (50 mL), and extracted with EtOAc (3*30 mL). The organic phase combined, dried over $Na_2SO_4$, filtered, and concentrated. The residue was purified by prep-HPLC (column: Phenomenex Gemini-NX C18 75*30 mm*3 um; mobile phase: [water (10 mM $NH_4HCO_3$)-ACN]; B %: 25%-50%, 6 min) to get N-(4-tert-butylphenyl)-N-[2-(cyclohexylamino)-2-oxo−1-(3-pyridyl)ethyl]-3-methyl-azetidine-3-carboxamide (200 mg, 345.85 umol) as a solid. MS (ESI) m/z 463.3 $[M+H]^+$. $^1H$ NMR (400 MHz, DMSO-$d_6$) δ ppm 0.86-1.21 (m, 15H) 1.42 (br s, 3H) 1.49-1.74 (m, 4H) 2.15-2.29 (m, 2H) 3.51 (br s, 1H) 3.53-3.64 (m, 2H) 5.95 (s, 1H) 6.95-7.42 (m, 6H) 7.93 (br d, J=7.46 Hz, 1H) 8.17-8.35 (m, 2H).

Step 3: N-(4-tert-butylphenyl)-1-cyano-N-[2-(cyclohexylamino)-2-oxo-1-(3-pyridyl)ethyl]-3-methyl-azetidine-3-carboxamide To a solution of N-(4-tert-butylphenyl)-N-[2-(cyclohexylamino)-2-oxo-1-(3-pyridyl)ethyl]-3-methyl-azetidine-3-carboxamide (100 mg, 216.16 umol, 1 eq) in DCM (3 mL) was added TEA (10.94 mg, 108.08 umol, 15.04 uL, 0.5 eq) and BrCN (110 mg, 1.04 mmol, 76.39 uL, 4.80 eq) at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Phenomenex Gemini-NX C18 75*30 mm*3 um; mobile phase: [water (10 mM NH4HCO3)-ACN]; B %: 30%-60%, 6 min) to get N-(4-tert-butylphenyl)-1-cyano-N-[2-(cyclohexylamino)-2-oxo-1-(3-pyridyl)ethyl]-3-methyl-azetidine-3-carboxamide (30 mg, 58.45 umol) as a solid. MS (ESI) m/z 488.1 $[M+H]^+$. $^1H$ NMR (400 MHz, DMSO-$d_6$) δ ppm 0.99-1.27 (m, 14H) 1.41 (s, 3H) 1.49-1.76 (m, 5H) 2.78-2.87 (m, 1H) 3.23 (br d, J=7.09 Hz, 1H) 3.51-3.65 (m, 1H) 4.28 (dd, J=13.69, 7.21 Hz, 2H) 5.95 (s, 1H) 6.69-7.51 (m, 6H) 7.97 (br d, J=7.58 Hz, 1H) 8.21-8.37 (m, 2H).

Example 23: Synthesis of Compound 1248

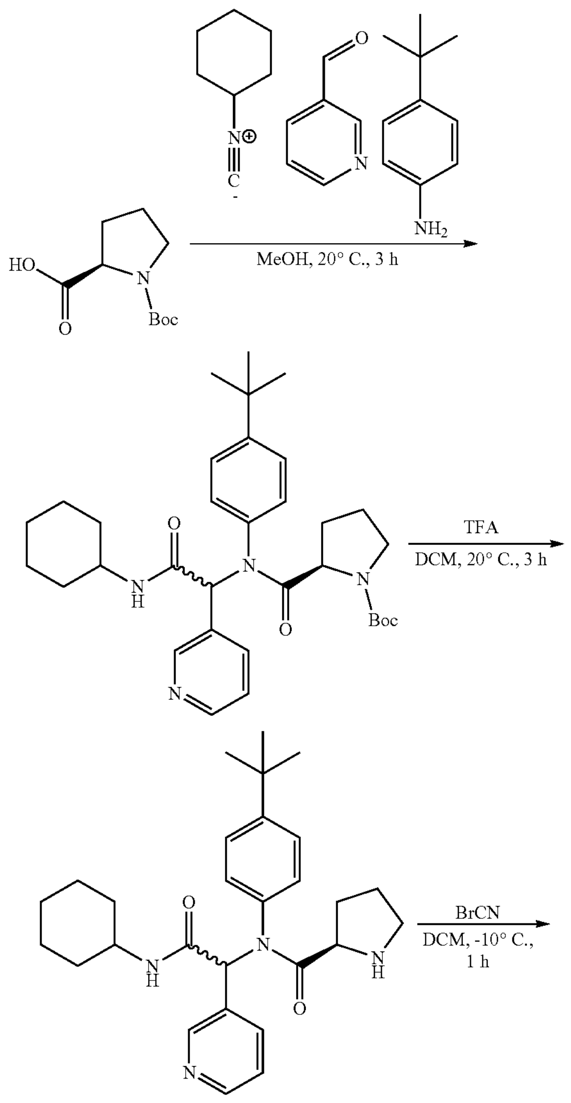

-continued

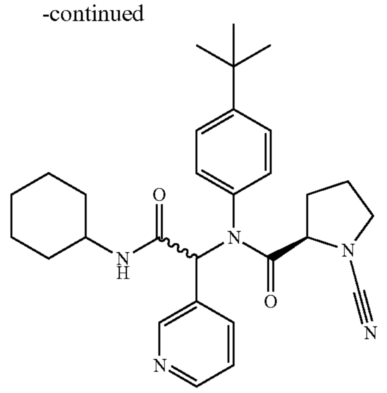

Step 1: (2R)-tert-butyl 2-((4-(tert-butyl)phenyl)(2-(cyclohexylamino)-2-oxo-1-(pyridin-3-yl)ethyl)carbamoyl)pyrrolidine-1-carboxylate A mixture of 4-tert-butylaniline (100 mg, 670.10 umol, 105.82 uL, 1 eq), pyridine-3-carbaldehyde (71.77 mg, 670.10 umol, 62.96 uL, 1 eq), (2R)-1-tert-butoxycarbonylpyrrolidine-2-carboxylic acid (144.24 mg, 670.10 umol, 1 eq) and isocyanocyclohexane (65.84 mg, 603.09 umol, 74.99 uL, 0.9 eq) in MeOH (2 mL) was stirred at 20° C. for 3 hours. The mixture was concentrated, and the residue was purified by prep-HPLC (column: Kromasil C18 (250*50 mm*10 um); mobile phase: [water (10 mM $NH_4HCO_3$)-ACN]; B %: 60%-85%, 10 min) to give (2R)-tert-butyl 2-((4-(tert-butyl)phenyl)(2-(cyclohexylamino)-2-oxo-1-(pyridin-3-yl)ethyl)carbamoyl)pyrrolidine-1-carboxylate (250 mg, 444.25 umol, 66.30% yield, 100% purity) and tert-butyl (2R)-2-[(4-tert-butylphenyl)-[2-(cyclohexylamino)-2-oxo-1-(3-pyridyl)ethyl]carbamoyl]pyrrolidine-1-carboxylate (260 mg, 461.01 umol, 68.80% yield, 99.78% purity). $^1H$ NMR (400 MHz, DMSO-$d_6$) δ ppm 1.14-1.27 (m, 14H) 1.42 (s, 9H) 1.56-1.87 (m, 9H) 3.22-3.41 (m, 2H) 3.59 (br d, J=7.28 Hz, 1H) 3.98 (br s, 1H) 5.90-6.23 (m, 1H) 7.00-7.79 (m, 7H) 8.20-8.37 (m, 2H); MS (ESI) m/z 563.3 $[M+H]^+$; Isomer 2: $^1H$ NMR (400 MHz, DMSO-$d_6$) δ ppm 0.84-1.30 (m, 14H) 1.43 (s, 9H) 1.53-1.93 (m, 9H) 3.20-3.41 (m, 2H) 3.47-3.73 (m, 1H) 3.87-4.06 (m, 1H) 5.76-6.22 (m, 1H) 6.88-7.73 (m, 7H) 8.17-8.41 (m, 2H); MS (ESI) m/z 563.3 $[M+H]^+$.

Step 2: tert-butyl (2R)-2-[(4-tert-butylphenyl)-[2-(cyclohexylamino)-2-oxo-1-(3-pyridyl)ethyl]carbamoyl]pyrrolidine-1-carboxylate A mixture of tert-butyl (2R)-2-[(4-tert-butylphenyl)-[2-(cyclohexylamino)-2-oxo-1-(3-pyridyl)ethyl]carbamoyl]pyrrolidine-1-carboxylate (250 mg, 444.25 umol, 1 eq) in DCM (2 mL) and TFA (0.4 mL) was stirred at 20° C. for 3 hours. The reaction was concentrated and purified by prep-HPLC (column: Phenomenex Luna C18 100*30 mm*5 um; mobile phase: [water (0.1% TFA)-ACN]; B %: 5%-50%, 7 min) to give (2R)-tert-butyl 2-((4-(tert-butyl)phenyl)(2-(cyclohexylamino)-2-oxo-1-(pyridin-3-yl)ethyl)carbamoyl) pyrrolidine-1-carboxylate (150 mg, 320.16 umol, 72.07% yield, 98.743% purity) as an oil. $^1H$ NMR (400 MHz, DMSO-$d_6$) δ ppm 0.97-1.15 (m, 3H) 1.18 (s, 9H) 1.22-1.92 (m, 11H) 3.03-3.16 (m, 1H) 3.22 (br d, J=4.77 Hz, 1H) 3.54-3.64 (m, 1H) 3.96-4.07 (m, 1H) 6.15 (s, 1H) 7.28 (br s, 2H) 7.41 (dd, J=7.97, 5.21 Hz, 1H) 7.67 (br d, J=8.03 Hz, 1H) 8.20 (d, J=7.65 Hz, 1H) 8.45-8.65 (m, 3H) 9.39 (br d, J=4.64 Hz, 1H) MS (ESI) m/z 463.3 [M+H]$^+$.

Step 3: (2R)—N-(4-tert-butylphenyl)-N-[2-(cyclohexylamino)-2-oxo-1-(3-pyridyl)ethyl]pyrrolidine-2-carboxamide A mixture of tert-butyl (2R)-2-[(4-tert-butylphenyl)-[2-(cyclohexylamino)-2-oxo-1-(3-pyridyl)ethyl]carbamoyl] pyrrolidine-1-carboxylate (260 mg, 462.02 umol, 1 eq) in DCM (2 mL) and TFA (0.4 mL) was stirred at 20° C. for 3 hours. The reaction was concentrated and the residue was purified by prep-HPLC (column: Phenomenex Gemini-NX 150*30 mm*5 um; mobile phase: [water (0.1% TFA)-ACN]; B %: 20%-50%, 9 min) to give (2R)—N-(4-tert-butylphenyl)-N-[2-(cyclohexylamino)-2-oxo-1-(3-pyridyl)ethyl]pyrrolidine-2-carboxamide (150 mg, 324.24 umol, 70.18% yield) as an oil. $^1$H NMR (400 MHz, DMSO-$d_6$) δ ppm 0.97-1.11 (m, 2H) 1.17 (s, 9H) 1.23-1.89 (m, 12H) 2.98-3.14 (m, 1H) 3.21 (br d, J=5.27 Hz, 1H) 3.54-3.66 (m, 1H) 3.96-4.06 (m, 1H) 6.13 (s, 1H) 7.31 (br dd, J=7.84, 5.08 Hz, 3H) 7.55 (br d, J=8.03 Hz, 1H) 8.17 (d, J=7.65 Hz, 1H) 8.37-8.44 (m, 2H) 8.48-8.62 (m, 1H) 9.28 (br d, J=4.39 Hz, 1H) MS (ESI) m/z 463.4 [M+H]$^+$.

Step 4: N-(4-(tert-butyl)phenyl)-1-cyano-N-(2-(cyclohexylamino)-2-oxo-1-(pyridin-3-yl)ethyl)pyrrolidine-2-carboxamide To a mixture of (2R)—N-(4-tert-butylphenyl)-N-[2-(cyclohexylamino)-2-oxo-1-(3-pyridyl)ethyl]pyrrolidine-2-carboxamide (100 mg, 216.16 umol, 1 eq) and TEA (43.75 mg, 432.32 umol, 60.17 uL, 2 eq) in DCM (10 mL) was added CNBr (137.37 mg, 1.30 mmol, 95.40 uL, 6 eq) in one portion at −10° C. The mixture was stirred at −10° C. for 1 hour. The residue was poured into ice-water (50 mL) and extracted with DCM (30 mL*3). The combined organic phase was washed with brine (90 mL*3), dried with anhydrous $Na_2SO_4$, filtered and concentrated in vacuum. The residue was purified by prep-HPLC (column: Phenomenex Gemini-NX C18 75*30 mm*3 um; mobile phase: [water (10 Mm $NH_4HCO_3$)-ACN]; B %: 42%-62%, 6 min) to afford (2R)—N-(4-tert-butylphenyl)-1-cyano-N-[2-(cyclohexylamino)-2-oxo-1-(3-pyridyl)ethyl]pyrrolidine-2-carboxamide (36.08 mg, 73.99 umol, 34.23% yield, 100% purity) as a solid. $^1$H NMR (400 MHz, DMSO-$d_6$) δ ppm 0.94-1.13 (m, 2H) 1.19 (s, 9H) 1.22-2.15 (m, 12H) 3.32-3.49 (m, 2H) 3.55-3.65 (m, 1H) 3.94-4.13 (m, 1H) 6.09 (s, 1H) 6.88-7.45 (m, 5H) 7.83 (br d, J=7.06 Hz, 1H) 8.17-8.34 (m, 2H) MS (ESI) m/z 488.3 [M+H]$^+$.

Step 5: N-(4-(tert-butyl)phenyl)-1-cyano-N-(2-(cyclohexylamino)-2-oxo-1-(pyridin-3-yl)ethyl)pyrrolidine-2-carboxamide To a mixture of (2R)—N-(4-tert-butylphenyl)-N-[2-(cyclohexylamino)-2-oxo-1-(3-pyridyl)ethyl]pyrrolidine-2-carboxamide (100 mg, 216.16 umol, 1 eq) and TEA (43.75 mg, 432.32 umol, 60.17 uL, 2 eq) in DCM (10 mL) was added CNBr (137.37 mg, 1.30 mmol, 95.40 uL, 6 eq) in one portion at −10° C. The mixture was stirred at −10° C. for 1 hours. The residue was poured into ice-water (50 mL) and extracted with DCM (30 mL*3). The combined organic phase was washed with brine (90 mL*3), dried with anhydrous $Na_2SO_4$, filtered and concentrated in vacuum. The residue was purified by prep-TLC (petroleum ether/EtOAc=0:2) to afford (2R)—N-(4-tert-butylphenyl)-1-cyano-N-[2-(cyclohexylamino)-2-oxo-1-(3-pyridyl)ethyl] pyrrolidine-2-carboxamide (37.22 mg, 76.23 umol, 35.27% yield, 99.87% purity) as a solid. $^1$H NMR (400 MHz, DMSO-$d_6$) δ ppm 1.00-1.19 (m, 2H) 1.22 (s, 9H) 1.23-2.40 (m, 12H) 3.31-3.48 (m, 2H) 3.56 (br d, J=7.28 Hz, 1H) 3.97 (br s, 1H) 5.96 (s, 1H) 6.96-7.40 (m, 5H) 7.72 (br s, 1H) 8.33 (s, 2H); MS (ESI) m/z 488.3 [M+H]$^+$.

Example 24: Synthesis of Compound 1249

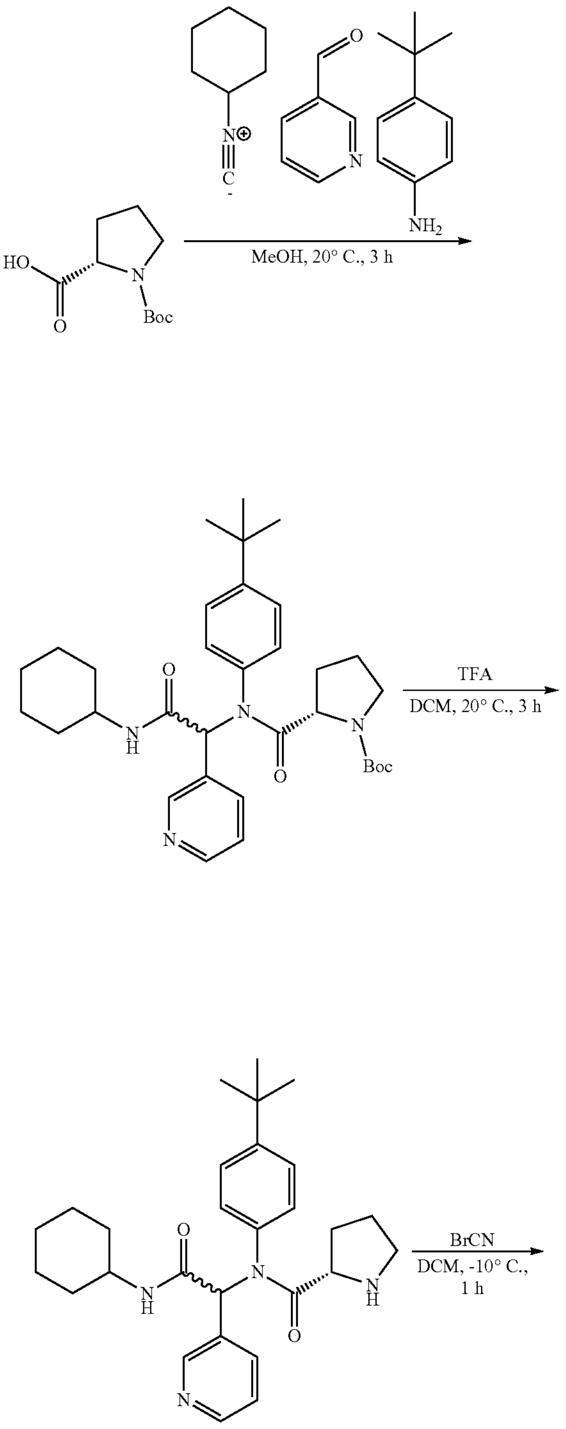

-continued

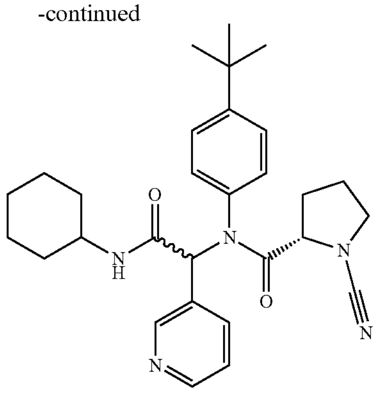

Step 1: (2S)-tert-butyl 2-((4-(tert-butyl)phenyl)(2-(cyclohexylamino)-2-oxo-1-(pyridin-3-yl)ethyl)carbamoyl)pyrrolidine-1-carboxylate A mixture of 4-tert-butylaniline (200 mg, 1.34 mmol, 211.64 uL, 1 eq), pyridine-3-carbaldehyde (143.55 mg, 1.34 mmol, 125.92 uL, 1 eq), (2S)-1-tert-butoxycarbonylpyrrolidine-2-carboxylic acid (288.47 mg, 1.34 mmol, 1 eq) and isocyanocyclohexane (131.68 mg, 1.21 mmol, 149.97 uL, 0.9 eq) in MeOH (0.5 mL) was stirred at 20° C. for 3 hours. The reaction was concentrated and purified by prep-HPLC (column: Kromasil C18 (250*50 mm*10 um); mobile phase: [water (10 mM NH4HCO3)-ACN]; B %: 60%-85%, 10 min) to give (2S)-tert-butyl 2-((4-(tert-butyl)phenyl)(2-(cyclohexylamino)-2-oxo-1-(pyridin-3-yl)ethyl)carbamoyl) pyrrolidine-1-carboxylate (230 mg, 408.71 umol, 30.50% yield, 100% purity) and (2S)-tert-butyl 2-((4-(tert-butyl) phenyl)(2-(cyclohexylamino)-2-oxo-1-(pyridin-3-yl)ethyl) carbamoyl)pyrrolidine-1-carboxylate (240 mg, 518.78 umol, 38.71% yield, 100% purity); Isomer 1: $^1$H NMR (400 MHz, DMSO-$d_6$): δ ppm 1.08-1.30 (m, 14H) 1.42 (s, 9H) 1.50-1.95 (m, 9H) 3.21-3.40 (m, 2H) 3.51-3.66 (m, 1H) 3.92-4.01 (m, 1H) 5.49-6.30 (m, 1H) 6.97-7.82 (m, 7H) 8.21-8.34 (m, 2H); MS (ESI) m/z 563.32 $[M+H]^+$; Isomer 2: $^1$H NMR (400 MHz, DMSO-$d_6$: 6 ppm 0.86-1.28 (m, 14H) 1.43 (s, 9H) 1.57-1.90 (m, 9H) 3.20-3.41 (m, 2H) 3.50-3.72 (m, 1H) 3.92-4.02 (m, 1H) 5.72-6.62 (m, 1H) 6.85-7.72 (m, 7H) 8.18-8.40 (m, 2H).

Step 2: (2S)—N-(4-tert-butylphenyl)-N-[2-(cyclohexylamino)-2-oxo-1-(3-pyridyl)ethyl]pyrrolidine-2-carboxamide To a mixture of tert-butyl (2S)-tert-butyl 2-((4-(tert-butyl) phenyl)(2-(cyclohexylamino)-2-oxo-1-(pyridin-3-yl)ethyl) carbamoyl)pyrrolidine-1-carboxylate (230 mg, 408.71 umol, 1 eq) in DCM (2 mL) was added TFA (0.4 mL) in one portion. The mixture was stirred at 20° C. for 3 hours. The reaction was concentrated and purified by prep-HPLC (column: Phenomenex Luna C18 100*30 mm*5 um; mobile phase: [water (0.1% TFA)-ACN]; B %: 15%-50%, 7 min) to give (2S)—N-(4-tert-butylphenyl)-N-[2-(cyclohexylamino)-2-oxo-1-(3-pyridyl)ethyl]pyrrolidine-2-carboxamide (130 mg, 273.46 umol, 66.91% yield, 97.314% purity) as an oil.

$^1$H NMR (400 MHz, DMSO-$d_6$) δ ppm 0.94-1.10 (m, 2H) 1.17 (s, 9H) 1.19-1.89 (m, 13H) 3.02-3.15 (m, 1H) 3.21 (br d, J=4.02 Hz, 1H) 3.53-3.65 (m, 1H) 3.93-3.97 (m, 1H) 6.12 (s, 1H) 7.27 (br dd, J=7.78, 5.02 Hz, 3H) 7.51 (br d, J=7.91 Hz, 1H) 8.18 (br d, J=7.65 Hz, 1H) 8.35-8.42 (m, 2H) 8.57 (br s, 1H) 9.39 (br s, 1H) MS (ESI) m/z 463.4 $[M+H]^+$.

Step 3: (2S)—N-(4-tert-butylphenyl)-N-[2-(cyclohexylamino)-2-oxo-1-(3-pyridyl)ethyl]pyrrolidine-2-carboxamid A mixture of (2S)-tert-butyl 2-((4-(tert-butyl)phenyl)(2-(cyclohexylamino)-2-oxo-1-(pyridin-3-yl)ethyl)carbamoyl) pyrrolidine-1-carboxylate (240 mg, 426.48 umol, 1 eq) in DCM (2 mL) and TFA (0.4 mL) was stirred at 20° C. for 3 hours. The reaction was concentrated and purified by prep-HPLC (column: Phenomenex Luna C18 100*30 mm*5 um; mobile phase: [water (0.1% TFA)-ACN]; B %: 15%-50%, 7 min) to give (2S)—N-(4-tert-butylphenyl)-N-[2-(cyclohexylamino)-2-oxo-1-(3-pyridyl)ethyl]pyrrolidine-2-carboxamide (160 mg, 343.01 umol, 80.43% yield, 99.177% purity) as an oil.

$^1$H NMR (400 MHz, DMSO-$d_6$) δ ppm 0.81-1.15 (m, 3H) 1.17 (s, 9H) 1.22-1.90 (m, 12H) 1.44-1.90 (m, 1H) 3.08-3.10 (m, 1H) 3.21-3.22 (m, 1H) 3.91-4.09 (m, 1H) 6.10 (s, 1H) 7.03-7.33 (m, 3H) 7.40-7.42 (m, 1H) 8.08-8.14 (m, 1H) 8.29-8.39 (m, 2H) 8.55 (s, 1H) 9.23 (s, 1H) MS (ESI) m/z 463.3 $[M+H]^+$.

Step 4: (2S)—N-(4-(tert-butyl)phenyl)-1-cyano-N-(2-(cyclohexylamino)-2-oxo-1-(pyridin-3-yl)ethyl) pyrrolidine-2-carboxamide To a mixture of (2S)—N-(4-tert-butylphenyl)-N-[2-(cyclohexylamino)-2-oxo-1-(3-pyridyl)ethyl]pyrrolidine-2-carboxamide (80 mg, 172.93 umol, 1 eq) and TEA (35.00 mg, 345.85 umol, 48.14 uL, 2 eq) in DCM (10 mL) was added CNBr (109.90 mg, 1.04 mmol, 76.32 uL, 6 eq) in one portion at −10° C. The mixture was stirred at −10° C. for 1 h. The residue was poured into ice-water (50 mL) and extracted with DCM (30 mL*3). The combined organic phase was washed with brine (90 mL*3), dried with anhydrous $Na_2SO_4$, filtered and concentrated in vacuum. The residue was purified by prep-HPLC (column: Phenomenex Gemini-NX C18 75*30 mm*3 um; mobile phase: [water (10 mM NH4HCO3)-ACN]; B %: 42%-62%, 6 min) to give (2S)—N-(4-(tert-butyl)phenyl)-1-cyano-N-(2-(cyclohexylamino)-2-oxo-1-(pyridin-3-yl)ethyl)pyrrolidine-2-carboxamide (16.6 mg, 33.54 umol, 19.40% yield, 98.531% purity) as a solid. 1249 Isomer 1: $^1$H NMR (400 MHz, DMSO-$d_6$) δ ppm 0.99-1.14 (m, 2H) 1.19 (s, 9H) 1.20-2.31 (m, 12H) 3.32-3.50 (m, 2H) 3.60 (br d, J=7.72 Hz, 1H) 3.95-4.02 (m, 1H) 6.09 (s, 1H) 6.88-7.45 (m, 5H) 7.83 (br d, J=6.17 Hz, 1H) 8.17-8.34 (m, 2H) MS (ESI) m/z 488.3 $[M+H]^+$.

Step 5: (2S)—N-(4-(tert-butyl)phenyl)-1-cyano-N-(2-(cyclohexylamino)-2-oxo-1-(pyridin-3-yl)ethyl) pyrrolidine-2-carboxamide To a mixture of (2S)—N-(4-tert-butylphenyl)-N-[2-(cyclohexylamino)-2-oxo-1-(3-pyridyl)ethyl]pyrrolidine-2-carboxamide (80 mg, 172.93 umol, 1 eq) and TEA (35.00 mg, 345.85 umol, 48.14 uL, 2 eq) in DCM (10 mL) was added CNBr (109.90 mg, 1.04 mmol, 76.32 uL, 6 eq) in one portion at −10° C. The mixture was stirred at −10° C. for 1 hour. The residue was poured into ice-water (50 mL) and extracted with DCM (30 mL*3). The combined organic phase was washed with brine (90 mL*3), dried with anhydrous $Na_2SO_4$, filtered and concentrated in vacuum. The residue was purified by prep-HPLC (column: Phenomenex Gemini-NX C18 75*30 mm*3 um; mobile phase: [water (10 mM $NH_4HCO_3$)-ACN]; B %: 40%-60%, 6 min) to afford (2S)—N-(4-(tert-butyl)phenyl)-1-cyano-N-(2-(cyclohexylamino)-2-oxo-1-(pyridin-3-yl)ethyl)pyrrolidine-2-carboxamide (48.89 mg, 99.92 umol, 57.78% yield, 99.66% purity) as a solid. $^1H$ NMR (400 MHz, DMSO-$d_6$) δ ppm 1.09-1.20 (m, 2H) 1.22 (s, 9H) 1.22-2.11 (m, 12H) 3.30-3.48 (m, 2H) 3.55 (br d, J=7.28 Hz, 1H) 3.97 (br s, 1H) 5.96 (s, 1H) 7.02-7.40 (m, 5H) 7.73 (br s, 1H) 8.30-8.36 (m, 2H); MS (ESI) m/z 488.3 $[M+H]^+$.

Example 25: Synthesis of Compound 136

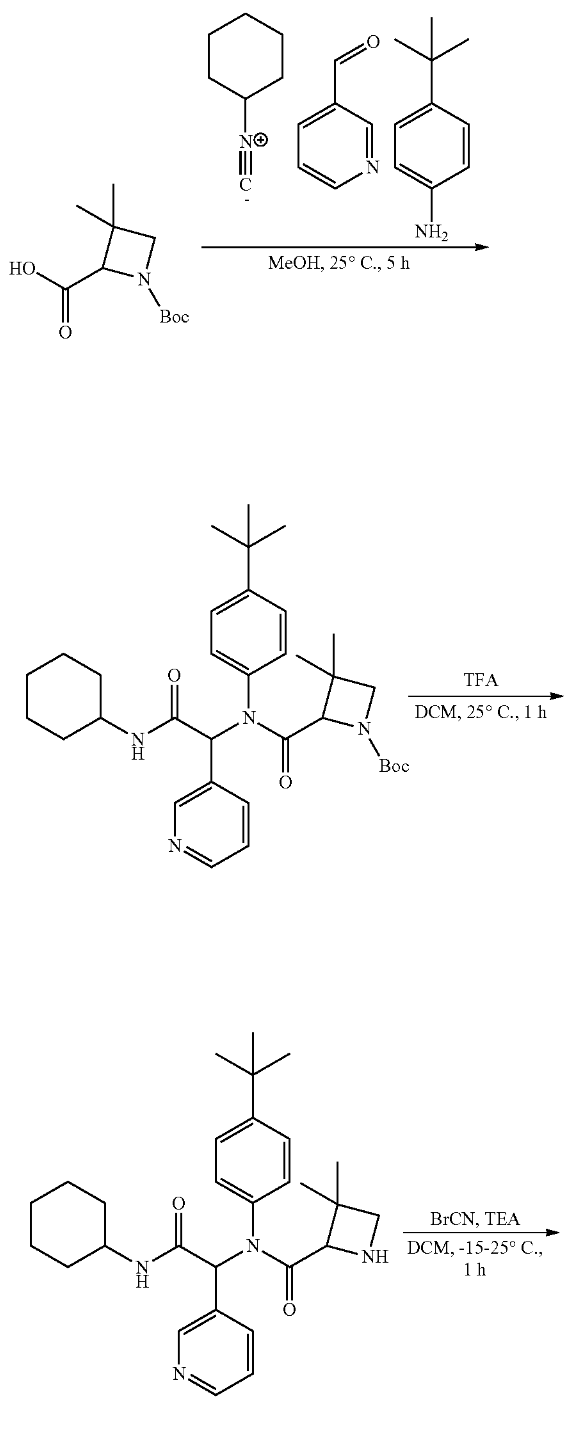

-continued

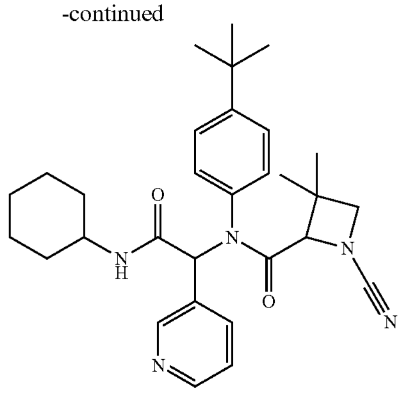

Step 1: tert-butyl 2-((4-(tert-butyl)phenyl)(2-(cyclohexylamino)-2-oxo-1-(pyridin-3-yl)ethyl)carbamoyl)-3,3-dimethylazetidine-1-carboxylate Pyridine-3-carbaldehyde (93.43 mg, 872.33 umol, 81.96 uL, 1 eq) and 4-tert-butylaniline (130.18 mg, 872.33 umol, 137.76 uL, 1 eq) in MeOH (2 mL) were stirred at 25° C. for 0.5 h, and then 1-tert-butoxycarbonyl-3,3-dimethyl-azetidine-2-carboxylic acid (200.00 mg, 872.33 umol, 1 eq) and isocyanocyclohexane (95.23 mg, 872.33 umol, 1 eq) were added. The resulting mixture was stirred at 25° C. for 4.5 h. The solution was concentrated to remove the MeOH. The crude was used to next step directly and without further purification. Tert-butyl 2-[(4-tert-butylphenyl)-[2-(cyclohexylamino)-2-oxo-1-(3-pyridyl) ethyl]carbamoyl]-3, 3-dimethyl-azetidine-1-carboxylate (500 mg, crude) was obtained as a solid. MS (ESI) m/z 577.4 $[M+H]^+$.

Step 2: N-(4-(tert-butyl)phenyl)-N-(2-(cyclohexylamino)-2-oxo-1-(pyridin-3-yl)ethyl)-3,3-dimethylazetidine-2-carboxamide Tert-butyl 2-[(4-tert-butylphenyl)-[2-(cyclohexylamino)-2-oxo-1-(3-pyridyl)ethyl]carbamoyl]-3,3-dimethyl-azetidine-1-carboxylate (500 mg, 866.90 umol, 1 eq) in DCM (5 mL)/TFA (3.85 g, 33.77 mmol, 2.50 mL, 38.95 eq) was stirred at 25° C. for 1 h. The solution was concentrated to remove the DCM. The residue was purified by prep-HPLC (neutral condition), column: Phenomenex luna C18 100*40 mm*5 um; mobile phase: [water (0.1% TFA)-ACN]; B %: 20%-35%, 8 min. N-(4-tert-butylphenyl)-N-[2-(cyclohexylamino)-2-oxo-1-(3-pyridyl)ethyl]-3,3-dimethyl-azetidine-2-carboxamide (170 mg, 356.65 umol, 41.14% yield, 100% purity) was obtained as an oil. $^1H$ NMR (400 MHz, METHANOL-$d_4$) δ=8.58-8.46 (m, 2H), 7.91-7.10 (m, 5H), 6.91-6.48 (m, 1H), 6.08 (s, 1H), 4.82 (s, 1H), 3.71-3.60 (m, 2H), 3.47 (d, J=10.1 Hz, 1H), 1.87 (br d, J=11.0 Hz, 1H), 1.81-1.57 (m, 4H), 1.43-1.02 (m, 14H), 0.60 (s, 3H); N-(4-tert-butylphenyl)-N-[2-(cyclohexylamino)-2-oxo-1-(3-pyridyl)ethyl]-3,3-dimethyl-azetidine-2-carboxamide (200 mg, 419.59 umol, 48.40% yield, 100% purity) was obtained as an oil, $^1H$ NMR (400 MHz, METHANOL-$d_4$) δ ppm 8.54-8.26 (m, 2H), 7.81 (br s, 2H), 7.56-7.19 (m, 3H), 6.87 (br s, 1H), 6.38-6.22 (m, 1H), 4.86-4.81 (m, 1H), 3.80-3.69 (m, 1H), 3.64 (d, J=9.9 Hz, 1H), 3.46 (d, J=10.1 Hz, 1H), 1.93 (br d, J=11.2 Hz, 1H), 1.86-1.59 (m, 4H), 1.46-1.05 (m, 15H), 0.55 (s, 3H). MS (ESI) m/z 477.4 $[M+H]^+$.

Step 3: N-(4-(tert-butyl)phenyl)-1-cyano-N-(2-(cyclohexylamino)-2-oxo-1-(pyridin-3-yl)ethyl)-3,3-dimethylazetidine-2-carboxamide A mixture of N-(4-tert-butylphenyl)-N-[2-(cyclohexylamino)-2-oxo-1-(3-pyridyl)ethyl]-3,3-dimethyl-azetidine-2-carboxamide (100 mg, 209.80 umol, 1 eq) and TEA (63.69 mg, 629.39 umol, 87.60 uL, 3 eq) in DCM (1 mL) was cooled to −15° C., and then a solution of BrCN (460 mg, 4.34 mmol, 319.44 uL, 20.70 eq) in DCM (0.2 mL) was added drop wise. The resulting solution was stirred at 0° C., and warmed to 25° C. for 1 h gradually. The solution was quenched with $H_2O$ (10 mL), extracted with DCM (20 mL*3), the combined organic phase was dried over $Na_2SO_4$, filtrated and concentrated. The residue was purified by prep-HPLC (neutral condition), column: Waters Xbridge Prep OBD C18 150*40 mm*10 um; mobile phase: [water (10 mM NH4HCO3)-ACN]; B %: 35%-65%, 8 min N-(4-tert-butylphenyl)-1-cyano-N-[2-(cyclohexylamino)-2-oxo-1-(3-pyridyl)ethyl]-3,3-dimethyl-azetidine-2-carboxamide (37 mg, 73.75 umol, 35.16% yield, 100% purity) was obtained as a solid. $^1H$ NMR (400 MHz, METHANOL-$d_4$) δ ppm 8.35 (dt, J=1.7, 4.8 Hz, 2H), 7.85-6.94 (m, 5H), 6.69-6.20 (m, 1H), 6.05 (s, 1H), 4.68 (s, 1H), 3.74-3.60 (m, 3H), 1.94 (br d, J=12.1 Hz, 1H), 1.82-1.56 (m, 4H), 1.43-1.25 (m, 3H), 1.24 (s, 9H), 1.21-0.99 (m, 5H), 0.62 (s, 3H). MS (ESI) m/z 502.2 $[M+H]^+$.

Step 4: N-(4-(tert-butyl)phenyl)-1-cyano-N-(2-(cyclohexylamino)-2-oxo-1-(pyridin-3-yl)ethyl)-3,3-dimethylazetidine-2-carboxamide A solution of N-(4-tert-butylphenyl)-N-[2-(cyclohexylamino)-2-oxo-1-(3-pyridyl)ethyl]-3,3-dimethyl-azetidine-2-carboxamide (101 mg, 211.89 umol, 1 eq) and TEA (64.32 mg, 635.68 umol, 88.48 uL, 3 eq) in DCM (1 mL) was cooled to −15° C., and then a solution of BrCN (44.89 mg, 423.79 umol, 31.17 uL, 2 eq) in DCM (0.2 mL) was added drop wise. The resulting solution was stirred at 0° C. and warmed to 25° C. for 1 h gradually. The solution was quenched with $H_2O$ (10 mL) and extracted with DCM (20 mL×3). The organic phase was combined, dried over $Na_2SO_4$, filtrated and concentrated to give a residue. The residue was purified by prep-HPLC (neutral condition), column: Waters Xbridge Prep OBD C18 150*40 mm*10 um; mobile phase: [water (10 mM NH4HCO3)-ACN]; B %: 45%-65%, 8 min N-(4-tert-butylphenyl)-1-cyano-N-[2-(cyclohexylamino)-2-oxo-1-(3-pyridyl)ethyl]-3,3-dimethyl-azetidine-2-carboxamide (25 mg, 49.83 umol, 23.52% yield, 100% purity) was obtained as a solid. $^1H$ NMR (400 MHz, METHANOL-$d_4$) δ ppm 8.35-8.22 (m, 2H), 7.92-7.11 (m, 5H), 6.78 (br s, 1H), 6.22 (s, 1H), 4.68 (s, 1H), 3.79-3.62 (m, 3H), 1.97 (br d, J=12.3 Hz, 1), 1.85-1.58 (m, 4H), 1.27 (s, 4H), 1.21 (s, 9H), 1.19-1.04 (m, 2H), 0.61 (s, 3H). MS (ESI) m/z 502.2 $[M+H]^+$.

Example 26: Synthesis of Compound 379

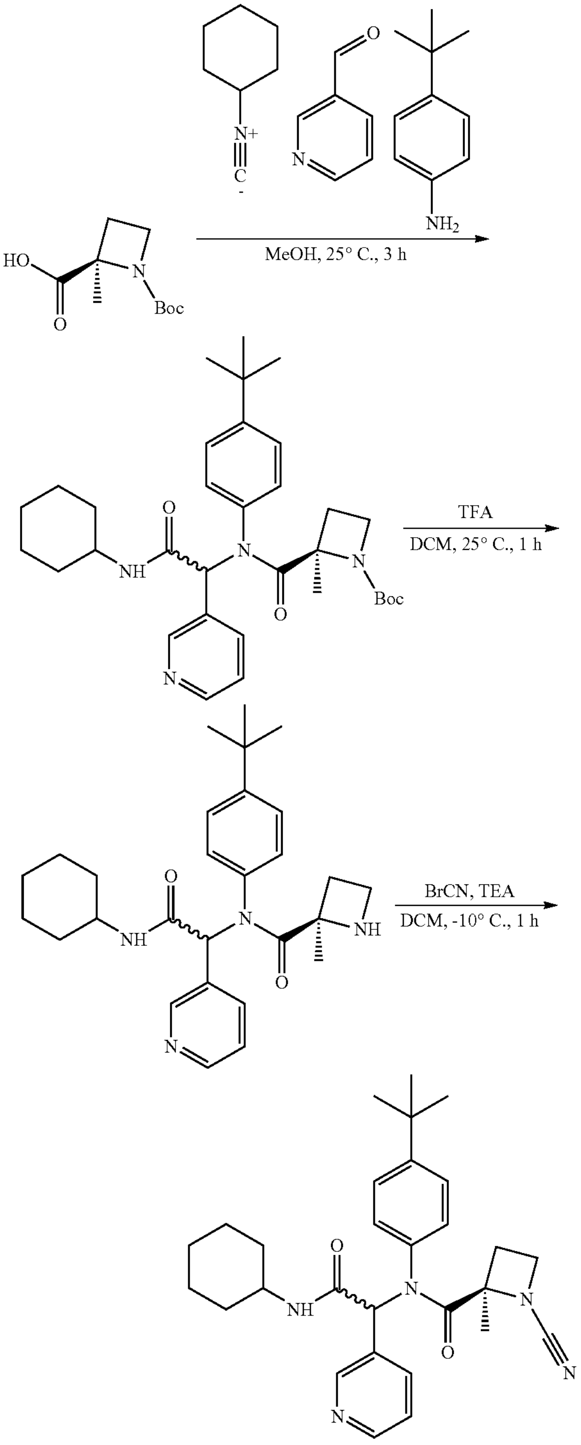

Step 1: (2R)-tert-butyl 2-((4-(tert-butyl)phenyl)(2-(cyclohexylamino)-2-oxo-1-(pyridin-3-yl)ethyl)carbamoyl)-2-methylazetidine-1-carboxylate A solution of pyridine-3-carbaldehyde (99.52 mg, 929.17 umol, 87.30 uL, 1 eq), 4-tert-butylaniline (138.66 mg, 929.17 umol, 146.73 uL, 1 eq), (2R)-1-tert-butoxycarbonyl-2-methyl-azetidine-2-carboxylic acid (200 mg, 929.17 umol, 1 eq) and isocyanocyclohexane (91.29 mg, 836.25 umol, 103.98 uL, 0.9 eq) in MeOH (4 mL) was stirred at 25° C. for 3 h. The reaction mixture was concentrated under reduced pressure, then purified by column chromatography ($SiO_2$, petroleum ether/EtOAc=10/1 to 1/1) to give the product (2R)-tert-butyl 2-((4-(tert-butyl)phenyl)(2-(cyclohexylamino)-2-oxo-1-(pyridin-3-yl)ethyl)carbamoyl)-2-methylazetidine-1-carboxylate (505 mg, 879.45 umol, 94.65% yield, 98% purity) as a solid. MS (ESI) m/z 563.3 $[M+H]^+$.

Step 2: (2R)—N-(4-(tert-butyl)phenyl)-N-(2-(cyclohexylamino)-2-oxo-1-(pyridin-3-yl)ethyl)-2-methylazetidine-2-carboxamide A solution of (2R)-tert-butyl 2-((4-(tert-butyl)phenyl)(2-(cyclohexylamino)-2-oxo-1-(pyridin-3-yl)ethyl)carbamoyl)-2-methylazetidine-1-carboxylate (505 mg, 879.45 umol, 98% purity, 1 eq) in DCM (9 mL) and TFA (3 mL) was stirred at 25° C. for 1 h. The reaction mixture was concentrated under reduced pressure and then purified by prep-HPLC (column: Phenomenex luna C18 250*50 mm*10 um; mobile phase: [water (0.1% TFA)-ACN]; B %: 20%-50%, 10 min) to give (2R)—N-(4-tert-butylphenyl)-N-[2-(cyclohexylamino)-2-oxo-1-(3-pyridyl)ethyl]-2-methyl-azetidine-2-carboxamide (382 mg, 825.72 umol, 93.89% yield, 100% purity) as a solid. MS (ESI) m/z 463.2 $[M+H]^+$. $^1H$ NMR (400 MHz, MeOD-$d_4$) δ ppm 8.51-8.38 (m, 2H), 7.85-7.63 (m, 2H), 7.53-7.32 (m, 2H), 7.18 (s, 1H), 6.76 (s, 1H), 6.19-6.07 (m, 1H), 3.97-3.83 (m, 1H), 3.78-3.66 (m, 1H), 3.65-3.53 (m, 1H), 3.04-2.86 (m, 1H), 1.96-1.85 (m, 1H), 1.82-1.57 (m, 7H), 1.57-1.45 (m, 1H), 1.43-1.25 (m, 3H), 1.22 (s, 9H), 1.19-1.02 (m, 2H).

Step 3: (2R)—N-(4-(tert-butyl)phenyl)-1-cyano-N-(2-(cyclohexylamino)-2-oxo-1-(pyridin-3-yl)ethyl)-2-methylazetidine-2-carboxamide To a solution of (2R)—N-(4-tert-butylphenyl)-N-[2-(cyclohexylamino)-2-oxo-1-(3-pyridyl)ethyl]-2-methyl-azetidine-2-carboxamide (260 mg, 562.01 umol, 100% purity, 1 eq) in DCM (3 mL) was added TEA (170.61 mg, 1.69 mmol, 234.67 uL, 3 eq) and BrCN (60.72 mg, 573.25 umol, 42.17 uL, 1.02 eq) under $N_2$ at −10° C. The resulting mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC (column: Waters Xbridge BEH C18 100*25 mm*5 um; mobile phase: [water (10 mM $NH_4HCO_3$)-ACN]; B %: 35%-75%, 10 min.) to give (2R)—N-(4-tert-butylphenyl)-1-cyano-N-[2-(cyclohexylamino)-2-oxo-1-(3-pyridyl)ethyl]-2-methyl-azetidine-2-carboxamide (80 mg, 164.06 umol, 29.19% yield, 100% purity) as a solid. MS (ESI) m/z 488.2 $[M+H]^+$. $^1H$ NMR (400 MHz, MeOD-$d_4$) δ ppm 8.34-8.24 (m, 2H), 7.72 (s, 1H), 7.52-7.45 (m, 1H), 7.36 (s, 1H), 7.21-6.93 (m, 2H), 6.63 (s, 1H), 6.08-5.99 (m, 1H), 3.83-3.61 (m, 3H), 2.78-2.54 (m, 1H), 2.02-1.89 (m, 1H), 1.83-1.57 (m, 7H), 1.50-1.24 (m, 4H), 1.22-1.18 (m, 9H), 1.18-0.97 (m, 2H).

Example 27: Synthesis of Compound 196

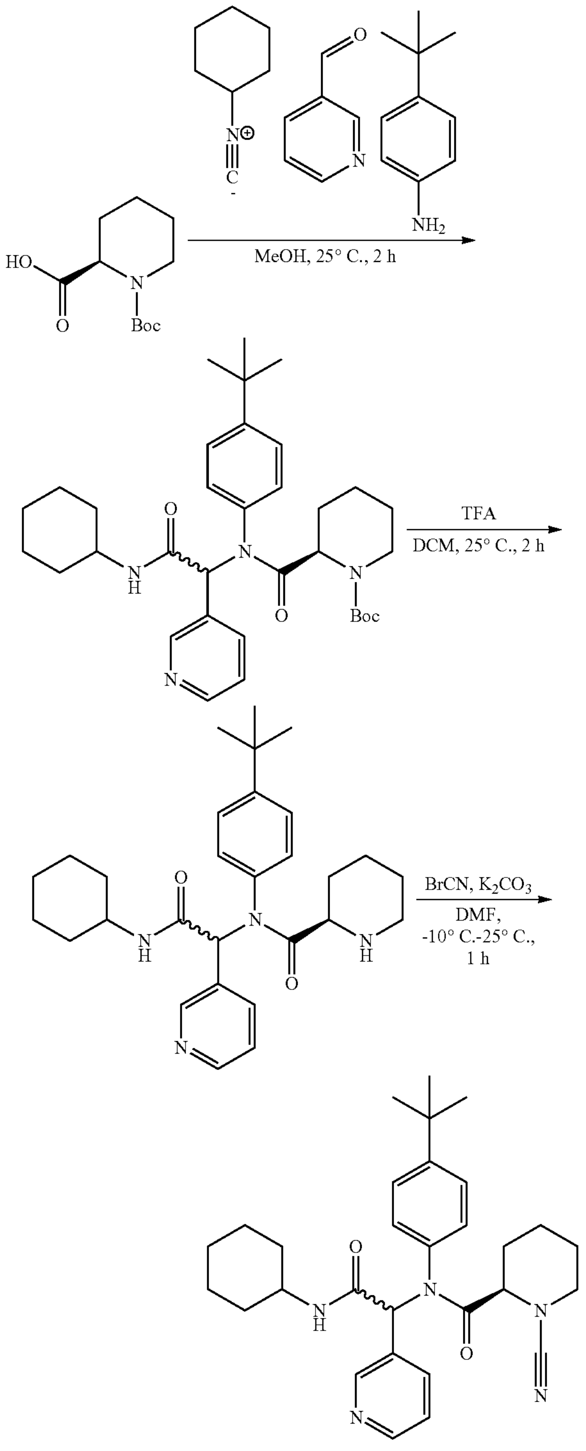

Step 1: tert-butyl (2R)-2-[(4-tert-butylphenyl)-[2-(cyclohexylamino)-2-oxo-1-(3-pyridyl)ethyl]carbamoyl]piperidine-1-carboxylate A solution of pyridine-3-carbaldehyde (233.59 mg, 2.18 mmol, 204.90 uL, 1 eq), 4-tert-butylaniline (325.45 mg, 2.18 mmol, 344.39 uL, 1 eq) in MeOH (3 mL) was stirred at 25° C. for 0.5 h. (2R)-1-tert-butoxycarbonylpiperidine-2-carboxylic acid (500 mg, 2.18 mmol, 1 eq) and isocyanocyclohexane (238.08 mg, 2.18 mmol, 271.16 uL, 1 eq) were added at 25° C. for 1.5 h. The solution was diluted with $H_2O$ (10 mL), and extracted with EtOAc (3*20 mL). The combined organic phase was dried over $Na_2SO_4$, filtrated and concentrated to give the crude: tert-butyl (2R)-2-[(4-tert-butylphenyl)-[2-(cyclohexylamino)-2-oxo-1-(3-pyridyl) ethyl]carbamoyl]piperidine-1-carboxylate (600 mg, crude) as an oil. MS (ESI) m/z 577.1 $[M+H]^+$.

Step 2: (2R)—N-(4-tert-butylphenyl)-N-[2-(cyclohexylamino)-2-oxo-1-(3-pyridyl)ethyl]piperidine-2-carboxamide and (2R)—N-(4-tert-butylphenyl)-N-[2-(cyclohexylamino)-2-oxo-1-(3-pyridyl)ethyl] piperidine-2-carboxamide To a solution of tert-butyl (2R)-2-[(4-tert-butylphenyl)-[2-(cyclohexylamino)-2-oxo-1-(3-pyridyl)ethyl]carbamoyl] piperidine-1-carboxylate (600.00 mg, 1.04 mmol, 1 eq) in DCM (4 mL) was added TFA (6.18 g, 54.21 mmol, 4.01 mL, 52.11 eq), and the resulting solution was stirred at 25° C. for 2 h. The solution was diluted with $H_2O$ (10 mL), extracted with EtOAc (3*20 mL), the combined organic phase was dried over $Na_2SO_4$, filtrated and concentrated to give the crude. The residue (600 mg) was purified by prep-HPLC (ET36162-287-P1: column: Waters Xbridge BEH C18 100*30 mm*10 um; mobile phase: [water (10 mM $NH_4HCO_3$)-ACN]; B %: 34%-64%, 10 min) to get (2R)—N-(4-tert-butylphenyl)-N-[2-(cyclohexylamino)-2-oxo-1-(3-pyridyl)ethyl]piperidine-2-carboxamide (200 mg, 398.61 umol, 38.32% yield, 95% purity) as a solid and (2R)—N-(4-tert-butylphenyl)-N-[2-(cyclohexylamino)-2-oxo-1-(3-pyridyl)ethyl]piperidine-2-carboxamide (200 mg, 398.61 umol, 38.32% yield, 95% purity) as a solid. MS (ESI) m/z 477.1 $[M+H]^+$.

Step 3: (2R)—N-(4-tert-butylphenyl)-N-[2-(cyclohexylamino)-2-oxo-1-(3-pyridyl)ethyl]piperidine-2-carboxamide The (2R)—N-(4-tert-butylphenyl)-N-[2-(cyclohexylamino)-2-oxo-1-(3-pyridyl)ethyl]piperidine-2-carboxamide (20 mg, 41.96 umol, 1 eq) was purified by prep-HPLC (column: Phenomenex Luna C18 100*30 mm*5 um; mobile phase: [water (0.1% TFA)-ACN]; B %: 20%-50%, 10 min) to get (2R)—N-(4-tert-butylphenyl)-N-[2-(cyclohexylamino)-2-oxo-1-(3-pyridyl)ethyl]piperidine-2-carboxamide (10 mg, 20.98 umol, 12.10% yield, 100% purity) as a solid. MS (ESI) m/z 477.1 $[M+H]^+$. $^1H$ NMR (400 MHz, METHANOL-$d_4$) δ ppm 1.01-1.28 (m, 14H) 1.29-1.42 (m, 2H) 1.57-1.79 (m, 8H) 1.86 (br d, J=12.23 Hz, 1H) 1.99 (br d, J=14.92 Hz, 1H) 2.94 (td, J=12.78, 3.06 Hz, 1H) 3.32-3.36 (m, 1H) 3.58-3.77 (m, 2H) 6.00 (s, 1H) 7.08-7.86 (m, 5H) 8.43 (br s, 2H).

Step 4: (2R)—N-(4-tert-butylphenyl)-N-[2-(cyclohexylamino)-2-oxo-1-(3-pyridyl)ethyl]piperidine-2-carboxamide The (2R)—N-(4-tert-butylphenyl)-N-[2-(cyclohexylamino)-2-oxo-1-(3-pyridyl)ethyl]piperidine-2-carboxamide (20 mg, 41.96 umol, 1 eq) was purified by prep-HPLC (column: Phenomenex Luna C18 100*30 mm*5 um; mobile phase: [water (0.1% TFA)-ACN]; B %: 20%-50%, 10 min) to get (2R)—N-(4-tert-butylphenyl)-N-[2-(cyclohexylamino)-2-oxo-1-(3-pyridyl)ethyl]piperidine-2-carboxamide (10 mg, 20.98 umol, 12.10% yield, 100% purity) as a solid. MS (ESI) m/z 477.1 $[M+H]^+$. $^1H$ NMR (400 MHz, METHANOL-$d_4$) δ ppm 1.04-1.26 (m, 13H) 1.28-1.43 (m, 2H) 1.56-1.81 (m, 8H) 1.89 (br d, J=10.64 Hz, 1H) 1.98-2.10 (m, 1H) 2.93 (td, J=12.75, 3.36 Hz, 1H) 3.35 (br d, J=1.34 Hz, 1H) 3.62-3.78 (m, 2H) 6.22 (s, 1H) 6.80 (br s, 1H) 7.08-7.82 (m, 5H) 8.40 (br d, J=3.79 Hz, 2H).

Step 5: (2R)—N-(4-tert-butylphenyl)-1-cyano-N-[2-(cyclohexylamino)-2-oxo-1-(3-pyridyl)ethyl]piperidine-2-carboxamide To a mixture of (2R)—N-(4-tert-butylphenyl)-N-[2-(cyclohexylamino)-2-oxo-1-(3-pyridyl)ethyl]piperidine-2-carboxamide (100 mg, 209.80 umol, 1 eq) in DMF (2 mL) was added $K_2CO_3$ (86.99 mg, 629.39 umol, 3 eq) and BrCN (44.44 mg, 419.59 umol, 30.86 uL, 2 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Phenomenex Gemini-NX C18 75*30 mm*3 um; mobile phase: [water (10 mM NH4HCO3)-ACN]; B %: 30%-60%, 6 min0) to get (2R)—N-(4-tert-butylphenyl)-1-cyano-N-[2-(cyclohexylamino)-2-oxo-1-(3-pyridyl)ethyl]piperidine-2-carboxamide (10 mg, 19.73 umol, 9.41% yield, 99% purity) as a solid. MS (ESI) m/z 502.1 $[M+H]^+$. $^1H$ NMR (400 MHz, METHANOL-$d_4$) δ ppm 1.03-1.23 (m, 3H) 1.26 (s, 9H) 1.29-1.43 (m, 3H) 1.52-1.82 (m, 9H) 1.90 (br d, J=12.59 Hz, 1H) 2.96-3.08 (m, 1H) 3.58-3.72 (m, 2H) 3.83 (t, J=5.26 Hz, 1H) 5.99 (s, 1H) 6.67 (br s, 1H) 7.05-7.75 (m, 5H) 8.25-8.43 (m, 2H).

Step 6: (2R)—N-(4-tert-butylphenyl)-1-cyano-N-[2-(cyclohexylamino)-2-oxo-1-(3-pyridyl)ethyl]piperidine-2-carboxamide To a mixture of (2R)—N-(4-tert-butylphenyl)-N-[2-(cyclohexylamino)-2-oxo-1-(3-pyridyl)ethyl]piperidine-2-carboxamide (100 mg, 209.80 umol, 1 eq) in DMF (2 mL) was added $K_2CO_3$ (86.99 mg, 629.39 umol, 3 eq), and BrCN (44.44 mg, 419.59 umol, 30.86 uL, 2 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Waters Xbridge BEH C18 100*25 mm*5 um; mobile phase: [water (10 mM $NH_4HCO_3$)-ACN]; B %: 35%-70%, 10 min) to get (2R)—N-(4-tert-butylphenyl)-1-cyano-N-[2-(cyclohexylamino)-2-oxo-1-(3-pyridyl)ethyl]piperidine-2-carboxamide (10 mg, 19.93 umol, 9.50% yield, 100% purity) as a solid. MS (ESI) m/z 502.1 $[M+H]^+$. $^1H$ NMR (400 MHz, METHANOL-$d_4$) δ ppm 1.02-1.24 (m, 11H) 1.24-1.44 (m, 4H) 1.50-1.88 (m, 9H) 1.94 (br d, J=12.72 Hz, 1H) 2.98-3.00 (m, 1H) 3.59-3.75 (m, 2H) 3.78 (dd, J=7.09, 4.16 Hz, 1H) 6.15 (s, 1H) 6.65 (br s, 1H) 7.08-7.76 (m, 5H) 8.22-8.33 (m, 2H).

Example 28: Synthesis of Compound 202

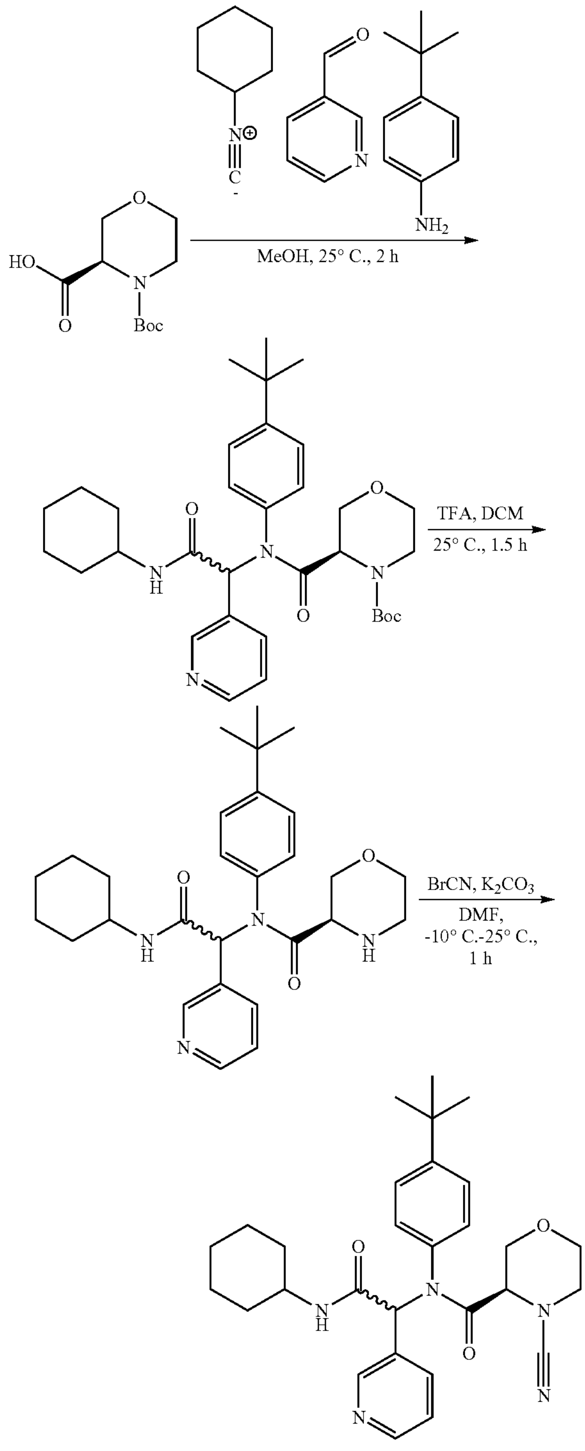

Step 1: tert-butyl (3R)-3-[(4-tert-butylphenyl)-[2-(cyclohexylamino)-2-oxo-1-(3-pyridyl)ethyl]carbamoyl]morpholine-4-carboxylate A solution of pyridine-3-carbaldehyde (138.96 mg, 1.30 mmol, 121.89 uL, 1 eq) and 4-tert-butylaniline (193.60 mg, 1.30 mmol, 204.87 uL, 1 eq) in MeOH (1 mL) was stirred at 25° C. for 0.5 h. The resulting mixture was added with (3R)-4-tert-butoxycarbonylmorpholine-3-carboxylic acid (300 mg, 1.30 mmol, 1 eq) and isocyanocyclohexane (141.63 mg, 1.30 mmol, 161.31 uL, 1 eq) and stirred 25° C. for 1.5 h. The solution was diluted with $H_2O$ (10 mL), extracted with EtOAc (3*20 mL), the combined organic phase was dried over $Na_2SO_4$, filtrated and concentrated to give the crude: tert-butyl (3R)-3-[(4-tert-butylphenyl)-[2-(cyclohexylamino)-2-oxo-1-(3-pyridyl)ethyl]carbamoyl] morpholine-4-carboxylate (600 mg, crude) as an oil. MS (ESI) m/z 579.1 $[M+H]^+$.

Step 2: (3R)—N-(4-tert-butylphenyl)-N-[2-(cyclohexylamino)-2-oxo-1-(3-pyridyl)ethyl]morpholine-3-carboxamide and (3R)—N-(4-tert-butylphenyl)-N-[2-(cyclohexylamino)-2-oxo-1-(3-pyridyl)ethyl] morpholine-3-carboxamide To a solution of tert-butyl (3R)-3-[(4-tert-butylphenyl)-[2-(cyclohexylamino)-2-oxo-1-(3-pyridyl)ethyl]carbamoyl] morpholine-4-carboxylate (100.00 mg, 172.79 umol, 1 eq) in DCM (2 mL) was added TFA (1 mL), and the resulting mixture was stirred 25° C. for 1.5 h. The solution was diluted with $H_2O$ (10 mL), extracted with EtOAc (3*20 mL), and the combined organic phase was dried over $Na_2SO_4$, filtrated and concentrated to give the crude. The residue was purified by prep-HPLC (column: Phenomenex luna C18 100*40 mm*5 um; mobile phase: [water (0.1% TFA)-ACN]; B %: 20%-37%, 8 min) to get (3R)—N-(4-tert-butylphenyl)-N-[2-(cyclohexylamino)-2-oxo-1-(3-pyridyl)ethyl]morpholine-3-carboxamide (30 mg, 62.05 umol, 35.91% yield, 99% purity) as a solid. MS (ESI) m/z 479.1 $[M+H]^+$. $^1H$ NMR (400 MHz, METHANOL-$d_4$) δ ppm 1.01-1.22 (m, 3H) 1.25-1.37 (m, 11H) 1.58-1.79 (m, 4H) 1.85 (br d, J=11.37 Hz, 1H) 3.15-3.29 (m, 2H) 3.54-3.72 (m, 3H) 3.85-4.03 (m, 3H) 6.01 (s, 1H) 6.59-6.98 (m, 1H) 7.20-7.86 (m, 5H) 8.45-8.52 (m, 2H). (3R)—N-(4-tert-butylphenyl)-N-[2-(cyclohexylamino)-2-oxo-1-(3-pyridyl)ethyl]morpholine-3-carboxamide (40 mg, 82.74 umol, 47.88% yield, 99% purity) as a solid. MS (ESI) m/z 479.1 $[M+H]^+$. $^1H$ NMR (400 MHz, METHANOL-$d_4$) δ ppm 1.04-1.20 (m, 2H) 1.24 (s, 9H) 1.27-1.44 (m, 3H) 1.58-1.81 (m, 4H) 1.83-1.95 (m, 1H) 3.15-3.28 (m, 2H) 3.52-3.75 (m, 3H) 3.84-4.04 (m, 3H) 6.22 (s, 1H) 6.84 (br s, 1H) 7.22-7.52 (m, 3H) 7.60-7.78 (m, 2H) 8.41 (br s, 2H).

Step 3: (3R)—N-(4-tert-butylphenyl)-4-cyano-N-[2-(cyclohexylamino)-2-oxo-1-(3-pyridyl)ethyl]morpholine-3-carboxamide To a mixture of (3R)—N-(4-tert-butylphenyl)-N-[2-(cyclohexylamino)-2-oxo-1-(3-pyridyl)ethyl]morpholine-3-carboxamide (100.00 mg, 208.93 umol, 1 eq) in DMF (2 mL) was added $K_2CO_3$ (86.63 mg, 626.80 umol, 3 eq) and BrCN (110.65 mg, 1.04 mmol, 76.84 uL, 5 eq) in one portion at −10° C. The resulting mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Waters Xbridge Prep OBD C18 150*40 mm*10 um; mobile phase: [water (10 mM NH4HCO3)-ACN]; B %: 40%-60%, 8 min) to get (3R)—N-(4-tert-butylphenyl)-4-cyano-N-[2-(cyclohexylamino)-2-oxo-1-(3-pyridyl)ethyl] morpholine-3-carboxamide (10 mg, 18.86 umol, 9.03% yield, 95% purity) as a solid. MS (ESI) m/z 504.1 $[M+H]^+$.

$^1$H NMR (400 MHz, METHANOL-$d_4$) δ ppm 1.04-1.19 (m, 2H) 1.22-1.27 (m, 9H) 1.29-1.41 (m, 3H) 1.52-1.80 (m, 4H) 1.91 (br d, J=12.23 Hz, 1H) 3.06-3.14 (m, 1H) 3.58-3.69 (m, 3H) 3.76 (s, 3H) 3.94 (t, J=4.16 Hz, 1H) 6.00 (s, 1H) 6.64 (br s, 1H) 6.99-7.78 (m, 5H) 8.34 (td, J=4.46, 1.83 Hz, 2H).

Step 4: (3R)—N-(4-tert-butylphenyl)-4-cyano-N-[2-(cyclohexylamino)-2-oxo-1-(3-pyridyl)ethyl]morpholine-3-carboxamide To a mixture of (3R)—N-(4-tert-butylphenyl)-N-[2-(cyclohexylamino)-2-oxo-1-(3-pyridyl)ethyl]morpholine-3-carboxamide (100.00 mg, 208.93 umol, 1 eq) in DMF (2 mL) was added $K_2CO_3$ (86.63 mg, 626.80 umol, 3 eq), BrCN (110.65 mg, 1.04 mmol, 76.84 uL, 5 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Phenomenex Gemini-NX 80*40 mm*3 um; mobile phase: [water (10 mM NH4HCO3)-ACN]; B %: 30%-50%, 8 min) to get (3R)—N-(4-tert-butylphenyl)-4-cyano-N-[2-(cyclohexylamino)-2-oxo-1-(3-pyridyl)ethyl]morpholine-3-carboxamide (10 mg, 19.86 umol, 9.50% yield, 100% purity) as a solid. MS (ESI) m/z 504.1 [M+H]$^+$. $^1$H NMR (400 MHz, METHANOL-$d_4$) δ ppm 1.01-1.18 (m, 2H) 1.23 (s, 9H) 1.27-1.43 (m, 3H) 1.57-1.82 (m, 4H) 1.93 (br d, J=10.76 Hz, 1H) 3.03-3.14 (m, 1H) 3.57-3.69 (m, 3H) 3.71-3.82 (m, 3H) 3.83-3.91 (m, 1H) 6.17 (s, 1H) 6.67 (br s, 1H) 7.09-7.75 (m, 5H) 8.17-8.39 (m, 2H).

Example 29: Synthesis of Compound 217

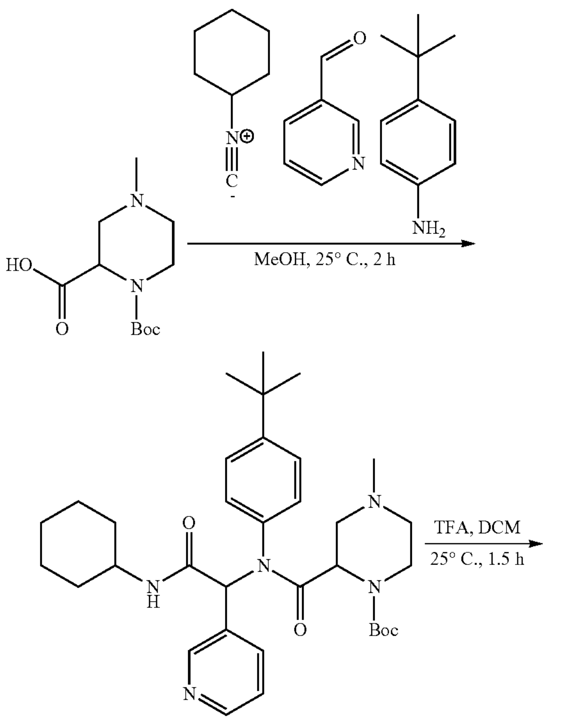

-continued

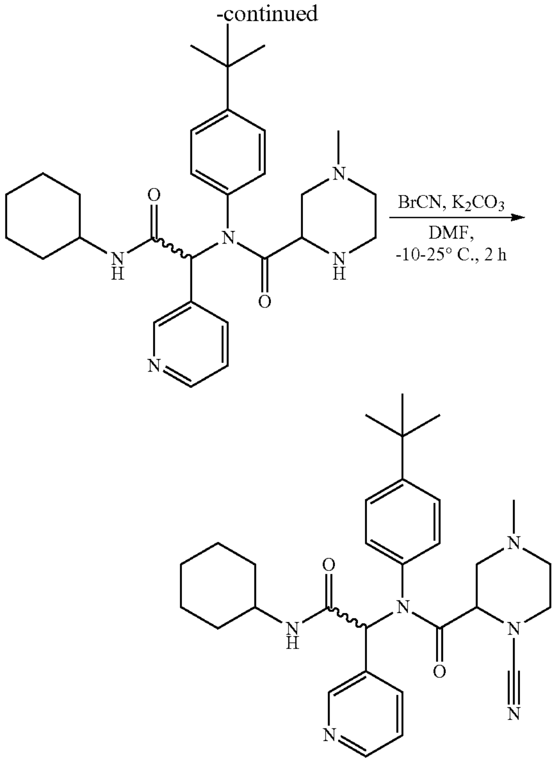

Step 1: tert-butyl 2-[(4-tert-butylphenyl)-[2-(cyclohexylamino)-2-oxo-1-(3-pyridyl)ethyl]carbamoyl]-4-methyl-piperazine-1-carboxylate A solution of pyridine-3-carbaldehyde (131.54 mg, 1.23 mmol, 115.38 uL, 1 eq) and 4-tert-butylaniline (183.27 mg, 1.23 mmol, 193.93 uL, 1 eq) in MeOH (3 mL) was stirred at 25° C. for 0.5 h, and then 1-tert-butoxycarbonyl-4-methyl-piperazine-2-carboxylic acid (300 mg, 1.23 mmol, 1 eq) and isocyanocyclohexane (134.07 mg, 1.23 mmol, 152.69 uL, 1 eq) were added at 25° C. for 1.5 h. The solution was diluted with $H_2O$ (10 mL), extracted with EtOAc (3*20 mL), the combined organic phase was dried over $Na_2SO_4$, filtrated and concentrated to give the crude. The residue was purified by flash silica gel chromatography to get tert-butyl 2-[(4-tert-butylphenyl)-[2-(cyclohexylamino)-2-oxo-1-(3-pyridyl)ethyl]carbamoyl]-4-methyl-piperazine-1-carboxylate (200 mg, 287.27 umol, 23.39% yield, 85% purity) as an oil. MS (ESI) m/z 592.1 [M+H]$^+$.

Step 2: N-(4-tert-butylphenyl)-N-[2-(cyclohexylamino)-2-oxo-1-(3-pyridyl)ethyl]-4-methyl-piperazine-2-carboxamide and N-(4-tert-butylphenyl)-N-[2-(cyclohexylamino)-2-oxo-1-(3-pyridyl)ethyl]-4-methyl-piperazine-2-carboxamide To a solution of tert-butyl 2-[(4-tert-butylphenyl)-[2-(cyclohexylamino)-2-oxo-1-(3-pyridyl)ethyl]carbamoyl]-4-methyl-piperazine-1-carboxylate (150 mg, 253.47 umol, 1 eq) in DCM (2 mL) was added TFA (1 mL) at 25° C. for 1.5 h. The solution was diluted with $H_2O$ (10 mL), extracted with EtOAc (3*20 mL), the combined organic phase was dried over $Na_2SO_4$, filtrated and concentrated to give a residue. The residue was purified by prep-HPLC (column: Waters Xbridge BEH C18 100*25 mm*5 um; mobile phase:

[water (10 mM NH4HCO3)-ACN]; B %: 30%-55%, 10 min) to get N-(4-tert-butylphenyl)-N-[2-(cyclohexylamino)-2-oxo-1-(3-pyridyl)ethyl]-4-methyl-piperazine-2-carboxamide (70 mg, 142.37 umol, 56.17% yield, 100% purity) as a solid. MS (ESI) m/z 492.1 $[M+H]^+$. $^1H$ NMR (400 MHz, METHANOL-$d_4$) δ ppm 1.06-1.23 (m, 3H) 1.25 (s, 9H) 1.28-1.42 (m, 2H) 1.56-1.78 (m, 4H) 1.82-2.00 (m, 3H) 2.14 (s, 3H) 2.46-2.64 (m, 2H) 2.83 (dd, J=11.37, 1.71 Hz, 1H) 2.89-3.00 (m, 1H) 3.41-3.50 (m, 1H) 3.64 (tt, J=10.77, 3.71 Hz, 1H) 5.97 (s, 1H) 6.65 (br s, 1H) 6.96-7.84 (m, 5H) 8.33 (td, J=5.41, 1.77 Hz, 2H). N-(4-tert-butylphenyl)-N-[2-(cyclohexylamino)-2-oxo-1-(3-pyridyl)ethyl]-4-methyl-piperazine-2-carboxamide (70 mg, 138.10 umol, 54.48% yield, 97% purity) was obtained as a solid. MS (ESI) m/z 492.1 $[M+H]^+$. $^1H$ NMR (400 MHz, METHANOL-$d_4$) δ ppm 1.02-1.19 (m, 2H) 1.21 (s, 9H) 1.24-1.45 (m, 3H) 1.57-1.81 (m, 4H) 1.87-2.01 (m, 3H) 2.17 (s, 3H) 2.49-2.68 (m, 2H) 2.86-3.06 (m, 2H) 3.45 (dd, J=10.64, 2.93 Hz, 1H) 3.71 (tt, J=10.79, 3.82 Hz, 1H) 6.14 (s, 1H) 6.70 (br s, 1H) 7.05-7.83 (m, 5H) 8.19-8.32 (m, 2H).

Step 3: N-(4-tert-butylphenyl)-1-cyano-N-[2-(cyclohexylamino)-2-oxo-1-(3-pyridyl)ethyl]-4-methyl-piperazine-2-carboxamide To a mixture of N-(4-tert-butylphenyl)-N-[2-(cyclohexylamino)-2-oxo-1-(3-pyridyl)ethyl]-4-methyl-piperazine-2-carboxamide (50 mg, 101.69 umol, 1 eq) in DMF (3 mL) was added $K_2CO_3$ (42.16 mg, 305.08 umol, 3 eq) and BrCN (17.23 mg, 162.71 umol, 11.97 uL, 2 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Waters Xbridge BEH C18 100*30 mm*10 um; mobile phase: [water (10 mM NH4HCO3)-ACN]; B %: 35%-60%, 8 min) to get N-(4-tert-butylphenyl)-1-cyano-N-[2-(cyclohexylamino)-2-oxo-1-(3-pyridyl)ethyl]-4-methyl-piperazine-2-carboxamide (10 mg, 19.35 umol, 19.03% yield, 100% purity) as a solid. MS (ESI) m/z 517.1 $[M+H]^+$. $^1H$ NMR (400 MHz, METHANOL-$d_4$) δ ppm 1.05-1.22 (m, 3H) 1.26 (s, 9H) 1.29-1.43 (m, 2H) 1.55-1.81 (m, 4H) 1.90 (br d, J=11.00 Hz, 1H) 2.20 (s, 3H) 2.34-2.60 (m, 4H) 2.99-3.14 (m, 1H) 3.56-3.75 (m, 2H) 3.96 (t, J=5.14 Hz, 1H) 6.00 (s, 1H) 6.45-6.81 (m, 1H) 6.95-7.83 (m, 5H) 8.21-8.50 (m, 2H).

Step 4: N-(4-tert-butylphenyl)-1-cyano-A-[2-(cyclohexylamino)-2-oxo-1-(3-pyridyl)ethyl]-4-methyl-piperazine-2-carboxamide To a mixture of N-(4-tert-butylphenyl)-N-[2-(cyclohexylamino)-2-oxo-1-(3-pyridyl)ethyl]-4-methyl-piperazine-2-carboxamide (40.00 mg, 81.36 umol, 1 eq) in DMF (2 mL) was added $K_2CO_3$ (33.73 mg, 244.07 umol, 3 eq) and BrCN (17.23 mg, 162.71 umol, 11.97 uL, 2 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Waters Xbridge BEH C18 100*30 mm*10 um; mobile phase: [water (10 mM NH4HCO3)-ACN]; B %: 30%-60%, 8 min) to get N-(4-tert-butylphenyl)-1-cyano-N-[2-(cyclohexylamino)-2-oxo-1-(3-pyridyl)ethyl]-4-methyl-piperazine-2-carboxamide (10 mg, 19.16 umol, 23.55% yield, 99% purity) as a solid. MS (ESI) m/z 517.1 $[M+H]^+$. $^1H$ NMR (400 MHz, METHANOL-$d_4$) δ ppm 1.23 (s, 11H) 1.24-1.44 (m, 3H) 1.58-1.82 (m, 4H) 1.94 (br d, J=12.47 Hz, 1H) 2.24 (s, 3H) 2.30 (ddd, J=11.89, 10.00, 3.42 Hz, 1H) 2.42 (dd, J=11.98, 8.93 Hz, 1H) 2.50-2.62 (m, 1H) 2.77 (dd, J=11.98, 2.45 Hz, 1H) 2.96-3.07 (m, 1H) 3.50 (dt, J=12.26, 3.59 Hz, 1H) 3.71 (tt, J=10.77, 3.90 Hz, 1H) 3.86 (dd, J=8.86, 3.24 Hz, 1H) 6.17 (s, 1H) 6.66 (br s, 1H) 7.09-7.79 (m, 5H) 8.28 (td, J=4.65, 1.83 Hz, 2H).

Example 30: Synthesis of Compound 232

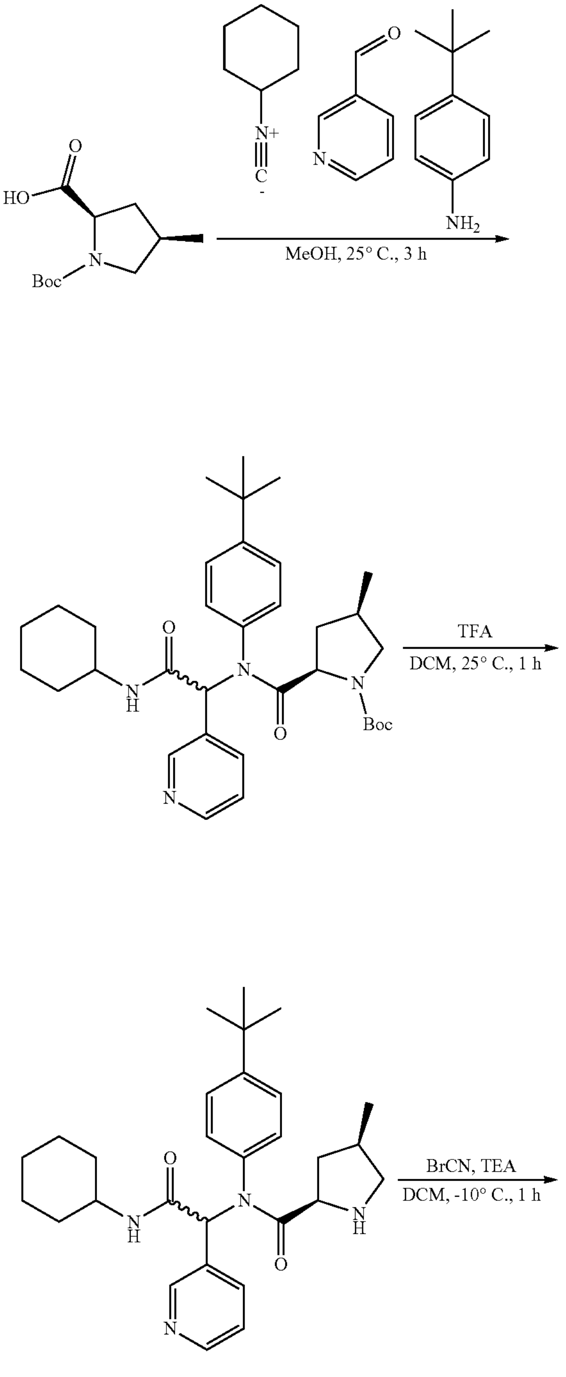

-continued

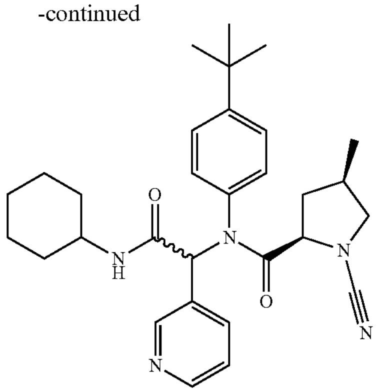

Step 1: (2R,4R)-tert-butyl 2-((4-(tert-butyl)phenyl) (2-(cyclohexylamino)-2-oxo-1-(pyridin-3-yl)ethyl) carbamoyl)-4-methylpyrrolidine-1-carboxylate A solution of pyridine-3-carbaldehyde (186.87 mg, 1.74 mmol, 163.92 uL, 1 eq), 4-tert-butylaniline (260.36 mg, 1.74 mmol, 275.51 uL, 1 eq), (2R,4R)-1-tert-butoxycarbonyl-4-methyl-pyrrolidine-2-carboxylic acid (400 mg, 1.74 mmol, 1 eq) and isocyanocyclohexane (171.42 mg, 1.57 mmol, 195.24 uL, 0.9 eq) in MeOH (8 mL) was stirred at 25° C. for 3 h. The reaction mixture was concentrated under reduced pressure, then purified by column chromatography ($SiO_2$, petroleum ether/EtOAc=10/1 to 1/1) to give the product (2R,4R)-tert-butyl 2-((4-(tert-butyl)phenyl)(2-(cyclohexylamino)-2-oxo-1-(pyridin-3-yl)ethyl)carbamoyl)-4-methylpyrrolidine-1-carboxylate (998 mg, 1.57 mmol, 90.25% yield, 91% purity) as a solid. MS (ESI) m/z 577.5 $[M+H]^+$.

Step 2: (2R,4R)-tert-butyl 2-((4-(tert-butyl)phenyl) (2-(cyclohexylamino)-2-oxo-1-(pyridin-3-yl)ethyl) carbamoyl)-4-methylpyrrolidine-1-carboxylate A solution of tert-butyl (2R,4R)-2-[(4-tert-butylphenyl)-[2-(cyclohexylamino)-2-oxo-1-(3-pyridyl)ethyl]carbamoyl]-4-methyl-pyrrolidine-1-carboxylate (998 mg, 1.57 mmol, 91% purity, 1 eq) in TFA (3 mL) and DCM (9 mL) was stirred at 25° C. for 1 h. The reaction mixture was concentrated under reduced pressure and then purified by prep-HPLC (column: Phenomenex luna C18 250*50 mm*10 um; mobile phase: [water (0.1% TFA)-ACN]; B %: 35%-45%, 10 min.) to give (2R,4R)—N-(4-tert-butylphenyl)-N-[2-(cyclohexylamino)-2-oxo-1-(3-pyridyl)ethyl]-4-methyl-pyrrolidine-2-carboxamide (370 mg, 776.25 umol, 98.60% yield, 100% purity) as a solid, and (2R,4R)—N-(4-tert-butylphenyl)-N-[2-(cyclohexylamino)-2-oxo-1-(3-pyridyl)ethyl]-4-methyl-pyrrolidine-2-carboxamide (361 mg, 757.37 umol, 96.20% yield, 100% purity) as a solid. MS (ESI) m/z 477.2 $[M+H]^+$. $^1H$ NMR (Isomer 1) (400 MHz, MeOD-$d_4$) S ppm 8.56-8.44 (m, 2H), 8.17 (d, J=7.6 Hz, 1H), 7.89-7.76 (m, 1H), 7.75-7.09 (m, 4H), 6.79 (s, 1H), 6.06 (s, 1H), 4.16 (t, J=9.0 Hz, 1H), 3.77-3.62 (m, 1H), 3.44-3.35 (m, 1H), 2.88 (t, J=10.6 Hz, 1H), 2.29-2.13 (m, 1H), 2.03-1.93 (m, 1H), 1.92-1.83 (m, 1H), 1.81-1.54 (m, 5H), 1.42-1.09 (m, 14H), 1.07 (d, J=6.6 Hz, 3H); $^1H$ NMR (Isomer 2) (400 MHz, MeOD-$d_4$) δ ppm 8.52-8.39 (m, 2H), 8.20 (d, J=7.2 Hz, 1H), 7.86-7.55 (m, 2H), 7.52-7.35 (m, 2H), 7.23 (s, 1H), 6.80 (s, 1H), 6.22 (s, 1H), 4.18 (t, J=8.8 Hz, 1H), 3.80-3.66 (m, 1H), 3.44-3.35 (m, 1H), 2.90 (t, J=10.7 Hz, 1H), 2.29-2.14 (m, 1H), 2.02-1.86 (m, 2H), 1.83-1.59 (m, 5H), 1.44-1.10 (m, 14H), 1.07 (d, J=6.6 Hz, 3H).

Step 3:(2R,4R)—N-(4-(tert-butyl)phenyl)-1-cyano-N-(2-(cyclohexylamino)-2-oxo-1-(pyridin-3-yl) ethyl)-4-methylpyrrolidine-2-carboxamide To a solution of (2R,4R)—N-(4-tert-butylphenyl)-N-[2-(cyclohexylamino)-2-oxo-1-(3-pyridyl)ethyl]-4-methyl-pyrrolidine-2-carboxamide (325 mg, 681.84 umol, 1 eq) in DCM (3 mL) was added TEA (206.99 mg, 2.05 mmol, 284.71 uL, 3 eq) and then BrCN (73.67 mg, 695.48 umol, 51.16 uL, 1.02 eq) under $N_2$ at −10° C. The resulting mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC (column: Waters Xbridge BEH C18 100*25 mm*5 um; mobile phase: [water (10 mM NH4HCO3)-ACN]; B %: 40%-75%, 10 min.) to give (2R, 4R)—N-(4-tert-butylphenyl)-1-cyano-N-[2-(cyclohexylamino)-2-oxo-1-(3-pyridyl)ethyl]-4-methyl-pyrrolidine-2-carboxamide (103.9 mg, 207.11 umol, 30.38% yield, 100% purity) as a solid. MS (ESI) m/z 502.2 $[M+H]^+$. $^1H$ NMR (Compounds 232 Isomer 1) (400 MHz, MeOD-$d_4$) S ppm 8.44-8.27 (m, 2H), 7.67 (s, 1H), 7.58-7.51 (m, 1H), 7.46 (s, 1H), 7.35-6.98 (m, 2H), 6.60 (s, 1H), 6.02 (s, 1H), 4.22-4.11 (m, 1H), 3.72-3.60 (m, 1H), 3.52 (t, J=8.0 Hz, 1H), 3.10 (t, J=9.6 Hz, 1H), 2.23-2.00 (m, 2H), 1.97-1.86 (m, 1H), 1.82-1.46 (m, 5H), 1.40-1.06 (m, 14H), 1.00 (d, J=6.4 Hz, 3H).

To a solution of (2R,4R)—N-(4-tert-butylphenyl)-N-[2-(cyclohexylamino)-2-oxo-1-(3-pyridyl)ethyl]-4-methyl-pyrrolidine-2-carboxamide (315 mg, 660.86 umol, 1 eq) in DCM (3 mL) was added TEA (200.62 mg, 1.98 mmol, 275.95 uL, 3 eq) and BrCN (71.40 mg, 674.08 umol, 49.58 uL, 1.02 eq) under $N_2$ at −10° C. The mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC (column: Waters Xbridge BEH C18 100*25 mm*5 um; mobile phase: [water (10 mM NH4HCO3)-ACN]; B %: 50%-80%, 10 min.) to give (2R, 4R)—N-(4-tert-butylphenyl)-1-cyano-N-[2-(cyclohexylamino)-2-oxo-1-(3-pyridyl)ethyl]-4-methyl-pyrrolidine-2-carboxamide (90.0 mg, 179.40 umol, 27.15% yield, 100% purity) as a solid. MS (ESI) m/z 502.2 $[M+H]^+$. $^1H$ NMR (Compound 232 Isomer 2) (400 MHz, MeOD-$d_4$) δ ppm 8.35-8.22 (m, 2H), 7.67 (s, 1H), 7.55-7.48 (m, 1H), 7.41 (s, 1H), 7.22-7.09 (m, 2H), 6.63 (s, 1H), 6.14 (s, 1H), 4.20-4.10 (m, 1H), 3.76-3.65 (m, 1H), 3.54 (t, J=8.0 Hz, 1H), 3.19-3.09 (m, 1H), 2.25-2.00 (m, 2H), 2.00-1.88 (m, 1H), 1.83-1.57 (m, 5H), 1.44-1.06 (m, 14H), 1.03 (d, J=6.4 Hz, 3H).

Example 31: Synthesis of Compound 238

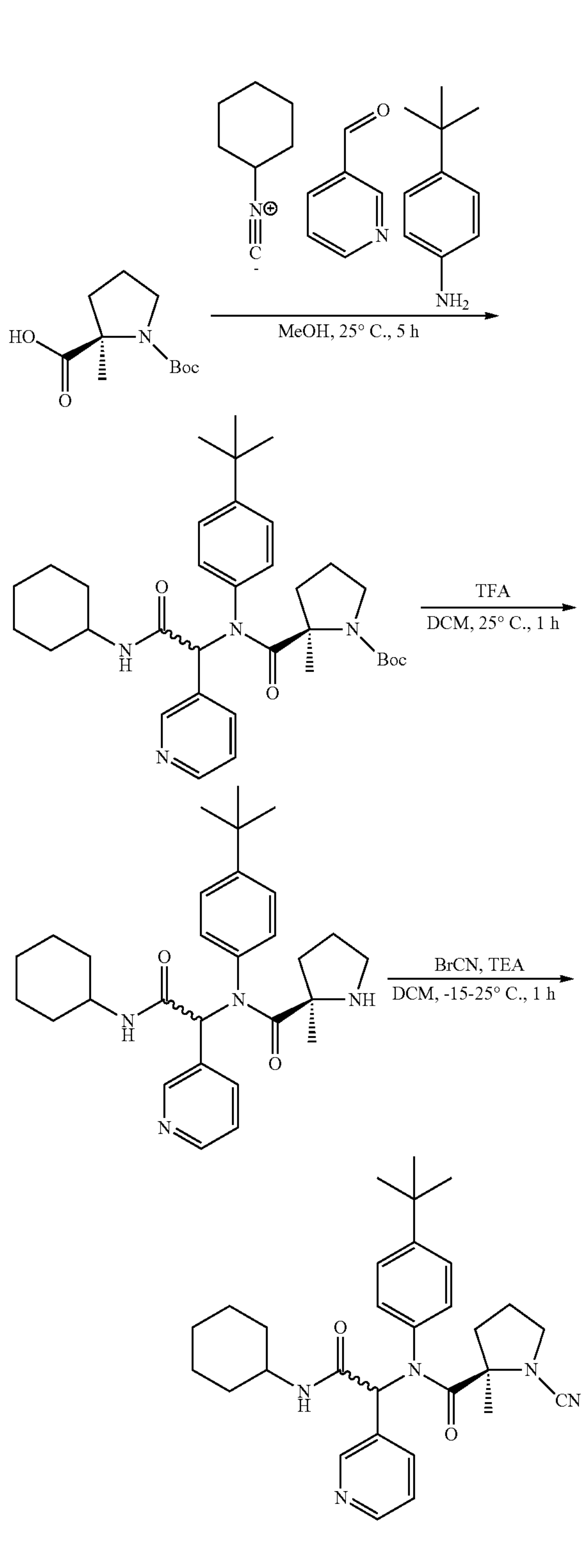

Step 1: (2R)-tert-butyl 2-((4-(tert-butyl)phenyl)(2-(cyclohexylamino)-2-oxo-1-(pyridin-3-yl)ethyl)carbamoyl)-2-methylpyrrolidine-1-carboxylate Pyridine-3-carbaldehyde (140.15 mg, 1.31 mmol, 122.94 uL, 1 eq) and 4-tert-butylaniline (195.27 mg, 1.31 mmol, 206.63 uL, 1 eq) in MeOH (3 mL) was stirred at 25° C. for 0.5 h, and then (2R)-1-tert-butoxycarbonyl-2-methyl-pyrrolidine-2-carboxylic acid (300 mg, 1.31 mmol, 1 eq) and isocyanocyclohexane (142.85 mg, 1.31 mmol, 162.69 uL, 1 eq) were added. The resulting solution was stirred at 25° C. for 4.5 h. The solution was concentrated to give a residue. The residue was used to next step directly and without further purification. Tert-butyl (2R)-2-[(4-tert-butylphenyl)-[2-(cyclohexylamino)-2-oxo-1-(3-pyridyl)ethyl]carbamoyl]-2-methyl-pyrrolidine-1-carboxylate (750 mg, crude) was obtained as a solid. MS (ESI) m/z 577.4 $[M+H]^+$.

Step 2: (2R)—N-(4-(tert-butyl)phenyl)-N-(2-(cyclohexylamino)-2-oxo-1-(pyridin-3-yl)ethyl)-2-methylpyrrolidine-2-carboxamide Tert-butyl (2R)-2-[(4-tert-butylphenyl)-[2-(cyclohexylamino)-2-oxo-1-(3-pyridyl)ethyl]carbamoyl]-2-methyl-pyrrolidine-1-carboxylate (750.00 mg, 1.30 mmol, 1 eq) in DCM (2 mL)/TFA (1.54 g, 13.51 mmol, 1 mL, 10.39 eq) was stirred at 25° C. for 1 h. Upon the reaction was finished, the solution was concentrated to remove the DCM, adjusted to pH=8-9 by $Na_2CO_3$· aq., and extracted with DCM (20 mL*3). The organic phase was combined, dried over $Na_2SO_4$, filtrated and concentrated to give the crude. The residue was purified by prep-HPLC (TFA condition), column: Phenomenex luna C18 250*50 mm*10 um; mobile phase: [water (0.1% TFA)-ACN]; B %: 25%-45%, 10 min. (2R)—N-(4-tert-butylphenyl)-N-[2-(cyclohexylamino)-2-oxo-1-(3-pyridyl)ethyl]-2-methyl-pyrrolidine-2-carboxamide (240 mg, 503.51 umol, 38.72% yield, 100% purity) was obtained as an oil, (2R)—N-(4-tert-butylphenyl)-N-[2-(cyclohexylamino)-2-oxo-1-(3-pyridyl)ethyl]-2-methyl-pyrrolidine-2-carboxamide (260 mg, 545.47 umol, 41.95% yield, 100% purity) was obtained as an oil. MS (ESI) m/z 477.3 $[M+H]^+$.

Step 3: (2R)—N-(4-(tert-butyl)phenyl)-1-cyano-N-(2-(cyclohexylamino)-2-oxo-1-(pyridin-3-yl)ethyl)-2-methylpyrrolidine-2-carboxamide To a mixture of (2R)—N-(4-tert-butylphenyl)-N-[2-(cyclohexylamino)-2-oxo-1-(3-pyridyl)ethyl]-2-methyl-pyrrolidine-2-carboxamide (100 mg, 209.80 umol, 1 eq) in DCM (1 mL) was added TEA (63.69 mg, 629.39 umol, 87.60 uL, 3 eq), and the solution was cooled to −15° C. BrCN (111.11 mg, 1.05 mmol, 77.16 uL, 5 eq) in DCM (0.2 mL) was added drop-wise and the solution was stirred at 0° C. and warmed to 25° C. gradually for 1 h. Upon the completion of the reaction, the solution was quenched with $H_2O$ at 0° C., extracted with DCM (20 mL*3), the combined organic phase was dried over $Na_2SO_4$, filtrated and concentrated to give a residue. The residue was purified by prep-HPLC (neutral condition), column: Phenomenex Gemini-NX 80*40 mm*3 um; mobile phase: [water (10 mM $NH_4HCO_3$)-ACN]; B %: 35%-55%, 8 min (2R)—N-(4-tert-butylphenyl)-1-cyano-N-[2-(cyclohexylamino)-2-oxo-1-(3-pyridyl)ethyl]-2-methyl-pyrrolidine-2-carboxamide (30 mg, 59.80 umol, 28.50% yield, 100% purity) was obtained as a solid. $^1H$ NMR (400 MHz, METHANOL-$d_4$) δ ppm 8.43-8.25 (m, 2H), 7.87-7.04 (m, 5H), 6.61 (br s, 1H), 6.00 (s, 1H), 4.20 (t, J=7.3 Hz, 1H), 3.89-3.79 (m, 1H), 3.67 (tt, J=3.7, 10.8 Hz, 1H), 2.16-2.02 (m, 1H), 1.99-1.88 (m, 3H), 1.81-1.56 (m, 4H), 1.44-1.27 (m, 4H), 1.26-1.22 (m, 12H), 1.21-1.03 (m, 2H). MS (ESI) m/z 502.2 $[M+H]^+$.

Step 4: (2R)—N-(4-(tert-butyl)phenyl)-1-cyano-N-(2-(cyclohexylamino)-2-oxo-1-(pyridin-3-yl)ethyl)-2-methylpyrrolidine-2-carboxamide To a mixture of (2R)—N-(4-tert-butylphenyl)-N-[2-(cyclohexylamino)-2-oxo-1-(3-pyridyl)ethyl]-2-methyl-pyrrolidine-2-carboxamide (100 mg, 209.80 umol, 1 eq) in DCM (1 mL) was added TEA (63.69 mg, 629.39 umol, 87.60 uL, 3 eq), and the solution was cooled to −15° C. Then, a solution of BrCN (111.11 mg, 1.05 mmol, 77.16 uL, 5 eq) in DCM (0.2 mL) was added drop-wise and the solution was stirred at 0° C., and then warmed to 25° C. gradually over 1 h. The solution was quenched with $H_2O$ at 0° C., extracted with DCM (20 mL*3), the combined organic phase was dried over $Na_2SO_4$, filtrated and concentrated to give a residue. The residue was purified by prep-HPLC (neutral condition), column: Phenomenex Gemini-NX 80*40 mm*3 um; mobile phase: [water (10 mM NH4HCO3)-ACN]; B %: 35%-55%, 8 min. (2R)—N-(4-tert-butylphenyl)-1-cyano-N-[2-(cyclohexylamino)-2-oxo-1-(3-pyridyl)ethyl]-2-methyl-pyrrolidine-2-carboxamide (30 mg, 59.80 umol, 28.50% yield, 100% purity) was obtained as a solid. Compound 238 Isomer 2, $^1$H NMR (400 MHz, METHANOL-$d_4$) δ ppm 8.31-8.24 (m, 2H), 7.77-7.07 (m, 5H), 6.63 (br s, 1H), 6.14 (s, 1H), 4.19 (dd, J=6.5, 7.8 Hz, 1H), 3.93-3.82 (m, 1H), 3.70 (tt, J=3.7, 10.8 Hz, 1H), 2.15-1.89 (m, 4H), 1.82-1.58 (m, 4H), 1.44-1.27 (m, 4H), 1.26-1.21 (m, 12H), 1.19-1.00 (m, 2H).

Example 32: Synthesis of Compound 244

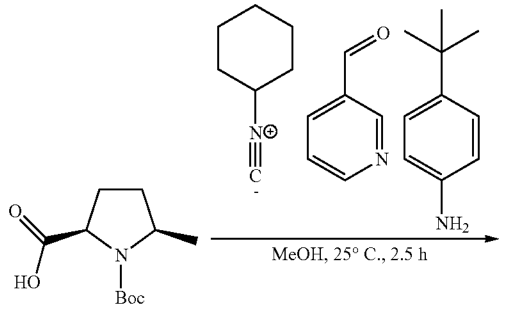

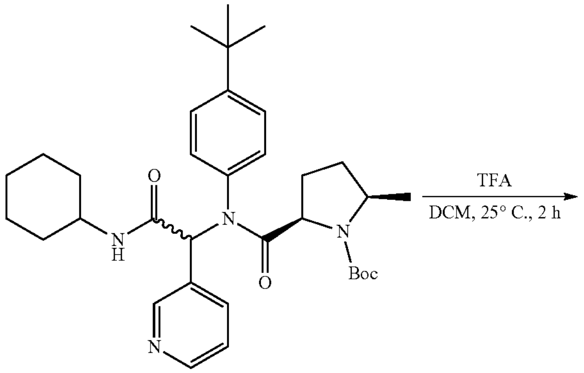

-continued

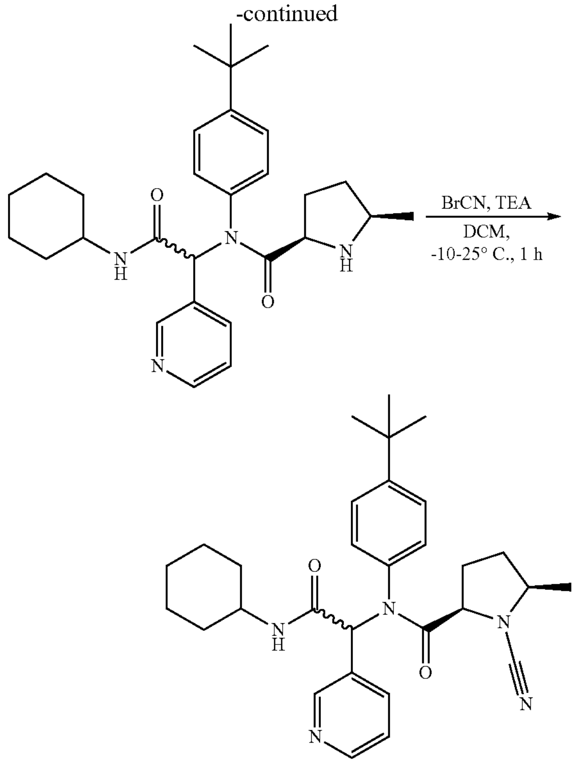

Step 1: tert-butyl (2R,5R)-2-[(4-tert-butylphenyl)-[2-(cyclohexylamino)-2-oxo-1-(3-pyridyl)ethyl]carbamoyl]-5-methyl-pyrrolidine-1-carboxylate A solution of pyridine-3-carbaldehyde (93.43 mg, 872.33 umol, 81.96 uL, 1 eq), and 4-tert-butylaniline (130.18 mg, 872.33 umol, 137.76 uL, 1 eq) in MeOH (1.2 mL) was stirred at 25° C. for 0.5 h, and then was added (2R,5R)-1-tert-butoxycarbonyl-5-methyl-pyrrolidine-2-carboxylic acid (200 mg, 872.33 umol, 1 eq) at 25° C. The reaction mixture was stirred at 25° C. for 0.5 h. Then the isocyanocyclohexane (95.23 mg, 872.33 umol, 108.46 uL, 1 eq) was added into the above solution at 0° C., and then the reaction mixture was stirred at 25° C. for another 1.5 h. The product was purified by prep-TLC ($SiO_2$, petroleum ether/EtOAc=1/1, $R_f$=0.20) and concentrated to get product. The residue was further purified by pre-HPLC. Tert-butyl (2R,5R)-2-[(4-tert-butylphenyl)-[2-(cyclohexylamino)-2-oxo-1-(3-pyridyl)ethyl]carbamoyl]-5-methyl-pyrrolidine-1-carboxylate (173 mg, 279.55 umol, 32.05% yield, 93.2% purity) was obtained as a solid. MS (ESI) m/z 577.3 $[M+H]^+$. Tert-butyl (2R,5R)-2-[(4-tert-butylphenyl)-[2-(cyclohexylamino)-2-oxo-1-(3-pyridyl) ethyl]carbamoyl]-5-methyl-pyrrolidine-1-carboxylate (200 mg, 318.67 umol, 36.53% yield, 91.9% purity) was obtained as a solid. Prep-HPLC condition: column: Phenomenex Gemini-NX 80*40 mm*3 um; mobile phase: [water (10 mM $NH_4HCO_3$)-ACN]; B %: 55%-75%, 8 min. MS (ESI) m/z 577.3 $[M+H]^+$.

Step 2: (2R,5R)—N-(4-tert-butylphenyl)-N-[2-(cyclohexylamino)-2-oxo-1-(3-pyridyl)ethyl]-5-methyl-pyrrolidine-2-carboxamide To a solution of tert-butyl (2R,5R)-2-[(4-tert-butylphenyl)-[2-(cyclohexylamino)-2-oxo-1-(3-pyridyl)ethyl]carbamoyl]-5-methyl-pyrrolidine-1-carboxylate (173 mg, 299.95 umol, 1 eq) in DCM (0.1 mL) was added TFA (436.73 mg, 3.83 mmol, 283.59 uL, 12.77 eq) at 25° C. The reaction mixture was stirred at 25° C. for 1 h. The reaction mixture was concentrated to get a residue (180 mg). The residue (50 mg) was purified by prep-HPLC to get the product (26.50 mg). The crude product (130 mg) was used the next step without purification. (2R,5R)—N-(4-tert-butylphenyl)-N-[2-(cyclohexylamino)-2-oxo-1-(3-pyridyl) ethyl]-5-methyl-pyrrolidine-2-carboxamide (26.50 mg, 44.55 umol, 14.85% yield) was obtained as the a solid. (2R,5R)—N-(4-tert-butylphenyl)-N-[2-(cyclohexyl amino)-2-oxo-1-(3-pyridyl)ethyl]-5-methyl-pyrrolidine-2-carboxamide (130 mg) was obtained as an oil. MS (ESI) m/z 477.2 $[M+H]^+$. Prep-HPLC condition: column: Phenomenex Gemini-NX 150*30 mm*5 um; mobile phase: [water (0.1% TFA)-ACN]; B %: 30%-60%, 9 min. $^1$H NMR (400 MHz, METHANOL-$d_4$) δ ppm 8.38-8.47 (m, 2H), 8.24 (br d, J=7.63 Hz, 1H), 7.74 (br d, J=8.11 Hz, 2H), 7.34-7.53 (m, 2H), 7.25 (br s, 1H), 6.79-6.79 (m, 1H), 6.81 (br s, 1H), 6.23 (s, 1H), 4.23 (dd, J=9.30, 6.68 Hz, 1H), 3.70-3.80 (m, 1H), 3.58-3.69 (m, 1H), 2.17-2.28 (m, 1H), 2.07 (td, J=12.19, 6.85 Hz, 1H), 1.92 (br d, J=12.52 Hz, 1H), 1.62-1.87 (m, 6H), 1.46-1.46 (m, 1H), 1.46-1.46 (m, 1H), 1.45 (d, J=6.56 Hz, 1H), 1.27-1.43 (m, 3H), 1.24 (s, 9H), 1.04-1.22 (m, 2H).

Step 3: (2R, 5R)—N-(4-tert-butylphenyl)-1-cyano-N-[2-(cyclohexylamino)-2-oxo-1-(3-pyridyl)ethyl]-5-methyl-pyrrolidine-2-carboxamide To a mixture of (2R,5R)—N-(4-tert-butylphenyl)-N-[2-(cyclohexylamino)-2-oxo-1-(3-pyridyl)ethyl]-5-methyl-pyrrolidine-2-carboxamide (130 mg, 220.09 umol, 1 eq, TFA) and TEA (66.81 mg, 660.26 umol, 91.90 uL, 3 eq) in DCM (0.9 mL) was added BrCN (78.92 mg, 745.08 umol, 54.81 uL, 3.39 eq) at 0° C. under $N_2$. The mixture was stirred at 0° C. for 0.5 h. The reaction mixture was concentrated to get the crude product. The crude residue was purified by prep-HPLC. (2R, 5R)—N-(4-tert-butylphenyl)-1-cyano-N-[2-(cyclohexylamino)-2-oxo-1-(3-pyridyl)ethyl]-5-methyl-pyrrolidine-2-carboxamide (26.10 mg, 52.03 umol, 23.64% yield, 100% purity) was obtained as a solid. MS (ESI) m/z 502.2 $[M+H]^+$. Prep-HPLC condition: column: Waters Xbridge BEH C18 100*30 mm*10 um; mobile phase: [water (10 mM $NH_4HCO_3$)-ACN]; B %: 40%-65%, 8 min. $^1$H NMR (400 MHz, METHANOL-$d_4$) δ ppm 8.25-8.33 (m, 2H), 7.70 (br s, 1H), 7.54 (br d, J=7.99 Hz, 1H), 7.40 (br s, 1H), 7.19 (dd, J=7.87, 4.89 Hz, 2H), 6.64-6.65 (m, 1H), 6.65 (br s, 1H), 6.15 (s, 1H), 4.17 (dd, J=8.46, 3.93 Hz, 1H), 3.65-3.79 (m, 2H), 2.16 (ddt, J=12.01, 7.78, 3.76, 3.76 Hz, 1H), 1.91-2.02 (m, 2H), 1.84-1.91 (m, 1H), 1.58-1.91 (m, 5H), 1.26-1.46 (m, 6H), 1.25-1.25 (m, 1H), 1.24 (s, 8H), 1.01-1.22 (m, 2H).

Step 4: (2R,5R)—N-(4-tert-butylphenyl)-N-[2-(cyclohexylamino)-2-oxo-1-(3-pyridyl)ethyl]-5-methyl-pyrrolidine-2-carboxamide To a solution of tert-butyl (2R,5R)-2-[(4-tert-butylphenyl)-[2-(cyclohexylamino)-2-oxo-1-(3-pyridyl) ethyl]carbamoyl]-5-methyl-pyrrolidine-1-carboxylate (200 mg, 346.76 umol, 1 eq) in DCM (1.2 mL) was added TFA (504.90 mg, 4.43 mmol, 327.85 uL, 12.77 eq) at 25° C. The reaction mixture was stirred at 25° C. for 1 h. The reaction mixture was concentrated to get a residue (200 mg). The residue (50 mg) was purified by pre-HPLC to get the product (30.60 mg). The product (150 mg) was used the next step without purification. (2R,5R)—N-(4-tert-butylphenyl)-N-[2-(cyclohexylamino)-2-oxo-1-(3-pyridyl)ethyl]-5-methyl-pyrrolidine-2-carboxamide (30.6 mg, 51.70 umol, 14.91% yield, 99.8% purity, TFA) was obtained as a solid. (2R, 5R)—N-(4-tert-butylphenyl)-N-[2-(cyclohexylamino)-2-oxo-1-(3-pyridyl)ethyl]-5-methyl-pyrrolidine-2-carboxamide (150 mg, crude) was obtained as an oil. MS (ESI) m/z 477.2 $[M+H]^+$ Prep-HPLC condition: column: Phenomenex Gemini-NX 150*30 mm*5 um; mobile phase: [water (0.1% TFA)-ACN]; B %: 30%-60%, 9 min). $^1$H NMR (400 MHz, METHANOL-$d_4$) δ ppm 1.04-1.22 (m, 2H) 1.24 (s, 9H) 1.27-1.43 (m, 3H) 1.45 (d, J=6.56 Hz, 1H) 1.46-1.46 (m, 1H) 1.46-1.46 (m, 1H) 1.62-1.87 (m, 6H) 1.92 (br d, J=12.52 Hz, 1H) 2.07 (td, J=12.19, 6.85 Hz, 1H) 2.17-2.28 (m, 1H) 3.58-3.69 (m, 1H) 3.70-3.80 (m, 1H) 4.23 (dd, J=9.30, 6.68 Hz, 1H) 6.23 (s, 1H) 6.81 (br s, 1H) 6.79-6.79 (m, 1H) 7.25 (br s, 1H) 7.34-7.53 (m, 2H) 7.74 (br d, J=8.11 Hz, 2H) 8.24 (br d, J=7.63 Hz, 1H) 8.38-8.47 (m, 2H).

Step 5: (2R,5R)—N-(4-tert-butylphenyl)-1-cyano-N-[2-(cyclohexylamino)-2-oxo-1-(3-pyridyl)ethyl]-5-methyl-pyrrolidine-2-carboxamide To a mixture of (2R,5R)—N-(4-tert-butylphenyl)-N-[2-(cyclohexylamino)-2-oxo-1-(3-pyridyl) ethyl]-5-methyl-pyrrolidine-2-carboxamide (150 mg, 253.95 umol, 1 eq, TFA) and TEA (77.09 mg, 761.84 umol, 106.04 uL, 3 eq) in DCM (0.9 mL) was added CNBr (90.07 mg, 850.35 umol, 62.55 uL, 3.35 eq) at 0° C. under $N_2$. The mixture was stirred at 0° C. for 0.5 h. The reaction mixture was concentrated to get the crude product. The crude residue was purified by pre-HPLC. (2R,5R)—N-(4-tert-butylphenyl)-1-cyano-N-[2-(cyclohexylamino)-2-oxo-1-(3-pyridyl)ethyl]-5-methyl-pyrrolidine-2-carboxamide (25.7 mg, 51.23 umol, 20.17% yield, 100% purity) was obtained as a solid. MS (ESI) m/z 502.2 $[M+H]^+$ Prep-HPLC condition: column: Waters Xbridge BEH C18 100*30 mm*10 um; mobile phase: [water (10 mM NH4HCO3)-ACN]; B %: 35%-65%, 8 min. $^1$H NMR (400 MHz, METHANOL-$d_4$) δ ppm 8.29-8.39 (m, 2H), 7.69 (br s, 1H), 7.56 (br d, J=7.99 Hz, 1H), 7.42 (br s, 1H), 7.22 (dd, J=7.87, 5.01 Hz, 2H), 6.42-6.89 (m, 1H), 6.02 (s, 1H), 4.18 (dd, J=8.52, 3.75 Hz, 1H), 3.63-3.78 (m, 2H), 1.82-2.09 (m, 4H), 1.59-1.82 (m, 5H), 1.38 (d, J=6.32 Hz, 3H), 1.29-1.44 (m, 1H), 1.29-1.44 (m, 1H), 1.29-1.44 (m, 1H), 1.27 (s, 9H), 1.02-1.25 (m, 3H).

Example 33: Synthesis of Compound 247

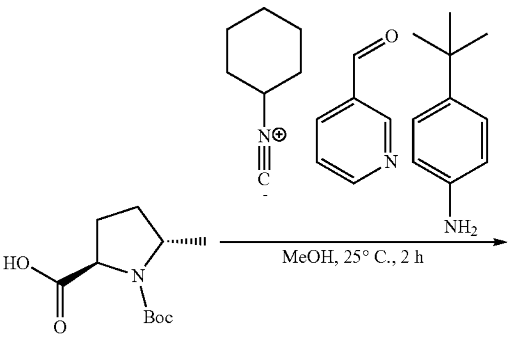

-continued

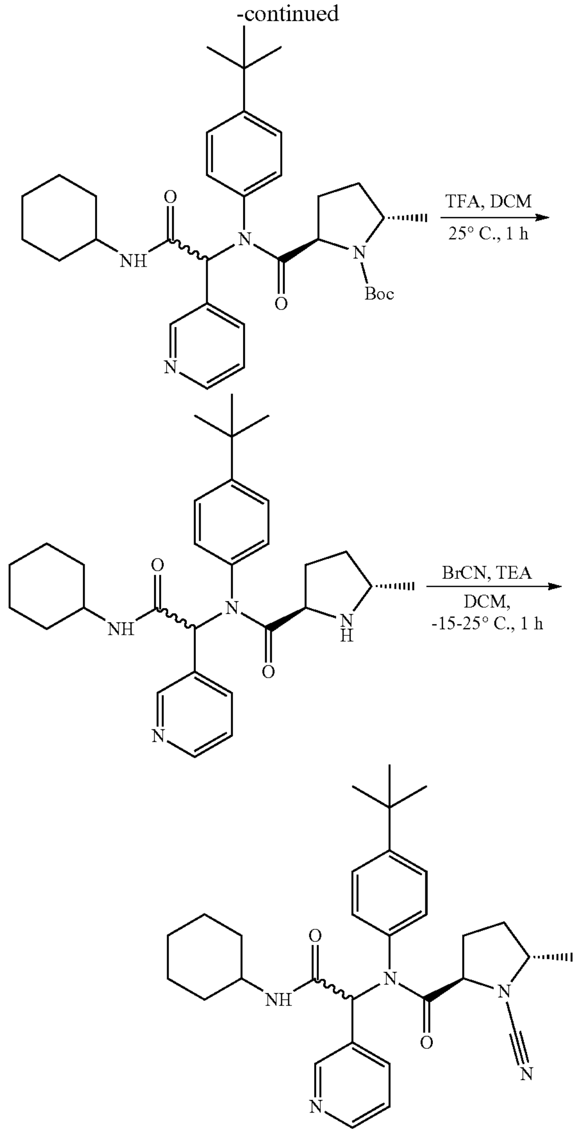

Step 1: (2R,5S)-tert-butyl 2-((4-(tert-butyl)phenyl)(2-(cyclohexylamino)-2-oxo-1-(pyridin-3-yl)ethyl)carbamoyl)-5-methylpyrrolidine-1-carboxylate Pyridine-3-carbaldehyde (46.72 mg, 436.16 umol, 40.98 uL, 1 eq), and 4-tert-butylaniline (65.09 mg, 436.16 umol, 68.88 uL, 1 eq) in MeOH (1 mL) were stirred at 25° C. for 0.5 h, and then (2R,5S)-1-tert-butoxycarbonyl-5-methyl-pyrrolidine-2-carboxylic acid (100 mg, 436.16 umol, 1 eq) and isocyanocyclohexane (47.62 mg, 436.16 umol, 54.23 uL, 1 eq) was added. The solution was stirred at 25° C. for 1.5 h, and then concentrated to remove the MeOH. The residue was purified by prep-HPLC (neutral condition), column: Waters Xbridge Prep OBD C18 150*40 mm*10 um; mobile phase: [water (10 mM $NH_4HCO_3$)-ACN]; B %: 55%-90%, 8 min. tert-butyl (2R,5S)-2-[(4-tert-butylphenyl)-[2-(cyclohexylamino)-2-oxo-1-(3-pyridyl)ethyl]carbamoyl]-5-methyl-pyrrolidine-1-carboxylate (120 mg, 208.06 umol, 47.70% yield, 100% purity) was obtained as a solid, tert-butyl (2R,5S)-2-[(4-tert-butylphenyl)-[2-(cyclohexylamino)-2-oxo-1-(3-pyridyl)ethyl]carbamoyl]-5-methyl-pyrrolidine-1-carboxylate (120 mg, 208.06 umol, 47.70% yield, 100% purity) was obtained as a solid. MS (ESI) m/z 577.4 $[M+H]^+$.

Step 2: (2R,5S)—N-(4-(tert-butyl)phenyl)-N-(2-(cyclohexylamino)-2-oxo-1-(pyridin-3-yl)ethyl)-5-methylpyrrolidine-2-carboxamide Tert-butyl (2R,5S)-2-[(4-tert-butylphenyl)-[2-(cyclohexylamino)-2-oxo-1-(3-pyridyl)ethyl]carbamoyl]-5-methyl-pyrrolidine-1-carboxylate (120 mg, 208.06 umol, 1 eq) in DCM (2 mL)/TFA (2.31 g, 20.26 mmol, 1.50 mL, 97.38 eq) was stirred at 25° C. for 1 h. The solution was concentrated to remove the DCM and TFA. The residue was purified by prep-HPLC (TFA condition), column: Phenomenex luna C18 80*40 mm*3 um; mobile phase: [water (0.1% TFA)-ACN]; B %: 15%-50%, 6 min (2R,5S)—N-(4-tert-butylphenyl)-N-[2-(cyclohexylamino)-2-oxo-1-(3-pyridyl)ethyl]-5-methyl-pyrrolidine-2-carboxamide (80 mg, 167.57 umol, 80.54% yield, 99.841% purity) was obtained as a solid. $^1H$ NMR (400 MHz, METHANOL-$d_4$) δ ppm 8.42 (br d, J=5.3 Hz, 2H), 8.20 (br d, J=7.1 Hz, 1H), 7.81-7.13 (m, 5H), 6.80 (br s, 1H), 6.21 (s, 1H), 4.20 (br t, J=8.3 Hz, 1H), 3.84-3.66 (m, 2H), 2.24-2.03 (m, 2H), 1.95-1.58 (m, 6H), 1.57-1.24 (m, 7H), 1.23 (s, 9H), 1.19-1.03 (m, 2H). MS (ESI) m/z 477.2 $[M+H]^+$.

Step 3: (2R,5S)—N-(4-(tert-butyl)phenyl)-N-(2-(cyclohexylamino)-2-oxo-1-(pyridin-3-yl)ethyl)-5-methylpyrrolidine-2-carboxamide Tert-butyl (2R,5S)-2-[(4-tert-butylphenyl)-[2-(cyclohexylamino)-2-oxo-1-(3-pyridyl)ethyl]carbamoyl]-5-methyl-pyrrolidine-1-carboxylate (120 mg, 208.06 umol, 1 eq) in DCM (2 mL)/TFA (2.31 g, 20.26 mmol, 1.50 mL, 97.38 eq) was stirred at 25° C. for 1 h. The solution was concentrated to remove the DCM and TFA. The residue was purified by prep-HPLC (TFA condition), column: Phenomenex luna C18 80*40 mm*3 um; mobile phase: [water (0.1% TFA)-ACN]; B %: 15%-55%, 7 min. (2R,5S)—N-(4-tert-butylphenyl)-N-[2-(cyclohexylamino)-2-oxo-1-(3-pyridyl)ethyl]-5-methyl-pyrrolidine-2-carboxamide (80 mg, 167.59 umol, 80.55% yield, 99.855% purity) was obtained as a solid. $^1H$ NMR (400 MHz, METHANOL-$d_4$) δ=8.50 (br s, 2H), 7.98-6.42 (m, 6H), 6.06 (br s, 1H), 4.19 (br t, J=8.2 Hz, 1H), 3.85-3.61 (m, 2H), 2.25-2.12 (m, 1H), 2.11-1.98 (m, 1H), 1.96-1.82 (m, 2H), 1.81-1.58 (m, 4H), 1.57-1.44 (m, 1H), 1.43-1.29 (m, 5H), 1.25 (d, J=1.8 Hz, 9H), 1.24-1.01 (m, 3H). MS (ESI) m/z 477.2 $[M+H]^+$.

Step 4: (2R,5S)—N-(4-(tert-butyl)phenyl)-1-cyano-N-(2-(cyclohexylamino)-2-oxo-1-(pyridin-3-yl)ethyl)-5-methylpyrrolidine-2-carboxamide A solution of (2R,5S)—N-(4-tert-butylphenyl)-N-[2-(cyclohexylamino)-2-oxo-1-(3-pyridyl)ethyl]-5-methyl-pyrrolidine-2-carboxamide (60 mg, 125.88 umol, 1 eq) in DCM (1 mL) and TEA (25.47 mg, 251.76 umol, 35.04 uL, 2 eq) was cooled to −10° C., and then a solution of BrCN (160 mg, 1.51 mmol, 111.11 uL, 12.00 eq) in DCM (0.2 mL) was added. The resulting solution was stirred at 0° C. and warmed to 25° C. gradually over 1 h. The solution was quenched with $H_2O$ at 0° C., extracted with DCM (20 mL*3), the combined organic phase was dried over $Na_2SO_4$, filtrated and concentrated to give a residue. The residue was purified by prep-HPLC (neutral condition), column: Waters Xbridge BEH C18 100*30 mm*10 um; mobile phase:

[water (10 mM NH4HCO3)-ACN]; B %: 40%-70%, 10 min (2R,5S)—N-(4-tert-butylphenyl)-1-cyano-N-[2-(cyclohexylamino)-2-oxo-1-(3-pyridyl)ethyl]-5-methyl-pyrrolidine-2-carboxamide (12 mg, 23.92 umol, 19.00% yield, 100% purity) was obtained as a solid. 1H NMR (400 MHz, METHANOL-$d_4$) δ=8.33-8.22 (m, 2H), 7.67 (br s, 1H), 7.52 (td, J=1.8, 7.9 Hz, 1H), 7.39 (br s, 1H), 7.17 (dd, J=4.9, 7.9 Hz, 2H), 6.63 (br s, 1H), 6.14 (s, 11H), 4.19 (dd, J=6.5, 7.8 Hz, 1H), 3.93-3.81 (m, 1H), 3.70 (tt, J=3.8, 10.9 Hz, 1H), 2.16-1.88 (m, 4H), 1.83-1.57 (m, 4H), 1.44-1.23 (m, 7H), 1.22 (s, 9H), 1.20-1.00 (m, 2H). MS (ESI) m/z 502.2 $[M+H]^+$.

Step 5: (2R,5S)—N-(4-(tert-butyl)phenyl)-1-cyano-N-(2-(cyclohexylamino)-2-oxo-1-(pyridin-3-yl)ethyl)-5-methylpyrrolidine-2-carboxamide A solution of (2R,5S)—N-(4-tert-butylphenyl)-N-[2-(cyclohexylamino)-2-oxo-1-(3-pyridyl)ethyl]-5-methyl-pyrrolidine-2-carboxamide (60 mg, 125.88 umol, 1 eq) in DCM (1 mL) and TEA (25.47 mg, 251.76 umol, 35.04 uL, 2 eq) was cooled to −15° C., and then a solution of BrCN (141.82 mg, 1.34 mmol, 98.48 uL, 10.64 eq) in DCM (0.2 mL) was added. The resulting solution was stirred at 0° C. and warmed to 25° C. gradually over 1 h. The solution was quenched with $H_2O$ at 0° C., extracted with DCM (20 mL*3), the combined organic phase was dried over $Na_2SO_4$, filtrated and concentrated to give the crude. The residue was purified by prep-HPLC (neutral condition), column: Waters Xbridge BEH C18 100*30 mm*10 um; mobile phase: [water (10 mM NH4HCO3)-ACN]; B %: 40%-70%, 10 min. (2R,5S)—N-(4-tert-butylphenyl)-1-cyano-N-[2-(cyclohexylamino)-2-oxo-1-(3-pyridyl)ethyl]-5-methyl-pyrrolidine-2-carboxamide (20 mg, 39.87 umol, 31.67% yield, 100% purity) was obtained as a solid. $^1H$ NMR (400 MHz, METHANOL-$d_4$) δ=8.41-8.23 (m, 2H), 7.86-6.34 (m, 6H), 6.01 (s, 1H), 4.20 (t, J=7.3 Hz, 1H), 3.90-3.79 (m, 1H), 3.67 (tt, J=3.7, 10.8 Hz, 1H), 2.08 (qd, J=6.0, 11.9 Hz, 1H), 2.00-1.88 (m, 3H), 1.81-1.56 (m, 4H), 1.45-1.26 (m, 4H), 1.25 (s, 9H), 1.24-1.02 (m, 5H). MS (ESI) m/z 502.2 $[M+H]^+$.

Example 34: Synthesis of Compound 254

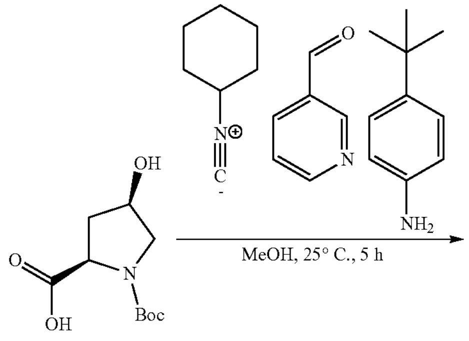

-continued

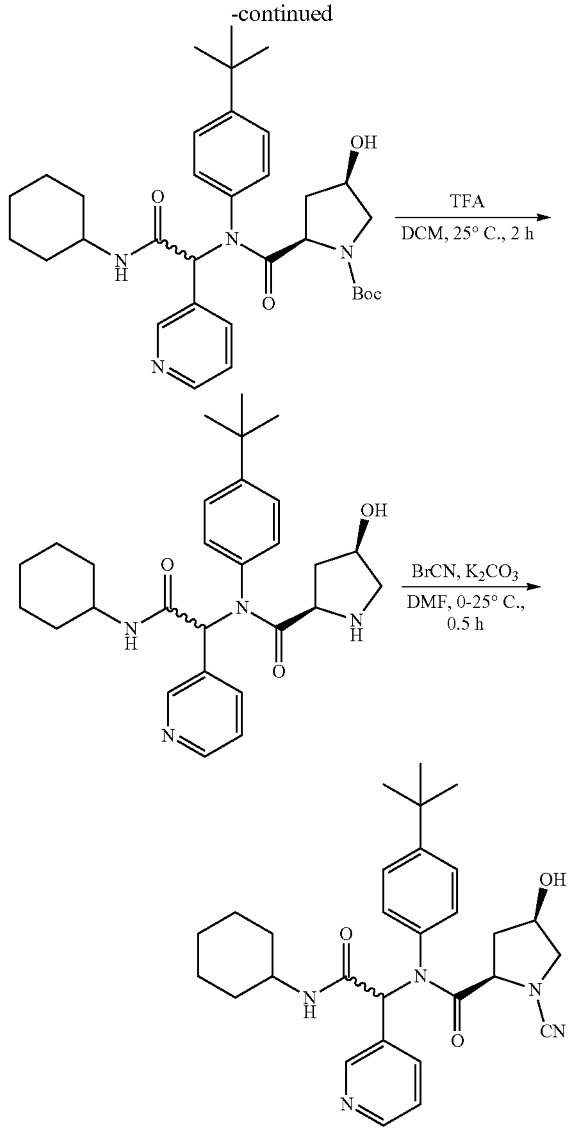

Step 1: methyl (2S)-2-amino-3-[(3S)-2-oxopyrrolidin-3-yl]propanoate;hydrochloride To a mixture of 4-tert-butylaniline (322.67 mg, 2.16 mmol, 341.45 uL, 1 eq) in MeOH (5 mL) was added pyridine-3-carbaldehyde (231.59 mg, 2.16 mmol, 203.15 uL, 1 eq). The mixture was stirred at 25° C. for 1 h, and then (2R, 4R)-1-tert-butoxycarbonyl-4-hydroxy-pyrrolidine-2-carboxylic acid (500 mg, 2.16 mmol, 1 eq) and isocyanocyclohexane (236.05 mg, 2.16 mmol, 268.85 uL, 1 eq) were added. The mixture was stirred at 25° C. for 4 h. The reaction mixture was filtered and concentrated under reduced pressure to give a residue tert-butyl(2R,4R)-2-[(4-tert-butylphenyl)-[2-(cyclohexylamino)-2-oxo-1-(3-pyridyl)ethyl]carbamoyl]-4-hydroxy-pyrrolidine-1-carboxylate (1 g, crude) as a an oil and used directly next step. MS (ESI) m/z 579.4 $[M+H]^+$.

Step 2: (2R,4R)—N-(4-tert-butylphenyl)-N-[2-(cyclohexylamino)-2-oxo-1-(3-pyridyl)ethyl]-4-hydroxy-pyrrolidine-2-carboxamide To a mixture of tert-butyl (2R,4R)-2-[(4-tert-butylphenyl)-[2-(cyclohexylamino)-2-oxo-1-(3-pyridyl)ethyl]carbamoyl]-4-hydroxy-pyrrolidine-1-carboxylate (222.22 mg, 345.58 umol, 90% purity, 1 eq) in DCM (8 mL) was added TFA (6.16 g, 54.02 mmol, 4.00 mL, 156.33 eq). The mixture was stirred at 25° C. for 2 h. The reaction mixture was filtered and concentrated under reduced pressure to give a residue. The mixture was purified by prep-HPLC to get the compound (2R,4R)—N-(4-tert-butylphenyl)-N-[2-(cyclohexylamino)-2-oxo-1-(3-pyridyl)ethyl]-4-hydroxyl-pyrrolidine-2-carboxamide (150 mg, 297.73 umol, 86.15% yield, 95% purity) and (2R,4R)—N-(4-tert-butylphenyl)-N-[2-(cyclohexylamino)-2-oxo-1-(3-pyridyl)ethyl]-4-hydroxy-pyrrolidine-2-carboxamide (100 mg, 198.49 umol, 57.44% yield, 95% purity) were obtained as a solid. MS (ESI) m/z 479.3 $[M+H]^+$ Prep-HPLC condition: column: Phenomenex luna C18 100*40 mm*5 um; mobile phase: [water (0.1% TFA)-ACN]; B %: 20%-34%, 8 min. Isomer 1: $^1H$ NMR (400 MHz, DMSO-$d_6$) δ=9.41 (br s, 1H), 8.59 (br s, 1H), 8.43-8.31 (m, 2H), 8.10 (d, J=7.7 Hz, 1H), 7.99-6.14 (m, 6H), 5.95 (s, 1H), 5.82-4.38 (m, 1H), 4.20 (br s, 1H), 4.07-3.94 (m, 1H), 3.62-3.59 (m, 1H), 3.10 (br s, 2H), 1.87-1.79 (m, 2H), 1.75-1.50 (m, 5H), 1.27-1.05 (m, 14H). Isomer 2: $^1H$ NMR (400 MHz, DMSO-$d_6$) δ=9.22 (br s, 1H), 8.63 (br s, 1H), 8.43-8.24 (m, 2H), 8.11 (d, J=7.7 Hz, 1H), 7.94-6.29 (m, 6H), 6.11 (s, 1H), 5.79-4.74 (m, 1H), 4.18 (br s, 1H), 4.02 (td, J=7.7, 15.5 Hz, 1H), 3.54-3.52 (m, 1H), 3.21-3.00 (m, 2H), 1.82-1.50 (m, 7H), 1.27-1.09 (m, 14H).

Step 3: (2R,4R)—N-(4-tert-butylphenyl)-1-cyano-N-[2-(cyclohexylamino)-2-oxo-1-(3-pyridyl) ethyl]-4-hydroxy-pyrrolidine-2-carboxamide To a mixture of (2R,4R)—N-(4-tert-butylphenyl)-N-[2-(cyclohexylamino)-2-oxo-1-(3-pyridyl)ethyl]-4-hydroxy-pyrrolidine-2-carboxamide (50 mg, 104.47 umol, 1 eq) in DMF (2 mL) was added BrCN (13.28 mg, 125.36 umol, 9.22 uL, 1.2 eq) and $K_2CO_3$ (28.88 mg, 208.93 umol, 2 eq) at 0° C. The mixture was stirred at 25° C. for 0.5 h. TLC and LCMS showed the reaction was completed. The reaction mixture was quenched by addition $H_2O$ (10 mL) at 0° C., and then filtered and concentrated under reduced pressure to give a residue. The mixture was purified by neutral prep-HPLC to get the compound (2R,4R)—N-(4-tert-butylphenyl)-1-cyano-N-[2-(cyclohexylamino)-2-oxo-1-(3-pyridyl) ethyl]-4-hydroxy-pyrrolidine-2-carboxamide (20 mg, 39.71 umol, 38.01% yield, 100% purity) as a solid. MS (ESI) m/z 504.3 $[M+H]^+$ Prep-HPLC: column: Waters Xbridge BEH C18 100*30 mm*10 um; mobile phase: [water (10 mM NH4HCO3)-ACN]; B %: 34%-64%, 101 min. Compound 254 Isomer 1: $^1H$ NMR (400 MHz, DMSO-$d_6$) δ=8.44-8.24 (m, 2H), 7.98 (d, J=7.7 Hz, 1H), 7.84-6.26 (m, 6H), 5.95 (s, 1H), 5.24 (d, J=5.9 Hz, 1H), 4.21-3.94 (m, 2H), 3.65-3.43 (m, 2H), 3.17 (dd, J=5.7, 9.0 Hz, 1H), 2.05-1.87 (m, 1H), 1.77-1.44 (m, 6H), 1.33-0.86 (m, 14H); Compounds 254 Isomer 2: $^1H$ NMR (400 MHz, DMSO-$d_6$) δ=8.38-8.22 (m, 2H), 8.05 (br d, J=7.6 Hz, 1H), 7.85-6.40 (m, 6H), 6.07 (s, 1H), 5.25 (d, J=6.0 Hz, 1H), 4.17-3.97 (m, 2H), 3.65-3.45 (m, 2H), 3.21-3.07 (m, 1H), 1.99-1.84 (m, 1H), 1.80-1.48 (m, 6H), 1.33-0.90 (m, 14H).

Example 35: Synthesis of Compound 255

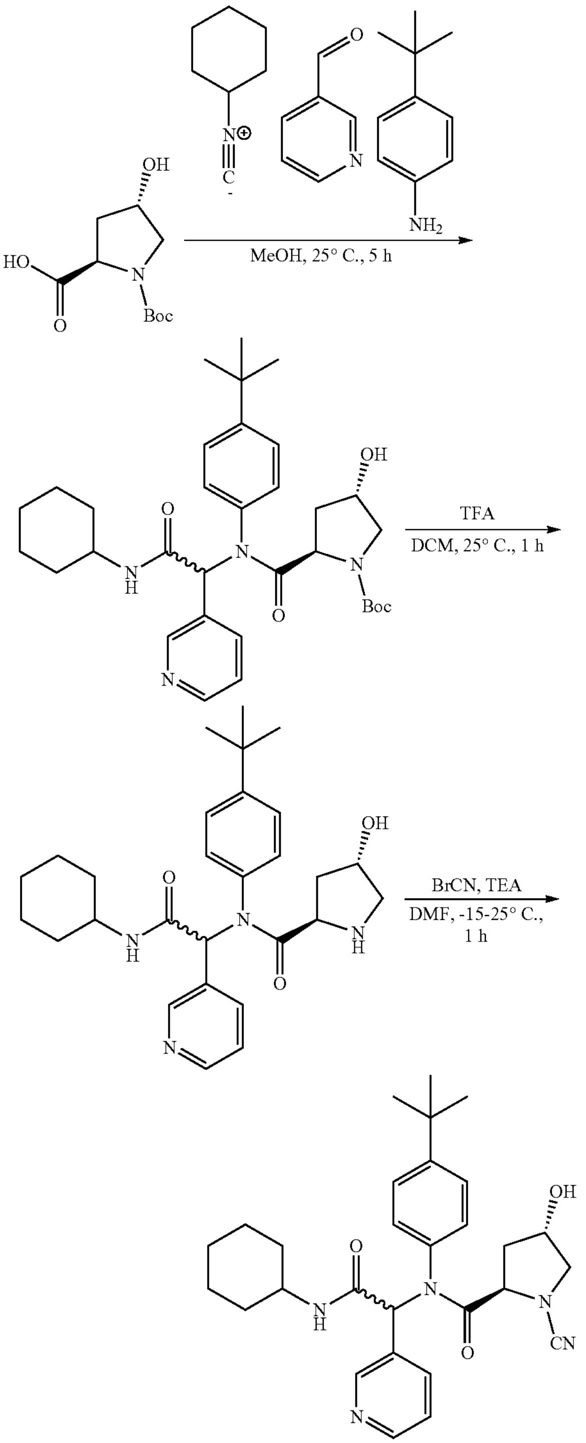

Step 1: (2R,4S)-tert-butyl 2-((4-(tert-butyl)phenyl)(2-(cyclohexylamino)-2-oxo-1-(pyridin-3-yl)ethyl)carbamoyl)-4-hydroxypyrrolidine-1-carboxylate Pyridine-3-carbaldehyde (231.59 mg, 2.16 mmol, 203.15 uL, 1 eq) and 4-tert-butylaniline (322.67 mg, 2.16 mmol, 341.45 uL, 1 eq) in MeOH (5 mL) were stirred at 25° C. for 0.5 h. Then, (2R,4S)-1-tert-butoxycarbonyl-4-hydroxy-pyrrolidine-2-carboxylic acid (500 mg, 2.16 mmol, 1 eq) and isocyanocyclohexane (236.05 mg, 2.16 mmol, 268.84 uL, 1 eq) were added and the solution was stirred at 25° C. for 4.5 h. The solution was concentrated to remove the solvent and give a product. The product was used to next step directly and without further purification. Tert-butyl (2R,4S)-2-[(4-tert-butylphenyl)-[2-(cyclohexylamino)-2-oxo-1-(3-pyridyl)ethyl]carbamoyl]-4-hydroxy-pyrrolidine-1-carboxylate (1.2 g) was obtained as a solid. MS (ESI) m/z 579.4 $[M+H]^+$.

Step 2: (2R,4S)—N-(4-(tert-butyl)phenyl)-N-(2-(cyclohexylamino)-2-oxo-1-(pyridin-3-yl)ethyl)-4-hydroxypyrrolidine-2-carboxamide Tert-butyl (2R,4S)-2-[(4-tert-butylphenyl)-[2-(cyclohexylamino)-2-oxo-1-(3-pyridyl)ethyl]carbamoyl]-4-hydroxy-pyrrolidine-1-carboxylate (1 g, 1.73 mmol, 1 eq) in DCM (2 mL)/TFA (1.54 g, 13.51 mmol, 1 mL, 7.82 eq) was stirred at 25° C. for 1 h. The solution was concentrated to remove the DCM and give a residue. The residue was purified by prep-HPLC (TFA condition), column: Phenomenex luna C18 250*50 mm*10 um; mobile phase: [water (0.1% TFA)-ACN]; B %: 25%-40%, 10 min. Give (2R,4S)—N-(4-tert-butylphenyl)-N-[2-(cyclohexylamino)-2-oxo-1-(3-pyridyl)ethyl]-4-hydroxy-pyrrolidine-2-carboxamide (260 mg, 543.22 umol, 31.44% yield, 100% purity) as an oil. Isomer 1, $^1H$ NMR (400 MHz, DMSO-$d_6$) δ ppm 9.68-9.44 (m, 1H), 8.84 (br s, 1H), 8.50-8.37 (m, 2H), 8.11 (d, J=7.7 Hz, 1H), 7.87-6.62 (m, 6H), 5.96 (s, 1H), 4.33 (br s, 1H), 4.10-3.97 (m, 1H), 3.65-3.48 (m, 1H), 3.25 (br dd, J=4.0, 11.2 Hz, 1H), 3.03 (br d, J=9.0 Hz, 1H), 2.07-1.94 (m, 1H), 1.76-1.47 (m, 6H), 1.37-0.90 (m, 14H), (2R,4S)—N-(4-tert-butylphenyl)-N-[2-(cyclohexylamino)-2-oxo-1-(3-pyridyl)ethyl]-4-hydroxy-pyrrolidine-2-carboxamide (280 mg, 585.01 umol, 33.86% yield, 100% purity) was obtained as an oil. Isomer 2, $^1H$ NMR (400 MHz, METHANOL-$d_4$) δ=8.51-8.37 (m, 2H), 8.25 (br d, J=7.7 Hz, 1H), 7.79 (br d, J=8.2 Hz, 1H), 7.66 (br s, 1H), 7.54-7.35 (m, 2H), 7.25 (br s, 1H), 6.83 (br s, 1H), 6.21 (s, 1H), 4.50 (br s, 1H), 4.35 (dd, J=7.7, 10.1 Hz, 1H), 3.79-3.64 (m, 1H), 3.45-3.37 (m, 1H), 3.26 (s, 1H), 2.22-2.10 (m, 1H), 1.94-1.57 (m, 6H), 1.38-1.03 (m, 14H). MS (ESI) m/z 479.3 $[M+H]^+$.

Step 3: (2R,4S)—N-(4-(tert-butyl)phenyl)-1-cyano-N-(2-(cyclohexylamino)-2-oxo-1-(pyridin-3-yl)ethyl)-4-hydroxypyrrolidine-2-carboxamide To a mixture of (2R,4S)—N-(4-tert-butylphenyl)-N-[2-(cyclohexylamino)-2-oxo-1-(3-pyridyl)ethyl]-4-hydroxy-pyrrolidine-2-carboxamide (100 mg, 208.93 umol, 1 eq) in DCM (1 mL) was added TEA (63.42 mg, 626.80 umol, 87.24 uL, 3 eq) and the solution was cooled to −15° C. and the solution of BrCN (110.65 mg, 1.04 mmol, 76.84 uL, 5 eq) in DCM (0.2 mL) was added. The resulting mixture was stirred at 0° C. and warmed to 25° C. gradually for 1 h. The solution was quenched with $H_2O$ at 0° C., extracted with DCM (3*20 mL), the combined organic phase was dried over $Na_2SO_4$, filtrated and concentrated to give the crude. The residue was purified by prep-HPLC (neutral condition), column: Phenomenex Gemini-NX 80*40 mm*3 um; mobile phase: [water (10 mM NH4HCO3)-ACN]; B %: 30%-50%, 8 min. (2R,4S)—N-(4-tert-butylphenyl)-1-cyano-N-[2-(cyclohexylamino)-2-oxo-1-(3-pyridyl)ethyl]-4-hydroxy-pyrrolidine-2-carboxamide (30 mg, 59.57 umol, 28.51% yield, 100% purity) was obtained as a solid. $^1H$ NMR (400 MHz, DMSO-$d_6$) δ=8.38-8.27 (m, 2H), 7.96 (d, J=7.7 Hz, 1H), 7.75-6.31 (m, 5H), 5.94 (s, 1H), 5.09 (d, J=3.5 Hz, 1H), 4.21 (br s, 1H), 4.07 (t, J=7.9 Hz, 1H), 3.59-3.44 (m, 2H), 3.21-3.13 (m, 1H), 1.92 (ddd, J=4.4, 8.6, 13.0 Hz, 1H), 1.77-1.48 (m, 6H), 1.36-1.21 (m, 2H), 1.20 (s, 9H), 1.17-0.92 (m, 3H). MS (ESI) m/z 504.3 $[M+H]^+$.

Step 4: (2R,4S)—N-(4-(tert-butyl)phenyl)-1-cyano-N-(2-(cyclohexylamino)-2-oxo-1-(pyridin-3-yl)ethyl)-4-hydroxypyrrolidine-2-carboxamide To a mixture of (2R,4S)—N-(4-tert-butylphenyl)-N-[2-(cyclohexylamino)-2-oxo-1-(3-pyridyl)ethyl]-4-hydroxy-pyrrolidine-2-carboxamide (101 mg, 211.02 umol, 1 eq) in DCM (1 mL) was added TEA (64.06 mg, 633.06 umol, 88.11 uL, 3 eq), the solution was cooled to −15° C., then the solution of BrCN (260 mg, 2.45 mmol, 180.56 uL, 11.63 eq) in DCM (0.5 mL) was added at 0° C. The solution was warmed to 25° C. gradually over 1 h. The solution was quenched with $H_2O$ at 0° C., extracted with DCM (20 mL*3), and the combined organic phase was dried over $Na_2SO_4$, filtrated and concentrated to give a residue. The residue was purified by prep-HPLC (neutral condition), column: Phenomenex Gemini-NX 80*40 mm*3 um; mobile phase: [water (10 mM $NH_4HCO_3$)-ACN]; B %: 30%-50%, 8 min. (2R,4S)—N-(4-tert-butylphenyl)-1-cyano-N-[2-(cyclohexylamino)-2-oxo-1-(3-pyridyl)ethyl]-4-hydroxy-pyrrolidine-2-carboxamide (35 mg, 69.49 umol, 32.93% yield, 100% purity) was obtained as a solid. Isomer 2, $^1H$ NMR (400 MHz, DMSO-$d_6$) δ=8.31-8.20 (m, 2H), 8.05 (d, J=7.7 Hz, 1H), 7.75-6.96 (m, 5H), 6.84-6.49 (m, 1H), 6.06 (s, 1H), 5.08 (d, J=3.7 Hz, 1H), 4.21 (br s, 1H), 4.11 (t, J=8.0 Hz, 1H), 3.64-3.47 (m, 2H), 3.25-3.16 (m, 1H), 1.91 (ddd, J=4.4, 8.5, 13.1 Hz, 1H), 1.79-1.45 (m, 6H), 1.34-1.19 (m, 3H), 1.17 (s, 9H), 1.12-0.89 (m, 2H).

Example 36: Synthesis of Compound 262

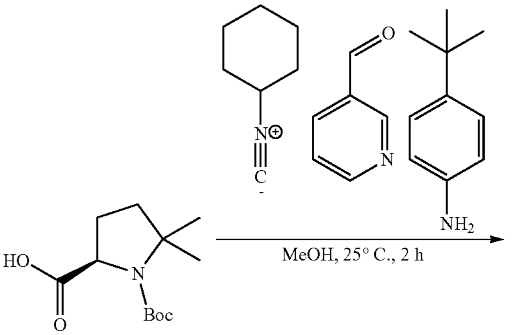

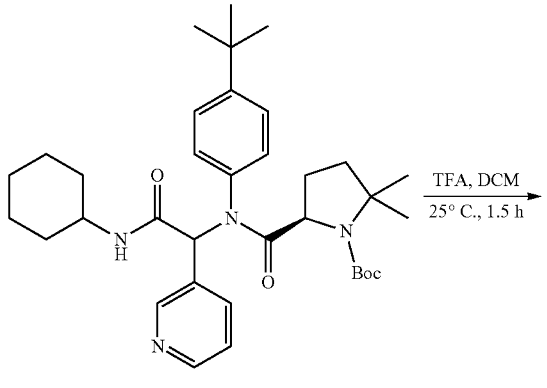

-continued

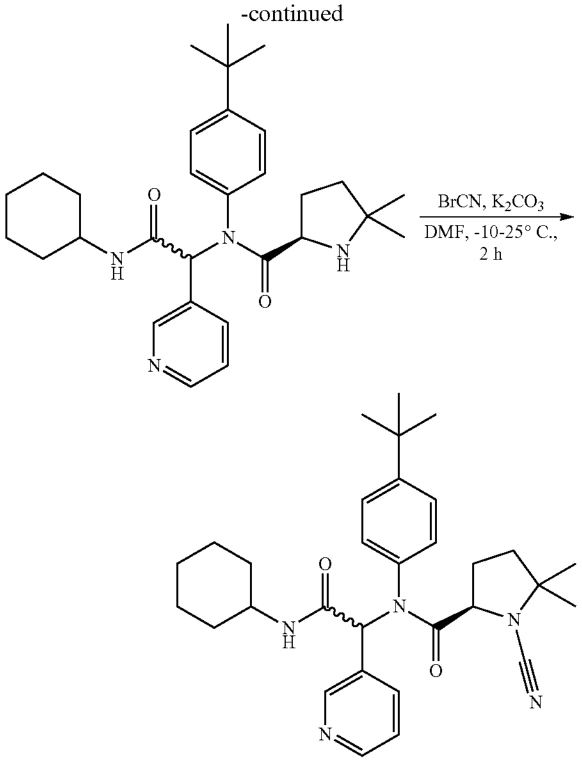

Step 1: tert-butyl (5R)-5-[(4-tert-butylphenyl)-[2-(cyclohexylamino)-2-oxo-1-(3-pyridyl)ethyl]carbamoyl]-2,2-dimethyl-pyrrolidine-1-carboxylate A solution of pyridine-3-carbaldehyde (184.90 mg, 1.73 mmol, 162.19 uL, 1.4 eq), and 4-tert-butylaniline (184.01 mg, 1.23 mmol, 194.72 uL, 1 eq) in MeOH (4 mL) were stirred at 25° C. for 0.5 h. (2R)-1-tert-butoxycarbonyl-5,5-dimethyl-pyrrolidine-2-carboxylic acid (300.00 mg, 1.23 mmol, 1 eq) and isocyanocyclohexane (134.61 mg, 1.23 mmol, 153.31 uL, 1 eq) were added, and the solution was stirred at 25° C. for 1.5 h. The resulting solution was diluted with $H_2O$ (10 mL), and extracted with EtOAc (3*20 mL). The combined organic phase was dried over $Na_2SO_4$, filtrated and concentrated to give a residue. The residue was purified by prep-TLC (petroleum ether/EtOAc=3:1) to get tert-butyl (5R)-5-[(4-tert-butylphenyl)-[2-(cyclohexylamino)-2-oxo-1-(3-pyridyl)ethyl]carbamoyl]-2,2-dimethyl-pyrrolidine-1-carboxylate (500 mg, 677.06 umol, 54.91% yield, 80% purity) as an oil. MS (ESI) m/z 591.1 $[M+H]^+$.

Step 2: (2R)—N-(4-tert-butylphenyl)-N-[2-(cyclohexylamino)-2-oxo-1-(3-pyridyl)ethyl]-5,5-dimethyl-pyrrolidine-2-carboxamide and (2R)—N-(4-tert-butylphenyl)-N-[2-(cyclohexylamino)-2-oxo-1-(3-pyridyl)ethyl]-5,5-dimethyl-pyrrolidine-2-carboxamide To a solution of tert-butyl (5R)-5-[(4-tert-butylphenyl)-[2-(cyclohexylamino)-2-oxo-1-(3-pyridyl)ethyl]carbamoyl]-2,2-dimethyl-pyrrolidine-1-carboxylate (400 mg, 677.06 umol, 1 eq) in DCM (4 mL) was added TFA (3.08 g, 27.01 mmol, 2.00 mL, 39.90 eq) at 25° C. for 1.5 h. The solution was purified by prep-HPLC (column: Phenomenex luna C18 100*40 mm*5 um; mobile phase: [water (0.1% TFA)-ACN]; B %: 23%-36%, 8 min) to get (2R)—N-(4-tert-butylphenyl)-N-[2-(cyclohexylamino)-2-oxo-1-(3-pyridyl)ethyl]-5,5-dimethyl-pyrrolidine-2-carboxamide (113.46 mg, 231.23 umol, 34.15% yield, 100% purity) as a solid. MS (ESI) m/z 491.1 $[M+H]^+$. $^1H$ NMR (400 MHz, METHANOL-$d_4$) δ ppm 1.01-1.26 (m, 12H) 1.26-1.42 (m, 6H) 1.49 (s, 3H) 1.58-1.96 (m, 8H) 2.13-2.27 (m, 1H) 3.59-3.76 (m, 1H) 4.23 (t, J=8.31 Hz, 1H) 6.04 (s, 1H) 6.70 (br s, 1H) 7.11-7.83 (m, 5H) 8.18 (br d, J=7.46 Hz, 1H) 8.32-8.56 (m, 2H). (2R)—N-(4-tert-butylphenyl)-N-[2-(cyclohexylamino)-2-oxo-1-(3-pyridyl)ethyl]-5,5-dimethyl-pyrrolidine-2-carboxamide (112.56 mg, 228.71 umol, 33.78% yield, 99.70% purity) as a solid. MS (ESI) m/z 491.1 $[M+H]^+$. $^1H$ NMR (400 MHz, METHANOL-$d_4$) δ ppm 1.03-1.25 (m, 12H) 1.25-1.44 (m, 6H) 1.48 (s, 3H) 1.59-1.98 (m, 8H) 2.14-2.37 (m, 1H) 3.66-3.81 (m, 1H) 4.22-4.32 (m, 1H) 6.22 (s, 1H) 6.81 (br s, 1H) 7.11-7.79 (m, 5H) 8.20 (br d, J=7.70 Hz, 1H) 8.39 (td, J=4.71, 1.59 Hz, 2H).

Step 3: (2R)—N-(4-tert-butylphenyl)-1-cyano-N-[2-(cyclohexylamino)-2-oxo-1-(3-pyridyl)ethyl]-5,5-dimethyl-pyrrolidine-2-carboxamide To a mixture of (2R)—N-(4-tert-butylphenyl)-N-[2-(cyclohexylamino)-2-oxo-1-(3-pyridyl)ethyl]-5,5-dimethyl-pyrrolidine-2-carboxamide (100 mg, 203.80 umol, 1 eq) in DMF (3 mL) was added $K_2CO_3$ (84.50 mg, 611.40 umol, 3 eq), BrCN (35.38 mg, 305.70 umol, 22.49 uL, 1.5 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Phenomenex Gemini-NX 80*40 mm*3 um; mobile phase: [water (10 mM $NH_4HCO_3$)-ACN]; B %: 40%-70%, 8 min) to get (2R)—N-(4-tert-butylphenyl)-1-cyano-N-[2-(cyclohexylamino)-2-oxo-1-(3-pyridyl)ethyl]-5,5-dimethyl-pyrrolidine-2-carboxamide (30 mg, 56.43 umol, 27.69% yield, 97% purity) as a solid. MS (ESI) m/z 516.1 $[M+H]^+$. $^1H$ NMR (400 MHz, METHANOL-$d_4$) δ ppm 1.02-1.43 (m, 18H) 1.56-1.80 (m, 5H) 1.83-2.09 (m, 4H) 3.67 (tt, J=10.77, 3.77 Hz, 1H) 4.21 (dd, J=7.64, 5.56 Hz, 1H) 6.00 (s, 1H) 6.26-6.96 (m, 1H) 7.00-7.80 (m, 5H) 8.24-8.44 (m, 2H).

Step 4: (2R)—N-(4-tert-butylphenyl)-1-cyano-N-[2-(cyclohexylamino)-2-oxo-1-(3-pyridyl)ethyl]-5,5-dimethyl-pyrrolidine-2-carboxamide To a mixture of (2R)—N-(4-tert-butylphenyl)-N-[2-(cyclohexylamino)-2-oxo-1-(3-pyridyl)ethyl]-5,5-dimethyl-pyrrolidine-2-carboxamide (100 mg, 203.80 umol, 1 eq) in DMF (3 mL) was added $K_2CO_3$ (84.50 mg, 611.40 umol, 3 eq) and BrCN (32.38 mg, 305.70 umol, 22.49 uL, 1.5 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Phenomenex Gemini-NX 80*40 mm*3 um; mobile phase: [water (10 mM $NH_4HCO_3$)-ACN]; B %: 40%-70%, 8 min) to get (2R)—N-(4-tert-butylphenyl)-1-cyano-N-[2-(cyclohexylamino)-2-oxo-1-(3-pyridyl)ethyl]-5,5-dimethyl-pyrrolidine-2-carboxamide (30 mg, 58.17 umol, 28.55% yield, 100% purity) as a solid. MS (ESI) m/z 516.1 $[M+H]^+$. $^1H$ NMR (400 MHz, METHANOL-$d_4$) δ ppm 1.00-1.19 (m, 2H) 1.20-1.26 (m, 12H) 1.26-1.46 (m, 6H) 1.56-1.82 (m, 5H) 1.86-2.00 (m, 3H) 2.07-2.20 (m, 1H) 3.60-3.82 (m, 1H) 4.20 (dd, J=7.58, 5.50 Hz, 1H) 6.13 (s, 1H) 6.62 (br s, 1H) 7.03-7.83 (m, 5H) 8.16-8.39 (m, 2H).

Example 37: Synthesis of Compound 268

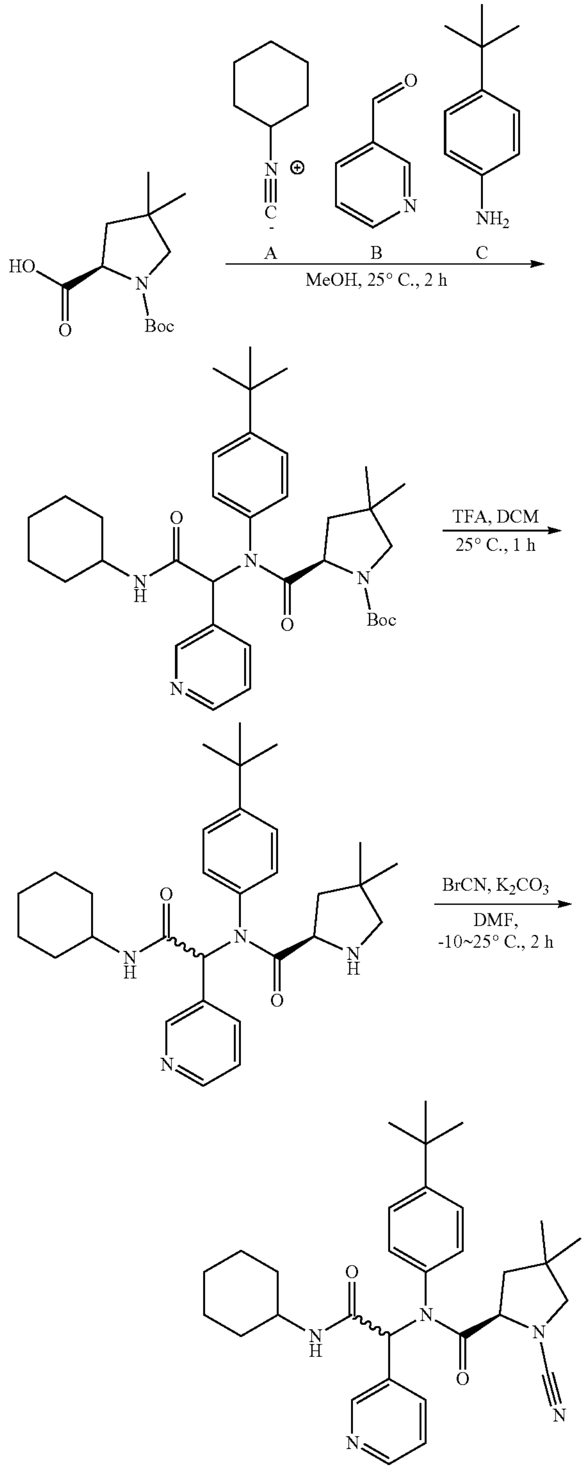

Step 1: tert-butyl (2R)-2-[(4-tert-butylphenyl)-[2-(cyclohexylamino)-2-oxo-1-(3-pyridyl)ethyl]carbamoyl]-4,4-dimethyl-pyrrolidine-1-carboxylate A solution of pyridine-3-carbaldehyde (123.27 mg, 1.15 mmol, 108.13 uL, 1.4 eq) and 4-tert-butylaniline (122.67 mg, 822.04 umol, 129.81 uL, 1 eq) in MeOH (1 mL) was stirred for 25° C. for 0.5 h, and then was added (2R)-1-tert-butoxycarbonyl-4,4-dimethyl-pyrrolidine-2-carboxylic acid (200 mg, 822.04 umol, 1 eq) and isocyanocyclohexane (89.74 mg, 822.04 umol, 102.21 uL, 1 eq). The resulting mixture was stirred at 25° C. for 1.5 h. The solution was diluted with $H_2O$ (10 mL), extracted with EtOAc (3*20 mL), the combined organic phase was dried over $Na_2SO_4$, filtrated and concentrated to give a residue. The residue was purified by prep-TLC (petroleum ether/ethyl acetate=3:1) to get tert-butyl (2R)-2-[(4-tert-butylphenyl)-[2-(cyclohexylamino)-2-oxo-1-(3-pyridyl)ethyl]carbamoyl]-4,4-dimethyl-pyrrolidine-1-carboxylate (400 mg, 541.64 umol, 65.89% yield, 80% purity) as an oil. MS (ESI) m/z 591.1 $[M+H]^+$.

Step 2: (2R)—N-(4-tert-butylphenyl)-N-[2-(cyclohexylamino)-2-oxo-1-(3-pyridyl)ethyl]-4,4-dimethyl-pyrrolidine-2-carboxamide and (2R)—N-(4-tert-butylphenyl)-N-[2-(cyclohexylamino)-2-oxo-1-(3-pyridyl)ethyl]-4,4-dimethyl-pyrrolidine-2-carboxamide To a solution of tert-butyl (2R)-2-[(4-tert-butylphenyl)-[2-(cyclohexylamino)-2-oxo-1-(3-pyridyl)ethyl]carbamoyl]-4,4-dimethyl-pyrrolidine-1-carboxylate (400 mg, 677.06 umol, 1 eq) in DCM (3 mL) was added with TFA (2.31 g, 20.26 mmol, 1.50 mL, 29.92 eq). The resulting mixture was stirred at 25° C. for 1.5 h. The solution was diluted with $H_2O$ (10 mL), extracted with EtOAc (3*20 mL), and the combined organic phase was dried over $Na_2SO_4$, filtrated and concentrated to give the crude. The crude was purified by prep-HPLC (column: Phenomenex luna C18 100*40 mm*5 um; mobile phase: [water (0.1% TFA)-ACN]; B %: 23%-35%, 8 min) to get (2R)—N-(4-tert-butylphenyl)-N-[2-(cyclohexylamino)-2-oxo-1-(3-pyridyl)ethyl]-4,4-dimethyl-pyrrolidine-2-carboxamide (150 mg, 290.41 umol, 42.89% yield, 95% purity) as a solid. MS (ESI) m/z 491.1 $[M+H]^+$. $^1H$ NMR (400 MHz, METHANOL-$d_4$) δ ppm 0.93 (s, 3H) 1.04-1.12 (m, 1H) 1.14 (s, 3H) 1.15-1.27 (m, 11H) 1.27-1.42 (m, 2H) 1.58-1.80 (m, 5H) 1.83-1.94 (m, 2H) 2.97-3.19 (m, 21H) 3.60-3.76 (m, 1H) 4.26 (t, J=8.86 Hz, 1H) 6.07 (s, 1H) 6.54-6.93 (m, 1H) 7.16-7.92 (m, 5H) 8.19 (br d, J=7.95 Hz, 1H) 8.42-8.58 (m, 2H). (2R)—N-(4-tert-butylphenyl)-N-[2-(cyclohexylamino)-2-oxo-1-(3-pyridyl)ethyl]-4,4-dimethyl-pyrrolidine-2-carboxamide (150 mg, 290.41 umol, 42.89% yield, 95% purity) as a solid. MS (ESI) m/z 491.1 $[M+H]^+$. 1H NMR (400 MHz, METHANOL-$d_4$) δ ppm 0.94 (s, 3H) 1.04-1.24 (m, 14H) 1.25-1.45 (m, 3H) 1.54-1.83 (m, 5H) 1.86-1.99 (m, 2H) 2.96-3.18 (m, 2H) 3.61-3.80 (m, 1H) 4.28 (t, J=8.80 Hz, 1H) 6.24 (s, 1H) 6.82 (br s, 1H) 7.18-7.87 (m, 5H) 8.22 (br d, J=7.58 Hz, 1H) 8.35-8.57 (m, 2H).

Step 3: (2R)—N-(4-tert-butylphenyl)-1-cyano-N-[2-(cyclohexylamino)-2-oxo-1-(3-pyridyl)ethyl]-4,4-dimethyl-pyrrolidine-2-carboxamide To a mixture of (2R)—N-(4-tert-butylphenyl)-N-[2-(cyclohexylamino)-2-oxo-1-(3-pyridyl)ethyl]-4,4-dimethyl-pyrrolidine-2-carboxamide (100 mg, 203.80 umol, 1 eq) in DCM (1 mL) was added TEA (61.87 mg, 611.40 umol, 85.10 uL, 3 eq) and BrCN (43.17 mg, 407.60 umol, 29.98 uL, 2 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Waters Xbridge BEH C18 100*30 mm*10 um; mobile phase: [water (10 mM $NH_4HCO_3$)-ACN]; B %: 40%-70%, 8 min) to get (2R)—N-(4-tert-butylphenyl)-1-cyano-N-[2-(cyclohexylamino)-2-oxo-1-(3-pyridyl)ethyl]-4,4-dimethyl-pyrrolidine-2-carboxamide (30 mg, 58.17 umol, 28.55% yield, 100% purity) as a solid. MS (ESI) m/z 516.1 $[M+H]^+$. $^1H$ NMR (400 MHz, DMSO-$d_6$) δ ppm 1.21-1.25 (m, 1H) 1.47-1.76 (m, 5H) 3.33 (quin, J=7.86 Hz, 1H) 4.121 (t, J=7.21 Hz, 1H) 4.22 (br t, J=7.09 Hz, 1H) 6.00 (br s, 1H) 6.94-7.48 (m, 6H) 8.09 (br d, J=7.58 Hz, 1H) 8.21-8.37 (m, 2H).

Step 4: (2R)—N-(4-tert-butylphenyl)-1-cyano-N-[2-(cyclohexylamino)-2-oxo-1-(3-pyridyl)ethyl]-4,4-dimethyl-pyrrolidine-2-carboxamide To a mixture of (2R)—N-(4-tert-butylphenyl)-N-[2-(cyclohexylamino)-2-oxo-1-(3-pyridyl)ethyl]-4,4-dimethyl-pyrrolidine-2-carboxamide (100 mg, 203.80 umol, 1 eq) in DCM (3 mL) was added TEA (61.87 mg, 611.40 umol, 85.10 uL, 3 eq), BrCN (43.17 mg, 407.60 umol, 29.98 uL, 2 eq) in one portion at −10° C. The mixture was stirred at 25° C. for 1 h. The aqueous phase was extracted with EtOAc (3*20 mL). The combined organic phase was washed with brine (3*20 mL), dried with anhydrous $Na_2SO_4$, filtered and concentrated in vacuum. The residue was purified by prep-HPLC (column: Waters Xbridge BEH C18 100*30 mm*10 um; mobile phase: [water (10 mM $NH_4HCO_3$)-ACN]; B %: 40%-70%, 8 min) to get (2R)—N-(4-tert-butylphenyl)-1-cyano-N-[2-(cyclohexylamino)-2-oxo-1-(3-pyridyl)ethyl]-4,4-dimethyl-pyrrolidine-2-carboxamide (30 mg, 58.17 umol, 28.55% yield, 100% purity) as a solid. MS (ESI) m/z 516.1 $[M+H]^+$. $^1H$ NMR (400 MHz, METHANOL-$d_4$) δ ppm 0.88 (s, 3H) 1.00-1.13 (m, 4H) 1.13-1.24 (m, 10H) 1.24-1.44 (m, 3H) 1.59-1.89 (m, 6H) 1.94 (br d, J=12.35 Hz, 1H) 3.15 (d, J=9.04 Hz, 1H) 3.35 (d, J=9.04 Hz, 1H) 3.62-3.80 (m, 1H) 4.20 (t, J=8.16 Hz, 1H) 6.14 (s, 1H) 6.65 (br s, 1H) 7.09-7.76 (m, 5H) 8.21-8.35 (in, 2H).

Example 38: Synthesis of Compound 278

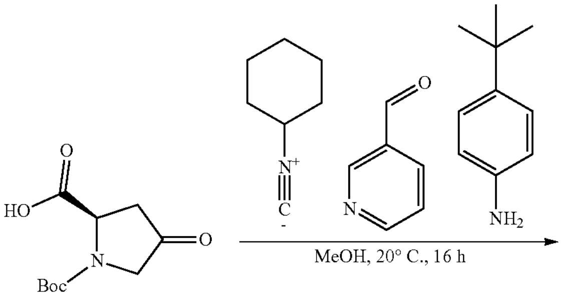

-continued

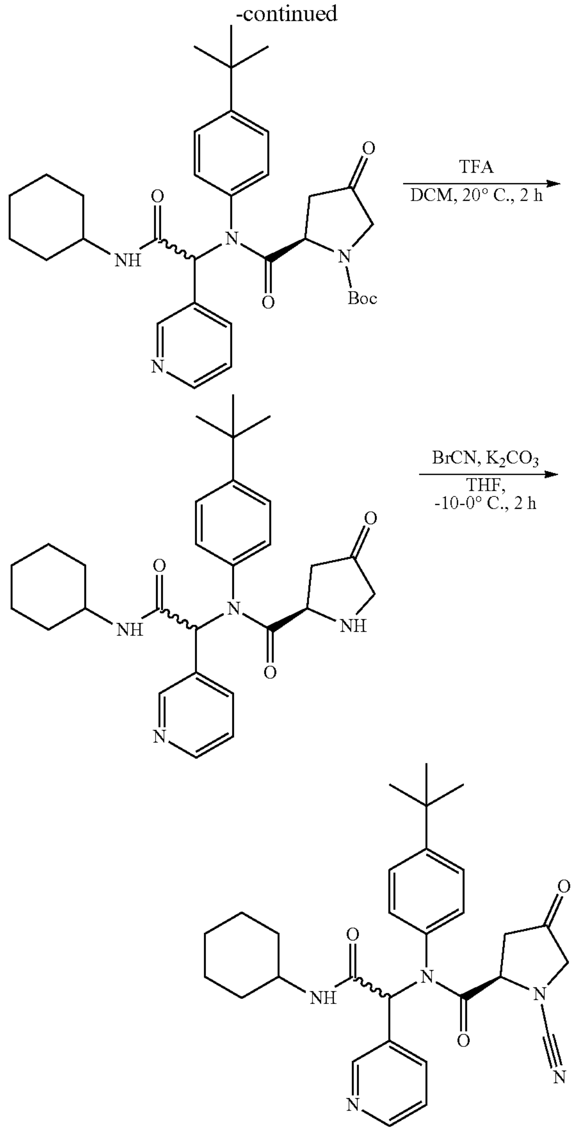

Step 1: tert-butyl (2R)-2-[(4-tert-butylphenyl)-[2-(cyclohexylamino)-2-oxo-1-(3-pyridyl)ethyl]carbamoyl]-4-oxo-pyrrolidine-1-carboxylate and tert-butyl (2R)-2-[(4-tert-butylphenyl)-[2-(cyclohexylamino)-2-oxo-1-(3-pyridyl)ethyl] carbamoyl]-4-oxo-pyrrolidine-1-carboxylate To a mixture of 4-tert-butylaniline (500 mg, 3.35 mmol, 529.10 uL, 1 eq) and pyridine-3-carbaldehyde (358.87 mg, 3.35 mmol, 314.80 uL, 1 eq) in MeOH (10 mL) was added (2R)-1-tert-butoxycarbonyl-4-oxo-pyrrolidine-2-carboxylic acid (768.03 mg, 3.35 mmol, 1 eq) and isocyanocyclohexane (365.77 mg, 3.35 mmol, 416.59 uL, 1 eq). The mixture was stirred at 20° C. for 16 h. The reaction was concentrated in vacuum and purified by prep-HPLC (column: Kromasil C18 (250*50 mm*10 um); mobile phase: [water (10 mM NH4HCO3)-ACN]; B %: 50%-80%, 10 min) to give tert-butyl (2R)-2-[(4-tert-butylphenyl)-[2-(cyclohexylamino)-2-oxo-1-(3-pyridyl)ethyl]carbamoyl]-4-oxo-pyrrolidine-1-carboxylate (450 mg, 780.27 umol, 23.29% yield, 100% purity) and tert-butyl (2R)-2-[(4-tert-butylphenyl)-[2-(cyclohexylamino)-2-oxo-1-(3-pyridyl)ethyl]carbamoyl]-4-oxo-pyrrolidine-1-carboxylate (430 mg, 745.59 umol, 22.25% yield, 100% purity). MS (ESI) m/z 577.2 $[M+H]^+$.

Step 2: (2R)—N-(4-(tert-butyl)phenyl)-N-(2-(cyclohexylamino)-2-oxo-1-(pyridin-3-yl)ethyl)-4-oxopyrrolidine-2-carboxamide To a mixture of (2R)-tert-butyl 2-((4-(tert-butyl)phenyl)(2-(cyclohexylamino)-2-oxo-1-(pyridin-3-yl)ethyl)carbamoyl)-4-oxopyrrolidine-1-carboxylate (450 mg, 780.27 umol, 1 eq) in DCM (10 mL) was added TFA (2 mL). The mixture was stirred at 20° C. for 2 h. The reaction was concentrated to give the crude and purified by prep-TLC (petroleum ether/EtOAc=0:1) to give (2R)—N-(4-(tert-butyl)phenyl)-N-(2-(cyclohexylamino)-2-oxo-1-(pyridin-3-yl)ethyl)-4-oxopyrrolidine-2-carboxamide (350 mg, 734.35 umol, 94.12% yield, 100% purity) as an oil. MS (ESI) m/z 476.3 $[M+H]^+$.

Step 3: (2R)—N-(4-tert-butylphenyl)-1-cyano-N-[2-(cyclohexylamino)-2-oxo-1-(3-pyridyl)ethyl]-4-oxo-pyrrolidine-2-carboxamide To a mixture of (2R)—N-(4-tert-butylphenyl)-N-[2-(cyclohexylamino)-2-oxo-1-(3-pyridyl)ethyl]-4-oxo-pyrrolidine-2-carboxamide (320 mg, 671.41 umol, 1 eq) and $K_2CO_3$ (278.38 mg, 2.01 mmol, 3 eq) in THF (8 mL) was added CNBr (71.12 mg, 671.41 umol, 49.39 uL, 1 eq) in one portion at −10° C. The mixture was stirred at 0° C. and stirred for 2 h. The reaction was concentrated and purified by prep-HPLC (column: Phenomenex Gemini-NX 80*40 mm*3 um; mobile phase: [water (10 mM $NH_4HCO_3$)-ACN]; B %: 30%-50%, 8 min) to give (2R)—N-(4-tert-butylphenyl)-1-cyano-N-[2-(cyclohexylamino)-2-oxo-1-(3-pyridyl)ethyl]-4-oxo-pyrrolidine-2-carboxamide (85.6 mg, 170.65 umol, 25.42% yield, 100% purity) as a solid. $^1H$ NMR (400 MHz, DMSO-$d_6$) δ ppm 8.30-8.31 (d, J=5.60 Hz, 2H), 7.98-8.00 (d, J=7.60 Hz, 1H), 7.30-7.32 (m, 2H), 7.08-7.10 (m, 3H), 5.93 (s, 1H), 4.32-4.35 (m, 1H), 3.87 (s, 2H), 3.56 (s, 1H), 2.63-2.65 (m, 2H), 1.66-1.69 (m, 3H), 1.50-1.58 (m, 2H), 1.26-1.27 (m, 2H), 1.18 (s, 9H), 0.95-1.18 (m, 3H). MS (ESI) m/z 501.3 $[M+H]^+$.

Step 4: (2R)—N-(4-(tert-butyl)phenyl)-N-(2-(cyclohexylamino)-2-oxo-1-(pyridin-3-yl)ethyl)-4-oxopyrrolidine-2-carboxamide To a mixture of (2R)-tert-butyl 2-((4-(tert-butyl)phenyl)(2-(cyclohexylamino)-2-oxo-1-(pyridin-3-yl)ethyl)carbamoyl)-4-oxopyrrolidine-1-carboxylate (430 mg, 745.59 umol, 1 eq) in DCM (5 mL) was added TFA (1 mL). The mixture was stirred at 20° C. for 2 h. The reaction was concentrated and purified by prep-HPLC (column: Phenomenex luna C18 250*50 mm*10 um; mobile phase: [water (0.1% TFA)-ACN]; B %: 25%-55%, 10 min) to give (2R)—N-(4-(tert-butyl)phenyl)-N-(2-(cyclohexylamino)-2-oxo-1-(pyridin-3-yl)ethyl)-4-oxopyrrolidine-2-carboxamide (320 mg, 671.41 umol, 90.05% yield, 100% purity) as an oil. MS (ESI) m/z 476.3 $[M+H]^+$.

Step 5: (2R)—N-(4-tert-butylphenyl)-1-cyano-N-[2-(cyclohexylamino)-2-oxo-1-(3-pyridyl)ethyl]-4-oxo-pyrrolidine-2-carboxamide To a mixture of (2R)—N-(4-tert-butylphenyl)-N-[2-(cyclohexylamino)-2-oxo-1-(3-pyridyl)ethyl]-4-oxo-pyrrolidine-2-carboxamide (350 mg, 734.35 umol, 1 eq) and $K_2CO_3$ (304.48 mg, 2.20 mmol, 3 eq) in THF (8 mL) was added CNBr (77.78 mg, 734.35 umol, 54.02 uL, 1 eq) in one portion at −10° C. The mixture was stirred at 0° C. and stirred for 2 h. The reaction was concentrate and purified by prep-HPLC (column: Phenomenex Gemini-NX C18 75*30 mm*3 um; mobile phase: [water (10 mM $NH_4HCO_3$)-ACN]; B %: 45%-65%, 8 min) to give (2R)—N-(4-tert-butylphenyl)-1-cyano-N-[2-(cyclohexylamino)-2-oxo-1-(3-pyridyl)ethyl]-4-oxo-pyrrolidine-2-carboxamide (10 mg, 19.94 umol, 2.71% yield, 100% purity) as a solid. MS (ESI) m/z 502.2 $[M+H]^+$. $^1H$ NMR (400 MHz, DMSO-$d_6$) δ ppm 8.30-8.31 (d, J=5.60 Hz, 2H), 7.99-8.01 (d, J=7.60 Hz, 1H), 7.23-7.32 (m, 3H), 6.74-7.11 (m, 3H), 5.88 (s, 1H), 4.32-4.35 (m, 1H), 3.87 (s, 2H), 3.56 (s, 1H), 3.55-3.56 (m, 2H), 2.64-2.65 (d, J=6.01 Hz, 2H), 1.66-1.69 (m, 3H), 1.54-1.55 (m, 2H), 1.23-1.26 (m, 2H), 1.18 (s, 9H), 0.92-1.12 (m, 3H).

Example 39: Synthesis of Compound 284

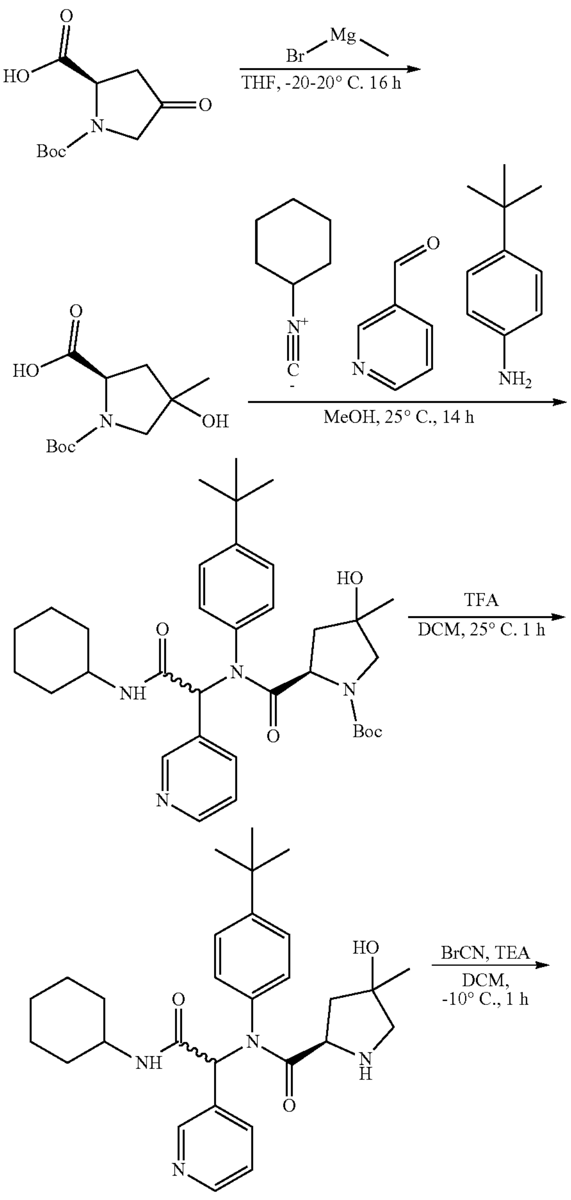

-continued

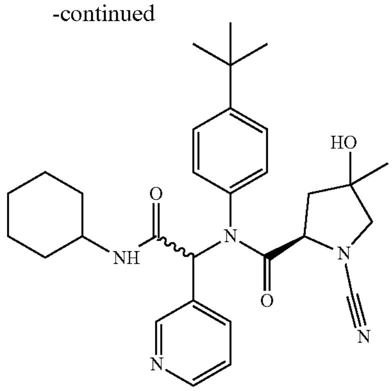

Step 1: (2R)-1-tert-butoxycarbonyl-4-hydroxy-4-methyl-pyrrolidine-2-carboxylic acid To a mixture of (2R)-1-tert-butoxycarbonyl-4-oxo-pyrrolidine-2-carboxylic acid (650 mg, 2.84 mmol, 1 eq) in THF (25 mL) was added methylmagnesium bromide (3 M, 2.36 mL, 2.5 eq) at −20° C. under $N_2$. The mixture was stirred at −20° C. for 1 h, then heated to 20° C. and stirred for 15 h. 1M HCl aq. (20 mL) was added and extracted with EtOAc (30 mL*3). The combined organic phase was washed with brine (90 mL), dried over $Na_2SO_4$, filtered, concentrated under reduced pressure and purified by prep-HPLC to give (2R)-1-tert-butoxycarbonyl-4-hydroxy-4-methyl-pyrrolidine-2-carboxylic acid (390 mg, 1.51 mmol, 52.93% yield, 95% purity) as an oil. MS (ESI) m/z 513.3 $[2M+Na]^+$.

Step 2: (2R,4R)-tert-butyl (2R)-tert-butyl 2-((4-(tert-butyl)phenyl)(2-(cyclohexylamino)-2-oxo-1-(pyridin-3-yl)ethyl)carbamoyl)-4-hydroxy-4-methylpyrrolidine-1-carboxylate To a solution of pyridine-3-carbaldehyde (126.64 mg, 1.18 mmol, 111.09 uL, 1 eq), 4-tert-butylaniline (176.45 mg, 1.18 mmol, 186.72 uL, 1 eq), (2R)-1-tert-butoxycarbonyl-4-hydroxy-4-methyl-pyrrolidine-2-carboxylic acid (290 mg, 1.18 mmol, 1 eq) and isocyanocyclohexane (116.17 mg, 1.06 mmol, 132.31 uL, 0.9 eq) in MeOH (9 mL) was stirred at 25° C. for 14 h. The reaction mixture was concentrated under reduced pressure, then purified by column chromatography ($SiO_2$, petroleum ether:EtOAc=10:1 to 1:1) to give the product (2R)-2-[(4-tert-butylphenyl)-[2-(cyclohexylamino)-2-oxo-1-(3-pyridyl)ethyl]carbamoyl]-4-hydroxy-4-methyl-pyrrolidine-1-carboxylate (621 mg, 995.25 umol, 84.17% yield, 95% purity) as a solid. MS (ESI) m/z 593.2 $[M+H]^+$.

Step 3: (2R)—N-(4-(tert-butyl)phenyl)-N-(2-(cyclohexylamino)-2-oxo-1-(pyridin-3-yl)ethyl)-4-hydroxy-4-methylpyrrolidine-2-carboxamide To a solution of (2R)-2-[(4-tert-butylphenyl)-[2-(cyclohexylamino)-2-oxo-1-(3-pyridyl)ethyl]carbamoyl]-4-hydroxy-4-methyl-pyrrolidine-1-carboxylate (810.00 mg, 1.37 mmol, 1 eq) in DCM (9 mL) was added TFA (4.62 g, 40.52 mmol, 3 mL, 29.65 eq), and the mixture was stirred at 25° C. for 1 h. The reaction mixture was concentrated under reduced pressure and then purified by prep-HPLC to give (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (218 mg, 433.65 umol, 31.74% yield, 98% purity) as a solid, and (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (66 mg, 131.29 umol, 9.61% yield, 98% purity) as a solid. MS (ESI) m/z 493.2 $[M+H]^+$. prep-HPLC condition: column: Phenomenex luna C18 250*50 mm*10 um; mobile phase: [water (0.1% TFA)-ACN]; B %: 30%-40%, 10 min.

Step 4: (2R)—N-(4-(tert-butyl)phenyl)-1-cyano-N-(2-(cyclohexylamino)-2-oxo-1-(pyridin-3-yl)ethyl)-4-hydroxy-4-methylpyrrolidine-2-carboxamide Compound 284 Isomer 1: To a solution of (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (208 mg, 432.76 umol, 1 eq) in DCM (2 mL) was added TEA (131.37 mg, 1.30 mmol, 180.70 uL, 3 eq) and then BrCN (46.75 mg, 441.41 umol, 32.47 uL, 1.02 eq) under N2 at −10° C. The mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R)—N-(4-(tert-butyl)phenyl)-1-cyano-N-(2-(cyclohexylamino)-2-oxo-1-(pyridin-3-yl)ethyl)-4-hydroxy-4-methylpyrrolidine-2-carboxamide (72.44 mg, 139.94 umol, 32.34% yield, 100% purity) as a solid. MS (ESI) m/z 518.2 $[M+H]^+$. prep-HPLC condition (Compound 284 Isomer 1): column: Phenomenex Gemini-NX 80*40 mm*3 um; mobile phase: [water (10 mM NH4HCO3)-ACN]; B %: 25%-55%, 8 min. $^1$H NMR (Compound 284 Isomer 1) (400 MHz, MeOD-$d_4$) δ ppm 8.41-8.27 (m, 2H), 7.71 (s, 1H), 7.58-7.52 (m, 1H), 7.45 (s, 1H), 7.31-7.06 (m, 2H), 6.58 (s, 1H), 6.03 (s, 1H), 4.33-4.23 (m, 1H), 3.75-3.62 (m, 1H), 3.55-3.45 (m, 1H), 3.37-3.32 (m, 1H), 2.07-1.99 (m, 1H), 1.98-1.88 (m, 2H), 1.81-1.56 (m, 4H), 1.44-1.01 (m, 17H).

Compound 284 Isomer 2: To a solution of (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (55 mg, 114.43 umol, 1 eq) in DCM (1 mL) was added TEA (34.74 mg, 343.29 umol, 47.78 uL, 3 eq), and then BrCN (12.36 mg, 116.72 umol, 8.59 uL, 1.02 eq) under $N_2$ at −10° C., the mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R)—N-(4-(tert-butyl)phenyl)-1-cyano-N-(2-(cyclohexylamino)-2-oxo-1-(pyridin-3-yl)ethyl)-4-hydroxy-4-methylpyrrolidine-2-carboxamide (26.54 mg, 51.27 umol, 44.80% yield, 100% purity) as a solid. MS (ESI) m/z 518.2 $[M+H]^+$. prep-HPLC condition (Compound 284 Isomer 2): column: Waters Xbridge BEH C18 100*30 mm*10 um; mobile phase: [water (10 mM NH4HCO3)-ACN]; B %: 36%-66%, 10 min. $^1$H NMR (Compound 284 Isomer 2) (400 MHz, MeOD-$d_4$) δ ppm 8.37-8.24 (m, 2H), 7.65 (s, 11H), 7.57-7.50 (m, 1H), 7.41 (s, 11H), 7.29-7.14 (m, 2H), 6.64 (s, 1H), 6.16 (s, 1H), 4.31-4.21 (m, 1H), 3.78-3.62 (m, 1H), 3.55-3.45 (m, 1H1), 3.36-3.32 (m, 1H), 2.18-2.08 (m, 1H), 2.00-1.89 (m, 2H), 1.82-1.57 (m, 4H), 1.41-1.04 (m, 17H).

Example 40: Synthesis of Compound 292

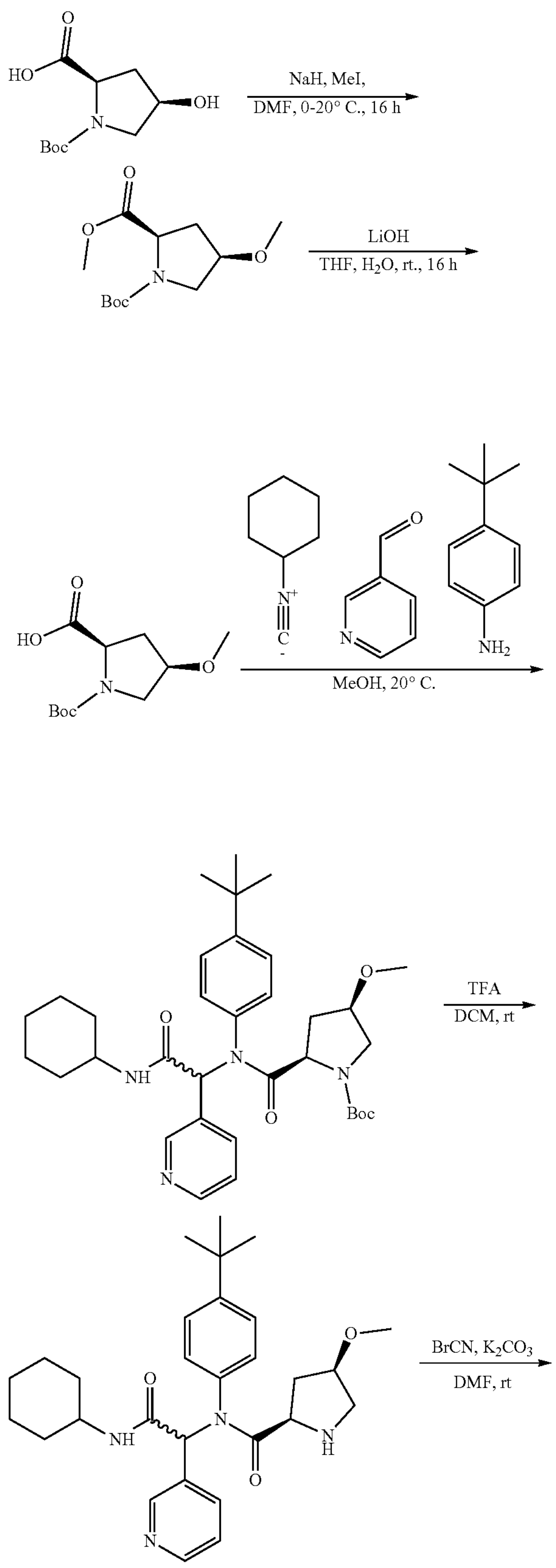

-continued

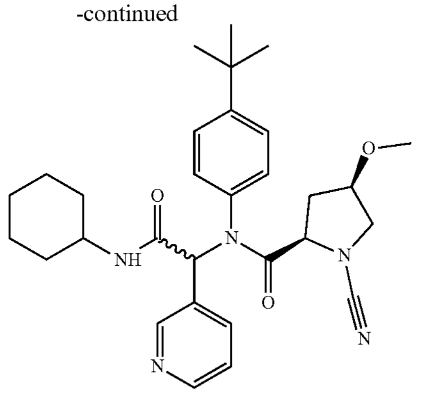

Step 1: (2R,4R)-1-tert-butyl 2-methyl 4-methoxypyrrolidine-1,2-dicarboxylate

To a solution of (2R,4R)-1-(tert-butoxycarbonyl)-4-hydroxypyrrolidine-2-carboxylic acid (1 g, 4.32 mmol, 1 eq) in DMF (10 mL) was added NaH (380.51 mg, 9.51 mmol, 60% purity, 2.2 eq) at 0° C., stirred 30 min, and then $CH_3I$ (1.35 g, 9.51 mmol, 592.26 uL, 2.2 eq) was added. The mixture was stirred at 20° C. for 15.5 h. Upon completion, the reaction mixture was quenched by addition water (30 mL) at 20° C., and then extracted with EtOAc (30 mL*3). The combined organic layers were washed with brine (30 mL*2), dried over ($Na_2SO_4$), filtered and concentrated under reduced pressure to give (2R,4R)-1-tert-butyl 2-methyl 4-methoxypyrrolidine-1,2-dicarboxylate (1.1 g, crude) as a an oil.

Step 2: (2R,4R)-1-(tert-butoxycarbonyl)-4-methoxypyrrolidine-2-carboxylic acid

To a solution of (2R,4R)-1-tert-butyl 2-methyl 4-methoxypyrrolidine-1,2-dicarboxylate (1.1 g, 4.24 mmol, 1 eq) in THF (5 mL) and $H_2O$ (2.5 mL) was added $LiOH \cdot H_2O$ (890.09 mg, 21.21 mmol, 5 eq). The mixture was stirred at 20° C. for 16 h. Upon completion, 1M HCl (~10 mL) was added, adjust pH to 7, and then extracted with EtOAc (50 mL*3). The combined organic layers were washed with brine (50 mL*2), dried over ($Na_2SO_4$), filtered and concentrated under reduced pressure to give (2R,4R)-1-(tert-butoxycarbonyl)-4-methoxypyrrolidine-2-carboxylic acid (920 mg, crude) as a solid. MS (ESI) m/z 244.0 $[M-H]^+$ $_1H$ NMR (400 MHz, DMSO-$d_6$) δ ppm 12.39 (s, 1H), 4.19-4.09 (m, 1H), 3.91 (d, J=3.3 Hz, 1H), 3.57-3.47 (m, 1H), 3.26-3.11 (m, 4H), 2.43-2.21 (m, 1H), 2.00 (d, J=3.3, 13.3 Hz, 1H), 1.42-1.32 (m, 9H).

Step 3: (2R,4R)-tert-butyl 2-((4-(tert-butyl)phenyl)(2-(cyclohexylamino)-2-oxo-1-(pyridin-3-yl)ethyl)carbamoyl)-4-methoxypyrrolidine-1-carboxylate A solution of 4-tert-butylaniline (300 mg, 2.01 mmol, 317.46 uL, 1 eq), pyridine-3-carbaldehyde (215.32 mg, 2.01 mmol, 188.88 uL, 1 eq) in MeOH (9 mL) was stirred for 1 h, then (2R,4R)-1-(tert-butoxycarbonyl)-4-methoxypyrrolidine-2-carboxylic acid (493.07 mg, 2.01 mmol, 1 eq) was added, stirred 10 min, and then isocyanocyclohexane (219.46 mg, 2.01 mmol, 249.95 uL, 1 eq) in MeOH (1 mL) was added. The mixture was stirred at 20° C. for 14 h 50 min. Upon completion, the reaction mixture was concentrated under reduced pressure to remove solvent. The residue was purified by prep-HPLC (column: Waters Xbridge Prep OBD C18 150*40 mm*10 um; mobile phase: [water (0.05% $NH_3H_2O$+10 mM $NH_4HCO_3$)-ACN]; B %: 60%-80%, 8 min) to give (2R,4R)-tert-butyl 2-((4-(tert-butyl)phenyl)(2-(cyclohexylamino)-2-oxo-1-(pyridin-3-yl)ethyl)carbamoyl)-4-methoxypyrrolidine-1-carboxylate (350 mg, 590.45 umol, 29.37% yield) and (2R,4R)-tert-butyl 2-((4-(tert-butyl)phenyl)(2-(cyclohexylamino)-2-oxo-1-(pyridin-3-yl) ethyl)carbamoyl)-4-methoxypyrrolidine-1-carboxylate (360 mg, 607.32 umol, 30.21% yield) as a solid. MS (ESI) m/z 593.4 $[M+H]^+$.

Step 4: (2R,4R)—N-(4-(tert-butyl)phenyl)-N-(2-(cyclohexylamino)-2-oxo-1-(pyridin-3-yl)ethyl)-4-methoxypyrrolidine-2-carboxamide Isomer 1: To a solution of (2R,4R)-tert-butyl 2-((4-(tert-butyl)phenyl)(2-(cyclohexylamino)-2-oxo-1-(pyridin-3-yl) ethyl)carbamoyl)-4-methoxypyrrolidine-1-carboxylate (350 mg, 590.45 umol, 1 eq) in DCM (5 mL) was added with TFA (2.31 g, 20.26 mmol, 1.5 mL, 34.31 eq). The mixture was stirred at 20° C. for 1 h. Upon completion, the reaction mixture was quenched by addition $NaHCO_3$ (30 mL) at 20° C., and then extracted with DCM (35 mL*3). The combined organic layers were washed with brine (35 mL*2), dried over ($Na_2SO_4$), filtered and concentrated under reduced pressure to give (2R,4R)—N-(4-(tert-butyl)phenyl)-N-(2-(cyclohexylamino)-2-oxo-1-(pyridin-3-yl)ethyl)-4-methoxypyrrolidine-2-carboxamide (290 mg, crude) as a solid. MS (ESI) m/z 493.4 $[M+H]^+$.

Isomer 2: To a solution of (2R,4R)-tert-butyl 2-((4-(tert-butyl)phenyl)(2-(cyclohexylamino)-2-oxo-1-(pyridin-3-yl) ethyl)carbamoyl)-4-methoxypyrrolidine-1-carboxylate (360 mg, 607.32 umol, 1 eq) in DCM (5 mL) was added TFA (1.85 g, 16.21 mmol, 1.20 mL, 26.69 eq). The mixture was stirred at 20° C. for 1 h. Upon completion, the reaction mixture was quenched by addition $NaHCO_3$ (30 mL) at 20° C., and then extracted with DCM (35 mL*3). The combined organic layers were washed with brine (35 mL*2), dried over ($Na_2SO_4$), filtered and concentrated under reduced pressure to give (2R,4R)—N-(4-(tert-butyl)phenyl)-N-(2-(cyclohexylamino)-2-oxo-1-(pyridin-3-yl)ethyl)-4-methoxypyrrolidine-2-carboxamide (270 mg, crude) as a solid. MS (ESI) m/z 493.4 $[M+H]^+$.

Step 5: (2R,4R)—N-(4-(tert-butyl)phenyl)-1-cyano-N-(2-(cyclohexylamino)-2-oxo-1-(pyridin-3-yl) ethyl)-4-methoxypyrrolidine-2-carboxamide Compound 292 Isomer 1: To a solution of (2R,4R)—N-(4-(tert-butyl)phenyl)-N-(2-(cyclohexylamino)-2-oxo-1-(pyridin-3-yl)ethyl)-4-methoxypyrrolidine-2-carboxamide (250 mg, 507.46 umol, 1 eq) in DMF (5 mL) was added $K_2CO_3$ (210.40 mg, 1.52 mmol, 3 eq), and then BrCN (64.50 mg, 608.95 umol, 44.79 uL, 1.2 eq) was added at −10° C. The mixture was stirred at −10° C. for 2 h. Upon completion, the reaction mixture was quenched by addition water (25 mL) at 20° C., and then extracted with EtOAc (35 mL*3). The combined organic layers were washed with brine (30 mL*2), dried over ($Na_2SO_4$), filtered and concentrated under reduced pressure to give a residue. The residue was purified by prep-HPLC ((column: Waters Xbridge Prep OBD C18 150*40 mm*10 um; mobile phase: [water (0.05% $NH_3H_2O$+10 mM $NH_4HCO_3$)-ACN]; B %: 45%-65%, 8 min)) to give (2R,4R)—N-(4-(tert-butyl)phenyl)-1-cyano-N-(2-(cyclohexylamino)-2-oxo-1-(pyridin-3-yl)ethyl)-4-methoxypyrrolidine-2-carboxamide (135 mg, 260.40 umol, 51.31% yield, 99.85% purity) as a solid. MS (ESI) m/z 518.3 $[M+H]^+$ Compound 292 Isomer 1: $^1H$ NMR (400 MHz, METHANOL-$d_4$) δ ppm 8.39-8.30 (m, 2H), 7.68 (s, 1H), 7.54 (d, J=8.1 Hz, 1H), 7.51 (s, 1H), 7.31-7.04 (m, 2H), 6.78-6.37 (m, 1H), 6.02 (s, 1H), 4.26 (d, J=5.7, 8.8 Hz, 1H), 3.88 (t, J=5.6 Hz, 1H), 3.70-3.57 (m, 2H), 3.49 (d, J=4.9, 9.7 Hz, 1H), 3.27 (s, 3H), 2.14-2.03 (m, 1H), 1.92 (d, J=5.4, 13.2 Hz, 2H), 1.80-1.57 (m, 4H), 1.41-1.28 (m, 2H), 1.27-1.04 (m, 12H).

Compound 292 Isomer 2: To a solution of (2R,4R)—N-(4-(tert-butyl)phenyl)-N-(2-(cyclohexylamino)-2-oxo-1-(pyridin-3-yl)ethyl)-4-methoxypyrrolidine-2-carboxamide (250 mg, 507.46 umol, 1 eq) in DMF (5 mL) was added $K_2CO_3$ (210.40 mg, 1.52 mmol, 3 eq), and then BrCN (64.50 mg, 608.95 umol, 44.79 uL, 1.2 eq) was added at −10° C. The mixture was stirred at −10° C. for 2 h. Upon completion, the reaction mixture was poured into water 30 mL at 20° C., and then extracted with EtOAc (35 mL*3). The combined organic layers were washed with brine (30 mL*2), dried over ($Na_2SO_4$), filtered and concentrated under reduced pressure to give a residue. The residue was purified by prep-HPLC ((column: Phenomenex Gemini-NX C18 75*30 mm*3 um; mobile phase: [water (0.05% $NH3H_2O$+10 mM $NH_4HCO_3$)-ACN]; B %: 40%-60%, 8 min)) to give (2R,4R)—N-(4-(tert-butyl)phenyl)-1-cyano-N-(2-(cyclohexylamino)-2-oxo-1-(pyridin-3-yl)ethyl)-4-methoxypyrrolidine-2-carboxamide (132 mg, 254.51 umol, 50.15% yield, 99.81% purity) as a solid. MS (ESI) m/z 518.3 $[M+H]^+$ Compound 292 Isomer 2: $^1H$ NMR (400 MHz, METHANOL-$d_4$) δ ppm 8.33-8.25 (m, 2H), 7.69 (s, 1H), 7.53 (d, J=7.9 Hz, 1H), 7.48-7.29 (m, 11H), 7.17 (d, J=4.9, 7.9 Hz, 2H), 6.66 (s, 11H), 6.17 (s, 11H), 4.20 (d, J=6.9, 8.4 Hz, 1H), 3.93-3.85 (m, 1H), 3.76-3.67 (m, 11H), 3.63 (d, J=6.2, 9.4 Hz, 1H), 3.46 (d, J=5.6, 9.3 Hz, 1H), 3.28 (s, 3H), 2.18-2.08 (m, 1H), 2.07-1.99 (m, 1H), 1.95 (d, J=11.9 Hz, 1H), 1.81-1.72 (m, 2H), 1.71-1.58 (m, 2H), 1.42-1.25 (m, 3H), 1.22 (s, 9H), 1.19-1.04 (m, 2H).

Example 41: Synthesis of Compound 293

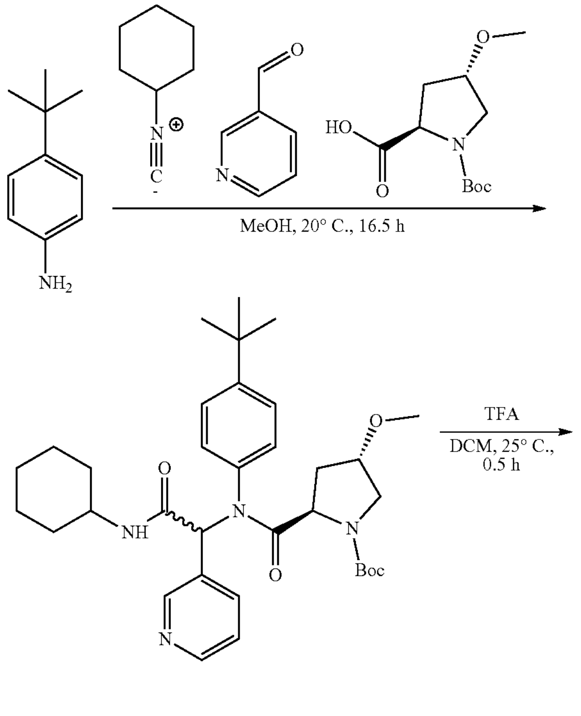

-continued

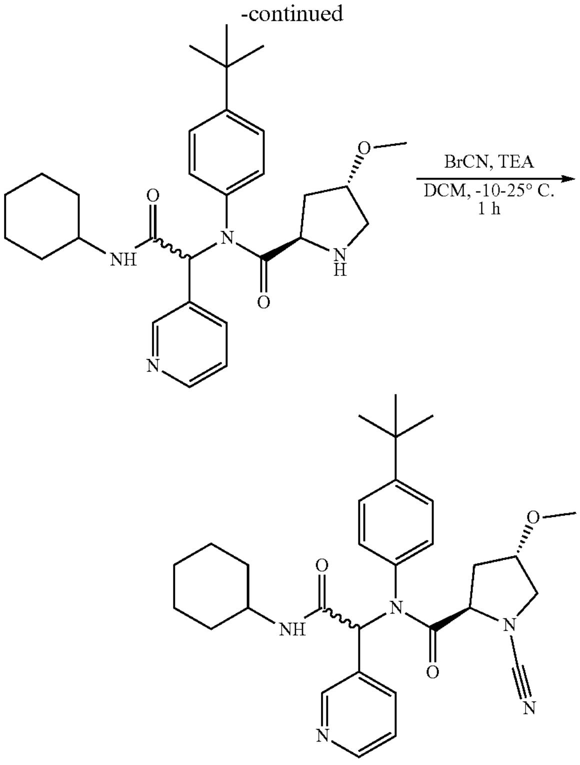

Step 1: (2R,4S)-tert-butyl2-((4-(tert-butyl)phenyl)(2-(cyclohexylamino)-2-oxo-1-(pyridin-3-yl)ethyl)carbamoyl)-4-methoxypyrrolidine-1-carboxylate 4-tert-Butylaniline (304.22 mg, 2.04 mmol, 321.93 uL, 1 eq) and pyridine-3-carbaldehyde (218.35 mg, 2.04 mmol, 191.53 uL, 1 eq) in MeOH (5 mL) was stirred at 25° C. for 30 min, and then (2R,4S)-1-tert-butoxycarbonyl-4-methoxy-pyrrolidine-2-carboxylic acid (500 mg, 2.04 mmol, 1 eq) was added. After stirring for 10 min, and isocyanocyclohexane (222.55 mg, 2.04 mmol, 253.47 uL, 1 eq) was added, and the mixture was stirred at 25° C. for 16 h. Upon completion, the mixture was concentrated under the reduced pressure to give a residue. The residue was purified by prep-HPLC to give the product tert-butyl(2R,4S)-2-[(4-tert-butylphenyl)-[2-(cyclohexylamino)-2-oxo-1-(3-pyridyl)ethyl]carbamoyl]-4-methoxy-pyrrolidine-1-carboxylate (460 mg, 776.02 umol, 38.07% yield). MS (ESI) m/z 593.3 $[M+H]^+$. Prep-HPLC condition: column: Kromasil C18 (250*50 mm*10 um); mobile phase: [water (10 mM $NH_4HCO_3$)-ACN]; B %: 50%-80%, 10 min. tert-butyl(2R,4S)-2-[(4-tert-butylphenyl)-[2-(cyclohexylamino)-2-oxo-1-(3-pyridyl)ethyl]carbamoyl]-4-methoxy-pyrrolidine-1-carboxylate (450 mg, 759.15 umol, 37.24% yield) as a solid. MS (ESI) m/z 593.3 $[M+H]^+$ Prep-HPLC condition: column: Kromasil C18 (250*50 mm*10 um); mobile phase: [water (10 mM $NH_4HCO_3$)-ACN]; B %: 50%-80%, 10 min.

Step 2: (2R,4S)—N-(4-(tert-butyl)phenyl)-N-(2-(cyclohexylamino)-2-oxo-1-(pyridin-3-yl)ethyl)-4-methoxypyrrolidine-2-carboxamide Isomer 1: tert-Butyl(2R,4S)-2-[(4-tert-butylphenyl)-[2-(cyclohexylamino)-2-oxo-1-(3-pyridyl)ethyl]carbamoyl]-4-methoxy-pyrrolidine-1-carboxylate (450 mg, 759.15 umol, 1 eq) in DCM (5 mL) was added with TFA (3.47 g, 30.39 mmol, 2.25 mL, 40.03 eq). The mixture was stirred at 25° C. for 0.5 h. Upon completion, the reaction mixture was quenched by addition sat. $NaHCO_3$ 10 mL, and then extracted with DCM (10 mL*3). The combined organic layers were washed with brine 10 mL, dried over $Na_2SO_4$, filtered and concentrated under reduced pressure affording the product (2R,4S)—N-(4-tert-butylphenyl)-N-[2-(cyclohexylamino)-2-oxo-1-(3-pyridyl)ethyl]-4-methoxy-pyrrolidine-2-carboxamide (350 mg, crude) as a solid. MS (ESI) m/z 493.2 $[M+H]^+$.

Isomer 2: tert-butyl(2R,4S)-2-[(4-tert-butylphenyl)-[2-(cyclohexylamino)-2-oxo-1-(3-pyridyl)ethyl]carbamoyl]-4-methoxy-pyrrolidine-1-carboxylate (450 mg, 759.15 umol, 1 eq) in DCM (5 mL) was added with TFA (3.47 g, 30.39 mmol, 2.25 mL, 40.03 eq). The mixture was stirred at 25° C. for 0.5 h. Upon completion, the reaction mixture was quenched by addition sat. $NaHCO_3$ 10 mL, and then extracted with DCM (10 mL*3). The combined organic layers were washed with brine 10 mL, dried over $Na_2SO_4$, filtered and concentrated under reduced pressure affording the product (2R,4S)—N-(4-tert-butylphenyl)-N-[2-(cyclohexylamino)-2-oxo-1-(3-pyridyl)ethyl]-4-methoxy-pyrrolidine-2-carboxamide (350 mg, crude) as a solid. MS (ESI) m/z 493.2 $[M+H]^+$.

Step 3:(2R,4S)—N-(4-(tert-butyl)phenyl)-1-cyano-N-(2-(cyclohexylamino)-2-oxo-1-(pyridin-3-yl)ethyl)-4-methoxypyrrolidine-2-carboxamide Compound 293 Isomer 1: To a solution of (2R,4S)—N-(4-tert-butylphenyl)-N-[2-(cyclohexylamino)-2-oxo-1-(3-pyridyl)ethyl]-4-methoxy-pyrrolidine-2-carboxamide (300 mg, 608.95 umol, 1 eq) in DCM (3 mL) was added with TEA (184.86 mg, 1.83 mmol, 254.27 uL, 3 eq), the solution was cooled to −10° C., and then a solution of BrCN (77.40 mg, 730.74 umol, 53.75 uL, 1.2 eq) in DCM (0.5 mL) was added. The resulting solution stirred for 1 h at 0° C. and warmed to 25° C. gradually. Upon completion, the reaction mixture was quenched by addition sat. $NaHCO_3$ 10 mL, and then extracted with DCM (10 mL*3). The combined organic layers were washed with brine 10 mL, dried over $Na_2SO_4$, filtered and concentrated under reduced pressure to give a residue. The residue was purified by prep-HPLC affording the product (2R,4S)—N-(4-tert-butylphenyl)-1-cyano-N-[2-(cyclohexylamino)-2-oxo-1-(3-pyridyl)ethyl]-4-methoxy-pyrrolidine-2-carboxamide (153 mg, 295.56 umol, 48.54% yield, 100% purity) as a solid. MS (ESI) m/z 518.2 $[M+H]^+$. Prep-HPLC condition: column: Waters Xbridge BEH C18 100*25 mm*5 um; mobile phase: [water (10 mM $NH_4HCO_3$)-ACN]; B %: 35%-65%, 10 min. $^1H$ NMR (400 MHz, MeOD-$d_4$) δ=8.36-8.19 (m, 2H), 7.68 (br d, J=4.8 Hz, 1H), 7.54-7.53 (m, 11H), 7.41 (br d, J=5.8 Hz, 1H), 7.18 (dd, J=5.0, 7.8 Hz, 2H), 6.65 (br d, J=4.8 Hz, 1H), 6.14 (s, 1H), 4.17 (t, J=8.0 Hz, 11H), 3.98 (br s, 11H), 3.76-3.59 (m, 2H), 3.49 (d, J=10.6 Hz, 11H), 3.15 (s, 3H), 2.13-1.97 (m, 2H), 1.96-1.89 (m, 1H), 1.82-1.57 (m, 4H), 1.38-1.05 (m, 14H).

Compound 293 Isomer 2: To a solution of (2R,4S)—N-(4-tert-butylphenyl)-N-[2-(cyclohexylamino)-2-oxo-1-(3-pyridyl)ethyl]-4-methoxy-pyrrolidine-2-carboxamide (300 mg, 608.95 umol, 1 eq) in DCM (1 mL) was added TEA (184.86 mg, 1.83 mmol, 254.27 uL, 3 eq), the solution was cooled to −10° C., then a solution of BrCN (77.40 mg, 730.74 umol, 53.75 uL, 1.2 eq) in DCM (0.5 mL) was added and the solution stirred for 1 h at 0° C. and warmed to 25° C. gradually. Upon completion, the reaction mixture was quenched by addition sat. $NaHCO_3$ 10 mL, and then extracted with DCM (10 mL*3). The combined organic layers were washed with brine 10 mL, dried over $Na_2SO_4$, filtered and concentrated under reduced pressure to give a residue. The residue was purified by prep-HPLC affording the product (2R,4S)—N-(4-tert-butylphenyl)-1-cyano-N-[2-(cyclohexylamino)-2-oxo-1-(3-pyridyl)ethyl]-4-methoxy-pyrrolidine-2-carboxamide (150 mg, 289.77 umol, 47.58% yield, 100% purity) as a solid. MS (ESI) m/z 518.2 $[M+H]^+$. Prep-HPLC condition: column: Waters Xbridge BEH C18 100*25 mm*5 um; mobile phase: [water (10 Mm $NH_4HCO_3$)-ACN]; B %: 35%-65%, 10 min. $^1H$ NMR (400 MHz, MeOD-$d_4$) δ=8.40-8.28 (m, 2H), 7.81-7.59 (m, 1H), 7.55 (td, J=1.8, 8.0 Hz, 1H), 7.51-7.33 (m, 1H), 7.20 (dd, J=5.0, 8.0 Hz, 2H), 6.76-6.46 (m, 1H), 6.02 (s, 11H), 4.17 (t, J=8.0 Hz, 1H), 3.96 (br d, J=2.8 Hz, 11H), 3.68 (tt, J=3.8, 10.8 Hz, 11H), 3.61 (dd, J=3.8, 10.8 Hz, 1H), 3.48 (d, J=10.8 Hz, 1H), 3.15 (s, 3H), 2.01 (dd, J=3.4, 8.4 Hz, 2H), 1.93 (br d, J=11.4 Hz, 1H), 1.80-1.57 (m, 4H), 1.38-1.06 (m, 14H).

Example 42: Synthesis of Compound 299

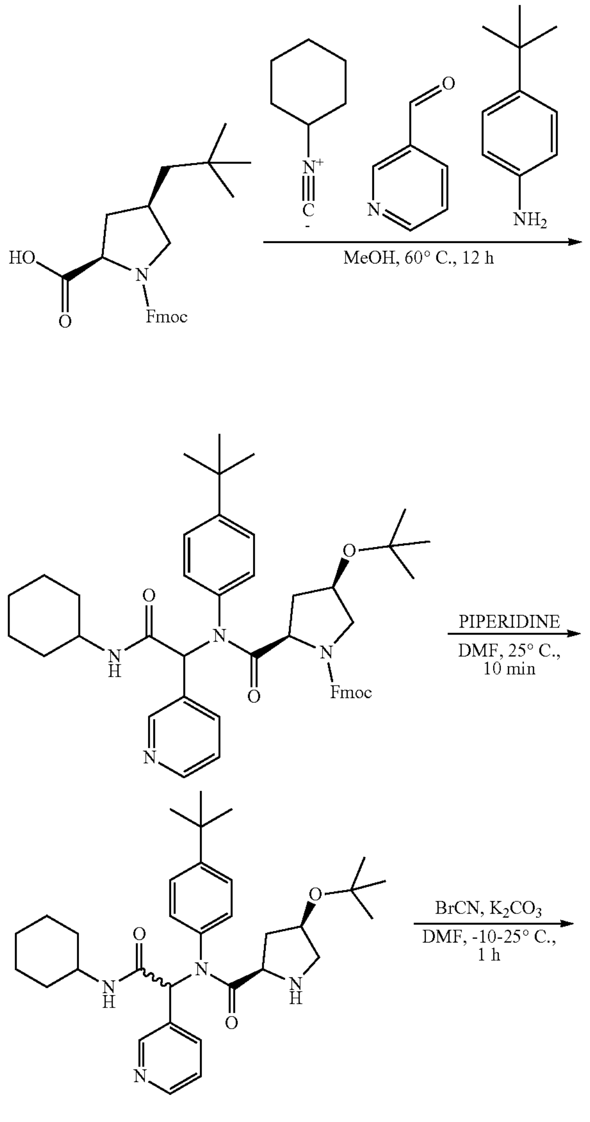

-continued

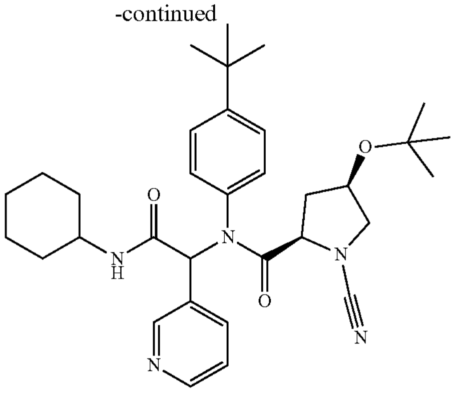

Step 1: (2R,4R)-(9H-fluoren-9-yl)methyl 4-(tert-butoxy)-2-((4-(tert-butyl)phenyl)(2-(cyclohexylamino)-2-oxo-1-(pyridin-3-yl)ethyl)carbamoyl)pyrrolidine-1-carboxylate To a solution of pyridine-3-carbaldehyde (130.79 mg, 1.22 mmol, 114.73 uL, 1 eq), 4-tert-butylaniline (182.22 mg, 1.22 mmol, 192.83 uL, 1 eq) in MeOH (6 mL), (2R,4R)-4-tert-butoxy-1-(9H-fluoren-9-ylmethoxycarbonyl)pyrrolidine-2-carboxylic acid (500 mg, 1.22 mmol, 1 eq) was added isocyanocyclohexane (133.30 mg, 1.22 mmol, 151.83 uL, 1.0 eq) in MeOH (1.5 mL). The mixture was stirred at 60° C. for 12 h, and the reaction mixture was concentrated under reduced pressure to give a residue. The residue was purified by column chromatography ($SiO_2$, petroleum ether: EtOAc=4/1 to 1/4) to get the product 9H-fluoren-9-ylmethyl (2R,4R)-4-tert-butoxy-2-[(4-tert-butylphenyl)-[2-(cyclohexylamino)-2-oxo-1-(3-pyridyl)ethyl]carbamoyl]pyrrolidine-1-carboxylate (750 mg, 990.79 umol, 81.14% yield) as a solid. MS (ESI) m/z 757.4 $[M+H]^+$.

Step 2: (2R,4R)-4-(tert-butoxy)-N-(4-(tert-butyl)phenyl)-N-(2-(cyclohexylamino)-2-oxo-1-(pyridin-3-yl)ethyl)pyrrolidine-2-carboxamide To a solution of 9H-fluoren-9-ylmethyl (2R,4R)-4-tert-butoxy-2-[(4-tert-butylphenyl)-[2-(cyclohexylamino)-2-oxo-1-(3-pyridyl)ethyl]carbamoyl]pyrrolidine-1-carboxylate (750 mg, 990.79 umol, 1 eq) in DMF (7.5 mL) was added drop-wise piperidine (1.29 g, 15.19 mmol, 1.5 mL, 15.33 eq), and the mixture was stirred at 25° C. for 10 min. The reaction mixture was quenched by addition $H_2O$ (40 mL) at 0° C., and then extracted with EtOAc (30 mL*3). The combined organic layers were washed with brine (30 mL), dried over $Na_2SO_4$, filtered and concentrated under reduced pressure to give a residue. The residue was purified by prep-HPLC (column: Phenomenex Gemini-NX 80*40 mm*3 um; mobile phase: [water (10 mM $NH_4HCO_3$)-ACN]; B %: 40%-60%, 8 min) to get the product (2R,4R)-4-tert-butoxy-N-(4-tert-butylphenyl)-N-[2-(cyclohexylamino)-2-oxo-1-(3-pyridyl)ethyl]pyrrolidine-2-carboxamide (100 mg, 187.01 umol, 18.87% yield) as a solid. MS (ESI) m/z 535.3 $[M+H]^+$. (2R,4R)-4-tert-butoxy-N-(4-tert-butylphenyl)-N-[2-(cyclohexylamino)-2-oxo-1-(3-pyridyl)ethyl]pyrrolidine-2-carboxamide (100 mg, 187.01 umol, 18.87% yield) as a solid. MS (ESI) m/z 535.3 $[M+H]^+$.

Step 3: (2R,4R)-4-(tert-butoxy)-N-(4-(tert-butyl)phenyl)-1-cyano-N-(2-(cyclohexylamino)-2-oxo-1-(pyridin-3-yl)ethyl)pyrrolidine-2-carboxamide A solution of (2R,4R)-4-tert-butoxy-N-(4-tert-butylphenyl)-N-[2-(cyclohexylamino)-2-oxo-1-(3-pyridyl)ethyl]pyrrolidine-2-carboxamide (90 mg, 168.31 umol, 1 eq) in DMF (1 mL) was cooled to −10° C., and then $K_2CO_3$ (69.79 mg, 504.93 umol, 3 eq) and BrCN (26.74 mg, 252.46 umol, 18.57 uL, 1.5 eq) was added. The mixture was allowed to warm to 25° C. and stirred for 1 h. The reaction mixture was quenched by addition $H_2O$ 20 mL at 0° C., and then extracted with EtOAc (15 mL*3). The combined organic layers were washed with brine 20 mL, dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 50%-75%, 10 min) to give the product (2R,4R)-4-tert-butoxy-N-(4-tert-butylphenyl)-1-cyano-N-[2-(cyclohexylamino)-2-oxo-1-(3-pyridyl)ethyl]pyrrolidine-2-carboxamide (44.14 mg, 78.86 umol, 46.85% yield, 100% purity) was obtained as a solid. 4H NMR (METHANOL-$d_4$, 400 MHz): δ ppm 8.24-8.46 (m, 2H), 8.03 (br d, J=7.8 Hz, 1H), 6.99-7.86 (m, 5H), 6.57 (s, 1H), 6.02 (s, 1H), 4.10-4.26 (m, 2H), 3.66 (td, J=7.3, 3.5 Hz, 1H), 3.56 (dd, J=9.0, 7.0 Hz, 1H), 3.25 (dd, J=9.0, 7.6 Hz, 1H), 2.05 (dt, J=12.7, 7.5 Hz, 1H), 1.92 (br d, J=10.6 Hz, 1H), 1.57-1.81 (m, 5H), 1.05-1.38 (m, 23H). MS (ESI) m/z 560.2 $[M+H]^+$.

To a solution of (2R,4R)-4-tert-butoxy-N-(4-tert-butylphenyl)-N-[2-(cyclohexylamino)-2-oxo-1-(3-pyridyl)ethyl]pyrrolidine-2-carboxamide (90 mg, 168.31 umol, 1 eq) in DMF (1 mL) was cooled to −10° C., and then $K_2CO_3$ (69.79 mg, 504.93 umol, 3 eq) and BrCN (26.74 mg, 252.46 umol, 18.57 uL, 1.5 eq) were added. The mixture was allowed to warm to 25° C. and stirred for 1 h. The reaction mixture was quenched by addition $H_2O$ 20 mL at 0° C., and then extracted with EtOAc (15 mL*3). The combined organic layers were washed with brine 20 mL, dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 50%-75%, 10 min) to give the product (2R,4R)-4-tert-butoxy-N-(4-tert-butylphenyl)-1-cyano-N-[2-(cyclohexylamino)-2-oxo-1-(3-pyridyl)ethyl]pyrrolidine-2-carboxamide (68.08 mg, 121.63 umol, 72.26% yield, 100% purity) as a solid. MS (ESI) m/z 560.2 $[M+H]^+$ $^1H$ NMR (METHANOL-$d_4$, 400 MHz): δ ppm 8.25-8.40 (m, 2H), 7.70 (br s, 1H), 7.54 (dt, J=7.9, 1.8 Hz, 1H), 7.42 (br s, 1H), 7.19 (dd, J=7.8, 4.7 Hz, 2H), 6.65 (br s, 1H), 6.17 (s, 1H), 4.10-4.29 (m, 2H), 3.73 (s, 1H), 3.58 (dd, J=8.7, 7.2 Hz, 1H), 3.27-3.31 (m, 1H), 2.04-2.16 (m, 1H), 1.96 (br d, J=1.6 Hz, 1H), 1.85-1.93 (m, 1H), 1.60-1.84 (m, 4H), 1.05-1.42 (m, 23H).

Example 43: Synthesis of Compound 307

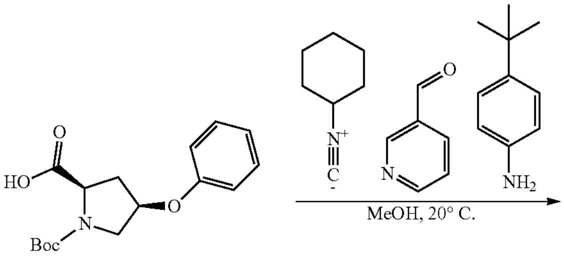

-continued

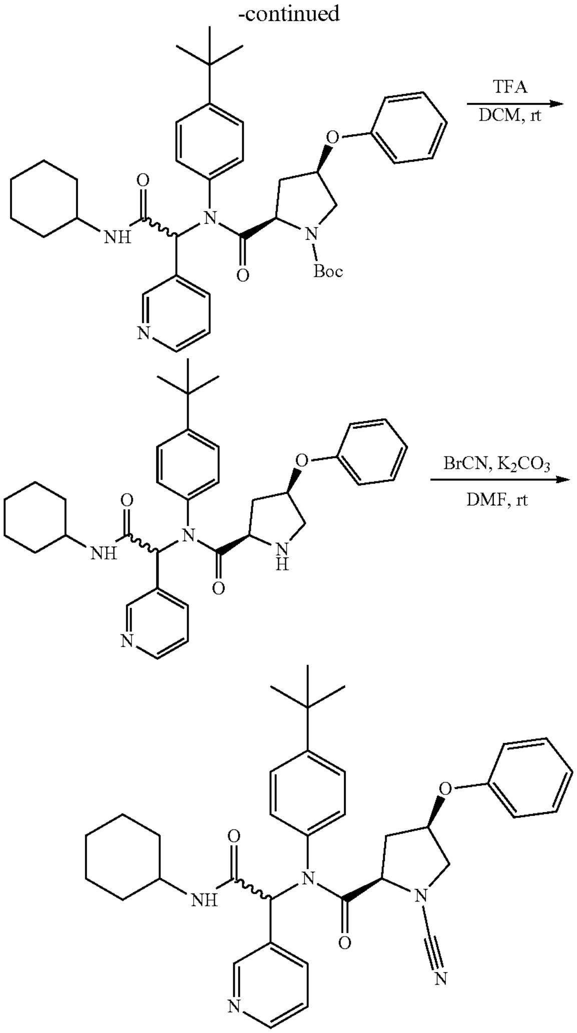

Step 1: (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate A solution of nicotinaldehyde (163.80 mg, 1.53 mmol, 143.68 uL, 1 eq), 4-(tert-butyl)aniline (228.21 mg, 1.53 mmol, 241.50 uL, 1 eq) in MeOH (6 mL) was stirred for 1 h, and then (2R,4R)-1-(tert-butoxycarbonyl)-4-phenoxypyrrolidine-2-carboxylic acid (470 mg, 1.53 mmol, 1 eq) was added and stirred for 10 min. Then, isocyanocyclohexane (166.95 mg, 1.53 mmol, 190.14 uL, 1 eq) in MeOH (1 mL) was added and the resulting mixture was stirred at 25° C. for 1 h 50 min. The reaction mixture was concentrated under reduced pressure to remove solvent. The residue was purified by prep-HPLC to give (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (320 mg, 464.24 umol, 30.36% yield, 95% purity) and (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (330 mg, 478.75 umol, 31.31% yield, 95% purity) as a solid. MS (ESI) m/z 655.2 $[M+H]^+$ Prep-HPLC condition: (column: Kromasil C18 (250*50 mm*10 um); mobile phase: [water (10 mM NH4HCO3)-ACN]; B %: 70%-90%, 10 min).

Step 2: (2R,4R)—N-(4-(tert-butyl)phenyl)-N-(2-(cyclohexylamino)-2-oxo-1-(pyridin-3-yl)ethyl)-4-phenoxypyrrolidine-2-carboxamide Isomer 1: To a solution of (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (320 mg, 488.67 umol, 1 eq) in DCM (5 mL), was added TFA (1.54 g, 13.51 mmol, 1 mL, 27.64 eq). The mixture was stirred at 25° C. for 1 hr. Then the reaction mixture was concentrated under reduced pressure to remove solvent to give (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (270 mg, crude) as a solid. MS (ESI) m/z 555.3 $[M+H]^+$.

Isomer 2: To a solution of (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (330 mg, 503.94 umol, 1 eq) in DCM (5 mL), was added TFA (1.54 g, 13.51 mmol, 1 mL, 26.80 eq). The mixture was stirred at 25° C. for 1 hr. The reaction mixture was concentrated under reduced pressure to remove solvent to give (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (270 mg, crude) as a solid. MS (ESI) m/z 555.3 $[M+H]^+$.

Step 3: (2R,4R)—N-(4-(tert-butyl)phenyl)-1-cyano-N-(2-(cyclohexylamino)-2-oxo-1-(pyridin-3-yl)ethyl)-4-phenoxypyrrolidine-2-carboxamide Compound 307 Isomer 1: To a solution of (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (250 mg, 450.68 umol, 1 eq) in DMF (5 mL) was added $K_2CO_3$ (186.86 mg, 1.35 mmol, 3 eq), and then BrCN (57.28 mg, 540.81 umol, 39.78 uL, 1.2 eq) was added at −10° C. The mixture was stirred at −10° C. for 2 h. The reaction mixture was quenched by addition water (20 mL) at 25° C., and then extracted with EtOAc (20 mL*3). The combined organic layers were washed with brine (20 mL*2), dried over $Na_2SO_4$, filtered and concentrated under reduced pressure to give a residue. The residue was purified by prep-HPLC to give (2R,4R)—N-(4-(tert-butyl)phenyl)-1-cyano-N-(2-(cyclohexylamino)-2-oxo-1-(pyridin-3-yl)ethyl)-4-phenoxypyrrolidine-2-carboxamide (110 mg, 189.74 umol, 42.10% yield, 100% purity) as a solid MS (ESI) m/z 580.2 $[M+H]^+$ Prep-HPLC condition: (column: Phenomenex Gemini-NX C18 75*30 mm*3 um; mobile phase: [water (0.05% NH3H2O+10 mM NH4HCO3)-ACN]; B %: 45%-40%, 8 min). $^1$H NMR (Compound 307 Isomer 1). $^1$H NMR (400 MHz, METHANOL-$d_4$) δ ppm 8.38-8.23 (m, 2H), 7.67 (s, 1H), 7.54 (d, J=8.0 Hz, 1H), 7.47-7.13 (m, 5H), 7.01-6.86 (m, 3H), 6.69 (s, 1H), 6.18 (s, 1H), 4.85 (s, 1H), 4.32 (d, J=6.1, 8.6 Hz, 1H), 3.83 (d, J=6.0, 9.7 Hz, 1H), 3.75-3.62 (m, 2H), 2.37-2.27 (m, 1H), 2.26-2.17 (m, 1H), 1.96 (d, J=11.9 Hz, 1H), 1.82-1.59 (m, 4H), 1.44-1.27 (m, 3H), 1.22 (s, 9H), 1.19-1.01 (m, 2H).

Compound 307 Isomer 2: To a solution of (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (250 mg, 450.68 umol, 1 eq) in DMF (5 mL), was added $K_2CO_3$ (186.86 mg, 1.35 mmol, 3 eq), and then BrCN (57.28 mg, 540.81 umol, 39.78 uL, 1.2 eq) was added at −10° C. The mixture was stirred at −10° C. for 2 hr. The reaction mixture was quenched by addition water (20 mL) at 25° C., and then extracted with EtOAc (20 mL*3). The combined organic layers were washed with brine (20 mL*2), dried over $Na_2SO_4$, filtered and concentrated under reduced pressure to give a residue. The residue was purified by prep-HPLC to give (2R,4R)—N-(4-(tert-butyl)phenyl)-1-cyano-N-(2-(cyclohexylamino)-2-oxo-1-(pyridin-3-yl)ethyl)-4-phenoxypyrrolidine-2-carboxamide (105 mg, 181.12 umol, 40.19% yield, 100% purity) as a solid. MS (ESI) m/z 580.2 $[M+H]^+$ Prep-HPLC condition: (column: Phenomenex Gemini-NX C18 75*30 mm*3 um; mobile phase: [water (0.05% NH3H2O+10 mM NH4HCO3)-ACN]; B %: 40%-65%, 8 min). $^1$H NMR (Compound 307 Isomer 2). $^1$H NMR (400 MHz, METHANOL-$d_4$) δ ppm 8.30 (d, J=1.2, 4.8 Hz, 1H), 8.20 (d, J=1.8 Hz, 1H), 7.68 (s, 1H), 7.55-7.30 (m, 4H), 7.17-6.87 (m, 5H), 5.96 (s, 2H), 4.94-4.90 (m, 1H), 4.43 (d, J=3.6, 8.8 Hz, 1H), 3.86-3.80 (m, 1H), 3.76-3.71 (m, 1H), 3.70-3.61 (m, 1H), 2.21-2.14 (m, 1H), 2.14-2.05 (m, 1H), 1.95 (d, J=11.2 Hz, 1H), 1.76 (d, J=13.4 Hz, 1H), 1.72-1.57 (m, 3H), 1.42-1.26 (m, 3H), 1.22 (s, 9H), 1.20-1.12 (m, 1H), 1.09-0.98 (m, 1H).

Example 44: Synthesis of Compound 308

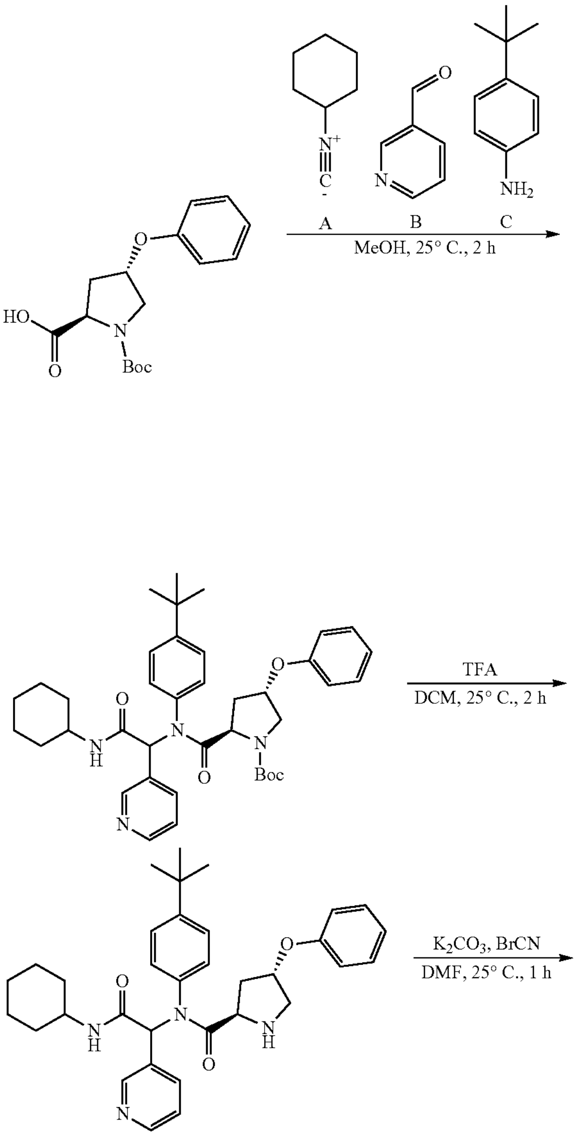

-continued

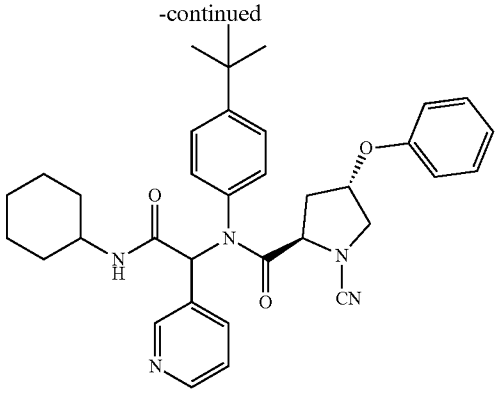

Step 1: tert-butyl (2R,4S)-2-[(4-tert-butylphenyl)-[2-(cyclohexylamino)-2-oxo-1-(3-pyridyl)ethyl]carbamoyl]-4-phenoxy-pyrrolidine-1-carboxylate To a mixture of 4-tert-butylaniline (242.78 mg, 1.63 mmol, 256.91 uL, 1 eq) in MeOH (5 mL) was added pyridine-3-carbaldehyde (174.25 mg, 1.63 mmol, 152.85 uL, 1 eq). The mixture was stirred at 25° C. for 30 min, and then (2R,4S)-1-tert-butoxycarbonyl-4-phenoxy-pyrrolidine-2-carboxylic acid (500 mg, 1.63 mmol, 1 eq) and isocyanocyclohexane (177.60 mg, 1.63 mmol, 202.28 uL, 1 eq) were added to the mixture. The mixture was stirred at 25° C. for 2 h. Upon completion, the reaction mixture was concentrated under reduced pressure to give a residue. The residue was purified by prep-HPLC (basic condition, column: Phenomenex Gemini-NX C18 75*30 mm*3 um; mobile phase: [water (0.05% NH3$H_2$O+10 mM $NH_4HCO_3$)-ACN]; B %: 55%-85%, 8 min). Compound tert-butyl (2R,4S)-2-[(4-tert-butylphenyl)-[2-(cyclohexylamino)-2-oxo-1-(3-pyridyl)ethyl]carbamoyl]-4-phenoxy-pyrrolidine-1-carboxylate (700 mg, 1.07 mmol, 65.71% yield) was obtained as an oil. MS (ESI) m/z 655.5 $[M+H]^+$.

Step 2: (2R,4S)—N-(4-tert-butylphenyl)-N-[2-(cyclohexylamino)-2-oxo-1-(3-pyridyl)ethyl]-4-phenoxy-pyrrolidine-2-carboxamide Isomer 1: A mixture of tert-butyl (2R,4S)-2-[(4-tert-butylphenyl)-[2-(cyclohexylamino)-2-oxo-1-(3-pyridyl)ethyl]carbamoyl]-4-phenoxy-pyrrolidine-1-carboxylate (350 mg, 534.48 umol, 1 eq) in DCM (3 mL) and TFA (1.5 mL) was stirred at 25° C. for 2 h. Upon completion, the reaction mixture was concentrated under reduced pressure to remove DCM and TFA. The residue was adjust to neutral by $NaHCO_3$ solution and diluted with $H_2O$ (30 mL) and extracted with DCM (20 mL*3). The combined organic layers were washed with brine (20 mL), dried over $Na_2SO_4$, filtered and concentrated under reduced pressure to give (2R,4S)—N-(4-tert-butylphenyl)-N-[2-(cyclohexylamino)-2-oxo-1-(3-pyridyl)ethyl]-4-phenoxy-pyrrolidine-2-carboxamide (280 mg, 504.76 umol, 94.44% yield) as a solid. MS (ESI) m/z 555.4 [M+H]+

Isomer 2: A mixture of tert-butyl (2R,4S)-2-[(4-tert-butylphenyl)-[2-(cyclohexylamino)-2-oxo-1-(3-pyridyl)ethyl]carbamoyl]-4-phenoxy-pyrrolidine-1-carboxylate (320 mg, 488.67 umol, 1 eq) in DCM (3 mL) and TFA (1.5 mL) was stirred at 25° C. for 2 h. Upon completion, the residue was adjust to neutral by $NaHCO_3$ solution and diluted with $H_2O$ (30 mL) and extracted with DCM (20 mL*3). The combined organic layers were washed with brine (20 mL), dried over $Na_2SO_4$, filtered and concentrated under reduced pressure to give (2R,4S)—N-(4-tert-butylphenyl)-N-[2-(cyclohexylamino)-2-oxo-1-(3-pyridyl)ethyl]-4-phenoxy-pyrrolidine-2-carboxamide (233 mg, 420.03 umol, 85.95% yield) as a an oil. MS (ESI) m/z 555.4$[M+H]^+$.

Step 3: (2R,4S)—N-(4-tert-butylphenyl)-1-cyano-N-[2-(cyclohexylamino)-2-oxo-1-(3-pyridyl)ethyl]-4-phenoxy-pyrrolidine-2-carboxamide Compound 308 Isomer 1: To a mixture of (2R,4S)—N-(4-tert-butylphenyl)-N-[2-(cyclohexylamino)-2-oxo-1-(3-pyridyl)ethyl]-4-phenoxy-pyrrolidine-2-carboxamide (230 mg, 414.62 umol, 1 eq) and BrCN (52.70 mg, 497.55 umol, 36.60 uL, 1.2 eq) in DMF (3 mL) was added $K_2CO_3$ (114.61 mg, 829.25 umol, 2 eq) at 0° C. The mixture was stirred at 25° C. for 1 h. Upon completion, the reaction mixture was quenched by addition $H_2O$ (10 mL) at 0° C., and then filtered and concentrated under reduced pressure to give a residue. The residue was purified by prep-HPLC (neutral condition, column: Phenomenex Gemini-NX C18 75*30 mm*3 um; mobile phase: [water (0.05% $NH_3H_2O$+10 mM $NH_4HCO_3$)-ACN]; B %: 50%-70%, 8 min) to give (2R,4S)—N-(4-tert-butylphenyl)-1-cyano-N-[2-(cyclohexylamino)-2-oxo-1-(3-pyridyl)ethyl]-4-phenoxy-pyrrolidine-2-carboxamide (62 mg, 106.95 umol, 25.79% yield) as a solid. MS (ESI) m/z 580.4 $[M+H]^+$ Compound 308 Isomer 1: $^1H$ NMR (400 MHz, METHANOL-$d_4$) δ=8.39-8.27 (m, 2H), 7.70 (br s, 1H), 7.56 (br d, J=7.9 Hz, 1H), 7.46 (br s, 1H), 7.26-7.16 (m, 3H), 7.10 (br s, 1H), 6.93 (t, J=7.4 Hz, 1H), 6.75 (d, J=7.9 Hz, 3H), 6.03 (s, 1H), 4.98 (br s, 1H), 4.29 (t, J=8.0 Hz, 1H), 3.84 (dd, J=3.6, 10.9 Hz, 1H), 3.76-3.63 (m, 1H), 3.57 (d, J=11.0 Hz, 1H), 2.28-2.06 (m, 2H), 1.93 (br d, J=11.9 Hz, 1H), 1.85-1.53 (m, 4H), 1.45-1.27 (m, 3H), 1.22 (s, 9H), 1.19-1.05 (m, 2H).

Compound 308 Isomer 2: To a mixture of (2R,4S)—N-(4-tert-butylphenyl)-N-[2-(cyclohexylamino)-2-oxo-1-(3-pyridyl)ethyl]-4-phenoxy-pyrrolidine-2-carboxamide (300 mg, 540.81 umol, 1 eq) and BrCN (68.74 mg, 648.98 umol, 47.74 uL, 1.2 eq) in DMF (6 mL) was added $K_2CO_3$ (149.49 mg, 1.08 mmol, 2 eq) at 0° C. The mixture was stirred at 25° C. for 1 h. Upon completion, the reaction mixture was quenched by addition $H_2O$ 10 mL at 0° C., and then filtered and concentrated under reduced pressure to give a residue. The residue was purified by prep-HPLC (basic condition, column: Phenomenex Gemini-NX C18 75*30 mm*3 um; mobile phase: [water (0.05% $NH_3H_2O$+10 mM $NH_4HCO_3$)-ACN]; B %: 50%-70%, 8 min) to give (2R,4S)—N-(4-tert-butylphenyl)-1-cyano-N-[2-(cyclohexylamino)-2-oxo-1-(3-pyridyl)ethyl]-4-phenoxy-pyrrolidine-2-carboxamide (56 mg, 96.60 umol, 17.86% yield) as a solid. MS (ESI) m/z 580.4 $[M+H]^+$ Compound 308 Isomer 2: $^1H$ NMR (400 MHz, METHANOL-$d_4$) δ=8.34-8.25 (m, 2H), 7.62 (br s, 1H), 7.53 (br d, J=7.9 Hz, 1H), 7.31 (br d, J=6.0 Hz, 1H), 7.26-7.11 (m, 4H), 6.93 (t, J=7.4 Hz, 1H), 6.75 (d, J=7.9 Hz, 2H), 6.67 (br d, J=5.5 Hz, 1H), 6.15 (s, 1H), 4.99 (br s, 1H), 4.29 (t, J=7.9 Hz, 1H), 3.88 (dd, J=3.7, 10.6 Hz, 1H), 3.78-3.66 (m, 1H), 3.59 (d, J=10.8 Hz, 1H), 2.28 (ddd, J=4.4, 8.8, 13.7 Hz, 1H), 2.12 (br dd, J=7.3, 13.7 Hz, 1H), 1.93 (br d, J=12.1 Hz, 1H), 1.84-1.56 (m, 4H), 1.44-1.21 (m, 4H), 1.19 (s, 9H), 1.11-0.99 (m, 1H).

Example 45: Synthesis of Compound 374

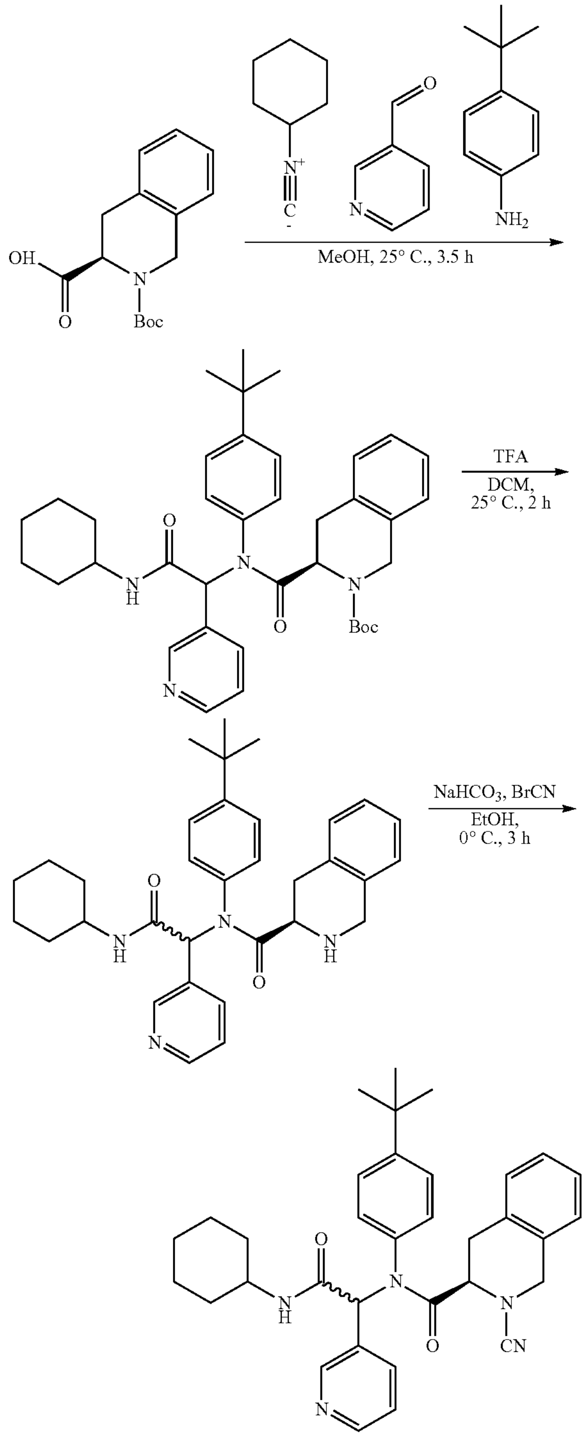

Step 1: tert-butyl (3R)-3-[(4-tert-butylphenyl)-[2-(cyclohexylamino)-2-oxo-1-(3-pyridyl)ethyl]carbamoyl]-3,4-dihydro-1H-isoquinoline-2-carboxylate To a mixture of 4-tert-butylaniline (269.07 mg, 1.80 mmol, 284.73 uL, 1 eq) in MeOH (5 mL) was added pyridine-3-carbaldehyde (193.12 mg, 1.80 mmol, 169.40 uL, 1 eq). The mixture was stirred at 25° C. for 30 min, TLC showed the reaction was completed. Then (3R)-2-tert-butoxycarbonyl-3,4-dihydro-1H-isoquinoline-3-carboxylic acid (500 mg, 1.80 mmol, 1 eq) and isocyanocyclohexane (196.83 mg, 1.80 mmol, 224.18 uL, 1 eq) was added to the mixture and the mixture was stirred at 25° C. for 3 h. Upon completion, the reaction mixture was filtered and concentrated under reduced pressure to give tert-butyl (3R)-3-[(4-tert-butylphenyl)-[2-(cyclohexylamino)-2-oxo-1-(3-pyridyl)ethyl]carbamoyl]-3,4-dihydro-1H-isoquinoline-2-carboxylate (1 g, 1.60 mmol, 88.77% yield) as a oil. MS (ESI) m/z 625.5 $[M+H]^+$.

Step 2: (3R)—N-(4-tert-butylphenyl)-N-[2-(cyclohexylamino)-2-oxo-1-(3-pyridyl)ethyl]-1,2,3,4-tetrahydroisoquinoline-3-carboxamide A mixture of tert-butyl (3R)-3-[(4-tert-butylphenyl)-[2-(cyclohexylamino)-2-oxo-1-(3-pyridyl)ethyl]carbamoyl]-3,4-dihydro-1H-isoquinoline-2-carboxylate (1 g, 1.60 mmol, 1 eq) in DCM (14 mL) and TFA (7 mL) was stirred at 25° C. for 2 h. Upon completion, the reaction mixture was concentrated under reduced pressure to remove DCM and TFA. The residue was adjusted to neutral pH with $NaHCO_3$ solution and diluted with $H_2O$ (30 mL) and extracted with DCM (20 mL*3). The combined organic layers were washed with solvent brine (20 mL), dried over $Na_2SO_4$, filtered and concentrated under reduced pressure to give a residue. The residue was purified by prep-HPLC (basic condition, column: Phenomenex Gemini-NX C18 75*30 mm*3 um; mobile phase: [water (0.05% $NH_3H_2O$+10 mM $NH_4HCO_3$)-ACN]; B %: 45%-65%, 8 min) to give (3R)—N-(4-tert-butylphenyl)-N-[2-(cyclohexylamino)-2-oxo-1-(3-pyridyl)ethyl]-1,2,3,4-tetrahydroisoquinoline-3-carboxamide (310 mg) as an oil and (3R)—N-(4-tert-butylphenyl)-N-[2-(cyclohexylamino)-2-oxo-1-(3-pyridyl)ethyl]-1,2,3,4-tetrahydroisoquinoline-3-carboxamide (390 mg) as an oil. MS (ESI) m/z 525.2 $[M+H]^+$. Isomer 1: $^1H$ NMR (400 MHz, METHANOL-$d_4$) δ=8.45-8.26 (m, 2H), 7.57 (td, J=1.8, 8.0 Hz, 2H), 7.22 (dd, J=4.6, 7.7 Hz, 3H), 7.04 (br s, 4H), 6.88-6.42 (m, 1H), 6.08 (s, 1H), 3.99 (d, J=16.4 Hz, 1H), 3.82-3.65 (m, 2H), 3.50 (dd, J=4.4, 10.6 Hz, 1H), 2.98-2.82 (m, 1H), 2.71 (dd, J=4.3, 16.1 Hz, 1H), 1.89 (br d, J=12.5 Hz, 1H), 1.78-1.52 (m, 4H), 1.51-1.27 (m, 3H), 1.17-1.04 (m, 2H); Isomer 2: $^1H$ NMR (400 MHz, METHANOL-$d_4$) δ=8.32-8.26 (m, 2H), 7.76 (br s, 1H), 7.53 (td, J=1.8, 8.0 Hz, 1H), 7.37 (br s, 1H), 7.24-7.17 (m, 1H), 7.14-7.03 (m, 3H), 7.01-6.91 (m, 2H), 6.85 (s, 1H), 4.00 (d, J=16.8 Hz, 1H), 3.80-3.63 (m, 2H), 3.47 (dd, J=4.4, 11.0 Hz, 1H), 3.04-2.84 (m, 1H), 2.81-2.71 (m, 1H), 1.94 (br d, J=12.6 Hz, 11H), 1.85-1.59 (m, 4H), 1.44-1.36 (m, 1H), 1.34-1.22 (m, 1H), 1.33-1.21 (m, 1H), 1.18 (s, 9H), 1.16-1.00 (m, 2H).

Step 3: (3R)—N-(4-tert-butylphenyl)-2-cyano-N-[2-(cyclohexylamino)-2-oxo-1-(3-pyridyl)ethyl]-3,4-dihydro-1H-isoquinoline-3-carboxamide Compound 374 Isomer 1: To a mixture of (3R)—N-(4-tert-butylphenyl)-N-[2-(cyclohexylamino)-2-oxo-1-(3-pyridyl)ethyl]-1,2,3,4-tetrahydroisoquinoline-3-carboxamide (80 mg, 152.47 umol, 1 eq) and BrCN (32.30 mg, 304.94 umol, 22.43 uL, 2 eq) in EtOH (2 mL) was added $NaHCO_3$ (38.43 mg, 457.41 umol, 17.79 uL, 3 eq) at 0° C. The mixture was stirred at 0° C. for 3 h. Upon completion, the reaction mixture was quenched by addition $H_2O$ (10 mL) at 0° C. The mixture was filtered and concentrated under reduced pressure to give residue. The residue was purified by prep-HPLC (neutral condition, column: Waters Xbridge BEH C18 100*30 mm*10 um; mobile phase: [water (10 mM $NH_4HCO_3$)-ACN]; B %: 50%-80%, 10 min) to give (3R)—N-(4-tert-butylphenyl)-2-cyano-N-[2-(cyclohexylamino)-2-oxo-1-(3-pyridyl)ethyl]-3,4-dihydro-1H-isoquinoline-3-carboxamide (31 mg, 56.39 umol, 36.99% yield) as a solid. MS (ESI) m/z 550.4[M+H]$^+$. Compound 374 Isomer 1: $^1$H NMR (400 MHz, METHANOL-$d_4$) δ=8.34-8.24 (m, 2H), 8.15-7.65 (m, 1H), 7.55 (br d, J=8.0 Hz, 1H), 7.42 (br s, 1H), 7.34-7.03 (m, 6H), 6.70 (br s, 1H), 6.14 (s, 1H), 4.55 (s, 1H), 4.24 (d, J=15.3 Hz, 1H), 4.06 (dd, J=5.6, 7.9 Hz, 1H), 3.80-3.56 (m, 1H), 3.20-3.06 (m, 1H), 3.02-2.90 (m, 1H), 1.87 (br d, J=11.2 Hz, 1H), 1.79-1.56 (m, 4H), 1.44-1.26 (m, 3H), 1.22 (s, 9H), 1.18-0.99 (m, 2H).

Compound 374 Isomer 2: To a mixture of (3R)—N-(4-tert-butylphenyl)-N-[2-(cyclohexylamino)-2-oxo-1-(3-pyridyl)ethyl]-1,2,3,4-tetrahydroisoquinoline-3-carboxamide (100 mg, 190.59 umol, 1 eq) and BrCN (40.37 mg, 381.17 umol, 28.04 uL, 2 eq) in EtOH (2 mL) was added $NaHCO_3$ (48.03 mg, 571.76 umol, 22.24 uL, 3 eq) at 0° C. The mixture was stirred at 0° C. for 3 h. Upon completion, the reaction mixture was quenched by addition $H_2O$ (10 mL) at 0° C., and then filtered and concentrated under reduced pressure to give a residue. The residue was purified by prep-HPLC (neutral condition, column: Waters Xbridge BEH C18 100*30 mm*10 um; mobile phase: [water (10 mM $NH_4HCO_3$)-ACN]; B %: 50%-80%, 10 min) to give (3R)—N-(4-tert-butylphenyl)-2-cyano-N-[2-(cyclohexylamino)-2-oxo-1-(3-pyridyl)ethyl]-3,4-dihydro-1H-isoquinoline-3-carboxamide (38 mg, 69.13 umol, 36.27% yield) as a solid. MS (ESI) m/z 550.4 [M+H]$^+$. Compound 374 Isomer 2: $^1$H NMR (400 MHz, METHANOL-$d_4$) 8=8.35-8.26 (m, 2H), 7.77 (br s, 1H), 7.55 (br d, J=7.9 Hz, 1H), 7.42 (br s, 1H), 7.30-7.13 (m, 5H), 7.09 (br d, J=6.1 Hz, 1H), 6.70 (br s, 1H), 6.14 (s, 1H), 4.55 (s, 1H), 4.24 (d, J=15.2 Hz, 1H), 4.06 (dd, J=5.6, 7.8 Hz, 1H), 3.78-3.60 (m, 1H), 3.14 (br dd, J=8.0, 16.2 Hz, 1H), 2.97 (br dd, J=5.5, 16.1 Hz, 1H), 1.87 (br d, J=12.0 Hz, 1H), 1.78-1.58 (m, 4H), 1.43-1.25 (m, 3H), 1.22 (s, 9H), 1.14-1.00 (m, 2H).

Example 46: Synthesis of Compound 910

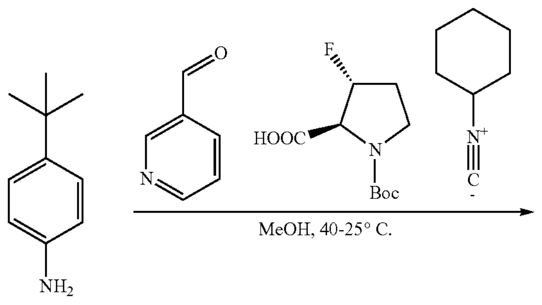

-continued

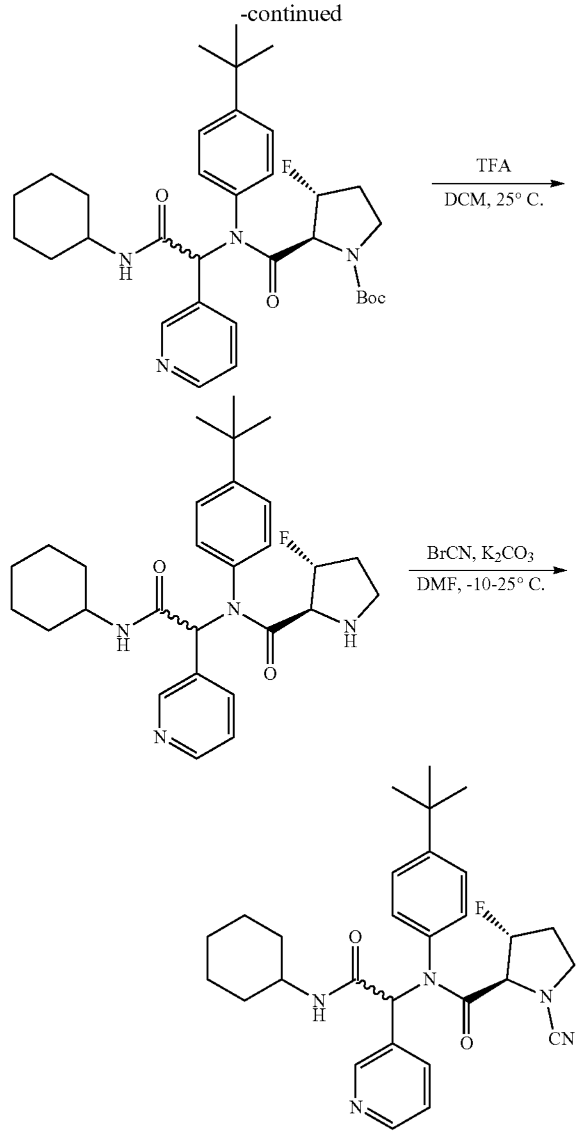

Step 1: (2S,3R)-tert-butyl 2-((4-(tert-butyl)phenyl)(2-(cyclohexylamino)-2-oxo-1-(pyridin-3-yl)ethyl)carbamoyl)-3-fluoropyrrolidine-1-carboxylate A mixture of 4-tert-butylaniline (285 mg, 1.91 mmol, 301.59 uL, 1 eq), pyridine-3-carbaldehyde (306.83 mg, 2.86 mmol, 269.15 uL, 1.5 eq) and MeOH (2.5 mL) was stirred at 25° C. for 0.5 h, and then (2S,3R)-1-tert-butoxycarbonyl-3-fluoro-pyrrolidine-2-carboxylic acid (445.43 mg, 1.91 mmol, 1 eq) was added. The reaction was cooled to −40° C., and the solution was stirred at −40° C. for 15 mi. Then, isocyanocyclohexane (208.49 mg, 1.91 mmol, 237.46 uL, 1 eq) w in MeOH (0.5 mL) was added at −40° C. drop-wise. The reaction mixture was warmed to 25° C. and stirred for another 16 h. Upon completion, the reaction mixture was concentrated under reduced pressure to give a residue. The residue was purified by prep-HPLC (column: Kromasil C18 (250*50 mm*10 um); mobile phase: [water (0.05% $NH_3H_2O$+10 mM $NH_4HCO_3$)-ACN]; B %: %-%, 10 min) to give two products. The tert-butyl (2S,3R)-2-[(4-tert-butylphenyl)-[2-(cyclohexylamino)-2-oxo-1-(3-pyridyl)

ethyl]carbamoyl]-3-fluoro-pyrrolidine-1-carboxylate (310 mg, 507.12 umol, 26.55% yield, 95% purity) was obtained, as a solid and used directly for next step. MS (ESI) m/z 581.3 $[M+H]^+$. The tert-butyl (2S,3R)-2-[(4-tert-butylphenyl)-[2-(cyclohexylamino)-2-oxo-1-(3-pyridyl)ethyl]carbamoyl]-3-fluoro-pyrrolidine-1-carboxylate (380 mg, 621.63 umol, 32.55% yield, 95% purity) was obtained, as a solid and used directly for next step. MS (ESI) m/z 581.3 $[M+H]^+$.

Step 2: (2S,3R)—N-(4-tert-butylphenyl)-N-[2-(cyclohexylamino)-2-oxo-1-(3-pyridyl)ethyl]-3-fluoro-pyrrolidine-2-carboxamide A mixture of tert-butyl (2S,3R)-2-[(4-tert-butylphenyl)-[2-(cyclohexylamino)-2-oxo-1-(3-pyridyl)ethyl]carbamoyl]-3-fluoro-pyrrolidine-1-carboxylate (290 mg, 499.37 umol, 1 eq), TFA (1.71 g, 14.98 mmol, 1.11 mL, 30 eq) and DCM (4 mL) was stirred at 25° C. for 16 h. Upon completion, the mixture was quenched by $NaHCO_3$ (50 mL) and extracted with DCM (30 mL*3). The combined organic layers were washed with brine (50 mL), dried over $Na_2SO_4$, filtered and concentrated under reduced pressure to give a residue (2S,3R)—N-(4-tert-butylphenyl)-N-[2-(cyclohexylamino)-2-oxo-1-(3-pyridyl)ethyl]-3-fluoro-pyrrolidine-2-carboxamide (215 mg, crude), as a solid. MS (ESI) m/z 481.3 $[M+H]^+$.

To a solution of tert-butyl tert-butyl (2S,3R)-2-[(4-tert-butylphenyl)-[2-(cyclohexylamino)-2-oxo-1-(3-pyridyl)ethyl]carbamoyl]-3-fluoro-pyrrolidine-1-carboxylate (360 mg, 619.91 umol, 1 eq) in DCM (4 mL) was added TFA (2.12 g, 18.60 mmol, 1.38 mL, 30 eq) and the mixture was stirred at 25° C. for 16 h. Upon completion, the mixture was quenched by $NaHCO_3$ (50 mL) and then extracted with EtOAc (30 mL*3). The combined organic layers were washed with brine (50 mL), dried over $Na_2SO_4$, filtered and concentrated under reduced pressure to give (2S,3R)—N-(4-tert-butylphenyl)-N-[2-(cyclohexylamino)-2-oxo-1-(3-pyridyl)ethyl]-3-fluoro-pyrrolidine-2-carboxamide (265 mg, crude), as a solid. MS (ESI) m/z 481.3 $[M+H]^+$.

Step3: (2S,3R)—N-(4-tert-butylphenyl)-1-cyano-N-[2-(cyclohexylamino)-2-oxo-1-(3-pyridyl)ethyl]-3-fluoro-pyrrolidine-2-carboxamide To a solution of (2S,3R)—N-(4-tert-butylphenyl)-N-[2-(cyclohexylamino)-2-oxo-1-(3-pyridyl)ethyl]-3-fluoro-pyrrolidine-2-carboxamide (200 mg, 416.13 umol, 1 eq) in DMF (1 mL) was added $K_2CO_3$ (172.54 mg, 1.25 mmol, 3 eq). The mixture was cooled at −10° C. and BrCN (88.15 mg, 832.27 umol, 61.22 uL, 2 eq) in DMF (1 mL) was added. Finally, the mixture solution was stirred for 1 h at −10° C. and warmed to 25° C. gradually. Upon completion, the mixture was quenched by $H_2O$ (20 mL) and then extracted with DCM (20 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 45%-75%, 10 min]; B %: 30%-60%, 10 min) to get the product (2S,3R)—N-(4-tert-butylphenyl)-1-cyano-N-[2-(cyclohexylamino)-2-oxo-1-(3-pyridyl)ethyl]-3-fluoro-pyrrolidine-2-carboxamide (18 mg, 35.60 umol, 8.55% yield, 100% purity), as a solid. MS (ESI) m/z 506.3 $[M+H]^+$. $^1H$ NMR (400 MHz, METHANOL-$d_4$) δ=8.33-8.26 (m, 2H), 7.82-7.62 (m, 1H), 7.57-7.51 (m, 1H), 7.49-7.31 (m, 1H), 7.24-7.15 (m, 2H), 6.82-6.61 (m, 1H), 6.13 (s, 1H), 5.47-5.17 (m, 1H), 4.37-4.20 (m, 1H), 3.89-3.49 (m, 3H), 2.45-2.09 (m, 2H), 1.98-1.83 (m, 11H), 1.83-1.72 (m, 2H), 1.72-1.55 (m, 2H), 1.46-0.96 (m, 15H).

To a solution of (2S,3R)—N-(4-tert-butylphenyl)-N-[2-(cyclohexylamino)-2-oxo-1-(3-pyridyl)ethyl]-3-fluoro-pyrrolidine-2-carboxamide (250 mg, 520.17 umol, 1 eq) in DMF (1 mL) was added $K_2CO_3$ (215.67 mg, 1.56 mmol, 3 eq). Then the mixture was cooled to −10° C. and BrCN (110.19 mg, 1.04 mmol, 76.52 uL, 2 eq) in DMF (1 mL) was added. Finally, the mixture solution was stirred for 1 h at −10° C. and warmed to 25° C. gradually. Upon completion, the mixture was quenched by $H_2O$ (20 mL) and then extracted with DCM (20 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 45%-75%, 9 min) to get the product (2S,3R)—N-(4-tert-butylphenyl)-1-cyano-N-[2-(cyclohexylamino)-2-oxo-1-(3-pyridyl)ethyl]-3-fluoro-pyrrolidine-2-carboxamide (31 mg, 61.31 umol, 11.79% yield, 100% purity), as a solid. MS (ESI) m/z 506.3 $[M+H]^+$. $^1H$ NMR (400 MHz, METHANOL-$d_4$) δ=8.42-8.25 (m, 2H), 7.90-7.50 (m, 2H), 7.50-7.31 (m, 1H), 7.30-7.06 (m, 2H), 6.98-6.38 (m, 1H), 5.98 (s, 1H), 5.38-5.15 (m, 1H), 4.25 (d, 1H), 3.87-3.45 (m, 3H), 2.48-2.05 (m, 2H), 2.01-1.85 (m, 1H), 1.83-1.49 (m, 4H), 1.46-0.93 (m, 15H).

Example 47: Synthesis of Compound 870

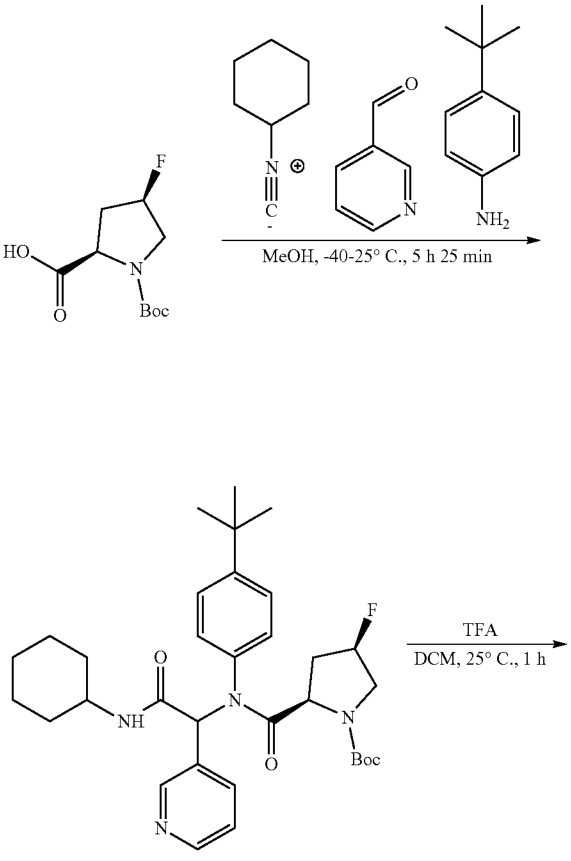

-continued

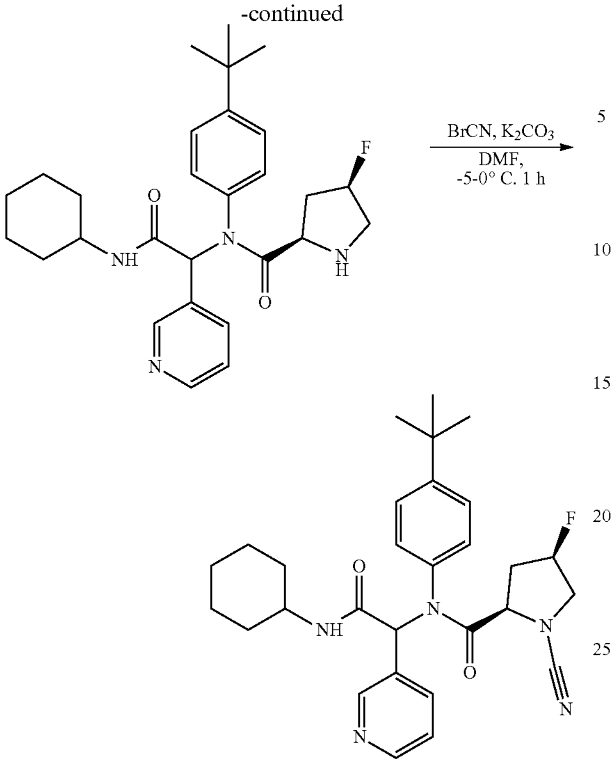

Step 1: tert-butyl (2R,4R)-2-[(4-tert-butylphenyl)-[2-(cyclohexylamino)-2-oxo-1-(3-pyridyl)ethyl]carbamoyl]-4-fluoro-pyrrolidine-1-carboxylate A mixture of pyridine-3-carbaldehyde (257.17 mg, 2.40 mmol, 225.59 uL, 1.4 eq) and 4-tert-butylaniline (255.93 mg, 1.72 mmol, 270.83 uL, 1 eq) in MeOH (5 mL) was heated to 25° C. and stirred for 0.5 h. Then, (2R,4R)-1-tert-butoxycarbonyl-4-fluoro-pyrrolidine-2-carboxylic acid (400 mg, 1.72 mmol, 1 eq) was added at −40° C. over 15 min, and then was added isocyanocyclohexane (187.22 mg, 1.72 mmol, 213.24 uL, 1 eq) in MeOH (1 mL). The mixture was stirred at 25° C. for 5 h. Upon completion, the reaction mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 55%-75%, 10 min) to get a product tert-butyl (2R,4R)-2-[(4-tert-butylphenyl)-[2-(cyclohexylamino)-2-oxo-1-(3-pyridyl)ethyl]carbamoyl]-4-fluoro-pyrrolidine-1-carboxylate (420 mg, 687.06 umol, 40.06% yield, 95% purity) as an oil. MS (ESI) m/z 581.4 $[M+H]^+$. To get tert-butyl (2R,4R)-2-[(4-tert-butylphenyl)-[2-(cyclohexylamino)-2-oxo-1-(3-pyridyl)ethyl]carbamoyl]-4-fluoro-pyrrolidine-1-carboxylate (520 mg, 850.65 umol, 49.60% yield, 95% purity) as an oil. MS (ESI) m/z 581.4 $[M+H]^+$.

Step 2: (2R,4R)—N-(4-tert-butylphenyl)-N-[2-(cyclohexylamino)-2-oxo-1-(3-pyridyl)ethyl]-4-fluoro-pyrrolidine-2-carboxamide A mixture of tert-butyl (2R,4R)-2-[(4-tert-butylphenyl)-[2-(cyclohexylamino)-2-oxo-1-(3-pyridyl)ethyl]carbamoyl]-4-fluoro-pyrrolidine-1-carboxylate (400 mg, 688.79 umol, 1 eq) in DCM (2 mL) was added TFA (1 mL) and stirred at 25° C. for 1 h. Upon completion, the reaction mixture was diluted with $Na_2CO_3$ (10 mL) and extracted with DCM (10 mL*3). The combined organic layers were washed with brine, dried over $Na_2SO_4$, filtered and concentrated under reduced pressure to give a residue to get the product (2R,4R)—N-(4-tert-butylphenyl)-N-[2-(cyclohexylamino)-2-oxo-1-(3-pyridyl)ethyl]-4-fluoro-pyrrolidine-2-carboxamide (350 mg, crude) as an oil. MS (ESI) m/z 481.3 $[M+H]^+$.

(2R,4R)—N-(4-tert-butylphenyl)-N-[2-(cyclohexylamino)-2-oxo-1-(3-pyridyl)ethyl]-4-fluoro-pyrrolidine-2-carboxamide A mixture of tert-butyl (2R,4R)-2-[(4-tert-butylphenyl)-[2-(cyclohexylamino)-2-oxo-1-(3-pyridyl)ethyl]carbamoyl]-4-fluoro-pyrrolidine-1-carboxylate (500 mg, 860.98 umol, 1 eq) in DCM (3 mL) was added with TFA (1.5 mL) and stirred at 25° C. for 1 h. Upon completion, the reaction mixture was diluted with $Na_2CO_3$ (10 mL) and extracted with DCM (10 mL*3). The combined organic layers were washed with brine, dried over $Na_2SO_4$, filtered and concentrated under reduced pressure to give a residue to get a product (2R,4R)—N-(4-tert-butylphenyl)-N-[2-(cyclohexylamino)-2-oxo-1-(3-pyridyl)ethyl]-4-fluoro-pyrrolidine-2-carboxamide (300 mg, crude). MS (ESI) m/z 481.2 $[M+H]^+$.

Step 3: (2R,4R)—N-(4-tert-butylphenyl)-1-cyano-N-[2-(cyclohexylamino)-2-oxo-1-(3-pyridyl)ethyl]-4-fluoro-pyrrolidine-2-carboxamide A mixture of (2R,4R)—N-(4-tert-butylphenyl)-N-[2-(cyclohexylamino)-2-oxo-1-(3-pyridyl)ethyl]-4-fluoro-pyrrolidine-2-carboxamide (350 mg, 728.23 umol, 1 eq) in DMF (3 mL) was added $K_2CO_3$ (301.95 mg, 2.18 mmol, 3 eq), then the mixture was cooled to −5° C. and BrCN (92.56 mg, 873.88 umol, 64.28 uL, 1.2 eq) in DMF (0.8 mL) was added drop-wise. The resulting mixture was stirred at 0° C. for 1 h. Upon completion, the reaction mixture was diluted with $H_2O$ (10 mL) and extracted with EtOAc (3 mL*3). The combined organic layers were washed with brine, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 35%-65%, 8 min) to get the product (2R,4R)—N-(4-tert-butylphenyl)-1-cyano-N-[2-(cyclohexylamino)-2-oxo-1-(3-pyridyl)ethyl]-4-fluoro-pyrrolidine-2-carboxamide (124.62 mg, 246.47 umol, 33.84% yield, 100% purity) as a solid. MS (ESI) m/z 506.3 $[M+H]^+$. $^1H$ NMR (400 MHz, METHANOL-$d_4$) δ=8.33-8.24 (m, 2H), 7.70 (br s, 1H), 7.58-7.51 (m, 1H), 7.36 (br s, 1H), 7.17 (dd, J=4.9, 7.8 Hz, 2H), 6.70 (br s, 1H), 6.19 (s, 1H), 5.25-5.00 (m, 1H), 4.32 (dd, J=3.8, 9.8 Hz, 1H), 3.85-3.61 (m, 3H), 2.45-2.30 (m, 1H), 2.28-2.06 (m, 1H), 2.00-1.88 (m, 1H), 1.82-1.72 (m, 2H), 1.70-1.57 (m, 2H), 1.40-1.08 (m, 14H).

(2R,4R)—N-(4-tert-butylphenyl)-1-cyano-N-[2-(cyclohexylamino)-2-oxo-1-(3-pyridyl)ethyl]-4-fluoro-pyrrolidine-2-carboxamide A mixture of (2R,4R)—N-(4-tert-butylphenyl)-N-[2-(cyclohexylamino)-2-oxo-1-(3-pyridyl)ethyl]-4-fluoro-pyrrolidine-2-carboxamide (300 mg, 624.20 umol, 1 eq) in DMF (3 mL) was added $K_2CO_3$ (258.81 mg, 1.87 mmol, 3 eq), and then the solution was cooled to −5° C. BrCN (79.34 mg, 749.04 umol, 55.10 uL, 1.2 eq) in DMF (0.8 mL) was added drop-wise, and the mixture was stirred at 0° C. for 1 h. Upon completion, the reaction mixture was diluted with $H_2O$ (10 mL) and extracted with EtOAc (3 mL*3). The combined organic layers were washed with brine, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 35%-65%, 8 min) to get the product (2R,4R)—N-(4-tert-butylphenyl)-1-cyano-N-[2-(cyclohexylamino)-2-oxo-1-(3-pyridyl) ethyl]-4-fluoro-pyrrolidine-2-carboxamide (134.62 mg, 266.24 umol, 42.65% yield, 100% purity) as a solid. MS (ESI) m/z 506.3 $[M+H]^+$. $^1H$ NMR (400 MHz, METHANOL-$d_4$) δ=8.38-8.27 (m, 2H), 7.71 (br s, 1H), 7.54 (td, J=1.8, 7.9 Hz, 1H), 7.49-7.30 (m, 1H), 7.19 (dd, J=4.9, 7.9 Hz, 2H), 6.84-6.27 (m, 1H), 6.01 (s, 1H), 5.22-5.03 (m, 1H), 4.38 (dd, J=3.0, 9.8 Hz, 1H), 3.86-3.61 (m, 3H), 2.33-2.03 (m, 2H), 1.97-1.88 (m, 1H), 1.79-1.57 (m, 4H), 1.39-1.03 (m, 14H).

Example 48: Synthesis of Compound 876

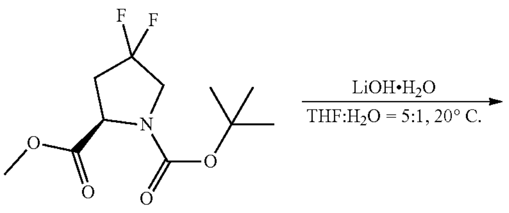

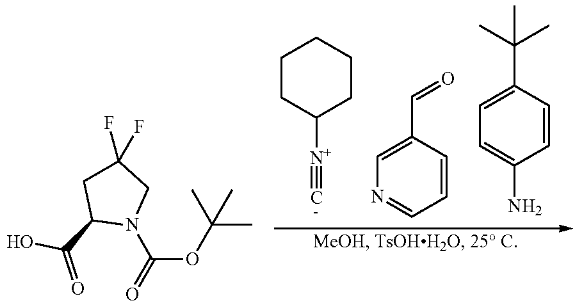

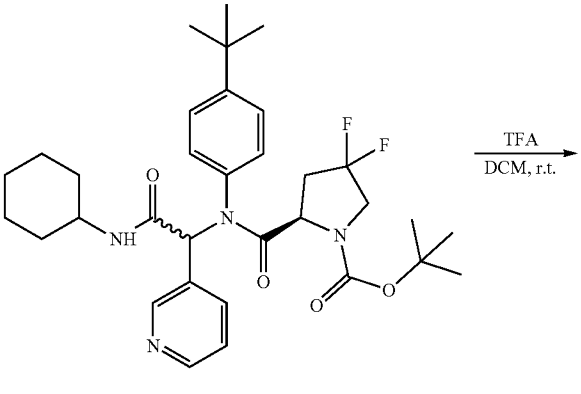

-continued

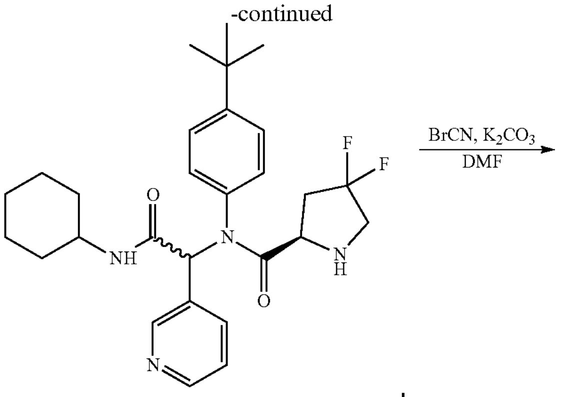

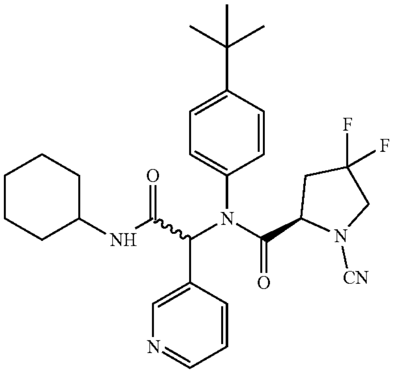

Step 1: (R)-1-(tert-butoxycarbonyl)-4,4-difluoropyrrolidine-2-carboxylic acid

A mixture of (R)-1-tert-butyl 2-methyl 4,4-difluoropyrrolidine-1,2-dicarboxylate (900 mg, 3.39 mmol, 1 eq) and LiOH·$H_2O$ (284.76 mg, 6.79 mmol, 2 eq) in THF (10 mL) and $H_2O$ (2 mL) was stirred at 20° C. for 1 h under $N_2$ atmosphere. Upon completion, the reaction mixture was concentrated under reduced pressure to give a residue. The reaction mixture was added (DCM:MeOH=10:1) 10 mL and stirred at 20° C. for 15 min, filtered and concentrated under reduced pressure to give (R)-1-(tert-butoxycarbonyl)-4,4-difluoropyrrolidine-2-carboxylic acid (750 mg, crude) as a solid. MS (ESI) m/z 195.9 $[M-55]^+$.

Step 2: (2R)-tert-butyl 2-((4-(tert-butyl)phenyl)(2-(cyclohexylamino)-2-oxo-1-(pyridin-3-yl)ethyl)carbamoyl)-4,4-difluoropyrrolidine-1-carboxylate A solution of pyridine-3-carbaldehyde (127.90 mg, 1.19 mmol, 112.20 uL, 1 eq), 4-tert-butylaniline (178.20 mg, 1.19 mmol, 188.58 uL, 1 eq) in MeOH (3 mL) was stirred at 25° C. for 15 min. (R)-1-(tert-butoxycarbonyl)-4,4-difluoropyrrolidine-2-carboxylic acid (300 mg, 1.19 mmol, 1 eq) and TsOH·$H_2O$ (567.86 mg, 2.99 mmol, 2.5 eq) were added to the reaction mixture. A solution of isocyanocyclohexane (117.33 mg, 1.07 mmol, 133.63 uL, 0.9 eq) in MeOH (1 mL) was added in batches (three times), and the resulting mixture was stirred at 25° C. for 4 h. Upon completion, the reaction mixture was concentrated under reduced pressure to give a residue. The residue was purified by prep-HPLC (neutral condition; column: Kromasil C18 (250*50 mm*10 um); mobile phase: [water (10 mM $NH_4HCO_3$)-ACN]; B %: 60%-90%, 10 min) to give the title product (2R)-tert-butyl 2-((4-(tert-butyl)phenyl)(2-(cyclohexylamino)-2-oxo-1-

(pyridin-3-yl)ethyl)carbamoyl)-4,4-difluoropyrrolidine-1-carboxylate (200 mg, 326.03 umol, 27.30% yield, 97.6% purity) as a solid, and (2R)-tert-butyl 2-((4-(tert-butyl)phenyl)(2-(cyclohexylamino)-2-oxo-1-(pyridin-3-yl)ethyl)carbamoyl)-4,4-difluoropyrrolidine-1-carboxylate (200 mg, 327.36 umol, 27.41% yield, 98% purity) as a solid. MS (ESI) m/z 599.3 $[M+H]^+$.

Step 3: (2R)—N-(4-(tert-butyl)phenyl)-N-(2-(cyclohexylamino)-2-oxo-1-(pyridin-3-yl)ethyl)-4,4-difluoropyrrolidine-2-carboxamide Isomer 1: A mixture of (2R)-tert-butyl 2-((4-(tert-butyl)phenyl)(2-(cyclohexylamino)-2-oxo-1-(pyridin-3-yl)ethyl)carbamoyl)-4,4-difluoropyrrolidine-1-carboxylate (190 mg, 317.34 umol, 1 eq) in DCM (4 mL) and TFA (1.5 mL) was stirred at 20° C. for 0.5 h under $N_2$ atmosphere. Upon completion, the reaction mixture was quenched by addition $NaHCO_3$ (20 mL), and extracted with DCM (15 mL*3). The combined organic layers were washed with brine (20 mL), dried over $Na_2SO_4$, filtered and concentrated under reduced pressure to give (2R)—N-(4-(tert-butyl)phenyl)-N-(2-(cyclohexylamino)-2-oxo-1-(pyridin-3-yl)ethyl)-4,4-difluoropyrrolidine-2-carboxamide (120 mg, crude) as an oil. MS (ESI) m/z 499.2 $[M+H]^+$.

Isomer 2: A mixture of (2R)-tert-butyl 2-((4-(tert-butyl)phenyl)(2-(cyclohexylamino)-2-oxo-1-(pyridin-3-yl)ethyl)carbamoyl)-4,4-difluoropyrrolidine-1-carboxylate (190 mg, 317.34 umol, 1 eq) in DCM (4 mL) and TFA (1.5 mL) was stirred at 20° C. for 0.5 h under $N_2$ atmosphere. Upon completion, the reaction mixture was quenched by addition $NaHCO_3$ (20 mL), and extracted with DCM (15 mL*3). The combined organic layers were washed with brine (20 mL), dried over $Na_2SO_4$, filtered and concentrated under reduced pressure to give (2R)—N-(4-(tert-butyl)phenyl)-N-(2-(cyclohexylamino)-2-oxo-1-(pyridin-3-yl)ethyl)-4,4-difluoropyrrolidine-2-carboxamide (125 mg, crude) as a an oil. MS (ESI) m/z 499.2 $[M+H]^+$ Step 4: (2R)—N-(4-(tert-butyl)phenyl)-1-cyano-N-(2-(cyclohexylamino)-2-oxo-1-(pyridin-3-yl)ethyl)-4,4-difluoropyrrolidine-2-carboxamide Compound 876 Isomer 1: To a solution of (2R)—N-(4-(tert-butyl)phenyl)-N-(2-(cyclohexylamino)-2-oxo-1-(pyridin-3-yl)ethyl)-4,4-difluoropyrrolidine-2-carboxamide (100 mg, 200.56 umol, 1 eq) and BrCN (42.49 mg, 401.12 umol, 29.50 uL, 2 eq) in DMF (2 mL) was added a solution of $K_2CO_3$ (83.16 mg, 601.68 umol, 3 eq) in DMF (0.5 mL) drop-wise at −10° C. under $N_2$. The reaction mixture was slowly warmed to 25° C. over 2 h. Upon completion, the reaction mixture was quenched by addition $H_2O$ (30 mL) and extracted with EtOAc (15 mL*3). The combined organic layers were washed with brine (20 mL), dried over $Na_2SO_4$, filtered and concentrated under reduced pressure to give a residue. The residue was purified by prep-HPLC (neutral condition; column: Waters Xbridge BEH C18 100*25 mm*5 um; mobile phase: [water (10 mM $NH_4HCO_3$)-ACN]; B %: 45%-75%, 10 min) to give (2R)—N-(4-(tert-butyl)phenyl)-1-cyano-N-(2-(cyclohexylamino)-2-oxo-1-(pyridin-3-yl)ethyl)-4,4-difluoropyrrolidine-2-carboxamide (44.03 mg, 84.09 umol, 41.93% yield, 100% purity) as a solid. MS (ESI) m/z 524.2 $[M+H]^+$. $^1H$ NMR (400 MHz, MeOD-$d_4$) δ ppm 8.30-8.27 (m, 2H), 7.68 (s, 1H), 7.53-7.51 (m, 1H), 7.42 (s, 1H), 7.19-7.16 (m, 2H), 6.67 (s, 1H), 6.15 (s, 1H), 4.41-4.38 (m, 1H), 3.97-3.90 (m, 1H), 3.81-3.70 (m, 2H), 2.64-2.51 (m, 1H), 2.41-2.31 (m, 1H), 1.95-1.92 (m, 1H), 1.78-1.60 (m, 4H), 1.39-1.03 (m, 14H).

Compound 876 Isomer 2: To a solution of (2R)—N-(4-(tert-butyl)phenyl)-N-(2-(cyclohexylamino)-2-oxo-1-(pyridin-3-yl)ethyl)-4,4-difluoropyrrolidine-2-carboxamide (125 mg, 250.70 umol, 1 eq) and BrCN (53.11 mg, 501.40 umol, 36.88 uL, 2 eq) in DMF (2 mL) was added a solution of $K_2CO_3$ (103.95 mg, 752.10 umol, 3 eq) in DMF (0.5 mL) drop-wise at −10° C. under $N_2$. The reaction mixture was slowly warmed to 25° C. over 2 h. Upon completion, the reaction mixture was quenched by addition $H_2O$ (30 mL) and extracted with EtOAc (15 mL*3). The combined organic layers were washed with brine (20 mL), dried over $Na_2SO_4$, filtered and concentrated under reduced pressure to give a residue. The residue was purified by prep-HPLC (neutral condition; column: Waters Xbridge BEH C18 100*25 mm*5 um; mobile phase: [water (10 mM $NH_4HCO_3$)-ACN]; B %: 45%-75%, 10 min) to give (2R)—N-(4-(tert-butyl)phenyl)-1-cyano-N-(2-(cyclohexylamino)-2-oxo-1-(pyridin-3-yl)ethyl)-4,4-difluoropyrrolidine-2-carboxamide (48.32 mg, 92.28 umol, 36.81% yield, 100% purity) as a solid. MS (ESI) m/z 524.2 $[M+H]^+$. $^1H$ NMR (400 MHz, MeOD-$d_4$) δ ppm 8.34-8.32 (m, 2H), 7.55-7.17 (m, 5H), 6.60 (s, 1H), 6.01 (s, 1H), 4.43-4.40 (m, 11H), 3.97-3.87 (m, 1H), 3.83-3.78 (m, 1H), 3.69-3.66 (m, 1H), 2.57-2.46 (m, 1H), 2.39-2.31 (m, 1H), 1.95-1.92 (m, 1H), 1.78-1.60 (m, 4H), 1.39-1.05 (m, 14H).

Example 49: Synthesis of Compound 885

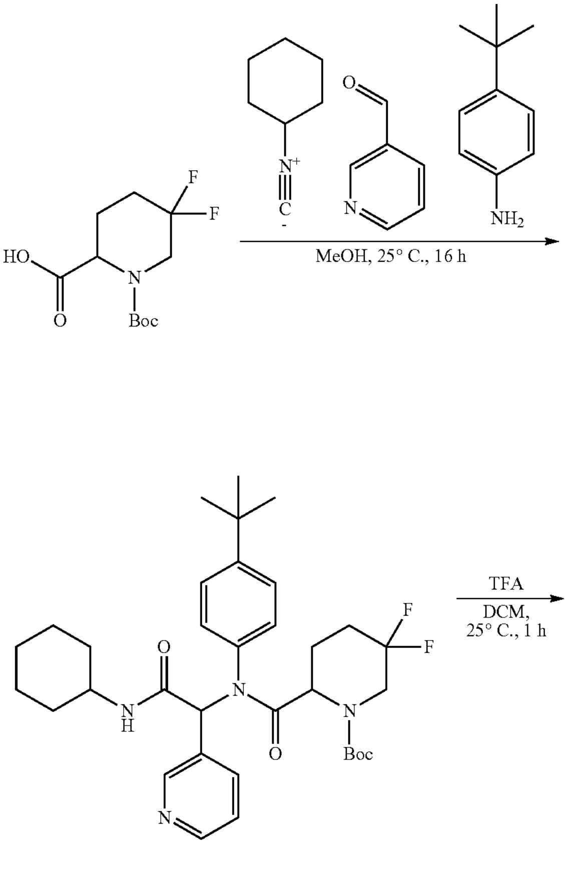

-continued

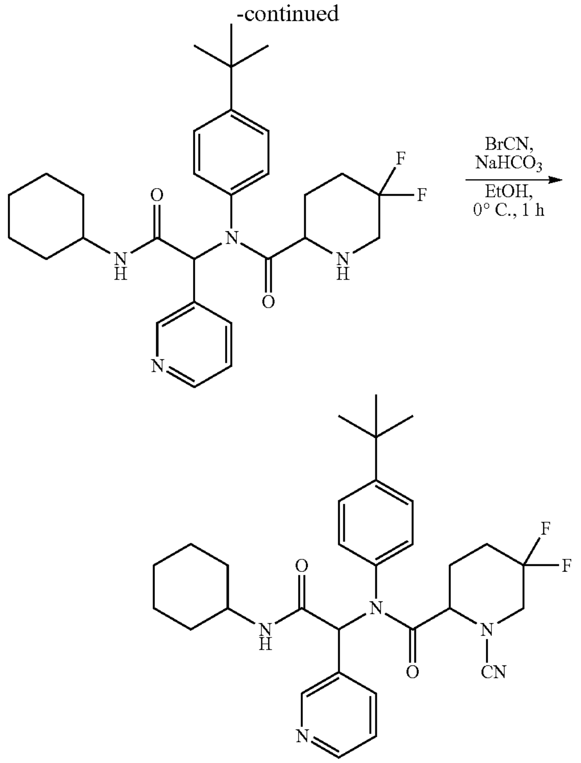

Step 1: tert-butyl2-((4-(tert-butyl)phenyl)(2-(cyclohexylamino)-2-oxo-1-(pyridin-3-yl)ethyl)carbamoyl)-5,5-difluoropiperidine-1-carboxylate A solution of 4-tert-butylaniline (281.30 mg, 1.88 mmol, 297.67 uL, 1 eq) and pyridine-3-carbaldehyde (201.90 mg, 1.88 mmol, 177.11 uL, 1 eq) in MeOH (8 mL) was stirred at 25° C. for 30 min, and then 1-tert-butoxycarbonyl-5,5-difluoro-piperidine-2-carboxylic acid (500 mg, 1.88 mmol, 1 eq) was added to the mixture. A solution of isocyanocyclohexane (185.20 mg, 1.70 mmol, 210.94 uL, 0.9 eq) in MeOH (1 mL) was added in portions. The mixture was stirred at 25° C. for 15.5 h. The reaction mixture was concentrated under reduced pressure and was purified by column ($SiO_2$, petroleum ether:ethyl acetate=1:10 to 4:1) to give a product tert-butyl 2-((4-(tert-butyl)phenyl)(2-(cyclohexylamino)-2-oxo-1-(pyridin-3-yl)ethyl)carbamoyl)-5,5-difluoropiperidine-1-carboxylate (1 g, 1.47 mmol, 77.92% yield, 90% purity) as a an oil. MS (ESI) m/z 613.3 $[M+H]^+$ Step 2: N-(4-(tert-butyl)phenyl)-N-(2-(cyclohexylamino)-2-oxo-1-(pyridin-3-yl)ethyl)-5,5-difluoropiperidine-2-carboxamide A solution of tert-butyl 2-((4-(tert-butyl)phenyl)(2-(cyclohexylamino)-2-oxo-1-(pyridin-3-yl)ethyl)carbamoyl)-5, 5-difluoropiperidine-1-carboxylate (1 g, 1.63 mmol, 1 eq) in TFA (3 mL) and DCM (10 mL) was stirred at 25° C. for 1 h. The reaction mixture was concentrated under reduced pressure and was adjust pH~7 with aq. $NaHCO_3$ (15 mL), then was extracted with DCM (5 mL*3), then was concentrated under reduced pressure and was purified by prep-HPLC to give N-(4-(tert-butyl)phenyl)-N-(2-(cyclohexylamino)-2-oxo-1-(pyridin-3-yl)ethyl)-5,5-difluoropiperidine-2-carboxamide (350 mg, 614.47 umol, 37.65% yield) as a gum and N-(4-(tert-butyl)phenyl)-N-(2-(cyclohexylamino)-2-oxo-1-(pyridin-3-yl)ethyl)-5,5-difluoropiperidine-2-carboxamide (350 mg, 614.47 umol, 37.65% yield, 90% purity) as a gum. prep-HPLC condition: column: Phenomenex luna C18 250*50 mm*10 um; mobile phase: [water (0.1% TFA)-ACN]; B %: 15%-45%, 10 min. $^1H$ NMR (Isomer 1) (400 MHz, MeOD-$d_4$) δ ppm 8.60-8.53 (m, 2H), 7.98-6.96 (m, 6H), 6.04 (s, 1H), 4.05-3.97 (m, 1H), 3.74-3.59 (m, 2H), 3.51 (td, J=12.6, 19.6 Hz, 1H), 2.17 (d, J=13.8 Hz, 2H), 1.99-1.56 (m, 8H), 1.41-1.29 (m, 3H), 1.26 (s, 9H), 1.25-1.22 (m, 2H). $^1H$ NMR (Isomer 2) (400 MHz, MeOD-$d_4$) δ ppm 8.44-8.36 (m, 2H), 7.70 (d, J=8.0 Hz, 2H), 7.51-6.71 (m, 4H), 6.23 (s, 1H), 4.02-3.93 (m, 1H), 3.78-3.61 (m, 2H), 3.57-3.42 (m, 2H), 2.27-2.13 (m, 2H), 1.99-1.58 (m, 8H), 1.41-1.28 (m, 3H), 1.27-1.21 (m, 9H), 1.20-1.13 (m, 1H).

Step 3: N-(4-(tert-butyl)phenyl)-1-cyano-N-(2-(cyclohexylamino)-2-oxo-1-(pyridin-3-yl)ethyl)-5,5-difluoropiperidine-2-carboxamide Compound 885 Isomer 1: To a solution of N-(4-(tert-butyl)phenyl)-N-(2-(cyclohexylamino)-2-oxo-1-(pyridin-3-yl)ethyl)-5, 5-difluoropiperidine-2-carboxamide (200 mg, 390.14 umol, 1 eq) in EtOH (4 mL) was added $NaHCO_3$ (98.32 mg, 1.17 mmol, 45.52 uL, 3 eq) at 0° C., and then was added BrCN (82.65 mg, 780.29 umol, 57.40 uL, 2 eq) at 0° C. The mixture was stirred at 0° C. for 1 h. The mixture was dried by blowing N2, added with water (6 mL) and extracted with DCM (2 mL*3). The resulting mixture was dried with $Na_2SO_4$, filtered and concentrated under reduced pressure and was purified by prep-HPLC to give N-(4-(tert-butyl)phenyl)-1-cyano-N-(2-(cyclohexylamino)-2-oxo-1-(pyridin-3-yl)ethyl)-5,5-difluoropiperidine-2-carboxamide (25 mg, 45.57 umol, 11.68% yield, 98.01% purity) as a solid. MS (ESI) m/z 538.3 $[M+H]^+$ prep-HPLC condition (Compound 885 Isomer 1): column: Waters Xbridge Prep OBD C18 150*40 mm*10 um; mobile phase: [water (10 mM $NH_4HCO_3$)-ACN]; B %: 50%-70%, 8 min. $^1H$ NMR (Compound 885 Isomer 1) (400 MHz, MeOD-$d_4$) δ ppm 8.35-8.27 (m, 2H), 7.78-7.06 (m, 5H), 6.68 (s, 1H), 6.02 (s, 1H), 4.08-4.01 (m, 1H), 3.99-3.85 (m, 11H), 3.70 (tt, J=3.8, 10.8 Hz, 11H), 3.40 (t, J=14.2 Hz, 11H), 2.42-2.22 (m, 11H), 2.13-1.99 (m, 2H), 1.97-1.87 (m, 2H), 1.76 (d, J=10.0 Hz, 2H), 1.71-1.57 (m, 2H), 1.44-1.26 (m, 3H), 1.23 (s, 9H), 1.20-1.01 (m, 2H).

Compound 885 Isomer 2: To a solution of N-(4-(tert-butyl)phenyl)-N-(2-(cyclohexylamino)-2-oxo-1-(pyridin-3-yl)ethyl)-5,5-difluoropiperidine-2-carboxamide (200 mg, 390.14 umol, 1 eq) in EtOH (4 mL) was added $NaHCO_3$ (98.32 mg, 1.17 mmol, 45.52 uL, 3 eq) at 0° C., and then was added BrCN (82.65 mg, 780.29 umol, 57.40 uL, 2 eq) at 0° C. The mixture was stirred at 0° C. for 1 h. The resulting mixture was dried by blowing $N_2$, added with water (6 mL), and extracted with DCM (2 mL*3). The solution was dried with $Na_2SO_4$, filtered and concentrated under reduced pressure and purified by prep-HPLC to give N-(4-(tert-butyl)phenyl)-1-cyano-N-(2-(cyclohexylamino)-2-oxo-1-(pyridin-3-yl)ethyl)-5,5-difluoropiperidine-2-carboxamide (25 mg, 46.50 umol, 11.92% yield, 100% purity) as a solid. MS (ESI) m/z 538.3 $[M+H]^+$ prep-HPLC condition: column: Waters Xbridge Prep OBD C18 150*40 mm*10 um; mobile phase: [water (10 mM $NH_4HCO_3$)-ACN]; B %: 45%-70%, 8 min. $^1H$ NMR (400 MHz, MeOD-$d_4$) δ ppm 8.28 (d, J=2.1 Hz, 2H), 7.71-7.11 (m, 5H), 6.71 (s, 1H), 6.13 (s, 1H), 4.07-3.93 (m, 2H), 3.77-3.66 (m, 1H), 3.44-3.33 (m, 1H), 2.30-1.86 (m, 5H), 1.77 (d, J=9.8 Hz, 2H), 1.72-1.57 (m, 2H), 1.45-1.25 (m, 3H), 1.22 (s, 9H), 1.19-1.01 (m, 2H).

Example 50: Synthesis of Compound 391

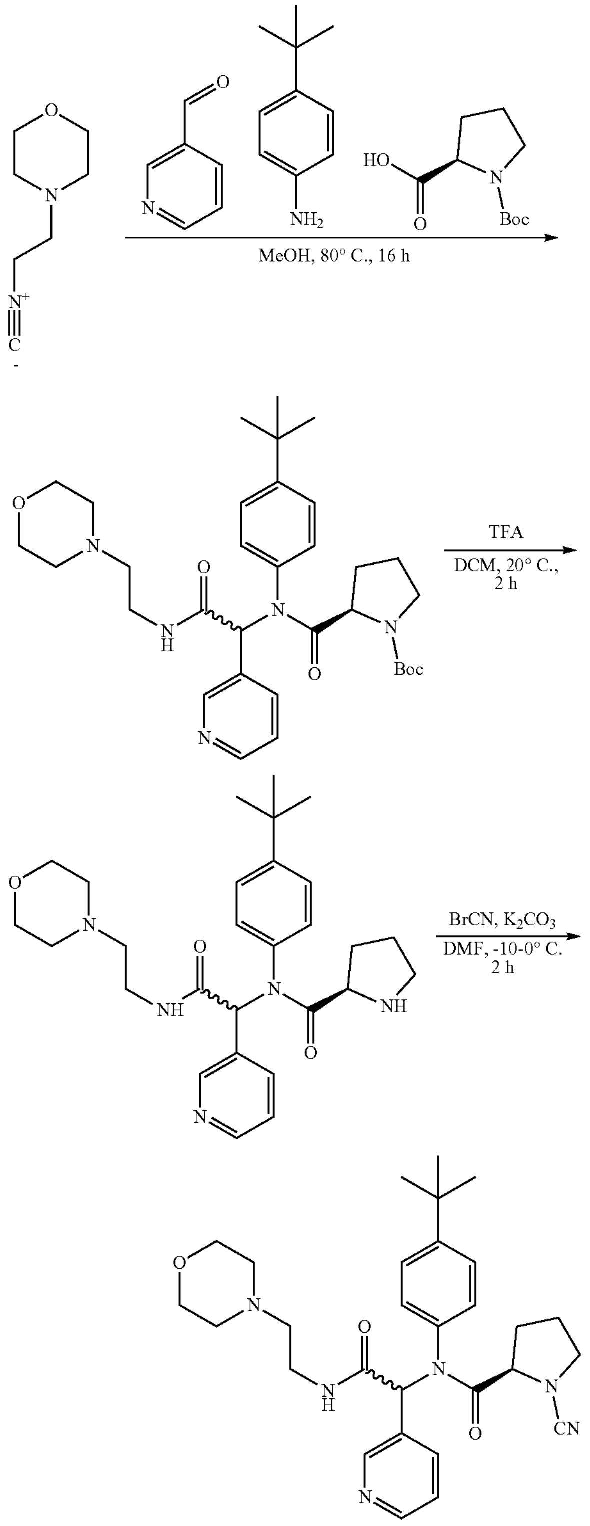

Step 1: tert-butyl (2R)-2-[(4-tert-butylphenyl)-[2-(2-morpholinoethylamino)-2-oxo-1-(3-pyridyl)ethyl] carbamoyl]pyrrolidine-1-carboxylate and tert-butyl (2R)-2-[(4-tert-butylphenyl)-[2-(2-morpholinoethyl-amino)-2-oxo-1-(3-pyridyl)ethyl]carbamoyl]pyrrolidine-1-carboxylate To a mixture of pyridine-3-carbaldehyde (100 mg, 933.62 umol, 87.72 uL, 1 eq) and 4-tert-butylaniline (139.33 mg, 933.62 umol, 147.44 uL, 1 eq) in MeOH (4 mL) was added (2R)-1-tert-butoxycarbonylpyrrolidine-2-carboxylic acid (200.96 mg, 933.62 umol, 1 eq) and 4-(2-isocyanoethyl) morpholine (130.88 mg, 933.62 umol, 128.31 uL, 1 eq). The mixture was stirred at 80° C. for 16 h. The reaction was concentrated and purified by prep-HPLC (column: Phenomenex Gemini-NX C18 75*30 mm*3 um; mobile phase: [water (10 mM NH4HCO3)-ACN]; B %: 35%-65%, 6 min) and prep-HPLC (column: Phenomenex luna c18 250 mm*100 mm*10 um; mobile phase: [water (0.1% TFA)-ACN]; B %: 40%-70%, 25 min) to give tert-butyl (2R)-2-[(4-tert-butylphenyl)-[2-(2-morpholinoethylamino)-2-oxo-1-(3-pyridyl)ethyl]carbamoyl]pyrrolidine-1-carboxylate (5 mg, 8.42 umol, 9.02e-1% yield) and tert-butyl (2R)-2-[(4-tert-butylphenyl)-[2-(2-morpholinoethylamino)-2-oxo-1-(3-pyridyl)ethyl]carbamoyl]pyrrolidine-1-carboxylate (5 mg, 8.42 umol, 9.02e-1% yield). MS (ESI) m/z 594.3 $[M+H]^+$ Step 2: (2R)—N-(4-tert-butylphenyl)-N-[2-(2-morpholinoethylamino)-2-oxo-1-(3-pyridyl)ethyl]pyrrolidine-2-carboxamide To a mixture of tert-butyl (2R)-2-[(4-tert-butylphenyl)-[2-(2-morpholinoethylamino)-2-oxo-1-(3-pyridyl)ethyl]carbamoyl]pyrrolidine-1-carboxylate (50 mg, 84.21 umol, 1 eq) in DCM (1 mL) was added TFA (0.2 mL). The mixture was stirred at 20° C. for 2 h. The residue was poured into $NaHCO_3$ aq. (10 mL) and extracted with DCM (30 mL*3). The combined organic phase was washed with brine (90 mL), dried with anhydrous $Na_2SO_4$, filtered and concentrated in vacuum and crude product was used directly without further purification to give (2R)—N-(4-tert-butylphenyl)-N-[2-(2-morpholinoethylamino)-2-oxo-1-(3-pyridyl)ethyl]pyrrolidine-2-carboxamide (40 mg, crude). MS (ESI) m/z 494.4 $[M+H]^+$.

Step 3: (2R)—N-(4-(tert-butyl)phenyl)-1-cyano-N-(2-((2-morpholinoethyl)amino)-2-oxo-1-(pyridin-3-yl)ethyl)pyrrolidine-2-carboxamide To a mixture of (2R)—N-(4-(tert-butyl)phenyl)-N-(2-((2-morpholinoethyl)amino)-2-oxo-1-(pyridin-3-yl)ethyl)pyrrolidine-2-carboxamide (30 mg, 49.20 umol, 1 eq) and CNBr (5.21 mg, 49.20 umol, 3.62 uL, 1 eq) in DMF (0.5 mL) was added $K_2CO_3$ (20.40 mg, 147.60 umol, 3 eq). The mixture was stirred at 0° C. and stirred for 2 h. The reaction was concentrated and purified by prep-HPLC (column: Phenomenex Luna C18 200*40 mm*10 um; mobile phase: [water (10 mM NH4HCO3)-ACN]; B %: 20%-50%, 8 min) to give (2R)—N-(4-(tert-butyl)phenyl)-1-cyano-N-(2-((2-morpholinoethyl)amino)-2-oxo-1-(pyridin-3-yl)ethyl)pyrrolidine-2-carboxamide (5.01 mg, 9.83 umol, 19.98% yield, 100% purity). MS (ESI) m/z 519.3 $[M+H]^+$. $^1H$ NMR (400 MHz, METHANOL-$d_4$) δ ppm 8.36-8.37 (m, 2H), 8.31 (s, 1H), 7.63-7.64 (m, 2H), 7.22-7.34 (m, 4H), 5.93 (s, 1H), 4.15-4.17 (m, 1H), 3.75-3.77 (m, 4H), 3.53-3.55 (m, 2H), 3.44-3.45 (m, 2H), 2.77-2.80 (m, 6H), 2.00-2.01 (m, 2H), 1.98-1.99 (m, 1H), 1.97-1.98 (m, 1H) 1.81 (s, 9H).

Step 4: (2R)—N-(4-tert-butylphenyl)-N-[2-(2-morpholinoethylamino)-2-oxo-1-(3-pyridyl)ethyl]pyrrolidine-2-carboxamide To a mixture of tert-butyl (2R)-2-[(4-tert-butylphenyl)-[2-(2-morpholinoethylamino)-2-oxo-1-(3-pyridyl)ethyl]carbamoyl]pyrrolidine-1-carboxylate (50 mg, 84.21 umol, 1 eq) in DCM (1 mL) was added TFA (0.2 mL). The mixture was stirred at 20° C. for 1 h. The reaction was concentrated and crude product was used directly without further purification to give (2R)—N-(4-tert-butylphenyl)-N-[2-(2-morpholinoethylamino)-2-oxo-1-(3-pyridyl)ethyl]pyrrolidine-2-carboxamide (50 mg, crude). MS (ESI) m/z 494.3 $[M+H]^+$ Step 5: (2R)—N-(4-(tert-butyl)phenyl)-1-cyano-N-(2-((2-morpholinoethyl)amino)-2-oxo-1-(pyridin-3-yl)ethyl)pyrrolidine-2-carboxamide To a mixture of (2R)—N-(4-(tert-butyl)phenyl)-N-(2-((2-morpholinoethyl)amino)-2-oxo-1-(pyridin-3-yl)ethyl)pyrrolidine-2-carboxamide (30 mg, 49.20 umol, 1 eq) and CNBr (5.21 mg, 49.20 umol, 3.62 uL, 1 eq) in DMF (0.5 mL) was added $K_2CO_3$ (20.40 mg, 147.60 umol, 3 eq). The mixture was stirred at 0° C. for 2 h. Upon The reaction was concentrated and purified by prep-HPLC (column: Phenomenex Luna C18 200*40 mm*10 um; mobile phase: [water (10 mM NH4HCO3)-ACN]; B %: 20%-50%, 8 min) to give (2R)—N-(4-(tert-butyl)phenyl)-1-cyano-N-(2-((2-morpholinoethyl)amino)-2-oxo-1-(pyridin-3-yl)ethyl)pyrrolidine-2-carboxamide (5.01 mg, 9.83 umol, 19.98% yield, 100% purity). MS (ESI) m/z 519.3 $[M+H]^+$. $^1H$ NMR (400 MHz, METHANOL-$d_4$) δ ppm 8.36-8.37 (m, 2H), 8.31 (s, 1H), 7.63-7.64 (m, 2H), 7.22-7.34 (m, 4H), 5.93 (s, 1H), 4.15-4.17 (m, 1H), 3.75-3.77 (m, 4H), 3.53-3.55 (m, 2H), 3.44-3.45 (m, 2H), 2.77-2.80 (m, 6H), 2.00-2.01 (m, 2H), 1.98-1.99 (m, 1H), 1.97-1.98 (m, 1H) 1.81 (s, 9H)

Example 51: Synthesis of Compound 403

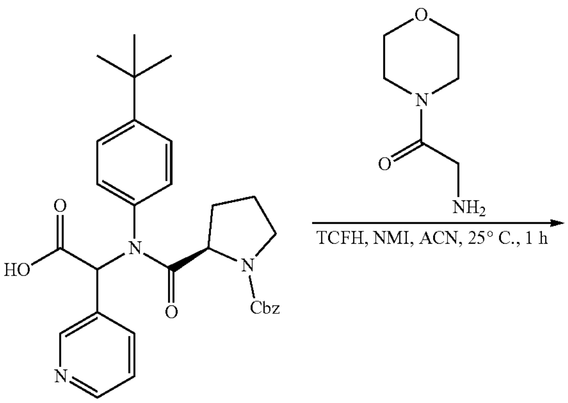

-continued

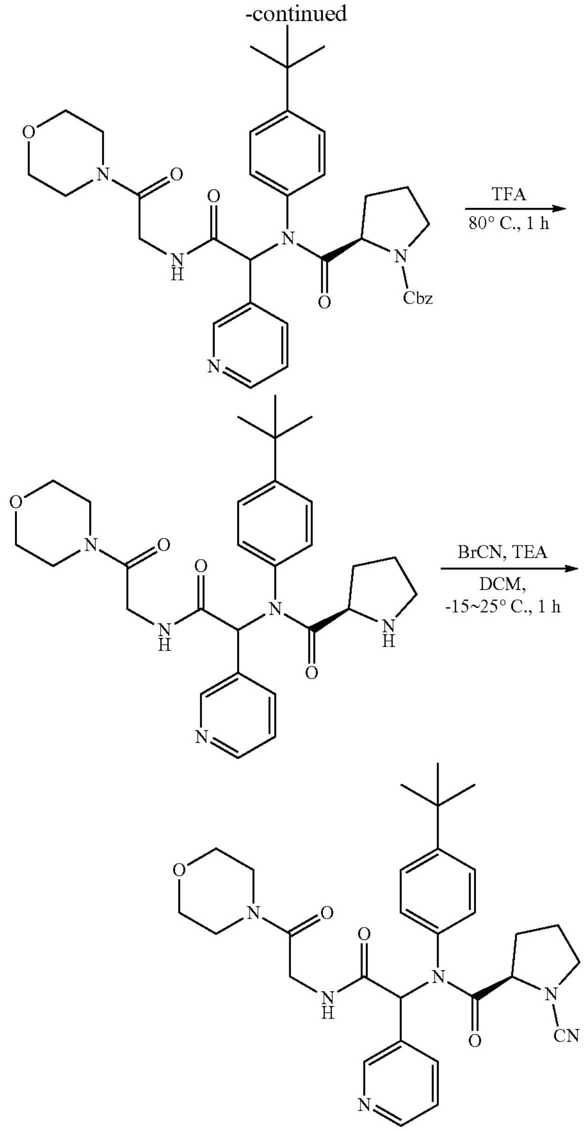

Step 1: (2R)-benzyl 2-((4-(tert-butyl)phenyl)(2-((2-morpholino-2-oxoethyl)amino)-2-oxo-1-(pyridin-3-yl)ethyl)carbamoyl)pyrrolidine-1-carboxylate 2-(N-[(2R)-1-benzyloxycarbonylpyrrolidine-2-carbonyl]-4-tert-butyl-anilino)-2-(3-pyridyl)acetic acid (200 mg, 387.90 umol, 1 eq), 2-amino-1-morpholino-ethanone (83.89 mg, 581.85 umol, 1.5 eq) in ACN (2 mL) was added 1-methyl-imidazole (111.47 mg, 1.36 mmol, 108.22 uL, 3.5 eq) and [chloro(dimethylamino)methylene]-dimethyl-ammonium;hexafluorophosphate (217.67 mg, 775.80 umol, 2 eq). The solution was stirred at 25° C. for 1 h. Upon completion, the solution was diluted with $H_2O$ (20 mL), extracted with EtOAc (50 mL*3), the combined organic phase was dried over $Na_2SO_4$, filtrated and concentrated to give a residue. The residue was used to next step directly and without further purification. Benzyl (2R)-2-[(4-tert-butylphenyl)-[2-[(2-morpholino-2-oxo-ethyl) amino]-2-oxo-1-(3-pyridyl) ethyl]carbamoyl]pyrrolidine-1-carboxylate (250 mg, crude) was obtained as an oil. MS (ESI) m/z 642.4 $[M+H]^+$.

Step 2: (2R)—N-(4-(tert-butyl)phenyl)-N-(2-((2-morpholino-2-oxoethyl)amino)-2-oxo-1-(pyridin-3-yl)ethyl)pyrrolidine-2-carboxamide A solution of benzyl (2R)-2-[(4-tert-butylphenyl)-[2-[(2-morpholino-2-oxo-ethyl) amino]-2-oxo-1-(3-pyridyl) ethyl] carbamoyl]pyrrolidine-1-carboxylate (250 mg, 389.56 umol, 1 eq) in TFA (5 mL) was stirred at 80° C. for 1 h. Upon completion, the solution was concentrated, diluted with the solution of $NaHCO_3$, extracted with EtOAc (30 mL*3). The combined organic phase was dried over $Na_2SO_4$, filtrated and concentrated to give a residue. The residue was used to next step directly and without further purification. (2R)—N-(4-tert-butylphenyl)-N-[2-[(2-morpholino-2-oxo-ethyl) amino]-2-oxo-1-(3-pyridyl) ethyl]pyrrolidine-2-carboxamide (150 mg, crude) was obtained as an oil. MS (ESI) m/z 508.2 $[M+H]^+$.

Step 3: (2R)—N-(4-(tert-butyl)phenyl)-1-cyano-N-(2-((2-morpholino-2-oxoethyl)amino)-2-oxo-1-(pyridin-3-yl)ethyl)pyrrolidine-2-carboxamide (2R)—N-(4-tert-butylphenyl)-N-[2-[(2-morpholino-2-oxo-ethyl)amino]-2-oxo-1-(3-pyridyl)ethyl]pyrrolidine-2-carboxamide (50 mg, 98.50 umol, 1 eq) in DCM (0.5 mL) was added with TEA (19.93 mg, 197.00 umol, 27.42 uL, 2 eq) and the solution was cooled to −15° C. Then, a solution of BrCN (10.43 mg, 98.50 umol, 7.25 uL, 1 eq) in DCM (0.2 mL) was added and the solution was stirred at 0° C. and warmed 25° C. for 1 h gradually. Upon completion, the solution was quenched with $H_2O$ (10 mL), extracted with EtOAc (20 mL*3), the combined organic phase was dried over $Na_2SO_4$, filtrated and concentrated to give the crude. The residue was purified by prep-HPLC (neutral condition), column: Waters Xbridge Prep OBD C18 150*40 mm*10 um; mobile phase: [water (10 mM $NH_4HCO_3$)-ACN]; B %: 25%-50%, 8 min. (2R)—N-(4-tert-butylphenyl)-1-cyano-N-[2-[(2-morpholino-2-oxo-ethyl)amino]-2-oxo-1-(3-pyridyl) ethyl]pyrrolidine-2-carboxamide (5 mg, 9.30 umol, 9.44% yield, 99.1% purity) was obtained as a solid, $^1H$ NMR (400 MHz, METHANOL-$d_4$) δ=8.44-8.27 (m, 2H), 7.81-6.49 (m, 6H), 6.38-6.04 (m, 1H), 4.29-3.99 (m, 3H), 3.67 (td, J=4.5, 9.0 Hz, 4H), 3.62-3.40 (m, 6H), 2.15-1.75 (m, 4H), 1.28-1.21 (m, 9H). MS (ESI) m/z 533.2 $[M+H]^+$.

Example 52: Synthesis of Compound 475

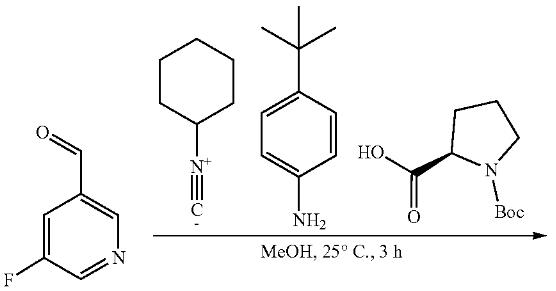

-continued

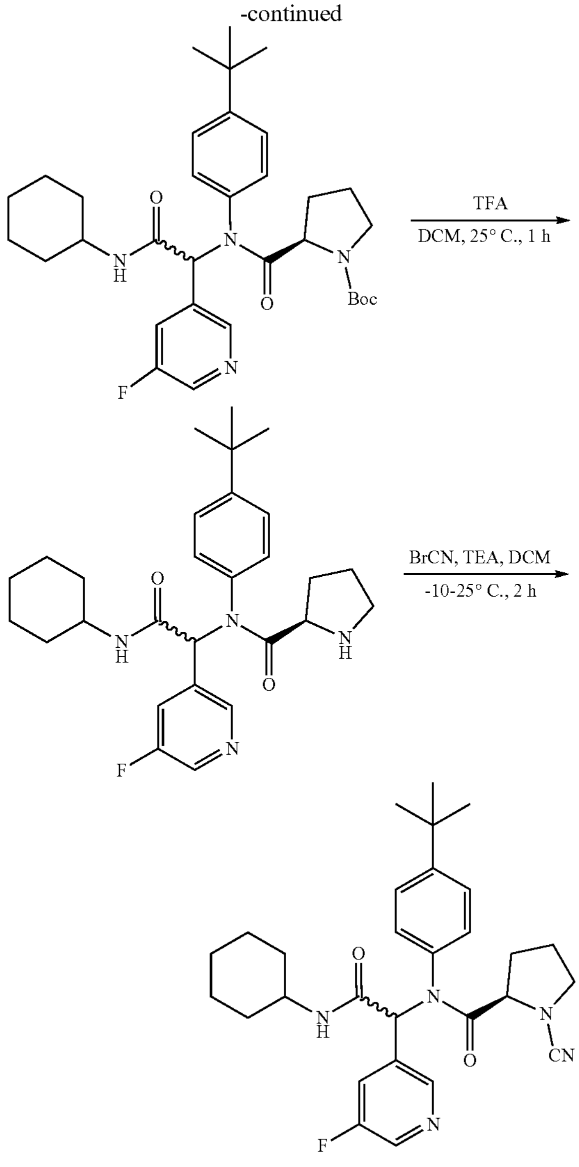

Step1:(2R)-tert-butyl2-((4-(tert-butyl)phenyl)(2-(cyclohexylamino)-1-(5-fluoropyridin-3-yl)-2-oxo-ethyl)carbamoyl)pyrrolidine-1-carboxylate A solution of 5-fluoronicotinaldehyde (400 mg, 3.20 mmol, 1 eq), 4-(tert-butyl)aniline (477.16 mg, 3.20 mmol, 504.93 uL, 1 eq) in MeOH (10 mL) was stirred at 25° C. for 1 h, and the mixture was added with (R)-1-(tert-butoxycarbonyl)pyrrolidine-2-carboxylic acid (688.23 mg, 3.20 mmol, 1 eq). The resulting mixture was stirred at 25° C. for 0.5 h, and the reaction was added with isocyanocyclohexane (314.15 mg, 2.88 mmol, 357.81 uL, 0.9 eq) for three times for 1.5 h at 25° C. Upon completion, the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: 60%-80%, 8 min) to give a product (2R)-tert-butyl 2-((4-(tert-butyl)phenyl)(2-(cyclohexylamino)-1-(5-fluoropyridin-3-yl)-2-oxoethyl)carbamoyl)pyrrolidine-1-carboxylate (300 mg, 516.59 umol, 16.16% yield) and (2R)-tert-butyl 2-((4-(tert-butyl)phenyl)(2-(cyclohexylamino)-1-(5-fluoropyridin-3-yl)-2-oxoethyl)carbamoyl) pyrrolidine-1-carboxylate (330 mg, 568.25 umol, 17.77% yield) as an oil. MS (ESI) m/z 581.3 [M+H]$^+$ Step2:(2R)—N-(4-(tert-butyl)phenyl)-N-(2-(cyclohexylamino)-1-(5-fluoropyridin-3-yl)-2-oxoethyl) pyrrolidine-2-carboxamide Isomer 1: To a solution of (2R)-tert-butyl 2-((4-(tert-butyl)phenyl)(2-(cyclohexylamino)-1-(5-fluoropyridin-3-yl)-2-oxoethyl)carbamoyl)pyrrolidine-1-carboxylate (300 mg, 516.59 umol, 1 eq) in DCM (7 mL) was added TFA (3.53 g, 31.00 mmol, 2.29 mL, 60 eq) and the mixture was stirred at 25° C. for 1 h. Upon completion, the mixture was quenched by the addition $NaHCO_3$ 50 mL and then extracted with EtOAc 30 mL*3. The combined organic layers were washed with brine (50 mL), dried over $Na_2SO_4$, filtered and concentrated under reduced pressure to give a residue, and the residue was purified by prep-HPLC (column: Waters Xbridge BEH C18 250*50 mm*10 um; mobile phase: [water (10 mM $NH_4HCO_3$)-ACN]; B %: 40%-70%, 10 min) to give the product (2R)—N-(4-(tert-butyl)phenyl)-N-(2-(cyclohexylamino)-1-(5-fluoropyridin-3-yl)-2-oxoethyl) pyrrolidine-2-carboxamide (200 mg, 416.13 umol, 80.55% yield) as a solid. MS (ESI) m/z 481.2 [M+H]$^+$ $^1$H NMR (400 MHz, DMSO-$d_6$) δ=8.39-8.31 (m, 1H), 8.21-8.13 (m, 1H), 8.09-8.00 (m, 1H), 7.68-6.68 (m, 5H), 6.14-5.94 (m, 1H), 3.64-3.42 (m, 2H), 3.00-2.90 (m, 1H), 1.79-1.35 (m, 10H), 1.27-1.01 (m, 15H).

Isomer 2: To a solution of (2R)-tert-butyl 2-((4-(tert-butyl)phenyl)(2-(cyclohexylamino)-1-(5-fluoropyridin-3-yl)-2-oxoethyl)carbamoyl)pyrrolidine-1-carboxylate (330 mg, 568.25 umol, 1 eq) in DCM (7.5 mL) was added TFA (3.89 g, 34.09 mmol, 2.52 mL, 60 eq) and the mixture was stirred at 25° C. for 1 h. Upon completion, the mixture was quenched by addition $NaHCO_3$ (50 mL) and then extracted with EtOAc (30 mL*3). The combined organic layers were washed with brine (50 mL), dried over $Na_2SO_4$, filtered and concentrated under reduced pressure to give a residue, and the crude product was purified by prep-HPLC (column: Waters Xbridge BEH C18 100*30 mm*10 um; mobile phase: [water (10 mM $NH_4HCO_3$)-ACN]; B %: 40%-70%, 10 min) to give the product (2R)—N-(4-(tert-butyl)phenyl)-N-(2-(cyclohexylamino)-1-(5-fluoropyridin-3-yl)-2-oxoethyl)pyrrolidine-2-carboxamide (225 mg, 468.15 umol, 82.38% yield) as a solid. MS (ESI) m/z 481.2 [M+H]$^+$ $^1$H NMR (400 MHz, DMSO-$d_6$) δ=8.39-8.32 (m, 1H), 8.21-8.14 (m, 1H), 8.02 (d, J=7.8 Hz, 1H), 7.22 (m, 5H), 6.13-5.90 (m, 1H), 3.64-3.47 (m, 2H), 3.01-2.91 (m, 11H), 1.73-1.41 (m, 10H), 1.25-1.02 (m, 15H).

Step 3: (2R)—N-(4-(tert-butyl)phenyl)-1-cyano-N-(2-(cyclohexylamino)-1-(5-fluoropyridin-3-yl)-2-oxoethyl)pyrrolidine-2-carboxamide Compound 475 Isomer 1: To a solution of (2R)—N-(4-(tert-butyl)phenyl)-N-(2-(cyclohexylamino)-1-(5-fluoropyridin-3-yl)-2-oxoethyl)pyrrolidine-2-carboxamide (170 mg, 353.71 umol, 1 eq) in DCM (2 mL) was added TEA (107.38 mg, 1.06 mmol, 147.70 uL, 3 eq) and the mixture was cooled at −10° C. BrCN (56.20 mg, 530.57 umol, 39.03 uL, 1.5 eq) in DCM (0.5 mL) and the mixture was stirred for 0.5 h at 0° C. and warmed to 25° C. for 1.5 h. Upon completion, the mixture was added into water (15 mL), extracted with DCM (10 mL*3), then was concentrated under reduced pressure and was purified by prep-HPLC (column: Waters Xbridge BEH C18 100*30 mm*10 um; mobile phase: [water (10 mM $NH_4HCO_3$)-ACN]; B %: 45%-75%, 10 min) to give (2R)—N-(4-(tert-butyl)phenyl)-1-cyano-N-(2-(cyclohexylamino)-1-(5-fluoropyridin-3-yl)-2-oxoethyl)pyrrolidine-2-carboxamide (22 mg, 43.51 umol, 12.30% yield) as a solid. MS (ESI) m/z 506.2 [M+H]$^+$ $^1$H NMR (400 MHz, MeOD-$d_4$) δ=8.24-8.16 (m, 2H), 7.67-7.08 (m, 4H), 6.85-6.58 (m, 1H), 6.15 (s, 1H), 4.15 (dd, J=5.2, 7.8 Hz, 1H), 3.78-3.64 (m, 1H), 3.63-3.53 (m, 1H), 3.49-3.41 (m, 1H), 2.13-1.57 (m, 9H), 1.45-1.00 (m, 14H).

Compound 475 Isomer 2: To a solution of (2R)—N-(4-(tert-butyl)phenyl)-N-(2-(cyclohexylamino)-1-(5-fluoropyridin-3-yl)-2-oxoethyl)pyrrolidine-2-carboxamide (220 mg, 457.75 umol, 1 eq) in DCM (2 mL) was added TEA (138.96 mg, 1.37 mmol, 191.14 uL, 3 eq) and the mixture was cooled at −10° C. Then, BrCN (72.73 mg, 686.62 umol, 50.51 uL, 1.5 eq) in DCM (0.5 mL) was added and the solution stirred for 0.5 h at 0° C. and warmed to 25° C. gradually for 1.5 h. Upon completion, the mixture was added into water (20 mL), extracted with DCM (10 mL*3), then concentrated under reduced pressure and was purified by prep-HPLC (prep-HPLC condition: column: Waters Xbridge BEH C18 100*30 mm*10 um; mobile phase: [water (10 mM $NH_4HCO_3$)-ACN]; B %: 45%-75%, 10 min) to give (2R)—N-(4-(tert-butyl)phenyl)-1-cyano-N-(2-(cyclohexylamino)-1-(5-fluoropyridin-3-yl)-2-oxoethyl)pyrrolidine-2-carboxamide (50 mg, 98.89 umol, 21.60% yield) as a solid. MS (ESI) m/z 506.2 [M+H]$^+$ $^1$H NMR (400 MHz, MeOD-$d_4$) δ=8.34-8.21 (m, 2H), 7.34 (m, 4H), 6.88-6.40 (m, 1H), 6.01 (s, 1H), 4.16 (br dd, J=4.8, 7.6 Hz, 1H), 3.72-3.62 (m, 1H), 3.61-3.54 (m, 1H), 3.47-3.39 (m, 1H), 2.00-1.59 (m, 9H), 1.38-1.10 (m, 14H).

Example 53: Synthesis of Compound 479

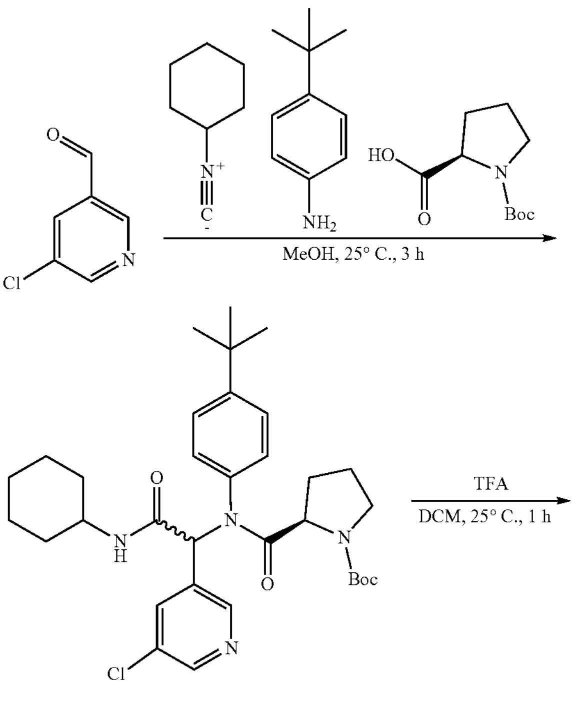

-continued

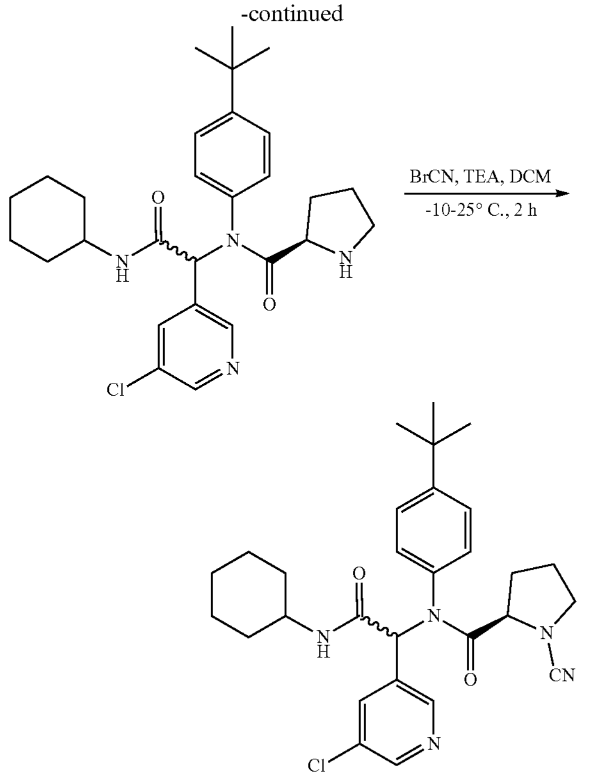

Step1:(2R)-tert-butyl2-((4-(tert-butyl)phenyl)(1-(5-chloropyridin-3-yl)-2-(cyclohexylamino)-2-oxo-ethyl)carbamoyl)pyrrolidine-1-carboxylate A solution of 4-(tert-butyl)aniline (421.69 mg, 2.83 mmol, 446.24 uL, 1 eq), 5-chloro-nicotinaldehyde (400 mg, 2.83 mmol, 1 eq) in MeOH (10 mL) was stirred at 25° C. for 1 h, and the mixture was added with (R)-1-(tert-butoxycarbonyl)pyrrolidine-2-carboxylic acid (608.23 mg, 2.83 mmol, 1 eq). The mixture was stirred at 25° C. for 0.5 h and the reaction was added isocyanocyclohexane (277.64 mg, 2.54 mmol, 316.21 uL, 0.9 eq) for three times and the mixture was stirred at 25° C. for 1.5 h. Upon completion, the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: 65%-85%, 8 min) to give a product (2R)-tert-butyl 2-((4-(tert-butyl)phenyl)(1-(5-chloropyridin-3-yl)-2-(cyclohexylamino)-2-oxoethyl)carbamoyl)pyrrolidine-1-carboxylate (120 mg, 200.94 umol, 7.11% yield) and (2R)-tert-butyl 2-((4-(tert-butyl)phenyl)(1-(5-chloropyridin-3-yl)-2-(cyclohexylamino)-2-oxoethyl)carbamoyl)pyrrolidine-1-carboxylate (270 mg, 452.12 umol, 16.00% yield) was obtained as an oil. MS (ESI) m/z 597.3 $[M+H]^+$ Step2:(2R)—N-(4-(tert-butyl)phenyl)-N-(1-(5-chloropyridin-3-yl)-2-(cyclohexylamino)-2-oxoethyl) pyrrolidine-2-carboxamide Isomer 1: To a solution of (2R)-tert-butyl 2-((4-(tert-butyl)phenyl)(1-(5-chloropyridin-3-yl)-2-(cyclohexylamino)-2-oxoethyl)carbamoyl)pyrrolidine-1-carboxylate (120 mg, 200.94 umol, 1 eq) in DCM (2.7 mL) was added TFA (1.37 g, 12.06 mmol, 892.68 uL, 60 eq) and the mixture was stirred at 25° C. for 1 h. Upon completion, the mixture was quenched by addition $NaHCO_3$ 20 mL and then extracted with EtOAc (10 mL*3). The combined organic layers were washed with brine (20 mL), dried over $Na_2SO_4$, filtered and concentrated under reduced pressure to give a residue, and residue was purified by prep-HPLC (column: Waters Xbridge BEH C18 100*30 mm*10 um; mobile phase: [water (10 mM $NH_4HCO_3$)-ACN]; B %: 40%-70%, 10 min) to give the product (2R)—N-(4-(tert-butyl)phenyl)-N-(1-(5-chloropyridin-3-yl)-2-(cyclohexylamino)-2-oxo-ethyl)pyrrolidine-2-carboxamide (80 mg, 160.94 umol, 80.09% yield) as a solid. MS (ESI) m/z 497.1 $[M+H]^+$ 11H NMR (400 MHz, MeOD-$d_4$) δ=8.32 (d, J=2.3 Hz, 1H), 8.25 (d, J=1.8 Hz, 1H), 8.06-7.02 (m, 4H), 6.63 (br s, 1H), 6.11 (s, 1H), 3.80-3.61 (m, 1H), 3.60-3.39 (m, 1H), 3.20-3.00 (m, 1H), 2.79-2.56 (m, 1H), 1.95-1.49 (m, 9H), 1.41-1.09 (m, 14H).

Isomer 2: To a solution of (2R)-tert-butyl 2-((4-(tert-butyl)phenyl)(1-(5-chloropyridin-3-yl)-2-(cyclohexylamino)-2-oxoethyl)carbamoyl)pyrrolidine-1-carboxylate (230 mg, 385.14 umol, 1 eq) in DCM (5.1 mL) was added TFA (2.63 g, 23.11 mmol, 1.71 mL, 60 eq) and the mixture was stirred at 25° C. for 1 h. Upon completion, the mixture was quenched by addition $NaHCO_3$ (50 mL) and then extracted with EtOAc (30 mL*3). The combined organic layers were washed with brine 50 mL, dried over $Na_2SO_4$, filtered and concentrated under reduced pressure to give a residue, and the residue was purified by prep-HPLC (column: Waters Xbridge BEH C18 100*30 mm*10 um; mobile phase: [water (10 mM $NH_4HCO_3$)-ACN]; B %: 40%-70%, 10 min) to give the product (2R)—N-(4-(tert-butyl)phenyl)-N-(1-(5-chloropyridin-3-yl)-2-(cyclohexylamino)-2-oxo-ethyl)pyrrolidine-2-carboxamide (150 mg, 301.77 umol, 78.35% yield) was obtained as a solid. MS (ESI) m/z 497.1 $[M+H]^+$ $^1H$ NMR (400 MHz, MeOD-$d_4$) δ=8.32 (br s, 1H), 8.36 (d, J=2.3 Hz, 1H), 8.11-6.20 (m, 5H), 6.16-5.86 (m, 1H), 3.71-3.61 (m, 1H), 3.56 (br d, J=7.0 Hz, 1H), 3.17-3.06 (m, 1H), 2.68 (br s, 1H), 1.91-1.60 (m, 9H), 1.26 (s, 14H).

Step3:(2R)—N-(4-(tert-butyl)phenyl)-N-(1-(5-chloropyridin-3-yl)-2-(cyclohexylamino)-2-oxoethyl)-1-cyanopyrrolidine-2-carboxamide Compound 479 Isomer 1: To a solution of (2R)—N-(4-(tert-butyl)phenyl)-N-(1-(5-chloropyridin-3-yl)-2-(cyclohexylamino)-2-oxoethyl)pyrrolidine-2-carboxamide (70 mg, 140.83 umol, 1 eq) in DCM (1 mL) was added TEA (42.75 mg, 422.48 umol, 58.80 uL, 3 eq), and then the mixture was cooled at −10° C. To the resulting mixture, BrCN (22.37 mg, 211.24 umol, 15.54 uL, 1.5 eq) in DCM (1 mL) was added and stirred for 0.5 h at 0° C. and warmed to 25° C. gradually for 1.5 h. Upon completion, the mixture was added into water (15 mL) and was extracted with DCM (10 mL*3), concentrated under reduced pressure and was purified by prep-HPLC (column: Waters Xbridge BEH C18 100*30 mm*10 um; mobile phase: [water (10 mM $NH_4HCO_3$)-ACN]; B %: 46%-76%, 10 min) to give (2R)—N-(4-(tert-butyl)phenyl)-N-(1-(5-chloropyridin-3-yl)-2-(cyclohexylamino)-2-oxoethyl)-1-cyanopyrrolidine-2-carboxamide (10 mg, 19.15 umol, 13.60% yield) as a solid. MS (ESI) m/z 522.1 $[M+H]^+$ $^1H$ NMR (400 MHz, MeOD-$d_4$) δ=8.32 (d, J=2.4 Hz, 1H), 8.26 (d, J=1.6 Hz, 1H), 7.79-7.11 (m, 4H), 6.65 (br s, 1H), 6.11 (s, 1H), 4.16 (dd, J=5.2, 7.9 Hz, 1H), 3.74-3.64 (m, 1H), 3.63-3.54 (m, 1H), 3.50-3.39 (m, 1H), 2.13-1.88 (m, 4H), 1.87-1.58 (m, 5H), 1.45-1.00 (m, 14H).

Compound 479 Isomer 2: To a solution of (2R)—N-(4-(tert-butyl)phenyl)-N-(1-(5-chloropyridin-3-yl)-2-(cyclohexylamino)-2-oxoethyl)pyrrolidine-2-carboxamide (120 mg, 241.41 umol, 1 eq) in DCM (1 mL) was added TEA (73.29 mg, 724.24 umol, 100.81 uL, 3 eq) and the mixture was cooled at −10° C. BrCN (38.36 mg, 362.12 umol, 26.64 uL, 1.5 eq) in DCM (0.5 mL) was added and the mixture was stirred for 0.5 h at 0° C. and warmed to 25° C. gradually for 1.5 h. Upon completion, the mixture was added into water (20 mL) and was extracted with DCM (10 mL*3), concentrated under reduced pressure, and was purified by prep-HPLC (column: Waters Xbridge BEH C18 100*30 mm*10 um; mobile phase: [water (10 mM $NH_4HCO_3$)-ACN]; B %: 45%-75%, 10 min) to give (2R)—N-(4-(tert-butyl)phenyl)-N-(1-(5-chloropyridin-3-yl)-2-(cyclohexylamino)-2-oxo-ethyl)-1-cyanopyrrolidine-2-carboxamide (30 mg, 57.46 umol, 23.80% yield) as a solid. MS (ESI) m/z 522.1 $[M+H]^+$ 1H NMR (400 MHz, MeOD-$d_4$) δ=8.37 (d, J=2.4 Hz, 1H), 8.31 (d, J=1.6 Hz, 1H), 7.49 (br t, J=2.0 Hz, 4H), 6.94-6.43 (m, 1H), 5.99 (s, 1H), 4.18 (dd, J=4.8, 7.6 Hz, 1H), 3.69-3.54 (m, 2H), 3.43 (br d, J=5.2 Hz, 1H), 2.02-1.88 (m, 4H), 1.83-1.60 (m, 5H), 1.39-1.13 (m, 14H).

Example 54: Synthesis of Compound 483

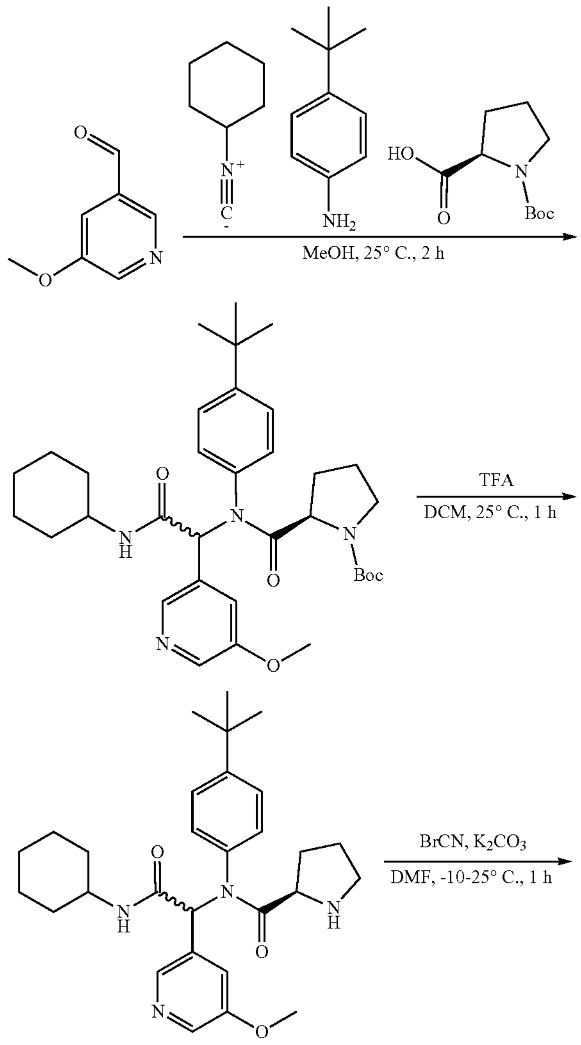

-continued

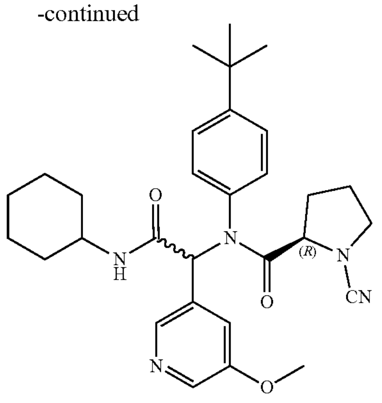

Step 1: (2R)-tert-butyl 2-((4-(tert-butyl)phenyl)(2-(cyclohexylamino)-1-(5-methoxypyridin-3-yl)-2-oxoethyl)carbamoyl)pyrrolidine-1-carboxylate A solution of 4-tert-butylaniline (272.05 mg, 1.82 mmol, 287.89 uL, 1 eq), 5-methoxypyridine-3-carbaldehyde (250 mg, 1.82 mmol, 1 eq), 1-tert-butoxycarbonylpyrrolidine-2-carboxylic acid (392.40 mg, 1.82 mmol, 1 eq) and isocyanocyclohexane (199.02 mg, 1.82 mmol, 226.67 uL, 1 eq) in MeOH (4 mL) was stirred at 25° C. for 2 h. The reaction mixture was concentrated under reduced pressure to give a residue. The residue was purified by column chromatography ($SiO_2$, petroleum ether/EtOAc=1/0 to 0/1) to get the product tert-butyl (2R)-2-[(4-tert-butylphenyl)-[2-(cyclohexylamino)-1-(5-methoxy-3-pyridyl)-2-oxo-ethyl]carbamoyl]pyrrolidine-1-carboxylate (800 mg, 1.35 mmol, 74.03% yield) was obtained as a solid: MS (ESI) m/z 593.3 $[M+H]^+$ Step 2: (2R)—N-(4-(tert-butyl)phenyl)-N-(2-(cyclohexylamino)-1-(5-methoxypyridin-3-yl)-2-oxoethyl) pyrrolidine-2-carboxamide To a solution of tert-butyl 2-[(4-tert-butylphenyl)-[2-(cyclohexylamino)-1-(5-methoxy-3-pyridyl)-2-oxo-ethyl]carbamoyl]pyrrolidine-1-carboxylate (100 mg, 168.70 umol, 1 eq) in DCM (1.5 mL) was added drop-wise TFA (770.00 mg, 6.75 mmol, 500.00 uL, 40.03 eq), then the mixture was stirred at 25° C. for 1 h. The reaction mixture was quenched by addition $H_2O$ (30 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Kromasil C18 (100×25 mm×5 um); mobile phase: [water (10 mM $NH_4HCO_3$)-ACN]; B %: 30%-60%, 10 min) to get the product (2R)—N-(4-tert-butylphenyl)-N-[2-(cyclohexylamino)-1-(5-methoxy-3-pyridyl)-2-oxo-ethyl]pyrrolidine-2-carboxamide (11.59 mg, 23.08 umol, 13.68% yield) as a solid. MS (ESI) m/z 493.2 $[M+H]^+$ $^1H$ NMR (METHANOL-$d_4$, 400 MHz): δ ppm 8.02 (d, J=2.8 Hz, 1H), 7.96 (d, J=1.6 Hz, 1H), 7.03-7.86 (m, 3H), 6.96 (dd, J=2.5, 1.9 Hz, 1H), 6.27-6.90 (m, 1H), 6.00 (s, 1H), 3.58-3.73 (m, 4H), 3.53 (t, J=6.7 Hz, 1H), 3.06-3.15 (m, 1H), 2.59-2.72 (m, 1H), 1.86-1.95 (m, 1H), 1.53-1.83 (m, 8H), 1.02-1.43 (m, 14H). (2R)—N-(4-tert-butylphenyl)-N-[2-(cyclohexylamino)-1-(5-methoxy-3-pyridyl)-2-oxo-ethyl]pyrrolidine-2-carboxamide (14.58 mg, 29.59 umol, 17.54% yield, 100% purity) was obtained as a solid. MS (ESI) m/z 493.2 $[M+H]^+$ $^1H$ NMR (METHANOL-$d_4$, 400 MHz): δ ppm 7.95-8.03 (m, 1H), 7.92 (d, J=1.6 Hz, 1H), 7.73 (br d, J=5.4 Hz, 1H), 7.41 (br s, 11H), 7.16 (br s, 1H), 6.92-7.00 (m, 11H), 6.60 (br d, J=3.4 Hz, 1H), 6.10 (s, 1H), 3.58-3.77 (m, 4H), 3.47 (t, J=7.3 Hz, 1H), 3.12 (dt, J=11.2, 5.6 Hz, 1H), 2.56-2.72 (m, 1H), 1.92 (br d, J=10.5 Hz, 1H), 1.52-1.89 (m, 8H), 1.02-1.42 (m, 14H).

Step 3: (2R)—N-(4-(tert-butyl)phenyl)-1-cyano-N-(2-(cyclohexylamino)-1-(5-methoxypyridin-3-yl)-2-oxoethyl)pyrrolidine-2-carboxamide A solution of (2R)—N-(4-tert-butylphenyl)-N-[2-(cyclohexylamino)-1-(5-methoxy-3-pyridyl)-2-oxo-ethyl]pyrrolidine-2-carboxamide (100 mg, 202.98 umol, 1 eq) in DMF (1 mL) was cooled to −10° C., and then $K_2CO_3$ (84.16 mg, 608.95 umol, 3.0 eq) and BrCN (25.80 mg, 243.58 umol, 17.92 uL, 1.2 eq) was added drop-wise at −10° C. The mixture was allowed to warm to 25° C. and stirred for 1 h. The reaction mixture was quenched by addition $H_2O$ (20 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100×25 mm×5 um; mobile phase: [water (10 mM $NH_4HCO_3$)-ACN]; B %: 40%-70%, 10 min) to get the product (2R)—N-(4-tert-butylphenyl)-1-cyano-N-[2-(cyclohexylamino)-1-(5-methoxy-3-pyridyl)-2-oxo-ethyl]pyrrolidine-2-carboxamide (24.93 mg, 48.16 umol, 23.73% yield, 100% purity) was obtained as a solid. MS (ESI) m/z 518.2 $[M+H]^+$ $_1$H NMR (METHANOL-$d_4$, 400 MHz): δ ppm 8.03 (d, J=2.4 Hz, 1H), 7.98 (s, 1H), 7.06-7.89 (m, 3H), 6.95-7.02 (m, 1H), 6.58 (br s, 1H), 5.96 (s, 1H), 4.17 (dd, J=7.6, 5.2 Hz, 1H), 3.53-3.72 (m, 5H), 3.44 (td, J=8.0, 5.3 Hz, 1H), 1.85-2.03 (m, 4H), 1.57-1.84 (m, 5H), 1.04-1.41 (m, 14H).

A solution of (2R)—N-(4-tert-butylphenyl)-N-[2-(cyclohexylamino)-1-(5-methoxy-3-pyridyl)-2-oxo-ethyl]pyrrolidine-2-carboxamide (100 mg, 202.98 umol, 1 eq) in DMF (1 mL) was cooled to −10° C., then $K_2CO_3$ (84.16 mg, 608.95 umol, 3.0 eq) and BrCN (25.80 mg, 243.58 umol, 17.92 uL, 1.2 eq) was added drop-wise at −10° C. The mixture was allowed to warm to 25° C. and stirred for 1 h. The reaction mixture was quenched by addition $H_2O$ (20 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100×25 mm×5 um; mobile phase: [water (10 mM $NH_4HCO_3$)-ACN]; B %: 40%-70%, 10 min) to get the product (2R)—N-(4-tert-butylphenyl)-1-cyano-N-[2-(cyclohexylamino)-1-(5-methoxy-3-pyridyl)-2-oxo-ethyl]pyrrolidine-2-carboxamide (22.98 mg, 44.39 umol, 21.87% yield, 100% purity) as a solid. MS (ESI) m/z 518.2 $[M+H]^+$ $^1$H NMR (METHANOL-$d_4$, 400 MHz): δ ppm 8.00 (d, J=2.7 Hz, 1H), 7.88-7.97 (m, 1H), 7.60-7.85 (m, 1H), 7.35-7.57 (m, 1H), 7.10-7.32 (m, 1H), 6.94-7.09 (m, 1H), 6.55-6.76 (m, 1H), 6.13 (s, 1H), 4.16 (dd, J=7.9, 5.2 Hz, 1H), 3.65-3.80 (m, 4H), 3.61 (dt, J=8.6, 6.8 Hz, 1H), 3.43-3.51 (m, 1H), 1.90-2.17 (m, 4H), 1.60-1.88 (m, 5H), 1.06-1.44 (m, 14H).

Example 55: Synthesis of Compound 587

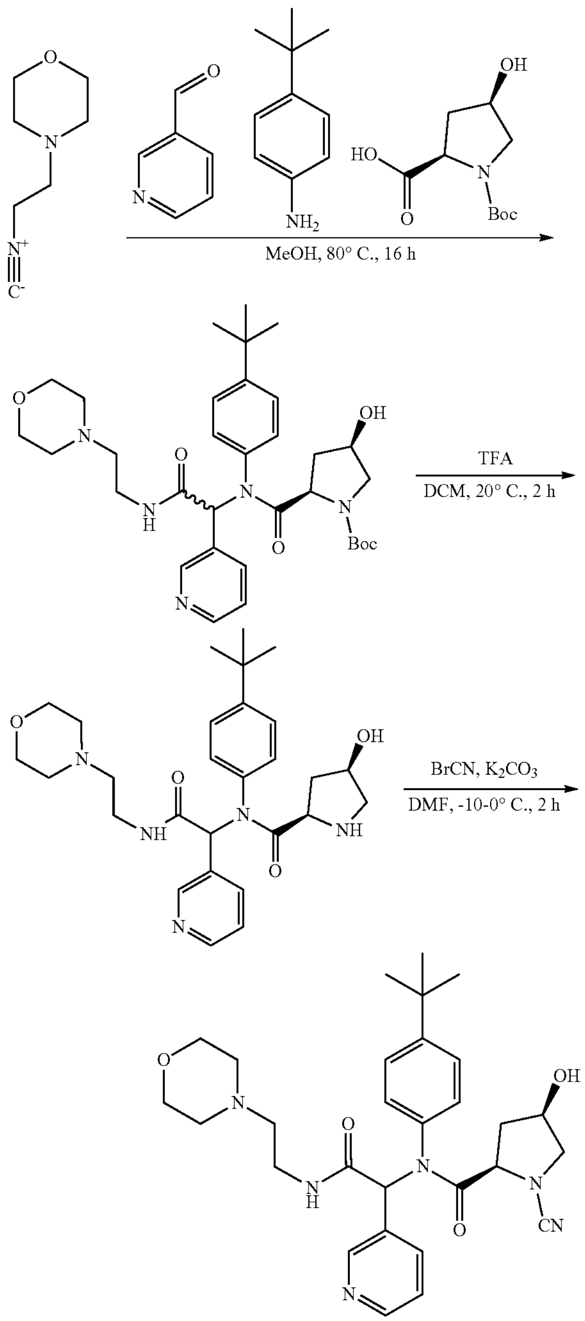

Step 1: tert-butyl (2R,5R)-2-[(4-tert-butylphenyl)-[2-(2-morpholinoethylamino)-2-oxo-1-(3-pyridyl)ethyl]carbamoyl]-5-hydroxy-pyrrolidine-1-carboxylate and tert-butyl (2R,5R)-2-[(4-tert-butylphenyl)-[2-(2-morpholinoethylamino)-2-oxo-1-(3-pyridyl)ethyl]carbamoyl]-5-hydroxy-pyrrolidine-1-carboxylate To a mixture of 4-tert-butylaniline (300 mg, 2.01 mmol, 317.46 uL, 1 eq) and pyridine-3-carbaldehyde (215.32 mg, 2.01 mmol, 188.88 uL, 1 eq) in MeOH (0.5 mL) was added (2R,5R)-1-tert-butoxycarbonyl-5-hydroxy-pyrrolidine-2-carboxylic acid (464.87 mg, 2.01 mmol, 1 eq) and 4-(2-isocyanoethyl)morpholine (281.81 mg, 2.01 mmol, 276.28 uL, 1 eq). The mixture was stirred at 80° C. and stirred for 16 h. Upon the completion of the reaction, the reaction was concentrated and purified by prep-HPLC (column: Kromasil C18 (250*50 mm*10 um); mobile phase: [water (10 mM $NH_4HCO_3$)-ACN]; B %: 35%-55%, 10 min) to give tert-butyl (2R,5R)-2-[(4-tert-butylphenyl)-[2-(2-morpholinoethylamino)-2-oxo-1-(3-pyridyl)ethyl]carbamoyl]-5-hydroxy-pyrrolidine-1-carboxylate (70 mg, 114.80 umol, 5.71% yield, 100% purity) and tert-butyl (2R,5R)-2-[(4-tert-butylphenyl)-[2-(2-morpholinoethylamino)-2-oxo-1-(3-pyridyl)ethyl]carbamoyl]-5-hydroxy-pyrrolidine-1-carboxylate (70 mg, 114.80 umol, 5.71% yield, 100% purity). MS (ESI) m/z 610.4 $[M+H]^+$ Step 2: (2R,5R)—N-(4-(tert-butyl)phenyl)-5-hydroxy-N-(2-((2-morpholinoethyl)amino)-2-oxo-1-(pyridin-3-yl)ethyl)pyrrolidine-2-carboxamide A mixture of (2R,5R)-tert-butyl 2-((4-(tert-butyl)phenyl)(2-((2-morpholinoethyl)amino)-2-oxo-1-(pyridin-3-yl)ethyl)carbamoyl)-5-hydroxypyrrolidine-1-carboxylate (20 mg, 32.80 umol, 1 eq) in TFA (0.1 mL) and DCM (1 mL) was stirred at 20° C. for 2 h. Upon the completion of the reaction, the solution was concentrated and purified by prep-HPLC (column: Phenomenex luna C18 100*40 mm*5 um; mobile phase: [water (0.1% TFA)-ACN]; B %: 5%-35%, 8 min) to give (2R,5R)—N-(4-(tert-butyl)phenyl)-5-hydroxy-N-(2-((2-morpholinoethyl)amino)-2-oxo-1-(pyridin-3-yl)ethyl)pyrrolidine-2-carboxamide (4 mg, 7.85 umol, 23.93% yield, 100% purity) as a solid. MS (ESI) m/z 510.2$[M+H]^+$ Step 3: (2R)—N-(4-tert-butylphenyl)-1-cyano-N-[2-(2-morpholinoethylamino)-2-oxo-1-(3-pyridyl)ethyl]pyrrolidine-2-carboxamide To a mixture of (2R,4R)—N-(4-(tert-butyl)phenyl)-4-hydroxy-N-(2-((2-morpholinoethyl)amino)-2-oxo-1-(pyridin-3-yl)ethyl)pyrrolidine-2-carboxamide (30 mg, 60.77 umol, 1 eq) and BrCN (12.87 mg, 121.55 umol, 8.94 uL, 2 eq) in DMF (0.5 mL) was added $K_2CO_3$ (25.20 mg, 182.32 umol, 3 eq) at −10° C. The mixture was stirred at 20° C. and stirred for 2 h. The reaction was concentrated and purified by prep-HPLC (column: Phenomenex Luna C18 200*40 mm*10 um; mobile phase: [water (10 mM $NH_4HCO_3$)-ACN]; B %: 20%-50%, 8 min) to give (2R,4R)—N-(4-(tert-butyl)phenyl)-1-cyano-4-hydroxy-N-(2-((2-morpholinoethyl)amino)-2-oxo-1-(pyridin-3-yl)ethyl)pyrrolidine-2-carboxamide (5.02 mg, 9.68 umol, 15.93% yield). MS (ESI) m/z 535.2 $[M+H]^+$. $^1$H NMR (400 MHz, METHANOL-$d_4$) δ ppm 8.32 (m, 2H), 7.58-7.60 (m, 1H), 7.21-7.31 (m, 4H), 7.19 (s, 1H), 6.17 (s, 1H), 4.27-4.24 (m, 2H), 3.56-3.57 (m, 1H), 3.42-3.43 (m, 3H), 2.62 (s, 6H), 2.11-2.13 (m, 1H), 2.03-2.09 (m, 1H), 1.23 (s, 9H)

Step 4: (2R,5R)—N-(4-(tert-butyl)phenyl)-5-hydroxy-N-(2-((2-morpholinoethyl)amino)-2-oxo-1-(pyridin-3-yl)ethyl)pyrrolidine-2-carboxamide A mixture of (2R,5R)-tert-butyl 2-((4-(tert-butyl)phenyl)(2-((2-morpholinoethyl)amino)-2-oxo-1-(pyridin-3-yl)ethyl)carbamoyl)-5-hydroxypyrrolidine-1-carboxylate (70 mg, 114.80 umol, 1 eq) in TFA (0.1 mL) and DCM (1 mL) was stirred at 20° C. for 16 h. The reaction was concentrated and purified by prep-HPLC (column: Phenomenex luna C18 100*40 mm*5 um; mobile phase: [water (0.1% TFA)-ACN]; B %: 5%-34%, 8 min) to give (2R,5R)—N-(4-(tert-butyl)phenyl)-5-hydroxy-N-(2-((2-morpholinoethyl)amino)-2-oxo-1-(pyridin-3-yl)ethyl)pyrrolidine-2-carboxamide (4 mg, 7.85 umol, 6.84% yield, 100% purity) as a solid. MS (ESI) m/z 510.2 $[M+H]^+$ Step 5: (2R,4R)—N-(4-(tert-butyl)phenyl)-1-cyano-4-hydroxy-N-(2-((2-morpholinoethyl)amino)-2-oxo-1-(pyridin-3-yl)ethyl)pyrrolidine-2-carboxamide To a mixture of (2R,4R)—N-(4-(tert-butyl)phenyl)-4-hydroxy-N-(2-((2-morpholinoethyl)amino)-2-oxo-1-(pyridin-3-yl)ethyl)pyrrolidine-2-carboxamide (30 mg, 60.77 umol, 1 eq) and BrCN (12.87 mg, 121.55 umol, 8.94 uL, 2 eq) in DMF (0.5 mL) was added $K_2CO_3$ (25.20 mg, 182.32 umol, 3 eq) at −10° C. The mixture was stirred at 0° C. 2 h. The reaction was concentrated and purified by prep-HPLC (column: Phenomenex Luna C18 200*40 mm*10 um; mobile phase: [water (10 mM $NH_4HCO_3$)-ACN]; B %: 20%-50%, 8 min) to give (2R,4R)—N-(4-(tert-butyl)phenyl)-1-cyano-4-hydroxy-N-(2-((2-morpholinoethyl)amino)-2-oxo-1-(pyridin-3-yl)ethyl)pyrrolidine-2-carboxamide (5.00 mg, 9.64 umol, 15.86% yield, 100% purity). MS (ESI) m/z 535.3 $[M+H]^+$. $^1$H NMR (400 MHz, METHANOL-$d_4$) δ ppm 8.37 (m, 2H), 7.58-7.62 (m, 1H), 7.26-7.34 (m, 4H), 7.23 (s, 1H), 5.96 (s, 1H), 4.23-4.27 (m, 2H), 3.71-3.73 (m, 4H), 3.46-3.57 (m, 1H), 3.41-3.46 (m, 3H), 2.69 (s, 6H), 2.08-2.09 (m, 1H), 2.06-2.07 (m, 1H), 1.25 (s, 9H).

Example 56: Synthesis of Compound 591

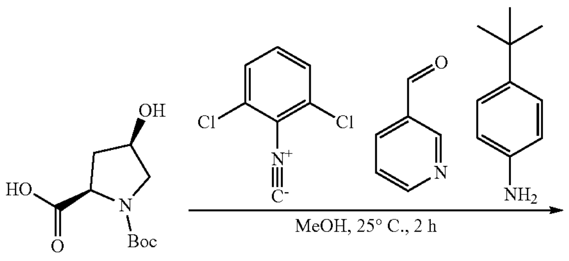

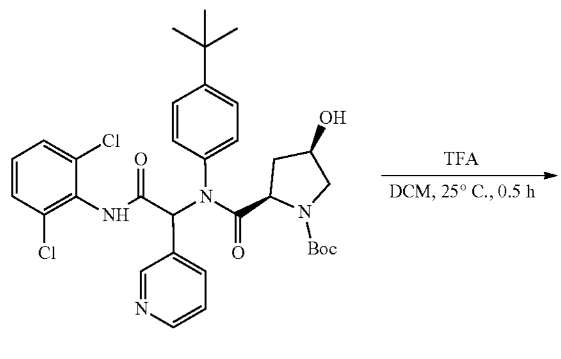

-continued

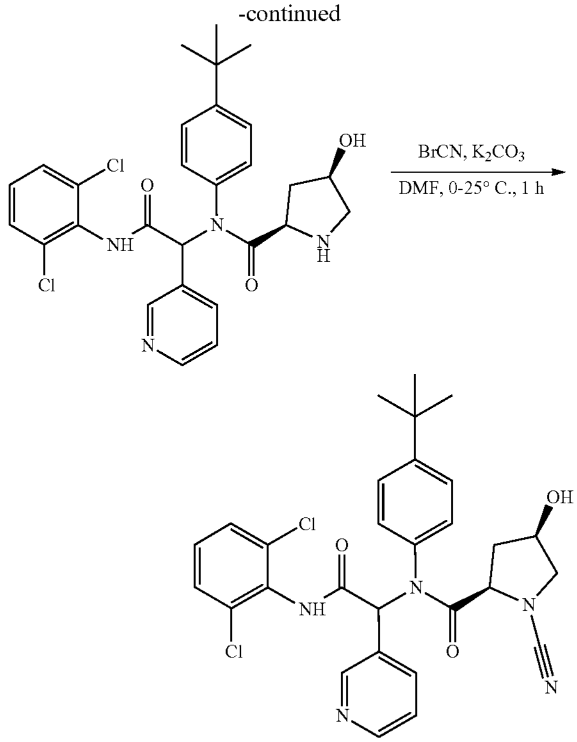

Step 1: (2R,4R)-tert-butyl 2-((4-(tert-butyl)phenyl)(2-((2,6-dichlorophenyl)amino)-2-oxo-1-(pyridin-3-yl)ethyl)carbamoyl)-4-hydroxypyrrolidine-1-carboxylate Pyridine-3-carbaldehyde (356.65 mg, 3.33 mmol, 312.85 uL, 1.1 eq), 4-tert-butylaniline (451.74 mg, 3.03 mmol, 478.03 uL, 1 eq) in MeOH (0.5 mL) was stirred at 25° C. for 0.5 h, and the (2R,4R)-1-tert-butoxycarbonyl-4-hydroxy-pyrrolidine-2-carboxylic acid (700.00 mg, 3.03 mmol, 1 eq) was added and stirred at 25° C. for 0.5 h. Then, the 1,3-dichloro-2-isocyano-benzene (520.69 mg, 3.03 mmol, 1 eq) was added and the solution was stirred at 25° C. for 1 h. Upon completion, the solution was concentrated to remove the MeOH. The residue was purified by prep-HPLC (TFA condition), column: Phenomenex luna C18 250*50 mm*10 um; mobile phase: [water (0.1% TFA)-ACN]; B %: 50%-70%, 10 min. tert-butyl (2R,4R)-2-[(4-tert-butylphenyl)-[2-(2,6-dichloroanilino)-2-oxo-1-(3-pyridyl)ethyl]carbamoyl]-4-hydroxy-pyrrolidine-1-carboxylate (240 mg, 374.07 umol, 12.36% yield, 100% purity) was obtained as an oil. MS (ESI) m/z 641.0 $[M+H]^+$.

Step 2: (2R,4R)—N-(4-(tert-butyl)phenyl)-N-(2-((2,6-dichlorophenyl)amino)-2-oxo-1-(pyridin-3-yl)ethyl)-4-hydroxypyrrolidine-2-carboxamide tert-Butyl (2R,4R)-2-[(4-tert-butylphenyl)-[2-(2,6-dichloroanilino)-2-oxo-1-(3-pyridyl)ethyl]carbamoyl]-4-hydroxy-pyrrolidine-1-carboxylate (130 mg, 202.62 umol, 1 eq) in DCM (0.5 mL)/TFA (2.50 g, 21.95 mmol, 1.62 mL, 108.32 eq) was stirred at 25° C. for 0.5 h. Upon completion, the solution was concentrated to remove the DCM and TFA, adjusted pH=8-9 by aqueous $Na_2CO_3$, extracted with DCM (20 mL*3), the combined organic phase was dried over $Na_2SO_4$, filtrated and concentrated to give the crude. The crude was used to next step directly and without further purification. (2R, 4R)—N-(4-tert-butylphenyl)-N-[2-(2,6-dichloroanilino)-2-oxo-1-(3-pyridyl)ethyl]-4-hydroxy-pyrrolidine-2-carboxamide (100 mg, crude) was obtained as a solid. MS (ESI) m/z 541.3 $[M+H]^+$.

Step 3: (2R,4R)—N-(4-(tert-butyl)phenyl)-1-cyano-N-(2-((2,6-dichlorophenyl)amino)-2-oxo-1-(pyridin-3-yl)ethyl)-4-hydroxypyrrolidine-2-carboxamide (2R, 4R)—N-(4-tert-butylphenyl)-N-[2-(2,6-dichloroanilino)-2-oxo-1-(3-pyridyl)ethyl]-4-hydroxy-pyrrolidine-2-carboxamide (30 mg, 55.40 umol, 1 eq) in DMF (0.5 mL) was added the $K_2CO_3$ (22.97 mg, 166.21 umol, 3 eq) and the solution was cooled to 0° C., then a solution of BrCN (8.80 mg, 83.11 umol, 6.11 uL, 1.5 eq) in DMF (0.2 mL) was added and the solution was stirred at 0° C. and warmed to 25° C. gradually for 1 h. Upon completion, the solution was quenched with $H_2O$ (10 mL), extracted with DCM (20 mL*3), the combined organic phase was dried over $Na_2SO_4$, filtrated and concentrated to give a residue. The residue was purified by prep-HPLC (neutral condition), column: Waters Xbridge BEH C18 100*25 mm*5 um; mobile phase: [water (10 mM $NH_4HCO_3$)-ACN]; B %: 30%-65%, 10 min. (2R, 4R)—N-(4-tert-butylphenyl)-1-cyano-N-[2-(2,6-dichloroanilino)-2-oxo-1-(3-pyridyl)ethyl]-4-hydroxy-pyrrolidine-2-carboxamide (6 mg, 10.29 umol, 18.58% yield, 97.198% purity) was obtained as a solid, $^1H$ NMR (400 MHz, DMSO-$d_6$) δ=10.26-10.12 (m, 1H), 8.49-8.30 (m, 2H), 7.85-6.96 (m, 8H), 6.85-6.47 (m, 1H), 6.46-6.24 (m, 1H), 5.24 (dd, J=6.1, 14.2 Hz, 1H), 4.20-3.92 (m, 2H), 3.56-3.43 (m, 1H), 3.23-3.10 (m, 1H), 2.03-1.88 (m, 1H), 1.83-1.61 (m, 1H), 1.19 (d, J=7.5 Hz, 9H) MS (ESI) m/z 566.0 $[M+H]^+$.

Example 57: Synthesis of Compound 595

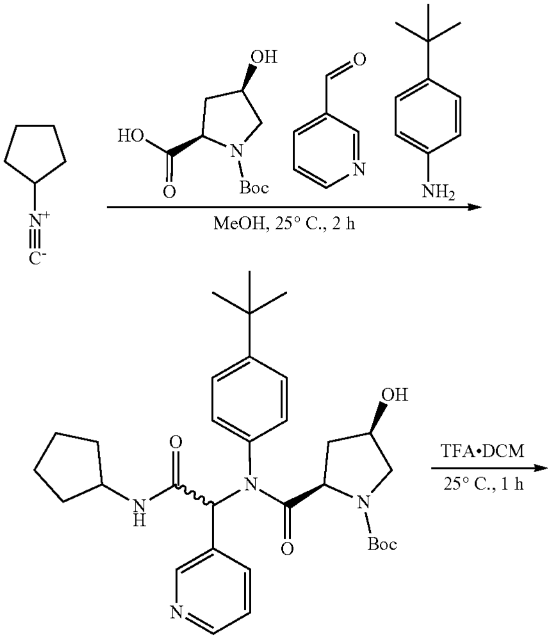

-continued

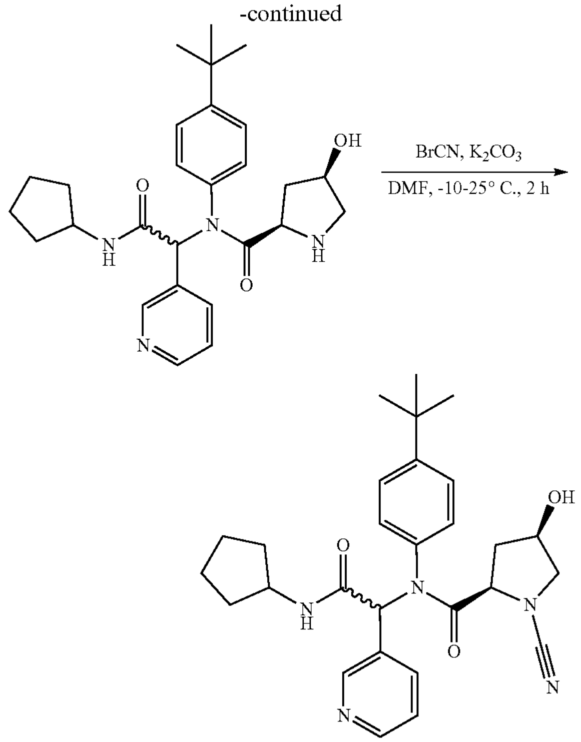

Step 1: tert-butyl (2R,4R)-2-[(4-tert-butylphenyl)-[2-(cyclopentylamino)-2-oxo-1-(3-pyridyl)ethyl]carbamoyl]-4-hydroxy-pyrrolidine-1-carboxylate A solution of pyridine-3-carbaldehyde (129.69 mg, 1.21 mmol, 113.77 uL, 1.4 eq), 4-tert-butylaniline (129.07 mg, 864.88 umol, 136.58 uL, 1 eq) in MeOH (1 mL) was stirred at 25° C. for 0.5 h, then was added (2R,4R)-1-tert-butoxycarbonyl-4-hydroxy-pyrrolidine-2-carboxylic acid (200 mg, 864.88 umol, 1 eq), isocyanocyclopentane (82.29 mg, 864.88 umol, 1 eq). The resulting mixture was stirred at 25° C. for 2 h. The solution was diluted with $H_2O$ (10 mL), extracted with EtOAc (20 mL*3), the combined organic phase was dried over $Na_2SO_4$, filtrated and concentrated to give the crude. The crude was purified by prep-TLC (petroleum ether/ethyl acetate=3:1) to get tert-butyl (2R,4R)-2-[(4-tert-butylphenyl)-[2-(cyclopentylamino)-2-oxo-1-(3-pyridyl)ethyl]carbamoyl]-4-hydroxy-pyrrolidine-1-carboxylate (350 mg, 495.83 umol, 57.33% yield, 80% purity) as an oil. MS (ESI) m/z 565.3 $[M+H]^+$ Step 2: (2R,4R)—N-(4-tert-butylphenyl)-N-[2-(cyclopentylamino)-2-oxo-1-(3-pyridyl)ethyl]-4-hydroxy-pyrrolidine-2-carboxamide A solution of tert-butyl (2R,4R)-2-[(4-tert-butylphenyl)-[2-(cyclopentylamino)-2-oxo-1-(3-pyridyl)ethyl]carbamoyl]-4-hydroxy-pyrrolidine-1-carboxylate (300 mg, 531.24 umol, 1 eq) in DCM (4 mL) was added with TFA (3.08 g, 27.01 mmol, 2.00 mL, 50.85 eq) and stirred at 25° C. for 1 h. The solution was diluted with $H_2O$ (10 mL), extracted with EtOAc (20 mL*3), the combined organic phase was dried over $Na_2SO_4$, filtrated and concentrated to give the crude. The crude was purified by prep-HPLC (column: Phenomenex luna C18 80*40 mm*3 um; mobile phase: [water (0.1% TFA)-ACN]; B %: 30%-34%, 3.5 min) to get (2R,4R)—N-(4-tert-butylphenyl)-N-[2-(cyclopentylamino)-2-oxo-1-(3-pyridyl)ethyl]-4-hydroxy-pyrrolidine-2-carboxamide (110 mg, 236.29 umol, 44.48% yield, 99.8% purity) as a solid and (2R,4R)—N-(4-tert-butylphenyl)-N-[2-(cyclopentylamino)-2-oxo-1-(3-pyridyl)ethyl]-4-hydroxy-pyrrolidine-2-carboxamide (110 mg, 236.76 umol, 44.57% yield, 100% purity) as a solid. MS (ESI) m/z 465.3 $[M+H]^+$ Step 3: (2R,4R)—N-(4-tert-butylphenyl)-1-cyano-N-[2-(cyclopentylamino)-2-oxo-1-(3-pyridyl)ethyl]-4-hydroxy-pyrrolidine-2-carboxamide To a mixture of (2R,4R)—N-(4-tert-butylphenyl)-N-[2-(cyclopentylamino)-2-oxo-1-(3-pyridyl)ethyl]-4-hydroxy-pyrrolidine-2-carboxamide (100 mg, 215.24 umol, 1 eq) in DMF (5 mL) was added $K_2CO_3$ (89.24 mg, 645.72 umol, 3 eq) and BrCN (34.20 mg, 322.86 umol, 23.75 uL, 1.5 eq) in one portion at −10° C. The mixture was stirred at 25° C. for 2 h. The aqueous phase was extracted with EtOAc (20 mL*3). The combined organic phase was washed with brine (20 mL*3), dried with anhydrous $Na_2SO_4$, filtered and concentrated in vacuum. The residue was purified by prep-HPLC (column: Phenomenex Gemini-NX 80*40 mm*3 um; mobile phase: [water (10 mM $NH_4HCO_3$)-ACN]; B %: 20%-50%, 8 min) to get (2R,4R)—N-(4-tert-butylphenyl)-1-cyano-N-[2-(cyclopentylamino)-2-oxo-1-(3-pyridyl)ethyl]-4-hydroxy-pyrrolidine-2-carboxamide (30 mg, 60.05 umol, 27.90% yield, 98% purity) as a solid. MS (ESI) m/z 490.1 $[M+H]^+$. $^1H$ NMR (400 MHz, METHANOL-$d_4$) δ ppm 8.23-8.46 (m, 2H), 7.03-7.86 (m, 5H), 6.58 (br s, 1H), 6.04 (s, 1H), 4.19-4.29 (m, 2H), 4.14 (quin, J=6.50 Hz, 1H), 3.57 (dd, J=9.48, 5.51 Hz, 1H), 3.43 (dd, J=9.48, 3.97 Hz, 1H), 2.04-2.16 (m, 1H), 1.79-2.03 (m, 3H), 1.48-1.76 (m, 5H), 1.32 (dt, J=12.90, 6.34 Hz, 1H), 1.25 (s, 9H).

Step 4: (2R)—N-(4-tert-butylphenyl)-1-cyano-N-[2-(cyclohexylamino)-2-oxo-1-(3-pyridyl)ethyl]-4,4-dimethyl-pyrrolidine-2-carboxamide To a mixture of (2R,4R)—N-(4-tert-butylphenyl)-N-[2-(cyclopentylamino)-2-oxo-1-(3-pyridyl)ethyl]-4-hydroxy-pyrrolidine-2-carboxamide (100 mg, 215.24 umol, 1 eq) in DMF (5 mL) was added $K_2CO_3$ (89.24 mg, 645.72 umol, 3 eq) and BrCN (34.20 mg, 322.86 umol, 23.75 uL, 1.5 eq) in one portion at −10° C. The mixture was stirred at 25° C. for 2 h. The aqueous phase was extracted with EtOAc (20 mL*3). The combined organic phase was washed with brine (20 mL*3), dried with anhydrous $Na_2SO_4$, filtered and concentrated in vacuum. The residue was purified by prep-HPLC (column: Phenomenex Gemini-NX 80*40 mm*3 um; mobile phase: [water (10 mM $NH_4$HCO3)-ACN]; B %: 20%-50%, 8 min) to get (2R,4R)—N-(4-tert-butylphenyl)-1-cyano-N-[2-(cyclopentylamino)-2-oxo-1-(3-pyridyl)ethyl]-4-hydroxy-pyrrolidine-2-carboxamide (30 mg, 60.05 umol, 27.90% yield, 98% purity) as a solid. MS (ESI) m/z 490.1 $[M+H]^+$. $^1H$ NMR (400 MHz, METHANOL-$d_4$) δ ppm 8.18-8.44 (m, 2H), 7.02-7.83 (m, 5H), 6.64 (br s, 1H), 6.16 (s, 1H), 4.07-4.30 (m, 3H), 3.57 (dd, J=9.37, 5.62 Hz, 1H), 3.36-3.48 (m, 1H), 2.09-2.21 (m, 1H), 1.80-2.07 (m, 3H), 1.45-1.78 (m, 5H), 1.17-1.41 (m, 10H).

Example 58: Synthesis of Compound 619

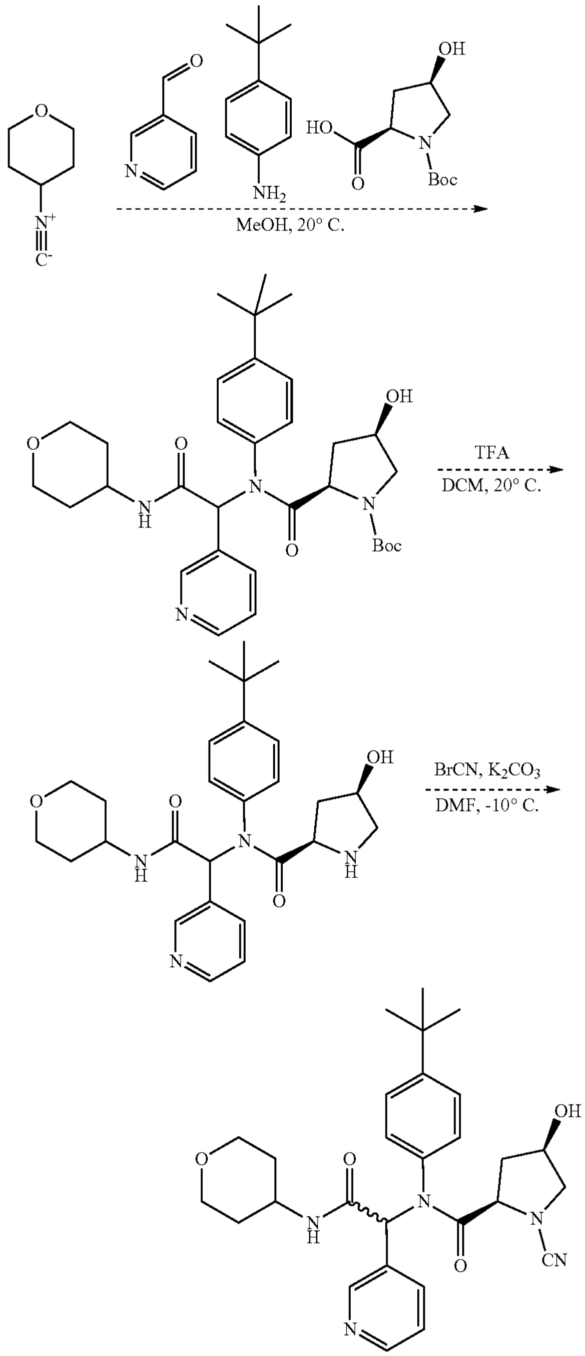

Step 1: (2R,4R)-tert-butyl 2-((4-(tert-butyl)phenyl)(2-oxo-1-(pyridin-3-yl)-2-((tetrahydro-2H-pyran-4-yl)amino)ethyl)carbamoyl)-4-hydroxypyrrolidine-1-carboxylate A solution of pyridine-3-carbaldehyde (200 mg, 1.87 mmol, 175.44 uL, 1 eq), 4-tert-butylaniline (278.65 mg, 1.87 mmol, 294.87 uL, 1 eq) in MeOH (9 mL) was stirred for 1 h, and then (2R,4R)-1-tert-butoxycarbonyl-4-hydroxy-pyrrolidine-2-carboxylic acid (431.79 mg, 1.87 mmol, 1 eq) was added. The solution was stirred for 10 min, then 4-isocyanotetrahydro-2H-pyran (207.53 mg, 1.87 mmol, 1 eq) in MeOH (1 mL) was added. The mixture was stirred at 25° C. for 14 h 50 min. Upon completion, the reaction mixture was concentrated under reduced pressure to remove solvent. The residue was purified by prep-HPLC (column: Waters Xbridge Prep OBD C18 150*40 mm*10 um; mobile phase: [water (0.05% NH3H2O+10 mM NH4HCO3)-ACN]; B %: 35%-55%, 8 min) to give (2R,4R)-tert-butyl 2-((4-(tert-butyl)phenyl)(2-oxo-1-(pyridin-3-yl)-2-((tetrahydro-2H-pyran-4-yl)amino)ethyl)carbamoyl)-4-hydroxy-pyrrolidine-1-carboxylate (320 mg, 551.05 umol, 29.51% yield) and (2R,4R)-tert-butyl 2-((4-(tert-butyl)phenyl)(2-oxo-1-(pyridin-3-yl)-2-((tetrahydro-2H-pyran-4-yl)amino)ethyl)carbamoyl)-4-hydroxypyrrolidine-1-carboxylate (305 mg, 525.22 umol, 28.13% yield) as a solid. MS (ESI) m/z 581.4 $[M+H]^+$ Step 2: (2R,4R)—N-(4-(tert-butyl)phenyl)-4-hydroxy-N-(2-oxo-1-(pyridin-3-yl)-2-((tetrahydro-2H-pyran-4-yl)amino)ethyl)pyrrolidine-2-carboxamide Isomer 1: To a solution of (2R,4R)-tert-butyl 2-((4-(tert-butyl)phenyl)(2-oxo-1-(pyridin-3-yl)-2-((tetrahydro-2H-pyran-4-yl)amino)ethyl)carbamoyl)-4-hydroxypyrrolidine-1-carboxylate (320 mg, 551.05 umol, 1 eq) in DCM (5 mL) was added TFA (1.64 g, 14.41 mmol, 1.07 mL, 26.14 eq). The mixture was stirred at 25° C. for 2 h. Upon completion, the reaction mixture was quenched by addition $NaHCO_3$ (30 mL) at 25° C., and then extracted with DCM (35 mL*3). The combined organic layers were washed with brine (35 mL*2), dried over $Na_2SO_4$, filtered and concentrated under reduced pressure to give (2R,4R)—N-(4-(tert-butyl)phenyl)-4-hydroxy-N-(2-oxo-1-(pyridin-3-yl)-2-((tetrahydro-2H-pyran-4-yl)amino)ethyl)pyrrolidine-2-carboxamide (260 mg, crude) as a solid. MS (ESI) m/z 481.3 $[M+H]^+$ Isomer 2: To a solution of (2R,4R)-tert-butyl 2-((4-(tert-butyl)phenyl)(2-oxo-1-(pyridin-3-yl)-2-((tetrahydro-2H-pyran-4-yl)amino)ethyl)carbamoyl)-4-hydroxypyrrolidine-1-carboxylate (305 mg, 525.22 umol, 1 eq) in DCM (5 mL) was added TFA (1.54 g, 13.51 mmol, 1 mL, 25.72 eq). The mixture was stirred at 25° C. for 2 h. Upon completion, the reaction mixture was quenched by addition $NaHCO_3$ (30 mL) at 25° C., and then extracted with DCM (35 mL*3). The combined organic layers were washed with brine (35 mL*2), dried over $Na_2SO_4$, filtered and concentrated under reduced pressure to give (2R,4R)—N-(4-(tert-butyl)phenyl)-4-hydroxy-N-(2-oxo-1-(pyridin-3-yl)-2-((tetrahydro-2H-pyran-4-yl)amino)ethyl)pyrrolidine-2-carboxamide (250 mg, crude) as a solid. MS (ESI) m/z 481.3 $[M+H]^+$ Step 3 (2R,4R)—N-(4-(tert-butyl)phenyl)-1-cyano-4-hydroxy-N-(2-oxo-1-(pyridin-3-yl)-2-((tetrahydro-2H-pyran-4-yl)amino)ethyl)pyrrolidine-2-carboxamide Compound 619 Isomer 1: To a solution of (2R,4R)—N-(4-(tert-butyl)phenyl)-4-hydroxy-N-(2-oxo-1-(pyridin-3-yl)-2-((tetrahydro-2H-pyran-4-yl)amino)ethyl)pyrrolidine-2-carboxamide (200 mg, 416.15 umol, 1 eq) in DMF (5 mL) was added $K_2CO_3$ (172.54 mg, 1.25 mmol, 3 eq), and then BrCN (52.89 mg, 499.38 umol, 36.73 uL, 1.2 eq) was added at −10° C. The mixture was stirred at −10° C. for 2 h. Upon completion, the reaction mixture was poured into water (30 mL) at 25° C., and then extracted with EtOAc (30 mL*3). The combined organic layers were washed with brine (30 mL*2), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM NH4HCO3)-ACN]; B %: 40%-60%, 8 min) to give (2R, 4R)—N-(4-(tert-butyl)phenyl)-1-cyano-4-hydroxy-N-(2-oxo-1-(pyridin-3-yl)-2-((tetrahydro-2H-pyran-4-yl)amino) ethyl)pyrrolidine-2-carboxamide (105 mg, 207.34 umol, 49.82% yield, 99.84% purity) as a solid. MS (ESI) m/z 506.2 $[M+H]^+$ Compound 619 Isomer 1: $^1H$ NMR (400 MHz, METHANOL-$d_4$) δ=8.30 (s, 2H), 7.78-7.58 (m, 1H), 7.54 (d, J=7.9 Hz, 1H), 7.49-7.31 (m, 1H), 7.30-7.05 (m, 2H), 6.83-6.48 (m, 1H), 6.17 (s, 1H), 4.30-4.16 (m, 2H), 4.01-3.90 (m, 2H), 3.90-3.82 (m, 1H), 3.58 (d, J=5.7, 9.4 Hz, 1H), 3.53-3.38 (m, 3H), 2.20-2.09 (m, 1H), 2.00 (d, J=5.4, 13.2 Hz, 1H), 1.91 (d, J=1.8, 13.0 Hz, 1H), 1.73 (d, J=1.9, 12.8 Hz, 1H), 1.63-1.50 (m, 1H), 1.44-1.31 (m, 1H), 1.28-1.17 (m, 9H).

Compound 619 Isomer 2: To a solution of (2R,4R)—N-(4-(tert-butyl)phenyl)-4-hydroxy-N-(2-oxo-1-(pyridin-3-yl)-2-((tetrahydro-2H-pyran-4-yl)amino)ethyl)pyrrolidine-2-carboxamide (200 mg, 416.15 umol, 1 eq) in DMF (5 mL) was added $K_2CO_3$ (172.54 mg, 1.25 mmol, 3 eq), and then BrCN (52.89 mg, 499.38 umol, 36.73 uL, 1.2 eq) was added at −10° C. The mixture was stirred at −10° C. for 2 hr. Upon completion, the reaction mixture was poured into water 30 mL at 25° C., and then extracted with EtOAc (30 mL*3). The combined organic layers were washed with brine (30 mL*2), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM NH4HCO3)-ACN]; B %: 40%-60%, 8 min) to give (2R, 4R)—N-(4-(tert-butyl)phenyl)-1-cyano-4-hydroxy-N-(2-oxo-1-(pyridin-3-yl)-2-((tetrahydro-2H-pyran-4-yl)amino) ethyl)pyrrolidine-2-carboxamide (102 mg, 200.31 umol, 48.13% yield, 99.29% purity) as a solid. MS (ESI) m/z 506.2 $[M+H]^+$ Compound 619 Isomer 2: $^1H$ NMR (400 MHz, METHANOL-$d_4$) δ=8.39-8.31 (m, 2H), 7.71 (s, 1H), 7.55 (d, J=8.1 Hz, 1H), 7.44 (s, 1H), 7.28-7.04 (m, 2H), 6.60 (s, 1H), 6.03 (s, 1H), 4.29-4.19 (m, 2H), 3.93 (s, J=5.0, 10.1 Hz, 2H), 3.88-3.82 (m, 1H), 3.57 (d, J=5.4, 9.5 Hz, 1H), 3.53-3.39 (m, 3H), 2.15-2.04 (m, 1H), 1.98-1.86 (m, 2H), 1.71 (d, J=1.8, 12.8 Hz, 1H), 1.62-1.48 (m, 1H), 1.44-1.31 (m, 1H), 1.24 (s, 911).

Example 59: Synthesis of Compound 627

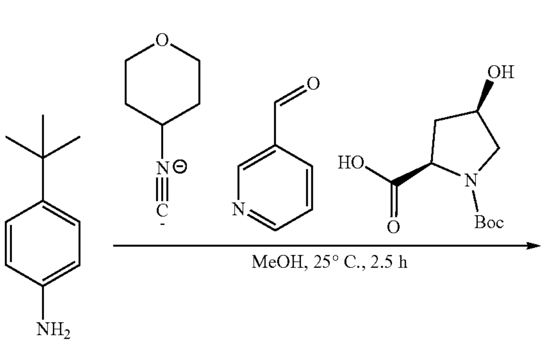

-continued

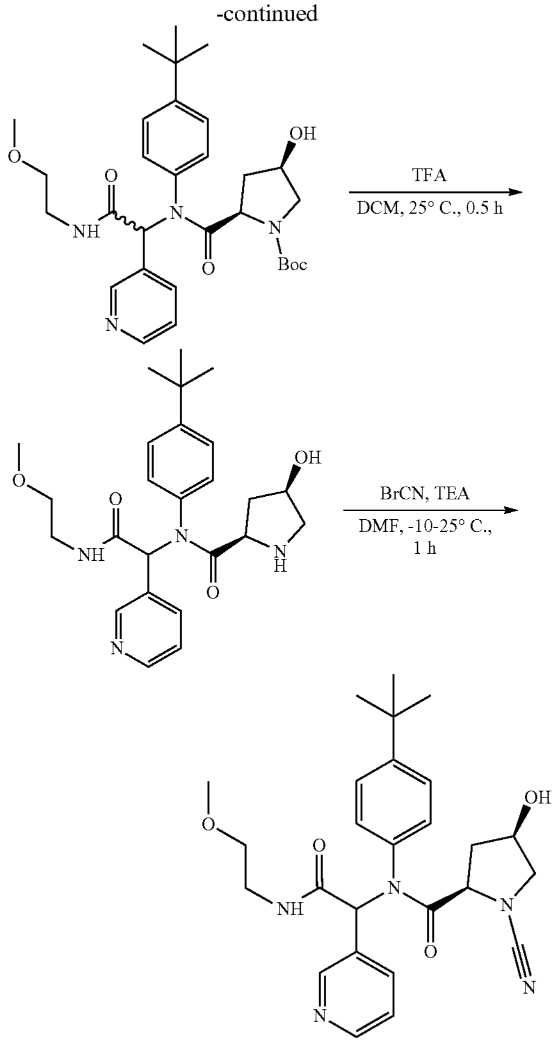

Step 1: (2R,4R)-tert-butyl2-((4-(tert-butyl)phenyl) (2-((2-methoxyethyl)amino)-2-oxo-1-(pyridin-3-yl) ethyl)carbamoyl)-4-hydroxypyrrolidine-1-carboxylate 4-tert-Butylaniline (263.03 mg, 1.76 mmol, 278.34 uL, 1 eq) and pyridine-3-carbaldehyde (188.79 mg, 1.76 mmol, 165.60 uL, 1 eq) in MeOH (5 mL) was stirred at 25° C. for 20 min, and then (2R,4R)-1-tert-butoxycarbonyl-4-hydroxy-pyrrolidine-2-carboxylic acid (407.58 mg, 1.76 mmol, 1 eq) was added. The resulting mixture was stirred for 10 min and then 1-isocyano-2-methoxy-ethane (150 mg, 1.76 mmol, 1 eq) was added. The mixture was stirred at 25° C. for 2 h. Upon completion, the mixture was concentrated under the reduced pressure to give a residue. The residue was purified by prep-HPLC affording the product tert-butyl(2R,4R)-2-[(4-tert-butylphenyl)-[2-(2-methoxyethylamino)-2-oxo-1-(3-pyridyl)ethyl]carbamoyl]-4-hydroxy-pyrrolidine-1-carboxylate (360 mg, 649.03 umol, 36.82% yield) MS (ESI) m/z 555.3 $[M+H]^+$ Prep-HPLC condition: column: Kromasil C18 (250*50 mm*10 um); mobile phase: [water (10 mM $NH_4HCO_3$)-ACN]; B %: 30%-70%, 10 min tert-butyl(2R, 4R)-2-[(4-tert-butylphenyl)-[2-(2-methoxyethylamino)-2-oxo-1-(3-pyridyl)ethyl]carbamoyl]-4-hydroxy-pyrrolidine-1-carboxylate (350 mg, 631.00 umol, 35.80% yield, - purity)

as an oil. MS (ESI) m/z 555.3 $[M+H]^+$ Prep-HPLC condition: column: Kromasil C18 (250*50 mm*10 um); mobile phase: [water (10 mM $NH_4HCO_3$)-ACN]; B %: 30%-70%, 10 min.

Step 2: (2R,4R)—N-(4-(tert-butyl)phenyl)-4-hydroxy-N-(2-((2-methoxyethyl)amino)-2-oxo-1-(pyridin-3-yl)ethyl)pyrrolidine-2-carboxamide Isomer 1: tert-Butyl(2R,4R)-2-[(4-tert-butylphenyl)-[2-(2-methoxyethylamino)-2-oxo-1-(3-pyridyl)ethyl]carbamoyl]-4-hydroxypyrrolidine-1-carboxylate (350 mg, 631.00 umol, 1 eq) in DCM (4 mL) was added TFA (3.08 g, 27.01 mmol, 2 mL, 42.81 eq). The mixture was stirred at 25° C. for 0.5 h. Upon completion, the reaction mixture was quenched by addition sat. $NaHCO_3$ (10 mL), and then extracted with DCM (10 mL*3). The combined organic layers were washed with brine 10 mL, dried over $Na_2SO_4$, filtered and concentrated under reduced pressure affording the product (2R, 4R)—N-(4-tert-butylphenyl)-4-hydroxy-N-[2-(2-methoxyethylamino)-2-oxo-1-(3-pyridyl)ethyl]pyrrolidine-2-carboxamide (160 mg, crude) as an oil. MS (ESI) m/z 455.1 $[M+H]^+$ Isomer 2: tert-Butyl(2R,4R)-2-[(4-tert-butylphenyl)-[2-(2-methoxyethylamino)-2-oxo-1-(3-pyridyl)ethyl]carbamoyl]-4-hydroxypyrrolidine-1-carboxylate (350 mg, 631.00 umol, 1 eq) in DCM (4 mL) was added TFA (3.08 g, 27.01 mmol, 2 mL, 42.81 eq). The mixture was stirred at 25° C. for 0.5 h. Upon completion, the reaction mixture was quenched by addition sat. $NaHCO_3$ (10 mL), and then extracted with DCM (10 mL*3). The combined organic layers were washed with brine (10 mL), dried over $Na_2SO_4$, filtered and concentrated under reduced pressure affording the product (2R, 4R)—N-(4-tert-butylphenyl)-4-hydroxy-N-[2-(2-methoxyethylamino)-2-oxo-1-(3-pyridyl)ethyl]pyrrolidine-2-carboxamide (150 mg, crude) as an oil. MS (ESI) m/z 455.1 $[M+H]^+$ Step 3: (2R,4R)—N-(4-(tert-butyl)phenyl)-1-cyano-4-hydroxy-N-(2-((2-methoxyethyl)amino)-2-oxo-1-(pyridin-3-yl)ethyl)pyrrolidine-2-carboxamide Compound 627 Isomer 1: (2R,4R)—N-(4-tert-butylphenyl)-4-hydroxy-N-[2-(2-methoxyethylamino)-2-oxo-1-(3-pyridyl)ethyl]pyrrolidine-2-carboxamide (150 mg, 329.99 umol, 1 eq) in DCM (2 mL) was added with TEA (100.17 mg, 989.97 umol, 137.79 uL, 3 eq) and the solution was cooled to −10° C. A solution of BrCN (41.94 mg, 395.99 umol, 29.13 uL, 1.2 eq) in DCM (0.5 mL) was added and the solution stirred for 1 h at 0° C. and warmed to 25° C. gradually. Upon completion, the reaction mixture was quenched by addition sat. $NaHCO_3$ 10 mL, and then extracted with DCM (10 mL*3). The combined organic layers were washed with brine (10 mL), dried over $Na_2SO_4$, filtered and concentrated under reduced pressure to give a residue. The residue was purified by prep-HPLC affording the product (2R,4R)—N-(4-tert-butylphenyl)-1-cyano-4-hydroxy-N-[2-(2-methoxyethylamino)-2-oxo-1-(3-pyridyl)ethyl]pyrrolidine-2-carboxamide (53.77 mg, 109.32 umol, 33.13% yield, 97.5% purity) as a solid. MS (ESI) m/z 480.2 $[M+H]^+$ Prep-HPLC condition: column: Waters Xbridge BEH C18 100*25 mm*5 um; mobile phase: [water (10 mM $NH_4HCO_3$)-ACN]; B %: 20%-50%, 10 min $^1H$ NMR (400 MHz, MeOD-$d_4$) δ=8.29 (d, J=2.4 Hz, 2H), 7.86-7.00 (m, 5H), 6.94-6.41 (m, 1H), 6.25 (s, 1H), 4.31-4.18 (m, 2H), 3.58 (dd, J=5.6, 9.4 Hz, 1H), 3.52-3.33 (m, 5H), 3.28 (s, 3H), 2.18-2.09 (m, 1H), 2.06-1.98 (m, 1H), 1.37-1.21 (m, 9H).

Compound 627 Isomer 2: (2R,4R)—N-(4-tert-butylphenyl)-4-hydroxy-N-[2-(2-methoxyethylamino)-2-oxo-1-(3-pyridyl)ethyl]pyrrolidine-2-carboxamide (150 mg, 329.99 umol, 1 eq) in DCM (2 mL) was added TEA (100.17 mg, 989.97 umol, 137.79 uL, 3 eq) and the solution was cooled to −10° C. A solution of BrCN (41.94 mg, 395.99 umol, 29.13 uL, 1.2 eq) in DCM (0.5 mL) was added and the solution stirred for 1 h at 0° C. and warmed to 25° C. gradually. Upon completion, the reaction mixture was quenched by addition sat. $NaHCO_3$ (10 mL), and then extracted with DCM (10 mL*3). The combined organic layers were washed with brine (10 mL), dried over $Na_2SO_4$, filtered and concentrated under reduced pressure to give a residue. The residue was purified by prep-HPLC affording the product (2R,4R)—N-(4-tert-butylphenyl)-1-cyano-4-hydroxy-N-[2-(2-methoxyethylamino)-2-oxo-1-(3-pyridyl)ethyl]pyrrolidine-2-carboxamide (53.07 mg, 103.47 umol, 31.36% yield, 93.5% purity) as a solid. MS (ESI) m/z 480.2 $[M+H]^+$ Prep-HPLC condition: column: Waters Xbridge BEH C18 100*25 mm*5 um; mobile phase: [water (10 mM $NH_4HCO_3$)-ACN]; B %: 20%-50%, 10 min $^1H$ NMR (400 MHz, MeOD-$d_4$) δ=8.45-8.15 (m, 2H), 7.75-7.17 (m, 5H), 6.66 (br s, 1H), 6.05 (s, 1H), 4.36-4.17 (m, 2H), 3.57 (dd, J=5.4, 9.6 Hz, 1H), 3.49-3.33 (m, 5H), 3.28 (s, 3H), 2.16-2.05 (m, 1H), 1.94 (td, J=4.6, 13.2 Hz, 1H), 1.38-1.24 (m, 9H)

Example 60: Synthesis of Compound 643

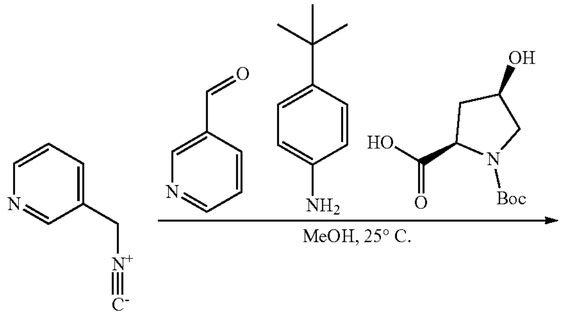

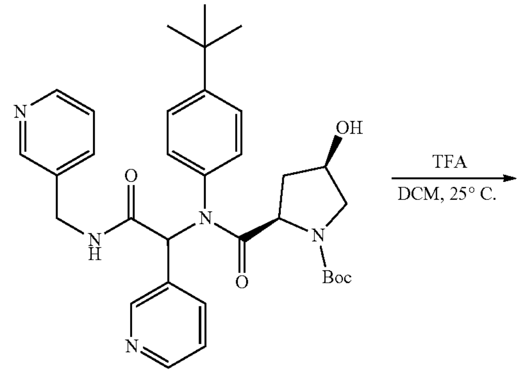

-continued

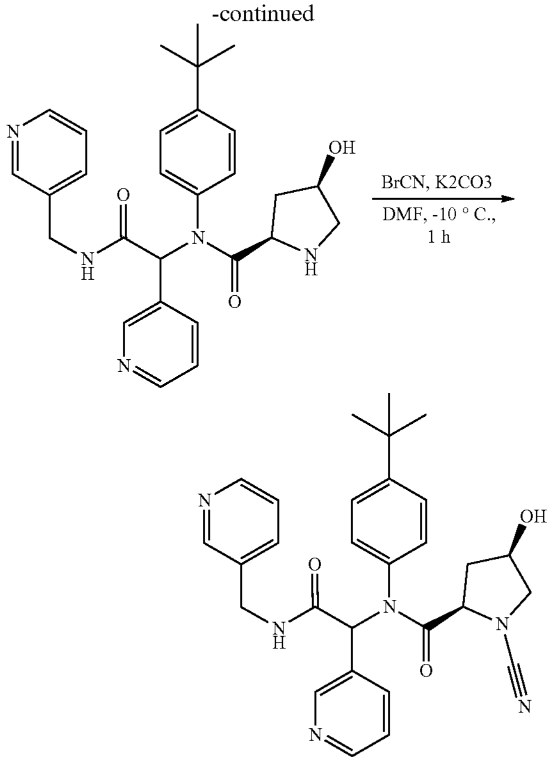

Step 1: (2R,4R)-tert-butyl 2-((4-(tert-butyl)phenyl)(2-oxo-1-(pyridin-3-yl)-2-((pyridin-3-ylmethyl)amino)ethyl)carbamoyl)-4-hydroxypyrrolidine-1-carboxylate A solution of pyridine-3-carbaldehyde (181.33 mg, 1.69 mmol, 159.06 uL, 1 eq), 4-tert-butylaniline (252.64 mg, 1.69 mmol, 267.35 uL, 1 eq), (2R,4R)-1-tert-butoxycarbonyl-4-hydroxy-pyrrolidine-2-carboxylic acid (391.49 mg, 1.69 mmol, 1 eq) and 3-(isocyanomethyl)pyridine (200 mg, 1.69 mmol, 1 eq) in MeOH (8 mL) was stirred at 25° C. for 14 h. The reaction mixture was concentrated under reduced pressure, then purified by prep-HPLC to give the product (2R,4R)-tert-butyl 2-((4-(tert-butyl)phenyl)(2-oxo-1-(pyridin-3-yl)-2-((pyridin-3-ylmethyl)amino)ethyl)carbamoyl)-4-hydroxypyrrolidine-1-carboxylate (330 mg, 533.43 umol, 31.51% yield, 95% purity) as a solid, and (2R,4R)-tert-butyl 2-((4-(tert-butyl)phenyl)(2-oxo-1-(pyridin-3-yl)-2-((pyridin 3-ylmethyl)amino)ethyl)carbamoyl)-4-hydroxypyrrolidine-1-carboxylate (321 mg, 518.88 umol, 30.65% yield, 95% purity) as a solid. MS (ESI) m/z 588.4 $[M+H]^+$ prep-HPLC condition: column: Kromasil C18 (250*50 mm*10 um); mobile phase: [water (10 mM NH4HCO3)-ACN]; B %: 30%-70%, 10 min.

Step 2: (2R,4R)—N-(4-(tert-butyl)phenyl)-4-hydroxy-N-(2-oxo-1-(pyridin-3-yl)-2-((pyridin-3-ylmethyl)amino)ethyl)pyrrolidine-2-carboxamide Isomer 1: A solution of (2R,4R)-tert-butyl 2-((4-(tert-butyl)phenyl)(2-oxo-1-(pyridin-3-yl)-2-((pyridin-3-ylmethyl)amino)ethyl)carbamoyl)-4-hydroxypyrrolidine-1-carboxylate (305 mg, 518.97 umol, 1 eq), and TFA (1.54 g, 13.51 mmol, 1 mL, 26.02 eq) in DCM (3 mL) was stirred at 25° C. for 1 h. The reaction mixture was concentrated under reduced pressure, adjusted to pH=7-8 with aq. $NaHCO_3$ (20 mL) and extracted with EtOAc (20.0*3 mL). The organic layers were washed with brine (20.0 mL), dried over $Na_2SO_4$, filtered, concentrated under reduced pressure to give (2R,4R)—N-(4-(tert-butyl)phenyl)-4-hydroxy-N-(2-oxo-1-(pyridin-3-yl)-2-((pyridin-3-ylmethyl)amino)ethyl)pyrrolidine-2-carboxamide (326 mg, crude) as a solid. MS (ESI) m/z 488.3 $[M+H]^+$.

Isomer 2: A solution of (2R,4R)-tert-butyl 2-((4-(tert-butyl)phenyl)(2-oxo-1-(pyridin-3-yl)-2-((pyridin-3-ylmethyl)amino)ethyl)carbamoyl)-4-hydroxypyrrolidine-1-carboxylate (311 mg, 529.17 umol, 1 eq), TFA (4.79 g, 42.00 mmol, 3.11 mL, 79.38 eq) in DCM (9 mL) was stirred at 25° C. for 0.5 h. The reaction mixture was concentrated under reduced pressure, adjusted to pH=7-8 with aq. $NaHCO_3$ (20 mL) and extracted with EtOAc (20.0*3 mL). The organic layers were washed with brine (20.0 mL), dried over $Na_2SO_4$, filtered, concentrated under reduced pressure to give (2R,4R)—N-(4-(tert-butyl)phenyl)-4-hydroxy-N-(2-oxo-1-(pyridin-3-yl)-2-((pyridin-3-ylmethyl)amino)ethyl)pyrrolidine-2-carboxamide (344 mg, crude) as a solid. MS (ESI) m/z 488.3 $[M+H]^+$.

Step 3: (2R,4R)—N-(4-(tert-butyl)phenyl)-1-cyano-4-hydroxy-N-(2-oxo-1-(pyridin-3-yl)-2-((pyridin-3-ylmethyl)amino)ethyl)pyrrolidine-2-carboxamide Compound 643 Isomer 1: To a solution of (2R,4R)—N-(4-(tert-butyl)phenyl)-4-hydroxy-N-(2-oxo-1-(pyridin-3-yl)-2-((pyridin-3-ylmethyl)amino)ethyl)pyrrolidine-2-carboxamide (305 mg, 625.52 umol, 1 eq) in DMF (3 mL) was added $K_2CO_3$ (259.35 mg, 1.88 mmol, 3 eq), and then BrCN (67.58 mg, 638.03 umol, 46.93 uL, 1.02 eq) under $N_2$ at −10° C. The resulting mixture was stirred at −10° C. for 1 h. Then, the mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R,4R)—N-(4-(tert-butyl)phenyl)-1-cyano-4-hydroxy-N-(2-oxo-1-(pyridin-3-yl)-2-((pyridin-3-ylmethyl)amino)ethyl)pyrrolidine-2-carboxamide (96.12 mg, 177.76 umol, 28.42% yield, 94.8% purity) as a solid. MS (ESI) m/z 513.1 $[M+H]^+$. prep-HPLC condition (Compound 643 Isomer 1): column: Waters Xbridge BEH C18 100*25 mm*5 um; mobile phase: [water (10 mM NH4HCO3)-ACN]; B %: 25%-55%, 10 min. $^1H$ NMR (400 MHz, MeOD-$d_4$) δ ppm 8.49-8.44 (m, 1H), 8.44-8.39 (m, 1H), 8.38-8.26 (m, 2H), 7.85-7.75 (m, 1H), 7.72-7.48 (m, 2H), 7.46-7.09 (m, 4H), 6.67 (s, 1H), 6.22 (s, 1H), 4.61-4.38 (m, 2H), 4.30-4.18 (m, 2H), 3.64-3.54 (m, 1H), 3.48-3.39 (m, 1H), 2.22-2.09 (m, 1H), 2.05-1.96 (m, 1H), 1.28-1.19 (m, 9H).

Compound 643 Isomer 2: To a solution of (2R,4R)—N-(4-(tert-butyl)phenyl)-4-hydroxy-N-(2-oxo-1-(pyridin-3-yl)-2-((pyridin-3-ylmethyl)amino)ethyl)pyrrolidine-2-carboxamide (324 mg, 664.49 umol, 1 eq) in DMF (3 mL) was added $K_2CO_3$ (275.51 mg, 1.99 mmol, 3 eq), and then BrCN (71.79 mg, 677.78 umol, 49.86 uL, 1.02 eq) under $N_2$ at −10° C. The resulting mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R,4R)—N-(4-(tert-butyl)phenyl)-1-cyano-4-hydroxy-N-(2-oxo-1-(pyridin-3-yl)-2-((pyridin-3-ylmethyl)amino)ethyl)pyrrolidine-2-carboxamide (50.91 mg, 80.55 umol, 12.12% yield, 81.1% purity) as a solid. MS (ESI) m/z 513.2 $[M+H]^+$. prep-HPLC condition (Compound 643 Isomer 2): column: Waters Xbridge BEH C18 100*25 mm*5 um; mobile phase: [water (10 mM NH4HCO3)-ACN]; B %: 25%-55%, 10 min. $^1H$ NMR (Compound 643 Isomer 2) (400 MHz, MeOD-$d_4$) δ ppm 8.49-8.44 (m, 1H), 8.43-8.38 (m, 1H), 8.37-8.26 (m, 2H), 7.86-7.75 (m, 1H), 7.70-7.50 (m, 2H), 7.44-7.17 (m, 4H), 6.67 (s, 1H), 6.02 (s, 1H), 4.56-4.37 (m, 2H), 4.32-4.18 (m, 2H), 3.63-3.54 in, 1H), 3.50-3.38 (m, 1H), 2.20-1.88 (m, 2H), 1.29-1.20 (m, 9H).

Example 61: Synthesis of Compound 647

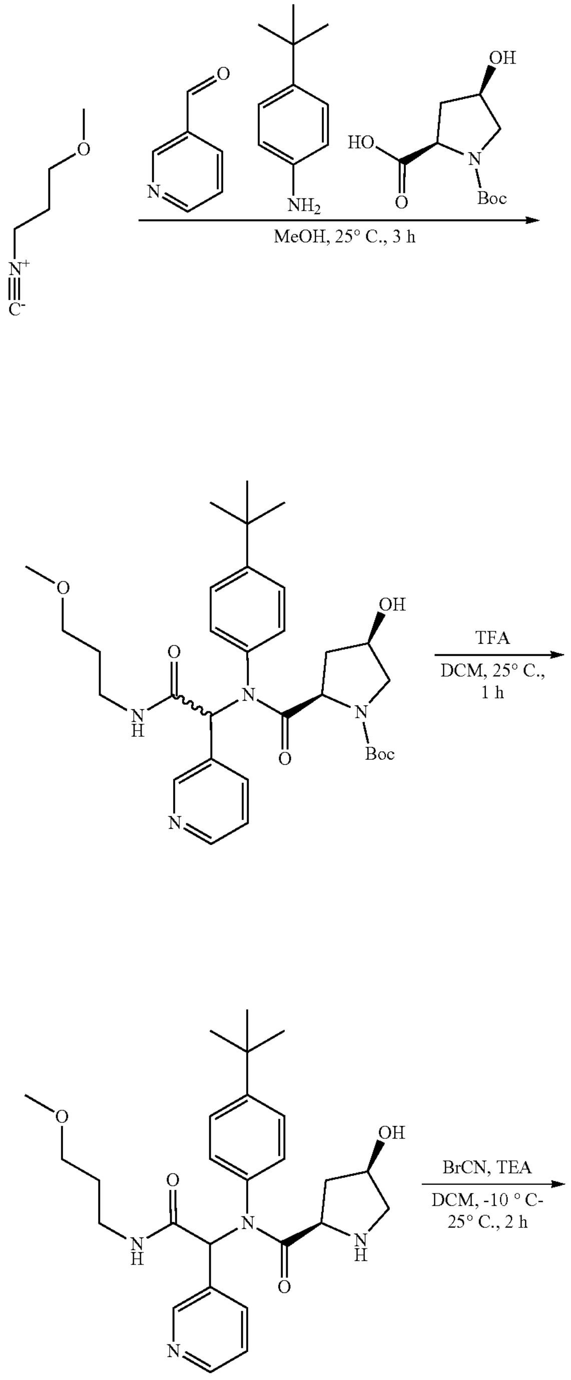

-continued

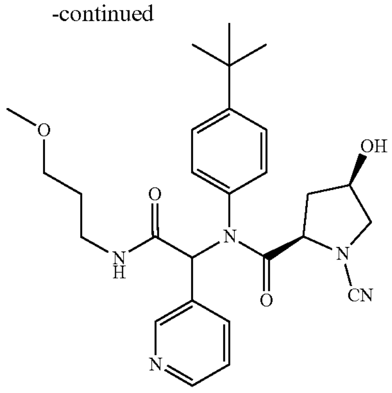

Step1:(2R,4R)-tert-butyl2-((4-(tert-butyl)phenyl)(2-((3-methoxypropyl)amino)-2-oxo-1-(pyridin-3-yl)ethyl)carbamoyl)-4-hydroxypyrrolidine-1-carboxylate A solution of nicotinaldehyde (348.16 mg, 3.25 mmol, 305.40 uL, 1 eq), 4-(tert-butyl)aniline (485.08 mg, 3.25 mmol, 513.31 uL, 1 eq) in MeOH (5 mL) was stirred at 25° C. for 1 h, and the mixture was added with (2R,4R)-1-(tert-butoxycarbonyl)-4-hydroxypyrrolidine-2-carboxylic acid (751.66 mg, 3.25 mmol, 1 eq) and then the reaction was stirred at 25° C. for 0.5 h. The resulting mixture was added with 1-isocyano-3-methoxypropane (290 mg, 2.93 mmol, 0.9 eq) and the mixture was stirred at 25° C. for 1.5 h. Upon completion, the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: %-%, 8 min) to give a product (2R,4R)-tert-butyl2-((4-(tert-butyl)phenyl)(2-((3-methoxypropyl)amino)-2-oxo-1-(pyridin-3-yl)ethyl)carbamoyl)-4-hydroxypyrrolidine-1-carboxylate (450 mg, 791.27 umol, 24.34% yield) and (2R,4R)-tert-butyl2-((4-(tert-butyl)phenyl)(2-((3-methoxypropyl)amino)-2-oxo-1-(pyridin-3-yl)ethyl)carbamoyl)-4-hydroxypyrrolidine-1-carboxylate (380 mg, 668.19 umol, 20.56% yield) as an oil. MS (ESI) m/z 569.3 $[M+H]^+$ Step2:(2R,4R)—N-(4-(tert-butyl)phenyl)-4-hydroxy-N-(2-((3-methoxypropyl)amino)-2-oxo-1-(pyridin-3-yl)ethyl)pyrrolidine-2-carboxamide Isomer 1: To a solution of (2R,4R)-tert-butyl 2-((4-(tert-butyl)phenyl)(2-((3-methoxypropyl)amino)-2-oxo-1-(pyridin-3-yl)ethyl)carbamoyl)-4-hydroxypyrrolidine-1-carboxylate (430 mg, 756.11 umol, 1 eq) in DCM (12 mL) was added TFA (5.17 g, 45.37 mmol, 3.36 mL, 60 eq), and the mixture was stirred at 25° C. for 1 h. Upon completion, the mixture was quenched by addition $NaHCO_3$ (100 mL) and then extracted with EtOAc (50*3 mL). The combined organic layers were washed with brine (100 mL), dried over $Na_2SO_4$, filtered and concentrated under reduced pressure to give a residue to give the crude product (2R,4R)—N-(4-(tert-butyl)phenyl)-4-hydroxy-N-(2-((3-methoxypropyl)amino)-2-oxo-1-(pyridin-3-yl)ethyl)pyrrolidine-2-carboxamide (270 mg, crude) as an oil. MS (ESI) m/z 469.3 $[M+H]^+$ Isomer 2: To a solution of (2R,4R)-tert-butyl 2-((4-(tert-butyl)phenyl)(2-((3-methoxypropyl)amino)-2-oxo-1-(pyridin-3-yl)ethyl)carbamoyl)-4-hydroxypyrrolidine-1-carboxylate (380 mg, 668.19 umol, 1 eq) in DCM (9 mL) was added TFA (4.57 g, 40.09 mmol, 2.97 mL, 60 eq) and the mixture was stirred at 25° C. for 1 h. Upon completion, the mixture was quenched by addition $NaHCO_3$ (100 mL) and then extracted with EtOAc (30 mL*3). The combined organic layers were washed with brine (100 mL), dried over $Na_2SO_4$, filtered and concentrated under reduced pressure to give the crude product (2R,4R)—N-(4-(tert-butyl)phenyl)-4-hydroxy-N-(2-((3-methoxypropyl)amino)-2-oxo-1-(pyridin-3-yl)ethyl)pyrrolidine-2-carboxamide (190 mg, crude) as an oil. MS (ESI) m/z 469.3 $[M+H]^+$ Step3:(2R,4R)—N-(4-(tert-butyl)phenyl)-1-cyano-4-hydroxy-N-(2-((3-methoxypropyl)amino)-2-oxo-1-(pyridin-3-yl)ethyl)pyrrolidine-2-carboxamide Compound 647 Isomer 1: To a solution of (2R,4R)—N-(4-(tert-butyl)phenyl)-4-hydroxy-N-(2-((3-methoxypropyl)amino)-2-oxo-1-(pyridin-3-yl)ethyl)pyrrolidine-2-carboxamide (260 mg, 554.86 umol, 1 eq) in DCM (0.5 mL) was added TEA (168.44 mg, 1.66 mmol, 231.69 uL, 3 eq), and the mixture was cooled at −10° C. BrCN (88.16 mg, 832.29 umol, 61.22 uL, 1.5 eq) in DCM (0.5 mL) was added, and the mixture was stirred for 0.5 h at 0° C. and warmed to 25° C. for 1.5 h. Upon completion, the mixture was quenched by addition $H_2O$ (50 mL) and then extracted with EtOAc (30*3 mL). The combined organic layers were washed with brine (30 mL), dried over $Na_2SO_4$, filtered and concentrated under reduced pressure to give a residue and was purified by prep-HPLC (column: Waters Xbridge BEH C18 100*30 mm*10 um; mobile phase: [water (10 mM $NH_4HCO_3$)-ACN]; B %: 26%-56%, 10 min) to give (2R,4R)—N-(4-(tert-butyl)phenyl)-1-cyano-4-hydroxy-N-(2-((3-methoxypropyl)amino)-2-oxo-1-(pyridin-3-yl)ethyl)pyrrolidine-2-carboxamide (15 mg, 30.39 umol, 5.48% yield) as an oil. MS (ESI) m/z 494.3 $[M+H]^+$ $^1H$ NMR (400 MHz, MeOD-$d_4$) δ=8.41-8.25 (m, 2H), 7.74-7.51 (m, 2H), 7.41-7.12 (m, 3H), 6.66 (br s, 1H), 6.52-6.48 (m, 1H), 4.28-4.18 (m, 2H), 3.58 (dd, J=5.6, 9.4 Hz, 1H), 3.45-3.32 (m, 5H), 3.29-3.25 (m, 3H), 2.18-1.95 (m, 2H), 1.82-1.66 (m, 2H), 1.31-1.20 (m, 9H).

Compound 647 Isomer 2: To a solution of (2R,4R)—N-(4-(tert-butyl)phenyl)-4-hydroxy-N-(2-((3-methoxypropyl)amino)-2-oxo-1-(pyridin-3-yl)ethyl)pyrrolidine-2-carboxamide (190 mg, 405.47 umol, 1 eq) in DCM (0.5 mL) was added TEA (123.09 mg, 1.22 mmol, 169.31 uL, 3 eq). The resulting mixture was cooled at −10° C., added with BrCN (64.42 mg, 608.21 umol, 44.74 uL, 1.5 eq) in DCM (0.5 mL) and the solution stirred for 0.5 h at 0° C. and warmed to 25° C. for 1.5 h. Upon completion, the mixture was quenched by addition $H_2O$ (10 mL) and then extracted with EtOAc (30 mL*3). The combined organic layers were washed with brine (10 mL), dried over $Na_2SO_4$, filtered and concentrated under reduced pressure to give a residue and was purified by prep-HPLC (column: Waters Xbridge BEH C18 100*30 mm*10 um; mobile phase: [water (10 mM $NH_4HCO_3$)-ACN]; B %: 26%-56%, 10 min) to give (2R,4R)—N-(4-(tert-butyl)phenyl)-1-cyano-4-hydroxy-N-(2-((3-methoxypropyl)amino)-2-oxo-1-(pyridin-3-yl)ethyl)pyrrolidine-2-carboxamide (30 mg, 60.78 umol, 14.99% yield) as an oil. MS (ESI) m/z 494.3 $[M+H]^+$ $^1H$ NMR (400 MHz, MeOD-$d_4$) δ=8.37 (br s, 2H), 7.65-7.49 (m, 2H), 7.40-7.16 (m, 3H), 6.69 (br s, 1H), 5.96 (s, 1H), 4.28-4.18 (m, 2H), 3.57 (m, 1H), 3.46-3.33 (m, 5H), 3.27-3.25 (m, 3H), 2.14-2.05 (m, 1H), 1.94 (td, J=4.6, 13.3 Hz, 1H), 1.73 (quin, J=6.4 Hz, 2H), 1.26-1.22 (m, 9H).

Example 62: Synthesis of Compound 659

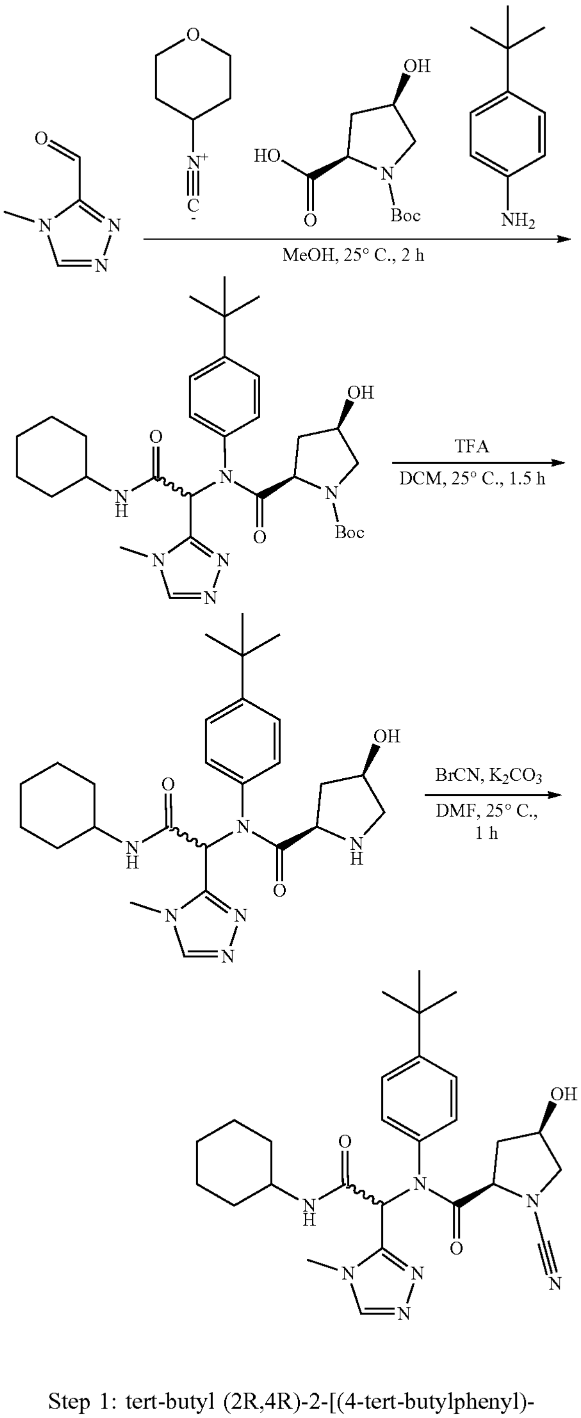

Step 1: tert-butyl (2R,4R)-2-[(4-tert-butylphenyl)-[2-(cyclohexylamino)-1-(4-methyl-1,2,4-triazol-3-yl)-2-oxo-ethyl]carbamoyl]-4-hydroxy-pyrrolidine-1-carboxylate A solution of 4-tert-butylaniline (193.60 mg, 1.30 mmol, 204.87 uL, 1 eq), 4-methyl-1,2,4-triazole-3-carbaldehyde (187.38 mg, 1.69 mmol, 1.3 eq) in MeOH (1 mL) was stirred at 25° C. for 0.5 h. (2R,4R)-1-tert-butoxycarbonyl-4-hydroxy-pyrrolidine-2-carboxylic acid 4-methyl-1,2,4-triazole-3-carbaldehyde (187.38 mg, 1.69 mmol, 1.3 eq) and isocyanocyclohexane (141.63 mg, 1.30 mmol, 161.31 uL, 1 eq) was added and stirred at 25° C. for 2 h. The solution was diluted with $H_2O$ (10 mL), extracted with EtOAc (20 mL*3), and the combined organic phase was dried over $Na_2SO_4$, filtrated and concentrated to give a residue. The residue was purified by prep-HPLC (column: Phenomenex Gemini-NX C18 75*30 mm*3 um; mobile phase: [water (0.1% TFA)-ACN]; B %: 30%-60%, 8 min) to get tert-butyl (2R,4R)-2-[(4-tert-butylphenyl)-[2-(cyclohexylamino)-1-(4-methyl-1,2,4-triazol-3-yl)-2-oxo-ethyl]carbamoyl]-4-hydroxy-pyrrolidine-1-carboxylate (150 mg, 231.67 umol, 17.86% yield, 90% purity) as an oil. MS (ESI) m/z 583.4 $[M+H]^+$ Step 2: (2R, 4R)—N-(4-tert-butylphenyl)-N-[2-(cyclohexylamino)-1-(4-methyl-1,2,4-triazol-3-yl)-2-oxo-ethyl]-4-hydroxy-pyrrolidine-2-carboxamide A solution of tert-butyl (2R,4R)-2-[(4-tert-butylphenyl)-[2-(cyclohexylamino)-1-(4-methyl-1,2,4-triazol-3-yl)-2-oxo-ethyl]carbamoyl]-4-hydroxy-pyrrolidine-1-carboxylate (150 mg, 257.41 umol, 1 eq) in DCM (4 mL) was stirred at 25° C. for 0.5 h. The resulting mixture was added with TFA (2.31 g, 20.26 mmol, 1.50 mL, 78.70 eq) and stirred at 25° C. for 1.5 h. The solution was diluted with $H_2O$ (10 mL), extracted with EtOAc (20 mL*3), the combined organic phase was dried over $Na_2SO_4$, filtrated and concentrated to give the residue: (2R,4R)—N-(4-tert-butylphenyl)-N-[2-(cyclohexylamino)-1-(4-methyl-1,2,4-triazol-3-yl)-2-oxo-ethyl]-4-hydroxy-pyrrolidine-2-carboxamide (130 mg) as an oil. MS (ESI) m/z 483.4 $[M+H]^+$ Step 3: N-(4-tert-butylphenyl)-1-cyano-N-[2-(cyclohexylamino)-2-oxo-1-(3-pyridyl)ethyl]-4-methyl-piperazine-2-carboxamide To a mixture of (2R,4R)—N-(4-tert-butylphenyl)-N-[2-(cyclohexylamino)-1-(4-methyl-1,2,4-triazol-3-yl)-2-oxo-ethyl]-4-hydroxy-pyrrolidine-2-carboxamide (100 mg, 207.20 umol, 1 eq) in DMF (1 mL) was added BrCN (32.92 mg, 310.81 umol, 22.86 uL, 1.5 eq), $K_2CO_3$ (85.91 mg, 621.61 umol, 3 eq) in one portion at −10° C. The mixture was stirred at 25° C. for 1 h. The solution was diluted with $H_2O$ (10 mL), extracted with EtOAc (20 mL*3), the combined organic phase was dried over $Na_2SO_4$, filtrated and concentrated to give a residue. The residue was purified by prep-HPLC (column: Waters Xbridge BEH C18 100*25 mm*5 um; mobile phase: [water (10 mM NH4HCO3)-ACN]; B %: 30%-50%, 10 min) to get (2R,4R)—N-(4-tert-butylphenyl)-1-cyano-N-[2-(cyclohexylamino)-1-(4-methyl-1,2,4-triazol-3-yl)-2-oxo-ethyl]-4-hydroxy-pyrrolidine-2-carboxamide (10 mg, 19.70 umol, 9.51% yield, 100% purity) and (2R,4R)—N-(4-tert-butylphenyl)-1-cyano-N-[2-(cyclohexylamino)-1-(4-methyl-1,2,4-triazol-3-yl)-2-oxo-ethyl]-4-hydroxy-pyrrolidine-2-carboxamide (10 mg, 18.52 umol, 8.94% yield, 94% purity) as a solid. MS (ESI) m/z 508.1 $[M+H]^+$ $^1H$ NMR (400 MHz, METHANOL-$d_4$) δ ppm 8.34 (s, 2H), 6.83-7.53 (m, 4H), 6.66 (s, 1H), 4.16-4.30 (m, 2H), 3.72 (s, 4H), 3.57 (dd, J=9.15, 5.84 Hz, 1H), 3.43 (br dd, J=9.37, 4.52 Hz, 1H), 2.03-2.23 (m, 2H), 1.52-1.90 (m, 5H), 1.28 (d, J=0.66 Hz, 12H), 1.09-1.24 (m, 2H); $^1H$ NMR of Compound 659 Isomer 1—$^1H$ NMR (400 MHz, METHANOL-$d_4$) δ ppm 8.34 (s, 2H), 6.83-7.53 (m, 4H), 6.66 (s, 1H), 4.16-4.30 (m, 2H), 3.72 (s, 4H), 3.57 (dd, J=9.15, 5.84 Hz, 1H), 3.43 (br dd, J=9.37, 4.52 Hz, 1H), 2.03-2.23 (m, 2H), 1.52-1.90 (m, 5H), 1.28 (d, J=0.66 Hz, 12H), 1.09-1.24 (m, 2H); $^1H$ NMR of Compound 659 Isomer 2—$^1H$ NMR (400 MHz, METHANOL-$d_4$) δ ppm 8.36 (s, 2H), 6.88-7.63 (m, 4H), 6.55 (s, 1H), 4.18-4.35 (m, 2H), 3.52-3.68 (m, 5H), 3.41 (br dd, J=9.48, 3.31 Hz, 1H), 1.99-2.13 (m, 1H), 1.89 (br d, J=13.45 Hz, 1H), 1.51-1.77 (m, 5H), 1.09-1.31 (m, 14H)

Example 63: Synthesis of Compound 663

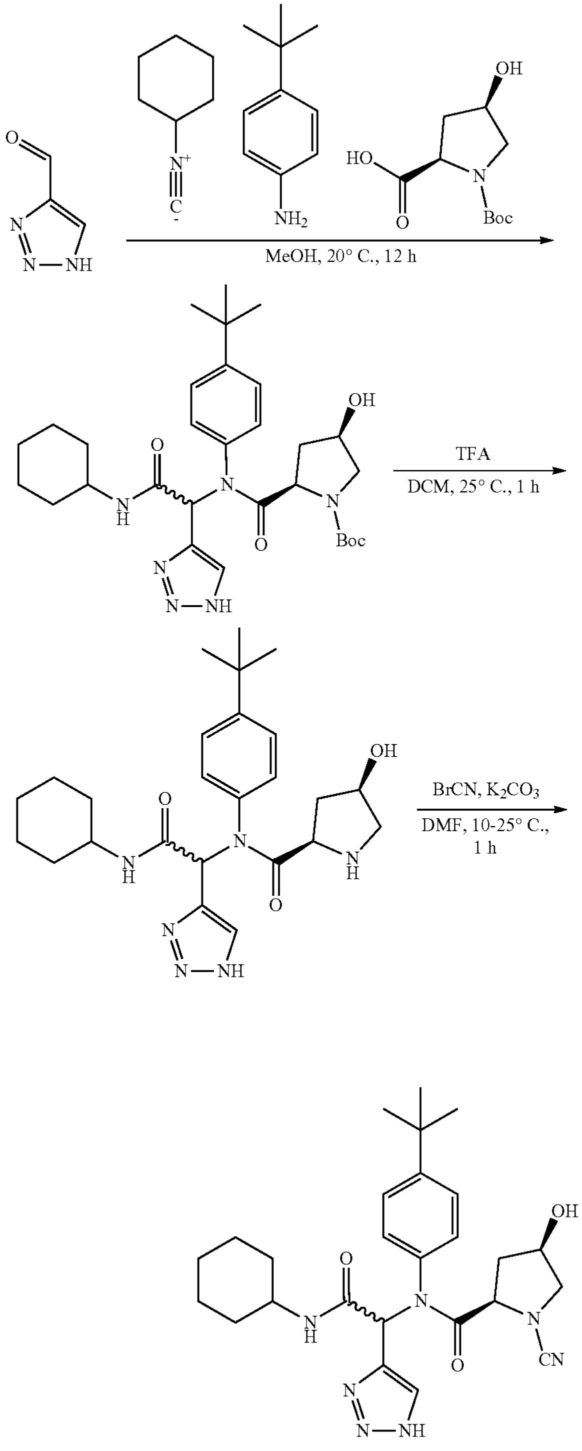

Step 1: (2R,4R)-tert-butyl 2-((4-(tert-butyl)phenyl)(2-(cyclohexylamino)-2-oxo-1-(1H-1,2,3-triazol-4-yl)ethyl)carbamoyl)-4-hydroxypyrrolidine-1-carboxylate To a solution of 4-tert-butylaniline (384.32 mg, 2.58 mmol, 406.69 uL, 1 eq), 1H-triazole-4-carbaldehyde (250 mg, 2.58 mmol, 1 eq), (2R,4R)-1-tert-butoxycarbonyl-4-hydroxy-pyrrolidine-2-carboxylic acid (595.53 mg, 2.58 mmol, 1 eq) and isocyanocyclohexane (281.14 mg, 2.58 mmol, 320.21 uL, 1 eq) in MeOH (6 mL), then the mixture was stirred at 25° C. for 12 h. The reaction mixture was concentrated under reduced pressure to give a residue. The residue was purified by prep-HPLC (column: Phenomenex Gemini-NX 80*40 mm*3 um; mobile phase: [water (10 mM $NH_4HCO_3$)-ACN]; B %: 30%-60%, 8 min) to give the product tert-butyl (2R,4R)-2-[(4-tert-butylphenyl)-[2-(cyclohexylamino)-2-oxo-1-(1H-triazol-4-yl)ethyl]carbamoyl]-4-hydroxy-pyrrolidine-1-carboxylate (400 mg, 703.35 umol, 27.31% yield) was obtained as a solid. MS (ESI) m/z 569.2 $[M+H]^+$ Step 2: (2R,4R)—N-(4-(tert-butyl)phenyl)-N-(2-(cyclohexylamino)-2-oxo-1-(1H-1,2,3-triazol-4-yl)ethyl)-4-hydroxypyrrolidine-2-carboxamide To a solution of tert-butyl (2R,4R)-2-[(4-tert-butylphenyl)-[2-(cyclohexylamino)-2-oxo-1-(1H-triazol-4-yl)ethyl]carbamoyl]-4-hydroxy-pyrrolidine-1-carboxylate (200 mg, 351.68 umol, 1 eq) in DCM (3 mL) was added drop-wise TFA (1.54 g, 13.51 mmol, 1 mL, 38.40 eq), the mixture was stirred at 25° C. for 1 h. The reaction mixture was concentrated under reduced pressure to give a residue. The residue was diluted with DCM (20 mL) and quenched by addition aq. $NaHCO_3$ (20 mL) at 0° C. to pH=8.0, and then extracted with DCM (20 mL*2). The combined organic layers were washed with brine (30 mL), dried over $Na_2SO_4$, filtered and concentrated under reduced pressure to give the product (2R,4R)—N-(4-tert-butylphenyl)-N-[2-(cyclohexylamino)-2-oxo-1-(1H-triazol-4-yl)ethyl]-4-hydroxy-pyrrolidine-2-carboxamide (140 mg, crude) was obtained as a solid. MS (ESI) m/z 469.2 $[M+H]^+$ Step 3: (2R,4R)—N-(4-(tert-butyl)phenyl)-1-cyano-N-(2-(cyclohexylamino)-2-oxo-1-(1H-1,2,3-triazol-4-yl)ethyl)-4-hydroxypyrrolidine-2-carboxamide To a solution of (2R,4R)—N-(4-tert-butylphenyl)-N-[2-(cyclohexylamino)-2-oxo-1-(1H-triazol-4-yl)ethyl]-4-hydroxy-pyrrolidine-2-carboxamide (100 mg, 213.41 umol, 1 eq) in DMF (1 mL) was cooled to −10° C., then $K_2CO_3$ (88.48 mg, 640.22 umol, 3.0 eq) and BrCN (29.39 mg, 277.43 umol, 20.41 uL, 1.3 eq) was added drop-wise at −10° C., then the mixture was allowed to warm to 25° C. and stirred for 1 h. The reaction mixture was quenched by addition $H_2O$ (20 mL) at 0° C., and then extracted with EtOAc (15 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 9 min) to give the product (2R,4R)—N-(4-tert-butylphenyl)-1-cyano-N-[2-(cyclohexylamino)-2-oxo-1-(1H-triazol-4-yl)ethyl]-4-hydroxy-pyrrolidine-2-carboxamide (32.05 mg, 64.93 umol, 30.43% yield, 100% purity) was obtained as a solid. $^1H$ NMR (METHANOL-$d_4$, 400 MHz): δ ppm 6.62-7.89 (m, 5H), 6.09-6.39 (m, 1H), 4.15-4.32 (m, 2H), 3.64-3.76 (m, 1H), 3.57 (dd, J=9.4, 5.6 Hz, 1H), 3.42 (dd, J=9.4, 4.4 Hz, 1H), 2.06-2.19 (m, 1H), 1.87-2.03 (m, 2H), 1.58-1.81 (m, 4H), 1.14-1.39 (m, 14H). MS (ESI) m/z 494.1 $[M+H]^+$ Example 64: Synthesis of Compound 675

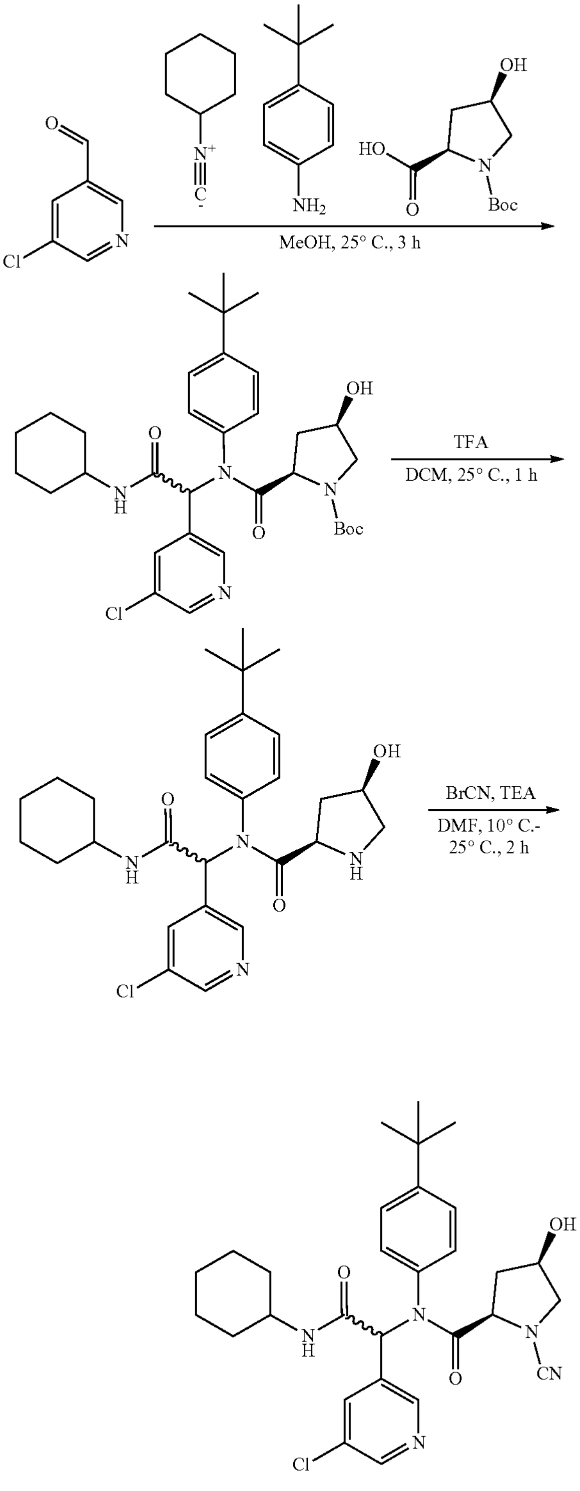

Step1:(2R,4R)-tert-butyl2-((4-(tert-butyl)phenyl)(1-(5-chloropyridin-3-yl)-2-(cyclohexylamino)-2-oxoethyl)carbamoyl)-4-hydroxypyrrolidine-1-carboxylate A solution of 5-chloronicotinaldehyde (400 mg, 2.83 mmol, 1 eq), 4-(tert-butyl)aniline (421.69 mg, 2.83 mmol, 446.24 uL, 1 eq) in MeOH (15 mL) was stirred at 25° C. for 1 h, and the mixture was added with (2R,4R)-1-(tert-butoxycarbonyl)-4-hydroxypyrrolidine-2-carboxylic acid (653.44 mg, 2.83 mmol, 1 eq), and then the mixture was stirred at 25° C. for 0.5 h. Isocyanocyclohexane (277.64 mg, 2.54 mmol, 316.21 uL, 0.9 eq) was added and the mixture was stirred at 25° C. for 1.5 h. Upon completion, the reaction mixture was concentrated under reduced pressure and was purified by column chromatography ($SiO_2$, petroleum ether: EtOAc=5:1) to give a product (2R,4R)-tert-butyl2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 23.09% yield) and (2R,4R)-tert-butyl2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 23.09% yield) as a solid. MS (ESI) m/z 613.3 $[M+H]^+$ Step2:(2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide Isomer 1: To a solution of (2R,4R)-tert-butyl 2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 1 eq) in DCM (9 mL) was added TFA (4.46 g, 39.14 mmol, 2.90 mL, 60 eq). The resulting mixture was stirred at 25° C. for 1 h. Upon completion, the mixture was quenched by addition $NaHCO_3$ (50 mL) and then extracted with EtOAc (30 mL*3). The combined organic layers were washed with brine (50 mL), dried over $Na_2SO_4$, filtered and concentrated under reduced pressure to give the crude product (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol) as a solid. MS (ESI) m/z 513.3 $[M+H]^+$ Isomer 2: To a solution of (2R,4R)-tert-butyl 2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 1 eq) in DCM (10 mL) was added TFA (4.46 g, 39.14 mmol, 2.90 mL, 60 eq) and the mixture was stirred at 25° C. for 1 h. Upon completion, the mixture was quenched by the addition $NaHCO_3$ (50 mL) and then extracted with (EtOAc 30 mL*3). The combined organic layers were washed with brine (50 mL), dried over $Na_2SO_4$, filtered and concentrated under reduced pressure to give the crude product (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol) as a solid. MS (ESI) m/z 513.3 $[M+H]^+$ Step 3:(2R,4R)—N-(4-(tert-butyl)phenyl)-N-(1-(5-chloropyridin-3-yl)-2-(cyclohexylamino)-2-oxoethyl)-1-cyano-4-hydroxypyrrolidine-2-carboxamide Compound 675 Isomer 1: To a solution of (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol, 1 eq) in DCM (3 mL) was added TEA (177.50 mg, 1.75 mmol, 244.15 uL, 3 eq) and the mixture was cooled at −10° C. BrCN (92.90 mg, 877.07 umol, 64.51 uL, 1.5 eq) in DCM (0.5 mL) was added and the mixture was stirred for 0.5 h at 0° C. and warmed to 25° C. gradually. Upon completion, the mixture was added into water (15 mL), extracted with DCM (10 mL*3), and concentrated under reduced pressure to be purified by prep-HPLC (column: Phenomenex Gemini-NX 80*40 mm*3 um; mobile phase: [water (10 mM $NH_4HCO_3$)-ACN]; B %: 30%-60%, 8 min) to give (2R,4R)—N-(4-(tert-butyl)phenyl)-N-(1-(5-chloropyridin-3-yl)-2-(cyclohexylamino)-2-oxoethyl)-1-cyano-4-hydroxypyrrolidine-2-carboxamide (30 mg, 55.75 umol, 9.54% yield) was obtained as a solid. MS (ESI) m/z 538.1 $[M+H]^+$ $^1H$ NMR (400 MHz, MeOD-$d_4$) δ=8.43-8.19 (m, 2H), 7.78-7.10 (m, 4H), 6.82-6.45 (m, 1H), 6.15 (s, 1H), 4.31-4.19 (m, 2H), 3.76-3.64 (m, 11H), 3.58 (dd, J=5.6, 9.4 Hz, 1H), 3.42 (dd, J=4.8, 9.2 Hz, 1H), 2.21-2.09 (m, 1H), 2.06-1.88 (m, 2H), 1.81-1.59 (m, 4H), 1.52-0.92 (m, 15H).

Compound 675 Isomer 2: To a solution of (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol, 1 eq) in DCM (3 mL) was added TEA (177.50 mg, 1.75 mmol, 244.15 uL, 3 eq) and the mixture was cooled at −10° C. BrCN (92.90 mg, 877.07 umol, 64.51 uL, 1.5 eq) in DCM (0.5 mL) was added and the mixture was stirred for 0.5 h at 0° C. and warmed to 25° C. gradually for 1.5 h. Upon completion, the mixture was added into water (20 mL) and was extracted with DCM (10 mL*3), concentrated under reduced pressure and purified by prep-HPLC (column: Phenomenex Gemini-NX 80*40 mm*3 um; mobile phase: [water (10 mM $NH_4HCO_3$)-ACN]; B %: 30%-60%, 8 min) to give (2R,4R)—N-(4-(tert-butyl)phenyl)-N-(1-(5-chloropyridin-3-yl)-2-(cyclohexylamino)-2-oxoethyl)-1-cyano-4-hydroxypyrrolidine-2 carboxamide (30 mg, 55.75 umol, 9.54% yield) as a solid. MS (ESI) m/z 538.1 $[M+H]^+$ H NMR (400 MHz, MeOD-$d_4$) δ=8.43-8.26 (m, 2H), 7.82-7.05 (m, 4H), 6.81-6.37 (m, 1H), 6.16 (s, 1H), 4.35-4.19 (m, 2H), 3.67 (tt, J=3.8, 10.8 Hz, 1H), 3.57 (dd, J=5.4, 9.6 Hz, 1H), 3.43 (dd, J=4.0, 9.4 Hz, 1H), 2.18-2.02 (m, 1H), 1.93 (td, J=4.4, 13.2 Hz, 2H), 1.79-1.59 (m, 4H), 1.51-0.96 (m, 15H).

Example 65: Synthesis of Compound 679

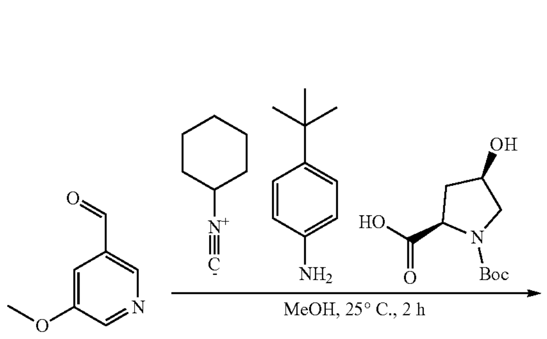

-continued

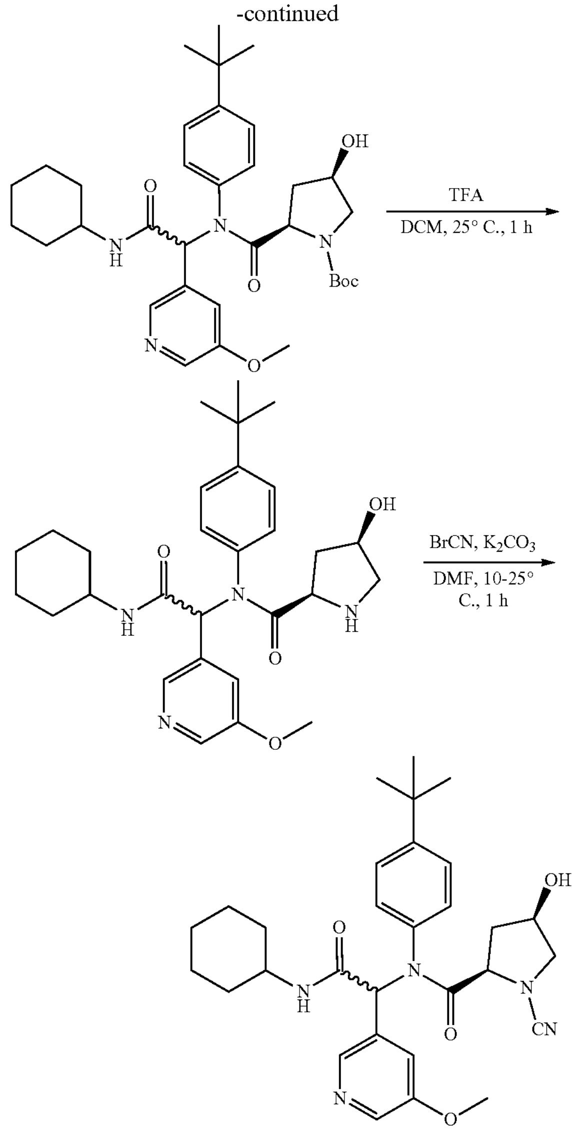

Step 1: (2R,4R)-tert-butyl 2-((4-(tert-butyl)phenyl) (2-(cyclohexylamino)-1-(5-methoxypyridin-3-yl)-2-oxoethyl)carbamoyl)-4-hydroxypyrrolidine-1-carboxylate A solution of 4-tert-butylaniline (272.05 mg, 1.82 mmol, 287.89 uL, 1 eq), 5-methoxypyridine-3-carbaldehyde (250 mg, 1.82 mmol, 1 eq), (2R,4R)-1-tert-butoxycarbonyl-4-hydroxy-pyrrolidine-2-carboxylic acid (421.56 mg, 1.82 mmol, 1 eq) and isocyanocyclohexane (199.02 mg, 1.82 mmol, 226.67 uL, 1 eq) in MeOH (4 mL) was stirred at 25° C. for 2 h. The reaction mixture was concentrated under reduced pressure to give a residue. The residue was purified by prep-HPLC (column: Phenomenex Gemini-NX 80×40 mm×3 um; mobile phase: [water (10 mM $NH_4HCO_3$)-ACN]; B %: 40%-60%, 8 min) to get the product tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (350 mg, 574.93 umol, 31.54% yield) was obtained as a solid and tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (350 mg, 574.93 umol, 31.54% yield) as a solid. MS (ESI) m/z 609.3 [M+H]$^+$ Step 2: (2R,4R)—N-(4-(tert-butyl)phenyl)-N-(2-(cyclohexylamino)-1-(5-methoxypyridin-3-yl)-2-oxoethyl)-4-hydroxypyrrolidine-2-carboxamide A solution of tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (80 mg, 131.41 umol, 1 eq) in DCM (1.5 mL) was added with TFA (770.00 mg, 6.75 mmol, 0.5 mL, 51.39 eq) drop-wise, and the mixture was stirred at 25° C. for 1 h. The reaction mixture was concentrated under reduced pressure to give a residue. The residue was purified by prep-HPLC (column: Phenomenex Gemini-NX 150×30 mm×5 um; mobile phase: [water (0.1% TFA)-ACN]; B %: 25%-55%, 9 min) to get the product (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (24.19 mg, 47.56 umol, 36.19% yield, 100% purity) as a solid. MS (ESI) m/z 509.2 [M+H]$^+$ 1H NMR (METHANOL-$d_4$, 400 MHz): δ ppm 8.15-8.21 (m, 1H), 8.12 (d, J=2.7 Hz, 1H), 8.03 (d, J=1.5 Hz, 1H), 7.20-7.89 (m, 3H), 7.16-7.20 (m, 1H), 6.76 (br s, 1H), 6.23 (s, 1H), 4.35 (dd, J=4.2, 2.3 Hz, 1H), 4.23 (t, J=8.4 Hz, 1H), 3.67-3.78 (m, 4H), 3.32 (br s, 1H), 3.19 (dd, J=11.7, 4.3 Hz, 1H), 2.05 (dd, J=8.7, 4.5 Hz, 2H), 1.92 (br d, J=12.3 Hz, 1H), 1.74-1.83 (m, 2H), 1.61-1.73 (m, 2H), 1.05-1.44 (m, 14H).

A solution of tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (80 mg, 131.41 umol, 1 eq) in DCM (1.5 mL) was added with drop-wise TFA (770.00 mg, 6.75 mmol, 0.5 mL, 51.39 eq), and the mixture was stirred at 25° C. for 1 h. The reaction mixture was concentrated under reduced pressure to give a residue. The residue was purified by prep-HPLC (column: Phenomenex Gemini-NX 150×30 mm×5 um; mobile phase: [water (0.1% TFA)-ACN]; B %: 25%-55%, 9 min) to get the product (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (26.23 mg, 51.57 umol, 39.24% yield, 100% purity) as a solid. MS (ESI) m/z 509.2 [M+H]$^+$ 1H NMR (METHANOL-$d_4$, 400 MHz): δ ppm 8.22 (br d, J=7.8 Hz, 1H), 8.12 (d, J=2.7 Hz, 1H), 8.03 (d, J=1.6 Hz, 1H), 7.12-7.92 (m, 3H), 7.04-7.11 (m, 1H), 6.61 (br s, 1H), 6.04 (s, 1H), 4.35 (tt, J=4.5, 2.5 Hz, 1H), 4.29 (dd, J=9.9, 6.5 Hz, 1H), 3.59-3.77 (m, 4H), 3.32-3.37 (m, 1H), 3.18 (dd, J=11.8, 4.2 Hz, 1H), 1.84-2.05 (m, 3H), 1.58-1.80 (m, 4H), 1.06-1.38 (m, 14H).

Step 3: (2R,4R)—N-(4-(tert-butyl)phenyl)-1-cyano-N-(2-(cyclohexylamino)-1-(5-methoxypyridin-3-yl)-2-oxoethyl)-4-hydroxypyrrolidine-2-carboxamide A solution of (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (90 mg, 176.94 umol, 1 eq) in DMF (1 mL) was cooled to −10° C., then $K_2CO_3$ (73.36 mg, 530.82 umol, 3.0 eq) and BrCN (25 mg, 236.03 umol, 17.36 uL, 1.33 eq) was added drop-wise at −10° C. The mixture was allowed to warm to 25° C. and stirred for 1 hr. The reaction mixture was quenched by addition $H_2O$ (20 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100×25 mm×5 um; mobile phase: [water (10 mM $NH_4HCO_3$)-ACN]; B %: 35%-65%, 10 min) to get the product (2R, 4R)—N-(4-tert-butylphenyl)-1-cyano-N-[2-(cyclohexylamino)-1-(5-methoxy-3-pyridyl)-2-oxo-ethyl]-4-hydroxy-pyrrolidine-2-carboxamide (20.55 mg, 38.51 umol, 21.76% yield, 100% purity) as a solid. MS (ESI) m/z 534.2 $[M+H]^+$ $_1$H NMR (METHANOL-$d_4$, 400 MHz): δ ppm 7.99 (d, J=2.7 Hz, 1H), 7.93 (d, J=1.6 Hz, 1H), 7.70 (br s, 1H), 7.44 (br s, 1H), 7.19 (br s, 1H), 6.94-7.04 (m, 1H), 6.62 (br s, 1H), 6.14 (s, 1H), 4.14-4.29 (m, 2H), 3.61-3.76 (m, 4H), 3.57 (dd, J=9.4, 5.6 Hz, 1H), 3.42 (dd, J=9.3, 4.8 Hz, 1H), 2.12-2.22 (m, 1H), 2.02 (dt, J=13.2, 5.4 Hz, 1H), 1.94 (br d, J=11.6 Hz, 1H), 1.59-1.81 (m, 4H), 1.07-1.40 (m, 14H).

To a solution of (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (90 mg, 176.94 umol, 1 eq) in DMF (1 mL) was cooled to −10° C., then $K_2CO_3$ (73.36 mg, 530.82 umol, 3.0 eq) and BrCN (25 mg, 236.03 umol, 17.36 uL, 1.33 eq) was added drop-wise at −10° C., then the mixture was allowed to warm to 25° C. and stirred for 1 h. The reaction mixture was quenched by addition $H_2O$ (20 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100×25 mm×5 um; mobile phase: [water (10 mM $NH_4HCO_3$)-ACN]; B %: 35%-65%, 10 min) to get the product (2R, 4R)—N-(4-tert-butylphenyl)-1-cyano-N-[2-(cyclohexylamino)-1-(5-methoxy-3-pyridyl)-2-oxo-ethyl]-4-hydroxy-pyrrolidine-2-carboxamide (27.60 mg, 51.72 umol, 29.23% yield, 100% purity) as a solid. MS (ESI) m/z 534.2 $[M+H]^+$ $_1$H NMR (METHANOL-$d_4$, 400 MHz): δ ppm 8.03 (d, J=2.8 Hz, 1H), 7.98 (d, J=1.7 Hz, 1H), 7.74 (br s, 1H), 7.49 (br s, 1H), 7.18 (br s, 1H), 6.94-7.05 (m, 1H), 6.56 (br s, 1H), 6.00 (s, 1H), 4.17-4.34 (m, 2H), 3.60-3.75 (m, 4H), 3.57 (dd, J=9.5, 5.4 Hz, 1H), 3.43 (dd, J=9.4, 4.0 Hz, 1H), 2.03-2.16 (m, 1H), 1.87-2.01 (m, 2H), 1.56-1.83 (m, 4H), 1.06-1.39 (m, 14H).

Example 66: Synthesis of Compound 992

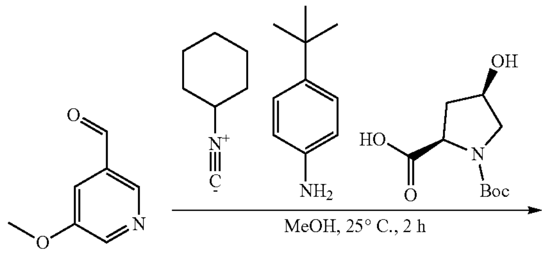

-continued

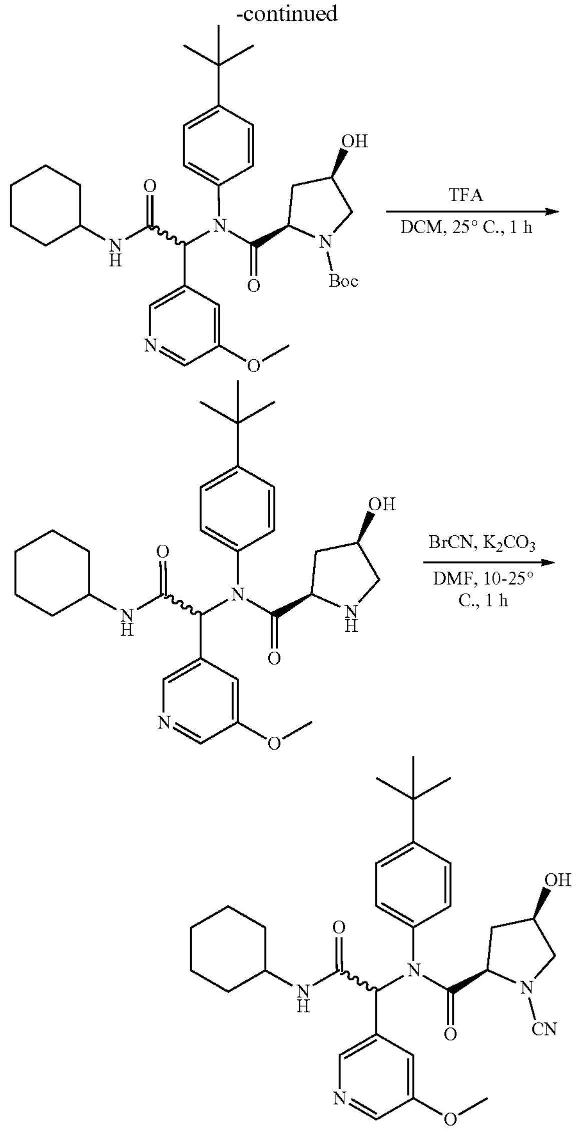

Step 1: (2R,4R)-tert-butyl 2-((4-(tert-butyl)phenyl)(2-(cyclohexylamino)-1-(5-methoxypyridin-3-yl)-2-oxoethyl)carbamoyl)-4-hydroxypyrrolidine-1-carboxylate A solution of 4-tert-butylaniline (272.05 mg, 1.82 mmol, 287.89 uL, 1 eq), 5-methoxypyridine-3-carbaldehyde (250 mg, 1.82 mmol, 1 eq), (2R,4R)-1-tert-butoxycarbonyl-4-hydroxy-pyrrolidine-2-carboxylic acid (421.56 mg, 1.82 mmol, 1 eq) and isocyanocyclohexane (199.02 mg, 1.82 mmol, 226.67 uL, 1 eq) in MeOH (4 mL) was stirred at 25° C. for 2 h. The reaction mixture was concentrated under reduced pressure to give a residue. The residue was purified by prep-HPLC (column: Phenomenex Gemini-NX 80×40 mm×3 um; mobile phase: [water (10 mM $NH_4HCO_3$)-ACN]; B %: 40%-60%, 8 min) to get the product tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (350 mg, 574.93 umol, 31.54% yield) as a solid, and tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (350 mg, 574.93 umol, 31.54% yield) was obtained as a solid. MS (ESI) m/z 609.3 [M+H]+

Step 2: (2R,4R)—N-(4-(tert-butyl)phenyl)-N-(2-(cyclohexylamino)-1-(5-methoxypyridin-3-yl)-2-oxoethyl)-4-hydroxypyrrolidine-2-carboxamide A solution of tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (80 mg, 131.41 umol, 1 eq) in DCM (1.5 mL) was added drop-wise with TFA (770.00 mg, 6.75 mmol, 0.5 mL, 51.39 eq), and the mixture was stirred at 25° C. for 1 h. The reaction mixture was concentrated under reduced pressure to give a residue. The residue was purified by prep-HPLC (column: Phenomenex Gemini-NX 150×30 mm×5 um; mobile phase: [water (0.1% TFA)-ACN]; B %: 25%-55%, 9 min) to get the product (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (24.19 mg, 47.56 umol, 36.19% yield, 100% purity) as a solid. MS (ESI) m/z 509.2 [M+H]+ H NMR (METHANOL-$d_4$, 400 MHz): δ ppm 8.15-8.21 (m, 1H), 8.12 (d, J=2.7 Hz, 1H), 8.03 (d, J=1.5 Hz, 1H), 7.20-7.89 (m, 3H), 7.16-7.20 (m, 1H), 6.76 (br s, 1H), 6.23 (s, 1H), 4.35 (dd, J=4.2, 2.3 Hz, 1H), 4.23 (t, J=8.4 Hz, 1H), 3.67-3.78 (m, 4H), 3.32 (br s, 1H), 3.19 (dd, J=11.7, 4.3 Hz, 1H), 2.05 (dd, J=8.7, 4.5 Hz, 2H), 1.92 (br d, J=12.3 Hz, 1H), 1.74-1.83 (m, 2H), 1.61-1.73 (m, 2H), 1.05-1.44 (m, 14H).

A solution of tert-butyl (2R,4R)-2-[(4-tert-butylphenyl)-[2-(cyclohexylamino)-1-(5-methoxy-3-pyridyl)-2-oxo-ethyl]carbamoyl]-4-hydroxy-pyrrolidine-1-carboxylate (80 mg, 131.41 umol, 1 eq) in DCM (1.5 mL) was added drop-wise TFA (770.00 mg, 6.75 mmol, 0.5 mL, 51.39 eq), and the mixture was stirred at 25° C. for 1 h. The reaction mixture was concentrated under reduced pressure to give a residue. The residue was purified by prep-HPLC (column: Phenomenex Gemini-NX 150×30 mm×5 um; mobile phase: [water (0.1% TFA)-ACN]; B %: 25%-55%, 9 min) to get the product (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (26.23 mg, 51.57 umol, 39.24% yield, 100% purity) as a solid. MS (ESI) m/z 509.2 [M+H]+ 1H NMR (METHANOL-$d_4$, 400 MHz): δ ppm 8.22 (br d, J=7.8 Hz, 1H), 8.12 (d, J=2.7 Hz, 1H), 8.03 (d, J=1.6 Hz, 1H), 7.12-7.92 (m, 3H), 7.04-7.11 (m, 1H), 6.61 (br s, 1H), 6.04 (s, 1H), 4.35 (tt, J=4.5, 2.5 Hz, 1H), 4.29 (dd, J=9.9, 6.5 Hz, 1H), 3.59-3.77 (m, 4H), 3.32-3.37 (m, 1H), 3.18 (dd, J=11.8, 4.2 Hz, 1H), 1.84-2.05 (m, 3H), 1.58-1.80 (m, 4H), 1.06-1.38 (m, 14H).

Step 3: (2R,4R)—N-(4-(tert-butyl)phenyl)-1-cyano-N-(2-(cyclohexylamino)-1-(5-methoxypyridin-3-yl)-2-oxoethyl)-4-hydroxypyrrolidine-2-carboxamide A solution of (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (90 mg, 176.94 umol, 1 eq) in DMF (1 mL) was cooled to −10° C., and then $K_2CO_3$ (73.36 mg, 530.82 umol, 3.0 eq) and BrCN (25 mg, 236.03 umol, 17.36 uL, 1.33 eq) was added drop-wise at −10° C. The mixture was allowed to warm to 25° C. and stirred for 1 hr. The reaction mixture was quenched by addition $H_2O$ (20 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100×25 mm×5 um; mobile phase: [water (10 mM $NH_4HCO_3$)-ACN]; B %: 35%-65%, 10 min) to get the product (2R,4R)—N-(4-tert-butylphenyl)-1-cyano-N-[2-(cyclohexylamino)-1-(5-methoxy-3-pyridyl)-2-oxo-ethyl]-4-hydroxy-pyrrolidine-2-carboxamide (20.55 mg, 38.51 umol, 21.76% yield, 100% purity) as a solid. MS (ESI) m/z 534.2 [M+H]+ 1H NMR (METHANOL-$d_4$, 400 MHz): δ ppm 7.99 (d, J=2.7 Hz, 1H), 7.93 (d, J=1.6 Hz, 1H), 7.70 (br s, 1H), 7.44 (br s, 1H), 7.19 (br s, 11H), 6.94-7.04 (m, 11H), 6.62 (br s, 1H), 6.14 (s, 1H), 4.14-4.29 (m, 2H), 3.61-3.76 (m, 4H), 3.57 (dd, J=9.4, 5.6 Hz, 1H), 3.42 (dd, J=9.3, 4.8 Hz, 1H), 2.12-2.22 (m, 1H), 2.02 (dt, J=13.2, 5.4 Hz, 1H), 1.94 (br d, J=11.6 Hz, 1H), 1.59-1.81 (m, 4H), 1.07-1.40 (m, 14H).

A solution of (2R,4R)—N-(4-tert-butylphenyl)-N-[2-(cyclohexylamino)-1-(5-methoxy-3-pyridyl)-2-oxo-ethyl]-4-hydroxy-pyrrolidine-2-carboxamide (90 mg, 176.94 umol, 1 eq) in DMF (1 mL) was cooled to −10° C., and then $K_2CO_3$ (73.36 mg, 530.82 umol, 3.0 eq) and BrCN (25 mg, 236.03 umol, 17.36 uL, 1.33 eq) was added drop-wise at −10° C. The mixture was allowed to warm to 25° C. and stirred for 1 h. The reaction mixture was quenched by addition $H_2O$ (20 mL) at 0° C., and then extracted with EtOAc (20 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100×25 mm×5 um; mobile phase: [water (10 mM $NH_4HCO_3$)-ACN]; B %: 35%-65%, 10 min) to get the product (2R,4R)—N-(4-tert-butylphenyl)-1-cyano-N-[2-(cyclohexylamino)-1-(5-methoxy-3-pyridyl)-2-oxo-ethyl]-4-hydroxy-pyrrolidine-2-carboxamide (27.60 mg, 51.72 umol, 29.23% yield, 100% purity) as a solid. MS (ESI) m/z 534.2 [M+H]+ 1H NMR (METHANOL-$d_4$, 400 MHz): δ ppm 8.03 (d, J=2.8 Hz, 1H), 7.98 (d, J=1.7 Hz, 1H), 7.74 (br s, 1H), 7.49 (br s, 1H), 7.18 (br s, 1H), 6.94-7.05 (m, 1H), 6.56 (br s, 1H), 6.00 (s, 1H), 4.17-4.34 (m, 2H), 3.60-3.75 (m, 4H), 3.57 (dd, J=9.5, 5.4 Hz, 1H), 3.43 (dd, J=9.4, 4.0 Hz, 1H), 2.03-2.16 (m, 1H), 1.87-2.01 (m, 2H), 1.56-1.83 (m, 4H), 1.06-1.39 (m, 14H).

Example 67: Synthesis of Compound 723

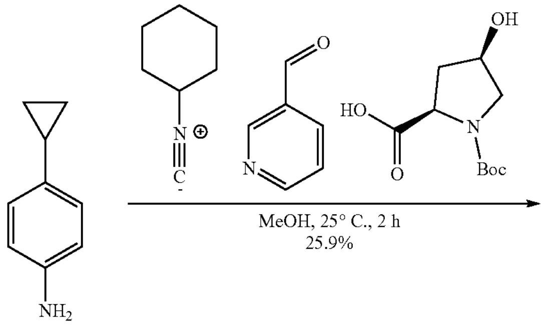

-continued

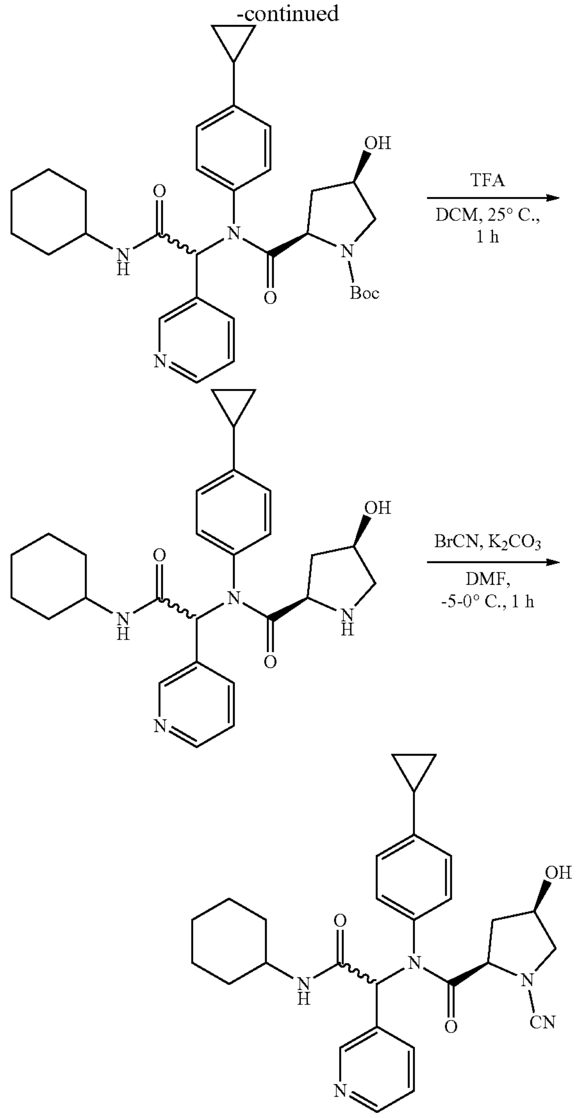

Step 1: (2R,4R)-tert-butyl 2-((2-(cyclohexylamino)-2-oxo-1-(pyridin-3-yl)ethyl)(4-cyclopropylphenyl) carbamoyl)-4-hydroxypyrrolidine-1-carboxylate A solution of 4-cyclopropylaniline (0.25 g, 1.88 mmol, 1 eq) and pyridine-3-carbaldehyde (241.26 mg, 2.25 mmol, 211.63 uL; 1.2 eq) in MeOH (4 mL) was stirred at 25° C. for 30 mins, and then (2R,4R)-1-tert-butoxycarbonyl-4-hydroxy-pyrrolidine-2-carboxylic acid (434.05 mg, 1.88 mmol, 1 eq) was added. After stirring 15 mins, the solution was cooled to −40° C. and isocyanocyclohexane (204.91 mg, 1.88 mmol, 233.38 uL, 1 eq) in MeOH (1 mL) was added drop-wise within 15 mins for 3 times. The resulting mixture was stirred at 25° C. for 1 h. Upon completion, the reaction mixture was concentrated under reduced pressure to give a residue. The residue was purified by column chromatography ($SiO_2$, petroleum ether:EtOAc=2:1 to 0:1) to give tert-butyl (2R,4R)-2-[[2-(cyclohexylamino)-2-oxo-1-(3-pyridyl)ethyl]-(4-cyclopropylphenyl)carbamoyl]-4-hydroxy-pyrrolidine-1-carboxylate (0.15 g, 239.92 umol, 12.78% yield, 90% purity) as a solid. MS (ESI) m/z 563.3 $[M+H]^+$. To give tert-butyl (2R,4R)-2-[[2-(cyclohexylamino)-2-oxo-1-(3-pyridyl)ethyl]-(4-cyclopropylphenyl) carbamoyl]-4-hydroxy-pyrrolidine-1-carboxylate (0.15 g, 253.24 umol, 13.49% yield, 95% purity) as a solid. MS (ESI) m/z 563.2 $[M+H]^+$.

Step 2: (2R,4R)—N-(2-(cyclohexylamino)-2-oxo-1-(pyridin-3-yl)ethyl)-N-(4-cyclopropylphenyl)-4-hydroxypyrrolidine-2-carboxamide To a solution of tert-butyl (2R,4R)-2-[[2-(cyclohexylamino)-2-oxo-1-(3-pyridyl)ethyl]-(4-cyclopropylphenyl) carbamoyl]-4-hydroxy-pyrrolidine-1-carboxylate (0.13 g, 231.03 umol, 1 eq) in DCM (1 mL) was added TFA (770.00 mg, 6.75 mmol, 0.5 mL, 29.23 eq), and the mixture was stirred at 25° C. for 1 h. Upon completion, the reaction mixture was dried by blowing $N_2$, diluted with sat. $NaHCO_3$ solution (15 mL) and extracted with DCM (5 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-N-(4-cyclopropylphenyl)-4-hydroxy-pyrrolidine-2-carboxamide (0.1 g, crude) as an oil.

(2R,4R)—N-[2-(cyclohexylamino)-2-oxo-1-(3-pyridyl) ethyl]-N-(4-cyclopropylphenyl)-4-hydroxy-pyrrolidine-2-carboxamide (0.03 g, 64.85 umol, 1 eq) was purified by prep-HPLC (column: Phenomenex Gemini-NX 150*30 mm*5 um; mobile phase: [water (0.1% TFA)-ACN]; B %: 10%-40%, 9 min) to give (2R,4R)—N-[2-(cyclohexylamino)-2-oxo-1-(3-pyridyl)ethyl]-N-(4-cyclopropylphenyl)-4-hydroxy-pyrrolidine-2-carboxamide (27.06 mg, 58.50 umol, 90.20% yield) as a solid. MS (ESI) m/z 463.1 $[M+H]^+$. $^1H$ NMR (400 MHz, MeOD-$d_4$) δ=8.51-8.39 (m, 2H), 8.16 (br d, J=7.9 Hz, 1H), 7.80 (br d, J=8.0 Hz, 1H), 7.63 (br s, 1H), 7.43 (dd, J=5.2, 7.9 Hz, 1H), 7.20-6.53 (m, 3H), 6.26 (s, 1H), 4.40-4.30 (m, 1H), 4.21 (t, J=8.5 Hz, 1H), 3.80-3.64 (m, 1H), 3.35-3.32 (m, 1H), 3.23-3.13 (m, 1H), 2.01 (dd, J=4.3, 8.6 Hz, 2H), 1.92 (br d, J=12.5 Hz, 1H), 1.86-1.58 (m, 5H), 1.42-1.05 (m, 5H), 1.02-0.91 (m, 2H), 0.68-0.52 (m, 2H).

(2R,4R)—N-(2-(cyclohexylamino)-2-oxo-1-(pyridin-3-yl)ethyl)-N-(4-cyclopropylphenyl)-4-hydroxypyrrolidine-2-carboxamide To a solution of tert-butyl (2R,4R)-2-[[2-(cyclohexylamino)-2-oxo-1-(3-pyridyl)ethyl]-(4-cyclopropylphenyl) carbamoyl]-4-hydroxy-pyrrolidine-1-carboxylate (0.13 g, 231.03 umol, 1 eq) in DCM (1 mL) was added TFA (770.00 mg, 6.75 mmol, 0.5 mL, 29.23 eq), and the mixture was stirred at 25° C. for 1 h. Upon completion, the reaction mixture was dried by blowing $N_2$, diluted with sat. $NaHCO_3$ solution (5 mL) and extracted with DCM (2 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-N-(4-cyclopropylphenyl)-4-hydroxy-pyrrolidine-2-carboxamide (0.1 g, crude) as an oil.

(2R,4R)—N-[2-(cyclohexylamino)-2-oxo-1-(3-pyridyl) ethyl]-N-(4-cyclopropylphenyl)-4-hydroxy-pyrrolidine-2-carboxamide (0.03 g, 64.85 umol, 1 eq) was purified by prep-HPLC (column: Phenomenex Gemini-NX 150*30 mm*5 um; mobile phase: [water (0.1% TFA)-ACN]; B %: 10%-40%, 9 min) to give (2R,4R)—N-[2-(cyclohexylamino)-2-oxo-1-(3-pyridyl)ethyl]-N-(4-cyclopropylphenyl)-4-hydroxy-pyrrolidine-2-carboxamide (21.48 mg, 46.43 umol, 71.60% yield, 100% purity) as a solid. MS (ESI) m/z 463.1 $[M+H]^+$. $^1H$ NMR (400 MHz, MeOD-$d_4$)

δ=8.52-8.39 (m, 2H), 8.17 (br d, J=8.0 Hz, 1H), 7.75 (br d, J=8.0 Hz, 1H), 7.64 (br s, 1H), 7.41 (dd, J=5.2, 7.9 Hz, 1H), 7.25-6.33 (m, 3H), 6.08 (s, 1H), 4.41-4.31 (m, 1H), 4.23 (dd, J=6.5, 10.1 Hz, 1H), 3.68 (br d, J=5.5 Hz, 11H), 3.34 (br s, 1H), 3.18 (dd, J=4.2, 11.8 Hz, 1H), 2.06-1.81 (m, 4H), 1.79-1.56 (m, 4H), 1.41-1.04 (m, 5H), 0.97 (dd, J=2.0, 8.4 Hz, 2H), 0.61 (dt, J=2.4, 5.1 Hz, 2H).

Step 3: (2R,4R)—N-(2-(cyclohexylamino)-2-oxo-1-(pyridin-3-yl)ethyl)-N-(4-cyclopropylphenyl)-4-hydroxypyrrolidine-2-carboxamide To a solution of (2R,4R)—N-[2-(cyclohexylamino)-2-oxo-1-(3-pyridyl)ethyl]-N-(4-cyclopropylphenyl)-4-hydroxy-pyrrolidine-2-carboxamide (0.07 g, 151.32 umol, 1 eq) in DMF (1.5 mL) was added $K_2CO_3$ (62.74 mg, 453.97 umol, 3 eq), and then the solution was cooled to −5° C. BrCN (19.23 mg, 181.59 umol, 13.36 uL, 1.2 eq) in DMF (0.5 mL) was added drop-wise, and the mixture was stirred at 0° C. for 1 h. Upon completion, the reaction mixture was diluted with water (10 mL) and extracted with EtOAc (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 25%-60%, 10 min) to give (2R,4R)-1-cyano-N-[2-(cyclohexylamino)-2-oxo-1-(3-pyridyl)ethyl]-N-(4-cyclopropylphenyl)-4-hydroxy-pyrrolidine-2-carboxamide (33.85 mg, 69.42 umol, 45.88% yield, 100% purity) as a solid. MS (ESI) m/z 488.1 $[M+H]^+$. $^1H$ NMR (400 MHz, MeOD-$d_4$) δ=8.30 (dt, J=1.7, 4.5 Hz, 2H), 7.72-7.57 (m, 1H), 7.54 (td, J=1.8, 7.9 Hz, 1H), 7.20 (dd, J=4.9, 7.9 Hz, 1H), 7.06 (br s, 1H), 6.82 (br d, J=2.6 Hz, 1H), 6.68-6.47 (m, 1H), 6.17 (s, 1H), 4.31-4.13 (m, 2H), 3.79-3.64 (m, 1H), 3.55-3.51 (m, 1H), 3.41 (dd, J=4.9, 9.3 Hz, 1H), 2.20-2.05 (m, 1H), 2.04-1.89 (m, 2H), 1.86-1.57 (m, 5H), 1.44-1.02 (m, 5H), 0.99-0.87 (m, 2H), 0.69-0.53 (m, 2H).

(2R,4R)—N-(2-(cyclohexylamino)-2-oxo-1-(pyridin-3-yl)ethyl)-N-(4-cyclopropylphenyl)-4-hydroxypyrrolidine-2-carboxamide To a solution of (2R,4R)—N-[2-(cyclohexylamino)-2-oxo-1-(3-pyridyl)ethyl]-N-(4-cyclopropylphenyl)-4-hydroxy-pyrrolidine-2-carboxamide (0.07 g, 151.32 umol, 1 eq) in DMF (1.5 mL) was added $K_2CO_3$ (62.74 mg, 453.97 umol, 3 eq), and then the solution was cooled to −5° C. BrCN (19.23 mg, 181.59 umol, 13.36 uL, 1.2 eq) in DMF (0.5 mL) was added drop-wise, and the mixture was stirred at 0° C. for 1 h. Upon completion, the reaction mixture was diluted with water (10 mL) and extracted with EtOAc (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 25%-60%, 10 min) to give (2R,4R)-1-cyano-N-[2-(cyclohexylamino)-2-oxo-1-(3-pyridyl)ethyl]-N-(4-cyclopropylphenyl)-4-hydroxy-pyrrolidine-2-carboxamide (20.53 mg, 42.10 umol, 27.82% yield, 100% purity) as a solid. MS (ESI) m/z 488.1 $[M+H]^+$. $^1H$ NMR (400 MHz, MeOD-$d_4$) δ=8.34 (br s, 2H), 7.67 (br s, 1H), 7.55 (br d, J=7.9 Hz, 1H), 7.22 (dd, J=5.0, 7.8 Hz, 1H), 7.10 (br dd, J=2.1, 3.1 Hz, 1H), 6.95-6.70 (m, 1H), 6.66-6.36 (m, 1H), 6.03 (s, 1H), 4.29-4.15 (m, 2H), 3.75-3.62 (m, 1H), 3.57 (dd, J=5.6, 9.5 Hz, 1H), 3.42 (dd, J=4.2, 9.5 Hz, 1H), 2.16-2.02 (m, 1H), 1.97-1.58 (m, 7H), 1.41-1.03 (m, 5H), 0.99-0.86 (m, 2H), 0.68-0.54 (m, 2H).

Example 68: Synthesis of Compound 735

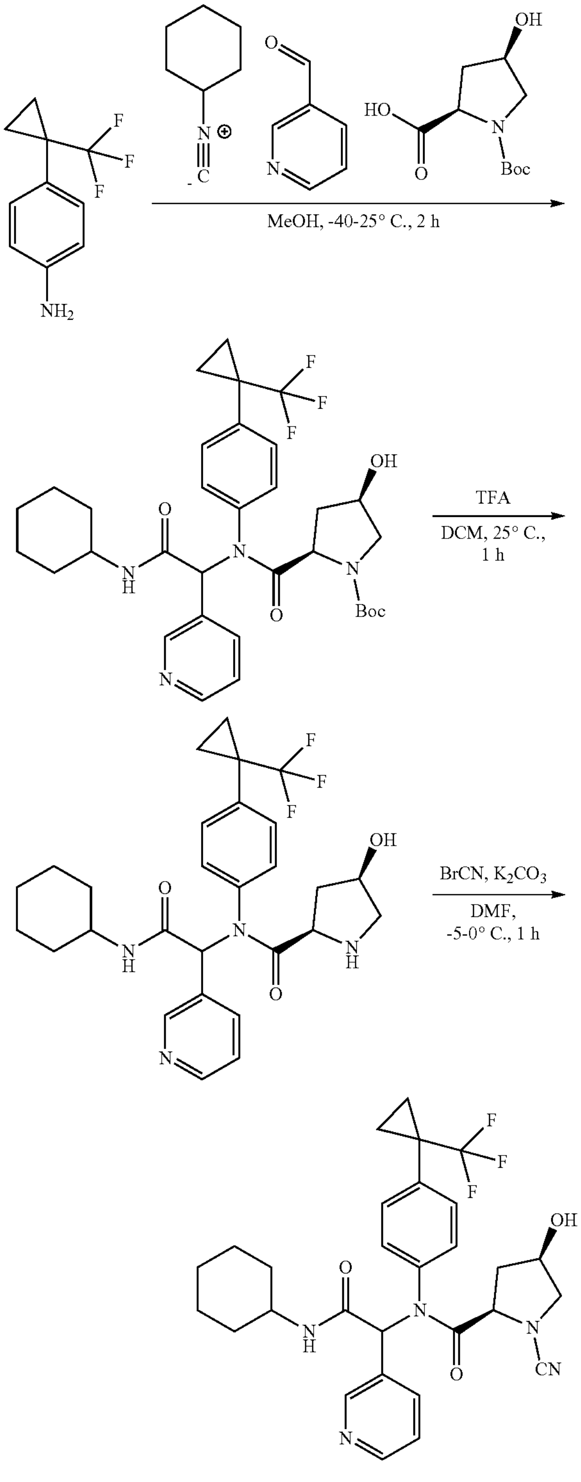

Step 1: (2R,4R)-tert-butyl 2-((2-(cyclohexylamino)-2-oxo-1-(pyridin-3-yl)ethyl)(4-(1-(trifluoromethyl)cyclopropyl)phenyl)carbamoyl)-4-hydroxypyrrolidine-1-carboxylate A solution of 4-[1-(trifluoromethyl)cyclopropyl]aniline (0.25 g, 1.24 mmol, 1 eq) and pyridine-3-carbaldehyde (159.72 mg, 1.49 mmol, 140.10 uL, 1.2 eq) in MeOH (3 mL) was stirred at 25° C. for 30 min. Then, (2R,4R)-1-tert-butoxycarbonyl-4-hydroxy-pyrrolidine-2-carboxylic acid (287.35 mg, 1.24 mmol, 1 eq) was added, and the resulting mixture was stirred for 15 min. The solution was cooled to −40° C. and isocyanocyclohexane (135.66 mg, 1.24 mmol, 154.51 uL, 1 eq) in MeOH (1 mL) was added drop-wise within 15 min for 3 times, and then the mixture was stirred at 25° C. for 1 h. Upon completion, the reaction mixture was concentrated under reduced pressure to give a residue. The residue was purified by column chromatography ($SiO_2$, petroleum ether:ethyl acetate=2:1 to 0:1) to give tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate (0.3 g, 451.88 umol, 36.37% yield, 95% purity) as a solid. MS (ESI) m/z 631.2 $[M+H]^+$. To give tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate (0.3 g, 451.88 umol, 36.37% yield, 95% purity) as a solid. MS (ESI) m/z 631.2 $[M+H]^+$.

Step 2: (2R,4R)—N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide To a solution of tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate (0.25 g, 396.39 umol, 1 eq) in DCM (2 mL) was added TFA (1.54 g, 13.51 mmol, 1 mL, 34.07 eq), and the mixture was stirred at 25° C. for 1 h. Upon completion, the reaction mixture was dried by blowing $N_2$, diluted with sat. $NaHCO_3$ solution (20 mL) and extracted with DCM (10 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (0.2 g, crude) as an oil.

(2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (0.07 g, 131.93 umol, 1 eq) was purified by prep-HPLC (column: Phenomenex Gemini-NX 150*30 mm*5 um; mobile phase: [water (0.1% TFA)-ACN]; B %: 15%-45%, 9 min) to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (23.49 mg, 44.27 umol, 33.56% yield, 100% purity) as a solid. MS (ESI) m/z 531.1 $[M+H]^+$. $^1H$ NMR (400 MHz, MeOD-$d_4$) δ=8.40 (dt, J=1.7, 4.5 Hz, 2H), 8.18 (br d, J=7.8 Hz, 1H), 7.69 (br d, J=8.0 Hz, 2H), 7.42 (br d, J=3.0 Hz, 2H), 7.33 (dd, J=5.2, 7.9 Hz, 1H), 6.98 (br s, 1H), 6.26 (s, 1H), 4.35 (br d, J=2.1 Hz, 1H), 4.23 (dd, J=7.3, 9.7 Hz, 1H), 3.73 (br d, J=1.9 Hz, 1H), 3.33 (br s, 1H), 3.24-3.12 (m, 1H), 2.09-1.97 (m, 2H), 1.91 (br d, J=13.0 Hz, 1H), 1.83-1.58 (m, 4H), 1.40-1.08 (m, 7H), 0.98 (br d, J=5.3 Hz, 2H).

(2R,4R)—N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide To a solution of tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate (0.25 g, 396.39 umol, 1 eq) in DCM (2 mL) was added TFA (1.54 g, 13.51 mmol, 1 mL, 34.07 eq), and the mixture was stirred at 25° C. for 1 h. Upon completion, the reaction mixture was dried by blowing $N_2$, diluted with sat. $NaHCO_3$ solution (20 mL) and extracted with DCM (10 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (0.2 g, crude) as an oil.

(2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (0.07 g, 131.93 umol, 1 eq) was purified by prep-HPLC (column: Phenomenex Gemini-NX 150*30 mm*5 um; mobile phase: [water (0.1% TFA)-ACN]; B %: 15%-45%, 9 min) to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (25.76 mg, 48.31 umol, 36.62% yield, 99.5% purity) as a solid. MS (ESI) m/z 531.2 $[M+H]^+$. $^1H$ NMR (400 MHz, MeOD-$d_4$) δ=8.52-8.41 (m, 2H), 7.99-7.56 (m, 2H), 7.55-7.19 (m, 3H), 7.19-6.51 (m, 1H), 6.09 (s, 1H), 4.41-4.32 (m, 1H), 4.27 (dd, J=6.9, 9.6 Hz, 1H), 3.74-3.61 (m, 1H), 3.34 (s, 1H), 3.19 (dd, J=4.3, 11.9 Hz, 1H), 2.04-1.93 (m, 2H), 1.86 (br d, J=10.1 Hz, 1H), 1.80-1.58 (m, 4H), 1.38-0.95 (m, 9H).

Step 3: (2R,4R)-1-cyano-N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide To a solution of (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (0.13 g, 245.01 umol, 1 eq) in DMF (2 mL) was added $K_2CO_3$ (101.59 mg, 735.04 umol, 3 eq). The solution was cooled to −5° C. and BrCN (31.14 mg, 294.02 umol, 21.63 uL, 1.2 eq) in DMF (1 mL) was added drop-wise, and then the mixture was stirred at 0° C. for 1 h. Upon completion, the reaction mixture was diluted with water (10 mL) and extracted with EtOAc (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 10 min) to give (2R,4R)-1-cyano-N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (81.23 mg, 146.20 umol, 59.67% yield, 100% purity) as a solid. MS (ESI) m/z 556.1 $[M+H]^+$. $^1H$ NMR (400 MHz, MeOD-$d_4$) δ=8.43-8.18 (m, 2H), 8.01-7.59 (m, 1H), 7.58-7.12 (m, 4H), 7.06-6.51 (m, 1H), 6.19 (s, 1H), 4.32-4.13 (m, 2H), 3.71 (ddd, J=3.9, 6.8, 10.6 Hz, 1H), 3.57 (dd, J=5.7, 9.4 Hz, 1H), 3.41 (dd, J=4.9, 9.3 Hz, 1H), 2.20-2.07 (m, 1H), 2.06-1.88 (m, 2H), 1.83-1.58 (m, 4H), 1.44-0.91 (m, 9H).

(2R,4R)-1-cyano-N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide To a solution of (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide (0.13 g, 245.01 umol, 1 eq) in DMF (2 mL) was added $K_2CO_3$ (101.59 mg, 735.04 umol, 3 eq), and the solution was cooled to −5° C. Then, BrCN (31.14 mg, 294.02 umol, 21.63 uL, 1.2 eq) in DMF (1 mL) was added drop-wise, and the mixture was stirred at 0° C. for 1 h. Upon completion, the reaction mixture was diluted with water (10 mL) and extracted with EtOAc (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 10 min) to give (2R, 4R)-1-cyano-N-[2-(cyclohexylamino)-2-oxo-1-(3-pyridyl) ethyl]-4-hydroxy-N-[4-[1-(trifluoromethyl)cyclopropyl] phenyl]pyrrolidine-2-carboxamide (89.41 mg, 160.93 umol, 65.68% yield, 100% purity) as a solid. MS (ESI) m/z 556.1 $[M+H]^+$. $^1H$ NMR (400 MHz, MeOD-$d_4$) δ=8.54-8.22 (m, 2H), 8.04-7.63 (m, 1H), 7.61-7.11 (m, 4H), 7.02-6.42 (m, 1H), 6.05 (s, 1H), 4.35-4.15 (m, 2H), 3.76-3.62 (m, 1H), 3.57 (dd, J=5.4, 9.5 Hz, 1H), 3.43 (dd, J=4.0, 9.5 Hz, 1H), 2.17-2.05 (m, 1H), 1.93 (td, J=4.3, 13.3 Hz, 2H), 1.83-1.54 (m, 4H), 1.44-0.94 (m, 9H).

Example 69: Synthesis of Compound 747b

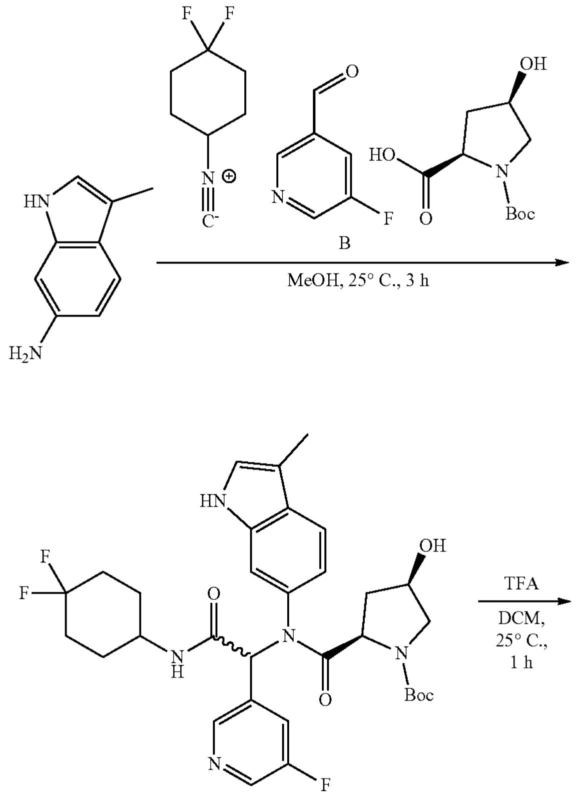

-continued

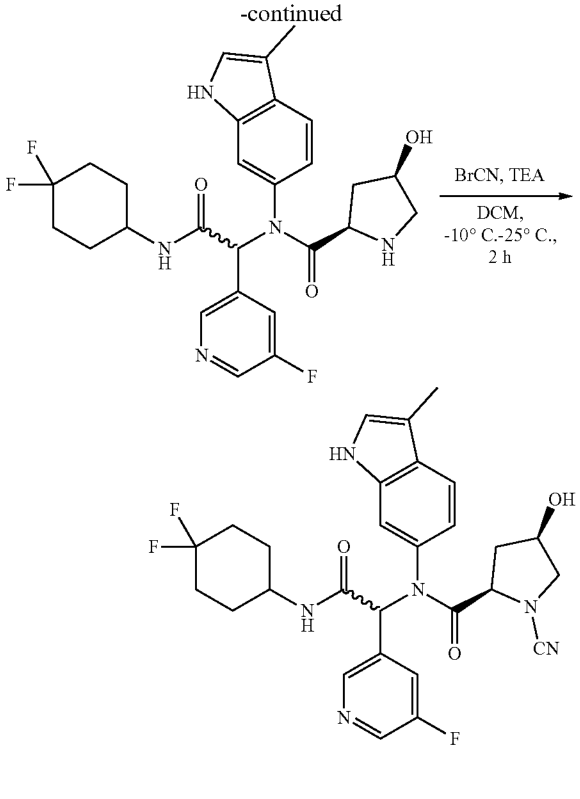

Step1:(2R,4R)-tert-butyl2-((2-((4,4-difluorocyclohexyl)amino)-1-(5-fluoropyridin-3-yl)-2-oxoethyl) (3-methyl-1H-indol-6-yl)carbamoyl)-4-hydroxypyrrolidine-1-carboxylate A solution of 3-methyl-1H-indol-6-amine (300 mg, 2.05 mmol, 1 eq), 5-fluoronicotinaldehyde (256.72 mg, 2.05 mmol, 1 eq) in MeOH (15 mL) was stirred at 25° C. for 1 h, and the mixture was added with (2R,4R)-1-(tert-butoxycarbonyl)-4-hydroxypyrrolidine-2-carboxylic acid (474.55 mg, 2.05 mmol, 1 eq). The resulting mixture was stirred at 25° C. for 0.5 h, at last, and the reaction was added with 1,1-difluoro-4-isocyanocyclohexane (268.08 mg, 1.85 mmol, 0.9 eq), and stirred at 25° C. for 1.5 h. Upon completion, the reaction mixture was concentrated under reduced pressure and was purified by prep-HPLC column: Phenomenex Gemini-NX 80*40 mm*3 um; mobile phase: [water (10 mM $NH_4HCO_3$)-ACN]; B %: 25%-55%, 8 min to give a product (2R,4R)-tert-butyl 2-((2-((4,4-difluorocyclohexyl)amino)-1-(5-fluoropyridin-3-yl)-2-oxoethyl)(3-methyl-1H-indol-6-yl)carbamoyl)-4-hydroxypyrrolidine-1-carboxylate (280 mg, 444.68 umol, 21.67% yield) and (2R,4R)-tert-butyl2-((2-((4,4-difluorocyclohexyl)amino)-1-(5-fluoropyridin-3-yl)-2-oxoethyl)(3-methyl-1H-indol-6-yl) carbamoyl)-4-hydroxypyrrolidine-1-carboxylate (200 mg, 317.63 umol, 15.48% yield) as a solid. MS (ESI) m/z 630.3 $[M+H]^+$

Step2:(2R,4R)—N-(2-((4,4-difluorocyclohexyl) amino)-1-(5-fluoropyridin-3-yl)-2-oxoethyl)-4-hydroxy-N-(3-methyl-1H-indol-6-yl)pyrrolidine-2-carboxamide Isomer 1: To a solution of (2R,4R)-tert-butyl 2-((2-((4,4-difluorocyclohexyl)amino)-1-(5-fluoropyridin-3-yl)-2-oxoethyl)(3-methyl-1H-indol-6-yl)carbamoyl)-4-hydroxypyrrolidine-1-carboxylate (280 mg, 444.68 umol, 1 eq) in DCM (5 mL) was added TFA (3.04 g, 26.68 mmol, 1.98 mL, 60 eq), and the mixture was stirred at 25° C. for 1 h. Upon completion, the mixture was quenched by addition $NaHCO_3$ (100 mL) and then extracted with EtOAc (50 mL*3). The combined organic layers were washed with brine 100 mL, dried over $Na_2SO_4$, filtered and concentrated under reduced pressure to give a residue to give the crude product (2R, 4R)—N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide (180 mg, crude) was obtained as an oil MS (ESI) m/z 530.2 $[M+H]^+$ Isomer 2: To a solution of (2R,4R)-tert-butyl 2-((2-((4,4-difluorocyclohexyl)amino)-1-(5-fluoropyridin-3-yl)-2-oxoethyl)(3-methyl-1H-indol-6-yl)carbamoyl)-4-hydroxypyrrolidine-1-carboxylate (200 mg, 317.63 umol, 1 eq) in DCM (6 mL) was added TFA (2.17 g, 19.06 mmol, 1.41 mL, 60 eq) and the mixture was stirred at 25° C. for 1 h. Upon completion, the mixture was quenched by addition $NaHCO_3$20 mL and then extracted with EtOAc (10 mL×3). The combined organic layers were washed with brine (100 mL), dried over $Na_2SO_4$, filtered and concentrated under reduced pressure to give the crude product ((2R,4R)—N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide (100 mg, crude) as an oil. MS (ESI) m/z 530.2 $[M+H]^+$ Step3:(2R,4R)-1-cyano-N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide Compound 747b Isomer 1: To a solution of (2R,4R)—N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide (180 mg, 339.91 umol, 1 eq) in DCM (3 mL) was added TEA (103.19 mg, 1.02 mmol, 141.93 uL, 3 eq) and the mixture was cooled at −10° C. Then, BrCN (54.01 mg, 509.86 umol, 37.50 uL, 1.5 eq) in DCM (0.5 mL) was added and the solution was stirred for 0.5 h at 0° C. and warmed to 25° C. for 1.5 h. Upon completion, the mixture was quenched by addition $H_2O$ (50 mL) and then extracted with EtOAc (30 mL*3). The combined organic layers were washed with brine 30 mL, dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 30%-60%, 10 min) to give (2R,4R)-1-cyano-N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide (35 mg, 63.11 umol, 18.57% yield) as a solid. MS (ESI) m/z 555.2 $[M+H]^+$ $^1H$ NMR (400 MHz, MeOD-$d_4$) δ=8.33-8.07 (m, 2H), 7.80-7.71 (m, 0.5H), 7.49 (m, 0.5H), 7.44-7.23 (m, 2H), 7.12-6.98 (m, 1H), 6.79 (m, 0.5H), 6.40 (m, 0.5H), 6.20 (m, 1H), 4.30-4.14 (m, 2H), 3.90 (br s, 1H), 3.58-3.51 (m, 1H), 3.41 (m, 1H), 2.23 (br d, J=12.6 Hz, 3H), 2.10-1.83 (m, 8H), 1.71-1.60 (m, 1H), 1.52-1.40 (m, 1H); $^1H$ NMR (400 MHz, DMSO-$d_6$) δ=10.74 (m, 1H), 8.27 (m, 1H), 8.19 (br s, 11H), 8.06 (m, 1H), 7.77-7.08 (m, 4H), 6.92-6.33 (m, 1H), 6.17 (br s, 11H), 5.05 (d, J=6.2 Hz, 1H), 4.06 (td, J=6.7, 13.0 Hz, 2H), 3.84 (br s, 1H), 3.49-3.41 (m, 1H), 3.22-3.16 (m, 1H), 2.20 (s, 3H), 2.10-1.68 (m, 9H), 1.67-1.34 (m, 2H).

Compound 747b Isomer 2: To a solution of 2R,4R)—N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide (100 mg, 188.84 umol, 1 eq) in DCM (3 mL) was added TEA (57.33 mg, 566.52 umol, 78.85 uL, 3 eq) and the mixture was cooled at −10° C. Then, BrCN (30.00 mg, 283.26 umol, 20.84 uL, 1.5 eq) in DCM (0.5 mL) was added and the mixture was stirred for 0.5 h at 0° C. and warmed to 25° C. for 1.5 h. Upon completion, the mixture was quenched by addition $H_2O$ (50 mL) and then extracted with EtOAc (30 mL*3). The combined organic layers were washed with brine (30 mL), dried over $Na_2SO_4$, filtered and concentrated under reduced pressure and was purified by prep-HPLC (column: Waters Xbridge BEH C18 100*30 mm*10 um; mobile phase: [water (10 mM $NH_4HCO_3$)-ACN]; B %: 30%-60%, 10 min) to give (2R, 4R)-1-cyano-N-(2-((4,4-difluorocyclohexyl)amino)-1-(5-fluoropyridin-3-yl)-2-oxoethyl)-4-hydroxy-N-(3-methyl-1H-indol-6-yl)pyrrolidine-2-carboxamide (30 mg, 54.10 umol, 28.65% yield) as a solid. MS (ESI) m/z 555.2 $[M+H]^+$ 1H NMR (400 MHz, MeOD-$d_4$) δ=8.35-8.12 (m, 2H), 7.82-7.72 (m, 0.5H), 7.57-7.47 (m, 0.5H), 7.46-7.20 (m, 2H), 7.13-6.99 (m, 1H), 6.82-6.72 (m, 0.5H), 6.41-6.32 (m, 0.5H), 6.22-6.03 (m, 1H), 4.33-4.14 (m, 2H), 3.87 (br s, 1H), 3.54 (m, 1H), 3.46-3.37 (m, 1H), 2.32-2.14 (m, 3H), 2.10-1.80 (m, 8H), 1.65 (m, 1H), 1.54-1.39 (m, 1H).

Example 70: Synthesis of Compound 755

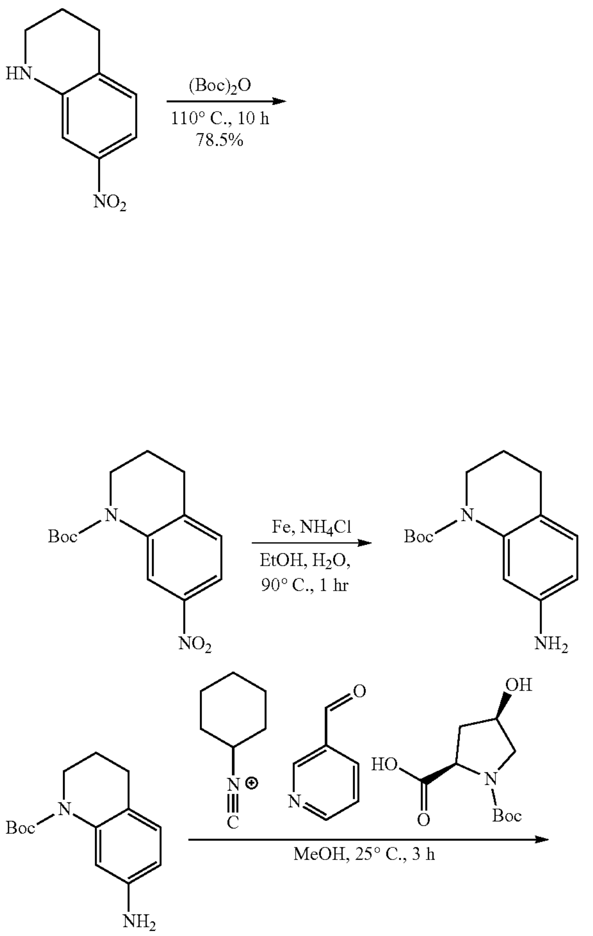

-continued

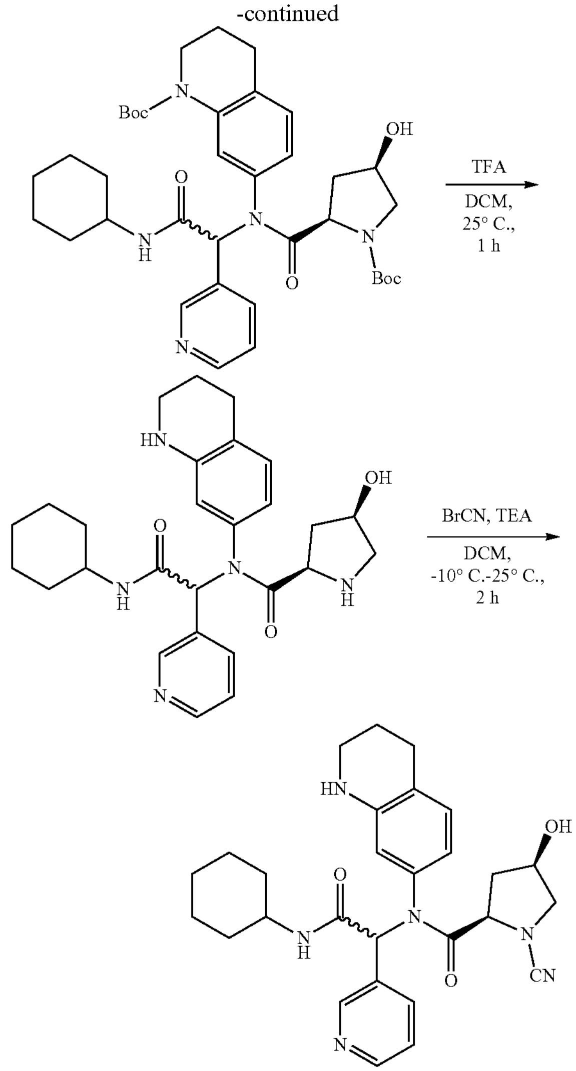

Step1: tert-butyl 7-nitro-3,4-dihydroquinoline-1(2H)-carboxylate

To a solution of 7-nitro-1,2,3,4-tetrahydroquinoline (2 g, 11.22 mmol, 1 eq) was added $Boc_2O$ (4.90 g, 22.45 mmol, 5.16 mL, 2 eq). The resulting mixture was stirred at 110° C. for 10 h. Upon completion, the mixture was quenched by addition $H_2O$ (300 mL) and then extracted with EtOAc (600 mL). The combined organic layers were washed with brine (200 mL), dried over $Na_2SO_4$, filtered and concentrated under reduced pressure to give a residue and was purified by column chromatography (SiO2, petroleum ether:EtOAc=10:1) to give a product tert-butyl 7-nitro-3,4-dihydroquinoline-1(2H)-carboxylate (2.5 g, 8.98 mmol, 80.03% yield) as a solid. MS (ESI) m/z 279.1 $[M+H]^+$ Step2: tert-butyl 7-amino-3,4-dihydroquinoline-1(2H)-carboxylate To a solution of tert-butyl 7-nitro-3,4-dihydroquinoline-1(2H)-carboxylate (2.45 g, 8.80 mmol, 1 eq) in EtOH (30 mL) and $H_2O$ (10 mL) was added Fe (4.92 g, 88.03 mmol, 10 eq), NH4Cl (4.71 g, 88.03 mmol, 10 eq) and the mixture was stirred at 90° C. for 1 h. Upon completion, the mixture was quenched by addition $H_2O$ (200 mL) and then extracted with EtOAc (100*3 mL). The combined organic layers were washed with brine (200 mL), dried over $Na_2SO_4$, filtered and concentrated under reduced pressure to give a residue tert-butyl 7-amino-3,4-dihydroquinoline-1(2H)-carboxylate (2 g, crude) as a solid. MS (ESI) m/z 249.2 $[M+H]^+$ Step3: tert-butyl7-((2R,4R)-1-(tert-butoxycarbonyl)-N-(2-(cyclohexylamino)-2-oxo-1-(pyridin-3-yl)ethyl)-4-hydroxypyrrolidine-2-carboxamido)-3,4-dihydroquinoline-1(2H)-carboxylate A solution of tert-butyl 7-amino-3,4-dihydroquinoline-1(2H)-carboxylate (300 mg, 1.21 mmol, 1 eq), nicotinaldehyde (129.40 mg, 1.21 mmol, 113.51 uL, 1 eq) in MeOH (15 mL) was stirred at 25° C. for 1 h and the mixture was added with (2R,4R)-1-(tert-butoxycarbonyl)-4-hydroxypyrrolidine-2-carboxylic acid (279.37 mg, 1.21 mmol, 1 eq). The resulting mixture was stirred at 25° C. for 0.5 h, isocyanocyclohexane (118.70 mg, 1.09 mmol, 135.19 uL, 0.9 eq) was added and the mixture was stirred at 25° C. for 1.5 h. Upon completion, the reaction mixture was concentrated under reduced pressure and purified by prep-HPLC column: Waters Xbridge Prep OBD C18 150*40 mm*10 um; mobile phase: [water (10 mM $NH_4HCO_3$)-ACN]; B %: 45%-75%, 8 min to give the product tert-butyl 7-((2R,4R)-1-(tert-butoxycarbonyl)-N-(2-(cyclohexylamino)-2-oxo-1-(pyridin-3-yl)ethyl)-4-hydroxypyrrolidine-2-carboxamido)-3,4-dihydroquinoline-1(2H)-carboxylate (370 mg, 545.86 umol, 45.18% yield) and tert-butyl7-((2R,4R)-1-(tert-butoxycarbonyl)-N-(2-(cyclohexylamino)-2-oxo-1-(pyridin-3-yl)ethyl)-4-hydroxypyrrolidine-2-carboxamido)-3,4-dihydroquinoline-1(2H)-carboxylate (330 mg, 486.85 umol, 40.30% yield) as an oil. MS (ESI) m/z 678.4 $[M+H]^+$ Step 4:(2R,4R)—N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide Isomer 1: To a solution of tert-butyl 7-((2R,4R)-1-(tert-butoxycarbonyl)-N-(2-(cyclohexylamino)-2-oxo-1-(pyridin-3-yl)ethyl)-4-hydroxypyrrolidine-2-carboxamido)-3,4-dihydroquinoline-1(2H)-carboxylate (370 mg, 545.86 umol, 1 eq) in DCM (8 mL) was added TFA (3.73 g, 32.75 mmol, 2.42 mL, 60 eq) and the mixture was stirred at 25° C. for 1 h. Upon completion, the mixture was quenched by addition $NaHCO_3$ (50 mL) and then extracted with EtOAc (20 mL*3). The combined organic layers were washed with brine (50 mL), dried over $Na_2SO_4$, filtered and concentrated under reduced pressure to give a residue to give (2R,4R)—N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide (200 mg, crude) was obtained as an oil. MS (ESI) m/z 478.4 $[M+H]^+$ Isomer 2: To a solution of tert-butyl 7-((2R,4R)-1-(tert-butoxycarbonyl)-N-(2-(cyclohexylamino)-2-oxo-1-(pyridin-3-yl)ethyl)-4-hydroxypyrrolidine-2-carboxamido)-3,4-dihydroquinoline-1(2H)-carboxylate (330 mg, 486.85 umol, 1 eq) in DCM (7 mL) was added TFA (3.33 g, 29.21 mmol, 2.16 mL, 60 eq). The resulting mixture was stirred at 25° C. for 1 h. Upon completion, the mixture was quenched by the addition of $NaHCO_3$ (50 mL) and then extracted with EtOAc (20 mL*3). The combined organic layers were washed with brine (50 mL), dried over $Na_2SO_4$, filtered and concentrated under reduced pressure to give a residue to give (2R,4R)—N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide (200 mg, crude) was obtained as an oil. MS (ESI) m/z 478.4 $[M+H]^+$ Step5:(2R,4R)-1-cyano-N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide Compound 755 Isomer 1: To a solution of (2R,4R)—N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide (100 mg, 209.38 umol, 1 eq) in DCM (1 mL) was added TEA (63.56 mg, 628.14 umol, 87.43 uL, 3 eq) and the mixture was cooled at −10° C. BrCN (33.27 mg, 314.07 umol, 23.10 uL, 1.5 eq) in DCM (0.5 mL) was added and the solution was stirred for 0.5 h at 0° C. and warmed to 25° C. for 1.5 h. Upon completion, the mixture was quenched by the addition $H_2O$ (20 mL) and then extracted with EtOAc (30 mL). The combined organic layers were washed with brine (20 mL), dried over $Na_2SO_4$, filtered and concentrated under reduced pressure to give a residue and was purified by prep-HPLC (column: Waters Xbridge BEH C18 100*30 mm*10 um; mobile phase: [water (10 mM $NH_4HCO_3$)-ACN]; B %: 25%-55%, 10 min) to give (2R,4R)-1-cyano-N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide (30 mg, 59.69 umol, 28.51% yield) as a solid. MS (ESI) m/z 503.3 $[M+H]^+$ $^1H$ NMR (400 MHz, MeOD-$d_4$) δ=8.33 (s, 2H), 7.61 (m, 1H), 7.23 (m, 1H), 6.81-6.58 (m, 2H), 6.06 (s, 1H), 5.81 (br s, 1H), 4.37-4.20 (m, 2H), 3.76-3.65 (m, 1H), 3.59 (dd, J=5.6, 9.4 Hz, 1H), 3.42 (dd, J=4.6, 9.2 Hz, 1H), 3.25-3.04 (m, 2H), 2.58 (br s, 2H), 2.21 (br s, 1H), 2.06-1.89 (m, 2H), 1.79-1.61 (m, 5H), 1.44-1.02 (m, 6H)

Compound 755 Isomer 2: To a solution of (2R,4R)—N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide (100 mg, 209.38 umol, 1 eq) in DCM (1 mL) was added TEA (63.56 mg, 628.14 umol, 87.43 uL, 3 eq) and the mixture was cooled at −10° C. BrCN (33.27 mg, 314.07 umol, 23.10 uL, 1.5 eq) in DCM (0.5 mL) was added and the solution was stirred for 0.5 h at 0° C. and warmed to 25° C. for 1.5 h. Upon completion, the mixture was quenched by addition $H_2O$ (20 mL) and then extracted with EtOAc (30 mL). The combined organic layers were washed with brine (20 mL), dried over $Na_2SO_4$, filtered and concentrated under reduced pressure to give a residue and was purified by prep-HPLC (column: Waters Xbridge BEH C18 100*30 mm*10 um; mobile phase: [water (10 mM $NH_4HCO_3$)-ACN]; B %: 25%-55%, 10 min) to give (2R,4R)-1-cyano-N-(2-(cyclohexylamino)-2-oxo-1-(pyridin-3-yl)ethyl)-4-hydroxy-N-(1,2,3,4-tetrahydroquinolin-7-yl)pyrrolidine-2-carboxamide (20 mg, 39.79 umol, 19.00% yield) as a solid. MS (ESI) m/z 503.3 $[M+H]^+$ $^1H$ NMR (400 MHz, MeOD-$d_4$) δ=8.49-8.27 (m, 2H), 7.64 (m, 1H), 7.25 (m, 1H), 6.95-6.47 (m, 2H), 5.92 (br s, 1H), 5.85-5.58 (m, 1H), 4.39-4.17 (m, 2H), 3.73-3.63 (m, 1H), 3.58 (m, 1H), 3.43 (m, 1H), 3.25-3.10 (m, 2H), 2.61 (br s, 2H), 2.17 (br s, 1H), 1.98-1.88 (m, 2H), 1.81-1.60 (m, 5H), 1.44-1.02 (m, 6H).

Example 71: Synthesis of Compound 759

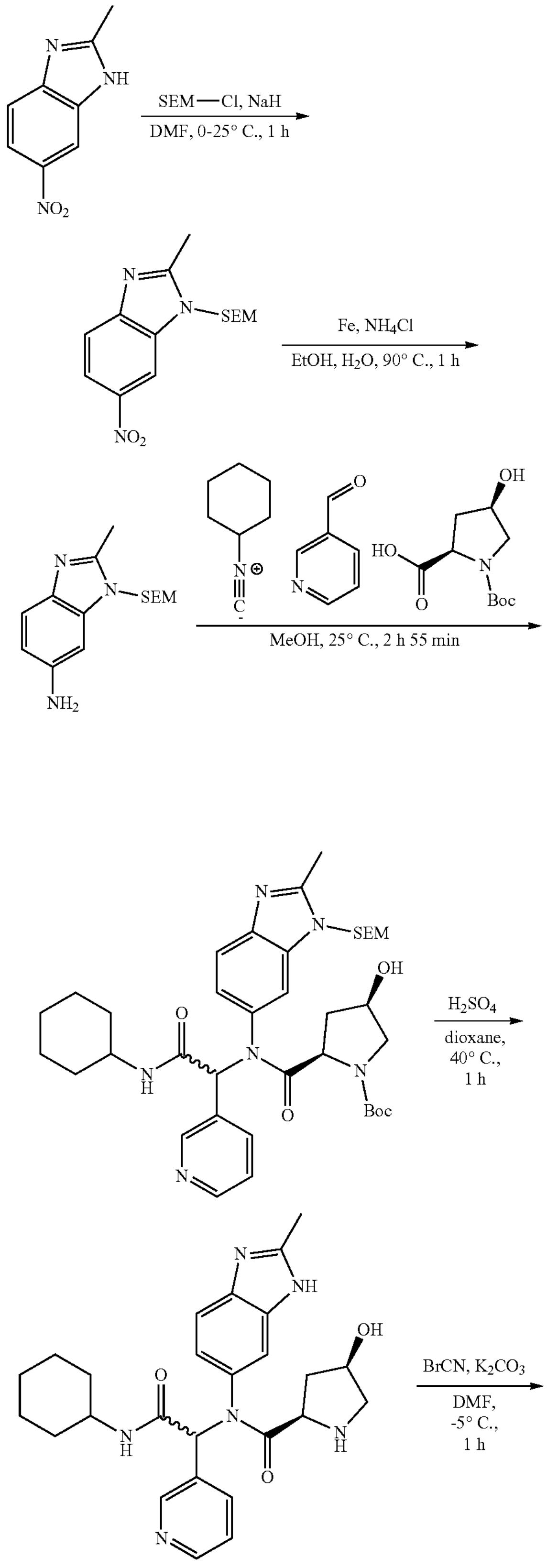

-continued

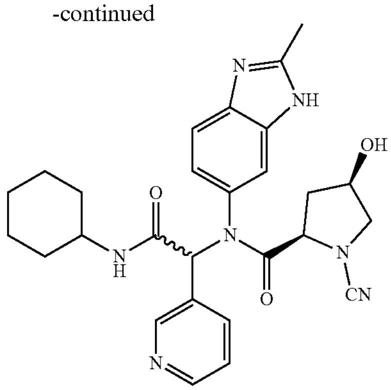

Step 1: 2-methyl-6-nitro-1-((2-(trimethylsilyl)ethoxy)methyl)-1H-benzo[d]imidazole To a solution of 2-methyl-6-nitro-1H-benzimidazole (1 g, 5.64 mmol, 1 eq) in THF (10 mL) was added NaH (270.94 mg, 6.77 mmol, 60% purity, 1.2 eq) at 0° C. Then, SEM-C1 (1.13 g, 6.77 mmol, 1.20 mL, 1.2 eq) was added drop-wise. The mixture was stirred at 25° C. for 1 h. Upon completion, the reaction mixture was then diluted with sat. $NH_4Cl$ (50 mL) and extracted with EtOAc (20 mL*3). The combined organic layers were dried over $Na_2SO_4$, filtered and concentrated under reduced pressure to give 2-methyl-6-nitro-1-((2-(trimethylsilyl)ethoxy)methyl)-1H-benzo[d]imidazole (1.7 g, crude) as a solid. MS (ESI) m/z 308.0 $[M+H]^+$.

Step 2: 2-methyl-1-((2-(trimethylsilyl)ethoxy)methyl)-1H-benzo[d]imidazol-6-amine To a solution of trimethyl-[2-[(2-methyl-6-nitro-benzimidazol-1-yl)methoxy]ethyl]silane (1.7 g, 5.53 mmol, 1 eq) in EtOH (15 mL) and $H_2O$ (5 mL) was added $NH_4Cl$ (1.48 g, 27.65 mmol, 5 eq) and Fe (1.54 g, 27.65 mmol, 5 eq). The mixture was stirred at 90° C. for 1 h. Upon completion, the reaction mixture was filtered and concentrated under reduced pressure to give a residue. The residue was purified by column chromatography ($SiO_2$, petroleum ether: EtOAc=2:1 to 0:1) to give 2-methyl-3-(2-trimethylsilylethoxymethyl)benzimidazol-5-amine (0.7 g, 2.40 mmol, 43.35% yield, 95% purity) as a solid. MS (ESI) m/z 278.1 $[M+H]^+$.

Step 3: (2R,4R)-tert-butyl 2-((2-(cyclohexylamino)-2-oxo-1-(pyridin-3-yl)ethyl)(2-methyl-1-((2-(trimethylsilyl)ethoxy)methyl)-1H-benzo[d]imidazol-6-yl)carbamoyl)-4-hydroxypyrrolidine-1-carboxylate To a solution of 2-methyl-3-(2-trimethylsilylethoxymethyl)benzimidazol-5-amine (0.2 g, 720.89 umol, 1 eq) in MeOH (3 mL) was added pyridine-3-carbaldehyde (77.21 mg, 720.89 umol, 67.73 uL, 1 eq). After stirring for 30 min, (2R,4R)-1-tert-butoxycarbonyl-4-hydroxy-pyrrolidine-2-carboxylic acid (166.70 mg, 720.89 umol, 1 eq) was added and stirred at 25° C. for 10 min. Isocyanocyclohexane (78.70 mg, 720.89 umol, 89.63 uL, 1 eq) in MeOH (1 mL) was added drop-wise for 3 times within 15 min, and the mixture was stirred at 25° C. for 2 h. Upon completion, the reaction mixture was concentrated under reduced pressure to give a residue. The residue was purified by column chromatography ($SiO_2$, petroleum ether:EtOAc=2:1 to 0:1) to give (2R,4R)-tert-butyl 2-((2-(cyclohexylamino)-2-oxo-1-(pyridin-3-yl)ethyl)(2-methyl-1-((2-(trimethylsilyl)ethoxy)methyl)-1H-benzo[d]imidazol-6-yl)carbamoyl)-4-hydroxypyrrolidine-1-carboxylate (0.35 g, 396.07 umol, 54.94% yield, 80% purity) as a an oil. MS (ESI) m/z 707.3 $[M+H]^+$.

Step 4: (2R,4R)—N-(2-(cyclohexylamino)-2-oxo-1-(pyridin-3-yl)ethyl)-4-hydroxy-N-(2-methyl-1H-benzo[d]imidazol-6-yl)pyrrolidine-2-carboxamide To a solution of tert-butyl (2R,4R)-2-[[2-(cyclohexylamino)-2-oxo-1-(3-pyridyl)ethyl]-[2-methyl-3-(2-trimethylsilylethoxymethyl)benzimidazol-5-yl]carbamoyl]-4-hydroxy-pyrrolidine-1-carboxylate (0.2 g, 282.91 umol, 1 eq) in dioxane (4 mL) was added $H_2SO_4$ (368.00 mg, 3.68 mmol, 200.00 uL, 98% purity, 13.00 eq), and the mixture was stirred at 40° C. for 1 h. Upon completion, the reaction mixture was concentrated under reduced pressure to give a residue. The residue was diluted with sat. $K_2CO_3$ (50 mL) to adjust pH=10, the aqueous layers were concentrated under reduced pressure to give (2R,4R)—N-[2-(cyclohexylamino)-2-oxo-1-(3-pyridyl)ethyl]-4-hydroxy-N-(2-methyl-3H-benzimidazol-5-yl)pyrrolidine-2-carboxamide (0.15 g, crude) as a solid. MS (ESI) m/z 477.2 $[M+H]^+$.

Step 5: (2R,4R)-1-cyano-N-(2-(cyclohexylamino)-2-oxo-1-(pyridin-3-yl)ethyl)-4-hydroxy-N-(2-methyl-1H-benzo[d]imidazol-6-yl)pyrrolidine-2-carboxamide To a solution of (2R,4R)—N-[2-(cyclohexylamino)-2-oxo-1-(3-pyridyl)ethyl]-4-hydroxy-N-(2-methyl-3H-benzimidazol-5-yl)pyrrolidine-2-carboxamide (0.15 g, 314.75 umol, 1 eq) in DMF (2 mL) was added $K_2CO_3$ (130.50 mg, 944.25 umol, 3 eq). Then, CNBr (40.01 mg, 377.70 umol, 27.78 uL, 1.2 eq) in DMF (0.5 mL) was added drop-wise at −5° C. and stirred at −5° C. for 1 h under $N_2$ atmosphere. Upon completion, the reaction mixture was diluted with water (20 mL) and extracted with EtOAc (10 mL*3). The combined organic layers were dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 17%-47%, 10 min) to give (2R,4R)-1-cyano-N-[2-(cyclohexylamino)-2-oxo-1-(3-pyridyl)ethyl]-4-hydroxy-N-(2-methyl-3H-benzimidazol-5-yl)pyrrolidine-2-carboxamide (8.67 mg, 17.29 umol, 5.49% yield, 100% purity) as a solid. MS (ESI) m/z 502.2 $[M+H]^+$. $^1H$ NMR (400 MHz, METHANOL-$d_4$) δ=8.49-8.18 (m, 2H), 8.02 (br s, 1H), 7.75-7.32 (m, 2H), 7.20-7.11 (m, 1H), 7.01-6.40 (m, 1H), 6.27-6.03 (m, 1H), 4.35-4.10 (m, 2H), 3.82-3.63 (in, 1H), 3.60-3.51 (m, 1H), 3.47-3.37 (m, 1H), 2.64-2.40 (m, 3H), 2.17-1.90 (m, 3H), 1.83-1.57 (m, 4H), 1.45-1.00 (m, 5H).

Example 72: Synthesis of Compound 763

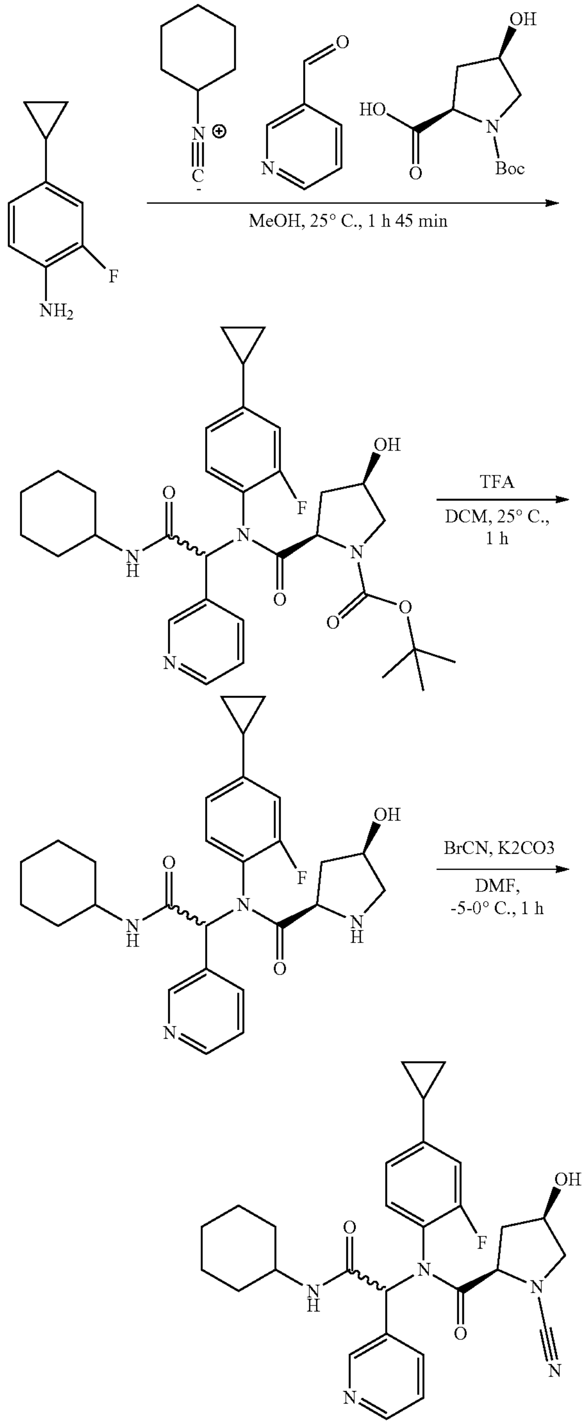

Step 1: tert-butyl (2R,4R)-2-[[2-(cyclohexylamino)-2-oxo-1-(3-pyridyl)ethyl]-(4-cyclopropyl-2-fluoro-phenyl)carbamoyl]-4-hydroxy-pyrrolidine-1-carboxylate A mixture of pyridine-3-carbaldehyde (212.55 mg, 1.98 mmol, 186.44 uL, 1.5 eq) and 4-cyclopropyl-2-fluoro-aniline (200 mg, 1.32 mmol, 1 eq) in MeOH (2 mL) was stirred at 25° C. for 0.5 h. (2R,4R)-1-tert-butoxycarbonyl-4-hydroxy-pyrrolidine-2-carboxylic acid (305.92 mg, 1.32 mmol, 1 eq) was added at −40° C. for 15 min, and then a solution of isocyanocyclohexane (144.42 mg, 1.32 mmol, 164.49 uL, 1 eq) was added. The resulting solution was slowly warmed to 25° C. and stirred for 1 h. Upon completion, the reaction mixture was concentrated under reduced pressure to give a residue. The crude was purified by prep-HPLC (column: Kromasil C18 (250*50 mm*10 um); mobile phase: [water (10 mM $NH_4HCO_3$)-ACN]; B %: 35%-75%, 10 min) to afford tert-butyl (2R,4R)-2-[[2-(cyclohexylamino)-2-oxo-1-(3-pyridyl)ethyl]-(4-cyclopropyl-2-fluoro-phenyl)carbamoyl]-4-hydroxy-pyrrolidine-1-carboxylate (123 mg, 201.23 umol, 15.21% yield, 95% purity) as a solid. MS (ESI) m/z 581.4 $[M+H]^+$, and tert-butyl (2R,4R)-2-[[2-(cyclohexylamino)-2-oxo-1-(3-pyridyl)ethyl]-(4-cyclopropyl-2-fluoro-phenyl)carbamoyl]-4-hydroxy-pyrrolidine-1-carboxylate (130 mg, 212.68 umol, 16.08% yield, 95% purity) as a solid. MS (ESI) m/z 581.4 $[M+H]^+$.

Step 2: (2R,4R)—N-[2-(cyclohexylamino)-2-oxo-1-(3-pyridyl)ethyl]-N-(4-cyclopropyl-2-fluoro-phenyl)-4-hydroxy-pyrrolidine-2-carboxamide tert-butyl (2R,4R)-2-[[2-(cyclohexylamino)-2-oxo-1-(3-pyridyl)ethyl]-(4-cyclopropyl-2-fluoro-phenyl)carbamoyl]-4-hydroxy-pyrrolidine-1-carboxylate (120 mg, 206.65 umol, 1 eq) in DCM (1.5 mL) was added with TFA (0.5 mL) at 25° C. for 1 h. Upon completion, the reaction mixture was diluted with $Na_2CO_3$ (10 mL) and extracted with DCM (10 mL*3). The combined organic layers were washed with brine, dried over $Na_2SO_4$, filtered and concentrated under reduced pressure to give a residue. The reaction mixture was concentrated under reduced pressure to give a residue to get the product (2R,4R)—N-[2-(cyclohexylamino)-2-oxo-1-(3-pyridyl)ethyl]-N-(4-cyclopropyl-2-fluoro-phenyl)-4-hydroxy-pyrrolidine-2-carboxamide (180 mg, crude) as an oil. MS (ESI) m/z 481.3 $[M+H]^+$.

(2R,4R)—N-[2-(cyclohexylamino)-2-oxo-1-(3-pyridyl)ethyl]-N-(4-cyclopropyl-2-fluoro-phenyl)-4-hydroxy-pyrrolidine-2-carboxamide tert-butyl (2R,4R)-2-[[2-(cyclohexylamino)-2-oxo-1-(3-pyridyl)ethyl]-(4-cyclopropyl-2-fluoro-phenyl)carbamoyl]-4-hydroxy-pyrrolidine-1-carboxylate (120 mg, 206.65 umol, 1 eq) in DCM (1.5 mL) was added with TFA (0.5 mL), and the resulting mixture was stirred at 25° C. for 1 h. Upon completion, the reaction mixture was diluted with $Na_2CO_3$ (10 mL) and extracted with DCM (10 mL*3). The combined organic layers were washed with brine, dried over $Na_2SO_4$, filtered and concentrated under reduced pressure to afford (2R,4R)—N-[2-(cyclohexylamino)-2-oxo-1-(3-pyridyl)ethyl]-N-(4-cyclopropyl-2-fluoro-phenyl)-4-hydroxy-pyrrolidine-2-carboxamide (190 mg, crude) was obtained as an oil. MS (ESI) m/z 481.3 $[M+H]^+$.

Step 3: (2R,4R)-1-cyano-N-[2-(cyclohexylamino)-2-oxo-1-(3-pyridyl)ethyl]-N-(4-cyclopropyl-2-fluoro-phenyl)-4-hydroxypyrrolidine-2-carboxamide (2R,4R)—N-[2-(cyclohexylamino)-2-oxo-1-(3-pyridyl)ethyl]-N-(4-cyclopropyl-2-fluoro-phenyl)-4-hydroxypyrrolidine-2-carboxamide (180 mg, 374.55 umol, 1 eq) in DMF (1.5 mL) was add with $K_2CO_3$ (155.30 mg, 1.12 mmol, 3 eq)

and then cooled to −5° C. Then, BrCN (47.61 mg, 449.46 umol, 33.06 uL, 1.2 eq) in DMF (0.5 mL) was added drop-wise, and the mixture was stirred at 0° C. for 1 h. Upon completion, the reaction mixture was diluted with $H_2O$ (10 mL) and extracted with EtOAc (10 mL*3). The combined organic layers were washed with brine, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 30%-55%, 8 min) to get the product (2R,4R)-1-cyano-N-[2-(cyclohexylamino)-2-oxo-1-(3-pyridyl)ethyl]-N-(4-cyclopropyl-2-fluoro-phenyl)-4-hydroxypyrrolidine-2-carboxamide (38.02 mg, 75.05 umol, 20.04% yield, 99.8% purity) as a solid. MS (ESI) m/z 506.1 $[M+H]^+$. $^1H$ NMR (400 MHz, METHANOL-$d_4$) δ=8.35-8.27 (m, 2H), 8.25-8.16 (m, 11H), 7.69 (s, 11H), 7.56 (br d, J=7.9 Hz, 1H), 7.20 (dd, J=4.9, 7.9 Hz, 1H), 6.95-6.87 (m, 1H), 6.60 (dd, J=1.7, 10.9 Hz, 1H), 6.16 (s, 1H), 4.23 (quin, J=5.7 Hz, 1H), 4.13-4.01 (m, 1H), 3.72 (tdt, J=3.7, 7.4, 10.9 Hz, 1H), 3.63-3.55 (m, 1H), 3.41 (dd, J=5.3, 9.3 Hz, 1H), 2.20-2.10 (m, 1H), 1.94 (br s, 2H), 1.85-1.59 (m, 5H), 1.40-1.05 (m, 5H), 0.98 (dd, J=2.0, 8.4 Hz, 2H), 0.66-0.56 (m, 2H).

(2R,4R)-1-cyano-N-[2-(cyclohexylamino)-2-oxo-1-(3-pyridyl)ethyl]-N-(4-cyclopropyl-2-fluoro-phenyl)-4-hydroxypyrrolidine-2-carboxamide (2R,4R)—N-[2-(cyclohexylamino)-2-oxo-1-(3-pyridyl)ethyl]-N-(4-cyclopropyl-2-fluoro-phenyl)-4-hydroxypyrrolidine-2-carboxamide (180 mg, 374.55 umol, 1 eq) in DMF (1.5 mL) and $K_2CO_3$ (155.30 mg, 1.12 mmol, 3 eq) was cooled to −5° C. BrCN (47.61 mg, 449.46 umol, 33.06 uL, 1.2 eq) in DMF (0.5 mL) was added drop-wise, and the mixture was stirred at 0° C. for 1 h. Upon completion, the reaction mixture was diluted with $H_2O$ (10 mL) and extracted with EtOAc (10 mL*3). The combined organic layers were washed with brine, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 30%-55%, 8 min) to get the product (2R,4R)-1-cyano-N-[2-(cyclohexylamino)-2-oxo-1-(3-pyridyl)ethyl]-N-(4-cyclopropyl-2-fluoro-phenyl)-4-hydroxypyrrolidine-2-carboxamide (30 mg, 59.34 umol, 15.84% yield, 100% purity) was obtained as a solid. MS (ESI) m/z 506.1 $[M+H]^+$. $^1H$ NMR (400 MHz, METHANOL-$d_4$) δ=8.39-8.30 (m, 2H), 7.77 (t, J=8.2 Hz, 1H), 7.55 (br d, J=8.2 Hz, 1H), 7.19 (dd, J=5.0, 7.8 Hz, 1H), 6.96 (dd, J=1.8, 8.4 Hz, 1H), 6.57 (dd, J=1.8, 11.2 Hz, 1H), 6.01 (s, 1H), 4.31-4.21 (m, 2H), 3.68 (s, 1H), 3.61-3.54 (m, 1H), 3.41 (dd, J=4.3, 9.4 Hz, 1H), 2.12-2.02 (m, 1H), 2.01-1.92 (m, 1H), 1.88-1.80 (m, 2H), 1.78-1.59 (m, 4H), 1.41-1.09 (m, 5H), 1.02-0.96 (m, 2H), 0.68-0.57 (m, 2H).

Example 73: Synthesis of Compound 767

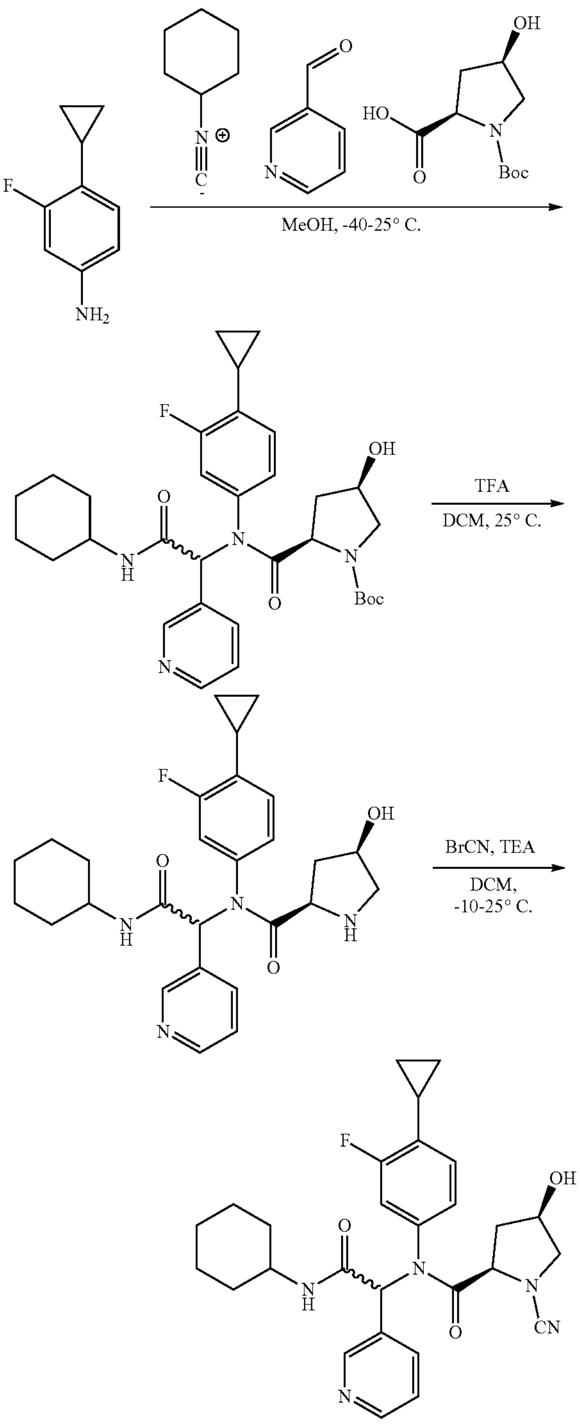

Step 1: (2R,4R)-tert-butyl 2-((2-(cyclohexylamino)-2-oxo-1-(pyridin-3-yl)ethyl)(4-cyclopropyl-3-fluorophenyl)carbamoyl)-4-hydroxypyrrolidine-1-carboxylate A mixture of 4-cyclopropyl-3-fluoro-aniline (200.00 mg, 1.32 mmol, 1 eq), pyridine-3-carbaldehyde (212.08 mg, 1.98 mmol, 186.04 uL, 1.5 eq) and MeOH (5 mL) was stirred at 25° C. for 0.5 h. To the resulting mixture was added (2R,4R)-1-tert-butoxycarbonyl-4-hydroxy-pyrrolidine-2-carboxylic acid (305.24 mg, 1.32 mmol, 1 eq) and cooled to −40° C. for 15 min. Isocyanocyclohexane (144.10 mg, 1.32 mmol, 164.12 uL, 1 eq) dissolved in MeOH (0.5 mL) was added at −40° C. drop-wise. The reaction mixture was stirred at 25° C. for 16 h. Upon completion, the reaction mixture was concentrated under reduced pressure to give a residue. The reaction mixture was purified by column chromatography ($SiO_2$, petroleum ether:EtOAc=5:1-0:1) to give two products. The tert-butyl (2R,4R)-2-[[2-(cyclohexylamino)-2-oxo-1-(3-pyridyl)ethyl]-(4-cyclopropyl-3-fluoro-phenyl) carbamoyl]-4-hydroxy-pyrrolidine-1-carboxylate (300 mg, 456.96 umol, 34.62% yield, 88.45% purity) was obtained, as a solid and used directly for next step. MS (ESI) m/z 581.2 $[M+H]^+$. The tert-butyl (2R,4R)-2-[[2-(cyclohexylamino)-2-oxo-1-(3-pyridyl)ethyl]-(4-cyclopropyl-3-fluoro-phenyl) carbamoyl]-4-hydroxy-pyrrolidine-1-carboxylate (300 mg, 446.78 umol, 33.85% yield, 86.48% purity) was obtained, as a solid and used directly for next step. MS (ESI) m/z 581.2 $[M+H]^+$.

Step 2: (2R,4R)—N-(2-(cyclohexylamino)-2-oxo-1-(pyridin-3-yl)ethyl)-N-(4-cyclopropyl-3-fluorophenyl)-4-hydroxypyrrolidine-2-carboxamide A mixture of tert-butyl (2S,3R)-2-[(4-tert-butylphenyl)-[2-(cyclohexylamino)-2-oxo-1-(3-pyridyl)ethyl]carbamoyl]-3-fluoro-pyrrolidine-1-carboxylate (280 mg, 482.15 umol, 1 eq), TFA (274.88 mg, 2.41 mmol, 178.49 uL, 5 eq) and DCM (2 mL) was stirred at 25° C. for 16 h. Upon completion, the reaction mixture was diluted with $NaHCO_3$ (50 mL) and extracted with DCM (30 mL*3). The combined organic layers were washed with brine (50 mL), dried over $Na_2SO_4$, filtered and concentrated under reduced pressure to give a residue (2R,4R)—N-[2-(cyclohexylamino)-2-oxo-1-(3-pyridyl)ethyl]-N-(4-cyclopropyl-3-fluoro-phenyl)-4-hydroxy-pyrrolidine-2-carboxamide (100 mg, crude), as a solid. MS (ESI) m/z 481.2 $[M+H]^+$.

A mixture of tert-butyl (2S,3R)-2-[(4-tert-butylphenyl)-[2-(cyclohexylamino)-2-oxo-1-(3-pyridyl)ethyl]carbamoyl]-3-fluoro-pyrrolidine-1-carboxylate (280 mg, 482.15 umol, 1 eq), TFA (274.88 mg, 2.41 mmol, 178.49 uL, 5 eq) and DCM (2 mL) was stirred at 25° C. for 16 h. Upon completion, the reaction mixture was diluted with $NaHCO_3$ (50 mL) and extracted with DCM (30 mL*3). The combined organic layers were washed with brine (50 mL), dried over $Na_2SO_4$, filtered and concentrated under reduced pressure to give (2R,4R)—N-[2-(cyclohexylamino)-2-oxo-1-(3-pyridyl)ethyl]-N-(4-cyclopropyl-3-fluoro-phenyl)-4-hydroxy-pyrrolidine-2-carboxamide (165 mg, crude), as a solid. MS (ESI) m/z 481.2 $[M+H]^+$ Step3: (2R,4R)-1-cyano-N-(2-(cyclohexylamino)-2-oxo-1-(pyridin-3-yl)ethyl)-N-(4-cyclopropyl-3-fluorophenyl)-4-hydroxypyrrolidine-2-carboxamide To a solution of (2R,4R)—N-[2-(cyclohexylamino)-2-oxo-1-(3-pyridyl)ethyl]-N-(4-cyclopropyl-3-fluoro-phenyl)-4-hydroxy-pyrrolidine-2-carboxamide (85 mg, 176.87 umol, 1 eq) in DCM (1 mL) was added TEA (53.69 mg, 530.62 umol, 73.85 uL, 3 eq) and the mixture was cooled at −10° C., and BrCN (37.47 mg, 353.74 umol, 26.02 uL, 2 eq) was added. Then the mixture solution was stirred at 0° C. for 1 h and warmed to 25° C. gradually. Upon completion, the mixture was quenched by addition $H_2O$ (20 mL) and then extracted with DCM (20 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 30%-60%, 10 min) to get the product (2R,4R)-1-cyano-N-[2-(cyclohexylamino)-2-oxo-1-(3-pyridyl)ethyl]-N-(4-cyclopropyl-3-fluoro-phenyl)-4-hydroxy-pyrrolidine-2-carboxamide (33.5 mg, 65.17 umol, 36.85% yield, 98.36% purity), as a solid. MS (ESI) m/z 506.2 $[M+H]^+$. $^1H$ NMR (400 MHz, METHANOL-$d_4$) δ=8.58-8.09 (m, 2H), 7.80-7.37 (m, 2H), 7.32-7.12 (m, 1H), 7.04-6.36 (m, 2H), 6.28-6.02 (m, 1H), 4.32-4.13 (m, 2H), 3.72 (br s, 11H), 3.58 (dd, J=5.6, 9.3 Hz, 1H), 3.41 (dd, J=5.0, 9.4 Hz, 1H), 2.12 (br d, J=6.5 Hz, 1H), 2.03-1.86 (m, 3H), 1.84-1.54 (m, 4H), 1.46-1.01 (m, 5H), 0.97 (br d, J=8.3 Hz, 2H), 0.65 (br s, 2H).

To a solution of (2R,4R)—N-[2-(cyclohexylamino)-2-oxo-1-(3-pyridyl)ethyl]-N-(4-cyclopropyl-3-fluoro-phenyl)-4-hydroxy-pyrrolidine-2-carboxamide (85 mg, 176.87 umol, 1 eq) in DCM (1 mL) was added TEA (53.69 mg, 530.62 umol, 73.85 uL, 3 eq) and the mixture was cooled at −10° C. Then, BrCN (37.47 mg, 353.74 umol, 26.02 uL, 2 eq) was added and stirred for 1 h at 0° C. and warmed to 25° C. gradually. Upon completion, the mixture was quenched by addition $H_2O$ (20 mL) and then extracted with DCM (20 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 30%-60%, 10 min) to get the product (2R,4R)-1-cyano-N-[2-(cyclohexylamino)-2-oxo-1-(3-pyridyl)ethyl]-N-(4-cyclopropyl-3-fluoro-phenyl)-4-hydroxy-pyrrolidine-2-carboxamide (40.25 mg, 78.62 umol, 26.06% yield, 98.76% purity), as a solid. MS (ESI) m/z 506.2 $[M+H]^+$. $^1H$ NMR (400 MHz, METHANOL-$d_4$) δ=8.54-8.19 (m, 2H), 7.75-7.44 (m, 2H), 7.35-7.15 (m, 1H), 7.09-6.21 (m, 2H), 6.18-5.93 (m, 11H), 4.38-4.09 (m, 2H), 3.77-3.63 (m, 1H), 3.62-3.54 (m, 1H), 3.47-3.39 (m, 1H), 2.19-1.87 (m, 4H), 1.83-1.52 (m, 4H), 1.45-0.90 (m, 7H), 0.80-0.52 (m, 2H).

Example 74: Synthesis of Compound 775

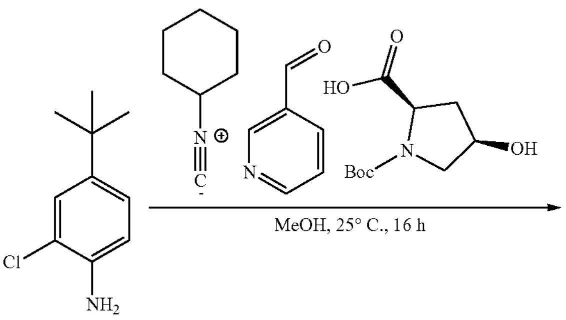

-continued

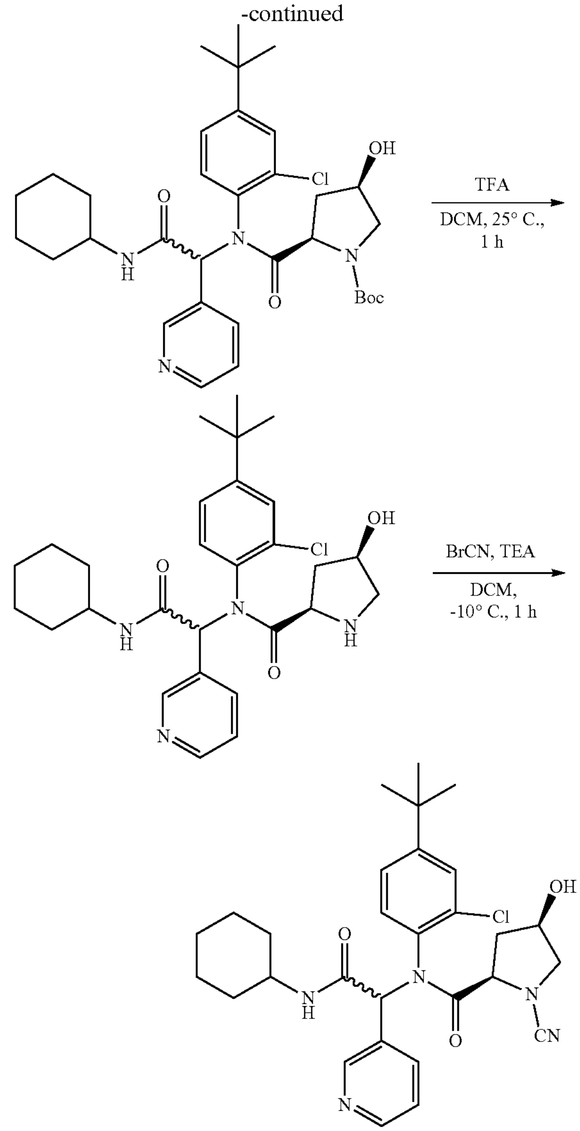

Step 1: (2R)-tert-butyl (2R,4R)-tert-butyl 2-((4-(tert-butyl)-2-chlorophenyl)(2-(cyclohexylamino)-2-oxo-1-(pyridin-3-yl)ethyl)carbamoyl)-4-hydroxypyrrolidine-1-carboxylate A solution of pyridine-3-carbaldehyde (174.94 mg, 1.63 mmol, 153.46 uL, 1 eq), 4-tert-butyl-2-chloro-aniline (300 mg, 1.63 mmol, 206.63 uL, 1 eq), (2R,4R)-1-tert-butoxycarbonyl-4-hydroxy-pyrrolidine-2-carboxylic acid (377.69 mg, 1.63 mmol, 1 eq) and isocyanocyclohexane (160.47 mg, 1.47 mmol, 182.77 uL, 0.9 eq) in MeOH (10 mL) was stirred at 25° C. for 16 h. The reaction mixture was concentrated under reduced pressure, then purified by prep-HPLC to give the product (2R,4R)-tert-butyl 2-((4-(tert-butyl)-2-chlorophenyl)(2-(cyclohexylamino)-2-oxo-1-(pyridin-3-yl)ethyl)carbamoyl)-4-hydroxypyrrolidine-1-carboxylate (614 mg, 1.00 mmol, 61.31% yield) as a solid. MS (ESI) m/z 613.4 $[M+H]^+$ prep-HPLC condition: column: Phenomenex luna C18 250*50 mm*10 um; mobile phase: [water (0.1% TFA)-ACN]; B %: 40%-60%, 10 min.

Step 2: (2R,4R)—N-(4-(tert-butyl)-2-chlorophenyl)-N-(2-(cyclohexylamino)-2-oxo-1-(pyridin-3-yl)ethyl)-4-hydroxypyrrolidine-2-carboxamide A solution of (2R,4R)-tert-butyl 2-((4-(tert-butyl)-2-chlorophenyl)(2-(cyclohexylamino)-2-oxo-1-(pyridin-3-yl)ethyl)carbamoyl)-4-hydroxypyrrolidine-1-carboxylate (154 mg, 228.54 umol, 91% purity, 1 eq) in TFA (2 mL) and DCM (6 mL) was stirred at 25° C. for 1 h. The reaction mixture was concentrated under reduced pressure and then purified by prep-HPLC to give (2R,4R)—N-(4-tert-butyl-2-chlorophenyl)-N-[2-(cyclohexylamino)-2-oxo-1-(3-pyridyl)ethyl]-4-hydroxy-pyrrolidine-2-carboxamide (115 mg, 212.93 umol, 93.17% yield, 95% purity) as a solid. MS (ESI) m/z 513.2 $[M+H]^+$. prep-HPLC condition: column: Phenomenex Gemini-NX 150*30 mm*5 um; mobile phase: [water (0.1% TFA)-ACN]; B %: 15%-45%, 9 min.

Step 3: (2R,4R)—N-(4-(tert-butyl)-2-chlorophenyl)-1-cyano-N-(2-(cyclohexylamino)-2-oxo-1-(pyridin-3-yl)ethyl)-4-hydroxypyrrolidine-2-carboxamide To a solution of (2R,4R)—N-(4-tert-butyl-2-chloro-phenyl)-N-[2-(cyclohexylamino)-2-oxo-1-(3-pyridyl)ethyl]-4-hydroxy-pyrrolidine-2-carboxamide (105 mg, 204.65 umol, 1 eq) in DCM (1.5 mL) was added TEA (62.13 mg, 613.95 umol, 85.45 uL, 3 eq) and then BrCN (22.11 mg, 208.74 umol, 15.35 uL, 1.02 eq) under $N_2$ at −10° C. The resulting mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R,4R)—N-(4-(tert-butyl)-2-chlorophenyl)-1-cyano-N-(2-(cyclohexylamino)-2-oxo-1-(pyridin-3-yl)ethyl)-4-hydroxypyrrolidine-2-carboxamide (30.1 mg, 55.94 umol, 27.33% yield, 100% purity) as a solid. MS (ESI) m/z 538.1 $[M+H]^+$. prep-HPLC condition: column: Phenomenex Gemini-NX 80*40 mm*3 um; mobile phase: [water (10 mM NH4HCO3)-ACN]; B %: 25%-55%, 8 min. $^1$H NMR (Compound 775) (400 MHz, MeOD-$d_4$) δ ppm 8.44-8.39 (m, 1H), 8.34-8.27 (m, 1H), 7.99 (d, J=8.4 Hz, 1H), 7.61-7.54 (m, 1H), 7.50-7.44 (m, 1H), 7.28-7.20 (m, 1H), 7.16-7.09 (m, 1H), 6.02-5.86 (m, 1H), 4.31-4.22 (m, 1H), 4.21-4.00 (m, 1H), 3.75-3.63 (m, 1H), 3.61-3.53 (m, 1H), 3.45-3.35 (m, 1H), 2.24-2.13 (m, 1H), 2.12-1.95 (m, 2H), 1.83-1.74 (m, 1H), 1.71-1.58 (m, 3H), 1.46-0.97 (m, 15H).

Example 75: Synthesis of Compound 779

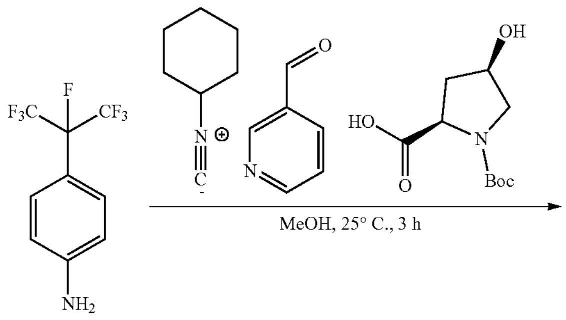

-continued

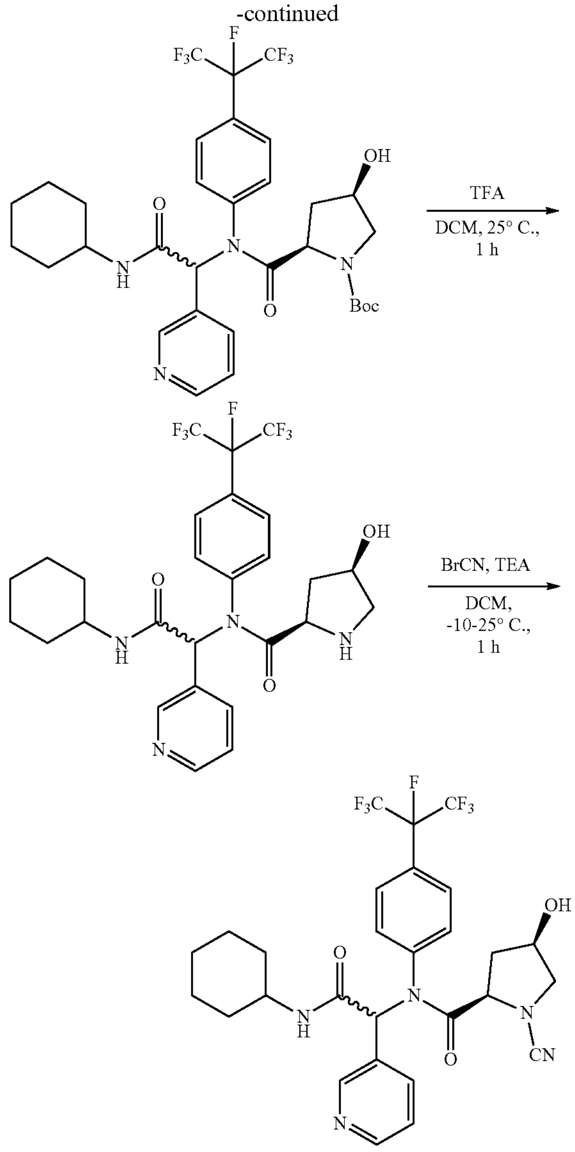

Step 1: (2R,4R)-tert-butyl2-((2-(cyclohexylamino)-2-oxo-1-(pyridin-3-yl)ethyl)(4-(perfluoropropan-2-yl)phenyl)carbamoyl)-4-hydroxypyrrolidine-1-carboxylate A solution of 4-[1,2,2,2-tetrafluoro-1-(trifluoromethyl) ethyl]aniline (451.71 mg, 1.73 mmol, 1 eq) and pyridine-3-carbaldehyde (222.33 mg, 2.08 mmol, 195.03 uL, 1.2 eq) in MeOH (8 mL) was stirred at 25° C. for 30 min. (2R,4R)-1-tert-butoxycarbonyl-4-hydroxy-pyrrolidine-2-carboxylic acid (400 mg, 1.73 mmol, 1 eq) was added to the mixture, followed by the addition of a solution of cyclohexanecarbonitrile (169.95 mg, 1.56 mmol, 184.93 uL, 0.9 eq) in MeOH (1 mL) in portions. The mixture was stirred at 25° C. for 3 h. The reaction mixture was concentrated under reduced pressure and purified by prep-HPLC ((column: Phenomenex luna C18 250*50 mm*10 um; mobile phase: [water (0.1% TFA)-ACN]; B %: 45%-65%, 10 min.) to give a product (2R,4R)-tert-butyl2-((2-(cyclohexylamino)-2-oxo-1-(pyridin-3-yl)ethyl)(4-(perfluoropropan-2-yl)phenyl) carbamoyl)-4-hydroxypyrrolidine-1-carboxylate (300 mg, 412.66 umol, 23.86% yield, 95% purity) and (2R,4R)-tert-butyl2-((2-(cyclohexylamino)-2-oxo-1-(pyridin-3-yl)ethyl) (4-(perfluoropropan-2-yl)phenyl)carbamoyl)-4-hydroxy-pyrrolidine-1-carboxylate (270 mg, 371.39 umol, 21.47% yield, 95% purity) as an oil. MS (ESI) m/z 691.1 $[M+H]^+$ Step 2: (2R,4R)—N-(2-(cyclohexylamino)-2-oxo-1-(pyridin-3-yl)ethyl)-4-hydroxy-N-(4-(perfluoropropan-2-yl)phenyl)pyrrolidine-2-carboxamide Isomer 1: A solution of (2R,4R)-2-[[2-(cyclohexylamino)-2-oxo-1-(3-pyridyl)ethyl]-[4-[1,2,2,2-tetrafluoro-1-(trifluoromethyl)ethyl]phenyl]carbamoyl]-4-hydroxy-pyrrolidine-1-carboxylate (300 mg, 434.38 umol, 1 eq) in TFA (1 mL) and DCM (3 mL) was stirred at 25° C. for 1 h. The reaction mixture was concentrated under reduced pressure and was adjust pH~7 with aq. $NaHCO_3$ (4 mL) and then extracted with DCM (2 mL*3). The resulting mixture was concentrated in vacuum to give (2R,4R)—N-(2-(cyclohexylamino)-2-oxo-1-(pyridin-3-yl)ethyl)-4-hydroxy-N-(4-(perfluoropropan-2-yl)phenyl)pyrrolidine-2-carboxamide (120 mg, 193.05 umol, 44.44% yield, 95% purity) as a solid. MS (ESI) m/z 591.1 $[M+H]^+$ Isomer 2: A solution of (2R,4R)-2-[[2-(cyclohexylamino)-2-oxo-1-(3-pyridyl)ethyl]-[4-[1,2,2,2-tetrafluoro-1-(trifluoromethyl)ethyl]phenyl]carbamoyl]-4-hydroxy-pyrrolidine-1-carboxylate (270 mg, 390.94 umol, 1 eq) in TFA (1 mL) and DCM (3 mL) was stirred at 25° C. for 1 h. The reaction mixture was concentrated under reduced pressure and adjusted to pH~7 with aq. $NaHCO_3$ (4 mL) and extracted with DCM (2 mL*3). The resulting mixture was concentrated in vacuum to give (2R,4R)—N-(2-(cyclohexylamino)-2-oxo-1-(pyridin-3-yl)ethyl)-4-hydroxy-N-(4-(perfluoropropan-2-yl)phenyl)pyrrolidine-2-carboxamide (100 mg, 160.87 umol, 41.15% yield, 95% purity) as a solid. MS (ESI) m/z 591.1 $[M+H]^+$ Step 3: (2R,4R)-1-cyano-N-(2-(cyclohexylamino)-2-oxo-1-(pyridin-3-yl)ethyl)-4-hydroxy-N-(4-(perfluoropropan-2-yl)phenyl)pyrrolidine-2-carboxamide Compound 779 Isomer 1: To a solution of (2R,4R)—N-[2-(cyclohexylamino)-2-oxo-1-(3-pyridyl)ethyl]-4-hydroxy-N-[4-[1,2,2,2-tetrafluoro-1-(trifluoromethyl)ethyl] phenyl]pyrrolidine-2-carboxamide (100 mg, 169.34 umol, 1 eq) (100 mg, 182.94 umol, 1 eq) in DCM (2 mL) was added TEA (51.41 mg, 508.02 umol, 70.71 uL, 3 eq) at −10° C. To the resulting solution was added BrCN (35.87 mg, 338.68 umol, 24.91 uL, 2 eq) at −10° C., and stirred at −10° C. to 20° C. for 1 h. The mixture was added with water (10 mL) and extracted with DCM 5 mL*2). The resulting mixture was concentrated under reduced pressure and was purified by prep-HPLC (column: Waters Xbridge BEH C18 100*25 mm*5 um; mobile phase: [water (10 mM $NH_4HCO_3$)-ACN]; B %: 35%-65%, 10 min.) to give (2R,4R)-1-cyano-N-(2-(cyclohexylamino)-2-oxo-1-(pyridin-3-yl)ethyl)-4-hydroxy-N-(4-(perfluoropropan-2-yl)phenyl)pyrrolidine-2-carboxamide (65 mg, 97.60 umol, 57.64% yield, 92.43% purity) as a solid. MS (ESI) m/z 616.1 $[M+H]^+$ $^1H$ NMR (Compound 779 Isomer 1) (400 MHz, MeOD-$d_4$) δ ppm 8.33 (d, J=1.6 Hz, 1H), 8.29 (d, J=4.8 Hz, 1H), 8.14-6.90 (m, 6H), 6.23 (s, 1H), 4.33-4.17 (m, 2H), 3.81-3.68 (m, 1H), 3.59 (dd, J=5.7, 9.4 Hz, 1H), 3.41 (dd, J=5.0, 9.4 Hz, 1H), 2.20-2.05 (m, 1H), 2.04-1.88 (m, 2H), 1.77 (d, J=9.7 Hz, 2H), 1.72-1.58 (m, 2H), 1.43-1.01 (m, 5H).

Compound 779 Isomer 2: To a solution of (2R,4R)—N-[2-(cyclohexylamino)-2-oxo-1-(3-pyridyl)ethyl]-4-hydroxy-N-[4-[1,2,2,2-tetrafluoro-1-(trifluoromethyl)ethyl] phenyl]pyrrolidine-2-carboxamide (100 mg, 169.34 umol, 1 eq) (100 mg, 182.94 umol, 1 eq) in DCM (3 mL) was added TEA (51.41 mg, 508.02 umol, 70.71 uL, 3 eq) at −10° C., and then was added BrCN (35.87 mg, 338.68 umol, 24.91 uL, 2 eq) at −10° C. The resulting mixture was stirred at −10° C. to 20° C. for 1 h. The mixture was added into water (10 mL) and was extracted with DCM (5 mL*2). The resulting mixture was concentrated under reduced pressure and was purified by prep-HPLC (column: Waters Xbridge BEH C18 100*25 mm*5 um; mobile phase: [water (10 mM $NH_4HCO_3$)-ACN]; B %: 35%-65%, 10 min.) to give (2R, 4R)-1-cyano-N-(2-(cyclohexylamino)-2-oxo-1-(pyridin-3-yl)ethyl)-4-hydroxy-N-(4-(perfluoropropan-2-yl)phenyl) pyrrolidine-2-carboxamide (56.44 mg, 85.01 umol, 50.20% yield, 92.71% purity) as a solid. MS (ESI) m/z 616.1 $[M+H]^+$ $^1H$ NMR (400 MHz, MeOD-$d_4$) δ ppm 8.39 (d, J=1.8 Hz, 1H), 8.36-8.30 (m, 1H), 8.16-6.68 (m, 6H), 6.10 (s, 1H), 4.33-4.21 (m, 2H), 3.75-3.63 (m, 1H), 3.58 (dd, J=5.4, 9.5 Hz, 1H), 3.43 (dd, J=4.0, 9.5 Hz, 1H), 2.16-2.06 (m, 1H), 1.96 (td, J=4.6, 13.3 Hz, 2H), 1.82-1.56 (m, 4H), 1.43-1.00 (m, 5H).

Example 76: Synthesis of Compound 791

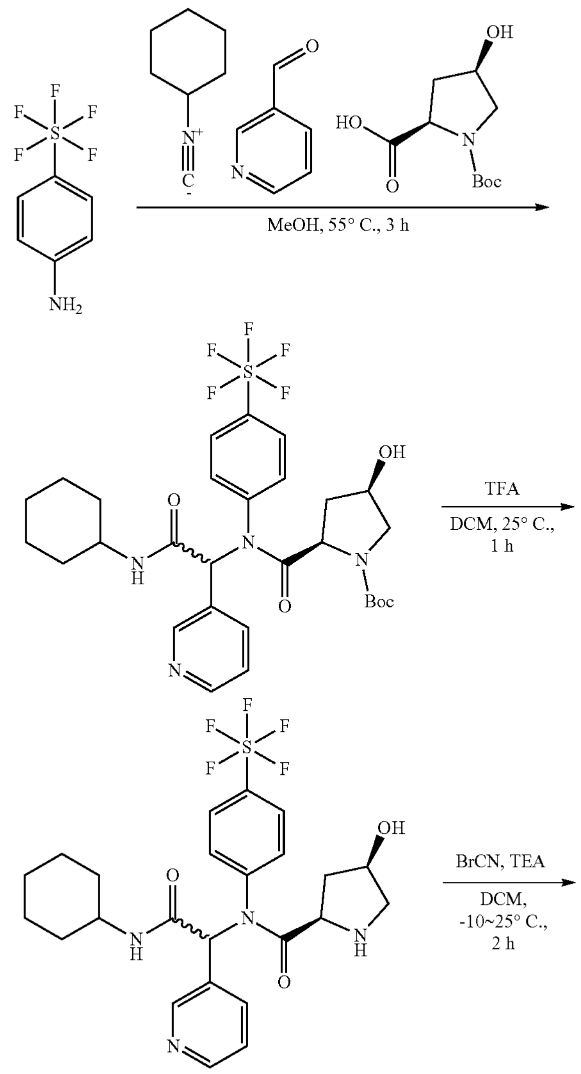

-continued

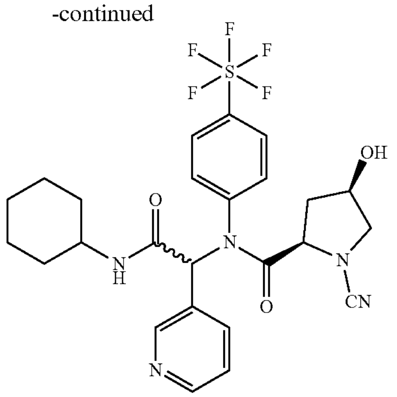

Step1: (2R,4R)-tert-butyl-2-[[2-(cyclohexylamino)-2-oxo-1-(3-pyridyl)ethyl]-[4-(pentafluoro-$\lambda^6$-sulfanyl)phenyl]carbamoyl]-4-hydroxy-pyrrolidine-1-carboxylate A solution of 4-(pentafluoro-$\lambda^6$-sulfanyl)aniline (700 mg, 3.19 mmol, 1 eq) and nicotinaldehyde (342.09 mg, 3.19 mmol, 300.08 uL, 1 eq) and in MeOH (30 mL) was stirred at 55° C. for 1 h. To the mixture was added (2R,4R)-1-(tert-butoxycarbonyl)-4-hydroxypyrrolidine-2-carboxylic acid (738.55 mg, 3.19 mmol, 1 eq), and then the mixture was stirred at 55° C. for 0.5 h. Isocyanocyclohexane (313.80 mg, 2.87 mmol, 357.40 uL, 0.9 eq) was added for three times, and the mixture was stirred at 55° C. for 1.5 h. Upon completion, the reaction mixture was concentrated under reduced pressure and was purified by column chromatography ($SiO_2$, petroleum ether:EtOAc=5:1) to give a product (2R,4R)-tert-butyl-2-[[2-(cyclohexylamino)-2-oxo-1-(3-pyridyl)ethyl]-[4-(pentafluoro-$\lambda^6$-sulfanyl)phenyl]carbamoyl]-4-hydroxy-pyrrolidine-1-carboxylate (210 mg, 323.73 umol, 14.19% yield) and (2R,4R)-tert-butyl-2-[[2-(cyclohexylamino)-2-oxo-1-(3-pyridyl)ethyl]-[4-(pentafluoro-$\lambda^6$-sulfanyl)phenyl]carbamoyl]-4-hydroxy-pyrrolidine-1-carboxylate (430 mg, 662.88 umol, 29.06% yield) as an oil. MS (ESI) m/z 649.2 $[M+H]^+$ Step2: (2R,4R)—N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide Isomer 1: To a solution of (2R,4R)-tert-butyl-2-[[2-(cyclohexylamino)-2-oxo-1-(3-pyridyl)ethyl]-[4-(pentafluoro-$\lambda^6$-sulfanyl)phenyl]carbamoyl]-4-hydroxy-pyrrolidine-1-carboxylate (190 mg, 292.90 umol, 1 eq) in DCM (4 mL) was added TFA (2.00 g, 17.57 mmol, 1.30 mL, 60 eq) and the mixture was stirred at 25° C. for 1 h. Upon completion, the mixture was quenched by addition $NaHCO_3$ aq. (50 mL) and then extracted with EtOAc (30 mL*3). The combined organic layers were washed with brine (50 mL), dried over $Na_2SO_4$, filtered and concentrated under reduced pressure to give the crude product (2R,4R)—N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide (70 mg, crude) was obtained as an oil. MS (ESI) m/z 549.2 $[M+H]^+$ Isomer 2: To a solution of (2R,4R)-tert-butyl-2-[[2-(cyclohexylamino)-2-oxo-1-(3-pyridyl)ethyl]-[4-(pentafluoro-$\lambda^6$-sulfanyl)phenyl]carbamoyl]-4-hydroxy-pyrrolidine-1-carboxylate (400 mg, 616.63 umol, 1 eq) in DCM (10 mL) was added TFA (4.22 g, 37.00 mmol, 2.74 mL, 60 eq) and the mixture was stirred at 25° C. for 1 h. Upon completion, the mixture was quenched by addition $NaHCO_3$ (50 mL) and then extracted with EtOAc (30 mL*3). The combined organic layers were washed with brine (50 mL), dried over $Na_2SO_4$, filtered and concentrated under reduced pressure to give the crude product (2R,4R)—N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide (190 mg, crude) was obtained as an oil. MS (ESI) m/z 549.2 $[M+H]^+$ Step3:(2R,4R)-1-cyano-N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide Compound 791 Isomer 1: To a solution of (2R,4R)—N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide (70 mg, 127.60 umol, 1 eq) in DCM (1.5 mL) was added TEA (38.74 mg, 382.81 umol, 53.28 uL, 3 eq) and the mixture was cooled at −10° C. BrCN (20.27 mg, 191.41 umol, 14.08 uL, 1.5 eq) in DCM (0.5 mL) was added, and the resulting mixture solution was stirred for 0.5 h at 0° C. and warmed to 25° C. gradually. The mixture was added into $H_2O$ (15 mL), extracted with DCM (10 mL*3), and then concentrated under reduced pressure and was purified by prep-HPLC (column: Waters Xbridge BEH C18 100*30 mm*10 um; mobile phase: [water (10 mM $NH_4HCO_3$)-ACN]; B %: 32%-62%, 10 min) to give (2R,4R)-1-cyano-N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide (10 mg, 17.43 umol, 13.66% yield) as a solid. MS (ESI) m/z 574.1 $[M+H]^+$ $^1H$ NMR (400 MHz, MeOD-$d_4$) δ=8.41-8.29 (m, 2H), 8.25-7.48 (m, 5H), 7.24 (dd, J=5.0, 7.9 Hz, 1H), 6.26 (s, 1H), 4.31-4.13 (m, 2H), 3.80-3.66 (m, 1H), 3.58 (dd, J=5.7, 9.3 Hz, 1H), 3.40 (dd, J=5.1, 9.2 Hz, 1H), 2.23-2.03 (m, 1H), 1.97 (td, J=5.8, 13.1 Hz, 2H), 1.83-1.56 (m, 4H), 1.39-1.07 (m, 5H).

Compound 791 Isomer 2: To a solution of (2R,4R)—N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide (160 mg, 291.67 umol, 1 eq) in DCM (4 mL) was added TEA (88.54 mg, 875.01 umol, 121.79 uL, 3 eq) and the mixture was cooled at −10° C. BrCN (46.34 mg, 437.50 umol, 32.18 uL, 1.5 eq) in DCM (0.5 mL) was added and the mixture solution was stirred for 0.5 h at 0° C. and warmed to 25° C. for 1.5 h. Upon completion, the mixture was added into $H_2O$ (20 mL) and was extracted with DCM (10 mL*3), then was concentrated under reduced pressure and was purified by prep-HPLC (column: Waters Xbridge BEH C18 100*30 mm*10 um; mobile phase: [water (10 mM $NH_4HCO_3$)-ACN]; B %: 32%-62%, 10 min) to give (2R,4R)-1-cyano-N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide (50 mg, 87.17 umol, 29.89% yield) as a solid. MS (ESI) m/z 574.1 $[M+H]^+$ $^1H$ NMR (400 MHz, MeOD-$d_4$) δ=8.42-8.32 (m, 2H), 8.23-7.22 (m, 5H), 6.12 (s, 1H), 4.59 (br s, 1H), 4.34-4.16 (m, 2H), 3.69-3.58 (in, 1H), 3.48-3.39 (m, 1H), 3.39-3.36 (m, 1H), 2.17-2.06 (m, 1H), 1.98-1.89 (m, 2H), 1.83-1.56 (m, 4H), 1.37-1.06 (m, 5H).

Example 77: Synthesis of Compound 815a

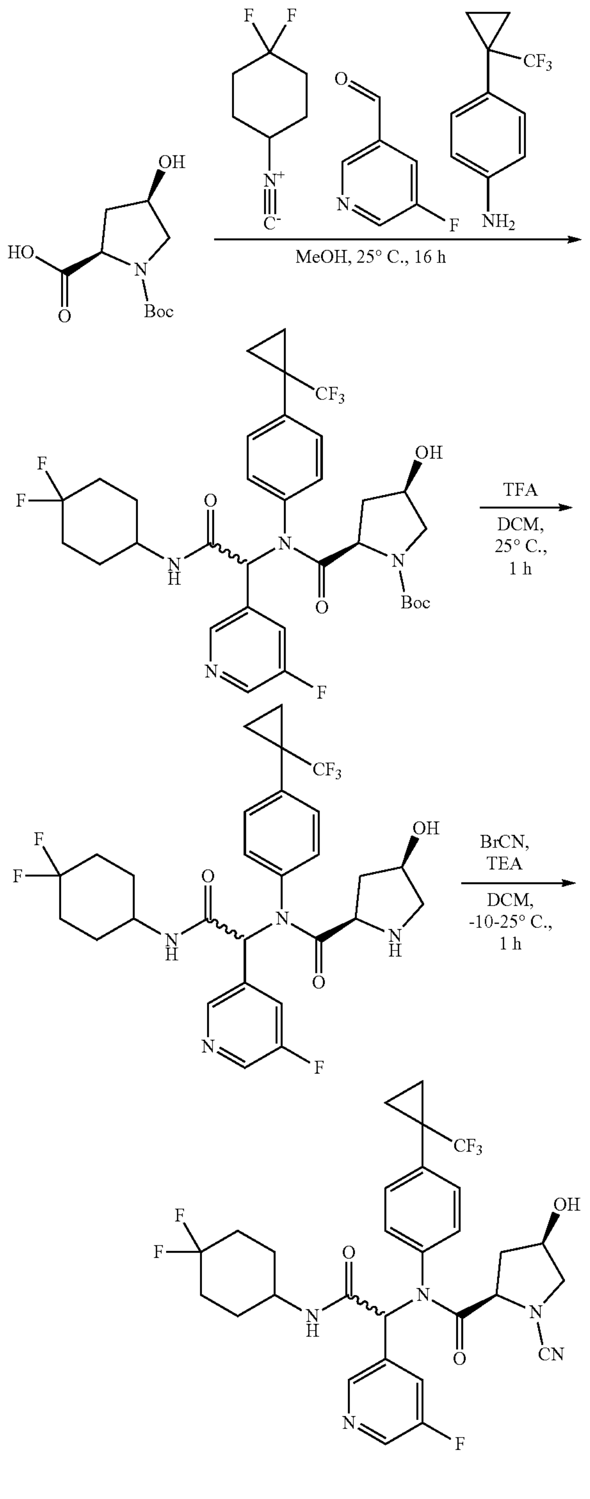

Step 1: (2R,4R)-tert-butyl2-((2-((4,4-difluorocyclohexyl)amino)-1-(5-fluoropyridin-3-yl)-2-oxoethyl)(4-(1-(trifluoromethyl)cyclopropyl)phenyl)carbamoyl)-4-hydroxypyrrolidine-1-carboxylate A solution of 4-[1-(trifluoromethyl)cyclopropyl]aniline (435.01 mg, 2.16 mmol, 1 eq) and 5-fluoropyridine-3-carbaldehyde (324.59 mg, 2.59 mmol, 1.2 eq) in MeOH (8 mL) was stirred at 25° C. for 30 min, then (2R,4R)-1-tert-butoxycarbonyl-4-hydroxy-pyrrolidine-2-carboxylic acid (500 mg, 2.16 mmol, 1 eq) was added to the mixture. Then, a solution of 4,4-difluorocyclohexanecarbonitrile (282.46 mg, 1.95 mmol, 0.9 eq) in MeOH (1 mL) was added in portions. The mixture was stirred at 25° C. for 16 h. The reaction mixture was concentrated under reduced pressure and was purified by prep-HPLC (column: Phenomenex luna C18 250*50 mm*10 um; mobile phase: [water (0.1% TFA)-ACN]; B %: 50%-70%, 10 min.) to give a product (2R,4R)-tert-butyl2-((2-((4,4-difluorocyclohexyl)amino)-1-(5-fluoropyridin-3-yl)-2-oxoethyl)(4-(1-(trifluoromethyl)cyclopropyl)phenyl)carbamoyl)-4-hydroxypyrrolidine-1-carboxylate (350 mg, 511.20 umol, 23.64% yield) and (2R,4R)-tert-butyl2-((2-((4,4-difluorocyclohexyl)amino)-1-(5-fluoropyridin-3-yl)-2-oxoethyl)(4-(1-(trifluoromethyl)cyclopropyl)phenyl)carbamoyl)-4-hydroxypyrrolidine-1-carboxylate (440 mg, 642.65 umol, 29.72% yield) as an oil. MS (ESI) m/z 685.3 $[M+H]^+$ Step 2: (2R,4R)—N-(2-((4,4-difluorocyclohexyl)amino)-1-(5-fluoropyridin-3-yl)-2-oxoethyl)-4-hydroxy-N-(4-(1-(trifluoromethyl)cyclopropyl)phenyl)pyrrolidine-2-carboxamide Isomer 1: A solution of (2R,4R)-tert-butyl2-((2-((4,4-difluorocyclohexyl)amino)-1-(5-fluoropyridin-3-yl)-2-oxoethyl)(4-(1-(trifluoromethyl)cyclopropyl)phenyl)carbamoyl)-4-hydroxypyrrolidine-1-carboxylate (350 mg, 511.20 umol, 1 eq) in TFA (1.5 mL) and DCM (4.5 mL) was stirred at 25° C. for 1 h. The reaction mixture was concentrated under reduced pressure and was adjust pH~7 with aq. $NaHCO_3$ (3 mL), and then extracted with DCM (1 mL*3). The resulting solution was concentrated in vacuum to give (2R,4R)—N-(2-((4,4-difluorocyclohexyl)amino)-1-(5-fluoropyridin-3-yl)-2-oxoethyl)-4-hydroxy-N-(4-(1-(trifluoromethyl)cyclopropyl)phenyl) pyrrolidine-2-carboxamide (180 mg, 292.53 umol, 57.22% yield, 95% purity) as a solid. MS (ESI) m/z 585.2 $[M+H]^+$ Isomer 2: A solution of (2R,4R)-tert-butyl2-((2-((4,4-difluorocyclohexyl)amino)-1-(5-fluoropyridin-3-yl)-2-oxoethyl)(4-(1-(trifluoromethyl)cyclopropyl)phenyl)carbamoyl)-4-hydroxypyrrolidine-1-carboxylate (440 mg, 642.65 umol, 1 eq) in TFA (1.5 mL) and DCM (4.5 mL) was stirred at 25° C. for 1 h. The reaction mixture was concentrated under reduced pressure and was adjust pH~7 with aq. $NaHCO_3$ (4 mL), and then extracted with DCM (2 mL*3). The resulting solution was concentrated in vacuum to give (2R,4R)—N-(2-((4,4-difluorocyclohexyl)amino)-1-(5-fluoropyridin-3-yl)-2-oxoethyl)-4-hydroxy-N-(4-(1-(trifluoromethyl)cyclopropyl)phenyl) pyrrolidine-2-carboxamide (280 mg, 479.00 umol, 74.54% yield) as a solid. MS (ESI) m/z 585.2 $[M+H]^+$ Step 3: (2R,4R)-1-cyano-N-(2-((4,4-difluorocyclohexyl)amino)-1-(5-fluoropyridin-3-yl)-2-oxoethyl)-4-hydroxy-N-(4-(1-(trifluoromethyl)cyclopropyl)phenyl)pyrrolidine-2-carboxamide Compound 815 Isomer 1: To a solution of (2R,4R)—N-(2-((4,4-difluorocyclohexyl)amino)-1-(5-fluoropyridin-3-yl)-2-oxoethyl)-4-hydroxy-N-(4-(1-(trifluoromethyl)cyclopropyl)phenyl) pyrrolidine-2-carboxamide (180 mg, 307.93 umol, 1 eq) in DCM (4 mL) was added TEA (93.48 mg, 923.78 umol, 128.58 uL, 3 eq) at −10° C. Then, BrCN (65.23 mg, 615.86 umol, 45.30 uL, 2 eq) was added at −10° C., and the mixture was stirred at −10° C. to 20° C. for 1 h. The mixture was added into water (6 mL), extracted with DCM (3 mL*2), and then concentrated under reduced pressure and purified by prep-HPLC (column: Waters Xbridge BEH C18 100*25 mm*5 um; mobile phase: [water (10 mM $NH_4HCO_3$)-ACN]; B %: 35%-65%, 10 min.) to give (2R,4R)-1-cyano-N-(2-(cyclohexylamino)-2-oxo-1-(pyridin-3-yl)ethyl)-4-hydroxy-N-(4-(perfluoropropan-2-yl)phenyl) pyrrolidine-2-carboxamide (100.29 mg, 157.34 umol, 51.10% yield, 95.63% purity) as a solid. MS (ESI) m/z 610.1 $[M+H]^+$ $^1H$ NMR (400 MHz, MeOD-$d_4$) δ ppm 8.26 (d, J=2.8 Hz, 1H), 8.21 (s, 1H), 7.87-6.68 (m, 5H), 6.18 (s, 1H), 4.29-4.17 (m, 2H), 3.88 (t, J=10.0 Hz, 1H), 3.58 (dd, J=5.6, 9.3 Hz, 1H), 3.45-3.36 (m, 1H), 2.15-1.79 (m, 8H), 1.70-1.58 (m, 1H), 1.52-1.40 (m, 1H), 1.37-1.29 (m, 2H), 1.01 (s, 2H).

Compound 815 Isomer 2: To a solution of (2R,4R)—N-(2-((4,4-difluorocyclohexyl)amino)-1-(5-fluoropyridin-3-yl)-2-oxoethyl)-4-hydroxy-N-(4-(1-(trifluoromethyl)cyclopropyl)phenyl) pyrrolidine-2-carboxamide (280 mg, 479.00 umol, 1 eq) in DCM (8 mL) was added TEA (145.41 mg, 1.44 mmol, 200.01 uL, 3 eq) at −10° C. Then, BrCN (101.47 mg, 958.00 umol, 70.47 uL, 2 eq) was added at −10° C., and the mixture was stirred at −10° C. to 20° C. for 1 h. The mixture was added into water (10 mL) and was extracted with DCM (6 mL*2). The resulting solution was concentrated under reduced pressure, and purified by prep-HPLC (column: Waters Xbridge BEH C18 100*25 mm*5 um; mobile phase: [water (10 mM $NH_4HCO_3$)-ACN]; B %: 35%-65%, 10 min.) to give (2R,4R)-1-cyano-N-(2-(cyclohexylamino)-2-oxo-1-(pyridin-3-yl)ethyl)-4-hydroxy-N-(4-(perfluoropropan-2-yl)phenyl)pyrrolidine-2-carboxamide (139.59 mg, 223.41 umol, 46.64% yield, 97.56% purity) as a solid. MS (ESI) m/z 616.1 $[M+H]^+$ $^1H$ NMR (400 MHz, MeOD-$d_4$) δ ppm 8.30 (d, J=2.7 Hz, 1H), 8.27-8.20 (m, 1H), 7.96-7.21 (m, 4H), 6.81 (s, 1H), 6.05 (s, 1H), 4.29-4.20 (m, 2H), 3.84 (t, J=10.1 Hz, 1H), 3.58 (dd, J=5.5, 9.5 Hz, 1H), 3.46-3.38 (m, 1H), 2.15-1.76 (m, 8H), 1.68-1.54 (m, 1H), 1.52-1.39 (m, 1H), 1.35 (s, 2H), 1.02 (s, 2H).

Example 78: Synthesis of Compound 1251

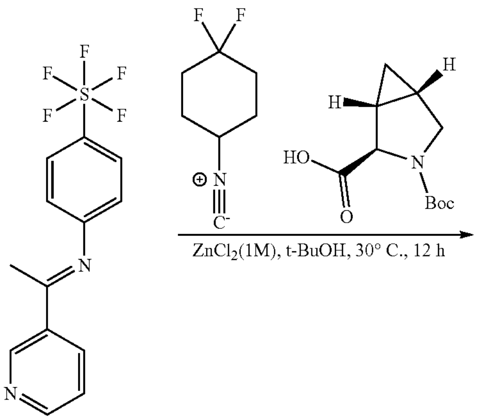

-continued

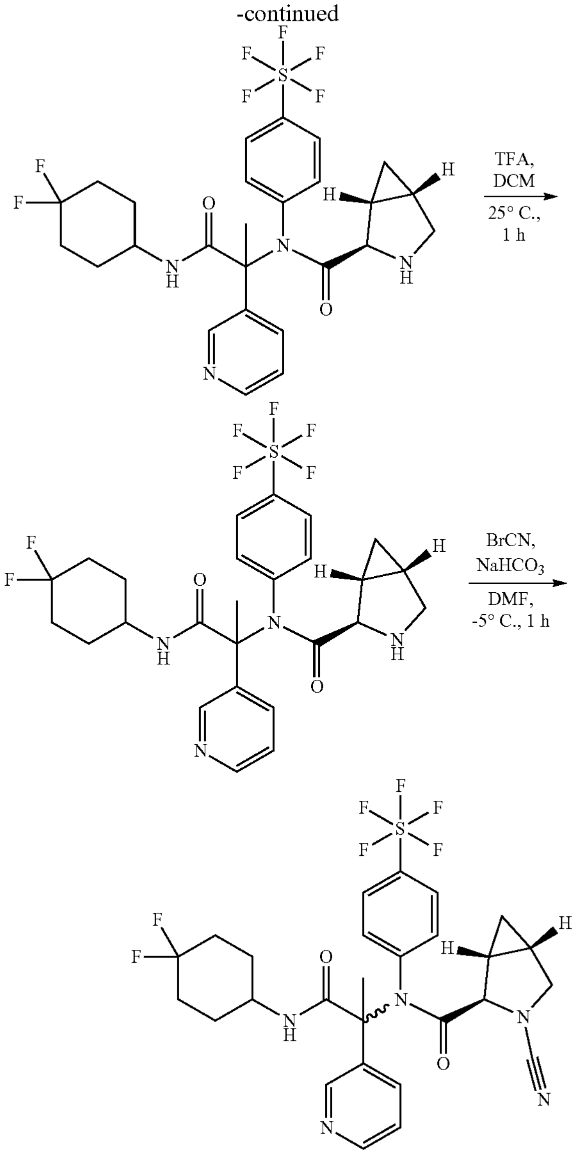

Step 1: tert-butyl (1R,2R,5S)-2-[[2-[(4,4-difluorocyclohexyl)amino]-1-methyl-2-oxo-1-(3-pyridyl)ethyl]-[4-(pentafluoro-$\lambda^6$-sulfanyl)phenyl]carbamoyl]-3-azabicyclo[3.1.0]hexane-3-carboxylate To a solution of (E)-N-[4-(pentafluoro-$\lambda^6$-sulfanyl)phenyl]-1-(3-pyridyl)ethanimine (425.46 mg, 1.32 mmol, 1 eq) in t-BuOH (4 mL) was added (1R,2R,5S)-3-tert-butoxycarbonyl-3-azabicyclo[3.1.0]hexane-2-carboxylic acid (300 mg, 1.32 mmol, 1 eq), 1,1-difluoro-4-isocyano-cyclohexane (191.61 mg, 1.32 mmol, 1 eq) and $ZnCl_2$ (1 M, 7.92 mL, 6 eq), and the resulting mixture was stirred at 30° C. for 12 h. Upon completion, the reaction mixture was diluted with $NaHCO_3$ (10 mL) and extracted with DCM (5 mL*3). The combined organic layers were washed with brine, dried over $Na_2SO_4$, filtered and concentrated under reduced pressure to give a residue. The residue was purified by prep-HPLC (column: Waters X bridge Prep OBD C18 150*40 mm*10 um; mobile phase: [water (10 mM $NH_4HCO_3$)-ACN]; B %: 55%-85%, 8 min) to get product tert-butyl (1R,2R,5S)-2-[[2-[(4,4-difluorocyclohexyl)amino]-1-methyl-2-oxo-1-(3-pyridyl)ethyl]-[4-(pentafluoro-$\lambda^6$-sulfanyl)phenyl]carbamoyl]-3-azabicyclo[3.1.0]hexane-3-carboxylate Isomer 1 (70 mg, 100.76 umol, 7.63% yield) as white solid. MS (ESI) m/z 695.2 $[M+H]^+$. Tert-butyl (1R,2R,5S)-2-[[2-[(4,4-difluorocyclohexyl)amino]-1-methyl-2-oxo-1-(3-pyridyl)ethyl]-[4-(pentafluoro-$\lambda^6$-sulfanyl)phenyl]carbamoyl]-3-azabicyclo[3.1.0]hexane-3-carboxylate Isomer 2 (40 mg, 57.58 umol, 4.36% yield) was obtained as white solid. MS (ESI) m/z 695.2 $[M+H]^+$.

Step 2: (1R,2R,5S)—N-[2-[(4,4-difluorocyclohexyl)amino]-1-methyl-2-oxo-1-(3-pyridyl)ethyl]-N-[4-(pentafluoro-$\lambda^6$-sulfanyl)phenyl]-3-azabicyclo[3.1.0]hexane-2-carboxamide Isomer 1

A solution of tert-butyl (1R,2R,5S)-2-[[2-[(4,4-difluorocyclohexyl)amino]-1-methyl-2-oxo-1-(3-pyridyl)ethyl]-[4-(pentafluoro-$\lambda^6$-sulfanyl)phenyl]carbamoyl]-3-azabicyclo[3.1.0]hexane-3-carboxylate Isomer 1 (67 mg, 96.44 umol, 1 eq) in TFA (0.5 mL) and DCM (1 mL) was stirred at 25° C. for 1 h. Upon completion, the reaction mixture was diluted with $NaHCO_3$ (10 mL) and extracted with DCM (3 mL*3). The combined organic layers were dried over $Na_2SO_4$, filtered and concentrated under reduced pressure to get the product (1R,2R,5S)—N-[2-[(4,4-difluorocyclohexyl)amino]-1-methyl-2-oxo-1-(3-pyridyl)ethyl]-N-[4-(pentafluoro-$\lambda^6$-sulfanyl)phenyl]-3-azabicyclo[3.1.0]hexane-2-carboxamide Isomer 1 (56 mg, crude) as yellow oil. MS (ESI) m/z 595.3 $[M+H]^+$.

(1R,2R,5S)—N-[2-[(4,4-difluorocyclohexyl)amino]-1-methyl-2-oxo-1-(3-pyridyl)ethyl]-N-[4-(pentafluoro-$\lambda^6$-sulfanyl)phenyl]-3-azabicyclo[3.1.0]hexane-2-carboxamide Isomer 2

A solution of tert-butyl (1R,2R,5S)-2-[[2-[(4,4-difluorocyclohexyl)amino]-1-methyl-2-oxo-1-(3-pyridyl)ethyl]-[4-(pentafluoro-$\lambda^6$-sulfanyl)phenyl]carbamoyl]-3-azabicyclo[3.1.0]hexane-3-carboxylate Isomer 2 (37 mg, 53.26 umol, 1 eq) in TFA (0.5 mL) and DCM (1 mL) was stirred at 25° C. for 1 h. Upon completion, the reaction mixture was diluted with $NaHCO_3$ (10 mL) and extracted with DCM (3 mL*3). The combined organic layers were dried over $Na_2SO_4$, filtered and concentrated under reduced pressure to get the product (1R,2R,5S)—N-[2-[(4,4-difluorocyclohexyl)amino]-1-methyl-2-oxo-1-(3-pyridyl)ethyl]-N-[4-(pentafluoro-$\lambda^6$-sulfanyl)phenyl]-3-azabicyclo[3.1.0]hexane-2-carboxamide Isomer 2 (30 mg, crude) as yellow oil. MS (ESI) m/z 595.3 $[M+H]^+$.

Step 3: (1R,2R,5S)-3-cyano-N-[2-[(4,4-difluorocyclohexyl)amino]-1-methyl-2-oxo-1-(3-pyridyl)ethyl]-N-[4-(pentafluoro-$\lambda^6$-sulfanyl)phenyl]-3-azabicyclo[3.1.0]hexane-2-carboxamide Isomer 1

A mixture of (1R,2R,5S)—N-[2-[(4,4-difluorocyclohexyl)amino]-1-methyl-2-oxo-1-(3-pyridyl)ethyl]-N-[4-(pentafluoro-$\lambda^6$-sulfanyl)phenyl]-3-azabicyclo[3.1.0]hexane-2-carboxamide Isomer 1 (56 mg, 94.18 umol, 1 eq) in DMF (1.5 mL) was added $NaHCO_3$ (23.74 mg, 282.55 umol, 10.99 uL, 3 eq), then the solution was cooled to −5° C. and BrCN (11.97 mg, 113.02 umol, 8.31 uL, 1.2 eq) in DMF (0.5 mL) was added drop-wise. The resulting mixture was stirred at −5° C. for 1 h. Upon completion, the reaction mixture was quenched with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 30%-60%, 8 min) to get the product (1R,2R,5S)-3-cyano-N-[2-[(4,4-difluorocyclohexyl)amino]-1-methyl-2-oxo-1-(3-pyridyl)ethyl]-N-[4-(pentafluoro-λ$^6$-sulfanyl)phenyl]-3-azabicyclo[3.1.0]hexane-2-carboxamide Isomer 1 (4.62 mg, 7.28 umol, 7.73% yield, 97.7% purity) as white solid. MS (ESI) m/z 620.2 $[M+H]^+$.

$^1$H NMR (400 MHz, METHANOL-$d_4$) δ=8.67 (d, J=2.1 Hz, 1H), 8.41 (d, J=4.8 Hz, 1H), 7.99-7.84 (m, 3H), 7.73 (br d, J=8.2 Hz, 1H), 7.45 (br t, J=7.2 Hz, 1H), 7.37 (dd, J=4.8, 8.2 Hz, 1H), 3.95 (br d, J=7.2 Hz, 1H), 3.87 (s, 1H), 3.80 (dd, J=3.8, 8.7 Hz, 1H), 3.40 (s, 1H), 2.10-2.01 (m, 2H), 1.98-1.84 (m, 7H), 1.78-1.58 (m, 4H), 0.80-0.66 (m, 1H), 0.29-0.15 (m, 1H).

(1R,2R,5S)-3-cyano-N-[2-[(4,4-difluorocyclohexyl) amino]-1-methyl-2-oxo-1-(3-pyridyl)ethyl]-N-[4-(pentafluoro-λ$^6$-sulfanyl)phenyl]-3-azabicyclo[3.1.0] hexane-2-carboxamide Isomer 2

A mixture of (1R,2R,5S)—N-[2-[(4,4-difluorocyclohexyl)amino]-1-methyl-2-oxo-1-(3-pyridyl)ethyl]-N-[4-(pentafluoro-λ$^6$-sulfanyl)phenyl]-3-azabicyclo[3.1.0] hexane-2-carboxamide Isomer 2 (30 mg, 50.46 umol, 1 eq) in DMF (1 mL) was added $NaHCO_3$ (12.72 mg, 151.37 umol, 5.89 uL, 3 eq), then the solution was cooled to −5° C. and BrCN (6.41 mg, 60.55 umol, 4.45 uL, 1.2 eq) in DMF (0.5 mL) was added drop-wise. The resulting mixture was stirred at −5° C. for 1 h. Upon completion, the reaction mixture was quenched with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 30%-60%, 8 min) to get the product (1R,2R,5S)-3-cyano-N-[2-[(4,4-difluorocyclohexyl)amino]-1-methyl-2-oxo-1-(3-pyridyl)ethyl]-N-[4-(pentafluoro-λ$^6$-sulfanyl)phenyl]-3-azabicyclo[3.1.0]hexane-2-carboxamide Isomer 2 (8.22 mg, 13.27 umol, 26.29% yield, 100% purity) as white solid. MS (ESI) m/z 620.2 $[M+H]^+$.

$^1$H NMR (400 MHz, METHANOL-$d_4$) δ=8.57 (d, J=2.1 Hz, 1H), 8.39-8.32 (m, 1H), 7.95-7.73 (m, 3H), 7.63-7.52 (m, 2H), 7.31 (dd, J=4.8, 8.2 Hz, 1H), 3.97 (br s, 1H), 3.88 (s, 1H), 3.82 (dd, J=3.9, 8.6 Hz, 1H), 3.40 (d, J=8.7 Hz, 1H), 2.17-1.79 (m, 9H), 1.78-1.52 (m, 4H), 0.74-0.66 (m, 1H), 0.25-0.17 (m, 1H).

Example 79: Synthesis of Compound 1123

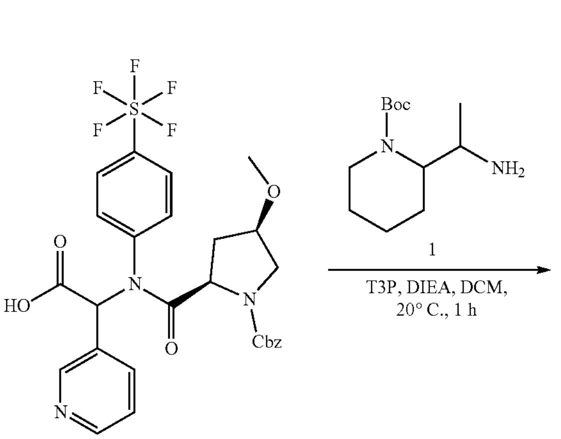

-continued

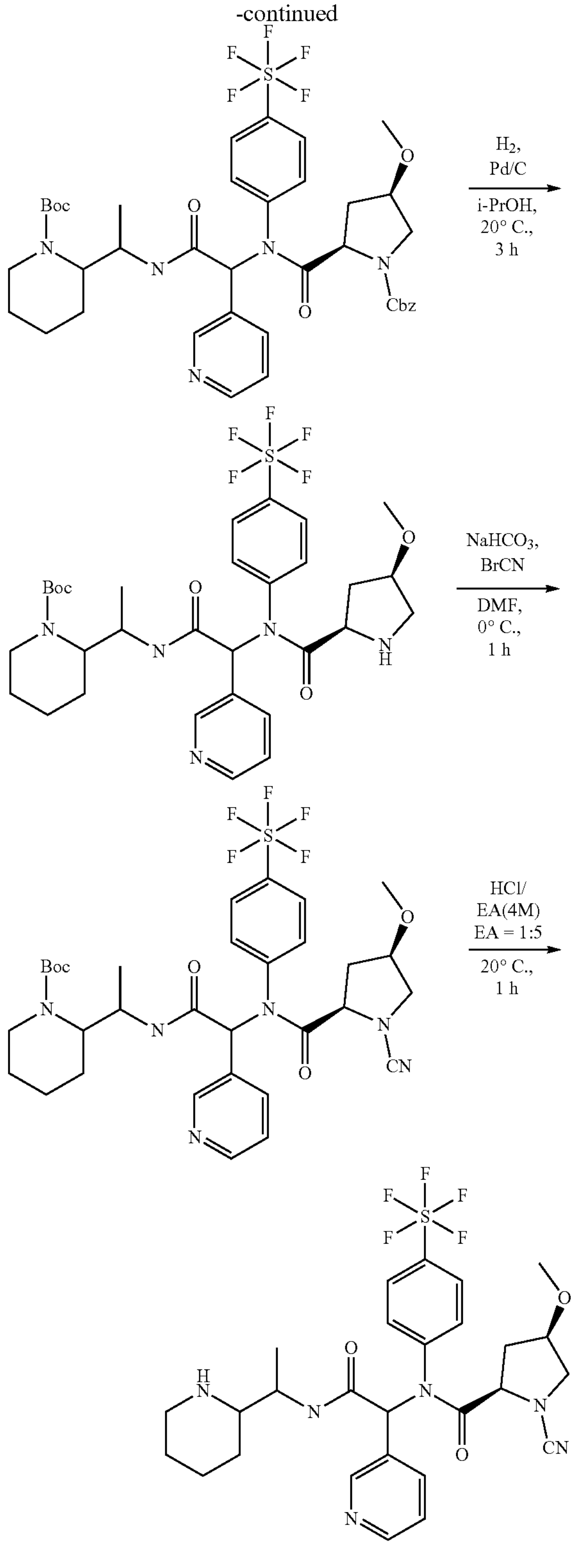

Step 1: tert-butyl 2-[1-[[2-[N-[(2R,4R)-1-benzyloxycarbonyl-4-methoxy-pyrrolidine-2-carbonyl]-4-(pentafluoro-λ6-sulfanyl)anilino]-2-(3-pyridyl) acetyl]amino]ethyl]piperidine-1-carboxylate A mixture of 2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetic acid (250 mg, 406.13 umol, 1 eq), tert-butyl 2-(1-aminoethyl)piperidine-1-carboxylate (139.10 mg, 609.19 umol, 1.5 eq), T3P (775.34 mg, 1.22 mmol, 724.61 uL, 50% purity, 3 eq), TEA (123.29 mg, 1.22 mmol, 169.58 uL, 3 eq) in DCM (5 mL) was degassed and purged with $N_2$ for 3 times, and then the mixture was stirred at 20° C. for 1 h under $N_2$ atmosphere. Upon completion, the solution was diluted with $H_2O$ (30 mL), extracted with DCM (30 mL*3), the combined organic phase was dried over $Na_2SO_4$, filtrated and concentrated to give the crude. The residue was purified by column chromatography ($SiO_2$, Petroleum ether/Ethyl acetate=20/1 to 5/1). Tert-butyl 2-[1-[[2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (275 mg, 332.98 umol, 81.99% yield, 100% purity) was obtained as yellow oil. MS (ESI) m/z 826.4 $[M+H]^+$.

Step 2: Tert-butyl 2-[1-[[2-[N-[(2R,4R)-4-methoxy-pyrrolidine-2-carbonyl]-4-(pentafluoro-λ6-sulfanyl) anilino]-2-(3-pyridyl)acetyl]amino]ethyl]piperidine-1-carboxylate Tert-butyl 2-[1-[[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl]amino]ethyl]piperidine-1-carboxylate (330 mg, 399.57 umol, 1 eq) in i-PrOH (6 mL) was added the Pd/C (330 mg, 399.57 umol, 10% purity, 1 eq) and the solution was stirred at $H_2$ (807.14 ug, 399.57 umol, 1 eq) for 3 h at 20° C. Upon completion, the solution was filtrated and concentrated to give the crude. The crude was used to next step directly and without further purification. Tert-butyl 2-[1-[[2-[N-[(2R,4R)-4-methoxypyrrolidine-2-carbonyl]-4-(pentafluoro-λ6-sulfanyl)anilino]-2-(3-pyridyl) acetyl]amino]ethyl]piperidine-1-carboxylate (300 mg, crude) was obtained as yellow oil. MS (ESI) m/z 692.2 $[M+H]^+$.

Step 3: tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl] piperidine-1-carboxylate Tert-butyl 2-[1-[[2-[N-[(2R,4R)-4-methoxypyrrolidine-2-carbonyl]-4-(pentafluoro-λ6-sulfanyl)anilino]-2-(3-pyridyl) acetyl]amino]ethyl]piperidine-1-carboxylate (300 mg, 433.68 umol, 1 eq), $NaHCO_3$ (109.30 mg, 1.30 mmol, 50.60 uL, 3 eq) in DMF (5 mL) was cooled to 0° C., then the solution of BrCN (55.12 mg, 520.42 umol, 38.28 uL, 1.2 eq) in DMF (1 mL) was added and the solution was stirred at 0° C. for 1 h. Upon completion, the solution was quenched with $H_2O$ (10 mL), extracted with EA (20 mL*3), the combined organic phase was dried over $Na_2SO_4$, filtrated and concentrated to give the crude. The aqueous phase was adjusted pH=12 by NaOH, and quenched by the solution of NaClO. The residue was purified by prep-HPLC (neutral condition), column: Waters Xbridge Prep OBD C18 150*40 mm*10 um; mobile phase: [water (10 mM $NH_4HCO_3$)-ACN]; B %: 45%-70%, 8 min. Tert-butyl 2-[1-[[2-[N-[(2R,4R)-1-cyano-4-methoxy-pyrrolidine-2-carbonyl]-4-(pentafluoro-λ6-sulfanyl)anilino]-2-(3-pyridyl)acetyl]amino]ethyl]piperidine-1-carboxylate (80 mg, 111.61 umol, 25.74% yield, 100% purity) was obtained as white solid. MS (ESI) m/z 717.1 $[M+H]^+$.

Step 4: (2R,4R)-1-cyano-4-methoxy-N-[2-oxo-2-[1-(2-piperidyl)ethylamino]-1-(3-pyridyl)ethyl]-N-[4-(pentafluoro-λ$^6$-sulfanyl)phenyl]pyrrolidine-2-carboxamide To a solution of tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (42 mg, 58.60 umol, 1 eq) in EtOAc (5 mL) was added HCl/EtOAc (4 M, 1 mL, 68.26 eq). The mixture was stirred at 20° C. for 1 h. The reaction mixture was concentrated under reduced pressure to remove solvent. The residue was purified by prep-HPLC (column: Phenomenex Luna C18 75*30 mm*3 um; mobile phase: [water (0.2% FA)-ACN]; B %: 1%-40%, 8 min) to give (2R,4R)-1-cyano-4-methoxy-N-[2-oxo-2-[1-(2-piperidyl)ethylamino]-1-(3-pyridyl)ethyl]-N-[4-(pentafluoro-λ$^6$-sulfanyl)phenyl]pyrrolidine-2-carboxamide (5 mg, 7.64 umol, 13.03% yield, 94.2% purity) as a yellow solid. MS (ESI) m/z 617.3 $[M+H]^+$. $^1H$ NMR (400 MHz, METHANOL-$d_4$) δ=8.69-8.18 (m, 3H), 7.88-7.40 (m, 4H), 7.36-7.17 (m, 1H), 6.06-5.78 (m, 1H), 4.50-3.41 (m, 6H), 3.33-3.28 (m, 1H), 3.32 (s, 2H), 3.19-2.91 (m, 2H), 2.21-0.90 (m, 11H).

Example 80: Synthesis of Compound 1174

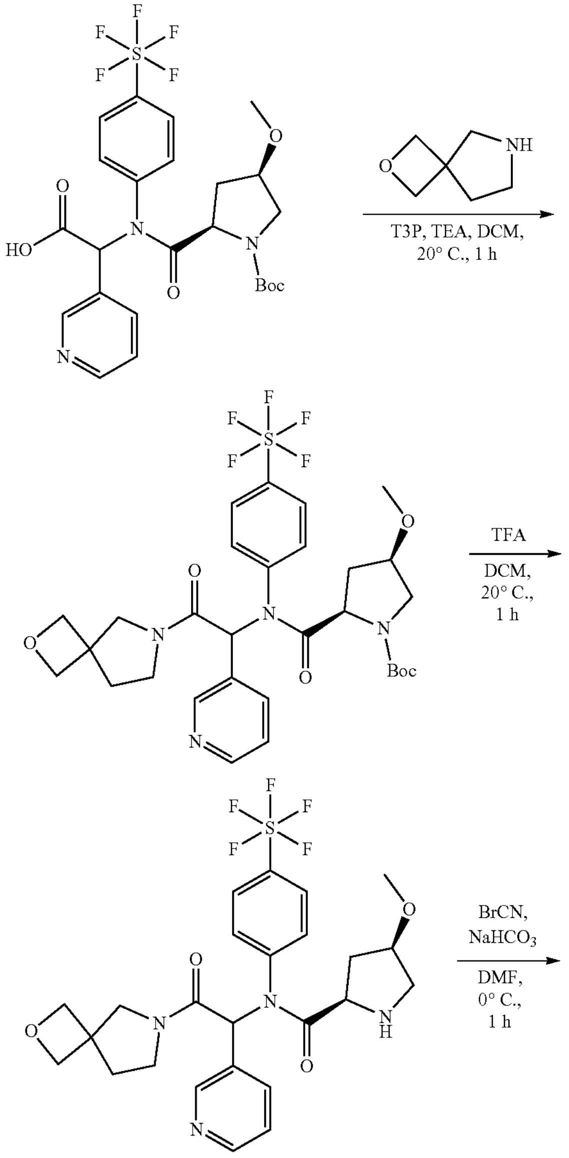

-continued

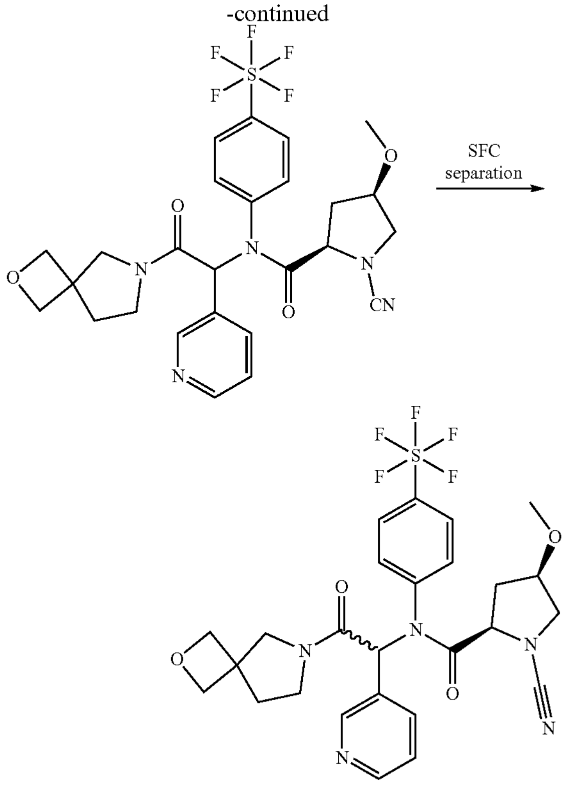

Step 1: tert-butyl (2R,4R)-4-methoxy-2-[[2-(2-oxa-7-azaspiro[3.4]octan-7-yl)-2-oxo-1-(3-pyridyl) ethyl]-[4-(pentafluoro-λ$^6$-sulfanyl)phenyl]carbamoyl]pyrrolidine-1-carboxylate To a solution of 2-oxa-7-azaspiro[3.4]octane (87.56 mg, 773.79 umol, 1.5 eq) and 2-[N-[(2R,4R)-1-tert-butoxycarbonyl-4-methoxy-pyrrolidine-2-carbonyl]-4-(pentafluoro-λ$^6$-sulfanyl)anilino]-2-(3-pyridyl)acetic acid (300 mg, 515.86 umol, 1 eq) in DCM (3 mL), T3P (1.31 g, 2.06 mmol, 1.23 mL, 50% purity, 4 eq) and TEA (208.80 mg, 2.06 mmol, 287.21 uL, 4 eq) were added. The mixture was stirred at 20° C. for 2 h. Upon completion, the reaction mixture was poured into $H_2O$ 25 mL at 20° C., and then extracted with DCM (20 mL*3). The combined organic layers were washed with brine (20 mL*2), dried over $Na_2SO_4$, filtered and concentrated under reduced pressure to give a residue. The crude product was purified by column (Platel, $SiO_2$, PE:EA=2:1 to 0:1) to give tert-butyl (2R,4R)-4-methoxy-2-[[2-(2-oxa-7-azaspiro[3.4]octan-7-yl)-2-oxo-1-(3-pyridyl) ethyl]-[4-(pentafluoro-λ$^6$-sulfanyl)phenyl]carbamoyl]pyrrolidine-1-carboxylate (217.5 mg, 250.70 umol, 48.60% yield, 78% purity) (1.5 g, 2.33 mmol, 25.50% yield, 50% purity) as a yellow solid. MS (ESI) m/z 677.2 $[M+H]^+$.

Step 2: (2R,4R)-4-methoxy-N-[2-(2-oxa-7-azaspiro [3.4]octan-7-yl)-2-oxo-1-(3-pyridyl)ethyl]-N-[4-(pentafluoro-λ$^6$-sulfanyl)phenyl]pyrrolidine-2-carboxamide To a solution of tert-butyl (2R,4R)-4-methoxy-2-[[2-(2-oxa-7-azaspiro[3.4]octan-7-yl)-2-oxo-1-(3-pyridyl)ethyl]-[4-(pentafluoro-λ6-sulfanyl)phenyl]carbamoyl]pyrrolidine-1-carboxylate (207 mg, 305.90 umol, 1 eq) in DCM (2 mL), TFA (1.54 g, 13.51 mmol, 1 mL, 44.15 eq) was added. The mixture was stirred at 20° C. for 1 h. Upon completion, the reaction mixture was poured into $NaHCO_3$ 25 mL at 0° C., and extracted with DCM 60 mL (20 mL*3). The combined organic layers were washed with brine 40 mL (20 mL*2), dried over $Na_2SO_4$, filtered and concentrated under reduced pressure to give (2R,4R)-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl]pyrrolidine-2-carboxamide (158 mg, crude) as a yellow solid. MS (ESI) m/z 577.2 $[M+H]^+$.

Step 3: (2R,4R)-1-cyano-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl]pyrrolidine-2-carboxamide To a solution of (2R,4R)-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl]pyrrolidine-2-carboxamide (158 mg, 274.03 umol, 1 eq) in DMF (1.5 mL), $NaHCO_3$ (69.06 mg, 822.09 umol, 31.97 uL, 3 eq) was added, and then BrCN (38 mg, 358.76 umol, 26.39 uL, 1.31 eq) in DMF (0.5 mL) was added at 0° C. The mixture was stirred at 0° C. for 1 h. Upon completion, the reaction mixture was quenched by addition $H_2O$ 25 mL at 20° C., and then extracted with EtOAc (25 mL*3). The combined organic layers were washed with brine (25 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 25%-60%, 8 min) to give (2R,4R)-1-cyano-4-methoxy-N-[2-(2-oxa-7-azaspiro [3.4]octan-7-yl)-2-oxo-1-(3-pyridyl)ethyl]-N-[4-(pentafluoro-λ$^6$-sulfanyl)phenyl]pyrrolidine-2-carboxamide (40 ng) as a white solid. MS (ESI) m/z 602.2 $[M+H]^+$.

Step 4: (2R,4R)-1-cyano-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl]pyrrolidine-2-carboxamide Isomer 1: (2R,4R)-1-cyano-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl]pyrrolidine-2-carboxamide (40 mg) was separated by SFC to give (2R,4R)-1-cyano-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl] pyrrolidine-2-carboxamide (15.1 mg, 24.85 umol, 9.07% yield, 99% purity) as a white solid. MS (ESI) m/z 602.2 $[M+H]^+$.

1H NMR (400 MHz, DMSO-$d_6$) δ=8.67 (s, 1H), 8.62-8.53 (m, 1H), 8.44-8.28 (m, 2H), 7.93-7.86 (m, 1H), 7.75 (s, 1H), 7.51-7.44 (m, 1H), 7.26 (d, J=9.4, 13.8 Hz, 1H), 7.20-7.13 (m, 1H), 6.44 (d, J=13.4 Hz, 1H), 4.55-4.30 (m, 4H), 4.04-3.84 (m, 3H), 3.68-3.44 (m, 3H), 3.32-3.16 (m, 5H), 2.16-1.91 (m, 3H), 1.71 (d, J=5.8, 11.8 Hz, 1H)

Isomer 2: To give (2R,4R)-1-cyano-4-methoxy-N-[2-(2-oxa-7-azaspiro[3.4]octan-7-yl)-2-oxo-1-(3-pyridyl)ethyl]-N-[4-(pentafluoro-λ$^6$-sulfanyl)phenyl]pyrrolidine-2-carboxamide (14.5 mg, 23.77 umol, 8.67% yield, 98.6% purity) as a white solid. MS (ESI) m/z 602.2 $[M+H]^+$.

1H NMR (400 MHz, DMSO-$d_6$) δ=8.46-8.33 (m, 2H), 7.78 (s, 3H), 7.46-7.12 (m, 3H), 6.33 (d, J=11.4 Hz, 1H), 4.59-4.25 (m, 4H), 4.09-3.83 (m, 3H), 3.69-3.44 (m, 3H), 3.32-3.26 (m, 2H), 3.18 (d, J=3.4 Hz, 3H), 2.20-1.97 (m, 3H), 1.80 (d, J=6.4, 12.8 Hz, 1H)

Example 81: Synthesis of Compound 1185

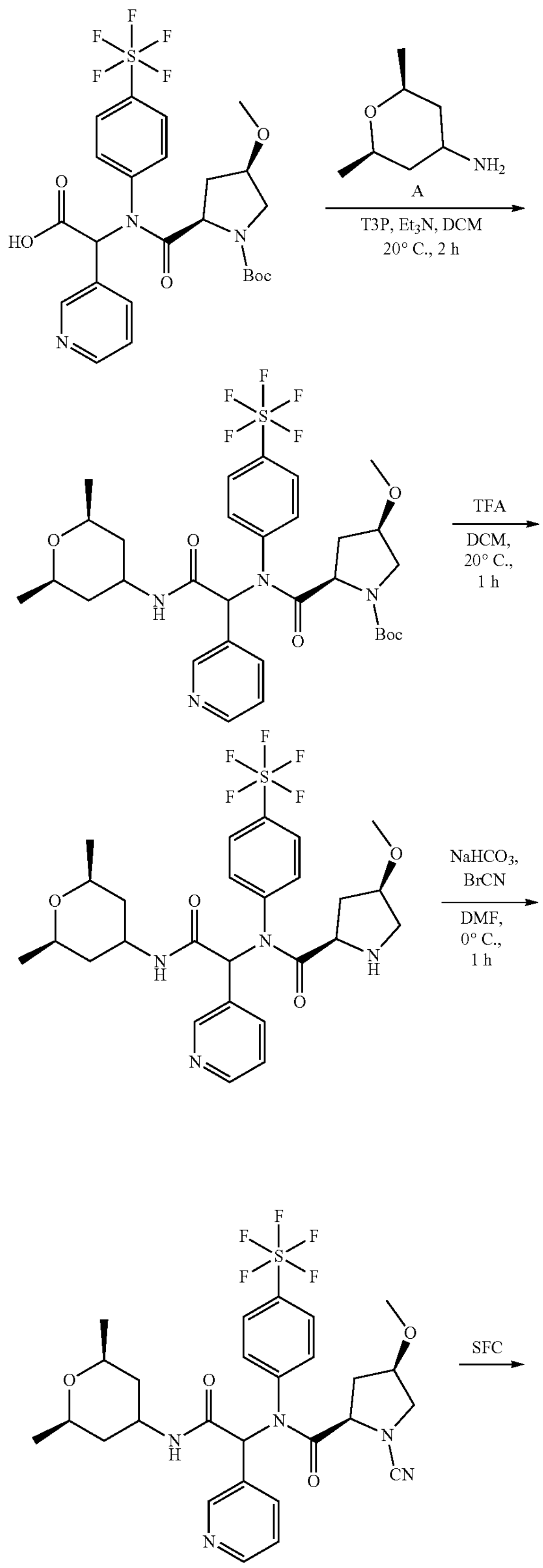

-continued

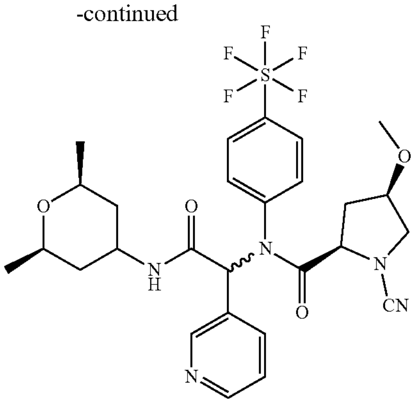

Step 1: tert-butyl (2R,4R)-2-[[2-[[(2R,6S)-2,6-dimethyltetrahydropyran-4-yl]amino]-2-oxo-1-(3-pyridyl)ethyl]-[4-(pentafluoro-λ$^6$-sulfanyl)phenyl]carbamoyl]-4-methoxy-pyrrolidine-1-carboxylate To a solution of 2-[N-[(2R,4R)-1-tert-butoxycarbonyl-4-methoxy-pyrrolidine-2-carbonyl]-4-(pentafluoro-λ6-sulfanyl)anilino]-2-(3-pyridyl)acetic acid (200 mg, 343.91 umol, 1 eq) and (2R,6S)-2,6-dimethyltetrahydropyran-4-amine (66.65 mg, 515.86 umol, 1.5 eq) in DCM (6 mL), $Et_3N$ (208.80 mg, 2.06 mmol, 287.20 uL, 6.0 eq) and T3P (656.55 mg, 1.03 mmol, 613.60 uL, 50% purity, 3.0 eq) were added drop-wise, and the mixture was stirred at 20° C. for 2 h. Upon completion, the reaction mixture was quenched by addition $H_2O$ 40 mL at 0° C., and then extracted with DCM (20 mL*3). The combined organic layers were washed with brine 30 mL, dried over $Na_2SO_4$, filtered and concentrated under reduced pressure to give a residue. The residue was purified by prep-TLC ($SiO_2$, DCM:MeOH=10:1) to get the product tert-butyl (2R,4R)-2-[[2-[[(2R,6S)-2,6-dimethyltetrahydropyran-4-yl]amino]-2-oxo-1-(3-pyridyl)ethyl]-[4-(pentafluoro-λ6-sulfanyl)phenyl]carbamoyl]-4-methoxy-pyrrolidine-1-carboxylate (0.12 g, 173.23 umol, 50.37% yield) as a yellow solid. MS (ESI) m/z 693.3 $[M+H]^+$.

Step 2: (2R,4R)—N-[2-[[(2R,6S)-2,6-dimethyltetrahydropyran-4-yl]amino]-2-oxo-1-(3-pyridyl)ethyl]-4-methoxy-N-[4-(pentafluoro-λ6-sulfanyl)phenyl]pyrrolidine-2-carboxamide To a solution of tert-butyl (2R,4R)-2-[[2-[[(2R,6S)-2,6-dimethyltetrahydropyran-4-yl]amino]-2-oxo-1-(3-pyridyl)ethyl]-[4-(pentafluoro-λ$^6$-sulfanyl)phenyl]carbamoyl]-4-methoxy-pyrrolidine-1-carboxylate (110 mg, 158.79 umol, 1 eq) in DCM (3 mL) was added dropwise TFA (1.54 g, 13.51 mmol, 1 mL, 85.06 eq). After addition, the mixture was stirred at 20° C. for 1 h. Upon completion, the reaction mixture was quenched by addition aq. $NaHCO_3$ 40 mL at 0° C., and then extracted with DCM (20 mL*3). The combined organic layers were washed with brine 40 mL, dried over $Na_2SO_4$, filtered and concentrated under reduced pressure to get the product (2R,4R)—N-[2-[[(2R,6S)-2,6-dimethyltetrahydropyran-4-yl]amino]-2-oxo-1-(3-pyridyl)ethyl]-4-methoxy-N-[4-(pentafluoro-λ$^6$-sulfanyl)phenyl]pyrrolidine-2-carboxamide (90 mg, crude) as a yellow solid. MS (ESI) m/z 593.2 $[M+H]^+$.

Step 3: (2R,4R)-1-cyano-N-[2-[[(2R,6S)-2,6-dimethyltetrahydropyran-4-yl]amino]-2-oxo-1-(3-pyridyl)ethyl]-4-methoxy-N-[4-(pentafluoro-λ$^6$-sulfanyl)phenyl]pyrrolidine-2-carboxamide A solution of (2R,4R)—N-[2-[[(2R,6S)-2,6-dimethyltetrahydropyran-4-yl]amino]-2-oxo-1-(3-pyridyl)ethyl]-4-methoxy-N-[4-(pentafluoro-λ6-sulfanyl)phenyl]pyrrolidine-2-carboxamide (80 mg, 134.99 umol, 1 eq) in DMF (2 mL) was cooled to 0° C., then $NaHCO_3$ (34.02 mg, 404.98 umol, 15.75 uL, 3.0 eq) and BrCN (17.16 mg, 161.99 umol, 11.92 uL, 1.2 eq) were added. The resulting mixture was stirred at 0° C. for 1 h. Upon completion, the reaction mixture was quenched by addition $H_2O$ 30 mL at 0° C., and then extracted with EA (15 mL*3). The combined organic layers were washed with brine 20 mL, dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 30%-55%, 8 min) to get the product (2R,4R)-1-cyano-N-[2-[[(2R,6S)-2,6-dimethyltetrahydropyran-4-yl]amino]-2-oxo-1-(3-pyridyl)ethyl]-4-methoxy-N-[4-(pentafluoro-λ$^6$-sulfanyl)phenyl]pyrrolidine-2-carboxamide (38 mg, 61.53 umol, 45.58% yield, 100% purity) as a white solid. MS (ESI) m/z 618.3 $[M+H]^+$ $^1$H NMR (DMSO-$d_6$, 400 MHz): δ ppm 8.43-8.20 (m, 3H), 8.17-6.83 (m, 6H), 6.34-6.08 (m, 1H), 4.14 (br t, J=7.6 Hz, 1H), 4.08-3.78 (m, 2H), 3.70-3.35 (m, 3H), 3.29-3.26 (m, 1H), 3.16 (s, 3H), 1.99-1.86 (m, 1H), 1.80-1.57 (m, 3H), 1.38-1.15 (m, 1H), 1.10-0.75 (m, 7H).

Step 4: (2R,4R)-1-cyano-N-[2-[[(2R,6S)-2,6-dimethyltetrahydropyran-4-yl]amino]-2-oxo-1-(3-pyridyl)ethyl]-4-methoxy-N-[4-(pentafluoro-λ$^6$-sulfanyl)phenyl]pyrrolidine-2-carboxamide (2R,4R)-1-cyano-N-[2-[[(2R,6S)-2,6-dimethyltetrahydropyran-4-yl]amino]-2-oxo-1-(3-pyridyl)ethyl]-4-methoxy-N-[4-(pentafluoro-λ$^6$-sulfanyl)phenyl]pyrrolidine-2-carboxamide (38 mg, 61.53 umol, 100% purity) was separated by SFC (column: DAICEL CHIRALPAK IC (250 mm*30 mm, 10 um); mobile phase: [0.1% $NH_3H_2O$ MeOH]; B %: 33%-33%, 6 min) to get the product (2R,4R)-1-cyano-N-[2-[[(2R,6S)-2,6-dimethyltetrahydropyran-4-yl]amino]-2-oxo-1-(3-pyridyl)ethyl]-4-methoxy-N-[4-(pentafluoro-?$^6$-sulfanyl)phenyl]pyrrolidine-2-carboxamide Isomer 1 (8 mg, 12.95 umol, 24.24% yield, 100% purity) as a white solid. MS (ESI) m/z 618.2 $[M+H]^+$ $^1$H NMR (DMSO-$d_6$, 400 MHz): δ ppm 8.40 (br d, J=6.2 Hz, 1H), 8.36-8.25 (m, 2H), 8.16-7.03 (m, 6H), 6.28 (s, 1H), 4.20-4.11 (m, 1H), 4.06 (br s, 1H), 3.88-3.78 (m, 1H), 3.68-3.56 (m, 2H), 3.28 (br dd, J=5.1, 9.2 Hz, 2H), 3.16 (s, 3H), 2.00-1.84 (m, 1H), 1.71 (td, J=6.1, 12.6 Hz, 1H), 1.61 (br d, J=13.3 Hz, 2H), 1.37-1.29 (m, 1H), 1.26-1.20 (m, 1H), 1.03 (d, J=6.1 Hz, 3H), 0.95 (d, J=6.1 Hz, 3H)

Example 82: Synthesis of Compound 1259

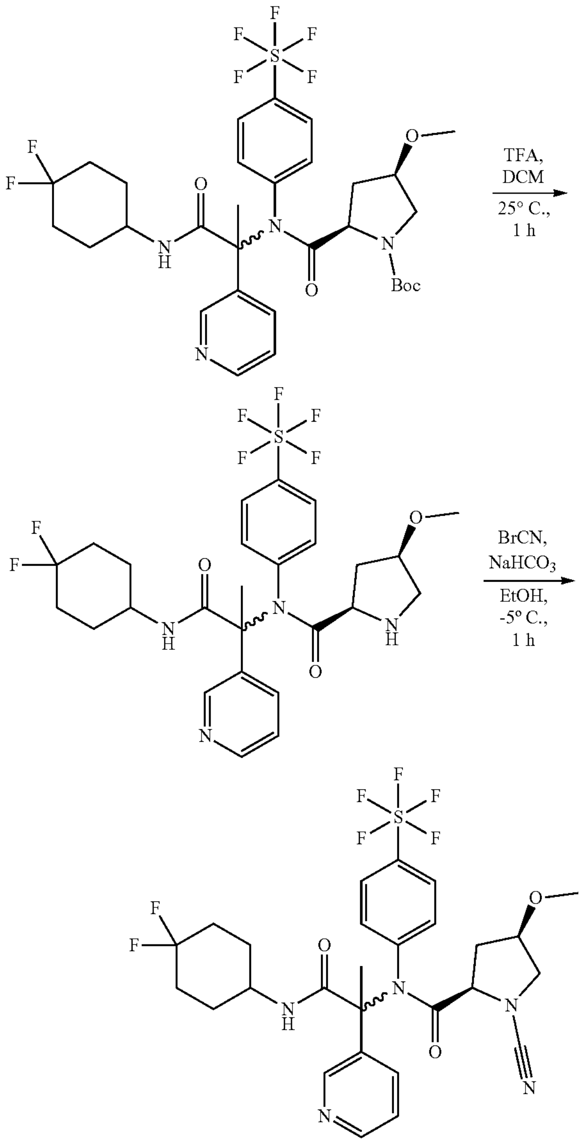

Step 1: (2R,4R)—N-[2-[(4,4-difluorocyclohexyl)amino]-1-methyl-2-oxo-1-(3-pyridyl)ethyl]-4-methoxy-N-[4-(pentafluoro-λ$^6$-sulfanyl)phenyl]pyrrolidine-2-carboxamide Isomer 1

A mixture of tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-methoxy-pyrrolidine-1-carboxylate Isomer 1 (1 g, 1.40 mmol, 1 eq) in DCM (10 mL) and TFA (5 mL) was stirred at 25° C. for 1 h. Upon completion, the reaction mixture was diluted with $NaHCO_3$ (50 mL) and extracted with DCM (20 mL*3). The combined organic layers were washed with brine, dried over $Na_2SO_4$, filtered and concentrated under reduced pressure to get product (2R,4R)—N-[2-[(4,4-difluorocyclohexyl)amino]-1-methyl-2-oxo-1-(3-pyridyl)ethyl]-4-methoxy-N-

[4-(pentafluoro-λ$^6$-sulfanyl)phenyl]pyrrolidine-2-carboxamide Isomer 1 (1 g, crude) as yellow oil. MS (ESI) m/z 613.3 $[M+H]^+$.

Step 2: (2R,4R)-1-cyano-N-[2-[(4,4-difluorocyclohexyl)amino]-1-methyl-2-oxo-1-(3-pyridyl)ethyl]-4-methoxy-N-[4-(pentafluoro-λ$^6$-sulfanyl)phenyl]pyrrolidine-2-carboxamide Isomer 1

A mixture of (2R,4R)—N-[2-[(4,4-difluorocyclohexyl)amino]-1-methyl-2-oxo-1-(3-pyridyl)ethyl]-4-methoxy-N-[4-(pentafluoro-λ$^6$-sulfanyl)phenyl]pyrrolidine-2-carboxamide Isomer 1 (1 g, 1.63 mmol, 1 eq) in EtOH (10 mL) was added $NaHCO_3$ (411.39 mg, 4.90 mmol, 190.46 uL, 3 eq), then the solution was cooled to −5° C. and BrCN (207.48 mg, 1.96 mmol, 144.09 uL, 1.2 eq) in EtOH (1 mL) was added drop-wise, the mixture was stirred at −5° C. for 1 h. Upon completion, the reaction mixture was quenched with water (50 mL) and extracted with EA (30 mL*3). The combined organic layers were dried over $Na_2SO_4$, filtered and concentrated under reduced pressure to give a residue. The residue was purified by prep-HPLC (column: Welch X timate C18 250*70 mm #10 um; mobile phase: [water (10 mM $NH_4HCO_3$)-ACN]; B %: 36%-66%, 20 min) to get the product (2R,4R)-1-cyano-N-[2-[(4,4-difluorocyclohexyl)amino]-1-methyl-2-oxo-1-(3-pyridyl)ethyl]-4-methoxy-N-[4-(pentafluoro-λ$^6$-sulfanyl)phenyl]pyrrolidine-2-carboxamide Isomer 1 (478.02 mg, 742.21 umol, 45.47% yield, 99% purity) as yellow solid. MS (ESI) m/z 638.2 $[M+H]^+$. $^1H$ NMR (400 MHz, METHANOL-$d_4$) δ=8.65 (d, J=2.4 Hz, 1H), 8.39 (s, 1H), 8.00-7.93 (m, 1H), 7.86 (br d, J=8.7 Hz, 2H), 7.62-7.48 (m, 2H), 7.35 (dd, J=4.8, 8.2 Hz, 1H), 4.13 (dd, J=5.6, 8.8 Hz, 1H), 3.89 (s, 2H), 3.60 (dd, J=5.9, 9.6 Hz, 1H), 3.45 (dd, J=4.9, 9.5 Hz, 1H), 3.28 (s, 3H), 2.17-2.01 (m, 3H), 1.99-1.84 (m, 8H), 1.73-1.53 (m, 2H).

Example 83: Synthesis of Compound 1261

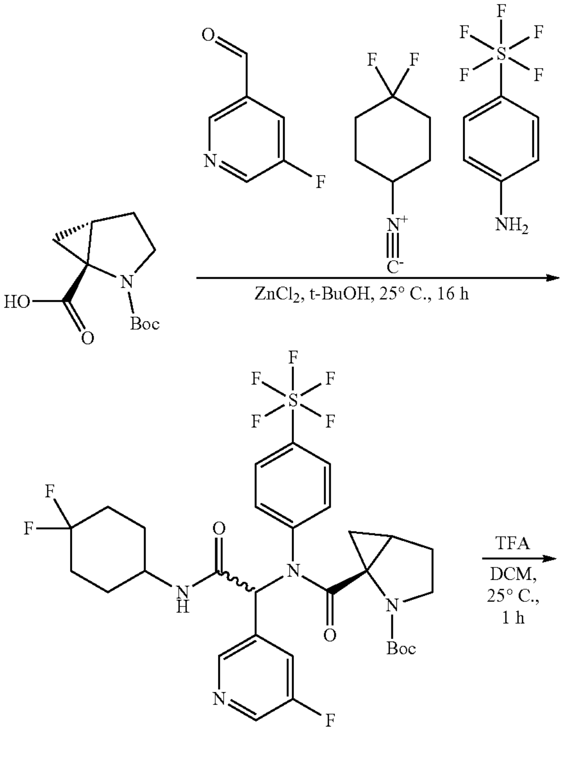

-continued

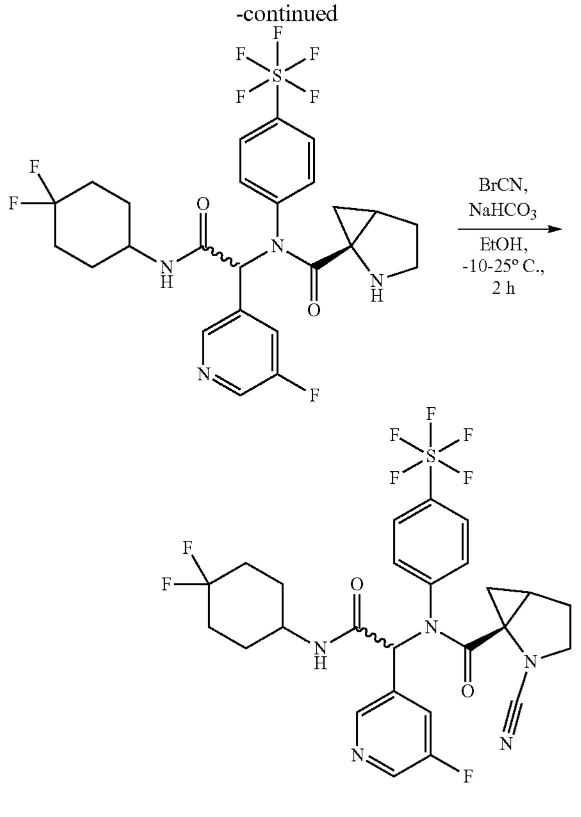

Step1: tert-butyl (1R,5S)-1-[[2-[(4,4-difluorocyclohexyl)amino]-1-(S-fluoro-3-pyridyl)-2-oxo-ethyl]-[4-(pentafluoro-2-sulfanyl)phenyl]carbamoyl]-2-azabicyclo[3.1.0]hexane-2-carboxylate To a solution of 4-(pentafluoro-λ$^6$-sulfanyl)aniline (289.33 mg, 1.32 mmol, 1 eq), 5-fluoropyridine-3-carbaldehyde (165.14 mg, 1.32 mmol, 1 eq) in t-BuOH (10 mL) was stirred at 25° C. for 8 h, and the mixture was added (1R,5S)-2-(tert-butoxycarbonyl)-2-azabicyclo[3.1.0]hexane-1-carboxylic acid (300 mg, 1.32 mmol, 1 eq), 1,1-difluoro-4-isocyano-cyclohexane (191.61 mg, 1.32 mmol, 1 eq), $ZnCl_2$ (1 M, 7.92 mL, 6 eq) and stirred at 25° C. for 8 h. Upon completion, the reaction was concentrated in the vacuum and was purified by prep-HPLC (column: Kromasil C18 (250*50 mm*10 um); mobile phase: [water (10 mM $NH_4HCO_3$)-ACN]; B %: 60%-80%, 10 min) to give product tert-butyl (1R,5S)-1-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2-azabicyclo[3.1.0]hexane-2-carboxylate (240 mg, 343.51 umol, 26.02% yield) was yellow oil. MS (ESI) m/z 699.2 $[M+H]^+$.

Step2: (1R,5S)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-azabicyclo[3.1.0]hexane-1-carboxamide To a solution of tert-butyl (1R,5S)-1-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2-azabicyclo[3.1.0]hexane-2-carboxylate (220 mg, 314.89 umol, 1 eq) in DCM (4.5 mL) was added TFA (2.15 g, 18.89 mmol, 1.40 mL, 60 eq) and the mixture was stirred at 25° C. for 1 h.

Upon completion, the mixture was quenched by addition $NaHCO_3$ (20 mL) and then extracted with DCM (10 mL*3). The combined organic layers were washed with brine (10 mL), dried over $Na_2SO_4$, filtered and concentrated under reduced pressure to give a crude product (1R,5S)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-azabicyclo[3.1.0]hexane-1-carboxamide (200 mg, crude) was yellow oil. MS (ESI) m/z 599.2 $[M+H]^+$.

Step3: (1R,5S)-2-cyano-N-[2-[(4,4-difluorocyclohexyl)amino]-1-(S-fluoro-3-pyridyl)-2-oxo-ethyl]-N-[4-(pentafluoro-λ$^6$-sulfanyl)phenyl]-2-azabicyclo[3.1.0]hexane-1-carboxamide To a solution of (1R,5S)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-azabicyclo[3.1.0]hexane-1-carboxamide (200 mg, 334.14 umol, 1 eq) in EtOH (5 mL) was added $NaHCO_3$ (84.21 mg, 1.00 mmol, 38.99 uL, 3 eq) and the mixture was cooled at −10° C. To the resulting mixture was added BrCN (38.93 mg, 367.55 umol, 27.04 uL, 1.1 eq) in EtOH (0.5 mL), and the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure and was purified by prep-HPLC (column: Phenomenex Luna C18 75*30 mm*3 um; mobile phase: [water (0.2% FA)-ACN]; B %: 40%-80%, 8 min) to give a product (1R,5S)-2-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-azabicyclo[3.1.0]hexane-1-carboxamide (110 mg, 176.41 umol, 52.79% yield, 100% purity) was yellow solid. MS (ESI) m/z 624.2 $[M+H]^+$ $^1H$ NMR (400 MHz, MeOD-$d_4$) δ=8.43-8.30 (m, 1H), 8.28-8.19 (m, 1H), 7.82-7.41 (m, 5H), 6.28-5.97 (m, 1H), 3.99-3.73 (m, 1H), 2.98-2.88 (m, 1H), 2.77-2.57 (m, 1H), 2.24-2.12 (m, 1H), 2.08-1.70 (m, 8H), 1.66-1.52 (m, 2H), 1.50-1.37 (m, 1H), 1.21-1.10 (m, 1H)

Example 84: Synthesis of Compound 1263

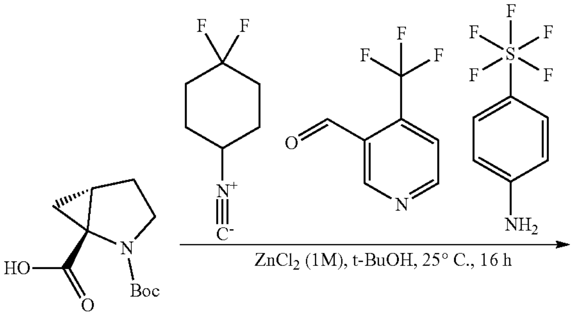

-continued

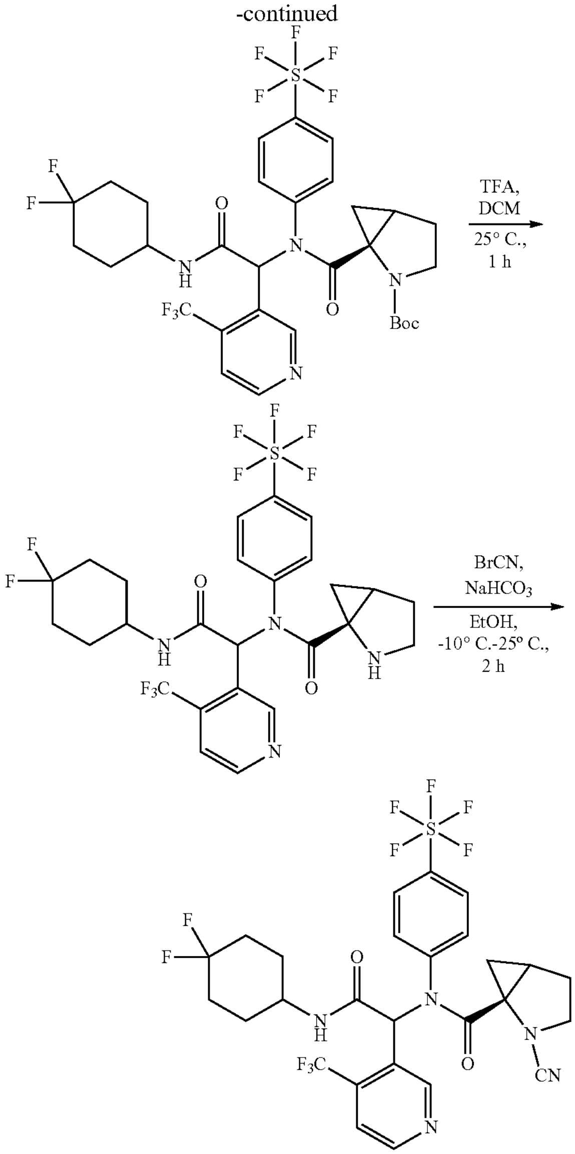

Step1: tert-butyl (1R,5S)-1-[[2-[(4,4-difluorocyclohexyl)amino]-2-oxo-1-[4-(trifluoromethyl)-3-pyridyl]ethyl]-[4-(pentafluoro-λ$^6$-sulfanyl)phenyl]carbamoyl]-2-azabicyclo[3.1.0]hexane-2-carboxylate A solution of 4-(pentafluoro-λ$^6$-sulfanyl)aniline (289.33 mg, 1.32 mmol, 1 eq) 4-(trifluoromethyl)pyridine-3-carbaldehyde (231.16 mg, 1.32 mmol, 1 eq) in t-BuOH (10 mL) was stirred at 25° C. for 8 h, and the reaction mixture was added with (1R,5S)-2-tert-butoxycarbonyl-2-azabicyclo[3.1.0]hexane-1-carboxylic acid (300 mg, 1.32 mmol, 1 eq) 1,1-difluoro-4-isocyano-cyclohexane (191.61 mg, 1.32 mmol, 1 eq) $ZnCl_2$ (1 M, 7.92 mL, 6 eq) and stirred at 80° C. for 8 h. Upon completion, the reaction was concentrated in the vacuum and was purified by prep-HPLC (column: Kromasil C18 (250*50 mm*10 um); mobile phase: [water (10 mM $NH_4HCO_3$)-ACN]; B %: 60%-80%, 10 min) to give product tert-butyl (1R,5S)-1-[[2-[(4,4-difluorocyclohexyl)amino]-2-oxo-1-[4-(trifluoromethyl)-3-pyridyl]ethyl]-[4-(pentafluoro-λ$^6$-sulfanyl)phenyl]carbamoyl]-2-azabicyclo

[3.1.0]hexane-2-carboxylate (50 mg, 66.78 umol, 5.06% yield) was yellow oil. MS (ESI) m/z 749.2 [M+H]+.

Step2: (1R,5S)—N-[2-[(4,4-difluorocyclohexyl) amino]-2-oxo-1-[4-(trifluoromethyl)-3-pyridyl] ethyl]-N-[4-(pentafluoro-A6-sulfanyl)phenyl]-2-azabicyclo[3.1.0]hexane-1-carboxamide To a solution of tert-butyl (1R,5S)-1-[[2-[(4,4-difluorocyclohexyl)amino]-2-oxo-1-[4-(trifluoromethyl)-3-pyridyl] ethyl]-[4-(pentafluoro-λ$^6$-sulfanyl)phenyl]carbamoyl]-2-azabicyclo[3.1.0]hexane-2-carboxylate (45 mg, 60.11 umol, 1 eq) in DCM (1 mL) was added TFA (411.21 mg, 3.61 mmol, 267.02 uL, 60 eq) and the mixture was stirred at 25° C. for 1 h. Upon completion, the mixture was quenched by addition $NaHCO_3$ (20 mL) and then extracted with DCM (10 mL*3). The combined organic layers were washed with brine (10 mL), dried over $Na_2SO_4$, filtered and concentrated under reduced pressure to give a crude product (1R,5S)—N-[2-[(4,4-difluorocyclohexyl)amino]-2-oxo-1-[4-(trifluoromethyl)-3-pyridyl]ethyl]-N-[4-(pentafluoro-λ$^6$-sulfanyl) phenyl]-2-azabicyclo[3.1.0]hexane-1-carboxamide (80 mg, crude) was yellow oil. MS (ESI) m/z 649.2 [M+H]+.

Step3: (1R,5S)-2-cyano-N-[2-[(4,4-difluorocyclohexyl)amino]-2-oxo-1-[4-(trifluoromethyl)-3-pyridyl]ethyl]-N-[4-(pentafluoro-λ$^6$-sulfanyl)phenyl]-2-azabicyclo[3.1.0]hexane-1-carboxamide To a solution of (1R,5S)—N-[2-[(4,4-difluorocyclohexyl) amino]-2-oxo-1-[4-(trifluoromethyl)-3-pyridyl]ethyl]-N-[4-(pentafluoro-λ$^6$-sulfanyl)phenyl]-2-azabicyclo[3.1.0] hexane-1-carboxamide (70 mg, 107.93 umol, 1 eq) in EtOH (1 mL) was added $NaHCO_3$ (27.20 mg, 323.80 umol, 12.59 uL, 3 eq) and the mixture was cooled at −10° C., then the mixture was added BrCN (12.58 mg, 118.72 umol, 8.73 uL, 1.1 eq) in EtOH (0.5 mL) and the mixture was warmed at 25° C. and stirred for 2 h. Upon completion, the mixture was quenched by addition $H_2O$ (20 mL) and then extracted with DCM (20 mL*3). The combined organic layers were washed with brine 20 mL, dried over $Na_2SO_4$, filtered and concentrated under reduced pressure and was purified by prep-HPLC (column: Phenomenex Luna C18 75*30 mm*3 um; mobile phase: [water (0.2% FA)-ACN]; B %: 40%-80%, 8 min) to give product (1R,5S)-2-cyano-N-[2-[(4,4-difluorocyclohexyl)amino]-2-oxo-1-[4-(trifluoromethyl)-3-pyridyl] ethyl]-N-[4-(pentafluoro-λ$^6$-sulfanyl)phenyl]-2-azabicyclo [3.1.0]hexane-1-carboxamide (20 mg, 29.69 umol, 27.51% yield, 100% purity) was white solid. MS (ESI) m/z 674.2 [M+H]+

$^1$H NMR (400 MHz, MeOD-d$_4$) δ=8.72-8.71 (m, 1H), 8.35 (s, 1H), 8.05-7.58 (m, 4H), 7.02 (br s, 1H), 6.39 (s, 1H), 3.78-3.73 (m, 1H), 2.96-2.89 (m, 1H), 2.67-2.55 (m, 1H), 2.24-2.15 (m, 1H), 2.03-1.70 (m, 8H), 1.64-1.52 (m, 1H), 1.49-1.34 (m, 2H), 1.18-1.15 (m, 1H)

Example 85: Synthesis of Compound 1265

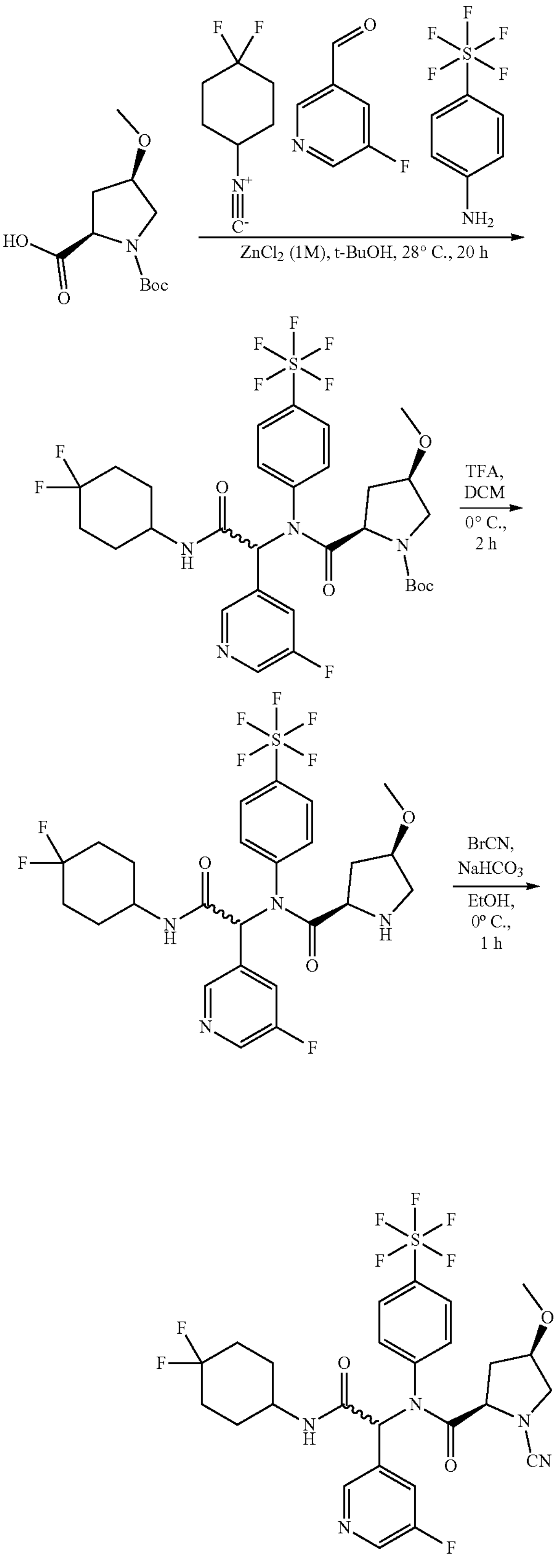

Step 1: tert-butyl (2R,4R)-2-[[2-[(4,4-difluorocyclohexyl)amino]-1-(S-fluoro-3-pyridyl)-2-oxo-ethyl]-[4-(pentafluoro-A6-sulfanyl)phenyl]carbamoyl]-4-methoxy-pyrrolidine-1-carboxylate To a mixture of 4-(pentafluoro-λ6-sulfanyl)aniline (400 mg, 1.83 mmol, 1 eq) in t-BuOH (4 mL) was added 5-fluoropyridine-3-carbaldehyde (251.14 mg, 2.00 mmol, 1.1 eq) in one portion. The mixture was stirred at 28° C. for 3 h. Then (2R,4R)-1-tert-butoxycarbonyl-4-methoxy-pyrrolidine-2-carboxylic acid (447.62 mg, 1.83 mmol, 1 eq) was added to the mixture and the mixture was stirred at 28° C. for 30 min, then 1,1-difluoro-4-isocyano-cyclohexane (264.91 mg, 1.83 mmol, 1 eq) was added to the mixture and stirred at 28° C. for 30 min. $ZnCl_2$ (746.26 mg, 5.48 mmol, 256.44 uL, 3 eq) was added to the mixture and the mixture was stirred at 28° C. for 16 h. Upon completion, the reaction mixture was concentrated under reduced pressure to give a residue. The crude product was purified by pre-HPLC (Column: column: Waters Xbridge Prep OBD C18 150*40 mm*10 um; mobile phase: [column: Welch Xtimate $C_{18}$ 250*70 mm #10 um; mobile phase: [water (10 mM $NH_4HCO_3$)-ACN]; B %: 40%-70%, 20 min). Compound tert-butyl(2R,4R)-2-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-4-methoxy-pyrrolidine-1-carboxylate Isomer 1 (160 mg, 223.25 umol, 12.23% yield) was obtained as a yellow solid. MS (ESI) m/z 717.3 [M+H]+

Compound tert-butyl(2R,4R)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-4-methoxy-pyrrolidine-1-carboxylate Isomer 1 (180 mg, 251.16 umol, 13.76% yield) was obtained as a yellow solid. MS (ESI) m/z 717.3 $[M+H]^+$ Step 2: (2R,4R)—N-[2-[(4,4-difluorocyclohexyl)amino]-1-(5-fluoro-3-pyridyl)-2-oxo-ethyl]-4-methoxy-N-[4-(pentafluoro-A6-sulfanyl)phenyl]pyrrolidine-2-carboxamide Isomer 1

To a mixture of tert-butyl(2R,4R)-2-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-4-methoxy-pyrrolidine-1-carboxylate Isomer 1 (140 mg, 1 umol, 1 eq) in DCM (4.5 mL) was added TFA (2.31 g, 20.26 mmol, 1.5 mL, 168.34 eq) in one portion. The mixture was stirred at 0° C. for 2 h. Upon completion, the reaction mixture was concentrated to get the crude product. (2R,4R)—N-[2-[(4,4-difluorocyclohexyl)amino]-1-(5-fluoro-3-pyridyl)-2-oxo-ethyl]-4-methoxy-N-[4-(pentafluoro-$\lambda^6$-sulfanyl)phenyl]pyrrolidine-2-carboxamide Isomer 1 (135 mg, crude) was obtained as light yellow oil and used directly next step. MS (ESI) m/z 617.2 $[M+H]^+$.

(2R,4R)—N-[2-[(4,4-difluorocyclohexyl)amino]-1-(5-fluoro-3-pyridyl)-2-oxo-ethyl]-4-methoxy-N-[4-(pentafluoro-A6-sulfanyl)phenyl]pyrrolidine-2-carboxamide Isomer 2

To a mixture of tert-butyl(2R,4R)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-4-methoxy-pyrrolidine-1-carboxylate Isomer 2 (160 mg, 223.25 umol, 1 eq) in DCM (4.5 mL) was added TFA (2.31 g, 20.26 mmol, 1.5 mL, 168.34 eq) in one portion. The mixture was stirred at 0° C. for 2 h. Upon completion, the reaction mixture was concentrated to get the crude product. (2R,4R)—N-[2-[(4,4-difluorocyclohexyl)amino]-1-(5-fluoro-3-pyridyl)-2-oxo-ethyl]-4-methoxy-N-[4-(pentafluoro-$\lambda^6$-sulfanyl)phenyl]pyrrolidine-2-carboxamide Isomer 2 (140 mg, crude) was obtained as light yellow oil and used directly next step. MS (ESI) m/z 617.2 $[M+H]^+$.

Step 3: (2R,4R)-1-cyano-N-[2-[(4,4-difluorocyclohexyl)amino]-1-(5-fluoro-3-pyridyl)-2-oxo-ethyl]-4-methoxy-N-[4-(pentafluoro-A6-sulfanyl)phenyl]pyrrolidine-2-carboxamide Isomer 1

To a mixture of (2R,4R)—N-[2-[(4,4-difluorocyclohexyl)amino]-1-(5-fluoro-3-pyridyl)-2-oxo-ethyl]-4-methoxy-N-[4-(pentafluoro-λ6-sulfanyl)phenyl]pyrrolidine-2-carboxamide Isomer 1 (135 mg, crude, 1 eq) and $NaHCO_3$ (128.76 mg, 1.53 mmol, 59.61 uL, 7 eq) in EtOH (2 mL) was added BrCN (46.38 mg, 437.91 umol, 32.21 uL, 2 eq) in one portion at 0° C. The mixture was stirred at 0° C. for 1 h. The residue was poured into water (2 mL) and extracted with ethyl acetate (2 mL*3). The combined organic phase was washed with brine (2 mL), dried with anhydrous $Na_2SO_4$, filtered and concentrated in vacuum to get the crude product. The crude product was purified by pre-HPLC. (column: Waters Xbridge BEH C18 100*30 mm*10 um; mobile phase: [column: Phenomenex Gemini-NX $C_{18}$ 75*30 mm*3 um; mobile phase: [water (0.2% FA)-ACN]; B %: 45%-75%, 8 min). (2R,4R)-1-cyano-N-[2-[(4,4-difluorocyclohexyl)amino]-1-(5-fluoro-3-pyridyl)-2-oxo-ethyl]-4-methoxy-N-[4-(pentafluoro-λ6-sulfanyl)phenyl]pyrrolidine-2-carboxamide Isomer 1 (65 mg, 99.82 umol, 46.27% yield, 98.53% purity) was obtained as a white solid. MS (ESI) m/z 642.2 $[M+H]^+$ $^1H$ NMR (400 MHz, DMSO-$d_6$) δ ppm 8.35-8.40 (m, 2H), 8.16 (s, 1H), 7.53-7.87 (m, 4H), 7.45 (br d, J=9.78 Hz, 1H), 6.16 (s, 1H), 4.18 (dd, J=8.82, 6.56 Hz, 1H), 3.83 (quin, J=5.72 Hz, 2H), 3.60 (dd, J=9.36, 6.02 Hz, 1H), 3.16 (s, 3H), 1.75-1.75 (m, 1H), 1.75-2.05 (m, 8H), 1.66-1.74 (m, 1H), 1.45-1.57 (m, 1H), 1.28-1.40 (m, 1H)

(2R,4R)-1-cyano-N-[2-[(4,4-difluorocyclohexyl)amino]-1-(5-fluoro-3-pyridyl)-2-oxo-ethyl]-4-methoxy-N-[4-(pentafluoro-A6-sulfanyl)phenyl]pyrrolidine-2-carboxamide Isomer 2

To a mixture of (2R,4R)—N-[2-[(4,4-difluorocyclohexyl)amino]-1-(5-fluoro-3-pyridyl)-2-oxo-ethyl]-4-methoxy-N-[4-(pentafluoro-$\lambda^6$-sulfanyl)phenyl]pyrrolidine-2-carboxamide Isomer 2 (140 mg, crude, 1 eq) and $NaHCO_3$ (133.52 mg, 1.59 mmol, 61.82 uL, 7 eq) in EtOH (2 mL) was added BrCN (48.10 mg, 454.13 umol, 33.40 uL, 2 eq) in one portion at 0° C. The mixture was stirred at 0° C. for 3 h. The residue was poured into water (2 mL) and extracted with ethyl acetate (2 mL*3). The combined organic phase was washed with brine (2 mL), dried with anhydrous $Na_2SO_4$, filtered and concentrated in vacuum to get the crude product. The crude product was purified by pre-HPLC. (column: Phenomenex Gemini-NX 80*40 mm*3 um; mobile phase: [column: Phenomenex Gemini-NX $C_{18}$ 75*30 mm*3 um; mobile phase: [water (0.2% FA)-ACN]; B %: 45%-65%, 8 min). (2R,4R)-1-cyano-N-[2-[(4,4-difluorocyclohexyl)amino]-1-(5-fluoro-3-pyridyl)-2-oxo-ethyl]-4-methoxy-N-[4-(pentafluoro-λ6-sulfanyl)phenyl]pyrrolidine-2-carboxamide Isomer 2 (63 mg, 98.69 umol, 43.25% yield, 98.67% purity) was obtained as a white solid. MS (ESI) m/z 642.2 $[M+H]^+$ $^1H$ NMR (400 MHz, DMSO-$d_6$) δ ppm 8.45 (d, J=2.74 Hz, 1H), 8.31 (d, J=7.39 Hz, 1H), 8.21 (s, 1H), 7.87 (br d, J=7.87 Hz, 2H), 7.39-7.60 (m, 2H), 6.02-6.07 (m, 1H), 6.04 (s, 1H), 4.17 (br d, J=6.08 Hz, 1H), 3.85 (dt, J=11.03, 5.45 Hz, 1H), 3.76 (br d, J=6.56 Hz, 1H), 3.57 (br dd, J=9.54, 5.96 Hz, 1H), 3.17 (s, 3H), 1.72 (br t, J=13.17 Hz, 2H), 1.65-2.12 (m, 9H), 1.22-1.47 (m, 2H)

Example 86: Synthesis of Compound 1267

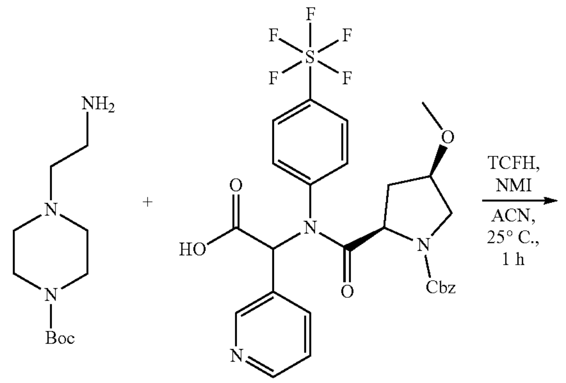

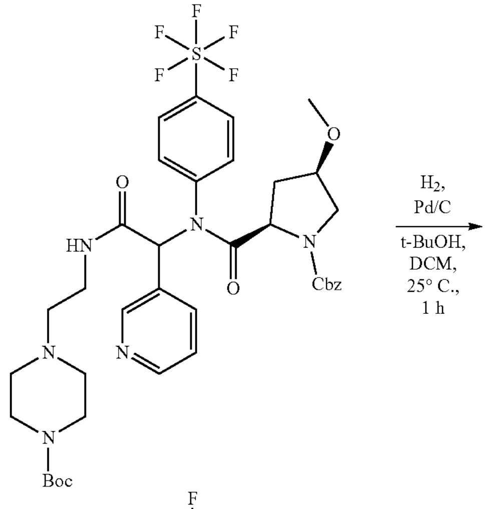

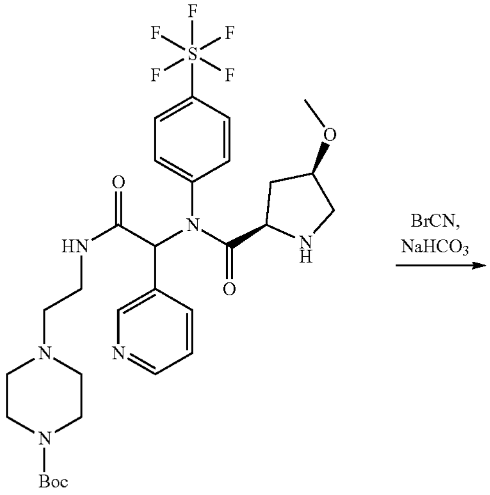

-continued

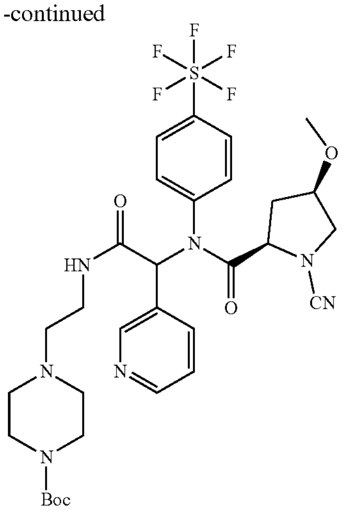

Step1: tert-butyl4-[2-[[2-[N-[(2R,4R)-1-benzyloxy-carbonyl-4-methoxy-pyrrolidine-2-carbonyl]-4-(pentafluoro-$\lambda^6$-sulfanyl)anilino]-2-(3-pyridyl)acetyl]amino]ethyl]piperazine-1-carboxylate To a solution of tert-butyl 4-(2-aminoethyl)piperazine-1-carboxylate (149.01 mg, 649.81 umol, 1 eq) 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (400 mg, 649.81 umol, 1 eq) in ACN (8 mL) was added 1-methylimidazole (186.73 mg, 2.27 mmol, 181.29 uL, 3.5 eq) [chloro(dimethylamino)methylene]-dimethyl-ammonium;hexafluorophosphate (237.02 mg, 844.75 umol, 1.3 eq) and the mixture was stirred at 25° C. for 1 h. Upon completion, the mixture was quenched by addition $H_2O$ (50 mL) and then extracted with EtOAc (20 mL*3). The combined organic layers were washed with brine (20 mL), dried over $Na_2SO_4$, filtered and concentrated under reduced pressure and was purified by prep-TLC ($SiO_2$, DCM:MeOH=10:1) to give product tert-butyl 4-[2-[[2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetyl]amino]ethyl]piperazine-1-carboxylate (430 mg, 520.03 umol, 80.03% yield) was yellow oil. MS (ESI) m/z 827.3 $[M+H]^+$ Step2: tert-butyl4-[2-[[2-[N-[(2R,4R)-4-methoxy-pyrrolidine-2-carbonyl]-4-(pentafluoro-$\lambda^6$-sulfanyl)anilino]-2-(3-pyridyl)acetyl]amino]ethyl]piperazine-1-carboxylate To a solution of tert-butyl 4-[2-[[2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetyl]amino]ethyl]piperazine-1-carboxylate (400 mg, 483.75 umol, 1 eq) in DCM (2 mL), t-BuOH (10 mL) was added Pd/C (500 mg, 483.75 umol, 10% purity, 1 eq) and the mixture was stirred at 25° C. for 1 h under $H_2$. Upon completion, the reaction was filtered and concentrated in vacuum to give product tert-butyl 4-[2-[[2-[N-[(2R,4R)-4-methoxypyrrolidine-2-carbonyl]-4-(pentafluoro-$\lambda^6$-sulfanyl)anilino]-2-(3-pyridyl)acetyl]amino]ethyl]piperazine-1-carboxylate (330 mg, crude) was yellow oil. MS (ESI) m/z 692.3 $[M+H]^+$

Step3: tert-butyl4-[2-[[2-[N-[(2R,4R)-1-cyano-4-methoxy-pyrrolidine-2-carbonyl]-4-(pentafluoro-$\lambda^6$-sulfanyl)anilino]-2-(3-pyridyl)acetyl]amino]ethyl]piperazine-1-carboxylate To a solution of tert-butyl 4-[2-[[2-[N-[(2R,4R)-4-methoxypyrrolidine-2-carbonyl]-4-(pentafluoro-$\lambda^6$-sulfanyl)anilino]-2-(3-pyridyl)acetyl]amino]ethyl]piperazine-1-carboxylate (200 mg, 288.71 umol, 1 eq) in EtOH (5 mL) was added $NaHCO_3$ (72.76 mg, 866.13 umol, 33.69 uL, 3 eq) and the mixture was cooled at −10° C. and the mixture was added BrCN (39.75 mg, 375.32 umol, 27.61 uL, 1.3 eq) in EtOH (1 mL) and the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue. The crude product was purified by prep-HPLC (column: Phenomenex Luna C18 200*40 mm*10 um; mobile phase: [water (0.2% FA)-ACN]; B %: 10%-50%, 8 min) to give product tert-butyl4-[2-[[2-[N-[(2R,4R)-1-cyano-4-methoxy-pyrrolidine-2-carbonyl]-4-(pentafluoro-$\lambda^6$-sulfanyl)anilino]-2-(3-pyridyl)acetyl]amino]ethyl]piperazine-1-carboxylate (30 mg, 40.75 umol, 14.11% yield, 97.488% purity) was yellow solid. MS (ESI) m/z 718.3 $[M+H]^+$ $^1H$ NMR (400 MHz, MeOD-$d_4$) δ=8.44-8.32 (m, 2H), 7.84-7.15 (m, 6H), 6.78-6.68 (m, 1H), 6.32-6.05 (m, 1H), 4.29-4.17 (m, 1H), 3.94-3.86 (m, 1H), 3.68-3.59 (m, 1H), 3.39-3.31 (m, 4H), 3.29-3.28 (m, 2H), 3.18 (s, 1H), 2.63-2.34 (m, 8H), 2.16-1.97 (m, 2H), 1.45 (s, 9H)

Example 87: Synthesis of Compound 1187

-continued

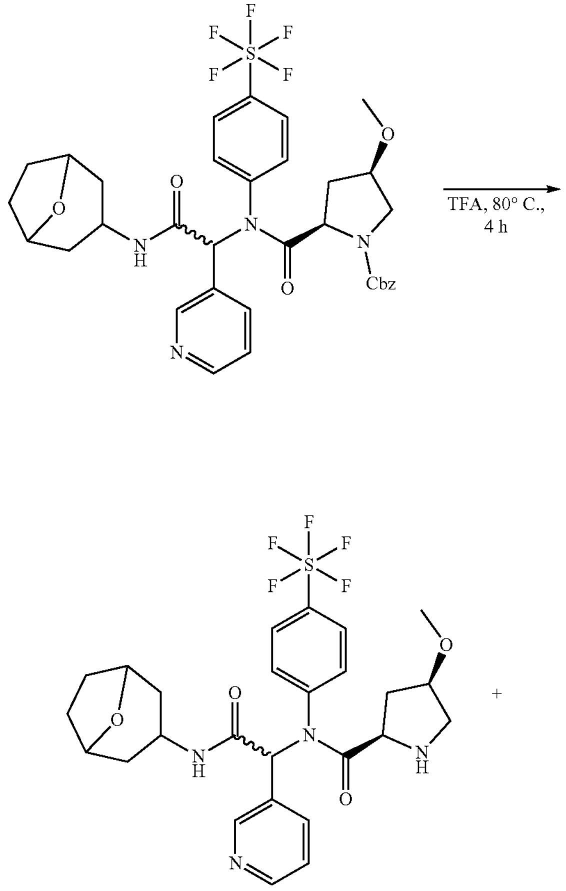

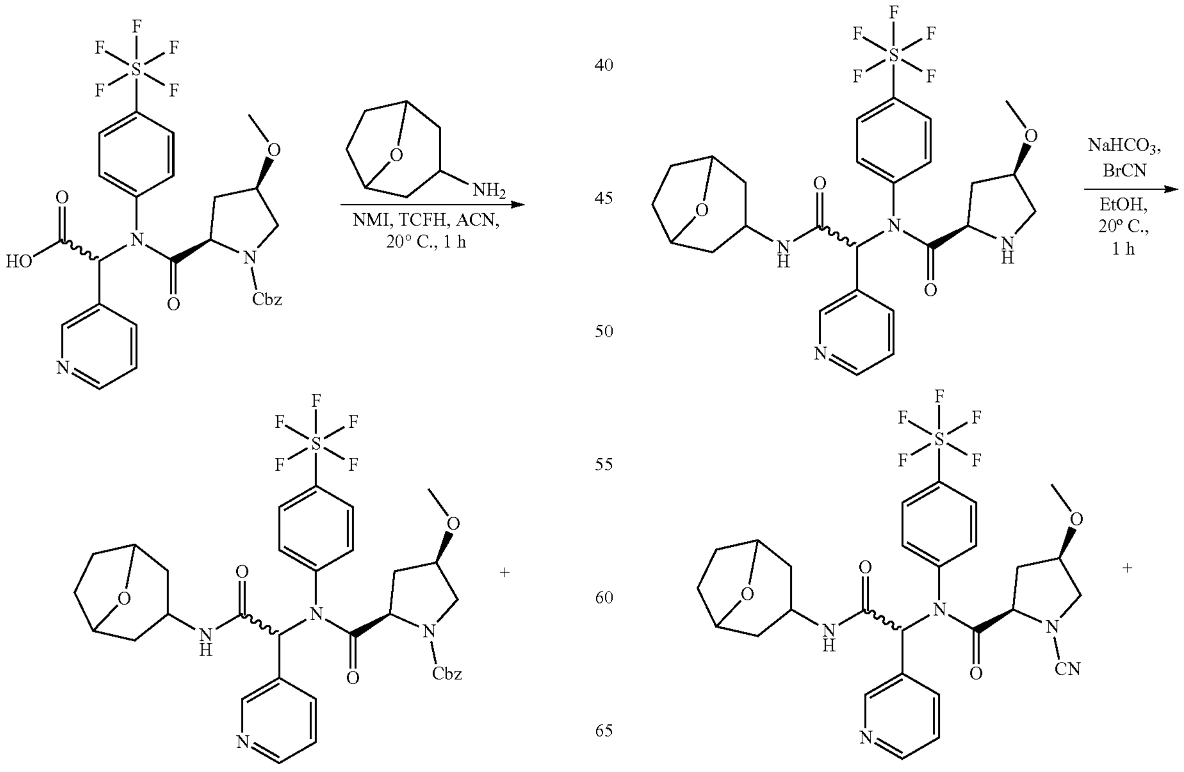

-continued

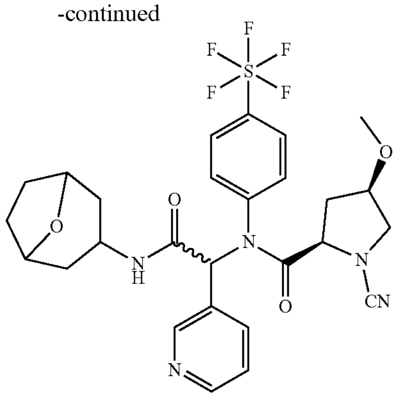

Step 1: benzyl (2R,4R)-4-methoxy-2-[[2-(8-oxabicyclo[3.2.1]octan-3-ylamino)-2-oxo-1-(3-pyridyl)ethyl]-[4-(pentafluoro-λ$^6$-sulfanyl)phenyl]carbamoyl]pyrrolidine-1-carboxylate A mixture of 8-oxabicyclo[3.2.1]octan-3-amine (217.00 mg, 1.71 mmol, 3.00 eq), 2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetic acid (350 mg, 568.58 umol, 1 eq), 1-methylimidazole (233.40 mg, 2.84 mmol, 226.60 uL, 5 eq) and [chloro(dimethylamino)methylene]-dimethyl-ammonium;hexafluorophosphate (319.06 mg, 1.14 mmol, 2 eq) in ACN (6 mL) was stirred at 20° C. for 1 h. Upon completion, the mixture was concentrated under reduced pressure to give a residue. The residue was purified by prep-HPLC (column: Waters Xbridge Prep OBD C18 150*40 mm*10 um; mobile phase: [water (0.05% $NH_3H_2O$+10 mM $NH_4HCO_3$)-ACN]; B %: 40%-65%, 8 min) to get benzyl (2R,4R)-4-methoxy-2-[[2-(8-oxabicyclo[3.2.1]octan-3-ylamino)-2-oxo-1-(3-pyridyl)ethyl]-[4-(pentafluoro-λ$^6$-sulfanyl)phenyl]carbamoyl]pyrrolidine-1-carboxylate isomer 1 (50 mg, 65.54 umol, 11.53% yield, 95% purity) as white solid MS (ESI) m/z 725.2 $[M+H]^+$; and to get benzyl (2R,4R)-4-methoxy-2-[[2-(8-oxabicyclo[3.2.1]octan-3-ylamino)-2-oxo-1-(3-pyridyl)ethyl]-[4-(pentafluoro-λ$^6$-sulfanyl)phenyl]carbamoyl]pyrrolidine-1-carboxylate isomer 2 (60 mg, 78.65 umol, 13.83% yield, 95% purity) as white solid MS (ESI) m/z 725.2 $[M+H]^+$.

Step 2: (2R,4R)-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide A mixture of benzyl (2R,4R)-4-methoxy-2-[[2-(8-oxabicyclo[3.2.1]octan-3-ylamino)-2-oxo-1-(3-pyridyl)ethyl]-[4-(pentafluoro-λ$^6$-sulfanyl)phenyl]carbamoyl]pyrrolidine-1-carboxylate (43 mg, 59.33 umol, 1 eq) in TFA (2.03 g, 17.80 mmol, 1.32 mL, 300 eq) was stirred at 80° C. for 4 h. Upon completion, the mixture was added $NaHCO_3$ (50 mL) and then extracted with EA (30 mL*3). The combined organic layers were washed with brine (50 mL), dried over $Na_2SO_4$, filtered and concentrated under reduced pressure to get the product (2R,4R)-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide (33 mg, crude) as yellow solid. MS (ESI) m/z 591.2 $[M+H]^+$.

A mixture of benzyl (2R,4R)-4-methoxy-2-[[2-(8-oxabicyclo[3.2.1]octan-3-ylamino)-2-oxo-1-(3-pyridyl)ethyl]-[4-(pentafluoro-λ$^6$-sulfanyl)phenyl]carbamoyl]pyrrolidine-1-carboxylate (52 mg, 71.75 umol, 1 eq) and TFA (2.45 g, 21.53 mmol, 1.59 mL, 300 eq) was stirred at 80° C. for 4 h. Upon completion, the mixture was added $NaHCO_3$ (50 mL) and then extracted with EA (30 mL*3). The combined organic layers were washed with brine (50 mL), dried over $Na_2SO_4$, filtered and concentrated under reduced pressure to get the product (2R,4R)-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide (40 mg, crude) as yellow solid MS (ESI) m/z 591.2 $[M+H]^+$.

Step 3: (2R,4R)-1-cyano-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide A solution of (2R,4R)-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide (30 mg, 50.80 umol, 1 eq) and $NaHCO_3$ (12.80 mg, 152.39 umol, 5.93 uL, 3 eq) in EtOH (2 mL) was cooled to 0° C., and then BrCN (5.38 mg, 50.80 umol, 3.74 uL, 1 eq) in EtOH (0.5 mL) was added. Finally, the mixture was stirred for 1 h and warmed to 20° C. gradually. Upon completion, the mixture was added $H_2O$ (30 mL) and then extracted with EA (30 mL*3). The combined organic layers were washed with brine (50 mL), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM $NH_4HCO_3$)-ACN]; B %: 30%-50%, 8 min) to give the product (2R,4R)-1-cyano-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide (18 mg, 29.24 umol, 57.56% yield, 100% purity) was obtained as white solid. MS (ESI) m/z 616.2 $[M+H]^+$.

$^1H$ NMR (400 MHz, METHANOL-$d_4$) δ=8.45-8.27 (m, 2H), 8.19-7.46 (m, 4H), 7.34-6.88 (m, 2H), 6.33 (s, 1H), 4.37-4.18 (m, 3H), 4.06-3.98 (m, 1H), 3.96-3.85 (m, 1H), 3.68-3.58 (m, 1H), 3.53-3.42 (m, 1H), 3.30-3.15 (m, 3H), 2.25-1.95 (m, 5H), 1.94-1.55 (m, 5H)

A solution of (2R,4R)-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide (36 mg, 60.95 umol, 1 eq) and $NaHCO_3$ (15.36 mg, 182.86 umol, 7.11 uL, 3 eq) in EtOH (2 mL) was cooled to 0° C., and then BrCN (6.46 mg, 60.95 umol, 4.48 uL, 1 eq) in EtOH (0.5 mL) was added into the solution. Finally, the mixture was stirred for 1 h and warmed to 20° C. gradually. Upon completion, the mixture was added $H_2O$ (30 mL) and then extracted with EA (30 mL*3). The combined organic layers were washed with brine (50 mL), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM $NH_4HCO_3$)-ACN]; B %: 30%-50%, 8 min) to give the product (2R,4R)-1-cyano-4-methoxy-N-[2-(8-oxabicyclo[3.2.1]octan-3-ylamino)-2-oxo-1-(3-pyridyl)ethyl]-N-[4-(pentafluoro-λ$^6$-sulfanyl)phenyl]pyrrolidine-2-carboxamide (18 mg, 28.88 umol, 47.38% yield, 98.77% purity) as white solid. MS (ESI) m/z 616.2 $[M+H]^+$.

$^1H$ NMR (400 MHz, METHANOL-$d_4$) δ=8.47-8.32 (m, 2H), 8.29-7.54 (m, 4H), 7.47-6.79 (m, 2H), 6.20 (s, 1H), 4.40-4.18 (m, 3H), 4.09-3.87 (m, 2H), 3.71-3.59 (m, 1H), 3.57-3.46 (m, 1H), 3.30-3.15 (m, 3H), 2.25-1.53 (m, 10H)

Example 88: Synthesis of Compound 1199

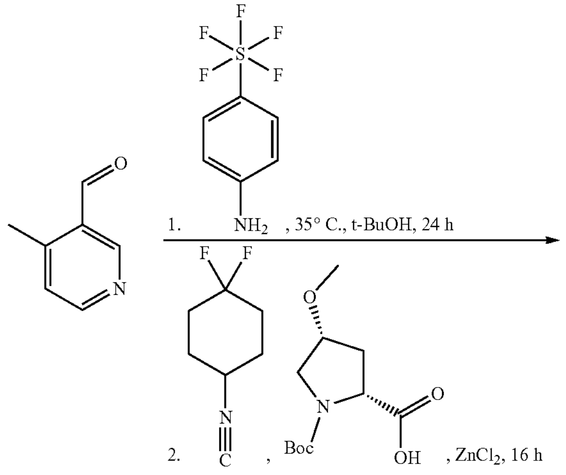

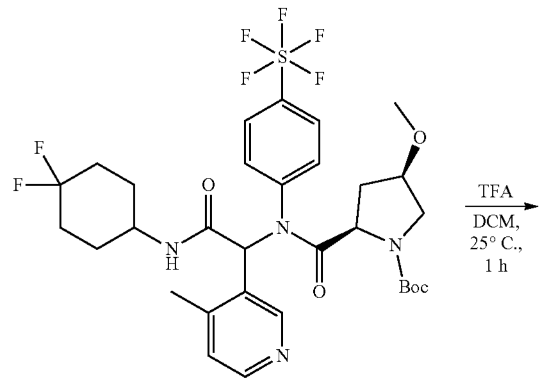

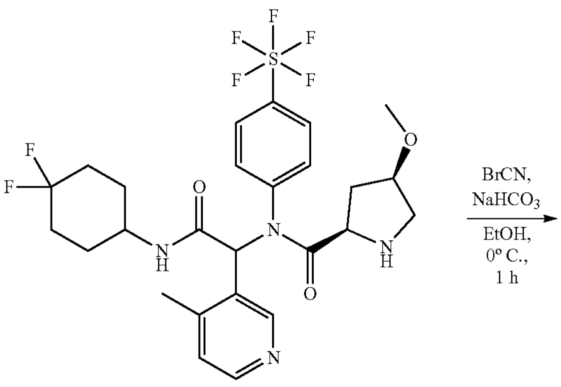

-continued

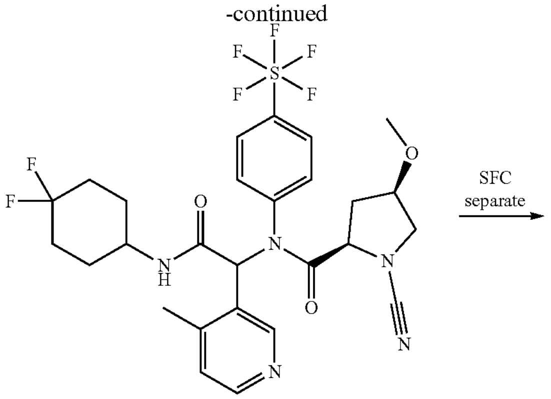

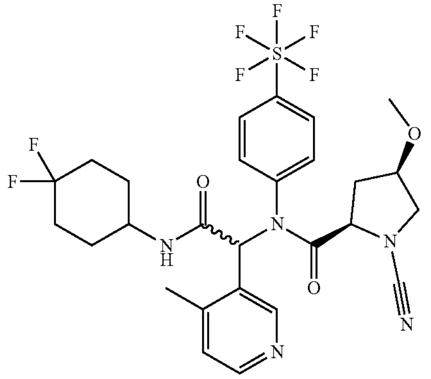

Step 1: tert-butyl(2R,4R)-2-[[2-[(4,4-difluorocyclohexyl)amino]-1-(4-methyl-3-pyridyl)-2-oxo-ethyl]-[4-(pentafluoro-λ6-sulfanyl)phenyl]carbamoyl]-4-methoxy-pyrrolidine-1-carboxylate A solution of 4-(pentafluoro-$\lambda^6$-sulfanyl) aniline (268.08 mg, 1.22 mmol, 1 eq) and 4-methylpyridine-3-carbaldehyde (177.80 mg, 1.47 mmol, 1.2 eq) in t-BuOH (6 mL) was stirred at 35° C. for 24 h, and then (2R,4R)-1-tert-butoxy-carbonyl-4-methoxy-pyrrolidine-2-carboxylic acid (300 mg, 1.22 mmol, 1 eq) was added to the mixture, followed a portion-wise addition of a solution of 1,1-difluoro-4-iso-cyano-cyclohexane (177.54 mg, 1.22 mmol, 1 eq) in t-BuOH (1 mL). To the resulting mixture was added $ZnCl_2$ (1 M, 3.67 mL, 3 eq). The mixture was stirred at 35° C. for 16 h. Upon completion of the reaction, the mixture was concentrated in vacuum and was purified by prep-HPLC (column: Kromasil C18 (250*50 mm*10 urn); mobile phase: [water (10 mM $NH_4HCO_3$)-ACN]; B %: 50%-70%, 10 min) to obtained tert-butyl (2R,4R)-2-[[2-[(4,4-difluoro-cyclohexyl)amino]-1-(4-methyl-3-pyridyl)-2-oxo-ethyl]-[4-(pentafluoro-$\lambda^6$-sulfanyl)phenyl]carbamoyl]-4-methoxy-pyrrolidine-1-carboxylate (200 mg, 280.62 umol, 22.94% yield, 100% purity) as a yellow solid. MS (ESI) m/z 713.3 $[M+H]^+$ Step 2: (2R,4R)—N-[2-[(4,4-difluorocyclohexyl) amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide A solution of tert-butyl (2R,4R)-2-[[2-[(4,4-difluorocyclohexyl)amino]-1-(4-methyl-3-pyridyl)-2-oxo-ethyl]-[4-(pentafluoro-$\lambda^6$-sulfanyl)phenyl]carbamoyl]-4-methoxy-pyrrolidine-1-carboxylate (200 mg, 280.62 umol, 1 eq) in DCM (4 mL) and TFA (2 mL), the mixture was stirred at 25° C. for 1 h. Upon completion of the reaction, the mixture was concentrated in vacuum and was adjust pH~8 with sat. $Na_2CO_3$ (10 mL), extracted with DCM (3 mL*3), and then concentrated in vacuum to obtain (2R,4R)—N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (200 mg, crude) as a yellow gum. MS (ESI) m/z 613.2 $[M+H]^+$ Step 3: (2R,4R)-1-cyano-N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide To a solution of (2R,4R)—N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (200 mg, 326.48 umol, 1 eq) in EtOH (1 mL) was added $NaHCO_3$ (82.28 mg, 979.43 umol, 38.09 uL, 3 eq). The resulting mixture was cooled to 0° C., and then BrCN (69.16 mg, 652.95 umol, 48.03 uL, 2 eq) was added. The resulting mixture was stirred at 0° C. for 1 h. Upon completion of the reaction, the mixture was dried by blowing $N_2$ and quenched by water (6 mL) and extracted with DCM (3 mL*2). The resulting mixture was concentrated in vacuum and purified by prep-HPLC (column: Waters Xbridge BEH C18 100*25 mm*5 um; mobile phase: [water (10 mM $NH_4HCO_3$)-ACN]; B %: 42%-62%, 10 min) to obtained (2R,4R)-1-cyano-N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (56 mg, 84.62 umol, 25.92% yield, 96.35% purity) as a yellow solid. MS (ESI) m/z 638.1 [M+H]

$^1$H NMR (400 MHz, MeOD-$d_4$) δ ppm 8.32-8.13 (m, 2H), 8.12-7.40 (m, 4H), 7.34-7.18 (m, 1H), 7.05-6.59 (m, 1H), 6.56-6.37 (m, 1H), 4.31-4.24 (m, 1H), 3.99-3.85 (m, 2H), 3.63 (dt, J=5.9, 10.1 Hz, 1H), 3.55-3.43 (m, 1H), 3.28 (d, J=4.1 Hz, 3H), 2.51 (d, J=9.1 Hz, 3H), 2.12-1.82 (m, 8H), 1.70-1.37 (m, 2H).

Step 4: (2R,4R)-1-cyano-N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (2R,4R)-1-cyano-N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (52 mg, 82.62 umol, 96.35% purity) was separated by SFC (column: REGIS(R,R)WHELK-O1 (250 mm*25 mm, 10 um); mobile phase: [Neu-ETOH]; B %: 30%-30%, 10 min) to obtain (2R,4R)-1-cyano-N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (Isomer 1: 20 mg, 30.56 umol, 37.48% yield, 97.44% purity) as a white solid. MS (ESI) m/z 638.2 $[M+H]^+$ $^1$H NMR (400 MHz, MeOD-$d_4$) δ ppm 8.31-7.47 (m, 5H), 7.23 (d, J=5.1 Hz, 1H), 6.96 (s, 1H), 6.53 (s, 1H), 4.27 (dd, J=6.5, 8.5 Hz, 1H), 4.00-3.87 (m, 2H), 3.65 (dd, J=6.0, 9.4 Hz, 1H), 3.46 (dd, J=5.3, 9.4 Hz, 1H), 3.29 (s, 3H), 2.50 (s, 3H), 2.14-1.84 (m, 8H), 1.70-1.40 (m, 2H).

(2R,4R)-1-cyano-N-[2-[(4,4-difluorocyclohexyl)amino]-1-(4-methyl-3-pyridyl)-2-oxo-ethyl]-4-methoxy-N-[4-(pentafluoro-$\lambda^6$-sulfanyl)phenyl]pyrrolidine-2-carboxamide (Isomer 2: 20 mg, 28.06 umol, 34.41% yield, 89.46% purity) was obtained as a white solid. MS (ESI) m/z 638.2 $[M+H]^+$ $^1$H NMR (400 MHz, MeOD-$d_4$) δ ppm 8.35-7.42 (m, 5H), 7.31 (d, J=5.1 Hz, 1H), 6.80-6.57 (m, 1H), 6.40 (s, 1H), 4.27 (dd, J=4.9, 8.8 Hz, 1H), 3.98-3.82 (m, 2H), 3.67-3.48 (m, 2H), 3.28 (s, 3H), 2.52 (s, 3H), 2.18-1.76 (m, 8H), 1.67-1.36 (m, 2H).

Example 99: Synthesis of Compound 1202

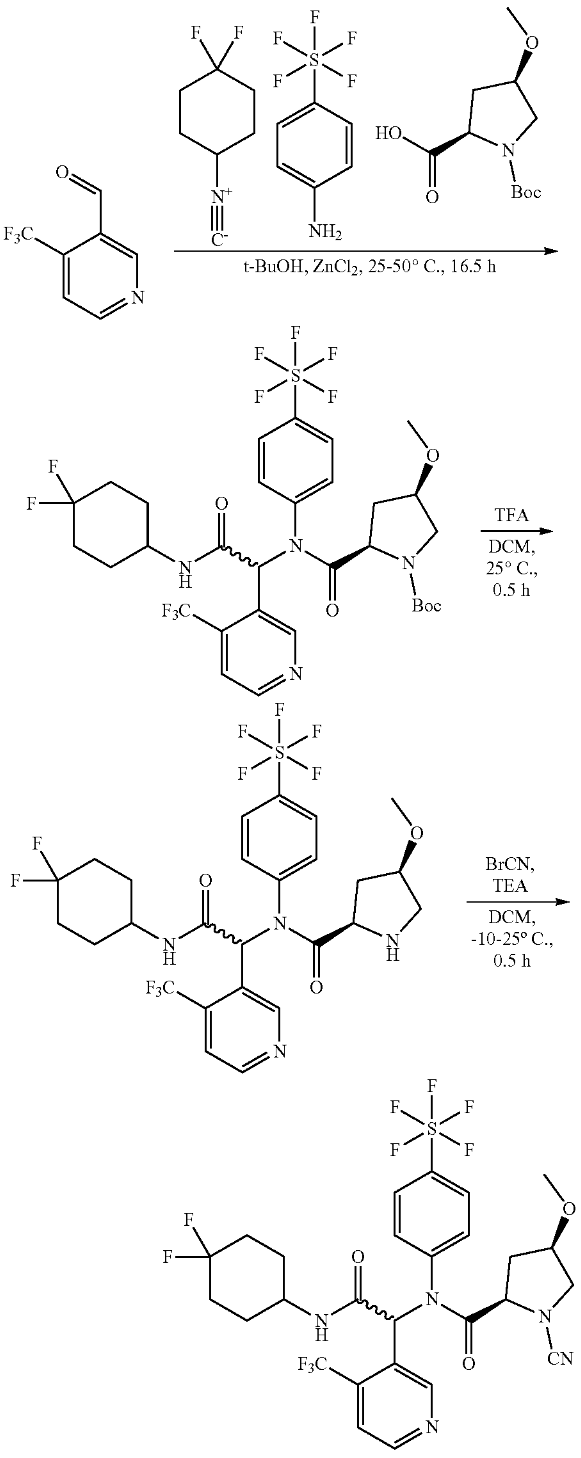

Step 1: tert-butyl(2R,4R)-2-[[2-[(4,4-difluorocyclohexyl)amino]-2-oxo-1-[4-(trifluoromethyl)-3-pyridyl]ethyl]-[4-(pentafluoro-λ6-sulfanyl)phenyl]carbamoyl]-4-methoxy-pyrrolidine-1-carboxylate 4-(pentafluoro-$\lambda^6$-sulfanyl) aniline (375.50 mg, 1.71 mmol, 1 eq) and 4-(trifluoromethyl) pyridine-3-carbaldehyde (300 mg, 1.71 mmol, 1 eq) in t-BuOH (5 mL) was stirred at 25° C. for 0.5 h. The resulting mixture was added with (2R,4R)-1-tert-butoxycarbonyl-4-methoxypyrrolidine-2-carboxylic acid (420.21 mg, 1.71 mmol, 1 eq), 1,1-difluoro-4-isocyano-cyclohexane (248.67 mg, 1.71 mmol, 1 eq) and $ZnCl_2$ (1 M, 5.14 mL, 3 eq), and then stirred at 50° C. for 16 h. Upon completion, the mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 55%-75%, 10 min) affording the product tert-butyl(2R,4R)-2-[[2-[(4,4-difluorocyclohexyl)amino]-2-oxo-1-[4-(trifluoromethyl)-3-pyridyl]ethyl]-[4-(pentafluoro-λ6-sulfanyl)phenyl]carbamoyl]-4-methoxy-pyrrolidine-1-carboxylate (150 mg, 195.65 umol, 11.42% yield) as a yellow solid. MS (ESI) m/z 767.2 $[M+H]^+$ and tert-butyl(2R,4R)-2-[[2-[(4,4-difluorocyclohexyl)amino]-2-oxo-1-[4-(trifluoromethyl)-3-pyridyl]ethyl]-[4-(pentafluoro-$\lambda^6$-sulfanyl)phenyl]carbamoyl]-4-methoxy-pyrrolidine-1-carboxylate (200 mg, 260.86 umol, 15.23% yield) as a yellow solid. MS (ESI) m/z 767.2 $[M+H]^+$ Step 2: (2R,4R)—N-[2-[(4,4-difluorocyclohexyl)amino]-2-oxo-1-[4-(trifluoromethyl)-3-pyridyl]ethyl]-4-methoxy-N-[4-(pentafluoro-λ6-sulfanyl)phenyl]pyrrolidine-2-carboxamide Isomer 1: To a solution of tert-butyl(2R,4R)-2-[[2-[(4,4-difluorocyclohexyl)amino]-2-oxo-1-[4-(trifluoromethyl)-3-pyridyl]ethyl]-[4-(pentafluoro-λ6-sulfanyl)phenyl]carbamoyl]-4-methoxy-pyrrolidine-1-carboxylate (140 mg, 182.60 umol, 1 eq) in DCM (4 mL) was added TFA (3.08 g, 27.01 mmol, 2 mL, 147.93 eq). The mixture was stirred at 25° C. for 0.5 h. Upon completion, the reaction mixture was quenched by addition aq. $NaHCO_3$ (10 mL), and then extracted with DCM (10 mL*3). The combined organic layers were washed with brine (10 mL), dried over $Na_2SO_4$, filtered and concentrated under reduced pressure affording the product (2R,4R)—N-[2-[(4,4-difluorocyclohexyl)amino]-2-oxo-1-[4-(trifluoromethyl)-3-pyridyl]ethyl]-4-methoxy-N-[4-(pentafluoro-$\lambda^6$-sulfanyl)phenyl]pyrrolidine-2-carboxamide (130 mg, crude) as a yellow solid.

Isomer 2: To a solution of tert-butyl(2R,4R)-2-[[2-[(4,4-difluorocyclohexyl)amino]-2-oxo-1-[4-(trifluoromethyl)-3-pyridyl]ethyl]-[4-(pentafluoro-λ6-sulfanyl)phenyl]carbamoyl]-4-methoxy-pyrrolidine-1-carboxylate (190 mg, 247.82 umol, 1 eq) in DCM (4 mL) was added TFA (3.08 g, 27.01 mmol, 2 mL, 109.00 eq). The mixture was stirred at 25° C. for 0.5 h. Upon completion, the reaction mixture was quenched by addition aq. $NaHCO_3$ (10 mL), and then extracted with DCM (10 mL*3). The combined organic layers were washed with brine (10 mL), dried over $Na_2SO_4$, filtered and concentrated under reduced pressure affording the product (2R,4R)—N-[2-[(4,4-difluorocyclohexyl)amino]-2-oxo-1-[4-(trifluoromethyl)-3-pyridyl]ethyl]-4-methoxy-N-[4-(pentafluoro-λ6-sulfanyl)phenyl]pyrrolidine-2-carboxamide (170 mg, crude) as a yellow solid.

Step 3: (2R,4R)-1-cyano-N-[2-[(4,4-difluorocyclohexyl)amino]-2-oxo-1-[4-(trifluoromethyl)-3-pyridyl]ethyl]-4-methoxy-N-[4-(pentafluoro-λ6-sulfanyl)phenyl]pyrrolidine-2-carboxamide Isomer 1: To a solution of (2R,4R)—N-[2-[(4,4-difluorocyclohexyl)amino]-2-oxo-1-[4-(trifluoromethyl)-3-pyridyl]ethyl]-4-methoxy-N-[4-(pentafluoro-6-sulfanyl)phenyl]pyrrolidine-2-carboxamide (120 mg, 180.03 umol, 1 eq) in DCM (3 mL) was added TEA (54.65 mg, 540.08 umol, 75.17 uL, 3 eq), and then the solution was cooled to −10° C. A solution of BrCN (20.98 mg, 198.03 umol, 14.57 uL, 1.1 eq) in DCM (1 mL) was added and stirred at 0° C. The reaction was warmed to 25° C. gradually for 0.5 h. Upon completion, the mixture was quenched by addition $H_2O$ (10 mL) and then extracted with DCM (10 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 40%-65%, 10 min) affording the product (2R,4R)-1-cyano-N-[2-[(4,4-difluorocyclohexyl)amino]-2-oxo-1-[4-(trifluoromethyl)-3-pyridyl]ethyl]-4-methoxy-N-[4-(pentafluoro-λ6-sulfanyl)phenyl]pyrrolidine-2-carboxamide (23 mg, 32.69 umol, 18.16% yield, 98.3% purity) as a yellow solid. MS (ESI) m/z 692.2 $[M+H]^+$ $^1$H NMR (400 MHz, METHANOL-$d_4$) δ=8.63 (d, J=5.2 Hz, 1H), 8.41-7.44 (m, 5H), 6.96 (br s, 1H), 6.69 (s, 1H), 4.24 (dd, J=6.4, 8.6 Hz, 1H), 3.99-3.82 (m, 2H), 3.64 (dd, J=6.0, 9.4 Hz, 1H), 3.47 (dd, J=5.2, 9.4 Hz, 1H), 3.29 (s, 3H), 2.15-1.78 (m, 8H), 1.67-1.55 (m, 1H), 1.54-1.40 (m, 1H).

Isomer 2: To a solution of (2R,4R)—N-[2-[(4,4-difluorocyclohexyl)amino]-2-oxo-1-[4-(trifluoromethyl)-3-pyridyl]ethyl]-4-methoxy-N-[4-(pentafluoro-λ6-sulfanyl)phenyl]pyrrolidine-2-carboxamide (160 mg, 240.03 umol, 1 eq) in DCM (3 mL) was added TEA (72.87 mg, 720.10 umol, 100.23 uL, 3 eq). The resulting solution was cooled to −10° C., and then a solution of BrCN (27.97 mg, 264.04 umol, 19.42 uL, 1.1 eq) in DCM (1 mL) was added, stirred at 0° C. and warmed to 25° C. gradually for 0.5 h. Upon completion, the mixture was quenched by addition $H_2O$ (10 mL) and then extracted with DCM (10 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 40%-65%, 10 min) affording the product (2R,4R)-1-cyano-N-[2-[(4,4-difluorocyclohexyl)amino]-2-oxo-1-[4-(trifluoromethyl)-3-pyridyl]ethyl]-4-methoxy-N-[4-(pentafluoro-λ6-sulfanyl)phenyl]pyrrolidine-2-carboxamide (13 mg, 16.88 umol, 7.03% yield, 89.8% purity) as a yellow solid. MS (ESI) m/z 692.2 $[M+H]^+$ $^1$H NMR (400 MHz, METHANOL-$d_4$) δ=8.68 (d, J=5.2 Hz, 1H), 8.44-7.40 (m, 5H), 7.21-6.54 (m, 1H), 6.48 (s, 1H), 4.28 (dd, J=5.2, 8.8 Hz, 1H), 3.90 (br t, J=4.8 Hz, 1H), 3.79 (br s, 1H), 3.61 (dd, J=5.8, 9.6 Hz, 1H), 3.51-3.40 (m, 1H), 3.25 (s, 3H), 2.15-1.77 (m, 8H), 1.55-1.38 (m, 2H).

Example 100: Synthesis of Compound 1274

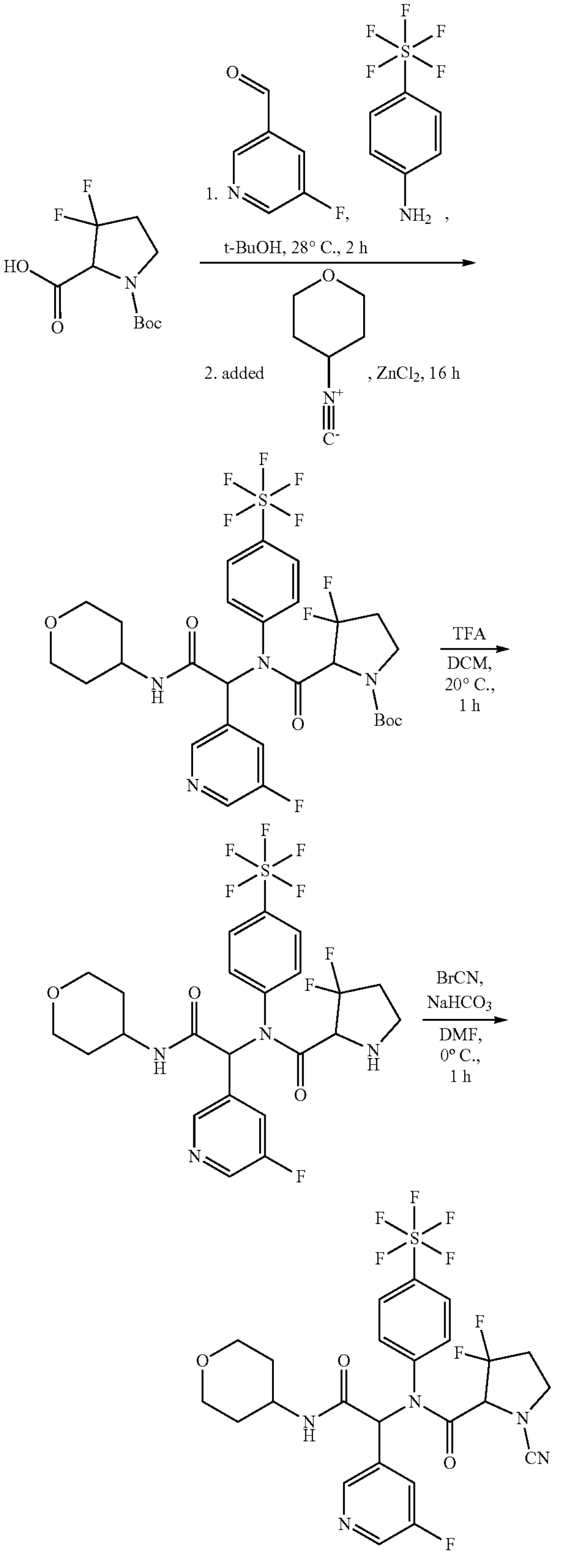

Step 1: tert-butyl3,3-difluoro-2-[[1-(5-fluoro-3-pyridyl)-2-oxo-2-(tetrahydropyran-4-ylamino)ethyl]-[4-(pentafluoro-λ6-sulfanyl)phenyl]carbamoyl]pyrrolidine-1-carboxylate A solution of 4-(pentafluoro-$\lambda^6$-sulfanyl)aniline (261.73 mg, 1.19 mmol, 1 eq) and 5-fluoropyridine-3-carbaldehyde (149.39 mg, 1.19 mmol, 1 eq) in t-BuOH (8 mL) was stirred at 28° C. for 2 h, and then 1-tert-butoxycarbonyl-3,3-difluoro-pyrrolidine-2-carboxylic acid (300 mg, 1.19 mmol, 1 eq) was added to the mixture. A solution of 4-isocyano-tetrahydropyran (132.72 mg, 1.19 mmol, 1 eq) in t-BuOH (1 mL) was added portion-wise, and then $ZnCl_2$ (1 M, 3.58 mL, 3 eq) was added to the mixture and stirred at 28° C. for 16 h. Upon completion, the mixture was concentrated in vacuum and was purified by prep-HPLC (column: Kromasil C18 (250*50 mm*10 um); mobile phase: [water (10 mM $NH_4HCO_3$)-ACN]; B %: 45%-65%, 10 min) to obtained tert-butyl 3,3-difluoro-2-[[1-(5-fluoro-3-pyridyl)-2-oxo-2-(tetrahydropyran-4-ylamino)ethyl]-[4-(pentafluoro-$\lambda^6$-sulfanyl)phenyl]carbamoyl]pyrrolidine-1-carboxylate (200 mg, 261.39 umol, 21.89% yield, 90% purity) as a yellow solid. MS (ESI) m/z 689.2 $[M+H]^+$ Step 2: 3,3-difluoro-N-[1-(5-fluoro-3-pyridyl)-2-oxo-2-(tetrahydropyran-4-ylamino)ethyl]-N-[4-(pentafluoro-$\lambda^6$-sulfanyl)phenyl]pyrrolidine-2-carboxamide A solution of tert-butyl 3,3-difluoro-2-[[1-(5-fluoro-3-pyridyl)-2-oxo-2-(tetrahydropyran-4-ylamino) ethyl]-[4-(pentafluoro-$\lambda^6$-sulfanyl)phenyl]carbamoyl]pyrrolidine-1-carboxylate (190 mg, 275.91 umol, 1 eq) in TFA (0.3 mL) and DCM (1 mL) was stirred at 20° C. for 1 h. Upon completion, the mixture was concentrated in vacuum and the pH was adjusted to ~7 with sat. $NaHCO_3$ (60 mL) and then extracted with DCM (20 mL*3), then was concentration in vacuum to obtained 3,3-difluoro-N-[1-(5-fluoro-3-pyridyl)-2-oxo-2-(tetrahydropyran-4-ylamino)ethyl]-N-[4-(pentafluoro-$\lambda^6$-sulfanyl)phenyl]pyrrolidine-2-carboxamide (160 mg, crude) as a yellow solid. MS (ESI) m/z 589.2 $[M+H]^+$ Step 3: 1-cyano-3,3-difluoro-N-[1-(5-fluoro-3-pyridyl)-2-oxo-2-(tetrahydropyran-4-ylamino)ethyl]-N-[4-(pentafluoro-$\lambda^6$-sulfanyl)phenyl]pyrrolidine-2-carboxamide To a solution of 3,3-difluoro-N-[1-(5-fluoro-3-pyridyl)-2-oxo-2-(tetrahydropyran-4-ylamino)ethyl]-N-[4-(pentafluoro-$\lambda^6$-sulfanyl) phenyl]pyrrolidine-2-carboxamide (150 mg, 254.88 umol, 1 eq) in DMF (3 mL) was added $NaHCO_3$ (64.23 mg, 764.64 umol, 29.74 uL, 3 eq), then the mixture was cooled to 0° C., then was added BrCN (80.99 mg, 764.64 umol, 56.24 uL, 3 eq) at 0° C., the mixture was stirred at 0° C. for 1 h. Upon the reaction complement, the mixture was dried by blowing $N_2$ and was quenched by water (30 mL) and was extracted with DCM (10 mL*2), then was concentration in vacuum and was purified by prep-HPLC (column: Phenomenex Luna C18 75*30 mm*3 um; mobile phase: [water (0.2% FA)-ACN]; B %: 30%-60%, 8 min) to obtained 1-cyano-3,3-difluoro-N-[1-(5-fluoro-3-pyridyl)-2-oxo-2-(tetrahydropyran-4-ylamino) ethyl]-N-[4-(pentafluoro-$\lambda^6$-sulfanyl)phenyl]pyrrolidine-2-carboxamide (53 mg, 86.39 umol, 33.89% yield, 100% purity) as a white solid. MS (ESI) m/z 614.0 $[M+H]^+$ $^1$H NMR (400 MHz, MeOD-$d_4$) δ ppm 8.35 (dd, J=2.7, 9.2 Hz, 1H), 8.28-7.57 (m, 4H), 7.47-7.35 (m, 1H), 6.97 (s, 1H), 6.28-6.12 (m, 1H), 4.53-4.41 (m, 1H), 4.02-3.79 (m, 4H), 3.71-3.59 (m, 1H), 3.54-3.40 (m, 2H), 2.63-2.33 (m, 2H), 1.93-1.85 (m, 1H), 1.78-1.68 (m, 1H), 1.61-1.47 (m, 1H), 1.44-1.30 (m, 1H).

Example 101: Synthesis of Compound 1096

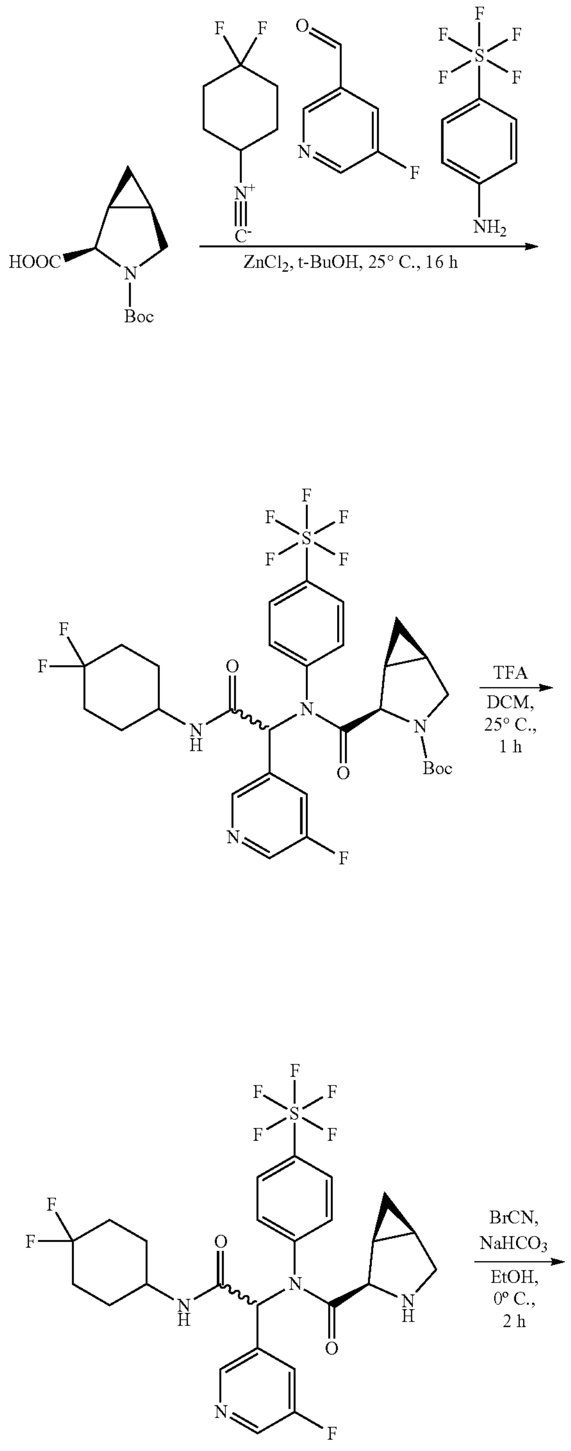

-continued

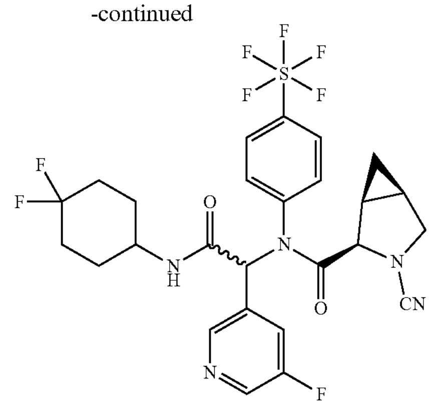

Step 1: tert-butyl (1S,2R,5R)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-3-azabicyclo[3.1.0]hexane-3-carboxylate To a solution of 4-(pentafluoro-$\lambda^6$-sulfanyl)aniline (86.80 mg, 396.03 umol, 1 eq) and 5-fluoropyridine-3-carbaldehyde (59.45 mg, 475.23 umol, 1.2 eq) in t-BuOH (2 mL) at 25° C. for 3 h, then was added (1S,2R,5R)-3-tert-butoxycarbonyl-3-azabicyclo[3.1.0]hexane-2-carboxylic acid (90 mg, 396.03 umol, 1 eq) at 25° C. The reaction mixture was stirred at 25° C. for 1 h. The solution of 1,1-difluoro-4-isocyano-cyclohexane (57.48 mg, 396.03 umol, 1 eq) and $ZnCl_2$ (1 M, 1.19 mL, 3 eq) was added drop wise into the above solution at 25° C. for 12 h. Upon completion, the solution was concentrated to get the crude product. The crude product was purified by HPLC (column: Phenomenex Gemini-NX C18 75*30 mm*3 um; mobile phase: [water (10 mM $NH_4HCO_3$)-ACN]; B %: 50%-70%, 8 min) to give tert-butyl (1S,2R,5R)-2-[[2-[(4,4-difluorocyclohexyl) amino]-1-(5-fluoro-3-pyridyl)-2-oxo-ethyl]-[4-(pentafluoro-$\lambda^6$-sulfanyl)phenyl]carbamoyl]-3-azabicyclo [3.1.0]hexane-3-carboxylate (Isomer 1: 43 mg, 55.39 umol, 13.99% yield, 90% purity) as light yellow solid.

To give tert-butyl (1S,2R,5R)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-3-azabicyclo [3.1.0]hexane-3-carboxylate (Isomer 2: 45 mg, 59.26 umol, 14.96% yield, 92% purity) as light yellow solid. MS (ESI) m/z 699.2 $[M+H]^+$ Isomer 1: Step 2: (1S,2R,5R)—N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]-3-azabicyclo[3.1.0]hexane-2-carboxamide To a mixture of tert-butyl (1S,2R,5R)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-3-azabicyclo[3.1.0]hexane-3-carboxylate (43 mg, 61.55 umol, 1 eq) in DCM (2 mL) was added TFA (1 mL) at 25° C. under $N_2$. Upon completion, the mixture was stirred at 25° C. for 1 h. Upon completion, the reaction mixture was concentrated to get (1S,2R,5R)—N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]-3-azabicyclo[3.1.0]hexane-2-carboxamide (46 mg, crude, TFA) as the light yellow oil and used directly next step. MS (ESI) m/z 599.2 $[M+H]^+$ Isomer 1: Step 3: (1S,2R,5R)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide To a mixture of (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (44 mg, 73.51 umol, 1 eq) and $NaHCO_3$ (43.23 mg, 514.58 umol, 20.01 uL, 7 eq) in EtOH (0.1 mL) was added BrCN (0.1 M, 1.47 mL, 2 eq) at 0° C. under $N_2$. The mixture was stirred at 0° C. for 2 h. Upon completion, the residue was poured into ice-water (2 mL) and stirred for 1 min. The aqueous phase was extracted with ethyl acetate (2 mL*2). The combined organic phase was washed with brine (2 mL), dried with anhydrous $Na_2SO_4$, filtered and concentrated in vacuum. The crude product was purified by prep-HPLC (column: Waters Xbridge Prep OBD C18 150*40 mm*10 um; mobile phase: [water (10 mM $NH_4HCO_3$)-ACN]; B %: 40%-60%, 8 min) to give (1S,2R,5R)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (14.53 mg, 22.80 umol, 31.02% yield, 97.861% purity) as the white solid. MS (ESI) m/z 624.2 $[M+H]^+$ $^1$H NMR (400 MHz, METHANOL-$d_4$) δ ppm 8.23-8.42 (m, 2H), 7.81 (br d, J=9.04 Hz, 3H), 7.44 (dt, J=9.26, 2.21 Hz, 1H), 6.92-7.34 (m, 1H), 6.14 (s, 1H), 4.27-4.39 (m, 1H), 3.83 (br t, J=10.25 Hz, 1H), 3.44-3.62 (m, 2H), 1.74-2.14 (m, 6H), 1.27-1.67 (m, 4H), 0.60-0.79 (m, 2H)

Isomer 2: Step 2: (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide To a mixture of tert-butyl (1S,2R,5R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.1.0]hexane-3-carboxylate (45 mg, 64.41 umol, 1 eq) in DCM (2 mL) was added TFA (1 mL) at 25° C. under $N_2$. The mixture was stirred at 25° C. for 1 h. Upon completion, the reaction mixture was concentrated to get (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (50 mg, crude, TFA) as the light yellow oil and used directly next step. MS (ESI) m/z 599.2 $[M+H]^+$ Isomer 2: Step 3: N-[1-[2-(4-tert-butyl-N-[(2R)-1-cyanopyrrolidine-2-carbonyl]anilino)-2-(3-pyridyl)acetyl]-4-piperidyl]carbamate To a mixture of (1S,2R,5R)—N-[2-[(4,4-difluorocyclohexyl)amino]-1-(5-fluoro-3-pyridyl)-2-oxo-ethyl]-N-[4-(pentafluoro-λ6-sulfanyl)phenyl]-3-azabicyclo[3.1.0]hexane-2-carboxamide (47 mg, 78.52 umol, 1 eq) and $NaHCO_3$ (46.18 mg, 549.66 umol, 21.38 uL, 7 eq) in EtOH (0.1 mL) was added BrCN (0.1 M, 1.57 mL, 2 eq) at 0° C. under $N_2$. The mixture was stirred at 0° C. for 2 h. Upon completion, the residue was poured into ice-water (2 mL) and stirred for 1 min. The aqueous phase was extracted with ethyl acetate (2 mL*2). The combined organic phase was washed with brine (2 mL), dried with anhydrous $Na_2SO_4$, filtered and concentrated in vacuum. The crude product was purified by prep-HPLC (column: Waters Xbridge Prep OBD C18 150*40 mm*10 um; mobile phase: [water (10 mM $NH_4HCO_3$)-ACN]; B %: 40%-60%, 8 min) to give (1S,2R,5R)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (6.06 mg, 9.53 umol, 12.14% yield, 98.085% purity) as the white solid. MS (ESI) m/z 624.2 $[M+H]^+$ $^1$H NMR (400 MHz, METHANOL-$d_4$) δ ppm 8.18-8.35 (m, 2H), 7.58-7.96 (m, 3H), 7.43 (dt, J=9.15, 2.04 Hz, 1H), 7.06-7.30 (m, 1H), 6.22 (s, 1H), 4.35 (d, J=4.63 Hz, 1H), 3.90 (br t, J=10.47 Hz, 1H), 3.49-3.62 (m, 2H), 1.78-2.15 (m, 6H), 1.59-1.71 (m, 1H), 1.41-1.57 (m, 2H), 1.27-1.37 (m, 1H), 0.65-0.75 (m, 2H).

Example 102: Synthesis of Compound 1097

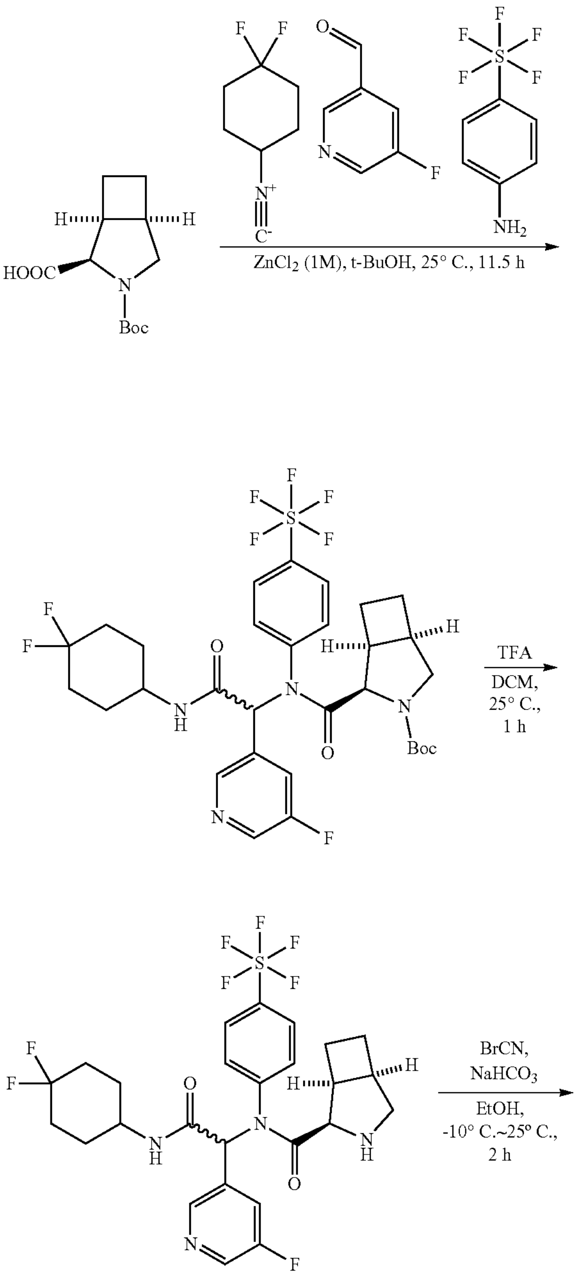

-continued

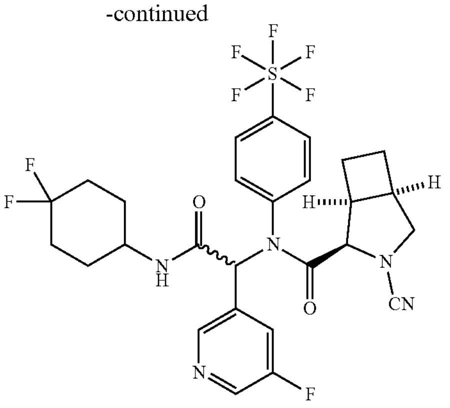

Step1: tert-butyl(1S,2R,5R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.2.0]heptane-3-carboxylate To a solution of 4-(pentafluoro-λ$^6$-sulfanyl)aniline (300 mg, 1.37 mmol, 1 eq), 5-fluoronicotinaldehyde (171.23 mg, 1.37 mmol, 1 eq) in t-BuOH (20 mL) was stirred at 25° C. for 1 h, then the mixture was added (1S,2R,5R)-3-(tert-butoxycarbonyl)-3-azabicyclo[3.2.0]heptane-2-carboxylic acid (330.26 mg, 1.37 mmol, 1 eq) and the mixture was stirred for 0.5 h, at last, the mixture was added 1,1-difluoro-4-isocyanocyclohexane (178.81 mg, 1.23 mmol, 0.9 eq) and $ZnCl_2$ (1 M, 8.21 mL, 6 eq) the mixture was stirred at 25° C. for 10 h. Upon completion, the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: 40%-70%, 8 min) to give a product tert-butyl (1S,2R,5R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.2.0]heptane-3-carboxylate (100 mg, 140.31 umol, 10.25% yield), tert-butyl (1S,2R,5R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.2.0]heptane-3-carboxylate (100 mg, 140.31 umol, 10.25% yield) as white solid. MS (ESI) m/z 713.2 [M+H].

Step2:(1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide Isomer 1: To a solution of tert-butyl (1S,2R,5R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.2.0]heptane-3-carboxylate (95 mg, 133.30 umol, 1 eq) in DCM (2 mL) was added TFA (911.94 mg, 8.00 mmol, 592.17 uL, 60 eq) and the mixture was stirred at 25° C. for 1 h. Upon completion, the mixture was quenched by addition $NaHCO_3$ (20 mL) and then extracted with EtOAc (10 mL*3). The combined organic layers were washed with brine (10 mL), dried over $Na_2SO_4$, filtered and concentrated under reduced pressure to give (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide (90 mg, crude) was yellow oil. MS (ESI) m/z 613.2 $[M+H]^+$ Isomer 2: To a solution of To a solution of tert-butyl (1S,2R,5R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.2.0]heptane-3-carboxylate (100 mg, 140.31 umol, 1 eq) in DCM (2 mL) was added TFA (959.93 mg, 8.42 mmol, 623.33 uL, 60 eq) and the mixture was stirred at 25° C. for 1 h. Upon completion, the mixture was quenched by addition $NaHCO_3$ (20 mL), and then extracted with EtOAc (10 mL*3). The combined organic layers were washed with brine (10 mL), dried over $Na_2SO_4$, filtered and concentrated under reduced pressure to give crude product (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide (95 mg, crude) was yellow oil. MS (ESI) m/z 613.2 $[M+H]^+$ Step3:(1S,2R,5R)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide Isomer 1: To a solution of (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide (90 mg, 146.92 umol, 1 eq) in EtOH (2 mL) was added $NaHCO_3$ (37.03 mg, 440.76 umol, 17.14 uL, 3 eq) and the mixture was cooled at −10° C. and added BrCN (20.23 mg, 191.00 umol, 14.05 uL, 1.3 eq) in EtOH (0.5 mL), and the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue and was purified by prep-HPLC (column: Phenomenex Gemini-NX C18 75*30 mm*3 um; mobile phase: [water (0.05% NH3H2O+10 mM $NH_4HCO_3$)-ACN]; B %: 40%-70%, 8 min) to give (1S,2R,5R)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide (30 mg, 44.60 umol, 30.39% yield, 94.79% purity) was white solid. MS (ESI) m/z 638.3 $[M+H]^+$ $^1H$ NMR (400 MHz, MeOD-$d_4$) δ=8.29-8.28 (m, 1H), 8.21-8.20 (m, 1H), 8.07-7.58 (m, 3H), 7.65-7.40 (m, 1H), 7.14 (s, 1H), 6.25 (s, 1H), 4.19-4.18 (m, 1H), 3.88 (s, 1H), 3.50-3.43 (m, 1H), 3.37-3.35 (m, 1H), 2.86 (s, 1H), 1.54-1.34 (m, 1H), 2.10-1.34 (m, 12H)

Isomer 2: To a solution of (1S,2R,5R)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide (90 mg, 146.92 umol, 1 eq) in EtOH (0.5 mL) was added $NaHCO_3$ (37.03 mg, 440.76 umol, 17.14 uL, 3 eq) and the mixture was cooled at −10° C. and added BrCN (20.23 mg, 191.00 umol, 14.05 uL, 1.3 eq) in EtOH (0.5 mL) and the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue and was purified by prep-HPLC (column: Waters Xbridge Prep OBD C18 150*40 mm*10 um; mobile phase: [water (0.05% NH3H2O+10 mM $NH_4HCO_3$)-ACN]; B %: 40%-70%, 8 min) to give (1S,2R,5R)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.2.0]heptane-2-carboxamide (20 mg, 28.72 umol, 19.54% yield, 91.53% purity) was white solid. MS (ESI) m/z 638.2 $[M+H]^+$ $^1H$ NMR (400 MHz, MeOD-$d_4$) δ=8.36-8.35 (m, 1H), 8.22 (s, 1H), 8.01-6.70 (m, 5H), 6.11 (s, 1H), 4.17-4.16 (m, 1H) 3.87-3.85 (m, 1H), 3.49-3.44 (m, 1H), 3.42-3.35 (m, 1H), 2.85 (s, 1H), 2.47-2.45 (m, 1H), 2.14-1.77 (m, 10H), 1.70-1.58 (m, 1H), 1.51-1.40 (m, 1H)

Example 103: Synthesis of Compound 1280

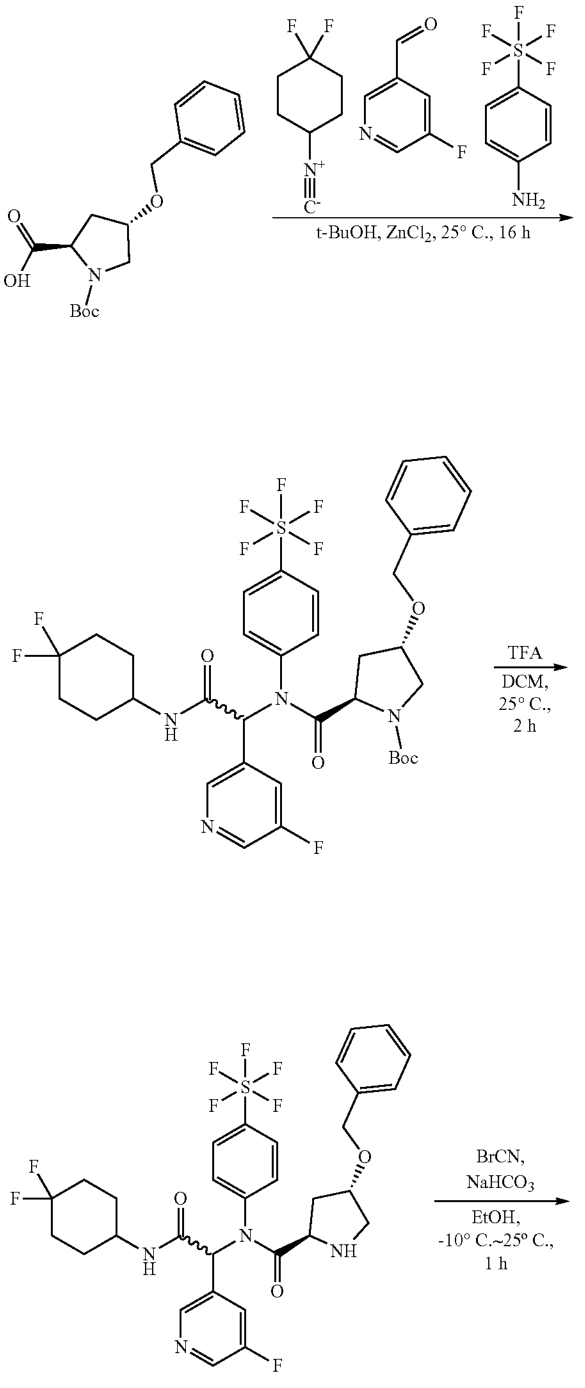

-continued

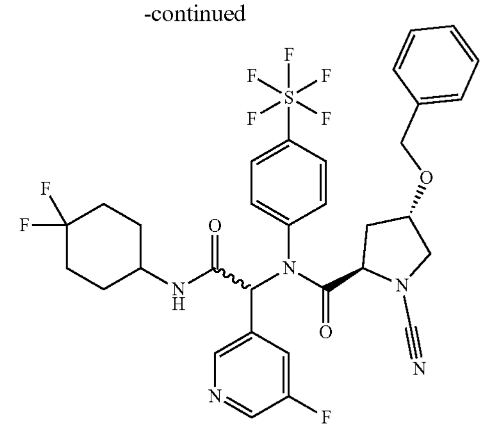

Step 1: tert-butyl (2R,4S)-4-benzyloxy-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate A solution of 4-(pentafluoro-$\lambda^6$-sulfanyl)aniline (204.60 mg, 933.51 umol, 1 eq), 5-fluoropyridine-3-carbaldehyde (116.78 mg, 933.51 umol, 1 eq) in t-BuOH (7 mL) was stirred at 25° C. for 2 h. To the resulting mixture was added (2R,4S)-4-benzyloxy-1-tert-butoxycarbonyl-pyrrolidine-2-carboxylic acid (300 mg, 933.51 umol, 1 eq), followed by an addition of 1,1-difluoro-4-isocyano-cyclohexane (135.50 mg, 933.51 umol, 1 eq) in t-BuOH (1 mL) in three batches. $ZnCl_2$ (1 M, 2.80 mL, 3 eq) was added, and the mixture was stirred at 25° C. for 14 h. Upon completion, the reaction mixture was concentrated in vacuo. The residue was purified by prep-HPLC (column: Waters Xbridge Prep OBD C18 150*40 mm*10 um; mobile phase: [water (10 mM $NH_4HCO_3$)-ACN]; B %: 55%-85%, 8 min) to give the title compound tert-butyl (2R,4S)-4-benzyloxy-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (150 mg, 189.21 umol, 20.27% yield, N/A purity) as a yellow oil. And tert-butyl (2R,4S)-4-benzyloxy-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (130 mg, 163.98 umol, 17.57% yield, N/A purity) as a yellow oil. MS (ESI) m/z 793.3 $[M+1]^+$ Step 2: (2R,4S)-4-benzyloxy-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide Isomer 1: A solution of tert-butyl (2R,4S)-4-benzyloxy-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (150 mg, 189.21 umol, 1 eq) in DCM (2 mL) and TFA (1 mL) was stirred at 25° C. for 2 h. Upon completion, the reaction mixture was quenched by addition of $NaHCO_3$ aq (30 mL) and extracted with DCM (15 mL*3). The combined organic layers were washed with brine (20 mL), dried over $Na_2SO_4$, filtered and concentrated under reduced pressure to give the title compound (2R,4S)-4-benzyloxy-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]pyrrolidine-2-carboxamide (100 mg, crude) as a yellow oil. MS (ESI) m/z 693.2 $[M+H]^+$ Isomer 2: A solution of tert-butyl (2R,4S)-4-benzyloxy-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]pyrrolidine-1-carboxylate (130 mg, 163.98 umol, 1 eq) in DCM (2 mL) and TFA (1 mL) was stirred at 25° C. for 1 h. Upon completion, the reaction mixture was quenched by addition $NaHCO_3$ aq (30 mL), and extracted with DCM (15 mL*3). The combined organic layers were washed with brine (20 mL), dried over $Na_2SO_4$, filtered and concentrated under reduced pressure to give the title compound (2R,4S)-4-benzyloxy-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]pyrrolidine-2-carboxamide (80 mg, crude) as a yellow oil. MS (ESI) m/z 693.2 $[M+H]^+$ Step 3: (2R,4S)-4-benzyloxy-1-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]pyrrolidine-2-carboxamide Isomer 1: To a solution of (2R,4S)-4-benzyloxy-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]pyrrolidine-2-carboxamide (100 mg, 144.37 umol, 1 eq) and $NaHCO_3$ (36.39 mg, 433.11 umol, 16.85 uL, 3 eq) in EtOH (1 mL) was added a solution of BrCN (30.58 mg, 288.74 umol, 21.24 uL, 2 eq) in EtOH (0.5 mL) drop-wise at −10° C. under $N_2$. The reaction mixture was slowly warmed to 25° C. for 1 h. Upon completion, the reaction mixture was quenched by addition $H_2O$ (15 mL) and extracted with EtOAc (5 mL*3). The combined organic layers were washed with brine (10 mL), dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 50%-90%, 8 min) to give the title compound (2R,4S)-4-benzyloxy-1-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]pyrrolidine-2-carboxamide (55 mg, 76.64 umol, 53.08% yield, 100% purity) as a white solid. MS (ESI) m/z 718.2 $[M+H]^+$ $^1$H NMR (400 MHz, MeOD-$d_4$) δ=8.30 (d, J=2.4 Hz, 1H), 8.20 (s, 1H), 8.12-7.58 (m, 3H), 7.41 (d, J=9.2 Hz, 1H), 7.30-7.17 (m, 6H), 6.22 (s, 1H), 4.44-4.33 (m, 2H), 4.24-4.21 (m, 2H), 3.96-3.85 (m, 1H), 3.66-3.65 (m, 1H), 3.56-3.53 (m, 1H), 2.10-1.86 (m, 8H), 1.65-1.62 (m, 1H), 1.51-1.47 (m, 1H).

Isomer 2: To a solution of (2R,4S)-4-benzyloxy-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]pyrrolidine-2-carboxamide (70 mg, 101.06 umol, 1 eq) and $NaHCO_3$ (25.47 mg, 303.18 umol, 11.79 uL, 3 eq) in EtOH (1 mL) was added a solution of BrCN (21.41 mg, 202.12 umol, 14.87 uL, 2 eq) in EtOH (0.5 mL) drop-wise at −10° C. under $N_2$. The reaction mixture was slowly warmed to 25° C. for 1 h. Upon completion, the reaction mixture was quenched by addition $H_2O$ (15 mL) and extracted with EtOAc (5 mL*3). The combined organic layers were washed with brine (10 mL), dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 40%-80%, 8 min) to give the title compound (2R,4S)-4-benzyloxy-1-cyano-N-[2-[(4,4-difluoro-cyclohexyl)amino]-1-(5-fluoro-3-pyridyl)-2-oxo-ethyl]-N-[4-(pentafluoro-λ$^6$-sulfanyl)phenyl]pyrrolidine-2-carboxamide (51 mg, 71.06 umol, 70.32% yield, 100% purity) as a white solid. MS (ESI) m/z 718.2 $[M+H]^+$ $^1$H NMR (400 MHz, MeOD-$d_4$) δ=8.34 (d, J=2.8 Hz, 1H), 8.24 (s, 1H), 8.05-7.52 (m, 3H), 7.43-7.17 (m, 7H), 6.09 (s, 1H), 4.45-4.34 (m, 2H), 4.22-4.20 (m, 2H), 3.95-3.84 (m, 1H), 3.63-3.62 (m, 1H), 3.59-3.45 (m, 1H), 2.12-1.82 (m, 8H), 1.66-1.62 (m, 1H), 1.50-1.47 (m, 1H).

Example 104: Synthesis of Compound 1210

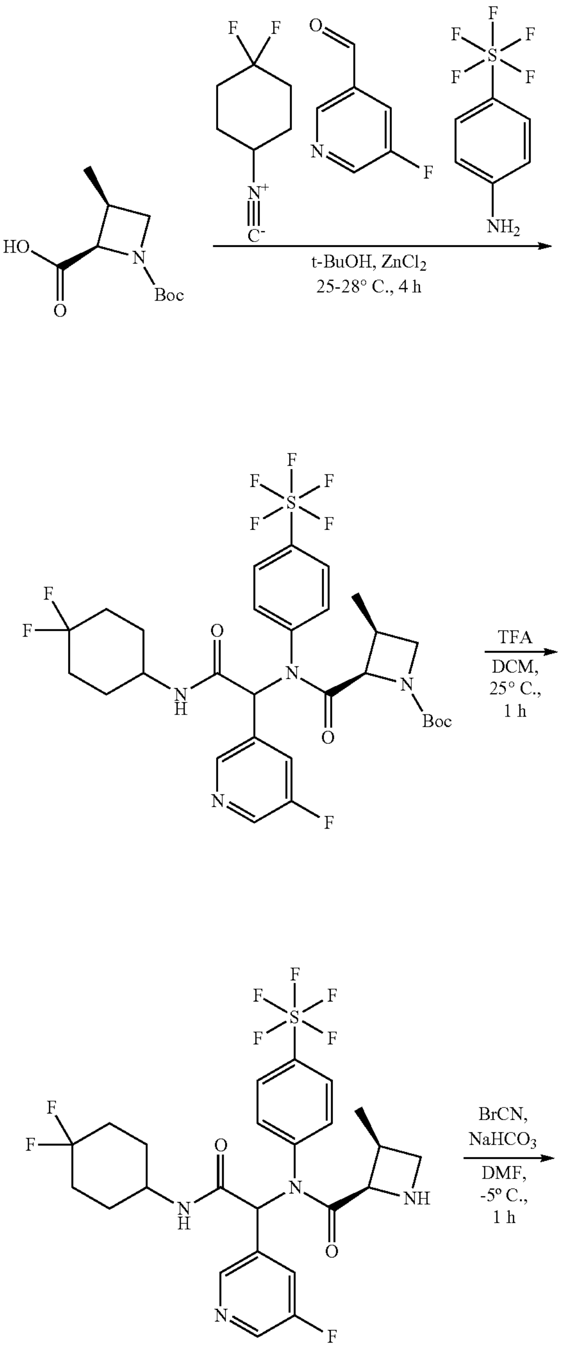

-continued

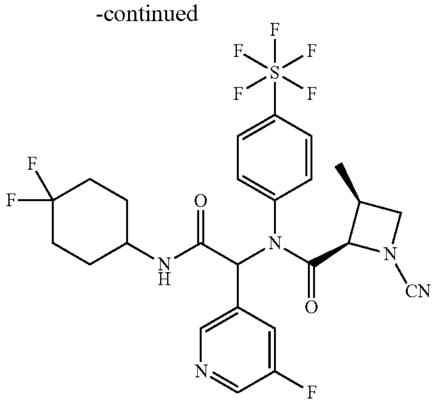

Step 1: tert-butyl (2R,3S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-methyl-azetidine-1-carboxylate A mixture of 5-fluoropyridine-3-carbaldehyde (342.47 mg, 2.74 mmol, 1.5 eq) and 4-(pentafluoro-λ$^6$-sulfanyl) aniline (400 mg, 1.83 mmol, 1 eq) in t-BuOH (6 mL) was stirred at 28° C. for 3 h. Then added (2R,3S)-1-tert-butoxycarbonyl-3-methyl-azetidine-2-carboxylic acid (400 mg, 1.86 mmol, 1.02 eq), 1,1-difluoro-4-isocyano-cyclohexane (264.90 mg, 1.83 mmol, 1 eq) and $ZnCl_2$ (1 M, 10.95 mL, 6 eq) was stirred at 25° C. for 1 h. Upon completion, the reaction mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 40%-75%, 10 min) to get product tert-butyl (2R,3S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-methyl-azetidine-1-carboxylate (490 mg, 713.60 umol, 39.10% yield) as yellow oil. MS (ESI) m/z 687.2 $[M+H]^+$.

Step 2: (2R,3S)—N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide A mixture of tert-butyl (2R,3S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-methyl-azetidine-1-carboxylate (480 mg, 699.04 umol, 1 eq) in DCM (6 mL) and TFA (3 mL) was stirred 25° C. for 1 h. Upon completion, the reaction mixture was diluted with $NaHCO_3$ (10 mL) and extracted with EA (10 mL*3). The combined organic layers were washed with brine, dried over $Na_2SO_4$, filtered and concentrated under reduced pressure to give a residue to get the product (2R,3S)—N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide (410 mg, crude) as yellow oil. MS (ESI) m/z 587.2 $[M+H]^+$.

Step 3: (2R,3S)-1-cyano-N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide A mixture of (2R,3S)—N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide (400 mg, 681.97 umol, 1 eq) in DMF (5 mL) was added $NaHCO_3$ (171.87 mg, 2.05 mmol, 79.57 uL, 3 eq), then the solution was cooled to −5° C. and BrCN (70.79 mg, 668.33 umol, 49.16 uL, 0.98 eq) in DMF (0.5 mL) was added drop-wise, the mixture was stirred at −5° C. for 1 h. Upon completion, the reaction mixture was quenched with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-70%, 8 min) to get the product (2R,3S)-1-cyano-N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide Isomer 1 (61.02 mg, 96.99 umol, 14.22% yield, 97.2% purity) as white solid. MS (ESI) m/z 612.2 $[M+H]^+$.

$^1$H NMR (400 MHz, METHANOL-$d_4$) δ=8.35 (d, J=2.4 Hz, 1H), 8.23 (s, 1H), 7.79 (br d, J=8.3 Hz, 2H), 7.66-7.25 (m, 3H), 6.14 (s, 1H), 4.91 (br d, J=8.2 Hz, 1H), 4.12 (s, 1H), 3.88 (br t, J=10.0 Hz, 1H), 3.59-3.48 (m, 1H), 2.46-2.33 (m, 1H), 2.12-1.92 (m, 4H), 1.89-1.79 (m, 2H), 1.71-1.57 (m, 1H), 1.52-1.39 (m, 1H), 1.26 (d, J=7.0 Hz, 3H).

To get the product (2R,3S)-1-cyano-N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide Isomer 2 (53.72 mg, 86.88 umol, 12.74% yield, 98.9% purity) as white solid. MS (ESI) m/z 612.2 $[M+H]^+$.

$^1$H NMR (400 MHz, METHANOL-$d_4$) δ=8.31 (d, J=2.6 Hz, 1H), 8.22 (s, 1H), 7.77 (br d, J=8.5 Hz, 2H), 7.57 (br s, 3H), 6.28 (s, 1H), 4.92 (d, J=8.2 Hz, 1H), 4.11 (s, 1H), 3.90 (br t, J=10.0 Hz, 1H), 3.54 (dd, J=4.4, 6.4 Hz, 1H), 2.43-2.30 (m, 1H), 2.12-1.81 (m, 6H), 1.74-1.60 (m, 1H), 1.55-1.39 (m, 1H), 1.31 (d, J=7.2 Hz, 3H).

Example 105: Synthesis of Compound 1212

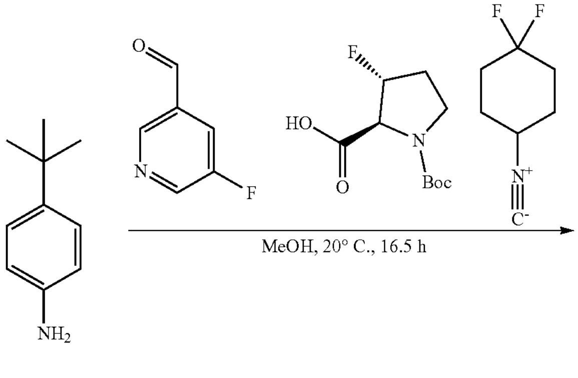

-continued

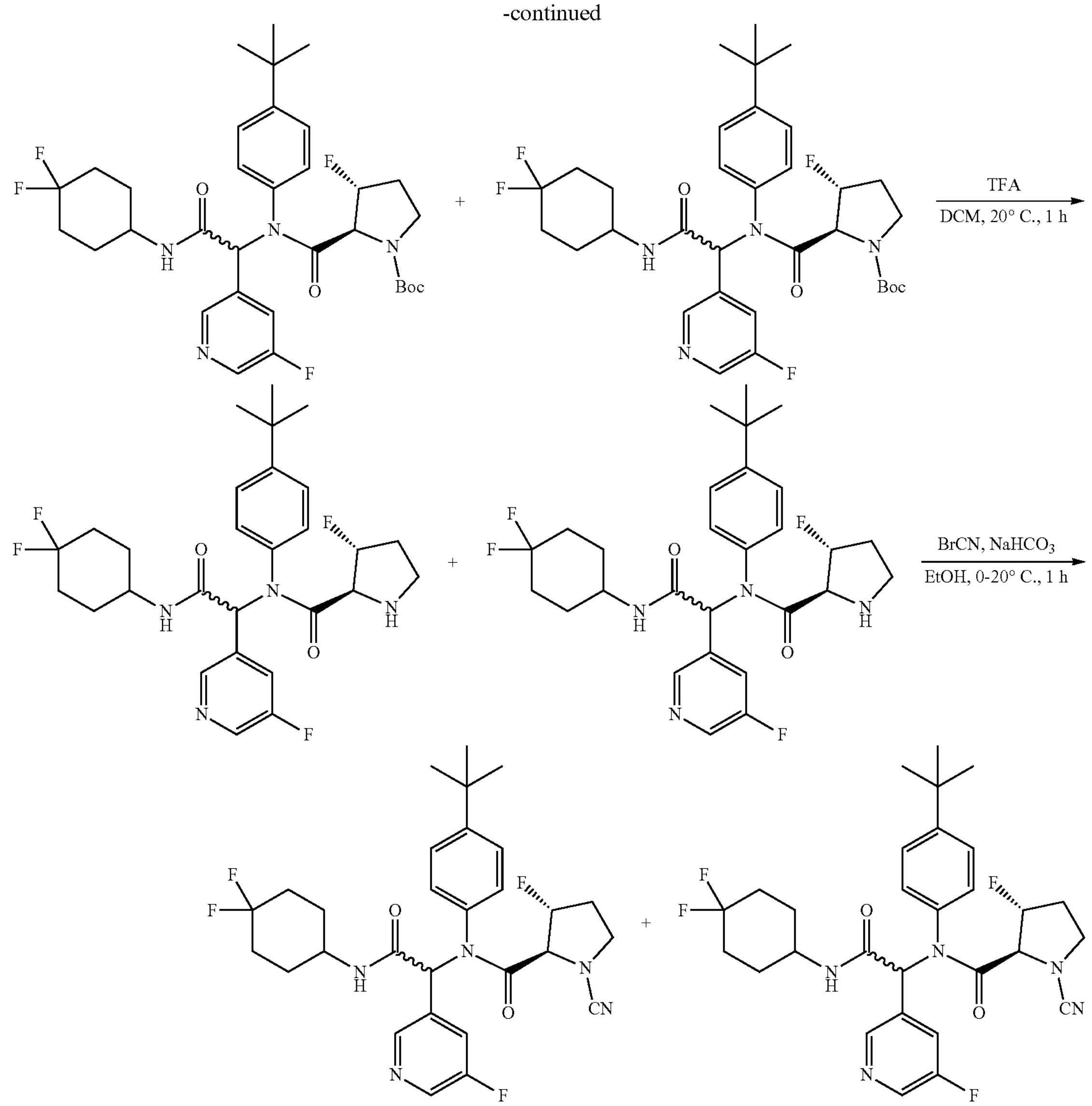

Step 1: tert-butyl (2S,3R)-2-[(4-tert-butylphenyl)-[2-[(4,4-difluorocyclohexyl)amino]-1-(5-fluoro-3-pyridyl)-2-oxo-ethyl]carbamoyl]-3-fluoro-pyrrolidine-1-carboxylate A solution of 4-tert-butylaniline (255.93 mg, 1.72 mmol, 270.83 uL, 1 eq) and 5-fluoropyridine-3-carbaldehyde (321.82 mg, 2.57 mmol, 1.5 eq) in MeOH (4 mL) was stirred at 20° C. for 0.5 h, and then 1,1-difluoro-4-isocyano-cyclohexane (248.93 mg, 1.72 mmol, 1 eq) in MeOH (0.5 mL) and (2S,3R)-1-tert-butoxycarbonyl-3-fluoro-pyrrolidine-2-carboxylic acid (400 mg, 1.72 mmol, 1 eq) were added. Finally, the mixture was stirred at 20° C. for 16 h. Upon completion, the mixture was concentrated under reduced pressure to give a residue. The residue was purified by prep-HPLC (column: Phenomenex Gemini-NX C18 75*30 mm*3 um; mobile phase: [water (0.05% $NH_3H_2O$+10 mM $NH_4HCO_3$)-ACN]; B %: 55%-75%, 8 min) to get tert-butyl (2S,3R)-2-[(4-tert-butylphenyl)-[2-[(4,4-difluorocyclohexyl)amino]-1-(5-fluoro-3-pyridyl)-2-oxo-ethyl]carbamoyl]-3-fluoro-pyrrolidine-1-carboxylate Isomer 1 (300 mg, 449.03 umol, 26.18% yield, 95% purity) as white solid MS (ESI) m/z 635.3 $[M+H]^+$ tert-butyl (2S,3R)-2-[(4-tert-butylphenyl)-[2-[(4,4-difluorocyclohexyl)amino]-1-(5-fluoro-3-pyridyl)-2-oxo-ethyl]carbamoyl]-3-fluoro-pyrrolidine-1-carboxylate Isomer 2 (300 mg, 449.03 umol, 26.18% yield, 95% purity) as white solid MS (ESI) m/z 635.3 $[M+H]^+$.

Step 2: (2S,3R)—N-(4-tert-butylphenyl)-N-[2-[(4,4-difluorocyclohexyl)amino]-1-(5-fluoro-3-pyridyl)-2-oxo-ethyl]-3-fluoro-pyrrolidine-2-carboxamide A mixture of tert-butyl (2S,3R)-2-[(4-tert-butylphenyl)-[2-[(4,4-difluorocyclohexyl)amino]-1-(5-fluoro-3-pyridyl)-2-oxo-ethyl]carbamoyl]-3-fluoro-pyrrolidine-1-carboxylate (300 mg, 472.66 umol, 1 eq) and TFA (1.62 g, 14.18 mmol, 1.05 mL, 30 eq) in DCM (3 mL) was stirred at 20° C. for 1 h. Upon completion, the mixture was added $NaHCO_3$ (50 mL) and then extracted with EA (30 mL*3). The combined organic layers were washed with brine (50 mL), dried over $Na_2SO_4$, filtered and concentrated under reduced pressure to get the product (2S,3R)—N-(4-tert-butylphenyl)-N-[2-[(4, 4-difluorocyclohexyl)amino]-1-(5-fluoro-3-pyridyl)-2-oxo-ethyl]-3-fluoro-pyrrolidine-2-carboxamide (210 mg, crude) as yellow solid. MS (ESI) m/z 535.3 $[M+H]^+$.

A mixture of tert-butyl (2S,3R)-2-[(4-tert-butylphenyl)-[2-[(4,4-difluorocyclohexyl)amino]-1-(5-fluoro-3-pyridyl)-2-oxo-ethyl]carbamoyl]-3-fluoro-pyrrolidine-1-carboxylate (300 mg, 472.66 umol, 1 eq) and TFA (1.62 g, 14.18 mmol, 1.05 mL, 30 eq) in DCM (3 mL) was stirred at 20° C. for 1 h. Upon completion, the mixture was added $NaHCO_3$ (50 mL) and then extracted with EA (30 mL*3). The combined organic layers were washed with brine (50 mL), dried over $Na_2SO_4$, filtered and concentrated under reduced pressure to get the product (2S,3R)—N-(4-tert-butylphenyl)-N-[2-[(4, 4-difluorocyclohexyl)amino]-1-(5-fluoro-3-pyridyl)-2-oxo-ethyl]-3-fluoro-pyrrolidine-2-carboxamide (210 mg, crude) as yellow solid. MS (ESI) m/z 535.3 $[M+H]^+$.

Step 3: (2S,3R)—N-(4-tert-butylphenyl)-1-cyano-N-[2-[(4,4-difluorocyclohexyl)amino]-1-(5-fluoro-3-pyridyl)-2-oxo-ethyl]-3-fluoro-pyrrolidine-2-carboxamide A solution of (2S,3R)—N-(4-tert-butylphenyl)-N-[2-[(4, 4-difluorocyclohexyl)amino]-1-(5-fluoro-3-pyridyl)-2-oxo-ethyl]-3-fluoro-pyrrolidine-2-carboxamide (200 mg, 374.12 umol, 1 eq) and $NaHCO_3$ (94.29 mg, 1.12 mmol, 43.65 uL, 3 eq) in EtOH (3 mL) was cooled to 0° C., and then BrCN (39.63 mg, 374.12 umol, 27.52 uL, 1 eq) in EtOH (0.5 mL) was added. Finally, the mixture was stirred for 1 h and warmed to 20° C. gradually. Upon completion, the mixture was added $H_2O$ (50 mL) and then extracted with EA (30 mL*3). The combined organic layers were washed with brine (50 mL), dried over $Na_2SO_4$, filtered and concentrated under reduced pressure to give a residue. The residue was purified by prep-HPLC (column: Waters Xbridge BEH C18 100*30 mm*10 um; mobile phase: [water (0.04% $NH_3H_2O$+10 mM $NH_4HCO_3$)-ACN]; B %: 35%-65%, 10 min)-ACN]; B %: 30%-50%, 8 min) to give the product (2S,3R)—N-(4-tert-butylphenyl)-1-cyano-N-[2-[(4,4-difluorocyclohexyl)amino]-1-(5-fluoro-3-pyridyl)-2-oxo-ethyl]-3-fluoro-pyrrolidine-2-carboxamide (120 mg, 214.44 umol, 57.32% yield, 100% purity) as white solid. MS (ESI) m/z 560.3 $[M+H]^+$.

1 $^1$H NMR (400 MHz, METHANOL-$d_4$) δ=8.29-8.16 (m, 2H), 7.82-7.15 (m, 4H), 6.76 (s, 1H), 6.13 (s, 1H), 5.43-5.23 (m, 1H), 4.30 (s, 1H), 3.95-3.82 (m, 1H), 3.82-3.72 (m, 1H), 3.67-3.56 (m, 1H), 2.39-2.13 (m, 2H), 2.12-1.77 (m, 6H), 1.70-1.55 (m, 1H), 1.52-1.38 (m, 1H), 1.24 (s, 9H)

A solution of (2S,3R)—N-(4-tert-butylphenyl)-N-[2-[(4, 4-difluorocyclohexyl)amino]-1-(5-fluoro-3-pyridyl)-2-oxo-ethyl]-3-fluoro-pyrrolidine-2-carboxamide (270 mg, 505.06 umol, 1 eq) and $NaHCO_3$ (127.29 mg, 1.52 mmol, 58.93 uL, 3 eq) in EtOH (3 mL) was cooled to 0° C., and then BrCN (53.50 mg, 505.06 umol, 37.15 uL, 1 eq) in EtOH (0.5 mL) was added into the solution. The mixture was stirred for 1 h and warmed to 20° C. gradually. Upon completion, the mixture was added $H_2O$ (50 mL) and then extracted with EA (30 mL*3). The combined organic layers were washed with brine (50 mL), dried over $Na_2SO_4$, filtered and concentrated under reduced pressure to give a residue. The residue was purified by prep-HPLC (column: Waters Xbridge BEH C18 100*30 mm*10 um; mobile. phase: [water (0.04% $NH_3H_2O$+10 mM $NH_4HCO_3$)-ACN]; B %: 35%-65%, 10 min)-ACN]; B %: 30%-50%, 8 min) to get the product (2S,3R)—N-(4-tert-butylphenyl)-1-cyano-N-[2-[(4,4-difluorocyclohexyl)amino]-1-(5-fluoro-3-pyridyl)-2-oxo-ethyl]-3-fluoro-pyrrolidine-2-carboxamide (120 mg, 214.44 umol, 42.46% yield, 100% purity) as white solid. MS (ESI) m/z 560.3 $[M+H]^+$.

$^1$H NMR (400 MHz, METHANOL-$d_4$) δ=8.36-8.17 (m, 2H), 7.87-7.09 (m, 4H), 6.78 (s, 1H), 5.99 (s, 1H), 5.44-5.17 (m, 1H), 4.28 (s, 1H), 3.95-3.69 (m, 2H), 3.67-3.52 (m, 1H), 2.43-2.12 (m, 2H), 2.12-1.73 (m, 6H), 1.70-1.54 (m, 1H), 1.53-1.37 (m, 1H), 1.26 (s, 9H)

Example 106: Synthesis of Compound 1232

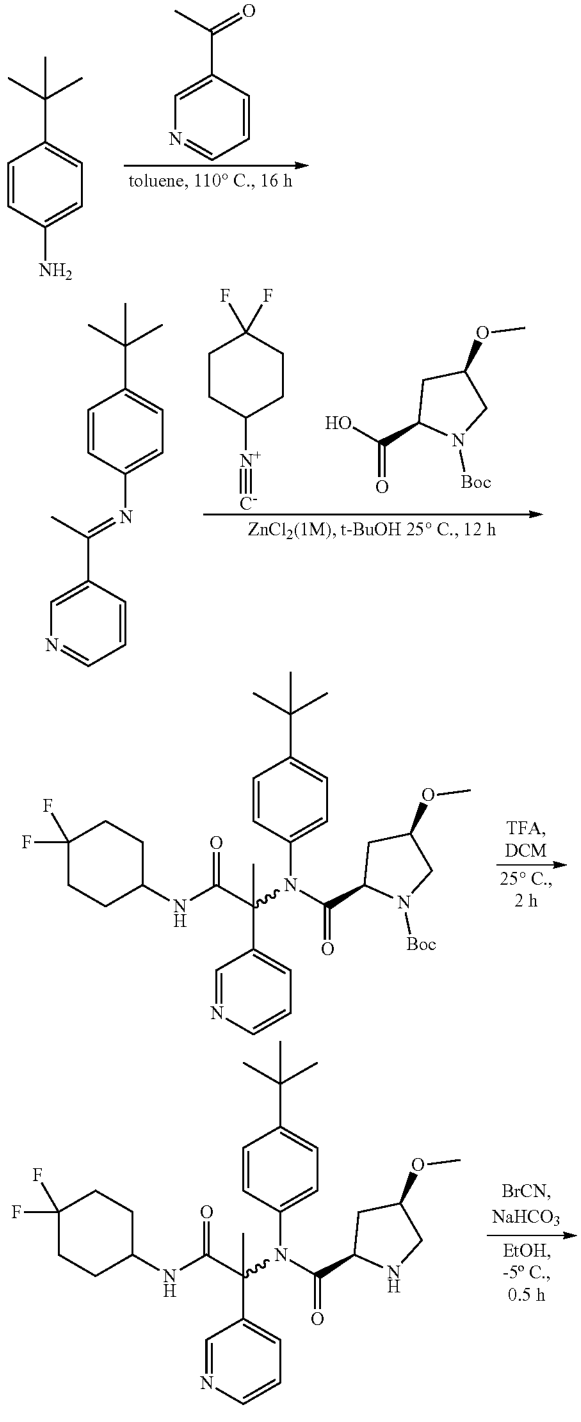

-continued

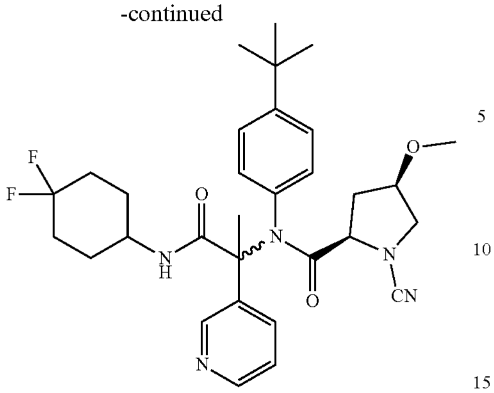

Step 1: (E)-4-(tert-butyl)-N-(1-(pyridin-3-yl)ethylidene)aniline

A mixture of 4-tert-butylaniline (10 g, 67.01 mmol, 10.58 mL, 1 eq) and 1-(3-pyridyl)ethanone (8.12 g, 67.01 mmol, 7.38 mL, 1 eq) in Tol. (100 mL) was stirred at 110° C. for 16 h and remove water by Dean-Stark trap. Upon completion, the reaction mixture was concentrated under reduced pressure to give a residue. The residue was purified by column chromatography ($SiO_2$, Petroleum ether/Ethyl acetate=10/1 to 6/1) to give (E)-N-(4-tert-butylphenyl)-1-(3-pyridyl)ethanimine (3 g, 10.70 mmol, 15.97% yield, 90% purity) as a yellow solid.

Step 2: (2R,4R)-tert-butyl 2-((4-(tert-butyl)phenyl)(1-((4,4-difluorocyclohexyl)amino)-1-oxo-2-(pyridin-3-yl)propan-2-yl)carbamoyl)-4-methoxypyrrolidine-1-carboxylate To a solution of 1,1-difluoro-4-isocyano-cyclohexane (575.18 mg, 3.96 mmol, 9.85 uL, 1 eq), (2R,4R)-1-tert-butoxycarbonyl-4-methoxy-pyrrolidine-2-carboxylic acid (971.94 mg, 3.96 mmol, 1 eq) and (E)-N-(4-tert-butylphenyl)-1-(3-pyridyl)ethanimine (1 g, 3.96 mmol, 1 eq) in t-BuOH (20 mL) was added $ZnCl_2$ (1 M, 23.78 mL, 6 eq), the mixture was stirred at 25° C. for 12 h. Upon completion, the reaction mixture was concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 45%-75%, 10 min) to give tert-butyl (2R,4R)-2-[(4-tert-butylphenyl)-[2-[(4,4-difluorocyclohexyl)amino]-1-methyl-2-oxo-1-(3-pyridyl)ethyl]carbamoyl]-4-methoxy-pyrrolidine-1-carboxylate Isomer 1 (0.15 g, 233.36 umol, 5.89% yield) as a yellow solid. MS (ESI) m/z 677.3 $[M+H]^+$.

To give tert-butyl (2R,4R)-2-[(4-tert-butylphenyl)-[2-[(4,4-difluorocyclohexyl)amino]-1-methyl-2-oxo-1-(3-pyridyl)ethyl]carbamoyl]-4-methoxy-pyrrolidine-1-carboxylate Isomer 2 (0.15 g, 233.36 umol, 5.89% yield) as a yellow solid. MS (ESI) m/z 677.4 $[M+H]^+$.

Step 3: (2R,4R)—N-(4-(tert-butyl)phenyl)-N-(1-((4,4-difluorocyclohexyl)amino)-1-oxo-2-(pyridin-3-yl)propan-2-yl)-4-methoxypyrrolidine-2-carboxamide Isomer 1

To a solution of tert-butyl (2R,4R)-2-[(4-tert-butylphenyl)-[2-[(4,4-difluorocyclohexyl)amino]-1-methyl-2-oxo-1-(3-pyridyl)ethyl]carbamoyl]-4-methoxy-pyrrolidine-1-carboxylate Isomer 1 (0.13 g, 202.25 umol, 1 eq) in DCM (2 mL) was added TFA (770.00 mg, 6.75 mmol, 0.5 mL, 33.39 eq), the mixture was stirred at 25° C. for 0.5 h. Upon completion, the reaction mixture was dried by blowing $N_2$ and then diluted with sat. $NaHCO_3$ (10 mL) and extracted with DCM (5 mL*3). The combined organic layers were dried over $Na_2SO_4$, filtered and concentrated under reduced pressure to give (2R,4R)—N-(4-tert-butylphenyl)-N-[2-[(4,4-difluorocyclohexyl)amino]-1-methyl-2-oxo-1-(3-pyridyl)ethyl]-4-methoxy-pyrrolidine-2-carboxamide Isomer 1 (0.11 g, crude) as a yellow oil.

(2R,4R)—N-(4-(tert-butyl)phenyl)-N-(1-((4,4-difluorocyclohexyl)amino)-1-oxo-2-(pyridin-3-yl)propan-2-yl)-4-methoxypyrrolidine-2-carboxamide Isomer 2: To a solution of tert-butyl (2R,4R)-2-[(4-tert-butylphenyl)-[2-[(4,4-difluorocyclohexyl)amino]-1-methyl-2-oxo-1-(3-pyridyl)ethyl]carbamoyl]-4-methoxy-pyrrolidine-1-carboxylate Isomer 2 (0.15 g, 233.36 umol, 1 eq) in DCM (2 mL) was added TFA (770.00 mg, 6.75 mmol, 0.5 mL, 28.94 eq), the mixture was stirred at 25° C. for 0.5 h. Upon completion, the reaction mixture was dried by blowing $N_2$ and then diluted with sat. $NaHCO_3$ (10 mL) and extracted with DCM (3 mL*3). The combined organic layers were dried over $Na_2SO_4$, filtered and concentrated under reduced pressure to give (2R,4R)—N-(4-tert-butylphenyl)-N-[2-[(4,4-difluorocyclohexyl)amino]-1-methyl-2-oxo-1-(3-pyridyl)ethyl]-4-methoxy-pyrrolidine-2-carboxamide Isomer 2 (0.13 g, crude) as a yellow oil.

Step 4: (2R,4R)—N-(4-(tert-butyl)phenyl)-1-cyano-N-(1-((4,4-difluorocyclohexyl)amino)-1-oxo-2-(pyridin-3-yl)propan-2-yl)-4-methoxypyrrolidine-2-carboxamide Isomer 1

To a solution of (2R,4R)—N-(4-tert-butylphenyl)-N-[2-[(4,4-difluorocyclohexyl)amino]-1-methyl-2-oxo-1-(3-pyridyl)ethyl]-4-methoxy-pyrrolidine-2-carboxamide Isomer 1 (0.11 g, 202.71 umol, 1 eq) in EtOH (1.5 mL) was added $NaHCO_3$ (51.09 mg, 608.12 umol, 23.65 uL, 3 eq), then BrCN (21.47 mg, 202.71 umol, 14.91 uL, 1 eq) in EtOH (0.5 mL) was added drop-wise at −5° C., the solution was stirred at −5° C. for 0.5 h under $N_2$ atmosphere. Upon completion, the reaction mixture was diluted with water (5 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 35%-65%, 8 min) to give (2R,4R)—N-(4-tert-butylphenyl)-1-cyano-N-[2-[(4,4-difluorocyclohexyl)amino]-1-methyl-2-oxo-1-(3-pyridyl)ethyl]-4-methoxy-pyrrolidine-2-carboxamide Isomer 1 (57.63 mg, 101.32 umol, 49.98% yield, 99.8% purity) as a white solid. MS (ESI) m/z 568.3 $[M+H]^+$.

$^1H$ NMR (400 MHz, METHANOL-$d_4$) δ=8.64 (d, J=2.1 Hz, 1H), 8.40 (dd, J=1.4, 4.8 Hz, 11H), 8.03-7.94 (M, 1H), 7.47 (ddd, J=2.3, 8.4, 12.7 Hz, 2H), 7.37 (dd, J=4.7, 8.0 Hz, 1H), 7.31 (dd, J=2.4, 8.3 Hz, 1H), 7.13 (dd, J=2.3, 8.2 Hz, 1H), 4.14 (dd, J=6.1, 8.8 Hz, 1H), 3.99-3.80 (m, 2H), 3.60 (dd, J=6.1, 9.5 Hz, 1H), 3.43 (dd, J=5.3, 9.5 Hz, 1H), 3.27 (s, 3H), 2.16-2.01 (m, 3H), 1.98-1.82 (m, 5H), 1.72 (s, 3H), 1.63 (br d, J=11.2 Hz, 2H), 1.31 (s, 9H).

(2R,4R)—N-(4-(tert-butyl)phenyl)-1-cyano-N-(1-((4,4-difluorocyclohexyl)amino)-1-oxo-2-(pyridin-3-yl)propan-2-yl)-4-methoxypyrrolidine-2-carboxamide Isomer 2

To a solution of (2R,4R)—N-(4-tert-butylphenyl)-N-[2-[(4,4-difluorocyclohexyl)amino]-1-methyl-2-oxo-1-(3-pyridyl)ethyl]-4-methoxy-pyrrolidine-2-carboxamide Isomer 2 (0.13 g, 239.56 umol, 1 eq) in EtOH (1.5 mL) was added $NaHCO_3$ (60.38 mg, 718.68 umol, 27.95 uL, 3 eq), then BrCN (25.37 mg, 239.56 umol, 17.62 uL, 1 eq) in EtOH (0.5 mL) was added drop-wise at −5° C., the solution was stirred at −5° C. for 0.5 h under $N_2$ atmosphere. Upon completion, the reaction mixture was diluted with water (5 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 35%-65%, 8 min) to give (2R, 4R)—N-(4-tert-butylphenyl)-1-cyano-N-[2-[(4,4-difluorocyclohexyl)amino]-1-methyl-2-oxo-1-(3-pyridyl)ethyl]-4-methoxy-pyrrolidine-2-carboxamide Isomer 2 (38.87 mg, 68.47 umol, 28.58% yield, 100% purity) as a white solid. MS (ESI) m/z 568.3 $[M+H]^+$.

$^1H$ NMR (400 MHz, METHANOL-$d_4$) δ=8.57 (d, J=1.7 Hz, 1H), 8.38 (br d, J=4.3 Hz, 1H), 7.88 (td, J=1.8, 8.2 Hz, 1H), 7.49 (dd, J=2.3, 8.3 Hz, 1H), 7.39 (dd, J=2.3, 8.4 Hz, 1H), 7.37-7.29 (m, 2H), 7.11 (dd, J=2.3, 8.3 Hz, 1H), 4.17 (dd, J=5.7, 8.7 Hz, 1H), 3.95 (br s, 1H), 3.87 (t, J=5.6 Hz, 1H), 3.60 (dd, J=5.9, 9.5 Hz, 1H), 3.44 (dd, J=4.9, 9.5 Hz, 1H), 3.27 (s, 3H), 2.14-2.01 (m, 4H), 1.99-1.83 (m, 4H), 1.76 (s, 3H), 1.74-1.57 (m, 2H), 1.29 (s, 9H).

Example 107: Synthesis of Compound 1122

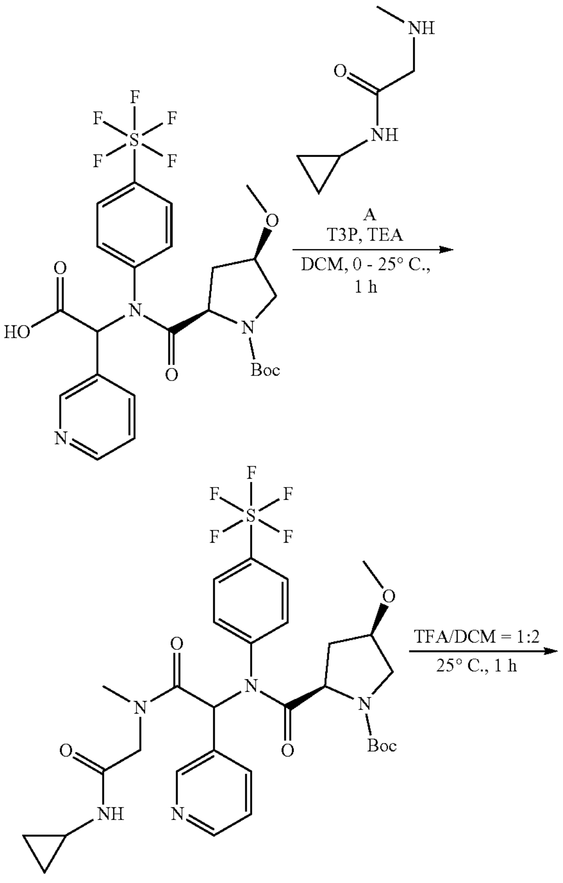

-continued

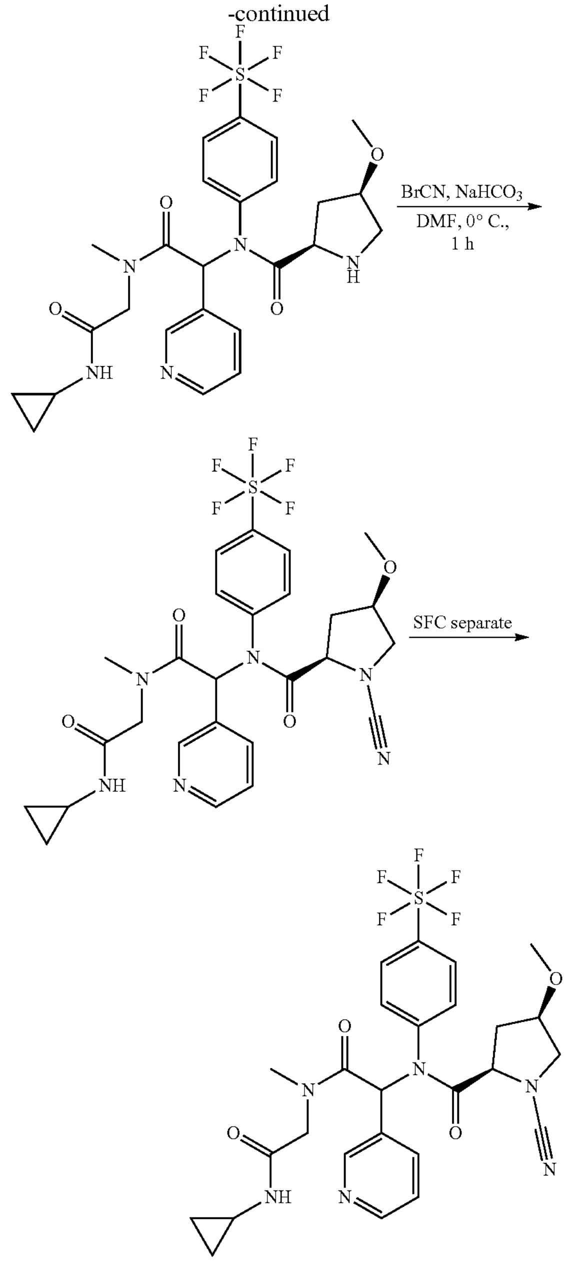

Step 1: tert-butyl(2R,4R)-2-[[2-[[2-(cyclopropylamino)-2-oxo-ethyl]-methyl-amino]-2-oxo-1-(3-pyridyl)ethyl]-[4-(pentafluoro-$\lambda^6$-sulfanyl)phenyl]carbamoyl]-4-methoxy-pyrrolidine-1-carboxylate To a solution of 2-[N-[(2R,4R)-1-tert-butoxycarbonyl-4-methoxy-pyrrolidine-2-carbonyl]-4-(pentafluoro-$\lambda^6$-sulfanyl)anilino]-2-(3-pyridyl) acetic acid (200 mg, 343.91 umol, 1 eq) and N-cyclopropyl-2-(methylamino) acetamide (132.24 mg, 1.03 mmol, 3 eq) in DCM (3 mL) was added TEA (104.40 mg, 1.03 mmol, 143.60 uL, 3 eq). The resulting mixture was then cooled to 0° C., added with T3P (328.27 mg, 515.86 umol, 306.80 uL, 50% purity, 1.5 eq) at 0° C., and stirred at 25° C. for 1 h. Upon completion, the mixture was quenched by water (40 mL) and was extracted with DCM (15 mL*3), then was concentrated in vacuum to obtained tert-butyl (2R,4R)-2-[[2-[[2-(cyclopropylamino)-

2-oxo-ethyl]-methyl-amino]-2-oxo-1-(3-pyridyl) ethyl]-[4-(pentafluoro-λ$^6$-sulfanyl)phenyl]carbamoyl]-4-methoxy-pyrrolidine-1-carboxylate (200 mg, crude) as a yellow gum. MS (ESI) m/z 692.3 $[M+H]^+$ Step 2: (2R,4R)—N-[2-[[2-(cyclopropylamino)-2-oxo-ethyl]-methyl-amino]-2-oxo-1-(3-pyridyl)ethyl]-4-methoxy-N-[4-(pentafluoro-λ$^6$-sulfanyl)phenyl]pyrrolidine-2-carboxamide A solution of tert-butyl (2R,4R)-2-[[2-[[2-(cyclopropylamino)-2-oxo-ethyl]-methyl-amino]-2-oxo-1-(3-pyridyl) ethyl]-[4-(pentafluoro-λ$^6$-sulfanyl)phenyl]carbamoyl]-4-methoxy-pyrrolidine-1-carboxylate (200 mg, 289.14 umol, 1 eq) in TFA (2 mL) and DCM (4 mL) was stirred at 25° C. for 1 h. Upon completion, the mixture was concentrated in vacuum and the pH was adjusted to ~8 with sat. $NaHCO_3$ (30 mL) and then was extracted with DCM (10 mL*3). The resulting mixture was concentrated in vacuum to obtain (2R,4R)—N-[2-[[2-(cyclopropylamino)-2-oxo-ethyl]-methyl-amino]-2-oxo-1-(3-pyridyl) ethyl]-4-methoxy-N-[4-(pentafluoro-λ$^6$-sulfanyl)phenyl]pyrrolidine-2-carboxamide (200 mg, crude) as a yellow gum. MS (ESI) m/z 592.2 $[M+H]^+$ Step 3: (2R,4R)-1-cyano-N-[2-[[2-(cyclopropylamino)-2-oxo-ethyl]-methyl-amino]-2-oxo-1-(3-pyridyl)ethyl]-4-methoxy-N-[4-(pentafluoro-λ$^6$-sulfanyl)phenyl]pyrrolidine-2-carboxamide To a solution of (2R,4R)—N-[2-[[2-(cyclopropylamino)-2-oxo-ethyl]-methyl-amino]-2-oxo-1-(3-pyridyl)ethyl]-4-methoxy-N-[4-(pentafluoro-λ$^6$-sulfanyl)phenyl]pyrrolidine-2-carboxamide (150 mg, 253.55 umol, 1 eq) in DMF (3 mL) was added $NaHCO_3$ (63.90 mg, 760.66 umol, 29.58 uL, 3 eq), and then the mixture was cooled to 0° C. BrCN (53.71 mg, 507.11 umol, 37.30 uL, 2 eq) was added at 0° C., and the mixture was stirred at 0° C. for 1 h. Upon the completion, the mixture was dried by blowing $N_2$ and was quenched by water (30 mL), extracted with DCM (15 mL*2), and then concentrated in vacuum. The crude product was purified by prep-HPLC (column: Waters Xbridge BEH C18 100*25 mm*5 um; mobile phase: [water (10 mM $NH_4HCO_3$)-ACN]; B %: 25%-50%, 10 min) to afford (2R,4R)-1-cyano-N-[2-[[2-(cyclopropylamino)-2-oxo-ethyl]-methyl-amino]-2-oxo-1-(3-pyridyl)ethyl]-4-methoxy-N-[4-(pentafluoro-λ$^6$-sulfanyl) phenyl]pyrrolidine-2-carboxamide (70 mg, 113.53 umol, 44.77% yield) as a yellow solid. MS (ESI) m/z 617.2 $[M+H]^+$ Step 4: (2R,4R)-1-cyano-N-[2-[[2-(cyclopropylamino)-2-oxo-ethyl]-methyl-amino]-2-oxo-1-(3-pyridyl)ethyl]-4-methoxy-N-[4-(pentafluoro-λ$^6$-sulfanyl)phenyl]pyrrolidine-2-carboxamide The (2R,4R)-1-cyano-N-[2-[[2-(cyclopropylamino)-2-oxo-ethyl]-methyl-amino]-2-oxo-1-(3-pyridyl) ethyl]-4-methoxy-N-[4-(pentafluoro-λ$^6$-sulfanyl)phenyl]pyrrolidine-2-carboxamide (70 mg, 113.53 umol) was separated by SFC (column: DAICEL CHIRALPAK IC (250 mm*30 mm, 10 um); mobile phase: [0.1% $NH_3H_2O$ ETOH]; B %: 40%-40%, 9 min) to obtained (2R,4R)-1-cyano-N-[2-[[2-(cyclopropylamino)-2-oxo-ethyl]-methyl-amino]-2-oxo-1-(3-pyridyl)ethyl]-4-methoxy-N-[4-(pentafluoro-26-sulfanyl) phenyl]pyrrolidine-2-carboxamide (Isomer 1: 35 mg, 98% purity) as a yellow solid. MS (ESI) m/z 617.2 $[M+H]^+$ $^1H$ NMR (400 MHz, MeOD-$d_4$) δ ppm 8.51-8.29 (m, 2H), 8.20-7.51 (m, 4H), 7.46-7.06 (m, 2H), 6.75-6.56 (m, 1H), 4.33-3.84 (m, 4H), 3.66 (dd, J=6.0, 9.5 Hz, 1H), 3.51-3.41 (m, 1H), 3.30-3.23 (m, 3H), 3.14-2.98 (m, 3H), 2.76-2.45 (m, 1H), 2.14-1.92 (m, 2H), 0.86-0.38 (m, 4H).

(2R,4R)-1-cyano-N-[2-[[2-(cyclopropylamino)-2-oxo-ethyl]-methyl-amino]-2-oxo-1-(3-pyridyl)ethyl]-4-methoxy-N-[4-(pentafluoro-λ$^6$-sulfanyl)phenyl]pyrrolidine-2-carboxamide (Isomer 2: 30 mg, 96% purity) as a yellow solid. MS (ESI) m/z 617.2 $[M+H]^+$ $^1H$ NMR (400 MHz, MeOD-$d_4$) S ppm 8.53-8.33 (m, 2H), 8.11-7.33 (m, 4H), 7.32-6.66 (m, 2H), 6.60-6.42 (m, 1H), 4.30-3.87 (m, 4H), 3.64 (dd, J=6.0, 9.7 Hz, 1H), 3.54-3.45 (m, 1H), 3.31-3.24 (m, 3H), 3.05-2.90 (m, 3H), 2.74-2.51 (m, 1H), 2.25-1.87 (m, 2H), 0.79-0.43 (m, 4H).

Example 108: Synthesis of Compound 1165

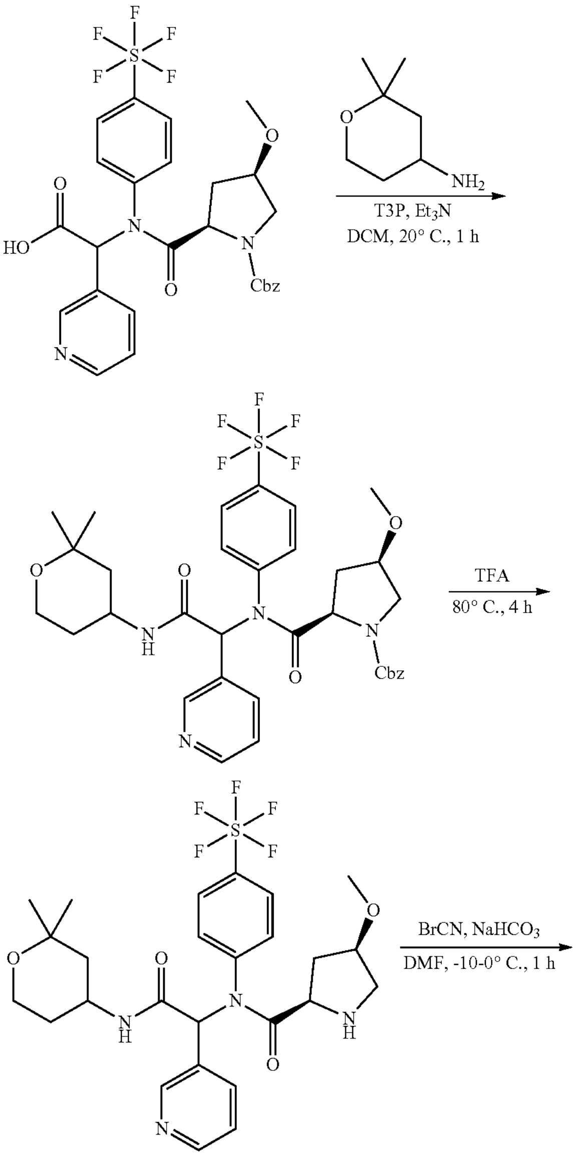

-continued

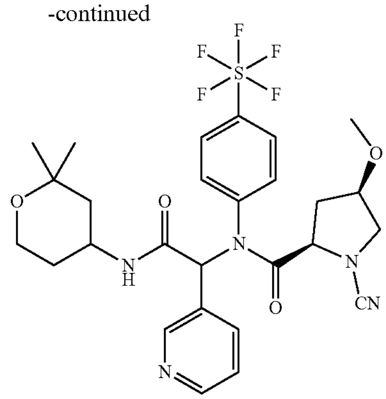

Step 1: benzyl (2R,4R)-2-[[2-[(2,2-dimethyltetrahydropyran-4-yl)amino]-2-oxo-1-(3-pyridyl)ethyl]-[4-(pentafluoro-$\lambda^6$-sulfanyl)phenyl]carbamoyl]-4-methoxy-pyrrolidine-1-carboxylate A solution of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (400 mg, 649.81 umol, 1 eq) and 2,2-dimethyltetrahydropyran-4-amine (125.93 mg, 974.71 umol, 1.5 eq) in DCM (6 mL) was added drop-wise $Et_3N$ (394.52 mg, 3.90 mmol, 542.67 uL, 6 eq) and T3P (1.24 g, 1.95 mmol, 1.16 mL, 50% purity, 3 eq), and the mixture was stirred at 20° C. for 1 h. The reaction mixture was quenched by addition $H_2O$ 40 mL at 0° C., and then extracted with DCM (20 mL*3). The combined organic layers were washed with brine 30 mL, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-70%, 8 min) to afford benzyl (2R,4R)-2-[[2-[(2,2-dimethyltetrahydropyran-4-yl)amino]-2-oxo-1-(3-pyridyl)ethyl]-[4-(pentafluoro-λ6-sulfanyl)phenyl]carbamoyl]-4-methoxy-pyrrolidine-1-carboxylate Isomer 1 (140 mg, 188.21 umol, 28.96% yield, 97.7% purity) as a yellow solid, MS (ESI) m/z 727.3 $[M+H]^+$; and benzyl (2R,4R)-2-[[2-[(2,2-dimethyltetrahydropyran-4-yl)amino]-2-oxo-1-(3-pyridyl)ethyl]-[4-(pentafluoro-$\lambda^6$-sulfanyl)phenyl]carbamoyl]-4-methoxy-pyrrolidine-1-carboxylate Isomer 2 (110 mg, 147.27 umol, 22.66% yield, 97.3% purity) was obtained as a yellow solid. MS (ESI) m/z 727.3 $[M+H]^+$ Step 2: (2R,4R)—N-[2-[(2,2-dimethyltetrahydropyran-4-yl)amino]-2-oxo-1-(3-pyridyl)ethyl]-4-methoxy-N-[4-(pentafluoro-$\lambda^6$-sulfanyl)phenyl]pyrrolidine-2-carboxamide A solution of benzyl (2R,4R)-2-[[2-[(2,2-dimethyltetrahydropyran-4-yl)amino]-2-oxo-1-(3-pyridyl)ethyl]-[4-(pentafluoro-$\lambda^6$-sulfanyl)phenyl]carbamoyl]-4-methoxy-pyrrolidine-1-carboxylate Isomer 1 (100 mg, 137.60 umol, 1 eq) in TFA (7.70 g, 67.53 mmol, 5.00 mL, 490.78 eq) was stirred at 80° C. for 4 h. The reaction mixture was diluted with DCM 10 mL and the mixture was quenched by addition aq. $NaHCO_3$ 50 mL at 0° C., and extracted with DCM (20 mL*3). The combined organic layers were washed with brine 30 mL, dried over $Na_2SO_4$, filtered and concentrated under reduced pressure to afford the product (2R,4R)—N-[2-[(2,2-dimethyltetrahydropyran-4-yl)amino]-2-oxo-1-(3-pyridyl)ethyl]-4-methoxy-N-[4-(pentafluoro-λ6-sulfanyl)phenyl]pyrrolidine-2-carboxamide Isomer 1 (80 mg, crude) as a yellow solid. MS (ESI) m/z 593.2 $[M+H]^+$ A solution of benzyl (2R,4R)-2-[[2-[(2,2-dimethyltetrahydropyran-4-yl)amino]-2-oxo-1-(3-pyridyl)ethyl]-[4-(pentafluoro-$\lambda^6$-sulfanyl)phenyl]carbamoyl]-4-methoxy-pyrrolidine-1-carboxylate Isomer 2 (100 mg, 137.60 umol, 1 eq) in TFA (7.70 g, 67.53 mmol, 5 mL, 490.78 eq) was stirred at 80° C. for 4 h. The reaction mixture was diluted with DCM 10 mL and the mixture was quenched by addition aq. $NaHCO_3$ 50 mL at 0° C. and extracted with DCM (20 mL*3). The combined organic layers were washed with brine 30 mL, dried over $Na_2SO_4$, filtered and concentrated under reduced pressure to get the product (2R,4R)—N-[2-[(2,2-dimethyltetrahydropyran-4-yl)amino]-2-oxo-1-(3-pyridyl)ethyl]-4-methoxy-N-[4-(pentafluoro-λ6-sulfanyl)phenyl]pyrrolidine-2-carboxamide Isomer 2 (80 mg, crude) was obtained as a yellow solid. MS (ESI) m/z 593.2 $[M+H]^+$ Step 3: (2R,4R)-1-cyano-N-[2-[(2,2-dimethyltetrahydropyran-4-yl)amino]-2-oxo-1-(3-pyridyl)ethyl]-4-methoxy-N-[4-(pentafluoro-$\lambda^6$-sulfanyl)phenyl]pyrrolidine-2-carboxamide To a solution of (2R,4R)—N-[2-[(2,2-dimethyltetrahydropyran-4-yl)amino]-2-oxo-1-(3-pyridyl)ethyl]-4-methoxy-N-[4-(pentafluoro-λ6-sulfanyl)phenyl]pyrrolidine-2-carboxamide Isomer 1 (80 mg, 134.99 umol, 1 eq) in DMF (1 mL) was added $NaHCO_3$ (34.02 mg, 404.98 umol, 15.75 uL, 3 eq) and BrCN (21.45 mg, 202.49 umol, 14.89 uL, 1.5 eq) in DMF (0.2 mL) at −10° C., and the mixture was stirred at 0° C. for 1 h. The reaction mixture was quenched by addition $H_2O$ 20 mL at 0° C., and then extracted with EA (15 mL*3). The combined organic layers were washed with brine 20 mL, dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 20%-60%, 8 min) to afford (2R,4R)-1-cyano-N-[2-[(2,2-dimethyltetrahydropyran-4-yl)amino]-2-oxo-1-(3-pyridyl)ethyl]-4-methoxy-N-[4-(pentafluoro-λ6-sulfanyl)phenyl]pyrrolidine-2-carboxamide (14.59 mg, 23.62 umol, 17.50% yield, 100% purity) as a white solid. MS (ESI) m/z 618.2 $[M+H]^+$ $^1H$ NMR (METHANOL-$d_4$, 400 MHz): δ ppm 8.34 (d, J=3.7 Hz, 2H), 7.55-8.27 (m, 4H), 7.24 (dd, J=7.7, 5.3 Hz, 2H), 6.22-6.26 (m, 1H), 4.14-4.26 (m, 2H), 3.90 (t, J=5.8 Hz, 1H), 3.62-3.78 (m, 3H), 3.43-3.49 (m, 1H), 3.28 (s, 3H), 2.06-2.13 (m, 1H), 1.99-2.05 (m, 1H), 1.88-1.93 (m, 1H), 1.68-1.75 (m, 1H), 1.35-1.50 (m, 1H), 1.26-1.30 (m, 3H), 1.13-1.24 (m, 4H).

To a solution of (2R,4R)—N-[2-[(2,2-dimethyltetrahydropyran-4-yl)amino]-2-oxo-1-(3-pyridyl)ethyl]-4-methoxy-N-[4-(pentafluoro-$\lambda^6$-sulfanyl)phenyl]pyrrolidine-2-carboxamide Isomer 2 (60 mg, 101.25 umol, 1 eq) in DMF (1 mL) was added $NaHCO_3$ (25.52 mg, 303.74 umol, 11.81 uL, 3 eq) and BrCN (16.09 mg, 151.87 umol, 11.17 uL, 1.5 eq) in DMF (0.2 mL) at −10° C., and the mixture was stirred at 0° C. for 1 h. The reaction mixture was quenched by addition $H_2O$ 20 mL at 0° C., and then extracted with EA (15 mL*3). The combined organic layers were washed with brine 20 mL, dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 20%-60%, 8 min) to get the product (2R,4R)-1-cyano-N-[2-[(2,2-dimethyltetrahydropyran-4-yl)amino]-2-oxo-1-

(3-pyridyl)ethyl]-4-methoxy-N-[4-(pentafluoro-λ6-sulfanyl)phenyl]pyrrolidine-2-carboxamide (14.24 mg, 23.06 umol, 22.77% yield, 100% purity) as a white solid. MS (ESI) m/z 618.2 $[M+H]^+$ $^1$H NMR (METHANOL-$d_4$, 400 MHz): δ ppm 8.33-8.47 (m, 2H), 6.83-8.26 (m, 6H), 6.07 (s, 1H), 4.25 (dd, J=8.7, 5.4 Hz, 1H), 4.11 (ddd, J=12.0, 7.9, 4.3 Hz, 1H), 3.88-3.96 (m, 1H), 3.57-3.77 (m, 3H), 3.50 (dd, J=9.7, 4.6 Hz, 1H), 3.28 (s, 3H), 2.06-2.17 (m, 1H), 1.82-2.00 (m, 2H), 1.68 (br dd, J=12.3, 1.8 Hz, 1H), 1.12-1.36 (m, 8H).

Example 109: Synthesis of Compound 1171

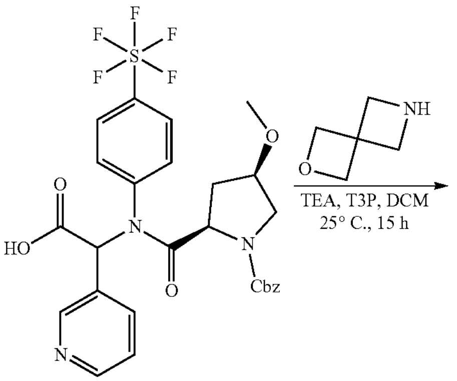

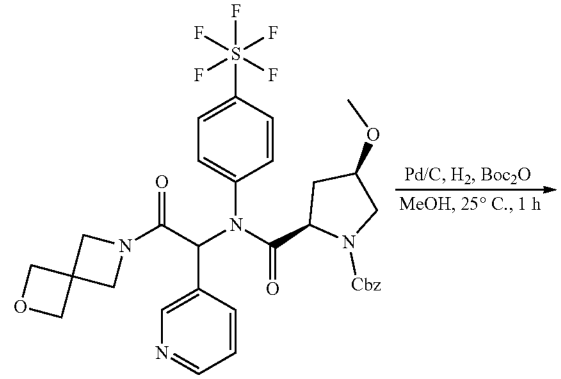

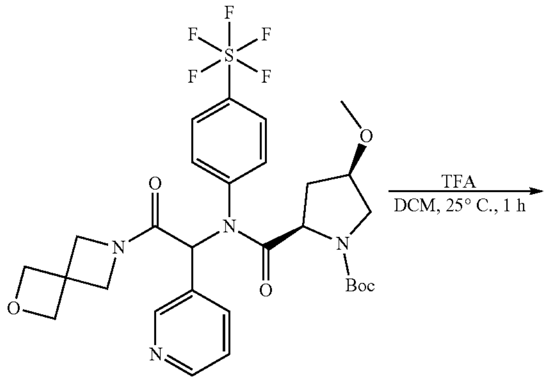

-continued

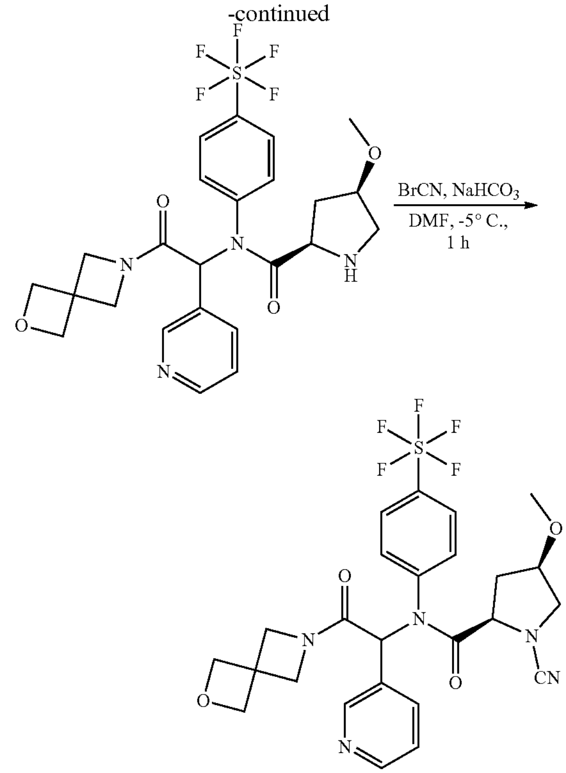

Step 1: benzyl (2R,4R)-4-methoxy-2-[[2-(2-oxa-6-azaspiro[3.3]heptan-6-yl)-2-oxo-1-(3-pyridyl)ethyl]-[4-(pentafluoro-$\lambda^6$-sulfanyl)phenyl]carbamoyl]pyrrolidine-1-carboxylate A mixture of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (400 mg, 649.81 umol, 1 eq) in DCM (6 mL) was added with 2-oxa-6-azaspiro[3.3]heptane (193.25 mg, 1.95 mmol, 3 eq), TEA (394.52 mg, 3.90 mmol, 542.67 uL, 6 eq) and T3P (620.27 mg, 974.71 umol, 579.69 uL, 50% purity, 1.5 eq), and the resulting mixture was stirred at 25° C. for 15 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-60%, 8 min) to get product benzyl (2R,4R)-4-methoxy-2-[[2-(2-oxa-6-azaspiro[3.3]heptan-6-yl)-2-oxo-1-(3-pyridyl)ethyl]-[4-(pentafluoro-$\lambda^6$-sulfanyl)phenyl]carbamoyl]pyrrolidine-1-carboxylate Isomer 1 (165 mg, 236.84 umol, 36.45% yield) as white oil. MS (ESI) m/z 697.2 $[M+H]^+$; and to get the product benzyl (2R,4R)-4-methoxy-2-[[2-(2-oxa-6-azaspiro[3.3]heptan-6-yl)-2-oxo-1-(3-pyridyl)ethyl]-[4-(pentafluoro-$\lambda^6$-sulfanyl)phenyl]carbamoyl]pyrrolidine-1-carboxylate Isomer 2 (125 mg, 179.42 umol, 27.61% yield) as white oil. MS (ESI) m/z 697.2$[M+H]^+$.

Step 2: tert-butyl (2R,4R)-4-methoxy-2-[[2-(2-oxa-6-azaspiro[3.3]heptan-6-yl)-2-oxo-1-(3-pyridyl)ethyl]-[4-(pentafluoro-$\lambda^6$-sulfanyl)phenyl]carbamoyl]pyrrolidine-1-carboxylate Isomer 1

A mixture of benzyl (2R,4R)-4-methoxy-2-[[2-(2-oxa-6-azaspiro[3.3]heptan-6-yl)-2-oxo-1-(3-pyridyl)ethyl]-[4-

(pentafluoro-λ$^6$-sulfanyl)phenyl]carbamoyl]pyrrolidine-1-carboxylate Isomer 1 (129 mg, 185.16 umol, 1 eq) in MeOH (3 mL) and $Boc_2O$ (60.62 mg, 277.74 umol, 63.81 uL, 1.5 eq) was added with Pd/C (258.00 mg, 218.64 umol, 10% purity, 1.18 eq). The suspension was degassed and purged with $H_2$ (374.03 ug, 185.16 umol, 1 eq) for 3 times. The mixture was stirred under $H_2$ (15 psi or atm) at 25° C. for 1 h. Upon completion, the reaction mixture was filtered and concentrated under reduced pressure to give a residue to get the product tert-butyl (2R,4R)-4-methoxy-2-[[2-(2-oxa-6-azaspiro[3.3]heptan-6-yl)-2-oxo-1-(3-pyridyl)ethyl]-[4-(pentafluoro-λ$^6$-sulfanyl)phenyl]carbamoyl]pyrrolidine-1-carboxylate Isomer 1 (120 mg, crude) as a yellow oil. MS (ESI) m/z 663.2 $[M+H]^+$.

tert-butyl (2R,4R)-4-methoxy-2-[[2-(2-oxa-6-azaspiro[3.3]heptan-6-yl)-2-oxo-1-(3-pyridyl)ethyl]-[4-(pentafluoro-λ$^6$-sulfanyl)phenyl]carbamoyl]pyrrolidine-1-carboxylate Isomer 2

A mixture of benzyl (2R,4R)-4-methoxy-2-[[2-(2-oxa-6-azaspiro[3.3]heptan-6-yl)-2-oxo-1-(3-pyridyl)ethyl]-[4-(pentafluoro-λ$^6$-sulfanyl)phenyl]carbamoyl]pyrrolidine-1-carboxylate Isomer 2 (108 mg, 155.02 umol, 1 eq) in MeOH (3 mL) and $Boc_2O$ (50.75 mg, 232.53 umol, 53.42 uL, 1.5 eq) was added with Pd/C (216.00 mg, 183.05 umol, 10% purity, 1.18 eq). The suspension was degassed and purged with $H_2$ (313.14 ug, 155.02 umol, 1 eq) for 3 times. The mixture was stirred under $H_2$ (15 psi or atm) at 25° C. for 1 h. Upon completion, the reaction mixture was filtered and concentrated under reduced pressure to give a residue to get the product tert-butyl (2R,4R)-4-methoxy-2-[[2-(2-oxa-6-azaspiro[3.3]heptan-6-yl)-2-oxo-1-(3-pyridyl)ethyl]-[4-(pentafluoro-λ$^6$-sulfanyl)phenyl]carbamoyl]pyrrolidine-1-carboxylate Isomer 2 (102 mg, crude) as yellow oil. MS (ESI) m/z 663.2 $[M+H]^+$.

Step 3: (2R,4R)-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 1

A mixture of tert-butyl (2R,4R)-4-methoxy-2-[[2-(2-oxa-6-azaspiro[3.3]heptan-6-yl)-2-oxo-1-(3-pyridyl)ethyl]-[4-(pentafluoro-λ$^6$-sulfanyl)phenyl]carbamoyl]pyrrolidine-1-carboxylate Isomer 1 (115 mg, 173.54 umol, 1 eq) in DCM (2 mL) and TFA (1 mL) was stirred at 25° C. for 1 h. Upon completion, the reaction mixture was diluted with $NaHCO_3$ (10 mL) and extracted with EA (10 mL*3). The combined organic layers were washed with brine, dried over $Na_2SO_4$, filtered and concentrated under reduced pressure to give a residue to get the product (2R,4R)-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 1 (93 mg, crude) as yellow oil. MS (ESI) m/z 563.2 $[M+H]^+$.

(2R,4R)-4-methoxy-N-[2-(2-oxa-6-azaspiro[3.3]heptan-6-yl)-2-oxo-1-(3-pyridyl)ethyl]-N-[4-(pentafluoro-46-sulfanyl)phenyl]pyrrolidine-2-carboxamide Isomer 2

A mixture of tert-butyl (2R,4R)-4-methoxy-2-[[2-(2-oxa-6-azaspiro[3.3]heptan-6-yl)-2-oxo-1-(3-pyridyl)ethyl]-[4-(pentafluoro-λ$^6$-sulfanyl)phenyl]carbamoyl]pyrrolidine-1-carboxylate Isomer 2 (97 mg, 146.38 umol, 1 eq) in DCM (2 mL) and TFA (1 mL) was stirred at 25° C. for 1 h. Upon completion, the reaction mixture was diluted with $NaHCO_3$ (10 mL) and extracted with DCM (10 mL*3). The combined organic layers were washed with brine, dried over $Na_2SO_4$, filtered and concentrated under reduced pressure to give a residue to afford the product (2R,4R)-4-methoxy-N-[2-(2-oxa-6-azaspiro[3.3]heptan-6-yl)-2-oxo-1-(3-pyridyl)ethyl]-N-[4-(pentafluoro-26-sulfanyl)phenyl]pyrrolidine-2-carboxamide Isomer 2 (75 mg, crude) as yellow oil. MS (ESI) m/z 563.2 $[M+H]^+$.

Step 4: (2R,4R)-1-cyano-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 1

A mixture of (2R,4R)-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 1 (93 mg, 165.32 umol, 1 eq) in DMF (1.5 mL) was added with $NaHCO_3$ (41.67 mg, 495.95 umol, 19.29 uL, 3 eq), and the solution was cooled to −5° C. BrCN (21.01 mg, 198.38 umol, 14.59 uL, 1.2 eq) in DMF (0.5 mL) was added drop-wise, and the mixture was stirred at −5° C. for 1 h. Upon completion, the reaction mixture was quenched with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-60%, 7 min) to afford (2R,4R)-1-cyano-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 1 (33.41 mg, 56.75 umol, 34.33% yield, 99.8% purity) as yellow solid. MS (ESI) m/z 588.2 $[M+H]^+$.

$^1$H NMR (400 MHz, METHANOL-$d_4$) δ=8.37 (s, 2H), 7.99-7.33 (m, 5H), 7.25 (dd, J=5.0, 7.9 Hz, 1H), 6.29 (s, 1H), 4.84 (s, 2H), 4.73-4.61 (m, 3H), 4.35 (d, J=10.3 Hz, 1H), 4.26-4.14 (m, 2H), 4.00-3.86 (m, 2H), 3.65 (dd, J=5.9, 9.4 Hz, 1H), 3.46 (dd, J=5.0, 9.4 Hz, 1H), 3.28 (s, 3H), 2.12-2.03 (m, 1H), 2.02-1.93 (m, 1H).

(2R,4R)-1-cyano-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 2

A mixture of (2R,4R)-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 2 (75 mg, 133.32 umol, 1 eq) in DMF (1.5 mL) was added with $NaHCO_3$ (33.60 mg, 399.96 umol, 15.56 uL, 3 eq), and then the solution was cooled to −5° C. BrCN (16.95 mg, 159.99 umol, 11.77 uL, 1.2 eq) in DMF (0.5 mL) was added drop-wise, and the mixture was stirred at −5° C. for 1 h. Upon completion, the reaction mixture was quenched with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-60%, 7 min) to get the product ((2R,4R)-1-cyano-4-methoxy-N-[2-(2-oxa-6-azaspiro[3.3]heptan-6-yl)-2-oxo-1-(3-pyridyl)ethyl]-N-[4-(pentafluoro-λ$^6$-sulfanyl)phenyl]pyrrolidine-2-carboxamide Isomer 2 (11.92 mg, 20.29 umol, 15.22% yield, 100% purity) as yellow solid. MS (ESI) m/z 563.2 $[M+H]^+$.

$^1$H NMR (400 MHz, METHANOL-$d_4$) δ=8.38 (s, 2H), 8.18-6.84 (m, 6H), 6.15 (s, 1H), 4.84 (s, 2H), 4.72-4.61 (m, 3H), 4.33 (d, J=11.0 Hz, 1H), 4.24 (dd, J=5.4, 8.9 Hz, 1H), 4.12 (d, J=10.7 Hz, 1H), 4.01 (d, J=9.0 Hz, 1H), 3.91 (t, J=5.4 Hz, 1H), 3.62 (dd, J=5.8, 9.8 Hz, 1H), 3.50 (dd, J=4.8, 9.4 Hz, 1H), 3.29 (s, 3H), 2.15-2.05 (m, 1H), 1.98-1.89 (m, 1H).

Example 110: Synthesis of Compound 1180

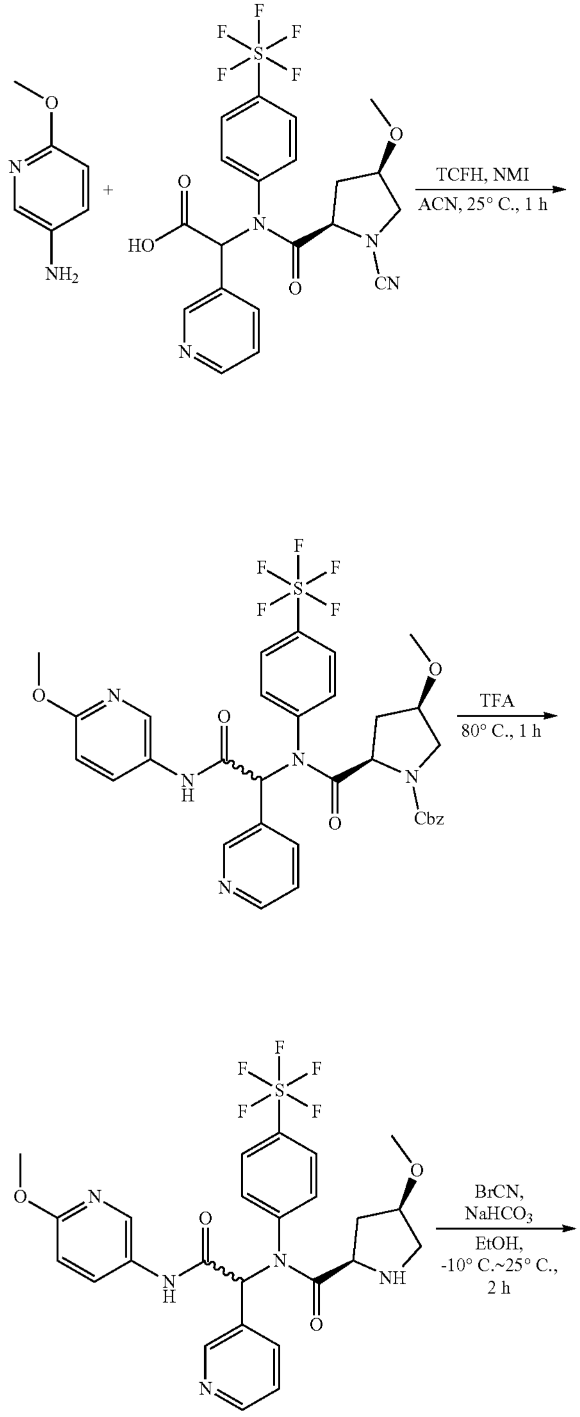

-continued

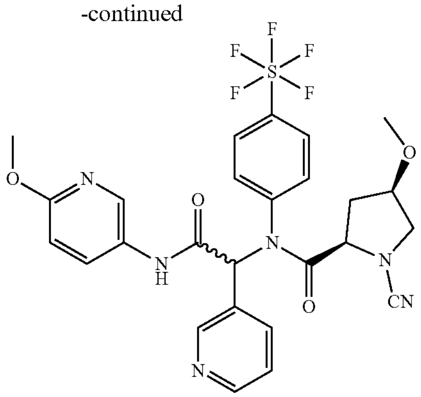

Step1: benzyl(2R,4R)-4-methoxy-2-[[2-[(6-methoxy-3-pyridyl)amino]-2-oxo-1-(3-pyridyl)ethyl]-[4-(pentafluoro-$\lambda^6$-sulfanyl)phenyl]carbamoyl]pyrrolidine-1-carboxylate To a solution of 6-methoxypyridin-3-amine (60.50 mg, 487.35 umol, 1 eq), 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (300 mg, 487.35 umol, 1 eq) in ACN (3 mL) was added 1-methylimidazole (140.05 mg, 1.71 mmol, 135.97 uL, 3.5 eq) [chloro(dimethylamino)methylene]-dimethyl-ammonium;hexafluorophosphate (177.76 mg, 633.56 umol, 1.3 eq) and the mixture was stirred at 25° C. for 1 h. Upon completion, the mixture was quenched by addition $H_2O$ (20 mL) and then extracted with EtOAc (10 mL*3). The combined organic layers were washed with brine (20 mL), dried over $Na_2SO_4$, filtered and concentrated under reduced pressure and was purified by column chromatography ($SiO_2$, DCM:MeOH=10:1) to give product benzyl (2R,4R)-4-methoxy-2-[[2-[(6-methoxy-3-pyridyl)amino]-2-oxo-1-(3-pyridyl)ethyl]-[4-(pentafluoro-$\lambda^6$-sulfanyl)phenyl]carbamoyl]pyrrolidine-1-carboxylate (200 mg, 277.13 umol, 56.86% yield) was yellow solid. MS (ESI) m/z 722.2 [M+H]$^+$ Step2: (2R,4R)-4-methoxy-N-[2-[(6-methoxy-3-pyridyl)amino]-2-oxo-1-(3-pyridyl)ethyl]-N-[4-(pentafluoro-$\lambda^6$-sulfanyl)phenyl]pyrrolidine-2-carboxamide To a solution of benzyl (2R,4R)-4-methoxy-2-[[2-[(6-methoxy-3-pyridyl)amino]-2-oxo-1-(3-pyridyl)ethyl]j-[4-(pentafluoro-$\lambda^6$-sulfanyl)phenyl]carbamoyl]pyrrolidine-1-carboxylate (200 mg, 277.13 umol, 1 eq) was added TFA (10 mL) and the mixture was stirred at 80° C. for 1 h. Upon completion, The reaction mixture was quenched by addition $NaHCO_3$ (50 mL) to adjust to pH=7, and extracted with DCM (20 mL*3): The combined organic layers were washed with brine (20 mL), dried over $Na_2SO_4$, filtered and concentrated under reduced pressure to give product (2R,4R)-4-methoxy-N-[2-[(6-methoxy-3-pyridyl)amino]-2-oxo-1-(3-pyridyl)ethyl]-N-[4-(pentafluoro-$\lambda^6$-sulfanyl)phenyl]pyrrolidine-2-carboxamide (180 mg, crude) was yellow oil. MS (ESI) m/z 588.2 [M+H]$^+$ Step3: (2R,4R)-1-cyano-4-methoxy-N-[2-[(6-methoxy-3-pyridyl)amino]-2-oxo-1-(3-pyridyl)ethyl]-N-[4-(pentafluoro-$\lambda^6$-sulfanyl)phenyl]pyrrolidine-2-carboxamide To a solution of (2R,4R)-4-methoxy-N-[2-[(6-methoxy-3-pyridyl)amino]-2-oxo-1-(3-pyridyl)ethyl]-N-[4-(pentafluoro-λ$^6$-sulfanyl)phenyl]pyrrolidine-2-carboxamide (180 mg, 306.35 umol, 1 eq) in EtOH (4 mL) was added $NaHCO_3$ (77.21 mg, 919.05 umol, 35.75 uL, 3 eq) and the mixture was cooled at −10° C. The mixture was added with BrCN (42.18 mg, 398.26 umol, 29.29 uL, 1.3 eq) in EtOH (0.5 mL), and then the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue. The crude product was purified by prep-HPLC (column: Phenomenex Luna C18 200*40 mm*10 um; mobile phase: [water (0.2% FA)-ACN]; B %: 40%-80%, 8 min) to give product (2R,4R)-1-cyano-4-methoxy-N-[2-[(6-methoxy-3-pyridyl)amino]-2-oxo-1-(3-pyridyl)ethyl]-N-[4-(pentafluoro-λ$^6$-sulfanyl) phenyl]pyrrolidine-2-carboxamide (5 mg, 8.16 umol, 2.66% yield, 100% purity) was yellow solid. MS (ESI) m/z 613.2 $[M+H]^+$ $^1$H NMR (400 MHz, MeOD-$d_4$) δ=8.46-8.45 (m, 1H), 8.42-8.41 (m, 1H), 8.29-8.28 (m, 1H), 7.98-7.54 (m, 6H), 7.27-7.26 (m, 1H), 6.78-6.77 (m, 1H), 6.26 (s, 1H), 4.30-4.29 (m, 1H), 3.95-3.90 (m, 1H), 3.88 (s, 3H), 3.63-3.62 (m, 1H), 3.53-3.51 (m, 1H), 3.29 (s, 3H), 2.19-2.09 (m, 1H), 2.03-1.95 (m, 1H)

(2R,4R)-1-cyano-4-methoxy-N-[2-[(6-methoxy-3-pyridyl)amino]-2-oxo-1-(3-pyridyl)ethyl]-N-[4-(pentafluoro-λ$^6$-sulfanyl)phenyl]pyrrolidine-2-carboxamide (20 mg, 29.83 umol, 9.74% yield, 91.37% purity) was yellow solid. MS (ESI) m/z 613.2 $[M+H]^+$ $^1$H NMR (400 MHz, MeOD-$d_4$) δ=8.48-8.35 (m, 3H), 8.31-7.26 (m, 6H), 6.80-6.79 (m, 1H), 6.75-6.74 (m, 1H), 6.44 (s, 1H), 4.30-4.28 (m, 1H), 3.94-3.85 (m, 4H), 3.65-3.63 (m, 1H), 3.52-3.45 (m, 1H), 3.30-3.27 (m, 3H), 2.18-2.01 (m, 2H)

Example 111: Synthesis of Compound 1195

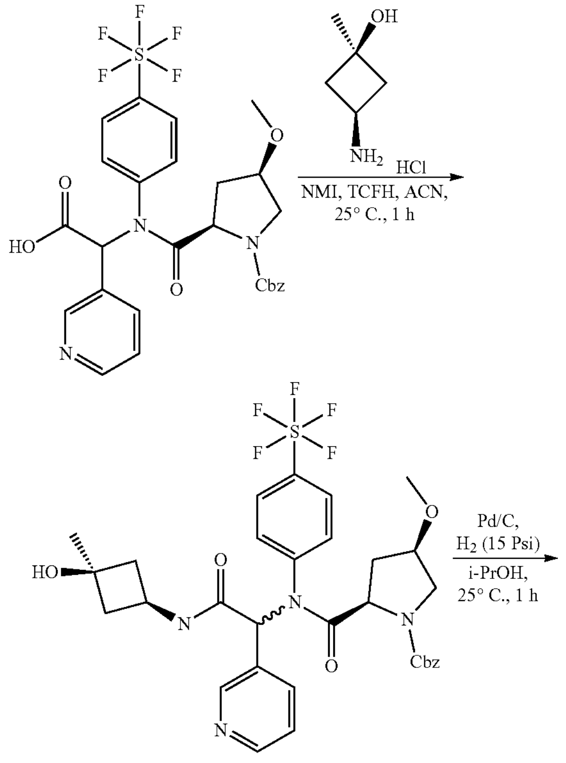

-continued

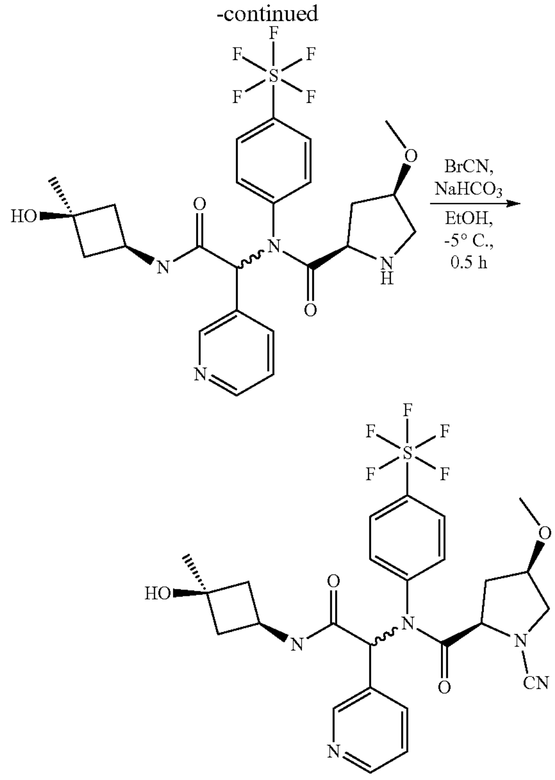

Step 1: benzyl (2R,4R)-2-[[2-[(3-hydroxy-3-methyl-cyclobutyl)amino]-2-oxo-1-(3-pyridyl)ethyl]-[4-(pentafluoro-λ$^6$-sulfanyl)phenyl]carbamoyl]-4-methoxy-pyrrolidine-1-carboxylate A mixture of 2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetic acid (0.4 g, 649.81 umol, 1 eq), 3-amino-1-methyl-cyclobutanol (268.25 mg, 1.95 mmol, 3 eq, HC), 1-methylimidazole (266.75 mg, 3.25 mmol, 258.98 uL, 5 eq), [chloro(dimethylamino)methylene]-dimethyl-ammonium;hexafluorophosphate (364.64 mg, 1.30 mmol, 2 eq) in ACN (5 mL) was stirred at 25° C. for 1 h. Upon completion, the reaction mixture was diluted with water (20 mL) and extracted with EA (10 mL*3). The combined organic layers were dried over $Na_2SO_4$, filtered and concentrated under reduced pressure to give a residue. The residue was purified by prep-HPLC (column: Waters Xbridge Prep OBD C18 150*40 dmm*10 um; mobile phase: [water (10 mM $NH_4HCO_3$)-ACN]; B %: 40%-60%, 8 min) to give benzyl (2R,4R)-2-[[2-[(3-hydroxy-3-methyl-cyclobutyl)amino]-2-oxo-1-(3-pyridyl)ethyl]-[4-(pentafluoro-λ$^6$-sulfanyl)phenyl]carbamoyl]-4-methoxy-pyrrolidine-1-carboxylate (0.15 g, 214.68 umol, 33.04% yield) as a white solid. MS (ESI) m/z 699.2 $[M+H]^+$.

Step 2: (2R,4R)—N-[2-[(3-hydroxy-3-methyl-cyclobutyl)amino]-2-oxo-1-(3-pyridyl)ethyl]-4-methoxy-N-[4-(pentafluoro-λ$^6$-sulfanyl)phenyl]pyrrolidine-2-carboxamide To a solution of benzyl (2R,4R)-2-[[2-[(3-hydroxy-3-methyl-cyclobutyl)amino]-2-oxo-1-(3-pyridyl)ethyl]-[4-(pentafluoro-λ$^6$-sulfanyl)phenyl]carbamoyl]-4-methoxy-pyrrolidine-1-carboxylate (0.15 g, 214.68 umol, 1 eq) in i-PrOH (3 mL) was added Pd/C (0.005 g, 214.68 umol, 10% purity, 1 eq), and the mixture was stirred at 25° C. for 1 h under $H_2$ (433.66 ug, 214.68 umol, 1 eq) at 15 Psi. Upon completion, the reaction mixture was filtered and concentrated under reduced pressure to give (2R,4R)—N-[2-[(3-hydroxy-3-methyl-cyclobutyl)amino]-2-oxo-1-(3-pyridyl)ethyl]-4-methoxy-N-[4-(pentafluoro-$\lambda^6$-sulfanyl)phenyl]pyrrolidine-2-carboxamide (0.13 g, crude) as a yellow oil.

Step 3: (2R,4R)-1-cyano-N-[2-[(3-hydroxy-3-methyl-cyclobutyl)amino]-2-oxo-1-(3-pyridyl)ethyl]-4-methoxy-N-[4-(pentafluoro-$\lambda^6$-sulfanyl)phenyl]pyrrolidine-2-carboxamide To a solution of (2R,4R)—N-[2-[(3-hydroxy-3-methyl-cyclobutyl)amino]-2-oxo-1-(3-pyridyl)ethyl]-4-methoxy-N-[4-(pentafluoro-$\lambda^6$-sulfanyl)phenyl]pyrrolidine-2-carboxamide (0.13 g, 230.26 umol, 1 eq) in EtOH (2 mL) was added $NaHCO_3$ (58.03 mg, 690.79 umol, 26.87 uL, 3 eq). BrCN (24.39 mg, 230.26 umol, 16.94 uL, 1 eq) in EtOH (0.5 mL) was added drop-wise at −5° C., and the mixture was stirred at −5° C. for 0.5 h under $N_2$ atmosphere. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 20%-60%, 8 min) to give (2R,4R)-1-cyano-N-[2-[(3-hydroxy-3-methyl-cyclobutyl)amino]-2-oxo-1-(3-pyridyl)ethyl]-4-methoxy-N-[4-(pentafluoro-$\lambda^6$-sulfanyl)phenyl]pyrrolidine-2-carboxamide (57.76 mg, 97.97 umol, 42.55% yield, 100% purity) as a yellow solid. MS (ESI) m/z 590.2 $[M+H]^+$.

$^1H$ NMR (400 MHz, METHANOL-$d_4$) δ=8.33 (dt, J=1.5, 4.5 Hz, 2H), 7.74 (br d, J=1.7 Hz, 3H), 7.56 (br d, J=8.1 Hz, 1H), 7.23 (dd, J=5.0, 7.9 Hz, 2H), 6.26 (s, 1H), 4.22 (dd, J=6.4, 8.7 Hz, 1H), 4.02-3.86 (m, 2H), 3.64 (dd, J=5.9, 9.5 Hz, 1H), 3.46 (dd, J=5.2, 9.5 Hz, 1H), 3.28 (s, 3H), 2.52-2.27 (m, 2H), 2.16-1.96 (m, 3H), 1.93-1.84 (m, 1H), 1.34 (s, 3H).

Example 112: Synthesis of Compound 1197

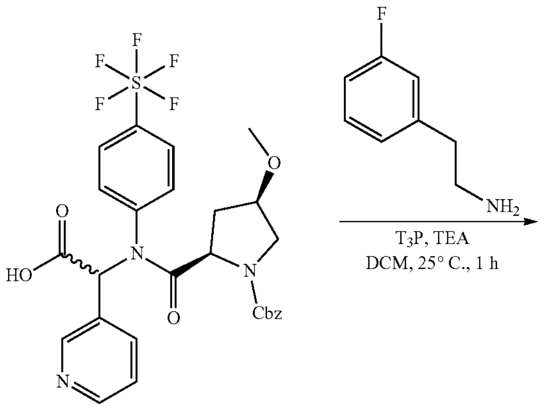

-continued

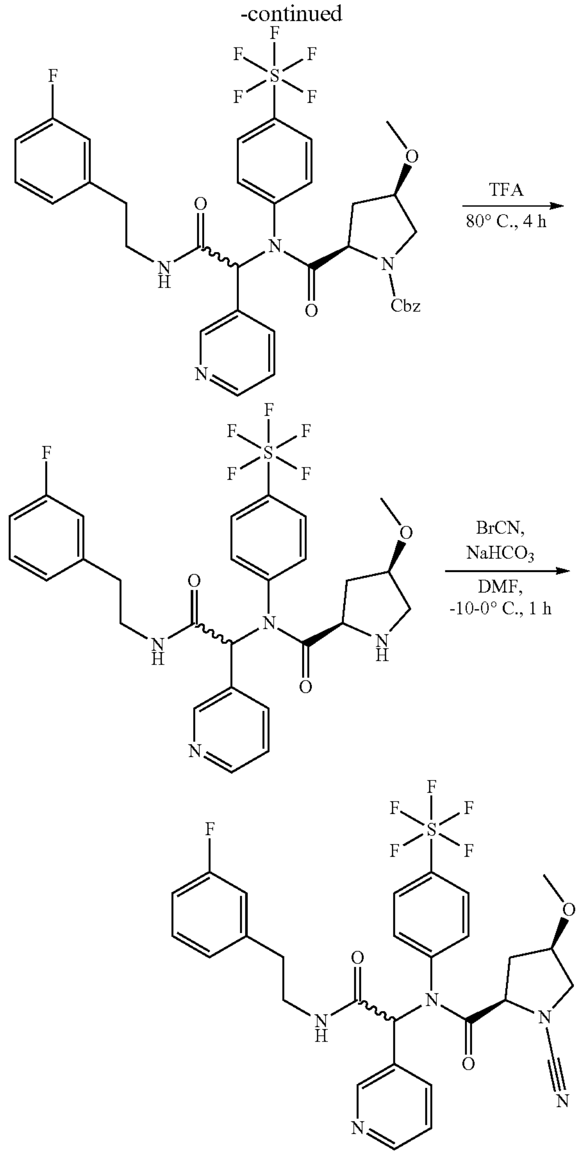

Step 1: (2R,4R)—N-[2-[2-(3-fluorophenyl)ethylamino]-2-oxo-1-(3-pyridyl)ethyl]-4-methoxy-N-[4-(pentafluoro-$\lambda^6$-sulfanyl)phenyl]pyrrolidine-2-carboxamide To a solution of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (400 mg, 649.81 umol, 1 eq) and 2-(3-fluorophenyl)ethanamine (135.65 mg, 974.71 umol, 126.78 uL, 1.5 eq) in DCM (8 mL) was added T3P (1.24 g, 1.95 mmol, 1.16 mL, 50% purity, 3 eq) and TEA (394.52 mg, 3.90 mmol, 542.67 uL, 6 eq), and then the mixture was stirred at 25° C. for 1 h. The residue was diluted with $H_2O$ 30 mL and extracted with DCM (20 mL*3). The combined organic layers were washed with brine 15 mL, the combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 45%-75%, 10 min) to afford benzyl (2R,4R)-2-[[2-[2-(3-fluorophenyl)ethylamino]-2-oxo-1-(3-pyridyl)ethyl]-[4-(pentafluoro-λ$^6$-sulfanyl)phenyl]carbamoyl]-4-methoxy-pyrrolidine-1-carboxylate Isomer 1 (120 mg, 162.88 umol, 25.07% yield) as a white solid, MS (ESI) m/z 737.2 $[M+H]^+$; and benzyl (2R,4R)-2-[[2-[2-(3-fluorophenyl)ethylamino]-2-oxo-1-(3-pyridyl)ethyl]-[4-(pentafluoro-λ$^6$-sulfanyl)phenyl]carbamoyl]-4-methoxy-pyrrolidine-1-carboxylate Isomer 2 (120 mg, 162.88 umol, 25.07% yield) was obtained as a white solid. MS (ESI) m/z 737.2 $[M+H]^+$ Step 2: (2R,4R)—N-[2-[2-(3-fluorophenyl)ethylamino]-2-oxo-1-(3-pyridyl)ethyl]-4-methoxy-N-[4-(pentafluoro-λ$^6$-sulfanyl)phenyl]pyrrolidine-2-carboxamide A solution of benzyl (2R,4R)-2-[[2-[2-(3-fluorophenyl)ethylamino]-2-oxo-1-(3-pyridyl)ethyl]-[4-(pentafluoro-λ$^6$-sulfanyl)phenyl]carbamoyl]-4-methoxy-pyrrolidine-1-carboxylate Isomer 1 (90 mg, 122.16 umol, 1 eq) in 2,2,2-trifluoroacetic acid (5.54 g, 48.62 mmol, 3.60 mL, 398.01 eq) was stirred at 80° C. for 4 h. The reaction mixture was quenched by addition aq. $NaHCO_3$ 40 mL at 0° C., and extracted with DCM (20 mL*3). The combined organic layers were dried over $Na_2SO_4$, filtered and concentrated under reduced pressure to afford (2R,4R)—N-[2-[2-(3-fluorophenyl)ethylamino]-2-oxo-1-(3-pyridyl)ethyl]-4-methoxy-N-[4-(pentafluoro-λ$^6$-sulfanyl)phenyl]pyrrolidine-2-carboxamide Isomer 1 ((120 mg, 59.74 umol, 40.01% yield, 30% purity) as a yellow solid. MS (ESI) m/z 603.2 $[M+H]^+$ A mixture of benzyl (2R,4R)-2-[[2-[2-(3-fluorophenyl)ethylamino]-2-oxo-1-(3-pyridyl)ethyl]-[4-(pentafluoro-λ$^6$-sulfanyl)phenyl]carbamoyl]-4-methoxy-pyrrolidine-1-carboxylate Isomer 2 (100 mg, 135.74 umol, 1 eq) in 2,2,2-trifluoroacetic acid (6.16 g, 54.02 mmol, 4 mL, 398.01 eq) was stirred at 80° C. for 4 h. The reaction mixture was quenched by $NaHCO_3$ 40 mL at 0° C., and extracted with DCM (20 mL*3). The combined organic layers were dried over $Na_2SO_4$, filtered and concentrated under reduced pressure to afford (2R,4R)—N-[2-[2-(3-fluorophenyl)ethylamino]-2-oxo-1-(3-pyridyl)ethyl]-4-methoxy-N-[4-(pentafluoro-λ$^6$-sulfanyl)phenyl]pyrrolidine-2-carboxamide Isomer 2 (70 mg, 69.70 umol, 46.68% yield) as a yellow liquid. MS (ESI) m/z 603.2 $[M+H]^+$ Step 3: (2R,4R)-1-cyano-N-[2-[2-(3-fluorophenyl)ethylamino]-2-oxo-1-(3-pyridyl)ethyl]-4-methoxy-N-[4-(pentafluoro-λ6-sulfanyl)phenyl]pyrrolidine-2-carboxamide To a solution of (2R,4R)—N-[2-[2-(3-fluorophenyl)ethylamino]-2-oxo-1-(3-pyridyl)ethyl]-4-methoxy-N-[4-(pentafluoro-λ6-sulfanyl)phenyl]pyrrolidine-2-carboxamide Isomer 1 (120.00 mg, 59.74 umol, 30% purity, 1 eq) in DMF (1 mL) was cooled to −10° C., and then $NaHCO_3$ (15.06 mg, 179.23 umol, 6.97 uL, 3 eq) and BrCN (9.49 mg, 89.61 umol, 6.59 uL, 1.5 eq) in DMF (0.2 mL) was added drop-wise. The resulting mixture was stirred at 0° C. for 1 h. The reaction mixture was quenched by addition $H_2O$ 20 mL at 0° C., and then extracted with EA (15 mL*3). The combined organic layers were washed with brine 20 mL, dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-75%, 8 min) to afford (2R,4R)-1-cyano-N-[2-[2-(3-fluorophenyl)ethylamino]-2-oxo-1-(3-pyridyl)ethyl]-4-methoxy- N-[4-(pentafluoro-λ6-sulfanyl)phenyl]pyrrolidine-2-carboxamide (10.55 mg, 16.76 umol, 28.05% yield, 99.7% purity) as a white solid. MS (ESI) m/z 628.2 $[M+H]^+$ $^1$H NMR (METHANOL-$d_4$, 400 MHz): δ ppm 8.33 (dd, J=4.9, 1.3 Hz, 1H), 8.27 (d, J=1.9 Hz, 1H), 6.67-8.02 (m, 10H), 6.23 (s, 1H), 4.21 (dd, J=8.7, 6.3 Hz, 1H), 3.91 (t, J=5.7 Hz, 1H), 3.59-3.68 (m, 2H), 3.40-3.52 (m, 2H), 3.29 (s, 3H), 2.81 (q, J=7.2 Hz, 2H), 2.08-2.08 (m, 1H), 1.96-2.15 (m, 1H)

A solution of (2R,4R)—N-[2-[2-(3-fluorophenyl)ethylamino]-2-oxo-1-(3-pyridyl)ethyl]-4-methoxy-N-[4-(pentafluoro-λ6-sulfanyl)phenyl]pyrrolidine-2-carboxamide Isomer 2 (70 mg, 116.17 umol, 1 eq) in DMF (1 mL) was cooled to −10° C., and then $NaHCO_3$ (29.28 mg, 348.50 umol, 13.55 uL, 3 eq) and BrCN (18.46 mg, 174.25 umol, 12.82 uL, 1.5 eq) in DMF (0.2 mL) were added drop-wise. The resulting mixture was stirred at 0° C. for 1 h, and then quenched by the addition $H_2O$ 20 mL at 0° C. and extracted with EA (15 mL*3). The combined organic layers were washed with brine 20 mL, dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 35%-70%, 8 min) to afford (2R,4R)-1-cyano-N-[2-[2-(3-fluorophenyl)ethylamino]-2-oxo-1-(3-pyridyl)ethyl]-4-methoxy-N-[4-(pentafluoro-λ6-sulfanyl)phenyl]pyrrolidine-2-carboxamide (18.09 mg, 28.54 umol, 24.56% yield, 99.0% purity) as a yellow solid. MS (ESI) m/z 628.2 [M+H]+

$^1$H NMR (METHANOL-$d_4$, 400 MHz): δ ppm 8.29-8.42 (m, 2H), 6.73-8.02 (m, 10H), 6.04 (s, 1H), 4.24 (dd, J=8.6, 5.7 Hz, 1H), 3.91 (t, J=5.4 Hz, 1H), 3.46-3.68 (m, 3H), 3.37-3.44 (m, 1H), 3.28 (s, 3H), 2.74-2.85 (m, 2H), 2.10 (ddd, J=13.4, 8.7, 6.2 Hz, 1H), 1.88-2.01 (m, 1H)

Example 113: Synthesis of Compound 1158

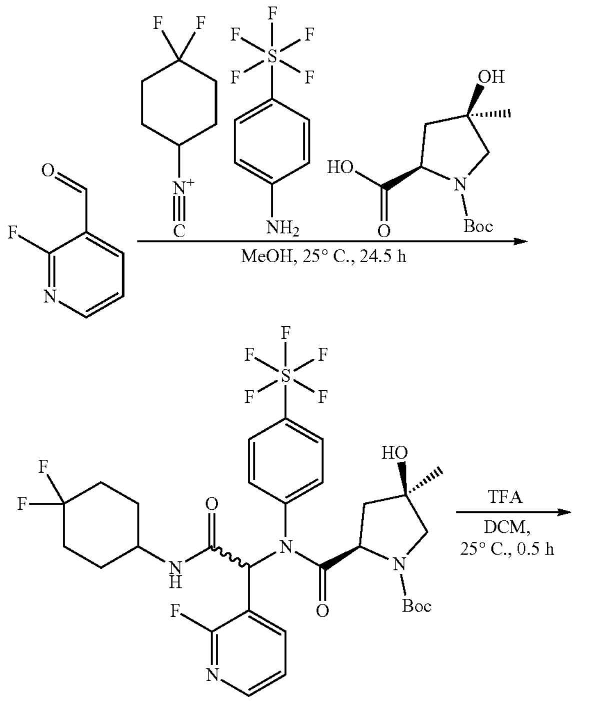

-continued

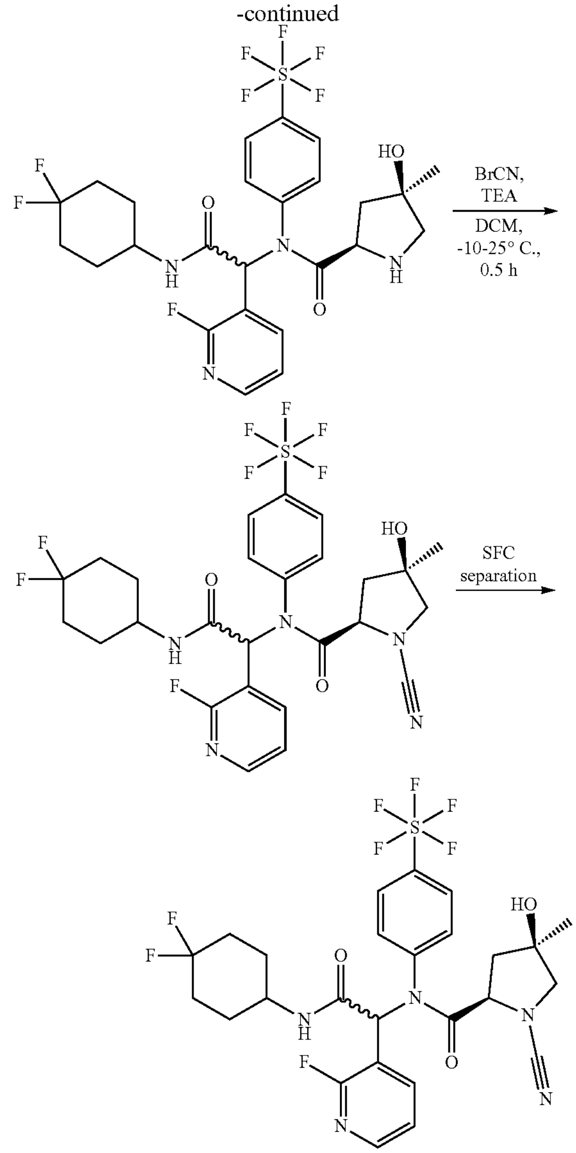

Step 1: tert-butyl(2R,4R)-2-[[2-[(4,4-difluorocyclohexyl)amino]-1-(2-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate 4-(pentafluoro-λ6-sulfanyl)aniline (525.60 mg, 2.40 mmol, 1 eq) and 2-fluoropyridine-3-carbaldehyde (300 mg, 2.40 mmol, 1 eq) in MeOH (8 mL) was stirred at 25° C. for 0.5 h. To the mixture was added (2R,4R)-1-tert-butoxycarbonyl-4-hydroxy-4-methylpyrrolidine-2-carboxylic acid (588.65 mg, 2.40 mmol, 1 eq) and 1,1-difluoro-4-isocyanocyclohexane (348.08 mg, 2.40 mmol, 1 eq) and the resulting mixture was stirred at 25° C. for 24 h. Upon completion, the mixture was concentrated under the reduced pressure to give a residue. The residue was purified by prep-HPLC (column: Kromasil C18 (250*50 mm*10 um); mobile phase: [water (10 mM $NH_4HCO_3$)-ACN]; B %: 55%-75%, 10 min) affording the product tert-butyl (2R,4R)-2-[[2-[(4,4-difluorocyclohexyl)amino]-1-(2-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (210 mg, crude) as a yellow oil. MS (ESI) m/z 717.2 $[M+H]^+$ Step 2: (2R,4R)—N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of tert-butyl (2R,4R)-2-[[2-[(4,4-difluorocyclohexyl)amino]-1-(2-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (200 mg, 279.06 umol, 1 eq) in DCM (3 mL) was added TFA (1.54 g, 13.51 mmol, 1 mL, 48.40 eq). The mixture was stirred at 25° C. for 0.5 h. Upon completion, the reaction mixture was quenched by the addition of sat. $NaHCO_3$ (10 mL), and then extracted with DCM (10 mL*3). The combined organic layers were washed with brine (10 mL), dried over $Na_2SO_4$, filtered and concentrated under reduced pressure affording the product (2R,4R)—N-[2-[(4,4-difluorocyclohexyl)amino]-1-(2-fluoro-3-pyridyl)-2-oxo-ethyl]-4-hydroxy-4-methyl-N-[4-(pentafluoro-2,6-sulfanyl)phenyl]pyrrolidine-2-carboxamide (150 mg, crude) as a yellow solid. MS (ESI) m/z 617.2 $[M+H]^+$ Step 3: (2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of (2R,4R)—N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (140 mg, 227.06 umol, 1 eq) in DCM (3 mL) was added TEA (68.93 mg, 681.19 umol, 94.81 uL, 3 eq), and the solution was cooled to −10° C. A solution of BrCN (28.86 mg, 272.48 umol, 20.04 uL, 1.2 eq) in DCM (0.5 mL) was added and the resulting mixture was stirred for 0.5 h at 0° C. and warmed to 25° C. gradually. Upon completion, the mixture was quenched by addition $H_2O$ (10 mL) and then extracted with DCM (10 mL*3). The combined organic layers were washed with brine (10 mL), dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 35%-65%, 8 min) to afford (2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (45 mg, 70.14 umol, 30.89% yield, 100% purity) as a white solid. MS (ESI) m/z 642.3 [M+H]+ $^1H$ NMR (400 MHz, METHANOL-$d_4$) δ=8.16-7.99 (m, 1H), 7.99-7.47 (m, 4H), 7.34-6.88 (m, 2H), 6.42-6.20 (m, 1H), 4.35-4.21 (m, 1H), 3.97-3.84 (m, 1H), 3.49 (d, J=9.4 Hz, 1H), 3.34 (d, J=9.4 Hz, 1H), 2.10-1.82 (m, 8H), 1.69-1.40 (m, 2H), 1.26 (d, J=10.0 Hz, 3H).

Step 4: (2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-%6-sulfanyl)phenyl]pyrrolidine-2-carboxamide (2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (36 mg, 56.11 umol) was separated by SFC (column: DAICEL CHIRALPAK AD (250 mm*30 mm, 10 um);

mobile phase: [0.1% $NH_3H_2O$ IPA]; B %: 30%-30%, 6 min) to afford (2R,4R)-1-cyano-N-[2-[(4,4-difluorocyclohexyl) amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (13.5 mg, 20.94 umol, 37.31% yield, 99.5% purity) as a white solid. MS (ESI) m/z 642.2 [M+H]+

$^1H$ NMR (400 MHz, METHANOL-$d_4$) δ=8.06 (d, J=4.4 Hz, 1H), 7.99-7.40 (m, 4H), 7.38-7.00 (m, 2H), 6.39 (s, 1H), 4.30 (dd, J=4.8, 9.2 Hz, 1H), 3.93 (br t, J=10.4 Hz, 1H), 3.50 (d, J=9.2 Hz, 1H), 3.35 (s, 1H), 2.11-1.82 (m, 8H), 1.71-1.57 (m, 1H), 1.56-1.42 (m, 1H), 1.24 (s, 3H).

(2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (12 mg, 18.44 umol, 32.87% yield, 98.6% purity) was obtained as a white solid. MS (ESI) m/z 642.3 $[M+H]^+$ $^1H$ NMR (400 MHz, METHANOL-$d_4$) δ=8.09 (br d, J=4.2 Hz, 1H), 8.00-7.49 (m, 4H), 7.38-6.87 (m, 2H), 6.28 (s, 1H), 4.25 (dd, J=5.4, 7.8 Hz, 1H), 3.90 (br t, J=10.0 Hz, 1H), 3.49 (d, J=9.2 Hz, 1H), 3.34 (d, J=9.4 Hz, 1H), 2.11-1.93 (m, 6H), 1.92-1.83 (m, 2H), 1.68-1.55 (m, 1H), 1.53-1.41 (m, 1H), 1.27 (s, 3H).

Example 114: Synthesis of Compound 1198

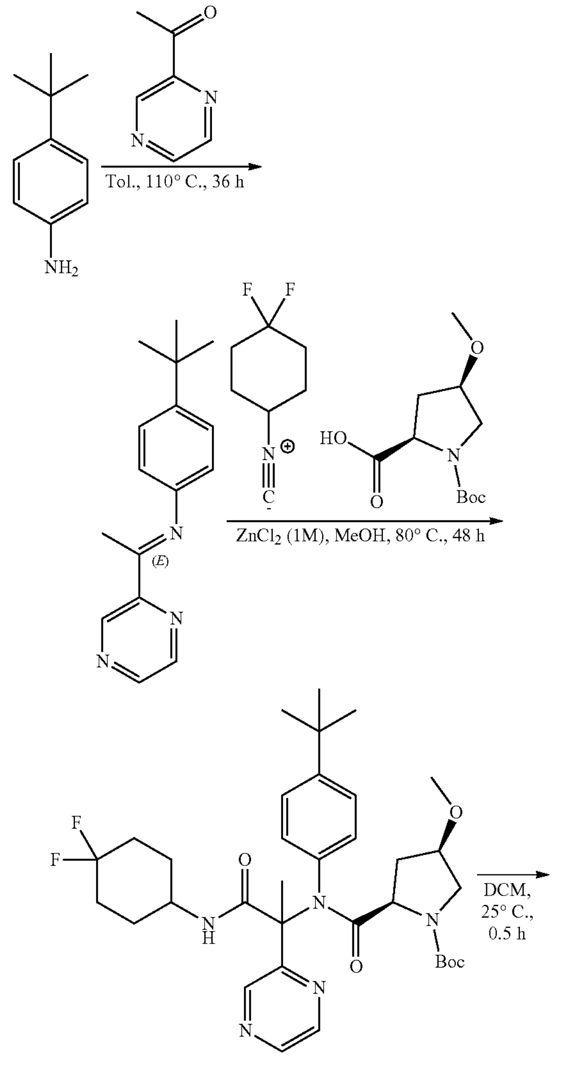

-continued

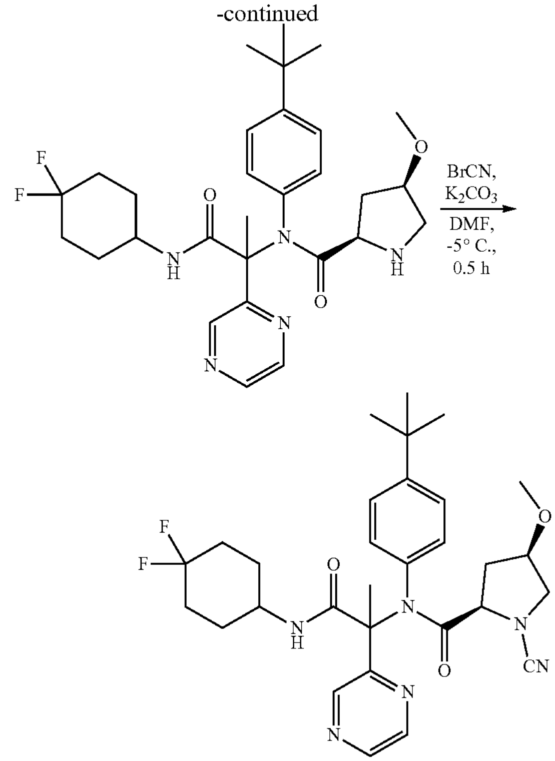

Step 1: (E)-4-(tert-butyl)-N-(1-(pyrazin-2-yl)ethylidene)aniline

A mixture of 4-tert-butylaniline (5 g, 33.50 mmol, 5.29 mL, 1 eq) and 1-pyrazin-2-ylethanone (4.09 g, 33.50 mmol, 8.98 uL, 1 eq) in toluene (70 mL) was stirred at 110° C. for 36 h and water was removed by Dean-Stark trap. Upon completion, the reaction mixture was concentrated under reduced pressure to give a residue. The residue was purified by column chromatography ($SiO_2$, Petroleum ether/Ethyl acetate=20/1 to 10/1) to give (Z)—N-(4-tert-butylphenyl)-1-pyrazin-2-yl-ethanimine (7 g, 13.82 mmol, 41.23% yield, 50% purity) as a yellow oil.

Step 2: (2R,4R)-tert-butyl 2-((4-(tert-butyl)phenyl) (1-((4,4-difluorocyclohexyl)amino)-1-oxo-2-(pyrazin-2-yl)propan-2-yl)carbamoyl)-4-methoxy-pyrrolidine-1-carboxylate To a solution of (E)-N-(4-tert-butylphenyl)-1-pyrazin-2-yl-ethanimine (1 g, 3.95 mmol, 1 eq) in MeOH (10 mL) was added (2R,4R)-1-tert-butoxycarbonyl-4-methoxy-pyrrolidine-2-carboxylic acid (968.15 mg, 3.95 mmol, 1 eq) and 1,1-difluoro-4-isocyano-cyclohexane (572.94 mg, 3.95 mmol, 1 eq). $ZnCl_2$ (1 M, 23.68 mL, 6 eq) was added, and the resulting mixture was stirred at 80° C. for 48 h. Upon completion, the reaction mixture was diluted with water (40 mL) and extracted with EA (20 mL*3). The combined organic layers were dried over $Na_2SO_4$, filtered and concentrated under reduced pressure to give a residue. The residue was purified by prep-HPLC (column: Kromasil C18 (250*50 mm*10 um); mobile phase: [water (0.05% $NH_3H_2O$+10 mM $NH_4HCO_3$)-ACN]; B %: 60%-90%, 10 min) and re-purified by prep-TLC (Petroleum ether:Ethyl acetate=0:1) to give tert-butyl (2R,4R)-2-[(4-tert-butylphenyl)-[2-[(4,4-difluorocyclohexyl)amino]-1-methyl-2-oxo-1-pyrazin-2-yl-ethyl]carbamoyl]-4-methoxy-pyrrolidine-1-carboxylate Isomer 1 (0.05 g, 73.78 umol, 1.87% yield, 95% purity) as a yellow solid, MS (ESI) m/z 644.4 $[M+H]^+$; and to give tert-butyl (2R,4R)-2-[(4-tert-butylphenyl)-[2-[(4,4-difluorocyclohexyl)amino]-1-methyl-2-oxo-1-pyrazin-2-yl-ethyl]carbamoyl]-4-methoxy-pyrrolidine-1-carboxylate Isomer 2 (0.07 g, 103.30 umol, 2.62% yield, 95% purity) as a yellow solid. MS (ESI) m/z 644.4 $[M+H]^+$.

Step 3: (2R,4R)—N-(4-(tert-butyl)phenyl)-N-(1-((4,4-difluorocyclohexyl)amino)-1-oxo-2-(pyrazin-2-yl)propan-2-yl)-4-methoxypyrrolidine-2-carboxamide Isomer 1

To a solution of tert-butyl (2R,4R)-2-[(4-tert-butylphenyl)-[2-[(4,4-difluorocyclohexyl)amino]-1-methyl-2-oxo-1-pyrazin-2-yl-ethyl]carbamoyl]-4-methoxy-pyrrolidine-1-carboxylate Isomer 1 (0.045 g, 69.90 umol, 1 eq) in DCM (1 mL) was added TFA (1.04 g, 9.12 mmol, 675.00 uL, 130.42 eq), and the mixture was stirred at 25° C. for 0.5 h. Upon completion, the reaction mixture was dried by blowing $N_2$ and then diluted with sat. $NaHCO_3$ (5 mL) and extracted with DCM (2 mL*3). The combined organic layers were dried over $Na_2SO_4$, filtered and concentrated under reduced pressure to give a residue to give (2R,4R)—N-(4-tert-butylphenyl)-N-[2-[(4,4-difluorocyclohexyl)amino]-1-methyl-2-oxo-1-pyrazin-2-yl-ethyl]-4-methoxy-pyrrolidine-2-carboxamide Isomer 1 (0.04 g, crude) as a yellow oil.

(2R,4R)—N-(4-(tert-butyl)phenyl)-N-(1-((4,4-difluorocyclohexyl)amino)-1-oxo-2-(pyrazin-2-yl)propan-2-yl)-4-methoxypyrrolidine-2-carboxamide Isomer 2

To a solution of tert-butyl (2R,4R)-2-[(4-tert-butylphenyl)-[2-[(4,4-difluorocyclohexyl)amino]-1-methyl-2-oxo-1-pyrazin-2-yl-ethyl]carbamoyl]-4-methoxy-pyrrolidine-1-carboxylate Isomer 2 (0.07 g, 108.74 umol, 1 eq) in DCM (1 mL) was added TFA (1.62 g, 14.18 mmol, 1.05 mL, 130.42 eq), and the mixture was stirred at 25° C. for 0.5 h. Upon completion, the reaction mixture was dried by blowing $N_2$ and then diluted with sat. $NaHCO_3$ (5 mL) and extracted with DCM (2 mL*3). The combined organic layers were dried over $Na_2SO_4$, filtered and concentrated under reduced pressure to give (2R,4R)—N-(4-tert-butylphenyl)-N-[2-[(4,4-difluorocyclohexyl)amino]-1-methyl-2-oxo-1-pyrazin-2-yl-ethyl]-4-methoxy-pyrrolidine-2-carboxamide Isomer 2 (0.06 g, crude) as a yellow oil.

Step 4: (2R,4R)—N-(4-(tert-butyl)phenyl)-1-cyano-N-(1-((4,4-difluorocyclohexyl)amino)-1-oxo-2-(pyrazin-2-yl)propan-2-yl)-4-methoxypyrrolidine-2-carboxamide Isomer 1

To a solution of (2R,4R)—N-(4-tert-butylphenyl)-N-[2-[(4,4-difluorocyclohexyl)amino]-1-methyl-2-oxo-1-pyrazin-2-yl-ethyl]-4-methoxy-pyrrolidine-2-carboxamide Isomer 1 (0.04 g, 73.58 umol, 1 eq) in EtOH (1 mL) was added $NaHCO_3$ (18.54 mg, 220.73 umol, 8.59 uL, 3 eq) and BrCN (7.79 mg, 73.58 umol, 5.41 uL, 1 eq) at −5° C. The resulting mixture was stirred at −5° C. for 0.5 h under $N_2$ atmosphere. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 45%-75%, 8 min) to give (2R,4R)—N-(4-tert-butylphenyl)-1-cyano-N-[2-[(4,4-difluorocyclohexyl)amino]-1-methyl-2-oxo-1-pyrazin-2-yl-ethyl]-4-methoxy-pyrrolidine-2-carboxamide Isomer 1 (18.17 mg, 31.70 umol, 43.08% yield, 99.2% purity) as a white solid. MS (ESI) m/z 569.4 $[M+H]^+$.

$^1H$ NMR (400 MHz, METHANOL-$d_4$) δ=9.04 (d, J=1.3 Hz, 1H), 8.62 (dd, J=1.5, 2.4 Hz, 1H), 8.55 (d, J=2.5 Hz, 1H), 7.73 (dd, J=2.3, 8.6 Hz, 1H), 7.65-7.56 (m, 2H), 7.48 (dd, J=2.4, 8.5 Hz, 1H), 4.22 (dd, J=6.8, 8.6 Hz, 1H), 3.97-3.82 (m, 2H), 3.59 (dd, J=6.1, 9.4 Hz, 1H), 3.37-3.33 (m, 1H), 3.26 (s, 3H), 2.22-2.13 (m, 1H), 2.10-1.87 (m, 7H), 1.70 (br d, J=11.8 Hz, 2H), 1.45-1.35 (m, 12H).

(2R,4R)—N-(4-(tert-butyl)phenyl)-1-cyano-N-(1-((4,4-difluorocyclohexyl)amino)-1-oxo-2-(pyrazin-2-yl)propan-2-yl)-4-methoxypyrrolidine-2-carboxamide Isomer 2

To a solution of (2R,4R)—N-(4-tert-butylphenyl)-N-[2-[(4,4-difluorocyclohexyl)amino]-1-methyl-2-oxo-1-pyrazin-2-yl-ethyl]-4-methoxy-pyrrolidine-2-carboxamide Isomer 2 (0.06 g, 110.37 umol, 1 eq) in EtOH (1 mL) was added $NaHCO_3$ (27.82 mg, 331.10 umol, 12.88 uL, 3 eq) and BrCN (11.69 mg, 110.37 umol, 8.12 uL, 1 eq) at −5° C. The resulting mixture was stirred at −5° C. for 0.5 h under $N_2$ atmosphere. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 45%-75%, 8 min) to give (2R,4R)—N-(4-tert-butylphenyl)-1-cyano-N-[2-[(4,4-difluorocyclohexyl)amino]-1-methyl-2-oxo-1-pyrazin-2-yl-ethyl]-4-methoxy-pyrrolidine-2-carboxamide Isomer 2 (24.72 mg, 43.08 umol, 39.03% yield, 99.1% purity) as a white solid. MS (ESI) m/z 569.4 $[M+H]^+$.

$^1H$ NMR (400 MHz, METHANOL-$d_4$) δ=9.00 (s, 1H), 8.61 (s, 1H), 8.55 (d, J=2.5 Hz, 1H), 7.73 (dd, J=2.1, 8.3 Hz, 1H), 7.65-7.59 (m, 1H), 7.56 (dd, J=2.1, 8.3 Hz, 1H), 7.43 (dd, J=2.3, 8.3 Hz, 1H), 4.33 (dd, J=5.4, 7.9 Hz, 1H), 3.97-3.84 (m, 2H), 3.56 (dd, J=5.7, 9.8 Hz, 1H), 3.43 (dd, J=3.6, 9.8 Hz, 1H), 3.26 (s, 3H), 2.10-1.87 (m, 8H), 1.79-1.67 (m, 2H), 1.42-1.33 (m, 12H).

Example 115: Synthesis of Compound 1298b

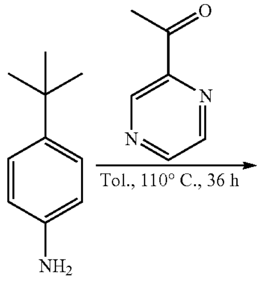

-continued

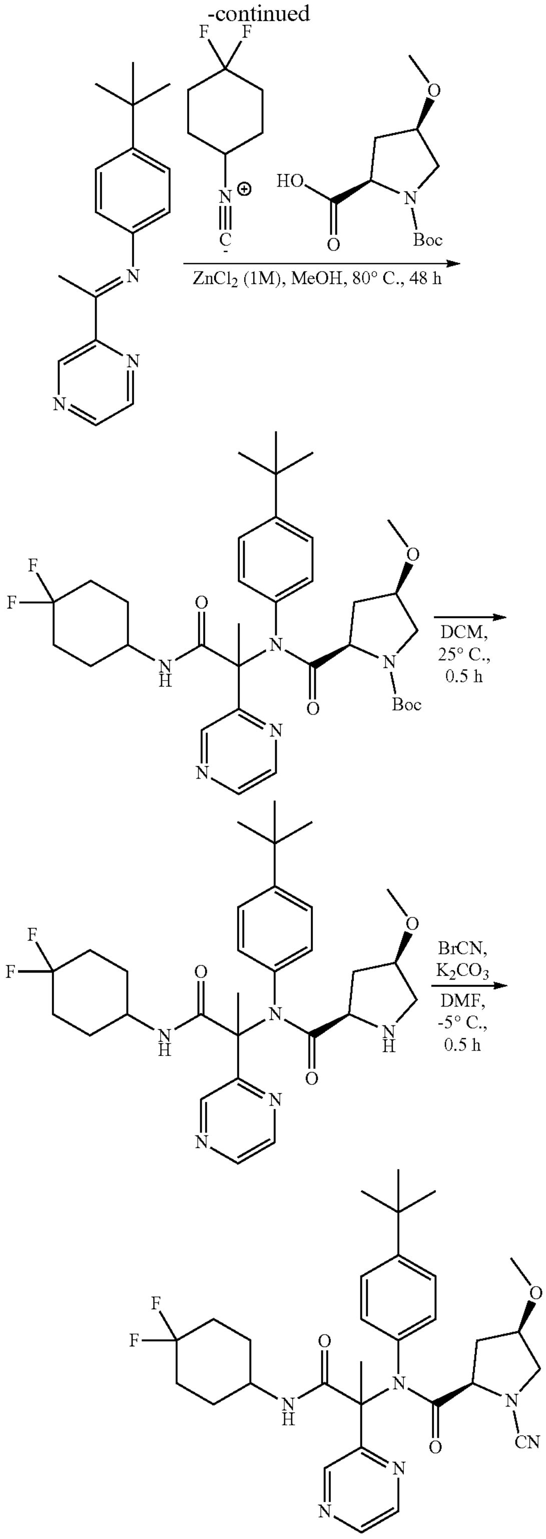

Step 1: (E)-N-[4-(pentafluoro-λ$^6$-sulfanyl)phenyl]-1-(3-pyridyl)ethanimine

To a solution of 4-(pentafluoro-λ$^6$-sulfanyl)aniline (2 g, 9.13 mmol, 1 eq) and 1-(3-pyridyl)ethanone (1.11 g, 9.13 mmol, 1.00 mL, 1 eq) in Tol. (30 mL) was added TosOH (78.57 mg, 456.26 umol, 0.05 eq). The mixture was stirred at 130° C. for 12 h and remove water by Dean-Stark trap. Upon completion, the reaction mixture was concentrated under reduced pressure to give a residue. The residue was purified by column chromatography ($SiO_2$, Petroleum ether/Ethyl acetate=10/1 to 1/1) to give (E)-N-[4-(pentafluoro-λ$^6$-sulfanyl)phenyl]-1-(3-pyridyl)ethanimine (1.5 g, 2.33 mmol, 25.50% yield, 50% purity) as a yellow oil. MS (ESI) m/z 323.1 $[M+H]^+$.

$^1H$ NMR (400 MHz, DMSO-$d_6$) δ=9.15 (d, J=1.7 Hz, 1H), 8.72 (dd, J=1.7, 4.7 Hz, 1H), 8.34 (td, J=1.9, 8.1 Hz, 1H), 7.93-7.84 (m, 2H), 7.55-7.50 (m, 1H), 7.07-6.96 (m, 2H), 2.26 (s, 3H).

Step 2: tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-methoxy-pyrrolidine-1-carboxylate To a solution of (E)-N-[4-(pentafluoro-2f-sulfanyl)phenyl]-1-(3-pyridyl)ethanimine (1 g, 3.10 mmol, 1 eq), 1,1-difluoro-4-isocyano-cyclohexane (450.36 mg, 3.10 mmol, 1 eq) and (2R,4R)-1-tert-butoxycarbonyl-4-methoxy-pyrrolidine-2-carboxylic acid (761.01 mg, 3.10 mmol, 1 eq) in t-BuOH (10 mL) was added $ZnCl_2$ (1 M, 18.62 mL, 6 eq), the mixture was stirred at 25° C. for 12 h. Upon completion, the reaction mixture was diluted with sat. $NaHCO_3$ (50 mL) and extracted with EA (20 mL*3). The combined organic layers were dried over $Na_2SO_4$, filtered and concentrated under reduced pressure to give a residue. The residue was purified by prep-HPLC (column: Kromasil C18 (250*50 mm*10 um); mobile phase: [water (0.05% $NH_3H_2O$+10 mM $NH_4HCO_3$)-ACN]; B %: 50%-70%, 10 min) and re-purified by prep-TLC ($SiO_2$, Petroleum ether:Ethyl acetate=0:1) to give tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-methoxy-pyrrolidine-1-carboxylate Isomer 1 (0.06 g, 67.35 umol, 2.17% yield, 80% purity) as a yellow solid. MS (ESI) m/z 713.3 $[M+H]^+$.

To give tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-methoxy-pyrrolidine-1-carboxylate Isomer 2 (0.07 g, 88.39 umol, 2.85% yield, 90% purity) as a yellow solid. MS (ESI) m/z 713.3 $[M+H]^+$.

Step 3: (2R,4R)—N-[2-[(4,4-difluorocyclohexyl)amino]-1-methyl-2-oxo-1-(3-pyridyl)ethyl]-4-methoxy-N-[4-(pentafluoro-λ$^6$-sulfanyl)phenyl]pyrrolidine-2-carboxamide Isomer 1

To a solution of tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-methoxy-pyrrolidine-1-carboxylate Isomer 1 (0.055 g, 77.17 umol, 1 eq) in DCM (1 mL) was added TFA (462.00 mg, 4.05 mmol, 0.3 mL, 52.51 eq), the mixture was stirred at 25° C. for 0.5 h. Upon completion, the reaction mixture was dried by blowing $N_2$ and then diluted with sat. $NaHCO_3$ (5 mL) and extracted with DCM (3 mL*3). The combined organic layers were dried over $Na_2SO_4$, filtered and concentrated under reduced pressure to give (2R,4R)—N-[2-[(4,4-difluorocyclohexyl)amino]-1-methyl-2-oxo-1-(3-pyridyl)ethyl]-4-methoxy-N-[4-(pentafluoro-λ$^6$-sulfanyl)phenyl]pyrrolidine- 2-carboxamide Isomer 1 (0.05 g, crude) as a yellow solid. MS (ESI) m/z 613.3 $[M+H]^+$.

(2R,4R)—N-[2-[(4,4-difluorocyclohexyl)amino]-1-methyl-2-oxo-1-(3-pyridyl)ethyl]-4-methoxy-N-[4-(pentafluoro-$\lambda^6$-sulfanyl)phenyl]pyrrolidine-2-carboxamide Isomer 2

To a solution of tert-butyl (2R,4R)-2-[[2-[(4,4-difluorocyclohexyl)amino]-1-methyl-2-oxo-1-(3-pyridyl)ethyl]-[4-(pentafluoro-$\lambda^6$-sulfanyl)phenyl]carbamoyl]-4-methoxy-pyrrolidine-1-carboxylate Isomer 2 (0.07 g, 98.22 umol, 1 eq) in DCM (1.5 mL) was added TFA (770.00 mg, 6.75 mmol, 0.5 mL, 68.76 eq), the mixture was stirred at 25° C. for 0.5 h. Upon completion, the reaction mixture was dried by blowing $N_2$, and then diluted with sat. $NaHCO_3$ (5 mL) and extracted with DCM (3 mL*3). The combined organic layers were dried over $Na_2SO_4$, filtered and concentrated under reduced pressure to give (2R,4R)—N-[2-[(4,4-difluorocyclohexyl)amino]-1-methyl-2-oxo-1-(3-pyridyl)ethyl]-4-methoxy-N-[4-(pentafluoro-$\lambda^6$-sulfanyl)phenyl]pyrrolidine-2-carboxamide Isomer 2 (0.06 g, crude) as a yellow solid. MS (ESI) m/z 613.2 $[M+H]^+$.

Step 4: (2R,4R)-1-cyano-N-[2-[(4,4-difluorocyclohexyl)amino]-1-methyl-2-oxo-1-(3-pyridyl)ethyl]-4-methoxy-N-[4-(pentafluoro-$\lambda^6$-sulfanyl)phenyl]pyrrolidine-2-carboxamide Isomer 1

To a solution of (2R,4R)—N-[2-[(4,4-difluorocyclohexyl) amino]-1-methyl-2-oxo-1-(3-pyridyl)ethyl]-4-methoxy-N-[4-(pentafluoro-$\lambda^6$-sulfanyl)phenyl]pyrrolidine-2-carboxamide Isomer 1 (0.05 g, 81.62 umol, 1 eq) in EtOH (2 mL) was added $NaHCO_3$ (20.57 mg, 244.86 umol, 9.52 uL, 3 eq), then BrCN (10.37 mg, 97.94 umol, 7.20 uL, 1.2 eq) in EtOH (0.5 mL) was added drop-wise at −5° C., the mixture was stirred at −5° C. for 0.5 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 30%-60%, 8 min) to give (2R,4R)-1-cyano-N-[2-[(4,4-difluorocyclohexyl)amino]-1-methyl-2-oxo-1-(3-pyridyl) ethyl]-4-methoxy-N-[4-(pentafluoro-$\lambda^6$-sulfanyl)phenyl] pyrrolidine-2-carboxamide Isomer 1 (17.93 mg, 27.73 umol, 33.97% yield, 98.6% purity) as a white solid. MS (ESI) m/z 638.2 $[M+H]^+$.

$^1$H NMR (400 MHz, METHANOL-$d_4$) δ=8.72-8.59 (m, 1H), 8.46-8.36 (m, 1H), 8.03-7.93 (m, 1H), 7.86 (br d, J=8.7 Hz, 2H), 7.68-7.46 (m, 2H), 7.43-7.28 (m, 1H), 4.13 (dd, J=5.7, 8.9 Hz, 1H), 4.00-3.85 (m, 2H), 3.60 (dd, J=6.0, 9.5 Hz, 1H), 3.49-3.42 (m, 1H), 3.28 (s, 3H), 2.15-1.82 (m, 1H), 1.73-1.53 (m, 2H).

(2R,4R)-1-cyano-N-[2-[(4,4-difluorocyclohexyl) amino]-1-methyl-2-oxo-1-(3-pyridyl)ethyl]-4-methoxy-N-[4-(pentafluoro-$\lambda^6$-sulfanyl)phenyl]pyrrolidine-2-carboxamide Isomer 2

To a solution of (2R,4R)—N-[2-[(4,4-difluorocyclohexyl) amino]-1-methyl-2-oxo-1-(3-pyridyl)ethyl]-4-methoxy-N-[4-(pentafluoro-λ6-sulfanyl)phenyl]pyrrolidine-2-carboxamide Isomer 2 (0.06 g, 97.94 umol, 1 eq) in EtOH (2 mL) was added $NaHCO_3$ (24.68 mg, 293.83 umol, 11.43 uL, 3 eq), then BrCN (12.45 mg, 117.53 umol, 8.65 uL, 1.2 eq) in EtOH (0.5 mL) was added drop-wise at −5° C., the mixture was stirred at −5° C. for 0.5 h under $N_2$ atmosphere. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 30%-60%, 8 min) to give (2R,4R)-1-cyano-N-[2-[(4,4-difluorocyclohexyl)amino]-1-methyl-2-oxo-1-(3-pyridyl)ethyl]-4-methoxy-N-[4-(pentafluoro-$\lambda^6$-sulfanyl)phenyl]pyrrolidine-2-carboxamide Isomer 2 (19.30 mg, 29.45 umol, 30.07% yield, 97.3% purity) as a yellow solid. MS (ESI) m/z 638.2 $[M+H]^+$.

$^1$H NMR (400 MHz, METHANOL-$d_4$) δ=8.58 (d, J=1.9 Hz, 1H), 8.38 (dd, J=1.3, 4.8 Hz, 1H), 7.95-7.82 (m, 2H), 7.79 (br d, J=7.9 Hz, 1H), 7.64 (br d, J=8.5 Hz, 1H), 7.42 (br d, J=8.5 Hz, 1H), 7.36-7.24 (m, 1H), 4.15 (dd, J=5.8, 8.7 Hz, 1H), 4.05-3.84 (m, 2H), 3.60 (dd, J=6.0, 9.5 Hz, 1H), 3.44 (br dd, J=5.0, 9.4 Hz, 1H), 3.27 (s, 3H), 2.17-1.82 (m, 1H), 1.79-1.54 (m, 2H).

Example 116: Synthesis of Compound 1288

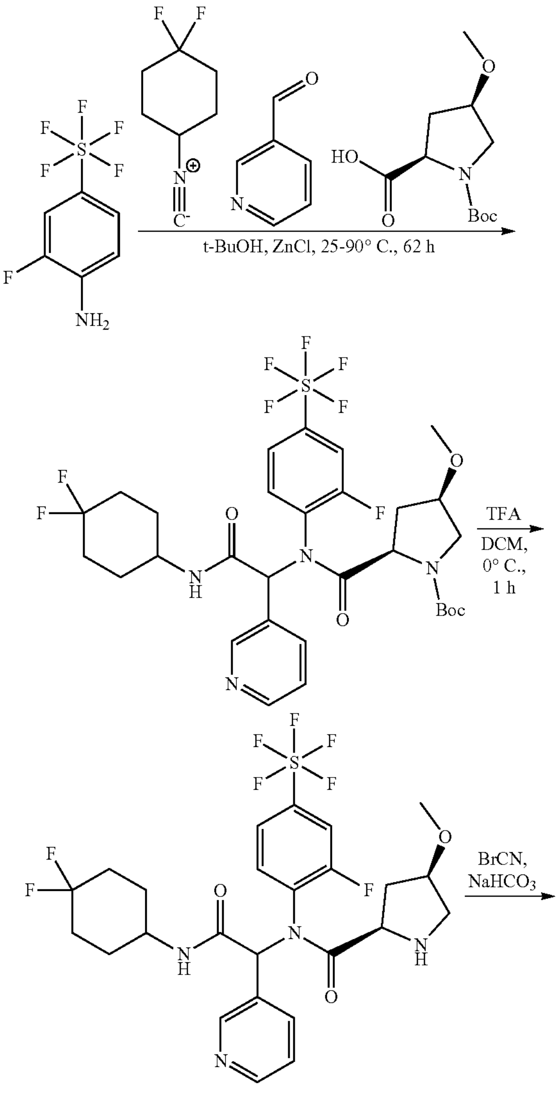

-continued

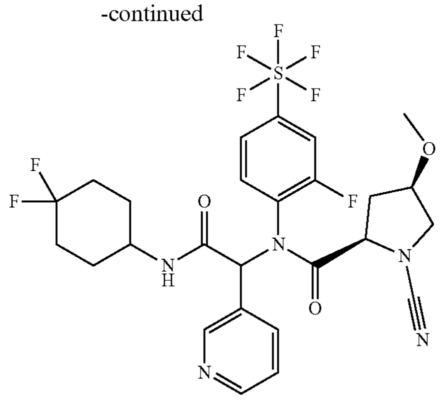

Step 1: tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-methoxy-pyrrolidine-1-carboxylate A solution of pyridine-3-carbaldehyde (474.21 mg, 4.43 mmol, 415.97 uL, 1.5 eq) and 2-fluoro-4-(pentafluoro-λ$^6$-sulfanyl)aniline (700 mg, 2.95 mmol, 1 eq) in t-BuOH (12 mL) was stirred at 90° C. for 48 h. (2R,4R)-1-tert-butoxycarbonyl-4-methoxy-pyrrolidine-2-carboxylic acid (1.45 g, 5.90 mmol, 2 eq), 1,1-difluoro-4-isocyano-cyclohexane (856.82 mg, 5.90 mmol, 2 eq) and $ZnCl_2$ (1 M, 8.85 mL, 3 eq) were added and the resulting mixture was stirred at 25° C. for 14 h. Upon completion, the reaction mixture was concentrated under reduced pressure and purified by prep-HPLC (column: Kromasil C18 (250*50 mm*10 um); mobile phase: [water (10 mM $NH_4HCO_3$)-ACN]; B %: 50%-70%, 10 min) to afford tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-methoxy-pyrrolidine-1-carboxylate Isomer 1 (465 mg, 583.94 umol, 19.78% yield, 90% purity) as light yellow solid. MS (ESI) m/z 717.3 [M+H]$^+$. Tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-methoxy-pyrrolidine-1-carboxylate Isomer 2 (655 mg, 731.15 umol, 24.77% yield, 80% purity) was obtained as light yellow solid. MS (ESI) m/z 717.3 [M+H]$^+$.

Step 2: (2R,4R)—N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide A solution of tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-methoxy-pyrrolidine-1-carboxylate Isomer 1 (455 mg, 571.38 umol, 90% purity, 1 eq), TFA (3.08 g, 27.01 mmol, 2 mL, 47.28 eq) in DCM (6 mL) was stirred at 0° C. for 1 h. Upon completion, the reaction mixture was concentrated under reduced pressure, the pH was adjusted to 7-8 with $NaHCO_3$ aq. (20 mL) and extracted with DCM (10 mL*3). The organic layers were washed with brine (10.0 mL), dried over $Na_2SO_4$, filtered, and concentrated under reduced pressure to afford (2R,4R)—N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide Isomer 1 (352 mg, crude) as yellow solid. MS (ESI) m/z 617.2 [M+H]$^+$.

A solution of tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-methoxy-pyrrolidine-1-carboxylate Isomer 2 (645 mg, 719.99 umol, 80% purity, 1 eq) and TFA (3.08 g, 27.01 mmol, 2 mL, 37.52 eq) in DCM (6 mL) was stirred at 0° C. for 1 h. Upon completion, the reaction mixture was concentrated under reduced pressure, pH was adjusted to 7~8 with $NaHCO_3$ aq. (20 mL) and extracted with DCM (10 mL*3). The organic layers were washed with brine (10.0 mL), dried over $Na_2SO_4$, filtered and concentrated under reduced pressure to give (2R,4R)—N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide Isomer 2 (443 mg, crude) as yellow solid. MS (ESI) m/z 617.2 [M+H]$^+$.

Step 3: (2R,4R)-1-cyano-N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide To a solution of (2R,4R)—N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-hydroxy-pyrrolidine-2-carboxamide Isomer 1 (352 mg, 570.90 umol, 1 eq) in EtOH (4 mL) was added $NaHCO_3$ (95.92 mg, 1.14 mmol, 44.41 uL, 2 eq), and then BrCN (66 mg, 623.10 umol, 45.83 uL, 1.09 eq) was added under $N_2$ at −10° C. The resulting mixture was stirred at −10° C. for 1 h. Upon completion, the mixture was concentrated under reduced pressure and purified by prep-HPLC (column: Waters Xbridge BEH C18 100*30 mm*10 um; mobile phase: [water (10 mM $NH_4HCO_3$)-ACN]; B %: 35%-65%, 10 min) to give (2R,4R)-1-cyano-N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide Isomer 1 (173.68 mg, 270.71 umol, 47.42% yield, 100% purity) as light yellow solid. MS (ESI) m/z 642.2 [M+H]$^+$.

$^1$H NMR (400 MHz, METHANOL-$d_4$) δ ppm 8.57-8.28 (m, 2H), 8.24-8.10 (m, 1H), 7.87-7.67 (m, 1H), 7.66-7.49 (m, 2H), 7.59-7.19 (m, 1H), 6.32-6.1928 (m, 1H), 4.18-4.05 (m, 1H), 4.03-3.85 (m, 2H), 3.71-3.58 (m, 1H), 3.57-3.45 (m, 1H), 3.29-3.17 (m, 3H), 2.27-1.75 (m, 8H), 1.74-1.35 (m, 2H).

$^1$H NMR (400 MHz, DMSO-$d_6$) δ ppm 8.51-8.24 (m, 2H), 8.24-8.00 (m, 2H), 7.81-7.58 (m, 2H), 7.41 (s, 1H), 7.16 (s, 1H), 6.22 (s, 1H), 4.16-3.98 (m, 1H), 3.97-3.74 (m, 2H), 3.67-3.55 (m, 1H), 3.40-3.27 (m, 1H), 3.21 (s, 3H), 2.21-1.72 (m, 8H), 1.68-1.32 (m, 2H).

To a solution of (2R,4R)—N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide Isomer 2 (443 mg, 718.50 umol, 1 eq) in EtOH (5 mL) was added $NaHCO_3$ (120.72 mg, 1.44 mmol, 55.89 uL, 2 eq), followed by the addition of BrCN (80 mg, 755.28 umol, 55.56 uL, 1.05 eq) under $N_2$ at −10° C. The resulting mixture was stirred at −10° C. for 1 h. Upon completion, the mixture was concentrated under reduced pressure and purified by prep-HPLC (column: Waters Xbridge BEH C18 100*30 mm*10 um; mobile phase: [water (10 mM $NH_4HCO_3$)-ACN]; B %: 35%-65%, 10 min) to give (2R,4R)-1-cyano-N-[2-[(4,4-difluorocyclohexyl)amino]-2-oxo-1-(3-pyridyl)ethyl]-N-[2-fluoro-4-(pentafluoro-λ$^6$-sulfanyl)phenyl]-4-methoxy-pyrrolidine-2-carboxamide Isomer 2 (130.76 mg, 199.94 umol, 27.83% yield, 98.1% purity) as light yellow solid. MS (ESI) m/z 642.2 [M+H]$^+$.

$^1$H NMR (400 MHz, MeOD-$d_4$) δ ppm 8.58-8.33 (m, 2H), 8.28-8.15 (m, 1H), 7.94-7.70 (m, 1H), 7.65-7.37 (m, 2H), 7.27-7.07 (m, 1H), 6.12-6.02 (m, 1H), 4.36-4.15 (m, 1H), 4.06-3.80 (m, 2H), 3.68-3.57 (m, 1H), 3.57-3.47 (m, 1H), 3.30-3.17 (m, 3H), 2.19-1.73 (m, 8H), 1.72-1.33 (m, 2H)

$^1$H NMR (400 MHz, DMSO-$d_6$) δ ppm 8.42 (s, 2H), 8.10 (s, 2H), 7.91-7.59 (m, 2H), 7.41 (s, 1H), 7.18 (s, 1H), 6.17-6.02 (m, 1H), 4.26-3.99 (m, 1H), 3.99-3.87 (m, 1H), 3.79 (s, 1H), 3.64-3.50 (m, 1H), 3.44-3.28 (m, 1H), 3.23-3.12 (m, 3H), 2.17-1.68 (m, 8H), 1.65-1.33 (m, 2H).

Example 117: Synthesis of Compound 1105

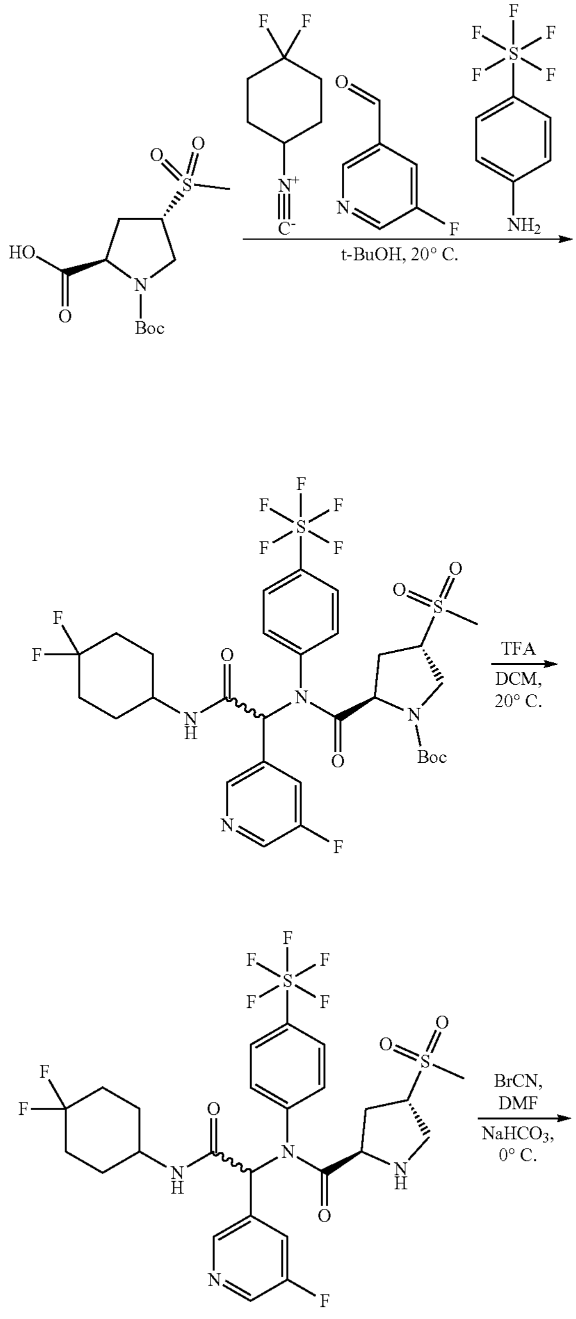

-continued

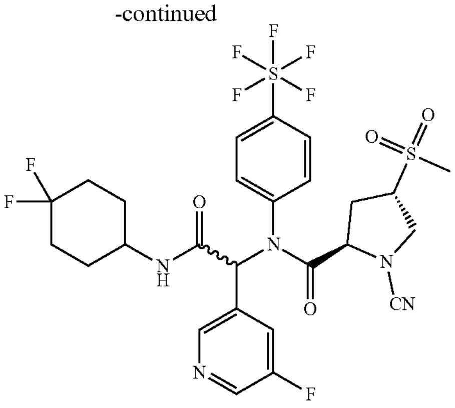

Step 1: tert-butyl (2R,4S)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-4-methylsulfonyl-pyrrolidine-1-carboxylate A solution of 4-(pentafluoro-$\lambda^6$-sulfanyl)aniline (300 mg, 1.37 mmol, 1 eq), 5-fluoropyridine-3-carbaldehyde (171.23 mg, 1.37 mmol, 1 eq) in t-BuOH (9 mL) was stirred for 1 h. To the solution was added (2R,4S)-1-tert-butoxycarbonyl-4-methylsulfonyl-pyrrolidine-2-carboxylic acid (401.51 mg, 1.37 mmol, 1 eq) and stirred for 10 min. 1,1-Difluoro-4-isocyano-cyclohexane (198.68 mg, 1.37 mmol, 1 eq) in t-BuOH (1 mL) was added, stirred for 10 min, followed by the addition of $ZnCl_2$ (1 M, 4.11 mL, 3 eq), and the resulting mixture was stirred at 20° C. for 14 h 40 min. Upon completion, the reaction mixture was concentrated under reduced pressure to remove solvent. The residue was purified by prep-HPLC (column: Kromasil C18 (250*50 mm*10 um); mobile phase: [water (10 mM $NH_4HCO_3$)-ACN]; B %: 50%-70%, 10 min) to afford tert-butyl (2R,4S)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-4-methylsulfonyl-pyrrolidine-1-carboxylate (297.7 mg, 389.28 umol, 28.44% yield) and tert-butyl (2R,4S)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-4-methylsulfonyl-pyrrolidine-1-carboxylate (227 mg, 283.92 umol, 20.74% yield) as a yellow solid. MS (ESI) m/z 765.2 $[M+H]^+$ Step 2: (2R,4S)—N-[2-[(4,4-difluorocyclohexyl)amino]-1-(5-fluoro-3-pyridyl)-2-oxo-ethyl]-4-methylsulfonyl-N-[4-(pentafluoro-$\lambda^6$-sulfanyl)phenyl]pyrrolidine-2-carboxamide Isomer 1: To a solution of tert-butyl (2R,4S)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-4-methylsulfonyl-pyrrolidine-1-carboxylate (297.7 mg, 389.28 umol, 1 eq) in DCM (6 mL) was added TFA (4.62 g, 40.52 mmol, 3 mL, 104.08 eq). The mixture was stirred at 20° C. for 1 h. Upon completion, the reaction mixture was added with $NaHCO_3$ (25 mL) at 20° C., and then extracted with DCM (20 mL*3). The combined organic layers were washed with brine (20 mL*2), dried over $Na_2SO_4$, filtered and concentrated to afford (2R,4S)—N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide (237.5 mg, crude) as a yellow oil. MS (ESI) m/z 665.1 $[M+H]^+$ Isomer 2: To a solution of tert-butyl (2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-methylsulfonyl-pyrrolidine-1-carboxylate (227 mg, 296.83 umol, 1 eq) in DCM (5 mL) was added TFA (3.85 g, 33.77 mmol, 2.5 mL, 113.75 eq). The mixture was stirred at 20° C. for 1 h. Upon completion, the reaction mixture was added with $NaHCO_3$ (25 mL) at 25° C., and then extracted with DCM (20 mL*3). The combined organic layers were washed with brine (20 mL*2), dried over $Na_2SO_4$, filtered and concentrated to afford (2R,4S)—N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide (190.9 mg, crude) as a yellow oil. MS (ESI) m/z 665.1 $[M+H]^+$ Step 3: (2R,4S)-1-cyano-N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide Isomer 1: To a solution of (2R,4S)—N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide (227.5 mg, 342.30 umol, 1 eq) and $NaHCO_3$ (86.27 mg, 1.03 mmol, 39.94 uL, 3 eq) in DMF (3 mL) was added BrCN (47.13 mg, 444.98 umol, 32.73 uL, 1.3 eq) in DMF (1 mL) at 0° C. The reaction mixture was stirred at 0° C. for 1 h. Upon completion, the reaction mixture was quenched by the addition of $H_2O$ (25 mL) at 25° C., and then extracted with EtOAc (25 mL*3). The combined organic layers were washed with brine (20 mL*2), dried over $Na_2SO_4$, filtered and concentrated to give a residue. The residue was purified by prep-HPLC (column: column: Phenomenex Luna C18 75*30 mm*3 um; mobile phase: [water (0.2% FA)-ACN]; B %: 30%-70%, 8 min), to give (2R,4S)-1-cyano-N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide (108.8 mg, 156.19 umol, 45.63% yield, 99% purity) as a white solid. MS (ESI) n/z 690.1 $[M+H]^+$ 1H NMR (400 MHz, MeOD-$d_4$) δ=8.39-8.16 (m, 2H), 8.08-6.97 (m, 5H), 6.22 (s, 1H), 4.39 (d, J=4.4, 8.4 Hz, 1H), 4.13-3.84 (m, 4H), 2.97 (s, 3H), 2.57-2.29 (m, 2H), 2.14-1.79 (m, 6H), 1.70-1.56 (m, 1H), 1.53-1.39 (n, 1H)

Isomer 2: To a solution of (2R,4S)—N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide (190.9 mg, 287.23 umol, 1 eq) and $NaHCO_3$ (72.39 mg, 861.68 umol, 33.51 uL, 3 eq) in DMF (3 mL) was added BrCN (39.55 mg, 373.40 umol, 27.47 uL, 1.3 eq) in DMF (1 mL) at 0° C. The mixture was stirred at 0° C. for 1 h. Upon completion, the reaction mixture was quenched by addition $H_2O$ (25 mL) at 25° C., and then extracted with EtOAc (25 mL*3). The combined organic layers were washed with brine (20 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-70%, 8 min) to give (2R,4S)-1-cyano-N-[2-[(4,4-difluorocyclohexyl)amino]-1-(5-fluoro-3-pyridyl)-2-oxo-ethyl]-4-methylsulfonyl-N-[4-(pentafluoro-λ$^6$-sulfanyl)phenyl]pyrrolidine-2-carboxamide (113.8 mg, 165.01 umol, 57.45% yield, 100% purity) as a white solid. MS (ESI) m/z 690.1 $[M+H]^+$ 1H NMR (400 MHz, MeOD-$d_4$) δ=8.35 (d, J=2.8 Hz, 1H), 8.25 (s, 1H), 7.81 (s, 2H), 6.10 (s, 1H), 4.36 (d, J=4.4, 7.8 Hz, 1H), 4.15-3.81 (m, 4H), 2.97 (s, 3H), 2.56-2.36 (m, 2H), 2.15-1.78 (m, 7H), 1.69-1.57 (m, 1H), 1.51-1.39 (m, 1H)

Example 118: Synthesis of Compound 1289

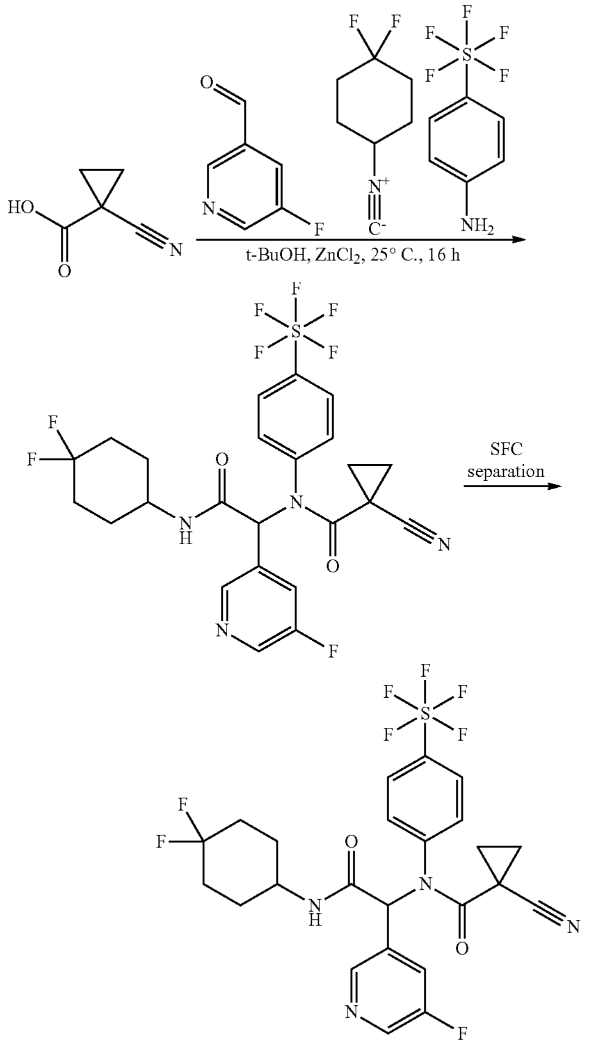

Step 1: 1-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]cyclopropanecarboxamide A solution of 5-fluoropyridine-3-carbaldehyde (281.51 mg, 2.25 mmol, 4.29 uL, 1 eq), 4-(pentafluoro-λ$^6$-sulfanyl)aniline (493.20 mg, 2.25 mmol, 1 eq) in t-BuOH (8 mL) stirred at 25° C. for 2 h. To the solution was added 1-cyanocyclopropanecarboxylic acid (250 mg, 2.25 mmol, 1 eq) and then a solution of 1,1-difluoro-4-isocyano-cyclohexane (326.62 mg, 2.25 mmol, 1 eq) was added t-BuOH (2 mL) in batches (three times). $ZnCl_2$ (1 M, 6.75 mL, 3 eq)

was added to the resulting mixture and then was stirred at 25° C. for 14 h. Upon completion, the reaction mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 45%-70%, 10 min) to afford 1-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]cyclopropanecarboxamide (155 mg, 261.83 umol, 11.64% yield, 98.4% purity) as a white solid. MS (ESI) m/z 583.2 $[M+1]^+$ $^1H$ NMR (400 MHz, MeOD-$d_4$) δ=8.35 (d, J=2.8 Hz, 1H), 8.21 (s, 1H), 7.77-7.75 (m, 2H), 7.55 (s, 2H), 7.42-7.39 (m, 1H), 6.10 (s, 1H), 3.91-3.82 (m, 1H), 2.07-1.84 (m, 7H), 1.79-1.71 (m, 1H), 1.62-1.51 (m, 1H), 1.48-1.45 (m, 3H).

Step 2: 1-cyano-N-[2-[(4,4-difluorocyclohexyl) amino]-1-(5-fluoro-3-pyridyl)-2-oxo-ethyl]-N-[4-(pentafluoro-$\lambda^6$-sulfanyl)phenyl]cyclopropanecarboxamide 1-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]cyclopropanecarboxamide (150 mg 98.4% purity) was separated by SFC (condition: column: DAICEL CHIRALPAK AD (250 mm*30 mm, 10 um); mobile phase: [0.1% $NH_3H_2O$ ETOH]; B %: 35%-35%, 6 min) to give 1-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]cyclopropanecarboxamide (65 mg, 109.80 umol, 42.64% yield, 98.4% purity) as a white solid. MS (ESI) m/z 583.2 $[M+H]^+$ $^1H$ NMR (400 MHz, MeOD-$d_4$) δ=8.35 (d, J=2.8 Hz, 1H), 8.21 (s, 1H), 7.78-7.75 (m, 2H), 7.55 (s, 2H), 7.42-7.39 (m, 1H), 6.10 (s, 1H), 3.91-3.82 (m, 1H), 2.07-1.84 (m, 7H), 1.79-1.71 (m, 1H), 1.62-1.51 (m, 1H), 1.48-1.45 (m, 3H).

1-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]cyclopropanecarboxamide (65 mg, 111.59 umol, 43.33% yield, 100% purity) was obtained as a white solid. MS (ESI) m/z 583.2 $[M+H]^+$ $^1H$ NMR (400 MHz, MeOD-$d_4$) δ=8.35 (d, J=2.8 Hz, 1H), 8.21 (s, 1H), 7.77-7.75 (m, 2H), 7.55 (s, 2H), 7.42-7.39 (m, 1H), 6.10 (s, 1H), 3.91-3.82 (m, 1H), 2.07-1.84 (m, 7H), 1.79-1.71 (m, 1H), 1.62-1.51 (m, 1H), 1.48-1.45 (m, 3H).

Example 119: Synthesis of Compound 1290

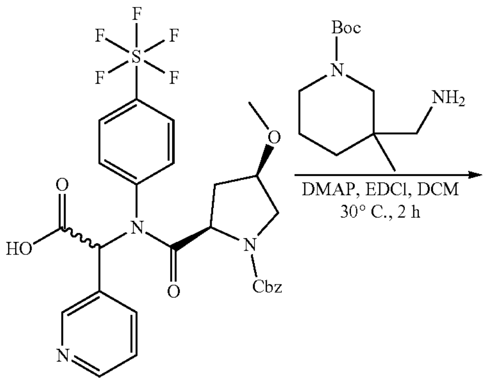

-continued

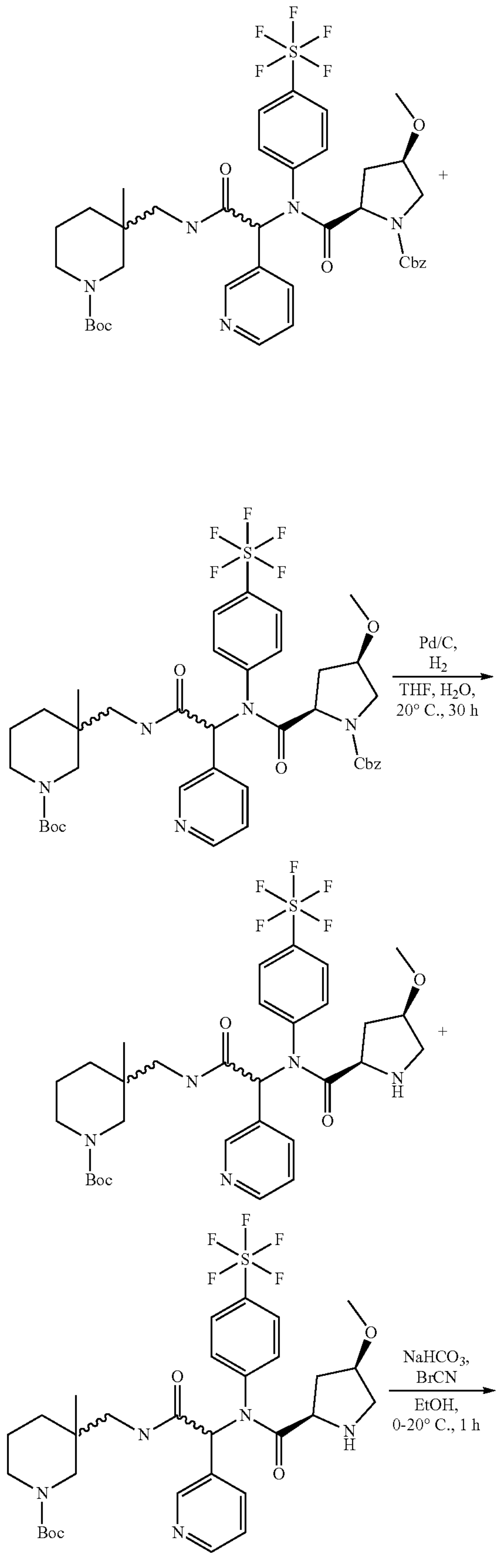

-continued

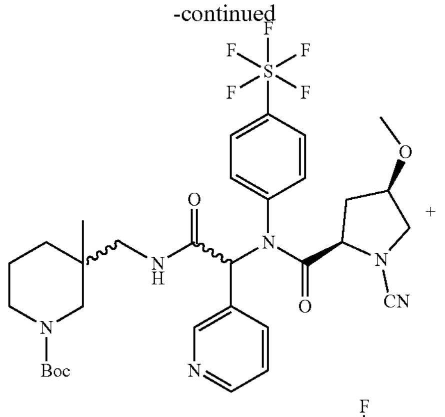

+

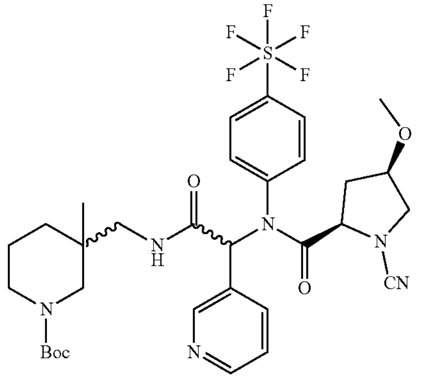

Step 1: tert-butyl 3-[[[2-[N-[(2R,4R)-1-benzyloxy-carbonyl-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate A mixture of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (300 mg, 487.35 umol, 1 eq), tert-butyl 3-(aminomethyl)-3-methyl-piperidine-1-carboxylate (333.83 mg, 1.46 mmol, 3 eq), DMAP (178.62 mg, 1.46 mmol, 3 eq) and EDCI (280.28 mg, 1.46 mmol, 3 eq) in DCM (3 mL) was stirred at 30° C. for 2 h. Upon completion, the mixture was added $H_2O$ (50 mL) and then extracted with EA (30 mL*3). The combined organic layers were washed with brine (50 mL), dried over $Na_2SO_4$, filtered and concentrated under reduced pressure to give a residue. The residue was purified by prep-HPLC (column: Kromasil C18 (250*50 mm*10 um); mobile phase: [water (0.05% $NH_3H_2O$+10 mM $NH_4HCO_3$)-ACN]; B %: 50%-70%, 10 min) to get two products tert-butyl 3-[[[2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 1 (80 mg, 96.87 umol, 19.88% yield) as white solid, MS (ESI) m/z 826.3 $[M+H]^+$; and tert-butyl3-[[[2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 2 (80 mg, 96.87 umol, 19.88% yield) as white solid. MS (ESI) m/z 826.3 $[M+H]^+$.

Step 2: tert-butyl3-[[[2-[N-[(2R,4R)-4-methoxypyrrolidine-2-carbonyl]-4-(pentafluoro-$\lambda^6$-sulfanyl)anilino]-2-(3-pyridyl)acetyl]amino]methyl]-3-methyl-piperidine-1-carboxylate A mixture of tert-butyl 3-[[[2-[N-[(2R,4R)-1-benzyloxy-carbonyl-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 1 (70 mg, 84.76 umol, 1 eq) and Pd/C (60 mg, 10% purity) in THF (0.8 mL) and $H_2O$ (0.2 mL) under $H_2$ (15 Psi) was stirred at 20° C. for 30 h. Upon completion, Pd/C was filtered, and then the reaction mixture was concentrated under reduced pressure to get the product tert-butyl3-[[[2-[N-[(2R,4R)-4-methoxypyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 1 (30 mg, 41.01 umol, 48.38% yield, 94.56% purity) as white solid. MS (ESI) m/z 692.3 $[M+H]^+$.

A mixture of tert-butyl 3-[[[2-[N-[(2R,4R)-1-benzyloxy-carbonyl-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 2 (70 mg, 84.76 umol, 1 eq) and Pd/C (70 mg, 10% purity) in THF (2 mL) and $H_2O$ (0.5 mL) under $H_2$ (15 Psi) was stirred at 20° C. for 30 h. Upon completion, Pd/C was filtered, and then the reaction mixture was concentrated under reduced pressure to get the product tert-butyl3-[[[2-[N-[(2R,4R)-4-methoxypyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 2 (35 mg, 42.66 umol, 50.33% yield, 84.31% purity) as white solid. MS (ESI) m/z 692.3 $[M+H]^+$.

Step 3: tert-butyl 3-[[[2-[N-[(2R,4R)-1-cyano-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate A solution of tert-butyl 3-[[[2-[N-[(2R,4R)-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 1 (30 mg, 43.37 umol, 1 eq) and $NaHCO_3$ (10.93 mg, 130.10 umol, 5.06 uL, 3 eq) in EtOH (1 mL) was cooled to 0° C. BrCN (8 mg, 75.53 umol, 5.56 uL, 1.74 eq) in EtOH (0.5 mL) was added into the solution, and then the mixture was stirred for 1 h and warmed to 20° C. gradually. Upon completion, the mixture was added with $H_2O$ (30 mL) and then extracted with EA (30 mL*3). The combined organic layers were washed with brine (30 mL), dried over $Na_2SO_4$, filtered and concentrated under reduced pressure to give a residue. The residue was purified by prep-HPLC (column: Phenomenex Gemini-NX C18 75*30 mm*3 um; mobile phase: [water (0.05% $NH_3H_2O$+10 mM $NH_4$—$CO_3$)-ACN]; B %: 45%-70%, 8 min) to afford tert-butyl 3-[[[2-[N-[(2R,4R)-1-cyano-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate (16 mg, 21.63 umol, 49.87% yield, 96.88% purity) as white solid. MS (ESI) m/z 717.3 $[M+H]^+$.

$^1H$ NMR (400 MHz, METHANOL-$d_4$) δ=8.45-8.28 (m, 2H), 8.02-7.50 (m, 4H), 7.48-6.83 (m, 2H), 6.27 (s, 1H), 4.33-4.15 (m, 1H), 4.01-3.84 (m, 1H), 3.69-3.58 (m, 1H), 3.56-3.41 (m, 2H), 3.39-3.33 (m, 1H), 3.29-3.25 (m, 3H), 3.24-3.16 (m, 1H), 3.15-2.82 (m, 3H), 2.18-1.92 (m, 2H), 1.61-1.24 (m, 13H), 0.91-0.75 (m, 3H)

A solution of tert-butyl 3-[[[2-[N-[(2R,4R)-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate Isomer 2 (35 mg, 50.60 umol, 1 eq) and $NaHCO_3$ (12.75 mg, 151.79 umol, 5.90 uL, 3 eq) in EtOH (1 mL) was cooled to 0° C., and then BrCN (6 mg, 56.65 umol, 4.17 uL, 1.12 eq) in EtOH (0.5 mL) was added to the solution. The resulting mixture was stirred for 1 h and warmed to 20° C. gradually. Upon completion, the mixture was added $H_2O$ (30 mL) and then extracted with EA (30 mL*3). The combined organic layers were washed with brine (30 mL), dried over $Na_2SO_4$, filtered and concentrated under reduced pressure to give a residue. The residue was purified by prep-HPLC (column: Phenomenex Gemini-NX C18 75*30 mm*3 um; mobile phase: [water (0.05% $NH_3H_2O$+10 mM $NH_4HCO_3$)-ACN]; B %: 45%-70%, 8 min) to afford tert-butyl 3-[[[2-[N-[(2R,4R)-1-cyano-4-methoxy-pyrrolidine-2-carbonyl]-4-(pentafluoro-$\lambda^6$-sulfanyl)anilino]-2-(3-pyridyl)acetyl]amino]methyl]-3-methyl-piperidine-1-carboxylate (13 mg, 16.20 umol, 32.02% yield, 89.33% purity) as a white solid. MS (ESI) m/z 717.3 $[M+H]^+$.

$^1$H NMR (400 MHz, METHANOL-$d_4$) δ=8.48-8.32 (m, 2H), 7.93-7.50 (m, 4H), 7.41-6.92 (m, 2H), 6.09 (s, 1H), 4.34-4.19 (m, 1H), 4.17-3.76 (m, 2H), 3.65-3.57 (m, 1H), 3.54-3.41 (m=2H), 3.28 (s, 3H), 3.25-3.19 (m, 1H), 3.15-2.86 (m, 3H), 2.16-2.01 (m, 1H), 2.00-1.86 (m, 1H), 1.54-1.36 (m, 13H), 0.91-0.74 (m, 3H)

Example 120: Synthesis of Compound 1170

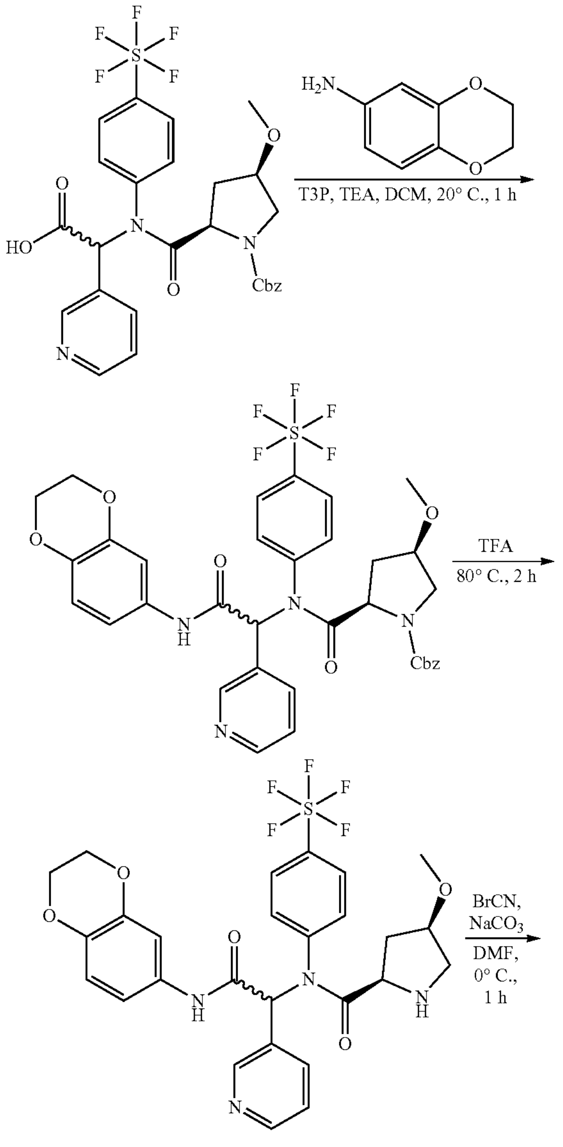

-continued

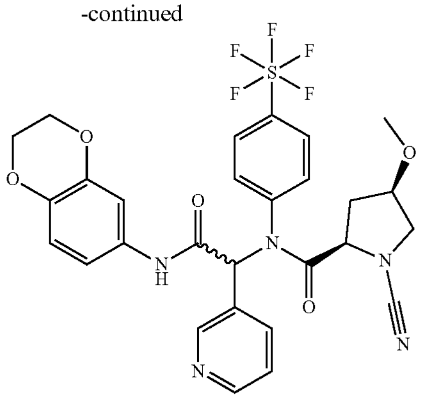

Step 1: benzyl (2R,4R)-2-[[2-(2,3-dihydro-1,4-benzodioxin-6-ylamino)-2-oxo-1-(3-pyridyl)ethyl]-[4-(pentafluoro-$\lambda^6$-sulfanyl)phenyl]carbamoyl]-4-methoxy-pyrrolidine-1-carboxylate A mixture of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (300 mg, 487.35 umol, 1 eq), 2,3-dihydro-1,4-benzodioxin-6-amine (110.50 mg, 731.03 umol, 89.84 uL, 1.5 eq), T3P (930.40 mg, 1.46 mmol, 869.54 uL, 50% purity, 3 eq), and TEA (147.94 mg, 1.46 mmol, 203.50 uL, 3 eq) in DCM (4 mL) was degassed and purged with $N_2$ for 3 times, and then the mixture was stirred at 20° C. for 1 h under $N_2$ atmosphere. Upon completion, the reaction mixture was poured into $H_2O$ (25 mL) at 25° C., and then extracted with DCM (20 mL*3). The combined organic layers were washed with brine (20 mL*2), dried over $Na_2SO_4$, filtered and concentrated under reduced pressure to give a residue. The residue was purified by prep-TLC ($SiO_2$, DCM:MeOH=10:1) to give benzyl (2R,4R)-2-[[2-(2,3-dihydro-1,4-benzodioxin-6-ylamino)-2-oxo-1-(3-pyridyl)ethyl]-[4-(pentafluoro-$\lambda^6$-sulfanyl)phenyl]carbamoyl]-4-methoxy-pyrrolidine-1-carboxylate (118 mg, 122.93 umol, 25.22% yield, 78% purity) and benzyl (2R,4R)-2-[[2-(2,3-dihydro-1,4-benzodioxin-6-ylamino)-2-oxo-1-(3-pyridyl)ethyl]-[4-(pentafluoro-$\lambda^6$-sulfanyl)phenyl]carbamoyl]-4-methoxy-pyrrolidine-1-carboxylate (112 mg, 142.11 umol, 29.16% yield, 95% purity) as a yellow oil. MS (ESI) m/z 749.2 $[M+H]^+$ Step 2: (2R,4R)—N-[2-(2,3-dihydro-1,4-benzodioxin-6-ylamino)-2-oxo-1-(3-pyridyl)ethyl]-4-methoxy-N-[4-(pentafluoro-$\lambda^6$-sulfanyl)phenyl]pyrrolidine-2-carboxamide Isomer 1: A solution of benzyl (2R,4R)-2-[[2-(2,3-dihydro-1,4-benzodioxin-6-ylamino)-2-oxo-1-(3-pyridyl)ethyl]-[4-(pentafluoro-$\lambda^6$-sulfanyl)phenyl]carbamoyl]-4-methoxy-pyrrolidine-1-carboxylate (98 mg, 130.89 umol, 1 eq) in TFA (3 mL) was stirred at 80° C. for 2 h. Upon completion, the reaction mixture was poured into $NaHCO_3$ (25 mL) at 20° C., and then extracted with DCM (20 mL*3). The combined organic layers were washed with brine (20 mL*2), dried over $Na_2SO_4$, filtered and concentrated under reduced pressure to give (2R,4R)—N-[2-(2,3-dihydro-1,4-benzodioxin-6-ylamino)-2-oxo-1-(3-pyridyl)ethyl]-4-methoxy-N-[4-(pentafluoro-$\lambda^6$-sulfanyl)phenyl]pyrrolidine-2-carboxamide (80 mg, crude) as a yellow oil. MS (ESI) m/z 615.2 $[M+H]^+$ Isomer 2: A solution of benzyl (2R,4R)-2-[[2-(2,3-dihydro-1,4-benzodioxin-6-ylamino)-2-oxo-1-(3-pyridyl)ethyl]-[4-(pentafluoro-λ$^6$-sulfanyl)phenyl]carbamoyl]-4-methoxy-pyrrolidine-1-carboxylate (112 mg, 149.59 umol, 1 eq) in TFA (3 mL) was stirred at 80° C. for 2 h. Upon completion, the reaction mixture was poured into $NaHCO_3$ (25 mL) at 20° C., and then extracted with DCM (20 mL*3). The combined organic layers were washed with brine (20 mL*2), dried over $Na_2SO_4$, filtered and concentrated under reduced pressure to give (2R,4R)—N-[2-(2,3-dihydro-1,4-benzodioxin-6-ylamino)-2-oxo-1-(3-pyridyl)ethyl]-4-methoxy-N-[4-(pentafluoro-λ$^6$-sulfanyl)phenyl]pyrrolidine-2-carboxamide (91 mg, crude) as a yellow oil. MS (ESI) m/z 615.2 $[M+H]^+$ Step 3: (2R,4R)-1-cyano-N-[2-(2,3-dihydro-1,4-benzodioxin-6-ylamino)-2-oxo-1-(3-pyridyl)ethyl]-4-methoxy-N-[4-(pentafluoro-λ$^6$-sulfanyl)phenyl] pyrrolidine-2-carboxamide Isomer 1: To a solution of (2R,4R)—N-[2-(2,3-dihydro-1,4-benzodioxin-6-ylamino)-2-oxo-1-(3-pyridyl)ethyl]-4-methoxy-N-[4-(pentafluoro-6-sulfanyl)phenyl]pyrrolidine-2-carboxamide (70 mg, 113.90 umol, 1 eq) and $NaHCO_3$ (28.70 mg, 341.70 umol, 13.29 uL, 3 eq) in DMF (3 mL) was added BrCN (15.68 mg, 148.07 umol, 10.89 uL, 1.3 eq) in DMF (0.5 mL) at 0° C. The resulting mixture was stirred at 0° C. for 1 h. Upon completion, the reaction mixture was quenched by addition $H_2O$ (25 mL) at 20° C., and then extracted with EtOAc (25 mL*3). The combined organic layers were washed with brine (25 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 20%-50%, 8 min) to give (2R,4R)-1-cyano-N-[2-(2,3-dihydro-1,4-benzodioxin-6-ylamino)-2-oxo-1-(3-pyridyl)ethyl]-4-methoxy-N-[4-(pentafluoro-λ$^6$-sulfanyl)phenyl]pyrrolidine-2-carboxamide (18.85 mg, 29.35 umol, 25.77% yield, 99.6% purity) as a white solid. MS (ESI) m/z 640.2 $[M+H]^+$ Isomer 1: 1H NMR (400 MHz, MeOD-$d_4$) δ=8.46-8.37 (m, 2H), 8.23-7.32 (m, 5H), 7.26 (d, J=4.8, 7.8 Hz, 1H), 7.17 (d, J=2.4 Hz, 1H), 6.89 (d, J=2.4, 8.8 Hz, 1H), 6.74 (d, J=8.8 Hz, 1H), 6.23 (s, 1H), 4.28 (d, J=5.8, 8.8 Hz, 1H), 4.23-4.18 (m, 4H), 3.92 (q, J=5.4 Hz, 1H), 3.62 (d, J=5.8, 9.8 Hz, 1H), 3.54-3.47 (m, 1H), 3.29 (s, 3H), 2.18-2.07 (m, 1H), 1.98 (d, J=4.8, 13.4 Hz, 1H)

Isomer 2: To a solution of (2R,4R)—N-[2-(2,3-dihydro-1,4-benzodioxin-6-ylamino)-2-oxo-1-(3-pyridyl)ethyl]-4-methoxy-N-[4-(pentafluoro-λ$^6$-sulfanyl)phenyl]pyrrolidine-2-carboxamide (81 mg, 131.80 umol, 1 eq) and $NaHCO_3$ (33.22 mg, 395.39 umol, 15.38 uL, 3 eq) in DMF (3 mL) was added BrCN (18.15 mg, 171.34 umol, 12.60 uL, 1.3 eq) in DMF (0.5 mL) at 0° C. The mixture was stirred at 0° C. for 1 h. Upon completion, the reaction mixture was quenched by addition $H_2O$ (25 mL) at 20° C., and then extracted with EtOAc (25 mL*3). The combined organic layers were washed with brine (25 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 25%-55%, 8 min) to give (2R,4R)-1-cyano-N-[2-(2,3-dihydro-1,4-benzodioxin-6-ylamino)-2-oxo-1-(3-pyridyl)ethyl]-4-methoxy-N-[4-(pentafluoro-λ$^6$-sulfanyl)phenyl]pyrrolidine-2-carboxamide (8.8 mg, 12.95 umol, 9.82% yield, 94.1% purity) as a white solid. MS (ESI) m/z 640.2 $[M+H]^+$ Isomer 2: 1H NMR (400 MHz, MeOD-$d_4$) δ=8.42-8.31 (m, 2H), 8.28-7.46 (m, 5H), 7.27-7.21 (m, 2H), 6.92 (d, J=2.4, 8.8 Hz, 1H), 6.76 (d, J=8.8 Hz, 1H), 6.41 (s, 1H), 4.28 (t, J=7.4 Hz, 1H), 4.24-4.20 (m, 4H), 3.93-3.87 (m, 1H), 3.64 (d, J=6.4, 9.4 Hz, 1H), 3.52-3.45 (m, 1H), 3.29-3.28 (m, 3H), 2.08 (t, J=6.8 Hz, 2H)

Example 121: Synthesis of Compound 1200

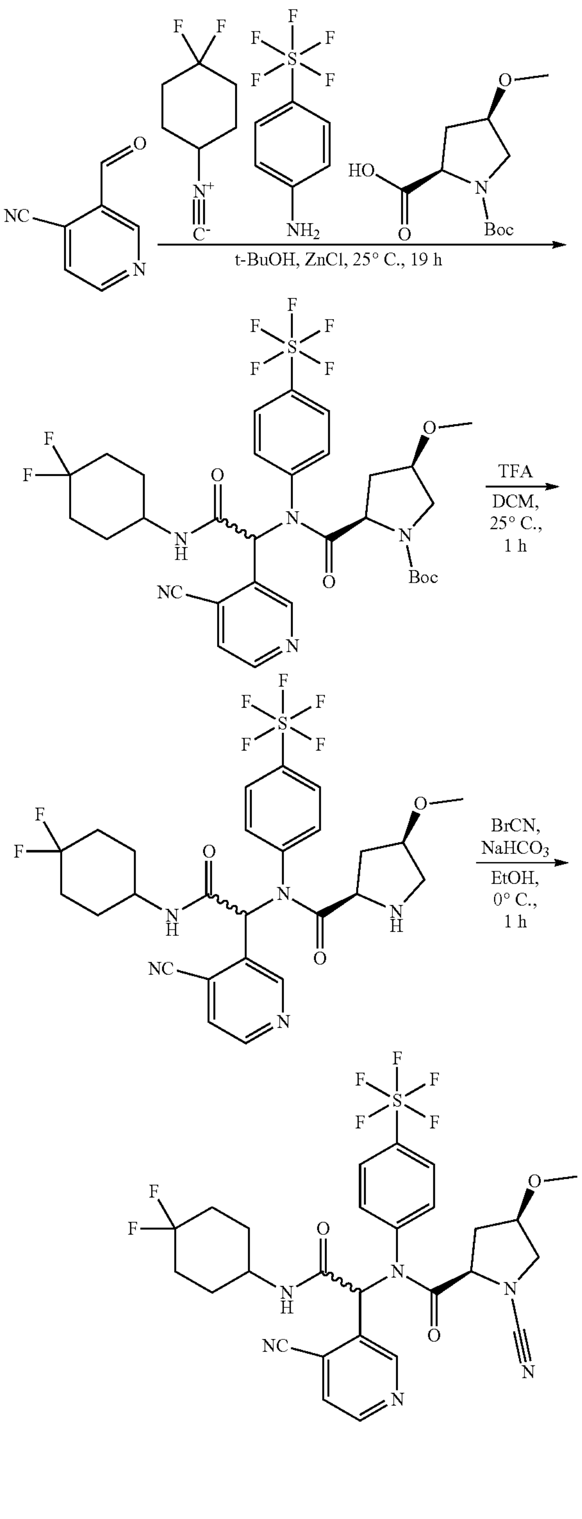

Step 1: tert-butyl (2R,4R)-2-[[1-(4-cyano-3-pyridyl)-2-[(4,4-difluorocyclohexyl)amino]-2-oxo-ethyl]-[4-(pentafluoro-λ6-sulfanyl)phenyl]carbamoyl]-4-methoxy-pyrrolidine-1-carboxylate 3-Formylpyridine-4-carbonitrile (135.63 mg, 1.03 mmol, 1.5 eq), 4-(pentafluoro-λ6-sulfanyl)aniline (150 mg, 684.38 umol, 1 eq) in t-BuOH (0.5 mL) was stirred at 25° C. for 2 h. To the solution was added (2R,4R)-1-tert-butoxycarbonyl-4-methoxy-pyrrolidine-2-carboxylic acid (167.86 mg, 684.38 umol, 1 eq) and 1,1-difluoro-4-isocyano-cyclohexane (99.34 mg, 684.38 umol, 1 eq), and then $ZnCl_2$ (1 M, 4.11 mL, 6 eq) was added. The resulting solution was stirred 25° C. for 17 h. Upon completion, the solution was diluted with $H_2O$ (20 mL), extracted with EA (30 mL*3), the combined organic phase was dried over $Na_2SO_4$, filtrated and concentrated to give the crude. The residue was purified by prep-TLC ($SiO_2$, PE:EA=1:1). tert-butyl (2R,4R)-2-[[1-(4-cyano-3-pyridyl)-2-[(4,4-difluorocyclohexyl)amino]-2-oxo-ethyl]-[4-(pentafluoro-%6-sulfanyl)phenyl]carbamoyl]-4-methoxy-pyrrolidine-1-carboxylate (60 mg, 82.91 umol, 10.00% yield, 100% purity) was obtained as yellow solid. MS (ESI) m/z 724.1 $[M+H]^+$.

Step 2: (2R,4R)—N-[1-(4-cyano-3-pyridyl)-2-[(4,4-difluorocyclohexyl)amino]-2-oxo-ethyl]-4-methoxy-N-[4-(pentafluoro-λ6-sulfanyl)phenyl]pyrrolidine-2-carboxamide To a solution of tert-butyl (2R,4R)-2-[[1-(4-cyano-3-pyridyl)-2-[(4,4-difluorocyclohexyl)amino]-2-oxo-ethyl]-[4-(pentafluoro-λ6-sulfanyl)phenyl]carbamoyl]-4-methoxy-pyrrolidine-1-carboxylate (50 mg, 69.09 umol, 1 eq) in DCM (0.5 mL) was added TFA (154.00 mg, 1.35 mmol, 0.1 mL, 19.55 eq), and the solution was stirred at 25° C. for 1 h. Upon completion, the solution was concentrated to remove the DCM, the pH was adjusted to 7-8 by $NaHCO_3$, extracted with DCM (20 mL*3), the combined organic phase was dried over $Na_2SO_4$, filtrated and concentrated to give the crude. The crude was used in the next step directly. (2R, 4R)—N-[1-(4-cyano-3-pyridyl)-2-[(4,4-difluorocyclohexyl)amino]-2-oxo-ethyl]-4-methoxy-N-[4-(pentafluoro-λ6-sulfanyl)phenyl]pyrrolidine-2-carboxamide (40 mg, crude) was obtained as yellow solid. MS (ESI) m/z 624.3 [M+H]*.

Step 3: (2R)—N-(4-(tert-butyl)phenyl)-1-cyano-N-(2-oxo-1-(pyridin-3-yl)-2-((pyridin-4-ylmethyl)amino)ethyl)pyrrolidine-2-carboxamide A solution of (2R,4R)—N-[1-(4-cyano-3-pyridyl)-2-[(4,4-difluorocyclohexyl)amino]-2-oxo-ethyl]-4-methoxy-N-[4-(pentafluoro-λ6-sulfanyl)phenyl]pyrrolidine-2-carboxamide (40 mg, 64.15 umol, 1 eq) and $NaHCO_3$ (16.17 mg, 192.44 umol, 7.48 uL, 3 eq) in EtOH (1 mL) was cooled to 0° C., and then BrCN (6.79 mg, 64.15 umol, 4.72 uL, 1 eq) was added to the solution and stirred at 0° C. for 1 h. Upon completion, the solution was quenched with $H_2O$ (10 mL), extracted with EA (20 mL*3), the combined organic phase was dried over $Na_2SO_4$, filtrated and concentrated to give the crude. The residue was purified by prep-HPLC (FA condition), column: Phenomenex Luna C18 75*30 mm*3 um; mobile phase: [water (0.2% FA)-ACN]; B %: 40%-70%, 8 min. (2R,4R)-1-cyano-N-[1-(4-cyano-3-pyridyl)-2-[(4,4-difluorocyclohexyl)amino]-2-oxo-ethyl]-4-methoxy-N-[4-(pentafluoro-λ6-sulfanyl)phenyl]pyrrolidine-2-carboxamide (3 mg, 4.38 umol, 14.20% yield, 94.7% purity) was obtained as white solid. $^1H$ NMR (400 MHz, METHANOL-$d_4$) δ=8.59 (d, J=5.1 Hz, 1H), 8.41 (s, 1H), 7.90-7.42 (m, 5H), 6.56 (s, 1H), 4.37 (dd, J=6.4, 8.3 Hz, 1H), 4.00-3.86 (m, 2H), 3.64 (dd, J=5.9, 9.6 Hz, 1H), 3.47 (dd, J=4.8, 9.6 Hz, 1H), 3.28 (s, 3H), 2.11-1.84 (m, 8H), 1.70-1.46 (m, 2H). MS (ESI) m/z 649.1 $[M+H]^+$.

Example 122: Synthesis of Compound 1211

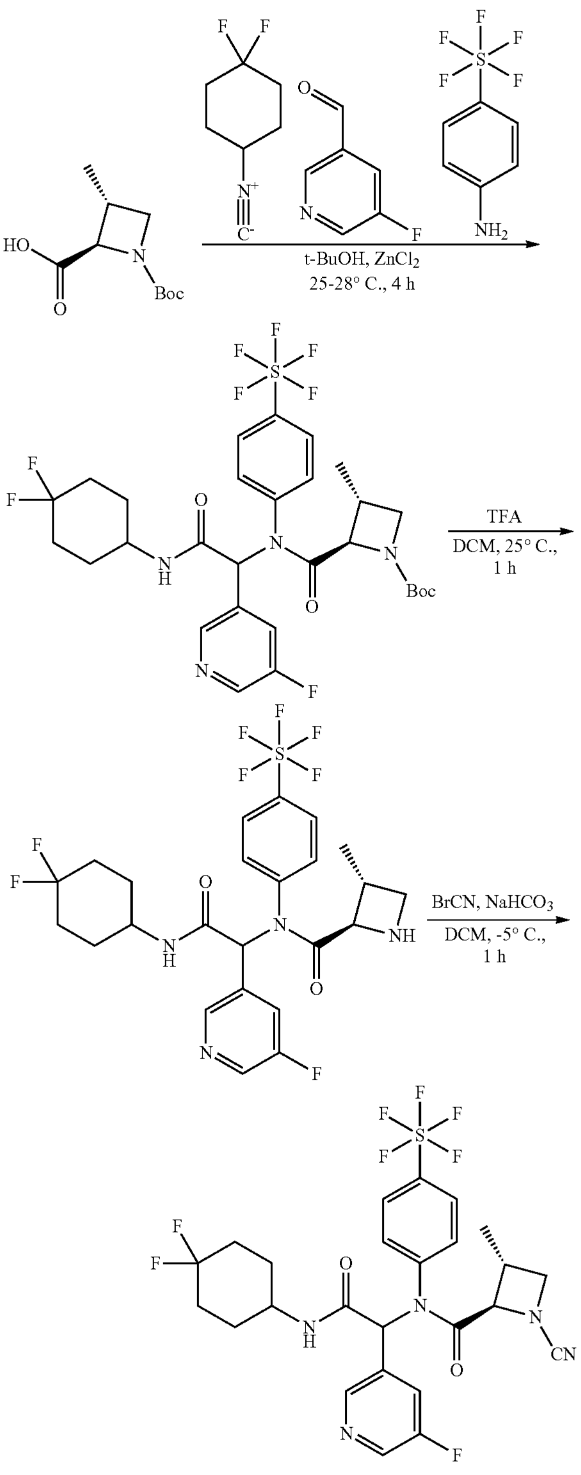

Step 1: tert-butyl (2R,3R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-methyl-azetidine-1-carboxylate A mixture of 5-fluoropyridine-3-carbaldehyde (282.53 mg, 2.26 mmol, 1.5 eq) and 4-(pentafluoro-λ$^6$-sulfanyl) aniline (330 mg, 1.51 mmol, 1 eq) in t-BuOH (6 mL) was stirred at 28° C. for 3 h. Then added (2R,3R)-1-tert-butoxycarbonyl-3-methyl-azetidine-2-carboxylic acid (324.08 mg, 1.51 mmol, 1 eq), 1,1-difluoro-4-isocyano-cyclohexane (218.54 mg, 1.51 mmol, 1 eq) and $ZnCl_2$ (1 M, 9.03 mL, 6 eq) was stirred at 25° C. for 1 h. Upon completion, the reaction mixture was diluted with $NaHCO_3$ (10 mL) and extracted with EA (10 mL*3). The combined organic layers were washed with brine, dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM $NH_4HCO_3$)-ACN]; B %: 45%-65%, 8 min) to afford tert-butyl (2R,3R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-methyl-azetidine-1-carboxylate (420 mg, 611.66 umol, 40.62% yield) as yellow oil. MS (ESI) m/z 687.2 [M+H]$^+$.

Step 2: (2R,3R)—N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide A mixture of tert-butyl (2R,3R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-methyl-azetidine-1-carboxylate (410 mg, 597.10 umol, 1 eq) in DCM (5 mL) and TFA (2.5 mL) was stirred at 25° C. for 1 h. Upon completion, the reaction mixture was diluted with $NaHCO_3$ (10 mL) and extracted with EA (10 mL*3). The combined organic layers were washed with brine, dried over $Na_2SO_4$, filtered and concentrated under reduced pressure to give a residue to get the product (2R,3R)—N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide (330 mg, crude) as yellow oil. MS (ESI) m/z 587.2 [M+H]$^+$.

Step 3: (2R,3R)-1-cyano-N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide To a mixture of (2R,3R)—N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide (320 mg, 545.57 umol, 1 eq) in DMF (4 mL) was added $NaHCO_3$ (137.50 mg, 1.64 mmol, 63.66 uL, 3 eq), and the resulting solution was cooled to −5° C. BrCN (69.35 mg, 654.69 umol, 48.16 uL, 1.2 eq) in DMF (0.5 mL) was added drop-wise, and then the mixture was stirred at −5° C. for 1 h. Upon completion, the reaction mixture was quenched with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-70%, 8 min) to get the product (2R,3R)-1-cyano-N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide Isomer 1 (46.02 mg, 75.25 umol, 13.79% yield, 100% purity) as white solid. MS (ESI) m/z 612.2 [M+H]$^+$.

$^1$H NMR (400 MHz, METHANOL-$d_4$) δ=8.37 (d, J=2.6 Hz, 1H), 8.27 (s, 1H), 8.02-7.59 (m, 3H), 7.56-7.23 (m, 2H), 6.16 (s, 1H), 4.43 (d, J=4.9 Hz, 1H), 4.22 (d, J=1.2 Hz, 1H), 3.90 (br t, J=10.0 Hz, 1H), 3.58 (br d, J=1.8 Hz, 1H), 2.76-2.61 (m, 1H), 2.15-1.94 (m, 4H), 1.89-1.79 (m, 2H), 1.73-1.60 (m, 1H), 1.56-1.40 (m, 1H), 0.71 (d, J=6.9 Hz, 3H).

To get the product (2R,3R)-1-cyano-N-[2-[(4,4-difluorocyclohexyl)amino]-1-(5-fluoro-3-pyridyl)-2-oxo-ethyl]-3-methyl-N-[4-(pentafluoro-λ$^6$-sulfanyl)phenyl]azetidine-2-carboxamide Isomer 2 (80.32 mg, 131.34 umol, 24.07% yield, 100% purity) as white solid. MS (ESI) m/z 612.2 [M+H]$^+$.

$^1$H NMR (400 MHz, METHANOL-$d_4$) δ=8.31 (d, J=2.6 Hz, 1H), 8.21 (s, 1H), 7.78 (br s, 3H), 7.42 (td, J=2.0, 9.2 Hz, 2H), 6.25 (s, 1H), 4.40 (d, J=4.5 Hz, 1H), 4.24 (s, 1H), 3.94 (br t, J=10.3 Hz, 1H), 3.57 (br d, J=1.9 Hz, 1H), 2.70-2.59 (m, 1H), 2.16-1.95 (m, 4H), 1.88 (br dd, J=5.1, 10.0 Hz, 2H), 1.73-1.60 (m, 1H), 1.54-1.42 (m, 1H), 0.68 (d, J=6.9 Hz, 3H).

Example 123: Synthesis of Compound 1297

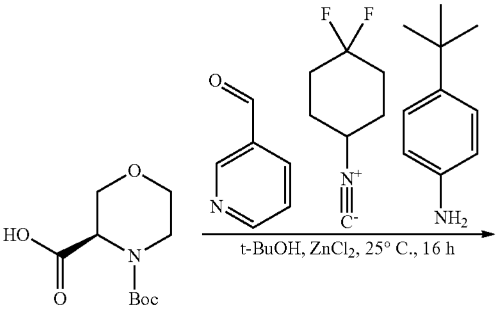

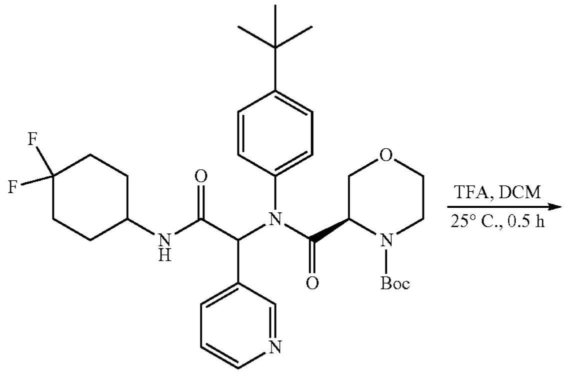

-continued

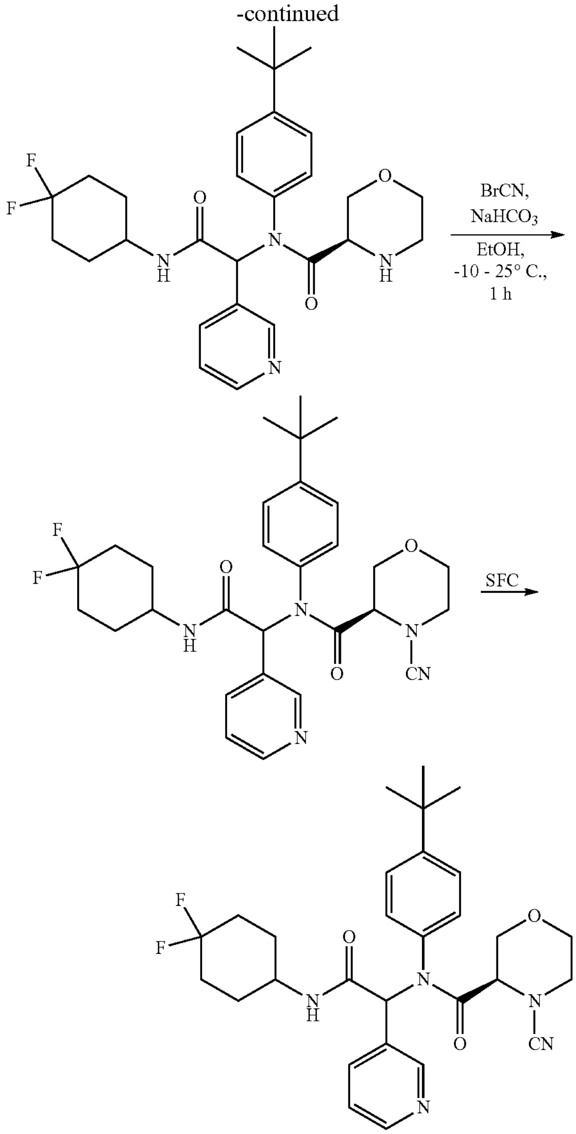

Step 1: tert-butyl (3R)-3-[(4-tert-butylphenyl)-[2-[(4,4-difluorocyclohexyl)amino]-2-oxo-1-(3-pyridyl)ethyl]carbamoyl]morpholine-4-carboxylate A solution of pyridine-3-carbaldehyde (463.19 mg, 4.32 mmol, 406.30 uL, 1 eq), 4-tert-butylaniline (645.34 mg, 4.32 mmol, 682.90 uL, 1 eq) in MeOH (20 mL) stirred at 25° C. for 30 min. (3R)-4-tert-butoxycarbonylmorpholine-3-carboxylic acid (1 g, 4.32 mmol, 1 eq) was added to the resulting mixture, and then 1,1-difluoro-4-isocyano-cyclohexane (627.69 mg, 4.32 mmol, 1 eq) in MeOH (2 mL) was added in batches (three times). The resulting mixture was stirred at 25° C. for 15 h 30 min. Upon completion, the reaction mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 60%-80%, 10 min) to give the title compound tert-butyl (3R)-3-[(4-tert-butylphenyl)-[2-[(4,4-difluorocyclohexyl)amino]-2-oxo-1-(3-pyridyl)ethyl]carbamoyl]morpholine-4-carboxylate (1.6 g, 2.57 mmol, 59.47% yield, 98.8% purity) as a yellow oil. MS (ESI) m/z 615.4 $[M+1]^+$ Step 2: (3R)—N-(4-tert-butylphenyl)-N-[2-[(4,4-difluorocyclohexyl)amino]-2-oxo-1-(3-pyridyl)ethyl]morpholine-3-carboxamide A mixture of tert-butyl (3R)-3-[(4-tert-butylphenyl)-[2-[(4,4-difluorocyclohexyl)amino]-2-oxo-1-(3-pyridyl)ethyl]carbamoyl]morpholine-4-carboxylate (1.6 g, 2.57 mmol, 98.8% purity, 1 eq) in DCM (10 mL) and TFA (5 mL) was stirred at 25° C. for 0.5 h under $N_2$ atmosphere. Upon completion, the reaction mixture was quenched by addition $NaHCO_3$ aq (150 mL), and extracted with DCM (80 mL*3). The combined organic layers were washed with brine (90 mL), dried over $Na_2SO_4$, filtered and concentrated under reduced pressure to give a the crude product (3R)—N-(4-tert-butylphenyl)-N-[2-[(4,4-difluorocyclohexyl)amino]-2-oxo-1-(3-pyridyl)ethyl]morpholine-3-carboxamide (1.05 g, crude) as a yellow oil. MS (ESI) m/z 515.3 $[M+H]^+$ Step 3: (3R)—N-(4-tert-butylphenyl)-4-cyano-N-[2-[(4,4-difluorocyclohexyl)amino]-2-oxo-1-(3-pyridyl)ethyl]morpholine-3-carboxamide To a solution of (3R)—N-(4-tert-butylphenyl)-N-[2-[(4,4-difluorocyclohexyl)amino]-2-oxo-1-(3-pyridyl)ethyl]morpholine-3-carboxamide (1 g, 1.94 mmol, 1 eq) and $NaHCO_3$ (489.73 mg, 5.83 mmol, 226.73 uL, 3 eq) in EtOH (10 mL) was added a solution of BrCN (411.66 mg, 3.89 mmol, 285.87 uL, 2 eq) in EtOH (2 mL) drop-wise at −10° C. under $N_2$. The reaction mixture was slowly warmed to 25° C. for 1 h. Upon completion, the reaction mixture was quenched by addition $H_2O$ (100 mL) and extracted with EtOAc (50 mL*3). The combined organic layers were washed with brine (100 mL), dried over $Na_2SO_4$, filtered and concentrated under reduced pressure to give a residue. The residue was purified by prep-HPLC (column: Kromasil C18 (250*50 mm*10 um); mobile phase: [water (10 mM $NH_4HCO_3$)-ACN]; B %: 40%-70%, 10 min) to give the title compound (3R)—N-(4-tert-butylphenyl)-4-cyano-N-[2-[(4,4-difluorocyclohexyl)amino]-2-oxo-1-(3-pyridyl)ethyl]morpholine-3-carboxamide (550 mg, 1.02 mmol, 52.38% yield, 99.87% purity) as a white solid. MS (ESI) m/z 540.3 $[M+H]^+$ Step 4: (3R)—N-(4-tert-butylphenyl)-4-cyano-N-[2-[(4,4-difluorocyclohexyl)amino]-2-oxo-1-(3-pyridyl)ethyl]morpholine-3-carboxamide The residue (550 mg, 99.87% purity) was separated by SFC (condition: column: Phenomenex-Cellulose-2 (250 mm*30 mm, 10 um); mobile phase: [0.1% $NH_3H_2O$ MEOH]; B %: 39%-39%, 7 min) to afford (3R)—N-(4-tert-butylphenyl)-4-cyano-N-[2-[(4,4-difluorocyclohexyl)amino]-2-oxo-1-(3-pyridyl)ethyl]morpholine-3-carboxamide (230 mg, 415.15 umol, 40.73% yield, 97.4% purity) as a white solid. MS (ESI) m/z 540.3 $[M+H]^+$ $^1H$ NMR (400 MHz, MeOD-$d_4$) δ=8.35-8.32 (m, 2H), 7.83-7.18 (m, 5H), 6.71 (s, 1H), 5.99 (s, 1H), 3.97-3.92 (m, 1H), 3.87-3.71 (m, 4H), 3.65-3.57 (m, 2H), 3.13-3.06 (m, 1H), 2.11-1.74 (m, 6H), 1.63-1.59 (m, 1H), 1.45-1.42 (m, 1H) 1.25 (s, 9H).

(3R)—N-(4-tert-butylphenyl)-4-cyano-N-[2-[(4,4-difluorocyclohexyl)amino]-2-oxo-1-(3-pyridyl)ethyl]morpholine-3-carboxamide (230 mg, 401.08 umol, 39.35% yield, 94.1% purity) was obtained as a white solid. MS (ESI) m/z 540.3 $[M+H]^+$ $^1H$ NMR (400 MHz, MeOD-$d_4$) δ=8.29-8.28 (m, 2H), 7.76-7.08 (m, 5H), 6.70 (s, 1H), 6.16 (s, 1H), 3.96-3.82 (m, 2H), 3.81-3.58 (m, 5H), 3.11-3.07 (m, 1H), 2.01-1.82 (m, 6H), 1.71-1.59 (m, 1H), 1.51-1.38 (m, 1H) 1.22 (s, 9H).

Example 124: Synthesis of Compound 1176

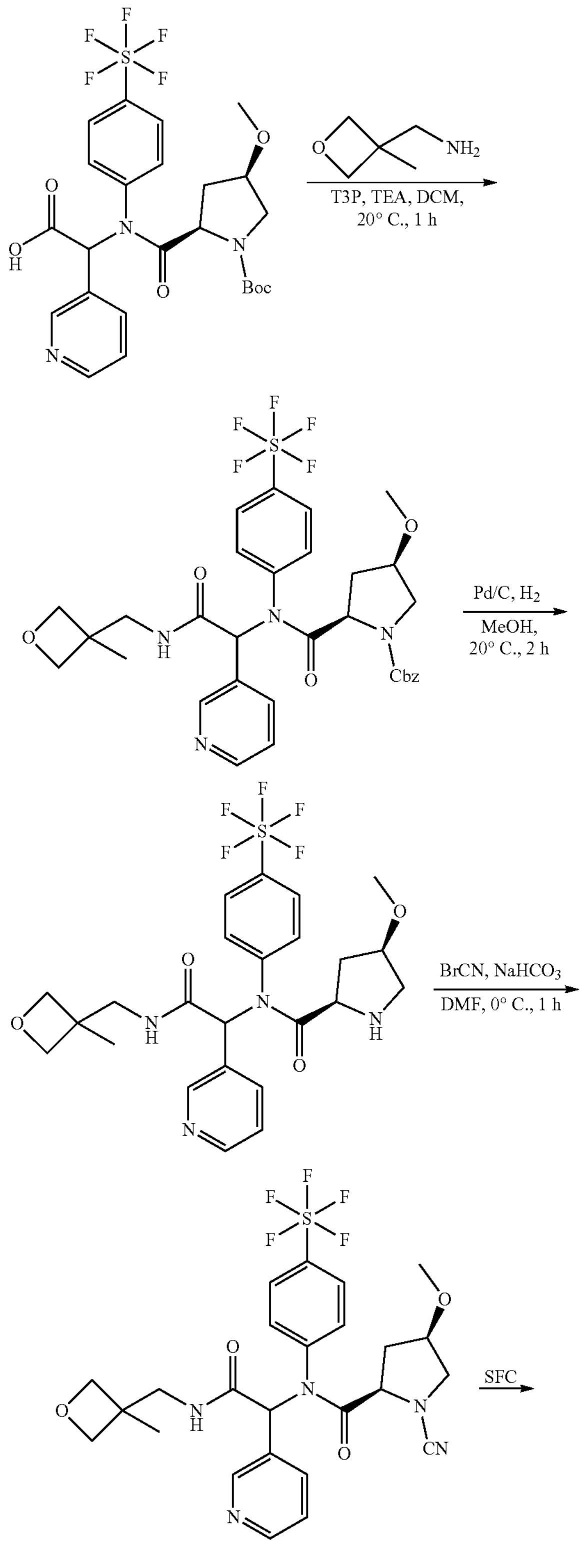

-continued

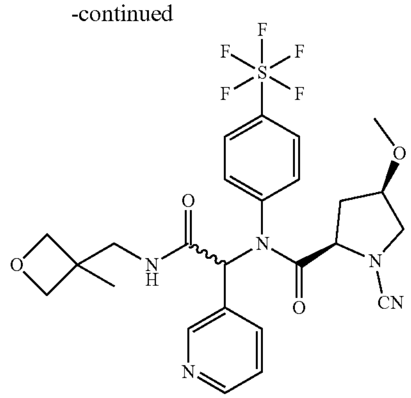

Step 1: benzyl (2R,4R)-4-methoxy-2-[[2-[(3-methyloxetan-3-yl)methylamino]-2-oxo-1-(3-pyridyl)ethyl]-[4-(pentafluoro-$\lambda^6$-sulfanyl)phenyl]carbamoyl]pyrrolidine-1-carboxylate A mixture of (3-methyloxetan-3-yl)methanamine (73.94 mg, 731.03 umol, 1.5 eq), 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (300 mg, 487.35 umol, 1 eq), T3P (930.40 mg, 1.46 mmol, 869.54 uL, 50% purity, 3 eq), TEA (147.94 mg, 1.46 mmol, 203.50 uL, 3 eq) in DCM (6 mL) was degassed and purged with $N_2$ for 3 times, and then the mixture was stirred at 20° C. for 1 h under $N_2$ atmosphere. Upon completion, the reaction mixture was poured into $H_2O$ 30 mL at 20° C., and then extracted with DCM (30 mL*3). The combined organic layers were washed with brine (30 mL*2), dried over $Na_2SO_4$, filtered and concentrated under reduced pressure to give a residue. The residue was purified by column chromatography ($SiO_2$, Petroleum ether/Ethyl acetate=1/0 to 0/1) to give benzyl (2R,4R)-4-methoxy-2-[[2-[(3-methyloxetan-3-yl)methylamino]-2-oxo-1-(3-pyridyl)ethyl]-[4-(pentafluoro-$\lambda^6$-sulfanyl)phenyl]carbamoyl]pyrrolidine-1-carboxylate (280 mg, 360.67 umol, 74.01% yield, 90% purity) as a yellow solid. MS (ESI) m/z 699.1 $[M+H]^+$ Step 2: (2R,4R)-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide To a solution of benzyl (2R,4R)-4-methoxy-2-[[2-[(3-methyloxetan-3-yl)methylamino]-2-oxo-1-(3-pyridyl)ethyl]-[4-(pentafluoro-$\lambda^6$-sulfanyl)phenyl]carbamoyl]pyrrolidine-1-carboxylate (230 mg, 329.18 umol, 1 eq) in MeOH (5 mL) was added Pd/C (230 mg, 329.18 umol, 10% purity, 1 eq) under $N_2$. The suspension was degassed under vacuum and purged with $H_2$ several times. The mixture was stirred under $H_2$ (15 Psi) at 20° C. for 2 h. Upon completion, the reaction mixture was filtered and concentrated to give (2R,4R)-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide (130 mg, crude) as a white solid. MS (ESI) m/z 565.2 [M+H].

Step 3: (2R,4R)-1-cyano-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide To a solution of (2R,4R)-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide (120 mg, 212.55 umol, 1 eq), $NaHCO_3$ (53.57 mg, 637.66 umol, 24.80 uL, 3 eq) in DMF (3 mL) was added BrCN (27.02 mg, 255.06 umol, 18.76 uL, 1.2 eq) in DMF (0.3 mL) at 0° C. The mixture was stirred at 0° C. for 1 h. Upon completion, the reaction mixture was quenched by the addition of $H_2O$ 25 mL at 20° C., and then extracted with EtOAc (25 mL*3). The combined organic layers were washed with brine (25 mL*2), dried over $N_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 20%-50%, 8 min) to give (2R,4R)-1-cyano-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide (50 mg, 73.70 umol, 34.67% yield, 86.9% purity) as a white solid. MS (ESI) m/z 590.2 $[M+H]^+$ Step 4: (2R,4R)-1-cyano-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide (2R,4R)-1-cyano-4-methoxy-N-[2-[(3-methyloxetan-3-yl)methylamino]-2-oxo-1-(3-pyridyl)ethyl]-N-[4-(pentafluoro-λ6-sulfanyl)phenyl]pyrrolidine-2-carboxamide (40 mg) was separated by SFC (column: DAICEL CHIRALPAK IC (250 mm*30 mm, 10 um); mobile phase: [Neu-ETOH]; B %: 43%-43%, 10 min) to afford (2R,4R)-1-cyano-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide (11.5 mg, 18.02 umol, 26.57% yield, 92.4% purity) as a white solid. MS (ESI) m/z 590.2 $[M+H]^+$ Isomer 1: $^1H$ NMR (400 MHz, MeOD-$d_4$) δ=8.35 (d, J=1.7, 4.6 Hz, 2H), 8.18-7.32 (m, 5H), 7.23 (d, J=4.9, 8.0 Hz, 1H), 6.29 (s, 1H), 4.51 (d, J=6.1, 8.5 Hz, 2H), 4.31 (d, J=3.0, 6.0 Hz, 2H), 4.23 (d, J=6.1, 8.8 Hz, 1H), 3.90 (t, J=5.7 Hz, 1H), 3.64 (d, J=6.0, 9.5 Hz, 1H), 3.58-3.52 (m, 1H), 3.50-3.41 (m, 2H1), 3.28 (s, 3H), 2.18-1.93 (m, 2H), 1.27 (s, 3H).

(2R,4R)-1-cyano-4-methoxy-N-[2-[(3-methyloxetan-3-yl)methylamino]-2-oxo-1-(3-pyridyl)ethyl]-N-[4-(pentafluoro-$\lambda^6$-sulfanyl)phenyl]pyrrolidine-2-carboxamide (12.5 mg, 15.99 umol, 23.56% yield, 75.4% purity) was obtained as a yellow solid. MS (ESI) m/z 590.2 $[M+H]^+$ Isomer 2: $^1H$ NMR (400 MHz, MeOD-$d_4$) δ=8.40 (s, 2H), 8.27-8.12 (m, 1H), 8.06-7.99 (m, 1H), 7.87-7.54 (m, 4H), 7.25 (d, J=5.1, 7.9 Hz, 1H), 6.11 (s, 1H), 4.50 (t, J=6.0 Hz, 2H), 4.30 (d, J=6.9 Hz, 2H), 3.91 (t, J=5.7 Hz, 1H), 3.61 (d, J=5.8, 9.7 Hz, 1H), 3.52-3.48 (m, 2H), 3.40 (s, 1H), 3.28 (s, 3H), 2.09 (d, J=2.0, 6.7 Hz, 1H), 1.95 (d, J=5.1 Hz, 1H), 1.26 (s, 3H).

Example 125: Synthesis of Compound 1182

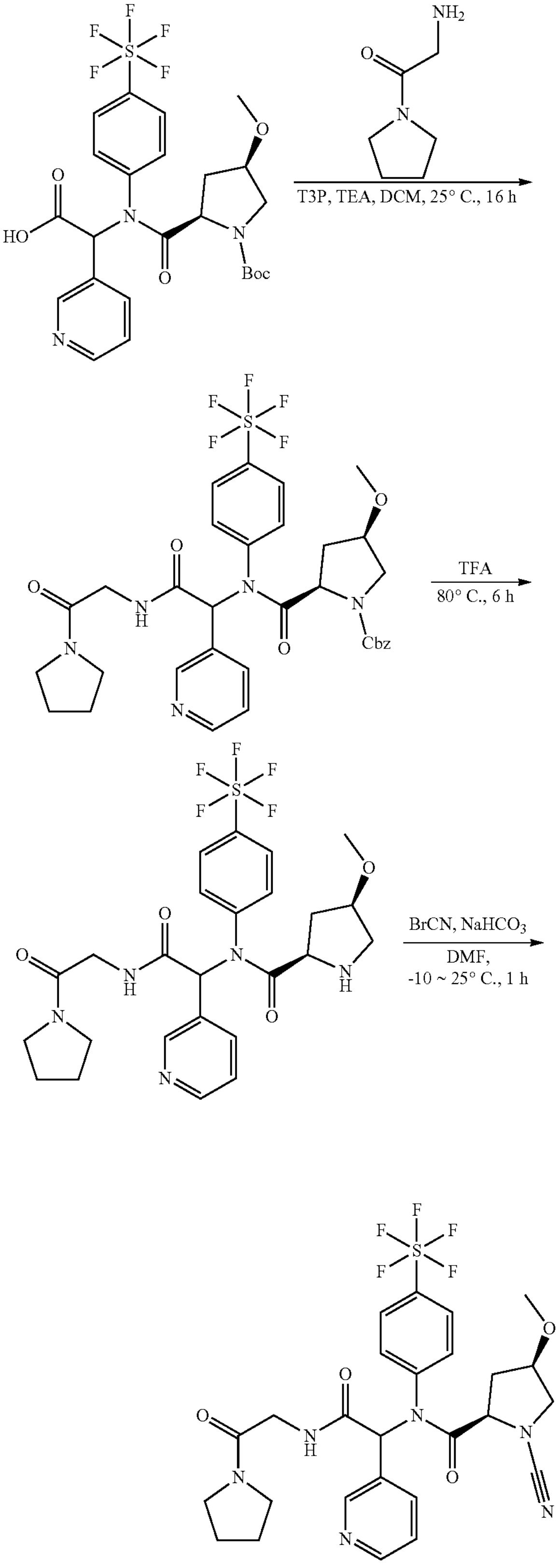

Step1: benzyl(2R,4R)-4-methoxy-2-[[2-oxo-2-[(2-oxo-2-pyrrolidin-1-yl-ethyl)amino]-1-(3-pyridyl)ethyl]-[4-(pentafluoro-$\lambda^6$-sulfanyl)phenyl]carbamoyl]pyrrolidine-1-carboxylate To a solution of 2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetic acid (250 mg, 406.13 umol, 1 eq) in DCM (5 mL) was added 2-amino-1-pyrrolidin-1-yl-ethanone (52.05 mg, 406.13 umol, 1 eq), T3P (387.67 mg, 609.19 umol, 362.31 uL, 50% purity, 1.5 eq), TEA (123.29 mg, 1.22 mmol, 169.58 uL, 3 eq) and the mixture was stirred at 25° C. for 1 h. Upon completion, the reaction was quenched by addition $H_2O$ (50 mL) and then extracted with DCM (20 mL*3). The combined organic layers were washed with brine (20 mL), dried over $Na_2SO_4$, filtered and concentrated under reduced pressure to give a residue and was purified by prep-HPLC (column: Phenomenex Gemini-NX 80*40 mm*3 um; mobile phase: [water (10 mM $NH_4HCO_3$)-ACN]; B %: 30%-50%, 8 min) to afford benzyl (2R,4R)-4-methoxy-2-[[2-oxo-2-[(2-oxo-2-pyrrolidin-1-yl-ethyl)amino]-1-(3-pyridyl)ethyl]-[4-(pentafluoro-λ6-sulfanyl)phenyl]carbamoyl]pyrrolidine-1-carboxylate (80 mg, 110.23 umol, 27.14% yield) was yellow solid. MS (ESI) m/z 726.2 $[M+H]^+$ Step 2: (2R,4R)-4-methoxy-N-[2-oxo-2-[(2-oxo-2-pyrrolidin-1-yl-ethyl)amino]-1-(3-pyridyl)ethyl]-N-[4-(pentafluoro-$\lambda^6$-sulfanyl)phenyl]pyrrolidine-2-carboxamide A solution of benzyl(2R,4R)-4-methoxy-2-[[2-oxo-2-[(2-oxo-2-pyrrolidin-1-yl-ethyl)amino]-1-(3-pyridyl)ethyl]-[4-(pentafluoro-λ6-sulfanyl)phenyl]carbamoyl]pyrrolidine-1-carboxylate (80 mg, 110.23 umol, 1 eq) in TFA (3 mL) was stirred at 80° C. for 6 h. Upon completion, the reaction mixture was quenched by addition $NaHCO_3$ (20 mL) and the pH was adjusted to 7, and then extracted with DCM (10 mL*3). The combined organic layers were washed with brine (20 mL), dried over $Na_2SO_4$, filtered and concentrated under reduced pressure to give (2R,4R)-4-methoxy-N-[2-oxo-2-[(2-oxo-2-pyrrolidin-1-yl-ethyl)amino]-1-(3-pyridyl)ethyl]-N-[4-(pentafluoro-λ6-sulfanyl)phenyl]pyrrolidine-2-carboxamide (58 mg, crude) was yellow oil. MS (ESI) m/z 592.2 $[M+H]^+$ Step3: (2R,4R)-1-cyano-4-methoxy-N-[2-oxo-2-[(2-oxo-2-pyrrolidin-1-yl-ethyl)amino]-1-(3-pyridyl)ethyl]-N-[4-(pentafluoro-λ6-sulfanyl)phenyl]pyrrolidine-2-carboxamide To a solution of (2R,4R)-4-methoxy-N-[2-oxo-2-[(2-oxo-2-pyrrolidin-1-yl-ethyl)amino]-1-(3-pyridyl)ethyl]-N-[4-(pentafluoro-λ6-sulfanyl)phenyl]pyrrolidine-2-carboxamide (58 mg, 98.04 umol, 1 eq) in EtOH (2 mL) was added $NaHCO_3$ (24.71 mg, 294.12 umol, 11.44 uL, 3 eq) and the mixture was cooled at −10° C. To the resulting mixture was added with BrCN (13.50 mg, 127.45 umol, 9.37 uL, 1.3 eq) in EtOH (0.5 mL) and the mixture was warmed at 25° C. and stirred for 2 h. Upon completion, the mixture was quenched by addition $H_2O$ 10 mL and then extracted with DCM (10 mL*3). The combined organic layers were washed with brine 10 mL, dried over $Na_2SO_4$, filtered and concentrated under reduced pressure to give a residue and was purified by prep-HPLC (column: Phenomenex Luna C18 200*40 mm*10 um; mobile phase: [water (0.2% FA)-ACN]; B %: 20%-50%, 8 min) to afford (2R,4R)-1-cyano-4-methoxy-N-[2-oxo-2-[(2-oxo-2-pyrrolidin-1-yl-ethyl)amino]-1-(3-pyridyl)ethyl]-N-[4-(pentafluoro-λ6-sulfanyl)phenyl]pyrrolidine-2-carboxamide (10 mg, 16.12 umol, 16.44% yield, 99.388% purity) was yellow solid. MS (ESI) m/z 617.2

Example 126: Synthesis of Compound 1299

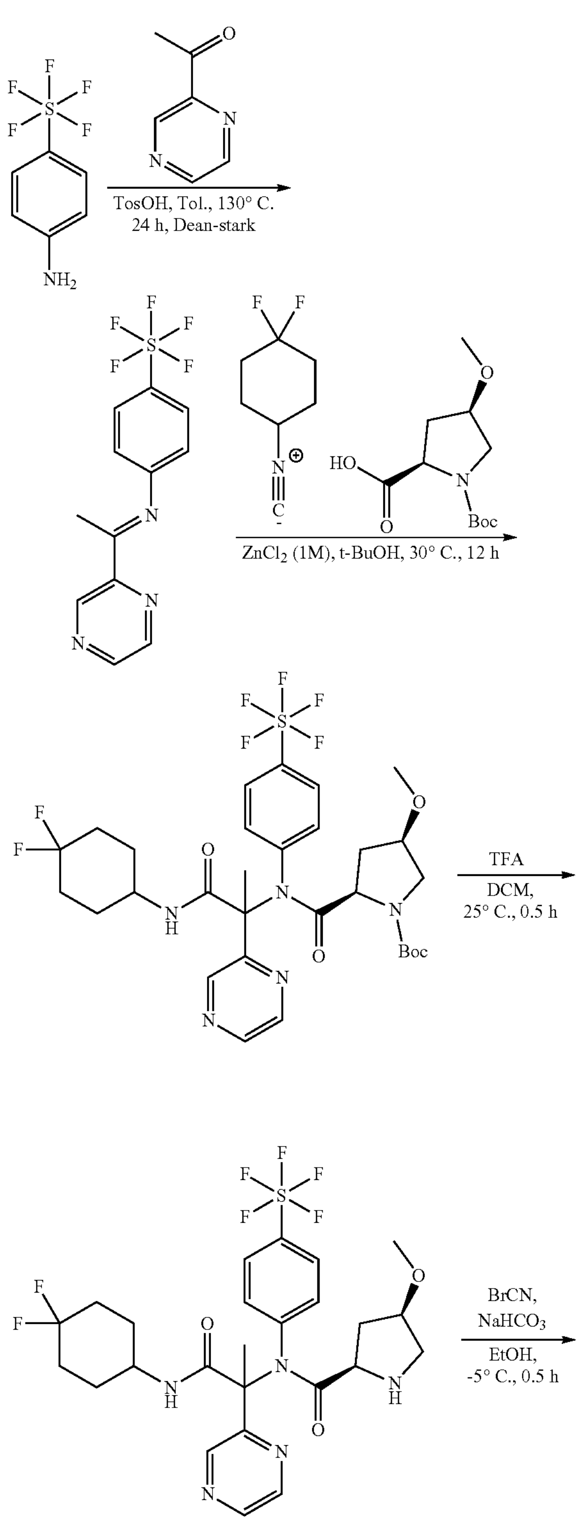

-continued

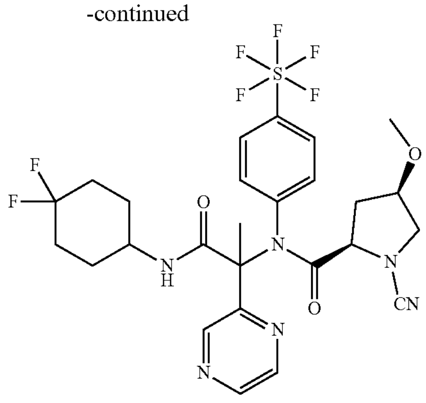

Step 1: (E)-N-[4-(pentafluoro-λ$^6$-sulfanyl)phenyl]-1-pyrazin-2-yl-ethanimine

To a solution of 4-(pentafluoro-λ$^6$-sulfanyl)aniline (2 g, 9.13 mmol, 1 eq) in toluene (30 mL) was added 1-pyrazin-2-ylethanone (1.11 g, 9.13 mmol, 502.45 uL, 1 eq) and TosOH (78.57 mg, 456.26 umol, 0.05 eq. The mixture was stirred at 130° C. for 24 h and water was removed by Dean-Stark trap. Upon completion, the reaction mixture was concentrated under reduced pressure to give (E)-N-[4-(pentafluoro-λ$^6$-sulfanyl)phenyl]-1-pyrazin-2-yl-ethanimine (3 g, crude) as a yellow solid. MS (ESI) m/z 324.1 $[M+H]^+$.

Step 2: tert-butyl (2R,4R)-2-[[2-[(4,4-difluorocyclohexyl)amino]-1-methyl-2-oxo-1-pyrazin-2-yl-ethyl]-[4-(pentafluoro-λ$^6$-sulfanyl)phenyl]carbamoyl]-4-methoxy-pyrrolidine-11-carboxylate To a solution of (E)-N-[4-(pentafluoro-λ$^6$-sulfanyl)phenyl]-1-pyrazin-2-yl-ethanimine (1 g, 3.09 mmol, 1 eq), 1,1-difluoro-4-isocyano-cyclohexane (448.98 mg, 3.09 mmol, 1 eq) and (2R,4R)-1-tert-butoxycarbonyl-4-methoxy-pyrrolidine-2-carboxylic acid (758.69 mg, 3.09 mmol, 1 eq) in t-BuOH (20 mL) was added $ZnCl_2$ (1 M, 18.56 mL, 6 eq), and the mixture was stirred at 30° C. for 12 h. Upon completion, the reaction mixture was diluted with sat. $NaHCO_3$ (50 mL) and extracted with EA (20 ml,*3). The combined organic layers were dried over $Na_2SO_4$, filtered and concentrated under reduced pressure to give a residue. The residue was purified by prep-HPLC (column: Kromasil C18 (250*50 mm*10 um); mobile phase: [water (10 mM $NH_4HCO_3$)-ACN]; B %: 60%-80%, 10 min) and re-purified by prep-TLC ($SiO_2$, Petroleum ether/Ethyl acetate=1/1) to give tert-butyl (2R,4R)-2-[[2-[(4,4-difluorocyclohexyl)amino]-1-methyl-2-oxo-1-pyrazin-2-yl-ethyl]-[4-(pentafluoro-λ$^6$-sulfanyl)phenyl]carbamoyl]-4-methoxy-pyrrolidine-1-carboxylate Isomer 1 (0.04 g, 50.44 umol, 1.63% yield, 90% purity) as a yellow solid. MS (ESI) m/z 714.3 $[M+H]^+$.

Tert-butyl (2R,4R)-2-[[2-[(4,4-difluorocyclohexyl)amino]-1-methyl-2-oxo-1-pyrazin-2-yl-ethyl]-[4-(pentafluoro-λ$^6$-sulfanyl)phenyl]carbamoyl]-4-methoxy-pyrrolidine-1-carboxylate Isomer 2 (0.06 g, 79.86 umol, 2.58% yield, 95% purity) was obtained as a yellow solid. MS (ESI) m/z 714.3 $[M+H]^+$.

Step 3: (2R,4R)—N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 1

To a solution of tert-butyl (2R,4R)-2-[[2-[(4,4-difluorocyclohexyl)amino]-1-methyl-2-oxo-1-pyrazin-2-yl-ethyl]-[4-(pentafluoro-λ$^6$-sulfanyl)phenyl]carbamoyl]-4-methoxy-pyrrolidine-1-carboxylate Isomer 1 (0.035 g, 49.04 umol, 1 eq) in DCM (1 mL) was added TFA (616.00 mg, 5.40 mmol, 0.4 mL, 110.17 eq), and the mixture was stirred at 25° C. for 0.5 h. Upon completion, the reaction mixture was dried by blowing $N_2$ and then diluted with sat. $NaHCO_3$ (10 mL) and extracted with DCM (5 mL*2). The combined organic layers were dried over $Na_2SO_4$, filtered and concentrated under reduced pressure to give (2R,4R)—N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 1 (0.03 g, crude) as a yellow oil.

(2R,4R)—N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 2

To a solution of tert-butyl (2R,4R)-2-[[2-[(4,4-difluorocyclohexyl)amino]-1-methyl-2-oxo-1-pyrazin-2-yl-ethyl]-[4-(pentafluoro-λ$^6$-sulfanyl)phenyl]carbamoyl]-4-methoxy-pyrrolidine-1-carboxylate (0.06 g, 84.07 umol, 1 eq) in DCM (0.5 mL) was added TFA (3.70 g, 32.42 mmol, 2.40 mL, 385.58 eq), and the mixture was stirred at 25° C. for 0.5 h. Upon completion, the reaction mixture was dried by blowing $N_2$ and then diluted with sat. $NaHCO_3$ (10 mL) and extracted with DCM (5 mL*2). The combined organic layers were dried over $Na_2SO_4$, filtered and concentrated under reduced pressure to give (2R,4R)—N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 2 (0.05 g, crude) as a yellow oil.

Step 4: (2R,4R)-1-cyano-N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 1

To a solution of (2R,4R)—N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 1 (0.03 g, 48.89 umol, 1 eq) in EtOH (1 mL) was added $NaHCO_3$ (12.32 mg, 146.68 umol, 5.70 uL, 3 eq). BrCN (5.18 mg, 48.89 umol, 3.60 uL, 1 eq) in EtOH (0.2 mL) was added drop-wise at −5° C., and the mixture was stirred at −5° C. for 0.5 h under $N_2$. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-80%, 8 min) to give (2R,4R)-1-cyano-N-[2-[(4,4-difluorocyclohexyl)amino]-1-methyl-2-oxo-1-pyrazin-2-yl-ethyl]-4-methoxy-N-[4-(pentafluoro-λ$^6$-sulfanyl)phenyl]pyrrolidine-2-carboxamide Isomer 1 (12.40 mg, 19.22 umol, 39.32% yield, 99% purity) as a white solid. MS (ESI) m/z 639.2 [M+H]).

$^1$H NMR (400 MHz, METHANOL-$d_4$) δ=9.05 (d, J=1.3 Hz, 1H), 8.98 (br d, J=7.5 Hz, 1H), 8.64 (dd, J=1.6, 2.5 Hz, 1H), 8.57 (d, J=2.5 Hz, 1H), 8.12-8.00 (m, 3H), 7.84 (br d, J=8.2 Hz, 1H), 4.21 (dd, J=6.4, 8.7 Hz, 1H), 4.03-3.83 (m, 2H), 3.59 (dd, J=6.1, 9.5 Hz, 1H), 3.35 (dd, J=5.5, 9.4 Hz, 1H), 3.28-3.16 (m, 3H), 2.23-2.13 (m, 1H), 2.11-1.85 (m, 7H), 1.71 (br d, J=12.0 Hz, 2H), 1.43 (s, 3H).

(2R,4R)-1-cyano-N-[2-[(4,4-difluorocyclohexyl)amino]-1-methyl-2-oxo-1-pyrazin-2-yl-ethyl]-4-methoxy-N-[4-(pentafluoro-$\lambda^6$-sulfanyl)phenyl]pyrrolidine-2-carboxamide Isomer 2

To a solution of (2R,4R)—N-[2-[(4,4-difluorocyclohexyl)amino]-1-methyl-2-oxo-1-pyrazin-2-yl-ethyl]-4-methoxy-N-[4-(pentafluoro-$\lambda^6$-sulfanyl)phenyl]pyrrolidine-2-carboxamide Isomer 2 (0.05 g, 81.49 umol, 1 eq) in EtOH (1.5 mL) was added $NaHCO_3$ (20.54 mg, 244.46 umol, 9.51 uL, 3 eq), and then BrCN (8.63 mg, 81.49 umol, 5.99 uL, 1 eq) in EtOH (0.5 mL) was added drop-wise at −5° C., the mixture was stirred at −5° C. for 0.5 h under $N_2$. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-80%, 8 min) to give (2R,4R)-1-cyano-N-[2-[(4,4-difluorocyclohexyl)amino]-1-methyl-2-oxo-1-pyrazin-2-yl-ethyl]-4-methoxy-N-[4-(pentafluoro-$\lambda^6$-sulfanyl)phenyl]pyrrolidine-2-carboxamide Isomer 2 (23.10 mg, 35.81 umol, 43.95% yield, 99% purity) as a white solid. MS (ESI) m/z 639.2 $[M+H]^+$.

$^1H$ NMR (400 MHz, METHANOL-$d_4$) δ=9.05-8.90 (m, 1H), 8.88-8.81 (m, 0.18H), 8.65-8.59 (m, 1H), 8.57 (d, J=2.6 Hz, 1H), 8.19-8.10 (m, 1H), 8.10-8.03 (m, 1H), 8.00 (dd, J=2.4, 8.8 Hz, 1H), 7.78 (br d, J=9.1 Hz, 1H), 4.36 (dd, J=4.3, 8.8 Hz, 1H), 4.00-3.84 (m, 2H), 3.56 (dd, J=5.4, 9.8 Hz, 1H), 3.44 (dd, J=3.3, 9.9 Hz, 1H), 3.27-3.17 (m, 3H), 2.11-1.86 (m, 8H), 1.79-1.63 (m, 2H), 1.55-1.38 (m, 3H).

Example 127: Synthesis of Compound 1207

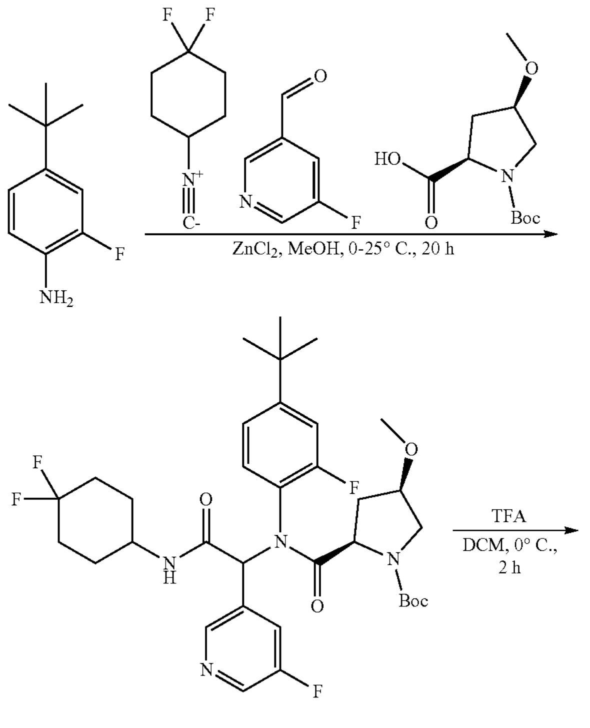

-continued

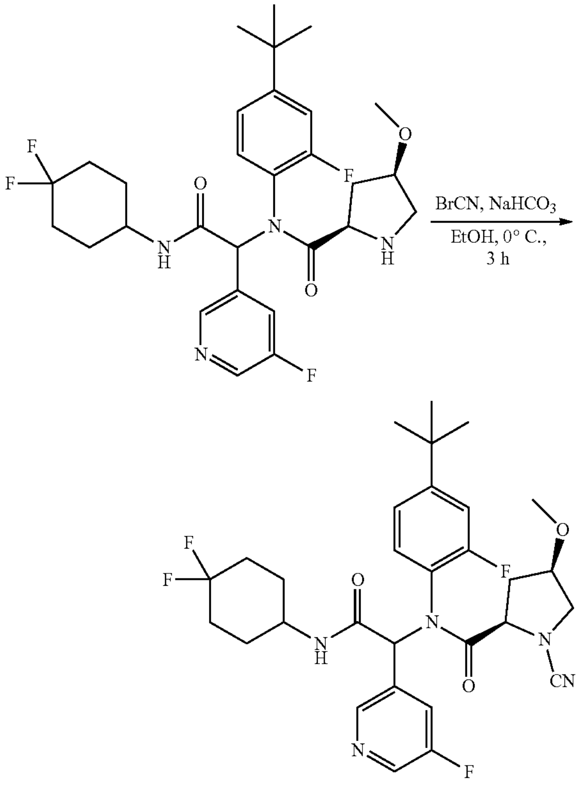

Step 1: tert-butyl (2R,4R)-2-[(4-tert-butyl-2-fluoro-phenyl)-[2-[(4,4-difluorocyclohexyl)amino]-1-(5-fluoro-3-pyridyl)-2-oxo-ethyl]carbamoyl]-4-methoxy-pyrrolidine-1-carboxylate To a mixture of 4-tert-butyl-2-fluoro-aniline (400 mg, 2.40 mmol, 1 eq) in t-BuOH (15 mL) was added 5-fluoro-pyridine-3-carbaldehyde (330.26 mg, 2.62 mmol, 1.1 eq) in one portion. The mixture was stirred at 28° C. for 3 h, and then (2R,4R)-1-tert-butoxycarbonyl-4-methoxy-pyrrolidine-2-carboxylic acid (1765.96 mg, 7.20 mmol, 3 eq) was added to the mixture. The mixture was stirred at 28° C. for 30 min, 1,1-difluoro-4-isocyano-cyclohexane (1045.08 mg, 3.60 mmol, 3 eq) was added and the mixture stirred at 28° C. for 30 min. $ZnCl_2$ (1962.72 mg, 14.40 mmol, 674.48 uL, 6 eq) was added and the mixture was stirred at 28° C. for 16 h. Upon completion, the reaction mixture was concentrated under reduced pressure to give a residue. The crude product was purified by pre-HPLC (Column: column: Waters Xbridge Prep OBD C18 150*40 mm*10 um; mobile phase: [water (10 mM $NH_4HCO_3$)-ACN]; B %: 40%-70%, 8 min). Compound tert-butyl (2R,4R)-2-[(4-tert-butyl-2-fluoro-phenyl)-[2-[(4,4-difluorocyclohexyl)amino]-1-(5-fluoro-3-pyridyl)-2-oxo-ethyl]carbamoyl]-4-methoxy-pyrrolidine-1-carboxylate Isomer 1 (174 mg, 261.76 umol, 10.91% yield) was obtained as a red solid. MS (ESI) m/z 665.2 $[M+H]^+$ Compound tert-butyl (2R,4R)-2-[(4-tert-butyl-2-fluoro-phenyl)-[2-[(4,4-difluorocyclohexyl)amino]-1-(5-fluoro-3-pyridyl)-2-oxo-ethyl]carbamoyl]-4-methoxy-pyrrolidine-1-carboxylate Isomer 2 (170 mg, 255.74 umol, 10.66% yield) was obtained as a yellow solid. MS (ESI) m/z 665.2 $[M+H]^+$ Step 2: (2R,4R)—N-(4-tert-butyl-2-fluoro-phenyl)-N-[2-[(4,4-difluorocyclohexyl)amino]-1-(5-fluoro-3-pyridyl)-2-oxo-ethyl]-4-methoxy-pyrrolidine-2-carboxamide Isomer 1

To a mixture of tert-butyl (2R,4R)-2-[(4-tert-butyl-2-fluoro-phenyl)-[2-[(4,4-difluorocyclohexyl)amino]-1-(5-fluoro-3-pyridyl)-2-oxo-ethyl]carbamoyl]-4-methoxy-pyrrolidine-1-carboxylate Isomer 1 (150 mg, 225.66 umol, 1 eq) in DCM (4.5 mL) was added TFA (2.31 g, 20.26 mmol, 1.5 mL, 168.34 eq) in one portion. The mixture was stirred at 0° C. for 2 h. Upon completion, the reaction mixture was concentrated to get the crude product. (2R,4R)—N-(4-tert-butyl-2-fluoro-phenyl)-N-[2-[(4,4-difluorocyclohexyl)amino]-1-(5-fluoro-3-pyridyl)-2-oxo-ethyl]-4-methoxy-pyrrolidine-2-carboxamide Isomer 1 (130 mg, crude) was obtained as light yellow oil and used directly next step. MS (ESI) m/z 565.4 $[M+H]^+$.

(2R,4R)—N-(4-tert-butyl-2-fluoro-phenyl)-N-[2-[(4,4-difluorocyclohexyl)amino]-1-(5-fluoro-3-pyridyl)-2-oxo-ethyl]-4-methoxy-pyrrolidine-2-carboxamide Isomer 2

To a mixture of tert-butyl (2R,4R)-2-[(4-tert-butyl-2-fluoro-phenyl)-[2-[(4,4-difluorocyclohexyl)amino]-1-(5-fluoro-3-pyridyl)-2-oxo-ethyl]carbamoyl]-4-methoxy-pyrrolidine-1-carboxylate Isomer 2 (150 mg, 225.66 umol, 1 eq) in DCM (4.5 mL) was added TFA (2.31 g, 20.26 mmol, 1.5 mL, 168.34 eq) in one portion. The mixture was stirred at 0° C. for 2 h. Upon completion, the reaction mixture was concentrated to get the crude product. (2R,4R)—N-(4-tert-butyl-2-fluoro-phenyl)-N-[2-[(4,4-difluorocyclohexyl)amino]-1-(5-fluoro-3-pyridyl)-2-oxo-ethyl]-4-methoxy-pyrrolidine-2-carboxamide Isomer 2 (120 mg, crude) was obtained as light yellow oil and used directly next step. MS (ESI) m/z 565.4 $[M+H]^+$.

Step 3: (2R,4R)—N-(4-tert-butyl-2-fluoro-phenyl)-1-cyano-N-[2-[(4,4-difluorocyclohexyl)amino]-1-(5-fluoro-3-pyridyl)-2-oxo-ethyl]-4-methoxy-pyrrolidine-2-carboxamide Isomer 1

To a mixture of (2R,4R)—N-(4-tert-butyl-2-fluoro-phenyl)-N-[2-[(4,4-difluorocyclohexyl)amino]-1-(5-fluoro-3-pyridyl)-2-oxo-ethyl]-4-methoxy-pyrrolidine-2-carboxamide Isomer 1 (130 mg, crude, 1 eq) and $NaHCO_3$ (145.07 mg, 1.73 mmol, 67.16 uL, 7.5 eq) in EtOH (2 mL) was added BrCN (48.78 mg, 460.49 umol, 33.87 uL, 2 eq) in one portion at 0° C. The mixture was stirred at 0° C. for 3 h. The residue was poured into water (2 mL) and extracted with ethyl acetate (2 mL*3). The combined organic phase was washed with brine (2 mL), dried with anhydrous $Na_2SO_4$, filtered and concentrated in vacuum to get the crude product. The crude product was purified by pre-HPLC. (column: Waters Xbridge BEH C18 100*30 mm*10 um; mobile phase: [water (10 mM $NH_4HCO_3$)-ACN]; B %: 35%-60%, 10 min) (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide Isomer 1 (32 mg, 54.27 umol, 23.57% yield, 100.0% purity) was obtained as a white solid. MS (ESI) m/z 590.3 $[M+H]^+$ $^1$H NMR (400 MHz, DMSO-$d_6$) δ ppm 8.32-8.47 (m, 2H), 8.14 (s, 1H), 7.85-7.95 (m, 1H), 7.22-7.32 (m, 2H), 6.92-7.00 (m, 1H), 6.08-6.18 (m, 1H), 3.99 (dd, J=8.71, 6.73 Hz, 1H), 3.80-3.93 (m, 2H), 3.61 (dd, J=9.37, 6.06 Hz, 1H), 3.27-3.32 (m, 1H), 3.03-3.18 (m, 3H), 1.81-2.10 (m, 6H), 1.68-1.80 (m, 2H), 1.45-1.58 (m, 1H), 1.30 (br dd, J=12.46, 6.28 Hz, 1H), 1.07-1.25 (m, 8H)

(2R,4R)—N-(4-tert-butyl-2-fluoro-phenyl)-1-cyano-N-[2-[(4,4-difluorocyclohexyl)amino]-1-(5-fluoro-3-pyridyl)-2-oxo-ethyl]-4-methoxy-pyrrolidine-2-carboxamide Isomer 1

To a mixture of (2R,4R)—N-(4-tert-butyl-2-fluoro-phenyl)-N-[2-[(4,4-difluorocyclohexyl)amino]-1-(5-fluoro-3-pyridyl)-2-oxo-ethyl]-4-methoxy-pyrrolidine-2-carboxamide Isomer 1 (120 mg, crude, 1 eq) and $NaHCO_3$ (133.91 mg, 1.59 mmol, 61.99 uL, 7.5 eq) in EtOH (2 mL) was added BrCN (45.02 mg, 425.07 umol, 31.27 uL, 2 eq) in one portion at 0° C. The mixture was stirred at 0° C. for 3 h. The residue was poured into water (2 mL) and extracted with ethyl acetate (2 mL*3). The combined organic phase was washed with brine (2 mL), dried with anhydrous $Na_2SO_4$, filtered and concentrated in vacuum to get the crude product. The crude product was purified by pre-HPLC. (column: Phenomenex Gemini-NX 80*40 mm*3 um; mobile phase: [water (10 mM $NH_4HCO_3$)-ACN]; B %: 30%-60%, 8 min) (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide Isomer 2 (25 mg, 42.40 umol, 19.95% yield, 100.0% purity) was obtained as a white solid. MS (ESI) m/z 590.3 [M+H]J $^1$H NMR (400 MHz, DMSO-$d_6$) δ ppm 8.34-8.51 (m, 1H), 8.32 (br d, J=7.28 Hz, 1H), 8.12-8.24 (m, 1H), 7.86-7.99 (m, 1H), 7.26-7.40 (m, 1H), 7.16-7.25 (m, 1H), 6.80-6.97 (m, 1H), 5.94-6.04 (m, 1H), 4.13 (dd, J=8.93, 6.06 Hz, 1H), 3.84-4.05 (m, 2H), 3.58 (dd, J=9.59, 6.06 Hz, 1H), 3.26-3.31 (m, 1H), 3.09-3.18 (m, 3H), 1.84-2.10 (m, 6H), 1.71-1.83 (m, 2H), 1.32-1.54 (m, 2H), 1.06-1.30 (in, 9H).

Example 129: Synthesis of Compound 1139

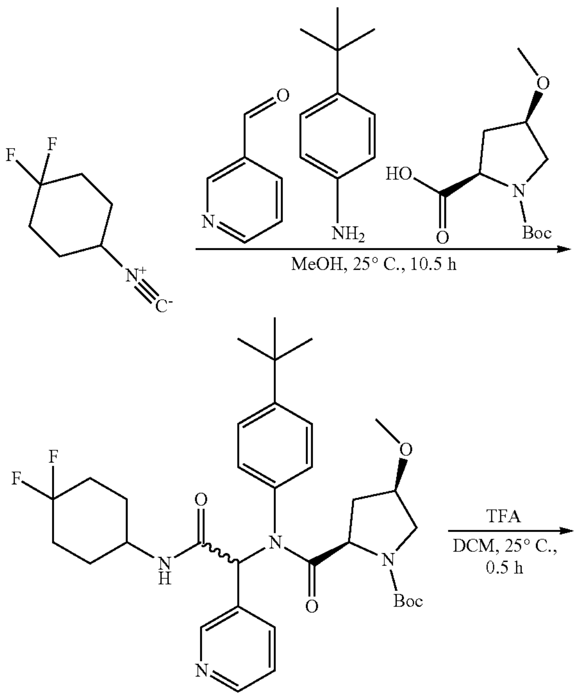

-continued

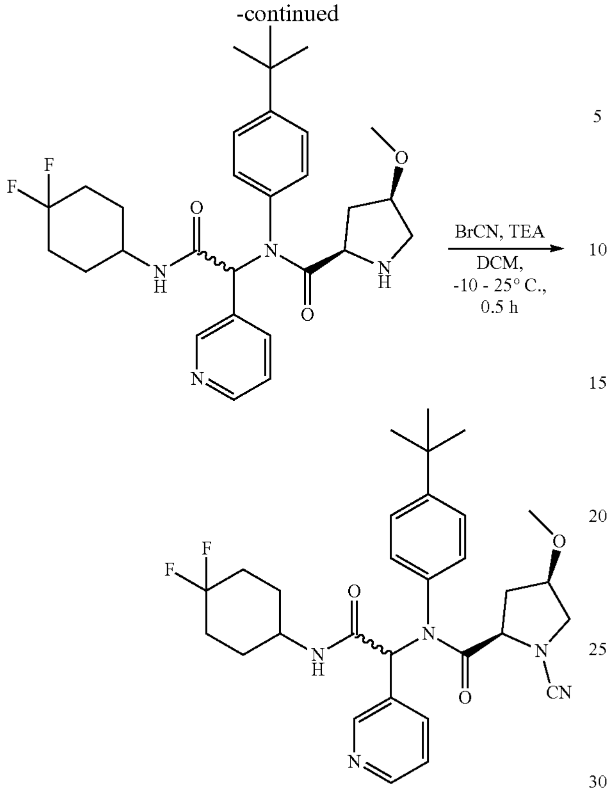

Step 1: (2R,4R)-tert-butyl2-((4-(tert-butyl)phenyl)(2-((4,4-difluorocyclohexyl)amino)-2-oxo-1-(pyridin-3-yl)ethyl)carbamoyl)-4-methoxypyrrolidine-1-carboxylate 4-tert-butylaniline (1.22 g, 8.15 mmol, 1.29 mL, 1 eq) and pyridine-3-carbaldehyde (873.40 mg, 8.15 mmol, 766.14 uL, 1 eq) in MeOH (30 mL) was stirred at 25° C. for 0.5 h. After the addition of (2R,4R)-1-tert-butoxycarbonyl-4-methoxy-pyrrolidine-2-carboxylic acid (2 g, 8.15 mmol, 1 eq) and 1,1-difluoro-4-isocyano-cyclohexane (1.18 g, 8.15 mmol, 1 eq), the mixture was stirred at 25° C. for 16 h. Upon completion, the mixture was concentrated under the reduced pressure to give a residue. The residue was purified by column chromatography ($SiO_2$, Petroleum ether:Ethyl acetate=5:1 to 0:1) affording the product tert-butyl(2R,4R)-2-[(4-tert-butylphenyl)-[2-[(4,4-difluorocyclohexyl)amino]-2-oxo-1-(3-pyridyl)ethyl]carbamoyl]-4-methoxy-pyrrolidine-1-carboxylate (1.5 g, 2.39 mmol, 29.26% yield) as a yellow solid. MS (ESI) m/z 629.3 $[M+H]^+$ Step 2: (2R,4R)—N-(4-(tert-butyl)phenyl)-N-(2-((4,4-difluorocyclohexyl)amino)-2-oxo-1-(pyridin-3-yl)ethyl)-4-methoxypyrrolidine-2-carboxamide To a solution of tert-butyl(2R,4R)-2-[(4-tert-butylphenyl)-[2-[(4,4-difluorocyclohexyl)amino]-2-oxo-1-(3-pyridyl)ethyl]carbamoyl]-4-methoxy-pyrrolidine-1-carboxylate (1.5 g, 2.39 mmol, 1 eq) in DCM (15 mL) was added TFA (7.70 g, 67.53 mmol, 5 mL, 28.31 eq), and the solution was stirred at 25° C. for 0.5 h. Upon completion, the reaction mixture was quenched by addition aq. $NaHCO_3$ (50 mL), and then extracted with DCM (30 mL*3). The combined organic layers were washed with brine (50 mL), dried over $Na_2SO_4$, filtered and concentrated under reduced pressure affording the product (2R,4R)—N-(4-tert-butylphenyl)-N-[2-[(4,4-difluorocyclohexyl)amino]-2-oxo-1-(3-pyridyl)ethyl]-4-methoxypyrrolidine-2-carboxamide (1 g, crude) as a yellow solid. MS (ESI) m/z 529.3 $[M+H]^+$ Step 3: (2R,4R)—N-(4-(tert-butyl)phenyl)-1-cyano-N-(2-((4,4-difluorocyclohexyl)amino)-2-oxo-1-(pyridin-3-yl)ethyl)-4-methoxypyrrolidine-2-carboxamide To a solution of (2R,4R)—N-(4-tert-butylphenyl)-N-[2-[(4,4-difluorocyclohexyl)amino]-2-oxo-1-(3-pyridyl)ethyl]-4-methoxypyrrolidine-2-carboxamide (1 g, 1.89 mmol, 1 eq) in DCM (10 mL) was added TEA (574.26 mg, 5.68 mmol, 789.90 uL, 3 eq), and the solution was cooled to −10° C. BrCN (240.44 mg, 2.27 mmol, 166.97 uL, 1.2 eq) in DCM (2 mL) was added and the solution stirred at 0° C. and warmed to 25° C. gradually. Upon completion, the mixture was quenched by addition $H_2O$ (30 mL) and then extracted with DCM (30 mL*3). The combined organic layers were washed with brine (30 mL), dried over $Na_2SO_4$, filtered and concentrated under reduced pressure to give a residue. The residue was purified by prep-HPLC (column: Kromasil C18 (250*50 mm*10 um); mobile phase: [water (10 mM $NH_4HCO_3$)-ACN]; B %: 40%-60%, 10 min) affording the product (2R,4R)—N-(4-tert-butylphenyl)-1-cyano-N-[2-[(4,4-difluorocyclohexyl)amino]-2-oxo-1-(3-pyridyl)ethyl]-4-methoxy-pyrrolidine-2-carboxamide (0.5 g, 903.11 umol, 47.74% yield, 100% purity) as a white solid. MS (ESI) m/z 554.3 $[M+H]^+$ $^1H$ NMR (400 MHz, METHANOL-$d_4$) δ=8.37-8.20 (m, 2H), 7.92-7.07 (m, 5H), 6.86-6.45 (m, 1H), 6.16 (s, 1H), 4.21 (dd, J=6.8, 8.6 Hz, 1H), 3.96-3.81 (m, 2H), 3.64 (dd, J=6.2, 9.4 Hz, 1H), 3.45 (dd, J=5.6, 9.4 Hz, 1H), 3.30-3.26 (m, 3H), 2.16-1.78 (m, 8H), 1.73-1.57 (m, 1H), 1.52-1.35 (m, 1H), 1.22 (s, 9H)

Example 130: Synthesis of Compound 1141

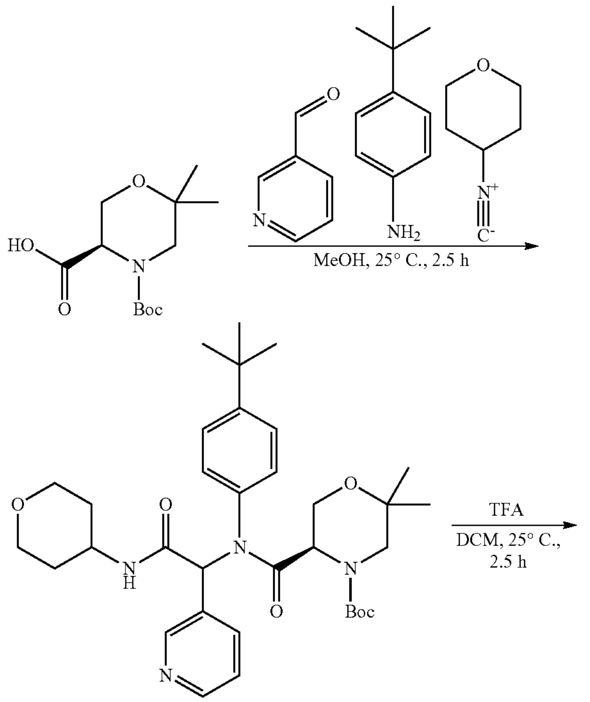

-continued

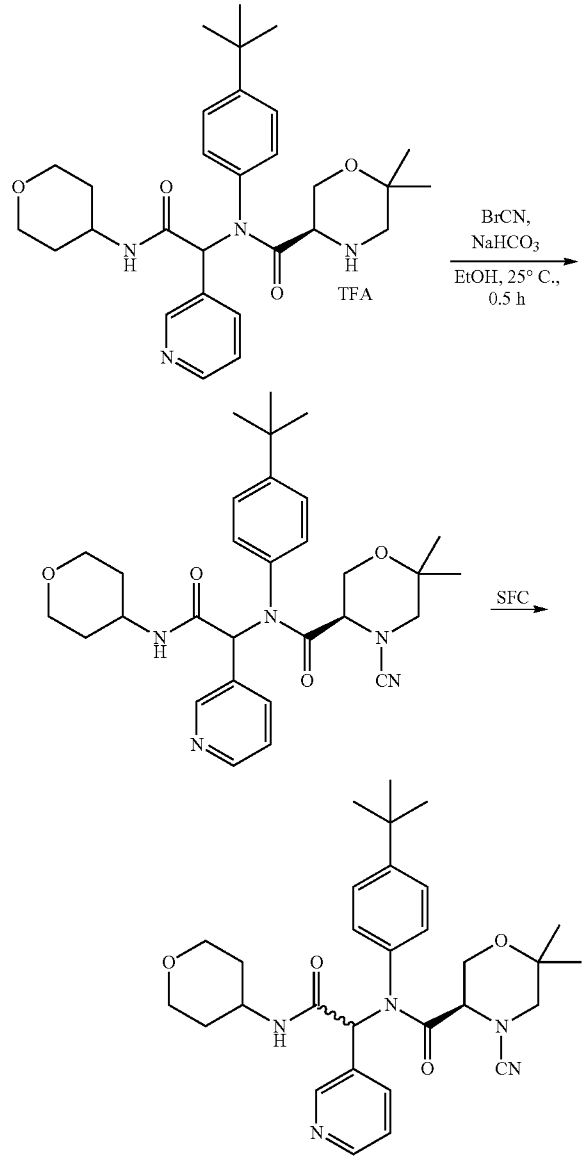

Step 1: tert-butyl(5R)-5-[(4-tert-butylphenyl)-[2-oxo-1-(3-pyridyl)-2-(tetrahydropyran-4-ylamino)ethyl]carbamoyl]-2,2-dimethyl-morpholine-4-carboxylate A solution of pyridine-3-carbaldehyde (185.88 mg, 1.74 mmol, 163.06 uL, 1 eq), 4-tert-butylaniline (310.78 mg, 2.08 mmol, 328.87 uL, 1.2 eq) in MeOH (1.2 mL) was stirred at 25° C. for 0.5 h, and then (3R)-4-tert-butoxycarbonyl-6,6-dimethyl-morpholine-3-carboxylic acid (450 mg, 1.74 mmol, 1 eq) was added at 25° C. and stirred at 25° C. for 0.5 h. Then the 4-isocyanotetrahydropyran (192.88 mg, 1.74 mmol, 1 eq) was added into the above solution at 0° C., and then the reaction mixture was stirred at 25° C. for 1.5 h. The solution was concentrated to get the crude product. The crude product was purified by prep-TLC and concentrated to get product. Tert-butyl(5R)-5-[(4-tert-butylphenyl)-[2-oxo-1-(3-pyridyl)-2-(tetrahydropyran-4-ylamino)ethyl]carbamoyl]-2,2-dimethyl-morpholine-4-carboxylate (0.7 g, crude) was obtained as light yellow solid. MS (ESI) m/z 609.4 $[M+H]^+$ Step 2: (3R)—N-(4-tert-butylphenyl)-6,6-dimethyl-N-[2-oxo-1-(3-pyridyl)-2-(tetrahydropyran-4-ylamino) ethyl]morpholine-3-carboxamide To a mixture of tert-butyl (5R)-5-[(4-tert-butylphenyl)-[2-oxo-1-(3-pyridyl)-2-(tetrahydropyran-4-ylamino)ethyl] carbamoyl]-2,2-dimethyl-morpholine-4-carboxylate (700 mg, 1.15 mmol, 1 eq) in DCM (9 mL) was added TFA (4.62 g, 40.52 mmol, 3.00 mL, 35.24 eq) at 25° C. under $N_2$. The mixture was stirred at 25° C. for 2.5 h. The reaction mixture was concentrated to get the crude product. (3R)—N-(4-tert-butylphenyl)-6,6-dimethyl-N-[2-oxo-1-(3-pyridyl)-2-(tetrahydropyran-4-ylamino)ethyl]morpholine-3-carboxamide (0.8 g, crude, TFA) as a yellow oil and was used directly next step. MS (ESI) m/z 509.4 $[M+H]^+$ Step 3: (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide To a mixture of (3R)—N-(4-tert-butylphenyl)-6,6-dimethyl-N-[2-oxo-1-(3-pyridyl)-2-(tetrahydropyran-4-ylamino)ethyl]morpholine-3-carboxamide (0.7 g, 1.38 mmol, 1 eq) and $NaHCO_3$ (867.07 mg, 10.32 mmol, 401.42 uL, 7.5 eq) in EtOH (7 mL) was added BrCN (196.79 mg, 1.86 mmol, 136.66 uL, 1.35 eq) in one portion at 0° C. The resulting mixture was stirred at 0° C. for 0.5 h. The residue was poured into water (3 mL) and extracted with ethyl acetate (2 mL*3). The combined organic phase was washed with brine (2 mL), dried with anhydrous $Na_2SO_4$, filtered and concentrated in vacuum to get the crude product. The crude product was purified by pre-HPLC. (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (85 mg, 90.0% purity) was obtained as a yellow solid. MS (ESI) m/z 534.3 $[M+H]^+$ Prep-HPLC condition: Column: Waters Xbridge BEH C18 100*25 mm*5 um; mobile phase: [water (10 mM NH4HCO3)-ACN]; B %: 30%-60%, 8 min $^1H$ NMR (400 MHz, DMSO-$d_6$) δ=8.52-8.06 (m, 3H), 7.90-6.55 (m, 6H), 6.13-5.90 (m, 1H), 3.88-3.59 (m, 6H), 3.49-3.37 (m, 1H), 3.31-3.25 (m, 1H), 2.94-2.82 (m, 1H), 1.75-1.56 (m, 2H), 1.49-1.29 (m, 2H), 1.28-0.99 (m, 15H)

Step 4: (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (85 mg, 90.0% purity) was separated by SFC to get the product Isomer 1: (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (8.85 mg, 16.58 umol, 1.21% yield, 100.0% purity) was obtained as a yellow solid. MS (ESI) m/z 534.3 $[M+H]^+$ Isomer 2: (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (21.17 mg, 39.00 umol, 2.83% yield, 98.3% purity) was obtained as a yellow solid. MS (ESI) m/z 534.3 $[M+H]^+$ Isomer 3: (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (7.78 mg, 14.58 umol, 1.06% yield, 100.0% purity) was obtained as a yellow solid. MS (ESI) m/z 534.3 $[M+H]^+$ Isomer 4: (3R)—N-(4-tert-butylphenyl)-4-cyano-6,6-dimethyl-N-[2-oxo-1-(3-pyridyl)-2-(tetrahydropyran-4-ylamino)ethyl]morpholine-3-carboxamide (18.38 mg, 33.61 umol, 2.44% yield, 97.6% purity) was obtained as a yellow solid. MS (ESI) m/z 534.3 $[M+H]^+$ SFC condition: column: DAICEL CHIRALCEL OJ (250 mm*30 mm, 10 um); mobile phase: [Neu-MeOH]; B %: 25%-25%, 15 min $^{1}$H NMR (400 MHz, DMSO-$d_6$) δ=8.50-7.98 (m, 3H), 7.78-6.30 (m, 6H), 5.92 (s, 1H), 3.97-3.41 (m, 18H), 2.89 (br d, J=11.9 Hz, 1H), 1.69-1.54 (m, 2H), 1.36-1.06 (m, 17H)

$^{1}$H NMR (400 MHz, DMSO-$d_6$) δ=8.44-8.07 (m, 3H), 7.72-6.43 (m, 6H), 6.20-5.97 (m, 1H), 3.94-3.54 (m, 91), 2.85 (br d, J=12.0 Hz, 1H), 1.73-1.61 (m, 1H), 1.48-1.03 (m, 18H)

$^{1}$H NMR (400 MHz, DMSO-$d_6$) δ=8.51-7.94 (m, 3H), 7.73-6.56 (m, 6H), 6.09 (s, 1H), 3.82 (br d, J=10.8 Hz, 3H), 3.76-3.57 (m, 6H), 2.86 (br d, J=12.2 Hz, 1H), 1.74-1.60 (m, 2H), 1.47-1.33 (m, 2H), 1.24-1.14 (m, 12H), 1.06 (s, 3H)

$^{1}$H NMR (400 MHz, DMSO-$d_6$) δ=8.33 (br d, J=10.4 Hz, 2H), 8.11 (br d, J=6.8 Hz, 1H), 7.63-6.92 (m, 6H), 5.92 (br s, 1H), 3.81-3.43 (m, 1H), 2.89 (br d, J=12.1 Hz, 1H), 1.75-1.51 (m, 1H), 1.74-0.94 (m, 161)

Example 131: Synthesis of Compound 1142

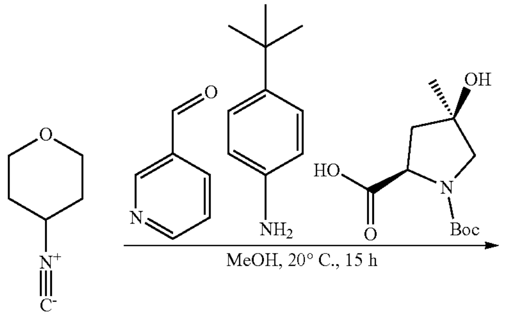

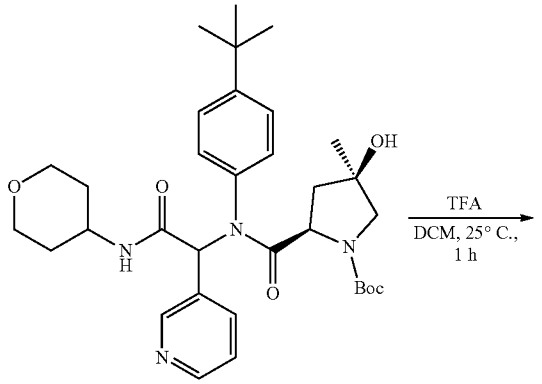

-continued

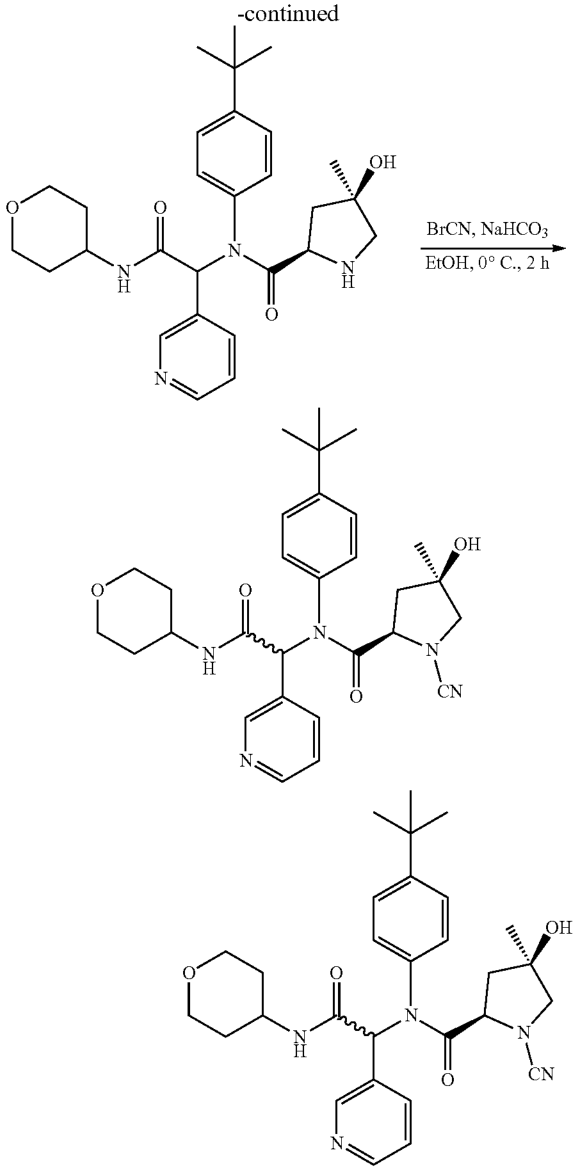

Step 1: tert-butyl (2R,4R)-2-[(4-tert-butylphenyl)-[2-oxo-1-(3-pyridyl)-2-(tetrahydropyran-4-ylamino)ethyl]carbamoyl]-4-hydroxy-4-methyl-pyrrolidine-1-carboxylate To a solution of 4-tert-butylaniline (350 mg, 2.35 mmol, 370.37 uL, 1 eq) in MeOH (12 mL) was added pyridine-3-carbaldehyde (251.21 mg, 2.35 mmol, 220.36 uL, 1 eq), and the resulting solution was stirred for 1 h. After (2R,4R)-1-tert-butoxycarbonyl-4-hydroxy-4-methyl-pyrrolidine-2-carboxylic acid (676.76 mg, 2.35 mmol, 85% purity, 1 eq) and 4-isocyanotetrahydropyran (260.66 mg, 2.35 mmol, 1 eq) were added, the solution was stirred for 15 h at 20° C. The reaction was cautiously concentrated to give crude. The crude was purified by pre-HPLC (column: AgelaDuraShell C18 250*80 mm*10 um; mobile phase: [water (10 mM $NH_4HCO_3$)-ACN]; B %: 40%-65%, 20 min) to afford tert-butyl (2R,4R)-2-[(4-tert-butylphenyl)-[2-oxo-1-(3-pyridyl)-2-(tetrahydropyran-4-ylamino)ethyl]carbamoyl]-4-hydroxy-4-methyl-pyrrolidine-1-carboxylate (Isomer 1: 250 mg, 399.33 umol, 17.03% yield, 95% purity) and tert-butyl (2R,4R)-2-[(4-tert-butylphenyl)-[2-oxo-1-(3-pyridyl)-2-(tetrahydropyran-4-ylamino)ethyl]carbamoyl]-4-hydroxy-4-methyl-pyrrolidine-1-carboxylate (Isomer 2: 240 mg, 383.38 umol, 16.34% yield, 95% purity) as a white solid. MS (ESI) m/z 595.1 $[M+H]^+$ Step 2: (2R,4R)—N-(4-tert-butylphenyl)-4-hydroxy-4-methyl-N-[2-oxo-1-(3-pyridyl)-2-(tetrahydropyran-4-ylamino)ethyl]pyrrolidine-2-carboxamide A solution of tert-butyl (2R,4R)-2-[(4-tert-butylphenyl)-[2-oxo-1-(3-pyridyl)-2-(tetrahydropyran-4-ylamino)ethyl]carbamoyl]-4-hydroxy-4-methyl-pyrrolidine-1-carboxylate (250 mg, 420.54 umol, 1 eq) in DCM (6 mL) and TFA (1.5 mL) was stirred for 1 h at 25° C. Upon completion, the reaction was cautiously concentrated to give crude (2R,4R)—N-(4-tert-butylphenyl)-4-hydroxy-4-methyl-N-[2-oxo-1-(3-pyridyl)-2-(tetrahydropyran-4-ylamino)ethyl]pyrrolidine-2-carboxamide (224 mg, crude) as a yellow oil used for the next step. MS (ESI) m/z 495.3 $[M+H]^+$ Step 3: (2R,4R)—N-(4-tert-butylphenyl)-1-cyano-4-hydroxy-4-methyl-N-[2-oxo-1-(3-pyridyl)-2-(tetrahydropyran-4-ylamino)ethyl]pyrrolidine-2-carboxamide A solution of (2R,4R)—N-(4-tert-butylphenyl)-4-hydroxy-4-methyl-N-[2-oxo-1-(3-pyridyl)-2-(tetrahydropyran-4-ylamino)ethyl]pyrrolidine-2-carboxamide (224 mg, 452.87 umol, 1 eq) in EtOH (6 mL) was added with $NaHCO_3$ (114.13 mg, 1.36 mmol, 52.84 uL, 3 eq) at 0° C. After BrCN (95.94 mg, 905.74 umol, 66.62 uL, 2 eq) was added, the solution was stirred for 2 h at 0° C. The reaction was quenched with $H_2O$ (20 mL) and extracted with EA (40 mL*3) and washed with brine (40 mL) and cautiously concentrated to give crude. The crude was prep-HPLC (column: Waters Xbridge BEH C18 100*30 mm*10 um; mobile phase: [water (10 mM $NH_4HCO_3$)-ACN]; B %: 20%-45%, 8 min) to afford (2R,4R)—N-(4-tert-butylphenyl)-1-cyano-4-hydroxy-4-methyl-N-[2-oxo-1-(3-pyridyl)-2-(tetrahydropyran-4-ylamino)ethyl]pyrrolidine-2-carboxamide (60 mg, 115.47 umol, 25.50% yield) as a yellow solid. MS (ESI) m/z 520.1 $[M+H]^+$.

Isomer 1: $^1H$ NMR (400 MHz, ACETONITRILE-$d_3$) δ ppm 8.24-8.43 (m, 2H) 6.94-7.68 (m, 5H) 6.62 (br d, J=7.72 Hz, 1H) 6.08 (s, 1H) 5.06 (s, 1H) 4.19 (dd, J=9.48, 2.65 Hz, 1H) 3.76-3.99 (m, 3H) 3.33-3.48 (in, 4H) 1.69-1.83 (m, 2H) 1.20-1.51 (m, 16H).

Step 4: (2R,4R)—N-(4-tert-butylphenyl)-4-hydroxy-4-methyl-N-[2-oxo-1-(3-pyridyl)-2-(tetrahydropyran-4-ylamino)ethyl]pyrrolidine-2-carboxamide A solution of tert-butyl (2R,4R)-2-[(4-tert-butylphenyl)-[2-oxo-1-(3-pyridyl)-2-(tetrahydropyran-4-ylamino)ethyl]carbamoyl]-4-hydroxy-4-methyl-pyrrolidine-1-carboxylate (240 mg, 403.54 umol, 1 eq) in DCM (6 mL) and TFA (1.5 mL) was stirred for 1 h at 25° C. The reaction was cautiously concentrated to give crude (2R,4R)—N-(4-tert-butylphenyl)-4-hydroxy-4-methyl-N-[2-oxo-1-(3-pyridyl)-2-(tetrahydropyran-4-ylamino)ethyl]pyrrolidine-2-carboxamide (224 mg, crude) as a yellow oil used for the next step. MS (ESI) m/z 495.3 $[M+H]^+$ Step 5: (2R,4R)—N-(4-tert-butylphenyl)-1-cyano-4-hydroxy-4-methyl-N-[2-oxo-1-(3-pyridyl)-2-(tetrahydropyran-4-ylamino)ethyl]pyrrolidine-2-carboxamide A solution of (2R,4R)—N-(4-tert-butylphenyl)-4-hydroxy-4-methyl-N-[2-oxo-1-(3-pyridyl)-2-(tetrahydropyran-4-ylamino)ethyl]pyrrolidine-2-carboxamide (224 mg, 452.87 umol, 1 eq) in EtOH (6 mL) was added with $NaHCO_3$ (114.13 mg, 1.36 mmol, 52.84 uL, 3 eq) at 0° C. After BrCN (95.94 mg, 905.74 umol, 66.62 uL, 2 eq) was added, the solution was stirred for 2 h at 0° C. The reaction was quenched with $H_2O$ (20 mL) and extracted with EA (40 mL*3) and washed with brine (40 mL) and cautiously concentrated to give crude. The crude was prep-HPLC (column: Waters Xbridge BEH C18 100*30 mm*10 um; mobile phase: [water (10 mM $NH_4HCO_3$)-ACN]; B %: 20%-45%, 8 min) to afford (2R,4R)—N-(4-tert-butylphenyl)-1-cyano-4-hydroxy-4-methyl-N-[2-oxo-1-(3-pyridyl)-2-(tetrahydropyran-4-ylamino)ethyl]pyrrolidine-2-carboxamide (40 mg, 76.98 umol, 17.00% yield) as a yellow solid. MS (ESI) m/z 520.1 $[M+H]^+$.

Isomer 2: $^1H$ NMR (400 MHz, ACETONITRILE-$d_3$) δ ppm 8.32-8.47 (m, 2H) 7.01-7.70 (m, 5H) 6.60 (br d, J=7.06 Hz, 1H) 5.97 (s, 1H) 5.33 (s, 1H) 4.20 (dd, J=9.04, 2.87 Hz, 1H) 3.77-3.98 (m, 3H) 3.31-3.49 (m, 4H) 1.69-1.86 (m, 2H) 1.20-1.54 (m, 16H).

Example 132: Synthesis of Compound 1303

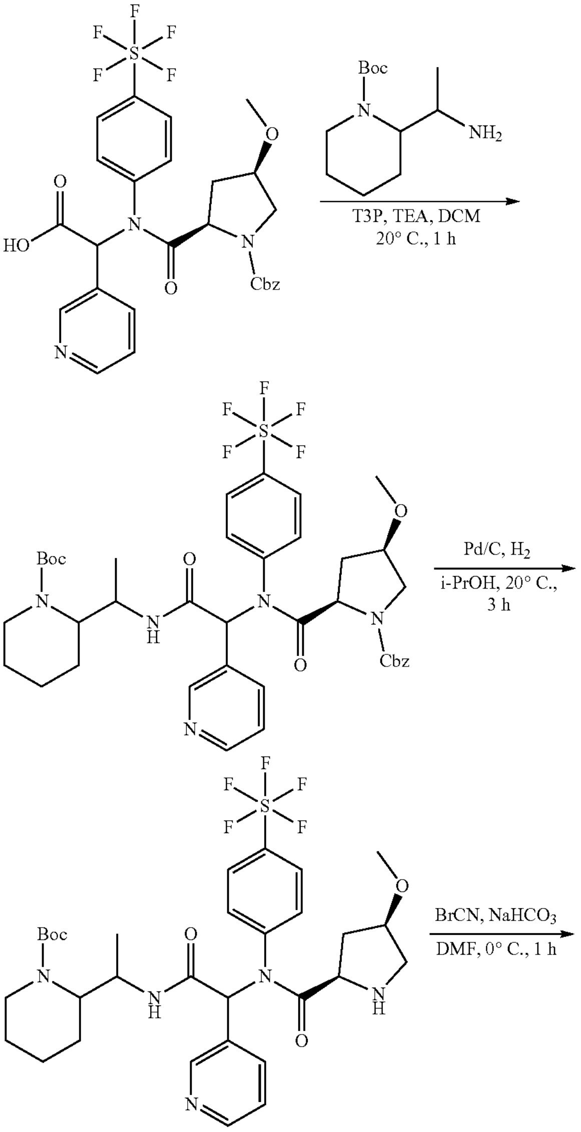

-continued

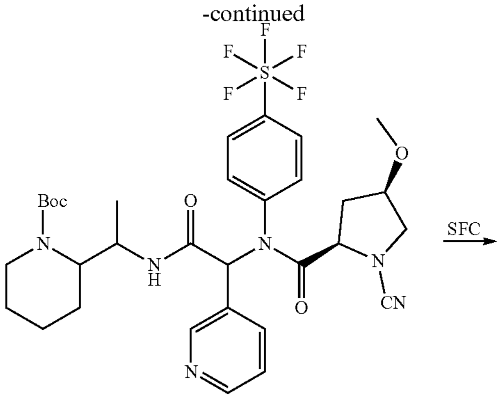

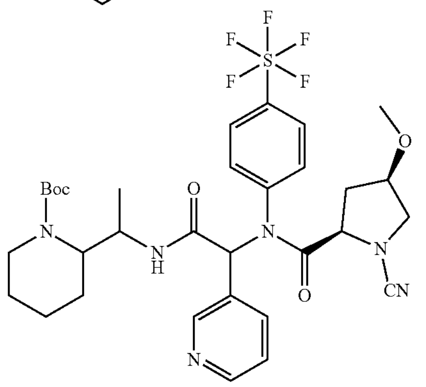

Step 1: tert-butyl 2-[1-[[2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate A mixture of tert-butyl 2-(1-aminoethyl)piperidine-1-carboxylate (111.28 mg, 487.35 umol, 1.5 eq), 2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetic acid (200 mg, 324.90 umol, 1 eq), T3P (620.27 mg, 974.71 umol, 579.69 uL, 50% purity, 3 eq), TEA (98.63 mg, 974.71 umol, 135.67 uL, 3 eq) in DCM (5 mL) was degassed and purged with $N_2$ for 3 times, and then the mixture was stirred at 20° C. for 1 h under $N_2$ atmosphere. Upon completion, the reaction mixture was quenched with $H_2O$ 25 mL at 20° C., and then extracted with DCM (25 mL*2). The combined organic layers were washed with brine (25 mL*2), dried over $Na_2SO_4$, filtered and concentrated under reduced pressure to give a residue. The residue was purified by column chromatography ($SiO_2$, petroleum ether/ethyl acetate=1/0 to 0/1) to give tert-butyl 2-[1-[[2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (240 mg, 261.54 umol, 80.50% yield, 90% purity) as a yellow solid. MS (ESI) m/z 826.2 [M+H]$^+$ Step 2: tert-butyl 2-[l-[[2-[N-[(2R,4R)-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate To a solution of tert-butyl 2-[1-[[2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (310 mg, 375.36 umol, 1 eq) in i-PrOH (6 mL) was added Pd/C (310 mg, 375.36 umol, 10% purity, 1 eq) under $N_2$. The suspension was degassed under vacuum and purged with $H_2$ several times. The mixture was stirred under $H_2$ (15 psi) at 20° C. for 3 h. Upon completion, the reaction mixture was filtered and concentrated under reduced pressure to give tert-butyl 2-[1-[[2-[N-[(2R,4R)-4-methoxypyrrolidine-2-carbonyl]-4-(pentafluoro-λ$^6$-sulfanyl)anilino]-2-(3-pyridyl)acetyl]amino]ethyl]piperidine-1-carboxylate (230 mg, crude) as a colorless oil. MS (ESI) m/z 692.2 [M+H]$^+$ Step 3: tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate To a solution of tert-butyl 2-[1-[[2-[N-[(2R,4R)-4-methoxypyrrolidine-2-carbonyl]-4-(pentafluoro-λ6-sulfanyl)anilino]-2-(3-pyridyl)acetyl]amino]ethyl]piperidine-1-carboxylate (220 mg, 318.03 umol, 1 eq), $NaHCO_3$ (3.64 mg, 43.37 umol, 1.69 uL, 3 eq) in DMF (5 mL) was added BrCN (40.42 mg, 381.64 umol, 28.07 uL, 1.2 eq) in DMF (1 mL) at 0° C., and the mixture was stirred at 0° C. for 1 h. Upon completion, the reaction mixture was poured into $H_2O$ 25 mL at 20° C., and then extracted with EtOAc (25 mL*3). The combined organic layers were washed with brine (25 mL*2), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM $NH_4HCO_3$)-ACN]; B %: 55%-75%, 8 min) to afford tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (28 mg, 39.06 umol, 12.28% yield, 100% purity) as a yellow solid. MS (ESI) m/z 717.3 [M+H]$^+$ Isomer 1: $^1$H NMR (400 MHz, MeOD-$d_4$) δ=8.39 (s, 2H), 8.13-7.09 (m, 6H), 6.05 (d, J=8.1 Hz, 1H), 4.61-4.42 (m, 1H), 4.24 (d, J=5.2 Hz, 1H), 3.98-3.86 (m, 2H), 3.64-3.58 (m, 1H), 3.51 (d, J=4.6, 9.7 Hz, 1H), 3.29-3.27 (m, 2H), 3.18 (d, J=4.5 Hz, 1H), 2.93-2.66 (m, 1H), 2.13-2.07 (m, 1H), 1.99-1.89 (m, 1H), 1.69-1.52 (m, 4H), 1.44 (d, J=3.0 Hz, 6H), 1.26 (d, J=6.6 Hz, 1H), 1.22-1.04 (m, 6H), 1.01-0.84 (m, 2H).

Tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (48 mg, 66.43 umol, 20.89% yield, 99.2% purity) was obtained as a yellow solid. MS (ESI) m/z 717.3 [M+H]$^+$ Isomer 2: $^1$H NMR (400 MHz, MeOD-$d_4$) δ=8.47-8.25 (m, 2H), 7.89-7.14 (m, 6H), 6.28-6.12 (m, 1H), 4.51 (d, J=6.6, 11.0 Hz, 1H), 4.27-4.19 (m, 1H), 4.10-3.88 (m, 3H), 3.67-3.60 (m, 1H), 3.48 (d, J=4.8, 9.6 Hz, 1H), 3.30-3.27 (m, 2H), 3.18 (d, J=4.2 Hz, 1H), 2.11-2.04 (m, 1H), 1.79 (d, J=12.9 Hz, 1H), 1.63 (d, J=7.9 Hz, 3H), 1.54-1.50 (m, 2H), 1.44 (s, 5H), 1.39 (d, J=7.3 Hz, 1H), 1.28 (d, J=6.4 Hz, 1H), 1.17-1.11 (m, 5H), 0.94 (t, J=7.3 Hz, 2H).

Tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (18 mg, 24.74 umol, 7.78% yield, 98.5% purity) was obtained as a yellow solid. MS (ESI) m/z 717.3 [M+H]$^+$ Isomer 3: $^1$H NMR (400 MHz, MeOD-$d_4$) δ=8.35 (d, J=13.2 Hz, 2H), 8.18-6.58 (m, 6H), 6.18 (s, 1H), 4.53 (d, J=3.0, 6.7 Hz, 1H), 4.23-4.11 (m, 1H), 4.08-3.96 (m, 2H), 3.91 (t, J=6.1 Hz, 1H), 3.72-3.59 (m, 1H), 3.54-3.43 (m, 1H), 3.28 (s, 2H), 3.19 (s, 1H), 2.18-2.06 (m, 1H), 2.04-1.93

(m, 1H), 1.80 (d, J=12.4 Hz, 1H), 1.66-1.61 (m, 4H), 1.54 (s, 6H), 1.42-1.36 (m, 2H), 1.18-1.12 (m, 1H), 1.17-1.12 (m, 1H), 1.10-1.07 (m, 2H), 0.94 (s, 2H).

Step 4: tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate Tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (40 mg) was separated by SFC (column: DAICEL CHIRALCEL OD (250 mm*30 mm, 10 um); mobile phase: [Neu-ETOH]; B %: 35%-35%, 15 min) to give tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (5.9 mg, 8.11 umol, 14.53% yield, 98.5% purity) as a white solid. MS (ESI) m/z 717.2 $[M+H]^+$ Isomer 1 of Isomer 2: $^1$H NMR (400 MHz, MeOD-$d_4$) δ=8.40-8.25 (m, 2H), 8.19-7.40 (m, 4H), 7.33-6.97 (m, 2H), 6.22-5.86 (m, 1H), 4.64-4.50 (m, 1H), 4.15 (t, J=8.0 Hz, 1H), 4.07-3.82 (m, 3H), 3.65 (d, J=3.9, 10.5 Hz, 1H), 3.52 (d, J=10.4 Hz, 1H), 3.22-3.13 (m, 3H), 3.06-2.81 (m, 1H), 2.09 (d, J=4.8, 8.6, 13.6 Hz, 1H), 1.97 (d, J=7.5 Hz, 1H), 1.77 (d, J=11.9 Hz, 2H), 1.64-1.60 (m, 3H), 1.54 (s, 2H), 1.49 (s, 1H), 1.40-1.34 (m, 2H), 1.26 (d, J=6.6 Hz, 2H), 1.13 (s, 4H), 0.96-0.92 (m, 21H).

Tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (25 mg, 34.57 umol, 61.94% yield, 99.1% purity) was obtained as a white solid. MS (ESI) m/z 717.2 $[M+H]^+$ Isomer 2 of Isomer 2: $^1$H NMR (400 MHz, MeOD-$d_4$) δ=8.48-8.25 (m, 2H), 8.08-7.40 (m, 4H), 7.23 (d, J=4.3, 8.0 Hz, 2H), 6.26-5.90 (m, 1H), 4.68-4.42 (m, 1H), 4.22 (d, J=6.3, 8.6 Hz, 1H), 4.10-3.78 (m, 3H), 3.67-3.59 (m, 1H), 3.48 (td, J=4.6, 9.5 Hz, 1H), 3.30-3.14 (m, 3H), 3.07-2.67 (m, 1H), 2.16-1.98 (m, 2H), 1.82-1.36 (m, 12H), 1.28 (d, J=6.6 Hz, 1H), 1.16-1.04 (m, 4H), 0.94 (t, J=7.3 Hz, 1H).

Tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (6.5 mg, 9.07 umol, 16.25% yield, 100% purity) was obtained as a white solid. MS (ESI) m/z 717.2 $[M+H]^+$ Isomer 3 of Isomer 2: $^1$H NMR (400 MHz, MeOD-$d_4$) δ=8.34 (d, J=1.6, 4.7 Hz, 2H), 7.58 (d, J=7.9 Hz, 4H), 7.24 (d, J=4.9, 7.9 Hz, 2H), 6.20 (s, 1H), 4.56-4.44 (m, 1H), 4.20 (d, J=6.4, 8.6 Hz, 1H), 4.06-3.89 (m, 3H), 3.64 (d, J=6.0, 9.5 Hz, 1H), 3.47 (d, J=5.2, 9.5 Hz, 1H), 3.29 (s, 3H), 2.89-2.66 (m, 1H), 2.05 (s, 2H), 1.62 (d, J=12.2 Hz, 2H), 1.44 (s, 10H), 1.33 (td, J=4.3, 13.0 Hz, 1H), 1.26-1.09 (m, 5H).

Tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (12 mg) was separated by SFC (column: DAICEL CHIRALPAK AD (250 mm*30 mm, 10 um); mobile phase: [0.1% $NH_3H_2O$ ETOH]; B %: 23%-23%, 10 min) to afford tert-butyl 2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (5.8 mg, 8.06 umol, 48.14% yield, 99.6% purity) as a white solid. MS (ESI) m/z 717.2 $[M+H]^+$ Isomer 1 of Isomer 3: $^1$H NMR (400 MHz, MeOD-$d_4$) δ=8.41-8.25 (m, 2H), 8.03-7.10 (m, 6H), 6.18 (s, 1H), 4.54 (d, J=3.7 Hz, 1H), 4.19 (d, J=6.3, 8.6 Hz, 1H), 4.11-3.84 (m, 3H), 3.66 (d, J=6.2, 9.2 Hz, 1H), 3.47 (d, J=5.7, 9.3 Hz, 1H), 3.28 (s, 3H), 3.01 (s, 1H), 2.11 (d, J=7.9 Hz, 1H), 2.05-1.96 (m, 1H), 1.80 (d, J=13.0 Hz, 1H), 1.71-1.60 (m, 4H), 1.54 (s, 9H), 1.44 (d, J=4.5 Hz, 1H), 1.09 (d, J=6.6 Hz, 3H).

Tert-butyl2-[1-[[2-[N-[(2R,4R)-1-cyano-4-methoxy-pyrrolidine-2-carbonyl]-4-(pentafluoro-λ$^6$-sulfanyl)anilino]-2-(3-pyridyl)acetyl]amino]ethyl]piperidine-1-carboxylate (2.5 mg, 3.47 umol, 20.71% yield, 99.4% purity) was obtained as a white solid. MS (ESI) m/z 717.2 $[M+H]^+$ Isomer 2 of Isomer 3: $^1$H NMR (400 MHz, MeOD-$d_4$) δ=8.42-8.29 (m, 2H), 7.56 (d, J=8.0 Hz, 4H), 7.40-6.72 (m, 2H), 6.17 (s, 1H), 4.53 (d, J=6.5, 10.4 Hz, 1H), 4.14 (t, J=7.7 Hz, 1H), 4.07-3.94 (m, 3H), 3.66 (d, J=3.9, 10.5 Hz, 1H), 3.51 (d, J=10.4 Hz, 1H), 3.19 (s, 3H), 3.02 (t, J=13.0 Hz, 1H), 2.14 (d, J=4.8, 8.2, 13.4 Hz, 1H), 1.97 (d, J=7.5, 13.6 Hz, 1H), 1.80 (d, J=12.8 Hz, 1H), 1.66-1.51 (m, 13H), 1.47-1.39 (m, 1H), 1.08 (d, J=6.6 Hz, 3H).

Example 131: Synthesis of Compound 1181

Step 1

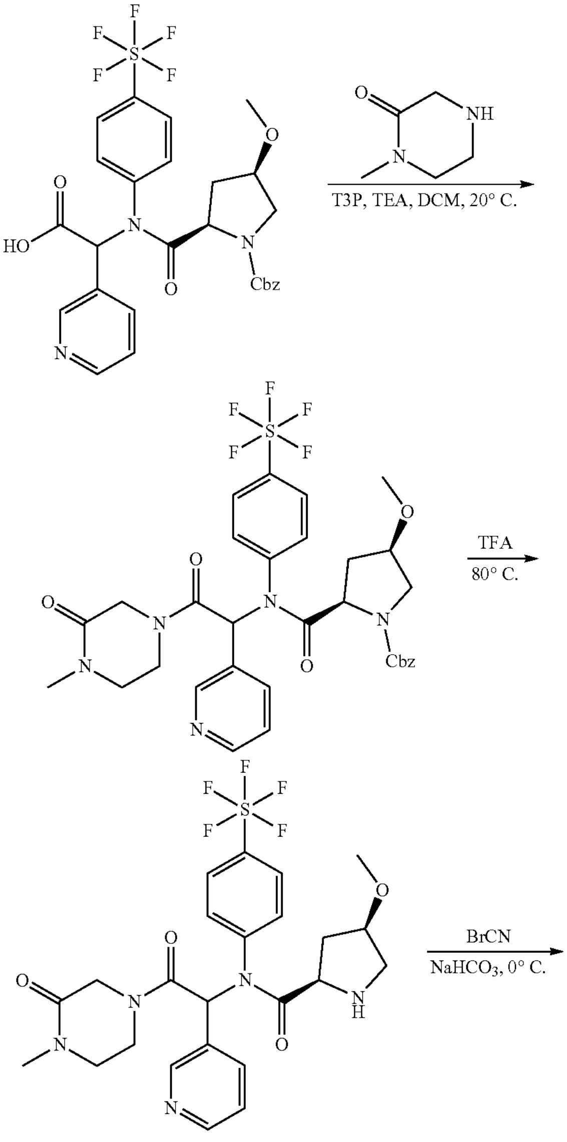

-continued

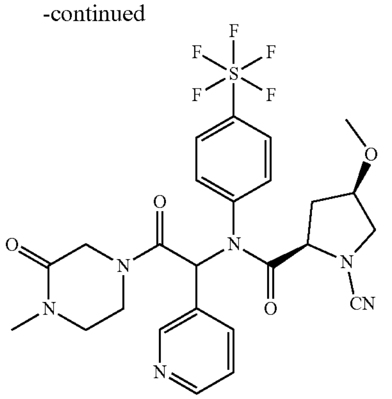

Step 1: benzyl (2R,4R)-4-methoxy-2-[[2-(4-methyl-3-oxo-piperazin-1-yl)-2-oxo-1-(3-pyridyl)ethyl]-[4-(pentafluoro-λ$^6$-sulfanyl)phenyl]carbamoyl]pyrrolidine-1-carboxylate A mixture of 2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetic acid (200 mg, 324.90 umol, 1 eq), 1-methylpiperazin-2-one (55.63 mg, 487.35 umol, 1.5 eq), T3P (620.27 mg, 974.71 umol, 579.69 uL, 50% purity, 3 eq), TEA (98.63 mg, 974.71 umol, 135.67 uL, 3 eq) in DCM (3 mL) was degassed and purged with $N_2$ for 3 times, and then the mixture was stirred at 25° C. for 1 h under $N_2$ atmosphere. Upon completion, the reaction mixture was poured into $H_2O$ 25 mL at 25° C., and then extracted with DCM (20 mL*3). The combined organic layers were washed with brine (20 mL*2), dried over $Na_2SO_4$, filtered and concentrated under reduced pressure to give a residue. The residue was purified by column chromatography ($SiO_2$, DCM:MeOH=30/1 to 10/1) to afford benzyl (2R,4R)-4-methoxy-2-[[2-(4-methyl-3-oxo-piperazin-1-yl)-2-oxo-1-(3-pyridyl)ethyl]-[4-(pentafluoro-λ$^6$-sulfanyl)phenyl]carbamoyl]pyrrolidine-1-carboxylate (191.2 mg, 268.65 umol, 82.69% yield) as a yellow solid. MS (ESI) m/z 712.2 $[M+H]^+$ Step 2: (2R,4R)-4-methoxy-N-[2-(4-methyl-3-oxo-piperazin-1-yl)-2-oxo-1-(3-pyridyl)ethyl]-N-[4-(pentafluoro-λ$^6$-sulfanyl)phenyl]pyrrolidine-2-carboxamide A solution of benzyl (2R,4R)-4-methoxy-2-[[2-(4-methyl-3-oxo-piperazin-1-yl)-2-oxo-1-(3-pyridyl)ethyl]-[4-(pentafluoro-λ$^6$-sulfanyl)phenyl]carbamoyl]pyrrolidine-1-carboxylate (171.6 mg, 241.11 umol, 1 eq) in TFA (1 mL) was stirred at 80° C. for 2 h. Upon completion, the reaction mixture was poured into $NaHCO_3$ (25 mL) at 25° C., and then extracted with DCM (20 mL*3). The combined organic layers were washed with brine (20 mL*2), dried over $Na_2SO_4$, filtered and concentrated under reduced pressure to give (2R,4R)-4-methoxy-N-[2-(4-methyl-3-oxo-piperazin-1-yl)-2-oxo-1-(3-pyridyl)ethyl]-N-[4-(pentafluoro-λ$^6$-sulfanyl)phenyl]pyrrolidine-2-carboxamide (129 mg, crude) as a yellow oil. MS (ESI) m/z 578.2 $[M+H]^+$ Step 3: (2R,4R)-1-cyano-4-methoxy-N-[2-(4-methyl-3-oxo-piperazin-1-yl)-2-oxo-1-(3-pyridyl)ethyl]-N-[4-(pentafluoro-λ$^6$-sulfanyl)phenyl]pyrrolidine-2-carboxamide To a solution of (2R,4R)-4-methoxy-N-[2-(4-methyl-3-oxo-piperazin-1-yl)-2-oxo-1-(3-pyridyl)ethyl]-N-[4-(pentafluoro-λ$^6$-sulfanyl)phenyl]pyrrolidine-2-carboxamide (109.1 mg, 188.90 umol, 1 eq) and $NaHCO_3$ (47.61 ng, 566.69 umol, 22.04 uL, 3 eq) in EtOH (3 mL) was added BrCN (26.01 mg, 245.56 umol, 18.06 uL, 1.3 eq) in EtOH (0.5 mL) at 0° C. The mixture was stirred at 0° C. for 1 h. Upon completion, the reaction mixture was quenched by addition $H_2O$ 25 mL at 20° C., and then extracted with EtOAc (25 mL*3). The combined organic layers were washed with brine (25 mL*2), dried over $Na_2SO_4$, filtered and concentrated under reduced pressure to give a residue. The residue was purified by prep-HPLC (column: Phenomenex Gemini-NX C18 75*30 mm*3 um; mobile phase: [water (0.05% $NH_3H_2O$+10 mM $NH_4HCO_3$)-ACN]; B %: 30%-50%, 8 min) to give (2R,4R)-1-cyano-4-methoxy-N-[2-(4-methyl-3-oxo-piperazin-1-yl)-2-oxo-1-(3-pyridyl)ethyl]-N-[4-(pentafluoro-λ$^6$-sulfanyl)phenyl]pyrrolidine-2-carboxamide (15.05 mg, 24.98 umol, 13.22% yield, 99.9% purity) as a yellow solid. MS (ESI) m/z 603.2 $[M+H]^+$ 1H NMR (400 MHz, MeOD-$d_4$) δ=8.48-8.33 (m, 2H), 8.23-7.49 (m, 4H), 7.26 (d, J 4.4, 7.4 Hz, 2H), 6.82-6.52 (m, 1H), 4.53-4.32 (m, 1H), 4.28-3.83 (m, 4H), 3.68-3.42 (m, 4H), 3.29 (d, J=2.8 Hz, 2H), 3.22-3.16 (m, 1H), 3.10-2.98 (m, 1H), 2.98-2.90 (m, 3H), 2.19-1.91 (m, 2H)

Example 132: Synthesis of Compound 1194

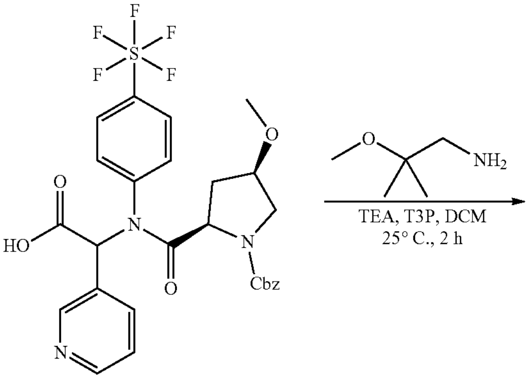

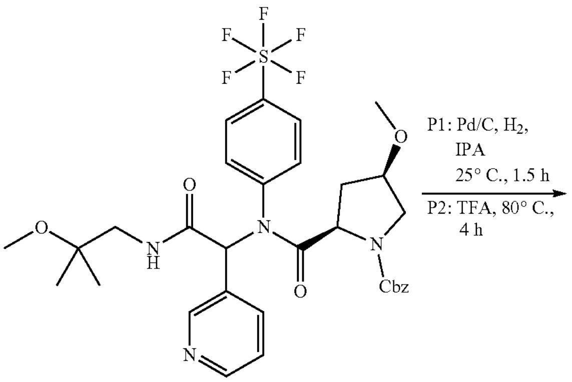

-continued

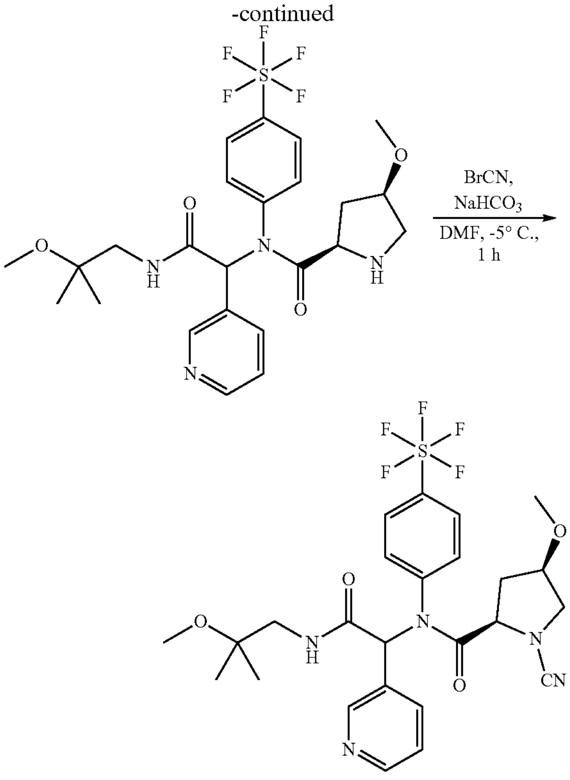

Step 1: benzyl (2R,4R)-4-methoxy-2-[[2-[(2-methoxy-2-methyl-propyl)amino]-2-oxo-1-(3-pyridyl)ethyl]-[4-(pentafluoro-$\lambda^6$-sulfanyl)phenyl]carbamoyl]pyrrolidine-1-carboxylate To a mixture of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (350 mg, 568.58 umol, 1 eq) in DCM (8 mL) was added 2-methoxy-2-methyl-propan-1-amine (175.97 mg, 1.71 mmol, 3 eq), TEA (345.21 mg, 3.41 mmol, 474.84 uL, 6 eq) and T3P (542.73 mg, 852.87 umol, 507.23 uL, 50% purity, 1.5 eq), and the resulting mixture was stirred at 25° C. for 2 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-60%, 8 min) to afford benzyl (2R,4R)-4-methoxy-2-[[2-[(2-methoxy-2-methyl-propyl)amino]-2-oxo-1-(3-pyridyl)ethyl]-[4-(pentafluoro-$\lambda^6$-sulfanyl)phenyl]carbamoyl]pyrrolidine-1-carboxylate Isomer 1 (179 mg, 255.45 umol, 44.93% yield) as white solid. MS (ESI) m/z 701.2 $[M+H]^+$.

Benzyl (2R,4R)-4-methoxy-2-[[2-[(2-methoxy-2-methyl-propyl)amino]-2-oxo-1-(3-pyridyl)ethyl]-[4-(pentafluoro-26-sulfanyl)phenyl]carbamoyl]pyrrolidine-1-carboxylate Isomer 2 (131 mg, 186.95 umol, 32.88% yield) was obtained as white solid. MS (ESI) m/z 701.2$[M+H]^+$.

Step 2: (2R,4R)-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 1

A mixture of benzyl (2R,4R)-4-methoxy-2-[[2-[(2-methoxy-2-methyl-propyl)amino]-2-oxo-1-(3-pyridyl)ethyl]-[4-(pentafluoro-$\lambda^6$-sulfanyl)phenyl]carbamoyl]pyrrolidine-1-carboxylate Isomer 1 (169 mg, 241.18 umol, 1 eq) in IPA (5 mL) was degassed and added with Pd/C (300 mg, 254.24 umol, 10% purity, 1.05 eq). The resulting solution was purged with $H_2$ (486.19 ug, 241.18 umol, 1 eq) and stirred under $H_2$ (15 psi or atm) at 25° C. for 1.5 h. Upon completion, the reaction mixture was filtered and concentrated under reduced pressure to afford (2R,4R)-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 1 (135 mg, crude) as white oil. MS (ESI) m/z 567.2 $[M+H]^+$.

(2R,4R)-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 2

A mixture of benzyl (2R,4R)-4-methoxy-2-[[2-[(2-methoxy-2-methyl-propyl)amino]-2-oxo-1-(3-pyridyl)ethyl]-[4-(pentafluoro-λ6-sulfanyl)phenyl]carbamoyl]pyrrolidine-1-carboxylate Isomer 2 (111 mg, 158.41 umol, 1 eq) in TFA (3 mL) was stirred at 80° C. for 4 h. Upon completion, the reaction mixture was base-modulated in saturated $NaHCO_3$ (5 mL) solution, and extracted with EA (3 mL*3). The combined organic layers were washed with brine, dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 10%-50%, 8 min) to get the product (2R,4R)-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 1 (25 mg, 44.12 umol, 27.85% yield) as white oil. MS (ESI) m/z 567.2 $[M+H]^+$.

Step 3: (2R,4R)-1-cyano-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 1

A mixture of (2R,4R)-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 1 (130 mg, 229.45 umol, 1 eq) in DMF (3 mL) was added with $NaHCO_3$ (57.83 mg, 688.34 umol, 26.77 uL, 3 eq), and then the solution was cooled to −5° C. After BrCN (29.16 mg, 275.33 umol, 20.25 uL, 1.2 eq) in DMF (0.5 mL) was added drop-wise, the mixture was stirred at −5° C. for 1 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 30%-60%, 8 min) to get the product (2R,4R)-1-cyano-4-methoxy-N-[2-[(2-methoxy-2-methyl-propyl)amino]-2-oxo-1-(3-pyridyl)ethyl]-N-[4-(pentafluoro-$\lambda^6$-sulfanyl)phenyl]pyrrolidine-2-carboxamide Isomer 1 (41.72 mg, 70.31 umol, 30.64% yield, 99.7% purity) as white solid. MS (ESI) m/z 592.2 $[M+H]^+$.

$^1H$ NMR (400 MHz, METHANOL-$d_4$) δ=8.53-8.00 (m, 3H), 7.75 (br s, 2H), 7.64-7.53 (m, 1H), 7.23 (dd, J=5.1, 7.6 Hz, 2H), 6.38-6.33 (m, 1H), 4.26-4.13 (m, 1H), 4.02-3.86 (m, 1H), 3.67-3.61 (m, 1H), 3.54-3.36 (m, 2H), 3.29-3.23

(m, 3H), 3.18 (t, J=2.8 Hz, 4H), 2.14-1.93 (m, 2H), 1.15-1.12 (m, 3H), 1.09-1.06 (m, 3H).

$^1$H NMR (400 MHz, DMSO-$d_6$) δ=8.33 (br s, 2H), 8.05 (br d, J=5.9 Hz, 1H), 7.83-7.72 (m, 2H), 7.55 (br d, J=2.1 Hz, 21H), 7.42 (br d, J=7.8 Hz, 1H), 7.18-7.10 (m, 1H), 6.34-6.30 (m, 1H), 4.11 (dd, J=6.9, 8.5 Hz, 1H), 3.87 (t, J=6.1 Hz, 1H), 3.60 (dd, J=6.2, 9.4 Hz, 1H), 3.35-3.24 (m, 2H), 3.19 (s, 2H), 3.18-3.13 (m, 1H), 3.10-3.07 (m, 4H), 2.07-1.92 (m, 1H), 1.78 (s, 1H), 1.07-1.03 (m, 3H), 1.02-0.97 (m, 3H).

(2R,4R)-1-cyano-4-methoxy-N-[2-[(2-methoxy-2-methyl-propyl)amino]-2-oxo-1-(3-pyridyl)ethyl]-N-[4-(pentafluoro-λ$^6$-sulfanyl)phenyl]pyrrolidine-2-carboxamide Isomer 2

A mixture of (2R,4R)-4-methoxy-N-[2-[(2-methoxy-2-methyl-propyl)amino]-2-oxo-1-(3-pyridyl)ethyl]-N-[4-(pentafluoro-λ$^6$-sulfanyl)phenyl]pyrrolidine-2-carboxamide Isomer 2 (25 mg, 44.12 umol, 1 eq) in DMF (1 mL) was added with $NaHCO_3$ (11.12 mg, 132.37 umol, 5.15 uL, 3 eq), and then the solution was cooled to −5° C. After BrCN (5.61 mg, 52.95 umol, 3.89 uL, 1.2 eq) in DMF (0.2 mL) was added drop-wise, the mixture was stirred at −5° C. for 1 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 30%-50%, 8 min) to get the product (2R,4R)-1-cyano-4-methoxy-N-[2-[(2-methoxy-2-methyl-propyl)amino]-2-oxo-1-(3-pyridyl) ethyl]-N-[4-(pentafluoro-λ$^6$-sulfanyl)phenyl]pyrrolidine-2-carboxamide Isomer 2 (5.12 mg, 8.63 umol, 19.56% yield, 99.7% purity) as yellow solid. MS (ESI) m/z 592.2 $[M+H]^+$.

$^1$H NMR (400 MHz, METHANOL-$d_4$) δ=8.39 (br d, J=1.8 Hz, 2H), 7.75 (br s, 3H), 7.59 (s, 1H), 7.25 (dd, J=4.9, 7.9 Hz, 2H), 6.19 (s, 1H), 4.28-4.10 (m, 1H), 4.03-3.87 (m, 1H), 3.61 (s, 1H), 3.50 (dd, J=4.2, 9.7 Hz, 2H), 3.29-3.27 (m, 3H), 3.19-3.15 (m, 4H), 2.15-2.06 (m, 1H), 2.05-1.90 (m, 1H), 1.14 (s, 3H), 1.07-1.04 (m, 3H).

Example 134: Synthesis of Compound 1196

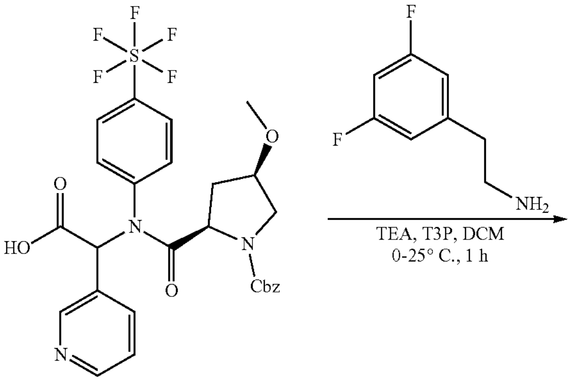

-continued

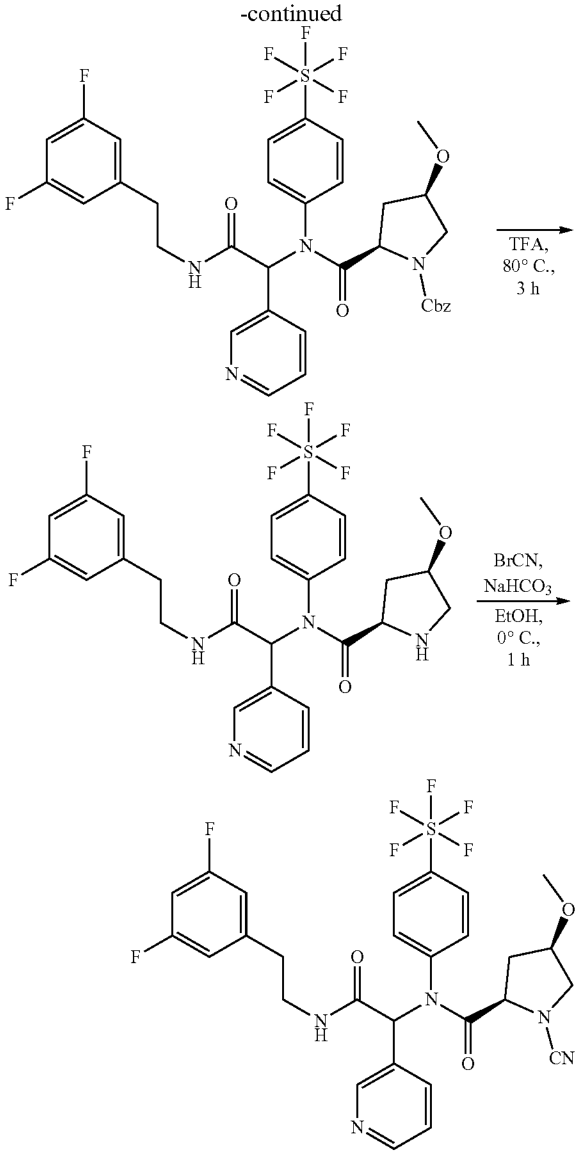

Step 1: benzyl(2R,4R)-2-[[2-[2-(3,5-difluorophenyl) ethylamino]-2-oxo-1-(3-pyridyl)ethyl]-[4-(pentafluoro-λ6-sulfanyl)phenyl]carbamoyl]-4-methoxy-pyrrolidine-1-carboxylate To a solution of 2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl) acetic acid (0.3 g, 487.35 umol, 1 eq) and 2-(3,5-difluorophenyl) ethanamine (153.19 mg, 974.71 umol, 2 eq) in DCM (5 mL) was added TEA (147.94 mg, 1.46 mmol, 203.50 uL, 3 eq), and the mixture was cooled to 0° C. After addition of T3P (465.20 mg, 731.03 umol, 434.77 uL, 50% purity, 1.5 eq) to the mixture at 0° C., the mixture was stirred at 25° C. for 1 h. Upon the reaction completion, the mixture was quenched by water (50 mL) and was extracted with DCM (15 mL*3), then was concentrated in vacuum to obtained benzyl (2R,4R)-2-[[2-[2-(3,5-difluorophenyl)ethylamino]-2-oxo-1-(3-pyridyl)ethyl]-[4-(pentafluoro-λ$^6$-sulfanyl)phenyl]carbamoyl]-4-methoxy-pyrrolidine-1-carboxylate (350 mg, crude) as a yellow gum. MS (ESI) m/z 755.2 $[M+H]^+$ Step 2: (2R,4R)—N-[2-[2-(3,5-difluorophenyl)ethylamino]-2-oxo-1-(3-pyridyl)ethyl]-4-methoxy-N-[4-(pentafluoro-λ6-sulfanyl)phenyl]pyrrolidine-2-carboxamide A solution of benzyl (2R,4R)-2-[[2-[2-(3,5-difluorophenyl)ethylamino]-2-oxo-1-(3-pyridyl) ethyl]-[4-(pentafluoro-$\lambda^6$-sulfanyl)phenyl]carbamoyl]-4-methoxy-pyrrolidine-1-carboxylate (350 mg, 463.75 umol, 1 eq) in TFA (6 mL) was stirred at 80° C. for 3 h. Upon completion, the mixture was concentrated in vacuum and the pH was adjusted to ~8 with sat. $Na_2CO_3$ (50 mL) and was extracted with DCM (15 mL*3), then was concentrated in vacuum to obtained (2R, 4R)—N-[2-[2-(3,5-difluorophenyl)ethylamino]-2-oxo-1-(3-pyridyl)ethyl]-4-methoxy-N-[4-(pentafluoro-λ6-sulfanyl) phenyl]pyrrolidine-2-carboxamide (300 mg, crude) as a yellow solid. MS (ESI) m/z 621.2 $[M+H]^+$ Step 3: (2R,4R)-1-cyano-N-[2-[2-(3,5-difluorophenyl)ethylamino]-2-oxo-1-(3-pyridyl)ethyl]-4-methoxy-N-[4-(pentafluoro-λ6-sulfanyl)phenyl]pyrrolidine-2-carboxamide To a solution of (2R,4R)—N-[2-[2-(3,5-difluorophenyl) ethylamino]-2-oxo-1-(3-pyridyl) ethyl]-4-methoxy-N-[4-(pentafluoro-$\lambda^6$-sulfanyl)phenyl]pyrrolidine-2-carboxamide (100 mg, 96.68 umol, 60% purity, 1 eq) in EtOH (1 mL) was added $NaHCO_3$ (24.37 mg, 290.05 umol, 11.28 uL, 3 eq), and then the mixture was cooled to 0° C. After the addition of BrCN (20.48 mg, 193.37 umol, 14.22 uL, 2 eq), the mixture was stirred at 0° C. for 1 h. Upon completion, the mixture was dried by blowing $N_2$ and was quenched by water (30 mL), then was extracted with DCM (10 mL*3), and concentrated in vacuum. The crude product was purified by prep-HPLC (column: Phenomenex Luna C18 75*30 mm*3 um; mobile phase: [water (0.2% FA)-ACN]; B %: 30%-70%, 8 min) to obtained (2R,4R)-1-cyano-N-[2-[2-(3,5-difluorophenyl)ethylamino]-2-oxo-1-(3-pyridyl)ethyl]-4-methoxy-N-[4-(pentafluoro-λ6-sulfanyl)phenyl]pyrrolidine-2-carboxamide (Isomer 1: 2.01 mg, 2.93 umol, 3.03% yield, 94% purity) as a yellow solid. MS (ESI) m/z 646.1 $[M+H]^+$ $^1$H NMR (Isomer 1) (400 MHz, MeOD-$d_4$) δ ppm 8.38 (dd, J=1.4, 4.9 Hz, 1H), 8.34-8.25 (m, 1H), 7.83-7.40 (m, 4H), 7.25-7.16 (m, 1H), 6.88-6.62 (m, 4H), 6.02 (s, 1H), 4.24 (dd, J=5.7, 8.8 Hz, 1H), 3.91 (q, J=5.5 Hz, 1H), 3.63-3.38 (m, 4H), 3.29-3.18 (m, 3H), 2.90-2.75 (m, 2H), 2.15-2.05 (m, 1H), 1.98-1.87 (m, 1H).

(2R,4R)-1-Cyano-N-[2-[2-(3,5-difluorophenyl)ethylamino]-2-oxo-1-(3-pyridyl)ethyl]-4-methoxy-N-[4-(pentafluoro-$\lambda^6$-sulfanyl)phenyl]pyrrolidine-2-carboxamide (Isomer 2: 2.35 mg, 3.35 umol, 3.46% yield, 92% purity) was obtained as a yellow solid. MS (ESI) m/z 646.1 $[M+H]^+$ $^1$H NMR (Isomer 2) (400 MHz, MeOD-$d_4$) δ ppm 8.35-8.25 (m, 2H), 7.84-7.37 (m, 4H), 7.18 (dd, J=4.9, 7.9 Hz, 1H), 6.87-6.66 (m, 4H), 6.21 (s, 1H), 4.25-4.12 (m, 1H), 4.02-3.87 (m, 1H), 3.69-3.57 (m, 2H), 3.51-3.39 (m, 2H), 3.30-3.16 (m, 3H), 2.86-2.75 (m, 2H), 2.16-1.97 (m, 2H).

Example 135: Synthesis of Compound 1055

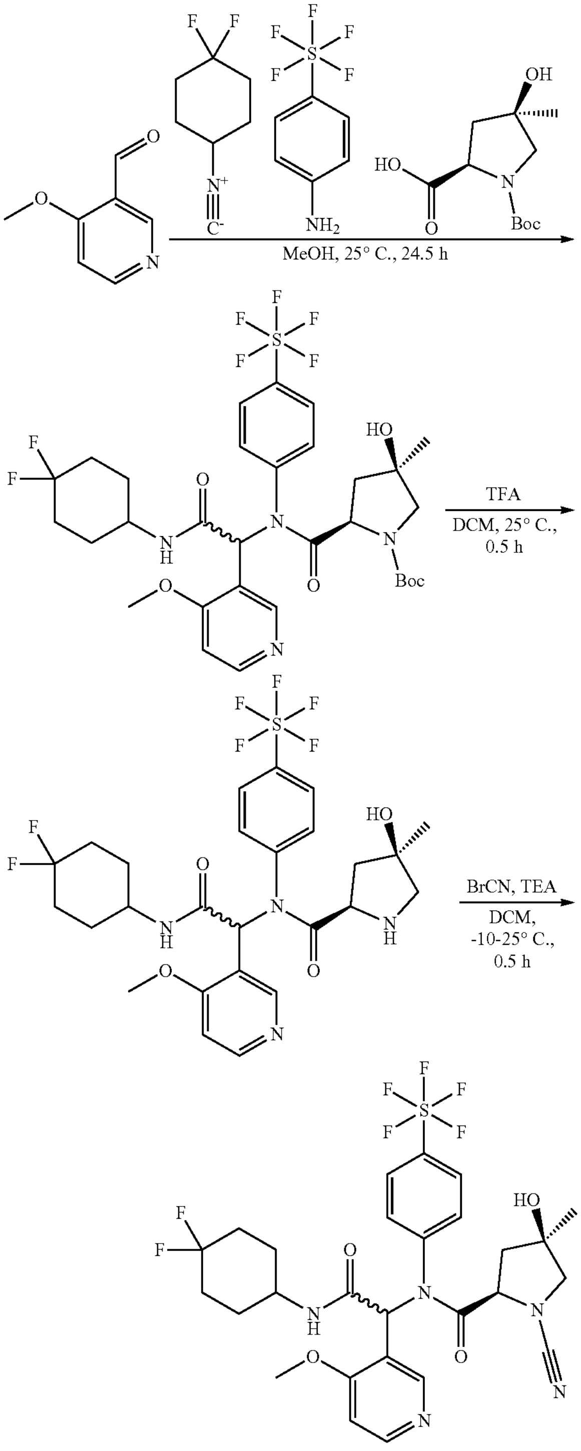

Step 1: tert-butyl(2R,4R)-2-[[2-[(4,4-difluorocyclohexyl)amino]-1-(4-methoxy-3-pyridyl)-2-oxo-ethyl]-[4-(pentafluoro-λ6-sulfanyl)phenyl]carbamoyl]-4-hydroxy-4-methyl-pyrrolidine-1-carboxylate A mixture of 4-(pentafluoro-λ6-sulfanyl)aniline (479.99 mg, 2.19 mmol, 1 eq) and 4-methoxypyridine-3-carbaldehyde (300.00 mg, 2.19 mmol, 1 eq) in MeOH (8 mL) was stirred at 25° C. for 0.5 h. After the addition of (2R,4R)-1-tert-butoxycarbonyl-4-hydroxy-4-methylpyrrolidine-2-carboxylic acid (537.15 mg, 2.19 mmol, 1 eq) and 1,1-difluoro-4-isocyano-cyclohexane (317.88 mg, 2.19 mmol, 1 eq), the mixture was stirred at 25° C. for 24 h. Upon completion, the mixture was concentrated under the reduced pressure to give a residue. The residue was purified by prep-HPLC (column: Kromasil C18 (250*50 mm*10 um); mobile phase: [water (10 mM $NH_4HCO_3$)-ACN]; B %: 50%-70%, 10 min) affording the product tert-butyl(2R,4R)-2-[[2-[(4,4-difluorocyclohexyl)amino]-1-(4-methoxy-3-pyridyl)-2-oxo-ethyl]-[4-(pentafluoro-λ6-sulfanyl)phenyl]carbamoyl]-4-hydroxy-4-methyl-pyrrolidine-1-carboxylate (150 mg, 205.84 umol, 9.40% yield) as a yellow oil. MS (ESI) m/z 729.0 $[M+H]^+$ Tert-butyl (2R,4R)-2-[[2-[(4,4-difluorocyclohexyl)amino]-1-(4-methoxy-3-pyridyl)-2-oxo-ethyl]-[4-(pentafluoro-λ6-sulfanyl)phenyl]carbamoyl]-4-hydroxy-4-methyl-pyrrolidine-1-carboxylate (150 mg, 205.84 umol, 9.40% yield) was obtained as a yellow oil. MS (ESI) m/z 729.0 $[M+H]^+$ Step 2: (2R,4R)—N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide To a solution of tert-butyl(2R,4R)-2-[[2-[(4,4-difluorocyclohexyl)amino]-1-(4-methoxy-3-pyridyl)-2-oxo-ethyl]-[4-(pentafluoro-λ6-sulfanyl)phenyl]carbamoyl]-4-hydroxy-4-methyl-pyrrolidine-1-carboxylate (130 mg, 178.40 umol, 1 eq) in DCM (3 mL) was added TFA (1.54 g, 13.51 mmol, 1 mL, 75.71 eq). The mixture was stirred at 25° C. for 0.5 h. Upon completion, the reaction mixture was quenched with sat. $NaHCO_3$ (10 mL), and then extracted with DCM (10 mL*3). The combined organic layers were washed with brine (10 mL), dried over $Na_2SO_4$, filtered and concentrated under reduced pressure affording the product (2R,4R)—N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide (110 mg, crude) as a yellow solid. MS (ESI) m/z 629.3 $[M+H]^+$ To a solution of tert-butyl(2R,4R)-2-[[2-[(4,4-difluorocyclohexyl)amino]-1-(4-methoxy-3-pyridyl)-2-oxo-ethyl]-[4-(pentafluoro-λ6-sulfanyl)phenyl]carbamoyl]-4-hydroxy-4-methyl-pyrrolidine-1-carboxylate (130 mg, 178.40 umol, 1 eq) in DCM (3 mL) was added TFA (1.54 g, 13.51 mmol, 1 mL, 75.71 eq), and the mixture was stirred at 25° C. for 0.5 h. Upon completion, the reaction mixture was quenched with sat. $NaHCO_3$ (10 mL), and then extracted with DCM (10 mL*3). The combined organic layers were washed with brine (10 mL), dried over $Na_2SO_4$, filtered and concentrated under reduced pressure affording the product (2R,4R)—N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide (110 mg, crude) as a yellow solid. MS (ESI) m/z 629.3 $[M+H]^+$ Step 3: (2R,4R)-1-cyano-N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide To a solution of (2R,4R)—N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide (100 mg, 159.08 umol, 1 eq) in DCM (3 mL) was added TEA (48.29 mg, 477.25 umol, 66.43 uL, 3 eq), and the solution was cooled to −10° C. After BrCN (20.22 mg, 190.90 umol, 14.04 uL, 1.2 eq) in DCM (1 mL) was added at 0° C., the solution was stirred and warmed to 25° C. gradually for 0.5 h. Upon completion, the mixture was quenched by addition $H_2O$ (10 mL) and then extracted with DCM (10 ml*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 35%-60%, 8 min) affording the product (2R,4R)-1-cyano-N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide (47 mg, 70.40 umol, 44.25% yield, 97.9% purity) as a white solid. MS (ESI) m/z 654.2 $[M+H]^+$ $^1H$ NMR (400 MHz, METHANOL-$d_4$) δ=8.25 (d, J=5.8 Hz, 1H), 7.96 (br s, 1H), 7.89 (s, 1H), 7.84-7.56 (m, 2H), 7.07 (br s, 1H), 6.97 (d, J=5.8 Hz, 1H), 6.46 (s, 1H), 4.27 (dd, J=4.4, 9.2 Hz, 1H), 4.00-3.88 (m, 4H), 3.50 (d, J=9.2 Hz, 1H), 3.35 (d, J=9.2 Hz, 1H), 2.11-1.84 (m, 8H), 1.63 (br dd, J=3.0, 10.4 Hz, 1H), 1.55-1.43 (m, 1H), 1.25 (s, 3H).

To a solution of (2R,4R)—N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide (100 mg, 159.08 umol, 1 eq) in DCM (3 mL) was added TEA (48.29 mg, 477.25 umol, 66.43 uL, 3 eq), and the solution was cooled to −10° C. After an addition of BrCN (20.22 mg, 190.90 umol, 14.04 uL, 1.2 eq) in DCM (1 mL) at 0° C., the solution was stirred and warmed to 25° C. gradually for 0.5 h. Upon completion, the mixture was quenched by addition $H_2O$ (10 mL) and then extracted with DCM (10 ml,*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 35%-60%, 8 min) affording the product (2R,4R)-1-cyano-N-[2-[(4,4-difluorocyclohexyl)amino]-1-(4-methoxy-3-pyridyl)-2-oxo-ethyl]-4-hydroxy-4-methyl-N-[4-(pentafluoro-λ6-sulfanyl)phenyl]pyrrolidine-2-carboxamide (47 mg, 67.23 umol, 42.26% yield, 93.5% purity) as a yellow solid. MS (ESI) m/z 654.2 $[M+H]^+$ $^1H$ NMR (400 MHz, METHANOL-$d_4$) δ=8.28 (d, J=5.8 Hz, 1H), 7.92 (s, 4H), 7.00 (d, J=5.8 Hz, 2H), 6.36 (s, 1H), 4.22 (t, J=6.8 Hz, 1H), 4.00-3.87 (m, 4H), 3.49 (d, J=9.2 Hz, 1H), 3.35 (d, J=9.4 Hz, 1H), 2.09-1.82 (m, 8H), 1.71-1.55 (m, 1H), 1.53-1.39 (m, 1H), 1.27 (s, 3H).

Example 136: Synthesis of Compound 1305

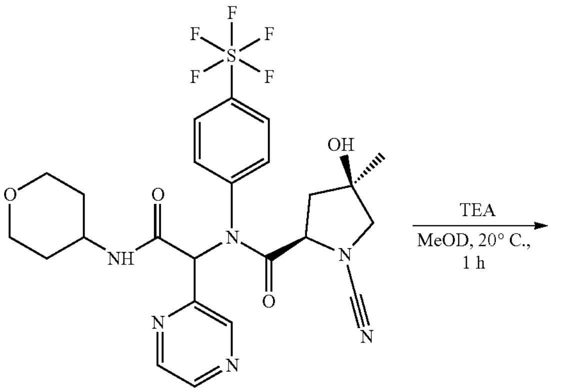

-continued

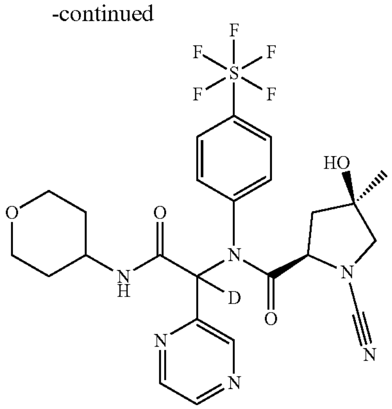

Step 1: (2R,4R)-1-cyano-N-[1-deuterio-2-oxo-1-pyrazin-2-yl-2-(tetrahydropyran-4-ylamino)ethyl]-4-hydroxy-4-methyl-N-[4-(pentafluoro-λ$^6$-sulfanyl)phenyl]pyrrolidine-2-carboxamide To a stirred solution of (2R,4R)-1-cyano-4-hydroxy-4-methyl-N-[2-oxo-1-pyrazin-2-yl-2-(tetrahydropyran-4-ylamino)ethyl]-N-[4-(pentafluoro-λ$^6$-sulfanyl)phenyl]pyrrolidine-2-carboxamide (30 mg, 50.80 umol, 1 eq) in MeOD (0.3 mL) was added TEA (5.14 mg, 50.80 umol, 7.07 uL, 1 eq) at 20° C., and then the mixture was stirred at 20° C. for 1 hr. The mixture was lyophilization from $D_2O$ (0.5 mL) to remove TEA and MeOD to give (2R,4R)-1-cyano-N-[1-deuterio-2-oxo-1-pyrazin-2-yl-2-(tetrahydropyran-4-ylamino)ethyl]-4-hydroxy-4-methyl-N-[4-(pentafluoro-26-sulfanyl)phenyl]pyrrolidine-2-carboxamide (21 mg, 30.88 umol, 60.80% yield, 87% purity) as a yellow solid. MS (ESI) m/z 519.3 $[M+H]^+$ $^1$H NMR (400 MHz, METHANOL-$d_4$) δ ppm 9.33-8.13 (m, 3H), 8.01-7.06 (m, 4H), 4.43-4.09 (m, 1H), 4.02-3.83 (m, 2H), 3.78-3.35 (m, 4H), 3.24-3.10 (m, 1H), 2.76-2.57 (m, 1H), 2.45-1.93 (m, 2H), 1.78-1.25 (m, 4H)

Example 137: Synthesis of Compound 1157

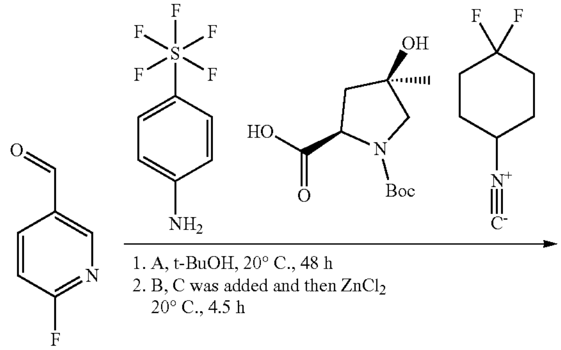

-continued

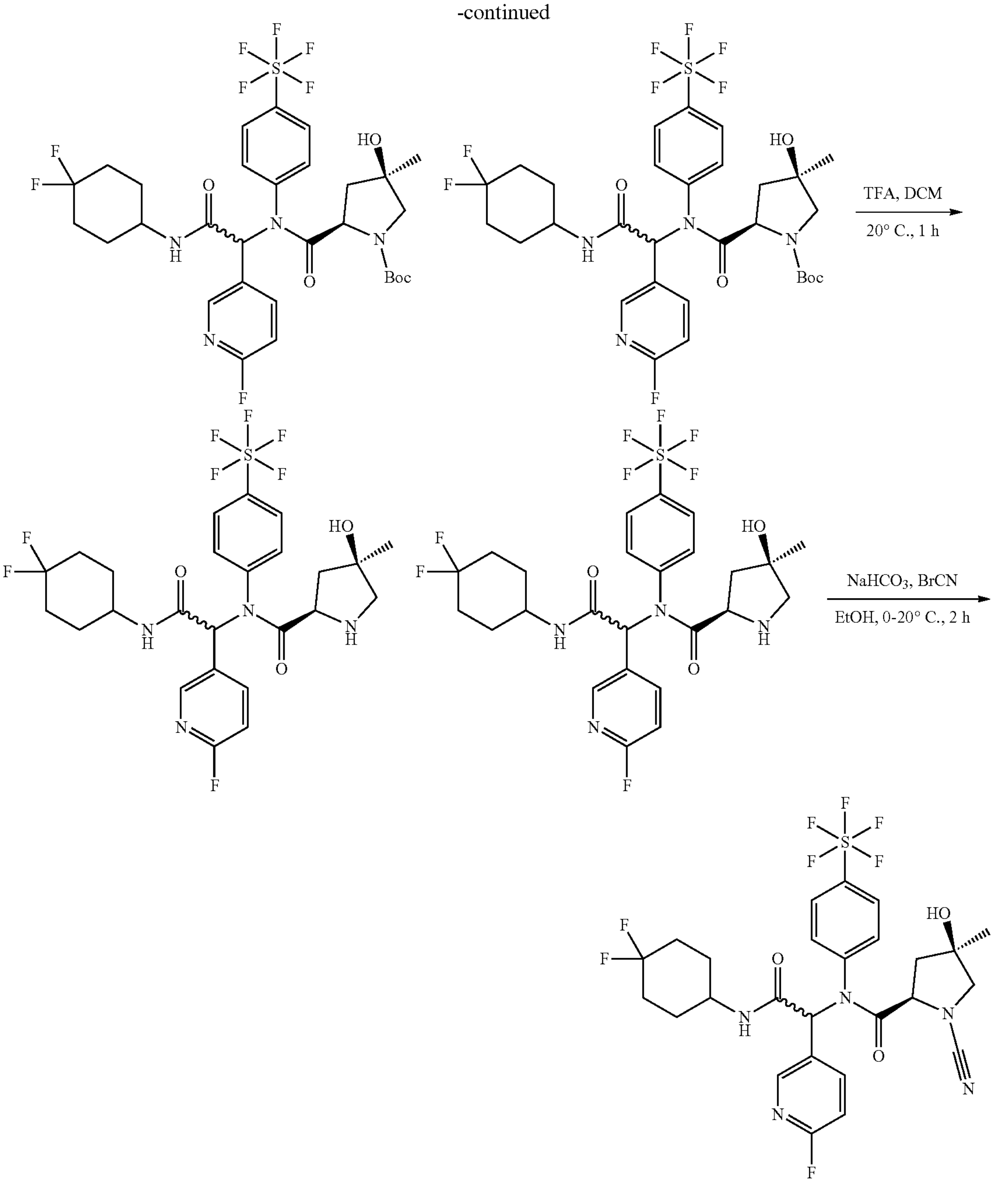

Step 1: tert-butyl (2R,4R)-2-[[2-[(4,4-difluorocyclohexyl)amino]-1-(6-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate A solution of 4-(pentafluoro-λ6-sulfanyl)aniline (350.40 mg, 1.60 mmol, 1 eq) and 6-fluoropyridine-3-carbaldehyde (300 mg, 2.40 mmol, 1.5 eq) in t-BuOH (15 mL) was stirred at 20° C. for 48 h, and then (2R,4R)-1-tert-butoxycarbonyl-4-hydroxy-4-methylpyrrolidine-2-carboxylic acid (392.12 mg, 1.60 mmol, 1 eq) and 1,1-difluoro-4-isocyano-cyclohexane (232.05 mg, 1.60 mmol, 1 eq) in t-BuOH (0.5 mL) were added into the solution. After 0.5 h, $ZnCl_2$/THF (1 M, 9.59 mL, 6 eq) was added into the solution. The resulting mixture was stirred at 20° C. for 4 h, and then the reaction mixture was concentrated under reduced pressure to remove solvent. The residue was purified by neutral prep-HPLC to get the product tert-butyl (2R,4R)-2-[[2-[(4,4-difluorocyclohexyl)amino]-1-(6-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (50 mg, 66.28 umol, 4.15% yield, 95% purity) was obtained as white solid. MS (ESI) in/z 717.2[M+H]$^+$.

Prep-HPLC condition: column: Kromasil C18 (250*50 mm*10 um); mobile phase: [water (0.05% $NH_3H_2O$+10 mM $NH_4HCO_3$)-ACN]; B %: 45%-65%, 10 min.

Compound tert-butyl (2R,4R)-2-[[2-[(4,4-difluorocyclohexyl)amino]-1-(6-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (49 mg, 64.95 umol, 4.06% yield, 95% purity) was obtained as white solid. MS (ESI) m/z 717.2[M+H]$^+$.

Step 2 Isomer 1: (2R,4R)—N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of tert-butyl (2R,4R)-2-[[2-[(4,4-difluorocyclohexyl)amino]-1-(6-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (47 mg, 65.58 umol, 1 eq) in DCM (0.4 mL) was added TFA (1.45 g, 12.70 mmol, 940.00 uL, 193.59 eq), and the mixture was stirred at 20° C. for 1 h. Upon completion, the reaction mixture was poured into Saturated sodium bicarbonate solution (5 ml) and extracted with DCM (2 mL*3). The combined organic layers were washed with brine (3 mL*1), dried over $Na_2SO_4$, filtered and concentrated under reduced pressure to give a residue to afford (2R,4R)—N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide (51 mg, crude) as white solid. MS (ESI) m/z 617.2 [M+H]$^+$.

Step 2 Isomer 2: (2R,4R)—N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of tert-butyl (2R,4R)-2-[[2-[(4,4-difluorocyclohexyl)amino]-1-(6-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (49 mg, 68.37 umol, 1 eq) in DCM (2 mL) was added TFA (770.00 mg, 6.75 mmol, 0.5 mL, 98.77 eq), and the mixture was stirred at 20° C. for 1 h. Upon completion, the reaction mixture was poured into saturated sodium bicarbonate solution (5 ml) and extracted with DCM (2 mL*3). The combined organic layers were washed with brine (3 mL*1), dried over $Na_2SO_4$, filtered and concentrated under reduced pressure to give a residue to afford (2R,4R)—N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide (51 mg, crude) as white solid. MS (ESI) m/z 617.2 [M+H]$^+$.

Step 3 Isomer 1: (2R,4R)-1-cyano-N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of (2R,4R)—N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide (47 mg, 76.23 umol, 1 eq) in EtOH (1 mL) was added $NaHCO_3$ (19.21 mg, 228.69 umol, 8.89 uL, 3 eq) then added BrCN (10.50 mg, 99.10 umol, 7.29 uL, 1.3 eq) at 0° C. The mixture was stirred at 0° C. for 1 h then stirred at 20° C. for 1 h. Upon completion, the reaction mixture was concentrated under reduced pressure to remove solvent. The residue was purified by neutral prep-HPLC to afford (2R,4R)-1-cyano-N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide (12.55 mg, 18.66 umol, 24.48% yield, 95.400% purity) as white solid. MS (ESI) m/z 642.3[M+H]$^+$.

Prep-HPLC condition: column: Waters Xbridge Prep OBD C18 150*40 mm*10 um; mobile phase: [water (10 mM $NH_4HCO_3$)-ACN]; B %: 35%-65%, 8 min.

$^1$H NMR (400 MHz, METHANOL-$d_4$) δ ppm 7.49-8.10 (m, 5H) 6.97-7.35 (m, 1H) 6.87 (dd, J=8.60, 2.43 Hz, 1H) 6.23 (s, 1H) 4.25 (dd, J=9.15, 4.74 Hz, 1H) 3.89 (br t, J=10.25 Hz, 1H) 3.49 (d, J=9.04 Hz, 1H) 3.34 (d, J=9.26 Hz, 1H) 1.81-2.13 (m, 8H) 1.57-1.73 (m, 1H) 1.39-1.55 (m, 1H) 1.25 (s, 3H).

Step 3 Isomer 2: (2R,4R)-1-cyano-N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of (2R,4R)—N-[2-[(4,4-difluorocyclohexyl)amino]-1-(6-fluoro-3-pyridyl)-2-oxo-ethyl]-4-hydroxy-4-methyl-N-[4-(pentafluoro-λ6-sulfanyl)phenyl]pyrrolidine-2-carboxamide (47 mg, 76.23 umol, 1 eq) in EtOH (1 mL) was added $NaHCO_3$ (19.21 mg, 228.69 umol, 8.89 uL, 3 eq). BrCN (10.50 mg, 99.10 umol, 7.29 uL, 1.3 eq) was added at 0° C., and the mixture was stirred at 0° C. for 1 h, and then stirred at 20° C. for 1 h. Upon completion, the reaction mixture was concentrated under reduced pressure to remove solvent. The residue was purified by neutral prep-HPLC to afford (2R,4R)-1-cyano-N-[2-[(4,4-difluorocyclohexyl)amino]-1-(6-fluoro-3-pyridyl)-2-oxo-ethyl]-4-hydroxy-4-methyl-N-[4-(pentafluoro-$λ^6$-sulfanyl)phenyl]pyrrolidine-2-carboxamide (10.50 mg, 15.29 umol, 20.06% yield, 93.416% purity) as white solid. MS (ESI) m/z 642.3[M+H]$^+$.

Prep-HPLC condition: column: Waters Xbridge Prep OBD C18 150*40 mm*10 um; mobile phase: [water (10 mM $NH_4HCO_3$)-ACN]; B %: 35%-65%, 8 min.

$^1$H NMR (400 MHz, METHANOL-$d_4$) δ ppm 7.51-8.40 (m, 5H) 6.93-7.50 (m, 1H) 6.88 (dd, J=8.60, 2.43 Hz, 1H) 6.10 (s, 1H) 4.26 (br dd, J=9.15, 3.86 Hz, 1H) 3.87 (br t, J=9.70 Hz, 1H) 3.49 (d, J=9.26 Hz, 1H) 3.35 (d, J=9.48 Hz, 1H) 1.75-2.13 (m, 8H) 1.56-1.71 (m, 1H) 1.37-1.52 (m, 1H) 1.26 (s, 3H).

Example 138: Synthesis of Compound 1158

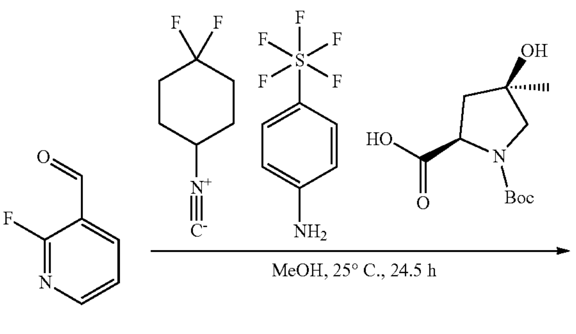

-continued

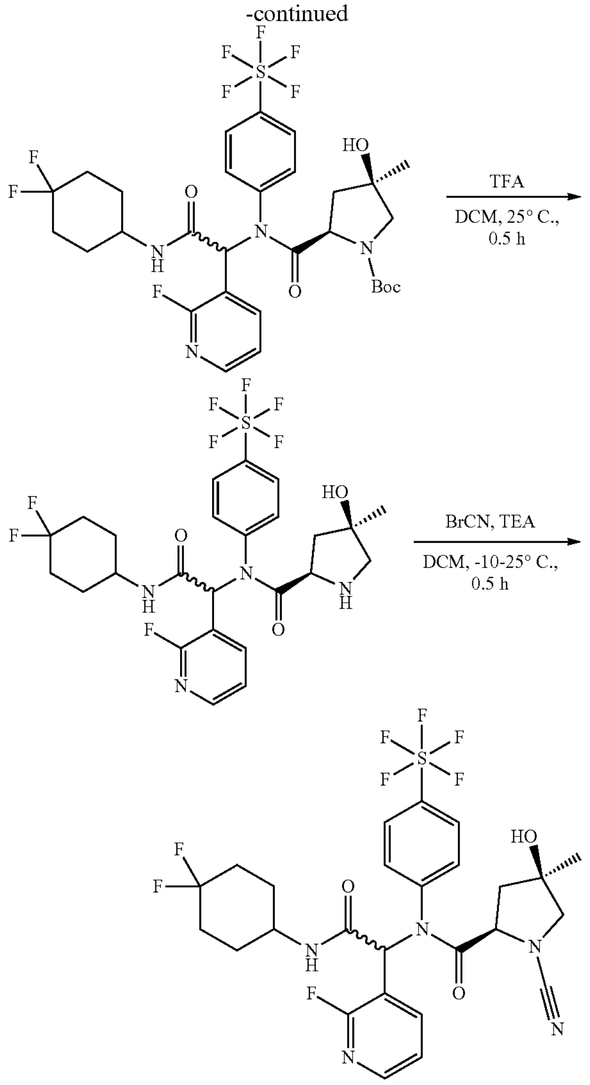

Step 1: tert-butyl(2R,4R)-2-[[2-[(4,4-difluorocyclohexyl)amino]-1-(2-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate 4-(pentafluoro-λ6-sulfanyl)aniline (525.60 mg, 2.40 mmol, 1 eq) and 2-fluoropyridine-3-carbaldehyde (300 mg, 2.40 mmol, 1 eq) in MeOH (8 mL) was stirred at 25° C. for 0.5 h. (2R,4R)-1-tert-butoxycarbonyl-4-hydroxy-4-methylpyrrolidine-2-carboxylic acid (588.65 mg, 2.40 mmol, 1 eq) and 1,1-difluoro-4-isocyano-cyclohexane (348.08 mg, 2.40 mmol, 1 eq) were added, and the mixture was stirred at 25° C. for 24 h. Upon completion, the mixture was concentrated under the reduced pressure to give a residue. The residue was purified by prep-HPLC (column: Kromasil C18 (250*50 mm*10 um); mobile phase: [water (10 mM $NH_4HCO_3$)-ACN]; B %: 55%-75%, 10 min) affording the product tert-butyl (2R,4R)-2-[[2-[(4,4-difluorocyclohexyl)amino]-1-(2-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (210 mg, crude) as a yellow oil. MS (ESI) m/z 717.2 $[M+H]^+$ Step 2: (2R,4R)—N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of tert-butyl (2R,4R)-2-[[2-[(4,4-difluorocyclohexyl)amino]-1-(2-fluoro-3-pyridyl)-2-oxo-ethyl]-[4-(pentafluoro-λ6-sulfanyl)phenyl]carbamoyl]-4-hydroxy-4-methyl-pyrrolidine-1-carboxylate (200 mg, 279.06 umol, 1 eq) in DCM (3 mL) was added TFA (1.54 g, 13.51 mmol, 1 mL, 48.40 eq), and the mixture was stirred at 25° C. for 0.5 h. Upon completion, the reaction mixture was quenched by addition sat. $NaHCO_3$ (10 mL), and then extracted with DCM (10 mL*3). The combined organic layers were washed with brine (10 mL), dried over $Na_2SO_4$, filtered and concentrated under reduced pressure affording the product (2R,4R)—N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (150 mg, crude) as a yellow solid. MS (ESI) m/z 617.2 $[M+H]^+$ Step 3: (2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide To a solution of (2R,4R)—N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (140 mg, 227.06 umol, 1 eq) in DCM (3 mL) was added TEA (68.93 mg, 681.19 umol, 94.81 uL, 3 eq), and then the solution was cooled to −10° C. BrCN (28.86 mg, 272.48 umol, 20.04 uL, 1.2 eq) in DCM (0.5 mL) was added at 0° C., and the solution was stirred and warmed to 25° C. gradually for 0.5 h. Upon completion, the mixture was quenched by the addition of $H_2O$ (10 mL) and then extracted with DCM (10 mL*3). The combined organic layers were washed with brine (10 mL), dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 35%-65%, 8 min) affording the product (2R,4R)-1-cyano-N-[2-[(4,4-difluorocyclohexyl)amino]-1-(2-fluoro-3-pyridyl)-2-oxo-ethyl]-4-hydroxy-4-methyl-N-[4-(pentafluoro-λ6-sulfanyl)phenyl]pyrrolidine-2-carboxamide (45 mg, 70.14 umol, 30.89% yield, 100% purity) as a white solid. MS (ESI) m/z 642.3 $[M+H]^+$ $^1H$ NMR (400 MHz, METHANOL-$d_4$) δ=8.16-7.99 (m, 1H), 7.99-7.47 (m, 4H), 7.34-6.88 (m, 2H), 6.42-6.20 (m, 1H), 4.35-4.21 (m, 1H), 3.97-3.84 (m, 1H), 3.49 (d, J=9.4 Hz, 1H), 3.34 (d, J=9.4 Hz, 1H), 2.10-1.82 (m, 8H), 1.69-1.40 (m, 2H), 1.26 (d, J=10.0 Hz, 3H).

Example 139: Synthesis of Compound 1307

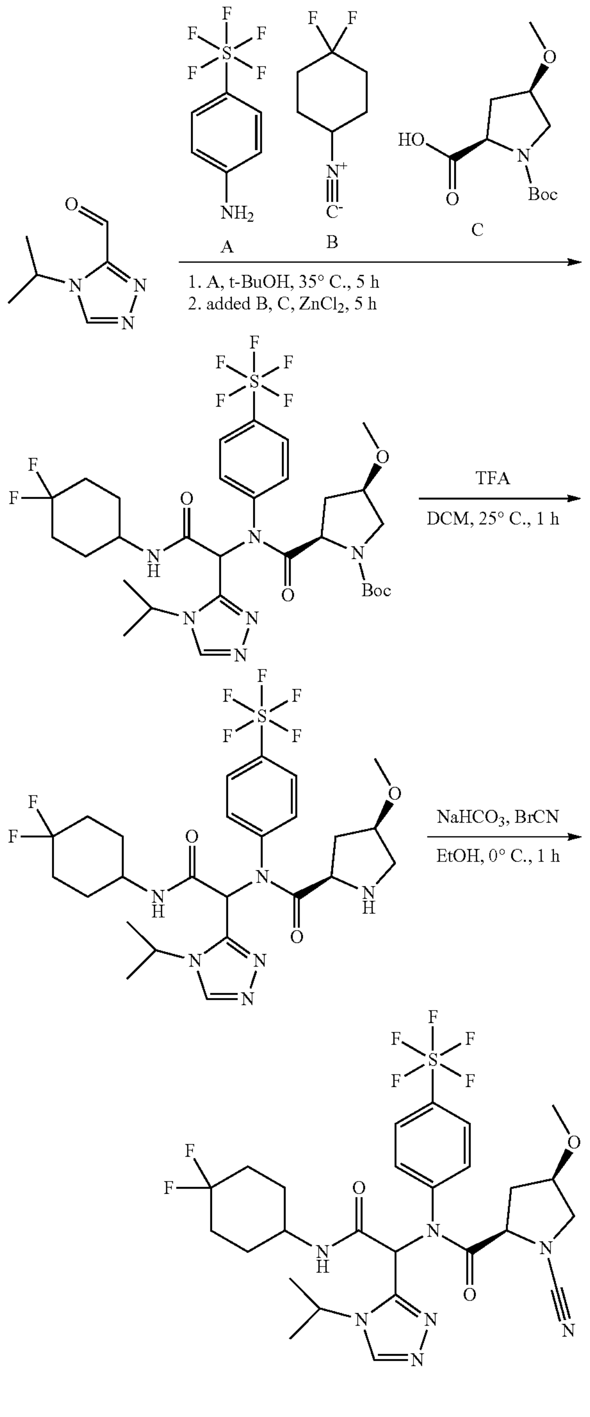

Step 1: tert-(2R,4R)-2-[[2-[(4,4-difluorocyclohexyl) amino]-1-(4-isopropyl-1,2,4-triazol-3-yl)-2-oxo-ethyl]-[4-(pentafluoro-$\lambda^6$-sulfanyl)phenyl]carbamoyl]-4-methoxy-pyrrolidine-1-carboxylate A solution of 4-(pentafluoro-$\lambda^6$-sulfanyl) aniline (268.08 mg, 1.22 mmol, 1 eq) and 4-isopropyl-1,2,4-triazole-3-carbaldehyde (204.25 mg, 1.47 mmol, 1.2 eq) in t-BuOH (5 mL) was stirred at 35° C. for 5 h. (2R,4R)-1-tert-butoxycarbonyl-4-methoxy-pyrrolidine-2-carboxylic acid (300 mg, 1.22 mmol, 1 eq) was added to the mixture, and then 1-difluoro-4-isocyano-cyclohexane (177.54 mg, 1.22 mmol, 1 eq) was added in portions. $ZnCl_2$ (1 M, 3.67 mL, 3 eq) was added to the mixture, and the mixture was stirred at 35° C. for 5 h. Upon the reaction completion, the mixture was concentrated in vacuum and was purified by prep-HPLC (column: Kromasil C18 (250*50 mm*10 um); mobile phase: [water (10 mM $NH_4HCO_3$)-ACN]; B %: 50%-80%, 10 min) to obtained tert-(2R,4R)-2-[[2-[(4,4-difluorocyclohexyl)amino]-1-(4-isopropyl-1,2,4-triazol-3-yl)-2-oxo-ethyl]-[4-(pentafluoro-$\lambda^6$-sulfanyl)phenyl]carbamoyl]-4-methoxy-pyrrolidine-1-carboxylate (100 mg, 136.85 umol, 11.19% yield) as a yellow solid. MS (ESI) m/z 731.3 $[M+H]^+$ Step 2: (2R,4R)—N-[2-[(4,4-difluorocyclohexyl) amino]-1-(4-isopropyl-1,2,4-triazol-3-yl)-2-oxo-ethyl]-4-methoxy-N-[4-(pentafluoro-λ6-sulfanyl) phenyl]pyrrolidine-2-carboxamide A solution of tert-butyl (2R,4R)-2-[[2-[(4,4-difluorocyclohexyl)amino]-1-(4-isopropyl-1,2,4-triazol-3-yl)-2-oxo-ethyl]-[4-(pentafluoro-$\lambda^6$-sulfanyl)phenyl]carbamoyl]-4-methoxy-pyrrolidine-1-carboxylate (100 mg, 136.85 umol, 1 eq) in TFA (0.5 mL) and DCM (1 mL) was stirred at 25° C. for 1 h. Upon completion, the mixture was concentrated in vacuum and the pH was adjusted to ~7 with sat. $NaHCO_3$ (6 mL), and then was extracted with DCM (2 mL*3). The resulting solution was concentrated in vacuum to obtain (2R,4R)—N-[2-[(4,4-difluorocyclohexyl)amino]-1-(4-isopropyl-1,2,4-triazol-3-yl)-2-oxo-ethyl]-4-methoxy-N-[4-(pentafluoro-$\lambda^6$-sulfanyl)phenyl]pyrrolidine-2-carboxamide (100 mg, crude) as a yellow solid. MS (ESI) m/z 631.3 $[M+H]^+$ Step 3: (2R,4R)-1-cyano-N-[2-[(4,4-difluorocyclohexyl)amino]-1-(4-isopropyl-1,2,4-triazol-3-yl)-2-oxo-ethyl]-4-methoxy-N-[4-(pentafluoro-λ6-sulfanyl)phenyl]pyrrolidine-2-carboxamide To a solution of (2R,4R)—N-[2-[(4,4-difluorocyclohexyl) amino]-1-(4-isopropyl-1,2,4-triazol-3-yl)-2-oxo-ethyl]-4-methoxy-N-[4-(pentafluoro-$\lambda^6$-sulfanyl)phenyl]pyrrolidine-2-carboxamide (100 mg, 158.57 umol, 1 eq) in EtOH (3 mL) was added $NaHCO_3$ (39.96 mg, 475.72 umol, 18.50 uL, 3 eq), and the mixture was cooled to 0° C. BrCN (33.59 mg, 317.15 umol, 23.33 uL, 2 eq) was added to the mixture and stirred at 0° C. for 1 h. Upon the reaction completion, the mixture was dried by blowing $N_2$, quenched with water (20 mL), extracted with DCM (10 mL*3), and then concentrated in vacuum and was purified by prep-HPLC (column: Waters Xbridge BEH C18 100*25 mm*5 um; mobile phase: [water (10 mM $NH_4HCO_3$)-ACN]; B %: 35%-55%, 10 min) and then was lyophilization and purified by prep-HPLC (column: Phenomenex Luna C18 75*30 mm*3 um; mobile phase: [water (0.2% FA)-ACN]; B %: 15%-50%, 8 min) to obtain (2R,4R)-1-cyano-N-[2-[(4,4-difluorocyclohexyl) amino]-1-(4-isopropyl-1,2,4-triazol-3-yl)-2-oxo-ethyl]-4-methoxy-N-[4-(pentafluoro-6-sulfanyl)phenyl]pyrrolidine-2-carboxamide (20 mg, 29.28 umol, 18.47% yield, 96% purity) as a white solid. MS (ESI) m/z 656.2 $[M+H]^+$ $^1H$ NMR (400 MHz, MeOD-$d_4$) δ ppm 8.64 (s, 1H), 7.70 (d, J=9.2 Hz, 2H), 7.23 (d, J=8.7 Hz, 2H), 4.52-4.29 (m, 2H), 4.18-3.99 (m, 2H), 3.80 (d, J=11.9 Hz, 1H), 3.55 (dd, J=4.6, 11.9 Hz, 1H), 3.39 (s, 3H), 2.71-2.54 (m, 2H), 2.17-1.65 (m, 8H), 1.43 (d, J=6.4 Hz, 3H), 1.27 (d, J=6.4 Hz, 3H).

Example 140: Synthesis of Compound 1131

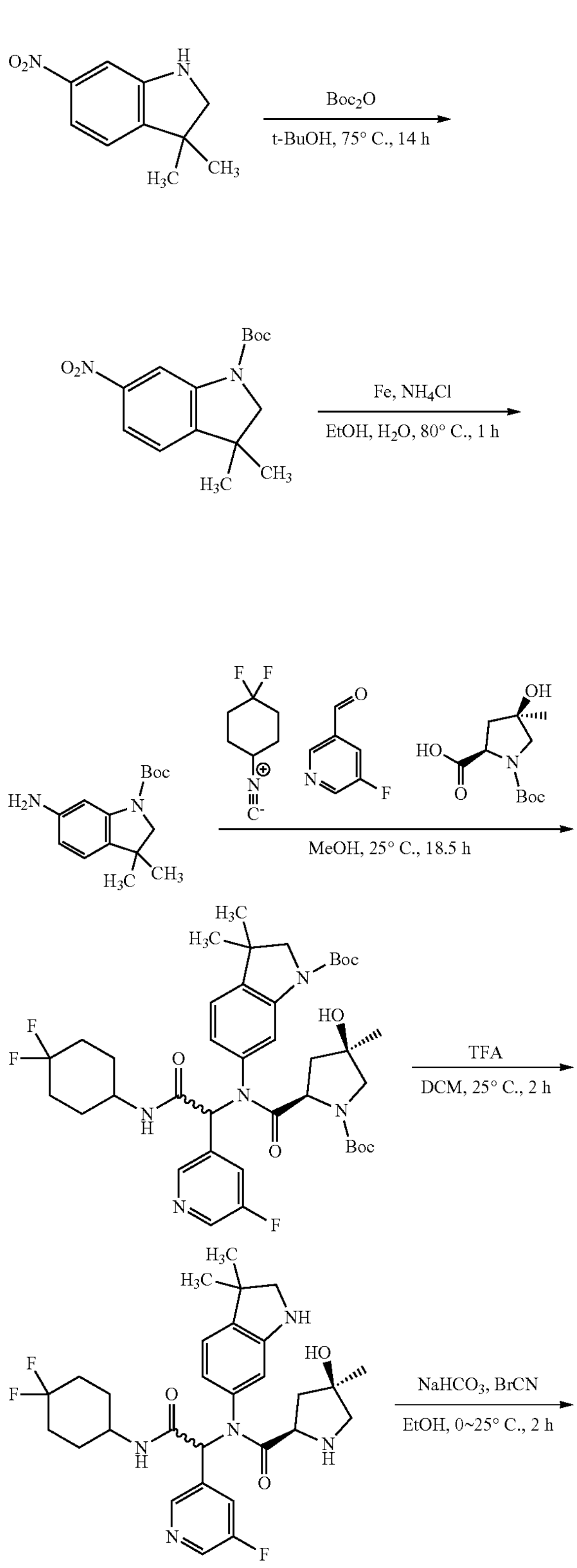

-continued

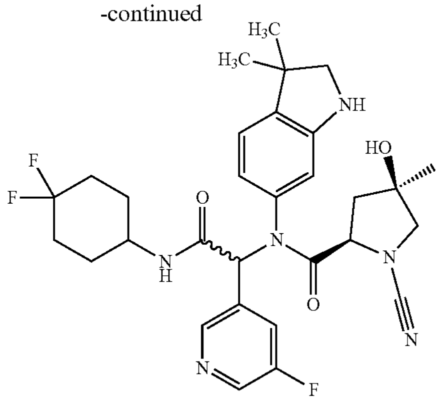

Step 1: tert-butyl 3,3-dimethyl-6-nitro-indoline-1-carboxylate

To a mixture of 3,3-dimethyl-6-nitro-indoline (500 mg, 2.60 mmol, 1 eq) in t-BuOH (3 mL) was added $Boc_2O$ (567.72 mg, 2.60 mmol, 597.60 uL, 1 eq) at 75° C. and stirred for 14 h at 75° C. Upon completion, the reaction mixture was concentrated under reduced pressure to give the crude product. The crude was purified by column chromatography ($SiO_2$, Petroleum ether/Ethyl acetate=30/1 to 20/1) to give tert-butyl 3,3-dimethyl-6-nitro-indoline-1-carboxylate (890 mg, 2.44 mmol, 93.63% yield, 80% purity) as a yellow oil. MS (ESI) m/z 237.1 $[M+H-56]^+$ Step 2: tert-butyl 6-amino-3,3-dimethyl-indoline-1-carboxylate To a solution of tert-butyl 3,3-dimethyl-6-nitro-indoline-1-carboxylate (890 mg, 2.44 mmol, 80% purity, 1 eq) in EtOH (8 mL) and $H_2O$ (2 mL) was added $NH_4Cl$ (390.85 mg, 7.31 mmol, 3 eq) in one portion at 25° C. The mixture was then heated to 80° C., and then Fe (680.08 mg, 12.18 mmol, 5 eq) was added and stirred for 1 h at 80° C. Upon completion, the reaction mixture was filtered and diluted with $H_2O$ 10 mL and extracted with EA 30 mL (10 mL*3). The combined organic layers were washed with brine 10 mL, dried over $Na_2SO_4$ and filtered and concentrated under reduced pressure to give the crude product. The crude was purified by column chromatography ($SiO_2$, Petroleum ether/Ethyl acetate=30/1 to 10/1) to give tert-butyl 6-amino-3,3-dimethyl-indoline-1-carboxylate (630 mg, 2.40 mmol, 98.60% yield) as a yellow oil. MS (ESI) m/z 263.1 $[M+H]^+$ Step 3: Tert-butyl 6-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-3,3-dimethyl-indoline-1-carboxylate To a mixture of tert-butyl 6-amino-3,3-dimethyl-indoline-1-carboxylate (630 mg, 2.40 mmol, 1 eq) in MeOH (7 mL) was added 5-fluoropyridine-3-carbaldehyde (300.42 mg, 2.40 mmol, 1 eq) in one portion, and stirred at 25° C. for 2 h. Then 1,1-difluoro-4-isocyano-cyclohexane (348.56 mg, 2.40 mmol, 1 eq) and (2R,4R)-1-tert-butoxycarbonyl-4-hydroxy-4-methyl-pyrrolidine-2-carboxylic acid (589.00 mg, 2.40 mmol, 1 eq) were added to the mixture and the mixture was stirred at 25° C. for 30 min, followed by the addition of $ZnCl_2$ (1 M, 7.20 mL, 3 eq). The reaction was stirred at 25° C. for 16 h, and then concentrated under reduced pressure to give the crude product. The crude was purified by prep-HPLC (Column: Kromasil C18 (250*50 mm*10 um); mobile phase: [water (0.05% $NH_3H_2O$+10 mM $NH_4HCO_3$)-ACN]; B %: 60%-85%, 10 min) to give tert-butyl 6-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-3,3-dimethyl-indoline-1-carboxylate (Isomer 1: 240 mg, 315.85 umol, 13.15% yield) as a yellow solid, and tert-butyl 6-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-3,3-dimethyl-indoline-1-carboxylate (Isomer 2: 200 mg, 263.21 umol, 10.96% yield) as a yellow solid. MS (ESI) m/z 760.4 $[M+H]^+$ Step 4: (2R,4R)—N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide Isomer 1:

A solution of tert-butyl 6-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-3,3-dimethyl-indoline-1-carboxylate (200 mg, 263.21 umol, 1 eq) in DCM (4 mL) was added TFA (1 mL) in one portion at 25° C. The mixture was stirred at 25° C. for 2 h. Upon completion, the reaction mixture was adjusted to neutral, and then diluted with $H_2O$ 10 mL and extracted with EA 30 mL (10 mL*3). The combined organic layers were washed with brine (10 mL), dried over $Na_2SO_4$, filtered and concentrated under reduced pressure to give (2R,4R)—N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide (120 mg, 214.43 umol, 81.47% yield) as a brown solid.

Isomer 2:

To a solution of tert-butyl 6-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-3,3-dimethyl-indoline-1-carboxylate (200 mg, 263.21 umol, 1 eq) in DCM (3 mL) was added TFA (1 mL) in one portion at 25° C. The mixture was stirred at 25° C. for 2 h. Upon completion, the reaction mixture was adjusted to neutral, and then diluted with $H_2O$ 10 mL and extracted with EA 30 mL (10 mL*3). The combined organic layers were washed with brine (10 mL), dried over $Na_2SO_4$, filtered and concentrated under reduced pressure to give (2R,4R)—N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide (120 mg, 214.43 umol, 81.47% yield) as a brown solid.

Step 5: (2R,4R)-1-cyano-N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide Isomer 1: To a mixture of (2R,4R)—N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide (200 mg, 357.38 umol, 1 eq) in EtOH (2 mL) was added $NaHCO_3$ (90.07 mg, 1.07 mmol, 41.70 uL, 3 eq) in one portion at 25° C. BrCN (18.93 mg, 178.69 umol, 13.14 uL, 0.5 eq) was added at 0° C. and stirred at 25° C. for 2 h. Upon completion, the reaction mixture was quenched with $H_2O$ 5 mL at 0° C., and the combined organic layers were concentrated under reduced pressure to give a residue. The residue was purified by prep-HPLC (column: Phenomenex Gemini-NX C18 75*30 mm*3 um; mobile phase: [water (0.05% $NH_3H_2O$+10 mM $NH_4HCO_3$)-ACN]; B %: 30%-60%, 8 min) to afford (2R,4R)-1-cyano-N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide (20 mg, 33.18 umol, 9.29% yield, 97% purity) as a white solid. MS (ESI) m/z 585.2 $[M+H]^+$ $^1H$ NMR (400 MHz, DMSO-$d_6$) δ=8.41-8.31 (m, 1H), 8.29-8.19 (m, 1H), 8.04-7.85 (m, 1H), 7.37-7.23 (m, 1H), 6.81 (br s, 1H), 6.62-5.68 (m, 3H), 5.53 (br s, 1H), 5.16 (br s, 1H), 4.20 (br t, J=7.2 Hz, 1H), 3.79 (br s, 1H), 3.36 (br d, J=9.0 Hz, 1H), 3.25 (d, J=8.8 Hz, 1H), 3.21-3.15 (m, 2H), 2.02-1.76 (m, 8H), 1.61-1.33 (m, 2H), 1.19-1.09 (m, 9H)

Isomer 2: To a mixture of (2R,4R)—N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide (120-mg, 214.43 umol, 1 eq) in EtOH (2 mL) was added $NaHCO_3$ (54.04 mg, 643.29 umol, 25.02 uL, 3 eq) in one portion at 25° C. The mixture was added with BrCN (22.71 mg, 214.43 umol, 15.77 uL, 1 eq) at 0° C. and stirred at 25° C. for 2 h. Upon completion, the reaction mixture was quenched by addition of 5 mL $H_2O$ 5 at 0° C., and concentrated under reduced pressure to give a crude. The crude was purified by prep-HPLC (column: Phenomenex Gemini-NX C18 75*30 mm*3 um; mobile phase: [water (0.05% $NH_3H_2O$+10 mM $NH_4HCO_3$)-ACN]; B %: 30%-60%, 8 min) to give (2R,4R)-1-cyano-N-[2-[(4,4-difluorocyclohexyl)amino]-1-(5-fluoro-3-pyridyl)-2-oxo-ethyl]-N-(3,3-dimethylindolin-6-yl)-4-hydroxy-4-methyl-pyrrolidine-2-carboxamide (18 mg, 30.79 umol, 14.36% yield) as a white solid. MS (ESI) m/z 585.2 $[M+H]^+$ $^1H$ NMR (400 MHz, DMSO-$d_6$) δ=8.42-8.32 (m, 1H), 8.29-8.20 (m, 1H), 8.03-7.82 (m, 1H), 7.39-7.23 (m, 1H), 6.95-5.65 (m, 4H), 5.53 (br s, 1H), 5.20-5.04 (m, 1H), 4.20 (br t, J=6.6 Hz, 1H), 3.79 (br s, 1H), 3.40-3.30 (m, 1H), 3.25 (d, J=8.8 Hz, 1H), 3.18 (br s, 2H), 1.99-1.73 (m, 8H), 1.60-1.36 (m, 2H), 1.19-1.13 (m, 9H)

Example 141: Synthesis of Compound 1095b

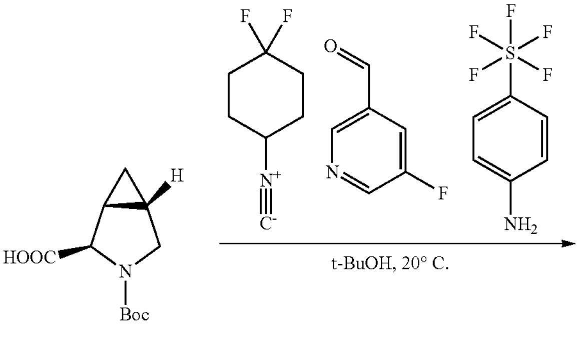

-continued

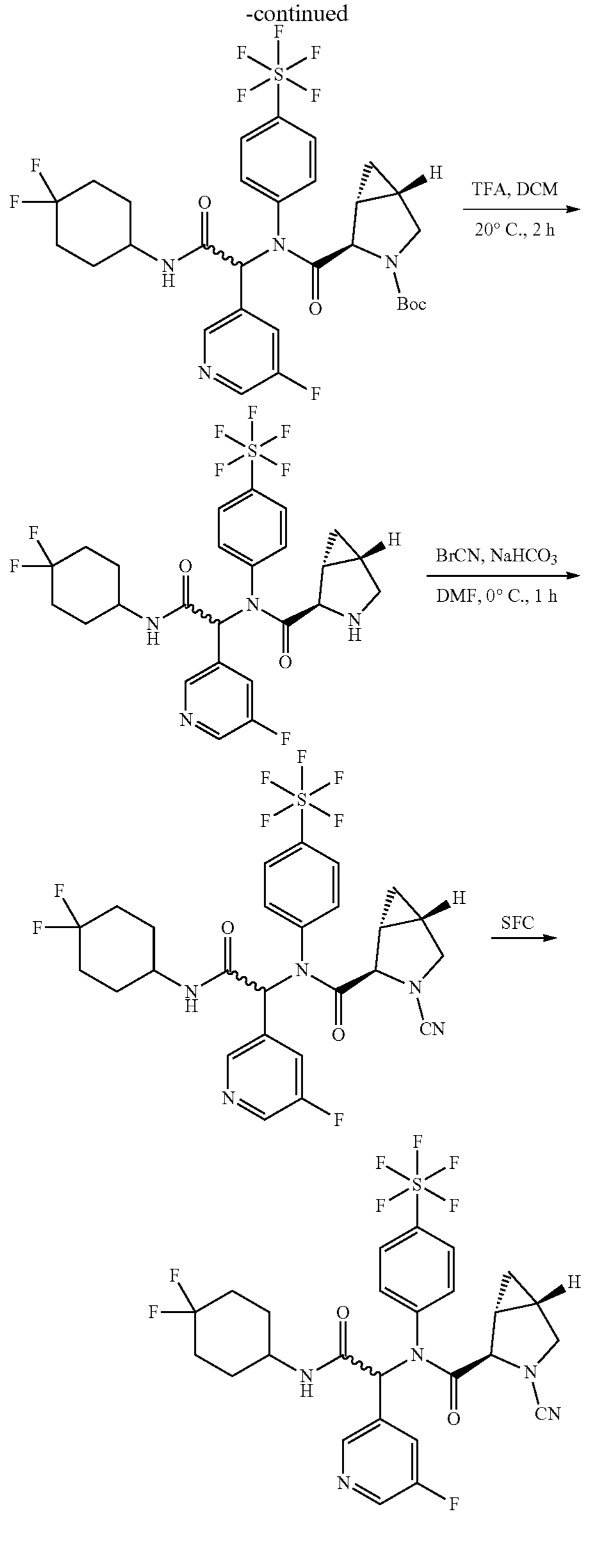

Step 1: tert-butyl (1R,2R,5S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.1.0]hexane-3-carboxylate A solution of 5-fluoropyridine-3-carbaldehyde (44.04 mg, 352.03 umol, 1 eq), 4-(pentafluoro-λ$^6$-sulfanyl)aniline (77.16 mg, 352.03 umol, 1 eq) in t-BuOH (4 mL) was stirred for 1 h, and (1R,2R,5S)-3-tert-butoxycarbonyl-3-azabicyclo[3.1.0]hexane-2-carboxylic acid (80 mg, 352.03 umol, 1 eq) was added. 1,1-difluoro-4-isocyano-cyclohexane (51.10 mg, 352.03 umol, 1 eq) in t-BuOH (1 mL) was added to the mixture and stirred 10 min. After the addition of $ZnCl_2$ (1 M, 1.06 mL, 3 eq), the mixture was stirred at 20° C. for 14 h 50 min. Upon completion, the reaction mixture was concentrated under reduced pressure and purified by prep-HPLC (column: Kromasil C18 (250*50 mm*10 um); mobile phase: [water (10 mM $NH_4HCO_3$)-ACN]; B %: 50%-80%, 10 min) to give tert-butyl (1R,2R,5S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.1.0]hexane-3-carboxylate (180 mg, 257.63 umol, 73.19% yield) as a yellow solid. MS (ESI) m/z 699.2 $[M+H]^+$ Step 2: (1R,2R,5S)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide To a solution of tert-butyl (1R,2R,5S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3-azabicyclo[3.1.0]hexane-3-carboxylate (180 mg, 257.63 umol, 1 eq) in DCM (4 mL) was added TFA (2.77 g, 24.31 mmol, 1.80 mL, 94.36 eq). The mixture was stirred at 20° C. for 2 h. Upon completion, the reaction mixture was concentrated under reduced pressure to remove solvent to give (1R,2R,5S)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (150 mg, crude) as a yellow solid. MS (ESI) m/z 599.1 $[M+H]^+$ Step 3: (1R,2R,5S)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide To a solution of (1R,2R,5S)—N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (140 mg, 233.90 umol, 1 eq), $NaHCO_3$ (58.95 mg, 701.69 umol, 27.29 uL, 3 eq) in DMF (3 mL) was added BrCN (29.73 mg, 280.68 umol, 20.65 uL, 1.2 eq) in DMF (0.3 mL) at 0° C. The mixture was stirred at 0° C. for 1 h. Upon completion, the reaction mixture was poured into $H_2O$ (20 mL) at 20° C., and then extracted with EtOAc (25 mL*3). The combined organic layers were washed with brine (20 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-70%, 8 min) to give (1R,2R,5S)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (85 mg, 135.36 umol, 57.87% yield, 99.3% purity) as a white solid. MS (ESI) m/z 624.3 $[M+H]^+$ $^1$H NMR (400 MHz, MeOD-$d_4$) δ=8.33 (d, J=2.6, 15.7 Hz, 1H), 8.23 (d, J=13.2 Hz, 1H), 7.99-7.26 (m, 5H), 6.28-6.07 (m, 1H), 4.07-3.97 (m, 1H), 3.95-3.80 (m, 2H), 3.43 (t, J=9.1 Hz, 1H), 2.17-1.56 (m, 9H), 1.46 (d, J=10.5 Hz, 1H), 0.77-0.67 (m, 1H), 0.31-0.19 (m, 1H).

Step 4: (1R,2R,5S)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (1R,2R,5S)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (75 mg) was separated by SFC (column: DAICEL CHIRALPAK AD (250 mm*30 mm, 10 um); mobile phase: [0.1% $NH_3H_2O$ ETOH]; B %: 30%-30%, 8 min) to give (1R,2R,5S)-3-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-3-azabicyclo[3.1.0]hexane-2-carboxamide (30.5 mg, 48.91 umol, 40.67% yield, 100% purity) as a white solid. MS (ESI) m/z 624.3 $[M+H]^+$ Isomer 1: $^1H$ NMR (400 MHz, MeOD-$d_4$) δ=8.31 (d, J=2.7 Hz, 1H), 8.22 (s, 1H), 8.06-7.17 (m, 5H), 6.24 (s, 1H), 4.04 (s, 1H), 3.96-3.83 (m, 2H), 3.44 (d, J=8.7 Hz, 1H), 2.10-1.63 (m, 9H), 1.52-1.39 (m, 1H), 0.79-0.68 (m, 1H), 0.25 (d, J=4.5 Hz, 1H).

(1R,2R,5S)-3-cyano-N-[2-[(4,4-difluorocyclohexyl)amino]-1-(5-fluoro-3-pyridyl)-2-oxo-ethyl]-N-[4-(pentafluoro-26-sulfanyl)phenyl]-3-azabicyclo[3.1.0]hexane-2-carboxamide (38.5 mg, 58.04 umol, 48.25% yield, 94% purity) as a white solid. MS (ESI) m/z 624.3 $[M+H]^+$ Isomer 2: $^1H$ NMR (400 MHz, MeOD-$d_4$) δ=8.35 (d, J=2.6 Hz, 1H), 8.25 (s, 1H), 7.97-7.23 (m, 5H), 6.10 (s, 1H), 4.01 (s, 1H), 3.83 (d, J=3.8, 8.8 Hz, 2H), 3.42 (d, J=8.9 Hz, 1H), 2.09-1.61 (m, 9H), 1.47 (s, 1H), 0.72 (d, J=5.8 Hz, 1H), 0.24 (br d, J=5.0 Hz, 1H).

Example 142: Synthesis of Compound 1135b

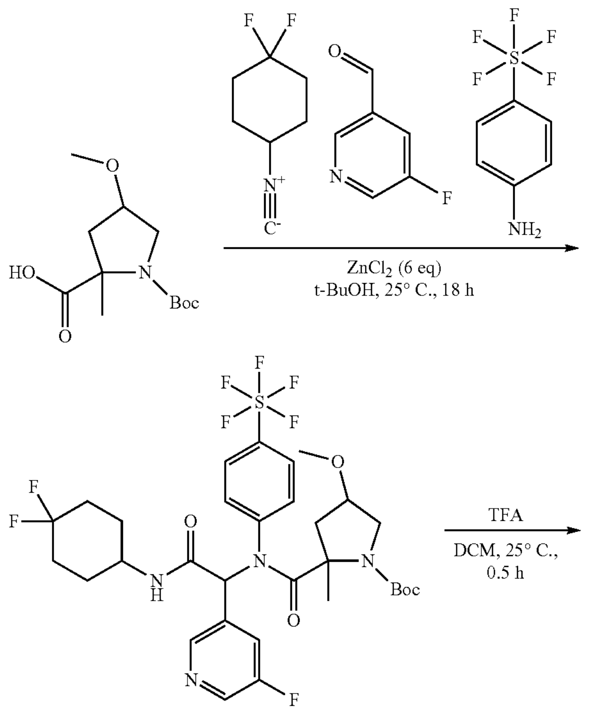

-continued

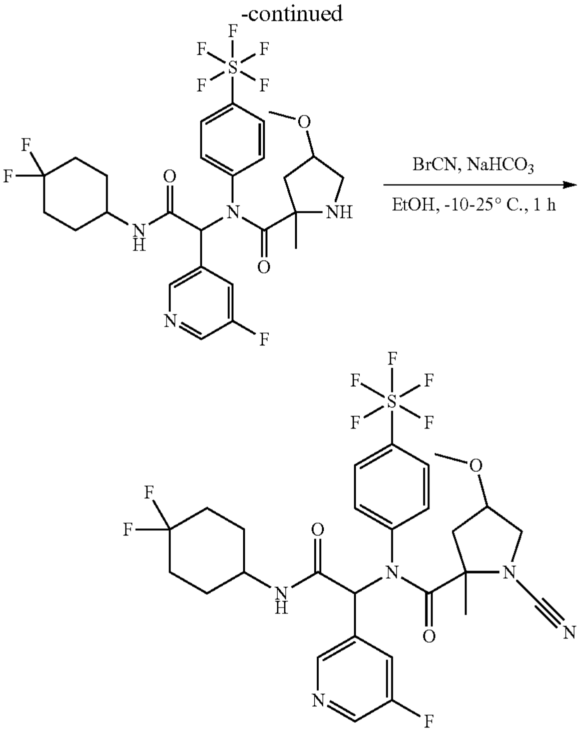

Step 1: tert-butyl 2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-methoxy-2-methyl-pyrrolidine-1-carboxylate A solution of 5-fluoropyridine-3-carbaldehyde (48.25 mg, 385.66 umol, 96.68 uL, 1 eq), 4-(pentafluoro-λ$^6$-sulfanyl)aniline (84.53 mg, 385.66 umol, 1 eq) in t-BuOH (1.0 mL) was stirred at 25° C. for 2 h. 1-Tert-butoxycarbonyl-4-methoxy-2-methyl-pyrrolidine-2-carboxylic acid (100 mg, 385.66 umol, 1 eq) was added, and a solution of 1,1-difluoro-4-isocyano-cyclohexane (50.38 mg, 347.09 umol, 0.9 eq) in t-BuOH (0.5 mL) in batches (three times). After the addition of $ZnCl_2$ (1 M, 2.31 mL, 6 eq), the reaction mixture was stirred at 25° C. for 16 h. Upon completion, the reaction mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 55%-75%, 10 min) to give the title compound tert-butyl 2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-methoxy-2-methyl-pyrrolidine-1-carboxylate (85 mg, 89.57 umol, 11.61% yield, 77% purity) as a yellow oil. MS (ESI) m/z 731.3 $[M+1]^+$ Step 2: N-[2-[(4,4-difluorocyclohexyl)amino]-1-(5-fluoro-3-pyridyl)-2-oxo-ethyl]-4-methoxy-2-methyl-N-[4-(pentafluoro-λ$^6$-sulfanyl)phenyl]pyrrolidine-2-carboxamide A mixture of tert-butyl 2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-methoxy-2-methyl-pyrrolidine-1-carboxylate (85 mg, 89.57 umol, 77% purity, 1 eq) in DCM (2 mL) and TFA (1 mL) was stirred at 25° C. for 0.5 h under $N_2$ atmosphere. Upon completion, the reaction mixture was quenched by addition $NaHCO_3$ aq (30 mL), and extracted with DCM (15 mL*3). The combined organic layers were washed with brine (20 mL), dried over $Na_2SO_4$, filtered and concentrated under reduced pressure to give a residue. The crude product N-[2-[(4,4-difluorocyclohexyl)amino]-1-(5-fluoro-3-pyridyl)-2-oxo-ethyl]-4-methoxy-2-methyl-N-[4-(pentafluoro-$\lambda^6$-sulfanyl)phenyl]pyrrolidine-2-carboxamide (50 mg, crude) as a yellow oil. MS (ESI) m/z 631.2 $[M+H]^+$ Step 3: 1-cyano-N-[2-[(4,4-difluorocyclohexyl)amino]-1-(5-fluoro-3-pyridyl)-2-oxo-ethyl]-4-methoxy-2-methyl-N-[4-(pentafluoro-$\lambda^6$-sulfanyl)phenyl]pyrrolidine-2-carboxamide To a solution of N-[2-[(4,4-difluorocyclohexyl)amino]-1-(5-fluoro-3-pyridyl)-2-oxo-ethyl]-4-methoxy-2-methyl-N-[4-(pentafluoro-$\lambda^6$-sulfanyl)phenyl]pyrrolidine-2-carboxamide (40 mg, 29.81 umol, 47% purity, 1 eq) and $NaHCO_3$ (7.51 mg, 89.44 umol, 3.48 uL, 3 eq) in EtOH (1 mL) was added drop-wise a solution of BrCN (4.74 mg, 44.72 umol, 3.29 uL, 1.5 eq) in EtOH (0.5 mL) at −10° C. under $N_2$. The reaction mixture was slowly warmed to 25° C. for 1 h. Upon completion, the reaction mixture was quenched by addition $H_2O$ (15 mL) and extracted with EtOAc (5 mL*3). The combined organic layers were washed with brine (10 mL), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-70%, 8 min) to give a 1-cyano-N-[2-[(4,4-difluorocyclohexyl)amino]-1-(5-fluoro-3-pyridyl)-2-oxo-ethyl]-4-methoxy-2-methyl-N-[4-(pentafluoro-$\lambda^6$-sulfanyl)phenyl]pyrrolidine-2-carboxamide (11.7 mg, 17.61 umol, 59.08% yield, 98.7% purity) as a white solid. MS (ESI) m/z 656.2 $[M+H]^+$ $^1H$ NMR (400 MHz, MeOD-$d_4$) δ=8.33-8.29 (m, 1H), 8.20-8.03 (m, 1H), 8.04-7.59 (m, 3H), 7.39-7.30 (m, 1H), 7.09 (s, 1H), 6.06-5.93 (m, 1H), 3.97-3.86 (m, 2H), 3.44-3.41 (m, 1H), 3.22 (s, 3H), 3.03-2.88 (m, 1H), 2.67-2.51 (m, 1H), 2.03-1.84 (m, 7H), 1.82-1.64 (m, 4H), 1.46-1.41 (m, 1H).

Example 143: Synthesis of Compound 1160

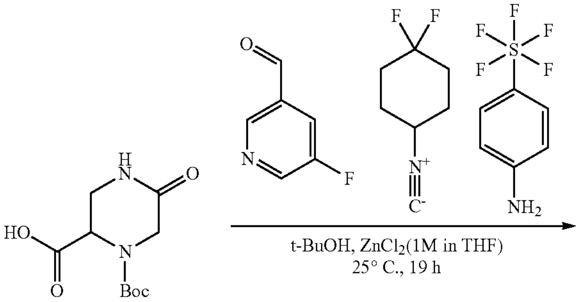

-continued

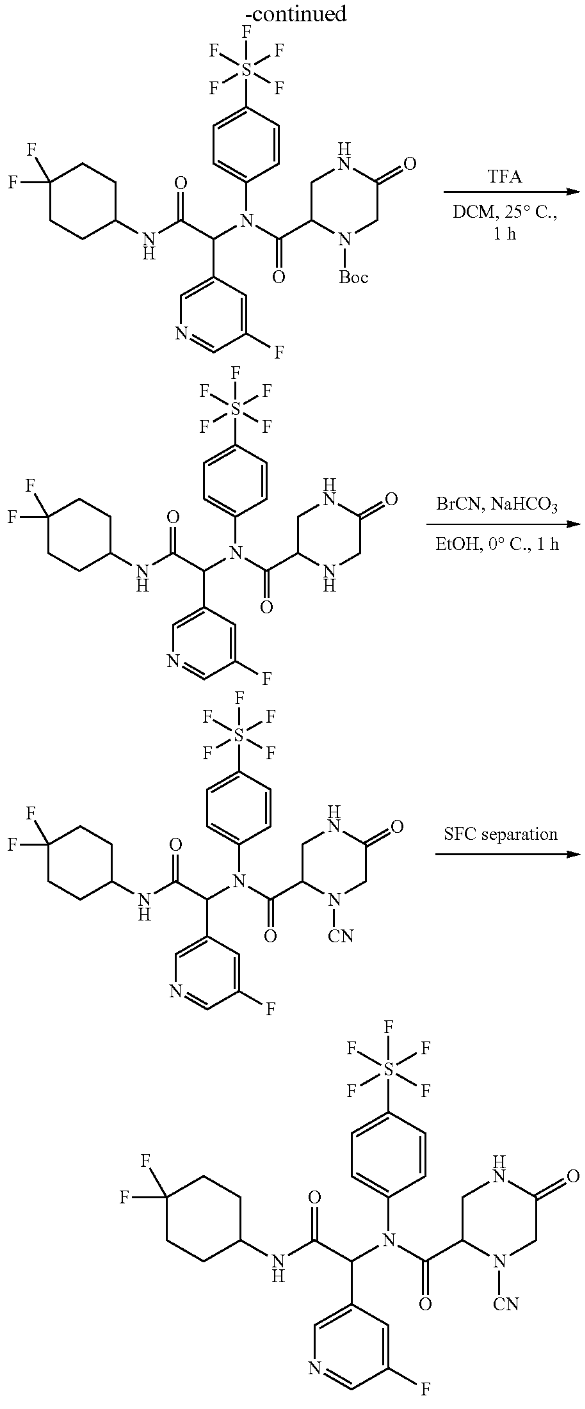

Step 1: tert-butyl2-[[2-[(4,4-difluorocyclohexyl)amino]-1-(S-fluoro-3-pyridyl)-2-oxo-ethyl]-[4-(pentafluoro-$\lambda^6$-sulfanyl)phenyl]carbamoyl]-5-oxo-piperazine-1-carboxylate 5-Fluoropyridine-3-carbaldehyde (307.32 mg, 2.46 mmol, 1.5 eq), 4-(pentafluoro-λ6-sulfanyl)aniline (358.95 mg, 1.64 mmol, 1 eq) in t-BuOH (1 mL) was stirred at 25° C. for 2 h, and then the 1-tert-butoxycarbonyl-5-oxo-piperazine-2-carboxylic acid (400 mg, 1.64 mmol, 1 eq) and 1,1-difluoro-4-isocyano-cyclohexane (237.71 mg, 1.64 mmol, 1 eq) were added and stirred for 10 min. $ZnCl_2$ (1 M, 9.83 mL, 6 eq) was added and the solution was stirred at 25° C. for 17 h. Upon completion, the solution was diluted with $H_2O$ (20 mL), extracted with EA (30 mL*3), the combined organic phase was dried over $Na_2SO_4$, filtrated and concentrated to give the crude. The residue was purified by prep-TLC ($SiO_2$, DCM:MeOH=10:1). Tert-butyl 2-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-5-oxo-piperazine-1-carboxylate (310 mg, 433.17 umol, 26.45% yield, 100% purity) was obtained as yellow solid. MS (ESI) m/z 716.1 $[M+H]^+$.

Step 2: N-[2-[(4,4-difluorocyclohexyl)amino]-1-(5-fluoro-3-pyridyl)-2-oxo-ethyl]-5-oxo-N-[4-(pentafluoro-λ6-sulfanyl)phenyl]piperazine-2-carboxamide Tert-butyl 2-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-5-oxo-piperazine-1-carboxylate (260 mg, 363.30 umol, 1 eq) in TFA (800.80 mg, 7.02 mmol, 520.00 uL, 19.33 eq)/DCM (2.5 mL) was stirred at 25° C. for 1 h. Upon completion, the solution was concentrated to remove the DCM and TFA, and the pH was adjusted to 7-8 by the addition of $NaHCO_3$ aq. The resulting mixture was extracted with EA (20 mL*3), the combined organic phase was dried over $Na_2SO_4$, filtrated and concentrated to give the crude. The crude was used to next step directly and without further purification. N-[2-[(4, 4-difluorocyclohexyl)amino]-1-(5-fluoro-3-pyridyl)-2-oxo-ethyl]-5-oxo-N-[4-(pentafluoro-6-sulfanyl) phenyl]piperazine-2-carboxamide (180 mg, crude) was obtained as yellow solid. MS (ESI) m/z 616.2 $[M+H]^+$.

Step 3: 1-cyano-N-[2-[(4,4-difluorocyclohexyl)amino]-1-(5-fluoro-3-pyridyl)-2-oxo-ethyl]-5-oxo-N-[4-(pentafluoro-$\lambda^6$-sulfanyl)phenyl]piperazine-2-carboxamide N-[2-[(4,4-difluorocyclohexyl)amino]-1-(5-fluoro-3-pyridyl)-2-oxo-ethyl]-5-oxo-N-[4-(pentafluoro-λ6-sulfanyl)phenyl]piperazine-2-carboxamide (180 mg, 292.43 umol, 1 eq) in DCM (1.5 mL) was added the $NaHCO_3$ (49.13 mg, 584.85 umol, 22.75 uL, 2 eq) and the solution was cooled to 0° C. After the addition of BrCN (30 mg, 283.23 umol, 20.83 uL, 9.69e-1 eq), the reaction was stirred at 0° C. for 1 h. Upon completion, the solution was quenched with $H_2O$ (10 mL), extracted with EA (20 mL*3), the combined organic phase was dried over $Na_2SO_4$, filtrated and concentrated to give the crude. The residue was purified by prep-HPLC (FA condition), column: Phenomenex Luna C18 200*40 mm*10 um; mobile phase: [water (0.2% FA)-ACN]; B %: 40%-80%, 8 min. 1-cyano-N-[2-[(4,4-difluorocyclohexyl)amino]-1-(5-fluoro-3-pyridyl)-2-oxo-ethyl]-5-oxo-N-[4-(pentafluoro-λ6-sulfanyl)phenyl]piperazine-2-carboxamide (65 mg, 100.87 umol, 34.49% yield, 99.399% purity) was obtained as white solid, $^1H$ NMR (400 MHz, METHANOL-$d_4$) δ=8.33 (dd, J=2.6, 6.9 Hz, 1H), 8.22 (s, 1H), 8.11-6.78 (m, 5H), 6.26-6.14 (m, 1H), 4.32 (td, J=4.1, 14.3 Hz, 1H), 4.20-4.09 (m, 1H), 3.97-3.78 (m, 2H), 3.58-3.46 (m, 2H), 2.12-1.77 (m, 6H), 1.70-1.38 (m, 2H). MS (ESI) m/z 641.2 $[M+H]^+$.

1-cyano-N-[2-[(4,4-difluorocyclohexyl)amino]-1-(5-fluoro-3-pyridyl)-2-oxo-ethyl]-5-oxo-N-[4-(pentafluoro-λ6-sulfanyl)phenyl]piperazine-2-carboxamide was separate by SFC, column: DAICEL CHIRALCEL OD (250 mm*30 mm, 10 um); mobile phase: [Neu-ETOH]; B %: 25%-50%, 15 min.

1-cyano-N-[2-[(4,4-difluorocyclohexyl)amino]-1-(5-fluoro-3-pyridyl)-2-oxo-ethyl]-5-oxo-N-[4-(pentafluoro-λ6-sulfanyl)phenyl]piperazine-2-carboxamide (3.5 mg, 5.46 umol, 23.33% yield, 100% purity) was obtained as white solid. $^1H$ NMR (400 MHz, METHANOL-$d_4$) δ=8.32 (d, J=2.6 Hz, 1H), 8.22 (s, 1H), 8.16-6.94 (m, 5H), 6.23 (s, 1H), 4.30 (t, J=4.3 Hz, 1H), 4.15 (d, J=16.5 Hz, 1H), 3.96-3.81 (m, 2H), 3.50 (d, J=4.2 Hz, 2H), 2.15-1.78 (m, 6H), 1.69-1.40 (m, 2H).

1-cyano-N-[2-[(4,4-difluorocyclohexyl)amino]-1-(5-fluoro-3-pyridyl)-2-oxo-ethyl]-5-oxo-N-[4-(pentafluoro-λ6-sulfanyl)phenyl]piperazine-2-carboxamide (3.5 mg, 5.37 umol, 22.93% yield, 98.277% purity) was obtained as white solid. $^1H$ NMR (400 MHz, METHANOL-$d_4$) δ=8.32 (br d, J=2.4 Hz, 1H), 8.22 (s, 1H), 8.14-6.80 (m, 5H), 6.23 (s, 1H), 4.30 (t, J=4.2 Hz, 1H), 4.15 (d, J=16.5 Hz, 1H), 3.97-3.80 (m, 2H), 3.50 (d, J=4.4 Hz, 2H), 2.14-1.78 (m, 6H), 1.70-1.40 (m, 2H).

1-cyano-N-[2-[(4,4-difluorocyclohexyl)amino]-1-(5-fluoro-3-pyridyl)-2-oxo-ethyl]-5-oxo-N-[4-(pentafluoro-2, 6-sulfanyl)phenyl]piperazine-2-carboxamide (2.02 mg, 3.15 umol, 13.47% yield) was obtained as white solid. $^1H$ NMR (400 MHz, METHANOL-$d_4$) δ=8.38-8.31 (m, 1H), 8.22 (s, 1H), 8.14-6.89 (m, 5H), 6.17 (s, 1H), 4.37-4.31 (m, 1H), 4.18-4.10 (m, 1H), 3.98-3.76 (m, 2H), 3.55 (dd, J=2.4, 3.8 Hz, 2H), 2.10-1.82 (m, 6H), 1.69-1.39 (In, 2H).

1-cyano-N-[2-[(4,4-difluorocyclohexyl)amino]-1-(5-fluoro-3-pyridyl)-2-oxo-ethyl]-5-oxo-N-[4-(pentafluoro-$\lambda^6$-sulfanyl)phenyl]piperazine-2-carboxamide (13 mg, 19.56 umol, 20.88% yield, 96.391% purity) was obtained as white solid. $^1H$ NMR (400 MHz, METHANOL-$d_4$) δ=8.34 (d, J=2.7 Hz, 1H), 8.22 (s, 1H), 8.14-6.60 (m, 5H), 6.17 (s, 1H), 4.33 (t, J=3.9 Hz, 1H), 4.15 (d, J=16.9 Hz, 1H), 3.96-3.77 (m, 2H), 3.57-3.51 (m, 2H), 2.13-1.80 (m, 6H), 1.70-1.37 (In, 2H).

Example 144: Synthesis of Compound 1161

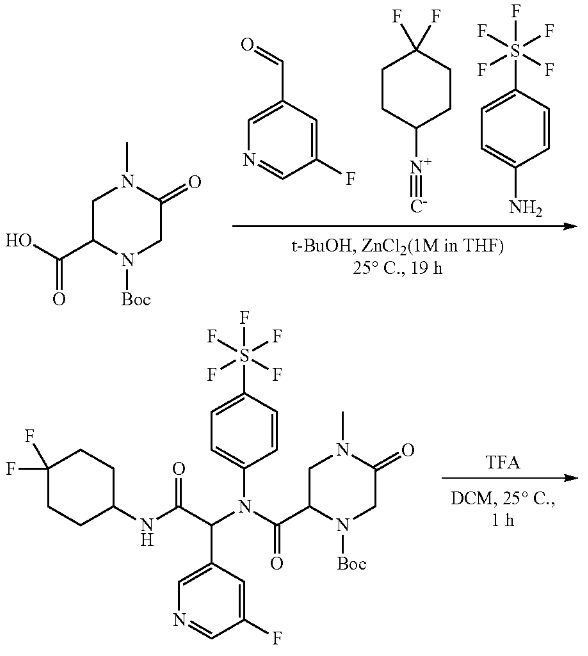

-continued

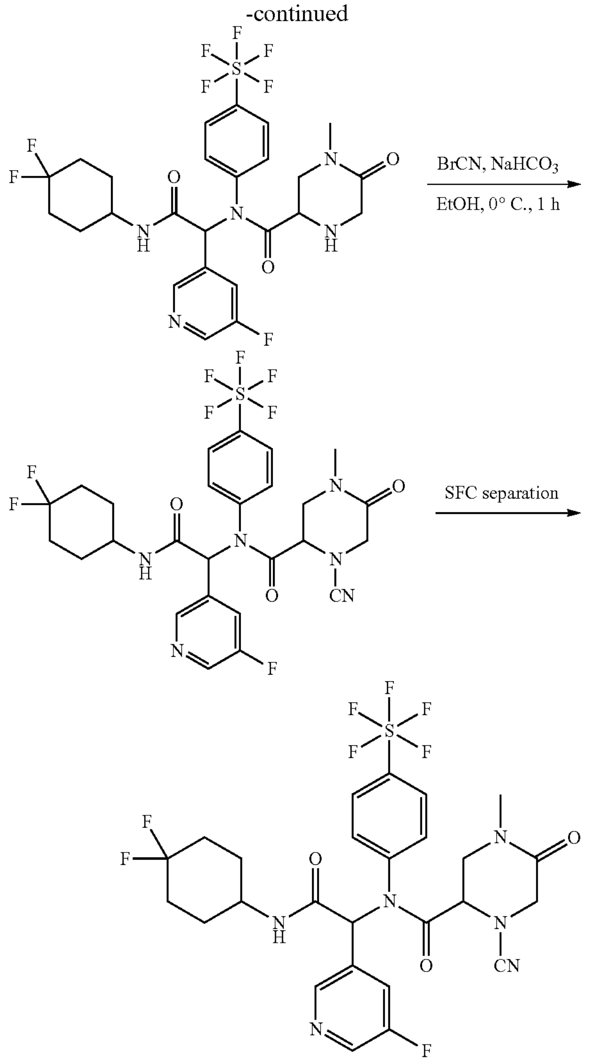

Step 1: tert-butyl 2-[[2-[(4,4-difluorocyclohexyl) amino]-1-(5-fluoro-3-pyridyl)-2-oxo-ethyl]-[4-(pentafluoro-$\lambda^6$-sulfanyl)phenyl]carbamoyl]-4-methyl-5-oxo-piperazine-1-carboxylate 5-Fluoropyridine-3-carbaldehyde (217.97 mg, 1.74 mmol, 1.5 eq), 4-(pentafluoro-λ6-sulfanyl)aniline (254.59 mg, 1.16 mmol, 1 eq) in t-BuOH (1 mL) was stirred at 25° C. for 2 h, and then the 1-tert-butoxycarbonyl-4-methyl-5-oxo-piperazine-2-carboxylic acid (300 mg, 1.16 mmol, 1 eq), 1,1-difluoro-4-isocyano-cyclohexane (168.60 mg, 1.16 mmol, 1 eq) was added. After the addition of $ZnCl_2$ (1 M, 6.97 mL, 6 eq), the solution was stirred at 25° C. for 17 h. Upon completion, the solution was diluted with $H_2O$ (20 mL), extracted with EA (50 mL*3), the combined organic phase was dried over $Na_2SO_4$, filtrated and concentrated to give the crude. The residue was purified by prep-TLC ($SiO_2$, DCM:MeOH=10:1). Tert-butyl 2-[[2-[(4, 4-difluorocyclohexyl) amino]-1-(5-fluoro-3-pyridyl)-2-oxo-ethyl]-[4-(pentafluoro-λ6-sulfanyl)phenyl]carbamoyl]-4-methyl-5-oxo-piperazine-1-carboxylate (550 mg, 753.75 umol, 64.89% yield, 100% purity) was obtained as yellow solid. MS (ESI) m/z 730.1 $[M+H]^+$.

Step 2: N-[2-[(4,4-difluorocyclohexyl)amino]-1-(5-fluoro-3-pyridyl)-2-oxo-ethyl]-4-methyl-5-oxo-N-[4-(pentafluoro-$\lambda^6$-sulfanyl)phenyl]piperazine-2-carboxamide Tert-butyl 2-[[2-[(4,4-difluorocyclohexyl)amino]-1-(5-fluoro-3-pyridyl)-2-oxo-ethyl]-[4-(pentafluoro-λ6-sulfanyl) phenyl]carbamoyl]-4-methyl-5-oxo-piperazine-1-carboxylate (500 mg, 685.23 umol, 1 eq) in TFA (3.08 g, 27.01 mmol, 2 mL, 39.42 eq)/DCM (10 mL) was stirred at 25° C. for 1 h. Upon completion, the solution was concentrated to remove the DCM and TFA, the pH was adjusted to 7-8 by the addition of $NaHCO_3$, extracted with EA (50 mL*3), the combined organic phase was dried over $Na_2SO_4$, filtrated and concentrated to give the crude. The crude was used to next step directly and without further purification. N-[2-[(4, 4-difluorocyclohexyl)amino]-1-(5-fluoro-3-pyridyl)-2-oxo-ethyl]-4-methyl-5-oxo-N-[4-(pentafluoro-46-sulfanyl)phenyl]piperazine-2-carboxamide (350 mg, crude) was obtained as yellow solid. MS (ESI) m/z 630.1 $[M+H]^+$.

Step 3: 1-cyano-N-[2-[(4,4-difluorocyclohexyl) amino]-1-(5-fluoro-3-pyridyl)-2-oxo-ethyl]-4-methyl-5-oxo-N-[4-(pentafluoro-$\lambda^6$-sulfanyl)phenyl] piperazine-2-carboxamide To a solution of N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl]piperazine-2-carboxamide (300 mg, 476.52 umol, 1 eq) in EtOH (1 mL) was added the $NaHCO_3$ (80.06 mg, 953.04 umol, 37.07 uL, 2 eq) and the solution was cooled to 0° C. After the addition of BrCN (160 mg, 1.51 mmol, 111.11 uL, 3.17 eq), the solution was stirred at 0° C. for 1 h. Upon completion, the solution was quenched with $H_2O$ (20 mL), extracted with EA (30 mL*3), the combined organic phase was dried over $Na_2SO_4$, filtrated and concentrated to give the crude. The residue was purified by prep-HPLC (FA condition), column: Phenomenex Luna C18 200*40 mm*10 um; mobile phase: [water (0.2% FA)-ACN]; B %: 40%-80%, 8 min. 1-cyano-N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl] piperazine-2-carboxamide (180 mg, 272.47 umol, 57.18% yield, 99.1% purity) was obtained as white solid. $^1H$ NMR (400 MHz, METHANOL-$d_4$) δ=8.33 (dd, J=2.6, 6.9 Hz, 1H), 8.22 (s, 1H), 8.11-6.78 (m, 5H), 6.26-6.14 (m, 1H), 4.32 (td, J=4.1, 14.3 Hz, 1H), 4.20-4.09 (m, 1H), 3.97-3.78 (m, 2H), 3.58-3.46 (m, 2H), 2.992 (s, 3H), 2.12-1.77 (m, 6H), 1.70-1.38 (m, 2H). MS (ESI) m/z 654.7 $[M+H]^+$.

1-cyano-N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl]piperazine-2-carboxamide was separate by SFC, column: DAICEL CHIRALCEL OD (250 mm*30 mm, 10 um); mobile phase: [Neu-MeOH]; B %: 25%-50%, 15 min, Isomer 3 and Isomer 4 were separate, Isomer 1 and Isomer 2 were separate second time, column: DAICEL CHIRALCEL OJ (250 mm*30 mm, 10 um); mobile phase: [Neu-IPA]; B %: 20%-20%, 8 min.

1-cyano-N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl]piperazine-2-carboxamide (16 mg, 24.05 umol, 44.98% yield, 98.395% purity) was obtained as white solid. $^1H$ NMR (400 MHz, METHANOL-$d_4$) δ=8.32 (d, J=2.7 Hz, 1H), 8.21 (s, 1H), 8.13-7.05 (m, 5H), 6.21 (s, 1H), 4.37 (t, J=4.1 Hz, 1H), 4.14 (d, J=16.3 Hz, 1H), 3.99-3.81 (m, 2H), 3.71-3.52 (m, 2H), 2.99 (s, 3H), 2.10-1.80 (m, 6H), 1.72-1.39 (m, 2H). MS (ESI) m/z 654.7 $[M+H]^+$.

1-cyano-N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl]piperazine-2-carboxamide (25 mg, 35.75 umol, 57.07% yield, 93.6% purity) was obtained as white solid. $^1$H NMR (400 MHz, METHANOL-$d_4$) δ=8.33 (d, J=2.6 Hz, 1H), 8.22 (s, 1H), 8.17-7.06 (m, 5H), 6.19 (s, 1H), 4.40 (dd, J=2.8, 4.5 Hz, 1H), 4.14 (d, J=17.2 Hz, 1H), 3.89 (br t, J=9.9 Hz, 1H), 3.79 (d, J=17.0 Hz, 1H), 3.74-3.58 (m, 2H), 2.99 (s, 3H), 2.12-1.79 (m, 6H), 1.67-1.39 (m, 2H). MS (ESI) m/z 654.7 $[M+H]^+$.

1-cyano-N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl]piperazine-2-carboxamide (20 Ing, 29.52 umol, 10.73% yield, 96.6% purity) was obtained as white solid, $^1$H NMR (400 MHz, METHANOL-$d_4$) δ=8.32 (d, J=2.6 Hz, 1H), 8.21 (s, 1H), 8.15-6.97 (m, 5H), 6.21 (s, 1H), 4.37 (t, J=3.9 Hz, 1H), 4.14 (d, J=16.5 Hz, 1H), 3.96-3.80 (m, 2H), 3.71-3.50 (m, 2H), 2.99 (s, 3H), 2.12-1.81 (m, 6H), 1.70-1.39 (m, 2H). MS (ESI) m/z 654.7 $[M+H]^+$.

1-cyano-N-[2-[(4,4-difluorocyclohexyl)amino]-1-(5-fluoro-3-pyridyl)-2-oxo-ethyl]-4-methyl-5-oxo-N-[4-(pentafluoro-λ6-sulfanyl)phenyl]piperazine-2-carboxamide (20 mg, 30.55 umol, 11.11% yield, 100% purity) was obtained as white solid, $^1$H NMR (400 MHz, METHANOL-$d_4$) δ=8.32 (d, J=2.7 Hz, 1H), 8.22 (s, 1H), 8.11-6.98 (m, 5H), 6.19 (s, 1H), 4.39 (dd, J=2.8, 4.6 Hz, 1H), 4.13 (d, J=17.0 Hz, 1H), 3.89 (br t, J=10.5 Hz, 1H), 3.79 (d, J=17.0 Hz, 1H), 3.74-3.59 (m, 2H), 2.99 (s, 3H), 2.13-1.77 (m, 6H), 1.68-1.38 (m, 2H). MS (ESI) m/z 654.7 $[M+H]^+$.

Example 145: Synthesis of Compound 1244

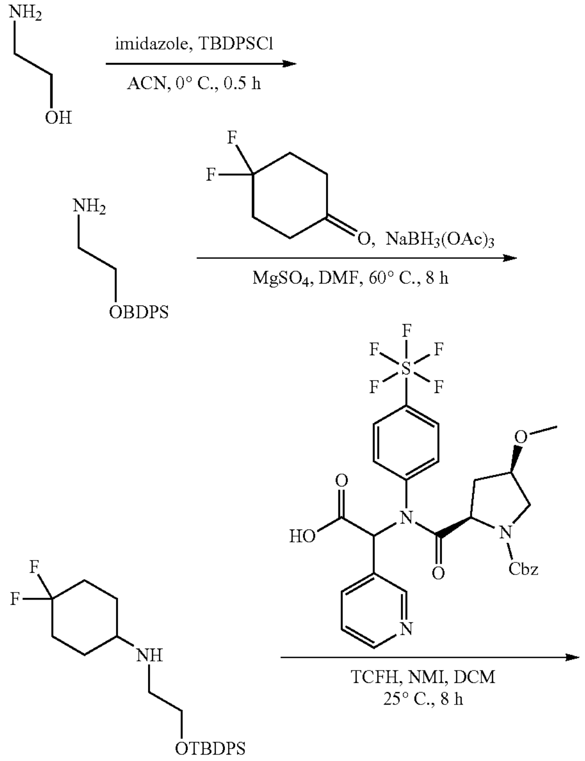

-continued

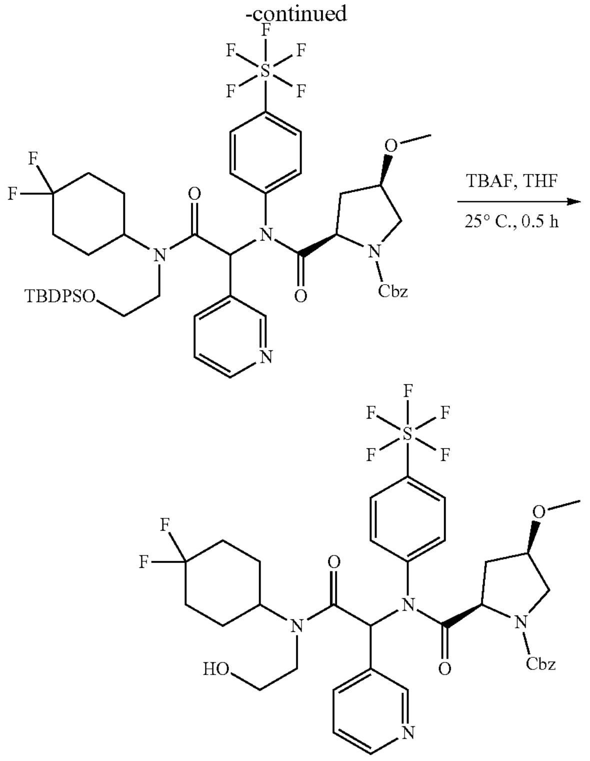

Step 1: 2-[tert-butyl(diphenyl)silyl]oxyethanamine

To a solution of 2-aminoethanol (1 g, 16.37 mmol, 990.10 uL, 1 eq) in ACN (40 mL) was added imidazole (2.45 g, 36.02 mmol, 2.2 eq) and TBDPSCl (4.95 g, 18.01 mmol, 4.63 mL, 1.1 eq). The mixture was stirred at 0° C. for 0.5 h. The mixture was quenched with a saturated aqueous sodium bicarbonate solution (80 ml), diluted with water (40 ml) and extracted with DCM (40 ml*3). The combined organic extracts were washed with brine (60 ml), dried ($Na_2SO_4$) and concentrated in vacuo. Compound 2-[tert-butyl (diphenyl)silyl]oxyethanamine (3 g, 10.02 mmol, 61.19% yield) was obtained as colorless oil and used directly next step. MS (ESI) m/z 300.2 $[M+H]^+$ Step 2: N-[2-[tert-butyl(diphenyl)silyl]oxyethyl]-4,4-difluoro-cyclohexanamine To a solution of 4,4-difluorocyclohexanone (1.38 g, 10.28 mmol, 1.1 eq), 2-[tert-butyl(diphenyl) silyl]oxyethanamine (2.8 g, 9.35 mmol, 1 eq) in DMF (30 mL) was added $MgSO_4$ (3.38 g, 28.05 mmol, 3 eq) and $NaBH(OAc)_3$ (3.96 g, 18.70 mmol, 2 eq) at 25° C. The mixture was stirred at 60° C. for 8 h. The reaction mixture was added with water (100 mL) and stirred for 5 min. The aqueous phase was extracted with ethyl acetate (30 mL*3). The combined organic phase was washed with brine (20 mL*3), dried with anhydrous $Na_2SO_4$, filtered and concentrated in vacuum. The crude product was purified by recrystallization with petroleum ether/ethyl acetate (5/1, 50 mL) and filtered to get the filter cake as the product. N-[2-[tert-butyl(diphenyl)silyl]oxyethyl]-4,4-difluoro-cyclohexanamine (1.56 g, 3.56 mmol, 38.06% yield, 95.26% purity) was obtained as the white solid and used directly next step. MS (ESI) m/z 418.2 $[M+H]^+$ Step 3: benzyl (2R,4R)-2-[[2-[2-[tert-butyl(diphenyl)silyl]oxyethyl-(4,4-difluorocyclohexyl)amino]-2-oxo-1-(3-pyridyl)ethyl]-[4-(pentafluoro-λ$^6$-sulfanyl)phenyl]carbamoyl]-4-methoxy-pyrrolidine-1-carboxylate To a mixture of N-[2-[tert-butyl(diphenyl)silyl]oxyethyl]-4,4-difluoro-cyclohexanamine (81.41 mg, 194.94 umol, 1.2 eq) and 2-[N-[(2R,4R)-1-benzyloxycarbonyl-4-methoxy-pyrrolidine-2-carbonyl]-4-(pentafluoro-λ$^6$-sulfanyl)anilino]-2-(3-pyridyl)acetic acid (100 mg, 162.45 umol, 1 eq) and 1-methylimidazole (93.37 mg, 1.14 mmol, 90.65 uL, 7 eq) in ACN (1 mL) was added [chloro(dimethylamino) methylene]-dimethyl-ammonium;hexafluorophosphate (182.32 mg, 649.81 umol, 4 eq) at 25° C. under $N_2$. The mixture was stirred at 25° C. for 8 h. The residue was added water (5 mL). The aqueous phase was extracted with ethyl acetate (3 mL*3). The combined organic phase was washed with brine (3 mL), dried with anhydrous $Na_2SO_4$, filtered and concentrated in vacuum. benzyl (2R,4R)-2-[[2-[2-[tert-butyl(diphenyl)silyl]oxyethyl-(4,4-difluorocyclohexyl) amino]-2-oxo-1-(3-pyridyl)ethyl]-[4-(pentafluoro-λ$^6$-sulfanyl)phenyl]carbamoyl]-4-methoxy-pyrrolidine-1-carboxylate (120 mg, crude) was obtained as the light yellow oil and used directly next step. MS (ESI) m/z 1015.4 $[M+H]^+$ Step 4: benzyl (2R,4R)-2-[[2-[(4,4-difluorocyclohexyl)-(2-hydroxyethyl)amino]-2-oxo-1-(3-pyridyl) ethyl]-[4-(pentafluoro-λ$^6$-sulfanyl)phenyl]carbamoyl]-4-methoxy-pyrrolidine-1-carboxylate To a mixture of benzyl (2R,4R)-2-[[2-[2-[tert-butyl(diphenyl)silyl]oxyethyl-(4,4-difluoro cyclohexyl)amino]-2-oxo-1-(3-pyridyl)ethyl]-[4-(pentafluoro-λ$^6$-sulfanyl)phenyl]carbamoyl]-4-methoxy-pyrrolidine-1-carboxylate (120 mg, 118.21 umol, 1 eq) in THF (1 mL) was added TBAF (1 M, 354.62 uL, 3 eq) at 25° C. under $N_2$. The mixture was stirred at 25° C. for 30 min. The residue was poured into water (3 mL) and stirred for 2 min. The aqueous phase was extracted with ethyl acetate (3 mL*3). The combined organic phase was washed with brine (3 mL*3), dried with anhydrous $Na_2SO_4$, filtered and concentrated in vacuum. The crude product was purified by pre-HPLC. Benzyl (2R,4R)-2-[[2-[(4,4-difluorocyclohexyl)-(2-hydroxyethyl) amino]-2-oxo-1-(3-pyridyl)ethyl]-[4-(pentafluoro-λ$^6$-sulfanyl)phenyl]carbamoyl]-4-methoxy-pyrrolidine-1-carboxylate (4 mg, 5.15 umol, 4.36% yield, 100% purity) was obtained as the white solid. MS (ESI) m/z 777.2 $[M+H]^+$ Prep-HPLC condition: column: Phenomenex Luna C18 75*30 mm*3 um; mobile phase: [water (0.225% FA)-ACN]; B %: 25%-60%, 8 min $^1$H NMR (400 MHz, METHANOL-$d_4$) δ ppm 8.36-8.59 (m, 2H), 8.16 (s, 1H), 8.10 (br s, 1H), 6.98-7.98 (m, 1H), 5.68-6.08 (m, 1H), 5.06-5.34 (m, 2H), 3.76-4.65 (m, 6H), 3.45-3.74 (m, 1H), 3.37 (td, J=10.36, 5.73 Hz, 1H), 3.17-3.29 (m, 1H), 2.93-3.15 (m, 2H), 2.66-2.90 (m, 1H), 1.69-2.35 (m, 8H), 1.38-1.58 (m, 2H)

Example 147: Synthesis of Compound 1309

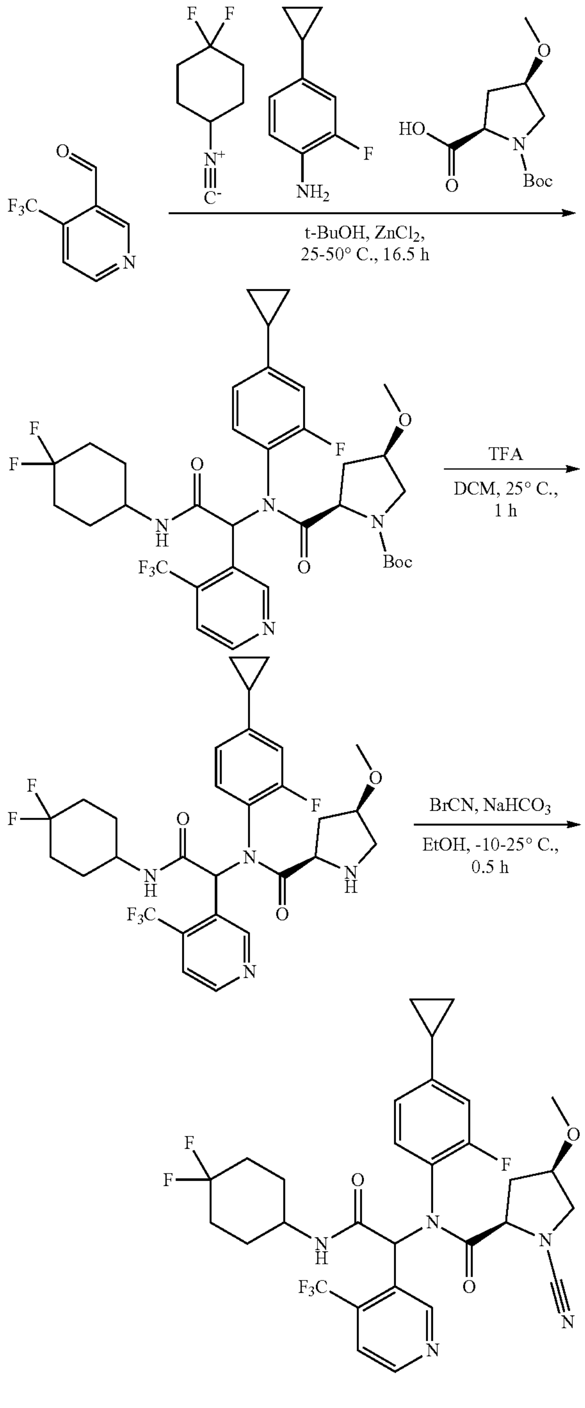

Step 1: (2R,4R)-tert-butyl2-((4-cyclopropyl-2-fluorophenyl)(2-((4,4-difluorocyclohexyl)amino)-2-oxo-1-(4-(trifluoromethyl)pyridin-3-yl)ethyl)carbamoyl)-4-methoxypyrrolidine-1-carboxylate 4-Cyclopropyl-2-fluoro-aniline (259.01 mg, 1.71 mmol, 1 eq) and 4-(trifluoromethyl)pyridine-3-carbaldehyde (300 mg, 1.71 mmol, 1 eq) in t-BuOH (5 mL) were stirred at 25° C. for 0.5 h. (2R,4R)-1-Tert-butoxycarbonyl-4-methoxypyrrolidine-2-carboxylic acid (420.21 g, 1.71 mol, 1 eq) 1,1-difluoro-4-isocyano-cyclohexane (248.67 mg, 1.71 mmol, 1 eq) and $ZnCl_2$ (1 M, 5.14 mL, 3 eq) were added, and the mixture was stirred at 50° C. for 16 h. Upon completion, the mixture was concentrated under the reduced pressure to give a residue. The residue was purified by prep-HPLC (column: Kromasil C18 (250*50 mm*10 um); mobile phase: [water (10 mM $NH_4HCO_3$)-ACN]; B %: 60%-80%, 10 min) to give tert-butyl(2R,4R)-2-[(4-cyclopropyl-2-fluoro-phenyl)-[2-[(4,4-difluorocyclohexyl)amino]-2-oxo-1-[4-(trifluoromethyl)-3-pyridyl]ethyl]carbamoyl]-4-methoxy-pyrrolidine-1-carboxylate Isomer 1 (140 mg, 200.37 umol) as a yellow oil. MS (ESI) m/z 699.3 $[M+H]^+$ Tert-butyl(2R,4R)-2-[(4-cyclopropyl-2-fluoro-phenyl)-[2-[(4,4-difluorocyclohexyl)amino]-2-oxo-1-[4-(trifluoromethyl)-3-pyridyl]ethyl]carbamoyl]-4-methoxy-pyrrolidine-1-carboxylate Isomer 2 (160 mg, 229.00 umol) was obtained as a yellow oil. MS (ESI) m/z 699.3 $[M+H]^+$ Step 2: (2R,4R)—N-(4-cyclopropyl-2-fluorophenyl)-N-(2-((4,4-difluorocyclohexyl)amino)-2-oxo-1-(4-(trifluoromethyl)pyridin-3-yl)ethyl)-4-methoxy-pyrrolidine-2-carboxamide Isomer 1

A mixture of tert-butyl(2R,4R)-2-[(4-cyclopropyl-2-fluoro-phenyl)-[2-[(4,4-difluorocyclohexyl)amino]-2-oxo-1-[4-(trifluoromethyl)-3-pyridyl]ethyl]carbamoyl]-4-methoxy-pyrrolidine-1-carboxylate Isomer 1 (140 mg, 200.37 umol, 1 eq) in DCM (5 mL) was added TFA (3.08 g, 27.01 mmol, 2 mL, 134.81 eq). The mixture was stirred at 25° C. for 1 h. Upon completion, the reaction mixture was quenched by addition sat. $NaHCO_3$ (30 mL), and then extracted with DCM (10 mL*3). The combined organic layers were washed with brine (30 mL), dried over $Na_2SO_4$, filtered and concentrated under reduced pressure to give (2R,4R)—N-(4-cyclopropyl-2-fluoro-phenyl)-N-[2-[(4,4-difluorocyclohexyl)amino]-2-oxo-1-[4-(trifluoromethyl)-3-pyridyl]ethyl]-4-methoxy-pyrrolidine-2-carboxamide Isomer 1 (120 mg, crude) as a yellow solid. MS (ESI) m/z 599.3 $[M+H]^+$ (2R,4R)—N-(4-cyclopropyl-2-fluorophenyl)-N-(2-((4,4-difluorocyclohexyl)amino)-2-oxo-1-(4-(trifluoromethyl)pyridin-3-yl)ethyl)-4-methoxypyrrolidine-2-carboxamide Isomer 2

To a mixture of tert-butyl(2R,4R)-2-[(4-cyclopropyl-2-fluoro-phenyl)-[2-[(4,4-difluorocyclohexyl)amino]-2-oxo-1-[4-(trifluoromethyl)-3-pyridyl]ethyl]carbamoyl]-4-methoxy-pyrrolidine-1-carboxylate Isomer 2 (160 mg, 229.00 umol, 1 eq) in DCM (5 mL) was added TFA (3.08 g, 27.01 mmol, 2 mL, 117.96 eq). The mixture was stirred at 25° C. for 1 h. Upon completion, the reaction mixture was quenched by addition sat. $NaHCO_3$ (30 mL), and then extracted with DCM (10 mL*3). The combined organic layers were washed with brine (30 mL), dried over $Na_2SO_4$, filtered and concentrated under reduced pressure to give (2R,4R)—N-(4-cyclopropyl-2-fluoro-phenyl)-N-[2-[(4,4-difluorocyclohexyl)amino]-2-oxo-1-[4-(trifluoromethyl)-3-pyridyl]ethyl]-4-methoxy-pyrrolidine-2-carboxamide Isomer 2 (130 mg, crude) as a yellow solid. MS (ESI) m/z 599.3 $[M+H]^+$ Step 3: (2R,4R)-1-cyano-N-(4-cyclopropyl-2-fluoro-phenyl)-N-(2-((4,4-difluorocyclohexyl)amino)-2-oxo-1-(4-(trifluoromethyl)pyridin-3-yl)ethyl)-4-methoxypyrrolidine-2-carboxamide Isomer 1

To a solution of (2R,4R)—N-(4-cyclopropyl-2-fluoro-phenyl)-N-[2-[(4,4-difluorocyclohexyl)amino]-2-oxo-1-[4-(trifluoromethyl)-3-pyridyl]ethyl]-4-methoxy-pyrrolidine-2-carboxamide Isomer 1 (120 mg, 200.47 umol, 1 eq) in EtOH (3 mL) was added $NaHCO_3$ (50.52 mg, 601.42 umol, 23.39 uL, 3 eq), and the reaction was cooled to −10° C. After the addition of a solution of BrCN (31.85 mg, 300.71 umol, 22.12 uL, 1.5 eq) in EtOH (1 mL), the solution stirred for 0.5 h at 0° C. and warmed to 25° C. gradually. Upon completion, the mixture was quenched by addition $H_2O$ (30 mL) and then extracted with DCM (10 mL*3). The combined organic layers were washed with brine (30 mL), dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 40%-60%, 8 min) to give (2R,4R)-1-cyano-N-(4-cyclopropyl-2-fluoro-phenyl)-N-[2-[(4,4-difluorocyclohexyl)amino]-2-oxo-1-[4-(trifluoromethyl)-3-pyridyl]ethyl]-4-methoxy-pyrrolidine-2-carboxamide Isomer 1 (51 mg, 81.78 umol, 40.80% yield, 100% purity) as a white solid. MS (ESI) m/z 624.3 $[M+H]^+$ $^1H$ NMR (400 MHz, METHANOL-$d_4$) δ=8.65-8.54 (m, 1H), 8.19-8.07 (m, 1H), 7.93-7.80 (m, 1H), 7.75-7.62 (m, 1H), 6.99 (dd, J=1.7, 8.3 Hz, 1H), 6.77-6.19 (m, 2H), 4.09-3.97 (m, 1H), 3.94-3.84 (m, 2H), 3.69-3.62 (m, 1H), 3.54-3.46 (m, 1H), 3.29-3.27 (m, 2H), 3.21-3.16 (m, 1H), 2.11-1.79 (in, 9H), 1.63-1.40 (m, 2H), 1.08-0.94 (m, 2H), 0.66 (tdd, J=2.4, 4.8, 7.2 Hz, 2H).

$^1H$ NMR (400 MHz, DMSO-$d_6$) δ=8.64 (br d, J=4.6 Hz, 1H), 8.13 (s, 1H), 8.06-7.90 (m, 1H), 7.82 (t, J=8.4 Hz, 1H), 7.71-7.62 (m, 1H), 6.98 (br d, J=8.4 Hz, 1H), 6.77-6.66 (m, 1H), 6.60-6.49 (m, 1H), 4.03-3.77 (m, 3H), 3.64-3.52 (m, 1H), 3.48-3.28 (m, 1H), 3.27-3.13 (m, 3H), 2.07-1.85 (m, 6H), 1.83-1.73 (m, 3H), 1.58-1.46 (m, 1H), 1.44-1.33 (m, 1H), 1.03-0.93 (m, 2H), 0.65 (br s, 2H).

(2R,4R)-1-cyano-N-(4-cyclopropyl-2-fluorophenyl)-N-(2-((4,4-difluorocyclohexyl)amino)-2-oxo-1-(4-(trifluoromethyl)pyridin-3-yl)ethyl)-4-methoxypyrrolidine-2-carboxamide Isomer 2

To a solution of (2R,4R)—N-(4-cyclopropyl-2-fluoro-phenyl)-N-[2-[(4,4-difluorocyclohexyl)amino]-2-oxo-1-[4-(trifluoromethyl)-3-pyridyl]ethyl]-4-methoxy-pyrrolidine-2-carboxamide Isomer 2 (120 mg, 200.47 umol, 1 eq) in EtOH (3 mL) was added $NaHCO_3$ (50.52 mg, 601.42 umol, 23.39 uL, 3 eq), and the solution was cooled to −10° C. A solution of BrCN (31.85 mg, 300.71 umol, 22.12 uL, 1.5 eq) in EtOH (1 mL) was added and the solution stirred for 0.5 h at 0° C. and warmed to 25° C. gradually. Upon completion, the mixture was quenched by addition $H_2O$ (30 mL) and then extracted with DCM (10 mL*3). The combined organic layers were washed with brine (30 mL), dried over $Na_2SO_4$, filtered and concentrated under reduced pressure to give a residue. The residue was purified by prep-HPLC (column: Waters Xbridge BEH C18 100*30 mm*10 um; mobile phase: [water (10 Mm $NH_4HCO_3$)-ACN]; B %: 40%-60%, 8 min) to give (2R,4R)-1-cyano-N-(4-cyclopropyl-2-fluoro-phenyl)-N-[2-[(4,4-difluorocyclohexyl)amino]-2-oxo-1-[4-(trifluoromethyl)-3-pyridyl]ethyl]-4-methoxy-pyrrolidine-2-carboxamide Isomer 2 (39 mg, 62.54 umol, 31.20% yield, 100% purity) as a white solid. MS (ESI) m/z 624.3 $[M+H]^+$ $^1H$ NMR (400 MHz, METHANOL-$d_4$) δ=8.78-8.57 (m, 1H), 8.30-8.14 (m, 1H), 7.90-7.22 (m, 2H), 7.08-6.93 (m, 1H), 6.68-6.59 (m, 1H), 6.55-6.21 (m, 1H), 4.32-4.15 (m, 1H), 3.99-3.74 (m, 2H), 3.65-3.54 (m, 1H), 3.52-3.42 (m, 1H), 3.23 (s, 2H), 3.20-3.16 (m, 1H), 2.15-1.70 (m, 9H), 1.61-1.21 (m, 2H), 1.11-1.00 (m, 2H), 0.78-0.64 (m, 2H).

$^1H$ NMR (400 MHz, DMSO-$d_6$) δ=8.80-8.63 (m, 1H), 8.35-8.18 (m, 1H), 8.08-7.91 (m, 1H), 7.79 (t, J=8.4 Hz, 1H), 7.69 (d, J=5.2 Hz, 1H), 7.10-6.92 (m, 1H), 6.75 (br d, J=12.0 Hz, 1H), 6.47-6.06 (m, 1H), 4.17-4.00 (m, 1H), 3.98-3.83 (m, 1H), 3.72 (br dd, J=2.4, 7.2 Hz, 1H), 3.61-3.54 (m, 1H), 3.38-3.23 (m, 1H), 3.18-3.12 (m, 3H), 2.07-1.61 (m, 9H), 1.50-1.29 (m, 2H), 1.10-0.91 (m, 2H), 0.79-0.61 (m, 2H).

Example 148: Synthesis of Compound 1311

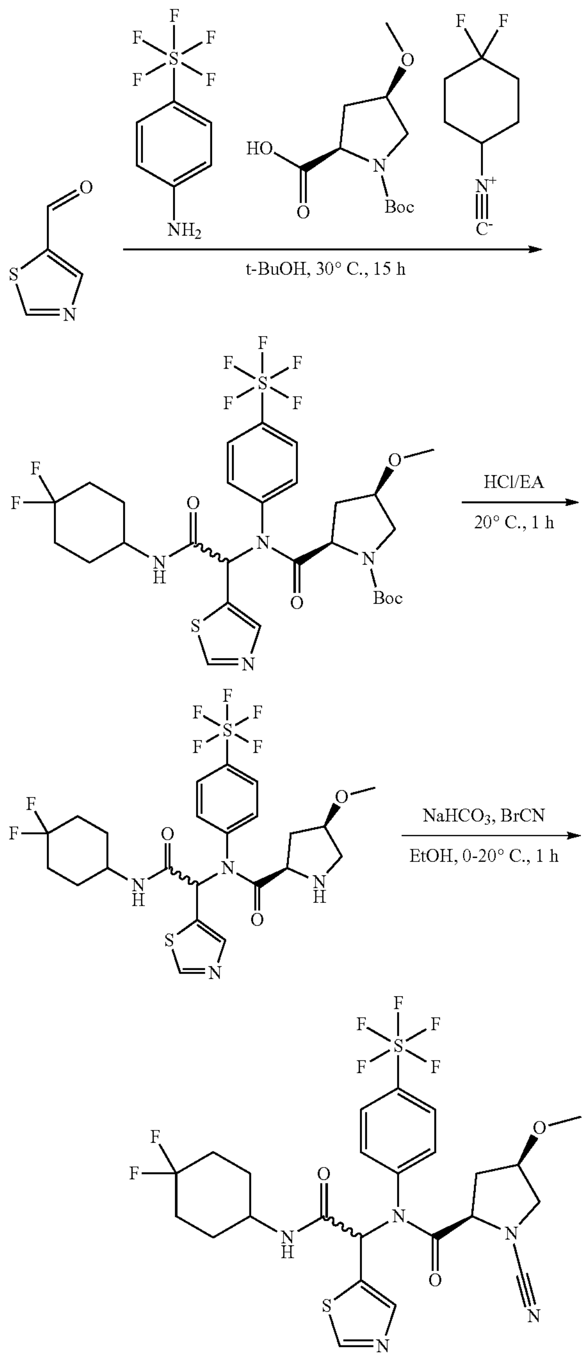

Step 1: tert-butyl (2R,4R)-2-[[2-[(4,4-difluorocyclohexyl)amino]-2-oxo-1-thiazol-5-yl-ethyl]-[4-(pentafluoro-λ$^6$-sulfanyl)phenyl]carbamoyl]-4-methoxy-pyrrolidine-1-carboxylate A solution of thiazole-5-carbaldehyde (200 mg, 1.77 mmol, 1 eq) and 4-(pentafluoro-λ$^6$-sulfanyl)aniline (309.96 mg, 1.41 mmol, 0.8 eq) in t-BuOH (5 mL) was stirred at 30° C. for 3 h, and then (2R,4R)-1-tert-butoxycarbonyl-4-methoxy-pyrrolidine-2-carboxylic acid (650.37 mg, 2.65 mmol, 1.5 eq), 1,1-difluoro-4-isocyano-cyclohexane (256.59 mg, 1.77 mmol, 1 eq) in t-BuOH (0.5 mL) and $ZnCl_2$/THF (1 M, 5.30 mL, 3 eq) were added to the solution. The mixture was stirred at 30° C. for 12 h. Upon completion, the reaction mixture was concentrated under reduced pressure to give a residue. Then the residue was purified by prep-HPLC (column: YMC-Actus Triart C18 100*30 mm*5 um; mobile phase: [water (10 mM $NH_4HCO_3$)-ACN]; B %: 55%-75%, 10 min) to afford tert-butyl(2R,4R)-2-[[2-[(4,4-difluorocyclohexyl)amino]-2-oxo-1-thiazol-5-yl-ethyl]-[4-(pentafluoro-λ$^6$-sulfanyl)phenyl]carbamoyl]-4-methoxy-pyrrolidine-1-carboxylate (180 mg, 242.65 umol, 13.73% yield, 95% purity) as a white solid. MS (ESI) m/z 705.2 $[M+H]^+$.

Step 2: (2R,4R)—N-[2-[(4,4-difluorocyclohexyl)amino]-2-oxo-1-thiazol-5-yl-ethyl]-4-methoxy-N-[4-(pentafluoro-λ$^6$-sulfanyl)phenyl]pyrrolidine-2-carboxamide A mixture of tert-butyl (2R,4R)-2-[[2-[(4,4-difluorocyclohexyl)amino]-2-oxo-1-thiazol-5-yl-ethyl]-[4-(pentafluoro-λ$^6$-sulfanyl)phenyl]carbamoyl]-4-methoxy-pyrrolidine-1-carboxylate (170 mg, 241.23 umol, 1 eq) and HCl/EtOAc (4 M, 10 mL, 165.82 eq) was stirred at 20° C. for 1 h. Upon completion, the mixture was added $NaHCO_3$ (50 mL) and then extracted with EA (30 mL*3). The combined organic layers were washed with brine (50 mL), dried over $Na_2SO_4$, filtered and concentrated under reduced pressure to give the product (2R,4R)—N-[2-[(4,4-difluorocyclohexyl)amino]-2-oxo-1-thiazol-5-yl-ethyl]-4-methoxy-N-[4-(pentafluoro-λ$^6$-sulfanyl)phenyl]pyrrolidine-2-carboxamide (145 mg, crude) as white solid. MS (ESI) m/z 605.1 $[M+H]^+$.

Step3: (2R,4R)-1-cyano-N-[2-[(4,4-difluorocyclohexyl)amino]-2-oxo-1-thiazol-5-yl-ethyl]-4-methoxy-N-[4-(pentafluoro-λ$^6$-sulfanyl)phenyl]pyrrolidine-2-carboxamide A solution of (2R,4R)—N-[2-[(4,4-difluorocyclohexyl)amino]-2-oxo-1-thiazol-5-yl-ethyl]-4-methoxy-N-[4-(pentafluoro-λ$^6$-sulfanyl)phenyl]pyrrolidine-2-carboxamide (140 mg, 231.56 umol, 1 eq) and $NaHCO_3$ (38.90 mg, 463.11 umol, 18.01 uL, 2 eq) in EtOH (2 mL) was cooled to 0° C., then BrCN (30 mg, 283.23 umol, 20.83 uL, 1.22 eq) in EtOH (0.1 mL) was added into the solution. Finally, the mixture was stirred for 1 h and warmed to 20° C. gradually. Upon completion, the mixture was added with $H_2O$ (10 mL) and then extracted with EA (10 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 35%-60%, 10 min) to give the product (2R,4R)-1-cyano-N-[2-[(4,4-difluorocyclohexyl)amino]-2-oxo-1-thiazol-5-yl-ethyl]-4-methoxy-N-[4-(pentafluoro-λ$^6$-sulfanyl)phenyl] pyrrolidine-2-carboxamide (56 mg, 82.84 umol, 35.78% yield, 93.14% purity) was obtained as white solid. MS (ESI) m/z 630.1 $[M+H]^+$.

$^1$H NMR (400 MHz, METHANOL-$d_4$) δ=8.97-8.83 (m, 1H), 7.94-7.34 (m, 5H), 6.56-6.34 (m, 1H), 4.30-4.20 (m, 1H), 3.95-3.75 (m, 2H), 3.68-3.58 (m, 1H), 3.53-3.44 (m, 1H), 3.29-3.17 (m, 3H), 2.11-1.81 (m, 8H), 1.72-1.47 (m, 2H).

Example 149: Synthesis of Compound 1313

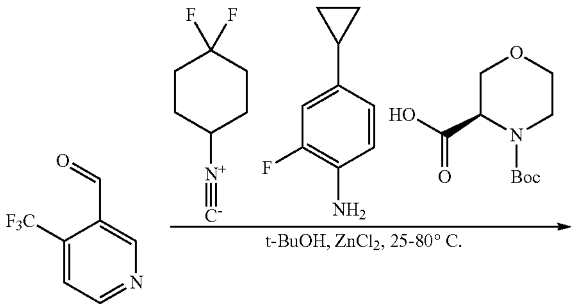

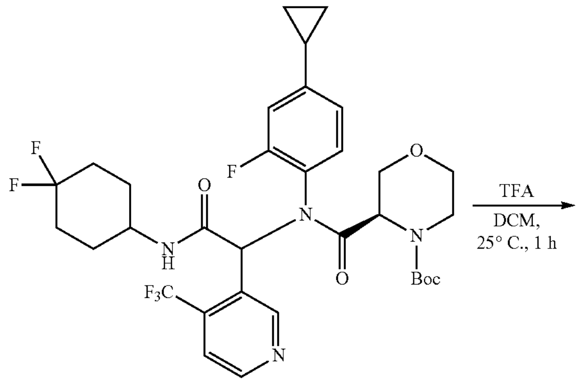

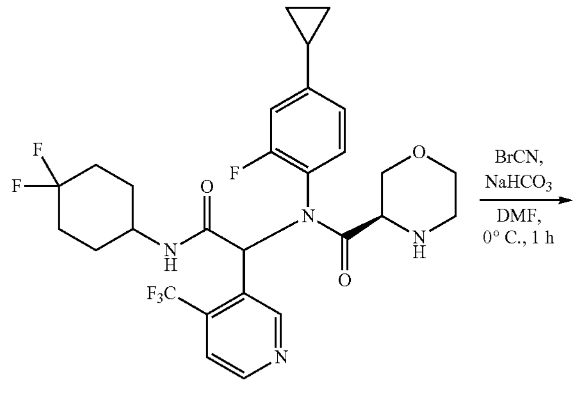

-continued

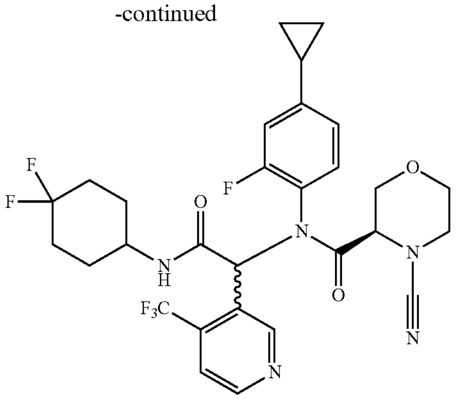

Step 1: (3R)-tert-butyl3-((4-cyclopropyl-2-fluorophenyl)(2-((4,4-difluorocyclohexyl)amino)-2-oxo-1-(4-(trifluoromethyl)pyridin-3-yl)ethyl)carbamoyl) morpholine-4-carboxylate A solution of 4-cyclopropyl-2-fluoro-aniline (280 mg, 1.85 mmol, 1 eq) and 4-(trifluoromethyl)pyridine-3-carbaldehyde (389.18 mg, 2.22 mmol, 1.2 eq) in t-BuOH (6 mL) was stirred at 25° C. for 2 h, and then (3R)-4-tert-butoxycarbonylmorpholine-3-carboxylic acid (856.57 mg, 3.70 mmol, 2 eq) was added to the mixture. 1,1-difluoro-4-isocyano-cyclohexane (537.66 mg, 3.70 mmol, 2 eq) was added in portions, followed by the addition of $ZnCl_2$ (1 M, 5.56 mL, 3 eq) to the mixture. The mixture was stirred at 80° C. for 5 h. Upon the reaction complement, the mixture was concentration in vacuum and was purified by column ($SiO_2$, PE:EA=1:0 to 2:1) and was repurification by prep-HPLC (column: Kromasil C18 (250*50 mm*10 um); mobile phase: [water (10 mM $NH_4HCO_3$)-ACN]; B %: 55%-75%, 10 min) to obtained (3R)-tert-butyl 3-((4-cyclopropyl-2-fluorophenyl)(2-((4,4-difluorocyclohexyl)amino)-2-oxo-1-(4-(trifluoromethyl)pyridin-3-yl)ethyl)carbamoyl)morpholine-4-carboxylate (190 mg, 249.76 umol, 13.49% yield, 90% purity) as a yellow oil. MS (ESI) m/z 685.4 $[M+H]^+$ Step 2: (3R)—N-(4-cyclopropyl-2-fluorophenyl)-N-(2-((4,4-difluorocyclohexyl)amino)-2-oxo-1-(4-(trifluoromethyl)pyridin-3-yl)ethyl)morpholine-3-carboxamide A solution of (3R)-tert-butyl 3-((4-cyclopropyl-2-fluorophenyl) (2-((4,4-difluorocyclohexyl)amino)-2-oxo-1-(4-(trifluoromethyl)pyridin-3-yl)ethyl)carbamoyl)morpholine-4-carboxylate (190 mg, 277.51 umol, 1 eq) in DCM (3 mL) and TFA (1 mL) was stirred at 25° C. for 1 h. Upon completion, the mixture was concentrated in vacuum and the pH was adjusted to ~7 with sat. $NaHCO_3$ (20 mL) and was extracted with DCM (10 mL*2) to obtain (3R)—N-(4-cyclopropyl-2-fluorophenyl)-N-(2-((4,4-difluorocyclohexyl)amino)-2-oxo-1-(4-(trifluoromethyl)pyridin-3-yl) ethyl)morpholine-3-carboxamide (150 mg, crude) as a yellow solid. MS (ESI) m/z 585.3 $[M+H]^+$ Step 3: (R)-4-cyano-N-(4-cyclopropyl-2-fluorophenyl)-N-(2-((4,4-difluorocyclohexyl)amino)-2-oxo-1-(4-(trifluoromethyl)pyridin-3-yl)ethyl)morpholine-3-carboxamide To a solution of (3R)—N-(4-cyclopropyl-2-fluorophenyl)-N-(2-((4,4-difluorocyclohexyl)amino)-2-oxo-1-(4-(trifluoromethyl) pyridin-3-yl)ethyl) morpholine-3-carboxamide (150 mg, 256.61 umol, 1 eq) in DMF (5 mL) was added $NaHCO_3$ (64.67 mg, 769.82 umol, 29.94 uL, 3 eq), and then the mixture was cooled to 0° C. After the addition of BrCN (67.95 mg, 641.52 umol, 47.19 uL, 2.5 eq), the mixture was stirred at 0° C. for 1 h. Upon completion, the mixture was quenched by water (10 mL), extracted with DCM (10 mL*2), and then concentrated in vacuum. The crude product was purified by prep-HPLC (column: Waters Xbridge BEH-C18 100*25 mm*5 um; mobile phase: [water (10 mM $NH_4HCO_3$)-ACN]; B %: 40%-64%, 10 min) to obtained (R)-4-cyano-N-(4-cyclopropyl-2-fluorophenyl)-N-(2-((4,4-difluorocyclohexyl)amino)-2-oxo-1-(4-(trifluoromethyl) pyridin-3-yl)ethyl)morpholine-3-carboxamide Isomer 1 (45 mg, 73.68 umol, 28.71% yield, 99.8% purity) as a white solid. MS (ESI) m/z 610.5 $[M+H]^+$ $^1H$ NMR (400 MHz, MeOD-$d_4$) δ ppm 8.61 (d, J=5.1 Hz, 1H), 8.14 (s, 1H), 7.86 (t, J=8.2 Hz, 1H), 7.69 (d, J=5.4 Hz, 1H), 7.02-6.91 (m, 1H), 6.73 (s, 1H), 6.63 (dd, J=1.8, 11.5 Hz, 1H), 3.96-3.57 (m, 7H), 3.19-3.07 (m, 1H), 2.11-1.71 (m, 7H), 1.66-1.52 (m, 1H), 1.49-1.35 (m, 1H), 1.09-0.95 (m, 2H), 0.77-0.60 (m, 2H).

$^1H$ NMR (400 MHz, DMSO-$d_6$, 273+80K) δ ppm 8.70-8.59 (m, 1H), 8.15 (s, 1H), 7.98 (d, J=6.8 Hz, 1H), 7.83 (t, J=8.0 Hz, 1H), 7.65 (d, J=5.2 Hz, 1H), 6.97 (d, J=7.6 Hz, 1H), 6.72 (d, J=10.6 Hz, 1H), 6.58 (s, 1H), 3.88-3.48 (m, 8H), 2.03-1.72 (m, 7H), 1.54 (d, J=12.2 Hz, 1H), 1.40 (s, 1H), 0.96 (d, J=7.6 Hz, 2H), 0.64 (s, 2H).

(R)-4-cyano-N-(4-cyclopropyl-2-fluorophenyl)-N-(2-((4,4-difluorocyclohexyl)amino)-2-oxo-1-(4-(trifluoromethyl) pyridin-3-yl)ethyl)morpholine-3-carboxamide Isomer 2 (45 mg, 73.68 umol, 28.71% yield, 99.8% purity) was obtained as a white solid. MS (ESI) m/z 610.5 $[M+H]^+$ $^1H$ NMR (400 MHz, MeOD-$d_4$) δ ppm 9.00-8.59 (m, 1H), 8.23 (s, 1H), 7.83 (t, J=8.4 Hz, 1H), 7.73 (d, J=5.6 Hz, 1H), 7.28-6.60 (m, 2H), 6.55-6.18 (m, 1H), 4.02-3.48 (m, 7H), 3.11 (dt, J=3.2, 9.3 Hz, 1H), 2.07-1.28 (m, 10H), 1.12-0.94 (m, 2H), 0.79-0.62 (m, 2H).

$^1H$ NMR (400 MHz, DMSO-$d_6$, 273+80K) δ ppm 8.96-8.61 (m, 1H), 8.23 (s, 1H), 7.99 (s, 1H), 7.78 (t, J=8.4 Hz, 1H), 7.69 (d, J=4.9 Hz, 1H), 7.38-7.00 (m, 1H), 6.98-6.70 (m, 1H), 6.44-6.06 (m, 1H), 3.94-3.35 (m, 8H), 2.05-1.17 (m, 1H), 1.07-0.90 (m, 2H), 0.68 (s, 2H).

Example 151: Synthesis of Compound 1315

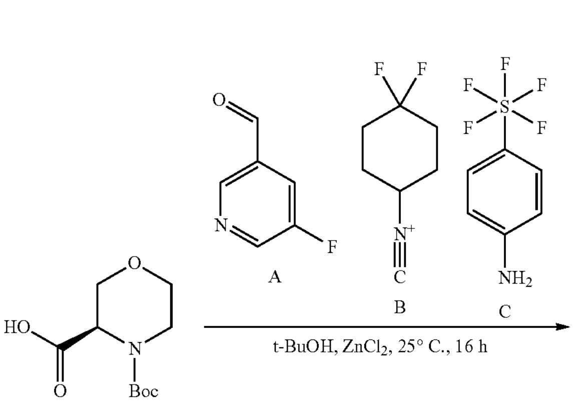

-continued

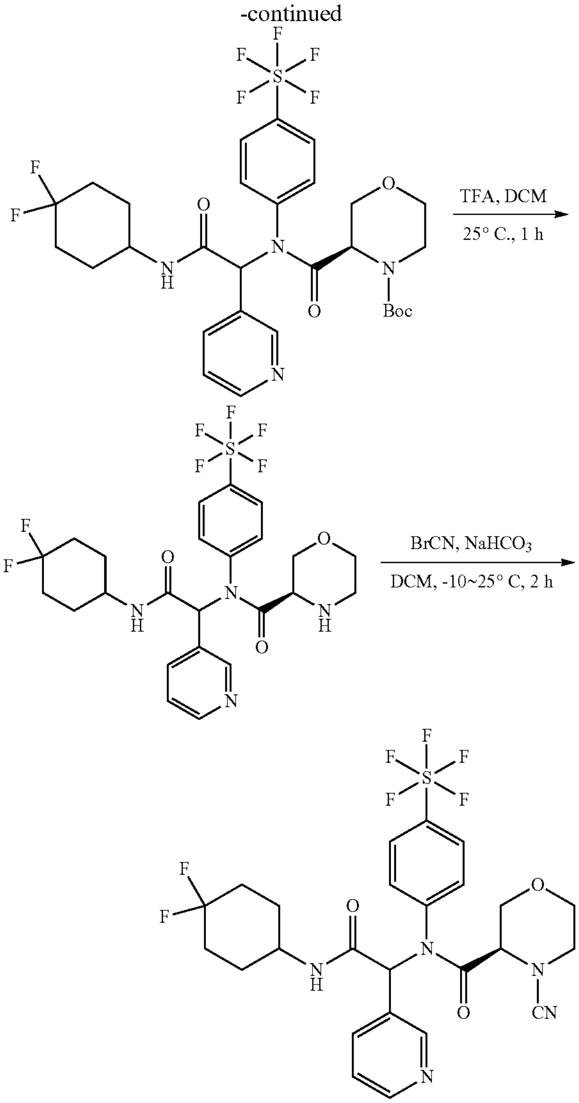

Step 1: tert-butyl(3R)-3-[[2-[(4,4-difluorocyclohexyl)amino]-2-oxo-1-(3-pyridyl)ethyl]-[4-(pentafluoro-$\lambda^6$-sulfanyl)phenyl]carbamoyl]morpholine-4-carboxylate A solution of 4-(pentafluoro-λ6-sulfanyl)aniline (1.42 g, 6.49 mmol, 1 eq) pyridine-3-carbaldehyde (694.78 mg, 6.49 mmol, 609.46 uL, 1 eq) in t-BuOH (20 mL) was stirred at 25° C. for 8 h, and the mixture was added with (3R)-4-tert-butoxycarbonylmorpholine-3-carboxylic acid (1.5 g, 6.49 mmol, 1 eq), 1,1-difluoro-4-isocyano-cyclohexane (941.53 mg, 6.49 mmol, 1 eq) $ZnCl_2$ (1 M, 38.92 mL, 6 eq), and stirred at 25° C. for 8 h. Upon completion, the reaction was concentrated in the vacuum and was purified by prep-HPLC (column: Kromasil C18 (250*50 mm*10 um); mobile phase: [water (10 mM $NH_4HCO_3$)-ACN]; B %: 45%-75%, 10 min) to give product tert-butyl(3R)-3-[[2-[(4,4-difluorocyclohexyl)amino]-2-oxo-1-(3-pyridyl)ethyl]-[4-(pentafluoro-λ6-sulfanyl)phenyl]carbamoyl]morpholine-4-carboxylate (1.4 g, 2.04 mmol, 31.52% yield) as yellow oil. MS (ESI) m/z 685.2 $[M+H]^+$.

Step 2: (3R)—N-[2-[(4,4-difluorocyclohexyl)amino]-2-oxo-1-(3-pyridyl)ethyl]-N-[4-(pentafluoro-A6-sulfanyl)phenyl]morpholine-3-carboxamide To a solution of tert-butyl (3R)-3-[[2-[(4,4-difluorocyclohexyl)amino]-2-oxo-1-(3-pyridyl)ethyl]-[4-(pentafluoro-λ6-sulfanyl)phenyl]carbamoyl]morpholine-4-carboxylate (1.3 g, 1.90 mmol, 1 eq) in DCM (25 mL) was added TFA (12.99 g, 113.92 mmol, 8.44 mL, 60 eq) and the mixture was stirred at 25° C. for 1 h. Upon completion, the mixture was quenched by addition $NaHCO_3$ (200 mL) and then extracted with EtOAc (100 mL*3). The combined organic layers were washed with brine (100 mL), dried over $Na_2SO_4$, filtered and concentrated under reduced pressure to give crude product (3R)—N-[2-[(4,4-difluorocyclohexyl)amino]-2-oxo-1-(3-pyridyl)ethyl]-N-[4-(pentafluoro-λ6-sulfanyl)phenyl]morpholine-3-carboxamide (1.1 g, crude) was yellow oil. MS (ESI) m/z 585.2 $[M+H]^+$.

Step 3: (3R)-4-cyano-N-[2-[(4,4-difluorocyclohexyl)amino]-2-oxo-1-(3-pyridyl)ethyl]-N-[4-(pentafluoro-26-sulfanyl)phenyl]morpholine-3-carboxamide To a solution of (3R)—N-[2-[(4,4-difluorocyclohexyl)amino]-2-oxo-1-(3-pyridyl)ethyl]-N-[4-(pentafluoro-λ6-sulfanyl)phenyl]morpholine-3-carboxamide (1.09 g, 1.86 mmol, 1 eq) in EtOH (10 mL) was added $NaHCO_3$ (469.94 mg, 5.59 mmol, 217.56 uL, 3 eq), and the mixture was cooled at −10° C. After the addition of BrCN (177.76 mg, 1.68 mmol, 123.44 uL, 0.9 eq) in EtOH (0.5 mL), the reaction was warmed to 25° C. and stirred for 2 h. Upon completion, the mixture was quenched by addition $H_2O$ (100 mL) and then extracted with DCM (100 mL*3). The combined organic layers were washed with brine 100 mL, dried over $Na_2SO_4$, filtered and concentrated under reduced pressure and purified by prep-HPLC (column: Kromasil C18 (250*50 mm*10 um); mobile phase: [water (10 mM NH4HCO3)-ACN]; B %: 30%-60%, 10 min) to give product (3R)-4-cyano-N-[2-[(4,4-difluorocyclohexyl)amino]-2-oxo-1-(3-pyridyl)ethyl]-N-[4-(pentafluoro-λ6-sulfanyl)phenyl]morpholine-3-carboxamide (460 mg, 701.82 umol, 37.64% yield, 93% purity) was yellow solid. MS (ESI) m/z 610.2 $[M+H]^+$ $^1H$ NMR (400 MHz, MeOD-$d_4$) δ=8.42-8.29 (m, 2H), 7.88-7.50 (m, 4H), 7.27-7.22 (m, 1H), 6.29-6.04 (m, 1H), 3.97-3.80 (m, 3H), 3.77-3.59 (m, 4H), 3.16-3.06 (m, 1H), 2.07-1.81 (m, 6H), 1.70-1.35 (m, 2H)

Example 152: Synthesis of Compound 1316

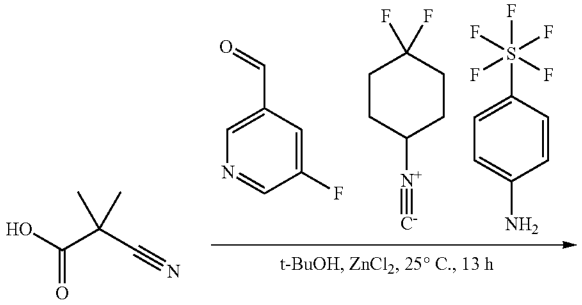

-continued

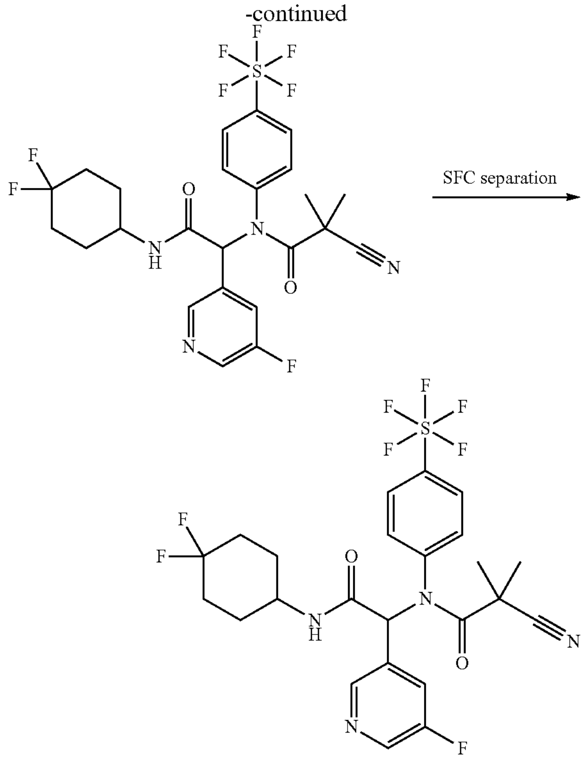

Step1: 2-cyano-N-[2-[(4,4-difluorocyclohexyl)amino]-1-(5-fluoro-3-pyridyl)-2-oxo-ethyl]-2-methyl-N-[4-(pentafluoro-26-sulfanyl)phenyl]propanamide A solution of 4-(pentafluoro-λ6-sulfanyl)aniline (484.41 mg, 2.21 mmol, 1 eq) 5-fluoropyridine-3-carbaldehyde (276.49 mg, 2.21 mmol, 1 eq) in t-BuOH (10 mL) was stirred at 25° C. for 2 h, and then was added 2-cyano-2-methylpropanoic acid (250 mg, 2.21 mmol, 1 eq), and 1,1-difluoro-4-isocyano-cyclohexane (288.72 mg, 1.99 mmol, 0.9 eq). The mixture was stirred at 25° C. for 1 h, $ZnCl_2$ (1 M, 13.26 mL, 6 eq) was added and the reaction was stirred at 25° C. for 10 h. Upon completion, the reaction was concentrated in the vacuum and was purified by prep-HPLC column: Waters Xbridge Prep OBD C18 150*40 mm*10 um; mobile phase: [water (10 mM $NH_4HCO_3$)-ACN]; B %: 45%-65%, 8 min to give provide 2-cyano-N-[2-[(4,4-difluorocyclohexyl)amino]-1-(5-fluoro-3-pyridyl)-2-oxo-ethyl]-2-methyl-N-[4-(pentafluoro-6-sulfanyl)phenyl]propanamide (200 mg, 342.16 umol, 15.48% yield, 100% purity) as white solid. MS (ESI) m/z 585.2 $[M+H]^+$.

Step 2: 2-cyano-N-[2-[(4,4-difluorocyclohexyl)amino]-1-(5-fluoro-3-pyridyl)-2-oxo-ethyl]-2-methyl-N-[4-(pentafluoro-λ6-sulfanyl)phenyl]propanamide 2-Cyano-N-[2-[(4,4-difluorocyclohexyl)amino]-1-(5-fluoro-3-pyridyl)-2-oxo-ethyl]-2-methyl-N-[4-(pentafluoro-λ6-sulfanyl)phenyl]propanamide (180 mg, 307.94 umol, 1 eq) was purified by SFC separation column: DAICEL CHIRALCEL OD (250 mm*30 mm, 10 um); mobile phase: [Neu-MeOH]; B %: 20%-20%, min to give product 2-cyano-N-[2-[(4,4-difluorocyclohexyl)amino]-1-(5-fluoro-3-pyridyl)-2-oxo-ethyl]-2-methyl-N-[4-(pentafluoro-λ6-sulfanyl)phenyl]propanamide (50 mg, 85.54 umol, 27.78% yield) as white solid. MS (ESI) m/z 585.2 $[M+H]^+$ $^1H$ NMR (400 MHz, MeOD-$d_4$) δ=8.32-8.31 (m, 1H), 8.19 (s, 1H), 8.00-7.08 (m, 5H), 6.08 (s, 1H), 3.89-3.85 (m, 1H), 2.07-1.78 (m, 6H), 1.59 (d, J=7.3 Hz, 7H), 1.50-1.37 (m, 1H)

2-Cyano-N-[2-[(4,4-difluorocyclohexyl)amino]-1-(5-fluoro-3-pyridyl)-2-oxo-ethyl]-2-methyl-N-[4-(pentafluoro-λ6-sulfanyl)phenyl]propanamide (50 mg, 85.54 umol, 27.78% yield) was obtained as white solid. MS (ESI) m/z 585.2 $[M+H]^+$ $^1H$ NMR (400 MHz, MrOD-$d_4$) δ=8.32-8.31 (m, 1H), 8.19 (s, 1H), 8.00-7.04 (m, 5H), 6.08 (s, 1H), 3.87-3.85 (m, 1H), 2.12-1.74 (m, 6H), 1.73-1.58 (m, 7H), 1.49-1.36 (m, 1H)

Example 153: Synthesis of Compound 1318

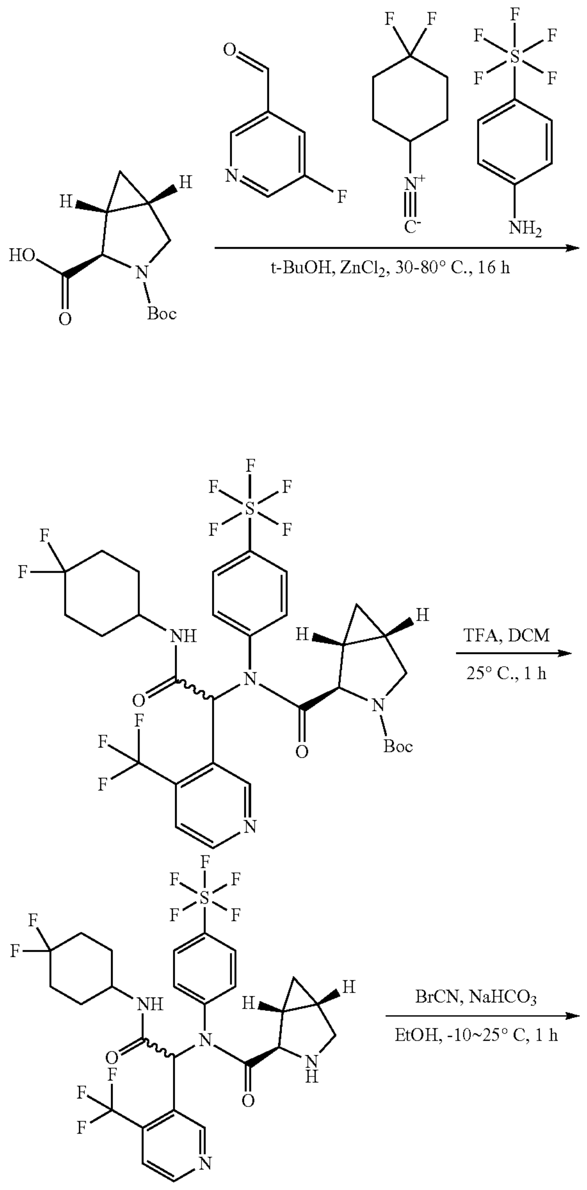

-continued

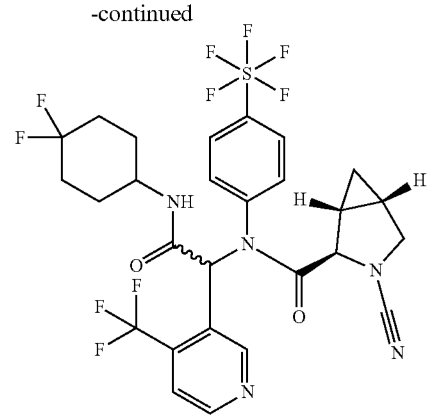

Step 1: tert-butyl (1R,2R,5S)-2-[[2-[(4,4-difluorocyclohexyl)amino]-2-oxo-1-[4-(trifluoromethyl)-3-pyridyl]ethyl]-[4-(pentafluoro-2-sulfanyl)phenyl]carbamoyl]-3-azabicyclo[3.1.0]hexane-3-carboxylate A solution of 4-(trifluoromethyl)pyridine-3-carbaldehyde (231.16 mg, 1.32 mmol, 1 eq), 4-(pentafluoro-$\lambda^6$-sulfanyl)aniline (289.33 mg, 1.32 mmol, 1 eq) in t-BuOH (10 mL) was stirred at 30° C. for 2 h. (1R,2R,5S)-3-tert-butoxycarbonyl-3-azabicyclo[3.1.0]hexane-2-carboxylic acid (300 mg, 1.32 mmol, 1 eq) was added to the reactant mixture. A solution of 1,1-difluoro-4-isocyano-cyclohexane (191.61 mg, 1.32 mmol, 1 eq) in t-BuOH (1 mL) was added in batches (three times), and then $ZnCl_2$ (1 M, 6.60 mL, 5 eq) was added and stirred at 80° C. for 14 h. Upon completion, the reaction mixture was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 65%-85%, 10 min) to afford tert-butyl (1R,2R,5S)-2-[[2-[(4,4-difluorocyclohexyl)amino]-2-oxo-1-[4-(trifluoromethyl)-3-pyridyl]ethyl]-[4-(pentafluoro-$\lambda^6$-sulfanyl)phenyl]carbamoyl]-3-azabicyclo[3.1.0]hexane-3-carboxylate (90 mg, 120.21 umol, 9.11% yield, N/A purity) and tert-butyl (1R,2R,5S)-2-[[2-[(4,4-difluorocyclohexyl)amino]-2-oxo-1-[4-(trifluoromethyl)-3-pyridyl]ethyl]-[4-(pentafluoro-$\lambda^6$-sulfanyl)phenyl]carbamoyl]-3-azabicyclo[3.1.0]hexane-3-carboxylate (120 mg, 160.28 umol, 12.14% yield, N/A purity) as a yellow oil. MS (ESI) m/z 741.2 $[M+H]^+$.

Step 2: (1R,2R,5S)—N-[2-[(4,4-difluorocyclohexyl)amino]-2-oxo-1-[4-(trifluoromethyl)-3-pyridyl]ethyl]-N-[4-(pentafluoro-$\lambda^6$-sulfanyl)phenyl]-3-azabicyclo[3.1.0]hexane-2-carboxamide Isomer 1: A solution of tert-butyl (1R,2R,5S)-2-[[2-[(4,4-difluorocyclohexyl)amino]-2-oxo-1-[4-(trifluoromethyl)-3-pyridyl]ethyl]-[4-(pentafluoro-$\lambda^6$-sulfanyl)phenyl]carbamoyl]-3-azabicyclo[3.1.0]hexane-3-carboxylate (90 mg, 120.21 umol, 1 eq) in TFA (1 mL) and DCM (2 mL) was stirred at 25° C. for 1 h. Upon completion, the reaction mixture was quenched by addition $NaHCO_3$ aq (15 mL), and extracted with DCM (10 mL*3). The combined organic layers were washed with brine (10 mL), dried over $Na_2SO_4$, filtered and concentrated under reduced pressure to afford a (1R,2R,5S)—N-[2-[(4,4-difluorocyclohexyl)amino]-2-oxo-1-[4-(trifluoromethyl)-3-pyridyl]ethyl]-N-[4-(pentafluoro- λ[6]-sulfanyl)phenyl]-3-azabicyclo[3.1.0]hexane-2-carboxamide (70 mg, crude) as a yellow oil. MS (ESI) m/z 641.2 $[M+H]^+$.

Isomer 2: A solution of tert-butyl (1R,2R,5S)-2-[[2-[(4,4-difluorocyclohexyl)amino]-2-oxo-1-[4-(trifluoromethyl)-3-pyridyl]ethyl]-[4-(pentafluoro-λ[6]-sulfanyl)phenyl]carbamoyl]-3-azabicyclo[3.1.0]hexane-3-carboxylate (120 mg, 160.28 umol, 1 eq) in TFA (1 mL) and DCM (2 mL) was stirred at 25° C. for 1 h. Upon completion, the reaction mixture was quenched by addition $NaHCO_3$ aq (20 mL), and extracted with DCM (15 mL*3). The combined organic layers were washed with brine (15 mL), dried over $Na_2SO_4$, filtered and concentrated under reduced pressure to give a (1R,2R,5S)—N-[2-[(4,4-difluorocyclohexyl)amino]-2-oxo-1-[4-(trifluoromethyl)-3-pyridyl]ethyl]-N-[4-(pentafluoro-λ[6]-sulfanyl)phenyl]-3-azabicyclo[3.1.0]hexane-2-carboxamide (100 mg, crude) as a yellow oil. MS (ESI) m/z 641.2 $[M+H]^+$.

Step 3: (1R,2R,5S)-3-cyano-N-[2-[(4,4-difluorocyclohexyl)amino]-2-oxo-1-[4-(trifluoromethyl)-3-pyridyl]ethyl]-N-[4-(pentafluoro-λ[6]-sulfanyl)phenyl]-3-azabicyclo[3.1.0]hexane-2-carboxamide Isomer 1: To a solution of (1R,2R,5S)—N-[2-[(4,4-difluorocyclohexyl)amino]-2-oxo-1-[4-(trifluoromethyl)-3-pyridyl]ethyl]-N-[4-(pentafluoro-λ[6]-sulfanyl)phenyl]-3-azabicyclo[3.1.0]hexane-2-carboxamide (60 mg, 92.51 umol, 1 eq) and $NaHCO_3$ (23.32 mg, 277.54 umol, 10.79 uL, 3 eq) in EtOH (1 mL) was added a solution of BrCN (14.70 mg, 138.77 umol, 10.21 uL, 1.5 eq) in EtOH (0.5 mL) drop-wise at −10° C. under $N_2$. The reaction mixture was slowly warmed and stirred to 25° C. for 1 h. Upon completion, the reaction mixture was quenched by addition $H_2O$ (20 mL) and extracted with EtOAc (10 mL*3). The combined organic layers were washed with brine (10 mL), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-80%, 8 min) to give a (1R,2R,5S)-3-cyano-N-[2-[(4,4-difluorocyclohexyl)amino]-2-oxo-1-[4-(trifluoromethyl)-3-pyridyl]ethyl]-N-[4-(pentafluoro-λ[6]-sulfanyl)phenyl]-3-azabicyclo[3.1.0]hexane-2-carboxamide (53 mg, 78.69 umol, 85.05% yield, 100% purity) as a white solid. MS (ESI) m/z 674.2 $[M+H]^+$.

$^1H$ NMR (400 MHz, MeOD-$d_4$) δ=8.68-8.60 (m, 1H), 8.43-7.48 (m, 5H), 7.26-6.79 (m, 1H), 6.72-6.52 (m, 1H), 4.03 (s, 1H), 3.98-3.84 (m, 2H), 3.49-3.40 (m, 1H), 2.09-1.45 (m, 10H), 0.77-0.68 (m, 1H), 0.29-0.21 (m, 1H).

Isomer 2: To a solution of (1R,2R,5S)—N-[2-[(4,4-difluorocyclohexyl)amino]-2-oxo-1-[4-(trifluoromethyl)-3-pyridyl]ethyl]-N-[4-(pentafluoro-λ[6]-sulfanyl)phenyl]-3-azabicyclo[3.1.0]hexane-2-carboxamide (90 mg, 138.77 umol, 1 eq) and $NaHCO_3$ (34.97 mg, 416.31 umol, 16.19 uL, 3 eq) in EtOH (1 mL) was added a solution of BrCN (23.52 mg, 222.03 umol, 16.33 uL, 1.6 eq) in EtOH (0.5 mL) drop-wise at −10° C. under $N_2$. The reaction mixture was slowly warmed and stirred to 25° C. for 1 h. Upon completion, the reaction mixture was quenched by addition $H_2O$ (30 mL) and extracted with EtOAc (15 mL*3). The combined organic layers were washed with brine (15 mL), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-80%, 8 min) to give a (1R,2R,5S)-3-cyano-N-[2-[(4,4-difluorocyclohexyl)amino]-2-oxo-1-[4-(trifluoromethyl)-3-pyridyl]ethyl]-N-[4-(pentafluoro-λ[6]-sulfanyl)phenyl]-3-azabicyclo[3.1.0]hexane-2-carboxamide (57 mg, 84.62 umol, 60.98% yield, 100% purity) as a white solid. MS (ESI) m/z 674.2 $[M+H]^+$.

$^1H$ NMR (400 MHz, MeOD-$d_4$) δ=8.74-8.61 (m, 1H), 8.33-7.34 (m, 6H), 6.72-6.49 (m, 1H), 4.01 (s, 1H), 3.93-3.80 (m, 2H), 3.46-3.38 (m, 1H), 2.03-1.48 (m, 10H), 0.77-0.68 (m, 1H), 0.29-0.22 (m, 1H).

Example 154: Synthesis of Compound 1175

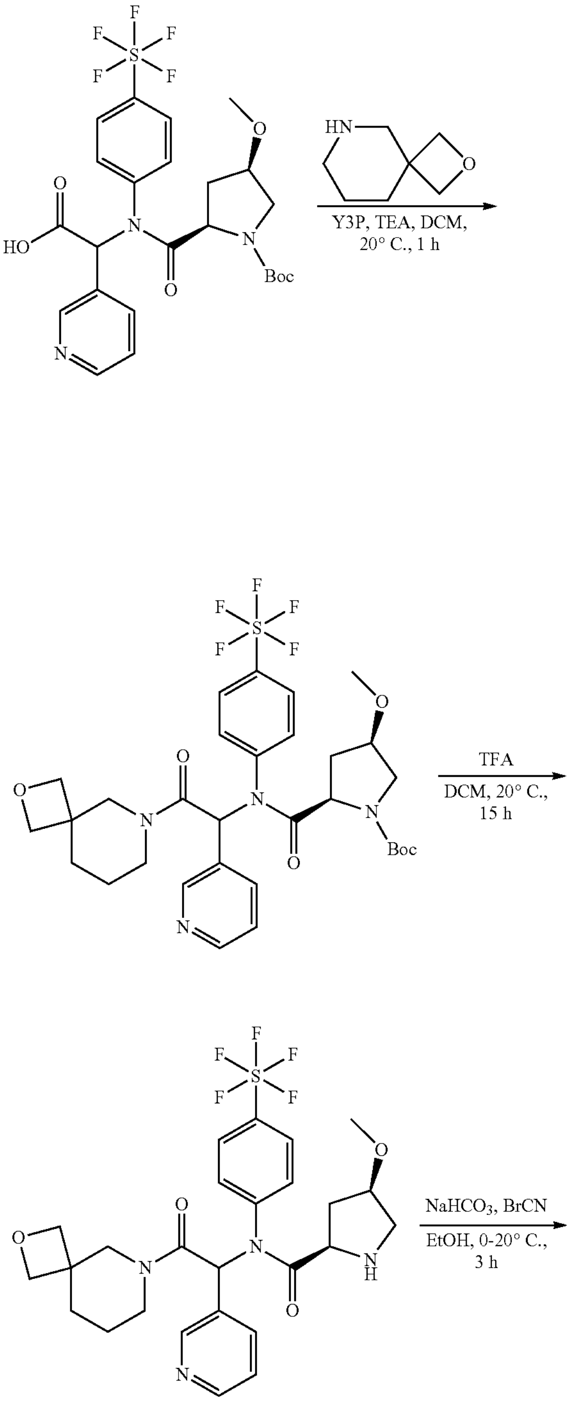

-continued

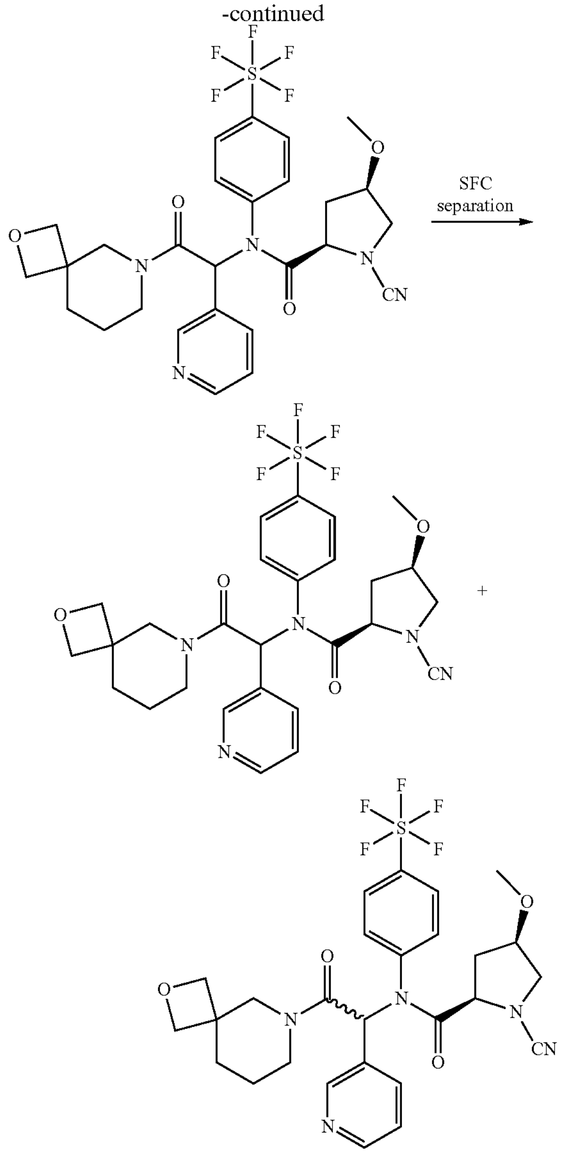

Step 1: tert-butyl (2R,4R)-4-methoxy-2-[[2-(2-oxa-8-azaspiro[3.5]nonan-8-yl)-2-oxo-1-(3-pyridyl)ethyl]-[4-(pentafluoro-$\lambda^6$-sulfanyl)phenyl]carbamoyl]pyrrolidine-1-carboxylate A solution of 2-[N-[(2R,4R)-1-tert-butoxycarbonyl-4-methoxy-pyrrolidine-2-carbonyl]-4-(pentafluoro-$\lambda^6$-sulfanyl)anilino]-2-(3-pyridyl)acetic acid (200 mg, 343.91 umol, 1 eq) 2-oxa-8-azaspiro[3.5]nonane (43.74 mg, 343.91 umol, 1 eq) and TEA (174.00 mg, 1.72 mmol, 239.34 uL, 5 eq) in DCM (3 mL) was cooled to 0° C., and then T3P (656.55 mg, 1.03 mmol, 613.60 uL, 50% purity, 3 eq) was added into the solution. The mixture was stirred for 1 h and warmed to 20° C. gradually. Upon completion, the mixture was added $H_2O$ (30 mL) and then extracted with EA (30 mL*3). The combined organic layers were washed with brine (30 mL), dried over $Na_2SO_4$, filtered and concentrated under reduced pressure to give a residue. Then the residue was purified by prep-TLC ($SiO_2$, DCM:MeOH=10:1) to give the product tert-butyl (2R,4R)-4-methoxy-2-[[2-(2-oxa-8-azaspiro[3.5]nonan-8-yl)-2-oxo-1-(3-pyridyl)ethyl]-[4-(pentafluoro-$\lambda^6$-sulfanyl)phenyl]carbamoyl]pyrrolidine-1-carboxylate (175 mg, 233.06 umol, 67.77% yield, 91.99% purity) as white solid. MS (ESI) m/z 691.2 $[M+H]^+$.

Step 2: (2R,4R)-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide A mixture of tert-butyl (2R,4R)-4-methoxy-2-[[2-(2-oxa-8-azaspiro[3.5]nonan-8-yl)-2-oxo-1-(3-pyridyl)ethyl]-[4-(pentafluoro-$\lambda^6$-sulfanyl)phenyl]carbamoyl]pyrrolidine-1-carboxylate (160 mg, 231.64 umol, 1 eq) and TFA (770.00 mg, 6.75 mmol, 0.5 mL, 29.15 eq) in DCM (2.5 mL) was stirred at 20° C. for 1.5 h. Upon completion, the mixture was added $NaHCO_3$ (50 mL) and then extracted with EA (30 mL*3). The combined organic layers were washed with brine (50 mL), dried over $Na_2SO_4$, filtered and concentrated under reduced pressure to give the product (2R,4R)-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (125 mg, crude) as white solid. MS (ESI) m/z 591.2 $[M+H]^+$.

Step 3: (2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-A-sulfanyl)phenyl]pyrrolidine-2-carboxamide To a solution of (2R,4R)-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (120 mg, 203.18 umol, 1 eq) and $NaHCO_3$ (34.14 mg, 406.36 umol, 15.80 uL, 2 eq) in EtOH (3 mL) was cooled to 0° C. was added BrCN (25 mg, 236.02 umol, 17.36 uL, 1.16 eq) in EtOH (0.5 mL). The mixture was stirred for 3 h and warmed to 20° C. gradually. Upon completion, the mixture was added $H_2O$ (30 mL) and then extracted with EA (30 mL*3). The combined organic layers were washed with brine (30 mL), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM $NH_4HCO_3$)-ACN]; B %: 30%-50%, 8 min) to give the product (2R,4R)-1-cyano-N-[2-[(4,4-difluorocyclohexyl)amino]-2-oxo-1-thiazol-5-yl-ethyl]-4-methoxy-N-[4-(pentafluoro-$\lambda^6$-sulfanyl)phenyl]pyrrolidine-2-carboxamide (40 mg, 64.98 umol, 31.83% yield, 99.51% purity) as white solid. MS (ESI) m/z 616.2 $[M+H]^+$.

$^1H$ NMR (400 MHz, DMSO-$d_6$) δ=8.41-8.30 (m, 2H), 7.78-7.69 (m, 2H), 7.65-7.33 (m, 3H), 7.19-7.11 (m, 1H), 6.65 (br s, 1H), 4.41-4.00 (m, 5H), 3.91-3.84 (m, 1H), 3.83-3.75 (m, 1H), 3.62-3.56 (m, 1H), 3.35-3.27 (m, 2H), 3.21-3.18 (m, 3H), 3.13-3.06 (m, 2H), 2.14-1.97 (m, 1H), 1.88-1.68 (m, 3H), 1.50-1.37 (m, 1H), 0.94-0.83 (m, 1H)

Step 4: (2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (2R,4R)-1-Cyano-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (40 mg, 64.98 umol, 1 eq) was further separated by SFC (column: REGIS (R, R) WHELK-O1 (250 mm*25 mm, 10 um); mobile phase: [Neu-MeOH]; B %: 40%-40%, 10 min)

to provide (2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-λ$^6$-sulfanyl)phenyl]pyrrolidine-2-carboxamide Isomer 1, 4 mg, 6.50 umol, 10.00% yield, 100% purity) as white solid. MS (ESI) m/z 616.2 $[M+H]^+$.

$^1$H NMR (400 MHz, DMSO-$d_6$) δ=8.42-8.31 (m, 2H), 7.85-7.36 (m, 5H), 7.35-7.10 (m, 1H), 6.68 (br s, 1H), 4.50-4.00 (m, 5H), 3.95-3.72 (m, 3H), 3.63-3.56 (m, 1H), 3.45-3.25 (m, 3H), 3.21-3.18 (m, 3H), 2.12-2.00 (m, 1H), 1.88-1.72 (m, 3H), 1.48-1.42 (m, 1H), 1.03-0.91 (m, 1H)

(2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-λ$^6$-sulfanyl)phenyl]pyrrolidine-2-carboxamide Isomer 2, 3 mg, 4.87 umol, 7.50% yield, 100% purity) was obtained as white solid. MS (ESI) m/z 616.2 $[M+H]^+$.

$^1$H NMR (400 MHz, DMSO-$d_6$) δ=8.47-8.31 (m, 2H), 7.75-7.37 (m, 5H), 7.22-7.10 (m, 1H), 6.60 (br s, 1H), 4.42-4.01 (m, 5H), 3.95-3.70 (m, 3H), 3.63-3.55 (m, 1H), 3.45-3.25 (m, 3H), 3.20-3.15 (m, 3H), 2.16-2.00 (m, 1H), 1.91-1.70 (m, 3H), 1.53-1.42 (m, 1H), 1.02-0.90 (m, 1H)

Example 155: Synthesis of Compound 1077

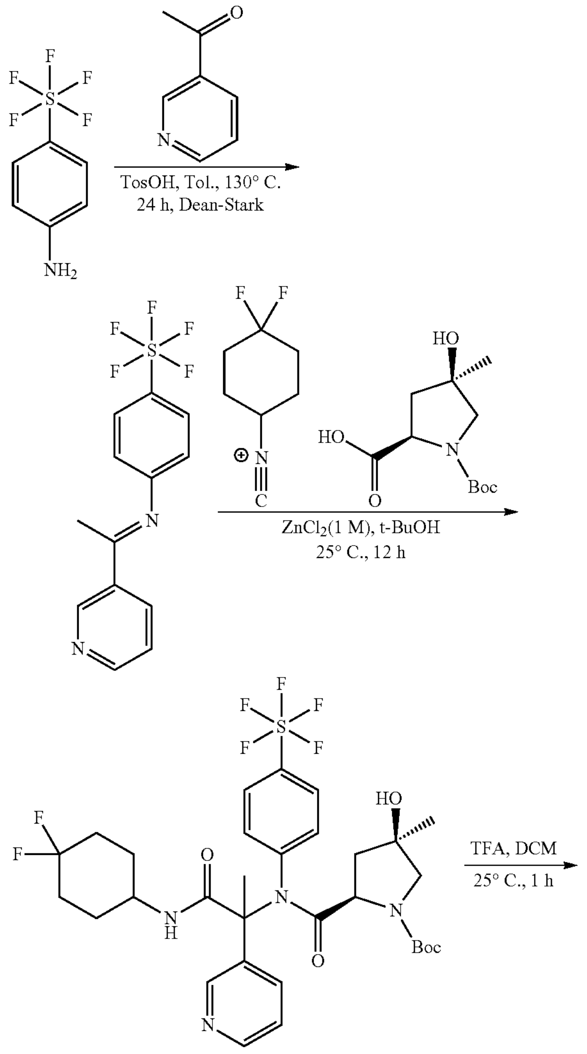

-continued

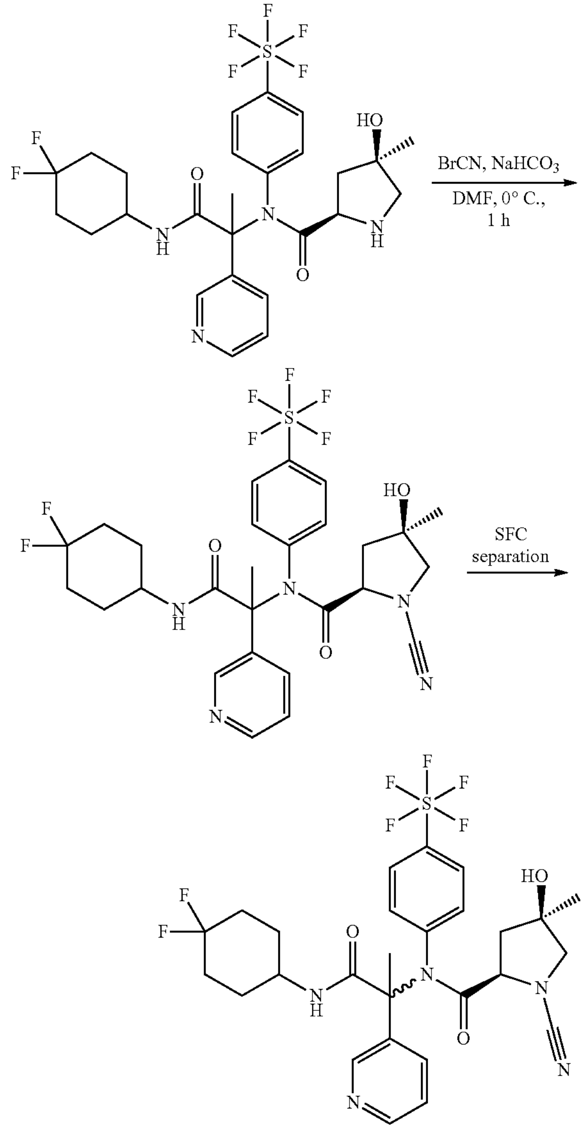

Step 1: (E)-N-[4-(pentafluoro-λ$^6$-sulfanyl)phenyl]-1-(3-pyridyl)ethanimine

To a solution of 4-(pentafluoro-λ$^6$-sulfanyl)aniline (30 g, 136.88 mmol, 1 eq) in toluene (400 mL) was added 1-(3-pyridyl)ethanone (16.58 g, 136.88 mmol, 15.07 mL, 1 eq) and TosOH (1.18 g, 6.84 mmol, 0.05 eq). The mixture was stirred at 130° C. for 24 h and then water was removed by Dean-Stark trap. Upon completion, the reaction mixture was concentrated under reduced pressure to give a residue. The residue was purified by column chromatography ($SiO_2$, petroleum ether/ethyl acetate=20/1 to 2/1) to give (E)-N-[4-(pentafluoro-λ$^6$-sulfanyl)phenyl]-1-(3-pyridyl)ethanimine (25 g, 54.30 mmol, 39.67% yield, 70% purity) as a yellow solid. MS (ESI) m/z 323.1 $[M+H]^+$.

$^1$H NMR (400 MHz, DMSO-$d_6$) δ=9.15 (d, J=1.8 Hz, 1H), 8.72 (dd, J=1.6, 4.8 Hz, 1H), 8.34 (td, J=1.9, 8.0 Hz, 1H), 7.89 (d, J=8.9 Hz, 2H), 7.52 (dd, J=4.8, 8.0 Hz, 1H), 7.02 (d, J=8.6 Hz, 2H), 2.63 (s, 1H), 2.26 (s, 3H).

Step 2: tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-hydroxy-4-methyl-pyrrolidine-1-carboxylate To a solution of (E)-N-[4-(pentafluoro-λ$^6$-sulfanyl)phenyl]-1-(3-pyridyl)ethanimine (3 g, 9.31 mmol, 1 eq), 1,1-difluoro-4-isocyano-cyclohexane (1.35 g, 9.31 mmol, 1 eq) and (2R,4R)-1-tert-butoxycarbonyl-4-hydroxy-4-methyl-pyrrolidine-2-carboxylic acid (2.28 g, 9.31 mmol, 1 eq) in t-BuOH (20 mL) was added $ZnCl_2$ (1 M, 55.85 mL, 6 eq), and the mixture was stirred at 25° C. for 12 h. Upon completion, the reaction mixture was diluted with sat. $NaHCO_3$ (100 mL) and extracted with EA (50 mL*3). The combined organic layers were dried over $Na_2SO_4$, filtered and concentrated under reduced pressure to give a residue. The residue was purified by prep-HPLC (column: Agela DuraShell C18 250*80 mm*10 um; mobile phase: [water (10 mM $NH_4HCO_3$)-ACN]; B %: 40%-65%, 20 min) to give tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-hydroxy-4-methyl-pyrrolidine-1-carboxylate (0.15 g, 136.80 umol, 1.47% yield, 65% purity) as a yellow oil. MS (ESI) m/z 713.3 $[M+H]^+$.

Step 3: (2R,4R)—N-[2-[(4,4-difluorocyclohexyl)amino]-1-methyl-2-oxo-1-(3-pyridyl)ethyl]-4-hydroxy-4-methyl-N-[4-(pentafluoro-2'-sulfanyl)phenyl]pyrrolidine-2-carboxamide To a solution of tert-butyl (2R,4R)-2-[[2-[(4,4-difluorocyclohexyl)amino]-1-methyl-2-oxo-1-(3-pyridyl)ethyl]-[4-(pentafluoro-λ$^6$-sulfanyl)phenyl]carbamoyl]-4-hydroxy-4-methyl-pyrrolidine-1-carboxylate (0.14 g, 196.43 umol, 1 eq) in DCM (2 mL) was added TFA (1.54 g, 13.51 mmol, 1 mL, 68.76 eq), the mixture was stirred at 25° C. for 1 h. Upon completion, the reaction mixture was dried by blowing $N_2$ to give a residue and then diluted with sat. $NaHCO_3$ (20 mL) and extracted with EA (10 mL*3). The combined organic layers were dried over $Na_2SO_4$, filtered and concentrated under reduced pressure to give (2R,4R)—N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide (0.12 g, crude) as a yellow oil. MS (ESI) m/z 613.3 $[M+H]^+$.

Step 4: (2R,4R)-1-cyano-N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide To a solution of (2R,4R)—N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide (0.12 g, 195.89 umol, 1 eq) and $NaHCO_3$ (49.37 mg, 587.66 umol, 22.86 uL, 3 eq) in DMF (2 mL) was added BrCN (24.90 mg, 235.06 umol, 17.29 uL, 1.2 eq) in DMF (0.5 mL) drop-wise at 0° C., and the mixture was stirred at 0° C. for 1 h under $N_2$ atmosphere. Upon completion, the reaction mixture was diluted with water (20 mL) and extracted with EA (10 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-60%, 8 min) to give (2R,4R)-1-cyano-N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide (28.34 mg, 43.11 umol, 22.01% yield, 97% purity) as a white solid. MS (ESI) m/z 638.3 $[M+H]^+$.

$^1$H NMR (400 MHz, METHANOL-$d_4$) δ=8.71-8.51 (m, 1H), 8.47-8.30 (m, 1H), 8.02-7.71 (m, 3H), 7.63-7.56 (m, 1H), 7.49-7.40 (m, 1H), 7.40-7.26 (m, 1H), 4.19-4.10 (m, 1H), 4.03-3.87 (m, 1H), 3.46 (dd, J=4.6, 9.2 Hz, 1H), 3.33 (br s, 1H), 2.17-1.81 (m, 1H), 1.77-1.53 (m, 2H), 1.24 (d, J=3.8 Hz, 3H);

$^1$H NMR (400 MHz, DMSO-$d_6$) δ=8.53-8.37 (m, 1H), 8.30 (dd, J=4.6, 11.6 Hz, 1H), 7.87-7.74 (m, 2H), 7.71 (br d, J=8.8 Hz, 1H), 7.57-7.50 (m, 1H), 7.42-7.29 (m, 1H), 7.25 (ddd, J=5.0, 8.1, 12.7 Hz, 1H), 4.01 (dd, J=5.3, 8.6 Hz, 1H), 3.75 (br d, J=2.7 Hz, 1H), 3.32-3.24 (m, 1H), 3.23-3.15 (m, 1H), 2.04-1.63 (m, 1H), 1.60-1.37 (m, 2H), 1.07 (d, J=4.2 Hz, 3H).

Step 4: (2R,4R)-1-cyano-N-[2-[(4,4-difluorocyclohexyl)amino]-1-methyl-2-oxo-1-(3-pyridyl)ethyl]-4-hydroxy-4-methyl-N-[4-(pentafluoro-As-sulfanyl)phenyl]pyrrolidine-2-carboxamide (2R,4R)-1-Cyano-N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide (26.12 mg, 40.97 umol, 1 eq) was separated by SFC (column: DAICEL CHIRALCEL OD (250 mm*30 mm, 10 um); mobile phase: [Neu-IPA]; B %: 20%-20%, 12 min) To give (2R,4R)-1-cyano-N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide Isomer 1 (12.96 mg, 18.50 umol, 45.15% yield, 91% purity) as a white solid. MS (ESI) m/z 638.2 $[M+H]^+$.

$^1$H NMR (400 MHz, DMSO-$d_6$) δ=8.59 (d, J=2.0 Hz, 1H), 8.41-8.34 (m, 1H), 7.91 (br d, J=8.8 Hz, 2H), 7.74 (br d, J=8.4 Hz, 1H), 7.67-7.60 (m, 1H), 7.57-7.38 (m, 2H), 7.24 (dd, J=4.9, 7.9 Hz, 1H), 5.12 (s, 1H), 4.00 (dd, J=5.8, 8.9 Hz, 1H), 3.85 (br dd, J=0.9, 9.0 Hz, 1H), 3.28 (s, 1H), 3.19 (d, J=8.8 Hz, 1H), 2.06-1.65 (m, 1H), 1.63-1.49 (m, 2H), 1.18-1.07 (m, 3H).

(2R,4R)-1-Cyano-N-[2-[(4,4-difluorocyclohexyl)amino]-1-methyl-2-oxo-1-(3-pyridyl)ethyl]-4-hydroxy-4-methyl-N-[4-(pentafluoro-λ$^6$-sulfanyl)phenyl]pyrrolidine-2-carboxamide Isomer 2 (8.65 mg, 12.21 umol, 29.80% yield, 90% purity) was obtained as a white solid. MS (ESI) m/z 638.2 $[M+H]^+$.

$^1$H NMR (400 MHz, DMSO-$d_6$) δ=8.50 (d, J=2.3 Hz, 1H), 8.41-8.28 (m, 1H), 7.90 (br d, J=8.2 Hz, 1H), 7.80 (br d, J=7.7 Hz, 1H), 7.68 (br dd, J=1.9, 6.1 Hz, 2H), 7.57 (d, J=7.9 Hz, 1H), 7.37 (br d, J=8.9 Hz, 1H), 7.20 (dd, J=4.7, 8.0 Hz, 1H), 5.14 (s, 1H), 4.00 (dd, J=6.3, 8.7 Hz, 1H), 3.89 (br d, J=7.3 Hz, 1H), 3.29-3.27 (m, 1H), 3.23-3.09 (m, 1H), 2.06-1.75 (m, 10H), 1.71-1.44 (m, 3H), 1.19-1.03 (m, 3H).

Example 157: Synthesis of Compound 1320

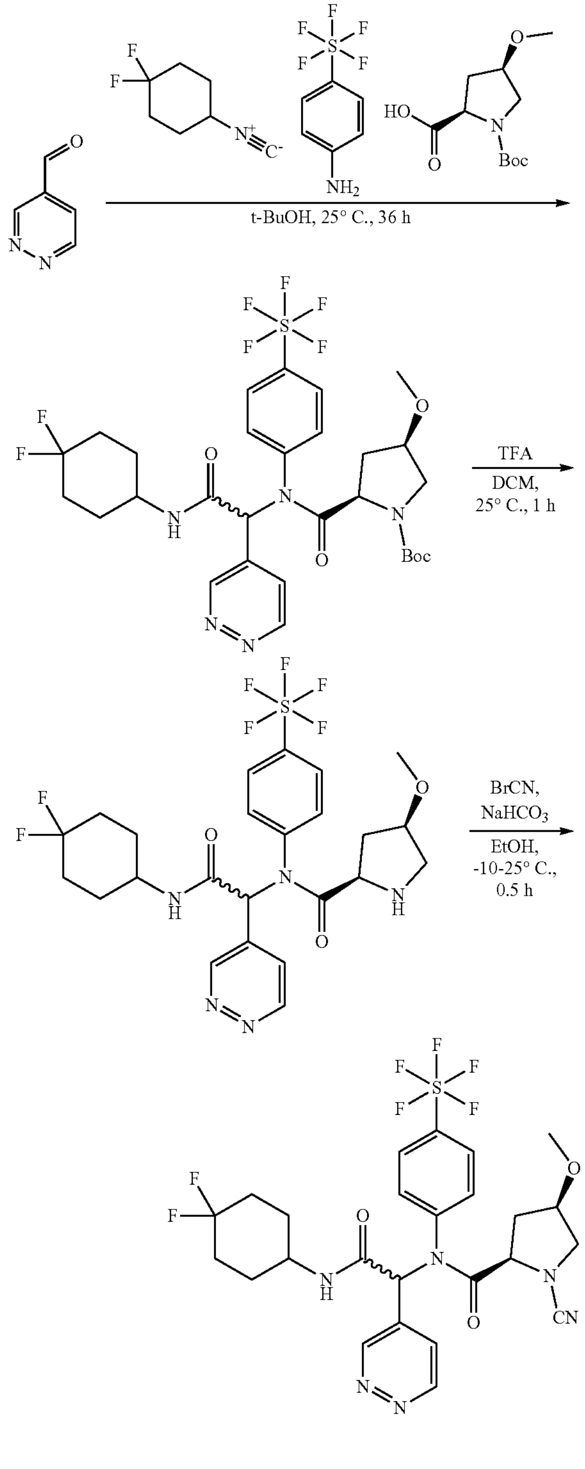

Step 1 tert-butyl(2R,4R)-2-[[2-[(4,4-difluorocyclohexyl)amino-2-oxo-1pyridazin-4-yl-ethyl]-[4-(pentafluoro-26-sulfanyl)phenylcarbamoyl]-4-methoxy-pyrrolidine-1-carboxylate A solution of 4-(pentafluoro-6-sulfanyl)aniline (648.82 mg, 2.96 mmol, 0.8 eq) and pyridazine-4-carbaldehyde (400 mg, 3.70 mmol, 1 eq) in t-BuOH (10 mL) was stirred at 25° C. for 12 h, then (2R,4R)-1-tert-butoxycarbonyl-4-methoxy-pyrrolidine-2-carboxylic acid (1.36 g, 5.55 mmol, 1.5 eq), and then 1,1-difluoro-4-isocyano-cyclohexane (537.10 mg, 3.70 mmol, 1 eq) in t-BuOH (2 mL) was added into the solution. TH/$ZnCl_2$ (1 M, 11.10 mL, 3 eq) was added into the mixture, and the mixture was stirred at 25° C. for 24 h. Upon completion, the reaction mixture was concentrated under the reduced pressure to give a residue. The residue was purified by prep-HPLC (column: Welch Xtimate C18 250*70 mm*10 um; mobile phase: [water (10 mM $NH_4HCO_3$)-ACN]; B %: 35%-70%, 20 min) affording tert-butyl (2R,4R)-2-[[2-[(4,4-difluorocyclohexyl)amino]-2-oxo-1-pyridazin-4-yl-ethyl]-[4-(pentafluoro-λ6-sulfanyl)phenyl]carbamoyl]-4-methoxy-pyrrolidine-1-carboxylate (450 mg, 643.15 umol) as a yellow solid. MS (ESI) m/z 700.3 $[M+H]^+$ Step 2: (2R,4R)—N-[2-[(4,4-difluorocyclohexyl)amino]-2-oxo-1-pyridazin-4-yl-ethyl]-4-methoxy-N-[4-(pentafluoro-λ6-sulfanyl)phenyl]pyrrolidine-2-carboxamide To a solution of tert-butyl (2R,4R)-2-[[2-[(4,4-difluorocyclohexyl)amino]-2-oxo-1-pyridazin-4-yl-ethyl]-[4-(pentafluoro-λ6-sulfanyl)phenyl]carbamoyl]-4-methoxy-pyrrolidine-1l-carboxylate (350 mg, 500.23 umol, 1 eq) in DCM (9 mL) was added TFA (4.04 g, 35.45 mmol, 2.62 mL, 70.87 eq). The mixture was stirred at 25° C. for 1 h. Upon completion, the mixture was concentrated under the reduced pressure to afford (2R,4R)—N-[2-[(4,4-difluorocyclohexyl)amino]-2-oxo-1-pyridazin-4-yl-ethyl]-4-methoxy-N-[4-(pentafluoro-λ6-sulfanyl)phenyl]pyrrolidine-2-carboxamide (300 mg, crude) as a yellow solid. MS (ESI) m/z 600.2 $[M+H]^+$ Step 3: (2R,4R)-1-cyano-N-[2-[(4,4-difluorocyclohexyl)amino]-2-oxo-1-pyridazin-4-yl-ethyl]-4-methoxy-N-[4-(pentafluoro-λ6-sulfanyl)phenyl]pyrrolidine-2-carboxamide To a solution of (2R,4R)—N-[2-[(4,4-difluorocyclohexyl)amino]-2-oxo-1-pyridazin-4-yl-ethyl]-4-methoxy-N-[4-(pentafluoro-λ6-sulfanyl)phenyl]pyrrolidine-2-carboxamide (300 mg, 500.36 umol, 1 eq) in EtOH (3 mL) was added $NaHCO_3$ (126.10 mg, 1.50 mmol, 58.38 uL, 3 eq), and the solution was cooled to −10° C. After the addition of BrCN (79.50 mg, 750.55 umol, 55.21 uL, 1.5 eq) in EtOH (1 mL), the solution was stirred for 0.5 h at 0° C. and warmed to 25° C. gradually. The mixture was quenched by addition $H_2O$ (50 mL) and then extracted with DCM (30 mL*3). The combined organic layers were washed with brine (50 mL), dried over $Na_2SO_4$, filtered and concentrated under reduced pressure to give a residue. The residue was purified by prep-HPLC (column: Waters Xbridge BEH C18 100*30 mm*10 um; mobile phase: [water (10 mM $NH_4HCO_3$)-ACN]; B %: 30%-60%, 8 min) affording (2R,4R)-1-cyano-N-[2-[(4,4-difluorocyclohexyl)amino]-2-oxo-1-pyridazin-4-yl-ethyl]-4-methoxy-N-[4-(pentafluoro-$\lambda^6$-sulfanyl)phenyl]pyrrolidine-2-carboxamide (5 mg, 7.74 umol, 9.67% yield, 96.7% purity) as a yellow solid. MS (ESI) m/z 625.2 $[M+H]^+$ $^1H$ NMR (400 MHz, DMSO-$d_6$) δ=9.47-9.19 (m, 2H), 8.06-7.79 (m, 3H), 7.62 (dd, J=2.6, 5.4 Hz, 1H), 7.25 (br d, J=8.6 Hz, 2H), 6.81 (br s, 1H), 4.18-3.92 (m, 2H), 3.57-3.48 (m, 1H), 3.47-3.35 (m, 1H), 3.26 (s, 3H), 2.60-2.52 (m, 1H), 2.13-2.03 (m, 1H), 2.00-1.11 (m, 7H), 0.74-0.48 (m, 2H).

Example 158: Synthesis of Compound 407

Step 1

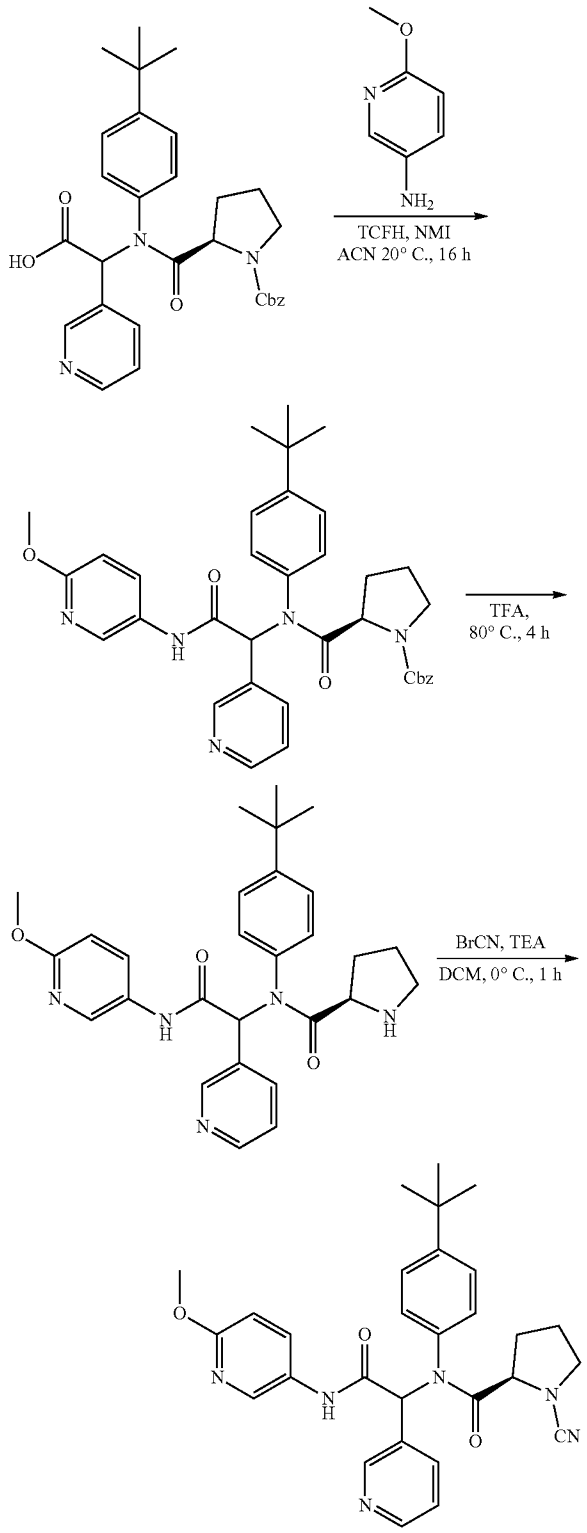

Step 1: (2R)-benzyl 2-((4-(tert-butyl)phenyl)(2-((6-methoxypyridin-3-yl)amino)-2-oxo-1-(pyridin-3-yl)ethyl)carbamoyl)pyrrolidine-1-carboxylate To a mixture of 2-(N-[(2R)-1-benzyloxycarbonylpyrrolidine-2-carbonyl]-4-tert-butyl-anilino)-2-(3-pyridyl)acetic acid (500 mg, 969.75 umol, 1 eq), 6-methoxypyridin-3-amine (240.77 mg, 1.94 mmol, 2 eq) in ACN (10 mL) was added 1-methylimidazole (398.10 mg, 4.85 mmol, 386.50 uL, 5 eq) and [chloro(dimethylamino)methylene]-dimethyl-ammonium;hexafluorophosphate (544.18 mg, 1.94 mmol, 2 eq) in one portion under $N_2$. The mixture was stirred at 20° C. and stirred for 16 h. Upon completion, the residue was concentrated under reduce pressure and give the residue. The residue was purified by prep-HPLC (column: Waters Xbridge Prep OBD C18 150*40 mm*10 um; mobile phase: [water (10 mM $NH_4HCO_3$)-ACN]; B %: 40%-70%, 8 min). Benzyl (2R)-2-[(4-tert-butylphenyl)-[2-[(6-methoxy-3-pyridyl)amino]-2-oxo-1-(3-pyridyl)ethyl]carbamoyl]pyrrolidine-1-carboxylate (100 mg, 160.84 umol, 16.59% yield, 100% purity) was obtained as white solid, Benzyl (2R)-2-[(4-tert-butylphenyl)-[2-[(6-methoxy-3-pyridyl)amino]-2-oxo-1-(3-pyridyl)ethyl]carbamoyl]pyrrolidine-1-carboxylate (100 mg, 160.84 umol, 16.59% yield, 100% purity) was obtained as white solid. MS (ESI) m/z 622.3 $[M+H]^+$.

Step 2: (2R)—N-(4-(tert-butyl)phenyl)-N-(2-((6-methoxypyridin-3-yl)amino)-2-oxo-1-(pyridin-3-yl)ethyl)pyrrolidine-2-carboxamide A mixture of benzyl (2R)-2-[(4-tert-butylphenyl)-[2-[(6-methoxy-3-pyridyl) amino]-2-oxo-1-(3-pyridyl) ethyl]carbamoyl]pyrrolidine-1-carboxylate (100 mg, 160.84 umol, 1 eq) in TFA (5 mL) was stirred at 80° C. for 4 h. Upon completion, the residue was concentrated to remove the TFA, and the pH was adjusted to 7-8 with saturated $NaHCO_3$ and extracted with DCM (10 mL*3). The combined organic phase was washed with brine (30 mL), dried with anhydrous $Na_2SO_4$, filtered and concentrated in vacuum. The crude product was used to next step directly and without further purification. (2R)—N-(4-tert-butylphenyl)-N-[2-[(6-methoxy-3-pyridyl) amino]-2-oxo-1-(3-pyridyl) ethyl]pyrrolidine-2-carboxamide (150 mg, crude) as brown oil. MS (ESI) m/z 488.3 $[M+H]^+$.

Step 3: (2R)—N-(4-(tert-butyl)phenyl)-1-cyano-N-(2-((6-methoxypyridin-3-yl)amino)-2-oxo-1-(pyridin-3-yl)ethyl)pyrrolidine-2-carboxamide (2R)—N-(4-tert-butylphenyl)-N-[2-[(6-methoxy-3-pyridyl)amino]-2-oxo-1-(3-pyridyl)ethyl]pyrrolidine-2-carboxamide (60 mg, 123.05 umol, 1 eq) in EtOH (1 mL) was added with $NaHCO_3$ (31.01 mg, 369.16 umol, 14.36 uL, 3 eq) and the solution was cooled to 0° C. After the addition of BrCN (57 mg, 538.14 umol, 39.58 uL, 4.37 eq), the reaction was stirred at 0° C. for 1 h. Upon completion, the solution was quenched with $H_2O$ (10 mL), extracted with EA (10 mL*3), the combined organic phase was dried over $Na_2SO_4$, filtrated and concentrated to give the crude. The residue was purified by prep-HPLC (neutral condition), column: Waters Xbridge Prep OBD C18 150*40 mm*10 um; mobile phase: [water (10 mM $NH_4HCO_3$)-ACN]; B %: 40%-60%, 8 min. (2R)—N-(4-tert-butylphenyl)-1-cyano-N-[2-[(6-methoxy-3-pyridyl)amino]-2-oxo-1-(3-pyridyl)ethyl]pyrrolidine-2-carboxamide (30 mg, 56.98 umol, 46.31% yield, 97.365% purity) was obtained as light yellow solid, $^1H$ NMR (400 MHz, METHANOL-$d_4$) δ=8.45-8.23 (m, 3H), 7.88 (dd, J=2.8, 8.9 Hz, 1H), 7.83-7.54 (m, 2H), 7.52-7.09 (m, 3H), 6.79 (d, J=8.8 Hz, 2H), 6.30 (s, 1H), 4.17 (dd, J=5.2, 7.8 Hz, 1H), 3.88 (s, 3H), 3.63-3.54 (m, 1H), 3.52-3.39 (m, 1H), 2.17-1.76 (m, 4H), 1.23 (s, 9H), MS (ESI) m/z 513.3 [M+H]$^+$.

(2R)—N-(4-tert-butylphenyl)-1-cyano-N-[2-[(6-methoxy-3-pyridyl) amino]-2-oxo-1-(3-pyridyl) ethyl]pyrrolidine-2-carboxamide (10 mg, 18.80 umol, 18.34% yield, 96.387% purity) was obtained as light yellow solid. $^1$H NMR (400 MHz, METHANOL-$d_4$) δ=8.42 (d, J=1.8 Hz, 1H), 8.36 (dd, J=1.4, 4.8 Hz, 1H), 8.26 (d, J=2.6 Hz, 1H), 7.90 (dd, J=2.7, 8.9 Hz, 1H), 7.83-7.55 (m, 2H), 7.51-7.18 (m, 3H), 6.77 (d, J=8.8 Hz, 2H), 6.16 (s, 1H), 4.19 (dd, J=4.7, 7.8 Hz, 1H), 3.88 (s, 3H), 3.64-3.53 (m, 1H), 3.50-3.39 (m, 1H), 2.07-1.78 (m, 4H), 1.25 (s, 9H).

Example 159: Synthesis of Compound 419

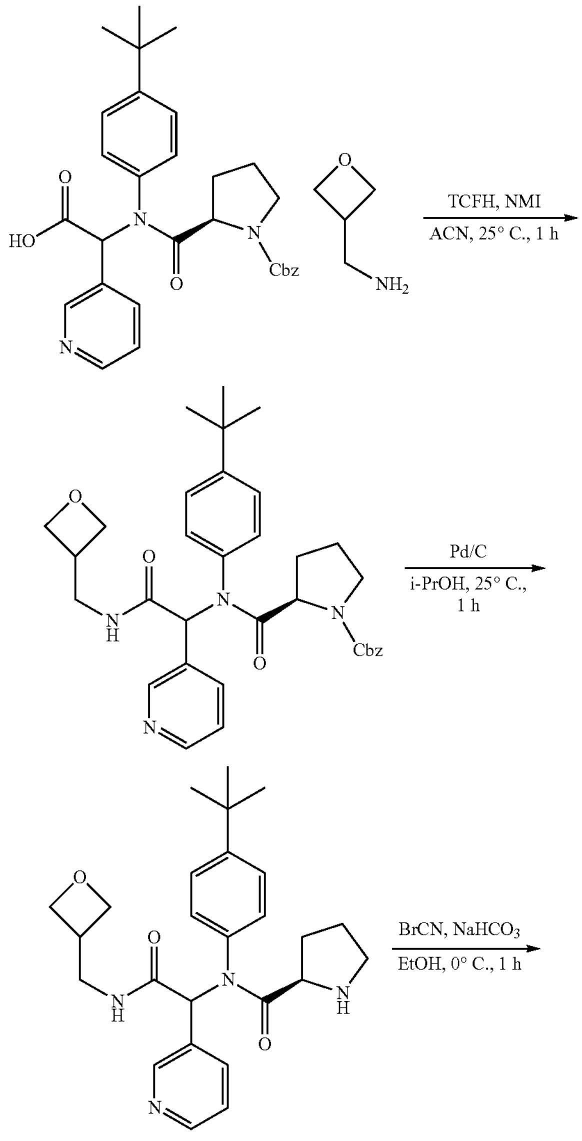

-continued

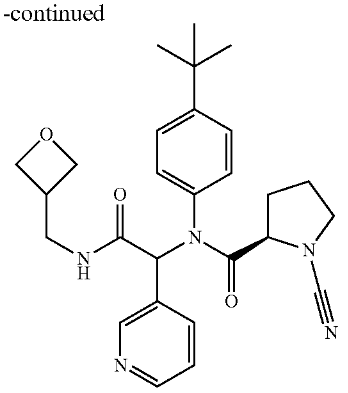

Step 1: benzyl (2R)-2-[(4-tert-butylphenyl)-[2-(oxetan-3-ylmethylamino)-2-oxo-1-(3-pyridyl)ethyl]carbamoyl]pyrrolidine-1-carboxylate To a mixture of 2-(N-[(2R)-1-benzyloxycarbonylpyrrolidine-2-carbonyl]-4-tert-butyl-anilino)-2-(3-pyridyl)acetic acid (200 mg, 387.90 umol, 1 eq) and oxetan-3-ylmethanamine (50.69 mg, 581.85 umol, 1.5 eq) in ACN (3 mL) was added 1-methylimidazole (111.46 mg, 1.36 mmol, 108.22 uL, 3.5 eq) [chloro(dimethylamino)methylene]-dimethyl-ammonium;hexafluorophosphate (217.67 mg, 775.80 umol, 2 eq) in one portion at 25° C. The mixture was stirred at 25° C. for 1 h. The reaction mixture was concentrated under reduced pressure to give the crude product. The crude product was purified by prep-HPLC (basic condition) to give benzyl (2R)-2-[(4-tert-butylphenyl)-[2-(oxetan-3-ylmethylamino)-2-oxo-1-(3-pyridyl)ethyl]carbamoyl]pyrrolidine-1-carboxylate (200 mg) as a white solid and benzyl (2R)-2-[(4-tert-butylphenyl)-[2-(oxetan-3-ylmethylamino)-2-oxo-1-(3-pyridyl)ethyl]carbamoyl]pyrrolidine-1-carboxylate (210 mg) as a white solid. MS (ESI) m/z 585.2 [M+H]$^+$. Column: Phenomenex Gemini-NX C18 75*30 mm*3 um; mobile phase: [water (0.05% $NH_3H_2O$+10 mM $NH_4HCO_3$)-ACN]; B %: 35%-55%, 8 min Step 2: (2R)—N-(4-tert-butylphenyl)-N-[2-(oxetan-3-ylmethylamino)-2-oxo-1-(3-pyridyl)ethyl]pyrrolidine-2-carboxamide Isomer 1: To a mixture of benzyl (2R)-2-[(4-tert-butylphenyl)-[2-(oxetan-3-ylmethylamino)-2-oxo-1-(3-pyridyl)ethyl]carbamoyl]pyrrolidine-1-carboxylate (190 mg, 324.95 umol, 1 eq) in i-PrOH (2 mL) was added Pd/C (190 mg, 10% purity) and stirred at 25° C. for 1 h under $H_2$. The reaction mixture was filtered and concentrated under reduced pressure to give crude (2R)—N-(4-tert-butylphenyl)-N-[2-(oxetan-3-ylmethylamino)-2-oxo-1-(3-pyridyl)ethyl]pyrrolidine-2-carboxamide (140 mg, 310.72 umol, 95.62% yield) as a yellow oil. MS (ESI) m/z 451.3 [M+H]$^+$ Isomer 2: A mixture of benzyl (2R)-2-[(4-tert-butylphenyl)-[2-(oxetan-3-ylmethylamino)-2-oxo-1-(3-pyridyl)ethyl]carbamoyl]pyrrolidine-1-carboxylate (210 mg, 359.16 umol, 1 eq) in i-PrOH (4 mL) was added Pd/C (210 mg, 10% purity) in one portion at 25° C. under $H_2$. The mixture was stirred at 25° C. for 1 h under $H_2$. The reaction mixture was filtered and concentrated under reduced pressure to give the crude (2R)—N-(4-tert-butylphenyl)-N-[2-(oxetan-3-ylmethylamino)-2-oxo-1-(3-pyridyl)ethyl]pyrrolidine-2-carboxamide (140 mg, 310.72 umol, 86.51% yield) as a yellow oil. MS (ESI) m/z 451.3 $[M+H]^+$

Step 3: (2R)—N-(4-tert-butylphenyl)-1-cyano-N-[2-(oxetan-3-ylmethylamino)-2-oxo-1-(3-pyridyl)ethyl] pyrrolidine-2-carboxamide Isomer 1: To a mixture of (2R)—N-(4-tert-butylphenyl)-N-[2-(oxetan-3-ylmethylamino)-2-oxo-1-(3-pyridyl)ethyl] pyrrolidine-2-carboxamide (120 mg, 266.33 umol, 1 eq) and $NaHCO_3$ (67.12 mg, 798.98 umol, 31.07 uL, 3 eq) in EtOH (2 mL) was added BrCN (56.42 mg, 532.66 umol, 39.18 uL, 2 eq) at 0° C. The mixture was stirred at 0° C. for 1 h. The reaction mixture was quenched by addition $H_2O$ 10 mL at 25° C., and concentrated under reduced pressure to give the crude product. The crude product was purified by prep-HPLC (neutral condition) to give (2R)—N-(4-tert-butylphenyl)-1-cyano-N-[2-(oxetan-3-ylmethylamino)-2-oxo-1-(3-pyridyl)ethyl]pyrrolidine-2-carboxamide (33 mg, 69.39 umol, 26.05% yield) as a yellow solid. MS (ESI) m/z 476.3 $[M+H]^+$ Column: Waters Xbridge BEH C18 100*30 mm*10 um; mobile phase: [water (10 mM $NH_4HCO_3$)-ACN]; B %: 25%-55%, 10 min $^1H$ NMR (400 MHz, METHANOL-$d_4$) δ=8.40-8.22 (m, 2H), 7.77-7.12 (m, 5H), 6.67 (br s, 1H), 6.21-5.87 (m, 1H), 4.72 (ddd, J=1.8, 6.2, 7.8 Hz, 2H), 4.46-4.34 (m, 2H), 4.20-4.09 (m, 1H), 3.65-3.39 (m, 4H), 3.24-3.07 (m, 1H), 2.15-1.78 (m, 4H), 1.27-1.20 (m, 9H)

Isomer 2: To a mixture of (2R)—N-(4-tert-butylphenyl)-N-[2-(oxetan-3-ylmethylamino)-2-oxo-1-(3-pyridyl)ethyl] pyrrolidine-2-carboxamide (130 mg, 288.52 umol, 1 eq) and $NaHCO_3$ (72.71 mg, 865.57 umol, 33.66 uL, 3 eq) in EtOH (2 mL) was added BrCN (61.12 mg, 577.04 umol, 42.45 uL, 2 eq) at 0° C. The mixture was stirred at 0° C. for 1 h. The reaction mixture was quenched by addition $H_2O$ 10 mL at 25° C., and concentrated under reduced pressure to give the crude product. The crude product was purified by prep-HPLC (neutral condition) to give (2R)—N-(4-tert-butylphenyl)-1-cyano-N-[2-(oxetan-3-ylmethylamino)-2-oxo-1-(3-pyridyl)ethyl]pyrrolidine-2-carboxamide (31.5 mg, 66.23 umol, 22.96% yield) as a yellow solid. MS (ESI) m/z 476.3 $[M+H]^+$ $^1H$ NMR (400 MHz, METHANOL-$d_4$) δ=8.43-8.25 (m, 2H), 7.75-7.11 (m, 5H), 7.08-6.43 (m, 1H), 6.20-5.87 (m, 1H), 4.73 (ddd, J=2.6, 6.3, 7.8 Hz, 2H), 4.48-4.35 (m, 2H), 4.22-4.09 (m, 1H), 3.63-3.39 (m, 4H), 3.26-3.11 (m, 1H), 2.14-1.77 (m, 4H), 1.27-1.21 (m, 9H)

Example 160: Synthesis of Compound 439

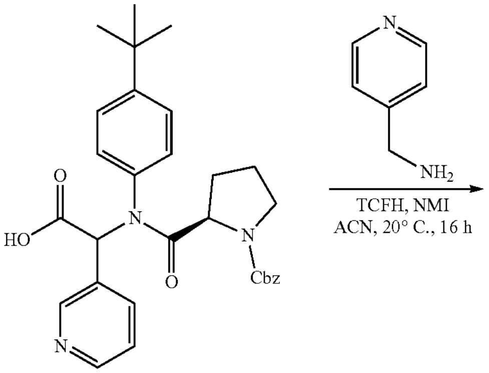

-continued

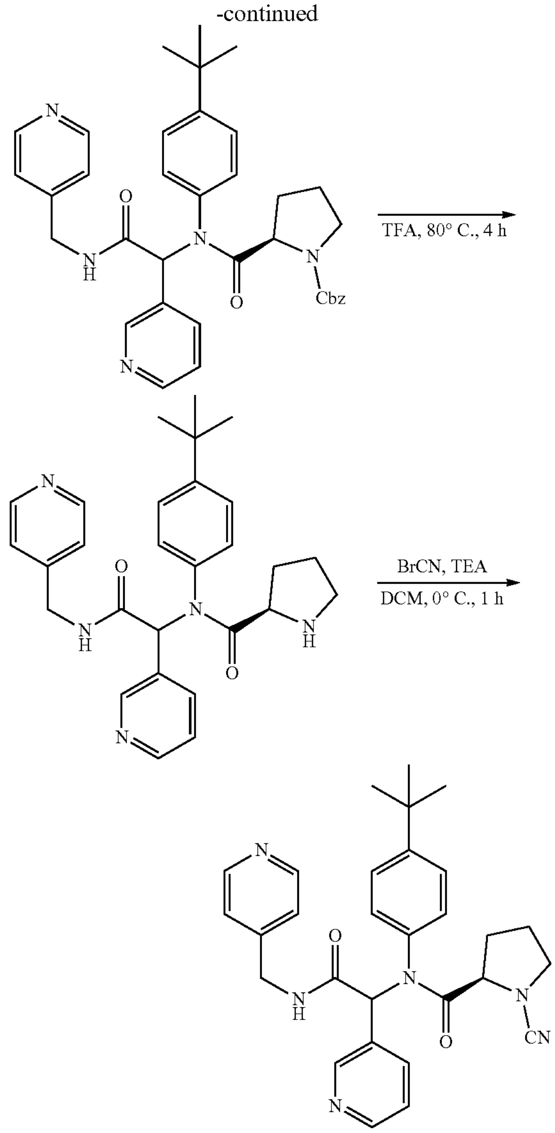

Step 1: (2R)-benzyl 2-((4-(tert-butyl)phenyl)(2-oxo-1-(pyridin-3-yl)-2-((pyridin-4-ylmethyl)amino)ethyl) carbamoyl)pyrrolidine-1-carboxylate To a mixture of 2-(N-[(2R)-1-benzyloxycarbonylpyrrolidine-2-carbonyl]-4-tert-butyl-anilino)-2-(3-pyridyl)acetic acid (500 mg, 969.75 umol, 1 eq) and 4-pyridylmethanamine (209.74 mg, 1.94 mmol, 196.02 uL, 2 eq) in ACN (10 mL) was added 1-methylimidazole (398.08 mg, 4.85 mmol, 386.49 uL, 5 eq) and [chloro(dimethylamino)methylene]-dimethyl-ammonium;hexafluorophosphate (544.18 mg, 1.94 mmol, 2 eq), and the reaction was stirred at 20° C. for 16 h. Upon completion, the residue was concentrated in vacuum. The residue was purified by prep-HPLC (column: Waters Xbridge Prep OBD C18 150*40 mm*10 um; mobile phase: [water (10 mM $NH_4HCO_3$)-ACN]; B %: 45%-65%, 8 min). Benzyl (2R)-2-[(4-tert-butylphenyl)-[2-oxo-1-(3-pyridyl)-2-(4-pyridylmethylamino)ethyl]carbamoyl]pyrrolidine-1-carboxylate (100 mg, 165.09 umol, 17.02% yield, N/A purity) was obtained as white solid and benzyl (2R)-2-[(4-tert-butylphenyl)-[2-oxo-1-(3-pyridyl)-2-(4-pyridylmethylamino)ethyl]carbamoyl]pyrrolidine-1-carboxylate (100 mg, 165.09 umol, 17.02% yield, N/A purity) was obtained as white solid. MS (ESI) m/z 606.3 [M+H]$^+$.

Step 2: (2R)—N-(4-(tert-butyl)phenyl)-N-(2-oxo-1-(pyridin-3-yl)-2-((pyridin-4-ylmethyl)amino)ethyl) pyrrolidine-2-carboxamide A mixture of benzyl (2R)-2-[(4-tert-butylphenyl)-[2-oxo-1-(3-pyridyl)-2-(4-pyridylmethylamino) ethyl]carbamoyl] pyrrolidine-1-carboxylate (100 mg, 165.09 umol, 1 eq) in TFA (4 mL) was stirred at 80° C. for 5 h. Upon completion, the residue was poured into $NaHCO_3$ (20 mL) and extracted with DCM (20 mL*3). The combined organic phase was washed with brine (30 mL), dried with anhydrous $Na_2SO_4$, filtered and concentrated in vacuum. The residue was used to next step directly and without further purification. (2R)—N-(4-tert-butylphenyl)-N-[2-oxo-1-(3-pyridyl)-2-(4-pyridylmethylamino) ethyl]pyrrolidine-2-carboxamide (60 mg, crude) was obtained as brown oil. MS (ESI) m/z 472.3 [M+H]$^+$.

Step 3: (2R)—N-(4-(tert-butyl)phenyl)-1-cyano-N-(2-oxo-1-(569yridine-3-yl)-2-((569yridine-4-ylmethyl)amino)ethyl)pyrrolidine-2-carboxamide To a solution of (2R)—N-(4-tert-butylphenyl)-N-[2-oxo-1-(3-pyridyl)-2-(4-pyridylmethylamino)ethyl]pyrrolidine-2-carboxamide (50 mg, 106.02 umol, 1 eq) in EtOH (0.5 mL) was added the $NaHCO_3$ (26.72 mg, 318.07 umol, 12.37 uL, 3 eq) and the solution was cooled to 0° C. BrCN (11.23 mg, 106.02 umol, 7.80 uL, 1 eq) was added and the solution was stirred at 0° C. for 1 h. Upon completion, the solution was quenched with $H_2O$ (10 mL), extracted with EA (10 mL*3), the combined organic phase was dried over $Na_2SO_4$, filtrated and concentrated to give the crude. The residue was purified by prep-HPLC (neutral condition), column: Phenomenex Gemini-NX 80*40 mm*3 um; mobile phase: [water (10 mM NH4HCO3)-ACN]; B %: 20%-50%, 8 min (2R)—N-(4-tert-butylphenyl)-1-cyano-N-[2-oxo-1-(3-pyridyl)-2-(4-pyridylmethylamino)ethyl]pyrrolidine-2-carboxamide (5 mg, 9.69 umol, 9.14% yield, 96.218% purity) was obtained as light yellow solid. $^1$H NMR (400 MHz, METHANOL-$d_4$) δ=8.49-8.40 (m, 2H), 8.39-8.25 (m, 2H), 7.71-7.14 (m, 7H), 6.96-6.50 (m, 1H), 6.29-5.94 (m, 1H), 4.61-4.57 (m, 1H), 4.45-4.33 (m, 1H), 4.22-4.11 (m, 1H), 3.66-3.55 (m, 1H), 3.52-3.41 (m, 1H), 2.13-1.76 (m, 4H), 1.27-1.20 (m, 9H). MS (ESI) m/z 497.3 [M+H]$^+$.

(2R)—N-(4-tert-butylphenyl)-1-cyano-N-[2-oxo-1-(3-pyridyl)-2-(4-pyridylmethylamino) ethyl]pyrrolidine-2-carboxamide (5 mg, 9.40 umol, 8.87% yield, 93.364% purity) was obtained as light yellow solid. $^1$H NMR (400 MHz, METHANOL-$d_4$) δ=8.52-8.29 (m, 4H), 7.77-6.53 (m, 8H), 6.26-6.01 (m, 1H), 4.56 (br d, J=6.4 Hz, 1H), 4.43-4.33 (m, 1H), 4.22-4.10 (m, 1H), 3.66-3.55 (m, 1H), 3.50-3.41 (m, 1H), 2.13-1.75 (m, 4H), 1.24 (d, J=11.5 Hz, 9H)

Example 161: Synthesis of Compound 459

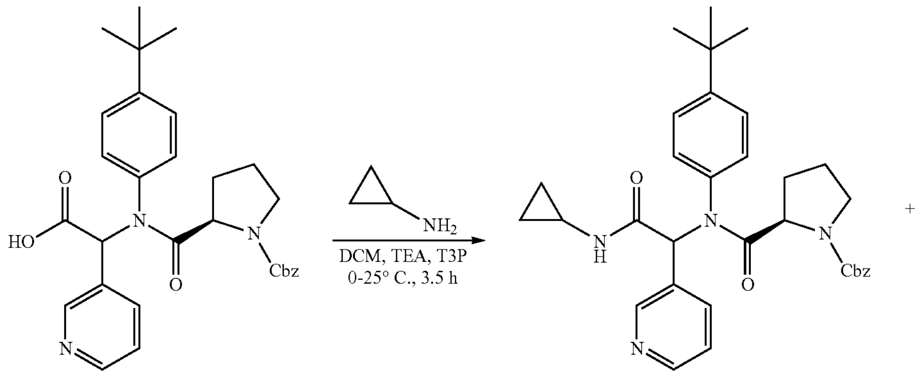

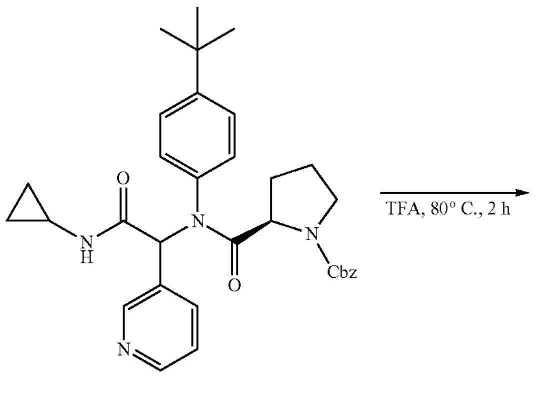

-continued

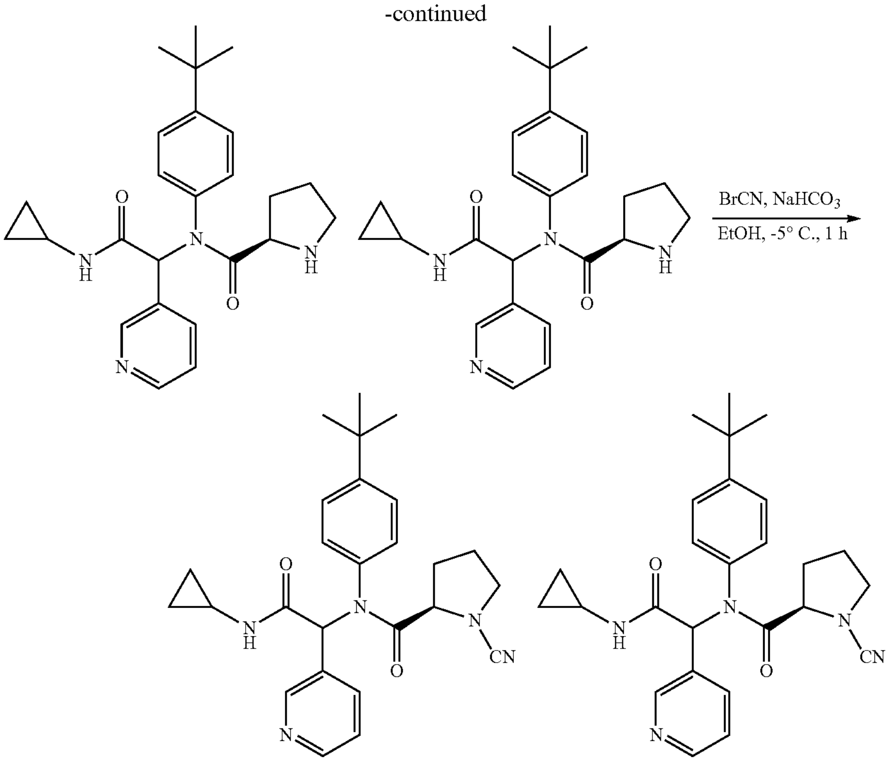

Step 1: benzyl (2R)-2-[(4-tert-butylphenyl)-[2-(cyclopropylamino)-2-oxo-1-(3-pyridyl)ethyl]carbamoyl]pyrrolidine-1-carboxylate A mixture of 2-(N-[(2R)-1-benzyloxycarbonylpyrrolidine-2-carbonyl]-4-tert-butyl-anilino)-2-(3-pyridyl)acetic acid (400 mg, 775.80 umol, 1 eq) in DCM (4 mL) was added with cyclopropanamine (354.35 mg, 6.21 mmol, 430.03 uL, 8 eq), TEA (471.02 mg, 4.65 mmol, 647.89 uL, 6 eq) and T3P (740.53 mg, 1.16 mmol, 692.08 uL, 50% purity, 1.5 eq) at 0° C. for 0.5 h. The mixture was stirred at 25° C. for 3 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-70%, 8 min) to get a product benzyl (2R)-2-[(4-tert-butylphenyl)-[2-(cyclopropylamino)-2-oxo-1-(3-pyridyl)ethyl]carbamoyl]pyrrolidine-1-carboxylate Isomer 1 (175 mg, 315.50 umol, 40.67% yield) as white solid. MS (ESI) m/z 555.2 $[M+H]^+$.

To get benzyl benzyl (2R)-2-[(4-tert-butylphenyl)-[2-(cyclopropylamino)-2-oxo-1-(3-pyridyl)ethyl]carbamoyl]pyrrolidine-1-carboxylate Isomer 2 (70 mg, 126.20 umol, 16.27% yield) as white solid. MS (ESI) m/z 555.2 $[M+H]^+$.

Step 2: (2R)—N-(4-tert-butylphenyl)-N-[2-(cyclopropylamino)-2-oxo-1-(3-pyridyl)ethyl]pyrrolidine-2-carboxamide Isomer 1

A mixture of benzyl (2R)-2-[(4-tert-butylphenyl)-[2-(cyclopropylamino)-2-oxo-1-(3-pyridyl)ethyl]carbamoyl]pyrrolidine-1-carboxylate Isomer 1 (180 mg, 324.51 umol, 1 eq) in TFA (3 mL) was stirred at 80° C. for 2 h. Upon completion, the reaction mixture was base-modulated in saturated $K_2CO_3$ (10 mL) solution, and extracted with EA (10 mL*3). The combined organic layers were washed with brine, dried over $Na_2SO_4$, filtered and concentrated under reduced pressure to give a residue to get the product (2R)—N-(4-tert-butylphenyl)-N-[2-(cyclopropylamino)-2-oxo-1-(3-pyridyl)ethyl]pyrrolidine-2-carboxamide Isomer 1 (150 mg, crude) as yellow oil. MS (ESI) m/z 421.2 $[M+H]^+$.

(2R)—N-(4-tert-butylphenyl)-N-[2-(cyclopropylamino)-2-oxo-1-(3-pyridyl)ethyl]pyrrolidine-2-carboxamide Isomer 2

A mixture of benzyl (2R)-2-[(4-tert-butylphenyl)-[2-(cyclopropylamino)-2-oxo-1-(3-pyridyl)ethyl]carbamoyl]pyrrolidine-1-carboxylate Isomer 2 (90 mg, 162.26 umol, 1 eq) in TFA (2 mL, the mixture was stirred at 80° C. for 2 h. Upon completion, the reaction mixture was base-modulated in saturated $K_2CO_3$ (10 mL) solution, and extracted with EA (10 mL*3). The combined organic layers were washed with brine, dried over $Na_2SO_4$, filtered and concentrated under reduced pressure to give a residue to get a product (2R)—N-(4-tert-butylphenyl)-N-[2-(cyclopropylamino)-2-oxo-1-(3-pyridyl)ethyl]pyrrolidine-2-carboxamide Isomer 2 (80 mg, crude) as yellow oil. MS (ESI) m/z 421.2 $[M+H]^+$.

Step 3: (2R)—N-(4-tert-butylphenyl)-1-cyano-N-[2-(cyclopropylamino)-2-oxo-1-(3-pyridyl)ethyl]pyrrolidine-2-carboxamide Isomer 1

A mixture of (2R)—N-(4-tert-butylphenyl)-N-[2-(cyclopropylamino)-2-oxo-1-(3-pyridyl)ethyl]pyrrolidine-2-carboxamide Isomer 1 (0.14 g, 332.90 umol, 1 eq) in EtOH (2 mL) was added $NaHCO_3$ (83.90 mg, 998.70 umol, 38.84 uL, 3 eq), and the solution was cooled to −5° C. After the addition of BrCN (38.79 mg, 366.19 umol, 26.94 uL, 1.1 eq) in EtOH (0.5 mL) drop-wise. The solution was stirred at −5° C. for 1 h under $N_2$. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-55%, 10 min) to get the product ((2R)—N-(4-tert-butylphenyl)-1-cyano-N-[2-(cyclopropylamino)-2-oxo-1-(3-pyridyl)ethyl]pyrrolidine-2-carboxamide Isomer 1 (51.32 mg, 114.49 umol, 34.39% yield, 99.4% purity) as yellow solid. MS (ESI) m/z 446.2 $[M+H]^+$.

$^1H$ NMR (400 MHz, METHANOL-$d_4$) δ=8.36-8.23 (m, 2H), 7.85-7.55 (m, 1H), 7.50 (td, J=1.8, 8.0 Hz, 1H), 7.39 (br s, 1H), 7.17 (dd, J=4.9, 7.9 Hz, 2H), 6.81-6.47 (m, 1H), 6.09 (s, 1H), 4.13 (dd, J=5.1, 7.9 Hz, 1H), 3.64-3.54 (m, 1H), 3.45 (dt, J=5.5, 7.9 Hz, 1H), 2.71 (td, J=3.5, 7.3 Hz, 1H), 2.16-1.75 (m, 4H), 1.27-1.19 (m, 9H), 0.78-0.67 (m, 2H), 0.53-0.45 (m, 1H), 0.42-0.36 (m, 1H).

(2R)—N-(4-tert-butylphenyl)-1-cyano-N-[2-(cyclopropylamino)-2-oxo-1-(3-pyridyl)ethyl]pyrrolidine-2-carboxamide Isomer 2

A mixture of (2R)—N-(4-tert-butylphenyl)-N-[2-(cyclopropylamino)-2-oxo-1-(3-pyridyl)ethyl]pyrrolidine-2-carboxamide Isomer 2 (0.08 g, 190.23 umol, 1 eq) in EtOH (2 mL) was added $NaHCO_3$ (47.94 mg, 570.69 umol, 22.20 uL, 3 eq), and the solution was cooled to −5° C. and BrCN (22.16 mg, 209.25 umol, 15.39 uL, 1.1 eq) in EtOH (0.5 mL) was added drop-wise. The solution was stirred at −5° C. for 1 h under $N_2$. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-55%, 10 min) to provide (2R)—N-(4-tert-butylphenyl)-1-cyano-N-[2-(cyclopropylamino)-2-oxo-1-(3-pyridyl)ethyl]pyrrolidine-2-carboxamide Isomer 2 (20.92 mg, 46.58 umol, 24.48% yield, 99.2% purity) as yellow solid. MS (ESI) m/z 446.2 $[M+H]^+$.

$^1H$ NMR (400 MHz, METHANOL-$d_4$) δ=8.44-8.17 (m, 2H), 7.89-6.37 (m, 6H), 6.25-5.67 (m, 1H), 4.13 (s, 1H), 3.56 (s, 1H), 3.49-3.39 (m, 1H), 2.67 (s, 1H), 2.22-1.75 (m, 4H), 1.27-1.17 (m, 9H), 0.76-0.65 (m, 2H), 0.53-0.44 (m, 1H), 0.43-0.35 (m, 1H).

Example 162: Synthesis of Compound 950

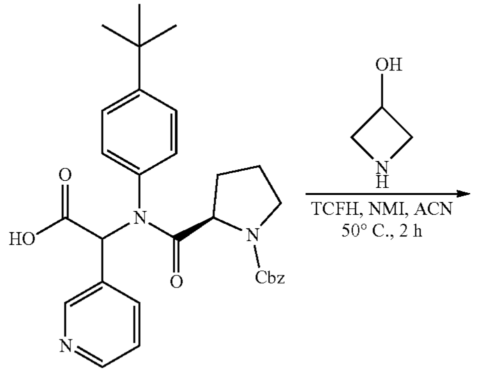

-continued

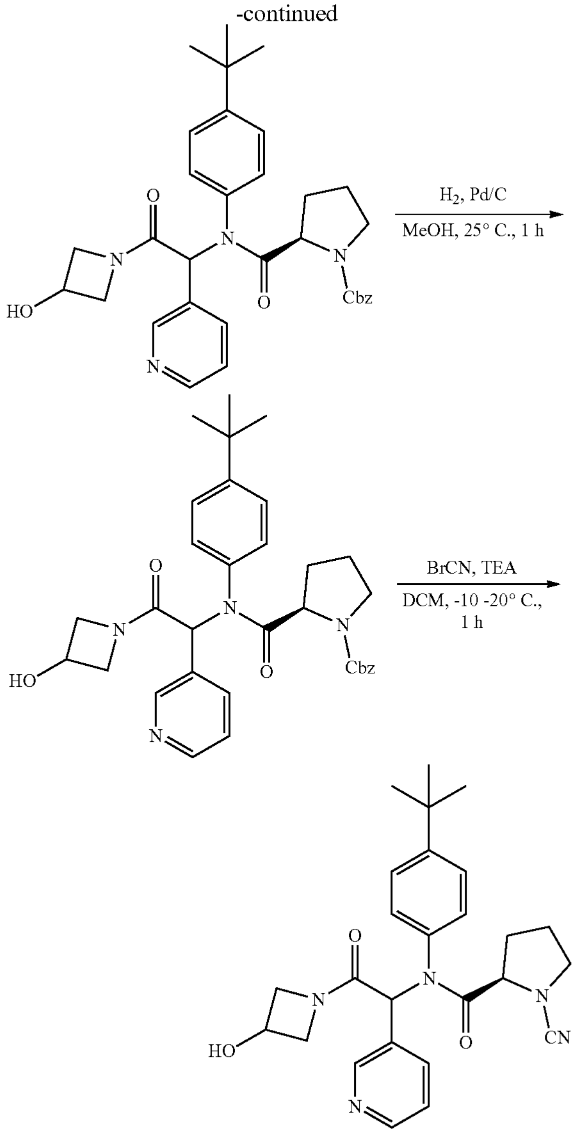

Step 1: (2R)-benzyl 2-((4-(tert-butyl)phenyl)(2-(3-hydroxyazetidin-1-yl)-2-oxo-1-(pyridin-3-yl)ethyl)carbamoyl)pyrrolidine-1-carboxylate A mixture of 2-(N-[(2R)-1-benzyloxycarbonylpyrrolidine-2-carbonyl]-4-tert-butyl-anilino)-2-(3-pyridyl)acetic acid (250 mg, 484.87 umol, 1 eq), azetidin-3-ol (70.88 mg, 969.75 umol, 61.14 uL, 2 eq), 1-methylimidazole (139.33 mg, 1.70 mmol, 135.27 uL, 3.5 eq), and [chloro(dimethylamino)methylene]-dimethyl-ammonium;hexafluorophosphate (244.88 mg, 872.77 umol, 1.8 eq) in ACN (5 mL) was degassed and purged with $N_2$ for 3 times, and then the mixture was stirred at 25° C. for 1 h under $N_2$ atmosphere. The reaction mixture was quenched by addition $H_2O$ 8 mL, and then extracted with ethyl acetate (4 mL*3). The combined organic layers were washed with brine 5 mL, dried over $Na_2SO_4$, filtered and concentrated under reduced pressure to afford benzyl (2R)-2-[(4-tert-butylphenyl)-[2-(3-hydroxyazetidin-1-yl)-2-oxo-1-(3-pyridyl)ethyl]carbamoyl]pyrrolidine-1-carboxylate (300 mg, crude) was obtained as yellow oil. MS (ESI) m/z 571.3 $[M+H]^+$.

Step 2: (2R)—N-(4-(tert-butyl)phenyl)-N-(2-(3-hydroxyazetidin-1-yl)-2-oxo-1-(pyridin-3-yl)ethyl) pyrrolidine-2-carboxamide To a solution of benzyl (2R)-2-[(4-tert-butylphenyl)-[2-(3-hydroxyazetidin-1-yl)-2-oxo-1-(3-pyridyl)ethyl]carbamoyl]pyrrolidine-1-carboxylate (200 mg, 350.46 umol, 1 eq) in MeOH (15 mL) was added Pd/C (10%, 0.02 g) under $N_2$ atmosphere. The suspension was degassed and purged with H2 for 3 times. The mixture was stirred under $H_2$ (15 Psi.) at 25° C. for 1 h. LCMS showed the reaction was complected, and desired MS was observed. The reaction mixture was filtered and concentrated under reduced pressure to give a residue to afford (2R)—N-(4-tert-butylphenyl)-N-[2-(3-hydroxyazetidin-1-yl)-2-oxo-1-(3-pyridyl)ethyl]pyrrolidine-2-carboxamide (200 mg, crude) was obtained as yellow oil. MS (ESI) m/z 451.3 $[M+H]^+$.

Step 3: (2R)—N-(4-(tert-butyl)phenyl)-1-cyano-N-(2-(3-hydroxyazetidin-1-yl)-2-oxo-1-(pyridin-3-yl) ethyl)pyrrolidine-2-carboxamide To a solution of (2R)—N-(4-tert-butylphenyl)-N-[2-(3-hydroxyazetidin-1-yl)-2-oxo-1-(3-pyridyl)ethyl]pyrrolidine-2-carboxamide (180 mg, 412.33 umol, 1 eq) in DMF (4 mL) was added $K_2CO_3$ (56.99 mg, 412.33 umol, 1 eq), followed by the addition of BrCN (131.02 mg, 1.24 mmol, 90.99 uL, 3 eq) at 0° C. The mixture was stirred at 20° C. for 1 h. The reaction mixture was concentrated under reduced pressure to remove solvent. The residue was purified by neutral prep-HPLC to get the product (2R)—N-(4-tert-butylphenyl)-1-cyano-N-[2-(3-hydroxyazetidin-1-yl)-2-oxo-1-(3-pyridyl)ethyl]pyrrolidine-2-carboxamide (2.55 mg, 5.52 umol, 1.34% yield, 100% purity) was obtained as white solid. MS (ESI) m/z 462.3$[M+H]^+$.

Prep-HPLC condition: column: Waters Xbridge Prep OBD C18 150*40 mm*10 um; mobile phase: [water (10 mM NH4HCO3)-ACN]; B %: 20%-50%, 8 min $^1$H NMR (400 MHz, METHANOL-$d_4$) δ ppm 8.34 (br d, J=14.90 Hz, 2H) 7.00-7.87 (m, 5H) 6.37-6.96 (m, 1H) 6.03-6.29 (m, 1H) 4.62-4.69 (m, 1H) 4.31-4.51 (m, 1H) 4.03-4.29 (m, 2H) 3.69-3.99 (m, 1H) 3.40-3.67 (m, 3H) 1.73-2.16 (m, 4H) 1.23 (d, J=9.89 Hz, 9H).

Example 163: Synthesis of Compound 955

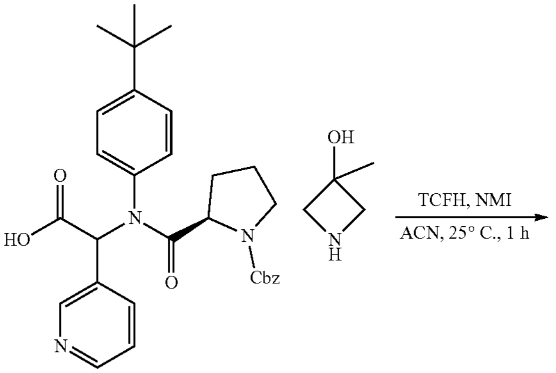

-continued

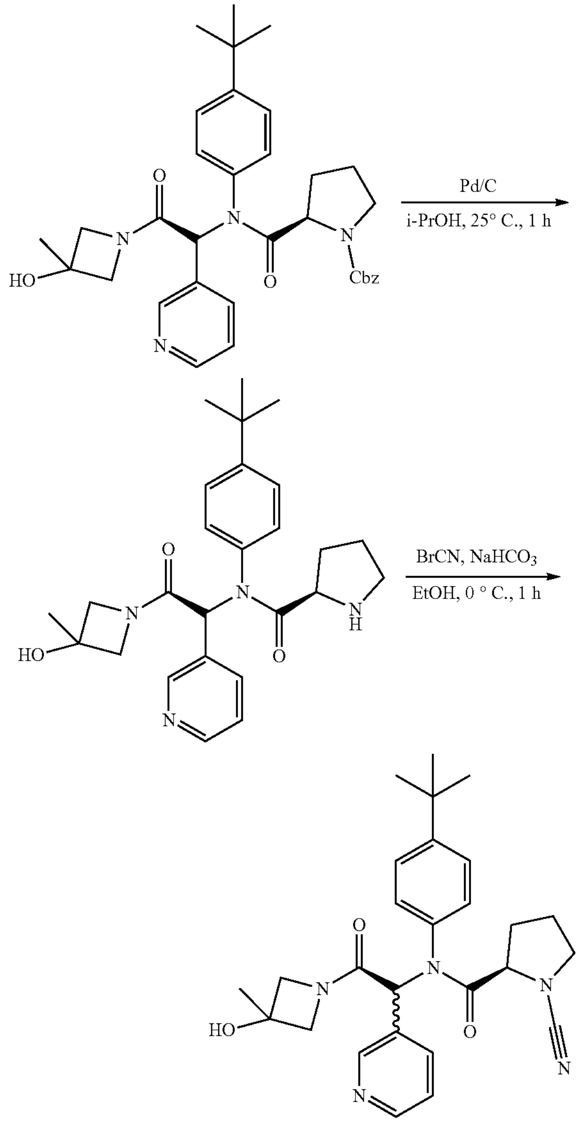

To a mixture of 2-(N-[(2R)-1-benzyloxycarbonylpyrrolidine-2-carbonyl]-4-tert-butyl-anilino)-2-(3-pyridyl)acetic acid (250 mg, 484.87 umol, 1 eq+100 mg, 193.95 umol, 1 eq) and 3-mnethylazetidin-3-ol (63.36 mg, 727.31 umol, 1.5 eq+33.79 mg, 387.89 umol, 2.00 eq) in ACN (3 mL+1 mL) was added 1-methylimidazole (139.33 mg, 1.70 mmol, 135.27 uL, 3.5 eq+63.69 mg, 775.80 umol, 61.84 uL, 4 eq) and [chloro(dimethylamino)methylene]-dimethyl-ammonium;hexafluorophosphate (272.09 mg, 969.75 umol, 2 eq+163.25 mg, 581.85 umol, 3 eq) in one portion at 25° C. The mixture was stirred at 25° C. for 1 h. The reaction mixture was concentrated under reduced pressure to give a residue. The crude product was purified by prep-HPLC (basic condition) to give benzyl (2R)-2-[(4-tert-butylphenyl)-[2-(3-hydroxy-3-methyl-azetidin-1-yl)-2-oxo-1-(3-pyridyl)ethyl]carbamoyl]pyrrolidine-1-carboxylate (170 mg) as a white solid and benzyl (2R)-2-[(4-tert-butylphenyl)-[2-(3-hydroxy-3-methyl-azetidin-1-yl)-2-oxo-1-(3-pyridyl)ethyl]carbamoyl]pyrrolidine-1-carboxylate (160 mg) as a white solid. MS (ESI) m/z 585.2 $[M+H]^+$ column: Phenomenex Gemini-NX C18 75*30 mm*3 um; mobile phase: [water (0.05% $NH_3H_2O$+10 mM $NH_4HCO_3$)-ACN]; B %: 40%-60%, 8 min

Step 2: (2R)—N-(4-tert-butylphenyl)-N-[2-(3-hydroxy-3-methyl-azetidin-1-yl)-2-oxo-1-(3-pyridyl)ethyl]pyrrolidine-2-carboxamide Isomer 1: To a mixture of benzyl (2R)-2-[(4-tert-butylphenyl)-[2-(3-hydroxy-3-methyl-azetidin-1-yl)-2-oxo-1-(3-pyridyl)ethyl]carbamoyl]pyrrolidine-1-carboxylate (170 mg, 290.75 umol, 1 eq) in i-PrOH (3 mL) was added Pd/C (170 mg, 10% purity, 1.00 eq) and stirred at 25° C. for 1 h under $H_2$. The reaction mixture was filtered and concentrated under reduced pressure to give crude (2R)—N-(4-tert-butylphenyl)-N-[2-(3-hydroxy-3-methyl-azetidin-1-yl)-2-oxo-1-(3-pyridyl)ethyl]pyrrolidine-2-carboxamide (75 mg, 166.46 umol, 57.25% yield) as a yellow oil. MS (ESI) m/z 451.2 $[M+H]^+$ Isomer 2: To a mixture of benzyl (2R)-2-[(4-tert-butylphenyl)-[2-(3-hydroxy-3-methyl-azetidin-1-yl)-2-oxo-1-(3-pyridyl)ethyl]carbamoyl]pyrrolidine-1-carboxylate (160 mg, 273.64 umol, 1 eq) in i-PrOH (3 mL) was added Pd/C (160 mg, 10% purity) and stirred at 25° C. for 1 h under $H_2$. The reaction mixture was filtered and concentrated under reduced pressure to give crude (2R)—N-(4-tert-butylphenyl)-N-[2-(3-hydroxy-3-methyl-azetidin-1-yl)-2-oxo-1-(3-pyridyl)ethyl]pyrrolidine-2-carboxamide (100 mg, 221.94 umol, 81.11% yield) as a yellow oil. MS (ESI) m/z 451.2 $[M+H]^+$

Step 3: (2R)—N-(4-tert-butylphenyl)-1-cyano-N-[2-(3-hydroxy-3-methyl-azetidin-1-yl)-2-oxo-1-(3-pyridyl)ethyl]pyrrolidine-2-carboxamide Isomer 1: To a mixture of (2R)—N-(4-tert-butylphenyl)-N-[2-(3-hydroxy-3-methyl-azetidin-1-yl)-2-oxo-1-(3-pyridyl)ethyl]pyrrolidine-2-carboxamide (70 mg, 155.36 umol, 1 eq) and $NaHCO_3$ (39.15 mg, 466.07 umol, 18.13 uL, 3 eq) in EtOH (2 mL) was added BrCN (32.91 mg, 310.72 umol, 22.86 uL, 2 eq) at 0° C. The mixture was stirred at 0° C. for 1 h. The reaction mixture was quenched by addition $H_2O$ 10 mL at 25° C., and concentrated under reduced pressure to give a residue. The crude product was purified by prep-HPLC (neutral condition) to give (2R)—N-(4-tert-butylphenyl)-1-cyano-N-[2-(3-hydroxy-3-methyl-azetidin-1-yl)-2-oxo-1-(3-pyridyl)ethyl]pyrrolidine-2-carboxamide (11.6 mg, 24.39 umol, 15.70% yield) as a yellow solid. MS (ESI) m/z 476.3 $[M+H]^+$ column: Waters Xbridge BEH C18 100*30 mm*10 um; mobile phase: [water (10 mM $NH_4HCO_3$)-ACN]; B %: 25%-55%, 10 min $^1H$ NMR (400 MHz, METHANOL-$d_4$) δ=8.33 (br s, 2H), 8.07-6.98 (m, 5H), 6.93-6.35 (m, 1H), 6.28-6.05 (m, 1H), 4.33 (br t, J=8.5 Hz, 1H), 4.20-3.94 (m, 2H), 3.93-3.74 (m, 1H), 3.72-3.39 (m, 3H), 2.19-1.73 (m, 4H), 1.61-1.05 (m, 12H)

Isomer 2: To a mixture of (2R)—N-(4-tert-butylphenyl)-N-[2-(3-hydroxy-3-methyl-azetidin-1-yl)-2-oxo-1-(3-pyridyl)ethyl]pyrrolidine-2-carboxamide (70 mg, 155.36 umol, 1 eq) and $NaHCO_3$ (39.15 mg, 466.07 umol, 18.13 uL, 3 eq) in EtOH (2 mL) was added BrCN (49.37 mg, 466.07 umol, 34.28 uL, 3 eq) at 0° C. The mixture was stirred at 0° C. for 2 h. The reaction mixture was quenched by addition $H_2O$ 10 mL at 0° C., and then filtered and concentrated under reduced pressure to give a residue. The crude product was purified by prep-HPLC (neutral condition) to give (2R)—N-(4-tert-butylphenyl)-1-cyano-N-[2-(3-hydroxy-3-methyl-azetidin-1-yl)-2-oxo-1-(3-pyridyl)ethyl]pyrrolidine-2-carboxamide (17.2 mg, 36.17 umol, 23.28% yield) as a yellow solid. MS (ESI) m/z 476.3 $[M+H]^+$ column: Waters Xbridge BEH C18 100*30 mm*10 um; mobile phase: [water (10 mM $NH_4HCO_3$)-ACN]; B %: 25%-55%, 10 min $^1H$ NMR (400 MHz, METHANOL-$d_4$) δ=8.79-8.09 (m, 2H), 8.04-6.99 (m, 5H), 6.95-6.34 (m, 1H), 6.29-6.05 (m, 1H), 4.60 (s, 1H), 4.39-4.27 (m, 1H), 4.14 (br dd, J=4.6, 7.5 Hz, 1H), 4.08-3.95 (m, 1H), 3.91-3.51 (m, 3H), 3.50-3.38 (m, 1H), 2.25-1.74 (m, 4H), 1.62-1.01 (m, 12H)

Example 164: Synthesis of Compound 1119

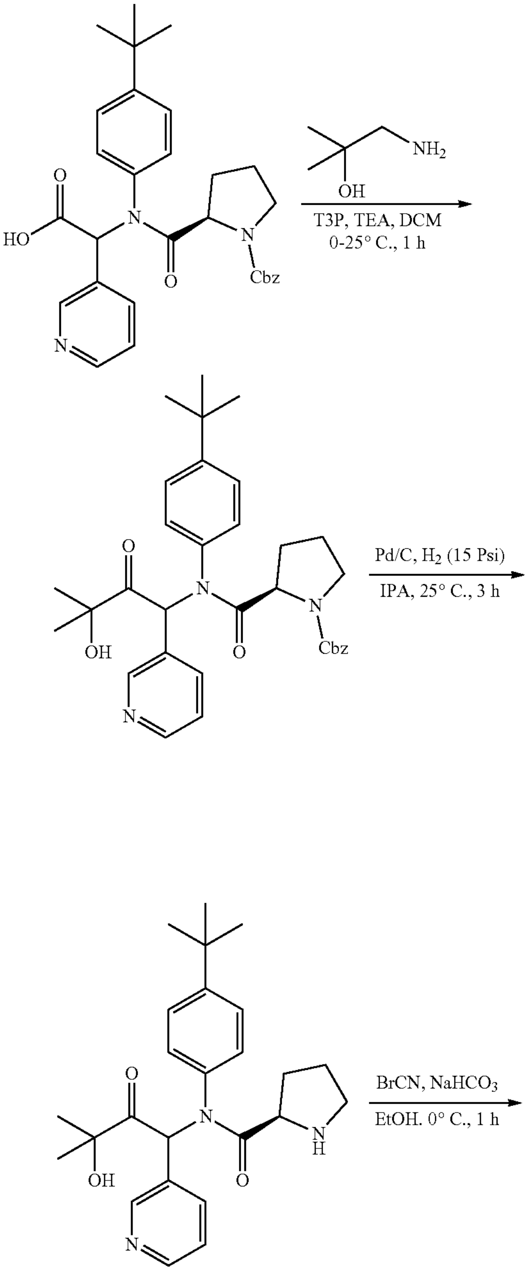

-continued

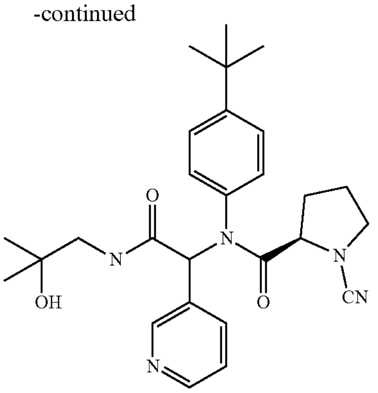

Step 1: (2R)-benzyl2-((4-(tert-butyl)phenyl)(2-((2-hydroxy-2-methylpropyl)amino)-2-oxo-1-(pyridin-3-yl) ethyl)carbamoyl)pyrrolidine-1-carboxylate To a solution of 2-((R)-1-((benzyloxy)carbonyl)-N-(4-(tert-butyl)phenyl)pyrrolidine-2-carboxamido)-2-(pyridin-3-yl)acetic acid (500 mg, 969.75 umol, 1 eq) and 1-amino-2-methyl-propan-2-ol (432.20 mg, 4.85 mmol, 5 eq) in DCM (10 mL) was added TEA (490.64 mg, 4.85 mmol, 674.88 uL, 5 eq), and the solution was cooled to 0° C. After the addition of T3P (925.66 mg, 1.45 mmol, 865.11 uL, 50% purity, 1.5 eq) drop-wise at 0° C., the mixture was stirred at 25° C. for 1 h. The mixture was quenched by water (6 mL) and then was extracted with DCM (5 mL*3), the combined organic layers were dried over $Na_2SO_4$, filtered and concentrated under reduced pressure to obtained (2R)-benzyl2-((4-(tert-butyl)phenyl)(2-((2-hydroxy-2-methylpropyl) amino)-2-oxo-1-(pyridin-3-yl)ethyl)carbamoyl)pyrrolidine-1-carboxylate (600 mg, 920.37 umol, 94.91% yield, 90% purity) as a pink oil. MS (ESI) m/z 587.3 $[M+H]^+$

Step 2: (2R)—N-(4-(tert-butyl)phenyl)-N-(2-((2-hydroxy-2-methylpropyl)amino)-2-oxo-1-(pyridin-3-yl)ethyl)pyrrolidine-2-carboxamide A solution of (2R)-benzyl2-((4-(tert-butyl)phenyl) (2-((2-hydroxy-2-methylpropyl)amino)-2-oxo-1-(pyridin-3-yl) ethyl)carbamoyl)pyrrolidine-1-carboxylate (550 mg, 937.42 umol, 1 eq) in IPA (8 mL), was added Pd/C (60 mg, 937.42 umol, 10% purity, 1 eq) at 25° C. under $H_2$ (15 Psi), the mixture was stirred at 25° C. for 3 h. The mixture was filtered and concentrated in vacuum to obtained (2R)—N-(4-(tert-butyl) phenyl)-N-(2-((2-hydroxy-2-methylpropyl) amino)-2-oxo-1-(pyridin-3-yl)ethyl)pyrrolidine-2-carboxamide (400 mg, crude) as a colorless oil. MS (ESI) m/z 453.2 $[M+H]^+$

Step 3: (2R)—N-(4-(tert-butyl)phenyl)-1-cyano-N-(2-(3-fluoroazetidin-1-yl)-2-oxo-1-(pyridin-3-yl) ethyl)pyrrolidine-2-carboxamide A solution of (2R)—N-(4-(tert-butyl)phenyl)-N-(2-((2-hydroxy-2-methylpropyl)amino)-2-oxo-1-(pyridin-3-yl) ethyl)pyrrolidine-2-carboxamide (400 mg, 883.81 umol, 1 eq) in EtOH (6 mL) was added with $NaHCO_3$ (222.74 mg, 2.65 mmol, 103.12 uL, 3 eq) at 0° C. After the addition of BrCN (187.23 mg, 1.77 mmol, 130.02 uL, 2 eq) at 0° C., the mixture was stirred at 0° C. for 1 h. The mixture was dried by blowing $N_2$ and then was quenched by water, then was extracted with DCM (3 mL*3), the organic phase was dried by $Na_2SO_4$, filtered and concentration in vacuum and was purified by prep-HPLC to obtained (2R)—N-(4-(tert-butyl) phenyl)-1-cyano-N-(2-(3-fluoroazetidin-1-yl)-2-oxo-1-(pyridin-3-yl)ethyl)pyrrolidine-2-carboxamide (110 mg, 223.41 umol, 25.28% yield, 97% purity) as a yellow solid. MS (ESI) m/z 478.3 $[M+H]^+$.

prep-HPLC conditions: column: Waters Xbridge BEH C18 100*25 mm*5 um; mobile phase: [water (10 mM $NH_4HCO_3$)-ACN]; B %: 25%-55%, 10 min.

1H NMR (400 MHz, METHANOL-$d_4$) δ=8.40-8.25 (m, 2H), 7.76-6.56 (m, 6H), 6.24-5.98 (m, 1H), 4.18-4.09 (m, 1H), 3.63-3.53 (m, 1H), 3.49-3.39 (m, 1H), 3.27-3.19 (m, 2H), 2.13-1.76 (m, 4H), 1.26-1.21 (m, 9H), 1.16 (s, 3H), 1.09 (s, 3H).

Example 165: Synthesis of Compound 1322

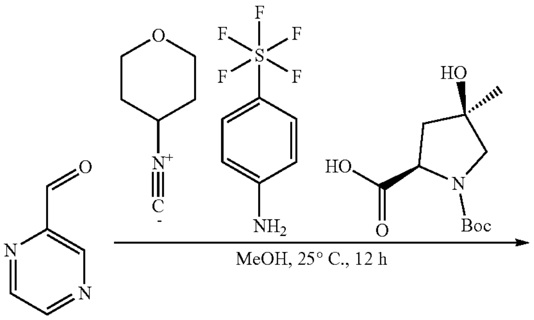

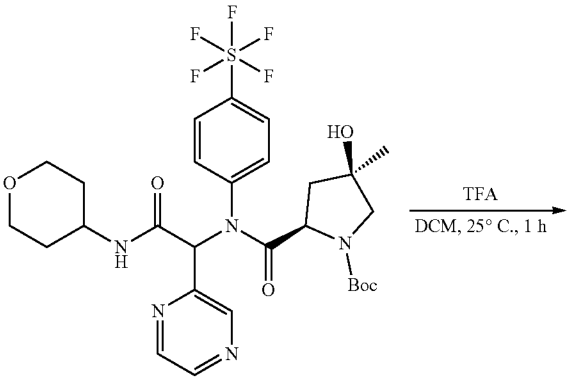

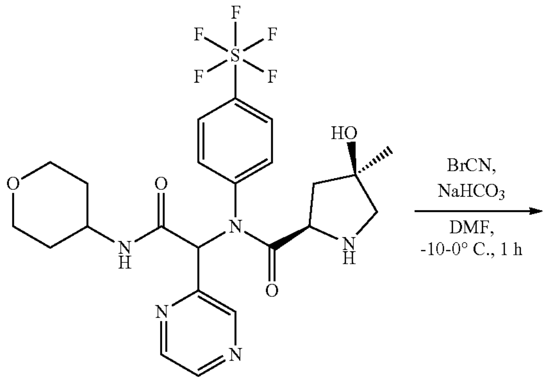

-continued

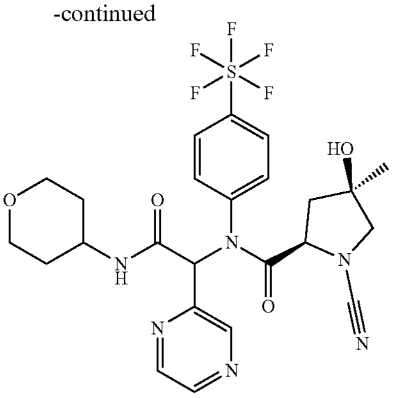

Step 1: tert-butyl (2R,4R)-4-hydroxy-4-methyl-2-[[2-oxo-1-pyrazin-2-yl-2-(tetrahydropyran-4-ylamino)ethyl]-[4-(pentafluoro-26-sulfanyl)phenyl]carbamoyl]pyrrolidine-1-carboxylate To a solution of pyrazine-2-carbaldehyde (150 mg, 1.39 mmol, 1 eq) and 4-(pentafluoro-λ6-sulfanyl)aniline (304.13 mg, 1.39 mmol, 1 eq) in MeOH (6 mL), was added drop-wise (2R,4R)-1-tert-butoxycarbonyl-4-hydroxy-4-methyl-pyrrolidine-2-carboxylic acid (425.43 mg, 1.39 mmol, 80% purity, 1 eq) and methylidyne(tetrahydropyran-4-yl)ammonium (155.62 mg, 1.39 mmol, 1 eq) in MeOH (2 mL), and then the mixture was stirred at 25° C. for 12 h. The reaction mixture was concentrated under reduced pressure to give a residue. The residue was purified by prep-HPLC (column: Phenomenex Gemini-NX 80*40 mm*3 um; mobile phase: [water (10 mM $NH_4HCO_3$)-ACN]; B %: 30%-50%, 8 min) to get the product tert-butyl (2R,4R)-4-hydroxy-4-methyl-2-[[2-oxo-1-pyrazin-2-yl-2-(tetrahydropyran-4-ylamino)ethyl]-[4-(pentafluoro-λ6-sulfanyl)phenyl]carbamoyl]pyrrolidine-1-carboxylate (110 mg, 153.68 umol, 11.07% yield, 93% purity) was obtained as a yellow solid. MS (ESI) m/z 666.2 $[M+H]^+$ Step 2: (2R,4R)-4-hydroxy-4-methyl-N-[2-oxo-1-pyrazin-2-yl-2-(tetrahydropyran-4-ylamino)ethyl]-N-[4-(pentafluoro-λ6-sulfanyl)phenyl]pyrrolidine-2-carboxamide To a solution of tert-butyl (2R,4R)-4-hydroxy-4-methyl-2-[[2-oxo-1-pyrazin-2-yl-2-(tetrahydropyran-4-ylamino)ethyl]-[4-(pentafluoro-λ6-sulfanyl)phenyl]carbamoyl]pyrrolidine-1-carboxylate (100 mg, 150.22 umol, 1 eq) in DCM (3.0 mL) was added drop-wise TFA (1.54 g, 13.51 mmol, 1.00 mL, 89.91 eq), and the mixture was stirred at 25° C. for 1 h. The reaction mixture was concentrated under reduced pressure to give a residue. The residue was diluted with 20 mL DCM and quenched by addition aq. $NaHCO_3$ at 0° C., and the pH was adjusted to 8.0, and then extracted with DCM (20 mL*2). The combined organic layers were washed with 30 mL brine, dried over $Na_2SO_4$, filtered and concentrated under reduced pressure to get the product (2R,4R)-4-hydroxy-4-methyl-N-[2-oxo-1-pyrazin-2-yl-2-(tetrahydropyran-4-ylamino)ethyl]-N-[4-(pentafluoro-λ6-sulfanyl)phenyl]pyrrolidine-2-carboxamide (80 mg, crude) was obtained as a yellow oil.

$^1H$ NMR (METHANOL-$d_4$, 400 MHz): δ ppm 8.56 (dd, J=15.2, 1.4 Hz, 1H), 8.45-8.53 (m, 1H), 8.39-8.45 (m, 1H), 7.45-7.86 (m, 4H), 3.84-3.96 (m, 3H), 3.72 (br d, J=5.7 Hz, 1H), 3.40-3.50 (m, 2H), 2.94 (br d, J=11.6 Hz, 1H), 2.53 (br d, J=11.9 Hz, 1H), 1.89-1.98 (m, 1H), 1.40-1.83 (m, 5H), 1.22-1.26 (m, 3H).

Step 3: (2R,4R)-1-cyano-4-hydroxy-4-methyl-N-[2-oxo-1-pyrazin-2-yl-2-(tetrahydropyran-4-ylamino)ethyl]-N-[4-(pentafluoro-λ6-sulfanyl)phenyl]pyrrolidine-2-carboxamide A solution of (2R,4R)-4-hydroxy-4-methyl-N-[2-oxo-1-pyrazin-2-yl-2-(tetrahydropyran-4-ylamino)ethyl]-N-[4-(pentafluoro-λ6-sulfanyl)phenyl]pyrrolidine-2-carboxamide (80 mg, 141.45 umol, 1 eq) in EtOH (3 mL) was cooled to −10° C., and then BrCN (22.47 mg, 212.18 umol, 15.61 uL, 1.5 eq) and $NaHCO_3$ (23.77 mg, 282.91 umol, 11.00 uL, 2.0 eq) was added drop-wise at −10° C. The mixture was stirred at 0° C. for 1 h and concentrated to provide a residue. The residue was purified by prep-HPLC (column: Phenomenex Luna C18 200*40 mm*10 um; mobile phase: [water (0.2% FA)-ACN]; B %: 20%-50%, 8 min) to get the product (2R,4R)-1-cyano-4-hydroxy-4-methyl-N-[2-oxo-1-pyrazin-2-yl-2-(tetrahydropyran-4-ylamino)ethyl]-N-[4-(pentafluoro-$λ^6$-sulfanyl)phenyl]pyrrolidine-2-carboxamide (25.72 mg, 41.20 umol, 29.13% yield, 94.6% purity) was obtained as a white solid. MS (ESI) m/z 591.2 $[M+H]^+$ $^1H$ NMR (METHANOL-$d_4$, 400 MHz): δ ppm 8.55-8.62 (m, 1H), 8.46-8.55 (m, 1H), 8.39-8.46 (m, 1H), 7.49-7.88 (m, 4H), 6.23-6.45 (m, 1H), 4.34 (br dd, J=9.4, 4.6 Hz, 1H), 3.85-3.97 (m, 3H), 3.43-3.51 (m, 3H), 3.34 (d, J=9.3 Hz, 1H), 2.09 (td, J=12.9, 4.6 Hz, 1H), 1.90-2.00 (m, 1H), 1.70-1.86 (m, 2H), 1.41-1.54 (m, 2H), 1.23-1.28 (m, 3H).

Example 166: Synthesis of Compound 1324

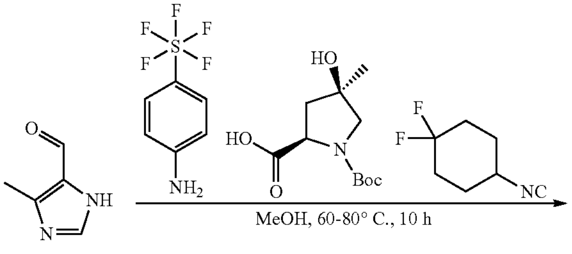

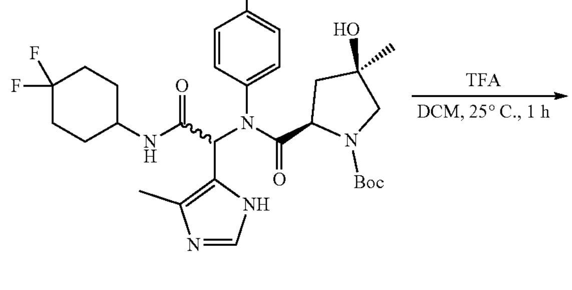

-continued

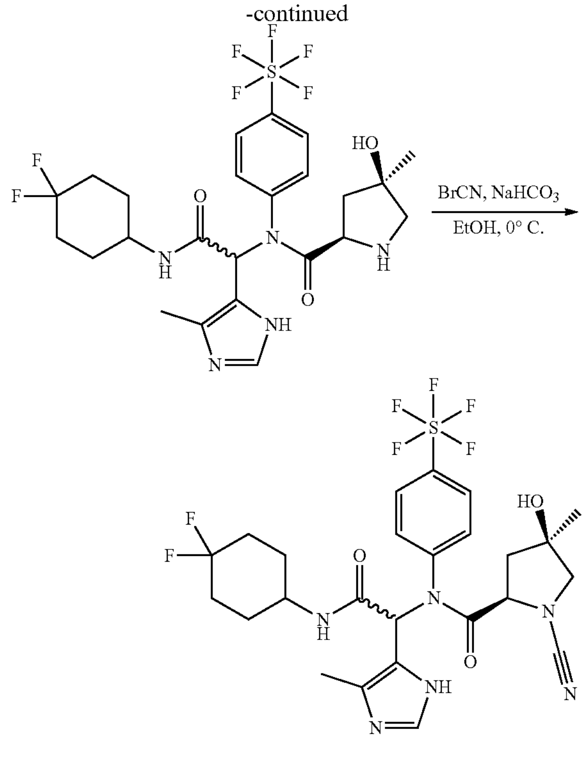

Step 1: tert-butyl(2R,4R)-2-[[2-[(4,4-difluorocyclohexyl)amino]-1-(4-methyl-1H-imidazol-5-yl)-2-oxo-ethyl]-[4-(pentafluoro-λ$^6$-sulfanyl)phenyl]carbamoyl]-4-hydroxy-4-methyl-pyrrolidine-1-carboxylate A solution of 4-(pentafluoro-λ$^6$-sulfanyl) aniline (214.46 mg, 978.51 umol, 1 eq) and 4-methyl-1H-imidazole-5-carbaldehyde (107.75 mg, 978.51 umol, 1 eq) in MeOH (8 mL) was stirred at 80° C. for 2 h, and then (2R,4R)-1-tert-butoxycarbonyl-4-hydroxy-4-methyl-pyrrolidine-2-carboxylic acid (300 mg, 978.51 umol, 80% purity, 1 eq) was added to the mixture. A solution of 1,1-difluoro-4-isocyano-cyclohexane (127.83 mg, 880.66 umol, 0.9 eq) in MeOH (1 mL) was added in portions and stirred at 60° C. for 8 h. The mixture was concentration in vacuum and was purified by prep-HPLC to obtained tert-butyl(2R,4R)-2-[[2-[(4,4-difluorocyclohexyl)amino]-1-(4-methyl-1H-imidazol-5-yl)-2-oxo-ethyl]-[4-(pentafluoro-λ6-sulfanyl)phenyl]carbamoyl]-4-hydroxy-4-methyl-pyrrolidine-1-carboxylate (Isomer 1: 120 mg, 153.91 umol, 15.73% yield, 90% purity) and tert-butyl(2R,4R)-2-[[2-[(4,4-difluorocyclohexyl)amino]-1-(4-methyl-1H-imidazol-5-yl)-2-oxo-ethyl]-[4-(pentafluoro-λ6-sulfanyl)phenyl]carbamoyl]-4-hydroxy-4-methyl-pyrrolidine-1-carboxylate (Isomer 2: 120 mg, 153.91 umol, 15.73% yield, 90% purity) as a colorless oil. MS (ESI) m/z 702.2 [M+H]$^+$ prep-HPLC condition: column: Phenomenex luna C18 250*50 mm*10 um; mobile phase: [water (0.1% TFA)-ACN]; B %: 30%-50%, 10 min.

Step 2: (2R,4R)—N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide Isomer 1: A solution of tert-butyl (2R,4R)-2-[[2-[(4,4-difluorocyclohexyl)amino]-1-(4-methyl-1H-imidazol-5-yl)-2-oxo-ethyl]-[4-(pentafluoro-λ$^6$-sulfanyl)phenyl]carbamoyl]-4-hydroxy-4-methyl-pyrrolidine-1-carboxylate (100 mg, 142.51 umol, 1 eq) in TFA (0.3 mL) and DCM (1 mL) was stirred at 25° C. for 1 h. The mixture was concentrated in vacuum, quenched by sat. $NaHCO_3$ (5 mL), pH was adjusted to ~8, and then was extracted with DCM (3 mL*3). The organic phase was dried by $Na_2SO_4$ and was filtered and concentration to obtained (2R,4R)—N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide (60 mg, crude) as a yellow gum. MS (ESI) m/z 602.1 [M+H]$^+$ Isomer 2: A solution of tert-butyl (2R,4R)-2-[[2-[(4,4-difluorocyclohexyl)amino]-1-(4-methyl-1H-imidazol-5-yl)-2-oxo-ethyl]-[4-(pentafluoro-λ$^6$-sulfanyl)phenyl]carbamoyl]-4-hydroxy-4-methyl-pyrrolidine-1-carboxylate (100 mg, 142.51 umol, 1 eq) in TFA (0.3 mL) and DCM (1 mL), the mixture was stirred at 25° C. for 1 h. The mixture was concentrated in vacuum, quenched by sat. $NaHCO_3$ (5 mL), adjusted pH-8, and then was extracted with DCM (3 mL*3). The organic phase was dried by $Na_2SO_4$ and was filtered and concentration to obtain (2R,4R)—N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide (50 mg, crude) as a yellow gum. MS (ESI) m/z 602.1 [M+H]$^+$ Step 3: (2R,4R)-1-cyano-N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ6-sulfanyl)phenyl]pyrrolidine-2-carboxamide Isomer 1: To a solution of (2R,4R)—N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide (50 mg, 83.11 umol, 1 eq) in EtOH (1 mL) was added $NaHCO_3$ (20.95 mg, 249.34 umol, 9.70 uL, 3 eq) at 0° C. BrCN (17.61 mg, 166.23 umol, 12.23 uL, 2 eq) was then added at 0° C., and the mixture was stirred at 0° C. for 1 h. The mixture was dried by blowing $N_2$ and was quenched by water, then was extracted with DCM (3 mL*3), then was dried by $Na_2SO_4$, filtered and concentration in vacuum and was purified by prep-HPLC to obtained (2R,4R)-1-cyano-N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide (15 mg, 23.94 umol, 28.80% yield, 100% purity) as a white solid.

prep-HPLC condition: column: Waters Xbridge BEH C18 100*25 mm*5 um; mobile phase: [water (10 mM $NH_4HCO_3$)-ACN]; B %: 25%-55%, 10 min.

$^1$H NMR (Isomer 1) (400 MHz, MeOD-$d_4$) δ ppm 8.10-7.49 (m, 3H), 7.34 (s, 1H), 7.13-6.77 (m, 1H), 6.30 (s, 1H), 4.21 (dd, J=4.3, 9.2 Hz, 1H), 3.89 (t, J=9.8 Hz, 1H), 3.49 (d, J=9.0 Hz, 1H), 3.34 (d, J=9.0 Hz, 1H), 2.01-1.98 (m, 1H), 2.17-1.81 (m, 12H), 1.69-1.44 (m, 2H), 1.25 (s, 3H).

Isomer 2: To a solution of (2R,4R)—N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide (50 mg, 83.11 umol, 1 eq) in EtOH (1 mL) was added $NaHCO_3$ (20.95 mg, 249.34 umol, 9.70 uL, 3 eq) at 0° C. After the addition of BrCN (17.61 mg, 166.23 umol, 12.23 uL, 2 eq) at 0° C., the mixture was stirred at 0° C. for 1 h. The mixture was dried by blowing $N_2$ and was quenched by water, then was extracted with DCM (3 mL*3), then was dried by $Na_2SO_4$, filtered and concentration in vacuum and was purified by prep-HPLC to obtained (2R,4R)-1-cyano-N-[2-[(4,4-difluorocyclohexyl)amino]-1-(4-methyl-1H-imidazol-5-yl)-2-oxo-ethyl]-4-hydroxy-4-methyl-N-[4-(pentafluoro-λ$^6$-sulfanyl)phenyl]pyrrolidine-2-carboxamide (15 mg, 23.72 umol, 28.54% yield, 99.1% purity) as a white solid.

prep-HPLC condition: column: Waters Xbridge BEH C18 100*25 mm*5 um; mobile phase: [water (10 mM $NH_4HCO_3$)-ACN]; B %: 25%-55%, 10 min.

$^1$H NMR (Isomer 1) (400 MHz, MeOD-$d_4$) δ ppm 8.32-7.53 (m, 3H), 7.46-7.31 (m, 1H), 7.18-6.53 (m, 1H), 6.31-6.14 (m, 1H), 4.32-4.16 (m, 1H), 3.88 (t, J=10.3 Hz, 1H), 3.49 (d, J=9.3 Hz, 1H), 3.34 (d, J=9.3 Hz, 1H), 2.22-1.72 (m, 12H), 1.70-1.40 (m, 2H), 1.25 (s, 3H).

Example 167: Synthesis of Compound 1087

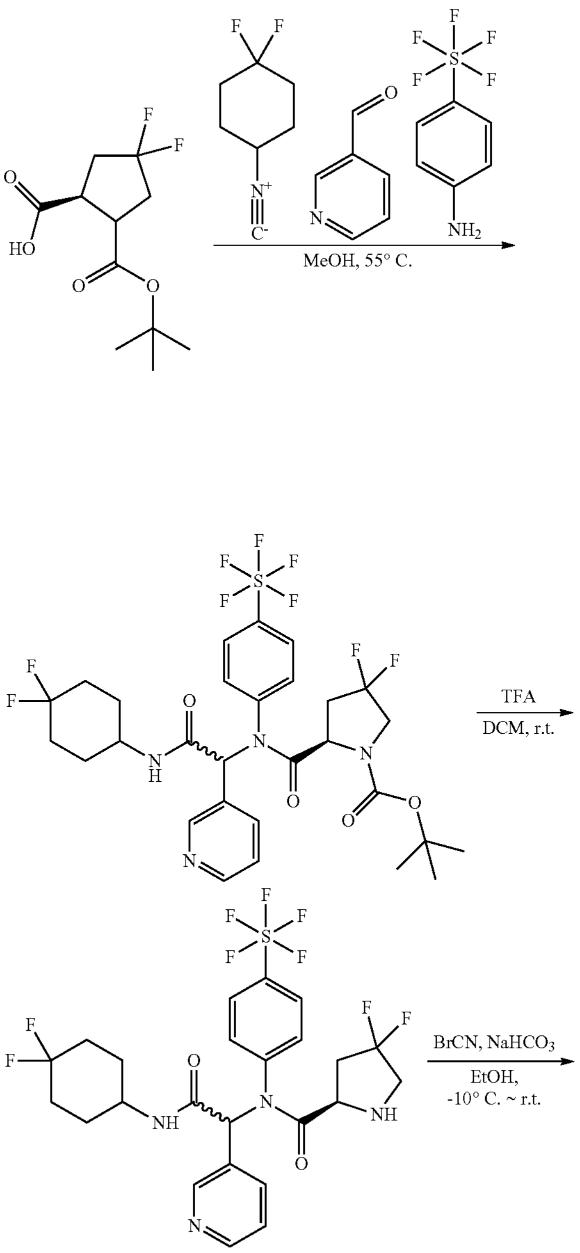

-continued

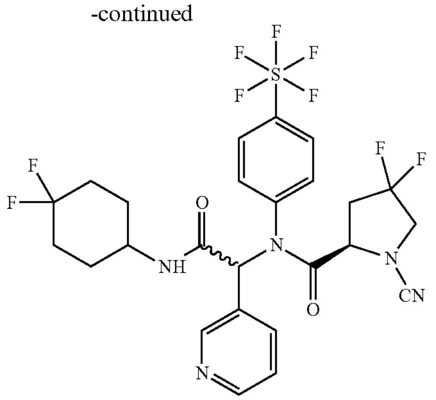

Step 1: tert-butyl (2R)-2-[[2-[(4,4-difluorocyclohexyl)amino]-2-oxo-1-(3-pyridyl)ethyl]-[4-(pentafluoro-λ6-sulfanyl)phenyl]carbamoyl]-4,4-difluoro-pyrrolidine-1-carboxylate A solution of pyridine-3-carbaldehyde (85.27 mg, 796.09 umol, 74.80 uL, 1 eq), 4-(pentafluoro-λ6-sulfanyl)aniline (174.48 mg, 796.09 umol, 1 eq) in MeOH (3 mL) stirred at 55° C. for 5 h. (2R)-1-tert-butoxycarbonyl-4,4-difluoro-pyrrolidine-2-carboxylic acid (200 mg, 796.09 umol, 1 eq) was added to the solution, followed by the addition of a solution of 1,1-difluoro-4-isocyano-cyclohexane (104.00 mg, 716.48 umol, 0.9 eq) in MeOH (1 mL) in batches (three times), and then the mixture was stirred at 55° C. for 19 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 55%-75%, 8 min) to give the title product tert-butyl (2R)-2-[[2-[(4,4-difluorocyclohexyl)amino]-2-oxo-1-(3-pyridyl)ethyl]-[4-(pentafluoro-λ6-sulfanyl)phenyl]carbamoyl]-4,4-difluoro-pyrrolidine-1-carboxylate (75 mg, 106.44 umol, 13.37% yield, N/A purity) as a yellow solid and tert-butyl (2R)-2-[[2-[(4,4-difluorocyclohexyl)amino]-2-oxo-1-(3-pyridyl)ethyl]-[4-(pentafluoro-λ6-sulfanyl)phenyl]carbamoyl]-4,4-difluoro-pyrrolidine-1-carboxylate (75 mg, 106.44 umol, 13.37% yield, N/A purity). MS (ESI) m/z 705.2 [M+1]$^+$ Step 2: (2R)—N-[2-[(4,4-difluorocyclohexyl)amino]-2-oxo-1-(3-pyridyl)ethyl]-4,4-difluoro-N-[4-(pentafluoro-L6-sulfanyl)phenyl]pyrrolidine-2-carboxamide Isomer: A mixture of tert-butyl (2R)-2-[[2-[(4,4-difluorocyclohexyl)amino]-2-oxo-1-(3-pyridyl)ethyl]-[4-(pentafluoro-λ6-sulfanyl)phenyl]carbamoyl]-4,4-difluoro-pyrrolidine-1-carboxylate (75 mg, 106.44 umol, 1 eq), in DCM (1 mL) and TFA (0.3 mL) was stirred at 20° C. for 0.5 h under $N_2$ atmosphere. Upon completion, the reaction mixture was quenched by addition $NaHCO_3$ (20 mL), and extracted with DCM (15 mL*3). The combined organic layers were washed with brine (20 mL), dried over $Na_2SO_4$, filtered and concentrated under reduced pressure to give a crude product (2R)—N-[2-[(4,4-difluorocyclohexyl)amino]-2-oxo-1-(3-pyridyl)ethyl]-4,4-difluoro-N-[4-(pentafluoro-λ6-sulfanyl)phenyl]pyrrolidine-2-carboxamide (55 mg, crude) as a yellow solid. MS (ESI) m/z 605.2 [M+H]$^+$ Isomer 2: A mixture of tert-butyl (2R)-2-[[2-[(4,4-difluorocyclohexyl)amino]-2-oxo-1-(3-pyridyl)ethyl]-[4-(pentafluoro-λ6-sulfanyl)phenyl]carbamoyl]-4,4-difluoro-pyrrolidine-1-carboxylate (75 mg, 106.44 umol, 1 eq) in DCM (1 mL) and TFA (0.3 mL) was stirred at 20° C. for 0.5 h under $N_2$ atmosphere. Upon completion, the reaction mixture was quenched by addition $NaHCO_3$ (20 mL), and extracted with DCM (15 mL*3). The combined organic layers were washed with brine (20 mL), dried over $Na_2SO_4$, filtered and concentrated under reduced pressure to give a crude product (2R)—N-[2-[(4,4-difluorocyclohexyl)amino]-2-oxo-1-(3-pyridyl)ethyl]-4,4-difluoro-N-[4-(pentafluoro-λ6-sulfanyl)phenyl]pyrrolidine-2-carboxamide (55 mg, crude) as a yellow solid. MS (ESI) m/z 605.2 $[M+H]^+$ Step 3: (2R)-1-cyano-N-[2-[(4,4-difluorocyclohexyl)amino]-2-oxo-1-(3-pyridyl)ethyl]-4,4-difluoro-N-[4-(pentafluoro-λ6-sulfanyl)phenyl]pyrrolidine-2-carboxamide Isomer 1: To a solution of (2R)—N-[2-[(4,4-difluorocyclohexyl)amino]-2-oxo-1-(3-pyridyl)ethyl]-4,4-difluoro-N-[4-(pentafluoro-λ6-sulfanyl)phenyl]pyrrolidine-2-carboxamide (55 mg, 90.98 umol, 1 eq) and $NaHCO_3$ (22.93 mg, 272.94 umol, 10.62 uL, 3 eq) in EtOH (1 mL) was added a solution of BrCN (14.45 mg, 136.47 umol, 10.04 uL, 1.5 eq) in EtOH (0.5 mL) drop-wise at −10° C. under $N_2$. The reaction mixture was slowly warmed to 25° C. for 1.5 h. Upon completion, the reaction mixture was quenched by addition $H_2O$ (30 mL) and extracted with EtOAc (15 mL*3). The combined organic layers were washed with brine (20 mL), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-60%, 8 min) to give (2R)-1-cyano-N-[2-[(4,4-difluorocyclohexyl)amino]-2-oxo-1-(3-pyridyl)ethyl]-4,4-difluoro-N-[4-(pentafluoro-λ6-sulfanyl)phenyl]pyrrolidine-2-carboxamide (36.36 mg, 55.16 umol, 60.63% yield, 95.5% purity) as a yellow solid. MS (ESI) m/z 630.2 $[M+H]^+$ $^1H$ NMR (400 MHz, MeOD-$d_4$) δ ppm 8.43-8.34 (m, 2H), 8.11-7.56 (m, 4H), 7.25-6.81 (m, 2H), 6.24 (s, 1H), 4.48-4.44 (m, 1H), 3.97-3.82 (m, 3H), 2.59-2.41 (m, 2H), 1.96-1.87 (m, 6H), 1.66-1.55 (m, 1H), 1.47-1.50 (m, 1H).

Isomer 2: To a solution of (2R)—N-[2-[(4,4-difluorocyclohexyl)amino]-2-oxo-1-(3-pyridyl)ethyl]-4,4-difluoro-N-[4-(pentafluoro-2,6-sulfanyl)phenyl]pyrrolidine-2-carboxamide (55 mg, 90.98 umol, 1 eq) and $NaHCO_3$ (22.93 mg, 272.94 umol, 10.62 uL, 3 eq) in EtOH (1 mL) was added a solution of BrCN (14.45 mg, 136.47 umol, 10.04 uL, 1.5 eq) in EtOH (0.5 mL) drop-wise at −10° C. under $N_2$. The reaction mixture was slowly warmed to 25° C. for 1.5 h. Upon completion, the reaction mixture was quenched by addition $H_2O$ (30 mL) and extracted with EtOAc (15 mL*3). The combined organic layers were washed with brine (20 mL), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 40%-80%, 8 min) to give (2R)-1-cyano-N-[2-[(4,4-difluorocyclohexyl)amino]-2-oxo-1-(3-pyridyl)ethyl]-4,4-difluoro-N-[4-(pentafluoro-6-sulfanyl)phenyl]pyrrolidine-2-carboxamide (27.52 mg, 39.52 umol, 43.44% yield, 90.4% purity) as a yellow solid. MS (ESI) m/z 630.2 $[M+H]^+$ $^1H$ NMR (400 MHz, MeOD-$d_4$) δ ppm 8.38-8.32 (m, 2H), 7.79-7.55 (m, 4H), 7.25-6.75 (m, 2H), 6.10 (s, 1H), 4.44-4.42 (m, 1H), 3.95-3.81 (m, 3H), 2.58-2.43 (m, 2H), 2.12-1.94 (m, 6H), 1.85-1.82 (m, 1H), 1.64-1.45 (m, 1H).

Example 168: Synthesis of Compound 1228

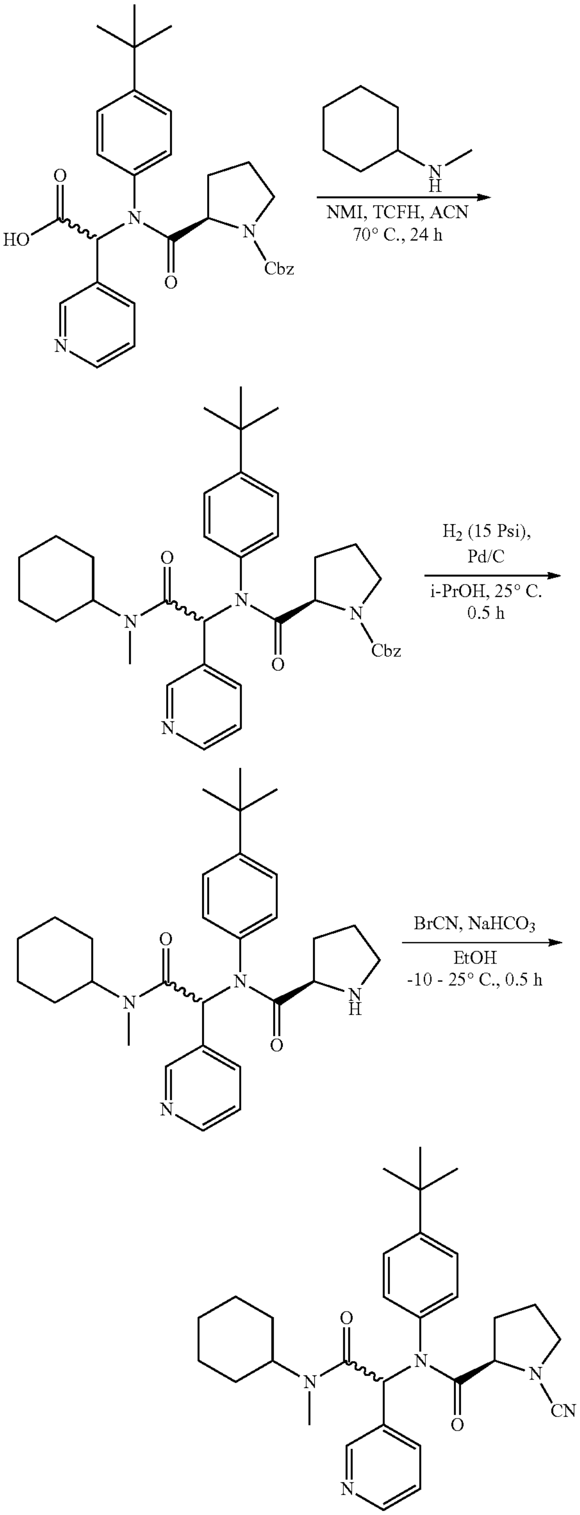

Step 1: (2R)-benzyl2-((4-(tert-butyl)phenyl)(2-(cyclohexyl(methyl)amino)-2-oxo-1-(pyridin-3-yl)ethyl)carbamoyl)pyrrolidine-1-carboxylate 2-(N-[(2R)-1-benzyloxycarbonylpyrrolidine-2-carbonyl]-4-tert-butyl-anilino)-2-(3-pyridyl)acetic acid (300 mg, 581.85 umol, 1 eq) in ACN (5 mL) was added N-methylcyclohexanamine (65.87 mg, 581.85 umol, 76.86 uL, 1 eq) 1-methylimidazole (143.32 mg, 1.75 mmol, 139.14 uL, 3 eq) and [chloro(dimethylamino)methylene]-dimethyl-ammonium;hexafluorophosphate (212.23 mg, 756.40 umol, 1.3 eq). The mixture was stirred at 70° C. for 24 h. Upon completion, the mixture was concentrated under the reduced pressure to give a residue. The residue was purified by prep-TLC ($SiO_2$, PE:EA=1:1) affording the product benzyl (2R)-2-[(4-tert-butylphenyl)-[2-[cyclohexyl(methyl)amino]-2-oxo-1-(3-pyridyl)ethyl]carbamoyl]pyrrolidine-1-carboxylate (70 mg, 114.61 umol, 19.70% yield) as a yellow oil.

Step 2: (2R)—N-(4-(tert-butyl)phenyl)-N-(2-(cyclohexyl(methyl)amino)-2-oxo-1-(pyridin-3-yl)ethyl)pyrrolidine-2-carboxamide A mixture of benzyl (2R)-2-[(4-tert-butylphenyl)-[2-[cyclohexyl(methyl)amino]-2-oxo-1-(3-pyridyl)ethyl]carbamoyl]pyrrolidine-1-carboxylate (70 mg, 114.61 umol, 1 eq) and Pd/C (30 mg, 10% purity, 1.00 eq) in i-PrOH (2 mL) was degassed and purged with $H_2$ (231.03 ug, 114.61 umol, 1 eq) for 3 times, and then the mixture was stirred at 25° C. for 0.5 hr under $H_2$ atmosphere. Upon completion the mixture was filtered and the filtrate concentrated under the reduced pressure affording the product (2R)—N-(4-tert-butylphenyl)-N-[2-[cyclohexyl(methyl)amino]-2-oxo-1-(3-pyridyl)ethyl]pyrrolidine-2-carboxamide (50 mg, crude) as a white solid. MS (ESI) m/z 477.3 $[M+H]^+$.

Step 3: (2R)—N-(4-(tert-butyl)phenyl)-1-cyano-N-(2-(cyclohexyl(methyl)amino)-2-oxo-1-(pyridin-3-yl)ethyl)pyrrolidine-2-carboxamide To a solution of (2R)—N-(4-tert-butylphenyl)-N-[2-[cyclohexyl(methyl)amino]-2-oxo-1-(3-pyridyl) ethyl]pyrrolidine-2-carboxamide (50 mg, 104.90 umol, 1 eq) in EtOH (1 mL) was added $NaHCO_3$ (26.44 mg, 314.70 umol, 12.24 uL, 3 eq), and the solution was cooled to −10° C. A solution of BrCN (11.11 mg, 104.90 umol, 7.72 uL, 1 eq) in EtOH (0.5 mL) was added and the solution stirred for 0.5 h at 0° C. and warmed to 25° C. gradually. Upon completion, the mixture was quenched by addition $H_2O$ (10 mL) and then extracted with DCM (10 mL*3). The combined organic layers were washed with brine (10 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 40%-75%, 10 min) to afford (2R)—N-(4-tert-butylphenyl)-1-cyano-N-[2-[cyclohexyl(methyl)amino]-2-oxo-1-(3-pyridyl)ethyl]pyrrolidine-2-carboxamide (2.71 mg, 5.16 umol, 4.92% yield, 95.6% purity) as a yellow solid. MS (ESI) m/z 502.3 $[M+H]^+$ $^1$H NMR (400 MHz, MeOD-$d_4$) δ=8.40-8.23 (m, 2H), 7.85-7.64 (m, 1H), 7.60-7.52 (m, 1H), 7.38 (br s, 1H), 7.24-7.08 (m, 2H), 6.75-6.45 (m, 2H), 4.15-4.12 (m, 1H), 4.10-3.57 (m, 1H), 3.49-3.40 (m, 1H), 2.94-2.72 (m, 3H), 2.14-0.13 (m, 24H).

Example 169: Synthesis of Compound 283

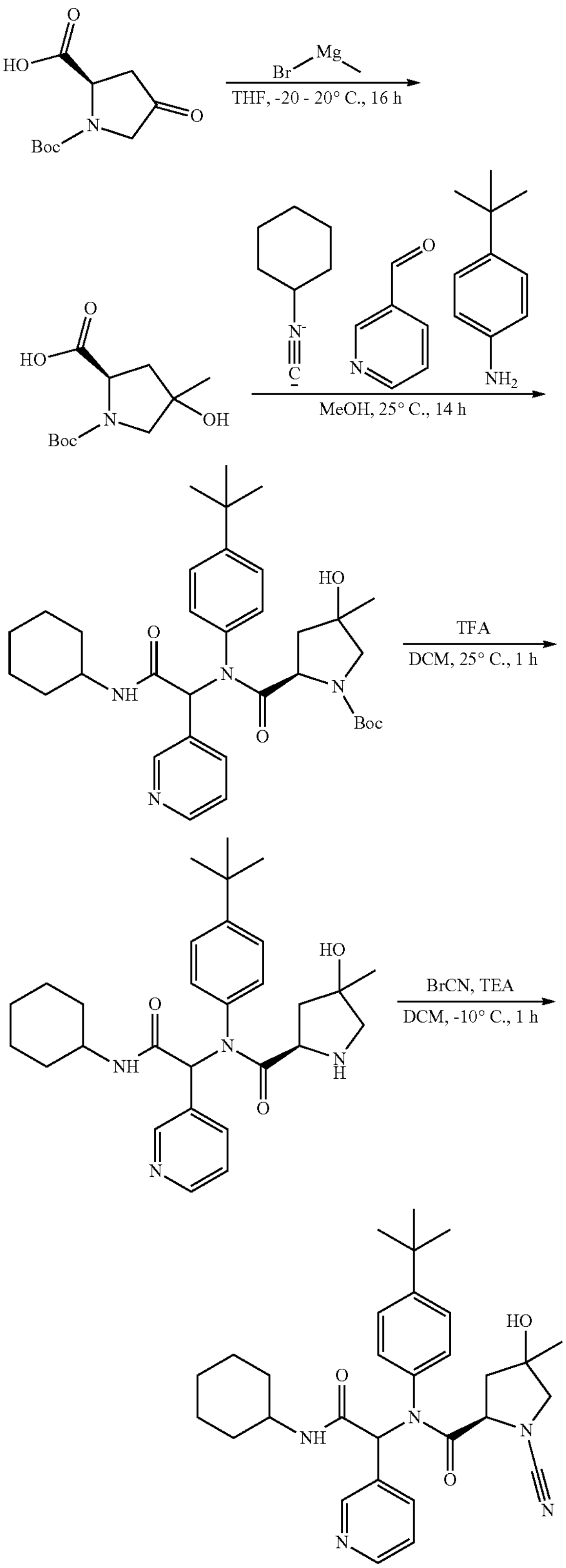

Step 1: (2R)-1-tert-butoxycarbonyl-4-hydroxy-4-methyl-pyrrolidine-2-carboxylic acid To a mixture of (2R)-1-tert-butoxycarbonyl-4-oxo-pyrrolidine-2-carboxylic acid (650 mg, 2.84 mmol, 1 eq) in THF (25 mL) was added methylmagnesium bromide (3 M, 2.36 mL, 2.5 eq) at −20° C. under $N_2$. The mixture was stirred at −20° C. for 1 h, then heated to 20° C. and stirred for 15 h. 1M HCl aq. (20 mL) was added and extracted with EtOAc (30 mL*3). The combined organic phase was washed with brine (90 mL), dried over $Na_2SO_4$, filtered, concentrated under reduced pressure and purified by prep-HPLC to give (2R)-1-tert-butoxycarbonyl-4-hydroxy-4-methyl-pyrrolidine-2-carboxylic acid (390 mg, 1.51 mmol, 52.93% yield, 95% purity) as yellow oil. MS (ESI) m/z 513.3 $[2M+Na]^+$.

Step 2: (2R,4R)-tert-butyl (2R)-tert-butyl 2-((4-(tert-butyl)phenyl)(2-(cyclohexylamino)-2-oxo-1-(pyridin-3-yl)ethyl)carbamoyl)-4-hydroxy-4-methylpyrrolidine-1-carboxylate To a solution of pyridine-3-carbaldehyde (126.64 mg, 1.18 mmol, 111.09 uL, 1 eq), 4-tert-butylaniline (176.45 mg, 1.18 mmol, 186.72 uL, 1 eq), (2R)-1-tert-butoxycarbonyl-4-hydroxy-4-methyl-pyrrolidine-2-carboxylic acid (290 mg, 1.18 mmol, 1 eq) and isocyanocyclohexane (116.17 mg, 1.06 mmol, 132.31 uL, 0.9 eq) in MeOH (9 mL) was stirred at 25° C. for 14 h. The reaction mixture was concentrated under reduced pressure, then purified by column chromatography ($SiO_2$, Petroleum ether:Ethyl acetate=10:1 to 1:1) to afford (2R)-2-[(4-tert-butylphenyl)-[2-(cyclohexylamino)-2-oxo-1-(3-pyridyl)ethyl]carbamoyl]-4-hydroxy-4-methyl-pyrrolidine-1-carboxylate (621 mg, 995.25 umol, 84.17% yield, 95% purity) as yellow solid. MS (ESI) m/z 593.2 $[M+H]^+$.

Step 3: (2R)—N-(4-(tert-butyl)phenyl)-N-(2-(cyclohexylamino)-2-oxo-1-(pyridin-3-yl)ethyl)-4-hydroxy-4-methylpyrrolidine-2-carboxamide To a solution of (2R)-2-[(4-tert-butylphenyl)-[2-(cyclohexylamino)-2-oxo-1-(3-pyridyl)ethyl]carbamoyl]-4-hydroxy-4-methyl-pyrrolidine-1-carboxylate (810.00 mg, 1.37 mmol, 1 eq) in DCM (9 mL) was added TFA (4.62 g, 40.52 mmol, 3 mL, 29.65 eq), and the mixture was stirred at 25° C. for 1 h. The reaction mixture was concentrated under reduced pressure and then purified by prep-HPLC to give (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (218 mg, 433.65 umol, 31.74% yield, 98% purity) as yellow solid, and (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (66 mg, 131.29 umol, 9.61% yield, 98% purity) as yellow solid. MS (ESI) m/z 493.2 $[M+H]^+$.

prep-HPLC condition: column: Phenomenex luna C18 250*50 mm*10 um; mobile phase: [water (0.1% TFA)-ACN]; B %: 30%-40%, 10 min.

Step 4: (2R)—N-(4-(tert-butyl)phenyl)-1-cyano-N-(2-(cyclohexylamino)-2-oxo-1-(pyridin-3-yl)ethyl)-4-hydroxy-4-methylpyrrolidine-2-carboxamide Isomer 1: To a solution of (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (208 mg, 432.76 umol, 1 eq) in DCM (2 mL) was added TEA (131.37 mg, 1.30 mmol, 180.70 uL, 3 eq) and then BrCN (46.75 mg, 441.41 umol, 32.47 uL, 1.02 eq) under $N_2$ at −10° C. After stirring the mixture at −10° C. for 1 h, the mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R)—N-(4-(tert-butyl)phenyl)-1-cyano-N-(2-(cyclohexylamino)-2-oxo-1-(pyridin-3-yl)ethyl)-4-hydroxy-4-methylpyrrolidine-2-carboxamide (72.44 mg, 139.94 umol, 32.34% yield, 100% purity) as white solid. MS (ESI) m/z 518.2 $[M+H]^+$.

prep-HPLC condition (Isomer 1): column: Phenomenex Gemini-NX 80*40 mm*3 um; mobile phase: [water (10 mM NH4HCO3)-ACN]; B %: 25%-55%, 8 min.

$^1$H NMR (Isomer 1) (400 MHz, MeOD-$d_4$) δ ppm 8.41-8.27 (m, 2H), 7.71 (s, 1H), 7.58-7.52 (m, 1H), 7.45 (s, 1H), 7.31-7.06 (m, 2H), 6.58 (s, 1H), 6.03 (s, 1H), 4.33-4.23 (m, 1H), 3.75-3.62 (m, 1H), 3.55-3.45 (m, 1H), 3.37-3.32 (m, 1H), 2.07-1.99 (m, 1H), 1.98-1.88 (m, 2H), 1.81-1.56 (m, 4H), 1.44-1.01 (m, 17H)

Isomer 2: To a solution of (2R)—N-(4-tert-butylphenyl)-N-[2-(cyclohexylamino)-2-oxo-1-(3-pyridyl)ethyl]-4-hydroxy-4-methyl-pyrrolidine-2-carboxamide (55 mg, 114.43 umol, 1 eq) in DCM (1 mL) was added TEA (34.74 mg, 343.29 umol, 47.78 uL, 3 eq) and then BrCN (12.36 mg, 116.72 umol, 8.59 uL, 1.02 eq) under $N_2$ at −10° C., the mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R)—N-(4-(tert-butyl)phenyl)-1-cyano-N-(2-(cyclohexylamino)-2-oxo-1-(pyridin-3-yl)ethyl)-4-hydroxy-4-methylpyrrolidine-2-carboxamide (26.54 mg, 51.27 umol, 44.80% yield, 100% purity) as white solid. MS (ESI) m/z 518.2 $[M+H]^+$. 100010411 prep-HPLC condition (Isomer 2): column: Waters Xbridge BEH C18 100*30 mm*10 um; mobile phase: [water (10 mM NH4HCO3)-ACN]; B %: 36%-66%, 10 min.

$^1$H NMR (Isomer 2) (400 MHz, MeOD-$d_4$) δ ppm 8.37-8.24 (m, 2H), 7.65 (s, 1H), 7.57-7.50 (m, 1H), 7.41 (s, 1H), 7.29-7.14 (m, 2H), 6.64 (s, 1H), 6.16 (s, 1H), 4.31-4.21 (m, 1H), 3.78-3.62 (m, 1H), 3.55-3.45 (m, 1H), 3.36-3.32 (m, 1H), 2.18-2.08 (m, 1H), 2.00-1.89 (m, 2H), 1.82-1.57 (m, 4H), 1.41-1.04 (m, 17H)

Example 171: Synthesis of Compound 307

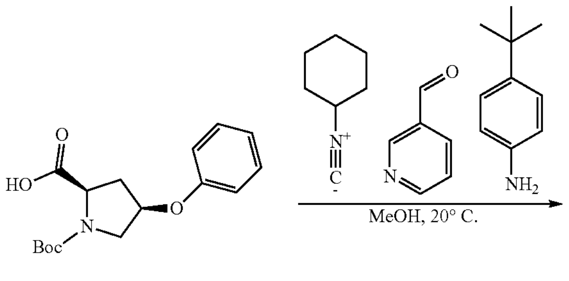

-continued

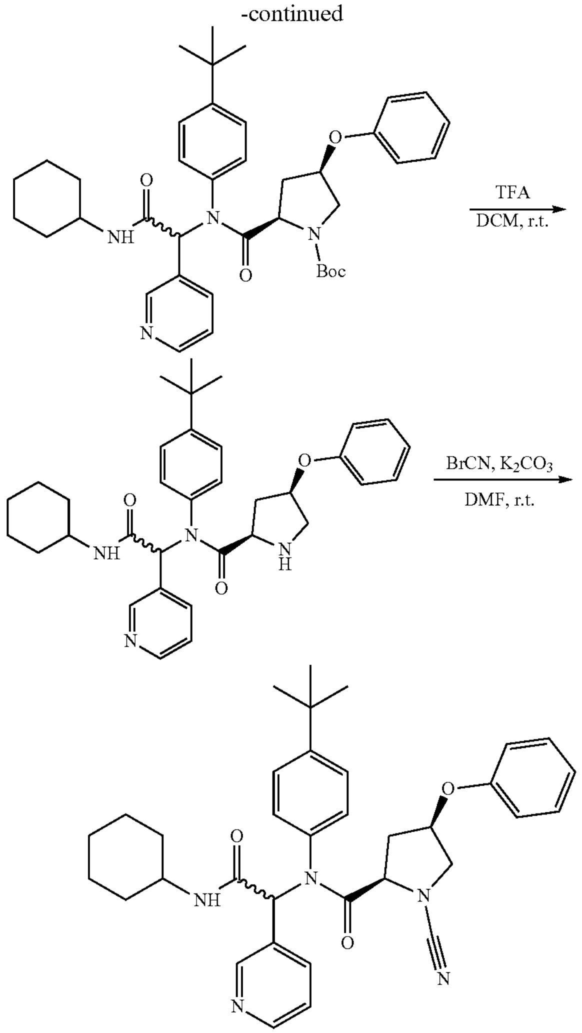

Step 1: (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate A solution of nicotinaldehyde (163.80 mg, 1.53 mmol, 143.68 uL, 1 eq), 4-(tert-butyl)aniline (228.21 mg, 1.53 mmol, 241.50 uL, 1 eq) in MeOH (6 mL) was stirred for 1 h, and then (2R,4R)-1-(tert-butoxycarbonyl)-4-phenoxypyrrolidine-2-carboxylic acid (470 mg, 1.53 mmol, 1 eq) was added. After stirring for 10 min, isocyanocyclohexane (166.95 mg, 1.53 mmol, 190.14 uL, 1 eq) in MeOH (1 mL) was added. The mixture was stirred at 25° C. for 1 h 50 min. The reaction mixture was concentrated under reduced pressure to remove solvent. The residue was purified by prep-HPLC to give (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (320 mg, 464.24 umol, 30.36% yield, 95% purity) and (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (330 mg, 478.75 umol, 31.31% yield, 95% purity) as a yellow solid. MS (ESI) m/z 655.2 $[M+H]^+$ Prep-HPLC condition: (column: Kromasil C18 (250*50 mm*10 um); mobile phase: [water (10 mM NH4HCO3)-ACN]; B %: 70%-90%, 10 min).

Step 2: (2R,4R)—N-(4-(tert-butyl)phenyl)-N-(2-(cyclohexylamino)-2-oxo-1-(pyridin-3-yl)ethyl)-4-phenoxypyrrolidine-2-carboxamide Isomer 1: To a solution of (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (320 mg, 488.67 umol, 1 eq) in DCM (5 mL) was added TFA (1.54 g, 13.51 mmol, 1 mL, 27.64 eq). The mixture was stirred at 25° C. for 1 hr. Then the reaction mixture was concentrated under reduced pressure to remove solvent to give (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (270 mg, crude) as a yellow solid. MS (ESI) m/z 555.3 [M+H]

Isomer 2: To a solution of (2R,4R)-tert-butyl 2-((4-(tert-butyl)phenyl)(2-(cyclohexylamino)-2-oxo-1-(pyridin-3-yl)ethyl)carbamoyl)-4-phenoxypyrrolidine-1-carboxylate (330 mg, 503.94 umol, 1 eq) in DCM (5 mL) was added TFA (1.54 g, 13.51 mmol, 1 mL, 26.80 eq). The mixture was stirred at 25° C. for 1 hr. The reaction mixture was concentrated under reduced pressure to remove solvent to afford (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (270 mg, crude) as a yellow solid. MS (ESI) m/z 555.3 $[M+H]^+$ Step 3: (2R,4R)—N-(4-(tert-butyl)phenyl)-1-cyano-N-(2-(cyclohexylamino)-2-oxo-1-(pyridin-3-yl)ethyl)-4-phenoxypyrrolidine-2-carboxamide Isomer 1: To a solution of (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (250 mg, 450.68 umol, 1 eq) in DMF (5 mL) was added $K_2CO_3$ (186.86 mg, 1.35 mmol, 3 eq), then BrCN (57.28 mg, 540.81 umol, 39.78 uL, 1.2 eq) was added at −10° C. The mixture was stirred at −10° C. for 2 hr. The reaction mixture was quenched by addition water (20 mL) at 25° C., and then extracted with EtOAc (20 mL*3). The combined organic layers were washed with brine (20 mL*2), dried over $[Na_2SO_4]$, filtered and concentrated under reduced pressure to give a residue. The residue was purified by prep-HPLC to give (2R,4R)—N-(4-(tert-butyl)phenyl)-1-cyano-N-(2-(cyclohexylamino)-2-oxo-1-(pyridin-3-yl)ethyl)-4-phenoxypyrrolidine-2-carboxamide (110 mg, 189.74 umol, 42.10% yield, 100% purity) as a white solid. MS (ESI) m/z 580.2 $[M+H]^+$ Prep-HPLC condition: (column: Phenomenex Gemini-NX C18 75*30 mm*3 um; mobile phase: [water (0.05% NH3H2O+10 mM NH4HCO3)-ACN]; B %: 45%-40%, 8 min).

$^1H$ NMR (Isomer 1). $^1H$ NMR (400 MHz, METHANOL-$d_4$) δ ppm 8.38-8.23 (m, 2H), 7.67 (s, 1H), 7.54 (d, J=8.0 Hz, 1H), 7.47-7.13 (m, 5H), 7.01-6.86 (m, 3H), 6.69 (s, 1H), 6.18 (s, 1H), 4.85 (s, 1H), 4.32 (d, J=6.1, 8.6 Hz, 1H), 3.83 (d, J=6.0, 9.7 Hz, 1H), 3.75-3.62 (m, 2H), 2.37-2.27 (m, 1H), 2.26-2.17 (m, 1H), 1.96 (d, J=11.9 Hz, 1H), 1.82-1.59 (m, 4H), 1.44-1.27 (m, 3H), 1.22 (s, 9H), 1.19-1.01 (m, 2H).

Isomer 2:

To a solution of (2R,4R)—N-(4-(tert-butyl)phenyl)-N-(2-(cyclohexylamino)-2-oxo-1-(pyridin-3-yl)ethyl)-4-phenoxypyrrolidine-2-carboxamide (250 mg, 450.68 umol, 1 eq) in DMF (5 mL), was added $K_2CO_3$ (186.86 mg, 1.35 mmol, 3 eq), then BrCN (57.28 mg, 540.81 umol, 39.78 uL, 1.2 eq) was added at −10° C. The mixture was stirred at −10° C. for 2 hr. The reaction mixture was quenched by addition water (20 mL) at 25° C., and then extracted with EtOAc (20 mL*3). The combined organic layers were washed with brine (20 mL*2), dried over [$Na_2SO_4$], filtered and concentrated under reduced pressure to give a residue. The residue was purified by prep-HPLC to give (2R,4R)—N-(4-(tert-butyl)phenyl)-1-cyano-N-(2-(cyclohexylamino)-2-oxo-1-(pyridin-3-yl)ethyl)-4-phenoxypyrrolidine-2-carboxamide (105 mg, 181.12 umol, 40.19% yield, 100% purity) as a white solid. MS (ESI) m/z 580.2 $[M+H]^+$ Prep-HPLC condition: (column: Phenomenex Gemini-NX C18 75*30 mm*3 um; mobile phase: [water (0.05% $NH3H_2O$+10 mM NH4HCO3)-ACN]; B %: 40%-65%, 8 min).

$^1$H NMR (Isomer 2). $^1$H NMR (400 MHz, METHANOL-$d_4$) δ ppm 8.30 (d, J=1.2, 4.8 Hz, 1H), 8.20 (d, J=1.8 Hz, 1H), 7.68 (s, 1H), 7.55-7.30 (m, 4H), 7.17-6.87 (m, 5H), 5.96 (s, 2H), 4.94-4.90 (m, 1H), 4.43 (d, J=3.6, 8.8 Hz, 1H), 3.86-3.80 (m, 1H), 3.76-3.71 (m, 1H), 3.70-3.61 (m, 1H), 2.21-2.14 (m, 1H), 2.14-2.05 (m, 1H), 1.95 (d, J=11.2 Hz, 1H), 1.76 (d, J=13.4 Hz, 1H), 1.72-1.57 (m, 3H), 1.42-1.26 (m, 3H), 1.22 (s, 9H), 1.20-1.12 (m, 1H), 1.09-0.98 (m, 1H).

Example 173: Synthesis of Compound 675

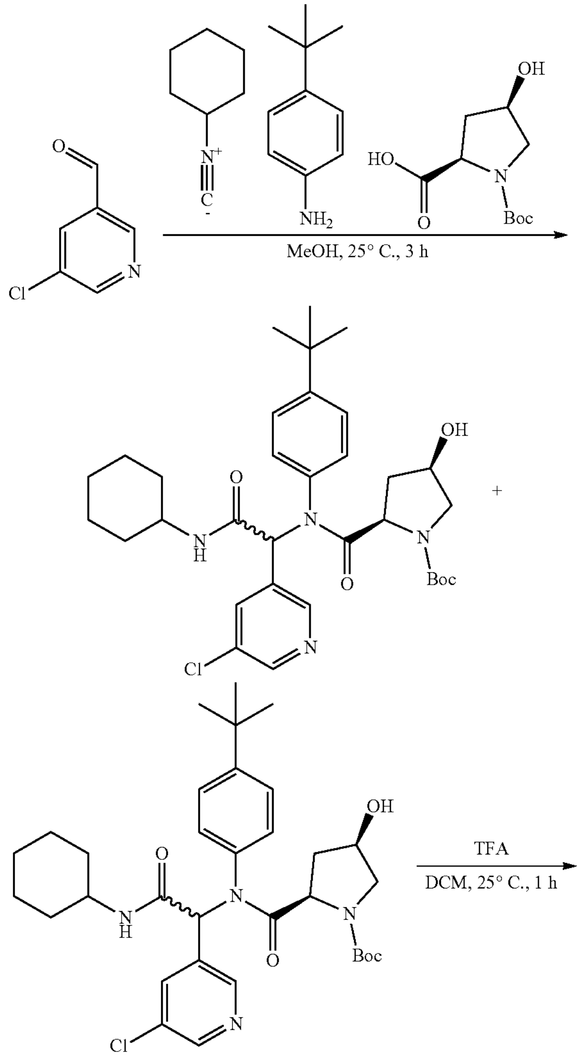

-continued

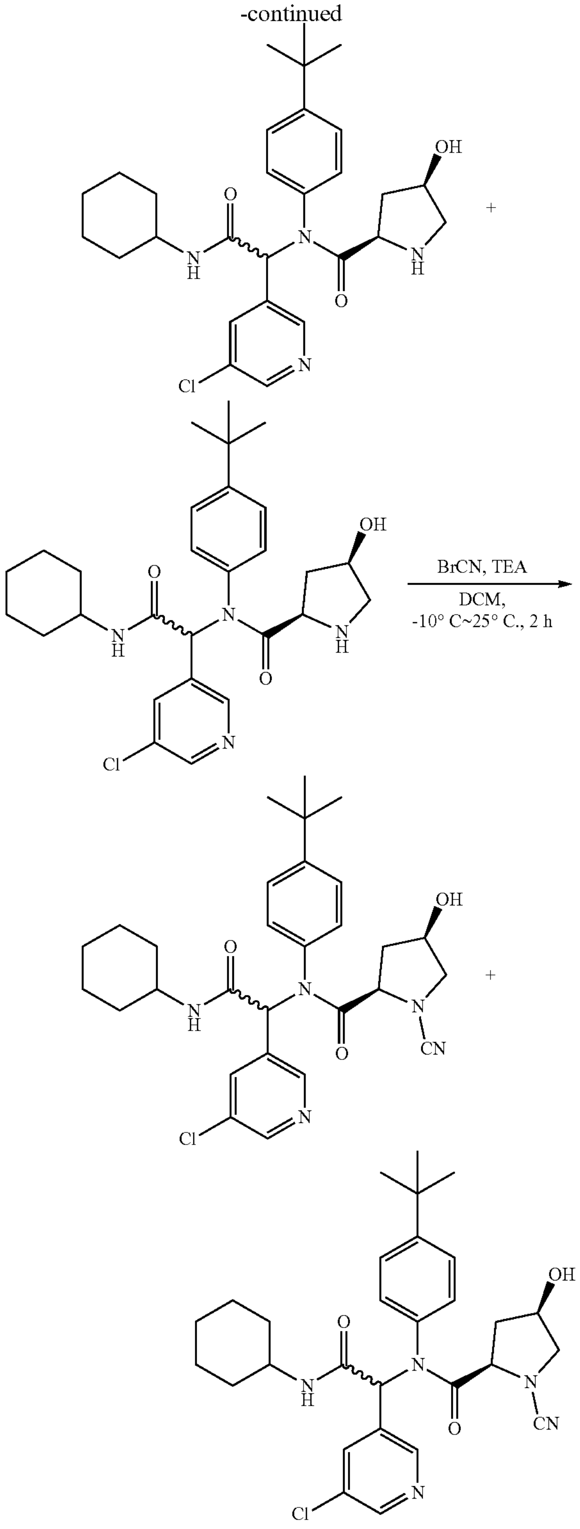

Step1: (2R,4R)-tert-butyl2-((4-(tert-butyl)phenyl)(1-(5-chloropyridin-3-yl)-2-(cyclohexylamino)-2-oxoethyl)carbamoyl)-4-hydroxypyrrolidine-1-carboxylate A solution of 5-chloronicotinaldehyde (400 mg, 2.83 mmol, 1 eq), 4-(tert-butyl)aniline (421.69 mg, 2.83 mmol, 446.24 uL, 1 eq) in MeOH (15 mL) was stirred at 25° C. for 1 h, and added (2R,4R)-1-(tert-butoxycarbonyl)-4-hydroxypyrrolidine-2-carboxylic acid (653.44 mg, 2.83 mmol, 1 eq) was added. After stirring for 0.5 h at 25° C., isocyanocyclohexane (277.64 mg, 2.54 mmol, 316.21 uL, 0.9 eq) was added and stirred at 25° C. for 1.5 h. Upon completion, the reaction mixture was concentrated under reduced pressure and was purified by column chromatography ($SiO_2$, petroleum ether:ethyl acetate=5:1) to give a product (2R,4R)-tert-butyl2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 23.09% yield) and (2R,4R)-tert-butyl2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 23.09% yield) as white solid. MS (ESI) m/z 613.3 $[M+H]^+$ Step 2: (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide Isomer 1: To a solution of (2R,4R)-tert-butyl 2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 1 eq) in DCM (9 mL) was added TFA (4.46 g, 39.14 mmol, 2.90 mL, 60 eq) and the mixture was stirred at 25° C. for 1 h. Upon completion, the mixture was quenched by addition $NaHCO_3$ (50 mL) and then extracted with EtOAc (30 mL*3). The combined organic layers were washed with brine (50 mL), dried over $Na_2SO_4$, filtered and concentrated under reduced pressure to give the crude product (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol) was obtained as white solid. MS (ESI) m/z 513.3 $[M+H]^+$ Isomer 2: To a solution of (2R,4R)-tert-butyl 2-((4-(tert-butyl)phenyl)(1-(5-chloropyridin-3-yl)-2-(cyclohexylamino)-2-oxoethyl)carbamoyl)-4-hydroxypyrrolidine-1-carboxylate (400 mg, 652.33 umol, 1 eq) in DCM (10 mL) was added TFA (4.46 g, 39.14 mmol, 2.90 mL, 60 eq) and the mixture was stirred at 25° C. for 1 h. Upon completion, the mixture was quenched by addition $NaHCO_3$ 50 mL and then extracted with EtOAc 30 mL*3. The combined organic layers were washed with brine 50 mL, dried over $Na_2SO_4$, filtered and concentrated under reduced pressure to give the crude product (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol) was obtained as white solid. MS (ESI) m/z 513.3 $[M+H]^+$ Step 3: (2R,4R)—N-(4-(tert-butyl)phenyl)-N-(1-(5-chloropyridin-3-yl)-2-(cyclohexylamino)-2-oxoethyl)-1-cyano-4-hydroxypyrrolidine-2-carboxamide Isomer 1: To a solution of (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol, 1 eq) in DCM (3 mL) was added TEA (177.50 mg, 1.75 mmol, 244.15 uL, 3 eq) and the mixture was cooled at −10° C. BrCN (92.90 mg, 877.07 umol, 64.51 uL, 1.5 eq) in DCM (0.5 mL) was added and the solution was stirred for 0.5 h at 0° C. and warmed to 25° C. gradually. Upon completion, the mixture was added into water (15 mL) and was extracted with DCM (10 mL*3), then was concentration under reduced pressure and was purified by prep-HPLC (column: Phenomenex Gemini-NX 80*40 mm*3 um; mobile phase: [water (10 mM $NH_4HCO_3$)-ACN]; B %: 30%-60%, 8 min) to afford (2R,4R)—N-(4-(tert-butyl)phenyl)-N-(1-(5-chloropyridin-3-yl)-2-(cyclohexylamino)-2-oxoethyl)-1-cyano-4-hydroxypyrrolidine-2-carboxamide (30 mg, 55.75 umol, 9.54% yield) was obtained as white solid. MS (ESI) m/z 538.1 $[M+H]^+$ $^1H$ NMR (400 MHz, MeOD-$d_4$) δ=8.43-8.19 (m, 2H), 7.78-7.10 (m, 4H), 6.82-6.45 (m, 1H), 6.15 (s, 1H), 4.31-4.19 (m, 2H), 3.76-3.64 (m, 1H), 3.58 (dd, J=5.6, 9.4 Hz, 1H), 3.42 (dd, J=4.8, 9.2 Hz, 1H), 2.21-2.09 (m, 1H), 2.06-1.88 (m, 2H), 1.81-1.59 (m, 4H), 1.52-0.92 (m, 15H)

Isomer 2:

To a solution of (2R,4R)—N-(4-(tert-butyl)phenyl)-N-(1-(5-chloropyridin-3-yl)-2-(cyclohexylamino)-2-oxoethyl)-4-hydroxypyrrolidine-2-carboxamide (300 mg, 584.72 umol, 1 eq) in DCM (3 mL) was added TEA (177.50 mg, 1.75 mmol, 244.15 uL, 3 eq) and the mixture was cooled at −10° C. and added BrCN (92.90 mg, 877.07 umol, 64.51 uL, 1.5 eq) in DCM (0.5 mL) and the solution was stirred for 0.5 h at 0° C. and warmed to 25° C. gradually for 1.5 h. Upon completion, the mixture was added into water (20 mL) and was extracted with DCM (10 mL*3), then was concentration under reduced pressure and was purified by prep-HPLC (column: Phenomenex Gemini-NX 80*40 mm*3 um; mobile phase: [water (10 mM $NH_4HCO_3$)-ACN]; B %: 30%-60%, 8 min) to afford (2R,4R)—N-(4-(tert-butyl)phenyl)-N-(1-(5-chloropyridin-3-yl)-2-(cyclohexylamino)-2-oxoethyl)-1-cyano-4-hydroxypyrrolidine-2-carboxamide (30 mg, 55.75 umol, 9.54% yield) was obtained as white solid. MS (ESI) m/z 538.1 $[M+H]^+$ $^1H$ NMR (400 MHz, MeOD-$d_4$) δ=8.43-8.26 (m, 2H), 7.82-7.05 (m, 4H), 6.81-6.37 (m, 1H), 6.16 (s, 1H), 4.35-4.19 (m, 2H), 3.67 (tt, J=3.8, 10.8 Hz, 1H), 3.57 (dd, J=5.4, 9.6 Hz, 1H), 3.43 (dd, J=4.0, 9.4 Hz, 1H), 2.18-2.02 (m, 1H), 1.93 (td, J=4.4, 13.2 Hz, 2H), 1.79-1.59 (m, 4H), 1.51-0.96 (m, 15H)

Example 174: Synthesis of Compound 723

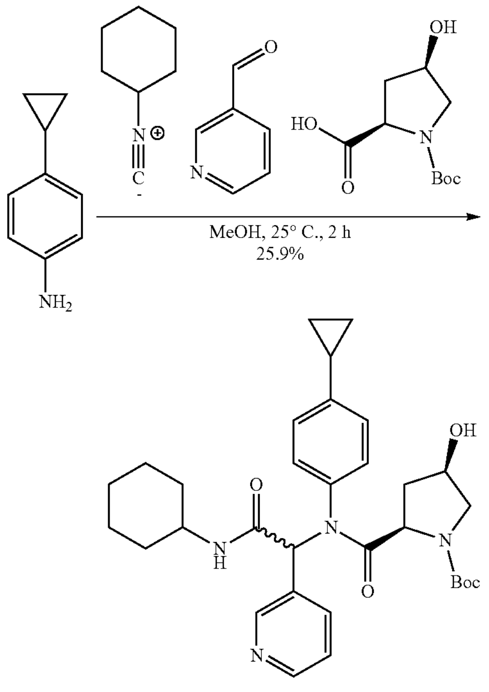

-continued

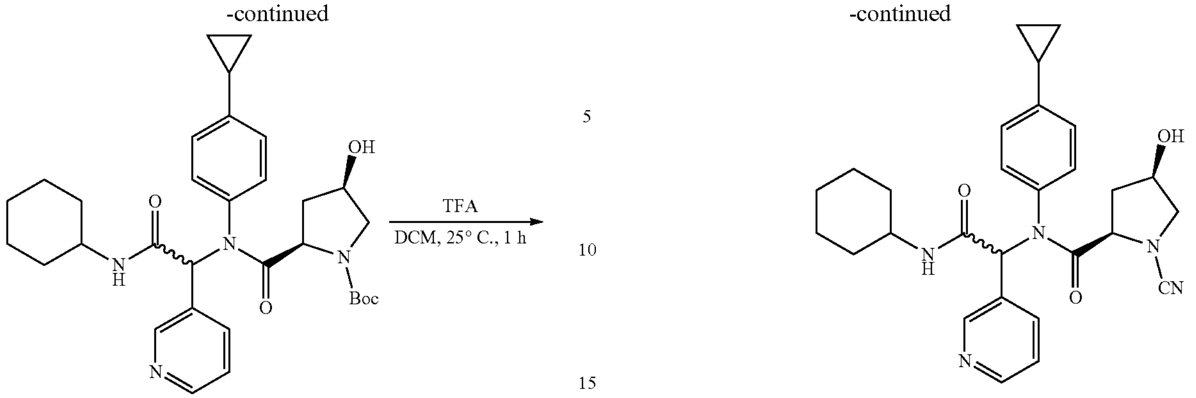

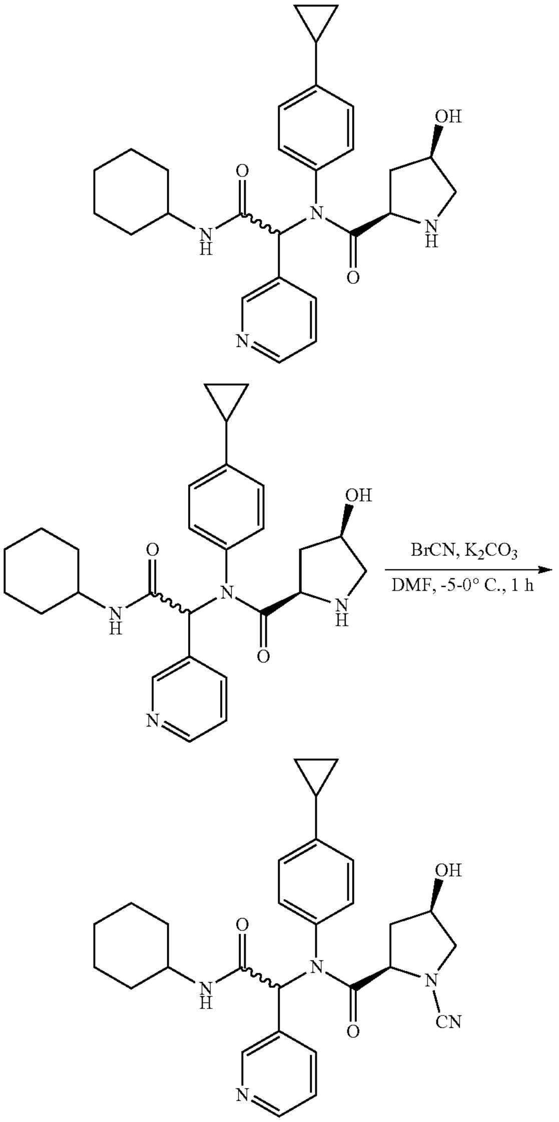

Step 1: (2R,4R)-tert-butyl2-((2-(cyclohexylamino)-2-oxo-1-(pyridin-3-yl)ethyl)(4-cyclopropylphenyl) carbamoyl)-4-hydroxypyrrolidine-1-carboxylate A solution of 4-cyclopropylaniline (0.25 g, 1.88 mmol, 1 eq) and pyridine-3-carbaldehyde (241.26 mg, 2.25 mmol, 211.63 uL, 1.2 eq) in MeOH (4 mL) was stirred at 25° C. for 30 mins, and then (2R,4R)-1-tert-butoxycarbonyl-4-hydroxy-pyrrolidine-2-carboxylic acid (434.05 mg, 1.88 mmol, 1 eq) was added. After stirring 15 mins, the solution was cooled to −40° C. and isocyanocyclohexane (204.91 mg, 1.88 mmol, 233.38 uL, 1 eq) in MeOH (1 mL) was added drop-wise within 15 mins for 3 times, and the mixture was stirred at 25° C. for 1 h. Upon completion, the reaction mixture was concentrated under reduced pressure to give a residue. The residue was purified by column chromatography ($SiO_2$, petroleum ether:ethyl acetate=2:1 to 0:1) to afford tert-butyl (2R,4R)-2-[[2-(cyclohexylamino)-2-oxo-1-(3-pyridyl)ethyl]-(4-cyclopropylphenyl)carbamoyl]-4-hydroxy-pyrrolidine-1-carboxylate Isomer 1 (0.15 g, 239.92 umol, 12.78% yield, 90% purity) as a yellow solid. MS (ESI) m/z 563.3 $[M+H]^+$.

Tert-butyl (2R,4R)-2-[[2-(cyclohexylamino)-2-oxo-1-(3-pyridyl)ethyl]-(4-cyclopropylphenyl)carbamoyl]-4-hydroxy-pyrrolidine-1-carboxylate Isomer 2 (0.15 g, 253.24 umol, 13.49% yield, 95% purity) was obtained as a yellow solid. MS (ESI) m/z 563.2 $[M+H]^+$.

Step 2: (2R,4R)—N-(2-(cyclohexylamino)-2-oxo-1-(pyridin-3-yl)ethyl)-N-(4-cyclopropylphenyl)-4-hydroxypyrrolidine-2-carboxamide Isomer 1

To a solution of tert-butyl (2R,4R)-2-[[2-(cyclohexylamino)-2-oxo-1-(3-pyridyl)ethyl]-(4-cyclopropylphenyl) carbamoyl]-4-hydroxy-pyrrolidine-1-carboxylate Isomer 1 (0.13 g, 231.03 umol, 1 eq) in DCM (1 mL) was added TFA (770.00 mg, 6.75 mmol, 0.5 mL, 29.23 eq), and the mixture was stirred at 25° C. for 1 h. Upon completion, the reaction mixture was dried by blowing $N_2$ and then diluted with sat. $NaHCO_3$ solution (15 mL) and extracted with DCM (5 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-N-(4-cyclopropylphenyl)-4-hydroxy-pyrrolidine-2-carboxamide Isomer 1 (0.1 g, crude) as a yellow oil.

(2R,4R)—N-[2-(cyclohexylamino)-2-oxo-1-(3-pyridyl) ethyl]-N-(4-cyclopropylphenyl)-4-hydroxy-pyrrolidine-2-carboxamide Isomer 1 (0.03 g, 64.85 umol, 1 eq) was purified by prep-HPLC (column: Phenomenex Gemini-NX 150*30 mm*5 um; mobile phase: [water (0.1% TFA)-ACN];

B %: 10%-40%, 9 min) to afford (2R,4R)—N-[2-(cyclohexylamino)-2-oxo-1-(3-pyridyl)ethyl]-N-(4-cyclopropylphenyl)-4-hydroxy-pyrrolidine-2-carboxamide Isomer 1 (27.06 mg, 58.50 umol, 90.20% yield) as a white solid. MS (ESI) m/z 463.1 $[M+H]^+$.

$^1$H NMR (400 MHz, MeOD-$d_4$) δ=8.51-8.39 (m, 2H), 8.16 (br d, J=7.9 Hz, 1H), 7.80 (br d, J=8.0 Hz, 1H), 7.63 (br s, 1H), 7.43 (dd, J=5.2, 7.9 Hz, 1H), 7.20-6.53 (m, 3H), 6.26 (s, 1H), 4.40-4.30 (m, 1H), 4.21 (t, J=8.5 Hz, 1H), 3.80-3.64 (m, 1H), 3.35-3.32 (m, 1H), 3.23-3.13 (m, 1H), 2.01 (dd, J=4.3, 8.6 Hz, 2H), 1.92 (br d, J=12.5 Hz, 1H), 1.86-1.58 (m, 5H), 1.42-1.05 (m, 5H), 1.02-0.91 (m, 2H), 0.68-0.52 (m, 2H).

(2R,4R)—N-(2-(cyclohexylamino)-2-oxo-1-(pyridin-3-yl)ethyl)-N-(4-cyclopropylphenyl)-4-hydroxy-pyrrolidine-2-carboxamide Isomer 2

To a solution of tert-butyl (2R,4R)-2-[[2-(cyclohexylamino)-2-oxo-1-(3-pyridyl)ethyl]-(4-cyclopropylphenyl) carbamoyl]-4-hydroxy-pyrrolidine-1-carboxylate Isomer 2 (0.13 g, 231.03 umol, 1 eq) in DCM (1 mL) was added TFA (770.00 mg, 6.75 mmol, 0.5 mL, 29.23 eq), and the mixture was stirred at 25° C. for 1 h. Upon completion, the reaction mixture was dried by blowing $N_2$ and then diluted with sat. $NaHCO_3$ solution (5 mL) and extracted with DCM (2 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-N-(4-cyclopropylphenyl)-4-hydroxy-pyrrolidine-2-carboxamide Isomer 2 (0.1 g, crude) as a yellow oil.

(2R,4R)—N-[2-(cyclohexylamino)-2-oxo-1-(3-pyridyl) ethyl]-N-(4-cyclopropylphenyl)-4-hydroxy-pyrrolidine-2-carboxamide Isomer 2 (0.03 g, 64.85 umol, 1 eq) was purified by prep-HPLC (column: Phenomenex Gemini-NX 150*30 mm*5 um; mobile phase: [water (0.1% TFA)-ACN]; B %: 10%-40%, 9 min) to give (2R,4R)—N-[2-(cyclohexylamino)-2-oxo-1-(3-pyridyl)ethyl]-N-(4-cyclopropylphenyl)-4-hydroxy-pyrrolidine-2-carboxamide Isomer 2 (21.48 mg, 46.43 umol, 71.60% yield, 100% purity) as a white solid. MS (ESI) m/z 463.1 $[M+H]^+$.

$^1$H NMR (400 MHz, MeOD-$d_4$) δ=8.52-8.39 (m, 2H), 8.17 (br d, J=8.0 Hz, 1H), 7.75 (br d, J=8.0 Hz, 1H), 7.64 (br s, 1H), 7.41 (dd, J=5.2, 7.9 Hz, 1H), 7.25-6.33 (m, 3H), 6.08 (s, 11H), 4.41-4.31 (m, 1H), 4.23 (dd, J=6.5, 10.1 Hz, 1H), 3.68 (br d, J=5.5 Hz, 1H), 3.34 (br s, 1H), 3.18 (dd, J=4.2, 11.8 Hz, 1H), 2.06-1.81 (m, 4H), 1.79-1.56 (m, 4H), 1:41-1.04 (m, 5H), 0.97 (dd, J=2.0, 8.4 Hz, 2H), 0.61 (dt, J=2.4, 5.1 Hz, 2H).

Step 3: (2R,4R)—N-(2-(cyclohexylamino)-2-oxo-1-(pyridin-3-yl)ethyl)-N-(4-cyclopropylphenyl)-4-hydroxypyrrolidine-2-carboxamide Isomer 1

To a solution of (2R,4R)—N-[2-(cyclohexylamino)-2-oxo-1-(3-pyridyl)ethyl]-N-(4-cyclopropylphenyl)-4-hydroxy-pyrrolidine-2-carboxamide Isomer 1 (0.07 g, 151.32 umol, 1 eq) in DMF (1.5 mL) was added $K_2CO_3$ (62.74 mg, 453.97 umol, 3 eq), and then the solution was cooled to −5° C. and BrCN (19.23 mg, 181.59 umol, 13.36 uL, 1.2 eq) in DMF (0.5 mL) was added drop-wise. After stirring the mixture at 0° C. for 1 h, the reaction mixture was diluted with water (10 mL) and extracted with ethyl acetate (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH4HCO_3$)-ACN]; B %: 25%-60%, 10 min) to give (2R,4R)-1-cyano-N-[2-(cyclohexylamino)-2-oxo-1-(3-pyridyl)ethyl]-N-(4-cyclopropylphenyl)-4-hydroxy-pyrrolidine-2-carboxamide Isomer 1 (33.85 mg, 69.42 umol, 45.88% yield, 100% purity) as a light yellow solid. MS (ESI) m/z 488.1 $[M+H]^+$.

$^1$H NMR (400 MHz, MeOD-$d_4$) δ=8.30 (dt, J=1.7, 4.5 Hz, 2H), 7.72-7.57 (m, 1H), 7.54 (td, J=1.8, 7.9 Hz, 1H), 7.20 (dd, J=4.9, 7.9 Hz, 1H), 7.06 (br s, 1H), 6.82 (br d, J=2.6 Hz, 1H), 6.68-6.47 (m, 1H), 6.17 (s, 1H), 4.31-4.13 (m, 2H), 3.79-3.64 (m, 1H), 3.55-3.51 (m, 1H), 3.41 (dd, J=4.9, 9.3 Hz, 1H), 2.20-2.05 (m, 1H), 2.04-1.89 (m, 2H), 1.86-1.57 (m, 5H), 1.44-1.02 (m, 5H), 0.99-0.87 (m, 2H), 0.69-0.53 (m, 2H).

(2R,4R)—N-(2-(cyclohexylamino)-2-oxo-1-(pyridin-3-yl)ethyl)-N-(4-cyclopropylphenyl)-4-hydroxy-pyrrolidine-2-carboxamide Isomer 2

To a solution of (2R,4R)—N-[2-(cyclohexylamino)-2-oxo-1-(3-pyridyl)ethyl]-N-(4-cyclopropylphenyl)-4-hydroxy-pyrrolidine-2-carboxamide Isomer 2 (0.07 g, 151.32 umol, 1 eq) in DMF (1.5 mL) was added $K_2CO_3$ (62.74 mg, 453.97 umol, 3 eq), and then the solution was cooled to −5° C. BrCN (19.23 mg, 181.59 umol, 13.36 uL, 1.2 eq) in DMF (0.5 mL) was added drop-wise, and the mixture was stirred at 0° C. for 1 h. Upon completion, the reaction mixture was diluted with water (10 mL) and extracted with ethyl acetate (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH4HCO_3$)-ACN]; B %: 25%-60%, 10 min) to give (2R,4R)-1-cyano-N-[2-(cyclohexylamino)-2-oxo-1-(3-pyridyl)ethyl]-N-(4-cyclopropylphenyl)-4-hydroxy-pyrrolidine-2-carboxamide Isomer 2 (20.53 mg, 42.10 umol, 27.82% yield, 100% purity) as a light yellow solid. MS (ESI) m/z 488.1 $[M+H]^+$.

$^1$H NMR (400 MHz, MeOD-$d_4$) δ=8.34 (br s, 2H), 7.67 (br s, 1H), 7.55 (br d, J=7.9 Hz, 1H), 7.22 (dd, J=5.0, 7.8 Hz, 1H), 7.10 (br dd, J=2.1, 3.1 Hz, 1H), 6.95-6.70 (m, 1H), 6.66-6.36 (m, 1H), 6.03 (s, 1H), 4.29-4.15 (m, 2H), 3.75-3.62 (m, 1H), 3.57 (dd, J=5.6, 9.5 Hz, 1H), 3.42 (dd, J=4.2, 9.5 Hz, 1H), 2.16-2.02 (m, 1H), 1.97-1.58 (m, 7H), 1.41-1.03 (m, 5H), 0.99-0.86 (m, 2H), 0.68-0.54 (m, 2H).

Example 175: Synthesis of Compound 735

Step 1

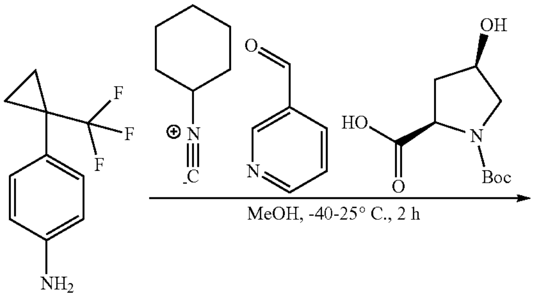

-continued

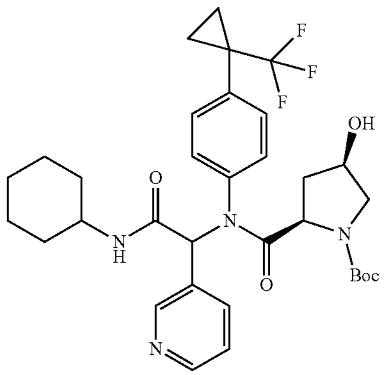

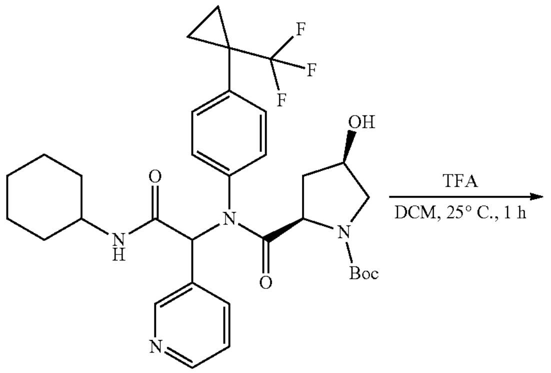

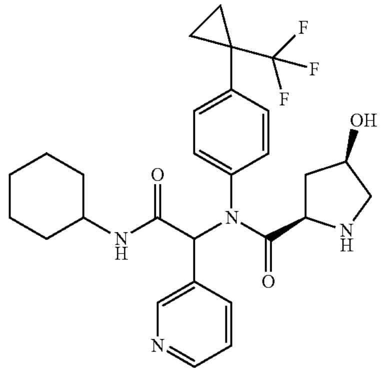

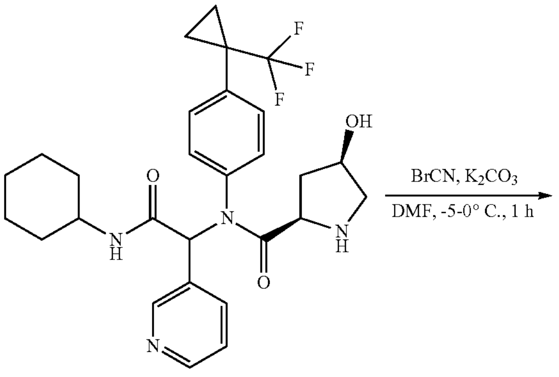

-continued

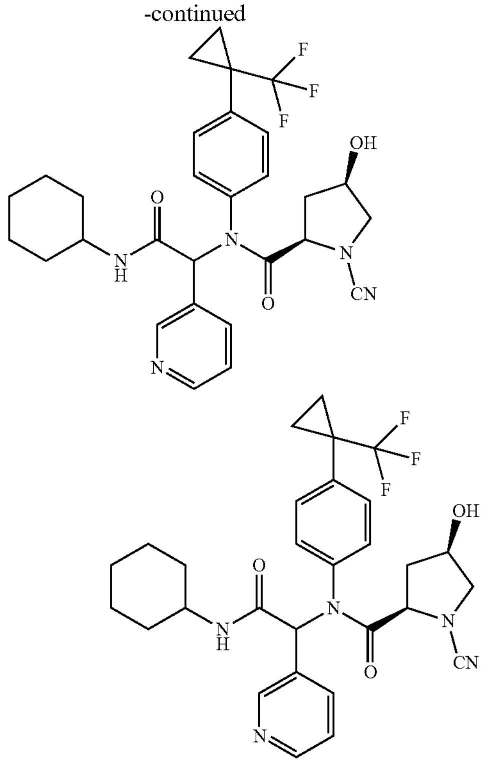

Step 1: (2R,4R)-tert-butyl 2-((2-(cyclohexylamino)-2-oxo-1-(pyridin-3-yl)ethyl)(4-(1-(trifluoromethyl)cyclopropyl)phenyl)carbamoyl)-4-hydroxypyrrolidine-1-carboxylate A solution of 4-[1-(trifluoromethyl)cyclopropyl]aniline (0.25 g, 1.24 mmol, 1 eq) and pyridine-3-carbaldehyde (159.72 mg, 1.49 mmol, 140.10 uL, 1.2 eq) in MeOH (3 mL) was stirred at 25° C. for 30 min, and then (2R,4R)-1-tert-butoxycarbonyl-4-hydroxy-pyrrolidine-2-carboxylic acid (287.35 mg, 1.24 mmol, 1 eq) was added. After stirring 15 min, the solution was cooled to −40° C. and isocyanocyclohexane (135.66 mg, 1.24 mmol, 154.51 uL, 1 eq) in MeOH (1 mL) was added drop-wise within 15 min for 3 times. After stirring the mixture at 25° C. for 1 h, the reaction mixture was concentrated under reduced pressure to give a residue. The residue was purified by column chromatography ($SiO_2$, petroleum ether:ethyl acetate=2:1 to 0:1) to give tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate Isomer 1 (0.3 g, 451.88 umol, 36.37% yield, 95% purity) as a yellow solid. MS (ESI) m/z 631.2 $[M+H]^+$.

Tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate Isomer 2 (0.3 g, 451.88 umol, 36.37% yield, 95% purity) was obtained as a yellow solid. MS (ESI) m/z 631.2 $[M+H]^+$.

Step 2: (2R,4R)—N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide Isomer 1

To a solution of tert-butyl (2R,4R)-2-[[2-(cyclohexylamino)-2-oxo-1-(3-pyridyl)ethyl]-[4-[1-(trifluoromethyl)

cyclopropyl]phenyl]carbamoyl]-4-hydroxy-pyrrolidine-1-carboxylate Isomer 1 (0.25 g, 396.39 umol, 1 eq) in DCM (2 mL) was added TFA (1.54 g, 13.51 mmol, 1 mL, 34.07 eq), and the mixture was stirred at 25° C. for 1 h. Upon completion, the reaction mixture was dried by blowing $N_2$ and then diluted with sat. $NaHCO_3$ solution (20 mL) and extracted with DCM (10 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 1 (0.2 g, crude) as a yellow oil.

(2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 1 (0.07 g, 131.93 umol, 1 eq) was purified by prep-HPLC (column: Phenomenex Gemini-NX 150*30 mm*5 um; mobile phase: [water (0.1% TFA)-ACN]; B %: 15%-45%, 9 min) to afford (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 1 (23.49 mg, 44.27 umol, 33.56% yield, 100% purity) as a white solid. MS (ESI) m/z 531.1 $[M+H]^+$.

$^1H$ NMR (400 MHz, MeOD-$d_4$) δ=8.40 (dt, J=1.7, 4.5 Hz, 2H), 8.18 (br d, J=7.8 Hz, 1H), 7.69 (br d, J=8.0 Hz, 2H), 7.42 (br d, J=3.0 Hz, 2H), 7.33 (dd, J=5.2, 7.9 Hz, 1H), 6.98 (br s, 1H), 6.26 (s, 1H), 4.35 (br d, J=2.1 Hz, 1H), 4.23 (dd, J=7.3, 9.7 Hz, 1H), 3.73 (br d, J=1.9 Hz, 1H), 3.33 (br s, 1H), 3.24-3.12 (m, 1H), 2.09-1.97 (m, 2H), 1.91 (br d, J=13.0 Hz, 1H), 1.83-1.58 (m, 4H), 1.40-1.08 (m, 7H), 0.98 (br d, J=5.3 Hz, 2H).

(2R,4R)—N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide Isomer 2

To a solution of tert-butyl (2R,4R)-2-[[2-(cyclohexylamino)-2-oxo-1-(3-pyridyl)ethyl]-[4-[1-(trifluoromethyl)cyclopropyl]phenyl]carbamoyl]-4-hydroxy-pyrrolidine-1-carboxylate Isomer 2 (0.25 g, 396.39 umol, 1 eq) in DCM (2 mL) was added TFA (1.54 g, 13.51 mmol, 1 mL, 34.07 eq), and the mixture was stirred at 25° C. for 1 h. Upon completion, the reaction mixture was dried by blowing $N_2$ and then diluted with sat. $NaHCO_3$ solution (20 mL) and extracted with DCM (10 mL*3). The combined organic layers were dried over $Na_2SO_4$, filtered and concentrated under reduced pressure to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 2 (0.2 g, crude) as a yellow oil.

(2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 2 (0.07 g, 131.93 umol, 1 eq) was purified by prep-HPLC (column: Phenomenex Gemini-NX 150*30 mm*5 um; mobile phase: [water (0.1% TFA)-ACN]; B %: 15%-45%, 9 min) to give (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 2 (25.76 mg, 48.31 umol, 36.62% yield, 99.5% purity) as a white solid. MS (ESI) m/z 531.2 $[M+H]^+$.

$^1H$ NMR (400 MHz, MeOD-$d_4$) δ=8.52-8.41 (m, 2H), 7.99-7.56 (m, 2H), 7.55-7.19 (m, 3H), 7.19-6.51 (m, 1H), 6.09 (s, 1H), 4.41-4.32 (m, 1H), 4.27 (dd, J=6.9, 9.6 Hz, 1H), 3.74-3.61 (m, 1H), 3.34 (s, 1H), 3.19 (dd, J=4.3, 11.9 Hz, 1H), 2.04-1.93 (m, 2H), 1.86 (br d, J=10.1 Hz, 1H), 1.80-1.58 (m, 4H), 1.38-0.95 (m, 9H).

Step 3: (2R,4R)-1-cyano-N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide Isomer 1

To a solution of (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 1 (0.13 g, 245.01 umol, 1 eq) in DMF (2 mL) was added $K_2CO_3$ (101.59 mg, 735.04 umol, 3 eq), and then the solution was cooled to −5° C. BrCN (31.14 mg, 294.02 umol, 21.63 uL, 1.2 eq) in DMF (1 mL) was added dropwise, and the mixture was stirred at 0° C. for 1 h. Upon completion, the reaction mixture was diluted with water (10 mL) and extracted with ethyl acetate (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 10 min) to give (2R,4R)-1-cyano-N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 1 (81.23 mg, 146.20 umol, 59.67% yield, 100% purity) as a light yellow solid. MS (ESI) m/z 556.1 $[M+H]^+$.

$^1H$ NMR (400 MHz, MeOD-$d_4$) δ=8.43-8.18 (m, 2H), 8.01-7.59 (m, 1H), 7.58-7.12 (m, 4H), 7.06-6.51 (m, 11H), 6.19 (s, 1H), 4.32-4.13 (m, 2H), 3.71 (ddd, J=3.9, 6.8, 10.6 Hz, 1H), 3.57 (dd, J=5.7, 9.4 Hz, 1H), 3.41 (dd, J=4.9, 9.3 Hz, 1H), 2.20-2.07 (m, 1H), 2.06-1.88 (m, 2H), 1.83-1.58 (m, 4H), 1.44-0.91 (m, 9H).

(2R,4R)-1-cyano-N-(2-(cyclohexylamino)-2-oxo-1-(pyridin-3-yl)ethyl)-4-hydroxy-N-(4-(1-(trifluoromethyl)cyclopropyl)phenyl)pyrrolidine-2-carboxamide Isomer 2

To a solution of (2R,4R)—N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 2 (0.13 g, 245.01 umol, 1 eq) in DMF (2 mL) was added $K_2CO_3$ (101.59 mg, 735.04 umol, 3 eq), and then the solution was cooled to −5° C. and BrCN (31.14 mg, 294.02 umol, 21.63 uL, 1.2 eq) in DMF (1 mL) was added dropwise. After stirring the mixture for 1 h at 0° C., the reaction mixture was diluted with water (10 mL) and extracted with ethyl acetate (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 10 min) to give (2R,4R)-1-cyano-N-[2-(cyclohexylamino)-2-oxo-1-(3-pyridyl)ethyl]-4-hydroxy-N-[4-[1-(trifluoromethyl)cyclopropyl]phenyl]pyrrolidine-2-carboxamide Isomer 2 (89.41 mg, 160.93 umol, 65.68% yield, 100% purity) as a light yellow solid. MS (ESI) m/z 556.1 $[M+H]^+$.

$^1H$ NMR (400 MHz, MeOD-$d_4$) δ=8.54-8.22 (m, 2H), 8.04-7.63 (m, 1H), 7.61-7.11 (m, 4H), 7.02-6.42 (m, 1H), 6.05 (s, 1H), 4.35-4.15 (m, 2H), 3.76-3.62 (m, 1H), 3.57 (dd, J=5.4, 9.5 Hz, 1H), 3.43 (dd, J=4.0, 9.5 Hz, 1H), 2.17-2.05 (m, 1H), 1.93 (td, J=4.3, 13.3 Hz, 2H), 1.83-1.54 (m, 4H), 1.44-0.94 (m, 9H).

Example 176: Synthesis of Compound 775

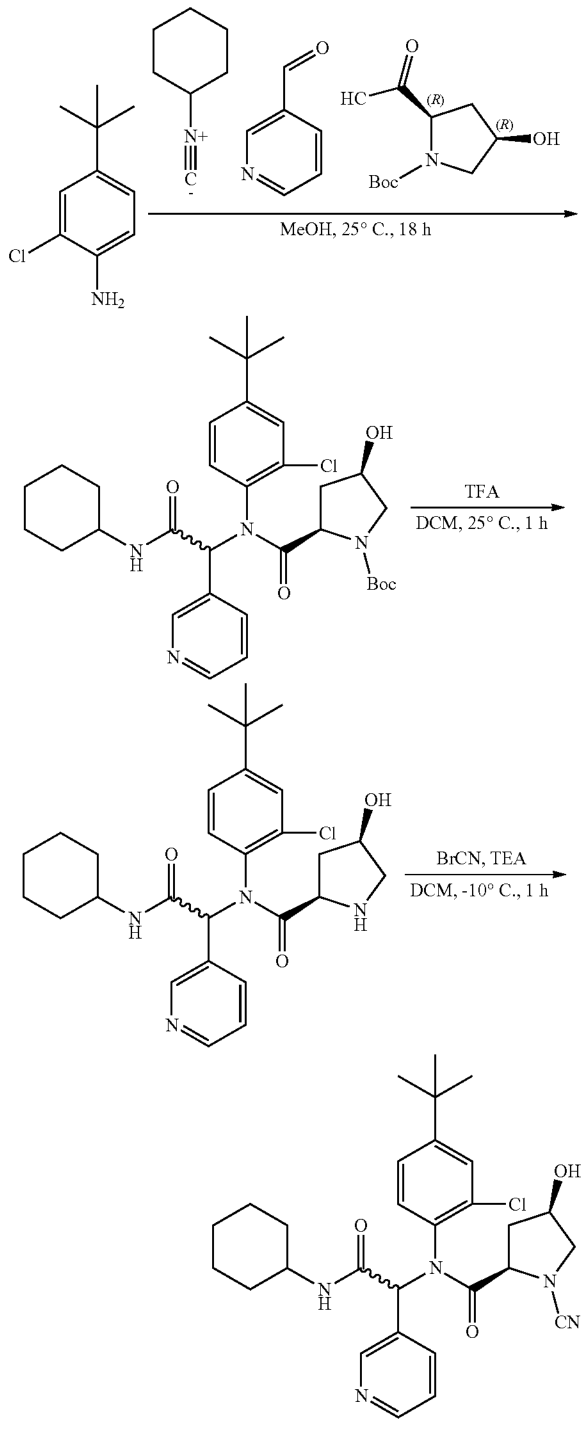

Step 1: (2R)-tert-butyl (2R,4R)-tert-butyl 2-((4-(tert-butyl)-2-chlorophenyl)(2-(cyclohexylamino)-2-oxo-1-(pyridin-3-yl)ethyl)carbamoyl)-4-hydroxypyrrolidine-1-carboxylate A solution of pyridine-3-carbaldehyde (174.94 mg, 1.63 mmol, 153.46 uL, 1 eq), 4-tert-butyl-2-chloro-aniline (300 mg, 1.63 mmol, 206.63 uL, 1 eq), (2R,4R)-1-tert-butoxycarbonyl-4-hydroxy-pyrrolidine-2-carboxylic acid (377.69 mg, 1.63 mmol, 1 eq) and isocyanocyclohexane (160.47 mg, 1.47 mmol, 182.77 uL, 0.9 eq) in MeOH (10 mL) was stirred at 25° C. for 16 h. The reaction mixture was concentrated under reduced pressure, then purified by prep-HPLC to give the product (2R,4R)-tert-butyl 2-((4-(tert-butyl)-2-chlorophenyl)(2-(cyclohexylamino)-2-oxo-1-(pyridin-3-yl)ethyl)carbamoyl)-4-hydroxypyrrolidine-1-carboxylate (614 mg, 1.00 mmol, 61.31% yield) as yellow solid. MS (ESI) m/z 613.4 $[M+H]^+$ prep-HPLC condition: column: Phenomenex luna C18 250*50 mm*10 um; mobile phase: [water (0.1% TFA)-ACN]; B %: 40%-60%, 10 min.

Step 2: (2R,4R)—N-(4-(tert-butyl)-2-chlorophenyl)-N-(2-(cyclohexylamino)-2-oxo-1-(pyridin-3-yl)ethyl)-4-hydroxypyrrolidine-2-carboxamide A solution of (2R,4R)-tert-butyl 2-((4-(tert-butyl)-2-chlorophenyl)(2-(cyclohexylamino)-2-oxo-1-(pyridin-3-yl)ethyl)carbamoyl)-4-hydroxypyrrolidine-1-carboxylate (154 mg, 228.54 umol, 91% purity, 1 eq) in TFA (2 mL) and DCM (6 mL) was stirred at 25° C. for 1 h. The reaction mixture was concentrated under reduced pressure and then purified by prep-HPLC to give (2R,4R)—N-(4-tert-butyl-2-chlorophenyl)-N-[2-(cyclohexylamino)-2-oxo-1-(3-pyridyl)ethyl]-4-hydroxy-pyrrolidine-2-carboxamide (115 mg, 212.93 umol, 93.17% yield, 95% purity) as white solid. MS (ESI) m/z 513.2 $[M+H]^+$.

prep-HPLC condition: column: Phenomenex Gemini-NX 150*30 mm*5 um; mobile phase: [water (0.1% TFA)-ACN]; B %: 15%-45%, 9 min.

Step 3: (2R,4R)—N-(4-(tert-butyl)-2-chlorophenyl)-1-cyano-N-(2-(cyclohexylamino)-2-oxo-1-(pyridin-3-yl)ethyl)-4-hydroxypyrrolidine-2-carboxamide To a solution of (2R,4R)—N-(4-tert-butyl-2-chloro-phenyl)-N-[2-(cyclohexylamino)-2-oxo-1-(3-pyridyl)ethyl]-4-hydroxy-pyrrolidine-2-carboxamide (105 mg, 204.65 umol, 1 eq) in DCM (1.5 mL) was added TEA (62.13 mg, 613.95 umol, 85.45 uL, 3 eq). BrCN (22.11 mg, 208.74 umol, 15.35 uL, 1.02 eq) was added under $N_2$ at −10° C., and the mixture was stirred at −10° C. for 1 h. The mixture was diluted with water (10.0 mL) and extracted with EtOAc (10.0 mL*3). The organic layers were washed with brine (10.0 mL), dried over $Na_2SO_4$, filtered, concentrated under reduced pressure and purified by prep-HPLC to give (2R,4R)—N-(4-(tert-butyl)-2-chlorophenyl)-1-cyano-N-(2-(cyclohexylamino)-2-oxo-1-(pyridin-3-yl)ethyl)-4-hydroxypyrrolidine-2-carboxamide (30.1 mg, 55.94 umol, 27.33% yield, 100% purity) as white solid. MS (ESI) m/z 538.1 $[M+H]^+$.

prep-HPLC condition: column: Phenomenex Gemini-NX 80*40 mm*3 um; mobile phase: [water (10 mM NH4HCO3)-ACN]; B %: 25%-55%, 8 min.

$^1H$ NMR (400 MHz, MeOD-$d_4$) δ ppm 8.44-8.39 (m, 1H), 8.34-8.27 (m, 1H), 7.99 (d, J=8.4 Hz, 1H), 7.61-7.54 (m, 1H), 7.50-7.44 (m, 1H), 7.28-7.20 (m, 1H), 7.16-7.09 (m, 1H), 6.02-5.86 (m, 1H), 4.31-4.22 (m, 1H), 4.21-4.00 (m, 1H), 3.75-3.63 (m, 1H), 3.61-3.53 (m, 1H), 3.45-3.35 (m, 11H), 2.24-2.13 (m, 1H), 2.12-1.95 (m, 2H), 1.83-1.74 (m, 1H), 1.71-1.58 (m, 3H), 1.46-0.97 (m, 15H).

Example 177: Synthesis of Compound 1326

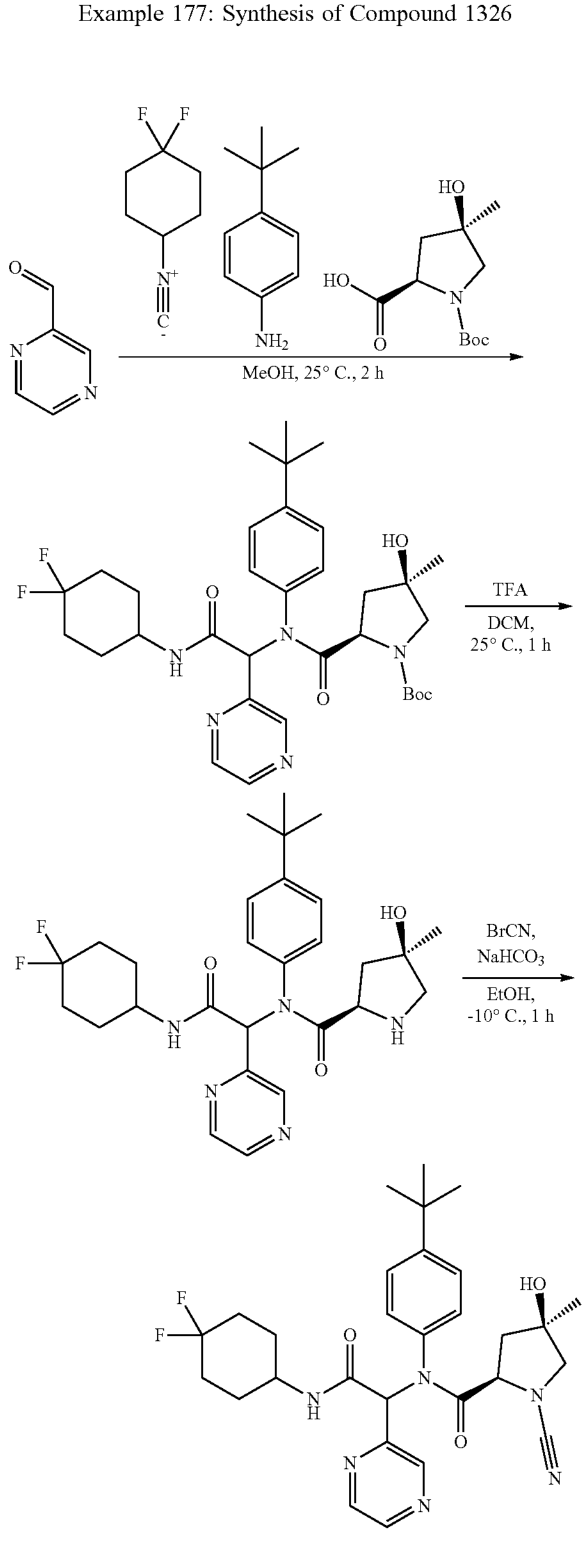

Step 1: (2R,4R)-tert-butyl 2-((4-(tert-butyl)phenyl)(2-((4,4-difluorocyclohexyl)amino)-2-oxo-1-(pyrazin-2-yl)ethyl)carbamoyl)-4-hydroxy-4-methylpyrrolidine-1-carboxylate To a solution of pyrazine-2-carbaldehyde (150 mg, 1.39 mmol, 1 eq) and 4-tert-butylaniline (207.08 mg, 1.39 mmol, 219.13 uL, 1 eq) in MeOH (6 mL), (2R,4R)-1-tert-butoxycarbonyl-4-hydroxy-4-methyl-pyrrolidine-2-carboxylic acid (425.43 mg, 1.39 mmol, 80% purity, 1 eq) and 1,1-difluoro-4-isocyano-cyclohexane (201.41 mg, 1.39 mmol, 1 eq) in MeOH (2 mL) was added drop-wise, and the mixture was stirred at 25° C. for 2 h. The reaction mixture was concentrated under reduced pressure to give a residue. The residue was purified by prep-HPLC (column: Waters Xbridge Prep OBD C18 150*40 mm*10 um; mobile phase: [water (0.05% $NH_3H2O$+10 mM $NH_4HCO_3$)-ACN]; B %: %-%, 8 min) to get the product tert-butyl (2R,4R)-2-[(4-tert-butylphenyl)-[2-[(4,4-difluorocyclohexyl)amino]-2-oxo-1-pyrazin-2-yl-ethyl]carbamoyl]-4-hydroxy-4-methyl-pyrrolidine-1-carboxylate (300 mg, 476.39 umol, 34.33% yield) as a yellow solid. MS (ESI) m/z 630.2 $[M+H]^+$ $^1$H NMR (400 MHz, METHANOL-$d_4$) 5 ppm 8.32-8.60 (m, 3H), 6.74-8.02 (m, 4H), 5.92-6.43 (m, 1H), 4.10-4.34 (m, 11H), 3.87 (t, J=10.1 Hz, 11H), 3.46 (d, J=10.3 Hz, 2H), 1.82-2.05 (m, 8H), 1.45-1.55 (m, 11H), 1.24-1.29 (m, 9H), 1.19 (s, 3H).

Step 2: (2R,4R)—N-(4-(tert-butyl)phenyl)-N-(2-(cyclohexylamino)-1-(S-methoxypyridin-3-yl)-2-oxoethyl)-4-hydroxypyrrolidine-2-carboxamide To a solution of tert-butyl (2R,4R)-2-[(4-tert-butylphenyl)-[2-[(4,4-difluorocyclohexyl)amino]-2-oxo-1-pyrazin-2-yl-ethyl]carbamoyl]-4-hydroxy-4-methyl-pyrrolidine-1-carboxylate (100 mg, 158.80 umol, 1 eq) in DCM (3.0 mL) was added TFA (1.54 g, 13.51 mmol, 1.00 mL, 85.05 eq) drop-wise, and the mixture was stirred at 25° C. for 1 h. The reaction mixture was quenched by addition $H_2O$ 30 mL at 0° C., and then extracted with DCM (20 mL*3). The combined organic layers were washed with brine 20 mL, dried over $Na_2SO_4$, filtered and concentrated under reduced pressure to get the product (2R,4R)—N-(4-tert-butylphenyl)-N-[2-[(4,4-difluorocyclohexyl)amino]-2-oxo-1-pyrazin-2-yl-ethyl]-4-hydroxy-4-methyl-pyrrolidine-2-carboxamide (80 mg, crude) was obtained as a yellow solid. MS (ESI) m/z 530.2 $[M+H]^+$ Step 3: (2R,4R)—N-(4-(tert-butyl)phenyl)-1-cyano-N-(2-((4,4-difluorocyclohexyl)amino)-2-oxo-1-(pyrazin-2-yl)ethyl)-4-hydroxy-4-methylpyrrolidine-2-carboxamide A solution of (2R,4R)—N-(4-tert-butylphenyl)-N-[2-[(4,4-difluorocyclohexyl)amino]-2-oxo-1-pyrazin-2-yl-ethyl]-4-hydroxy-4-methyl-pyrrolidine-2-carboxamide (80 mg, 151.05 umol, 1 eq) in EtOH (3 mL) was cooled to −10° C., and then $NaHCO_3$ (25.38 mg, 302.10 umol, 11.75 uL, 2.0 eq) and BrCN (24.00 mg, 226.58 umol, 16.67 uL, 1.5 eq) were added drop-wise at −10° C. The mixture was stirred at −10° C. for 1 h. The reaction mixture was filtered to give a residue. The residue was purified by prep-HPLC (column: Phenomenex Luna C18 75*30 mm*3 um; mobile phase: [water (0.2% FA)-ACN]; B %: 40%-70%, 8 min) to get the product (2R,4R)—N-(4-tert-butylphenyl)-1-cyano-N-[2-[(4,4-difluorocyclohexyl)amino]-2-oxo-1-pyrazin-2-yl-ethyl]-4-hydroxy-4-methyl-pyrrolidine-2-carboxamide (31.1 mg, 54.50 umol, 36.08% yield, 97.2% purity) was obtained as a white solid. MS (ESI) m/z 555.3 $[M+H]^+$ $^1$H NMR (METHANOL-$d_4$, 400 MHz): δ ppm 8.50-8.57 (m, 1H), 8.35-8.47 (m, 2H), 6.77-7.75 (m, 4H), 6.10-6.37 (m, 1H), 4.28-4.41 (m, 1H), 3.75-3.93 (m, 1H), 3.47 (t, J=8.8 Hz, 1H), 3.33-3.37 (m, 1H), 1.79-2.15 (m, 8H), 1.43-1.61 (m, 2H), 1.22-1.29 (m, 12H).

Example 178: Synthesis of Compound 415

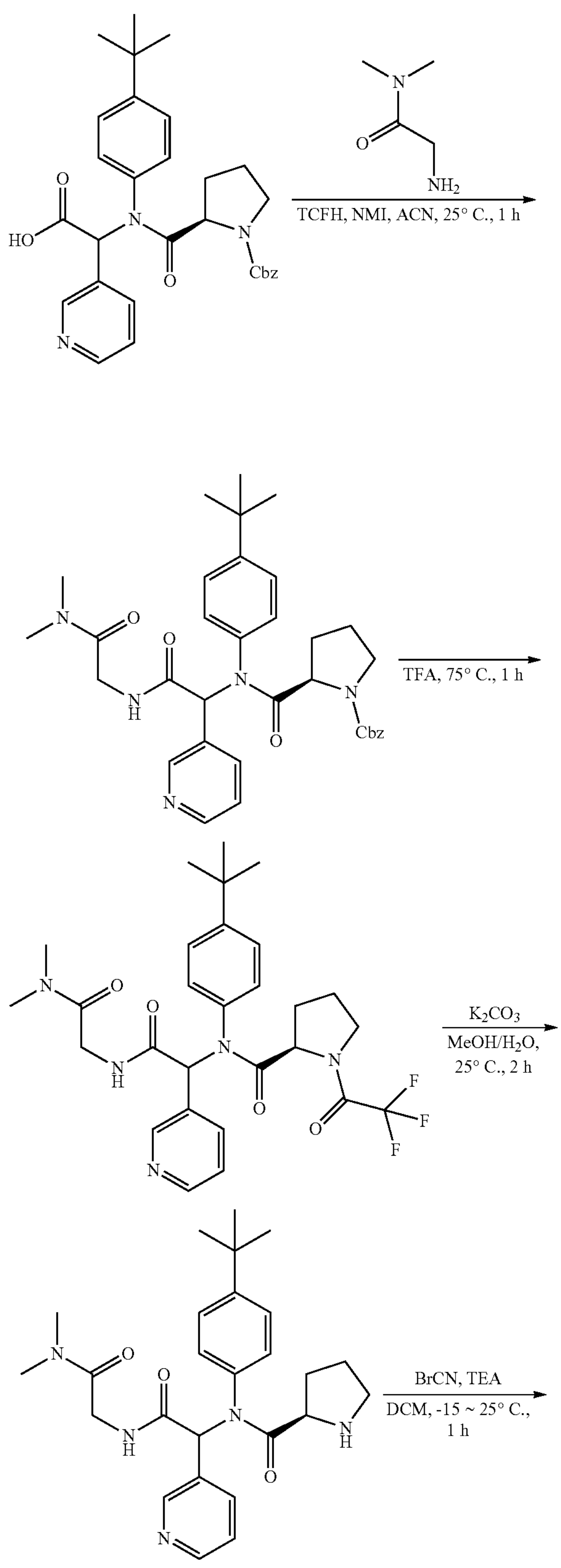

-continued

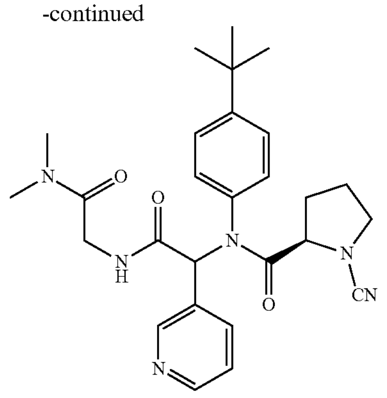

Step 1: (2R)-benzyl 2-((4-(tert-butyl)phenyl)(2-((2-(dimethylamino)-2-oxoethyl)amino)-2-oxo-1-(pyridin-3-yl)ethyl)carbamoyl)pyrrolidine-1-carboxylate To a solution of 2-(N-[(2R)-1-benzyloxycarbonylpyrrolidine-2-carbonyl]-4-tert-butyl-anilino)-2-(3-pyridyl)acetic acid (200 mg, 387.90 umol, 1 eq), 2-amino-N,N-dimethylacetamide (79.24 mg, 775.80 umol, 2 eq) in ACN (2 mL) was added the 1-methylimidazole (111.47 mg, 1.36 mmol, 108.22 uL, 3.5 eq) and [chloro(dimethylamino)methylene]-dimethyl-ammonium;hexafluorophosphate (217.67 mg, 775.80 umol, 2 eq), and the solution was stirred at 25° C. for 1 h. Upon completion, the solution was diluted with $H_2O$ (20 mL) and extracted with EA (30 mL*3). The combined organic phase was dried over $Na_2SO_4$, filtrated and concentrated to give the crude. The crude was used to next step directly and without further purification. Benzyl (2R)-2-[(4-tert-butylphenyl)-[2-[[2-(dimethylamino)-2-oxo-ethyl] amino]-2-oxo-1-(3-pyridyl) ethyl]carbamoyl]pyrrolidine-1-carboxylate (210 mg, crude) was obtained as yellow oil. MS (ESI) m/z 600.4 $[M+H]^+$.

Step 2: (2R)—N-(4-(tert-butyl)phenyl)-N-(2-((2-(dimethylamino)-2-oxoethyl)amino)-2-oxo-1-(pyridin-3-yl)ethyl)-1-(2,2,2-trifluoroacetyl)pyrrolidine-2-carboxamide Benzyl (2R)-2-[[2-[[2-(dimethylamino)-2-oxo-ethyl] amino]-2-oxo-1-(3-pyridyl) ethyl]-(4-isopropylphenyl) carbamoyl]pyrrolidine-1-carboxylate (210 mg, 358.55 umol, 1 eq) in TFA (5 mL) and the solution was stirred at 75° C. for 1 h. Upon completion, the solution was concentrated to remove the TFA, diluted with the solution of $NaHCO_3$, extracted with EA (30 mL*3); the combined organic phase was dried over $Na_2SO_4$, filtrated and concentrated to give the crude. The crude was used to next step directly and without further purification. (2R)—N-(4-tert-butylphenyl)-N-[2-[[2-(dimethylamino)-2-oxo-ethyl]amino]-2-oxo-1-(3-pyridyl) ethyl]-1-(2, 2, 2-trifluoroacetyl) pyrrolidine-2-carboxamide (200 mg, crude) was obtained as a yellow oil. MS (ESI) m/z 562.2 $[M+H]^+$.

Step 3: (2R)—N-(4-(tert-butyl)phenyl)-N-(2-((2-(dimethylamino)-2-oxoethyl)amino)-2-oxo-1-(pyridin-3-yl)ethyl)pyrrolidine-2-carboxamide (2R)—N-(4-tert-butylphenyl)-N-[2-[[2-(dimethylamino)-2-oxo-ethyl]amino]-2-oxo-1-(3-pyridyl)ethyl]-1-(2,2,2-trifluoroacetyl)pyrrolidine-2-carboxamide (180 mg, 320.52 umol, 1 eq) in MeOH (2 mL)/$H_2O$ (0.4 mL) was added the $K_2CO_3$ (88.59 mg, 641.03 umol, 2 eq) and the solution was stirred at 25° C. for 2 h. Upon completion, the solution was diluted with $H_2O$ (20 mL), extracted with EA (30 mL*3). The combined organic phase was dried over $Na_2SO_4$, filtrated and concentrated to give the crude. The crude was used to next step directly and without further purification. (2R)—N-(4-tert-butylphenyl)-N-[2-[[2-(dimethylamino)-2-oxo-ethyl]amino]-2-oxo-1-(3-pyridyl) ethyl]pyrrolidine-2-carboxamide (110 mg, crude) was obtained as a yellow oil. MS (ESI) m/z 466.3 $[M+H]^+$.

Step 4: (2R)—N-(4-(tert-butyl)phenyl)-1-cyano-N-(2-((2-(dimethylamino)-2-oxoethyl)amino)-2-oxo-1-(pyridin-3-yl)ethyl)pyrrolidine-2-carboxamide (2R)—N-(4-tert-butylphenyl)-N-[2-[[2-(dimethylamino)-2-oxo-ethyl]amino]-2-oxo-1-(3-pyridyl)ethyl]pyrrolidine-2-carboxamide (50 mg, 107.39 umol, 1 eq) in DCM (1.5 mL) was added the TEA (32.60 mg, 322.17 umol, 44.84 uL, 3 eq) and the solution was cooled to −15° C. A solution of BrCN (170 mg, 1.60 mmol, 118.06 uL, 14.95 eq) in DCM (0.3 mL) was added and the solution was stirred at 0° C. and warmed to 25° C. for 1 h gradually. Upon completion, the solution was quenched with $H_2O$ (10 mL), extracted with EA (20 mL*3), the combined organic phase was dried over $Na_2SO_4$, filtrated and concentrated to give the crude. The residue was purified by prep-HPLC (neutral condition), column: Phenomenex Gemini-NX 80*40 mm*3 um; mobile phase: [water (10 mM $NH_4HCO_3$)-ACN]; B %: 25%-45%, 8 min. (2R)—N-(4-tert-butylphenyl)-1-cyano-N-[2-[[2-(dimethylamino)-2-oxo-ethyl]amino]-2-oxo-1-(3-pyridyl)ethyl]pyrrolidine-2-carboxamide (6 mg, 11.82 umol, 11.01% yield, 96.64% purity) was obtained as white solid. $^1H$ NMR (400 MHz, METHANOL-$d_4$) δ=8.44-8.28 (m, 2H), 7.73-7.60 (m, 1H), 7.48-7.04 (m, 4H), 7.01-6.48 (m, 1H), 6.45-5.96 (m, 1H), 4.30-3.96 (m, 3H), 3.64-3.53 (m, 1H), 3.50-3.39 (m, 1H), 3.04 (d, J=1.1 Hz, 3H), 2.93 (s, 3H), 2.15-1.77 (m, 4H), 1.25 (d, J=13.0 Hz, 9H).

-continued

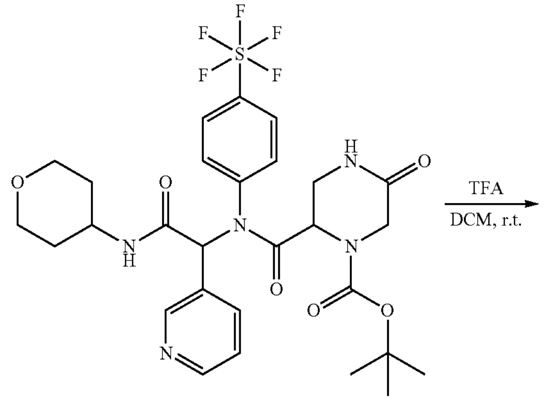

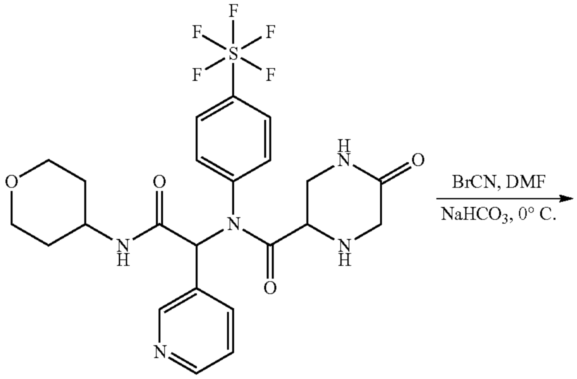

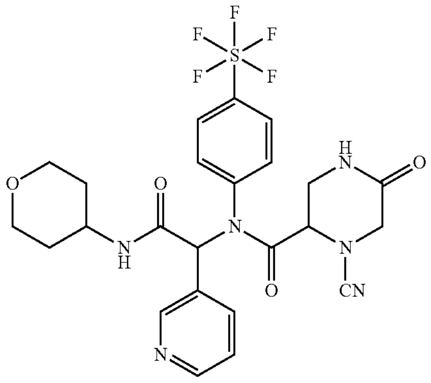

Example 179: Synthesis of Compound 811

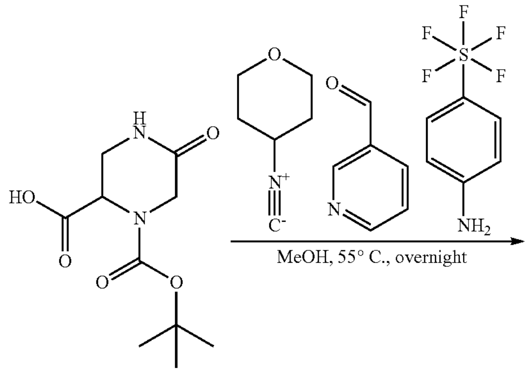

Step 1: tert-butyl (2R)-5-oxo-2-[[2-oxo-1-(3-pyridyl)-2-(tetrahydropyran-4-ylamino)ethyl]-[4-(pentafluoro-$\lambda^6$-sulfanyl)phenyl]carbamoyl]piperazine-1-carboxylate A solution of pyridine-3-carbaldehyde (175.41 mg, 1.64 mmol, 153.87 uL, 1 eq), 4-(pentafluoro-$\lambda^6$-sulfanyl)aniline (358.95 mg, 1.64 mmol, 1 eq) in MeOH (8 mL) was stirred for 1 h, and then 1-tert-butoxycarbonyl-5-oxo-piperazine-2-carboxylic acid (400 mg, 1.64 mmol, 1 eq) was added. After stirring for 10 min, 4-isocyanotetrahydropyran (182.02 mg, 1.64 mmol, 1 eq) in MeOH (1 mL) was added. The mixture was stirred at 55° C. for 14 h 50 min. Upon completion, the reaction mixture was concentrated under reduced pressure to remove solvent. The residue was purified by prep-HPLC (column: Kromasil C18 (250*50 mm*10 um); mobile phase: [water (10 mM NH4HCO3)-ACN]; B %: 40%-60%, 10 min) to give tert-butyl (2R)-5-oxo-2-[[2-oxo-1-(3-pyridyl)-2-(tetrahydropyran-4-ylamino)ethyl]-[4-(pentafluoro-$\lambda^6$-sulfanyl)phenyl]carbamoyl]piperazine-1-carboxylate (350 mg, 527.38 umol, 32.20% yield) as a yellow solid. MS (ESI) m/z 664.1 $[M+H]^+$ Step 2: 5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide To a solution of tert-butyl 5-oxo-2-[[2-oxo-1-(3-pyridyl)-2-(tetrahydropyran-4-ylamino)ethyl]-[4-(pentafluoro-$\lambda^6$-sulfanyl)phenyl]carbamoyl]piperazine-1-carboxylate (350 mg, 527.38 umol, 1 eq) in DCM (5 mL) was added TFA (3.08 g, 27.01 mmol, 2 mL, 51.22 eq). The mixture was stirred at 25° C. for 2 h. Upon completion, the reaction mixture was poured into $NaHCO_3$ 25 mL at 20° C., and then extracted with DCM (25 mL*3). The combined organic layers were washed with brine (25 mL*2), dried over $Na_2SO_4$, filtered and concentrated under reduced pressure to give 5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide (250 mg, crude) as a yellow solid. MS (ESI) m/z 564.1 $[M+H]^+$ Step 3: 1-cyano-5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide To a solution of 5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide (240 mg, 425.88 umol, 1 eq) in DMF (5 mL) was added $NaHCO_3$ (107.33 mg, 1.28 mmol, 49.69 uL, 3 eq). BrCN (58.64 mg, 553.64 umol, 40.72 uL, 1.3 eq) was added at 0° C., and the mixture was stirred at 0° C. for 2 h. Upon completion, the reaction mixture was poured into water 15 mL at 20° C., and then extracted with EtOAc (20 mL*3). The combined organic layers were washed with brine (15 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 15%-40%, 8 min) to give 1-cyano-5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide (100 mg, 163.98 umol, 38.50% yield, 96.51% purity) as a white solid. MS (ESI) m/z 589.2 $[M+H]^+$ Isomer 1: $^1H$ NMR (400 MHz, METHANOL-$d_4$) δ=8.42-8.32 (m, 2H), 8.26-7.64 (m, 3H), 7.62-7.51 (m, 1H), 7.25 (d, J=4.9, 7.9 Hz, 2H), 6.30-6.12 (m, 1H), 4.39-4.25 (m, 1H), 4.16 (d, J=11.8, 16.7 Hz, 1H), 4.01-3.79 (m, 4H), 3.61-3.39 (In, 4H), 1.89 (d, J=1.5, 13.3 Hz, 1H), 1.81-1.70 (m, 1H), 1.54 (d, J=5.9, 11.5 Hz, 1H), 1.44-1.29 (m, 1H).

Example 180: Synthesis of Compound 812

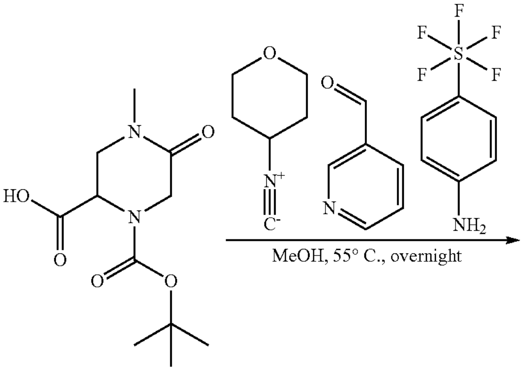

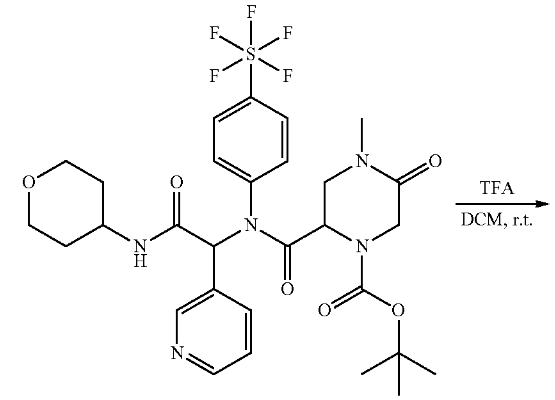

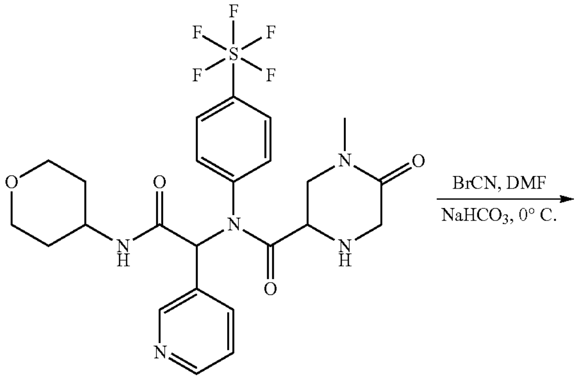

-continued

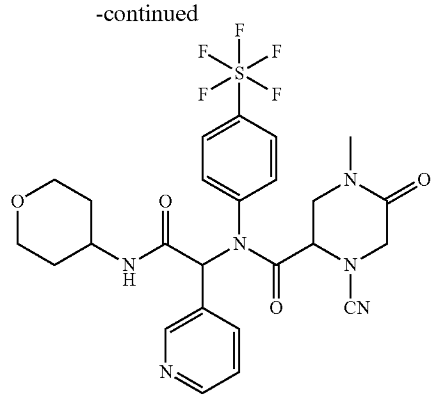

Step 1: tert-butyl (2R)-4-methyl-5-oxo-2-[[2-oxo-1-(3-pyridyl)-2-(tetrahydropyran-4-ylamino)ethyl]-[4-(pentafluoro-$\lambda^6$-sulfanyl)phenyl]carbamoyl]piperazine-1-carboxylate To a solution of pyridine-3-carbaldehyde (165.89 mg, 1.55 mmol, 145.52 uL, 1 eq), 4-(pentafluoro-$\lambda^6$-sulfanyl) aniline (339.45 mg, 1.55 mmol, 1 eq) in MeOH (4 mL), stirred 1 h, then 1-tert-butoxycarbonyl-4-methyl-5-oxo-piperazine-2-carboxylic acid (400 mg, 1.55 mmol, 1 eq) was added, stirred 10 min, then 4-isocyanotetrahydropyran (172.13 mg, 1.55 mmol, 1 eq) in MeOH (1 mL) was added. The mixture was stirred at 55° C. for 14 h 50 min. Upon completion, the reaction mixture was concentrated under reduced pressure to remove solvent. The residue was purified by prep-HPLC (column: Waters Xbridge Prep OBD C18 150*40 mm*10 um; mobile phase: [water (0.05% NH3H2O+10 mM NH4HCO3)-ACN]; B %: 30%-55%, 8 min) to give tert-butyl (2R)-4-methyl-5-oxo-2-[[2-oxo-1-(3-pyridyl)-2-(tetrahydropyran-4-ylamino)ethyl]-[4-(pentafluoro-$\lambda^6$-sulfanyl)phenyl]carbamoyl]piperazine-1-carboxylate (300 mg, 442.69 umol, 28.58% yield) as a yellow solid. MS (ESI) m/z 678.3 $[M+H]^+$ Step 2: 4-methyl-5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide To a solution of tert-butyl 4-methyl-5-oxo-2-[[2-oxo-1-(3-pyridyl)-2-(tetrahydropyran-4-ylamino)ethyl]-[4-(pentafluoro-$\lambda^6$-sulfanyl)phenyl]carbamoyl]piperazine-1-carboxylate (300 mg, 442.69 umol, 1 eq) in DCM (6 mL) was added TFA (3.08 g, 27.01 mmol, 2 mL, 61.02 eq). The mixture was stirred at 25° C. for 2 hr. Upon completion, the reaction mixture was poured into $NaHCO_3$ 20 mL at 20° C., and then extracted with DCM (25 mL*3). The combined organic layers were washed with brine (25 mL*2), dried over $Na_2SO_4$, filtered and concentrated under reduced pressure to give 4-methyl-5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide (220 mg, crude) as a yellow solid. MS (ESI) m/z 578.1 $[M+H]^+$ Step 3: 1-cyano-4-methyl-S-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide To a solution of 4-methyl-5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide (200 mg, 346.28 umol, 1 eq) in DMF (5 mL) was added $NaHCO_3$ (87.27 mg, 1.04 mmol, 40.40 uL, 3 eq). BrCN (55.02 mg, 519.42 umol, 38.21 uL, 1.5 eq) was added at 0° C., and the mixture was stirred at 0° C. for 2 hr. Upon completion, the reaction mixture was poured into water 15 mL at 20° C., and then extracted with EtOAc (20 mL*3). The combined organic layers were washed with brine (15 mL*2), dried over $Na_2SO_4$, filtered and concentrated under reduced pressure to give a residue. The residue was purified by prep-HPLC (column: Phenomenex Gemini-NX C18 75*30 mm*3 um; mobile phase: [water (10 mM NH4HCO3)-ACN]; B %: 30%-50%, 8 min) to give 1-cyano-4-methyl-5-oxo-N-[2-oxo-1-(3-pyridyl)-2-(tetrahydropyran-4-ylamino)ethyl]-N-[4-(pentafluoro-$\lambda^6$-sulfanyl)phenyl]piperazine-2-carboxamide (90 mg, 126.96 umol, 36.66% yield, 85% purity) as a white solid. MS (ESI) m/z 603.2 $[M+H]^+$ $^1H$ NMR (400 MHz, METHANOL-$d_4$) δ 8.35 (d, J=1.7, 3.2 Hz, 2H), 8.19-7.93 (m, 1H), 7.85-7.65 (m, 2H), 7.62-7.53 (m, 1H), 7.25 (d, J=5.1, 7.9 Hz, 1H), 7.20-6.96 (m, 1H), 6.20 (d, J=11.9 Hz, 1H), 4.41-4.31 (m, 1H), 4.20-4.09 (m, 1H), 4.03-3.76 (m, 4H), 3.69-3.43 (m, 4H), 2.99 (s, 3H), 1.88 (d, J=1.9, 12.9 Hz, 1H), 1.80-1.73 (m, 1H), 1.60-1.47 (m, 1H), 1.44-1.32 (m, 1H).

Example 181: Synthesis of Compound 947

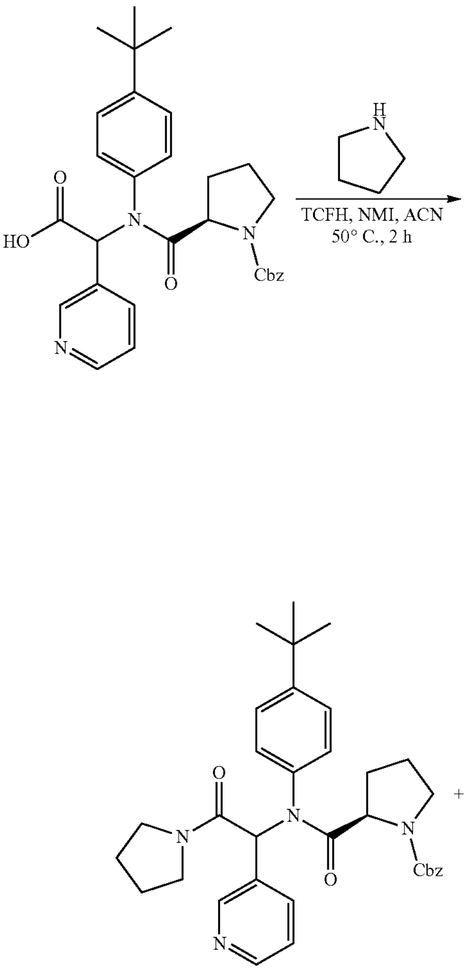

-continued

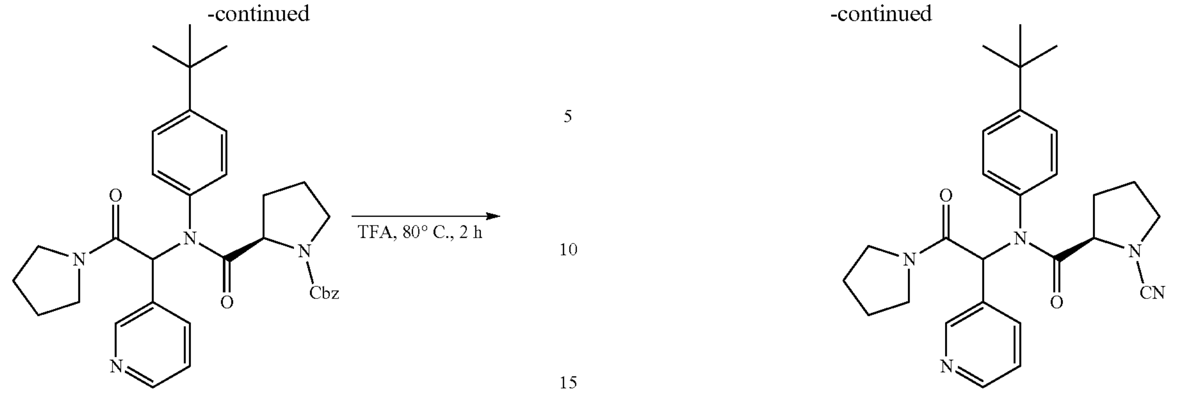

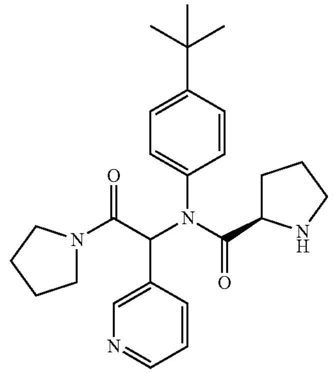

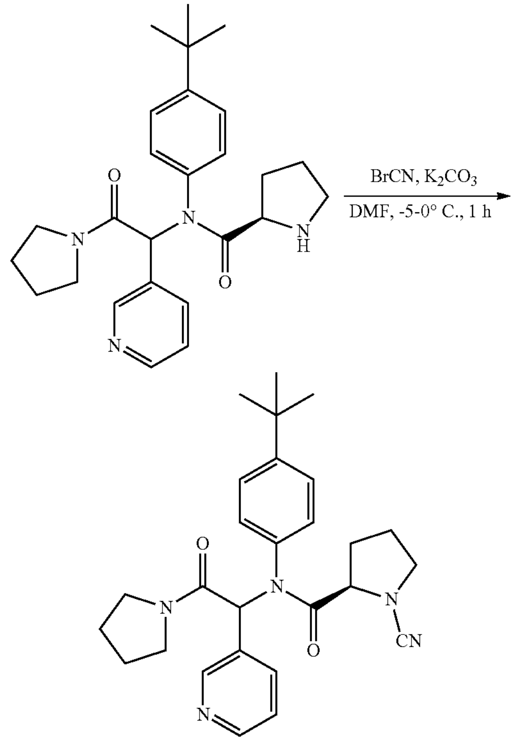

Step 1: benzyl (2R)-2-[(4-tert-butylphenyl)-[2-oxo-1-(3-pyridyl)-2-pyrrolidin-1-yl-ethyl]carbamoyl]pyrrolidine-1-carboxylate A mixture of 2-(N-[(2R)-1-benzyloxycarbonylpyrrolidine-2-carbonyl]-4-tert-butyl-anilino)-2-(3-pyridyl)acetic acid (400 mg, 775.80 umol, 1 eq) in ACN (3 mL) was added with pyrrolidine (165.53 mg, 2.33 mmol, 194.28 uL, 3.0 eq), 1-methylimidazole (318.46 mg, 3.88 mmol, 309.19 uL, 5 eq) and [chloro(dimethylamino)methylene]-dimethyl-ammonium;hexafluorophosphate (435.34 mg, 1.55 mmol, 2.0 eq). After stirring the mixture at 50° C. for 2 h, the reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 45%-65%, 8 min) to get a product benzyl (2R)-2-[(4-tert-butylphenyl)-[2-oxo-1-(3-pyridyl)-2-pyrrolidin-1-yl-ethyl]carbamoyl]pyrrolidine-1-carboxylate Isomer 1 (118 mg, 207.49 umol, 26.75% yield) as yellow solid. MS (ESI) m/z 569.3 $[M+H]^+$.

To get benzyl (2R)-2-[(4-tert-butylphenyl)-[2-oxo-1-(3-pyridyl)-2-pyrrolidin-1-yl-ethyl]carbamoyl]pyrrolidine-1-carboxylate Isomer 2 (110 mg, 193.42 umol, 24.93% yield) as yellow solid. MS (ESI) m/z 569.2 $[M+H]^+$.

Step 2: (2R)—N-(4-tert-butylphenyl)-N-[2-oxo-1-(3-pyridyl)-2-pyrrolidin-1-yl-ethyl]pyrrolidine-2-carboxamide Isomer 1

A mixture of benzyl (2R)-2-[(4-tert-butylphenyl)-[2-oxo-1-(3-pyridyl)-2-pyrrolidin-1-yl-ethyl]carbamoyl]pyrrolidine-1-carboxylate Isomer 1 (100 mg, 175.84 umol, 1 eq) in TFA (3 mL), the mixture at 80° C. for 2 h. Upon completion, the reaction mixture was base-modulated in saturated $NaHCO_3$ (10 mL) solution, and extracted with DCM (10 mL*3). The combined organic layers were washed with brine (50 mL), dried over $Na_2SO_4$, filtered and concentrated under reduced pressure to give a residue to get the product (2R)—N-(4-tert-butylphenyl)-N-[2-oxo-1-(3-pyridyl)-2-pyrrolidin-1-yl-ethyl]pyrrolidine-2-carboxamide Isomer 1 (200 mg, crude) as white oil. MS (ESI) m/z 435.2 $[M+H]^+$.

(2R)—N-(4-tert-butylphenyl)-N-[2-oxo-1-(3-pyridyl)-2-pyrrolidin-1-yl-ethyl]pyrrolidine-2-carboxamide Isomer 2

A mixture of benzyl (2R)-2-[(4-tert-butylphenyl)-[2-oxo-1-(3-pyridyl)-2-pyrrolidin-1-yl-ethyl]carbamoyl]pyrrolidine-1-carboxylate Isomer 2 (100 mg, 175.84 umol, 1 eq) in TFA (3 mL) was stirred at 80° C. for 2 h. Upon completion, the reaction mixture was base-modulated in saturated $NaHCO_3$ (10 mL) solution, and extracted with DCM (10 mL*3). The combined organic layers were washed with brine (50 mL), dried over $Na_2SO_4$, filtered and concentrated under reduced pressure to give a residue to get a product (2R)—N-(4-tert-butylphenyl)-N-[2-oxo-1-(3-pyridyl)-2-pyrrolidin-1-yl-ethyl]pyrrolidine-2-carboxamide Isomer 2 (160 mg, crude) as white oil. MS (ESI) m/z 435.2 $[M+H]^+$.

Step 3: (2R)—N-(4-tert-butylphenyl)-1-cyano-N-[2-oxo-1-(3-pyridyl)-2-pyrrolidin-1-yl-ethyl]pyrrolidine-2-carboxamide Isomer 1

To a mixture of (2R)—N-(4-tert-butylphenyl)-N-[2-oxo-1-(3-pyridyl)-2-pyrrolidin-1-yl-ethyl]pyrrolidine-2-carboxamide Isomer 1 (180 mg, 414.20 umol, 1 eq) in DMF (2 mL) was added $K_2CO_3$ (171.73 mg, 1.24 mmol, 3 eq), and then the solution was cooled to −5° C. BrCN (52.65 mg, 497.04 umol, 36.56 uL, 1.2 eq) in DMF (1 mL) was added drop-wise, and then the mixture was stirred at 0° C. for 1 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Gemini-NX C18 75*30 mm*3 um; mobile phase: [water (0.05% NH3$H_2O$+10 mM $NH_4HCO_3$)-ACN]; B %: 30%-60%, 8 min) to get the product (2R)—N-(4-tert-butylphenyl)-1-cyano-N-[2-oxo-1-(3-pyridyl)-2-pyrrolidin-1-yl-ethyl]pyrrolidine-2-carboxamide Isomer 1 (32.35 mg, 67.29 umol, 16.25% yield, 95.6% purity) as yellow solid. MS (ESI) m/z 460.2 $[M+H]^+$.

$^1H$ NMR (400 MHz, METHANOL-$d_4$) δ=8.35 (d, J=1.8 Hz, 1H), 8.30 (dd, J=1.4, 5.0 Hz, 1H), 7.70 (br s, 1H), 7.59 (td, J=1.8, 7.9 Hz, 1H), 7.37 (br s, 1H), 7.23-7.09 (m, 2H), 6.67 (br s, 1H), 6.37 (s, 1H), 4.15 (dd, J=5.2, 7.8 Hz, 1H), 3.84-3.74 (m, 1H), 3.59 (s, 2H), 3.50-3.38 (m, 2H), 2.99 (td, J=6.4, 10.1 Hz, 1H), 2.17-1.70 (m, 8H), 1.34-1.12 (m, 9H).

(2R)—N-(4-tert-butylphenyl)-1-cyano-N-[2-oxo-1-(3-pyridyl)-2-pyrrolidin-1-yl-ethyl]pyrrolidine-2-carboxamide Isomer 2

To a mixture of (2R)—N-(4-tert-butylphenyl)-N-[2-oxo-1-(3-pyridyl)-2-pyrrolidin-1-yl-ethyl]pyrrolidine-2-carboxamide Isomer 2 (150 mg, 345.17 umol, 1 eq) in DMF (2 mL) was added $K_2CO_3$ (143.11 mg, 1.04 mmol, 3 eq), and the solution was cooled to −5° C. BrCN (43.87 mg, 414.20 umol, 30.47 uL, 1.2 eq) in DMF (1 mL) was added drop-wise, and the mixture was stirred at 0° C. for 1 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Gemini-NX C18 75*30 mm*3 urn; mobile phase: [water (0.05% $NH_3H_2O$+10 mM $NH_4HCO_3$)-ACN]; B %: 20%-50%, 8 min) to get the product (2R)—N-(4-tert-butylphenyl)-1-cyano-N-[2-oxo-1-(3-pyridyl)-2-pyrrolidin-1-yl-ethyl]pyrrolidine-2-carboxamide Isomer 2 (21.62 mg, 45.16 umol, 13.08% yield, 96% purity) as yellow solid. MS (ESI) m/z 460.3 $[M+H]^+$.

$^1H$ NMR (400 MHz, METHANOL-$d_4$) δ=8.38 (d, J=1.8 Hz, 1H), 8.34 (dd, J=1.5, 5.1 Hz, 1H), 7.98-7.62 (m, 1H), 7.56 (td, J=1.8, 7.9 Hz, 1H), 7.46 (br s, 1H), 7.26-7.05 (m, 2H), 6.72-6.40 (m, 1H), 6.30 (s, 1H), 4.14 (dd, J=4.5, 7.8 Hz, 1H), 3.80 (br d, J=2.9 Hz, 1H), 3.67-3.52 (m, 2H), 3.50-3.35 (m, 2H), 3.09 (br d, J=10.1 Hz, 1H), 2.06-1.74 (m, 8H), 1.30-1.18 (m, 9H).

Example 182: Synthesis of Compound 952

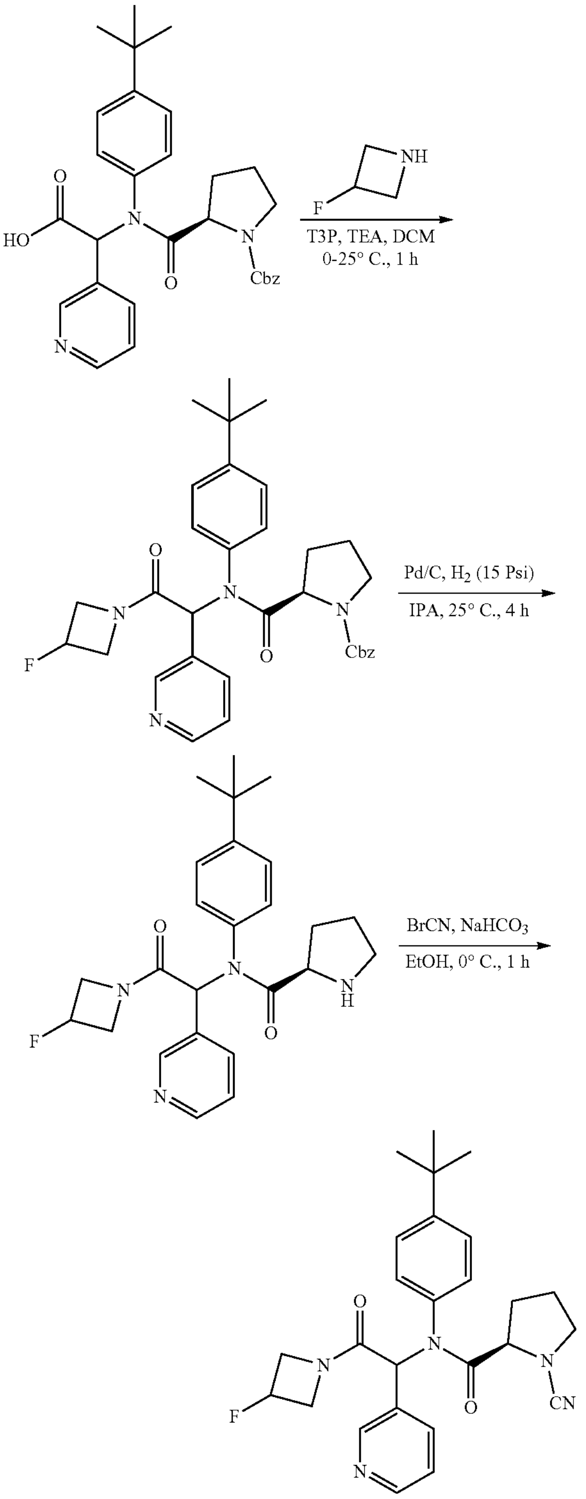

Step 1: (2R)-benzyl 2-((4-(tert-butyl)phenyl)(2-(3-fluoroazetidin-1-yl)-2-oxo-1-(pyridin-3-yl)ethyl) carbamoyl)pyrrolidine-1-carboxylate To a solution of 2-(N-[(2R)-1-benzyloxycarbonyl pyrrolidine-2-carbonyl]-4-tert-butyl-anilino)-2-(3-pyridyl) acetic acid (300 mg, 581.85 umol, 1 eq) and 3-fluoroazetidine (218.44 mg, 2.91 mmol, 5 eq) in DCM (8 mL) was added TEA (294.39 mg, 2.91 mmol, 404.93 uL, 5 eq) at 0° C., and then T3P (555.40 mg, 872.77 umol, 519.06 uL, 50% purity, 1.5 eq) was added at 0° C. The mixture was stirred at 25° C. for 1 h. The mixture was quenched by water (6 mL) and then extracted with DCM (2 mL*3). The combined organic layers were dried over $Na_2SO_4$, filtered and concentrated under reduced pressure and was purified by column ($SiO_2$, PE:EA=2:1 to 0:1) to obtained (2R)-benzyl2-((4-(tert-butyl) phenyl)(2-(3-fluoroazetidin-1-yl)-2-oxo-1-(pyridin-3-yl) ethyl) carbamoyl)pyrrolidine-1-carboxylate (270 mg, 424.33 umol, 72.93% yield, 90% purity) as a yellow oil. MS (ESI) m/z 573.2 $[M+H]^+$ Step 2: (2R)—N-(4-(tert-butyl)phenyl)-N-(2-(3-fluoroazetidin-1-yl)-2-oxo-1-(pyridin-3-yl)ethyl) pyrrolidine-2-carboxamide A solution of (2R)-benzyl2-((4-(tert-butyl)phenyl)(2-(3-fluoroazetidin-1-yl)-2-oxo-1-(pyridin-3-yl) ethyl) carbamoyl) pyrrolidine-1-carboxylate (220 mg, 384.17 umol, 1 eq) in isopropanol (3 mL), was added Pd/C (25 mg, 10% purity, 1 eq) at 25° C. under $H_2$ (15 Psi), and the mixture was stirred at 25° C. for 4 h. The mixture was filtered and concentration in vacuum to obtained (2R)—N-(4-(tert-butyl)phenyl)-N-(2-(3-fluoroazetidin-1-yl)-2-oxo-1-(pyridin-3-yl)ethyl)pyrrolidine-2-carboxamide (150 mg, 307.84 umol, 80.13% yield, 90% purity) as a colorless gum. MS (ESI) m/z 439.2 $[M+H]^+$ Step 3: (2R)—N-(4-(tert-butyl)phenyl)-1-cyano-N-(2-(3-fluoroazetidin-1-yl)-2-oxo-1-(pyridin-3-yl) ethyl)pyrrolidine-2-carboxamide To a solution of (2R)—N-(4-(tert-butyl)phenyl)-N-(2-(3-fluoroazetidin-1-yl)-2-oxo-1-(pyridin-3-yl)ethyl) pyrrolidine-2-carboxamide (150 mg, 342.05 umol, 1 eq) in EtOH (3 mL) was added $NaHCO_3$ (86.20 mg, 1.03 mmol, 39.91 uL, 3 eq) at 0° C. After the addition of BrCN (72.46 mg, 684.09 umol, 50.32 uL, 2 eq) at 0° C., the mixture was stirred at 0° C. for 1 h. The mixture was dried by blowing $N_2$, and then was quenched by water and extracted with DCM (5 mL*3), then was concentration in vacuum and was purified by prep-HPLC to obtained (2R)—N-(4-(tert-butyl) phenyl)-1-cyano-N-(2-(3-fluoroazetidin-1-yl)-2-oxo-1-(pyridin-3-yl)ethyl)pyrrolidine-2-carboxamide (49.97 mg, 107.15 umol, 31.33% yield, 99.4% purity) obtained as a yellow solid. MS (ESI) m/z 464.2 $[M+H]^+$ prep-HPLC conditions: column: Waters Xbridge BEH C18 100*25 mm*5 um; mobile phase: [water (10 mM $NH_4HCO_3$)-ACN]; B %: 25%-65%, 10 min.

$^1H$ NMR (400 MHz, METHANOL-$d_4$) δ=8.44-8.25 (m, 2H), 7.83-7.47 (m, 2H), 7.40 (d, J=14.7 Hz, 1H), 7.28-7.08 (m, 2H), 6.67 (s, 1H), 6.24-6.09 (m, 1H), 5.53-5.13 (m, 1H), 4.87-4.68 (m, 1H), 4.62 (s, 1H), 4.59-4.37 (m, 1H), 4.29-3.73 (m, 3H), 3.65-3.53 (m, 1H), 3.51-3.39 (m, 1H), 2.12-1.77 (m, 4H), 1.35-1.13 (m, 9H).

Example 183: Synthesis of Compound 959

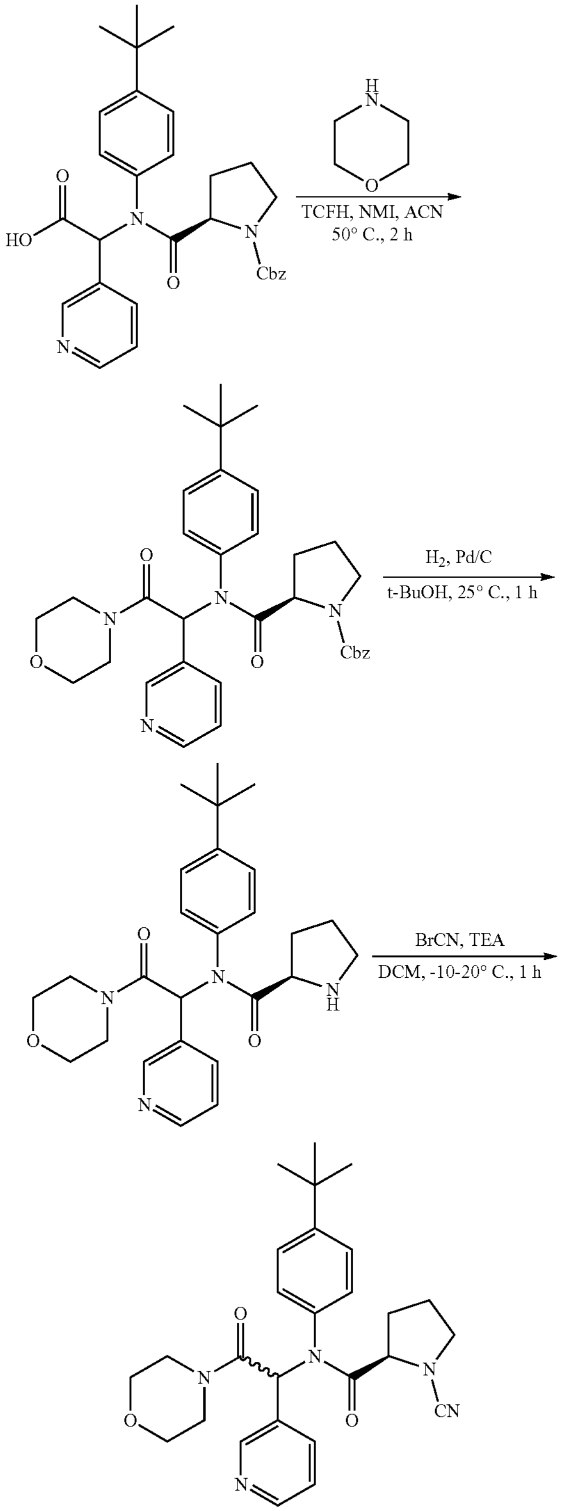

-continued

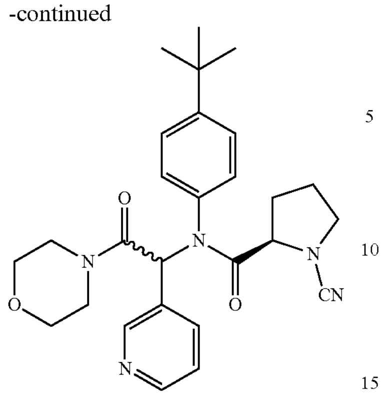

Step 1: (2R)-benzyl 2-((4-(tert-butyl)phenyl)(2-morpholino-2-oxo-1-(pyridin-3-yl)ethyl)carbamoyl)pyrrolidine-1-carboxylate A mixture of 2-(N-[(2R)-1-benzyloxycarbonylpyrrolidine-2-carbonyl]-4-tert-butyl-anilino)-2-(3-pyridyl)acetic acid (250 mg, 484.87 umol, 1 eq), morpholine (84.48 mg, 969.75 umol, 85.34 uL, 2 eq), 1-methyl-1H-imidazole (139.33 mg, 1.70 mmol, 135.27 uL, 3.5 eq), [chloro(dimethylamino)methylene]-dimethyl-ammonium;hexafluorophosphate (244.88 mg, 872.77 umol, 1.8 eq) in ACN (5 mL) was degassed and purged with $N_2$ for 3 times, and then the mixture was stirred at 25° C. for 1 h under $N_2$ atmosphere. Upon completion, the reaction mixture was quenched by addition 8 mL $H_2O$, and then extracted with ethyl acetate (4 mL*3). The combined organic layers were washed with brine 5 mL, dried over $Na_2SO_4$, filtered and concentrated under reduced pressure to afford benzyl (2R)-2-[(4-tert-butylphenyl)-[2-morpholino-2-oxo-1-(3-pyridyl)ethyl]carbamoyl]pyrrolidine-1-carboxylate (300 mg, crude) was obtained as yellow oil. MS (ESI) m/z 585.3 $[M+H]^+$.

Step 2: (2R)—N-(4-(tert-butyl)phenyl)-N-(2-morpholino-2-oxo-1-(pyridin-3-yl)ethyl)pyrrolidine-2-carboxamide To a solution of benzyl (2R)-2-[(4-tert-butylphenyl)-[2-morpholino-2-oxo-1-(3-pyridyl)ethyl]carbamoyl]pyrrolidine-1-carboxylate (250 mg, 427.57 umol, 1 eq) in t-BuOH (25 mL) was added Pd/C (10%, 0.2 g) under $N_2$ atmosphere. The suspension was degassed and purged with $H_2$ for 3 times. The mixture was stirred under H2 (15 Psi.) at 25° C. for 1 h. LCMS showed the reaction was completed, and desired MS was observed. The reaction mixture was filtered and concentrated under reduced pressure to give a residue to get the product (2R)—N-(4-tert-butylphenyl)-N-[2-morpholino-2-oxo-1-(3-pyridyl)ethyl]pyrrolidine-2-carboxamide (250 mg, crude) was obtained as colorless oil. MS (ESI) m/z 451.3 $[M+H]^+$.

Step 3: (2R)—N-(4-(tert-butyl)phenyl)-1-cyano-N-(2-morpholino-2-oxo-1-(pyridin-3-yl)ethyl)pyrrolidine-2-carboxamide To a solution of (2R)—N-(4-tert-butylphenyl)-N-[2-morpholino-2-oxo-1-(3-pyridyl)ethyl]pyrrolidine-2-carboxamide (200 mg, 443.88 umol, 1 eq) in DCM (3 mL) was added TEA (89.83 mg, 887.76 umol, 123.57 uL, 2 eq). After the addition of BrCN (141.05 mg, 1.33 mmol, 97.95 uL, 3 eq) at −10° C., the mixture was stirred at 20° C. for 1 h. The reaction mixture was concentrated under reduced pressure to remove solvent. The residue was purified by FA prep-HPLC to get the product (2R)—N-(4-tert-butylphenyl)-1-cyano-N-[2-morpholino-2-oxo-1-(3-pyridyl)ethyl]pyrrolidine-2-carboxamide (23.65 mg, 49.33 umol, 11.11% yield, 99.2% purity) was obtained as white solid. MS (ESI) m/z 476.2 $[M+H]^+$.

Prep-HPLC condition: column: Phenomenex Luna C18 200*40 mm*10 um; mobile phase: [water (0.2% FA)-ACN]; B %: 20%-60%, 8 min $^1H$ NMR (400 MHz, METHANOL-$d_4$) δ ppm 8.28-8.44 (m, 2H) 7.54-7.91 (m, 2H) 7.45 (br s, 1H) 7.03-7.29 (m, 2H) 6.56 (s, 2H) 4.14 (dd, J=7.69, 4.71 Hz, 1H) 3.52-3.82 (m, 7H) 3.39-3.49 (m, 1H) 3.17-3.30 (m, 2H) 1.74-2.14 (m, 4H) 1.24 (s, 9H).

(2R)—N-(4-tert-butylphenyl)-1-cyano-N-[2-morpholino-2-oxo-1-(3-pyridyl)ethyl]pyrrolidine-2-carboxamide (23.57 mg, 48.37 umol, 10.90% yield, 97.6% purity) was obtained as white solid. MS (ESI) m/z 476.2$[M+H]^+$.

$^1H$ NMR (400 MHz, METHANOL-$d_4$) δ ppm 8.32-8.46 (m, 2H) 7.51-7.88 (m, 2H) 7.00-7.51 (m, 3H) 6.48-6.95 (m, 2H) 4.16 (dd, J=7.99, 5.13 Hz, 1H) 3.54-3.81 (m, 7H) 3.41-3.51 (m, 1H) 3.20-3.30 (m, 2H) 2.05-2.16 (m, 1H) 1.96-2.05 (m, 1H) 1.87-1.96 (m, 1H) 1.75-1.86 (m, 1H) 1.22 (s, 9H).

Example 184: Synthesis of Compound 961

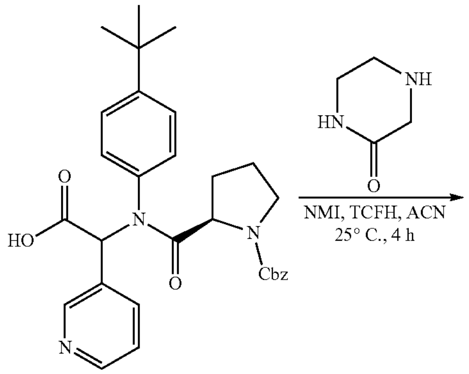

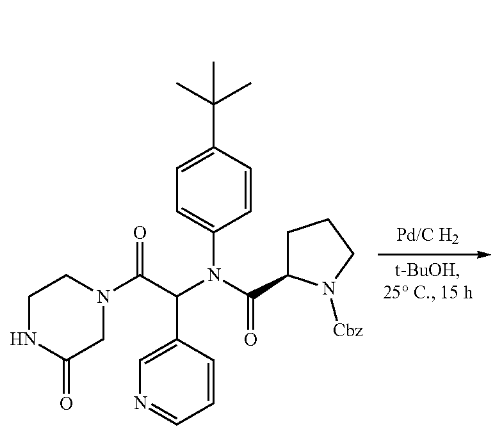

-continued

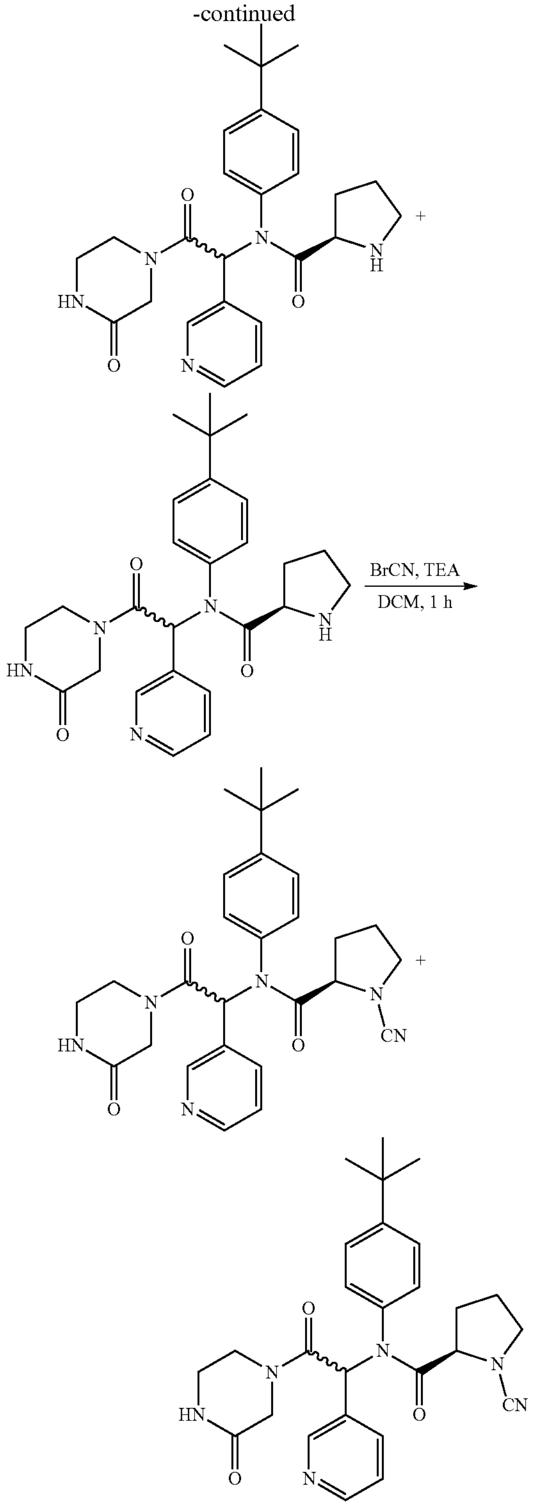

Step 1: (2R)-benzyl2-((4-(tert-butyl)phenyl)(2-oxo-2-(3-oxopiperazin-1-yl)-1-(pyridin-3-yl)ethyl)carbamoyl)pyrrolidine-1-carboxylate A solution of 2-(N-[(2R)-1-benzyloxycarbonylpyrrolidine-2-carbonyl]-4-tert-butyl-anilino)-2-(3-pyridyl)acetic acid (450 mg, 872.77 umol, 1 eq), piperazin-2-one (262.14 mg, 2.62 mmol, 3 eq), 1-methylimidazole (358.27 mg, 4.36 mmol, 347.84 uL, 5 eq) and [chloro(dimethylamino)methylene]-dimethyl-ammonium;hexafluorophosphate (489.76 mg, 1.75 mmol, 2 eq) in ACN (5 mL) was stirred at 25° C. for 4 h. Upon completion, the mixture was added $H_2O$ (30 mL) and then extracted with DCM (30 mL*3). The combined organic layers were washed with brine (50 mL), dried over $Na_2SO_4$, filtered and concentrated under reduced pressure to give a residue. The benzyl (2R)-2-[(4-tert-butylphenyl)-[2-oxo-2-(3-oxopiperazin-1-yl)-1-(3-pyridyl)ethyl]carbamoyl]pyrrolidine-1-carboxylate (420 mg, crude) was obtained, as yellow solid and used directly for next step. MS (ESI) m/z 598.3 $[M+H]^+$.

Step 2: (2R)—N-(4-(tert-butyl)phenyl)-N-(2-oxo-2-(3-oxopiperazin-1-yl)-1-(pyridin-3-yl)ethyl)pyrrolidine-2-carboxamide To a solution of benzyl (2R)-2-[(4-tert-butylphenyl)-[2-(3-methyl-4-oxo-imidazolidin-1-yl)-2-oxo-1-(3-pyridyl)ethyl]carbamoyl]pyrrolidine-1-carboxylate (420 mg, 702.69 umol, 1 eq) in t-BuOH (6 mL) was added Pd/C (100 mg, 10% purity) and the mixture was stirred at 25° C. for 16 h under $H_2$ (15 PSI). Upon completion, Pd/C was filtered, and the filtered solution was concentrated under reduced pressure to give a residue. The residue was purified by prep-HPLC (column: Kromasil C18 (250*50 mm*10 um); mobile phase: [water (10 mM $NH_4HCO_3$)-ACN]; B %: 20%-40%, 10 min). (2R)—N-(4-tert-butylphenyl)-N-[2-(3-methyl-4-oxo-imidazolidin-1-yl)-2-oxo-1-(3-pyridyl)ethyl]pyrrolidine-2-carboxamide (105 mg, 215.18 umol, 30.62% yield, 95% purity) was obtained as yellow solid. MS (ESI) m/z 464.3 $[M+H]^+$.

(2R)—N-(4-tert-butylphenyl)-N-[2-(3-methyl-4-oxo-imidazolidin-1-yl)-2-oxo-1-(3-pyridyl)ethyl]pyrrolidine-2-carboxamide (104 mg, 213.13 umol, 30.33% yield, 95% purity) was obtained as yellow solid. MS (ESI) m/z 464.3 $[M+H]^+$.

Step 3: (2R)—N-(4-(tert-butyl)phenyl)-1-cyano-N-(2-oxo-2-(3-oxopiperazin-1-yl)-1-(pyridin-3-yl)ethyl)pyrrolidine-2-carboxamide To a solution of (2R)—N-(4-tert-butylphenyl)-N-[2-oxo-2-(3-oxopiperazin-1-yl)-1-(3-pyridyl)ethyl]pyrrolidine-2-carboxamide (105 mg, 226.50 umol, 1 eq) and TEA (34.38 mg, 339.75 umol, 47.29 uL, 1.5 eq) in DCM (2 mL) was added BrCN (28.79 mg, 271.80 umol, 19.99 uL, 1.2 eq) which was dissolved in DCM (0.5 mL) at −10° C. and mixture was stirred at 25° C. for 1 h. Upon completion, the mixture was added $H_2O$ (30 mL) and then extracted with EA (30 mL*3). The combined organic layers were washed with brine (50 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 20%-50%, 10 min) to afford product (2R)—N-(4-tert-butylphenyl)-1-cyano-N-[2-oxo-2-(3-oxopiperazin-1-yl)-1-(3-pyridyl)ethyl]pyrrolidine-2-carboxamide (26.5 mg, 53.56 umol, 23.65% yield, 98.75% purity) as white solid MS (ESI) m/z 489.3 $[M+H]^+$.

$^1H$ NMR (400 MHz, METHANOL-$d_4$) δ=8.48-8.23 (m, 2H), 7.89-7.49 (m, 2H), 7.49-7.02 (m, 3H), 6.89-6.42 (m, 2H), 4.49-4.30 (m, 1H), 4.19-3.72 (m, 3H), 3.66-3.52 (m, 1H), 3.52-3.34 (m, 3H), 3.02-2.85 (m, 1H), 2.22-1.65 (m, 4H), 1.27-1.12 (m, 9H)

A solution of (2R)—N-(4-tert-butylphenyl)-N-[2-oxo-2-(3-oxopiperazin-1-yl)-1-(3-pyridyl)ethyl]pyrrolidine-2-carboxamide (104 mg, 224.35 umol, 1 eq) and TEA (22.70 mg, 224.35 umol, 31.23 uL, 1 eq) in DCM (2 mL) was cooled −10° C. BrCN (28.52 mg, 269.21 umol, 19.80 uL, 1.2 eq) in DCM (0.5 mL) was added and stirred at 25° C. for 1 h. Upon completion, the mixture was added $H_2O$ (30 mL) and then extracted with EA (30 mL*3). The combined organic layers were washed with brine (30 mL), dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 25%-50%, 8 min). The (2R)—N-(4-tert-butylphenyl)-1-cyano-N-[2-oxo-2-(3-oxopiperazin-1-yl)-1-(3-pyridyl)ethyl]pyrrolidine-2-carboxamide (25.2 mg, 51.58 umol, 22.99% yield, 100% purity) was obtained as white solid. MS (ESI) m/z 489.3 $[M+H]^+$.

$^1H$ NMR (400 MHz, METHANOL-$d_4$) δ=8.49-8.26 (m, 2H), 7.90-7.65 (m, 1H), 7.64-7.31 (m, 2H), 7.28-6.99 (m, 2H), 6.73-6.35 (m, 2H), 4.48-4.33 (m, 1H), 4.18-4.13 (m, 1H), 4.12-3.68 (m, 2H), 3.52 (m, 4H), 3.29-2.91 (m, 1H), 2.09-1.71 (m, 4H), 1.28-1.11 (m, 9H).

Example 185: Synthesis of Compound 967

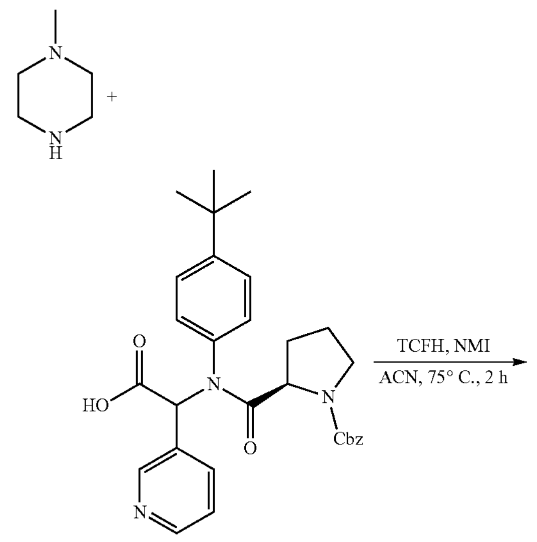

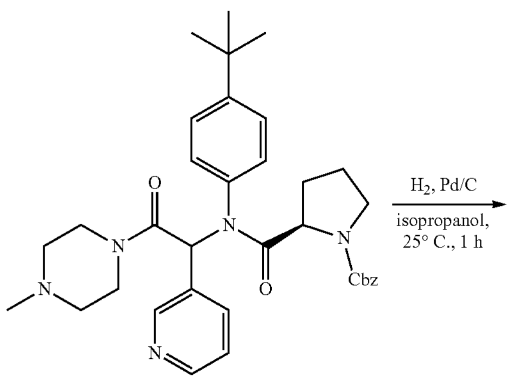

-continued

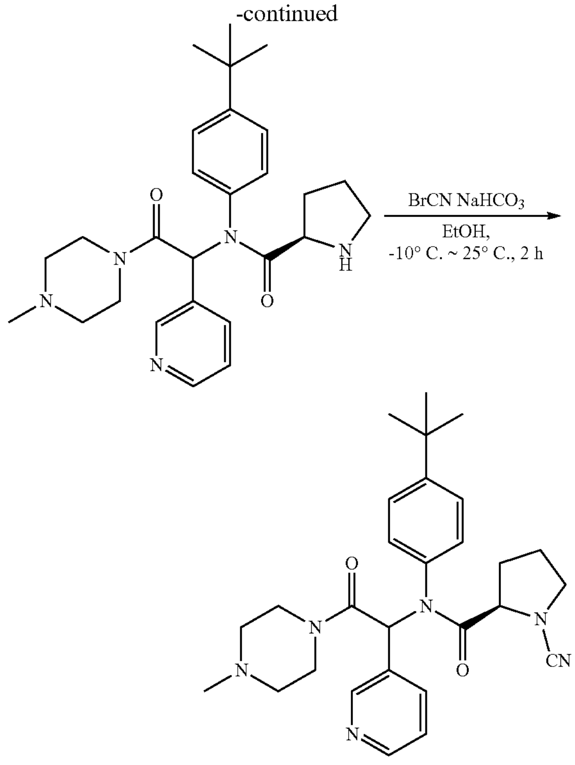

Step 1: (2R)-benzyl2-((4-(tert-butyl)phenyl)(2-(4-methylpiperazin-1-yl)-2-oxo-1-(pyridin-3-yl)ethyl)carbamoyl)pyrrolidine-1-carboxylate To a solution of 1-methylpiperazine (77.71 mg, 775.80 umol, 86.05 uL, 1 eq), 2-((R)-1-((benzyloxy)carbonyl)-N-(4-(tert-butyl)phenyl)pyrrolidine-2-carboxamido)-2-(pyridin-3-yl)acetic acid (400.00 mg, 775.80 umol, 1 eq) in ACN (15 mL) was added [chloro(dimethylamino)methylene]-dimethyl-ammonium;hexafluorophosphate (282.97 mg, 1.01 mmol, 1.3 eq) and 1-methylimidazole (191.09 mg, 2.33 mmol, 185.52 uL, 3 eq). After stirring at 75° C. for 2 h, the mixture was concentrated in the vacuum and quenched by addition $H_2O$ 50 mL and then extracted with EtOAc 20 mL*3. The combined organic layers were washed with brine 50 mL, dried over $Na_2SO_4$, filtered and concentrated under reduced pressure to give a residue and was purified by column chromatography (SiO2, DCM:MeOH=10:1) to give a product (2R)-benzyl 2-((4-(tert-butyl)phenyl)(2-(4-methylpiperazin-1-yl)-2-oxo-1-(pyridin-3-yl)ethyl)carbamoyl)pyrrolidine-1-carboxylate (340 mg, 568.80 umol, 73.32% yield) as yellow oil. MS (ESI) m/z 598.3 $[M+H]^+$ Step 2: (2R)—N-(4-(tert-butyl)phenyl)-N-(2-(4-methylpiperazin-1-yl)-2-oxo-1-(pyridin-3-yl)ethyl)pyrrolidine-2-carboxamide Isomer 1 and Isomer 2: to a solution of benzyl (2R)-benzyl 2-((4-(tert-butyl)phenyl)(2-(4-methylpiperazin-1-yl)-2-oxo-1-(pyridin-3-yl)ethyl)carbamoyl)pyrrolidine-1-carboxylate (320 mg, 535.35 umol, 1 eq) in isopropanol (5 mL) was added Pd/C (200 mg, 10% purity) and the mixture was stirred at 25° C. for 1 h under $H_2$. Upon completion, the mixture was filtered and concentrated in vacuum to afford (2R)—N-(4-(tert-butyl)phenyl)-N-(2-(4-methylpiperazin-1-yl)-2-oxo-1-(pyridin-3-yl)ethyl)pyrrolidine-2-carboxamide (180 mg, crude) as a yellow oil. MS (ESI) m/z 464.3 $[M+H]^+$ Step 3: (2R,4R)-1-cyano-N-[2-(cyclohexylamino)-2-oxo-1-(3-pyridyl)ethyl]-4-hydroxy-N-[4-(pentafluoro-$\lambda^6$-sulfanyl)phenyl]pyrrolidine-2-carboxamide Isomer 1 and Isomer 2

To a solution of (2R)—N-(4-(tert-butyl)phenyl)-N-(2-(4-methylpiperazin-1-yl)-2-oxo-1-(pyridin-3-yl)ethyl)pyrrolidine-2-carboxamide (150 mg, 323.55 umol, 1 eq) in EtOH (1 mL) was added $NaHCO_3$ (81.54 mg, 970.64 umol, 37.75 uL, 3 eq). The mixture was cooled to −10° C. and BrCN (51.41 mg, 485.32 umol, 35.70 uL, 1.5 eq) in EtOH (0.5 mL) was added. After stirring for 0.5 h at 0° C. and warmed to 25° C. gradually, the mixture was quenched by addition $H_2O$ 50 mL and then extracted with EtOAc 30 mL*3. The combined organic layers were washed with brine 30 mL, dried over $Na_2SO_4$, filtered and concentrated under reduced pressure to afford (2R)—N-(4-(tert-butyl)phenyl)-1-cyano-N-(2-(4-methylpiperazin-1-yl)-2-oxo-1-(pyridin-3-yl)ethyl) pyrrolidine-2-carboxamide (30 mg, 61.40 umol, 18.98% yield) as yellow solid.

$^1H$ NMR (400 MHz, MeOD-$d_4$) δ=8.39-8.27 (m, 2H), 7.83-7.25 (m, 3H), 7.20 (m, 7.9 Hz, 2H), 6.77-6.43 (m, 2H), 4.20-4.11 (m, 1H), 4.00-3.69 (m, 2H), 3.67-3.53 (m, 2H), 3.52-3.32 (m, 2H), 2.89-2.58 (m, 3H), 2.41-2.16 (m, 4H), 2.09-1.78 (m, 4H), 1.22 (d, J=8.8 Hz, 9H)

Example 187: Synthesis of Compound 427

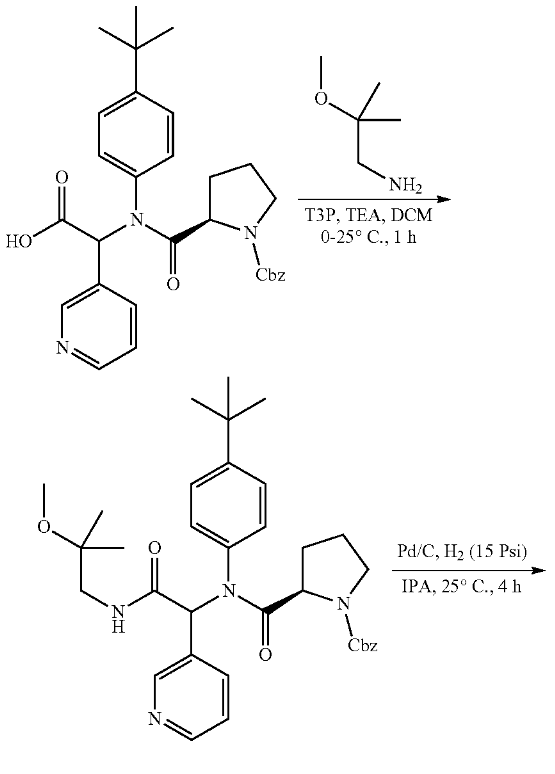

-continued

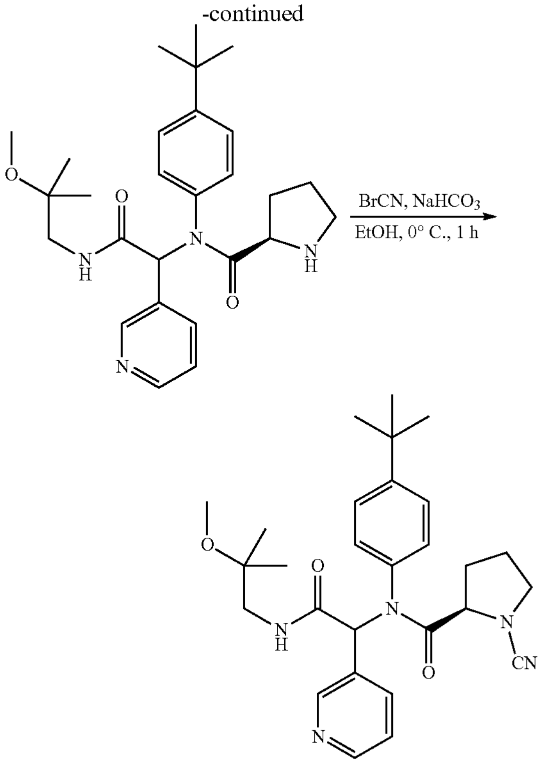

Step 1: (2R)-benzyl2-((4-(tert-butyl)phenyl)(2-((2-methoxy-2-methylpropyl)amino)-2-oxo-1-(pyridin-3-yl)ethyl)carbamoyl)pyrrolidine-1-carboxylate To a solution of 2-(N-[(2R)-1-benzyloxycarbonylpyrrolidine-2-carbonyl]-4-tert-butyl-anilino)-2-(3-pyridyl) acetic acid (400 mg, 775.80 umol, 1 eq) and 2-methoxy-2-methyl-propan-1-amine (400.17 mg, 3.88 mmol, 5 eq) in DCM (8 mL), was added TEA (392.51 mg, 3.88 mmol, 539.90 uL, 5 eq) at 0° C. After the addition of T3P (740.53 mg, 1.16 mmol, 692.09 uL, 50% purity, 1.5 eq) at 0° C., the mixture was stirred at 25° C. for 1 h. The mixture was quenched by water (21 mL) and then was extracted with DCM (7 mL*3), the combined organic layers were dried over $Na_2SO_4$, filtered and concentrated under reduced pressure to obtained (2R)-benzyl 2-((4-(tert-butyl)phenyl)(2-((2-methoxy-2-methylpropyl)amino)-2-oxo-1-(pyridin-3-yl)ethyl)carbamoyl)pyrrolidine-1-carboxylate (450 mg, crude) as a pink oil.

Step 2: (2R)—N-(4-(tert-butyl)phenyl)-N-(2-((2-methoxy-2-methylpropyl)amino)-2-oxo-1-(pyridin-3-yl)ethyl)pyrrolidine-2-carboxamide To a solution of (2R)-benzyl 2-((4-(tert-butyl)phenyl)(2-((2-methoxy-2-methylpropyl)amino)-2-oxo-1-(pyridin-3-yl)ethyl)carbamoyl)pyrrolidine-1-carboxylate (400 mg, 665.84 umol, 1 eq) in IPA (5 mL) was added Pd/C (40 mg, 10% purity) under H2 (15 Psi), the mixture was stirred at 25° C. for 4 h. The mixture was filtered and concentrated in vacuum to obtain (2R)—N-(4-(tert-butyl)phenyl)-N-(2-((2-methoxy-2-methylpropyl)amino)-2-oxo-1-(pyridin-3-yl) ethyl)pyrrolidine-2-carboxamide (300 mg, crude) as a colorless gum. MS (ESI) m/z 467.3 $[M+H]^+$ Step 3: (2R)—N-(4-(tert-butyl)phenyl)-1-cyano-N-(2-((2-methoxy-2-methylpropyl)amino)-2-oxo-1-(pyridin-3-yl)ethyl)pyrrolidine-2-carboxamide A solution of (2R)—N-(4-(tert-butyl)phenyl)-N-(2-((2-methoxy-2-methylpropyl)amino)-2-oxo-1-(pyridin-3-yl)ethyl)pyrrolidine-2-carboxamide (300 mg, 642.93 umol, 1 eq) in EtOH (8 mL) was added with $NaHCO_3$ (162.03 mg, 1.93 mmol, 75.01 uL, 3 eq) at 0° C. After adding BrCN (136.20 mg, 1.29 mmol, 94.58 uL, 2 eq) into the mixture at 0° C., the mixture was stirred at 0° C. for 1 h. The mixture was dried by blowing $N_2$, and then was quenched by water and extracted with DCM (10 mL*3), then was concentrated in vacuum and was purified by prep-HPLC to obtain (2R)—N-(4-(tert-butyl)phenyl)-1-cyano-N-(2-((2-methoxy-2-methylpropyl)amino)-2-oxo-1-(pyridin-3-yl)ethyl)pyrrolidine-2-carboxamide (Isomer 1: 27 mg, 54.92 umol, 8.54% yield, 100% purity) and (2R)—N-(4-(tert-butyl)phenyl)-1-cyano-N-(2-((2-methoxy-2-methylpropyl)amino)-2-oxo-1-(pyridin-3-yl)ethyl)pyrrolidine-2-carboxamide (Isomer 2: 47 mg, 95.60 umol, 14.87% yield, 100% purity) as a yellow solid. MS (ESI) m/z 492.3 $[M+H]^+$ prep-HPLC conditions: column: Waters Xbridge BEH C18 100*25 mm*5 um; mobile phase: [water (10 mM $NH4HCO_3$)-ACN]; B %: 25%-55%, 10 min.

$^1$H NMR (Isomer 1, 400 MHz, Methanol-$d_4$) δ ppm 8.41-8.25 (m, 2H), 7.85-7.03 (m, 5H), 6.64 (s, 1H), 6.06 (s, 1H), 4.14 (dd, J=4.8, 7.6 Hz, 1H), 3.62-3.54 (m, 1H), 3.50-3.35 (m, 2H), 3.27-3.21 (m, 1H), 3.16 (s, 3H), 2.06-1.75 (m, 4H), 1.25 (s, 9H), 1.14 (s, 3H), 1.05 (s, 3H).

$^1$H NMR (Isomer 2, 400 MHz, Methanol-$d_4$) δ ppm 8.31 (d, J=1.8 Hz, 1H), 8.28 (dd, J=1.2, 4.8 Hz, 1H), 7.79-7.09 (m, 5H), 6.64 (s, 1H), 6.24 (s, 1H), 4.13 (dd, J=5.1, 7.8 Hz, 1H), 3.63-3.54 (m, 1H), 3.49-3.36 (m, 2H), 3.21 (d, J=13.8 Hz, 1H), 3.16 (s, 3H), 2.13-1.87 (m, 3H), 1.86-1.75 (m, 1H), 1.22 (s, 9H), 1.13 (s, 3H), 1.05 (s, 3H).

Example 188: Synthesis of Compound 435

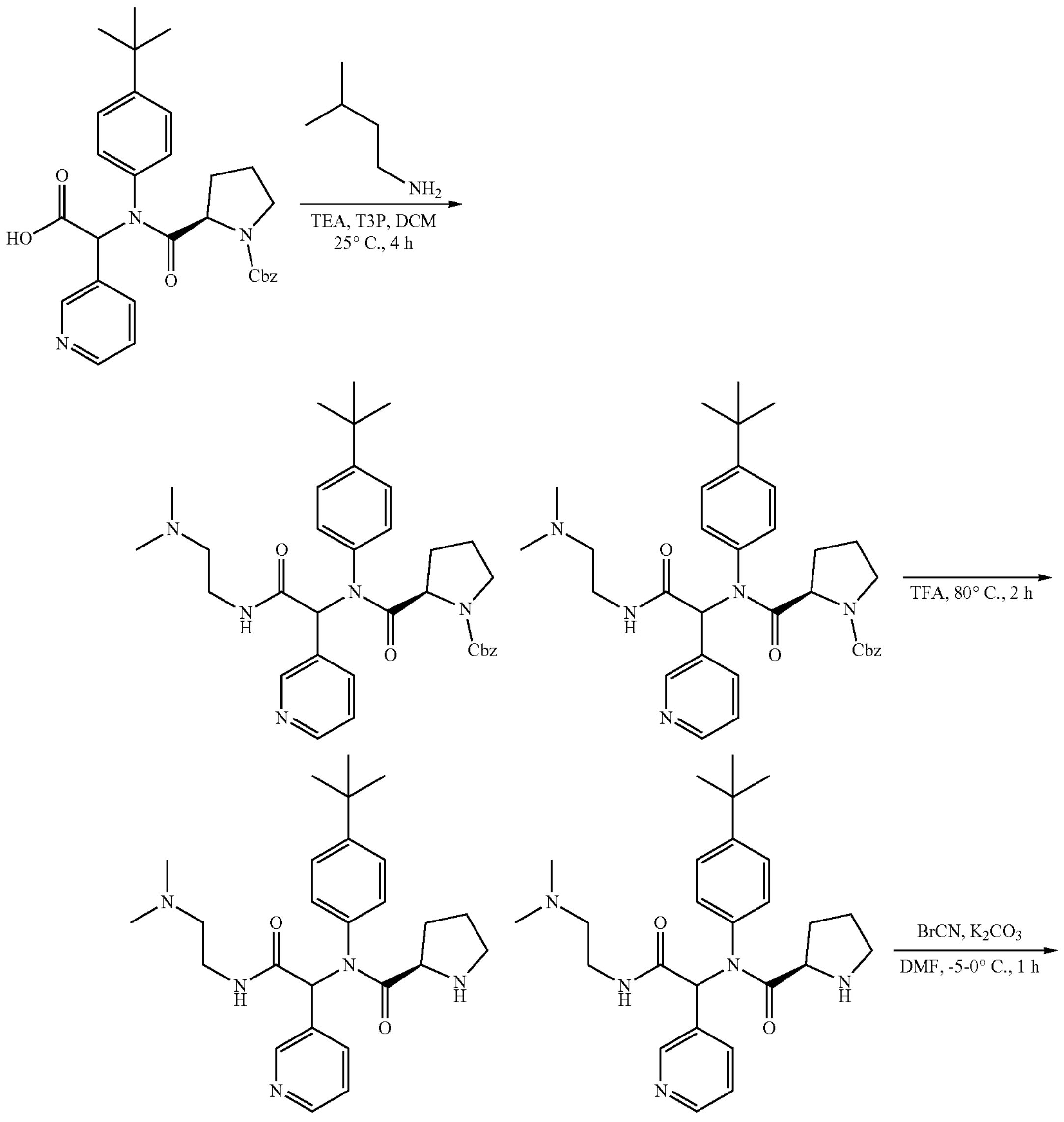

-continued

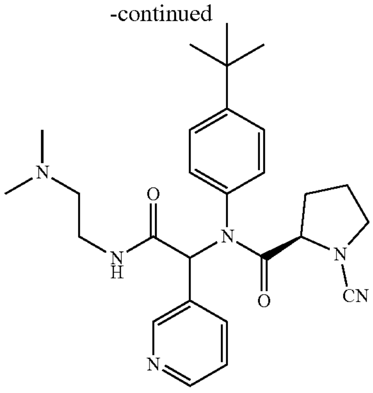

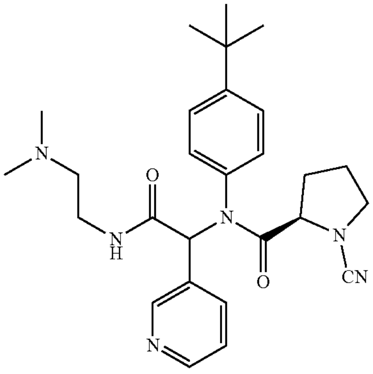

Step 1: benzyl (2R)-2-[(4-tert-butylphenyl)-[2-[2-(dimethylamino)ethylamino]-2-oxo-1-(3-pyridyl)ethyl]carbamoyl]pyrrolidine-1-carboxylate A mixture of 2-(N-[(2R)-1-benzyloxycarbonylpyrrolidine-2-carbonyl]-4-tert-butyl-anilino)-2-(3-pyridyl)acetic acid (400 mg, 775.80 umol, 1 eq) in DCM (4 mL), and then N',N'-dimethylethane-1,2-diamine (547.10 mg, 6.21 mmol, 677.94 uL, 8 eq), TEA (471.02 mg, 4.65 mmol, 647.89 uL, 6 eq) was added. After adding T3P (740.53 mg, 1.16 mmol, 692.08 uL, 50% purity, 1.5 eq), the mixture was stirred at 25° C. for 4 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-70%, 8 min) to provide benzyl (2R)-2-[(4-tert-butylphenyl)-[2-[2-(dimethylamino)ethylamino]-2-oxo-1-(3-pyridyl)ethyl]carbamoyl]pyrrolidine-1-carboxylate Isomer 1 (160 mg, 273.16 umol, 35.21% yield) as white solid. MS (ESI) m/z 586.3 $[M+H]^+$.

Benzyl (2R)-2-[(4-tert-butylphenyl)-[2-[2-(dimethylamino)ethylamino]-2-oxo-1-(3-pyridyl)ethyl]carbamoyl]pyrrolidine-1-carboxylate Isomer 2 (110 mg, 187.80 umol, 24.21% yield) was obtained as white solid. MS (ESI) m/z 586.3 $[M+H]^+$.

Step 2: (2R)—N-(4-tert-butylphenyl)-N-[2-[2-(dimethylamino)ethylamino]-2-oxo-1-(3-pyridyl)ethyl]pyrrolidine-2-carboxamide Isomer 1

A mixture of benzyl (2R)-2-[(4-tert-butylphenyl)-[2-[2-(dimethylamino)ethylamino]-2-oxo-1-(3-pyridyl)ethyl]carbamoyl]pyrrolidine-1-carboxylate Isomer 1 (150 mg, 256.09 umol, 1 eq) in TFA (2 mL) was stirred at 80° C. for 2 h. Upon completion, the reaction mixture was base-modulated in saturated $K_2CO_3$ (10 mL) solution, and extracted with EA (10 mL*3). The combined organic layers were washed with brine, dried over $Na_2SO_4$, filtered and concentrated under reduced pressure to give a residue to provide (2R)—N-(4-tert-butylphenyl)-N-[2-[2-(dimethylamino)ethylamino]-2-oxo-1-(3-pyridyl)ethyl]pyrrolidine-2-carboxamide Isomer 1 (125 mg, crude) as white oil. MS (ESI) m/z 452.2 $[M+H]^+$.

(2R)—N-(4-tert-butylphenyl)-N-[2-[2-(dimethylamino)ethylamino]-2-oxo-1-(3-pyridyl)ethyl]pyrrolidine-2-carboxamide Isomer 2

A mixture of benzyl (2R)-2-[(4-tert-butylphenyl)-[2-[2-(dimethylamino)ethylamino]-2-oxo-1-(3-pyridyl)ethyl]carbamoyl]pyrrolidine-1-carboxylate Isomer 2 (110 mg, 187.80 umol, 1 eq) in TFA (2 mL), the mixture at 80° C. for 2 h. Upon completion, the reaction mixture was base-modulated in saturated $K_2CO_3$ (10 mL) solution, and extracted with EA (10 mL*3). The combined organic layers were washed with brine, dried over $Na_2SO_4$, filtered and concentrated under reduced pressure to give a residue to get a product (2R)—N-(4-tert-butylphenyl)-N-[2-[2-(dimethylamino)ethylamino]-2-oxo-1-(3-pyridyl)ethyl]pyrrolidine-2-carboxamide Isomer 2 (90 mg, crude) as a white oil. MS (ESI) m/z 452.2 $[M+H]^+$.

Step 3: (2R)—N-(4-tert-butylphenyl)-1-cyano-N-[2-[2-(dimethylamino)ethylamino]-2-oxo-1-(3-pyridyl)ethyl]pyrrolidine-2-carboxamide Isomer 1

A mixture of (2R)—N-(4-tert-butylphenyl)-N-[2-[2-(dimethylamino)ethylamino]-2-oxo-1-(3-pyridyl)ethyl]pyrrolidine-2-carboxamide Isomer 1 (0.12 g, 265.72 umol, 1 eq) in DMF (2 mL) was added $K_2CO_3$ (110.18 mg, 797.16 umol, 3 eq), and the solution was cooled to −5° C. After adding BrCN (30.96 mg, 292.29 umol, 21.50 uL, 1.1 eq) in DMF (0.5 mL) drop-wise, the mixture was stirred at 0° C. for 1 h under $N_2$. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 20%-40%, 8 min) to provide (2R)—N-(4-tert-butylphenyl)-1-cyano-N-[2-[2-(dimethylamino)ethylamino]-2-oxo-1-(3-pyridyl)ethyl]pyrrolidine-2-carboxamide Isomer 1 (8.32 mg, 16.69 umol, 6.28% yield, 95.6% purity) as white solid. MS (ESI) m/z 477.2 $[M+H]^+$.

$^1H$ NMR (400 MHz, METHANOL-$d_4$) δ=8.49 (br s, 1H), 8.40-8.24 (m, 2H), 7.61 (td, J=1.8, 8.0 Hz, 1H), 7.47-7.14 (m, 4H), 6.00 (s, 1H), 4.16 (dd, J=5.2, 7.8 Hz, 1H), 3.67-3.53 (m, 2H), 3.51-3.41 (m, 2H), 2.98 (q, J=6.2 Hz, 2H), 2.70 (s, 6H), 2.12-1.76 (m, 4H), 1.24 (s, 9H).

(2R)—N-(4-tert-butylphenyl)-1-cyano-N-[2-[2-(dimethylamino)ethylamino]-2-oxo-1-(3-pyridyl)ethyl]pyrrolidine-2-carboxamide Isomer 2

A mixture of (2R)—N-(4-tert-butylphenyl)-N-[2-[2-(dimethylamino)ethylamino]-2-oxo-1-(3-pyridyl)ethyl]pyrrolidine-2-carboxamide Isomer 2 (0.08 g, 177.15 umol, 1 eq) in DMF (2 mL) was added $K_2CO_3$ (73.45 mg, 531.44 umol, 3 eq), and the solution was cooled to −5° C. After adding BrCN (20.64 mg, 194.86 umol, 14.33 uL, 1.1 eq) in DMF (0.5 mL) drop-wise, the solution was stirred at 0° C. for 1 h under $N_2$. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 5%-45%, 8 min) to afford (2R)—N-(4-tert-butylphenyl)-1-cyano-N-[2-[2-(dimethylamino)ethylamino]-2-oxo-1-(3-pyridyl)ethyl]pyrrolidine-2-carboxamide Isomer 2 (7.32 mg, 14.38 umol, 8.11% yield, 93.6% purity) as white solid. MS (ESI) m/z 477.3 $[M+H]^+$.

$^1H$ NMR (400 MHz, METHANOL-$d_4$) δ=8.51 (s, 1H), 8.36 (br s, 2H), 7.66-7.51 (m, 1H), 7.47-7.03 (m, 4H), 6.05-5.84 (m, 1H), 4.24-4.12 (m, 1H), 3.83-3.69 (m, 1H), 3.66-3.37 (m, 3H), 3.22-2.99 (m, 2H), 2.83 (s, 6H), 2.10-1.76 (m, 4H), 1.26-1.22 (m, 9H).

Example 189: Synthesis of Compound 946b

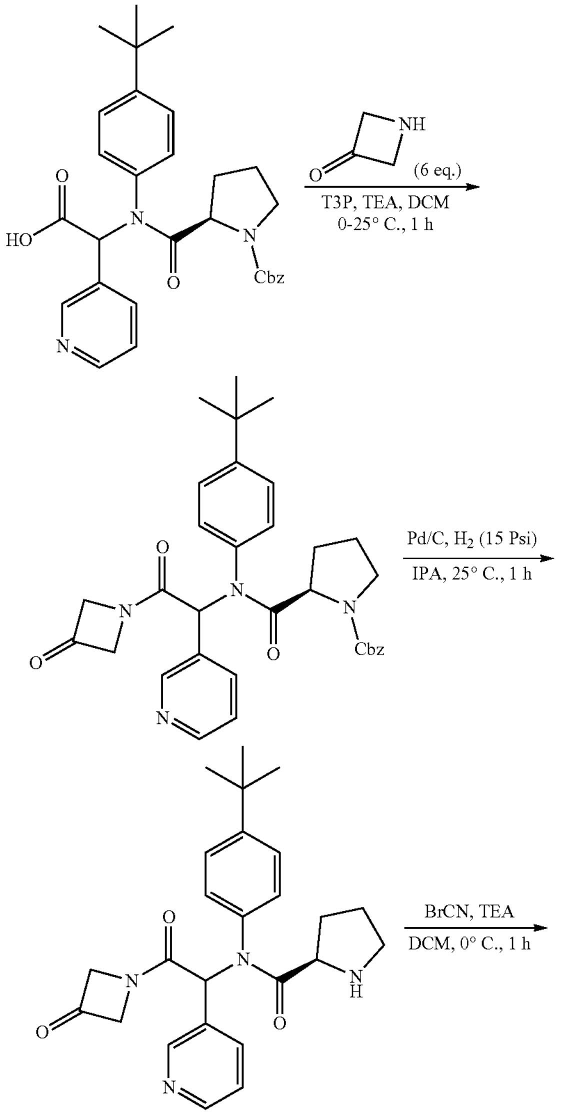

-continued

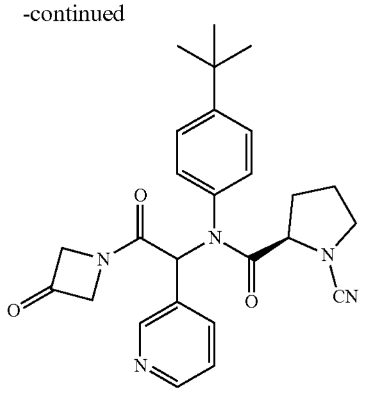

Step 1: (2R)-benzyl2-((4-(tert-butyl)phenyl)(2-oxo-2-(3-oxoazetidin-1-yl)-1-(pyridin-3-yl)ethyl)carbamoyl)pyrrolidine-1-carboxylate To a solution of 2-((R)-1-((benzyloxy)carbonyl)-N-(4-(tert-butyl)phenyl)pyrrolidine-2-carboxamido)-2-(pyridine-3-yl) acetic acid (300 mg, 581.85 umol, 1 eq), azetidin-3-one (206.78 mg, 2.91 mmol, 5 eq), and TEA (294.38 mg, 2.91 mmol, 404.93 uL, 5 eq) in DCM (8 mL) was added TEA (294.38 mg, 2.91 mmol, 404.93 uL, 5 eq). The mixture was cooled to 0° C., and T3P (555.40 mg, 872.77 umol, 519.06 uL, 50% purity, 1.5 eq) was added at 0° C., then the mixture was stirred at 25° C. for 1 h under $N_2$ atmosphere. The mixture was quenched by water (6 mL) and then was extracted with DCM (2 mL*3), the combined organic layers were dried over $Na_2SO_4$, filtered and concentrated under reduced pressure to give a residue and was purified by prep-TLC($SiO_2$, EA) to obtained (2R)-benzyl 2-((4-(tert-butyl)phenyl)(2-oxo-2-(3-oxoazetidin-1-yl)-1-(pyridin-3-yl)ethyl)carbamoyl) pyrrolidine-1-carboxylate (90 mg, 126.61 umol, 21.76% yield, 80% purity) as a yellow oil. MS (ESI) m/z 569.2, 587.3 $[M+H, M+H_2O]^+$ Step 2: (2R)—N-(4-(tert-butyl)phenyl)-N-(2-oxo-2-(3-oxoazetidin-1-yl)-1-(pyridin-3-yl)ethyl)pyrrolidine-2-carboxamide A solution of (2R)-benzyl 2-((4-(tert-butyl)phenyl)(2-oxo-2-(3-oxoazetidin-1-yl)-1-(pyridin-3-yl)ethyl) carbamoyl)pyrrolidine-1-carboxylate (90 mg, 158.27 umol, 1 eq) in isopropanol (2 mL), was added Pd/C (10 mg, 10% purity) at 25° C. under $H_2$ (15 Psi), and the mixture was stirred at 25° C. for 1 h. The mixture was filtered and concentration in vacuum to obtained (2R)—N-(4-(tert-butyl)phenyl)-N-(2-oxo-2-(3-oxoazetidin-1-yl)-1-(pyridin-3-yl)ethyl)pyrrolidine-2-carboxamide (60 mg, crude) as a colorless oil. MS (ESI) m/z 435.4, 453.4 $[M+H, M+H_2O]^+$ Step 3: (2R)—N-(4-(tert-butyl)phenyl)-1-cyano-N-(2-oxo-2-(3-oxoazetidin-1-yl)-1-(pyridin-3-yl)ethyl) pyrrolidine-2-carboxamide To a solution of (2R)—N-(4-(tert-butyl)phenyl)-N-(2-oxo-2-(3-oxoazetidin-1-yl)-1-(pyridin-3-yl)ethyl) pyrrolidine-2-carboxamide (40 mg, 92.05 umol, 1 eq) in DCM (1 mL) was added TEA (27.94 mg, 276.16 umol, 38.44 uL, 3 eq) at 0° C. After adding BrCN (19.50 mg, 184.11 umol, 13.54 uL, 2 eq) at 0° C., the mixture was stirred at 0° C. for 1 h. The mixture was dried by blowing $N_2$, and then was quenched by water and extracted with DCM (5 mL*3), and then was concentration in vacuum and was purified by prep-HPLC to obtained (2R)—N-(4-(tert-butyl)phenyl)-1-cyano-N-(2-oxo-2-(3-oxoazetidin-1-yl)-1-(pyridin-3-yl)ethyl)pyrrolidine-2-carboxamide (2.7 mg, 5.11 umol, 5.55% yield, 87% purity) as a yellow solid. MS (ESI) m/z 460.2, 478.2 $[M+H, M+H_2O]^+$ prep-HPLC conditions: column: Waters Xbridge BEH C18 100*25 mm*5 um; mobile phase: [water (10 mM $NH_4HCO_3$)-ACN]; B %: 20%-60%, 10 min.

$^1$H NMR (400 MHz, Methanol-$d_4$) δ ppm 8.35 (dd, J=3.8, 16.8 Hz, 2H), 7.73-7.09 (m, 5H), 6.90-6.45 (m, 1H), 6.29-6.08 (m, 1H), 4.68-4.29 (m, 1H), 4.15 (d, J=6.2 Hz, 1H), 4.06-3.77 (m, 1H), 3.71-3.36 (m, 3H), 3.26-2.89 (m, 1H), 2.17-1.74 (m, 4H), 1.31-1.19 (m, 9H).

Example 190: Synthesis of Compound 962

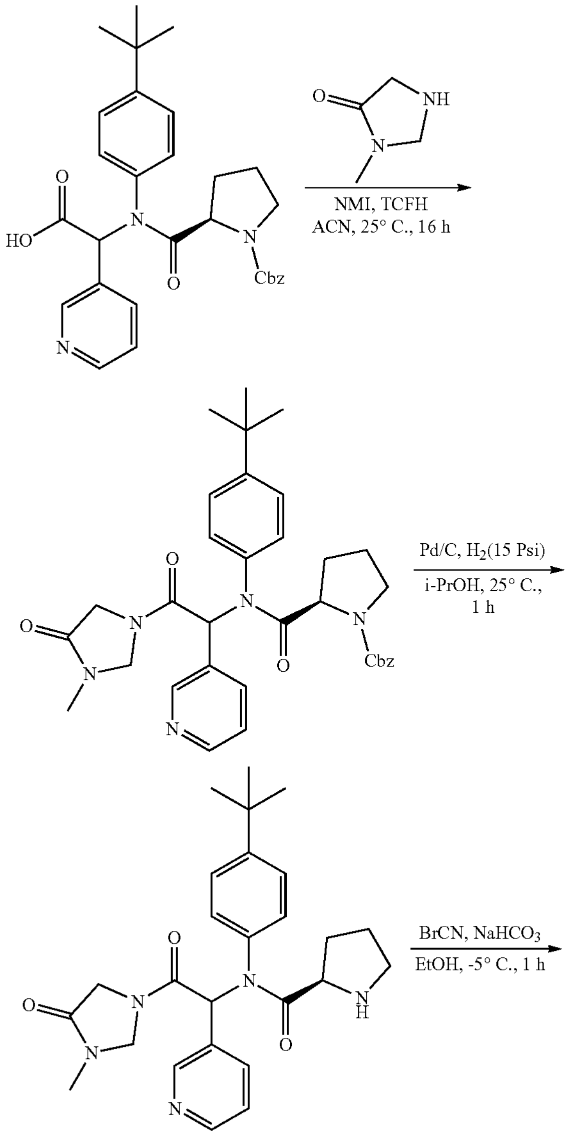

-continued

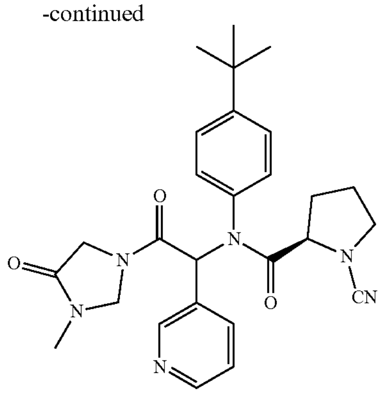

Step 1: (2R)-benzyl2-((4-(tert-butyl)phenyl)(2-(3-methyl-4-oxoimidazolidin-1-yl)-2-oxo-1-(pyridin-3-yl)ethyl)carbamoyl)pyrrolidine-1-carboxylate 2-(N-[(2R)-1-benzyloxycarbonylpyrrolidine-2-carbonyl]-4-tert-butyl-anilino)-2-(3-pyridyl)acetic acid (250 mg, 339.41 umol, 70% purity, 1 eq) was dissolved in ACN (5 mL), and then 3-methylimidazolidin-4-one (50.97 mg, 509.12 umol, 1.5 eq), 1-methylimidazole (139.33 mg, 1.70 mmol, 135.28 uL, 5 eq) [chloro(dimethylamino)methylene]-dimethyl-ammonium;hexafluorophosphate (190.46 mg, 678.82 umol, 2 eq) were added into the solution. The mixture was stirred at 25° C. for 16 h, and then $H_2O$ (30 mL) was added and extracted with DCM (30 mL*3). The combined organic layers were washed with brine (50 mL), dried over $Na_2SO_4$, filtered and concentrated under reduced pressure to give a residue. The residue was purified by prep-TLC (dichloromethane:methanol=10:1) to give benzyl (2R)-2-[(4-tert-butylphenyl)-[2-(3-methyl-4-oxo-imidazolidin-1-yl)-2-oxo-1-(3-pyridyl)ethyl]carbamoyl]pyrrolidine-1-carboxylate (0.07 g, 99.55 umol, 59.50% yield, 85% purity) as a yellow oil. MS (ESI) m/z 598.3 $[M+H]^+$.

Step 2: (2R)—N-(4-(tert-butyl)phenyl)-N-(2-(3-methyl-4-oxoimidazolidin-1-yl)-2-oxo-1-(pyridin-3-yl)ethyl)pyrrolidine-2-carboxamide To a solution of benzyl (2R)-2-[(4-tert-butylphenyl)-[2-(3-methyl-4-oxo-imidazolidin-1-yl)-2-oxo-1-(3-pyridyl)ethyl]carbamoyl]pyrrolidine-1-carboxylate (0.07 g, 117.12 umol, 1 eq) in i-PrOH (2 mL) was added Pd/C (0.02 g, 117.12 umol, 10% purity, 1 eq). The mixture was stirred at 25° C. for 1 h at 15 Psi under $H_2$ (236.57 ug, 117.12 umol, 1 eq). Upon completion, the reaction mixture was filtered and the filtrate was concentrated under reduced pressure to give (2R)—N-(4-tert-butylphenyl)-N-[2-(3-methyl-4-oxo-imidazolidin-1-yl)-2-oxo-1-(3-pyridyl)ethyl]pyrrolidine-2-carboxamide (0.05 g, crude) as a yellow oil. MS (ESI) m/z 464.2 $[M+H]^+$.

Step 3: (2R)—N-(4-(tert-butyl)phenyl)-1-cyano-N-(2-(3-methyl-4-oxoimidazolidin-1-yl)-2-oxo-1-(pyridin-3-yl)ethyl)pyrrolidine-2-carboxamide To a solution of (2R)—N-(4-tert-butylphenyl)-N-[2-(3-methyl-4-oxo-imidazolidin-1-yl)-2-oxo-1-(3-pyridyl)ethyl]pyrrolidine-2-carboxamide (0.04 g, 86.29 umol, 1 eq) in EtOH (1 mL) was added $NaHCO_3$ (21.75 mg, 258.86 umol, 10.07 uL, 3 eq), and the solution was cooled to −5° C. and BrCN (9.14 mg, 86.29 umol, 6.35 uL, 1 eq) in EtOH (0.5 mL). The mixture was stirred at −5° C. for 1 h. Upon completion, the reaction mixture was diluted with water (10 mL) and extracted with EA (5 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 25%-55%, 10 min) to give (2R)—N-(4-tert-butylphenyl)-1-cyano-N-[2-(3-methyl-4-oxo-imidazolidin-1-yl)-2-oxo-1-(3-pyridyl)ethyl]pyrrolidine-2-carboxamide (10.49 mg, 21.47 umol, 24.88% yield, 100% purity) as a white solid. MS (ESI) m/z 489.2 $[M+H]^+$.

$^1H$ NMR (400 MHz, METHANOL-$d_4$) δ=8.45-8.28 (m, 2H), 7.83-7.02 (m, 5H), 6.89-6.44 (m, 1H), 6.37-6.20 (m, 1H), 5.41-4.98 (m, 1H), 4.87-4.76 (m, 1H), 4.69-4.43 (m, 1H), 4.21-4.13 (m, 1H), 4.03-3.52 (m, 2H), 3.50-3.39 (m, 1H), 2.96-2.81 (m, 3H), 2.12-1.74 (m, 4H), 1.29-1.17 (m, 9H).

$^1H$ NMR (400 MHz, DMSO-$d_6$) δ=8.44-8.25 (m, 2H), 7.44 (br d, J=7.9 Hz, 1H), 7.32-6.83 (m, 5H), 6.39-6.14 (m, 1H), 5.23-4.81 (m, 1H), 4.80-4.59 (m, 1H), 4.54-4.23 (m, 1H), 4.10-3.72 (m, 2H), 3.46-3.33 (m, 2H), 2.78 (br s, 3H), 1.96-1.66 (m, 4H), 1.23-1.14 (m, 9H).

Example 191: Synthesis of Compound 975

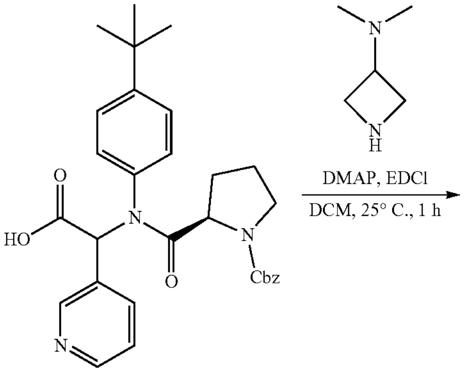

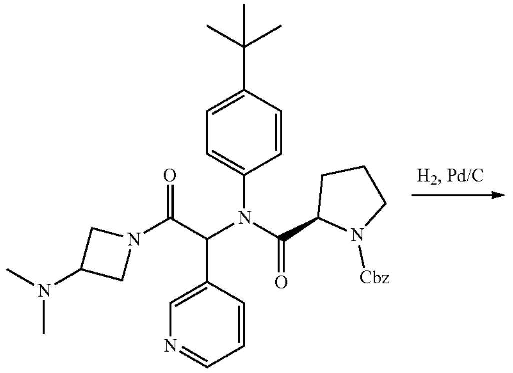

-continued

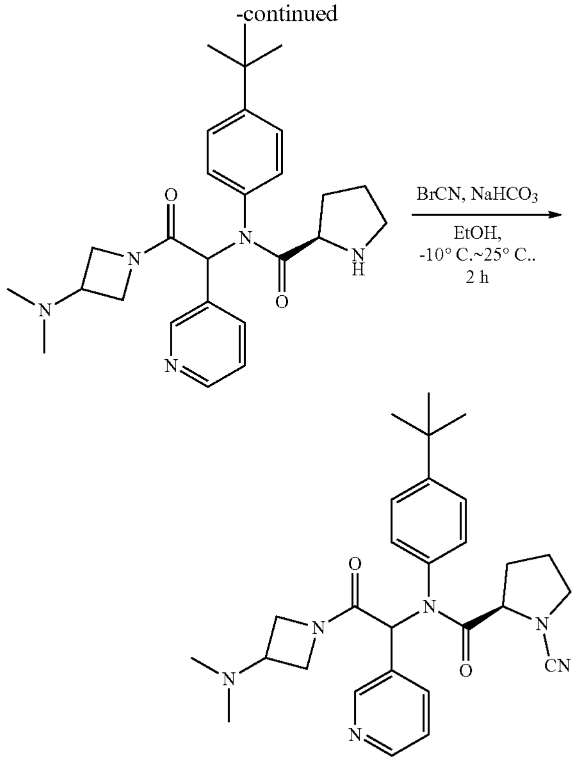

Step 1: (2R)-benzyl2-((4-(tert-butyl)phenyl)(2-(3-(dimethylamino)azetidin-1-yl)-2-oxo-1-(pyridin-3-yl)ethyl)carbamoyl)pyrrolidine-1-carboxylate To a solution of N,N-dimethylazetidin-3-amine (134.28 mg, 775.80 umol, 1 eq, 2HCl) 2-((R)-1-((benzyloxy)carbonyl)-N-(4-(tert-butyl)phenyl)pyrrolidine-2-carboxamido)-2-(pyridin-3-yl)acetic acid (400 mg, 775.80 umol, 1 eq) in DCM (15 mL) was added DMAP (379.11 mg, 3.10 mmol, 4 eq), EDCI (297.44 mg, 1.55 mmol, 2 eq) and the mixture was stirred at 25° C. for 1 h. Upon completion, the mixture was quenched by addition $H_2O$ (50 mL) and then extracted with DCM (50 mL*3). The combined organic layers were washed with brine (50 mL), dried over $Na_2SO_4$, filtered and concentrated under reduced pressure and was purified by prep-TLC ($SiO_2$, DCM:MeOH=10:1) to afford (2R)-benzyl 2-((4-(tert-butyl)phenyl)(2-(3-(dimethylamino)azetidin-1-yl)-2-oxo-1-(pyridin-3-yl)ethyl)carbamoyl)pyrrolidine-1-carboxylate (320 mg, 535.35 umol, 69.01% yield) was yellow oil. MS (ESI) m/z 598.3 $[M+H]^+$ Step 2: (2R)—N-(4-(tert-butyl)phenyl)-N-(2-(3-(dimethylamino)azetidin-1-yl)-2-oxo-1-(pyridin-3-yl)ethyl)pyrrolidine-2-carboxamide To a solution of (2R)-benzyl 2-((4-(tert-butyl)phenyl)(2-(3-(dimethylamino)azetidin-1-yl)-2-oxo-1-(pyridin-3-yl) ethyl)carbamoyl)pyrrolidine-1-carboxylate (310 mg, 518.62 umol, 1 eq) in isopropanol (10 mL) was added Pd/C (300 mg, 10% purity) and the mixture was stirred at 25° C. for 1 h under $H_2$. Upon completion, the reaction was filtered and concentrated in vacuum to give product (2R)—N-(4-(tert-butyl)phenyl)-N-(2-(3-(dimethylamino)azetidin-1-yl)-2-oxo-1-(pyridin-3-yl)ethyl)pyrrolidine-2-carboxamide (200 mg, crude) was yellow oil. MS (ESI) m/z 464.3 $[M+H]^+$ Step 3: (2R)—N-(4-(tert-butyl)phenyl)-1-cyano-N-(2-(3-(dimethylamino)azetidin-1-yl)-2-oxo-1-(pyridin-3-yl)ethyl)pyrrolidine-2-carboxamide To a solution of (2R)—N-(4-(tert-butyl)phenyl)-N-(2-(3-(dimethylamino)azetidin-1-yl)-2-oxo-1-(pyridin-3-yl)ethyl) pyrrolidine-2-carboxamide (180 mg, 388.25 umol, 1 eq) in EtOH (1 mL) was added $NaHCO_3$ (97.85 mg, 1.16 mmol, 45.30 uL, 3 eq) and the mixture was cooled at −10° C. and added BrCN (61.69 mg, 582.38 umol, 42.84 uL, 1.5 eq) in EtOH (0.5 mL). The mixture was stirred for 0.5 h at 0° C. and warmed to 25° C. gradually. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue. The crude product was purified by prep-HPLC (column: Phenomenex Luna C18 75*30 mm*3 um; mobile phase: [water (0.2% FA)-ACN]; B %: 10%-50%, 8 min) to afford (2R)—N-(4-(tert-butyl)phenyl)-1-cyano-N-(2-(3-(dimethylamino)azetidin-1-yl)-2-oxo-1-(pyridin-3-yl)ethyl) pyrrolidine-2-carboxamide (50 mg, 102.33 umol, 26.36% yield) was yellow solid. MS (ESI) m/z 489.3 $[M+H]^+$ $^1H$ NMR (400 MHz, MeOD-$d_4$) δ=8.40-8.29 (m, 2H), 7.84-6.50 (m, 6H), 6.24-6.15 (m, 1H), 4.56-4.55 (m, 1H), 4.29-4.00 (m, 3H), 3.88-3.68 (m, 1H), 3.60-3.58 (m, 1H), 3.50-3.33 (m, 2H), 2.42-2.30 (m, 3H), 2.23-2.17 (m, 31H), 2.10-1.77 (m, 4H), 1.25-1.22 (m, 9H)

$^1H$ NMR (400 MHz, DMSO-$d_6$) δ=8.41-8.29 (m, 2H), 7.39-7.28 (m, 1H), 7.32-6.91 (m, 5H), 6.19-6.08 (m, 1H), 4.35-3.64 (m, 5H), 3.47-3.45 (m, 1H), 3.42-3.32 (m, 2H), 2.18-1.95 (m, 6H), 1.93-1.67 (m, 4H), 1.25-1.18 (m, 9H)

Example 192: Synthesis of Compound 1101

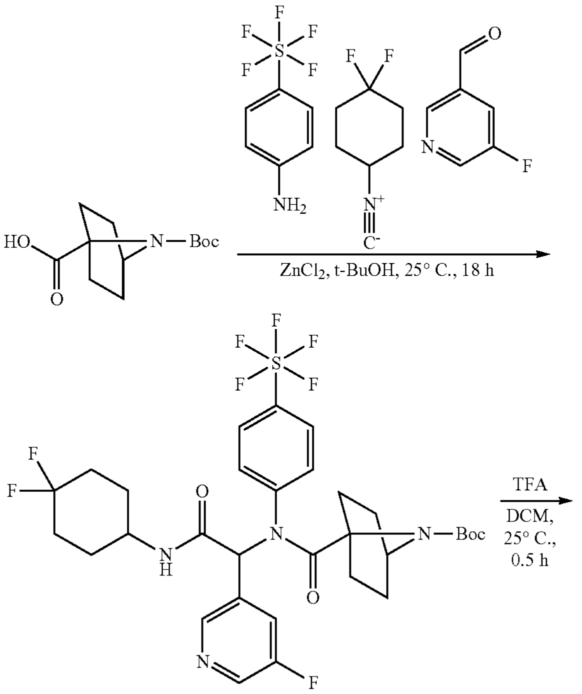

-continued

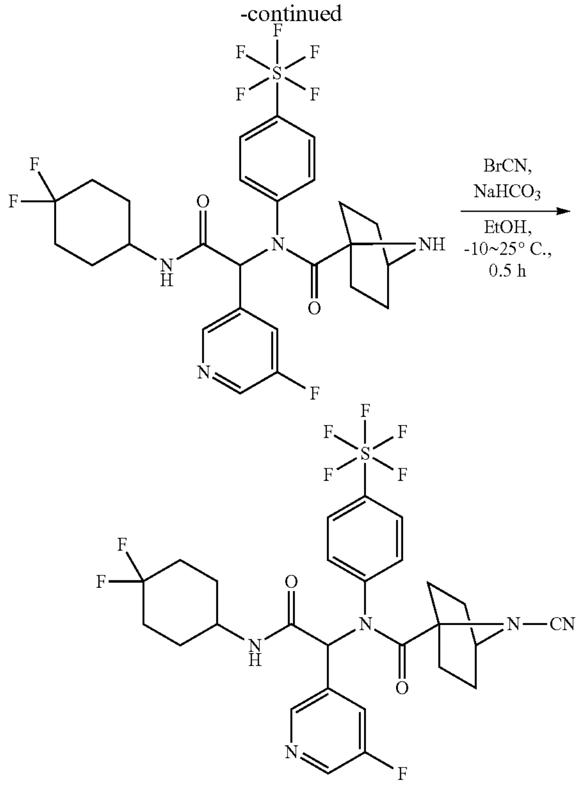

Step 1: tert-butyl 1-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-7-azabicyclo[2.2.1]heptane-7-carboxylate A solution of 5-fluoropyridine-3-carbaldehyde (155.54 mg, 1.24 mmol, 3.89 uL, 1 eq), 4-(pentafluoro-λ6-sulfanyl) aniline (272.51 mg, 1.24 mmol, 1 eq) in t-BuOH (6 mL) was stirred at 25° C. for 2 h. 7-tert-butoxycarbonyl-7-azabicyclo [2.2.1]heptane-1-carboxylic acid (300 mg, 1.24 mmol, 1 eq) was added to the reactant mixture, and then a solution of 1,1-difluoro-4-isocyano-cyclohexane (162.43 mg, 1.12 mmol, 0.9 eq) in t-BuOH (1 mL) was added in batches (three times). After adding $ZnCl_2$ (0.5 M, 14.92 mL, 6 eq), mixture was stirred at 25° C. for 16 h. The reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 55%-85%, 8 min) to give the title compound tert-butyl 1-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-7-azabicyclo [2.2.1]heptane-7-carboxylate (400 mg, 561.25 umol, 45.14% yield, N/A purity) was obtained as a yellow solid. MS (ESI) m/z 713.2 $[M+1]^+$ Step 2: N-[2-[(4,4-difluorocyclohexyl)amino]-1-(5-fluoro-3-pyridyl)-2-oxo-ethyl]-N-[4-(pentafluoro-16-sulfanyl)phenyl]-7-azabicyclo[2.2.1]heptane-1-carboxamide A mixture of tert-butyl 1-[[2-[(4,4-difluorocyclohexyl) amino]-1-(5-fluoro-3-pyridyl)-2-oxo-ethyl]-[4-(pentafluoro-λ6-sulfanyl)phenyl]carbamoyl]-7-azabicyclo [2.2.1]heptane-7-carboxylate (400 mg, 561.25 umol, 1 eq) in DCM (4 mL) and TFA (1.5 mL) was stirred at 25° C. for 0.5 h under $N_2$ atmosphere. Upon completion, the reaction mixture was quenched by addition $NaHCO_3$ (40 mL), and extracted with DCM (20 mL*3). The combined organic layers were washed with brine (20 mL), dried over $Na_2SO_4$, filtered and concentrated under reduced pressure to give a crude product N-[2-[(4,4-difluorocyclohexyl)amino]-1-(5-fluoro-3-pyridyl)-2-oxo-ethyl]-N-[4-(pentafluoro-λ6-sulfanyl)phenyl]-7-azabicyclo[2.2.1]heptane-1-carboxamide (300 mg, crude) was obtained as a yellow solid. MS (ESI) m/z 613.2 $[M+H]^+$ Step 3: 7-cyano-N-[2-[(4,4-difluorocyclohexyl)amino]-1-(5-fluoro-3-pyridyl)-2-oxo-ethyl]-N-[4-(pentafluoro-26-sulfanyl)phenyl]-7-azabicyclo[2.2.1]heptane-1-carboxamide To a solution of N-[2-[(4,4-difluorocyclohexyl)amino]-1-(5-fluoro-3-pyridyl)-2-oxo-ethyl]-N-[4-(pentafluoro-λ6-sulfanyl)phenyl]-7-azabicyclo[2.2.1]heptane-1-carboxamide (290 mg, 473.41 umol, 1 eq) and $NaHCO_3$ (119.31 mg, 1.42 mmol, 55.24 uL, 3 eq) in EtOH (4 mL) was added a solution of BrCN (75.22 mg, 710.11 umol, 52.23 uL, 1.5 eq) in EtOH (1 mL) drop-wise at −10° C. under $N_2$. The reaction mixture was slowly warmed to 25° C. for 2 h. Upon completion, the reaction mixture was quenched by addition $H_2O$ (60 mL) and extracted with EA (30 mL*3). The combined organic layers were washed with brine (30 mL), dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 40%-80%, 8 min) to give 7-cyano-N-[2-[(4,4-difluorocyclohexyl)amino]-1-(5-fluoro-3-pyridyl)-2-oxo-ethyl]-N-[4-(pentafluoro-λ6-sulfanyl)phenyl]-7-azabicyclo[2.2.1]heptane-1-carboxamide (130 mg, 203.89 umol, 43.07% yield, 100% purity) as a white solid. MS (ESI) m/z 638.2 $[M+H]^+$ $^1H$ NMR (400 MHz, MeOD-$d_4$) δ ppm 8.37 (d, J=7.2 Hz, 1H), 8.31 (d, J=2.8 Hz, 1H), 8.19 (s, 1H), 8.07 (s, 1H), 7.89 (s, 1H), 7.61 (s, 1H), 7.37-7.34 (m, 1H), 7.07 (s, 1H), 6.15 (s, 1H), 3.95-3.87 (m, 2H), 2.03-1.93 (m, 10H), 1.68-1.44 (m, 4H), 1.18-1.32 (m, 1H), 1.06-1.12 (m, 1H).

Example 193: Synthesis of Compound 1133a

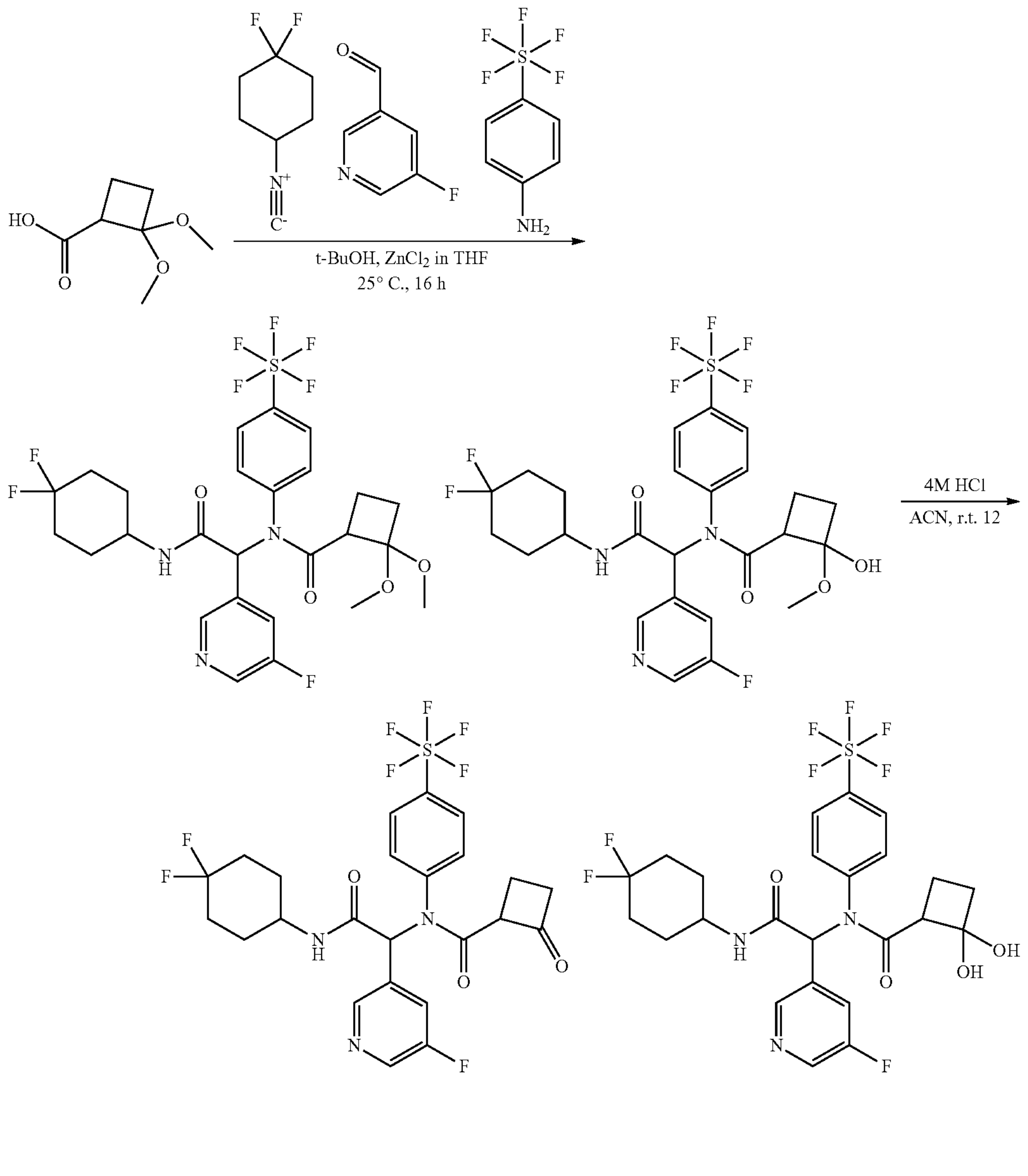

Step 1: tert-butyl N-[2-[(4,4-difluorocyclohexyl) amino]-1-(5-fluoro-3-pyridyl)-2-oxo-ethyl]-2-hydroxy-2-methoxy-N-[4-(pentafluoro-λ6-sulfanyl) phenyl]cyclobutanecarboxamide A solution of 5-fluoropyridine-3-carbaldehyde (234.32 mg, 1.87 mmol, 1 eq), 4-(pentafluoro-λ6-sulfanyl)aniline (410.52 mg, 1.87 mmol, 1 eq) in t-BuOH (10 mL) was stirred at 25° C. for 2 h, and 2,2-dimethoxycyclobutanecarboxylic acid (300 mg, 1.87 mmol, 1 eq) was added to the reactant mixture. A solution of 1,1-difluoro-4-isocyano-cyclohexane (244.68 mg, 1.69 mmol, 0.9 eq) in t-BuOH (1 mL) was added in batches (three times), followed by the addition of $ZnCl_2$ (0.5 M, 22.48 mL, 6 eq). After stirring the mixture for 14 h at 25° C., the mixture was concentrated under reduced pressure to give a residue. The residue was purified by column chromatography ($SiO_2$, petroleum ether/ethyl acetate=30/1 to 1/1) to give N-[2-[(4,4-difluorocyclohexyl)amino]-1-(5-fluoro-3-pyridyl)-2-oxo-ethyl]-2,2-dimethoxy-N-[4-(pentafluoro-λ6-sulfanyl)phenyl] cyclobutanecarboxamide (N/A purity) and N-[2-[(4,4-difluorocyclohexyl)amino]-1-(5-fluoro-3-pyridyl)-2-oxo-ethyl]-2-hydroxy-2-methoxy-N-[4-(pentafluoro-λ6-sulfanyl)phenyl]cyclobutanecarboxamide (600 mg, 524.65 umol, 28.01% yield, 54% purity) as a yellow solid. MS (ESI) m/z 618.2 $[M+1]^+$ Step 2: N-[2-[(4,4-difluorocyclohexyl)amino]-1-(5-fluoro-3-pyridyl)-2-oxo-ethyl]-2,2-dihydroxy-N-[4-(pentafluoro-λ6-sulfanyl)phenyl]cyclobutanecarboxamide To a solution of N-[2-[(4,4-difluorocyclohexyl)amino]-1-(5-fluoro-3-pyridyl)-2-oxo-ethyl]-2-hydroxy-2-methoxy-N-[4-(pentafluoro-λ6-sulfanyl)phenyl]cyclobutanecarboxamide (540 mg, 480.93 umol, 55% purity, 1 eq) in ACN (6 mL) was added HCl (4 M, 2 mL, 16.63 eq) under $N_2$. The reaction mixture was stirred at 20° C. for 16 h. Upon completion, the reaction mixture was concentrated under reduced pressure to give a residue. The residue was purified by prep-HPLC (column: Phenomenex Gemini-NX C18 80*30 mm*5 um; mobile phase: [water (0.2% FA)-ACN]; B %: 50%-70%, 8 min) to afford N-[2-[(4,4-difluorocyclohexyl) amino]-1-(5-fluoro-3-pyridyl)-2-oxo-ethyl]-2-oxo-N-[4-(pentafluoro-λ6-sulfanyl)phenyl]cyclobutanecarboxamide (N/A purity) and N-[2-[(4,4-difluorocyclohexyl) amino]-1-(5-fluoro-3-pyridyl)-2-oxo-ethyl]-2,2-dihydroxy-N-[4-(pentafluoro-λ6-sulfanyl)phenyl] cyclobutanecarboxamide (100 mg, 163.37 umol, 33.97% yield, 98.6% purity) as a white solid. MS (ESI) m/z 604.2 $[M+H]^+$ $^1H$ NMR (400 MHz, DMSO-$d_6$) δ ppm 11.99 (s, 1H), 8.39 (d, J=2.8 Hz, 1H), 8.29 (d, J=3.6 Hz, 1H), 8.15 (s, 1H), 7.81 (d, J=8.8 Hz, 2H), 7.51 (s, 2H), 7.40-7.37 (m, 1H), 6.11 (s, 1H), 3.91-3.71 (m, 1H), 2.18-1.64 (m, 12H), 1.52-1.46 (m, 1H), 1.41-1.35 (m, 1H).

Example 195: Synthesis of Compound 1149b

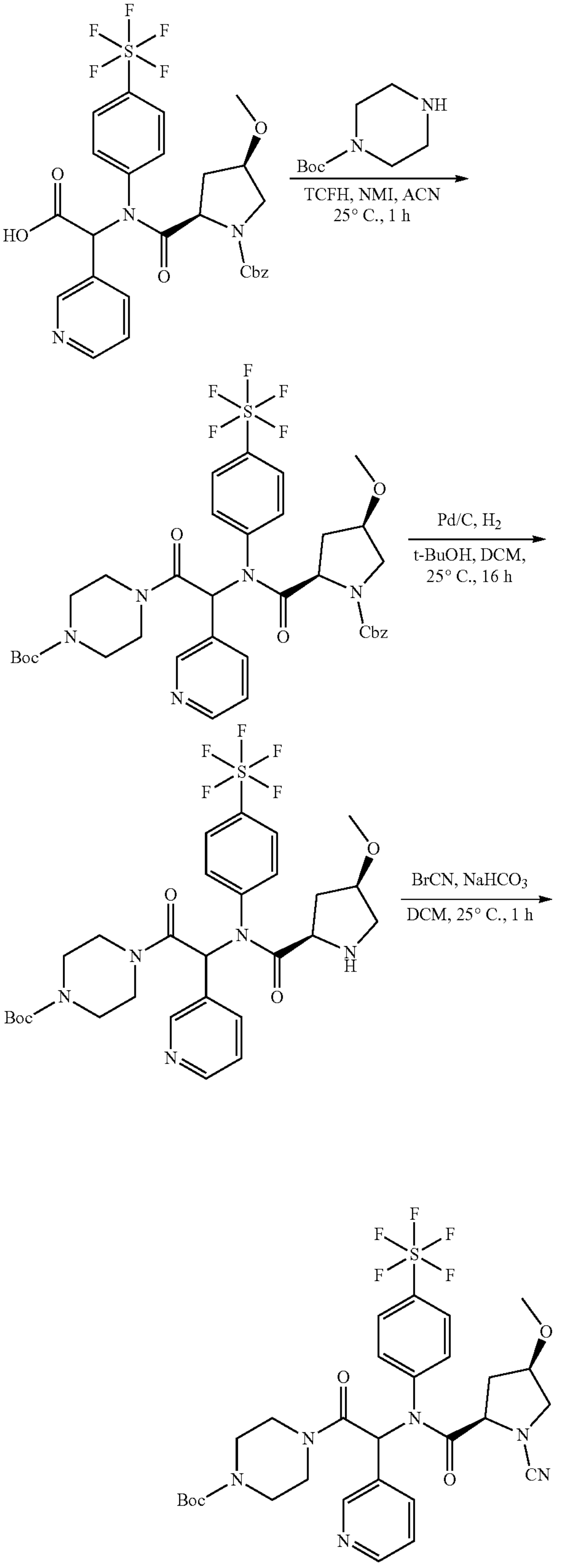

Step 1: tert-butyl-4-[2-[N-[(2R,4R)-1-benzyloxycarbonyl-4-methoxy-pyrrolidine-2-carbonyl]-4-(pentafluoro-26-sulfanyl)anilino]-2-(3-pyridyl)acetyl]piperazine-1-carboxylate A mixture of 2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetic acid (400 mg, 649.81 umol, 1 eq), tert-butyl piperazine-1-carboxylate (181.54 mg, 974.71 umol, 1.5 eq), 1-methylimidazole (266.76 mg, 3.25 mmol, 258.99 uL, 5 eq), [chloro(dimethylamino)methylene]-dimethyl-ammonium;hexafluorophosphate (364.64 mg, 1.30 mmol, 2 eq) and ACN (4 mL) was stirred at 25° C. for 1 h. The reaction mixture was diluted with $H_2O$ (30 mL) and extracted with DCM (30 mL*3). The combined organic layers were washed with brine (50 mL), dried over $Na_2SO_4$, filtered and concentrated under reduced pressure to give a residue. The residue was purified by column chromatography ($SiO_2$, petroleum ether/ethyl acetate=30/70) to get the product tert-butyl-4-[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl]piperazine-1-carboxylate (350 mg, 433.14 umol, 66.66% yield, 97% purity), as yellow solid. MS (ESI) m/z 784.4 $[M+H]^+$ Step 2: tert-butyl-4-[2-[N-[(2R,4R)-4-methoxypyrrolidine-2-carbonyl]-4-(pentafluoro-26-sulfanyl)anilino]-2-(3-pyridyl)acetyl]piperazine-1-carboxylate To a solution of tert-butyl-4-[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl]piperazine-1-carboxylate (340 mg, 433.78 umol, 1 eq) in t-BuOH (10 mL) and DCM (2 mL) was added Pd/C (300 mg, 10% purity) under $N_2$. The suspension was degassed under vacuum and purged with $H_2$ several times. The mixture was stirred under $H_2$ (15 psi) at 25° C. for 16 hours. The reaction mixture was filtered and the filter liquor was concentrated to get the product tert-butyl-4-[2-[N-[(2R,4R)-4-methoxypyrrolidine-2-carbonyl]-4-(pentafluoro-λ6-sulfanyl)anilino]-2-(3-pyridyl)acetyl]piperazine-1-carboxylate (340 mg, crude), as yellow solid. MS (ESI) m/z 650.2 $[M+H]^+$ Step 3: butyl-4-[2-[N-[(2R,4R)-1-cyano-4-methoxy-pyrrolidine-2-carbonyl]-4-(pentafluoro-λ6-sulfanyl)anilino]-2-(3-pyridyl)acetyl]piperazine-1-carboxylate To a mixture of tert-butyl-4-[2-[N-[(2R,4R)-4-methoxy-pyrrolidine-2-carbonyl]-4-(pentafluoro-λ6-sulfanyl)anilino]-2-(3-pyridyl)acetyl]piperazine-1-carboxylate (340 mg, 523.34 umol, 1 eq) and $NaHCO_3$ (131.89 mg, 1.57 mmol, 61.06 uL, 3 eq) in EtOH (4 mL), BrCN (83.15 mg, 785.01 umol, 57.74 uL, 1.5 eq) was added at 0° C., then the mixture was stirred at 25° C. for 1 h. The reaction mixture was diluted with $H_2O$ (30 mL) and extracted with EtOAc (30 mL*3). The combined organic layers were washed with brine (50 mL), dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH4HCO_3$)-ACN]; B %: 45%-55%, 8 min) to get the product tert-butyl-4-[2-[N-[(2R,4R)-1-cyano-4-methoxy-pyrrolidine-2-carbonyl]-4-(pentafluoro-λ6-sulfanyl)anilino]-2-(3-pyridyl)acetyl]piperazine-1-carboxylate (80 mg, 118.57 umol, 22.66% yield, 100% purity), as yellow solid. MS (ESI) m/z 675.3 $[M+H]^+$.

$^1H$ NMR (400 MHz, DMSO-$d_6$) δ=8.46-8.31 (m, 2H), 8.25-7.55 (m, 3H), 7.52-7.38 (m, 1H), 7.33-6.88 (m, 2H), 6.75-6.65 (m, 1H), 4.19-4.01 (m, 1H), 3.96-3.77 (m, 1H), 3.70-3.43 (m, 4H), 3.32-3.01 (m, 8H), 2.81-2.67 (m, 1H), 2.05-1.87 (m, 1H), 1.80-1.65 (m, 1H), 1.37 (s, 9H)

Example 196: Synthesis of Compound 1156

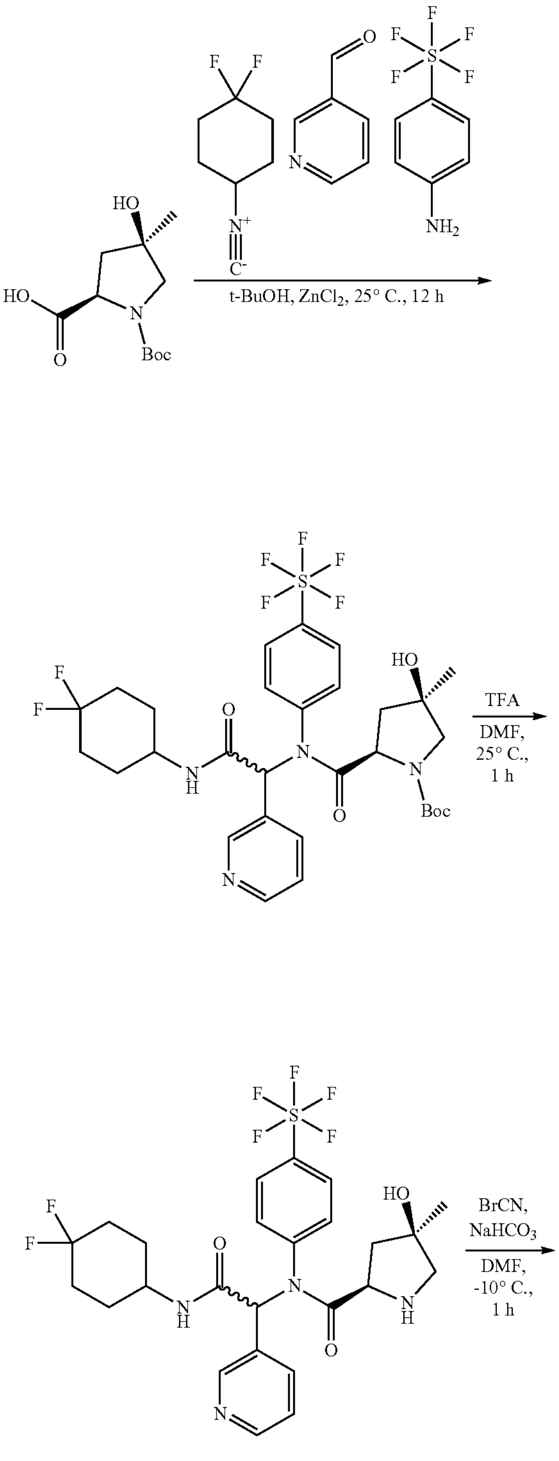

-continued

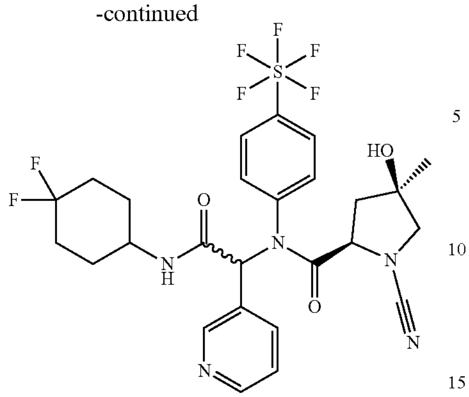

Step 1: tert-butyl (2R,4R)-2-[[2-[(4,4-difluorocyclohexyl)amino]-2-oxo-1-(3-pyridyl)ethyl]-[4-(pentafluoro-λ6-sulfanyl)phenyl]carbamoyl]-4-hydroxy-4-methyl-pyrrolidine-1-carboxylate To a solution of pyridine-3-carbaldehyde (150 mg, 1.40 mmol, 131.58 uL, 1 eq) and 4-(pentafluoro-λ6-sulfanyl) aniline (306.94 mg, 1.40 mmol, 1 eq) in t-BuOH (4 mL) was added (2R,4R)-1-tert-butoxycarbonyl-4-hydroxy-4-methyl-pyrrolidine-2-carboxylic acid (429.36 mg, 1.40 mmol, 80% purity, 1 eq) and 1,1-difluoro-4-isocyano-cyclohexane (203.27 mg, 1.40 mmol, 1 eq) in t-BuOH (1 mL) was added drop-wise. After adding $ZnCl_2$ (1 M, 4.20 mL, 3 eq) was added drop-wise, the mixture was stirred at 25° C. for 12 h. The reaction mixture was concentrated under reduced pressure to give a residue. The residue was purified by prep-TLC ($SiO_2$, PE/EA=0/1) and by prep-HPLC (column: Waters Xbridge BEH C18 100*25 mm*5 um; mobile phase: [water (10 mM $NH_4HCO_3$)-ACN]; B %: 45%-75%, 10 min) to give the product tert-butyl (2R,4R)-2-[[2-[(4,4-difluorocyclohexyl)amino]-2-oxo-1-(3-pyridyl)ethyl]-[4-(pentafluoro-λ6-sulfanyl)phenyl]carbamoyl]-4-hydroxy-4-methyl-pyrrolidine-1-carboxylate (200 mg, 148.85 umol, 10.63% yield, 52% purity) was obtained as a white solid. MS (ESI) m/z 699.3 $[M+H]^+$ Tert-butyl (2R,4R)-2-[[2-[(4,4-difluorocyclohexyl) amino]-2-oxo-1-(3-pyridyl)ethyl]-[4-(pentafluoro-λ6-sulfanyl)phenyl]carbamoyl]-4-hydroxy-4-methyl-pyrrolidine-1-carboxylate (80 mg, 108.77 umol, 7.77% yield, 95% purity) was obtained as a white solid. MS (ESI) m/z 699.3 $[M+H]^+$ Step 2: (2R,4R)—N-[2-[(4,4-difluorocyclohexyl) amino]-2-oxo-1-(3-pyridyl)ethyl]-4-hydroxy-4-methyl-N-[4-(pentafluoro-λ6-sulfanyl)phenyl]pyrrolidine-2-carboxamide To a solution of tert-butyl (2R,4R)-2-[[2-[(4,4-difluorocyclohexyl)amino]-2-oxo-1-(3-pyridyl)ethyl]-[4-(pentafluoro-λ6-sulfanyl)phenyl]carbamoyl]-4-hydroxy-4-methyl-pyrrolidine-1-carboxylate (200 mg, 148.85 umol, 52% purity, 1 eq) in DCM (3.0 mL) was added drop-wise TFA (1.53 g, 13.38 mmol, 990.82 uL, 89.91 eq), the mixture was stirred at 25° C. for 1 h. The reaction mixture was concentrated under reduced pressure to give a residue. The residue was diluted with DCM 20 mL and quenched by addition aq. $NaHCO_3$ 2 mL and $H_2O$ 15 mL at 0° C. to pH=8.0, and then extracted with DCM (20 mL*2). The combined organic layers were washed with brine 30 mL, dried over $Na_2SO_4$, filtered and concentrated under reduced pressure to give the product (2R,4R)—N-[2-[(4,4-difluorocyclohexyl)amino]-2-oxo-1-(3-pyridyl)ethyl]-4-hydroxy-4-methyl-N-[4-(pentafluoro-λ6-sulfanyl)phenyl]pyrrolidine-2-carboxamide (100 mg, crude) was obtained as a yellow solid. MS (ESI) m/z 599.2 $[M+H]^+$ To a solution of tert-butyl (2R,4R)-2-[[2-[(4,4-difluorocyclohexyl)amino]-2-oxo-1-(3-pyridyl)ethyl]-[4-(pentafluoro-λ6-sulfanyl)phenyl]carbamoyl]-4-hydroxy-4-methyl-pyrrolidine-1-carboxylate (80 mg, 114.50 umol, 1 eq) in DCM (3.0 mL) was added drop-wise TFA (1.54 g, 13.51 mmol, 1 mL, 117.96 eq), the mixture was stirred at 25° C. for 1 h. The reaction mixture was concentrated under reduced pressure to give a residue. The residue was diluted with 20 mL DCM and quenched by addition 2 mL $NaHCO_3$ (aq) and $H_2O$ 15 mL at 0° C. to pH=8.0, and then extracted with DCM (20 mL*2). The combined organic layers were washed with brine 30 mL, dried over $Na_2SO_4$, filtered and concentrated under reduced pressure to afford (2R,4R)—N-[2-[(4,4-difluorocyclohexyl)amino]-2-oxo-1-(3-pyridyl) ethyl]-4-hydroxy-4-methyl-N-[4-(pentafluoro-λ6-sulfanyl) phenyl]pyrrolidine-2-carboxamide (60 mg, crude) as a white solid. MS (ESI) m/z 599.1 $[M+H]^+$ Step 3: (2R,4R)-1-cyano-N-[2-[(4,4-difluorocyclohexyl)amino]-2-oxo-1-(3-pyridyl)ethyl]-4-hydroxy-4-methyl-N-[4-(pentafluoro-λ6-sulfanyl)phenyl] pyrrolidine-2-carboxamide A solution of (2R,4R)—N-[2-[(4,4-difluorocyclohexyl) amino]-2-oxo-1-(3-pyridyl)ethyl]-4-hydroxy-4-methyl-N-[4-(pentafluoro-λ6-sulfanyl)phenyl]pyrrolidine-2-carboxamide (90 mg, 81.19 umol, 54% purity, 1 eq) in DMF (1.5 mL) was cooled to −10° C., and then $NaHCO_3$ (20.46 mg, 243.58 umol, 9.47 uL, 3.0 eq) and BrCN (12.90 mg, 121.79 umol, 8.96 uL, 1.5 eq) was added drop-wise at −10° C. The mixture was stirred at −10° C. for 1 h, and the reaction mixture was quenched by addition $H_2O$ 20 mL at 0° C. and extracted with DCM (10 mL*3). The combined organic layers were washed with brine 15 mL, dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-70%, 8 min) to give the product (2R,4R)-1-cyano-N-[2-[(4,4-difluorocyclohexyl) amino]-2-oxo-1-(3-pyridyl)ethyl]-4-hydroxy-4-methyl-N-[4-(pentafluoro-λ6-sulfanyl)phenyl]pyrrolidine-2-carboxamide (24.05 mg, 38.57 umol, 47.50% yield, 100% purity) was obtained as a yellow solid.

$^1H$ NMR (DMSO-$d_6$, 400 MHz): δ ppm 8.33-8.37 (m, 1H), 8.28-8.33 (m, 2H), 6.99-8.07 (m, 6H), 6.01 (s, 1H), 4.09 (br d, J=4.3 Hz, 1H), 3.77 (br d, J=4.6 Hz, 1H), 3.28-3.34 (m, 11H), 3.17-3.26 (m, 1H), 1.71-2.00 (m, 8H), 1.47 (br s, 1H), 1.22-1.33 (m, 11H), 1.11 (s, 3H). MS (ESI) m/z 624.2 $[M+H]^+$ A solution of (2R,4R)—N-[2-[(4,4-difluorocyclohexyl) amino]-2-oxo-1-(3-pyridyl)ethyl]-4-hydroxy-4-methyl-N-[4-(pentafluoro-λ6-sulfanyl)phenyl]pyrrolidine-2-carboxamide (60 mg, 100.24 umol, 1 eq) in DMF (1.5 mL) was cooled to −10° C., and then $NaHCO_3$ (25.26 mg, 300.71 umol, 11.70 uL, 3.0 eq) and BrCN (15.93 mg, 150.36 umol, 11.06 uL, 1.5 eq) were added drop-wise at −10° C. The mixture was stirred at −10° C. for 1 h. The reaction mixture was quenched by addition $H_2O$ 20 mL at 0° C., and then extracted with DCM (10 mL*3). The combined organic layers were washed with brine 15 mL, dried over $Na_2SO_4$, filtered and concentrated under reduced pressure to give a residue. The residue was purified by prep-HPLC (column:

Phenomenex Luna C18 75*30 mm*3 um; mobile phase: [water (0.2% FA)-ACN]; B %: 30%-70%, 8 min) to give the product (2R,4R)-1-cyano-N-[2-[(4,4-difluorocyclohexyl) amino]-2-oxo-1-(3-pyridyl)ethyl]-4-hydroxy-4-methyl-N-[4-(pentafluoro-6-sulfanyl)phenyl]pyrrolidine-2-carboxamide (25.1 mg, 40.25 umol, 40.16% yield, 100% purity) was obtained as a white solid.

$^1$H NMR (METHANOL-$d_4$, 400 MHz): δ ppm 8.41 (br d, J=7.6 Hz, 1H), 8.31-8.38 (m, 2H), 6.76-8.23 (m, 6H), 6.24 (s, 1H), 4.25 (dd, J=9.2, 4.6 Hz, 1H), 3.83-3.98 (m, 1H), 3.50 (d, J=9.2 Hz, 1H), 3.34 (d, J=9.2 Hz, 1H), 1.81-2.12 (m, 8H), 1.66 (br s, 1H), 1.48 (br s, 1H), 1.25 (s, 3H). MS (ESI) m/z 624.2 $[M+H]^+$ Example 197: Synthesis of Compound 823a

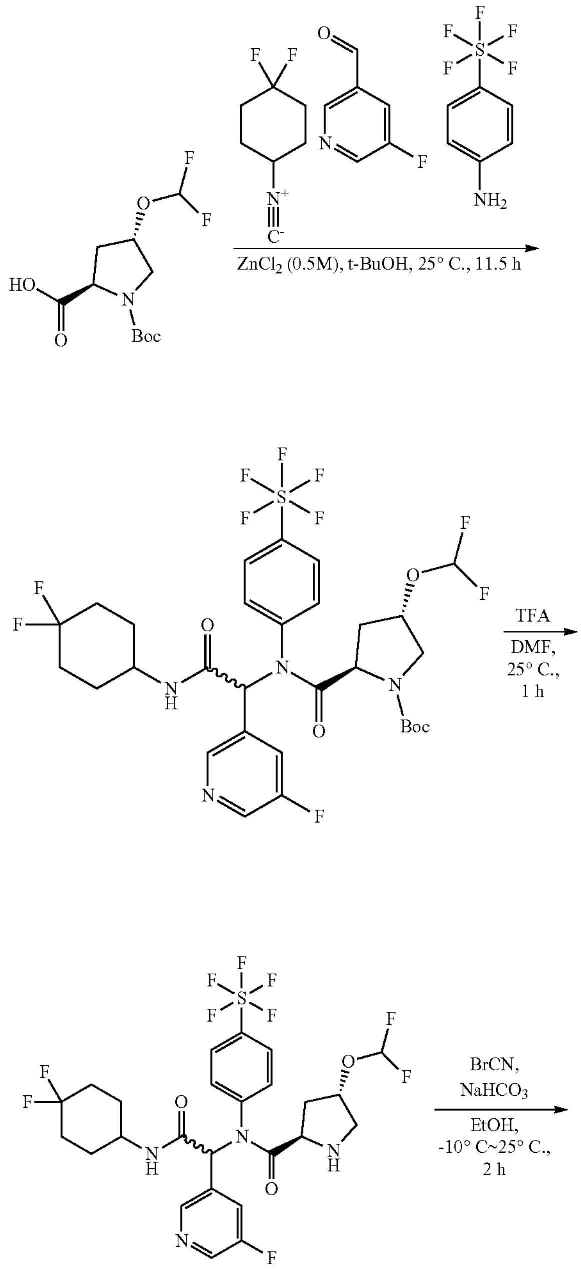

-continued

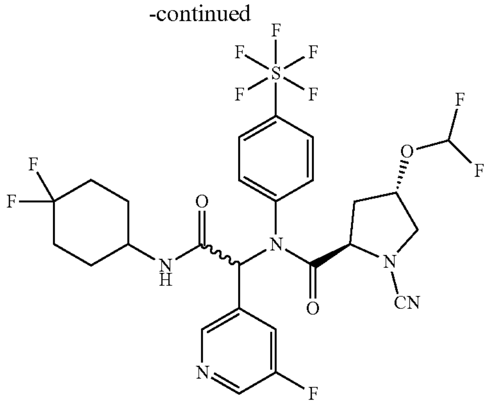

Step 1: tert-butyl(2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-(difluoromethoxy)pyrrolidine-1-carboxylate A solution of 4-(pentafluoro-λ$^6$-sulfanyl)aniline (300 mg, 1.37 mmol, 1 eq) and 5-fluoronicotinaldehyde (171.23 mg, 1.37 mmol, 1 eq) in t-BuOH (10 mL) was stirred at 25° C. for 1 h, and the mixture was added with (2R,4S)-1-(tert-butoxycarbonyl)-4-(difluoromethoxy)pyrrolidine-2-carboxylic acid (384.97 mg, 1.37 mmol, 1 eq). The reaction was stirred for 0.5 h and added with 1,1-difluoro-4-isocyanocyclohexane (178.81 mg, 1.23 mmol, 0.9 eq), $ZnCl_2$ (0.5 M, 2.74 mL, 1 eq). The mixture was stirred at 25° C. for 10 h. Upon completion, the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: 45%-65%, 8 min) to give a product tert-butyl(2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-(difluoromethoxy)pyrrolidine-1-carboxylate (130 mg, 172.72 umol, 12.62% yield) as yellow oil.

Tert-butyl(2R,4S)-2-[[2-[(4,4-difluorocyclohexyl) amino]-1-(5-fluoro-3-pyridyl)-2-oxo-ethyl]-[4-(pentafluoro-λ$^6$-sulfanyl)phenyl]carbamoyl]-4-(difluoromethoxy)pyrrolidine-1-carboxylate (150 mg, 199.29 umol, 14.56% yield) was obtained as yellow oil. MS (ESI) m/z 753.3 $[M+H]^+$ Step 2: (2R,4S)—N-[2-[(4,4-difluorocyclohexyl) amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide Isomer 1: To a solution of tert-butyl(2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-(difluoromethoxy)pyrrolidine-1-carboxylate (130 mg, 172.72 umol, 1 eq) in DCM (2 mL) was added TFA (1.18 g, 10.36 mmol, 767.30 uL, 60 eq) and the mixture was stirred at 25° C. for 1 h. Upon completion, the mixture was quenched by addition $NaHCO_3$ (20 mL) and then extracted with EtOAc (10 mL*3). The combined organic layers were washed with brine (10 mL), dried over $Na_2SO_4$, filtered and concentrated under reduced pressure to give a residue to give the crude product (2R,4S)—N-[2-[(4,4-difluorocyclohexyl)amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide (105 mg, crude) was yellow oil. MS (ESI) m/z 653.3 $[M+H]^+$ Isomer 2: To a solution of tert-butyl(2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-(difluoromethoxy)pyrrolidine-1-carboxylate (140 mg, 186.01 umol, 1 eq) in DCM (2.5 mL) was added TFA (1.27 g, 11.16 mmol, 826.32 uL, 60 eq) and the mixture was stirred at 25° C. for 1 h. Upon completion, the mixture was quenched by addition $NaHCO_3$ (20 mL), and then extracted with EtOAc (10 mL*3). The combined organic layers were washed with brine (10 mL), dried over $Na_2SO_4$, filtered and concentrated under reduced pressure to give crude product (2R,4S)—N-[2-[(4,4-difluorocyclohexyl)amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide (90 mg, crude) was yellow oil. MS (ESI) m/z 653.3 $[M+H]^+$ Step 3: (2R,4S)-1-cyano-N-[2-[(4,4-difluorocyclohexyl)amino]-1-(5-fluoro-3-pyridyl)-2-oxo-ethyl]-4-(difluoromethoxy)-N-[4-(pentafluoro-2'-sulfanyl)phenyl]pyrrolidine-2-carboxamide Isomer 1: To a solution of (2R,4S)—N-[2-[(4,4-difluorocyclohexyl)amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide (100 mg, 153.25 umol, 1 eq) in EtOH (1 mL) was added $NaHCO_3$ (38.62 mg, 459.74 umol, 17.88 uL, 3 eq) and the mixture was cooled at −10° C. After adding BrCN (24.35 mg, 229.87 umol, 16.91 uL, 1.5 eq) in EtOH (0.5 mL), the mixture was warmed to 25° C. and stirred for 2 h. Upon completion, the mixture was quenched by addition $H_2O$ (20 mL) and then extracted with EtOAc (10 mL*3). The combined organic layers were washed with brine (20 mL), dried over $Na_2SO_4$, filtered and concentrated under reduced pressure and was purified by prep-HPLC (Waters Xbridge BEH C18 100*30 mm*10 um; mobile phase: [water (10 mM $NH_4HCO_3$)-ACN]; B %: 43%-73%, 10 min) to give (2R,4S)-1-cyano-N-[2-[(4,4-difluorocyclohexyl)amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide (50 mg, 73.79 umol, 48.15% yield) was white solid. MS (ESI) m/z 678.2 $[M+H]^+$ $^1$H NMR (400 MHz, MeOD-$d_4$) δ=8.37-8.28 (m, 1H), 8.27-8.19 (m, 1H), 8.07-7.57 (m, 3H), 7.42-7.40 (m, 2H), 6.54-6.11 (m, 2H), 4.34-4.22 (m, 1H), 3.95-3.76 (m, 2H), 3.60-3.50 (m, 1H), 2.33-2.23 (m, 1H), 2.15-1.79 (m, 8H), 1.70-1.58 (m, 1H), 1.53-1.41 (m, 1H)

Isomer 2: To a solution of (2R,4S)—N-[2-[(4,4-difluorocyclohexyl)amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide (90 mg, 137.92 umol, 1 eq) in EtOH (1 mL) was added $NaHCO_3$ (34.76 mg, 413.76 umol, 16.09 uL, 3 eq) and the mixture was cooled at −10° C. After adding BrCN (21.91 mg, 206.88 umol, 15.22 uL, 1.5 eq) in EtOH (0.5 mL), the mixture solution warmed to 25° C. and stirred for 2 h. Upon completion, the mixture was quenched by addition $H_2O$ (20 mL) and then extracted with EtOAc (10 mL*3). The combined organic layers were washed with brine (20 mL), dried over $Na_2SO_4$, filtered and concentrated under reduced pressure and was purified by prep-HPLC (column: Waters Xbridge BEH C18 100*30 mm*10 um; mobile phase: [water (10 mM $NH_4HCO_3$)-ACN]; B %: 43%-73%, 10 min) to give (2R,4S)-1-cyano-N-[2-[(4,4-difluorocyclohexyl)amino]-1-(5-fluoro-3-pyridyl)-2-oxo-ethyl]-4-(difluoromethoxy)-N-[4-(pentafluoro-λ$^6$-sulfanyl)phenyl]pyrrolidine-2-carboxamide (50 mg, 73.79 umol, 53.50% yield) was white solid. MS (ESI) m/z 678.2 $[M+H]^+$ $^1$H NMR (400 MHz, MeOD-$d_4$) δ=8.37-8.30 (m, 1H), 8.27-8.20 (m, 1H), 8.04-7.60 (m, 3H), 7.54-7.09 (m, 2H), 6.57-6.11 (m, 2H), 4.31-4.21 (m, 1H), 3.88-3.80 (m, 1H), 3.83-3.76 (m, 1H), 3.58-3.51 (m, 1H), 2.37-2.25 (m, 1H), 2.14-1.77 (m, 8H), 1.69-1.58 (m, 1H), 1.53-1.40 (m, 1H)

Example 198: Synthesis of Compound 993c

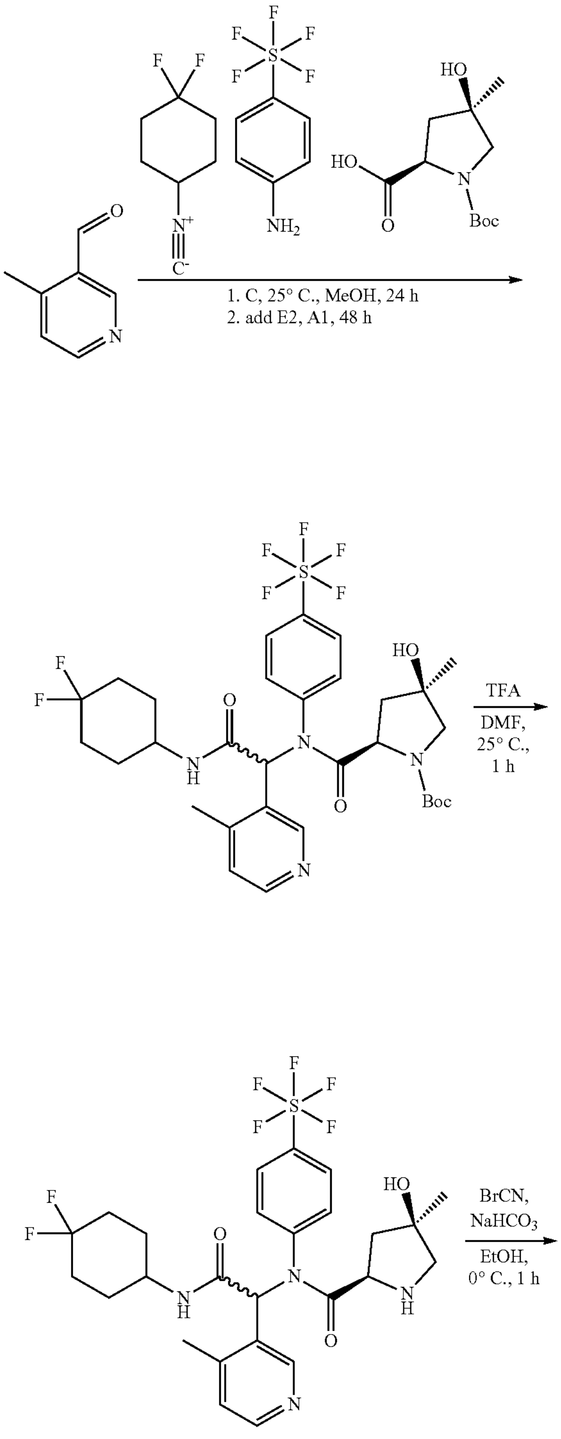

-continued

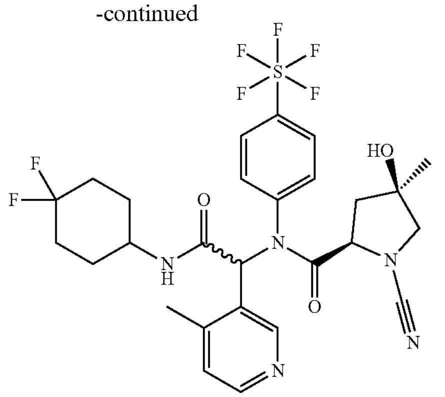

Step 1: tert-butyl(2R,4R)-2-[[2-[(4,4-difluorocyclohexyl)amino]-1-(4-methyl-3-pyridyl)-2-oxo-ethyl]-[4-(pentafluoro-λ6-sulfanyl)phenyl]carbamoyl]-4-hydroxy-4-methyl-pyrrolidine-1-carboxylate A solution of 4-(pentafluoro-$\lambda^6$-sulfanyl)aniline (180.93 mg, 825.52 umol, 1 eq) and 4-methylpyridine-3-carbaldehyde (200 mg, 1.65 mmol, 2 eq) in MeOH (6 mL) was stirred at 25° C. for 24 h. (2R,4R)-1-tert-butoxycarbonyl-4-hydroxy-4-methyl-pyrrolidine-2-carboxylic acid (202.48 mg, 825.52 umol, 1 eq) was added to the mixture, and a solution of 1,1-difluoro-4-isocyano-cyclohexane (107.84 mg, 742.96 umol, 0.9 eq) in MeOH (1 mL) was added in portions. The mixture was stirred at 25° C. for 48 h. The mixture was concentration in vacuum. The crude product was purified by prep-HPLC and prep-TLC($SiO_2$, PE:EA=1:1) to obtain tert-butyl(2R,4R)-2-[[2-[(4,4-difluorocyclohexyl)amino]-1-(4-methyl-3-pyridyl)-2-oxo-ethyl]-[4-(pentafluoro-$\lambda^6$-sulfanyl)phenyl]carbamoyl]-4-hydroxy-4-methyl-pyrrolidine-1-carboxylate (30 mg, 37.88 umol, 4.59% yield, 90% purity) as a colourless gum. MS (ESI) m/z 713.1 $[M+H]^+$.

prep-HPLC condition: column: Kromasil C18 (250*50 mm*10 um); mobile phase: [water (10 mM NH4HCO3)-ACN]; B %: 50%-70%, 10 min.

Step 2: (2R,4R)—N-[2-[(4,4-difluorocyclohexyl)amino]-1-(4-methyl-3-pyridyl)-2-oxo-ethyl]-4-hydroxy-4-methyl-N-[4-(pentafluoro-λ6-sulfanyl)phenyl]pyrrolidine-2-carboxamide A solution of tert-butyl (2R,4R)-2-[[2-[(4,4-difluorocyclohexyl)amino]-1-(4-methyl-3-pyridyl)-2-oxo-ethyl]-[4-(pentafluoro-$\lambda^6$-sulfanyl)phenyl]carbamoyl]-4-hydroxy-4-methyl-pyrrolidine-1-carboxylate (30 mg, 42.09 umol, 1 eq) in DCM (0.3 mL) and TFA (0.1 mL) was stirred at 25° C. for 1 h. The mixture was concentration in vacuum and was adjust pH-7 with sat. $NaHCO_3$ (5 mL) and extracted with DCM (2 mL*3) to obtain (2R,4R)—N-[2-[(4,4-difluorocyclohexyl)amino]-1-(4-methyl-3-pyridyl)-2-oxo-ethyl]-4-hydroxy-4-methyl-N-[4-(pentafluoro-$\lambda^6$-sulfanyl)phenyl]pyrrolidine-2-carboxamide (30 mg, crude) as a yellow solid.

Step 3: (2R,4R)-1-cyano-N-[2-[(4,4-difluorocyclohexyl)amino]-1-(4-methyl-3-pyridyl)-2-oxo-ethyl]-4-hydroxy-4-methyl-N-[4-(pentafluoro-λ6-sulfanyl)phenyl]pyrrolidine-2-carboxamide To a solution of (2R,4R)—N-[2-[(4,4-difluorocyclohexyl)amino]-1-(4-methyl-3-pyridyl)-2-oxo-ethyl]-4-hydroxy-4-methyl-N-[4-(pentafluoro-$\lambda^6$-sulfanyl)phenyl]pyrrolidine-2-carboxamide (30 mg, 48.97 umol, 1 eq) in EtOH (1 mL) was added $NaHCO_3$ (12.34 mg, 146.91 umol, 5.71 uL, 3 eq). The solution was cooled to 0° C., BrCN (5.19 mg, 48.97 umol, 3.60 uL, 1 eq) was added at 0° C., and the mixture was stirred at 0° C. for 1 h. The mixture was dried by blowing $N_2$ and was quenched by water (2 mL) and was extracted with DCM (1 mL*2), then was concentration in vacuum. The crude product was purified by prep-HPLC (column: Phenomenex Gemini-NX C18 75*30 mm*3 um; mobile phase: [water (0.05% $NH_3H_2O$+10 mM $NH_4HCO_3$)-ACN]; B %: 40%-60%, 8 min) to obtained (2R,4R)-1-cyano-N-[2-[(4,4-difluorocyclohexyl) amino]-1-(4-methyl-3-pyridyl)-2-oxo-ethyl]-4-hydroxy-4-methyl-N-[4-(pentafluoro-λ6-sulfanyl) phenyl]pyrrolidine-2-carboxamide (5.5 mg, 8.63 umol, 17.61% yield, 100% purity) as a white solid. MS (ESI) m/z 638.1 $[M+H]^+$ prep-HPLC condition: column: Phenomenex Gemini-NX C18 75*30 mm*3 um; mobile phase: [water (0.05% $NH_3H_2O$+10 mM $NH_4HCO_3$)-ACN]; B %: 40%-60%, 8 min.

$^1$H NMR (400 MHz, MeOD-$d_4$) δ ppm 8.41-8.30 (m, 1H), 8.30-7.47 (m, 5H), 7.29 (d, J=5.2 Hz, 1H), 6.91-6.85 (m, 1H), 6.95-6.59 (m, 1H), 6.43 (s, 1H), 4.27 (t, J=6.4 Hz, 1H), 3.92 (s, 1H), 3.50 (d, J=9.4 Hz, 1H), 3.35 (d, J=9.4 Hz, 1H), 2.51 (s, 3H), 2.14-1.75 (m, 9H), 1.68-1.54 (m, 1H), 1.51-1.37 (m, 1H), 1.26 (s, 3H).

Example 199: Synthesis of Compound 1098

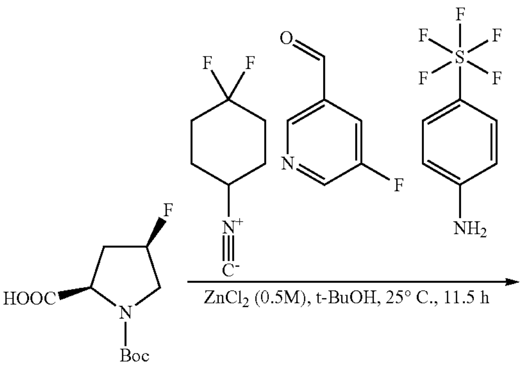

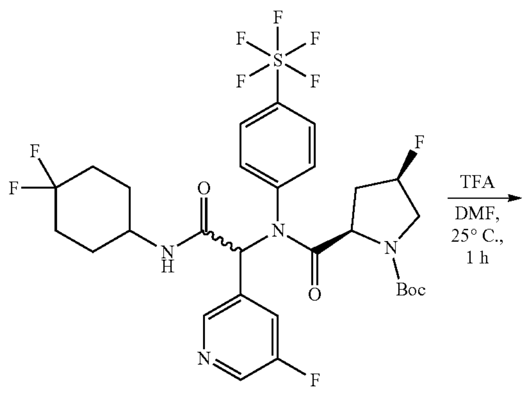

-continued

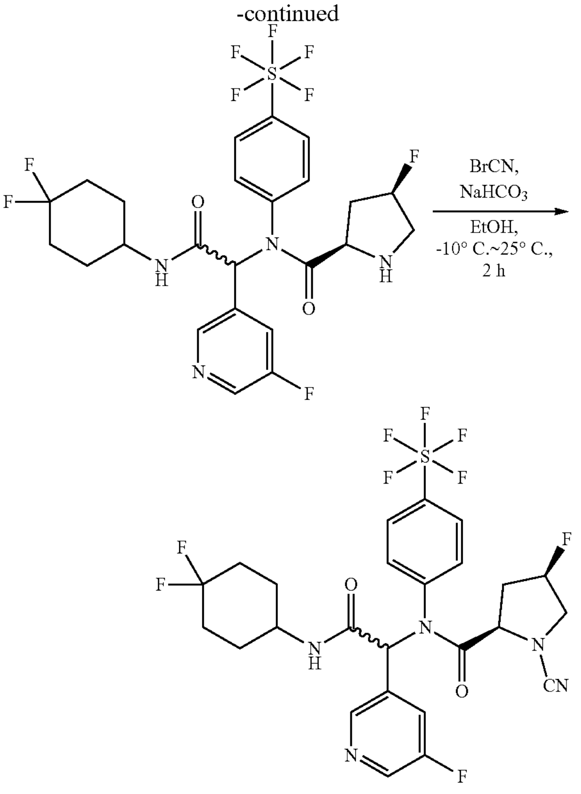

Step 1: tert-butyl(2R,4R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate A solution of 4-(pentafluoro-λ$^6$-sulfanyl)aniline (300 mg, 1.37 mmol, 1 eq) 5-fluoronicotinaldehyde (171.23 mg, 1.37 mmol, 1 eq) in t-BuOH (1 mL) was stirred at 25° C. for 1 h and was added (2R,4R)-1-(tert-butoxycarbonyl)-4-fluoro-pyrrolidine-2-carboxylic acid (319.25 mg, 1.37 mmol, 1 eq). The reaction was stirred for 0.5 h, and 1,1-difluoro-4-isocyanocyclohexane (178.81 mg, 1.23 mmol, 0.9 eq), $ZnCl_2$ (0.5 M, 2.74 mL, 1 eq) were added. After the mixture was stirred at 25° C. for 10 h, the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: 45%-65%, 8 min) to give a product tert-butyl (2R,4R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate (320 mg, 454.13 umol, 33.18% yield) was yellow oil. MS (ESI) m/z 705.2 $[M+H]^+$ Step 2: (2R,4R)—N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide To a solution of tert-butyl (2R,4R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate (300 mg, 425.75 umol, 1 eq) in DCM (6 mL) was added TFA (2.91 g, 25.54 mmol, 1.89 mL, 60 eq) and the mixture was stirred at 25° C. for 1 h. Upon completion, the mixture was quenched by addition $NaHCO_3$ (20 mL) and then extracted with EtOAc (10 mL*3). The combined organic layers were washed with brine (10 mL), dried over $Na_2SO_4$, filtered and concentrated under reduced pressure to give a residue to give the crude product (2R,4R)—N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide (220 mg, crude) was yellow oil. MS (ESI) m/z 605.2 $[M+H]^+$ Step 3: (2R,4R)-1-cyano-N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide To a solution of (2R,4R)—N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide (210 mg, 347.38 umol, 1 eq) in EtOH (5 mL) was added $NaHCO_3$ (87.55 mg, 1.04 mmol, 40.53 uL, 3 eq) and the mixture was cooled at −10° C. After BrCN (47.83 mg, 451.59 umol, 33.22 uL, 1.3 eq) in EtOH (0.5 mL) was added, the resulting solution was warmed to 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure and was purified by prep-HPLC (column: Phenomenex Gemini-NX 80*40 mm*3 um; mobile phase: [water (10 mM $NH_4HCO_3$)-ACN]; B %: 30%-50%, 8 min) to give (2R,4R)-1-cyano-N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide (30 mg, 47.65 umol, 13.72% yield) was white solid.

(2R,4R)-1-cyano-N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide (30 mg, 47.65 umol, 13.72% yield) was white solid. MS (ESI) m/z 630.2 $[M+H]^+$ $^1$H NMR (400 MHz, MeOD-$d_4$) δ=8.35-8.34 (m, 1H), 8.24 (s, 1H), 8.09-7.34 (m, 5H), 6.09 (s, 1H), 5.23-5.05 (m, 1H), 4.38-4.37 (m, 1H), 3.90-3.62 (m, 3H), 2.36-2.08 (m, 2H), 2.09-1.79 (m, 6H), 1.69-1.55 (m, 1H), 1.52-1.38 (m, 1H). MS (ESI) m/z 630.2 $[M+H]^+$ $^1$H NMR (400 MHz, MeOD-$d_4$) δ=8.30-8.28 (m, 1H), 8.25-8.21 (m, 1H), 7.99-7.44 (m, 5H), 6.35-6.05 (m, 1H), 5.23-5.04 (m, 1H), 4.38-4.36 (m, 1H), 3.95-3.62 (m, 3H), 2.37-2.11 (m, 2H), 2.06-1.83 (m, 6H), 1.71-1.58 (m, 1H), 1.53-1.42 (m, 1H)

Example 200: Synthesis of Compound 1099

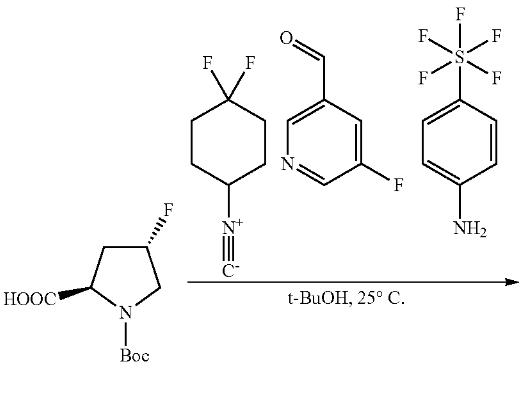

-continued

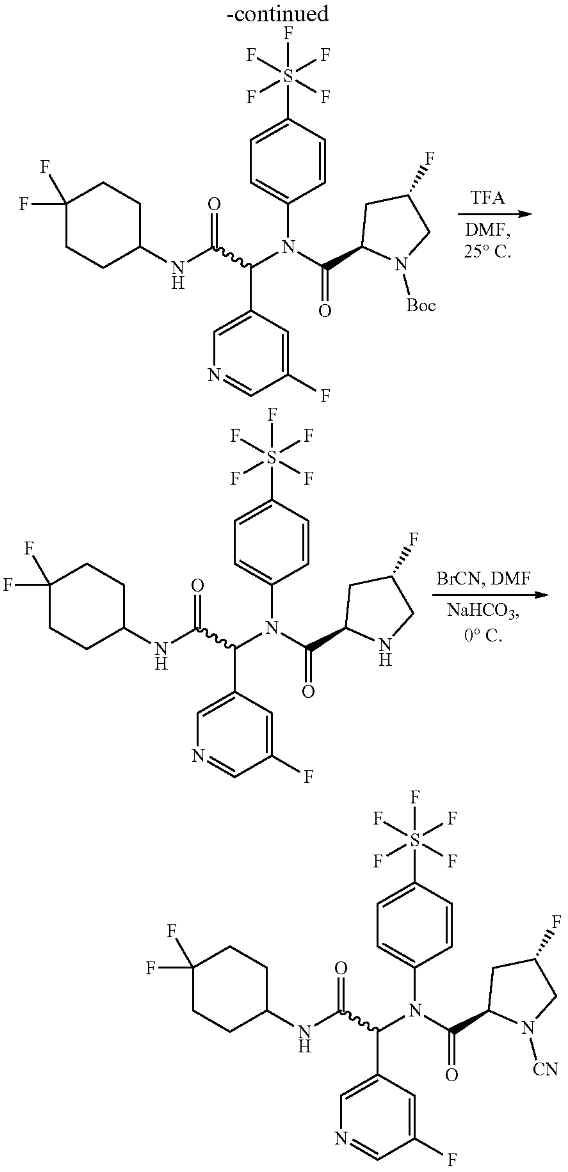

Step 1: tert-butyl (2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate A solution of 4-(pentafluoro-λ6-sulfanyl)aniline (300 mg, 1.37 mmol, 1 eq), 5-fluoropyridine-3-carbaldehyde (171.23 mg, 1.37 mmol, 1 eq) in t-BuOH (9 mL) was stirred for 1 h, and then (2R,4S)-1-tert-butoxycarbonyl-4-fluoro-pyrrolidine-2-carboxylic acid (319.25 mg, 1.37 mmol, 1 eq) was added. After stirring for 10 min, 1,1-difluoro-4-isocyano-cyclohexane (198.68 mg, 1.37 mmol, 1 eq) in t-BuOH (1 mL) was added and further stirred for 10 min. $ZnCl_2$ (1 M, 4.11 mL, 3 eq) was added, and the mixture was stirred at 25° C. for 14 h 40 min. Upon completion, the reaction mixture was concentrated under reduced pressure to remove solvent. The residue was purified by prep-HPLC (column: Kromasil C18 (250*50 mm*10 um); mobile phase: [water (10 mM $NH_4HCO_3$)-ACN]; B %: 55%-75%, 10 min) to give tert-butyl(2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate (200 mg, 274.18 umol, 20.03% yield, 96.60% purity) and tert-butyl(2R,4S)-2-[[2-[(4,4-difluorocyclohexyl)amino]-1-(5-fluoro-3-pyridyl)-2-oxo-ethyl]-[4-(pentafluoro-λ6-sulfanyl)phenyl]carbamoyl]-4-fluoro-pyrrolidine-1-carboxylate (195 mg, 238.35 umol, 17.41% yield, 86.13% purity) as a white solid. MS (ESI) m/z 705.2 $[M+H]^+$ Step 2: (2R,4S)—N-[2-[(4,4-difluorocyclohexyl)amino]-1-(5-fluoro-3-pyridyl)-2-oxo-ethyl]-4-fluoro-N-[4-(pentafluoro-λ6-sulfanyl)phenyl]pyrrolidine-2-carboxamide Isomer 1: To a solution of tert-butyl (2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate (200 mg, 283.83 umol, 1 eq) in DCM (5 mL), was added TFA (3.85 g, 33.77 mmol, 2.5 mL, 118.96 eq). The mixture was stirred at 25° C. for 1 h. Upon completion, the reaction mixture was poured into $NaHCO_3$ (25 mL) at 25° C., and then extracted with DCM (20 mL*3). The combined organic layers were washed with brine (20 mL*2), dried over $Na_2SO_4$, filtered and concentrated to give (2R,4S)—N-[2-[(4,4-difluorocyclohexyl)amino]-1-(5-fluoro-3-pyridyl)-2-oxo-ethyl]-4-fluoro-N-[4-(pentafluoro-%6-sulfanyl)phenyl]pyrrolidine-2-carboxamide (142 mg, crude) as a yellow oil. MS (ESI) m/z 605.2 $[M+H]^+$ Isomer 2: To a solution of tert-butyl (2R,4S)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-4-fluoro-pyrrolidine-1-carboxylate (200 mg, 283.83 umol, 1 eq) in DCM (5 mL) was added TFA (3.85 g, 33.77 mmol, 2.5 mL, 118.96 eq). The mixture was stirred at 25° C. for 1 h. Upon completion, the reaction mixture was poured into $NaHCO_3$ (25 mL) at 25° C., and then extracted with DCM (20 mL*3). The combined organic layers were washed with brine (20 mL*2), dried over $Na_2SO_4$, filtered and concentrated to give (2R,4S)—N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide (142 mg, crude) as a yellow oil. MS (ESI) m/z 605.2 $[M+H]^+$ Step 3: (2R,4R)—N-(4-(tert-butyl)phenyl)-1-cyano-4-hydroxy-N-(2-oxo-1-(pyridin-3-yl)-2-((tetrahydro-2H-pyran-4-yl)amino)ethyl)pyrrolidine-2-carboxamide Isomer 1: To a solution of (2R,4S)—N-[2-[(4,4-difluorocyclohexyl)amino]-1-(5-fluoro-3-pyridyl)-2-oxo-ethyl]-4-fluoro-N-[4-(pentafluoro-λ$^6$-sulfanyl)phenyl]pyrrolidine-2-carboxamide (132 mg, 218.35 umol, 1 eq), and $NaHCO_3$ (55.03 mg, 655.05 umol, 25.48 uL, 3 eq) in DMF (3 mL), BrCN (30.07 mg, 283.86 umol, 20.88 uL, 1.3 eq) in DMF (0.5 mL) was added at 0° C. The mixture was stirred at 0° C. for 1 h. Upon completion, the reaction mixture was quenched by addition water 20 mL at 25° C., and then extracted with EtOAc (25 mL*3). The combined organic layers were washed with brine (20 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (0.2% FA)-ACN]; B %: 30%-70%, 8 min) to give (2R,4S)-1-cyano-N-[2-[(4,4-difluorocyclohexyl)amino]-1-(5-fluoro-3-pyridyl)-2-oxo-ethyl]-4-fluoro-N-[4-

(pentafluoro-λ6-sulfanyl)phenyl]pyrrolidine-2-carboxamide (63.7 mg, 101.18 umol, 46.34% yield, 100% purity) as a white solid. MS (ESI) m/z 630.2 $[M+H]^+$ Isomer 1: $^1H$ NMR (400 MHz, MeOD-$d_4$) δ=8.32 (s, 1H), 8.21 (s, 1H), 8.11-7.59 (m, 3H), 7.42 (d, J=9.4 Hz, 2H), 6.23 (s, 1H), 5.30 (s, 1H), 4.32 (s, 1H), 3.94-3.65 (m, 3H), 2.34-1.80 (m, 8H), 1.65 (s, 1H), 1.48 (s, 1H).

Isomer 2: To a solution of (2R,4S)—N-[2-[(4,4-difluorocyclohexyl)amino]-1-(5-fluoro-3-pyridyl)-2-oxo-ethyl]-4-fluoro-N-[4-(pentafluoro-26-sulfanyl)phenyl]pyrrolidine-2-carboxamide (120 mg, 198.50 umol, 1 eq), $NaHCO_3$ (50.03 mg, 595.50 umol, 23.16 uL, 3 eq) in DMF (3 mL) was added BrCN (27.33 mg, 258.05 umol, 18.98 uL, 1.3 eq) in DMF (0.5 mL) at 0° C. The mixture was stirred at 0° C. for 1 h. Upon completion, the reaction mixture was quenched by addition $H_2O$ (20 mL) at 25° C., and then extracted with EtOAc (25 mL*3). The combined organic layers were washed with brine (20 mL*2), dried over $Na_2SO_4$, filtered and concentrated to give a residue. The residue was purified by prep-HPLC (column: Phenomenex Luna C18 75*30 mm*3 um; mobile phase: [water (0.2% FA)-ACN]; B %: 30%-70%, 8 min) to give (2R,4S)-1-cyano-N-[2-[(4,4-difluorocyclohexyl)amino]-1-(5-fluoro-3-pyridyl)-2-oxo-ethyl]-4-fluoro-N-[4-(pentafluoro-λ6-sulfanyl)phenyl]pyrrolidine-2-carboxamide (55 mg, 87.15 umol, 43.90% yield, 99.75% purity) as a white solid. MS (ESI) m/z 630.2 $[M+H]^+$ Isomer 2: $^1H$ NMR (400 MHz, MeOD-$d_4$) δ=8.37 (s, 1H), 8.27 (s, 1H), 8.17-6.88 (m, 5H), 6.13 (s, 1H), 5.40-5.14 (m, 1H), 4.29 (t, J=7.8 Hz, 1H), 3.94-3.64 (m, 3H), 2.38-2.18 (m, 2H), 2.10-1.83 (m, 6H), 1.70-1.59 (m, 1H), 1.54-1.40 (m, 1H)

Example 201: Synthesis of Compound 1122

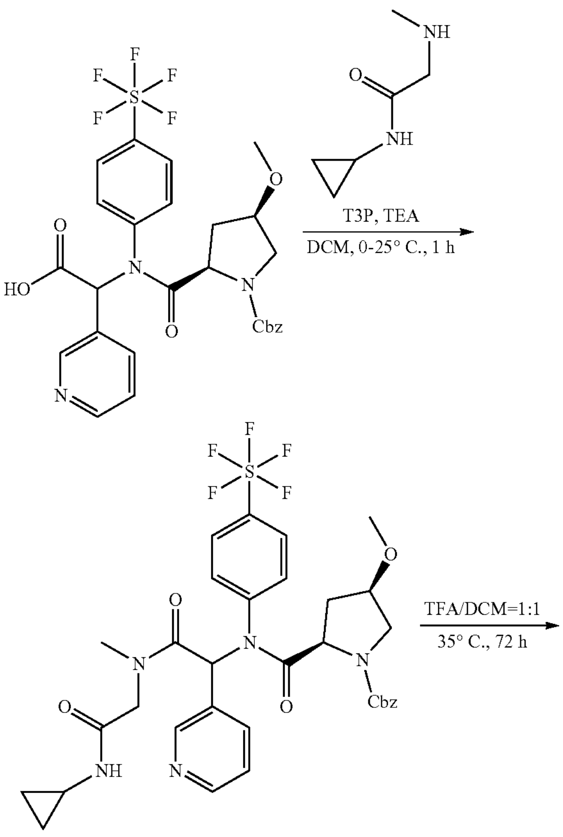

-continued

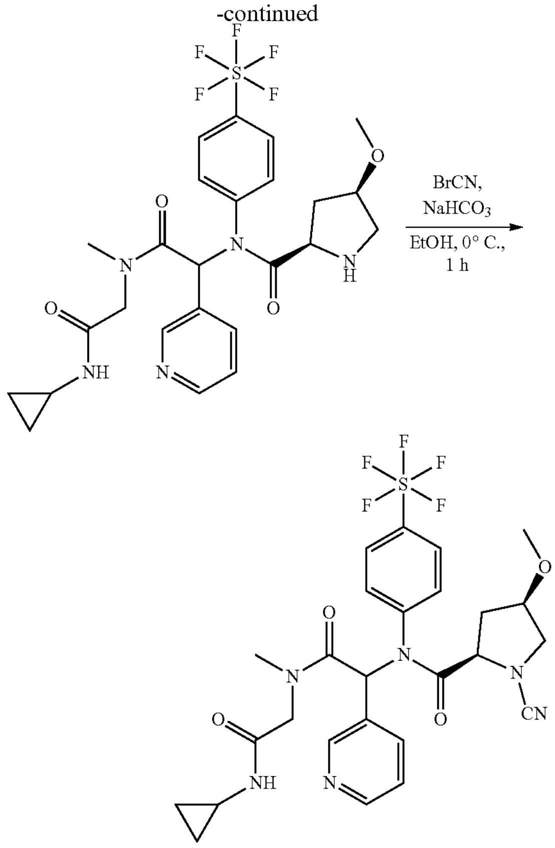

Step 1: benzyl(2R,4R)-2-[[2-[[2-(cyclopropylamino)-2-oxo-ethyl]-methyl-amino]-2-oxo-1-(3-pyridyl)ethyl]-[4-(pentafluoro-$\lambda^6$-sulfanyl) phenyl] carbamoyl]-4-methoxy-pyrrolidine-1-carboxylate To a solution of 2-[N-[(2R,4R)-1-benzyloxycarbonyl-4-methoxy-pyrrolidine-2-carbonyl]-4-(pentafluoro-$\lambda^6$-sulfanyl) anilino]-2-(3-pyridyl) acetic acid (200 mg, 324.90 umol, 1 eq) and N-cyclopropyl-2-(methylamino) acetamide (124.93 mg, 974.71 umol, 3 eq) in DCM (3 mL) was added TEA (164.38 mg, 1.62 mmol, 226.11 uL, 5 eq), and then the mixture was cooled to 0° C. After adding T3P (310.13 mg, 487.35 umol, 289.84 uL, 50% purity, 1.5 eq) at 0° C., the mixture was stirred at 25° C. for 1 h. Upon completion, the mixture was quenched by water (3 mL) and was extracted with DCM (2 mL*3), then the organic phase was concentration in vacuum to obtained benzyl (2R,4R)-2-[[2-[[2-(cyclopropylamino)-2-oxo-ethyl]-methyl-amino]-2-oxo-1-(3-pyridyl)ethyl]-[4-(pentafluoro-$\lambda^6$-sulfanyl) phenyl] carbamoyl]-4-methoxy-pyrrolidine-1-carboxylate (200 mg, crude) as a light yellow gum. MS (ESI) m/z 726.2 $[M+H]^+$ Step 2: (2R,4R)—N-[2-[[2-(cyclopropylamino)-2-oxo-ethyl]-methyl-amino]-2-oxo-1-(3-pyridyl)ethyl]-4-methoxy-N-[4-(pentafluoro-$\lambda^6$-sulfanyl) phenyl] pyrrolidine-2-carboxamide A solution of benzyl (2R,4R)-2-[[2-[[2-(cyclopropylamino)-2-oxo-ethyl]-methyl-amino]-2-oxo-1-(3-pyridyl) ethyl]-[4-(pentafluoro-$\lambda^6$-sulfanyl)phenyl]carbamoyl]-4-methoxy-pyrrolidine-1-carboxylate (150 mg, 206.69 umol, 1 eq) in TFA (4 mL) and DCM (4 mL) was stirred at 35° C.

for 72 h. Upon completion, the mixture was quenched by sat. $NaHCO_3$ (15 mL) to adjust pH-7 and was extracted with DCM (5 mL*3), concentrated in vacuum to obtained (2R,4R)—N-[2-[[2-(cyclopropylamino)-2-oxo-ethyl]-methyl-amino]-2-oxo-1-(3-pyridyl) ethyl]-4-methoxy-N-[4-(pentafluoro-$\lambda^6$-sulfanyl)phenyl]pyrrolidine-2-carboxamide (100 mg, crude) as a yellow oil. MS (ESI) m/z 592.2 $[M+H]^+$ Step 3: (2R,4R)-1-cyano-N-[2-[[2-(cyclopropylamino)-2-oxo-ethyl]-methyl-amino]-2-oxo-1-(3-pyridyl)ethyl]-4-methoxy-N-[4-(pentafluoro-$\lambda^6$-sulfanyl)phenyl]pyrrolidine-2-carboxamide To a solution of (2R,4R)—N-[2-[[2-(cyclopropylamino)-2-oxo-ethyl]-methyl-amino]-2-oxo-1-(3-pyridyl)ethyl]-4-methoxy-N-[4-(pentafluoro-$\lambda^6$-sulfanyl)phenyl]pyrrolidine-2-carboxamide (100 mg, 101.42 umol, 60% purity, 1 eq) in EtOH (2 mL) was added $NaHCO_3$ (25.56 mg, 304.26 umol, 11.83 uL, 3 eq), and the mixture was cooled to 0° C. BrCN (21.49 mg, 202.84 umol, 14.92 uL, 2 eq) was added at 0° C., and the mixture was stirred at 0° C. for 1 h. Upon completion, the mixture was dried by blowing $N_2$ and was quenched by water (3 mL) and was extracted with DCM (1 mL*2), then was concentration in vacuum. The crude product was purified by prep-HPLC (column: Waters Xbridge Prep OBD C18 150*40 mm*10 um; mobile phase: [water (10 mM $NH_4HCO_3$)-ACN]; B %: 20%-50%, 8 min) to obtained (2R,4R)-1-cyano-N-[2-[[2-(cyclopropylamino)-2-oxo-ethyl]-methyl-amino]-2-oxo-1-(3-pyridyl) ethyl]-4-methoxy-N-[4-(pentafluoro-$\lambda^6$-sulfanyl) phenyl]pyrrolidine-2-carboxamide (16 mg, 25.95 umol, 25.59% yield, 100% purity) as a yellow solid. MS (ESI) m/z 617.1 $[M+H]^+$ $^1H$ NMR (400 MHz, MeOD-$d_4$) δ ppm 8.53-8.32 (m, 2H), 8.25-7.50 (m, 4H), 7.49-6.75 (m, 2H), 6.61-6.55 (m, 1H), 4.33-3.85 (m, 4H), 3.70-3.58 (m, 1H), 3.57-3.43 (m, 1H), 3.30-3.12 (m, 3H), 3.08-2.97 (m, 3H), 2.75-2.45 (m, 1H), 2.24-1.87 (m, 2H), 0.85-0.37 (m, 4H).

Example 202: Synthesis of Compound 1127

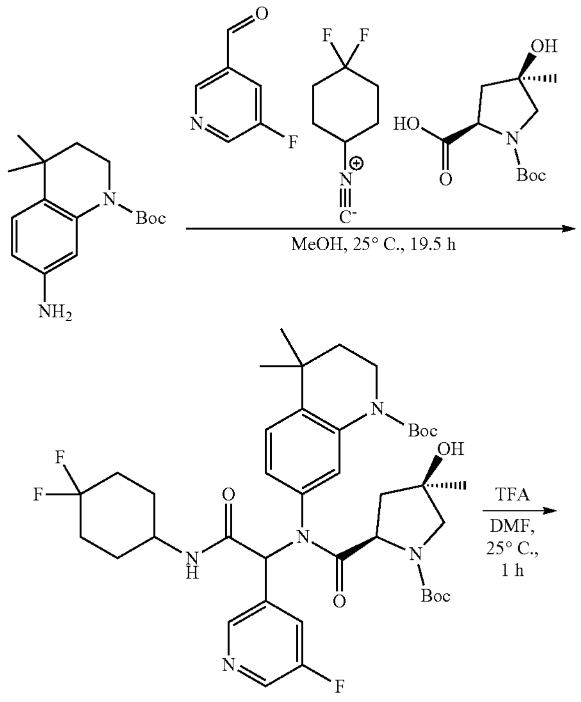

-continued

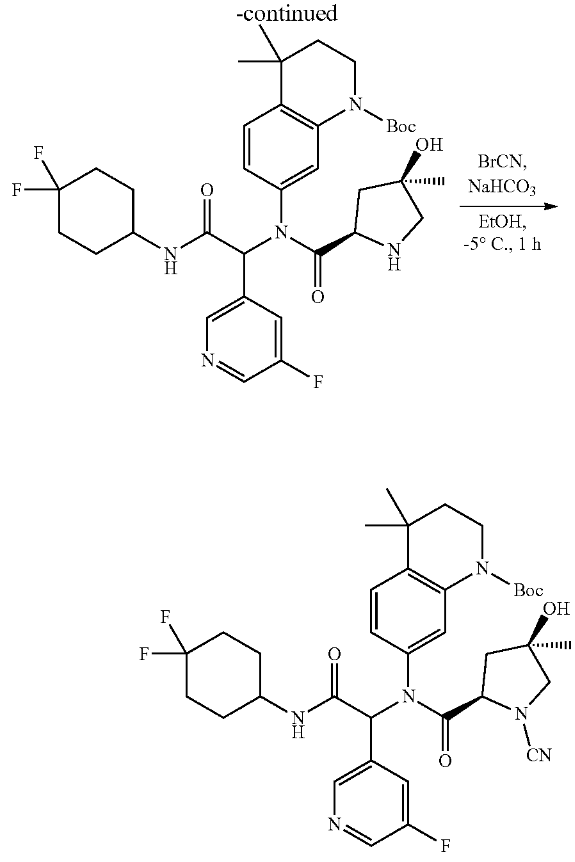

Step 1: tert-butyl 7-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-4,4-dimethyl-2,3-dihydroquinoline-1-carboxylate A mixture of tert-butyl 7-amino-4,4-dimethyl-2,3-dihydroquinoline-1-carboxylate (350 mg, 1.27 mmol, 1 eq) and 5-fluoropyridine-3-carbaldehyde (237.64 mg, 1.90 mmol, 1.5 eq) in MeOH (7 mL) was stirred at 25° C. for 1.5 h. (2R,4R)-1-tert-butoxycarbonyl-4-hydroxy-4-methyl-pyrrolidine-2-carboxylic acid (388.27 mg, 1.27 mmol, 80% purity, 1 eq) and 1,1-difluoro-4-isocyano-cyclohexane (183.82 mg, 1.27 mmol, 1 eq) were added and stirred at 25° C. for 18 h. Upon completion, the reaction mixture was concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 60%-80%, 8 min) to provide tert-butyl 7-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl] amino]-4,4-dimethyl-2,3-dihydroquinoline-1-carboxylate Isomer 1 (240 mg, 310.13 umol, 24.49% yield) as white solid. MS (ESI) m/z 774.4 $[M+H]^+$.

Tert-butyl 7-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-4,4-dimethyl-2,3-dihydroquinoline-1-carboxylate Isomer 2 (205 mg, 264.90 umol, 20.92% yield) was obtained as white solid. MS (ESI) m/z 774.4$[M+H]^+$.

Step 2: (2R,4R)—N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 1

A mixture of tert-butyl 7-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-4,4-dimethyl-2,3-dihydroquinoline-1-carboxylate Isomer 1 (300 mg, 387.66 umol, 1 eq) in DCM (4 mL) and TFA (2 mL) was stirred 25° C. for 1 h. Upon completion, the reaction mixture was diluted with $NaHCO_3$ (10 mL) and extracted with EA (10 mL*3). The combined organic layers were washed with brine, dried over $Na_2SO_4$, filtered and concentrated under reduced pressure to give a residue to get the product (2R,4R)—N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 1 (220 mg, crude) as yellow oil. MS (ESI) m/z 574.3 $[M+H]^+$.

(2R,4R)—N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 2

A mixture of tert-butyl 7-[[(2R,4R)-1-tert-butoxycarbonyl-4-hydroxy-4-methyl-pyrrolidine-2-carbonyl]-[2-[(4,4-difluorocyclohexyl)amino]-1-(5-fluoro-3-pyridyl)-2-oxo-ethyl]amino]-4,4-dimethyl-2,3-dihydroquinoline-1-carboxylate Isomer 2 (245 mg, 316.59 umol, 1 eq) in DCM (4 mL) and TFA (2 mL) was stirred at 25° C. for 1 h. Upon completion, the reaction mixture was diluted with $NaHCO_3$ (10 mL) and extracted with EA (10 mL*3). The combined organic layers were washed with brine, dried over $Na_2SO_4$, filtered and concentrated under reduced pressure to give a residue to get the product (2R,4R)—N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 2 (180 mg, crude) as yellow oil. MS (ESI) m/z 574.3 $[M+H]^+$.

Step 3: (2R,4R)-1-cyano-N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 1

A mixture of (2R,4R)—N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 1 (210 mg, 366.08 umol, 1 eq) in EtOH (3 mL) was added with $NaHCO_3$ (92.26 mg, 1.10 mmol, 42.71 uL, 3 eq), and then the mixture was cooled to −5° C. After adding BrCN (19.39 mg, 183.04 umol, 13.46 uL, 0.5 eq) in EtOH (0.5 mL) drop-wise, the mixture was stirred at −5° C. for 1 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-60%, 8 min) to get the product (2R,4R)-1-cyano-N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 1 (55.32 mg, 88.43 umol, 24.16% yield, 95.7% purity) as yellow solid. MS (ESI) m/z 599.3 $[M+H]^+$.

$^1H$ NMR (400 MHz, METHANOL-$d_4$) δ=8.28 (br s, 1H), 8.23 (s, 1H), 7.36 (br d, J=9.1 Hz, 11H), 7.19-6.72 (m, 2H), 6.04 (s, 1H), 5.94-5.79 (m, 1H), 4.40 (br dd, J=4.4, 8.3 Hz, 1H), 3.86 (br s, 1H), 3.49 (br d, J=9.3 Hz, 1H), 3.36 (br d, J=9.3 Hz, 1H), 3.25 (br d, J=1.5 Hz, 2H), 2.16-1.76 (m, 8H), 1.63 (br d, J=8.9 Hz, 3H), 1.48 (br s, 1H), 1.27 (s, 3H), 1.24-1.09 (m, 6H).

(2R,4R)-1-cyano-N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 2

A mixture of (2R,4R)—N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 2 (170 mg, 296.35 umol, 1 eq) in EtOH (3 mL) was added with $NaHCO_3$ (74.69 mg, 889.05 umol, 34.58 uL, 3 eq), and then the mixture was cooled to −5° C. After adding BrCN (15.69 mg, 148.17 umol, 10.90 uL, 0.5 eq) in EtOH (0.5 mL) drop-wise, the mixture was stirred at −5° C. for 1 h. Upon completion, the reaction mixture was diluted with water (10 mL) and extracted with EA (3 mL*3). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-60%, 8 min) to get the product (2R,4R)-1-cyano-N-[2-[(4,4-difluorocyclohexyl)amino]-1-(5-fluoro-3-pyridyl)-2-oxo-ethyl]-N-(4,4-dimethyl-2,3-dihydro-1H-quinolin-7-yl)-4-hydroxy-4-methyl-pyrrolidine-2-carboxamide Isomer 2 (44.42 mg, 72.20 umol, 24.36% yield, 97.3% purity) as yellow solid. MS (ESI) m/z 599.3 $[M+H]^+$.

$^1H$ NMR (400 MHz, METHANOL-$d_4$) δ=8.41-8.13 (m, 2H), 7.41 (br d, J=9.2 Hz, 1H), 7.27-6.63 (m, 2H), 6.05-5.90 (m, 1H), 5.86 (br d, J=1.1 Hz, 1H), 4.46-4.36 (m, 1H), 3.89-3.79 (m, 1H), 3.51-3.46 (m, 1H), 3.36 (br d, J=9.3 Hz, 1H), 3.26-3.12 (m, 2H), 2.11-1.92 (m, 6H), 1.83 (br d, J=12.9 Hz, 2H), 1.63 (br d, J=3.1 Hz, 3H), 1.47 (br dd, J=3.4, 11.0 Hz, 1H), 1.26 (s, 3H), 1.24-1.11 (m, 6H).

Example 203: Synthesis of Compound 1136a

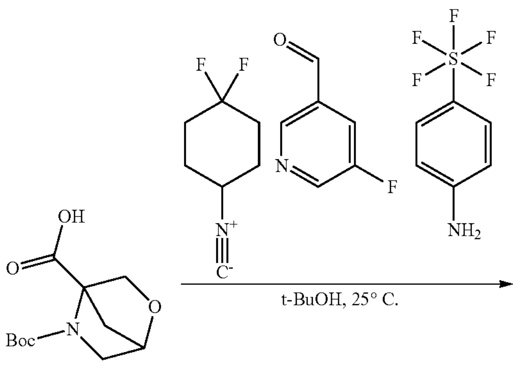

-continued

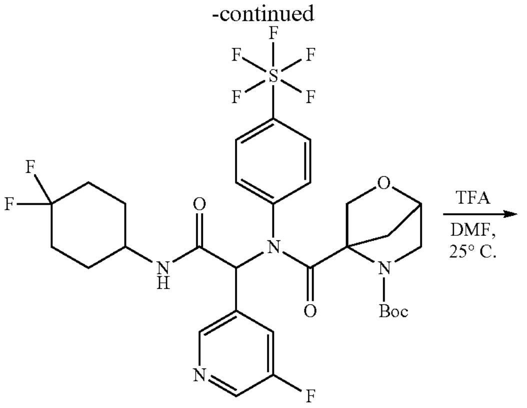

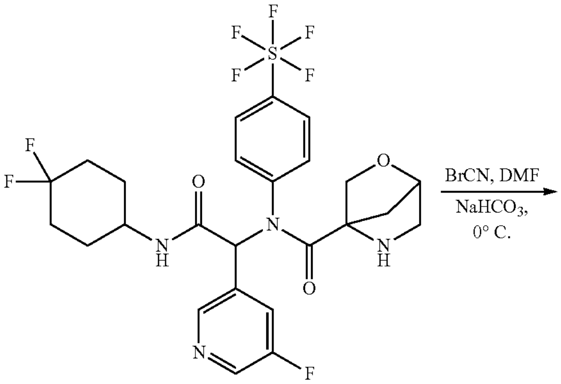

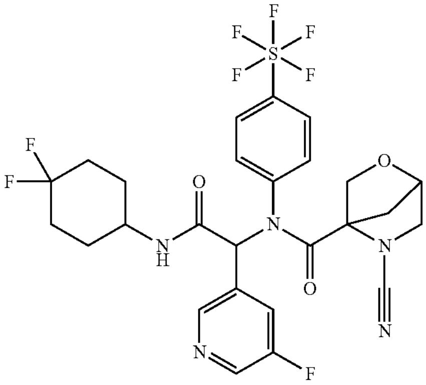

Step 1: tert-butyl 4-[[2-[(4,4-difluorocyclohexyl) amino]-1-(5-fluoro-3-pyridyl)-2-oxo-ethyl]-[4-(pentafluoro-λ$^6$-sulfanyl)phenyl]carbamoyl]-2-oxa-5-azabicyclo[2.2.1]heptane-5-carboxylate A solution of 4-(pentafluoro-λ$^6$-sulfanyl)aniline (300 mg, 1.37 mmol, 1 eq) and 5-fluoropyridine-3-carbaldehyde (171.23 mg, 1.37 mmol, 1 eq) in t-BuOH (9 mL) was stirred for 1 h, and then 5-tert-butoxycarbonyl-2-oxa-5-azabicyclo [2.2.1]heptane-4-carboxylic acid (332.96 mg, 1.37 mmol, 1 eq) was added. After stirring for 10 min, 1,1-difluoro-4-isocyano-cyclohexane (198.68 mg, 1.37 mmol, 1 eq) in t-BuOH (1 mL) was added and stirred for 10 min more. $ZnCl_2$ (1 M, 4.11 mL, 3 eq) was added, and the mixture was stirred at 25° C. for 14 h 40 min. Upon completion, the reaction mixture was concentrated under reduced pressure to remove solvent. The residue was purified by prep-HPLC (column: Kromasil C18 (250*50 mm*10 um); mobile phase: [water (10 mM NH4HCO3)-ACN]; B %: 55%-75%, 10 min) to give tert-butyl 4-[[2-[(4,4-difluorocyclohexyl) amino]-1-(5-fluoro-3-pyridyl)-2-oxo-ethyl]-[4-(pentafluoro-λ$^6$-sulfanyl)phenyl]carbamoyl]-2-oxa-5-azabicyclo [2.2.1]heptane-5-carboxylate (260 mg, 363.81 umol, 26.58% yield) as a white solid. MS (ESI) m/z 715.2 $[M+H]^+$ Step 2: N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-oxa-5-azabicyclo[2.2.1]heptane-4-carboxamide To a solution of tert-butyl 4-[[2-[(4,4-difluorocyclohexyl) amino]-1-(5-fluoro-3-pyridyl)-2-oxo-ethyl]-[4-(pentafluoro-λ$^6$-sulfanyl)phenyl]carbamoyl]-2-oxa-5-azabicyclo [2.2.1]heptane-5-carboxylate (260 mg, 363.81 umol, 1 eq) in DCM (6 mL) was added TFA (4.62 g, 40.52 mmol, 3 mL, 111.37 eq). The mixture was stirred at 25° C. for 1 h. Upon completion, the reaction mixture was poured into $NaHCO_3$ 25 mL at 25° C., and then extracted with DCM (20 mL*3). The combined organic layers were washed with brine (20 mL*2), dried over $Na_2SO_4$, filtered and concentrated to give N-[2-[(4,4-difluorocyclohexyl)amino]-1-(5-fluoro-3-pyridyl)-2-oxo-ethyl]-N-[4-(pentafluoro-λ6-sulfanyl)phenyl]-2-oxa-5-azabicyclo[2.2.1]heptane-4-carboxamide (210 mg, crude) as a yellow oil. MS (ESI) m/z 615.2 $[M+H]^+$ Step 3: (2R,4R)—N-(4-(tert-butyl)phenyl)-1-cyano-4-hydroxy-N-(2-oxo-1-(pyridin-3-yl)-2-((tetrahydro-2H-pyran-4-yl)amino)ethyl)pyrrolidine-2-carboxamide To a solution of N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-oxa-5-azabicyclo[2.2.1]heptane-4-carboxamide (200 mg, 325.44 umol, 1 eq), $NaHCO_3$ (82.02 mg, 976.32 umol, 37.97 uL, 3 eq) in DMF (3.5 mL), BrCN (44.81 mg, 423.07 umol, 31.12 uL, 1.3 eq) in DMF (0.8 mL) was added at 0° C. The mixture was stirred at 0° C. for 1 h. Upon completion, the reaction mixture was quenched by addition $H_2O$ 25 mL at 25° C., and then extracted with EtOAc (25 mL*3). The combined organic layers were washed with brine (20 mL*2), dried over $Na_2SO_4$, filtered and concentrated to give a residue. The residue was purified by prep-HPLC (column: Phenomenex Luna C18 75*30 mm*3 um; mobile phase: [water (0.2% FA)-ACN]; B %: 35%-70%, 8 min) to give 5-cyano-N-[2-[(4,4-difluorocyclohexyl)amino]-1-(5-fluoro-3-pyridyl)-2-oxo-ethyl]-N-[4-(pentafluoro-λ$^6$-sulfanyl)phenyl]-2-oxa-5-azabicyclo[2.2.1]heptane-4-carboxamide (92 mg, 142.53 umol, 43.79% yield, 99.08% purity) was obtained as a white solid. MS (ESI) m/z 640.2 $[M+H]^+$ $^1$H NMR (400 MHz, MeOD-$d_4$) δ=8.35 (s, 1H), 8.25-8.18 (m, 1H), 8.11 (s, 1H), 7.90 (s, 1H), 7.63 (s, 1H), 7.45-7.33 (m, 1H), 7.09 (s, 1H), 6.19-6.07 (m, 1H), 4.44 (s, 1H), 4.23-4.06 (m, 2H), 3.87 (t, J=9.8 Hz, 1H), 3.27 (s, 1H), 3.04 (d, J=9.8 Hz, 1H), 2.14-2.04 (m, 2H), 1.97 (d, J=9.4 Hz, 3H), 1.87-1.79 (m, 2H), 1.67-1.56 (m, 1H), 1.50-1.41 (m, 1H), 1.30 (d, J=10.4 Hz, 1H).

Example 204: Synthesis of Compound 1140

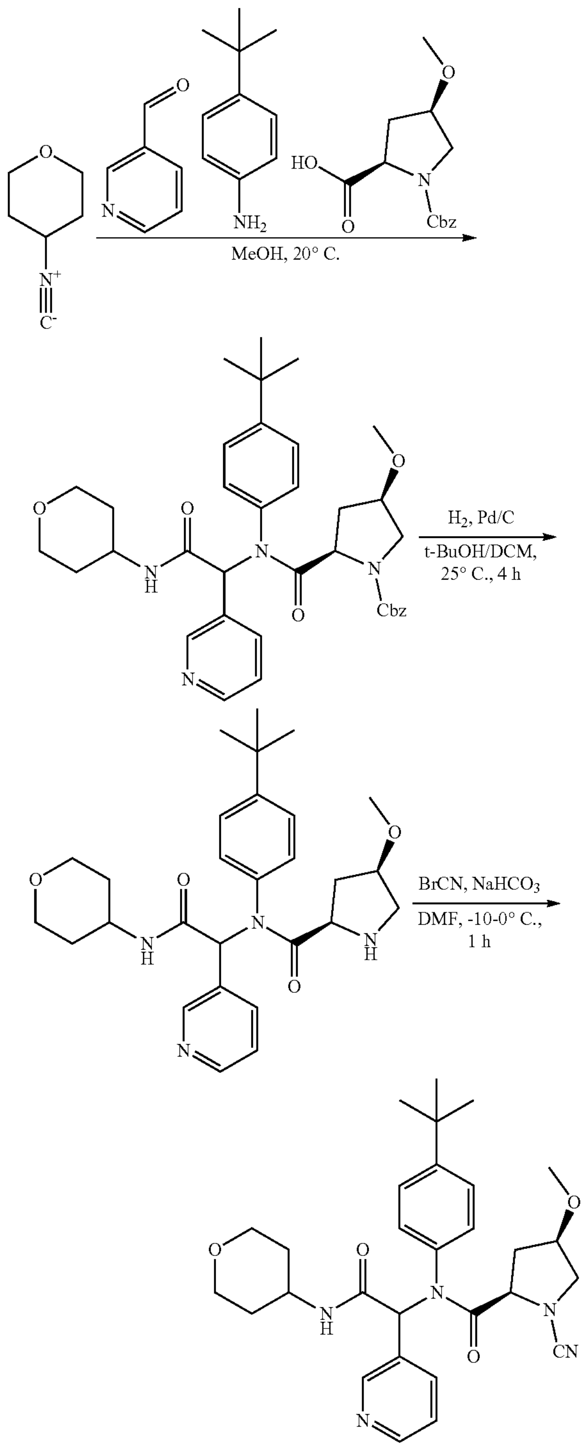

Step 1: (2R,4R)-benzyl 2-((4-(tert-butyl)phenyl)(2-oxo-1-(pyridin-3-yl)-2-((tetrahydro-2H-pyran-4-yl)amino)ethyl)carbamoyl)-4-methoxypyrrolidine-1-carboxylate To a solution of pyridine-3-carbaldehyde (150 mg, 1.40 mmol, 131.58 uL, 1 eq) and (2R,4R)-1-benzyloxycarbonyl-4-methoxy-pyrrolidine-2-carboxylic acid (391.12 mg, 1.40 mmol, 1 eq) in MeOH (6 mL), then 4-tert-butylaniline (208.99 mg, 1.40 mmol, 221.15 uL, 1 eq) was added 4-isocyanotetrahydropyran (155.65 mg, 1.40 mmol, 1 eq) in MeOH (2 mL) drop-wise. The mixture was stirred at 25° C. for 12 h, and the residue was purified by prep-HPLC (column: Waters Xbridge Prep OBD C18 150*40 mm*10 um; mobile phase: [water (10 mM $NH_4HCO_3$)-ACN]; B %: 40%-60%, 8 min) to afford benzyl (2R,4R)-2-[(4-tert-butylphenyl)-[2-oxo-1-(3-pyridyl)-2-(tetrahydropyran-4-ylamino)ethyl]carbamoyl]-4-methoxy-pyrrolidine-1-carboxylate (200 mg, 318.09 umol, 22.71% yield) was obtained as a white solid. MS (ESI) m/z 629.3 $[M+H]^+$ Benzyl (2R,4R)-2-[(4-tert-butylphenyl)-[2-oxo-1-(3-pyridyl)-2-(tetrahydropyran-4-ylamino)ethyl]carbamoyl]-4-methoxy-pyrrolidine-1-carboxylate (200 mg, 318.09 umol, 22.71% yield, N/A purity) was obtained as a white solid. MS (ESI) m/z 629.3 $[M+H]^+$ Step 2: (2R,4R)—N-(4-(tert-butyl)phenyl)-4-methoxy-N-(2-oxo-1-(pyridin-3-yl)-2-((tetrahydro-2H-pyran-4-yl)amino)ethyl)pyrrolidine-2-carboxamide To a solution of benzyl (2R,4R)-2-[(4-tert-butylphenyl)-[2-oxo-1-(3-pyridyl)-2-(tetrahydropyran-4-ylamino)ethyl]carbamoyl]-4-methoxy-pyrrolidine-1-carboxylate (100 mg, 159.04 umol, 1 eq) in t-BuOH (5 mL) and DCM (1 mL) was added Pd/C (100 mg, 47.71 umol, 10% purity, 0.3 eq) under $H_2$ atmosphere. The suspension was degassed and purged with $H_2$ for 3 times. The mixture was stirred under H2 (15 Psi) at 25° C. for 4 h, and the reaction mixture was filtered and the filtrate was concentrated under reduced pressure to get the (2R,4R)—N-(4-tert-butylphenyl)-4-methoxy-N-[2-oxo-1-(3-pyridyl)-2-(tetrahydropyran-4-ylamino)ethyl]pyrrolidine-2-carboxamide (60 mg, crude) was obtained as a yellow oil. MS (ESI) m/z 495.3 $[M+H]^+$ To a solution of benzyl (2R,4R)-2-[(4-tert-butylphenyl)-[2-oxo-1-(3-pyridyl)-2-(tetrahydropyran-4-ylamino)ethyl]carbamoyl]-4-methoxy-pyrrolidine-1-carboxylate (100 mg, 159.04 umol, 1 eq) in t-BuOH (5 mL) and DCM (1 mL) was added Pd/C (100 mg, 47.71 umol, 10% purity, 0.3 eq) under $H_2$ atmosphere. The suspension was degassed and purged with $H_2$ for 3 times. The mixture was stirred under H2 (15 Psi) at 25° C. for 4 h. The reaction mixture was filtered and the filtrate was concentrated under reduced pressure to get the (2R,4R)—N-(4-tert-butylphenyl)-4-methoxy-N-[2-oxo-1-(3-pyridyl)-2-(tetrahydropyran-4-ylamino)ethyl]pyrrolidine-2-carboxamide (60 mg, crude) was obtained as a yellow oil. MS (ESI) m/z 495.3 $[M+H]^+$ Step 3: (2R,4R)—N-(4-(tert-butyl)phenyl)-1-cyano-4-methoxy-N-(2-oxo-1-(pyridin-3-yl)-2-((tetrahydro-2H-pyran-4-yl)amino)ethyl)pyrrolidine-2-carboxamide A solution of (2R,4R)—N-(4-tert-butylphenyl)-4-methoxy-N-[2-oxo-1-(3-pyridyl)-2-(tetrahydropyran-4-ylamino)ethyl]pyrrolidine-2-carboxamide (50 mg, 101.09 umol, 1 eq) in DMF (2 mL) was cooled to −10° C., and then $NaHCO_3$ (25.48 mg, 303.26 umol, 11.79 uL, 3.0 eq) and BrCN (16.06 mg, 151.63 umol, 11.15 uL, 1.5 eq) in DMF (0.4 mL) were added drop-wise at −10° C. The mixture was stirred at 0° C. for 1 h, and then the reaction mixture was quenched by addition 20 mL $H_2O$ at 0° C., and then extracted with 45 mL DCM. The combined organic layers were washed with brine 20 mL, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 25%-60%, 8 min) to get the product (2R,4R)—N-(4-tert-butylphenyl)-1-cyano-4-methoxy-N-[2-oxo-1-(3-pyridyl)-2-(tetrahydropyran-4-ylamino)ethyl]pyrrolidine-2-carboxamide (22.6 mg, 43.49 umol, 43.02% yield, 100% purity) was obtained as a yellow solid.

$^1$H NMR (METHANOL-$d_4$, 400 MHz): δ ppm 8.26-8.32 (m, 2H), 6.48-7.87 (m, 6H), 6.16 (s, 1H), 4.20 (dd, J=8.7, 6.7 Hz, 1H), 3.83-3.99 (m, 4H), 3.64 (dd, J=9.4, 6.2 Hz, 1H), 3.43-3.53 (m, 3H), 3.28 (s, 3H), 2.07-2.18 (m, 1H), 2.03 (d, J=6.6 Hz, 1H), 1.88-1.96 (m, 1H), 1.69-1.78 (m, 1H), 1.51-1.62 (m, 1H), 1.37 (br d, J=7.7 Hz, 1H), 1.20-1.25 (m, 9H) MS (ESI) m/z 520.4 $[M+H]^+$ To a solution of (2R,4R)—N-(4-tert-butylphenyl)-4-methoxy-N-[2-oxo-1-(3-pyridyl)-2-(tetrahydropyran-4-ylamino)ethyl]pyrrolidine-2-carboxamide (50 mg, 101.09 umol, 1 eq) in DMF (2 mL) was cooled to −10° C., and then $NaHCO_3$ (25.48 mg, 303.26 umol, 11.79 uL, 3.0 eq) and BrCN (16.06 mg, 151.63 umol, 11.15 uL, 1.5 eq) in DMF (0.4 mL) was added drop-wise at −10° C. The mixture was stirred at 0° C. for 1 h. The reaction mixture was quenched by addition $H_2O$ 20 mL at 0° C., and then extracted with DCM 45 mL. The combined organic layers were washed with brine 20 mL, dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM NH4HCO$_3$)-ACN]; B %: 25%-60%, 8 min) to get the product (2R,4R)—N-(4-tert-butylphenyl)-1-cyano-4-methoxy-N-[2-oxo-1-(3-pyridyl)-2-(tetrahydropyran-4-ylamino)ethyl]pyrrolidine-2-carboxamide (24.05 mg, 46.28 umol, 45.78% yield, 100% purity) was obtained as a white solid.

$^1$H NMR (METHANOL-$d_4$, 400 MHz): δ ppm 8.30-8.40 (m, 2H), 6.41-7.88 (m, 6H), 6.01 (s, 1H), 4.26 (dd, J=8.8, 5.7 Hz, 1H), 3.82-3.95 (m, 4H), 3.61 (dd, J=9.7, 5.9 Hz, 1H), 3.41-3.51 (m, 3H), 3.27 (s, 3H), 2.08 (ddd, J=13.3, 8.8, 6.4 Hz, 1H), 1.84-1.97 (m, 2H), 1.66-1.74 (m, 1H), 1.49-1.60 (m, 1H), 1.33-1.42 (m, 1H), 1.25 (s, 9H) MS (ESI) m/z 520.4 $[M+H]^+$ Example 205: Synthesis of Compound 1163c

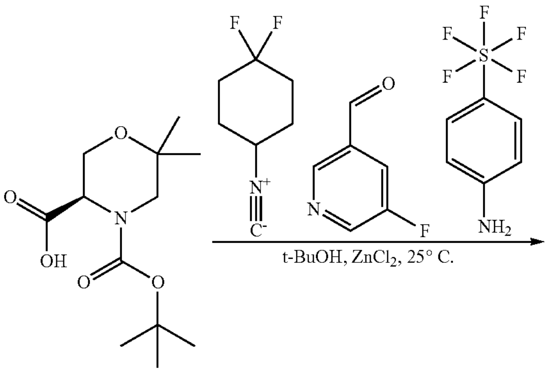

-continued

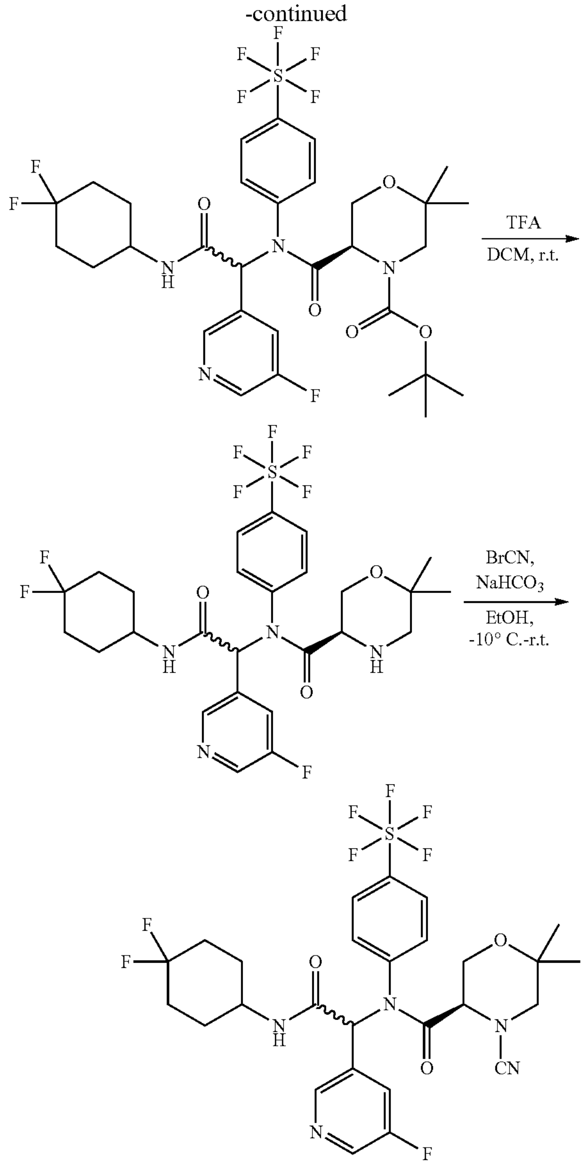

Step 1: tert-butyl (5R)—S-[[2-[(4,4-difluorocyclohexyl)amino]-2-oxo-1-(3-pyridyl)ethyl]-[4-(pentafluoro-λ$^6$-sulfanyl)phenyl]carbamoyl]-2,2-dimethyl-morpholine-4-carboxylate A solution of 4-(pentafluoro-λ$^6$-sulfanyl)aniline (338.11 mg, 1.54 mmol, 1 eq), pyridine-3-carbaldehyde (165.23 mg, 1.54 mmol, 144.94 uL, 1 eq) in t-BuOH (8 mL) was stirred at 25° C. for 2 h. (3R)-4-tert-butoxycarbonyl-6,6-dimethyl-morpholine-3-carboxylic acid (400 mg, 1.54 mmol, 1 eq) was added to the reactant mixture, and then a solution of 1,1-difluoro-4-isocyano-cyclohexane (201.52 mg, 1.39 mmol, 0.9 eq) in t-BuOH (1 mL) in batches (three times). After adding $ZnCl_2$ (1 M, 9.26 mL, 6 eq), the mixture was stirred at 25° C. for 14 h. Upon completion, the reaction mixture was concentrated under reduced pressure to give a residue. The residue was purified by column chromatography ($SiO_2$, Petroleum ether/Ethyl acetate=10/1 to 0/1) to give the title compound tert-butyl (5R)-5-[[2-[(4,4-difluorocyclohexyl)amino]-2-oxo-1-(3-pyridyl)ethyl]-[4-(pentafluoro-$\lambda^6$-sulfanyl)phenyl]carbamoyl]-2,2-dimethyl-morpholine-4-carboxylate (700 mg, 491.08 umol, 31.83% yield, 50% purity) as a yellow oil. MS (ESI) m/z 713.2 $[M+1]^+$ Step 2: (3R)—N-[2-[(4,4-difluorocyclohexyl)amino]-2-oxo-1-(3-pyridyl)ethyl]-6,6-dimethyl-N-[4-(pentafluoro-$\lambda^6$-sulfanyl)phenyl]morpholine-3-carboxamide A mixture of tert-butyl (5R)-5-[[2-[(4,4-difluorocyclohexyl)amino]-2-oxo-1-(3-pyridyl)ethyl]-[4-(pentafluoro-$\lambda^6$-sulfanyl)phenyl]carbamoyl]-2,2-dimethyl-morpholine-4-carboxylate (680 mg, 477.05 umol, 50% purity, 1 eq) in DCM (5 mL) and TFA (3 mL) was stirred at 25° C. for 0.5 h under $N_2$ atmosphere. Upon completion, the reaction mixture was quenched by addition $NaHCO_3$ aq (60 mL), and extracted with DCM (40 mL*3). The combined organic layers were washed with brine (60 mL), dried over $Na_2SO_4$, filtered and concentrated under reduced pressure to give a (3R)—N-[2-[(4,4-difluorocyclohexyl)amino]-2-oxo-1-(3-pyridyl)ethyl]-6,6-dimethyl-N-[4-(pentafluoro-$\lambda^6$-sulfanyl)phenyl]morpholine-3-carboxamide (400 mg, crude) as a yellow oil. MS (ESI) m/z 613.2 $[M+H]^+$ Step 3: (3R)-4-cyano-N-[2-[(4,4-difluorocyclohexyl)amino]-2-oxo-1-(3-pyridyl)ethyl]-6,6-dimethyl-N-[4-(pentafluoro-2f-sulfanyl)phenyl]morpholine-3-carboxamide To a solution of (3R)—N-[2-[(4,4-difluorocyclohexyl)amino]-2-oxo-1-(3-pyridyl)ethyl]-6,6-dimethyl-N-[4-(pentafluoro-$\lambda^6$-sulfanyl)phenyl]morpholine-3-carboxamide (390 mg, 305.58 umol, 48% purity, 1 eq) and BrCN (48.55 mg, 458.37 umol, 33.72 uL, 1.5 eq) in EtOH (5 mL) was added a solution of $NaHCO_3$ (77.01 mg, 916.75 umol, 35.65 uL, 3 eq) in EtOH (1 mL) drop-wise at −10° C. under $N_2$. The reaction mixture was slowly warmed to 25° C. for 1 h. Upon completion, the reaction mixture was quenched by addition $H_2O$ (60 mL) and extracted with EtOAc (35 mL*3). The combined organic layers were washed with brine (50 mL), dried over $Na_2SO_4$, filtered and concentrated under reduced pressure to give a residue. The residue was purified by prep-HPLC (column: Phenomenex Luna C18 200*40 mm*10 um; mobile phase: [water (0.2% FA)-ACN]; B %: 40%-80%, 8 min) to give the title compound (3R)-4-cyano-N-[2-[(4,4-difluorocyclohexyl)amino]-2-oxo-1-(3-pyridyl)ethyl]-6,6-dimethyl-N-[4-(pentafluoro-$\lambda^6$-sulfanyl)phenyl]morpholine-3-carboxamide (42 mg, 62.58 umol, 20.48% yield, 95% purity) as a white solid. MS (ESI) m/z 638.2 $[M+H]^+$ $^1H$ NMR (400 MHz, MeOD-$d_4$) δ ppm 8.35-8.32 (m, 2H), 8.01-7.23 (m, 6H), 6.13 (s, 1H), 3.90-3.81 (m, 4H), 3.49-3.45 (m, 1H), 2.94-2.90 (m, 1H), 2.02-1.81 (m, 6H), 1.71-1.62 (m, 1H), 1.51-1.47 (m, 1H), 1.24-1.20 (m, 6H).

(3R)-4-cyano-N-[2-[(4,4-difluorocyclohexyl)amino]-2-oxo-1-(3-pyridyl)ethyl]-6,6-dimethyl-N-[4-(pentafluoro-$\lambda^6$-sulfanyl)phenyl]morpholine-3-carboxamide (68 mg, 105.16 umol, 34.41% yield, 98.6% purity) was obtained as a white solid. MS (ESI) m/z 638.2 $[M+H]^+$ $^1H$ NMR (400 MHz, MeOD-$d_4$) δ ppm 8.35-8.32 (m, 2H), 8.21-7.55 (m, 4H), 7.45-6.81 (m, 2H), 6.23 (s, 1H), 3.89-3.78 (m, 4H), 3.37-3.34 (m, 1H), 2.91-2.88 (m, 1H), 2.02-1.83 (m, 6H), 1.71-1.64 (m, 1H), 1.51-1.46 (m, 1H), 1.30 (s, 3H), 1.15 (s, 3H).

Example 206: Synthesis of Compound 1230

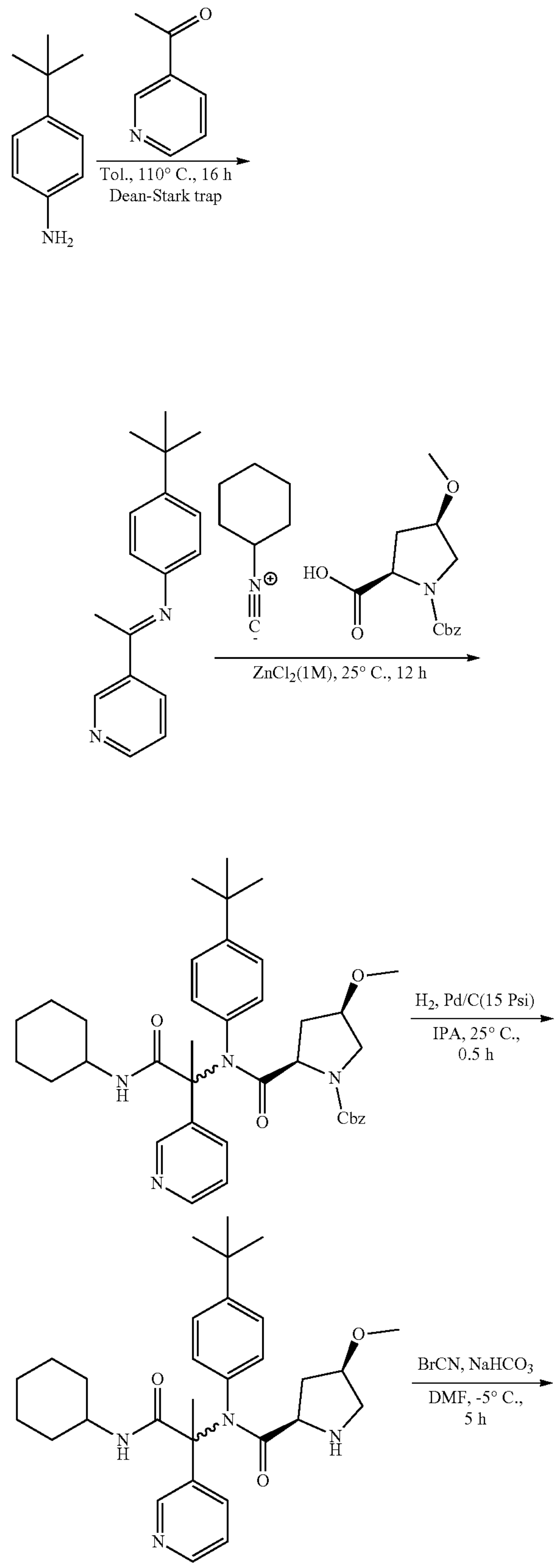

-continued

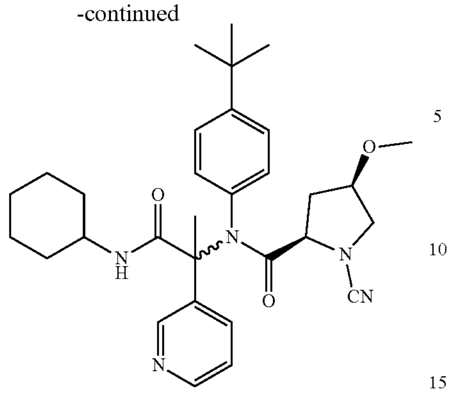

Step 1: (E)-4-(tert-butyl)-N-(1-(pyridin-3-yl)ethylidene)aniline

A mixture of 4-tert-butylaniline (5 g, 33.50 mmol, 5.29 mL, 1 eq) and 1-(3-pyridyl)ethanone (4.06 g, 33.50 mmol, 3.69 mL, 1 eq) in toluene (50 mL) was stirred at 110° C. for 16 h. Water was removed by Dean-Stark trap, and the reaction mixture was concentrated under reduced pressure to give a residue. The residue was purified by column chromatography ($SiO_2$, petroleum ether:ethyl acetate=10:1 to 6:1) to give (E)-N-(4-tert-butylphenyl)-1-(3-pyridyl)ethanimine (2 g, 7.13 mmol, 21.29% yield, 90% purity) as a yellow solid. MS (ESI) m/z 253.2 $[M+H]^+$.

Step 2: (2R,4R)-benzyl 2-((4-(tert-butyl)phenyl)(1-(cyclohexylamino)-1-oxo-2-(pyridin-3-yl)propan-2-yl)carbamoyl)-4-methoxypyrrolidine-1-carboxylate To a solution of isocyanocyclohexane (432.60 mg, 3.96 mmol, 492.71 uL, 1 eq), (2R,4R)-1-benzyloxycarbonyl-4-methoxy-pyrrolidine-2-carboxylic acid (1.11 g, 3.96 mmol, 1 eq) and (E)-N-(4-tert-butylphenyl)-1-(3-pyridyl)ethanimine (1 g, 3.96 mmol, 1 eq) in t-BuOH (15 mL) was added $ZnCl_2$ (1 M, 23.78 mL, 6 eq). The mixture was stirred at 25° C. for 12 h. Upon completion, the reaction mixture was concentrated under reduced pressure to give a residue. The residue was purified by prep-HPLC (column: Agela DuraShell C18 250*70 mm*10 um; mobile phase: [water (10 mM $NH_4HCO_3$)-ACN]; B %: 63%-85%, 20 min) to give benzyl (2R,4R)-2-[(4-tert-butylphenyl)-[2-(cyclohexylamino)-1-methyl-2-oxo-1-(3-pyridyl)ethyl]carbamoyl]-4-methoxy-pyrrolidine-1-carboxylate Isomer 1 (0.06 g, 92.94 umol, 2.35% yield, 99.264% purity) as a white solid. MS (ESI) m/z 641.3 $[M+H]^+$.

$^1$H NMR (400 MHz, METHANOL-$d_4$) δ=8.66 (dd, J=1.8, 14.5 Hz, 1H), 8.50-8.32 (m, 1H), 8.04-7.86 (m, 1H), 7.54-7.45 (m, 1H), 7.45-7.19 (m, 8H), 7.07 (br dd, J=2.2, 8.2 Hz, 1H), 5.40-5.07 (m, 2H), 4.19-4.00 (m, 1H), 3.91-3.61 (m, 3H), 3.28 (d, J=6.4 Hz, 3H), 2.30-2.16 (m, 1H), 2.00-1.58 (m, 8H), 1.49-1.09 (m, 16H).

Benzyl (2R,4R)-2-[(4-tert-butylphenyl)-[2-(cyclohexylamino)-1-methyl-2-oxo-1-(3-pyridyl)ethyl]carbamoyl]-4-methoxy-pyrrolidine-1-carboxylate Isomer 2 (0.06 g, 91.98 umol, 2.32% yield, 98.235% purity) was obtained as a white solid. MS (ESI) m/z 641.3 $[M+H]^+$.

$^1$H NMR (400 MHz, METHANOL-$d_4$) δ=8.67 (d, J=1.8 Hz, 1H), 8.40 (br d, J=4.8 Hz, 1H), 7.97 (br d, J=8.2 Hz, 1H), 7.80-7.26 (m, 10H), 5.29-5.09 (m, 2H), 4.03 (br t, J=8.2 Hz, 1H), 3.93-3.64 (m, 3H), 3.23 (s, 3H), 2.33-2.16 (m, 1H), 2.05-1.55 (m, 8H), 1.48-1.10 (m, 16H).

Step 3: (2R,4R)—N-(4-(tert-butyl)phenyl)-N-(1-(cyclohexylamino)-1-oxo-2-(pyridin-3-yl)propan-2-yl)-4-methoxypyrrolidine-2-carboxamide Isomer 1

To a solution of benzyl (2R,4R)-2-[(4-tert-butylphenyl)-[2-(cyclohexylamino)-1-methyl-2-oxo-1-(3-pyridyl)ethyl]carbamoyl]-4-methoxy-pyrrolidine-1-carboxylate Isomer 1 (50.00 mg, 78.03 umol, 1 eq) in i-PrOH (0.5 mL) was added Pd/C (0.02 g, 78.03 umol, 10% purity, 1 eq), and the mixture was stirred at 25° C. for 0.5 h under $H_2$ (157.61 ug, 78.03 umol, 1 eq) at 15 Psi. Upon completion, the reaction mixture was filtered and concentrated under reduced pressure to give (2R,4R)—N-(4-tert-butylphenyl)-N-[2-(cyclohexylamino)-1-methyl-2-oxo-1-(3-pyridyl)ethyl]-4-methoxy-pyrrolidine-2-carboxamide Isomer 1 (0.05 g, crude) as a yellow solid. MS (ESI) m/z 507.3 $[M+H]^+$.

(2R,4R)—N-(4-(tert-butyl)phenyl)-N-(1-(cyclohexylamino)-1-oxo-2-(pyridin-3-yl)propan-2-yl)-4-methoxypyrrolidine-2-carboxamide Isomer 2

To a solution of benzyl (2R,4R)-2-[(4-tert-butylphenyl)-[2-(cyclohexylamino)-1-methyl-2-oxo-1-(3-pyridyl)ethyl]carbamoyl]-4-methoxy-pyrrolidine-1-carboxylate Isomer 2 (60.00 mg, 93.63 umol, 1 eq) in i-PrOH (0.5 mL) was added Pd/C (0.02 g, 10% purity), and the mixture was stirred at 25° C. for 0.5 h under $H_2$ (189.14 ug, 93.63 umol, 1 eq) at 15 Psi. Upon completion, the reaction mixture was filtered and concentrated under reduced pressure to give (2R,4R)—N-(4-tert-butylphenyl)-N-[2-(cyclohexylamino)-1-methyl-2-oxo-1-(3-pyridyl)ethyl]-4-methoxy-pyrrolidine-2-carboxamide Isomer 2 (0.06 g, crude) as a yellow solid. MS (ESI) m/z 507.4 $[M+H]^+$.

Step 4: (2R,4R)—N-(4-(tert-butyl)phenyl)-1-cyano-N-(1-(cyclohexylamino)-1-oxo-2-(pyridin-3-yl)propan-2-yl)-4-methoxypyrrolidine-2-carboxamide Isomer 1

To a solution of (2R,4R)—N-(4-tert-butylphenyl)-N-[2-(cyclohexylamino)-1-methyl-2-oxo-1-(3-pyridyl)ethyl]-4-methoxy-pyrrolidine-2-carboxamide Isomer 1 (0.05 g, 98.68 umol, 1 eq) in DMF (1 mL) was added $NaHCO_3$ (24.87 mg, 296.05 umol, 11.51 uL, 3 eq) and BrCN (20.90 mg, 197.36 umol, 14.52 uL, 2 eq) under $N_2$ at −5° C. The mixture was stirred at −5° C. for 0.5 h under $N_2$ atmosphere. Upon completion, the reaction mixture was diluted with water (5 mL) and extracted with EA (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 40%-70%, 10 min) to give (2R,4R)—N-(4-tert-butylphenyl)-1-cyano-N-[2-(cyclohexylamino)-1-methyl-2-oxo-1-(3-pyridyl)ethyl]-4-methoxy-pyrrolidine-2-carboxamide Isomer 1 (18.26 mg, 32.19 umol, 32.62% yield, 93.743% purity) as a yellow solid. MS (ESI) m/z 532.2 $[M+H]^+$.

$^1$H NMR (400 MHz, METHANOL-$d_4$) δ=8.64 (d, J=2.0 Hz, 1H), 8.41 (dd, J=1.3, 4.8 Hz, 1H), 7.99 (td, J=1.8, 8.2 Hz, 1H), 7.55-7.44 (m, 2H), 7.38 (dd, J=4.9, 8.1 Hz, 1H), 7.29 (br d, J=8.2 Hz, 1H), 7.19 (br d, J=8.1 Hz, 1H), 4.15 (dd, J=6.3, 8.6 Hz, 1H), 3.87 (t, J=6.0 Hz, 1H), 3.77 (br s, 1H), 3.59 (dd, J=6.1, 9.4 Hz, 1H), 3.42 (dd, J=5.4, 9.4 Hz,

1H), 3.27 (s, 3H), 2.10 (br dd, J=1.7, 6.7 Hz, 1H), 1.94-1.84 (m, 3H), 1.74 (br d, J=11.6 Hz, 2H), 1.71-1.58 (m, 4H), 1.44-1.17 (m, 14H).

(2R,4R)—N-(4-(tert-butyl)phenyl)-1-cyano-N-(1-(cyclohexylamino)-1-oxo-2-(pyridin-3-yl)propan-2-yl)-4-methoxypyrrolidine-2-carboxamide Isomer 2

To a solution of (2R,4R)—N-(4-tert-butylphenyl)-N-[2-(cyclohexylamino)-1-methyl-2-oxo-1-(3-pyridyl)ethyl]-4-methoxy-pyrrolidine-2-carboxamide Isomer 2 (0.06 g, 118.42 umol, 1 eq) in DMF (1 mL) was added $NaHCO_3$ (29.85 mg, 355.26 umol, 13.82 uL, 3 eq) and BrCN (15.05 mg, 142.10 umol, 10.45 uL, 1.2 eq) at −5° C. under $N_2$ atmosphere, and the mixture was stirred at −5° C. for 0.5 h under $N_2$ atmosphere. Upon completion, the reaction mixture was diluted with water (5 mL) and extracted with EA (3 mL*3). The combined organic layers were dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 40%-70%, 10 min) to give (2R,4R)—N-(4-tert-butylphenyl)-1-cyano-N-[2-(cyclohexylamino)-1-methyl-2-oxo-1-(3-pyridyl)ethyl]-4-methoxy-pyrrolidine-2-carboxamide Isomer 2 (15.81 mg, 29.56 umol, 24.96% yield, 99.4% purity) as a yellow solid. MS (ESI) m/z 532.3 $[M+H]^+$.

$^1$H NMR (400 MHz, METHANOL-$d_4$) δ=8.56 (d, J=1.8 Hz, 1H), 8.38 (dd, J=1.4, 4.8 Hz, 11H), 7.92-7.83 (m, 11H), 7.51 (dd, J 2.3, 8.3 Hz, 11H), 7.43 (dd, J=2.3, 8.3 Hz, 1H), 7.35 (dd, J=4.8, 8.2 Hz, 1H), 7.26 (dd, J=2.3, 8.3 Hz, 1H), 7.21 (dd, J=2.1, 8.3 Hz, 1H), 4.15 (dd, J=5.7, 8.8 Hz, 11H), 3.94-3.74 (m, 2H), 3.59 (dd, J=5.8, 9.5 Hz, 11H), 3.43 (dd, J=4.8, 9.5 Hz, 1H), 3.27 (s, 3H), 2.19-2.07 (m, 1H), 2.02-1.88 (m, 3H), 1.83-1.71 (m, 2H), 1.71-1.58 (m, 4H), 1.45-1.18 (m, 14H)

Example 207: Synthesis of Compound 1288a

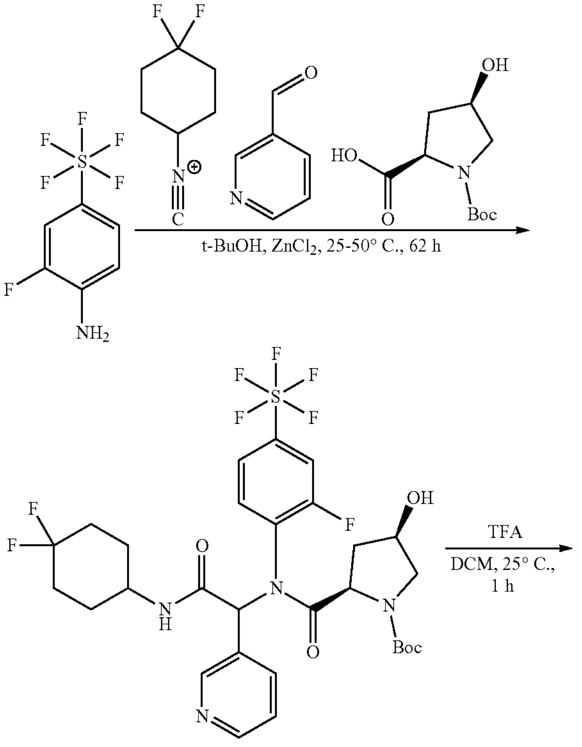

-continued

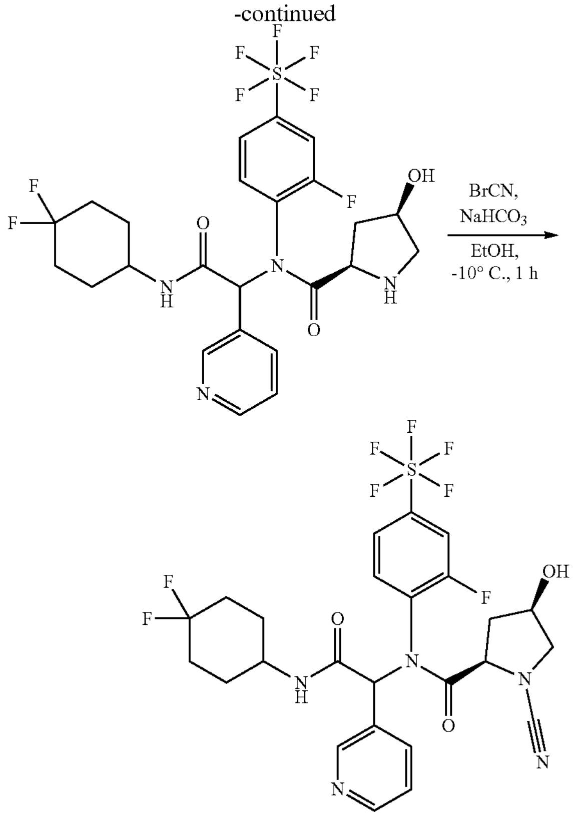

Step 1: tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-hydroxy-pyrrolidine-1-carboxylate A solution of pyridine-3-carbaldehyde (338.72 mg, 3.16 mmol, 297.12 uL, 1.5 eq) and 2-fluoro-4-(pentafluoro-λ$^6$-sulfanyl)aniline (500 mg, 2.11 mmol, 1 eq) in t-BuOH (10 mL) was stirred at 90° C. for 48 h. Then, (2R,4R)-1-tert-butoxycarbonyl-4-hydroxy-pyrrolidine-2-carboxylic acid (487.52 mg, 2.11 mmol, 1 eq), 1,1-difluoro-4-isocyano-cyclohexane (306.01 mg, 2.11 mmol, 1 eq) and $ZnCl_2$ (1 M, 6.32 mL, 3 eq) were added and stirred at 25° C. for 14 h. Upon completion, the reaction mixture was concentrated under reduced pressure and purified by prep-HPLC (column: Kromasil C18 (250*50 mm*10 um); mobile phase: [water (10 mM $NH_4HCO_3$)-ACN]; B %: 55%-75%, 10 min) to give tert-butyl (2R,4R)-2-[[2-[(4,4-difluorocyclohexyl)amino]-2-oxo-1-(3-pyridyl)ethyl]-[2-fluoro-4-(pentafluoro-λ$^6$-sulfanyl)phenyl]carbamoyl]-4-hydroxy-pyrrolidine-1-carboxylate Isomer 1 (190 mg, 243.36 umol, 11.54% yield, 90% purity) as light yellow solid. MS (ESI) m/z 703.2 $[M+H]^+$.

Tert-butyl (2R,4R)-2-[[2-[(4,4-difluorocyclohexyl) amino]-2-oxo-1-(3-pyridyl)ethyl]-[2-fluoro-4-(pentafluoro-λ$^6$-sulfanyl)phenyl]carbamoyl]-4-hydroxy-pyrrolidine-1-carboxylate Isomer 2 (150 mg, 192.13 umol, 9.11% yield, 90% purity) was obtained as light yellow solid. MS (ESI) m/z 703.2 $[M+H]^+$.

Step 2: (2R,4R)—N-[2-[(4,4-difluorocyclohexyl) amino]-2-oxo-1-(3-pyridyl)ethyl]-N-[2-fluoro-4-(pentafluoro-A-sulfanyl)phenyl]-4-hydroxy-pyrrolidine-2-carboxamide A solution of tert-butyl (2R,4R)-2-[[2-[(4,4-difluorocyclohexyl)amino]-2-oxo-1-(3-pyridyl)ethyl]-[2-fluoro-4-

(pentafluoro-$\lambda^6$-sulfanyl)phenyl]carbamoyl]-4-hydroxy-pyrrolidine-1-carboxylate Isomer 1 (180 mg, 256.17 umol, 1 eq), TFA (770.00 mg, 6.75 mmol, 0.5 mL, 26.36 eq) in DCM (1.5 mL) was stirred at 25° C. for 1 h. Upon completion, the reaction mixture was concentrated under reduced pressure, the pH was adjusted to 7-8 with $NaHCO_3$ aq. (10 mL) and extracted with EtOAc (10 mL*3). The organic layers were washed with brine (10.0 mL), dried over $Na_2SO_4$, filtered, concentrated under reduced pressure and purified by prep-TLC ($SiO_2$, DCM:MeOH=10:1) to give (2R,4R)—N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide Isomer 1 (60 mg, crude) as yellow solid. MS (ESI) m/z 603.2 $[M+H]^+$.

A solution of tert-butyl (2R,4R)-2-[[2-[(4,4-difluorocyclohexyl)amino]-2-oxo-1-(3-pyridyl)ethyl]-[2-fluoro-4-(pentafluoro-$\lambda^6$-sulfanyl)phenyl]carbamoyl]-4-hydroxy-pyrrolidine-1-carboxylate Isomer 2 (140 mg, 199.24 umol, 1 eq), and TFA (770.00 mg, 6.75 mmol, 0.5 mL, 33.89 eq) in DCM (1.5 mL) was stirred at 25° C. for 1 h. Upon completion, the reaction mixture was concentrated under reduced pressure, the pH was adjusted to 7-8 with $NaHCO_3$ aq. (10 mL) and extracted with EtOAc (10 mL*3). The organic layers were washed with brine (10.0 mL), dried over $Na_2SO_4$, filtered, concentrated under reduced pressure and purified by prep-TLC ($SiO_2$, DCM:MeOH=10:1) to give (2R,4R)—N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide Isomer 2 (80 mg, crude) as yellow solid. MS (ESI) m/z 603.2 $[M+H]^+$.

Step 3: (2R,4R)-1-cyano-N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide To a solution of (2R,4R)—N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide Isomer 1 (50 mg, 82.98 umol, 1 eq) in EtOH (1 mL) was added $NaHCO_3$ (13.94 mg, 165.96 umol, 6.45 uL, 2 eq), and then BrCN (9.7 mg, 91.58 umol, 6.74 uL, 1.1 eq) was added under $N_2$ at −10° C. The mixture was stirred at −10° C. for 1 h. Upon completion, the mixture was concentrated under reduced pressure and purified by prep-HPLC (column: Waters Xbridge BEH C18 100*30 mm*10 um; mobile phase: [water (10 mM $NH_4HCO_3$)-ACN]; B %: 25%-55%, 10 min) to give (2R,4R)-1-cyano-N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide Isomer 1 (23.83 mg, 37.53 umol, 45.23% yield, 98.83% purity) as white solid. MS (ESI) m/z 628.1 $[M+H]^+$.

$^1H$ NMR (400 MHz, MeOD-$d_4$) δ ppm 8.44-8.31 (m, 2H), 8.14 (t, J=8.4 Hz, 1H), 7.78-7.71 (m, 1H), 7.65-7.50 (m, 2H), 7.30-7.18 (m, 1H), 6.26 (s, 1H), 4.34-4.22 (m, 1H), 4.21-4.08 (m, 1H), 3.98-3.85 (m, 1H), 3.68-3.54 (m, 1H), 3.48-3.37 (m, 1H), 2.31-1.78 (m, 8H), 1.74-1.58 (m, 1H), 1.56-1.39 (m, 1H).

A solution of (2R,4R)—N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide Isomer 2 (70 mg, 116.17 umol, 1 eq) in EtOH (1 mL) was added with $NaHCO_3$ (19.52 mg, 232.35 umol, 9.04 uL, 2 eq), and then BrCN (13.5 mg, 127.45 umol, 9.38 uL, 1.1 eq) was added under $N_2$ at −10° C. The mixture was stirred at −10° C. for 1 h. Upon completion, the mixture was concentrated under reduced pressure and purified by prep-HPLC (column: Waters Xbridge BEH C18 100*30 mm*10 um; mobile phase: [water (10 mM $NH_4HCO_3$)-ACN]; B %: 25%-55%, 10 min) to give (2R,4R)-1-cyano-N-[2-[(4,4-difluorocyclohexyl)amino]-2-oxo-1-(3-pyridyl)ethyl]-N-[2-fluoro-4-(pentafluoro-$\lambda^6$-sulfanyl)phenyl]-4-hydroxy-pyrrolidine-2-carboxamide Isomer 2 (19.13 mg, 30.48 umol, 26.24% yield, 100% purity) as white solid. MS (ESI) m/z 628.1 $[M+H]^+$.

$^1H$ NMR (400 MHz, MeOD-$d_4$) δ ppm 8.47-8.33 (m, 2H), 8.23 (t, J=8.4 Hz, 1H), 7.85-7.77 (m, 1H), 7.64-7.48 (m, 2H), 7.27-7.18 (m, 1H), 6.09 (s, 1H), 4.34-4.19 (m, 2H), 3.93-3.81 (m, 1H), 3.65-3.55 (m, 1H), 3.45-3.38 (m, 1H), 2.18-1.74 (m, 8H), 1.71-1.35 (m, 2H)

Example 208: Synthesis of Compound 997c

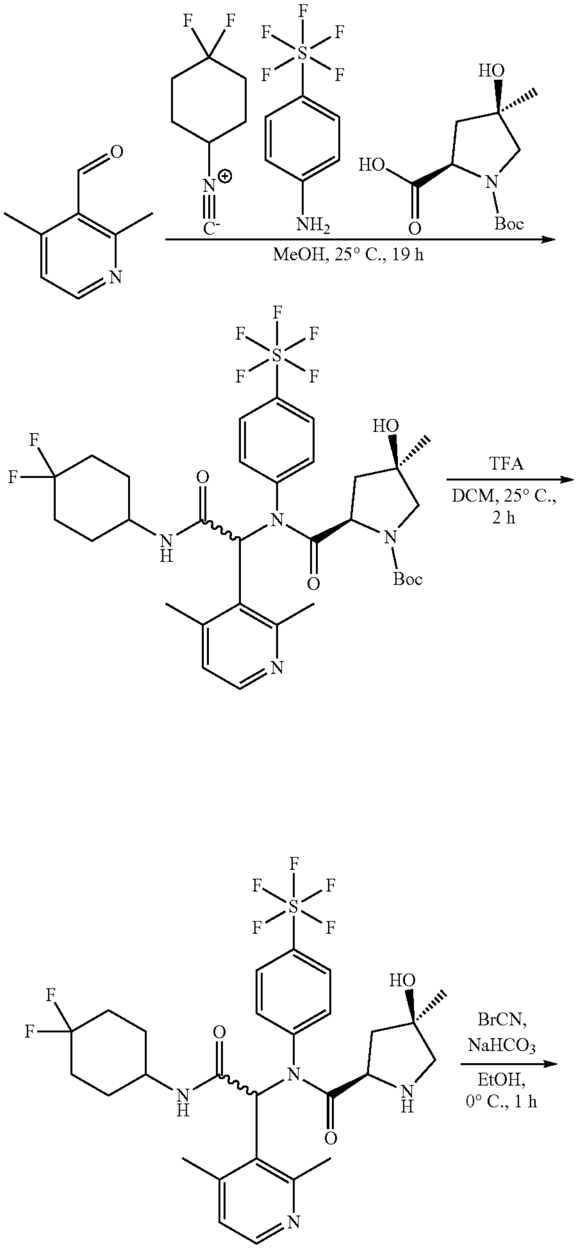

-continued

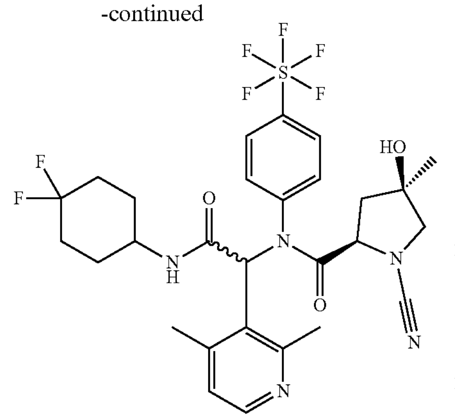

Step 1: (2R,4R)-2-[[2-[(4,4-difluorocyclohexyl) amino]-1-(2,4-dimethyl-3-pyridyl)-2-oxo-ethyl]-[4-(pentafluoro-$\lambda^6$-sulfanyl)phenyl]carbamoyl]-4-hydroxy-4-methyl-pyrrolidine-1-carboxylate A solution of 2,4-dimethylpyridine-3-carbaldehyde (300 mg, 2.22 mmol, 1 eq), 4-(pentafluoro-26-sulfanyl)aniline (486.47 mg, 2.22 mmol, 1 eq) in MeOH (1 mL) was stirred at 25° C. for 2 h, and then the (2R,4R)-1-tert-butoxycarbonyl-4-hydroxy-4-methyl-pyrrolidine-2-carboxylic acid (680.49 mg, 2.22 mmol, 80% purity, 1 eq) was added. 1,1-difluoro-4-isocyano-cyclohexane (322.17 mg, 2.22 mmol, 1 eq) was added, and then the solution was stirred at 25° C. for 17 h. Upon completion, the solution was concentrated to give the residue. The residue was purified by prep-HPLC (neutral condition), column: Waters Xbridge Prep OBD C18 150*40 mm*10 um; mobile phase: [water (10 mM $NH_4HCO_3$)-ACN]; B %: 45%-75%, 8 min. Tert-butyl (2R,4R)-2-[[2-[(4,4-difluorocyclohexyl)amino]-1-(2,4-dimethyl-3-pyridyl)-2-oxo-ethyl]-[4-(pentafluoro-λ6-sulfanyl)phenyl]carbamoyl]-4-hydroxy-4-methyl-pyrrolidine-1-carboxylate (300 mg, 412.80 umol, 18.60% yield, 100% purity) was obtained as white solid. MS (ESI) m/z 727.3 $[M+H]^+$.

Step 2: (2R,4R)—N-[2-[(4,4-difluorocyclohexyl) amino]-1-(2,4-dimethyl-3-pyridyl)-2-oxo-ethyl]-4-hydroxy-4-methyl-N-[4-(pentafluoro-λ6-sulfanyl) phenyl]pyrrolidine-2-carboxamide Tert-butyl (2R,4R)-2-[[2-[(4,4-difluorocyclohexyl) amino]-1-(2,4-dimethyl-3-pyridyl)-2-oxo-ethyl]-[4-(pentafluoro-λ6-sulfanyl)phenyl]carbamoyl]-4-hydroxy-4-methyl-pyrrolidine-1-carboxylate (270 mg, 371.52 umol, 1 eq) in DCM (5 mL)/TFA (1.54 g, 13.51 mmol, 1 mL, 36.35 eq) was stirred at 25° C. for 2 h. Upon completion, the solution was concentrated to remove the DCM and TFA, the pH was adjusted to 7-8 by $NaHCO_3$. aq. and extracted with EA (20*3 mL). The combined organic phase was dried over $Na_2SO_4$, filtrated and concentrated to give the crude. The crude was used to next step directly and without further purification. (2R, 4R)—N-[2-[(4,4-difluorocyclohexyl) amino]-1-(2,4-dimethyl-3-pyridyl)-2-oxo-ethyl]-4-hydroxy-4-methyl-N-[4-(pentafluoro-λ6-sulfanyl)phenyl]pyrrolidine-2-carboxamide (220 mg, crude) was obtained as yellow solid. MS (ESI) m/z 627.3 $[M+H]^+$.

Step 3: (2R,4R)-1-cyano-N-[2-[(4,4-difluorocyclohexyl)amino]-1-(2,4-dimethyl-3-pyridyl)-2-oxo-ethyl]-4-hydroxy-4-methyl-N-[4-(pentafluoro-$\lambda^6$-sulfanyl)phenyl]pyrrolidine-2-carboxamide (2R,4R)—N-[2-[(4,4-difluorocyclohexyl)amino]-1-(2,4-dimethyl-3-pyridyl)-2-oxo-ethyl]-4-hydroxy-4-methyl-N-[4-(pentafluoro-$\lambda^6$-sulfanyl)phenyl]pyrrolidine-2-carboxamide (220 mg, 351.09 umol, 1 eq) in EtOH (2.5 mL) was added the $NaHCO_3$ (58.99 mg, 702.17 umol, 27.31 uL, 2 eq) and the solution was cooled to 0° C. After adding BrCN (37.19 mg, 351.09 umol, 25.82 uL, 1 eq), the solution was stirred at 0° C. for 1 h. Upon completion, the solution was quenched with $H_2O$ (10 mL), extracted with EA (20*3 mL), and the combined organic phase was dried over $Na_2SO_4$, filtrated and concentrated to give the crude. The residue was purified by prep-HPLC (basic condition), column: Phenomenex Gemini-NX C18 75*30 mm*3 um; mobile phase: [water (0.05% $NH_3H_2O$+10 mM $NH_4HCO_3$)-ACN]; B %: 30%-60%, 8 min. (2R,4R)-1-cyano-N-[2-[(4,4-difluorocyclohexyl)amino]-1-(2,4-dimethyl-3-pyridyl)-2-oxo-ethyl]-4-hydroxy-4-methyl-N-[4-(pentafluoro-$\lambda^6$-sulfanyl)phenyl] pyrrolidine-2-carboxamide (60 mg, 89.81 umol, 25.58% yield, 97.539% purity) was obtained as white solid, $^1H$ NMR (400 MHz, METHANOL-$d_4$) δ=8.21 (t, J=5.6 Hz, 2H), 7.98 (br d, J=6.4 Hz, 1H), 7.65-7.47 (m, 1H), 7.08 (br s, 1H), 6.68 (d, J=14.3 Hz, 1H), 6.53-6.25 (m, 1H), 4.45-4.12 (m, 1H), 3.87 (br s, 1H), 3.51 (dd, J=2.5, 9.2 Hz, 1H), 3.40-3.32 (m, 1H), 3.09-1.34 (m, 16H), 1.26 (d, J=15.2 Hz, 3H). MS (ESI) m/z 652.1 $[M+H]^+$.

Example 209: Synthesis of Compound 1086b

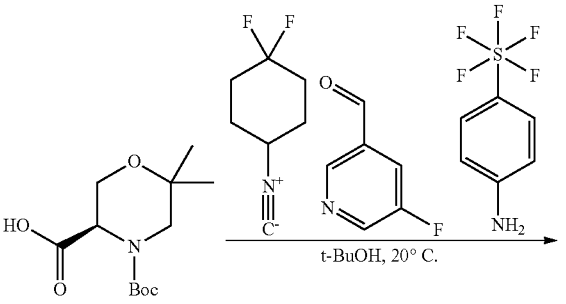

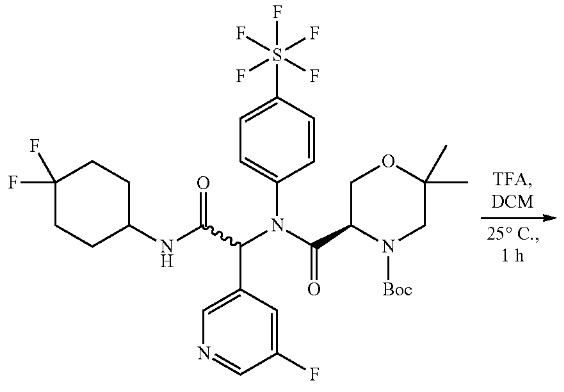

-continued

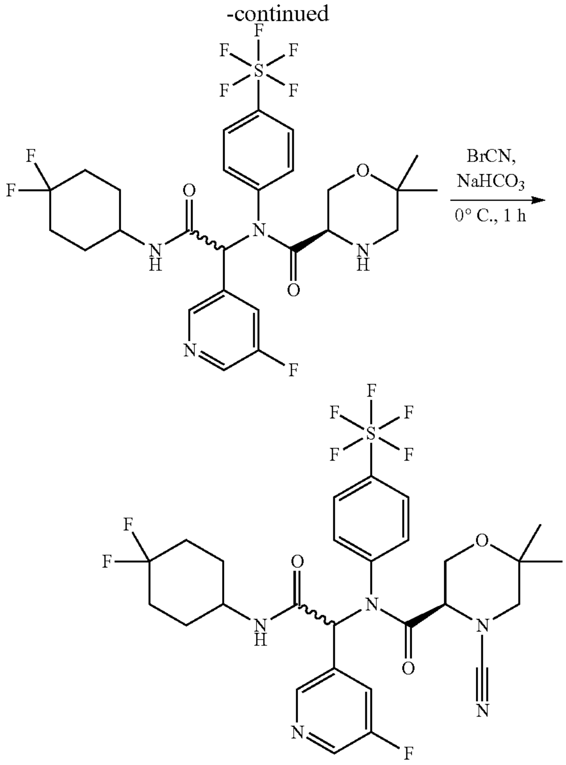

Step 1: tert-butyl (5R)-5-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2,2-dimethyl-morpholine-4-carboxylate A solution of 4-(pentafluoro-λ$^6$-sulfanyl)aniline (300 mg, 1.37 mmol, 1 eq), 5-fluoropyridine-3-carbaldehyde (171.23 mg, 1.37 mmol, 1 eq) in t-BuOH (9 mL) was stirred for 1 h, and then (3R)-4-tert-butoxycarbonyl-6,6-dimethyl-morpholine-3-carboxylic acid (354.92 mg, 1.37 mmol, 1 eq) was added. After stirring for another 10 min, 1,1-difluoro-4-isocyano-cyclohexane (198.68 mg, 1.37 mmol, 1 eq) in t-BuOH (1 mL) was added, stirred 10 min, and then $ZnCl_2$ (1 M, 4.11 mL, 3 eq) was added. The mixture was stirred at 25° C. for 14 h 40 min. Upon completion, the reaction mixture was concentrated under reduced pressure to remove solvent. The residue was purified by prep-HPLC (column: Kromasil C18 (250*50 mm*10 um); mobile phase: [water (10 mM $NH_4HCO_3$)-ACN]; B %: 60%-80%, 10 min) to give tert-butyl (5R)-5-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2,2-dimethyl-morpholine-4-carboxylate (120 mg, 159.30 umol, 11.64% yield, 97% purity); and tert-butyl (5R)-5-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2,2-dimethyl-morpholine-4-carboxylate (150 mg, 199.12 umol, 14.55% yield, 97% purity) as a yellow solid. MS (ESI) m/z 731.2 [M+H]+

Step 2: (3R)—N-[2-[(4,4-difluorocyclohexyl)amino]-1-(5-fluoro-3-pyridyl)-2-oxo-ethyl]-6,6-dimethyl-N-[4-(pentafluoro-λ$^6$-sulfanyl)phenyl]morpholine-3-carboxamide Isomer 1: To a solution of tert-butyl (5R)-5-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2,2-dimethyl-morpholine-4-carboxylate (120 mg, 164.22 umol, 1 eq) in DCM (2 mL) was added TFA (1.54 g, 13.51 mmol, 1 mL, 82.24 eq). The mixture was stirred at 25° C. for 1 h. Upon completion, the reaction mixture was poured into $NaHCO_3$ (25 mL) at 25° C., and then extracted with DCM (25 mL*3). The combined organic layers were washed with brine (25 mL*2), dried over $Na_2SO_4$, filtered and concentrated to give (3R)—N-[2-[(4,4-difluorocyclohexyl)amino]-1-(5-fluoro-3-pyridyl)-2-oxo-ethyl]-6,6-dimethyl-N-[4-(pentafluoro-λ$^6$-sulfanyl)phenyl]morpholine-3-carboxamide (103 mg, crude) as a yellow solid. MS (ESI) m/z 631.2 $[M+H]^+$ Isomer 2: To a solution of tert-butyl (5R)-5-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-2,2-dimethyl-morpholine-4-carboxylate (150 mg, 205.28 umol, 1 eq) in DCM (3 mL) was added TFA (2.31 g, 20.26 mmol, 1.5 mL, 98.69 eq). The mixture was stirred at 25° C. for 1 h. Upon completion, the reaction mixture was poured into $NaHCO_3$ (25 mL) at 25° C., and then extracted with DCM (25 mL*3). The combined organic layers were washed with brine (25 mL*2), dried over $Na_2SO_4$, filtered and concentrated to give (3R)—N-[2-[(4,4-difluorocyclohexyl)amino]-1-(5-fluoro-3-pyridyl)-2-oxo-ethyl]-6,6-dimethyl-N-[4-(pentafluoro-%$^6$-sulfanyl)phenyl]morpholine-3-carboxamide (129 mg, crude) as a yellow solid. MS (ESI) m/z 631.2 $[M+H]^+$ Step 3: (3R)-4-cyano-N-[2-[(4,4-difluorocyclohexyl)amino]-1-(5-fluoro-3-pyridyl)-2-oxo-ethyl]-6,6-dimethyl-N-[4-(pentafluoro-λ$^6$-sulfanyl)phenyl]morpholine-3-carboxamide Isomer 1: To a solution of (3R)—N-[2-[(4,4-difluorocyclohexyl)amino]-1-(5-fluoro-3-pyridyl)-2-oxo-ethyl]-6,6-dimethyl-N-[4-(pentafluoro-λ$^6$-sulfanyl)phenyl]morpholine-3-carboxamide (103 mg, 163.34 umol, 1 eq), $NaHCO_3$ (41.16 mg, 490.02 umol, 19.06 uL, 3 eq) in DMF (1 mL), BrCN (22.49 mg, 212.34 umol, 15.62 uL, 1.3 eq) in DMF (0.1 mL) was added at 0° C. The mixture was stirred at 0° C. for 1 h. Upon completion, the reaction mixture was poured into $H_2O$ (25 mL) at 25° C., and then extracted with EtOAc (25 mL*3). The combined organic layers were washed with brine (25 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (10 mM $NH_4HCO_3$)-ACN]; B %: 40%-70%, 8 min) to give (3R)-4-cyano-N-[2-[(4,4-difluorocyclohexyl)amino]-1-(5-fluoro-3-pyridyl)-2-oxo-ethyl]-6,6-dimethyl-N-[4-(pentafluoro-λ$^6$-sulfanyl)phenyl]morpholine-3-carboxamide (36 mg, 54.22 umol, 33.20% yield, 98.75% purity) as a white solid. MS (ESI) m/z 656.2 $[M+H]^+$ Isomer 1: $^1H$ NMR (400 MHz, METHANOL-$d_4$) δ=8.32 (d, J=2.5 Hz, 1H), 8.20 (s, 1H), 8.11-7.12 (m, 5H), 6.23 (s, 1H), 4.02-3.71 (m, 4H), 3.37 (d, J=12.4 Hz, 1H), 2.91 (d, J=12.4 Hz, 1H), 2.13-1.77 (m, 6H), 1.72-1.57 (m, 1H), 1.52-1.39 (m, 1H), 1.29 (s, 3H), 1.16 (s, 3H).

Isomer 2: To a solution of (3R)—N-[2-[(4,4-difluorocyclohexyl)amino]-1-(5-fluoro-3-pyridyl)-2-oxo-ethyl]-6,6-dimethyl-N-[4-(pentafluoro-λ$^6$-sulfanyl)phenyl]morpholine-3-carboxamide (119 mg, 188.71 umol, 1 eq), and $NaHCO_3$ (47.56 mg, 566.13 umol, 22.02 uL, 3 eq) in DMF (1 mL), BrCN (25.99 mg, 245.32 umol, 18.05 uL, 1.3 eq) in DMF (0.1 mL) was added at 0° C. The mixture was stirred at 0° C. for 1 h. Upon completion, the reaction mixture was poured into $H_2O$ (20 mL) at 25° C., and then extracted with EtOAc (25 mL*3). The combined organic layers were washed with brine (20 mL*2), dried over $Na_2SO_4$, filtered and concentrated under reduced pressure to give a residue. The residue was purified by prep-HPLC (column: Phenomenex Luna C18 75*30 mm*3 um; mobile phase: [water (10 mM $NH_4HCO_3$)-ACN]; B %: 40%-70%, 8 min) to give (3R)-4-cyano-N-[2-[(4,4-difluorocyclohexyl)amino]-1-(5-fluoro-3-pyridyl)-2-oxo-ethyl]-6,6-dimethyl-N-[4-(pentafluoro-$\lambda^6$-sulfanyl)phenyl]morpholine-3-carboxamide (38 mg, 56.12 umol, 29.74% yield, 96.83% purity) as a white solid. MS (ESI) m/z 656.2 $[M+H]^+$ Isomer 2: $^1H$ NMR (400 MHz, METHANOL-$d_4$) δ=8.35 (d, J=2.7 Hz, 1H), 8.23 (s, 1H), 8.13-6.96 (m, 5H), 6.13 (s, 1H), 3.96-3.74 (m, 4H), 3.46 (d, J=12.5 Hz, 1H), 2.93 (d, J=12.5 Hz, 1H), 2.08-1.79 (m, 6H), 1.64 (s, 1H), 1.51-1.40 (m, 1H), 1.22 (d, J=16.0 Hz, 6H).

Example 210: Synthesis of Compound 1094

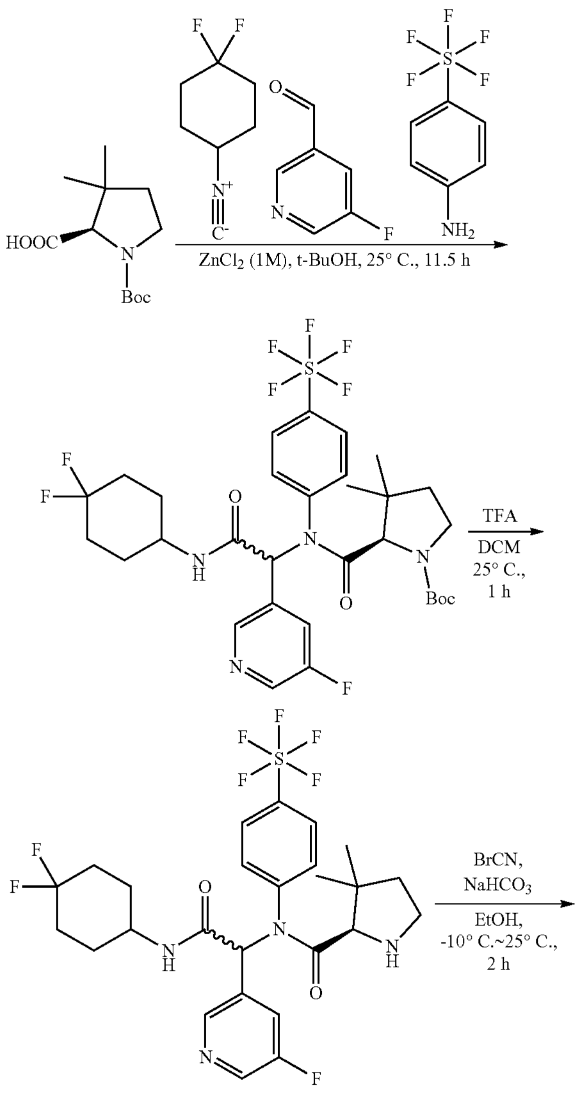

-continued

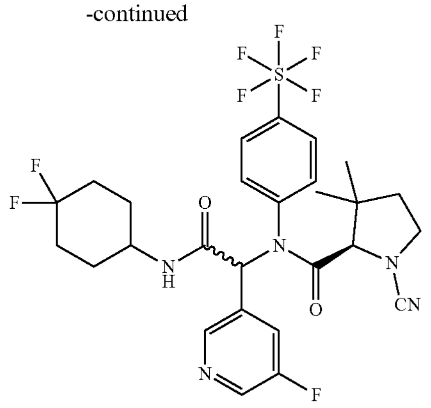

Step 1. tert-butyl(2R)-2-[[2-[(4,4-difluorocyclohexyl)amino]-1-(5-(fluoro-3-pyridyl)-2-oxo-ethyl)-[4-(pentafluoro-$\lambda^6$-sulfanyl)phenyl]carbamoyl]-3,3-dimethyl-pyrrolidine-1-carboxylate A solution of]5-fluoronicotinaldehyde (171.23 mg, 1.37 mmol, 1 eq), 4-(pentafluoro-$\lambda^6$-sulfanyl)aniline (300 mg, 1.37 mmol, 1 eq) in t-BuOH (15 mL) was stirred at 25° C. for 1 h, and the mixture was added with (R)-1-(tert-butoxycarbonyl)-3,3-dimethylpyrrolidine-2-carboxylic acid (333.02 mg, 1.37 mmol, 1 eq). The mixture was stirred at 25° C. for 0.5 h, and then added with 1,1-difluoro-4-isocyanocyclohexane (178.81 mg, 1.23 mmol, 0.9 eq) and $ZnCl_2$ (1 M, 8.21 mL, 6 eq). The mixture was stirred at 25° C. for 10 h, and the reaction mixture was concentrated under reduced pressure and was purified by prep-HPLC (column: Phenomenex Gemini-NX 80*40 mm*3 um; mobile phase: [water (10 mM $NH_4HCO_3$)-ACN]; B %: 45%-75%, 8 min) to give a product tert-butyl(2R)-2-[[2-[(4,4-difluorocyclohexyl)amino]-1-(5-fluoro-3-pyridyl)-2-oxo-ethyl]-[4-(pentafluoro-%$^6$-sulfanyl)phenyl]carbamoyl]-3,3-dimethyl-pyrrolidine-1-carboxylate (170 mg, 237.86 umol, 17.38% yield); tert-butyl(2R)-2-[[2-[(4,4-difluorocyclohexyl) amino]-1-(5-fluoro-3-pyridyl)-2-oxo-ethyl]-[4-(pentafluoro-$\lambda^6$-sulfanyl)phenyl]carbamoyl]-3,3-dimethyl-pyrrolidine-1-carboxylate (120 mg, 167.90 umol, 12.27% yield) as yellow solid. MS (ESI) m/z 715.2 $[M+H]^+$ Step 2: (2R)—N-[2-[(4,4-difluorocyclohexyl) amino]-J-(5-fluoro-3-pyridyl)-2-oxo-ethyl]-3,3-dimethyl-N-[4-(pentafluoro-$\lambda^6$-sulfanyl)phenyl]pyrrolidine-2-carboxamide Isomer 1: To a solution of tert-butyl (2R)-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]-3,3-dimethyl-pyrrolidine-1-carboxylate (150 mg, 209.88 umol, 1 eq) in DCM (3 mL) was added TFA (1.44 g, 12.59 mmol, 932.36 uL, 60 eq) and the mixture was stirred at 25° C. for 1 h. Upon completion, the mixture was quenched by addition $NaHCO_3$ (20 mL) and then extracted with EtOAc (10 mL*3). The combined organic layers were washed with brine (10 mL), dried over $Na_2SO_4$, filtered and concentrated under reduced pressure to give a residue to give the crude product (2R)—N-[2-[(4,4-difluorocyclohexyl)amino]-1-(5-fluoro-3-pyridyl)-2-oxo-ethyl]-3,3-dimethyl-N-[4-(pentafluoro-$\lambda^6$-sulfanyl)phenyl]pyrrolidine-2-carboxamide (140 mg, crude) was yellow oil. MS (ESI) m/z 615.2 $[M+H]^+$ Isomer 2: To a solution of tert-butyl (2R)-2-[[2-[(4,4-difluorocyclohexyl)amino]-1-(5-fluoro-3-pyridyl)-2-oxo-ethyl]-[4-(pentafluoro-λ$^6$-sulfanyl)phenyl]carbamoyl]-3,3-dimethyl-pyrrolidine-1-carboxylate (120 mg, 167.90 umol, 1 eq) in DCM (2.5 mL) was added TFA (1.15 g, 10.07 mmol, 745.89 uL, 60 eq) and the mixture was stirred at 25° C. for 1 h. Upon completion, the mixture was quenched by addition $NaHCO_3$ (20 mL), and then extracted with EtOAc (10 mL*3). The combined organic layers were washed with brine (10 mL), dried over $Na_2SO_4$, filtered and concentrated under reduced pressure to give crude product (2R)—N-[2-[(4,4-difluorocyclohexyl)amino]-1-(5-fluoro-3-pyridyl)-2-oxo-ethyl]-3,3-dimethyl-N-[4-(pentafluoro-λ$^6$-sulfanyl)phenyl]pyrrolidine-2-carboxamide (110 mg, crude) was yellow oil. MS (ESI) m/z 615.2 [M+H]$^+$ Step 3: (2R)-1-cyano-N-[2-[(4,4-difluorocyclohexyl)amino]-1-(5-fluoro-3-pyridyl)-2-oxo-ethyl]-3,3-dimethyl-N-[4-(pentafluoro-λ$^6$-sulfanyl)phenyl]pyrrolidine-2-carboxamide Isomer 1: To a solution of (2R)—N-[2-[(4,4-difluorocyclohexyl)amino]-1-(5-fluoro-3-pyridyl)-2-oxo-ethyl]-3,3-dimethyl-N-[4-(pentafluoro-λ$^6$-sulfanyl)phenyl]pyrrolidine-2-carboxamide (130 mg, 211.52 umol, 1 eq) in EtOH (2 mL) was added $NaHCO_3$ (53.31 mg, 634.57 umol, 24.68 uL, 3 eq), and the mixture was cooled at −10° C. After adding BrCN (33.61 mg, 317.28 umol, 23.34 uL, 1.5 eq) in EtOH (0.5 mL), the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue and was purified by prep-HPLC (column: Phenomenex Gemini-NX C18 75*30 mm*3 um; mobile phase: [water (10 mM $NH_4HCO_3$)-ACN]; B %: 45%-65%, 8 min) to give (2R)-1-cyano-N-[2-[(4,4-difluorocyclohexyl)amino]-1-(5-fluoro-3-pyridyl)-2-oxo-ethyl]-3,3-dimethyl-N-[4-(pentafluoro-%6-sulfanyl)phenyl]pyrrolidine-2-carboxamide (40 mg, 62.54 umol, 29.57% yield) was white solid. MS (ESI) m/z 640.3 [M+H]$^+$ $^1$H NMR (400 MHz, MeOD-d$_4$) δ=8.30-8.29 (m, 1H), 8.19 (s, 1H), 7.98-7.02 (m, 5H), 6.23 (s, 1H), 4.26-4.18 (m, 1H), 3.90-3.87 (m, 1H), 2.11-1.81 (m, 9H), 1.75-1.59 (m, 2H), 1.49-1.40 (m, 4H), 1.26-1.25 (m, 3H)

Isomer 2: To a solution of (2R)—N-[2-[(4,4-difluorocyclohexyl)amino]-1-(5-fluoro-3-pyridyl)-2-oxo-ethyl]-3,3-dimethyl-N-[4-(pentafluoro-λ$^6$-sulfanyl)phenyl]pyrrolidine-2-carboxamide (110 mg, 178.98 umol, 1 eq) in EtOH (2 mL) was added $NaHCO_3$ (45.11 mg, 536.94 umol, 20.88 uL, 3 eq) and the mixture was cooled at −10° C. The mixture was added with BrCN (28.44 mg, 268.47 umol, 19.75 uL, 1.5 eq) in EtOH (0.5 mL), and then the mixture was warmed at 25° C. and stirred for 2 h. Upon completion, the mixture was quenched by addition $H_2O$ (50 mL) and then extracted with DCM (30 mL*3). The combined organic layers were washed with brine (30 mL), dried over $Na_2SO_4$, filtered and concentrated under reduced pressure to give a residue and was purified by prep-HPLC (column: Phenomenex Gemini-NX C18 75*30 mm*3 um; mobile phase: [water (10 mM $NH_4HCO_3$)-ACN]; B %: 45%-65%, 8 min) to give (2R)-1-cyano-N-[2-[(4,4-difluorocyclohexyl)amino]-1-(5-fluoro-3-pyridyl)-2-oxo-ethyl]-3,3-dimethyl-N-[4-(pentafluoro-λ$^6$-sulfanyl)phenyl]pyrrolidine-2-carboxamide (40 mg, 53.39 umol, 29.83% yield) was white solid. MS (ESI) m/z 640.3 [M+H]$^+$ $^1$H NMR (400 MHz, MeOD-d$_4$) δ=8.35-8.34 (m, 1H), 8.24 (s, 1H), 7.91-7.20 (m, 5H), 6.08 (s, 1H), 4.24-4.15 (m, 1H), 3.89-3.87 (m, 1H), 2.12-1.81 (m, 9H), 1.76-1.57 (m, 2H), 1.50-1.40 (m, 4H), 1.26-1.25 (m, 3H)

Example 211: Synthesis of Compound 1100

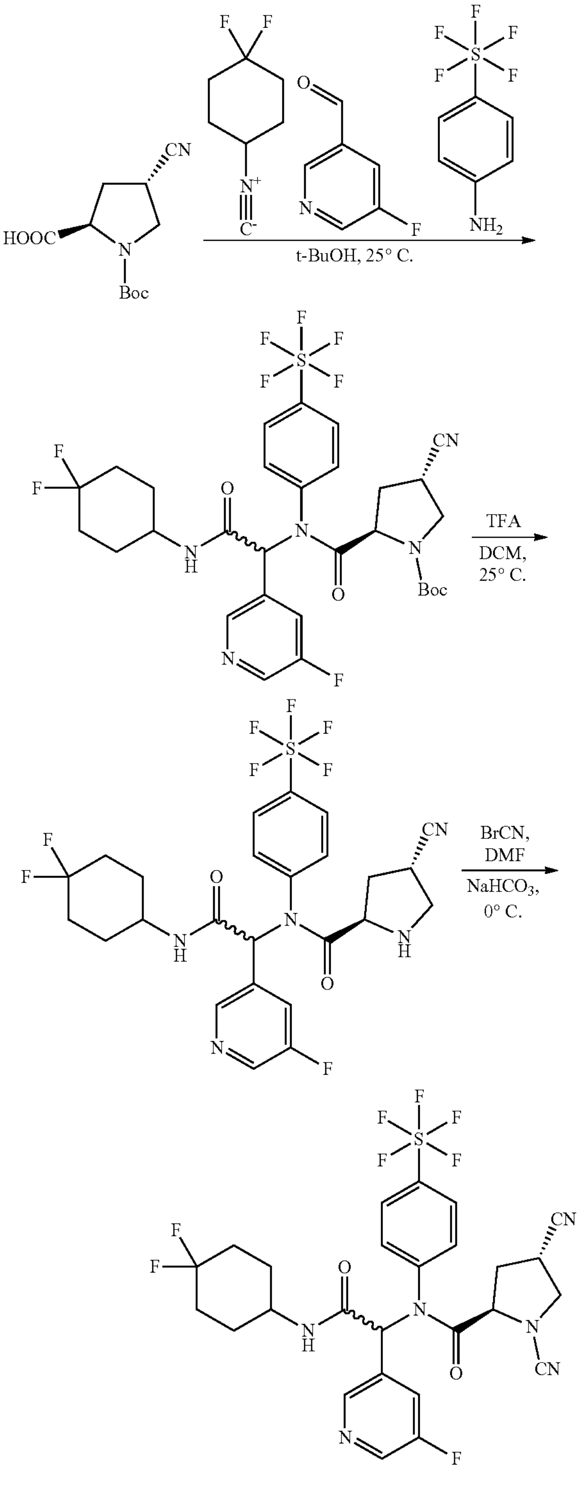

Step 1: tert-butyl (2R,4S)-4-cyano-2-[[2-[(4,4-difluorocyclohexyl)amino]-J-(5-fluoro-3-pyridyl)-2-oxo-ethyl]-[4-(pentafluoro-$\lambda^6$-sulfanyl)phenyl]carbamoyl]pyrrolidine-1-carboxylate A solution of 4-(pentafluoro-λ6-sulfanyl) aniline (218.94 mg, 998.94 umol, 1 eq) 5-fluoropyridine-3-carbaldehyde (124.97 mg, 998.94 umol, 1 eq) in t-BuOH (9 mL) was stirred for 1 h, and then (2R,4S)-1-tert-butoxycarbonyl-4-cyano-pyrrolidine-2-carboxylic acid (240 mg, 998.94 umol, 1 eq) was added, stirred 10 min. 1,1-difluoro-4-isocyano-cyclohexane (145.00 mg, 998.94 umol, 1 eq) in t-BuOH (1 mL) was added, stirred 10 min, and then $ZnCl_2$ (1 M, 3.00 mL, 3 eq) was added. The mixture was stirred at 25° C. for 14 h 40 min. Upon completion, the reaction mixture was concentrated under reduced pressure to remove solvent. The residue was purified by prep-HPLC (column: Kromasil C18 (250*50 mm*10 um); mobile phase: [water (10 mM $NH_4HCO_3$)-ACN]; B %: 55%-75%, 10 min) to give tert-butyl (2R,4S)-4-cyano-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (148 mg, 197.15 umol, 19.74% yield) and tert-butyl (2R,4S)-4-cyano-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (150 mg, 200.66 umol, 20.09% yield) as a white solid. MS (ESI) m/z 712.2 $[M+H]^+$ Step 2: (2R,4S)-4-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide Isomer 1: To a solution of tert-butyl (2R,4S)-4-cyano-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (148 mg, 207.96 umol, 1 eq) in DCM (5 mL) was added TFA (3.85 g, 33.77 mmol, 2.5 mL, 162.36 eq). The mixture was stirred at 20° C. for 1 h. Upon completion, the reaction mixture was poured into $NaHCO_3$ (25 mL) at 25° C., and then extracted with DCM (20 mL*3). The combined organic layers were washed with brine (20 mL*2), dried over $Na_2SO_4$, filtered and concentrated to give (2R,4S)-4-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide (115.2 mg, crude) as a yellow solid. MS (ESI) m/z 612.2 $[M+H]^+$ Isomer 2: To a solution of tert-butyl (2R,4S)-4-cyano-2-[[2-[(4,4-difluorocyclohexyl)amino]-1-(5-fluoro-3-pyridyl)-2-oxo-ethyl]-[4-(pentafluoro-$\lambda^6$-sulfanyl)phenyl]carbamoyl]pyrrolidine-1-carboxylate (150 mg, 210.77 umol, 1 eq) in DCM (5 mL) was added TFA (3.85 g, 33.77 mmol, 2.5 mL, 160.20 eq). The mixture was stirred at 20° C. for 1 h. Upon completion, the reaction mixture was poured into $NaHCO_3$ (25 mL) at 25° C., and then extracted with DCM (20 mL*3). The combined organic layers were washed with brine (20 mL*2), dried over $Na_2SO_4$, filtered and concentrated to give (2R,4S)-4-cyano-N-[2-[(4,4-difluorocyclohexyl)amino]-1-(5-fluoro-3-pyridyl)-2-oxo-ethyl]-N-[4-(pentafluoro-_A-sulfanyl)phenyl]pyrrolidine-2-carboxamide (126.2 mg, crude) as a yellow solid. MS (ESI) m/z 612.2 $[M+H]^+$ Step 3: (2S,3R)-1-cyano-N-[2-[(4,4-difluorocyclohexyl)amino]-1-(5-fluoro-3-pyridyl)-2-oxo-ethyl]-3-fluoro-N-[4-(pentafluoro-λ6-sulfanyl)phenyl]pyrrolidine-2-carboxamide Isomer 1: To a solution of (2R,4S)-4-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide (115.2 mg, 188.37 umol, 1 eq) and $NaHCO_3$ (47.47 mg, 565.12 umol, 21.98 uL, 3 eq) in DMF (3 mL), was added BrCN (25.9 mg, 244.52 umol, 17.99 uL, 1.3 eq) in DMF (0.5 mL) at 0° C. The mixture was stirred at 0° C. for 1 h. Upon completion, the reaction mixture was quenched by addition $H_2O$ (25 mL) at 20° C., and then extracted with EtOAc (25 mL*3). The combined organic layers were washed with brine (25 mL*2), dried over $Na_2SO_4$, filtered and concentrated to give a residue. The residue was purified by prep-HPLC (column: Phenomenex Luna C18 75*30 mm*3 um; mobile phase: [water (0.2% FA)-ACN]; B %: 30%-70%, 8 min) to give (2R,4S)-1,4-dicyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide (57 mg, 84.58 umol, 44.90% yield, 94.46% purity) as a white solid. MS (ESI) m/z 637.2 $[M+H]^+$ $^1H$ NMR (400 MHz, METHANOL-$d_4$) 5=8.31 (d, J=2.8 Hz, 1H), 8.20 (s, 1H), 8.05-7.02 (m, 5H), 6.26-6.15 (m, 1H), 4.37 (d, J=4.4, 8.4 Hz, 1H), 3.91 (d, J=7.8, 9.4 Hz, 2H), 3.70 (d, J=6.4, 9.4 Hz, 1H), 3.51 (q, J=7.4 Hz, 1H), 2.54-2.43 (m, 1H), 2.21 (d, J=8.4, 13.4 Hz, 1H), 2.12-1.78 (m, 6H), 1.68-1.57 (m, 1H), 1.51-1.39 (m, 1H)

Isomer 2: To a solution of (2R,4S)-4-cyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide (116.2 mg, 190.01 umol, 1 eq), $NaHCO_3$ (47.89 mg, 570.03 umol, 22.17 uL, 3 eq) in DMF (3 mL), was added BrCN (26.2 mg, 247.35 umol, 18.19 uL, 1.3 eq) in DMF (0.5 mL) at 0° C. The mixture was stirred at 0° C. for 1 h. Upon completion, the reaction mixture was quenched by addition $H_2O$ (25 mL) at 20° C., and then extracted with EtOAc (25 mL*3). The combined organic layers were washed with brine (25 mL*2), dried over $Na_2SO_4$, filtered and concentrated to give a residue. The residue was purified by prep-HPLC (column: Phenomenex Luna C18 75*30 mm*3 um; mobile phase: [water (0.2% FA)-ACN]; B %: 30%-70%, 8 min), to give (2R,4S)-1,4-dicyano-N-[2-[(4,4-difluorocyclohexyl)amino]-1-(5-fluoro-3-pyridyl)-2-oxo-ethyl]-N-[4-(pentafluoro-$\lambda^6$-sulfanyl)phenyl]pyrrolidine-2-carboxamide (52.5 mg, 80.23 umol, 42.23% yield, 97.28% purity) as a white solid. MS (ESI) m/z 637.2 $[M+H]^+$ $^1H$ NMR (400 MHz, METHANOL-$d_4$) δ=8.35 (d, J=2.8 Hz, 1H), 8.24 (s, 1H), 8.15-7.30 (m, 5H), 6.08 (s, 1H), 4.32 (d, J=3.8, 8.4 Hz, 1H), 3.95-3.82 (m, 2H), 3.73-3.64 (m, 11H), 3.56 (q, J=7.4 Hz, 1H), 2.51 (d, J=3.8, 7.4, 13.4 Hz, 11H), 2.30-2.17 (m, 11H), 2.11-1.78 (m, 7H), 1.68-1.57 (m, 1H), 1.49-1.39 (m, 1H)

Example 213: Synthesis of Compound 1148d

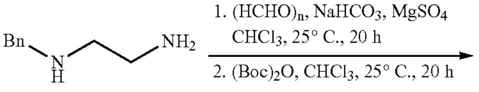

-continued

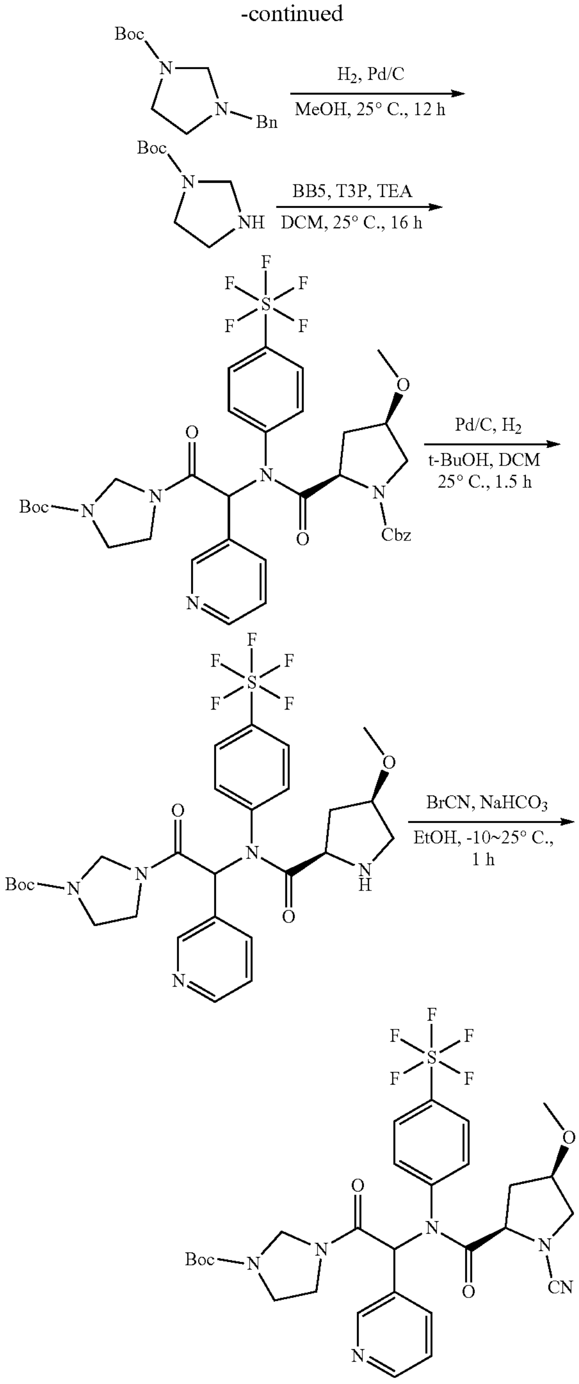

Step 1: tert-butyl 3-benzylimidazolidine-1-carboxylate

A mixture of formaldehyde (399.65 mg, 13.31 mmol, 366.65 uL, 1 eq) MgSO4 (6.41 g, 53.24 mmol, 4 eq), $NaHCO_3$ (3.69 g, 43.92 mmol, 1.71 mL, 3.3 eq) and N'-benzylethane-1,2-diamine (2 g, 13.31 mmol, 2.00 mL, 1 eq) in $CHCl_3$ (30 mL) under $N_2$ was stirred at 25° C. for 20 h. Boc2O (2.90 g, 13.31 mmol, 3.06 mL, 1 eq) was added and stirred for 20 h. Upon completion, the reaction mixture was quenched by addition $H_2O$ (150 mL), and extracted with DCM (50 mL*3). The combined organic layers were washed with brine (50 mL*2), dried over $Na_2SO_4$, filtered and concentrated under reduced pressure to give a residue. The residue was purified by column chromatography ($SiO_2$, petroleum ether/ethyl acetate=1/0 to 1/1) to give tert-butyl 3-benzylimidazolidine-1-carboxylate (2.8 g, 9.61 mmol, 72.17% yield, 90% purity) as a yellow oil. MS (ESI) m/z 263.2 $[M+1]^+$.

Step 2: tert-butyl imidazolidine-1-carboxylate

To a solution of tert-butyl 3-benzylimidazolidine-1-carboxylate (1.35 g, 5.15 mmol, 1 eq) in MeOH (2 mL) was added Pd/C (2 g, 10% purity) under Ar. The suspension was degassed under vacuum and purged with $H_2$ (10.37 mg, 5.15 mmol, 1 eq) several times. The mixture was stirred under $H_2$ (10.37 mg, 5.15 mmol, 1 eq) (15 psi) at 25° C. for 12 h. Upon completion, the reaction mixture was filtered and the filter was concentrated to give tert-butyl imidazolidine-1-carboxylate (600 mg, crude) as a yellow oil.

Step 3: tert-butyl 3-[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl] imidazolidine-1-carboxylate To a solution of 2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetic acid (350 mg, 568.58 umol, 1 eq) and tert-butyl imidazolidine-1-carboxylate (195.85 mg, 1.14 mmol, 2 eq) in DCM (3 mL) was added T3P (1.09 g, 1.71 mmol, 1.01 mL, 50% purity, 3 eq) and TEA (517.81 mg, 5.12 mmol, 712.25 uL, 9 eq). The mixture was stirred at 25° C. for 24 h. Upon completion, the reaction mixture was quenched by addition $H_2O$ (60 mL) and extracted with DCM (30 mL*3). The combined organic layers were washed with brine (30 mL), dried over $Na_2SO_4$, filtered and concentrated under reduced pressure to give a residue. The residue was purified by prep-TLC ($SiO_2$, petroleum ether/ethyl acetate=0/1) to give tert-butyl 3-[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl] imidazolidine-1-carboxylate (160 mg, 195.38 umol, 34.36% yield, 94% purity) as a yellow oil. MS (ESI) m/z 770.2 $[M+H]^+$ Tert-butyl 3-[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl]imidazolidine-1-carboxylate (75 mg, 91.58 umol, 16.11% yield, 94% purity) was obtained as a yellow oil. MS (ESI) m/z 770.2 $[M+H]^+$ Step 4: tert-butyl 3-[2-[N-[(2R,4R)-4-methoxypyrrolidine-2-carbonyl]-4-(pentafluoro-λ6-sulfanyl) anilino]-2-(3-pyridyl)acetyl]imidazolidine-1-carboxylate Isomer 1: To a solution of tert-butyl 3-[2-[N-[(2R,4R)-1-benzyloxycarbonyl-4-methoxy-pyrrolidine-2-carbonyl]-4-(pentafluoro-46-sulfanyl)anilino]-2-(3-pyridyl)acetyl]imidazolidine-1-carboxylate (150 mg, 194.86 umol, 1 eq) in t-BuOH (1 mL) and DCM (0.2 mL) was added Pd/C (100 mg, 10% purity) under $N_2$. The suspension was degassed under vacuum and purged with $H_2$ (392.82 ug, 194.86 umol, 1 eq) several times. The mixture was stirred under $H_2$ (392.82 ug, 194.86 umol, 1 eq) (15 psi) at 25° C. for 1.5 h. Upon completion, the reaction mixture was filtered and concentrated under reduced pressure to give tert-butyl 3-[2-[N-[(2R,4R)-4-methoxypyrrolidine-2-carbonyl]-4-(pentafluoro-%6-sulfanyl)anilino]-2-(3-pyridyl)acetyl]imidazolidine-1-carboxylate (100 mg, crude) as a yellow oil. MS (ESI) m/z 636.2 [M+H]+

Isomer 2: To a solution of tert-butyl 3-[2-[N-[(2R,4R)-1-benzyloxycarbonyl-4-methoxy-pyrrolidine-2-carbonyl]-4-(pentafluoro-λ6-sulfanyl)anilino]-2-(3-pyridyl)acetyl]imidazolidine-1-carboxylate (75 mg, 97.43 umol, 1 eq) in t-BuOH (1 mL) and DCM (0.2 mL) was added Pd/C (80 mg, 10% purity) under $N_2$. The suspension was degassed under vacuum and purged with $H_2$ (196.41 ug, 97.43 umol, 1 eq) several times. The mixture was stirred under $H_2$ (196.41 ug, 97.43 umol, 1 eq) (15 psi) at 25° C. for 1.5 h. Upon completion, the reaction mixture was filtered and concentrated under reduced pressure to give tert-butyl 3-[2-[N-[(2R,4R)-4-methoxypyrrolidine-2-carbonyl]-4-(pentafluoro-λ6-sulfanyl)anilino]-2-(3-pyridyl)acetyl] imidazolidine-1-carboxylate (55 mg, crude) as a yellow oil. MS (ESI) m/z 636.2 [M+H]+

Step 5: tert-butyl 3-[2-[N-[(2R,4R)-1-cyano-4-methoxy-pyrrolidine-2-carbonyl]-4-(pentafluoro-26-sulfanyl)anilino]-2-(3-pyridyl)acetyl]imidazolidine-1-carboxylate Isomer 1: To a solution of tert-butyl 3-[2-[N-[(2R,4R)-4-methoxypyrrolidine-2-carbonyl]-4-(pentafluoro-λ6-sulfanyl)anilino]-2-(3-pyridyl)acetyl]imidazolidine-1-carboxylate (100 mg, 113.27 umol, 72% purity, 1 eq) and $NaHCO_3$ (28.55 mg, 339.81 umol, 13.22 uL, 3 eq) in EtOH (1 mL) was added a solution of BrCN (24.00 mg, 226.54 umol, 16.66 uL, 2 eq) in EtOH (0.5 mL) drop-wise at −10° C. under $N_2$. The reaction mixture was slowly warmed to 25° C. for 1 h. Upon completion, the reaction mixture was quenched by addition $H_2O$ (30 mL) and extracted with EA (15 mL*3). The combined organic layers were washed with brine (20 mL); dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 35%-65%, 10 min) to give tert-butyl 3-[2-[N-[(2R,4R)-1-cyano-4-methoxy-pyrrolidine-2-carbonyl]-4-(pentafluoro-λ6-sulfanyl)anilino]-2-(3-pyridyl) acetyl]imidazolidine-1-carboxylate (35 mg, 52.98 umol, 46.77% yield, 100% purity) as a yellow solid. MS (ESI) m/z 661.2 [M+H]+

$^1H$ NMR (400 MHz, MeOD-$d_4$) δ=8.42-8.36 (m, 2H), 8.12-7.45 (m, 4H), 7.27-6.86 (m, 2H), 6.55-6.42 (m, 1H), 5.11-4.85 (m, 1H), 4.79-4.41 (m, 1H), 4.27-4.25 (m, 1H), 4.12-3.95 (m, 1H), 3.92-3.90 (m, 1H), 3.76-3.47 (m, 4.5H), 3.30-3.18 (m, 3.5H), 2.08-1.99 (m, 2H), 1.48-1.42 (m, 9H).

$^1H$ NMR (400 MHz, DMSO-$d_6$) δ=8.40-8.36 (m, 2H), 7.78-7.76 (m, 2H), 7.51-7.50 (m, 3H), 7.19-7.15 (m, 1H), 6.49-6.35 (m, 1H), 5.11-4.56 (m, 1.6H), 4.38-4.12 (m, 1.3H), 3.87-3.67 (m, 2H), 3.59-3.30 (m, 5H), 3.19-3.09 (m, 3H), 2.04-2.01 (m, 1H), 1.80-1.76 (m, 1H), 1.42 (s, 9H).

Isomer 2: To a solution of tert-butyl 3-[2-[N-[(2R,4R)-4-methoxypyrrolidine-2-carbonyl]-4-(pentafluoro-λ6-sulfanyl)anilino]-2-(3-pyridyl)acetyl]imidazolidine-1-carboxylate (50 mg, 23.52 umol, 29.9% purity, 1 eq) and $NaHCO_3$ (5.93 mg, 70.56 umol, 2.74 uL, 3 eq) in EtOH (1 mL) was added a solution of BrCN (4.98 mg, 47.04 umol, 3.46 uL, 2 eq) in EtOH (0.5 mL) drop-wise at −10° C. under $N_2$. The reaction mixture was slowly warmed to 25° C. for 1 h. Upon completion, the reaction mixture was quenched by addition $H_2O$ (30 mL) and extracted with EA (15 mL*3). The combined organic layers were washed with brine (20 mL), dried over $Na_2SO_4$, filtered and concentrated under reduced pressure to give a residue. The residue was purified by prep-HPLC (column: Waters Xbridge BEH C18 100*25 mm*Sum; mobile phase: [water (10 mM $NH_4HCO_3$)-ACN]; B %: 35%-65%, 10 min) to give tert-butyl 3-[2-[N-[(2R, 4R)-1-cyano-4-methoxy-pyrrolidine-2-carbonyl]-4-(pentafluoro-λ6-sulfanyl)anilino]-2-(3-pyridyl)acetyl]imidazolidine-1-carboxylate (2.12 mg, 2.81 umol, 11.97% yield, 87.7% purity) as a yellow solid. MS (ESI) m/z 661.2 [M+H]+

$^1H$ NMR (400 MHz, MeOD-$d_4$) δ=8.42-8.36 (m, 2H), 8.19-7.43 (m, 4H), 7.41-6.77 (m, 2H), 6.44-6.26 (m, 1H), 5.13-4.95 (m, 1H), 4.73-4.41 (m, 1H), 4.29-4.13 (m, 1H), 4.11-3.99 (m, 1H), 3.92-3.81 (m, 1H), 3.61-3.49 (m, 4.5H), 3.30-3.29 (m, 3.5H), 2.25-1.97 (m, 2H), 1.47-1.43 (m, 9H).

$^1H$ NMR (400 MHz, DMSO-$d_6$) δ=8.42-8.38 (m, 2H), 7.77-7.75 (m, 2H), 7.48-7.42 (m, 3H), 7.20-7.17 (m, 1H), 6.37-6.36 (m, 1H), 5.03-4.54 (m, 2H), 4.34-4.06 (m, 11H), 4.02-3.78 (m, 2H), 3.66-3.43 (m, 4H), 3.32-3.30 (m, 1H), 3.20-3.12 (m, 3H), 2.19-2.09 (m, 1H), 1.85-1.82 (m, 1H), 1.41 (s, 9H).

Example 215: Synthesis of Compound 1175

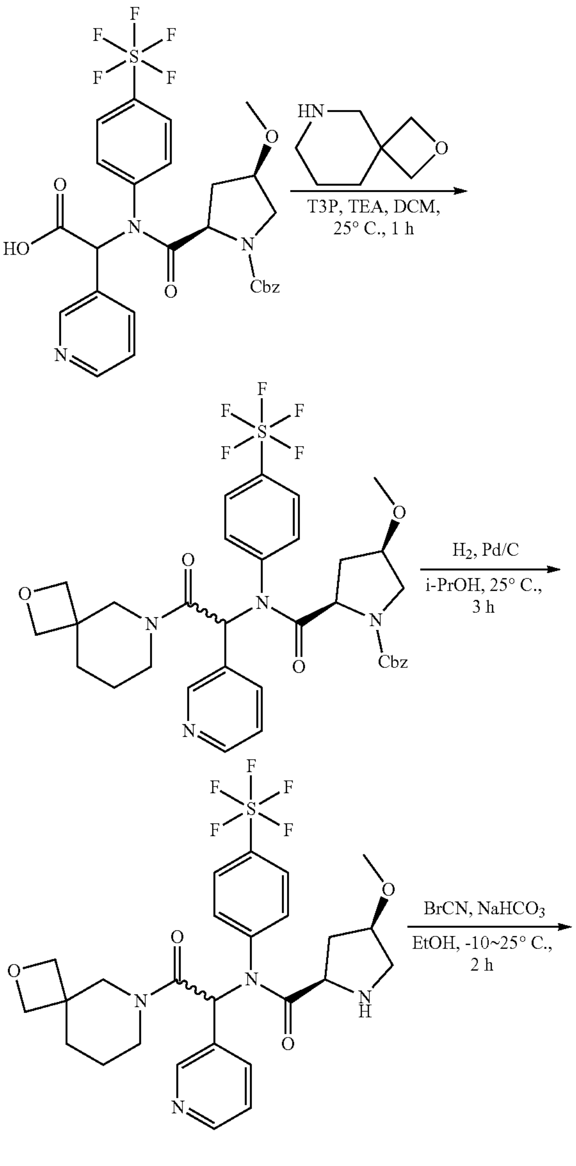

-continued

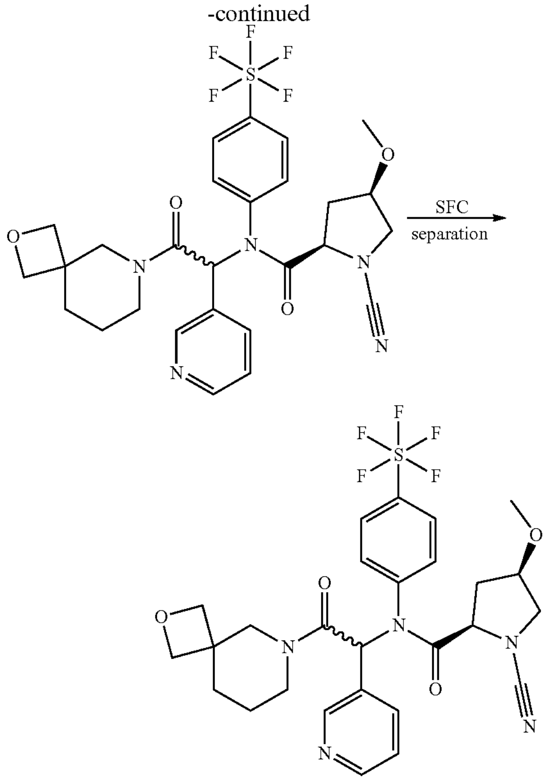

Step1: benzyl (2R,4R)-4-methoxy-2-[[2-(2-oxa-8-azaspiro[3.5]nonan-8-yl)-2-oxo-1-(3-pyridyl)ethyl]-[4-(pentafluoro-$\lambda^6$-sulfanyl)phenyl]carbamoyl]pyrrolidine-1-carboxylate A solution of 2-[N-[(2R,4R)-1-benzyloxycarbonyl-4-methoxy-pyrrolidine-2-carbonyl]-4-(pentafluoro-$\lambda^6$-sulfanyl)anilino]-2-(3-pyridyl)acetic acid (300 mg, 487.35 umol, 1 eq) in DCM (6 mL) was added 2-oxa-8-azaspiro[3.5] nonane (61.98 mg, 487.35 umol, 1 eq), T3P (403.17 mg, 633.56 umol, 376.80 uL, 50% purity, 1.3 eq), TEA (147.94 mg, 1.46 mmol, 203.50 uL, 3 eq) was stirred at 25° C. for 1 h. Upon completion, the mixture was quenched by addition $H_2O$ (50 mL) and then extracted with DCM (30 mL*3). The combined organic layers were washed with brine (50 mL), dried over $Na_2SO_4$, filtered and concentrated under reduced pressure and was purified by prep-TLC ($SiO_2$, DCM:MeOH=10:1) to give product benzyl (2R,4R)-4-methoxy-2-[[2-(2-oxa-8-azaspiro[3.5]nonan-8-yl)-2-oxo-1-(3-pyridyl)ethyl]-[4-(pentafluoro-λ6-sulfanyl)phenyl]carbamoyl]pyrrolidine-1-carboxylate (270 mg, 372.55 umol, 76.44% yield) as yellow oil. MS (ESI) m/z 725.2 $[M+H]^+$ Step2: (2R,4R)-4-methoxy-N-[2-oxo-2-[(2-oxo-2-pyrrolidin-1-yl-ethyl)amino]-1-(3-pyridyl)ethyl]-N-[4-(pentafluoro-$\lambda^6$-sulfanyl)phenyl]pyrrolidine-2-carboxamide To a solution of benzyl (2R,4R)-4-methoxy-2-[[2-(2-oxa-8-azaspiro[3.5]nonan-8-yl)-2-oxo-1-(3-pyridyl)ethyl]-[4-(pentafluoro-$\lambda^6$-sulfanyl)phenyl]carbamoyl]pyrrolidine-1-carboxylate (240 mg, 331.15 umol, 1 eq) in isopropanol (10 mL) was added Pd/C (30 mg, 331.15 umol, 10% purity, 1 eq) and the mixture was stirred at 25° C. for 3 h under $H_2$ (667.57 ug, 331.15 umol, 1 eq) at 15 Psi. Upon completion, the reaction was filtered and concentrated in vacuum to give crude product (2R,4R)-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (150 mg, crude) as yellow oil. MS (ESI) m/z 591.2 $[M+H]^+$ Step 3: (2R,4R)-1-cyano-4-methoxy-N-[2-oxo-2-[(2-oxo-2-pyrrolidin-1-yl-ethyl)amino]-1-(3-pyridyl)ethyl]-N-[4-(pentafluoro-2'-sulfanyl)phenyl]pyrrolidine-2-carboxamide To a solution of (2R,4R)-4-methoxy-N-[2-(2-oxa-8-azaspiro[3.5]nonan-8-yl)-2-oxo-1-(3-pyridyl)ethyl]-N-[4-(pentafluoro-λ6-sulfanyl)phenyl]pyrrolidine-2-carboxamide (140 mg, 237.05 umol, 1 eq) in EtOH (5 mL) was added $NaHCO_3$ (59.74 mg, 711.14 umol, 27.66 uL, 3 eq) and the mixture was cooled at −10° C. After adding BrCN (27.62 mg, 260.75 umol, 19.18 uL, 1.1 eq) in EtOH (0.5 mL), the mixture was warmed to 25° C. and stirred for 2 h. Upon completion, the mixture was quenched by addition $H_2O$ (50 mL) and then extracted with DCM (30 mL*3). The combined organic layers were washed with brine (50 mL), dried over $Na_2SO_4$, filtered and concentrated under reduced pressure and was purified by prep-TLC ($SiO_2$, DCM:MeOH=10:1) to give product (2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (60 mg, 70.38 umol, 29.69% yield, 72.21% purity). MS (ESI) m/z 616.2 $[M+H]^+$ Step4: (2R,4R)-1-cyano-4-methoxy-N-[2-oxo-2-[(2-oxo-2-pyrrolidin-1-yl-ethyl)amino]-1-(3-pyridyl)ethyl]-N-[4-(pentafluoro-$\lambda^6$-sulfanyl)phenyl]pyrrolidine-2-carboxamide (2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide was separated by SFC (column: REGIS(S,S) WHELK-O1 (250 mm*25 mm, 10 um); mobile phase: [Neu-MeOH]; B %: 40%-40%, 15 min) to afford (2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-$?^6$-sulfanyl)phenyl]pyrrolidine-2-carboxamide (20 mg, 30.86 umol, 31.67% yield, 95% purity) MS (ESI) m/z 616.2 $[M+H]^+$ $^1H$ NMR (400 MHz, MeOD-$d_4$) δ=8.45-8.25 (m, 2H), 8.19-7.50 (m, 4H), 7.34-6.96 (m, 2H), 6.95-6.68 (m, 1H), 4.51-4.28 (m, 3H), 4.25-4.16 (m, 2H), 3.93-3.86 (m, 1H), 3.72-3.61 (m, 2H), 3.56-3.43 (m, 2H), 3.30-3.28 (m, 3H), 3.22-3.10 (m, 1H), 2.15-1.92 (m, 3H), 1.83-1.73 (m, 1H), 1.69-1.65 (m, 1H), 1.59-1.34 (m, 1H), 1.29-1.12 (m, 1H).

(2R,4R)-1-cyano-4-methoxy-N-[2-(2-oxa-8-azaspiro[3.5]nonan-8-yl)-2-oxo-1-(3-pyridyl)ethyl]-N-[4-(pentafluoro-$\lambda^6$-sulfanyl)phenyl]pyrrolidine-2-carboxamide (6 mg, 8.67 umol, 8.90% yield, 89% purity) was obtained as yellow solid. MS (ESI) m/z 616.2 $[M+H]^+$ $^1H$ NMR (400 MHz, MeOD-$d_4$) δ=8.50-8.32 (m, 2H), 8.30-7.44 (m, 4H), 7.42-6.82 (m, 2H), 6.80-6.56 (m, 1H), 4.55-4.32 (m, 2H), 4.29-4.04 (m, 3H), 3.95-3.87 (m, 1H), 3.74-3.60 (m, 2H), 3.60-3.46 (m, 2H), 3.30-3.28 (m, 3H), 3.23-3.16 (m, 1H), 2.18-2.06 (m, 1H), 2.00-1.88 (m, 2H), 1.84-1.73 (m, 1H), 1.70-1.59 (m, 1H), 1.31-1.27 (m, 1H), 1.18-0.97 (m, 1H).

Example 216: Synthesis of Compound 1328

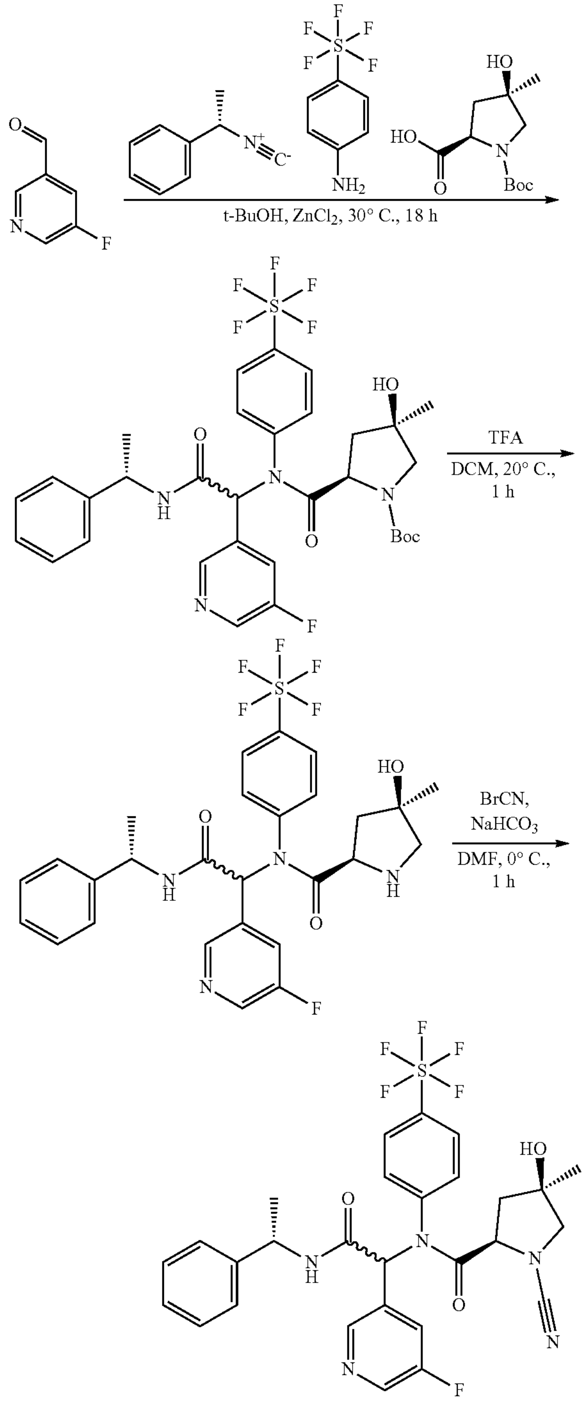

Step 1: tert-butyl(2R,4R)-2-[[1-(5-fluoro-3-pyridyl)-2-oxo-2-[[(1S)-1-phenylethyl]amino]ethyl]-[4-(pentafluoro-$\lambda^6$-sulfanyl)phenyl]carbamoyl]-4-hydroxy-4-methyl-pyrrolidine-1-carboxylate A solution of 4-(pentafluoro-$\lambda^6$-sulfanyl) aniline (300 mg, 1.37 mmol, 1 eq) and 5-fluoronicotinaldehyde (171.23 mg, 1.37 mmol, 1 eq) in t-BuOH (8 mL) was stirred at 30° C. for 2 h, and then (2R,4R)-1-tert-butoxycarbonyl-4-hydroxy-4-methyl-pyrrolidine-2-carboxylic acid (335.72 mg, 1.37 mmol, 1 eq) was added to the mixture. Then, [(1S)-1-isocyanoethyl]benzene (179.55 mg, 1.37 mmol, 1 eq) was added in portions, followed by the addition of $ZnCl_2$ (1 M, 4.11 mL, 3 eq). The mixture was stirred at 30° C. for 16 h. Upon completion of reaction, the mixture was concentrated in vacuum and was purified by prep-HPLC (column: Waters Xbridge C18 150*50 mm*10 um; mobile phase: [water (10 mM $NH_4HCO_3$)-ACN]; B %: 55%-75%, 10 min) to obtain tert-butyl(2R,4R)-2-[[1-(5-fluoro-3-pyridyl)-2-oxo-2-[[(1S)-1-phenylethyl]amino]ethyl]-[4-(pentafluoro-$\lambda^6$-sulfanyl)phenyl]carbamoyl]-4-hydroxy-4-methyl-pyrrolidine-1-carboxylate Isomer 1 (130 mg, 166.50 umol, 12.16% yield, 90% purity) as a light yellow solid. MS (ESI) m/z 703.4 $[M+H]^+$.

Tert-butyl (2R,4R)-2-[[1-(5-fluoro-3-pyridyl)-2-oxo-2-[[(1S)-1-phenylethyl]amino]ethyl]-[4-(pentafluoro-$\lambda^6$-sulfanyl)phenyl]carbamoyl]-4-hydroxy-4-methyl-pyrrolidine-1-carboxylate Isomer 2 (150 mg, 192.11 umol, 14.04% yield, 90% purity) was obtained as a light yellow solid. MS (ESI) m/z 703.4 $[M+H]^+$.

Step 2: (2R,4R)—N-[1-(5-fluoro-3-pyridyl)-2-oxo-2-[[(1S)-1-phenylethyl]amino]ethyl]-4-hydroxy-4-methyl-N-[4-(pentafluoro-26-sulfanyl)phenyl]pyrrolidine-2-carboxamide Isomer 1

A solution of tert-butyl (2R,4R)-2-[[1-(5-fluoro-3-pyridyl)-2-oxo-2-[[(1S)-1-phenylethyl]amino]ethyl]-[4-(pentafluoro-$\lambda^6$-sulfanyl)phenyl]carbamoyl]-4-hydroxy-4-methyl-pyrrolidine-1-carboxylate Isomer 1 (130 mg, 185.00 umol, 1 eq) in DCM (1 mL) and TFA (0.3 mL) was stirred at 20° C. for 1 h. Upon the reaction completion, the mixture was concentrated in vacuum to obtain (2R,4R)—N-[1-(5-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 1 (110 mg, crude, HCl) as a yellow gum. MS (ESI) m/z 603.2 $[M+H]^+$.

(2R,4R)—N-[1-(S-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 2

A solution of tert-butyl (2R,4R)-2-[[1-(5-fluoro-3-pyridyl)-2-oxo-2-[[(1S)-1-phenylethyl]amino]ethyl]-[4-(pentafluoro-$\lambda^6$-sulfanyl)phenyl]carbamoyl]-4-hydroxy-4-methyl-pyrrolidine-1-carboxylate Isomer 2 (150.00 mg, 213.46 umol, 1 eq) in DCM (1 mL) and TFA (0.3 mL) was stirred at 20° C. for 1 h. Upon the reaction completion, the mixture was concentrated in vacuum to obtain (2R, 4R)—N-[1-(5-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl) phenyl]pyrrolidine-2-carboxamide Isomer 2 (130 mg, crude, HC) as a yellow gum. MS (ESI) m/z 603.2 $[M+H]^+$.

Step 3: (2R,4R)-1-cyano-N-[1-(S-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 1

To a solution of (2R,4R)—N-[1-(5-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 1 (110 mg, 182.55 umol, 1 eq) in DMF (1.5 mL) was added $NaHCO_3$ (46.01 mg, 547.64 umol, 21.30 uL, 3 eq), and then the mixture was cooled to 0° C. After adding BrCN (48.34 mg, 456.36 umol, 33.57 uL, 2.5 eq) at 0° C., the mixture was stirred at 0° C. for 1 h. Upon the reaction completion, the mixture was quenched by addition $H_2O$ (1 mL) and was dried by blowing $N_2$ and was purified by prep-HPLC (column: Waters Xbridge BEH C18 100*25 mm*5 um; mobile phase: [water (10 mM $NH_4HCO_3$)-ACN]; B %: 35%-65%, 10 min) to obtained (2R,4R)-1-cyano-N-[1-(5-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 1 (10 mg, 15.93 umol, 8.73% yield, 88.9% purity) as a white solid. MS (ESI) m/z 628.2 $[M+H]^+$.

$^1$H NMR (400 MHz, MeOD-$d_4$) δ ppm 8.37-8.23 (m, 2H), 7.76 (s, 2H), 7.52-6.64 (m, 8H), 6.38 (s, 1H), 5.08 (q, J=7.0 Hz, 1H), 4.24 (dd, J=4.6, 9.2 Hz, 1H), 3.49 (d, J=9.2 Hz, 1H), 3.34 (s, 1H), 2.02 (dd, J=4.6, 13.2 Hz, 1H), 1.92-1.82 (m, 1H), 1.38 (d, J=7.0 Hz, 3H), 1.23 (s, 3H).

(2R,4R)-1-cyano-N-[1-(S-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 2

To a solution of (2R,4R)—N-[1-(5-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 2 (130 mg, 215.74 umol, 1 eq) in DMF (1.5 mL) was added $NaHCO_3$ (54.37 mg, 647.21 umol, 25.17 uL, 3 eq), and then the mixture was cooled to 0° C. After adding BrCN (57.13 mg, 539.34 umol, 39.67 uL, 2.5 eq) at 0° C., the mixture was stirred at 0° C. for 1 h. Upon the reaction completion, the mixture was quenched by addition $H_2O$ (1 mL) and was dried by blowing $N_2$ and was purified by prep-HPLC (column: Waters Xbridge BEH C18 100*25 mm*5 um; mobile phase: [water (10 mM $NH_4HCO_3$)-ACN]; B %: 35%-65%, 10 min) to obtained (2R,4R)-1-cyano-N-[1-(5-fluoro-3-pyridyl)-2-oxo-2-[[(1S)-1-phenylethyl]amino]ethyl]-4-hydroxy-4-methyl-N-[4-(pentafluoro-$\lambda^6$-sulfanyl)phenyl]pyrrolidine-2-carboxamide Isomer 2 (40 mg, 63.73 umol, 29.54% yield, 95.8% purity) as a white solid. MS (ESI) m/z 628.2 $[M+H]^+$.

$^1$H NMR (400 MHz, MeOD-$d_4$) δ ppm 8.31 (d, J=2.4 Hz, 1H), 8.13 (s, 1H), 7.75 (s, 2H), 7.57-6.64 (m, 8H), 6.21 (s, 1H), 5.05 (q, J=7.0 Hz, 1H), 4.27 (dd, J=3.8, 9.2 Hz, 1H), 3.51 (d, J=9.2 Hz, 1H), 3.38-3.33 (m, 1H), 2.10-1.89 (m, 2H), 1.47 (d, J=7.0 Hz, 3H), 1.26 (s, 3H).

Example 217: Synthesis of Compound 1330

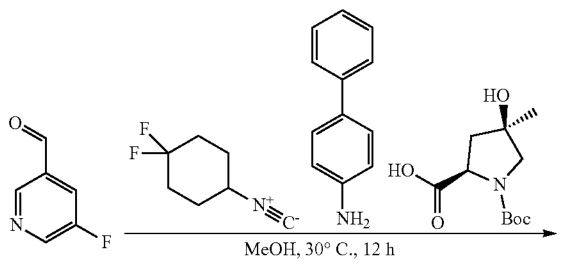

-continued

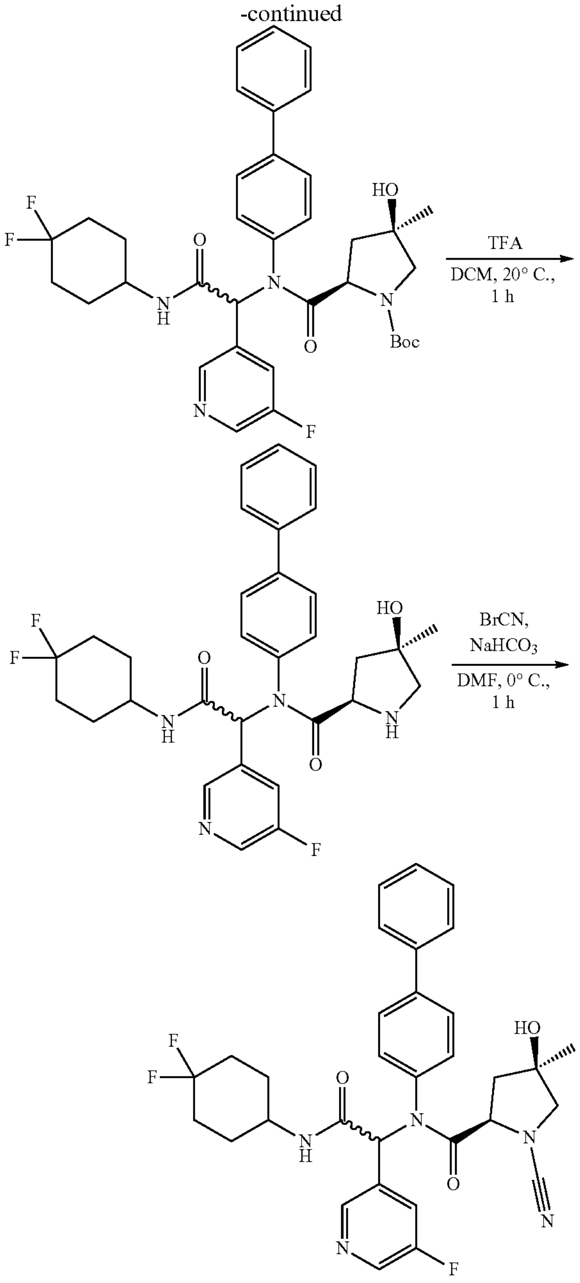

(2R,4R)-tert-butyl2-([1,1'-biphenyl]-4-yl(2-((4,4-difluorocyclohexyl)amino)-1-(S-fluoropyridin-3-yl)-2-oxoethyl)carbamoyl)-4-hydroxy-4-methylpyrrolidine-1-carboxylate A solution of 4-phenylaniline (300 mg, 1.77 mmol, 1 eq) and 5-fluoropyridine-3-carbaldehyde (221.78 mg, 1.77 mmol, 1 eq) in MeOH (10 mL) was stirred at 30° C. for 16 h, and then (2R,4R)-1-tert-butoxycarbonyl-4-hydroxy-4-methyl-pyrrolidine-2-carboxylic acid (434.82 mg, 1.77 mmol, 1 eq) was added to the mixture. After adding 1,1-difluoro-4-isocyano-cyclohexane (257.32 mg, 1.77 mmol, 1 eq) in portions, the mixture was stirred at 30° C. for 16 h. Upon completion, the mixture was concentrated in vacuum and was purified by prep-HPLC (column: Waters Xbridge C18 150*50 mm*10 um; mobile phase: [water (10 mM $NH_4HCO_3$)-ACN]; B %: 55%-75%, 10 min) to obtain (2R,4R)-tert-butyl 2-([1,1'-biphenyl]-4-yl (2-((4,4-difluorocyclohexyl) amino)-1-(5-fluoropyridin-3-yl)-2-oxoethyl) carbamoyl)-4-hydroxy-4-methylpyrrolidine-1-carboxylate Isomer 1 (300 mg, 404.96 umol, 22.84% yield, 90% purity) as a yellow gum. MS (ESI) m/z 667.4 $[M+H]^+$.

(2R,4R)-tert-butyl 2-([1,1'-biphenyl]-4-yl (2-((4,4-difluorocyclohexyl)amino)-1-(5-fluoropyridin-3-yl)-2-oxoethyl) carbamoyl)-4-hydroxy-4-methylpyrrolidine-1-carboxylate Isomer 2 (300 mg, 404.96 umol, 22.84% yield, 90% purity) was obtained as a yellow gum. MS (ESI) m/z 667.4 $[M+H]^+$.

Step 2: (2R,4R)—N-([1,1'-biphenyl]-4-yl)-N-(2-((4,4-difluorocyclohexyl)amino)-1-(5-fluoropyridin-3-yl)-2-oxoethyl)-4-hydroxy-4-methylpyrrolidine-2-carboxamide Isomer 1

A solution of (2R,4R)-tert-butyl 2-([1,1'-biphenyl]-4-yl (2-((4,4-difluorocyclohexyl) amino)-1-(5-fluoropyridin-3-yl)-2-oxoethyl)carbamoyl)-4-hydroxy-4-methylpyrrolidine-1-carboxylate Isomer 1 (300.00 mg, 449.96 umol, 1 eq) in DCM (3 mL) and TFA (1 mL) was stirred at 25° C. for 1 h. Upon completion of reaction, the mixture was concentrated in vacuum to obtain (2R, 4R)—N-([1,1'-biphenyl]-4-yl)-N-(2-((4,4-difluorocyclohexyl)amino)-1-(5-fluoropyridin-3-yl)-2-oxoethyl)-4-hydroxy-4-methylpyrrolidine-2-carboxamide Isomer 1 (250 mg, crude, HCl) as a yellow gum.

(2R,4R)—N-([1,1'-biphenyl]-4-yl)-N-(2-((4,4-difluorocyclohexyl)amino)-1-(5-fluoropyridin-3-yl)-2-oxoethyl)-4-hydroxy-4-methylpyrrolidine-2-carboxamide Isomer 2

A solution of (2R,4R)-tert-butyl 2-([1,1'-biphenyl]-4-yl (2-((4,4-difluorocyclohexyl) amino)-1-(5-fluoropyridin-3-yl)-2-oxoethyl)carbamoyl)-4-hydroxy-4-methylpyrrolidine-1-carboxylate Isomer 2 (300.00 mg, 449.96 umol, 1 eq) in DCM (3 mL) and TFA (1 mL) was stirred at 25° C. for 1 h. Upon completion of reaction, the mixture was concentrated in vacuum to obtained (2R, 4R)—N-([1,1'-biphenyl]-4-yl)-N-(2-((4,4-difluorocyclohexyl)amino)-1-(5-fluoropyridin-3-yl)-2-oxoethyl)-4-hydroxy-4-methylpyrrolidine-2-carboxamide Isomer 2 (250 mg, crude, HCl) as a yellow gum.

Step 3: (2R,4R)—N-([1,1'-biphenyl]-4-yl)-1-cyano-N-(2-((4,4-difluorocyclohexyl)amino)-1-(5-fluoropyridin-3-yl)-2-oxoethyl)-4-hydroxy-4-methylpyrrolidine-2-carboxamide Isomer 1

To a solution of (2R, 4R)—N-([1,1'-biphenyl]-4-yl)-N-(2-((4,4-difluorocyclohexyl)amino)-1-(5-fluoropyridin-3-yl)-2-oxoethyl)-4-hydroxy-4-methylpyrrolidine-2-carboxamide Isomer 1 (250 mg, 441.22 umol, 1 eq) in DMF (2 mL) was added $NaHCO_3$ (111.20 mg, 1.32 mmol, 51.48 uL, 3 eq), and then the mixture was cooled to 0° C. After adding BrCN (116.84 mg, 1.10 mmol, 81.14 uL, 2.5 eq) at 0° C., the mixture was stirred at 0° C. for 1 h. Upon completion of reaction, the mixture was quenched by addition $H_2O$ (1 mL) and was dried by blowing $N_2$ and was purified by prep-HPLC (column: Waters Xbridge BEH C18 100*25 mm*5 um; mobile phase: [water (10 mM $NH_4HCO_3$)-ACN]; B %: 40%-65%, 10 min) to obtained (2R,4R)—N-([1,1'-biphenyl]-4-yl)-1-cyano-N-(2-((4,4-difluorocyclohexyl)amino)-1-(5-fluoropyridin-3-yl)-2-oxoethyl)-4-hydroxy-4-methylpyrrolidine-2-carboxamide Isomer 1 (10 mg, 16.36 umol, 3.71% yield, 96.8% purity) as a white solid. MS (ESI) m/z 592.2 $[M+H]^+$.

$^1H$ NMR (400 MHz, MeOD-$d_4$) δ ppm 8.36-8.19 (m, 2H), 7.95-7.30 (m, 9H), 6.90 (s, 11H), 6.23 (s, 1H), 4.33 (dd, J=4.6, 9.2 Hz, 1H), 3.91 (t, J=10.4 Hz, 1H), 3.51 (d, J=9.2 Hz, 1H), 3.35 (d, J=9.2 Hz, 1H), 2.17-1.79 (m, 8H), 1.74-1.59 (m, 1H), 1.55-1.41 (m, 1H), 1.25 (s, 3H).

(2R,4R)—N-([1,1'-biphenyl]-4-yl)-1-cyano-N-(2-((4,4-difluorocyclohexyl)amino)-1-(5-fluoropyridin-3-yl)-2-oxoethyl)-4-hydroxy-4-methylpyrrolidine-2-carboxamide Isomer 2

To a solution of (2R, 4R)—N-([1,1'-biphenyl]-4-yl)-N-(2-((4,4-difluorocyclohexyl)amino)-1-(5-fluoropyridin-3-yl)-2-oxoethyl)-4-hydroxy-4-methylpyrrolidine-2-carboxamide Isomer 2 (250 mg, 441.22 umol, 1 eq) in DMF (2 mL) was added $NaHCO_3$ (111.20 mg, 1.32 mmol, 51.48 uL, 3 eq), and then the mixture was cooled to 0° C. After adding BrCN (116.84 mg, 1.10 mmol, 81.14 uL, 2.5 eq) at 0° C., the mixture was stirred at 0° C. for 1 h. Upon completion of reaction, the mixture was quenched by addition $H_2O$ (1 mL), dried with using $N_2$ and was purified by prep-HPLC (column: Waters Xbridge BEH C18 100*25 mm*Sum; mobile phase: [water (10 mM $NH_4HCO_3$)-ACN]; B %: 40%-65%, 10 min) to obtained (2R,4R)—N-([1,1'-biphenyl]-4-yl)-1-cyano-N-(2-((4,4-difluorocyclohexyl)amino)-1-(5-fluoropyridin-3-yl)-2-oxoethyl)-4-hydroxy-4-methylpyrrolidine-2-carboxamide Isomer 1 (50 mg, 83.16 umol, 20.06% yield, 98.4% purity) as a white solid. MS (ESI) m/z 592.2 $[M+H]^+$.

$^1H$ NMR (400 MHz, MeOD-$d_4$) δ ppm 8.35-8.23 (m, 2H), 8.11-7.23 (m, 9H), 6.84 (s, 1H), 6.10 (s, 1H), 4.40-4.29 (m, 1H), 3.88 (t, J=10.2 Hz, 1H), 3.51 (d, J=9.2 Hz, 1H), 3.35 (d, J=9.4 Hz, 11H), 2.16-1.77 (m, 8H), 1.71-1.59 (m, 1H), 1.53-1.40 (m, 1H), 1.25 (s, 3H).

Example 218: Synthesis of Compound 1345

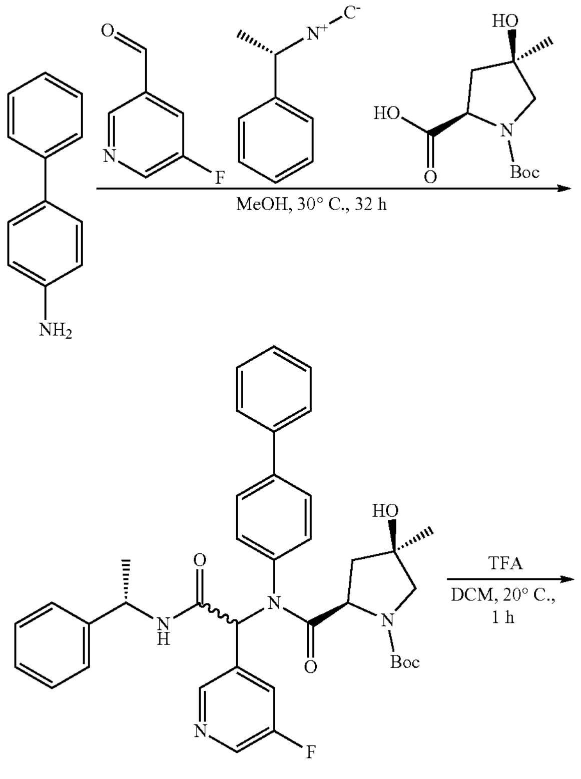

-continued

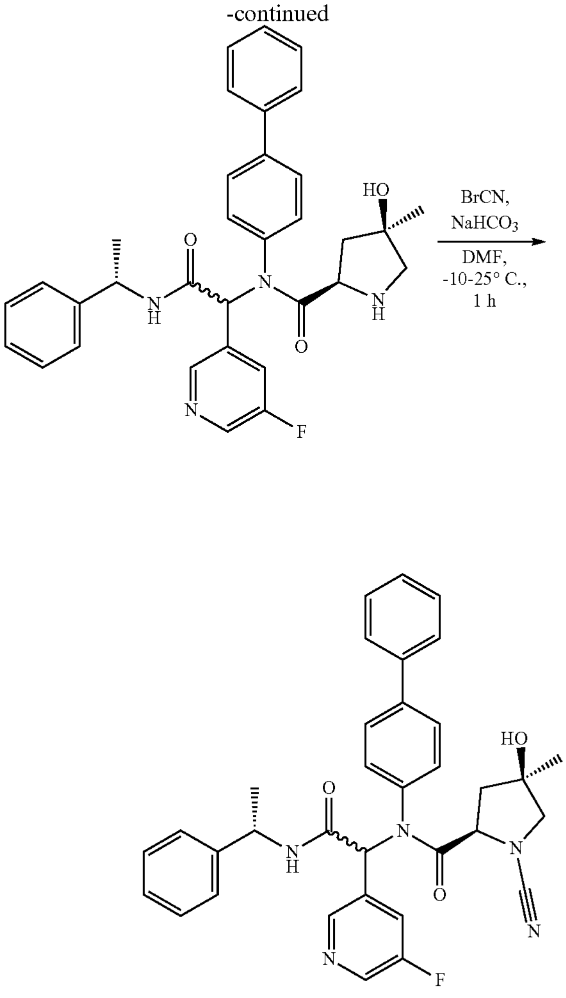

Step 1: (2R,4R)-tert-butyl2-([1,1'-biphenyl]-4-yl(1-(5-fluoropyridin-3-yl)-2-oxo-2-(((S)-1-phenylethyl)amino)ethyl)carbamoyl)-4-hydroxy-4-methylpyrrolidine-1-carboxylate 5-Fluoropyridine-3-carbaldehyde (221.78 mg, 1.77 mmol, 1 eq) and 4-phenylaniline (300 mg, 1.77 mmol, 1 eq) in MeOH (10 mL) was stirred at 30° C. for 16 h, and then was added (2R,4R)-1-tert-butoxycarbonyl-4-hydroxy-4-methyl-pyrrolidine-2-carboxylic acid (434.82 mg, 1.77 mmol, 1 eq) and a solution of [(1S)-1-isocyanoethyl]benzene (232.55 mg, 1.77 mmol, 1 eq) in MeOH (3 mL). The mixture was stirred at 30° C. for 16 h. Upon completion, the mixture was concentrated under the reduced pressure to give a residue. The residue was purified by prep-HPLC (column: Welch Xtimate C18 250*70 mm #10 um; mobile phase: [water (10 mM $NH_4HCO_3$)-ACN]; B %: 60%-90%, 20 min) to give tert-butyl(2R,4R)-2-[[1-(5-fluoro-3-pyridyl)-2-oxo-2-[[(1S)-1-phenylethyl]amino]ethyl]-(4-phenylphenyl)carbamoyl]-4-hydroxy-4-methyl-pyrrolidine-1-carboxylate Isomer 1 (360 mg, 551.51 umol, 31.11% yield) as a yellow solid. MS (ESI) m/z 653.3 $[M+H]^+$ Tert-butyl(2R,4R)-2-[[1-(5-fluoro-3-pyridyl)-2-oxo-2-[[(1S)-1-phenylethyl]amino]ethyl]-(4-phenylphenyl)carbamoyl]-4-hydroxy-4-methyl-pyrrolidine-1-carboxylate Isomer 2 (360 mg, 551.51 umol, 31.11% yield) was obtained as a yellow solid. MS (ESI) m/z 653.3 $[M+H]^+$.

Step 2: (2R,4R)—N-([1,1'-biphenyl]-4-yl)-N-(1-(S-fluoropyridin-3-yl)-2-oxo-2-(((S)-1-phenylethyl)amino)ethyl)-4-hydroxy-4-methylpyrrolidine-2-carboxamide Isomer 1

To a solution of tert-butyl (2R,4R)-2-[[1-(5-fluoro-3-pyridyl)-2-oxo-2-[[(1S)-1-phenylethyl]amino]ethyl]-(4-phenylphenyl)carbamoyl]-4-hydroxy-4-methyl-pyrrolidine-1-carboxylate (350 mg, 536.19 umol, 1 eq) in DCM (5 mL) was added TFA (3.08 g, 27.01 mmol, 2 mL, 50.38 eq). The mixture was stirred at 20° C. for 1 h. Upon completion, the reaction mixture was quenched by addition sat. $NaHCO_3$ (10 mL), and then extracted with DCM (10 mL*3). The combined organic layers were washed with brine (10 mL), dried over $Na_2SO_4$, filtered and concentrated under reduced pressure to give (2R,4R)—N-[1-(5-fluoro-3-pyridyl)-2-oxo-2-[[(1S)-1-phenylethyl]amino]ethyl]-4-hydroxy-4-methyl-N-(4-phenylphenyl)pyrrolidine-2-carboxamide Isomer 1 (320 mg, crude) as a yellow oil. MS (ESI) m/z 553.3 $[M+H]^+$ (2R,4R)—N-([1,1'-biphenyl]-4-yl)-N-(1-(5-fluoropyridin-3-yl)-2-oxo-2-(((S)-1-phenylethyl)amino)ethyl)-4-hydroxy-4-methylpyrrolidine-2-carboxamide Isomer 2

To a solution of tert-butyl(2R,4R)-2-[[1-(5-fluoro-3-pyridyl)-2-oxo-2-[[(1S)-1-phenylethyl]amino]ethyl]-(4-phenylphenyl)carbamoyl]-4-hydroxy-4-methyl-pyrrolidine-1-carboxylate (350 mg, 536.19 umol, 1 eq) in DCM (5 mL) was added TFA (3.08 g, 27.01 mmol, 2 mL, 50.38 eq). The mixture was stirred at 20° C. for 1 h. Upon completion, the reaction mixture was quenched by addition sat. $NaHCO_3$ (10 mL), and then extracted with DCM (10 mL*3). The combined organic layers were washed with brine (10 mL), dried over $Na_2SO_4$, filtered and concentrated under reduced pressure affording (2R,4R)—N-[1-(5-fluoro-3-pyridyl)-2-oxo-2-[[(1S)-1-phenylethyl]amino]ethyl]-4-hydroxy-4-methyl-N-(4-phenylphenyl)pyrrolidine-2-carboxamide Isomer 2 (320 mg, crude) as a yellow oil. MS (ESI) m/z 553.3 $[M+H]^+$ Step 3: (2R,4R)—N-([1,1'-biphenyl]-4-yl)-1-cyano-N-(1-(5-fluoropyridin-3-yl)-2-oxo-2-(((S)-1-phenylethyl)amino)ethyl)-4-hydroxy-4-methylpyrrolidine-2-carboxamide Isomer 1

To a solution of (2R,4R)—N-[1-(5-fluoro-3-pyridyl)-2-oxo-2-[[(1S)-1-phenylethyl]amino]ethyl]-4-hydroxy-4-methyl-N-(4-phenylphenyl)pyrrolidine-2-carboxamide (300 mg, 542.85 umol, 1 eq) in EtOH (3 mL) was added $NaHCO_3$ (136.81 mg, 1.63 mmol, 63.34 uL, 3 eq). The solution was cooled to −10° C., and then a solution of BrCN (86.25 mg, 814.28 umol, 59.89 uL, 1.5 eq) in EtOH (1 mL) was added. The solution was stirred for 1 h at 0° C. and warmed to 25° C. gradually. Upon completion, the mixture was quenched by addition $H_2O$ (30 mL) and then extracted with DCM (30 mL*3). The combined organic layers were washed with brine (30 mL), dried over $Na_2SO_4$, filtered and concentrated under reduced pressure to give a residue. The residue was purified by prep-HPLC (column: Waters Xbridge BEH C18 100*25 mm*5 um; mobile phase: [water (10 mM $NH_4HCO_3$)-ACN]; B %: 30%-60%, 10 min) affording (2R,4R)-1-cyano-N-[1-(5-fluoro-3-pyridyl)-2-oxo-2-[[(1S)-1-phenylethyl]amino]ethyl]-4-hydroxy-4-methyl-N-(4-phenylphenyl)pyrrolidine-2-carboxamide Isomer 1 (110 mg, 187.57 umol, 34.55% yield, 98.5% purity) as a white solid. MS (ESI) m/z 578.3 $[M+H]^+$ $^1H$ NMR (400 MHz, METHANOL-$d_4$) δ=8.40-8.19 (m, 2H), 7.54 (br d, J=7.6 Hz, 4H), 7.50-7.32 (m, 9H), 7.28-7.22 (m, 1H), 7.05-6.69 (m, 1H), 6.37 (s, 1H), 5.19-4.98 (m, 1H), 4.31 (dd, J=4.8, 9.0 Hz, 1H), 3.51 (d, J=9.4 Hz, 1H), 3.36-3.32 (m, 1H), 2.16-1.83 (m, 2H), 1.39 (d, J=7.0 Hz, 3H), 1.23 (s, 3H)

(2R,4R)—N-([1,1'-biphenyl]-4-yl)-1-cyano-N-(1-(5-fluoropyridin-3-yl)-2-oxo-2-(((S)-1-phenylethyl)amino)ethyl)-4-hydroxy-4-methylpyrrolidine-2-carboxamide Isomer 2

To a solution of (2R,4R)—N-[1-(5-fluoro-3-pyridyl)-2-oxo-2-[[(1S)-1-phenylethyl]amino]ethyl]-4-hydroxy-4-methyl-N-(4-phenylphenyl)pyrrolidine-2-carboxamide (300 mg, 542.85 umol, 1 eq) in EtOH (3 mL) was added $NaHCO_3$ (136.81 mg, 1.63 mmol, 63.34 uL, 3 eq), and then the solution was cooled to −10° C. A solution of BrCN (86.25 mg, 814.28 umol, 59.89 uL, 1.5 eq) in EtOH (1 mL) was added, and the solution stirred for 1 h at 0° C. and warmed to 25° C. gradually. Upon completion, the mixture was quenched by addition $H_2O$ (30 mL) and then extracted with DCM (30 mL*3). The combined organic layers were washed with brine (30 mL), dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 40%-60%, 8 min) affording (2R,4R)-1-cyano-N-[1-(5-fluoro-3-pyridyl)-2-oxo-2-[[(1S)-1-phenylethyl]amino]ethyl]-4-hydroxy-4-methyl-N-(4-phenylphenyl)pyrrolidine-2-carboxamide Isomer 2 (105 mg, 181.41 umol, 33.42% yield, 99.8% purity) as a white solid. MS (ESI) m/z 578.3 $[M+H]^+$.

$^1H$ NMR (400 MHz, METHANOL-$d_4$) δ=8.27 (d, J=2.8 Hz, 1H), 8.18 (s, 1H), 7.96-7.76 (m, 1H), 7.74-7.58 (m, 1H), 7.57-7.50 (m, 2H), 7.46-7.30 (m, 4H), 7.24-7.07 (m, 6H), 6.89-6.66 (m, 1H), 6.20 (s, 1H), 5.06 (d, J=7.0 Hz, 1H), 4.35 (dd, J=4.0, 9.4 Hz, 1H), 3.52 (d, J=9.2 Hz, 11H), 3.36 (d, J=9.2 Hz, 11H), 2.12-1.92 (m, 2H), 1.48 (d, J=7.0 Hz, 3H), 1.26 (s, 3H).

Example 219: Synthesis of Compound 1353

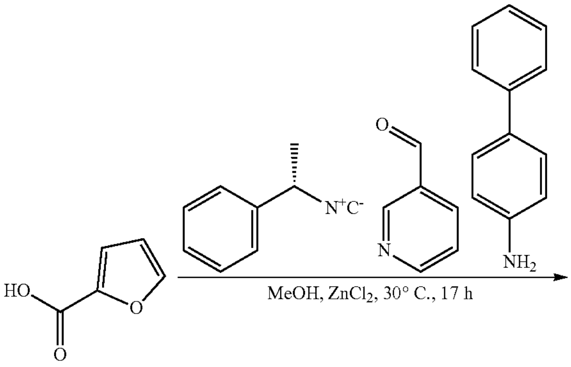

-continued

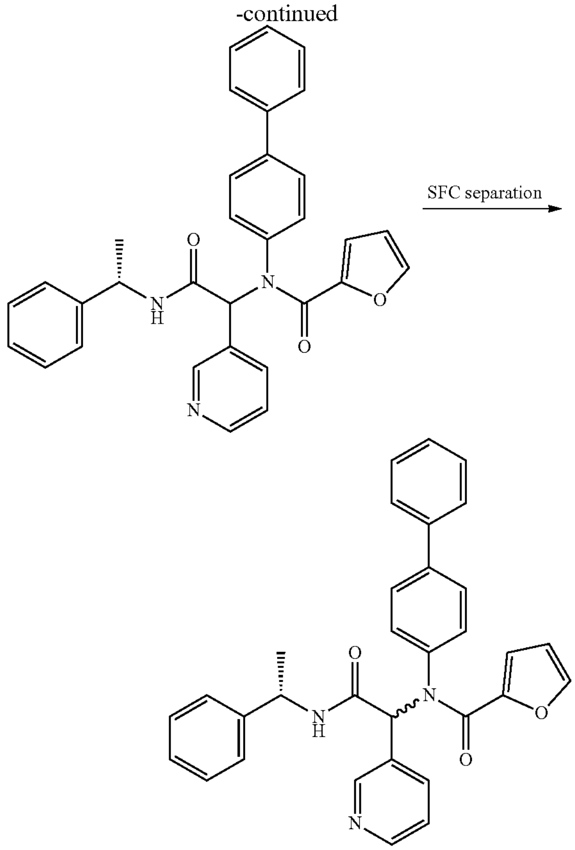

Step 1: N-[2-oxo-2-[[(1S)-1-phenylethyl]amino]-1-(3-pyridyl)ethyl]-N-(4-phenylphenyl)furan-2-carboxamide A solution of 4-phenylaniline (301.96 mg, 1.78 mmol, 1 eq) and pyridine-3-carbaldehyde (191.13 mg, 1.78 mmol, 167.65 uL, 1 eq) in MeOH (15 mL) was stirred for 12 h, and then furan-2-carboxylic acid (200 mg, 1.78 mmol, 1 eq) was added. The resulting mixture was stirred for 1 h, [(1S)-1-isocyanoethyl]benzene (234.07 mg, 1.78 mmol, 1 eq) in MeOH (1 mL) was added, and then $ZnCl_2$ (2 M, 2.68 mL, 3 eq) was added. The mixture was stirred at 30° C. for 4 h. Upon completion, the reaction mixture was concentrated under reduced pressure to remove solvent. The residue was purified by prep-HPLC (column: Waters Xbridge C18 150*50 mm*10 um; mobile phase: [water (10 mM $NH_4HCO_3$)-ACN]; B %: 45%-65%, 10 min) to give N-[2-oxo-2-[[(1S)-1-phenylethyl]amino]-1-(3-pyridyl)ethyl]-N-(4-phenylphenyl)furan-2-carboxamide (600 mg, 1.16 mmol, 64.76% yield, 96.6% purity) as a yellow solid. MS (ESI) m/z 502.2 $[M+H]^+$ Step 2: N-[2-oxo-2-[[(1S)-1-phenylethyl]amino]-1-(3-pyridyl)ethyl]-N-(4-phenylphenyl)furan-2-carboxamide Isomer 1:

N-[2-oxo-2-[[(1S)-1-phenylethyl]amino]-1-(3-pyridyl)ethyl]-N-(4-phenylphenyl)furan-2-carboxamide (400 mg) was separated by SFC (column: DAICEL CHIRALPAK AD (250 mm*30 mm, 10 um); mobile phase: [0.1% $NH_3H_2O$ IPA]; B %: 55%-55%, 10 min) to give N-[2-oxo-2-[[(1S)-

1-phenylethyl]amino]-1-(3-pyridyl)ethyl]-N-(4-phenylphenyl)furan-2-carboxamide (167.8 mg, 334.55 umol, 41.95% yield, 100% purity) as a white solid. MS (ESI) m/z 502.2 $[M+H]^+$.

1H NMR (400 MHz, METHANOL-$d_4$) δ=8.45 (d, J=2.4 Hz, 1H), 8.36 (d, J=1.4 Hz, 1H), 7.68 (d, J=1.8 Hz, 1H), 7.57-7.53 (m, 2H), 7.53-7.29 (m, 12H), 7.28-7.23 (m, 2H), 6.39 (s, 1H), 6.26 (d, J=1.8 Hz, 1H), 5.69 (d, J=3.4 Hz, 1H), 5.09 (d, J=7.4 Hz, 1H), 1.37 (d, J=7.4 Hz, 3H)

Isomer 2:

To give N-[2-oxo-2-[[(1S)-1-phenylethyl]amino]-1-(3-pyridyl)ethyl]-N-(4-phenylphenyl)furan-2-carboxamide (150 mg, 268.85 umol, 33.71% yield, 89.9% purity) as a white solid. MS (ESI) m/z 502.2 $[M+H]^+$.

1H NMR (400 MHz, METHANOL-$d_4$) δ=8.37-8.28 (m, 2H), 7.55-7.26 (m, 11H), 7.22-7.09 (m, 6H), 6.36 (s, 1H), 6.28 (d, J=1.8 Hz, 1H), 5.71 (d, J=3.4 Hz, 1H), 5.09 (d, J=7.4 Hz, 1H), 1.50 (d, J=7.4 Hz, 3H)

Example 220: Synthesis of Compound 1355

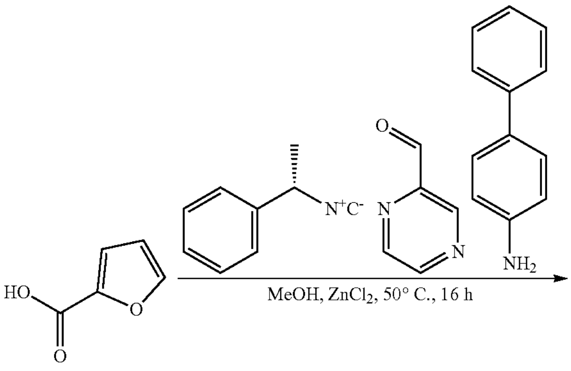

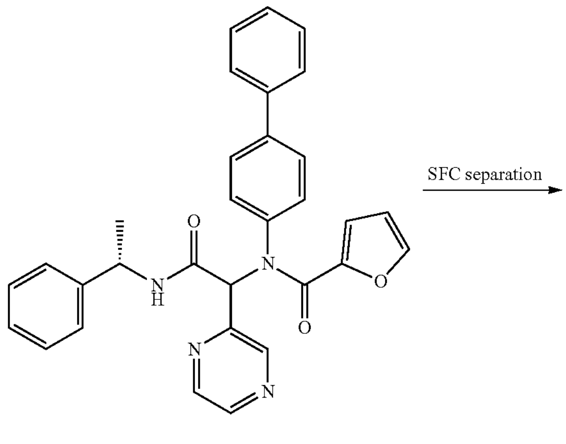

-continued

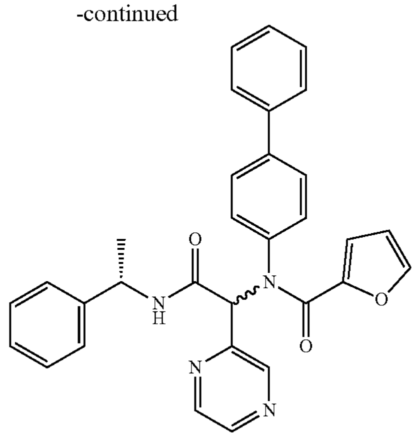

Step 1: N-[2-oxo-2-[[(1S)-1-phenylethyl]amino]-1-pyrazin-2-yl-ethyl]-N-(4-phenylphenyl)furan-2-carboxamide To a solution of 4-phenylaniline (301.96 mg, 1.78 mmol, 1 eq) and pyrazine-2-carbaldehyde (192.89 mg, 1.78 mmol, 1 eq) in MeOH (15 mL) was added furan-2-carboxylic acid (200 mg, 1.78 mmol, 1 eq). After stirring for 3 h, [(1S)-1-isocyanoethyl]benzene (234.07 mg, 1.78 mmol, 1 eq) in MeOH (1 mL) was added, and then $ZnCl_2$ (2 M, 2.68 mL, 3 eq) was added. The mixture was stirred at 50° C. for 13 h. Upon completion, the reaction mixture was concentrated under reduced pressure to remove solvent. The residue was purified by prep-HPLC (column: Waters Xbridge C18 150*50 mm*10 um; mobile phase: [water (10 mM $NH_4HCO_3$)-ACN]; B %: 45%-65%, 10 min) to give N-[2-oxo-2-[[(1S)-1-phenylethyl]amino]-1-pyrazin-2-yl-ethyl]-N-(4-phenylphenyl)furan-2-carboxamide (600 mg, 1.18 mmol, 66.30% yield, 99.1% purity) as a yellow solid. MS (ESI) m/z 503.2 $[M+H]^+$

Step 2: N-[2-oxo-2-[[(1S)-1-phenylethyl]amino]-1-pyrazin-2-yl-ethyl]-N-(4-phenylphenyl)furan-2-carboxamide Isomer 1:

N-[2-oxo-2-[[(1S)-1-phenylethyl]amino]-1-pyrazin-2-yl-ethyl]-N-(4-phenylphenyl)furan-2-carboxamide (400 mg) was separated by SFC (column: REGIS(S,S) WHELK-O1 (250 mm*25 mm, 10 um); mobile phase: [0.1% $NH_3H_2O$ ETOH]; B %: 60%-60%, 8 min) to give N-[2-oxo-2-[[(1S)-1-phenylethyl]amino]-1-pyrazin-2-yl-ethyl]-N-(4-phenylphenyl)furan-2-carboxamide (167 mg, 331.63 umol, 41.67% yield, 99.8% purity) as a white solid. MS (ESI) m/z 503.2 $[M+H]^+$.

1H NMR (400 MHz, METHANOL-$d_4$) δ=8.60 (d, J=1.4 Hz, 1H), 8.55-8.49 (m, 1H), 8.43-8.37 (m, 1H), 8.35 (d, J=1.4 Hz, 1H), 7.57-7.47 (m, 5H), 7.44-7.26 (m, 6H), 7.26-7.17 (m, 4H), 6.50 (s, 1H), 6.30 (d, J=1.8 Hz, 1H), 5.80-5.76 (m, 1H), 5.10 (d, J=7.4 Hz, 1H), 1.49-1.40 (m, 3H)

1H NMR (400 MHz, DMSO-$d_6$) δ=8.83-8.73 (m, 1H), 8.55-8.50 (m, 1H), 8.45-8.40 (m, 2H), 7.73-7.68 (m, 1H), 7.63 (d, J=7.8 Hz, 2H), 7.60-7.52 (m, 2H), 7.47-7.16 (m, 10H), 6.51 (s, 1H), 6.38-6.33 (m, 1H), 5.67-5.59 (m, 1H), 5.06-4.92 (m, 1H), 1.38-1.28 (m, 3H)

Isomer 2:

N-[2-oxo-2-[[(1S)-1-phenylethyl]amino]-1-pyrazin-2-yl-ethyl]-N-(4-phenylphenyl)furan-2-carboxamide (161 mg, 319.40 umol, 40.13% yield, 99.7% purity) was obtained as a white solid. MS (ESI) m/z 503.2 $[M+H]^+$.

1H NMR (400 MHz, METHANOL-$d_4$) δ=8.60 (d, J=1.4 Hz, 1H), 8.55-8.49 (m, 1H), 8.44-8.37 (m, 1H), 8.35 (d, J=1.4 Hz, 1H), 7.58-7.48 (m, 5H), 7.45-7.30 (m, 8H), 7.27-7.18 (m, 2H), 6.50 (s, 1H), 6.29 (d, J=1.8 Hz, 1H), 5.77 (d, J=3.5 Hz, 1H), 5.10 (d, J=7.0 Hz, 1H), 1.48-1.40 (m, 3H)

1H NMR (400 MHz, DMSO-$d_6$) δ=8.83-8.70 (m, 1H), 8.59 (s, 1H), 8.55-8.50 (m, 1H), 8.46-8.40 (m, 1H), 7.72-7.68 (m, 1H), 7.63 (d, J=7.8 Hz, 2H), 7.59-7.51 (m, 2H), 7.47-7.16 (m, 10H), 6.51 (s, 1H), 6.38-6.33 (m, 1H), 5.66-5.59 (m, 1H), 5.02 (t, J=7.4 Hz, 1H), 1.39-1.22 (m, 3H)

Example 221: Synthesis of Compound 1336

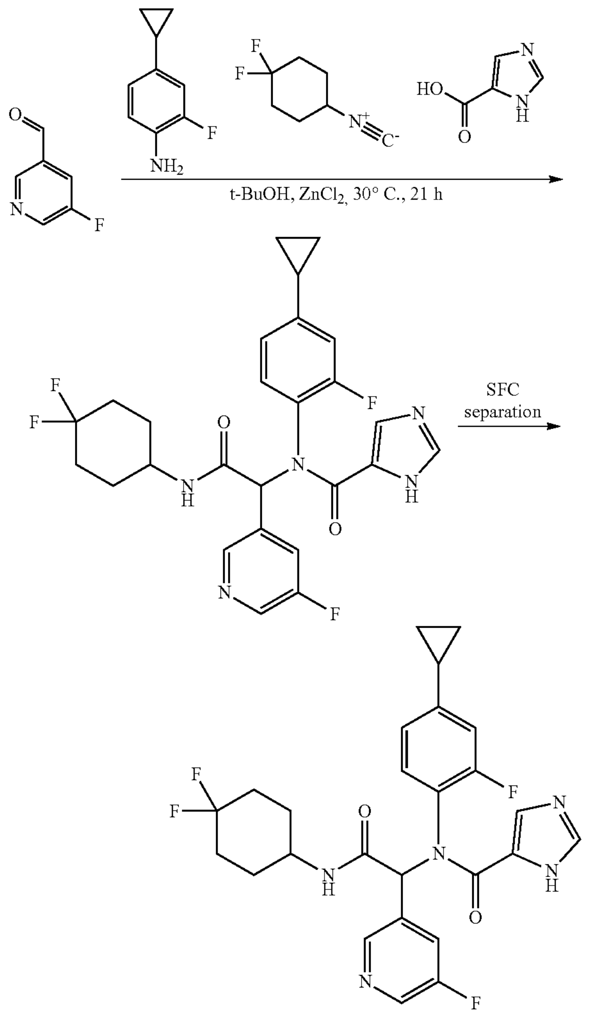

Step 1: N-(4-cyclopropyl-2-fluorophenyl)-N-(2-((4,4-difluorocyclohexyl)amino)-1-(5-fluoropyridin-3-yl)-2-oxoethyl)-1H-imidazole-5-carboxamide A mixture of 5-fluoropyridine-3-carbaldehyde (250 mg, 2.00 mmol, 1 eq) and 4-cyclopropyl-2-fluoro-aniline (211.48 mg, 1.40 mmol, 0.7 eq) in t-BuOH (5 mL) was stirred at 30° C. for 5 h. 1H-Imidazole-5-carboxylic acid (223.99 mg, 2.00 mmol, 1 eq), 1,1-difluoro-4-isocyano-cyclohexane (290.07 mg, 2.00 mmol, 1 eq) in t-BuOH (0.5 mL) and $ZnCl_2$ (1 M, 6.00 mL, 3 eq) were added into the resulting mixture and was stirred at 30° C. for 16 h. Upon completion, the reaction mixture was concentrated, and then purified by prep-HPLC (column: Welch Xtimate C18 250*70 mm #10 um); mobile phase: water (10 mM $NH_4HCO_3$)-ACN]; B %: 25%-55%, 10 min). N-(4-cyclopropyl-2-fluoro-phenyl)-N-[2-[(4,4-difluorocyclohexyl) amino]-1-(5-fluoro-3-pyridyl)-2-oxo-ethyl]-1H-imidazole-5-carboxamide (150 mg, 247.33 umol, 12.38% yield, 85% purity) was obtained as white solid. MS (ESI) m/z 516.3 $[M+H]^+$

Step 2: N-(4-cyclopropyl-2-fluorophenyl)-N-(2-((4,4-difluorocyclohexyl)amino)-1-(5-fluoropyridin-3-yl)-2-oxoethyl)-1H-imidazole-5-carboxamide N-(4-Cyclopropyl-2-fluoro-phenyl)-N-[2-[(4,4-difluoro-cyclohexyl)amino]-1-(5-fluoro-3-pyridyl)-2-oxo-ethyl]-1H-imidazole-5-carboxamide was separated by SFC (column: DAICEL CHIRALPAK AD (250 mm*30 mm, 10 um); mobile phase: [Neu-ETOH]; B %: 35%-35%, 12 min), then purified by prep-HPLC (column: Waters Xbridge BEH C18 100*25 mm*5 um; mobile phase: [water (10 mM $NH_4HCO_3$)-ACN]; B %: 25%-55%, 10 min) to afford N-(4-cyclopropyl-2-fluoro-phenyl)-N-[2-[(4,4-difluorocyclo-hexyl)amino]-1-(5-fluoro-3-pyridyl)-2-oxo-ethyl]-1H-imidazole-5-carboxamide Isomer 1 (17 mg, 32.75 umol, 42.20% yield, 99.3% purity) as a white solid. MS (ESI) m/z 516.2 $[M+H]^+$ $^1$H NMR (400 MHz, MeOD-$d_4$) δ=8.46-8.19 (m, 2H), 7.83-7.53 (m, 2H), 7.42 (br d, J=8.8 Hz, 1H), 7.09-6.53 (m, 2H), 6.27 (br s, 1H), 6.10-5.39 (m, 1H), 3.88 (br t, J=9.4 Hz, 1H), 2.09 (br s, 3H), 1.93 (br s, 4H), 1.74-1.60 (m, 1H), 1.54-1.41 (m, 1H), 1.02 (br d, J=7.2 Hz, 2H), 0.67 (br s, 2H).

Purified by prep-HPLC (column: Waters Xbridge BEH C18 100*25 mm*5 um; mobile phase: [water (10 Mm $NH_4HCO_3$)-ACN]; B %: 25%-55%, 10 min) to give N-(4-cyclopropyl-2-fluoro-phenyl)-N-[2-[(4,4-difluorocyclo-hexyl)amino]-1-(5-fluoro-3-pyridyl)-2-oxo-ethyl]-1H-imidazole-5-carboxamide Isomer 2 (17 mg, 32.98 umol, 42.50% yield) as a white solid. MS (ESI) m/z 516.2 $[M+H]^+$ $^1$H NMR (400 MHz, MeOD-$d_4$) δ=8.47-8.19 (m, 2H), 7.81-7.57 (m, 2H), 7.42 (br d, J=8.8 Hz, 1H), 7.10-6.54 (m, 2H), 6.27 (br s, 1H), 6.11-5.34 (m, 1H), 4.00-3.70 (m, 1H), 2.16-1.96 (m, 3H), 1.95-1.78 (m, 4H), 1.73-1.41 (m, 2H), 1.02 (br d, J=7.0 Hz, 2H), 0.67 (br s, 2H).

Example 222: Synthesis of Compound 1337

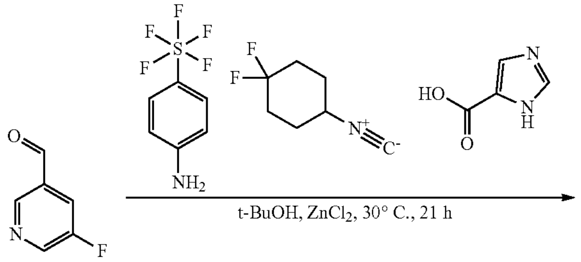

-continued

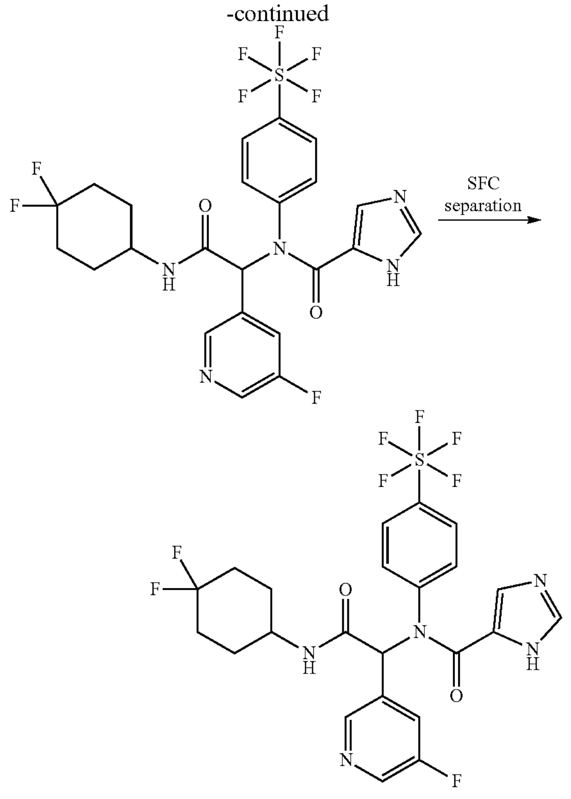

Step 1: N-[2-[(4,4-difluorocyclohexyl)amino]-1-(5-fluoro-3-pyridyl)-2-oxo-ethyl]-N-[4-(pentafluoro-λ6-sulfanyl)phenyl]-JH-imidazole-5-carboxamide A mixture of 5-fluoropyridine-3-carbaldehyde (300 mg, 2.40 mmol, 1 eq) and 4-(pentafluoro-λ6-sulfanyl) aniline (367.92 mg, 1.68 mmol, 0.7 eq) in t-BuOH (5 mL) was stirred at 30° C. for 5 h. 1H-imidazole-5-carboxylic acid (268.79 mg, 2.40 mmol, 1 eq), 1,1-difluoro-4-isocyano-cyclohexane (348.08 mg, 2.40 mmol, 1 eq) in t-BuOH (0.5 mL) and $ZnCl_2$ (1 M, 7.19 mL, 3 eq) were added to the resulting mixture and was stirred at 30° C. for 16 h. Upon completion, the reaction mixture was concentrated and purified by prep-HPLC (column: Kromasil C18 (250*50 mm*10 um); mobile phase: [water (0.05% $NH_3H_2O$+10 mM $NH_4HCO_3$)-ACN]; B %: 25%-55%, 10 min). N-[2-[(4,4-difluorocyclohexyl)amino]-1-(5-fluoro-3-pyridyl)-2-oxo-ethyl]-N-[4-(pentafluoro-λ6-sulfanyl)phenyl]-1H-imidazole-5-carboxamide (100 mg, 171.38 umol, 7.15% yield, 100% purity) was obtained as white solid. MS (ESI) m/z 584.2 $[M+H]^+$ Step 2: N-[2-[(4,4-difluorocyclohexyl)amino]-1-(5-fluoro-3-pyridyl)-2-oxo-ethyl]-N-[4-(pentafluoro-λ6-sulfanyl)phenyl]-JH-imidazole-5-carboxamide N-[2-[(4,4-difluorocyclohexyl)amino]-1-(5-fluoro-3-pyridyl)-2-oxo-ethyl]-N-[4-(pentafluoro-λ6-sulfanyl)phenyl]-1H-imidazole-5-carboxamide was separated by SFC (C (column: DAICEL CHIRALPAK AD (250 mm*30 mm, 10 um); mobile phase: [Neu-ETOH]; B %: 18%-18%, 15 min), then purified by prep-HPLC (column: Waters Xbridge BEH C18 100*25 mm*5 um; mobile phase: [water (10 mM $NH_4HCO_3$)-ACN]; B %: 30%-55%, 10 min) to give N-[2-[(4,4-difluorocyclohexyl)amino]-1-(5-fluoro-3-pyridyl)-2-oxo-ethyl]-N-[4-(pentafluoro-λ6-sulfanyl)phenyl]-1H-imidazole-5-carboxamide Isomer 1 (27 mg, 45.72 umol, 66.69% yield, 98.8% purity) as a white solid. MS (ESI) m/z 584.2 $[M+H]^+$ $^1$H NMR (400 MHz, MeOD-$d_4$) δ=8.35 (d, J=2.6 Hz, 1H), 8.27 (s, 1H), 7.88-7.32 (m, 6H), 6.72 (br d, J=3.6 Hz, 0.5H), 6.35 (br s, 1H), 5.62-5.38 (m, 0.5H), 3.89 (br t, J=10.4 Hz, 1H), 2.10-1.82 (m, 6H), 1.71-1.42 (m, 2H).

$^1$H NMR (400 MHz, DMSO-$d_6$) δ=12.95 (br s, 0.4H), 12.33 (br d, J=2.8 Hz, 0.4H), 8.48-8.42 (m, 1H), 8.31 (br s, 1H), 8.26-8.21 (m, 1H), 7.96-7.83 (m, 1H), 7.74-7.27 (m, 5H), 6.52-6.15 (m, 0.4H), 5.31 (br s, 1H), 3.87-3.70 (m, 1H), 2.08-1.60 (m, 6H), 1.58-1.29 (m, 2H).

Purified by prep-HPLC (column: Waters Xbridge BEH C18 100*25 mm*5 um; mobile phase: [water (10 mM $NH_4HCO_3$)-ACN]; B %: 30%-55%, 10 min) to give N-[2-[(4,4-difluorocyclohexyl)amino]-1-(5-fluoro-3-pyridyl)-2-oxo-ethyl]-N-[4-(pentafluoro-λ6-sulfanyl)phenyl]-1H-imidazole-5-carboxamide Isomer 2 (30 mg, 51.41 umol, 75.00% yield, 100% purity) as a white solid. MS (ESI) m/z 584.2 $[M+H]^+$ $^1$H NMR (400 MHz, MeOD-$d_4$) 5=8.35 (d, J=2.8 Hz, 1H), 8.27 (s, 1H), 7.87-7.32 (m, 6H), 6.72 (br s, 0.4H), 6.35 (br s, 1H), 5.49 (br s, 0.4H), 3.89 (br t, J=10.2 Hz, 1H), 2.11-1.81 (m, 6H), 1.74-1.41 (in, 2H)

$^1$H NMR (400 MHz, DMSO-$d_6$) δ=13.05-12.85 (m, 0.4H), 12.45-12.22 (m, 0.4H), 8.44 (d, J=2.6 Hz, 1H), 8.41-8.26 (m, 1H), 8.23 (s, 1H), 7.89 (br d, J=7.2 Hz, 1H), 7.62 (br s, 5H), 6.49-6.21 (m, 1H), 5.31 (br s, 0.3H), 3.93-3.66 (m, 1H), 2.08-1.62 (m, 6H), 1.58-1.29 (m, 2H)

Example 223: Synthesis of Compound 1338

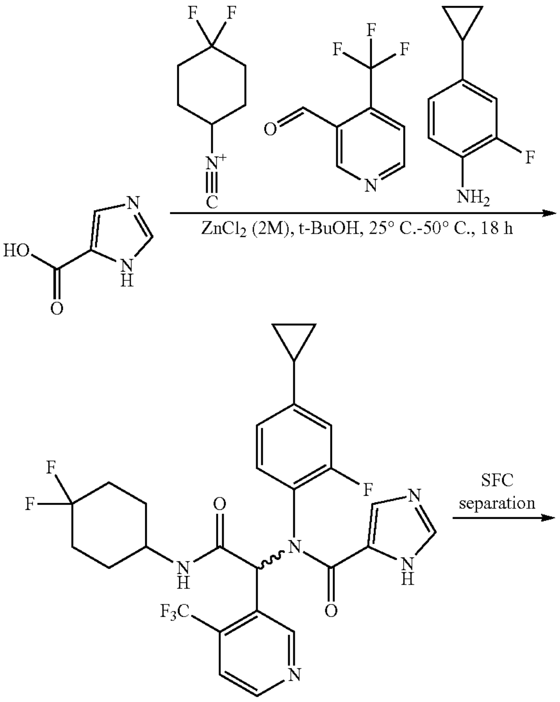

-continued

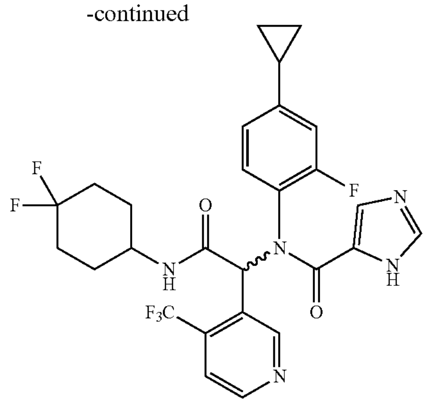

Step1: N-(4-cyclopropyl-2-fluorophenyl)-N-(2-((4,4-difluorocyclohexyl)amino)-2-oxo-1-(4-(trifluoromethyl)pyridin-3-yl)ethyl)-1H-imidazole-5-carboxamide To a solution of 4-cyclopropyl-2-fluoro-aniline (404.63 mg, 2.68 mmol, 1 eq), 4-(trifluoromethyl)pyridine-3-carbaldehyde (468.68 mg, 2.68 mmol, 1 eq) in t-BuOH (20 mL) was stirred at 25° C. for 2 h, then the mixture was added 1H-imidazole-5-carboxylic acid (300 mg, 2.68 mmol, 1 eq), 1,1-difluoro-4-isocyano-cyclohexane (388.49 mg, 2.68 mmol, 1 eq), $ZnCl_2$ (2 M, 4.01 mL, 3 eq), and stirred at 50° C. for 16 h. Upon completion, the reaction was concentrated in the vacuum and was purified by prep-HPLC (column: Waters Xbridge C18 150*50 mm*10 um; mobile phase: [water (10 mM $NH_4HCO_3$)-ACN]; B %: 50%-70%, 10 min) to give product N-(4-cyclopropyl-2-fluorophenyl)-N-(2-((4,4-difluorocyclohexyl)amino)-2-oxo-1-(4-(trifluoromethyl)pyridin-3-yl)ethyl)-1H-imidazole-5-carboxamide (35 mg, 61.89 umol, 2.31% yield) as yellow oil. MS (ESI) m/z 566.2 $[M+H]^+$.

Step 2: N-(4-cyclopropyl-2-fluorophenyl)-N-(2-((4,4-difluorocyclohexyl)amino)-2-oxo-1-(4-(trifluoromethyl)pyridin-3-yl)ethyl)-1H-imidazole-5-carboxamide N-(4-Cyclopropyl-2-fluorophenyl)-N-(2-((4,4-difluorocyclohexyl)amino)-2-oxo-1-(4-(trifluoromethyl)pyridin-3-yl)ethyl)-1H-imidazole-5-carboxamide was separated by SFC (column: DAICEL CHIRALPAK AD (250 mm*30 mm, 10 um); mobile phase: [0.1% $NH_3H_2O$ MEOH]; B %: 24%-24%, 8 min.) to give product N-(4-cyclopropyl-2-fluorophenyl)-N-(2-((4,4-difluorocyclohexyl)amino)-2-oxo-1-(4-(trifluoromethyl)pyridin-3-yl)ethyl)-1H-imidazole-5-carboxamide (7 mg, 12.31 umol, 46.41% yield, 99.44% purity) MS (ESI) m/z 566.1 $[M+H]^+$.

$^1H$ NMR (400 MHz, DMSO-$d_6$) δ=13.02-12.09 (m, 1H), 9.07-8.09 (m, 3H), 7.91-7.34 (m, 3H), 7.12-6.54 (m, 3H), 5.76-5.23 (m, 1H), 3.96-3.63 (m, 11H), 2.06-1.67 (m, 7H), 1.56-1.22 (m, 2H), 1.07-0.90 (m, 2H), 0.76-0.55 (m, 2H).

$^1H$ NMR (400 MHz, DMSO-$d_6$) δ=12.63-12.10 (m, 1H), 8.76-7.90 (m, 3H), 7.79-7.12 (m, 3H), 7.06-6.54 (m, 3H), 5.52 (br s, 1H), 3.75 (br s, 1H), 2.04-1.63 (m, 7H), 1.47-1.29 (m, 2H), 0.99 (br s, 2H), 0.68 (br s, 2H).

N-(4-cyclopropyl-2-fluorophenyl)-N-(2-((4,4-difluorocyclohexyl)amino)-2-oxo-1-(4-(trifluoromethyl)pyridin-3-yl)ethyl)-1H-imidazole-5-carboxamide (7 mg, 12.31 umol, 46.42% yield, 99.48% purity) was obtained as a yellow solid. MS (ESI) m/z 566.1 $[M+H]^+$.

$^1H$ NMR (400 MHz, DMSO-$d_6$) δ=12.99-12.11 (m, 1H), 9.07-8.06 (m, 3H), 7.91-7.31 (m, 3H), 7.14-6.53 (m, 3H), 5.71-5.27 (m, 1H), 3.87-3.64 (m, 1H), 2.02-1.52 (m, 7H), 1.44-1.20 (m, 2H), 1.05-0.90 (m, 2H), 0.78-0.56 (m, 2H).

$^1H$ NMR (400 MHz, DMSO-$d_6$) δ=12.71-11.94 (m, 1H), 8.78-7.79 (m, 3H), 7.72-7.29 (m, 3H), 7.13-6.59 (m, 3H), 5.54 (br s, 1H), 3.74 (br s, 1H), 2.03-1.62 (m, 7H), 1.49-1.26 (m, 2H), 0.99 (br s, 2H), 0.74-0.58 (m, 2H).

Example 224: Synthesis of Compound 1347

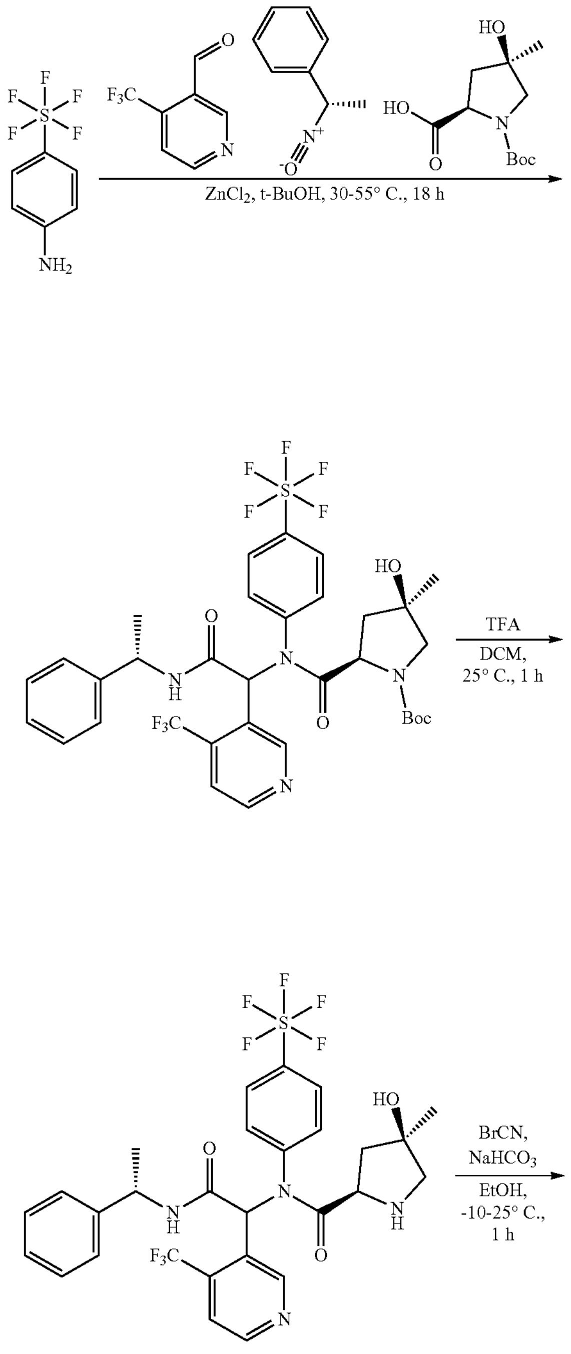

-continued

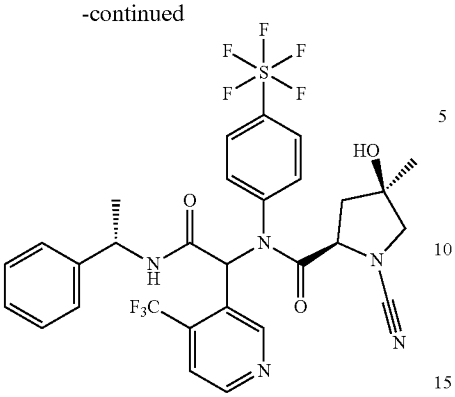

Step 1: tert-butyl (2R,4R)-4-hydroxy-4-methyl-2-[[2-oxo-2-[[(1S)-1-phenylethyl]amino]-1-[4-(trifluoromethyl)-3-pyridyl]ethyl]-[4-(pentafluoro-λ6-sulfanyl)phenyl]carbamoyl]pyrrolidine-1-carboxylate A solution of 4-(pentafluoro-$\lambda^6$-sulfanyl)aniline (300 mg, 1.37 mmol, 1 eq), 4-(trifluoromethyl)pyridine-3-carbaldehyde (311.59 mg, 1.78 mmol, 1.3 eq) in t-BuOH (8 mL) was stirred at 30° C. for 8 h. (2R,4R)-1-Tert-butoxycarbonyl-4-hydroxy-4-methyl-pyrrolidine-2-carboxylic acid (335.72 mg, 1.37 mmol, 1 eq) was added to the resulting mixture. Then, a solution of [(1S)-1-isocyanoethyl]benzene (161.59 mg, 1.23 mmol, 0.9 eq) in t-BuOH (1 mL) was added in batches (three times), followed by the addition of $ZnCl_2$ (2 M, 2.05 mL, 3 eq). The mixture was stirred at 55° C. for 8 h. Upon completion, the reaction mixture was concentrated under reduced pressure to give a residue. The residue was purified by prep-HPLC (column: Waters Xbridge C18 150*50 mm*10 um; mobile phase: [water (10 mM $NH_4HCO_3$)-ACN]; B %: 50%-80%, 10 min) and the residue was purified by column chromatography ($SiO_2$, Petroleum ether/Ethyl acetate=10/1 to 0/1) to give a compound tert-butyl (2R,4R)-4-hydroxy-4-methyl-2-[[2-oxo-2-[[(1S)-1-phenylethyl]amino]-1-[4-(trifluoromethyl)-3-pyridyl]ethyl]-[4-(pentafluoro-$\lambda^6$-sulfanyl)phenyl]carbamoyl]pyrrolidine-1-carboxylate (50 mg, 65.43 umol, 4.78% yield, 98.5% purity) as a yellow solid. MS (ESI) m/z 753.2 $[M+1]^+$.

Step 2: (2R,4R)-4-hydroxy-4-methyl-N-[2-oxo-2-[[(1S)-1-phenylethyl]amino]-1-[4-(trifluoromethyl)-3-pyridyl]ethyl]-N-[4-(pentafluoro-26-sulfanyl)phenyl]pyrrolidine-2-carboxamide A solution of tert-butyl (2R,4R)-4-hydroxy-4-methyl-2-[[2-oxo-2-[[(1S)-1-phenylethyl]amino]-1-[4-(trifluoromethyl)-3-pyridyl]ethyl]-[4-(pentafluoro-$\lambda^6$-sulfanyl)phenyl]carbamoyl]pyrrolidine-1-carboxylate (50 mg, 66.43 umol, 1 eq) in TFA (0.5 mL) and DCM (1 mL) was stirred at 25° C. for 1 h. Upon completion, the reaction mixture was quenched by addition of $NaHCO_3$ aq (20 mL), and then extracted with DCM (15 mL*3). The combined organic layers were washed with brine (15 mL), dried over $Na_2SO_4$, filtered and concentrated under reduced pressure to give a residue (2R,4R)-4-hydroxy-4-methyl-N-[2-oxo-2-[[(1S)-1-phenylethyl]amino]-1-[4-(trifluoromethyl)-3-pyridyl]ethyl]-N-[4-(pentafluoro-$\lambda^6$-sulfanyl)phenyl]pyrrolidine-2-carboxamide (35 mg, crude) as a yellow solid. MS (ESI) m/z 653.2 $[M+H]^+$.

Step 3: (2R,4R)-1-cyano-4-hydroxy-4-methyl-N-[2-oxo-2-[[(1S)-1-phenylethyl]amino]-1-[4-(trifluoromethyl)-3-pyridyl]ethyl]-N-[4-(pentafluoro-26-sulfanyl)phenyl]pyrrolidine-2-carboxamide To a solution of (2R,4R)-4-hydroxy-4-methyl-N-[2-oxo-2-[[(1S)-1-phenylethyl]amino]-1-[4-(trifluoromethyl)-3-pyridyl]ethyl]-N-[4-(pentafluoro-$\lambda^6$-sulfanyl)phenyl]pyrrolidine-2-carboxamide (25 mg, 38.31 umol, 1 eq) and $NaHCO_3$ (9.65 mg, 114.93 umol, 4.47 uL, 3 eq) in EtOH (1 mL) was added a solution of BrCN (8.12 mg, 76.62 umol, 5.64 uL, 2 eq) in EtOH (0.25 mL) drop-wise at −10° C. under $N_2$. The reaction mixture was stirred at 25° C. for another 1 h. Upon completion, the reaction mixture was quenched by addition $H_2O$ (10 mL) and then extracted with EtOAc (5 mL*3). The combined organic layers were washed with brine (5 mL), dried over $Na_2SO_4$, filtered and concentrated under reduced pressure to give a residue. The residue was purified by prep-HPLC (column: Phenomenex Luna C18 150*30 mm*5 um; mobile phase: [water (0.2% FA)-ACN]; B %: 35%-80%, 8 min) to give a compound (2R,4R)-1-cyano-4-hydroxy-4-methyl-N-[2-oxo-2-[[(1S)-1-phenylethyl]amino]-1-[4-(trifluoromethyl)-3-pyridyl]ethyl]-N-[4-(pentafluoro-$\lambda^6$-sulfanyl)phenyl]pyrrolidine-2-carboxamide (3 mg, 4.29 umol, 11.19% yield, 96.8% purity) as a white solid. MS (ESI) m/z 678.2 $[M+H]^+$ $^1H$ NMR (400 MHz, MeOD_$d_4$) δ ppm 8.66-8.65 (m, 1H), 8.51-8.30 (m, 1H), 8.13-7.55 (m, 4H), 7.40-6.85 (m, 6H), 6.78-6.60 (m, 1H), 5.13-5.11 (m, 1H), 4.24-4.21 (m, 1H), 3.50-3.48 (m, 1H), 3.33-3.31 (m, 1H), 2.03-1.87 (m, 2H), 1.41-1.39 (m, 3H), 1.22 (s, 1H).

Example 226: Synthesis of Compound 137a, 137b and 137c

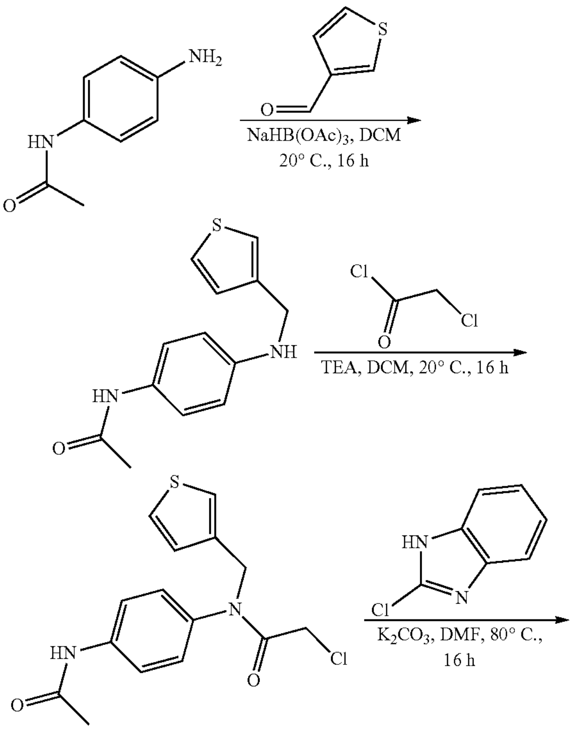

-continued

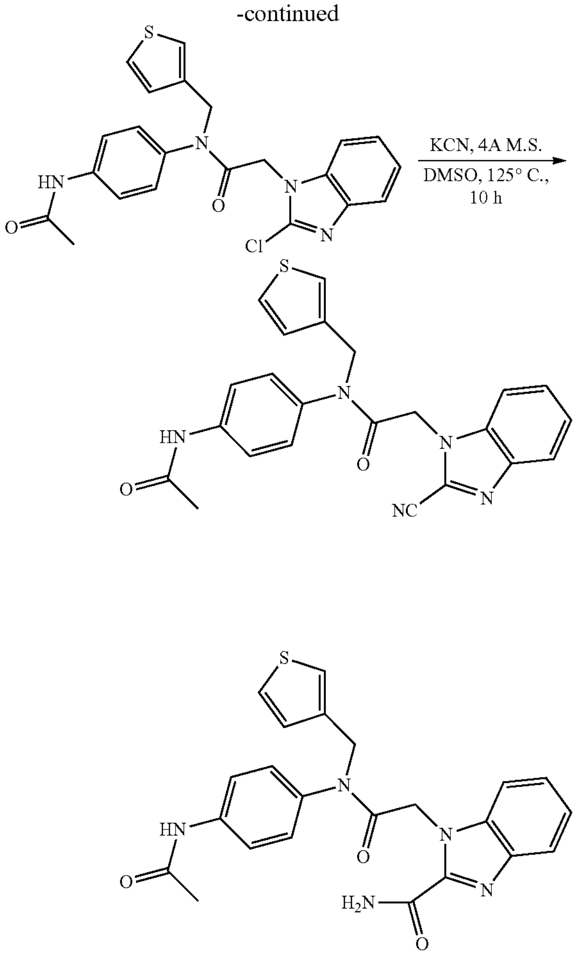

Step 1: N-[4-(3-thienylmethylamino)phenyl]acetamide

To a solution of N-(4-aminophenyl)acetamide (3 g, 19.98 mmol, 1 eq) in DCM (30 mL) was added thiophene-3-carbaldehyde (2.24 g, 19.98 mmol, 1.82 mL, 1 eq) and $NaBH(OAc)_3$ (8.47 g, 39.95 mmol, 2 eq) at 20° C. The resulting mixture was stirred at 20° C. for 16 h. Upon completion, the reaction was added sat. $Na_2CO_3$ (30 mL) and extracted with DCM (30 mL*3). The organic phase was combined, dried over $Na_2SO_4$, filtered and concentrated in vacuo. The crude was triturated with petroleum ether/ethyl acetate=5/1 (30 mL) at 20° C. for 10 min. filtered and concentrated in vacuo to dryness give N-[4-(3-thienylmethylamino)phenyl]acetamide (4.5 g, 18.27 mmol, 91.45% yield, assumed 100% purity) as a white solid.

Step 2: N-(4-acetamidophenyl)-2-chloro-N-(3-thienylmethyl)acetamide

To a solution of N-[4-(3-thienylmethylamino)phenyl]acetamide (2.00 g, 8.12 mmol, 1 eq) in DCM (20 mL) was added TEA (1.64 g, 16.24 mmol, 2.26 mL, 2 eq), and then was added 2-chloroacetyl chloride (1.10 g, 9.74 mmol, 774.65 uL, 1.2 eq) at 0° C. The resulting reaction mixture was stirred at 20° C. for 16 h. Upon completion of the reaction, the reaction mixture was quenched by $H_2O$ (30 mL) at 0° C., and then added sat. $Na_2CO_3$ 10 mL for pH-8, diluted with ethyl acetate (30 mL) and extracted with ethyl acetate (30 mL*3). The combined organic layers dried over $Na_2SO_4$, filtered and concentrated under reduced pressure to give N-(4-acetamidophenyl)-2-chloro-N-(3-thienylmethyl)acetamide (2.6 g, crude) as a black brown oil. The crude was used directly in next step without purification.

Step 3: N-(4-acetamidophenyl)-2-(2-chlorobenzimidazol-1-yl)-N-(3-thienylmethyl)acetamide N-(4-acetamidophenyl)-2-chloro-N-(3-thienylmethyl)acetamide (1.30 g, 4.03 mmol, 1 eq) was dissolved in DMF (10 mL), and then 2-chloro-1H-benzimidazole (737.36 mg, 4.83 mmol, 1.2 eq), $K_2CO_3$ (834.89 mg, 6.04 mmol, 1.5 eq) and LiBr (524.64 mg, 6.04 mmol, 151.63 uL, 1.5 eq) was added to the resulting mixture at 20° C. The resulting mixture was stirred for 16 h at 80° C., and then the mixture was poured into water (30 mL). The residue was extracted with ethyl acetate (10 mL*3), combined the organic phase dried over $Na_2SO_4$, filtered and concentrated in vacuo to dryness. The residue was purified by prep-HPLC (column: Waters Xbridge Prep OBD C18 150*40 mm*10 um; mobile phase: [water (10 mM NH4HCO3)-ACN]; B %: 25%-45%, 8 min) to give N-(4-acetamidophenyl)-2-(2-chlorobenzimidazol-1-yl)-N-(3-thienylmethyl)acetamide (700 mg, 1.59 mmol, 39.60% yield, 100% purity) as a white solid. MS (ESI) m/z 439.0 $[M+H]^+$. $^1H$ NMR (400 MHz, DMSO-$d_6$) δ ppm 10.12 (s, 1H), 7.67 (br d, J=8.6 Hz, 2H), 7.62-7.45 (m, 3H), 7.37-7.20 (m, 5H), 6.94 (d, J=4.8 Hz, 1H), 4.82 (s, 4H), 2.05 (s, 3H).

Step 4: N-(4-acetamidophenyl)-2-(2-cyanobenzimidazol-1-yl)-N-(3-thienylmethyl)acetamide N-(4-acetamidophenyl)-2-(2-chlorobenzimidazol-1-yl)-N-(3-thienylmethyl)acetamide (400.00 mg, 911.31 umol, 1 eq) and 4A M.S. (400 mg, 4.00 mmol, 4.39 eq) was dissolved in DMSO (3 mL). To the resulting mixture was added cyanopotassium (296.70 mg, 4.56 mmol, 195.20 uL, 5 eq), and then the mixture was stirred for 10 h at 125° C. Upon completion of the reaction, the residue was diluted with ethyl acetate (10 mL) and $H_2O$ (20 mL), and then extracted with ethyl acetate (10 mL*2). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 30%-55%, 8 min) to give N-(4-acetamidophenyl)-2-(2-cyanobenzimidazol-1-yl)-N-(3-thienylmethyl)acetamide (200 mg, 465.66 umol, 51.10% yield, 100% purity) as a white solid MS (ESI) m/z 430.1 $[M+H]^+$. $^1H$ NMR (400 MHz, DMSO-$d_6$) δ ppm 10.13 (s, 1H), 7.82 (d, J=8.2 Hz, 1H), 7.73-7.62 (m, 3H), 7.56-7.46 (m, 2H), 7.44-7.37 (m, 1H), 7.35-7.21 (m, 3H), 6.96 (d, J=4.8 Hz, 1H), 5.08 (s, 2H), 4.84 (s, 2H), 2.06 (s, 3H).

1-[2-[4-Acetamido-N-(3-thienylmethyl)anilino]-2-oxo-ethyl]benzimidazole-2-carboxamide (50 mg, 106.14 umol, 11.65% yield, 95% purity) was obtained as a white solid. MS (ESI) m/z 448.0 $[M+H]^+$. $^1H$ NMR (400 MHz, DMSO-$d_6$) δ ppm 10.07 (s, 1H), 8.26 (s, 1H), 7.84-7.60 (m, 5H), 7.50-7.43 (m, 1H), 7.38-7.17 (m, 5H), 6.96 (d, J=4.6 Hz, 1H), 5.18 (s, 2H), 4.78 (s, 2H), 2.03 (s, 3H).

Example 227: Synthesis of Compound 137d, 137e and 137f

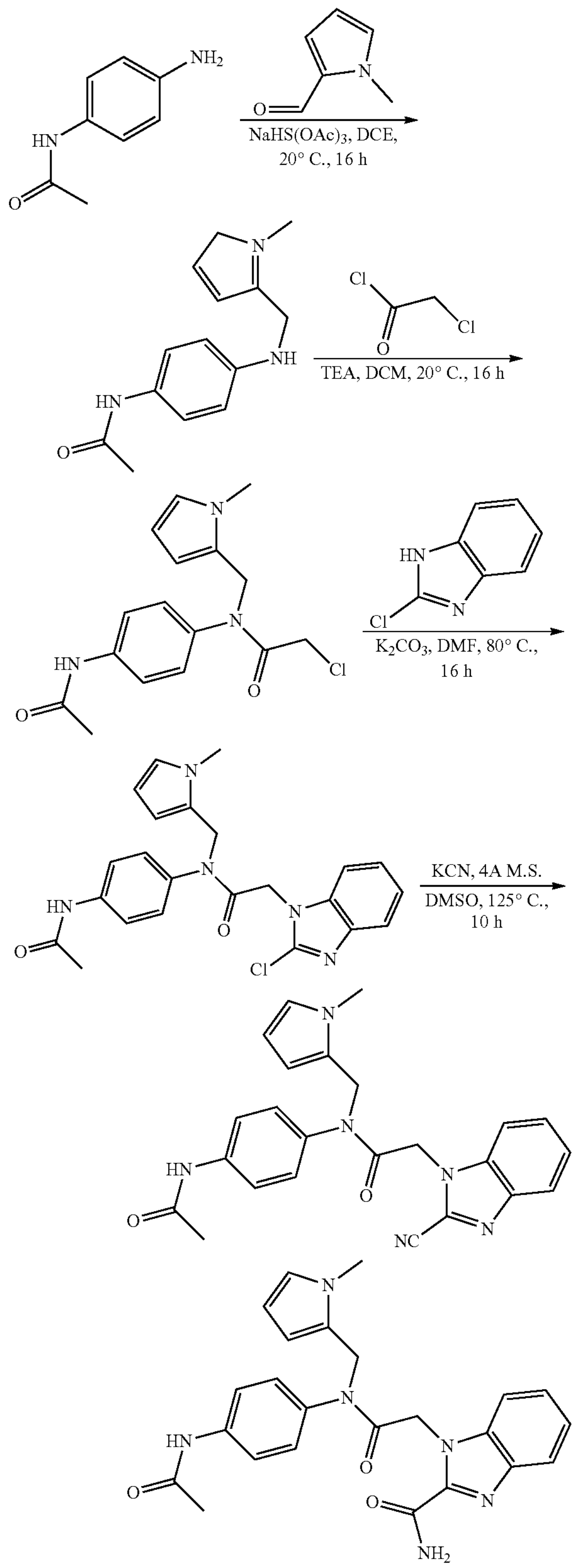

Step 1: N-[4-[(I-methylpyrrol-2-yl)methylamino]phenyl]acetamide

To a solution of N-(4-aminophenyl)acetamide (3 g, 19.98 mmol, 1 eq) in. DCE (30 mL) was added 1-methylpyrrole-2-carbaldehyde (2.18 g, 19.98 mmol, 1 eq) and NaBH$(OAc)_3$ (8.47 g, 39.95 mmol, 2 eq) at 20° C. After stirring the reaction at 20° C. for 16 h, the reaction mixture was quenched by addition $H_2O$ (30 mL) at 0° C., and then added sat. $Na_2CO_3$ (10 mL) for pH~8, diluted with DCM (20 mL) and extracted with DCM (20 mL*2). The combined organic layers dried over $Na_2SO_4$, filtered and concentrated under reduced pressure to give a residue. The residue was purified by column chromatography ($SiO_2$, petroleum ether/ethyl acetate=50/1 to 0/1) give N-[4-[(1-methylpyrrol-2-yl)methylamino]phenyl]acetamide (4.5 g, 18.50 mmol, 92.59% yield, assumed 100% purity) as a light yellow gum.

Step 2: N-(4-acetamidophenyl)-2-chloro-N-[(1-methylpyrrol-2-yl)methyl]acetamide

To a solution of N-[4-[(1-methylpyrrol-2-yl)methylamino]phenyl]acetamide (1 g, 4.11 mmol, 1 eq) in DCM (10 mL) was added 2-chloroacetyl chloride (557.05 mg, 4.93 mmol, 392.29 uL, 1.2 eq) and TEA (831.79 mg, 8.22 mmol, 1.14 mL, 2 eq) at 20° C. After stirring the reaction at 20° C. for 16 h, the reaction mixture was quenched by addition $H_2O$ (10 mL) at 0° C., and then added sat. $Na_2CO_3$ (20 mL) for pH-8, diluted with ethyl acetate (10 mL) and extracted with ethyl acetate (10 mL*3). The combined organic layers dried over $Na_2SO_4$, filtered and concentrated under reduced pressure to give N-(4-acetamidophenyl)-2-chloro-N-[(1-methylpyrrol-2-yl)methyl]acetamide (1.3 g, crude) as a black brown oil. The crude was used directly in next step without purification.

Step 3: N-(4-acetamidophenyl)-2-(2-chlorobenzimidazol-1-yl)-N-[(1-methylpyrrol-2-yl)methyl]acetamide N-(4-acetamidophenyl)-2-chloro-N-[(1-methylpyrrol-2-yl)methyl]acetamide (1 g, 3.13 mmol, 1 eq) was dissolved in DMF (10 mL), and then to the solution was added 2-chloro-1H-benzimidazole (572.56 mg, 3.75 mmol, 1.2 eq), $K_2CO_3$ (648.29 mg, 4.69 mmol, 1.5 eq) and LiBr (407.38 mg, 4.69 mmol, 117.74 uL, 1.5 eq) at 20° C. After stirring the mixture for 16 h at 80° C., the reaction mixture was quenched with water (100 mL), and then extracted with ethyl acetate (50 mL*3). The organic phase was combined, dried over $Na_2SO_4$, filtrated, and concentrated in vacuo to dryness. The residue was purified by flash silica gel chromatography (ISCO®; 25 g SepaFlash® Silica Flash Column, Eluent of 0~100% ethyl acetate/petroleum ether gradient @ 80 mL/min). N-(4-acetamidophenyl)-2-(2-chlorobenzimidazol-1-yl)-N-[(1-methylpyrrol-2-yl)methyl]acetamide (900 mg, 2.06 mmol, 66.03% yield, assumed 100% purity) was obtained as a yellow solid.

Step 4: N-(4-acetamidophenyl)-2-(2-cyanobenzimidazol-1-yl)-N-[(1-methylpyrrol-2-yl)methyl]acetamide N-(4-acetamidophenyl)-2-(2-chlorobenzimidazol-1-yl)-N-[(1-methylpyrrol-2-yl)methyl]acetamide (500.00 mg, 1.15 mmol, 1 eq) and 4A M.S. (500 mg, 5.00 mmol, 4.36 eq) was dissolved in DMSO (3 mL). Cyanopotassium (373.45 mg, 5.74 mmol, 245.69 uL, 5 eq) was added to the resulting mixture, and then the mixture was stirred for 10 h at 125° C. Upon completion of the reaction, the residue was diluted with ethyl acetate (10 mL) and $H_2O$ (20 mL) extracted with ethyl acetate (10 mL*2). The combined organic layers were dried over $Na_2SO_4$, filtered and concentrated under reduced pressure to give a residue. The residue was purified by prep-HPLC (column: Waters Xbridge Prep OBD C18 150*40 mm*10 um; mobile phase: [water (10 mM $NH_4HCO_3$)-ACN]; B %: 25%-45%, 8 min) to yield N-(4-acetamidophenyl)-2-(2-cyanobenzimidazol-1-yl)-N-[(1-methylpyrrol-2-yl)methyl]acetamide (200 mg, 468.97 umol, 40.88% yield, 100% purity) as a white solid. MS (ESI) m/z 427.1 $[M+H]^+$. $^1H$ NMR (400 MHz, DMSO-$d_6$) δ ppm 10.11 (s, 1H), 7.81 (d, J=8.2 Hz, 1H), 7.72-7.59 (m, 3H), 7.50 (t, J=7.6 Hz, 1H), 7.43-7.34 (m, 11H), 7.17 (d, J=8.7 Hz, 2H), 6.66 (s, 1H), 5.80 (t, J=3.0 Hz, 1H), 5.66 (br s, 1H), 5.01 (s, 2H), 4.85 (s, 2H), 3.42 (s, 3H), 2.06 (s, 3H).

Example 228: Synthesis of Compound 137g

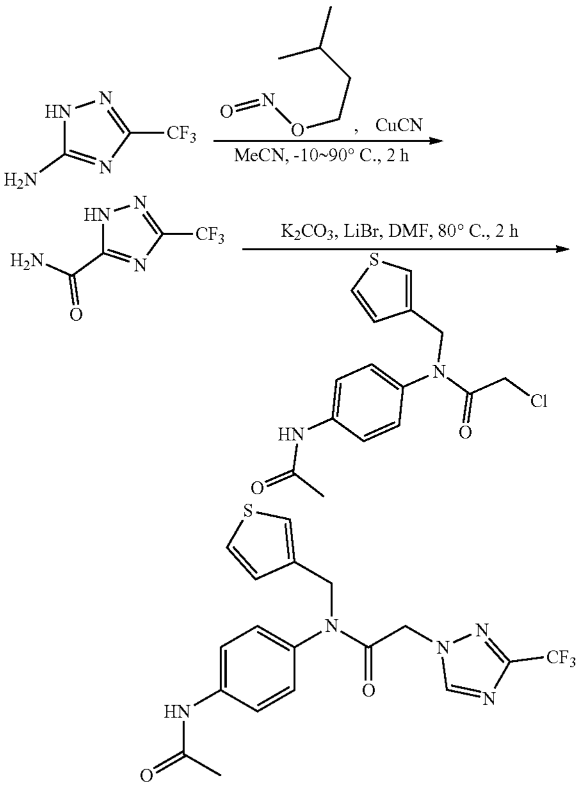

Step 1: 3-(trifluoromethyl)-1H-1,2,4-triazole-5-carboxamide

To a mixture of 5-(trifluoromethyl)-4H-1,2,4-triazol-3-amine (4 g, 26.30 mmol, 1 eq) in ACN (40 mL) was added CuCN (2.59 g, 28.93 mmol, 6.32 mL, 1.1 eq) and isopentyl nitrite (4.31 g, 36.82 mmol, 4.96 mL, 1.4 eq) at −10° C. The resulting mixture was stirred for 0.5 hours, and then stirred at 90° C. for 2 h. Upon completion of reaction, the mixture was filtered and concentrated. The crude was purified by TFA prep-HPLC to get the compound 3-(trifluoromethyl)-1H-1,2,4-triazole-5-carboxamide (300 mg, 1.50 mmol, 5.70% yield, 90% purity) as a green oil. (ESI) m/z 181 $[M+H]^+$ Step 2: N-(4-acetamidophenyl)-N-(3-thienylmethyl)-2-[3-(trifluoromethyl)-1,2,4-triazol-1-yl]acetamide To a mixture of 3-(trifluoromethyl)-1H-1,2,4-triazole-5-carboxamide (11.16 mg, 55.76 umol, 90% purity, 1.2 eq) and N-(4-acetamidophenyl)-2-chloro-N-(3-thienylmethyl)acetamide (16.67 mg, 46.47 umol, 90% purity, 1 eq) in DMF (1 mL) was added LiBr (6.05 mg, 69.70 umol, 1.75 uL, 1.5 eq) and $K_2CO_3$ (12.84 mg, 92.93 umol, 2 eq). The mixture was stirred at 80° C. for 2 h. Upon the reaction completion, the mixture was filtered directly and purified by neutral prep-HPLC to get the compound N-(4-acetamidophenyl)-N-(3-thienylmethyl)-2-[3-(trifluoromethyl)-1,2,4-triazol-1-yl]acetamide (10 mg, 23.62 umol, 50.83% yield, 100% purity) as a white solid. (ESI) m/z 424.0 $[M+H]^+$ column: Waters Xbridge BEH C18 100*30 mm*10 um; mobile phase: [water (10 mM NH4HCO3)-ACN]; B %: 28%-58%, 6 min $^1H$ NMR (400 MHz, DMSO-$d_6$) δ=10.09 (s, 1H), 8.71 (s, 1H), 7.66-7.58 (m, 2H), 7.48 (dd, J=3.1, 4.9 Hz, 1H), 7.28-7.19 (m, 3H), 6.98-6.91 (m, 1H), 4.99 (s, 2H), 4.85-4.78 (m, 2H), 2.05 (s, 3H).

Example 229: Synthesis of Compound 141d, 141e and 141f

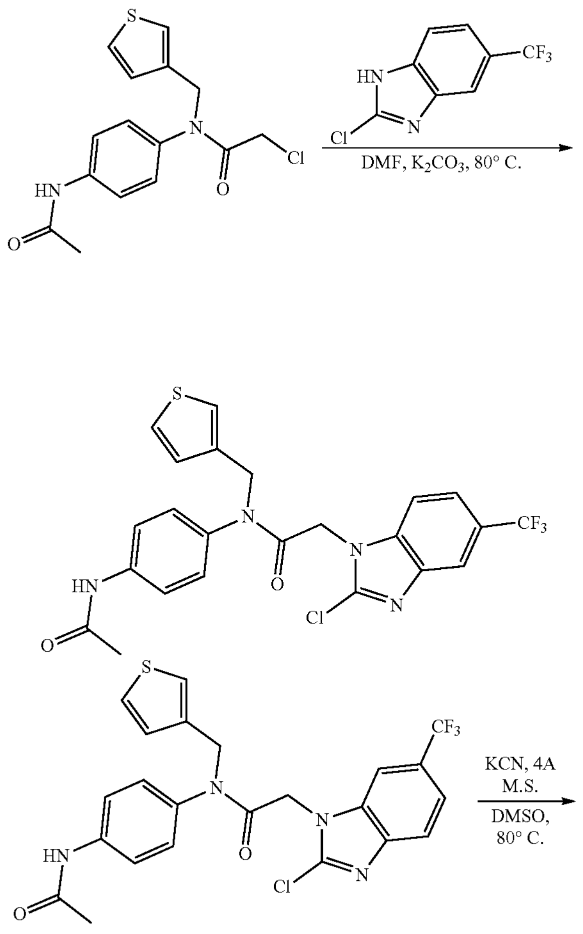

-continued

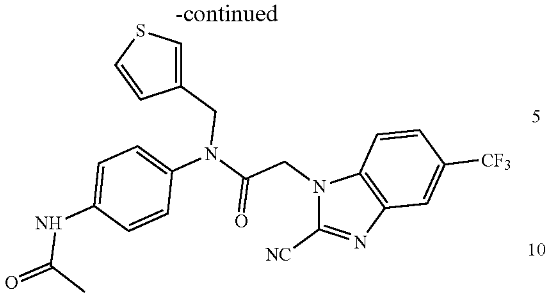

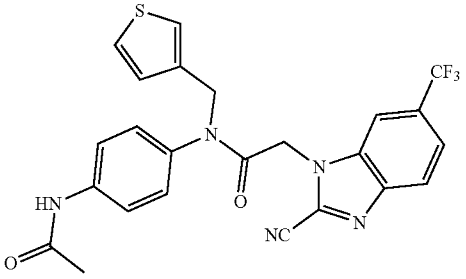

Step 1: N-(4-acetamidophenyl)-2-[2-chloro-5-(trifluoromethyl)benzimidazol-1-yl]-N-(3-thienylmethyl)acetamide and N-(4-acetamidophenyl)-2-[2-chloro-6-(trifluoromethyl)benzimidazol-1-yl]-N-(3-thienylmethyl)acetamide To a solution of N-(4-acetamidophenyl)-2-chloro-N-(3-thienylmethyl)acetamide (1 g, 3.10 mmol, 1.5 eq) in DMF (15 mL) was added 2-chloro-5-(trifluoromethyl)-1H-benzimidazole (455.54 mg, 2.07 mmol, 1 eq), $K_2CO_3$ (856.27 mg, 6.20 mmol, 3 eq), LiBr (269.03 mg, 3.10 mmol, 77.75 uL, 1.5 eq), and then the mixture was stirred at 80° C. for 4 h. The mixture was extracted with ethyl acetate (3*20 mL). The combined organic fractions were washed with water (3*20 mL), dried ($Na_2SO_4$), filtered and the solvent was evaporated under reduced pressure to give crude product. The residue was purified by prep-HPLC (column: Phenomenex Gemini-NX 80*40 mm*3 um; mobile phase: [water (10 mM $NH_4HCO_3$)-ACN]; B %: 30%-50%, 8 min) to get 800 mg isomers. The isomers was separated by SFC (600 mg) (column: DAICEL CHIRALPAK IG (250 mm*30 mm, 10 um); mobile phase: [0.1% NH3H2O ETOH]; B %: 40%-40%, min) to give N-(4-acetamidophenyl)-2-[2-chloro-5-(trifluoromethyl)benzimidazol-1-yl]-N-(3-thienylmethyl)acetamide (200 mg, 374.81 umol, 18.15% yield, 95% purity). MS (ESI) m/z 507.1 $[M+H]^+$. $^1H$ NMR (400 MHz, DMSO-$d_6$) δ ppm 1.17 (t, J=7.27 Hz, 3H) 2.06 (s, 3H) 2.99-3.18 (m, 2H) 4.83 (s, 2H) 4.96 (s, 2H) 6.95 (d, J=4.89 Hz, 1H) 7.24 (d, J=1.71 Hz, 1H) 7.31 (d, J=8.68 Hz, 2H) 7.50 (dd, J=4.77, 2.93 Hz, 1H) 7.57 (d, J=8.44 Hz, 1H) 7.67 (d, J=8.68 Hz, 2H) 7.80 (d, J=8.44 Hz, 1H) 8.15 (s, 1H) 10.14 (s, 1H).

N-(4-acetamidophenyl)-2-[2-chloro-6-(trifluoromethyl)benzimidazol-1-yl]-N-(3-thienylmethyl)acetamide (200 mg, 374.81 umol, 18.15% yield, 95% purity). MS (ESI) m/z 507.1 $[M+H]^+$. $^1H$ NMR (400 MHz, DMSO-$d_6$) δ ppm 2.05 (s, 3H) 4.82 (s, 2H) 4.92 (s, 2H) 6.94 (d, J=4.89 Hz, 1H) 7.25 (br s, 1H) 7.31 (d, J=8.68 Hz, 2H) 7.49 (dd, J=4.77, 3.06 Hz, 1H) 7.62-7.69 (m, 3H) 7.82 (d, J=8.68 Hz, 1H) 7.99 (s, 1H) 10.11 (s, 1H)

Step 2: N-(4-acetamidophenyl)-2-[2-cyano-5-(trifluoromethyl)benzimidazol-1-yl]-N-(3-thienylmethyl)acetamide To a solution of N-(4-acetamidophenyl)-2-[2-chloro-5-(trifluoromethyl)benzimidazol-1-yl]-N-(3-thienylmethyl)acetamide (200 mg, 394.53 umol, 1 eq) in DMSO (1 mL) was added 4A MS (50 mg, 394.53 umol, 1 eq), KCN (20 mg, 307.15 umol, 13.16 uL, 0.8 eq) and the mixture was stirred for 3 h at 80° C. The mixture was poured into water (30 mL), filtrated, washed with water (3*5 mL) and dried to afford the crude of $P_1$. the mixture was extracted with ethyl acetate (3*5 mL). The combined organic fractions were washed with water (5 mL×3), dried ($Na_2SO_4$), filtered and the solvent was evaporated under reduced pressure to give crude product. The crude was purified by prep-HPLC (column: Waters Xbridge Prep OBD C18 150*40 mm*10 um; mobile phase: [water (10 mM $NH_4HCO_3$)-ACN]; B %: 40%-60%, 8 min) to afford N-(4-acetamidophenyl)-2-[2-cyano-5-(trifluoromethyl)benzimidazol-1-yl]-N-(3-thienylmethyl)acetamide (30 mg, 57.29 umol, 14.52% yield, 95% purity) as a white solid. MS (ESI) m/z 498.1 $[M+H]^+$. $^1H$ NMR (400 MHz, DMSO-$d_6$) δ ppm 2.07 (s, 3H) 4.86 (s, 2H) 5.23 (s, 2H) 6.98 (dd, J=4.95, 1.04 Hz, 1H) 7.24-7.32 (m, 3H) 7.51 (dd, J=4.95, 3.00 Hz, 1H) 7.66-7.75 (m, 3H) 8.05 (d, J=8.56 Hz, 1H) 8.35 (s, 1H) 10.14 (s, 1H)

Step 3: N-(4-acetamidophenyl)-2-[2-cyano-5-(trifluoromethyl)benzimidazol-1-yl]-N-(3-thienylmethyl)acetamide To a solution of N-(4-acetamidophenyl)-2-[2-chloro-6-(trifluoromethyl)benzimidazol-1-yl]-N-(3-thienylmethyl)acetamide (200.00 mg, 394.53 umol, 1 eq) in DMSO (1.5 mL) was added 4A MS (50 mg, 394.53 umol, 1 eq) and KCN (70 mg, 1.07 mmol, 46.05 uL, 2.72 eq). After stirring for 3 h at 80° C., the resulting mixture was extracted with ethyl acetate (3*20 mL). The combined organic fractions were washed with water (3*20 mL), dried ($Na_2SO_4$), filtered and the solvent was evaporated under reduced pressure to give crude product. The crude product was purified by prep-HPLC (column: Waters Xbridge Prep OBD C18 150*40 mm*10 um; mobile phase: [water (10 mM $NH_4HCO_3$)-ACN]; B %: 40%-60%, 8 min) to afford N-(4-acetamidophenyl)-2-[2-cyano-6-(trifluoromethyl)benzimidazol-1-yl]-N-(3-thienylmethyl)acetamide (30 mg, 57.29 umol, 14.52% yield, 95% purity) as a white solid. MS (ESI) m/z 498.1 $[M+H]^+$. $^1H$ NMR (400 MHz, DMSO-$d_6$) δ ppm 2.06 (s, 3H) 4.85 (s, 2H) 5.17 (s, 2H) 6.97 (dd, J=5.01, 1.10 Hz, 1H) 7.25 (d, J=1.96 Hz, 1H) 7.30 (d, J=8.80 Hz, 2H) 7.50 (dd, J=4.89, 2.93 Hz, 1H) 7.67 (d, J=8.80 Hz, 2H) 7.84 (dd, J=8.80, 1.22 Hz, 1H) 7.99 (d, J=8.80 Hz, 1H) 8.26 (s, 1H) 10.12 (s, 1H).

Example 230: Synthesis of Compound 142, 142a and 142b

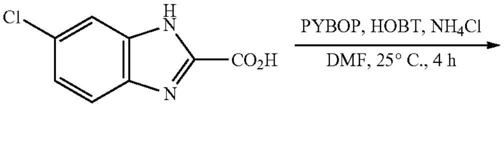

-continued

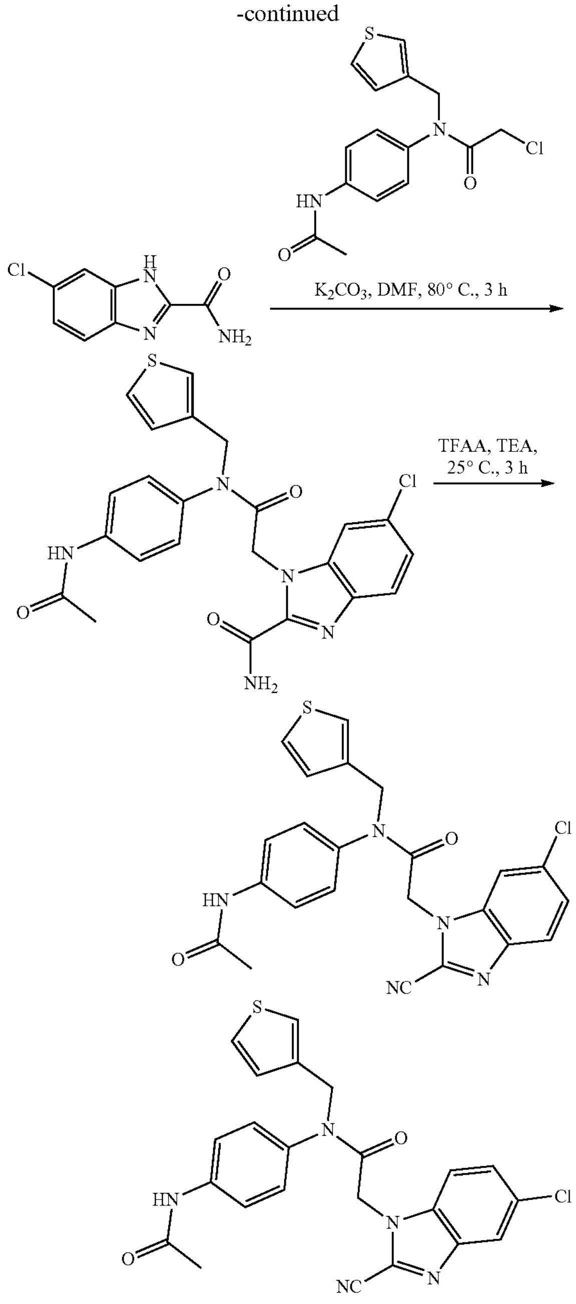

Step 1: 6-chloro-1H-benzimidazole-2-carboxamide

To a solution of 6-chloro-1H-benzimidazole-2-carboxylic acid (500 mg, 2.54 mmol, 1 eq) in DMF (5 mL) was added PYBOP (1.99 g, 3.82 mmol, 1.5 eq), $NH_4Cl$ (272.09 mg, 5.09 mmol, 2 eq), HOBt (515.49 mg, 3.82 mmol, 1.5 eq) and DIEA (1.31 g, 10.17 mmol, 1.77 mL, 4 eq). After stirring the reaction at 25° C. for 3 h, the mixture was poured into water (30 mL), filtrated, washed with water (3*5 mL). The mixture was extracted with ethyl acetate (3*5 mL). The combined organic fractions were washed with water (3*5 mL), dried ($Na_2SO_4$), filtered and the solvent was evaporated under reduced pressure to give a residue. The residue was purified by flash silica gel chromatography (ISCO®; 25 g Sepa-Flash® Silica Flash Column, Eluent of 0-100% ethyl acetate/petroleum ether gradient @ 80 mL/min) to get 6-chloro-1H-benzimidazole-2-carboxamide (380 mg, 1.65 mmol, 64.93% yield, 85% purity) as white solid). MS (ESI) m/z 196.1 $[M+H]^+$ Step 2: 1-[2-[4-acetamido-N-(3-thienylmethyl)anilino]-2-oxo-ethyl]-6-chloro-benzimidazole-2-carboxamide and 1-[2-[4-acetamido-N-(3-thienylmethyl)anilino]-2-oxo-ethyl]-5-chloro-benzimidazole-2-carboxamide To a solution of N-(4-acetamidophenyl)-2-chloro-N-(3-thienylmethyl)acetamide (330.06 mg, 1.02 mmol, 1 eq) in DMF (5 mL) was added 6-chloro-1H-benzimidazole-2-carboxamide (200 mg, 1.02 mmol, 1 eq), $K_2CO_3$ (423.93 mg, 3.07 mmol, 3 eq), and LiBr (133.19 mg, 1.53 mmol, 38.50 uL, 1.5 eq). After stirring at 80° C. for 3 h, the mixture was extracted with ethyl acetate (3*30 mL). The combined organic fractions were washed with water (3*30 mL), dried ($Na_2SO_4$), filtered and the solvent was evaporated under reduced pressure to give crude product. The residue was purified by prep-HPLC (column: Waters Xbridge BEH C18 100*30 mm*10 um; mobile phase: [water (10 mM $NH_4HCO_3$)-ACN]; B %: 28%-58%, 6 min to give 90 mg isomers. The isomers was separated by SFC (column: DAICEL CHIRALCEL OJ (250 mm*30 mm, 10 um); mobile phase: [0.1% $NH_3H_2O$ ETOH]; B %: 40%-40%, 10 min) to afford 1-[2-[4-acetamido-N-(3-thienylmethyl)anilino]-2-oxo-ethyl]-6-chloro-benzimidazole-2-carboxamide (30 mg, 59.13 umol, 5.78% yield, 95% purity) as a white solid and 1-[2-[4-acetamido-N-(3-thienylmethyl)anilino]-2-oxo-ethyl]-5-chloro-benzimidazole-2-carboxamide (30 mg, 59.13 umol, 5.78% yield, 95% purity) as white solid. MS (ESI) m/z 482.1 $[M+H]^+$ Step 3: N-(4-acetamidophenyl)-2-(6-chloro-2-cyano-benzimidazol-1-yl)-N-(3-thienylmethyl)acetamide A solution of 1-[2-[4-acetamido-N-(3-thienylmethyl)anilino]-2-oxo-ethyl]-6-chloro-benzimidazole-2-carboxamide (20.00 mg, 41.50 umol, 1 eq) in THF (1 mL) was added TEA (10.50 mg, 103.74 umol, 14.44 uL, 2.5 eq), and TFAA (17.43 mg, 83.00 umol, 11.54 uL, 2 eq) was stirred at 25° C. for 2 h. The solution was diluted with $H_2O$ (10 mL) extracted with ethyl acetate (3*20 mL), the combined organic phase was dried over $Na_2SO_4$, filtrated and concentrated to give the crude. The crude was purified by prep-HPLC (column: Waters Xbridge BEH C18 100*30 mm*10 um; mobile phase: [water (10 mM $NH_4HCO_3$)-ACN]; B %: 25%-55%, 8 min) to afford N-(4-acetamidophenyl)-2-(6-chloro-2-cyano-benzimidazol-1-yl)-N-(3-thienylmethyl)acetamide (10 mg, 20.48 umol, 49.34% yield, 95% purity) as a white solid. MS (ESI) m/z 464.1 $[M+H]^+$. $^1H$ NMR (400 MHz, CHLOROFORM-$d_6$) δ ppm 2.22 (s, 3H) 4.76 (s, 2H) 4.87 (s, 2H) 6.99 (d, J=4.85 Hz, 1H) 7.02-7.08 (m, 3H) 7.28-7.32 (m, 2H) 7.33-7.41 (m, 2H) 7.63 (br d, J=8.38 Hz, 2H) 7.77 (d, J=8.82 Hz, 1H)

Step 4: N-(4-acetamidophenyl)-2-(5-chloro-2-cyano-benzimidazol-1-yl)-N-(3-thienylmethyl)acetamide To a solution of 1-[2-[4-acetamido-N-(3-thienylmethyl)anilino]-2-oxo-ethyl]-5-chloro-benzimidazole-2-carboxamide (20.00 mg, 41.50 umol, 1 eq) in THF (1 mL) was added TEA (10.50 mg, 103.74 umol, 14.44 uL, 2.5 eq) and TFAA (17.43 mg, 83.00 umol, 11.54 uL, 2 eq). After stirring at 25° C. for 2 h, the solution was diluted with $H_2O$ (10 mL), extracted with ethyl acetate (3*20 mL), the combined organic phase was dried over $Na_2SO_4$, filtrated and concentrated to give the crude. The aqueous phase was quenched with the solution of NaClO, and the solution was adjusted pH=12 by the solution of NaOH (2 M). The crude was purified by prep-HPLC (column: Waters Xbridge BEH C18 100*30 mm*10 um; mobile phase: [water (10 mM $NH_4HCO_3$)-ACN]; B %: 25%-55%, 8 min) to get N-(4-acetamidophenyl)-2-(5-chloro-2-cyano-benzimidazol-1-yl)-N-(3-thienylmethyl)acetamide (10 mg, 20.48 umol, 49.34% yield, 95% purity) as white solid. MS (ESI) m/z 464.1 $[M+H]^+$. $^1H$ NMR (400 MHz, CHLOROFORM-$d_6$) δ ppm 2.23 (s, 3H) 4.79 (s, 2H) 4.86 (s, 2H) 6.97 (d, J=4.85 Hz, 1H) 7.03 (s, 2H) 7.05 (s, 1H) 7.23 (d, J=8.82 Hz, 1H) 7.28-7.34 (m, 2H) 7.44 (dd, J=8.71, 1.65 Hz, 1H) 7.62 (br d, J=8.60 Hz, 2H) 7.85 (d, J=1.54 Hz, 1H) 7.83-7.87 (m, 1H)

Example 231: Synthesis of Compound 145a and 145b

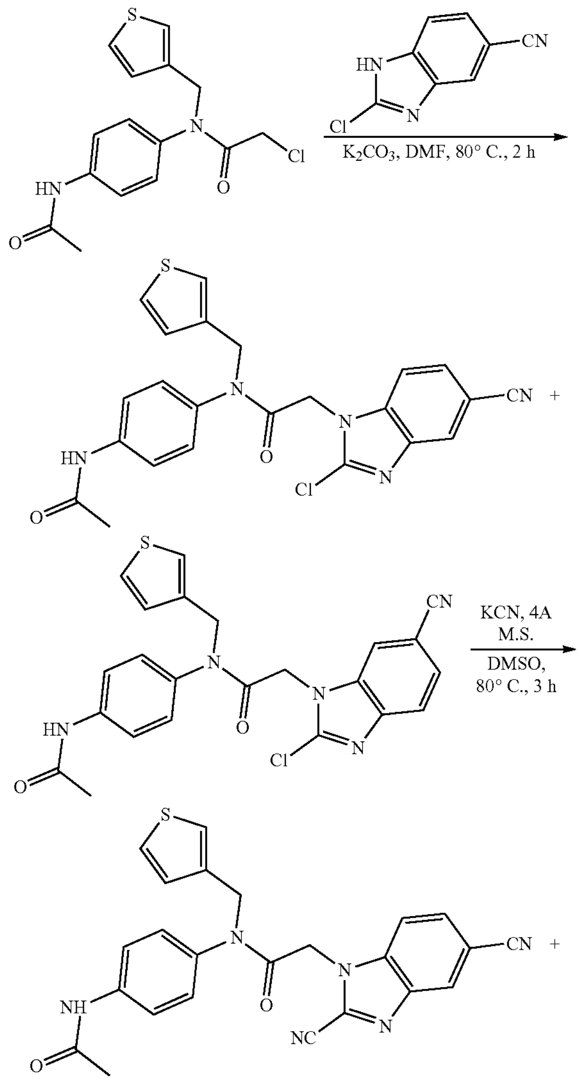

-continued

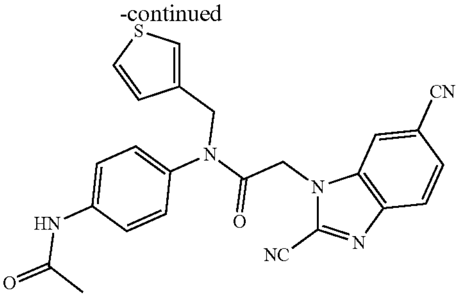

Step 1: N-(4-acetamidophenyl)-2-(2-chloro-6-cyano-benzimidazol-1-yl)-N-(3-thienylmethyl)acetamide and N-(4-acetamidophenyl)-2-(2-chloro-5-cyano-benzimidazol-1-yl)-N-(3-thienylmethyl)acetamide To a solution of N-(4-acetamidophenyl)-2-chloro-N-(3-thienylmethyl)acetamide (600 mg, 1.86 mmol, 1 eq) and 2-chloro-3H-benzimidazole-5-carbonitrile (264.07 mg, 1.49 mmol, 0.8 eq) in DMF (4 mL) was added LiBr (242.14 mg, 2.79 mmol, 69.98 uL, 1.5 eq), $K_2CO_3$ (256.88 mg, 1.86 mmol, 1 eq), and then the resulting mixture was stirred at 80° C. for 2 h. HPLC and LCMS showed the desired MS was detected. The solution was diluted with the saturated $H_2O$ (20 mL), extracted with ethyl acetate (3*10 mL), the combined organic phase was dried over $Na_2SO_4$, filtrated and concentrated to give the crude. The residue was purified by column chromatography ($SiO_2$, petroleum ether/ethyl acetate=0/1) and SFC to afford N-(4-acetamidophenyl)-2-(2-chloro-6-cyano-benzimidazol-1-yl)-N-(3-thienylmethyl) acetamide (49.73 mg, 104.44 umol, 5.62% yield, 97.43% purity) (white solid) and N-(4-acetamidophenyl)-2-(2-chloro-5-cyano-benzimidazol-1-yl)-N-(3-thienylmethyl)acetamide (26 mg, 53.44 umol, 2.88% yield, 95.36% purity) as a white solid.

145a: $^1H$ NMR (400 MHz, DMSO-$d_6$): δ ppm 2.06 (s, 3H), 4.82 (s, 2H), 4.90 (s, 2H), 5.75 (s, 1H), 6.95 (dd, J=4.93, 1.21 Hz, 1H), 7.25 (d, J=1.75 Hz, 1H), 7.32 (d, J=8.77 Hz, 2H), 7.50 (dd, J=4.93, 2.96 Hz, 1H), 7.63-7.69 (m, 3H), 7.79 (d, J=8.33 Hz, 1H), 8.30 (d, J=0.88 Hz, 1H), 10.12 (s, 1H). MS (ESI) m/z 464.0 $[M+H]^+$ 145b: $^1H$ NMR (400 MHz, DMSO-$d_6$): δ ppm 2.04 (s, 3H), 4.80 (s, 2H), 4.90 (s, 2H), 6.93 (dd, J=4.82, 1.10 Hz, 1H), 7.23 (d, J=1.75 Hz, 1H), 7.29 (d, J=8.77 Hz, 2H), 7.48 (dd, J=4.82, 3.07 Hz, 1H), 7.65 (d, J=8.77 Hz, 2H), 7.70-7.74 (m, 1H), 7.78-7.82 (m, 1H), 8.18 (d, J=0.88 Hz, 1H), 10.10 (s, 1H). MS (ESI) m/z 464.1 $[M+H]^+$ Step 2: N-(4-acetamidophenyl)-2-(2,5-dicyanobenzimidazol-1-yl)-N-(3-thienylmethyl)acetamide and N-(4-acetamidophenyl)-2-(2,6-dicyanobenzimidazol-1-yl)-N-(3-thienylmethyl)acetamide To a mixture of N-(4-acetamidophenyl)-2-(2-chloro-6-cyano-benzimidazol-1-yl)-N-(3-thienylmethyl)acetamide and N-(4-acetamidophenyl)-2-(2-chloro-5-cyano-benzimidazol-1-yl)-N-(3-thienylmethyl)acetamide (400 mg, 862.18 umol, 1 eq) in DMSO (4 mL) was added KCN (680 mg, 10.44 mmol, 447.37 uL, 12.11 eq) and 4A MS (400.00 mg, 4.00 mmol, 4.64 eq). The resulting solution was stirred at 80° C. for 3 h. HPLC and LCMS showed the reaction was finished. $H_2O$ (50 mL) was added and extracted with ethyl acetate (30 mL*3), the combined organic phases were washed with NaCl aq (90 mL*2) to give the crude. The crude product was purified by prep-HPLC (column: Phenomenex luna C18 80*40 mm*3 um; mobile phase: [water (0.04% HCl)-ACN]; B %: 40%-60%, 7 min) and SFC (column: DAICEL CHIRALCEL OD (250 mm*50 mm, 10 um); mobile phase: [0.1% NH3H2O ETOH]; B %: 38%-38%, min) to afford N-(4-acetamidophenyl)-2-(2,5-dicyano-benzimidazol-1-yl)-N-(3-thienylmethyl)acetamide (8.24 mg, 18.06 umol, 2.09% yield, 99.603% purity) as a white solid, and N-(4-acetamidophenyl)-2-(2,6-dicyanobenzimidazol-1-yl)-N-(3-thienylmethyl)acetamide (7.48 mg, 16.38 umol, 1.90% yield, 99.544% purity) as a white solid.

HNMR: S2A_12_P1: $^1$H NMR (400 MHz, DMSO-$d_6$) δ ppm 2.06 (s, 3H) 4.85 (s, 2H) 5.15 (s, 2H) 6.97 (s, 1H) 7.29-7.31 (m, 3H) 7.51 (s, 1H) 7.62-7.69 (s, 2H) 7.78-7.80 (s, 1H) 7.80-7.81 (s, 1H) 8.50 (s, 1H) 10.13 (s, 1H). MS (ESI) m/z 455.2 $[M+H]^+$ HNMR: S2A_12_P2: $^1$H NMR (400 MHz, DMSO-$d_6$) δ ppm 2.05 (s, 3H) 4.84 (s, 2H) 5.15 (s, 2H) 6.95 (s, 1H) 7.28-7.30 (m, 3H) 7.49 (s, 1H) 7.66-7.68 (s, 2H) 7.91-7.92 (m, 2H) 8.48 (s, 1H) 10.13 (s, 1H). MS (ESI) m/z 455.2 $[M+H]^+$ Example 232: Synthesis of Compound 151

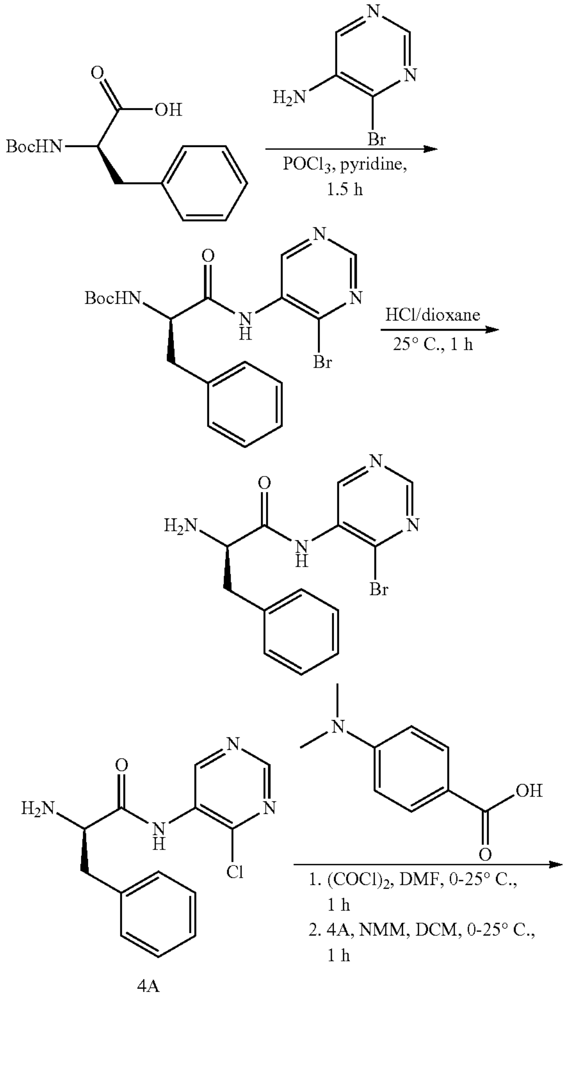

4A

-continued

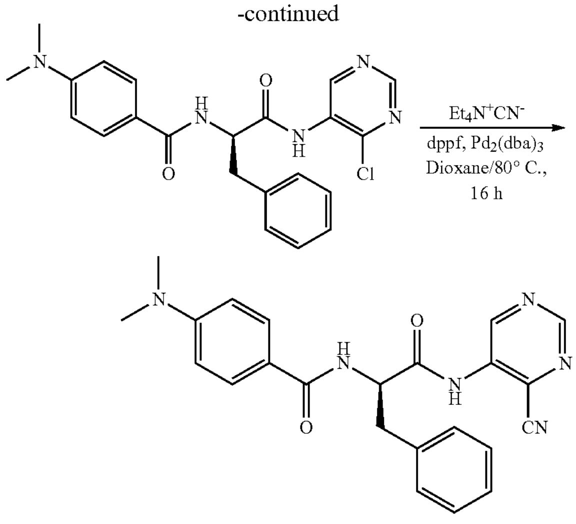

Step 1: (R)-tert-butyl (1-((4-bromopyrimidin-S-yl) amino)-1-oxo-3-phenylpropan-2-yl)carbamate A solution of (R)-2-((tert-butoxycarbonyl)amino)-3-phenylpropanoic acid (300 mg, 1.13 mmol, 1 eq) and 4-bromopyrimidin-5-amine (196.75 mg, 1.13 mmol, 1 eq) in pyridine (5 mL) was cooled to −15° C., and $POCl_3$ (190.72 mg, 1.24 mmol, 115.59 uL, 1.1 eq) was added dropwise with vigorous stirring. The mixture was stirred for 1.5 h at −15° C. The resulting mixture was poured into brine (20 mL), and then extracted with ethyl acetate (10 mL*3). The combined organic phase was washed with saturated $NaHCO_3$, filtrate was concentrated under reduced pressure. The crude was purified by prep-TLC (petroleum ether:ethyl acetate=2:1) to get the (R)-tert-butyl (1-((4-bromopyrimidin-5-yl)amino)-1-oxo-3-phenylpropan-2-yl)carbamate (280 mg, 664.63 umol, 58.78% yield) as a yellow oil.

Step 2: (R)-2-amino-N-(4-chloropyrimidin-5-yl)-3-phenylpropanamide

To a stirred solution of (R)-tert-butyl (1-((4-bromopyrimidin-5-yl)amino)-1-oxo-3-phenylpropan-2-yl)carbamate (280 mg, 664.63 umol, 1 eq) was added HCl/dioxane (4 M, 166.16 uL, 1 eq). After stirring for 25° C. for 1 h, the mixture was concentrated in vacuum to afford (R)-2-amino-N-(4-chloropyrimidin-5-yl)-3-phenylpropanamide (170 mg, crude) as a yellow oil.

Step 3: (R)—N-(1-((4-chloropyrimidin-5-yl)amino)-1-oxo-3-phenylpropan-2-yl)-4-(dimethylamino)benzamide To a stirred solution of oxalyl dichloride (2.31 g, 18.16 mmol, 1.59 mL, 3 eq) in DCM (20 mL) was added 4-(dimethylamino)benzoic acid (1 g, 6.05 mmol, 1 eq) and 3 drops DMF at 0° C., and the mixture was stirred at 25° C. for 1 h. Upon completion reaction, the mixture was concentrated in vacuum directly to obtain the 4-(dimethylamino) benzoyl chloride. To a stirred solution of 4-(dimethylamino) benzoyl chloride (151.30 mg, 823.93 umol, 1.2 eq) in DCM (10 mL) was added (R)-2-amino-N-(4-chloropyrimidin-5-yl)-3-phenylpropanamide (190 mg, 686.61 umol, 1 eq) and 4-methylmorpholine (173.62 mg, 1.72 mmol, 188.72 uL, 2.5 eq) at 0° C., and then the mixture was stirred at 25° C. for 1 h. The reaction was poured into $H_2O$ (30 mL). The mixture was extracted with DCM (10 mL*3). The organic layer was concentrated in vacuum directly to get crude, the crude was purified by prep-TLC (petroleum ether:ethyl acetate=2:1) to obtain a residue. The residue was purified by prep-HPLC (column: Waters Xbridge BEH C18 100*25 mm*5 um; mobile phase: [water (10 mM $NH_4HCO_3$)-ACN]; B %: 25%-60%, 10 min) to afford (R)—N-(1-((4-chloropyrimidin-5-yl)amino)-1-oxo-3-phenylpropan-2-yl)-4-(dimethylamino)benzamide (17 mg, 39.74 umol, 5.79% yield, 99.08% purity) as a white solid. MS (ESI) m/z 424.1 $[M+H]^+$. $^1H$ NMR (400 MHz, METHANOL-$d_4$) δ ppm 9.25 (s, 1H), 8.72 (s, 1H), 7.72-7.64 (m, 2H), 7.38-7.18 (m, 5H), 6.76-6.68 (m, 2H), 5.05-4.99 (m, 1H), 3.38-3.32 (m, 1H), 3.24-3.16 (m, 1H), 3.02 (s, 6H).

Step 4: (R)—N-(1-((4-cyanopyrimidin-5-yl)amino)-1-oxo-3-phenylpropan-2-yl)-4-(dimethylamino)benzamide To a stirred solution of (R)—N-(1-((4-chloropyrimidin-5-yl)amino)-1-oxo-3-phenylpropan-2-yl)-4-(dimethylamino)benzamide (200.00 mg, 424.63 umol, 90% purity, 1 eq) in dioxane (3 mL) was added tetraethylammonium; cyanide (132.71 mg, 849.27 umol, 2 eq), DPPF (4.71 mg, 8.49 umol, 0.02 eq) and $Pd_2(dba)_3$ (38.88 mg, 42.46 umol, 0.1 eq). The resulting mixture was stirred at 80° C. for 16 h. Upon reaction completion, the mixture was poured into $H_2O$ (10 mL), and then the mixture was filtered through celite pad, and the mixture was extracted with ethyl acetate (10 mL*3), the organic layer was concentrated in vacuum directly to get the crude. The product was purified by prep-HPLC (column: Phenomenex Luna C18 100*30 mm*5 um; mobile phase: [water (0.1% TFA)-ACN]; B %: 25%-55%, 10 min) to afford (R)—N-(1-((4-cyanopyrimidin-5-yl)amino)-1-oxo-3-phenylpropan-2-yl)-4-(dimethylamino)benzamide (5.5 mg, 13.27 umol, 3.13% yield, 100% purity) as a white solid. MS (ESI) m/z 415.0 $[M+H]^+$.

$^1H$ NMR (400 MHz, METHANOL-$d_4$) δ ppm 9.27 (s, 1H), 9.05 (s, 1H), 7.86-7.59 (m, 2H), 7.45-7.26 (m, 4H), 7.26-7.18 (m, 1H), 6.86-6.67 (m, 2H), 5.05-4.96 (m, 1H), 3.40-3.36 (m, 1H), 3.26-3.17 (m, 1H), 3.03 (s, 6H).

Example 233: Synthesis of Compound 152

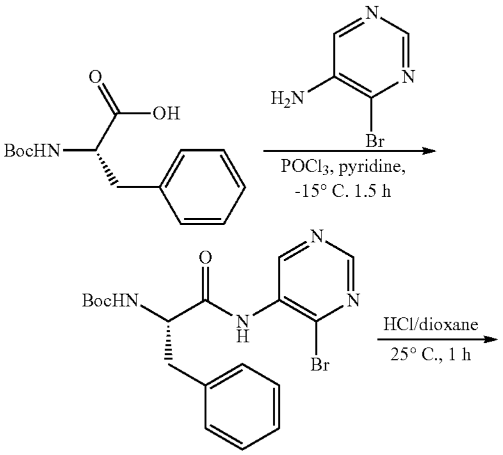

-continued

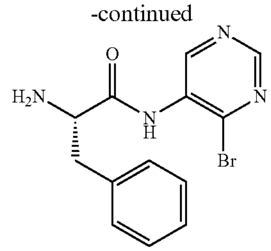

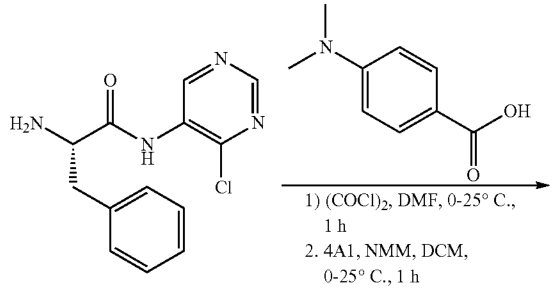

4A1

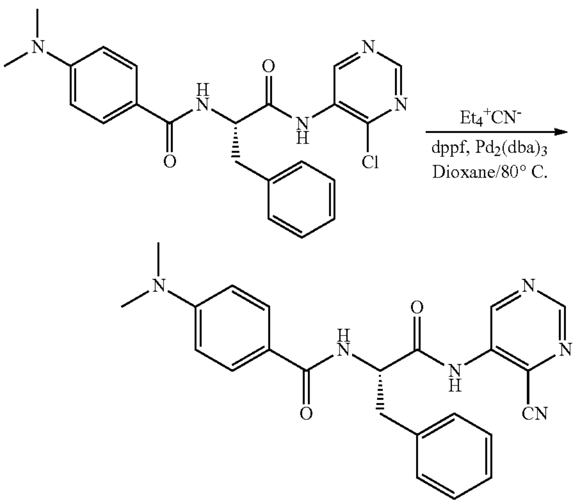

Step 1: (S)-tert-butyl (1-((4-bromopyrimidin-5-yl)amino)-1-oxo-3-phenylpropan-2-yl)carbamate A solution of (S)-2-((tert-butoxycarbonyl)amino)-3-phenylpropanoic acid (1.52 g, 5.75 mmol, 1 eq) and 4-bromopyrimidin-5-amine (1 g, 5.75 mmol, 1 eq) in pyridine (100 mL) was cooled to −15° C., and then $POCl_3$ (944.00 mg, 6.16 mmol, 572.12 uL, 1.07 eq) was added dropwise with vigorous stirring. The mixture was stirred for 1.5 h at −15° C. Upon reaction completion, the reaction was poured into brine (300 mL). The mixture was extracted with ethyl acetate (200 mL*3). The combined organic phase was washed with saturated $NaHCO_3$, filtrate was concentrated under reduced pressure. The crude was purified by prep-TLC (petroleum ether:ethyl acetate=2:1) to get the (S)-tert-butyl (1-((4-bromopyrimidin-5-yl)amino)-1-oxo-3-phenylpropan-2-yl)carbamate (420 mg, 996.94 umol, 17.35% yield) as yellow oil. MS (ESI) m/z 421.1 $[M-56]^+$ Step 2: (S)-2-amino-N-(4-chloropyrimidin-5-yl)-3-phenylpropanamide To a stirred solution of (S)-tert-butyl (1-((4-bromopyrimidin-5-yl)amino)-1-oxo-3-phenylpropan-2-yl)carbamate (420.00 mg, 996.94 umol, 1 eq) was added HCl/dioxane (4 M, 4.98 mL, 20 eq). After stirring at 25° C. for 1 h, the mixture was concentrated in vacuum directly to afford (S)-2-amino-N-(4-chloropyrimidin-5-yl)-3-phenylpropanamide (270 mg, crude) used directly. MS (ESI) m/z 577.4 $[M+H]^+$ Step 3: (S)—N-(1-((4-chloropyrimidin-5-yl)amino)-1-oxo-3-phenylpropan-2-yl)-4-(dimethylamino)benzamide To a stirred solution of oxalyl dichloride (2.31 g, 18.16 mmol, 1.59 mL, 3 eq) in DCM (20 mL) was added 4-(dimethylamino)benzoic acid (1 g, 6.05 mmol, 1 eq) and 3 drops DMF at 0° C., and the mixture was stirred at 25° C. for 1 h. Upon reaction completion, the mixture was concentrated in vacuum directly to get the 4-(dimethylamino) benzoyl chloride. To a stirred solution of 4-(dimethylamino) benzoyl chloride (215.01 mg, 1.17 mmol, 1.2 eq) in DCM (10 mL) was added (S)-2-amino-N-(4-chloropyrimidin-5-yl)-3-phenylpropanamide (270 mg, 975.71 umol, 1 eq) and 4-methylmorpholine (246.73 mg, 2.44 mmol, 268.19 uL, 2.5 eq) at 0° C. After stirring at 25° C. for 1 h, the reaction was poured into $H_2O$ (30 mL). The mixture was extracted with DCM (10 mL*3). The organic layer was concentrated in vacuum directly to get crude, the crude was purified by prep-TLC (petroleum ether:ethyl acetate=2:1) to obtain a residue. The residue was purified by prep-HPLC (column: Waters Xbridge Prep OBD C18 150*40 mm*10 um; mobile phase: [water (10 mM NH4HCO3)-ACN]; B %: 30%-60%, 8 min) to afford (S)—N-(1-((4-chloropyrimidin-5-yl) amino)-1-oxo-3-phenylpropan-2-yl)-4-(dimethylamino) benzamide (18.77 mg, 43.48 umol, 4.46% yield, 98.2% purity) as a white solid for delivery. MS (ESI) m/z 424.1 $[M+H]^+$. $^1H$ NMR (400 MHz, METHANOL-$d_4$) δ ppm 9.25 (s, 1H), 8.71 (m, 1H), 7.71-7.65 (m, 2H), 7.38-7.32 (m, 2H), 7.32-7.26 (m, 2H), 7.24-7.18 (m, 1H), 6.75-6.68 (m, 2H), 5.06-4.97 (m, 1H), 3.39-3.32 (m, 1H), 3.25-3.16 (m, 1H), 3.02 (s, 6H).

Step 4: (S)—N-(1-((4-cyanopyrimidin-S-yl)amino)-1-oxo-3-phenylpropan-2-yl)-4-(dimethylamino)benzamide To a stirred solution of (S)—N-(1-((4-chloropyrimidin-5-yl)amino)-1-oxo-3-phenylpropan-2-yl)-4-(dimethylamino) benzamide (200 mg, 424.63 umol, 90% purity, 1 eq) in dioxane (2 mL) was added tetraethylammonium;cyanide (132.71 mg, 849.27 umol, 2 eq), DPPF (4.71 mg, 8.49 umol, 0.02 eq) and $Pd_2(dba)_3$ (38.88 mg, 42.46 umol, 0.1 eq). After stirring at 80° C. for 14 h, the mixture was poured into $H_2O$ (10 mL), and then the mixture was filtered through celite pad, and the mixture was extracted with ethyl acetate (10 mL*3), the organic layer was concentrated in vacuum directly to get the crude. The product was purified by prep-HPLC (column: Phenomenex Gemini-NX 150*30 mm*5 um; mobile phase: [water (0.1% TFA)-ACN]; B %: 40%-70%, 9 min) to afford (S)—N-(1-((4-cyanopyrimidin-5-yl)amino)-1-oxo-3-phenylpropan-2-yl)-4-(dimethylamino)benzamide (5.92 mg, 13.39 umol, 3.15% yield, 93.74% purity) as a white solid. MS (ESI) m/z 415.1 $[M+H]^+$. $^1H$ NMR (400 MHz, METHANOL-$d_4$) δ ppm 9.27 (s, 1H), 9.05 (s, 1H), 7.75-7.67 (m, 2H), 7.39-7.33 (m, 2H), 7.33-7.27 (m, 2H), 7.25-7.19 (m, 1H), 6.81-6.74 (m, 2H), 5.03-4.97 (m, 1H), 3.40-3.34 (m, 1H), 3.26-3.18 (m, 1H), 3.04 (s, 6H).

Example 234: Synthesis of Compound 152a

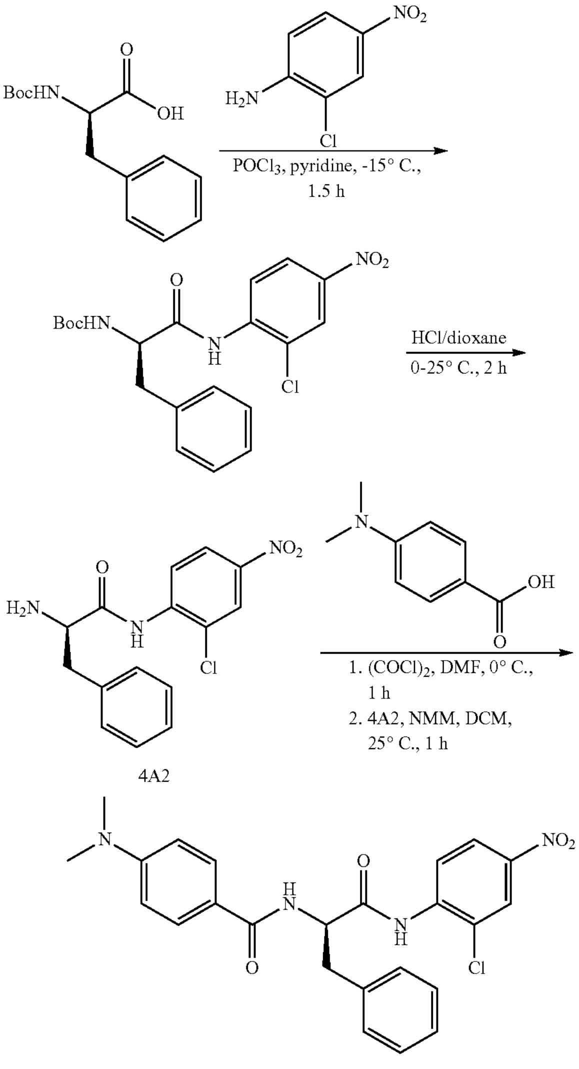

4A2

Step 1: (R)-tert-butyl (1-((2-chloro-4-nitrophenyl) amino)-1-oxo-3-phenylpropan-2-yl)carbamate A solution of (R)-2-((tert-butoxycarbonyl)amino)-3-phenylpropanoic acid (2.65 g, 9.99 mmol, 1 eq) and 2-chloro-4-nitro-aniline (1.72 g, 9.99 mmol, 1 eq) in pyridine (30 mL) was cooled to −15° C., and then $POCl_3$ (1.53 g, 9.99 mmol, 928.20 uL, 1 eq) was added dropwise with vigorous stirring. After stirring for 1.5 h at −15° C., the reaction was quenched by pouring into ice-water (100 mL). The mixture was extracted with ethyl acetate (50 mL*3). The combined organic phase was washed with saturated $NaHCO_3$ (50 mL) and brine (30 mL). The organic phase was dried over $MgSO_4$ and filtered, and the filtrate was concentrated under reduced pressure. The residue was purified by prep-TLC (petroleum ether:ethyl acetate=1:1) to afford (R)-tert-butyl (1-((2-chloro-4-nitrophenyl)amino)-1-oxo-3-phenylpropan-2-yl)carbamate (900 mg, 2.14 mmol, 21.46% yield) as a white solid. MS (ESI) m/z 421.1 $[M+H]^+$ Step 2: (R)-2-amino-N-(2-chloro-4-nitrophenyl)-3-phenylpropanamide To a stirred solution of (R)-tert-butyl (1-((2-chloro-4-nitrophenyl)amino)-1-oxo-3-phenylpropan-2-yl)carbamate (500.00 mg, 1.19 mmol, 1 eq) was added HCl/dioxane (4 M, 9.53 mL, 20 eq) at 0° C. After stirring at 25° C. for 2 h, the mixture was concentrated in vacuum directly to get the (R)-2-amino-N-(2-chloro-4-nitrophenyl)-3-phenylpropanamide (410 mg, crude) used directly. MS (ESI) m/z 320.1 $[M+H]^+$ Step 3: (R)—N-(1-((2-chloro-4-nitrophenyl)amino)-1-oxo-3-phenylpropan-2-yl)-4-(dimethylamino)benzamide To a stirred solution of oxalyl dichloride (2.31 g, 18.16 mmol, 1.59 mL, 3 eq) in DCM (20 mL) was added 4-(dimethylamino)benzoic acid (1 g, 6.05 mmol, 1 eq) and 3 drops DMF at 0° C. After stirring at 25° C. for 1 h, the mixture was concentrated in vacuum directly to get the 4-(dimethylamino)benzoyl chloride. To a stirred solution of 4-(dimethylamino)benzoyl chloride (327.36 mg, 1.78 mmol, 1.5 eq) in DCM (10 mL) was added (R)-2-amino-N-(2-chloro-4-nitrophenyl)-3-phenylpropanamide (380.00 mg, 1.19 mmol, 1 eq) and 4-methylmorpholine (300.52 mg, 2.97 mmol, 326.65 uL, 2.5 eq) at 0° C., and then the mixture was stirred at 25° C. for 1 h. The reaction was poured into $H_2O$ (30 mL), and then the mixture was extracted with DCM (20 mL*3). The organic layer was concentrated in vacuum directly to get crude, the crude was purified by prep-HPLC (column: Phenomenex Gemini-NX 80*40 mm*3 um; mobile phase: [water (10 mM NH4HCO3)-ACN]; B %: 50%-80%, 8 min) to afford (R)—N-(1-((2-chloro-4-nitrophenyl)amino)-1-oxo-3-phenylpropan-2-yl)-4-(dimethylamino)benzamide (91.71 mg, 184.95 umol, 15.56% yield, 94.16% purity) as a white solid. MS (ESI) m/z 467.0 $[M+H]^+$ $^1H$ NMR (400 MHz, CHLOROFORM-d) δ ppm 9.23 (s, 1H), 8.66-8.54 (m, 1H), 8.21-8.16 (m, 1H), 8.12-8.04 (m, 11H), 7.61-7.48 (m, 2H), 7.27 (s, 4H), 7.21-7.20 (m, 1H), 6.62-6.55 (m, 2H), 6.39-6.32 (m, 1H), 5.07-4.94 (m, 1H), 3.33-3.21 (m, 2H), 3.04 (s, 6H).

Example 235: Synthesis of Compound 154

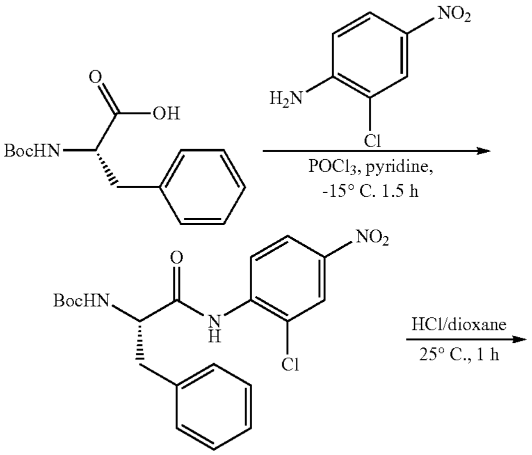

-continued

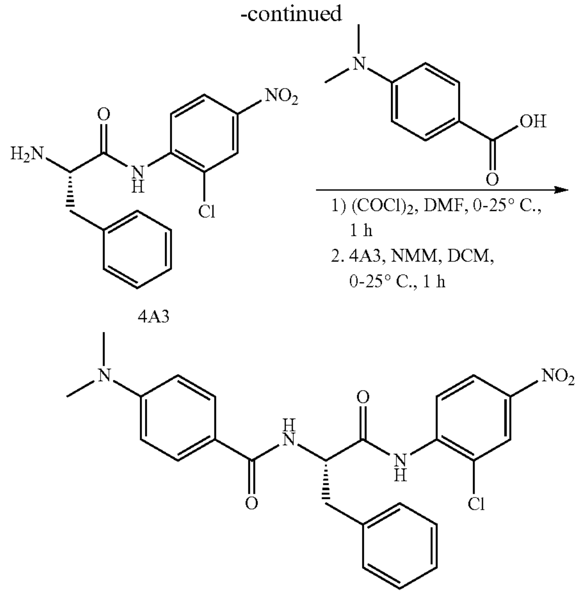

4A3

Step 1: (S)-tert-butyl (1-((2-chloro-4-nitrophenyl)amino)-1-oxo-3-phenylpropan-2-yl)carbamate A solution of (S)-2-((tert-butoxycarbonyl)amino)-3-phenylpropanoic acid (1 g, 3.77 mmol, 1 eq) and 2-chloro-4-nitro-aniline (650.46 mg, 3.77 mmol, 1 eq) in pyridine (50 mL) was cooled to −15° C., and then $POCl_3$ (1.72 g, 11.22 mmol, 1.04 mL, 2.98 eq) was added dropwise with vigorous stirring. After stirring for 1.5 h at −15° C., the reaction was quenched by pouring into ice-water (100 mL). The mixture was extracted with ethyl acetate (50 mL*3). The combined organic phase was washed with saturated $NaHCO_3$ (50 mL) and brine (30 mL). The organic phase was dried over $MgSO_4$ and filtered, and the filtrate was concentrated under reduced pressure. The residue was purified by flash silica gel column chromatography ($SiO_2$, petroleum ether:ethyl acetate=1:1) to afford (S)-tert-butyl (1-((2-chloro-4-nitrophenyl)amino)-1-oxo-3-phenylpropan-2-yl)carbamate (800 mg, 1.91 mmol, 50.55% yield) as a yellow oil. MS (ESI) m/z 364.0 $[M-56]^+$ Step 2: (S)-2-amino-N-(2-chloro-4-nitrophenyl)-3-phenylpropanamide To a stirred solution of (S)-tert-butyl (1-((2-chloro-4-nitrophenyl)amino)-1-oxo-3-phenylpropan-2-yl)carbamate (800 mg, 1.91 mmol, 1 eq) was added HCl/dioxane (4 M, 9.53 mL, 20 eq). After stirring at 25° C. for 1 h, the mixture was concentrated in vacuum directly to afford (S)-2-amino-N-(2-chloro-4-nitrophenyl)-3-phenylpropanamide (610 mg, crude) used directly. MS (ESI) m/z 320.0 $[M+H]^+$ Step 3: (S)—N-(1-((2-chloro-4-nitrophenyl)amino)-1-oxo-3-phenylpropan-2-yl)-4-(dimethylamino)benzamide To a stirred solution of oxalyl dichloride (2.31 g, 18.16 mmol, 1.59 mL, 3 eq) in DCM (20 mL) was added 4-(dimethylamino)benzoic acid (1 g, 6.05 mmol, 1 eq) and 3 drops DMF at 0° C. After stirring at 25° C. for 1 h, the mixture was concentrated in vacuum directly to get the 4-(dimethylamino)benzoyl chloride. To a stirred solution of 4-(dimethylamino)benzoyl chloride (525.50 mg, 2.86 mmol, 1.5 eq) in DCM (10 mL) was added (S)-2-amino-N-(2-chloro-4-nitrophenyl)-3-phenylpropanamide (610.00 mg, 1.91 mmol, 1 eq) and 4-methylmorpholine (482.43 mg, 4.77 mmol, 524.38 uL, 2.5 eq) at 0° C., and the mixture was stirred at 25° C. for 1 h. The reaction was poured into $H_2O$ (30 mL). The mixture was extracted with DCM (20 mL*3). The organic layer was concentrated in vacuum directly to get crude, the crude was purified by prep-HPLC (column: Phenomenex Gemini-NX C18 75*30 mm*3 um; mobile phase: [water (10 mM $NH_4HCO_3$)-ACN]; B %: 45%-65%, 6 min) to afford (S)—N-(1-((2-chloro-4-nitrophenyl) amino)-1-oxo-3-phenylpropan-2-yl)-4-(dimethylamino) benzamide (122.8 mg, 255.48 umol, 13.39% yield, 97.14% purity) as a white solid. MS (ESI) m/z 467.0 $[M+H]^+$ $^1H$ NMR (400 MHz, CHLOROFORM-d) δ ppm 9.18 (s, 11H), 8.69-8.62 (m, 11H), 8.26-8.22 (m, 1H), 8.17-8.10 (m, 1H), 7.64-7.56 (m, 2H), 7.37-7.30 (m, 4H), 7.30-7.27 (m, 1H), 6.69-6.58 (m, 2H), 6.46-6.37 (m, 1H), 5.14-5.01 (m, 1H), 3.37-3.31 (m, 2H), 3.04 (s, 6H).

Example 236: Evaluation of Broad-Spectrum Coronaviral $3CL_{pro}$ Inhibitors

CoV $3CL_{pro}$'s representing members from each of the α, β, γ phylogenetic groups and subgroups can be expressed and purified to high purity to be assayed for inhibition by the designed library: FIPV-, PEDV-, and NL63-$3CL_{pro}$ from the α-CoV lineage, HKU1-, OC43-, SARS-, HKU4-, HKU5-, and HKU9-3CLpro from the β-CoV lineage, and IBV-3CLpro from the γ CoV lineage (St. John, et al., Bioorg Med Chem Lett 2015, 25(22):5072-5077; Grum-Tokars, et al., Virus Res 2008, 133(1):63-73). The compounds can tested against all ten 3CLpro's individually to determine inhibition. For example, the enzymatic activity of a given 3CLpro in the presence of a library member at a concentration of 100 μM is measured using a synthetic FRET peptide substrate containing the consensus nsp4-nsp5 cleavage site known for 3CLpro's: HilyteFluor™-488-ESATLQSGLRKAK-(QXL 520)-$NH_2$ (AnaSpec, Inc.). $IC_{50}$ values are then determined for compounds that produced greater than 50% inhibition of a given 3CLpro at 100 μM.

Example 237: Evaluation of Antiviral Activity of Compounds Against COVID-19 (nCoV-2019, SARS-CoV2) Mpro in the Enzymatic Assay Compounds were assayed using standard methods to assess compound activity and IC50. As an exemplary for assessment of the SARS-COV2 Mpro, the C-His6-tagged Mpro (NC045512) was cloned, expressed in *E. coli* and purified. The assay buffer contained 20 mM of Tris-HCl (pH 7.3), 100 mM of NaCl, 1 mM of EDTA, 5 mM of TCEP and 0.1% BSA. The final concentrations of the Mpro protein and substrate were 25 nM and 25 μM, respectively, in the Mpro enzymatic assay. The Km of the Mpro substrate for the protease was 13.5 M.

The compounds were added to an assay plate. For 100% inhibition control (HPE, hundred percent effect), 1 μM GC376 was added. For no inhibition control (ZPE, zero percent effect), no compound was added. Each activity testing point had a relevant background control to normalize the fluorescence interference of compound.

IC50 values of compounds were calculated with the GraphPad Prism software using the nonlinear regression model of log(inhibitor) vs. response—Variable slope (four parameters). The inhibition activity was calculated using the formula below, IC50 values is calculated using the Inhibition % data.

Inhibition %=[(Sample−Average ZPE)/(Average HPE-Average ZPE)]*100%#

#HEP: Hundred percent effect controls. Containing substrate+enzyme+1 uM GC376.

ZPE: Zero percent effective controls. Containing enzyme+substrate, no compound.

Sample: Compound activity testing wells. Containing compound+enzyme+substrate.

BG: Compound background control wells. Containing compound+substrate, no enzyme.

Example 238: Evaluation of Antiviral Activity of Compounds Against Human Coronavirus (HCov) 229E and OC43 in the Cytopathic Effect (CPE) Assays Compounds were assayed using standard methods against multiple coronaviral strains, including HCoV 229E and OC43 strains. The antiviral activity of compounds was calculated based on the protection of the virus-induced CPE at each concentration normalized by the virus control.

Reagents and instruments used in this assay include luminescent cell viability assay kit CellTiter Glo (Promega) and Microplate Reader Synergy2 (BioTek).

Virus—HCoV 229E

Cytopathic effect (CPE) was measured by CellTiter Glo following the manufacturer's manual. The antiviral activity of compounds was calculated based on the protection of the virus-induced CPE at each concentration normalized by the virus control.

Virus—HCov OC43

Reference compound used was remdesivir; detection reagent: CellTiter Glo.) The CPE were measured by CellTiter Glo following the manufacturer's manual. The antiviral activity of compounds was calculated based on the protection of the virus-induced CPE at each concentration normalized by the virus control.

The cytotoxicity of compounds was assessed under the same conditions, but without virus infection, in parallel. Cell viability was measured with CellTiter Glo. The antiviral activity and cytotoxicity of compounds were expressed as % Inhibition and % Viability, respectively, and calculated with formulas.

Table 2, Table 3, Table 4 and Table 5 below show activity data. In some embodiments, certain stereoisomers of disclosed compounds may have significant activity as compared to other stereoisomers of the same compound, for example, the R, R-stereoisomer may have significant activity as compared to, for example, the S, R-stereoisomer and/or to the racemate.

TABLE 2

Activity data for compounds.

| Compound No. | 229E Mpro $EC_{50}$ | COVID-19 Mpro $IC_{50}$ |
|---|---|---|
| 100 | C | B |
| 100a | | A |
| 102a | | A |
| 103 | C | B |
| 104 | | C |
| 105 | B | A |
| 105a | | A |
| 109 | C | A |

TABLE 2-continued

Activity data for compounds.

| Compound No. | 229E Mpro $EC_{50}$ | COVID-19 Mpro $IC_{50}$ |
|---|---|---|
| 110 | A | A |
| 117 | C | A |
| 118 | C | A |
| 120 Isomer 1 | B | A |
| 120 Isomer 2 | B | B |
| 122 | A | |
| 123 | D | D |
| 124 | B | A |
| 123a | A | A |
| 124a | A | A |
| 125 | B | B |
| 126 | A | A |
| 127 | A | A |
| 128 | C | B |
| 129 | A | A |
| 129a | A | A |
| 130a | D | D |
| 130b | C | A |
| 130c | A | A |
| 130d | A | A |
| 131a | A | A |
| 131b | A | A |
| 131c | A | A |
| 131d | A | A |
| 226 | D | D |
| 254 | D | D |
| 254 Isomer 1 | D | C |
| 254 Isomer 2 | D | D |
| 403 | D | D |
| 415 | D | C |
| 443 | D | C |
| 455 | D | C |
| 591 | C | C |
| 663 | D | C |
| 759 | A | A |
| 775 | C | B |
| 811 | D | D |
| 813 | D | D |
| 832 | C | |
| 833 | C | C |
| 846 | D | |
| 853 | C | C |
| 899 | | A |
| 950 | C | C |
| 952 | D | C |
| 962 | C | B |
| 966 | A | A |
| 967 | D | C |
| 969 | D | D |
| 975 | C | B |
| 136 Isomer 4 | D | D |
| 136a | A | A |
| 136b | A | A |
| 136c | A | A |
| 200 Isomer 1 | A | A |
| 200 Isomer 2 | A | A |
| 202 Isomer 1 | D | D |
| 202 Isomer 2 | D | D |
| 206 Isomer 1 | A | A |
| 206 Isomer 2 | A | A |
| 208 Isomer 1 | C | B |
| 208 Isomer 2 | D | D |
| 217 Isomer 2 | D | D |
| 217 Isomer 2.1 | D | D |
| 217 Isomer 2.2 | A | A |
| 223 Isomer 2 | D | C |
| 232 Isomer 2 | D | C |
| 236 Isomer 1 | A | A |
| 236 Isomer 2 | A | A |
| 239 Isomer 1 | B | A |
| 239 Isomer 2 | D | D |
| 244 Isomer 1 | D | C |
| 247 Isomer 1 | D | C |
| 252 Isomer 1 | A | A |
| 252 Isomer 2 | A | A |
| 255 Isomer 1 | D | C |
| 255 Isomer 2 | D | D |
| 255a Isomer 1 | A | A |
| 255a Isomer 2 | A | A |
| 262 Isomer 1 | A | A |
| 262 Isomer 2 | D | C |
| 268 Isomer 2 | D | D |
| 272 Isomer 1 | A | A |
| 272 Isomer 2 | A | A |
| 278 Isomer 1 | D | C |
| 278 Isomer 2 | D | C |
| 284 Isomer 1 | D | C |
| 284 Isomer 2 | D | D |
| 292 Isomer 1 | D | C |
| 292 Isomer 2 | D | D |
| 293 Isomer 1 | D | D |
| 293 Isomer 2 | C | B |
| 299 Isomer 1 | B | B |
| 299 Isomer 2 | D | D |
| 307 Isomer 1 | D | D |
| 307 Isomer 2 | C | A |
| 308 Isomer 1 | A | A |
| 308 Isomer 2 | D | D |
| 371a Isomer 1 | D | D |
| 371a Isomer 2 | A | A |
| 373a Isomer 1 | A | A |
| 373a Isomer 2 | A | A |
| 374 Isomer 1 | A | A |
| 374 Isomer 2 | D | D |
| 383 Isomer 2 | D | C |
| 387 Isomer 2 | D | D |
| 391 Isomer 1 | D | D |
| 391 Isomer 2 | C | B |
| 407 Isomer 1 | D | D |
| 407 Isomer 2 | B | A |
| 419 Isomer 1 | D | D |
| 419 Isomer 2 | D | C |
| 427 Isomer 1 | C | B |
| 427 Isomer 2 | D | D |
| 435 Isomer 1 | D | C |
| 435 Isomer 2 | D | B |
| 439 Isomer 1 | D | C |
| 439 Isomer 2 | D | C |
| 459 Isomer 1 | D | C |
| 459 Isomer 2 | D | C |
| 471 Isomer 2 | D | B |
| 475 Isomer 1 | D | D |
| 475 Isomer 2 | C | B |
| 527 Isomer 1 | D | C |
| 579 Isomer 1 | D | D |
| 579 Isomer 2 | C | A |
| 583 Isomer 1 | D | D |
| 583 Isomer 2 | D | D |
| 587 Isomer 1 | D | D |
| 587 Isomer 2 | D | C |
| 595 Isomer 1 | D | C |
| 595 Isomer 2 | D | D |
| 619 Isomer 1 | D | D |
| 619 Isomer 2 | D | C |
| 627 Isomer 1 | D | D |
| 627 Isomer 2 | D | C |
| 643 Isomer 1 | D | D |
| 643 Isomer 2 | D | C |
| 647 Isomer 1 | D | D |
| 647 Isomer 2 | D | D |
| 659 Isomer 1 | D | C |
| 659 Isomer 2 | D | C |
| 667 Isomer 1 | D | D |
| 667 Isomer 2 | D | C |
| 671 Isomer 1 | D | D |
| 671 Isomer 2 | D | D |
| 675 Isomer 1 | D | D |
| 675 Isomer 2 | D | C |
| 679 Isomer 1 | D | D |
| 679 Isomer 2 | D | B |
| 683 Isomer 1 | C | C |
| 683 Isomer 2 | C | A |

TABLE 2-continued

| Activity data for compounds. | | |
|---|---|---|
| Compound No. | 229E Mpro $EC_{50}$ | COVID-19 Mpro $IC_{50}$ |
| 690a | A | A |
| 690b | A | A |
| 711a | D | D |
| 723 Isomer 1 | D | D |
| 723 Isomer 2 | C | B |
| 735 Isomer 1 | D | D |
| 735 Isomer 2 | D | C |
| 747b Isomer 1 | D | D |
| 747b Isomer 2 | D | C |
| 755 Isomer 1 | D | D |
| 755 Isomer 2 | C | B |
| 763 Isomer 1 | D | D |
| 763 Isomer 2 | C | B |
| 767 Isomer 1 | D | D |
| 767 Isomer 2 | D | C |
| 771 Isomer 1 | D | D |
| 771 Isomer 2 | C | C |
| 779 Isomer 1 | D | D |
| 779 Isomer 2 | C | C |
| 791 Isomer 1 | D | D |
| 791 Isomer 2 | D | C |
| 810 Isomer 1 | D | D |
| 810 Isomer 2 | C | A |
| 810 Isomer 3 | D | C |
| 810 Isomer 4 | D | C |
| 812 Isomer 1 | D | D |
| 812 Isomer 2 | C | C |
| 812 Isomer 3 | D | C |
| 815a Isomer 1 | D | D |
| 815a Isomer 2 | D | D |
| 817 Isomer 1 | D | D |
| 817 Isomer 2 | D | D |
| 823a Isomer 1 | D | D |
| 823a Isomer 2 | D | D |
| 841 Isomer 1 | D | D |
| 841 Isomer 1.2 | A | A |
| 841 Isomer 2 | A | |
| 841 Isomer 2.1 | C | B |
| 841a Isomer 1 | D | D |
| 841a Isomer 2 | D | C |
| 846 Isomer 1.1 | D | B |
| 846 Isomer 1.2 | B | A |
| 870 Isomer 1 | D | D |
| 870 Isomer 2 | D | C |
| 876 Isomer 1 | D | C |
| 876 Isomer 2 | D | B |
| 885 Isomer 1 | B | A |
| 885 Isomer 2 | D | D |
| 899a | | A |
| 910 Isomer 1 | D | D |
| 910 Isomer 2 | D | B |
| 946b | C | B |
| 947 Isomer 1 | D | C |
| 947 Isomer 2 | C | A |
| 948 Isomer 1 | C | C |
| 948 Isomer 2 | C | A |
| 954 Isomer 1 | A | A |
| 954b | C | C |
| 954b Isomer 2 | B | A |
| 955 Isomer 1 | C | C |
| 955 Isomer 2 | C | B |
| 957 Isomer 1 | C | C |
| 957 Isomer 2 | B | A |
| 959 Isomer 1 | C | A |
| 959 Isomer 2 | D | C |
| 961 Isomer 1 | D | C |
| 961 Isomer 2 | C | A |
| 966b | C | B |
| 990e Isomer 1 | D | D |
| 990e Isomer 2 | D | D |
| 993c | D | D |
| 997c | D | B |
| 1007c Isomer 1 | D | D |
| 1007c Isomer 2 | D | C |
| 1011c Isomer 1 | D | D |
| 1011c Isomer 2 | D | D |

TABLE 2-continued

| Activity data for compounds. | | |
|---|---|---|
| Compound No. | 229E Mpro $EC_{50}$ | COVID-19 Mpro $IC_{50}$ |
| 1077 | D | D |
| 1077 Isomer 1 | D | B |
| 1077 Isomer 2 | D | D |
| 1086b Isomer 1 | D | D |
| 1086b Isomer 2 | D | C |
| 1087 Isomer 1 | D | D |
| 1087 Isomer 2 | D | C |
| 1088 Isomer 1 | D | D |
| 1088 Isomer 2 | D | D |
| 1092 Isomer 1 | D | D |
| 1092 Isomer 2 | D | D |
| 1094 Isomer 1 | D | D |
| 1094 Isomer 2 | C | B |
| 1095b | D | D |
| 1095b Isomer 1 | D | D |
| 1095b Isomer 2 | D | D |
| 1096 Isomer 1 | D | C |
| 1096 Isomer 2 | D | D |
| 1097 Isomer 1 | D | D |
| 1097 Isomer 1.1 | D | D |
| 1097 Isomer 1.2 | A | A |
| 1097 Isomer 2 | C | B |
| 1097 Isomer 2.1 | C | B |
| 1097 Isomer 2.2 | C | B |
| 1098 Isomer 1 | D | C |
| 1098 Isomer 2 | D | D |
| 1099 Isomer 1 | D | D |
| 1099 Isomer 2 | D | D |
| 1100 Isomer 1 | D | D |
| 1100 Isomer 2 | D | D |
| 1105 Isomer 1 | D | D |
| 1105 Isomer 2 | D | D |
| 1101 | C | A |
| 1114 | C | B |
| 1119 | D | C |
| 1122 | D | D |
| 1123 | D | D |
| 1141 | D | D |
| 1158 | D | D |
| 1160 | D | D |
| 1161 | D | D |
| 1174 | D | C |
| 1175 | D | C |
| 1182 | D | D |
| 1185 | D | D |
| 1185 | D | D |
| 1188 | D | C |
| 1199 | D | D |
| 1120 Isomer 1 | D | D |
| 1120 Isomer 2 | D | C |
| 1121b Isomer 1 | C | B |
| 1121b Isomer 2 | D | C |
| 1122 Isomer 1 | D | D |
| 1122 Isomer 2 | D | B |
| 1127 Isomer 1 | D | D |
| 1127 Isomer 2 | D | D |
| 1131 Isomer 1 | D | D |
| 1131 Isomer 2 | D | D |
| 1133a | A | A |
| 1135b | A | A |
| 1136b | C | C |
| 1139 Isomer 1 | D | D |
| 1139 Isomer 2 | D | D |
| 1140 Isomer 1 | D | D |
| 1140 Isomer 2 | D | C |
| 1141 Isomer 1 | B | C |
| 1141 Isomer 2 | D | D |
| 1141 Isomer 3 | B | A |
| 1141 Isomer 4 | D | B |
| 1142 Isomer 1 | D | D |
| 1142 Isomer 2 | D | C |
| 1148b Isomer 2 | D | B |
| 1148d Isomer 1 | D | C |
| 1149b | D | D |
| 1154 Isomer 1 | D | C |
| 1154 Isomer 2 | D | D |

TABLE 2-continued

Activity data for compounds.

| Compound No. | 229E Mpro $EC_{50}$ | COVID-19 Mpro $IC_{50}$ |
|---|---|---|
| 1156 Isomer 1 | D | C |
| 1156 Isomer 2 | D | D |
| 1157 Isomer 1 | D | D |
| 1157 Isomer 2 | D | C |
| 1158 Isomer 1 | D | D |
| 1158 Isomer 2 | D | C |
| 1160 Isomer 1 | D | D |
| 1160 Isomer 2 | C | C |
| 1160 Isomer 3 | D | C |
| 1160 Isomer 4 | D | C |
| 1161 Isomer 1 | D | D |
| 1161 Isomer 2 | C | C |
| 1161 Isomer 3 | C | C |
| 1161 Isomer 4 | C | C |
| 1163 Isomer 1 | D | C |
| 1163 Isomer 2 | D | D |
| 1165 Isomer 1 | D | D |
| 1165 Isomer 2 | D | B |
| 1170 Isomer 1 | C | B |
| 1170 Isomer 2 | D | D |
| 1171 Isomer 1 | D | B |
| 1171 Isomer 1 | D | D |
| 1174 Isomer 1 | D | C |
| 1174 Isomer 2 | D | B |
| 1175 Isomer 1 | D | D |
| 1175 Isomer 2 | D | B |
| 1176 Isomer 1 | D | D |
| 1176 Isomer 2 | D | B |
| 1180 Isomer 1 | C | C |
| 1180 Isomer 2 | D | D |
| 1187 Isomer 1 | D | D |
| 1187 Isomer 2 | D | D |
| 1194 Isomer 1 | D | D |
| 1194 Isomer 2 | D | B |
| 1195 Isomer 1 | D | D |
| 1195 Isomer 2 | D | C |
| 1196 Isomer 1 | D | C |
| 1196 Isomer 2 | D | D |
| 1197 Isomer 1 | D | D |
| 1197 Isomer 2 | D | C |
| 1198 Isomer 1 | C | B |
| 1198 Isomer 2 | D | D |
| 1199 Isomer 1 | D | D |
| 1199 Isomer 2 | D | D |
| 1200 | D | D |
| 1202 Isomer 1 | D | D |
| 1202 Isomer 2 | D | D |
| 1207 Isomer 1 | B | C |
| 1207 Isomer 2 | A | A |
| 1210 Isomer 1 | D | B |
| 1210 Isomer 2 | D | D |
| 1211 Isomer 1 | D | C |
| 1211 Isomer 2 | D | D |
| 1212 Isomer 1 | D | D |
| 1212 Isomer 2 | D | D |
| 1228 | D | C |
| 1230 Isomer 1 | C | A |
| 1230 Isomer 2 | D | D |
| 1232 Isomer 1 | C | C |
| 1232 Isomer 2 | D | D |
| 1244 | A | A |
| 1251 Isomer 2 | D | D |
| 1251 Isomer 1 | D | C |
| 1259 Isomer 1 | D | C |
| 1259 Isomer 2 | D | D |
| 1261 | C | A |
| 1263 | B | A |
| 1265 Isomer 1 | D | D |
| 1265 Isomer 2 | D | D |
| 1267 | D | C |
| 1274 | D | D |
| 1280 Isomer 1 | D | D |
| 1280 Isomer 2 | C | A |
| 1288 Isomer 1 | D | D |
| 1288 Isomer 2 | D | D |
| 1288a Isomer 1 | D | D |
| 1288a Isomer 2 | D | C |
| 1289 Isomer 1 | A | A |
| 1289 Isomer 2 | A | A |
| 1289 | A | A |
| 1305 | A | A |
| 1307 | A | A |
| 1311 | D | D |
| 1315 | D | D |
| 1320 | A | A |
| 1322 | D | D |
| 1326 | D | D |
| 1347 | D | D |
| 1419 | D | D |
| 1290 Isomer 1 | D | D |
| 1290 Isomer 2 | C | B |
| 1293 Isomer 1 | D | D |
| 1293 Isomer 2 | D | D |
| 1293 Isomer 3 | D | C |
| 1293 Isomer 4 | D | B |
| 1297 Isomer 1 | D | C |
| 1297 Isomer 2 | D | D |
| 1299 Isomer 1 | D | C |
| 1299 Isomer 2 | D | D |
| 1303 Isomer 1 | D | C |
| 1303 Isomer 2 | D | D |
| 1303 Isomer 2.1 | C | C |
| 1303 Isomer 2.2 | D | D |
| 1303 Isomer 3 | D | D |
| 1303 Isomer 3.1 | D | D |
| 1303 Isomer 3.2 | B | A |
| 1309 Isomer 1 | D | D |
| 1309 Isomer 2 | D | C |
| 1313 Isomer 1 | D | D |
| 1313 Isomer 2 | D | C |
| 1315 Isomer 1 | D | D |
| 1315 Isomer 2 | D | C |
| 1316 Isomer 1 | B | A |
| 1316 Isomer 2 | A | A |
| 1318 Isomer 1 | D | D |
| 1318 Isomer 2 | D | D |
| 1324 Isomer 1 | B | A |
| 1324 Isomer 2 | B | B |
| 1328 Isomer 1 | D | D |
| 1328 Isomer 2 | D | C |
| 1330 Isomer 1 | D | D |
| 1330 Isomer 2 | C | C |
| 1336 Isomer 1 | C | B |
| 1336 Isomer 2 | B | B |
| 1337 Isomer 1 | C | B |
| 1337 Isomer 2 | C | B |
| 1338 Isomer 1 | D | C |
| 1338 Isomer 2 | B | C |
| 1345 Isomer 1 | D | D |
| 1345 Isomer 2 | B | C |
| 1349 Isomer 1 | D | D |
| 1349 Isomer 2 | C | C |
| 1351 Isomer 1 | D | D |
| 1351 Isomer 2 | C | C |
| 1353 Isomer 1 | D | D |
| 1353 Isomer 2 | A | A |
| 1355 Isomer 1 | C | D |
| 1355 Isomer 2 | C | D |

A > 30 μM, B > 10 μM and ≤ 30 μM, C ≥ 2 μM and ≤ 10 μM, D < 2 μM.

TABLE 3

Activity data for compounds.

| Compound No. | 229E CPE $EC_{50}$ |
|---|---|
| 100 | C |
| 103 | B |
| 105 | C |

TABLE 3-continued

| Activity data for compounds. | |
|---|---|
| Compound No. | 229E CPE $EC_{50}$ |
| 109 | C |
| 117 | C |
| 118 | D |
| 123 | D |
| 124 | B |
| 125 | C |
| 128 | C |
| 1248 Isomer 1 | D |
| 1248 Isomer 2 | C |
| 133 Isomer R1 | C |
| 136 Isomer 4 | C |
| 202 Isomer 1 | D |
| 202 Isomer 2 | D |
| 208 Isomer 1 | C |
| 208 Isomer 2 | D |
| 217 Isomer 2 | D |
| 223 Isomer 2 | C |
| 226 | C |
| 232 Isomer 2 | D |
| 238 Isomer 1 | C |
| 238 Isomer 2 | D |
| 244 Isomer 1 | D |
| 244 Isomer 1.2 | D |
| 247 Isomer 1 | D |
| 254 | D |
| 254 Isomer 1 | C |
| 254 Isomer 2.1 | D |
| 254 Isomer 2.2 | D |
| 255 Isomer 1 | B |
| 255 Isomer 2 | D |
| 262 | D |
| 268 Isomer 2 | D |
| 278 Isomer 2 | C |
| 284 Isomer 2 | D |
| 292 Isomer 2 | D |
| 293 Isomer 1 | D |
| 299 Isomer 2 | D |
| 307 Isomer 1 | D |
| 308 Isomer 2 | D |
| 371 | D |
| 374 | D |
| 382 Isomer 2 | D |
| 383 Isomer 2 | D |
| 386 Isomer 2 | D |
| 387 Isomer 2 | D |
| 391 | C |
| 403 | C |
| 407 | D |
| 415 | C |
| 419 Isomer 1 | C |
| 427 Isomer 2 | D |
| 435 Isomer 1 | C |
| 459 Isomer 1 | D |
| 471 Isomer 2 | D |
| 475 | D |
| 527 Isomer 1 | D |
| 579 Isomer 1 | D |
| 583 Isomer 1 | D |
| 583 Isomer 2 | C |
| 587 Isomer 1 | D |
| 587 Isomer 2 | C |
| 591 | C |
| 595 Isomer 1 | C |
| 619 Isomer 1 | C |
| 619 Isomer 2 | D |
| 627 Isomer 1 | C |
| 627 Isomer 2 | C |
| 647 Isomer 2 | C |
| 659 Isomer 1 | D |
| 659 Isomer 2 | C |
| 663 | D |
| 666 Isomer 1 | D |
| 666 Isomer 2 | D |
| 671 Isomer 1 | D |
| 671 Isomer 2 | D |
| 674 Isomer 1 | D |

TABLE 3-continued

| Activity data for compounds. | |
|---|---|
| Compound No. | 229E CPE $EC_{50}$ |
| 679 Isomer 1 | D |
| 679 Isomer 2 | C |
| 723 Isomer 1 | D |
| 723 Isomer 2 | C |
| 747b Isomer 1 | C |
| 755 Isomer 1 | D |
| 755 Isomer 2 | D |
| 759 | D |
| 763 Isomer 2 | D |
| 767 Isomer 1 | C |
| 779 Isomer 1 | C |
| 791 Isomer 2 | D |
| 811 Isomer 1 | D |
| 811 Isomer 3 | C |
| 813 Isomer 1 | D |
| 813 Isomer 3 | D |
| 815 Isomer 1 | D |
| 815 Isomer 2 | D |
| 839 Isomer 1 | C |
| 846 Isomer 1 | D |
| 846 Isomer 1.1 | D |
| 846 Isomer 1.2 | B |
| 839 Isomer 1.1 | C |
| 870 Isomer 1 | D |
| 870 Isomer 2 | C |
| 876 Isomer 1 | D |
| 885 | C |
| 910 | D |
| 952 | C |
| 959 | C |
| 967 | C |
| 969 | C |
| 988 | D |
| 992 | C |
| 1008 Isomer 1 | C |
| 1008 Isomer 2 | C |
| 1119 | C |
| 1133 | D |
| 1139 Isomer 1 | D |
| 1139 Isomer 2 | C |
| 1149 | D |
| 1156 Isomer 1 | D |
| 1156 Isomer 2 | C |

A > 30 μM, B > 10 μM and ≤ 30 μM, C ≥ 2 μM and ≤ 10 μM, D < 2 μM.

TABLE 4

| Activity data for compounds. | |
|---|---|
| Compound No. | 229E $CC_{50}$ |
| 100 | A |
| 103 | A |
| 105 | A |
| 109 | A |
| 117 | A |
| 118 | A |
| 123 | A |
| 124 | A |
| 125 | B |
| 136 Isomer 4 | C |
| 202 Isomer 2 | A |
| 217 Isomer 2 | A |
| 223 Isomer 2 | A |
| 232 Isomer 2 | B |
| 244 Isomer 1 | A |
| 244 Isomer 1.2 | A |
| 254 Isomer 2 | A |
| 268 Isomer 2 | B |
| 382 Isomer 2 | A |
| 386 Isomer 2 | A |
| 471 Isomer 2 | C |
| 527 Isomer 1 | A |

TABLE 4-continued

| Activity data for compounds. | |
|---|---|
| Compound No. | 229E $CC_{50}$ |
| 583 Isomer 1 | A |
| 583 Isomer 2 | A |
| 666 Isomer 1 | B |
| 666 Isomer 2 | B |
| 671 Isomer 1 | B |
| 671 Isomer 2 | B |
| 674 Isomer 1 | A |
| 679 Isomer 1 | A |
| 679 Isomer 2 | B |

A > 30 μM, B > 10 μM and ≤ 30 μM, C ≥ 2 μM and ≤ 10 μM, D < 2 μM.

TABLE 5

| Activity data for compounds. | |
|---|---|
| Patent No. | OC43 IC50 (uM) MEDIAN |
| 226 | C |
| 403 | C |
| 415 | C |
| 443 | B |
| 455 | B |
| 591 | A |
| 663 | C |
| 759 | A |
| 775 | A |
| 811 | D |
| 813 | D |
| 853 | C |
| 950 | B |
| 952 | C |
| 962 | B |
| 966 | A |
| 967 | C |
| 969 | C |
| 975 | B |
| 1077 | D |
| 1101 | A |
| 1114 | A |
| 1119 | C |
| 1122 | D |
| 1123 | D |
| 1141 | C |
| 1158 | D |
| 1160 | D |
| 1161 | D |
| 1174 | D |
| 1175 | D |
| 1182 | D |
| 1185 | D |
| 1185 | D |
| 1188 | D |
| 1199 | D |
| 1200 | D |
| 1228 | B |
| 1244 | A |
| 1261 | A |
| 1263 | A |
| 1267 | D |
| 1274 | D |
| 1289 | A |
| 1305 | A |
| 1307 | A |
| 1311 | D |
| 1315 | D |
| 1320 | A |
| 1322 | D |
| 1326 | D |
| 1347 | D |
| 1419 | C |
| 1007c Isomer 1 | C |
| 1007c Isomer 2 | C |
| 1011c Isomer 1 | D |

TABLE 5-continued

| Activity data for compounds. | |
|---|---|
| Patent No. | OC43 IC50 (uM) MEDIAN |
| 1011c Isomer 2 | D |
| 1077 Isomer 1 | C |
| 1077 Isomer 2 | D |
| 1086b Isomer 1 | D |
| 1086b Isomer 2 | C |
| 1087 Isomer 1 | D |
| 1087 Isomer 2 | A |
| 1088 Isomer 1 | D |
| 1088 Isomer 2 | C |
| 1092 Isomer 1 | D |
| 1092 Isomer 2 | C |
| 1094 Isomer 1 | D |
| 1094 Isomer 2 | B |
| 1095b | D |
| 1095b Isomer 1 | D |
| 1095b Isomer 2 | D |
| 1096 Isomer 1 | C |
| 1096 Isomer 2 | D |
| 1097 Isomer 1 | D |
| 1097 Isomer 1.1 | D |
| 1097 Isomer 1.2 | A |
| 1097 Isomer 2 | C |
| 1097 Isomer 2.1 | B |
| 1097 Isomer 2.2 | B |
| 1098 Isomer 1 | C |
| 1098 Isomer 2 | D |
| 1099 Isomer 1 | D |
| 1099 Isomer 2 | C |
| 1100 Isomer 1 | D |
| 1100 Isomer 2 | D |
| 1105 Isomer 1 | D |
| 1105 Isomer 2 | D |
| 1120 Isomer 1 | C |
| 1120 Isomer 2 | B |
| 1121b Isomer 1 | A |
| 1121b Isomer 2 | C |
| 1122 Isomer 1 | D |
| 1122 Isomer 2 | C |
| 1127 Isomer 1 | D |
| 1127 Isomer 2 | D |
| 1131 Isomer 1 | D |
| 1131 Isomer 2 | C |
| 1133a | A |
| 1135b | A |
| 1136b | A |
| 1139 Isomer 1 | D |
| 1139 Isomer 2 | C |
| 1140 Isomer 1 | D |
| 1140 Isomer 2 | C |
| 1141 Isomer 1 | C |
| 1141 Isomer 2 | C |
| 1141 Isomer 3 | A |
| 1141 Isomer 4 | B |
| 1142 Isomer 1 | D |
| 1142 Isomer 2 | B |
| 1148b Isomer 2 | C |
| 1148d Isomer 1 | D |
| 1149b | D |
| 1154 Isomer 1 | C |
| 1154 Isomer 2 | D |
| 1156 Isomer 1 | C |
| 1156 Isomer 2 | D |
| 1157 Isomer 1 | D |
| 1157 Isomer 2 | C |
| 1158 Isomer 1 | D |
| 1158 Isomer 2 | D |
| 1160 Isomer 1 | D |
| 1160 Isomer 2 | C |
| 1160 Isomer 3 | C |
| 1160 Isomer 4 | C |
| 1161 Isomer 1 | D |
| 1161 Isomer 2 | C |
| 1161 Isomer 3 | B |
| 1161 Isomer 4 | C |
| 1163 Isomer 1 | B |
| 1163 Isomer 2 | D |

TABLE 5-continued

Activity data for compounds.

| Patent No. | OC43 IC50 (uM) MEDIAN |
|---|---|
| 1165 Isomer 1 | D |
| 1165 Isomer 2 | C |
| 1170 Isomer 1 | C |
| 1170 Isomer 2 | D |
| 1171 Isomer 1 | C |
| 1171 Isomer 1 | D |
| 1174 Isomer 1 | D |
| 1174 Isomer 2 | B |
| 1175 Isomer 1 | D |
| 1175 Isomer 2 | C |
| 1176 Isomer 1 | D |
| 1176 Isomer 2 | C |
| 1180 Isomer 1 | C |
| 1180 Isomer 2 | D |
| 1187 Isomer 1 | D |
| 1187 Isomer 2 | D |
| 1194 Isomer 1 | D |
| 1194 Isomer 2 | C |
| 1195 Isomer 1 | D |
| 1195 Isomer 2 | D |
| 1196 Isomer 1 | C |
| 1196 Isomer 2 | D |
| 1197 Isomer 1 | D |
| 1197 Isomer 2 | C |
| 1198 Isomer 1 | C |
| 1198 Isomer 2 | D |
| 1199 Isomer 1 | D |
| 1199 Isomer 2 | D |
| 1202 Isomer 1 | D |
| 1202 Isomer 2 | D |
| 1207 Isomer 1 | B |
| 1207 Isomer 2 | A |
| 1210 Isomer 1 | B |
| 1210 Isomer 2 | D |
| 1211 Isomer 1 | D |
| 1211 Isomer 2 | D |
| 1212 Isomer 1 | D |
| 1212 Isomer 2 | D |
| 1230 Isomer 1 | A |
| 1230 Isomer 2 | D |
| 1232 Isomer 1 | C |
| 1232 Isomer 2 | D |
| 1251 Isomer 1 | C |
| 1251 Isomer 2 | D |
| 1259 Isomer 1 | C |
| 1259 Isomer 2 | D |
| 1265 Isomer 1 | D |
| 1265 Isomer 2 | D |
| 1280 Isomer 1 | D |
| 1280 Isomer 2 | C |
| 1288 Isomer 1 | D |
| 1288 Isomer 2 | C |
| 1288a Isomer 1 | D |
| 1288a Isomer 2 | C |
| 1289 Isomer 1 | A |
| 1289 Isomer 2 | A |
| 1290 Isomer 1 | C |
| 1290 Isomer 2 | C |
| 1293 Isomer 1 | C |
| 1293 Isomer 2 | D |
| 1293 Isomer 3 | C |
| 1293 Isomer 4 | C |
| 1297 Isomer 1 | B |
| 1297 Isomer 2 | D |
| 1299 Isomer 1 | C |
| 1299 Isomer 2 | D |
| 1303 Isomer 1 | C |
| 1303 Isomer 2 | D |
| 1303 Isomer 2.1 | B |
| 1303 Isomer 2.2 | D |
| 1303 Isomer 3 | D |
| 1303 Isomer 3.1 | D |
| 1303 Isomer 3.2 | A |
| 1309 Isomer 1 | D |
| 1309 Isomer 2 | C |
| 1313 Isomer 1 | D |

TABLE 5-continued

Activity data for compounds.

| Patent No. | OC43 IC50 (uM) MEDIAN |
|---|---|
| 1313 Isomer 2 | C |
| 1315 Isomer 1 | D |
| 1315 Isomer 2 | C |
| 1316 Isomer 1 | A |
| 1316 Isomer 2 | A |
| 1318 Isomer 1 | D |
| 1318 Isomer 2 | D |
| 1324 Isomer 1 | A |
| 1324 Isomer 2 | C |
| 1328 Isomer 1 | D |
| 1328 Isomer 2 | C |
| 1330 Isomer 1 | D |
| 1330 Isomer 2 | B |
| 1336 Isomer 1 | A |
| 1336 Isomer 2 | A |
| 1337 Isomer 1 | A |
| 1337 Isomer 2 | A |
| 1338 Isomer 1 | C |
| 1338 Isomer 2 | B |
| 1345 Isomer 1 | D |
| 1345 Isomer 2 | B |
| 1349 Isomer 1 | D |
| 1349 Isomer 2 | C |
| 1351 Isomer 1 | D |
| 1351 Isomer 2 | C |
| 1353 Isomer 1 | A |
| 1353 Isomer 2 | A |
| 1355 Isomer 1 | A |
| 1355 Isomer 2 | A |
| 202 Isomer 2 | D |
| 208 Isomer 2 | C |
| 217 Isomer 2.1 | C |
| 217 Isomer 2.2 | A |
| 232 Isomer 2 | C |
| 254 Isomer 2 | D |
| 262 Isomer 1 | A |
| 262 Isomer 2 | B |
| 268 Isomer 2 | C |
| 272 Isomer 1 | A |
| 272 Isomer 2 | A |
| 278 Isomer 1 | B |
| 278 Isomer 2 | B |
| 284 Isomer 1 | B |
| 284 Isomer 2 | D |
| 292 Isomer 1 | C |
| 292 Isomer 2 | D |
| 293 Isomer 1 | D |
| 293 Isomer 2 | B |
| 299 Isomer 1 | B |
| 299 Isomer 2 | C |
| 307 Isomer 1 | D |
| 307 Isomer 2 | C |
| 308 Isomer 1 | A |
| 308 Isomer 2 | A |
| 371a Isomer 1 | A |
| 371a Isomer 2 | A |
| 373a Isomer 1 | A |
| 373a Isomer 2 | A |
| 374 Isomer 1 | A |
| 374 Isomer 2 | C |
| 391 Isomer 1 | D |
| 391 Isomer 2 | B |
| 407 Isomer 1 | C |
| 407 Isomer 2 | A |
| 419 Isomer 1 | C |
| 419 Isomer 2 | C |
| 427 Isomer 1 | A |
| 427 Isomer 2 | C |
| 435 Isomer 1 | C |
| 435 Isomer 2 | B |
| 439 Isomer 1 | B |
| 439 Isomer 2 | B |
| 459 Isomer 1 | C |
| 459 Isomer 2 | B |
| 471 Isomer 2 | C |
| 475 Isomer 1 | C |

TABLE 5-continued

Activity data for compounds.

| Patent No. | OC43 IC50 (uM) MEDIAN |
|---|---|
| 475 Isomer 2 | B |
| 527 Isomer 1 | C |
| 579 Isomer 1 | D |
| 579 Isomer 2 | B |
| 583 Isomer 1 | D |
| 583 Isomer 2 | D |
| 587 Isomer 1 | D |
| 587 Isomer 2 | C |
| 595 Isomer 1 | C |
| 595 Isomer 2 | D |
| 619 Isomer 1 | D |
| 619 Isomer 2 | C |
| 627 Isomer 1 | D |
| 627 Isomer 2 | B |
| 643 Isomer 1 | D |
| 643 Isomer 2 | C |
| 647 Isomer 1 | D |
| 647 Isomer 2 | C |
| 659 Isomer 1 | B |
| 659 Isomer 2 | C |
| 667 Isomer 1 | D |
| 667 Isomer 2 | D |
| 675 Isomer 1 | D |
| 675 Isomer 2 | C |
| 679 Isomer 1 | D |
| 679 Isomer 2 | C |
| 683 Isomer 1 | C |
| 683 Isomer 2 | B |
| 690a | A |
| 690b | A |
| 711a | D |
| 723 Isomer 1 | D |
| 723 Isomer 2 | C |
| 735 Isomer 1 | D |
| 735 Isomer 2 | C |
| 747b Isomer 1 | D |
| 747b Isomer 2 | C |
| 755 Isomer 1 | D |
| 755 Isomer 2 | C |
| 763 Isomer 1 | D |
| 763 Isomer 2 | C |
| 767 Isomer 1 | D |
| 767 Isomer 2 | C |
| 771 Isomer 1 | D |
| 771 Isomer 2 | B |
| 779 Isomer 1 | D |
| 779 Isomer 2 | C |
| 791 Isomer 1 | D |
| 791 Isomer 2 | D |
| 810 Isomer 1 | D |
| 810 Isomer 2 | A |
| 810 Isomer 3 | C |
| 810 Isomer 4 | C |
| 812 Isomer 1 | D |
| 812 Isomer 2 | B |
| 812 Isomer 3 | C |
| 815a Isomer 1 | D |
| 815a Isomer 2 | D |
| 817 Isomer 1 | D |
| 817 Isomer 2 | C |
| 823a Isomer 1 | D |
| 823a Isomer 2 | C |
| 870 Isomer 1 | D |
| 870 Isomer 2 | D |
| 876 Isomer 1 | B |
| 876 Isomer 2 | A |
| 885 Isomer 1 | A |
| 885 Isomer 2 | C |
| 910 Isomer 1 | D |
| 910 Isomer 2 | C |
| 946b | B |
| 947 Isomer 1 | C |
| 947 Isomer 2 | A |
| 948 Isomer 1 | C |
| 948 Isomer 2 | A |
| 954 Isomer 1 | A |

TABLE 5-continued

Activity data for compounds.

| Patent No. | OC43 IC50 (uM) MEDIAN |
|---|---|
| 954b | C |
| 954b Isomer 2 | A |
| 955 Isomer 1 | C |
| 955 Isomer 2 | B |
| 957 Isomer 1 | B |
| 957 Isomer 2 | A |
| 959 Isomer 1 | B |
| 959 Isomer 2 | C |
| 961 Isomer 1 | C |
| 961 Isomer 2 | B |
| 966b | B |
| 990e Isomer 1 | D |
| 990e Isomer 2 | D |
| 993c | C |
| 997c | C |

A > 30 μM, B > 10 μM and ≤ 30 μM, C ≥ 2 μM and ≤ 10 μM, D < 2 μM.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:

1. A compound represented by Formula I:

(Formula I)

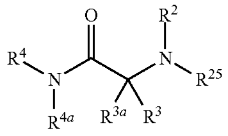

or a pharmaceutically acceptable salt or stereoisomer thereof, wherein:

$R^{25}$ is —C(O)$R^1$, $R^1$ is 4-7 membered heterocyclyl, wherein $R^1$ is optionally substituted by one, two or three substituents each selected from $R^a$, $R^2$ is $C_6$-$C_{14}$aryl, wherein $R^2$ is optionally substituted by one, two or three substituents each selected from $R^5$;

wherein $C_6$-$C_{14}$aryl may optionally be fused with one or more carbocyclyl or heterocyclyl groups, and wherein $C_6$-$C_{14}$aryl designates the number of carbon atoms in the aryl ring system;

$R^3$ is 5-6 membered monocyclic heteroaryl, wherein the 5-6 membered monocyclic heteroaryl contains at least one ring nitrogen and may have one, two or three optional substituents each selected from $R^a$;

$R^{3a}$ is selected from the group consisting of hydrogen and $C_1$-$C_6$alkyl;

$R^4$ is selected from the group consisting of $C_3$-$C_{10}$cycloalkyl and $C_1$-$C_6$alkyl-($C_6$-$C_{14}$aryl), wherein the $C_3$-$C_{10}$cycloalkyl is optionally substituted by one, two or three substituents each selected from $R^a$;

$R^{4a}$ is hydrogen;

$R^5$ is independently selected, for each occurrence, from the group consisting of halogen, $SF_5$, $C_1$-$C_6$alkyl, $C_3$-$C_{10}$cycloalkyl, and $C_6$-$C_{14}$aryl;

$R^a$ is independently selected, for each occurrence, from the group consisting of halogen, hydroxyl, cyano, —$OR^{aa}$, $C_1$-$C_6$alkyl, $C_1$-$C_6$haloalkyl, and $C_1$-$C_6$alkoxy; and $R^{aa}$ is $C_1$-$C_6$haloalkyl.

2. The compound of claim 1, wherein $R^1$ is a warhead selected from the group consisting of:

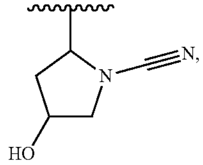
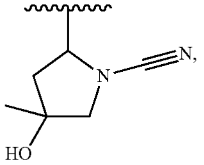
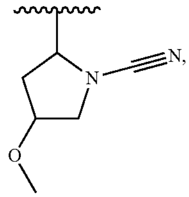
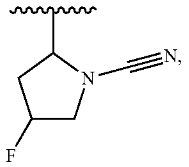
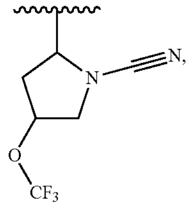
and
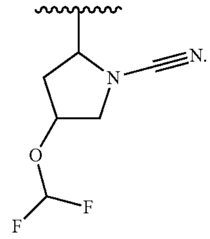

3. The compound of claim 1, wherein $R^2$ is selected from the group consisting of:

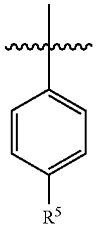
and
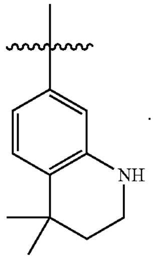
.

4. The compound of claim 1, wherein $R^3$ is selected from the group consisting of:

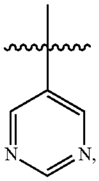
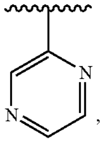
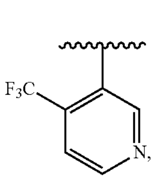
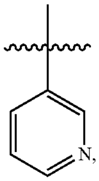
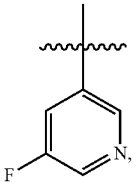
and
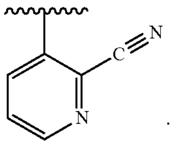
.

5. The compound of claim 1, wherein $R^{3a}$ is selected from the group consisting of hydrogen and $CH_3$.

6. The compound of claim 1, wherein $R^4$ is selected from the group consisting of:

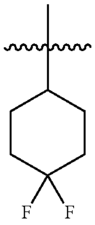
and
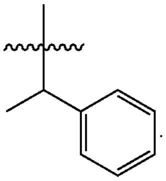
.

7. The compound of claim 1, wherein $R^5$ is selected from the group consisting of:

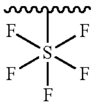
,
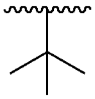
,
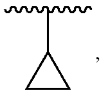
, and
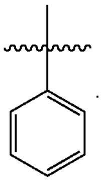
.

8. A protease inhibitor compound selected from the group consisting of:

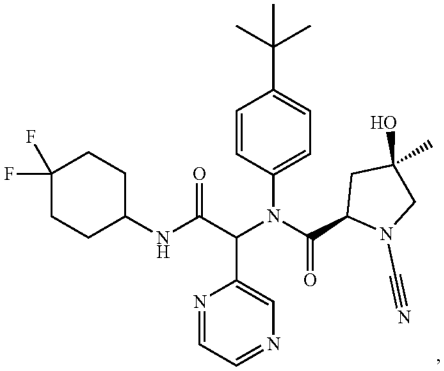
,

-continued
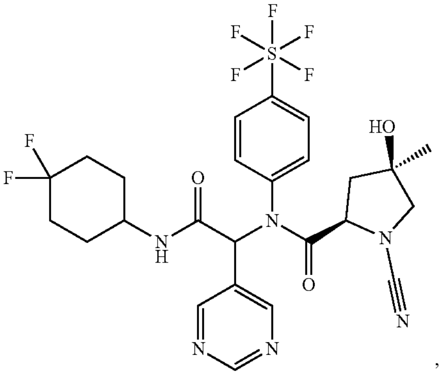
,
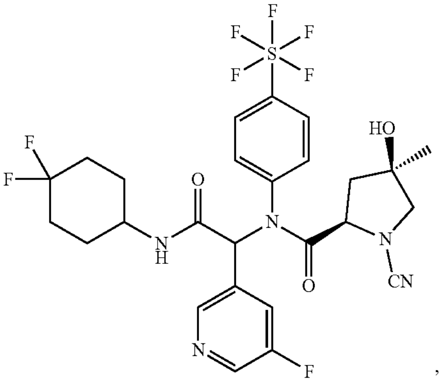
,
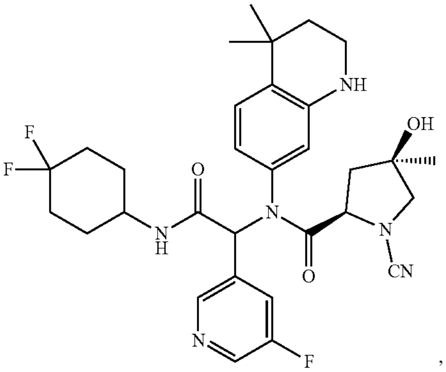
,
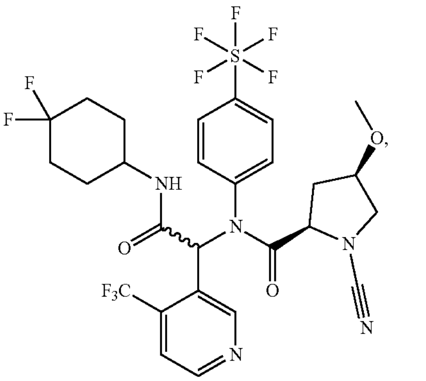
-continued
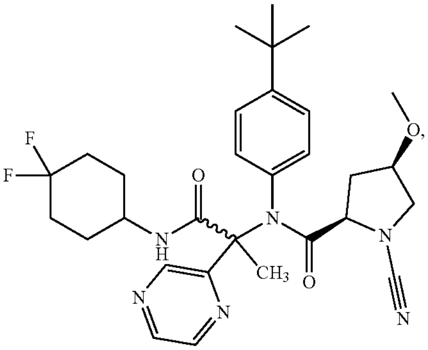
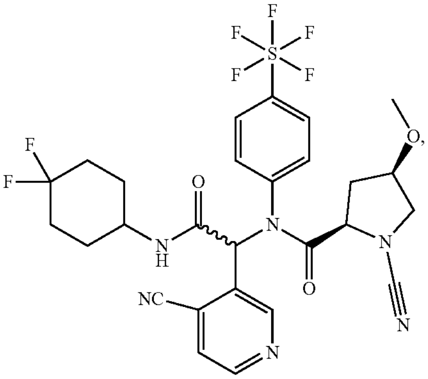
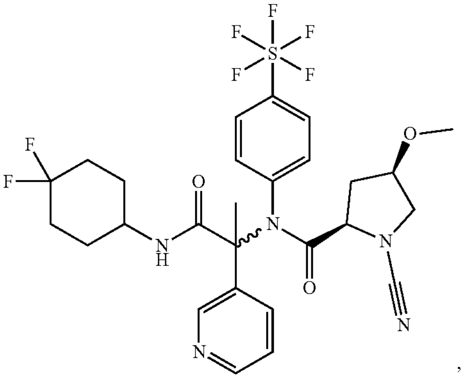
,
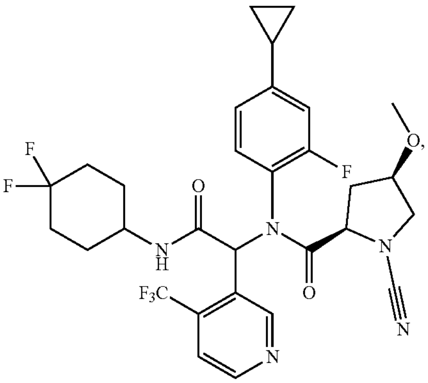

-continued

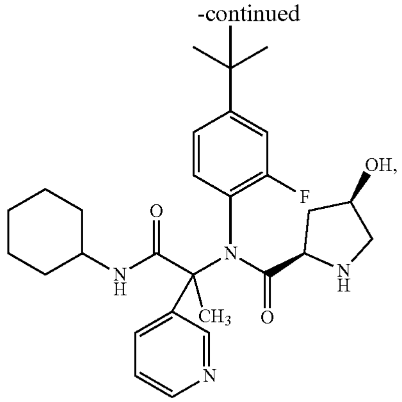

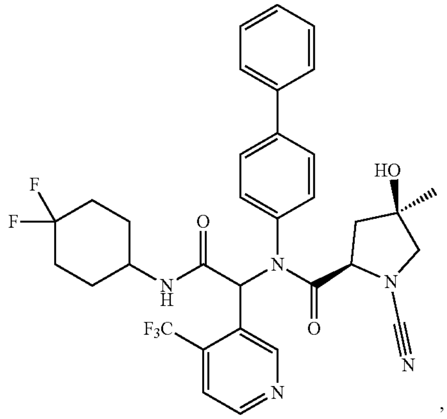

, and

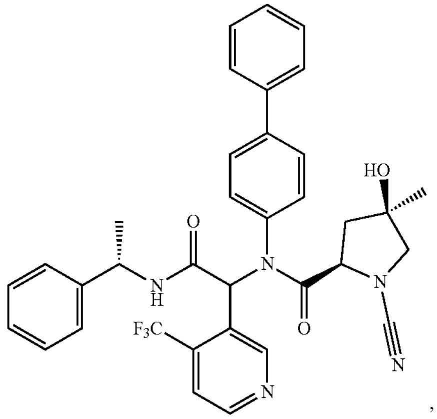

, or a pharmaceutically acceptable salt or stereoisomer thereof.

9. A protease inhibitor compound selected from the group consisting of:

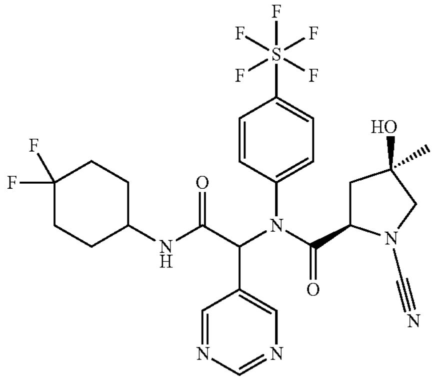

and

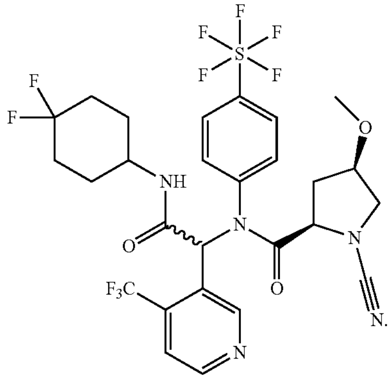

10. A pharmaceutical composition comprising a compound of claim 1 and a pharmaceutically acceptable excipient.

11. The pharmaceutical composition of claim 10, further comprising a second active agent.

12. A method of ameliorating or treating a viral infection in a patient in need thereof, comprising administering to the patient a therapeutically effective amount a compound of claim 1.

13. A method of ameliorating or treating SARS-CoV-2 (COVID-19) in a patient in need thereof, comprising administering to the patient a therapeutically effective amount a compound of claim 1.

14. The method of claim 13, further comprising administering an additional anti-viral therapeutic.

* * * * *